US009805994B1

(12) United States Patent
Lam et al.

(10) Patent No.: US 9,805,994 B1
(45) Date of Patent: Oct. 31, 2017

(54) MESH-STYLE NCEM PADS, AND PROCESS FOR MAKING SEMICONDUCTOR DIES, CHIPS, AND WAFERS USING IN-LINE MEASUREMENTS FROM SUCH PADS

(71) Applicant: PDF Solutions, Inc., San Jose, CA (US)

(72) Inventors: Stephen Lam, Freemont, CA (US); Dennis Ciplickas, San Jose, CA (US); Tomasz Brozek, Morgan Hill, CA (US); Jeremy Cheng, San Jose, CA (US); Simone Comensoli, Darfo Boario Terme (IT); Indranil De, Mountain View, CA (US); Kelvin Doong, Hsinchu (TW); Hans Eisenmann, Tutzing (DE); Timothy Fiscus, New Galilee, PA (US); Jonathan Haigh, Pittsburgh, PA (US); Christopher Hess, Belmont, CA (US); John Kibarian, Los Altos Hills, CA (US); Sherry Lee, Monte Sereno, CA (US); Marci Liao, Santa Clara, CA (US); Sheng-Che Lin, Hsinchu (TW); Hideki Matsuhashi, Santa Clara, CA (US); Kimon Michaels, Monte Sereno, CA (US); Conor O'Sullivan, Campbell, CA (US); Markus Rauscher, Munich (DE); Vyacheslav Rovner, Pittsburgh, PA (US); Andrzej Strojwas, Pittsburgh, PA (US); Marcin Strojwas, Pittsburgh, PA (US); Carl Taylor, Pittsburgh, PA (US); Rakesh Vallishayee, Dublin, CA (US); Larg Weiland, Hollister, CA (US); Nobuharu Yokoyama, Tokyo (JP)

(73) Assignee: PDF Solutions, Inc., San Jose, CA (US)

( * ) Notice: Subject to any disclaimer, the term of this patent is extended or adjusted under 35 U.S.C. 154(b) by 0 days.

(21) Appl. No.: 15/090,274

(22) Filed: Apr. 4, 2016

Related U.S. Application Data

(63) Continuation-in-part of application No. 14/612,841, filed on Feb. 3, 2015.

(Continued)

(51) Int. Cl.

| | |
|---|---|
| ***H01L 23/58*** | (2006.01) |
| ***H01L 21/66*** | (2006.01) |
| ***H01L 27/02*** | (2006.01) |

(52) U.S. Cl.
CPC .......... *H01L 22/32* (2013.01); *H01L 27/0207* (2013.01)

(58) Field of Classification Search
CPC ...................................................... H01L 22/32

(Continued)

(56) References Cited

U.S. PATENT DOCUMENTS

| | | | |
|---|---|---|---|
| 5,008,727 | A | 4/1991 | Katsura et al. |
| 5,576,223 | A | 11/1996 | Zeininger et al. |

(Continued)

FOREIGN PATENT DOCUMENTS

| | | |
|---|---|---|
| WO | WO/03/019456 | 3/2003 |
| WO | WO/03/034492 | 4/2003 |

(Continued)

OTHER PUBLICATIONS

S.-C. Lei et al., "Contact leakage and open monitoring with an advanced e-beam inspection system," Proc. SPIE 6518, Apr. 5, 2007.

(Continued)

*Primary Examiner* — Calvin Lee
(74) *Attorney, Agent, or Firm* — David Garrod

(57) ABSTRACT

Wafers, chips, or dies that contain fill cells with structures configured to obtain in-line data via non-contact electrical (Continued)

measurements ("NCEM"). Such NCEM-enabled fill cells may target/expose a variety of open-circuit, short-circuit, leakage, or excessive resistance failure modes, and may include NCEM pads that comprise a mesh of GATECNT and AACNT stripes. Such wafers, chips, or dies may include Designs of Experiments ("DOEs"), comprised of multiple NCEM-enabled fill cells, in at least two variants, all targeted to the same failure mode(s).

18 Claims, 2550 Drawing Sheets

Related U.S. Application Data

(60) Provisional application No. 62/268,463, filed on Dec. 16, 2015.

(58) Field of Classification Search
USPC ........................................ 438/11-18; 257/48
See application file for complete search history.

(56) References Cited

U.S. PATENT DOCUMENTS

| | | | |
|---|---|---|---|
| 5,576,833 | A | 11/1996 | Miyoshi et al. |
| 5,773,315 | A | 6/1998 | Jarvis |
| 5,959,459 | A | 9/1999 | Satya et al. |
| 6,061,814 | A | 5/2000 | Sugasawara et al. |
| 6,091,249 | A | 7/2000 | Talbot et al. |
| 6,236,222 | B1 | 5/2001 | Sur, Jr. et al. |
| 6,297,644 | B1 | 10/2001 | Jarvis et al. |
| 6,388,315 | B1 | 5/2002 | Clark et al. |
| 6,433,561 | B1 | 8/2002 | Satya et al. |
| 6,452,412 | B1 | 9/2002 | Jarvis et al. |
| 6,509,197 | B1 | 1/2003 | Satya et al. |
| 6,524,873 | B1 | 2/2003 | Satya et al. |
| 6,539,106 | B1 | 3/2003 | Gallarda et al. |
| 6,576,923 | B2 | 6/2003 | Satya et al. |
| 6,633,174 | B1 | 10/2003 | Satya et al. |
| 6,636,064 | B1 | 10/2003 | Satya et al. |
| 6,771,806 | B1 | 8/2004 | Satya et al. |
| 6,815,345 | B2 | 11/2004 | Zhao et al. |
| 6,844,550 | B1 | 1/2005 | Yin et al. |
| 6,861,666 | B1 | 3/2005 | Weiner et al. |
| 6,897,444 | B1 | 5/2005 | Adler |
| 6,949,765 | B2 | 9/2005 | Song et al. |
| 6,967,110 | B2 | 11/2005 | Guldi et al. |
| 7,026,175 | B2 | 4/2006 | Li et al. |
| 7,101,722 | B1 | 9/2006 | Wang et al. |
| 7,105,436 | B2 | 9/2006 | Zhao et al. |
| 7,137,092 | B2 | 11/2006 | Maeda |
| 7,198,963 | B2 | 4/2007 | Verma et al. |
| 7,217,579 | B2 | 5/2007 | Ben-Porath et al. |
| 7,223,616 | B2 * | 5/2007 | Duan ..................... H01L 22/34 257/48 |
| 7,256,055 | B2 | 8/2007 | Aghababazadeh et al. |
| 7,280,945 | B1 | 10/2007 | Weiner et al. |
| 7,456,636 | B2 | 11/2008 | Patterson et al. |
| 7,474,107 | B2 | 1/2009 | Patterson et al. |
| 7,514,681 | B1 | 4/2009 | Marella et al. |
| 7,518,190 | B2 | 4/2009 | Cote et al. |
| 7,592,827 | B1 | 9/2009 | Brozek |
| 7,642,106 | B2 | 1/2010 | Bae et al. |
| 7,655,482 | B2 | 2/2010 | Satya et al. |
| 7,656,170 | B2 | 2/2010 | Pinto et al. |
| 7,679,083 | B2 | 3/2010 | Jansen et al. |
| 7,705,666 | B1 | 4/2010 | Hsu et al. |
| 7,733,109 | B2 | 6/2010 | Ahsan et al. |
| 7,736,916 | B2 | 6/2010 | Aghababazadeh et al. |
| 7,772,866 | B2 | 8/2010 | Patterson et al. |
| 7,893,703 | B2 | 2/2011 | Rzepiela et al. |
| 7,895,548 | B2 | 2/2011 | Lin et al. |
| 7,902,548 | B2 | 3/2011 | Lim et al. |
| 7,930,660 | B2 | 4/2011 | Ruderer et al. |
| 7,939,348 | B2 | 5/2011 | Lim et al. |
| 8,039,837 | B2 | 10/2011 | Patterson et al. |
| 8,063,402 | B2 | 11/2011 | Sokel et al. |
| 8,089,297 | B2 | 1/2012 | Xiao et al. |
| 8,339,449 | B2 | 12/2012 | Lim et al. |
| 8,344,745 | B2 | 1/2013 | Aghababazadeh et al. |
| 8,350,583 | B2 | 1/2013 | Cote et al. |
| 8,399,266 | B2 | 3/2013 | Mo |
| 8,421,009 | B2 | 4/2013 | Xiao |
| 8,575,955 | B1 | 11/2013 | Brozek |
| 8,754,372 | B2 | 6/2014 | Xiao et al. |
| 8,779,400 | B2 | 7/2014 | Shichi et al. |
| 8,927,989 | B2 | 1/2015 | Arnold et al. |
| 9,222,969 | B2 | 12/2015 | Liu et al. |
| 2002/0093350 | A1 | 7/2002 | Yamada |
| 2004/0084671 | A1 | 5/2004 | Song et al. |
| 2004/0133868 | A1 | 7/2004 | Ichimiya |
| 2005/0272174 | A1 | 12/2005 | Duan et al. |
| 2006/0164881 | A1 | 7/2006 | Oki |
| 2006/0202231 | A1 | 9/2006 | Yamamoto |
| 2007/0296435 | A1 | 12/2007 | Eldridge et al. |
| 2008/0246030 | A1 | 10/2008 | Satya et al. |
| 2008/0267489 | A1 | 10/2008 | Xiao et al. |
| 2008/0312875 | A1 | 12/2008 | Yu et al. |
| 2009/0057664 | A1 | 3/2009 | Lim et al. |
| 2009/0102501 | A1 | 4/2009 | Guldi et al. |
| 2010/0055809 | A1 | 3/2010 | Pak et al. |
| 2010/0258798 | A1 | 10/2010 | Sokel et al. |
| 2011/0013826 | A1 | 1/2011 | Xiao |
| 2011/0080180 | A1 | 4/2011 | Lavoie et al. |
| 2012/0286341 | A1 | 11/2012 | Chen et al. |
| 2013/0020639 | A1 | 1/2013 | Thompson et al. |
| 2014/0151699 | A1 | 6/2014 | Wu et al. |
| 2015/0356232 | A1 | 12/2015 | Bomholt et al. |

FOREIGN PATENT DOCUMENTS

| | | |
|---|---|---|
| WO | WO/03/104921 | 12/2003 |
| WO | WO/2004/057649 | 7/2004 |
| WO | 2005/020297 | 5/2005 |
| WO | WO/2006/123281 | 11/2006 |
| WO | 2009/090516 | 8/2009 |
| WO | WO/2015/192069 | 12/2015 |

OTHER PUBLICATIONS

H. Xiao et al., "Capturing Buried Defects in Metal Interconnections with Electron Beam Inspection System," Proc. SPIE 8681, Apr. 18, 2013.

T. Newell et al., "Detection of Electrical Defects with SEMVision in Semiconductor Production Mode Manufacturing," Proc. of SPIE vol. 9778, Feb. 21, 2016.

C. Hess et al., "Scribe Characterization Vehicle Test Chip for Ultra Fast Product Wafer Yield Monitoring," 2006 IEEE International Conference on Microelectronic Test Structures, Mar. 6, 2006.

J. Cong et al., "Optimizing routability in large-scale mixed-size placement," Design Automation Conference (ASP-DAC), Jan. 22, 2013.

C. Menezes et al., "Design of regular layouts to improve predictability," Proceedings of the 6th IEEE International Caribbean Conference on Devices, Circuits and Systems, Apr. 26, 2006.

X. Meng et al., "Novel Decoupling Capacitor Designs for sub-90nm CMOS Technology," Proceedings of the 7th IEEE International Symposium on Quality Electronic Design, Mar. 27, 2006.

T. Jungeblut et al., "A modular design flow for very large design space explorations," CDNLive! EMEA 2010, May 4, 2010.

R. J. Baker, "CMOS: circuit design, layout, and simulation," 3rd ed., John Wiley & Sons, Inc., 2010.

X. Meng et al., "Layout of Decoupling Capacitors in IP Blocks for 90-nm CMOS," IEEE Trans. on VLSI, Oct. 3, 2008.

W. T. Lee, "Engineering a Device for Electron-Beam Probing," IEEE Design & Test of Computers, Jun. 1989.

B. Vandewalle et al., "Design technology co-optimization for a robust 10nm Metal1 solution for Logic design and SRAM," Proc. SPIE, Mar. 28, 2014.

(56) References Cited

OTHER PUBLICATIONS

A. J. Fixi et al., "Laser Stimulated Electron-Beam Prober for 15ps Resolution Internal Waveform Measurements of a 5 Gb/s ECL Circuit," Reliability Physics Symposium, Mar. 23, 1993.
J. M. Sebeson et al., "Noncontact Testing of Interconnections in Film Integrated Circuits Using an Electron Beam," Reliability Physics Symposium, Apr. 1973.
L. Remy et al., "Definition of an Innovative Filling Structure for Digital Blocks: the DFM Filler Cell," ICECS 2009, Dec. 13, 2009.
J. C. Eidson, "Fast electron-beam lithography: High blanking speeds may make this new system a serious challenger in producing submicrometer ICs," IEEE Spectrum, Jul. 1981.
M. T. Moreira, "Design and Implementation of a Standard Cell Library for Building Asynchronous Asics," Pontificia Universidade Católica Do Rio Grande Do Sul, 2010.
P. De Bisschop et al., "Joint-Optimization of Layout and Litho for SRAM and Logic towards the 20 nm node, using 193i," Proc. SPIE, Mar. 23, 2011.
Written Opinion of International Searching Authority, Applic. No. PCT/US2015/035647, dated Oct. 7, 2015.
International Search Report, Applic. No. PCT/US2015/035647, dated Oct. 7, 2015.
M. Gupta, "Design and Implementation of a Scribe Line Measurement Transistor Test Array Structure in 14nm FinFET CMOS Technology," M.S. Thesis, Univ. of Texas at Austin, May 2015.
O.D. Patterson et al., "In-Line Process Window Monitoring using Voltage Contrast Inspection," 2008 IEEE/SEMI Advanced Semiconductor Manufacturing Conference, May 5, 2008.
J. Jau et al., "A Novel Method for In-line Process Monitoring by Measuring the Gray Level Values of SEM Images," IEEE International Symposium on Semiconductor Manufacturing, Sep. 13, 2005.
M. Saito et al., "Study of ADI (After Develop Inspection) Using Electron Beam," Proc. of SPIE vol. 6152, Feb. 19, 2006.
H.Y. Li et al., "Built-in Via Module Test Structure for Backend Interconnection In-line Process Monitor," Proceedings of the 12th International Symposium on the Physical and Failure Analysis of Integrated Circuits, Jun. 27, 2005.
Y. Hamamura et al., "An Advanced Defect-Monitoring Test Structure for Electrical Screening and Defect Localization," IEEE Transactions on Semiconductor Manufacturing, May 10, 2004.
O.D. Patterson et al., "Voltage Contrast Test Structure for Measurement of Mask Misalignment," Advanced Semiconductor Manufacturing Conference (ASMC), 2010 IEEE/SEMI , pp. 334-340, Jul. 11, 2010.
O.D. Patterson et al., "Test Structure and e-Beam Inspection Methodology for In-line Detection of (Non-visual) Missing Spacer Defects," Advanced Semiconductor Manufacturing Conference, 2007 IEEE/SEMI , pp. 48-53, Jun. 11, 2007.
H. Xiao et al., "Inspection of 32nm imprinted patterns with an advanced e-beam inspection system," Proc. SPIE 7488, Photomask Technology 2009, Sep. 23, 2009.
S.-M. Chon et al., "Development of Automated Contact Inspection System using In-line CD SEM," 2001 IEEE International Semiconductor Manufacturing Symposium, Oct. 8, 2001.
O.D. Patterson et al., "Rapid Reduction of Gate-Level Electrical Defectivity using Voltage Contrast Test Structures," 2003 IEEEI/SEMI Advanced Semiconductor Manufacturing Conference and Workshop, Mar. 31, 2003.
J.-L. Baltzinger et al., "E-beam inspection of dislocations: product monitoring and process change validation," IEEE Conference and Workshop Advanced Semiconductor Manufacturing, May 4, 2004.
K. Mai et al., "SPC Based In-line Reticle Monitoring on Product Wafers," 2005 IEEE/SEMI Advanced Semiconductor Manufacturing Conference and Workshop, Apr. 11, 2005.
C. Holfeld et al., "Wafer Inspection as Alternative Approach to Mask Defect Qualification," Proc. SPIE 6730, Photomask Technology 2007, Oct. 25, 2007.
O.D. Patterson et al., "Detection of Resistive Shorts and Opens using Voltage Contrast Inspection," 17th Annual SEMI/IEEE Advanced Semiconductor Manufacturing Conference, May 22, 2006.
O.D. Patterson et al., "Enhancement of Voltage Contrast Inspection Signal Using Scan Direction," International Symposium on Semiconductor Manufacturing, Oct. 15, 2007.
O.D. Patterson et al., "In-Line Process Window Monitoring using Voltage Contrast Inspection," IEEE/SEMI Advanced Semiconductor Manufacturing Conference, May 5, 2008.
O.D. Patterson et al., "Methodology for Trench Capacitor Etch Optimization using Voltage Contrast Inspection and Special Processing," ASMC 2010, Jul. 11, 2010.
X.J. Zhou et al., "Characterization of Contact Module Failure Mechanisms for SOI Technology using E-beam Inspection and In-line TEM," ASMC 2010, Jul. 11, 2010.
H.-C. Liao et al., "Blind Contact Detection in the Irregularly Periphery Area Using Leap & Scan e-Beam Inspection," Presentation Slides, International Symposium on Semiconductor Manufacturing (ISSM) and e-Manufacturing and Design Collaboration Symposium (eMDC), Sep. 5, 2011.
C. Boye et al., "E-Beam Inspection for Combination Use of Defect Detection and CD Measurement," 23rd Annual SEMI Advanced Semiconductor Manufacturing Conference (ASMC), May 15, 2012.
O.D. Patterson et al., "E-Beam Inspection for Detection of Sub-Design Rule Physical Defects," ASMC 2012, May 15, 2012.
O.D. Patterson et al., "Early Detection of Systematic Patterning Problems for a 22nm SOI Technology using E-Beam Hot Spot Inspection," ASMC 2013, May 14, 2013.
B. Donovan et al., "Early Detection of Electrical Defects in Deep Trench Capacitors using Voltage Contrast Inspection," ASMC 2013, May 14, 2013.
Presentation entitled, "tau-Metrix, Inc: A Product Yield Enhancement Company," 2009.
Li, "Innovative E-Beam Applications for Advanced Technology Nano-defect Era," SEMATECH Symposium Taiwan 2012, Oct. 18, 2012.
T. Marwah, "System-on-Chip Design and Test with Embedded Debug Capabilities," M.S. Thesis, Univ. of Tenn. at Knoxville, Aug. 2006.
M. Bhushan et al., "Microelectronic Test Structures for CMOS Technology," DOI 10.1007/978-1-4419-9377-9_1, (c) Springer Science+Business Media, LLC, 2011.
M. Muehlberghuber et al., "Red Team vs. Blue Team Hardware Trojan Analysis: Detection of a Hardware Trojan on an Actual ASIC," Proceedings of the 2nd International Workshop on Hardware and Architectural Support for Security and Privacy, Jun. 24, 2013.

* cited by examiner

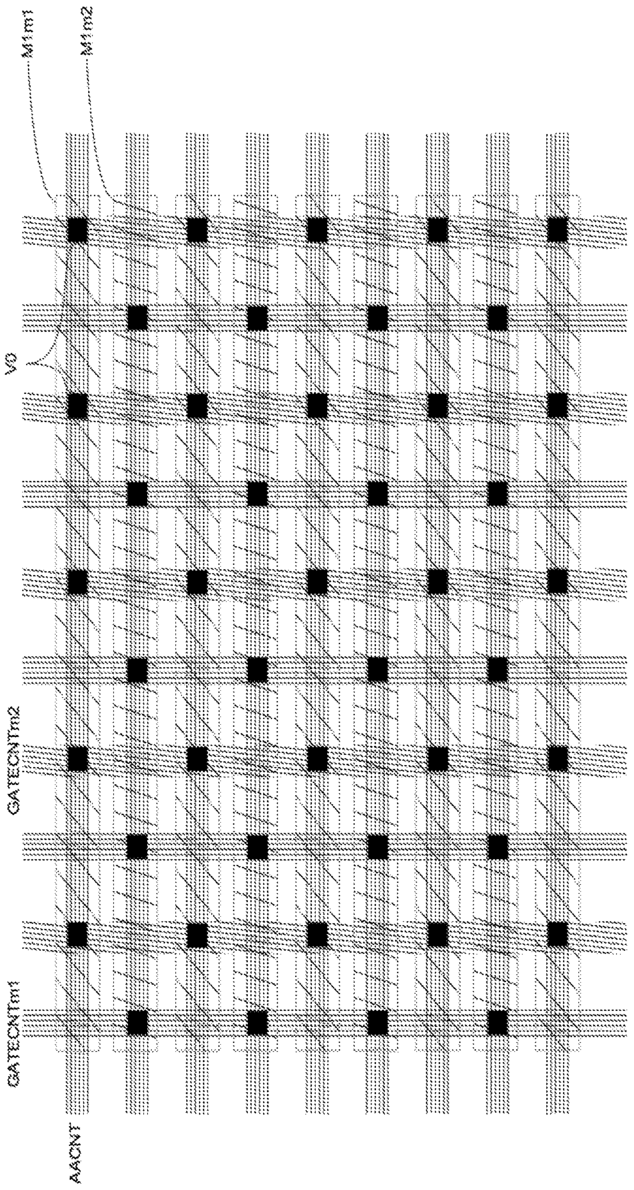
FIG. 9AAA

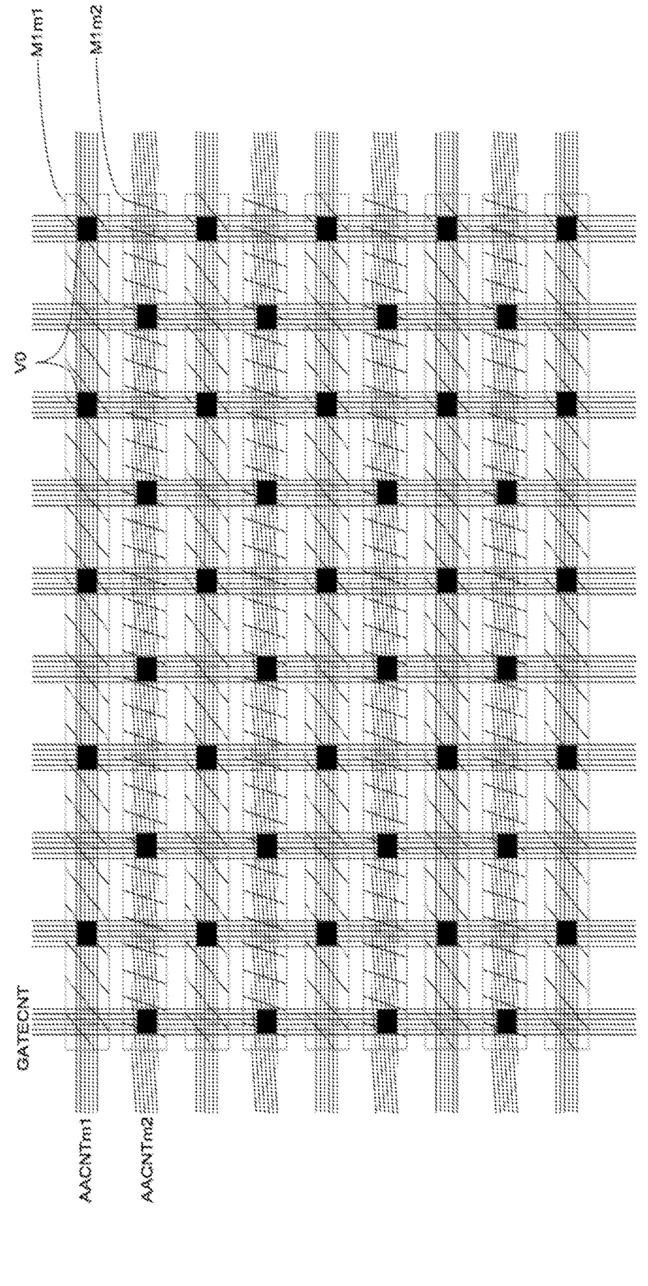
FIG. 9BBB

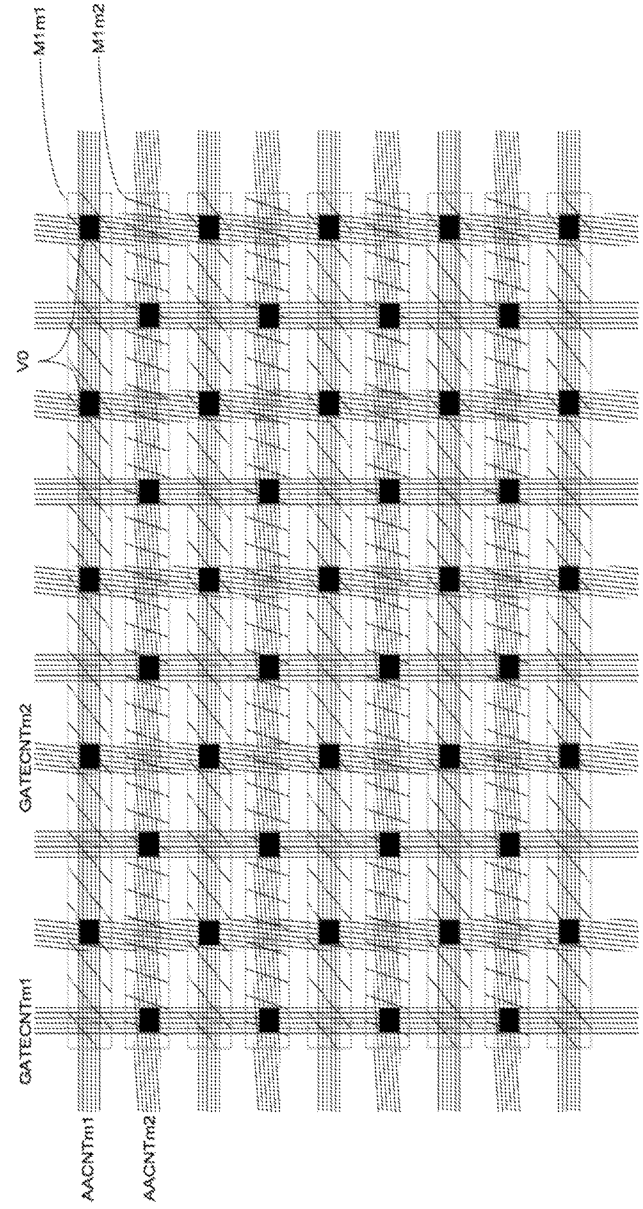
FIG. 9CCC

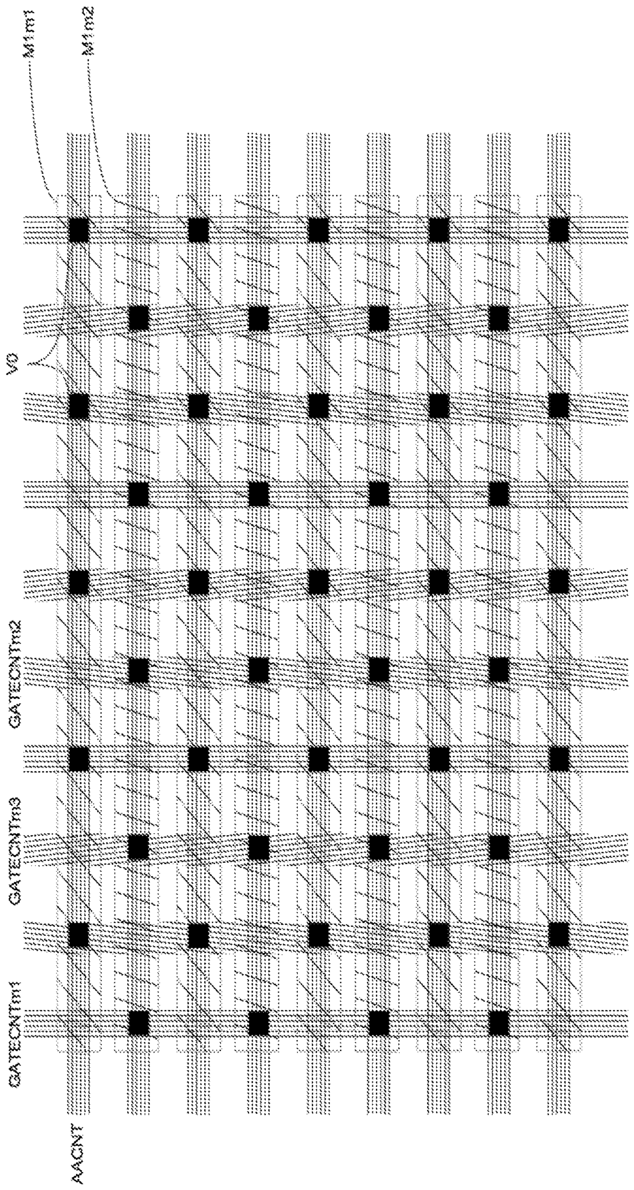
FIG. 9DDD

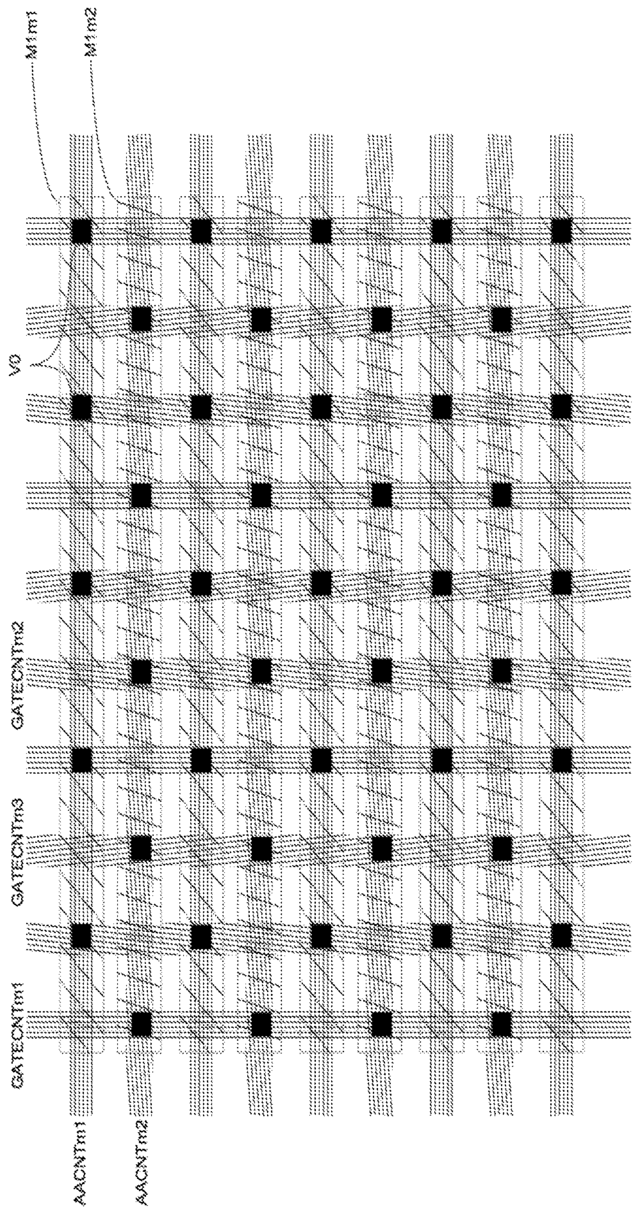
FIG. 9EEE

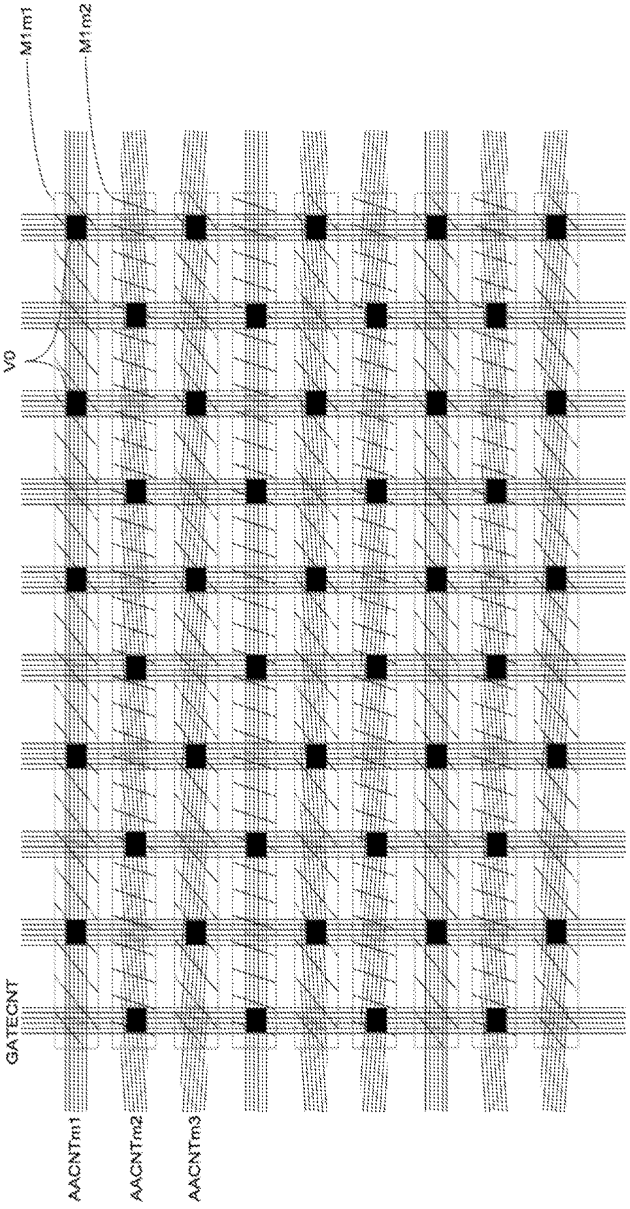
FIG. 9FFF

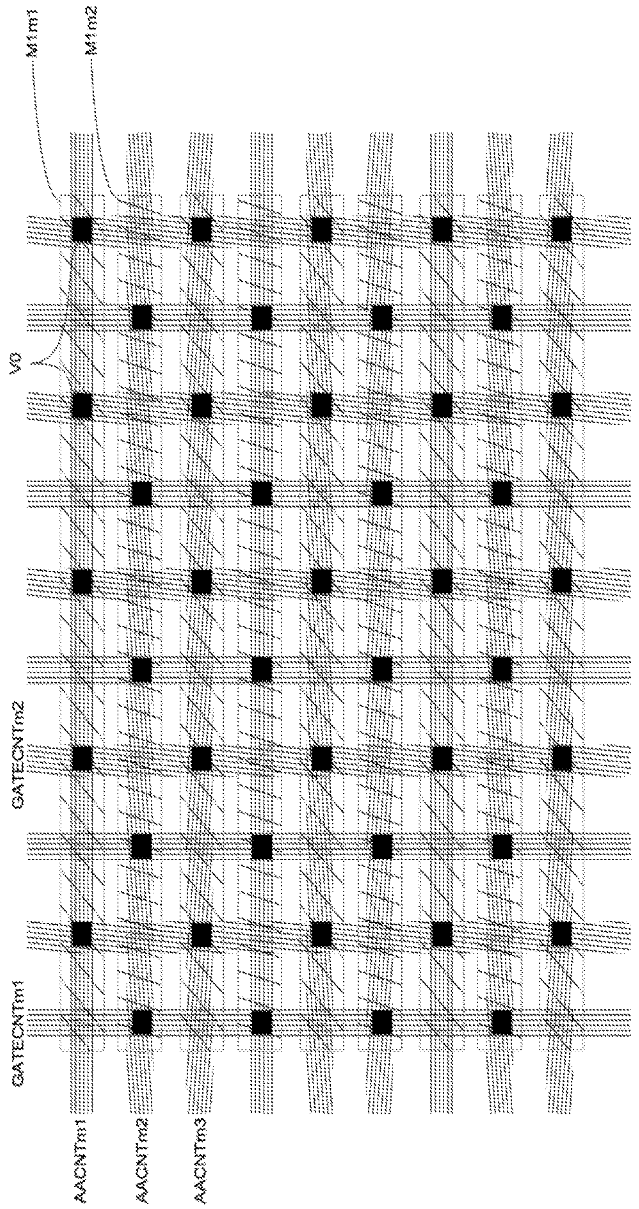
FIG. 9GGG

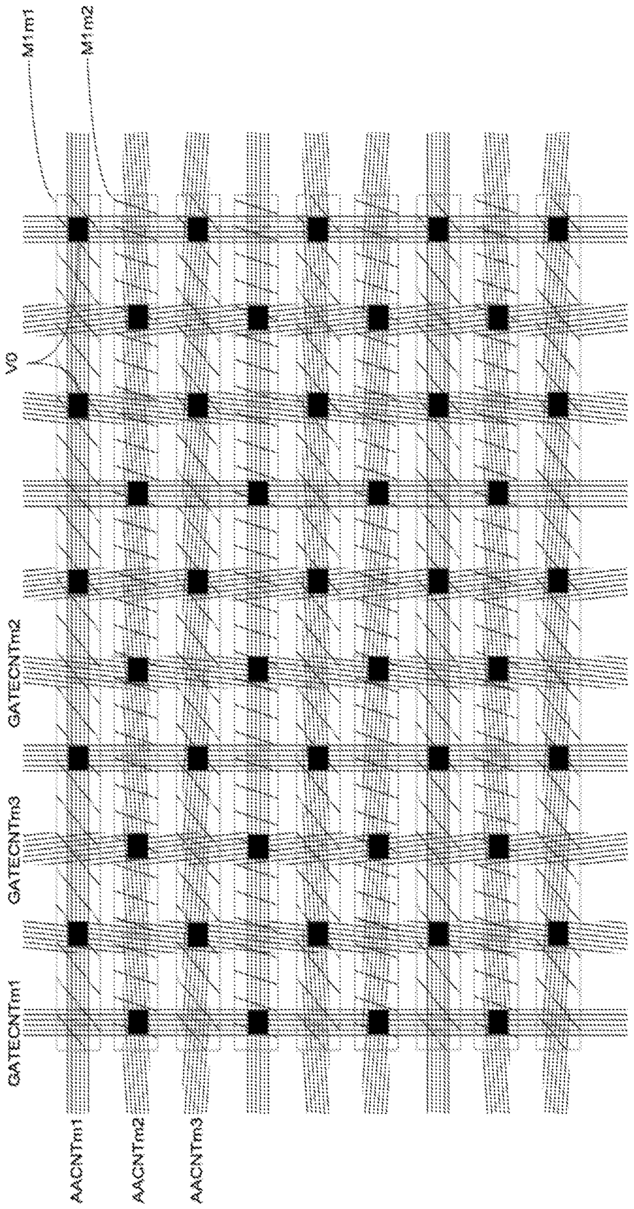
FIG. 9HHH

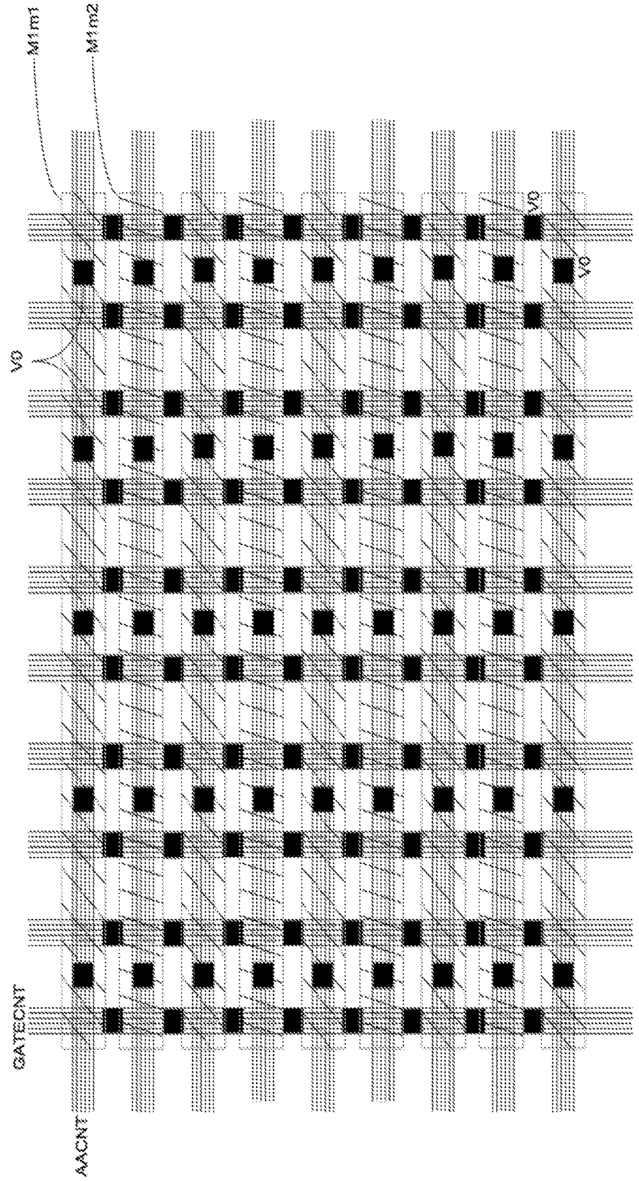
FIG. 9III

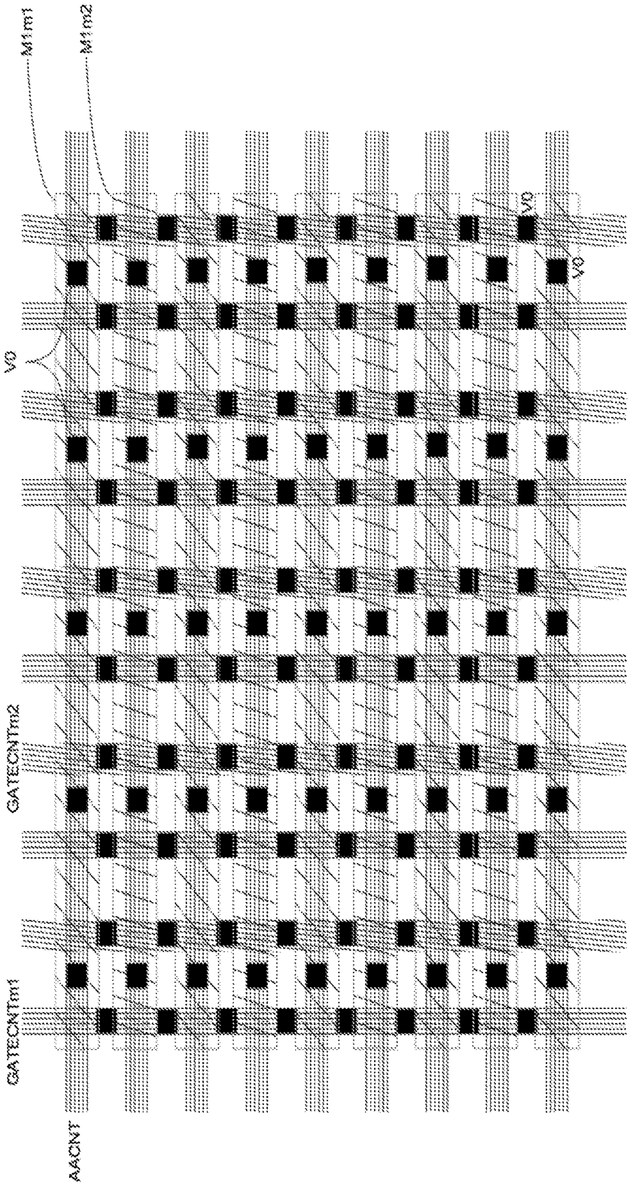
FIG. 9JJJ

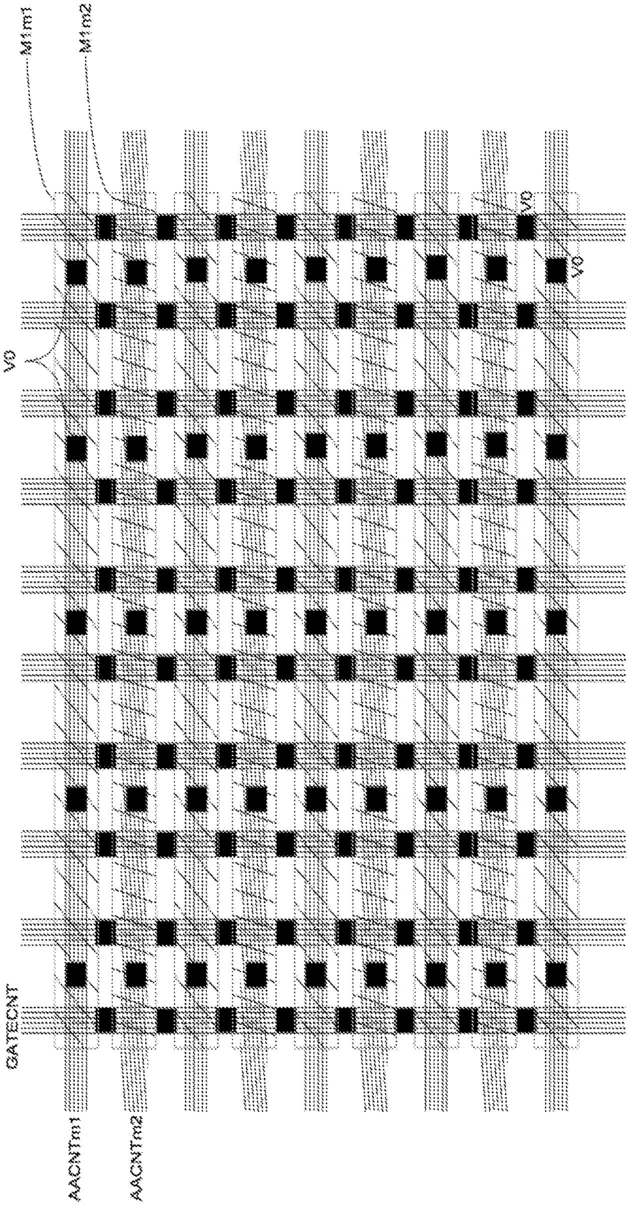
FIG. 9KKK

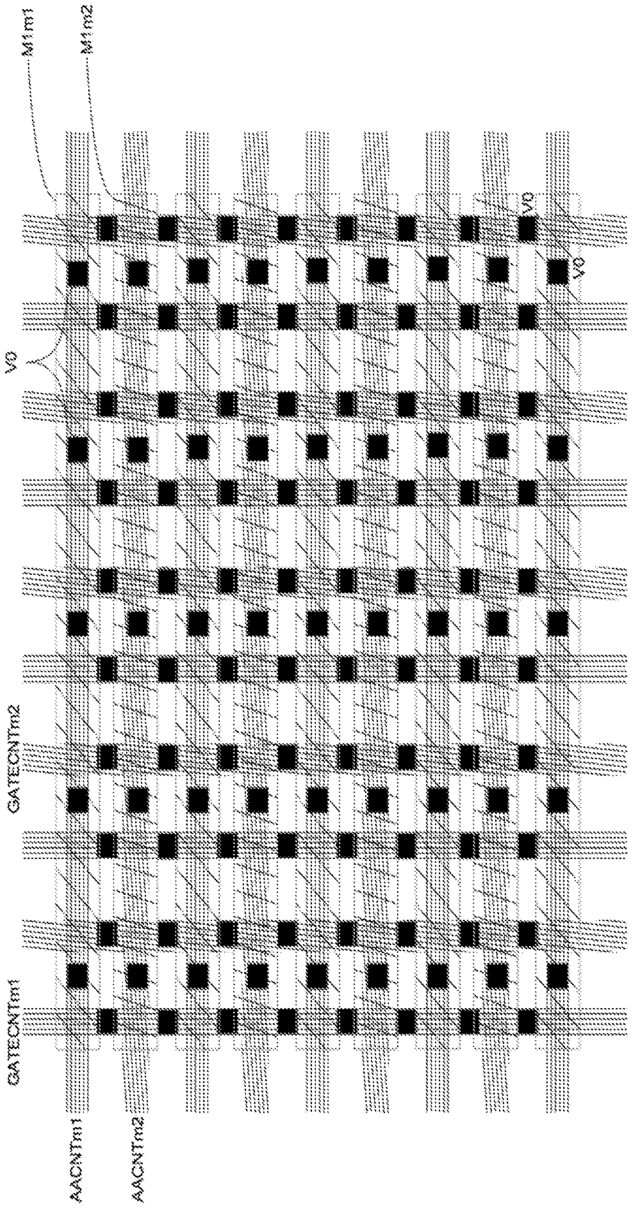
FIG. 9LLL

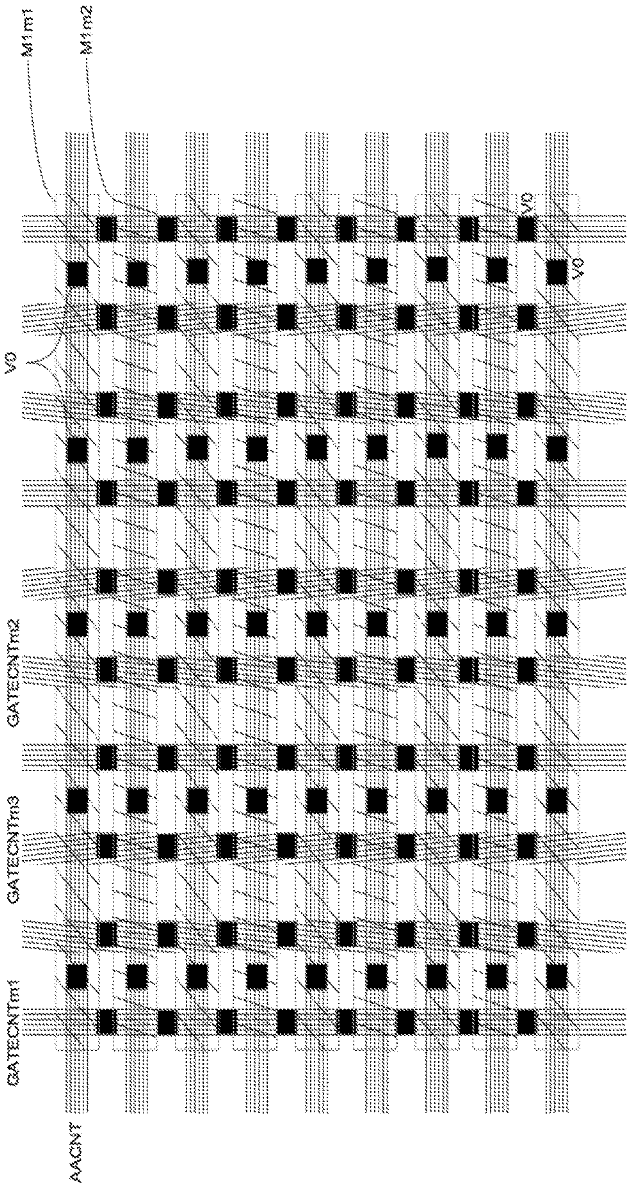
FIG. 9MMM

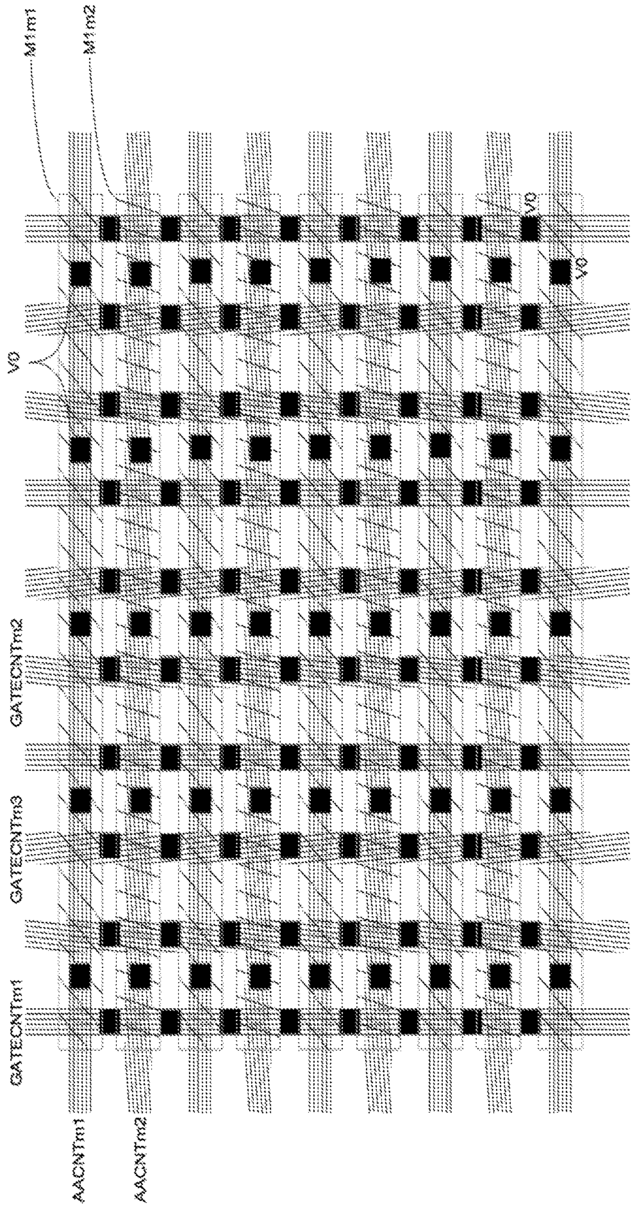
FIG. 9NNN

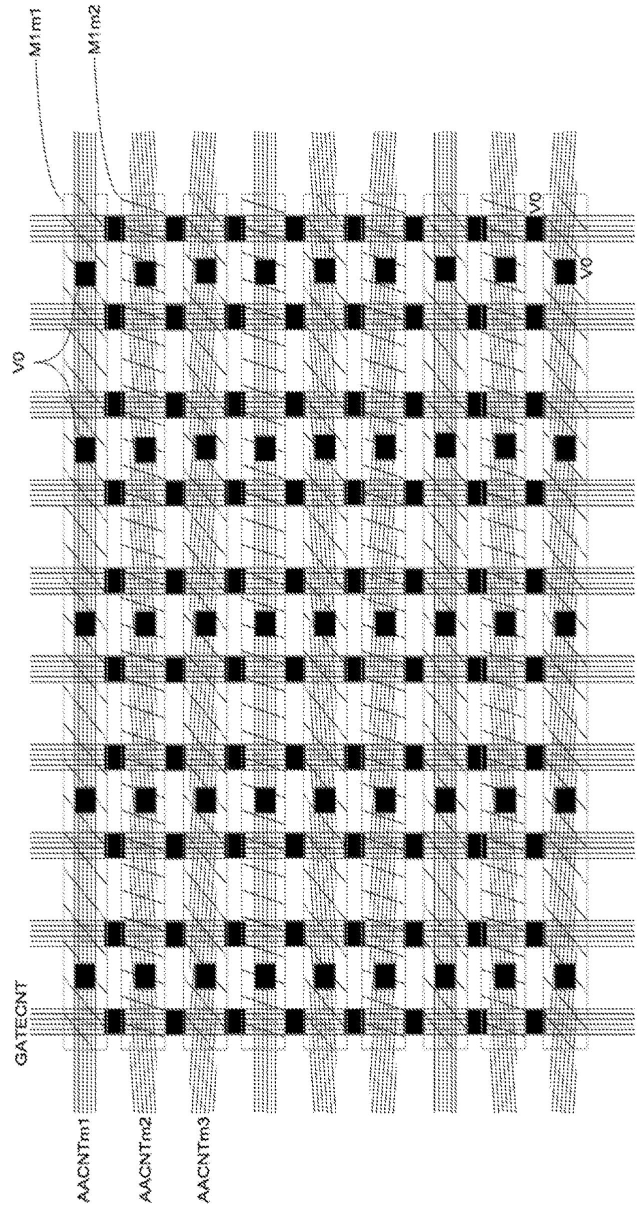
FIG. 9000

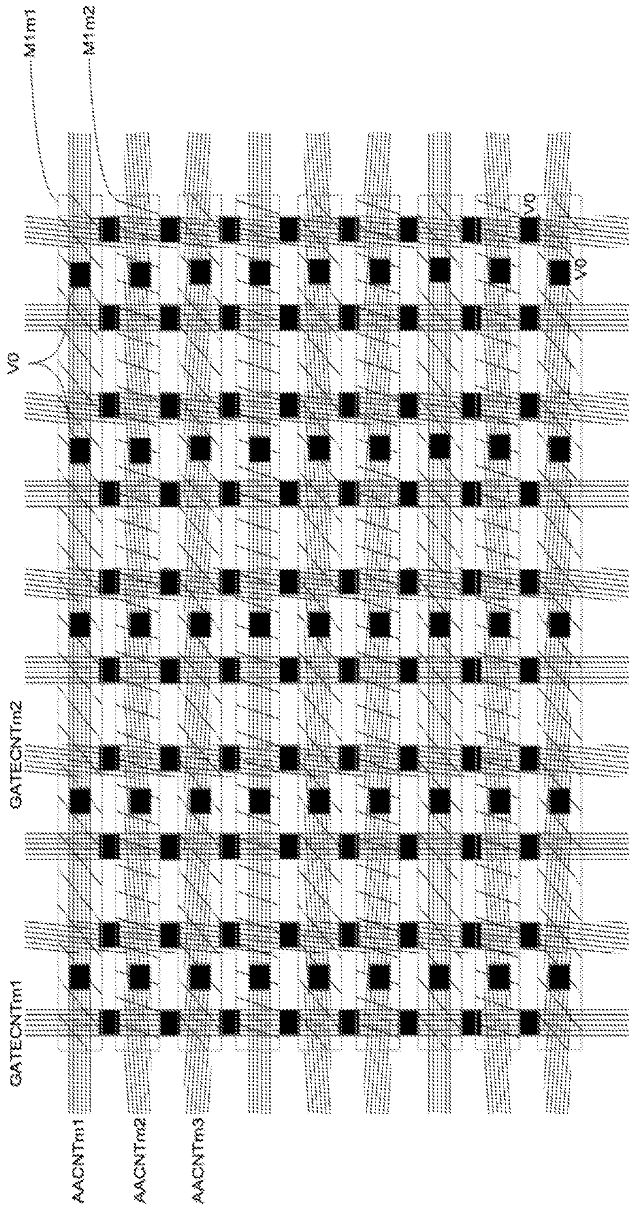
FIG. 9PPP

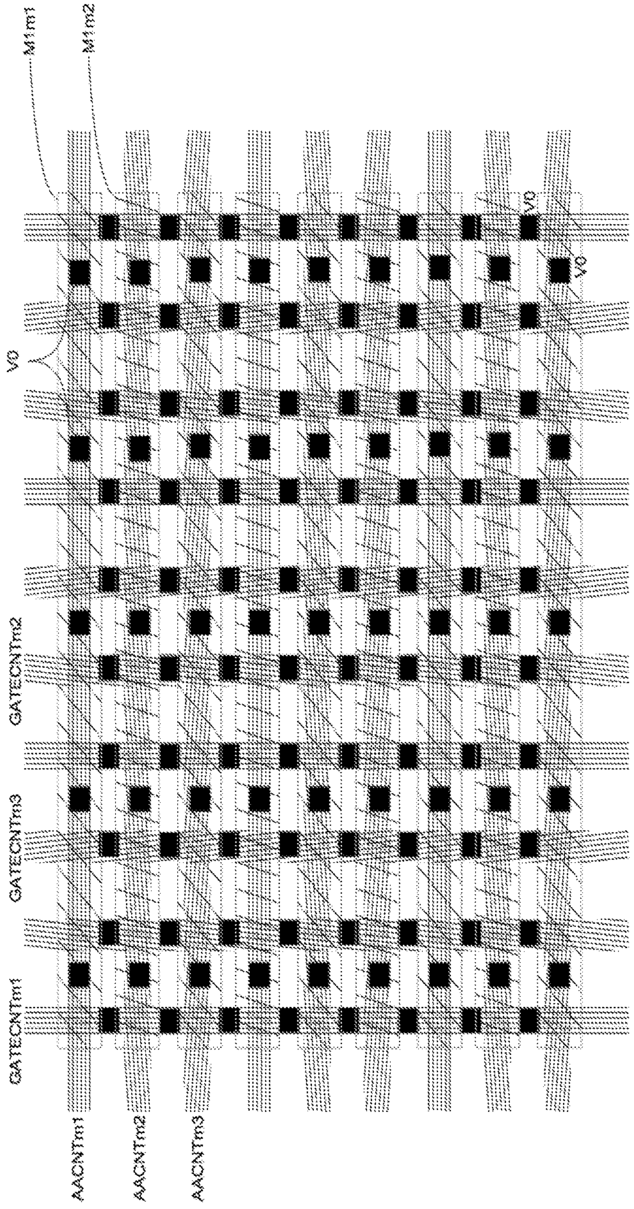
FIG. 9QQQ

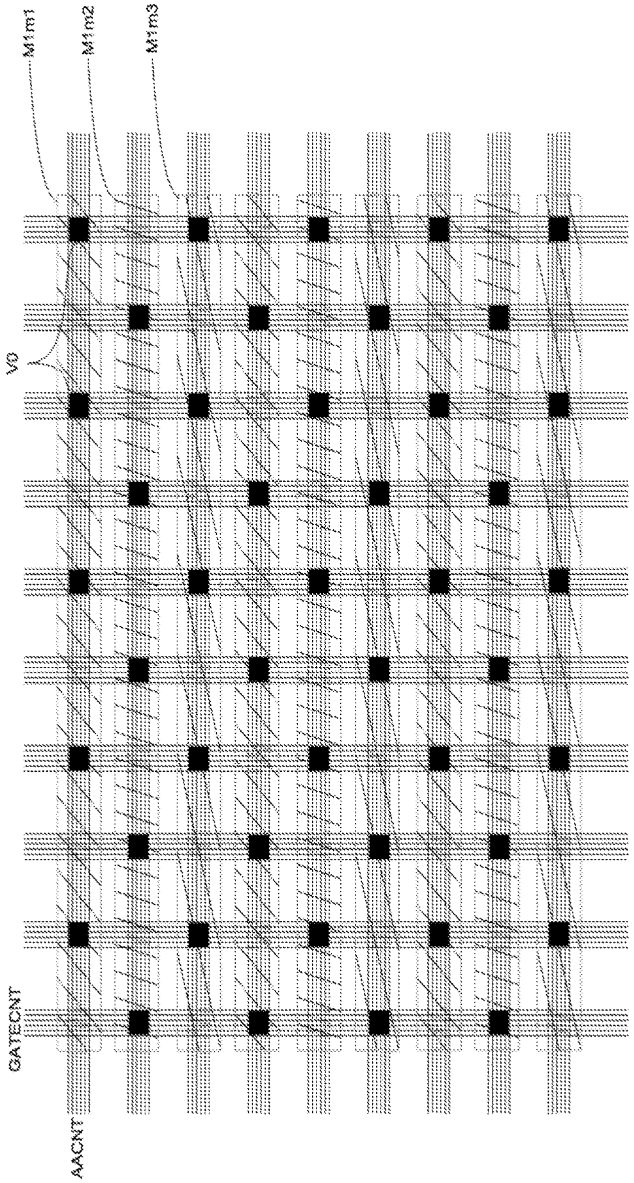
FIG. 9RRR

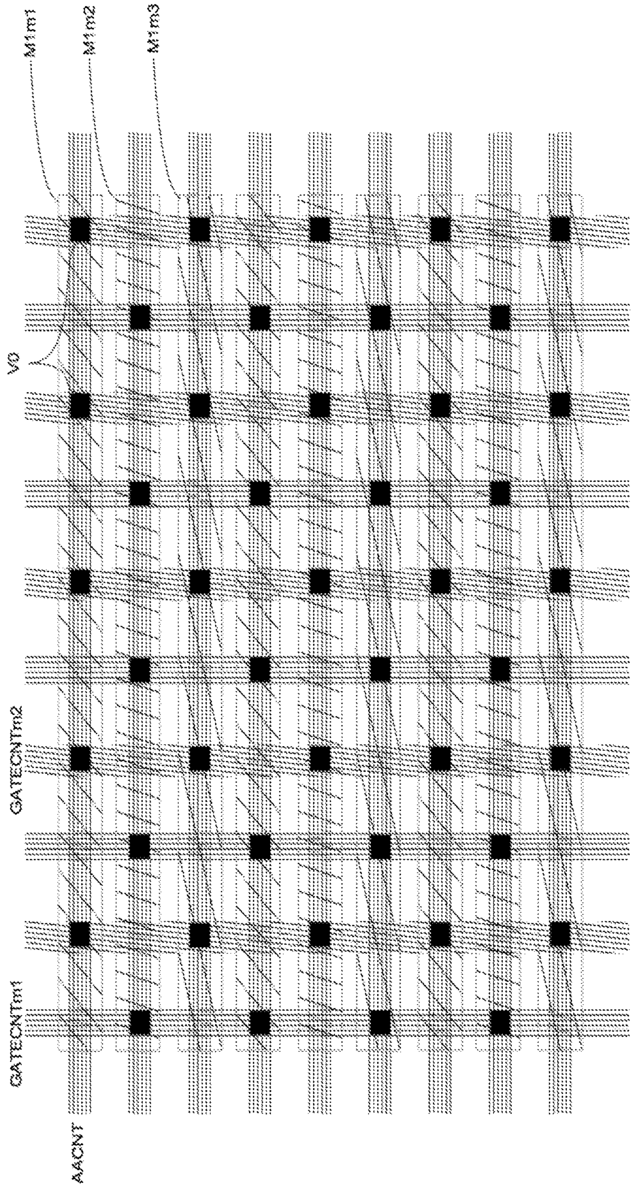
FIG. 9SSS

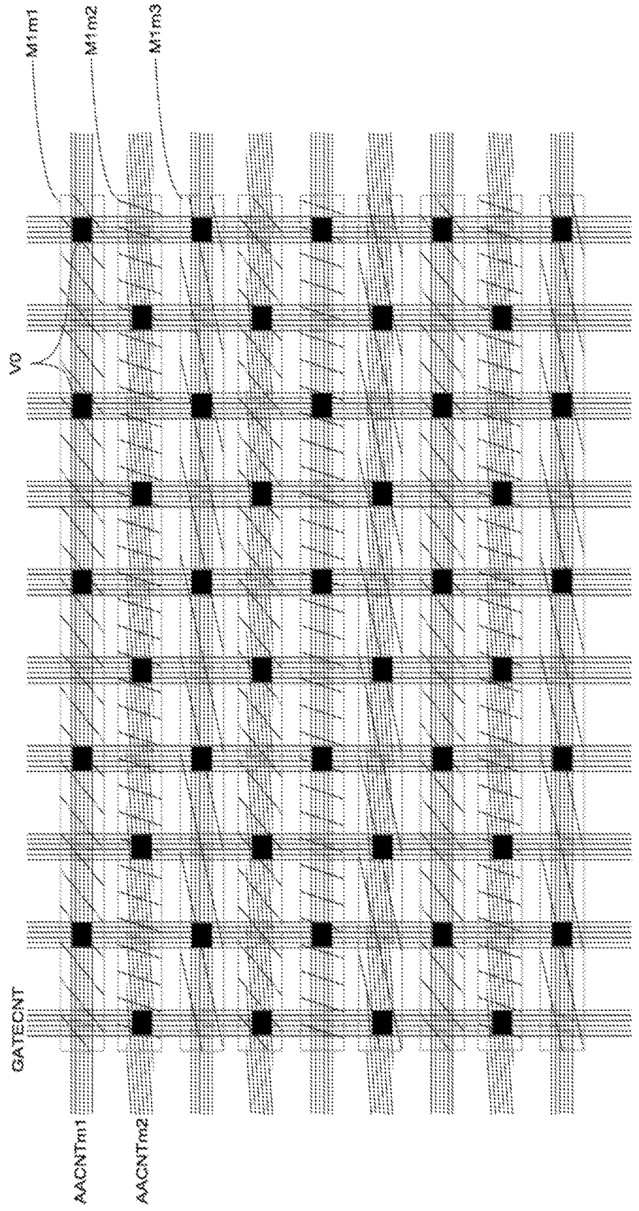
FIG. 9TTT

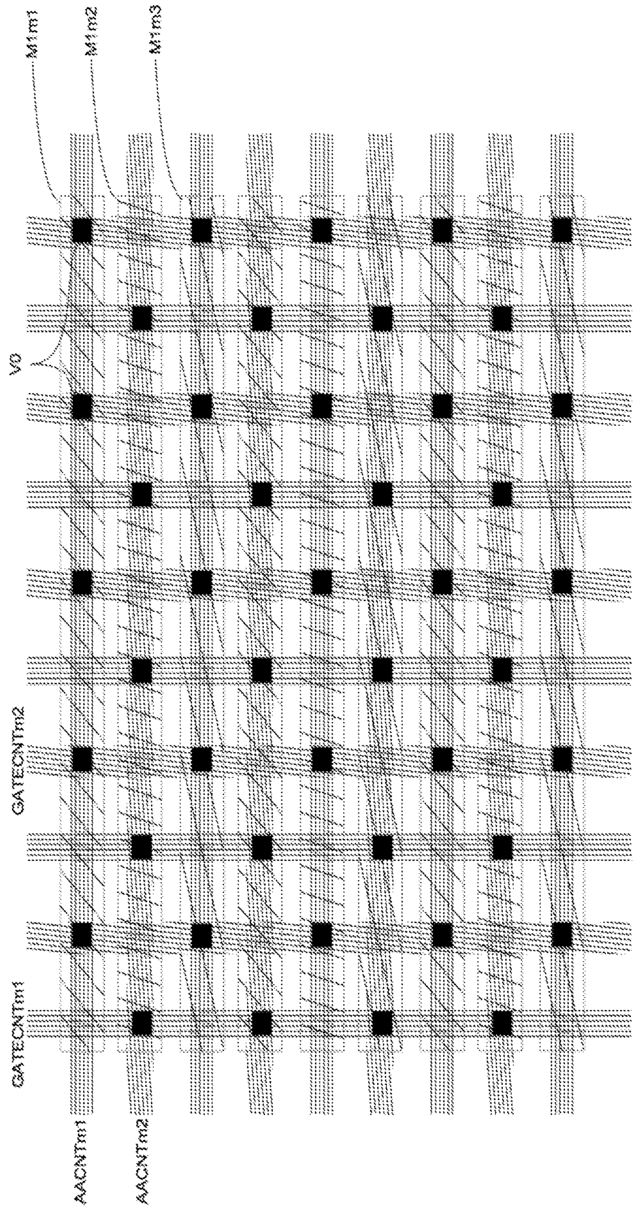
FIG. 9UUU

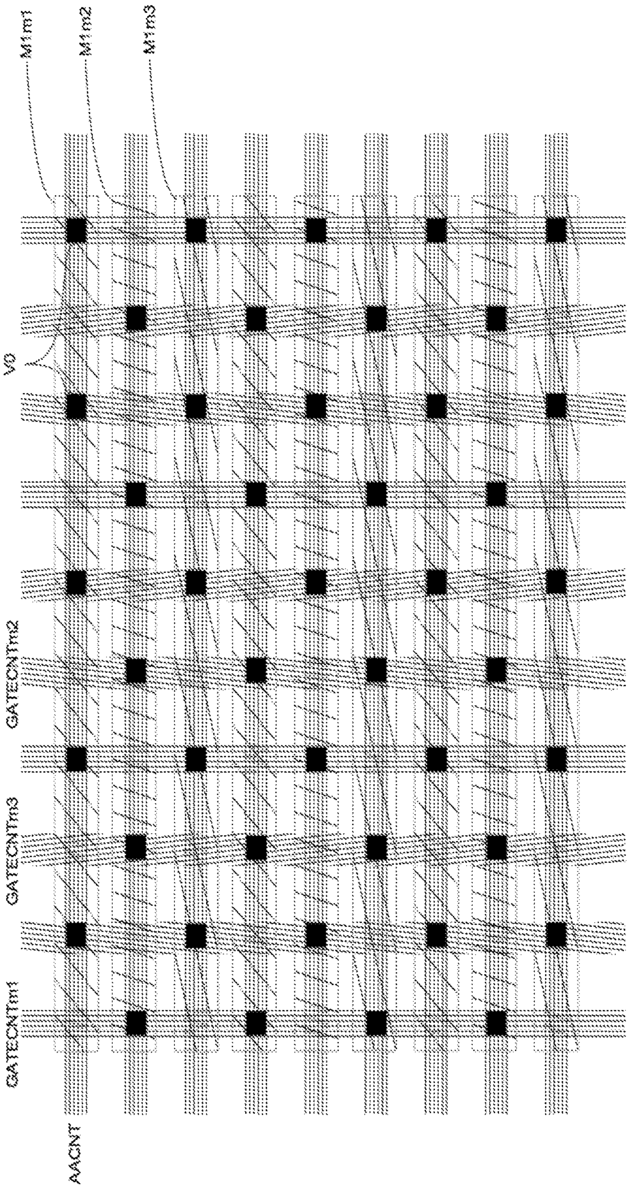
FIG. 9VVV

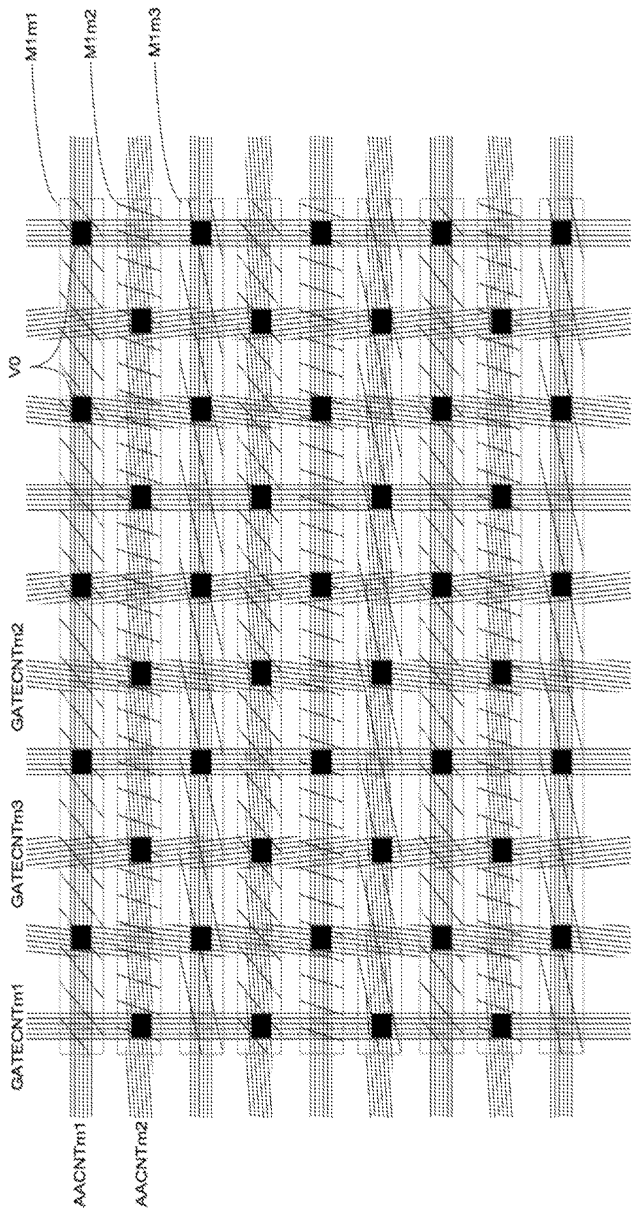
FIG. 9WWW

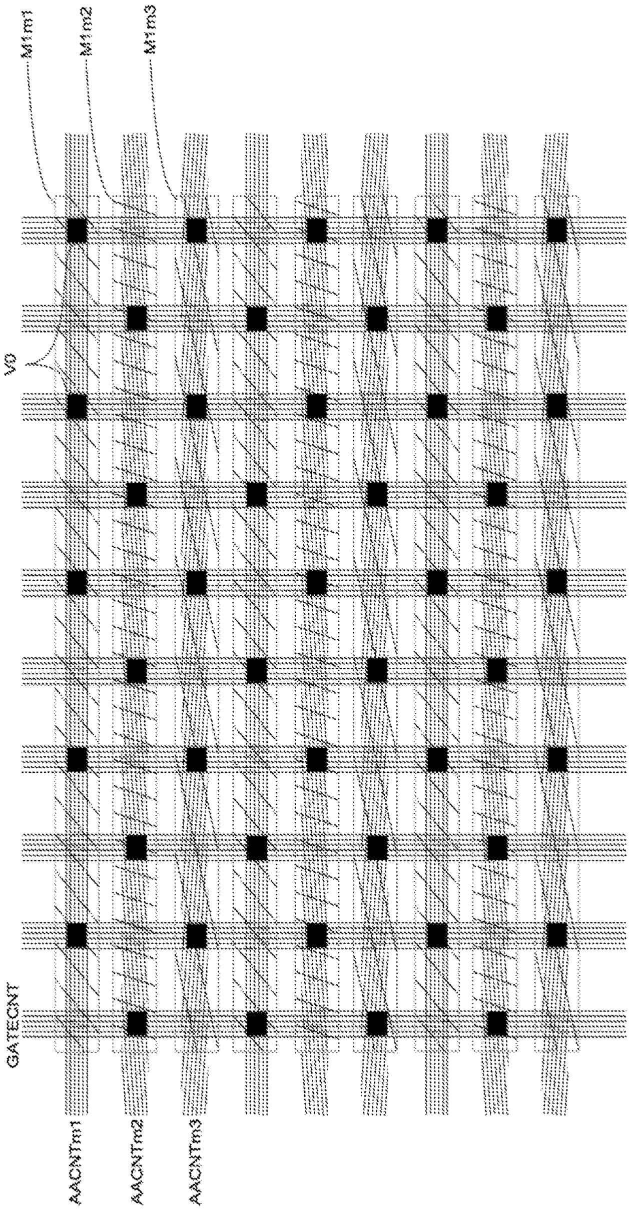
FIG. 9XXX

U.S. Patent Oct. 31, 2017 Sheet 80 of 2550 US 9,805,994 B1
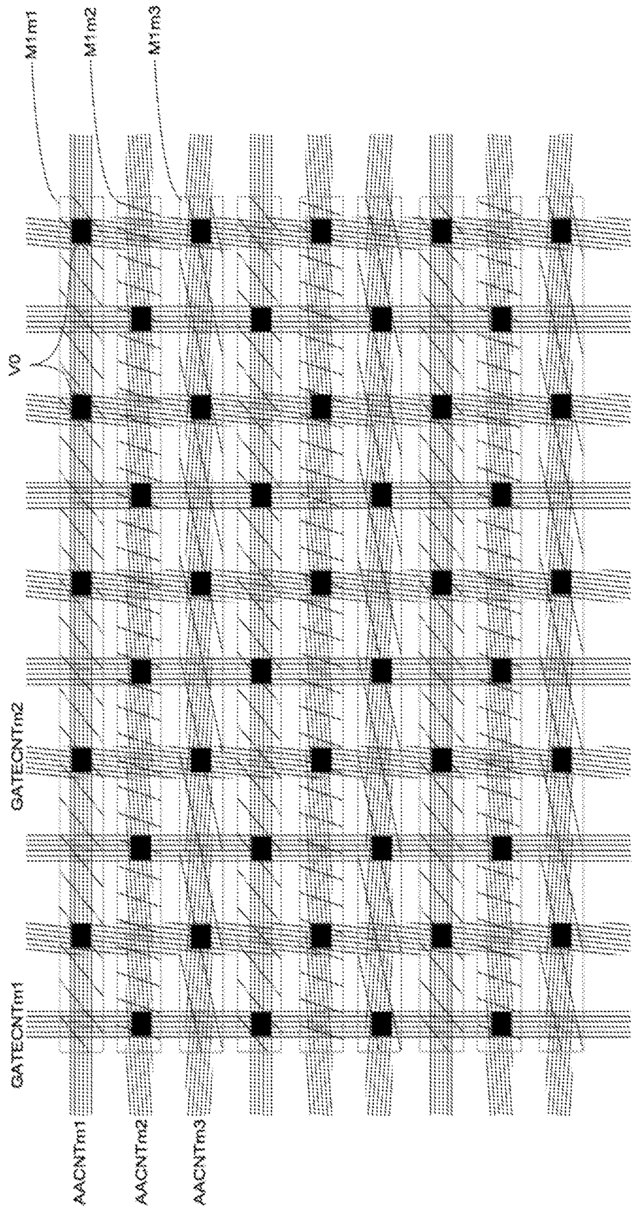
FIG. 9YYY

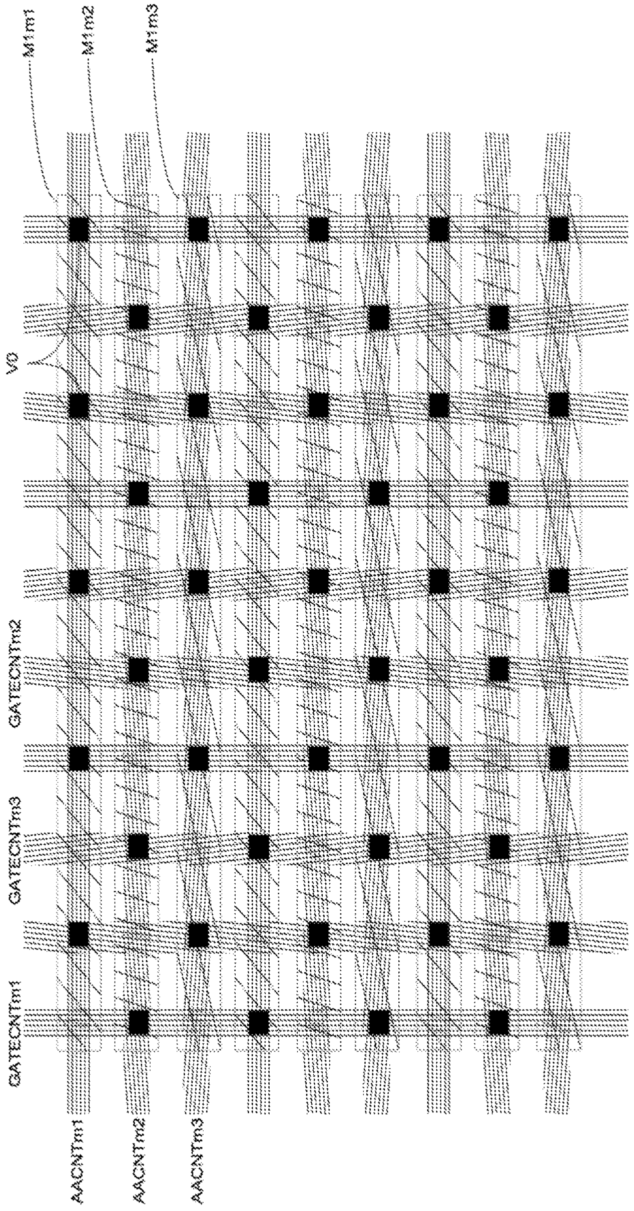
FIG. 9ZZZ

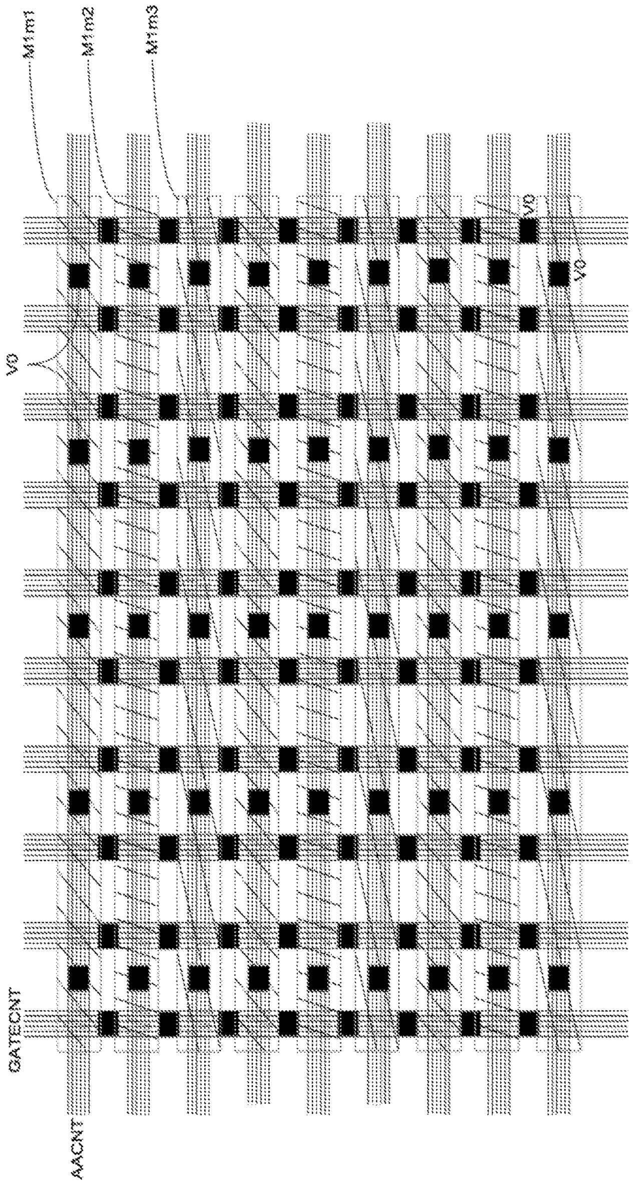
FIG. 9AAAA

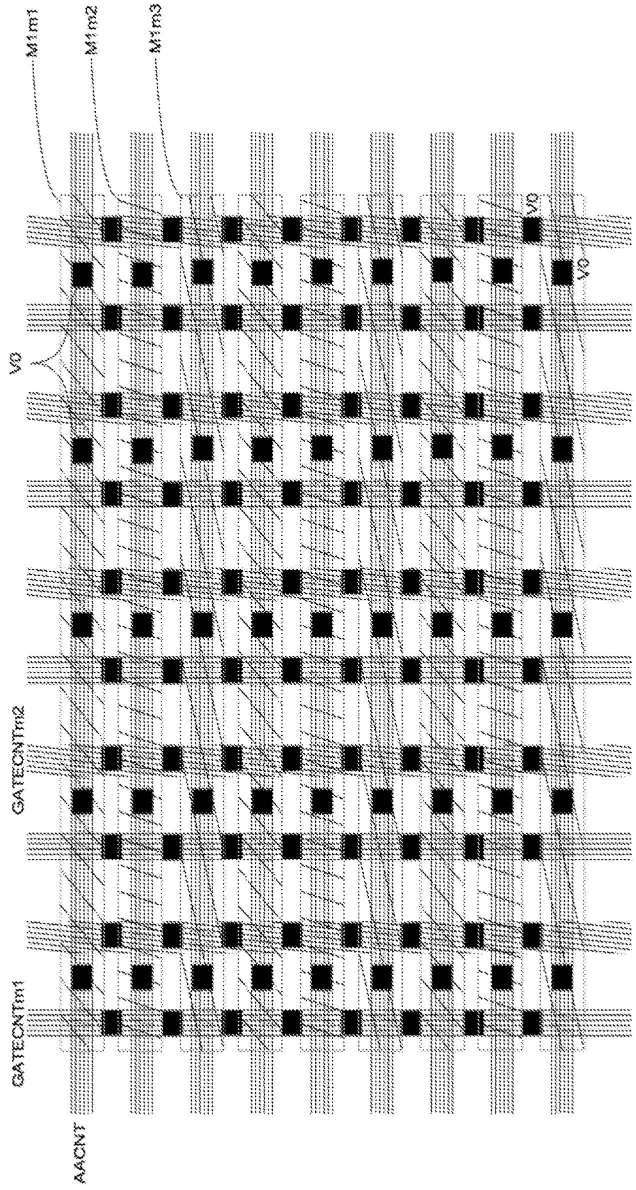
FIG. 9BBBB

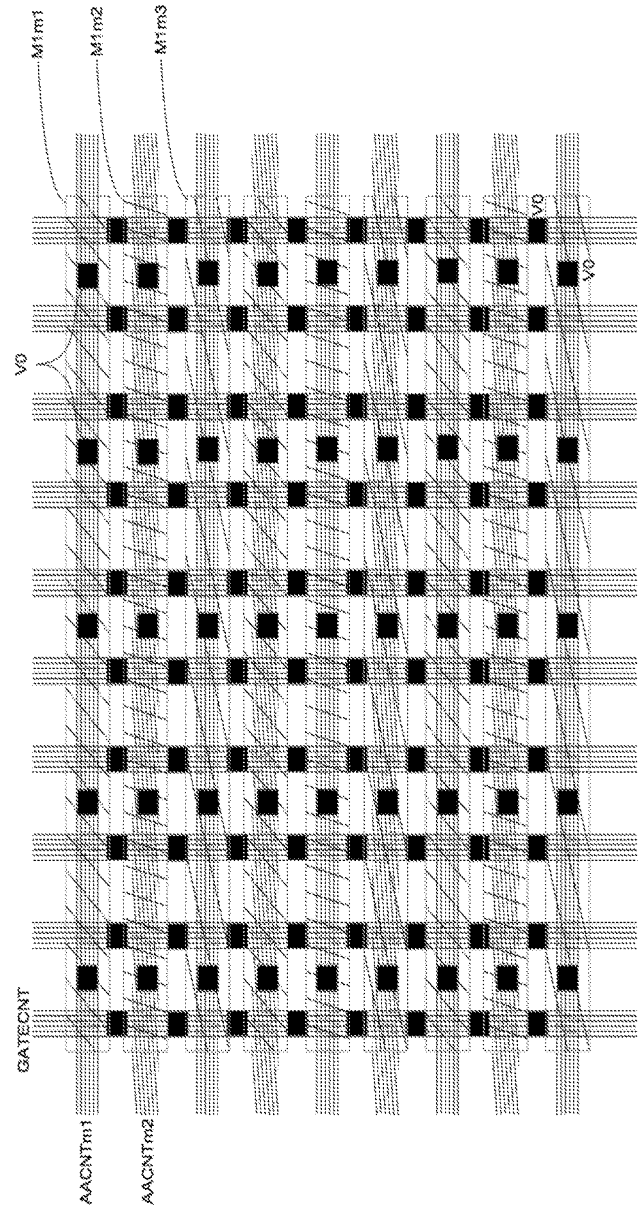
FIG. 9CCCC

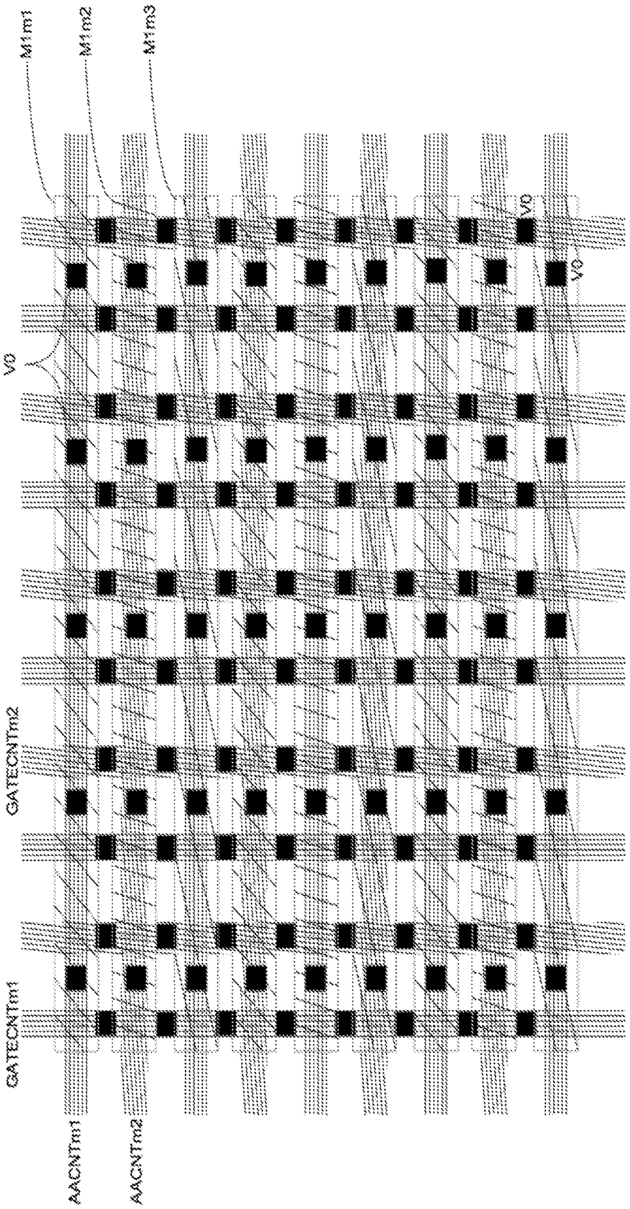
FIG. 9DDDD

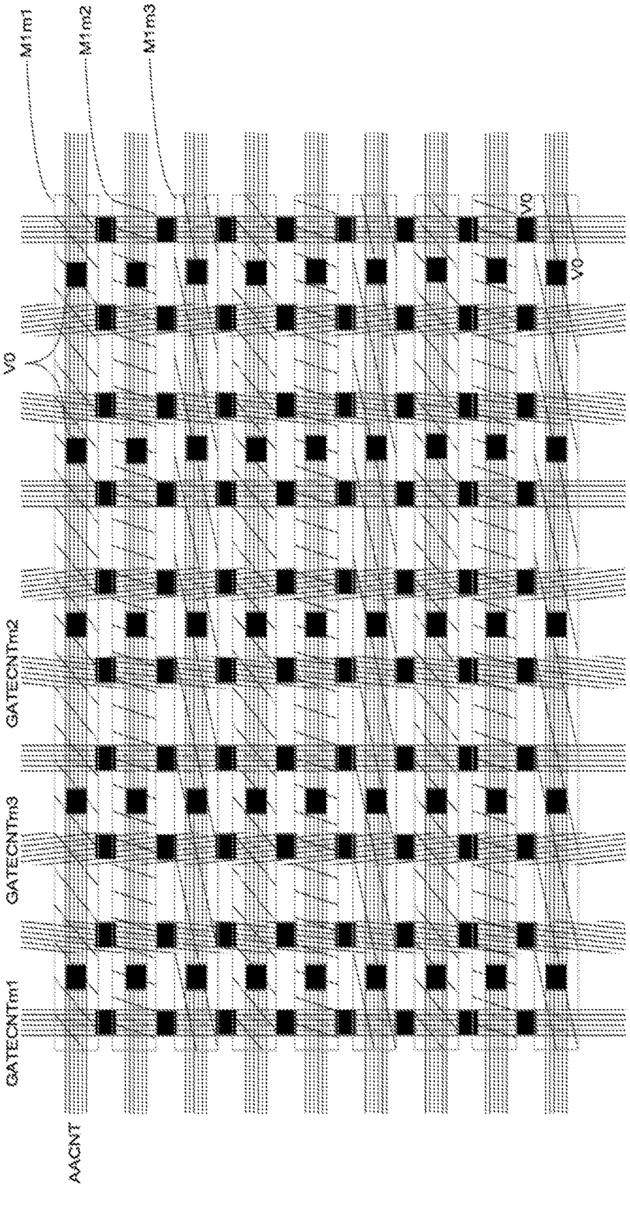
FIG. 9EEEE

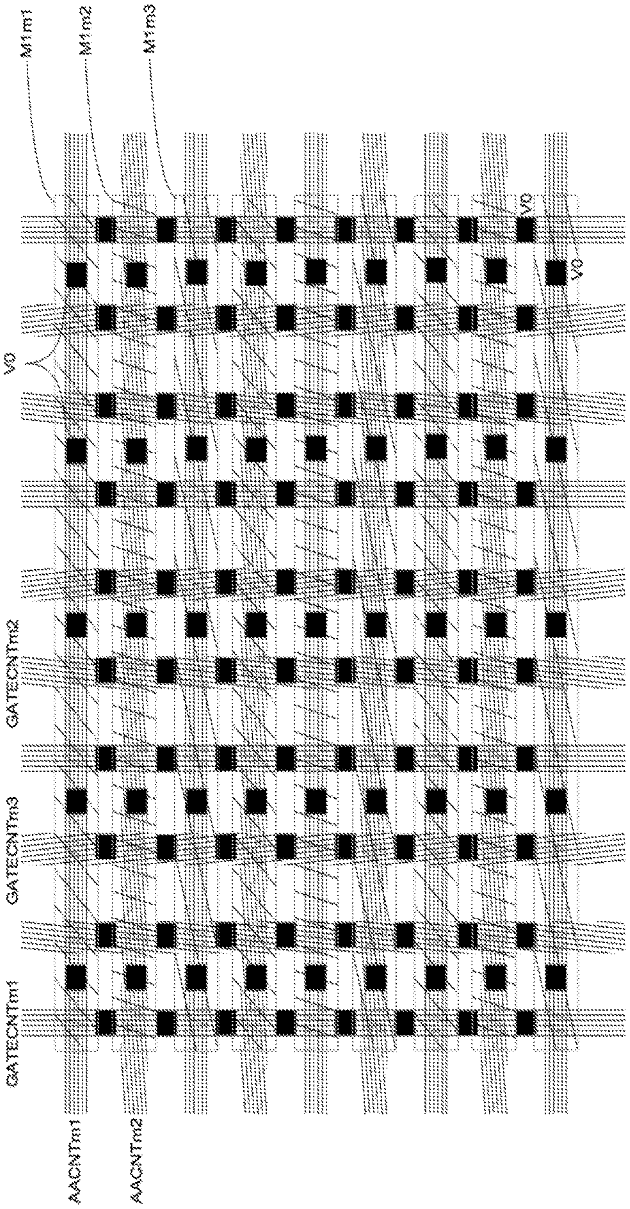
FIG. 9FFFF

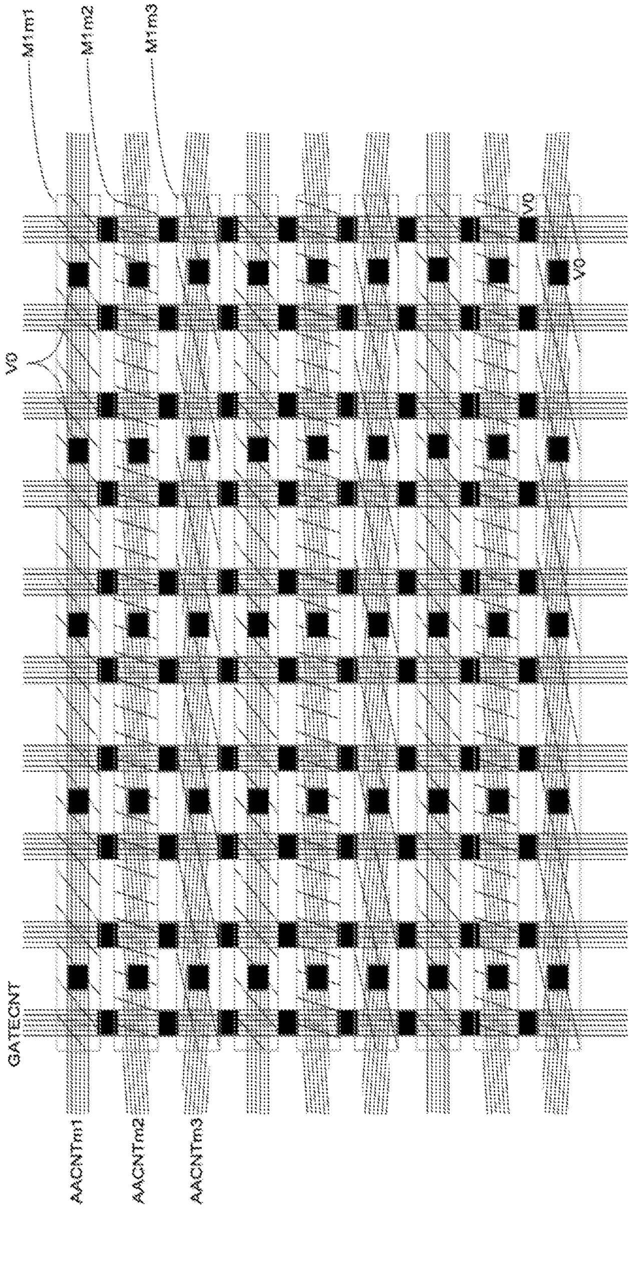
FIG. 9GGGG

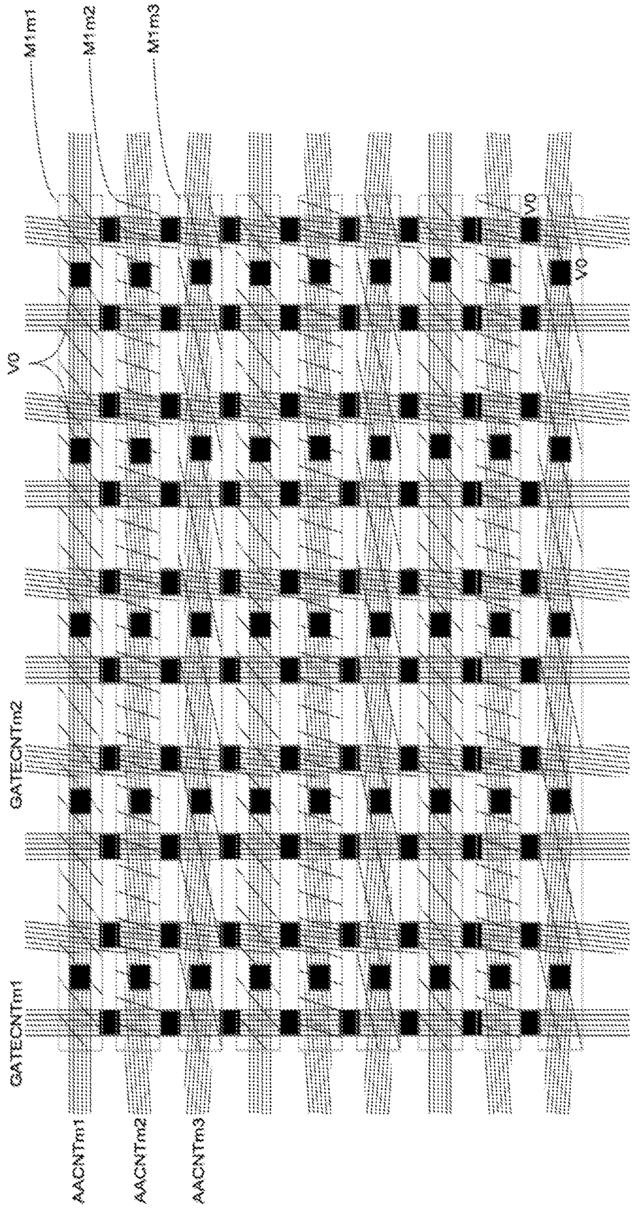
FIG. 9HHHH

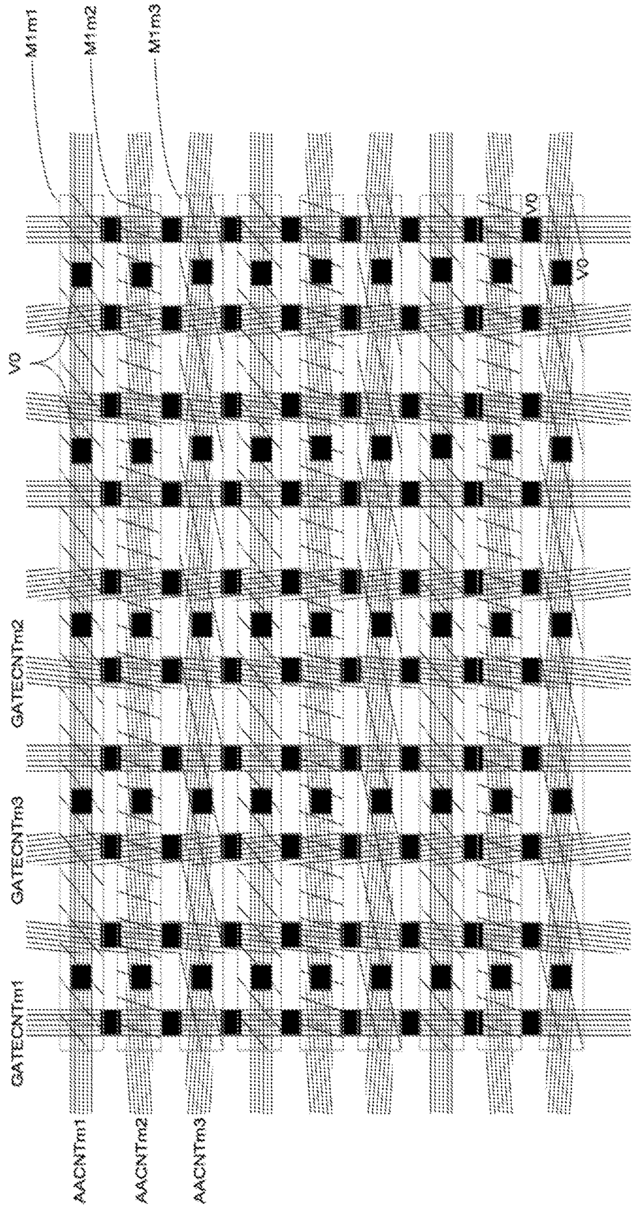
FIG. 9IIII

Tip-to-tip short (example 1)

Tip-to-tip short (example 2)

Side-to-side short

L-shape interlayer short (example 1)

L-shape interlayer short (example 2)

L-shape interlayer short (example 3)

L-shape interlayer short (example 4)

L-shape interlayer short (example 5)

Corner short (example 2)

Corner short (example 3)

Interlayer overlap short

Merged via short

Stitch open (example 1)

Stitch open (example 2)

Metal island open (plan view)

Metal island open (cross-sectional view)

1st variant

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

*M* PDF Solutions, Inc.

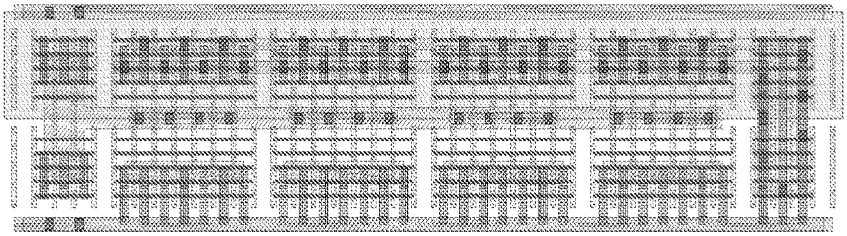
FIG. 1000A
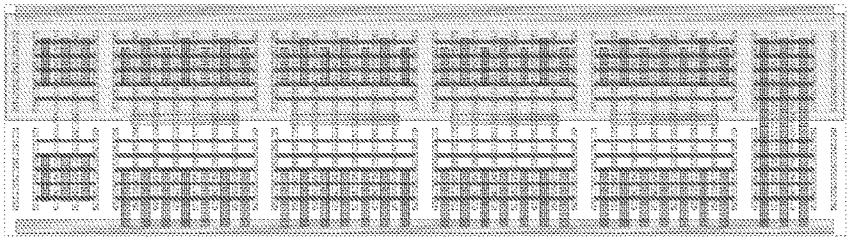
FIG. 1000B
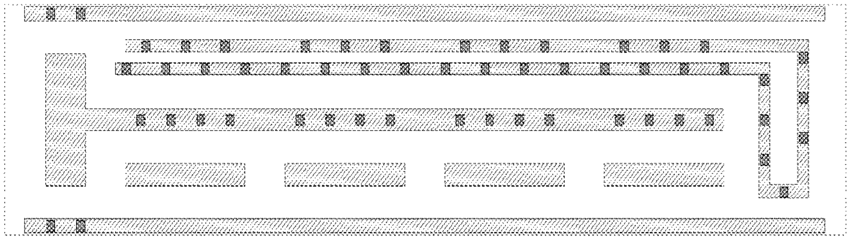
FIG. 1000C

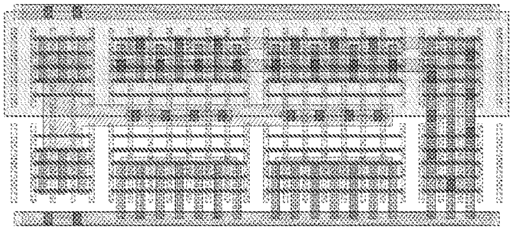
FIG. 1001A
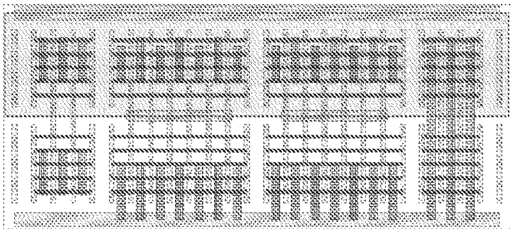
FIG. 1001B
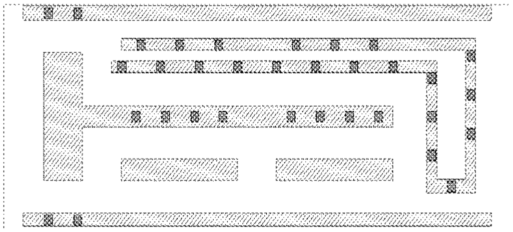
FIG. 1001C

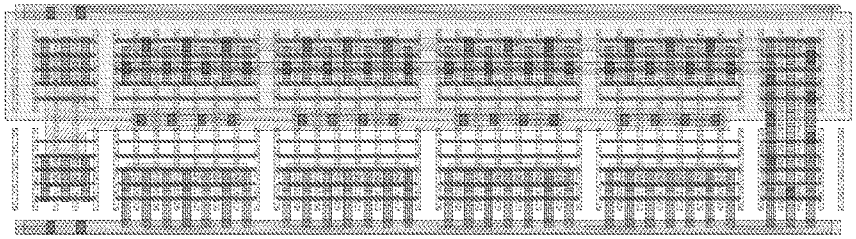
FIG. 1002A
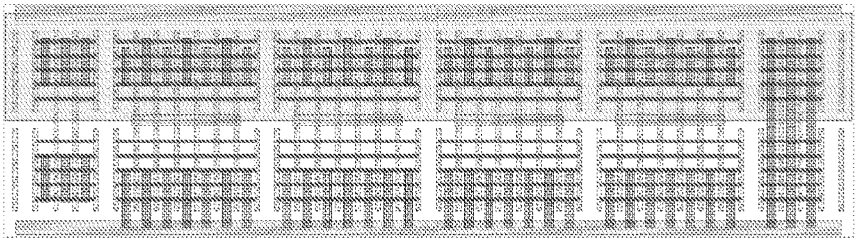
FIG. 1002B
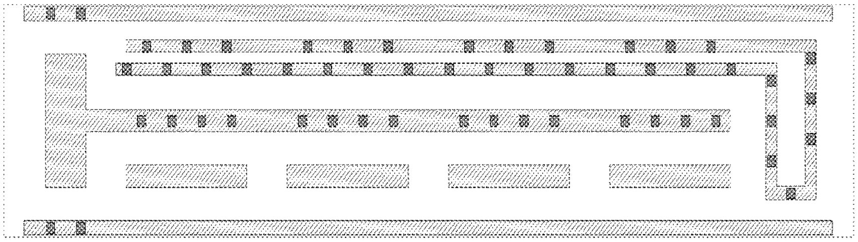
FIG. 1002C
*M* PDF Solutions, Inc.

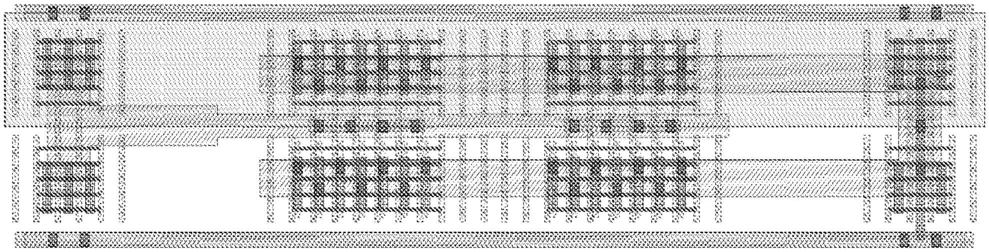
FIG. 1003A
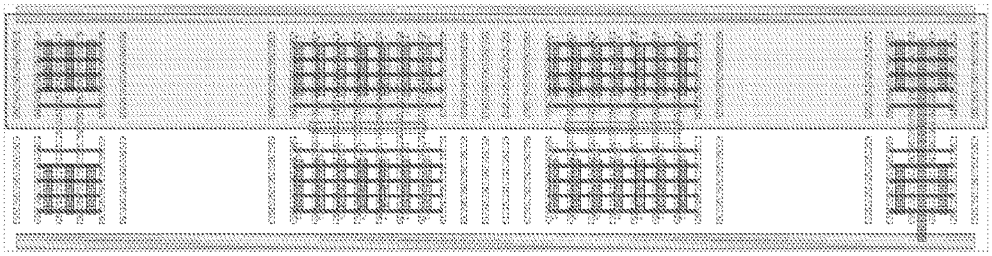
FIG. 1003B
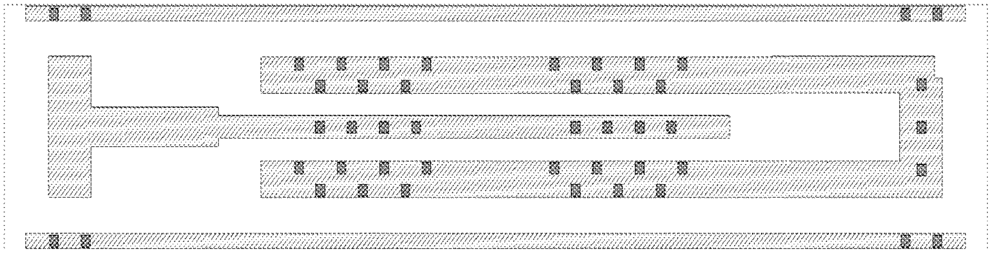
FIG. 1003C
*M* PDF Solutions, Inc.

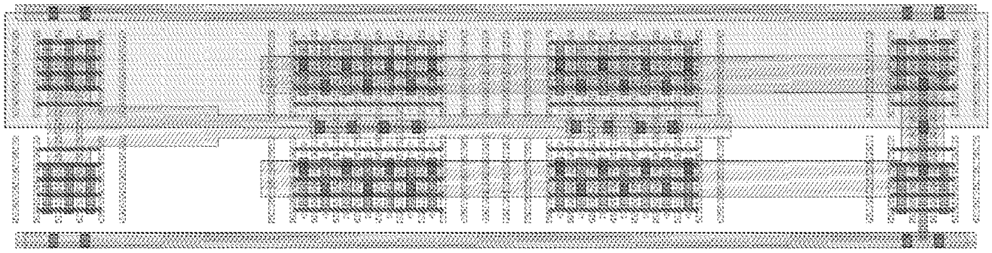
FIG. 1004A
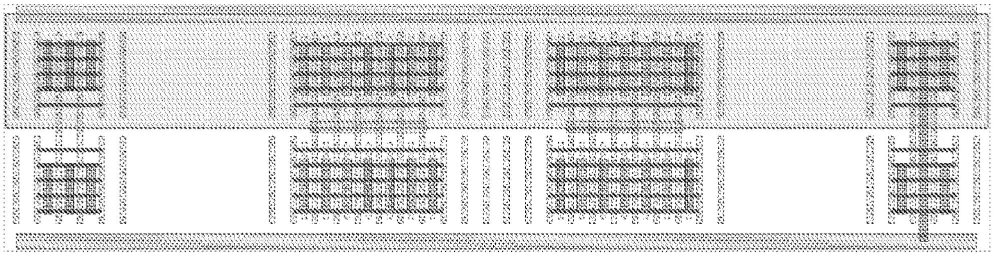
FIG. 1004B
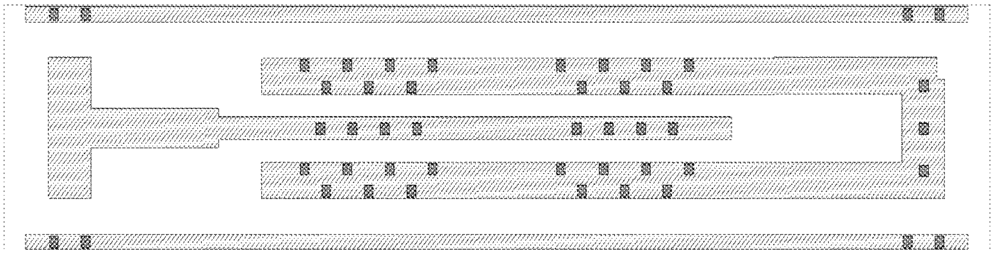
FIG. 1004C
*M* PDF Solutions, Inc.

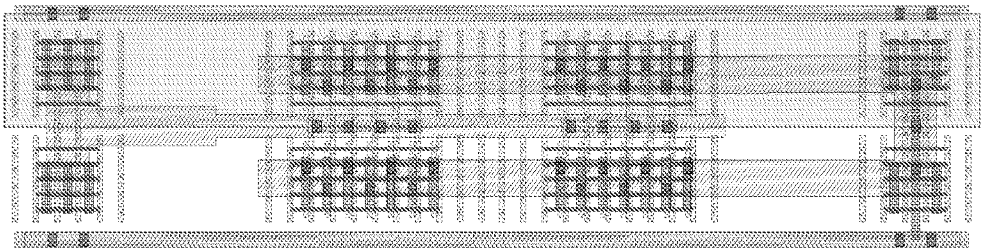
FIG. 1005A
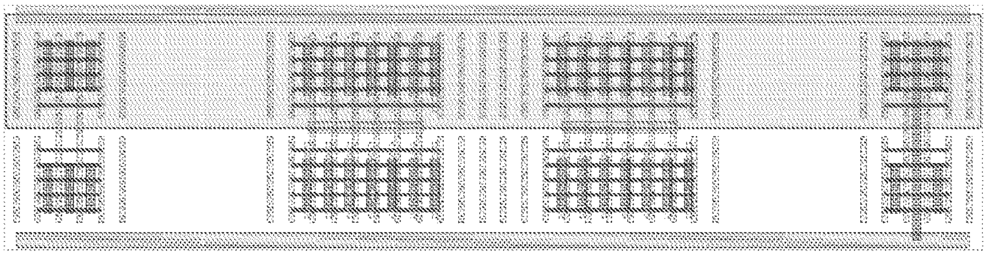
FIG. 1005B
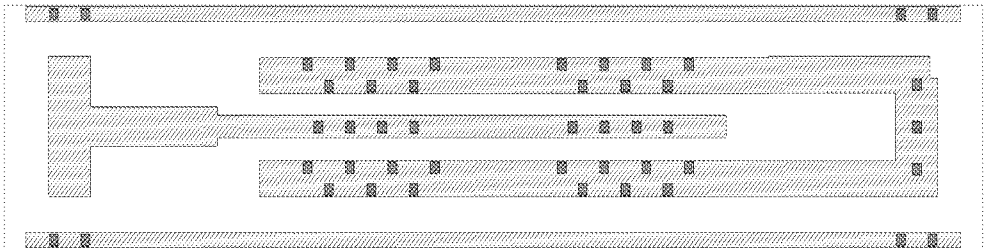
FIG. 1005C
*M* PDF Solutions, Inc.

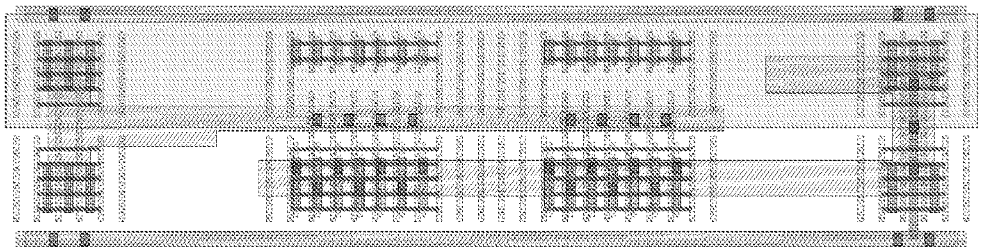
FIG. 1006A
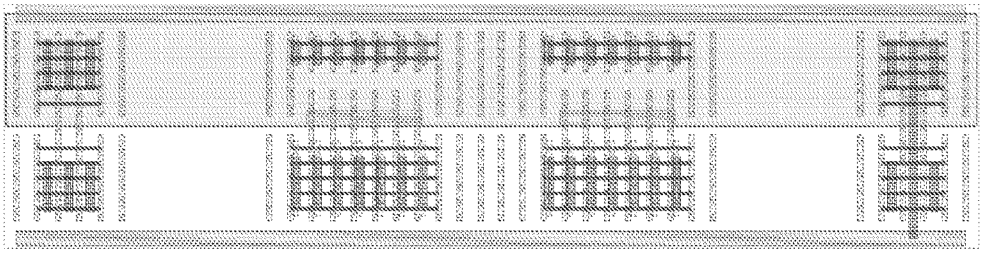
FIG. 1006B
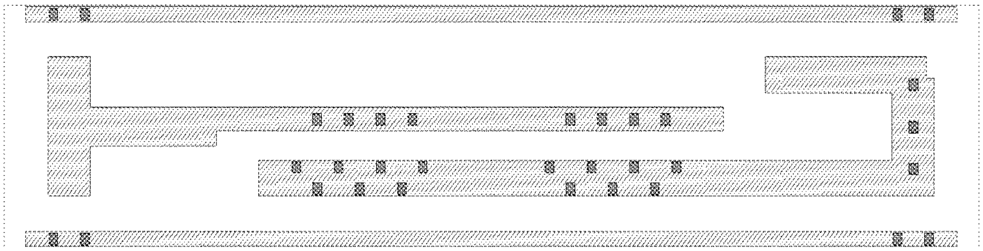
FIG. 1006C

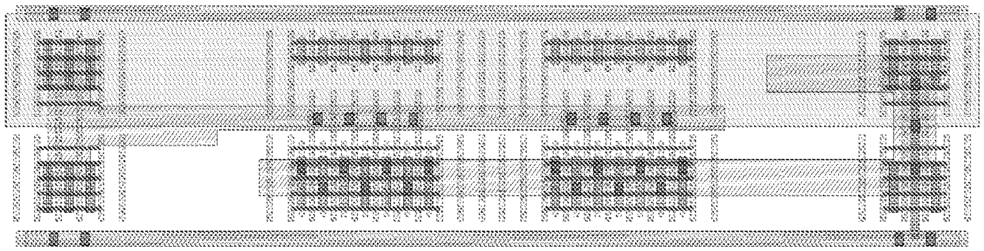
FIG. 1007A
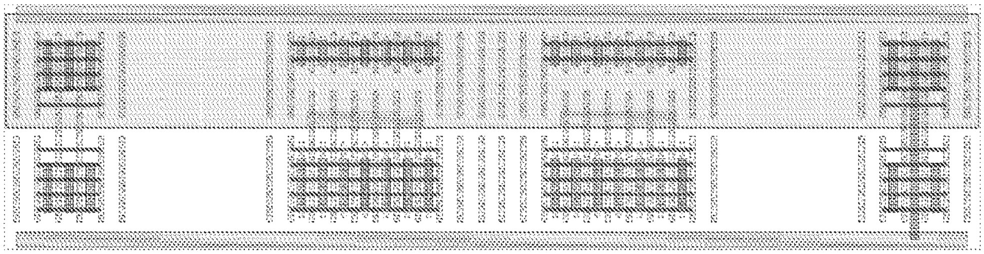
FIG. 1007B
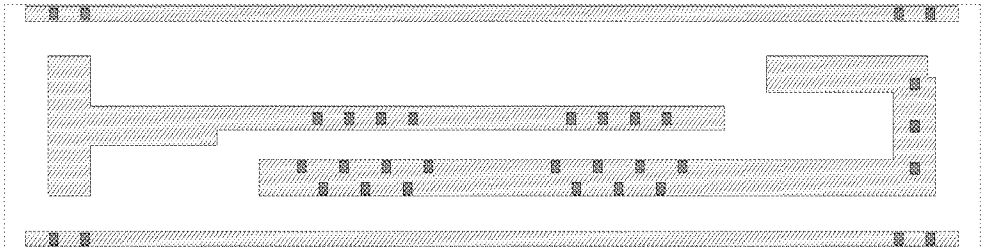
FIG. 1007C
*M* PDF Solutions, Inc.

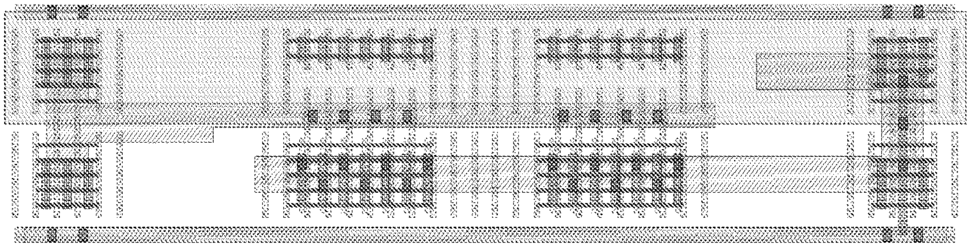
FIG. 1008A
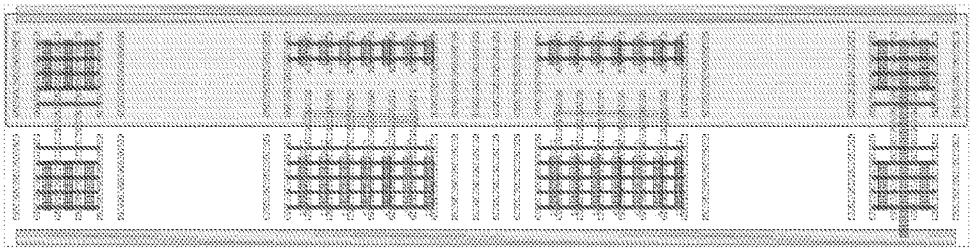
FIG. 1008B
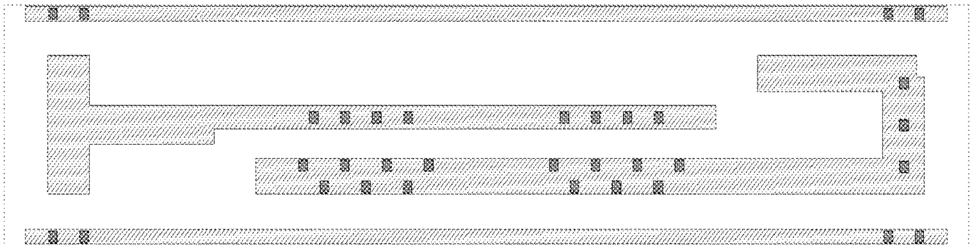
FIG. 1008C
*M* PDF Solutions, Inc.

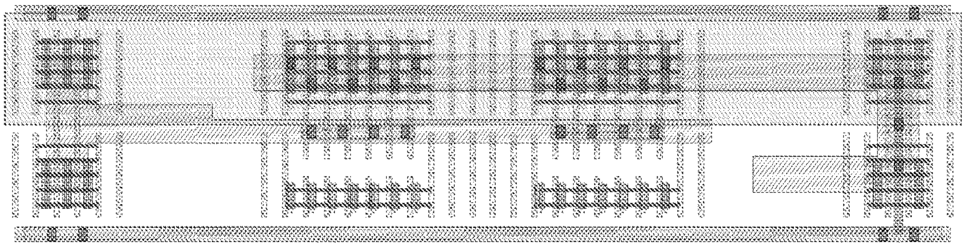
FIG. 1009A
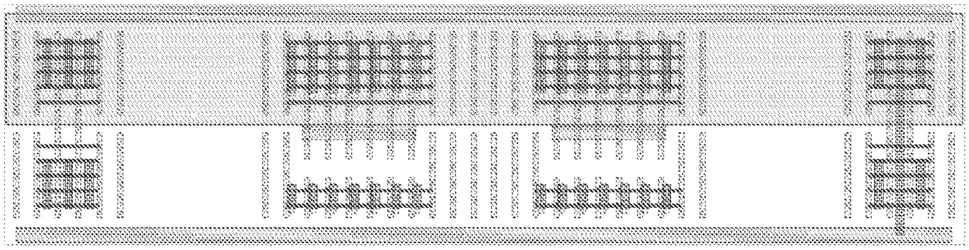
FIG. 1009B
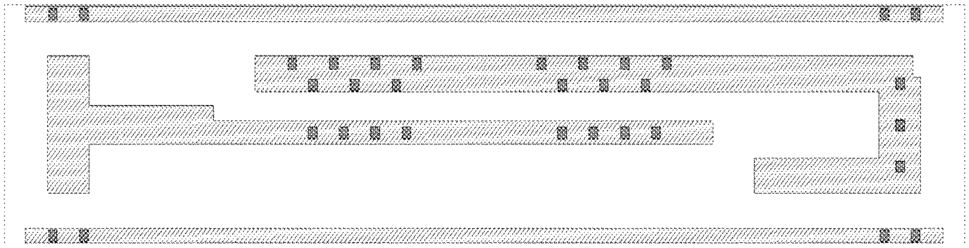
FIG. 1009C
*M* PDF Solutions, Inc.

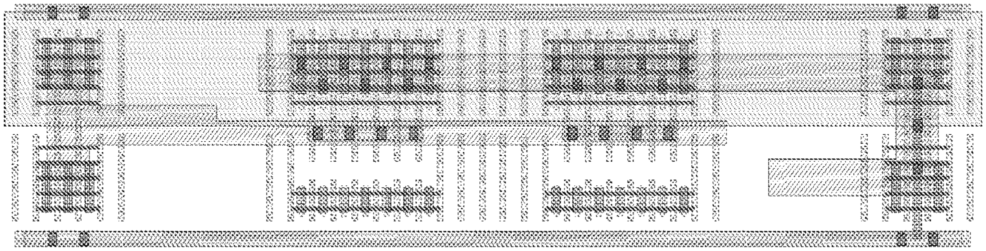
FIG. 1010A
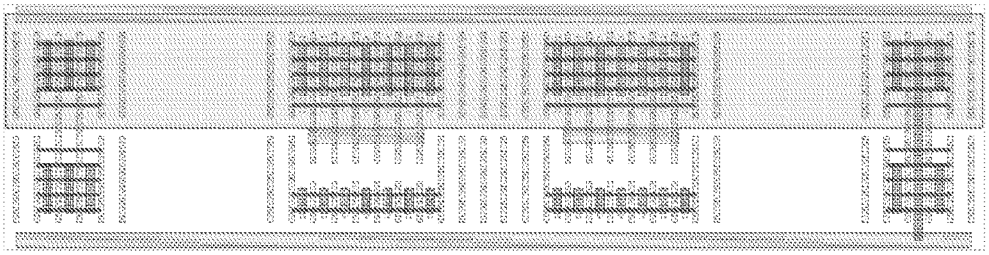
FIG. 1010B
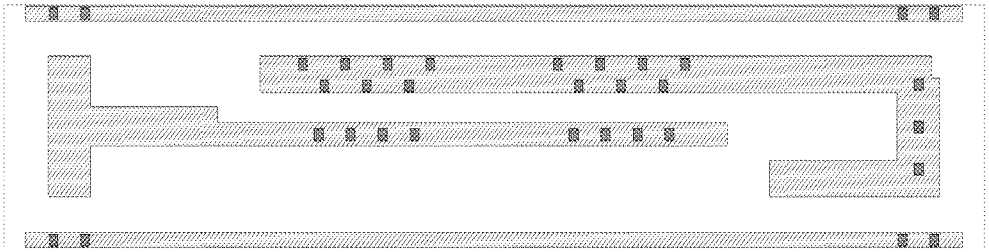
FIG. 1010C
*M* PDF Solutions, Inc.

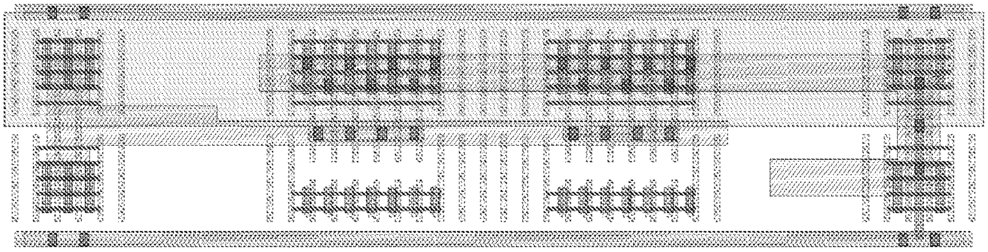
FIG. 1011A
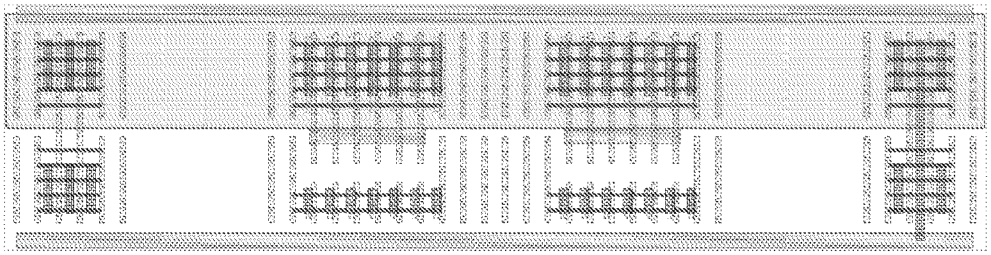
FIG. 1011B
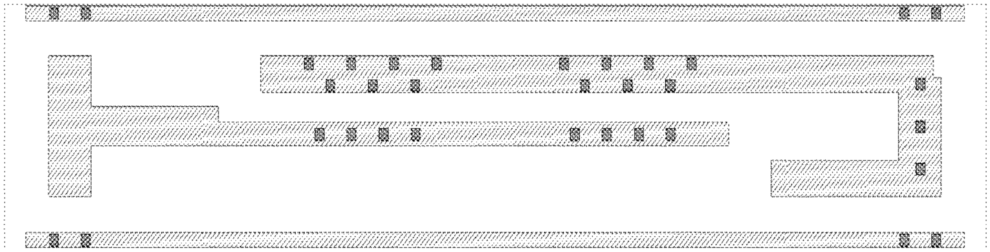
FIG. 1011C
*M* PDF Solutions, Inc.

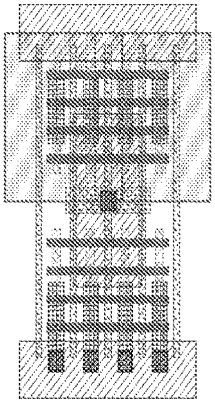
FIG. 1012A
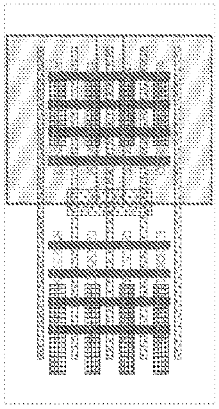
FIG. 1012B
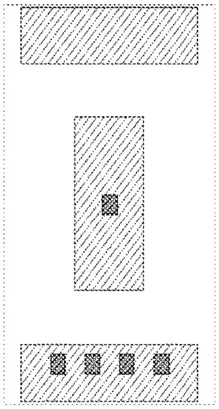
FIG. 1012C
*M* PDF Solutions, Inc.

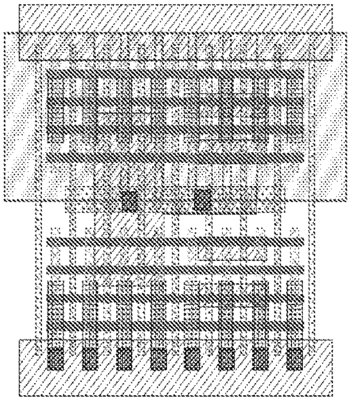
FIG. 1013A
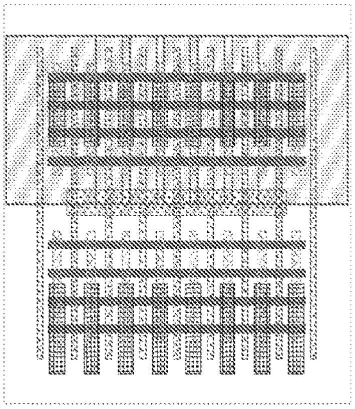
FIG. 1013B
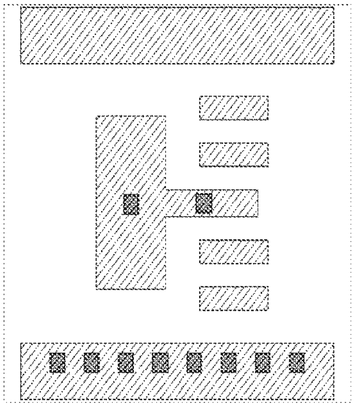
FIG. 1013C

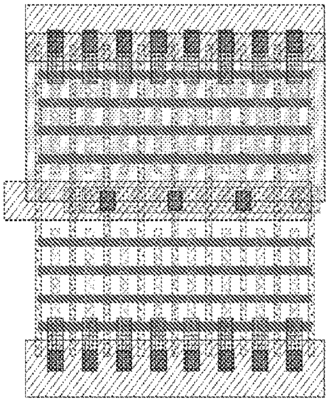
FIG. 1014A
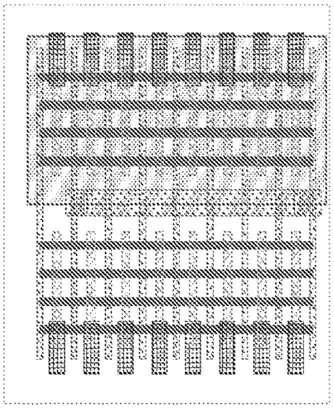
FIG. 1014B
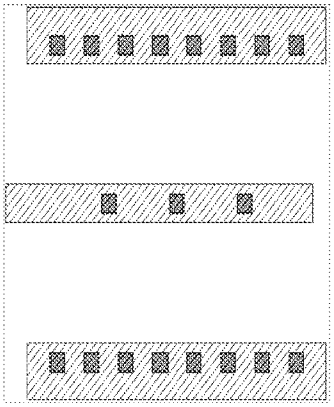
FIG. 1014C

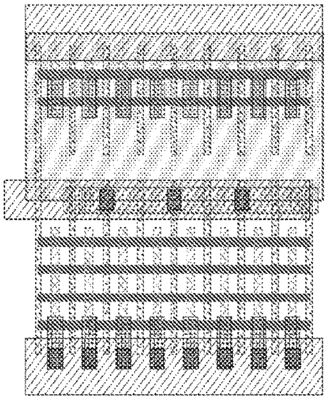
FIG. 1015A
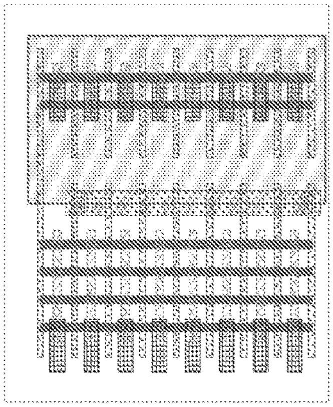
FIG. 1015B
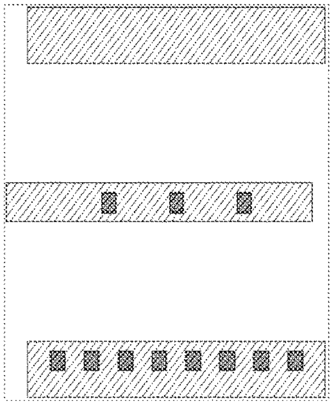
FIG. 1015C

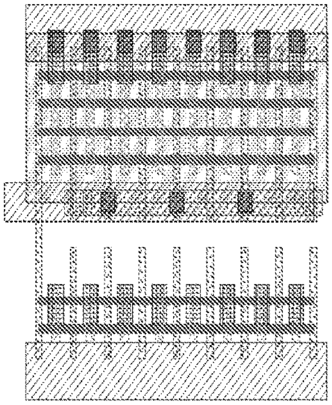
FIG. 1016A
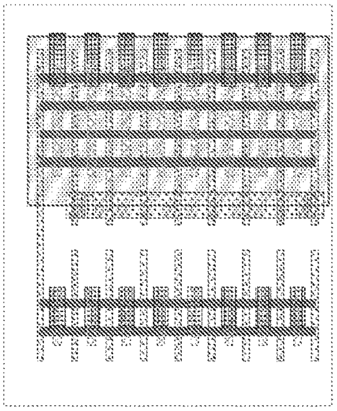
FIG. 1016B
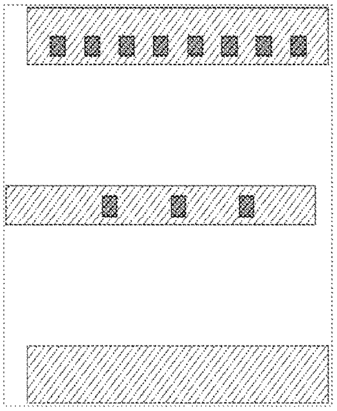
FIG. 1016C

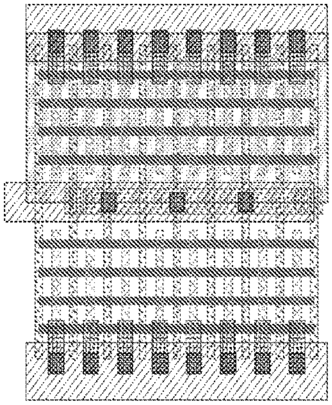
FIG. 1017A
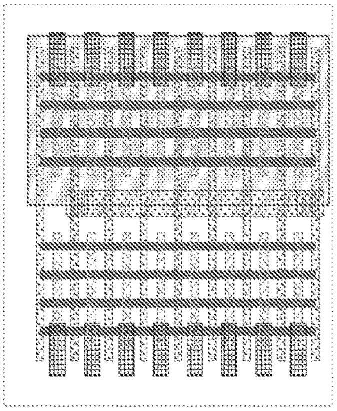
FIG. 1017B
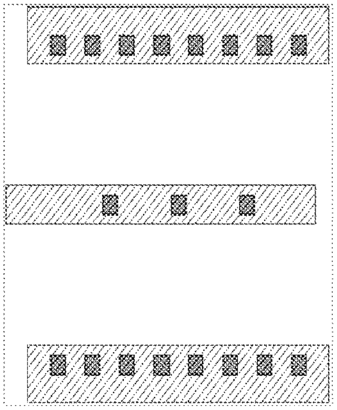
FIG. 1017C

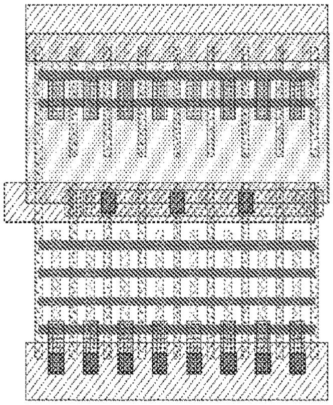
FIG. 1018A
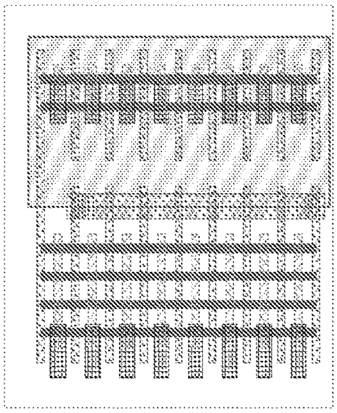
FIG. 1018B
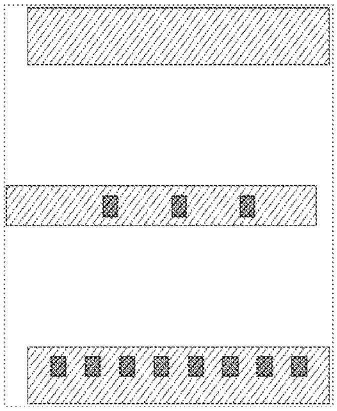
FIG. 1018C

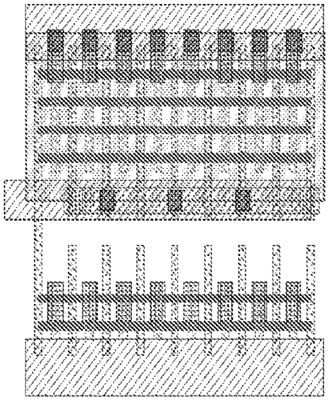
FIG. 1019A
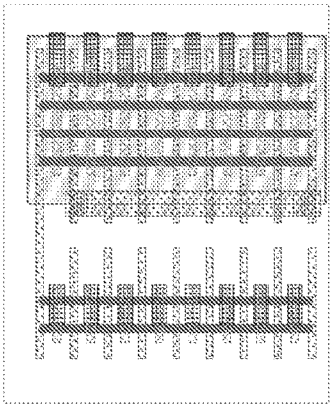
FIG. 1019B
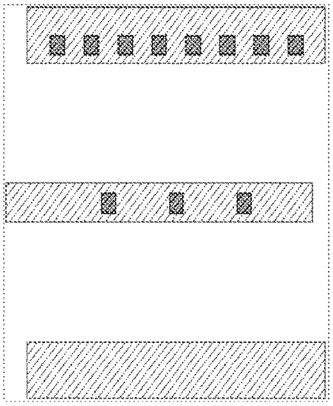
FIG. 1019C

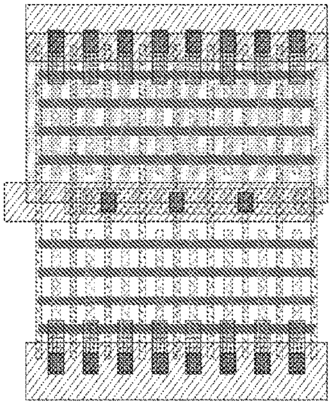
FIG. 1020A
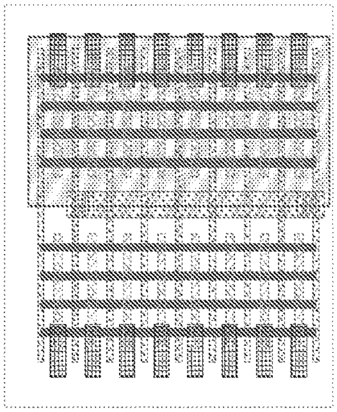
FIG. 1020B
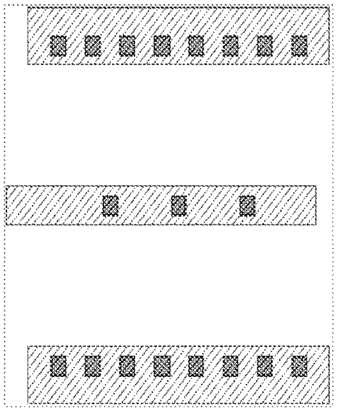
FIG. 1020C

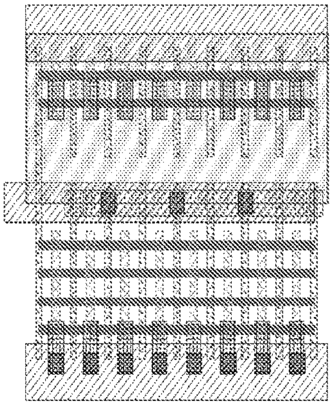
FIG. 1021A
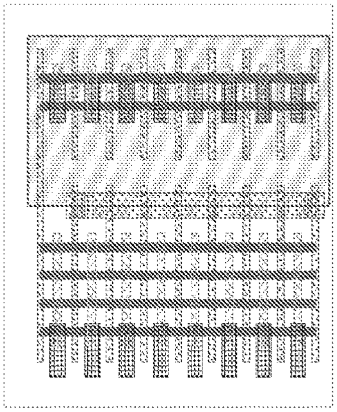
FIG. 1021B
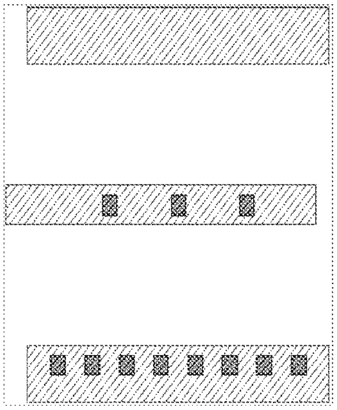
FIG. 1021C

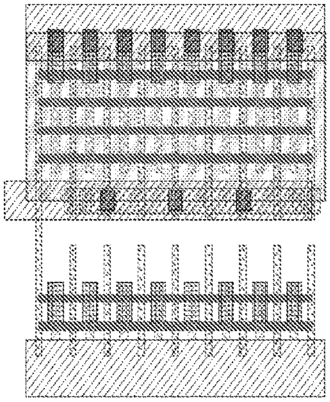
FIG. 1022A
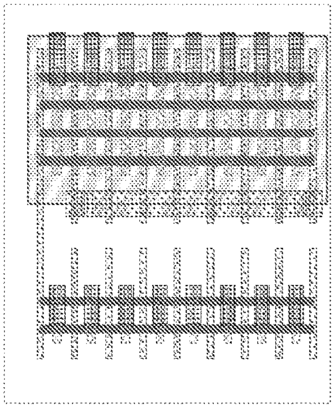
FIG. 1022B
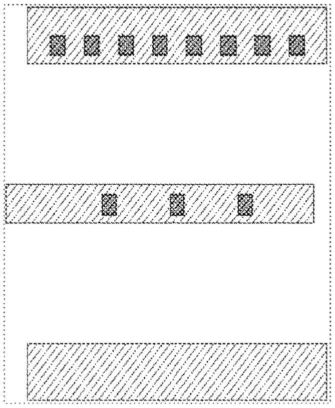
FIG. 1022C

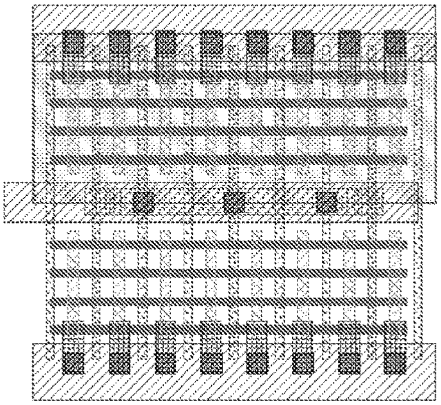
FIG. 1023A
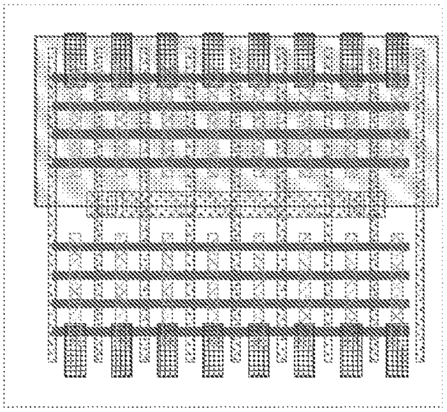
FIG. 1023B
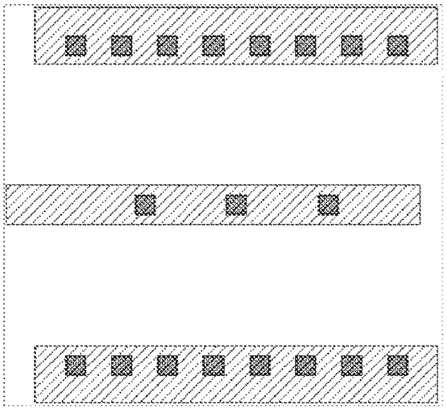
FIG. 1023C
*M* PDF Solutions, Inc.

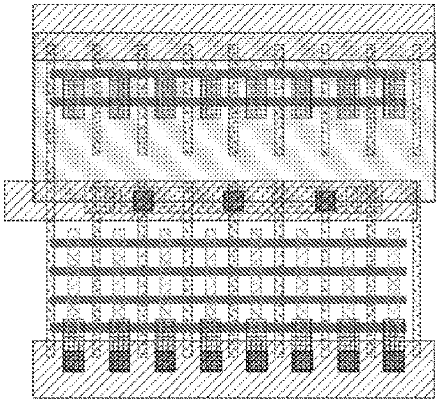
FIG. 1024A
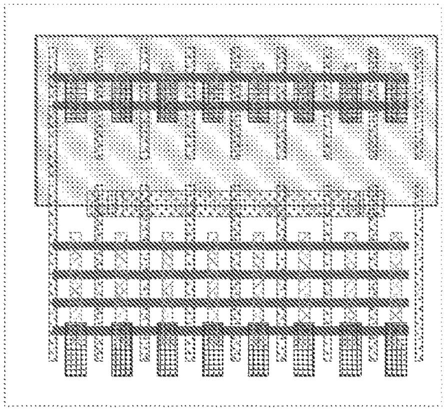
FIG. 1024B
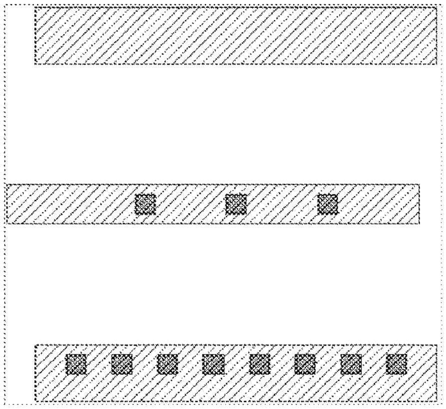
FIG. 1024C

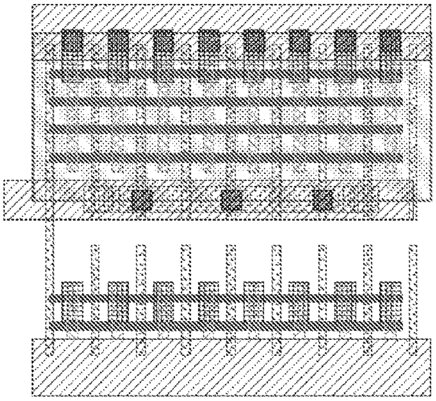
FIG. 1025A
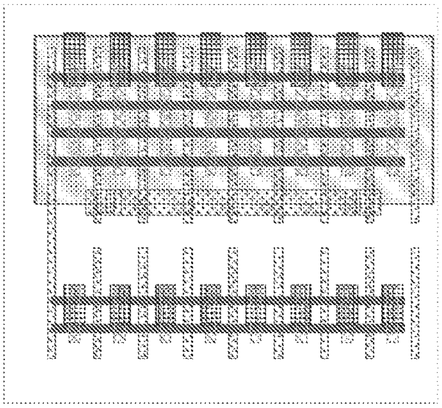
FIG. 1025B
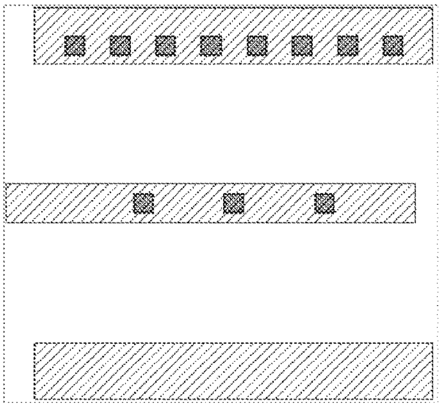
FIG. 1025C

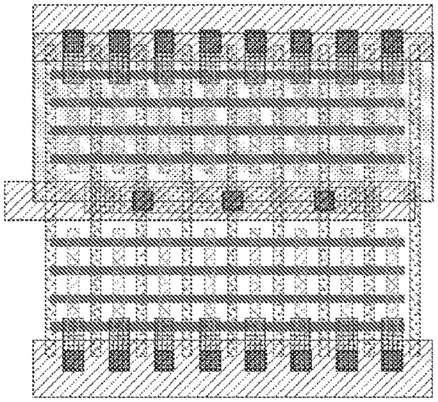
FIG. 1026A
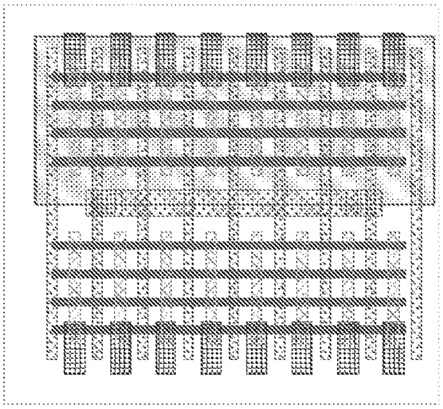
FIG. 1026B
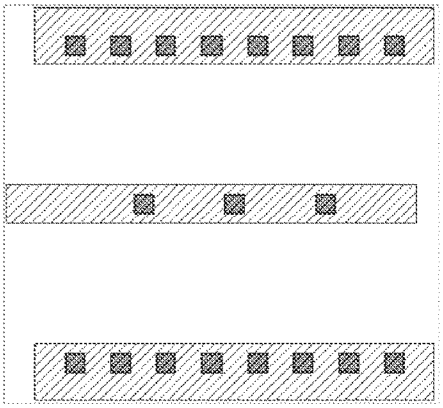
FIG. 1026C
*M* PDF Solutions, Inc.

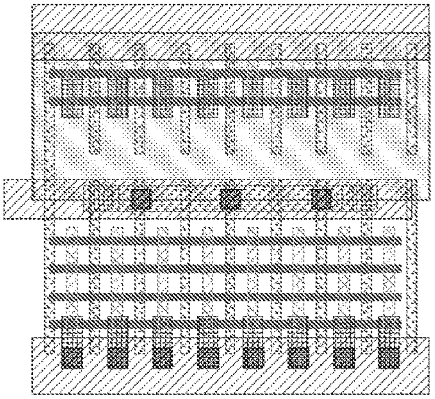
FIG. 1027A
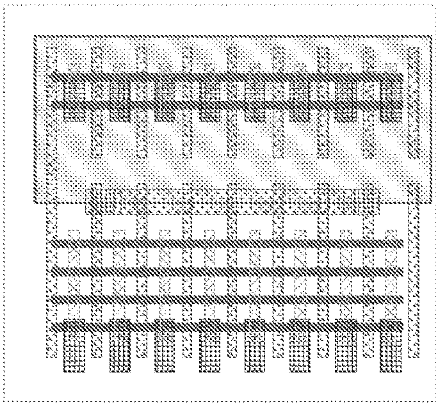
FIG. 1027B
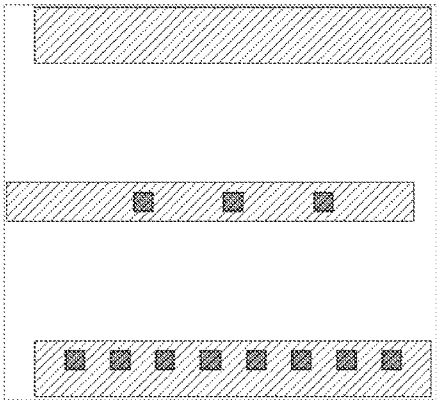
FIG. 1027C
*M* PDF Solutions, Inc.

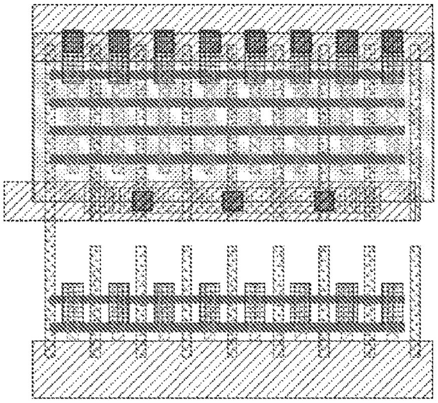
FIG. 1028A
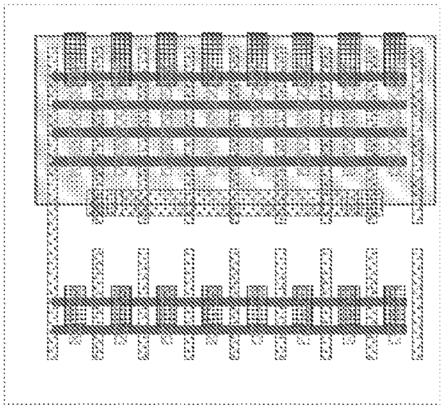
FIG. 1028B
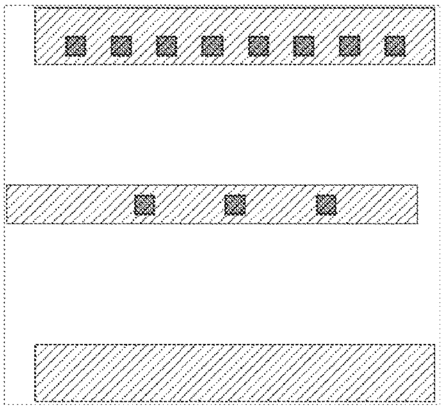
FIG. 1028C

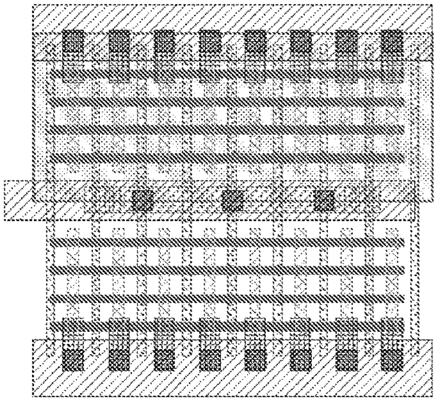
FIG. 1029A
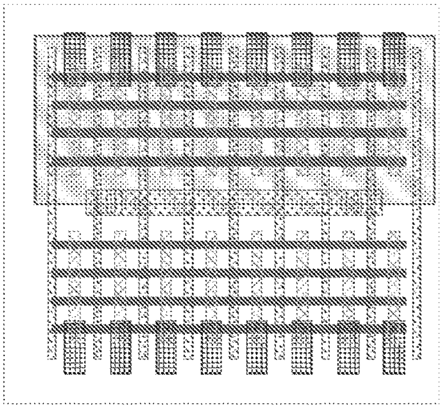
FIG. 1029B
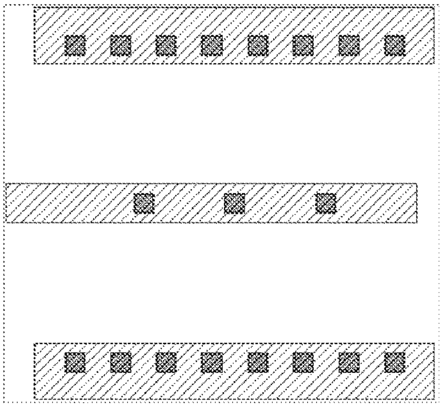
FIG. 1029C
*M* PDF Solutions, Inc.

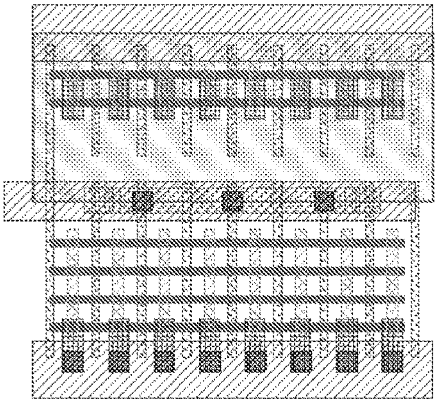
FIG. 1030A
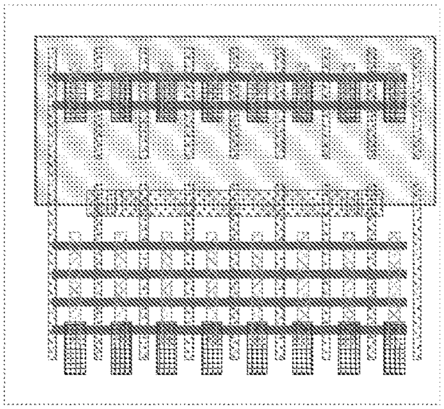
FIG. 1030B
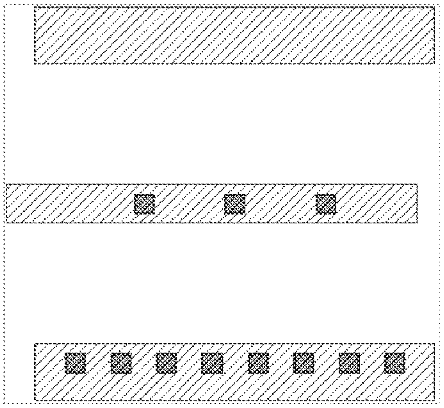
FIG. 1030C

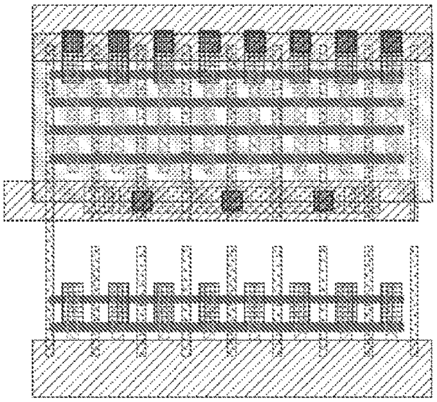
FIG. 1031A
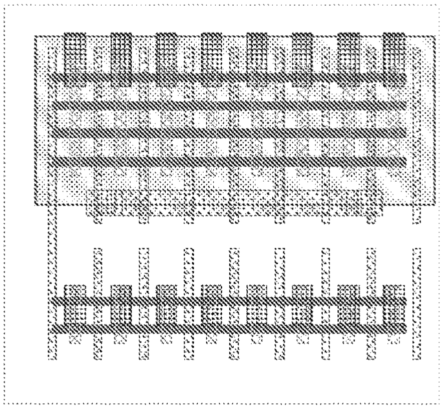
FIG. 1031B
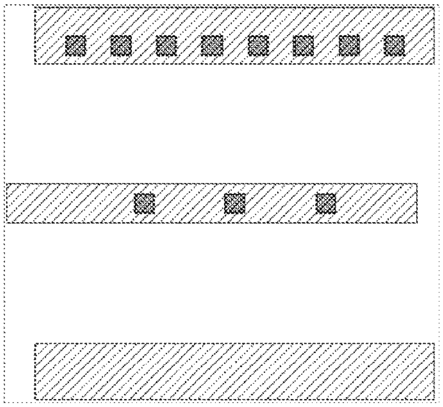
FIG. 1031C

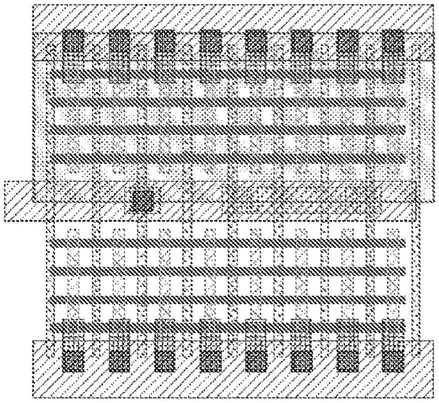
FIG. 1032A
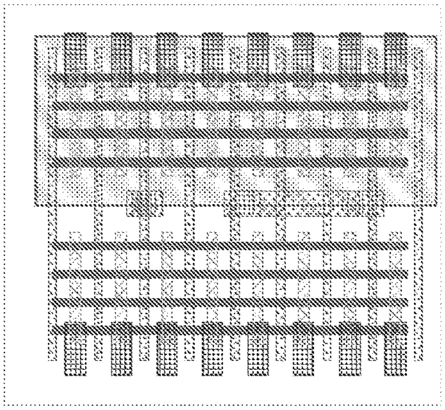
FIG. 1032B
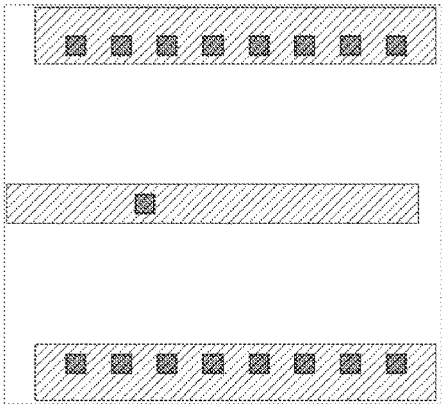
FIG. 1032C
*M* PDF Solutions, Inc.

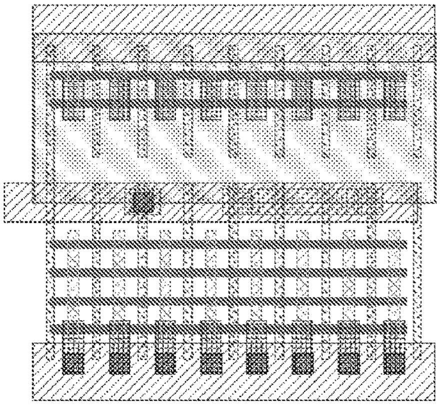
FIG. 1033A
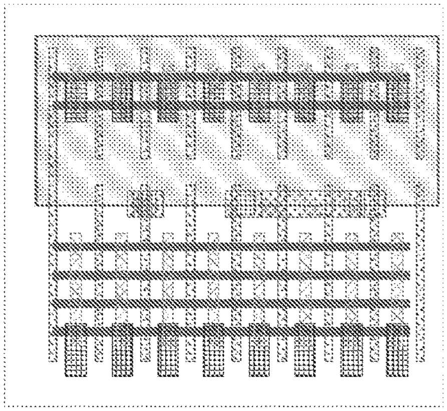
FIG. 1033B
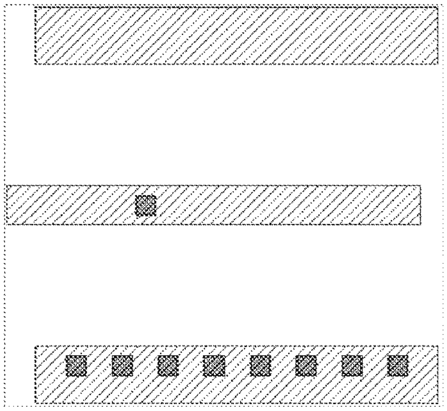
FIG. 1033C

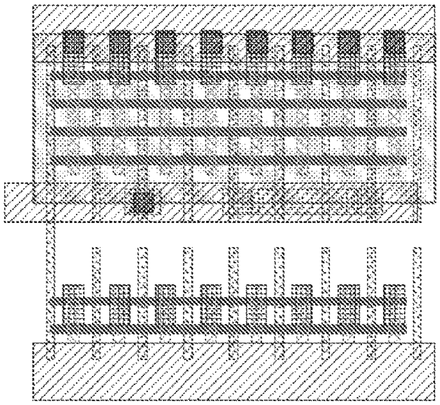
FIG. 1034A
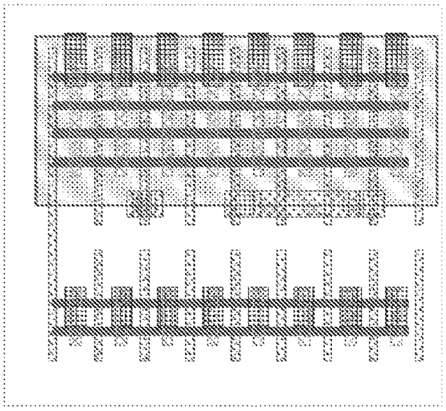
FIG. 1034B
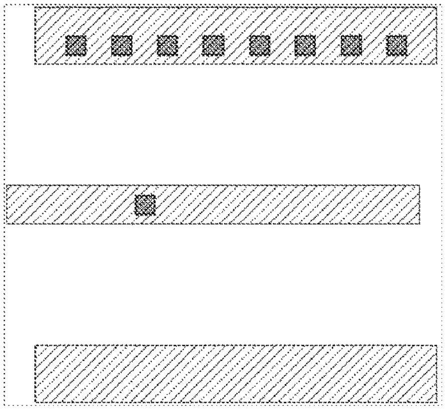
FIG. 1034C

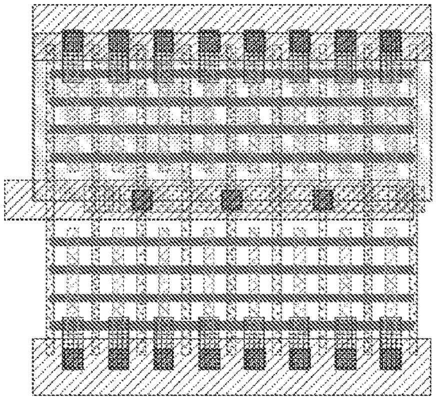
FIG. 1035A
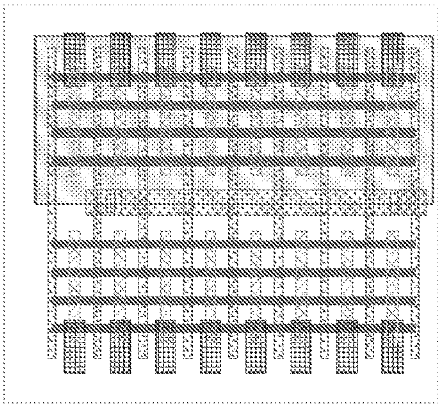
FIG. 1035B
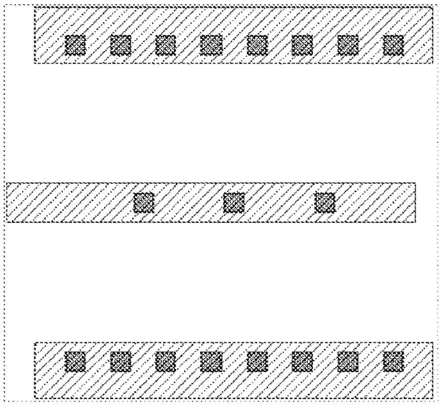
FIG. 1035C
*M* PDF Solutions, Inc.

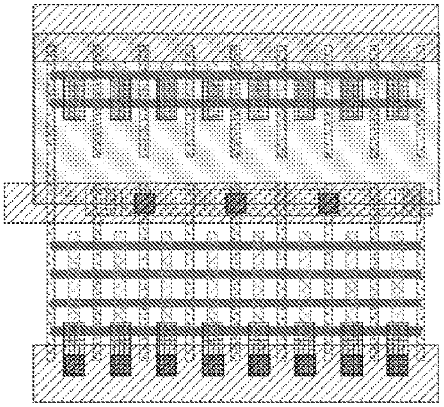
FIG. 1036A
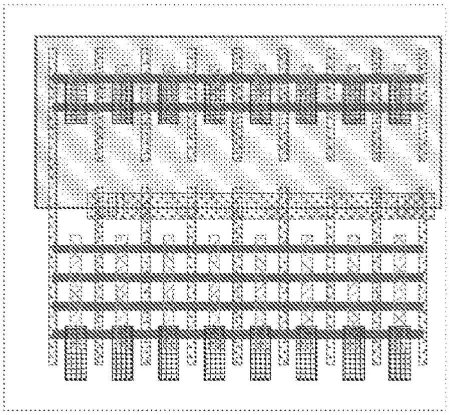
FIG. 1036B
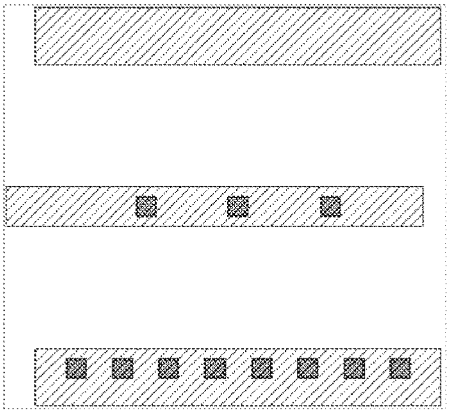
FIG. 1036C
*M* PDF Solutions, Inc.

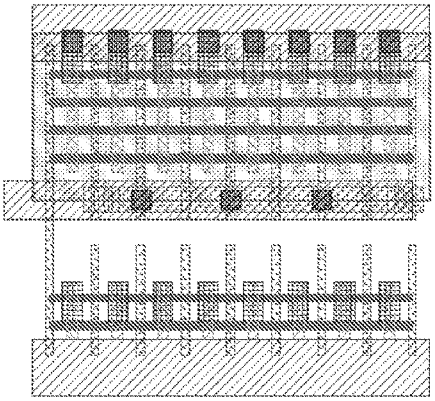
FIG. 1037A
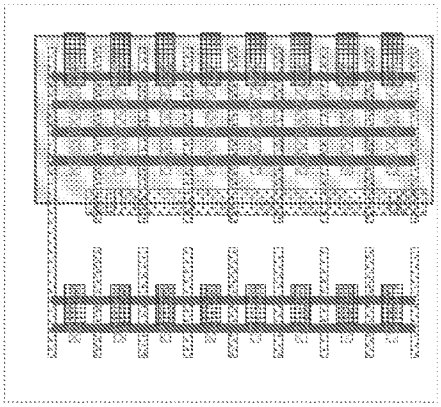
FIG. 1037B
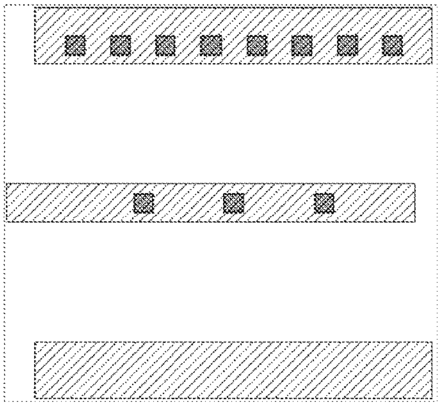
FIG. 1037C

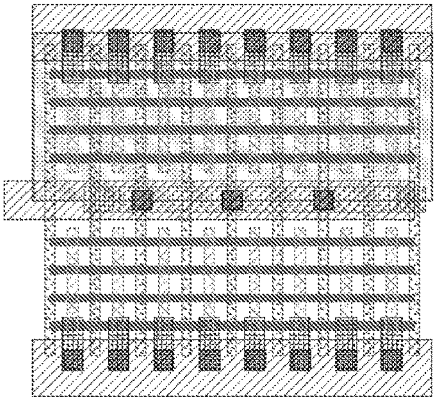
FIG. 1038A
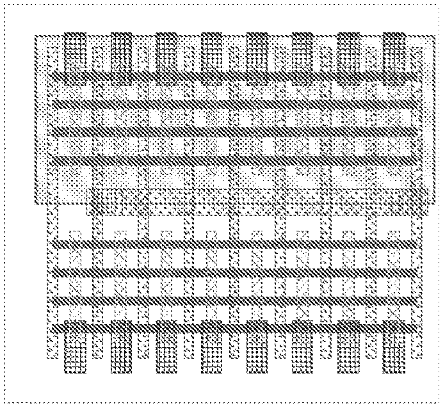
FIG. 1038B
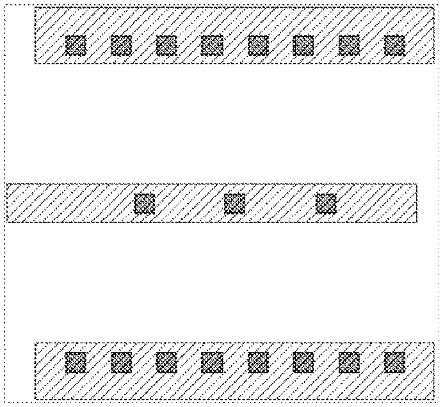
FIG. 1038C
*M* PDF Solutions, Inc.

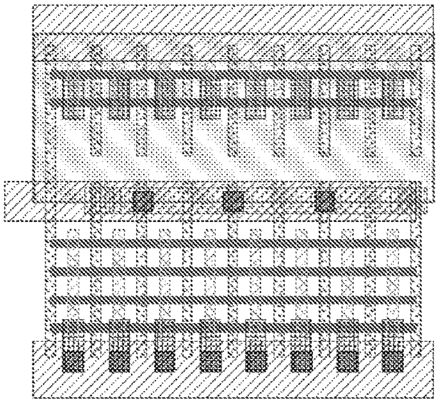
FIG. 1039A
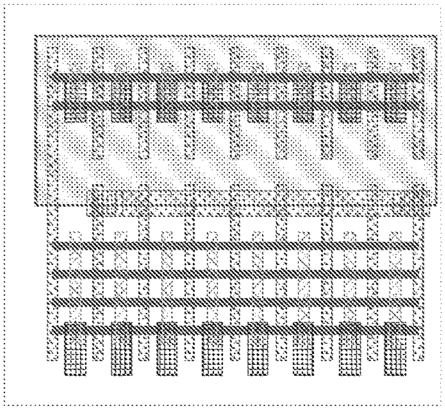
FIG. 1039B
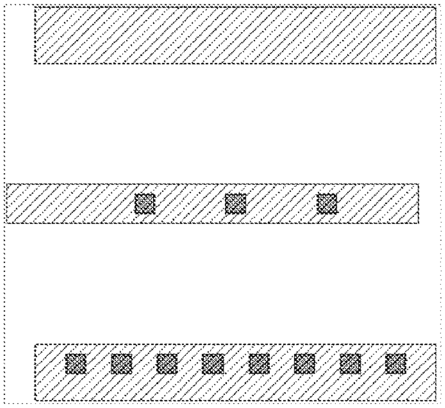
FIG. 1039C
*M* PDF Solutions, Inc.

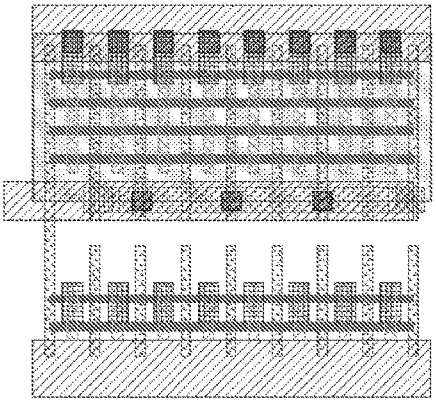
FIG. 1040A
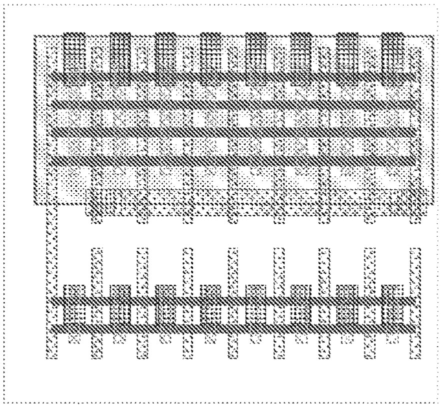
FIG. 1040B
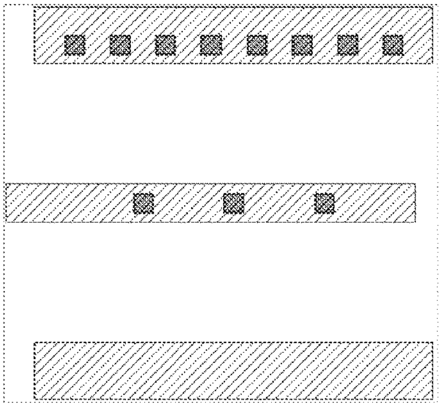
FIG. 1040C

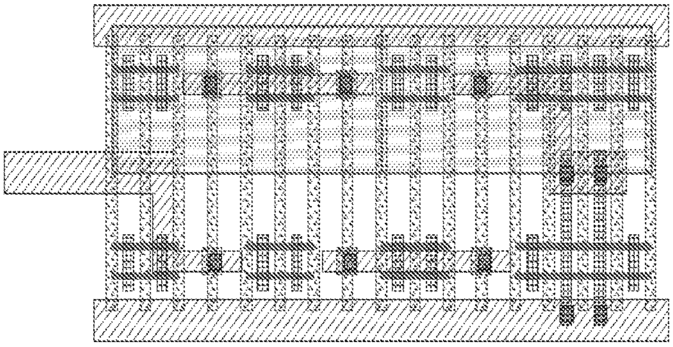
FIG. 1041A
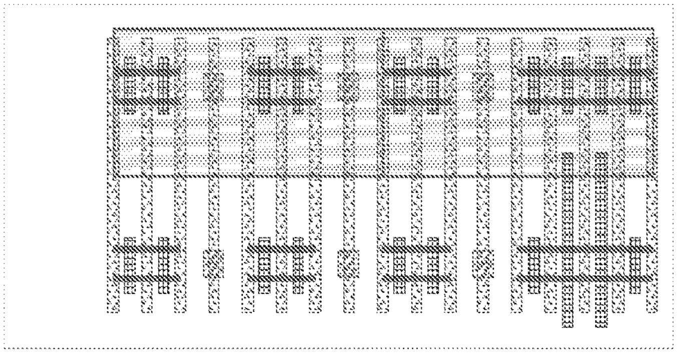
FIG. 1041B
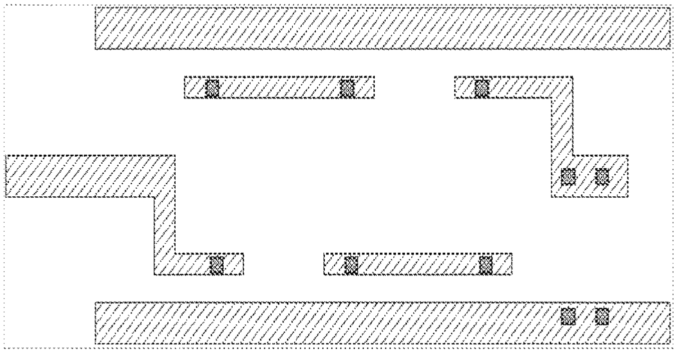
FIG. 1041C

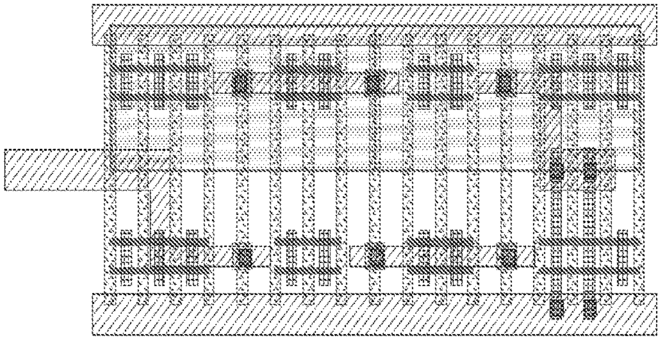
FIG. 1042A
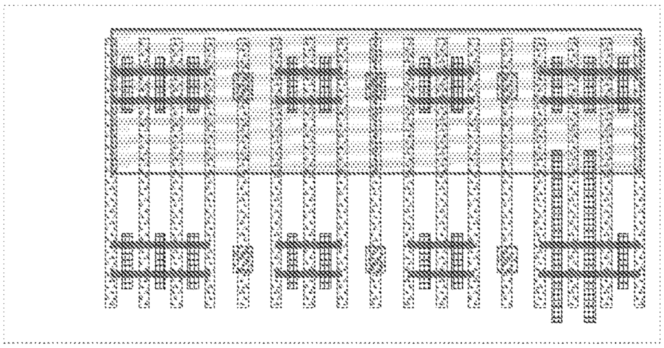
FIG. 1042B
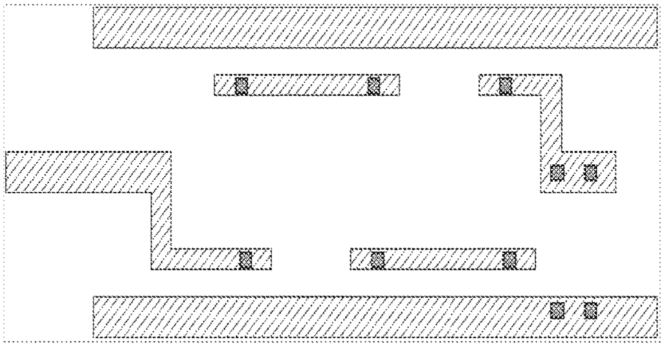
FIG. 1042C

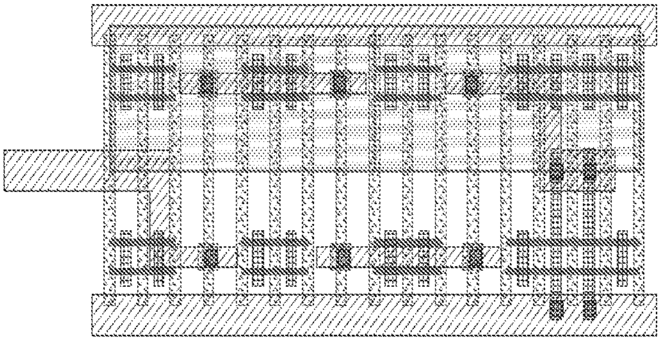
FIG. 1043A
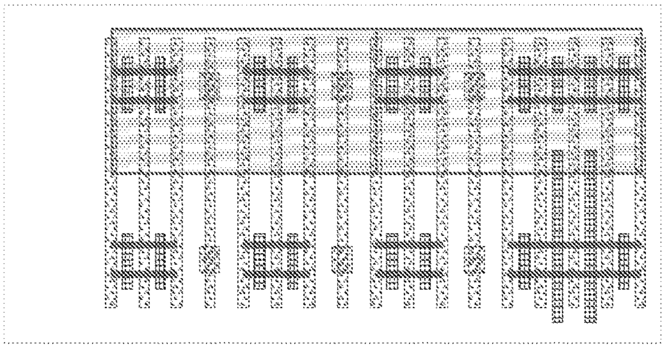
FIG. 1043B
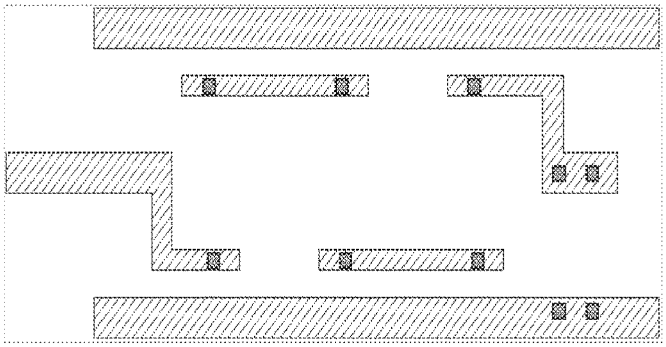
FIG. 1043C

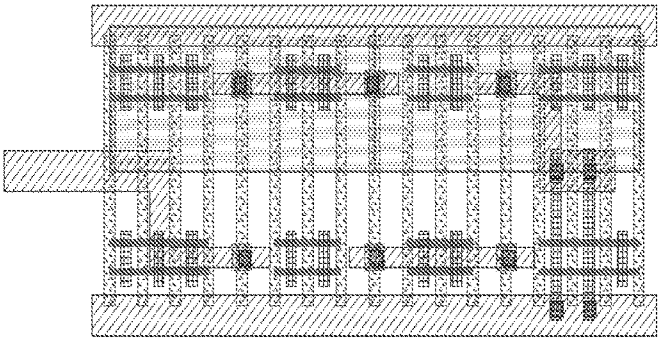
FIG. 1044A
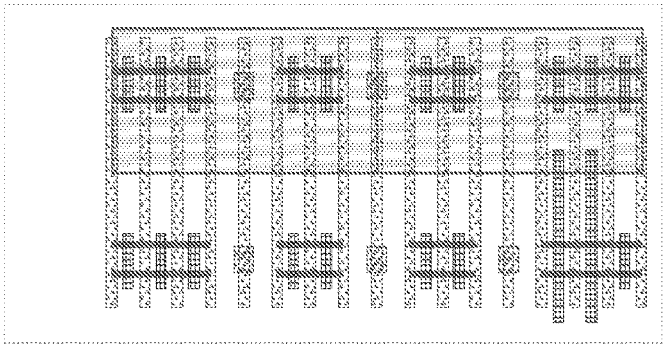
FIG. 1044B
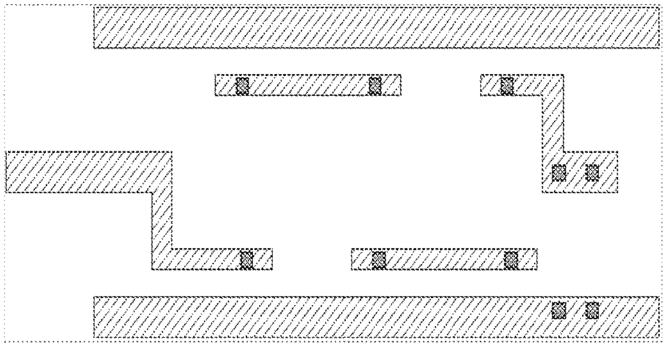
FIG. 1044C
*M* PDF Solutions, Inc.

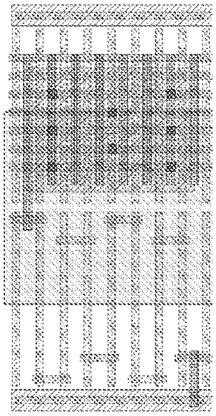
FIG. 1045A
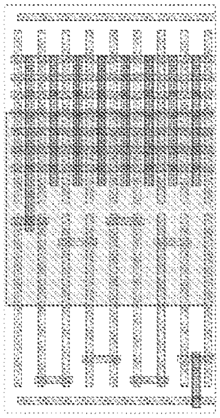
FIG. 1045B
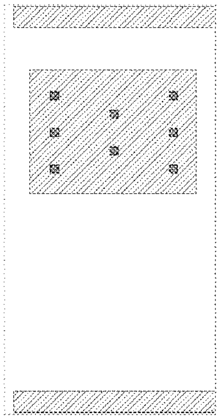
FIG. 1045C

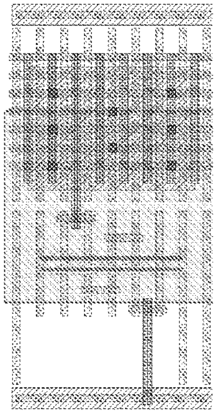
FIG. 1046A
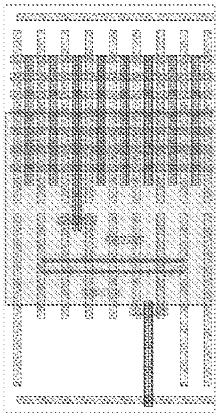
FIG. 1046B
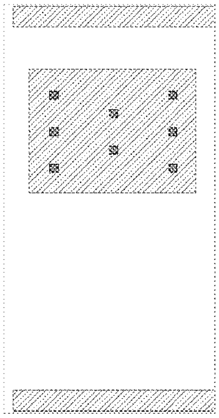
FIG. 1046C

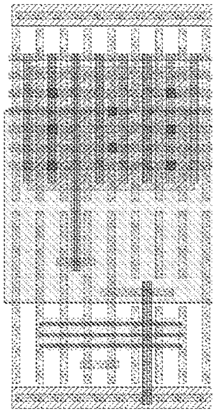
FIG. 1047A
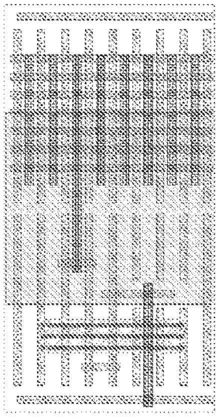
FIG. 1047B
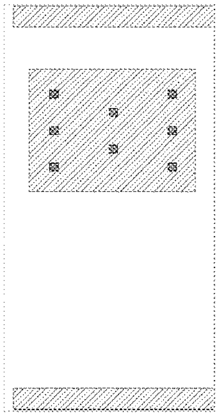
FIG. 1047C

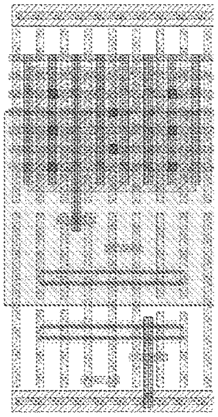
FIG. 1048A
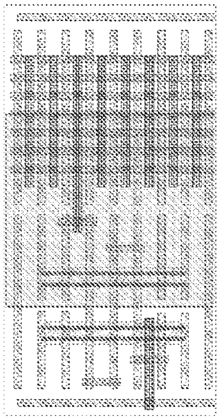
FIG. 1048B
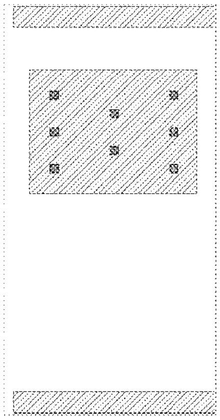
FIG. 1048C
*M* PDF Solutions, Inc.

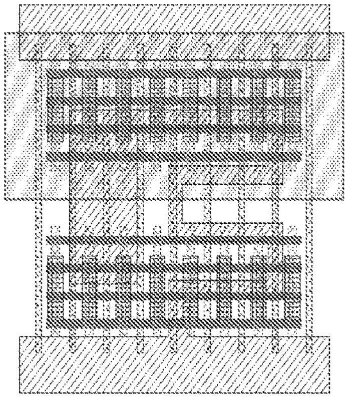
FIG. 1049A
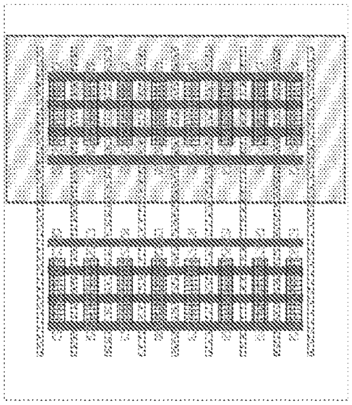
FIG. 1049B
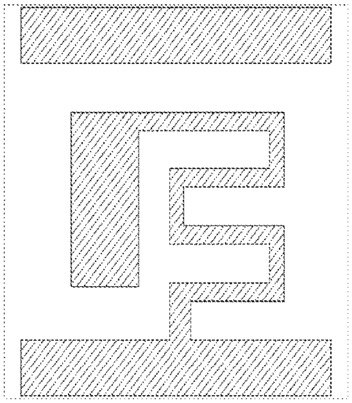
FIG. 1049C

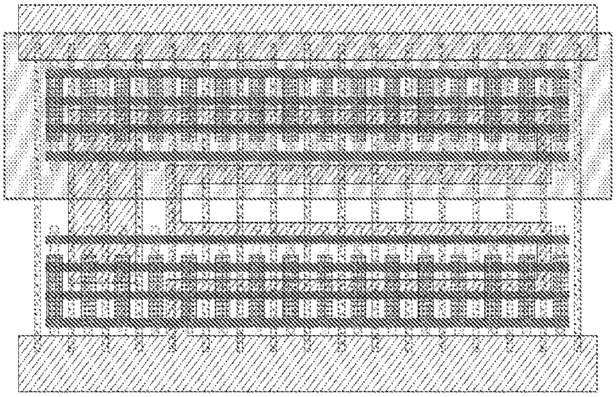
FIG. 1050A
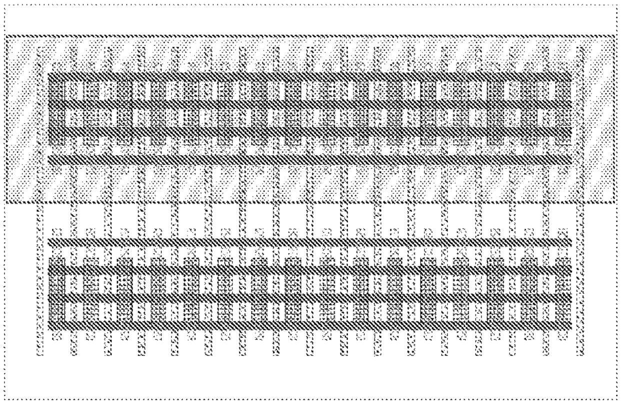
FIG. 1050B
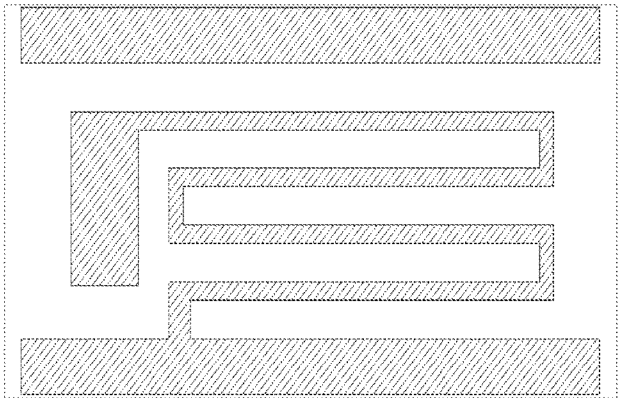
FIG. 1050C

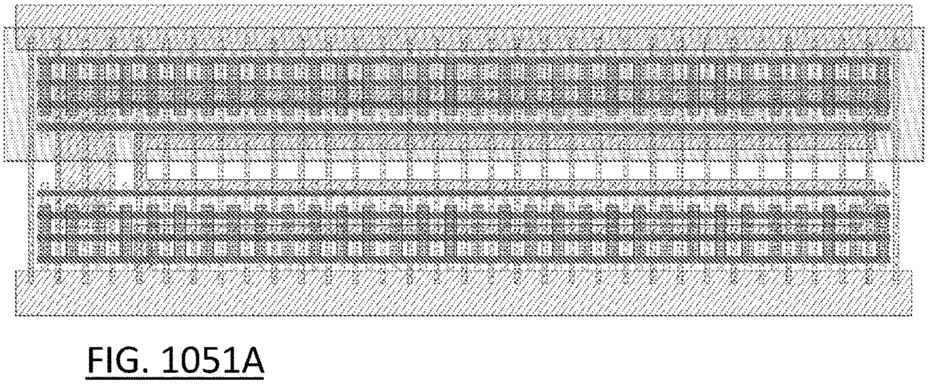
FIG. 1051A
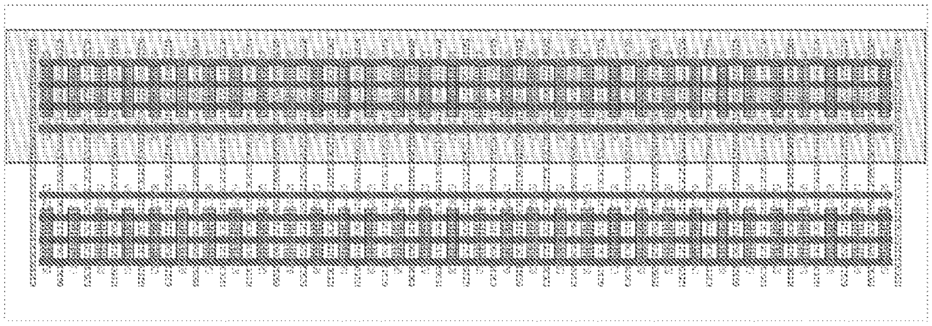
FIG. 1051B
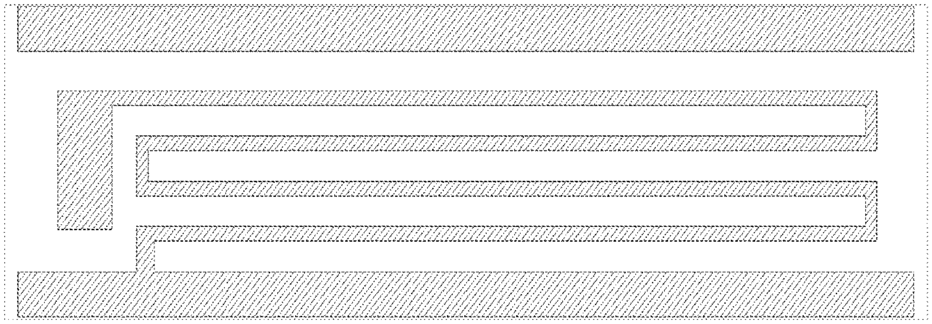
FIG. 1051C

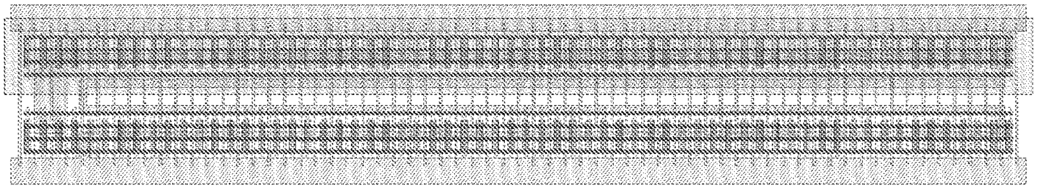
FIG. 1052A
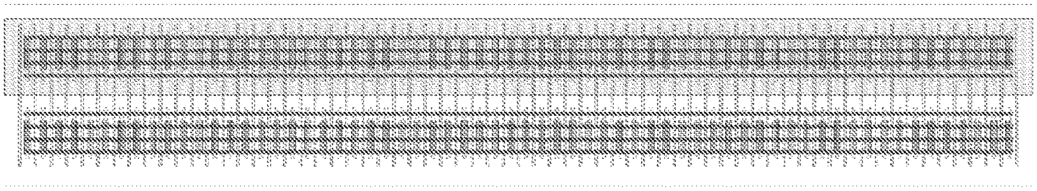
FIG. 1052B
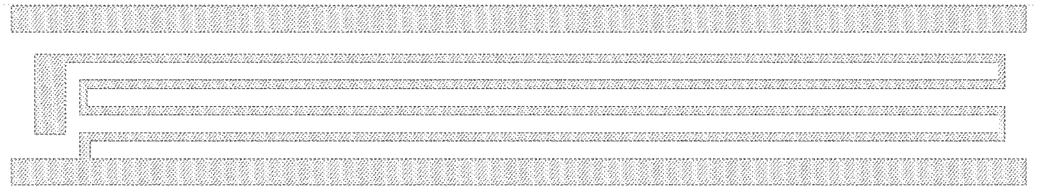
FIG. 1052C

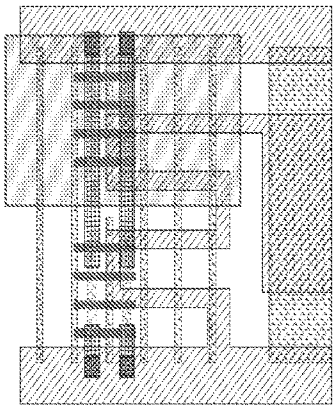
FIG. 1053A
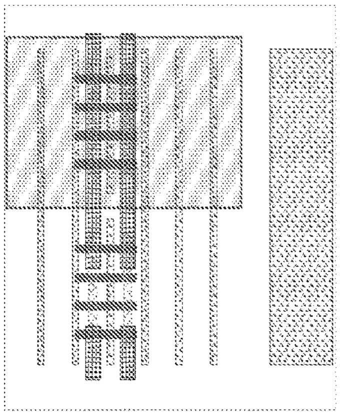
FIG. 1053B
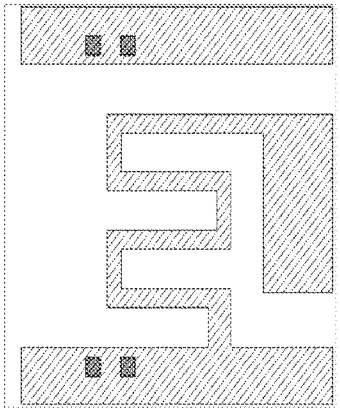
FIG. 1053C

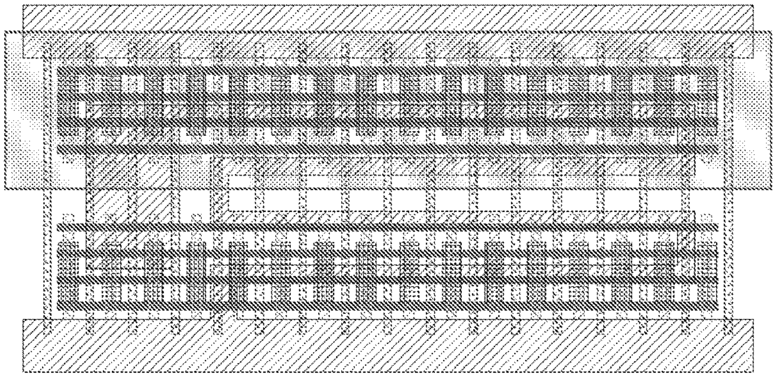
FIG. 1054A
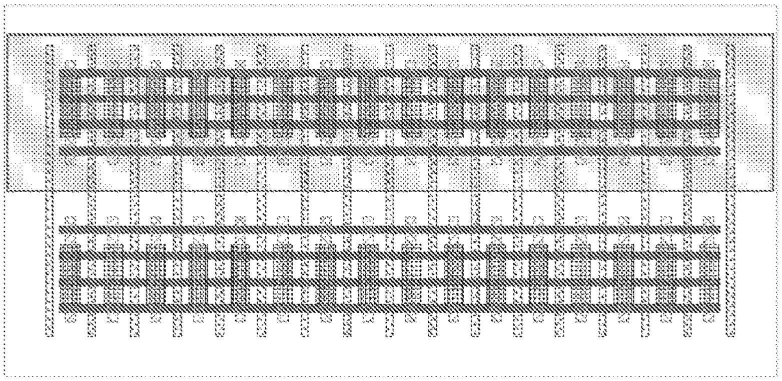
FIG. 1054B
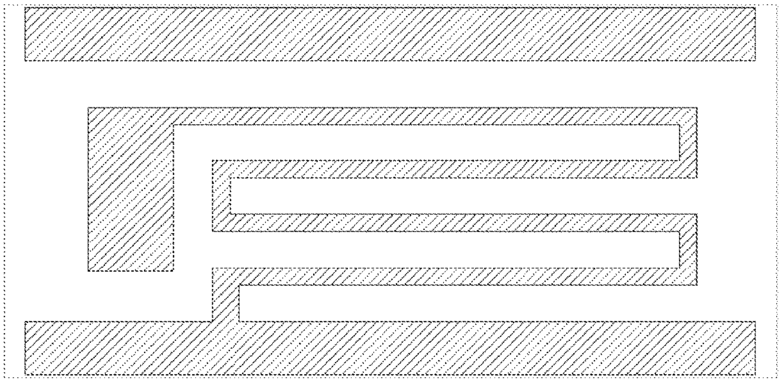
FIG. 1054C

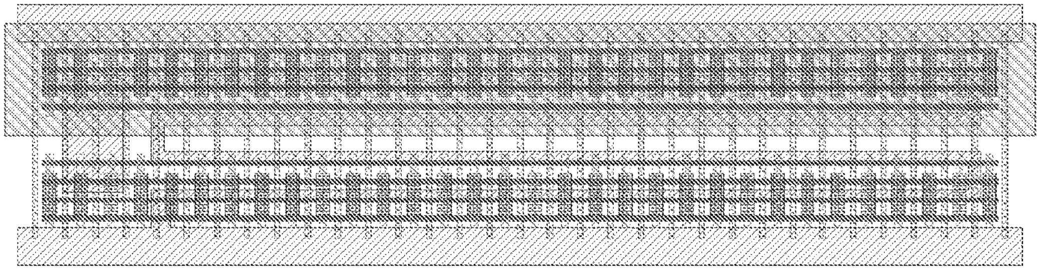
FIG. 1055A
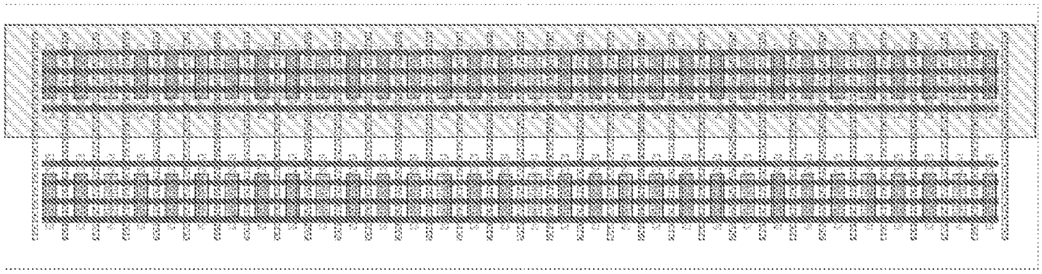
FIG. 1055B
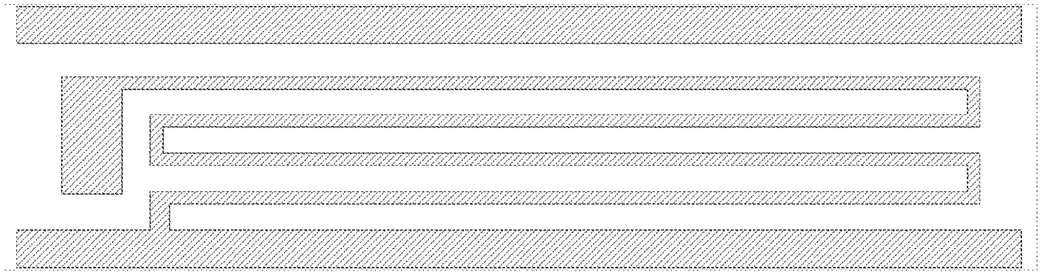
FIG. 1055C
*M* PDF Solutions, Inc.

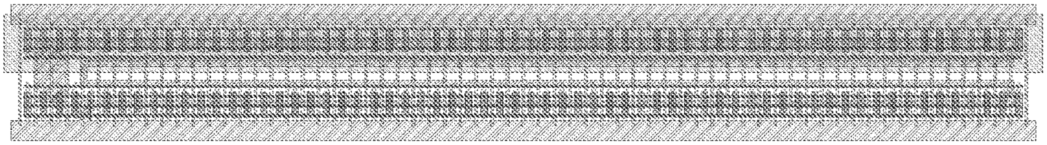
FIG. 1056A
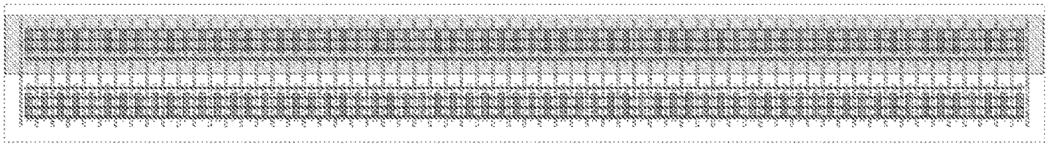
FIG. 1056B
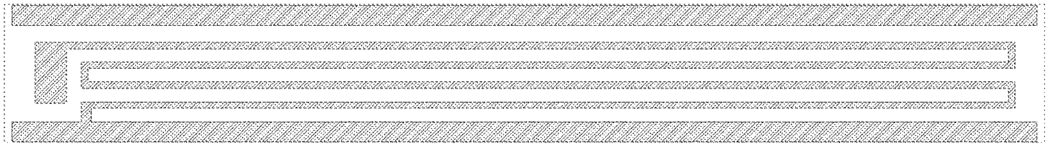
FIG. 1056C
*M* PDF Solutions, Inc.

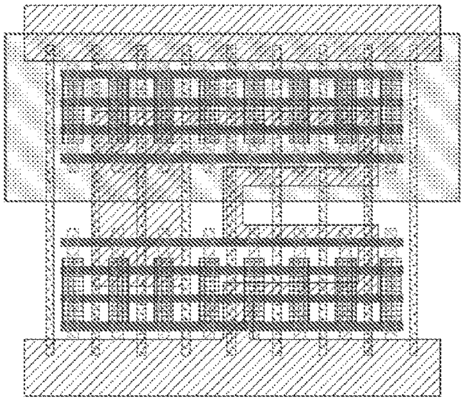
FIG. 1057A
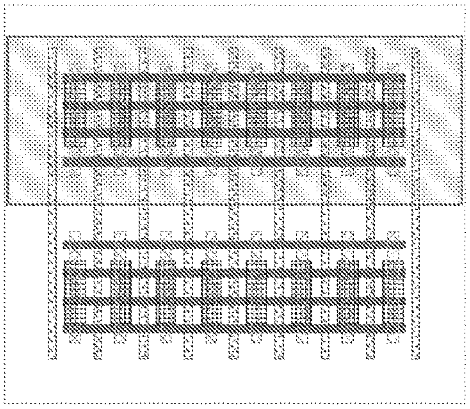
FIG. 1057B
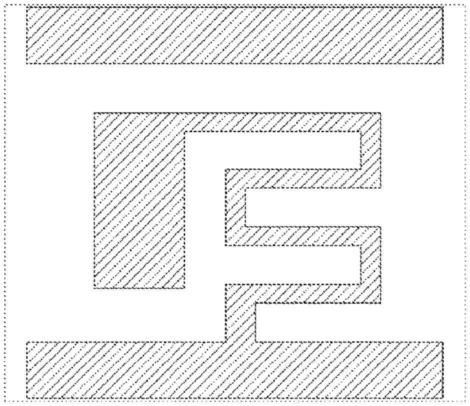
FIG. 1057C

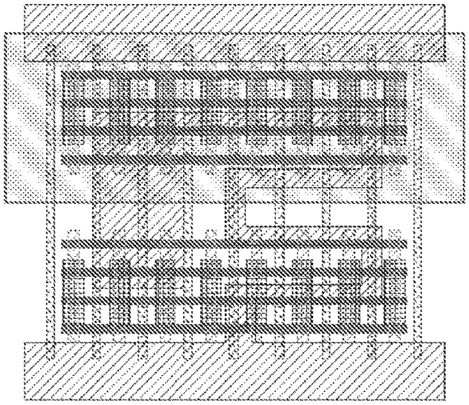
FIG. 1058A
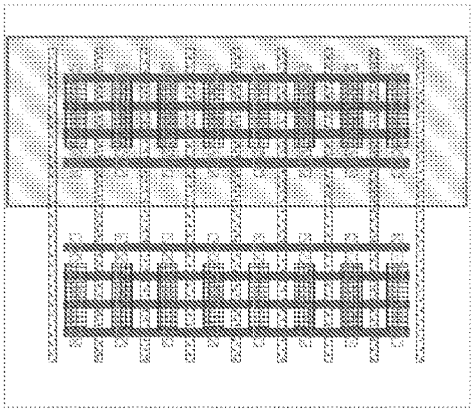
FIG. 1058B
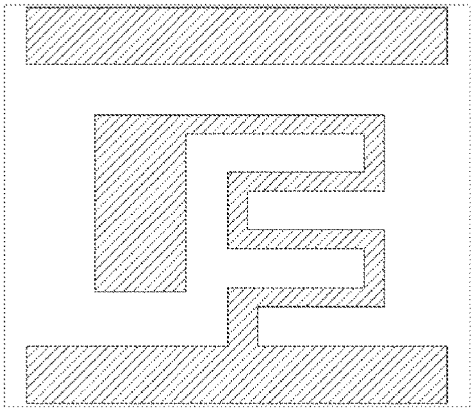
FIG. 1058C

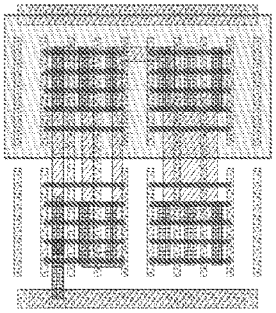
FIG. 1059A
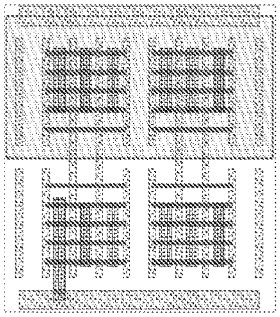
FIG. 1059B
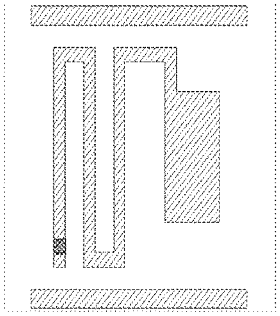
FIG. 1059C

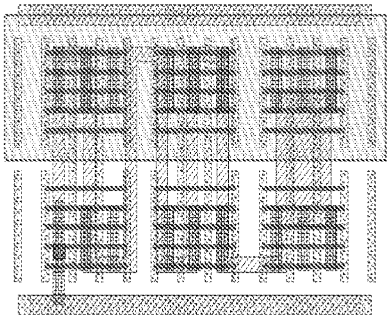
FIG. 1060A
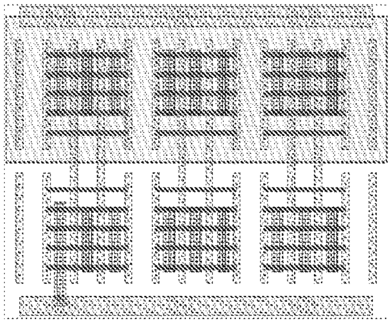
FIG. 1060B
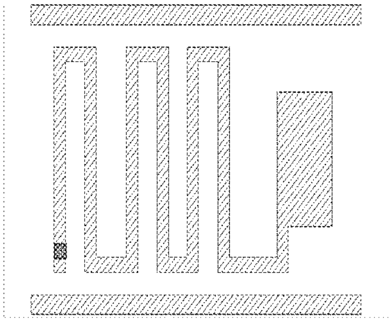
FIG. 1060C

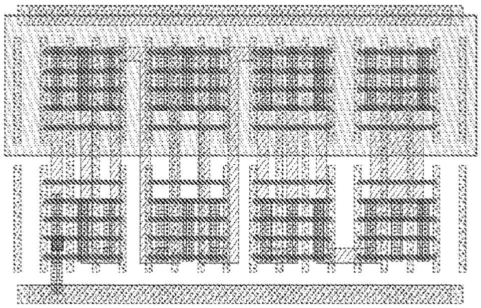
FIG. 1061A
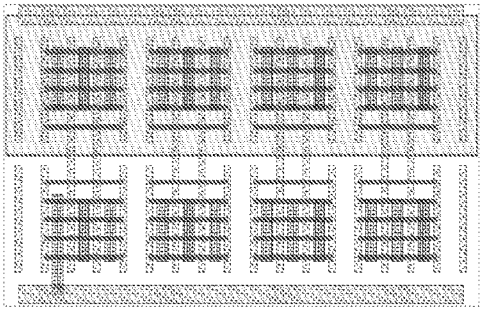
FIG. 1061B
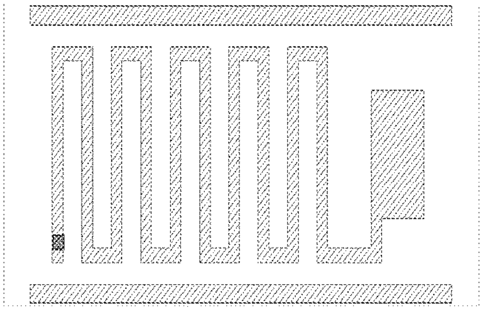
FIG. 1061C

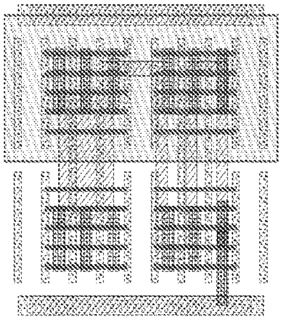
FIG. 1062A
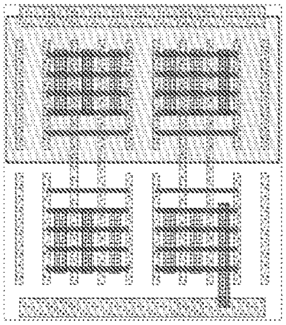
FIG. 1062B
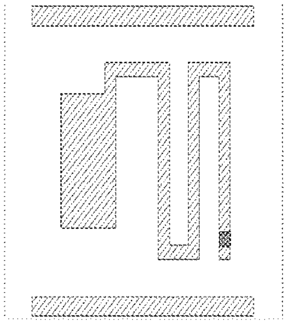
FIG. 1062C

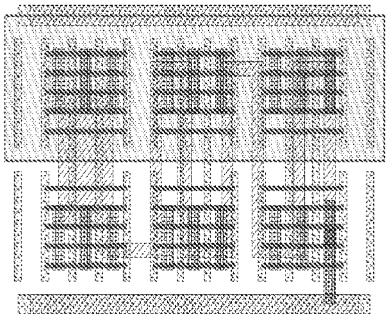
FIG. 1063A
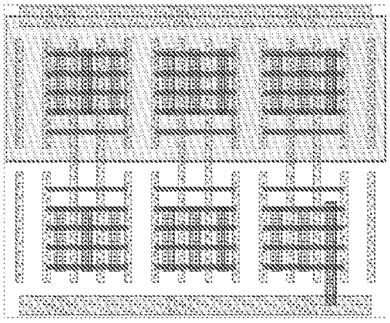
FIG. 1063B
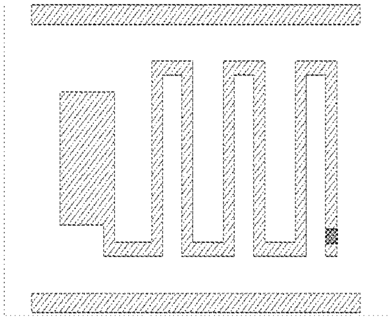
FIG. 1063C

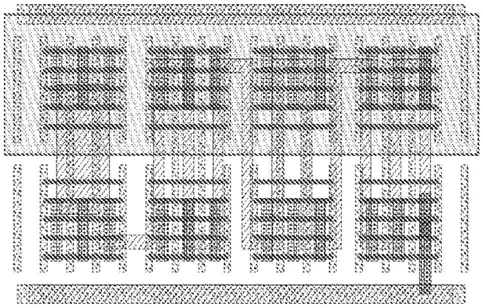
FIG. 1064A
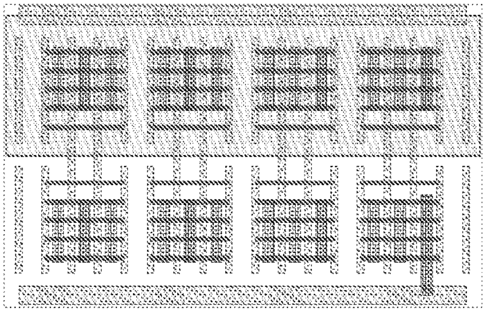
FIG. 1064B
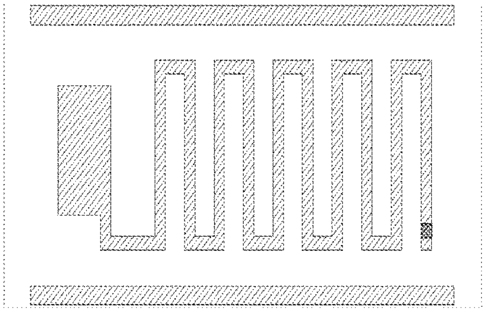
FIG. 1064C

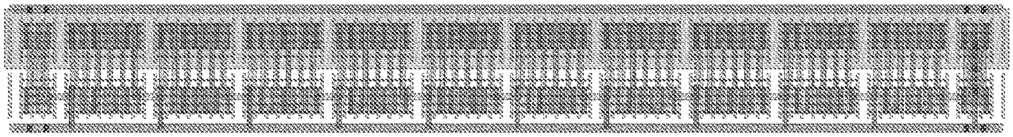
FIG. 1065A
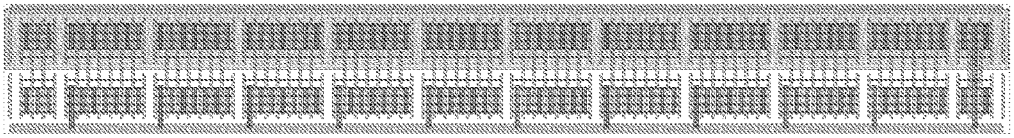
FIG. 1065B
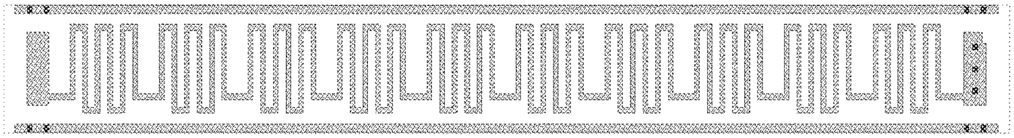
FIG. 1065C

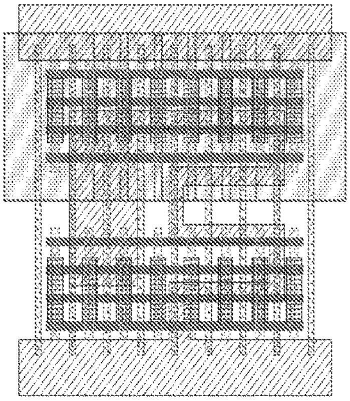
FIG. 1066A
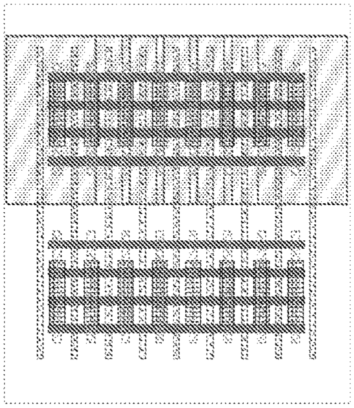
FIG. 1066B
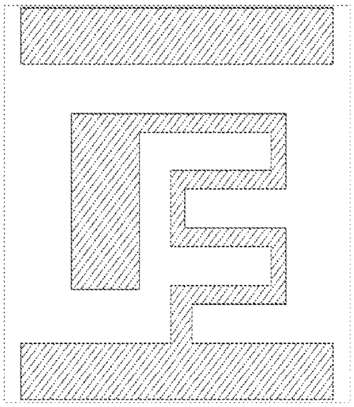
FIG. 1066C

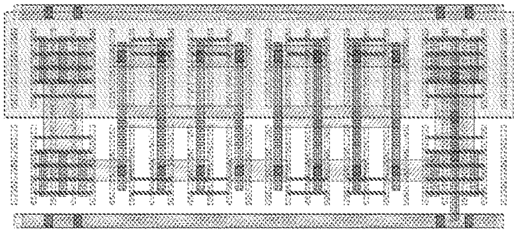
FIG. 1067A
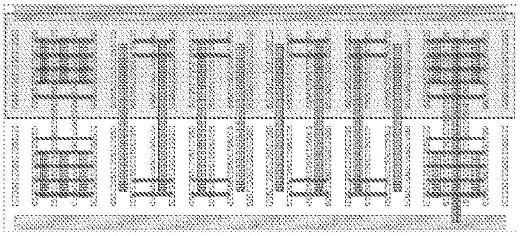
FIG. 1067B
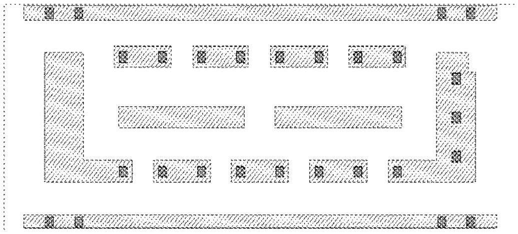
FIG. 1067C
*M* PDF Solutions, Inc.

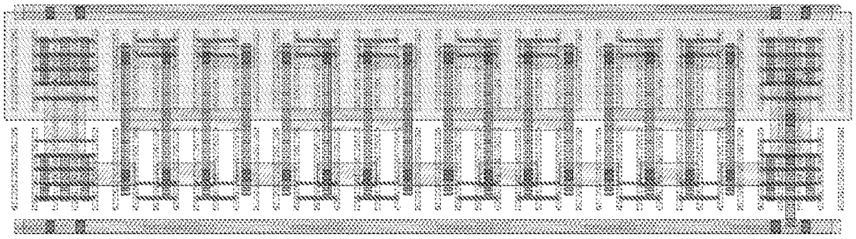
FIG. 1068A
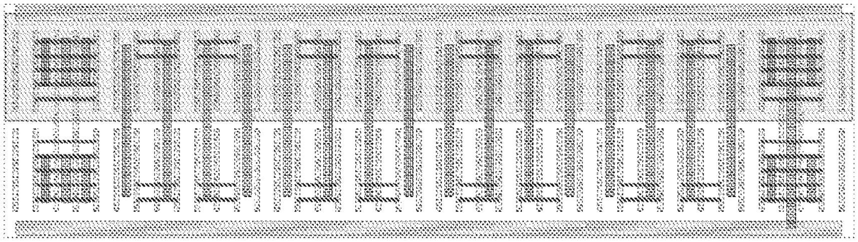
FIG. 1068B
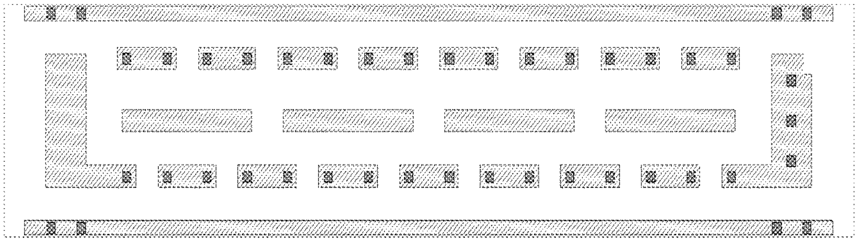
FIG. 1068C
*M* PDF Solutions, Inc.

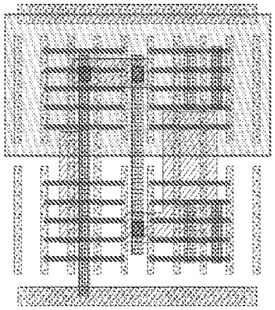
FIG. 1069A
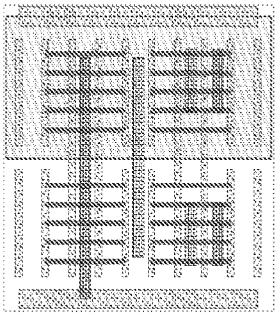
FIG. 1069B
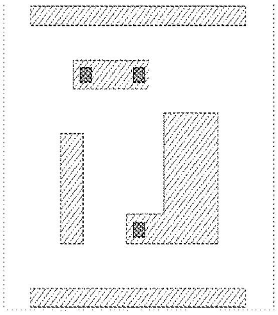
FIG. 1069C
*M* PDF Solutions, Inc.

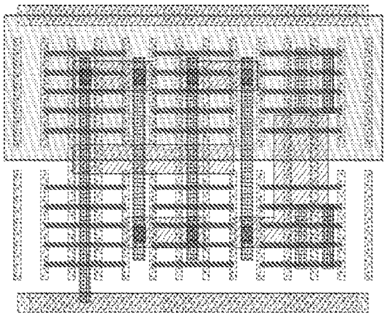
FIG. 1070A
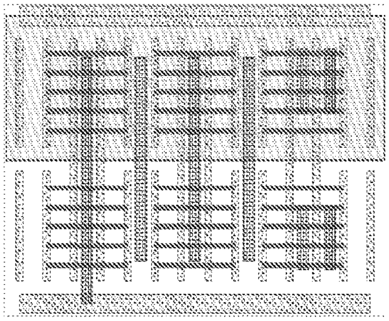
FIG. 1070B
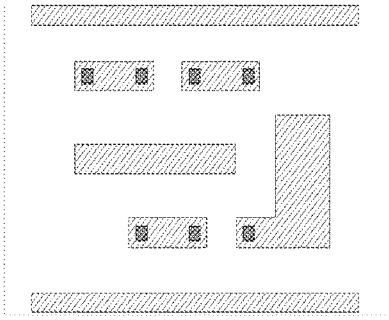
FIG. 1070C
*M* PDF Solutions, Inc.

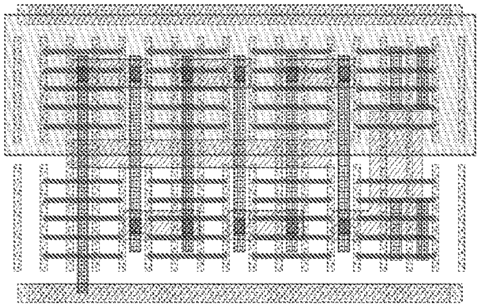
FIG. 1071A
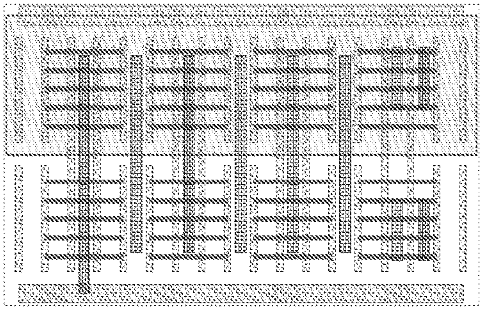
FIG. 1071B
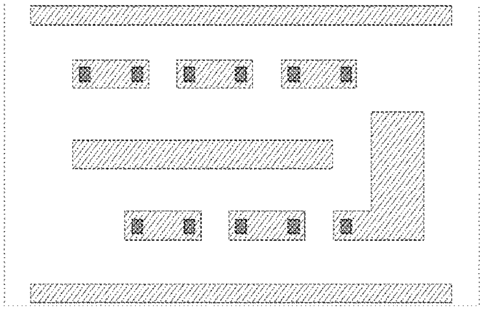
FIG. 1071C

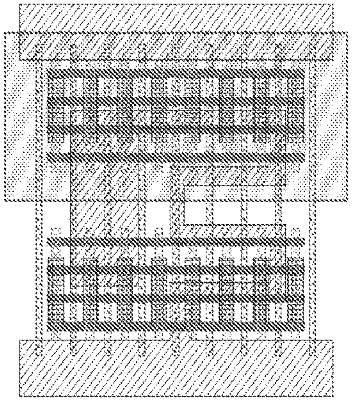
FIG. 1072A
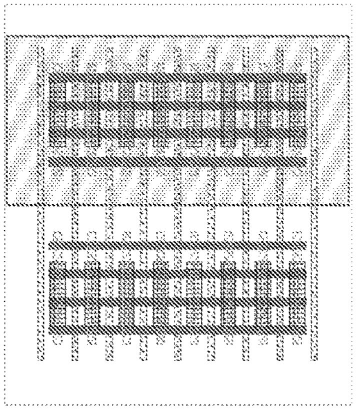
FIG. 1072B
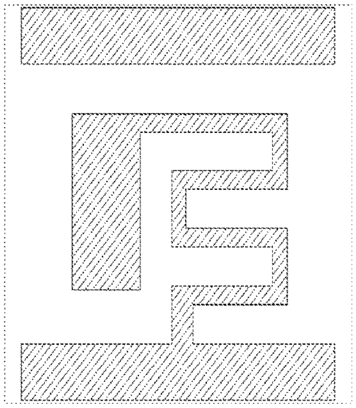
FIG. 1072C

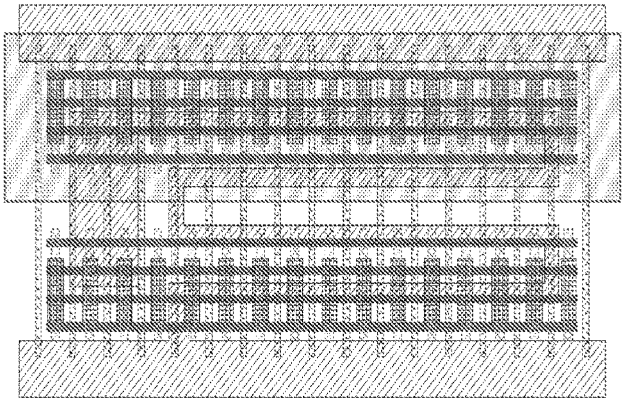
FIG. 1073A
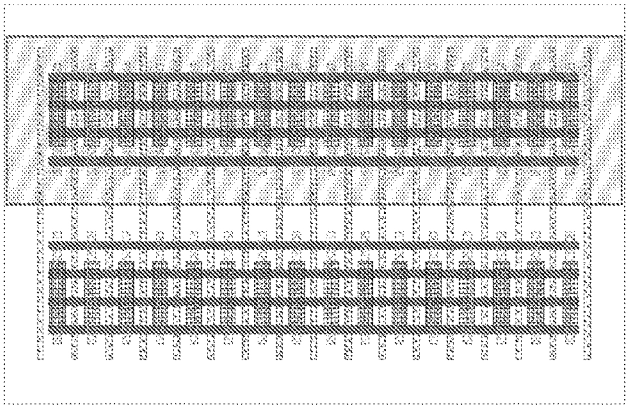
FIG. 1073B
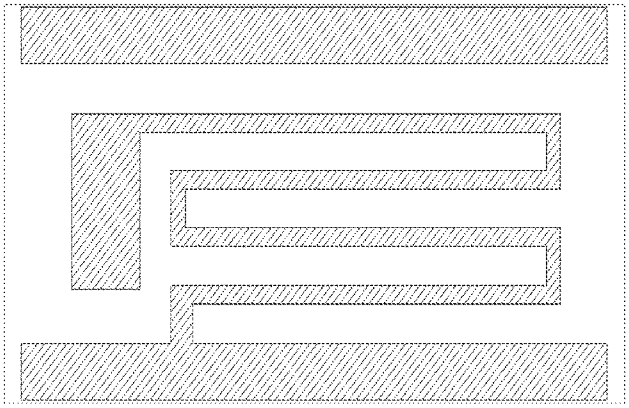
FIG. 1073C
*M* PDF Solutions, Inc.

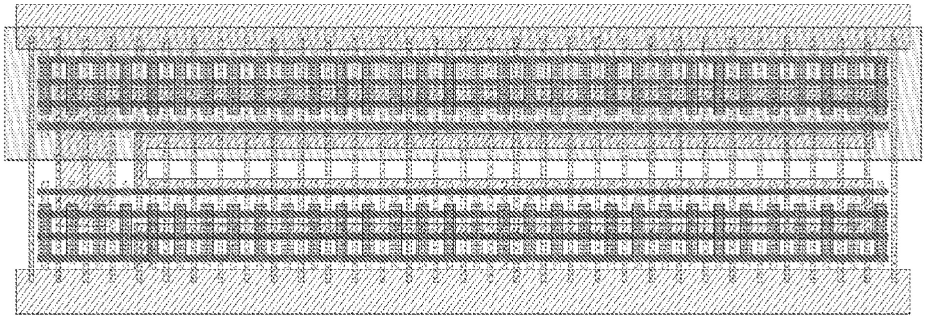
FIG. 1074A
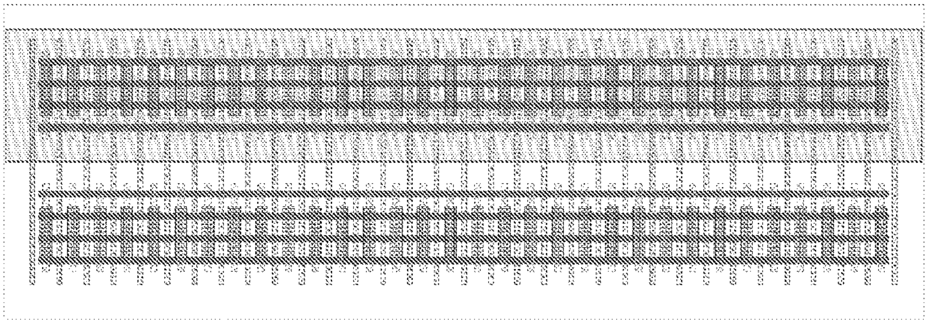
FIG. 1074B
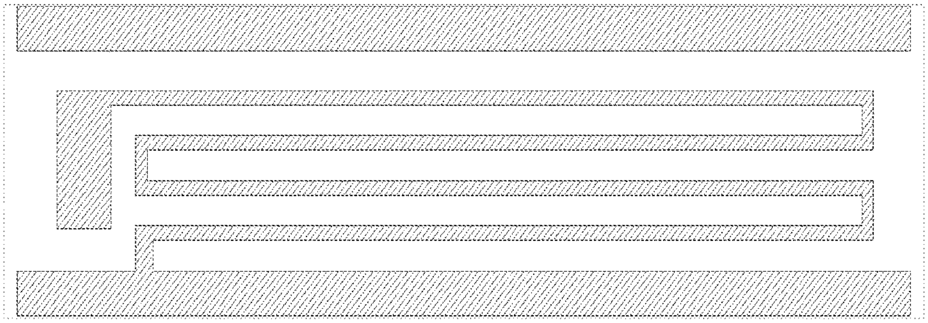
FIG. 1074C

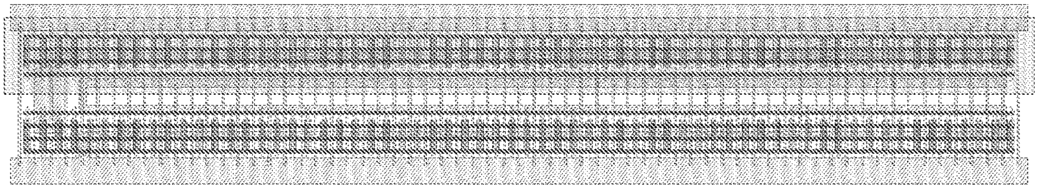
FIG. 1075A
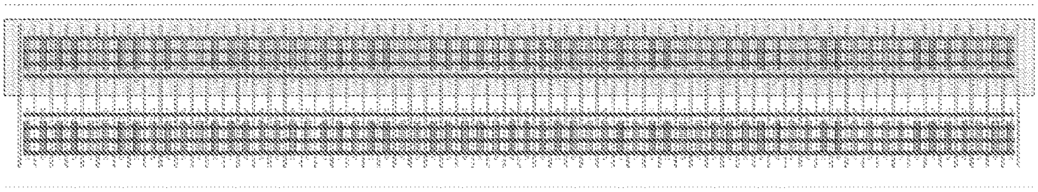
FIG. 1075B
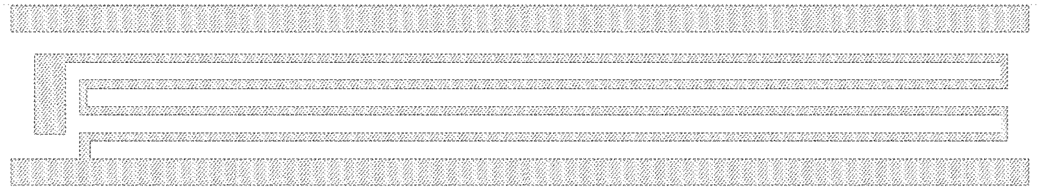
FIG. 1075C

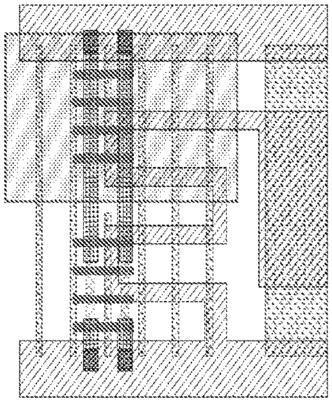
FIG. 1076A
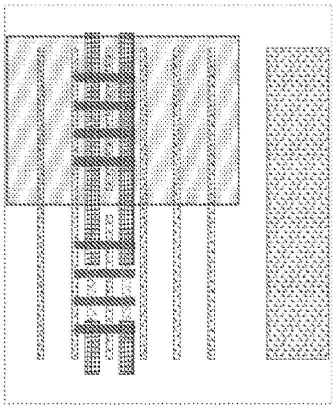
FIG. 1076B
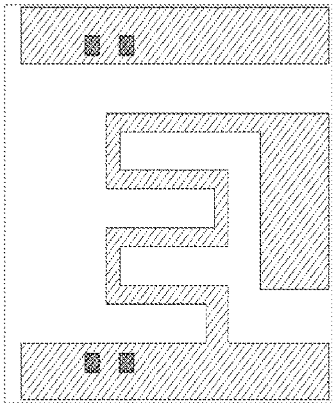
FIG. 1076C
*M* PDF Solutions, Inc.

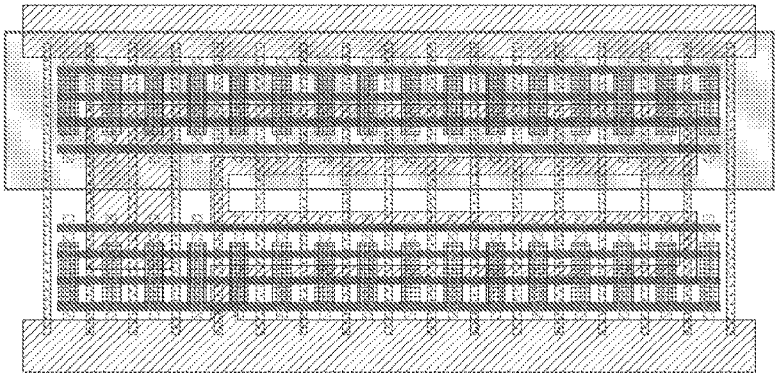
FIG. 1077A
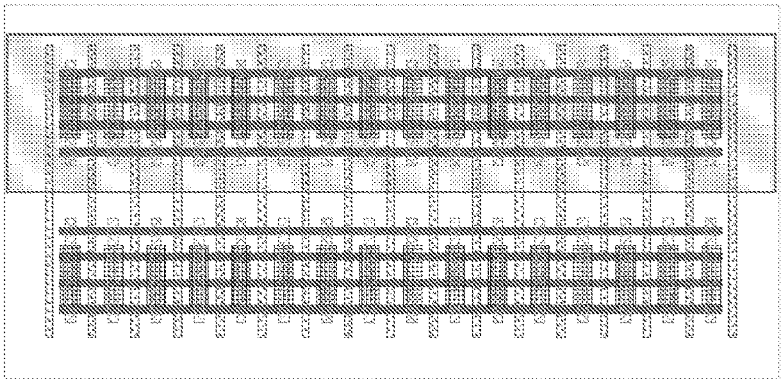
FIG. 1077B
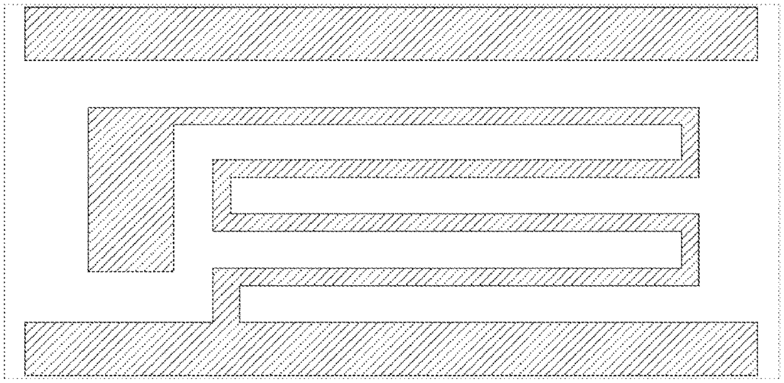
FIG. 1077C
*M* PDF Solutions, Inc.

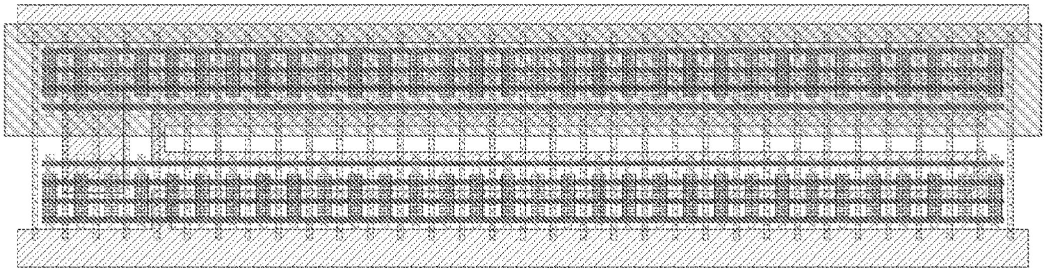
FIG. 1078A
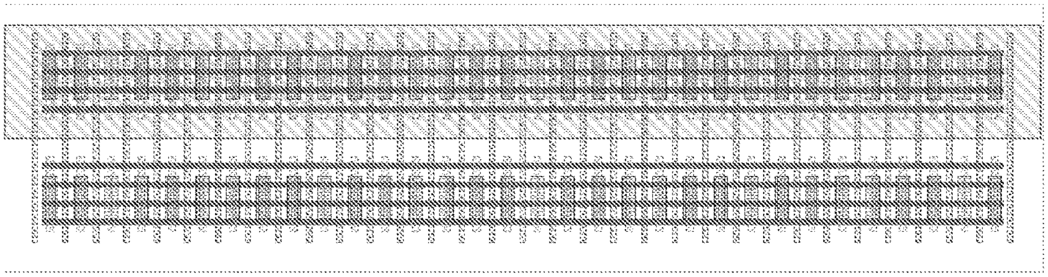
FIG. 1078B
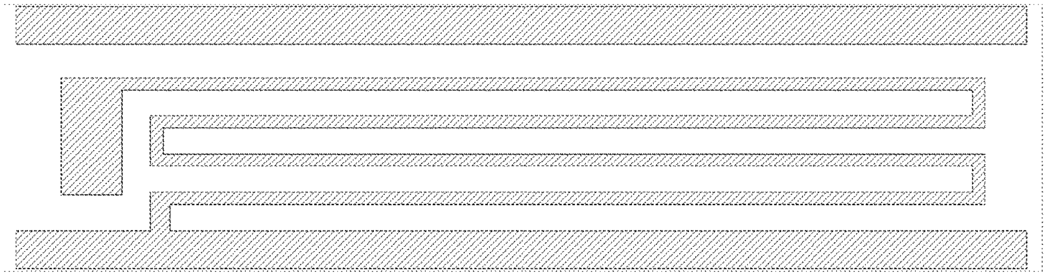
FIG. 1078C

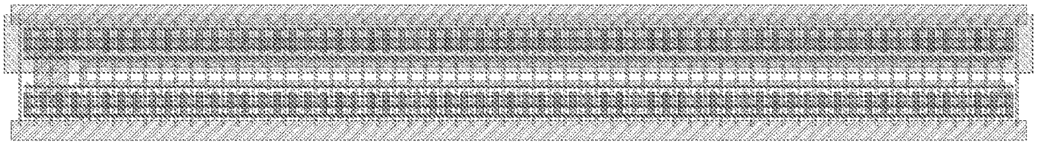
FIG. 1079A
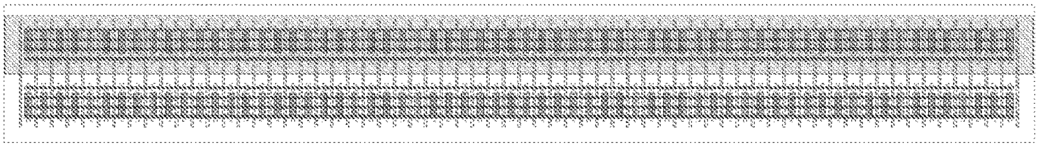
FIG. 1079B
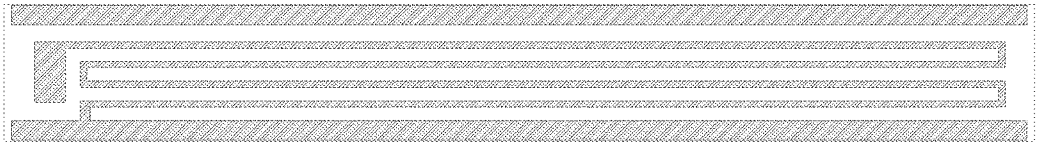
FIG. 1079C

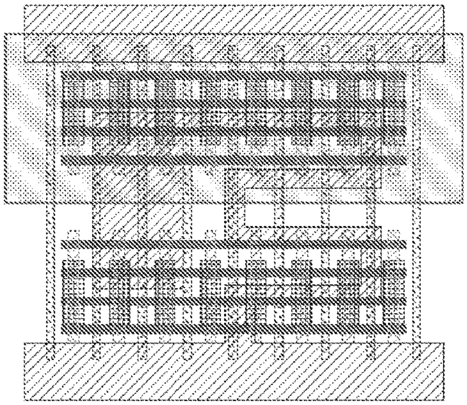
FIG. 1080A
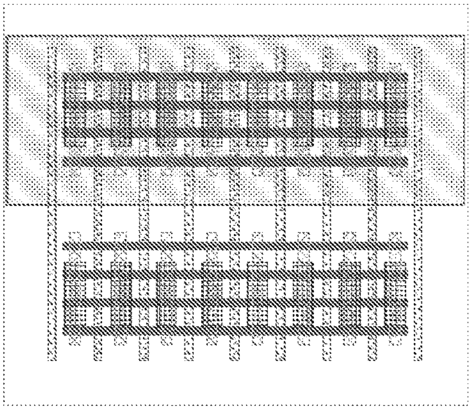
FIG. 1080B
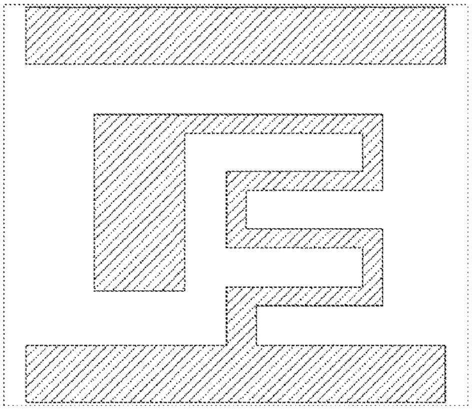
FIG. 1080C
*M* PDF Solutions, Inc.

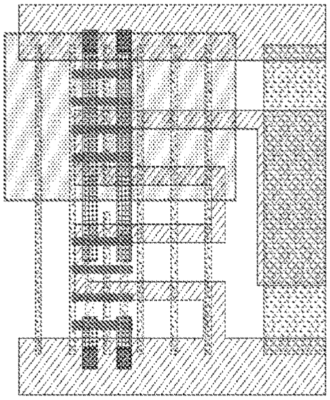
FIG. 1081A
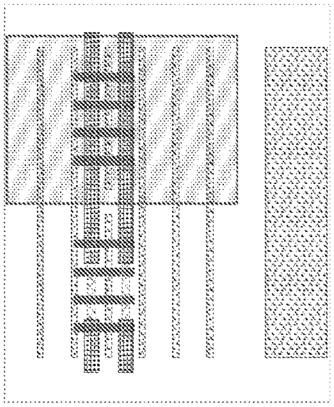
FIG. 1081B
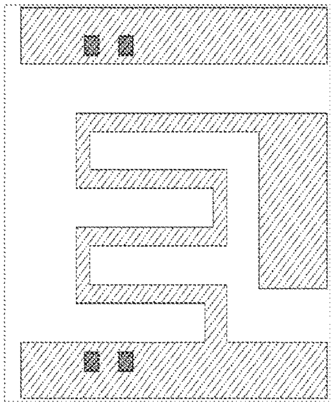
FIG. 1081C

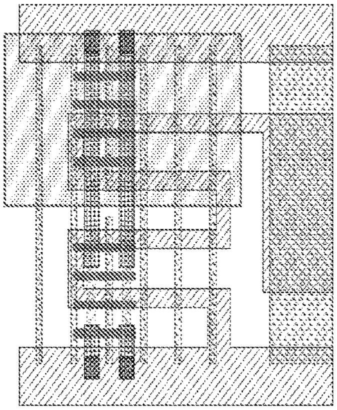
FIG. 1082A
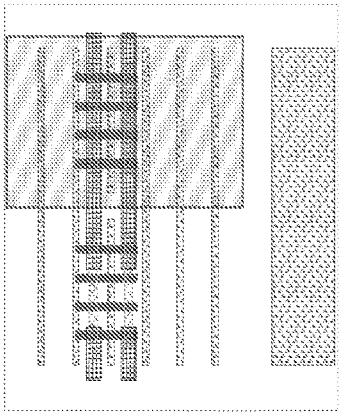
FIG. 1082B
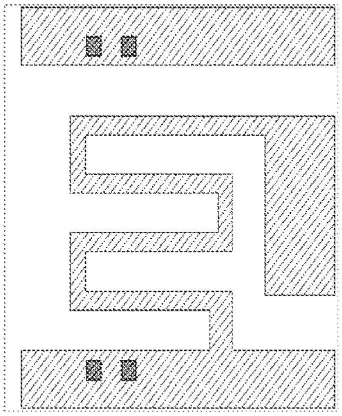
FIG. 1082C

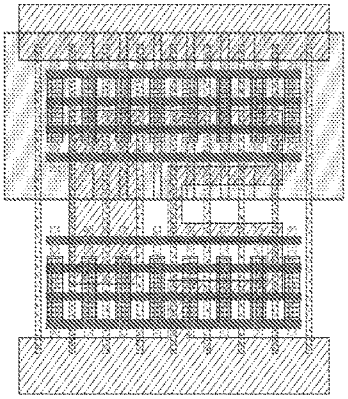
FIG. 1083A
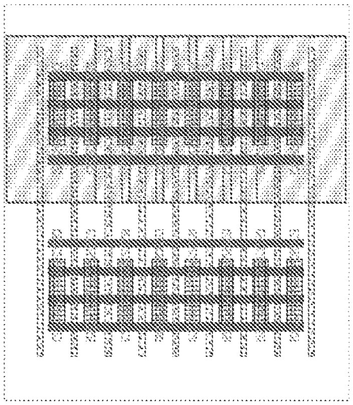
FIG. 1083B
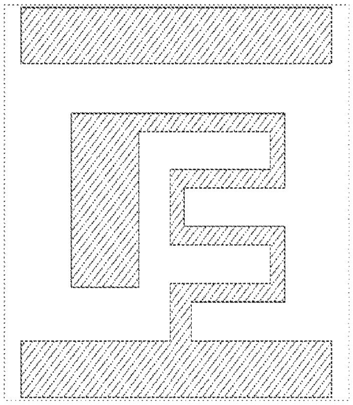
FIG. 1083C
*M* PDF Solutions, Inc.

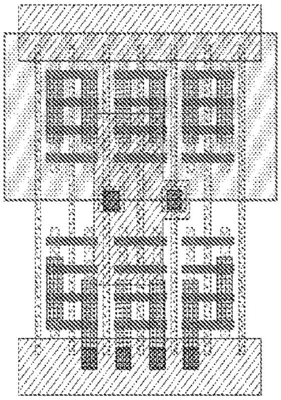
FIG. 1084A
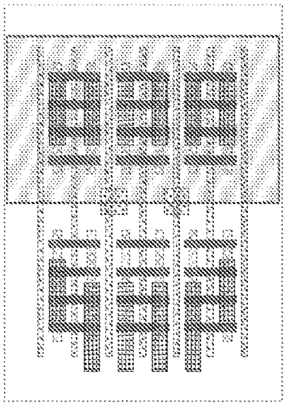
FIG. 1084B
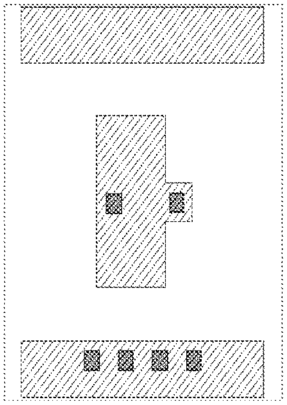
FIG. 1084C
*M* PDF Solutions, Inc.

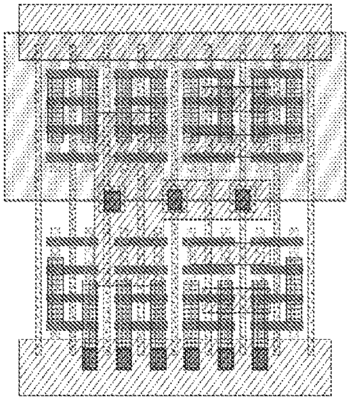
FIG. 1085A
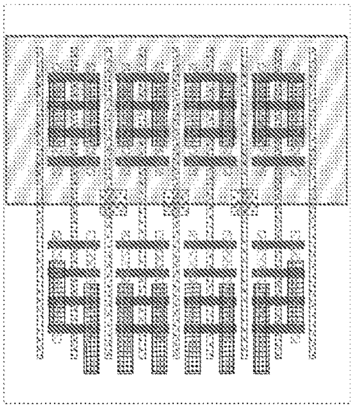
FIG. 1085B
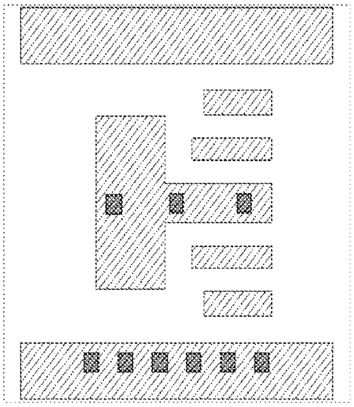
FIG. 1085C
*M* PDF Solutions, Inc.

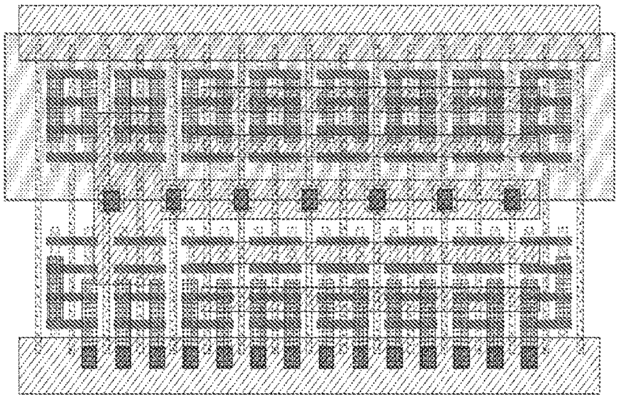
FIG. 1086A
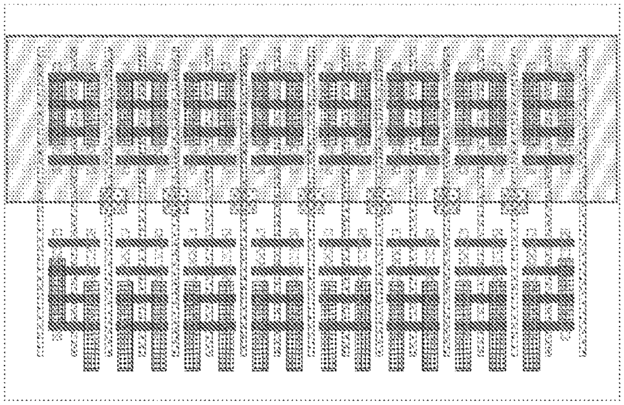
FIG. 1086B
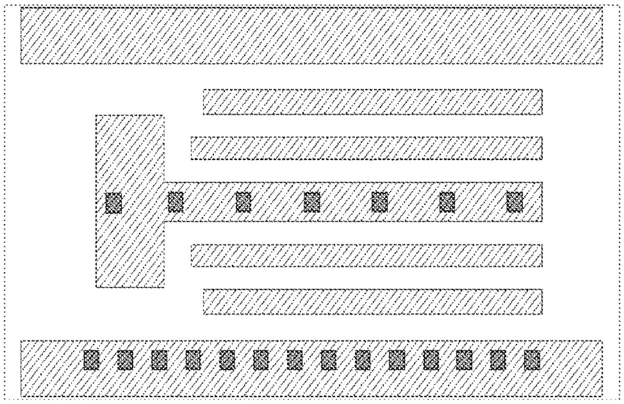
FIG. 1086C

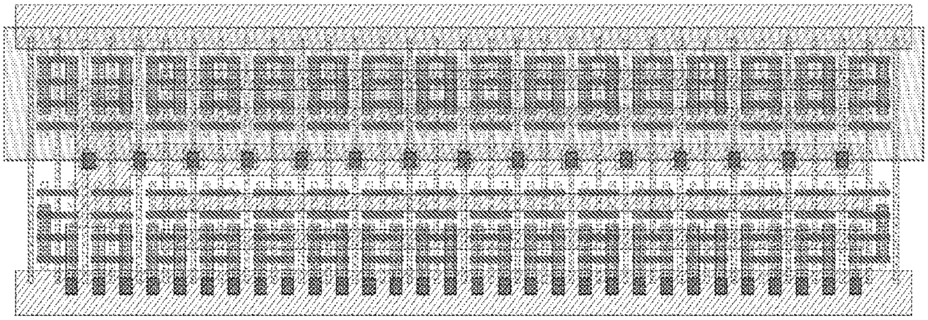
FIG. 1087A
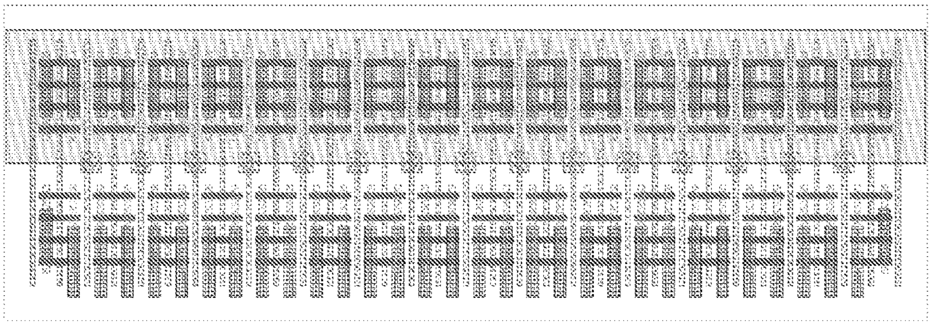
FIG. 1087B
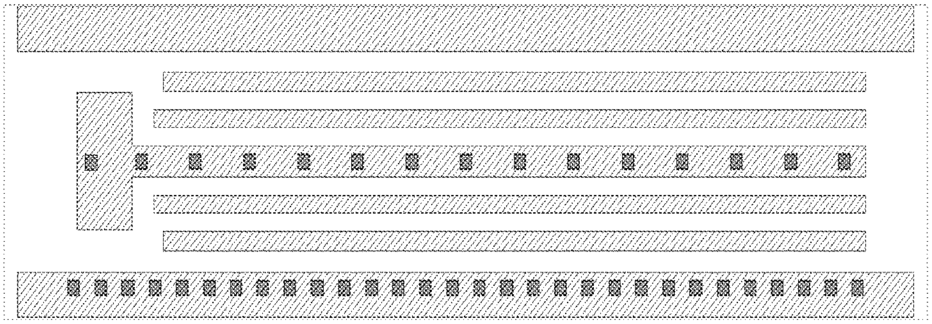
FIG. 1087C

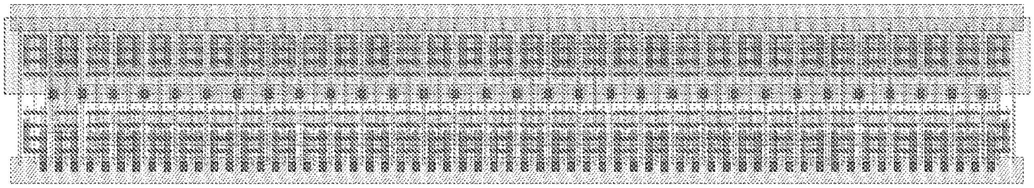
FIG. 1088A
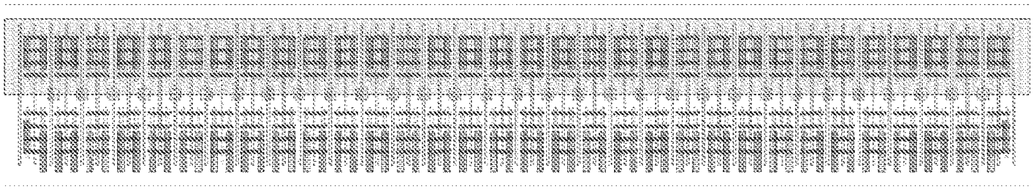
FIG. 1088B
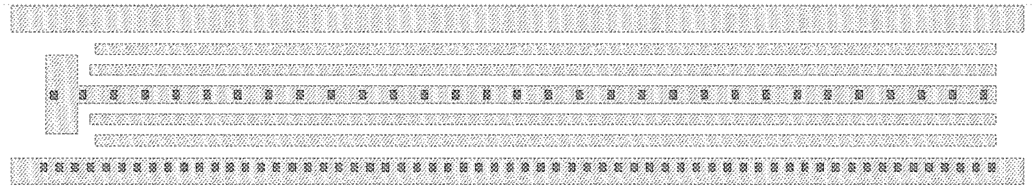
FIG. 1088C

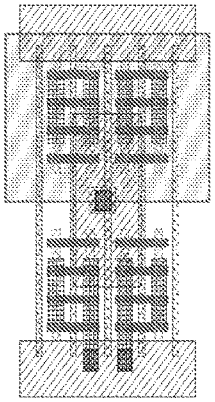
FIG. 1089A
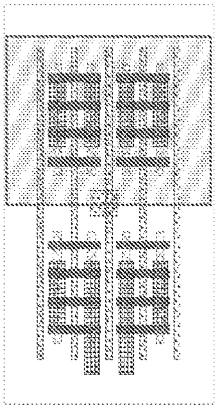
FIG. 1089B
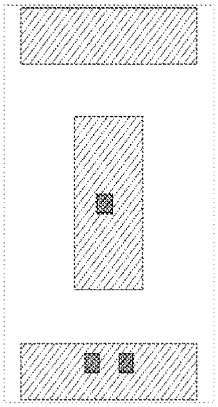
FIG. 1089C
*M* PDF Solutions, Inc.

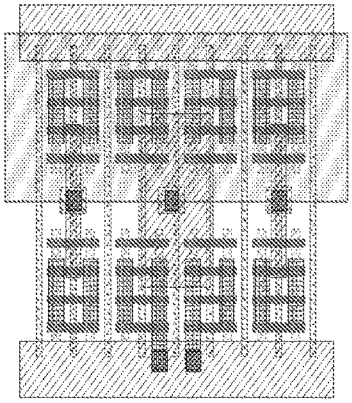
FIG. 1090A
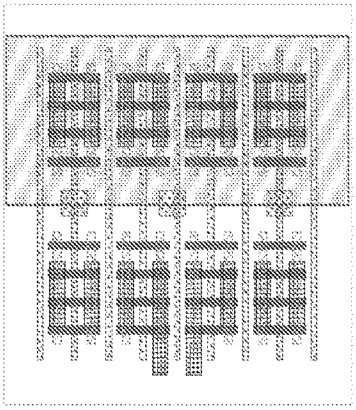
FIG. 1090B
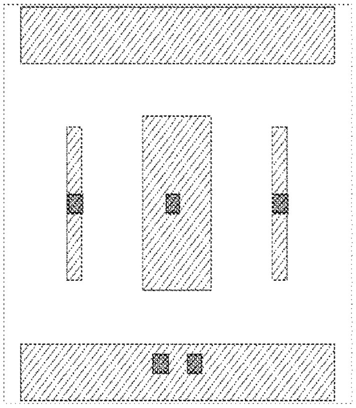
FIG. 1090C
*M* PDF Solutions, Inc.

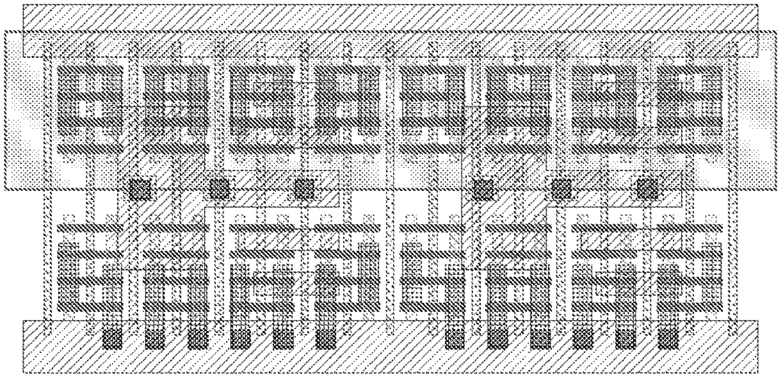
FIG. 1091A
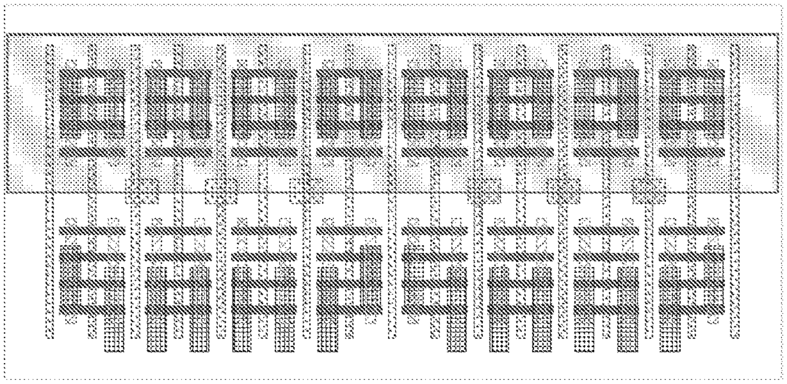
FIG. 1091B
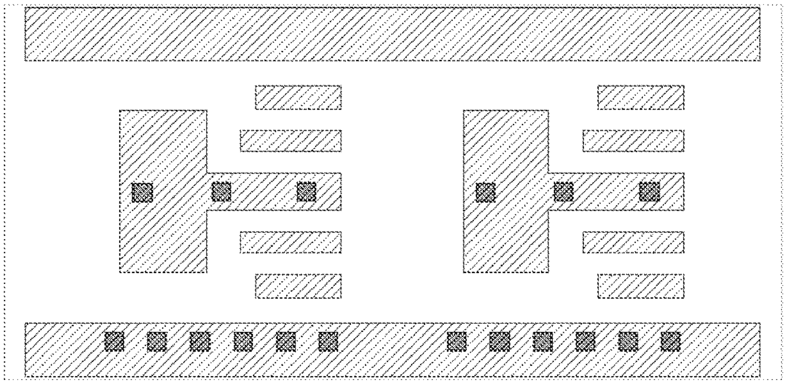
FIG. 1091C
*M* PDF Solutions, Inc.

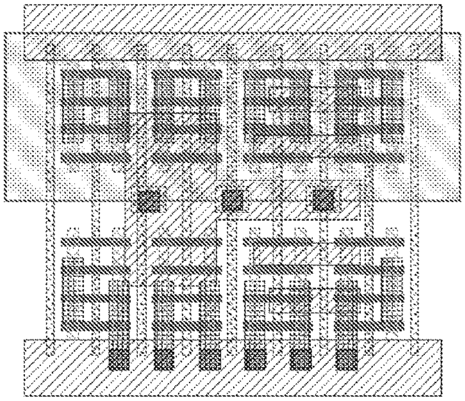
FIG. 1092A
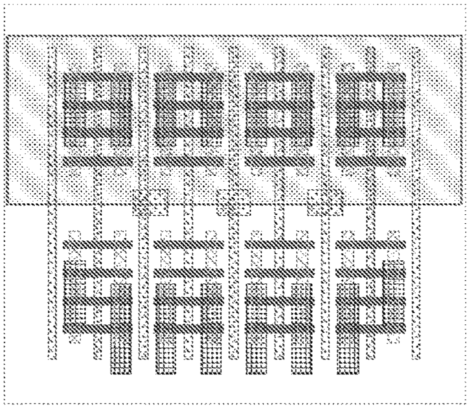
FIG. 1092B
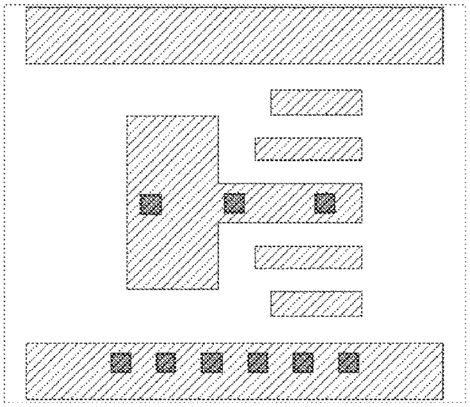
FIG. 1092C

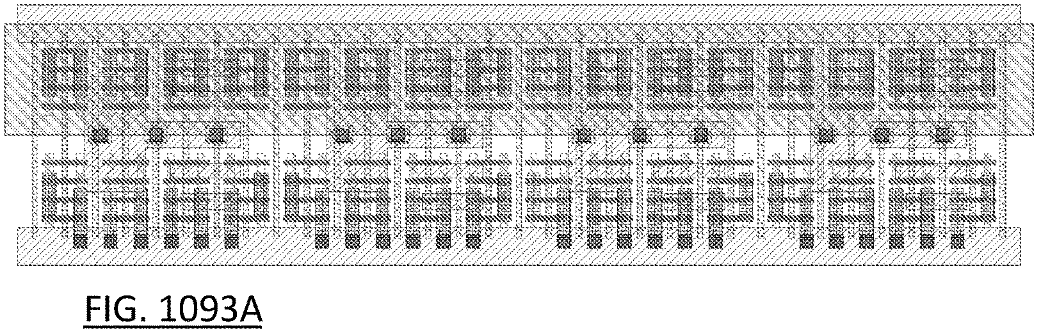
FIG. 1093A
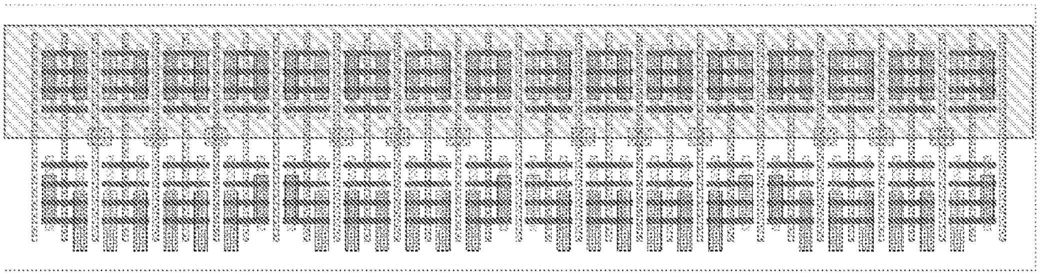
FIG. 1093B
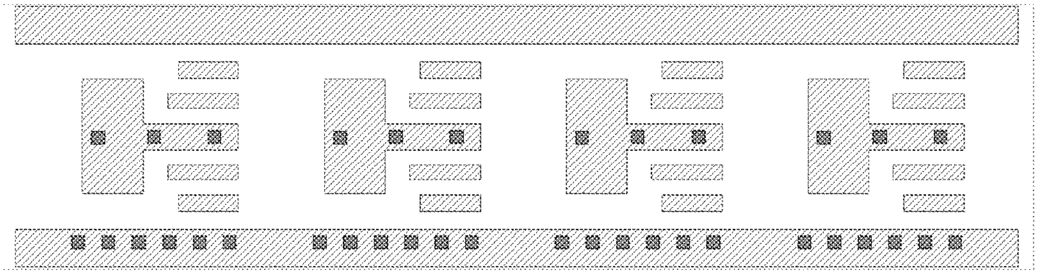
FIG. 1093C

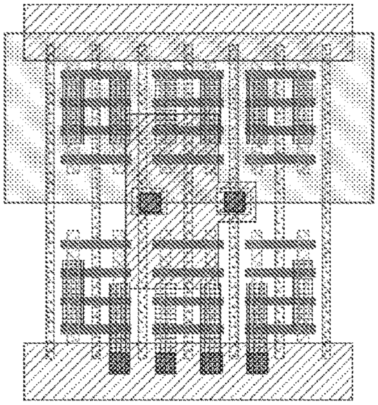
FIG. 1094A
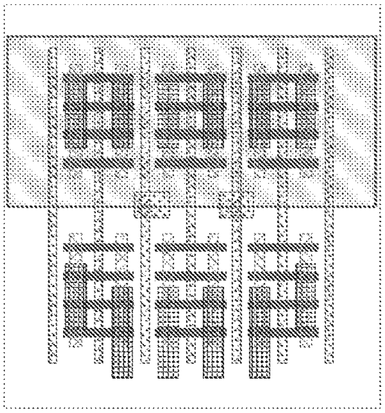
FIG. 1094B
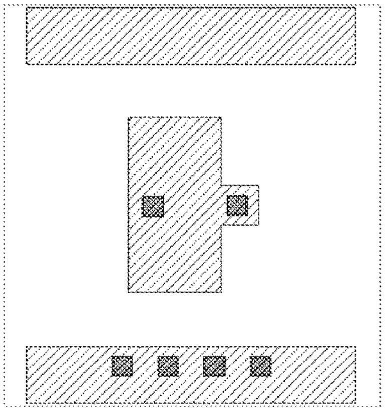
FIG. 1094C

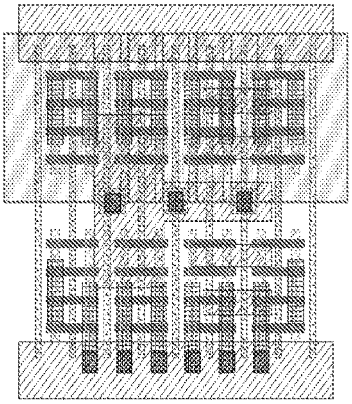
FIG. 1095A
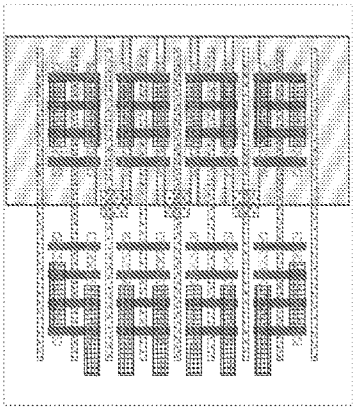
FIG. 1095B
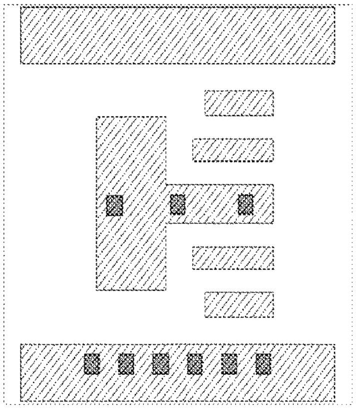
FIG. 1095C
*M* PDF Solutions, Inc.

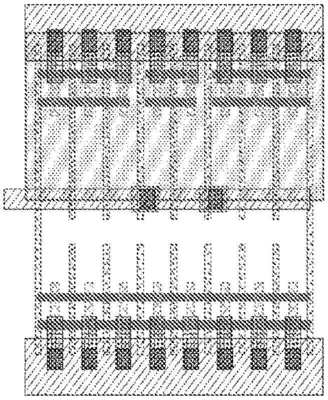
FIG. 1096A
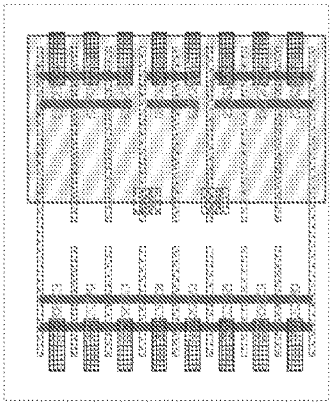
FIG. 1096B
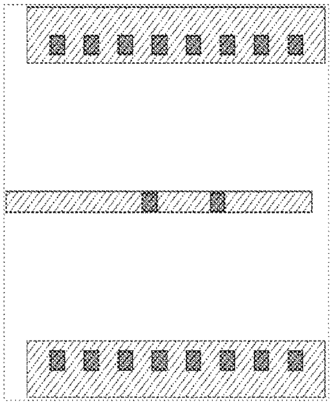
FIG. 1096C

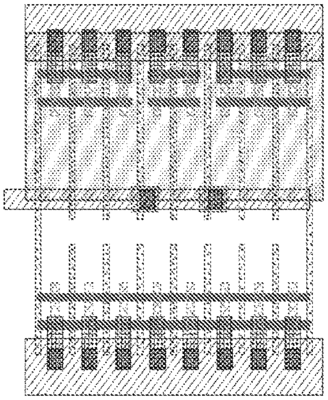
FIG. 1097A
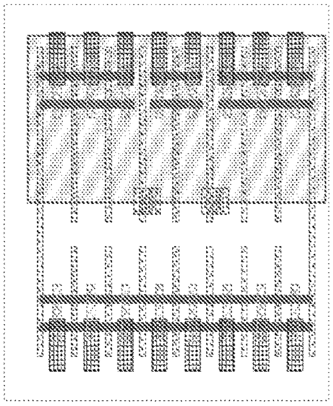
FIG. 1097B
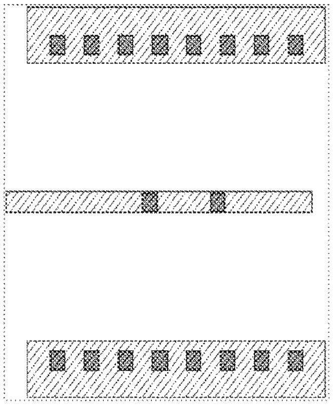
FIG. 1097C
*M* PDF Solutions, Inc.

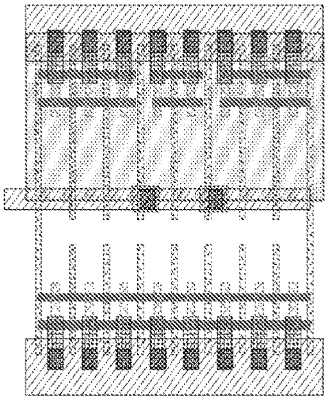
FIG. 1098A
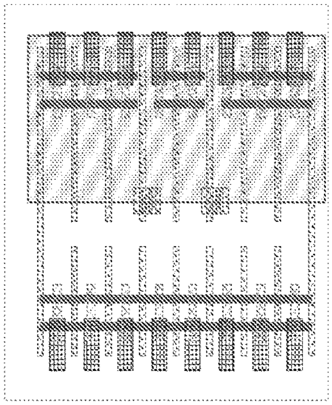
FIG. 1098B
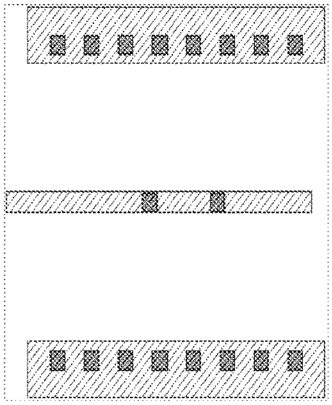
FIG. 1098C
*M* PDF Solutions, Inc.

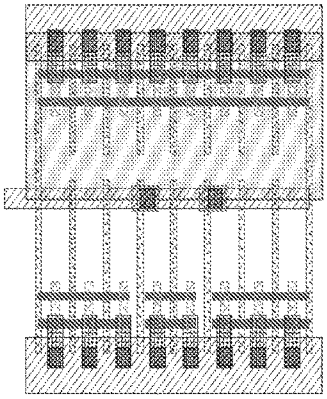
FIG. 1099A
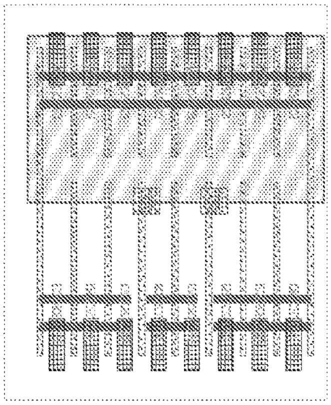
FIG. 1099B
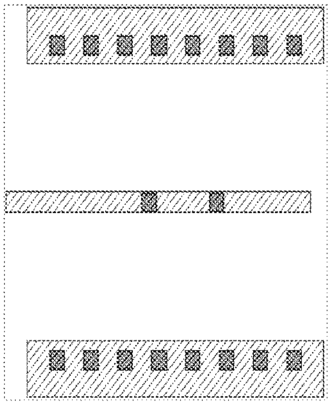
FIG. 1099C
*M* PDF Solutions, Inc.

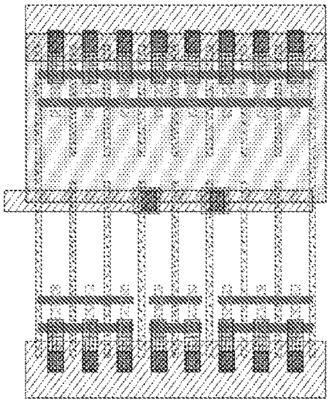
FIG. 1100A
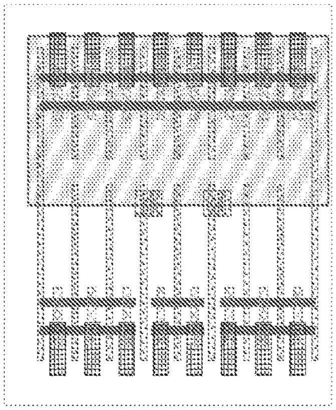
FIG. 1100B
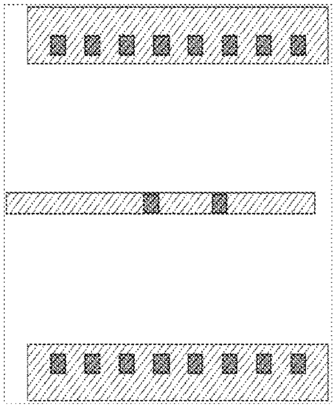
FIG. 1100C
*M* PDF Solutions, Inc.

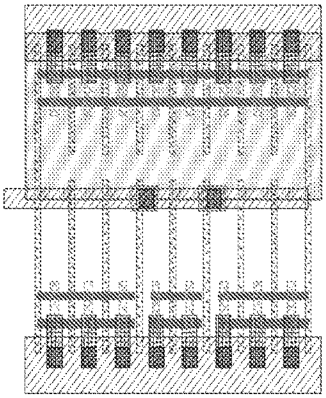
FIG. 1101A
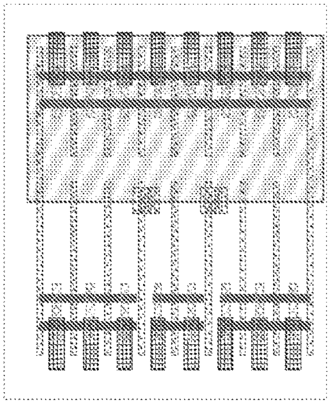
FIG. 1101B
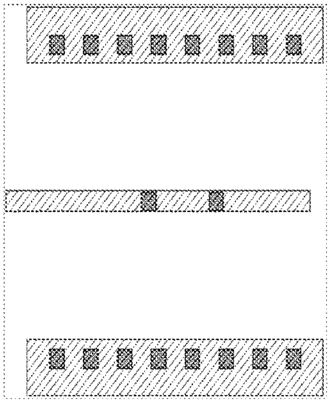
FIG. 1101C
*M* PDF Solutions, Inc.

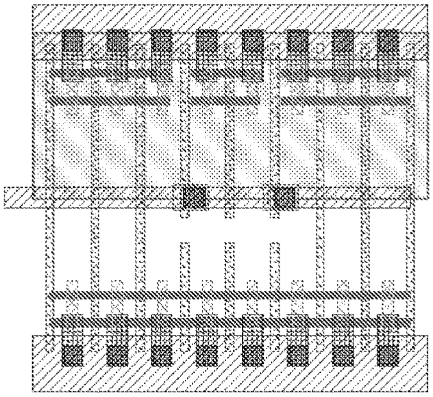
FIG. 1102A
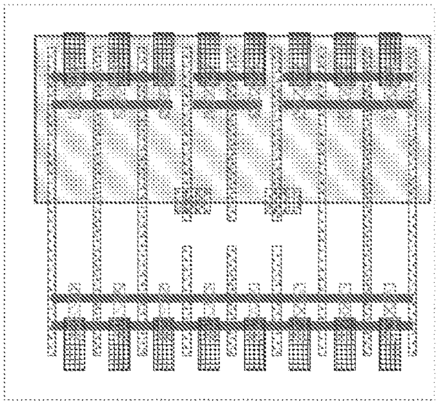
FIG. 1102B
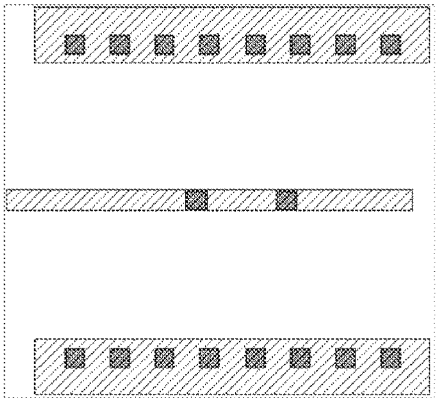
FIG. 1102C

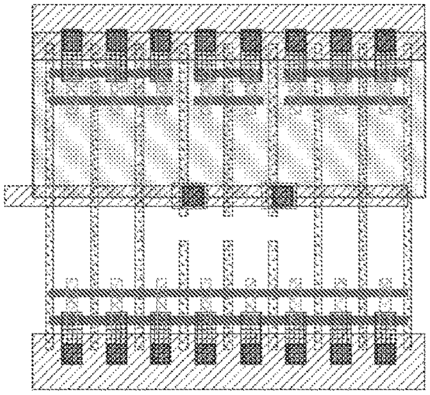
FIG. 1103A
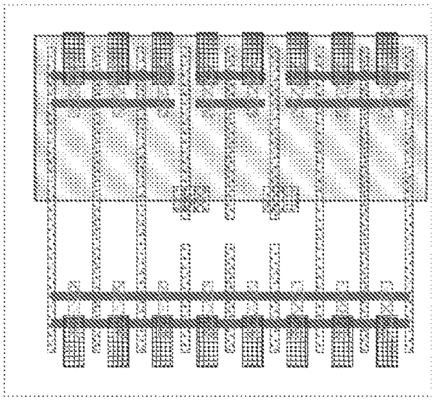
FIG. 1103B
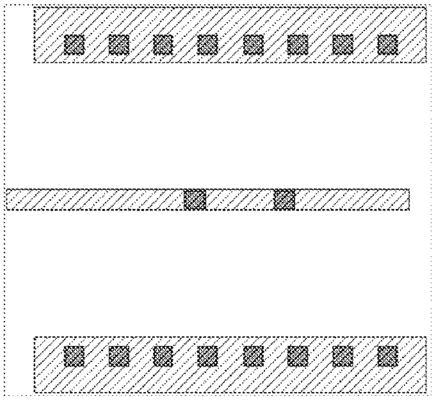
FIG. 1103C

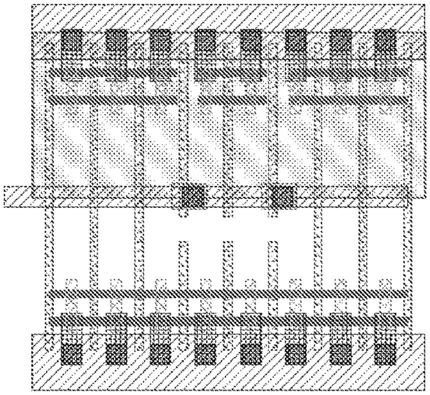
FIG. 1104A
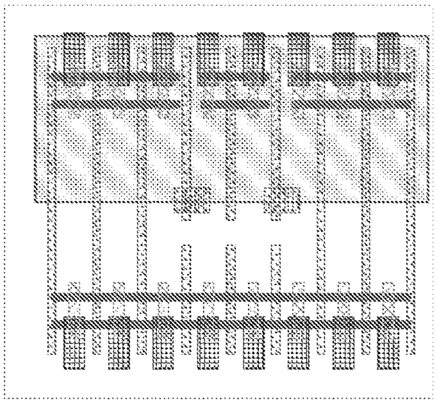
FIG. 1104B
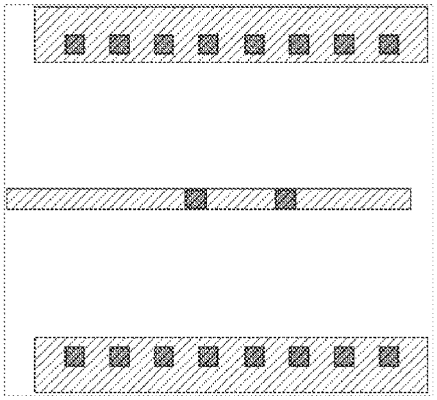
FIG. 1104C

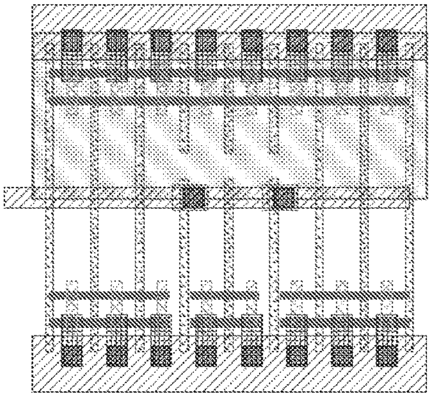
FIG. 1105A
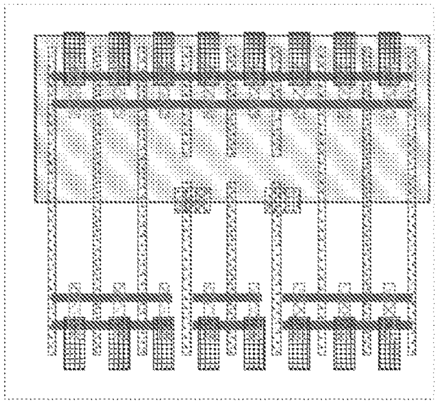
FIG. 1105B
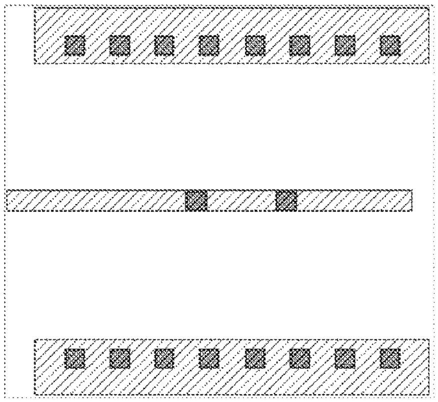
FIG. 1105C
*M* PDF Solutions, Inc.

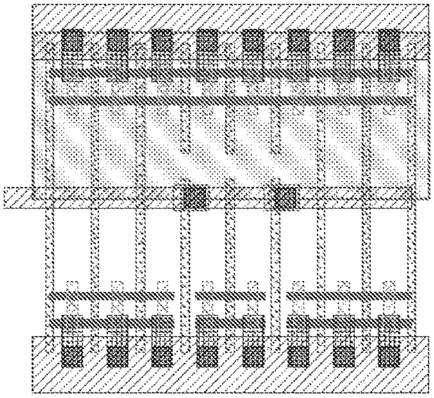
FIG. 1106A
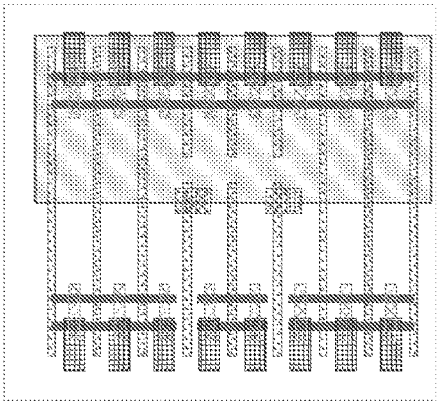
FIG. 1106B
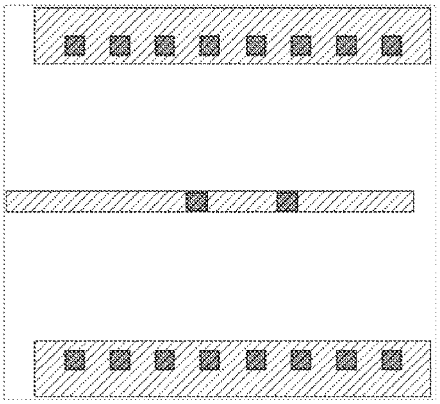
FIG. 1106C

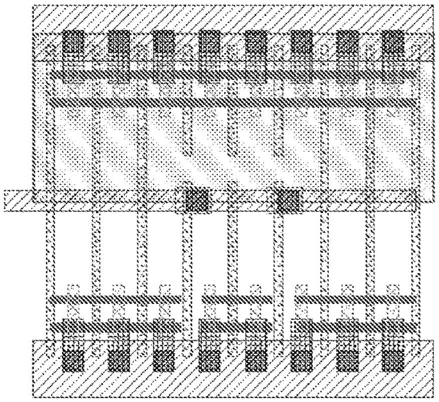
FIG. 1107A
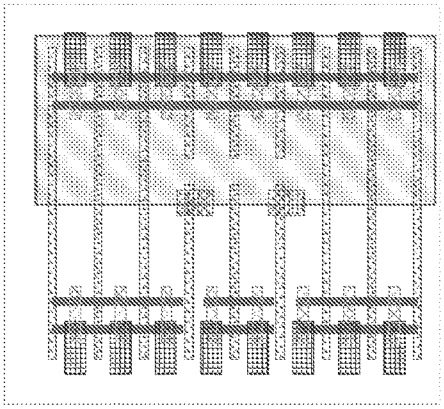
FIG. 1107B
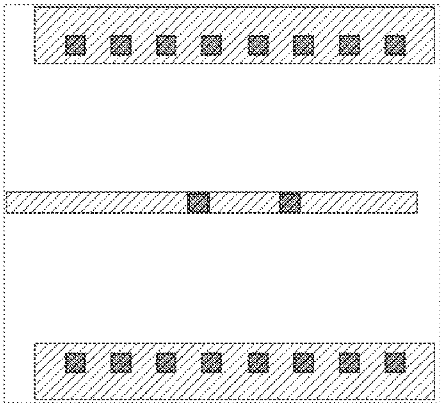
FIG. 1107C

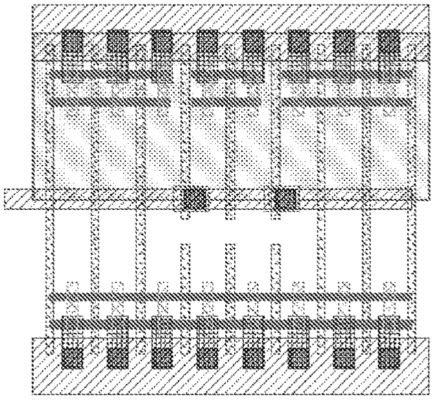
FIG. 1108A
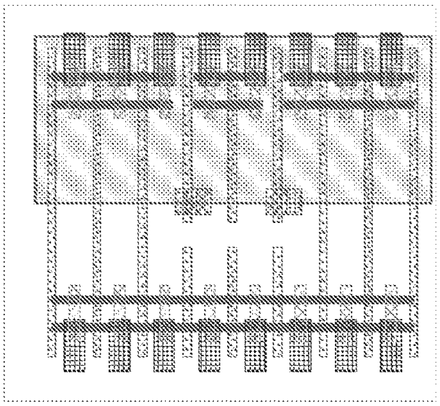
FIG. 1108B
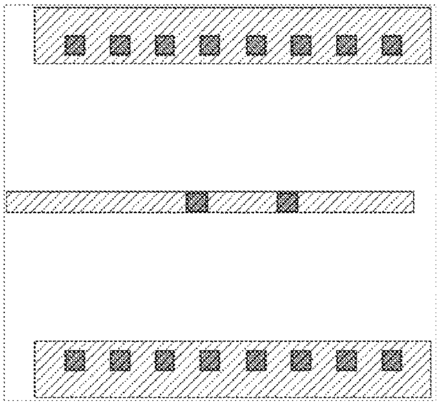
FIG. 1108C

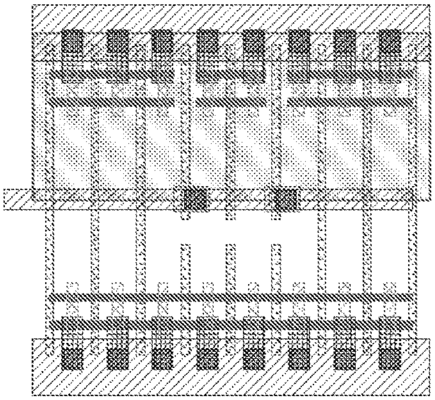
FIG. 1109A
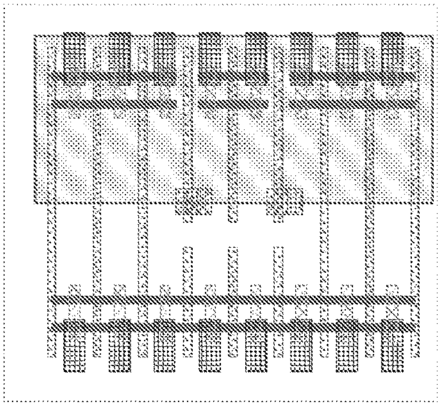
FIG. 1109B
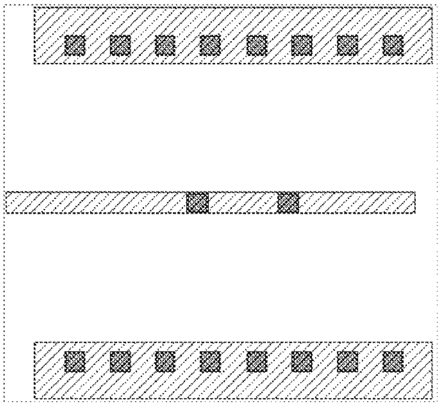
FIG. 1109C
*M* PDF Solutions, Inc.

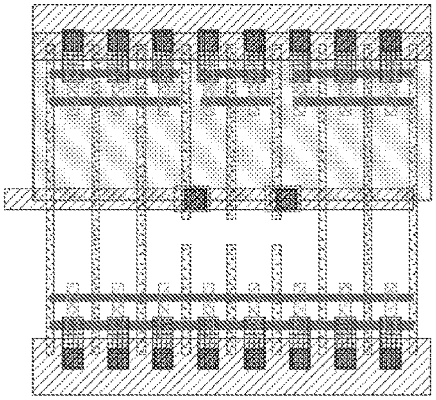
FIG. 1110A
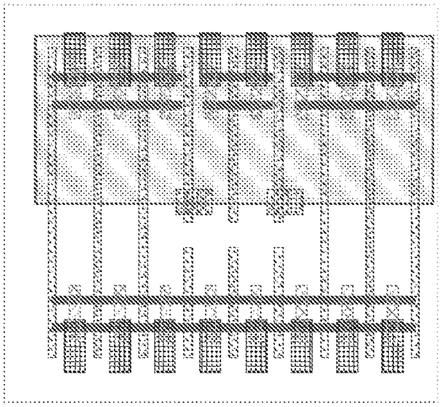
FIG. 1110B
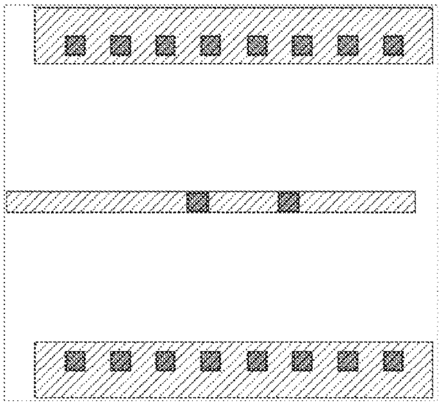
FIG. 1110C

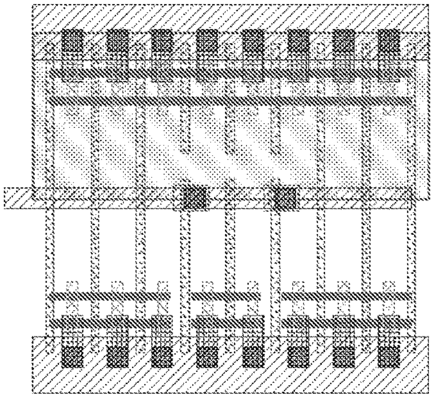
FIG. 1111A
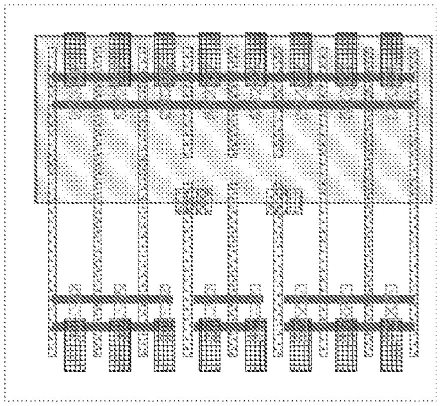
FIG. 1111B
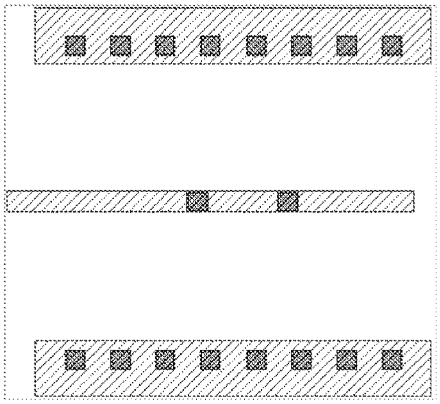
FIG. 1111C

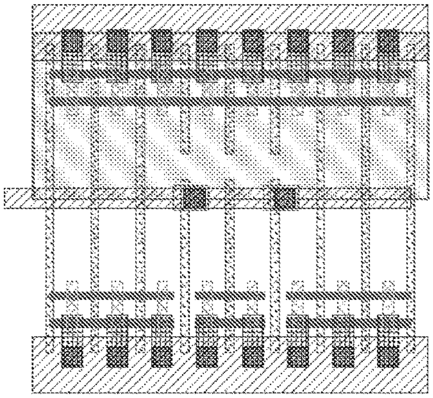
FIG. 1112A
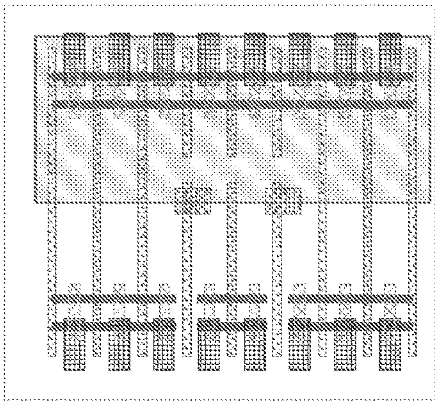
FIG. 1112B
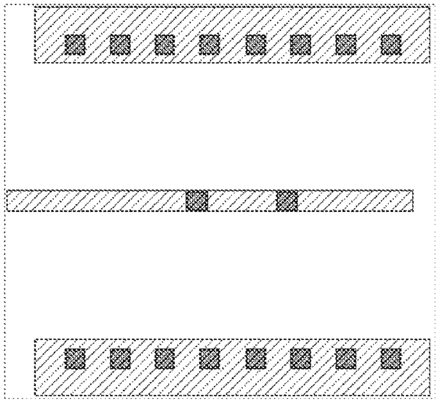
FIG. 1112C
*M* PDF Solutions, Inc.

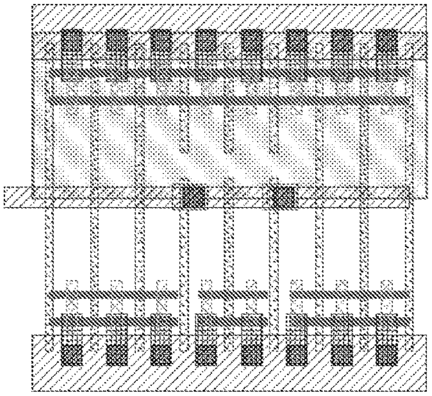
FIG. 1113A
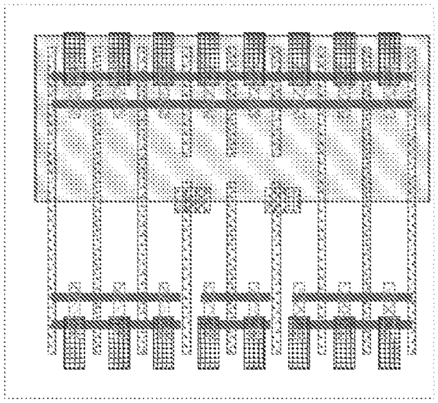
FIG. 1113B
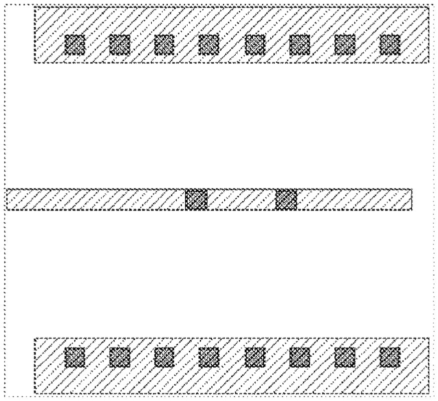
FIG. 1113C

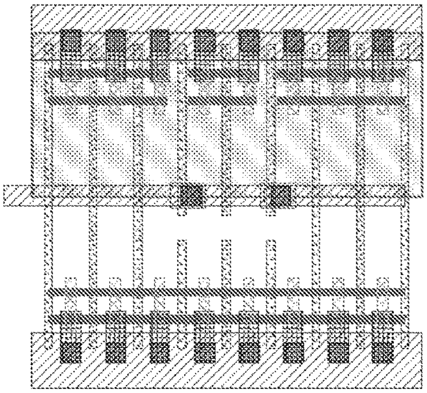
FIG. 1114A
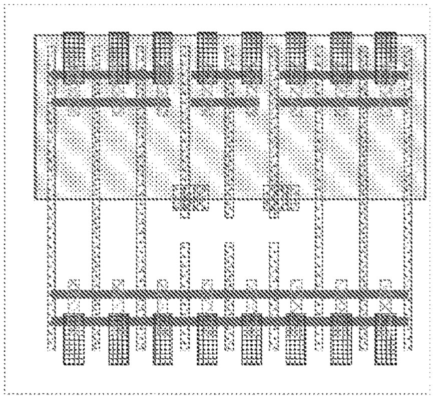
FIG. 1114B
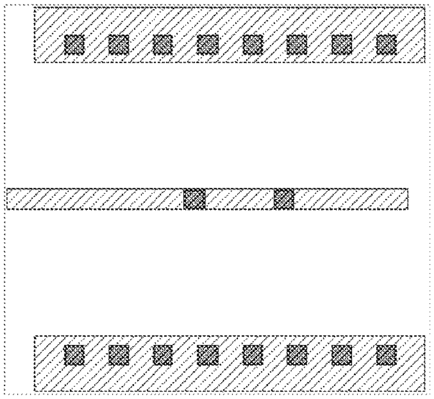
FIG. 1114C

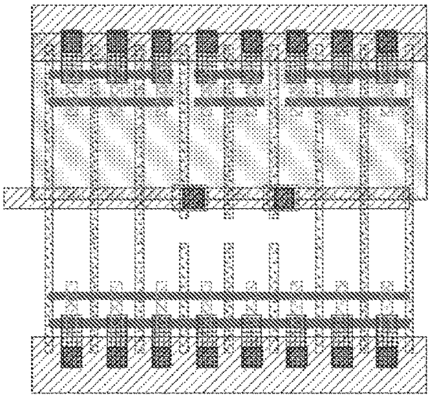
FIG. 1115A
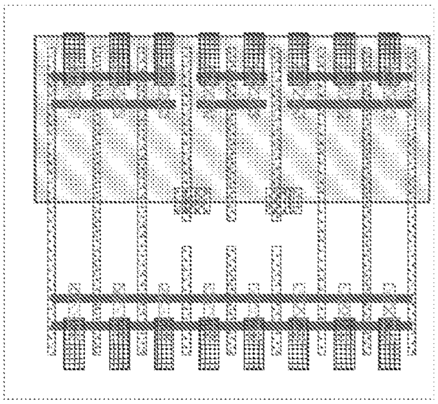
FIG. 1115B
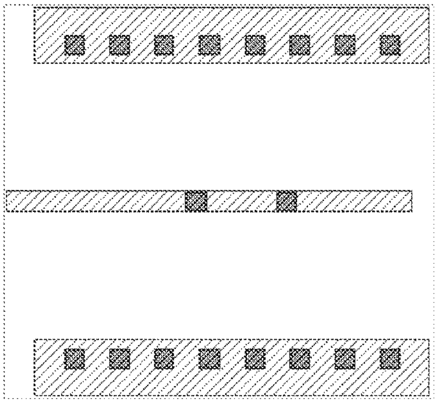
FIG. 1115C

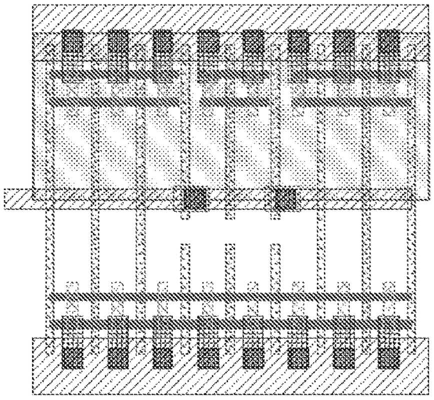
FIG. 1116A
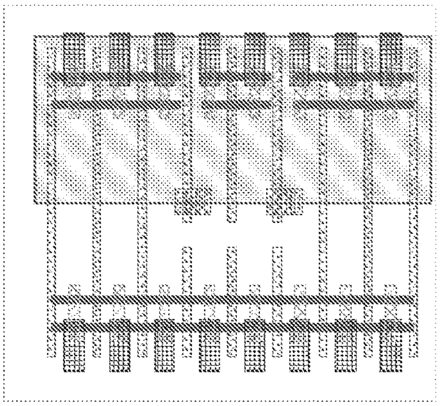
FIG. 1116B
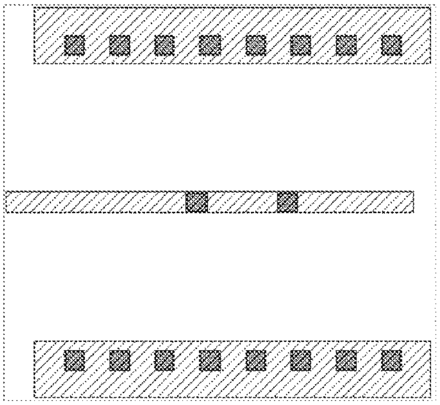
FIG. 1116C

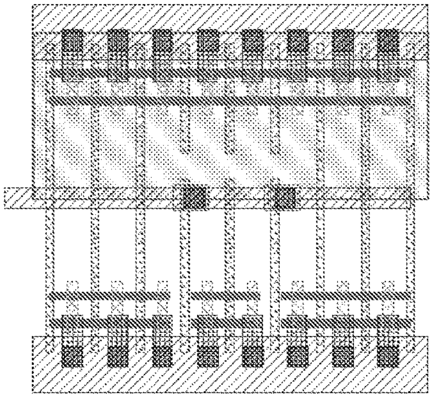
FIG. 1117A
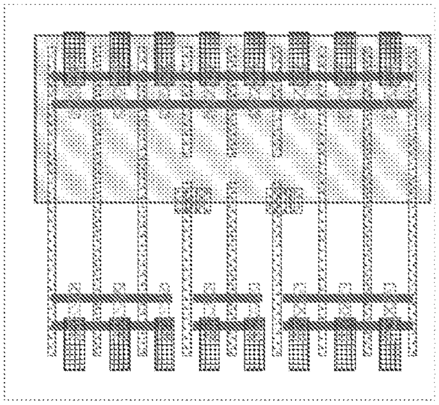
FIG. 1117B
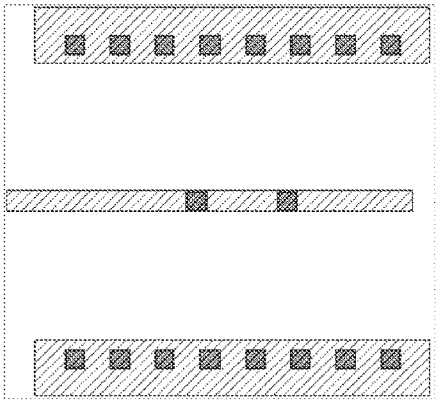
FIG. 1117C

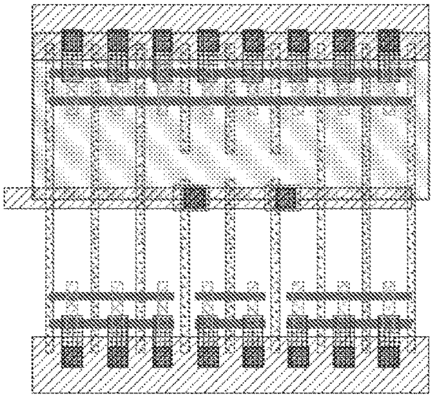
FIG. 1118A
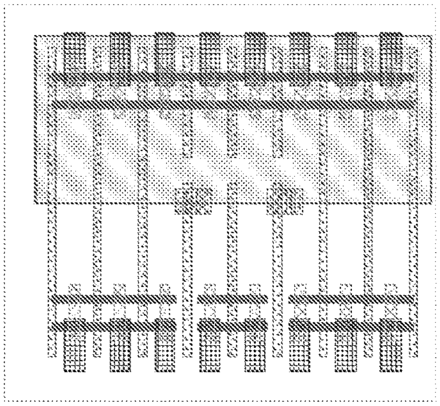
FIG. 1118B
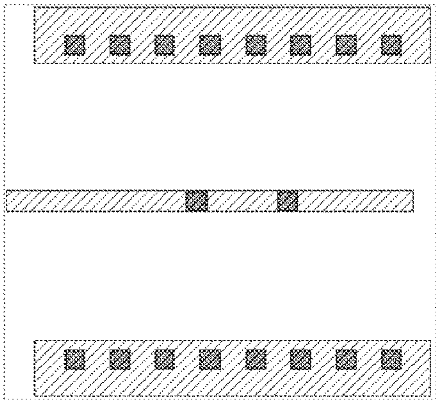
FIG. 1118C
*M* PDF Solutions, Inc.

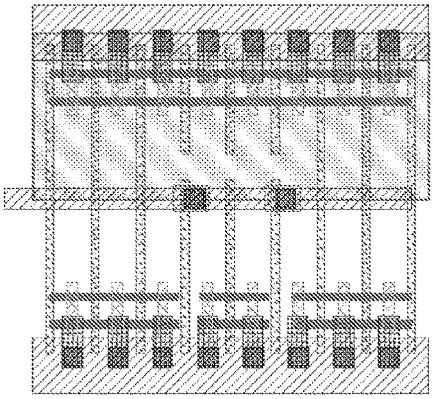
FIG. 1119A
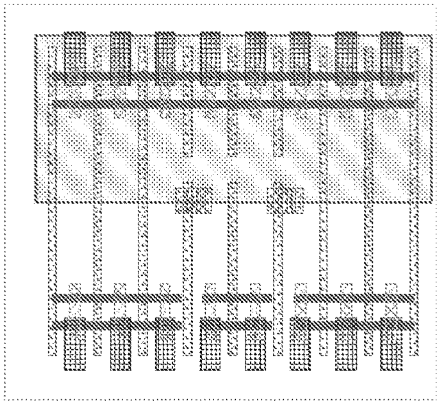
FIG. 1119B
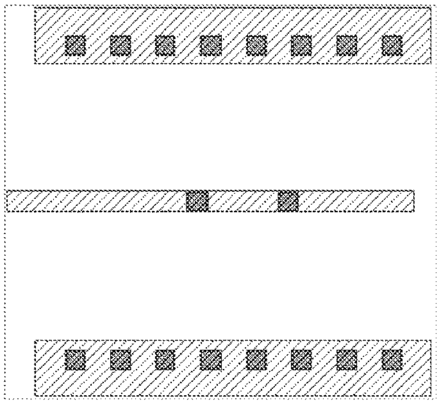
FIG. 1119C
*M* PDF Solutions, Inc.

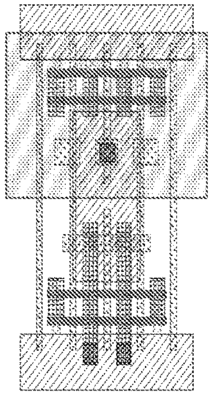
FIG. 1120A
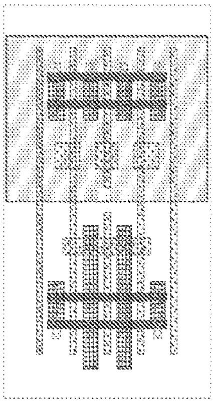
FIG. 1120B
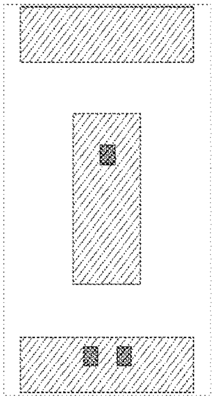
FIG. 1120C

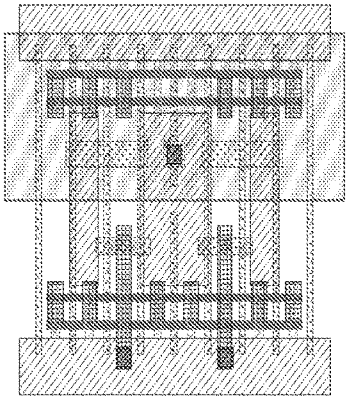
FIG. 1121A
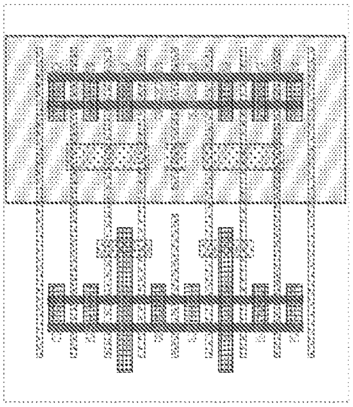
FIG. 1121B
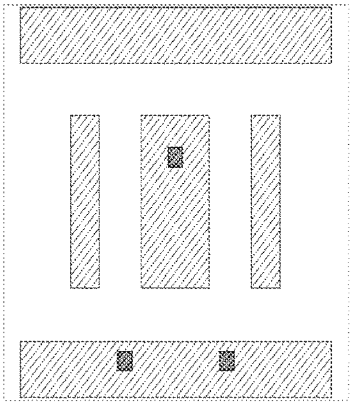
FIG. 1121C

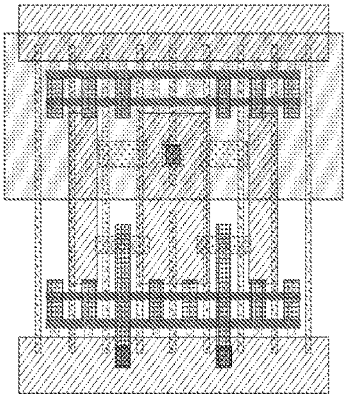
FIG. 1122A
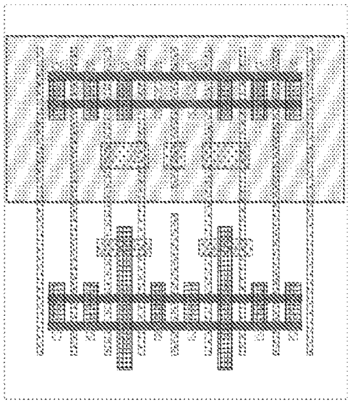
FIG. 1122B
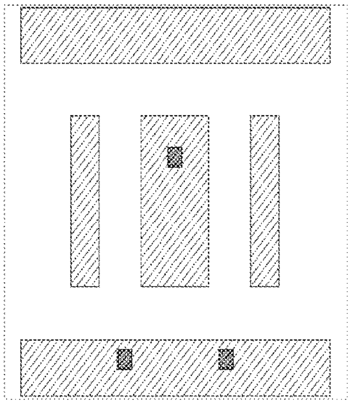
FIG. 1122C

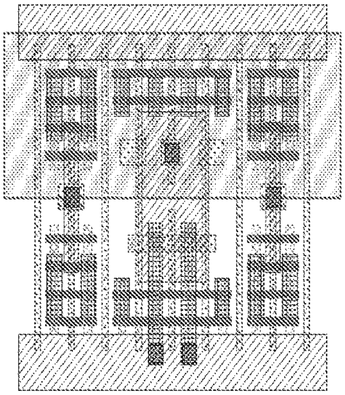
FIG. 1123A
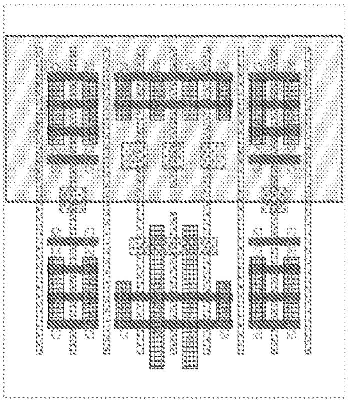
FIG. 1123B
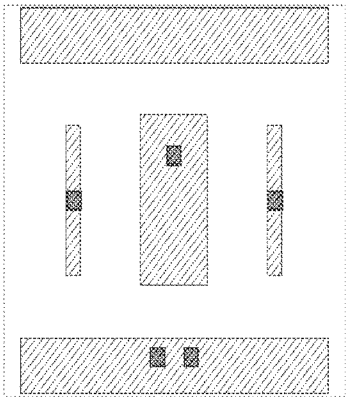
FIG. 1123C

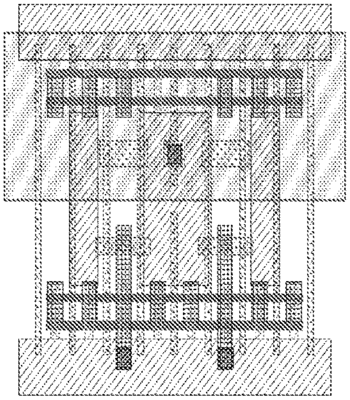
FIG. 1124A
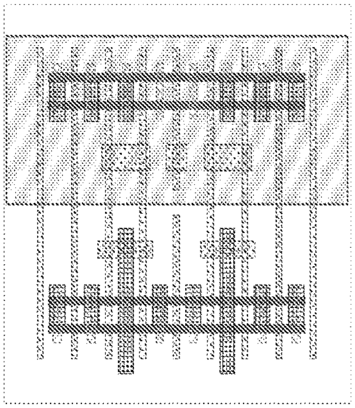
FIG. 1124B
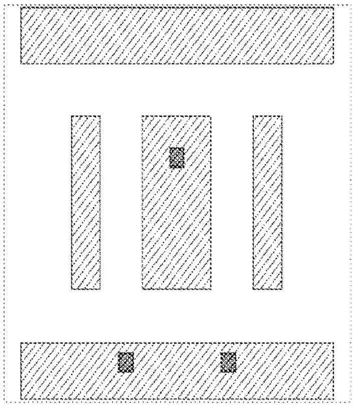
FIG. 1124C

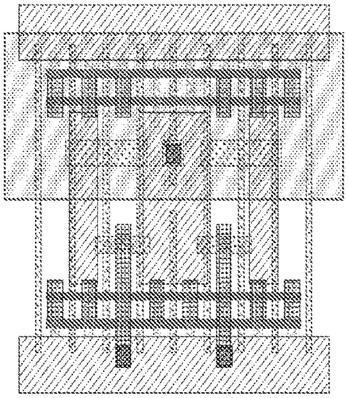
FIG. 1125A
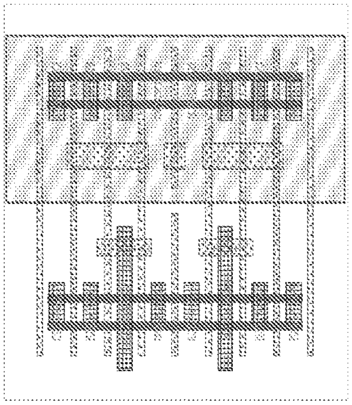
FIG. 1125B
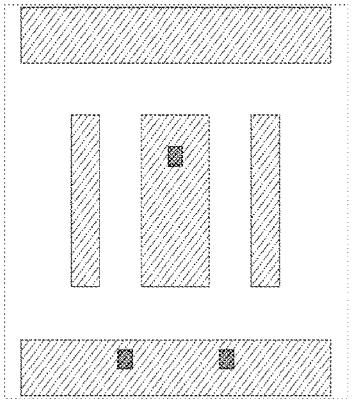
FIG. 1125C
*M* PDF Solutions, Inc.

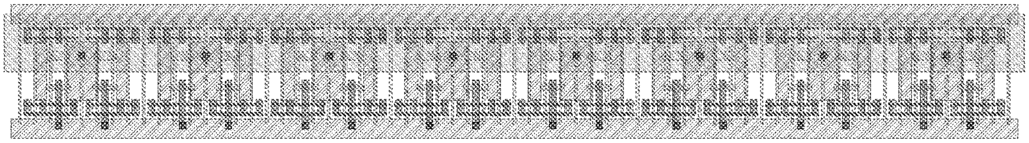
FIG. 1126A
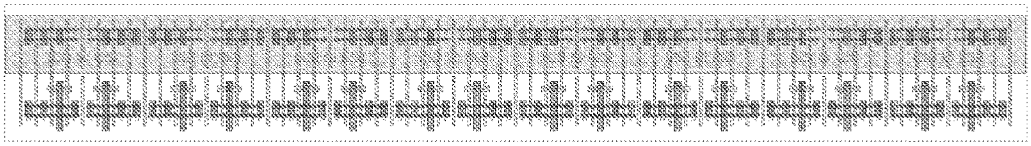
FIG. 1126B
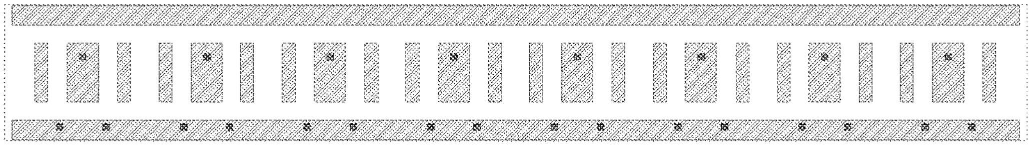
FIG. 1126C

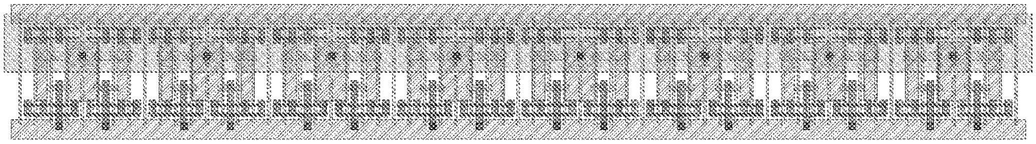
FIG. 1127A
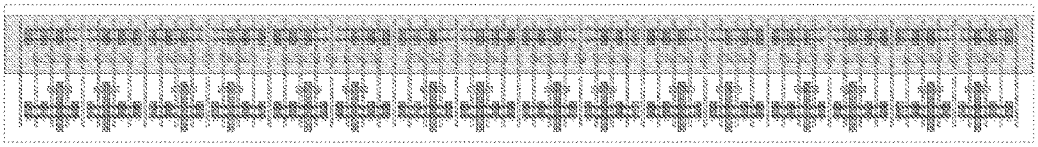
FIG. 1127B
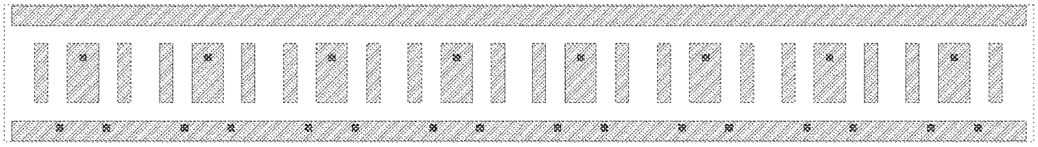
FIG. 1127C

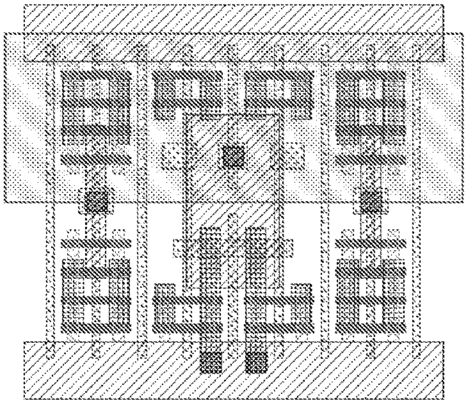
FIG. 1128A
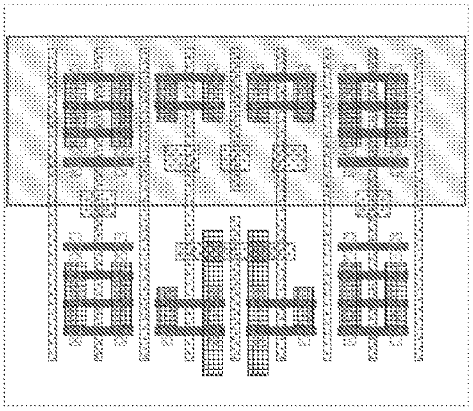
FIG. 1128B
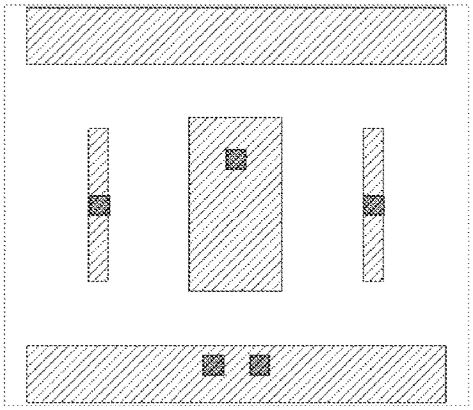
FIG. 1128C

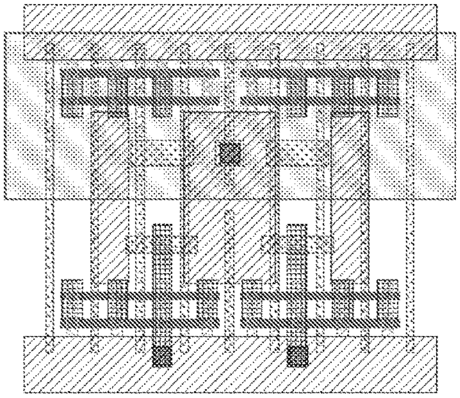
FIG. 1129A
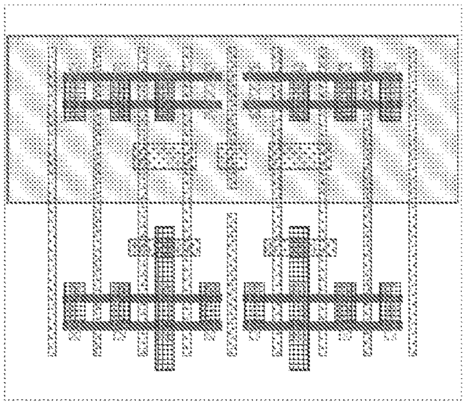
FIG. 1129B
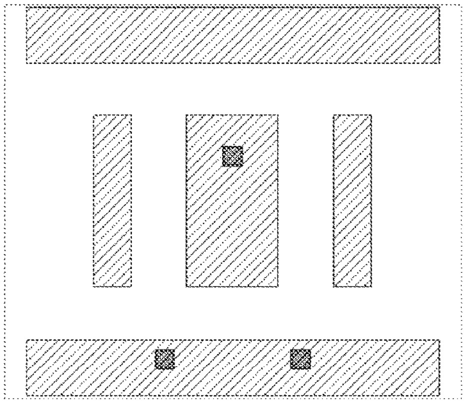
FIG. 1129C

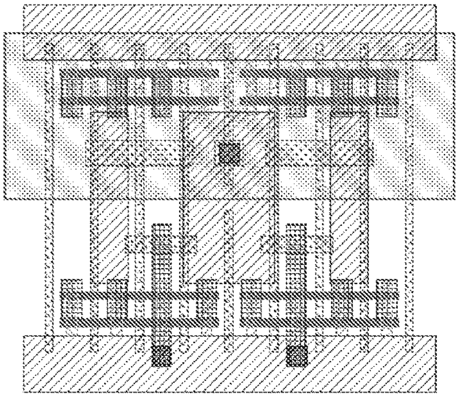
FIG. 1130A
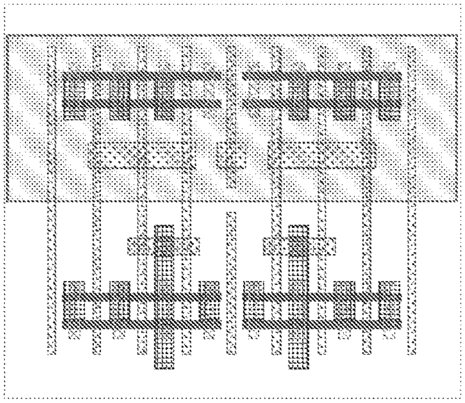
FIG. 1130B
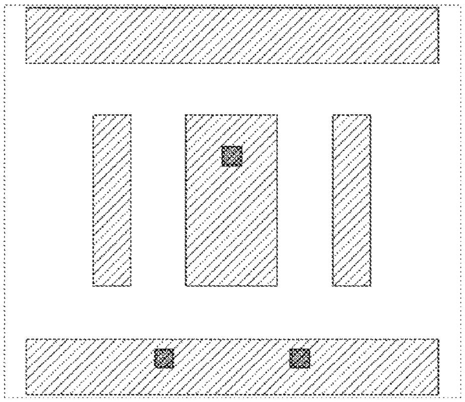
FIG. 1130C

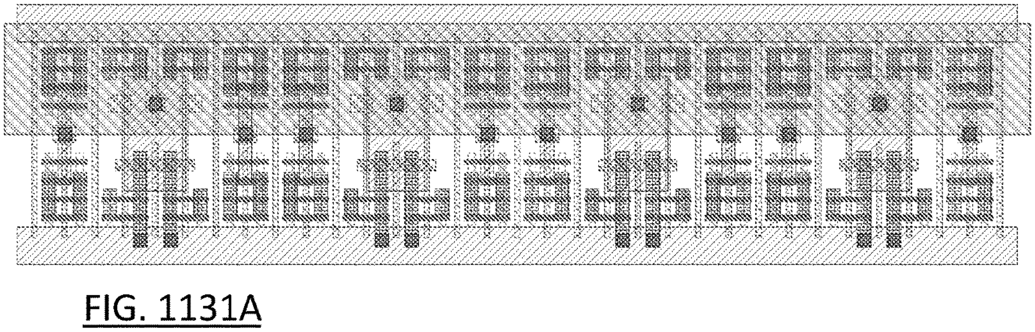
FIG. 1131A
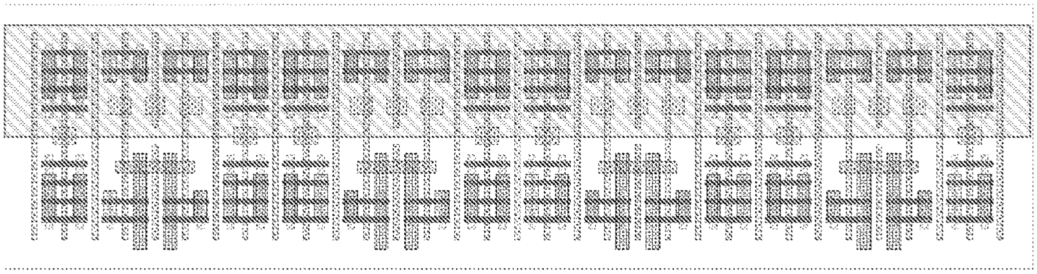
FIG. 1131B
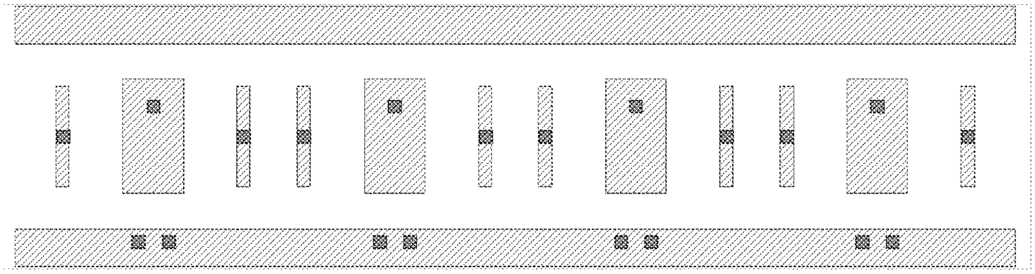
FIG. 1131C

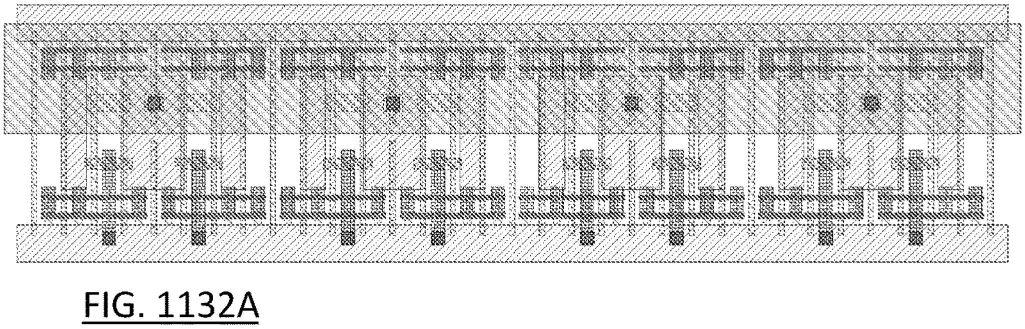
FIG. 1132A
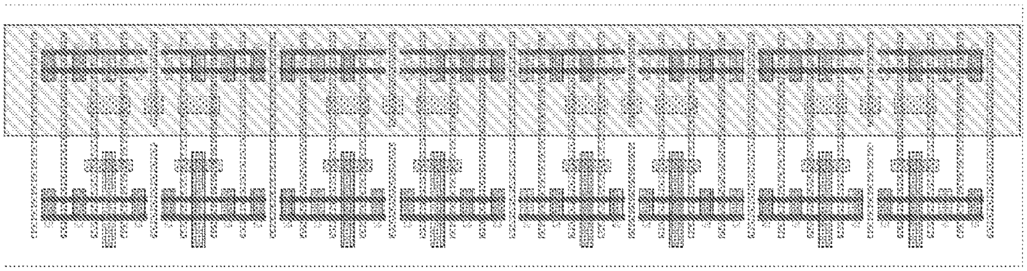
FIG. 1132B
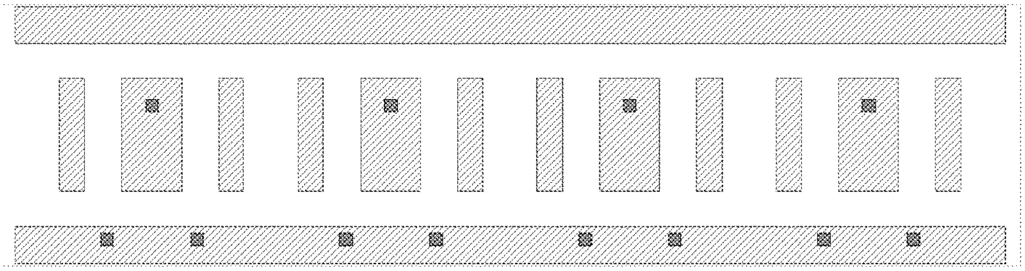
FIG. 1132C

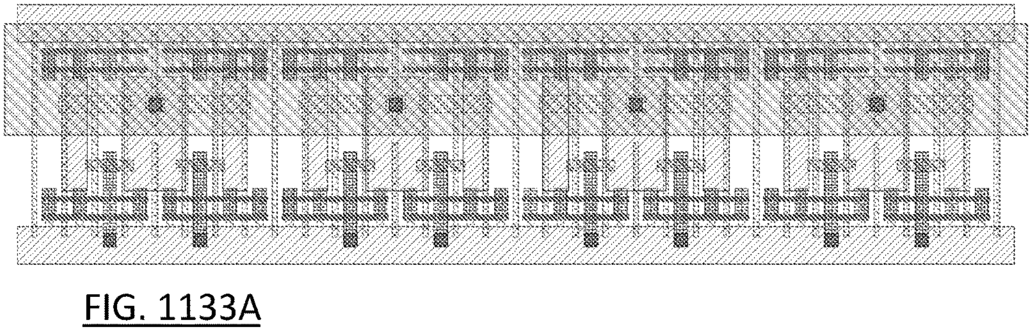
FIG. 1133A
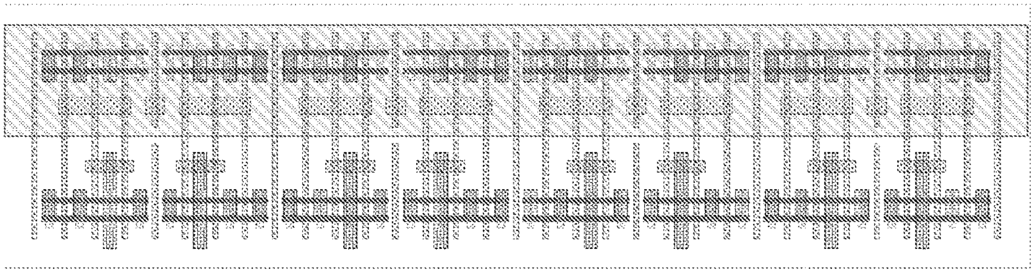
FIG. 1133B
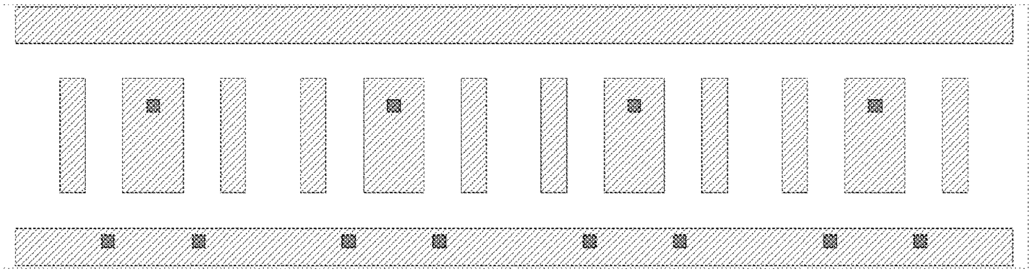
FIG. 1133C

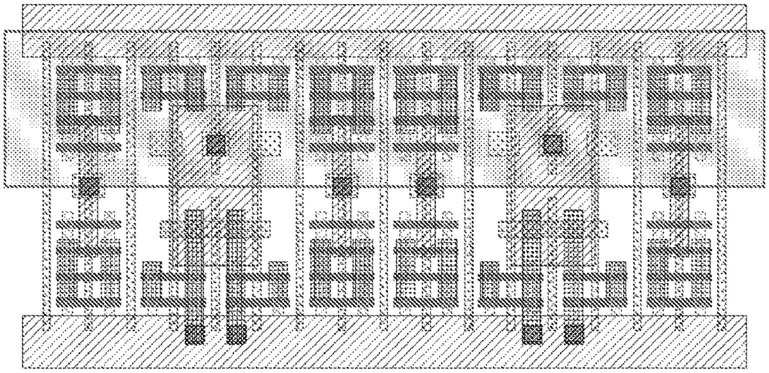
FIG. 1134A
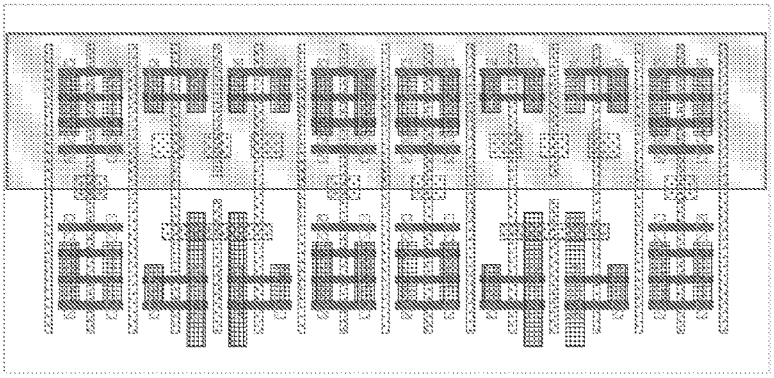
FIG. 1134B
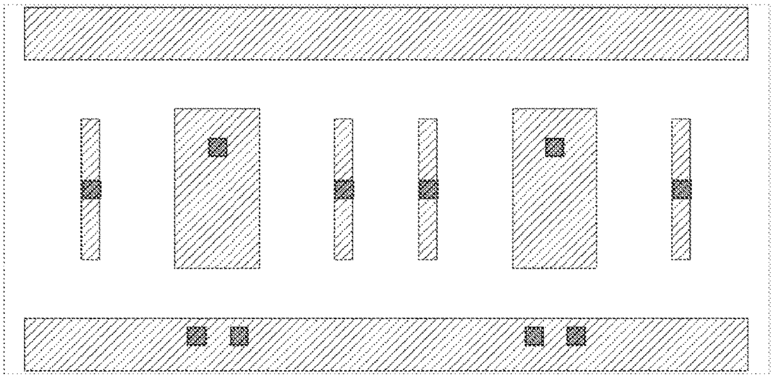
FIG. 1134C
*M* PDF Solutions, Inc.

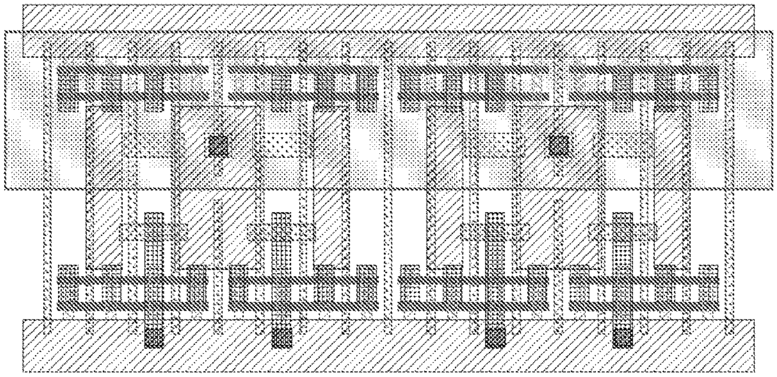
FIG. 1135A
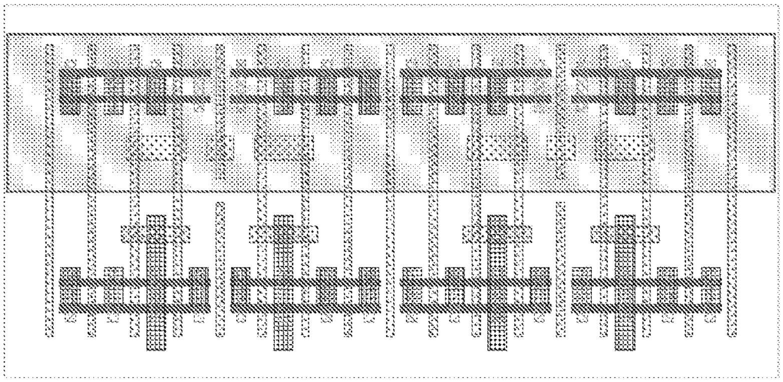
FIG. 1135B
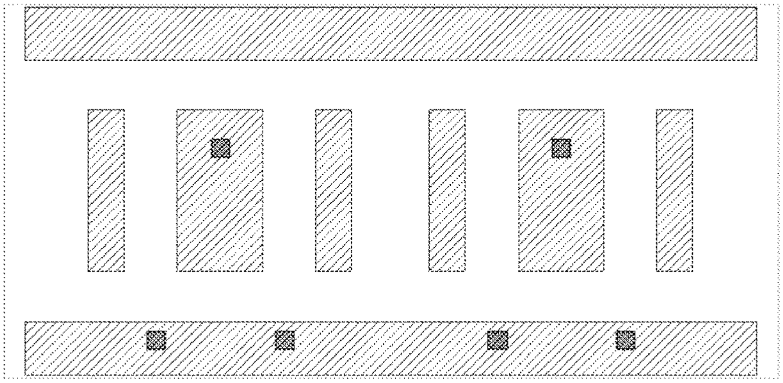
FIG. 1135C
*M* PDF Solutions, Inc.

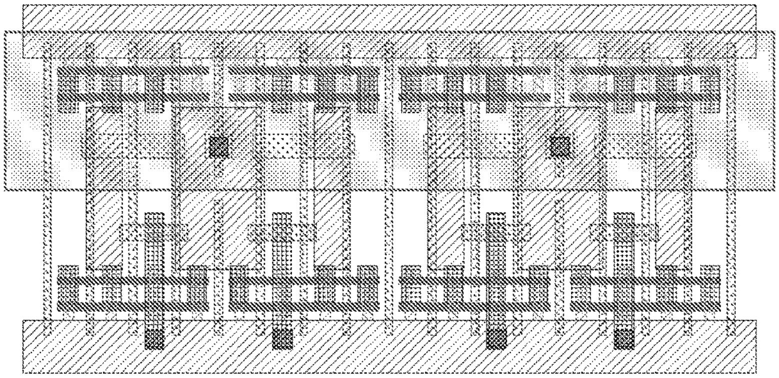
FIG. 1136A
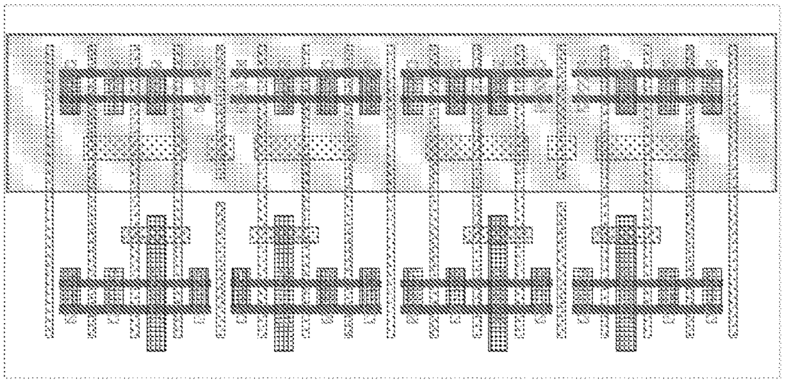
FIG. 1136B
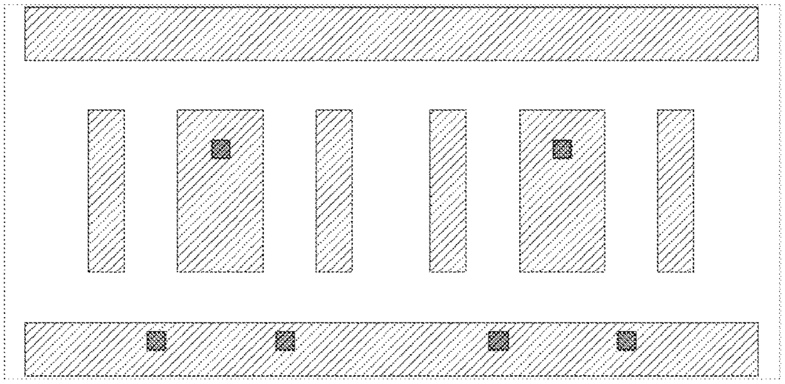
FIG. 1136C

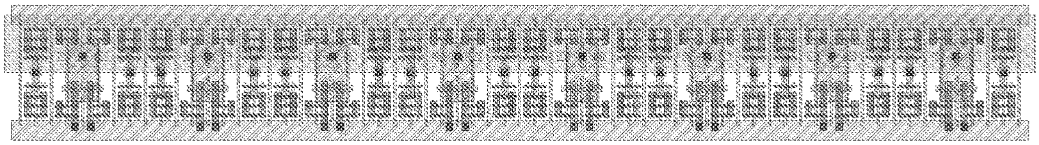
FIG. 1137A
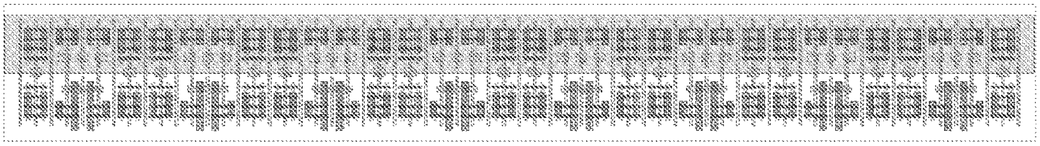
FIG. 1137B
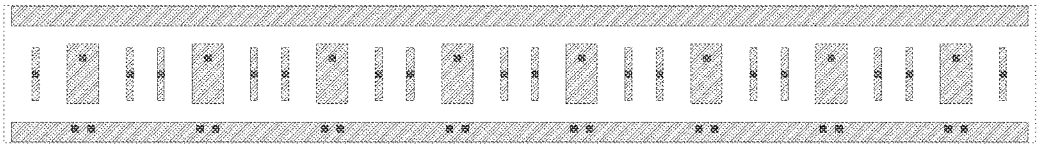
FIG. 1137C

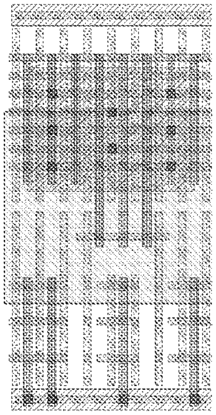
FIG. 1138A
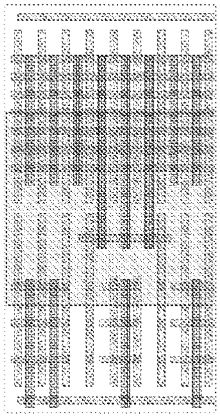
FIG. 1138B
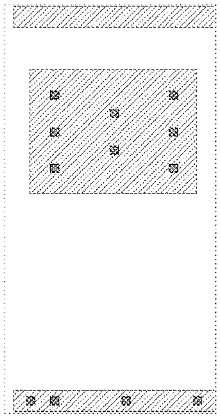
FIG. 1138C

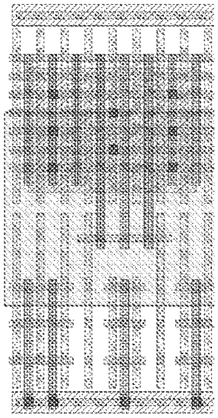
FIG. 1139A
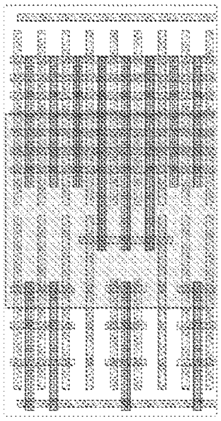
FIG. 1139B
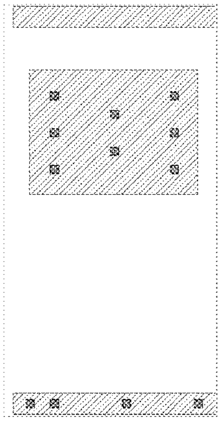
FIG. 1139C

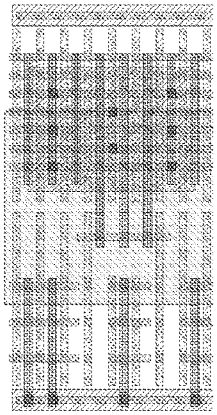
FIG. 1140A
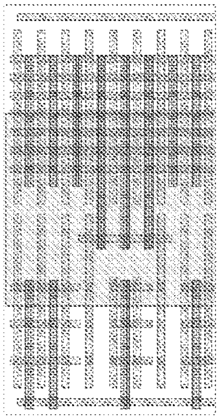
FIG. 1140B
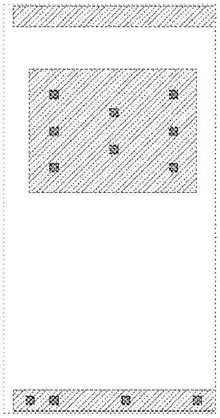
FIG. 1140C
*M* PDF Solutions, Inc.

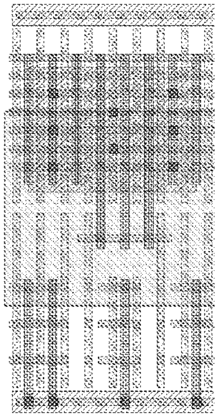
FIG. 1141A
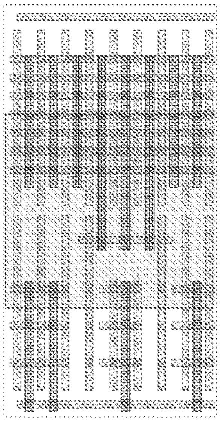
FIG. 1141B
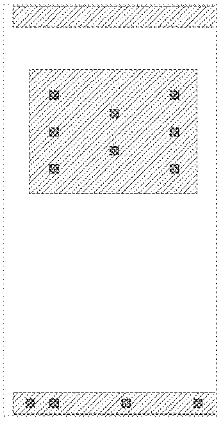
FIG. 1141C

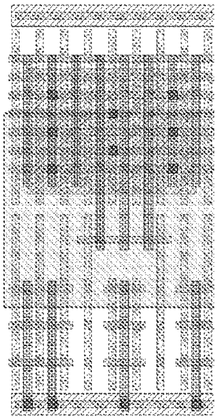
FIG. 1142A
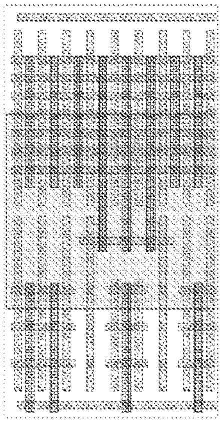
FIG. 1142B
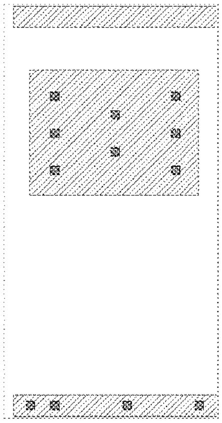
FIG. 1142C

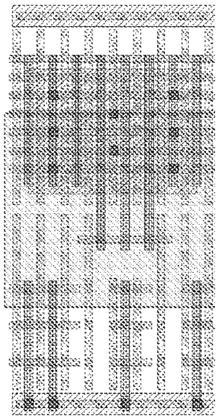
FIG. 1143A
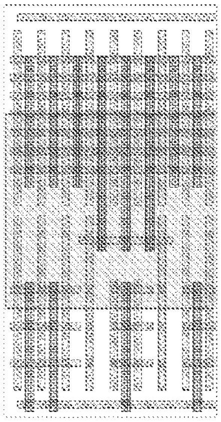
FIG. 1143B
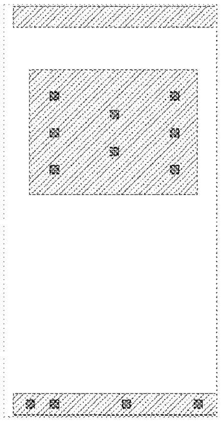
FIG. 1143C

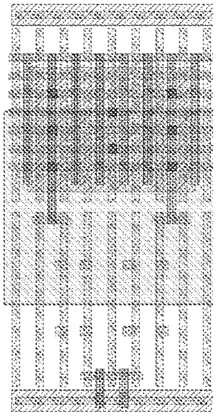
FIG. 1144A
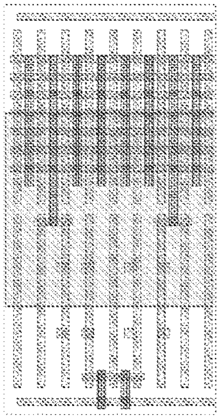
FIG. 1144B
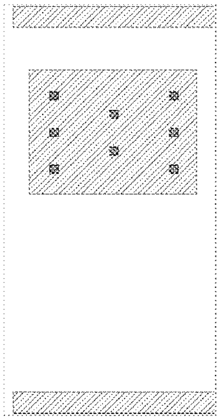
FIG. 1144C

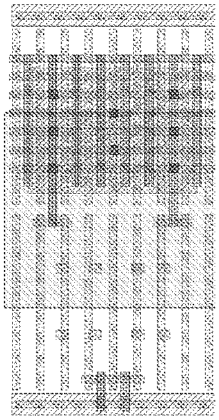
FIG. 1145A
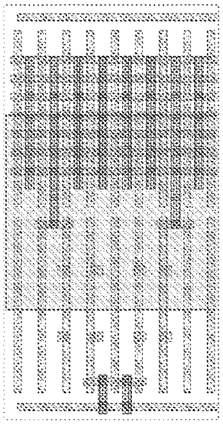
FIG. 1145B
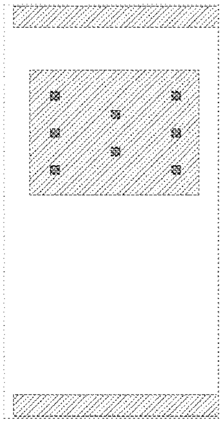
FIG. 1145C

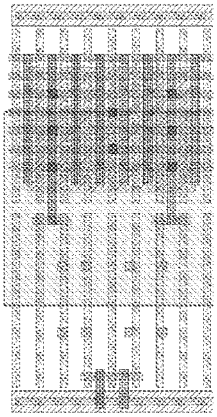
FIG. 1146A
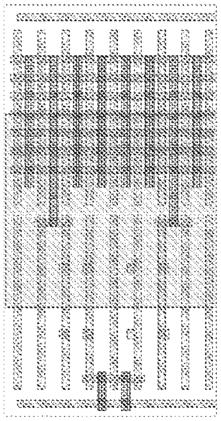
FIG. 1146B
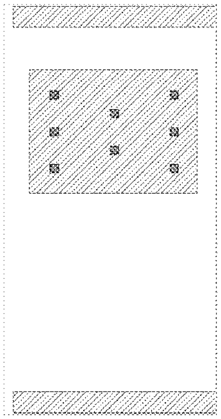
FIG. 1146C

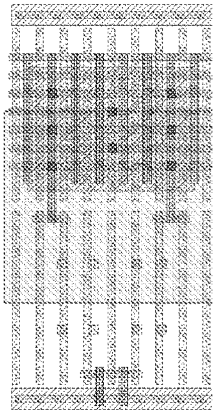
FIG. 1147A
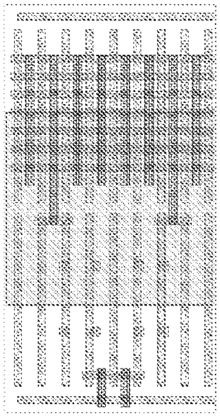
FIG. 1147B
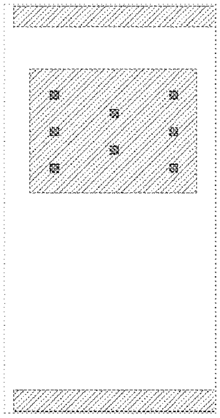
FIG. 1147C

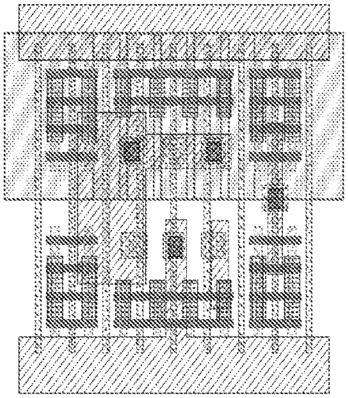
FIG. 1148A
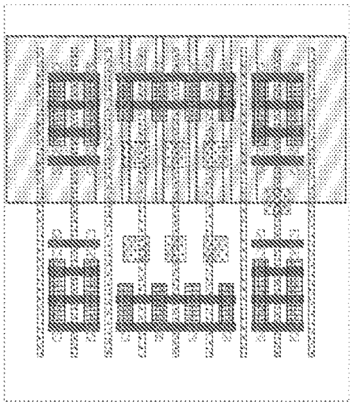
FIG. 1148B
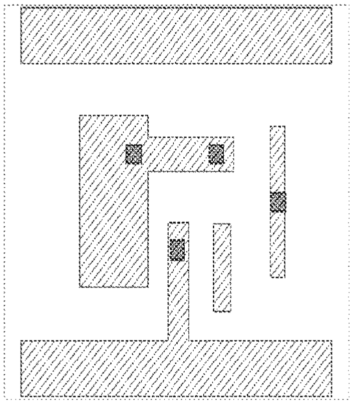
FIG. 1148C
*M* PDF Solutions, Inc.

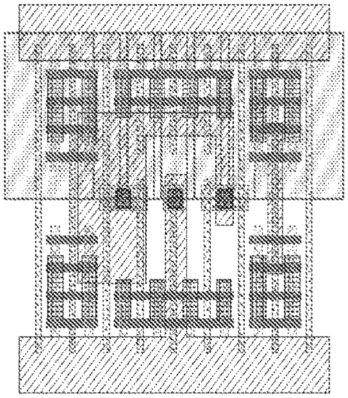
FIG. 1149A
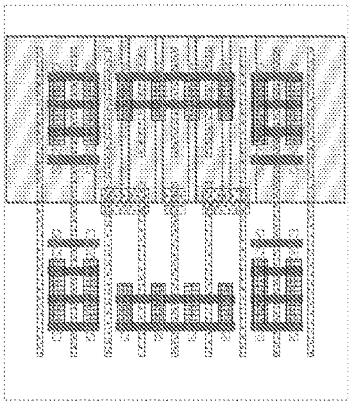
FIG. 1149B
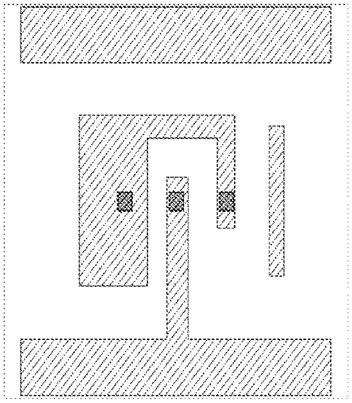
FIG. 1149C

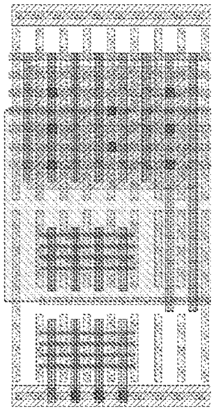
FIG. 1150A
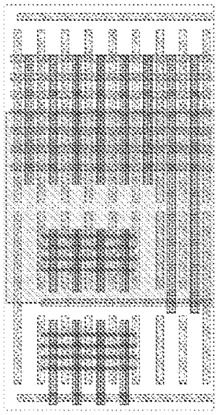
FIG. 1150B
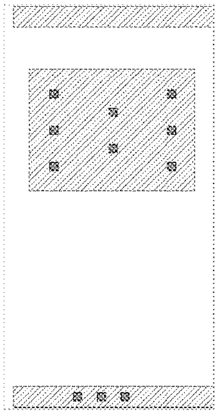
FIG. 1150C

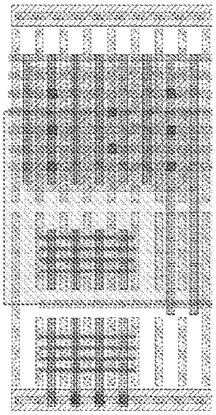
FIG. 1151A
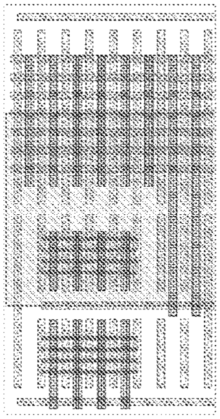
FIG. 1151B
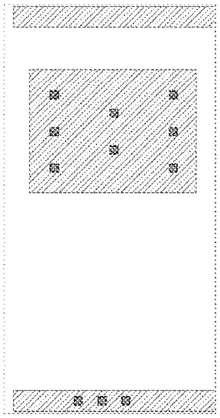
FIG. 1151C

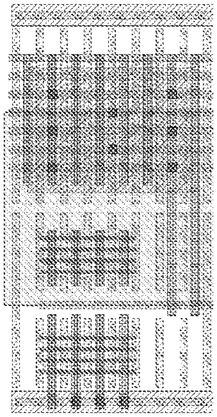
FIG. 1152A
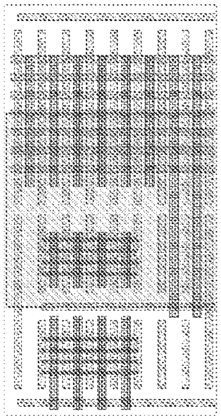
FIG. 1152B
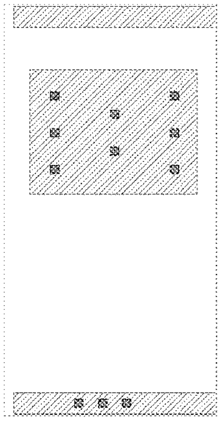
FIG. 1152C
*M* PDF Solutions, Inc.

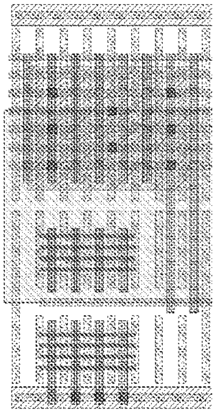
FIG. 1153A
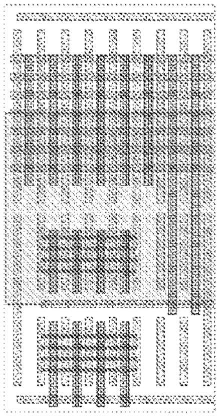
FIG. 1153B
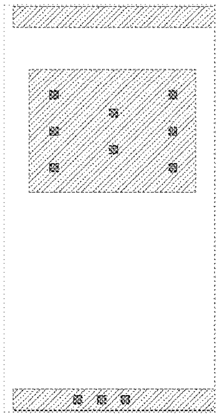
FIG. 1153C

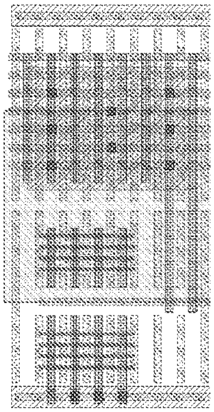
FIG. 1154A
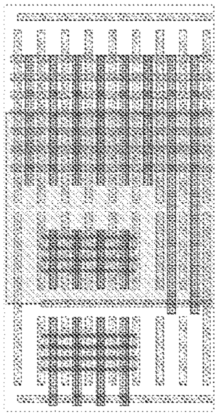
FIG. 1154B
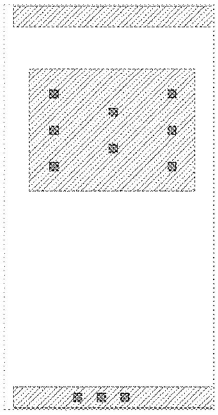
FIG. 1154C

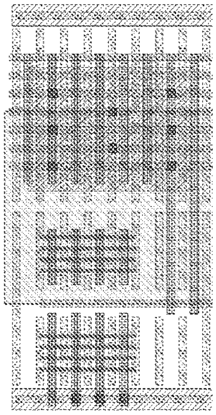
FIG. 1155A
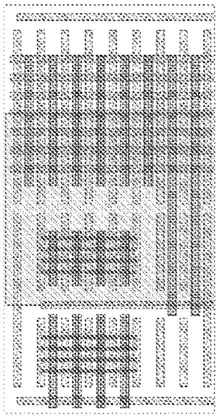
FIG. 1155B
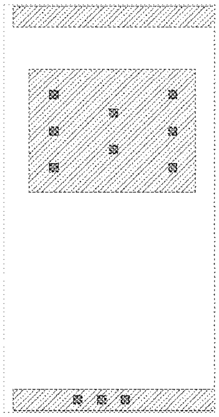
FIG. 1155C

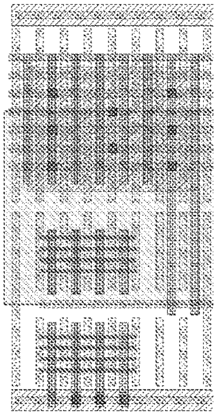
FIG. 1156A
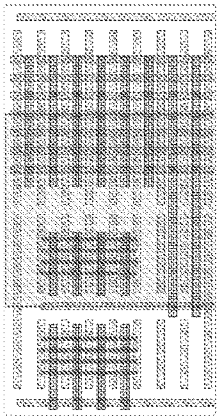
FIG. 1156B
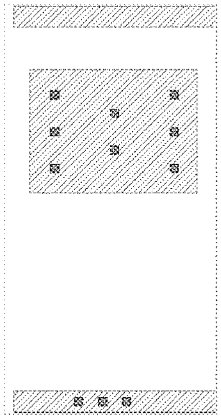
FIG. 1156C
*M* PDF Solutions, Inc.

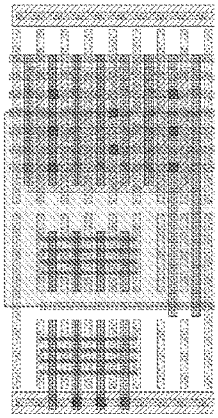
FIG. 1157A
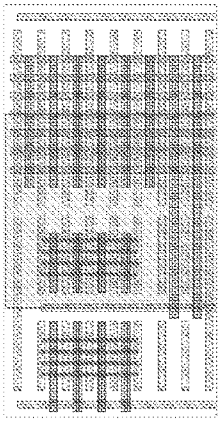
FIG. 1157B
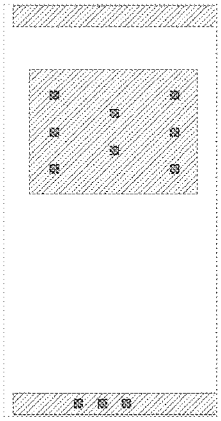
FIG. 1157C
*M* PDF Solutions, Inc.

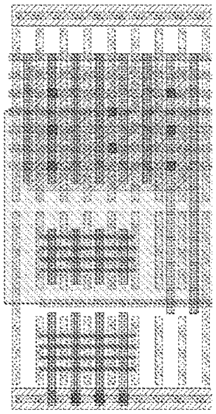
FIG. 1158A
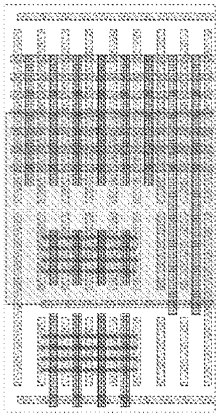
FIG. 1158B
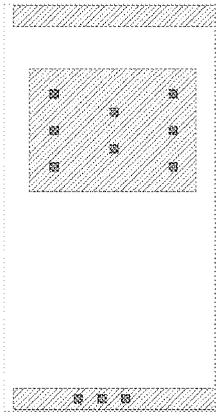
FIG. 1158C

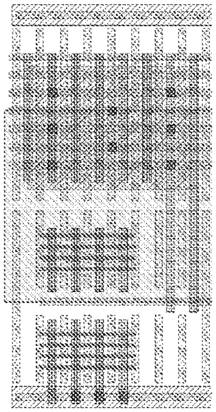
FIG. 1159A
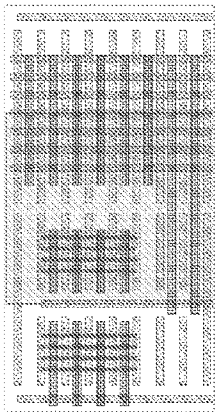
FIG. 1159B
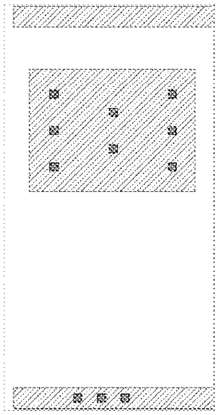
FIG. 1159C

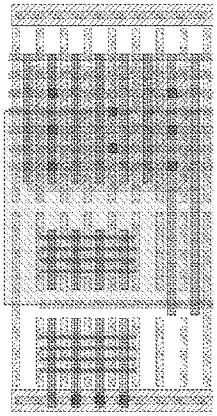
FIG. 1160A
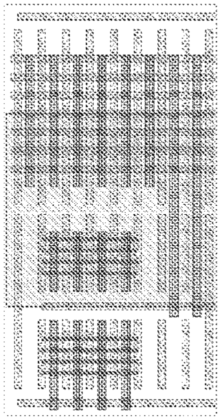
FIG. 1160B
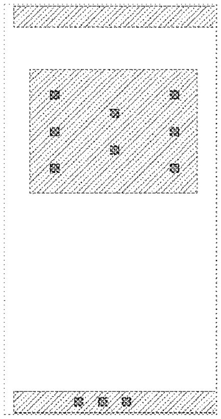
FIG. 1160C

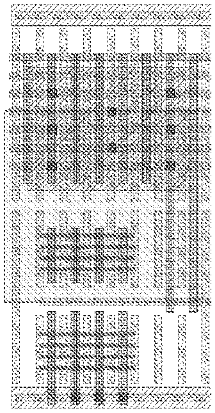
FIG. 1161A
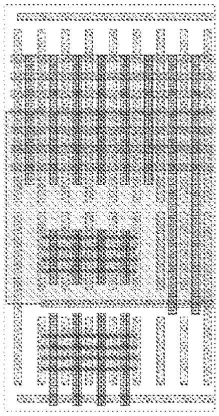
FIG. 1161B
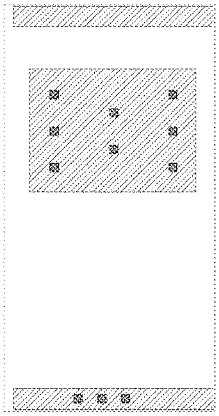
FIG. 1161C

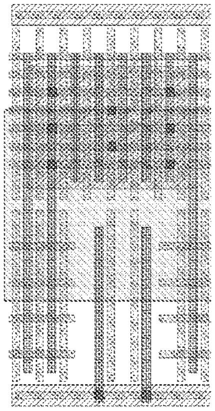
FIG. 1162A
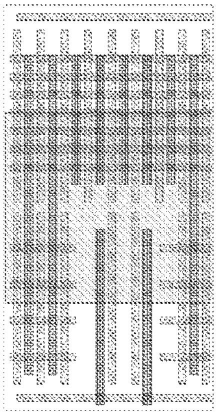
FIG. 1162B
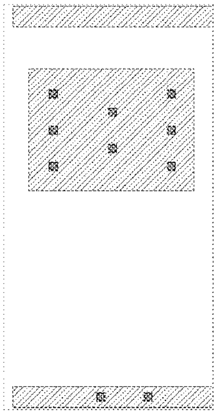
FIG. 1162C

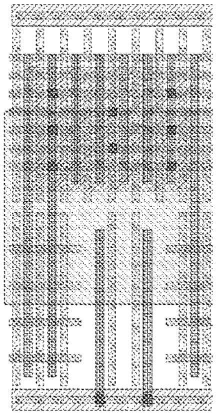
FIG. 1163A
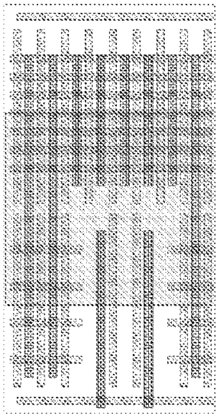
FIG. 1163B
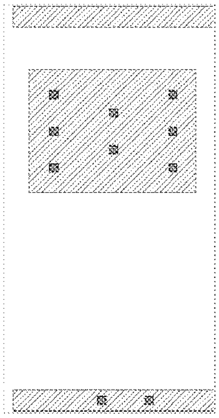
FIG. 1163C

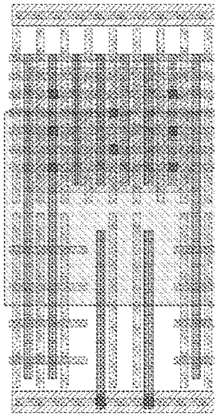
FIG. 1164A
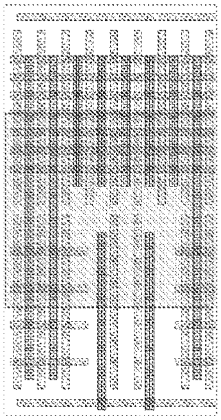
FIG. 1164B
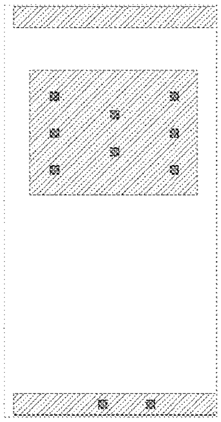
FIG. 1164C

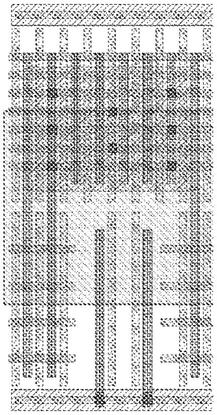
FIG. 1165A
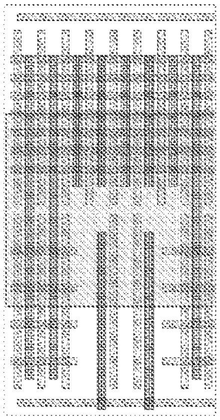
FIG. 1165B
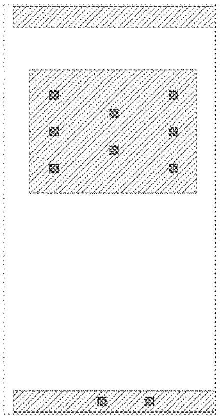
FIG. 1165C

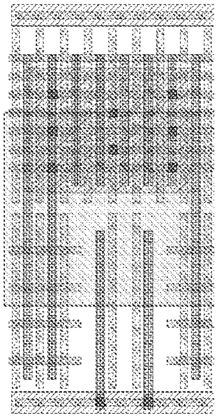
FIG. 1166A
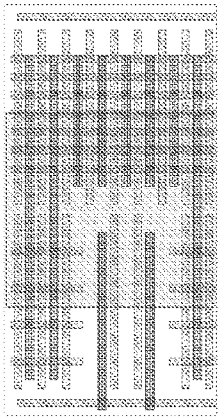
FIG. 1166B
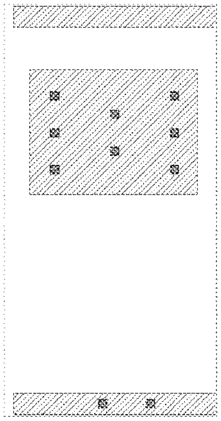
FIG. 1166C

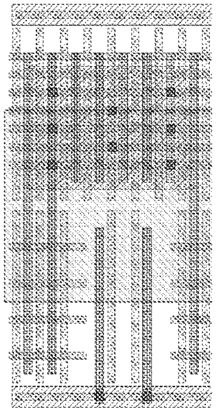
FIG. 1167A
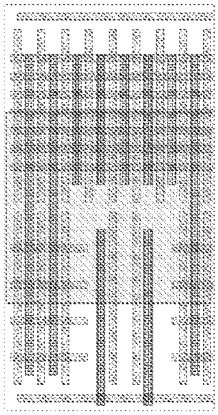
FIG. 1167B
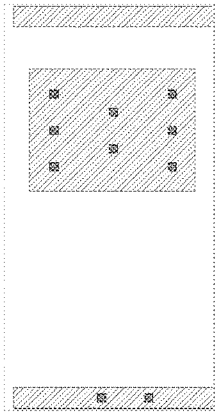
FIG. 1167C

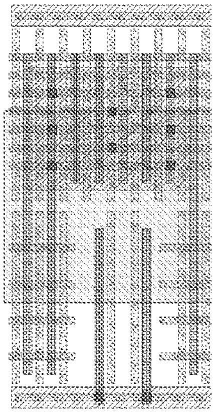
FIG. 1168A
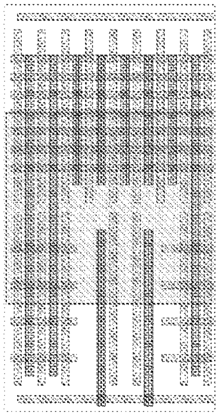
FIG. 1168B
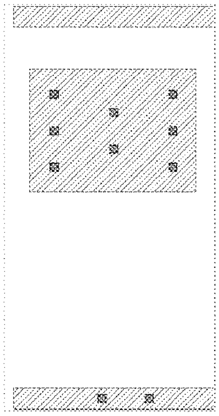
FIG. 1168C
*M* PDF Solutions, Inc.

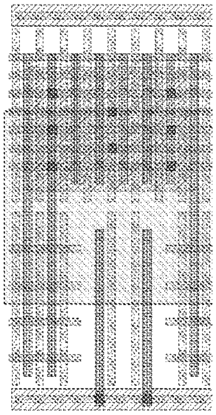
FIG. 1169A
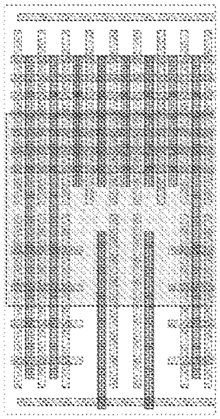
FIG. 1169B
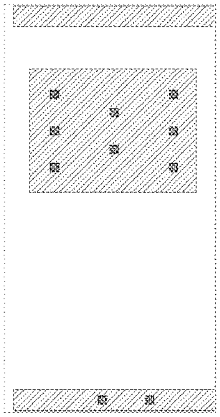
FIG. 1169C

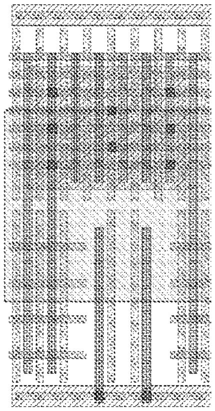
FIG. 1170A
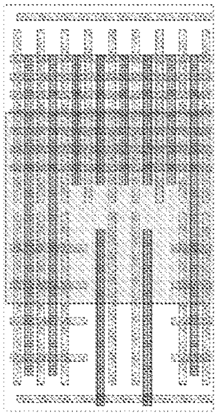
FIG. 1170B
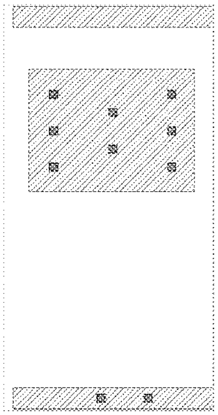
FIG. 1170C

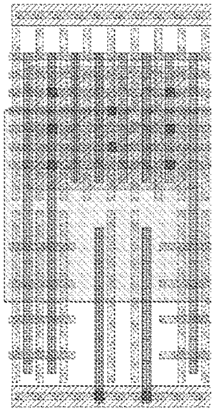
FIG. 1171A
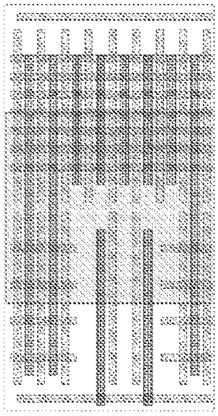
FIG. 1171B
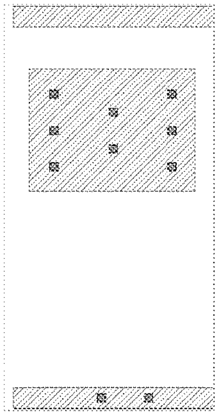
FIG. 1171C

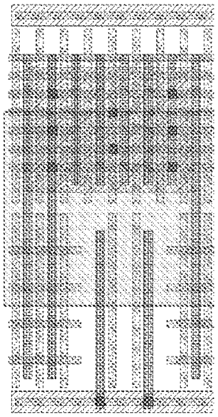
FIG. 1172A
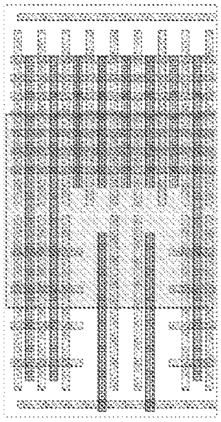
FIG. 1172B
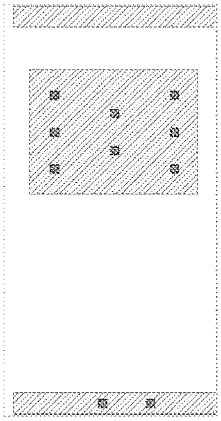
FIG. 1172C

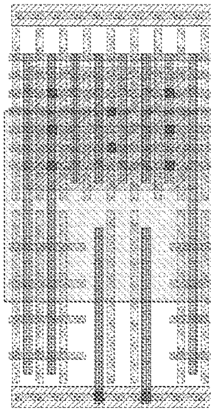
FIG. 1173A
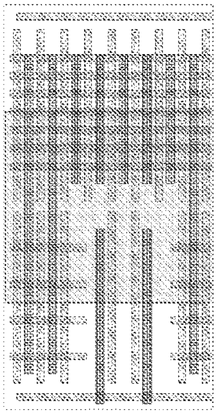
FIG. 1173B
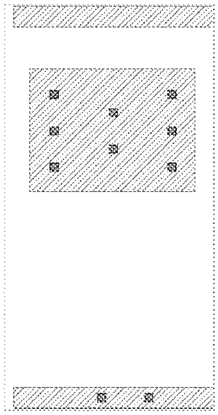
FIG. 1173C

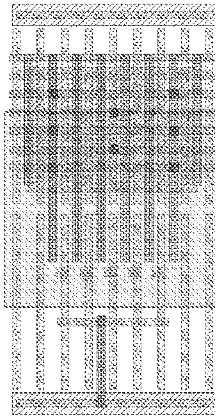
FIG. 1174A
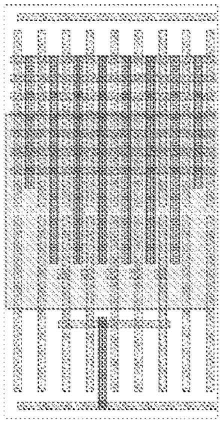
FIG. 1174B
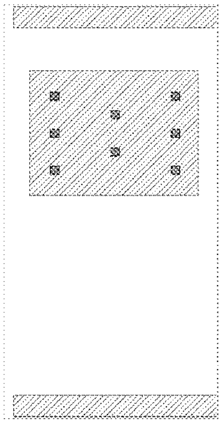
FIG. 1174C

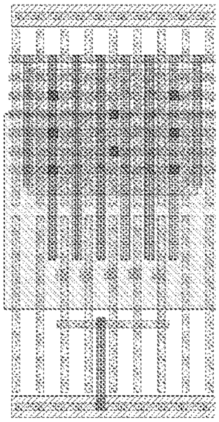
FIG. 1175A
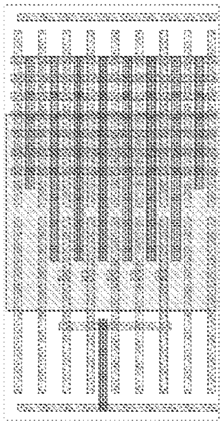
FIG. 1175B
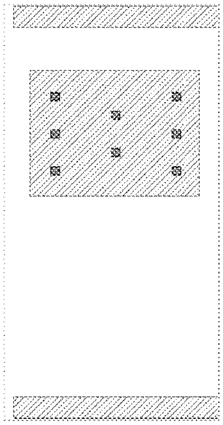
FIG. 1175C

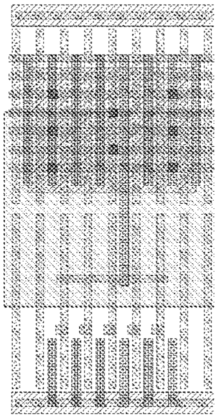
FIG. 1176A
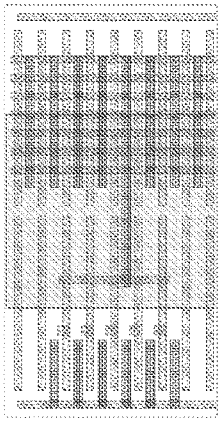
FIG. 1176B
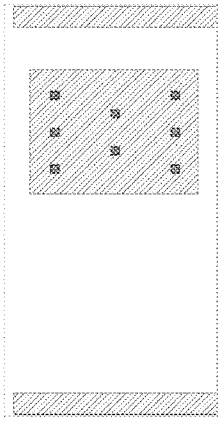
FIG. 1176C

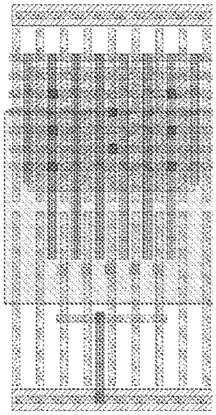
FIG. 1177A
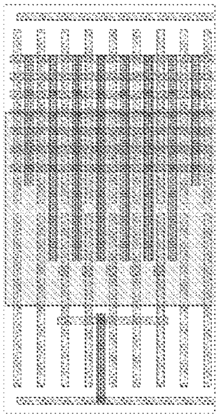
FIG. 1177B
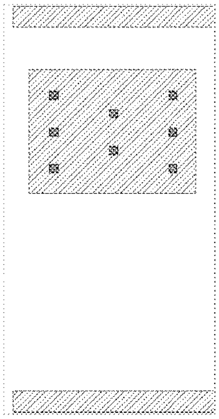
FIG. 1177C

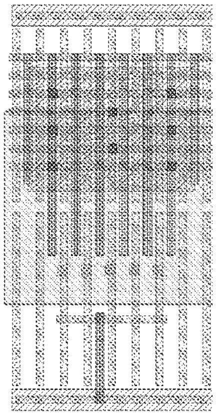
FIG. 1178A
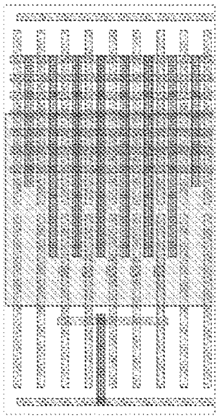
FIG. 1178B
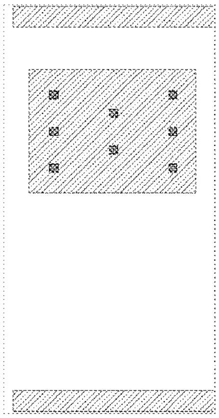
FIG. 1178C

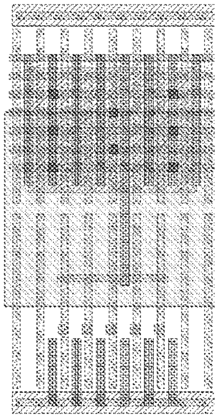
FIG. 1179A
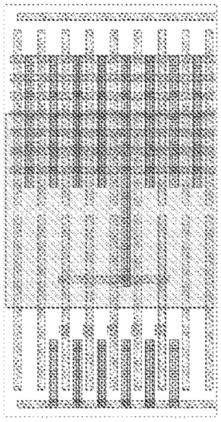
FIG. 1179B
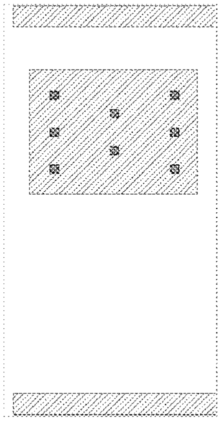
FIG. 1179C

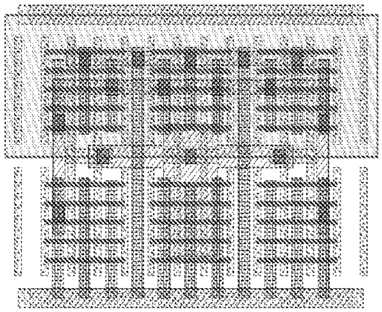
FIG. 1180A
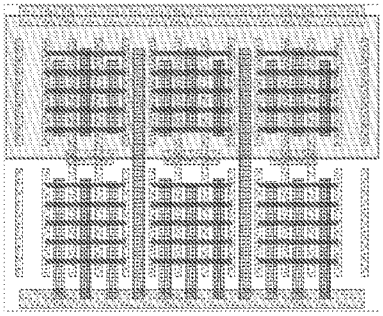
FIG. 1180B
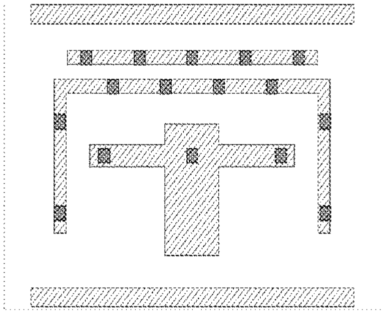
FIG. 1180C

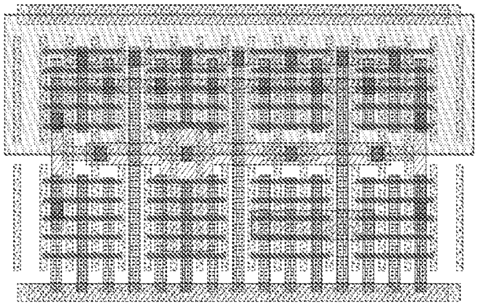
FIG. 1181A
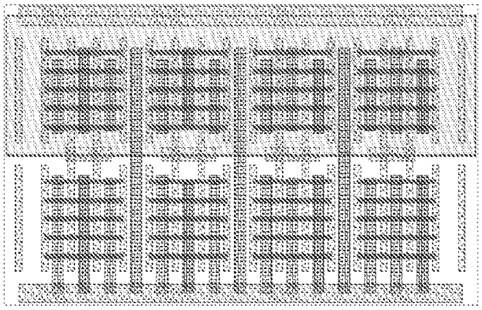
FIG. 1181B
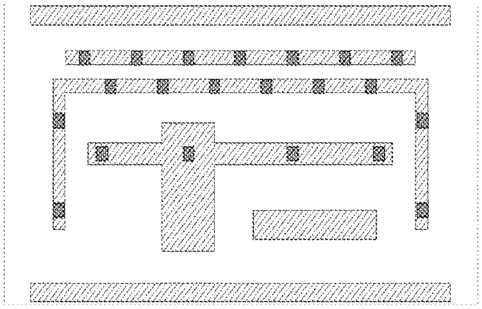
FIG. 1181C
*M* PDF Solutions, Inc.

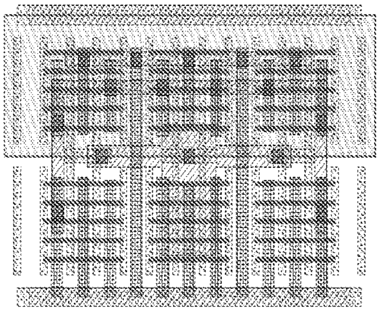
FIG. 1182A
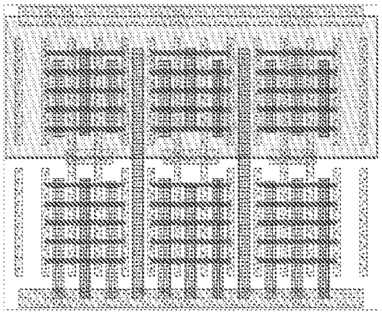
FIG. 1182B
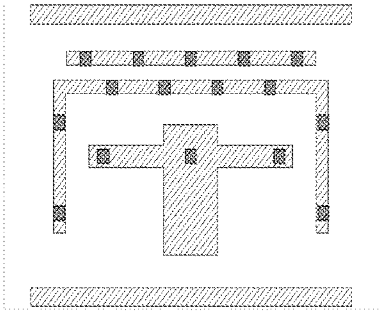
FIG. 1182C

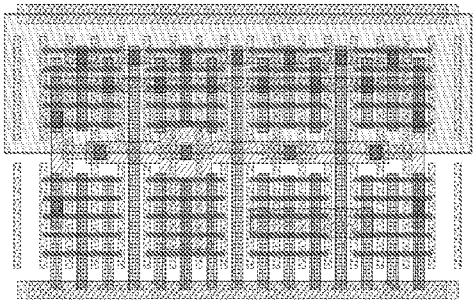
FIG. 1183A
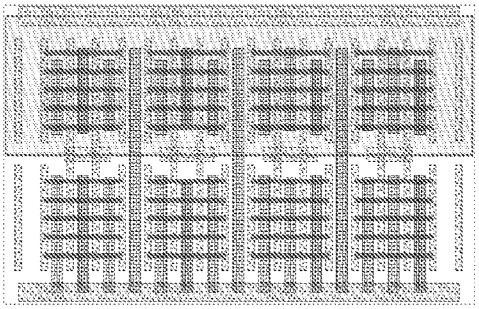
FIG. 1183B
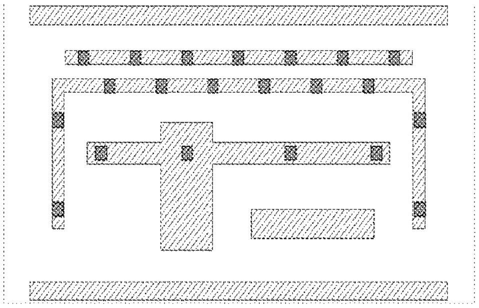
FIG. 1183C

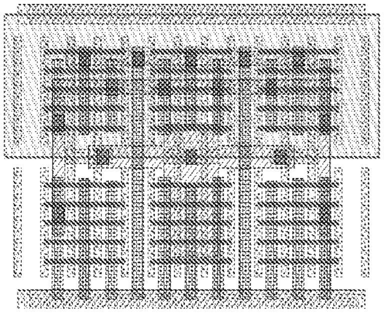
FIG. 1184A
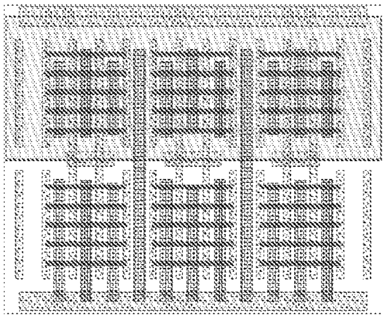
FIG. 1184B
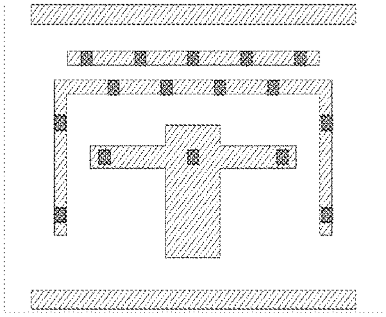
FIG. 1184C

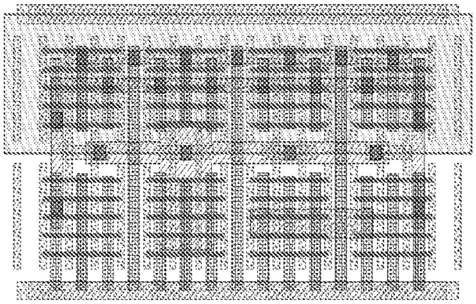
FIG. 1185A
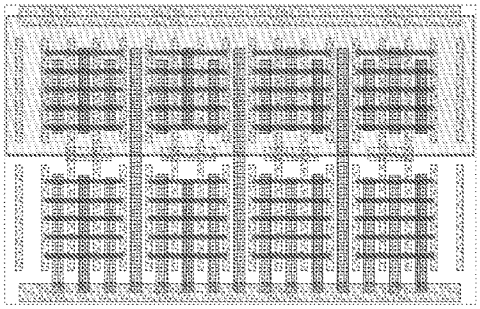
FIG. 1185B
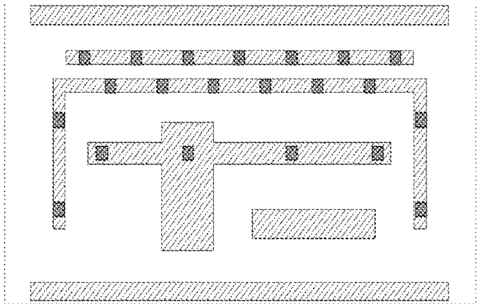
FIG. 1185C

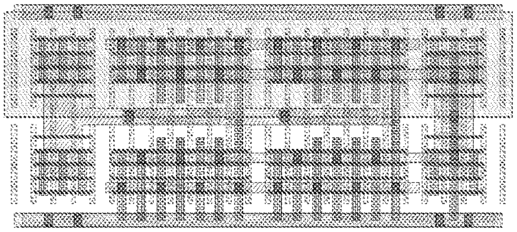
FIG. 1186A
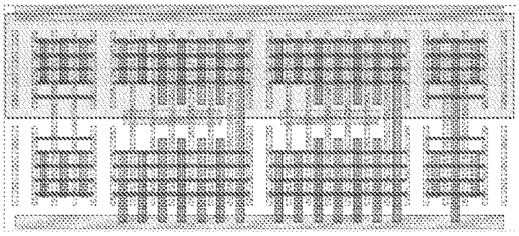
FIG. 1186B
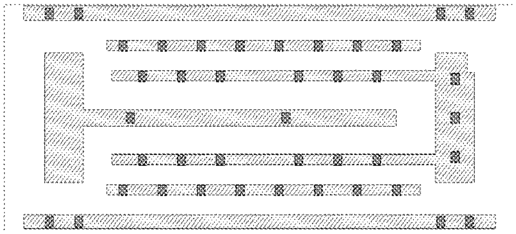
FIG. 1186C

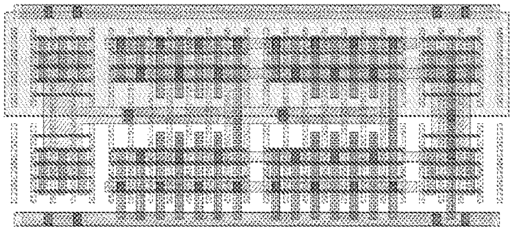
FIG. 1187A
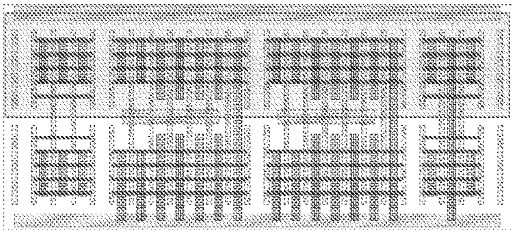
FIG. 1187B
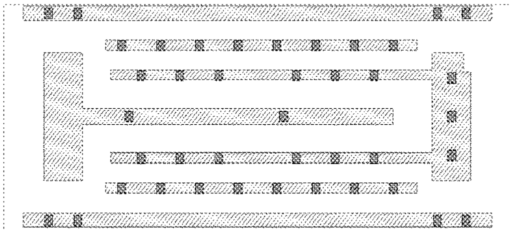
FIG. 1187C

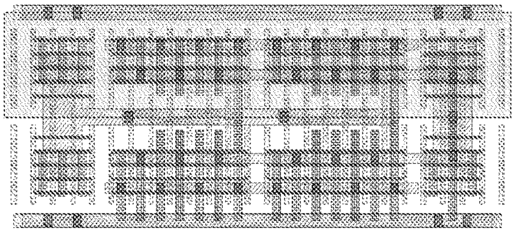
FIG. 1188A
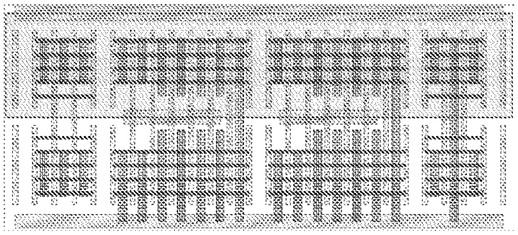
FIG. 1188B
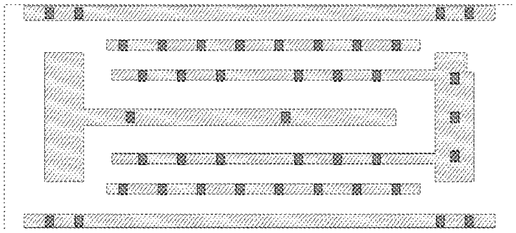
FIG. 1188C

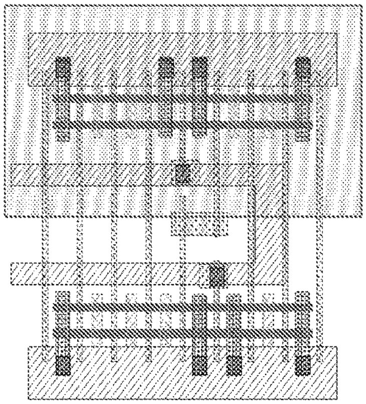
FIG. 1189A
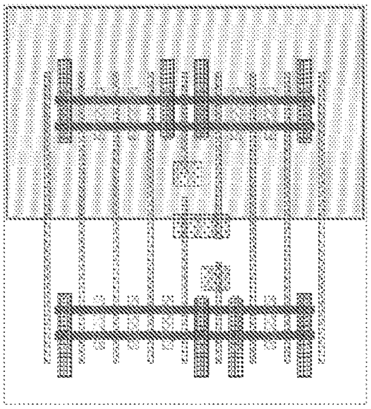
FIG. 1189B
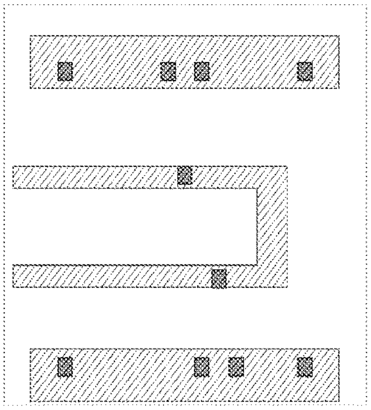
FIG. 1189C

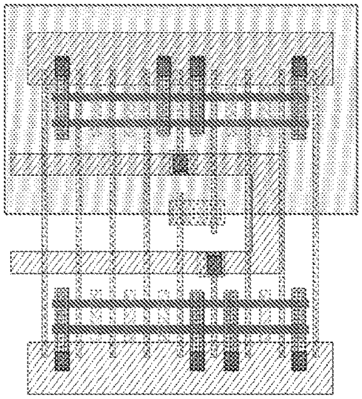
FIG. 1190A
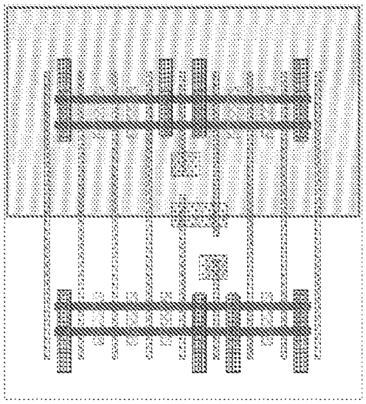
FIG. 1190B
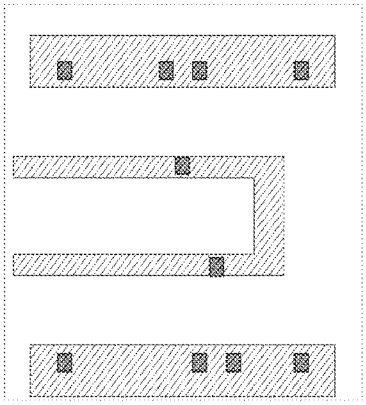
FIG. 1190C
*M* PDF Solutions, Inc.

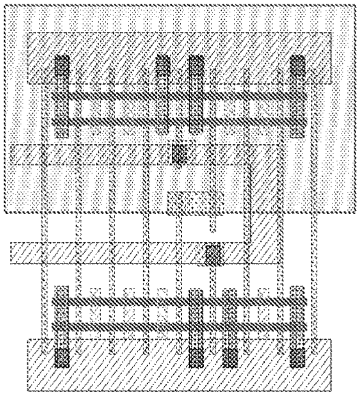
FIG. 1191A
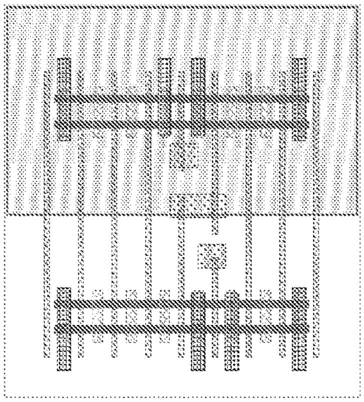
FIG. 1191B
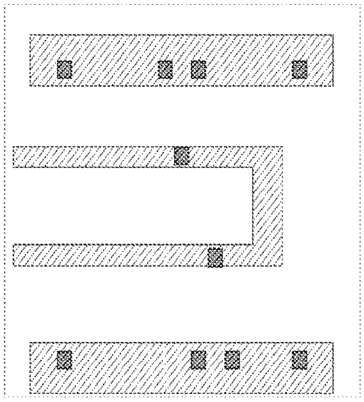
FIG. 1191C

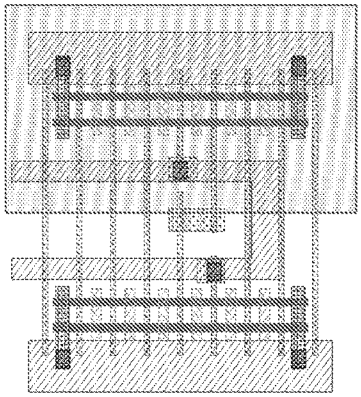
FIG. 1192A
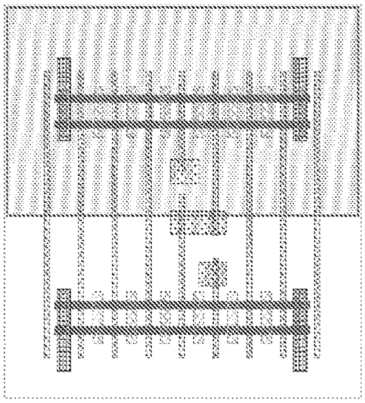
FIG. 1192B
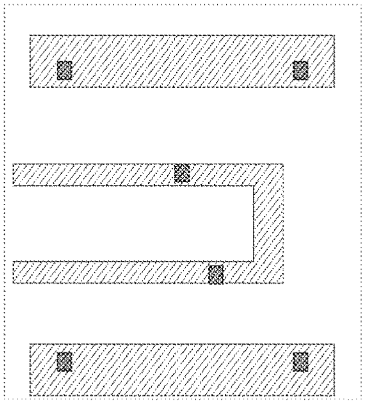
FIG. 1192C

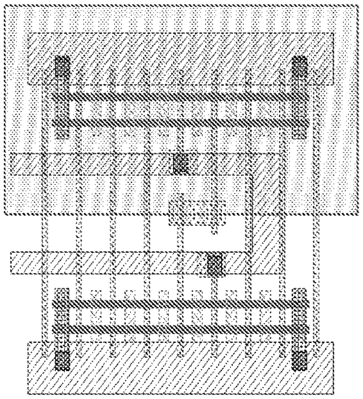
FIG. 1193A
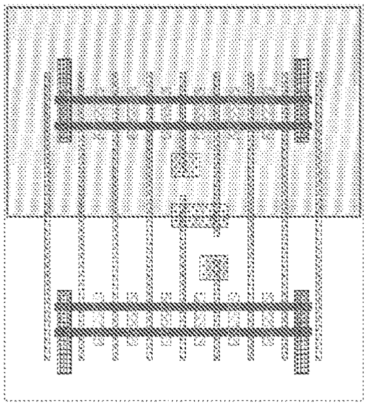
FIG. 1193B
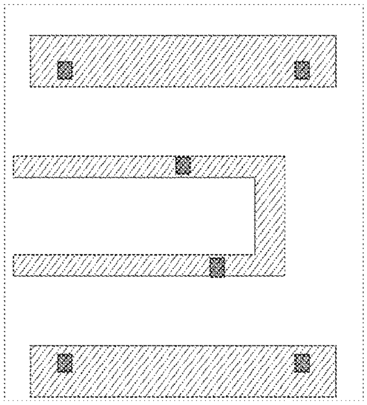
FIG. 1193C
*M* PDF Solutions, Inc.

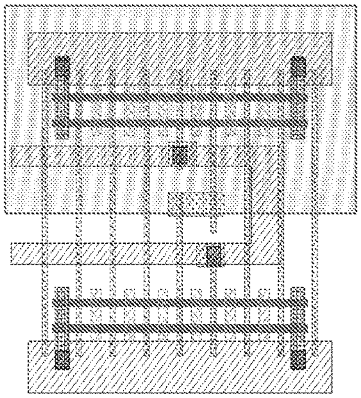
FIG. 1194A
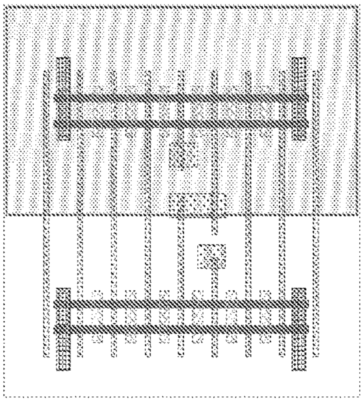
FIG. 1194B
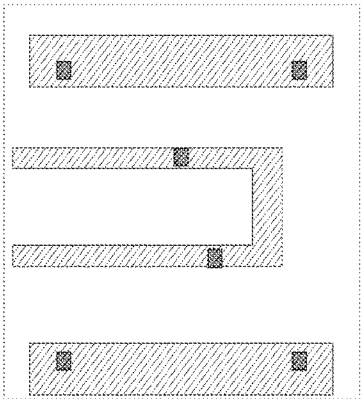
FIG. 1194C

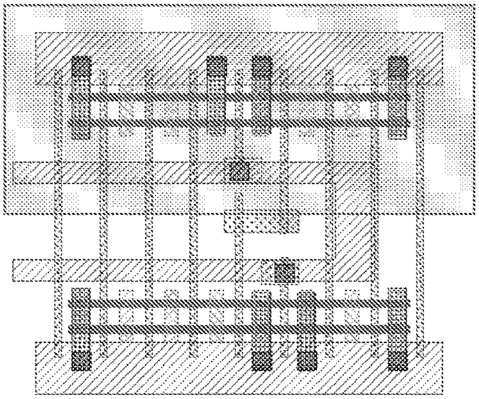
FIG. 1195A
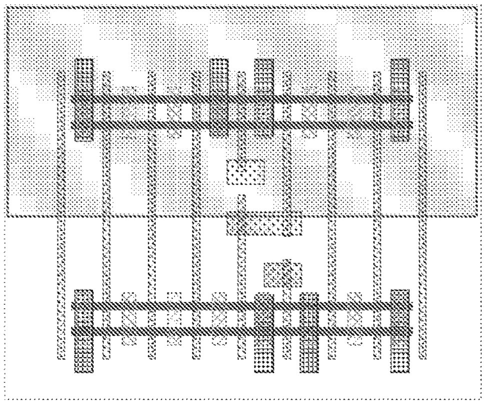
FIG. 1195B
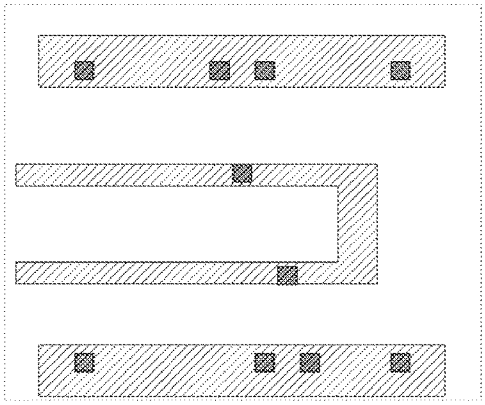
FIG. 1195C

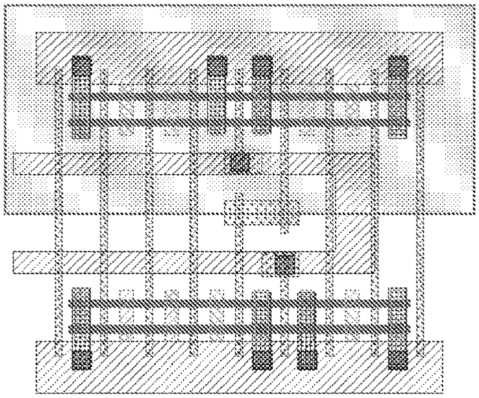
FIG. 1196A
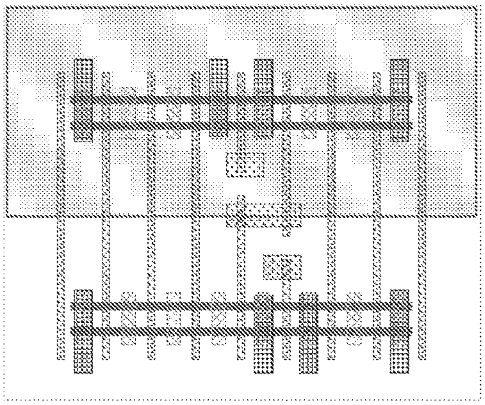
FIG. 1196B
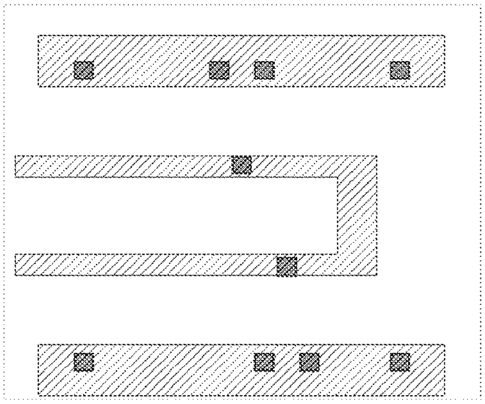
FIG. 1196C

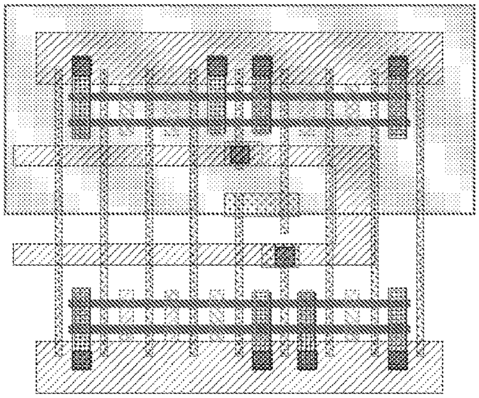
FIG. 1197A
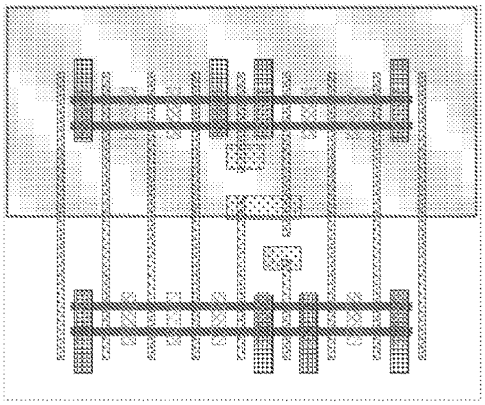
FIG. 1197B
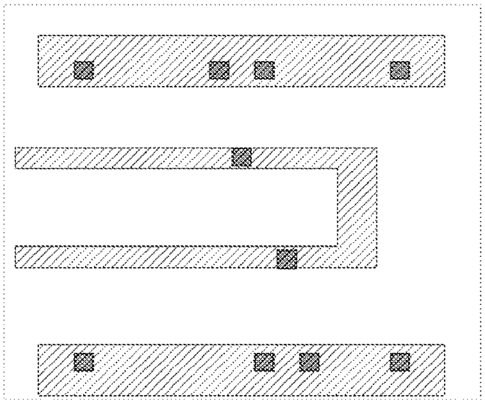
FIG. 1197C
*M* PDF Solutions, Inc.

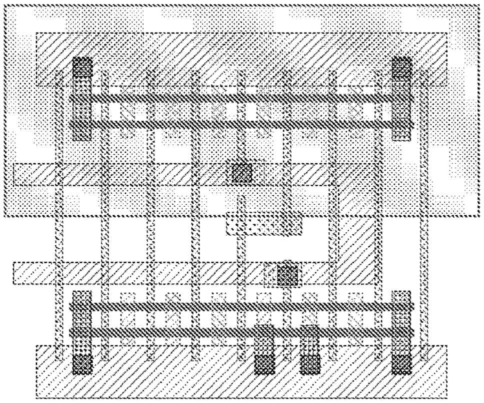
FIG. 1198A
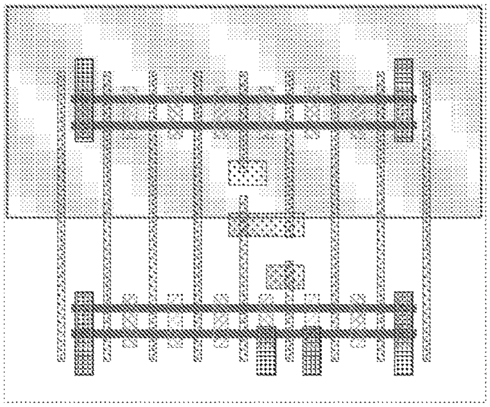
FIG. 1198B
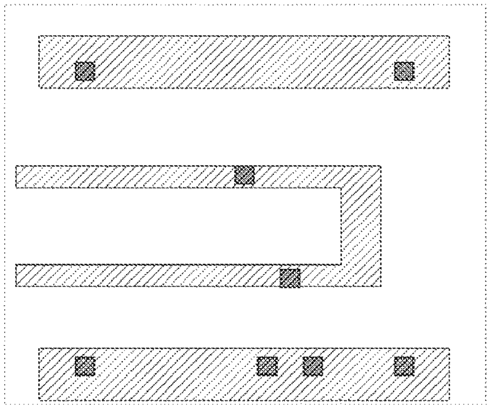
FIG. 1198C

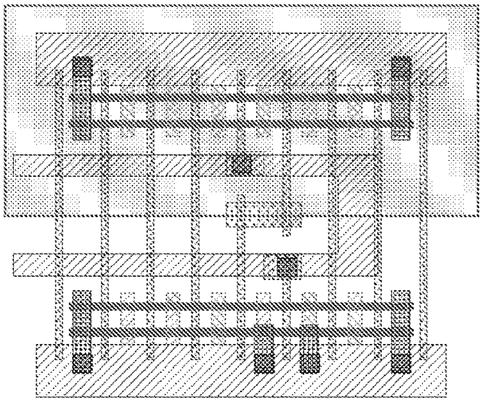
FIG. 1199A
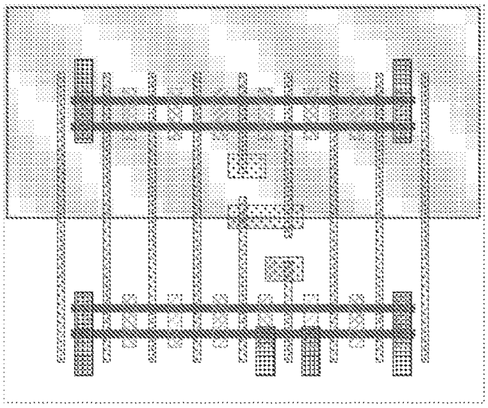
FIG. 1199B
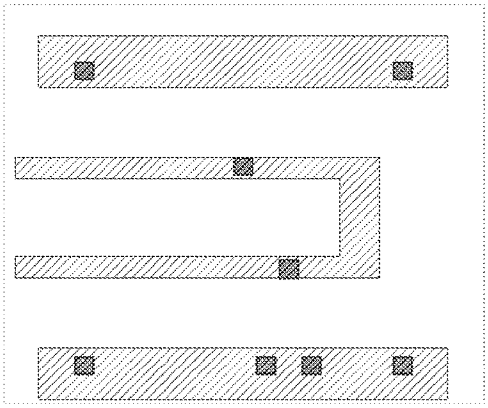
FIG. 1199C
*M* PDF Solutions, Inc.

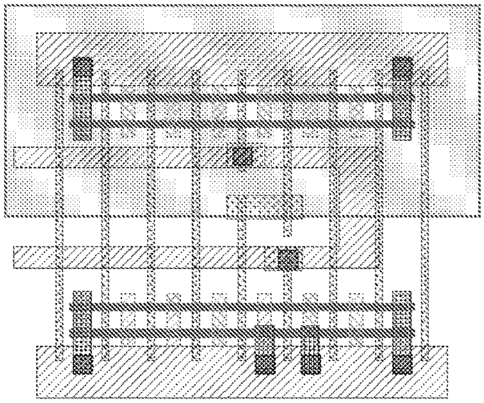
FIG. 1200A
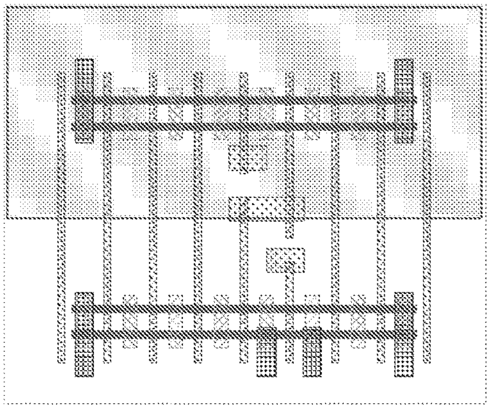
FIG. 1200B
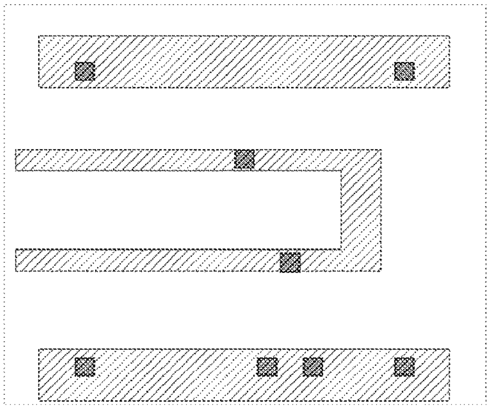
FIG. 1200C
*M* PDF Solutions, Inc.

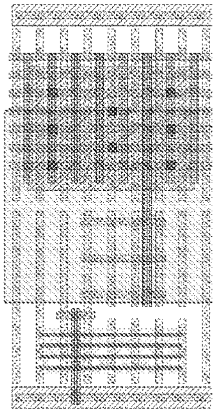
FIG. 1201A
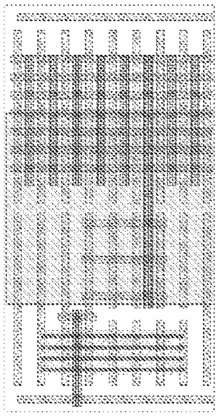
FIG. 1201B
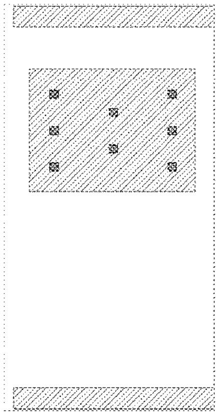
FIG. 1201C

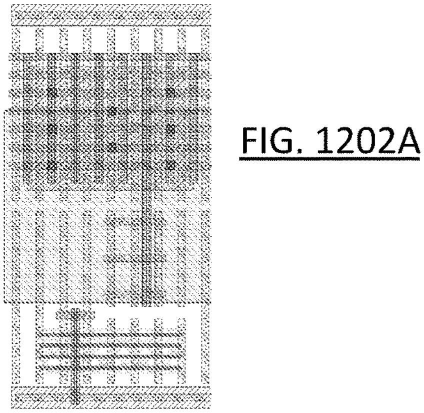
FIG. 1202A
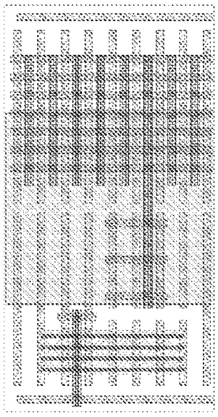
FIG. 1202B
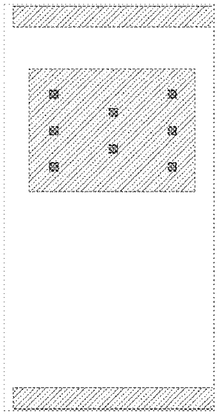
FIG. 1202C

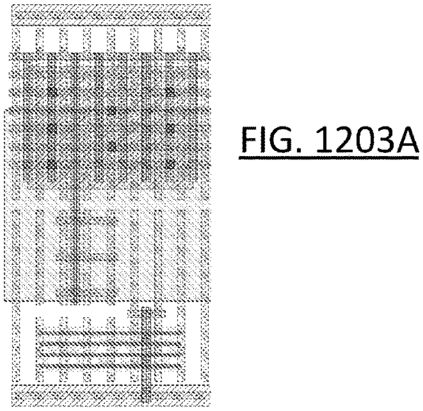
FIG. 1203A
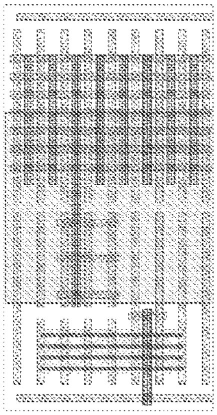
FIG. 1203B
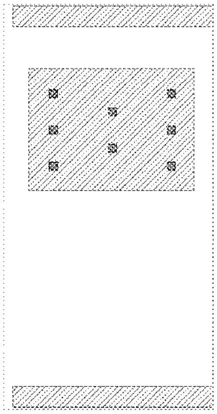
FIG. 1203C
*M* PDF Solutions, Inc.

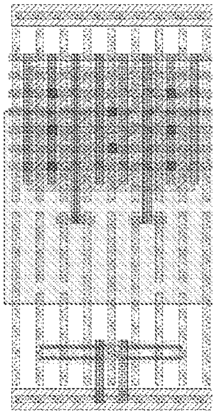
FIG. 1204A
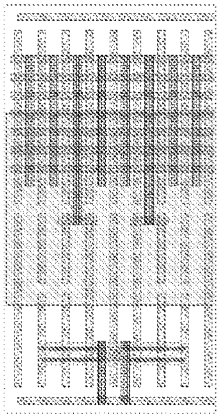
FIG. 1204B
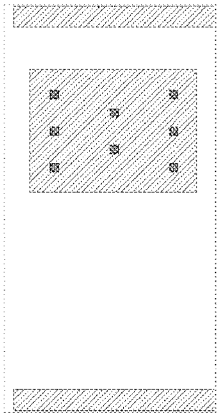
FIG. 1204C

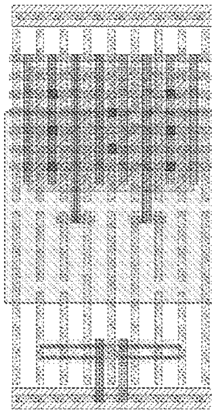
FIG. 1205A
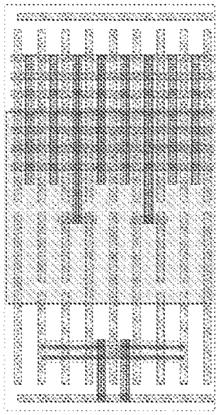
FIG. 1205B
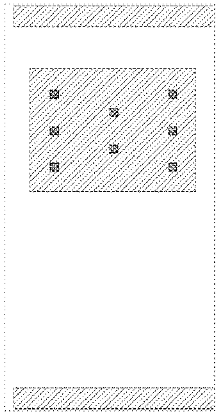
FIG. 1205C

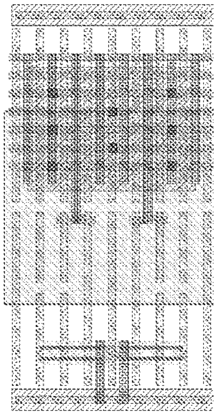
FIG. 1206A
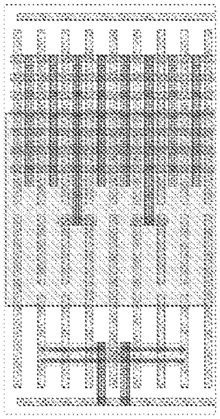
FIG. 1206B
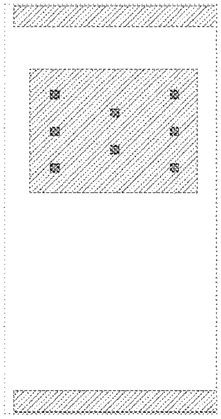
FIG. 1206C

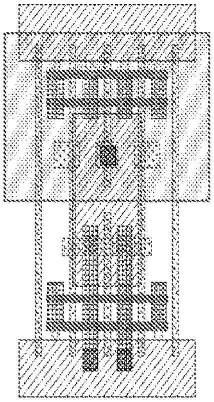
FIG. 1207A
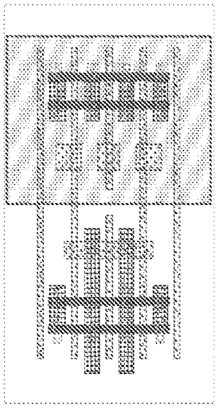
FIG. 1207B
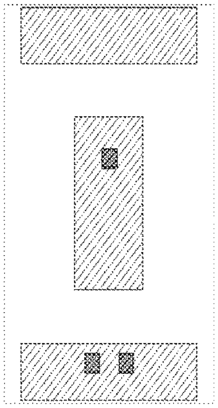
FIG. 1207C

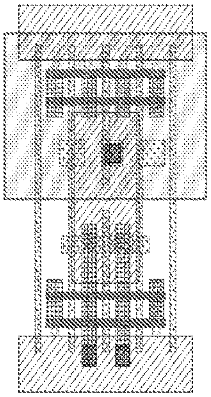
FIG. 1208A
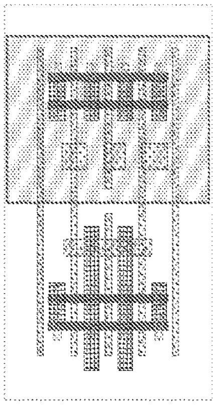
FIG. 1208B
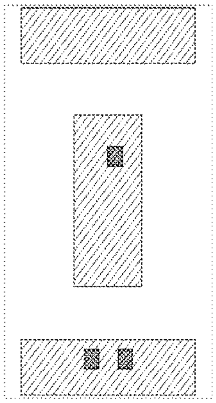
FIG. 1208C

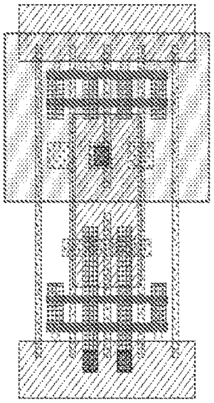
FIG. 1209A
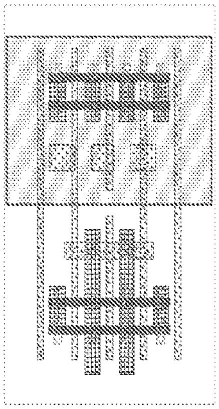
FIG. 1209B
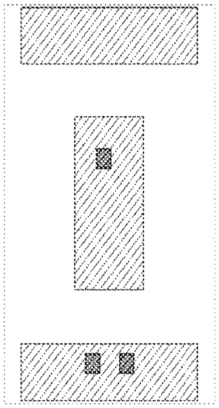
FIG. 1209C

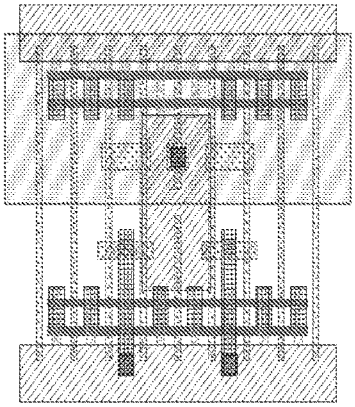
FIG. 1210A
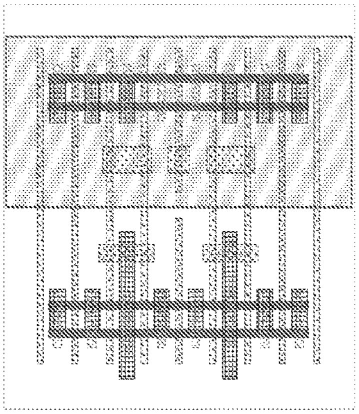
FIG. 1210B
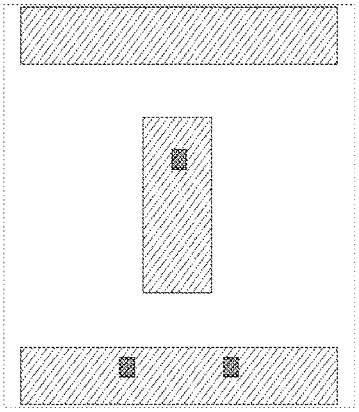
FIG. 1210C
*M* PDF Solutions, Inc.

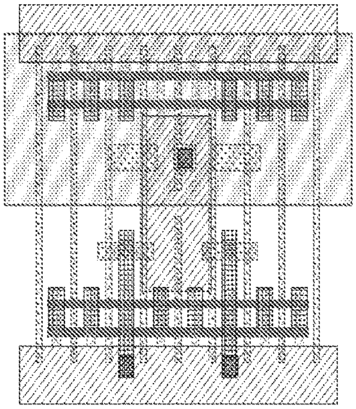
FIG. 1211A
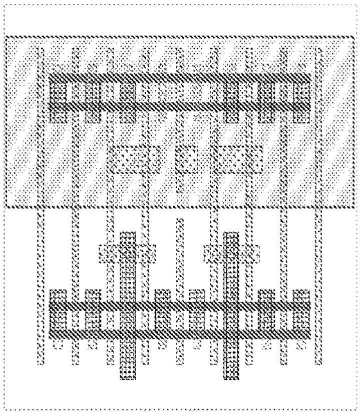
FIG. 1211B
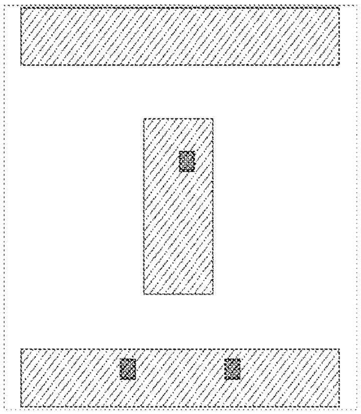
FIG. 1211C
*M* PDF Solutions, Inc.

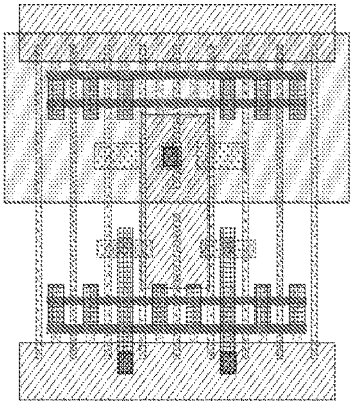
FIG. 1212A
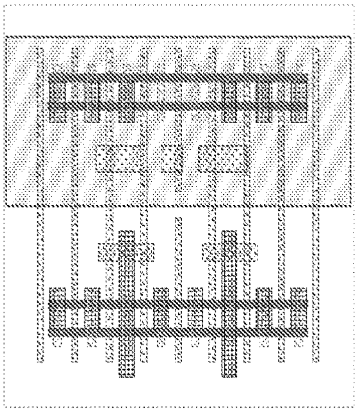
FIG. 1212B
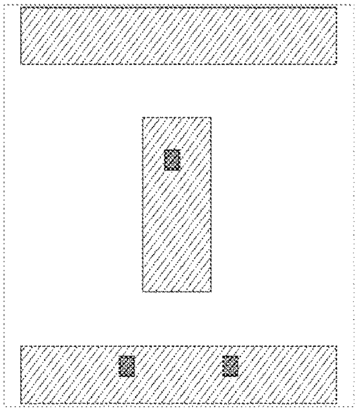
FIG. 1212C

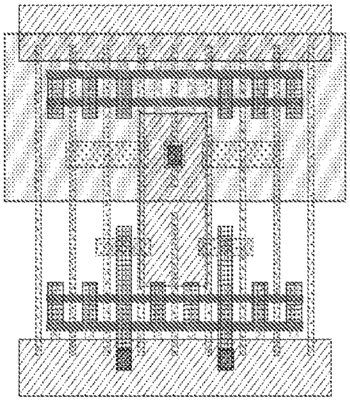
FIG. 1213A
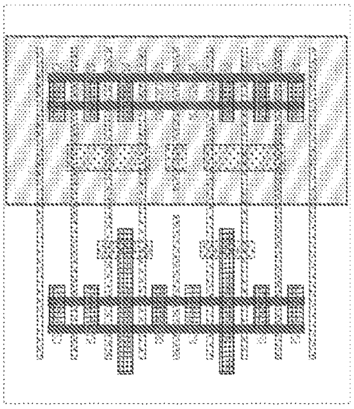
FIG. 1213B
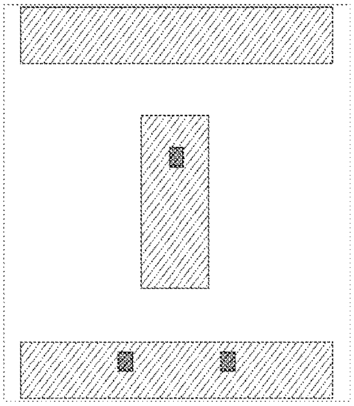
FIG. 1213C
*M* PDF Solutions, Inc.

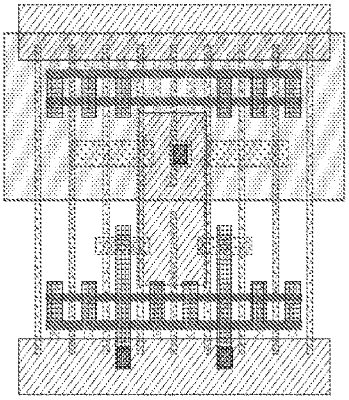
FIG. 1214A
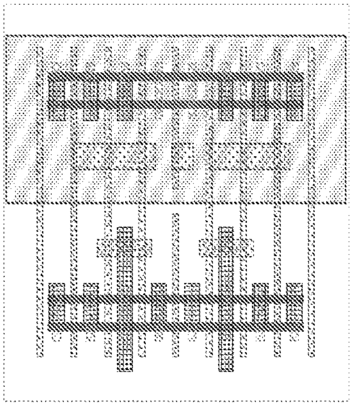
FIG. 1214B
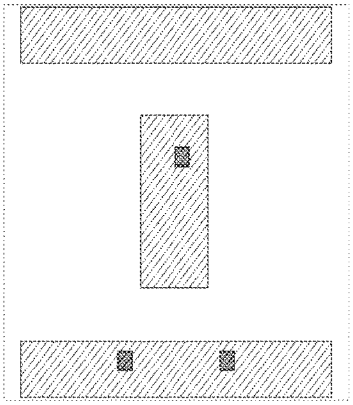
FIG. 1214C

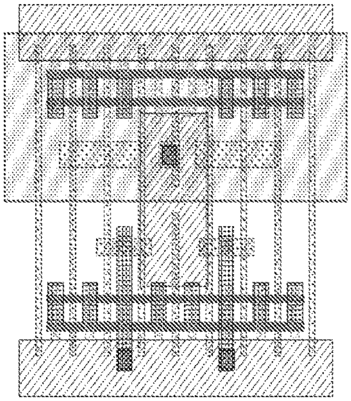
FIG. 1215A
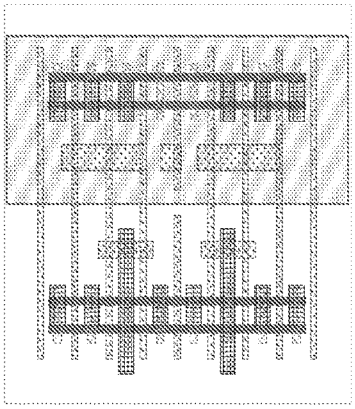
FIG. 1215B
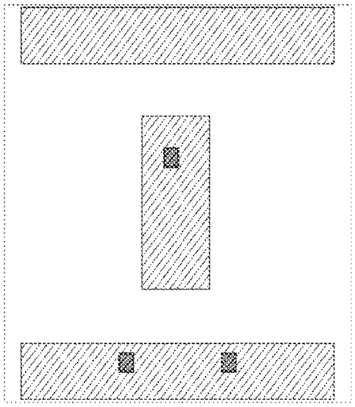
FIG. 1215C
*M* PDF Solutions, Inc.

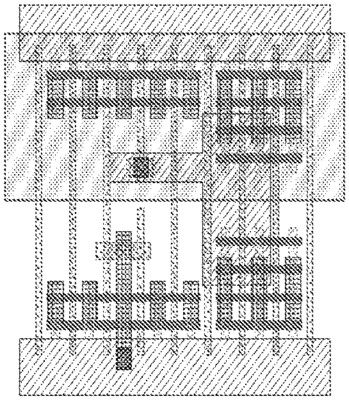
FIG. 1216A
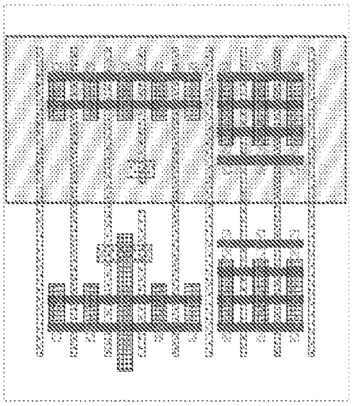
FIG. 1216B
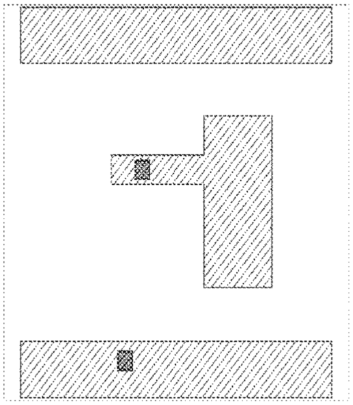
FIG. 1216C
*M* PDF Solutions, Inc.

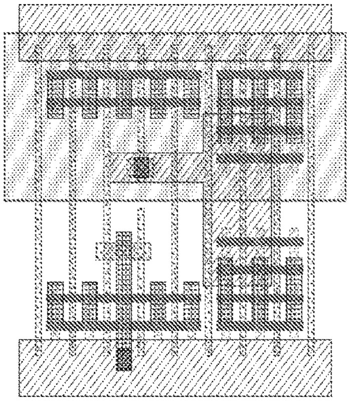
FIG. 1217A
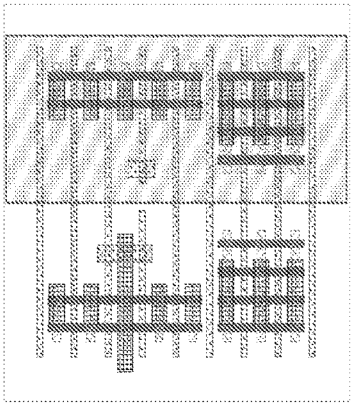
FIG. 1217B
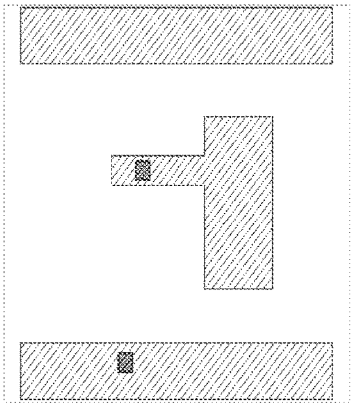
FIG. 1217C

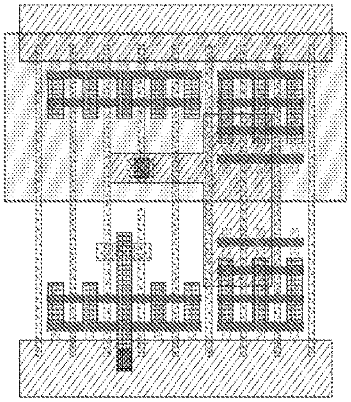
FIG. 1218A
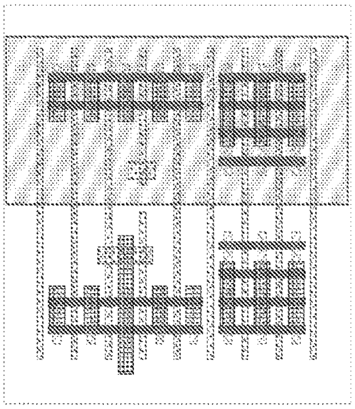
FIG. 1218B
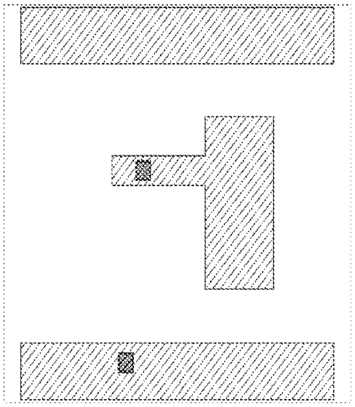
FIG. 1218C

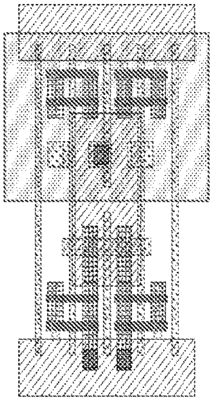
FIG. 1219A
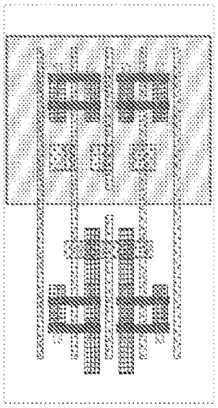
FIG. 1219B
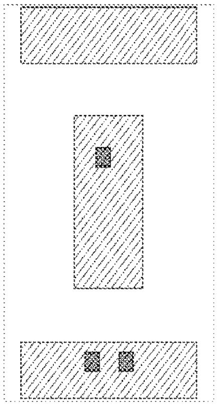
FIG. 1219C

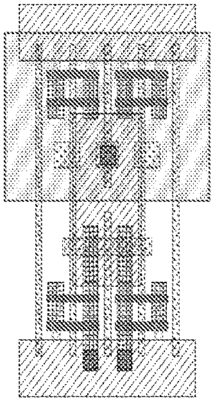
FIG. 1220A
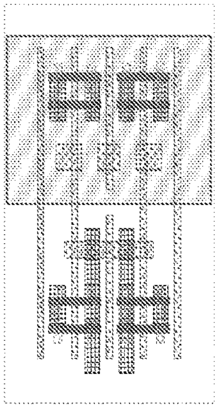
FIG. 1220B
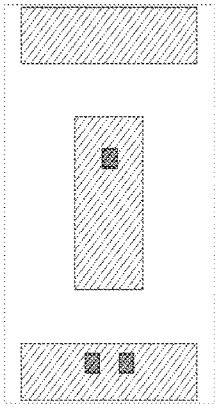
FIG. 1220C

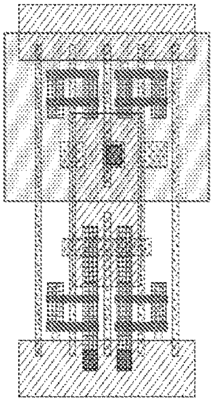
FIG. 1221A
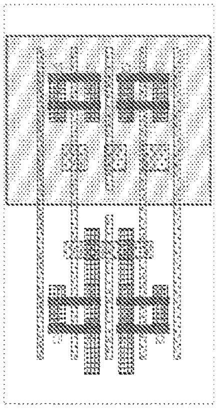
FIG. 1221B
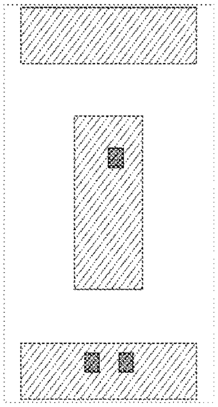
FIG. 1221C
*M* PDF Solutions, Inc.

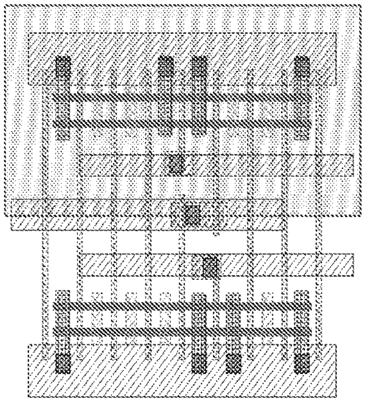
FIG. 1222A
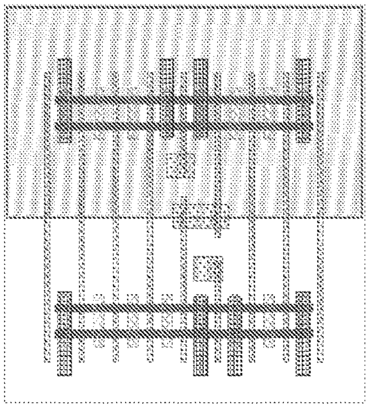
FIG. 1222B
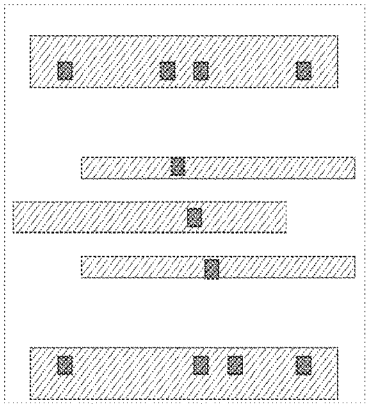
FIG. 1222C

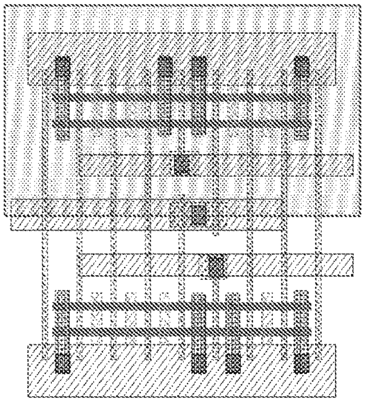
FIG. 1223A
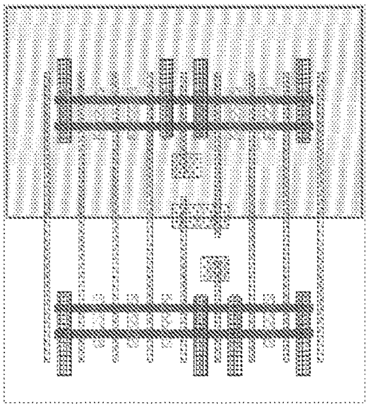
FIG. 1223B
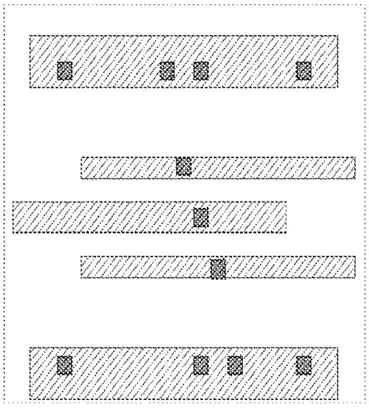
FIG. 1223C

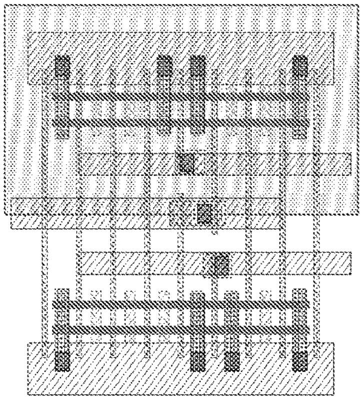
FIG. 1224A
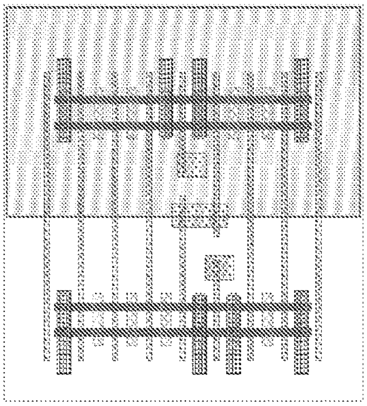
FIG. 1224B
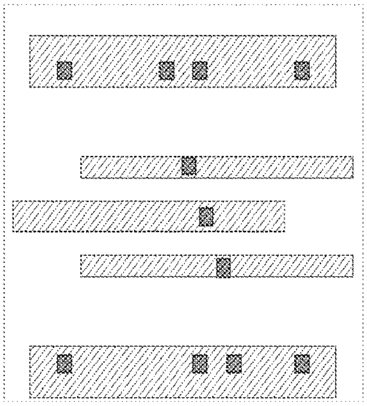
FIG. 1224C

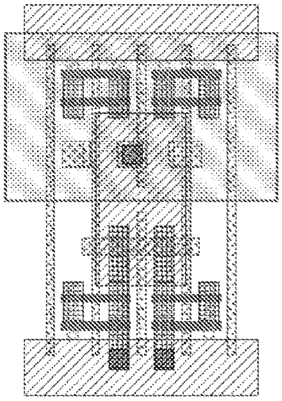
FIG. 1225A
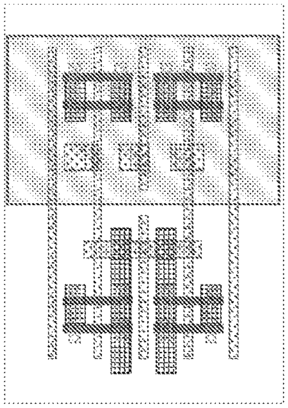
FIG. 1225B
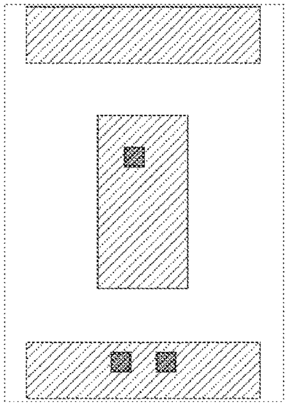
FIG. 1225C
*M* PDF Solutions, Inc.

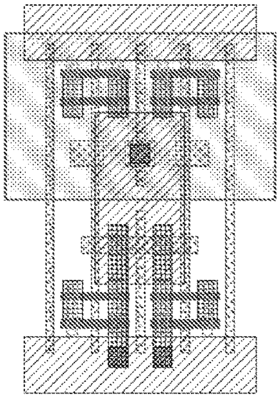
FIG. 1226A
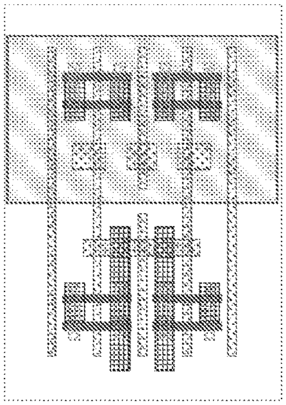
FIG. 1226B
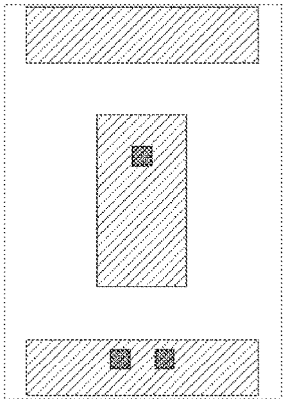
FIG. 1226C

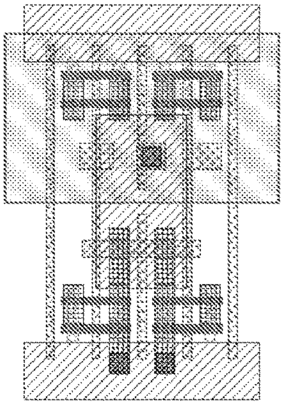
FIG. 1227A
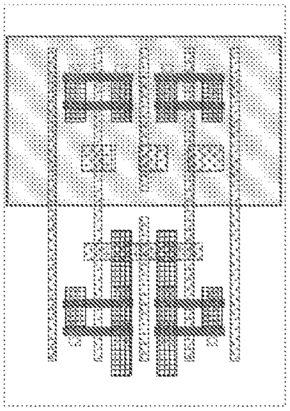
FIG. 1227B
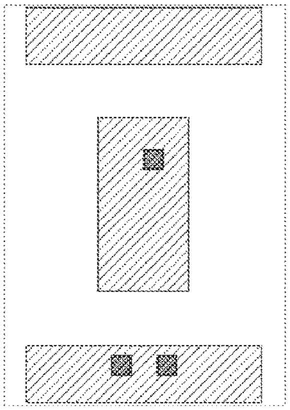
FIG. 1227C
*M* PDF Solutions, Inc.

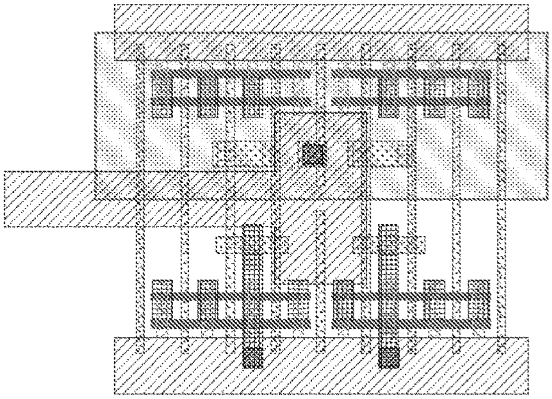
FIG. 1228A
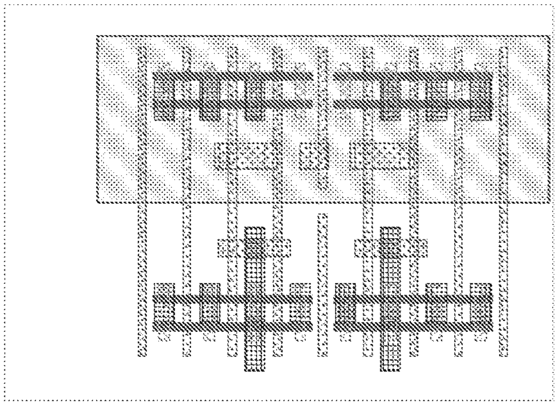
FIG. 1228B
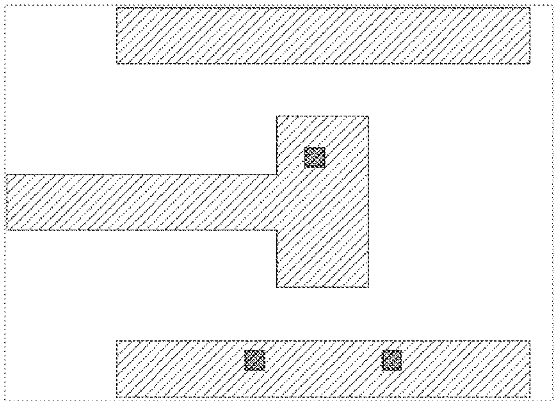
FIG. 1228C

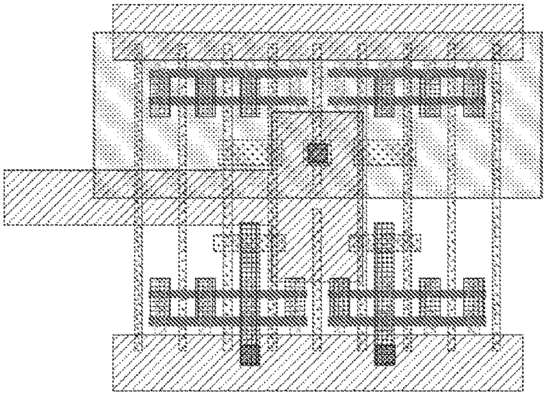
FIG. 1229A
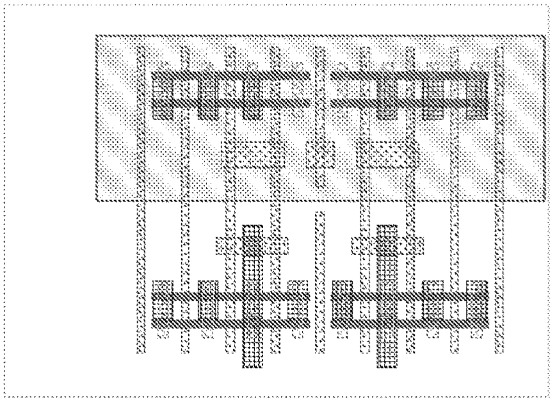
FIG. 1229B
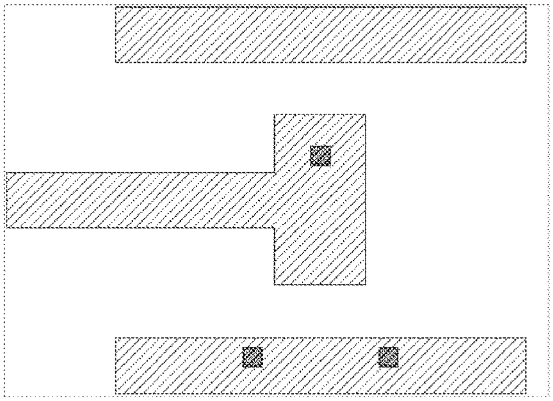
FIG. 1229C
*M* PDF Solutions, Inc.

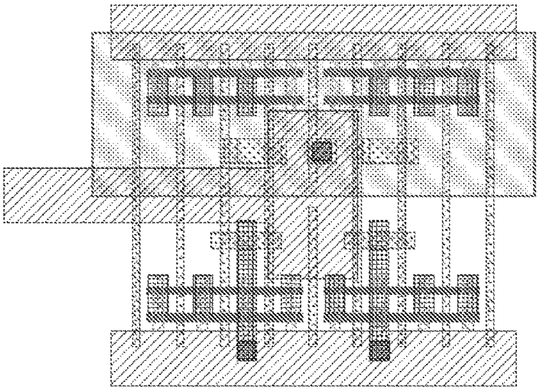
FIG. 1230A
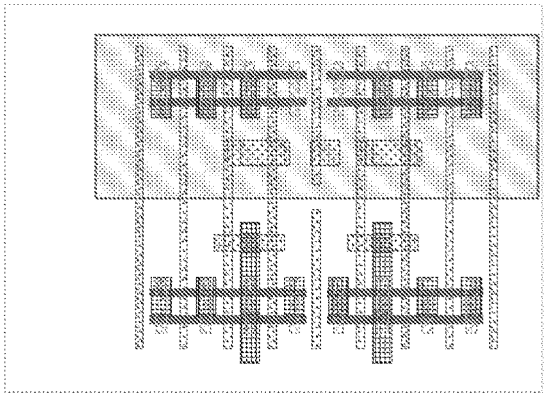
FIG. 1230B
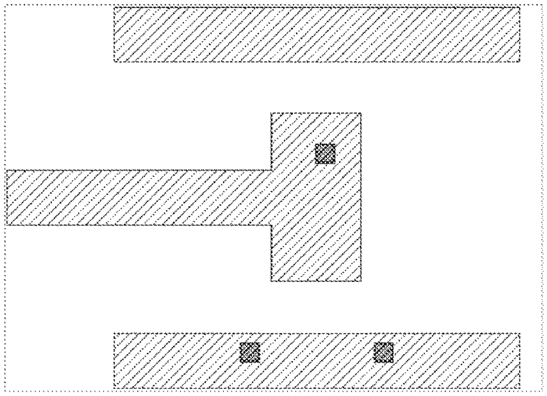
FIG. 1230C

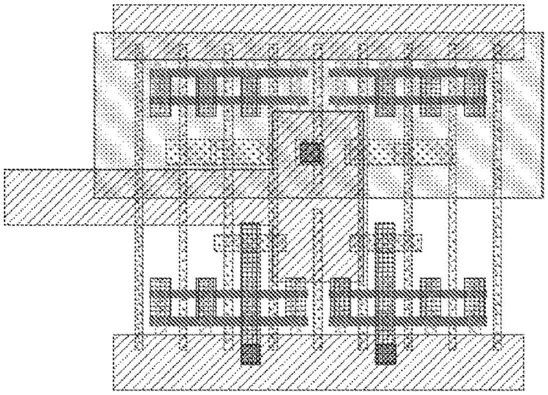
FIG. 1231A
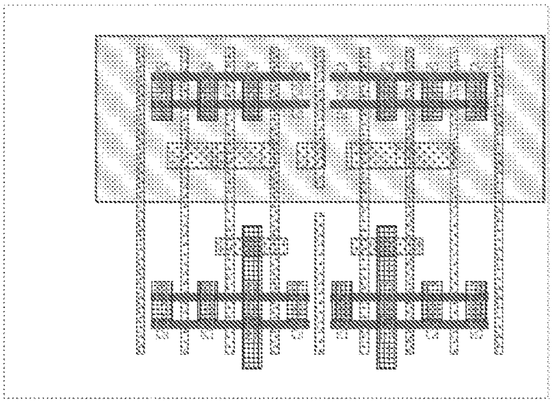
FIG. 1231B
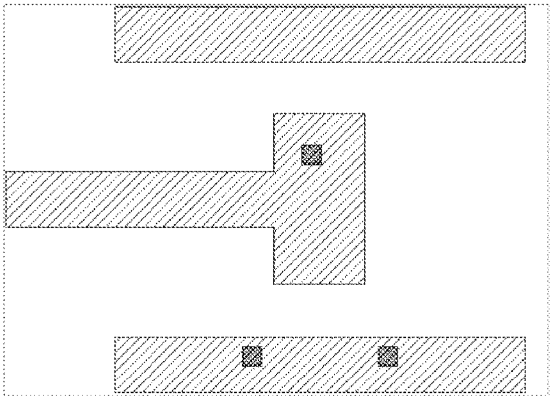
FIG. 1231C

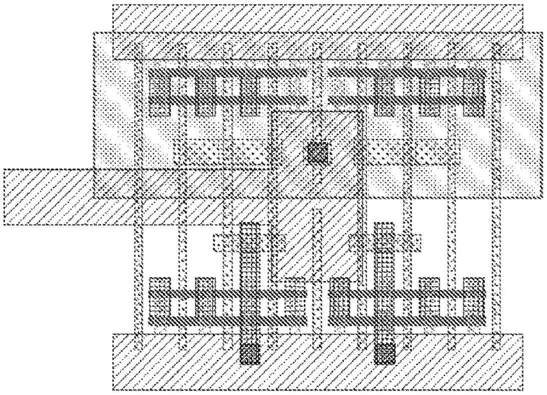
FIG. 1232A
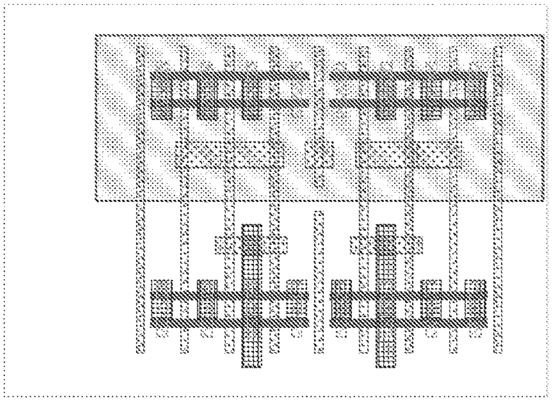
FIG. 1232B
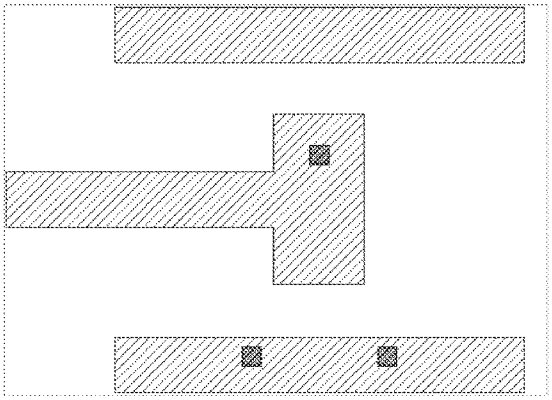
FIG. 1232C

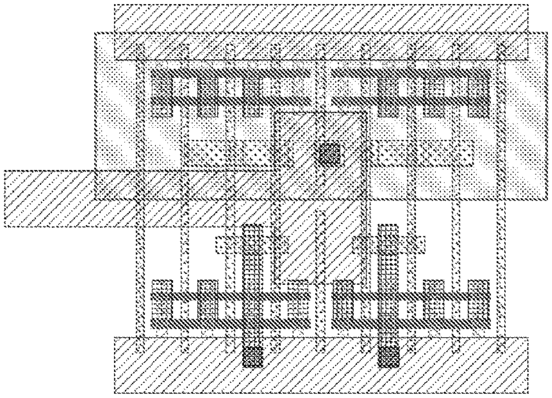
FIG. 1233A
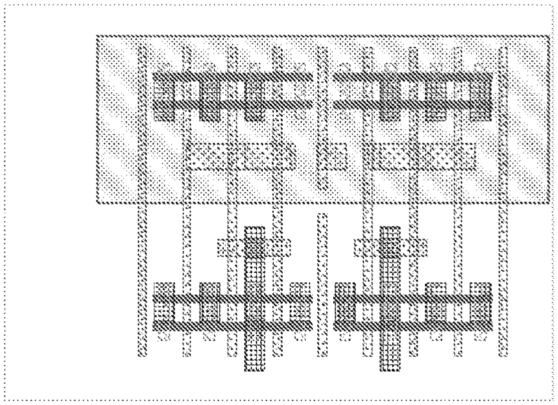
FIG. 1233B
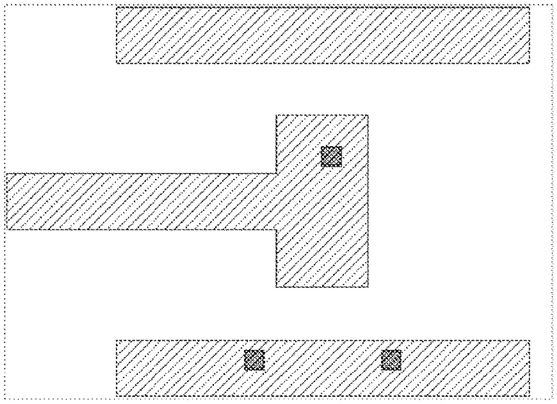
FIG. 1233C

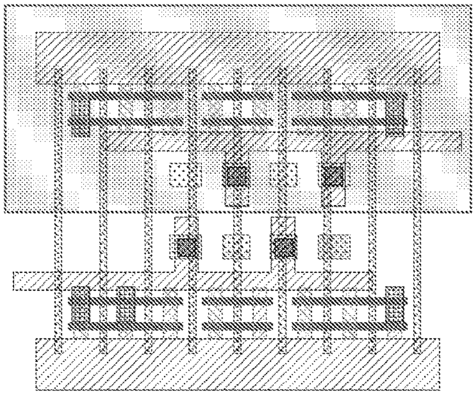
FIG. 1234A
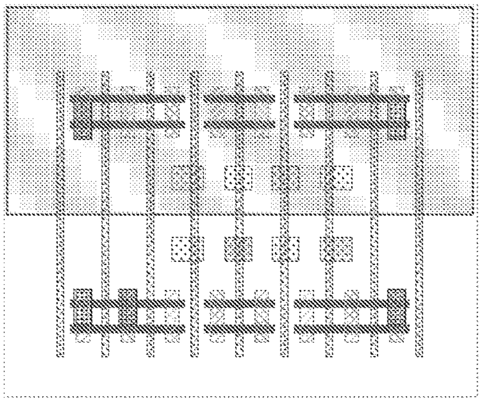
FIG. 1234B
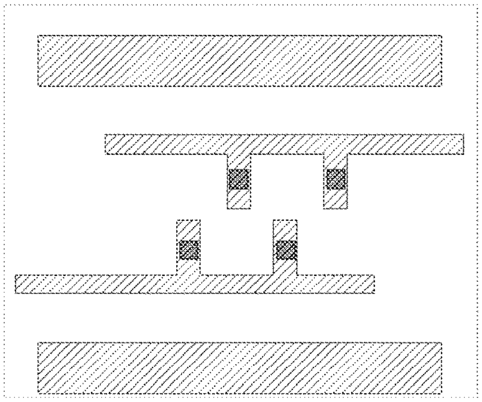
FIG. 1234C

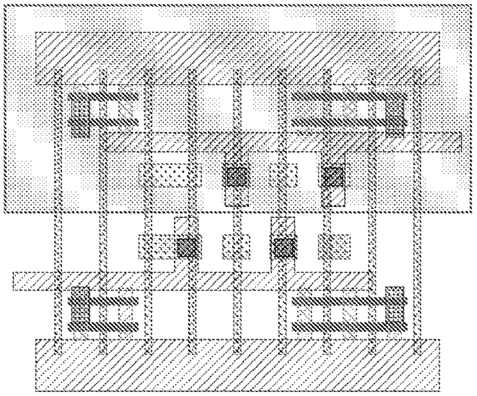
FIG. 1235A
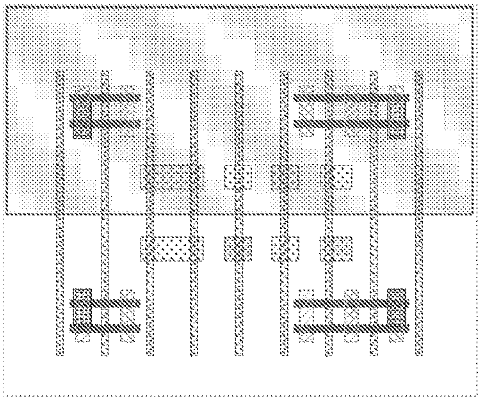
FIG. 1235B
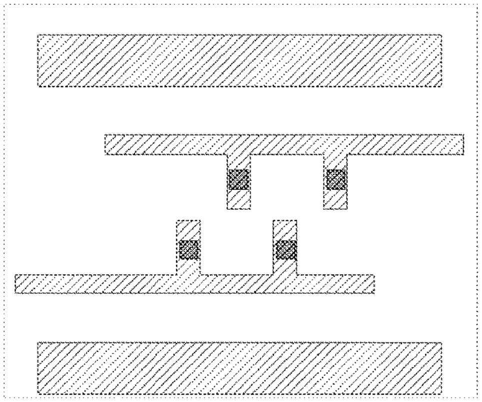
FIG. 1235C

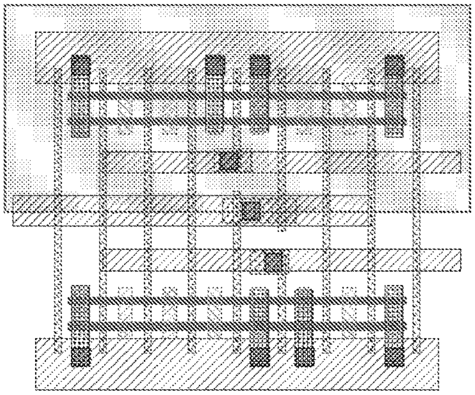
FIG. 1236A
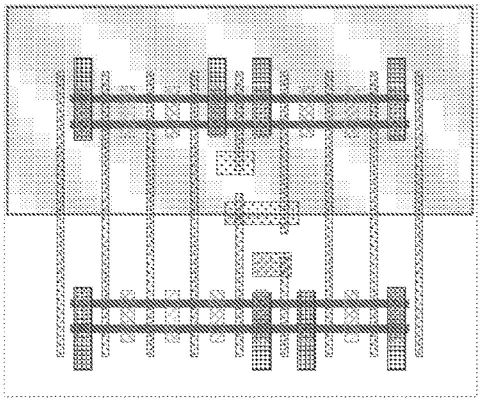
FIG. 1236B
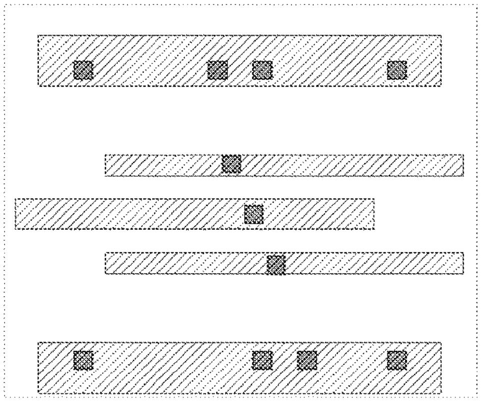
FIG. 1236C
*M* PDF Solutions, Inc.

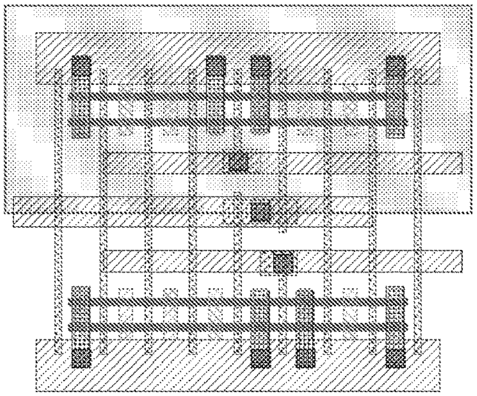
FIG. 1237A
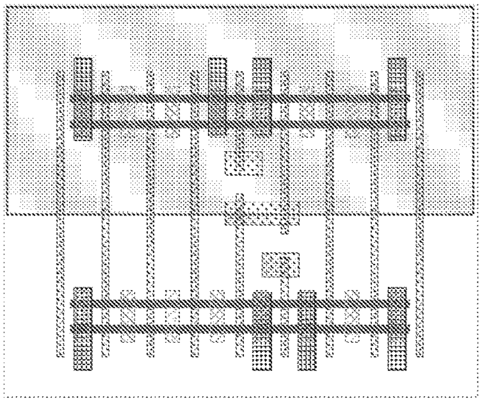
FIG. 1237B
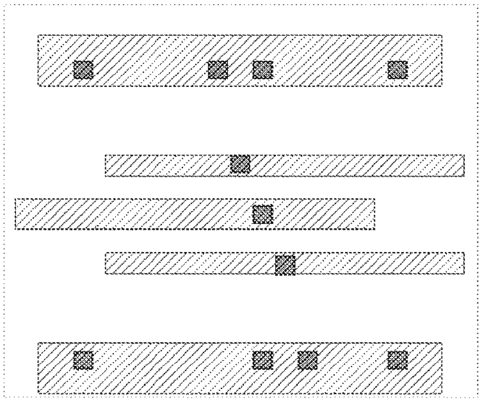
FIG. 1237C
*M* PDF Solutions, Inc.

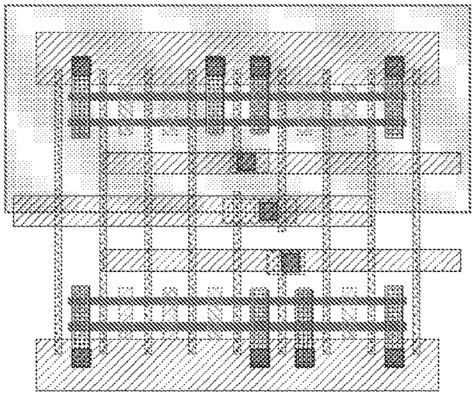
FIG. 1238A
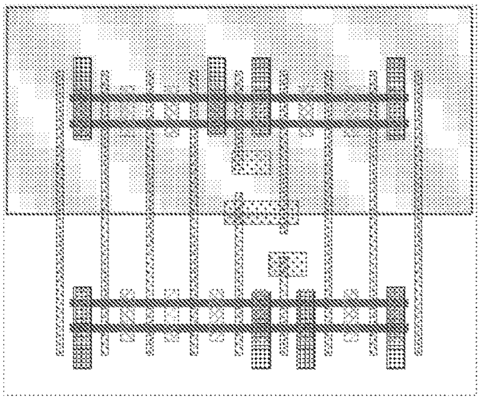
FIG. 1238B
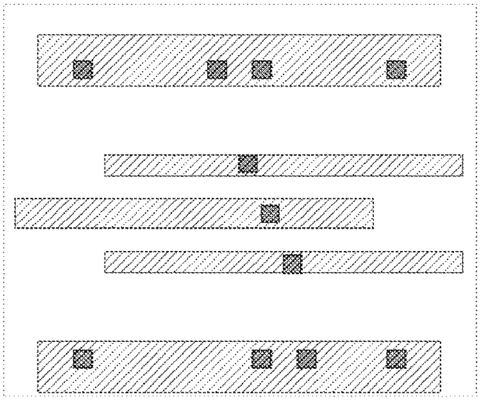
FIG. 1238C

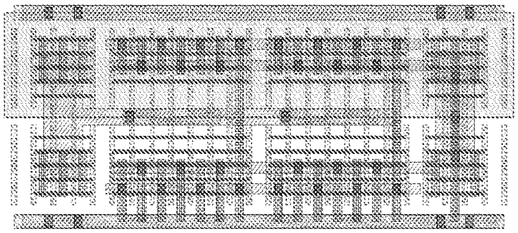
FIG. 1239A
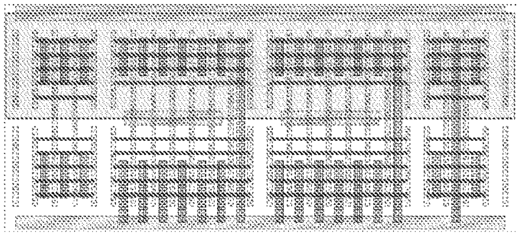
FIG. 1239B
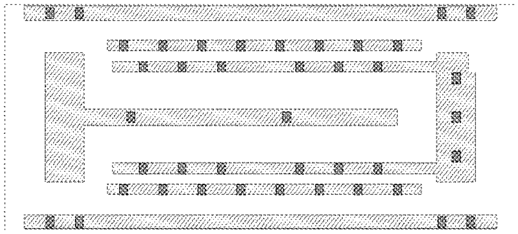
FIG. 1239C
*M* PDF Solutions, Inc.

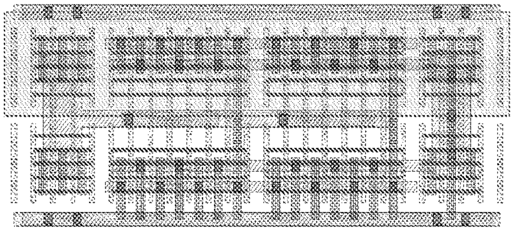
FIG. 1240A
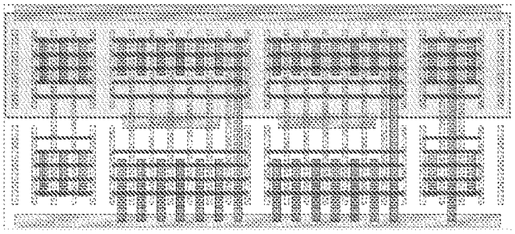
FIG. 1240B
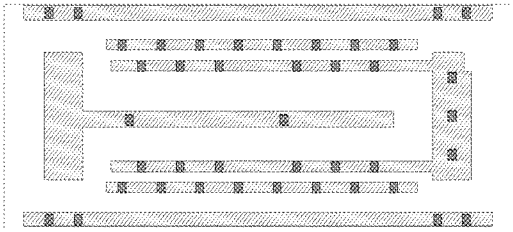
FIG. 1240C

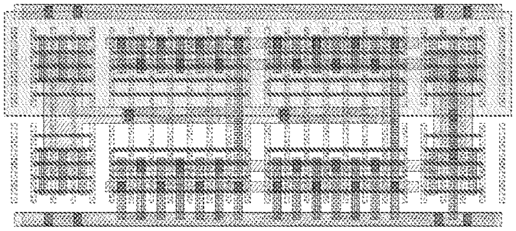
FIG. 1241A
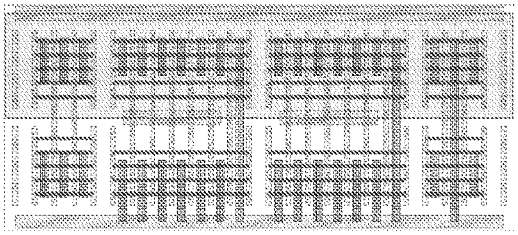
FIG. 1241B
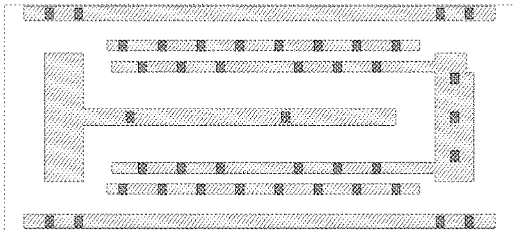
FIG. 1241C

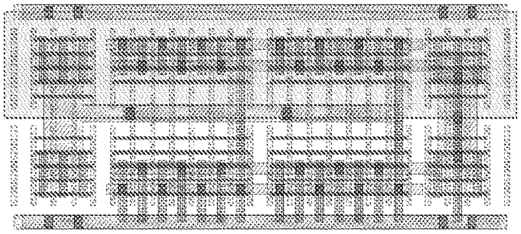
FIG. 1242A
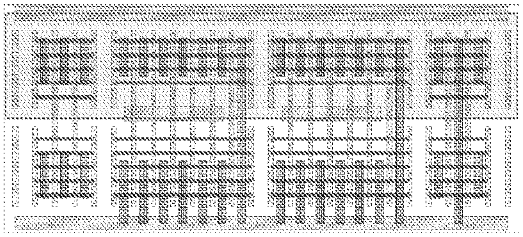
FIG. 1242B
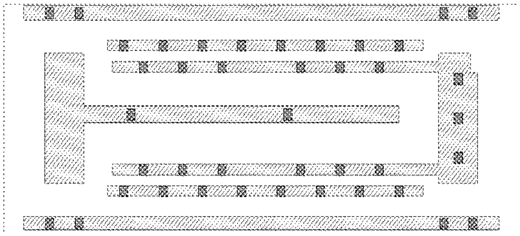
FIG. 1242C
*M* PDF Solutions, Inc.

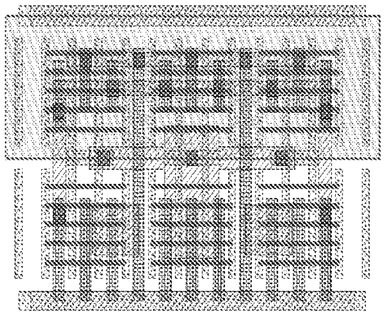
FIG. 1243A
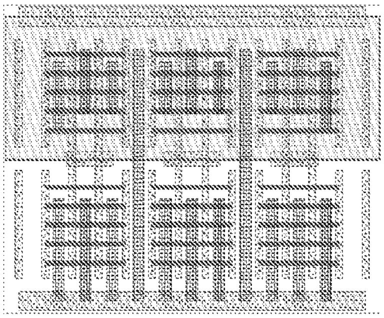
FIG. 1243B
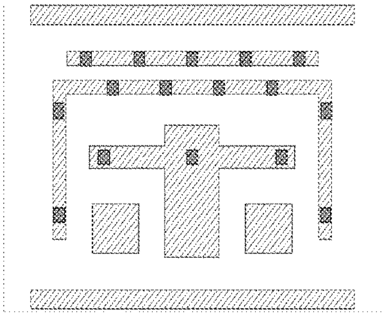
FIG. 1243C
*M* PDF Solutions, Inc.

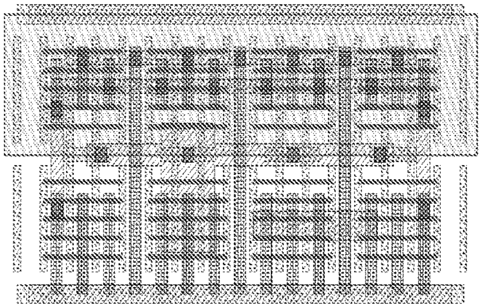
FIG. 1244A
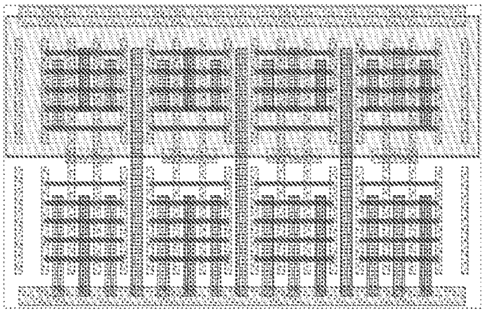
FIG. 1244B
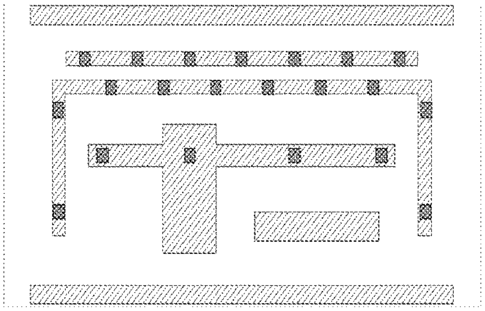
FIG. 1244C

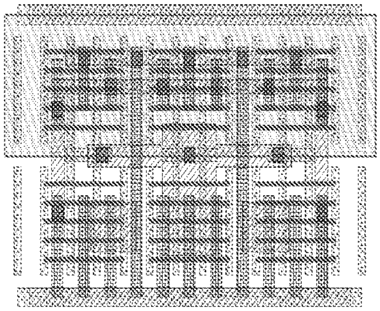
FIG. 1245A
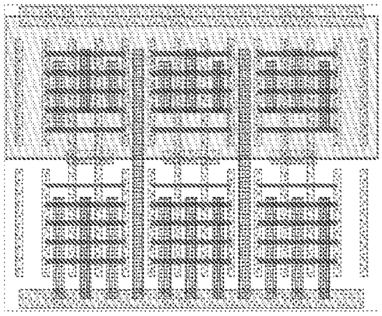
FIG. 1245B
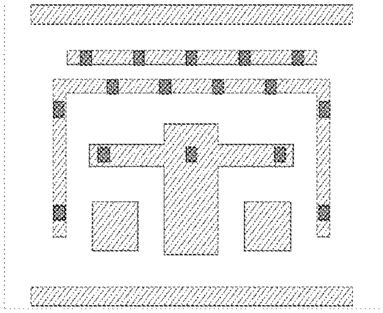
FIG. 1245C

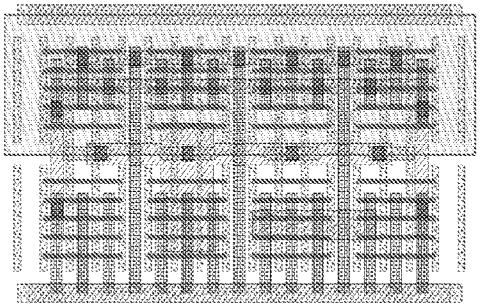
FIG. 1246A
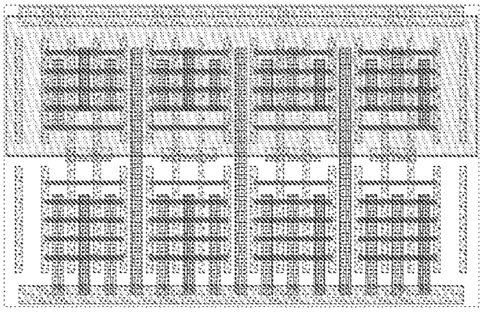
FIG. 1246B
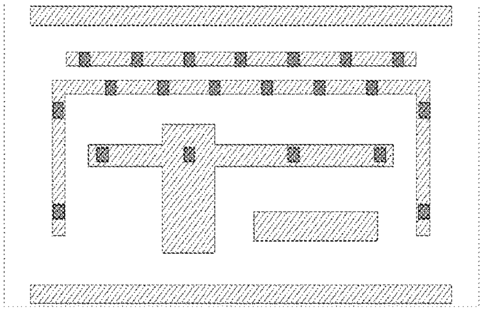
FIG. 1246C

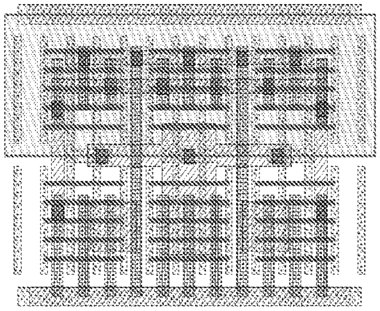
FIG. 1247A
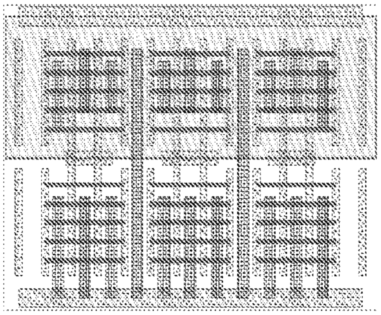
FIG. 1247B
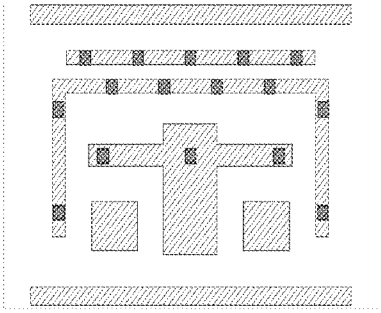
FIG. 1247C

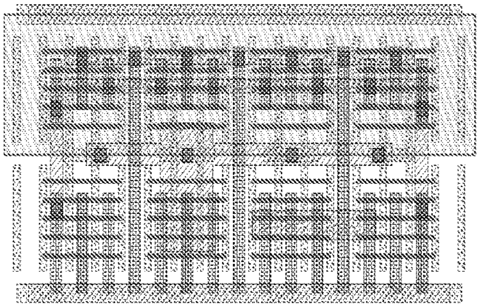
FIG. 1248A
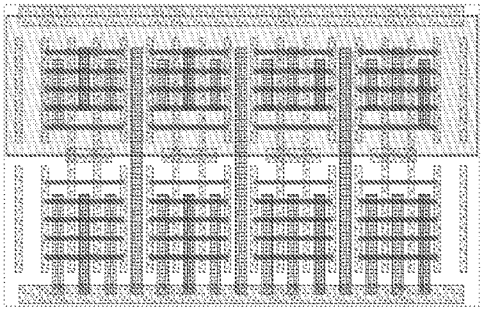
FIG. 1248B
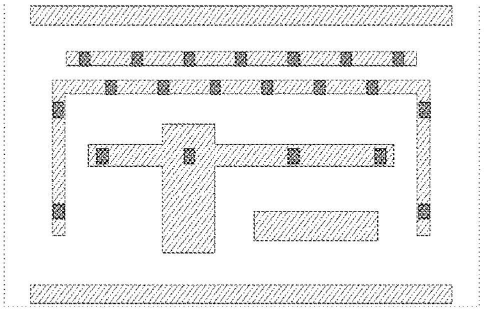
FIG. 1248C
*M* PDF Solutions, Inc.

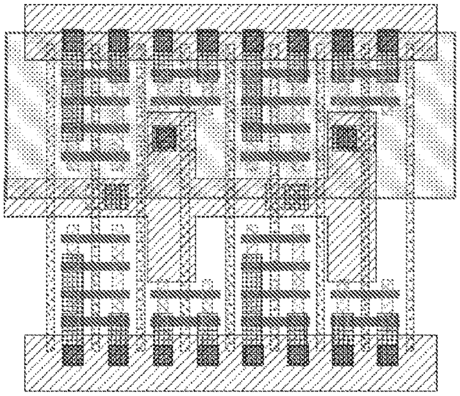
FIG. 1249A
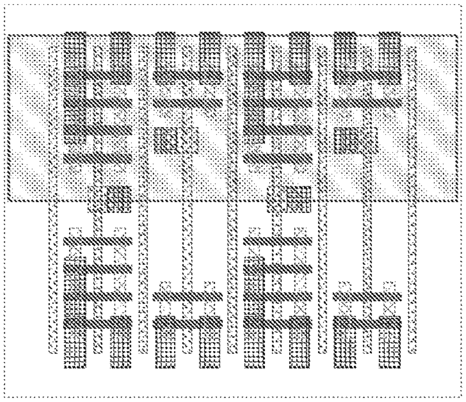
FIG. 1249B
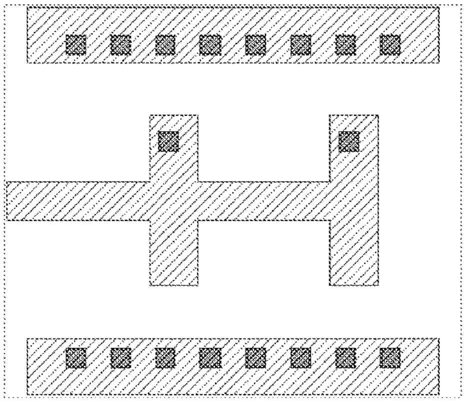
FIG. 1249C
*M* PDF Solutions, Inc.

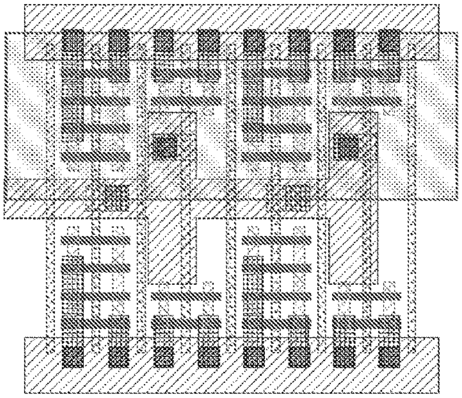
FIG. 1250A
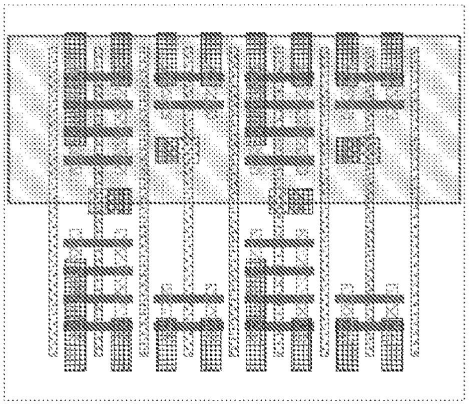
FIG. 1250B
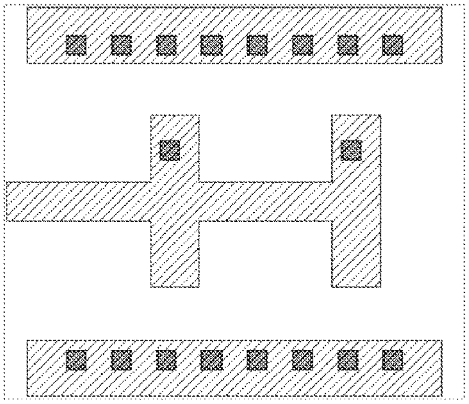
FIG. 1250C

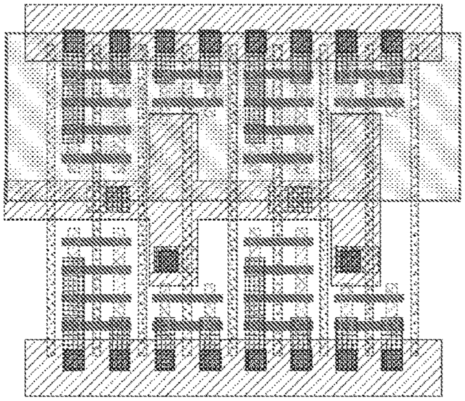
FIG. 1251A
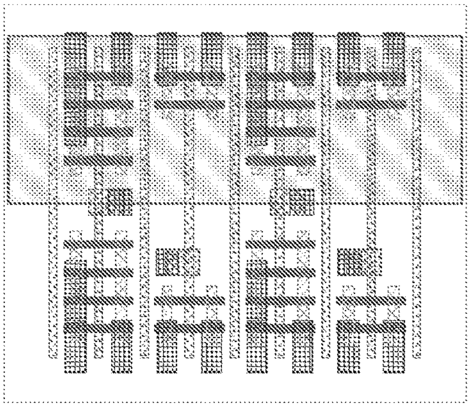
FIG. 1251B
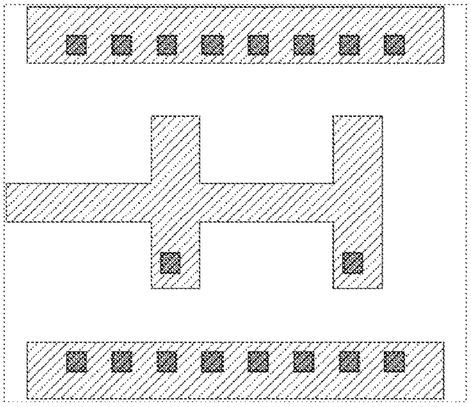
FIG. 1251C
*M* PDF Solutions, Inc.

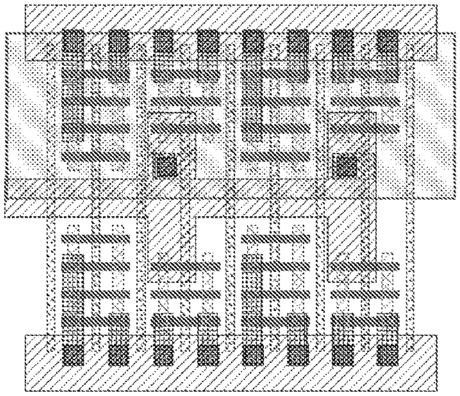
FIG. 1252A
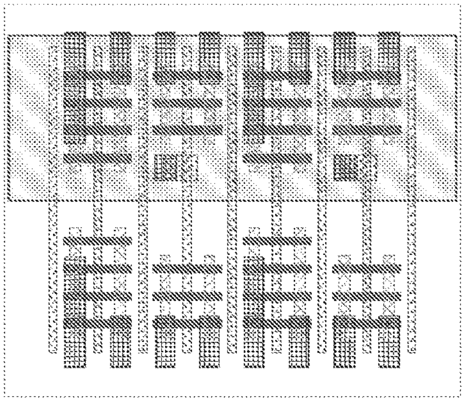
FIG. 1252B
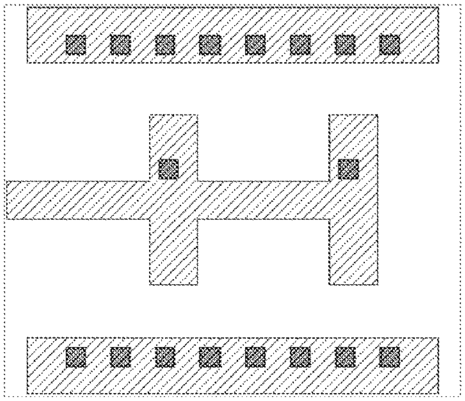
FIG. 1252C

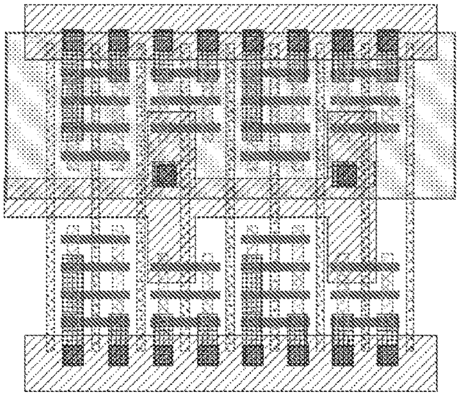
FIG. 1253A
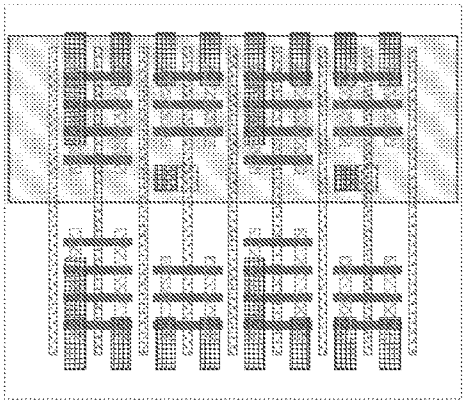
FIG. 1253B
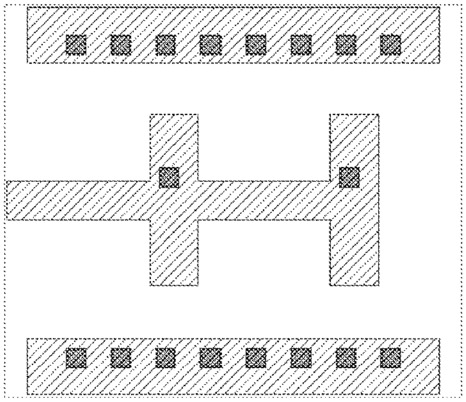
FIG. 1253C

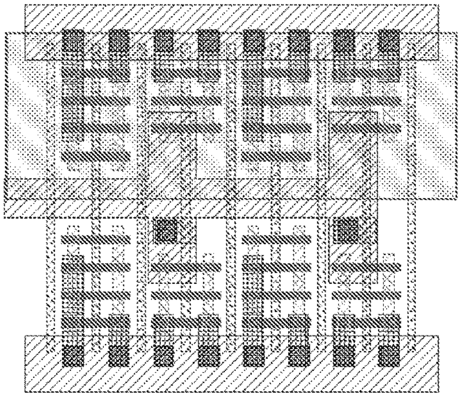
FIG. 1254A
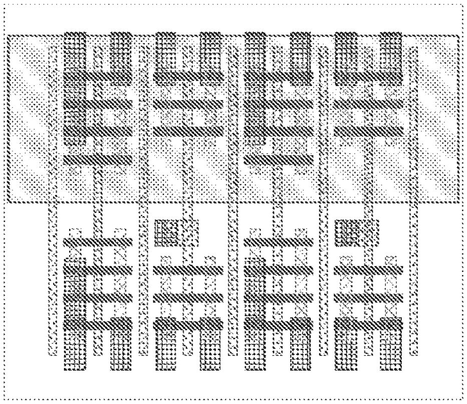
FIG. 1254B
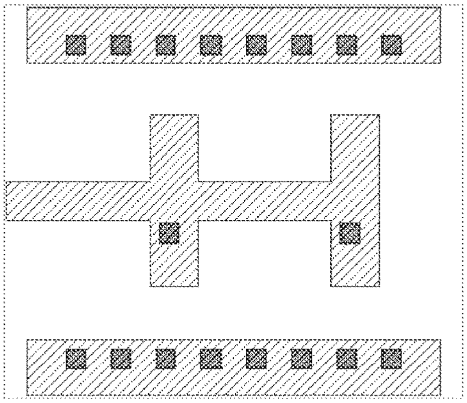
FIG. 1254C

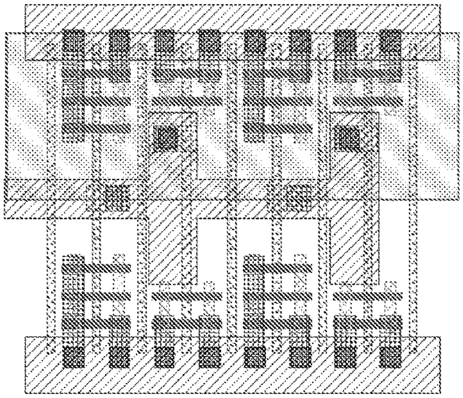
FIG. 1255A
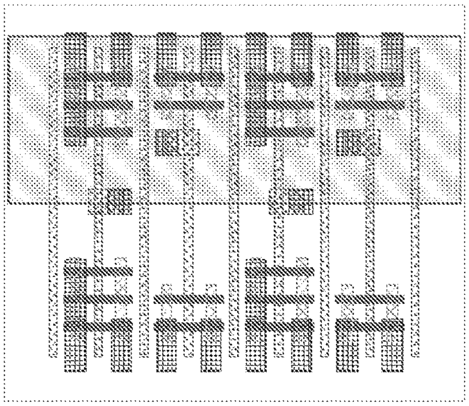
FIG. 1255B
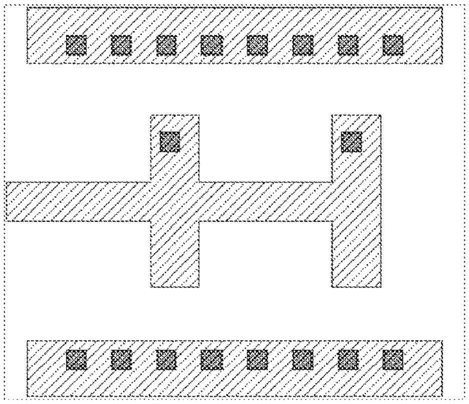
FIG. 1255C

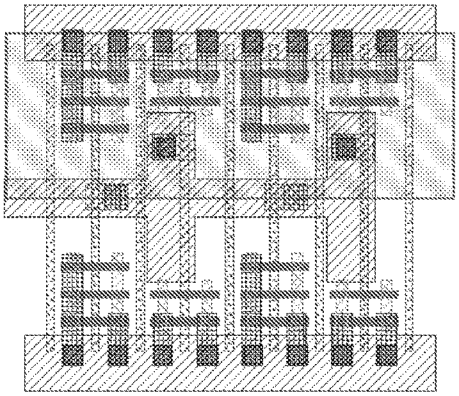
FIG. 1256A
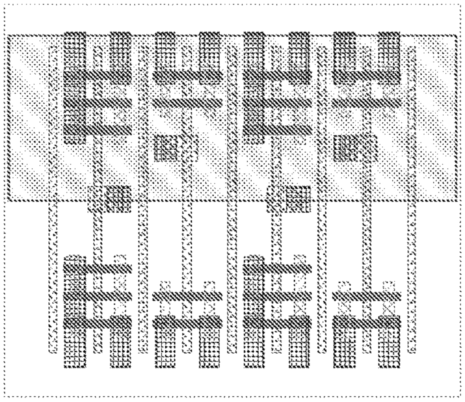
FIG. 1256B
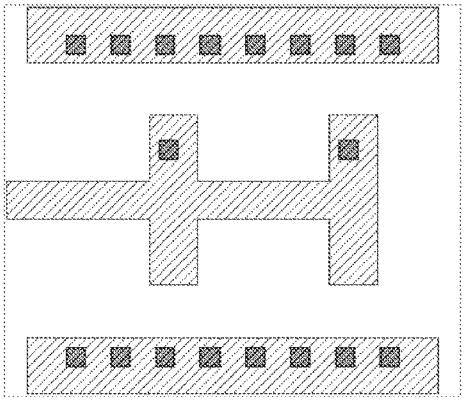
FIG. 1256C

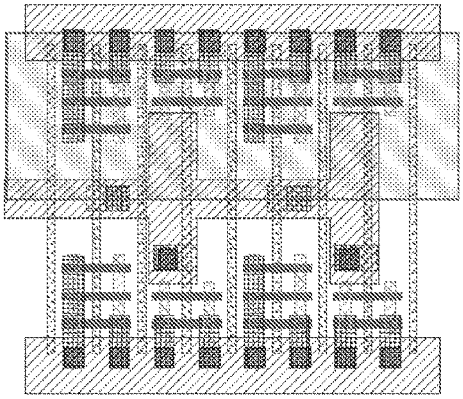
FIG. 1257A
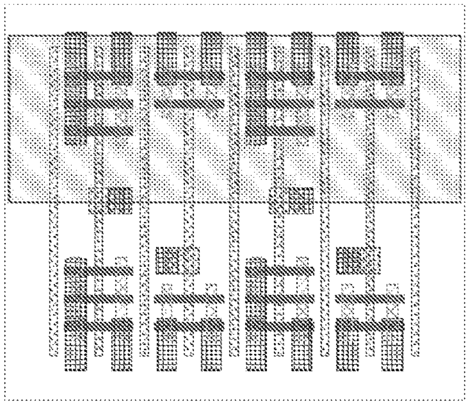
FIG. 1257B
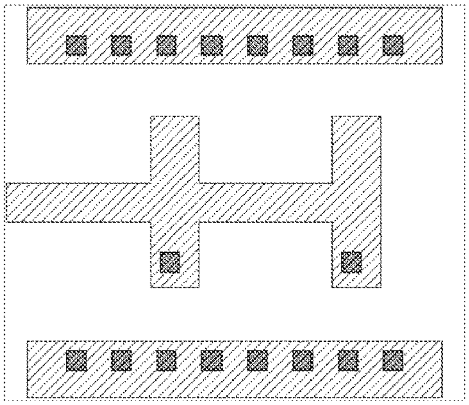
FIG. 1257C
*M* PDF Solutions, Inc.

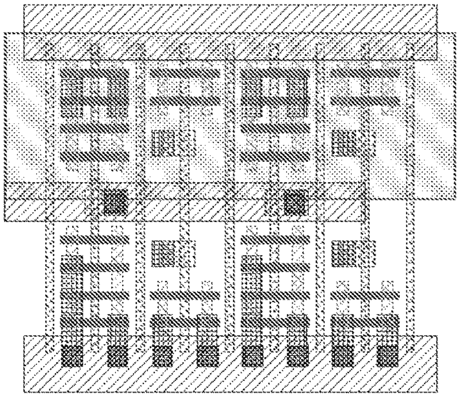
FIG. 1258A
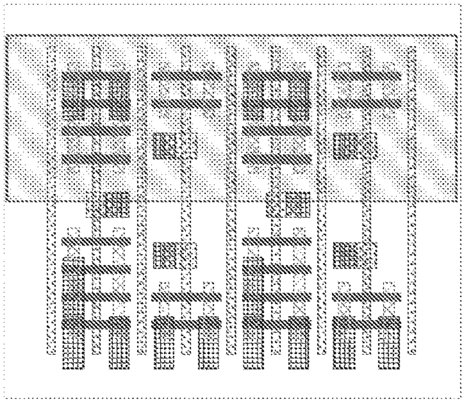
FIG. 1258B
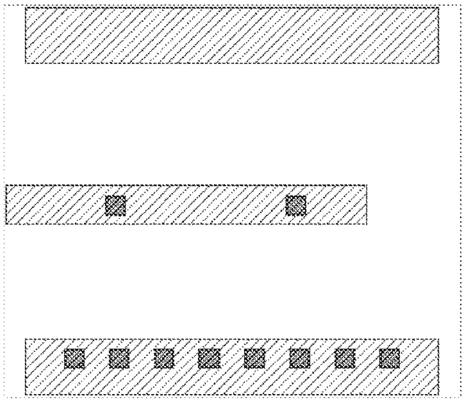
FIG. 1258C
*M* PDF Solutions, Inc.

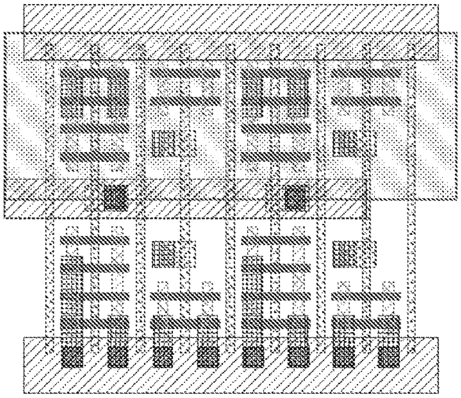
FIG. 1259A
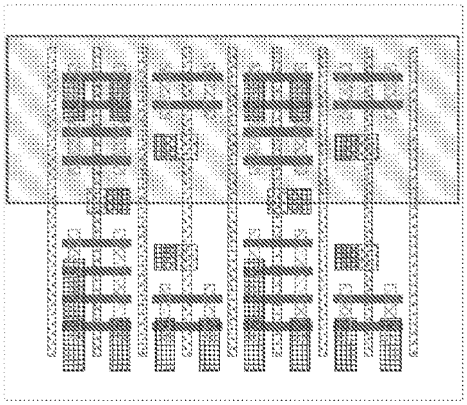
FIG. 1259B
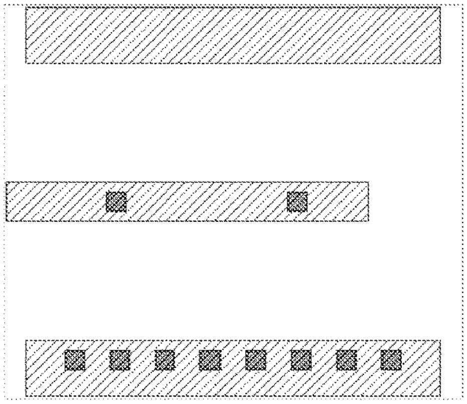
FIG. 1259C

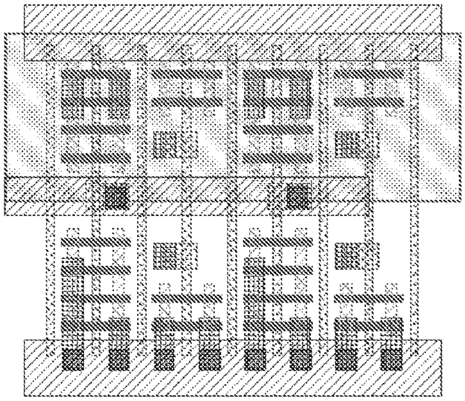
FIG. 1260A
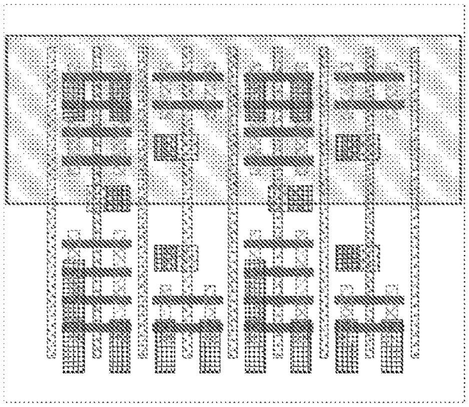
FIG. 1260B
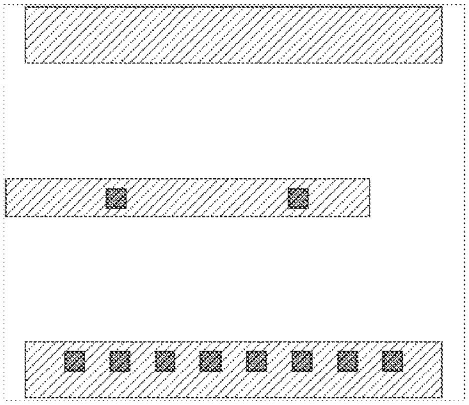
FIG. 1260C
*M* PDF Solutions, Inc.

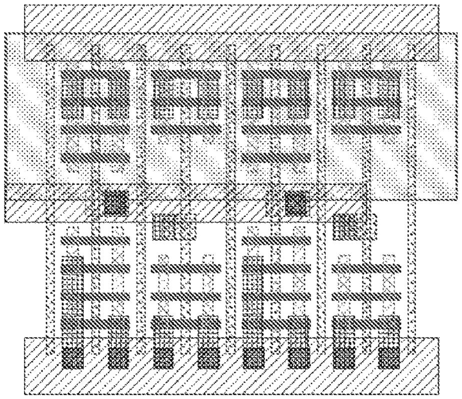
FIG. 1261A
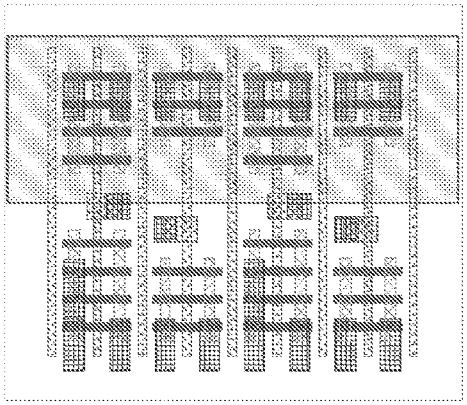
FIG. 1261B
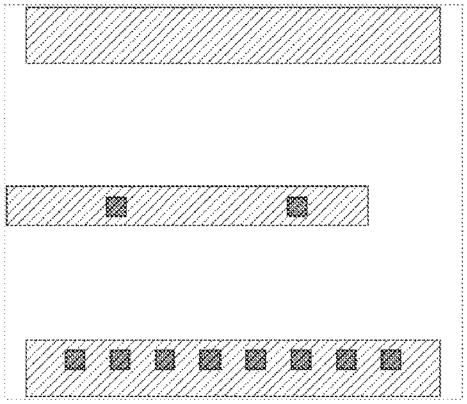
FIG. 1261C
*M* PDF Solutions, Inc.

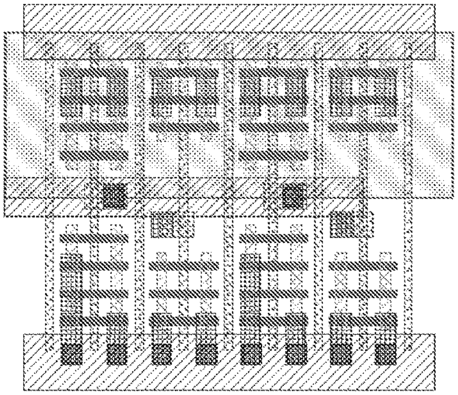
FIG. 1262A
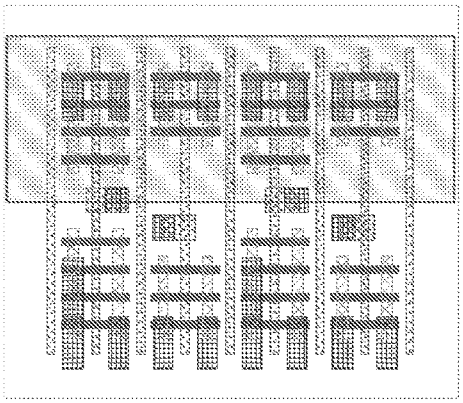
FIG. 1262B
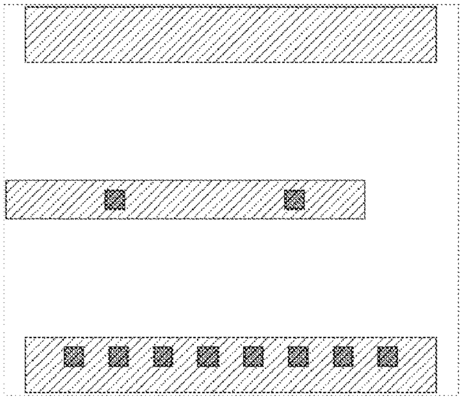
FIG. 1262C

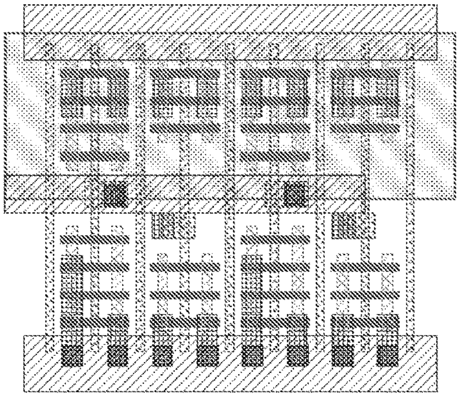
FIG. 1263A
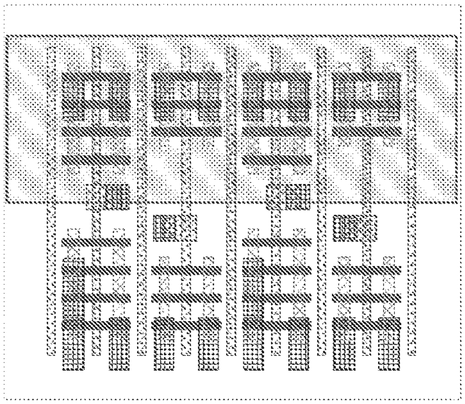
FIG. 1263B
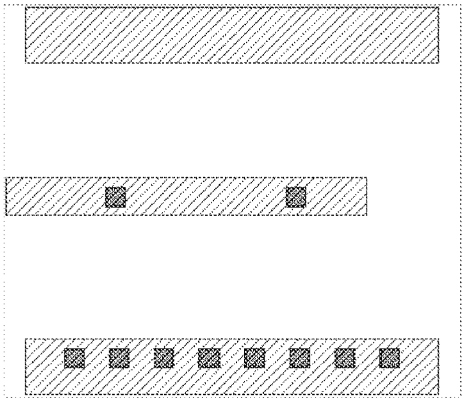
FIG. 1263C

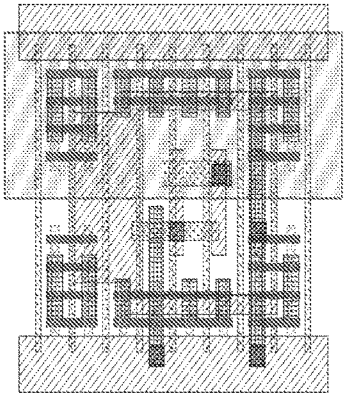
FIG. 1264A
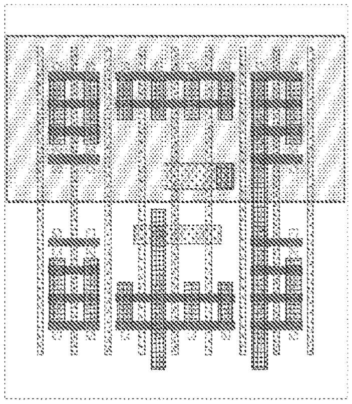
FIG. 1264B
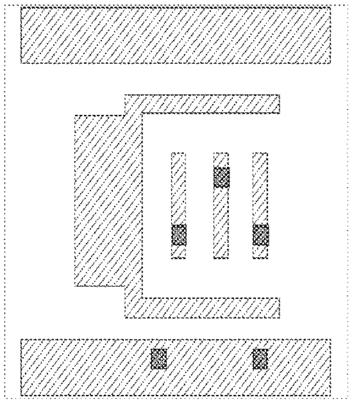
FIG. 1264C

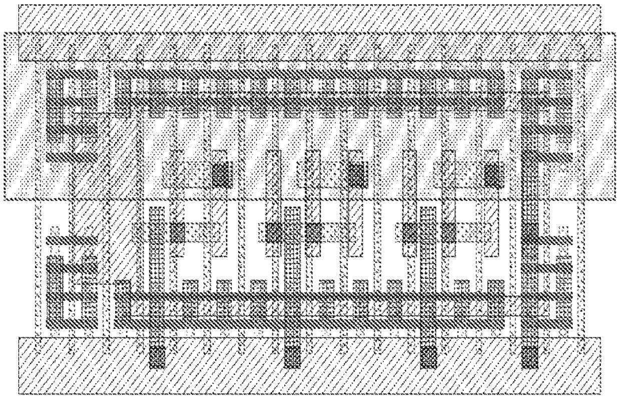
FIG. 1265A
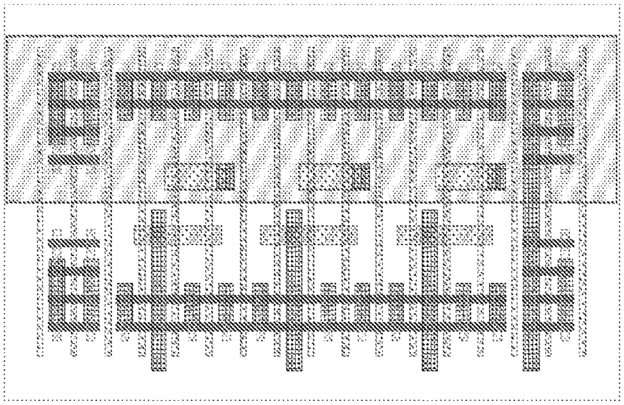
FIG. 1265B
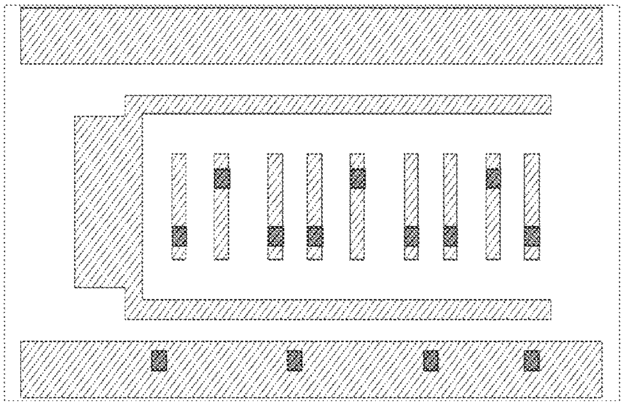
FIG. 1265C

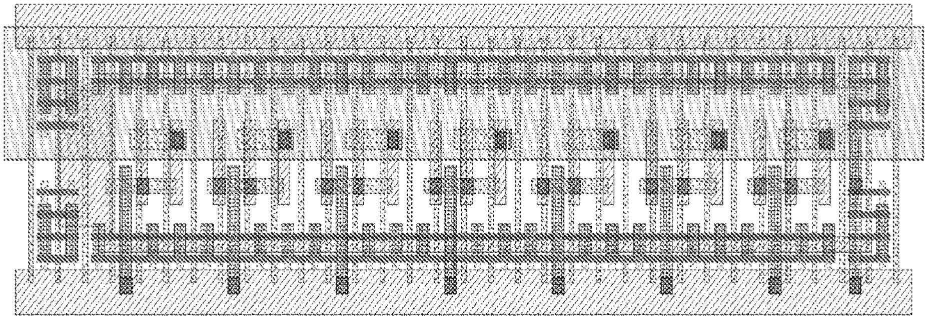
FIG. 1266A
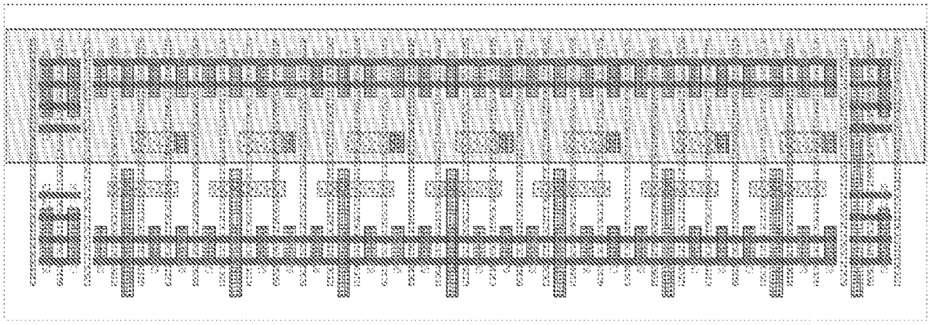
FIG. 1266B
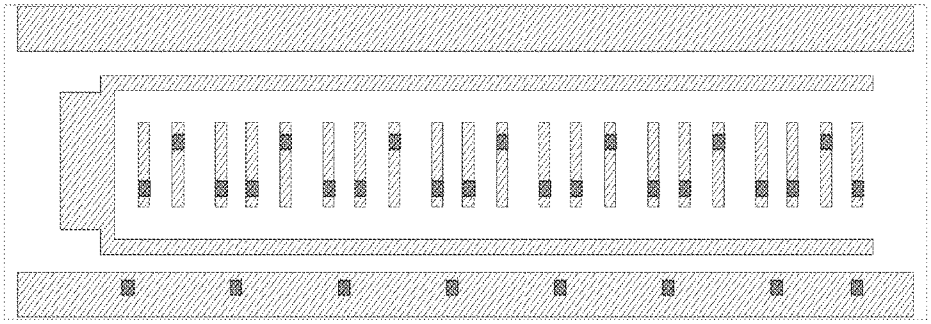
FIG. 1266C

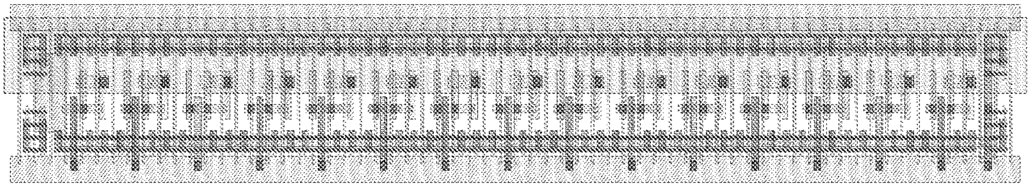
FIG. 1267A
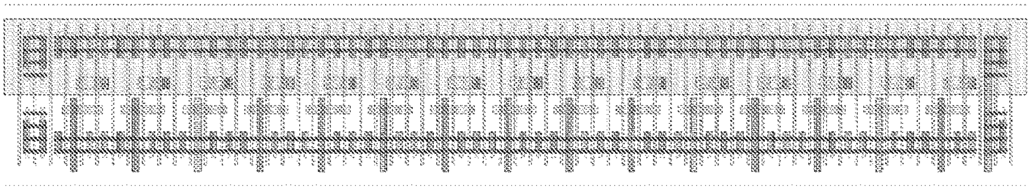
FIG. 1267B
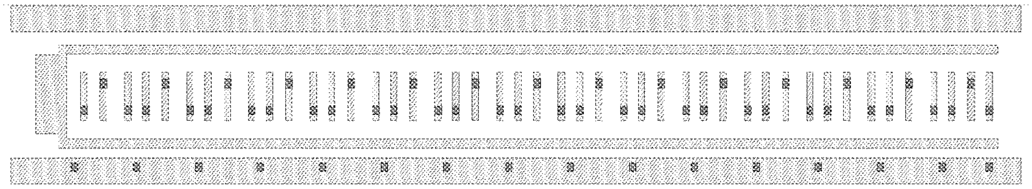
FIG. 1267C

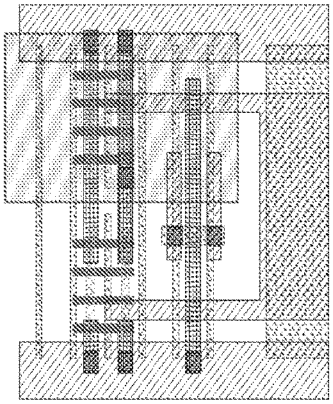
FIG. 1268A
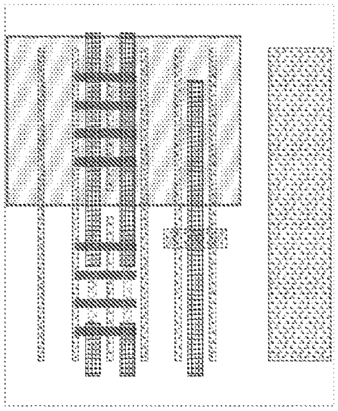
FIG. 1268B
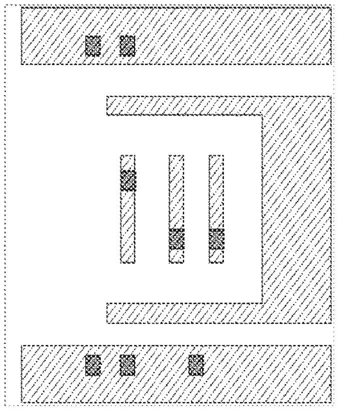
FIG. 1268C
*M* PDF Solutions, Inc.

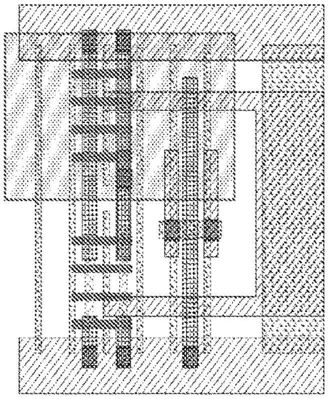
FIG. 1269A
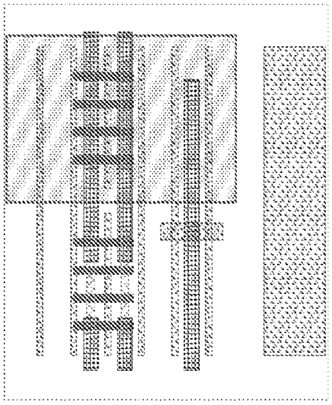
FIG. 1269B
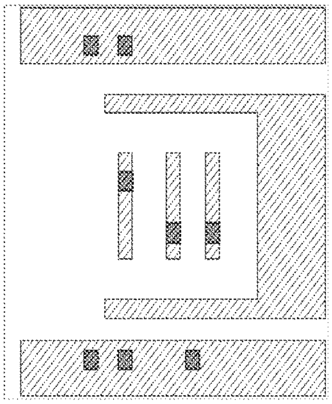
FIG. 1269C

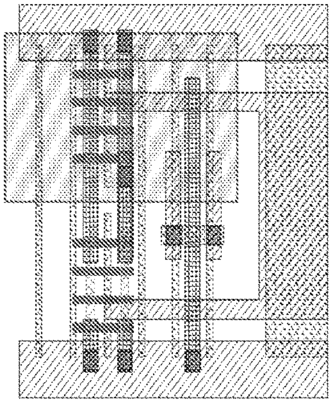
FIG. 1270A
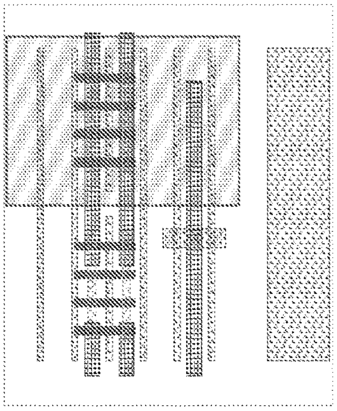
FIG. 1270B
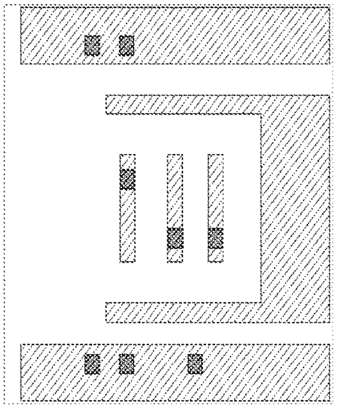
FIG. 1270C

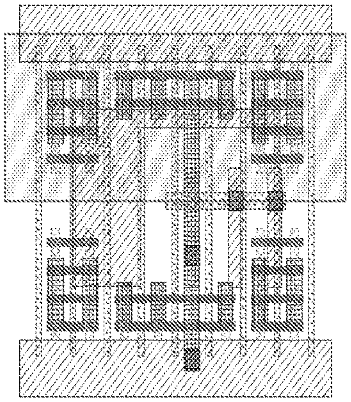
FIG. 1271A
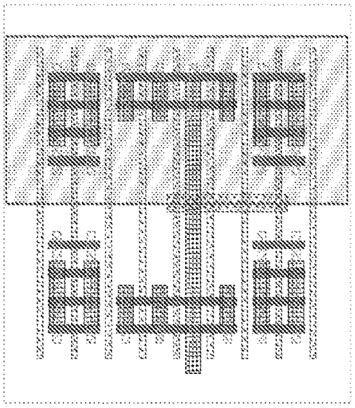
FIG. 1271B
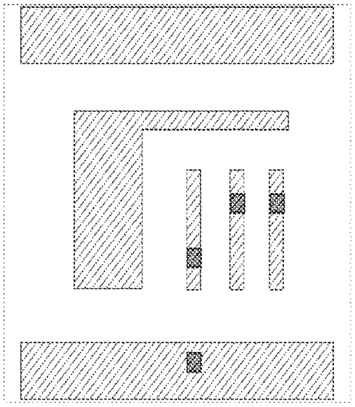
FIG. 1271C

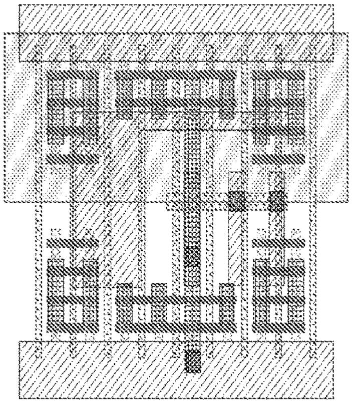
FIG. 1272A
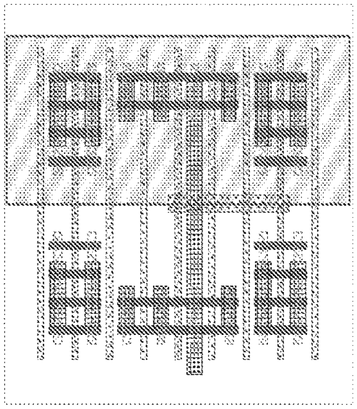
FIG. 1272B
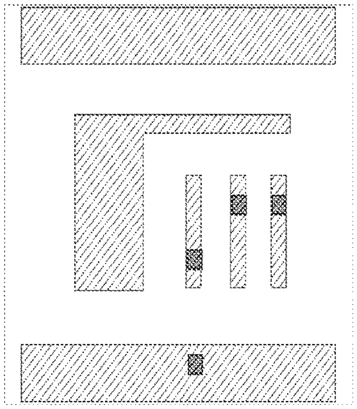
FIG. 1272C

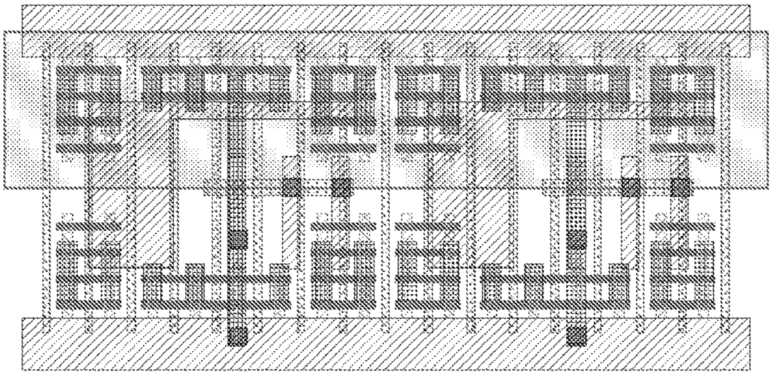
FIG. 1273A
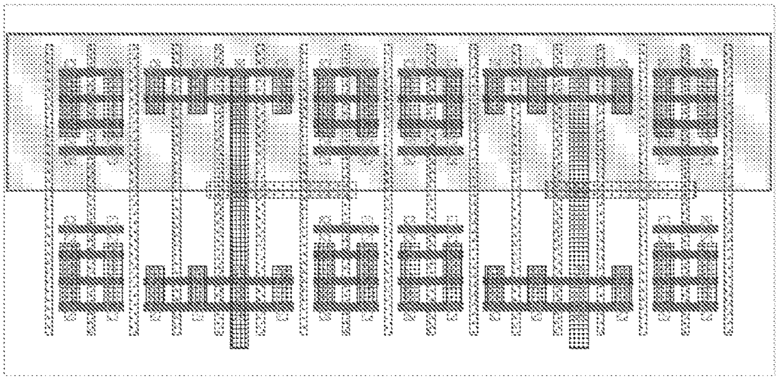
FIG. 1273B
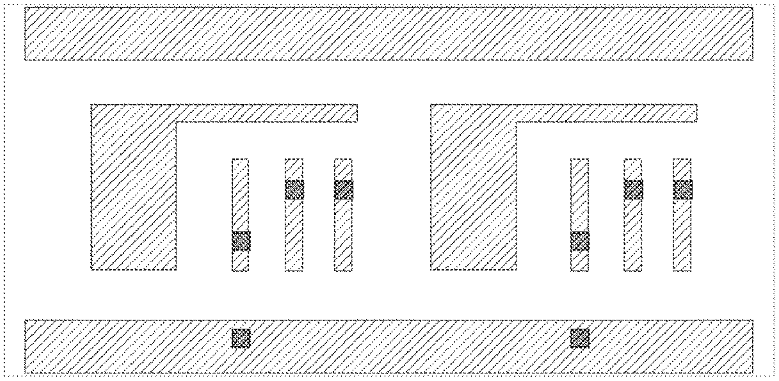
FIG. 1273C

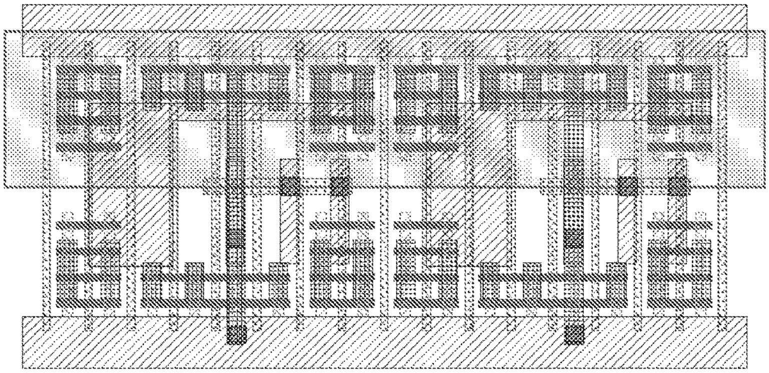
FIG. 1274A
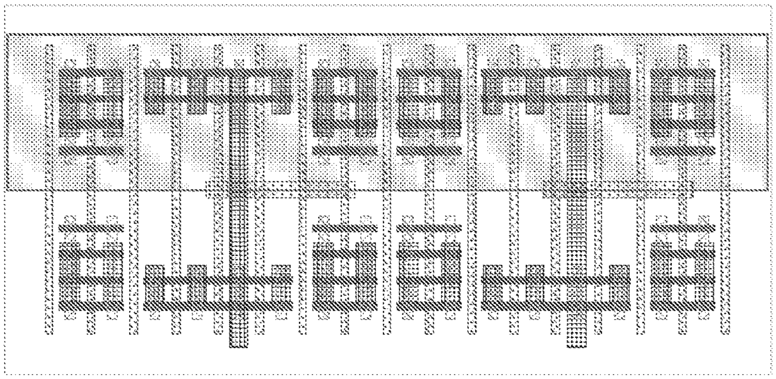
FIG. 1274B
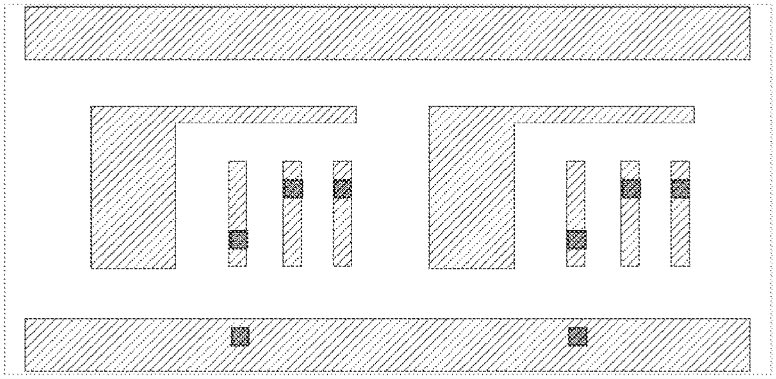
FIG. 1274C
*M* PDF Solutions, Inc.

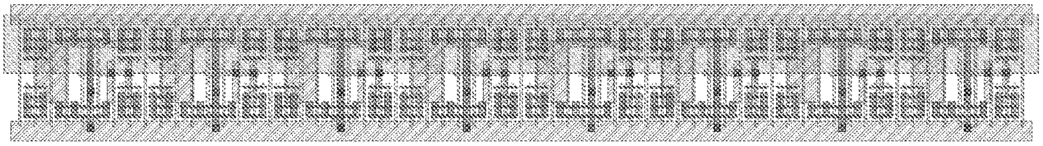
FIG. 1275A
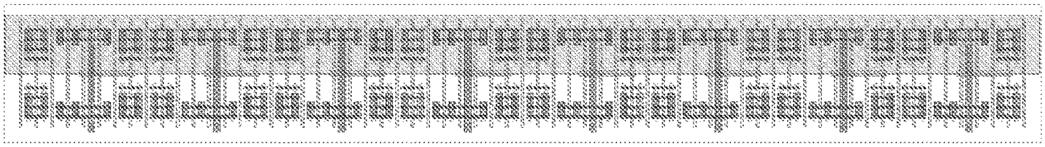
FIG. 1275B
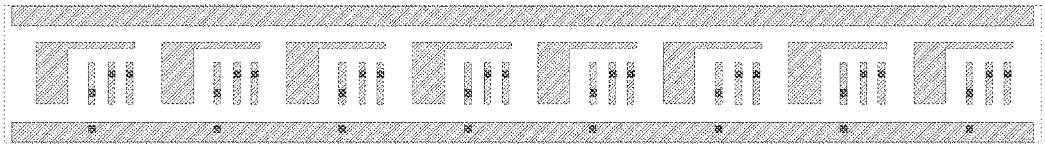
FIG. 1275C

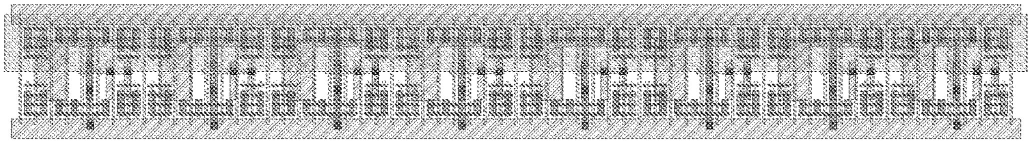
FIG. 1276A
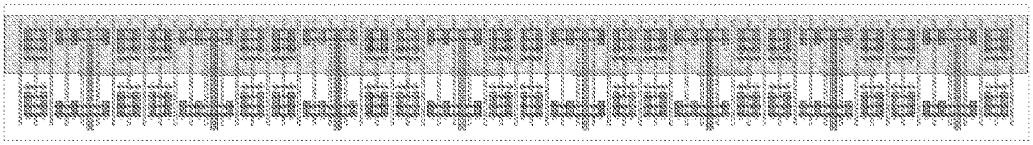
FIG. 1276B
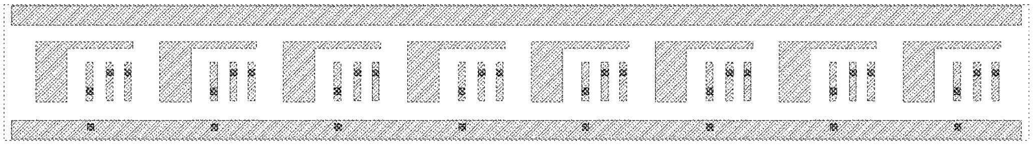
FIG. 1276C

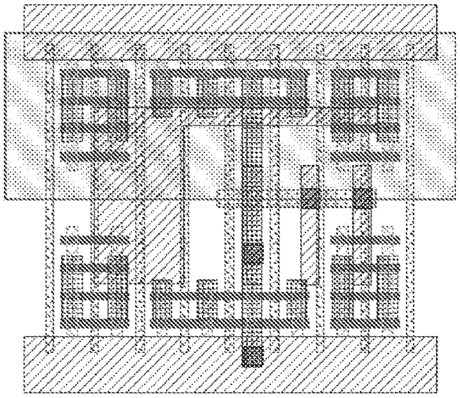
FIG. 1277A
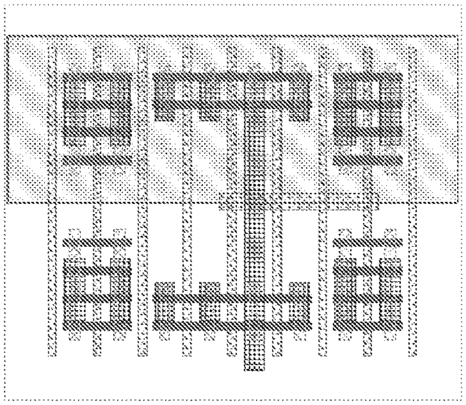
FIG. 1277B
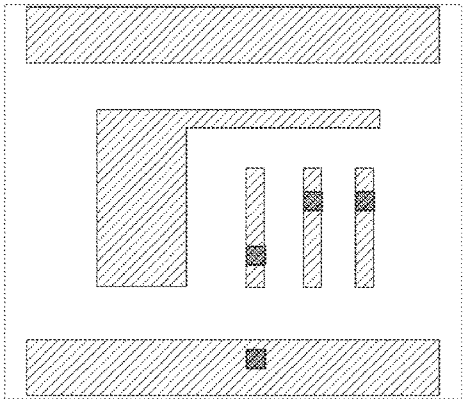
FIG. 1277C
*M* PDF Solutions, Inc.

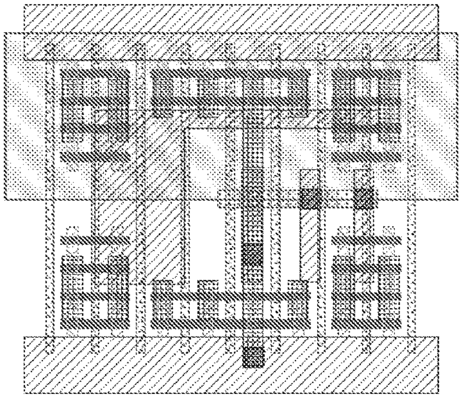
FIG. 1278A
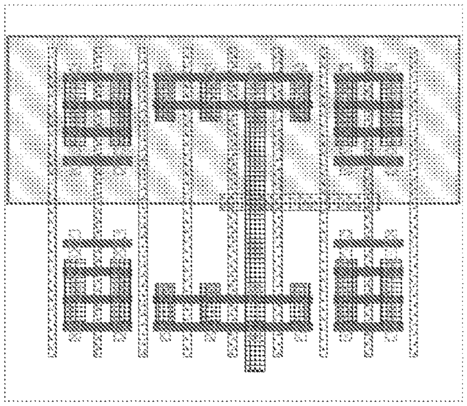
FIG. 1278B
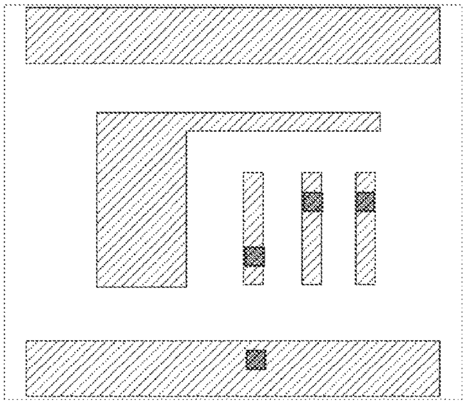
FIG. 1278C

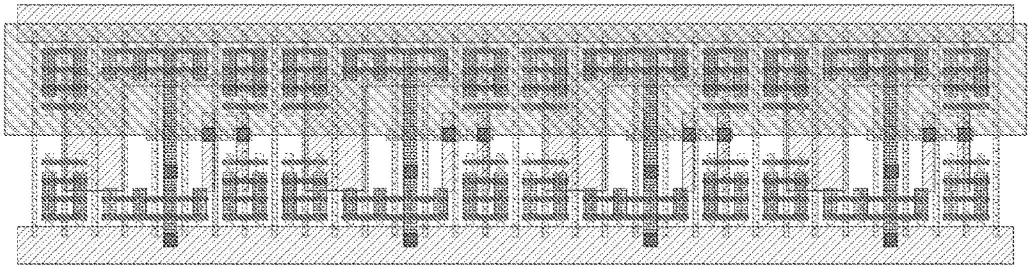
FIG. 1279A
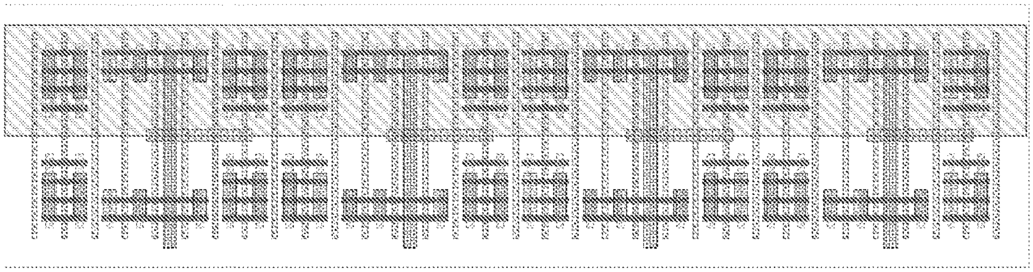
FIG. 1279B
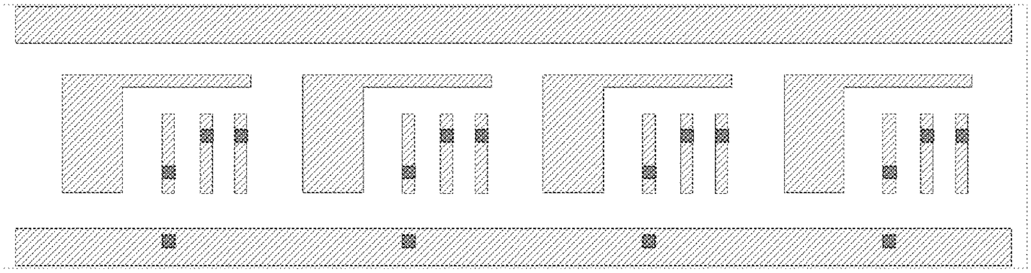
FIG. 1279C

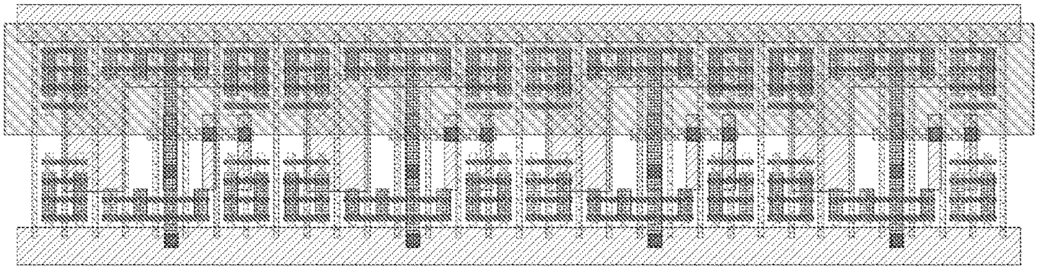
FIG. 1280A
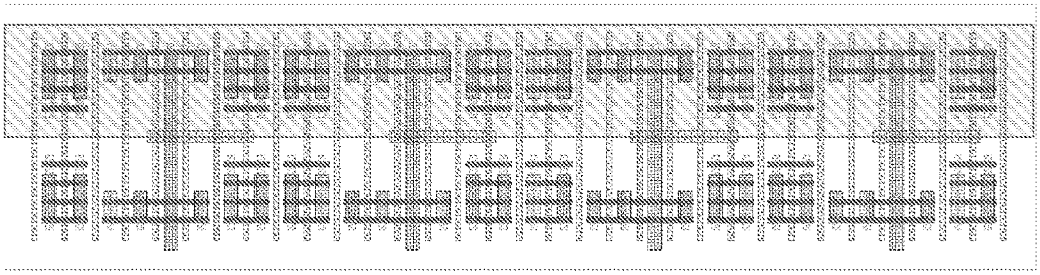
FIG. 1280B
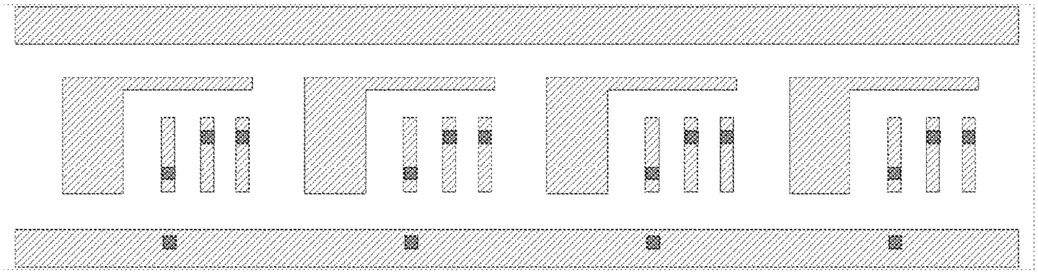
FIG. 1280C

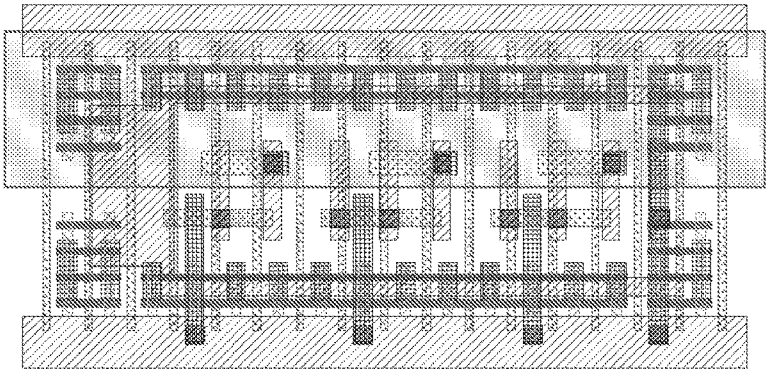
FIG. 1281A
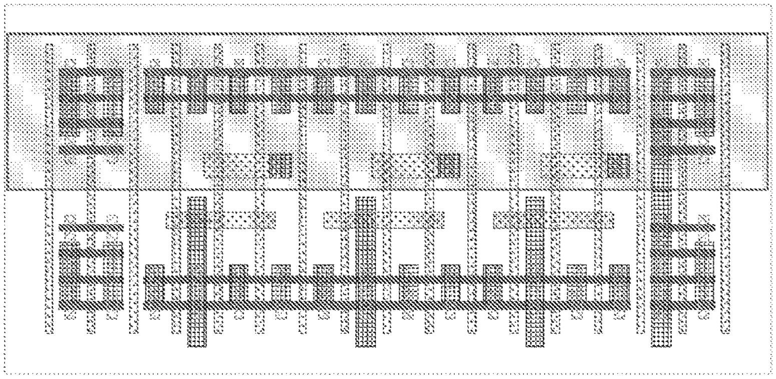
FIG. 1281B
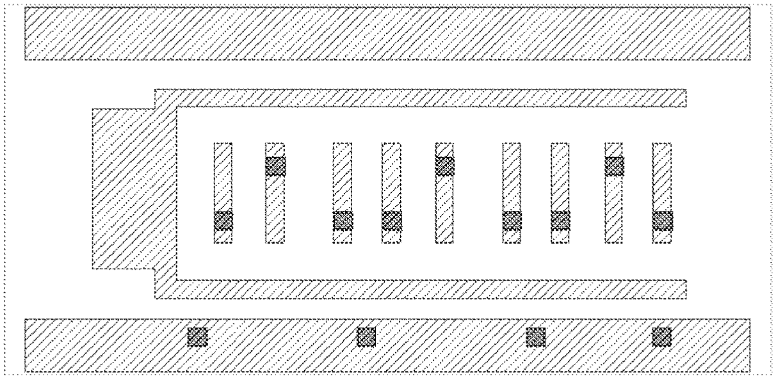
FIG. 1281C
*M* PDF Solutions, Inc.

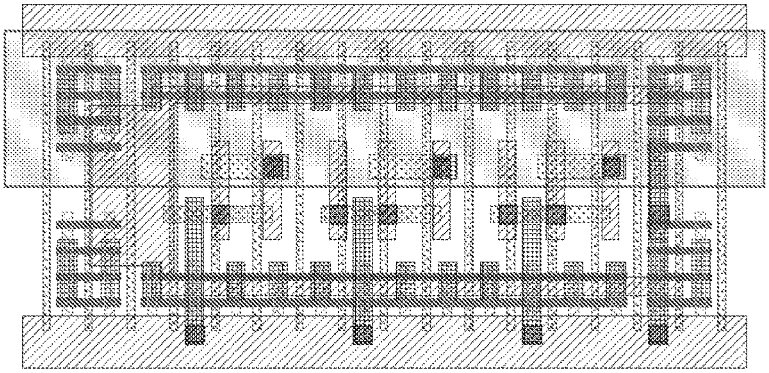
FIG. 1282A
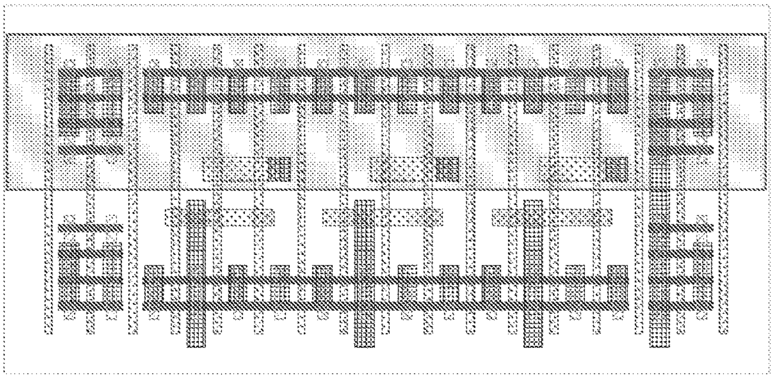
FIG. 1282B
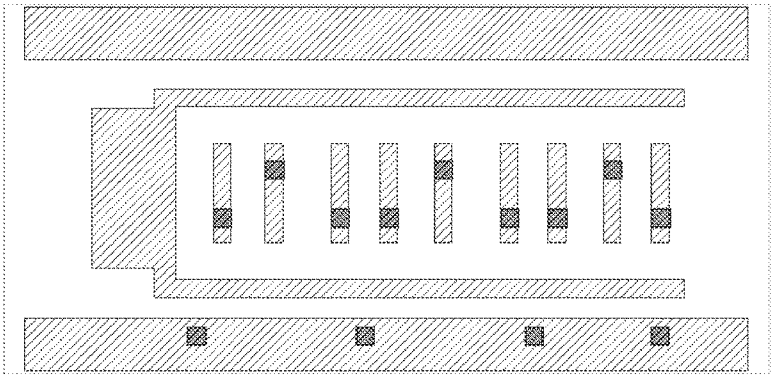
FIG. 1282C

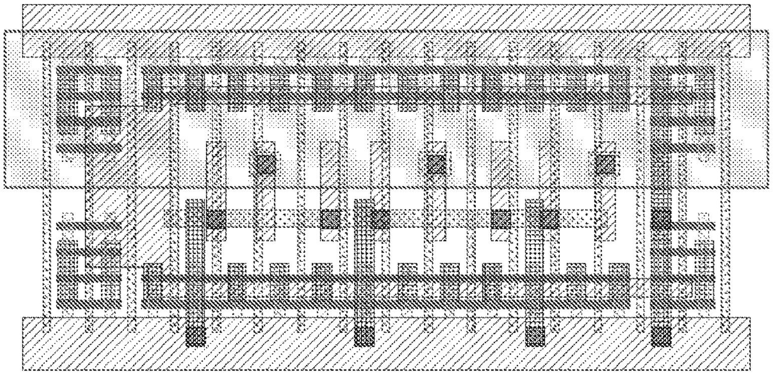
FIG. 1283A
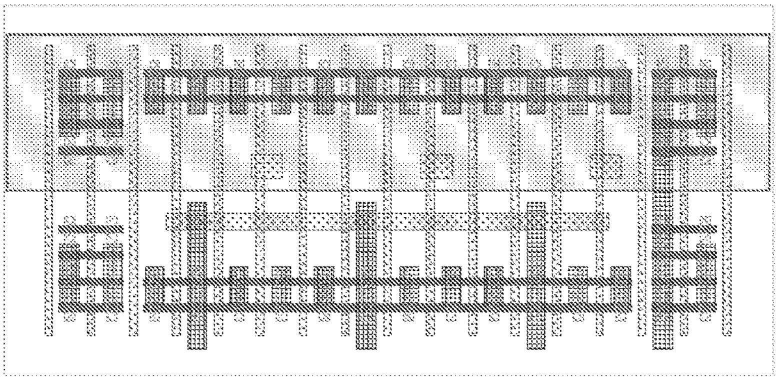
FIG. 1283B
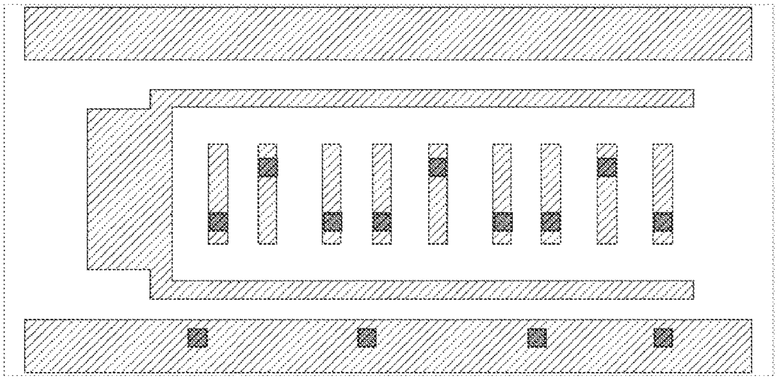
FIG. 1283C
*M* PDF Solutions, Inc.

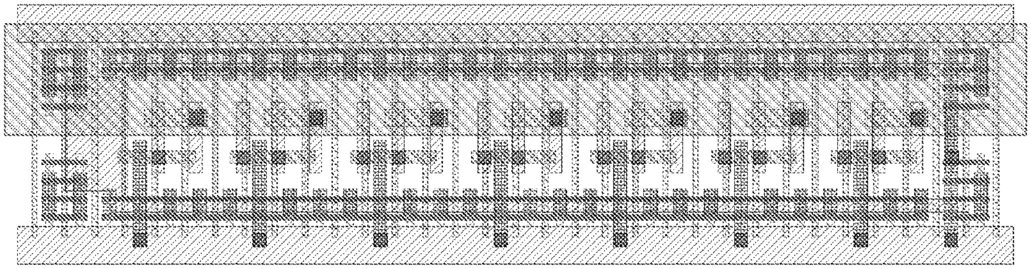
FIG. 1284A
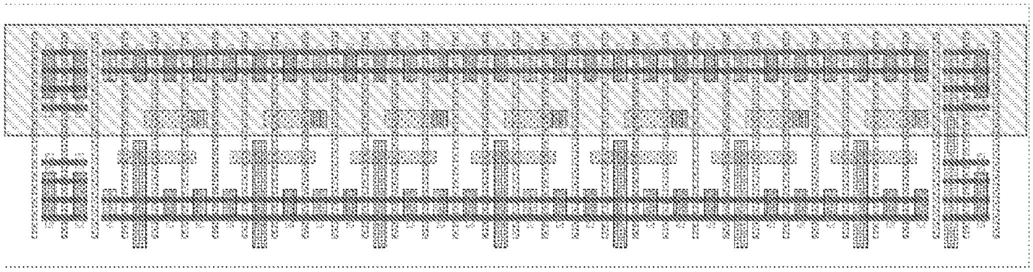
FIG. 1284B
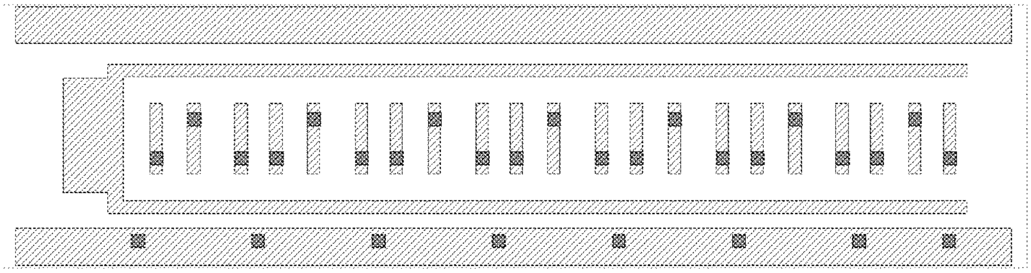
FIG. 1284C

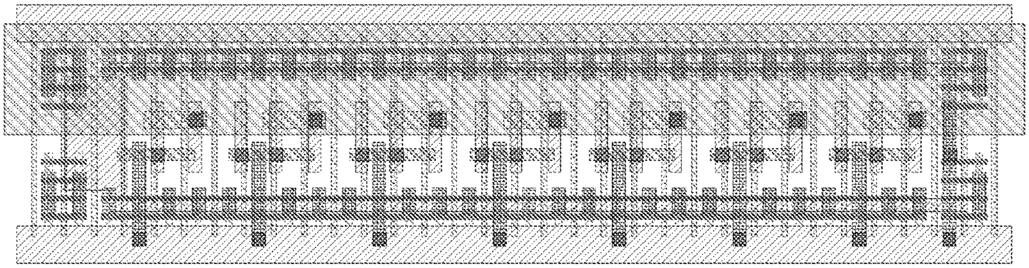
FIG. 1285A
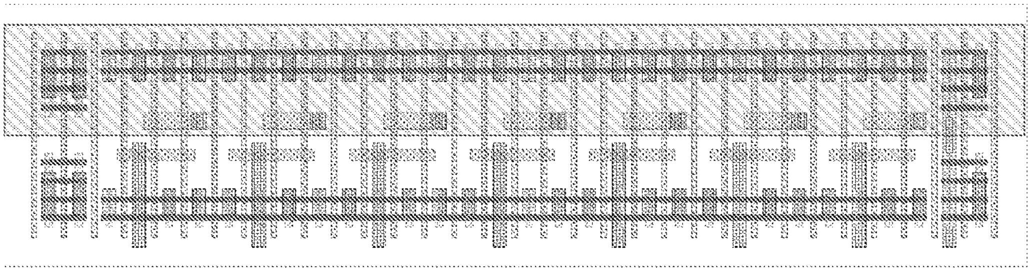
FIG. 1285B
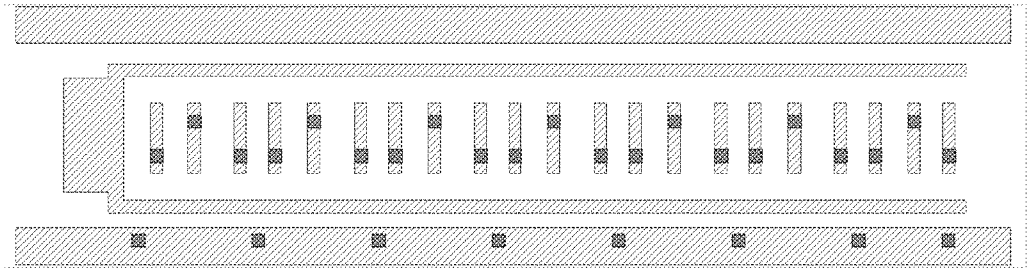
FIG. 1285C

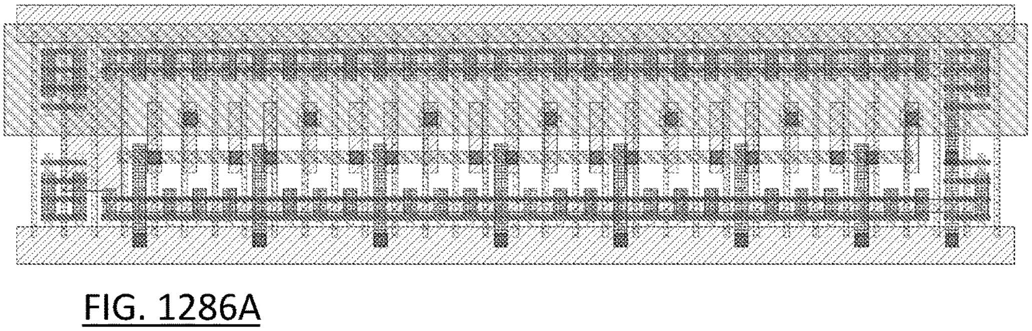
FIG. 1286A
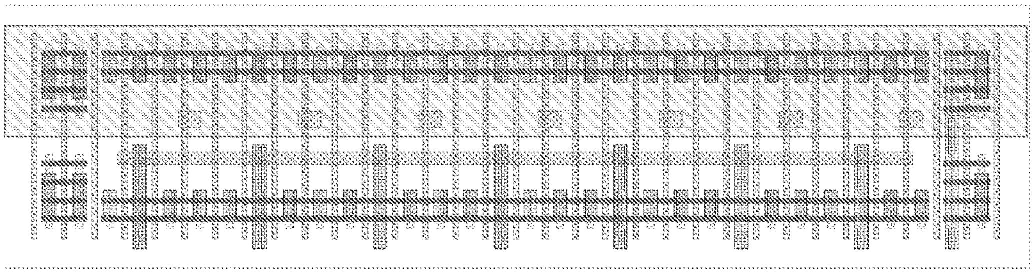
FIG. 1286B
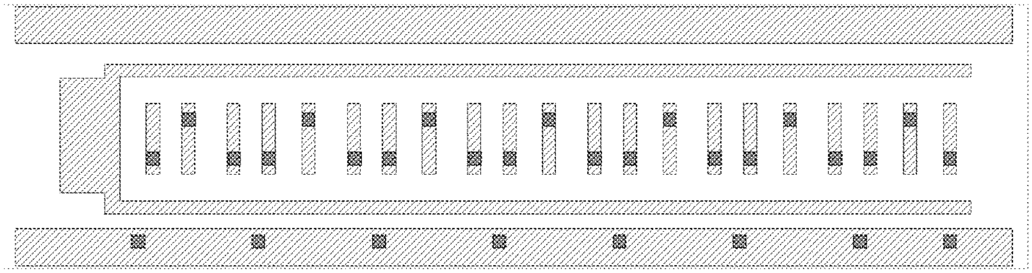
FIG. 1286C

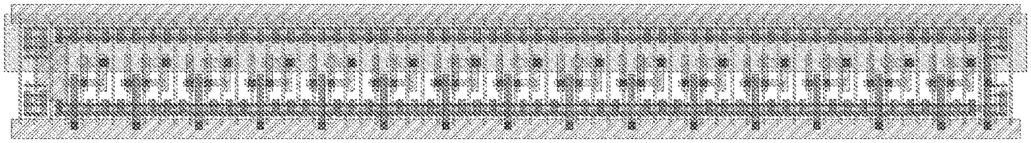
FIG. 1287A
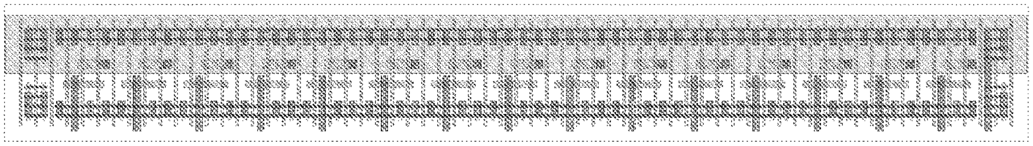
FIG. 1287B
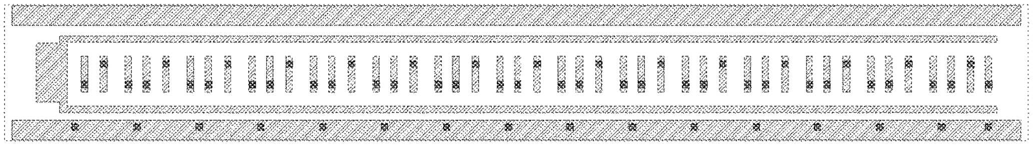
FIG. 1287C

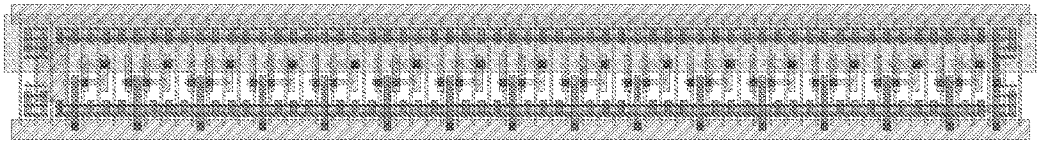
FIG. 1288A
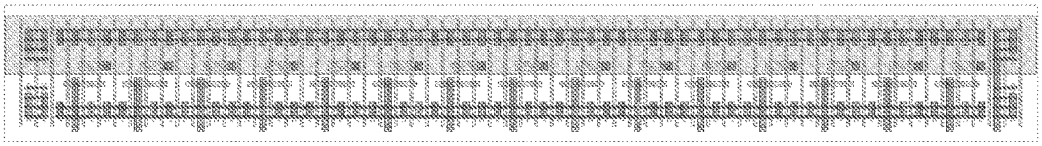
FIG. 1288B
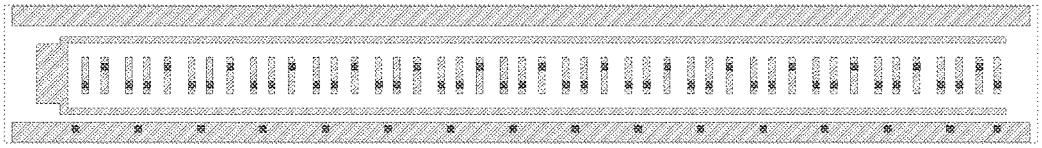
FIG. 1288C

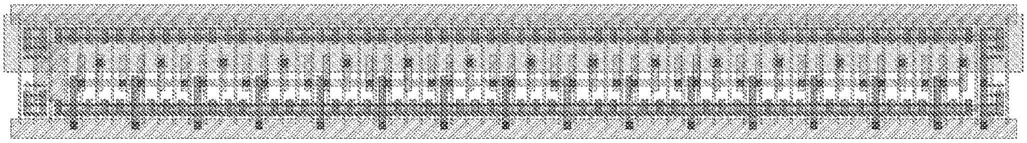
FIG. 1289A
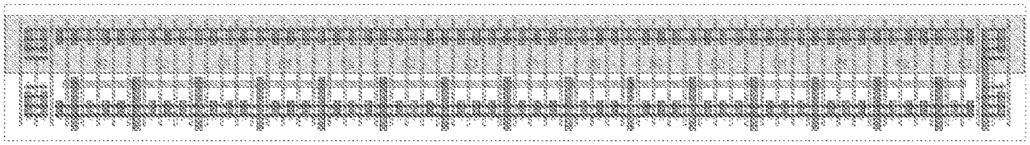
FIG. 1289B
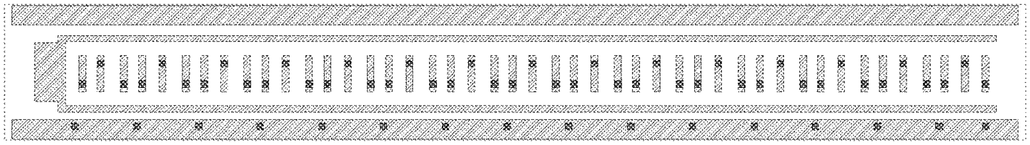
FIG. 1289C

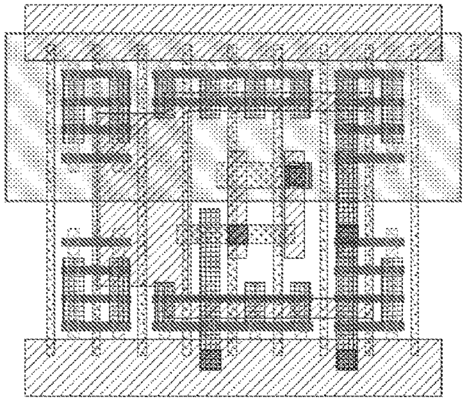
FIG. 1290A
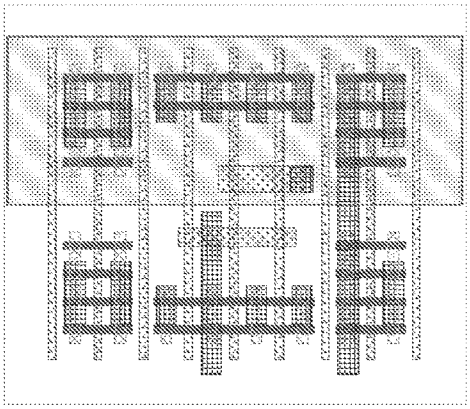
FIG. 1290B
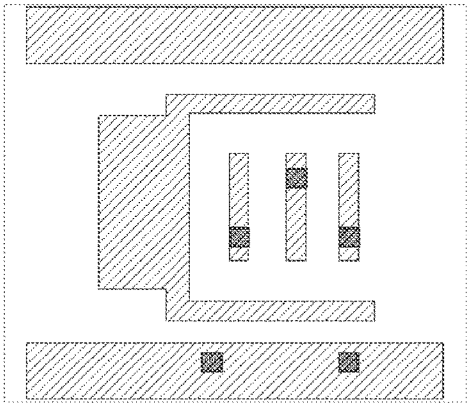
FIG. 1290C
*M* PDF Solutions, Inc.

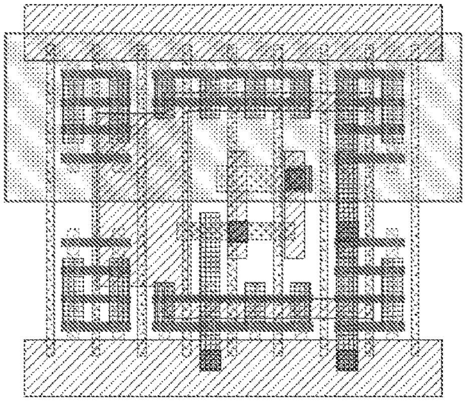
FIG. 1291A
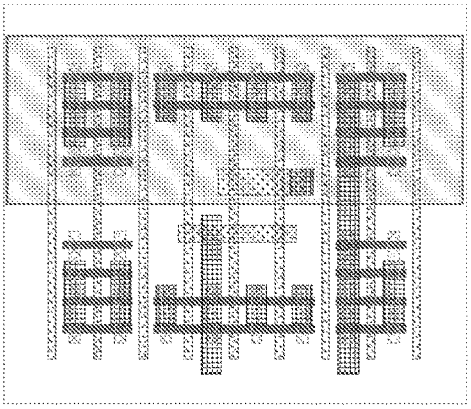
FIG. 1291B
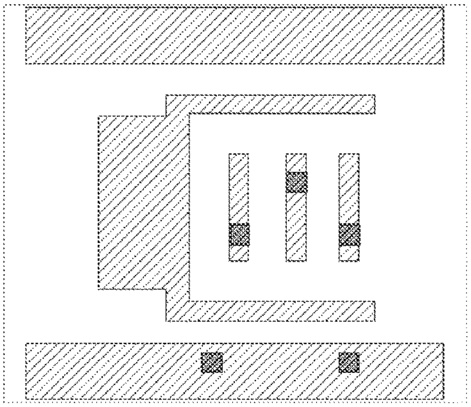
FIG. 1291C
*M* PDF Solutions, Inc.

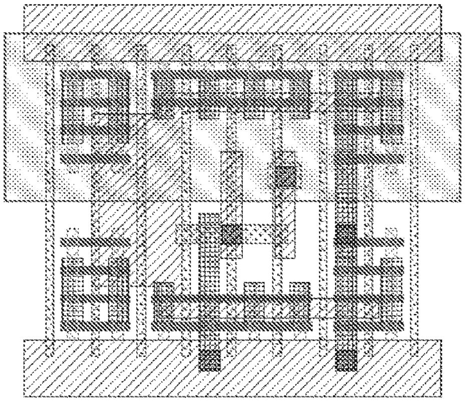
FIG. 1292A
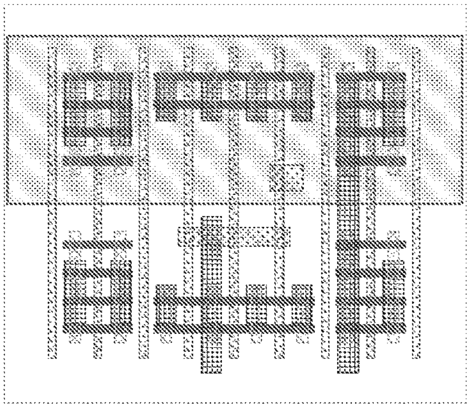
FIG. 1292B
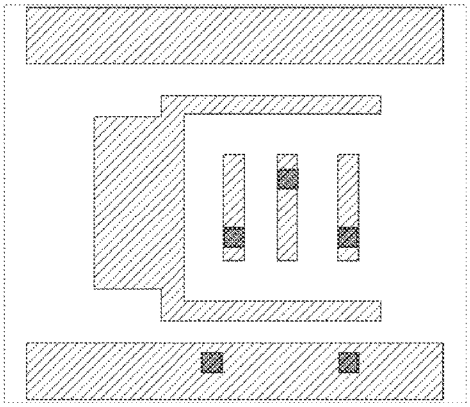
FIG. 1292C
*M* PDF Solutions, Inc.

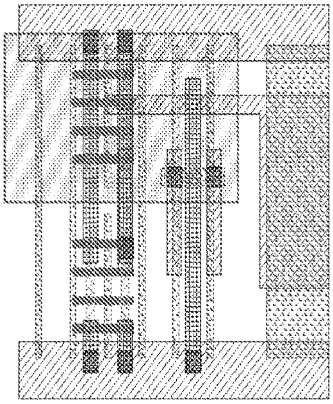
FIG. 1293A
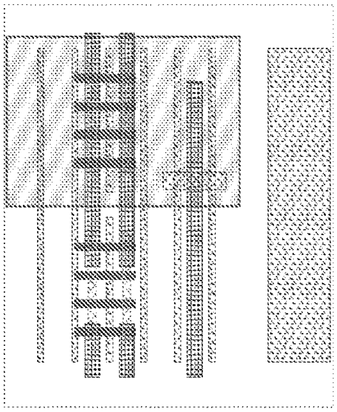
FIG. 1293B
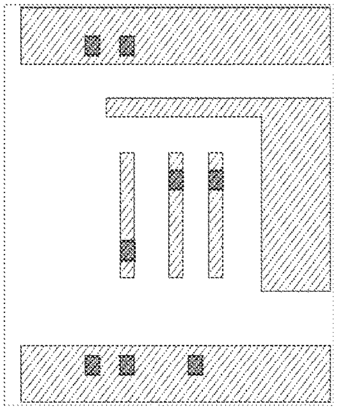
FIG. 1293C

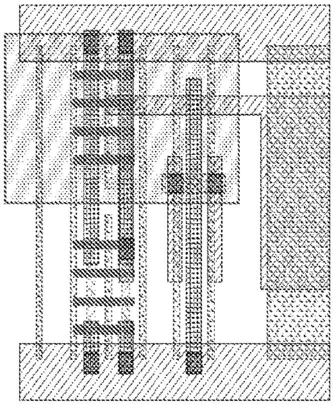
FIG. 1294A
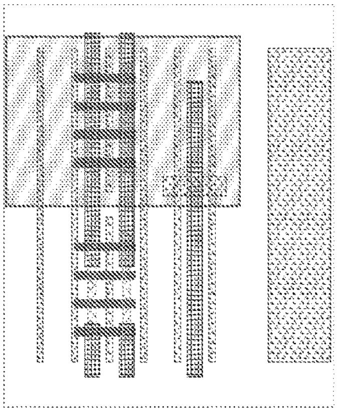
FIG. 1294B
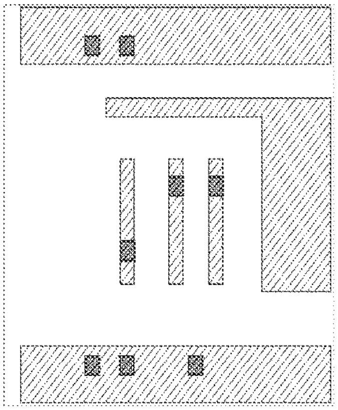
FIG. 1294C

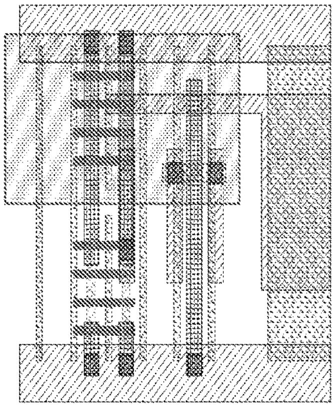
FIG. 1295A
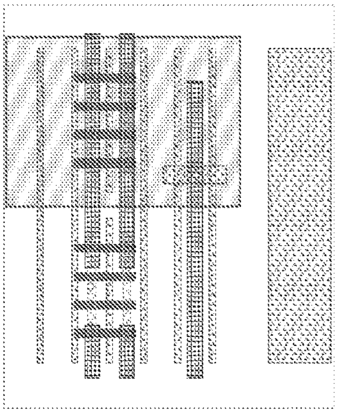
FIG. 1295B
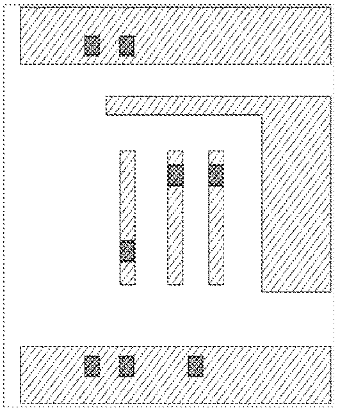
FIG. 1295C

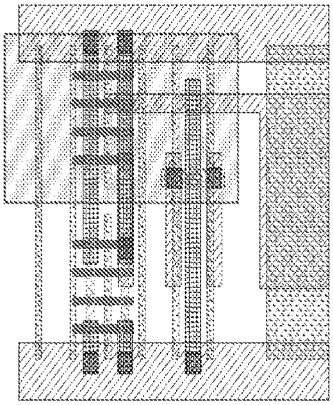
FIG. 1296A
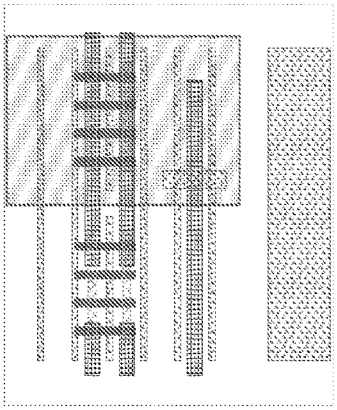
FIG. 1296B
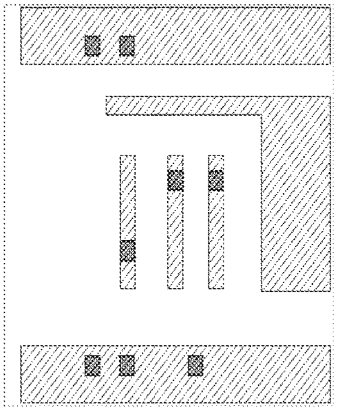
FIG. 1296C
*M* PDF Solutions, Inc.

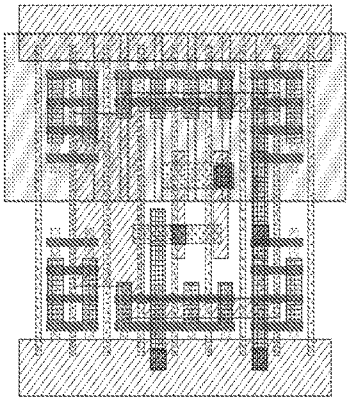
FIG. 1297A
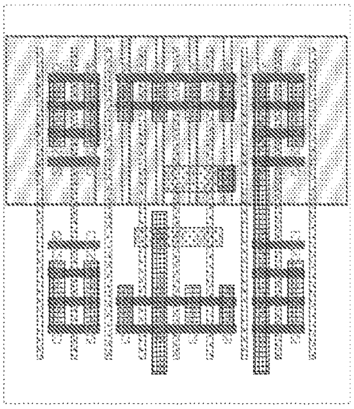
FIG. 1297B
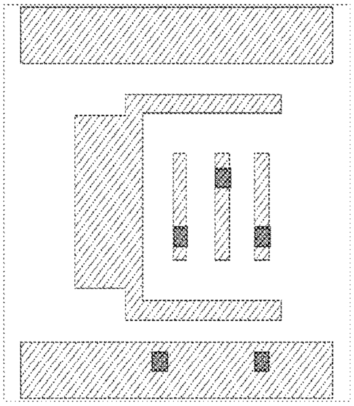
FIG. 1297C

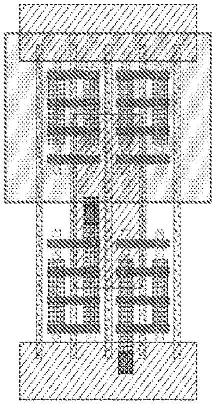
FIG. 1298A
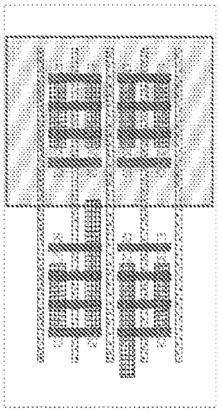
FIG. 1298B
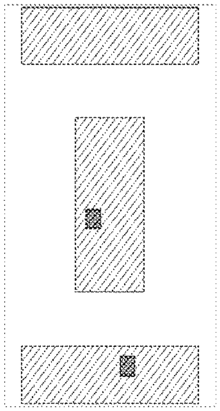
FIG. 1298C

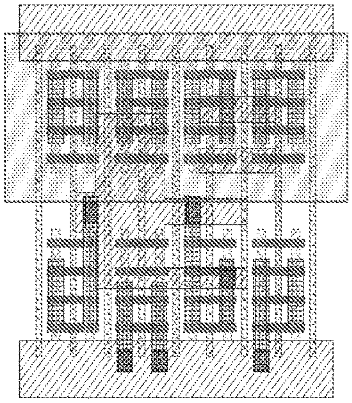
FIG. 1299A
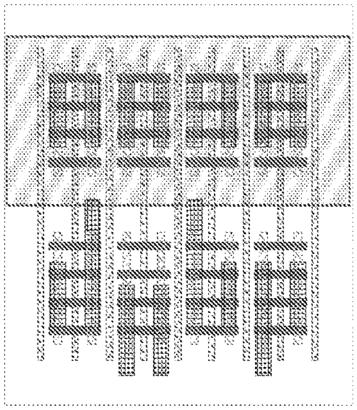
FIG. 1299B
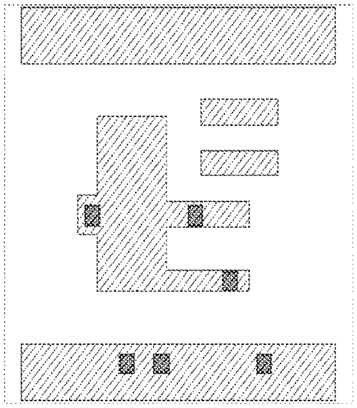
FIG. 1299C

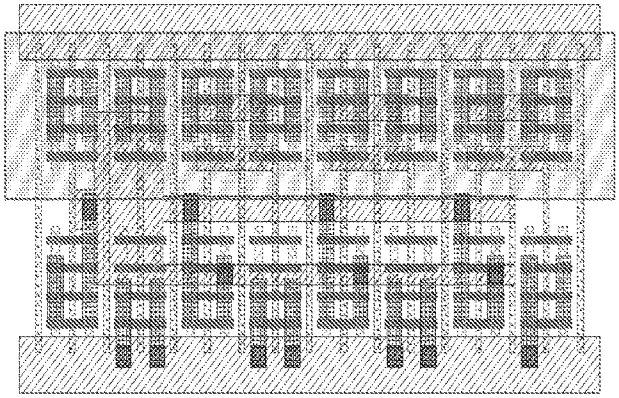
FIG. 1300A
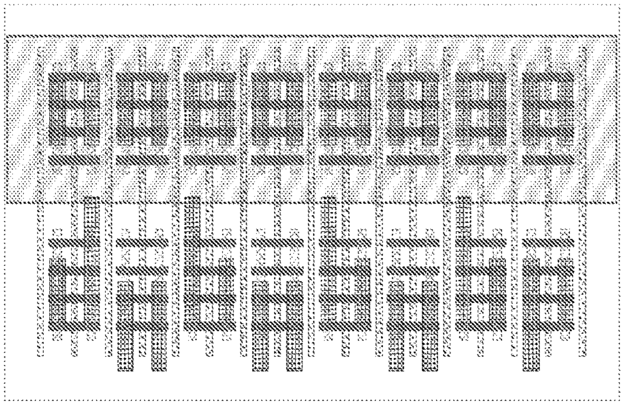
FIG. 1300B
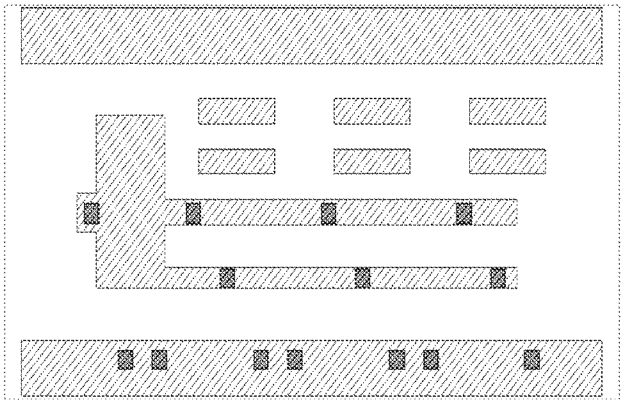
FIG. 1300C
*M* PDF Solutions, Inc.

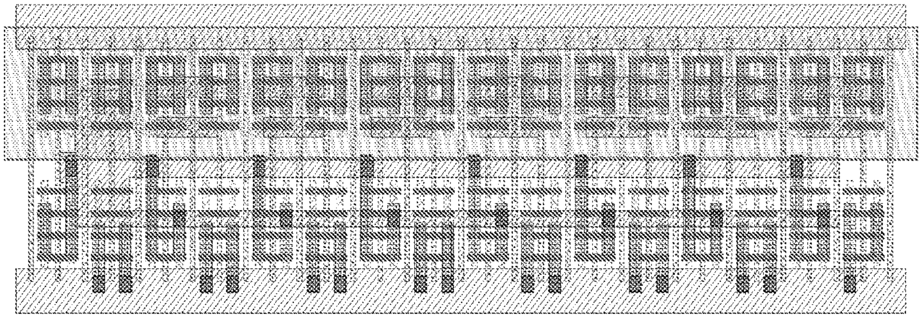
FIG. 1301A
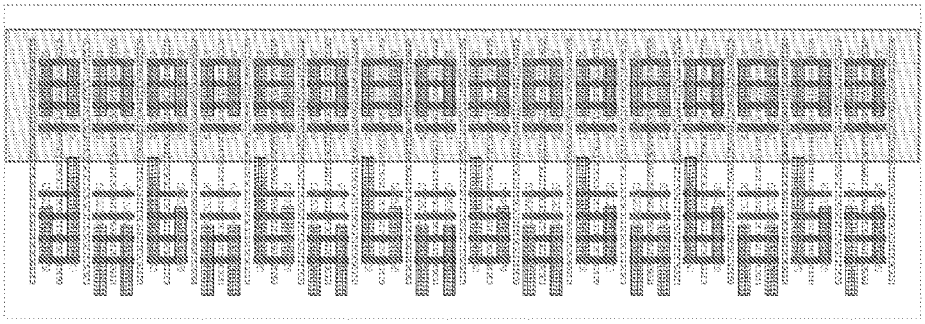
FIG. 1301B
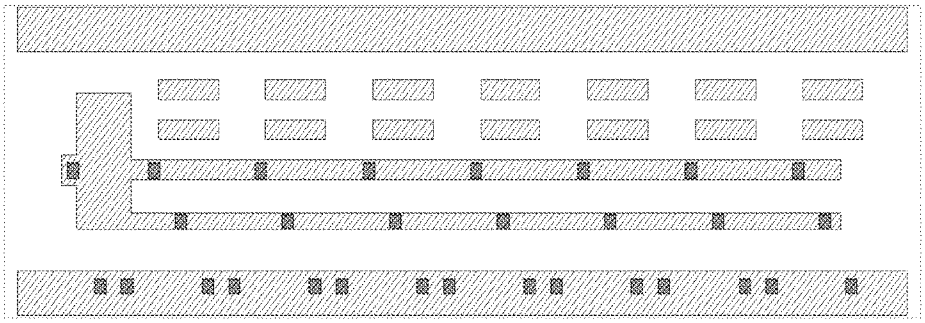
FIG. 1301C
*M* PDF Solutions, Inc.

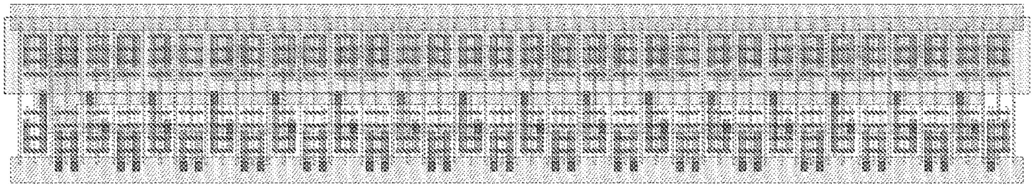
FIG. 1302A
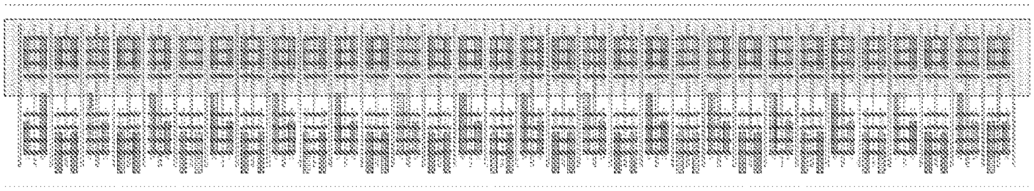
FIG. 1302B
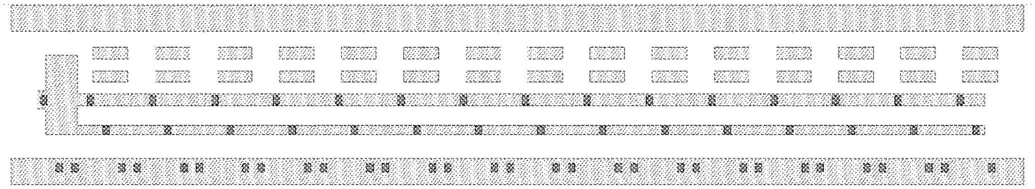
FIG. 1302C

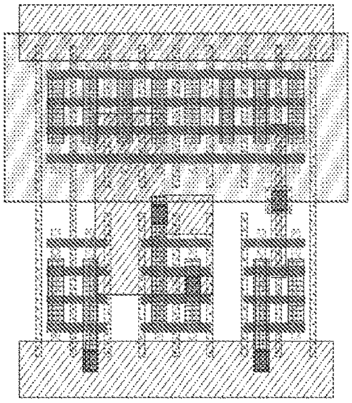
FIG. 1303A
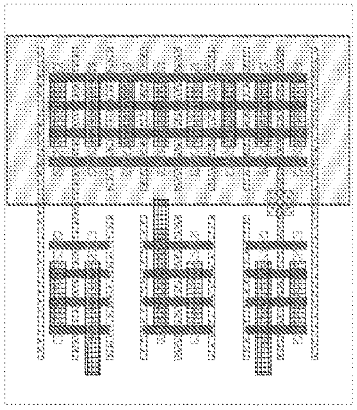
FIG. 1303B
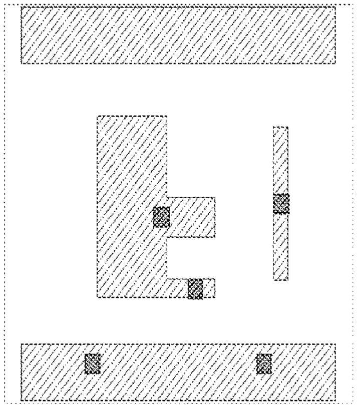
FIG. 1303C
*M* PDF Solutions, Inc.

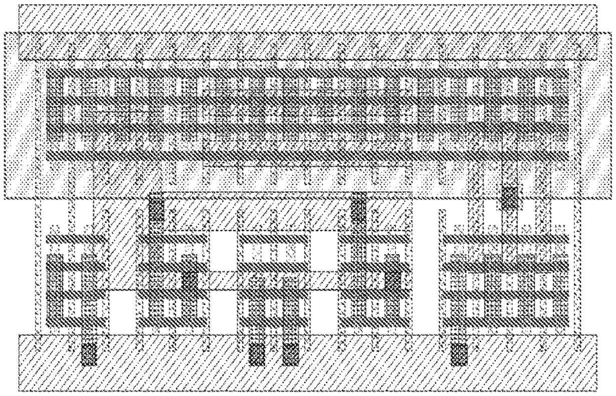
FIG. 1304A
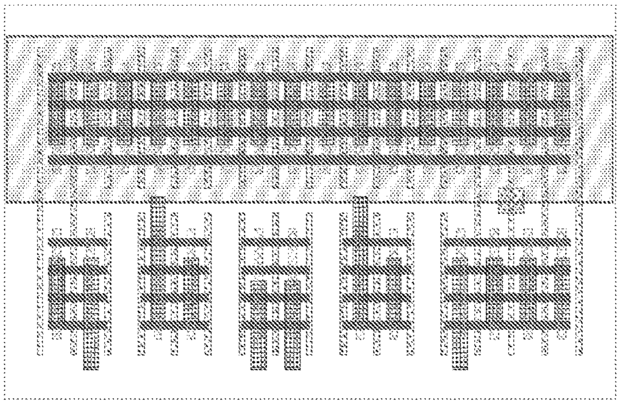
FIG. 1304B
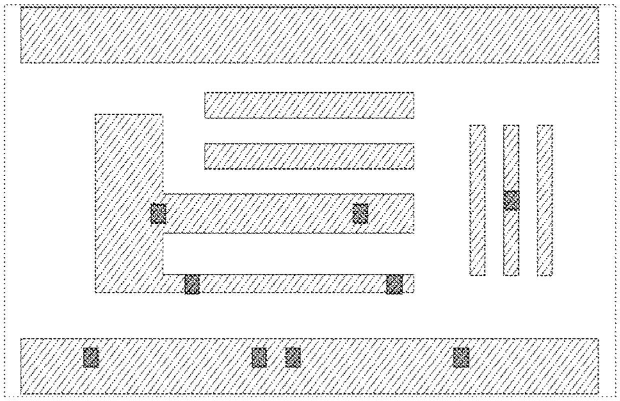
FIG. 1304C

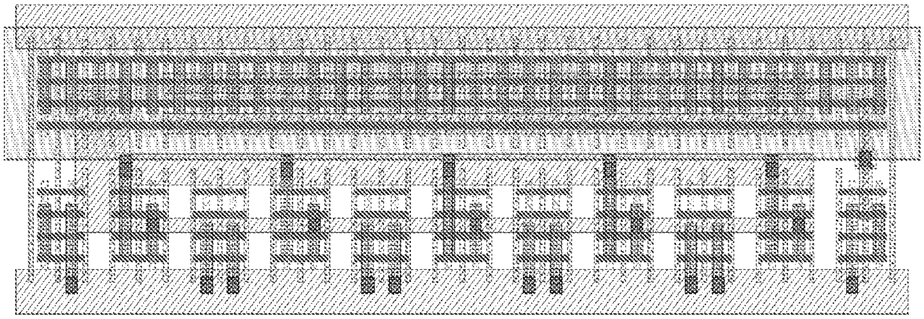
FIG. 1305A
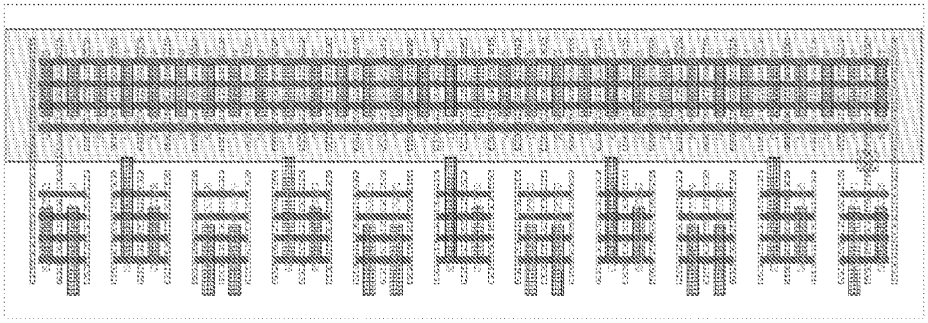
FIG. 1305B
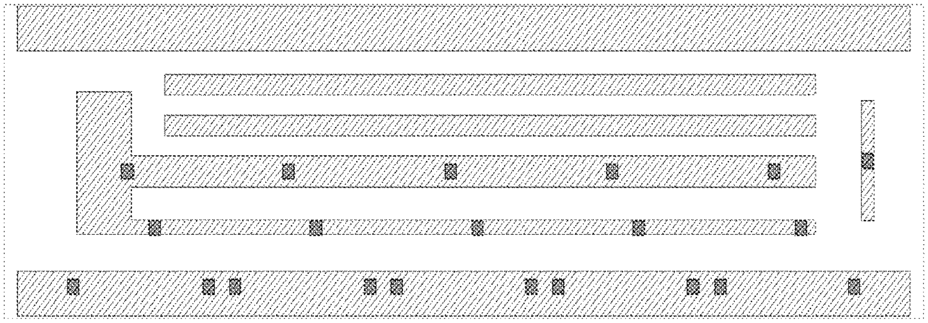
FIG. 1305C
*M* PDF Solutions, Inc.

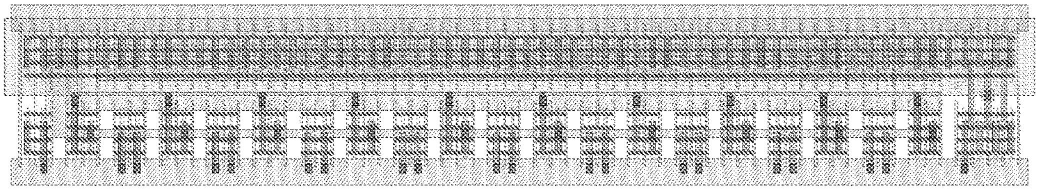
FIG. 1306A
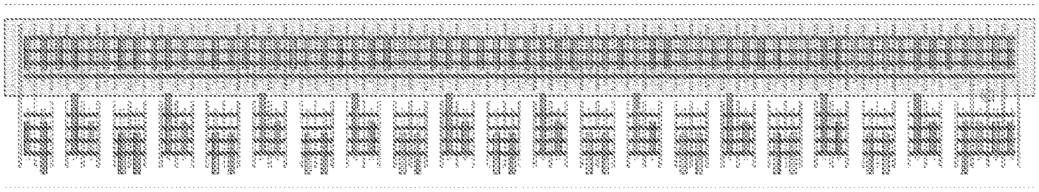
FIG. 1306B
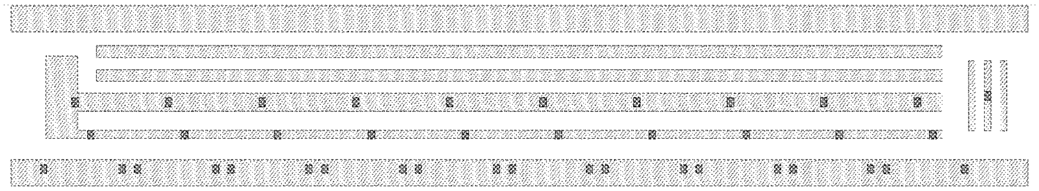
FIG. 1306C
*M* PDF Solutions, Inc.

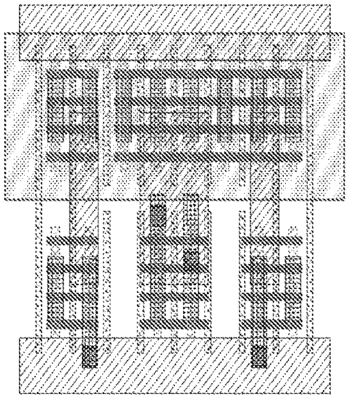
FIG. 1307A
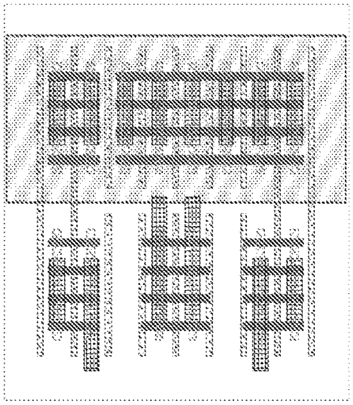
FIG. 1307B
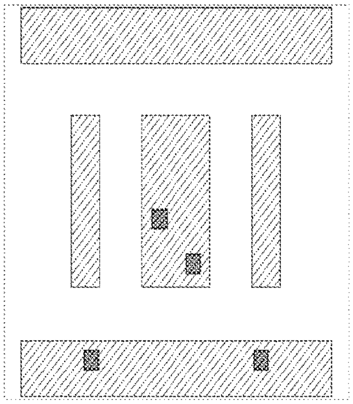
FIG. 1307C

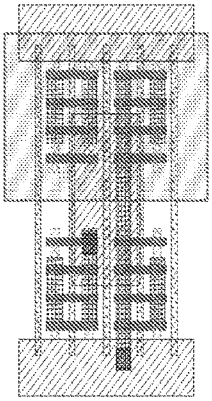
FIG. 1308A
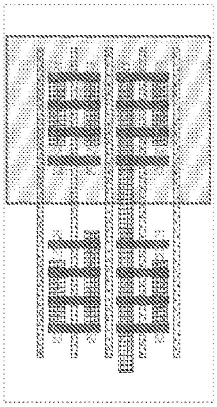
FIG. 1308B
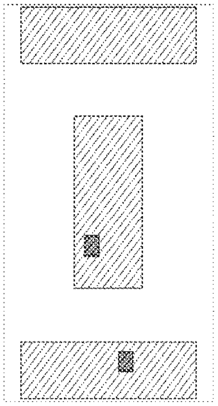
FIG. 1308C

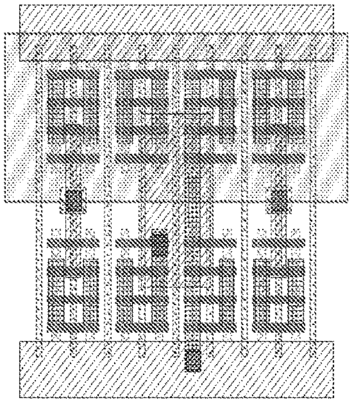
FIG. 1309A
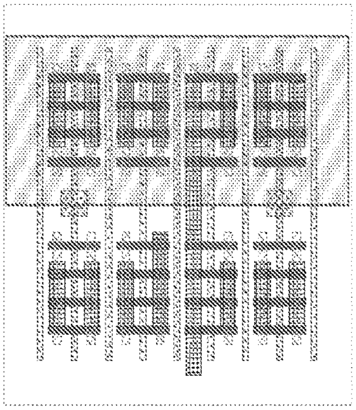
FIG. 1309B
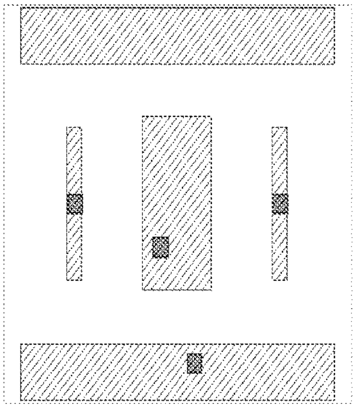
FIG. 1309C

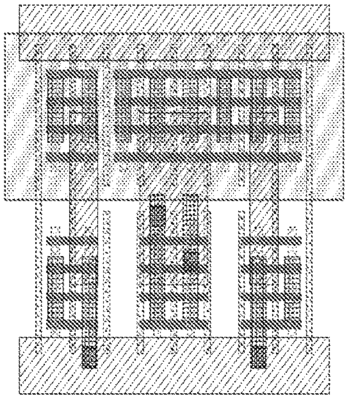
FIG. 1310A
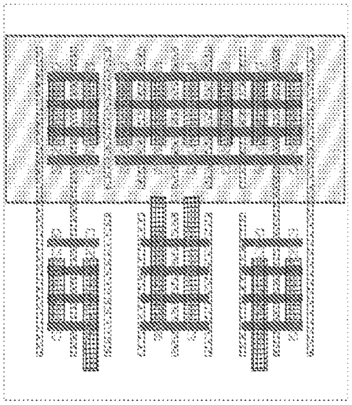
FIG. 1310B
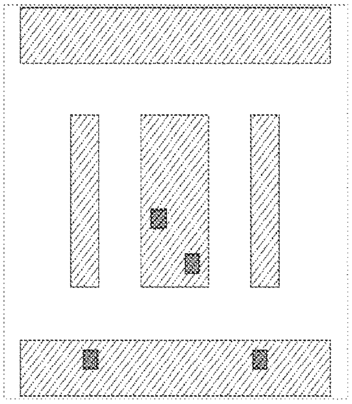
FIG. 1310C

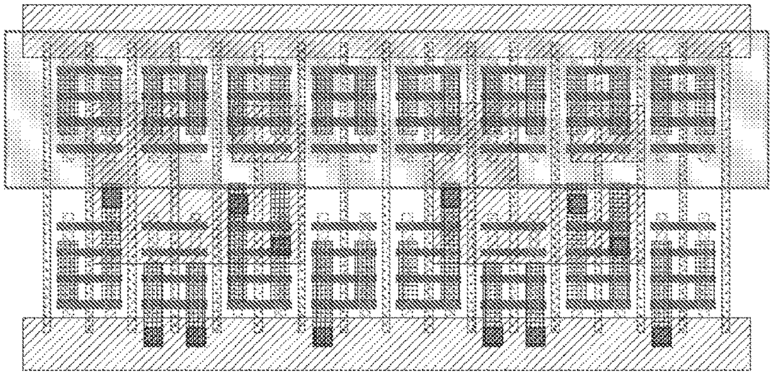
FIG. 1311A
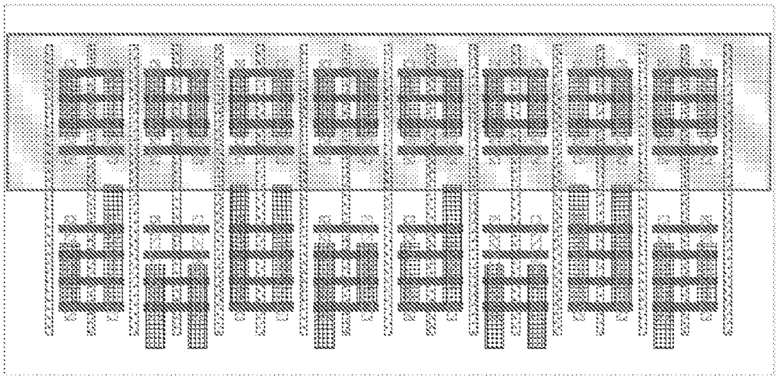
FIG. 1311B
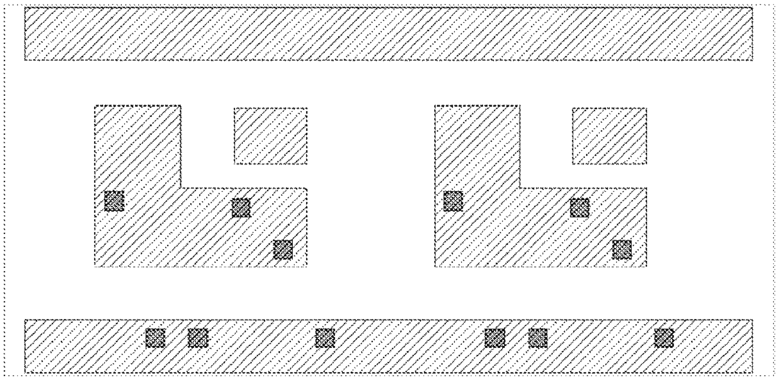
FIG. 1311C

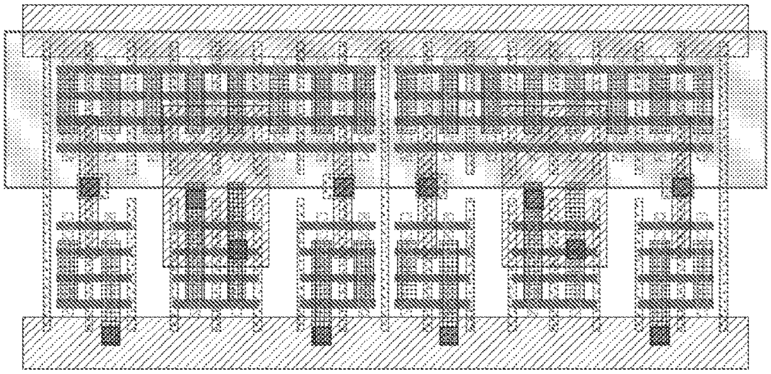
FIG. 1312A
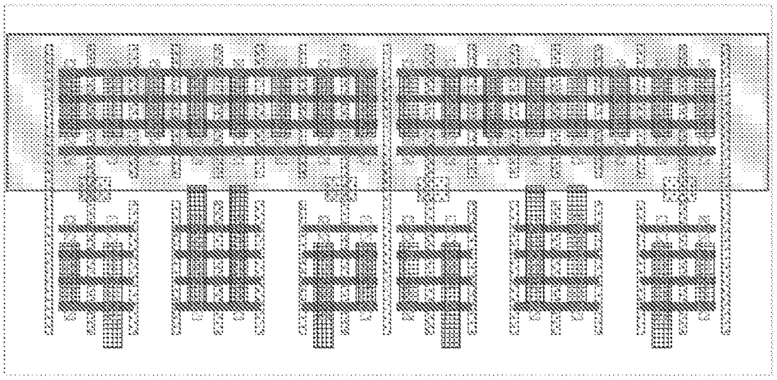
FIG. 1312B
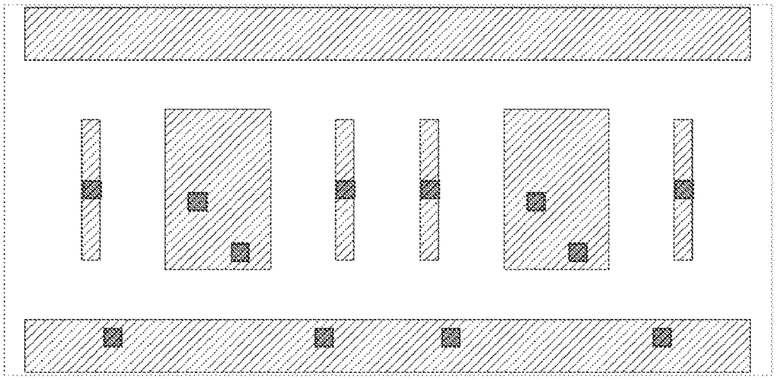
FIG. 1312C

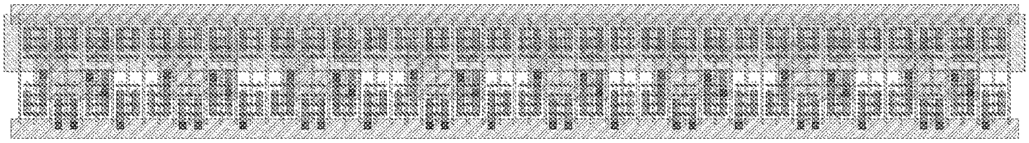
FIG. 1313A
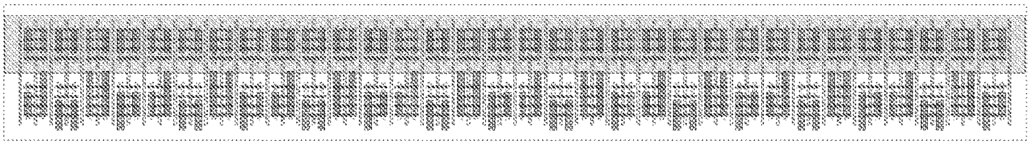
FIG. 1313B
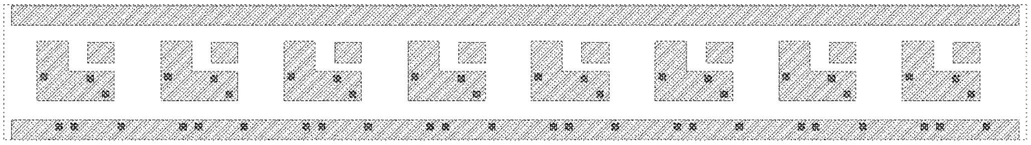
FIG. 1313C

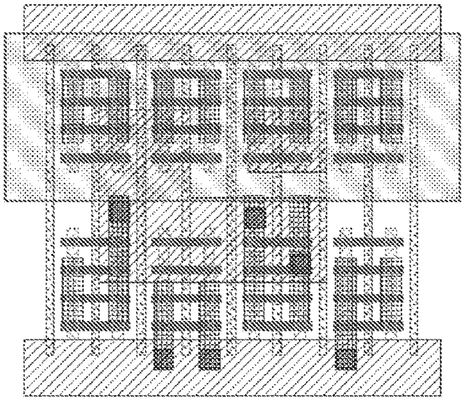
FIG. 1314A
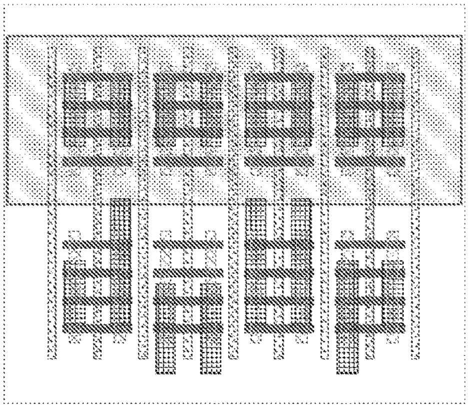
FIG. 1314B
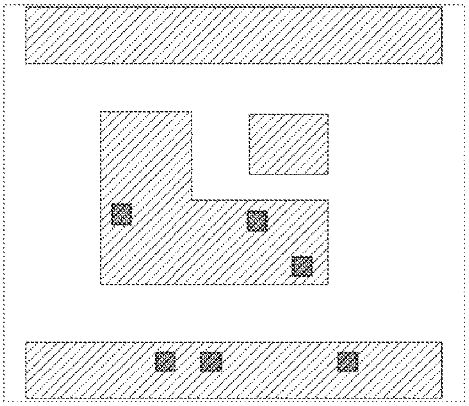
FIG. 1314C

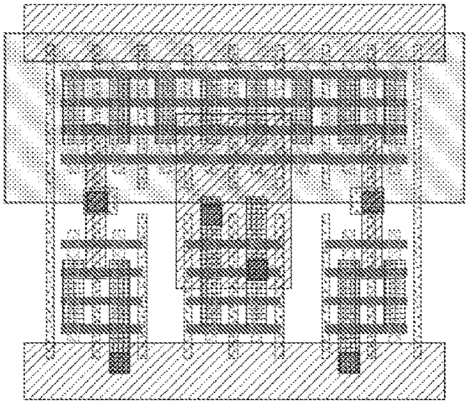
FIG. 1315A
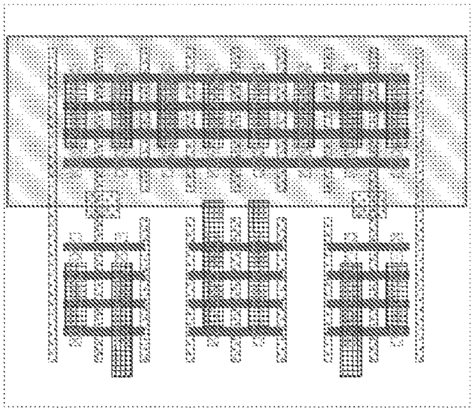
FIG. 1315B
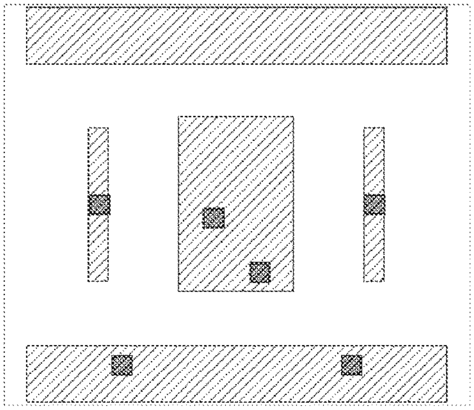
FIG. 1315C

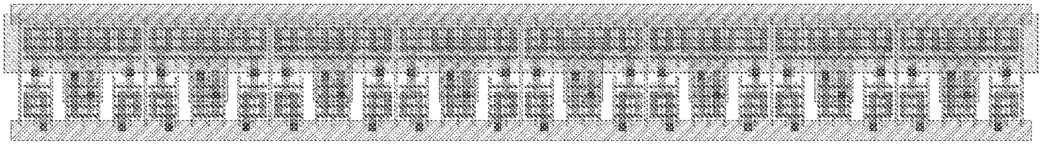
FIG. 1316A
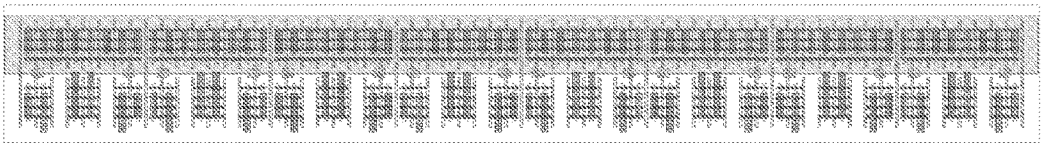
FIG. 1316B
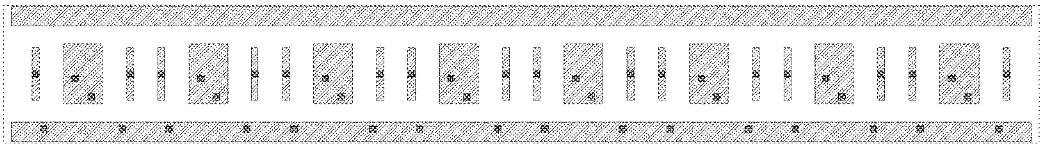
FIG. 1316C

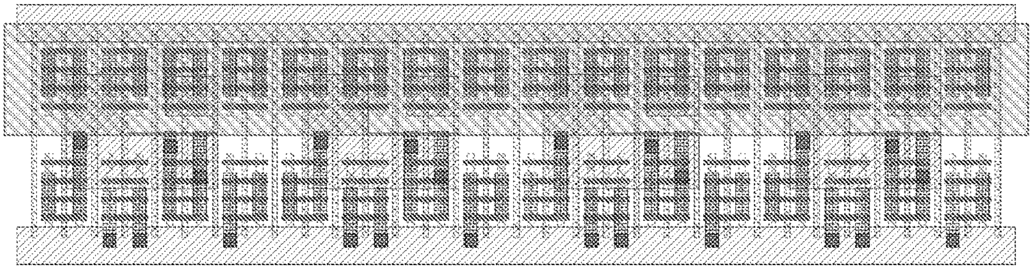
FIG. 1317A
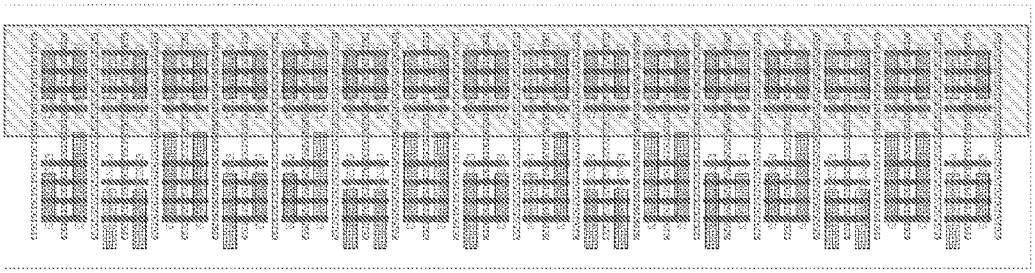
FIG. 1317B
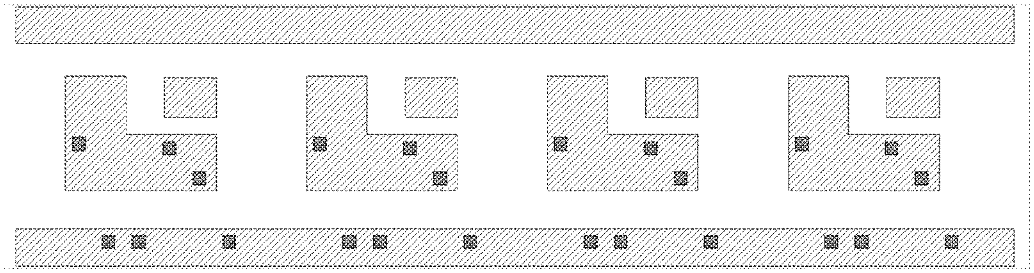
FIG. 1317C
*M* PDF Solutions, Inc.

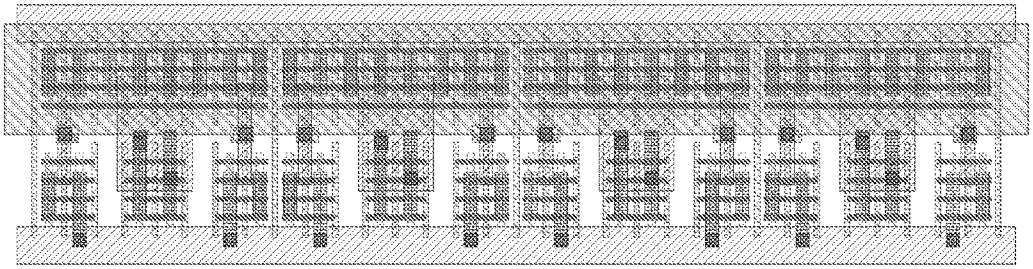
FIG. 1318A
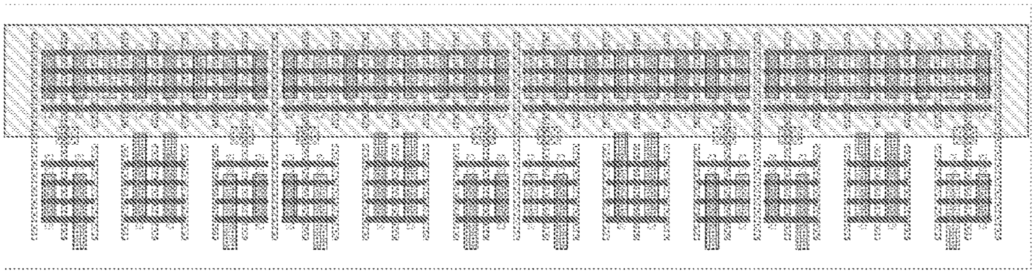
FIG. 1318B
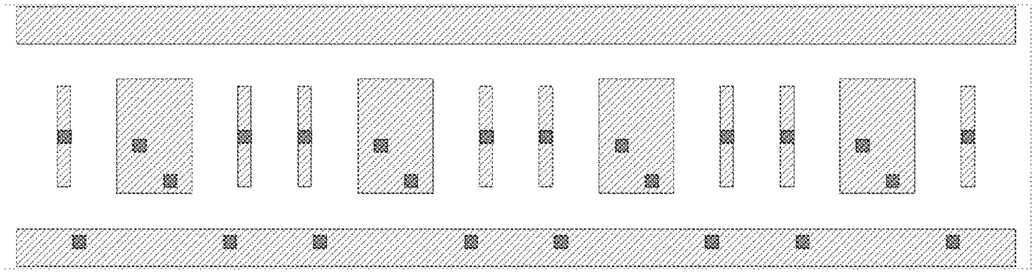
FIG. 1318C

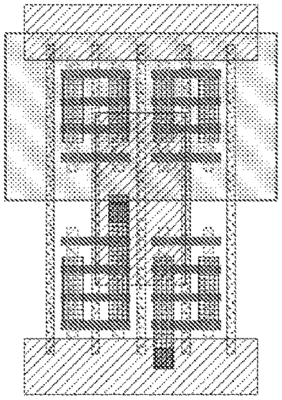
FIG. 1319A
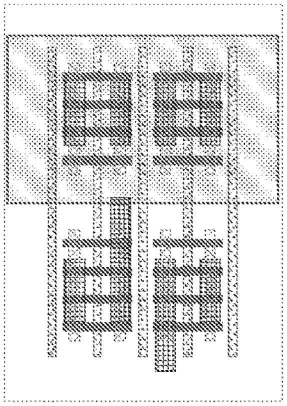
FIG. 1319B
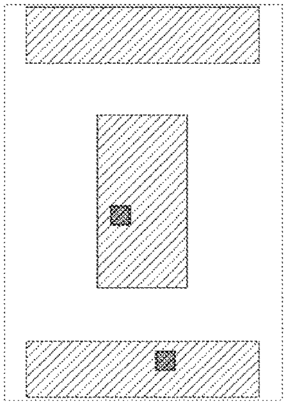
FIG. 1319C
*M* PDF Solutions, Inc.

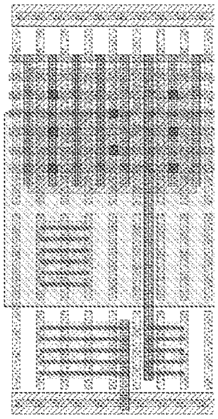
FIG. 1320A
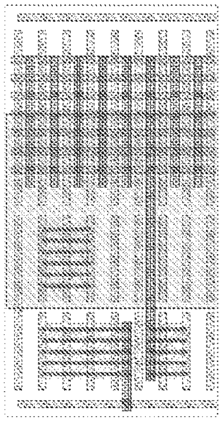
FIG. 1320B
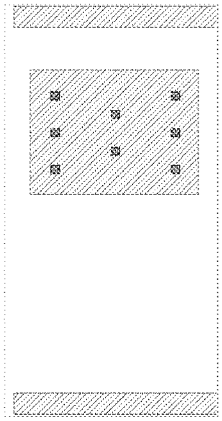
FIG. 1320C
*M* PDF Solutions, Inc.

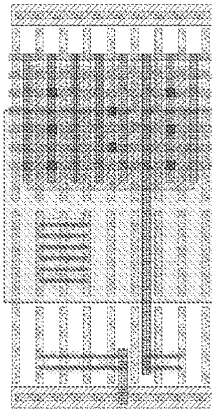
FIG. 1321A
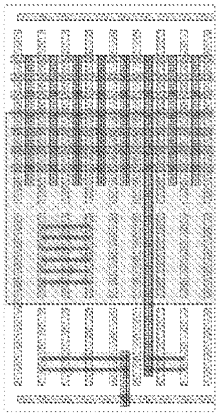
FIG. 1321B
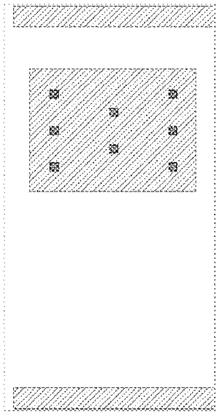
FIG. 1321C

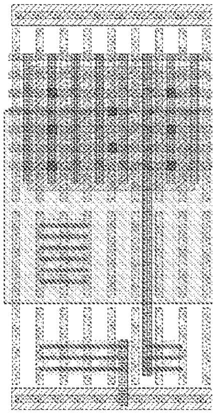
FIG. 1322A
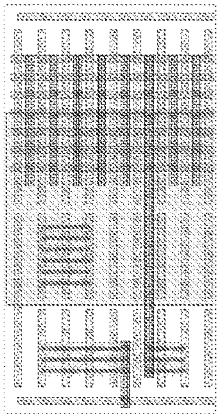
FIG. 1322B
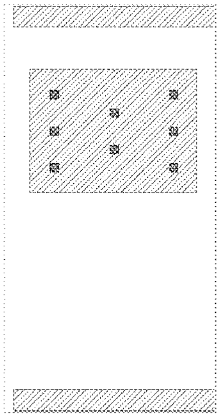
FIG. 1322C

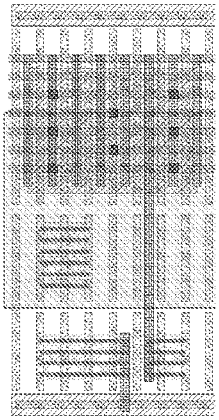
FIG. 1323A
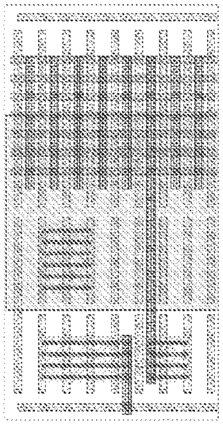
FIG. 1323B
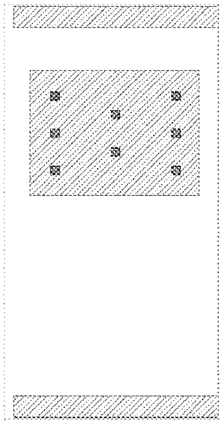
FIG. 1323C
*M* PDF Solutions, Inc.

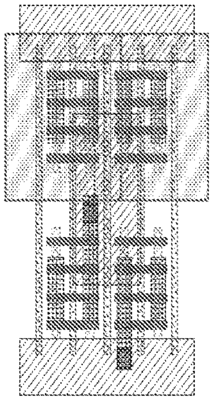
FIG. 1324A
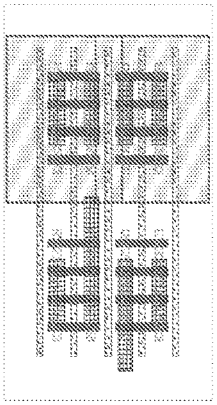
FIG. 1324B
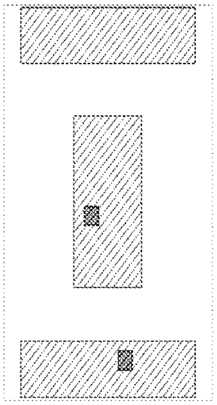
FIG. 1324C
*M* PDF Solutions, Inc.

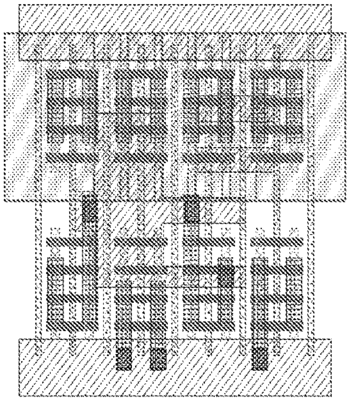
FIG. 1325A
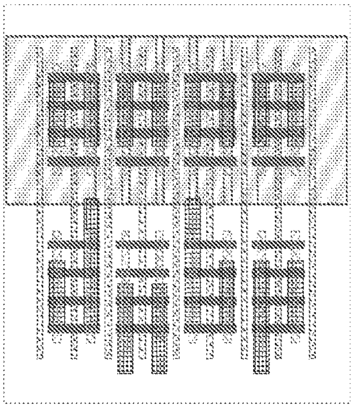
FIG. 1325B
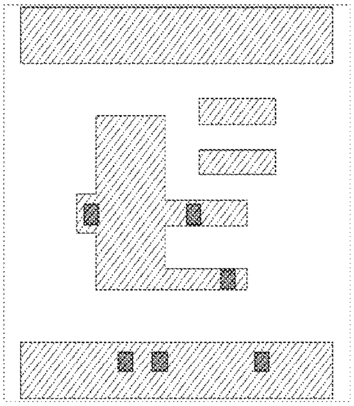
FIG. 1325C

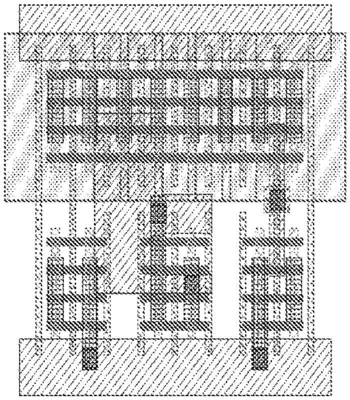
FIG. 1326A
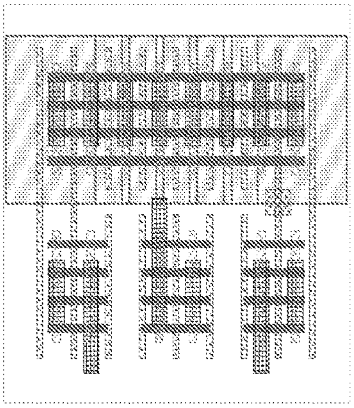
FIG. 1326B
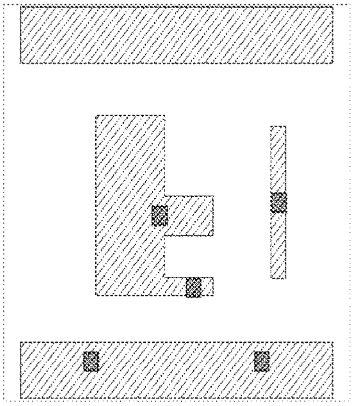
FIG. 1326C

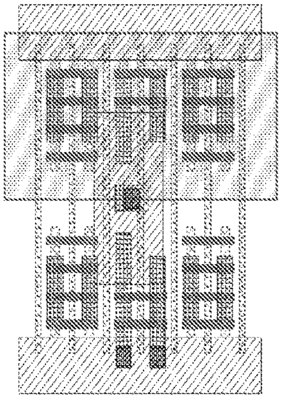
FIG. 1327A
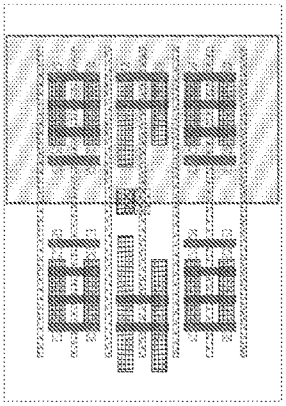
FIG. 1327B
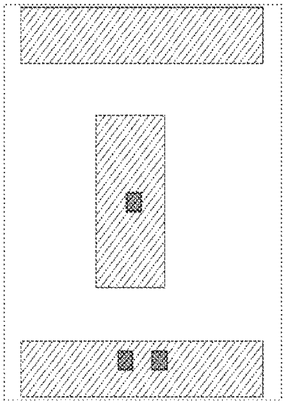
FIG. 1327C

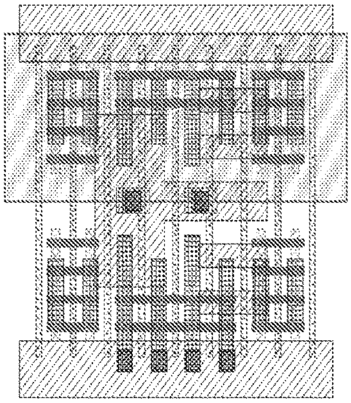
FIG. 1328A
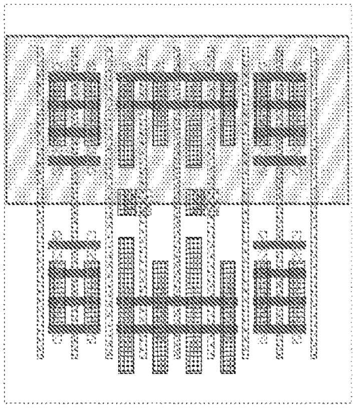
FIG. 1328B
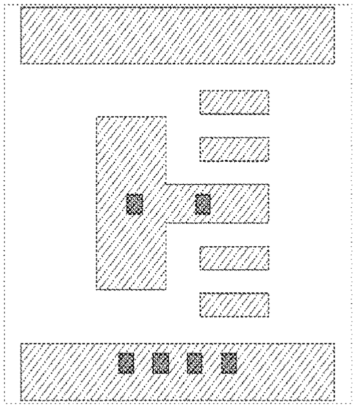
FIG. 1328C

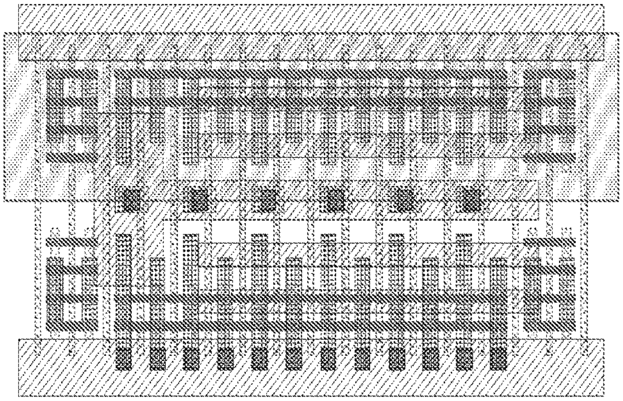
FIG. 1329A
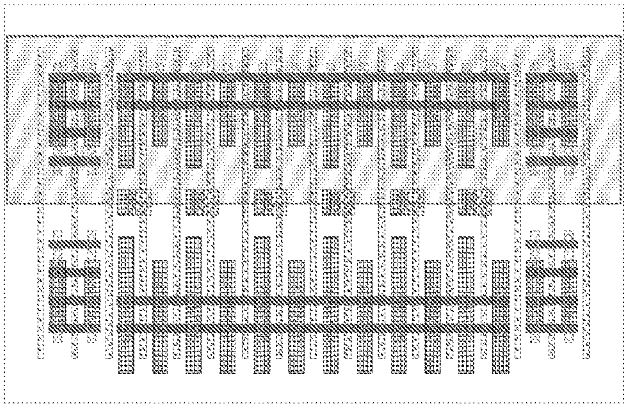
FIG. 1329B
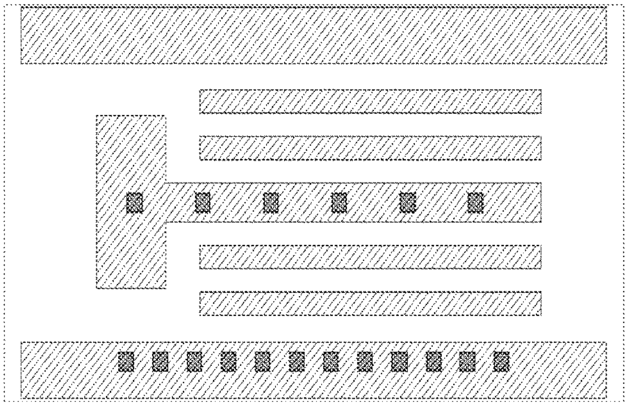
FIG. 1329C
*M* PDF Solutions, Inc.

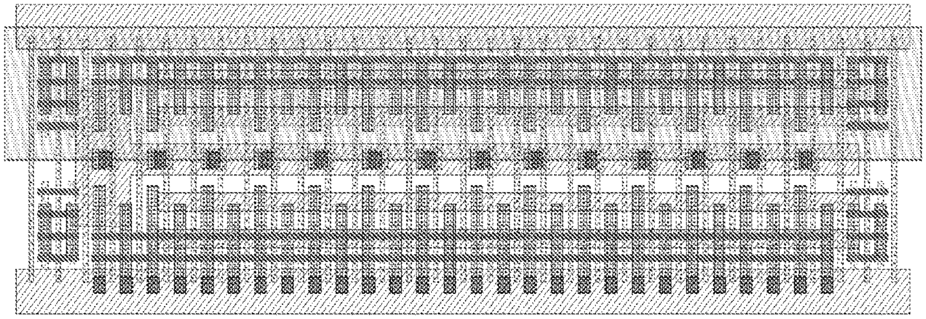
FIG. 1330A
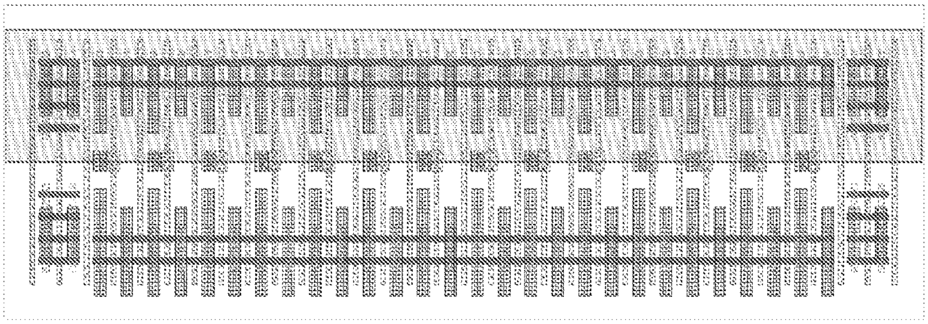
FIG. 1330B
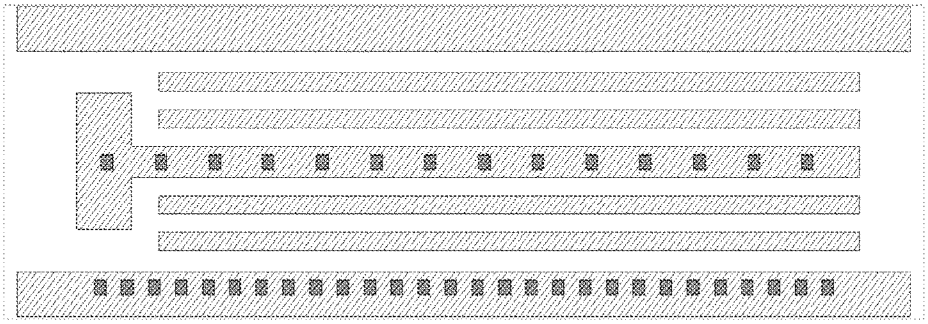
FIG. 1330C

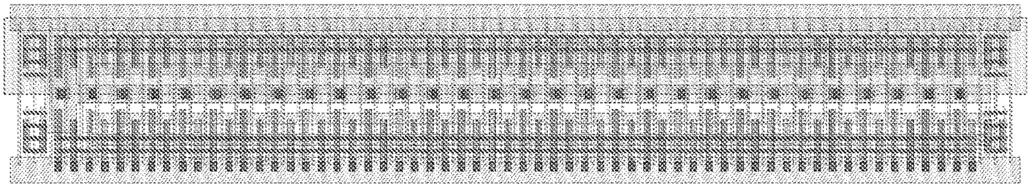
FIG. 1331A
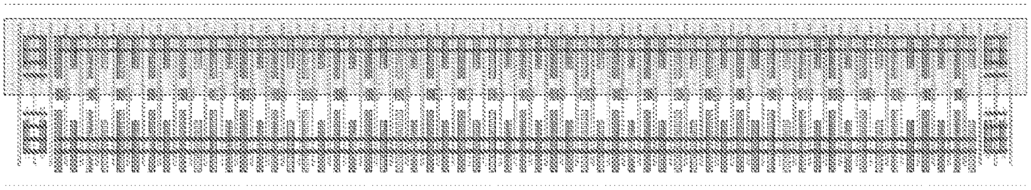
FIG. 1331B
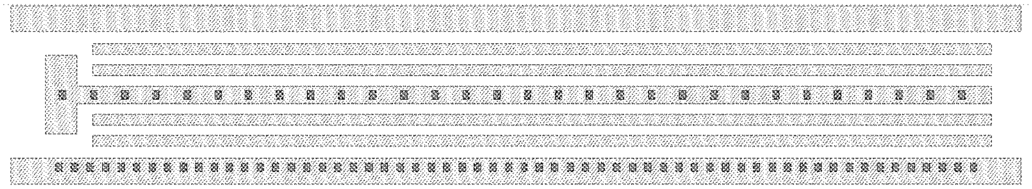
FIG. 1331C

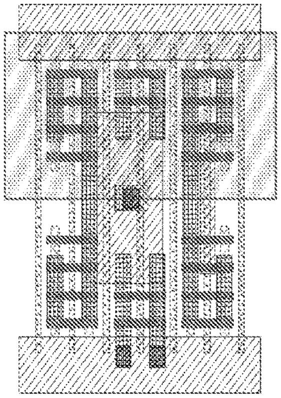
FIG. 1332A
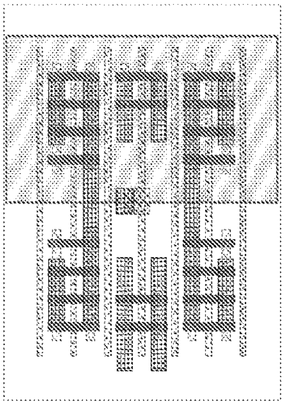
FIG. 1332B
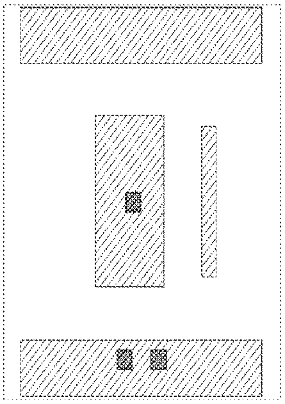
FIG. 1332C

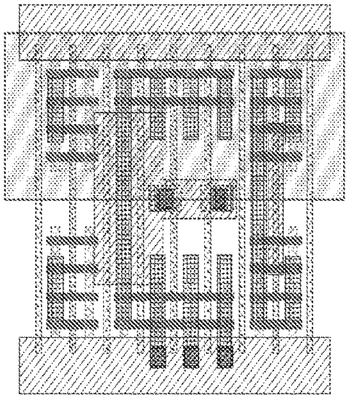
FIG. 1333A
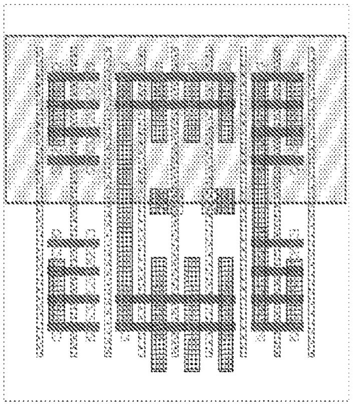
FIG. 1333B
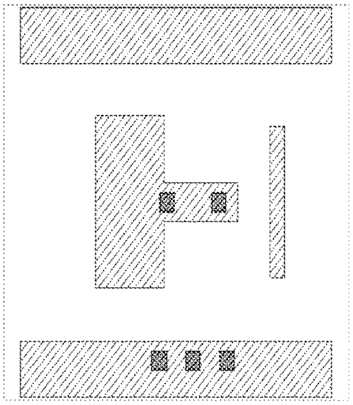
FIG. 1333C

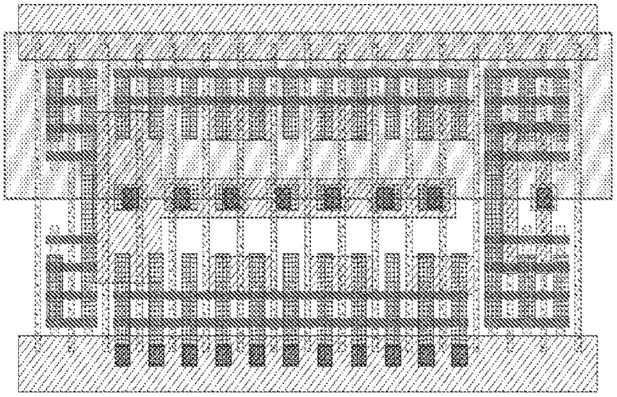
FIG. 1334A
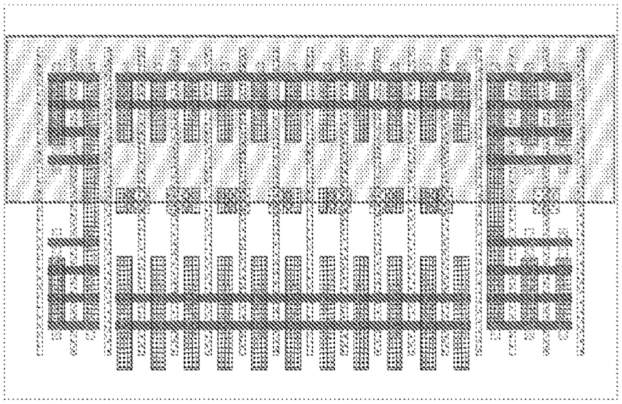
FIG. 1334B
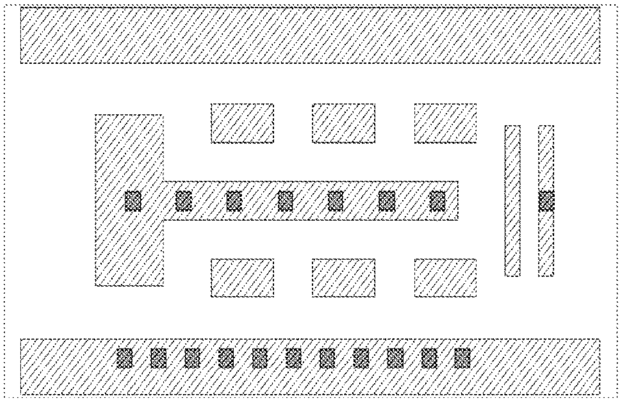
FIG. 1334C

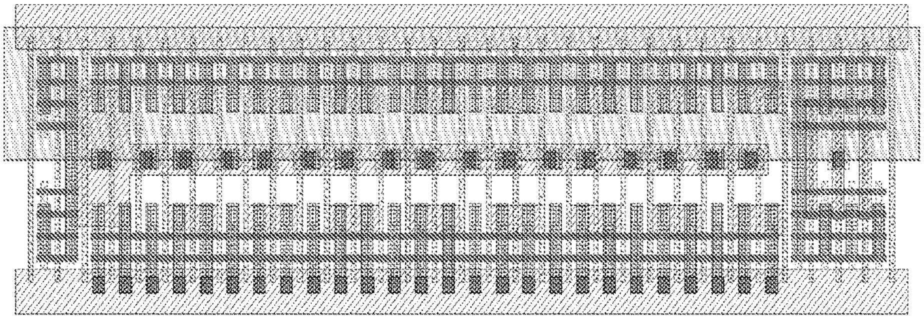
FIG. 1335A
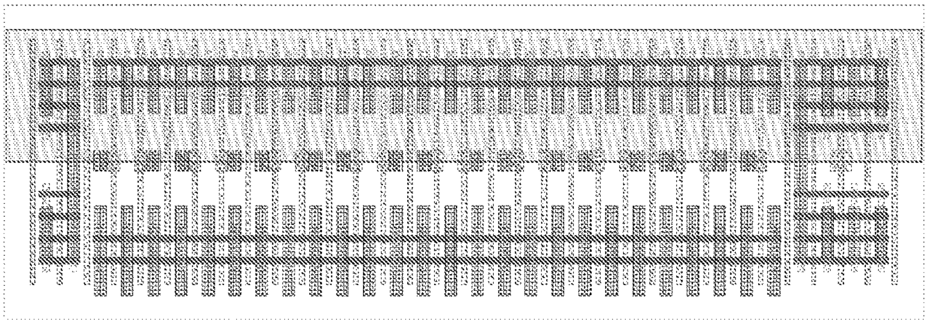
FIG. 1335B
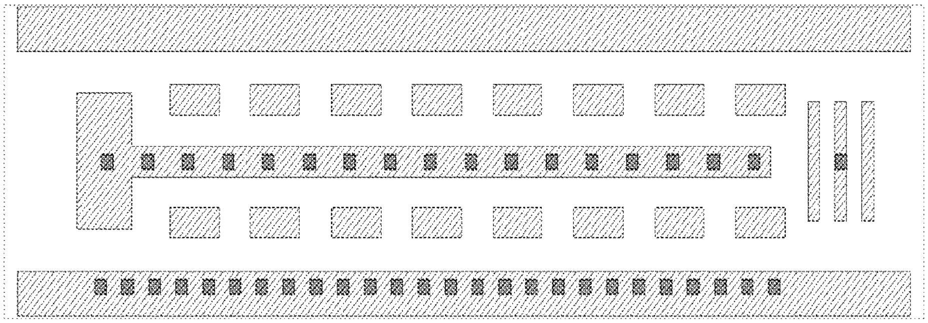
FIG. 1335C
*M* PDF Solutions, Inc.

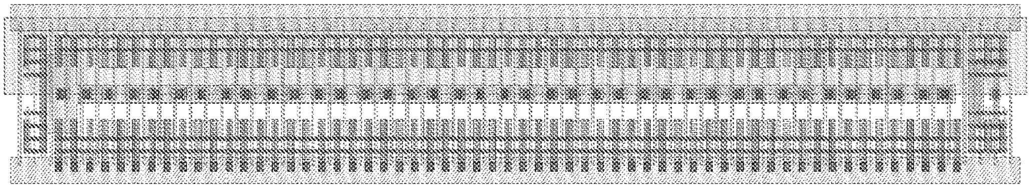
FIG. 1336A
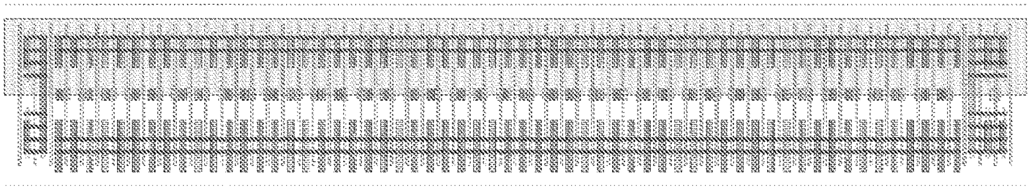
FIG. 1336B
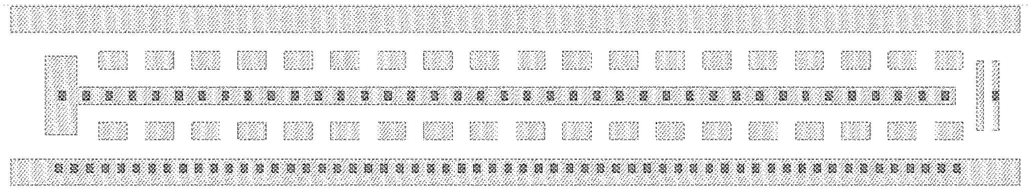
FIG. 1336C

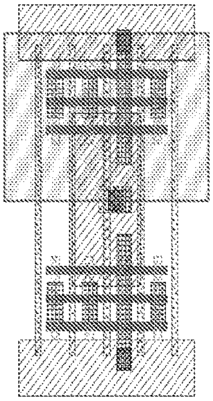
FIG. 1337A
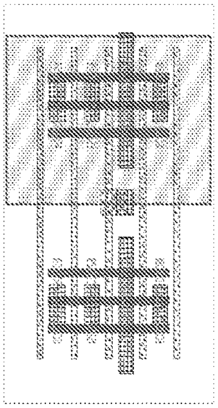
FIG. 1337B
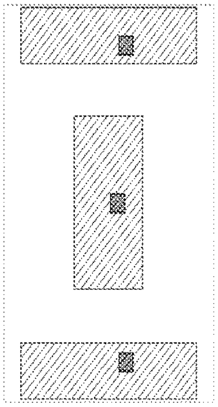
FIG. 1337C

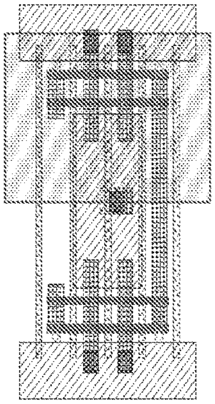
FIG. 1338A
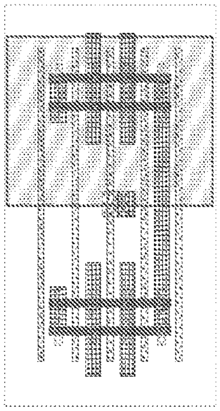
FIG. 1338B
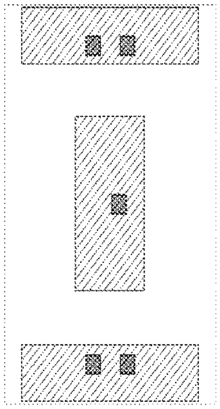
FIG. 1338C

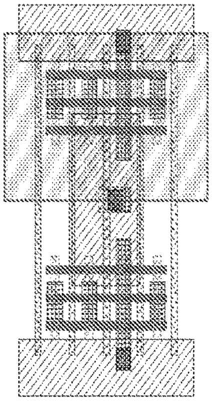
FIG. 1339A
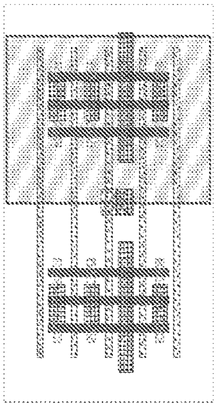
FIG. 1339B
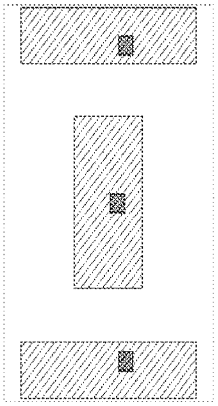
FIG. 1339C

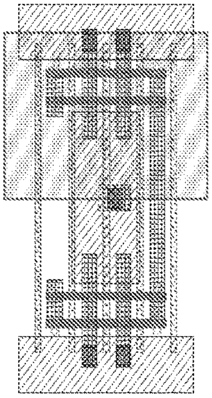
FIG. 1340A
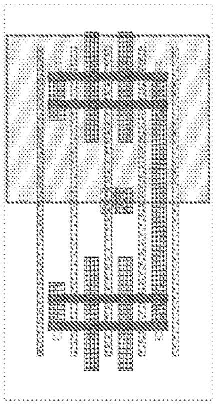
FIG. 1340B
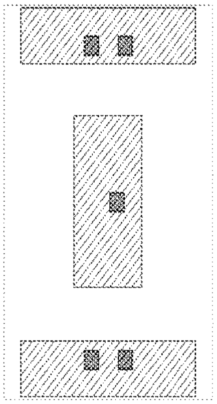
FIG. 1340C
*M* PDF Solutions, Inc.

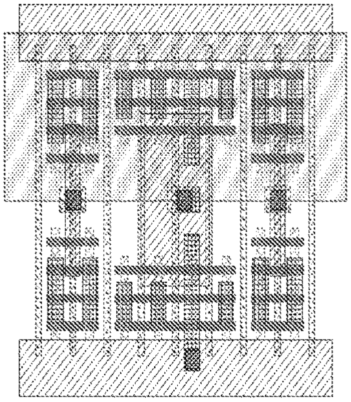
FIG. 1341A
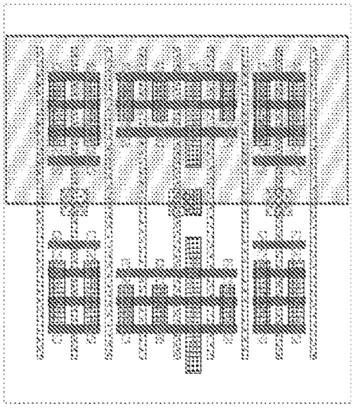
FIG. 1341B
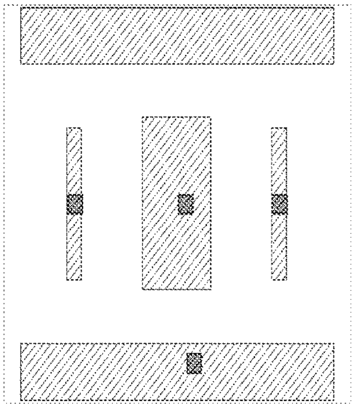
FIG. 1341C

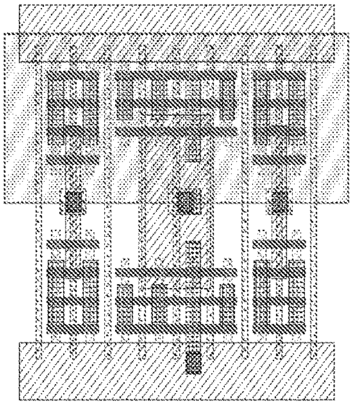
FIG. 1342A
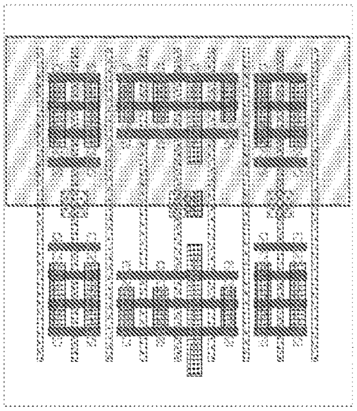
FIG. 1342B
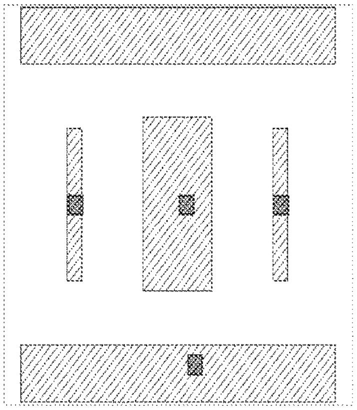
FIG. 1342C

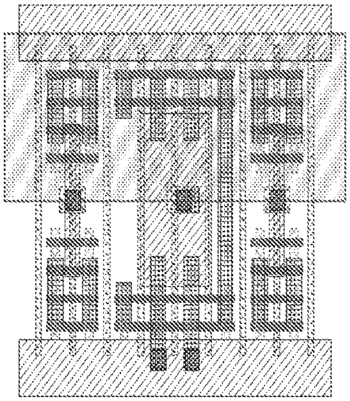
FIG. 1343A
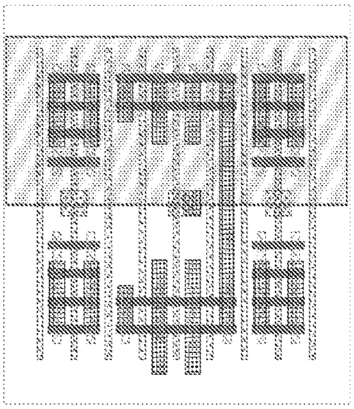
FIG. 1343B
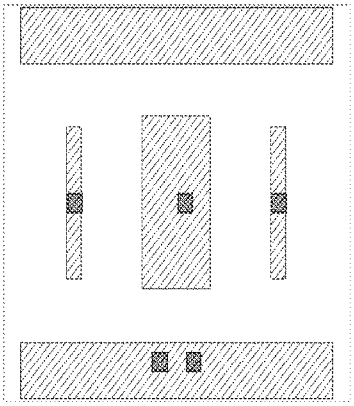
FIG. 1343C

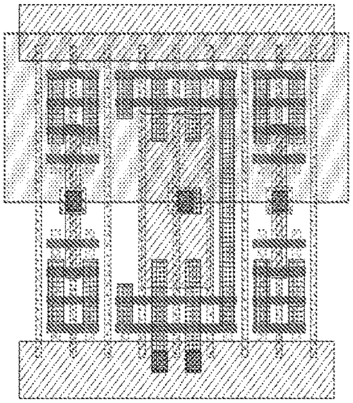
FIG. 1344A
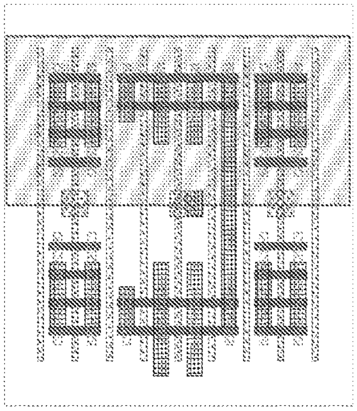
FIG. 1344B
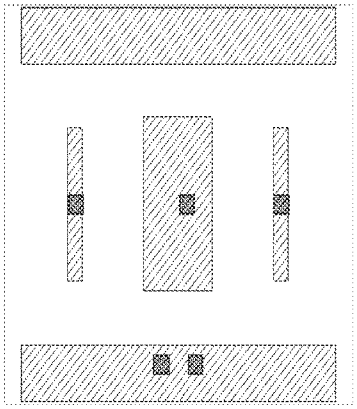
FIG. 1344C

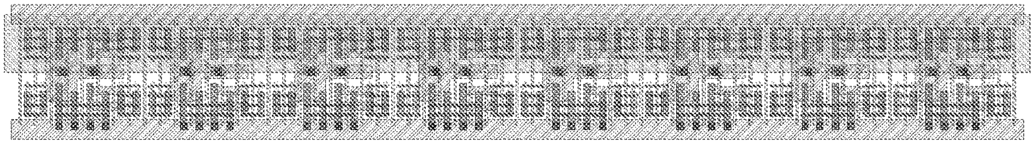
FIG. 1345A
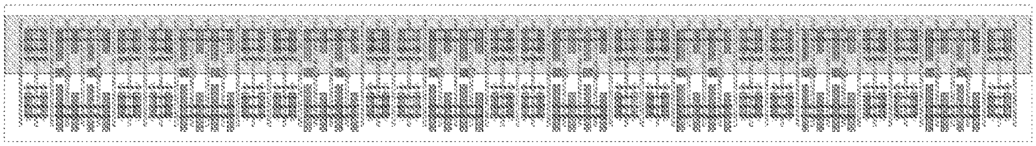
FIG. 1345B
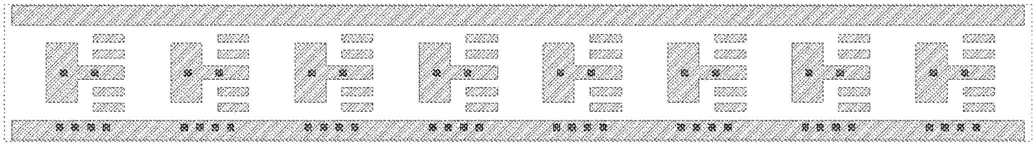
FIG. 1345C

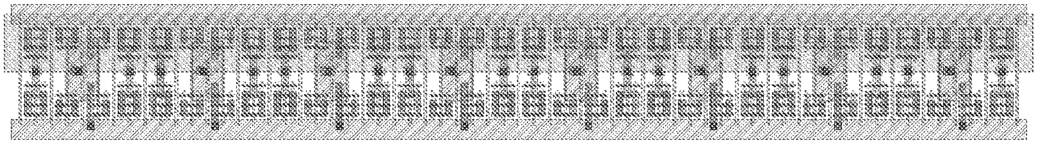
FIG. 1346A
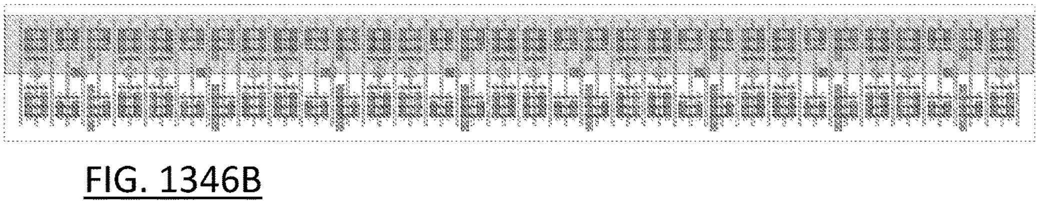
FIG. 1346B
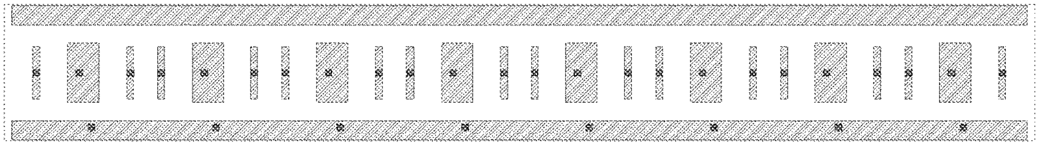
FIG. 1346C

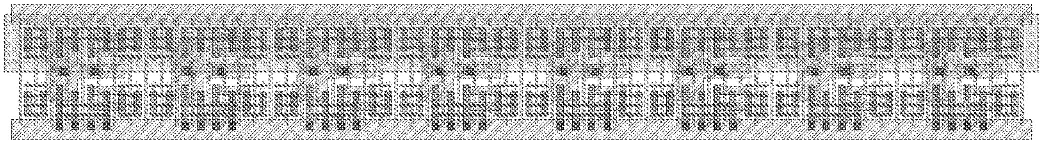
FIG. 1347A
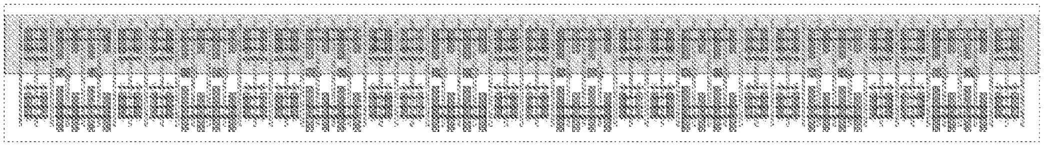
FIG. 1347B
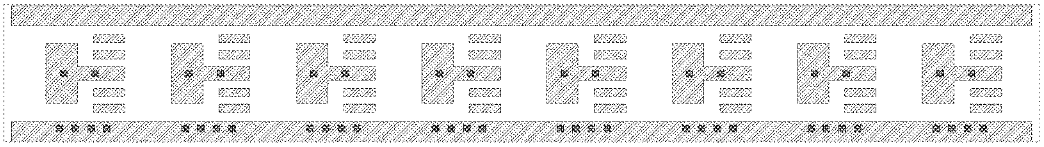
FIG. 1347C

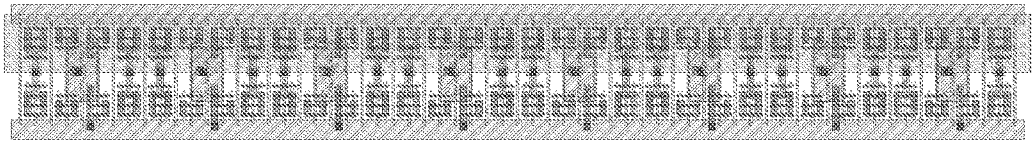
FIG. 1348A
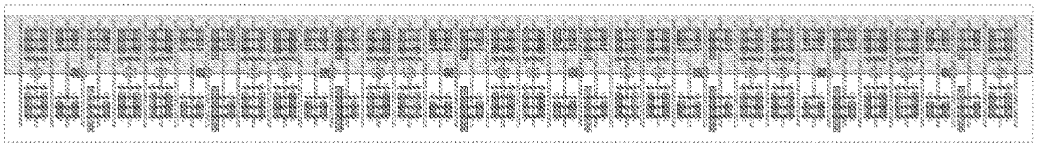
FIG. 1348B
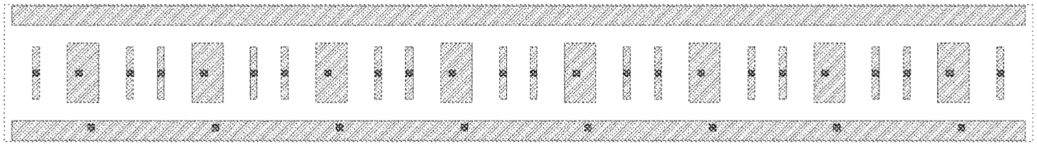
FIG. 1348C

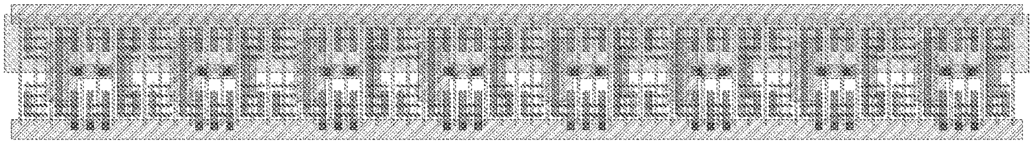
FIG. 1349A
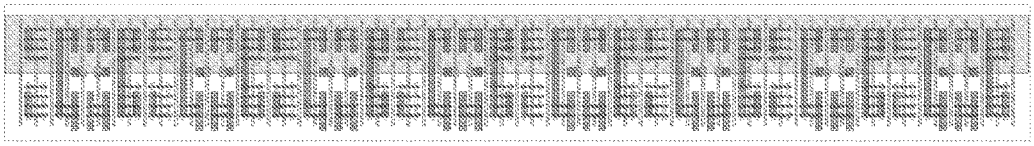
FIG. 1349B
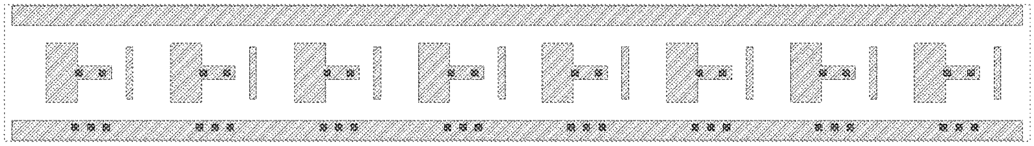
FIG. 1349C

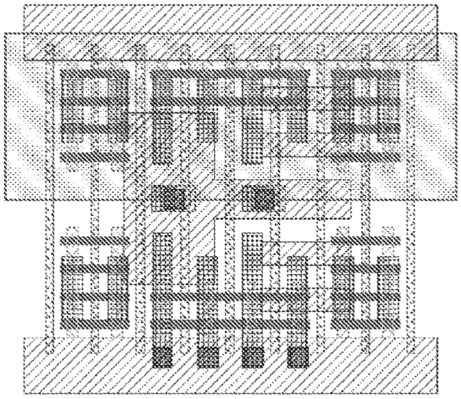
FIG. 1350A
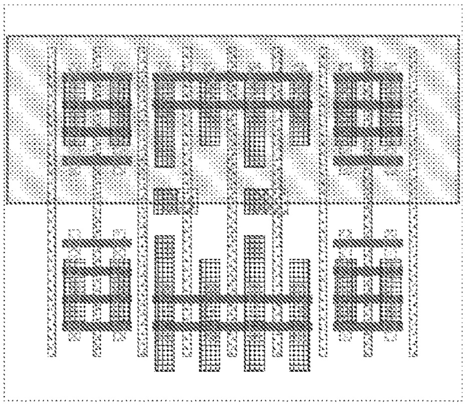
FIG. 1350B
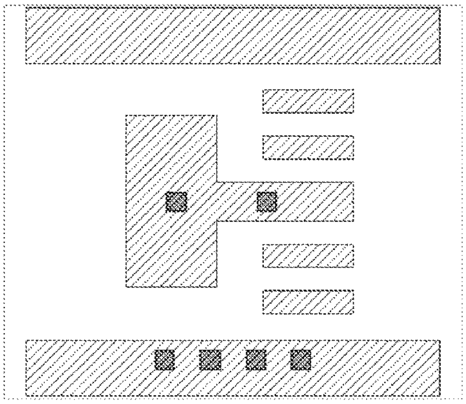
FIG. 1350C
*M* PDF Solutions, Inc.

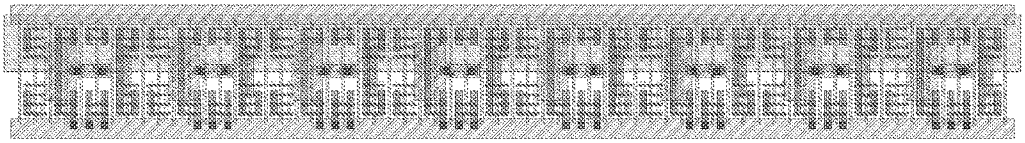
FIG. 1351A
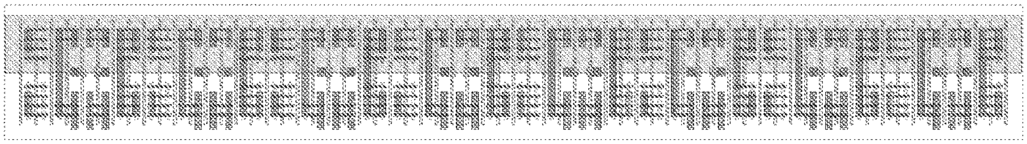
FIG. 1351B
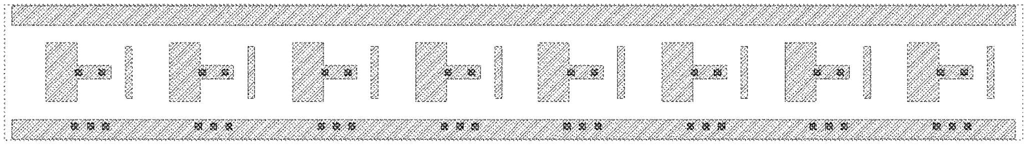
FIG. 1351C

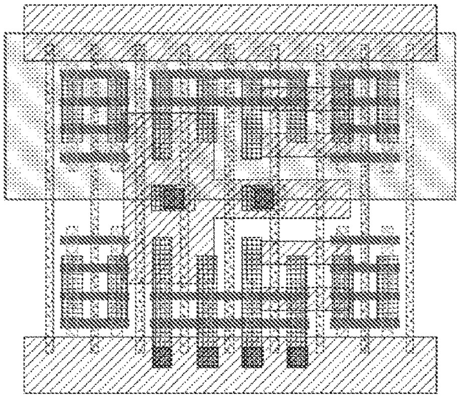
FIG. 1352A
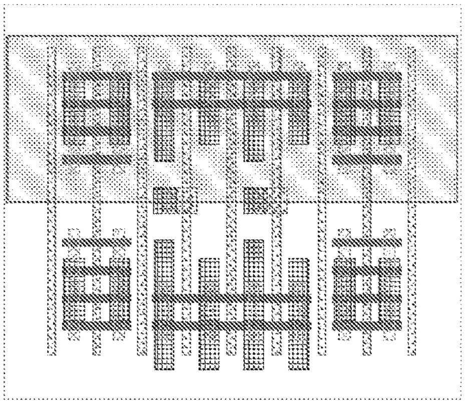
FIG. 1352B
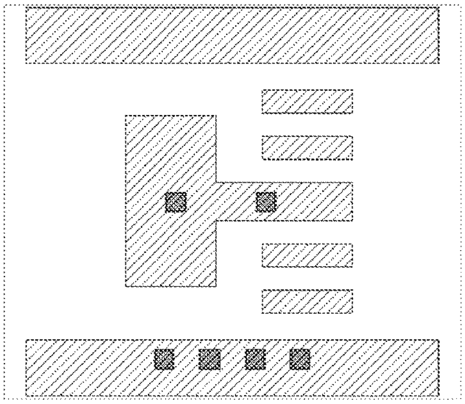
FIG. 1352C
*M* PDF Solutions, Inc.

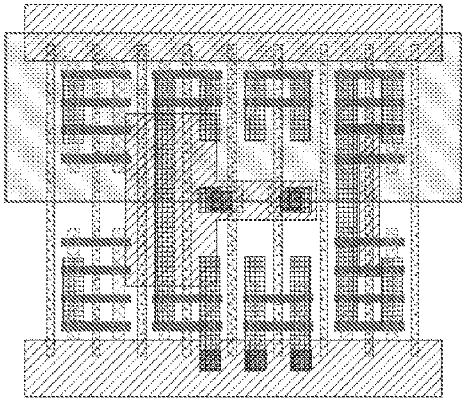
FIG. 1353A
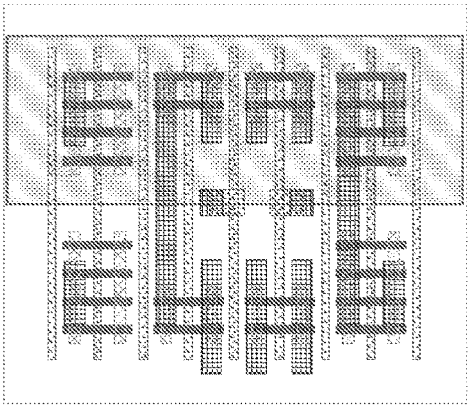
FIG. 1353B
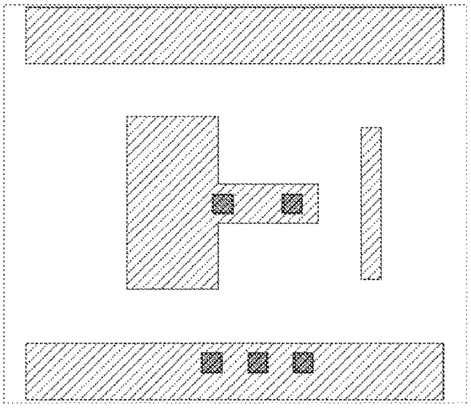
FIG. 1353C

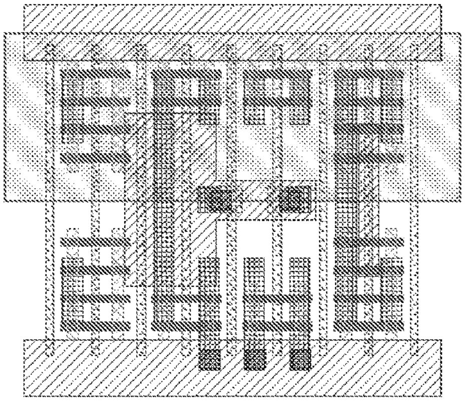
FIG. 1354A
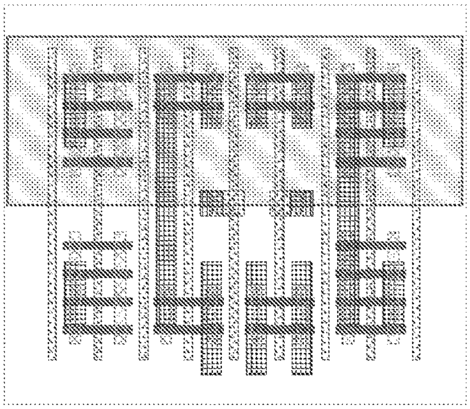
FIG. 1354B
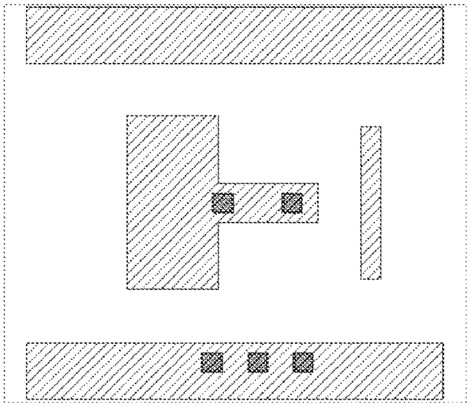
FIG. 1354C

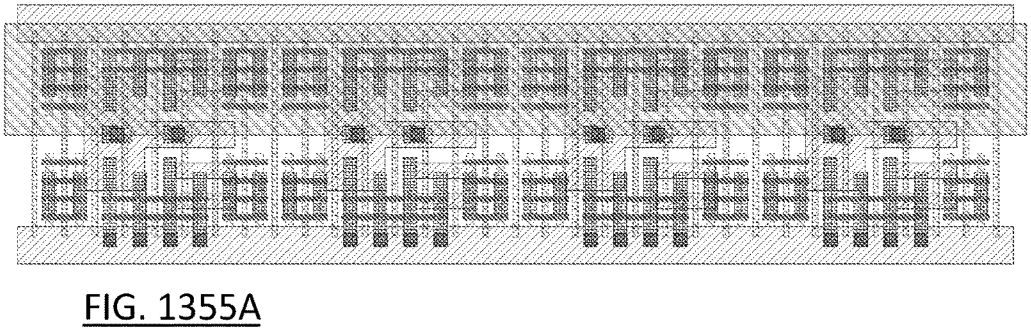
FIG. 1355A
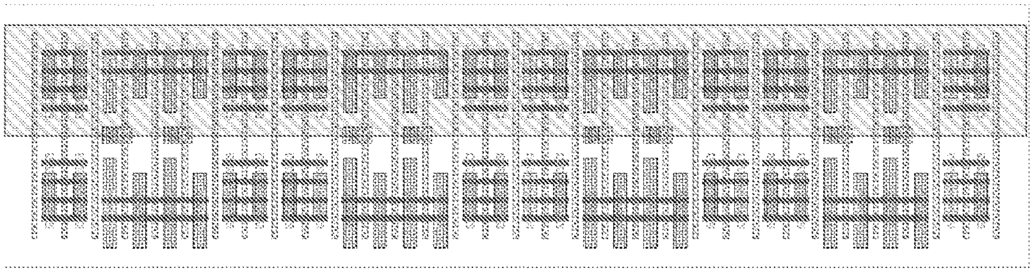
FIG. 1355B
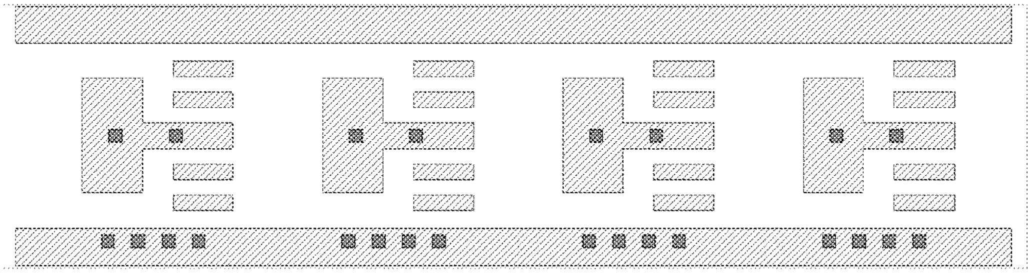
FIG. 1355C

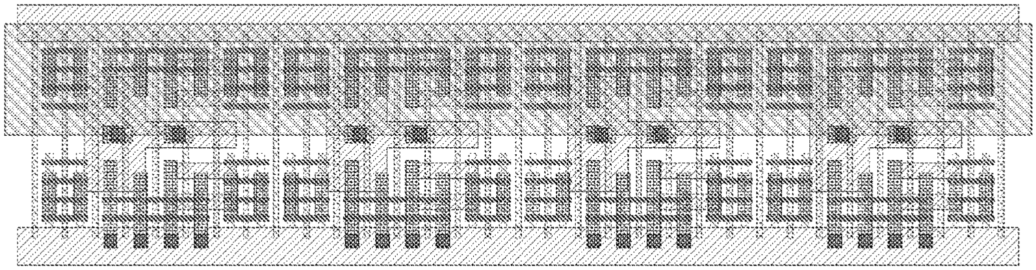
FIG. 1356A
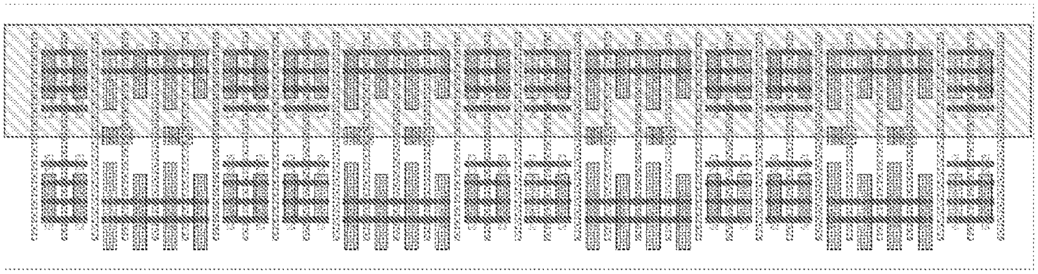
FIG. 1356B
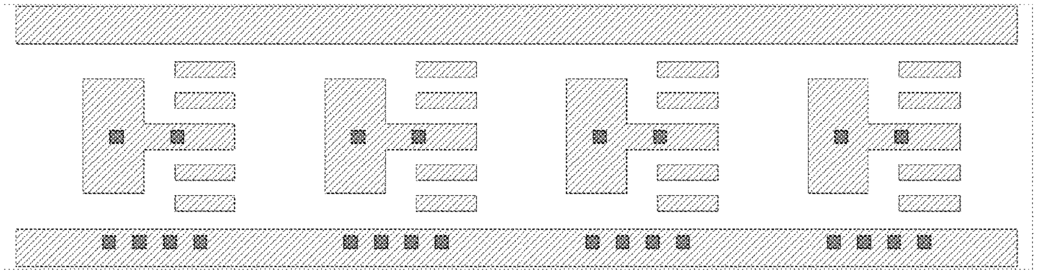
FIG. 1356C

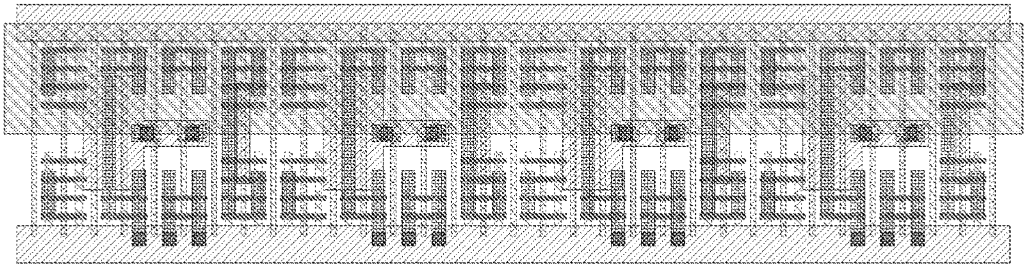
FIG. 1357A
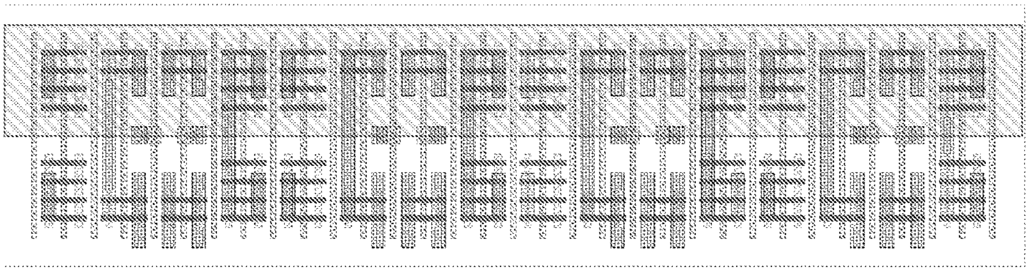
FIG. 1357B
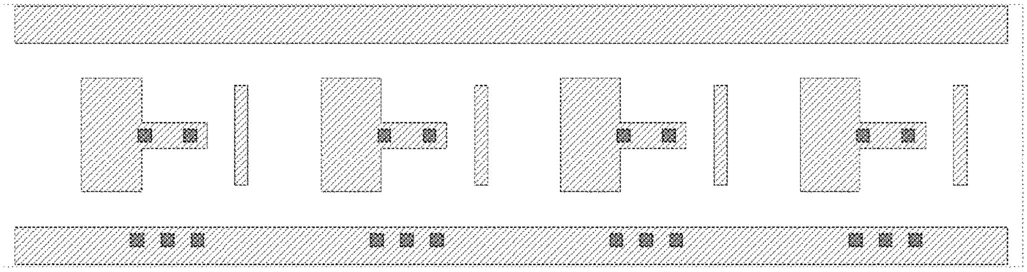
FIG. 1357C

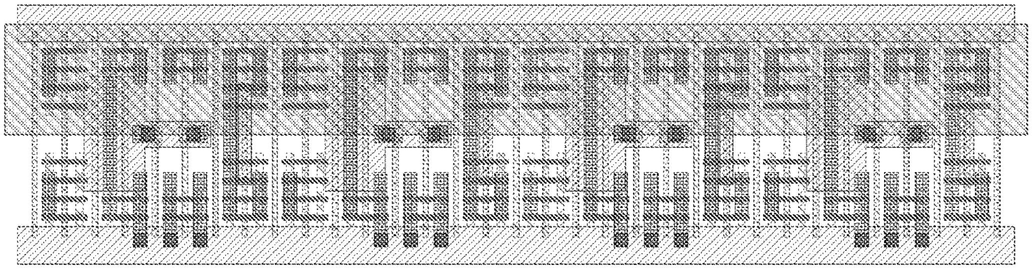
FIG. 1358A
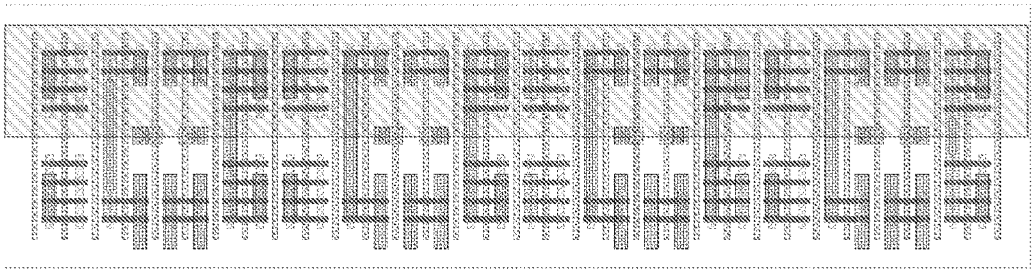
FIG. 1358B
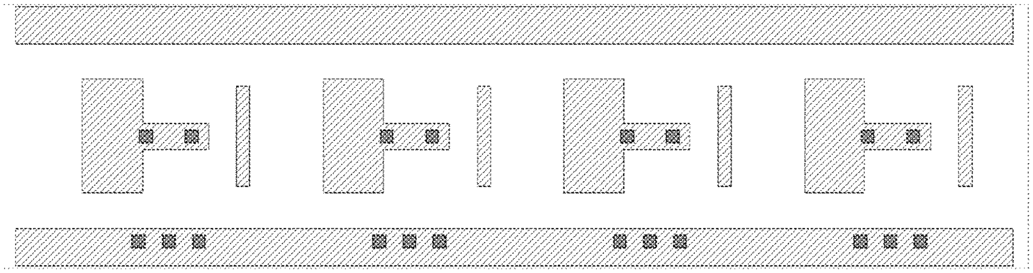
FIG. 1358C

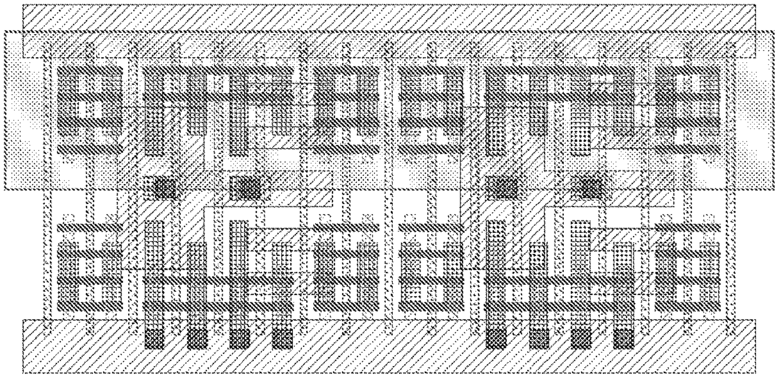
FIG. 1359A
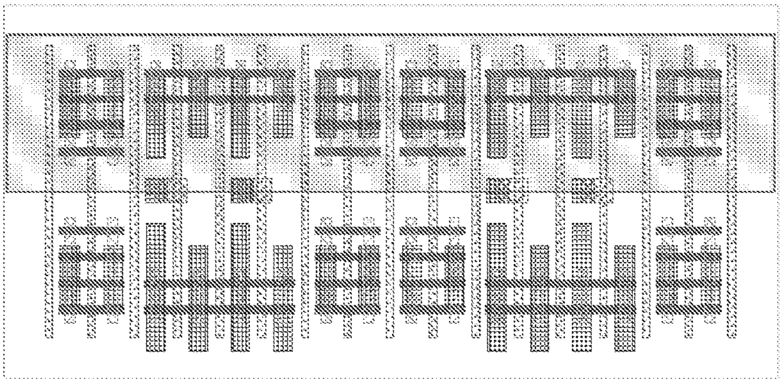
FIG. 1359B
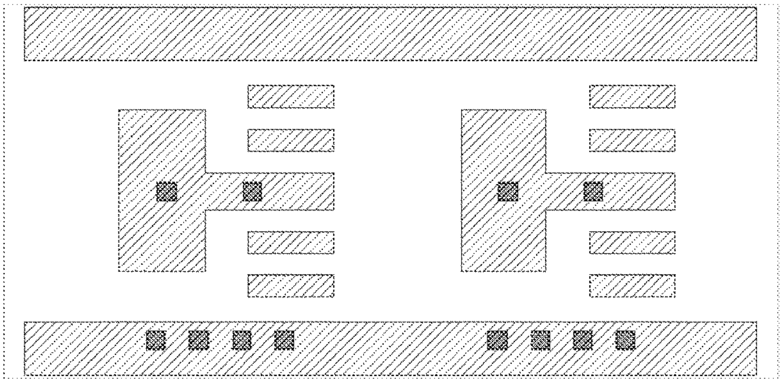
FIG. 1359C

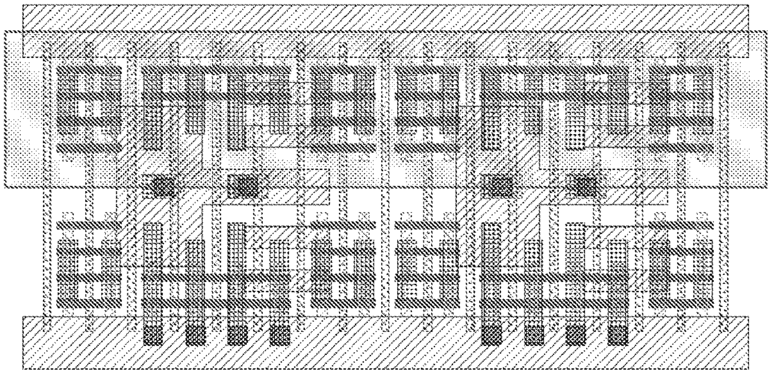
FIG. 1360A
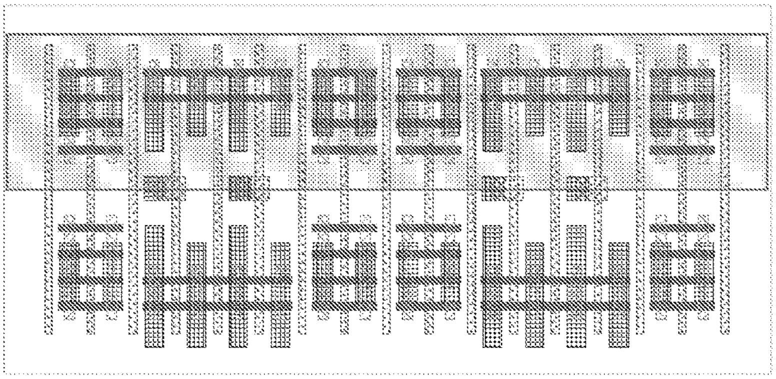
FIG. 1360B
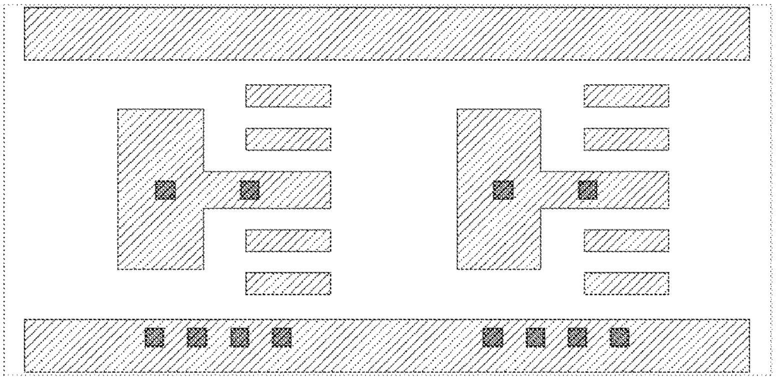
FIG. 1360C

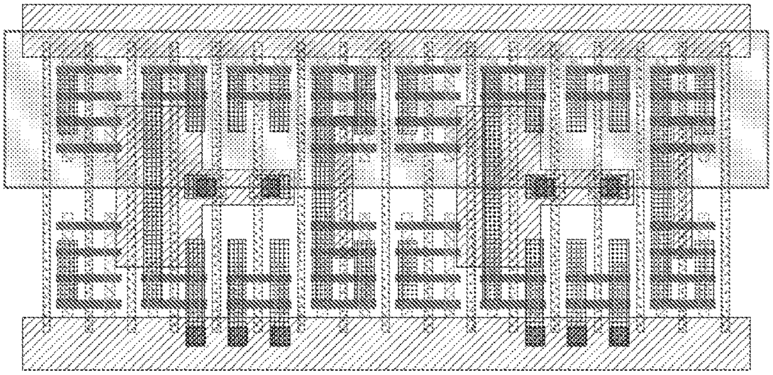
FIG. 1361A
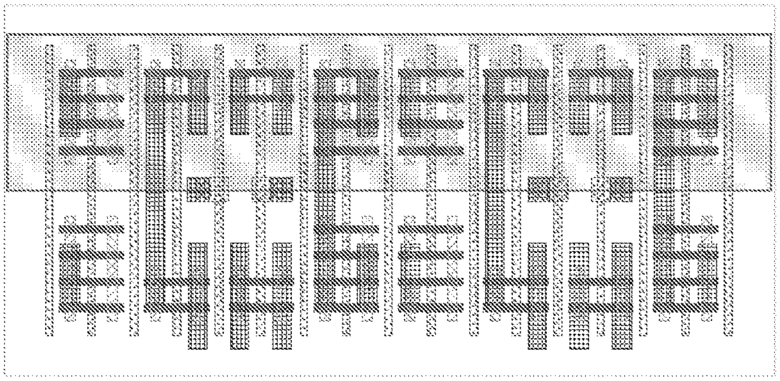
FIG. 1361B
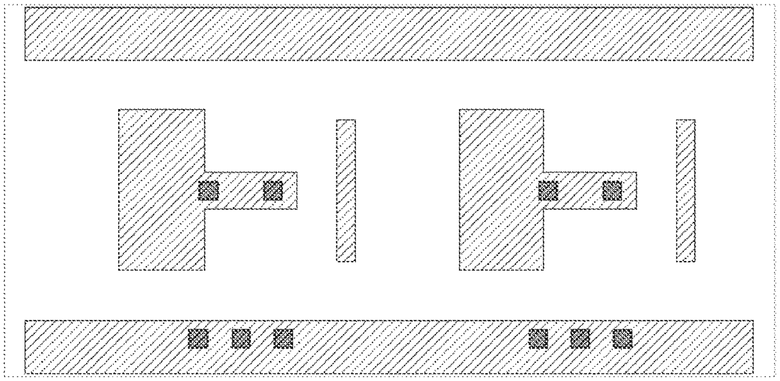
FIG. 1361C

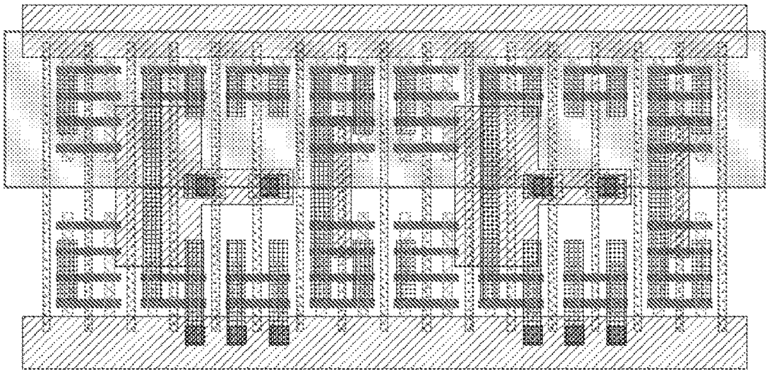
FIG. 1362A
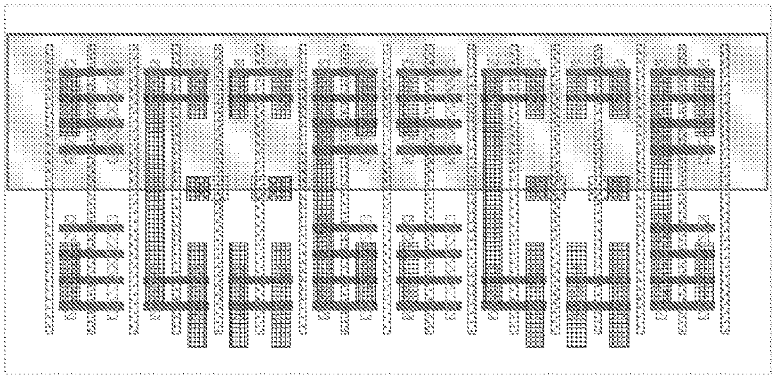
FIG. 1362B
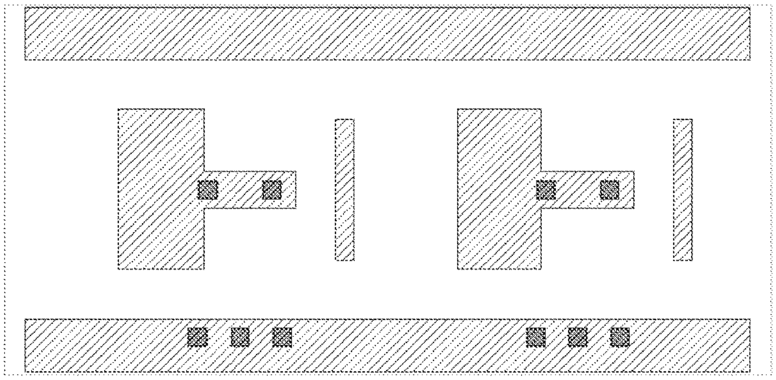
FIG. 1362C

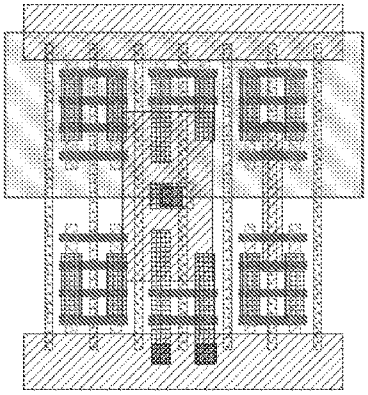
FIG. 1363A
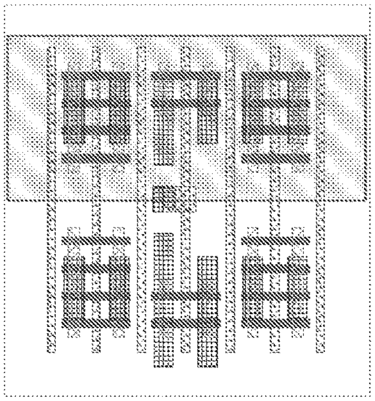
FIG. 1363B
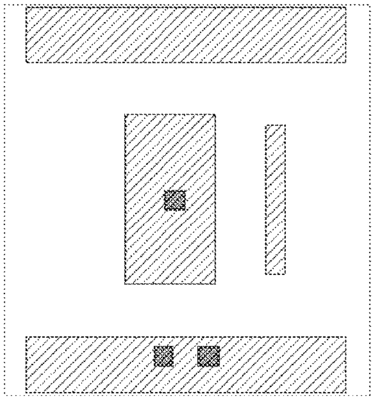
FIG. 1363C
*M* PDF Solutions, Inc.

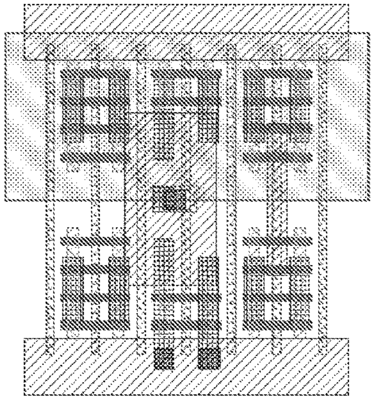
FIG. 1364A
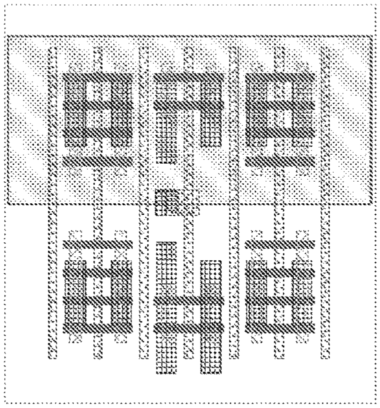
FIG. 1364B
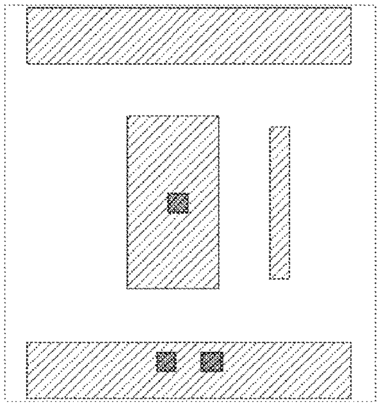
FIG. 1364C

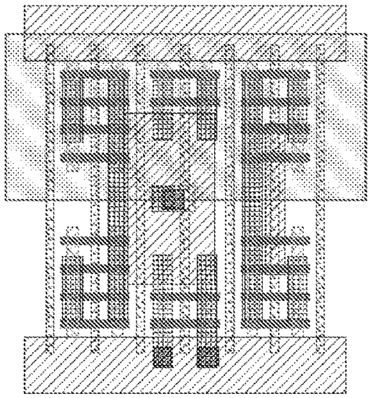
FIG. 1365A
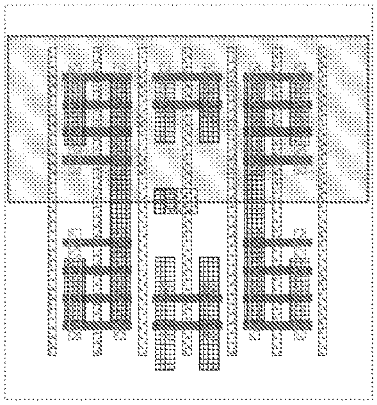
FIG. 1365B
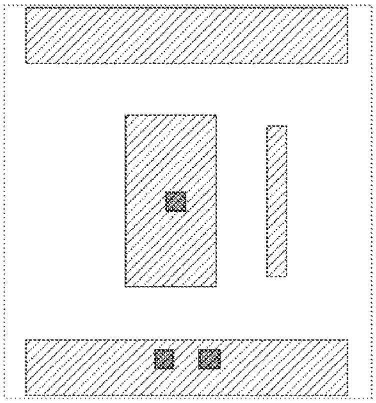
FIG. 1365C

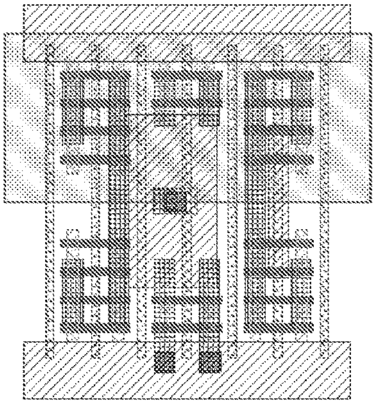
FIG. 1366A
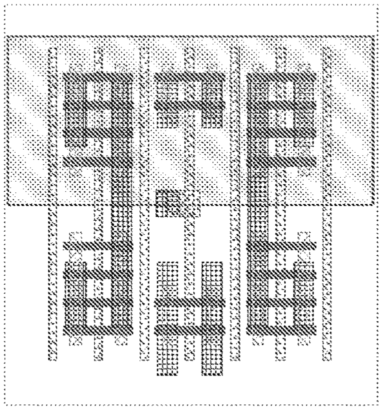
FIG. 1366B
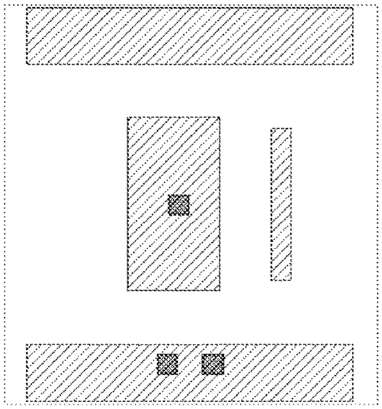
FIG. 1366C

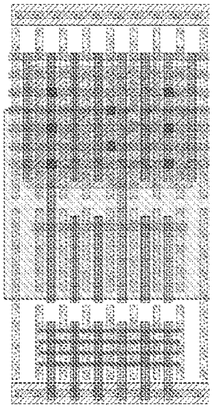
FIG. 1367A
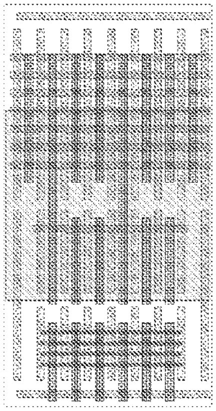
FIG. 1367B
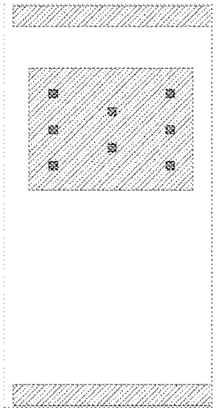
FIG. 1367C

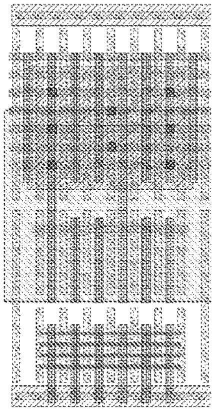
FIG. 1368A
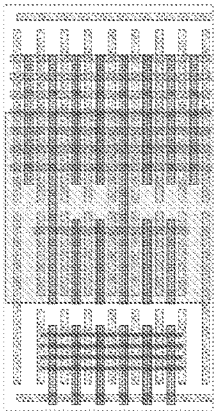
FIG. 1368B
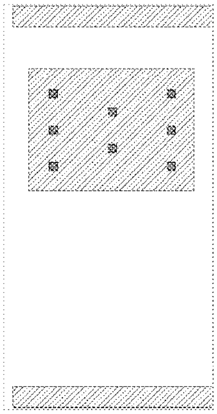
FIG. 1368C

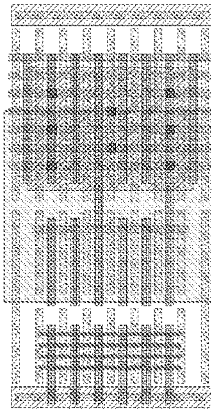
FIG. 1369A
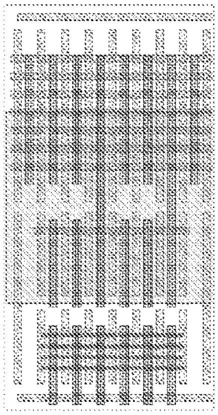
FIG. 1369B
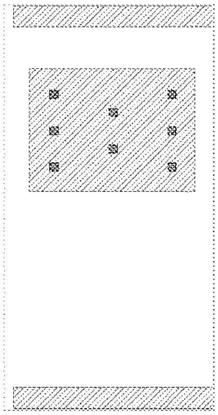
FIG. 1369C

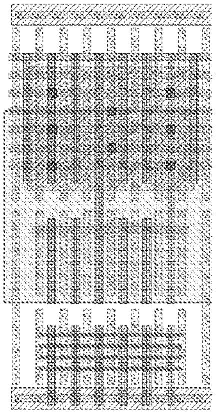
FIG. 1370A
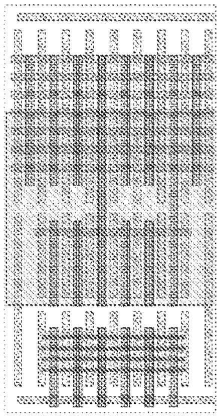
FIG. 1370B
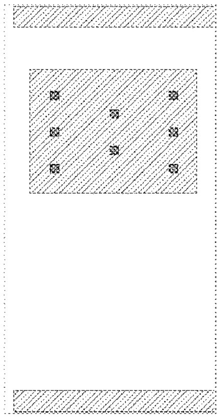
FIG. 1370C

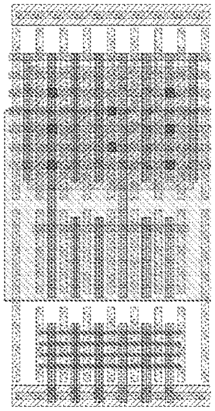
FIG. 1371A
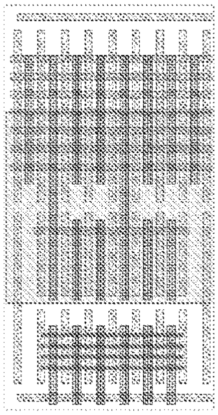
FIG. 1371B
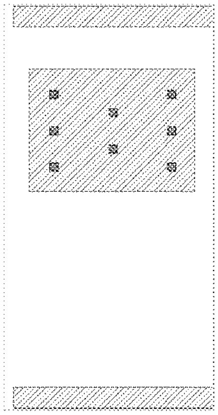
FIG. 1371C

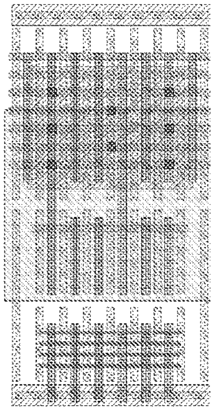
FIG. 1372A
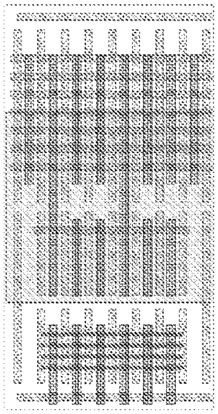
FIG. 1372B
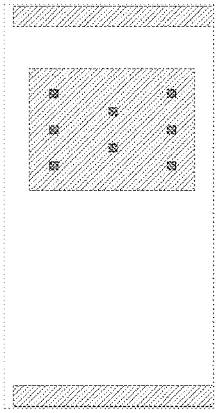
FIG. 1372C

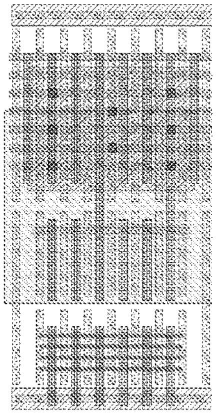
FIG. 1373A
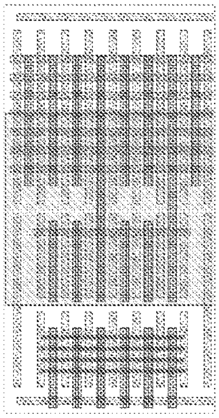
FIG. 1373B
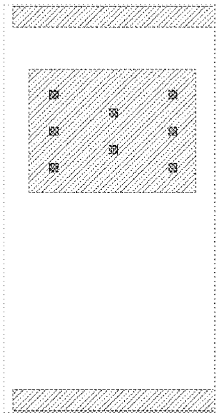
FIG. 1373C
*M* PDF Solutions, Inc.

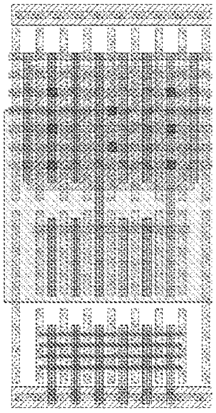
FIG. 1374A
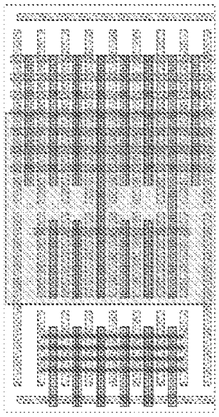
FIG. 1374B
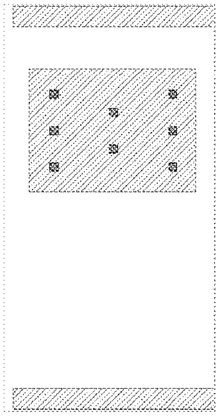
FIG. 1374C
*M* PDF Solutions, Inc.

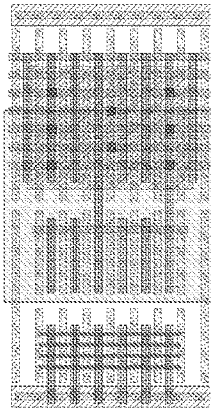
FIG. 1375A
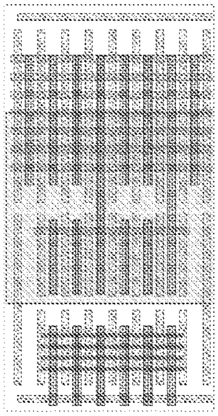
FIG. 1375B
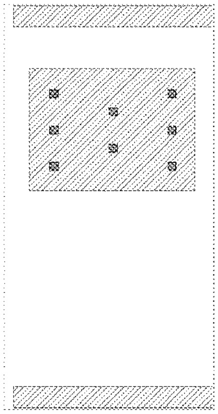
FIG. 1375C

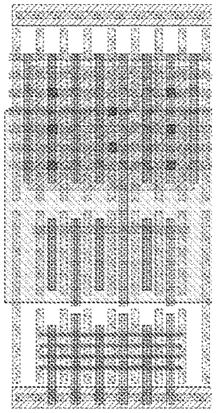
FIG. 1376A
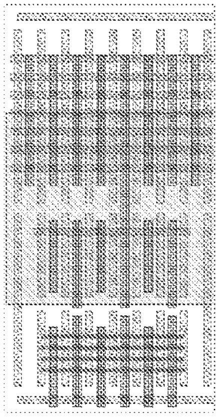
FIG. 1376B
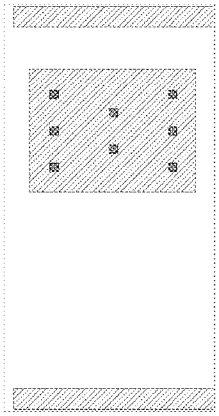
FIG. 1376C

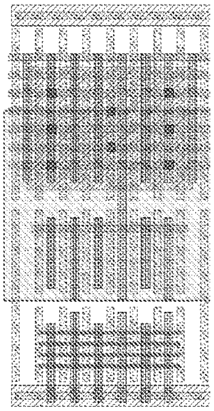
FIG. 1377A
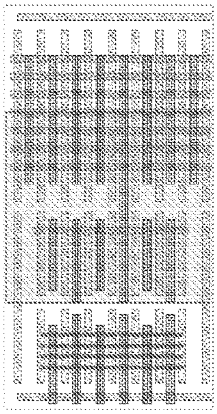
FIG. 1377B
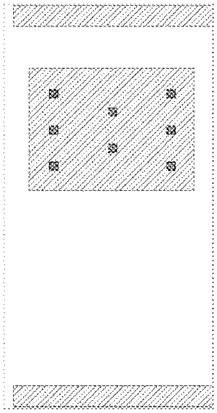
FIG. 1377C
*M* PDF Solutions, Inc.

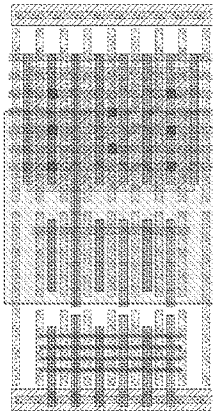
FIG. 1378A
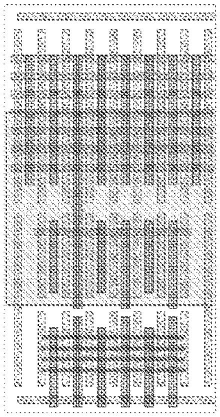
FIG. 1378B
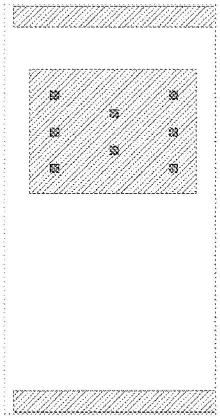
FIG. 1378C

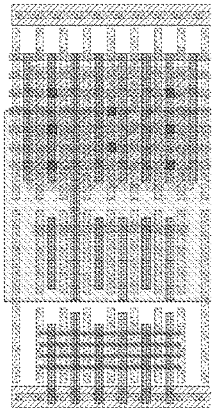
FIG. 1379A
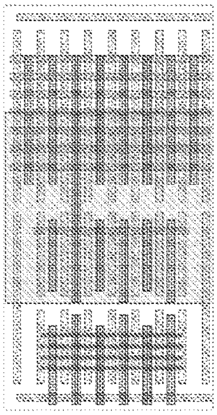
FIG. 1379B
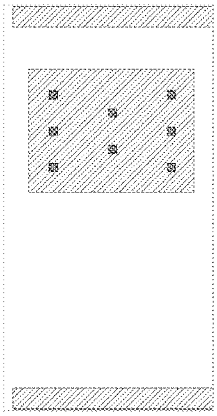
FIG. 1379C

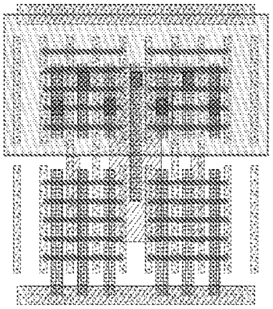
FIG. 1380A
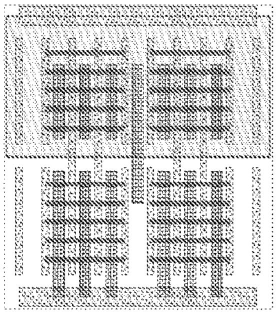
FIG. 1380B
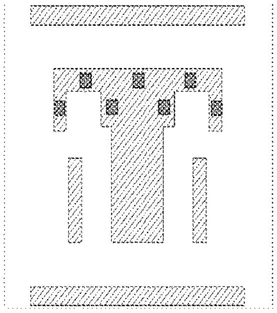
FIG. 1380C

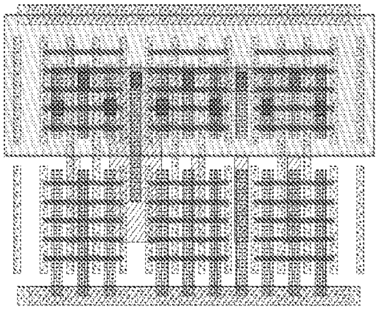
FIG. 1381A
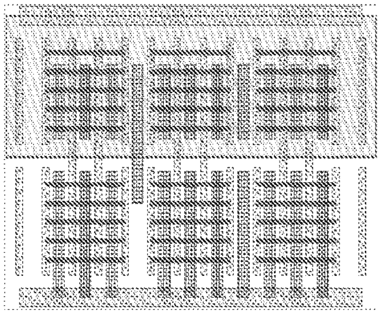
FIG. 1381B
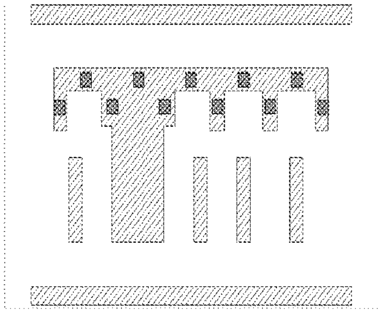
FIG. 1381C

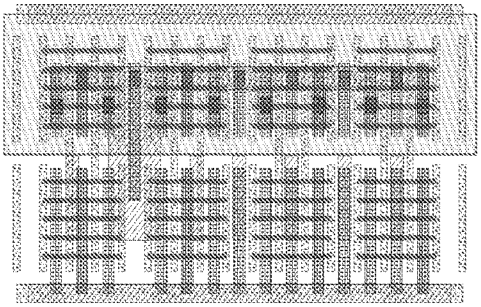
FIG. 1382A
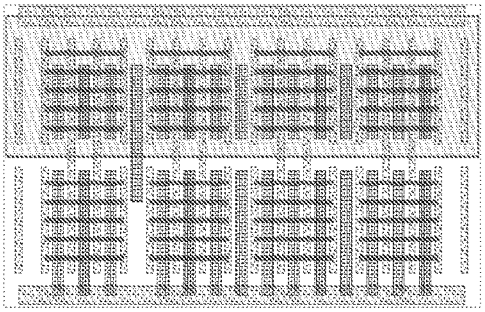
FIG. 1382B
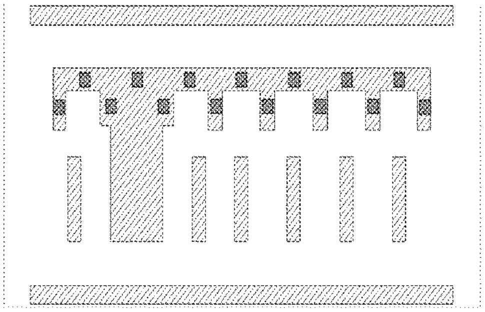
FIG. 1382C

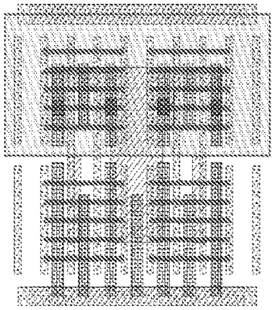
FIG. 1383A
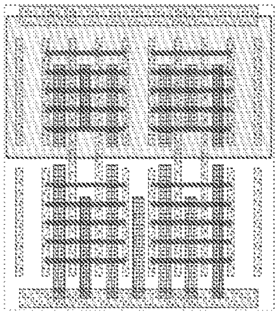
FIG. 1383B
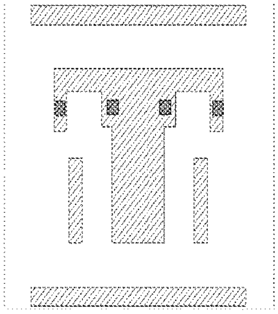
FIG. 1383C

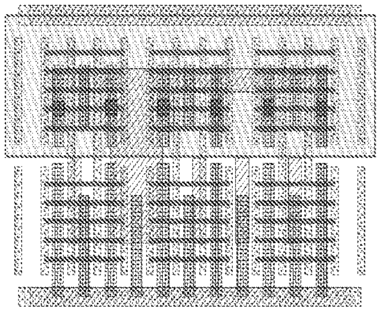
FIG. 1384A
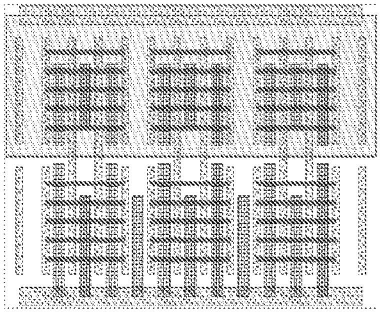
FIG. 1384B
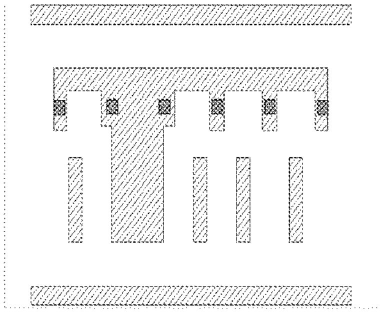
FIG. 1384C

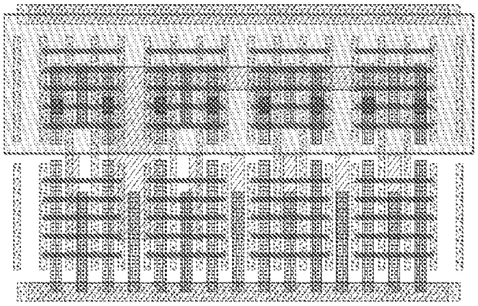
FIG. 1385A
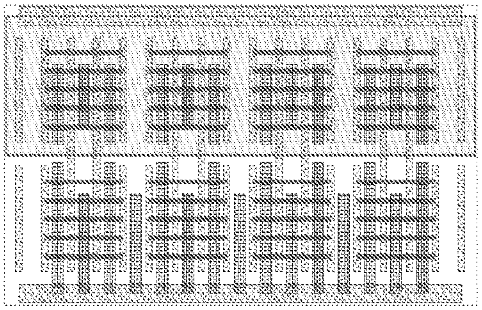
FIG. 1385B
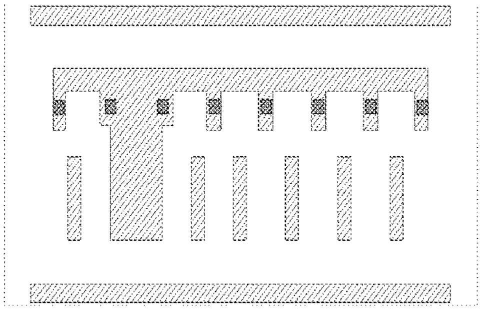
FIG. 1385C
*M* PDF Solutions, Inc.

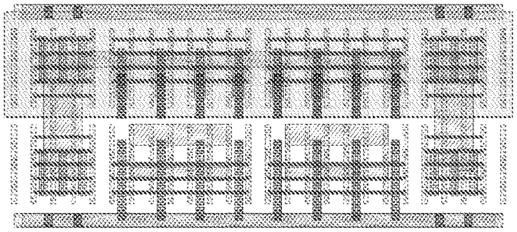
FIG. 1386A
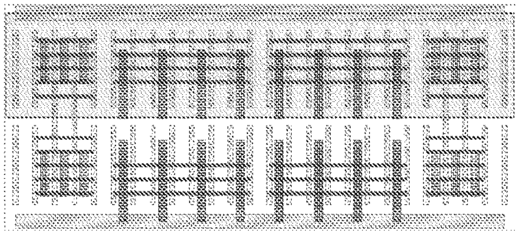
FIG. 1386B
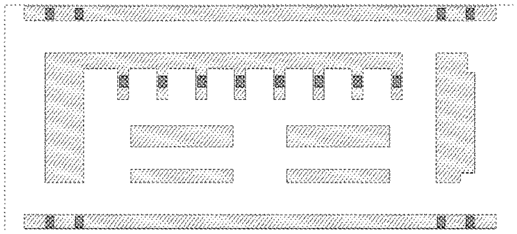
FIG. 1386C

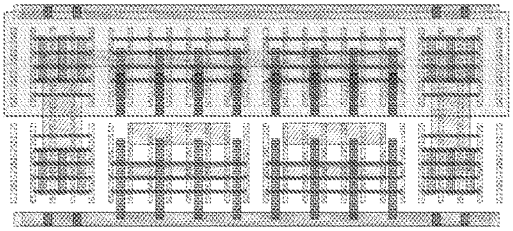
FIG. 1387A
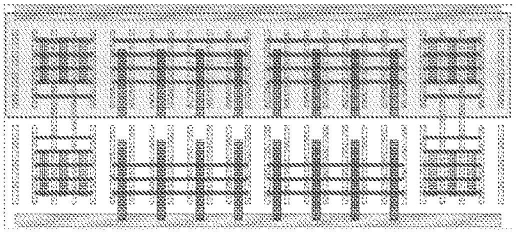
FIG. 1387B
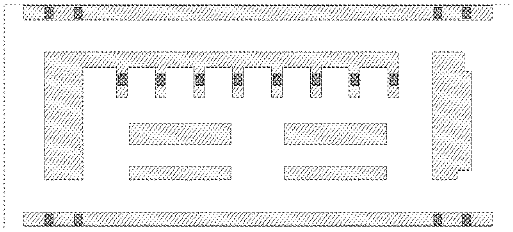
FIG. 1387C

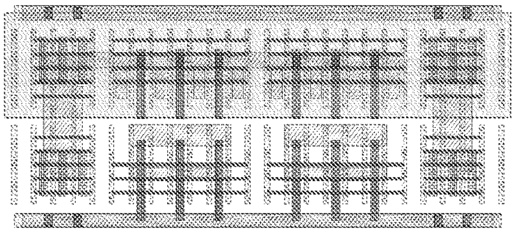
FIG. 1388A
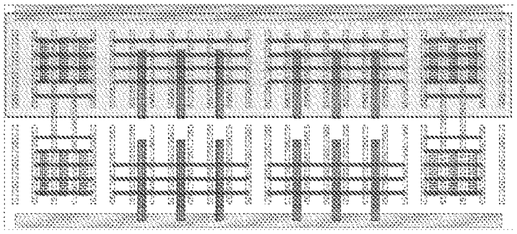
FIG. 1388B
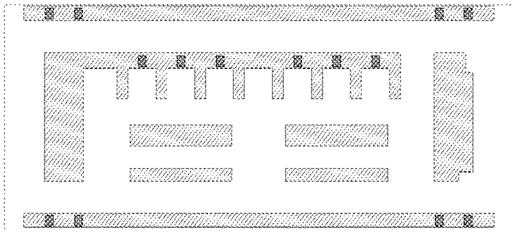
FIG. 1388C

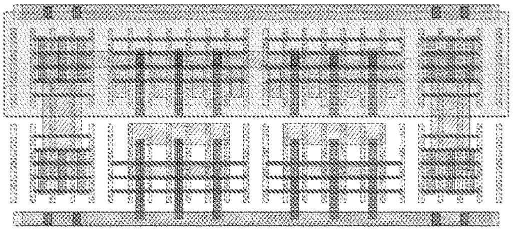
FIG. 1389A
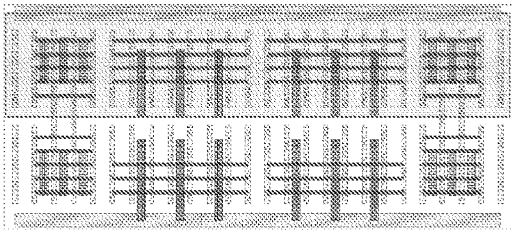
FIG. 1389B
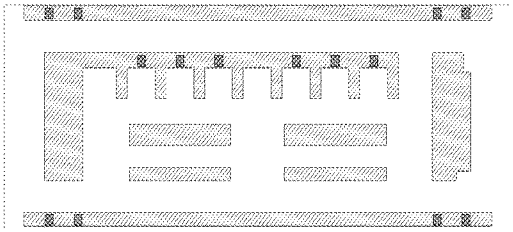
FIG. 1389C

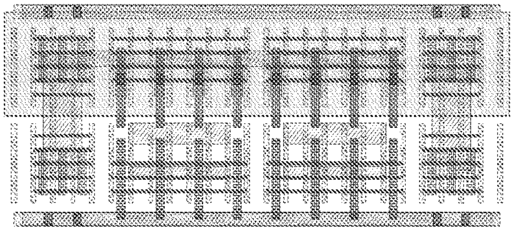
FIG. 1390A
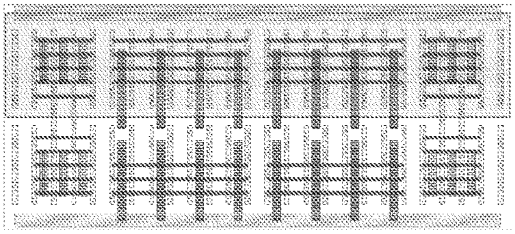
FIG. 1390B
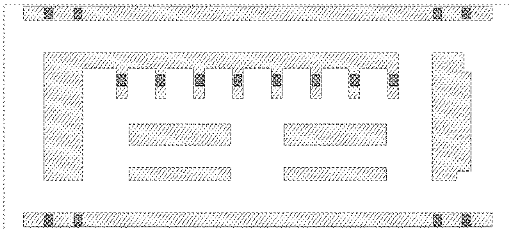
FIG. 1390C
*M* PDF Solutions, Inc.

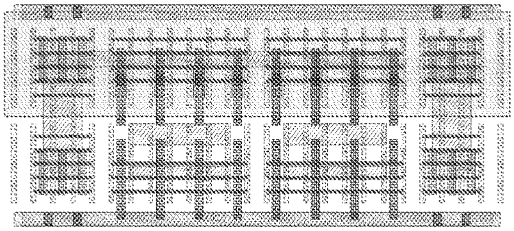
FIG. 1391A
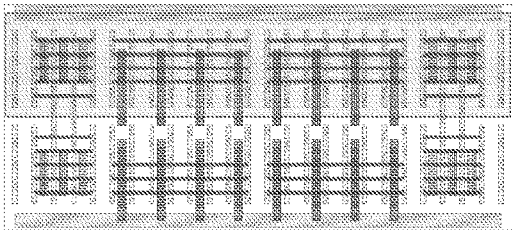
FIG. 1391B
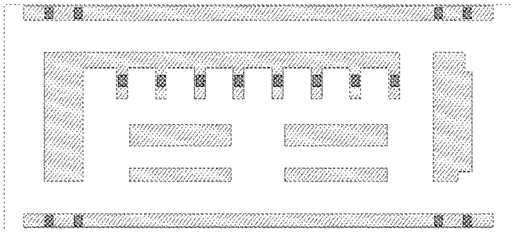
FIG. 1391C
*M* PDF Solutions, Inc.

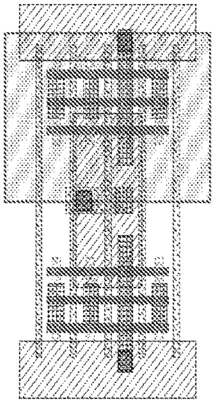
FIG. 1392A
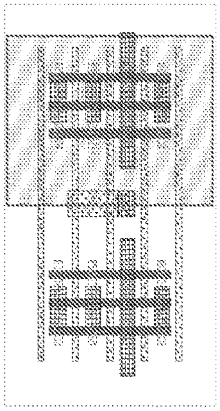
FIG. 1392B
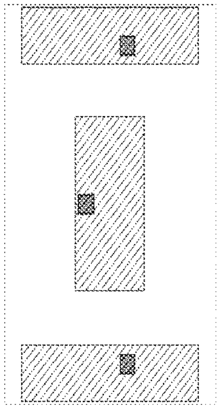
FIG. 1392C

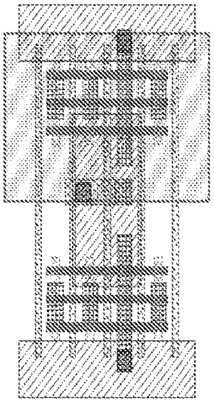
FIG. 1393A
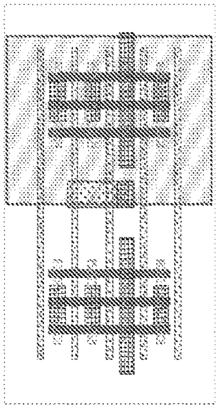
FIG. 1393B
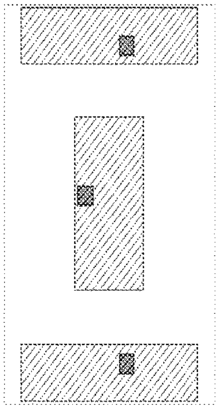
FIG. 1393C

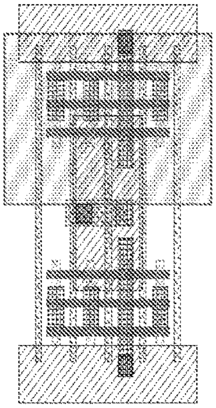
FIG. 1394A
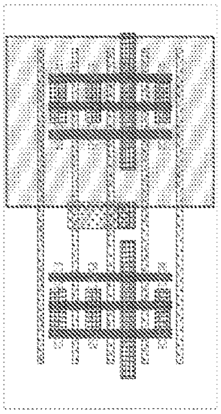
FIG. 1394B
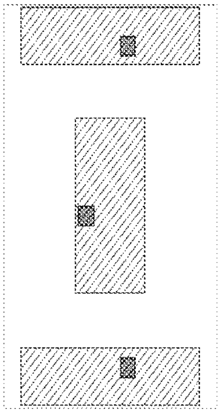
FIG. 1394C

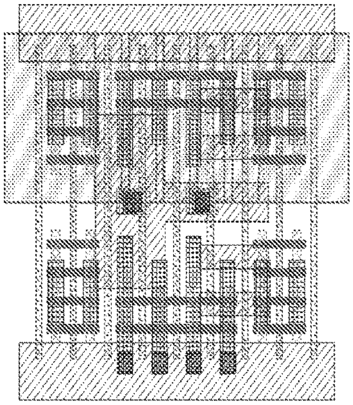
FIG. 1395A
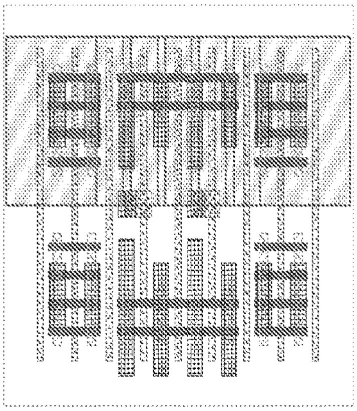
FIG. 1395B
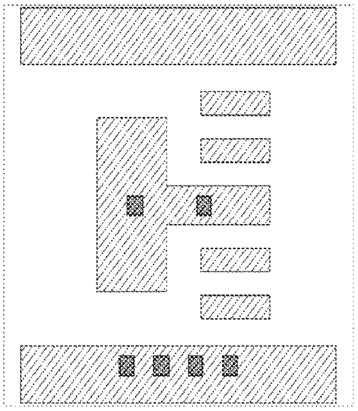
FIG. 1395C
*M* PDF Solutions, Inc.

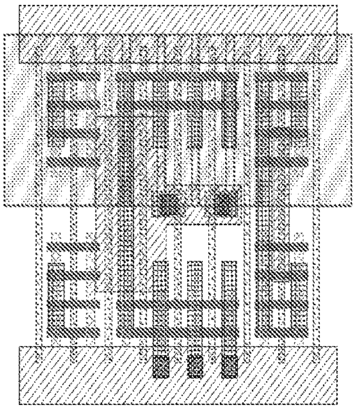
FIG. 1396A
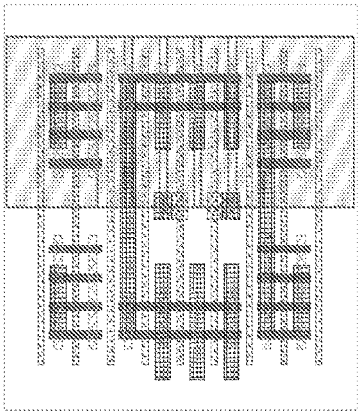
FIG. 1396B
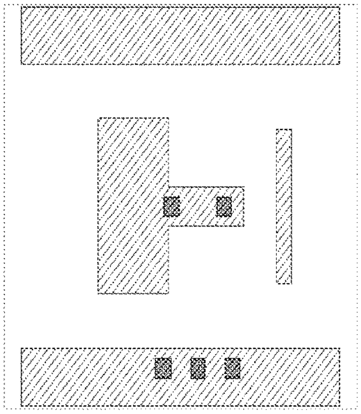
FIG. 1396C

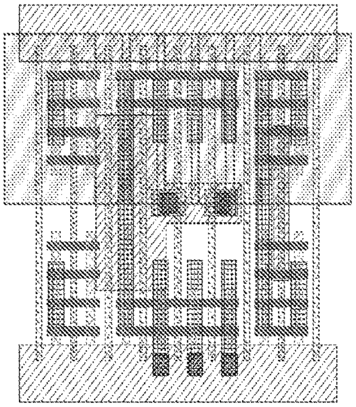
FIG. 1397A
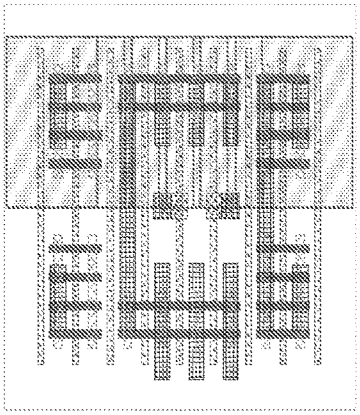
FIG. 1397B
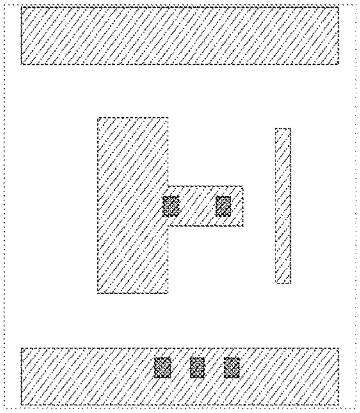
FIG. 1397C

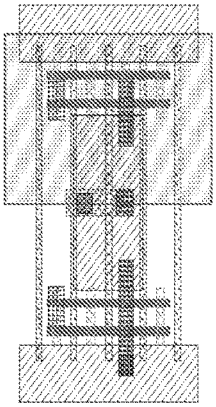
FIG. 1398A
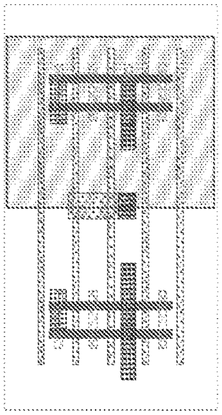
FIG. 1398B
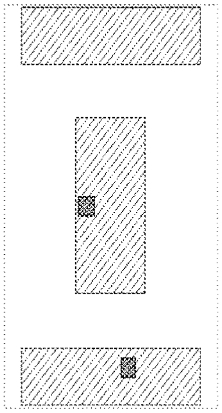
FIG. 1398C
*M* PDF Solutions, Inc.

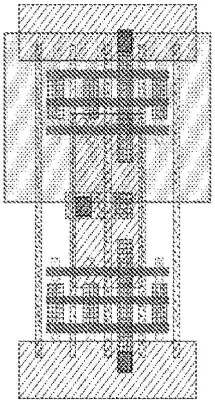
FIG. 1399A
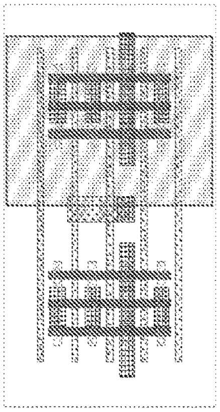
FIG. 1399B
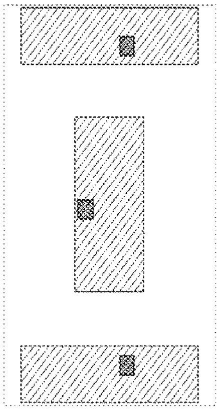
FIG. 1399C

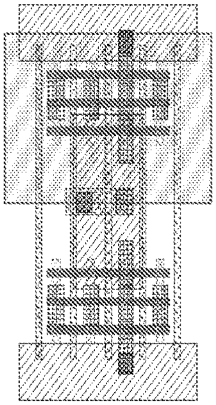
FIG. 1400A
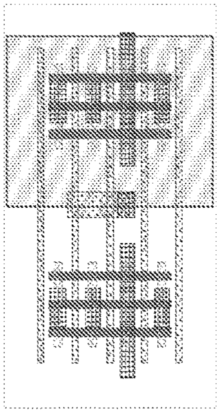
FIG. 1400B
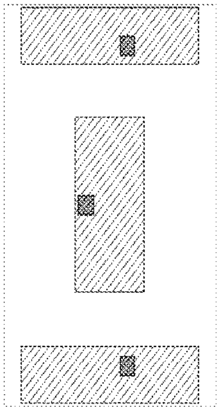
FIG. 1400C

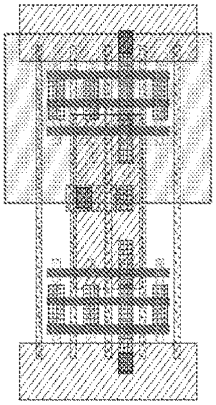
FIG. 1401A
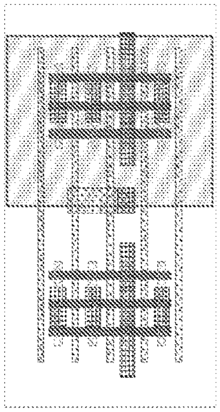
FIG. 1401B
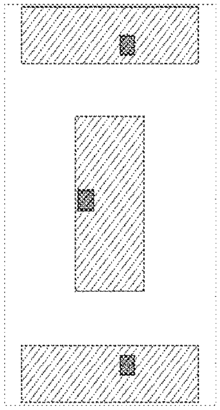
FIG. 1401C
*M* PDF Solutions, Inc.

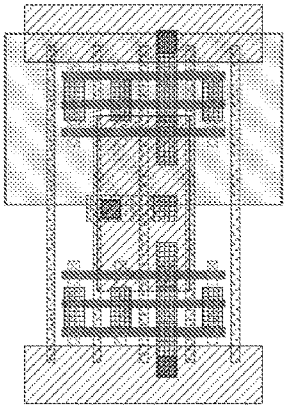
FIG. 1402A
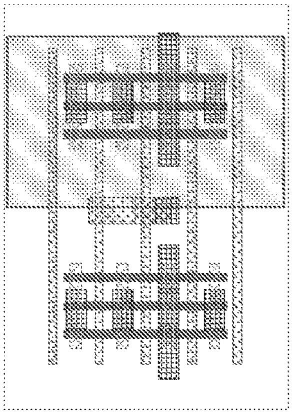
FIG. 1402B
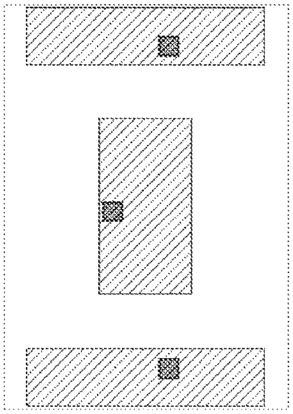
FIG. 1402C

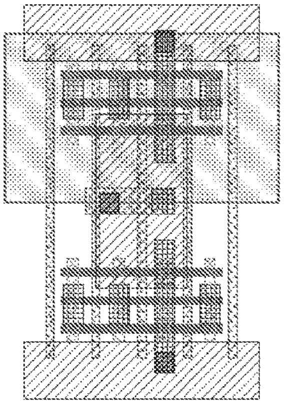
FIG. 1403A
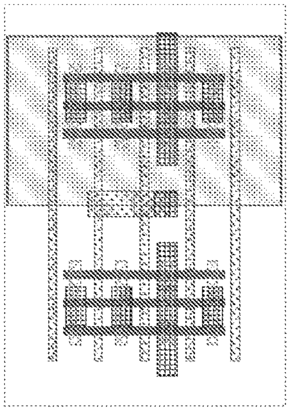
FIG. 1403B
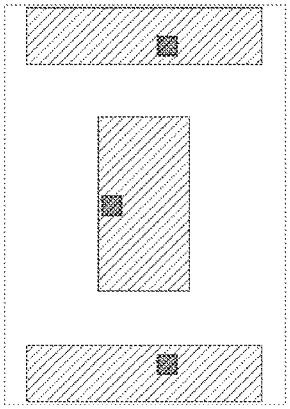
FIG. 1403C

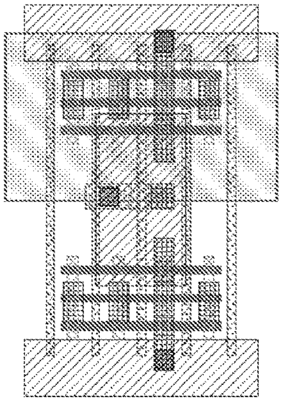
FIG. 1404A
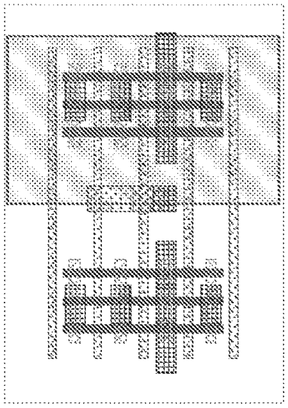
FIG. 1404B
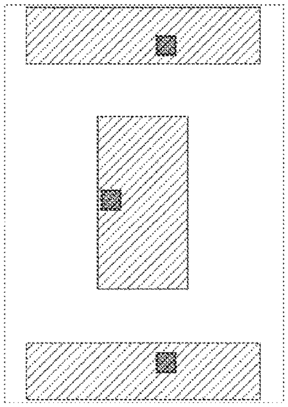
FIG. 1404C
*M* PDF Solutions, Inc.

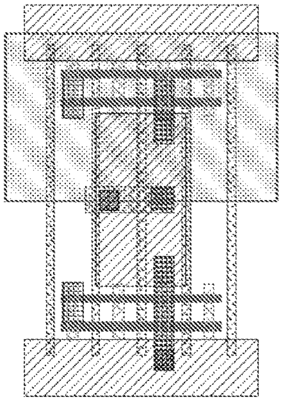
FIG. 1405A
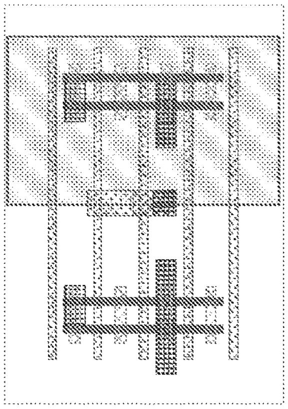
FIG. 1405B
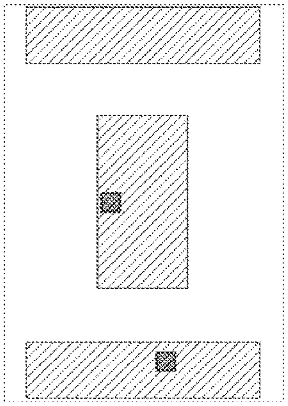
FIG. 1405C

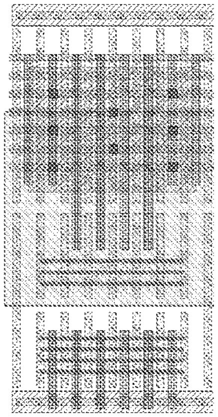
FIG. 1406A
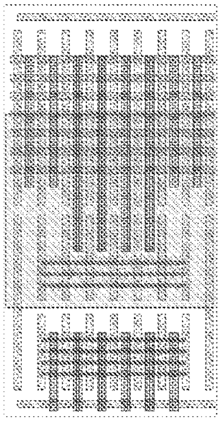
FIG. 1406B
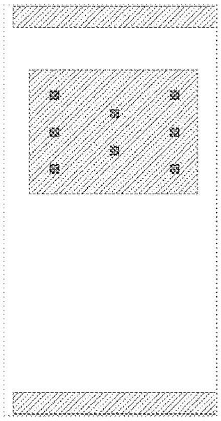
FIG. 1406C
*M* PDF Solutions, Inc.

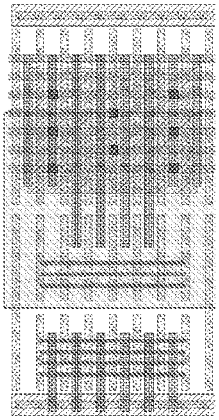
FIG. 1407A
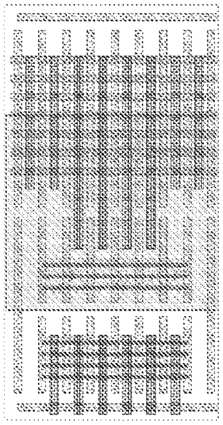
FIG. 1407B
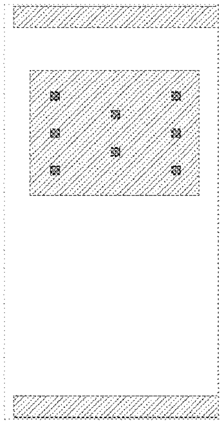
FIG. 1407C

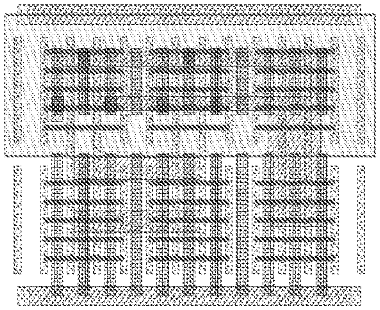
FIG. 1408A
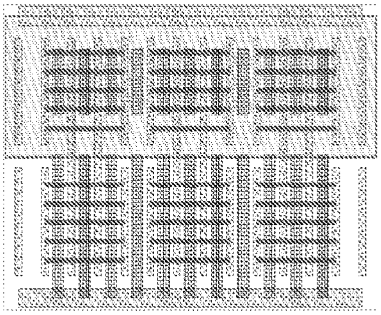
FIG. 1408B
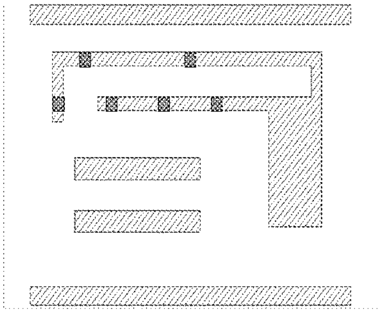
FIG. 1408C

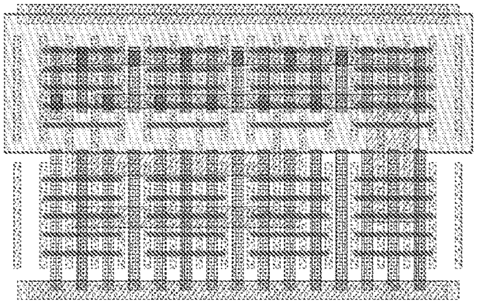
FIG. 1409A
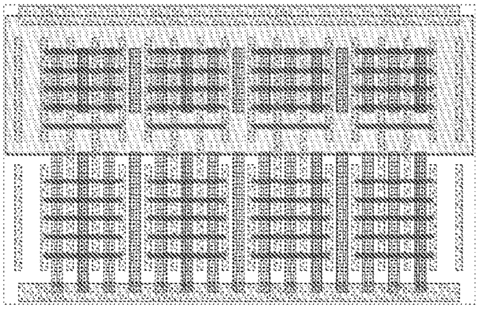
FIG. 1409B
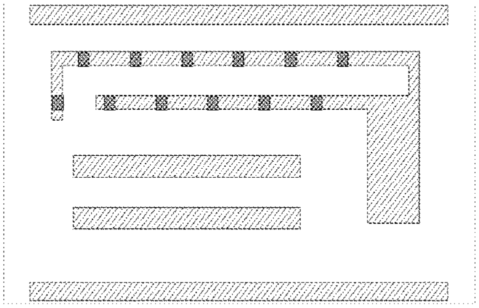
FIG. 1409C

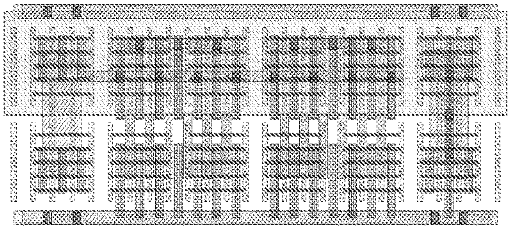
FIG. 1410A
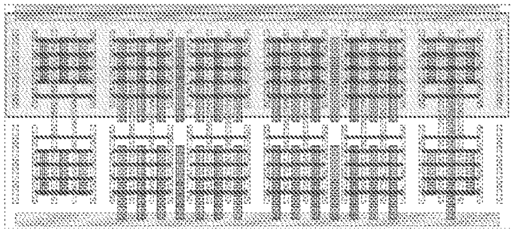
FIG. 1410B
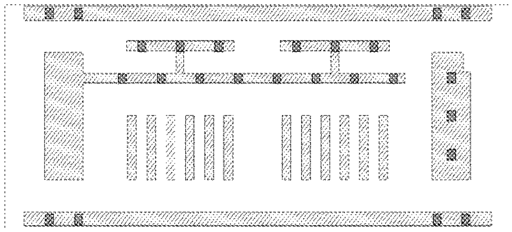
FIG. 1410C

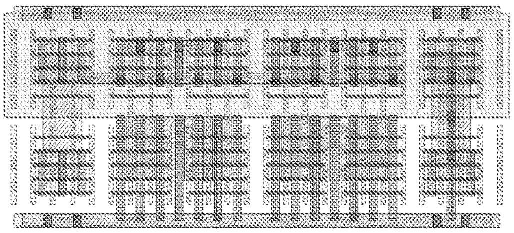
FIG. 1411A
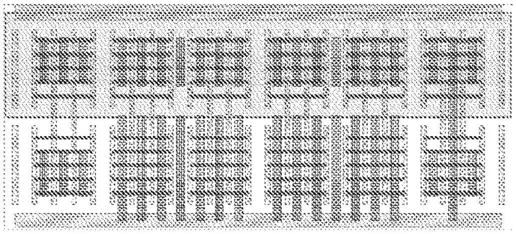
FIG. 1411B
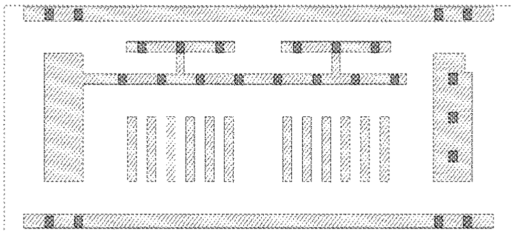
FIG. 1411C

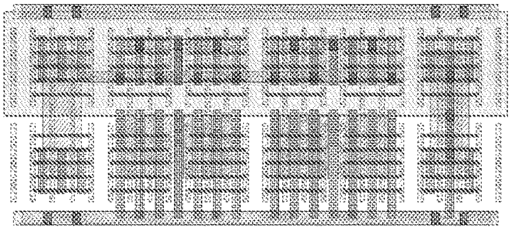
FIG. 1412A
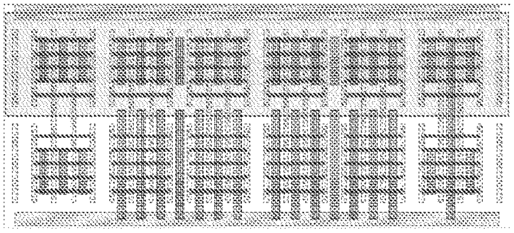
FIG. 1412B
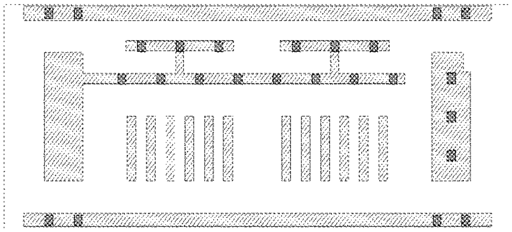
FIG. 1412C
*M* PDF Solutions, Inc.

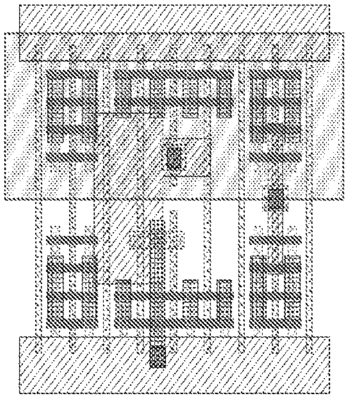
FIG. 1413A
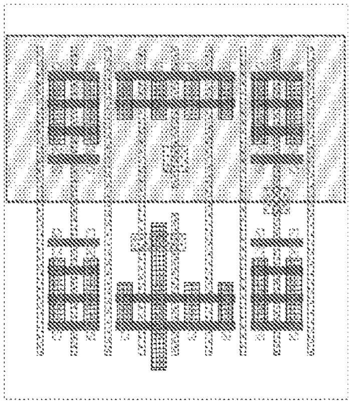
FIG. 1413B
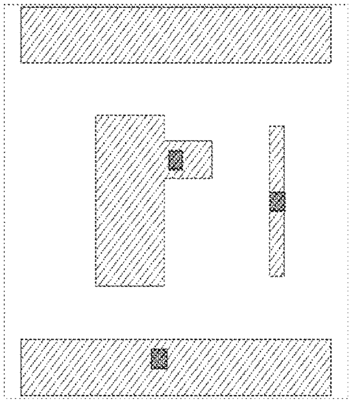
FIG. 1413C
*M* PDF Solutions, Inc.

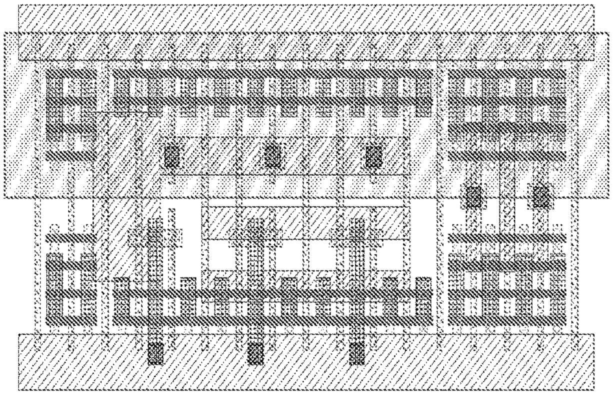
FIG. 1414A
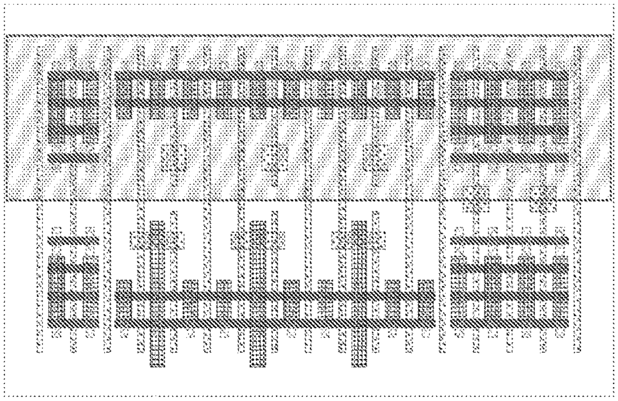
FIG. 1414B
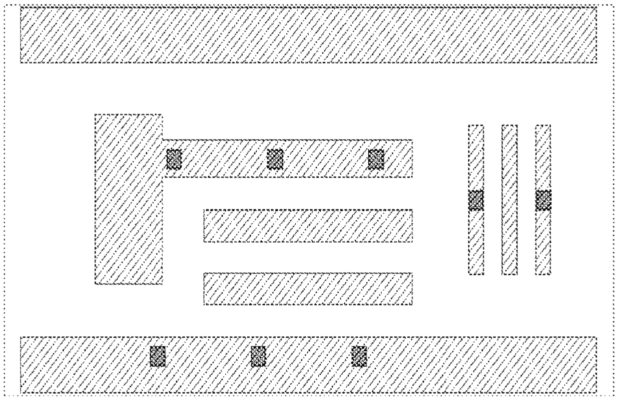
FIG. 1414C

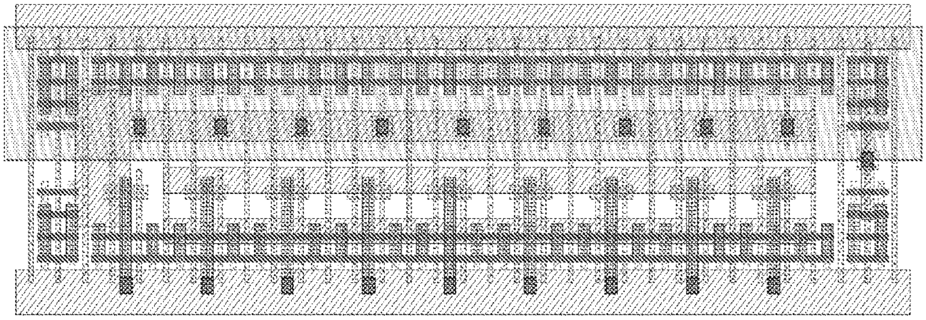
FIG. 1415A
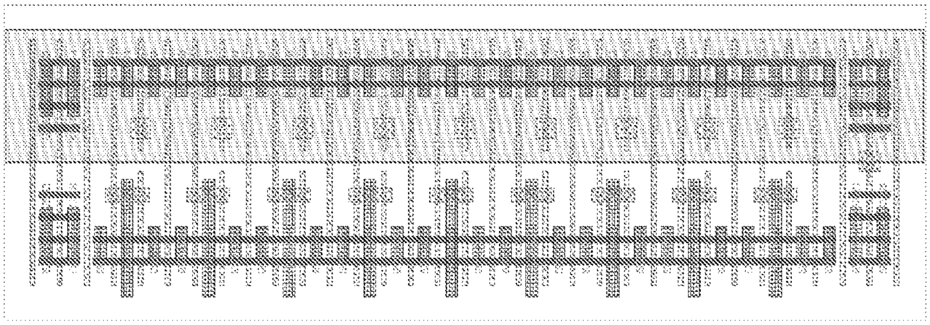
FIG. 1415B
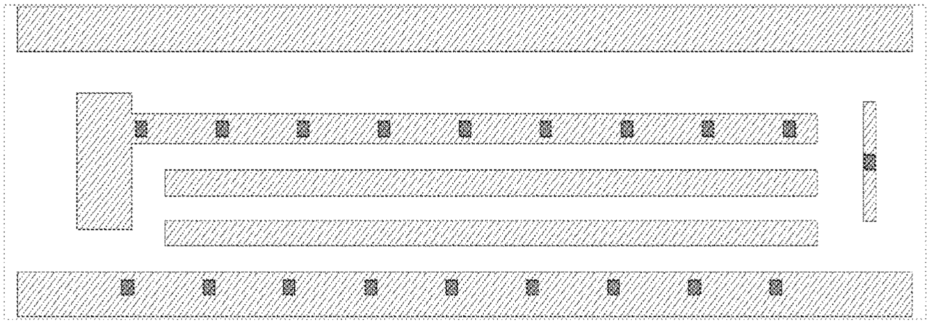
FIG. 1415C

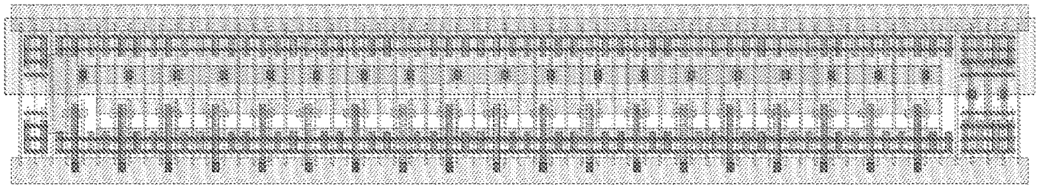
FIG. 1416A
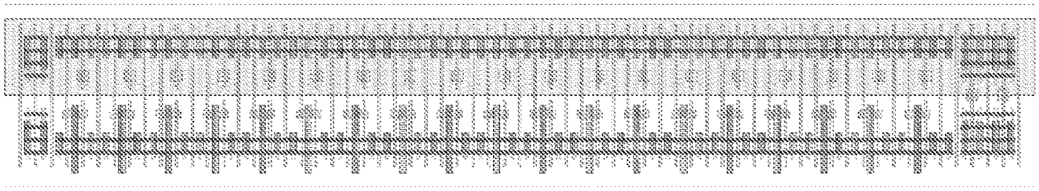
FIG. 1416B
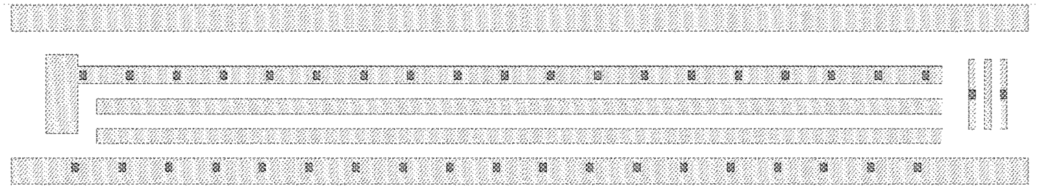
FIG. 1416C

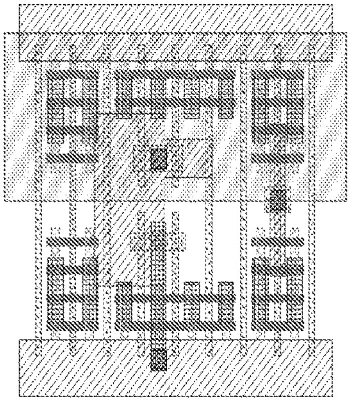
FIG. 1417A
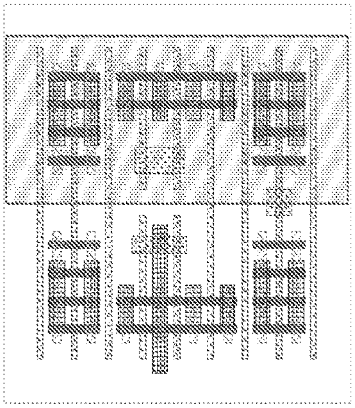
FIG. 1417B
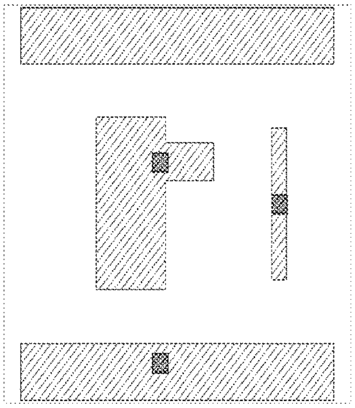
FIG. 1417C
*M* PDF Solutions, Inc.

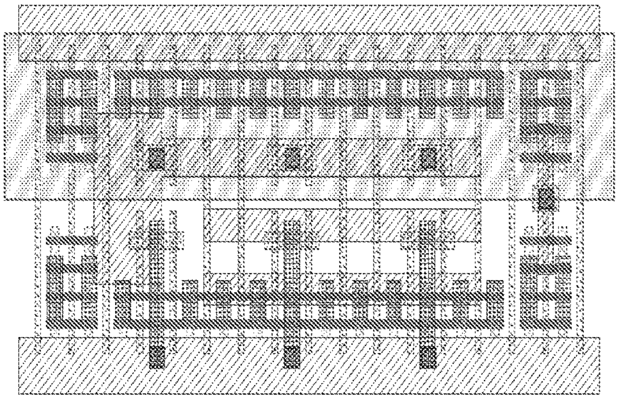
FIG. 1418A
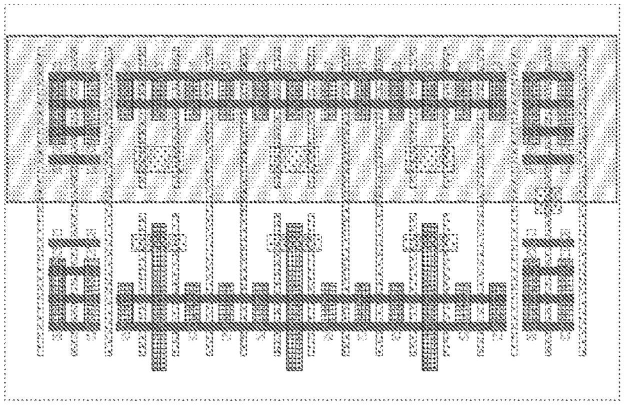
FIG. 1418B
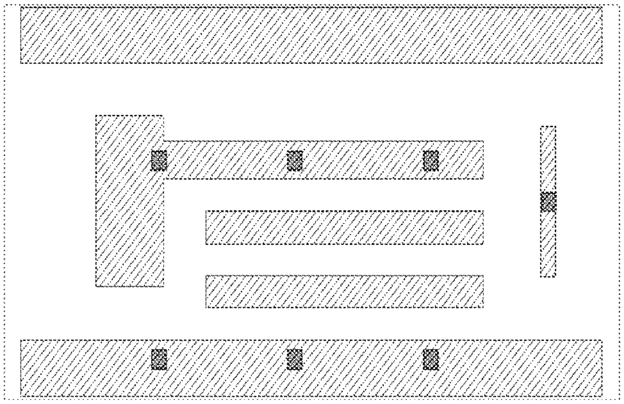
FIG. 1418C

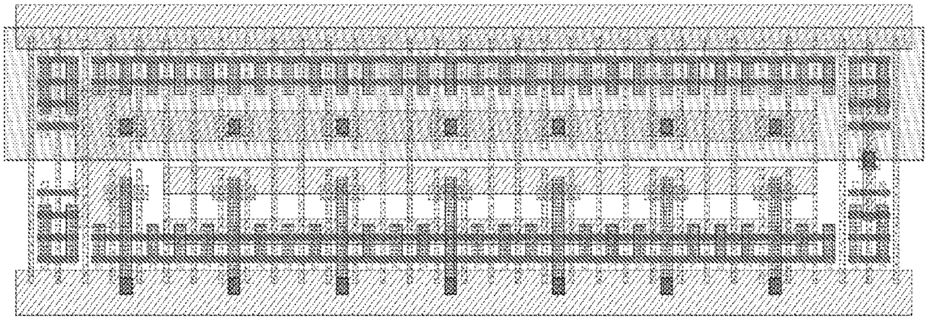
FIG. 1419A
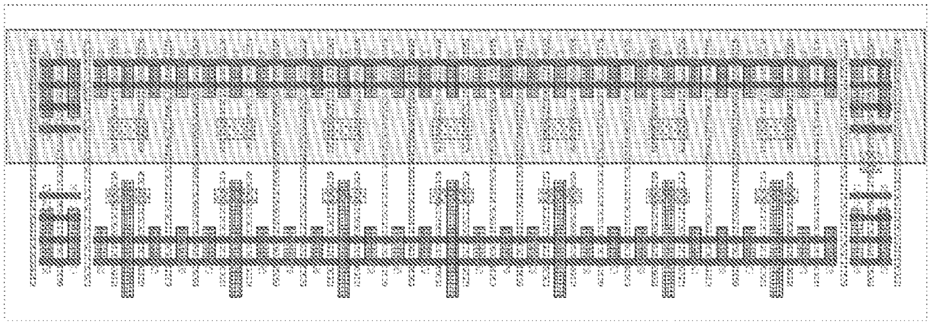
FIG. 1419B
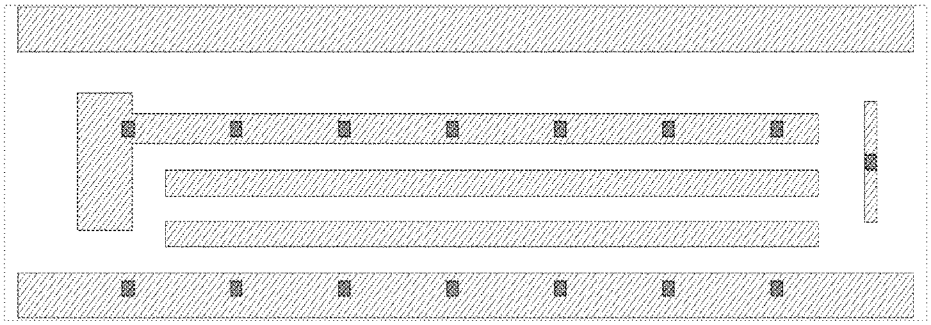
FIG. 1419C
*M* PDF Solutions, Inc.

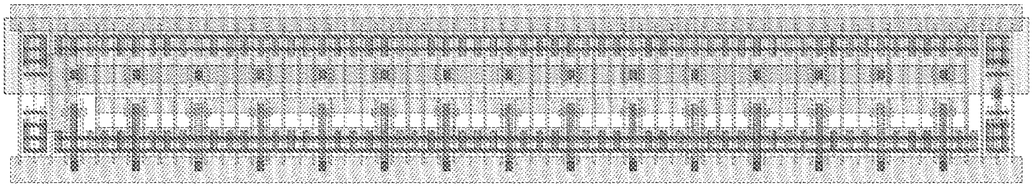
FIG. 1420A
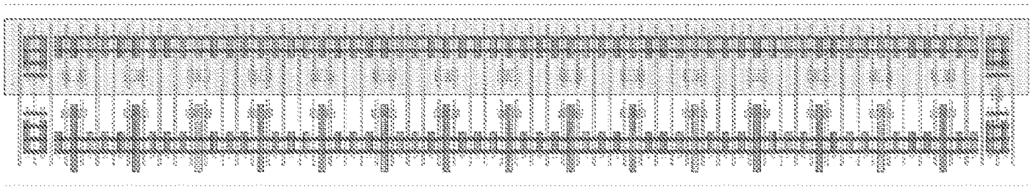
FIG. 1420B
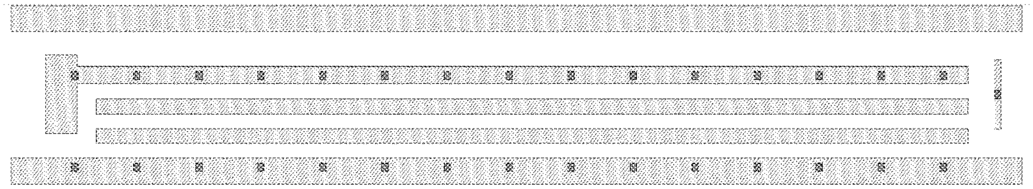
FIG. 1420C

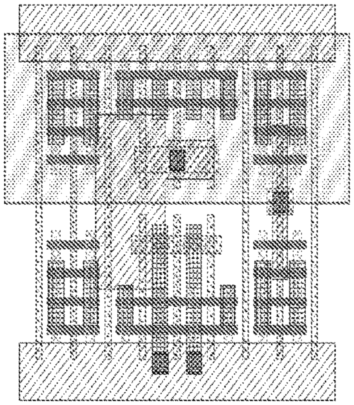
FIG. 1421A
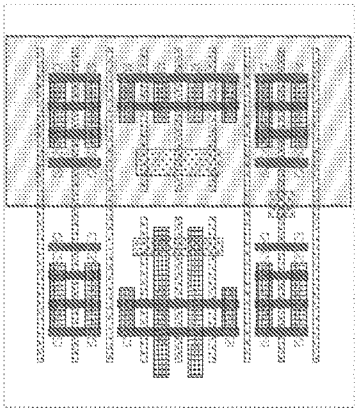
FIG. 1421B
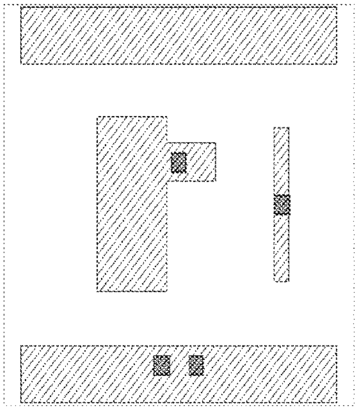
FIG. 1421C

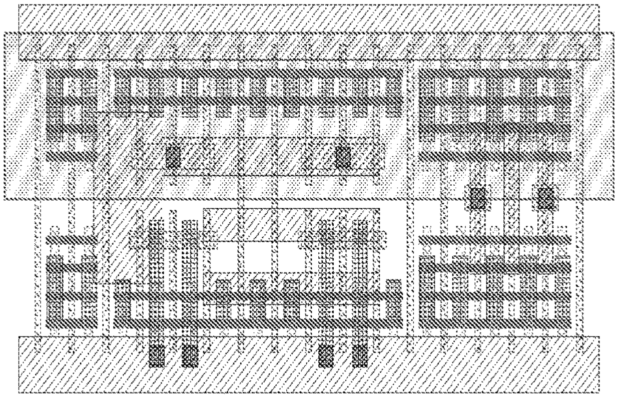
FIG. 1422A
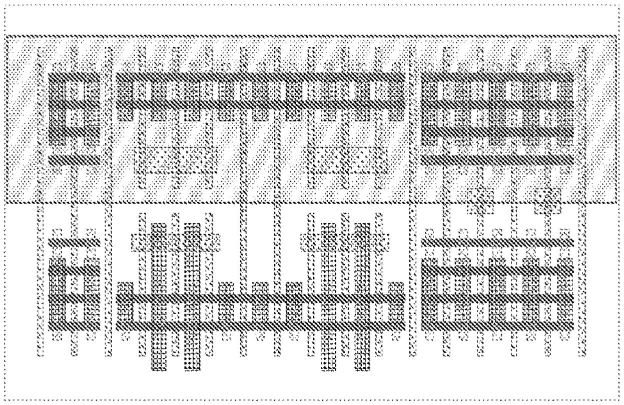
FIG. 1422B
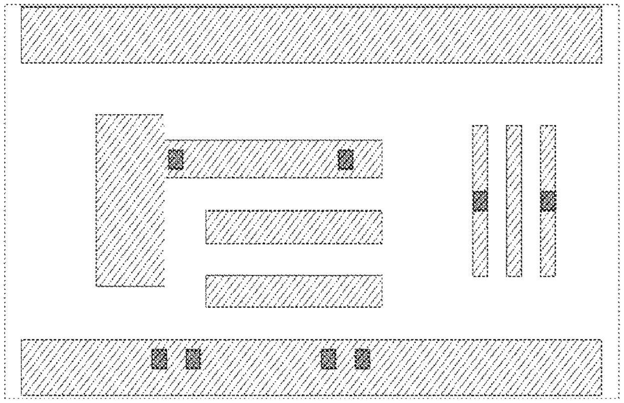
FIG. 1422C
*M* PDF Solutions, Inc.

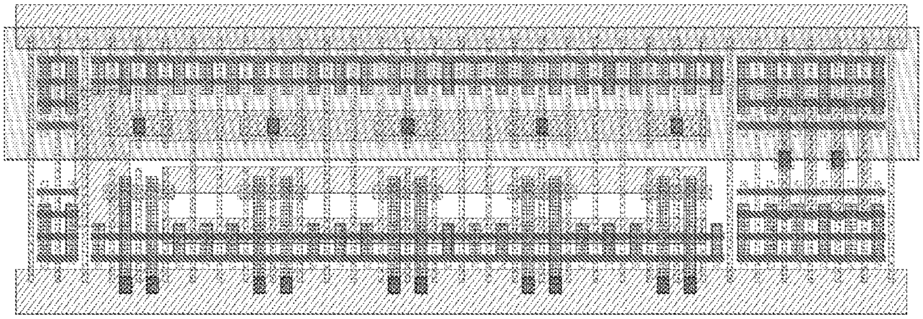
FIG. 1423A
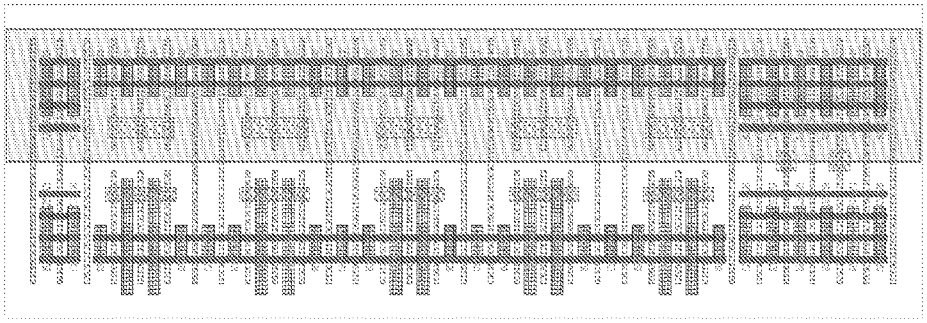
FIG. 1423B
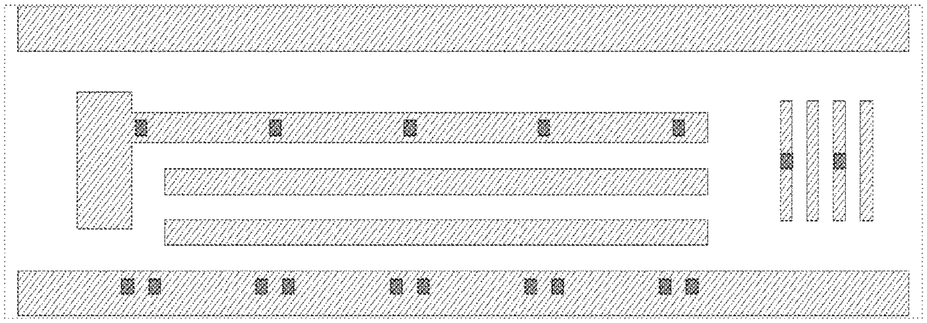
FIG. 1423C
*M* PDF Solutions, Inc.

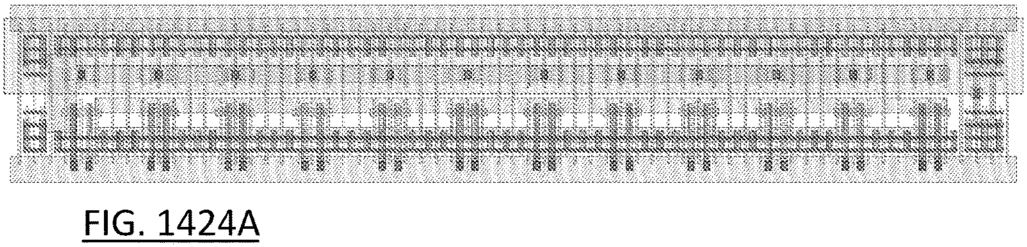
FIG. 1424A
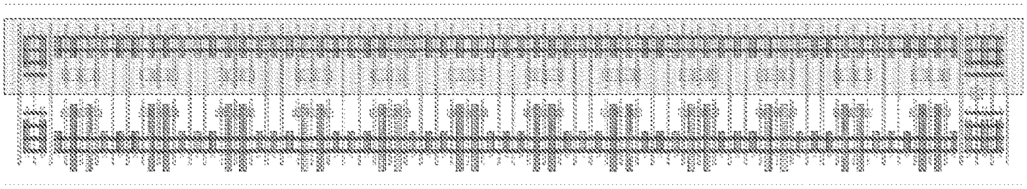
FIG. 1424B
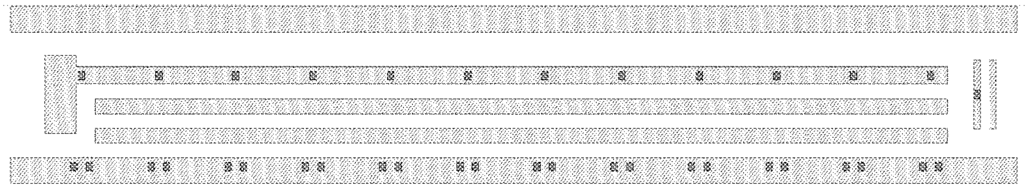
FIG. 1424C

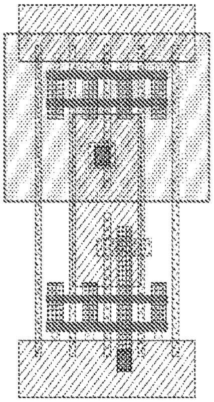
FIG. 1425A
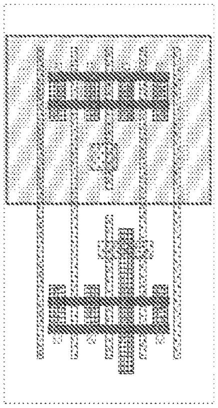
FIG. 1425B
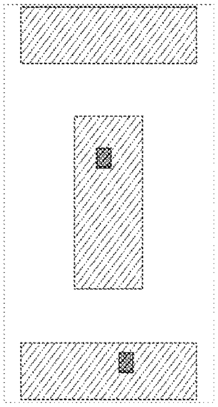
FIG. 1425C

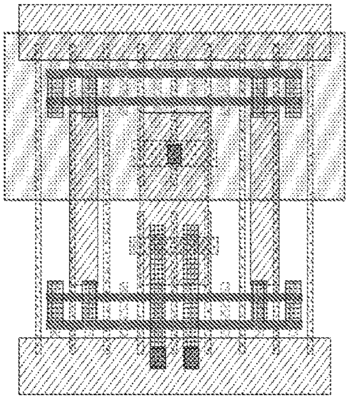
FIG. 1426A
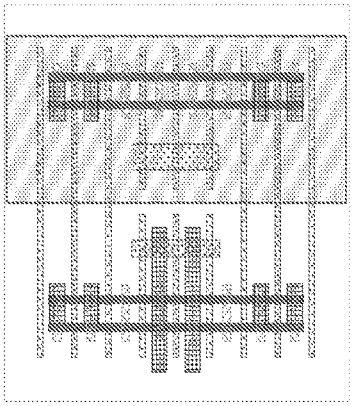
FIG. 1426B
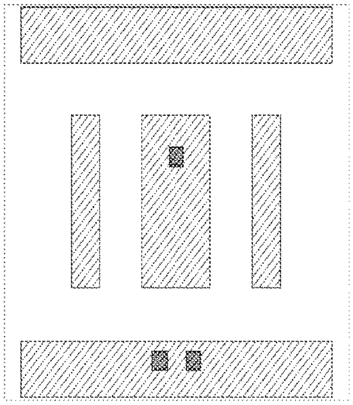
FIG. 1426C

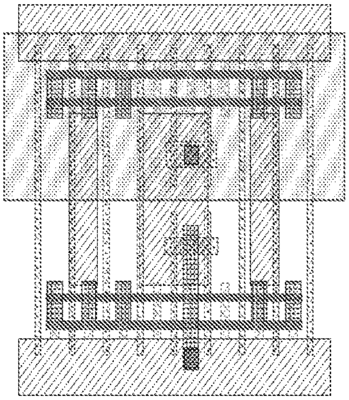
FIG. 1427A
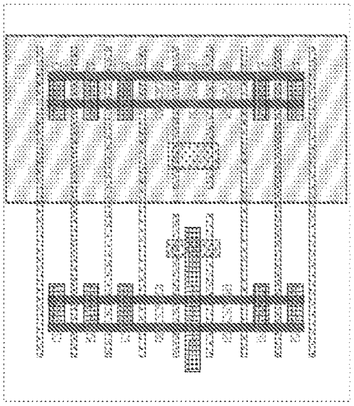
FIG. 1427B
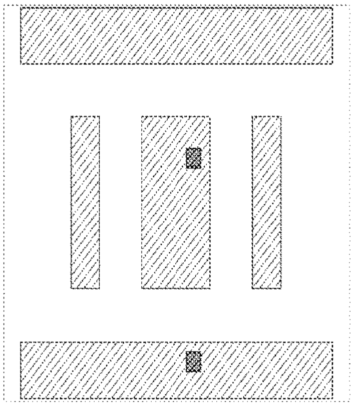
FIG. 1427C

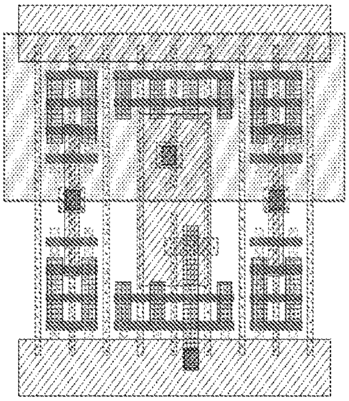
FIG. 1428A
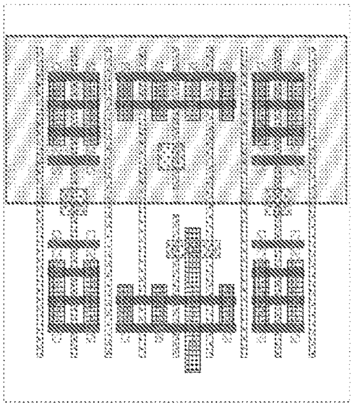
FIG. 1428B
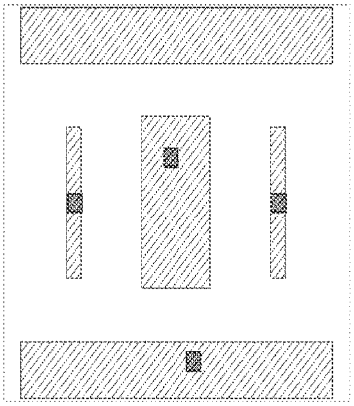
FIG. 1428C
*M* PDF Solutions, Inc.

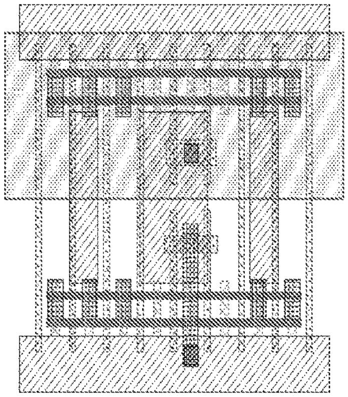
FIG. 1429A
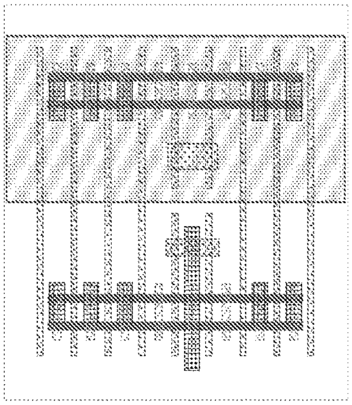
FIG. 1429B
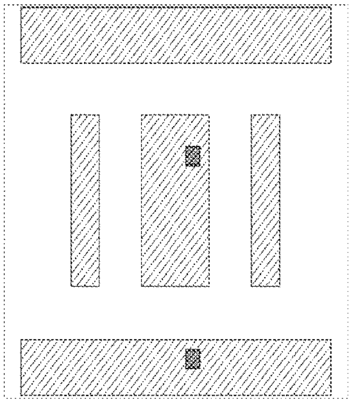
FIG. 1429C

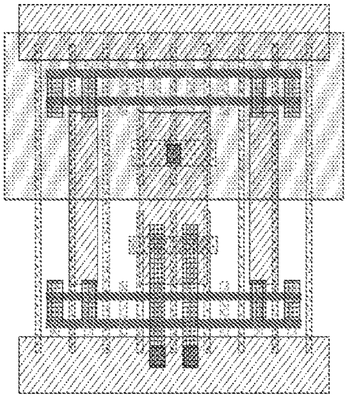
FIG. 1430A
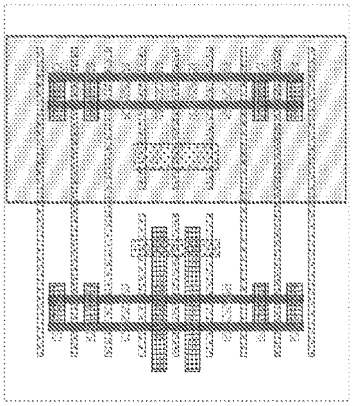
FIG. 1430B
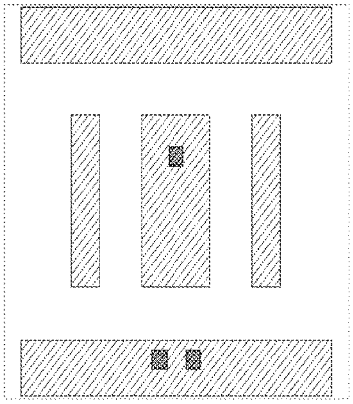
FIG. 1430C

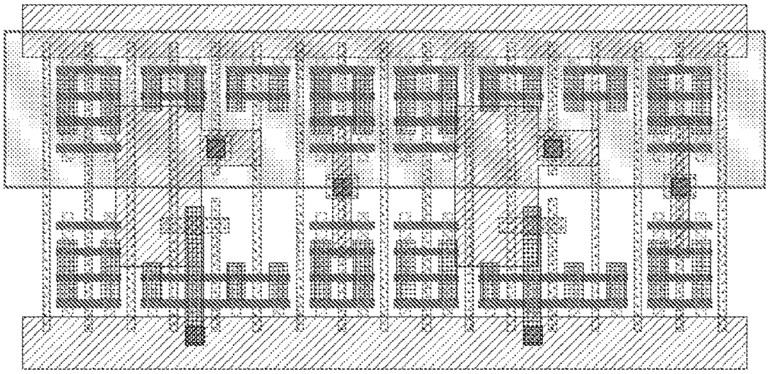
FIG. 1431A
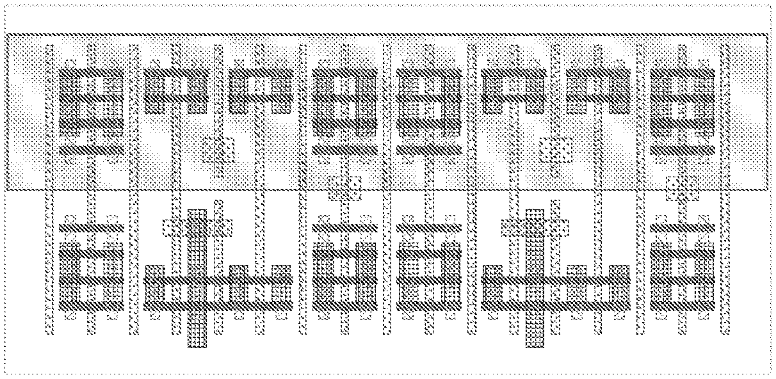
FIG. 1431B
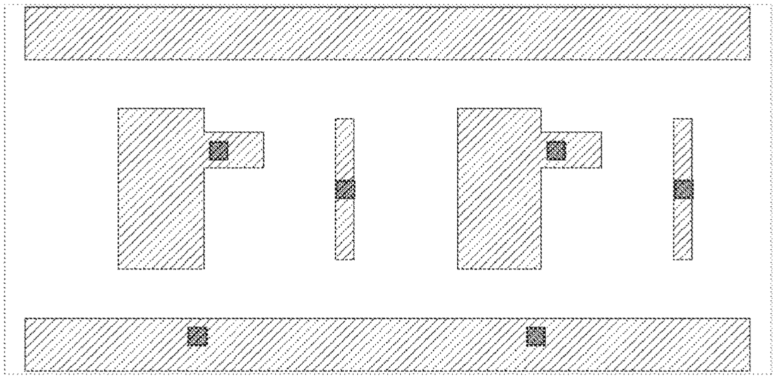
FIG. 1431C

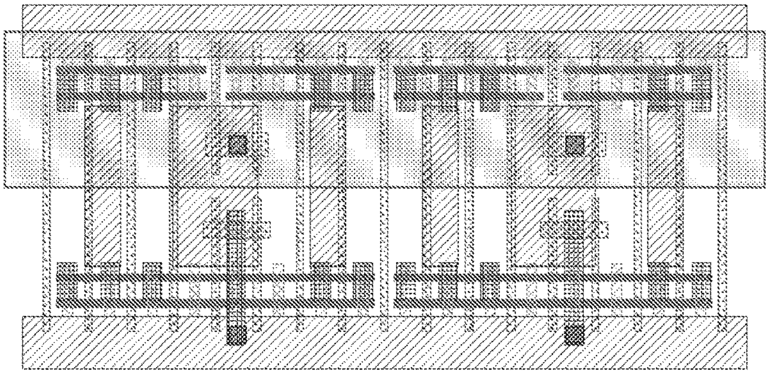
FIG. 1432A
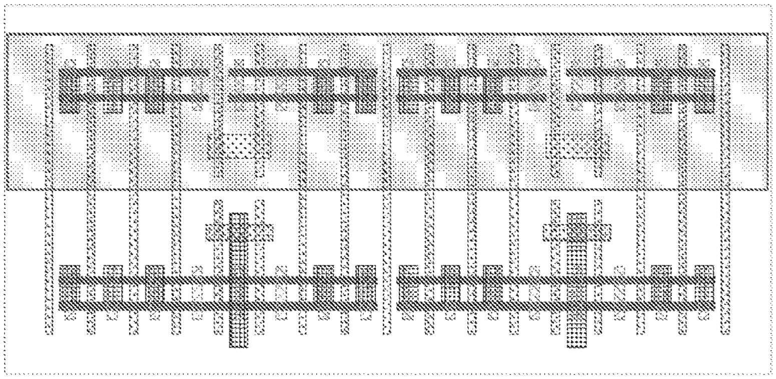
FIG. 1432B
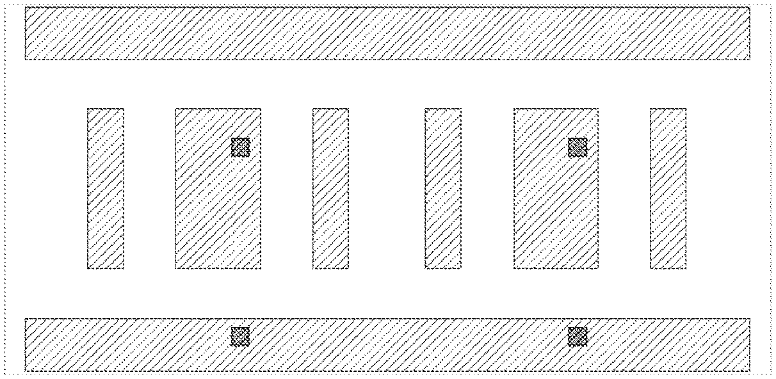
FIG. 1432C
*M* PDF Solutions, Inc.

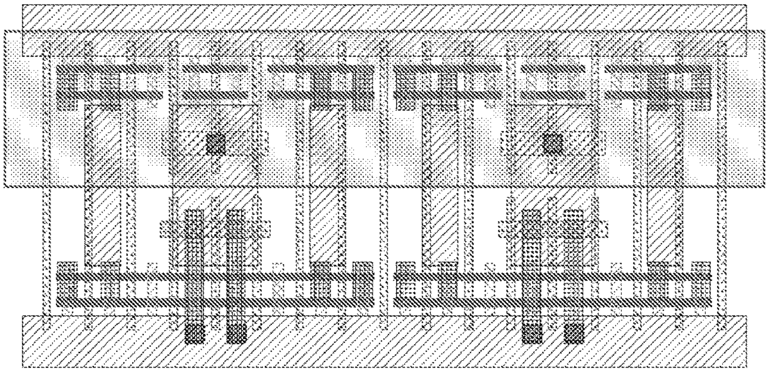
FIG. 1433A
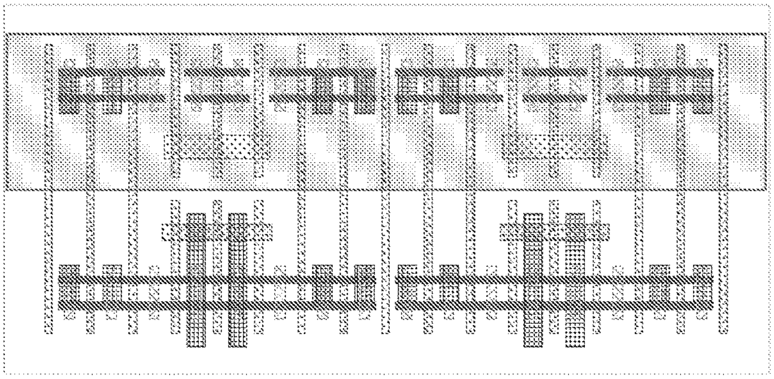
FIG. 1433B
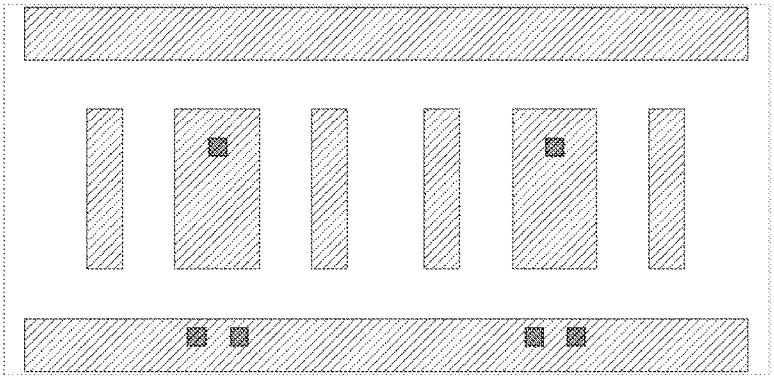
FIG. 1433C
*M* PDF Solutions, Inc.

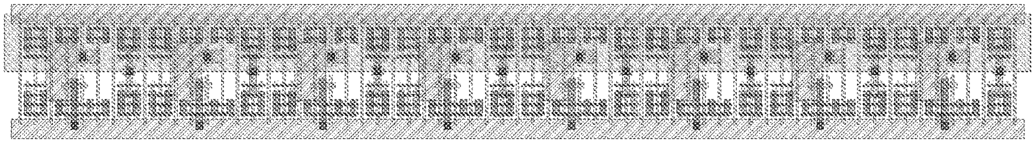
FIG. 1434A
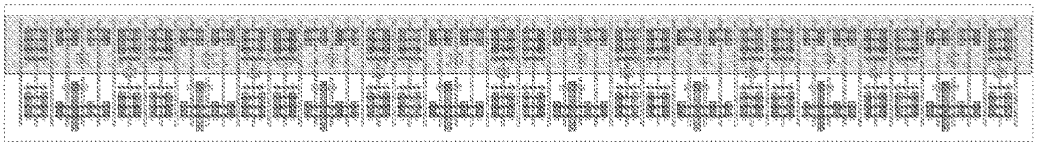
FIG. 1434B
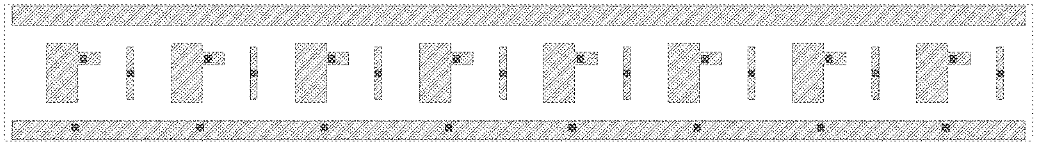
FIG. 1434C

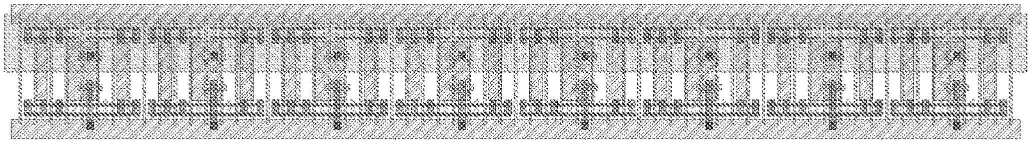
FIG. 1435A
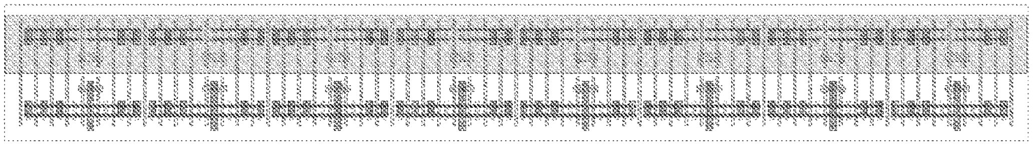
FIG. 1435B
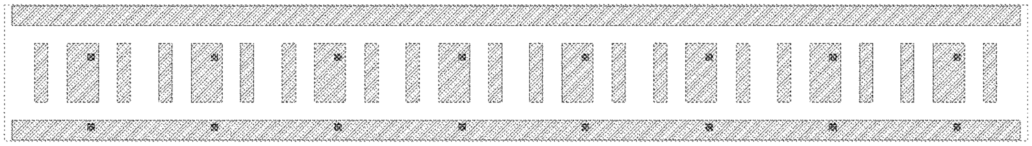
FIG. 1435C

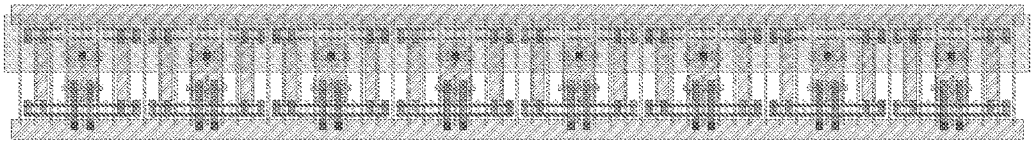
FIG. 1436A
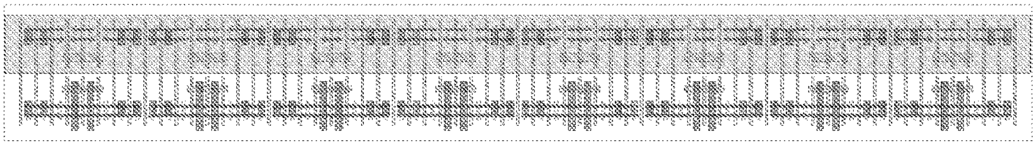
FIG. 1436B
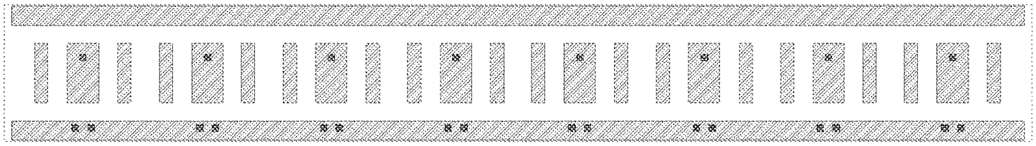
FIG. 1436C
*M* PDF Solutions, Inc.

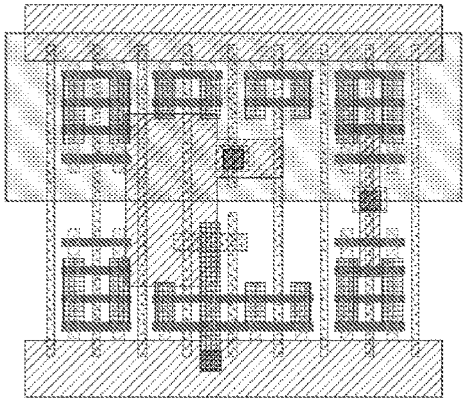
FIG. 1437A
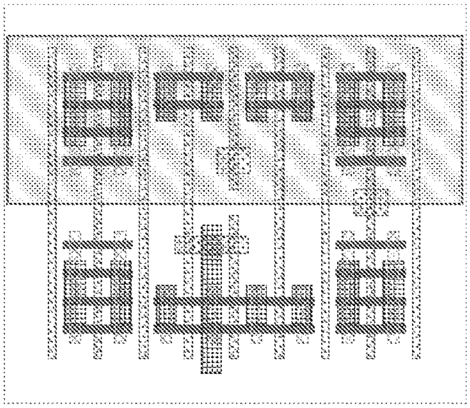
FIG. 1437B
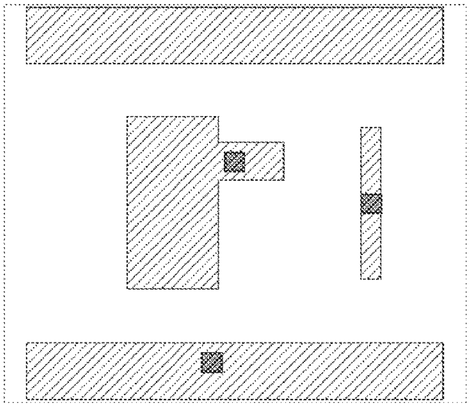
FIG. 1437C

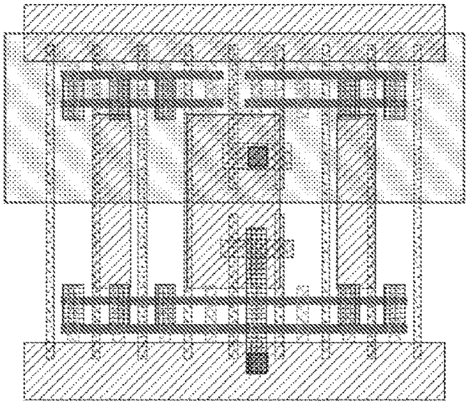
FIG. 1438A
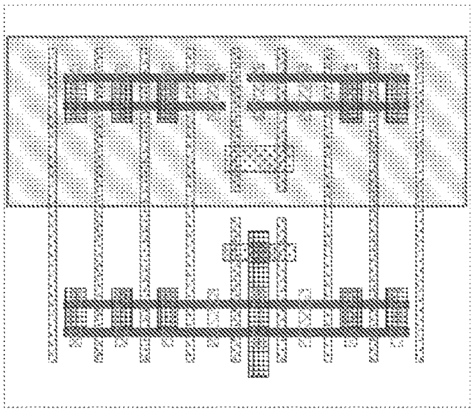
FIG. 1438B
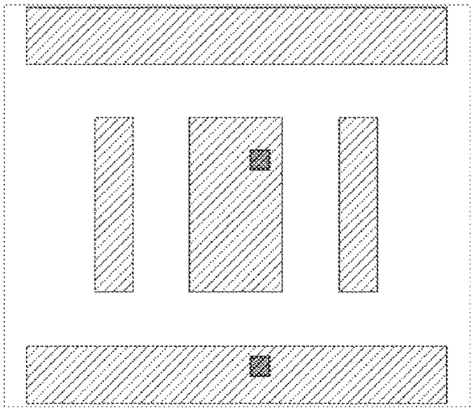
FIG. 1438C
*M* PDF Solutions, Inc.

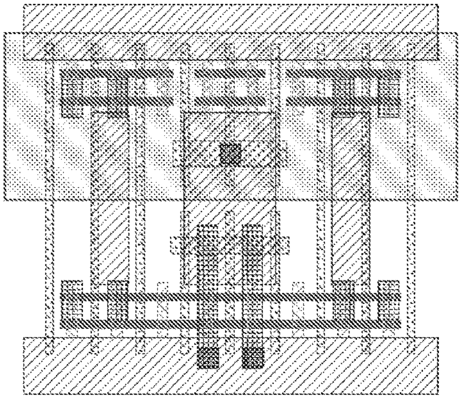
FIG. 1439A
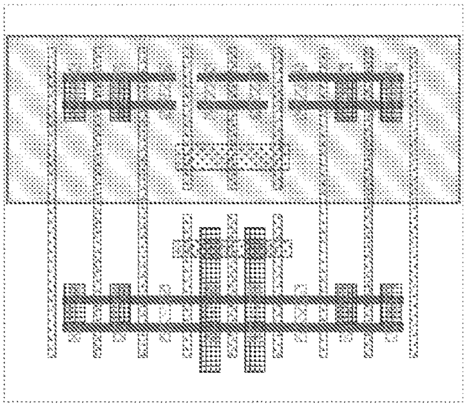
FIG. 1439B
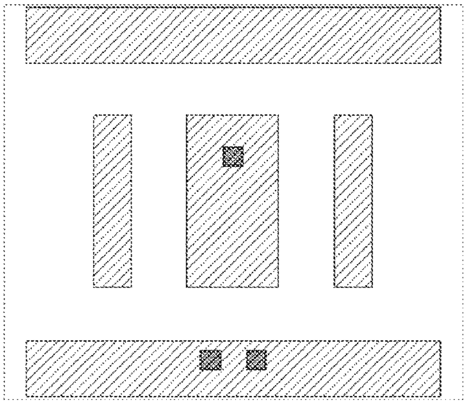
FIG. 1439C

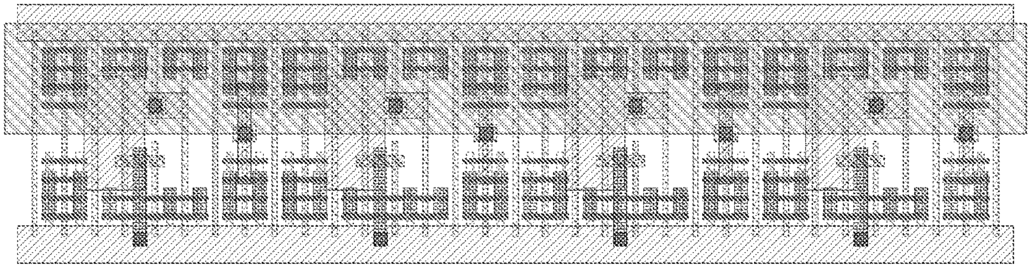
FIG. 1440A
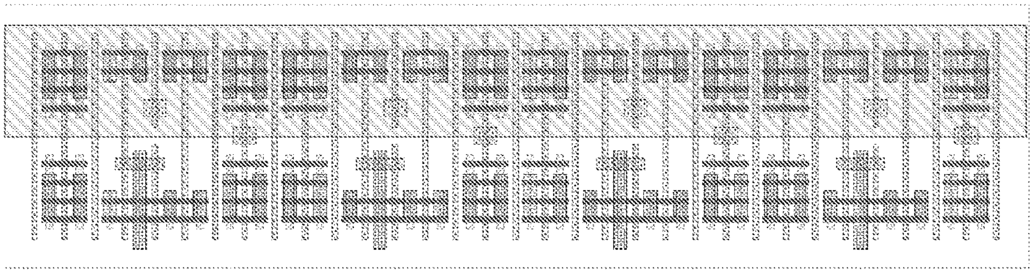
FIG. 1440B
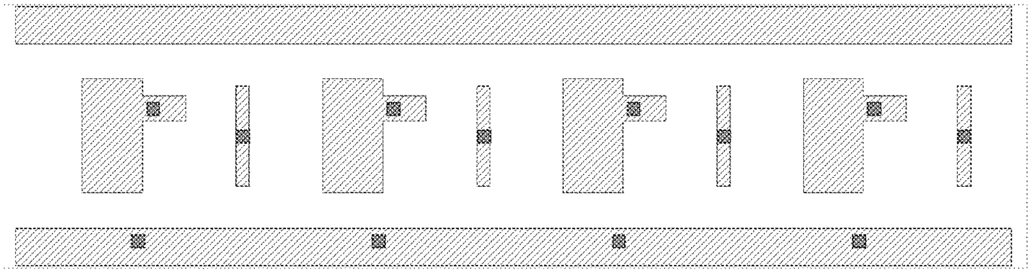
FIG. 1440C

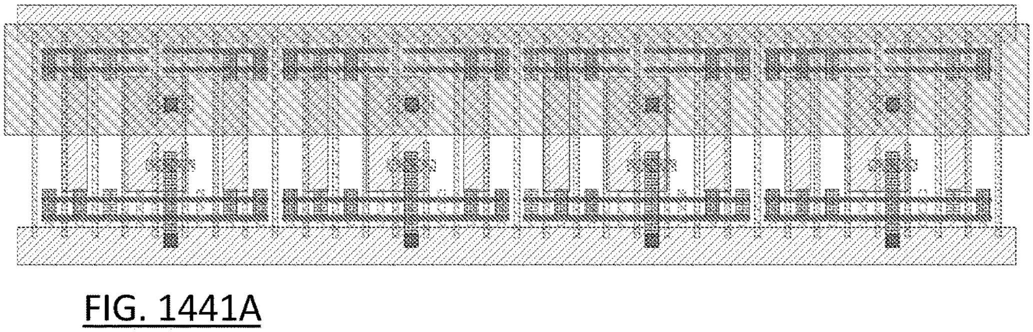
FIG. 1441A
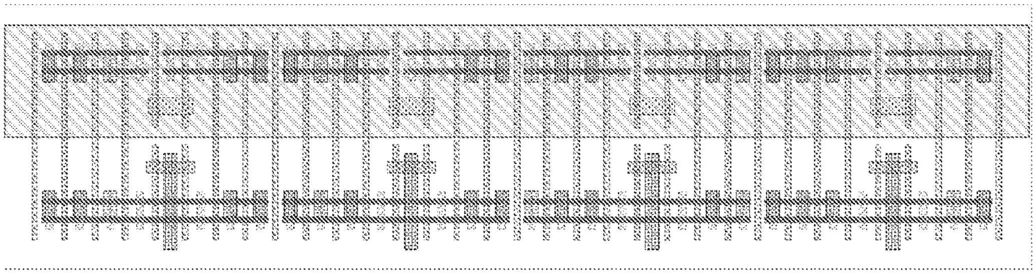
FIG. 1441B
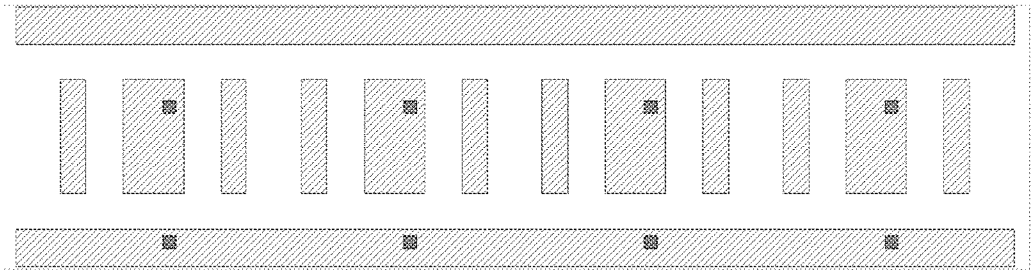
FIG. 1441C

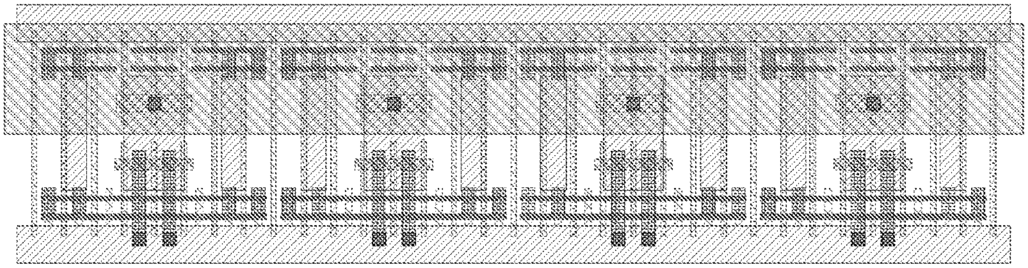
FIG. 1442A
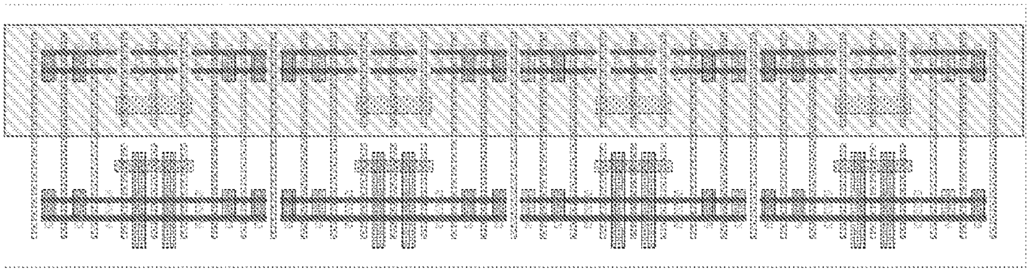
FIG. 1442B
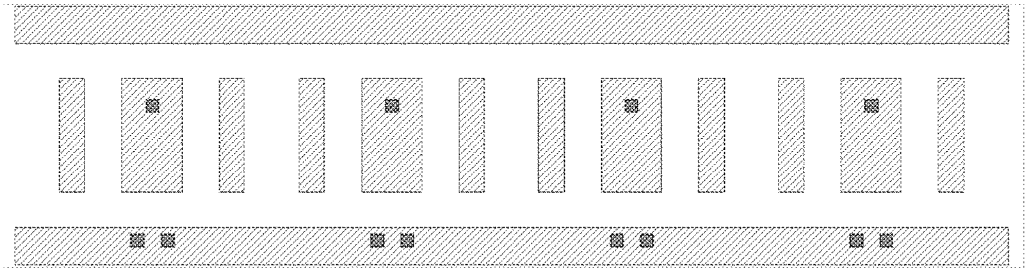
FIG. 1442C

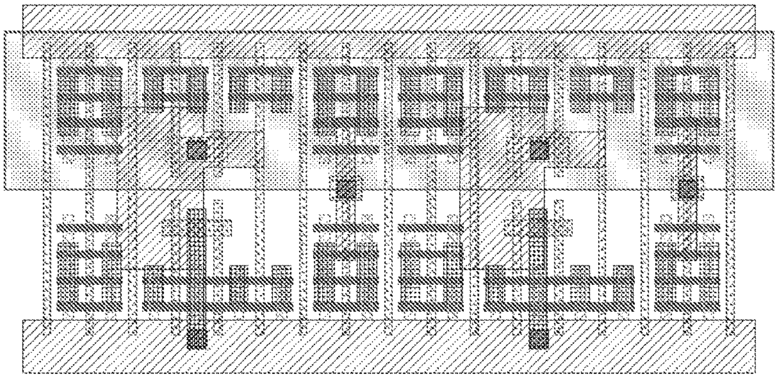
FIG. 1443A
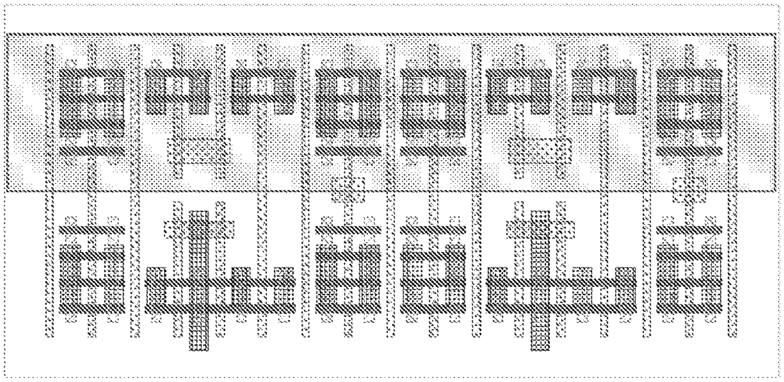
FIG. 1443B
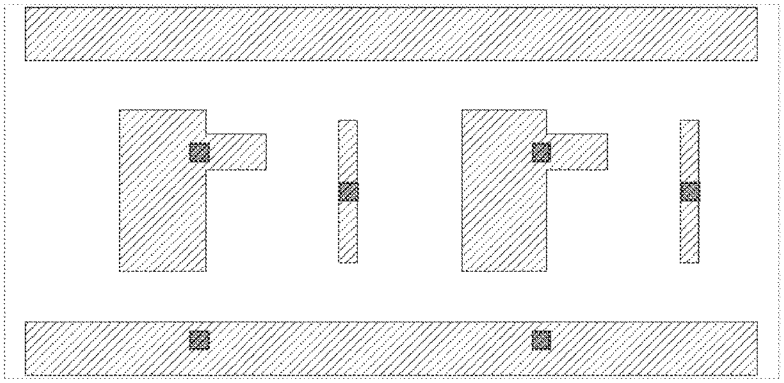
FIG. 1443C

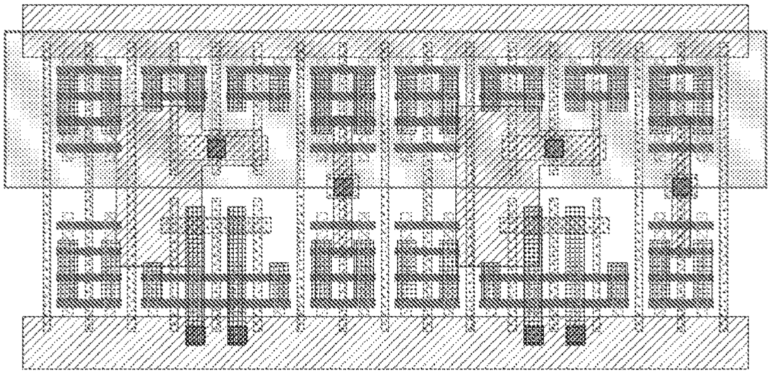
FIG. 1444A
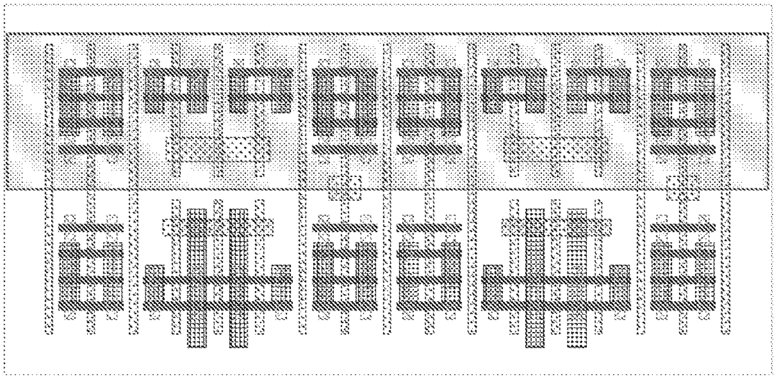
FIG. 1444B
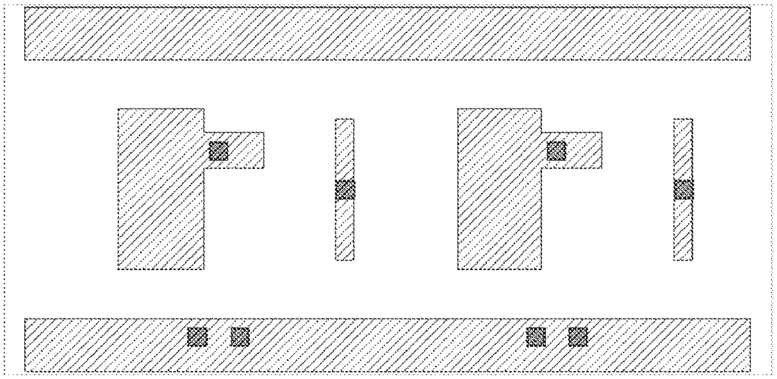
FIG. 1444C

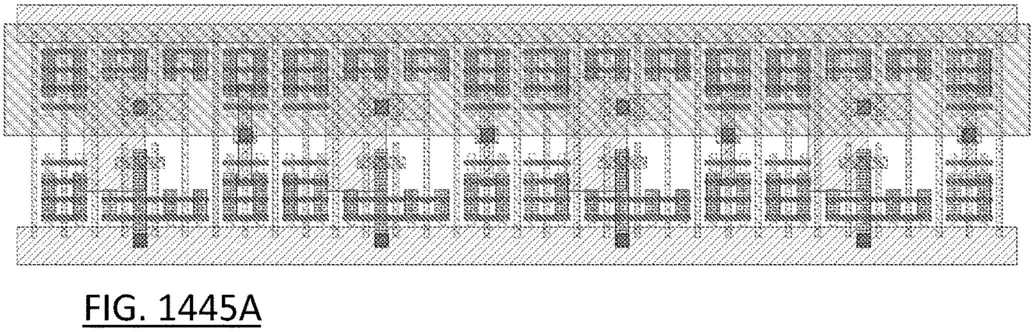
FIG. 1445A
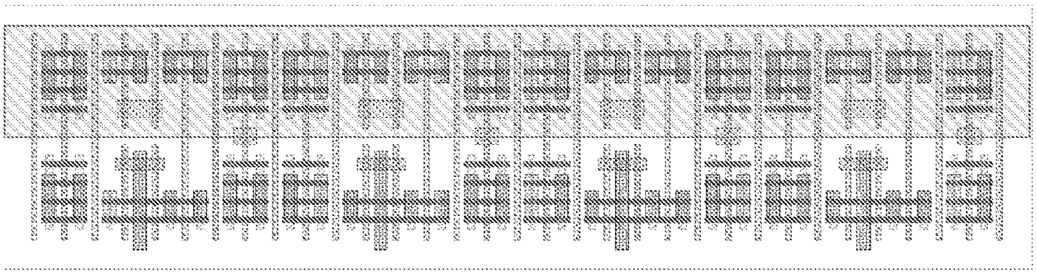
FIG. 1445B
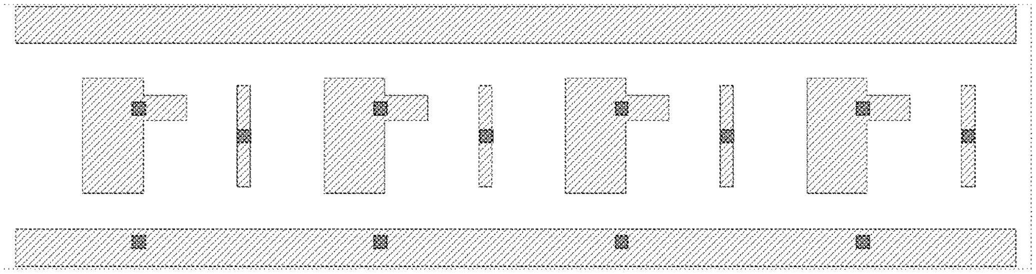
FIG. 1445C

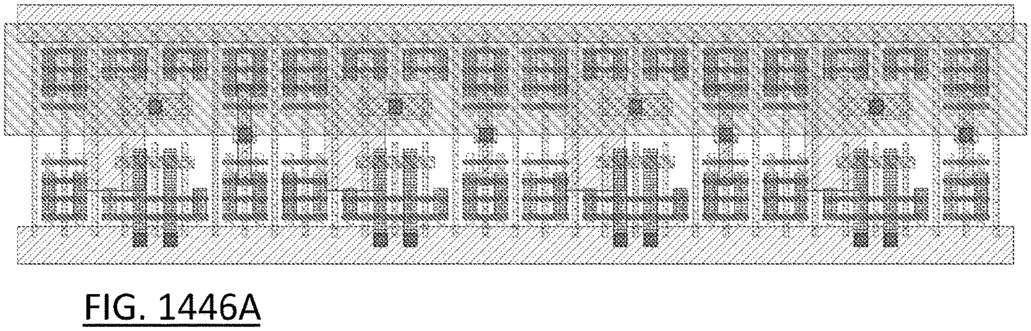
FIG. 1446A
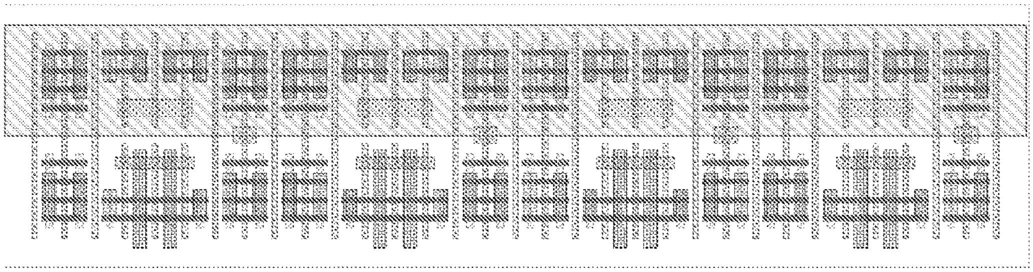
FIG. 1446B
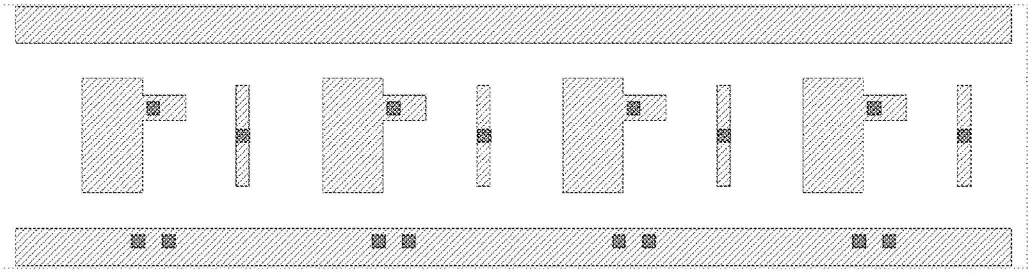
FIG. 1446C

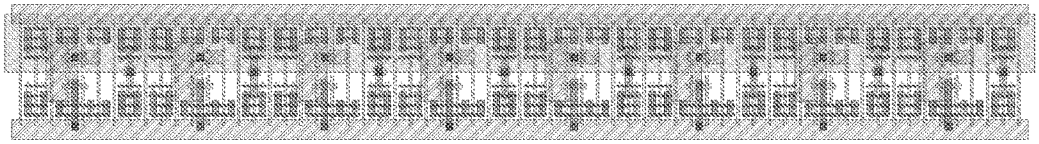
FIG. 1447A
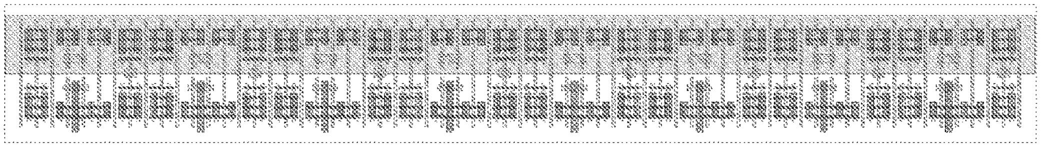
FIG. 1447B
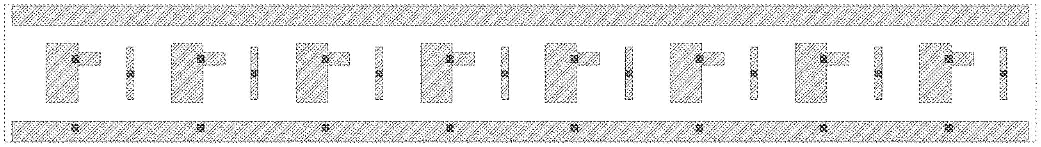
FIG. 1447C

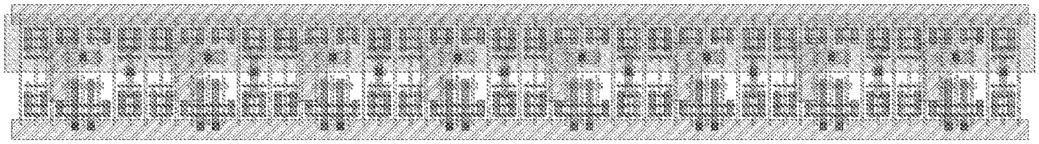
FIG. 1448A
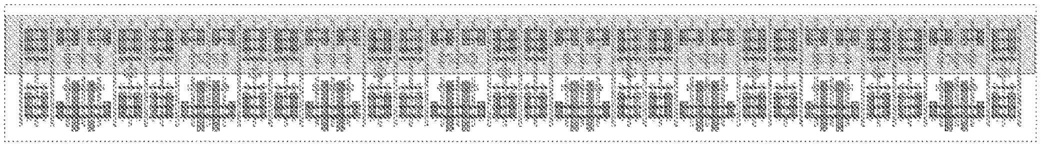
FIG. 1448B
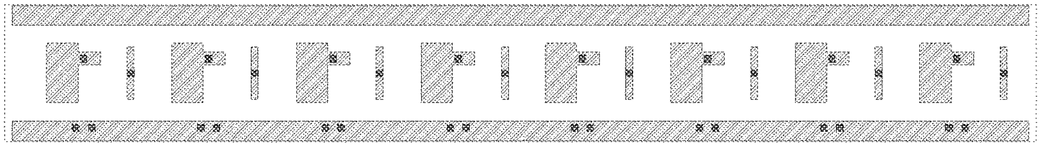
FIG. 1448C
*M* PDF Solutions, Inc.

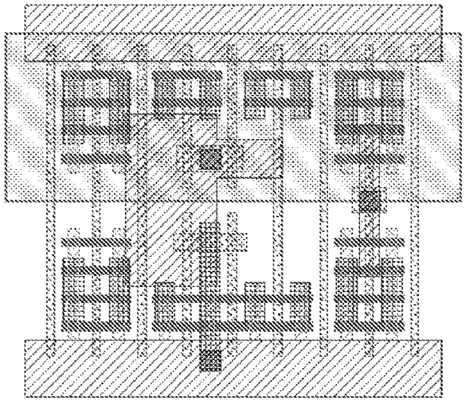
FIG. 1449A
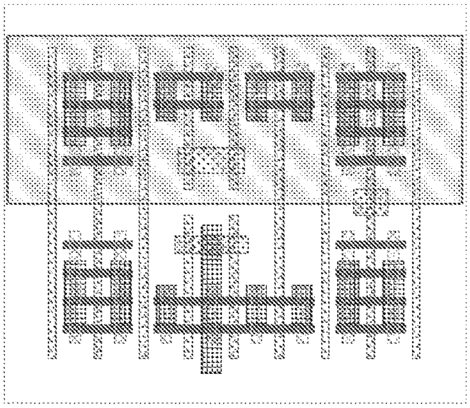
FIG. 1449B
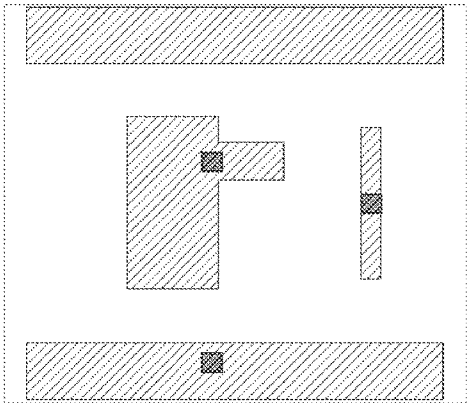
FIG. 1449C

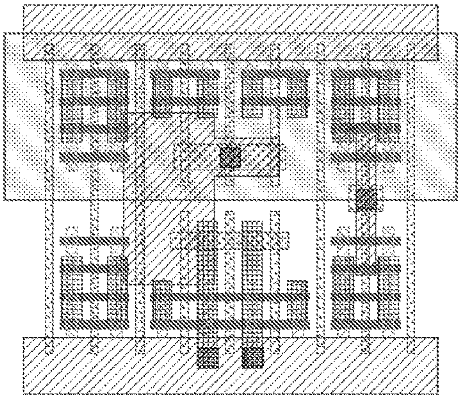
FIG. 1450A
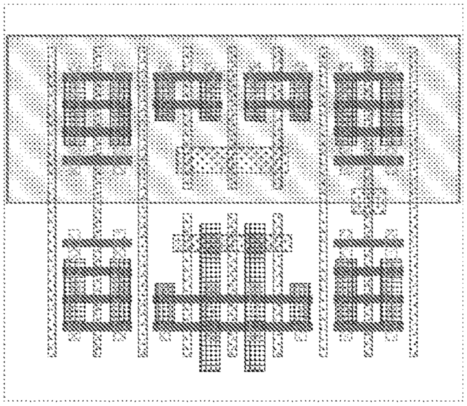
FIG. 1450B
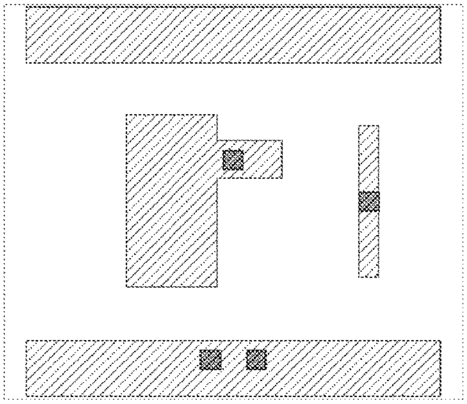
FIG. 1450C

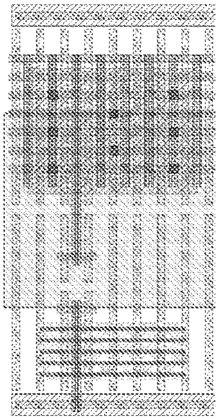
FIG. 1451A
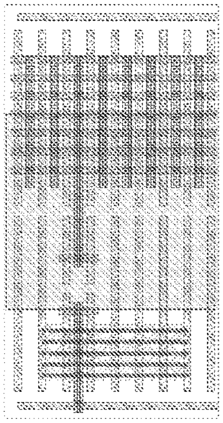
FIG. 1451B
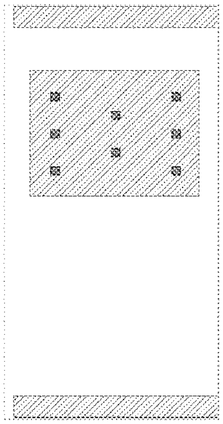
FIG. 1451C
*M* PDF Solutions, Inc.

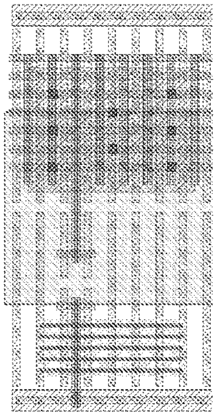
FIG. 1452A
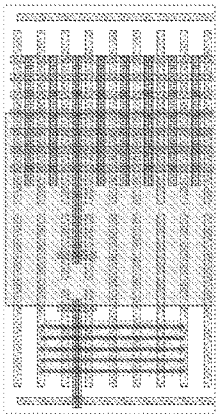
FIG. 1452B
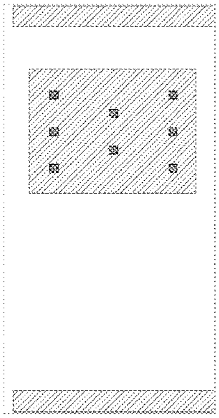
FIG. 1452C

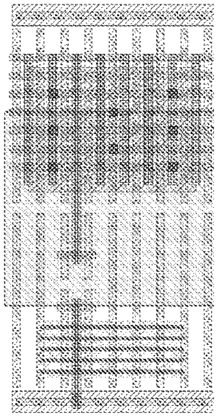
FIG. 1453A
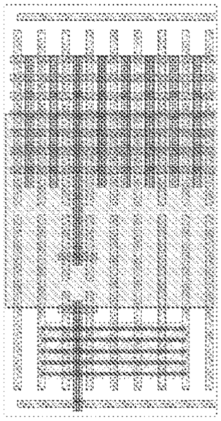
FIG. 1453B
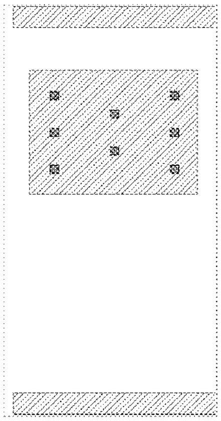
FIG. 1453C

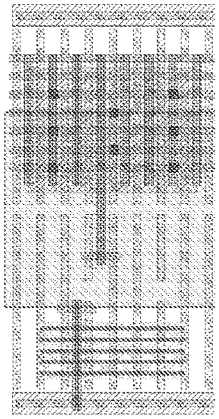
FIG. 1454A
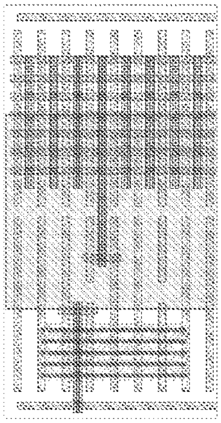
FIG. 1454B
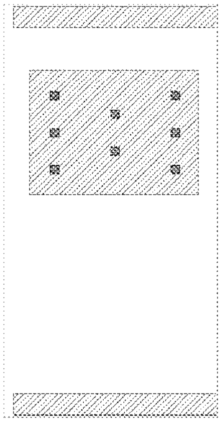
FIG. 1454C

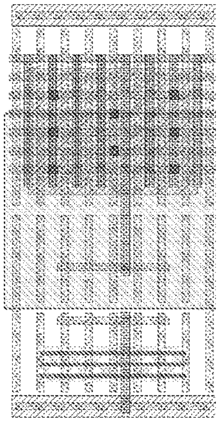
FIG. 1455A
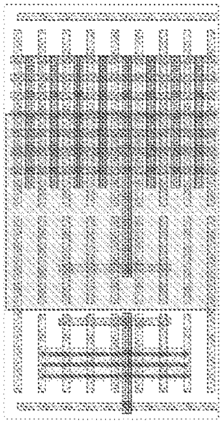
FIG. 1455B
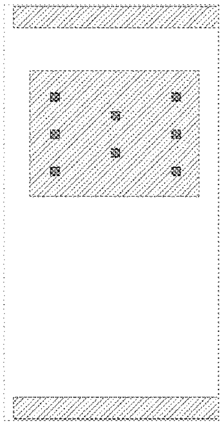
FIG. 1455C

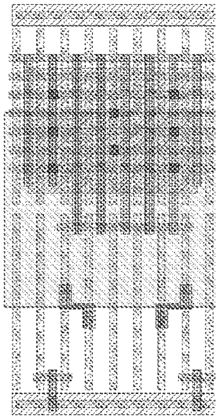
FIG. 1456A
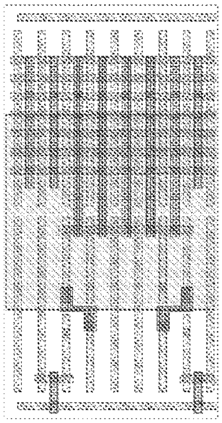
FIG. 1456B
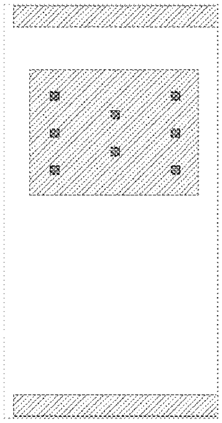
FIG. 1456C

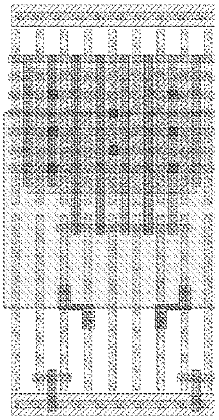
FIG. 1457A
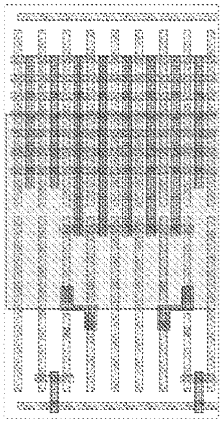
FIG. 1457B
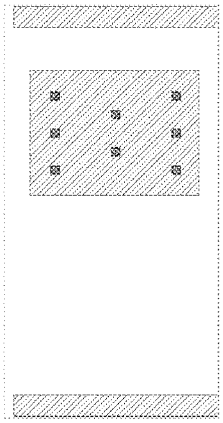
FIG. 1457C

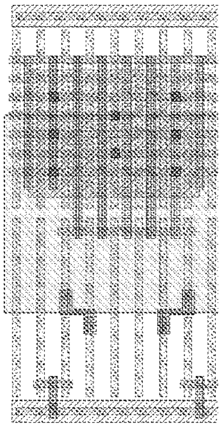
FIG. 1458A
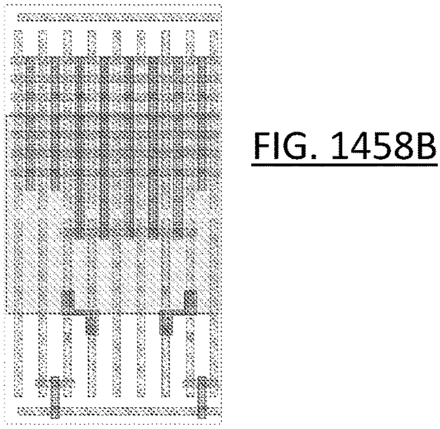
FIG. 1458B
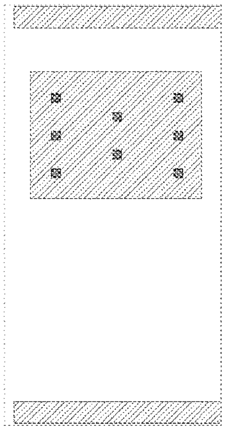
FIG. 1458C
*M* PDF Solutions, Inc.

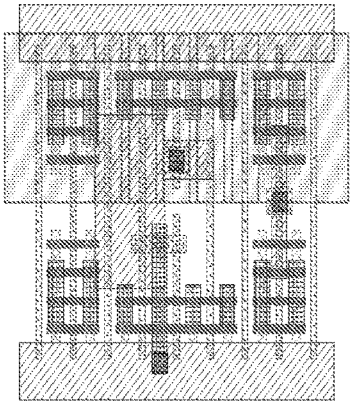
FIG. 1459A
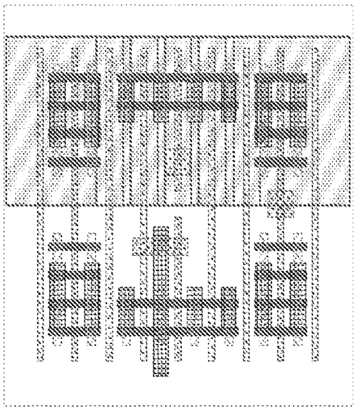
FIG. 1459B
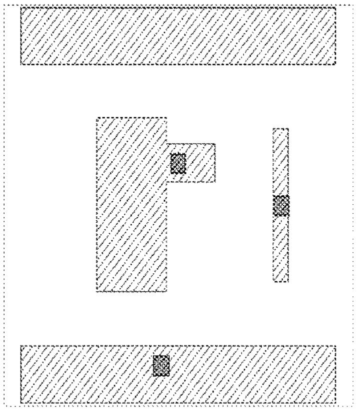
FIG. 1459C

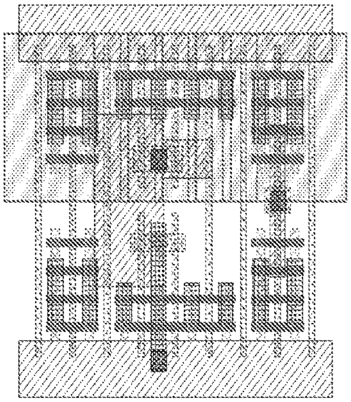
FIG. 1460A
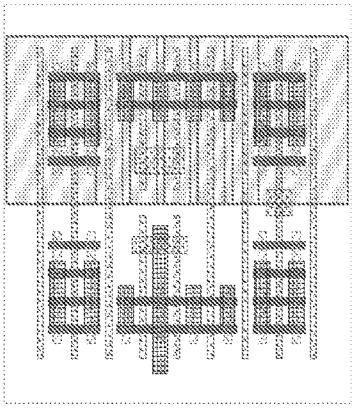
FIG. 1460B
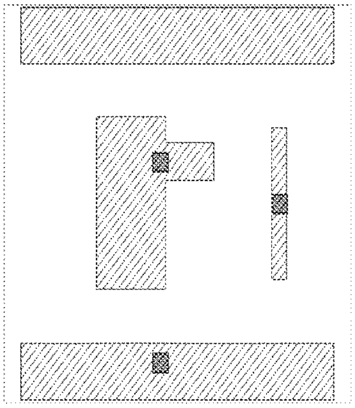
FIG. 1460C
*M* PDF Solutions, Inc.

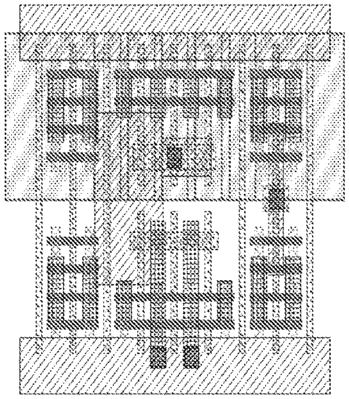
FIG. 1461A
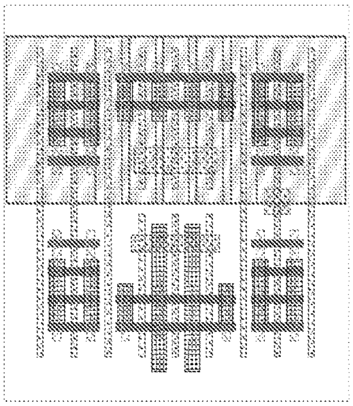
FIG. 1461B
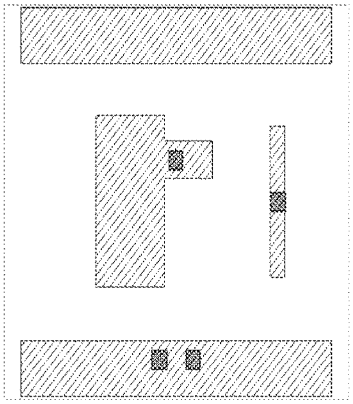
FIG. 1461C
*M* PDF Solutions, Inc.

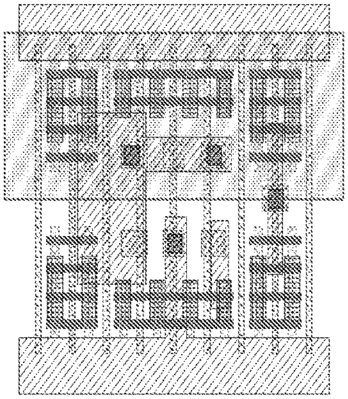
FIG. 1462A
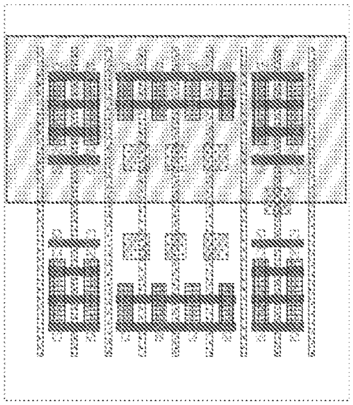
FIG. 1462B
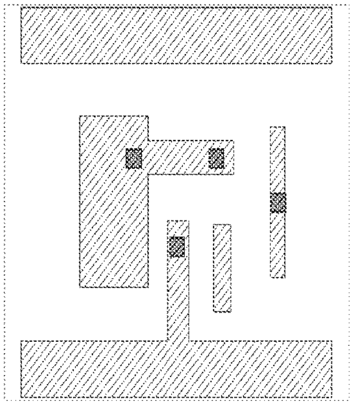
FIG. 1462C

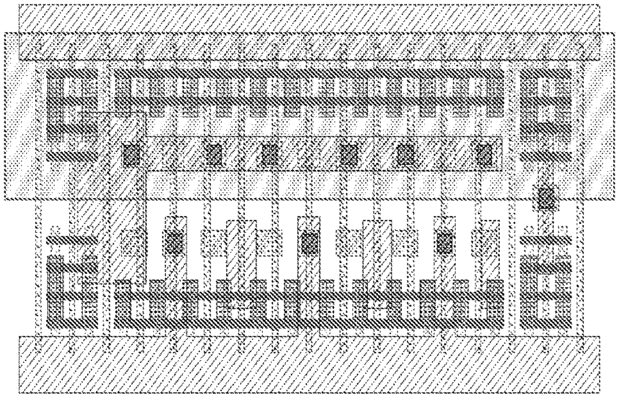
FIG. 1463A
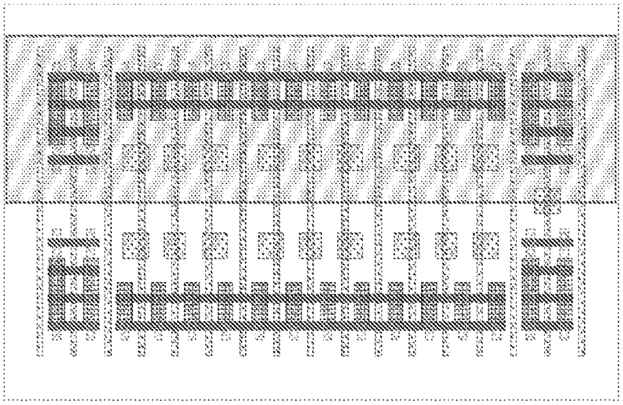
FIG. 1463B
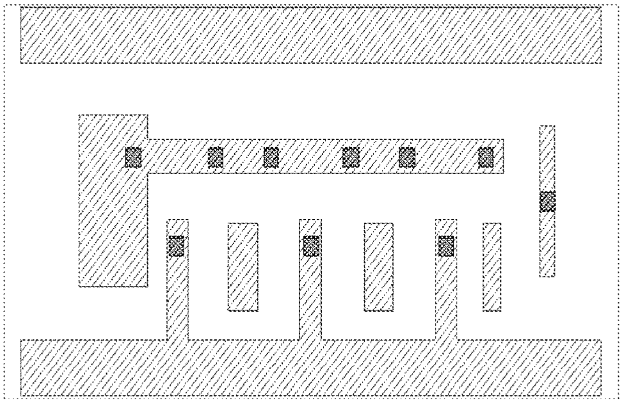
FIG. 1463C

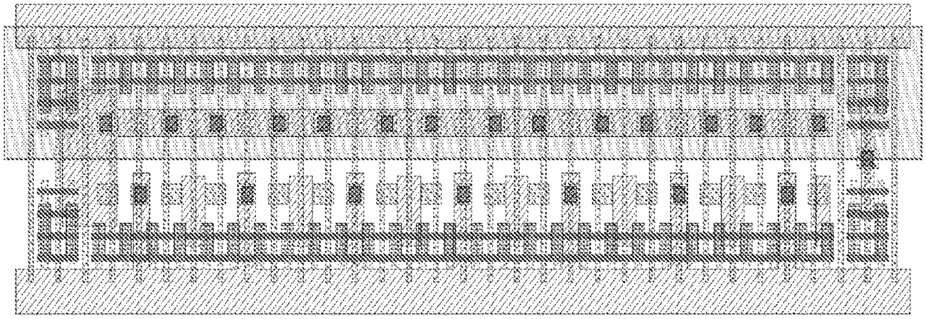
FIG. 1464A
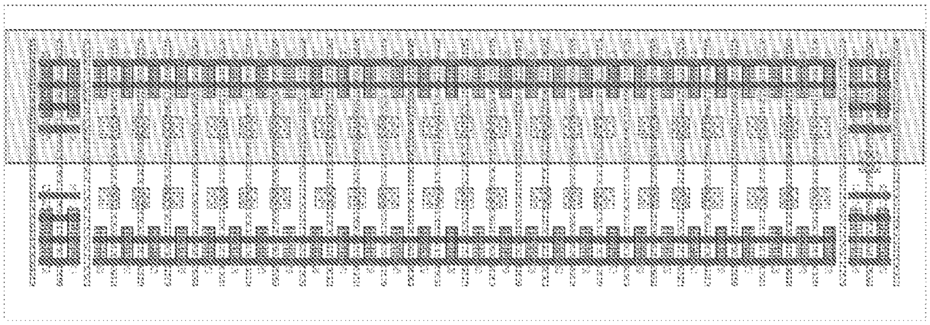
FIG. 1464B
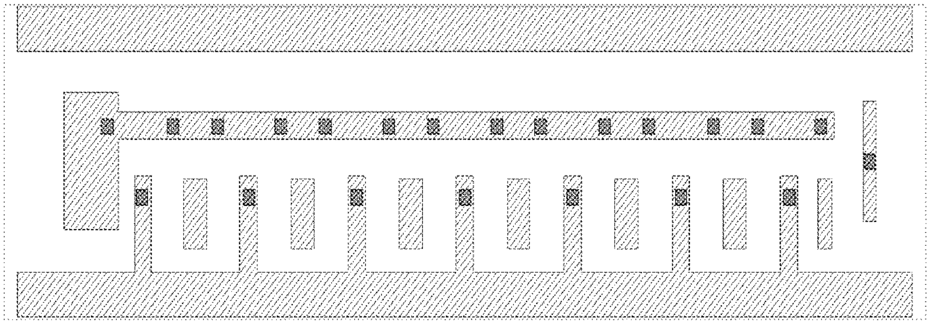
FIG. 1464C

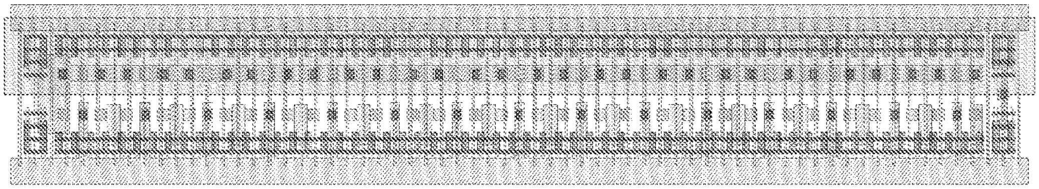
FIG. 1465A
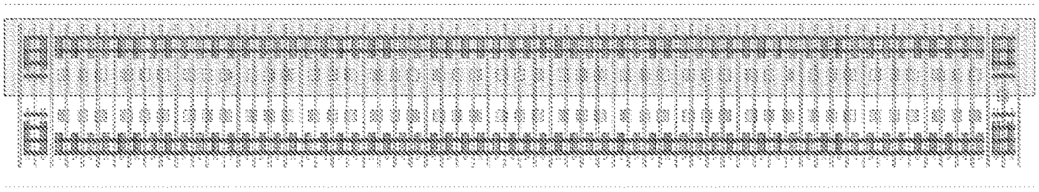
FIG. 1465B
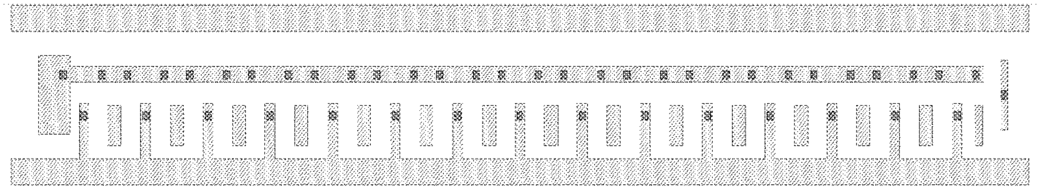
FIG. 1465C

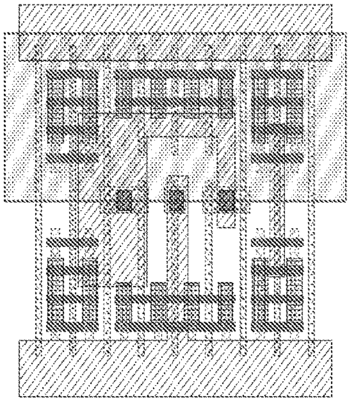
FIG. 1466A
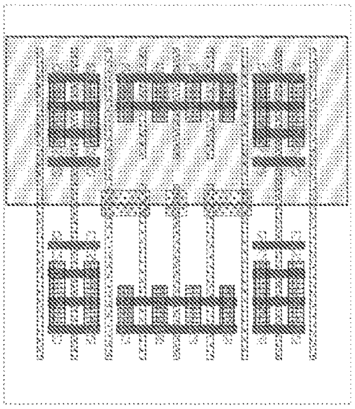
FIG. 1466B
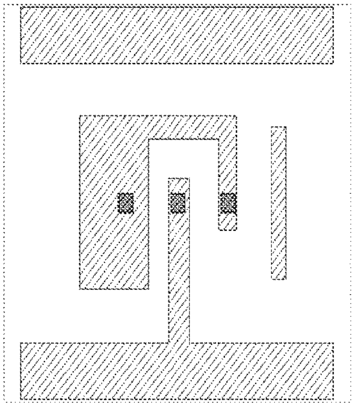
FIG. 1466C

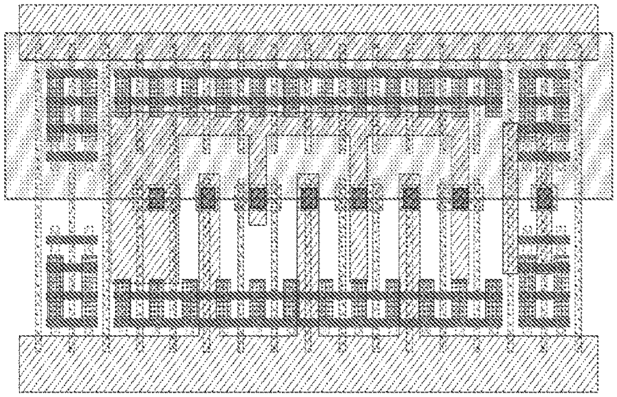
FIG. 1467A
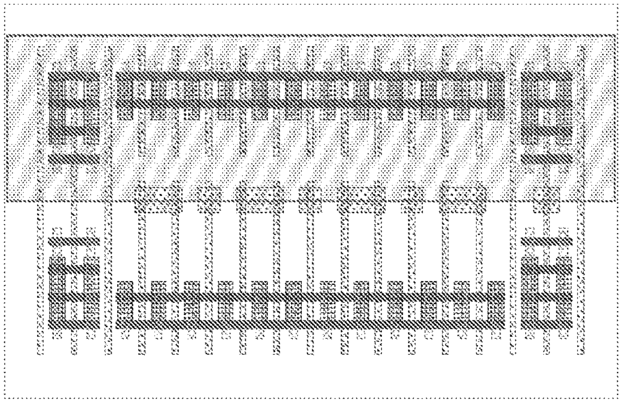
FIG. 1467B
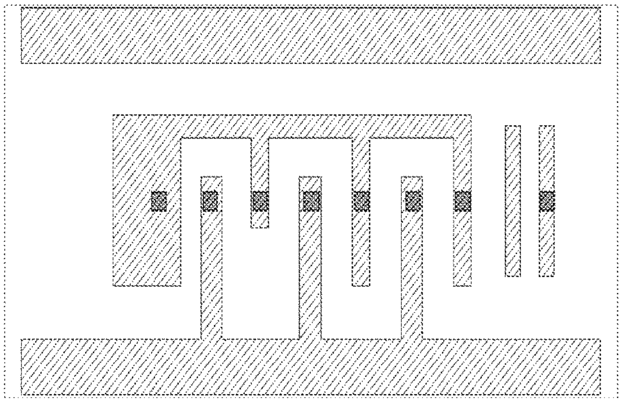
FIG. 1467C

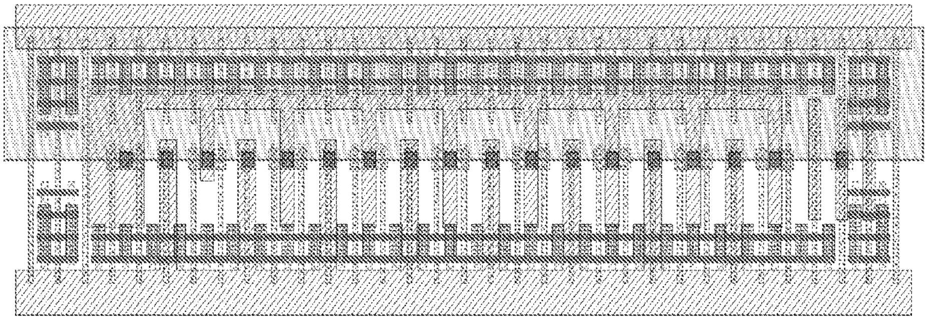
FIG. 1468A
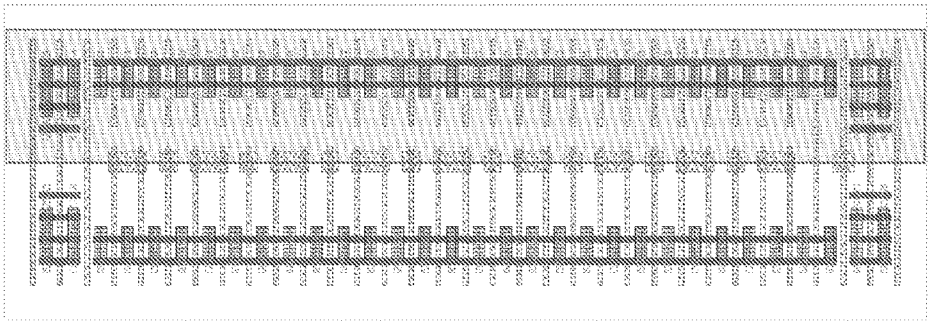
FIG. 1468B
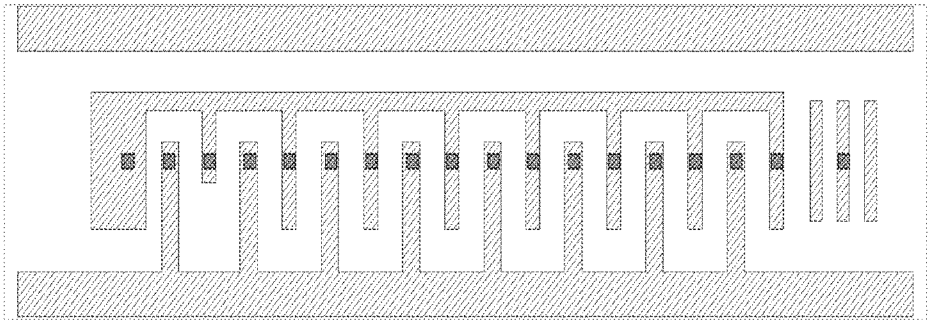
FIG. 1468C
*M* PDF Solutions, Inc.

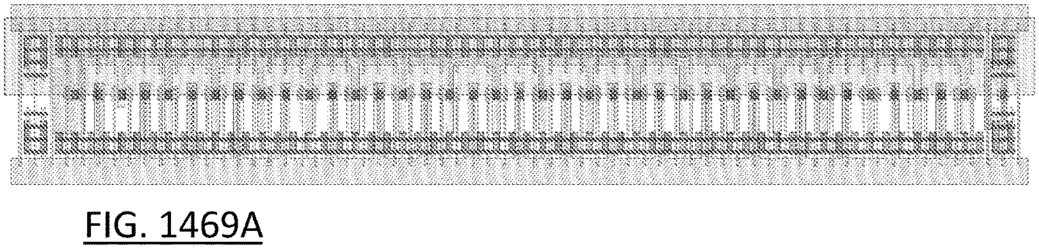
FIG. 1469A
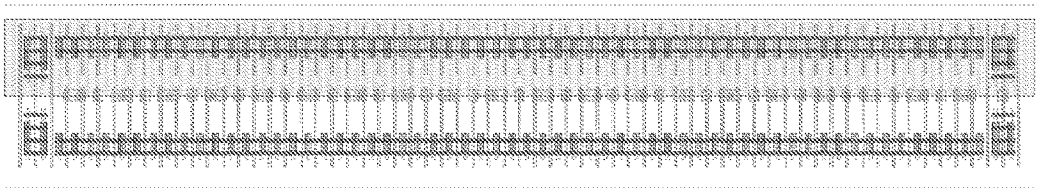
FIG. 1469B
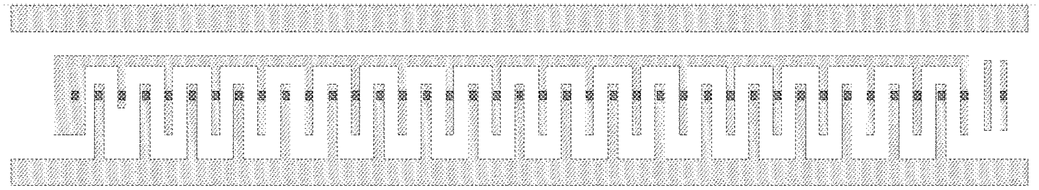
FIG. 1469C

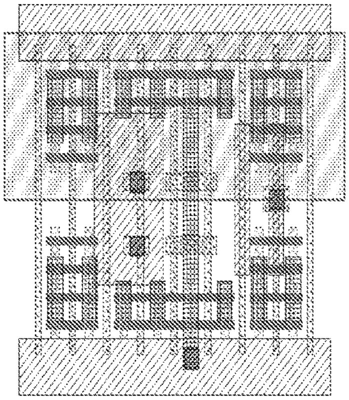
FIG. 1470A
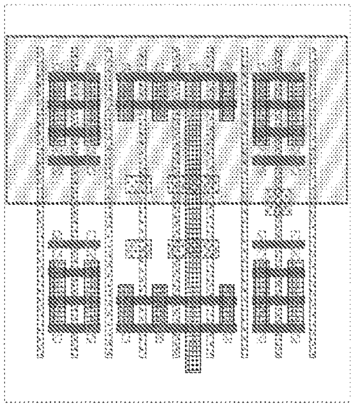
FIG. 1470B
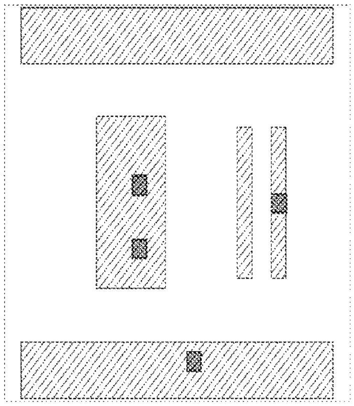
FIG. 1470C
*M* PDF Solutions, Inc.

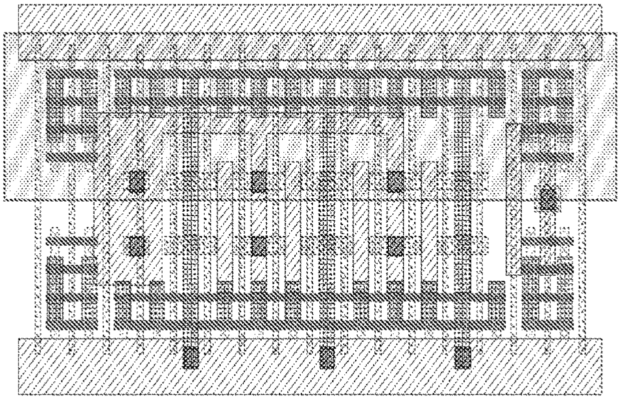
FIG. 1471A
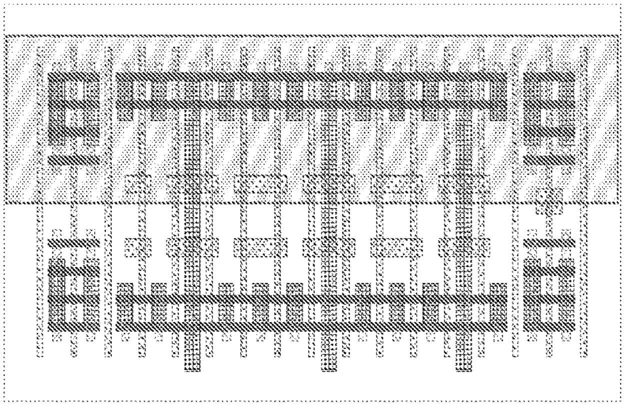
FIG. 1471B
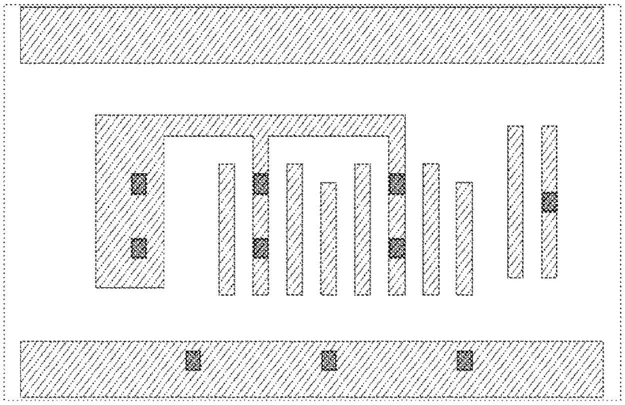
FIG. 1471C

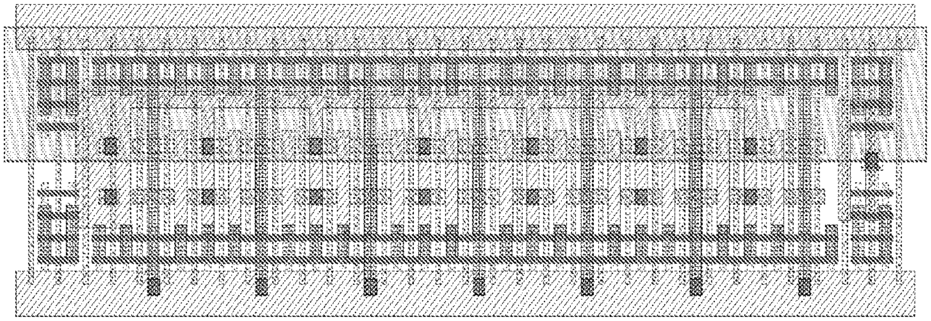
FIG. 1472A
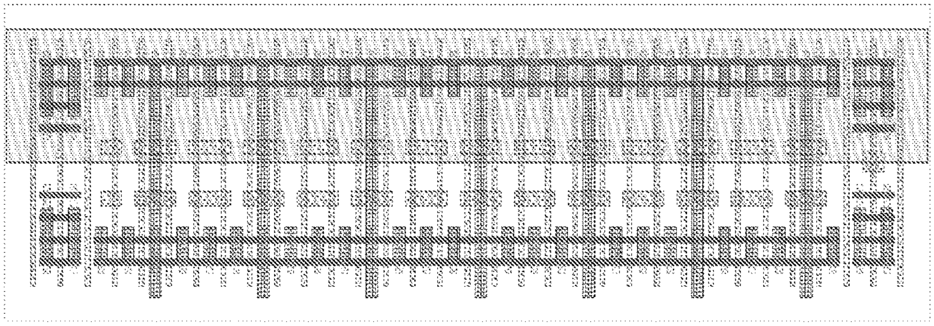
FIG. 1472B
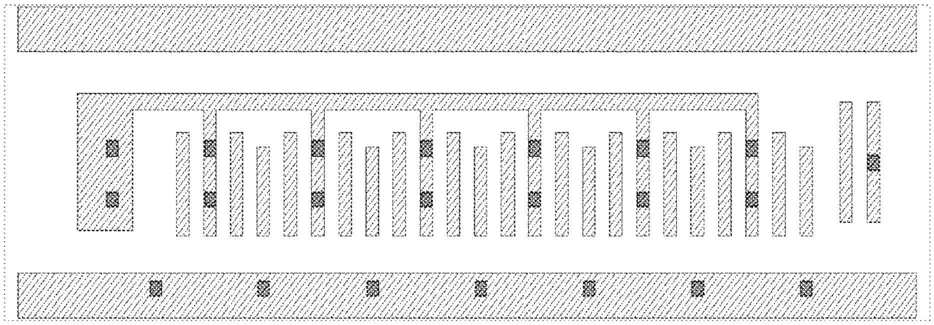
FIG. 1472C
*M* PDF Solutions, Inc.

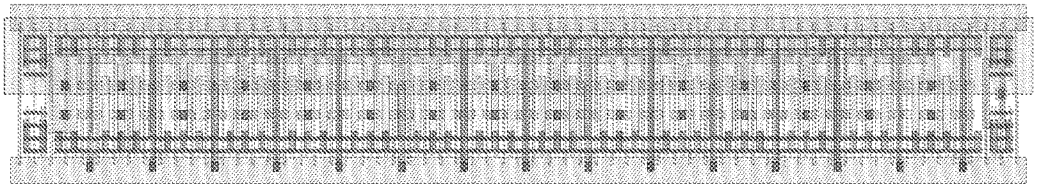
FIG. 1473A
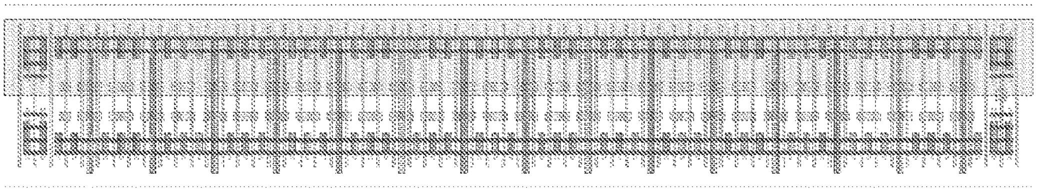
FIG. 1473B
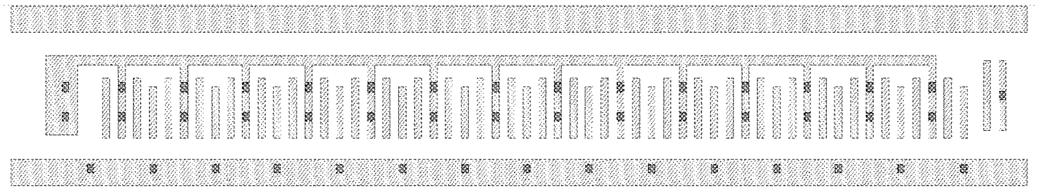
FIG. 1473C

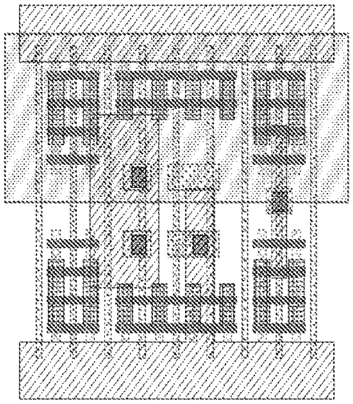
FIG. 1474A
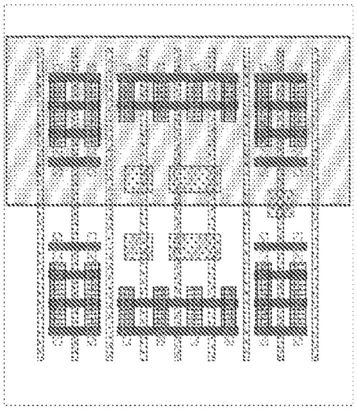
FIG. 1474B
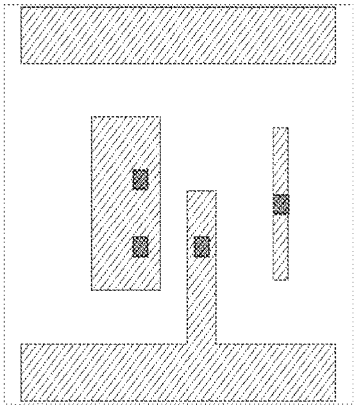
FIG. 1474C

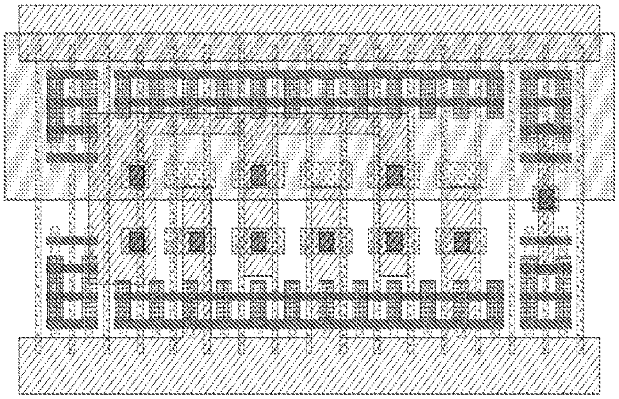
FIG. 1475A
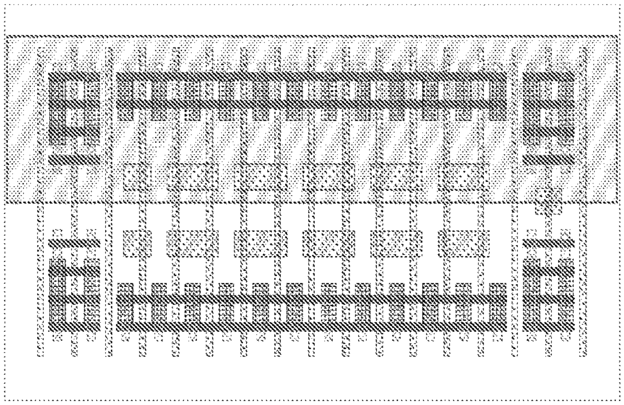
FIG. 1475B
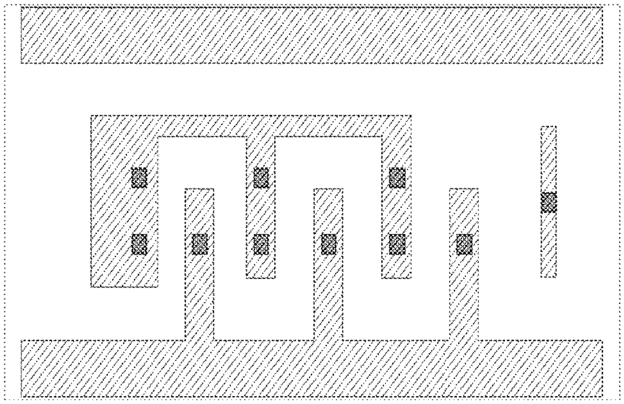
FIG. 1475C

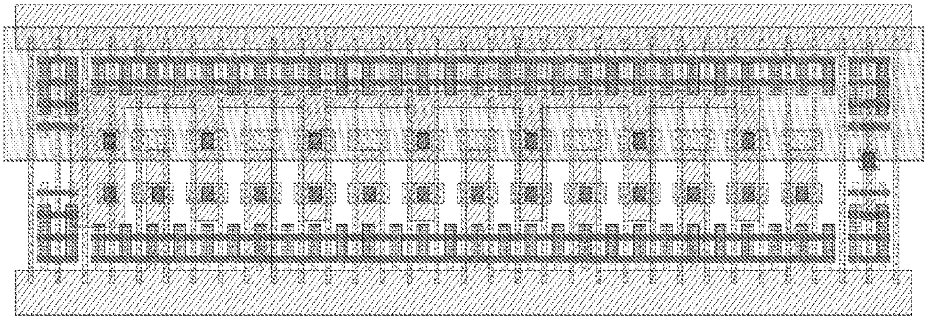
FIG. 1476A
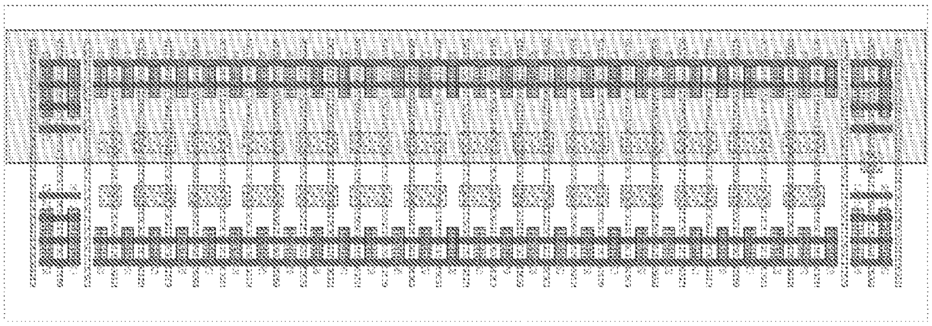
FIG. 1476B
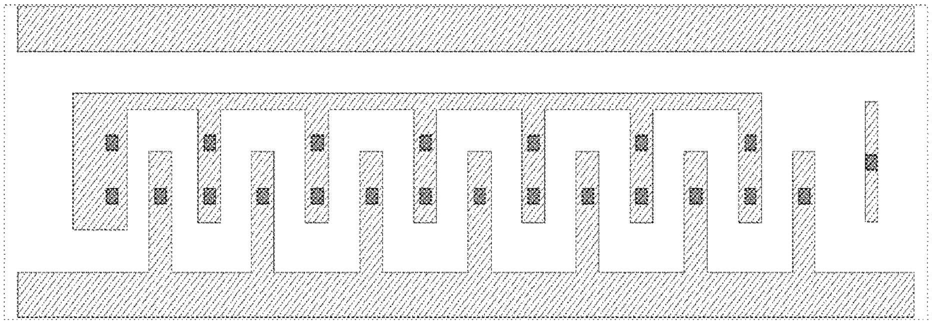
FIG. 1476C

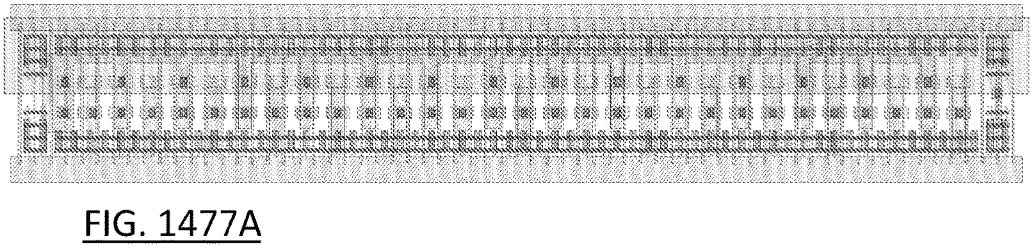
FIG. 1477A
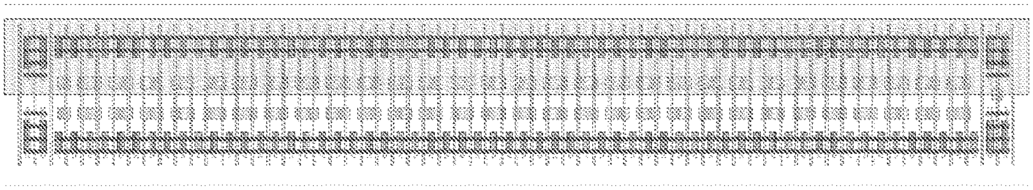
FIG. 1477B
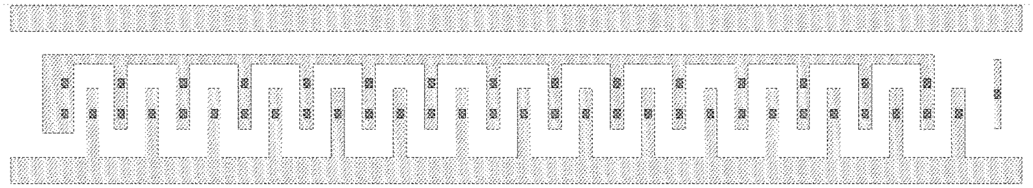
FIG. 1477C

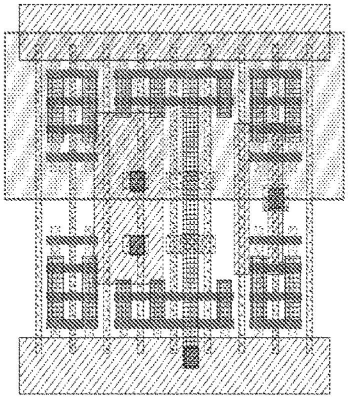
FIG. 1478A
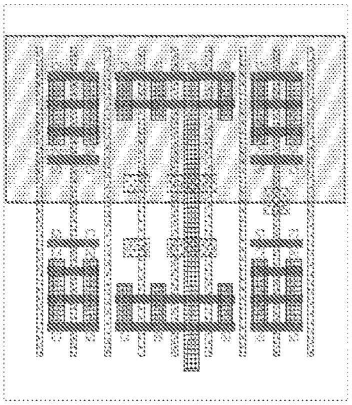
FIG. 1478B
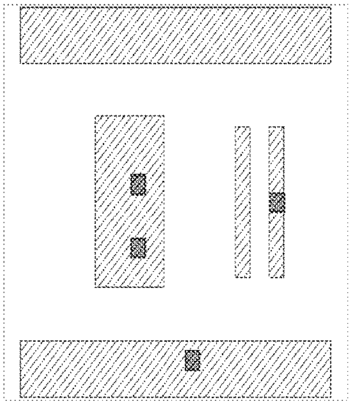
FIG. 1478C

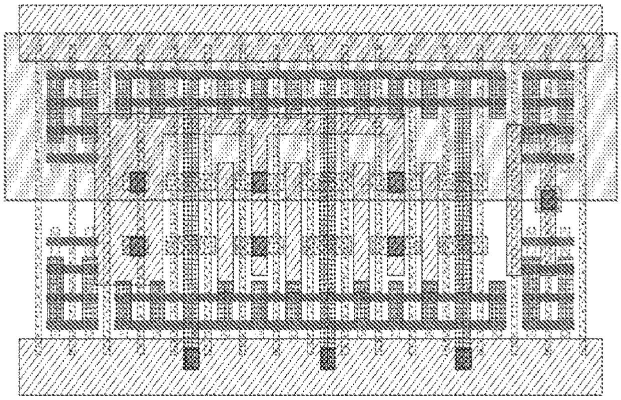
FIG. 1479A
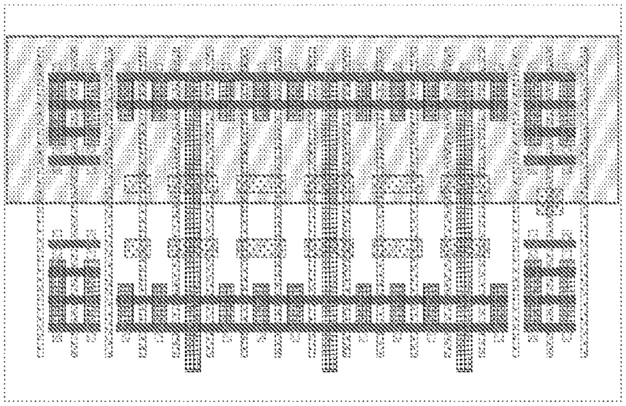
FIG. 1479B
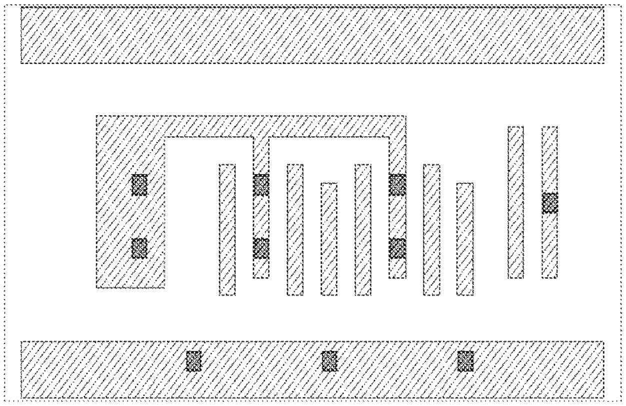
FIG. 1479C
*M* PDF Solutions, Inc.

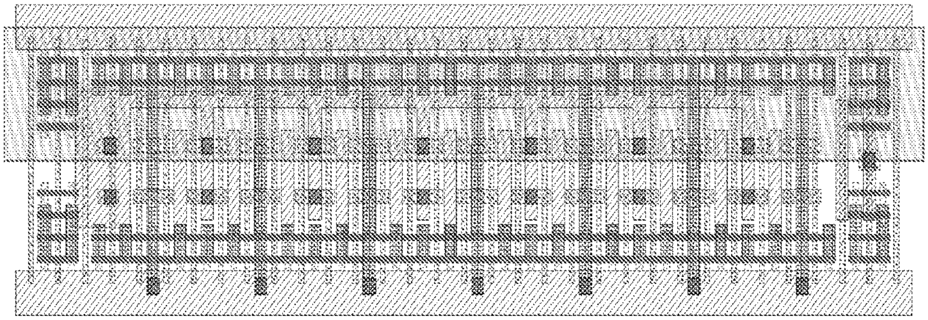
FIG. 1480A
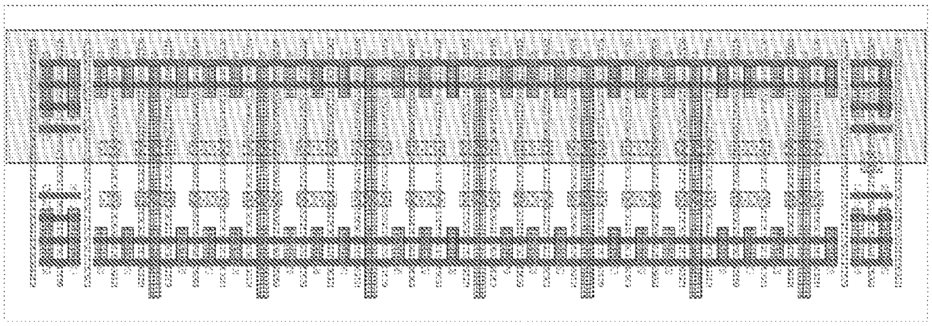
FIG. 1480B
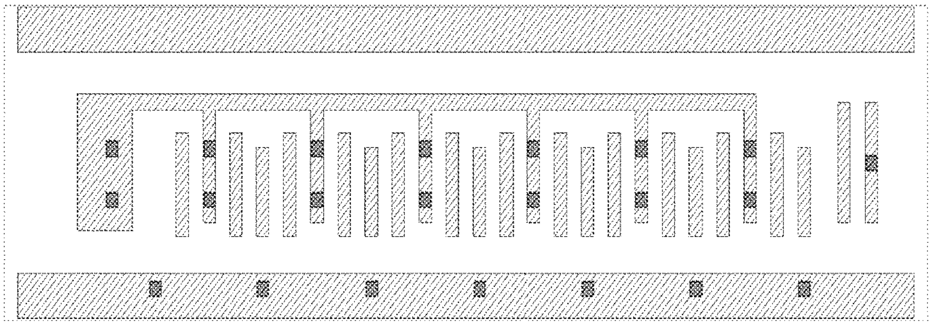
FIG. 1480C

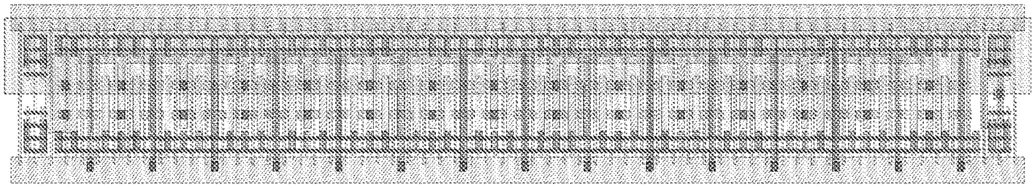
FIG. 1481A
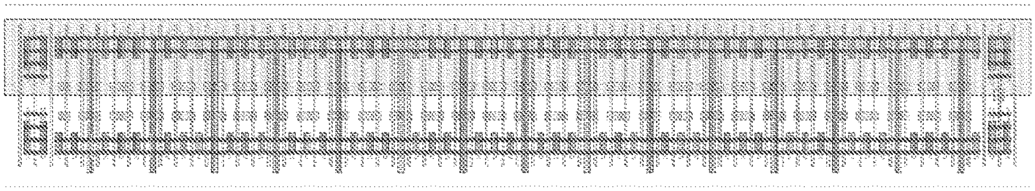
FIG. 1481B
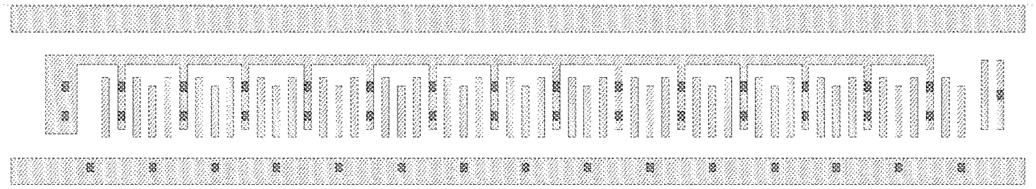
FIG. 1481C

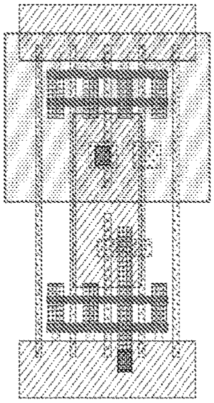
FIG. 1482A
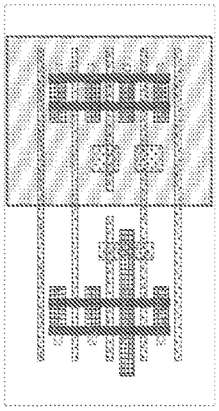
FIG. 1482B
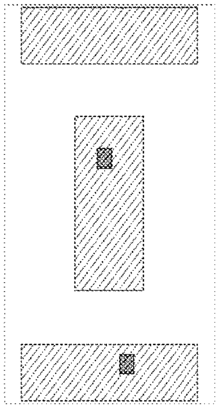
FIG. 1482C

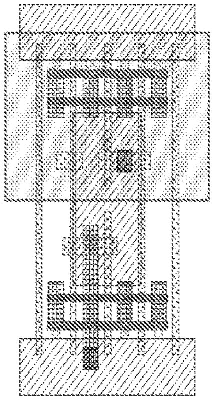
FIG. 1483A
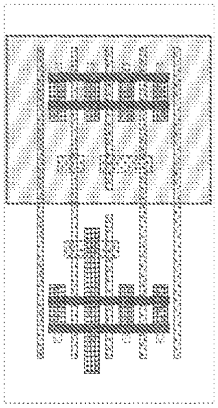
FIG. 1483B
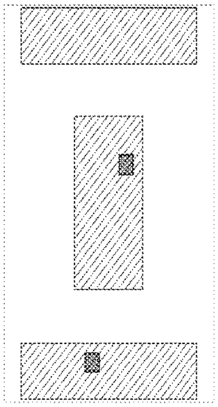
FIG. 1483C

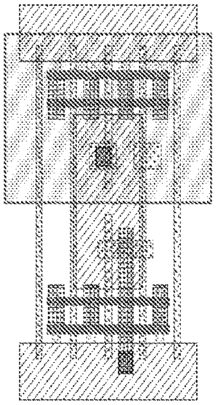
FIG. 1484A
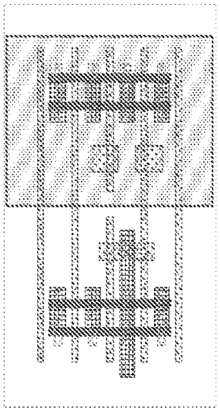
FIG. 1484B
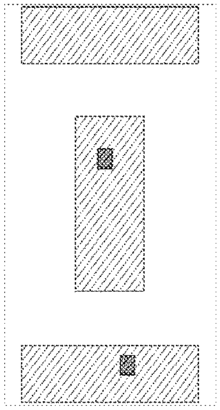
FIG. 1484C

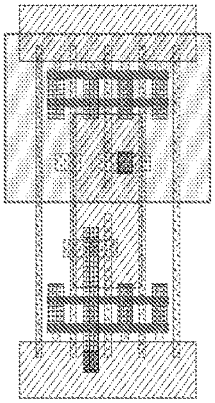
FIG. 1485A
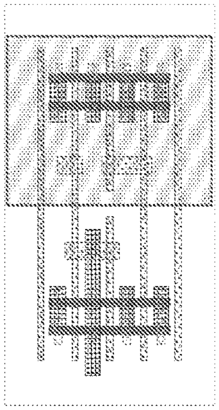
FIG. 1485B
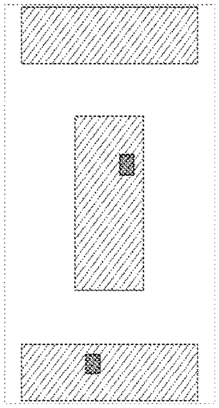
FIG. 1485C
*M* PDF Solutions, Inc.

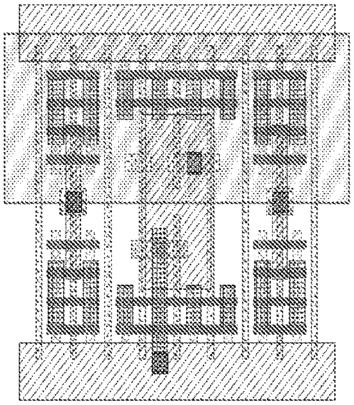
FIG. 1486A
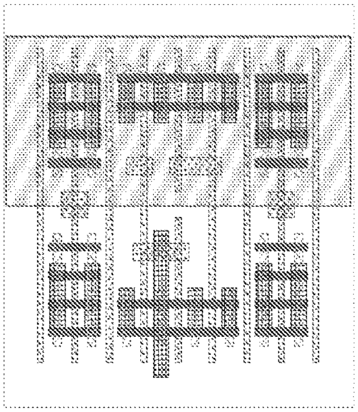
FIG. 1486B
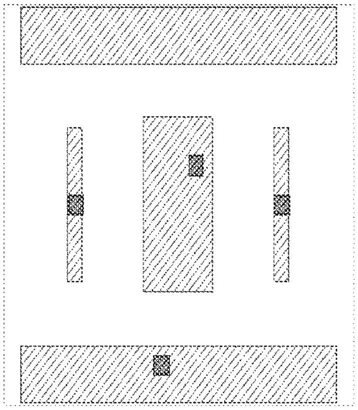
FIG. 1486C

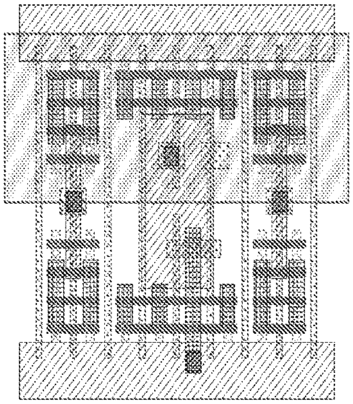
FIG. 1487A
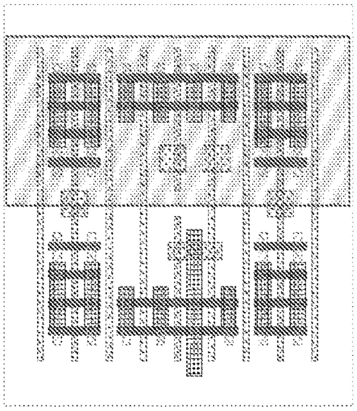
FIG. 1487B
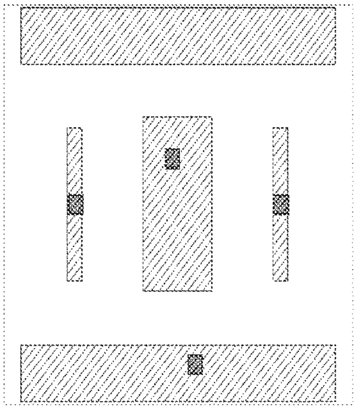
FIG. 1487C

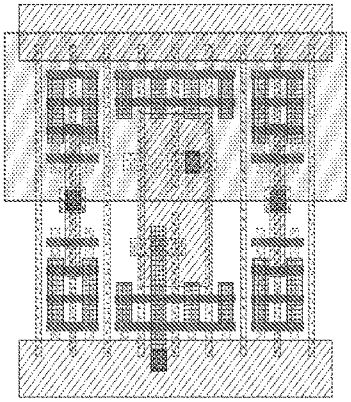
FIG. 1488A
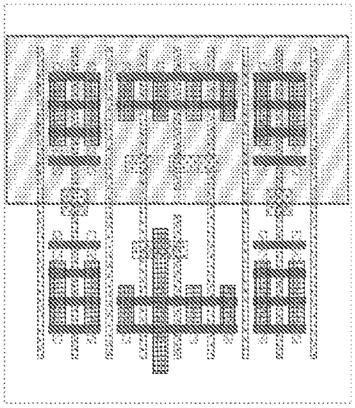
FIG. 1488B
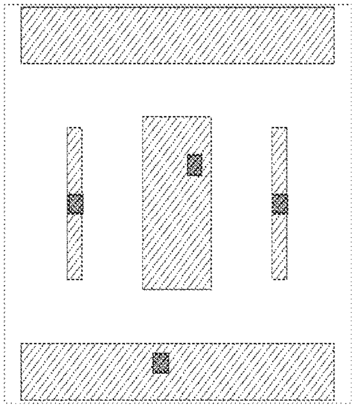
FIG. 1488C
*M* PDF Solutions, Inc.

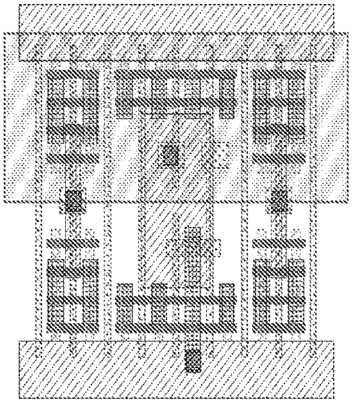
FIG. 1489A
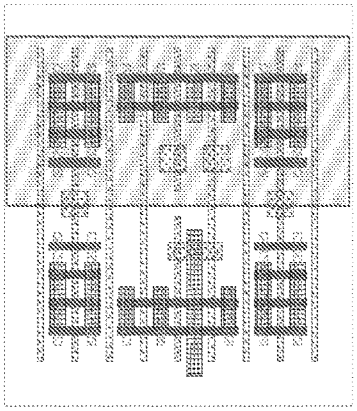
FIG. 1489B
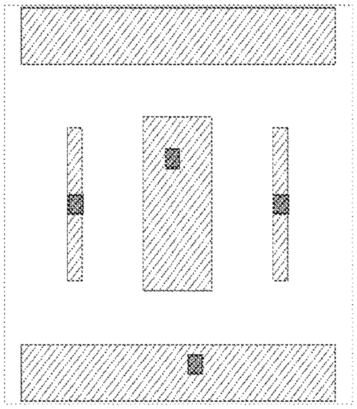
FIG. 1489C

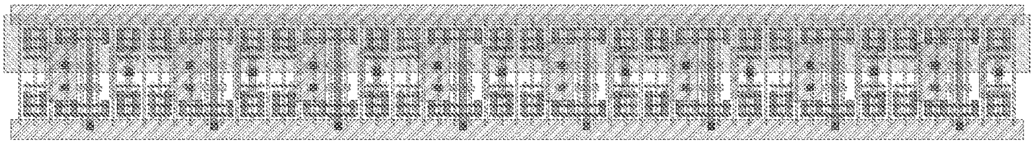
FIG. 1490A
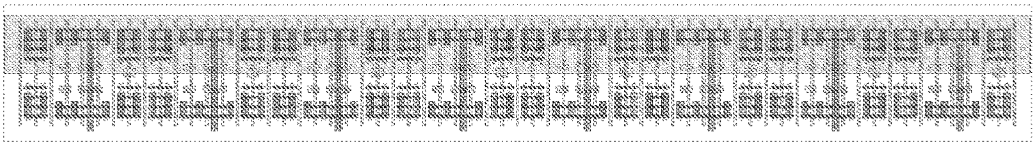
FIG. 1490B
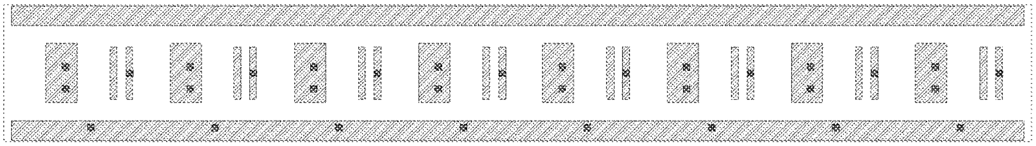
FIG. 1490C

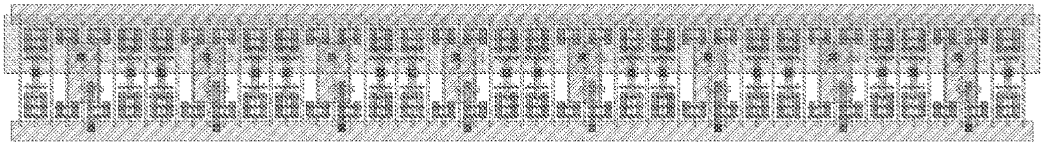
FIG. 1491A
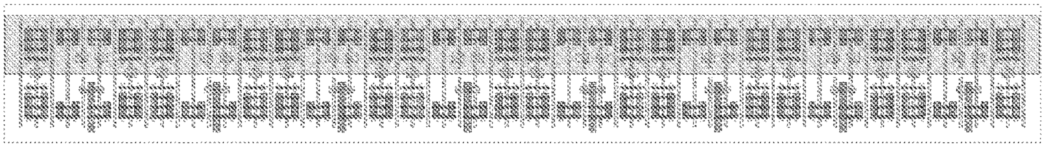
FIG. 1491B
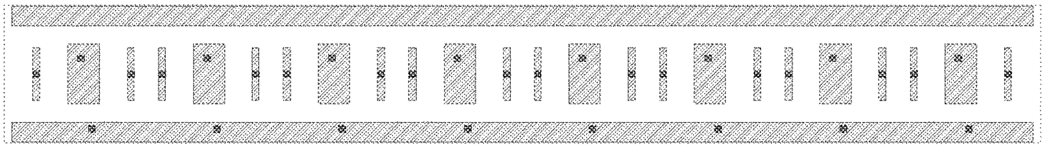
FIG. 1491C
*M* PDF Solutions, Inc.

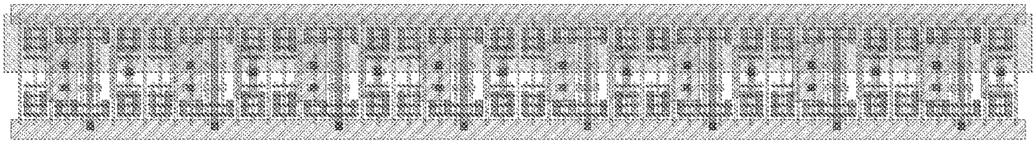
FIG. 1492A
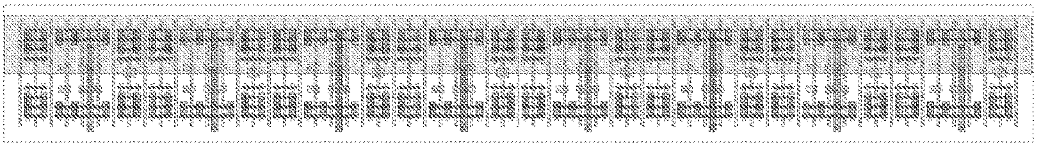
FIG. 1492B
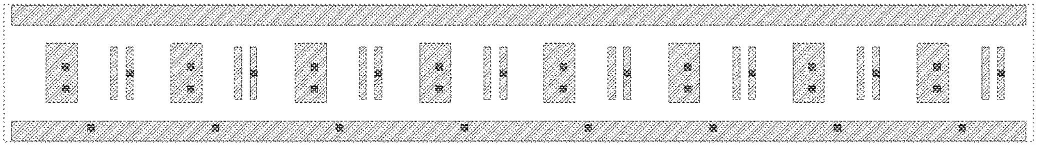
FIG. 1492C

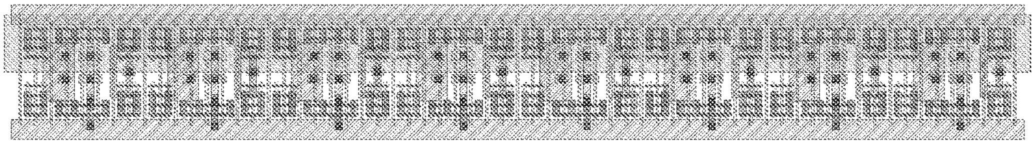
FIG. 1493A
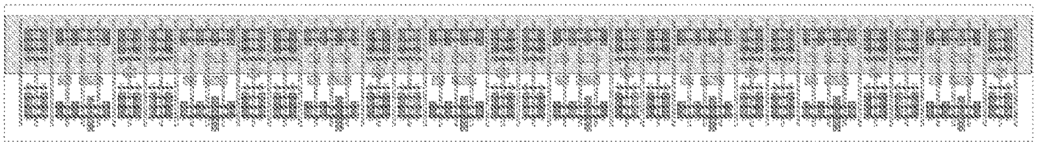
FIG. 1493B
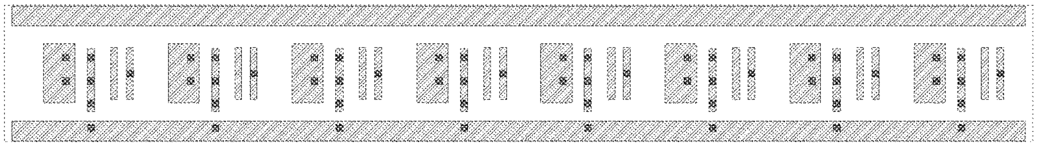
FIG. 1493C
*M* PDF Solutions, Inc.

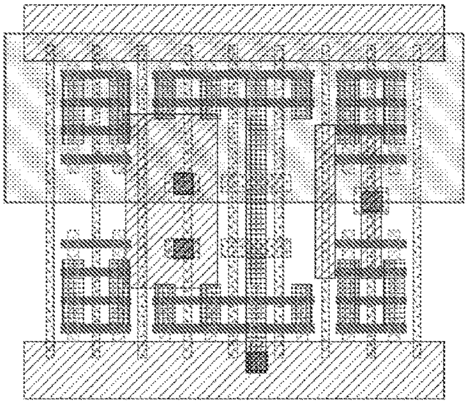
FIG. 1494A
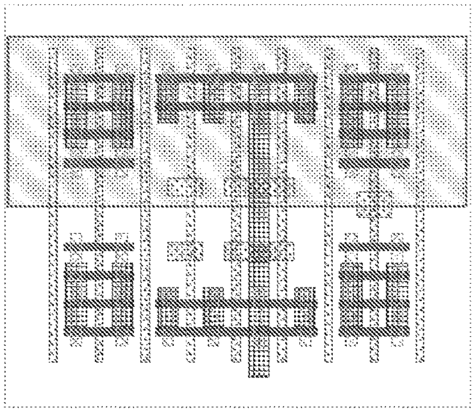
FIG. 1494B
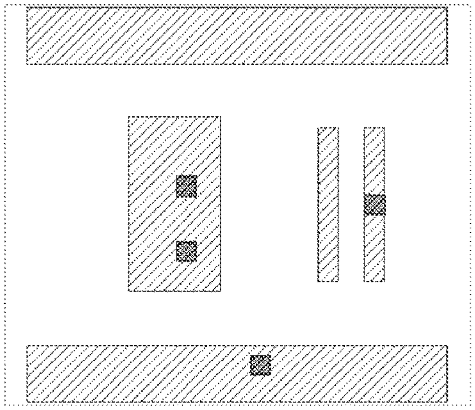
FIG. 1494C

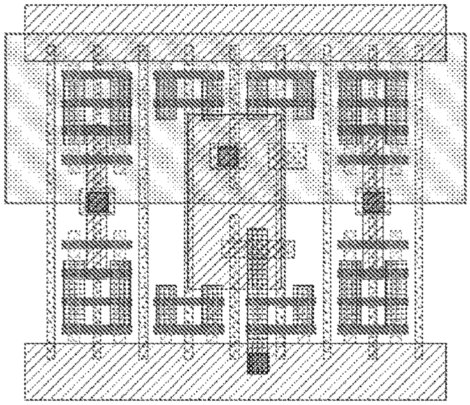
FIG. 1495A
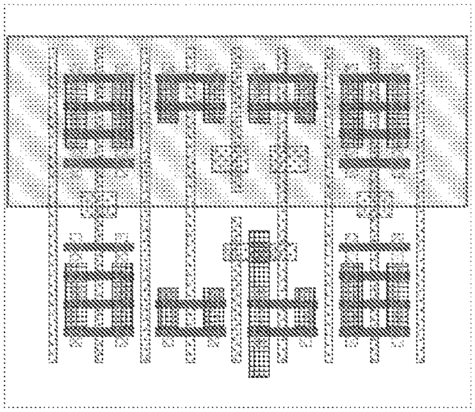
FIG. 1495B
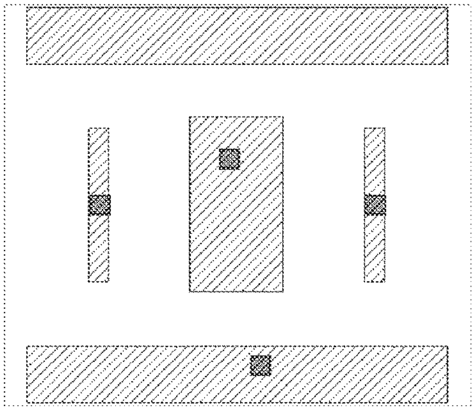
FIG. 1495C

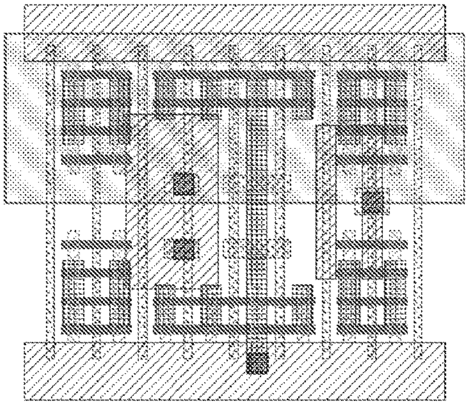
FIG. 1496A
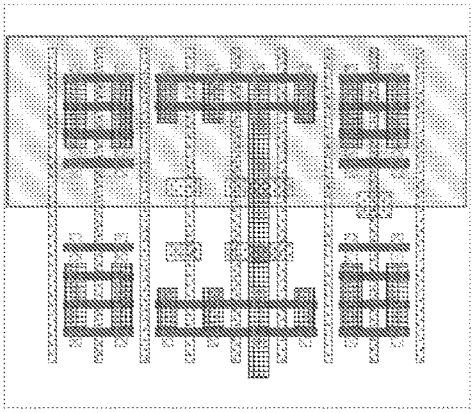
FIG. 1496B
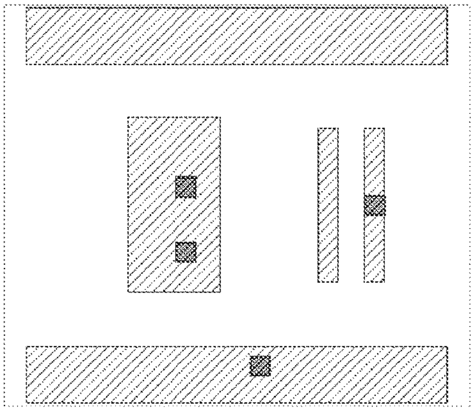
FIG. 1496C

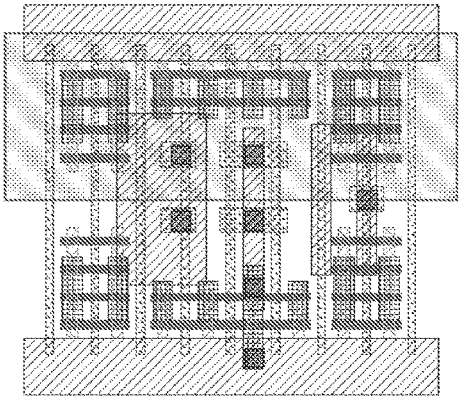
FIG. 1497A
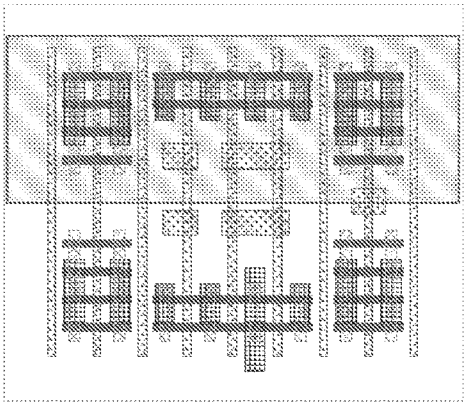
FIG. 1497B
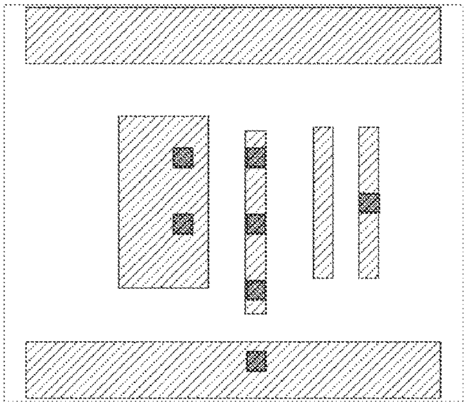
FIG. 1497C

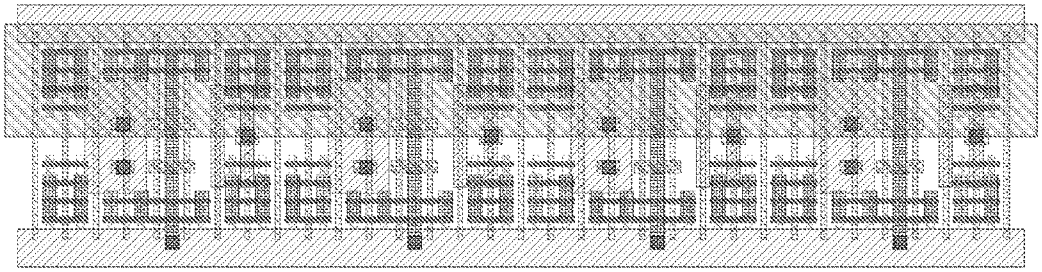
FIG. 1498A
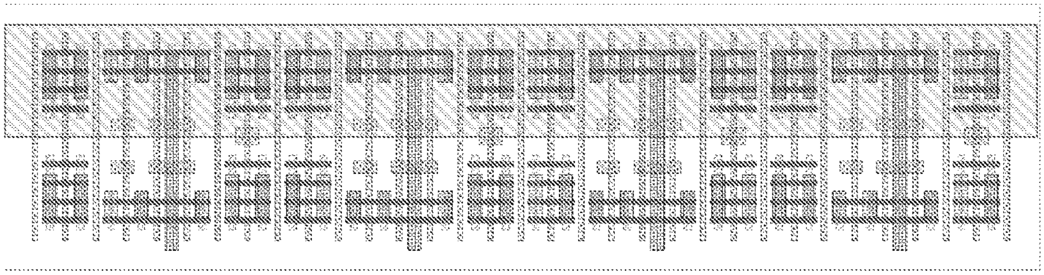
FIG. 1498B
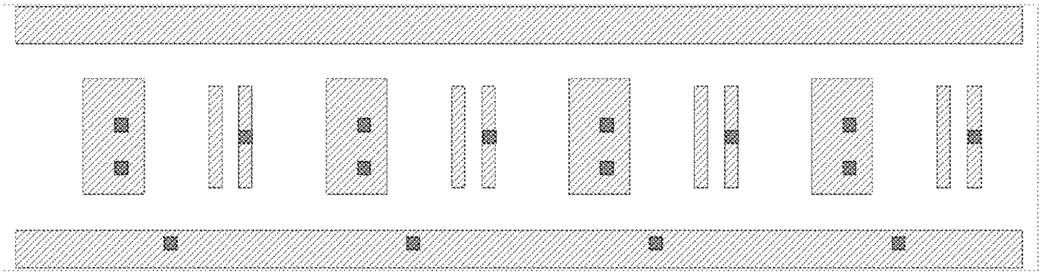
FIG. 1498C

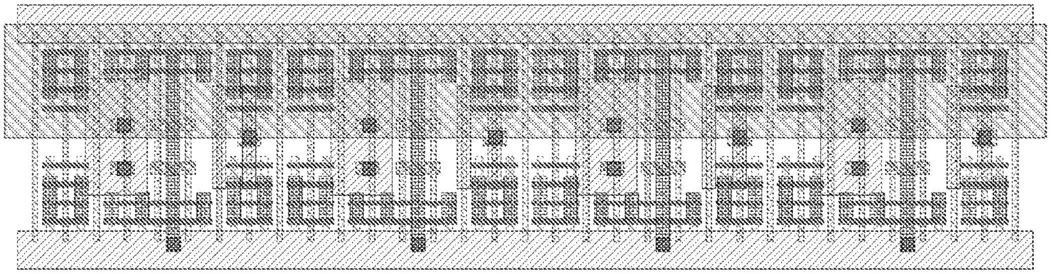
FIG. 1499A
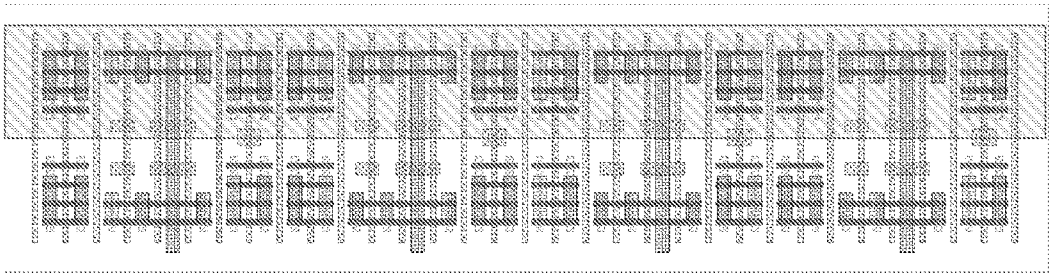
FIG. 1499B
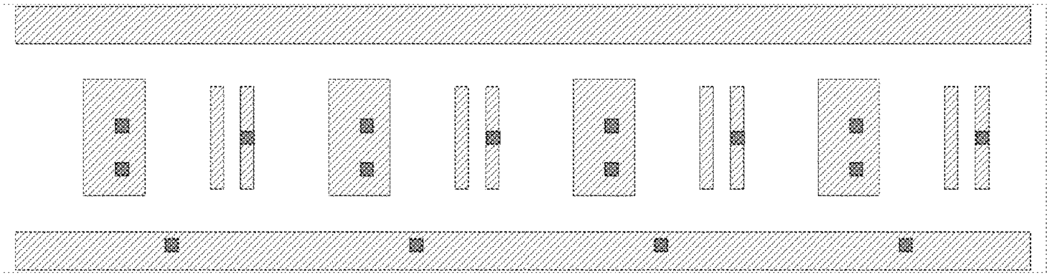
FIG. 1499C
*M* PDF Solutions, Inc.

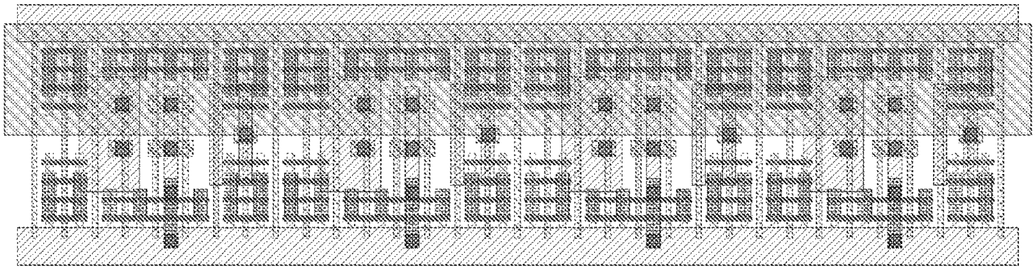
FIG. 1500A
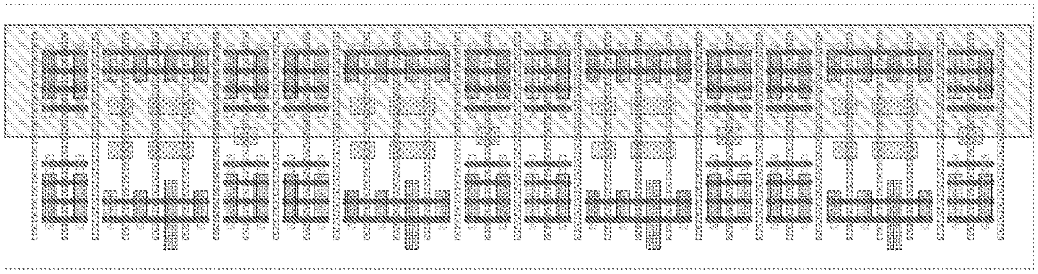
FIG. 1500B
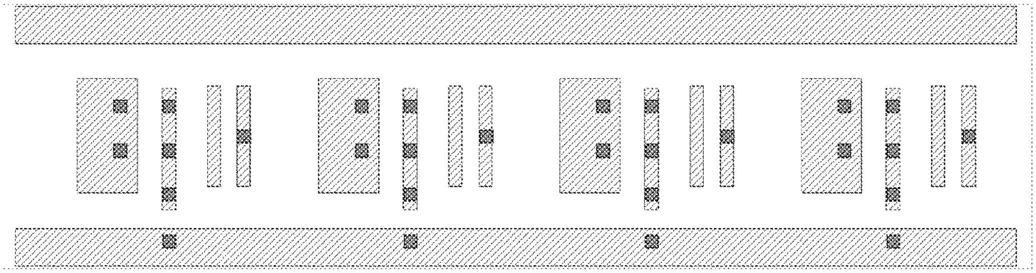
FIG. 1500C

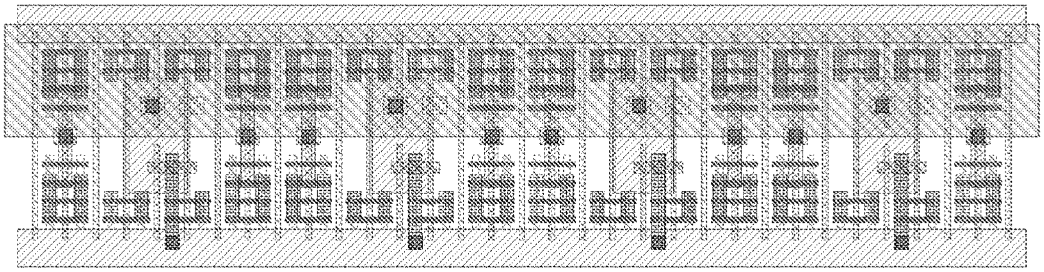
FIG. 1501A
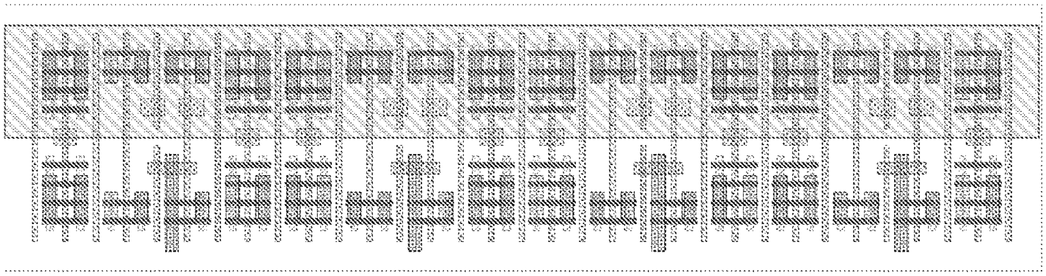
FIG. 1501B
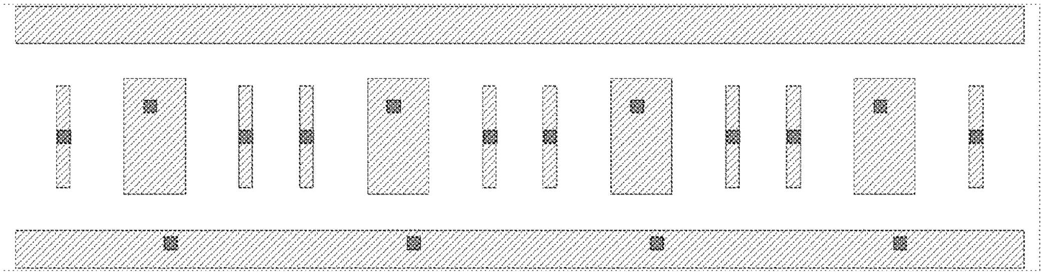
FIG. 1501C
*M* PDF Solutions, Inc.

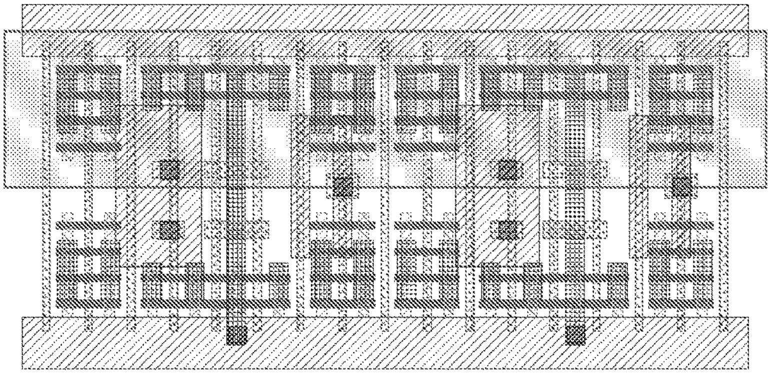
FIG. 1502A
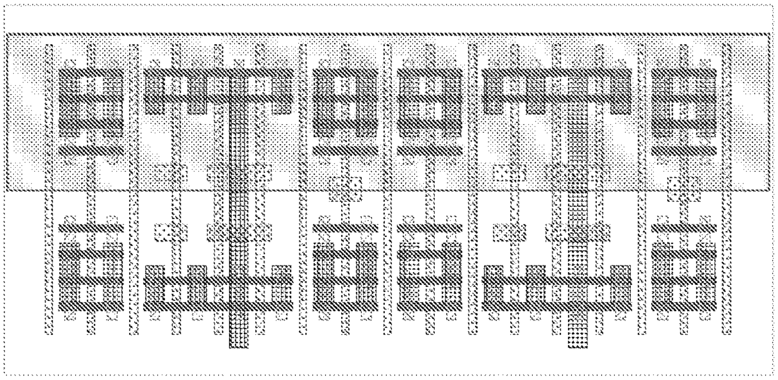
FIG. 1502B
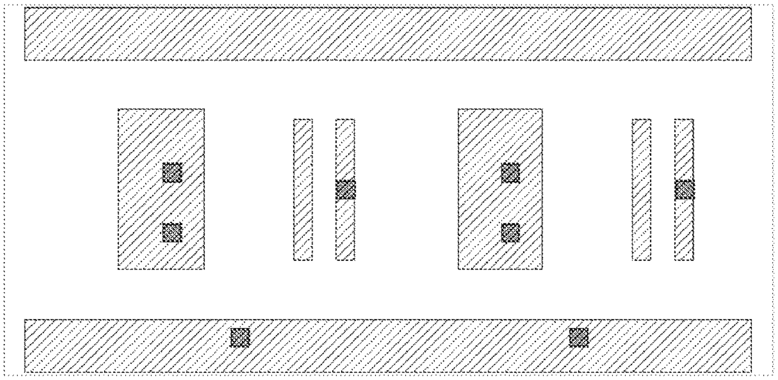
FIG. 1502C
*M* PDF Solutions, Inc.

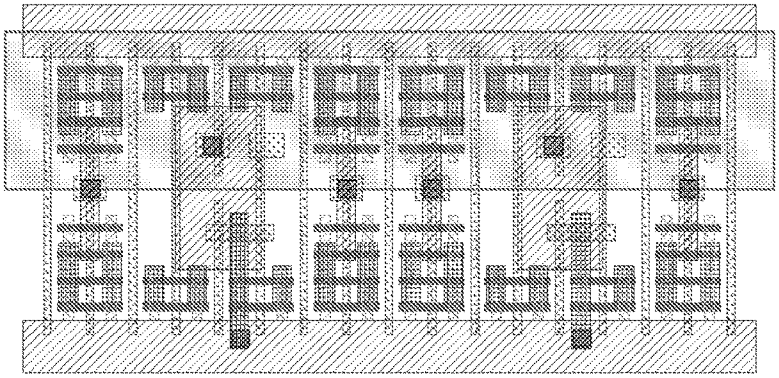
FIG. 1503A
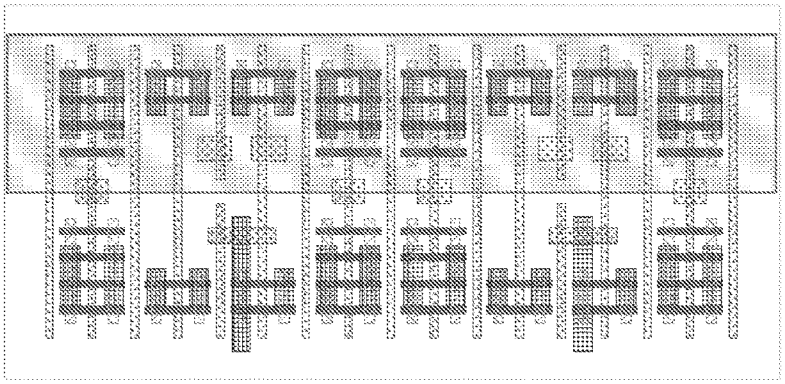
FIG. 1503B
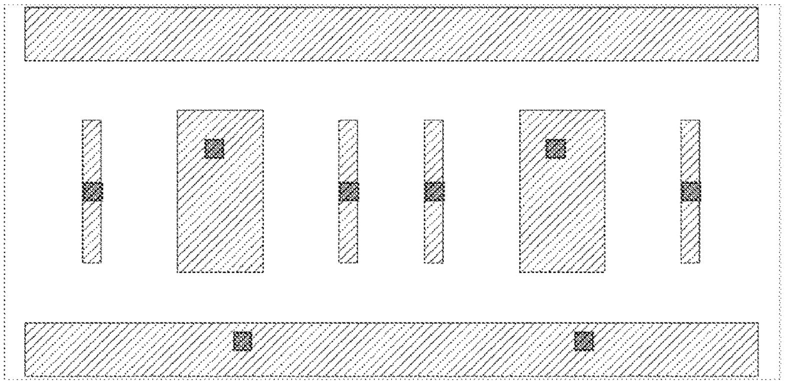
FIG. 1503C

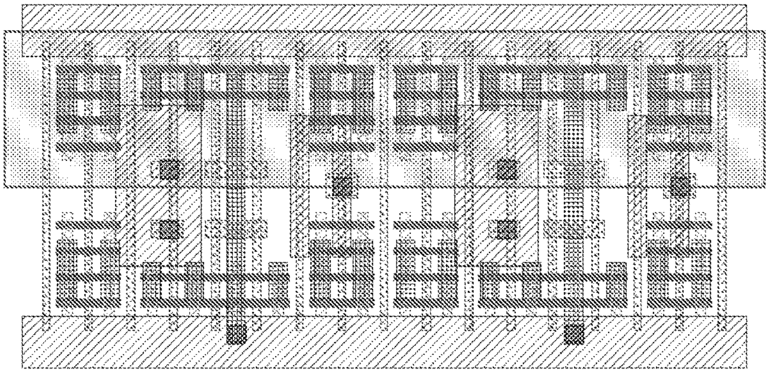
FIG. 1504A
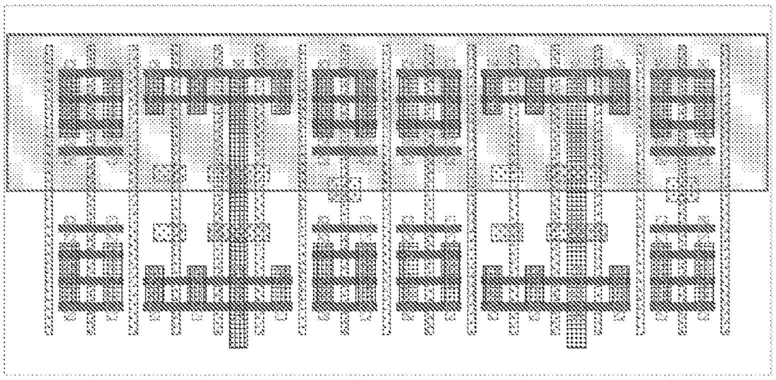
FIG. 1504B
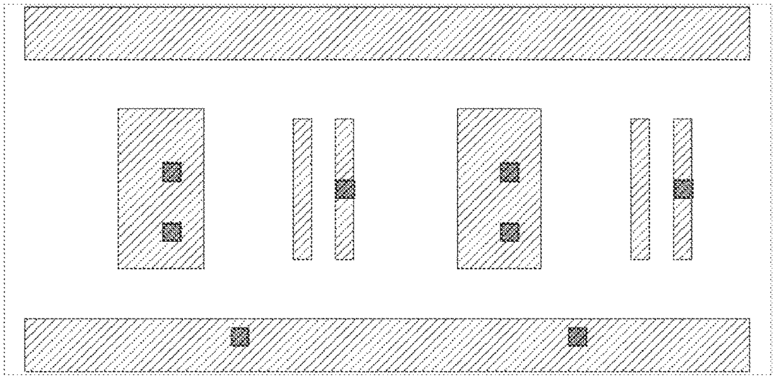
FIG. 1504C
*M* PDF Solutions, Inc.

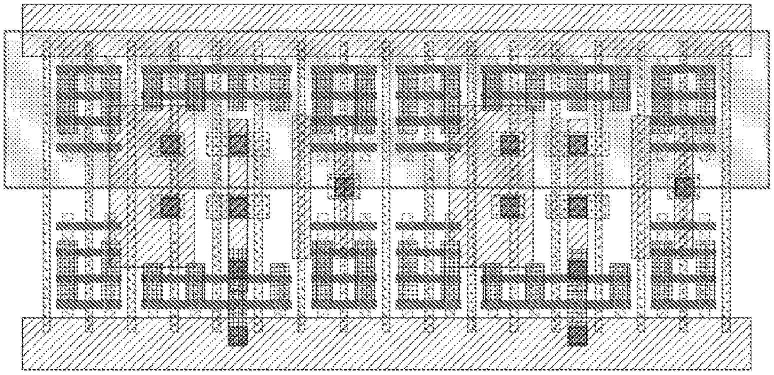
FIG. 1505A
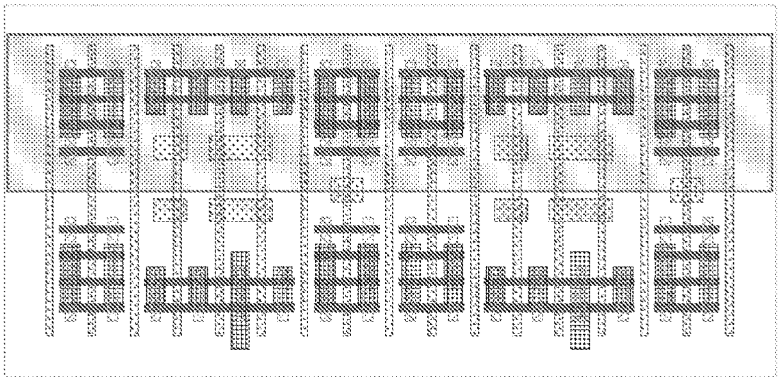
FIG. 1505B
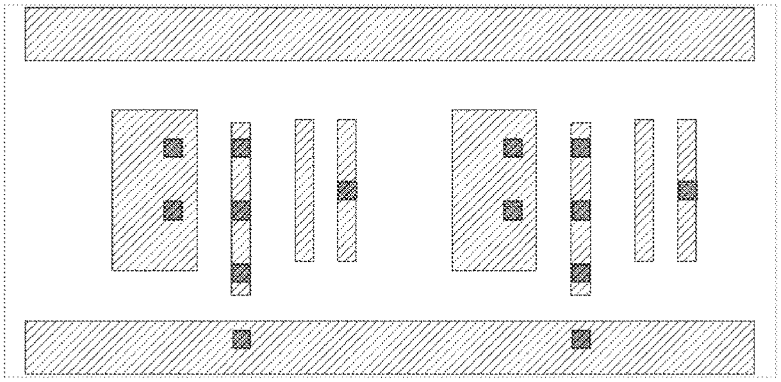
FIG. 1505C

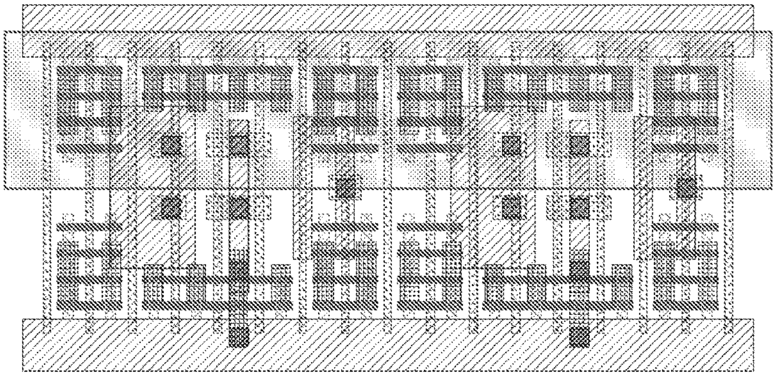
FIG. 1506A
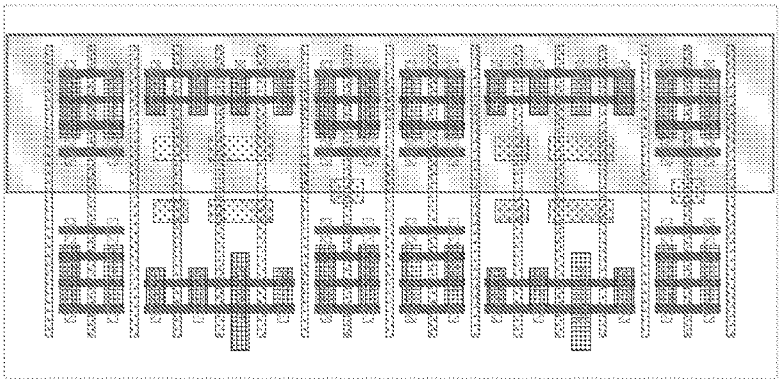
FIG. 1506B
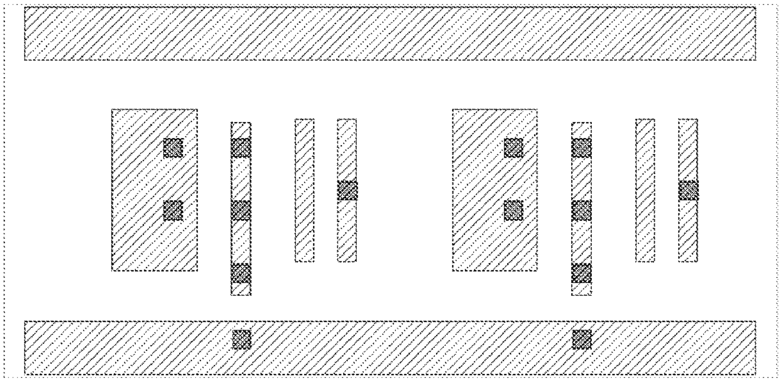
FIG. 1506C

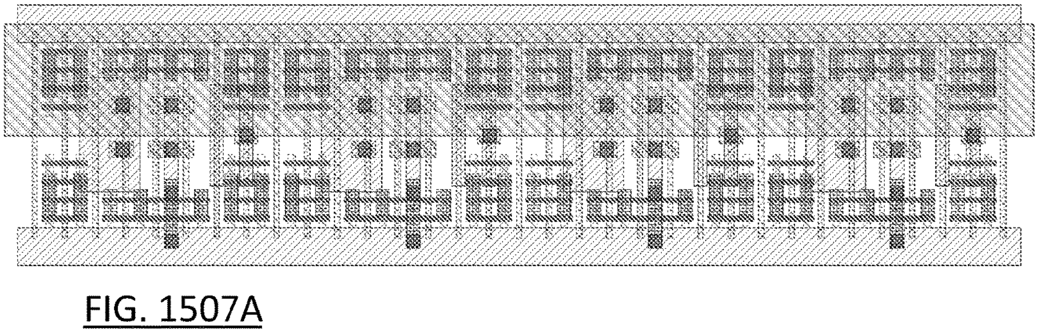
FIG. 1507A
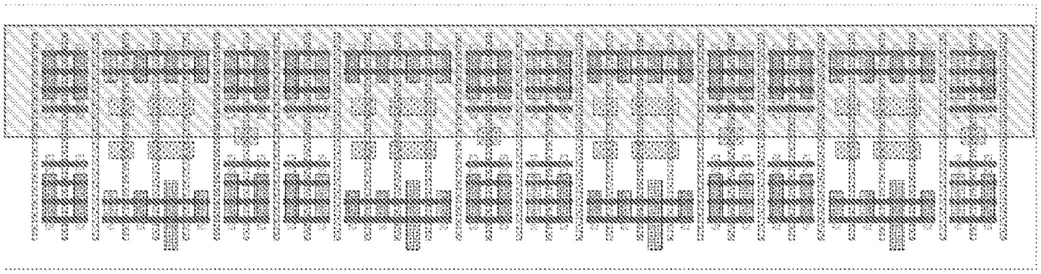
FIG. 1507B
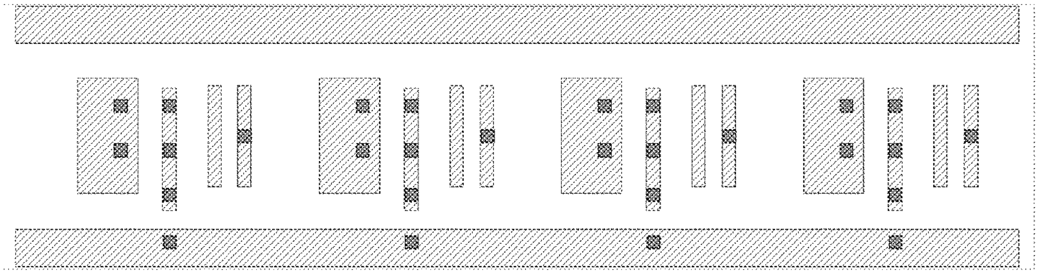
FIG. 1507C

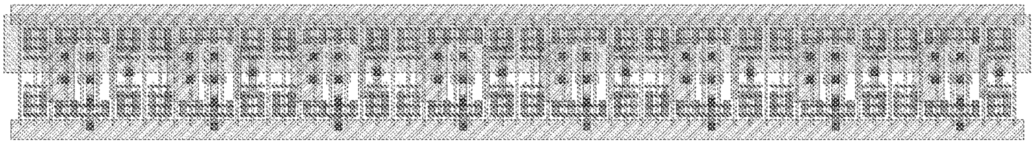
FIG. 1508A
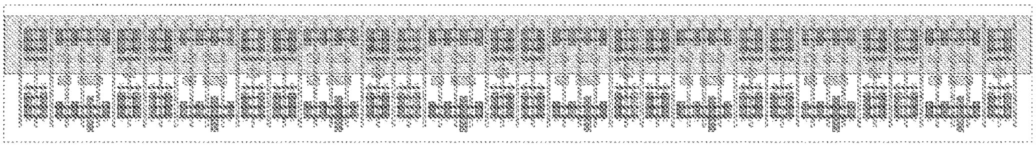
FIG. 1508B
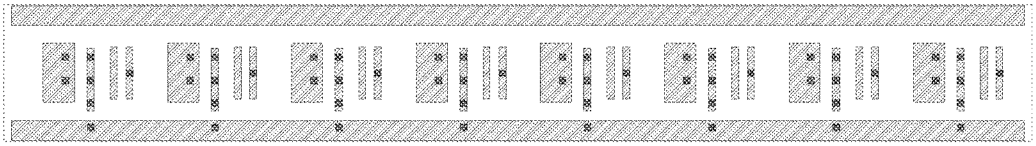
FIG. 1508C

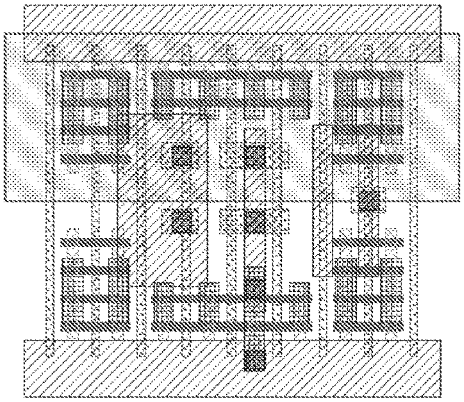
FIG. 1509A
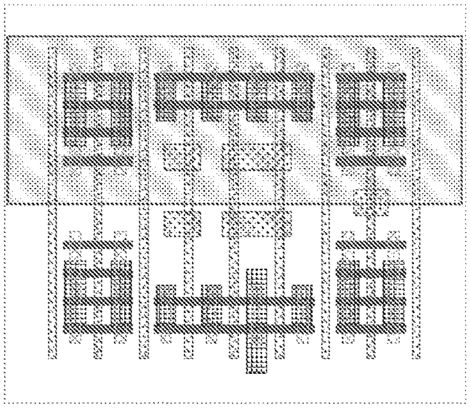
FIG. 1509B
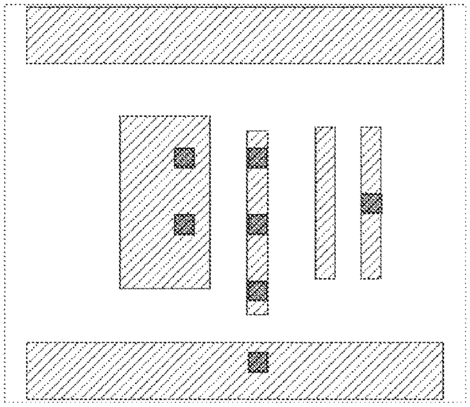
FIG. 1509C

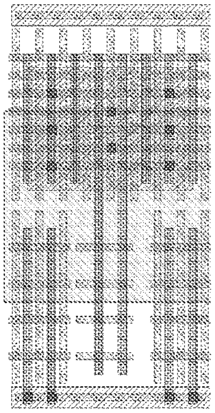
FIG. 1510A
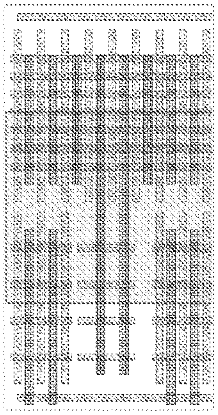
FIG. 1510B
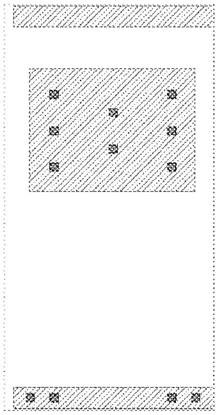
FIG. 1510C
*M* PDF Solutions, Inc.

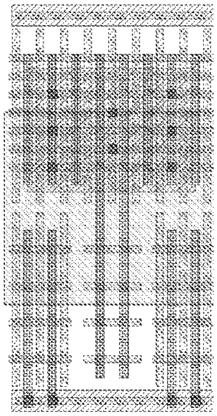
FIG. 1511A
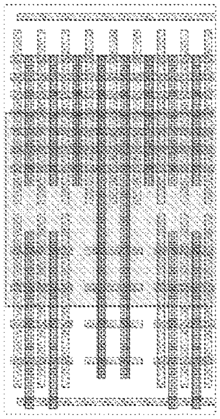
FIG. 1511B
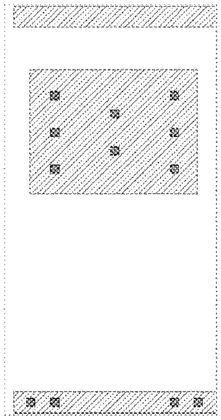
FIG. 1511C

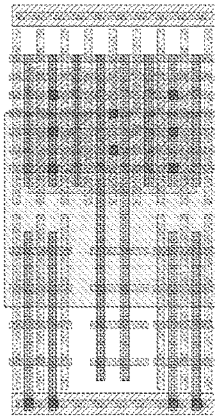
FIG. 1512A
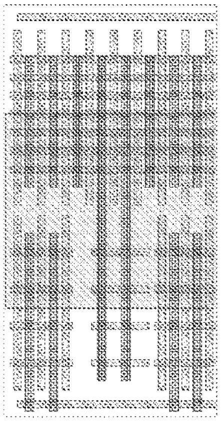
FIG. 1512B
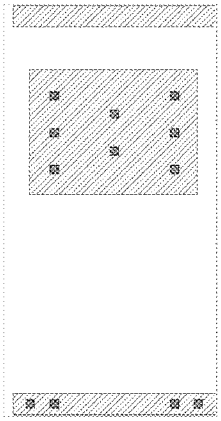
FIG. 1512C

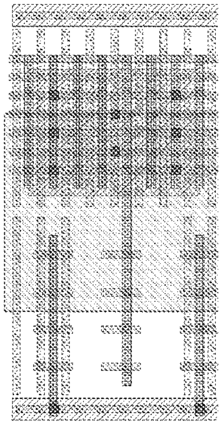
FIG. 1513A
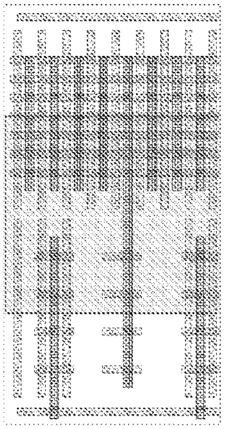
FIG. 1513B
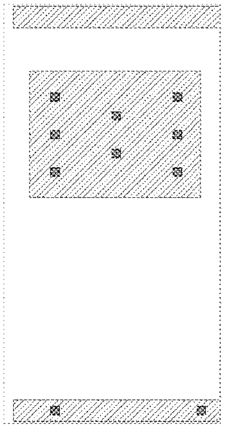
FIG. 1513C

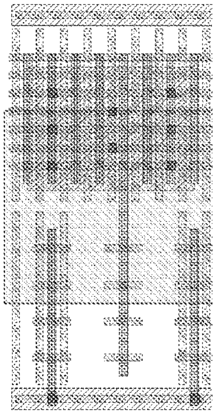
FIG. 1514A
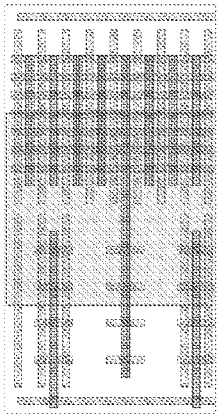
FIG. 1514B
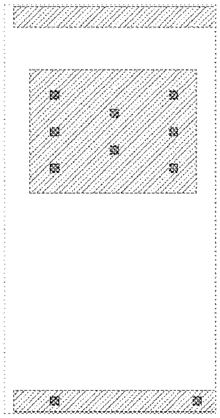
FIG. 1514C
*M* PDF Solutions, Inc.

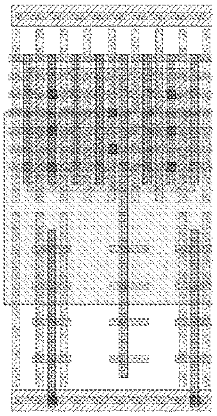
FIG. 1515A
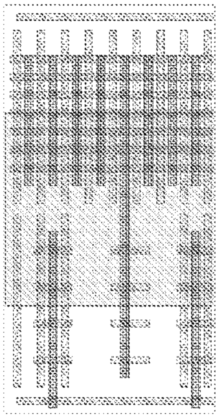
FIG. 1515B
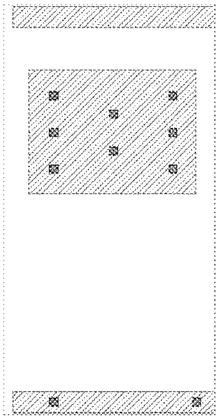
FIG. 1515C

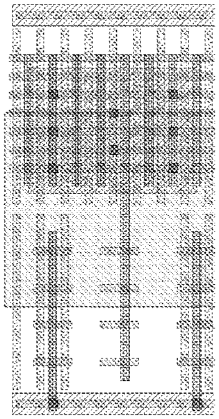
FIG. 1516A
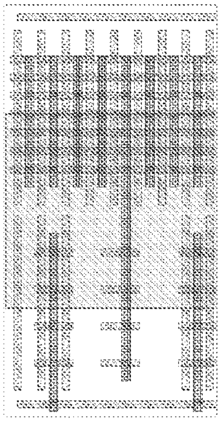
FIG. 1516B
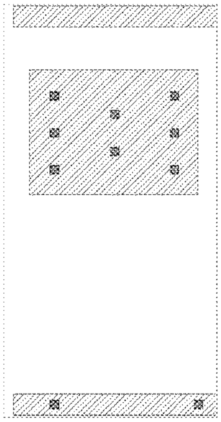
FIG. 1516C

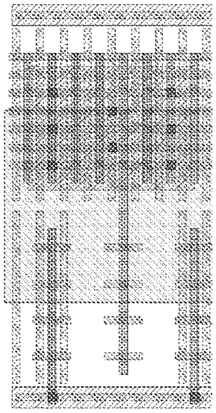
FIG. 1517A
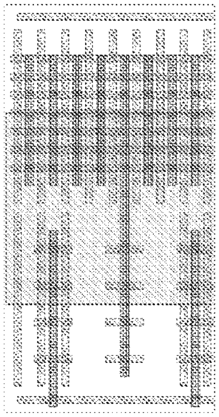
FIG. 1517B
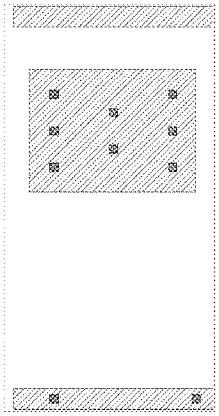
FIG. 1517C

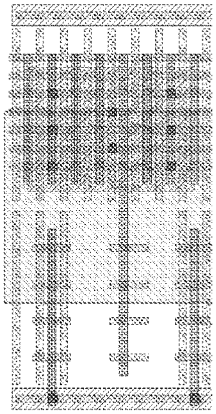
FIG. 1518A
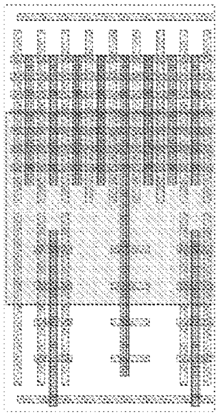
FIG. 1518B
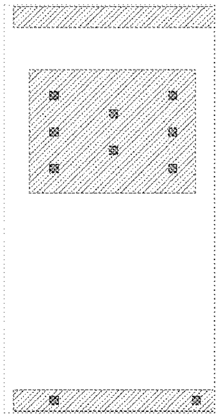
FIG. 1518C

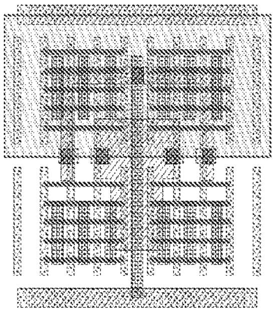
FIG. 1519A
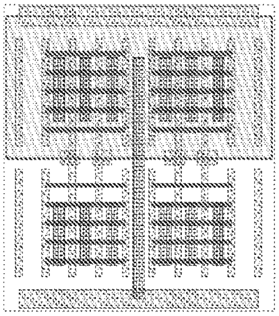
FIG. 1519B
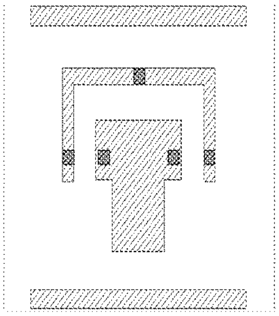
FIG. 1519C

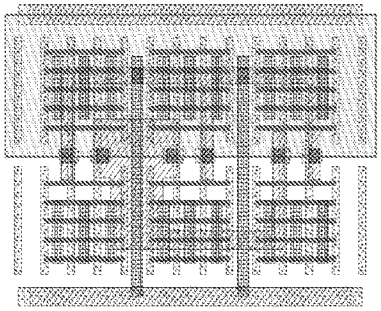
FIG. 1520A
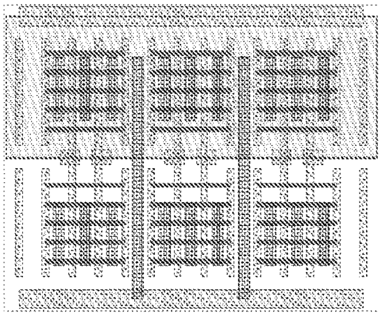
FIG. 1520B
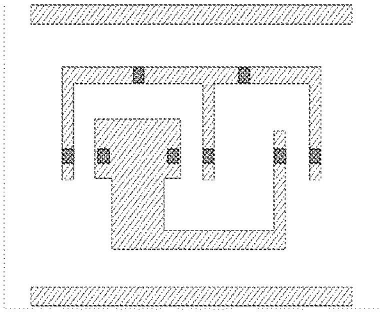
FIG. 1520C

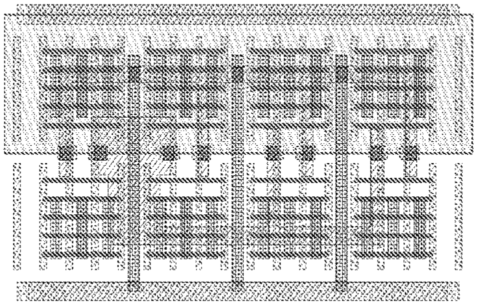
FIG. 1521A
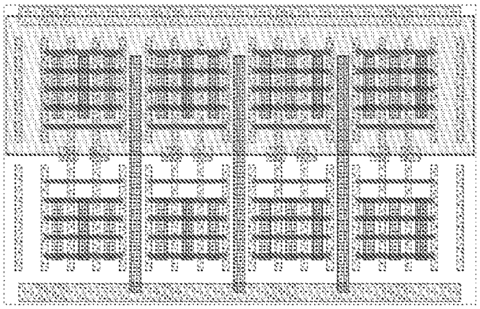
FIG. 1521B
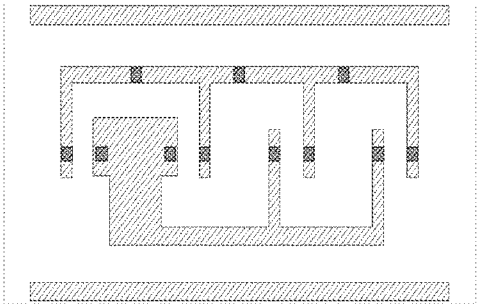
FIG. 1521C

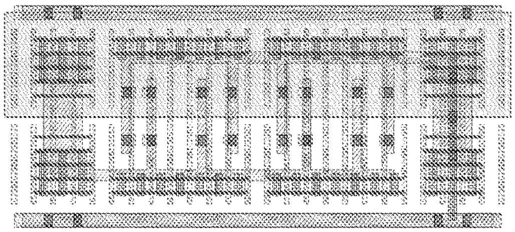
FIG. 1522A
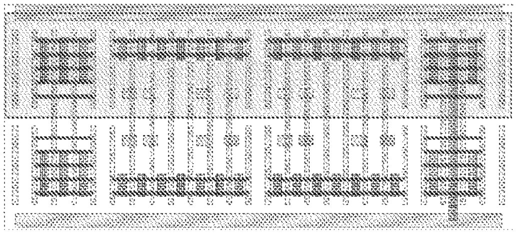
FIG. 1522B
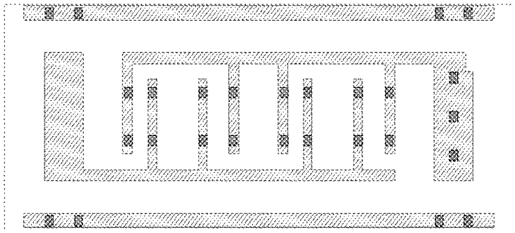
FIG. 1522C

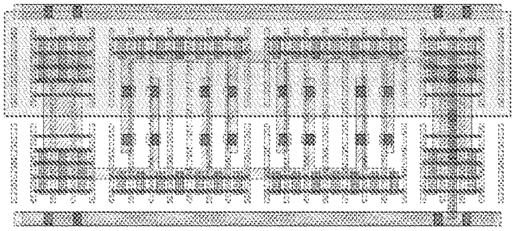
FIG. 1523A
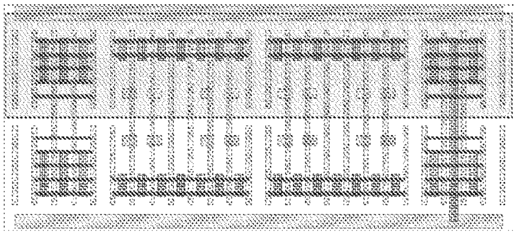
FIG. 1523B
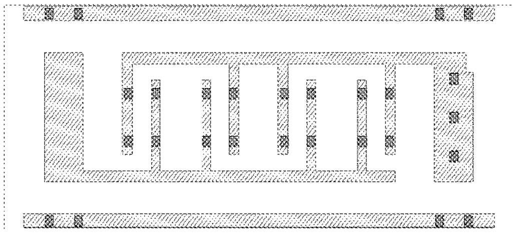
FIG. 1523C
*M* PDF Solutions, Inc.

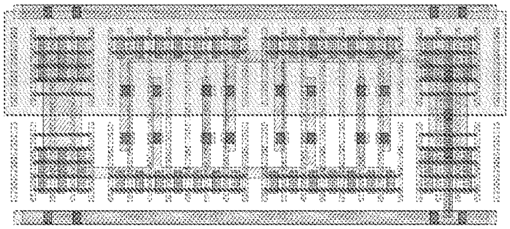
FIG. 1524A
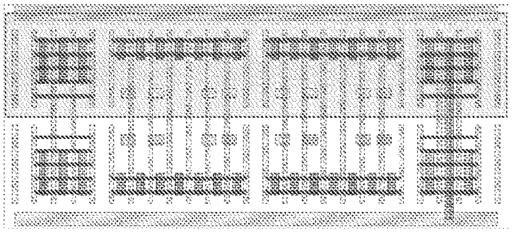
FIG. 1524B
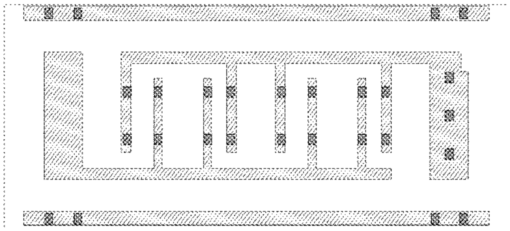
FIG. 1524C

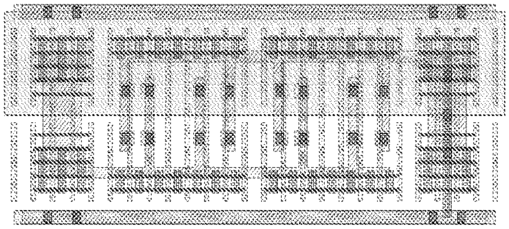
FIG. 1525A
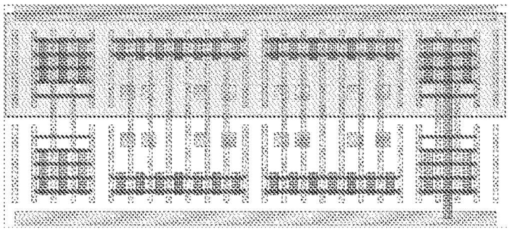
FIG. 1525B
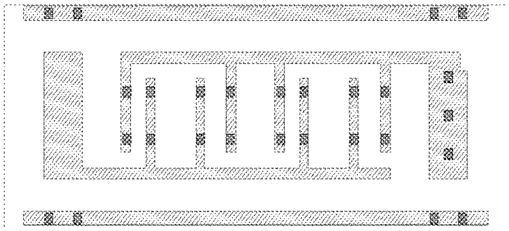
FIG. 1525C

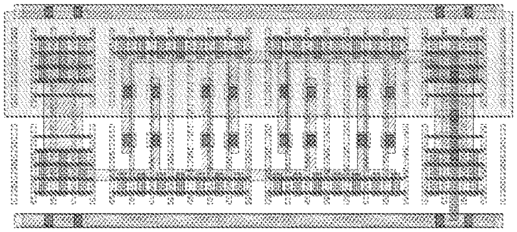
FIG. 1526A
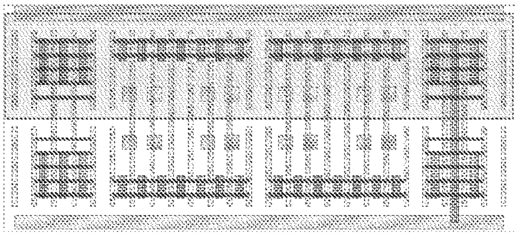
FIG. 1526B
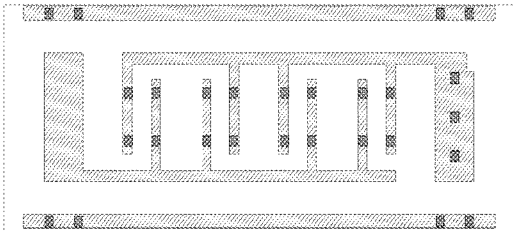
FIG. 1526C
*M* PDF Solutions, Inc.

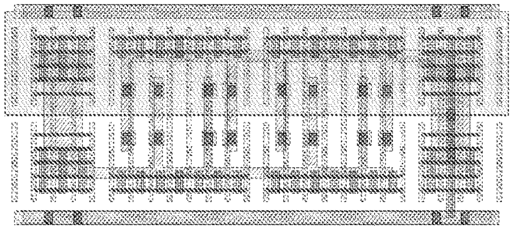
FIG. 1527A
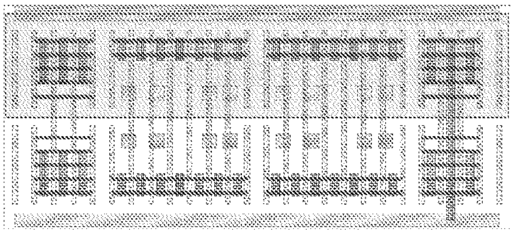
FIG. 1527B
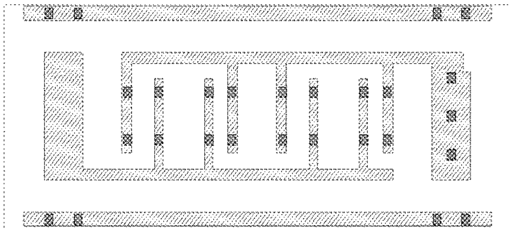
FIG. 1527C

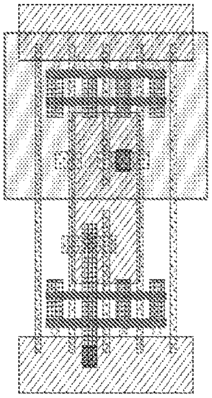
FIG. 1528A
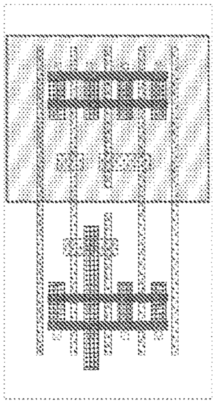
FIG. 1528B
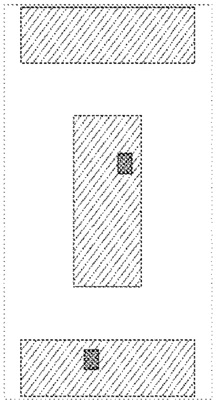
FIG. 1528C

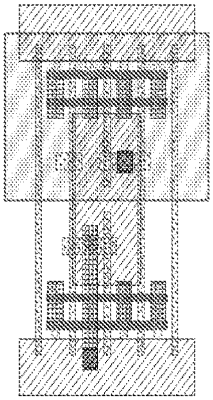
FIG. 1529A
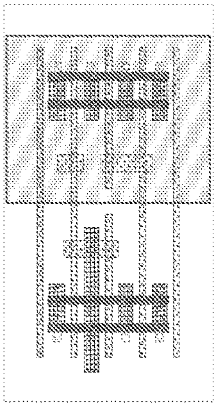
FIG. 1529B
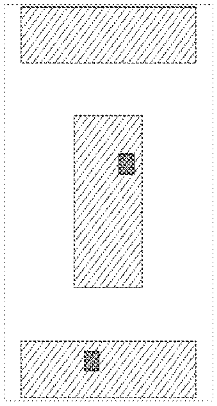
FIG. 1529C

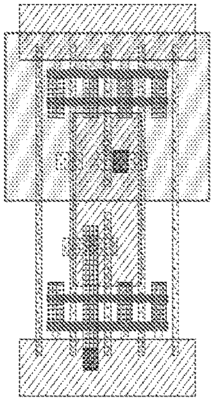
FIG. 1530A
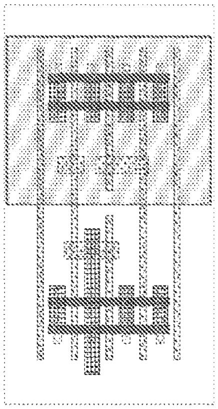
FIG. 1530B
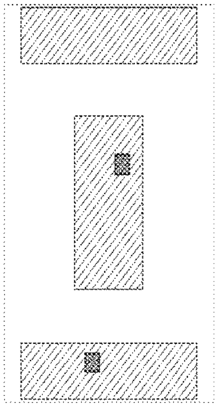
FIG. 1530C

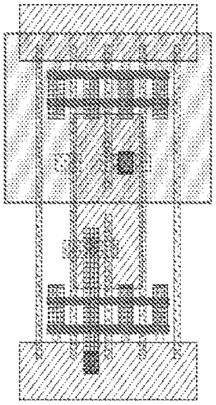
FIG. 1531A
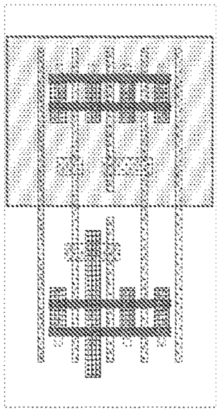
FIG. 1531B
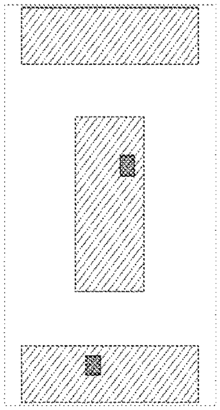
FIG. 1531C

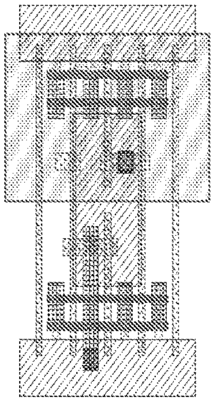
FIG. 1532A
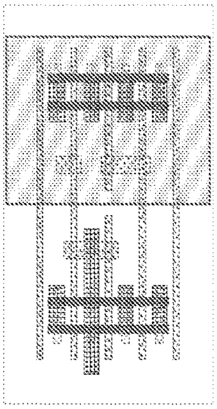
FIG. 1532B
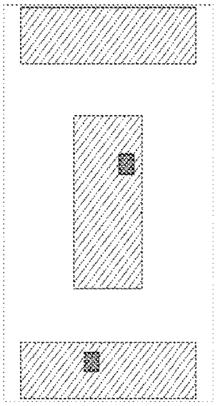
FIG. 1532C

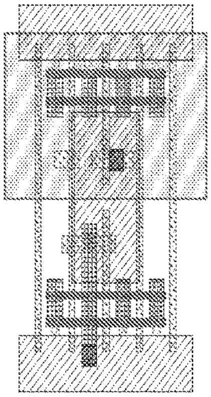
FIG. 1533A
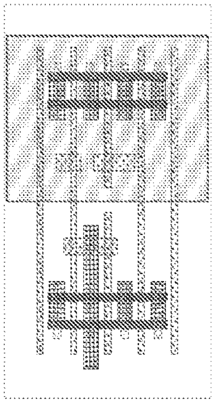
FIG. 1533B
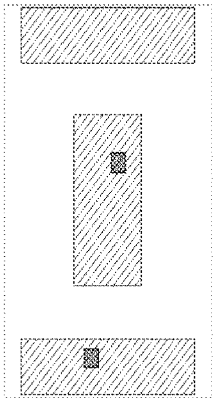
FIG. 1533C

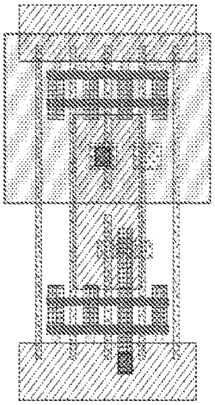
FIG. 1534A
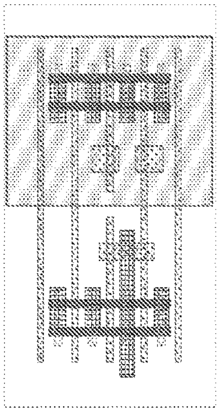
FIG. 1534B
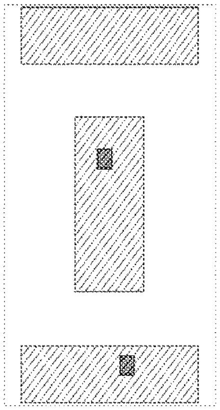
FIG. 1534C

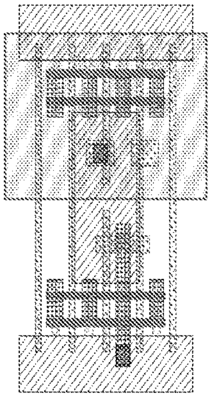
FIG. 1535A
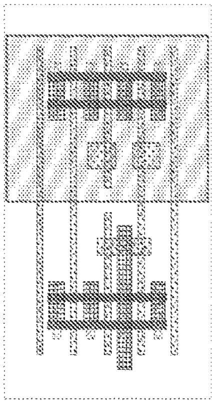
FIG. 1535B
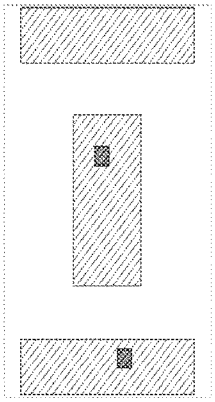
FIG. 1535C
*M* PDF Solutions, Inc.

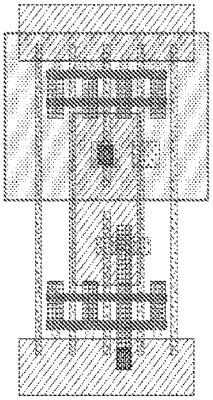
FIG. 1536A
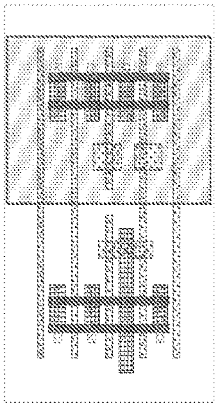
FIG. 1536B
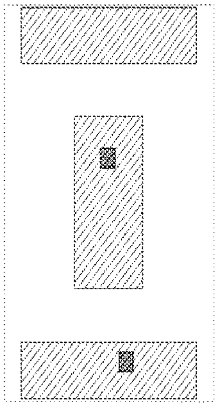
FIG. 1536C

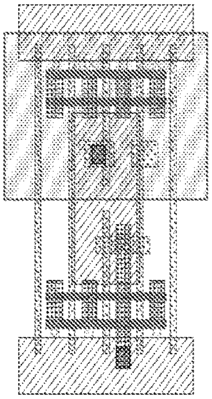
FIG. 1537A
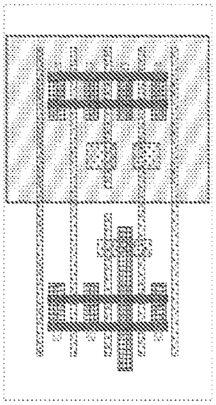
FIG. 1537B
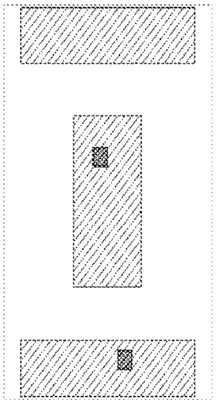
FIG. 1537C

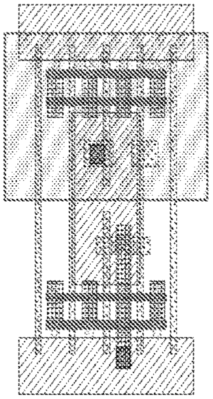
FIG. 1538A
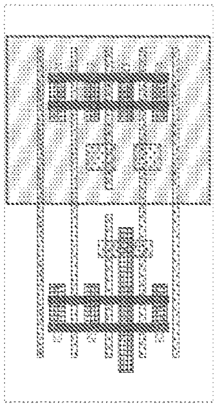
FIG. 1538B
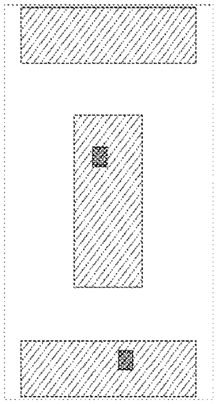
FIG. 1538C
*M* PDF Solutions, Inc.

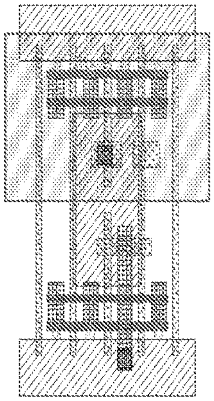
FIG. 1539A
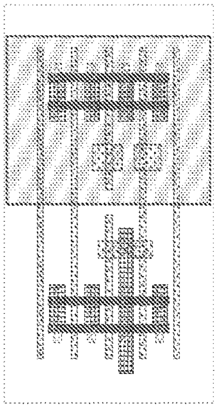
FIG. 1539B
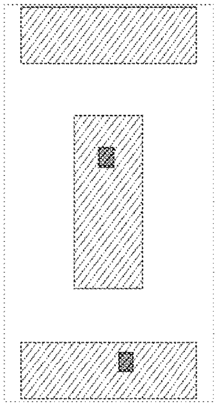
FIG. 1539C

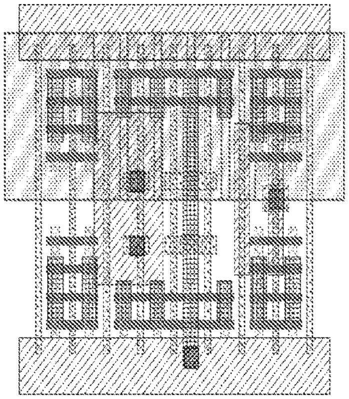
FIG. 1540A
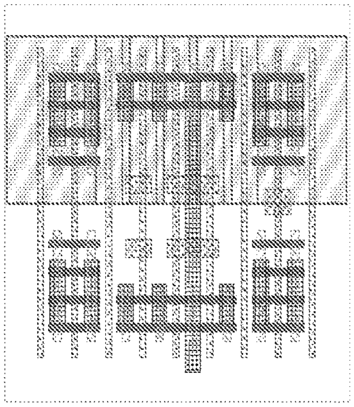
FIG. 1540B
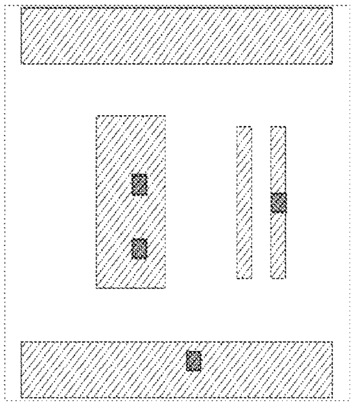
FIG. 1540C

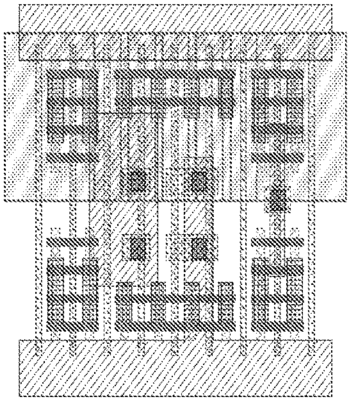
FIG. 1541A
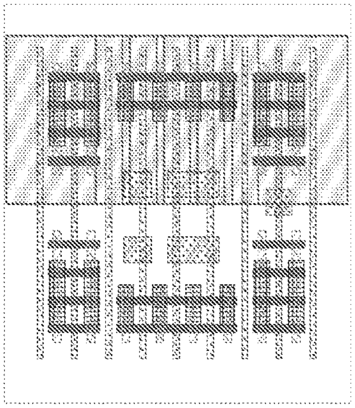
FIG. 1541B
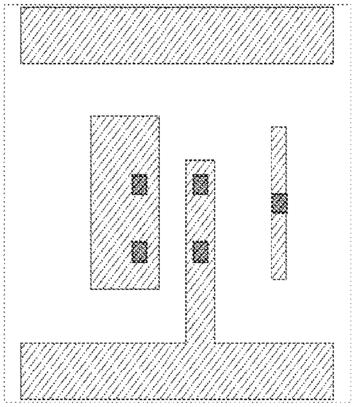
FIG. 1541C

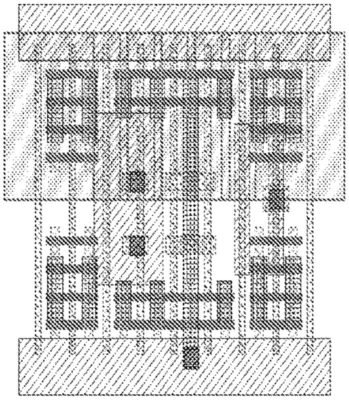
FIG. 1542A
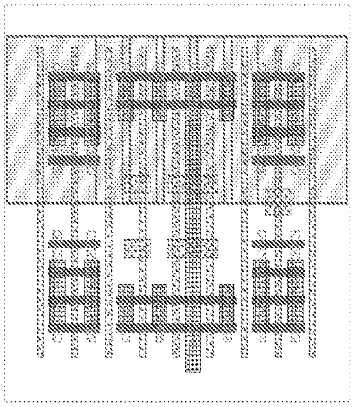
FIG. 1542B
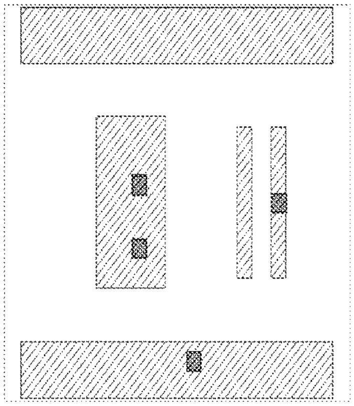
FIG. 1542C

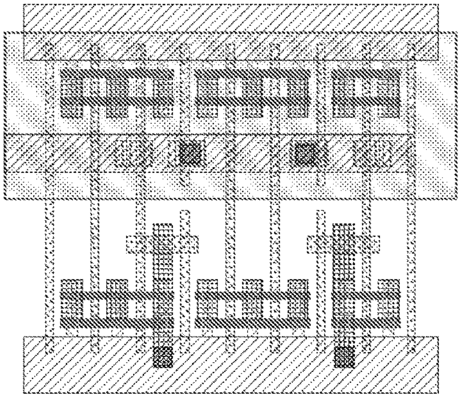
FIG. 1543A
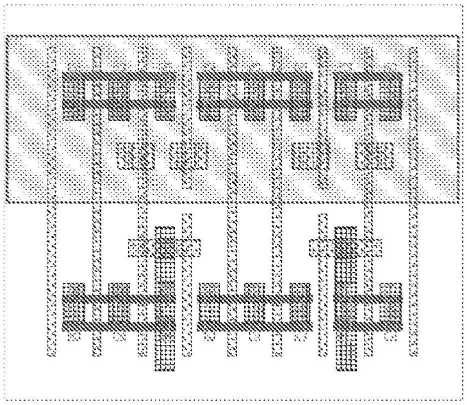
FIG. 1543B
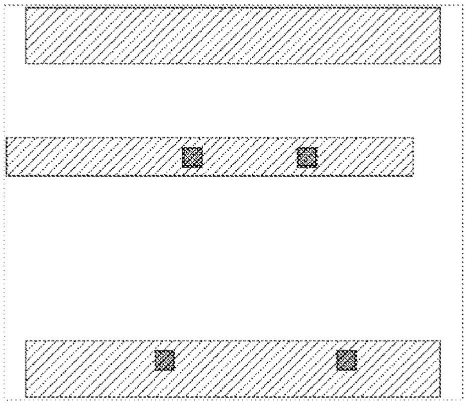
FIG. 1543C

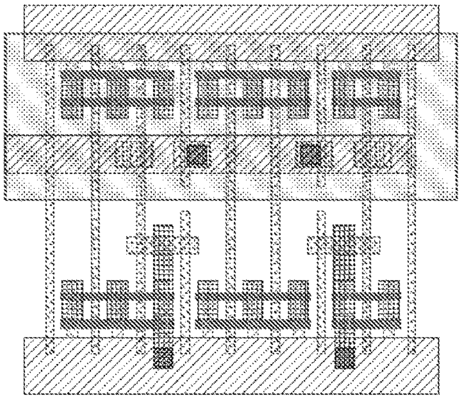
FIG. 1544A
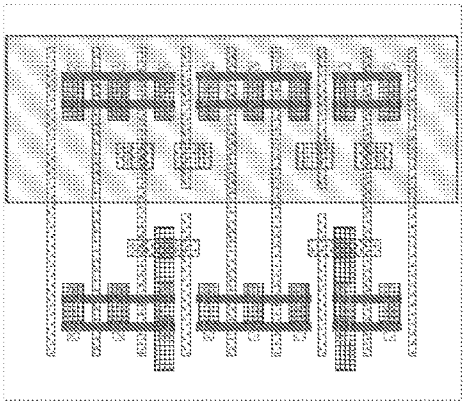
FIG. 1544B
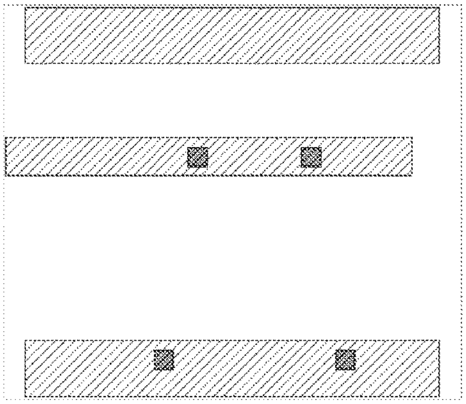
FIG. 1544C
*M* PDF Solutions, Inc.

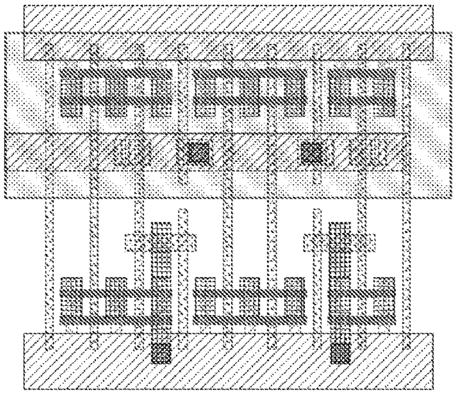
FIG. 1545A
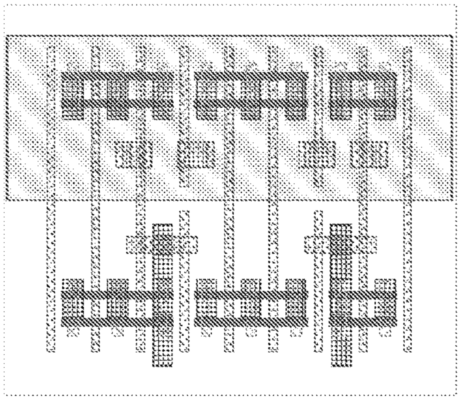
FIG. 1545B
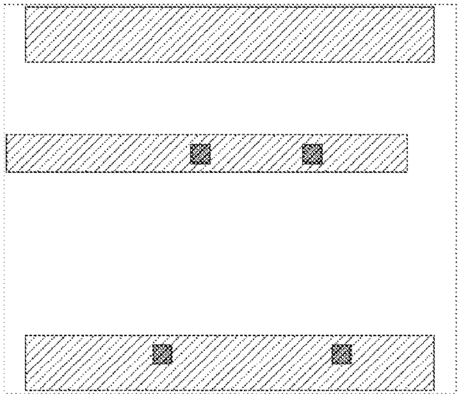
FIG. 1545C

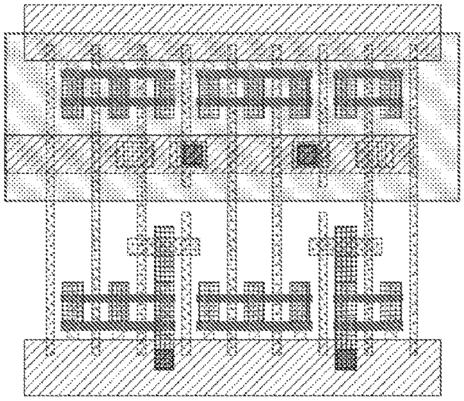
FIG. 1546A
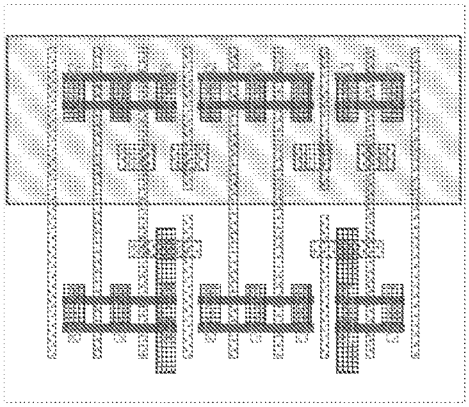
FIG. 1546B
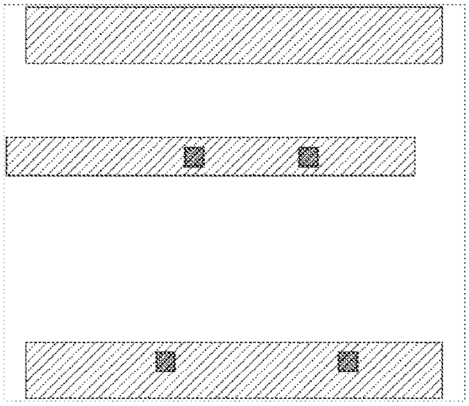
FIG. 1546C
*M* PDF Solutions, Inc.

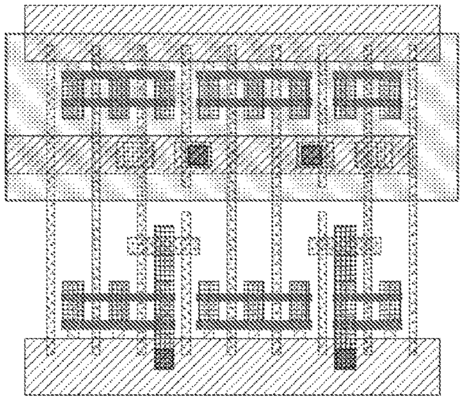
FIG. 1547A
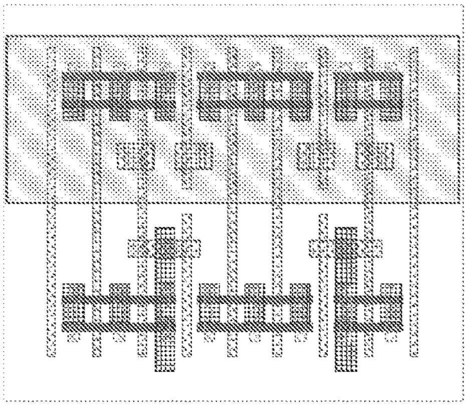
FIG. 1547B
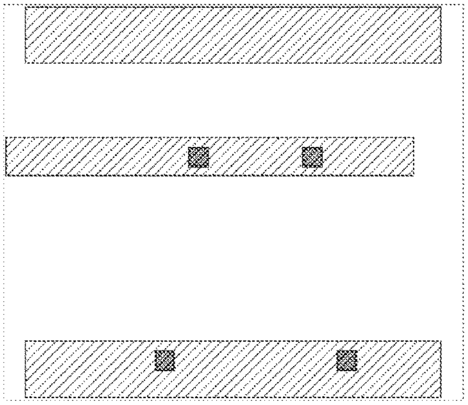
FIG. 1547C
*M* PDF Solutions, Inc.

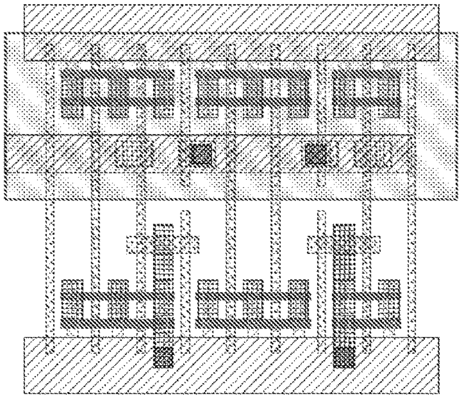
FIG. 1548A
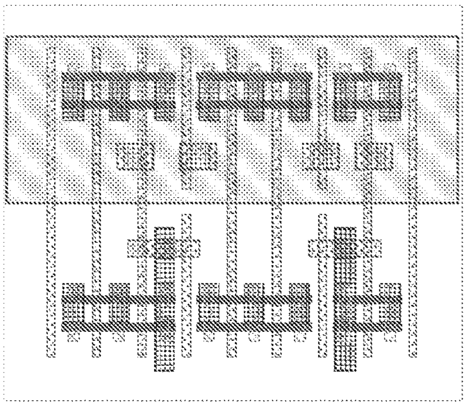
FIG. 1548B
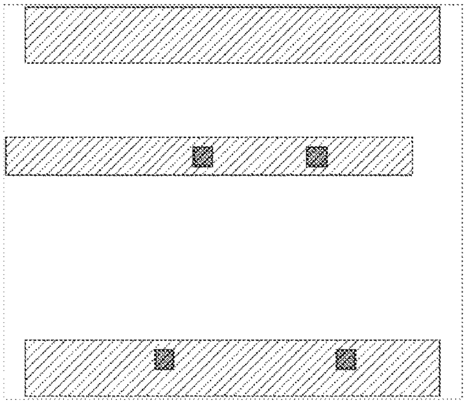
FIG. 1548C

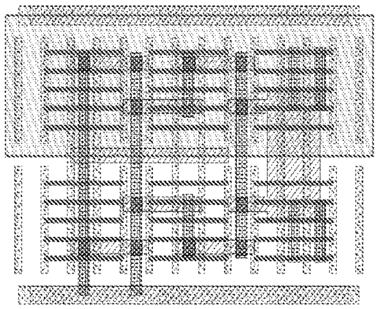
FIG. 1549A
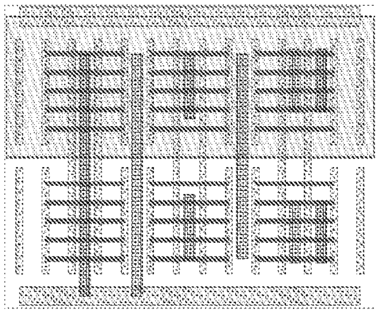
FIG. 1549B
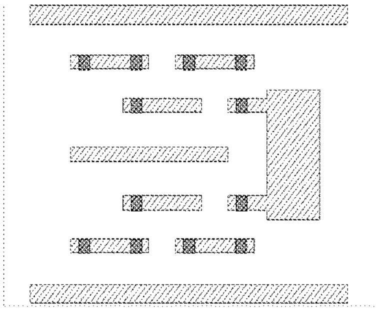
FIG. 1549C

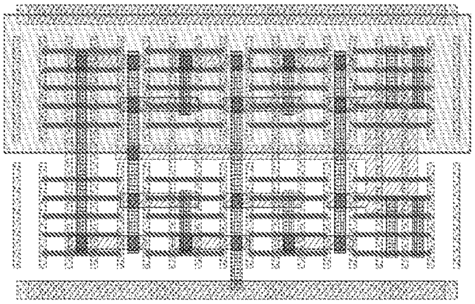
FIG. 1550A
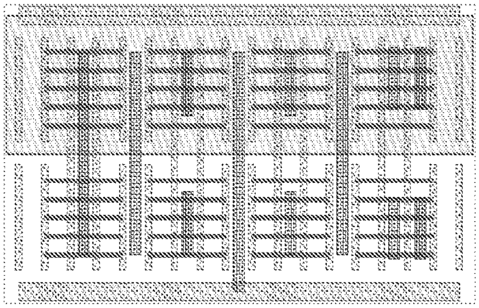
FIG. 1550B
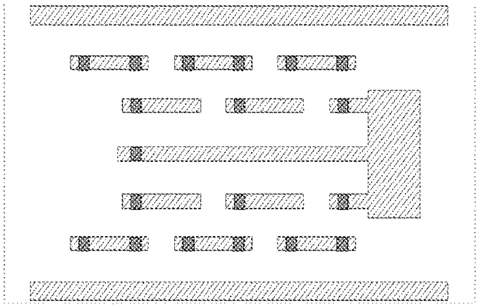
FIG. 1550C

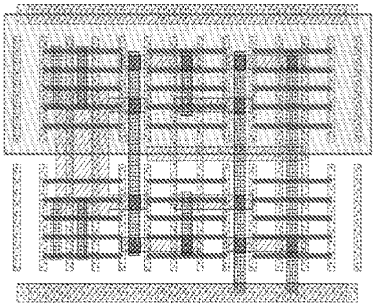
FIG. 1551A
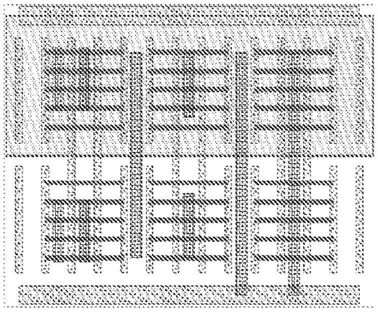
FIG. 1551B
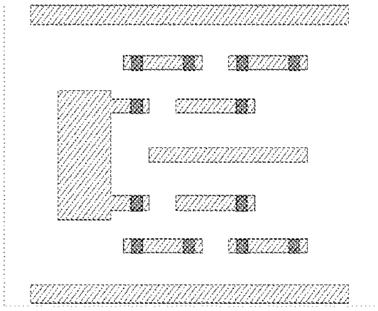
FIG. 1551C
*M* PDF Solutions, Inc.

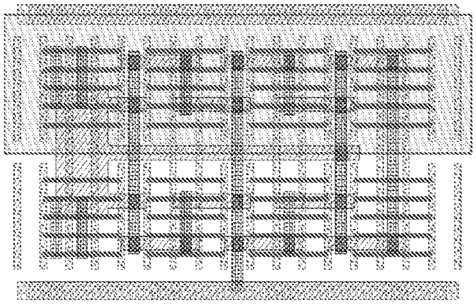
FIG. 1552A
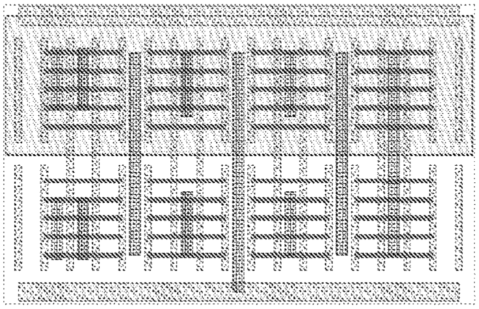
FIG. 1552B
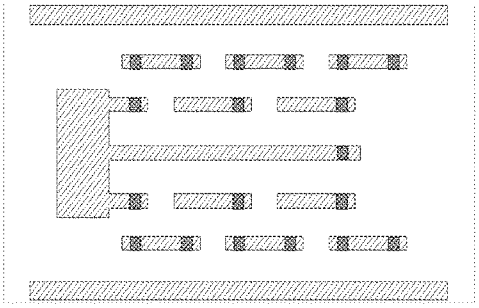
FIG. 1552C

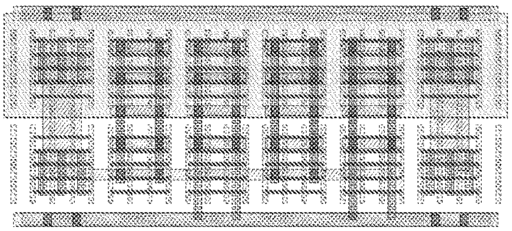
FIG. 1553A
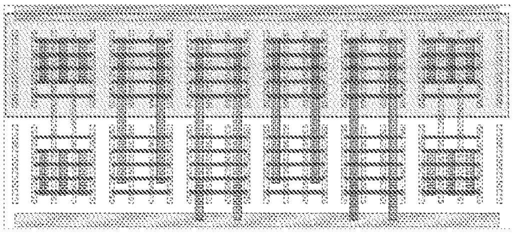
FIG. 1553B
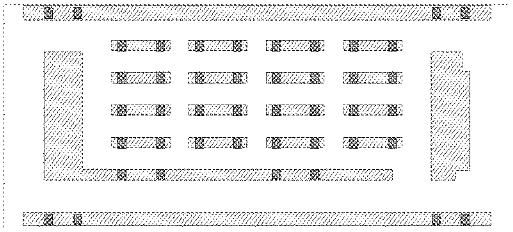
FIG. 1553C

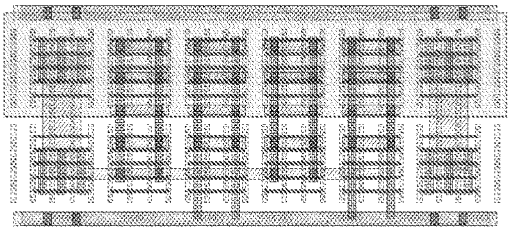
FIG. 1554A
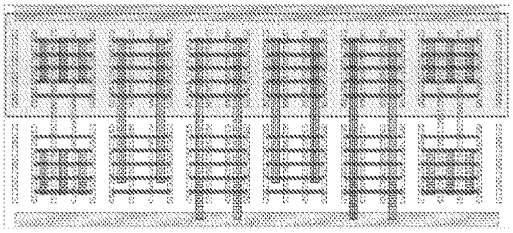
FIG. 1554B
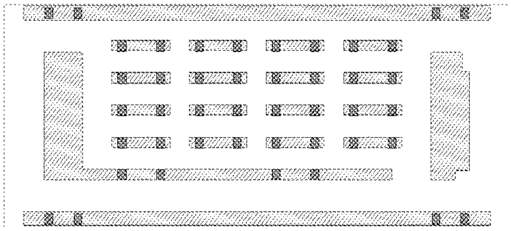
FIG. 1554C
*M* PDF Solutions, Inc.

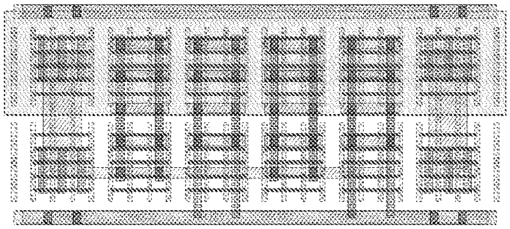
FIG. 1555A
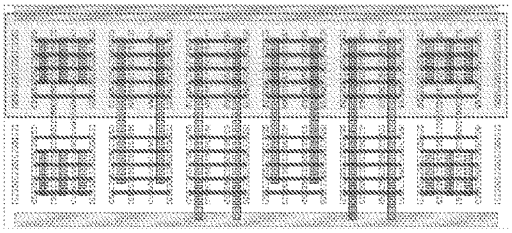
FIG. 1555B
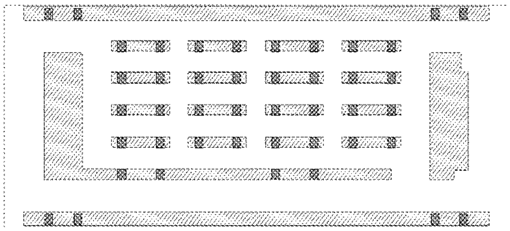
FIG. 1555C
*M* PDF Solutions, Inc.

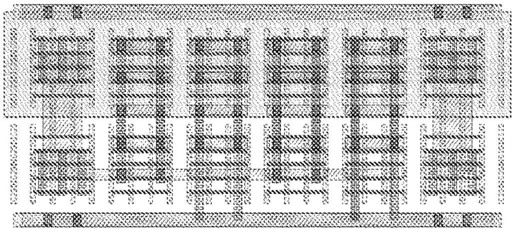
FIG. 1556A
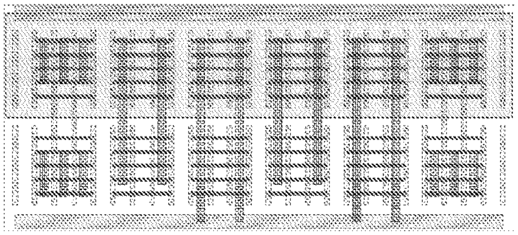
FIG. 1556B
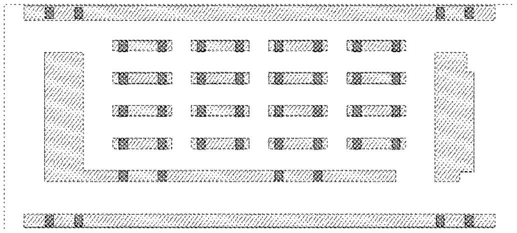
FIG. 1556C

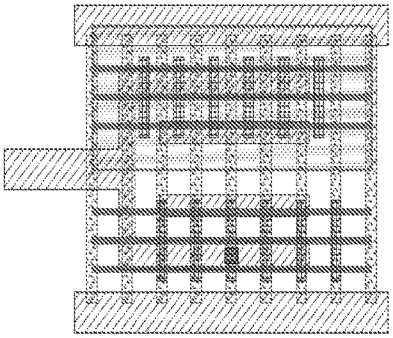
FIG. 1557A
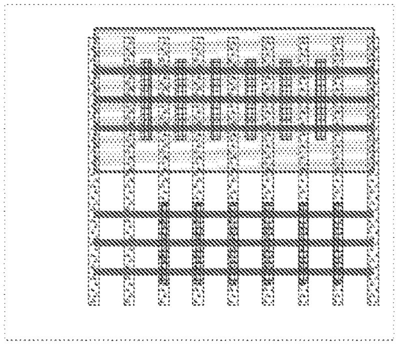
FIG. 1557B
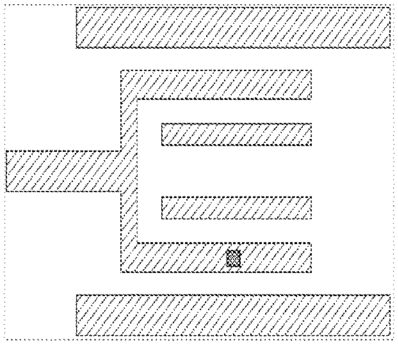
FIG. 1557C
*M* PDF Solutions, Inc.

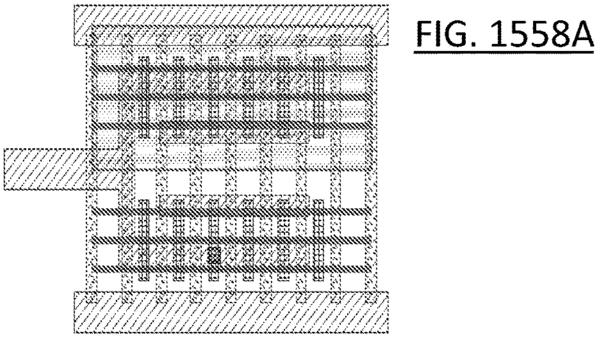
FIG. 1558A
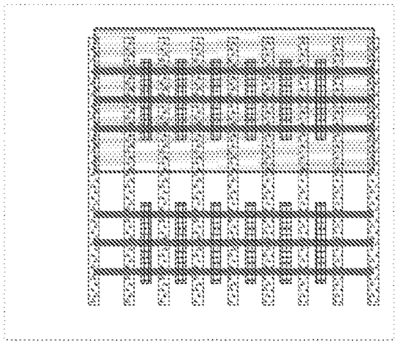
FIG. 1558B
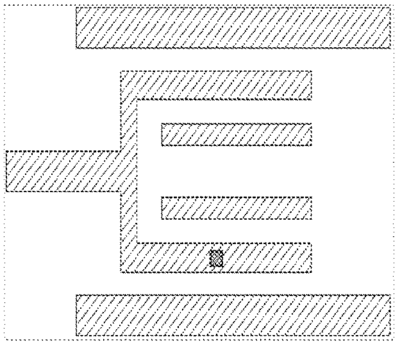
FIG. 1558C

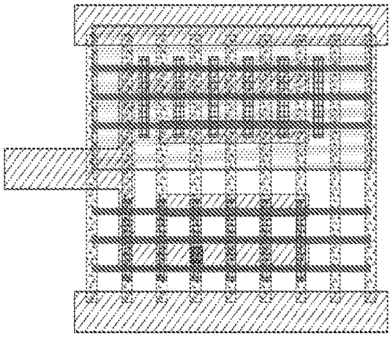
FIG. 1559A
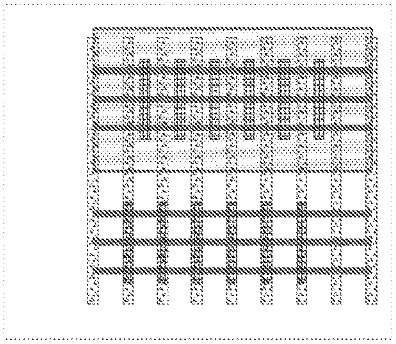
FIG. 1559B
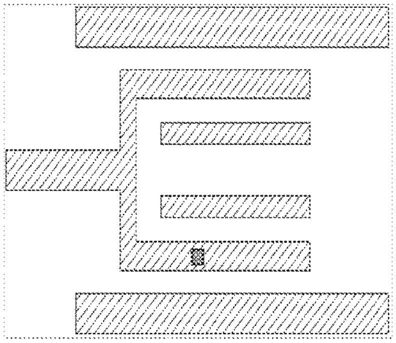
FIG. 1559C

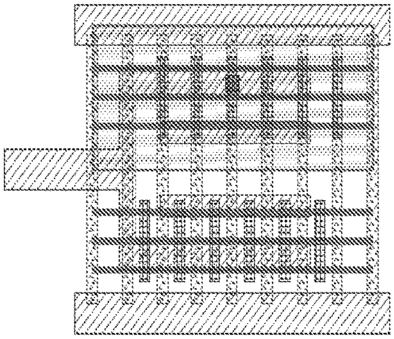
FIG. 1560A
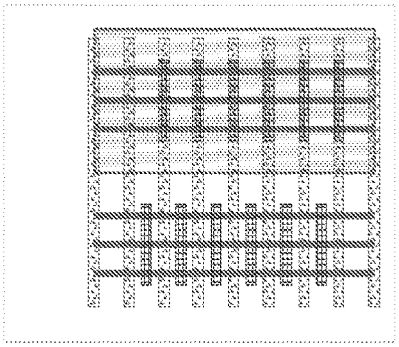
FIG. 1560B
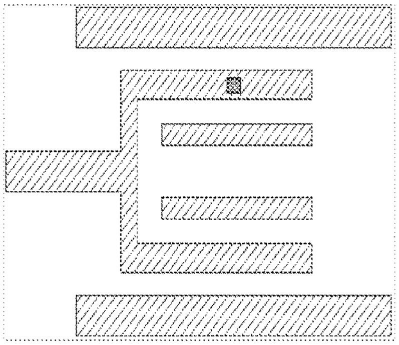
FIG. 1560C
*M* PDF Solutions, Inc.

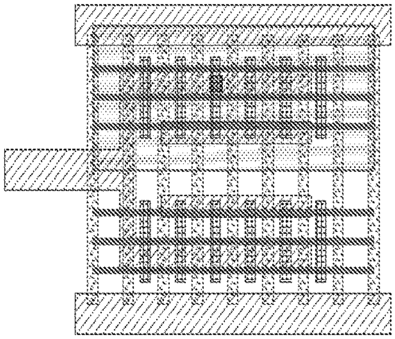
FIG. 1561A
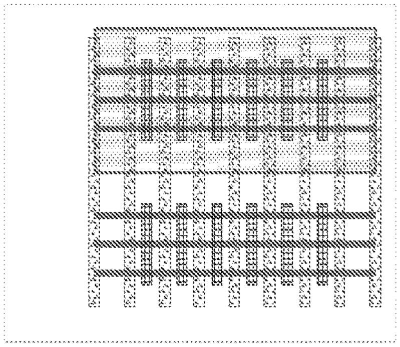
FIG. 1561B
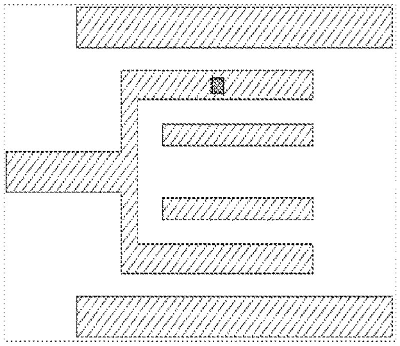
FIG. 1561C

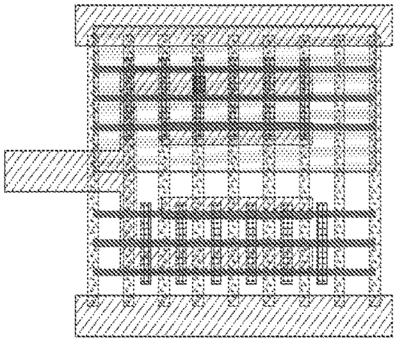
FIG. 1562A
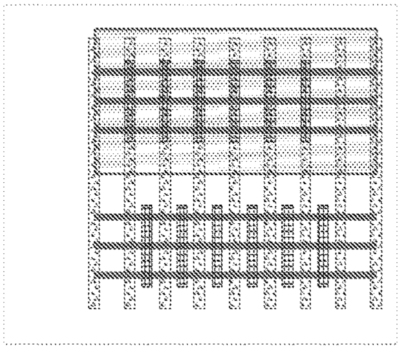
FIG. 1562B
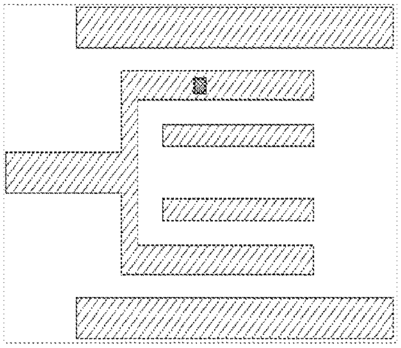
FIG. 1562C

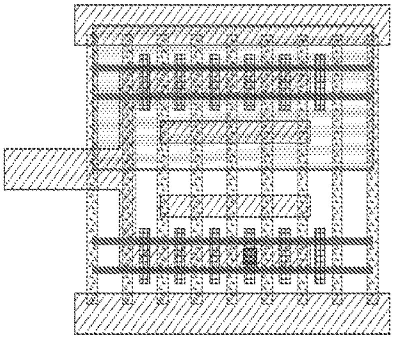
FIG. 1563A
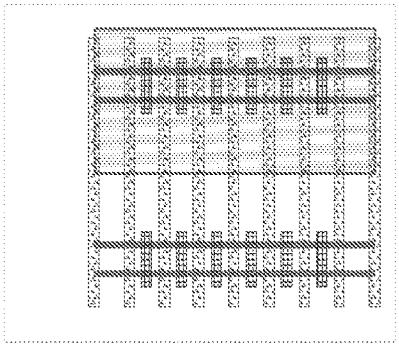
FIG. 1563B
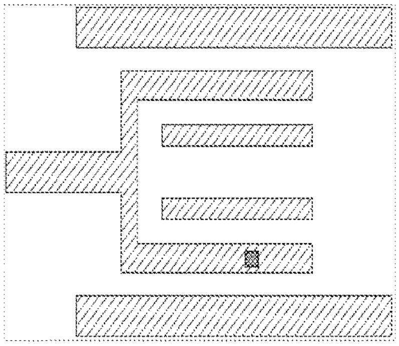
FIG. 1563C

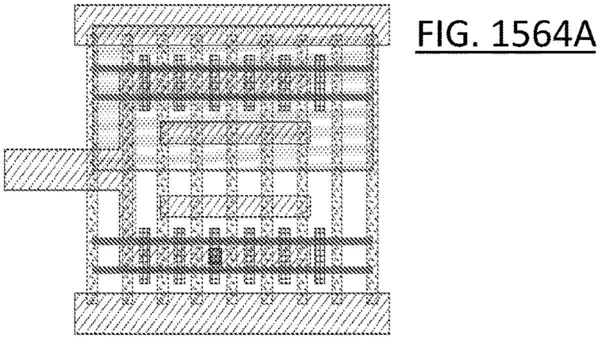
FIG. 1564A
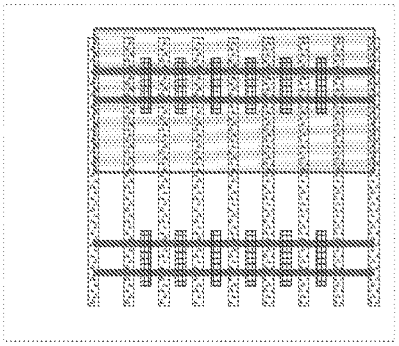
FIG. 1564B
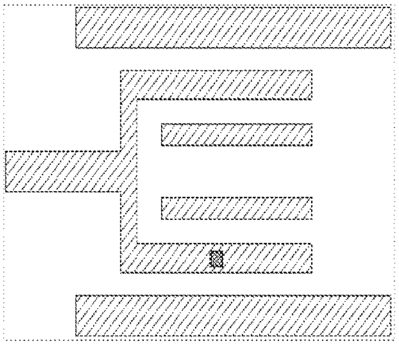
FIG. 1564C
*M* PDF Solutions, Inc.

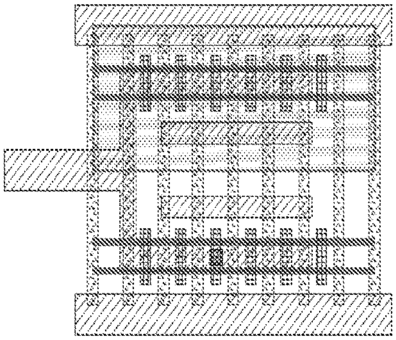
FIG. 1565A
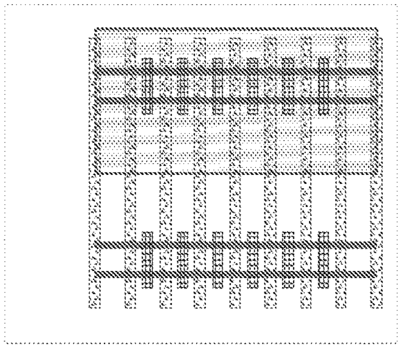
FIG. 1565B
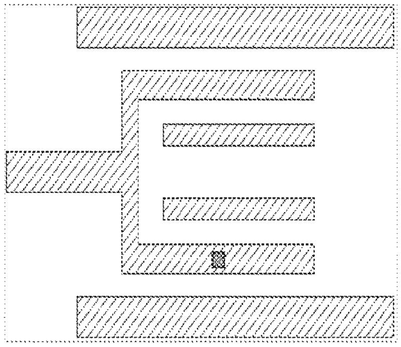
FIG. 1565C
*M* PDF Solutions, Inc.

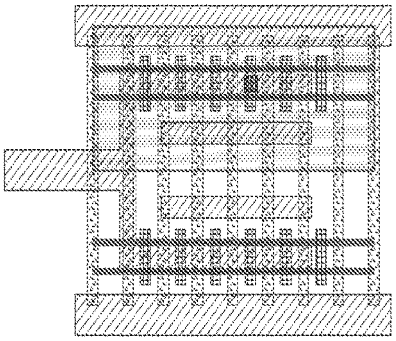
FIG. 1566A
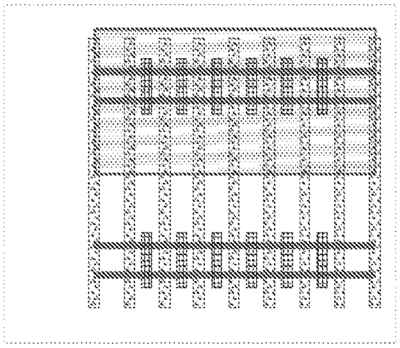
FIG. 1566B
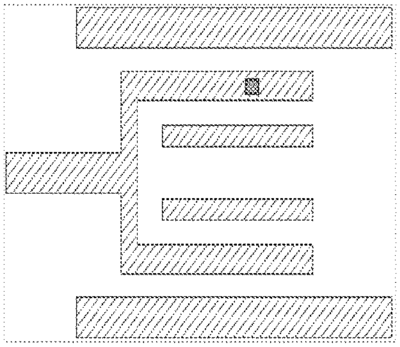
FIG. 1566C

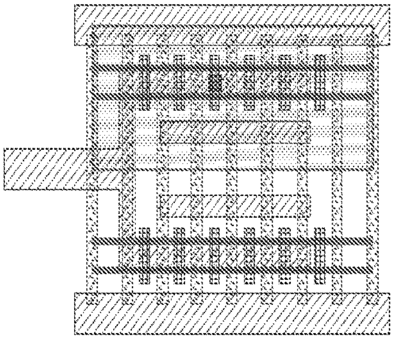
FIG. 1567A
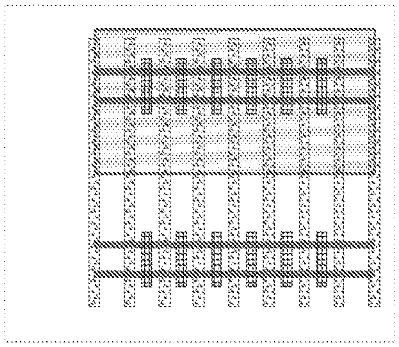
FIG. 1567B
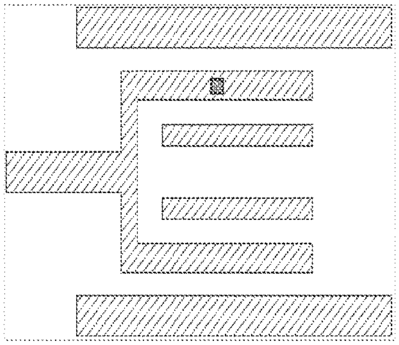
FIG. 1567C

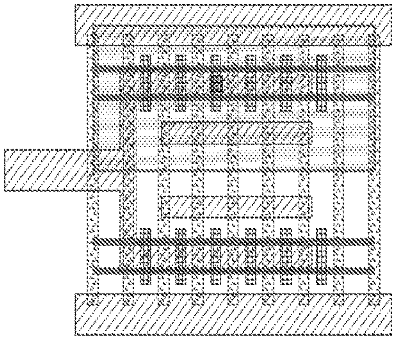
FIG. 1568A
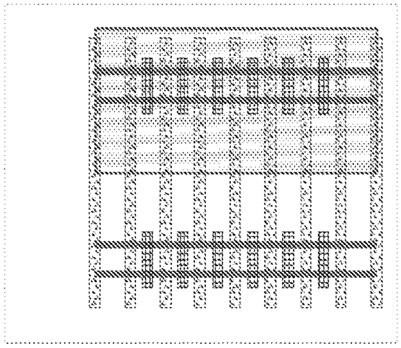
FIG. 1568B
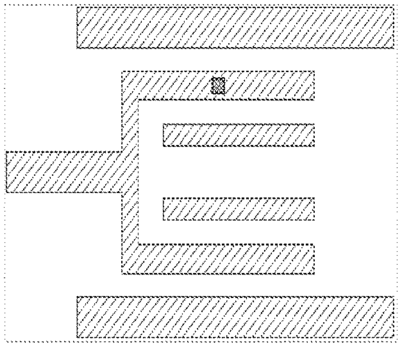
FIG. 1568C

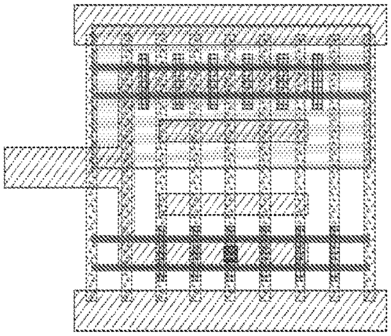
FIG. 1569A
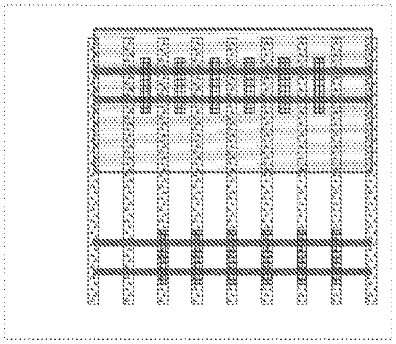
FIG. 1569B
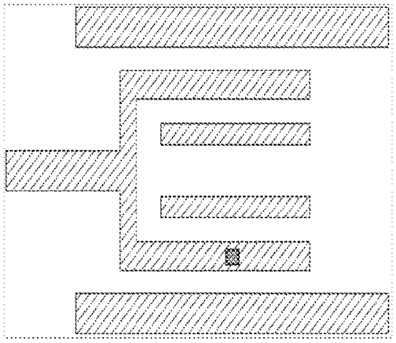
FIG. 1569C

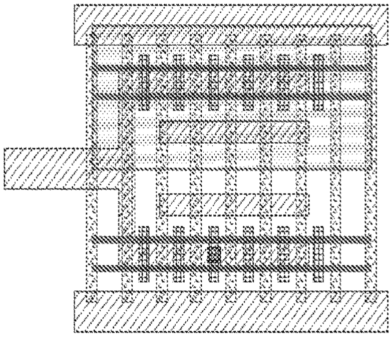
FIG. 1570A
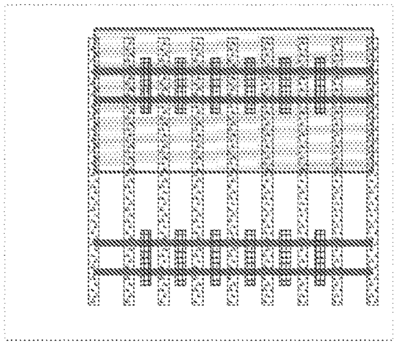
FIG. 1570B
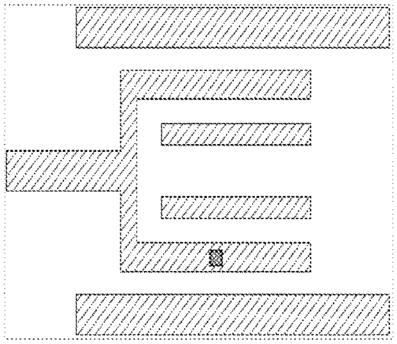
FIG. 1570C

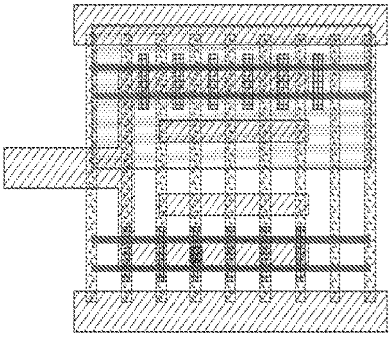
FIG. 1571A
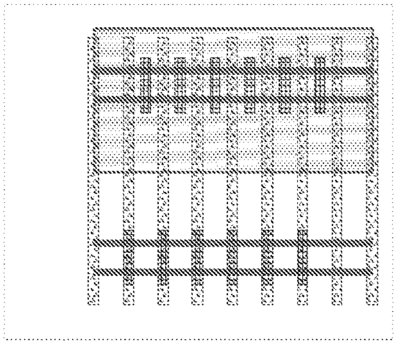
FIG. 1571B
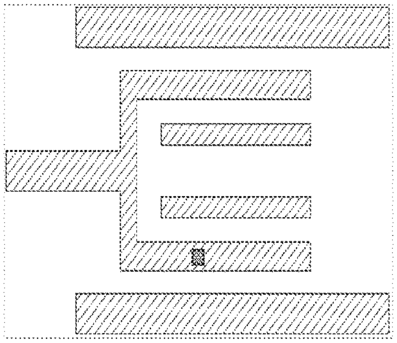
FIG. 1571C
*M* PDF Solutions, Inc.

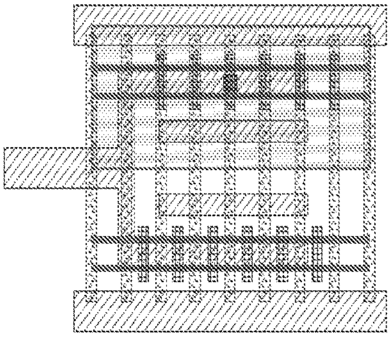
FIG. 1572A
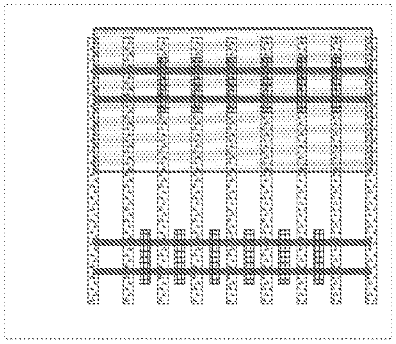
FIG. 1572B
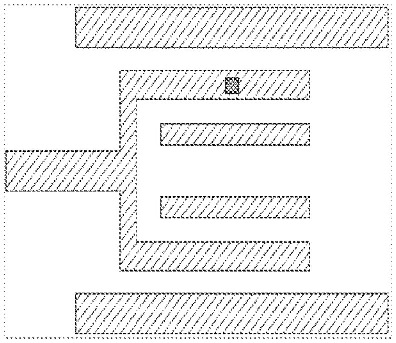
FIG. 1572C

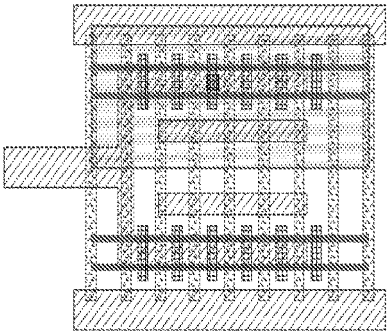
FIG. 1573A
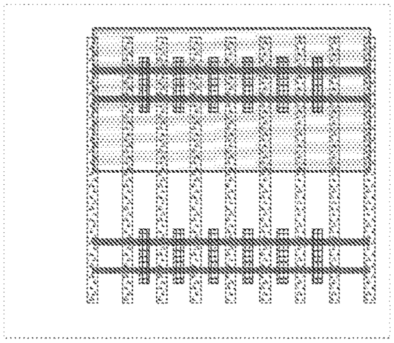
FIG. 1573B
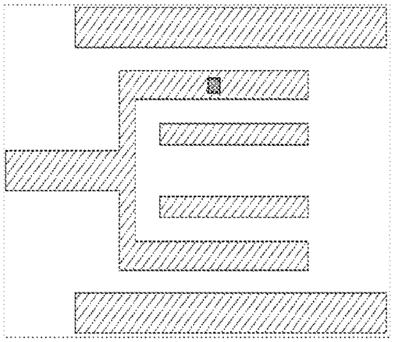
FIG. 1573C

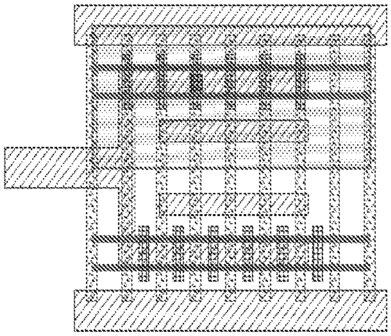
FIG. 1574A
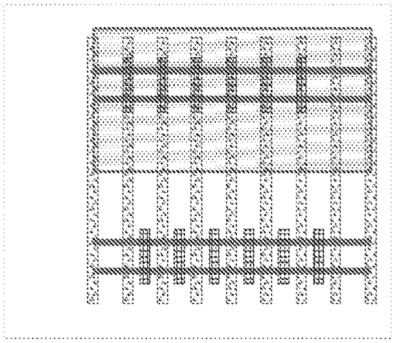
FIG. 1574B
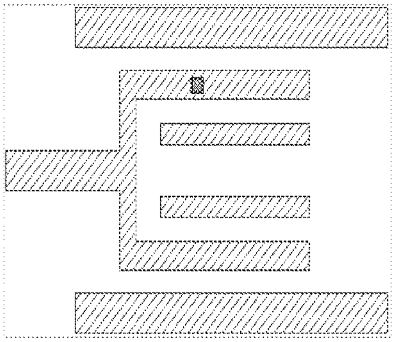
FIG. 1574C

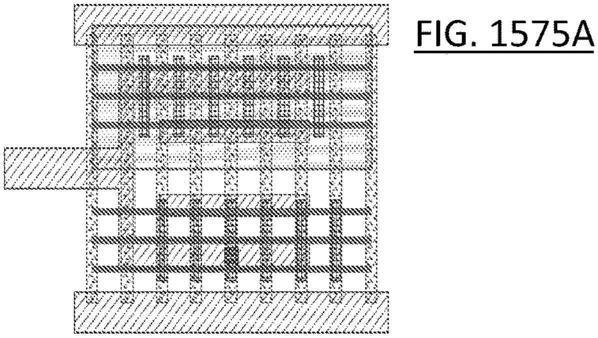
FIG. 1575A
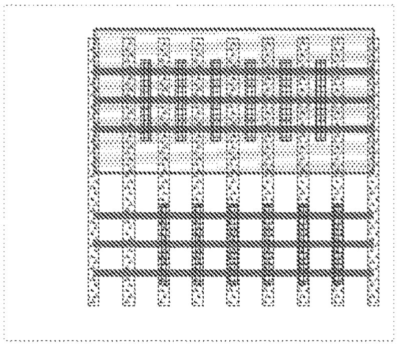
FIG. 1575B
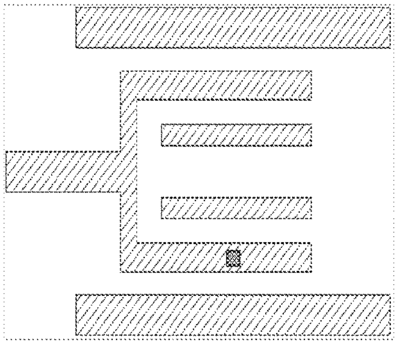
FIG. 1575C

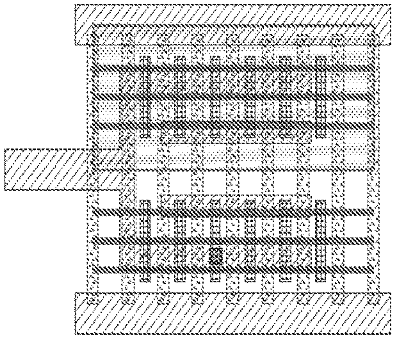
FIG. 1576A
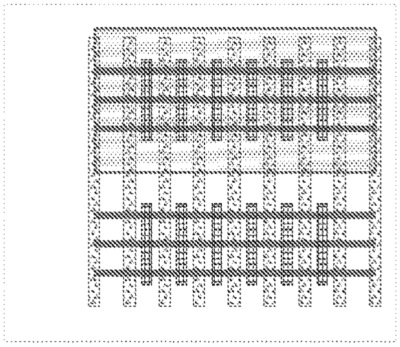
FIG. 1576B
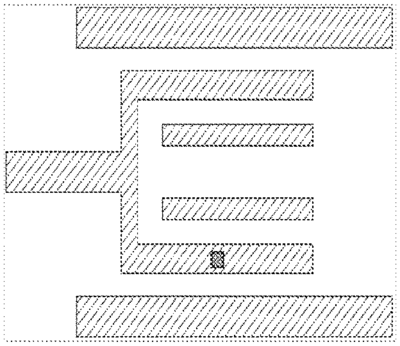
FIG. 1576C
*M* PDF Solutions, Inc.

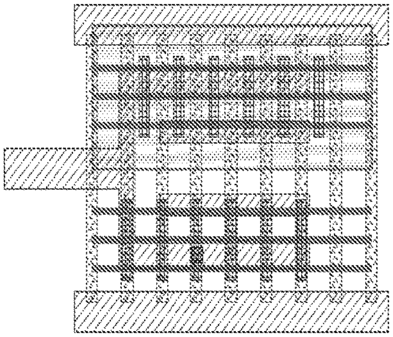
FIG. 1577A
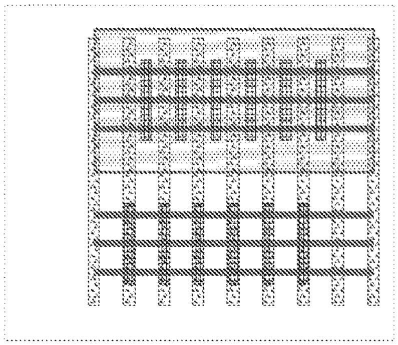
FIG. 1577B
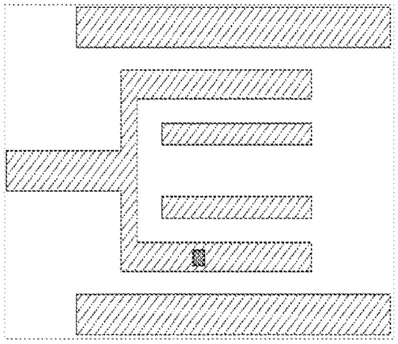
FIG. 1577C

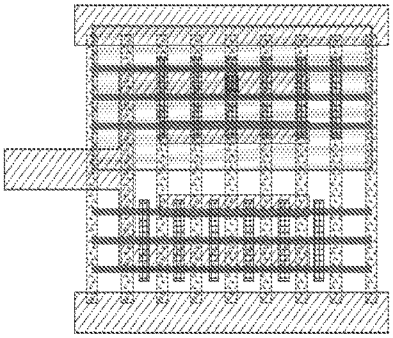
FIG. 1578A
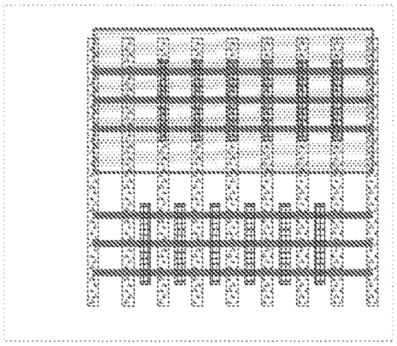
FIG. 1578B
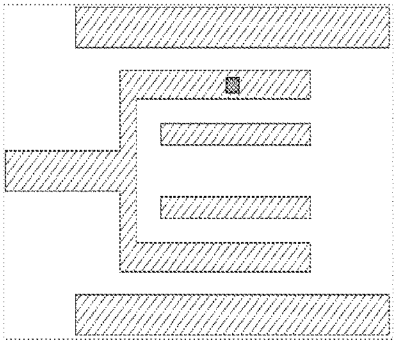
FIG. 1578C
*M* PDF Solutions, Inc.

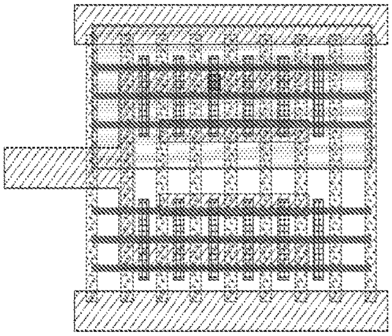
FIG. 1579A
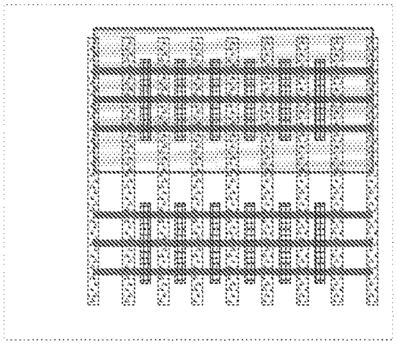
FIG. 1579B
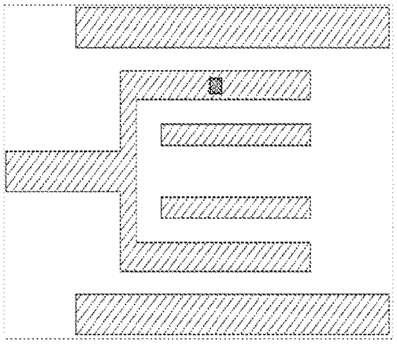
FIG. 1579C

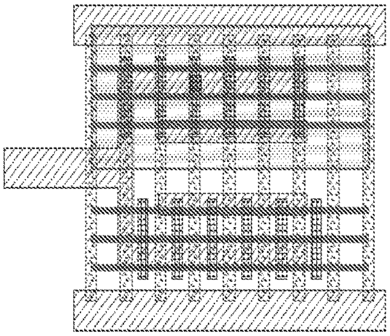
FIG. 1580A
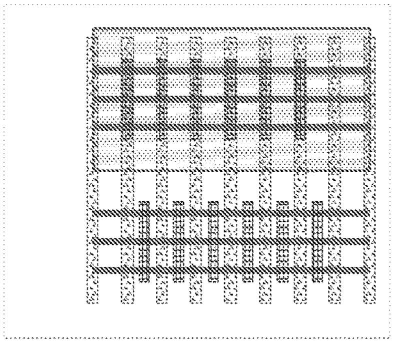
FIG. 1580B
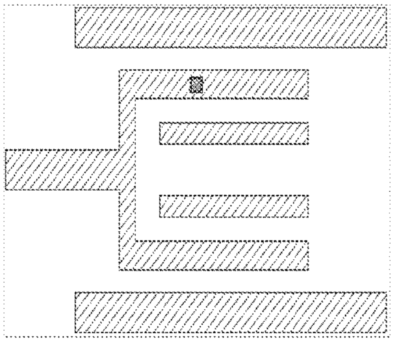
FIG. 1580C

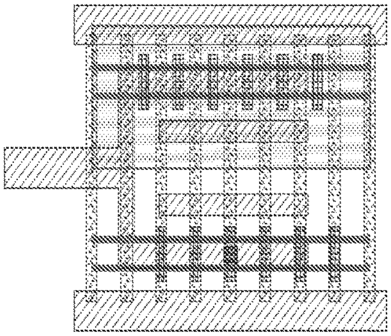
FIG. 1581A
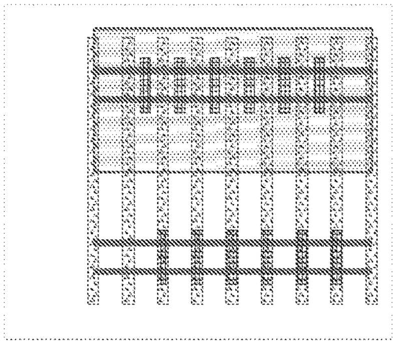
FIG. 1581B
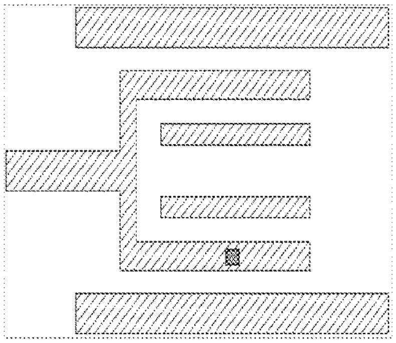
FIG. 1581C

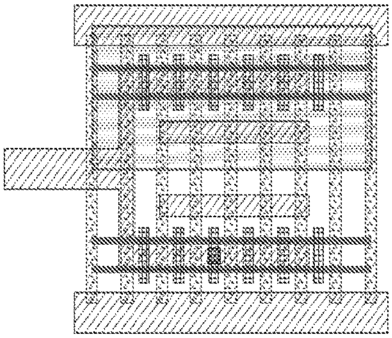
FIG. 1582A
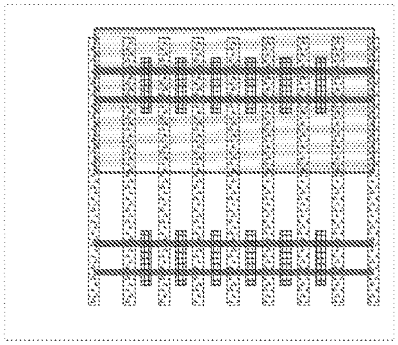
FIG. 1582B
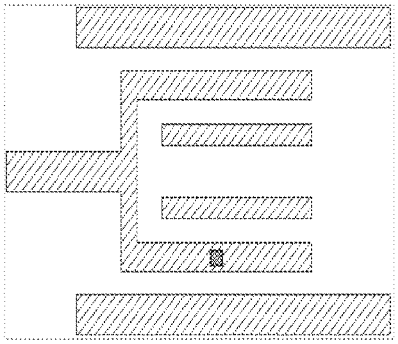
FIG. 1582C

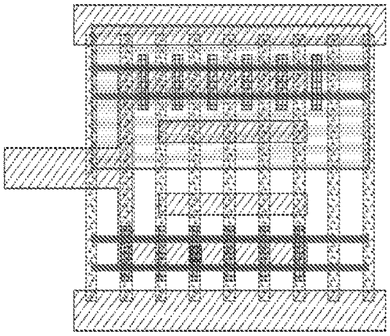
FIG. 1583A
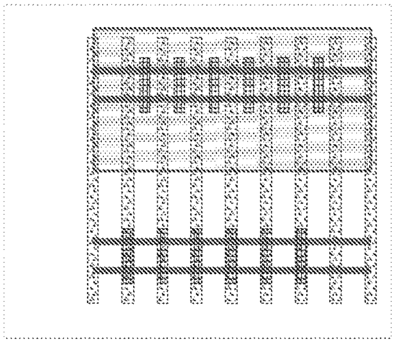
FIG. 1583B
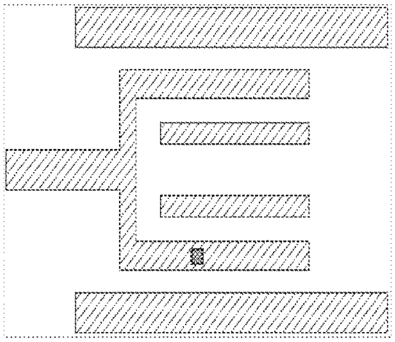
FIG. 1583C

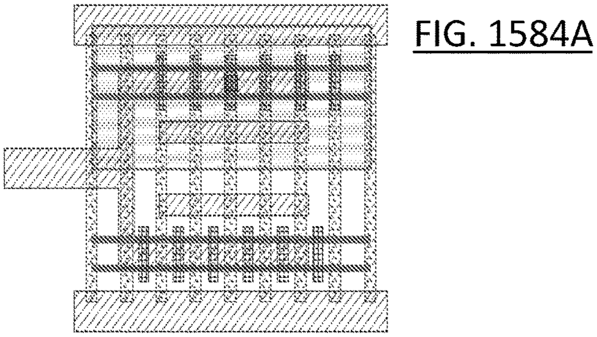
FIG. 1584A
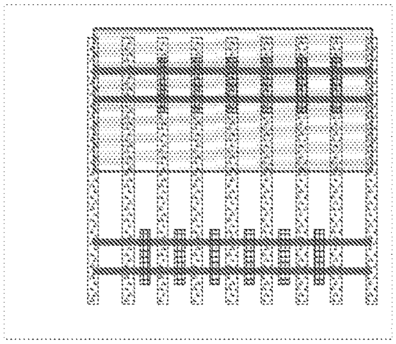
FIG. 1584B
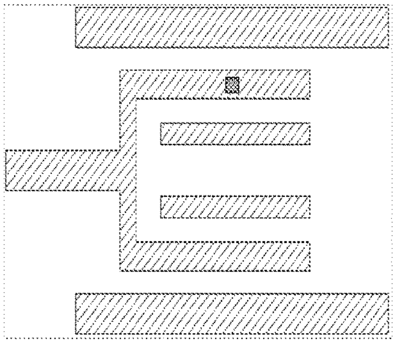
FIG. 1584C
*M* PDF Solutions, Inc.

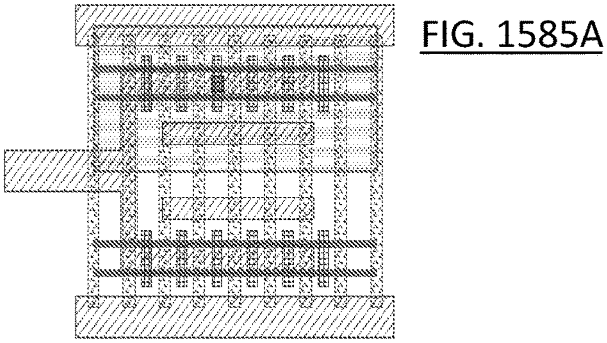
FIG. 1585A
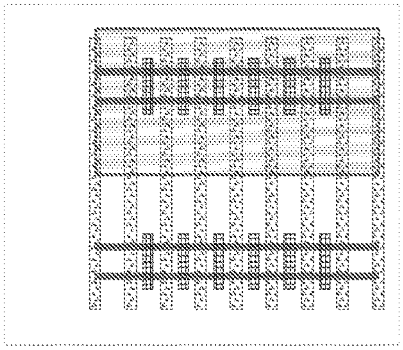
FIG. 1585B
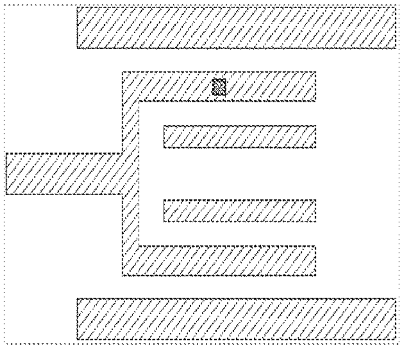
FIG. 1585C

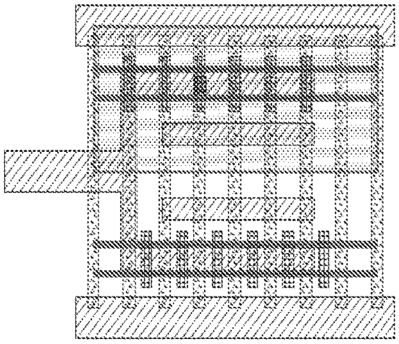
FIG. 1586A
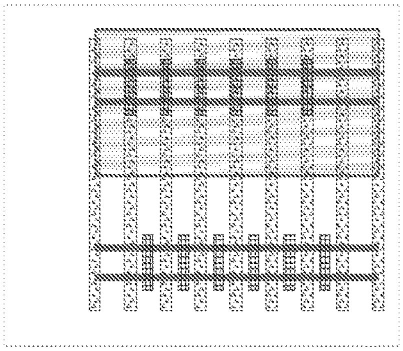
FIG. 1586B
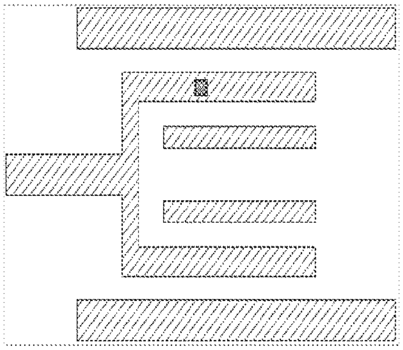
FIG. 1586C
*M* PDF Solutions, Inc.

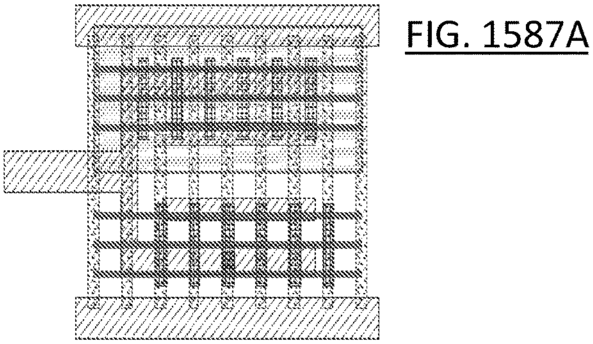
FIG. 1587A
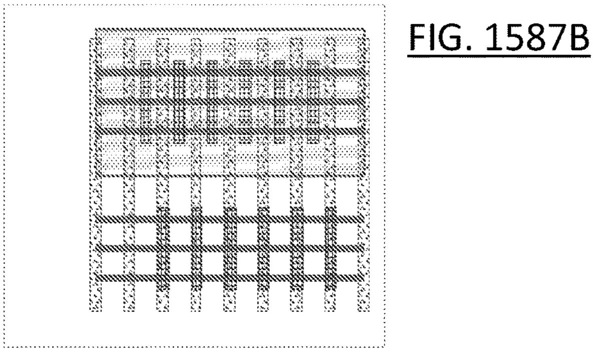
FIG. 1587B
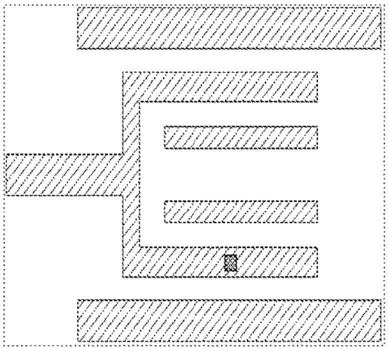
FIG. 1587C

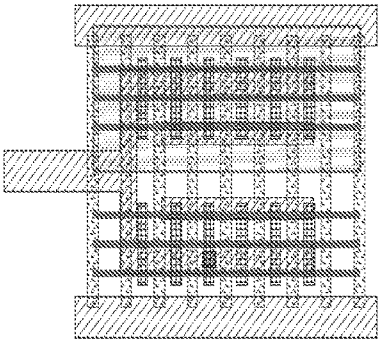
FIG. 1588A
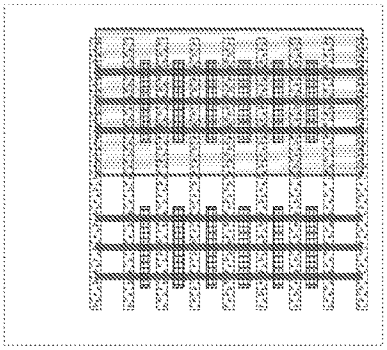
FIG. 1588B
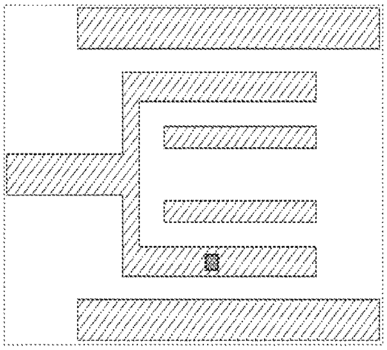
FIG. 1588C

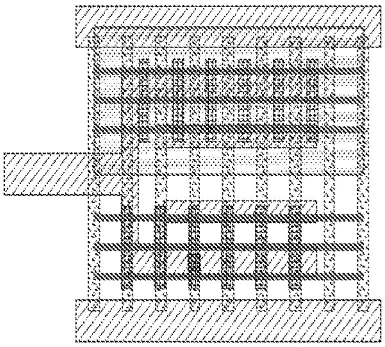
FIG. 1589A
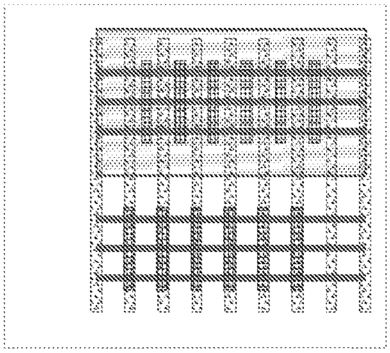
FIG. 1589B
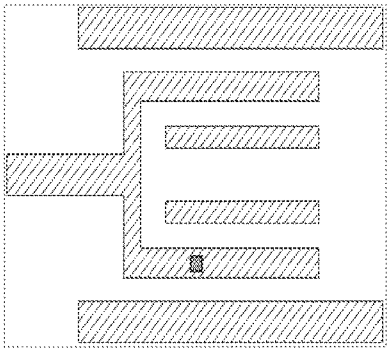
FIG. 1589C

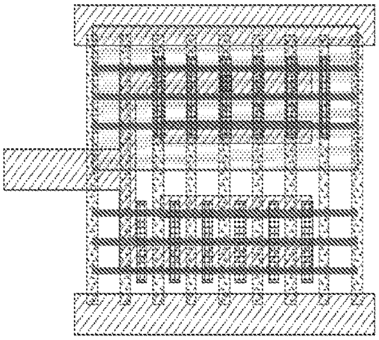
FIG. 1590A
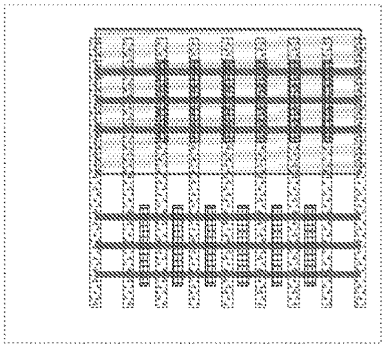
FIG. 1590B
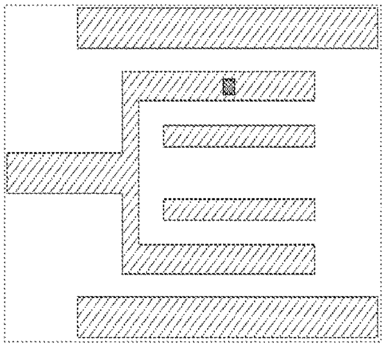
FIG. 1590C

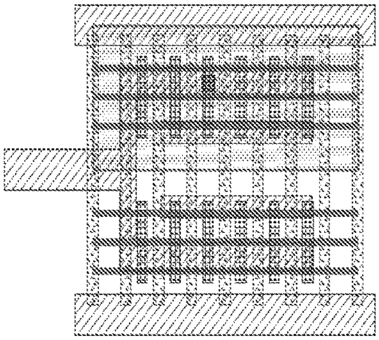
FIG. 1591A
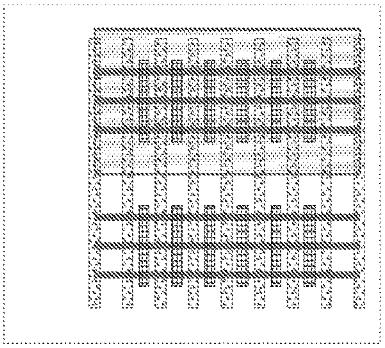
FIG. 1591B
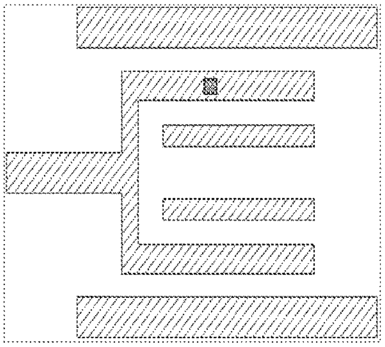
FIG. 1591C
*M* PDF Solutions, Inc.

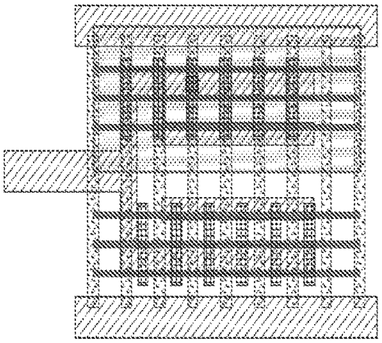
FIG. 1592A
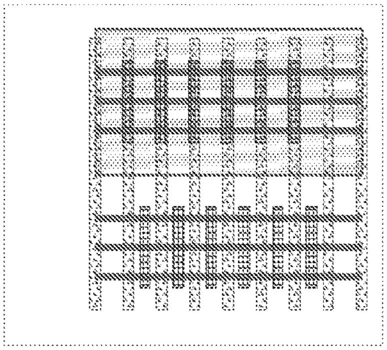
FIG. 1592B
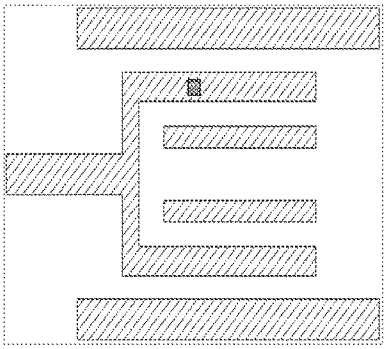
FIG. 1592C
*M* PDF Solutions, Inc.

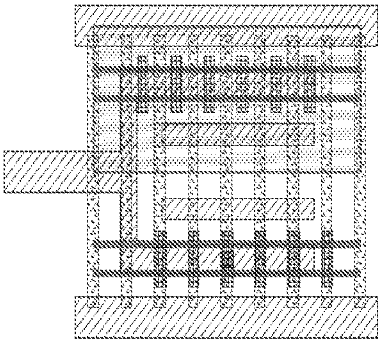
FIG. 1593A
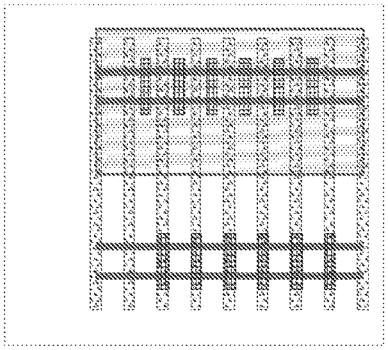
FIG. 1593B
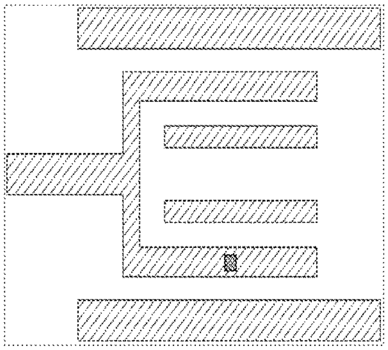
FIG. 1593C
*M* PDF Solutions, Inc.

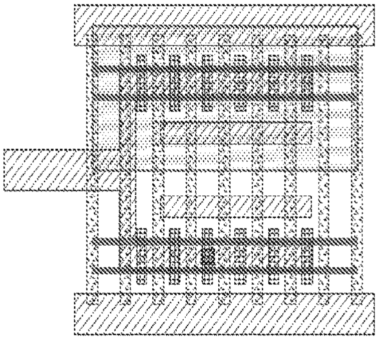
FIG. 1594A
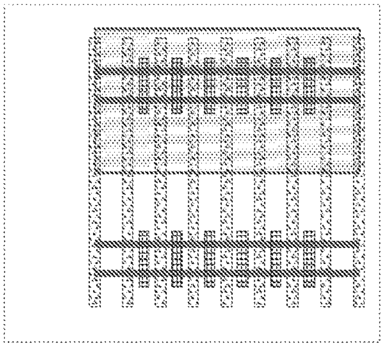
FIG. 1594B
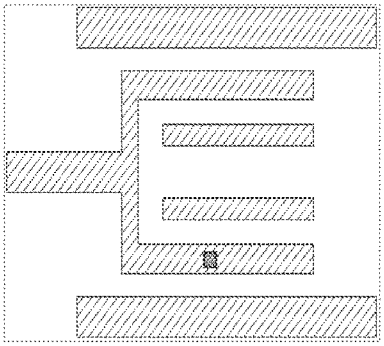
FIG. 1594C

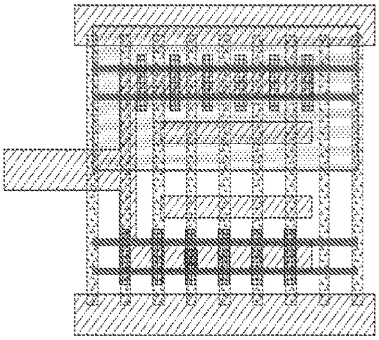
FIG. 1595A
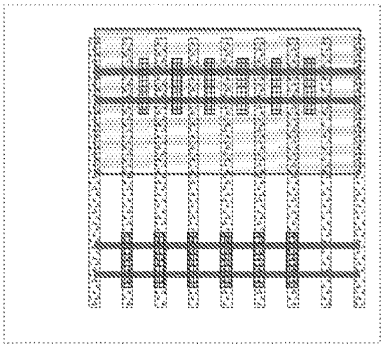
FIG. 1595B
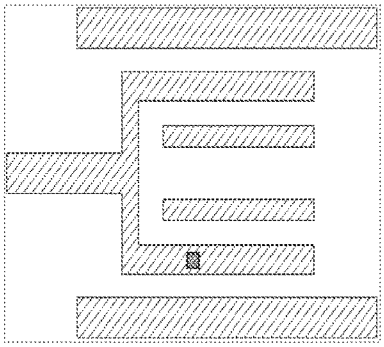
FIG. 1595C

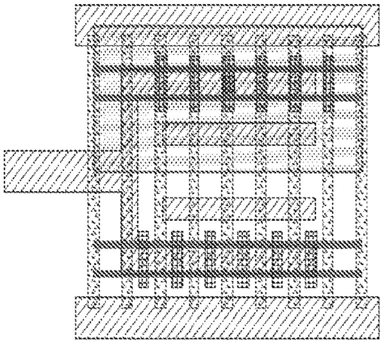
FIG. 1596A
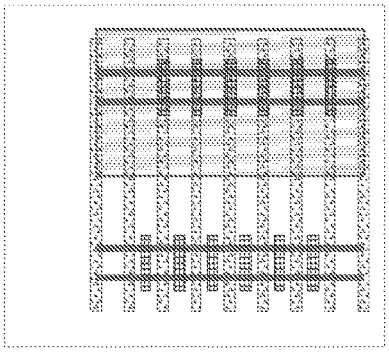
FIG. 1596B
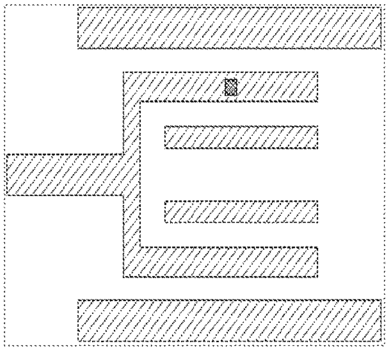
FIG. 1596C

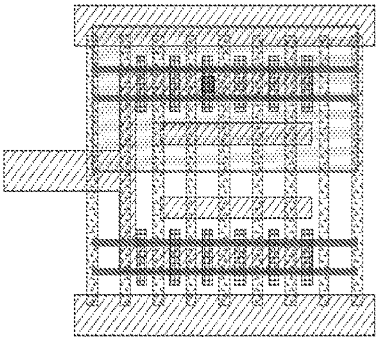
FIG. 1597A
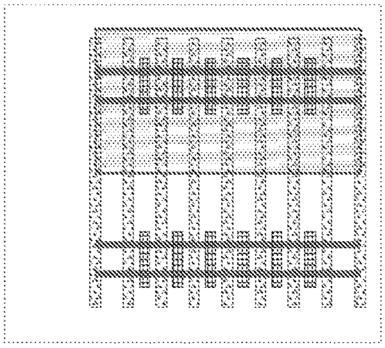
FIG. 1597B
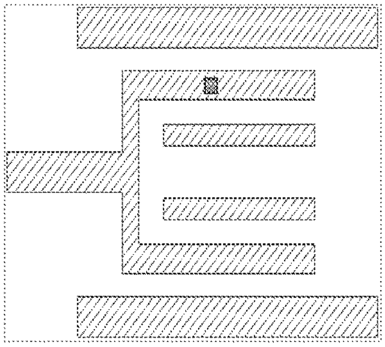
FIG. 1597C

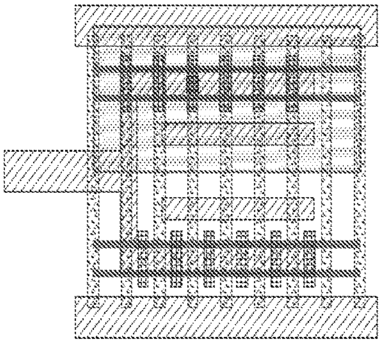
FIG. 1598A
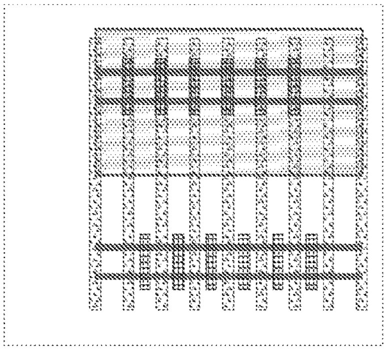
FIG. 1598B
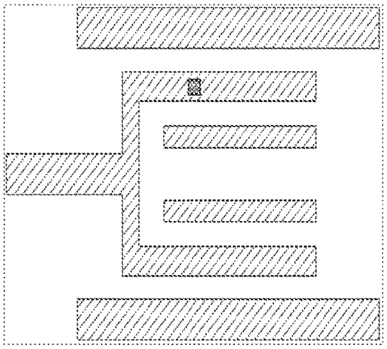
FIG. 1598C

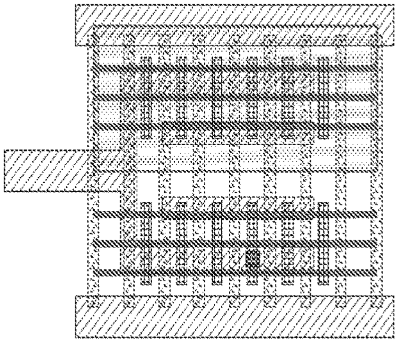
FIG. 1599A
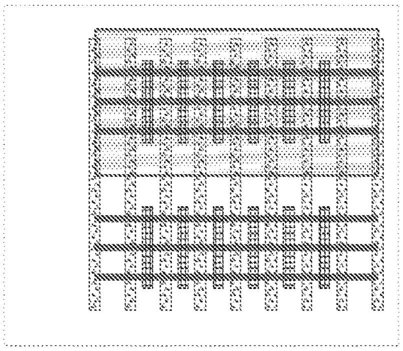
FIG. 1599B
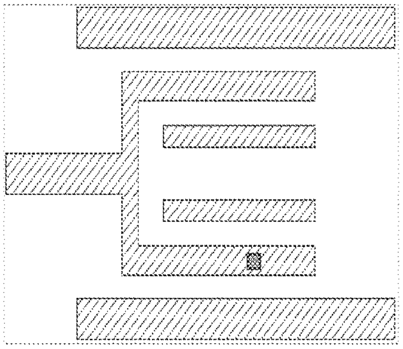
FIG. 1599C

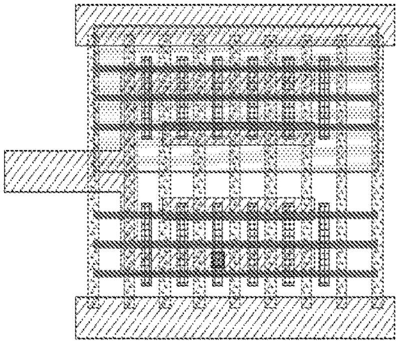
FIG. 1600A
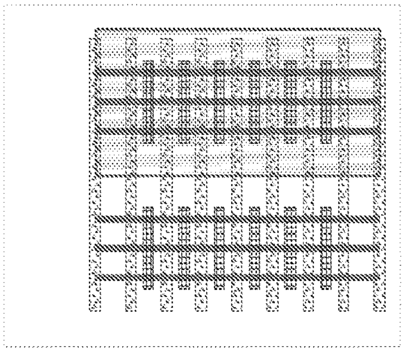
FIG. 1600B
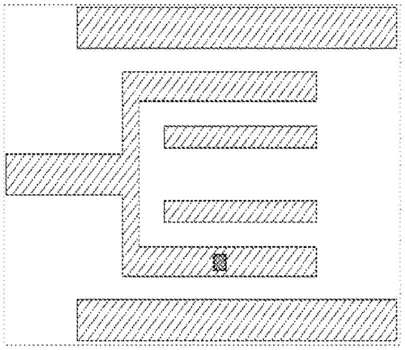
FIG. 1600C

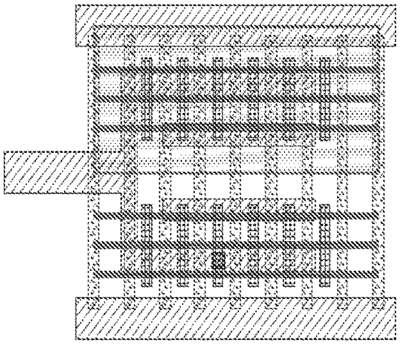
FIG. 1601A
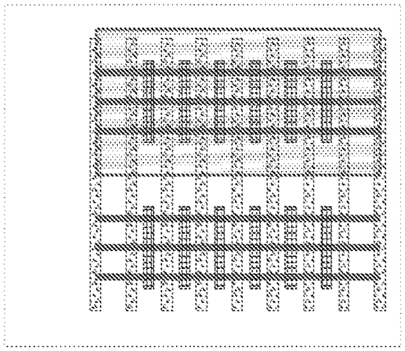
FIG. 1601B
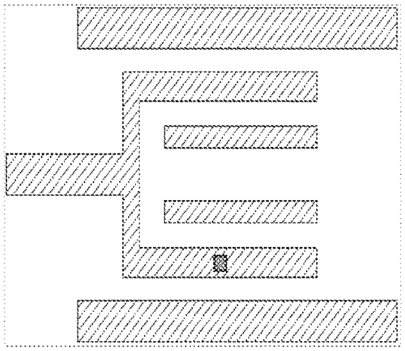
FIG. 1601C

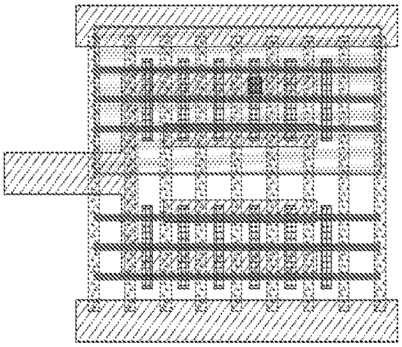
FIG. 1602A
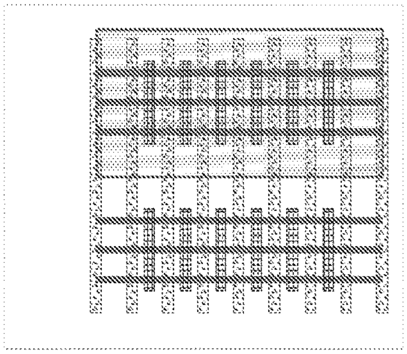
FIG. 1602B
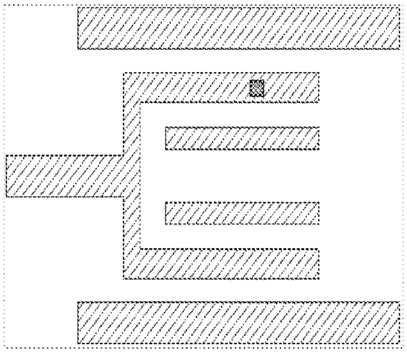
FIG. 1602C

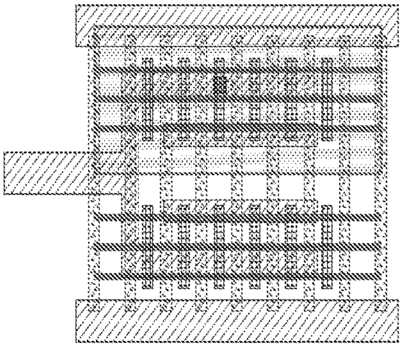
FIG. 1603A
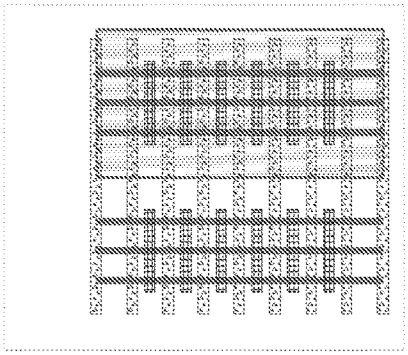
FIG. 1603B
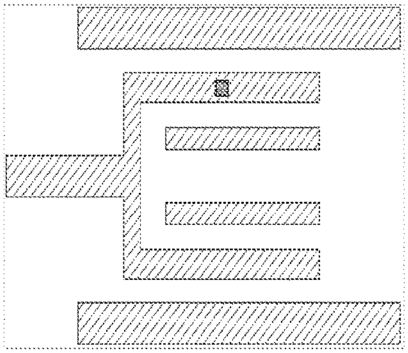
FIG. 1603C

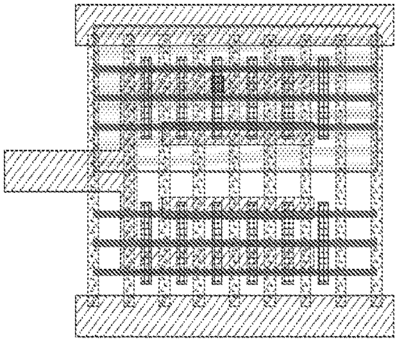
FIG. 1604A
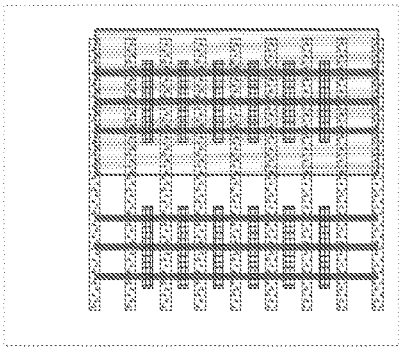
FIG. 1604B
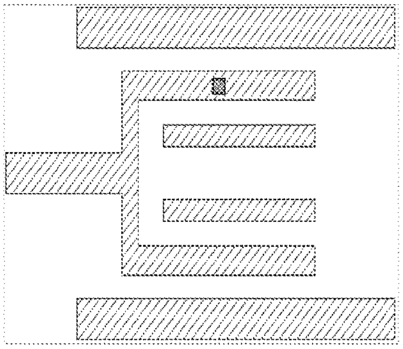
FIG. 1604C

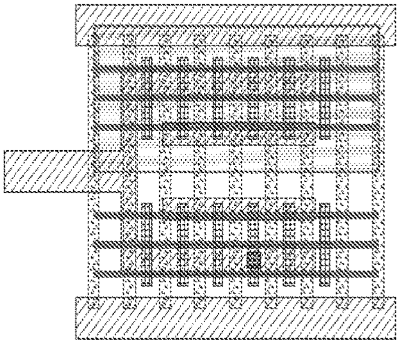
FIG. 1605A
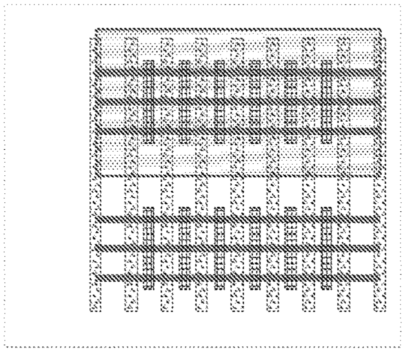
FIG. 1605B
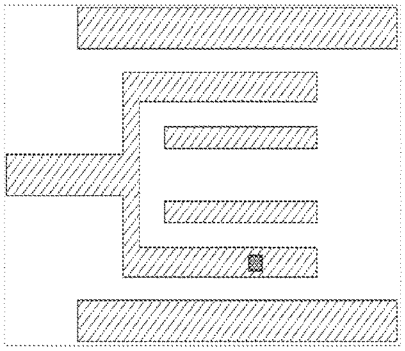
FIG. 1605C
*M* PDF Solutions, Inc.

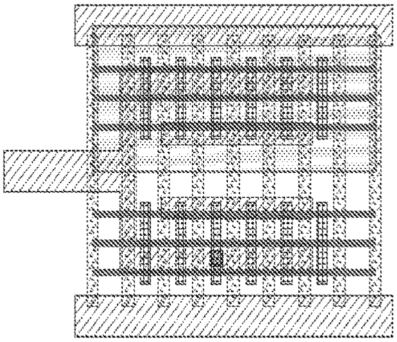
FIG. 1606A
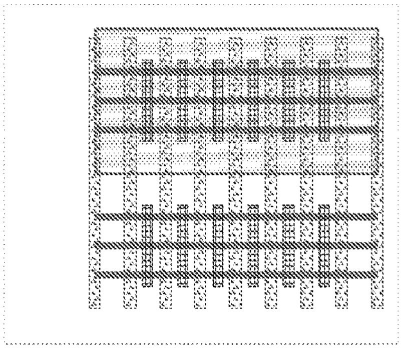
FIG. 1606B
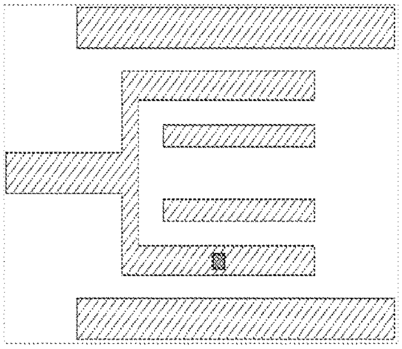
FIG. 1606C

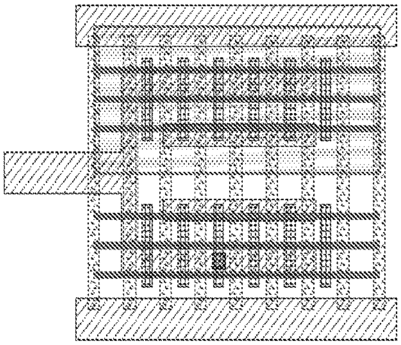
FIG. 1607A
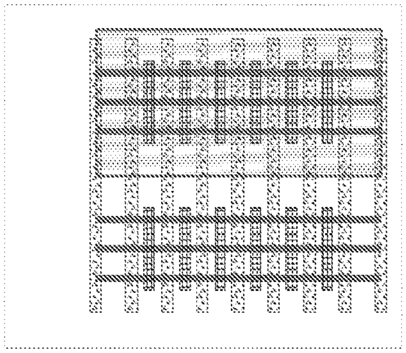
FIG. 1607B
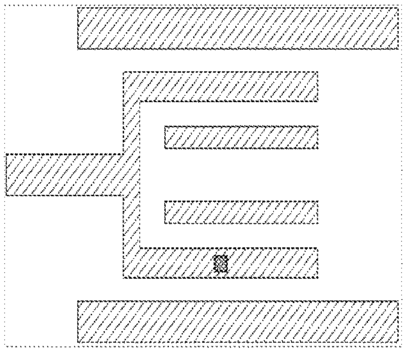
FIG. 1607C

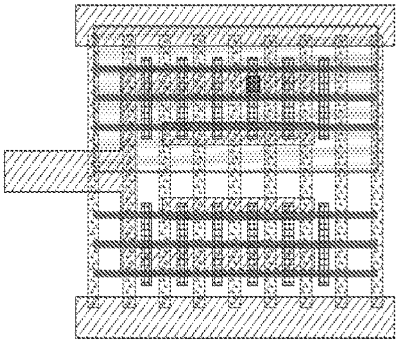
FIG. 1608A
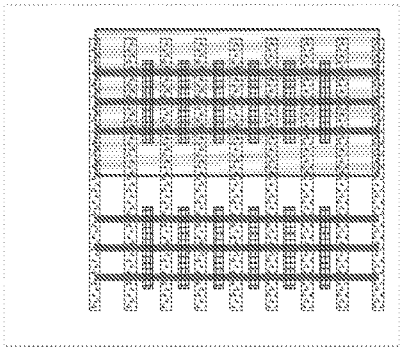
FIG. 1608B
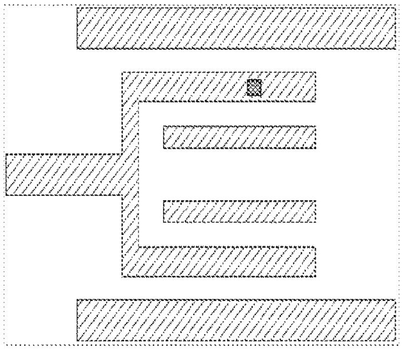
FIG. 1608C

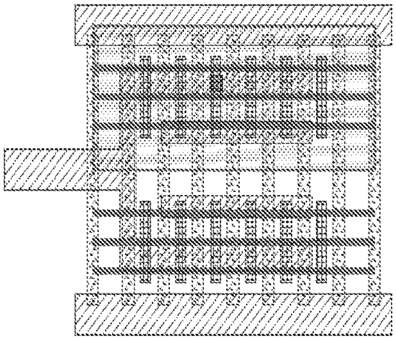
FIG. 1609A
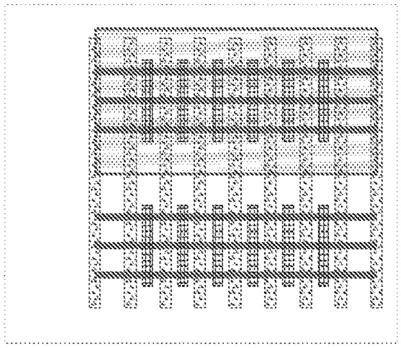
FIG. 1609B
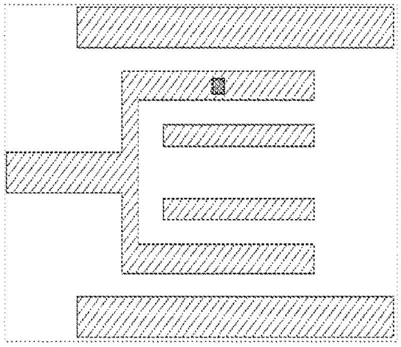
FIG. 1609C
*M* PDF Solutions, Inc.

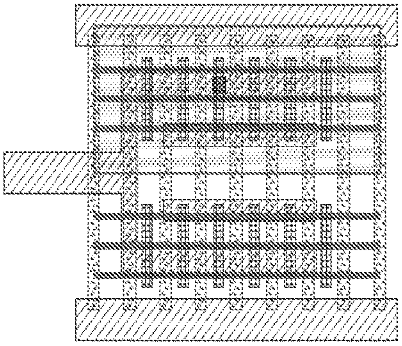
FIG. 1610A
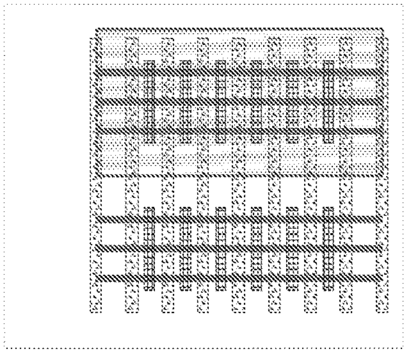
FIG. 1610B
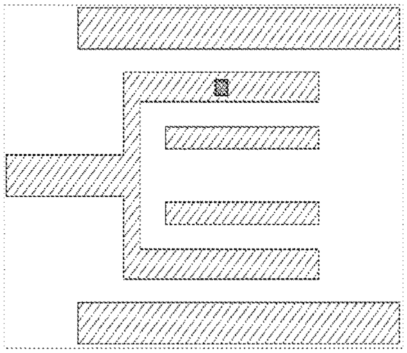
FIG. 1610C

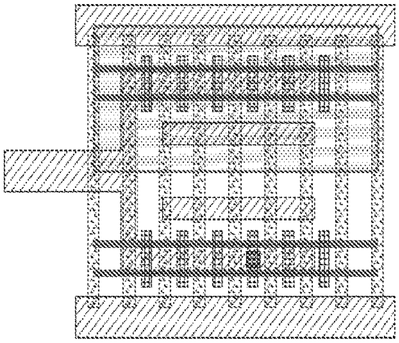
FIG. 1611A
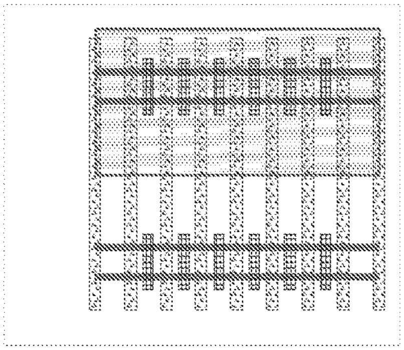
FIG. 1611B
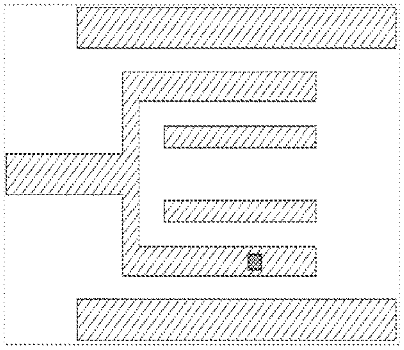
FIG. 1611C

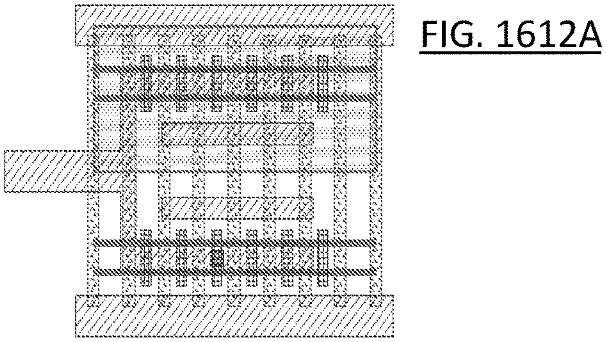
FIG. 1612A
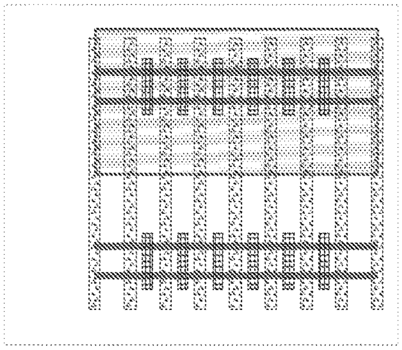
FIG. 1612B
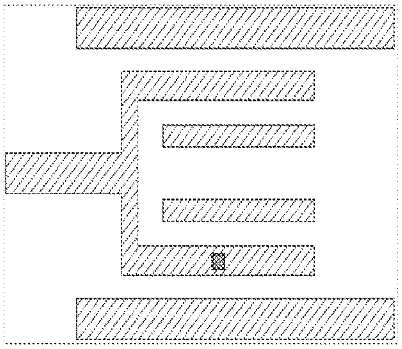
FIG. 1612C
*M* PDF Solutions, Inc.

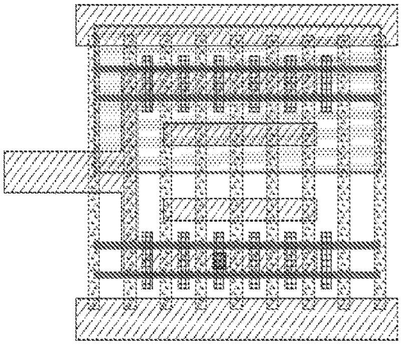
FIG. 1613A
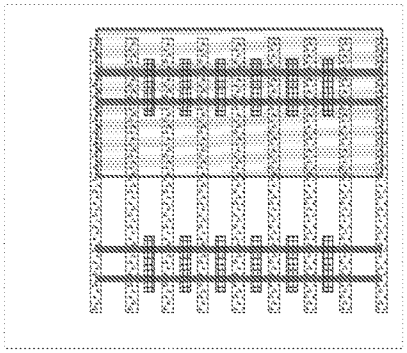
FIG. 1613B
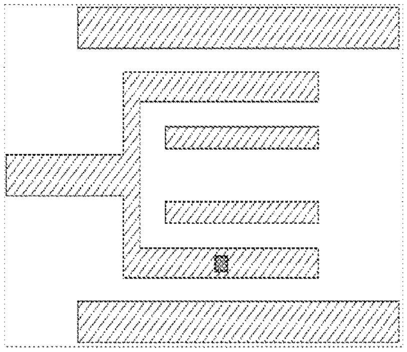
FIG. 1613C

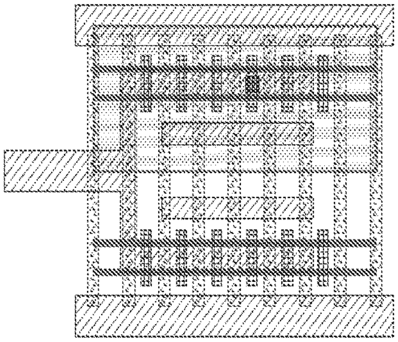
FIG. 1614A
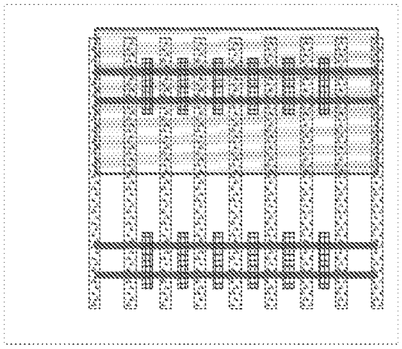
FIG. 1614B
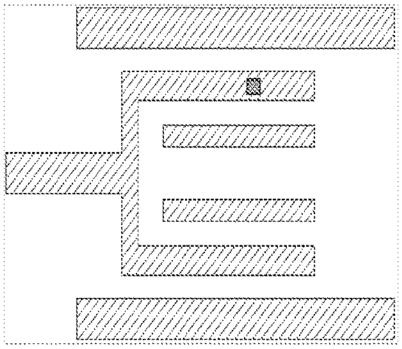
FIG. 1614C

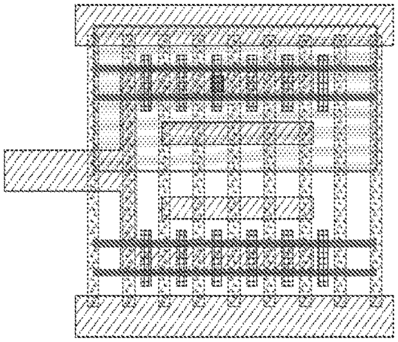
FIG. 1615A
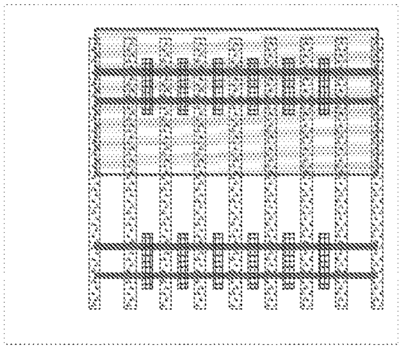
FIG. 1615B
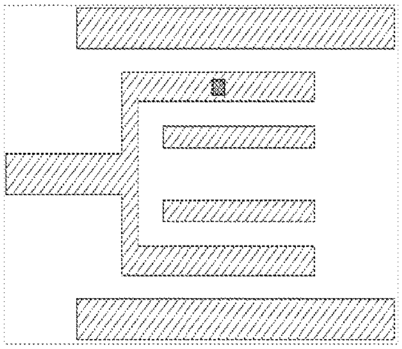
FIG. 1615C
*M* PDF Solutions, Inc.

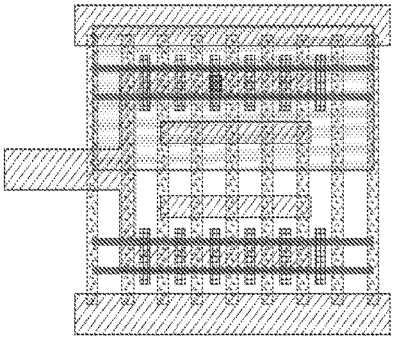
FIG. 1616A
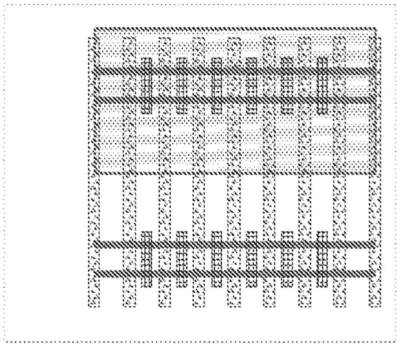
FIG. 1616B
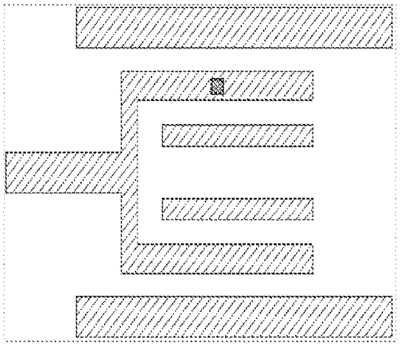
FIG. 1616C
*M* PDF Solutions, Inc.

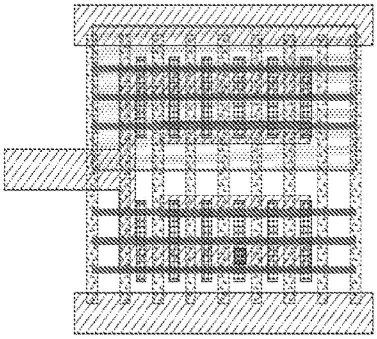
FIG. 1617A
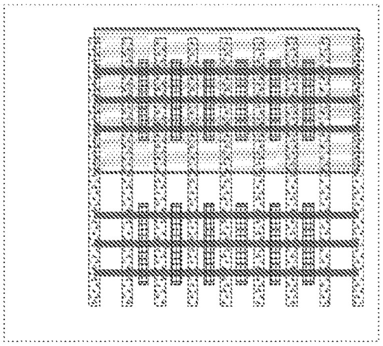
FIG. 1617B
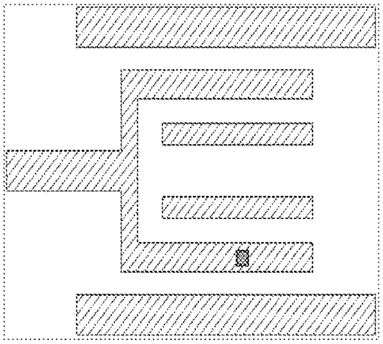
FIG. 1617C

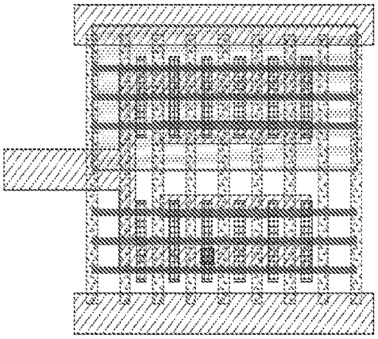
FIG. 1618A
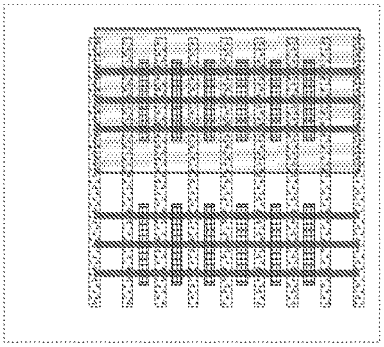
FIG. 1618B
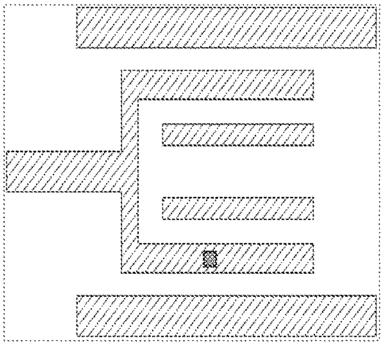
FIG. 1618C

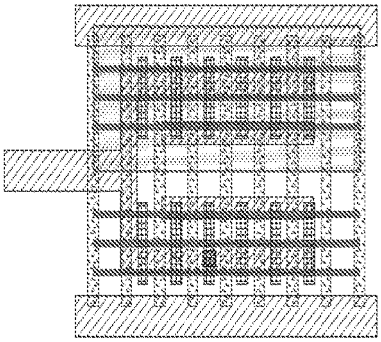
FIG. 1619A
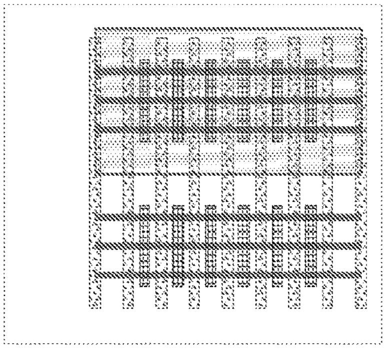
FIG. 1619B
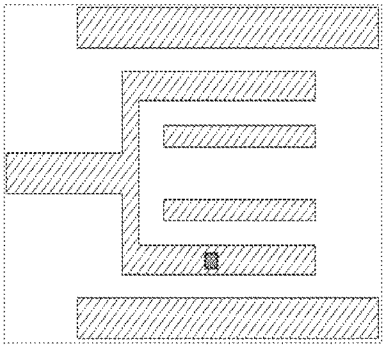
FIG. 1619C

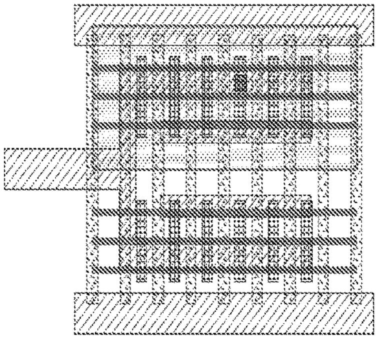
FIG. 1620A
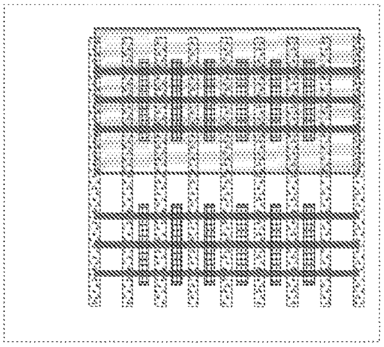
FIG. 1620B
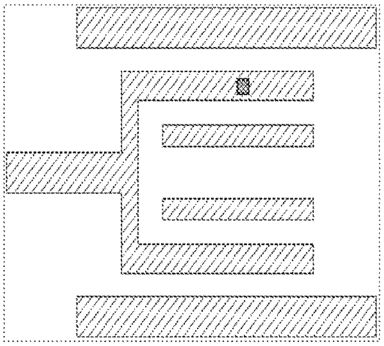
FIG. 1620C
*M* PDF Solutions, Inc.

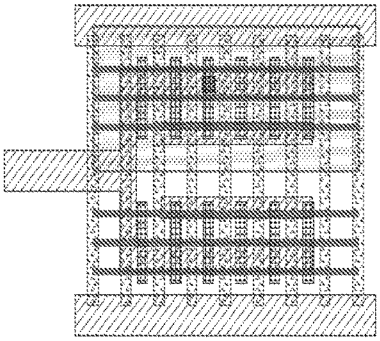
FIG. 1621A
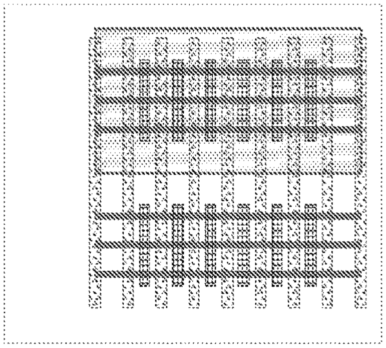
FIG. 1621B
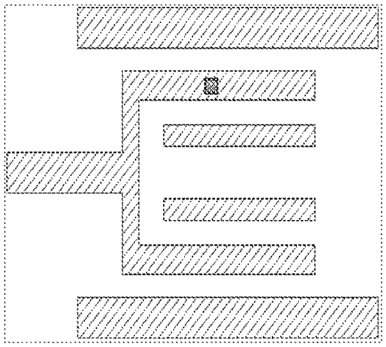
FIG. 1621C

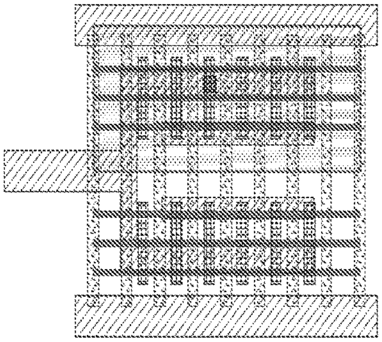
FIG. 1622A
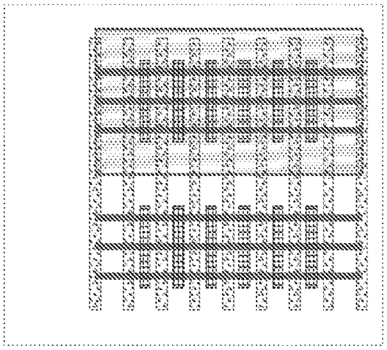
FIG. 1622B
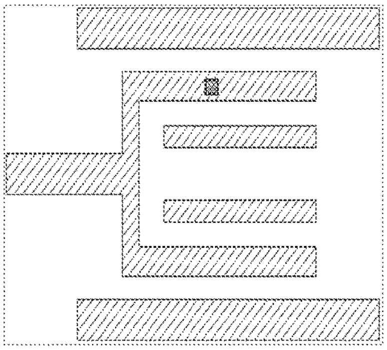
FIG. 1622C

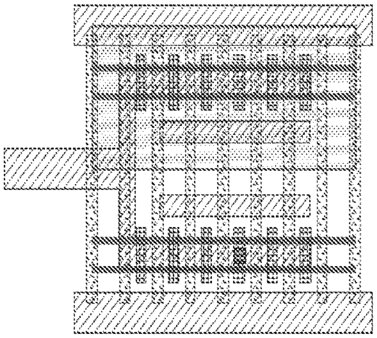
FIG. 1623A
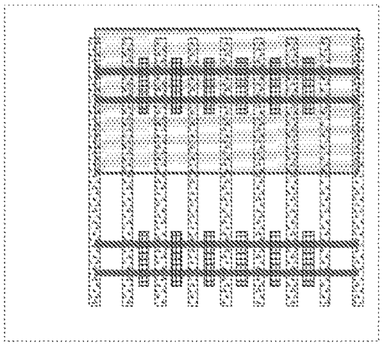
FIG. 1623B
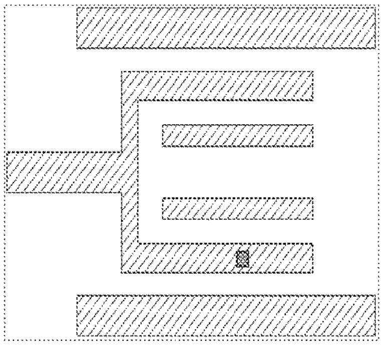
FIG. 1623C
*M* PDF Solutions, Inc.

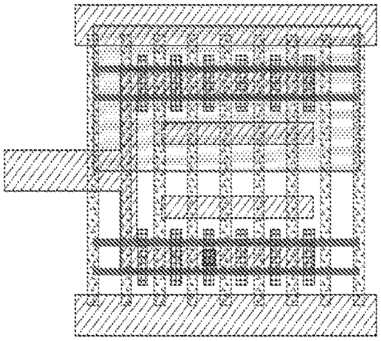
FIG. 1624A
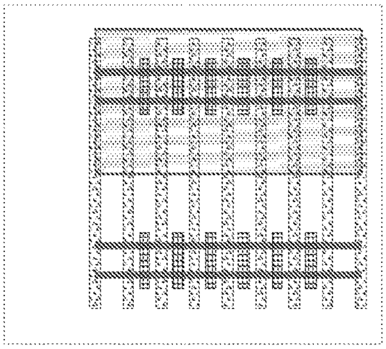
FIG. 1624B
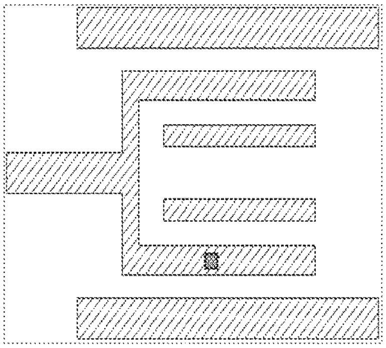
FIG. 1624C

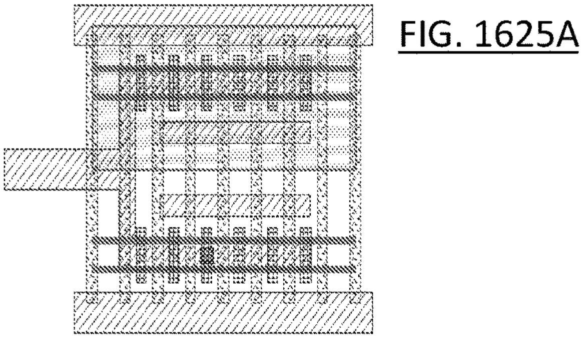
FIG. 1625A
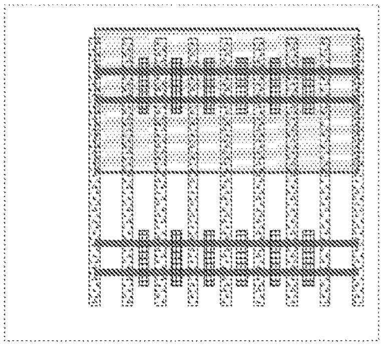
FIG. 1625B
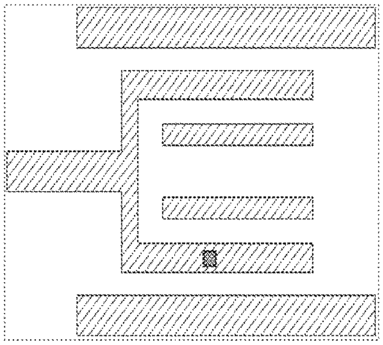
FIG. 1625C

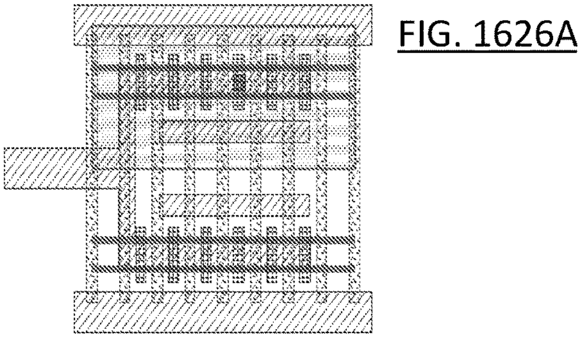
FIG. 1626A
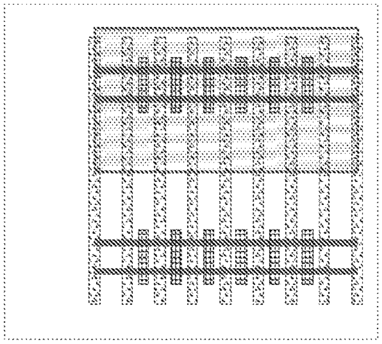
FIG. 1626B
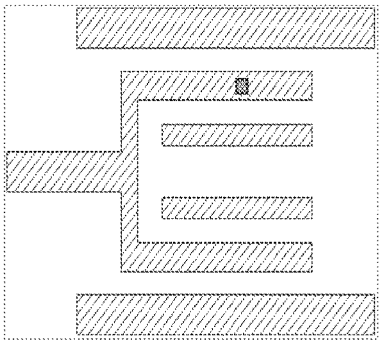
FIG. 1626C

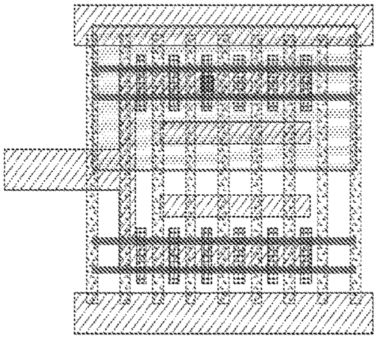
FIG. 1627A
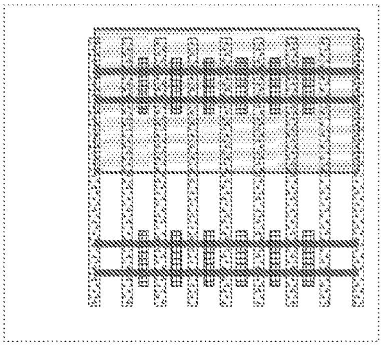
FIG. 1627B
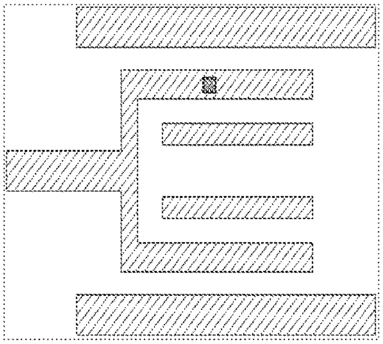
FIG. 1627C

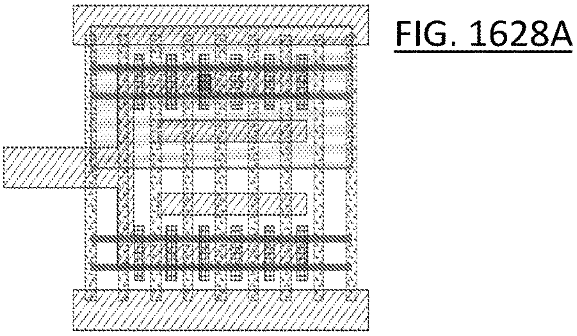
FIG. 1628A
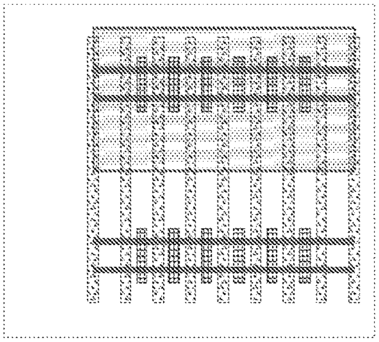
FIG. 1628B
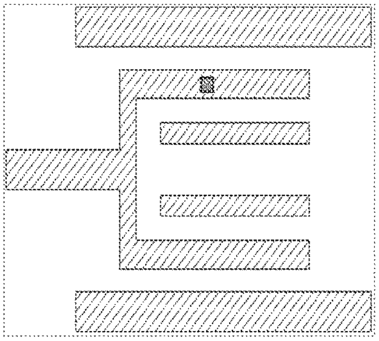
FIG. 1628C

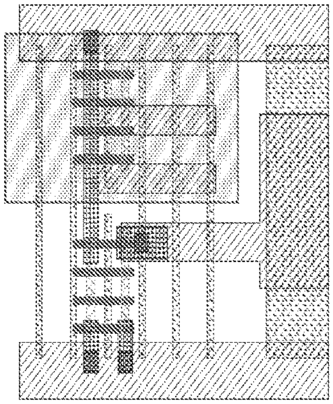
FIG. 1629A
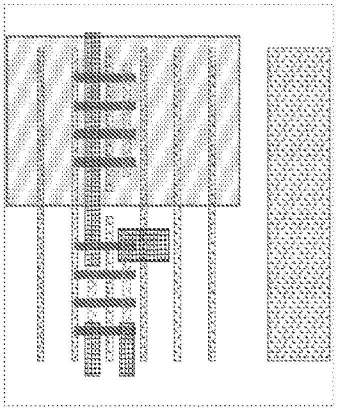
FIG. 1629B
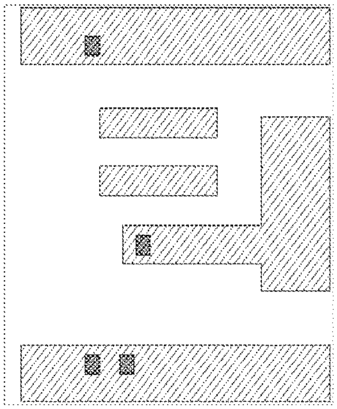
FIG. 1629C

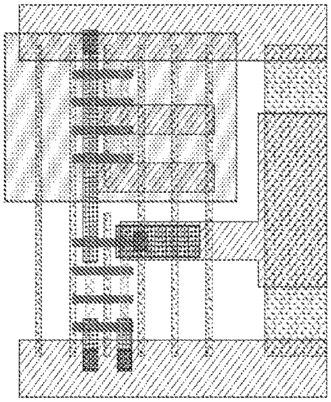
FIG. 1630A
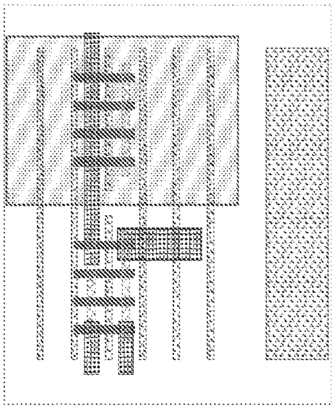
FIG. 1630B
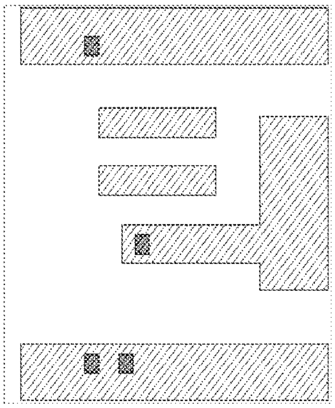
FIG. 1630C
*M* PDF Solutions, Inc.

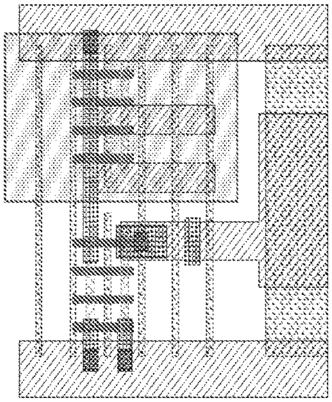
FIG. 1631A
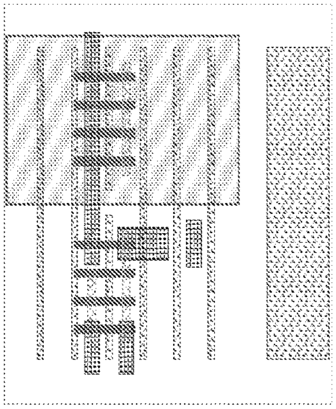
FIG. 1631B
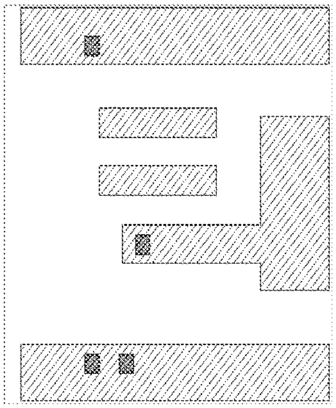
FIG. 1631C
*M* PDF Solutions, Inc.

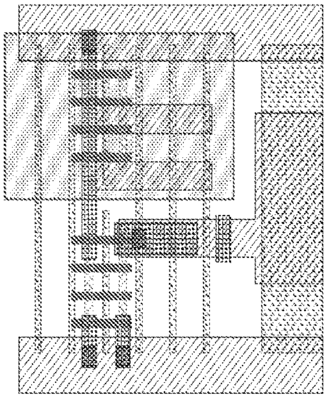
FIG. 1632A
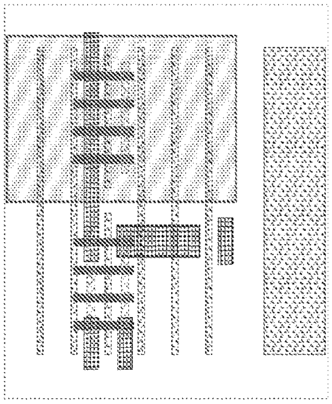
FIG. 1632B
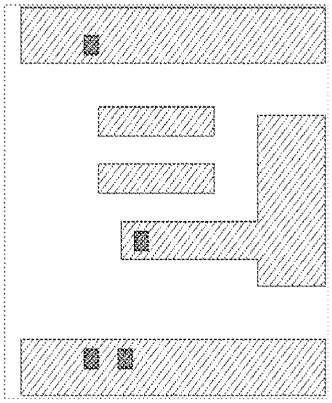
FIG. 1632C

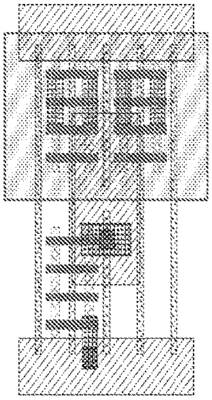
FIG. 1633A
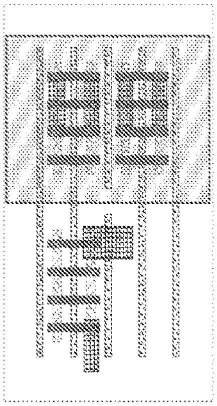
FIG. 1633B
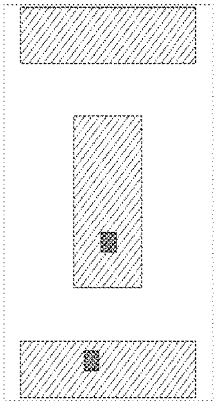
FIG. 1633C

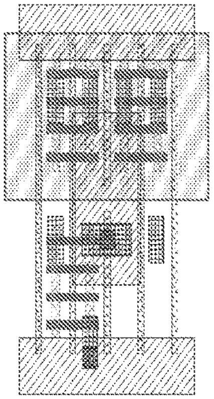
FIG. 1634A
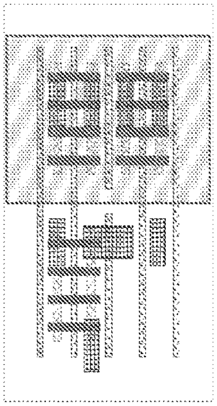
FIG. 1634B
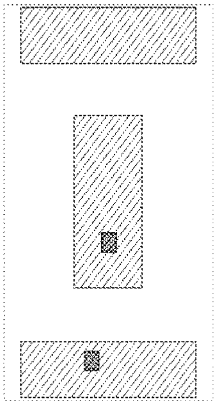
FIG. 1634C

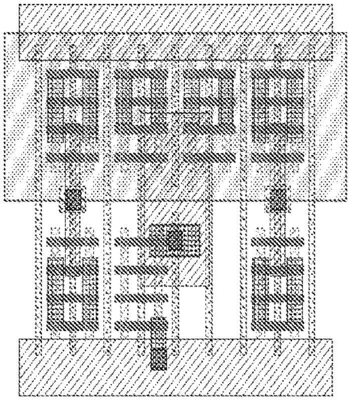
FIG. 1635A
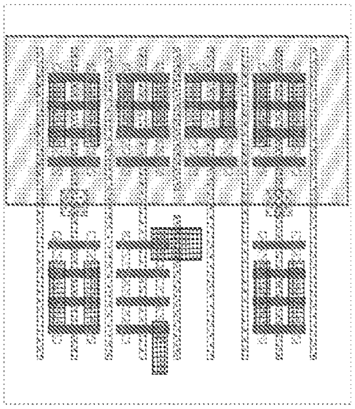
FIG. 1635B
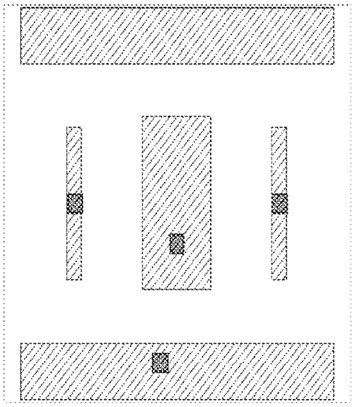
FIG. 1635C

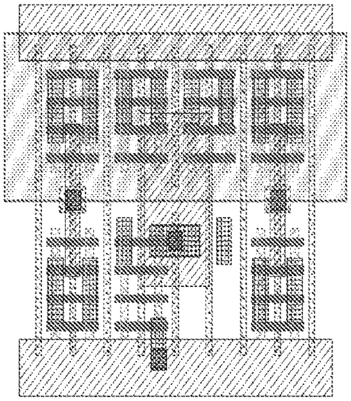
FIG. 1636A
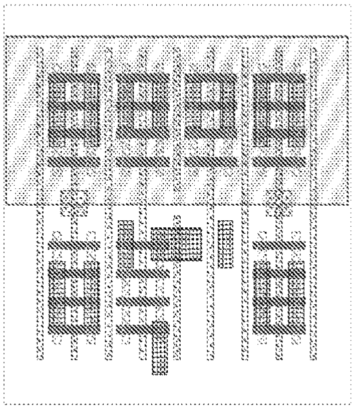
FIG. 1636B
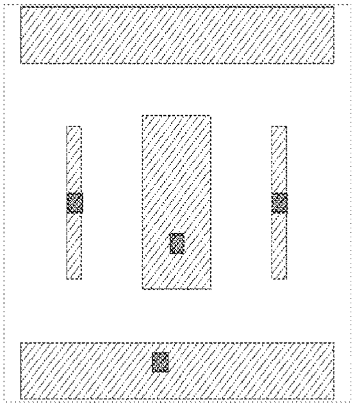
FIG. 1636C

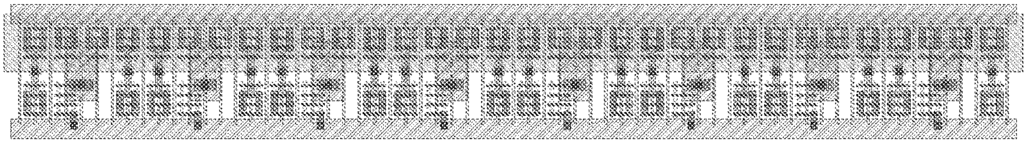
FIG. 1637A
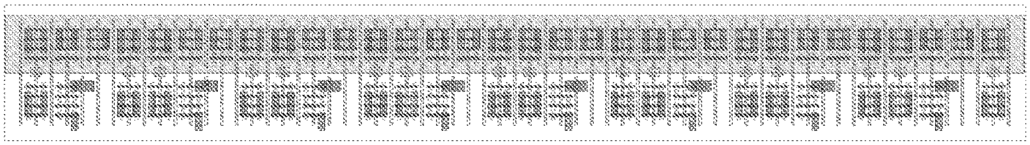
FIG. 1637B
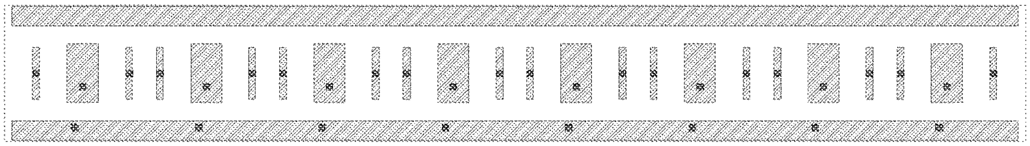
FIG. 1637C

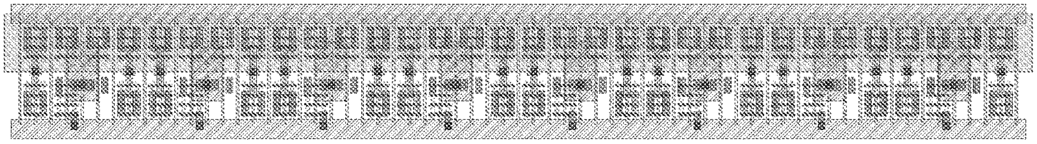
FIG. 1638A
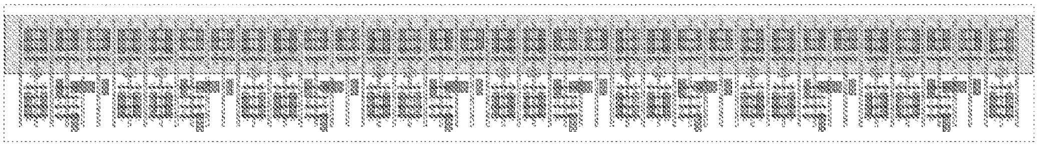
FIG. 1638B
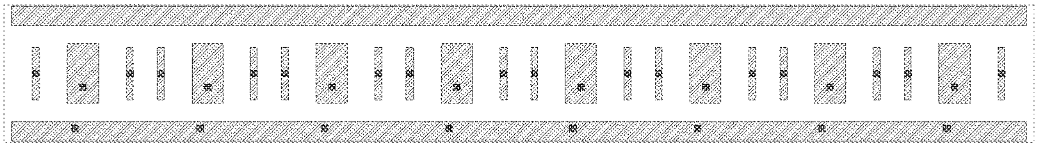
FIG. 1638C

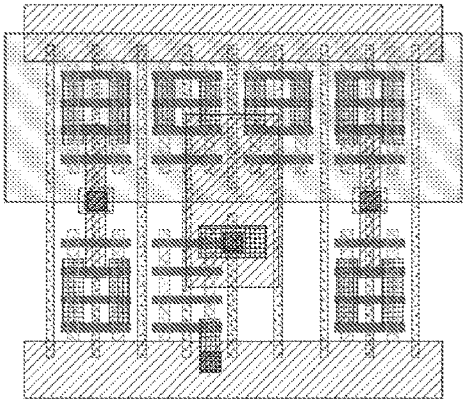
FIG. 1639A
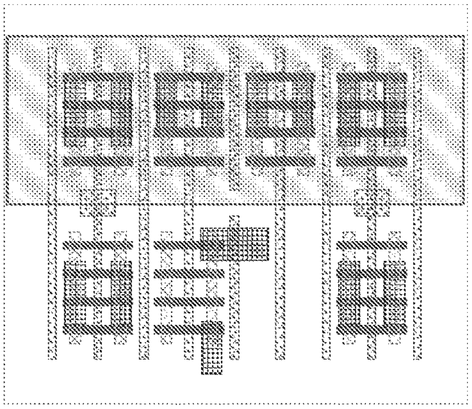
FIG. 1639B
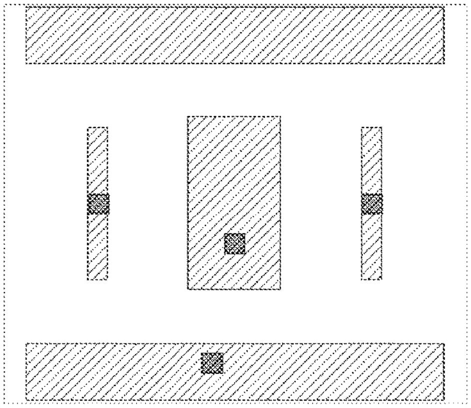
FIG. 1639C

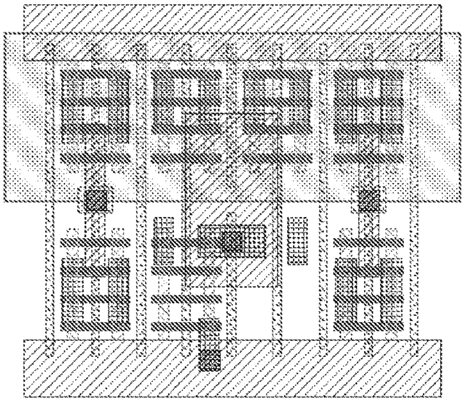
FIG. 1640A
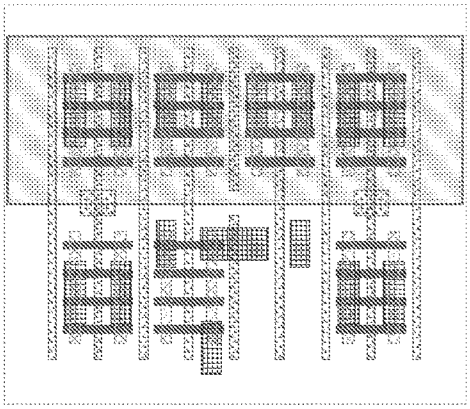
FIG. 1640B
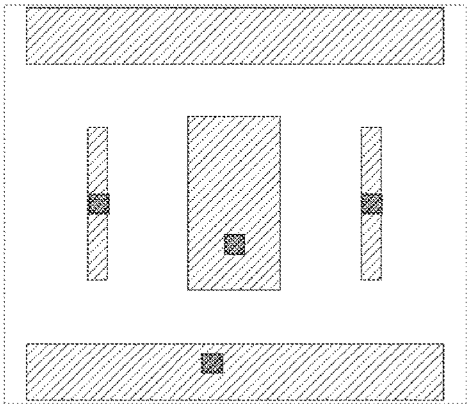
FIG. 1640C
*M* PDF Solutions, Inc.

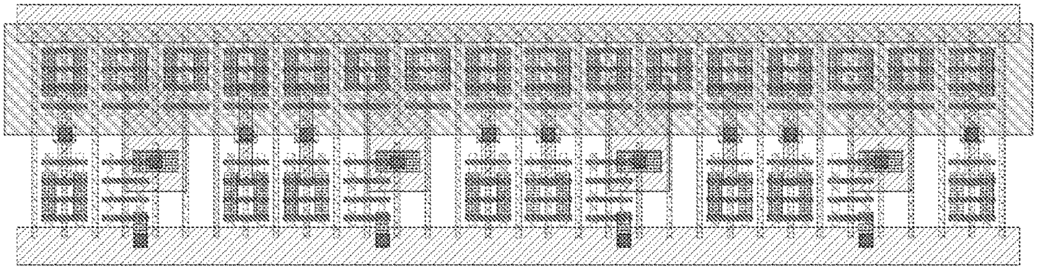
FIG. 1641A
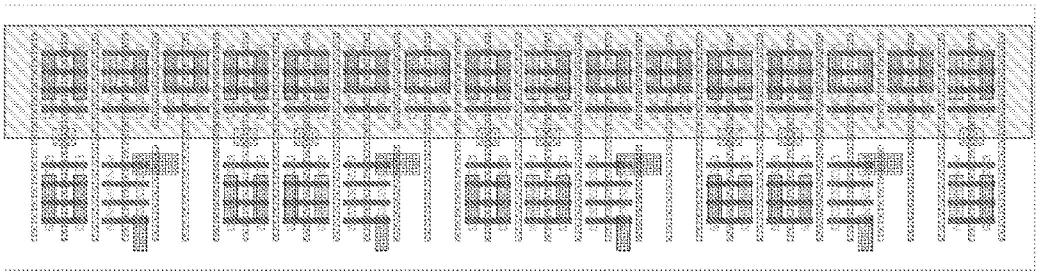
FIG. 1641B
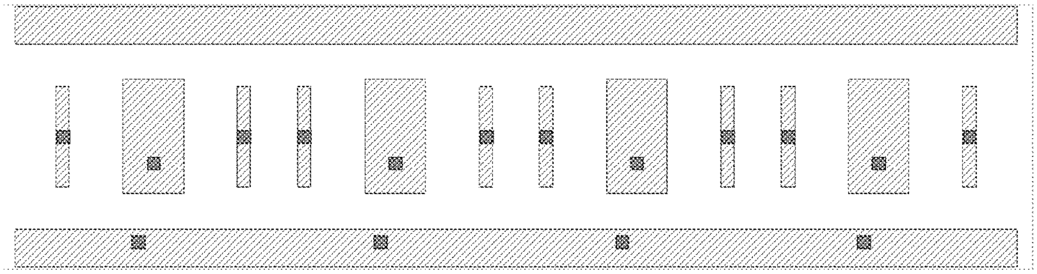
FIG. 1641C

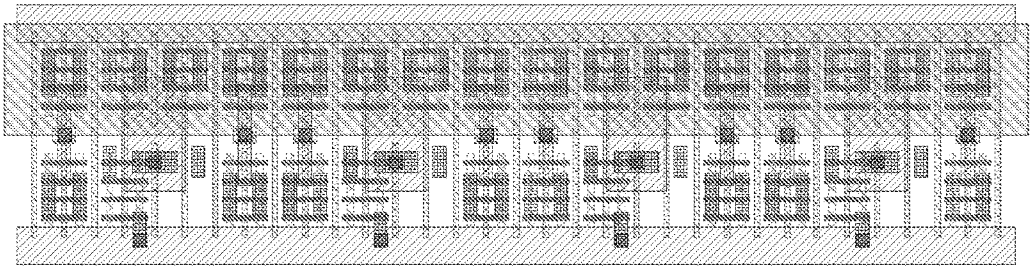
FIG. 1642A
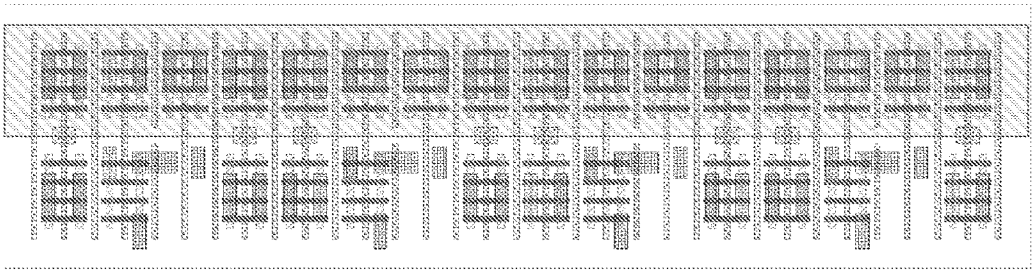
FIG. 1642B
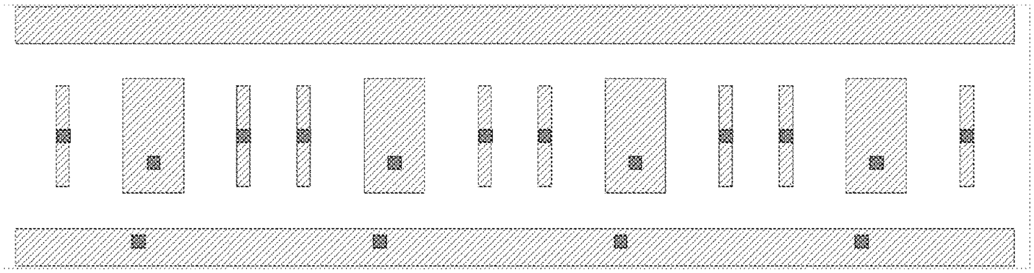
FIG. 1642C

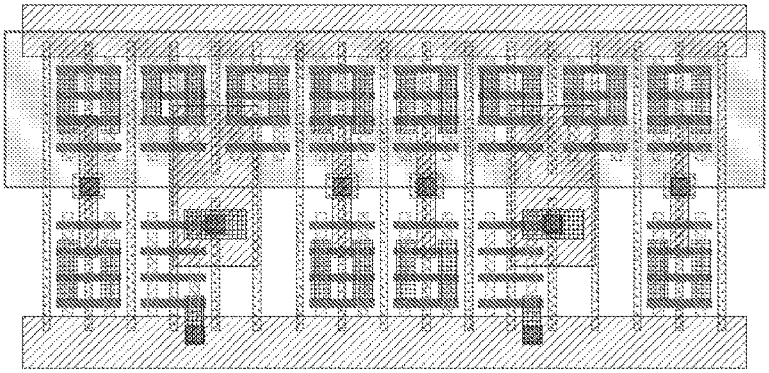
FIG. 1643A
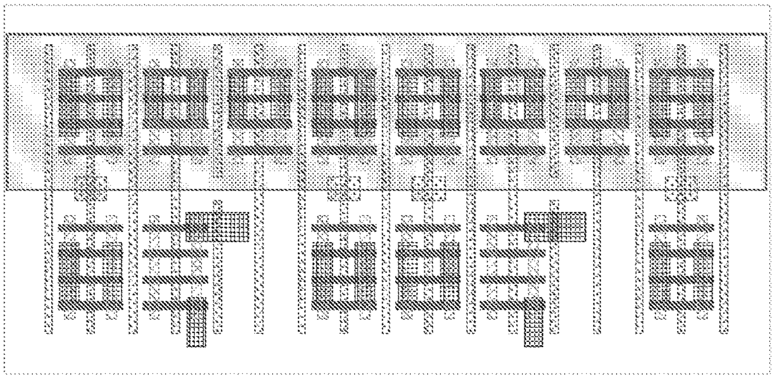
FIG. 1643B
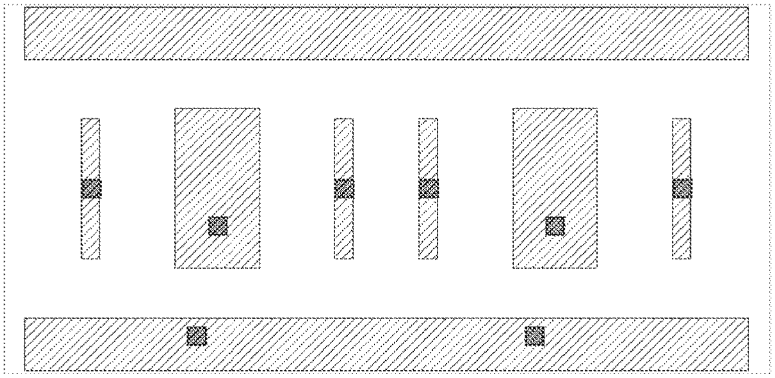
FIG. 1643C
*M* PDF Solutions, Inc.

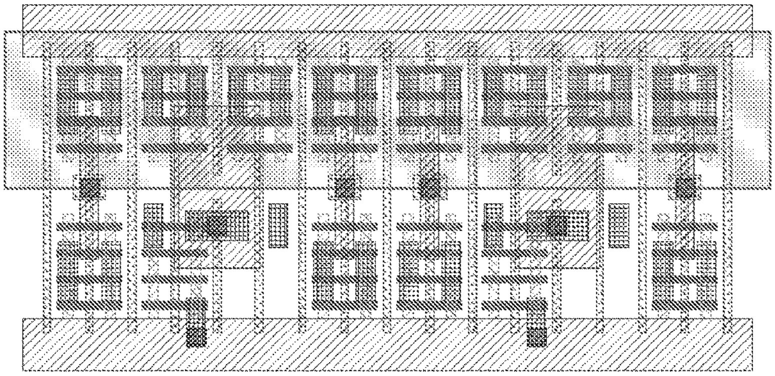
FIG. 1644A
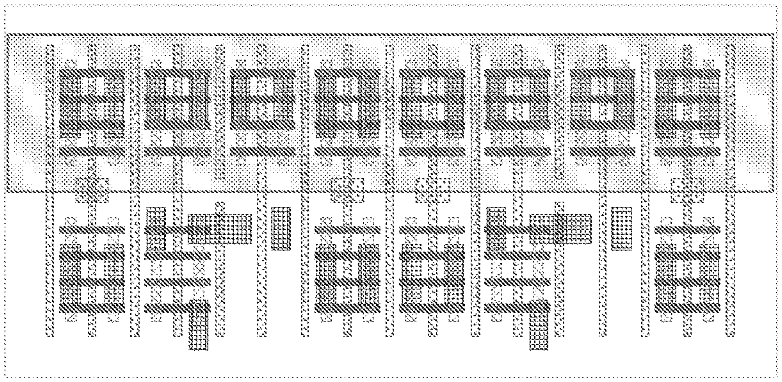
FIG. 1644B
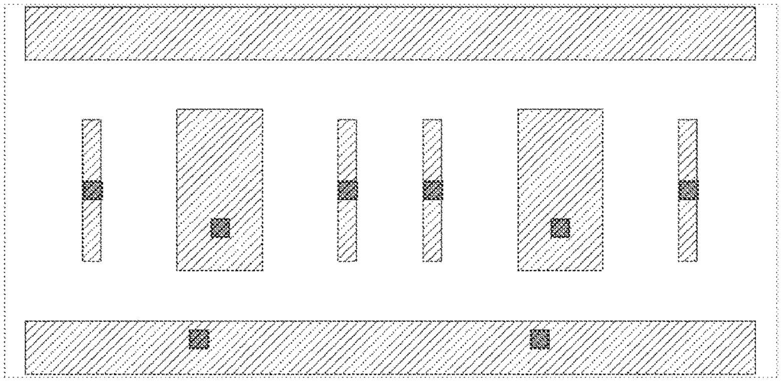
FIG. 1644C

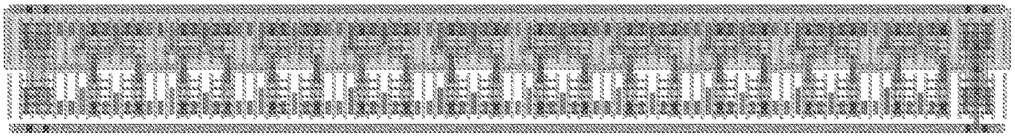
FIG. 1645A
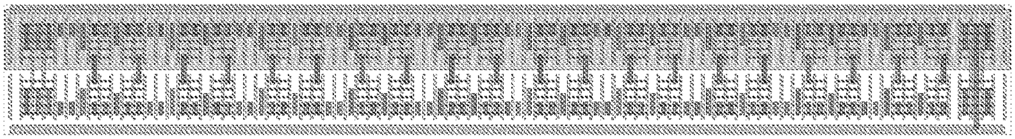
FIG. 1645B
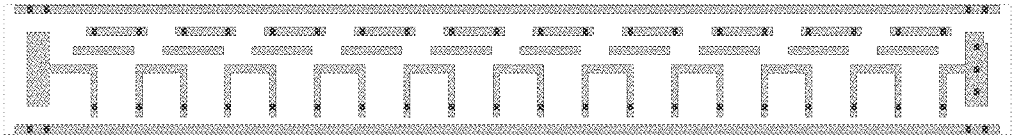
FIG. 1645C

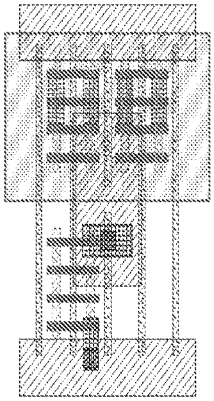
FIG. 1646A
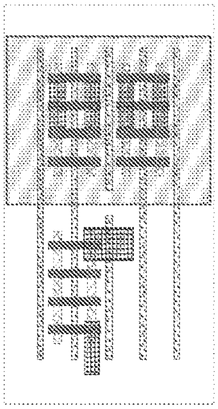
FIG. 1646B
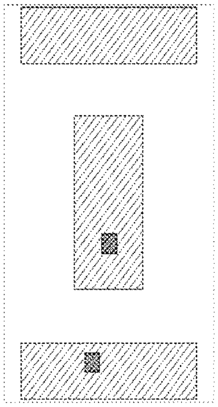
FIG. 1646C

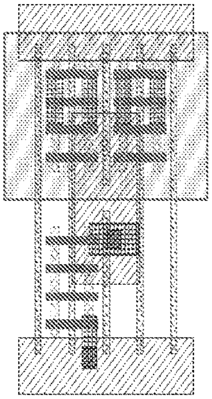
FIG. 1647A
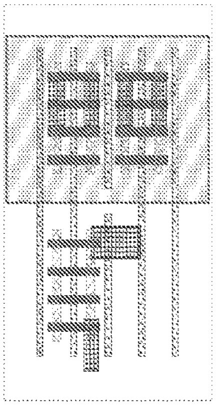
FIG. 1647B
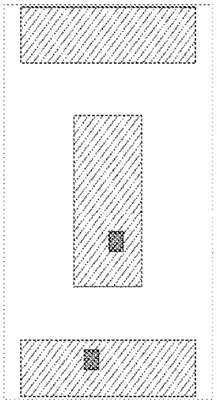
FIG. 1647C

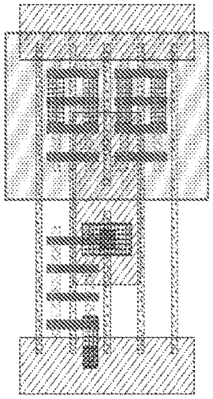
FIG. 1648A
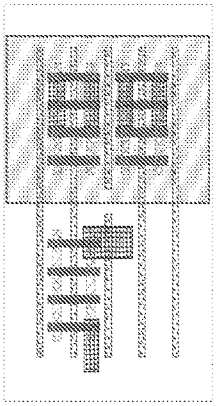
FIG. 1648B
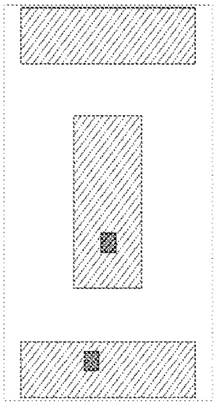
FIG. 1648C

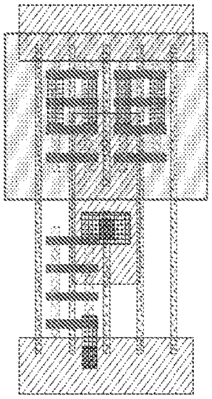
FIG. 1649A
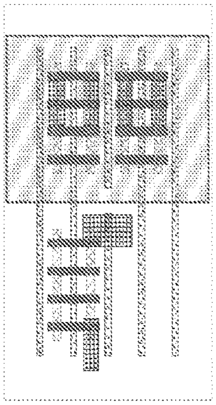
FIG. 1649B
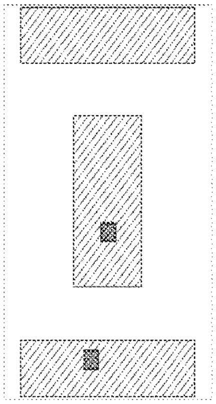
FIG. 1649C

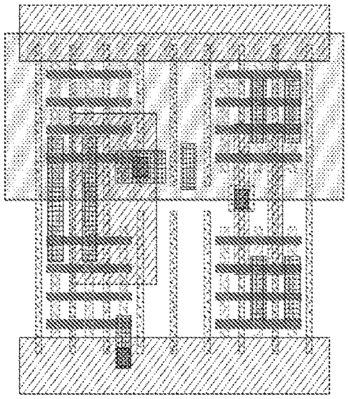
FIG. 1650A
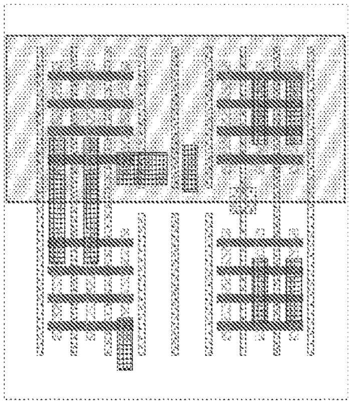
FIG. 1650B
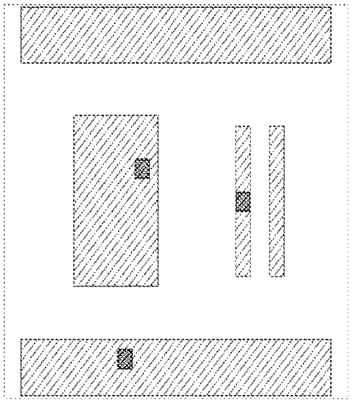
FIG. 1650C
*M* PDF Solutions, Inc.

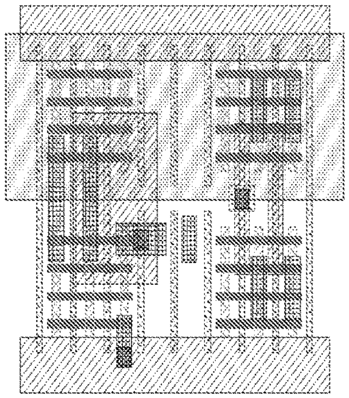
FIG. 1651A
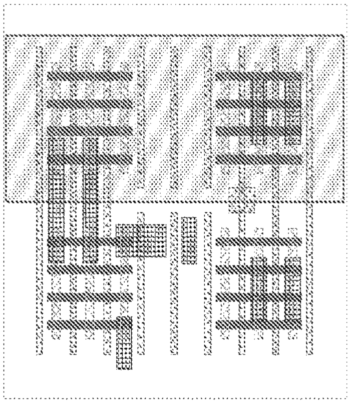
FIG. 1651B
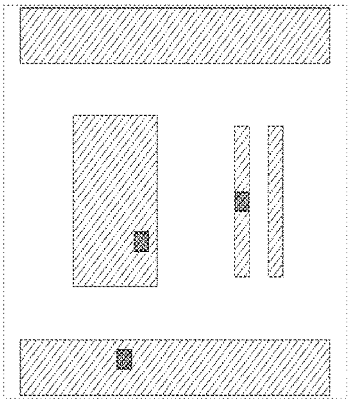
FIG. 1651C
*M* PDF Solutions, Inc.

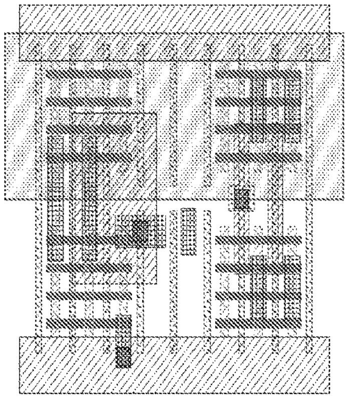
FIG. 1652A
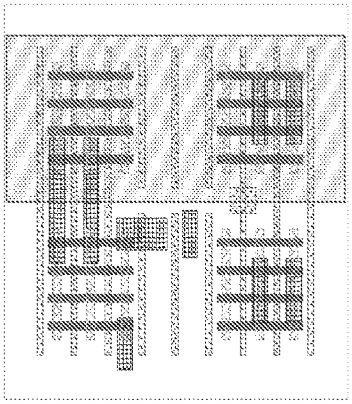
FIG. 1652B
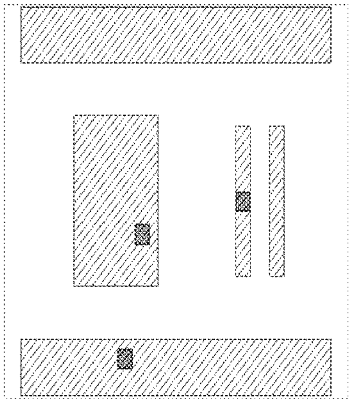
FIG. 1652C

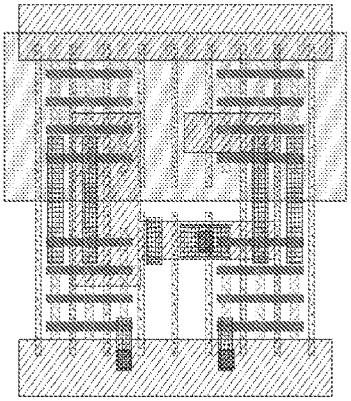
FIG. 1653A
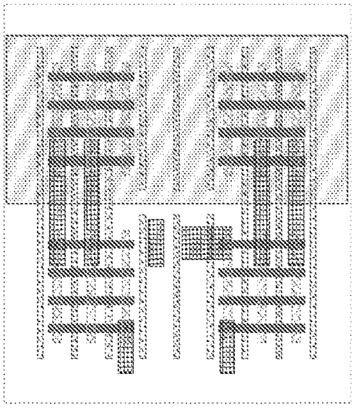
FIG. 1653B
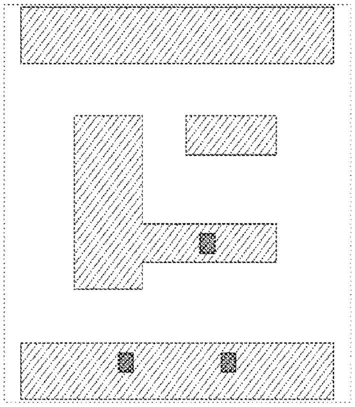
FIG. 1653C

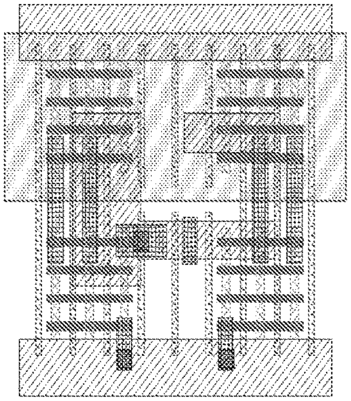
FIG. 1654A
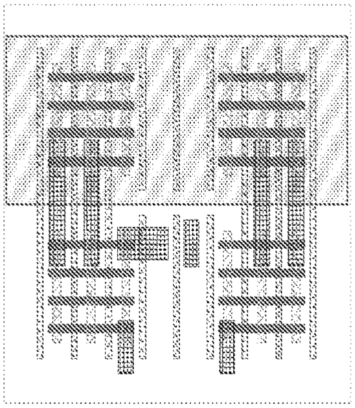
FIG. 1654B
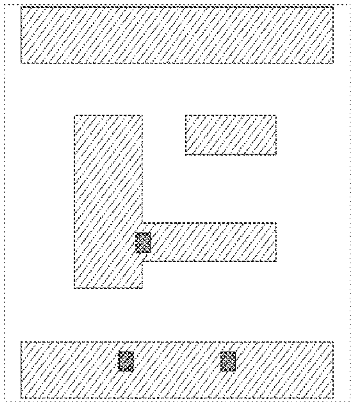
FIG. 1654C

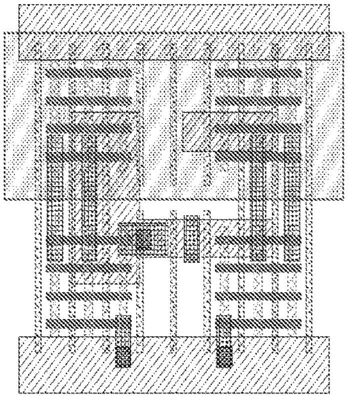
FIG. 1655A
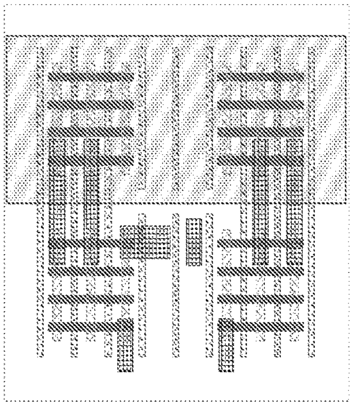
FIG. 1655B
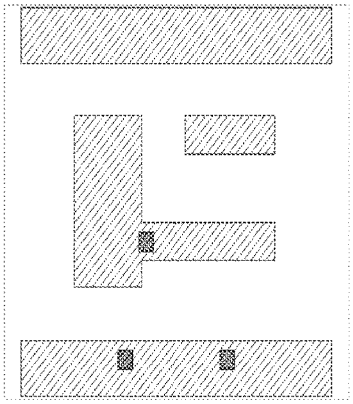
FIG. 1655C

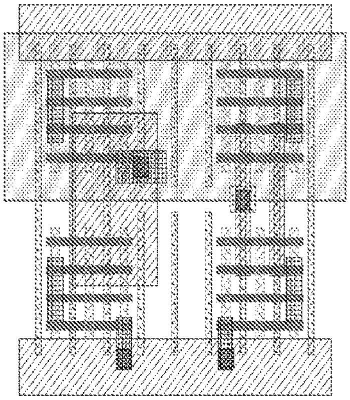
FIG. 1656A
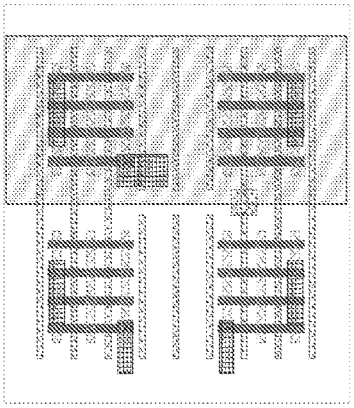
FIG. 1656B
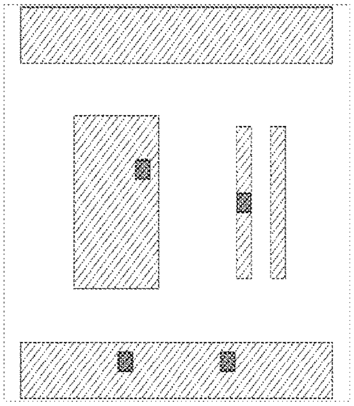
FIG. 1656C

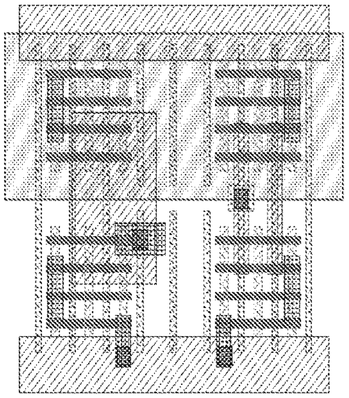
FIG. 1657A
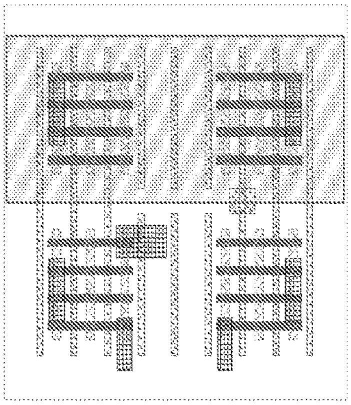
FIG. 1657B
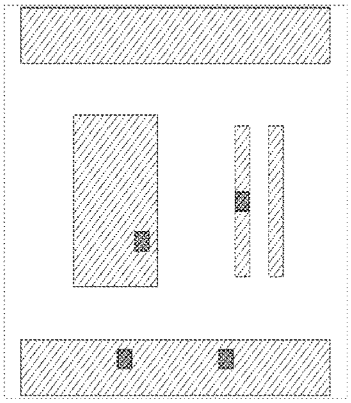
FIG. 1657C

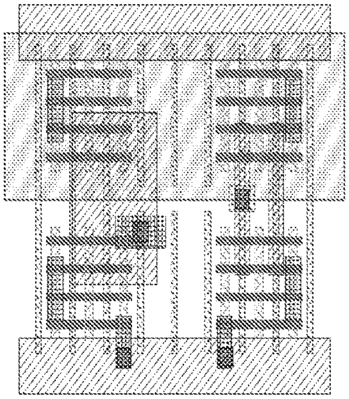
FIG. 1658A
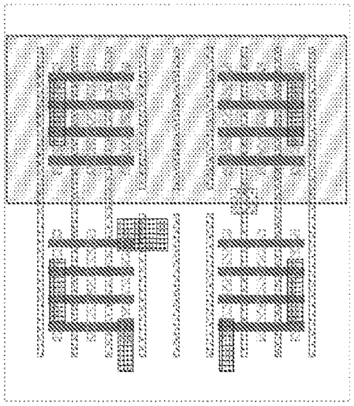
FIG. 1658B
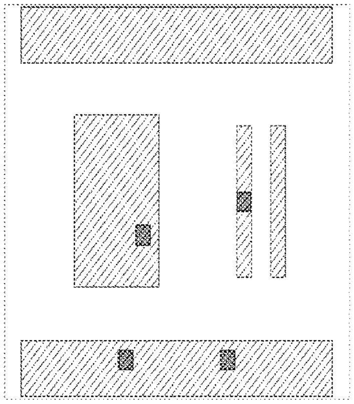
FIG. 1658C

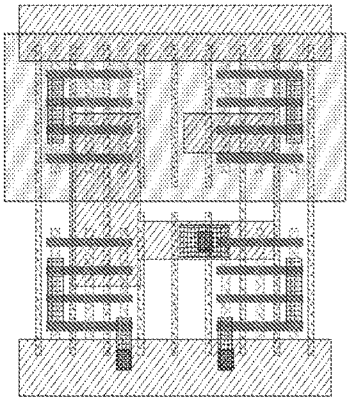
FIG. 1659A
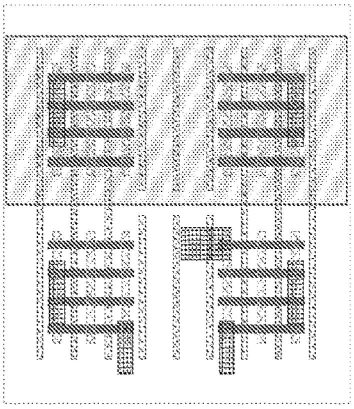
FIG. 1659B
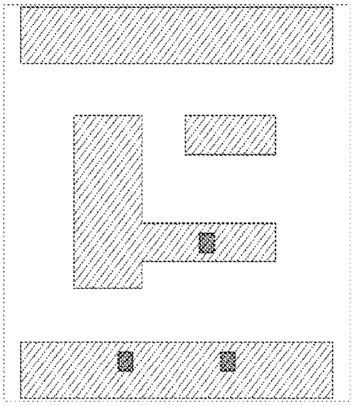
FIG. 1659C

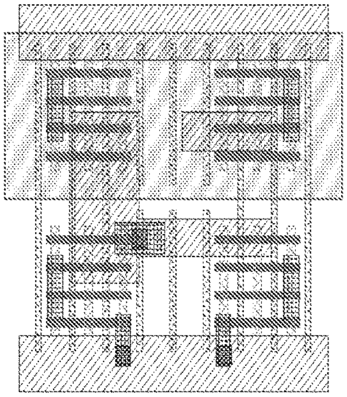
FIG. 1660A
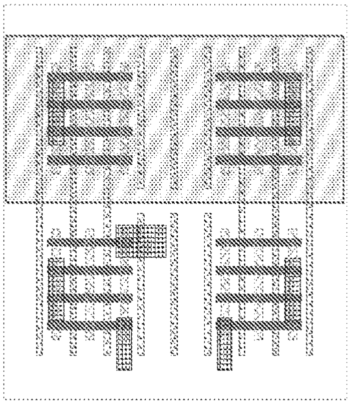
FIG. 1660B
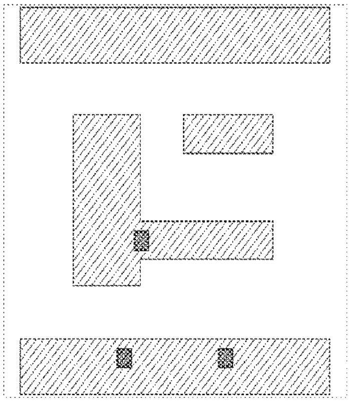
FIG. 1660C

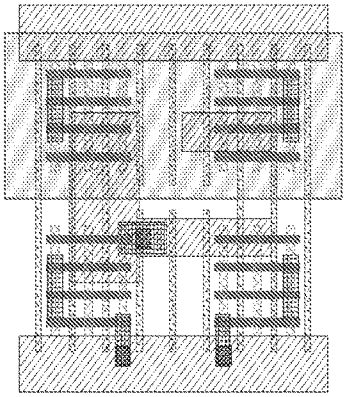
FIG. 1661A
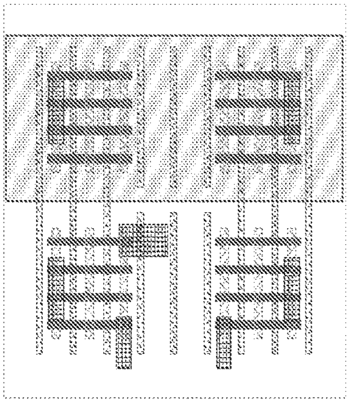
FIG. 1661B
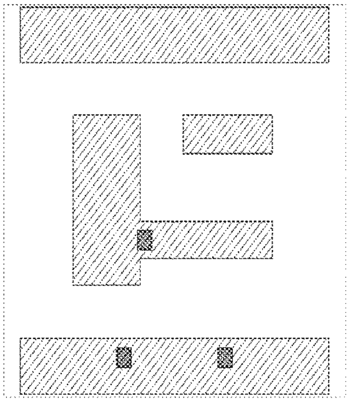
FIG. 1661C

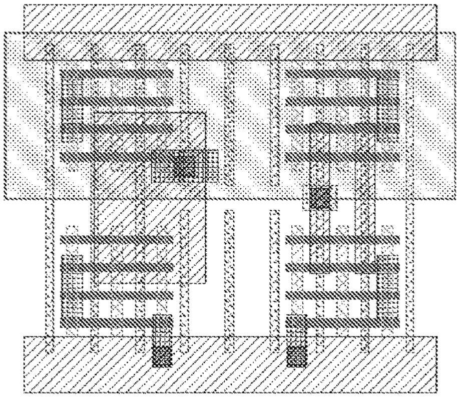
FIG. 1662A
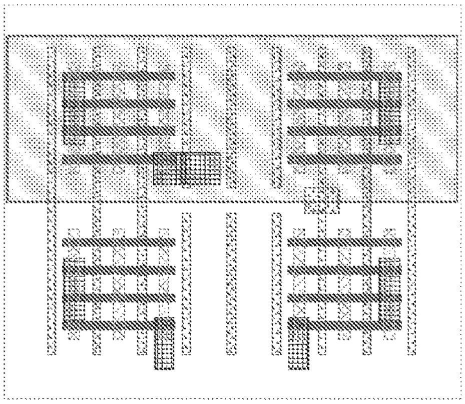
FIG. 1662B
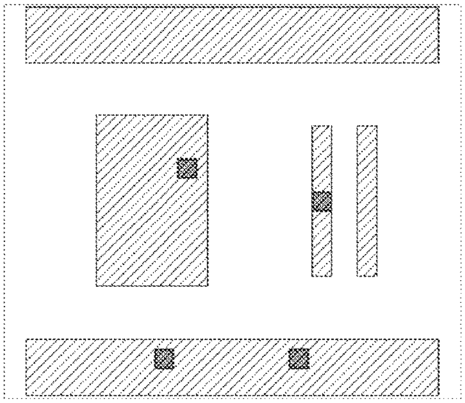
FIG. 1662C

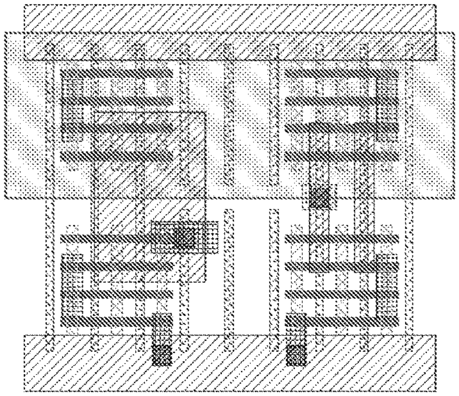
FIG. 1663A
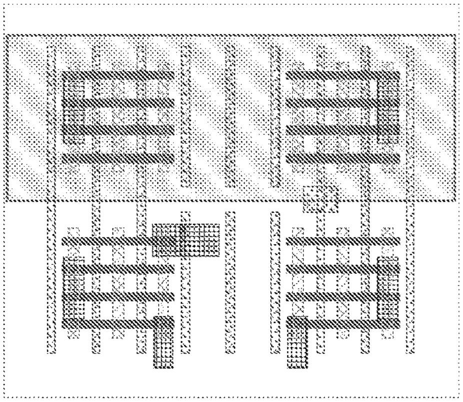
FIG. 1663B
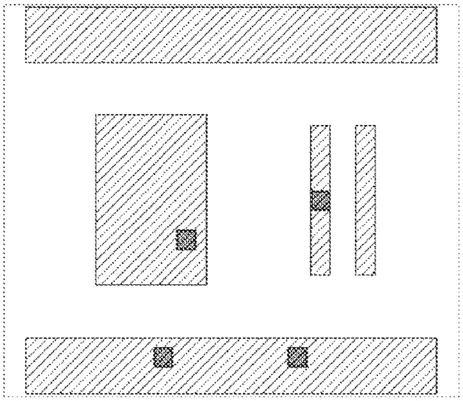
FIG. 1663C
*M* PDF Solutions, Inc.

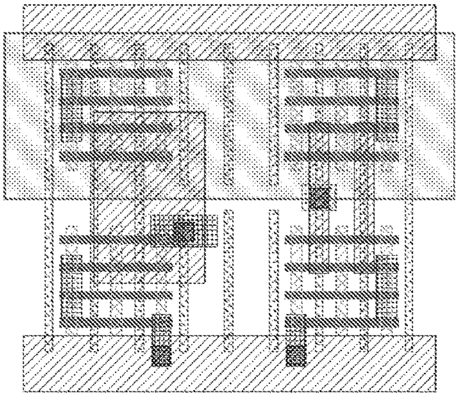
FIG. 1664A
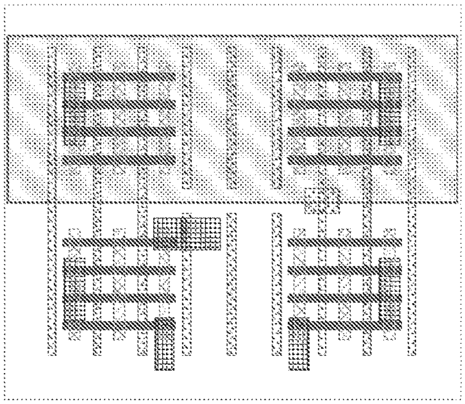
FIG. 1664B
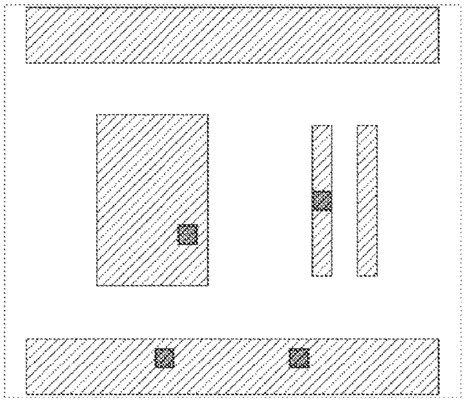
FIG. 1664C

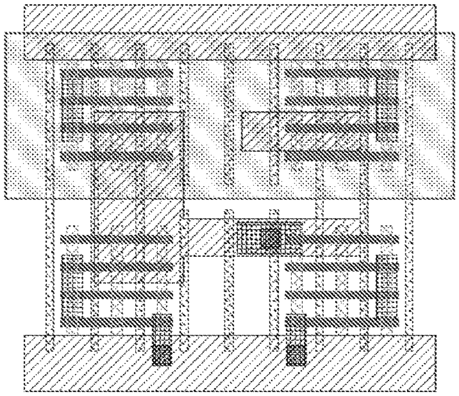
FIG. 1665A
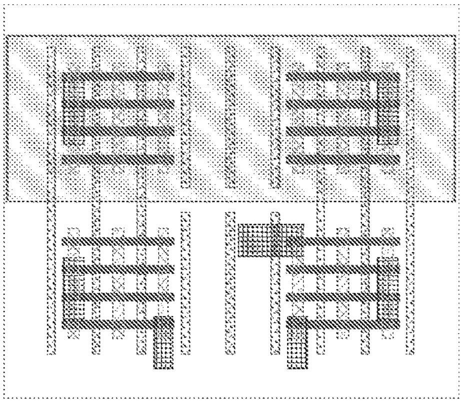
FIG. 1665B
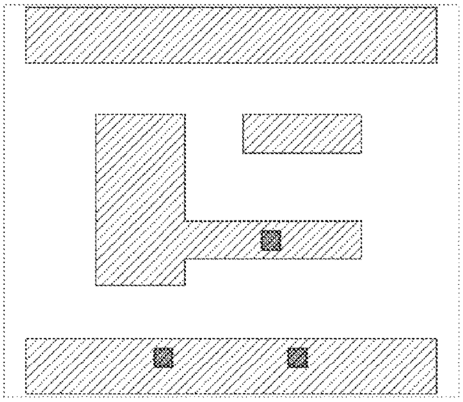
FIG. 1665C

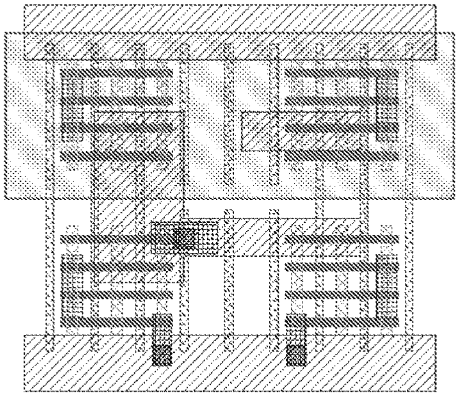
FIG. 1666A
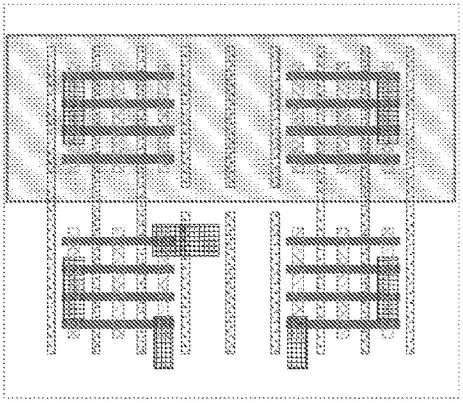
FIG. 1666B
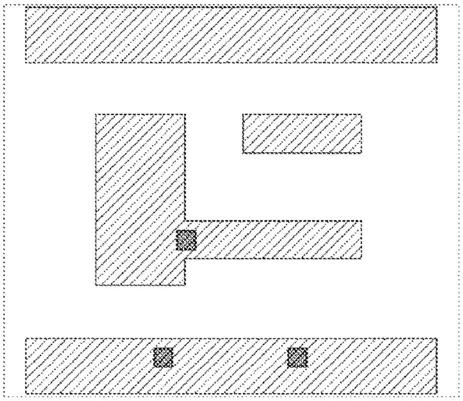
FIG. 1666C

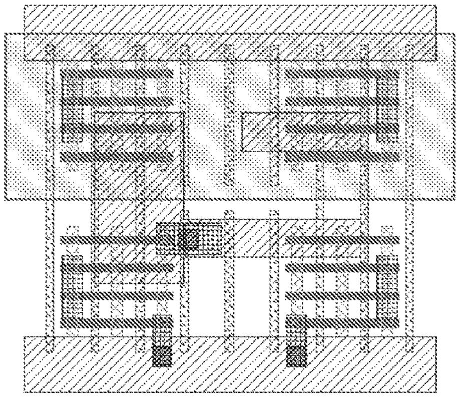
FIG. 1667A
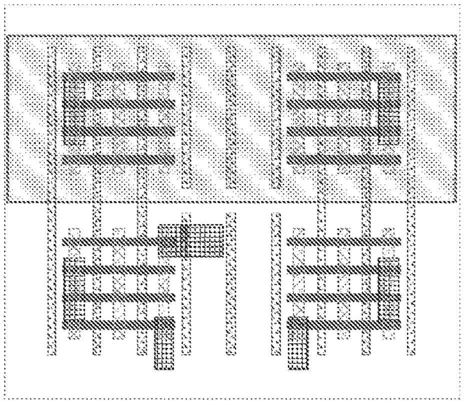
FIG. 1667B
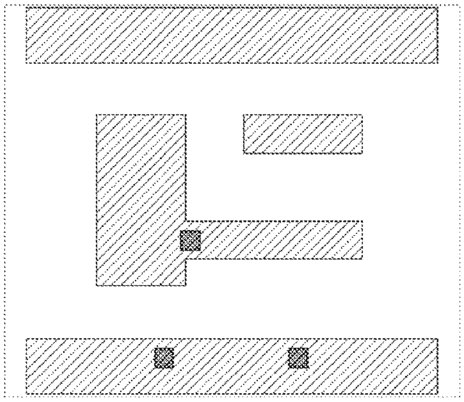
FIG. 1667C

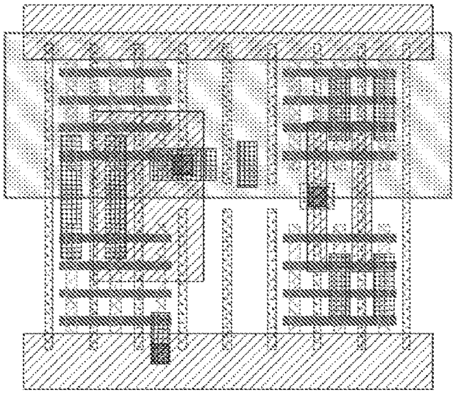
FIG. 1668A
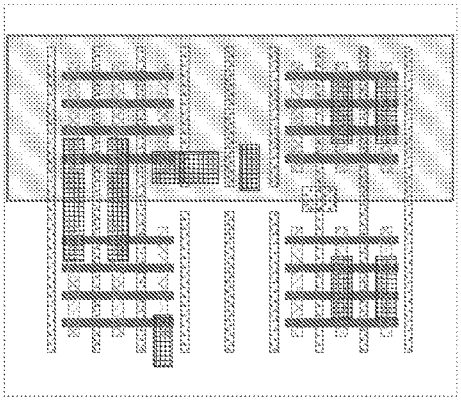
FIG. 1668B
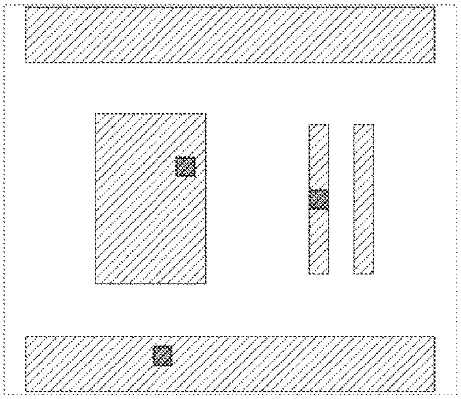
FIG. 1668C

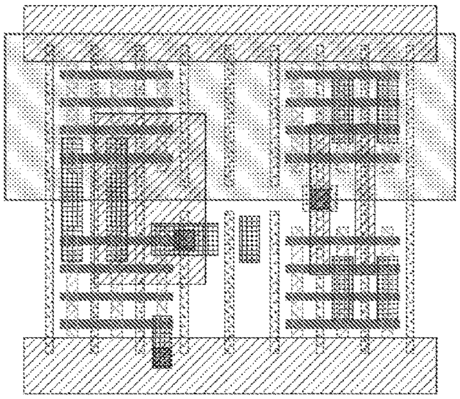
FIG. 1669A
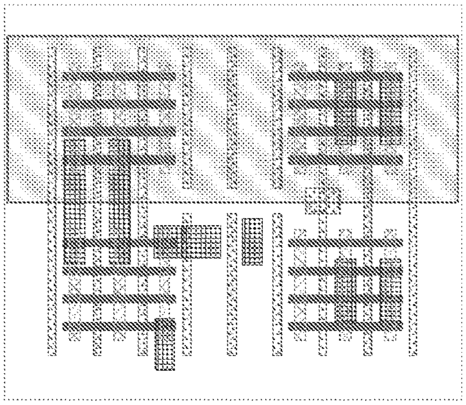
FIG. 1669B
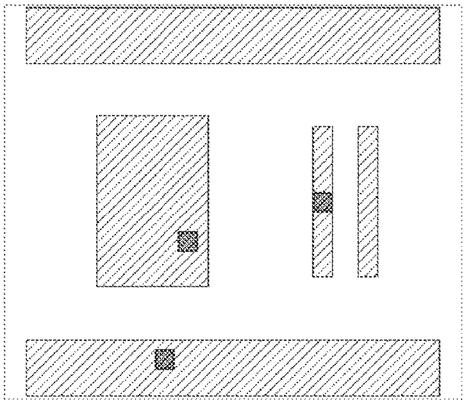
FIG. 1669C

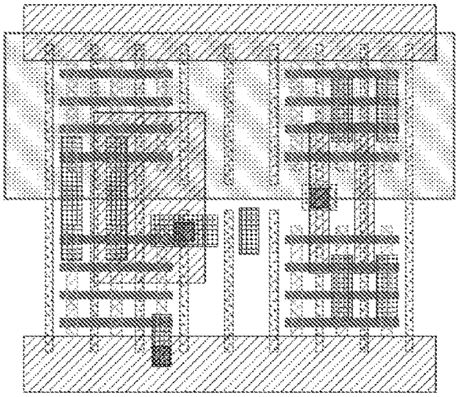
FIG. 1670A
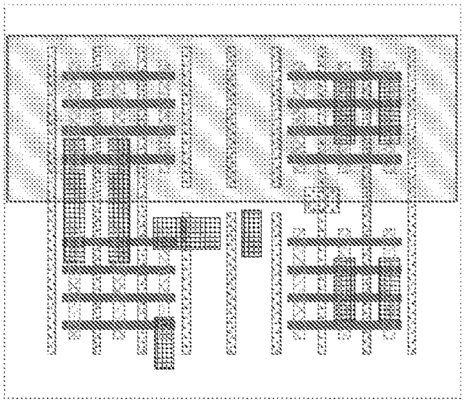
FIG. 1670B
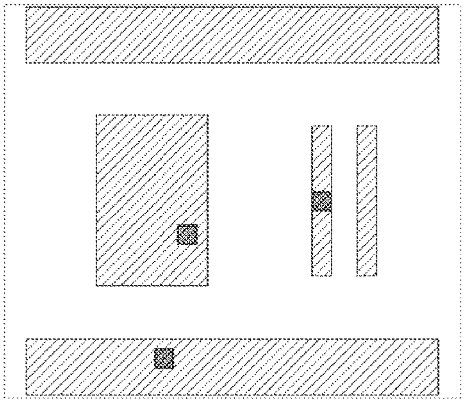
FIG. 1670C

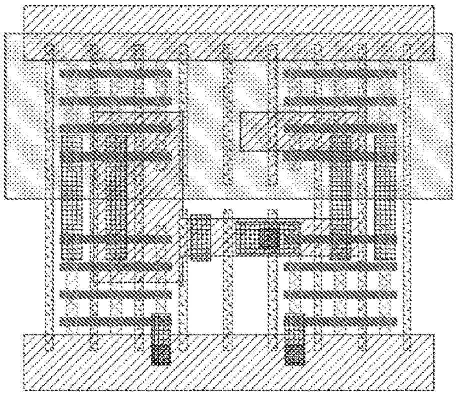
FIG. 1671A
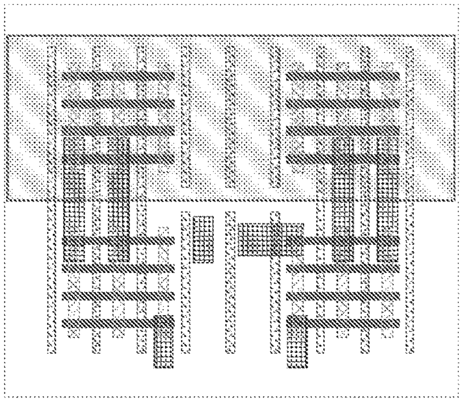
FIG. 1671B
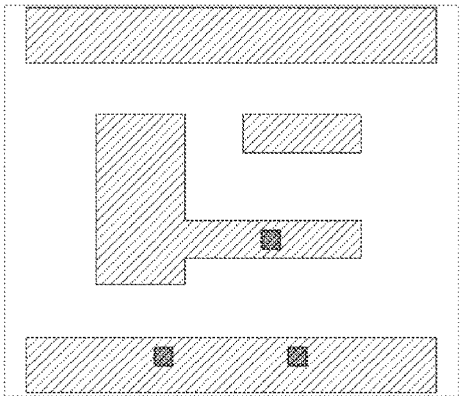
FIG. 1671C

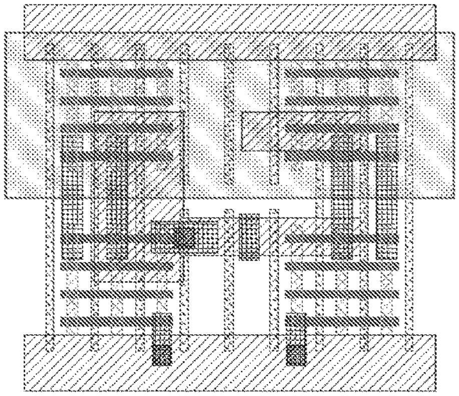
FIG. 1672A
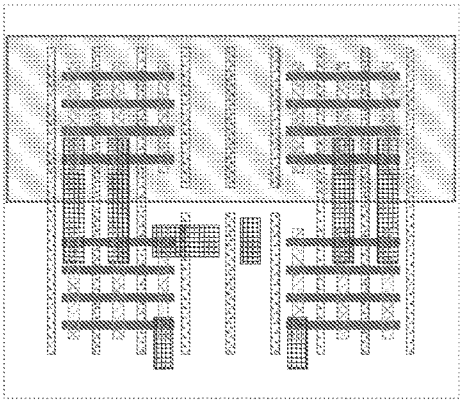
FIG. 1672B
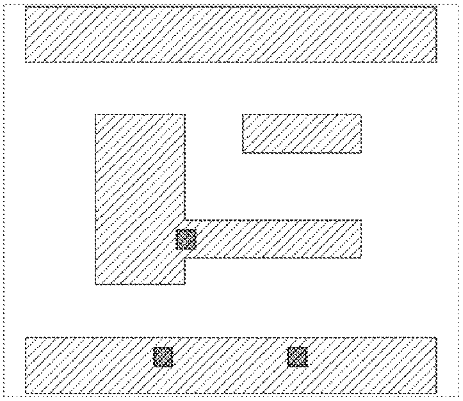
FIG. 1672C

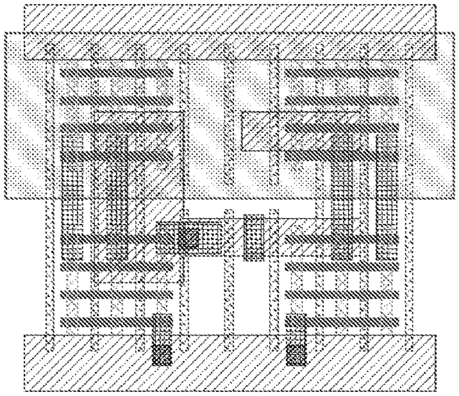
FIG. 1673A
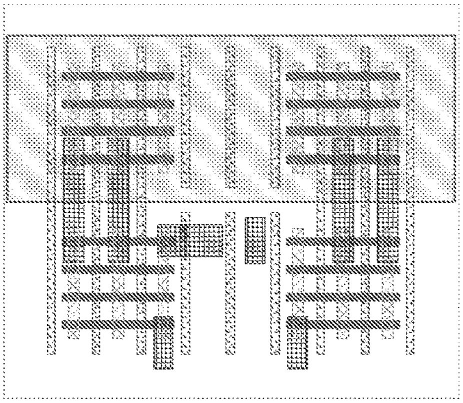
FIG. 1673B
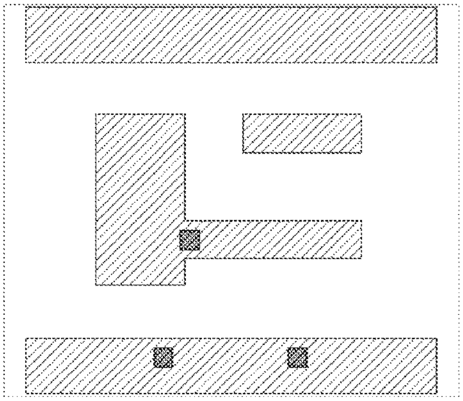
FIG. 1673C

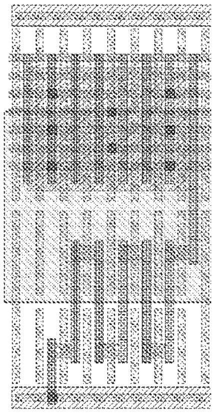
FIG. 1674A
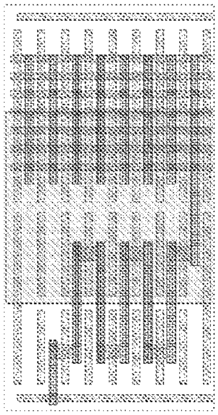
FIG. 1674B
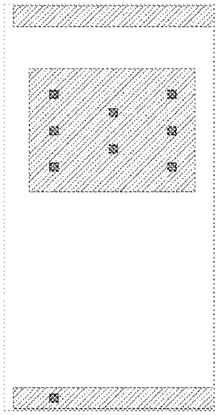
FIG. 1674C
*M* PDF Solutions, Inc.

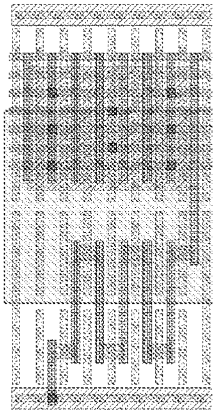
FIG. 1675A
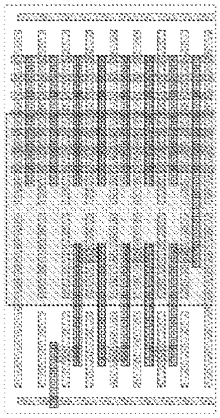
FIG. 1675B
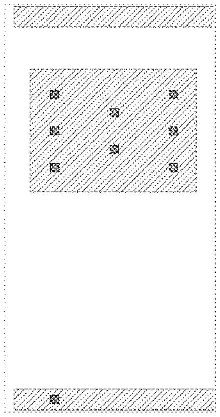
FIG. 1675C

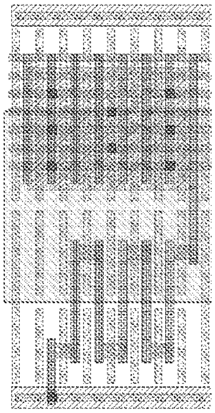
FIG. 1676A
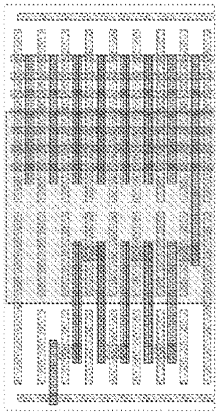
FIG. 1676B
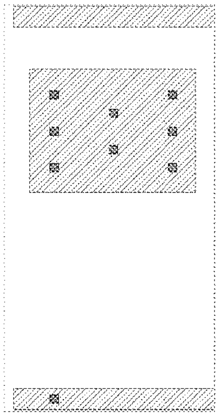
FIG. 1676C

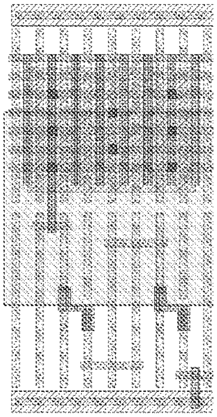
FIG. 1677A
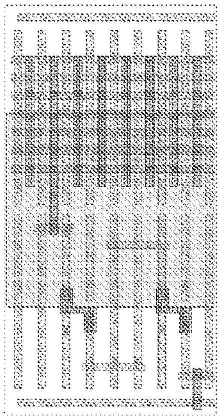
FIG. 1677B
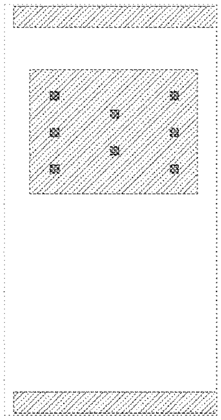
FIG. 1677C

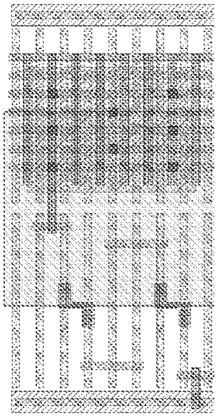
FIG. 1678A
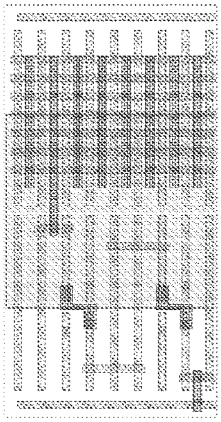
FIG. 1678B
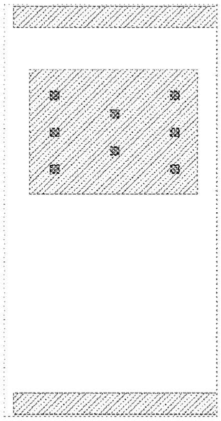
FIG. 1678C

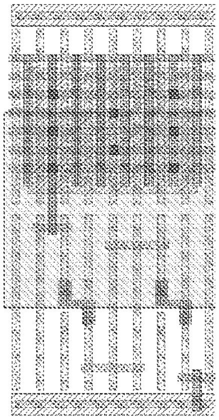
FIG. 1679A
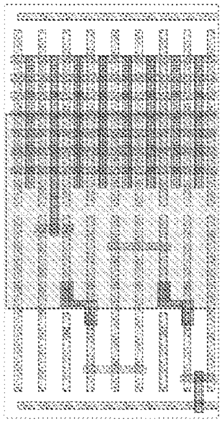
FIG. 1679B
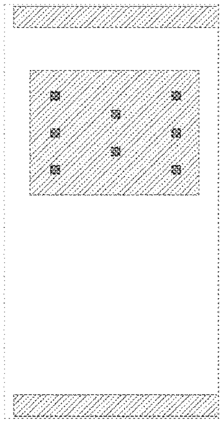
FIG. 1679C

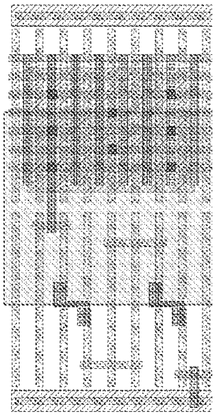
FIG. 1680A
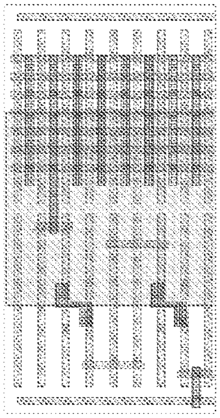
FIG. 1680B
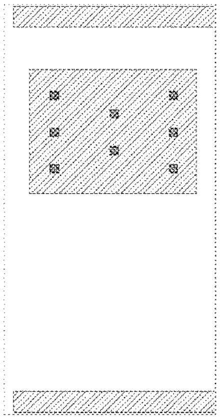
FIG. 1680C

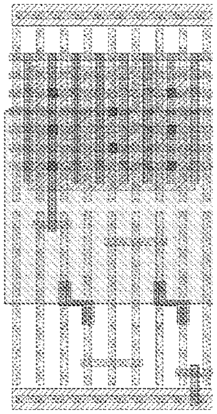
FIG. 1681A
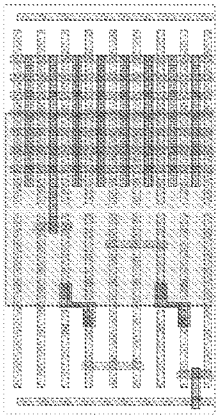
FIG. 1681B
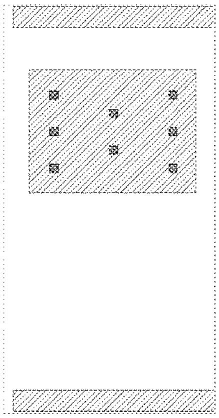
FIG. 1681C
*M* PDF Solutions, Inc.

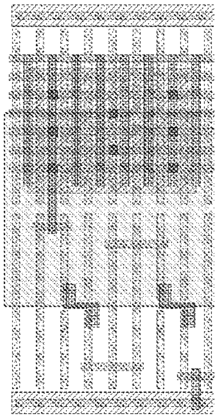
FIG. 1682A
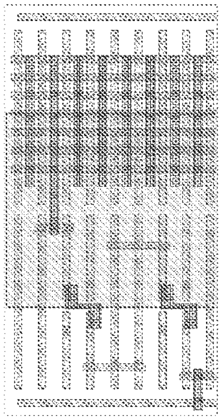
FIG. 1682B
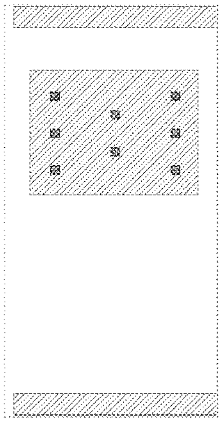
FIG. 1682C

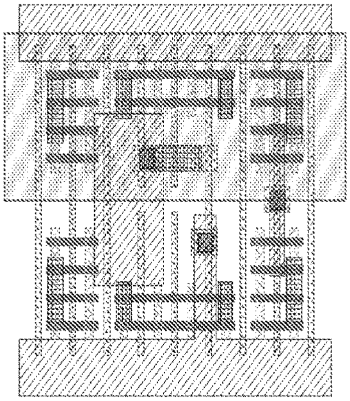
FIG. 1683A
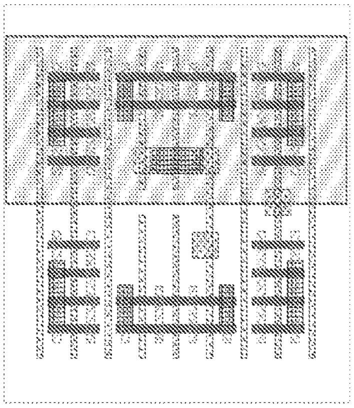
FIG. 1683B
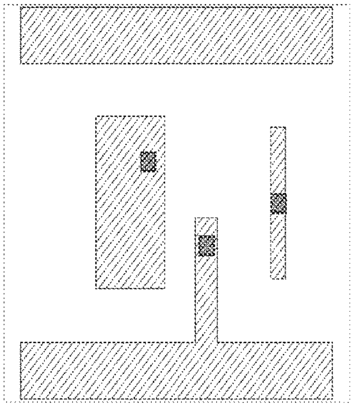
FIG. 1683C

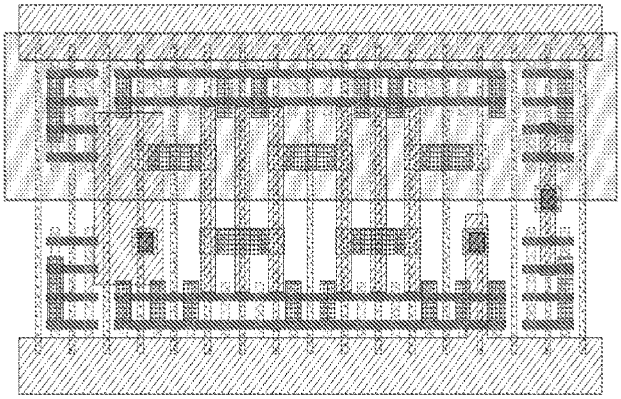
FIG. 1684A
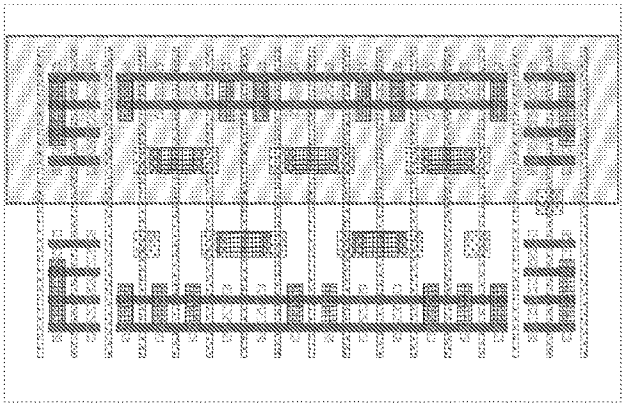
FIG. 1684B
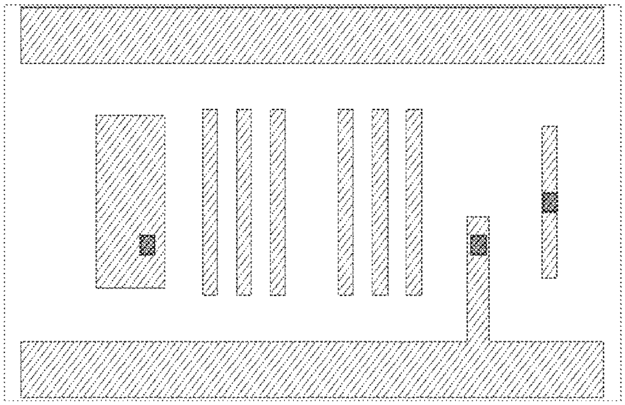
FIG. 1684C
*M* PDF Solutions, Inc.

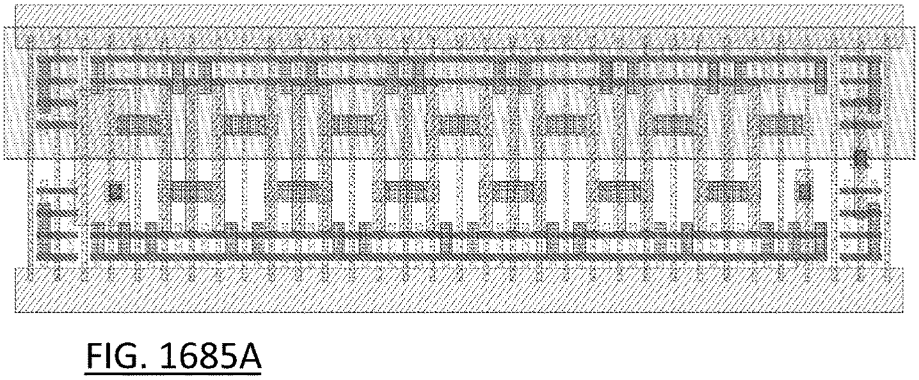
FIG. 1685A
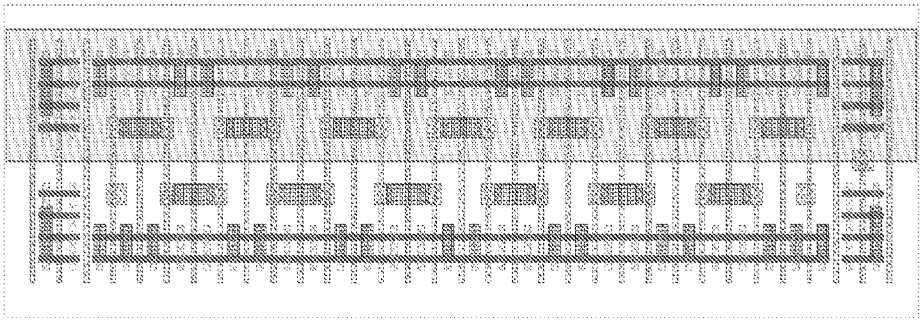
FIG. 1685B
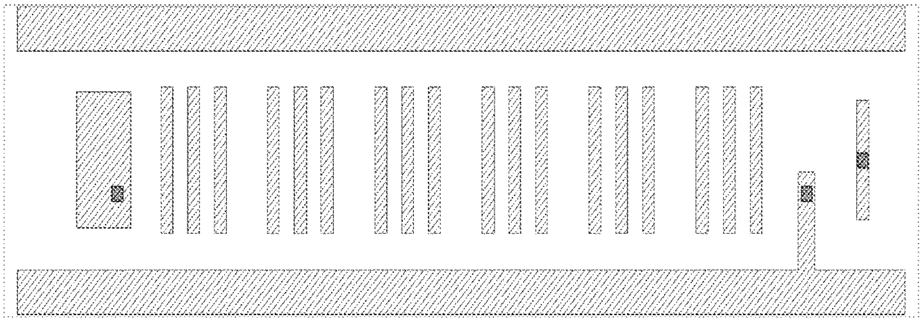
FIG. 1685C

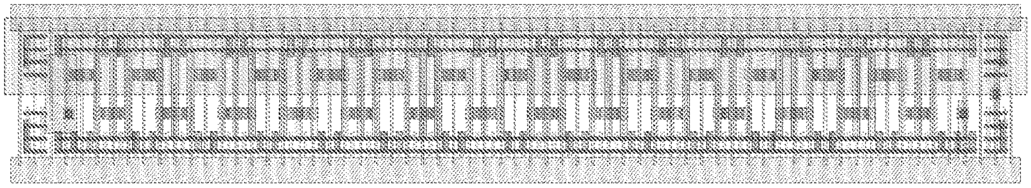
FIG. 1686A
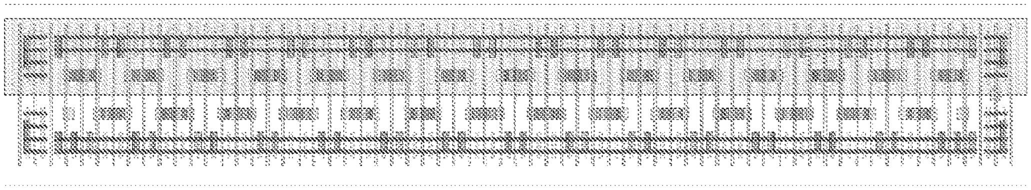
FIG. 1686B
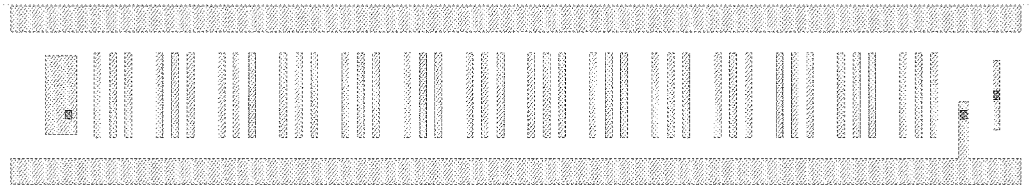
FIG. 1686C

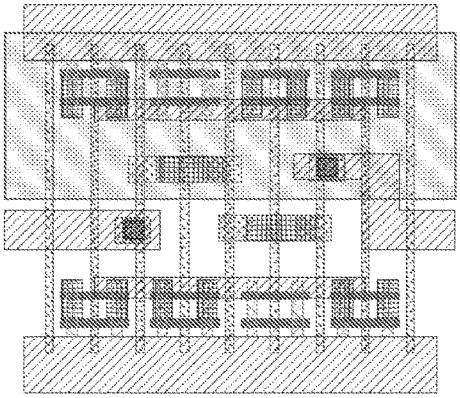
FIG. 1687A
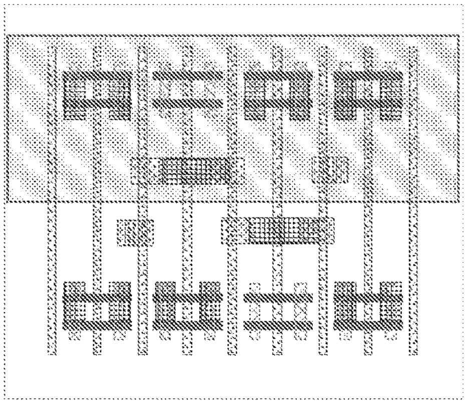
FIG. 1687B
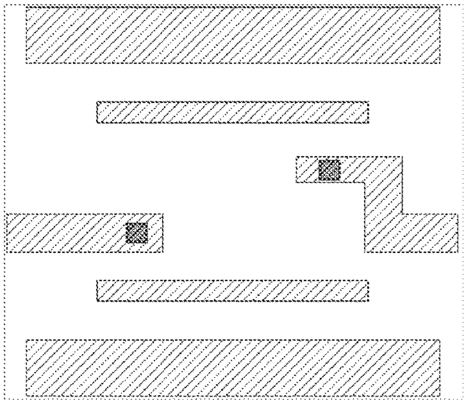
FIG. 1687C

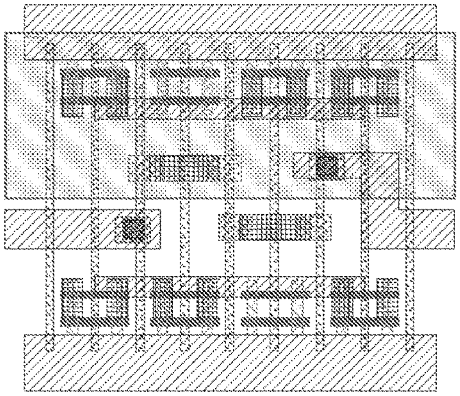
FIG. 1688A
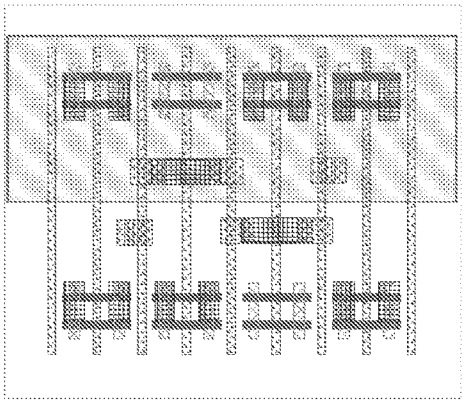
FIG. 1688B
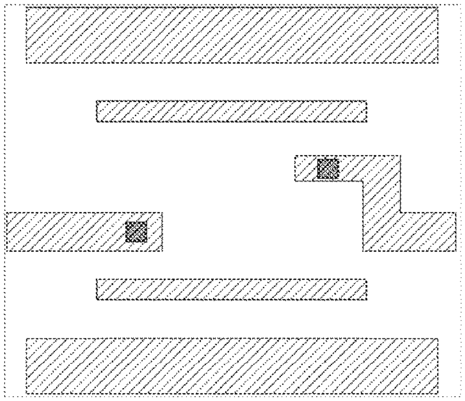
FIG. 1688C

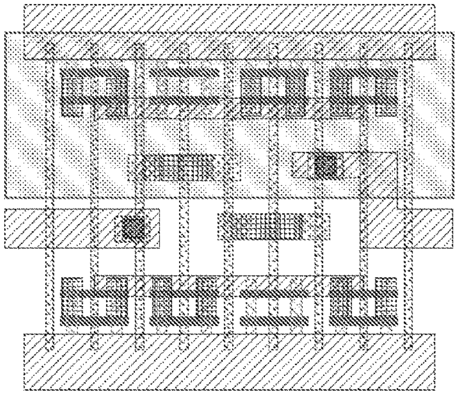
FIG. 1689A
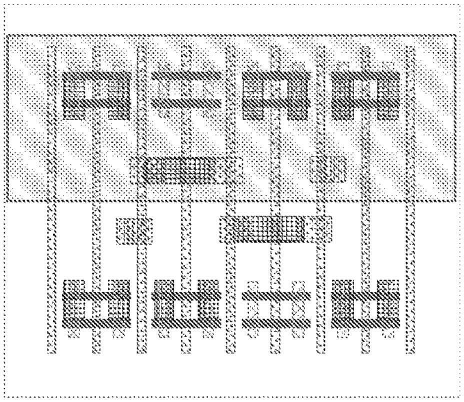
FIG. 1689B
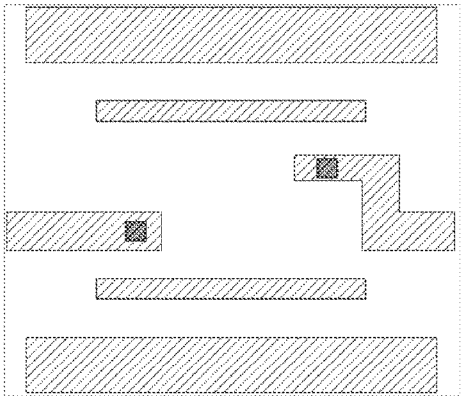
FIG. 1689C

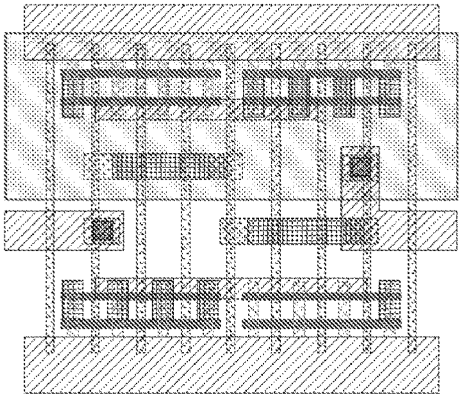
FIG. 1690A
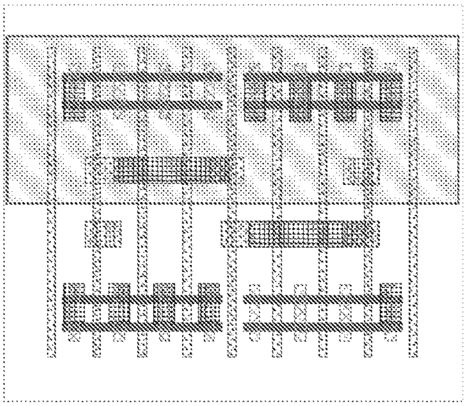
FIG. 1690B
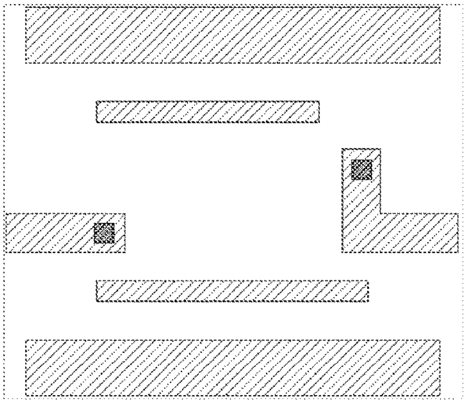
FIG. 1690C

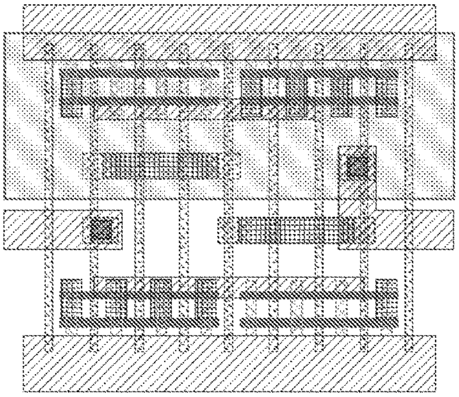
FIG. 1691A
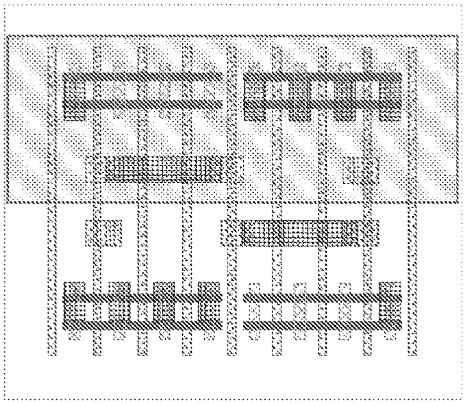
FIG. 1691B
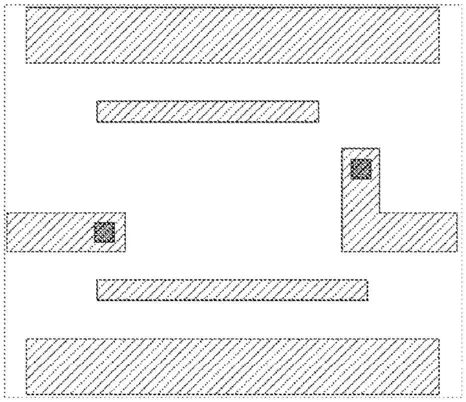
FIG. 1691C

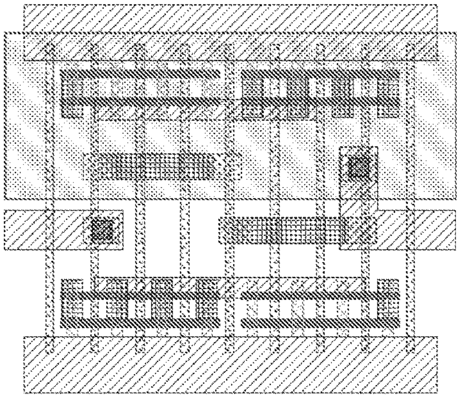
FIG. 1692A
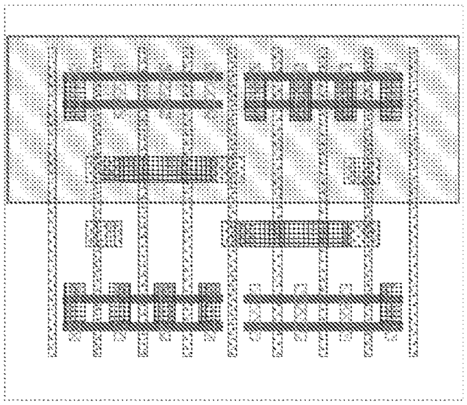
FIG. 1692B
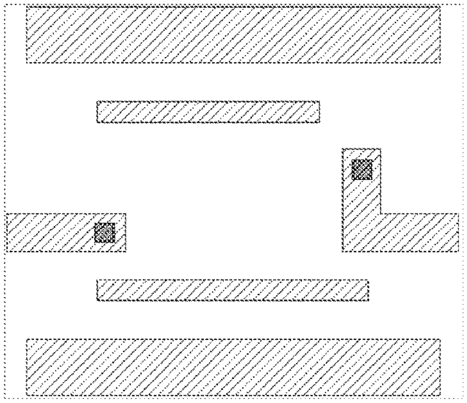
FIG. 1692C

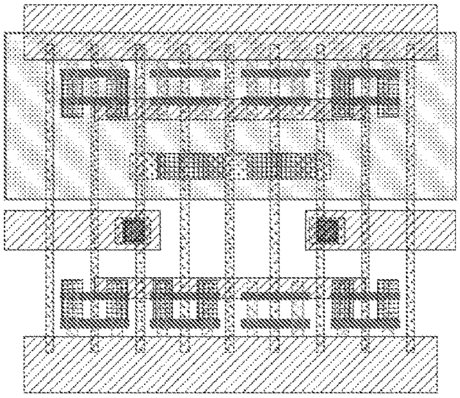
FIG. 1693A
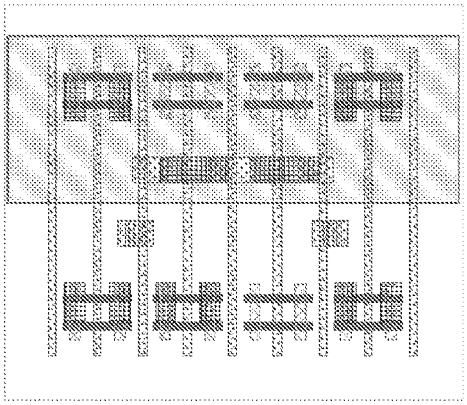
FIG. 1693B
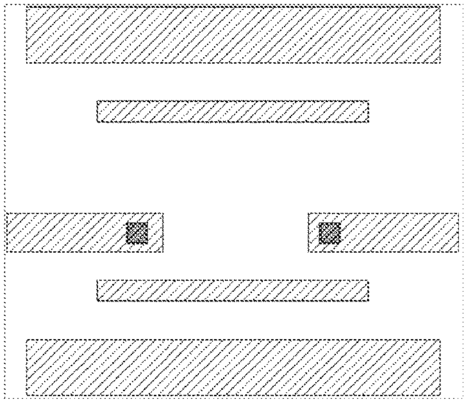
FIG. 1693C

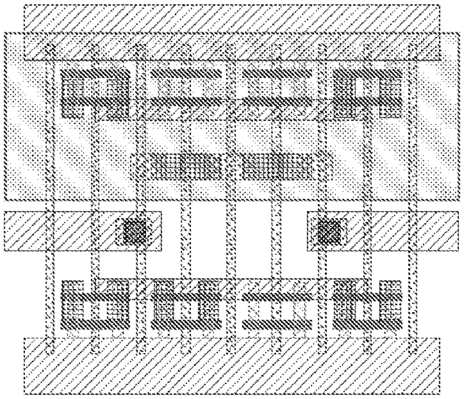
FIG. 1694A
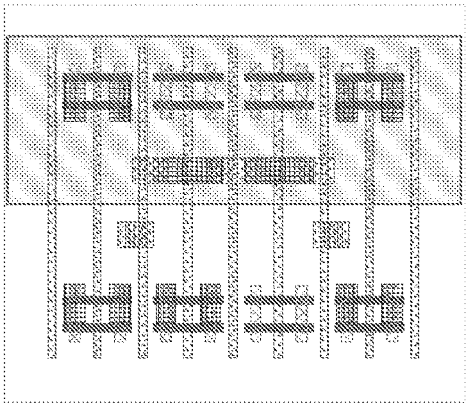
FIG. 1694B
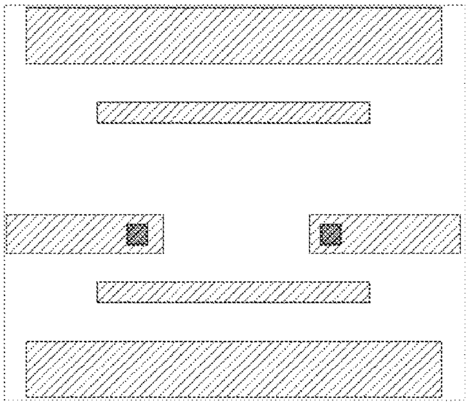
FIG. 1694C
*M* PDF Solutions, Inc.

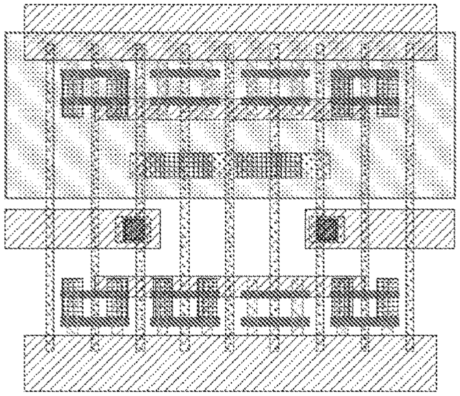
FIG. 1695A
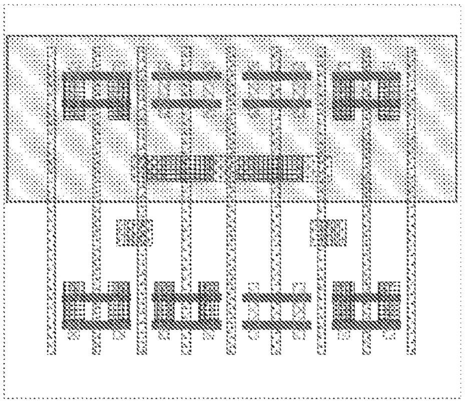
FIG. 1695B
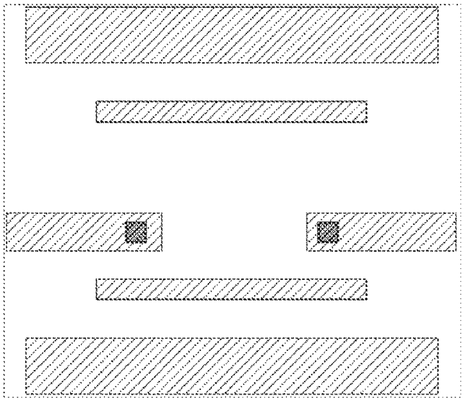
FIG. 1695C

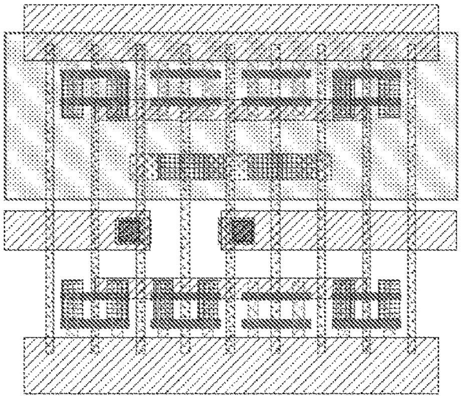
FIG. 1696A
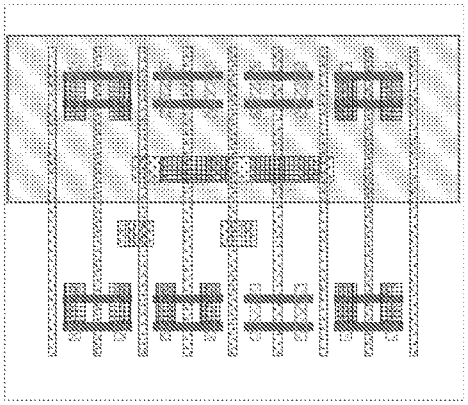
FIG. 1696B
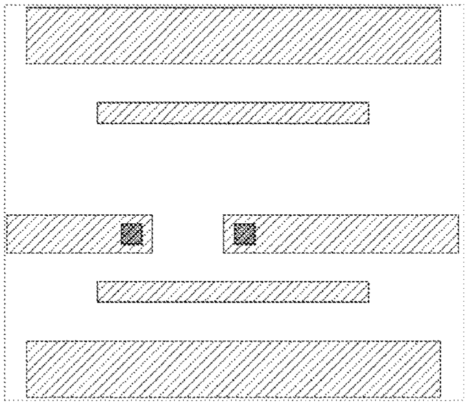
FIG. 1696C

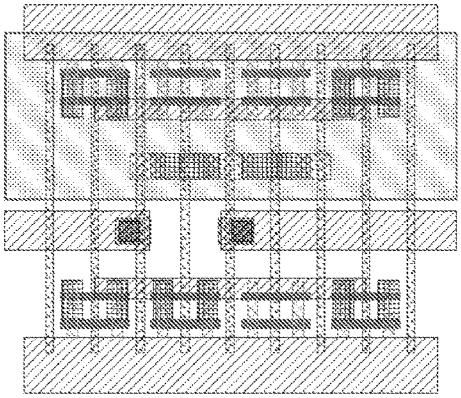
FIG. 1697A
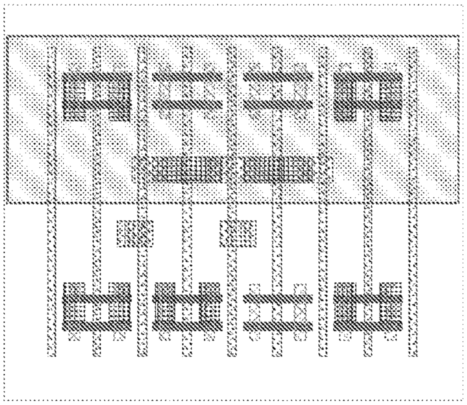
FIG. 1697B
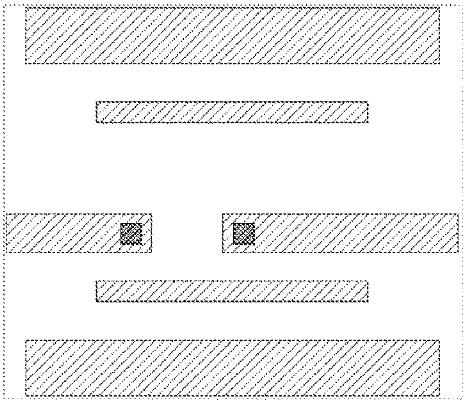
FIG. 1697C
*M* PDF Solutions, Inc.

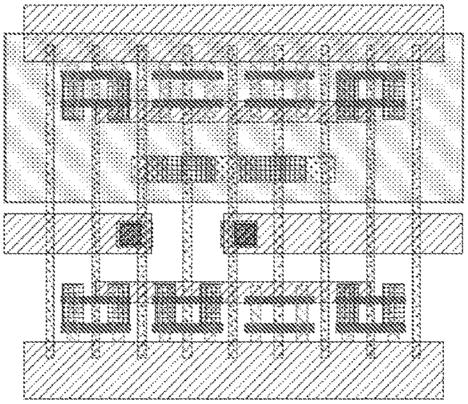
FIG. 1698A
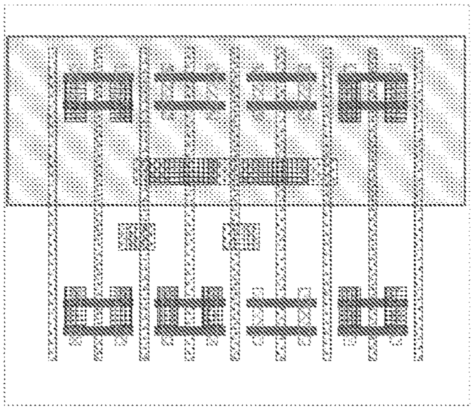
FIG. 1698B
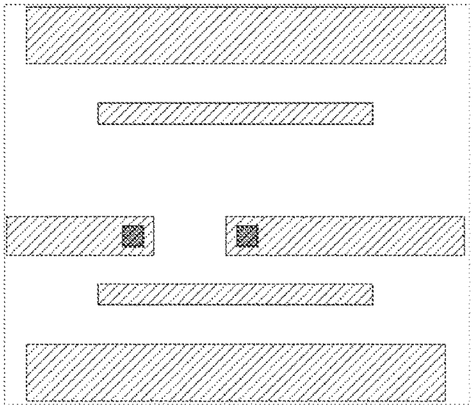
FIG. 1698C

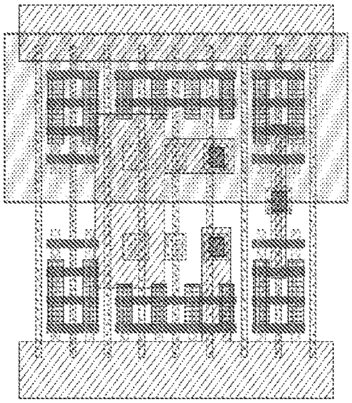
FIG. 1699A
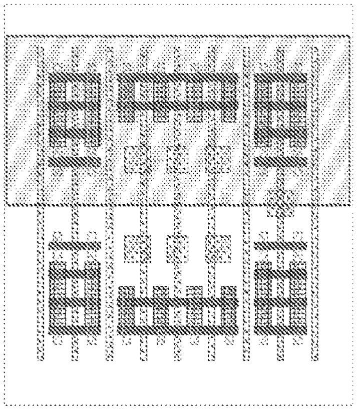
FIG. 1699B
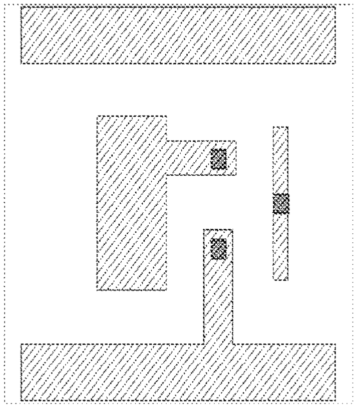
FIG. 1699C

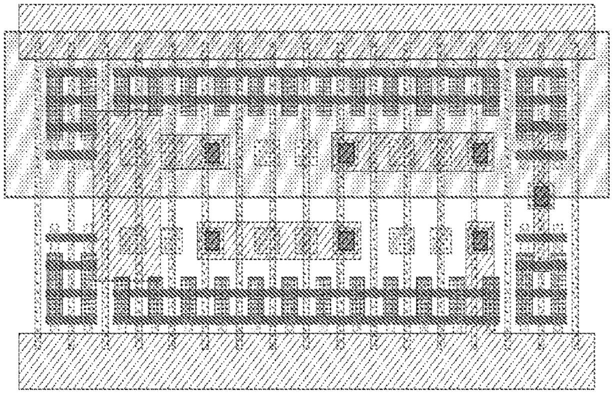
FIG. 1700A
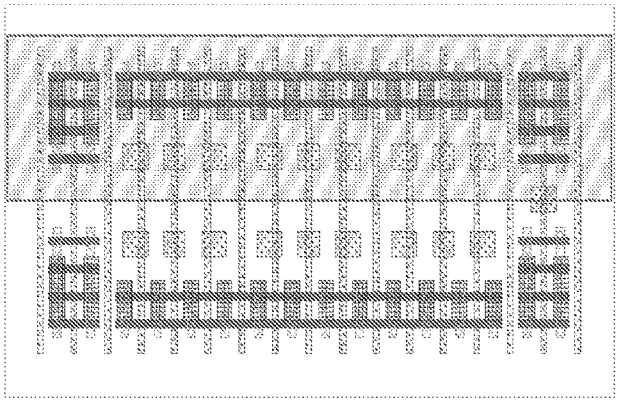
FIG. 1700B
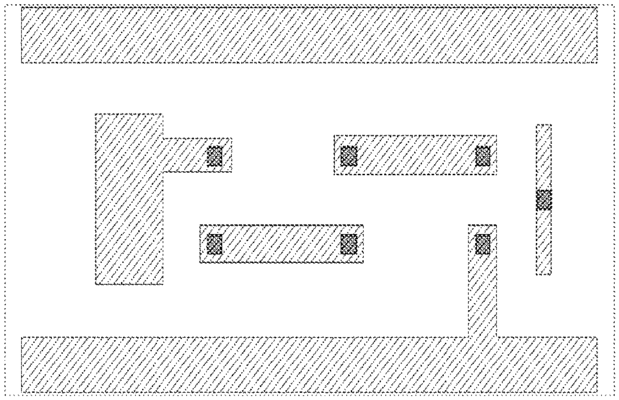
FIG. 1700C
*M* PDF Solutions, Inc.

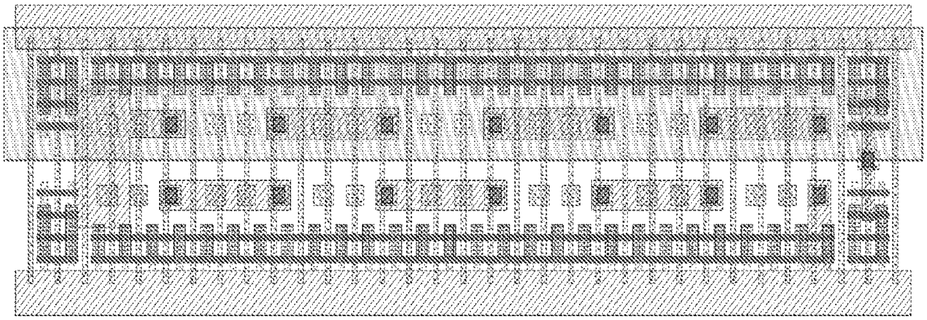
FIG. 1701A
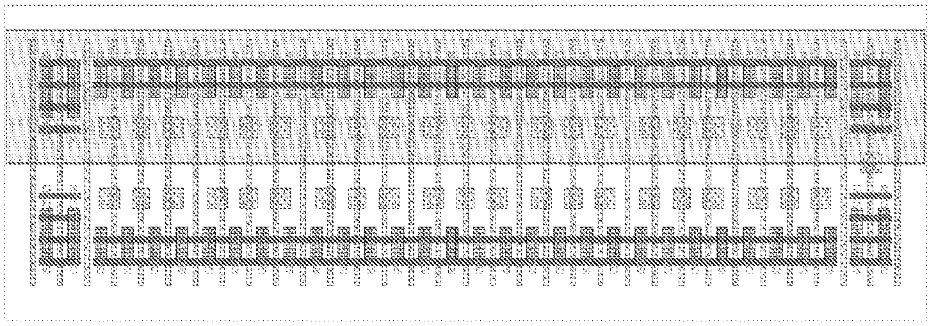
FIG. 1701B
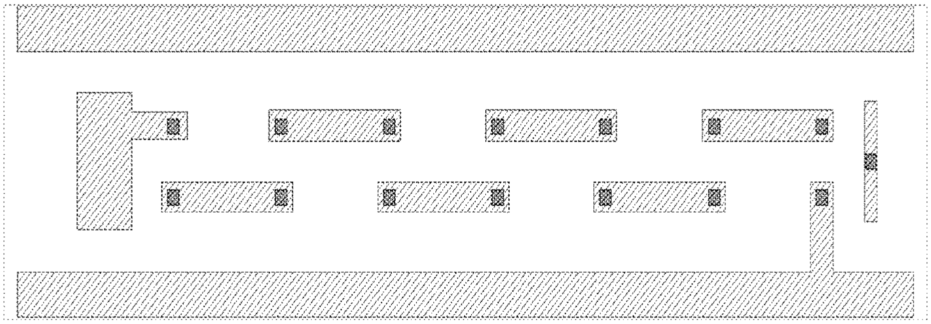
FIG. 1701C
*M* PDF Solutions, Inc.

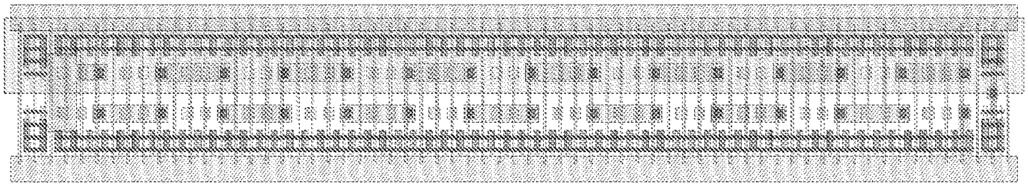
FIG. 1702A
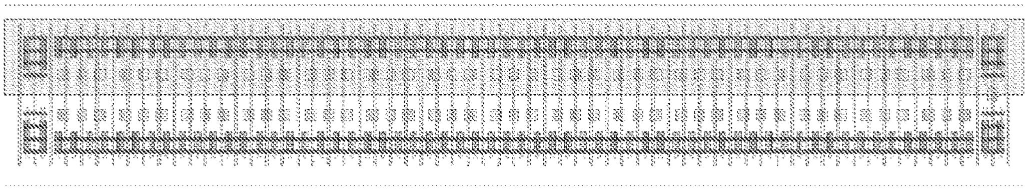
FIG. 1702B
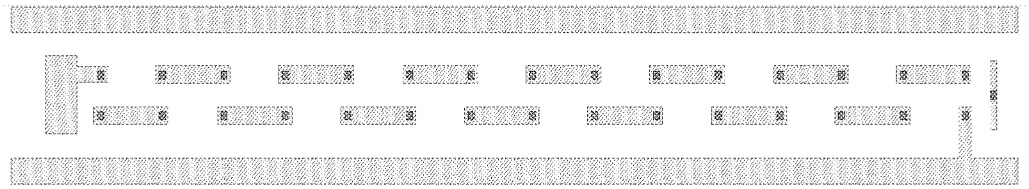
FIG. 1702C

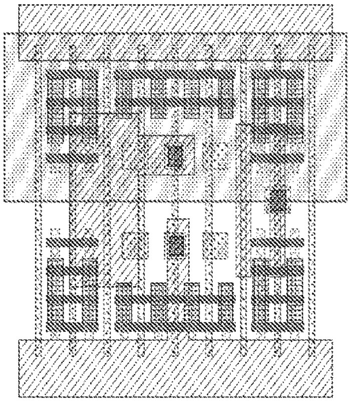
FIG. 1703A
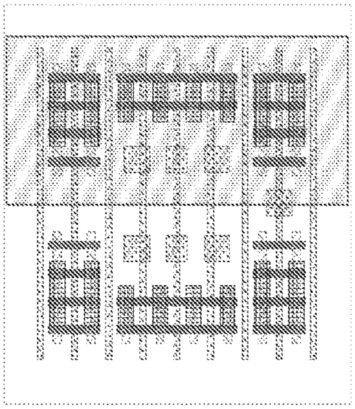
FIG. 1703B
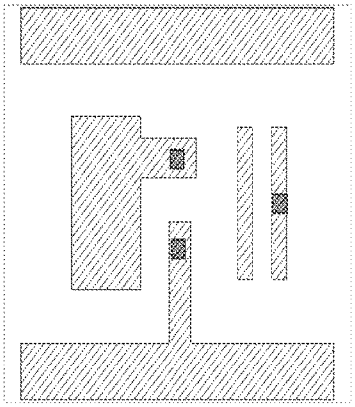
FIG. 1703C

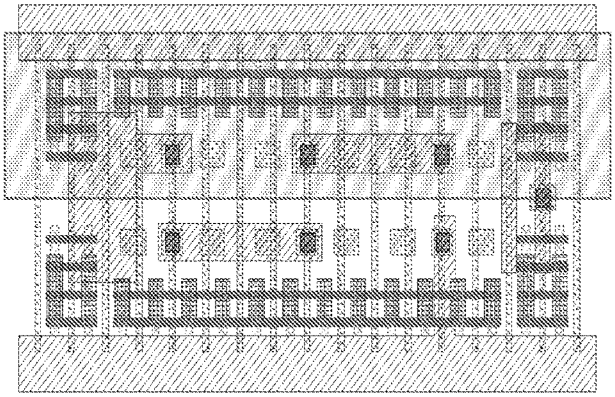
FIG. 1704A
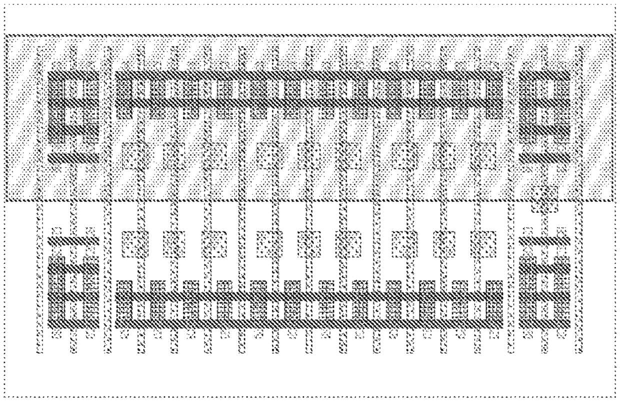
FIG. 1704B
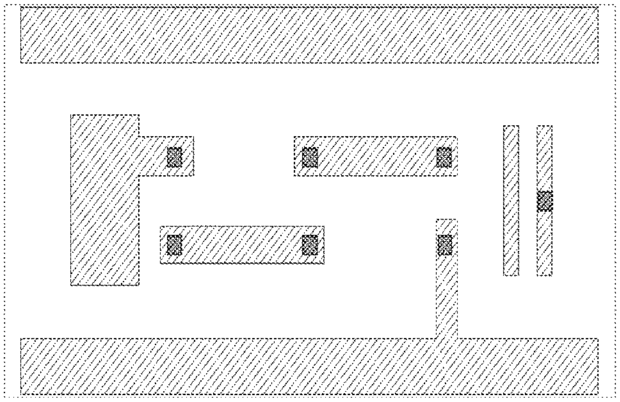
FIG. 1704C
*M* PDF Solutions, Inc.

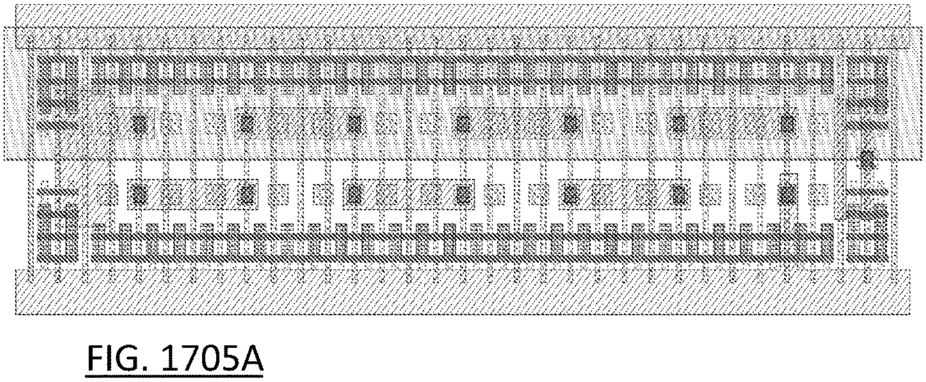
FIG. 1705A
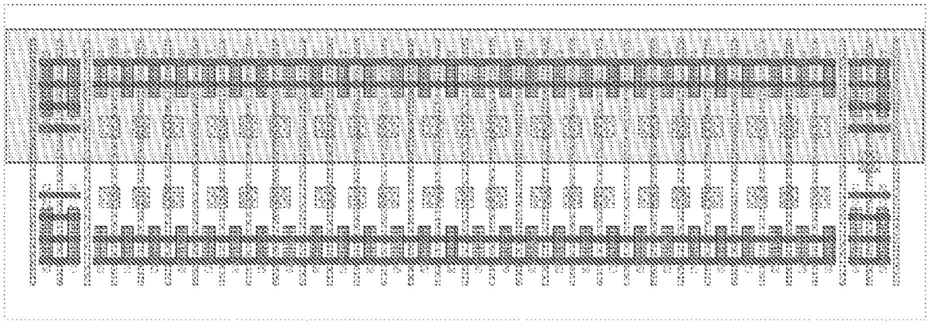
FIG. 1705B
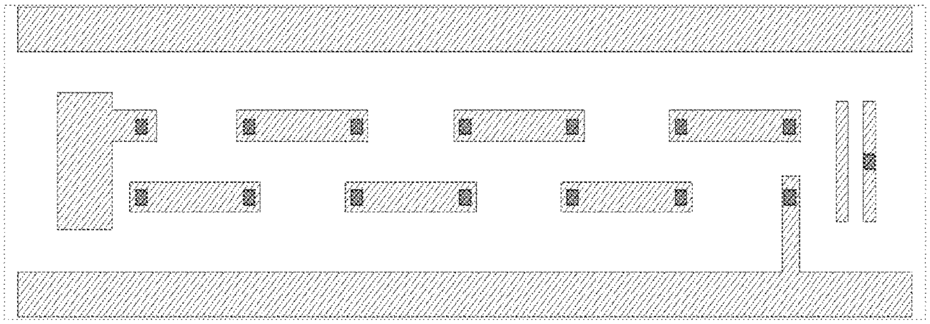
FIG. 1705C

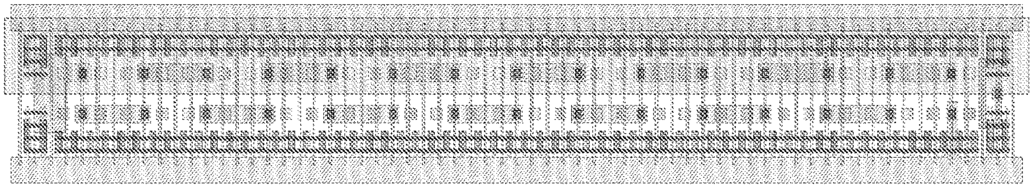
FIG. 1706A
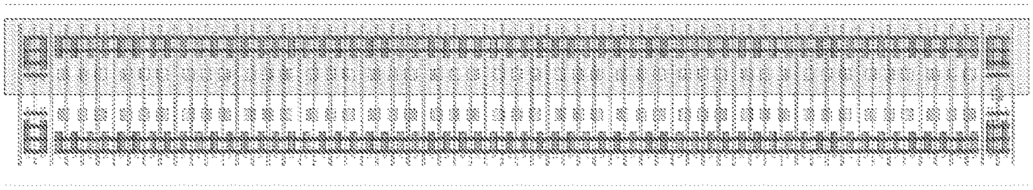
FIG. 1706B
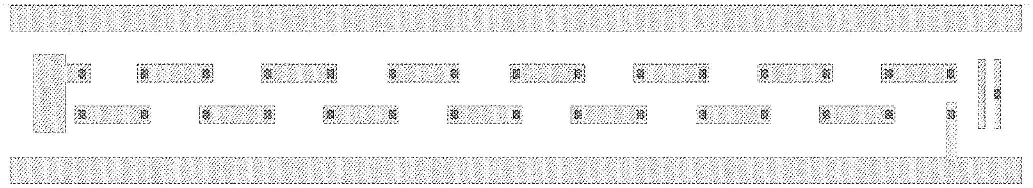
FIG. 1706C
*M* PDF Solutions, Inc.

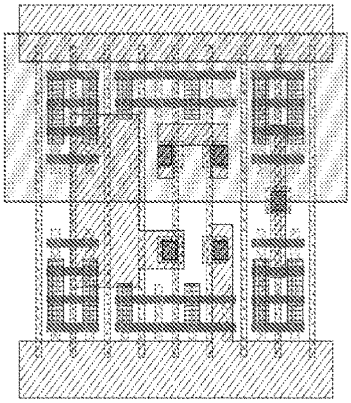
FIG. 1707A
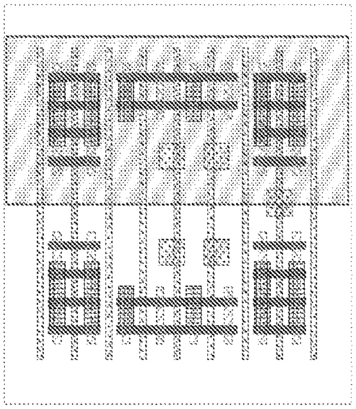
FIG. 1707B
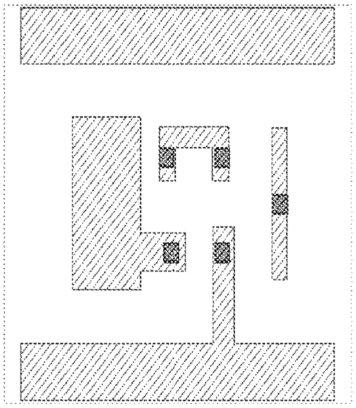
FIG. 1707C

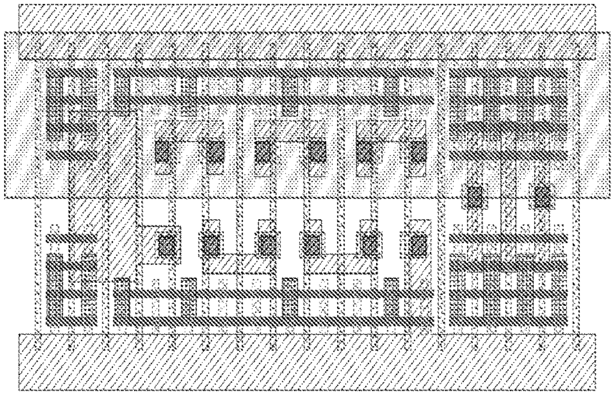
FIG. 1708A
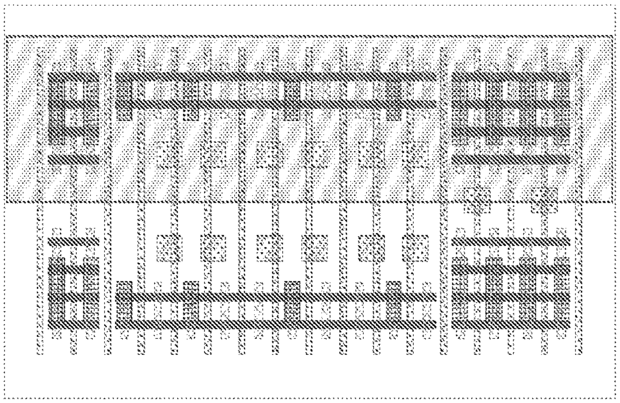
FIG. 1708B
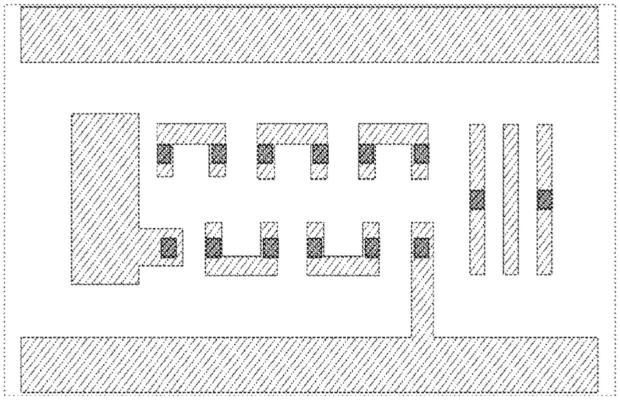
FIG. 1708C

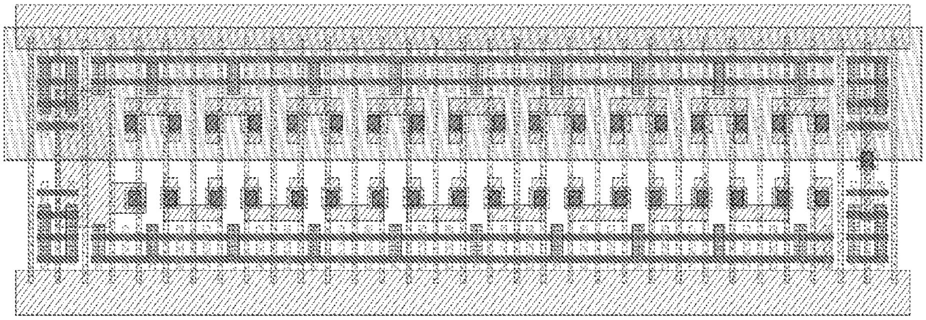
FIG. 1709A
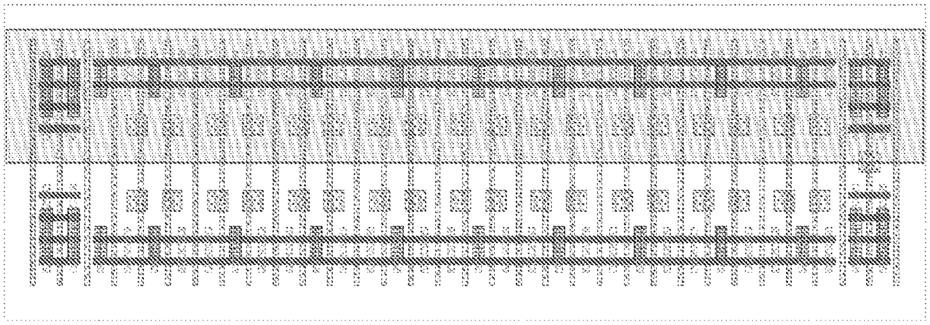
FIG. 1709B
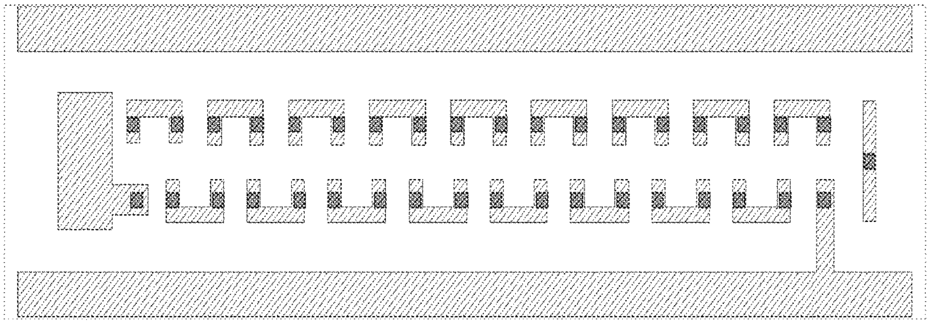
FIG. 1709C

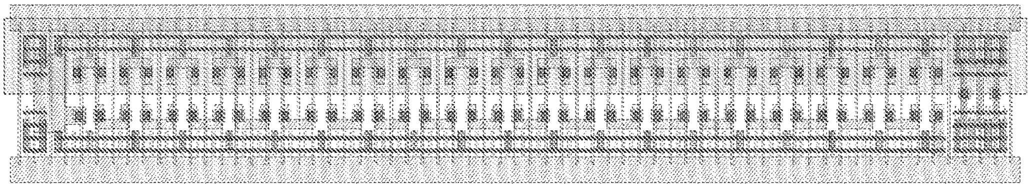
FIG. 1710A
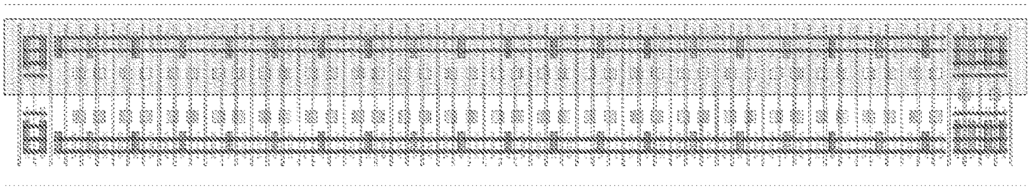
FIG. 1710B
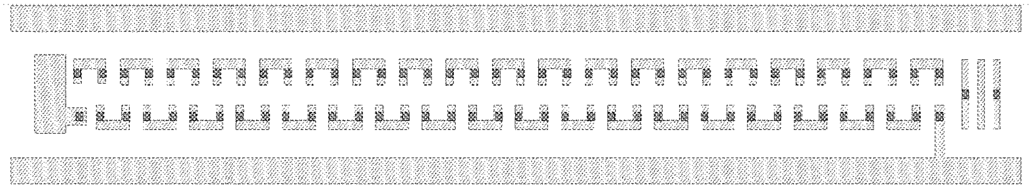
FIG. 1710C

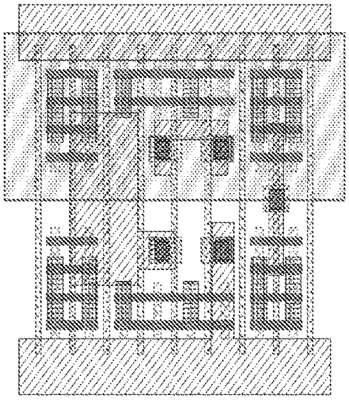
FIG. 1711A
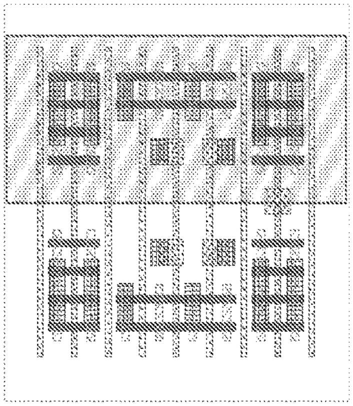
FIG. 1711B
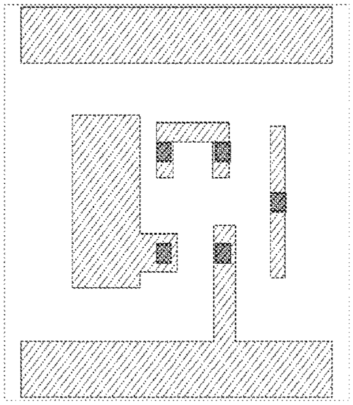
FIG. 1711C

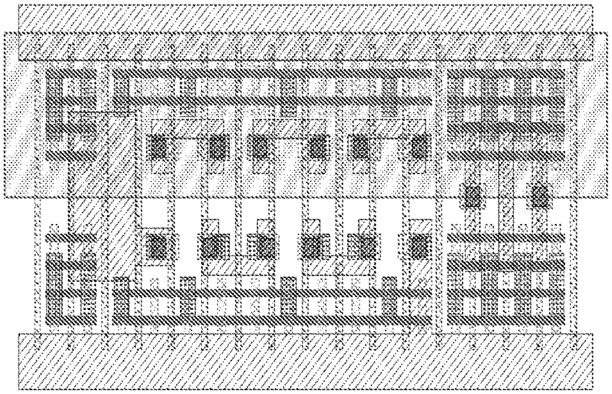
FIG. 1712A
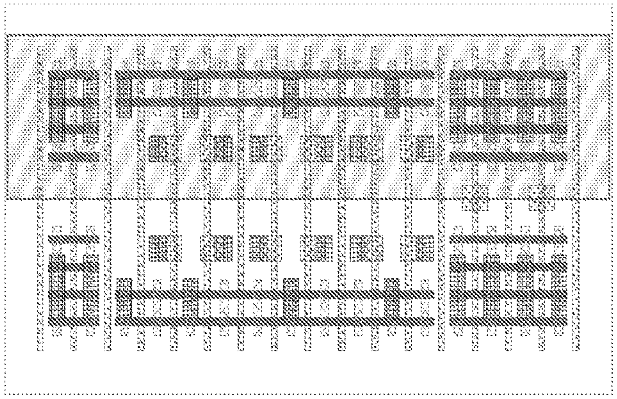
FIG. 1712B
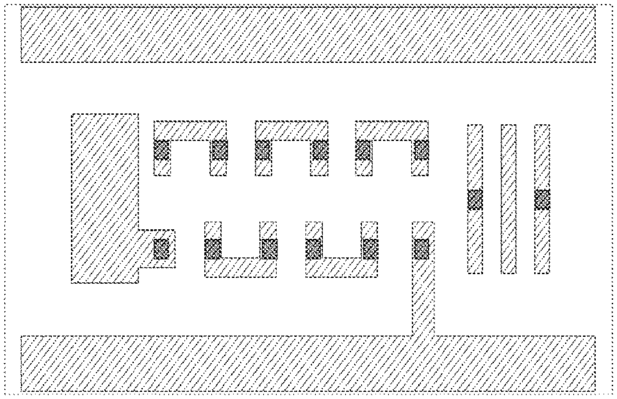
FIG. 1712C

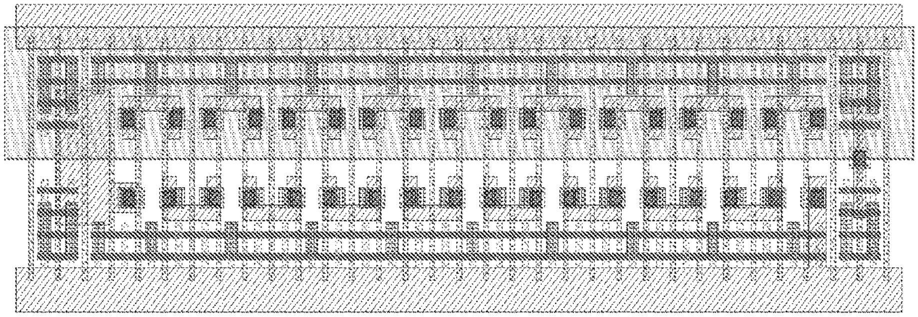
FIG. 1713A
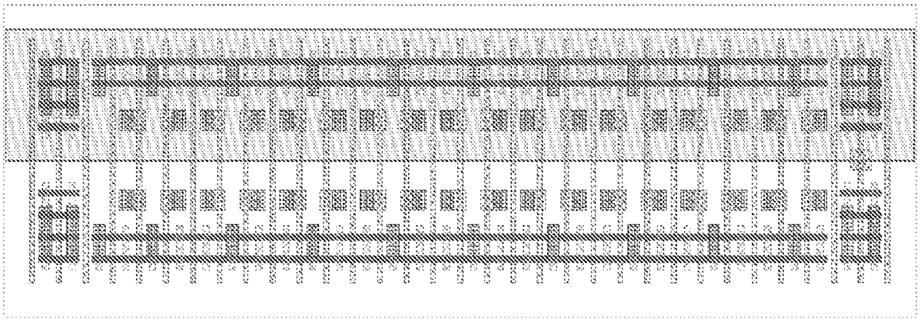
FIG. 1713B
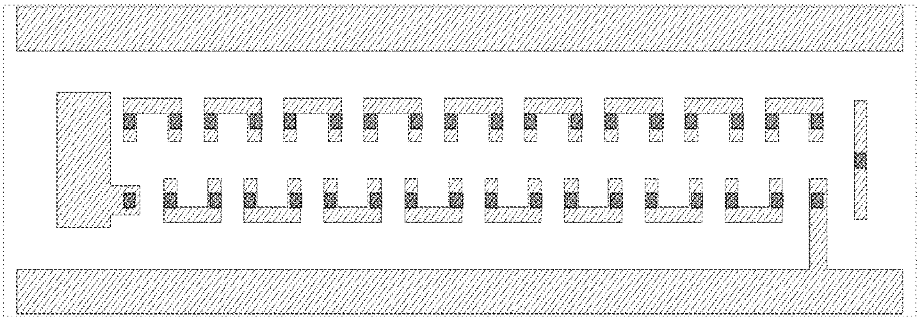
FIG. 1713C

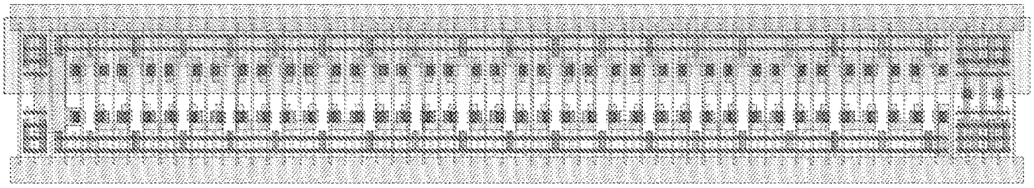
FIG. 1714A
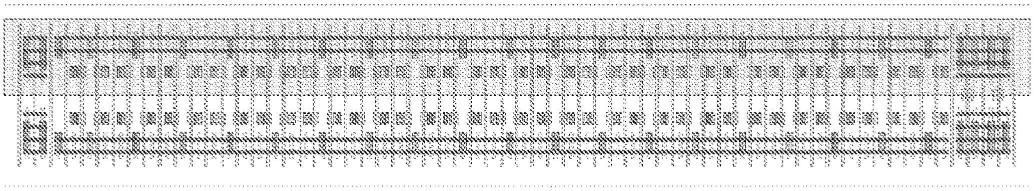
FIG. 1714B
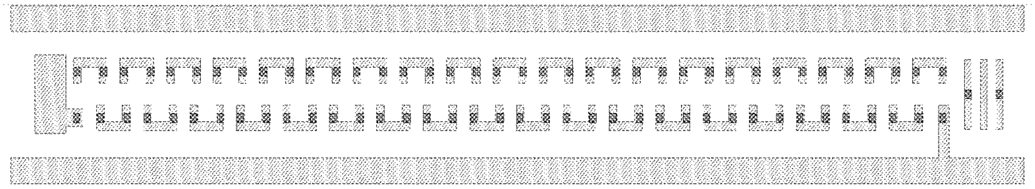
FIG. 1714C

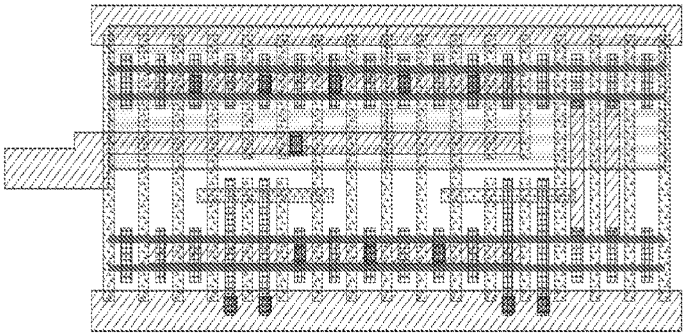
FIG. 1715A
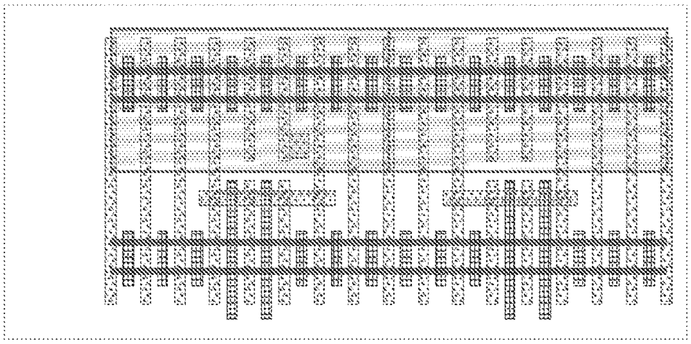
FIG. 1715B
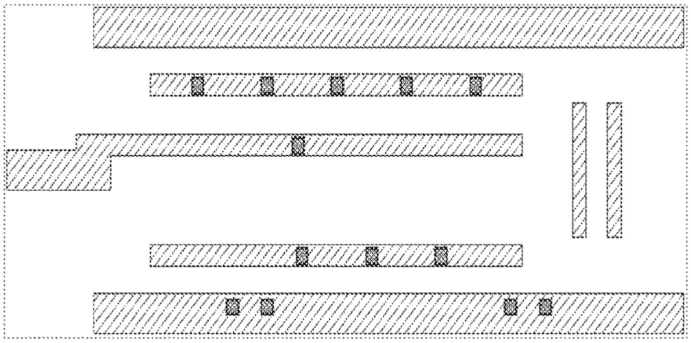
FIG. 1715C

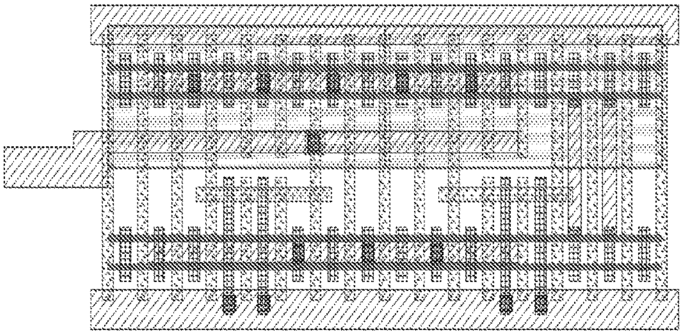
FIG. 1716A
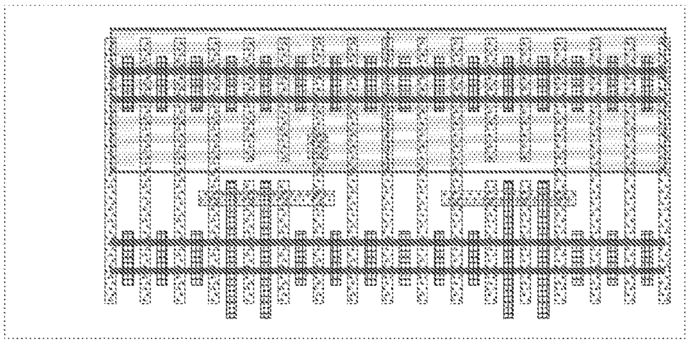
FIG. 1716B
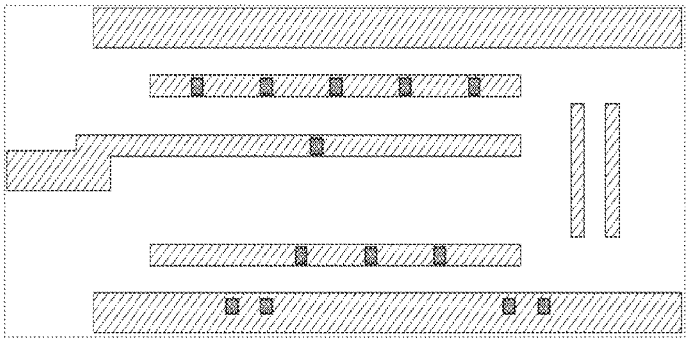
FIG. 1716C

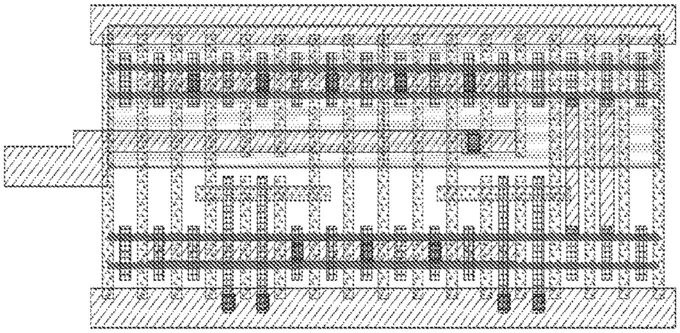
FIG. 1717A
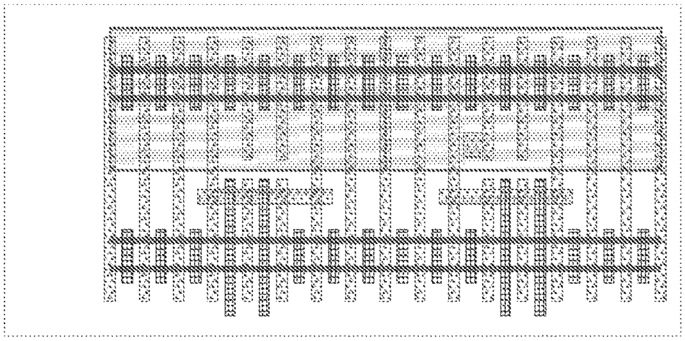
FIG. 1717B
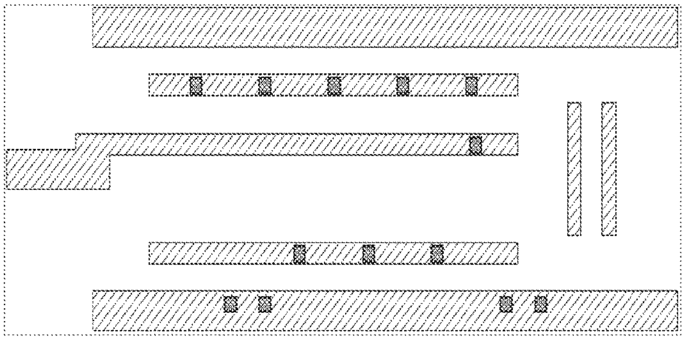
FIG. 1717C
*M* PDF Solutions, Inc.

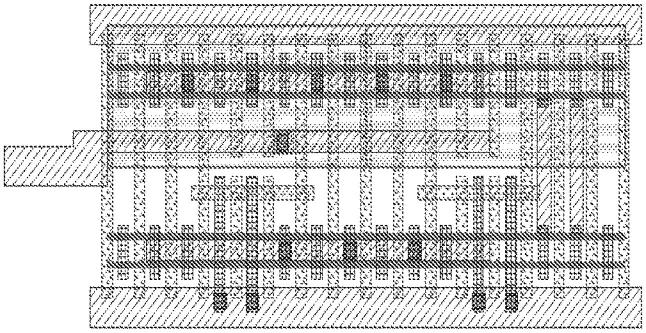
FIG. 1718A
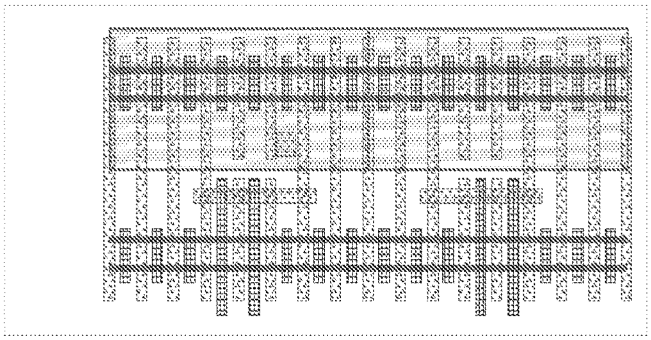
FIG. 1718B
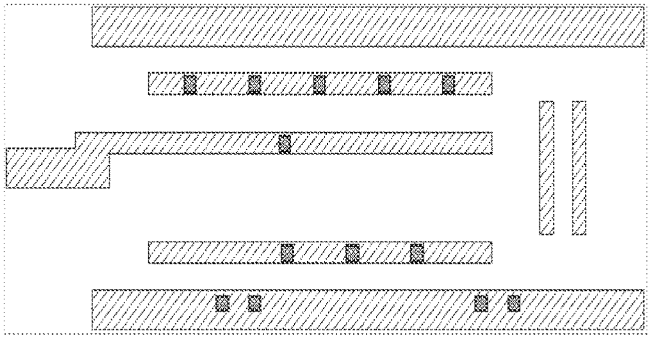
FIG. 1718C

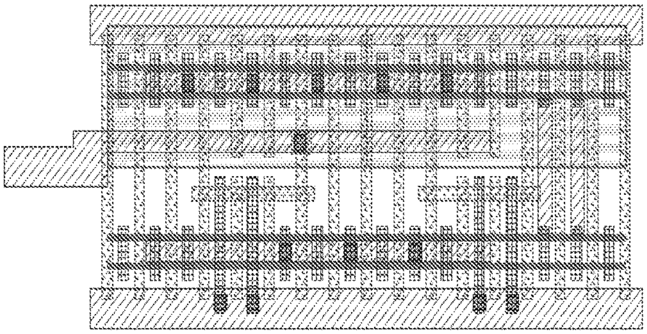
FIG. 1719A
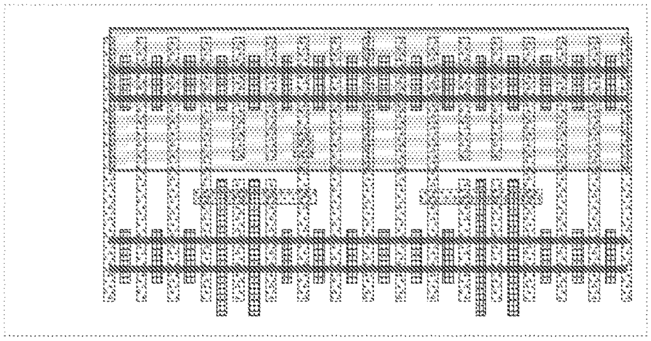
FIG. 1719B
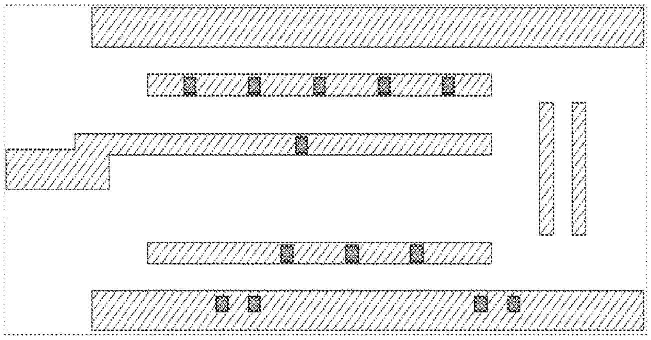
FIG. 1719C

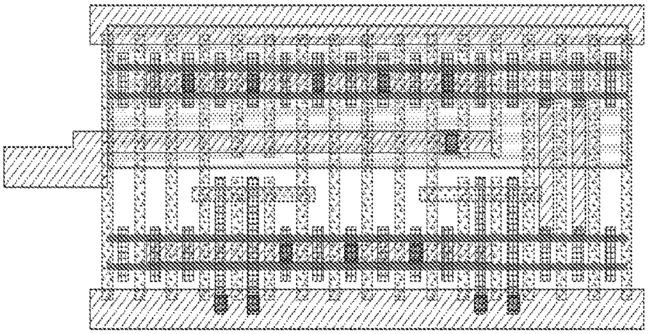
FIG. 1720A
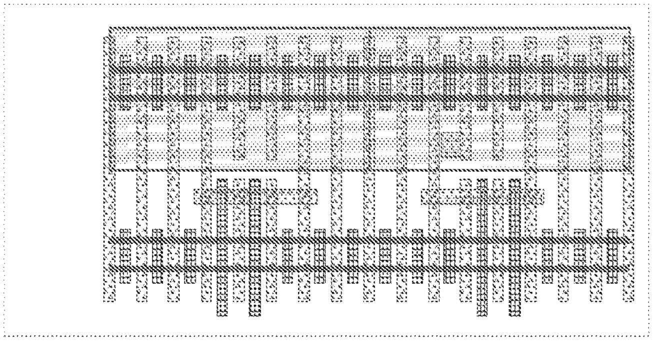
FIG. 1720B
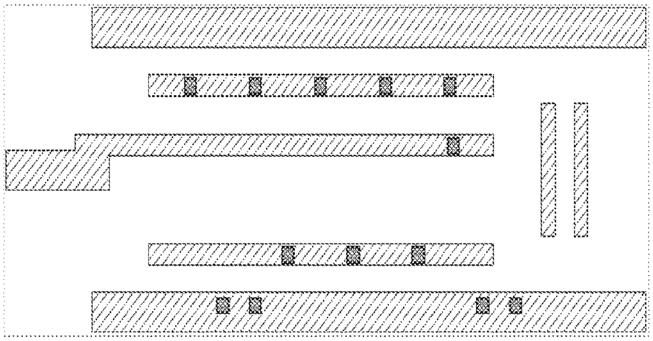
FIG. 1720C
*M* PDF Solutions, Inc.

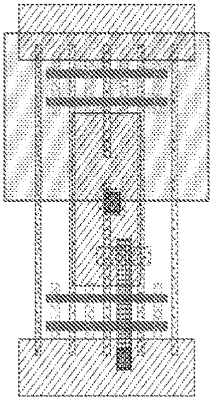
FIG. 1721A
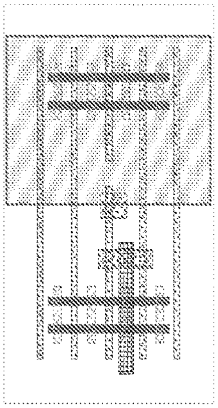
FIG. 1721B
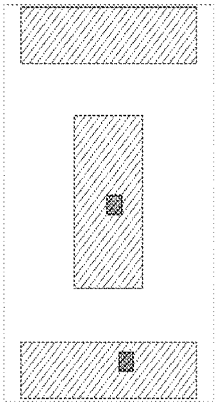
FIG. 1721C

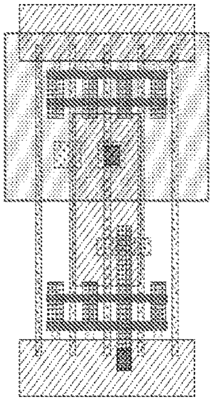
FIG. 1722A
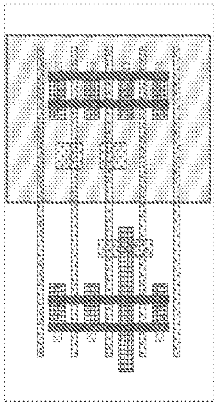
FIG. 1722B
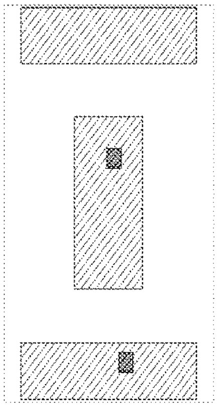
FIG. 1722C

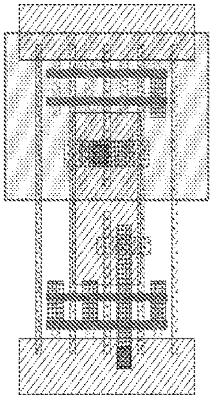
FIG. 1723A
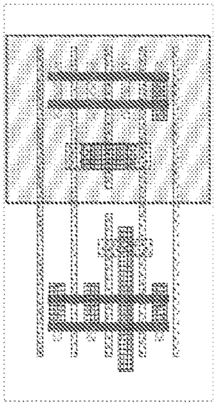
FIG. 1723B
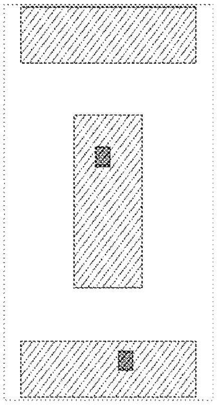
FIG. 1723C

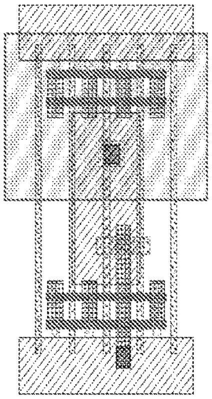
FIG. 1724A
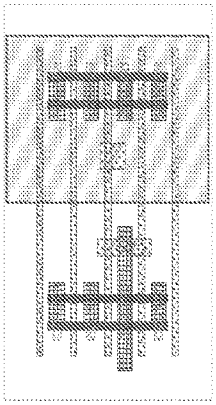
FIG. 1724B
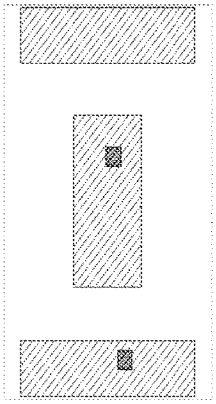
FIG. 1724C

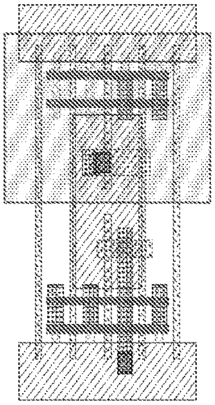
FIG. 1725A
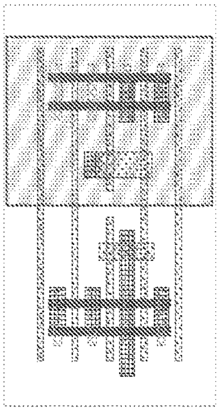
FIG. 1725B
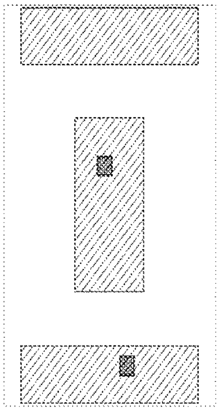
FIG. 1725C

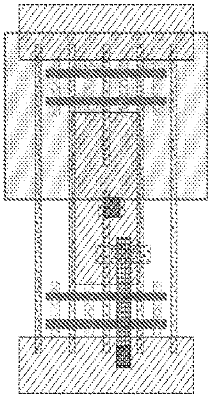
FIG. 1726A
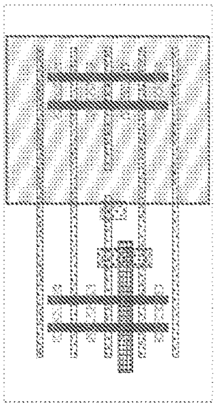
FIG. 1726B
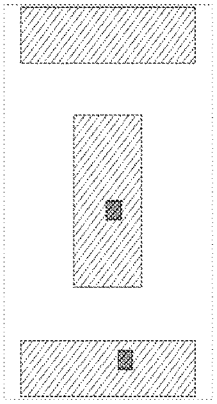
FIG. 1726C
*M* PDF Solutions, Inc.

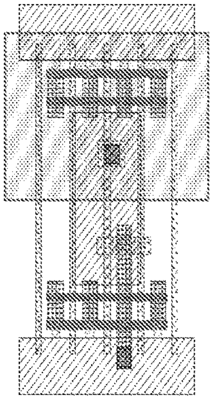
FIG. 1727A
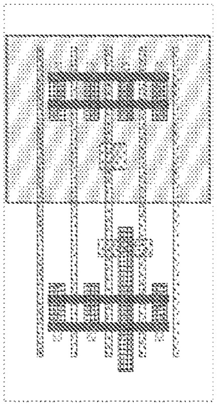
FIG. 1727B
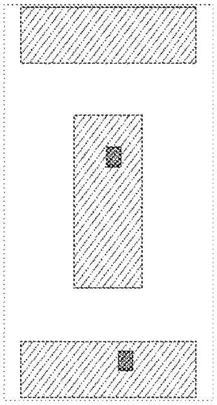
FIG. 1727C

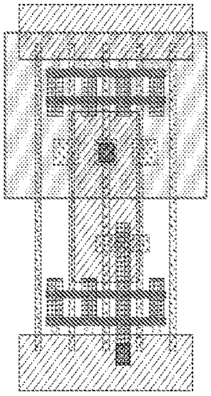
FIG. 1728A
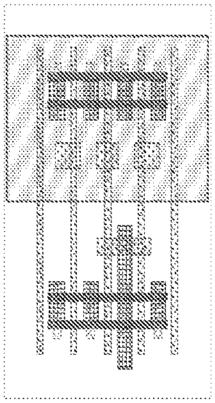
FIG. 1728B
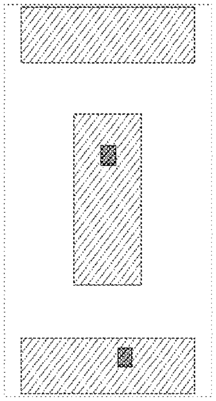
FIG. 1728C

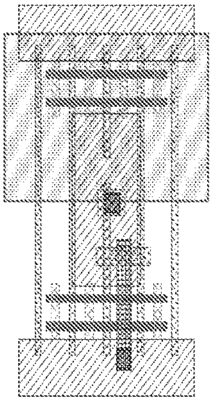
FIG. 1729A
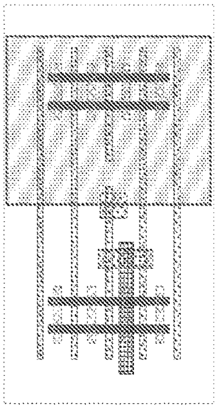
FIG. 1729B
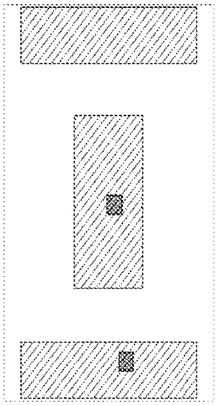
FIG. 1729C
*M* PDF Solutions, Inc.

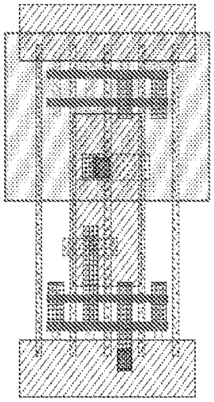
FIG. 1730A
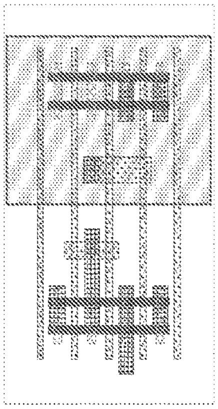
FIG. 1730B
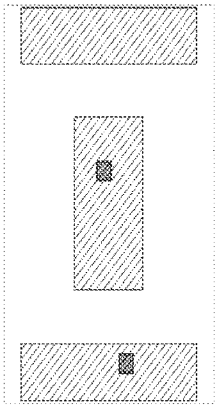
FIG. 1730C

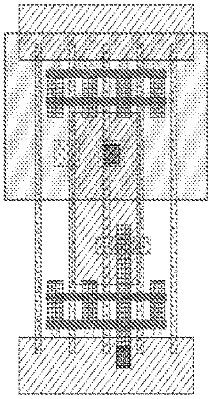
FIG. 1731A
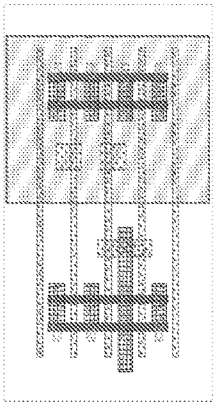
FIG. 1731B
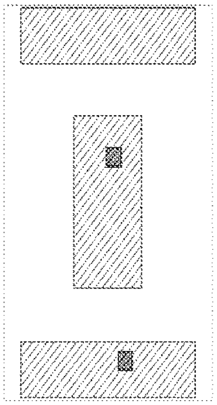
FIG. 1731C

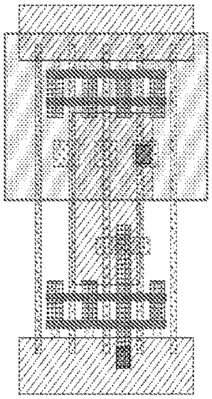
FIG. 1732A
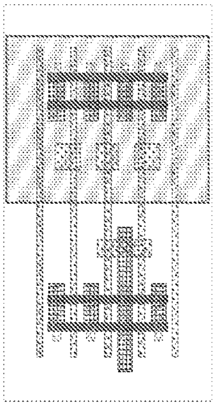
FIG. 1732B
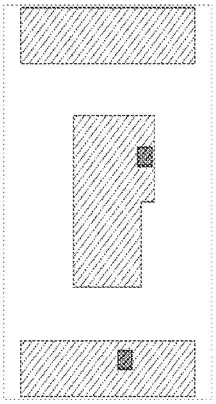
FIG. 1732C

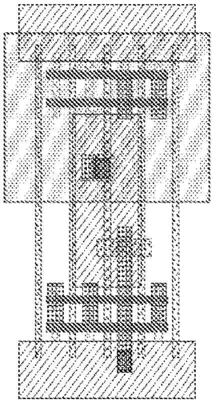
FIG. 1733A
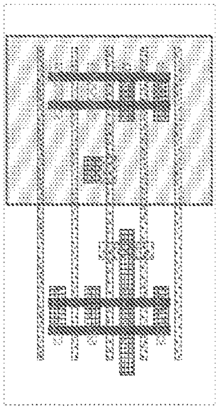
FIG. 1733B
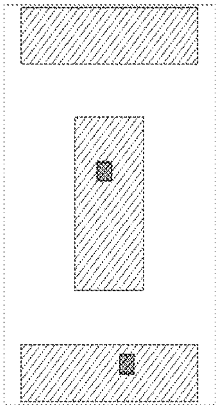
FIG. 1733C
*M* PDF Solutions, Inc.

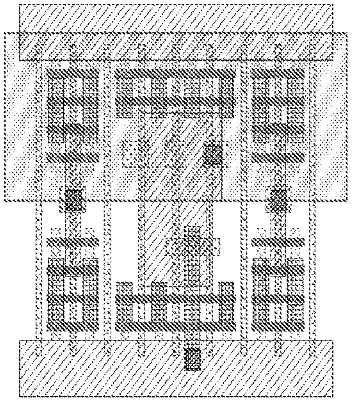
FIG. 1734A
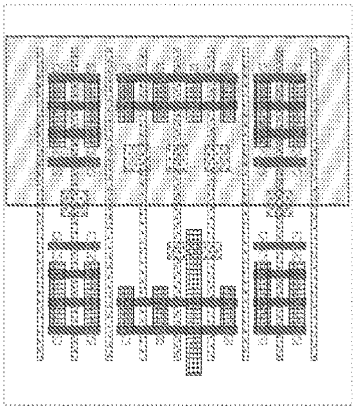
FIG. 1734B
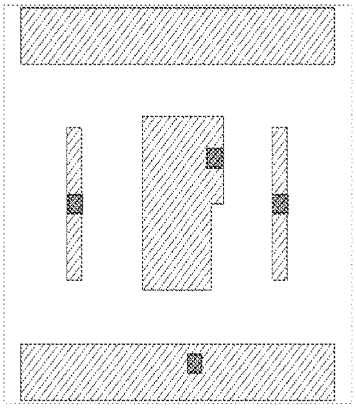
FIG. 1734C
*M* PDF Solutions, Inc.

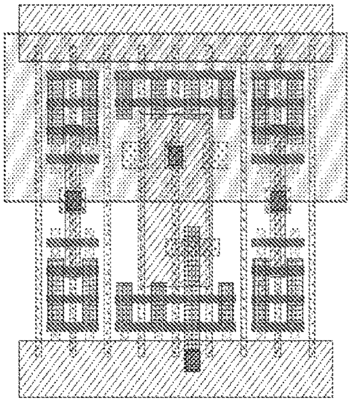
FIG. 1735A
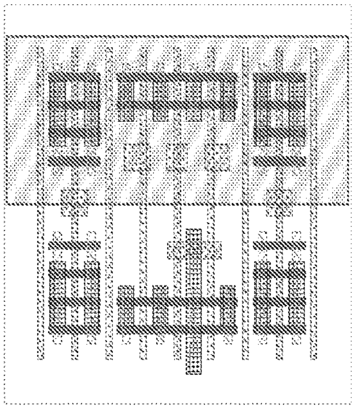
FIG. 1735B
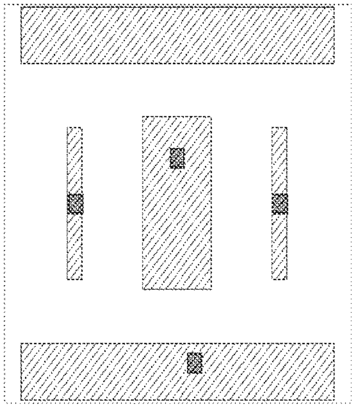
FIG. 1735C
*M* PDF Solutions, Inc.

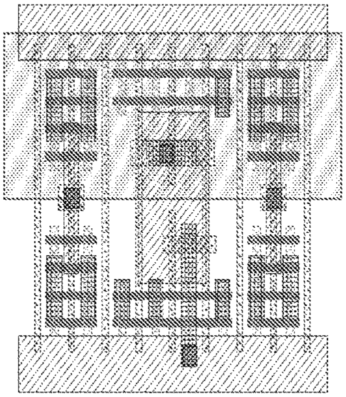
FIG. 1736A
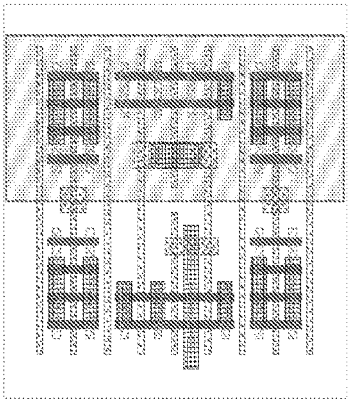
FIG. 1736B
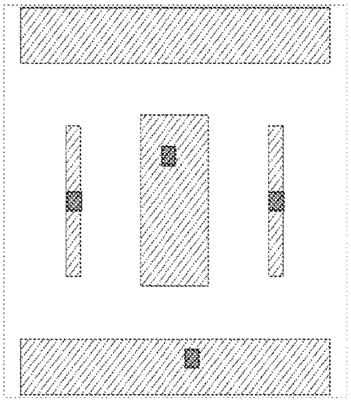
FIG. 1736C

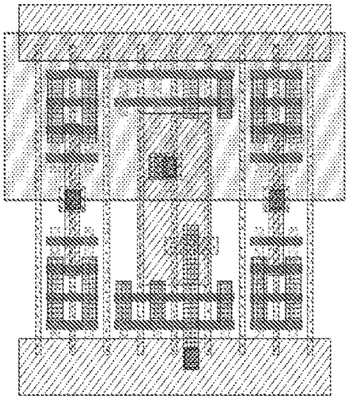
FIG. 1737A
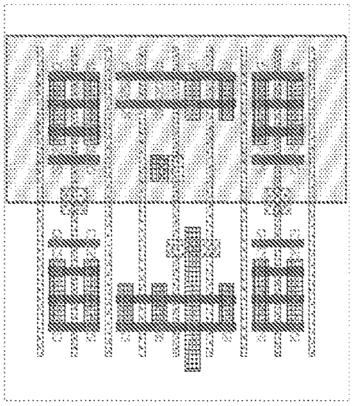
FIG. 1737B
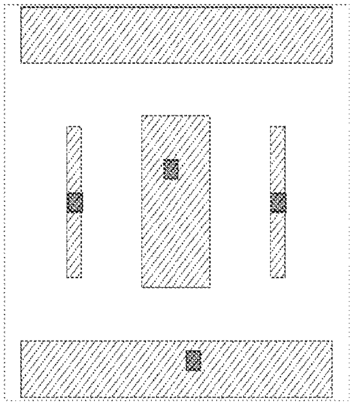
FIG. 1737C

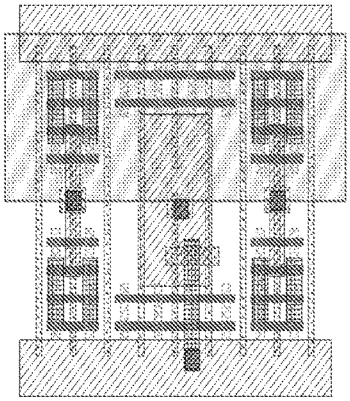
FIG. 1738A
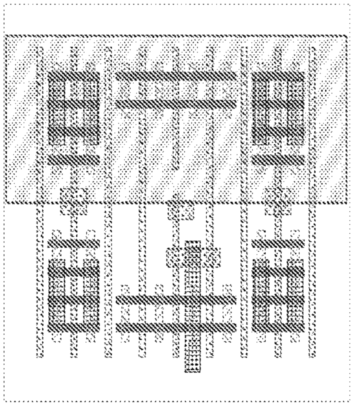
FIG. 1738B
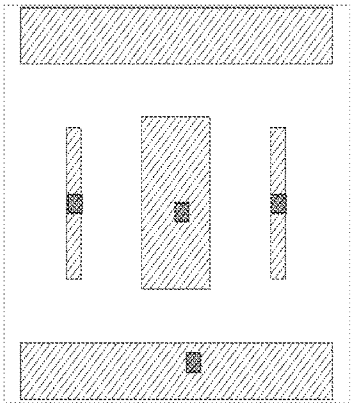
FIG. 1738C
*M* PDF Solutions, Inc.

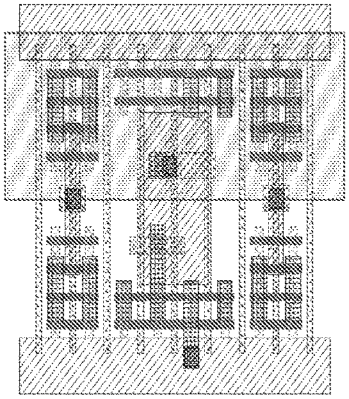
FIG. 1739A
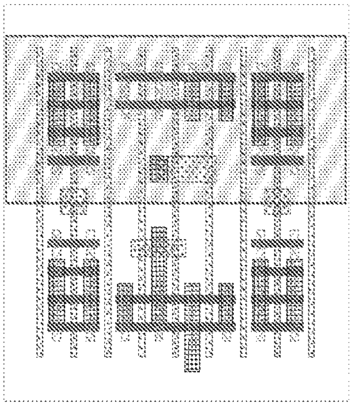
FIG. 1739B
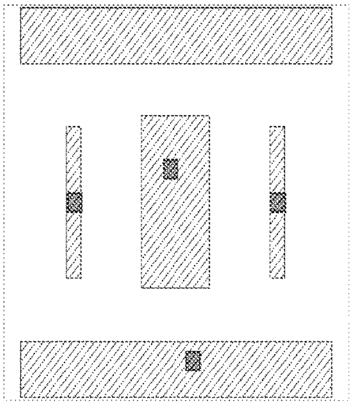
FIG. 1739C
*M* PDF Solutions, Inc.

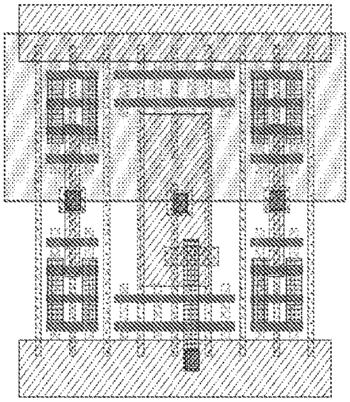
FIG. 1740A
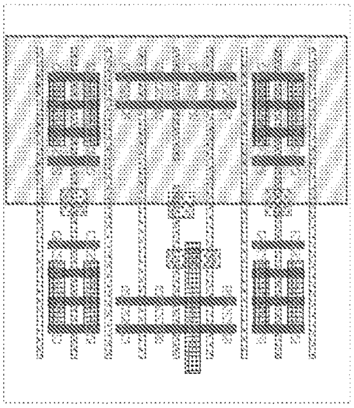
FIG. 1740B
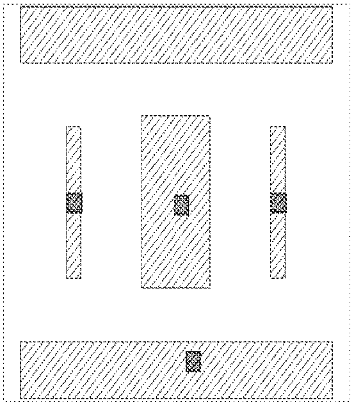
FIG. 1740C

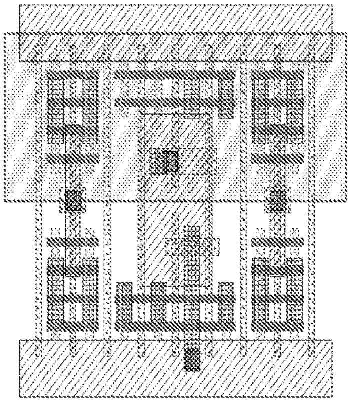
FIG. 1741A
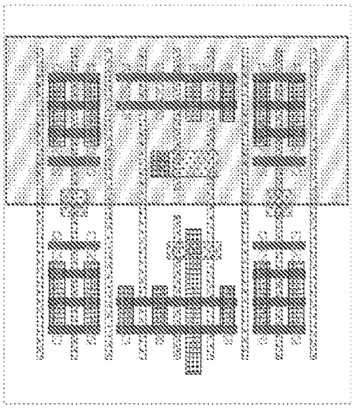
FIG. 1741B
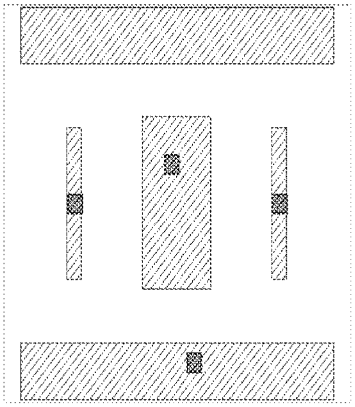
FIG. 1741C

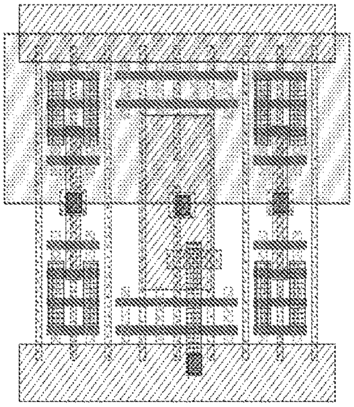
FIG. 1742A
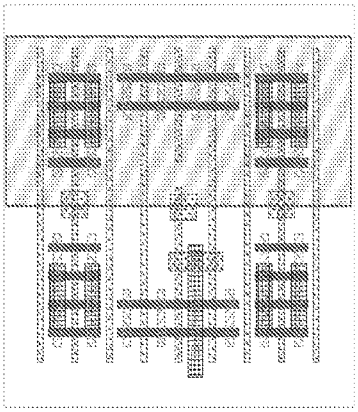
FIG. 1742B
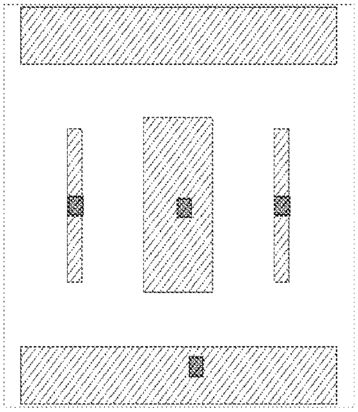
FIG. 1742C

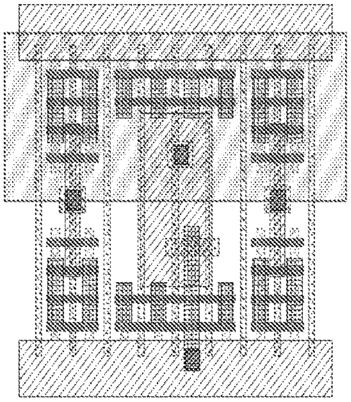
FIG. 1743A
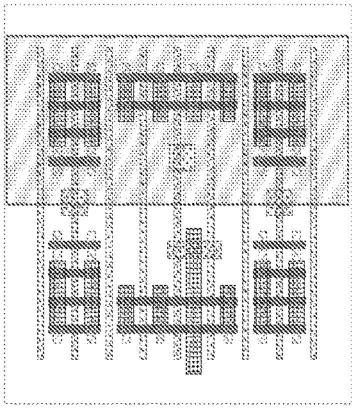
FIG. 1743B
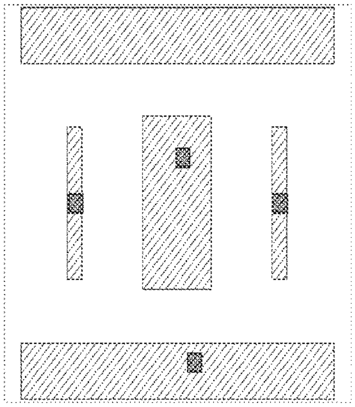
FIG. 1743C

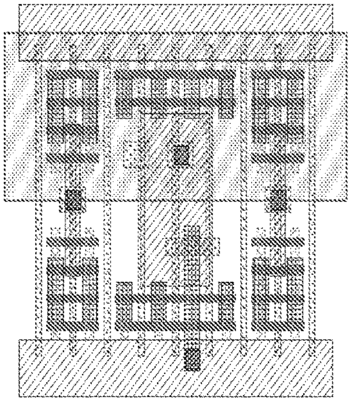
FIG. 1744A
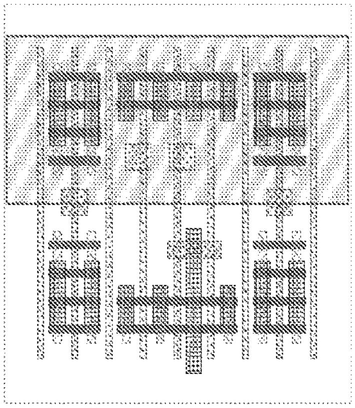
FIG. 1744B
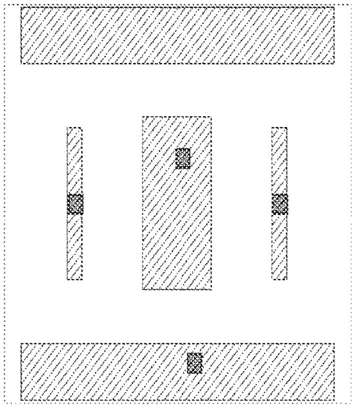
FIG. 1744C

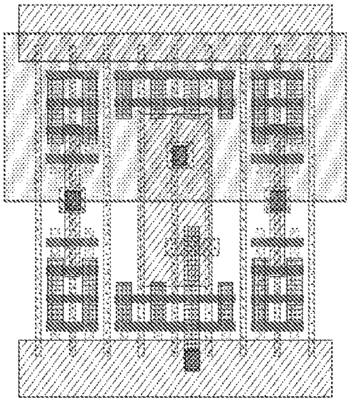
FIG. 1745A
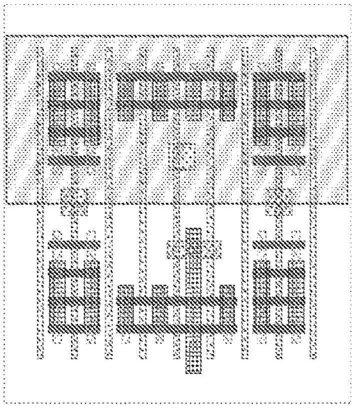
FIG. 1745B
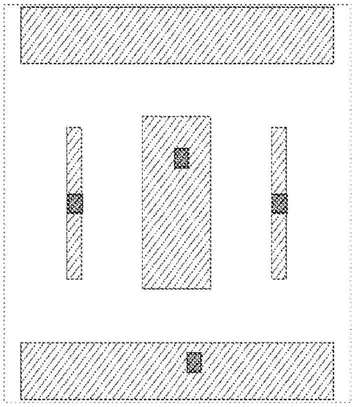
FIG. 1745C
*M* PDF Solutions, Inc.

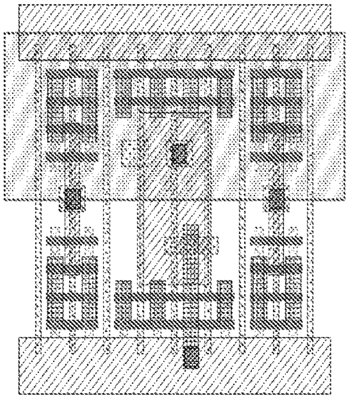
FIG. 1746A
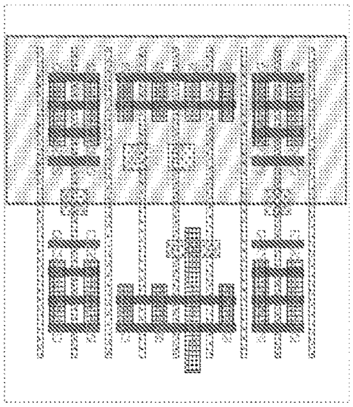
FIG. 1746B
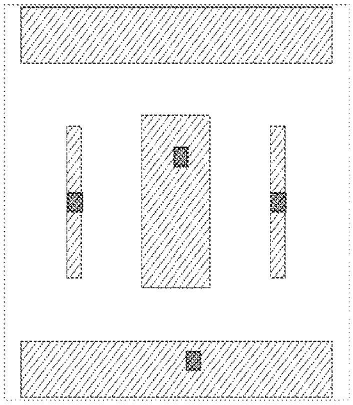
FIG. 1746C

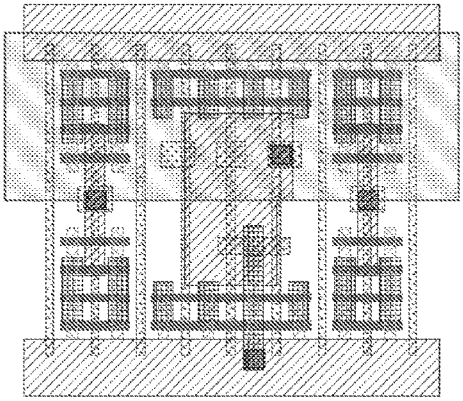
FIG. 1747A
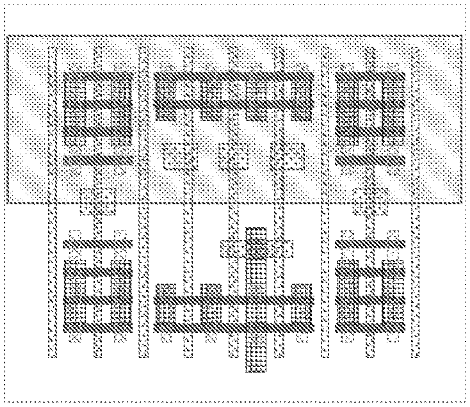
FIG. 1747B
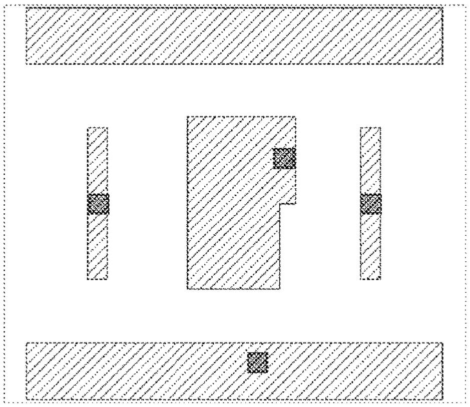
FIG. 1747C

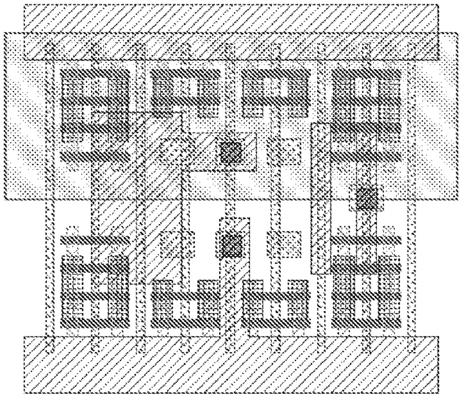
FIG. 1748A
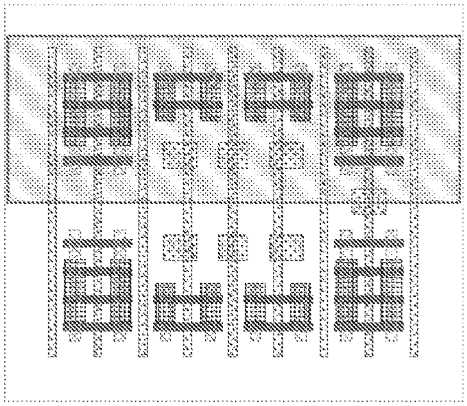
FIG. 1748B
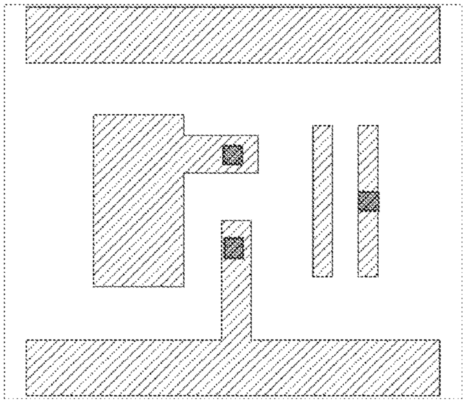
FIG. 1748C
*M* PDF Solutions, Inc.

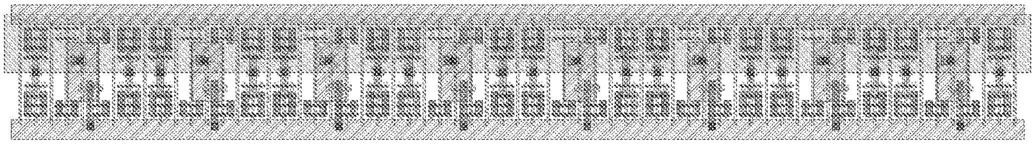
FIG. 1749A
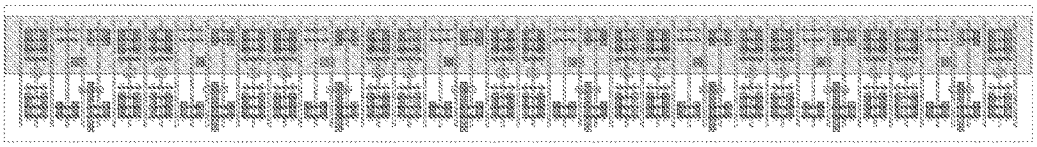
FIG. 1749B
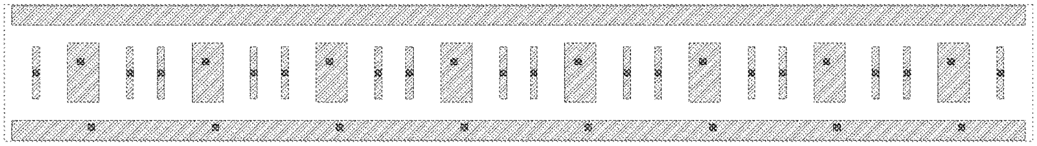
FIG. 1749C

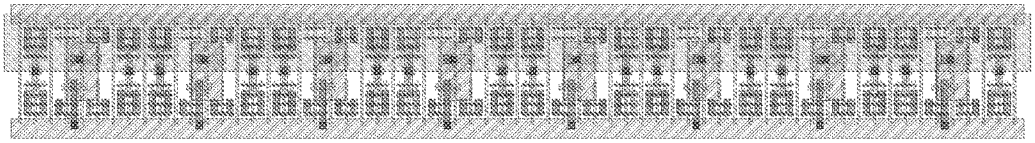
FIG. 1750A
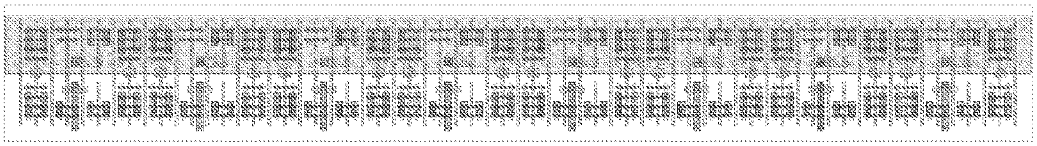
FIG. 1750B
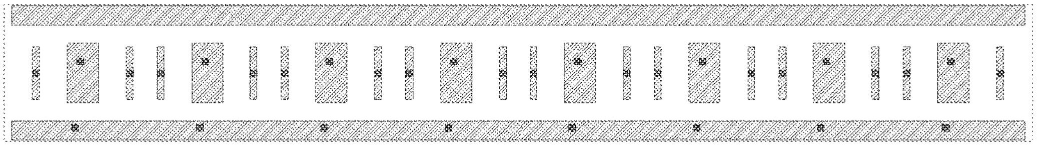
FIG. 1750C
*M* PDF Solutions, Inc.

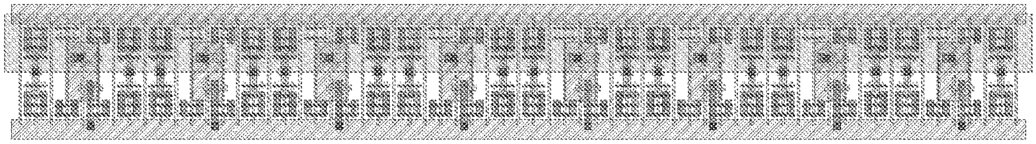
FIG. 1751A
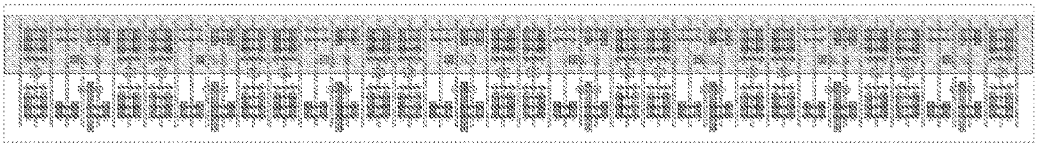
FIG. 1751B
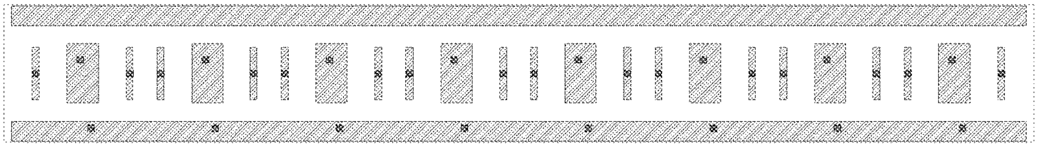
FIG. 1751C

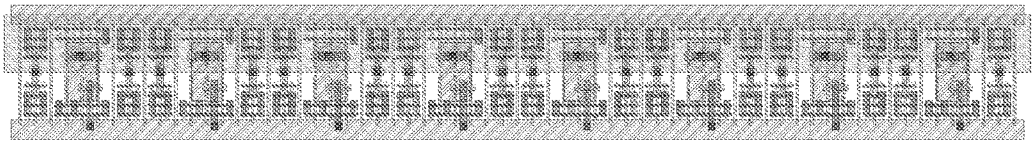
FIG. 1752A
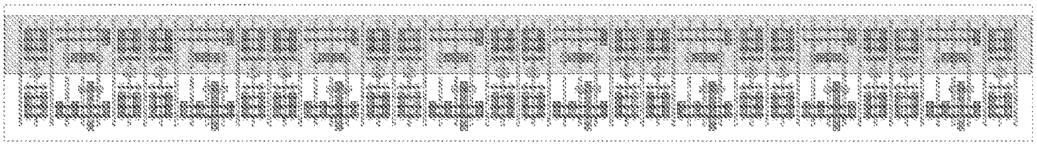
FIG. 1752B
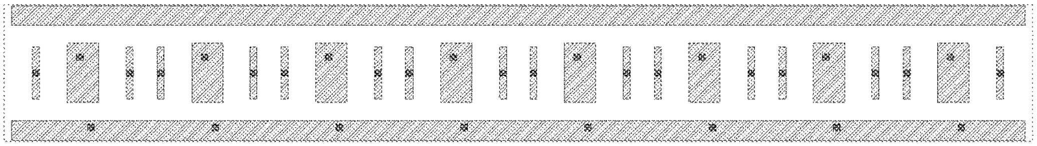
FIG. 1752C

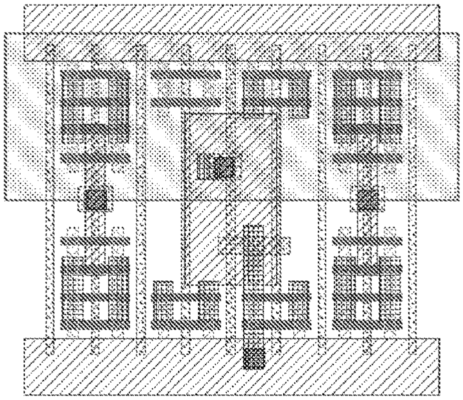
FIG. 1753A
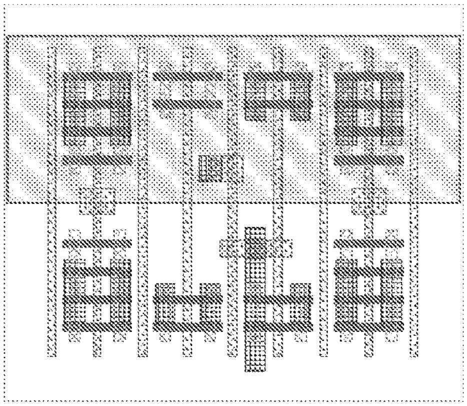
FIG. 1753B
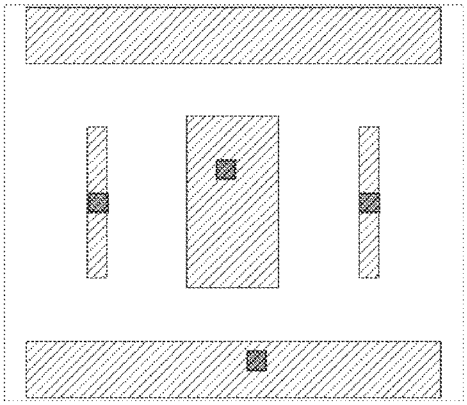
FIG. 1753C
*M* PDF Solutions, Inc.

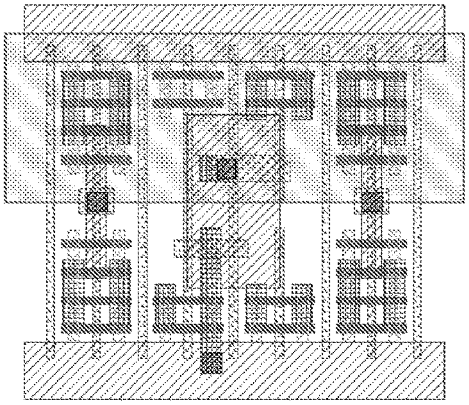
FIG. 1754A
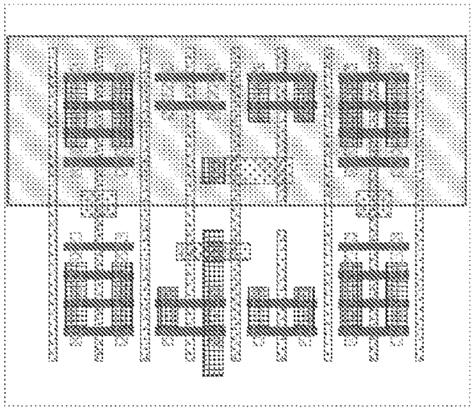
FIG. 1754B
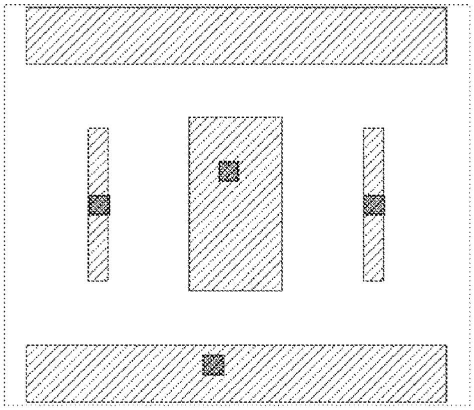
FIG. 1754C
*M* PDF Solutions, Inc.

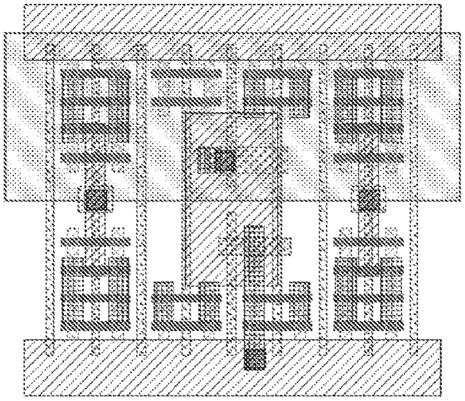
FIG. 1755A
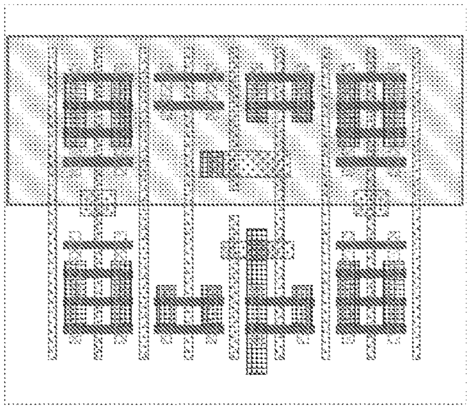
FIG. 1755B
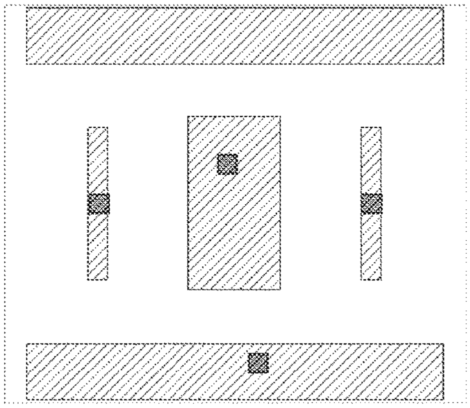
FIG. 1755C

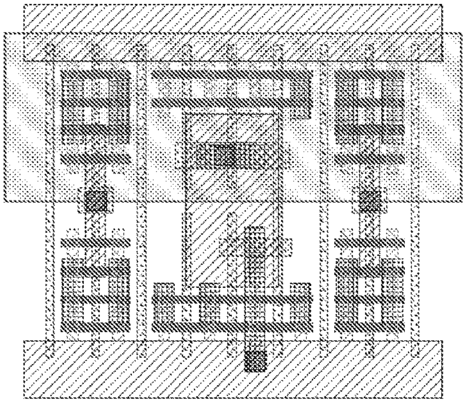
FIG. 1756A
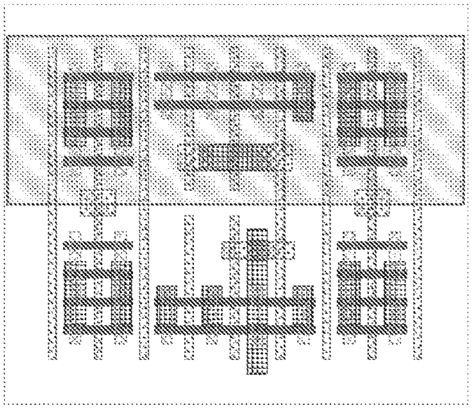
FIG. 1756B
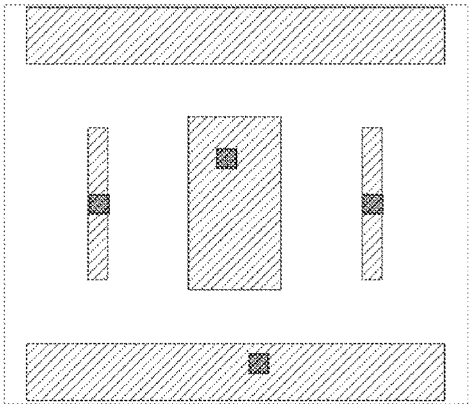
FIG. 1756C

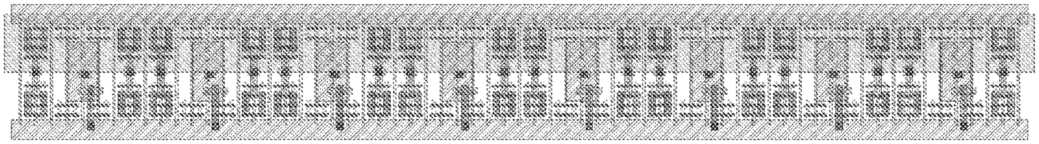
FIG. 1757A
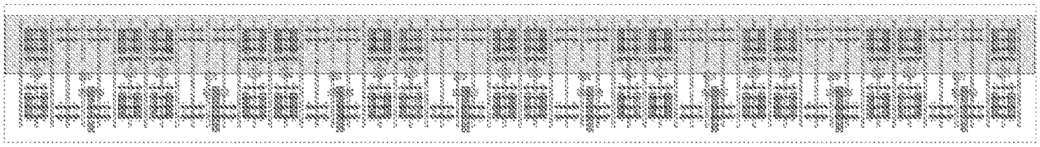
FIG. 1757B
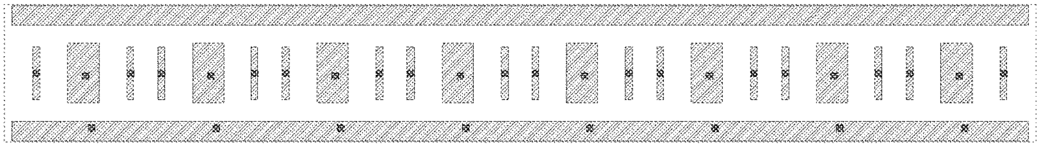
FIG. 1757C

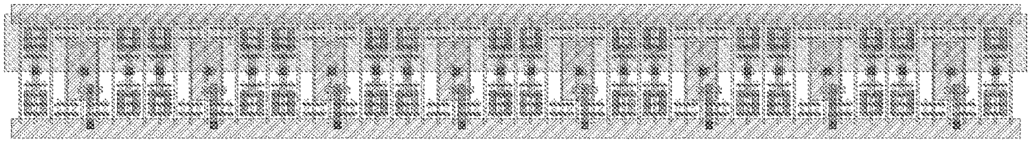
FIG. 1758A
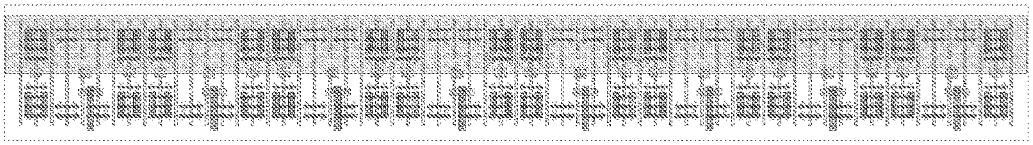
FIG. 1758B
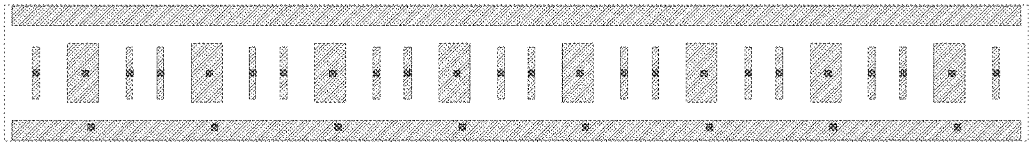
FIG. 1758C

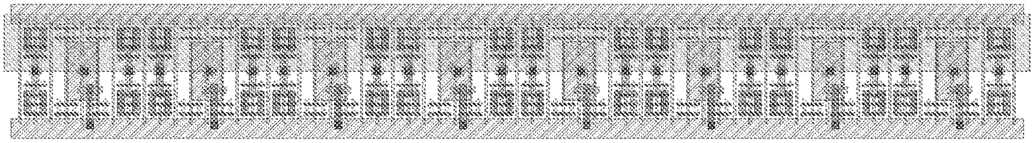
FIG. 1759A
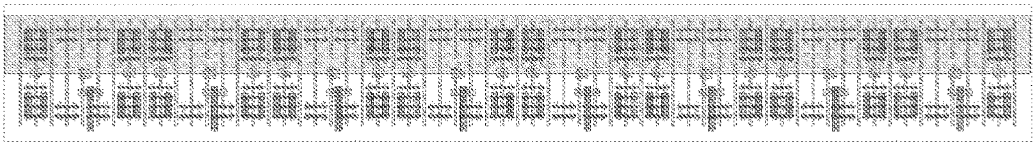
FIG. 1759B
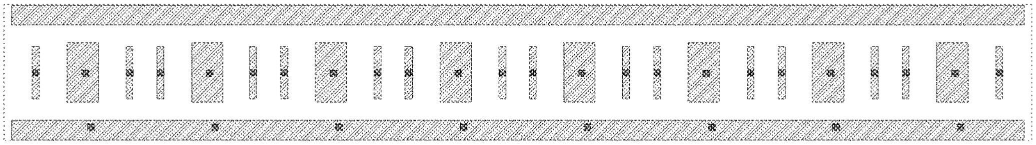
FIG. 1759C

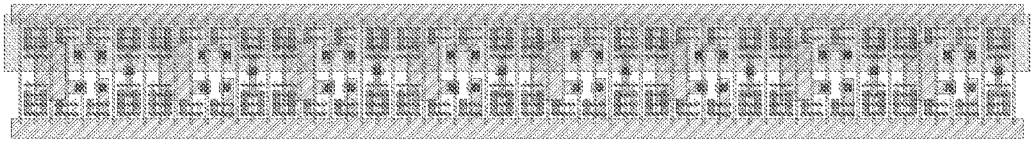
FIG. 1760A
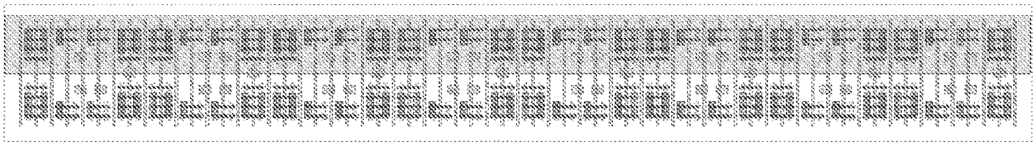
FIG. 1760B
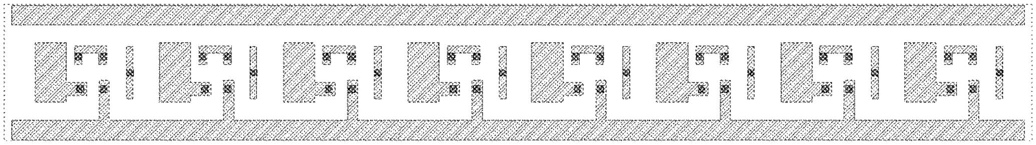
FIG. 1760C
*M* PDF Solutions, Inc.

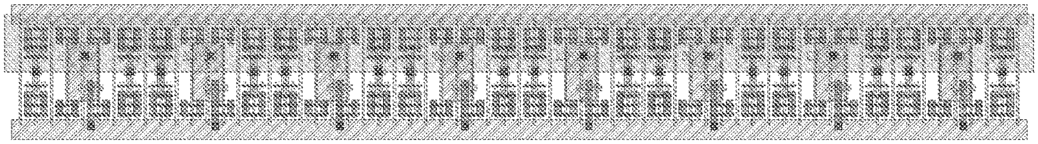
FIG. 1761A
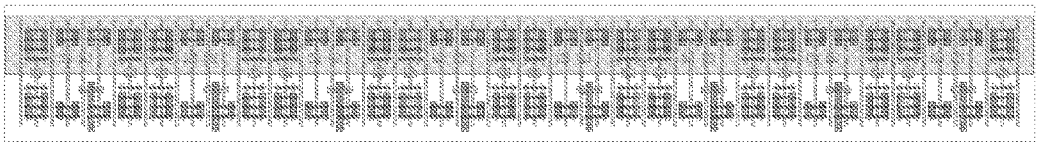
FIG. 1761B
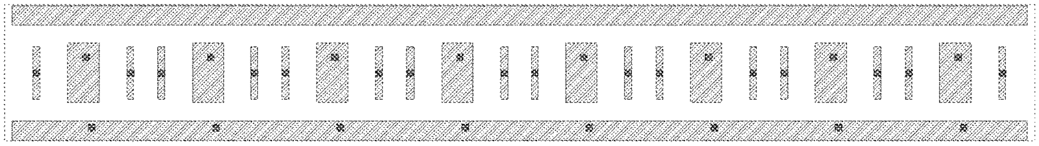
FIG. 1761C
*M* PDF Solutions, Inc.

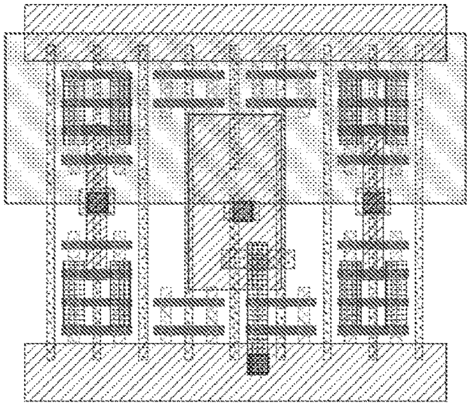
FIG. 1762A
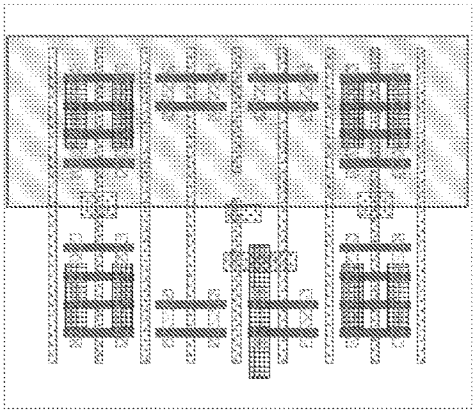
FIG. 1762B
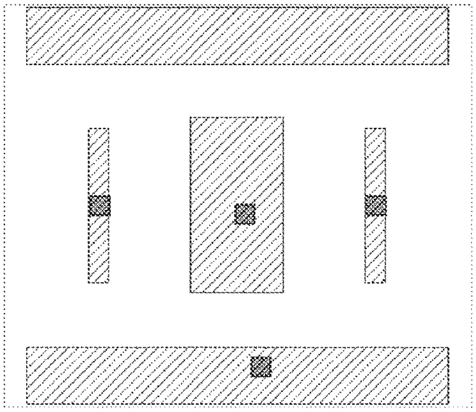
FIG. 1762C

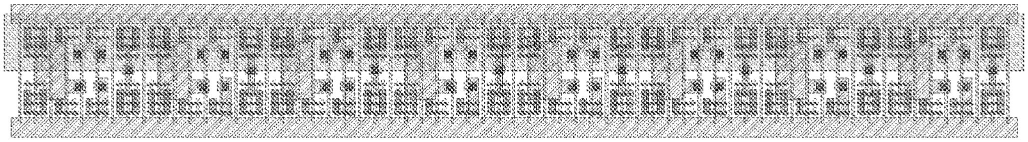
FIG. 1763A
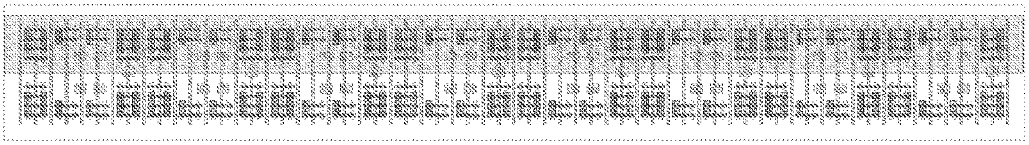
FIG. 1763B
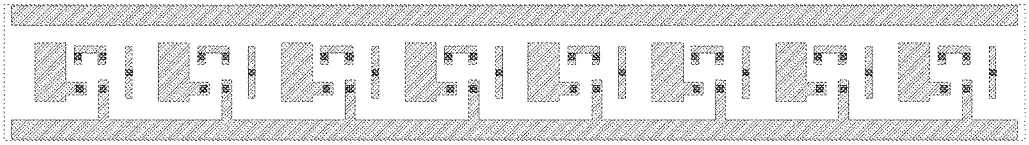
FIG. 1763C

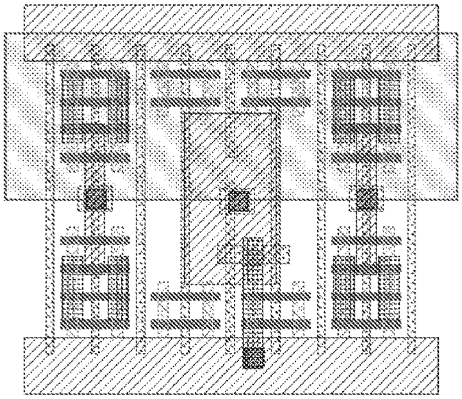
FIG. 1764A
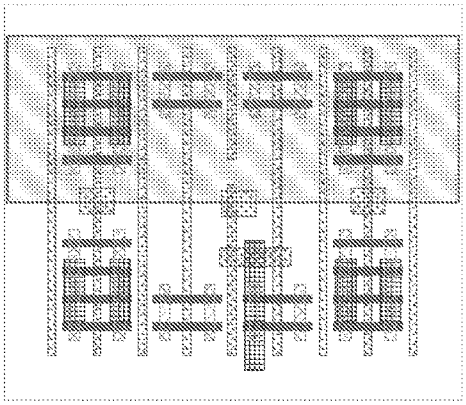
FIG. 1764B
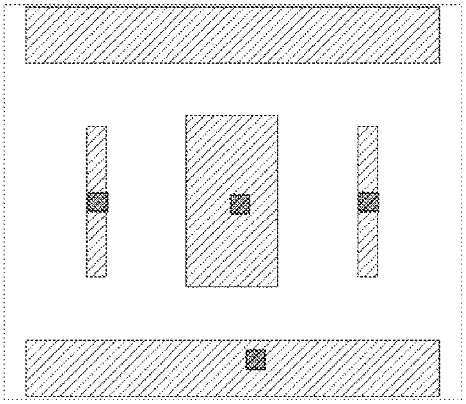
FIG. 1764C

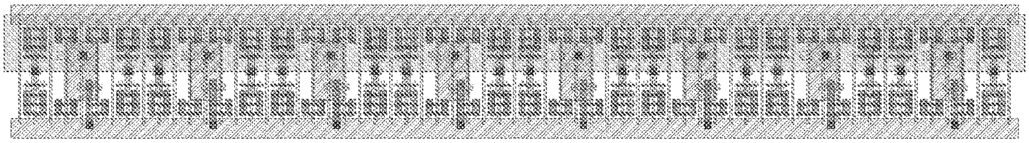
FIG. 1765A
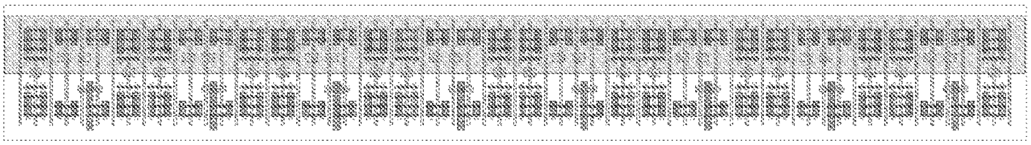
FIG. 1765B
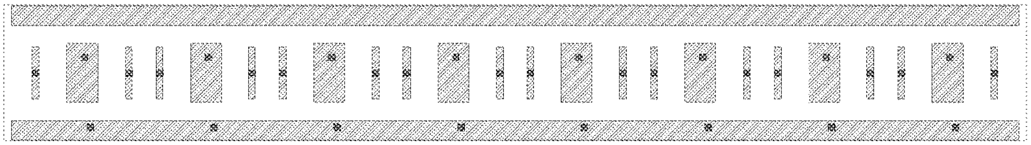
FIG. 1765C

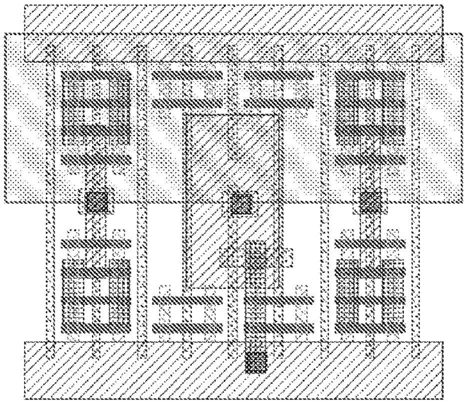
FIG. 1766A
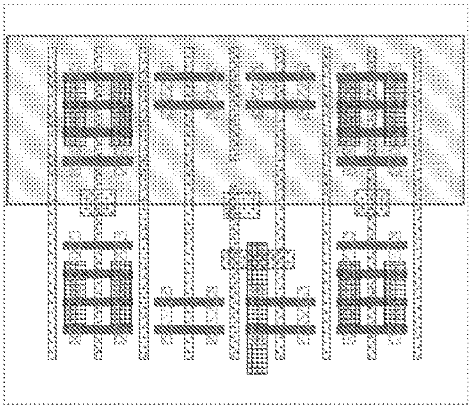
FIG. 1766B
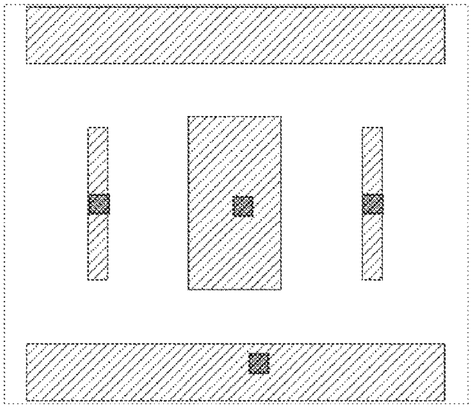
FIG. 1766C

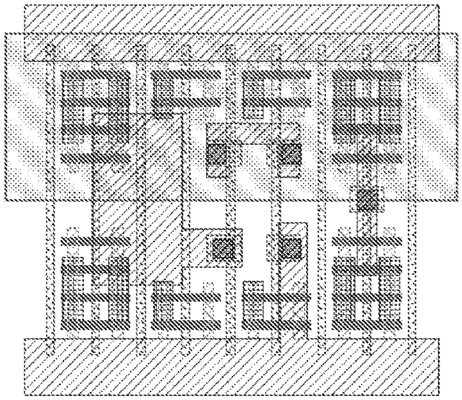
FIG. 1767A
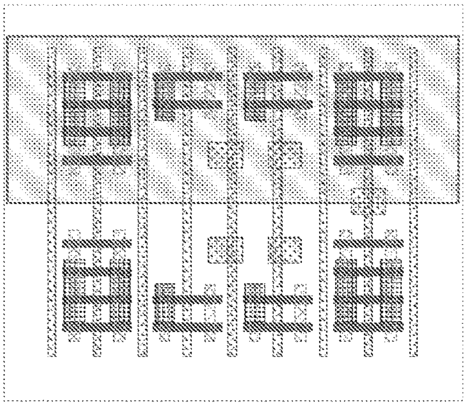
FIG. 1767B
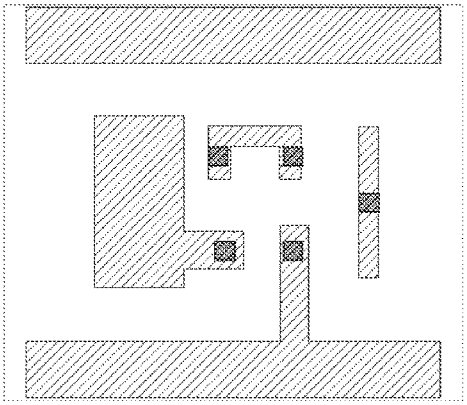
FIG. 1767C
*M* PDF Solutions, Inc.

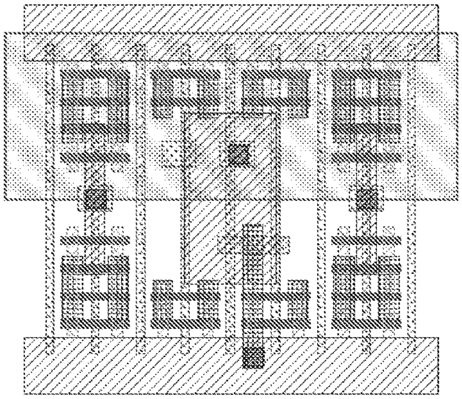
FIG. 1768A
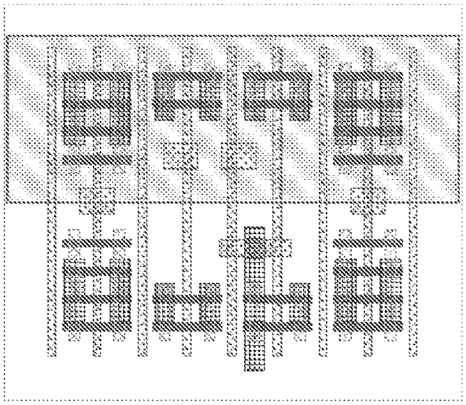
FIG. 1768B
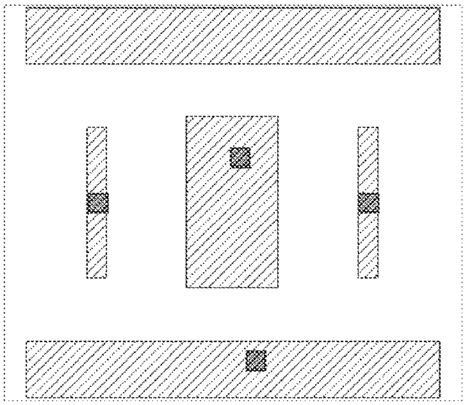
FIG. 1768C

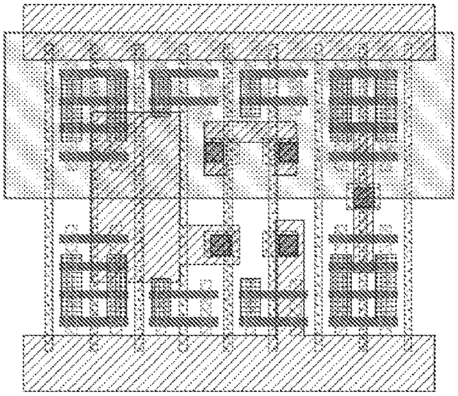
FIG. 1769A
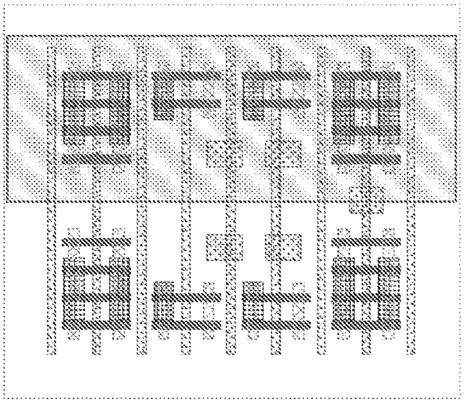
FIG. 1769B
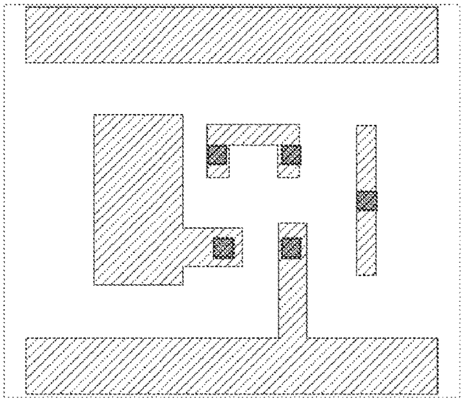
FIG. 1769C

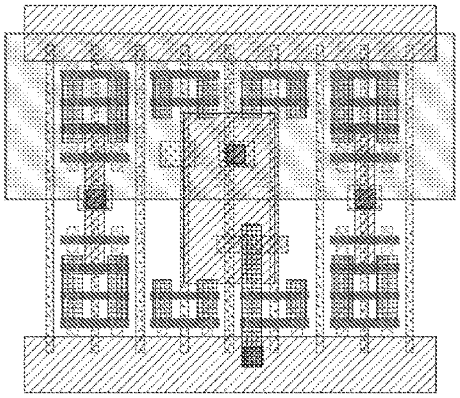
FIG. 1770A
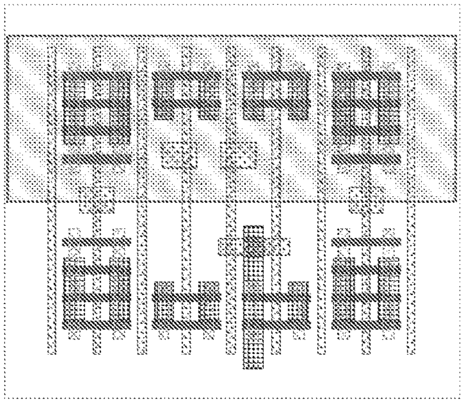
FIG. 1770B
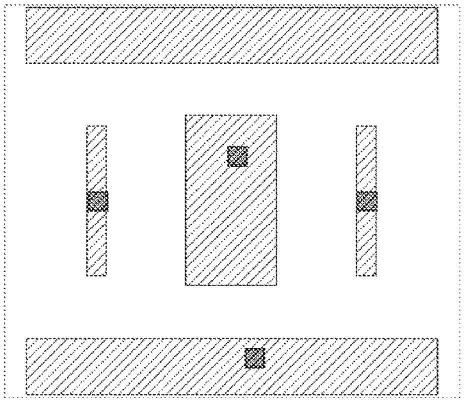
FIG. 1770C

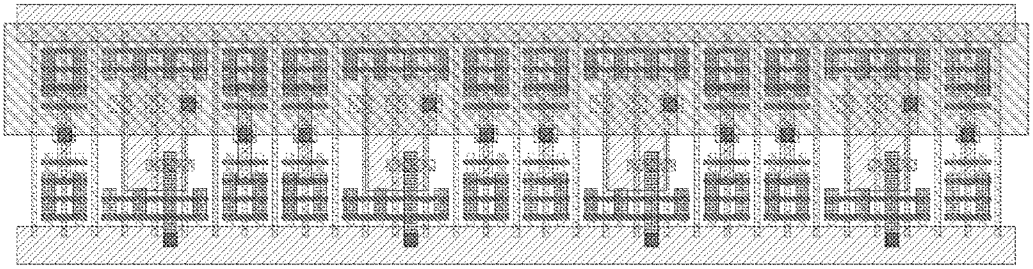
FIG. 1771A
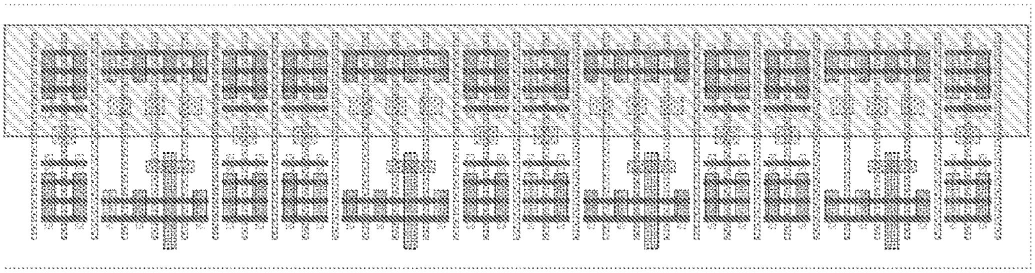
FIG. 1771B
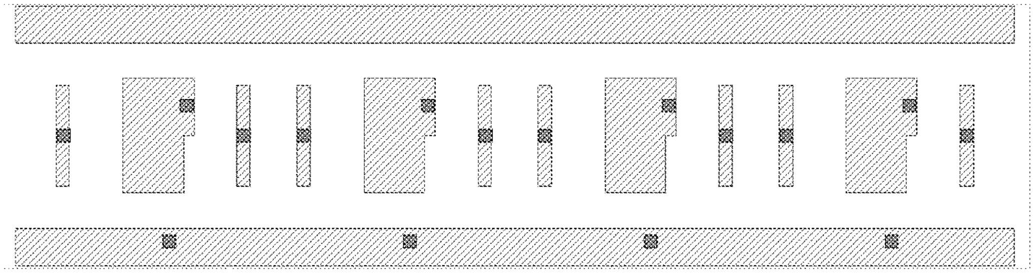
FIG. 1771C
*M* PDF Solutions, Inc.

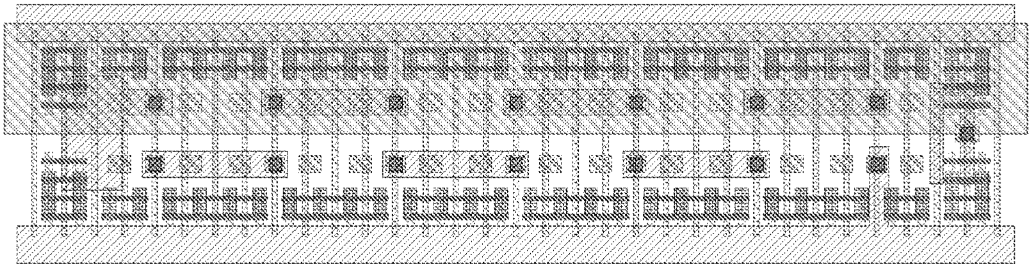
FIG. 1772A
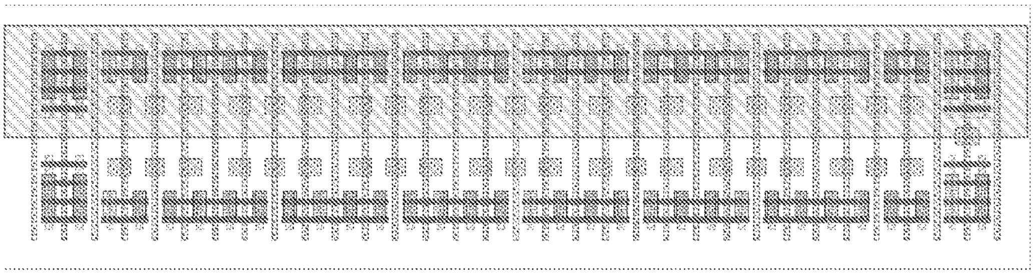
FIG. 1772B
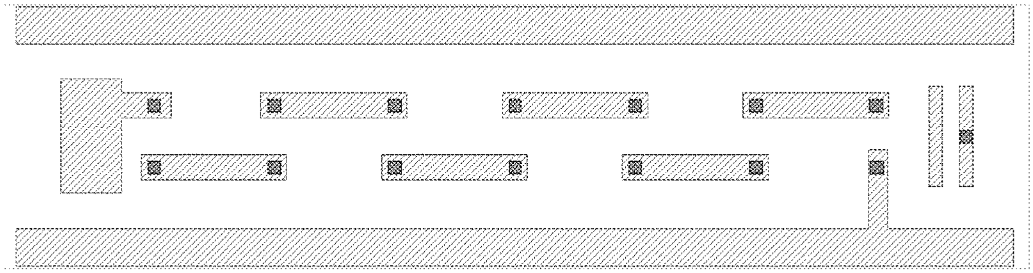
FIG. 1772C

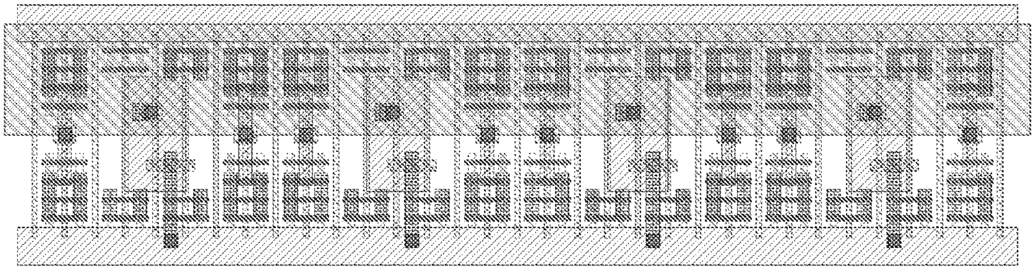
FIG. 1773A
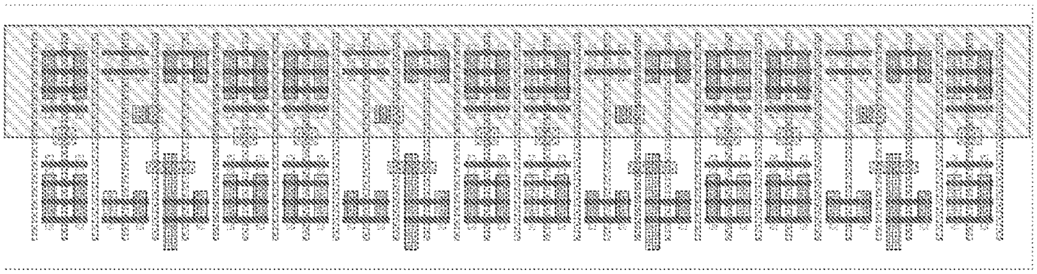
FIG. 1773B
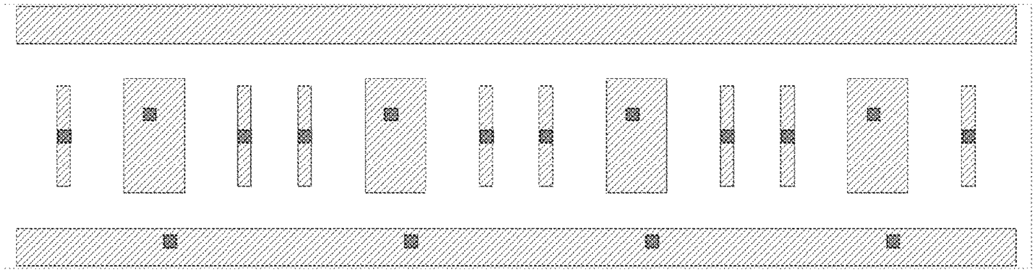
FIG. 1773C

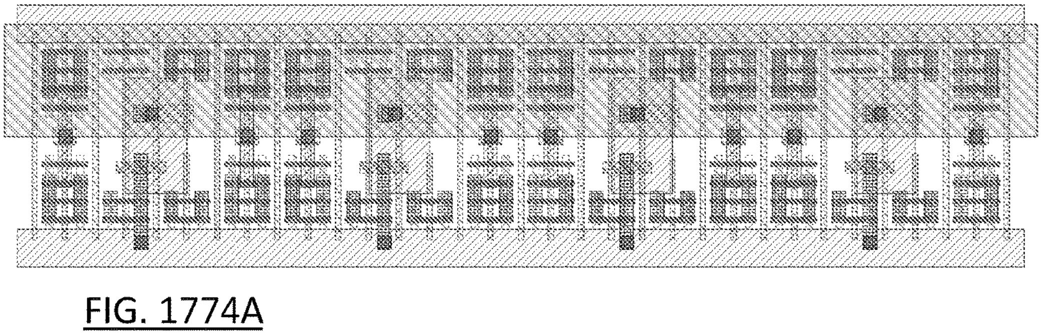
FIG. 1774A
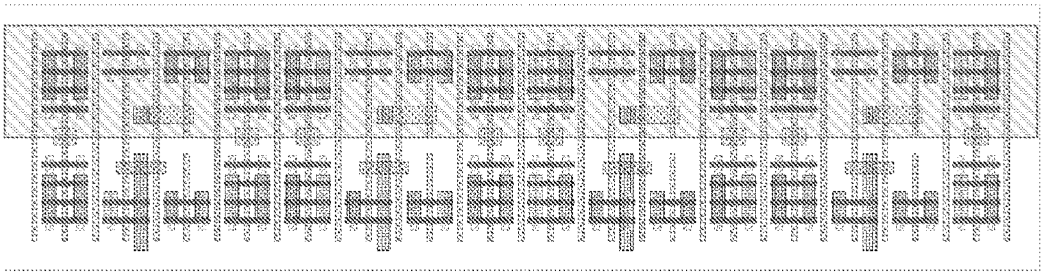
FIG. 1774B
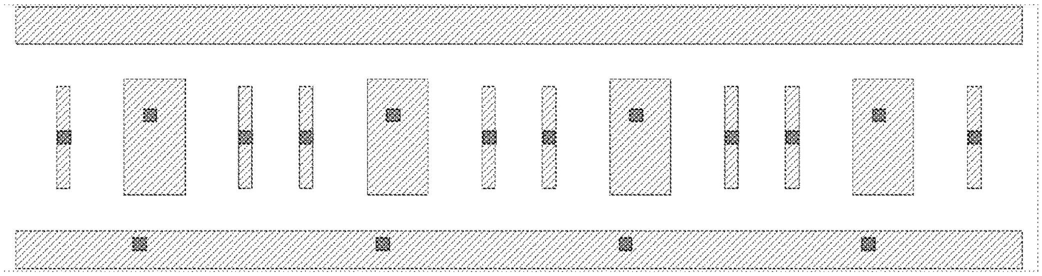
FIG. 1774C
*M* PDF Solutions, Inc.

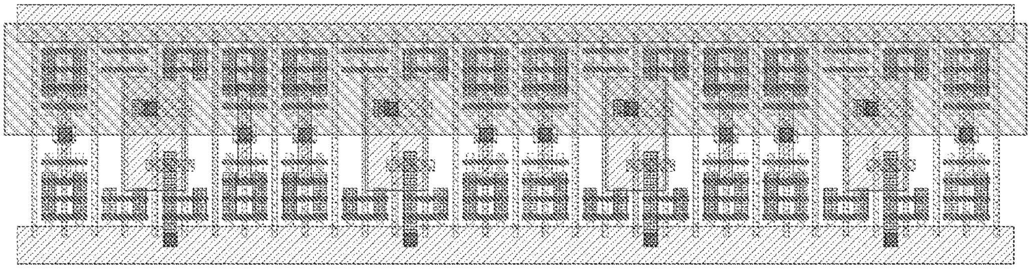
FIG. 1775A
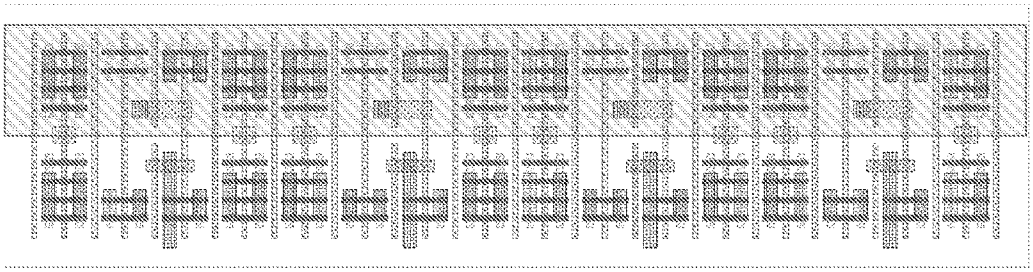
FIG. 1775B
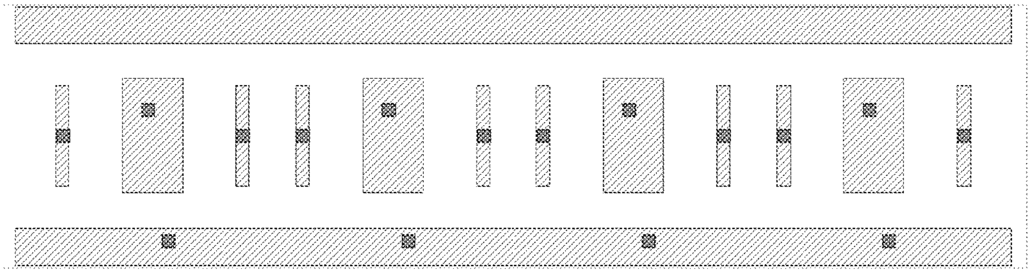
FIG. 1775C

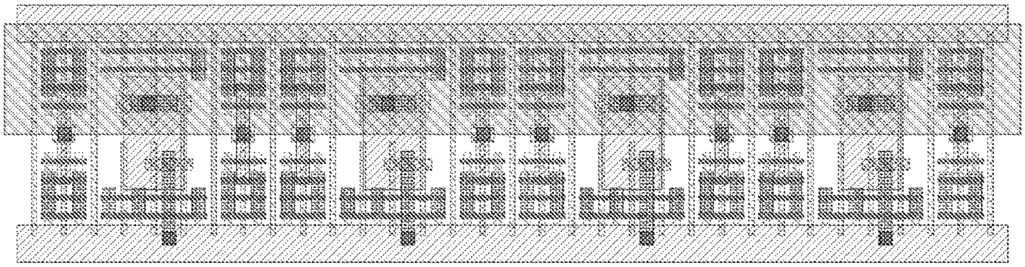
FIG. 1776A
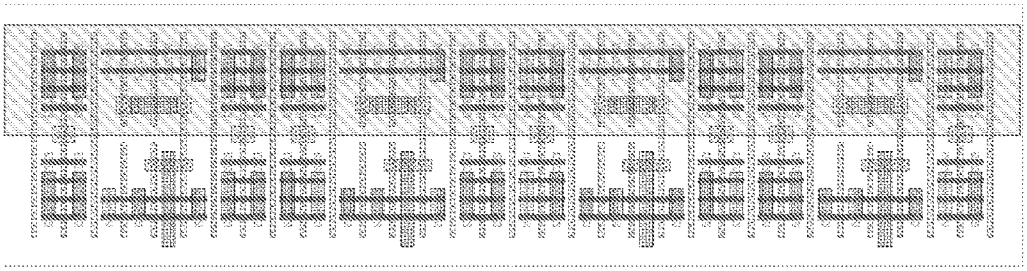
FIG. 1776B
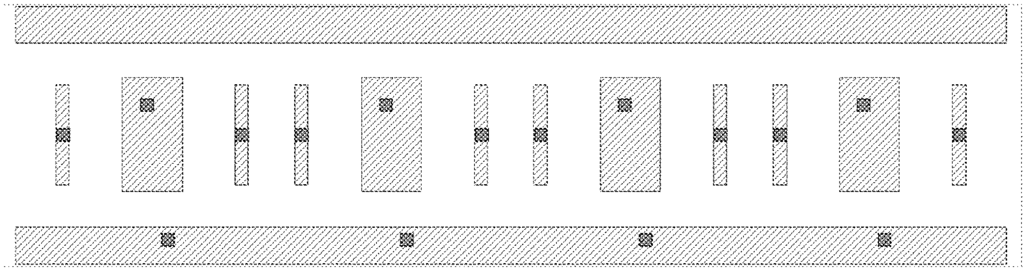
FIG. 1776C

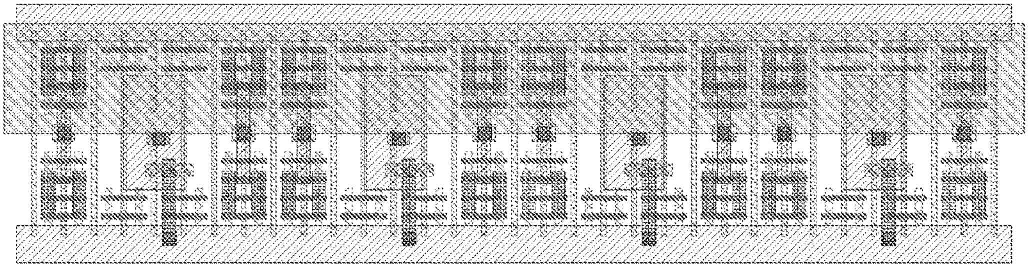
FIG. 1777A
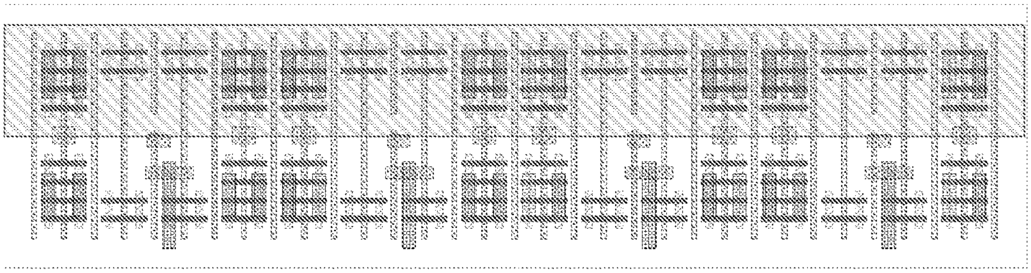
FIG. 1777B
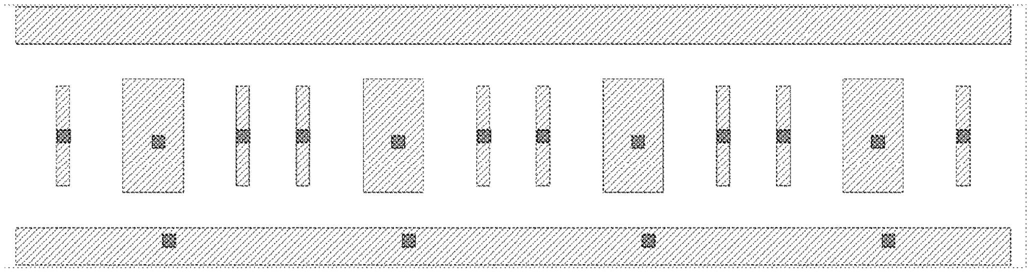
FIG. 1777C
*M* PDF Solutions, Inc.

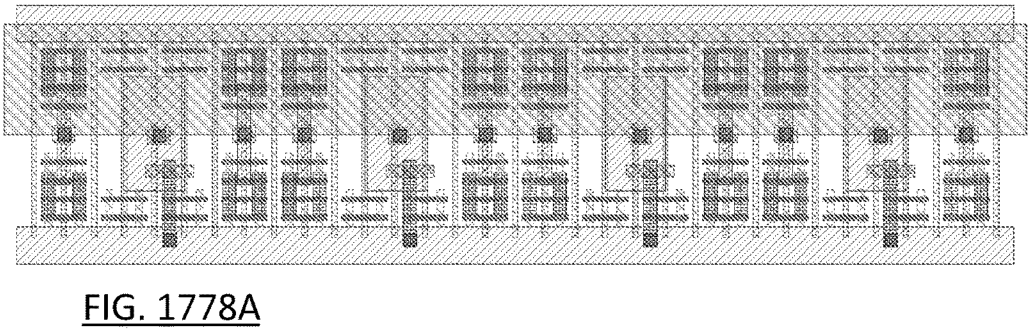
FIG. 1778A
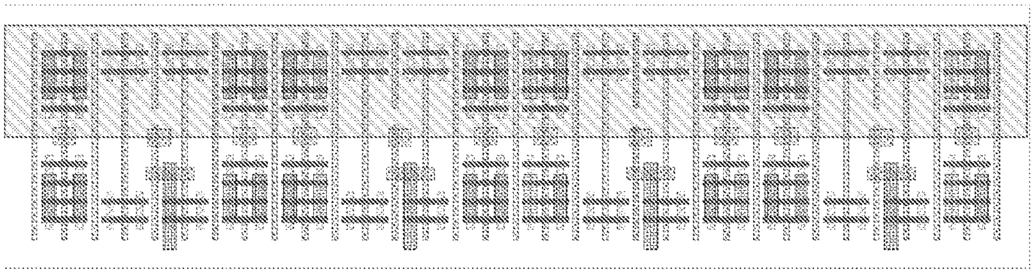
FIG. 1778B
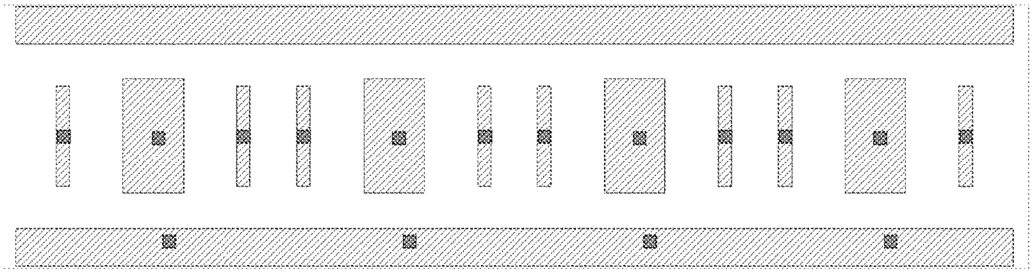
FIG. 1778C

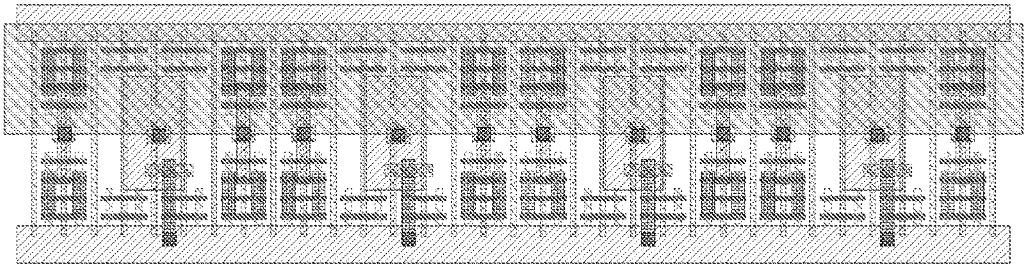
FIG. 1779A
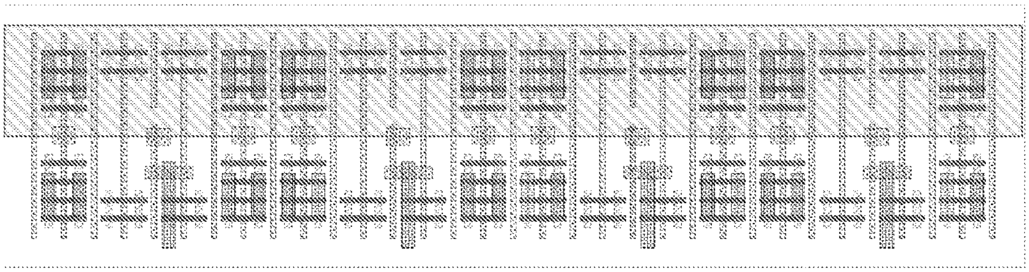
FIG. 1779B
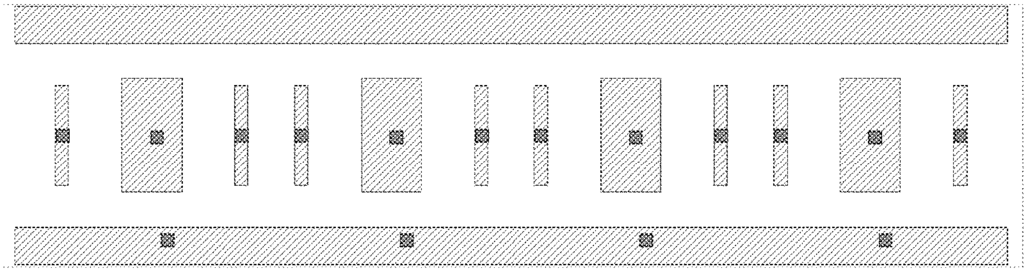
FIG. 1779C
*M* PDF Solutions, Inc.

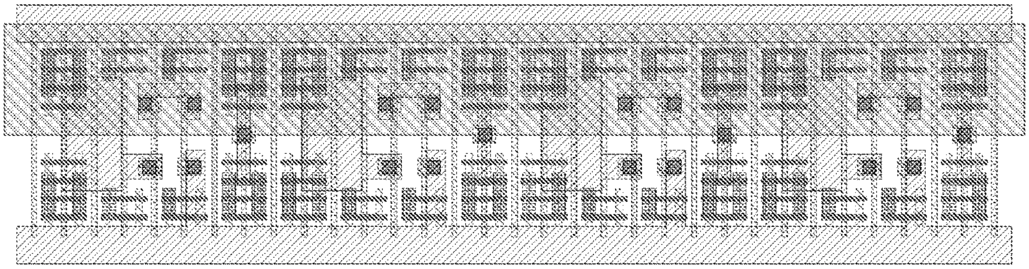
FIG. 1780A
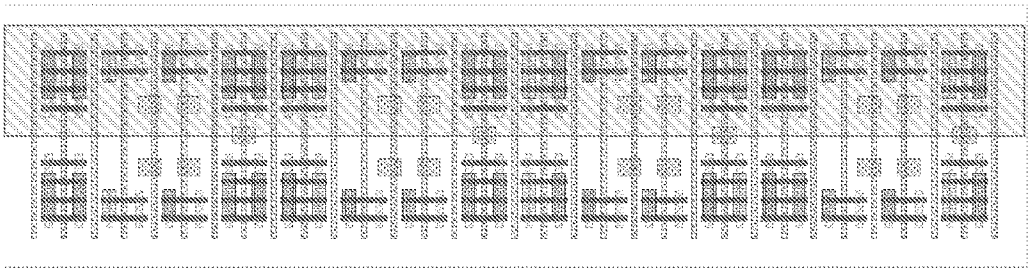
FIG. 1780B
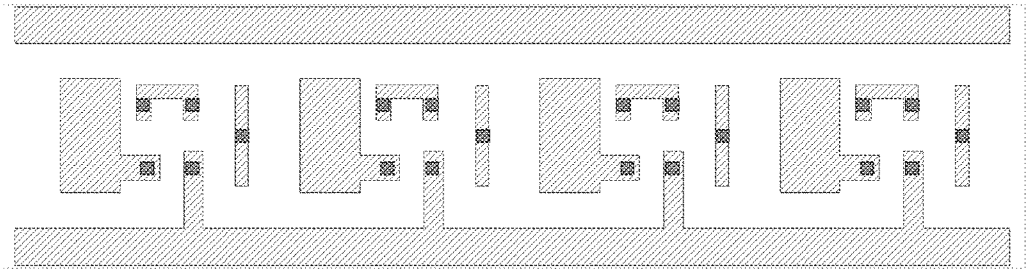
FIG. 1780C

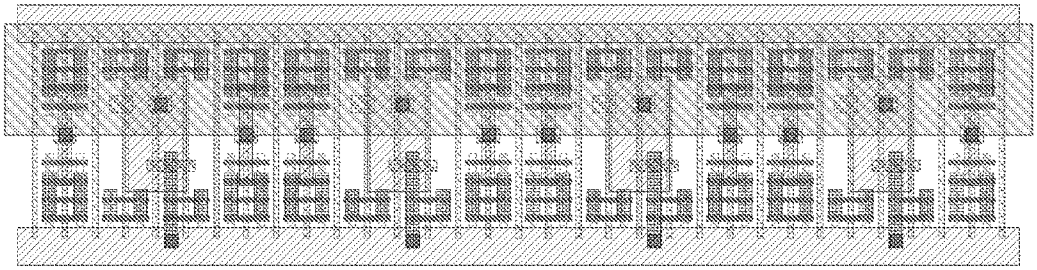
FIG. 1781A
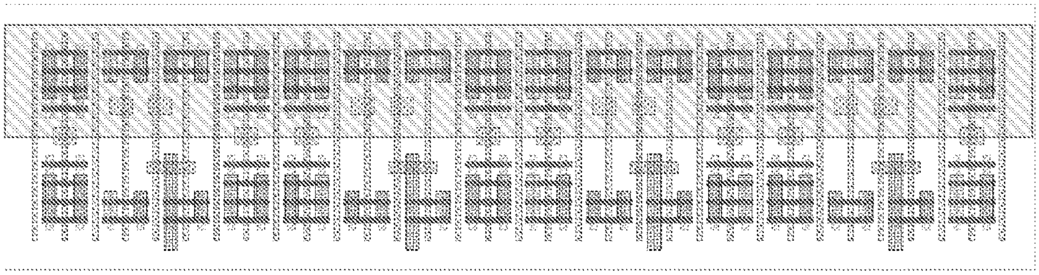
FIG. 1781B
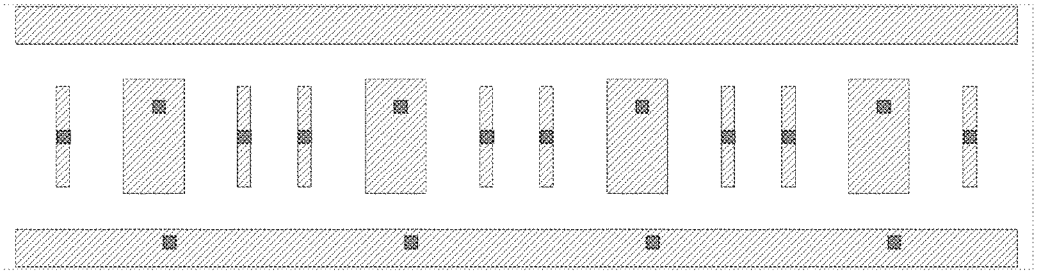
FIG. 1781C
*M* PDF Solutions, Inc.

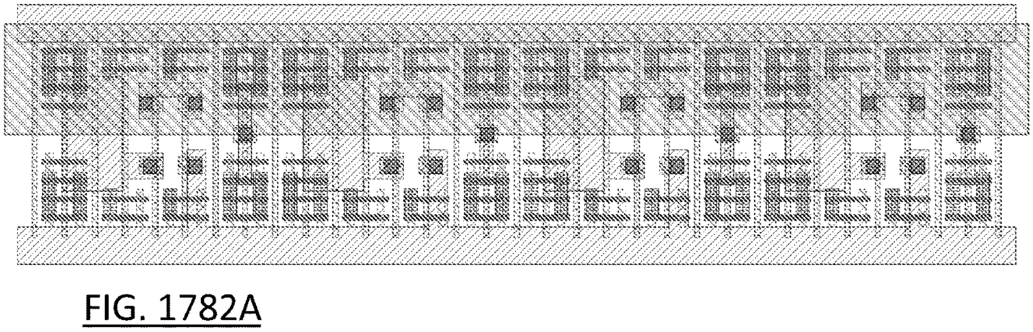
FIG. 1782A
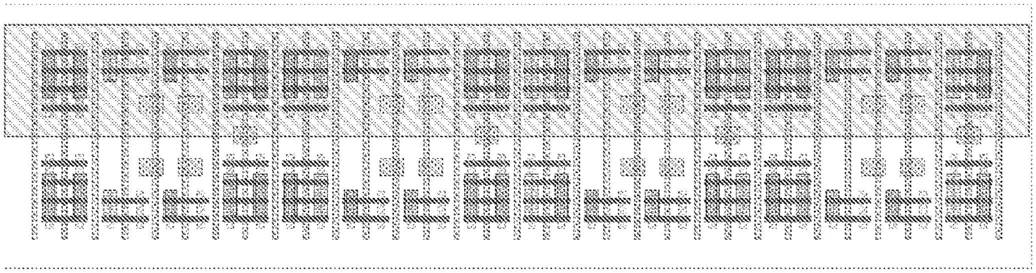
FIG. 1782B
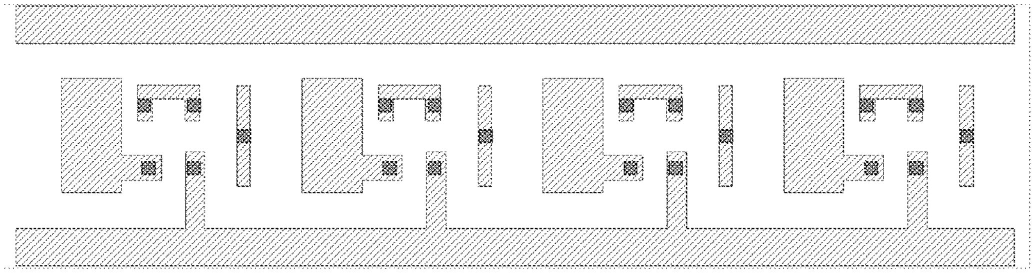
FIG. 1782C

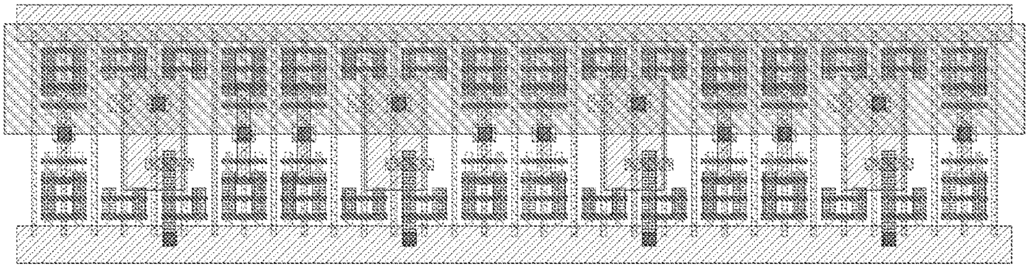
FIG. 1783A
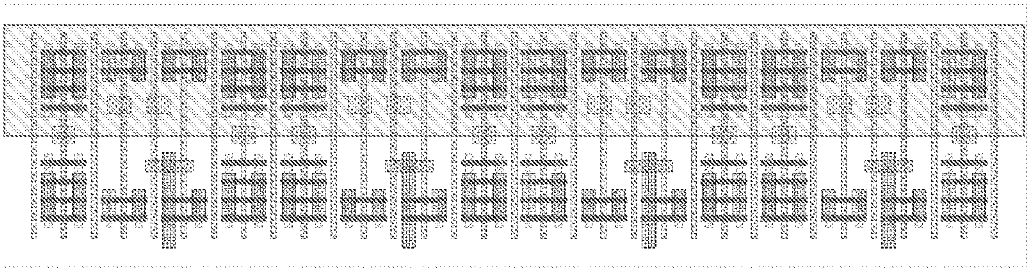
FIG. 1783B
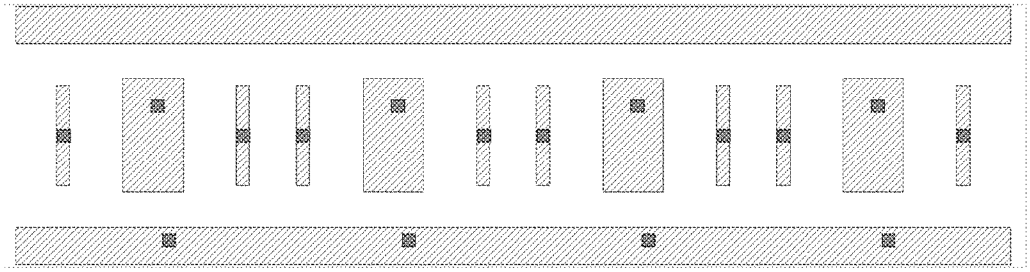
FIG. 1783C

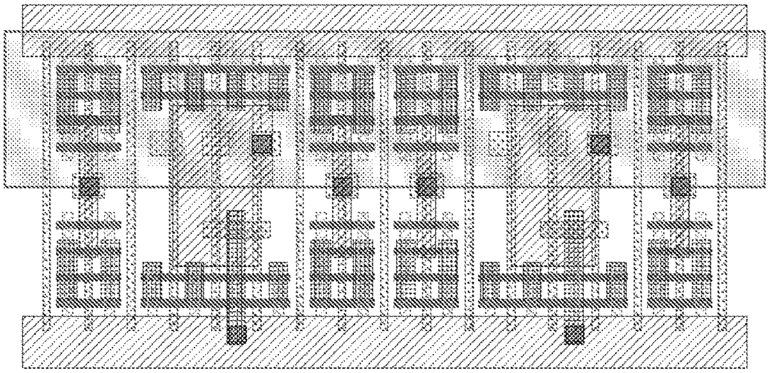
FIG. 1784A
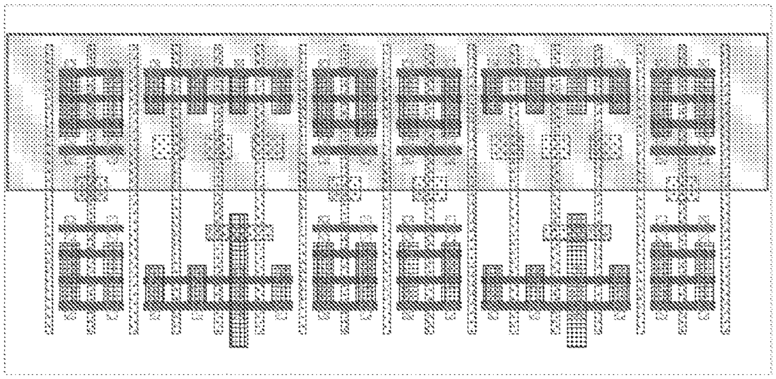
FIG. 1784B
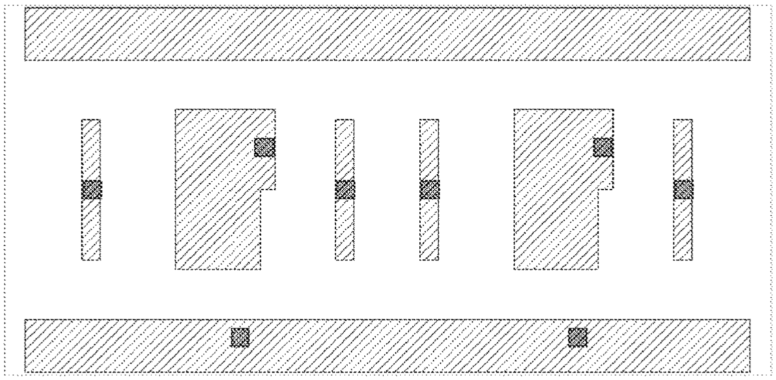
FIG. 1784C

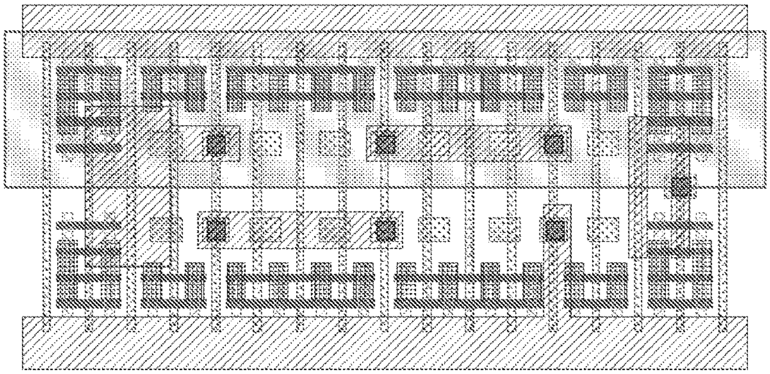
FIG. 1785A
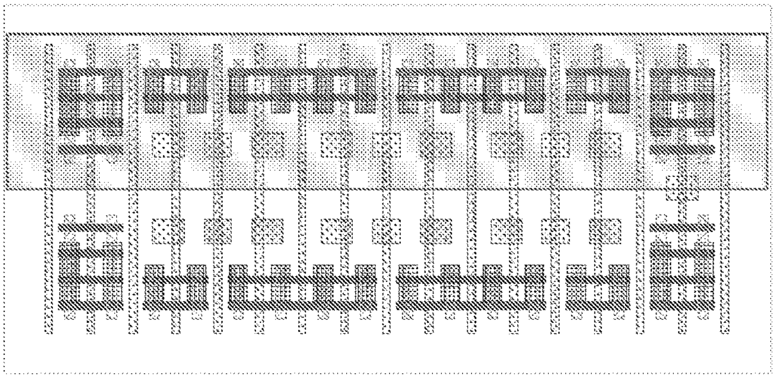
FIG. 1785B
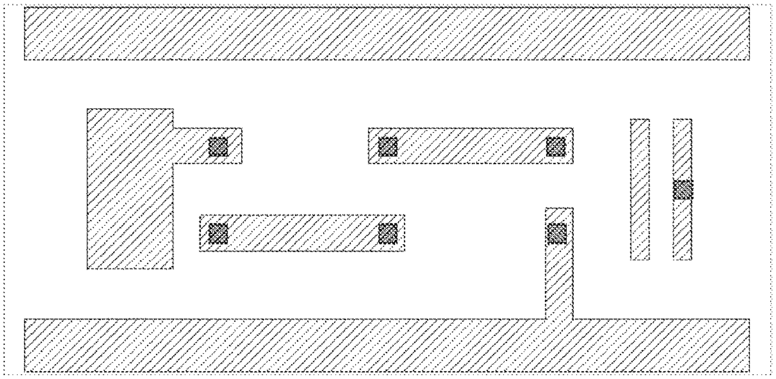
FIG. 1785C

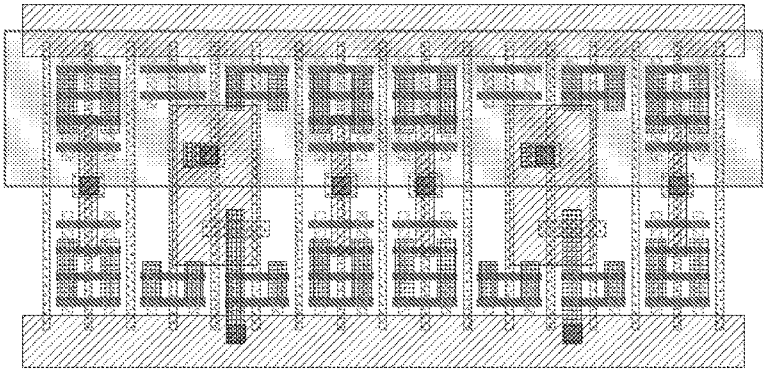
FIG. 1786A
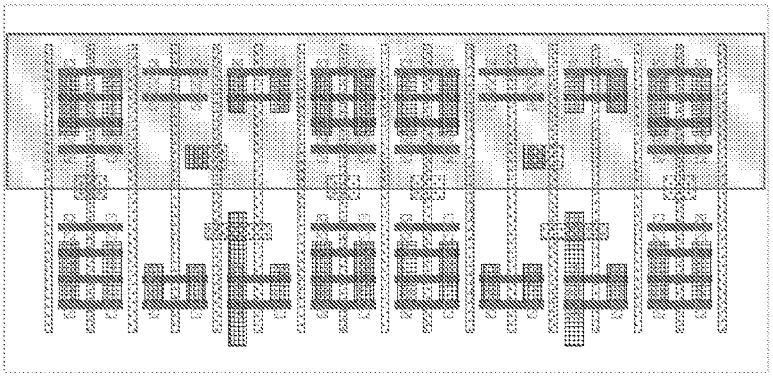
FIG. 1786B
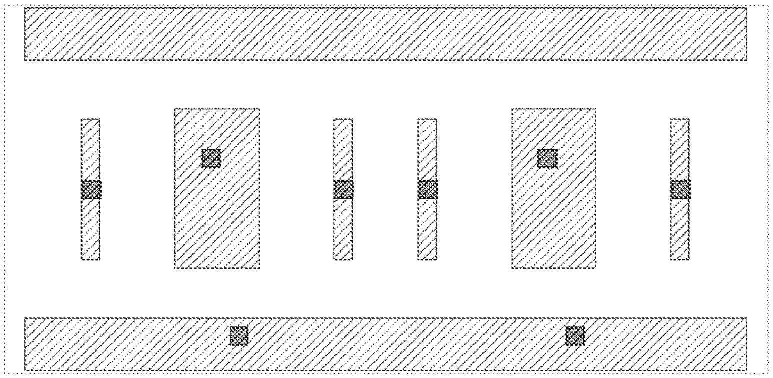
FIG. 1786C
*M* PDF Solutions, Inc.

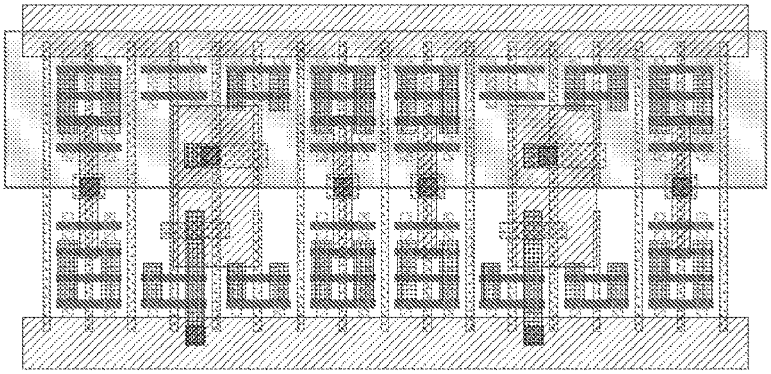
FIG. 1787A
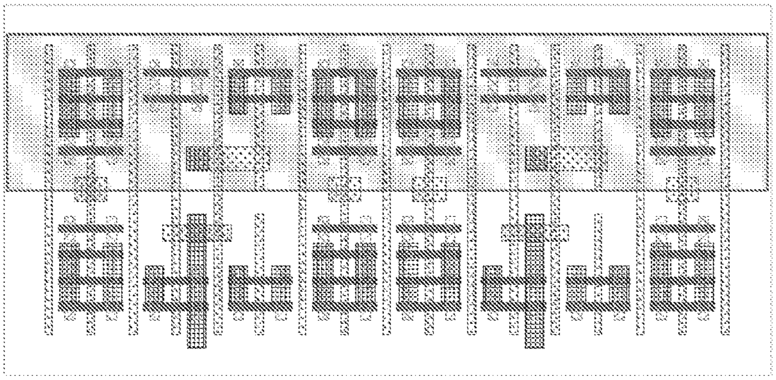
FIG. 1787B
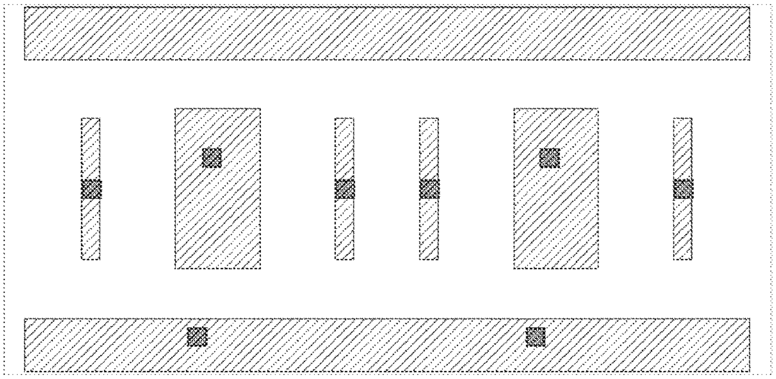
FIG. 1787C
*M* PDF Solutions, Inc.

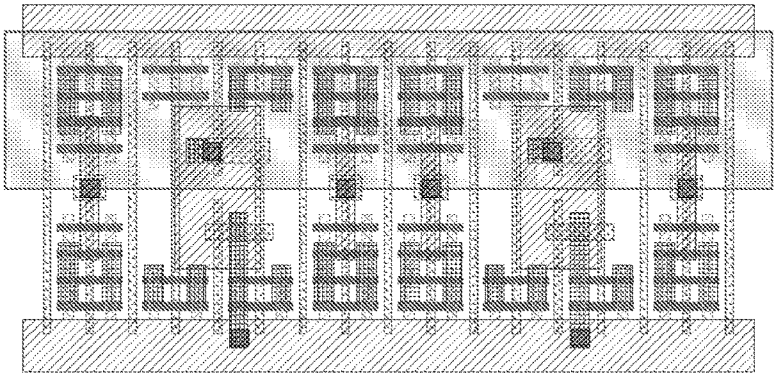
FIG. 1788A
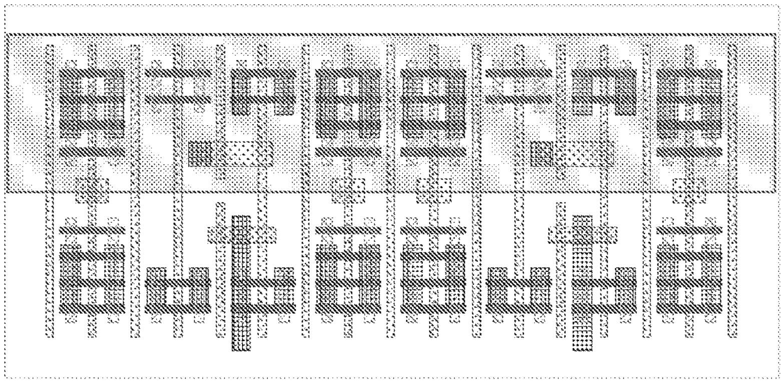
FIG. 1788B
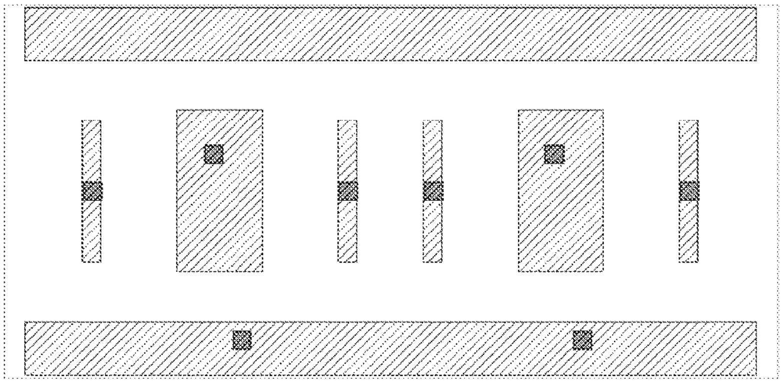
FIG. 1788C
*M* PDF Solutions, Inc.

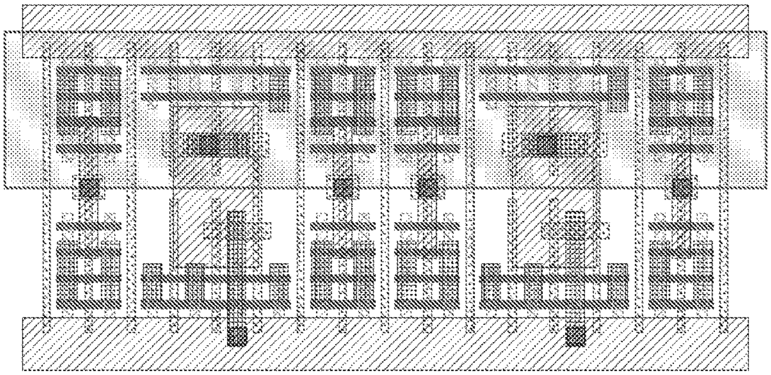
FIG. 1789A
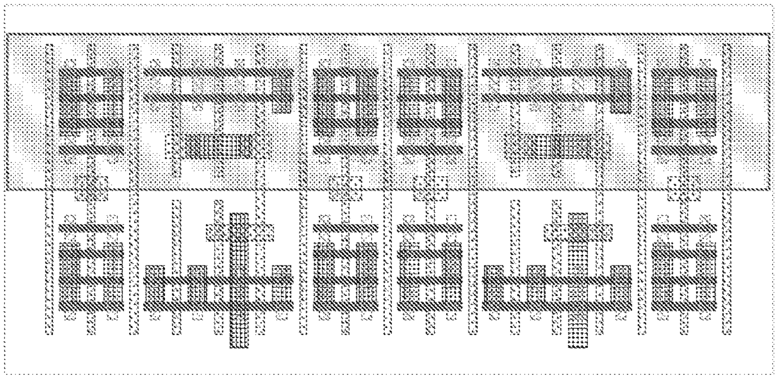
FIG. 1789B
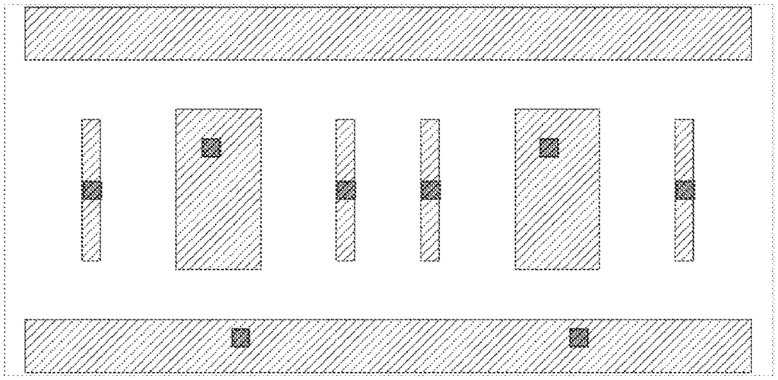
FIG. 1789C
*M* PDF Solutions, Inc.

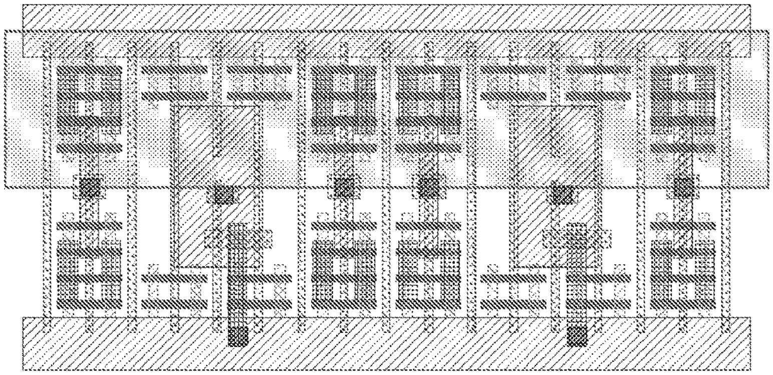
FIG. 1790A
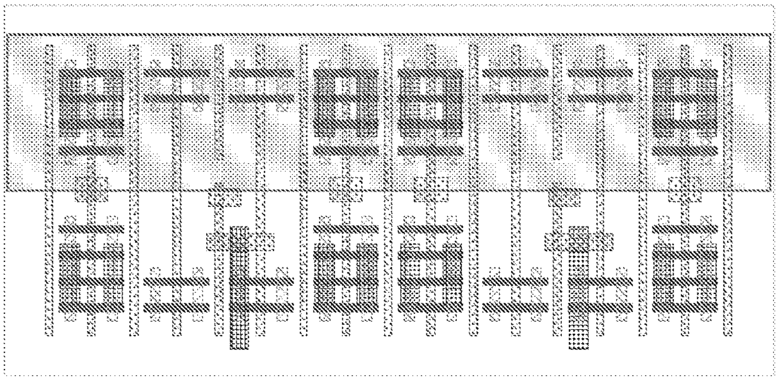
FIG. 1790B
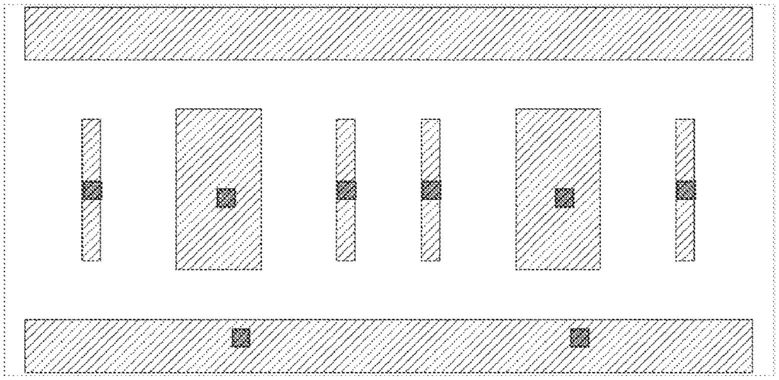
FIG. 1790C
*M* PDF Solutions, Inc.

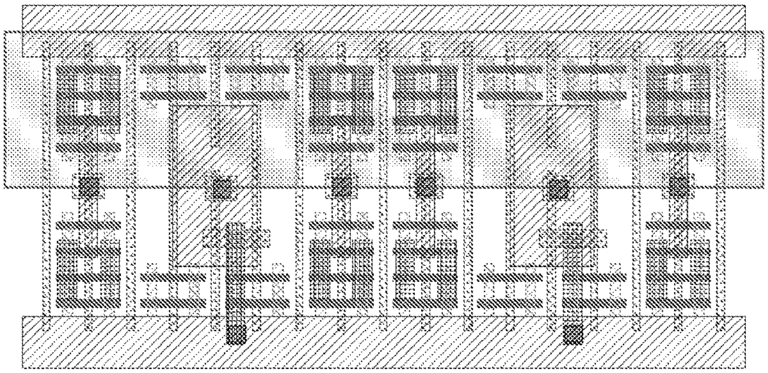
FIG. 1791A
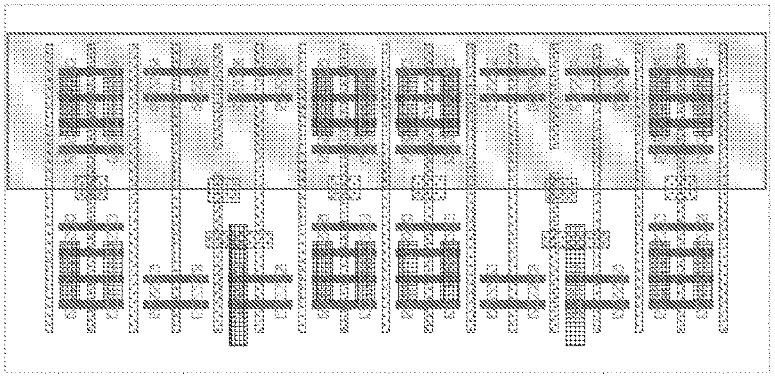
FIG. 1791B
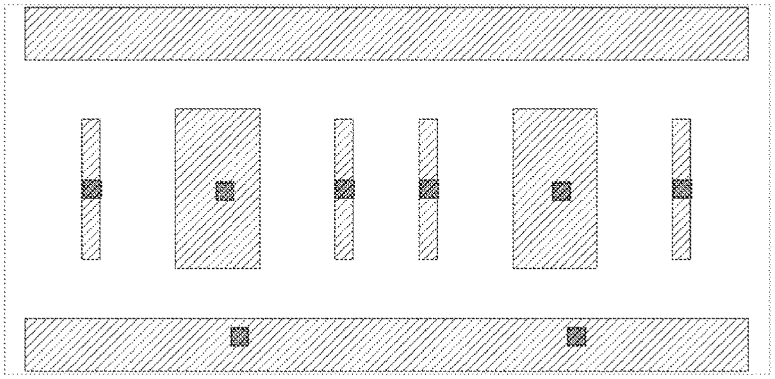
FIG. 1791C
*M* PDF Solutions, Inc.

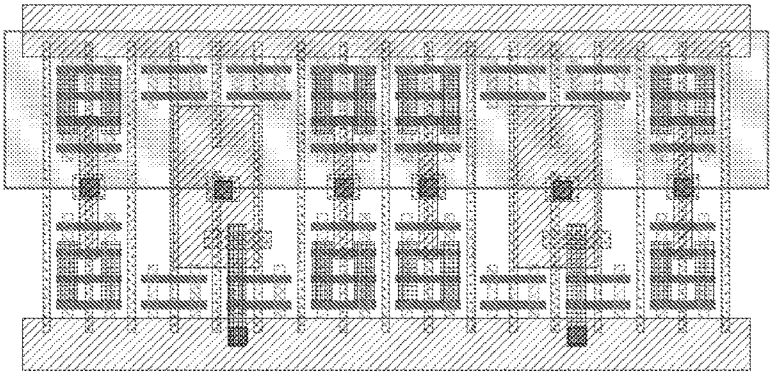
FIG. 1792A
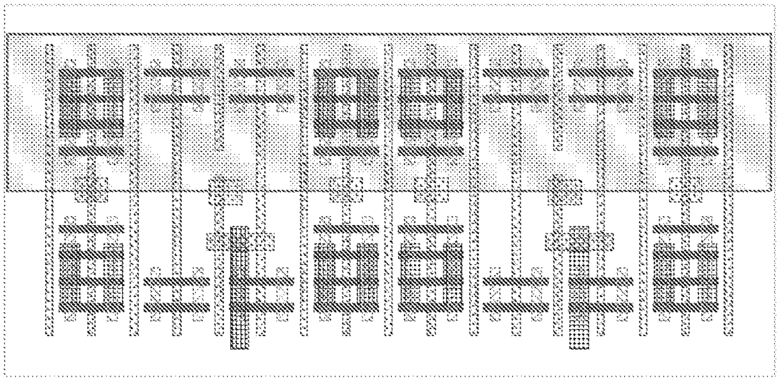
FIG. 1792B
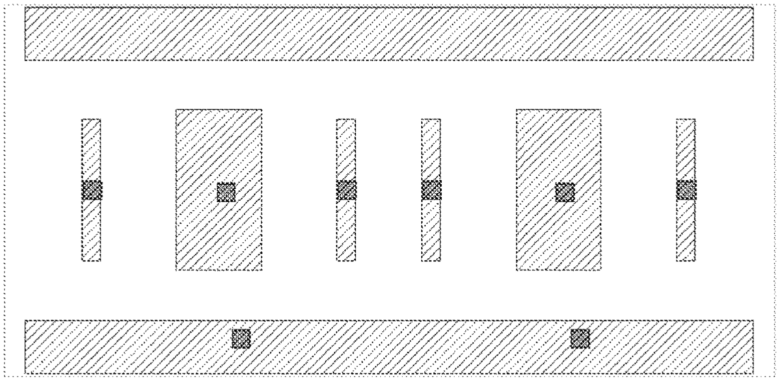
FIG. 1792C

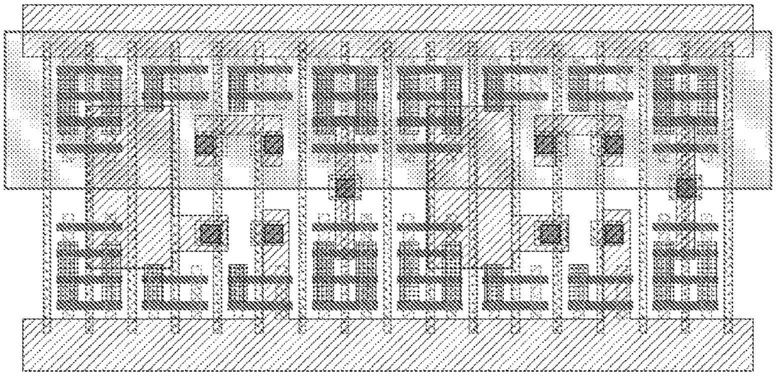
FIG. 1793A
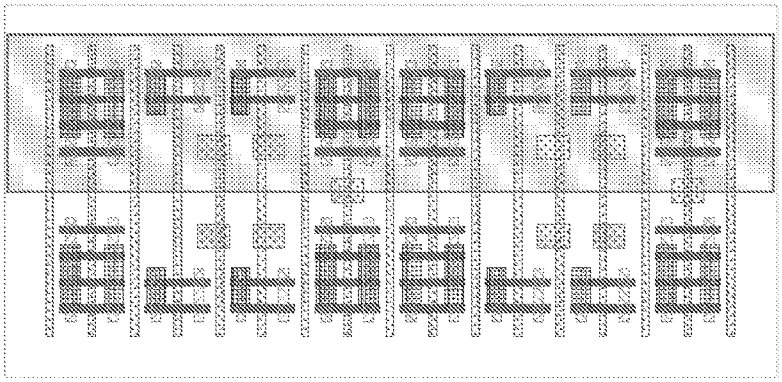
FIG. 1793B
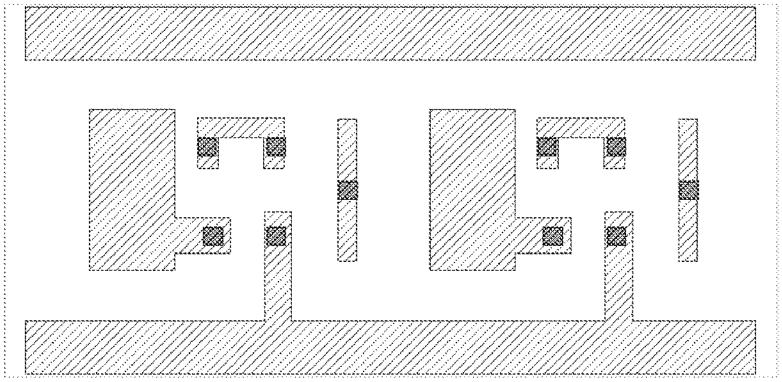
FIG. 1793C

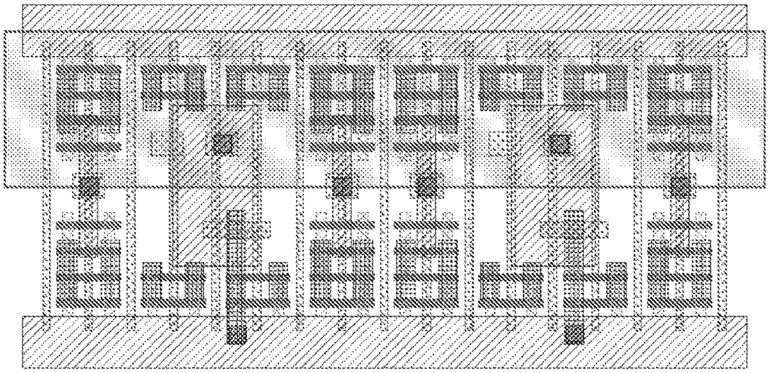
FIG. 1794A
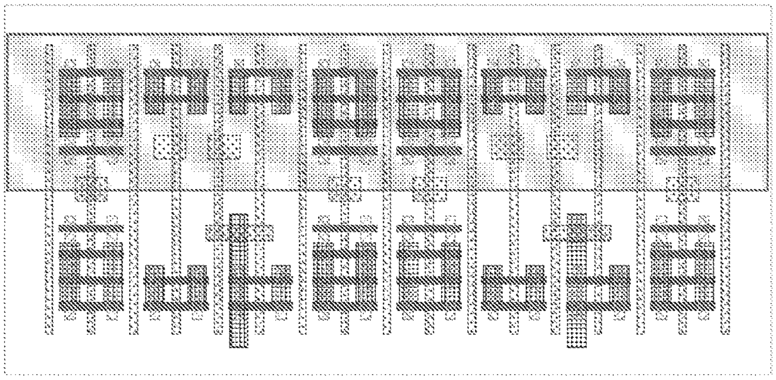
FIG. 1794B
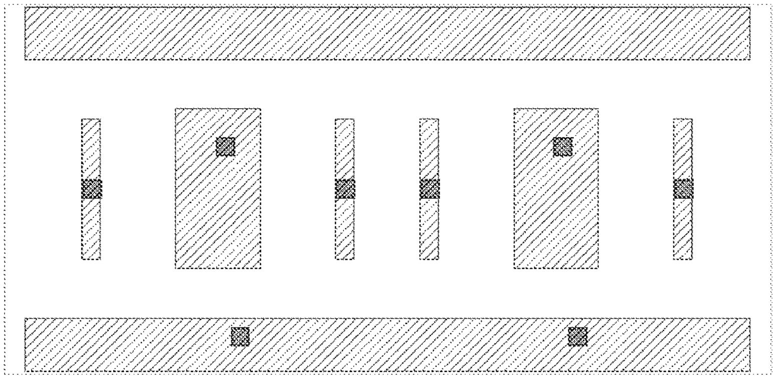
FIG. 1794C
*M* PDF Solutions, Inc.

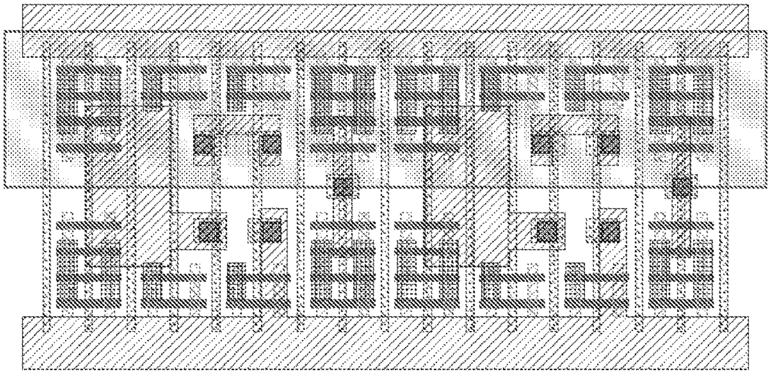
FIG. 1795A
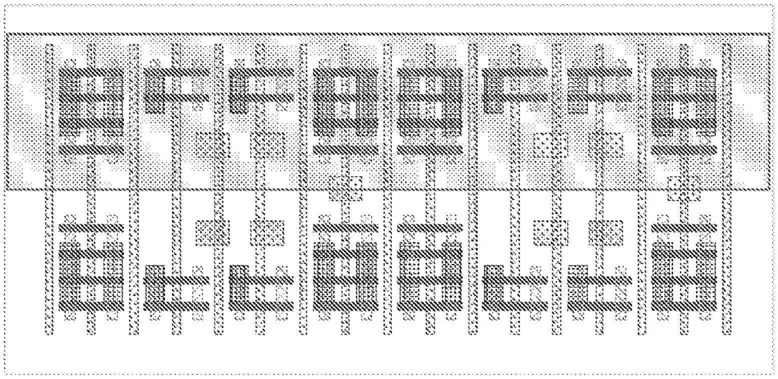
FIG. 1795B
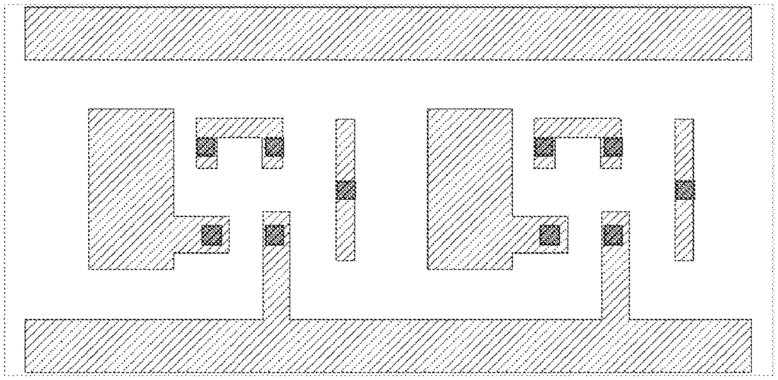
FIG. 1795C

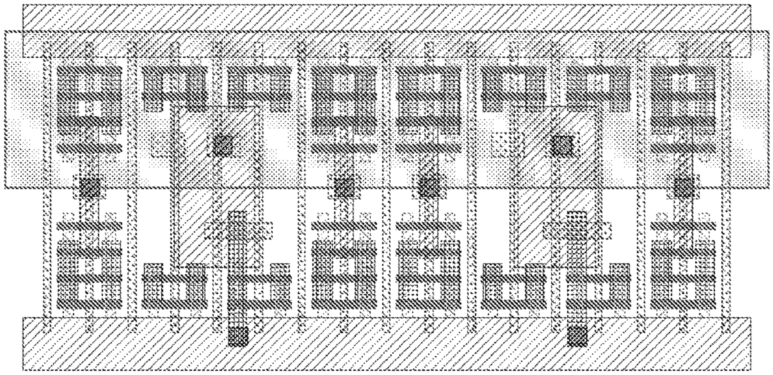
FIG. 1796A
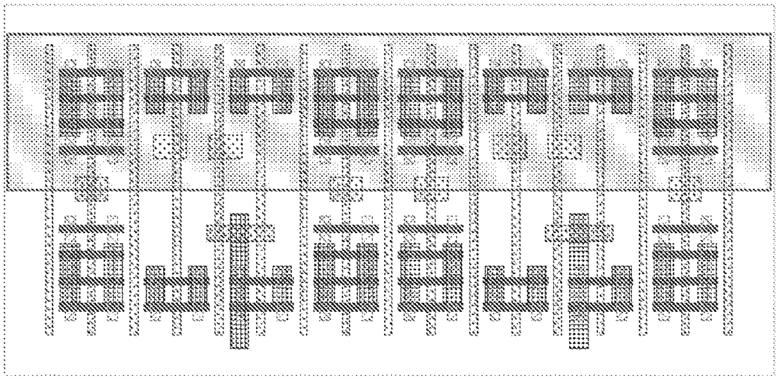
FIG. 1796B
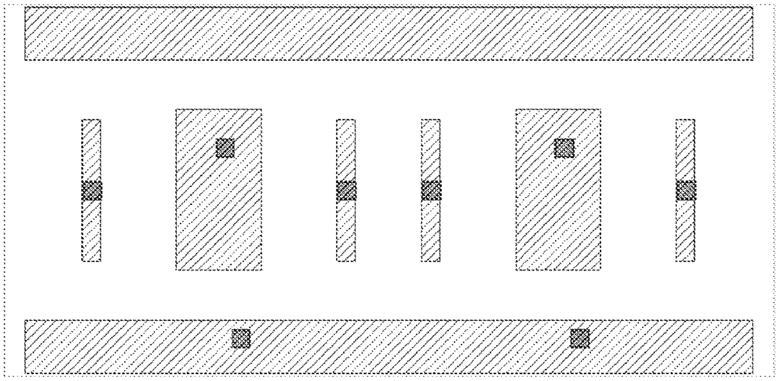
FIG. 1796C
*M* PDF Solutions, Inc.

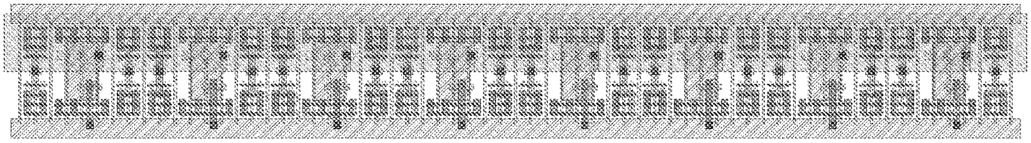
FIG. 1797A
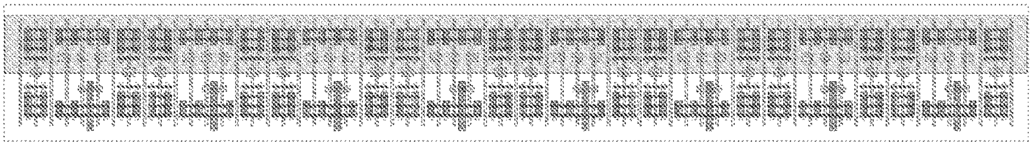
FIG. 1797B
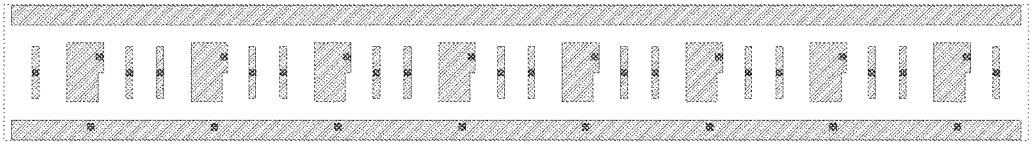
FIG. 1797C
*M* PDF Solutions, Inc.

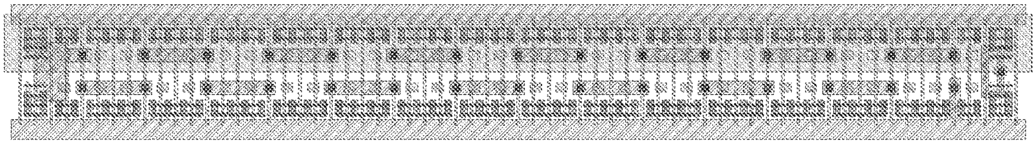
FIG. 1798A
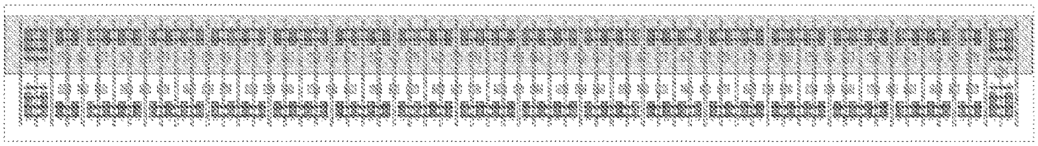
FIG. 1798B
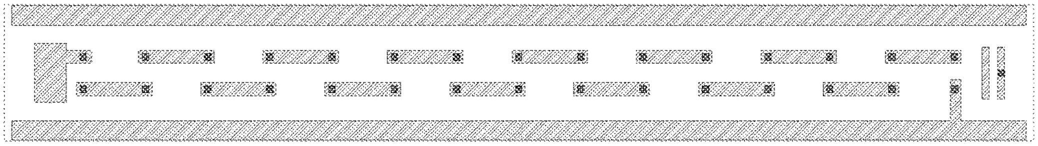
FIG. 1798C

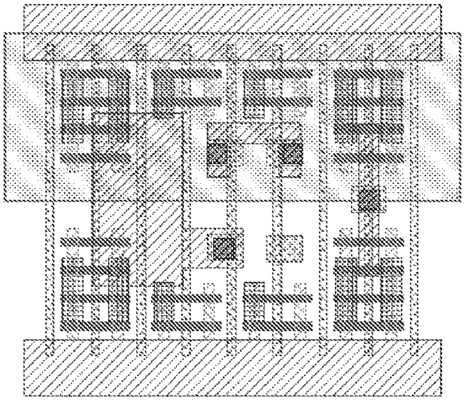
FIG. 1799A
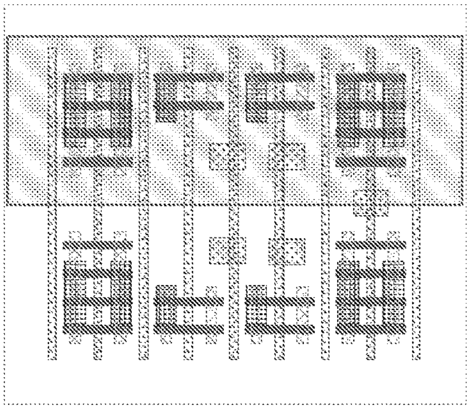
FIG. 1799B
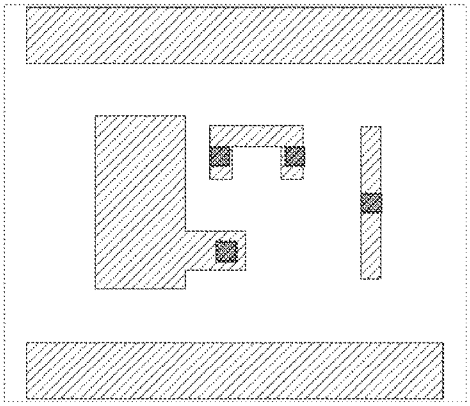
FIG. 1799C

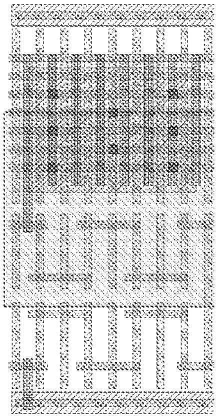
FIG. 1800A
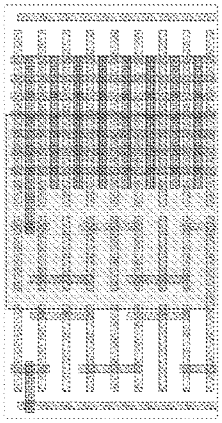
FIG. 1800B
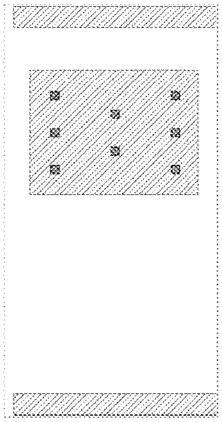
FIG. 1800C

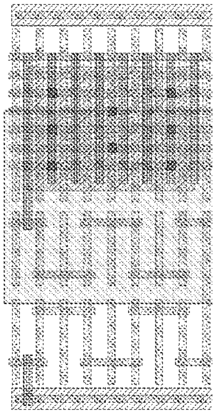
FIG. 1801A
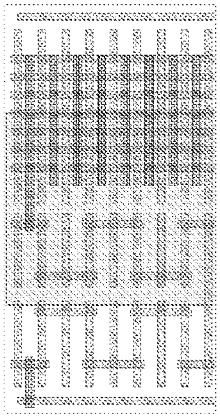
FIG. 1801B
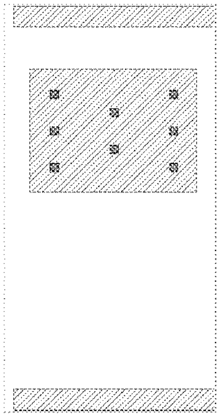
FIG. 1801C

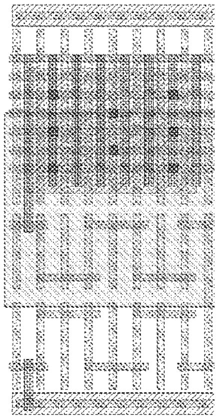
FIG. 1802A
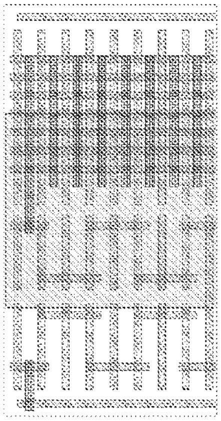
FIG. 1802B
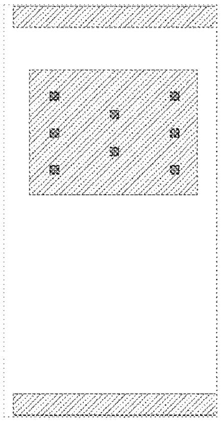
FIG. 1802C
*M* PDF Solutions, Inc.

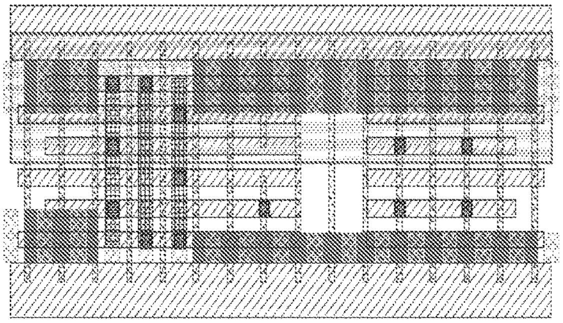
FIG. 1803A
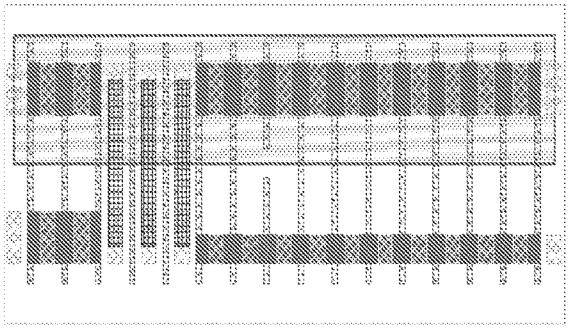
FIG. 1803B
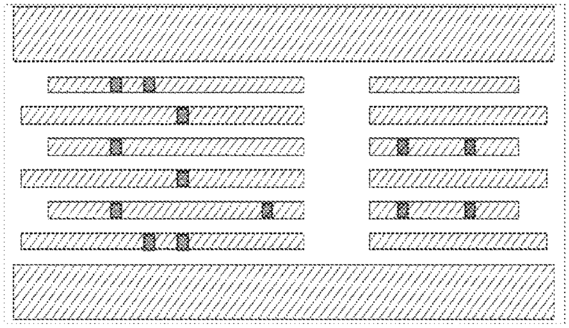
FIG. 1803C

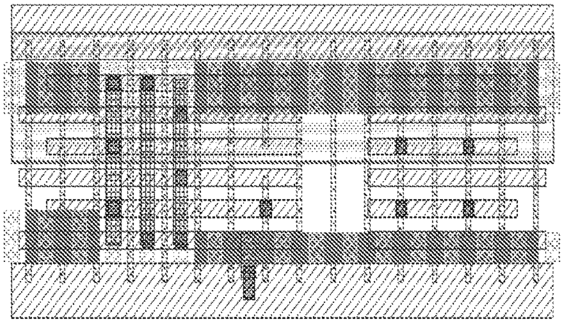
FIG. 1804A
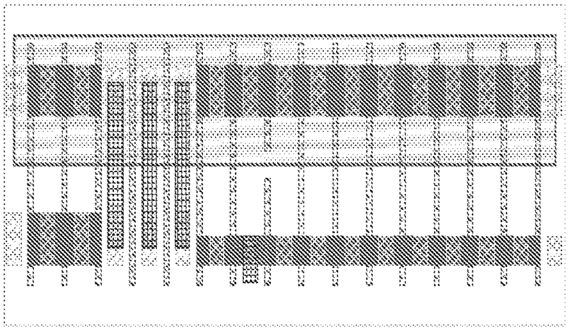
FIG. 1804B
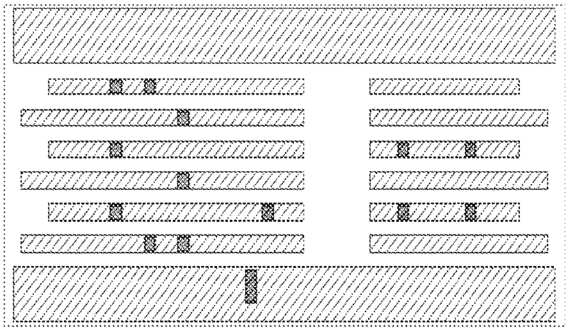
FIG. 1804C

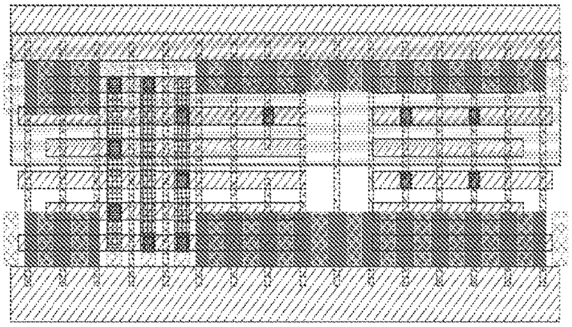
FIG. 1805A
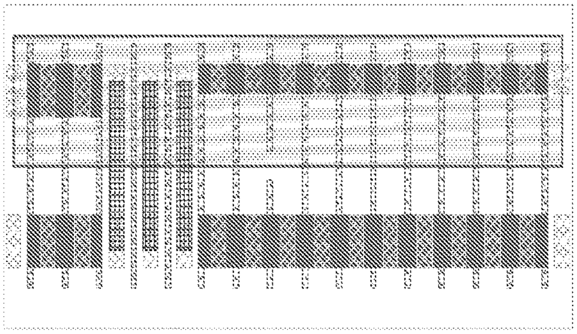
FIG. 1805B
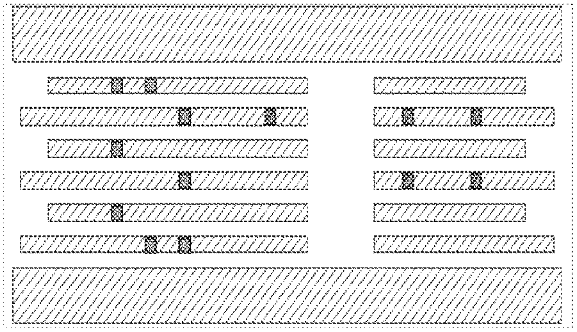
FIG. 1805C

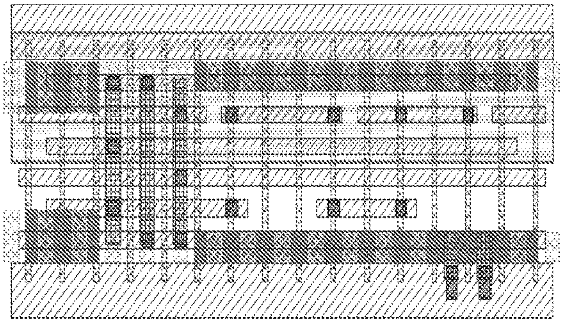
FIG. 1806A
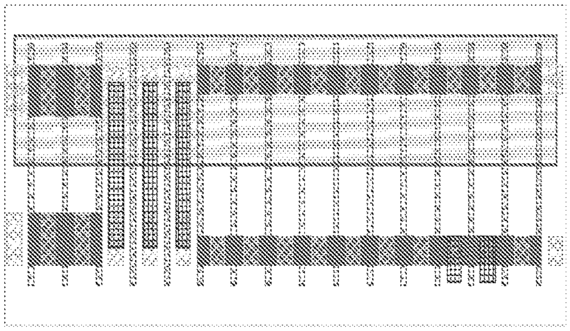
FIG. 1806B
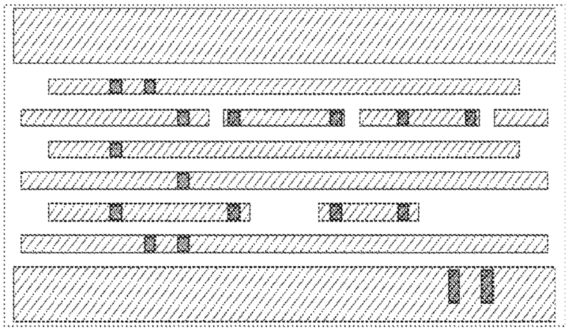
FIG. 1806C

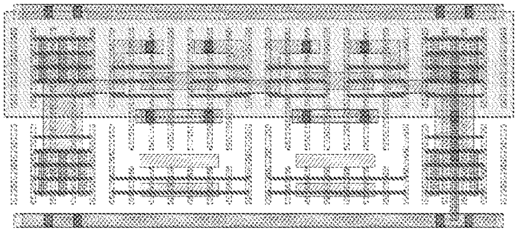
FIG. 1807A
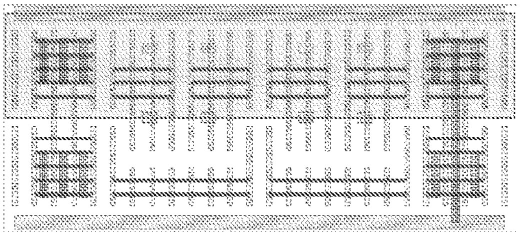
FIG. 1807B
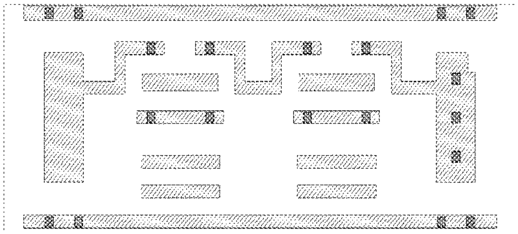
FIG. 1807C

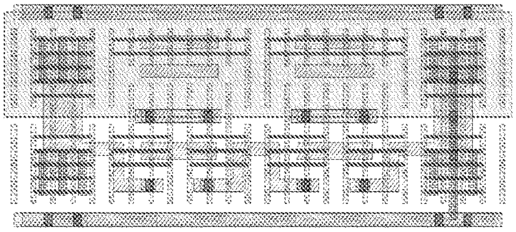
FIG. 1808A
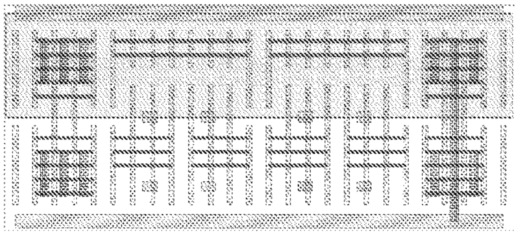
FIG. 1808B
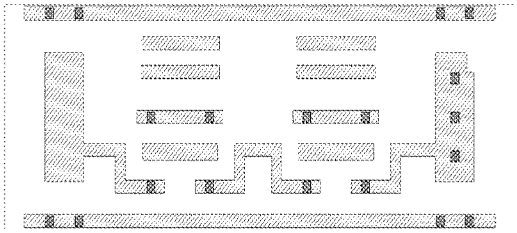
FIG. 1808C

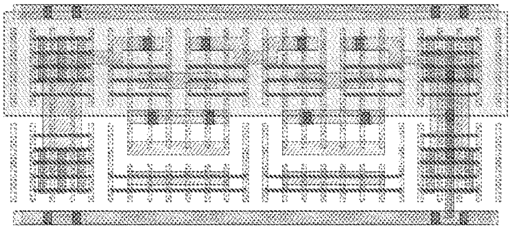
FIG. 1809A
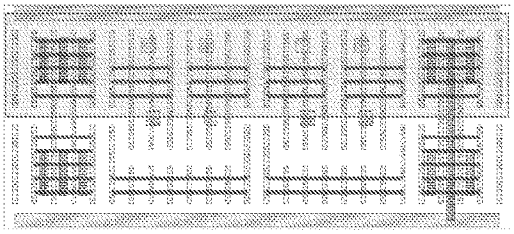
FIG. 1809B
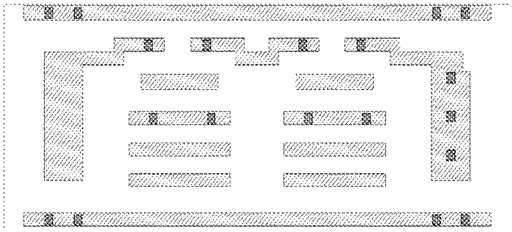
FIG. 1809C
*M* PDF Solutions, Inc.

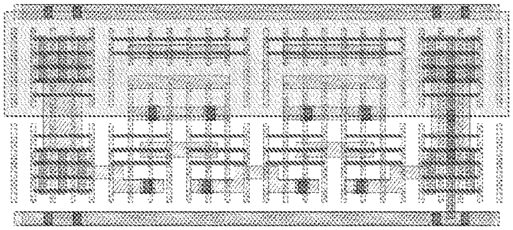
FIG. 1810A
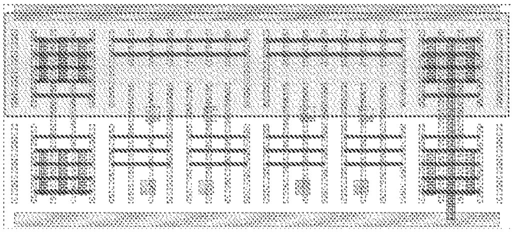
FIG. 1810B
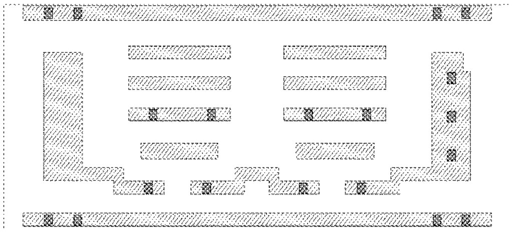
FIG. 1810C

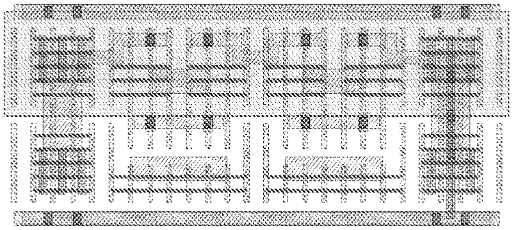
FIG. 1811A
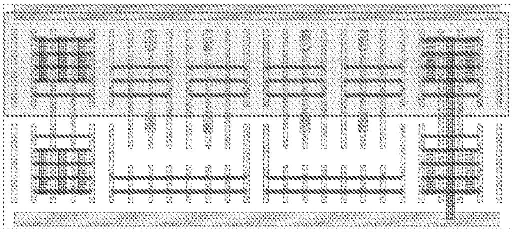
FIG. 1811B
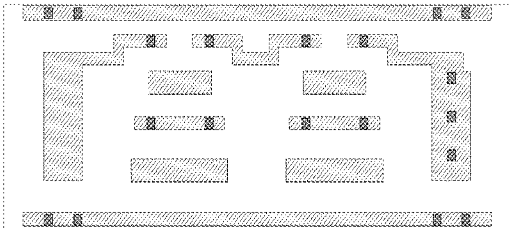
FIG. 1811C

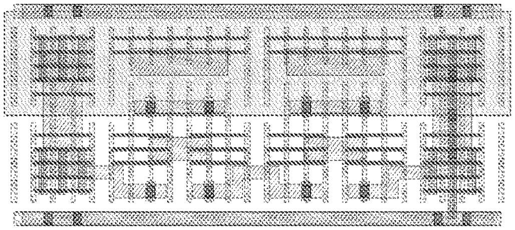
FIG. 1812A
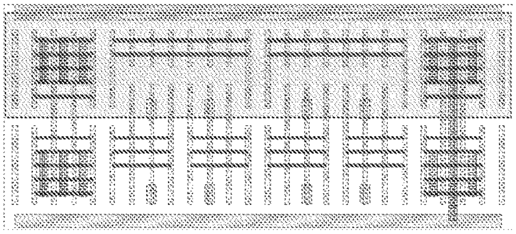
FIG. 1812B
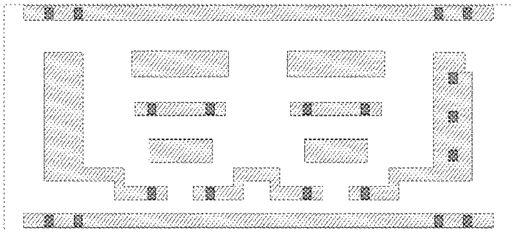
FIG. 1812C

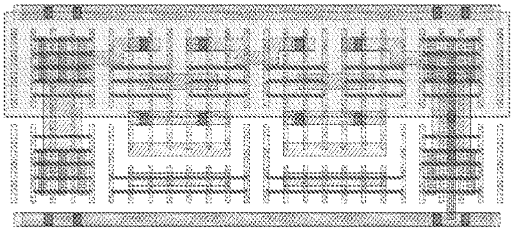
FIG. 1813A
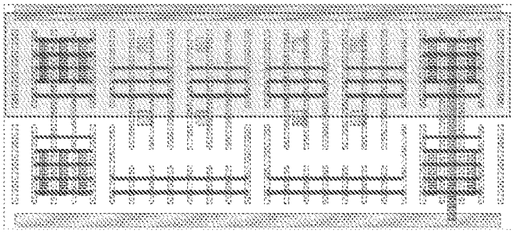
FIG. 1813B
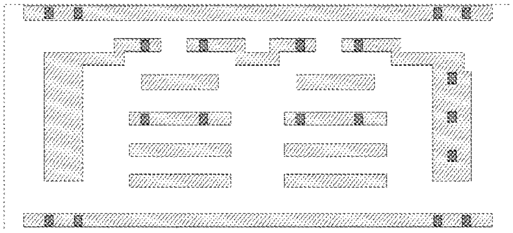
FIG. 1813C

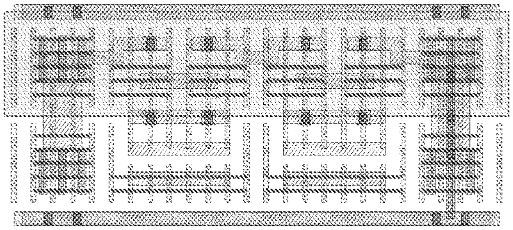
FIG. 1814A
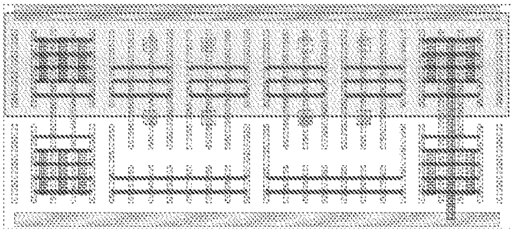
FIG. 1814B
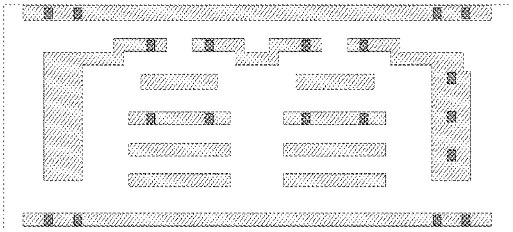
FIG. 1814C

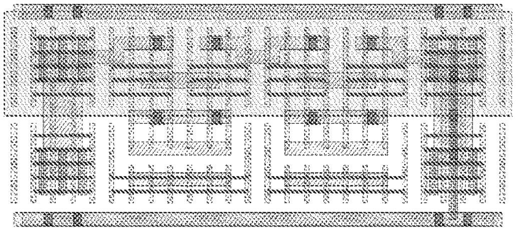
FIG. 1815A
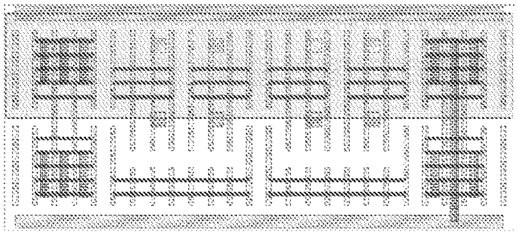
FIG. 1815B
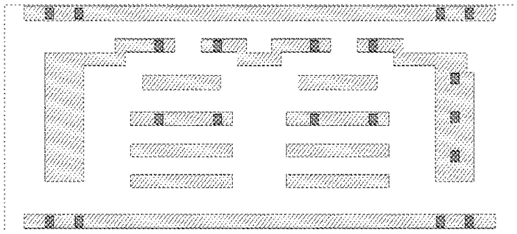
FIG. 1815C

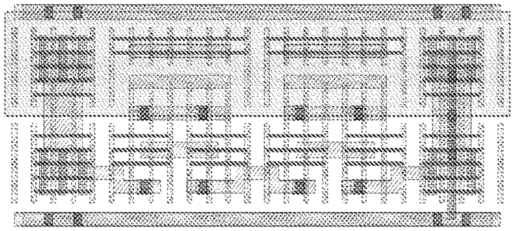
FIG. 1816A
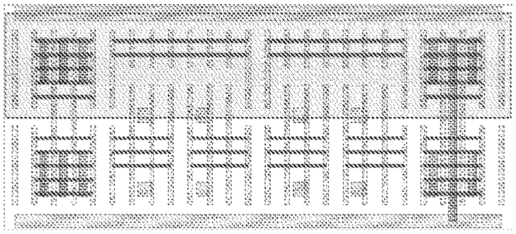
FIG. 1816B
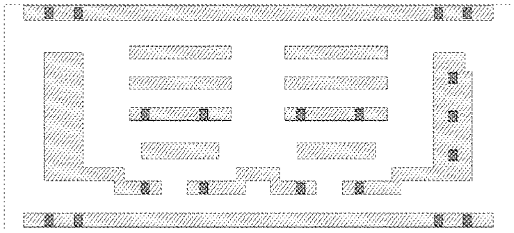
FIG. 1816C

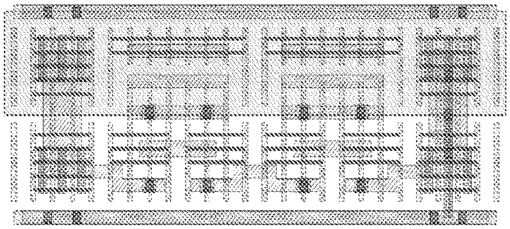
FIG. 1817A
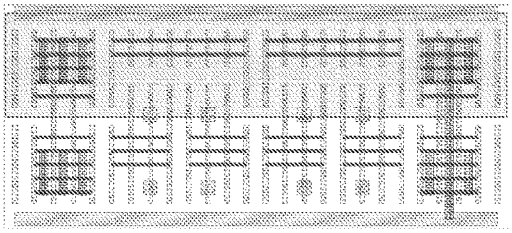
FIG. 1817B
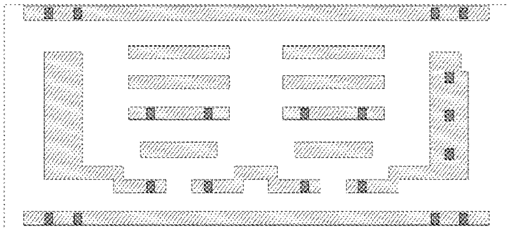
FIG. 1817C

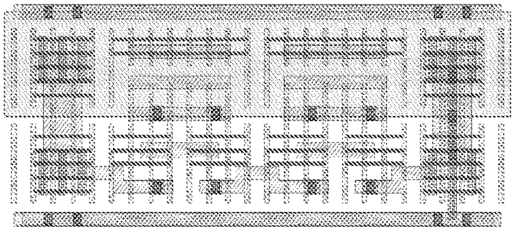
FIG. 1818A
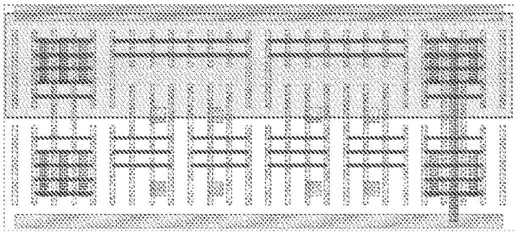
FIG. 1818B
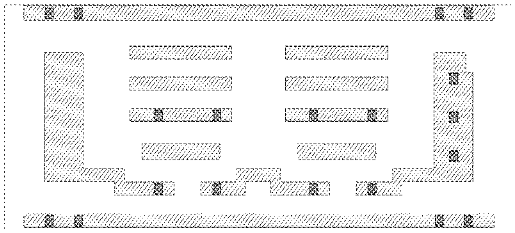
FIG. 1818C

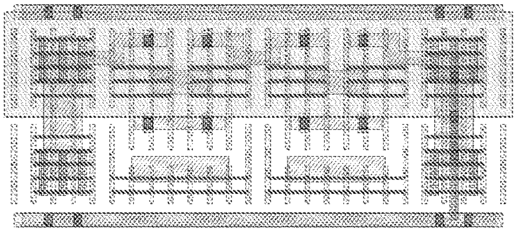
FIG. 1819A
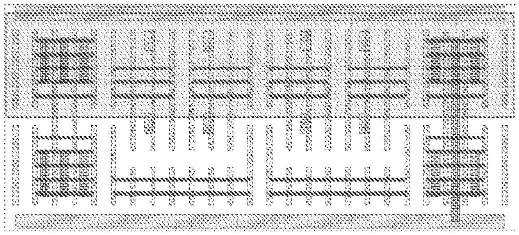
FIG. 1819B
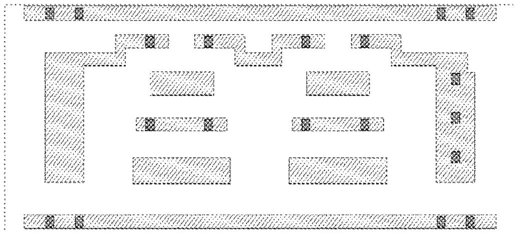
FIG. 1819C

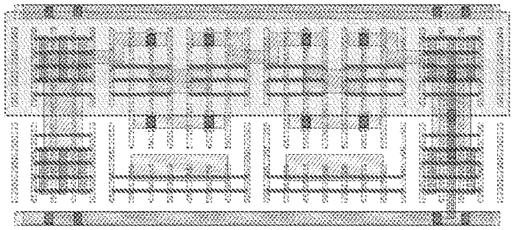
FIG. 1820A
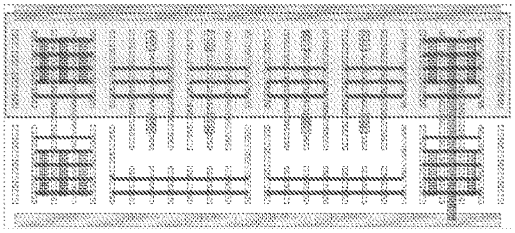
FIG. 1820B
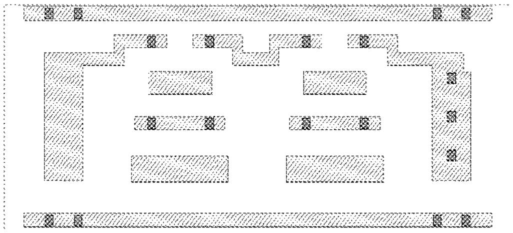
FIG. 1820C

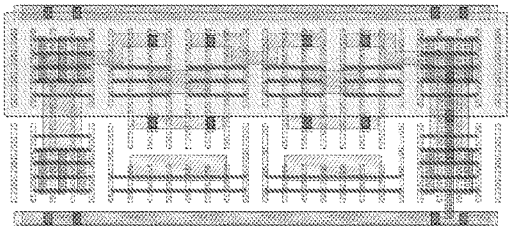
FIG. 1821A
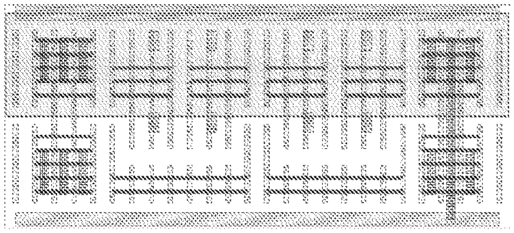
FIG. 1821B
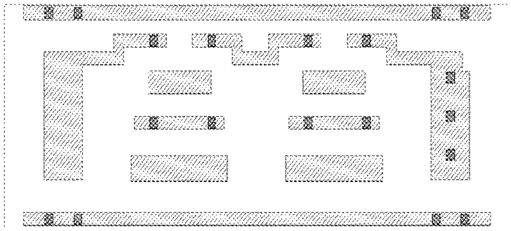
FIG. 1821C

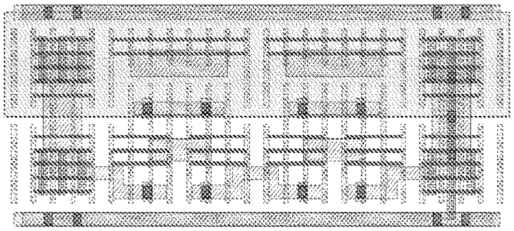
FIG. 1822A
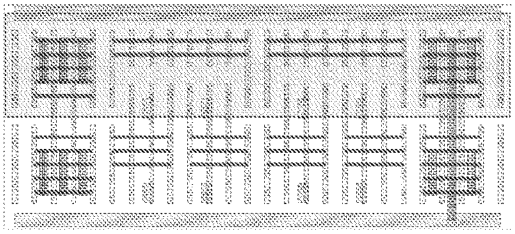
FIG. 1822B
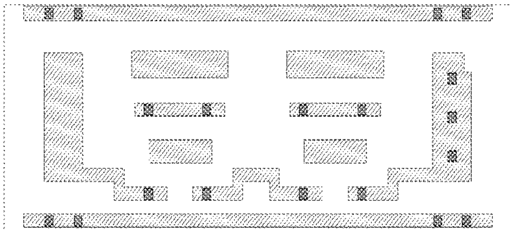
FIG. 1822C

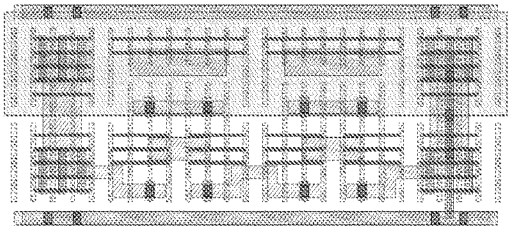
FIG. 1823A
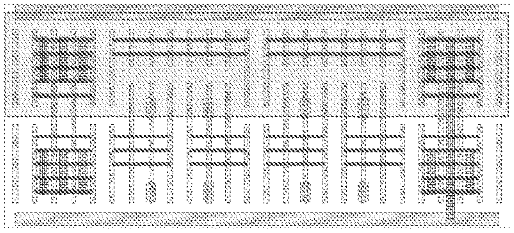
FIG. 1823B
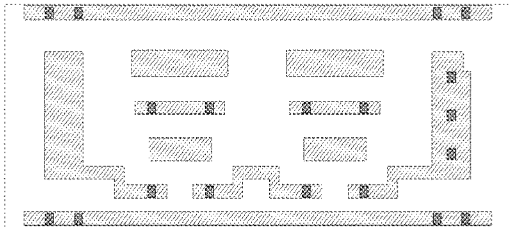
FIG. 1823C

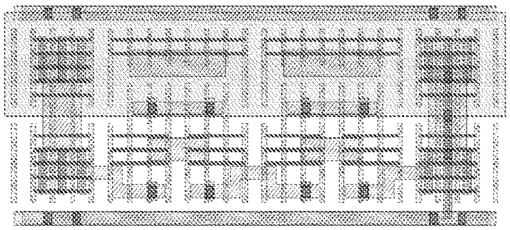
FIG. 1824A
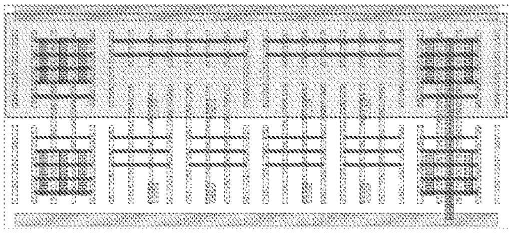
FIG. 1824B
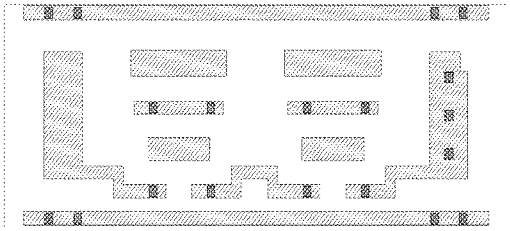
FIG. 1824C

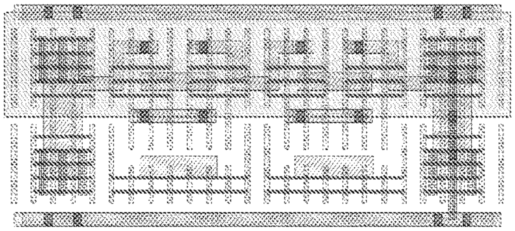
FIG. 1825A
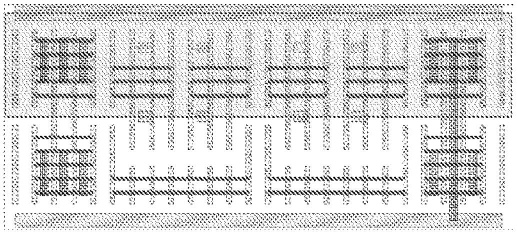
FIG. 1825B
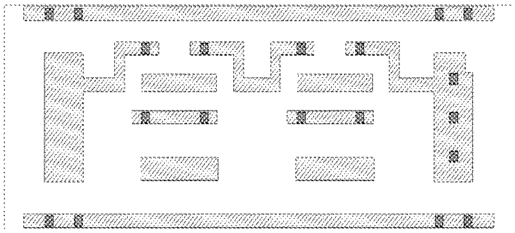
FIG. 1825C

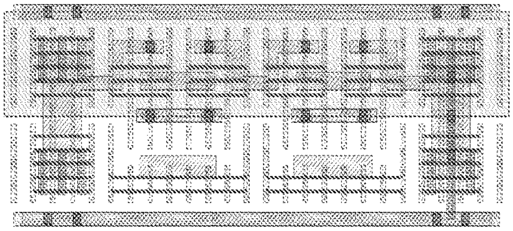
FIG. 1826A
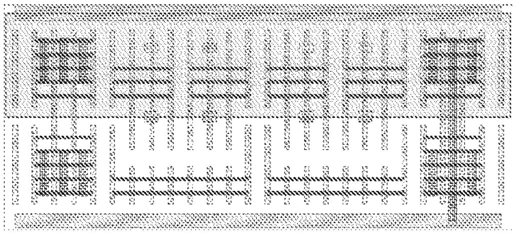
FIG. 1826B
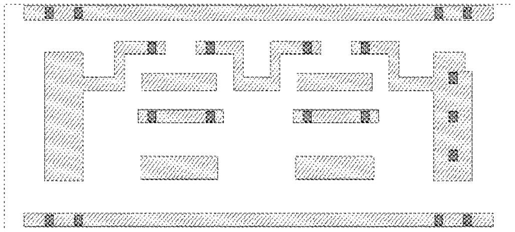
FIG. 1826C

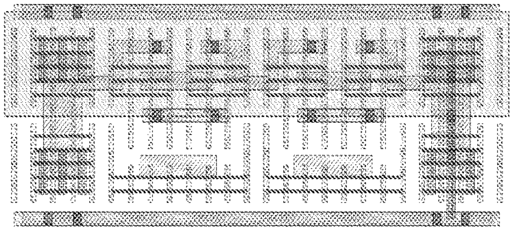
FIG. 1827A
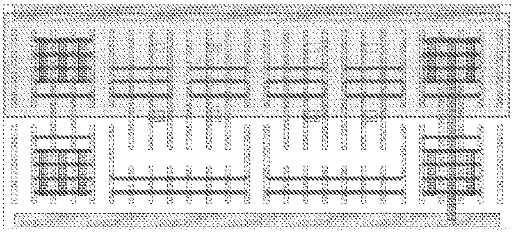
FIG. 1827B
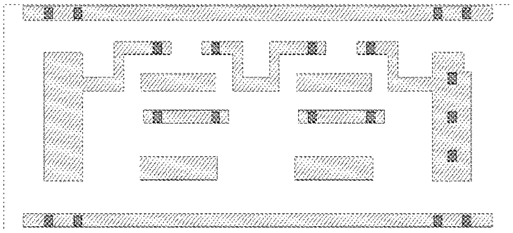
FIG. 1827C

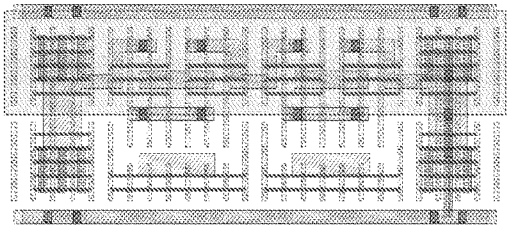
FIG. 1828A
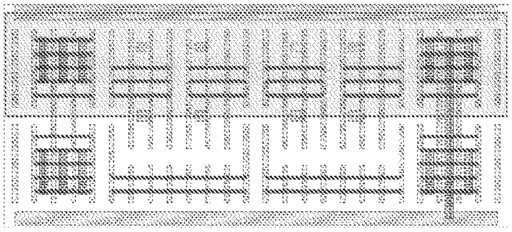
FIG. 1828B
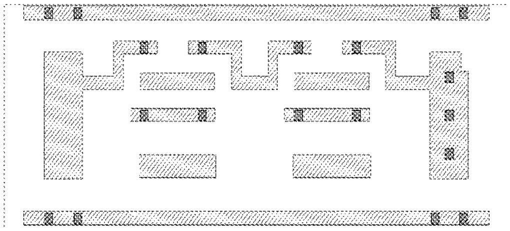
FIG. 1828C
*M* PDF Solutions, Inc.

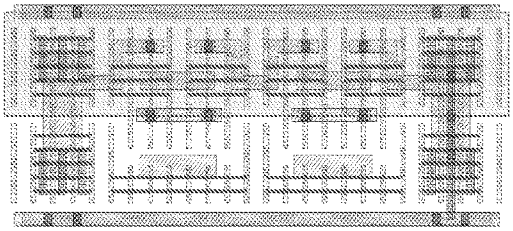
FIG. 1829A
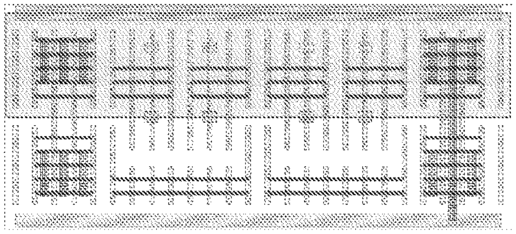
FIG. 1829B
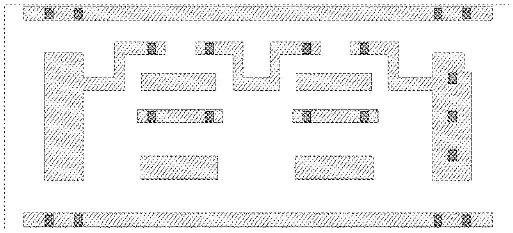
FIG. 1829C

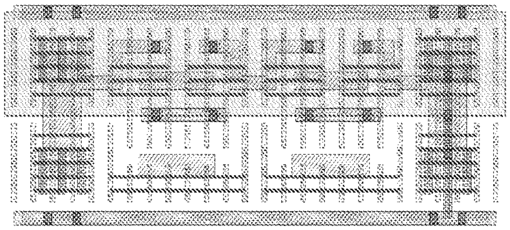
FIG. 1830A
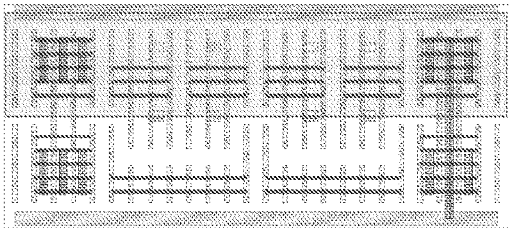
FIG. 1830B
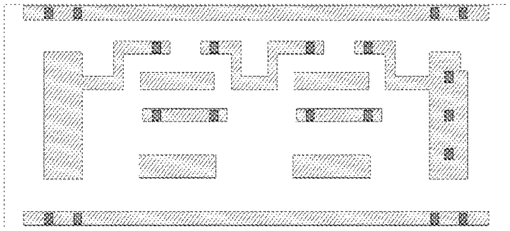
FIG. 1830C
*M* PDF Solutions, Inc.

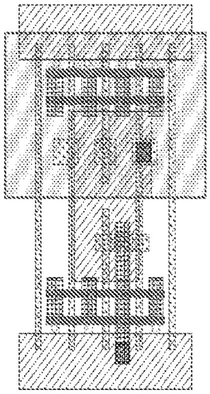
FIG. 1831A
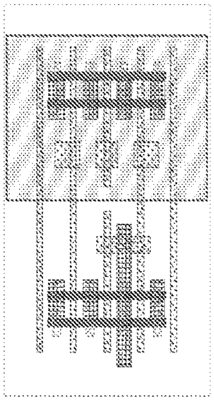
FIG. 1831B
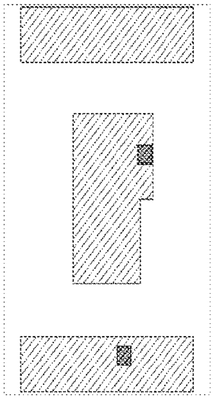
FIG. 1831C

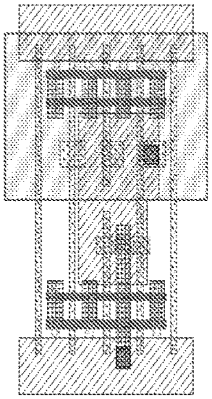
FIG. 1832A
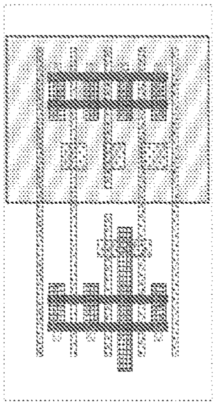
FIG. 1832B
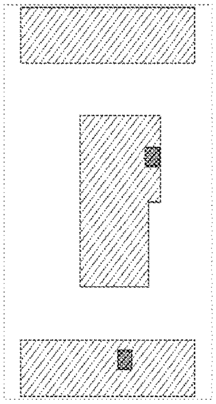
FIG. 1832C

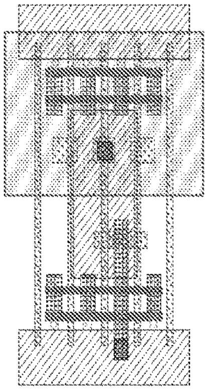
FIG. 1833A
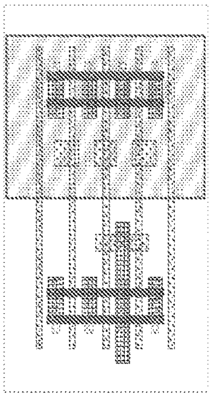
FIG. 1833B
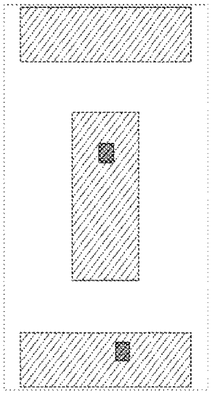
FIG. 1833C

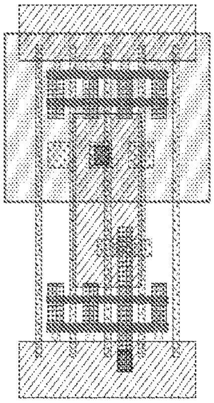
FIG. 1834A
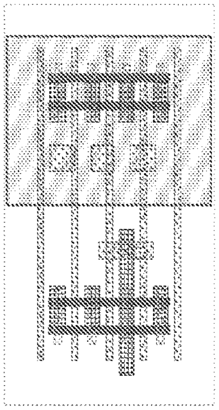
FIG. 1834B
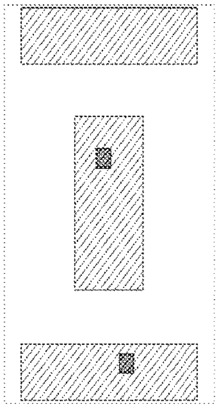
FIG. 1834C

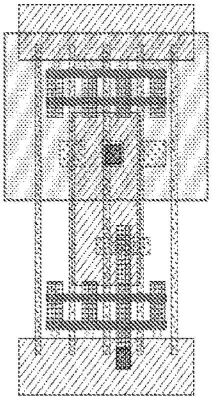
FIG. 1835A
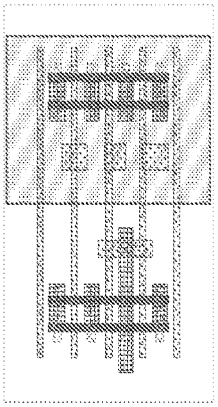
FIG. 1835B
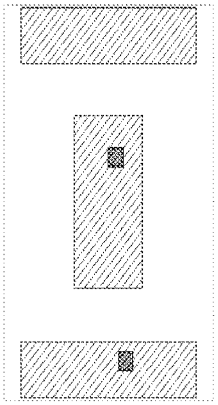
FIG. 1835C

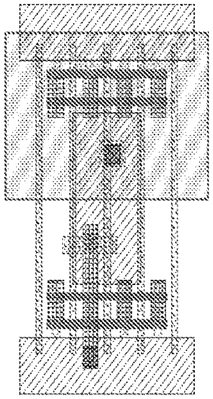
FIG. 1836A
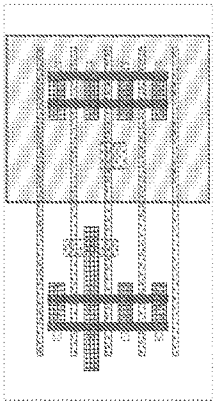
FIG. 1836B
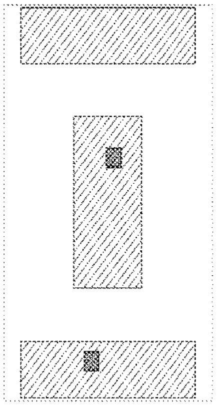
FIG. 1836C
*M* PDF Solutions, Inc.

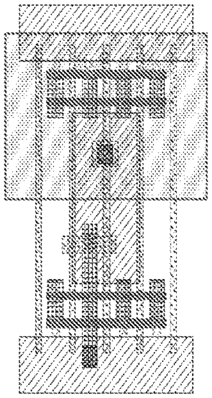
FIG. 1837A
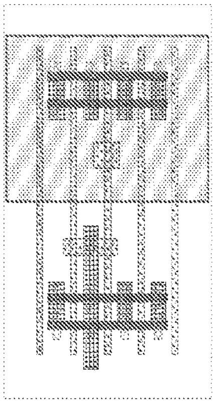
FIG. 1837B
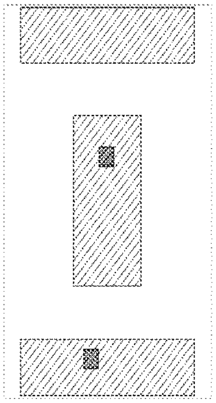
FIG. 1837C

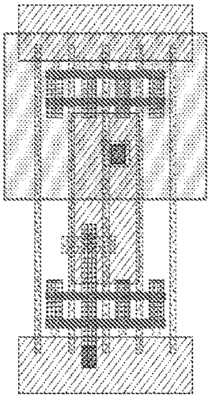
FIG. 1838A
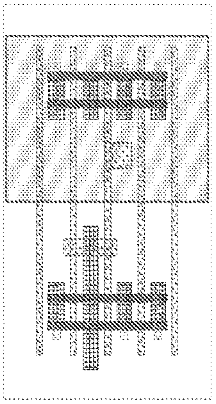
FIG. 1838B
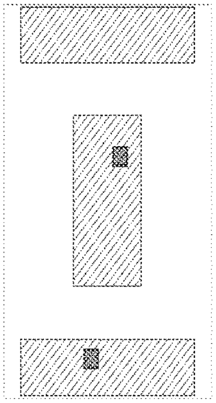
FIG. 1838C

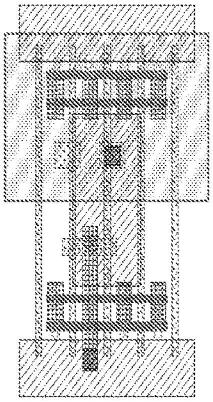
FIG. 1839A
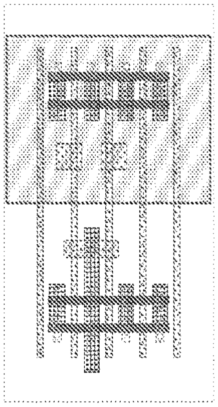
FIG. 1839B
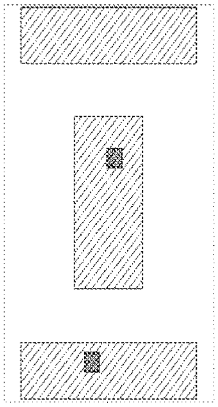
FIG. 1839C

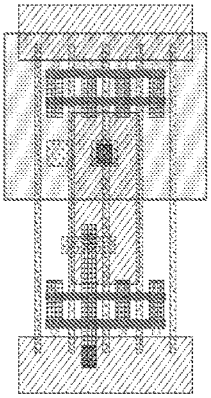
FIG. 1840A
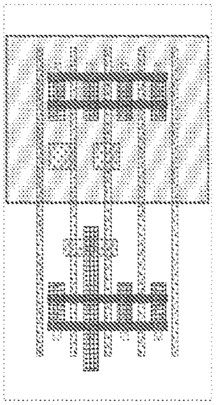
FIG. 1840B
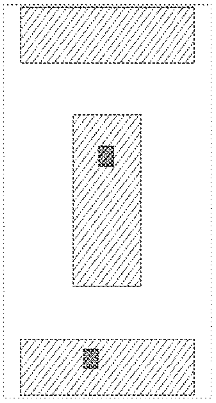
FIG. 1840C

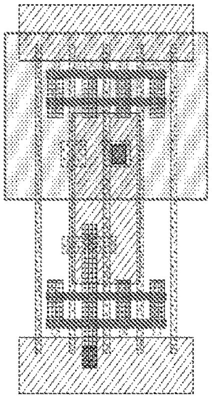
FIG. 1841A
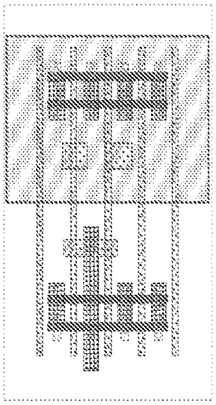
FIG. 1841B
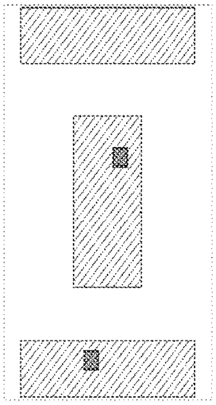
FIG. 1841C

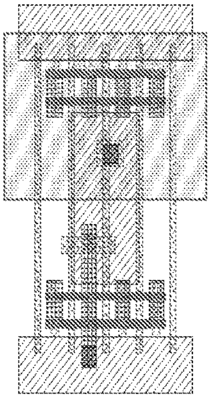
FIG. 1842A
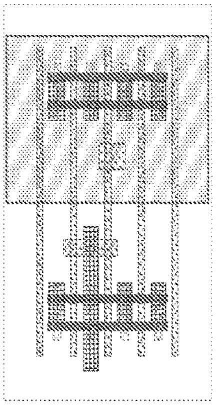
FIG. 1842B
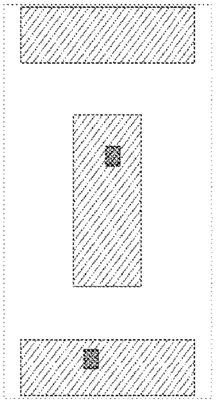
FIG. 1842C

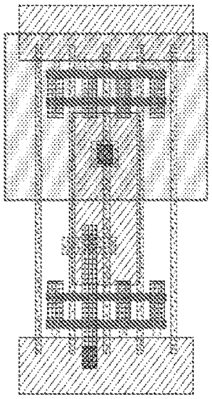
FIG. 1843A
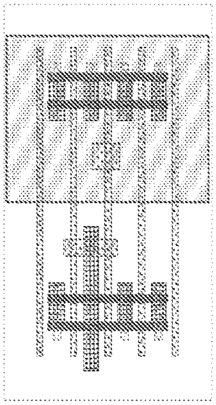
FIG. 1843B
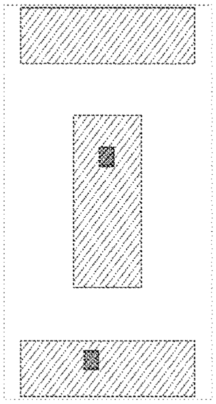
FIG. 1843C

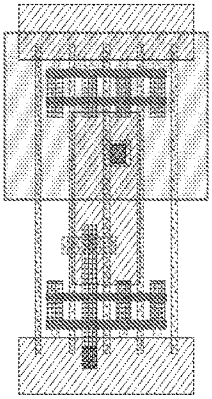
FIG. 1844A
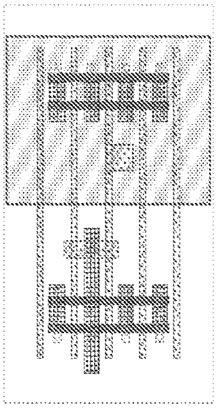
FIG. 1844B
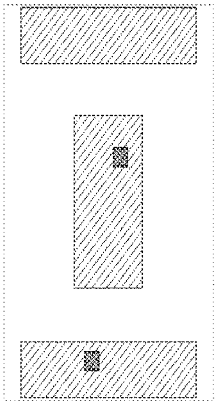
FIG. 1844C

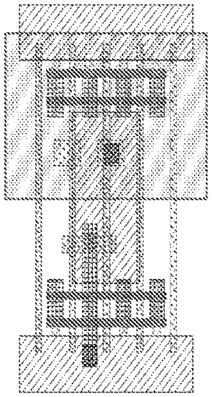
FIG. 1845A
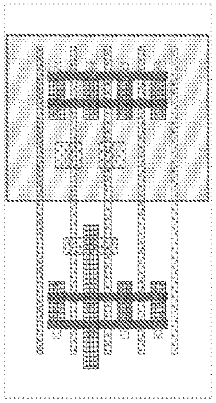
FIG. 1845B
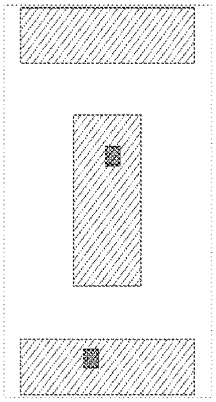
FIG. 1845C

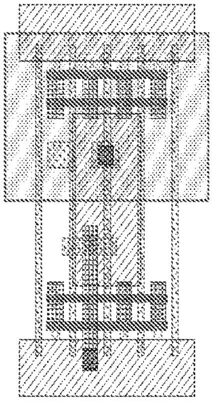
FIG. 1846A
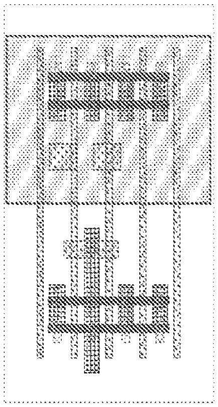
FIG. 1846B
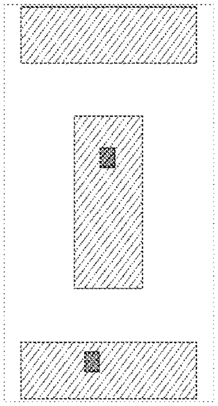
FIG. 1846C

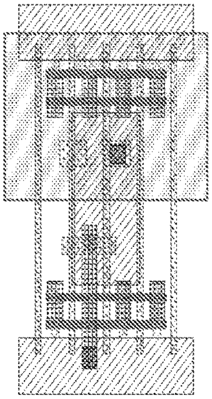
FIG. 1847A
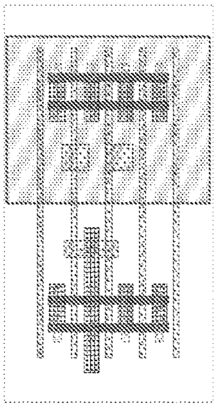
FIG. 1847B
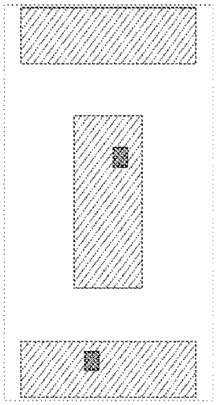
FIG. 1847C

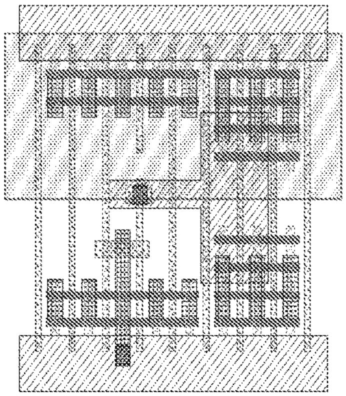
FIG. 1848A
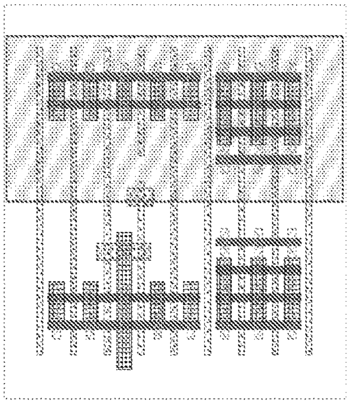
FIG. 1848B
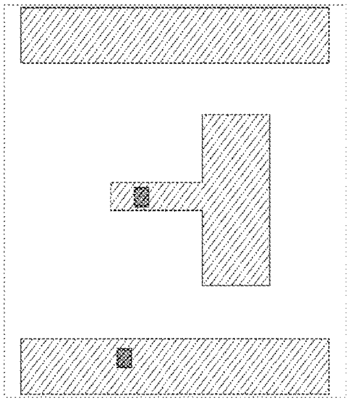
FIG. 1848C

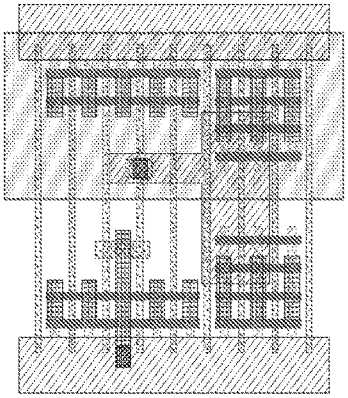
FIG. 1849A
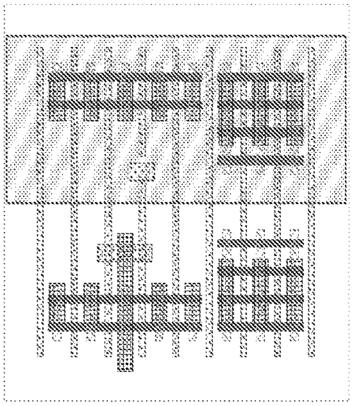
FIG. 1849B
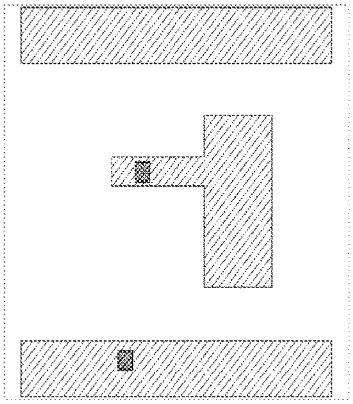
FIG. 1849C

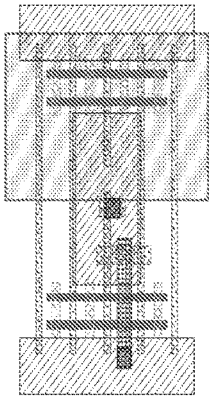
FIG. 1850A
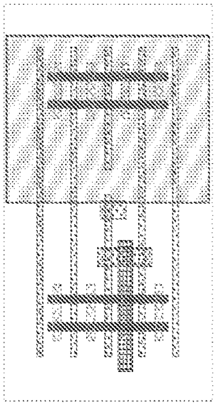
FIG. 1850B
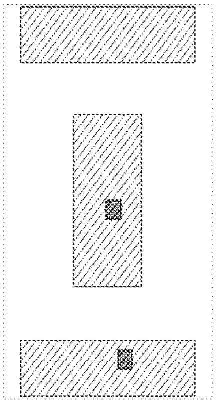
FIG. 1850C

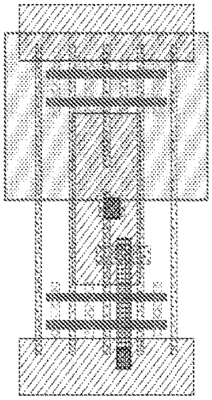
FIG. 1851A
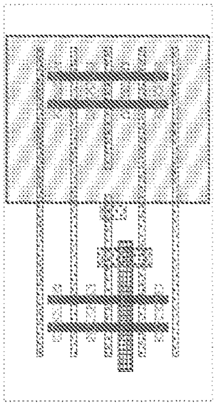
FIG. 1851B
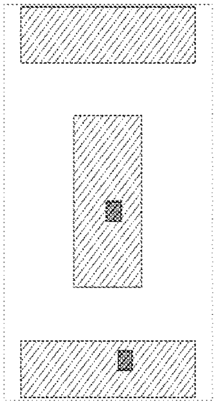
FIG. 1851C

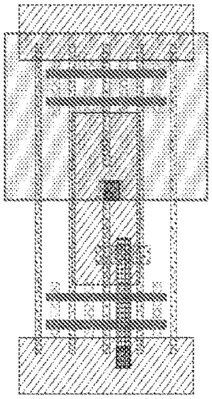
FIG. 1852A
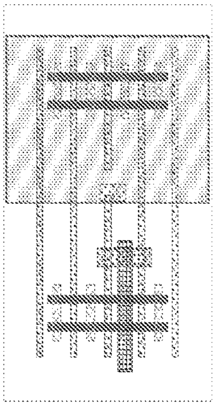
FIG. 1852B
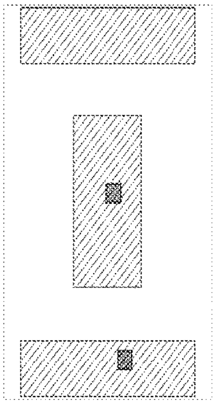
FIG. 1852C
*M* PDF Solutions, Inc.

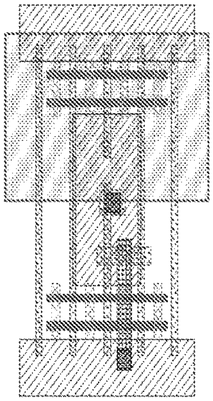
FIG. 1853A
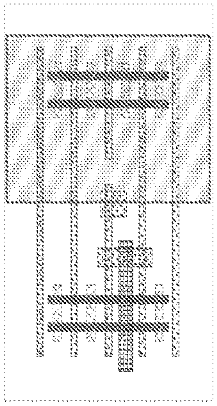
FIG. 1853B
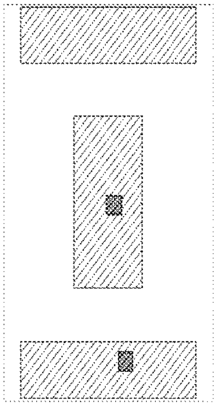
FIG. 1853C

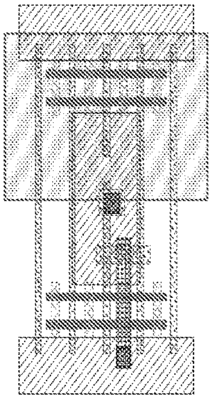
FIG. 1854A
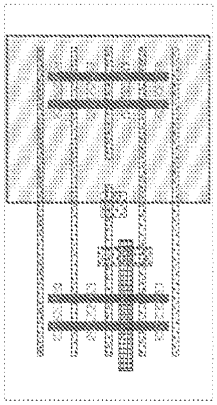
FIG. 1854B
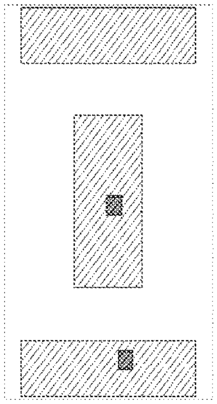
FIG. 1854C
*M* PDF Solutions, Inc.

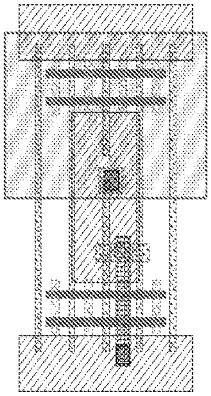
FIG. 1855A
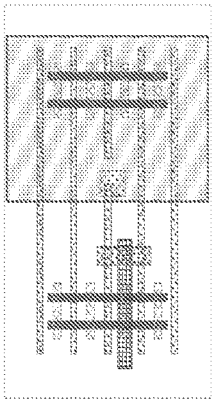
FIG. 1855B
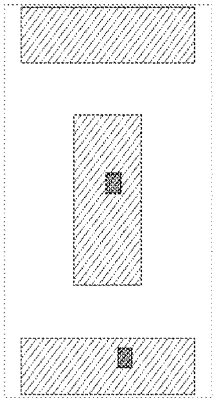
FIG. 1855C
*M* PDF Solutions, Inc.

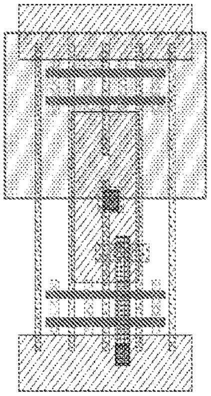
FIG. 1856A
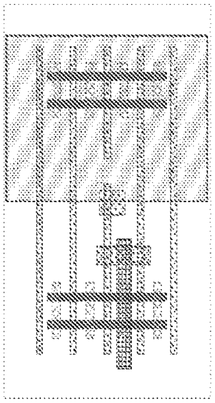
FIG. 1856B
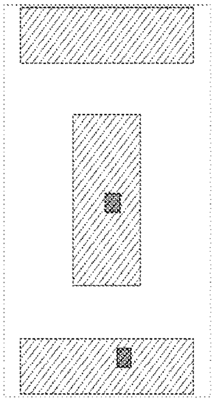
FIG. 1856C
*M* PDF Solutions, Inc.

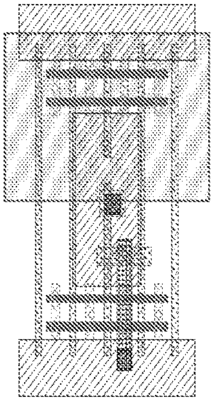
FIG. 1857A
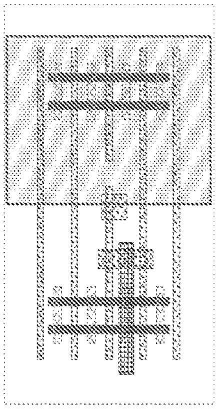
FIG. 1857B
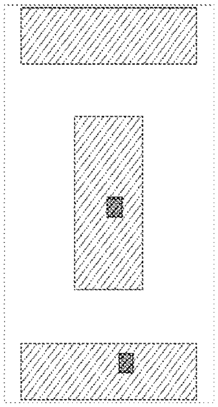
FIG. 1857C

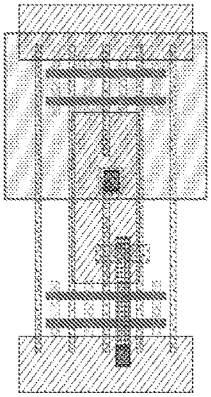
FIG. 1858A
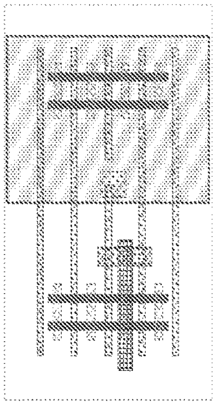
FIG. 1858B
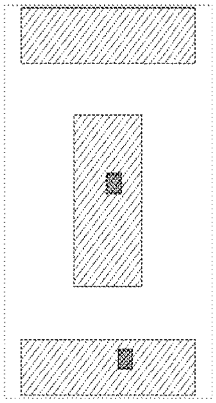
FIG. 1858C

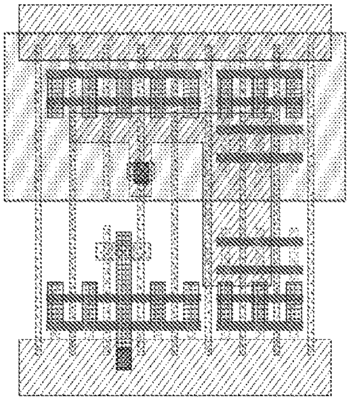
FIG. 1859A
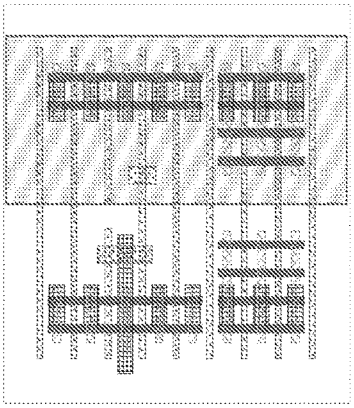
FIG. 1859B
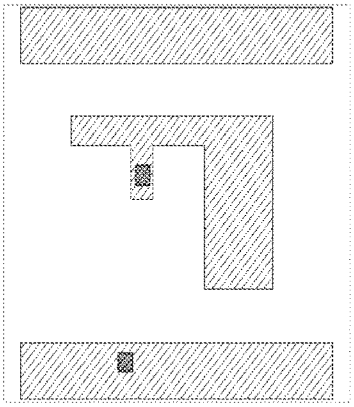
FIG. 1859C

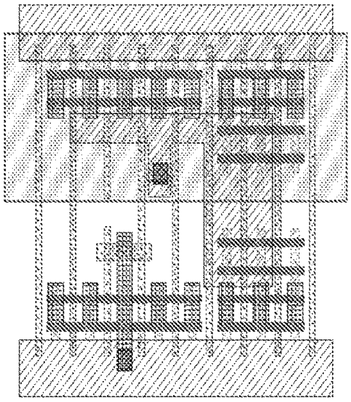
FIG. 1860A
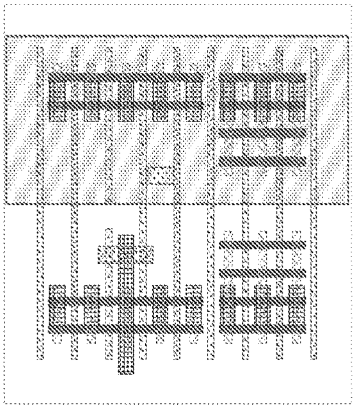
FIG. 1860B
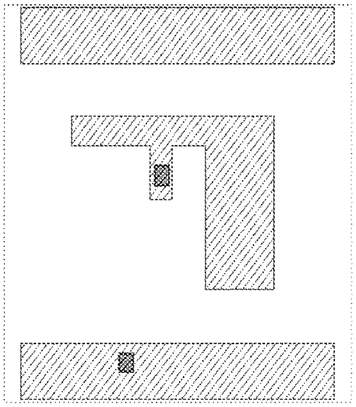
FIG. 1860C

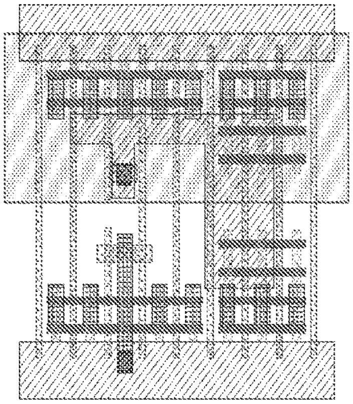
FIG. 1861A
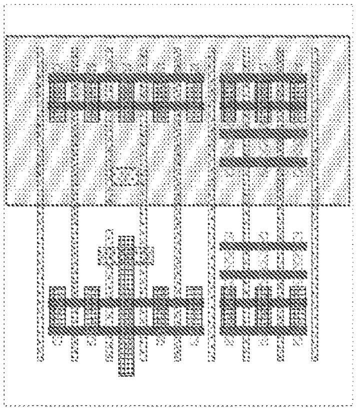
FIG. 1861B
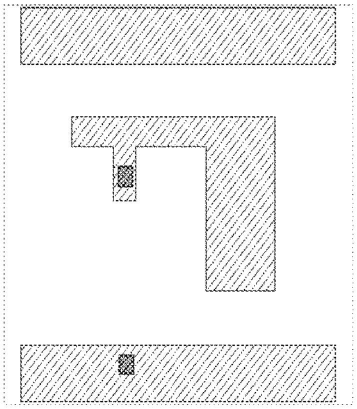
FIG. 1861C

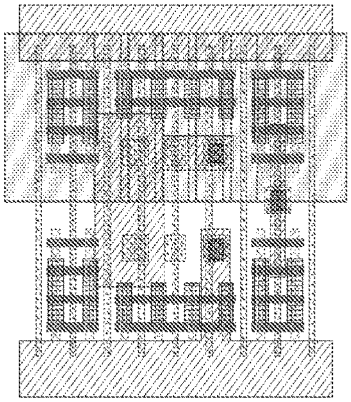
FIG. 1862A
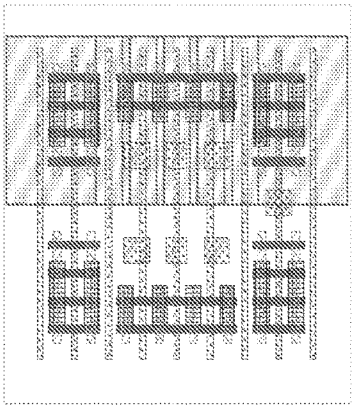
FIG. 1862B
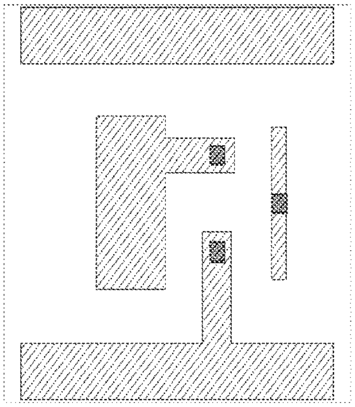
FIG. 1862C

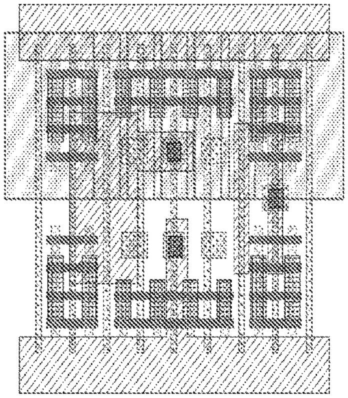
FIG. 1863A
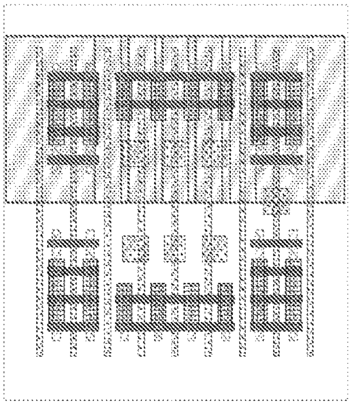
FIG. 1863B
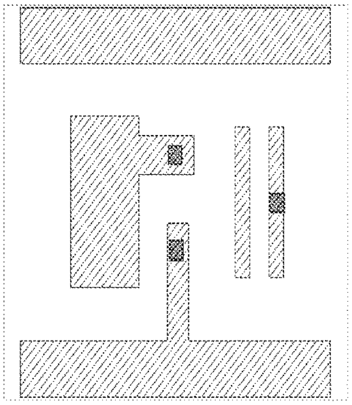
FIG. 1863C

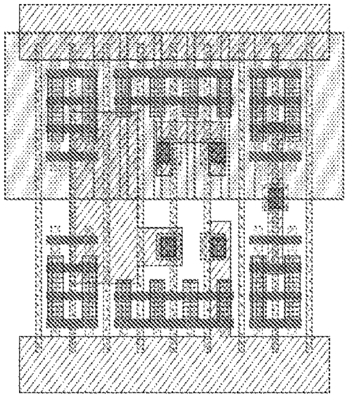
FIG. 1864A
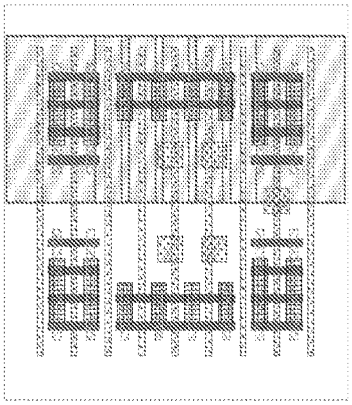
FIG. 1864B
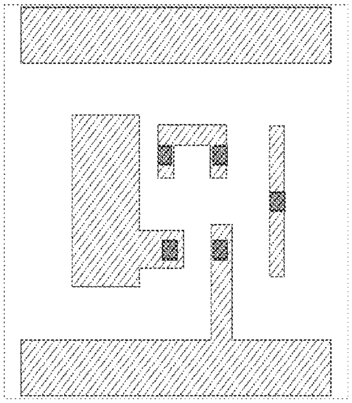
FIG. 1864C

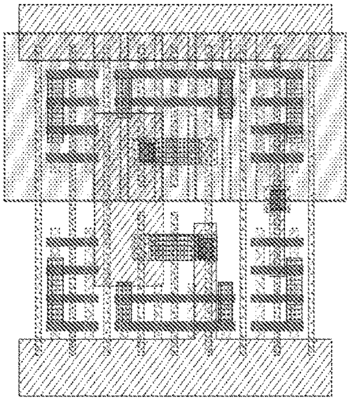
FIG. 1865A
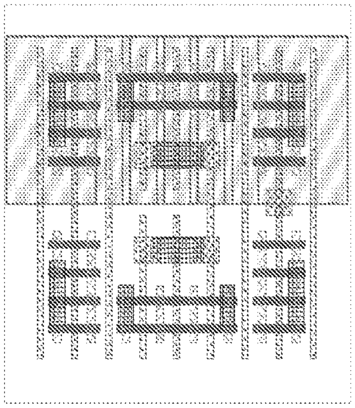
FIG. 1865B
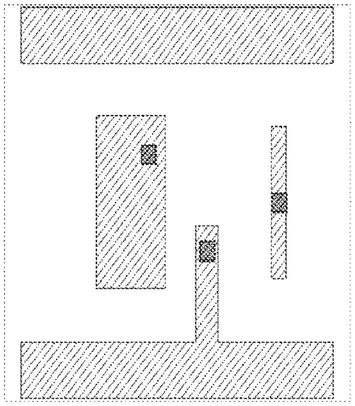
FIG. 1865C

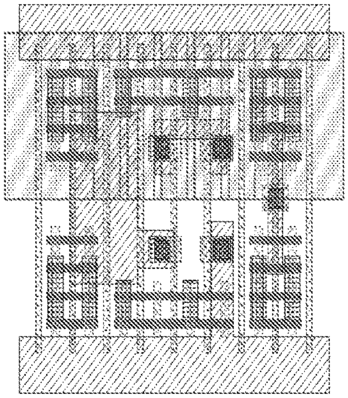
FIG. 1866A
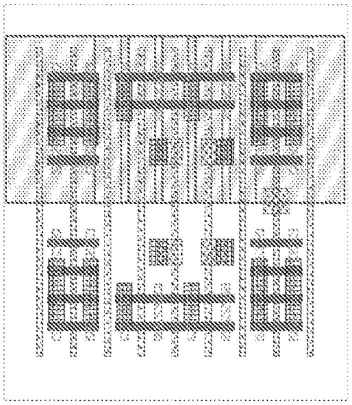
FIG. 1866B
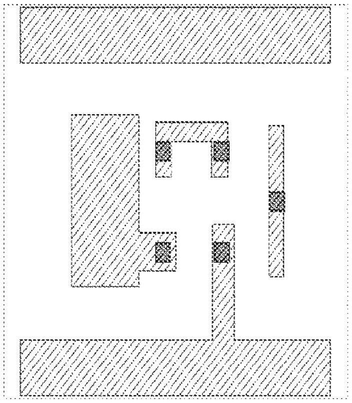
FIG. 1866C

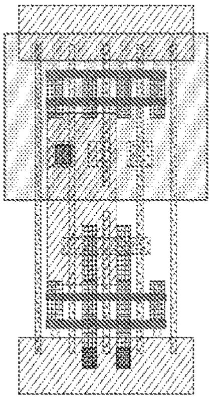
FIG. 1867A
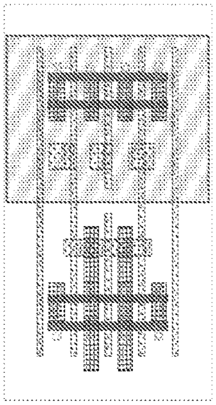
FIG. 1867B
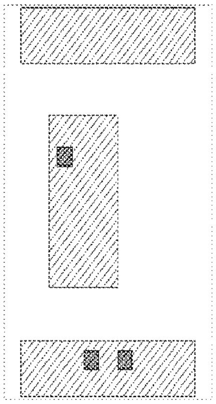
FIG. 1867C

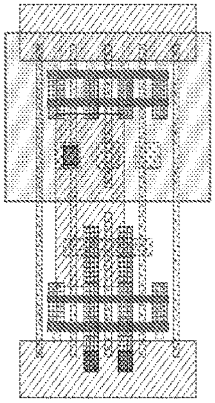
FIG. 1868A
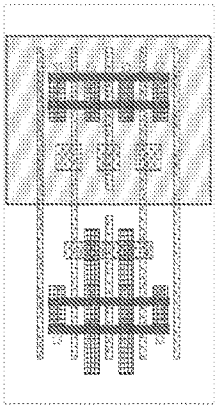
FIG. 1868B
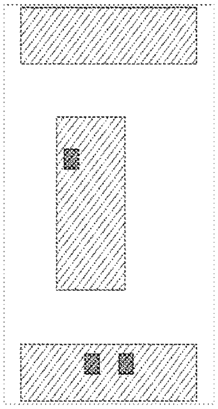
FIG. 1868C

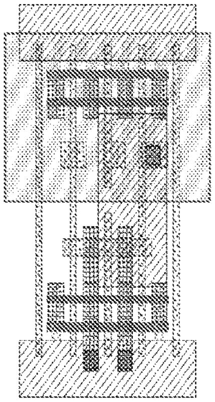
FIG. 1869A
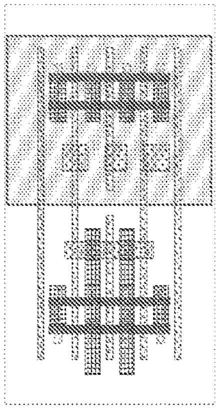
FIG. 1869B
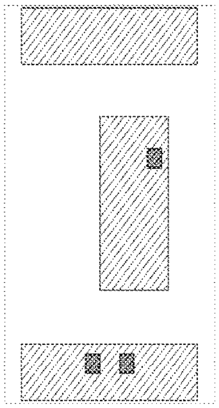
FIG. 1869C

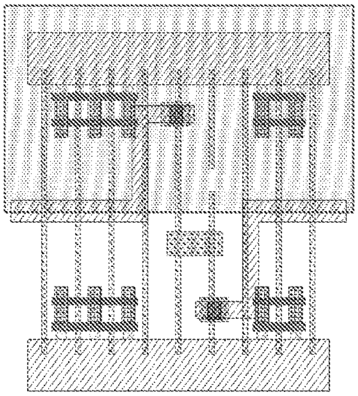
FIG. 1870A
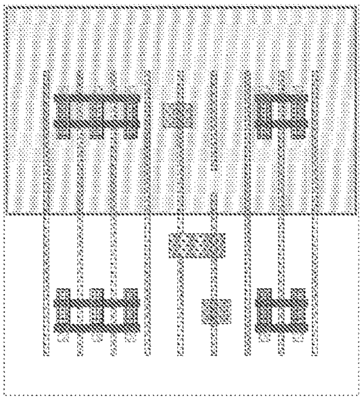
FIG. 1870B
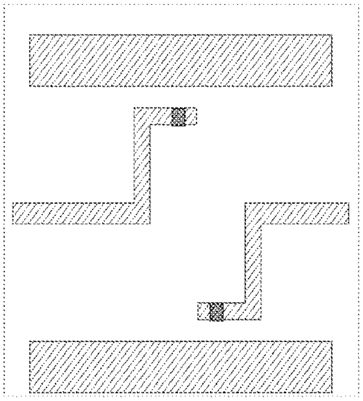
FIG. 1870C
*M* PDF Solutions, Inc.

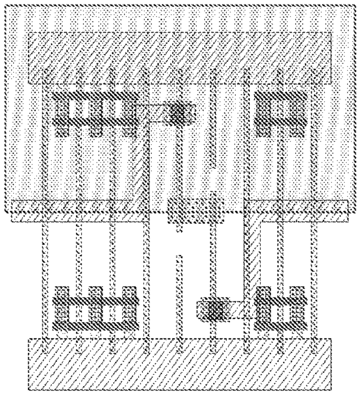
FIG. 1871A
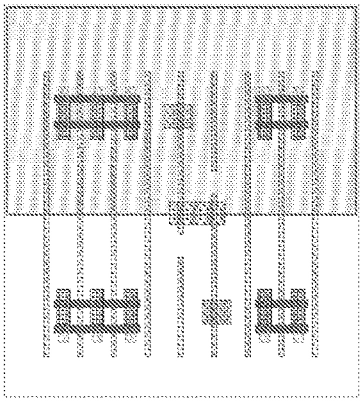
FIG. 1871B
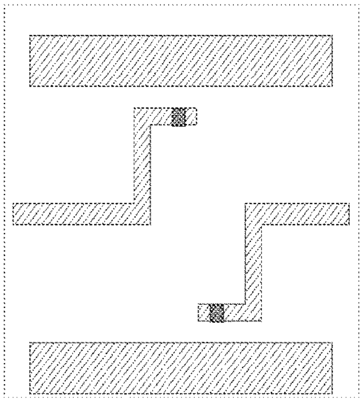
FIG. 1871C

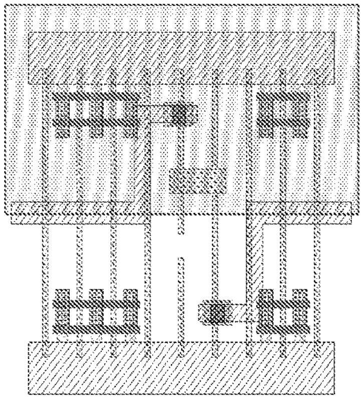
FIG. 1872A
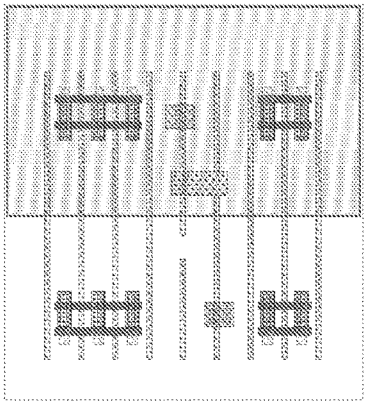
FIG. 1872B
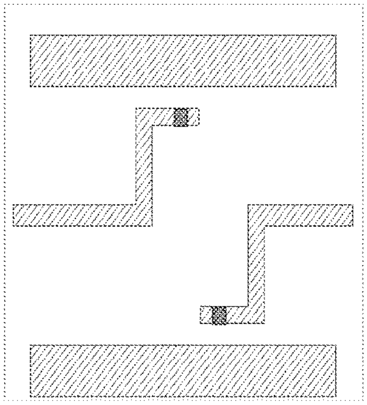
FIG. 1872C

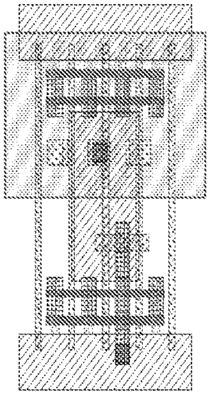
FIG. 1873A
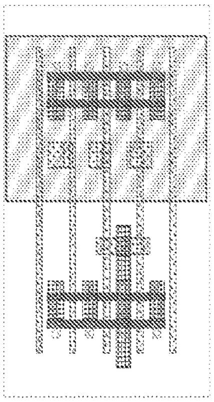
FIG. 1873B
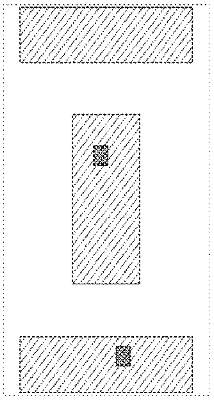
FIG. 1873C

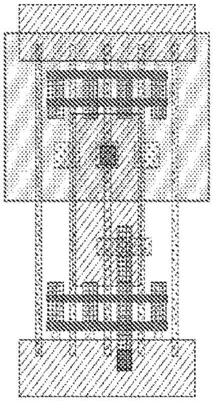
FIG. 1874A
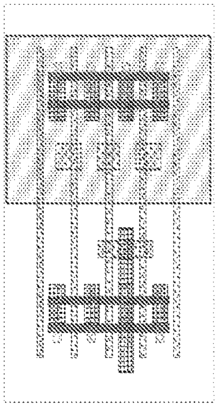
FIG. 1874B
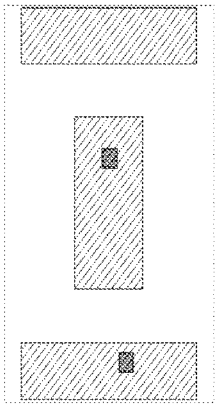
FIG. 1874C

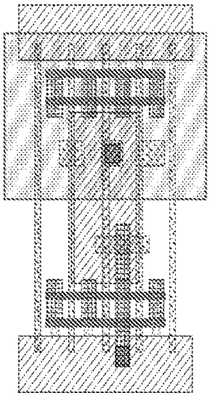
FIG. 1875A
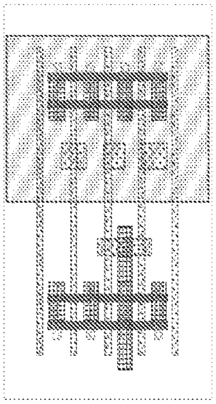
FIG. 1875B
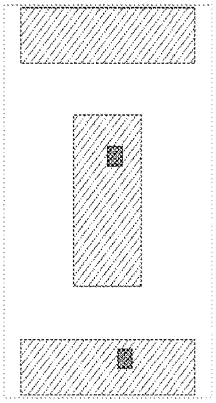
FIG. 1875C

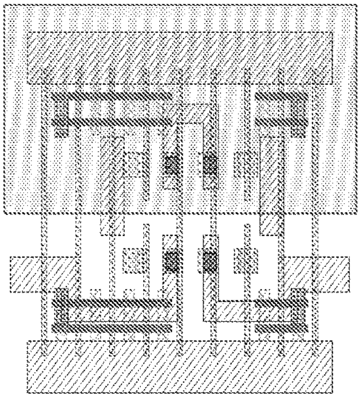
FIG. 1876A
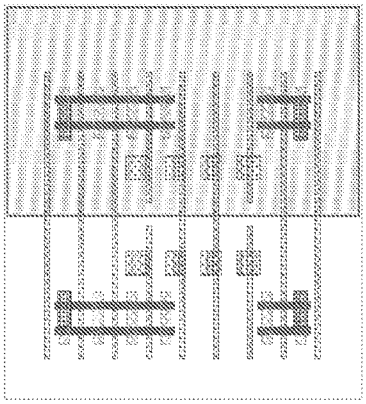
FIG. 1876B
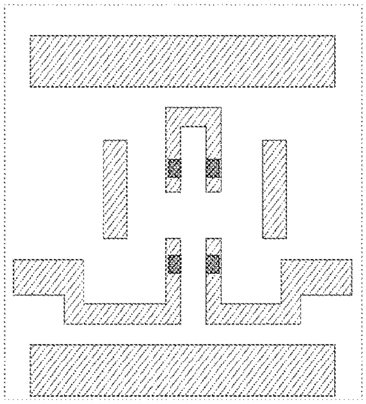
FIG. 1876C
*M* PDF Solutions, Inc.

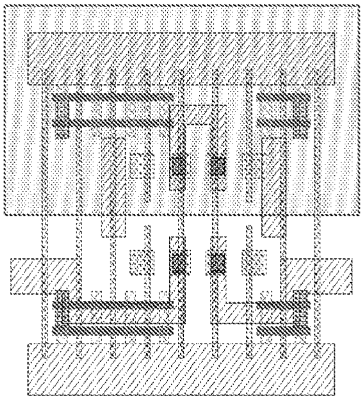
FIG. 1877A
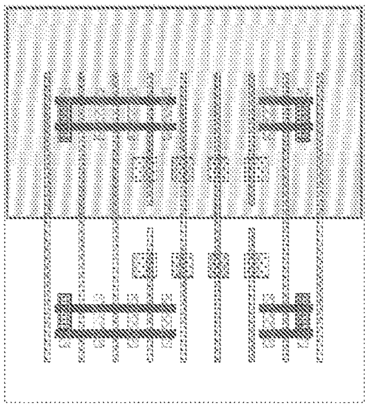
FIG. 1877B
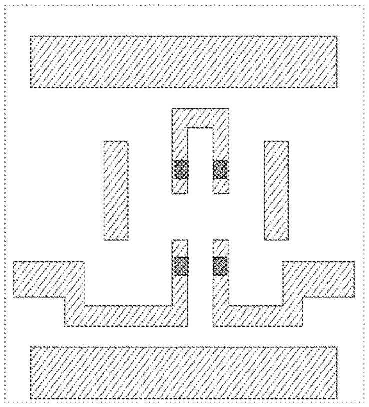
FIG. 1877C

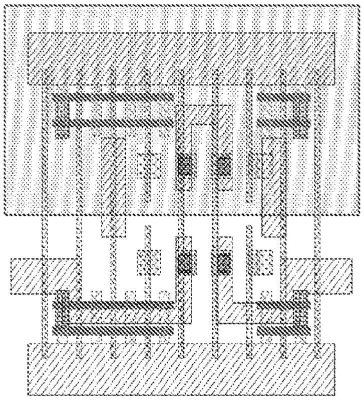
FIG. 1878A
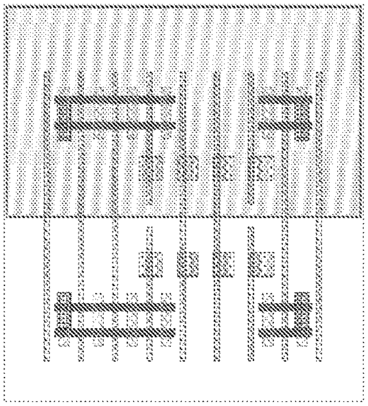
FIG. 1878B
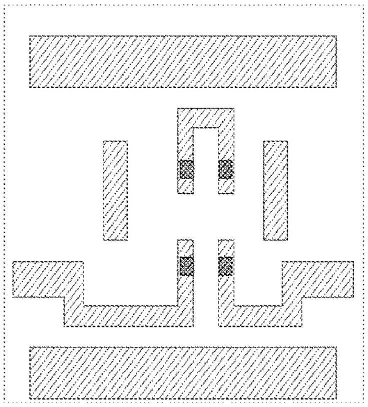
FIG. 1878C

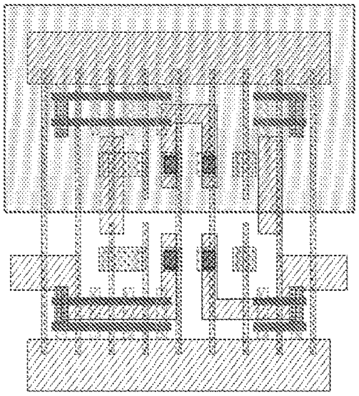
FIG. 1879A
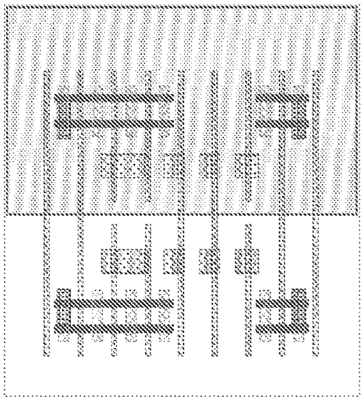
FIG. 1879B
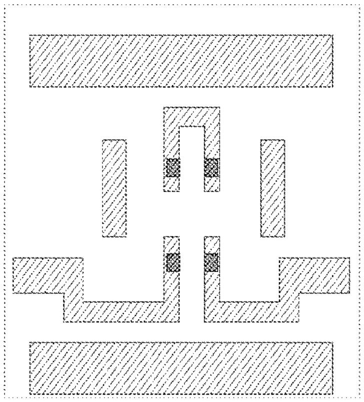
FIG. 1879C

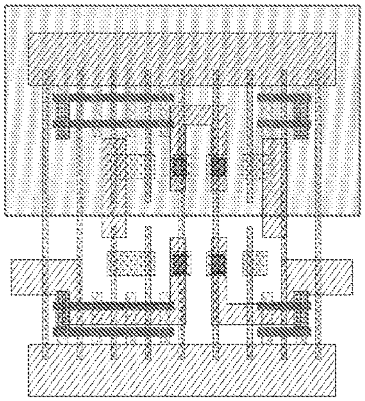
FIG. 1880A
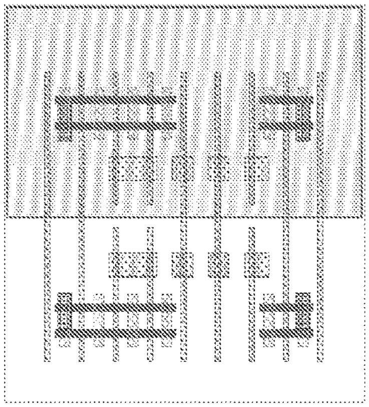
FIG. 1880B
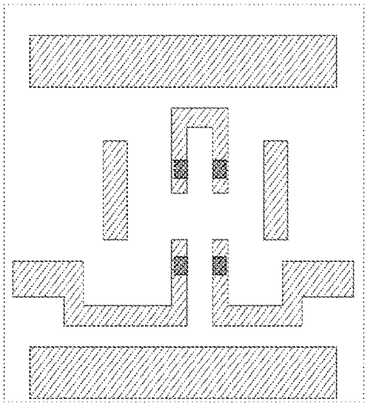
FIG. 1880C

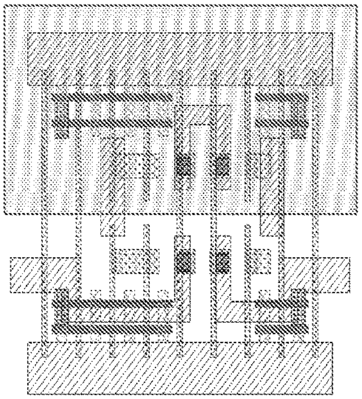
FIG. 1881A
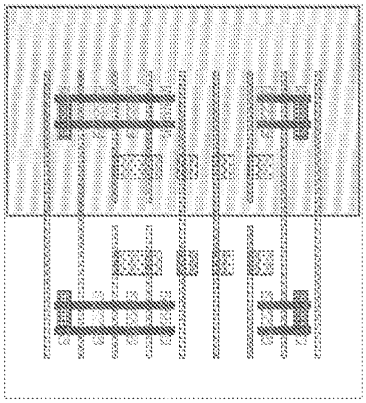
FIG. 1881B
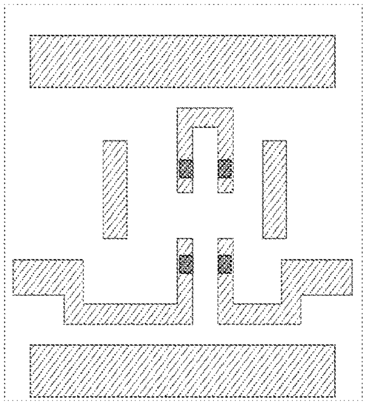
FIG. 1881C

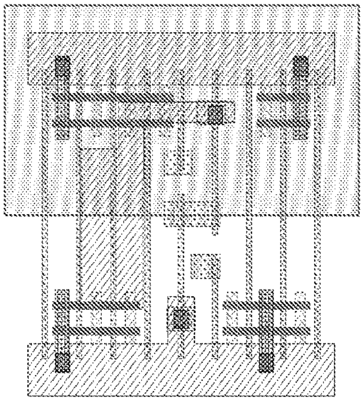
FIG. 1882A
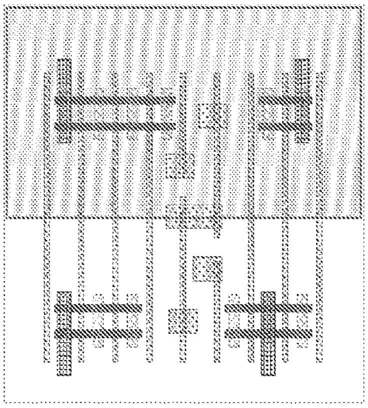
FIG. 1882B
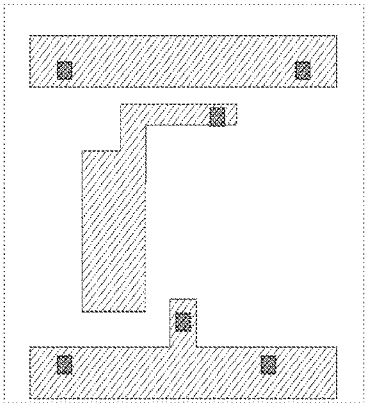
FIG. 1882C

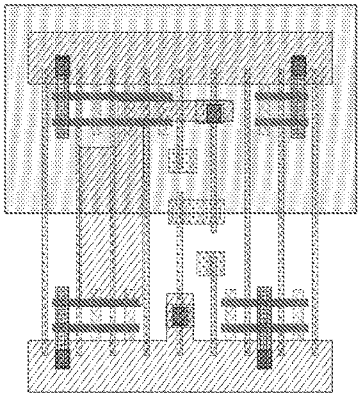
FIG. 1883A
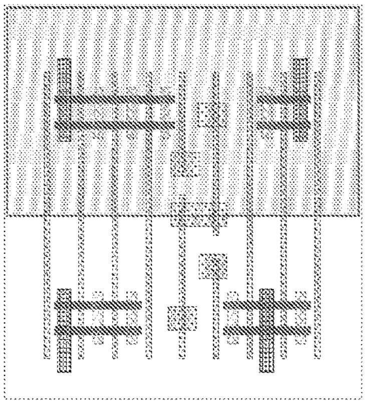
FIG. 1883B
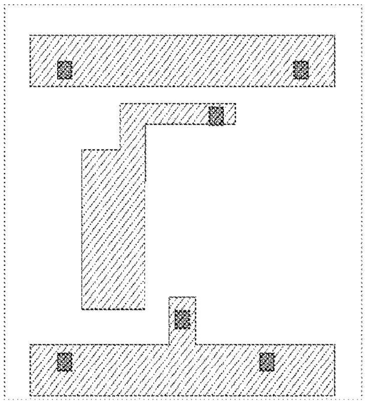
FIG. 1883C

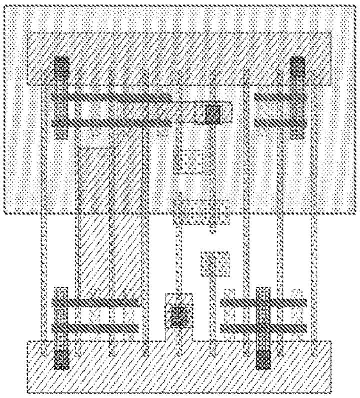
FIG. 1884A
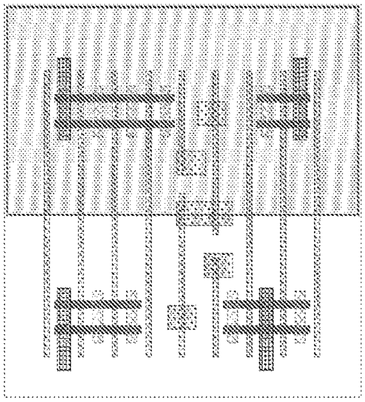
FIG. 1884B
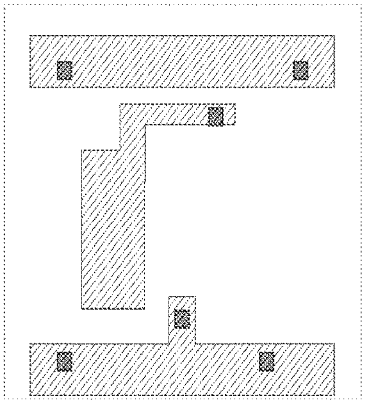
FIG. 1884C

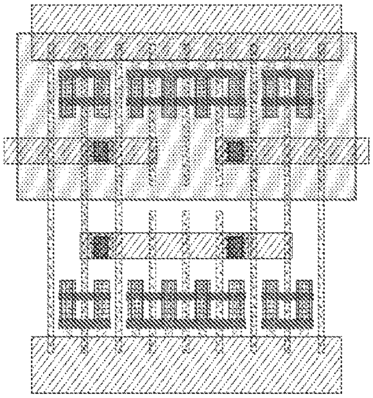
FIG. 1885A
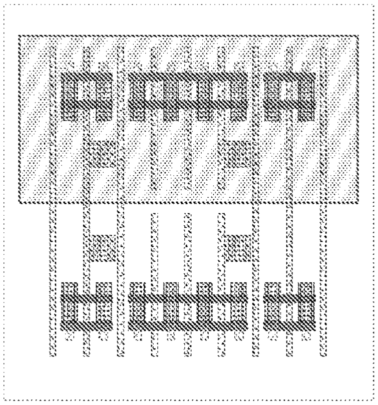
FIG. 1885B
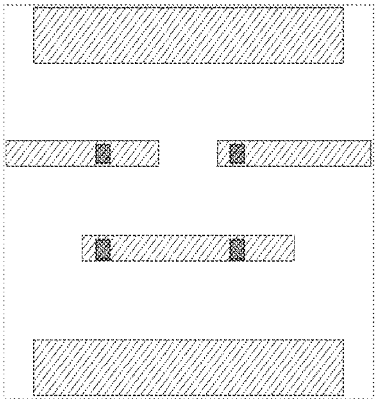
FIG. 1885C

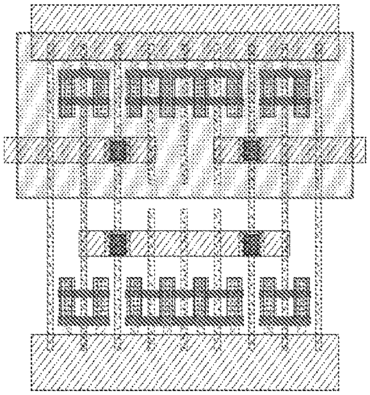
FIG. 1886A
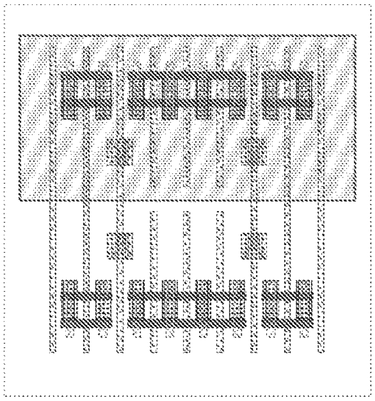
FIG. 1886B
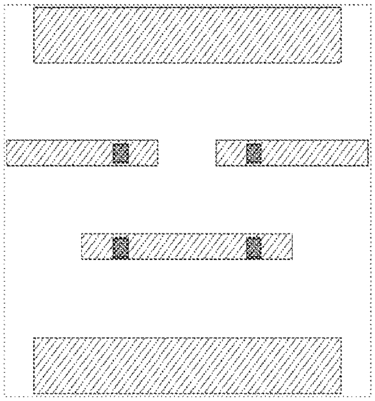
FIG. 1886C

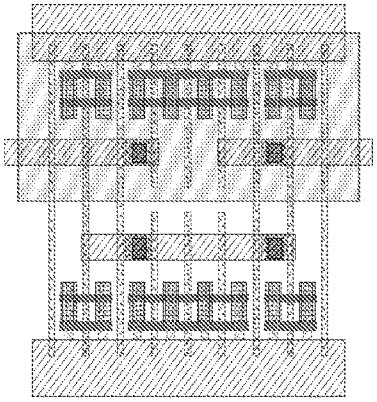
FIG. 1887A
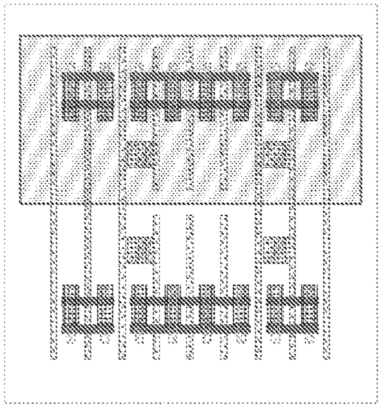
FIG. 1887B
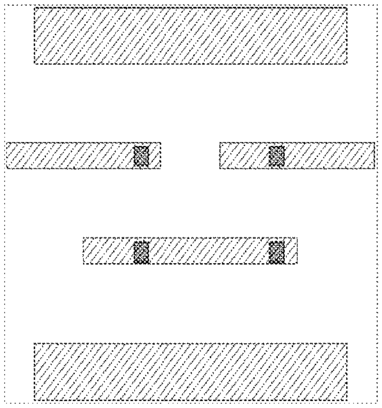
FIG. 1887C

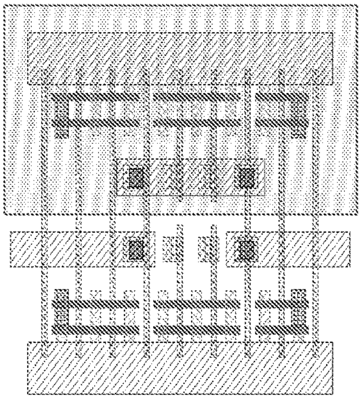
FIG. 1888A
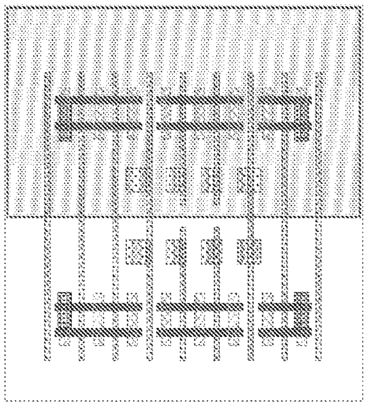
FIG. 1888B
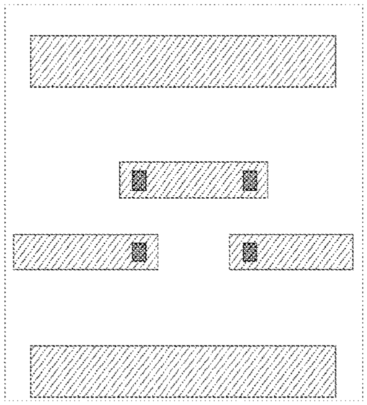
FIG. 1888C

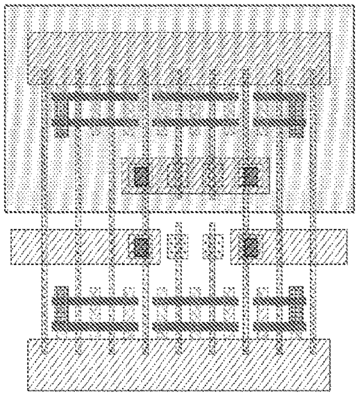
FIG. 1889A
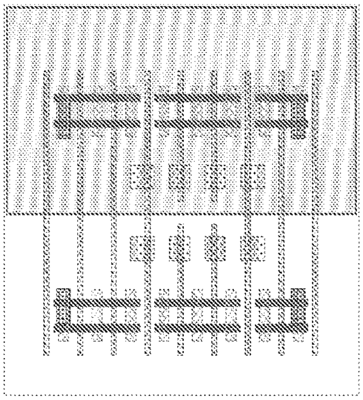
FIG. 1889B
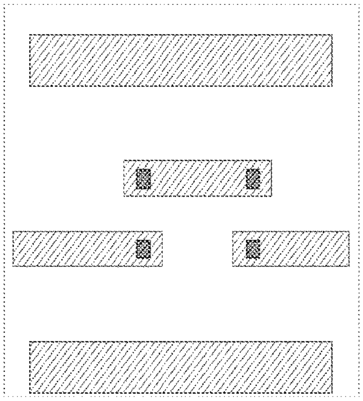
FIG. 1889C

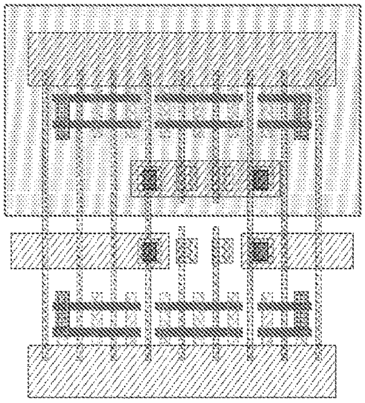
FIG. 1890A
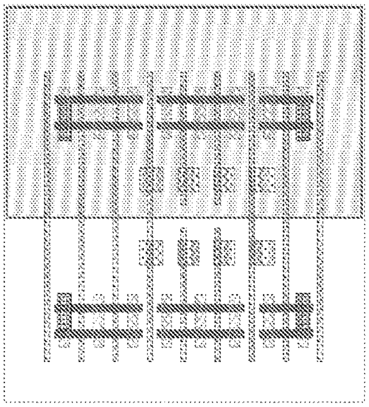
FIG. 1890B
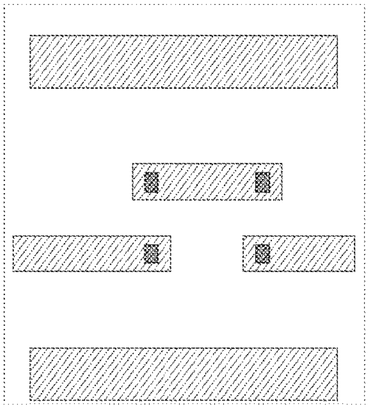
FIG. 1890C
*M* PDF Solutions, Inc.

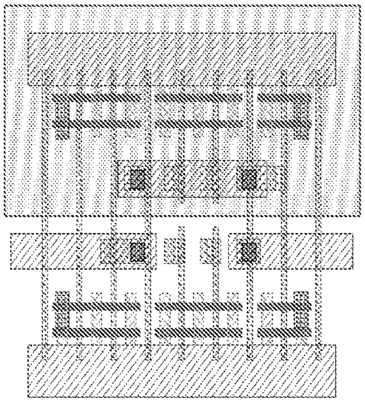
FIG. 1891A
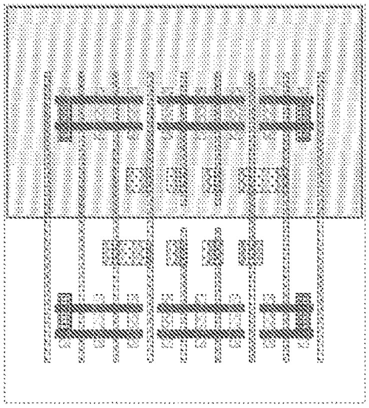
FIG. 1891B
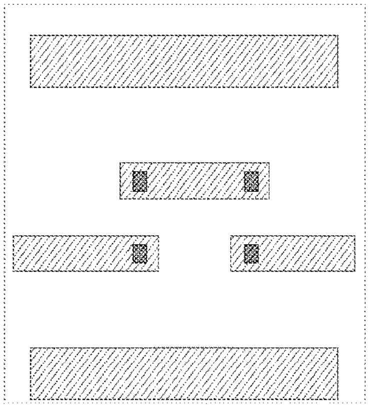
FIG. 1891C

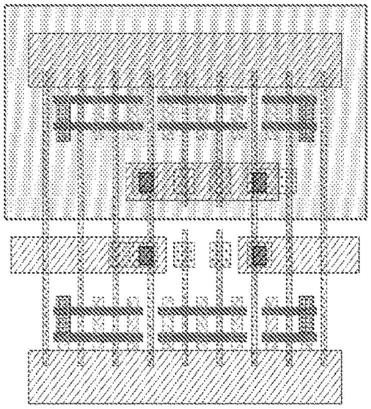
FIG. 1892A
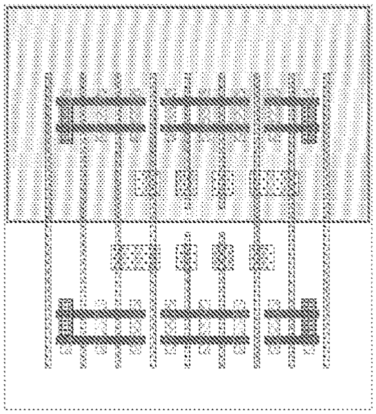
FIG. 1892B
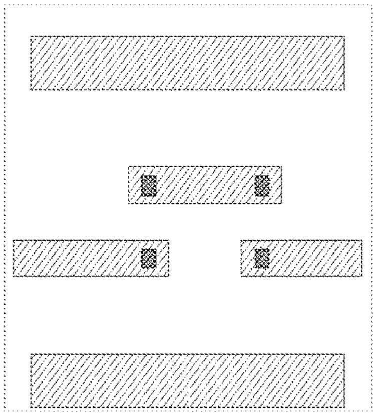
FIG. 1892C

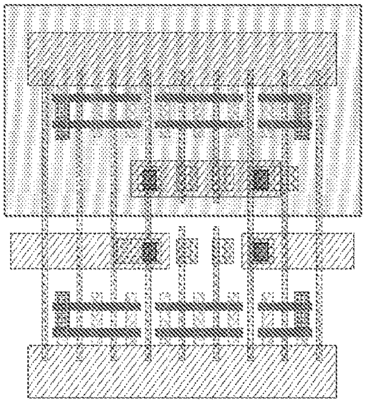
FIG. 1893A
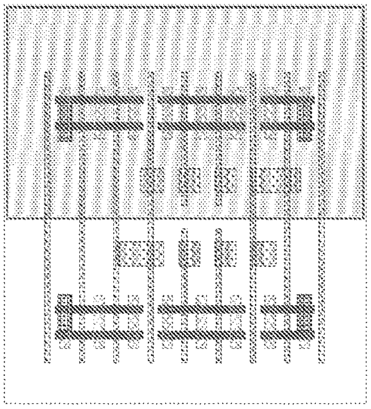
FIG. 1893B
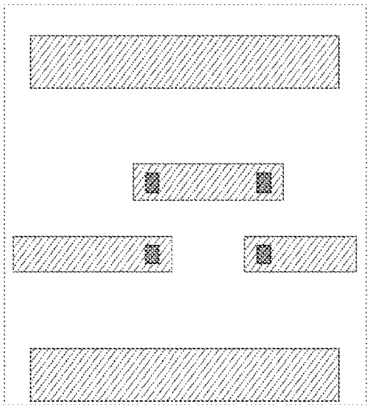
FIG. 1893C

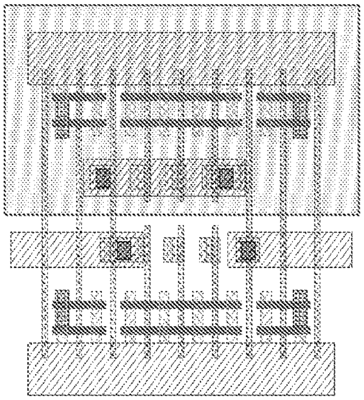
FIG. 1894A
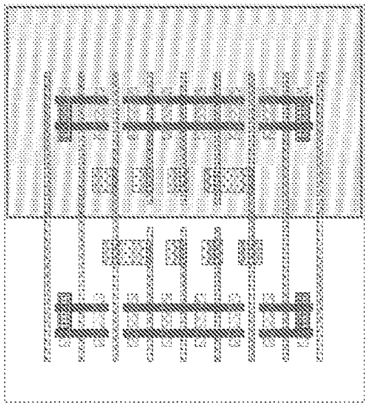
FIG. 1894B
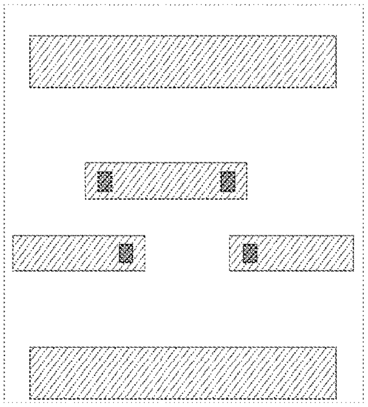
FIG. 1894C

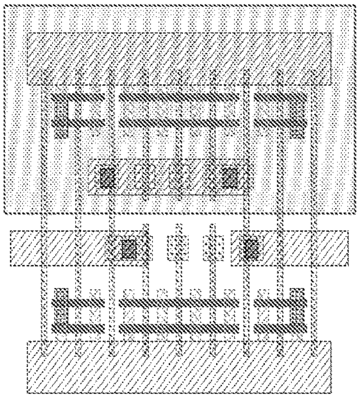
FIG. 1895A
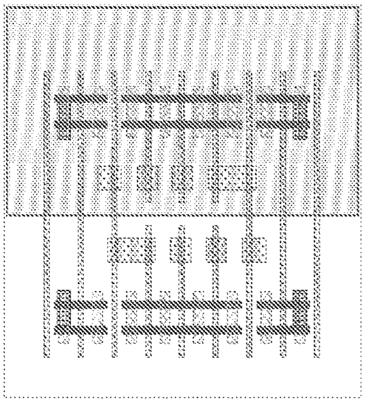
FIG. 1895B
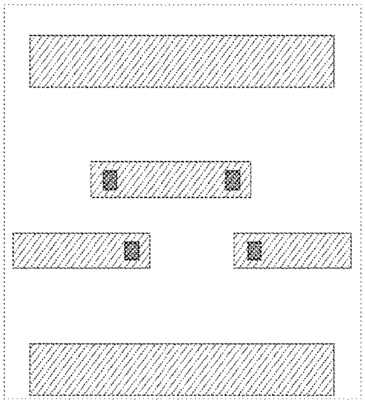
FIG. 1895C

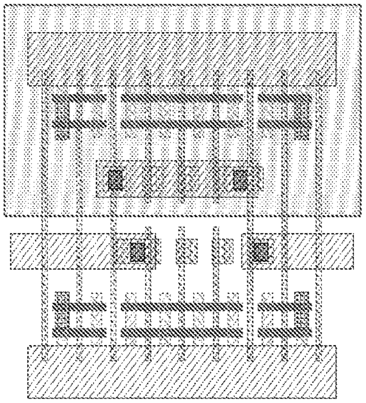
FIG. 1896A
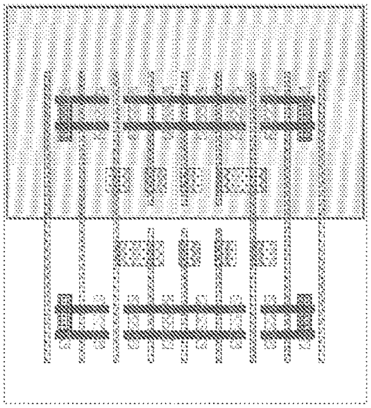
FIG. 1896B
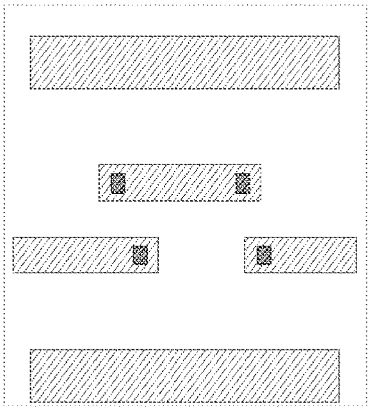
FIG. 1896C

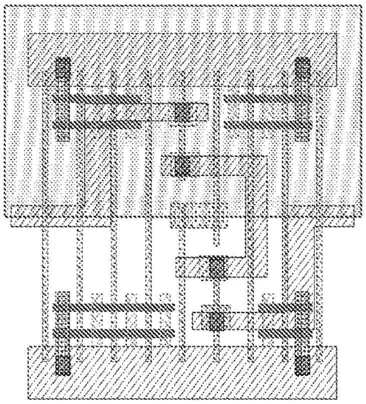
FIG. 1897A
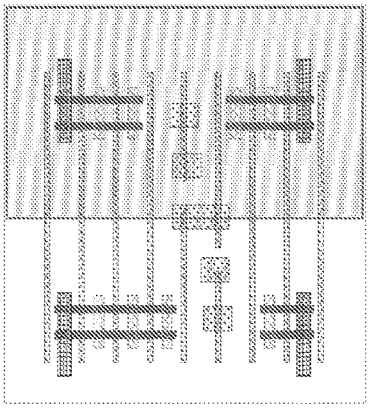
FIG. 1897B
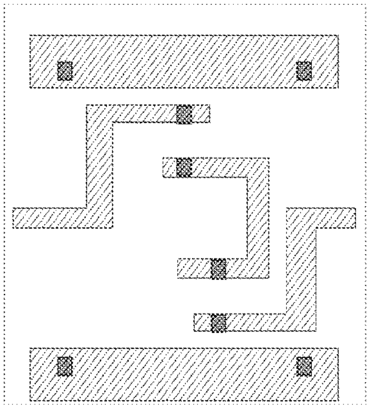
FIG. 1897C

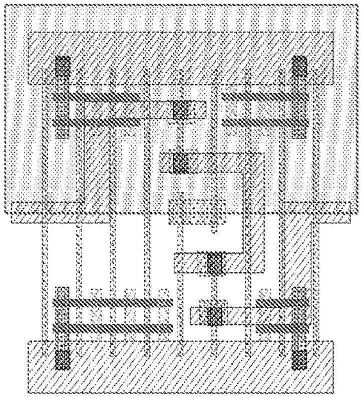
FIG. 1898A
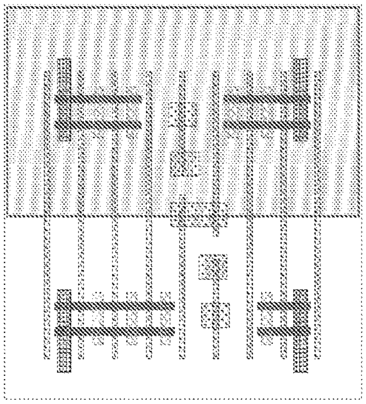
FIG. 1898B
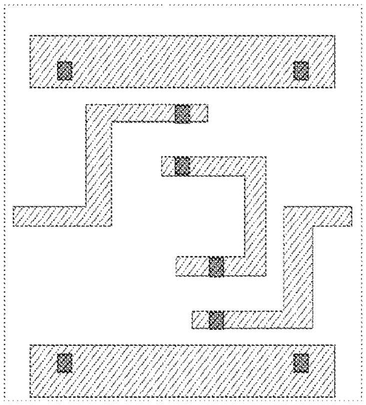
FIG. 1898C

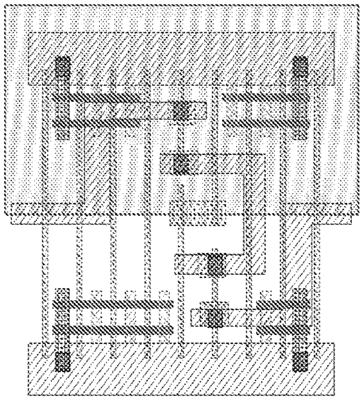
FIG. 1899A
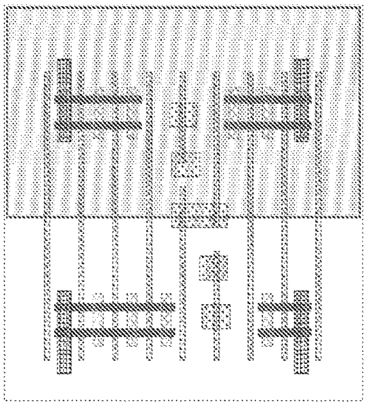
FIG. 1899B
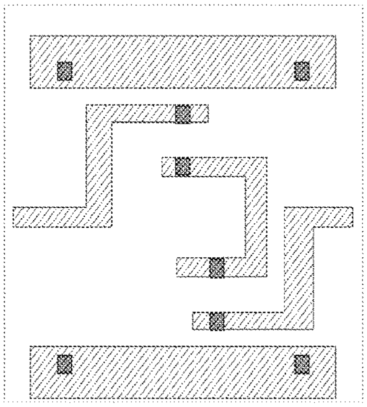
FIG. 1899C

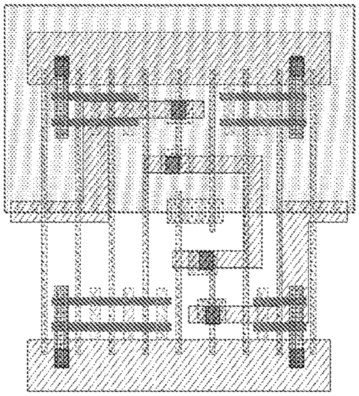
FIG. 1900A
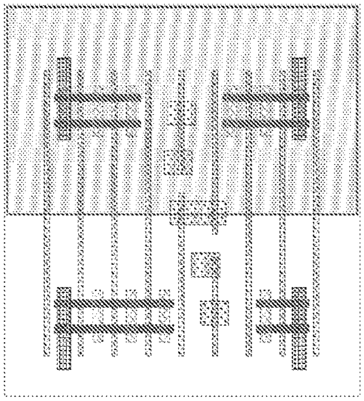
FIG. 1900B
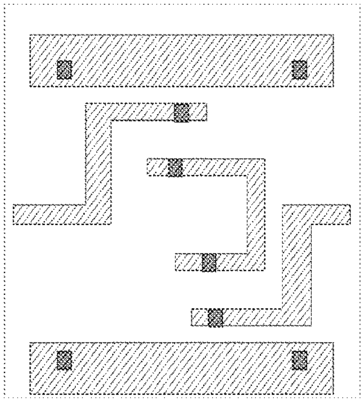
FIG. 1900C
*M* PDF Solutions, Inc.

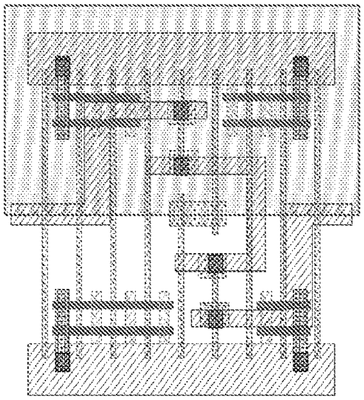
FIG. 1901A
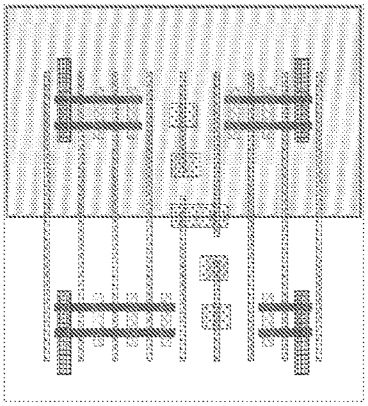
FIG. 1901B
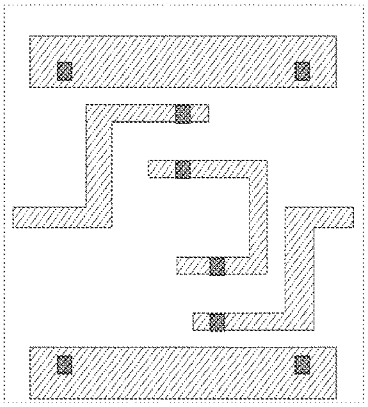
FIG. 1901C

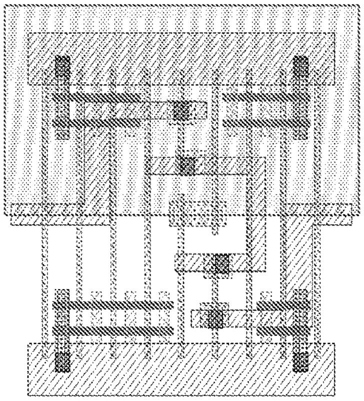
FIG. 1902A
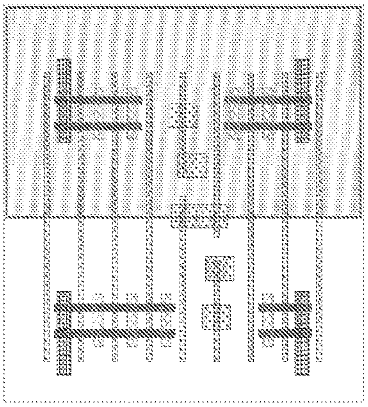
FIG. 1902B
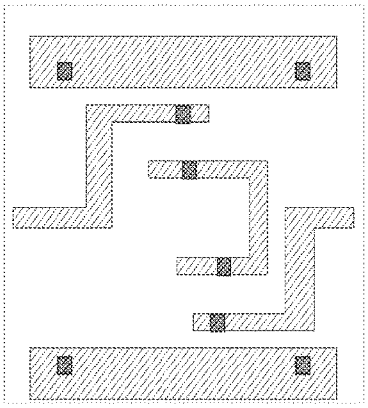
FIG. 1902C

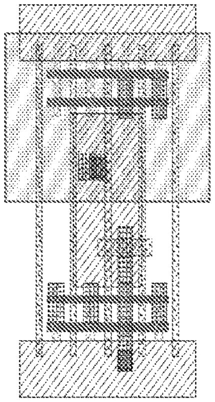
FIG. 1903A
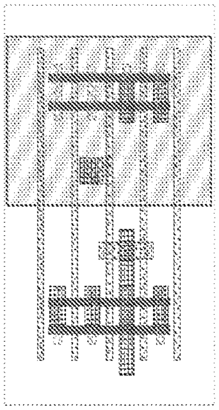
FIG. 1903B
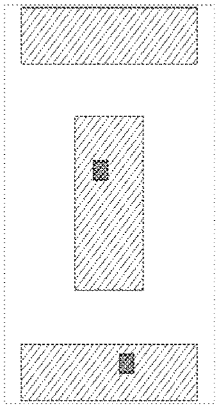
FIG. 1903C

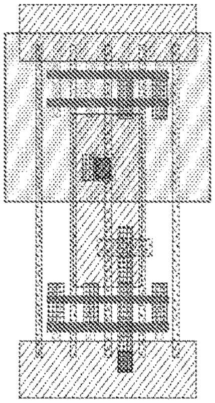
FIG. 1904A
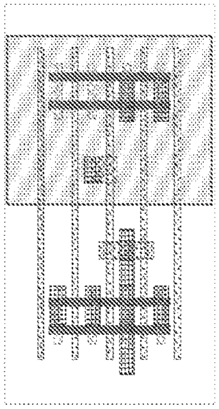
FIG. 1904B
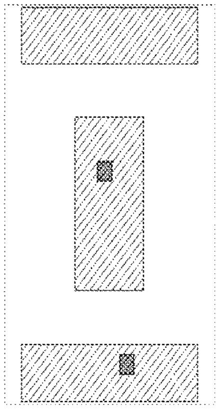
FIG. 1904C
*M* PDF Solutions, Inc.

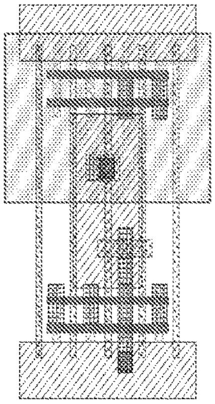
FIG. 1905A
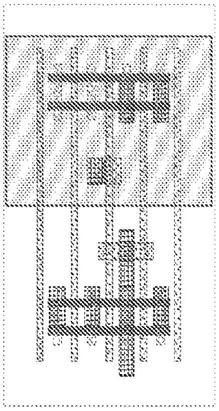
FIG. 1905B
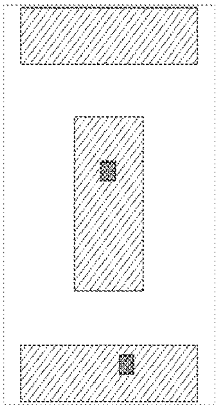
FIG. 1905C

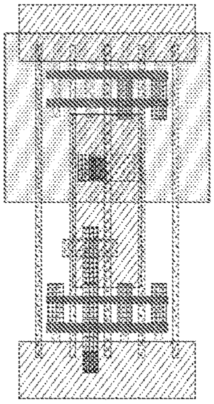
FIG. 1906A
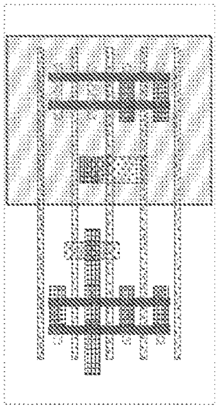
FIG. 1906B
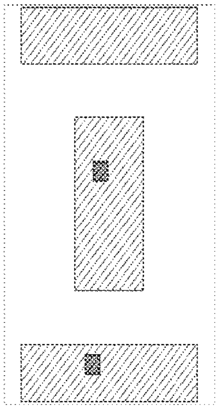
FIG. 1906C
*M* PDF Solutions, Inc.

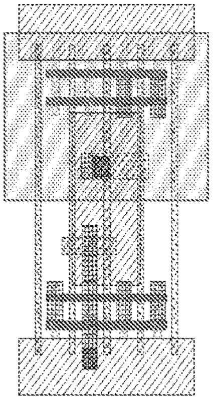
FIG. 1907A
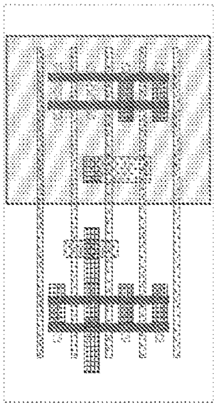
FIG. 1907B
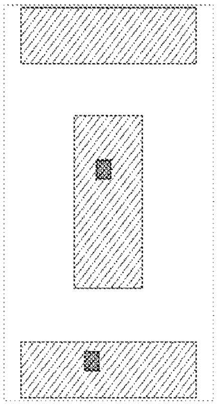
FIG. 1907C

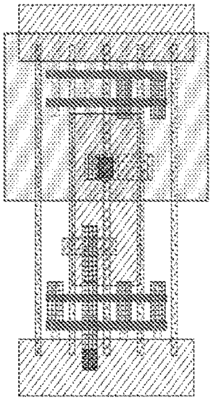
FIG. 1908A
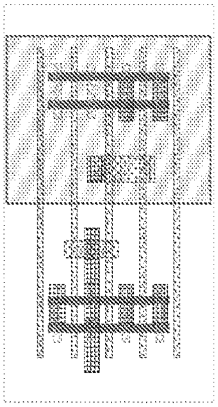
FIG. 1908B
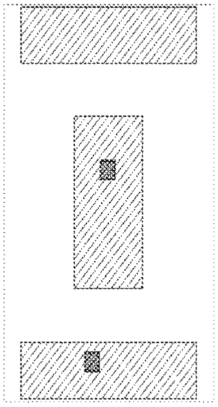
FIG. 1908C

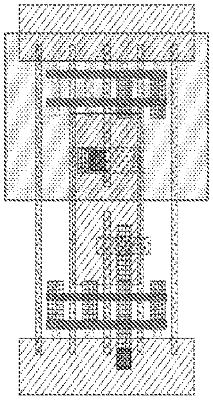
FIG. 1909A
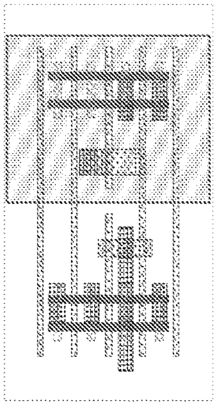
FIG. 1909B
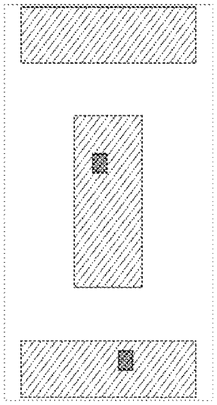
FIG. 1909C

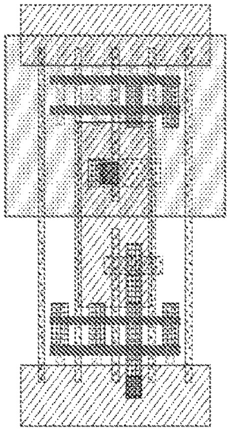
FIG. 1910A
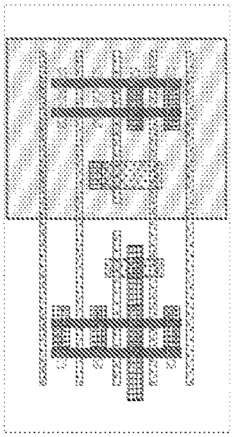
FIG. 1910B
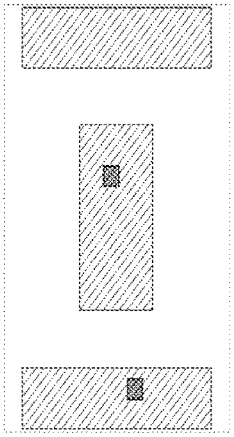
FIG. 1910C

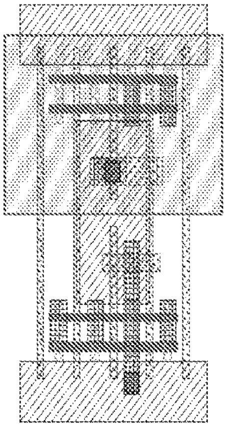
FIG. 1911A
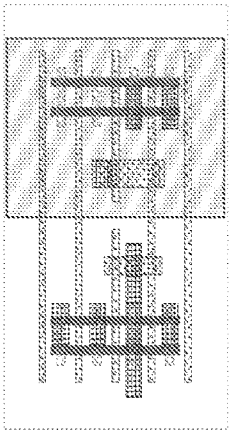
FIG. 1911B
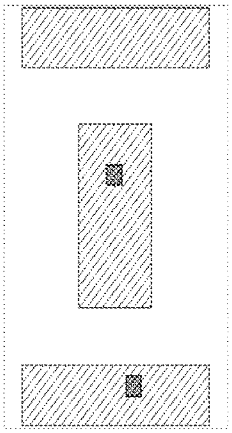
FIG. 1911C

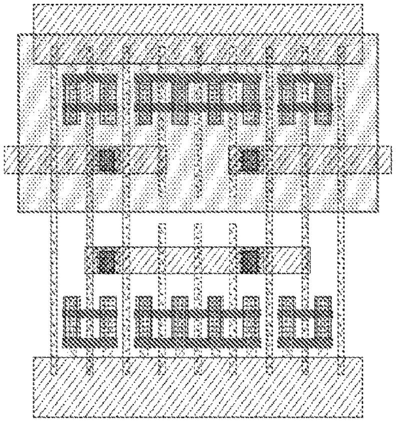
FIG. 1912A
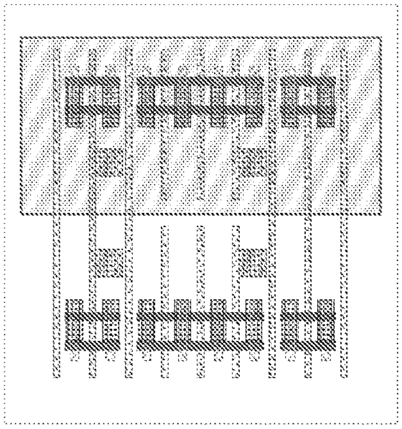
FIG. 1912B
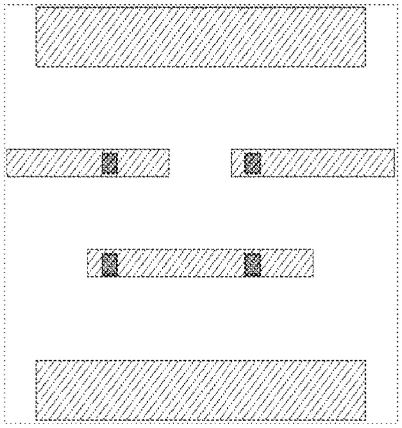
FIG. 1912C

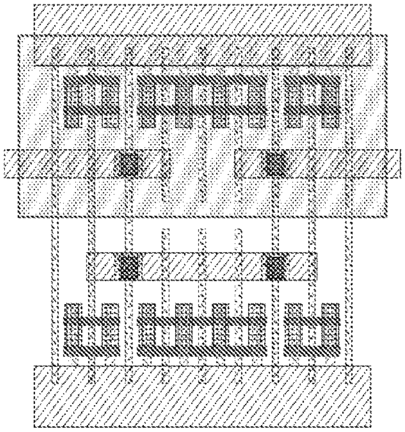
FIG. 1913A
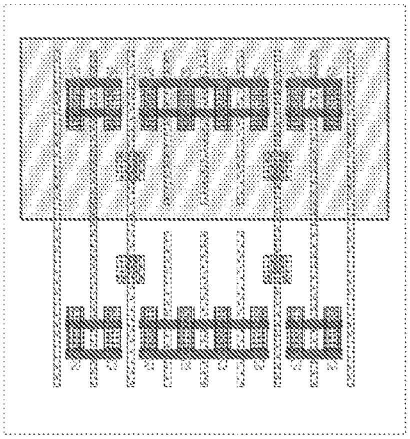
FIG. 1913B
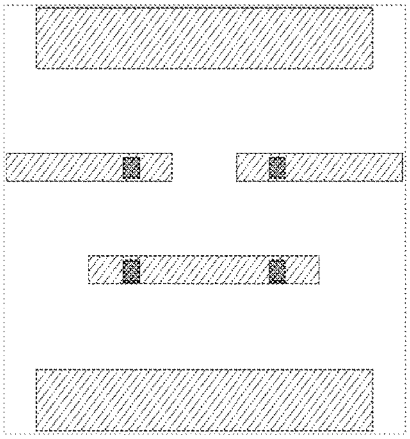
FIG. 1913C

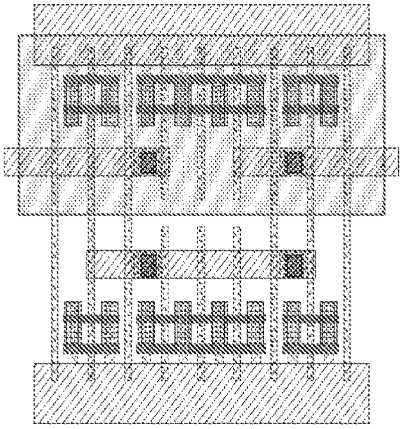
FIG. 1914A
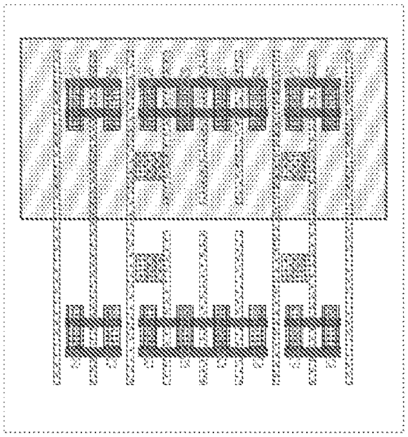
FIG. 1914B
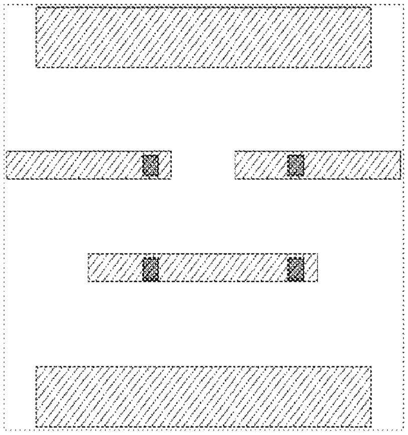
FIG. 1914C

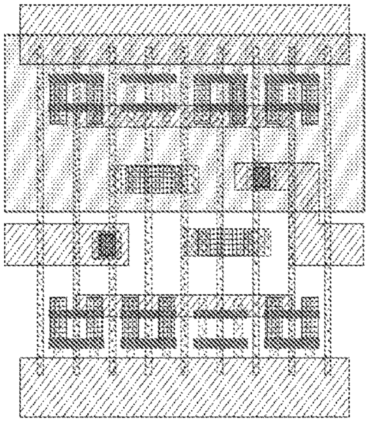
FIG. 1915A
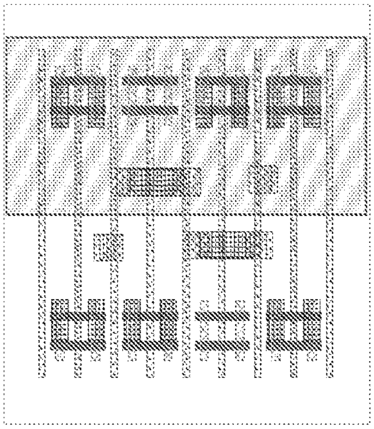
FIG. 1915B
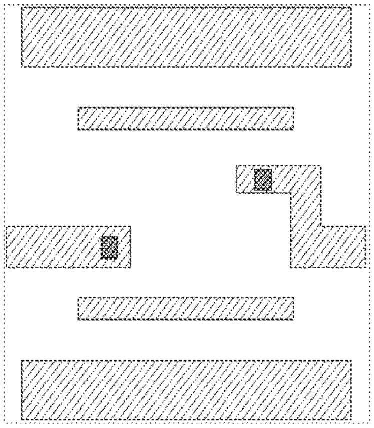
FIG. 1915C

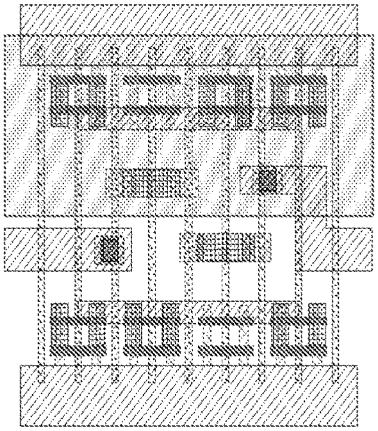
FIG. 1916A
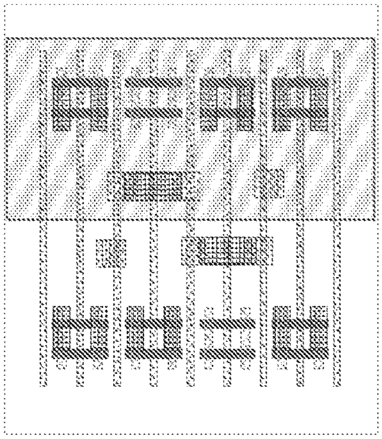
FIG. 1916B
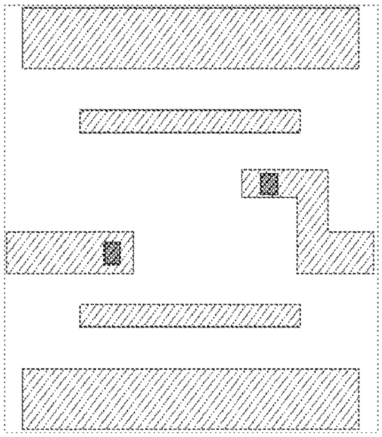
FIG. 1916C
*M* PDF Solutions, Inc.

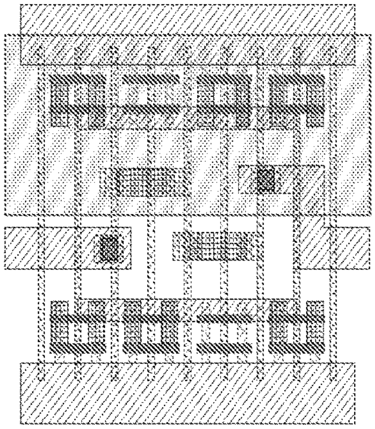
FIG. 1917A
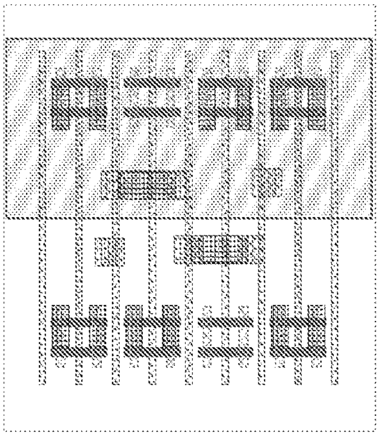
FIG. 1917B
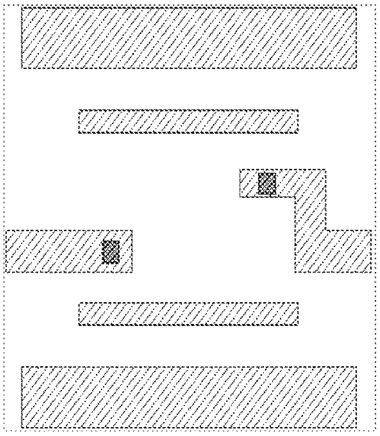
FIG. 1917C

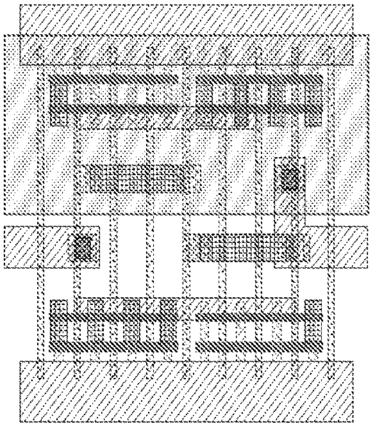
FIG. 1918A
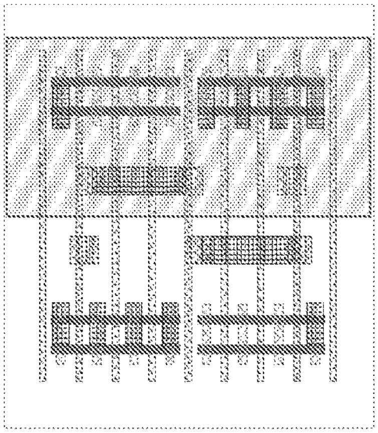
FIG. 1918B
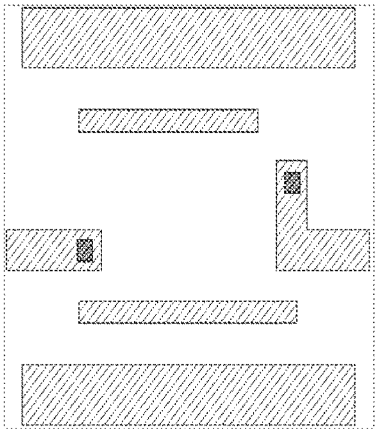
FIG. 1918C
*M* PDF Solutions, Inc.

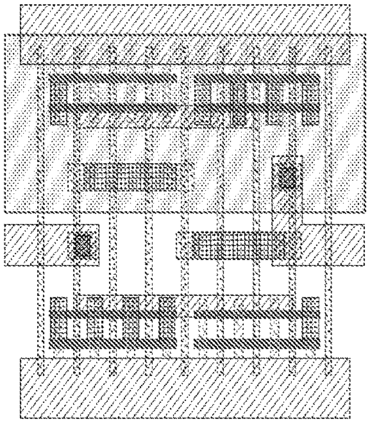
FIG. 1919A
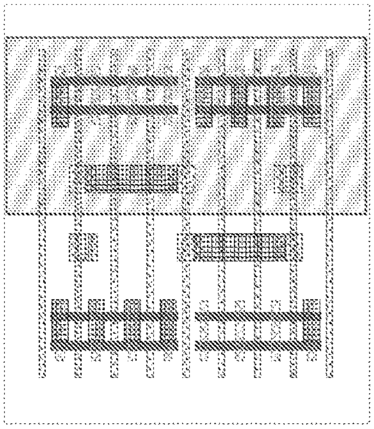
FIG. 1919B
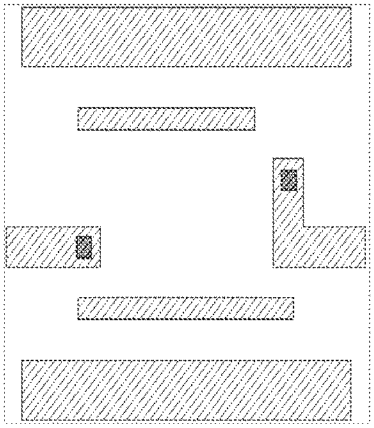
FIG. 1919C

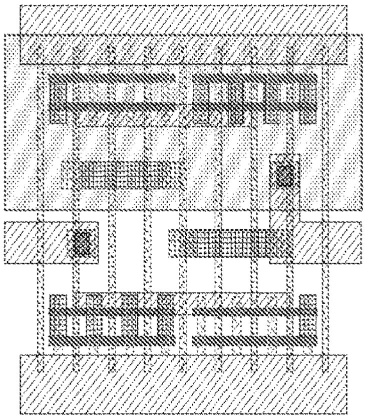
FIG. 1920A
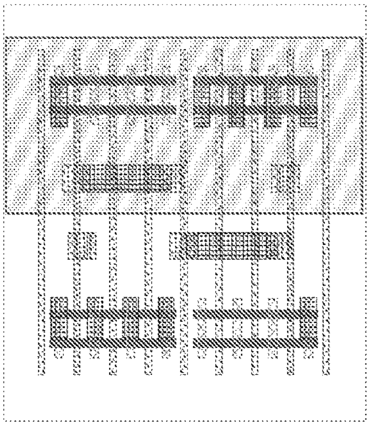
FIG. 1920B
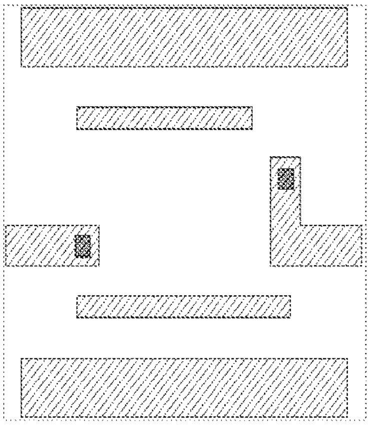
FIG. 1920C
*M* PDF Solutions, Inc.

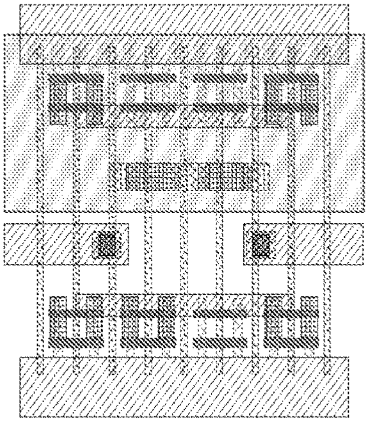
FIG. 1921A
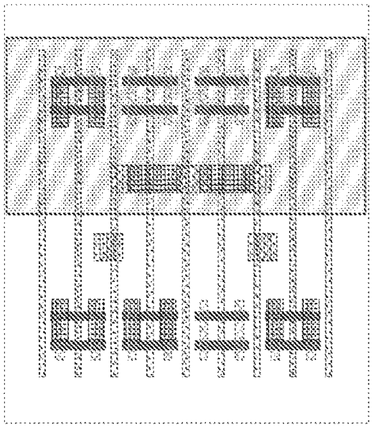
FIG. 1921B
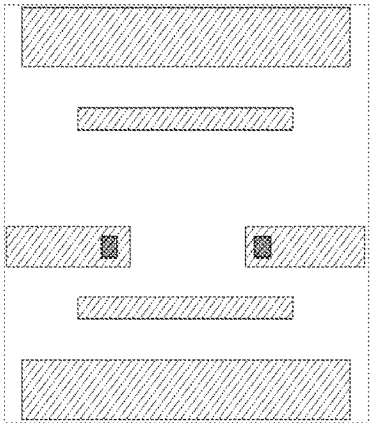
FIG. 1921C

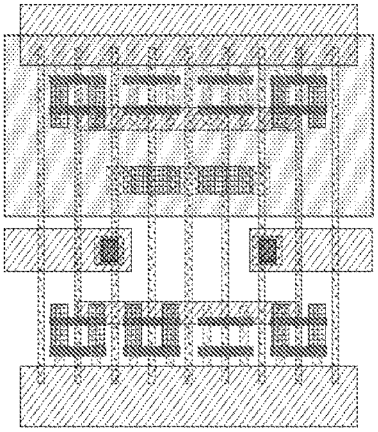
FIG. 1922A
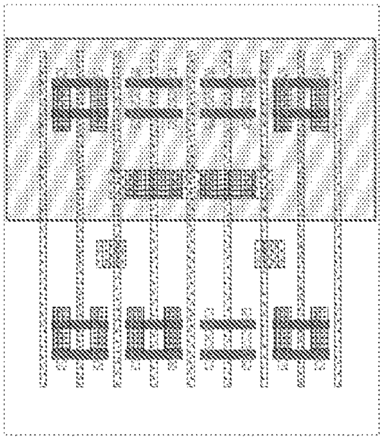
FIG. 1922B
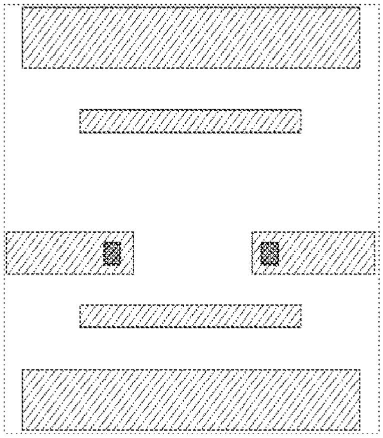
FIG. 1922C

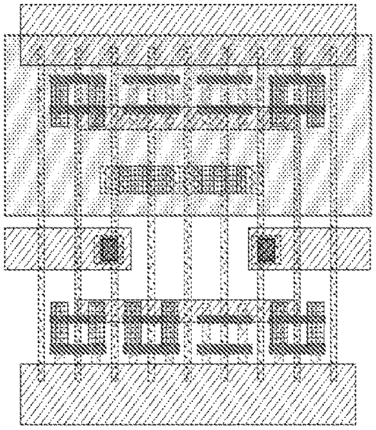
FIG. 1923A
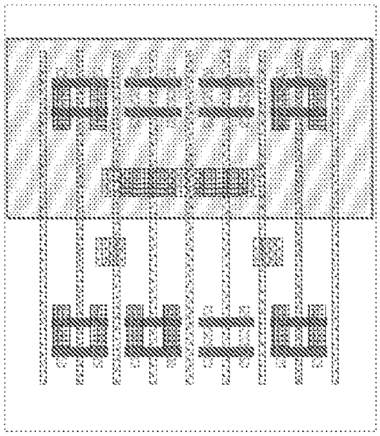
FIG. 1923B
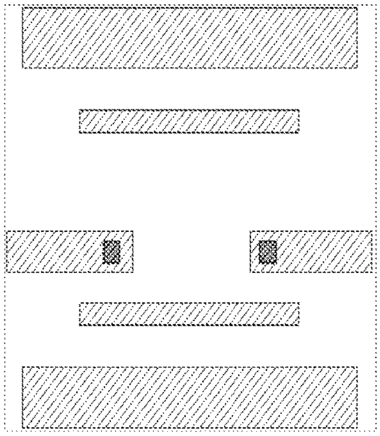
FIG. 1923C

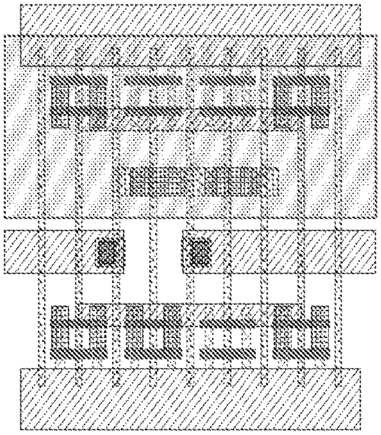
FIG. 1924A
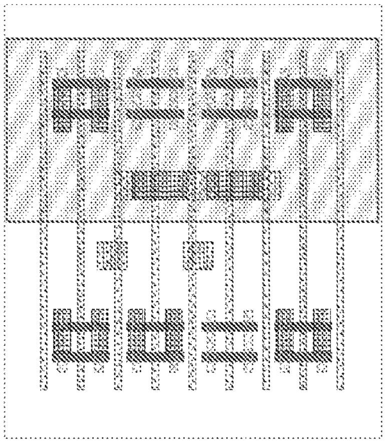
FIG. 1924B
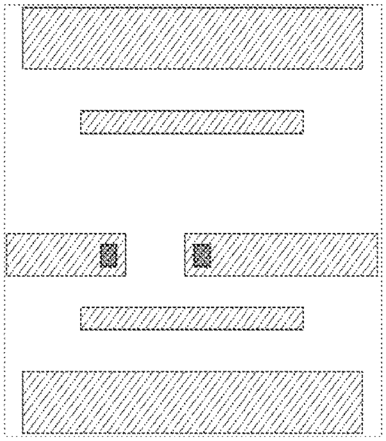
FIG. 1924C

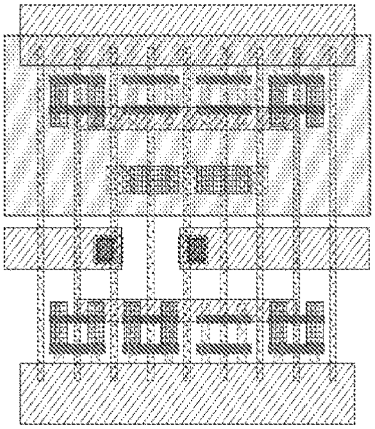
FIG. 1925A
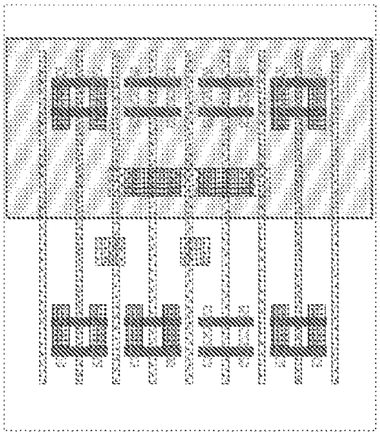
FIG. 1925B
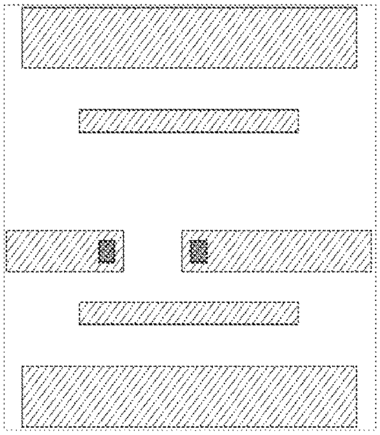
FIG. 1925C
*M* PDF Solutions, Inc.

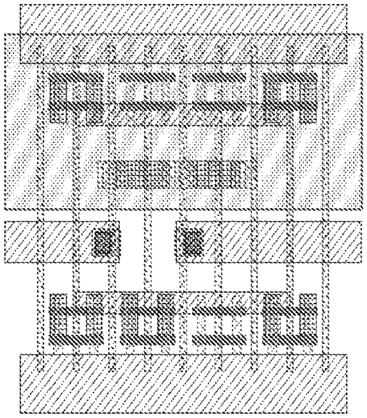
FIG. 1926A
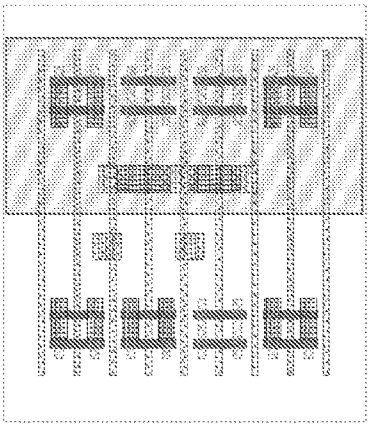
FIG. 1926B
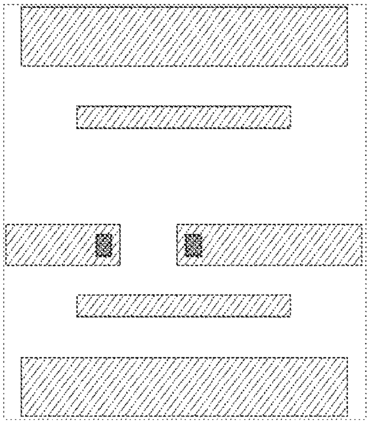
FIG. 1926C

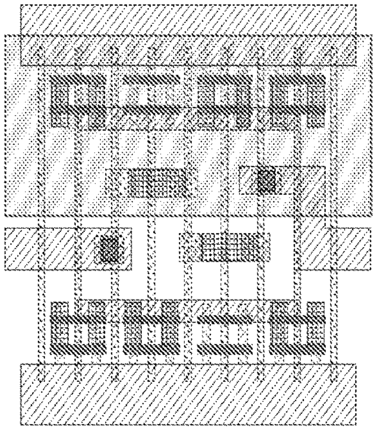
FIG. 1927A
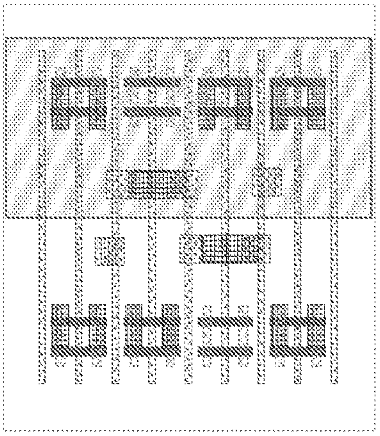
FIG. 1927B
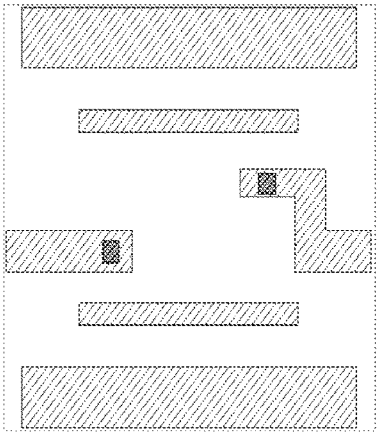
FIG. 1927C

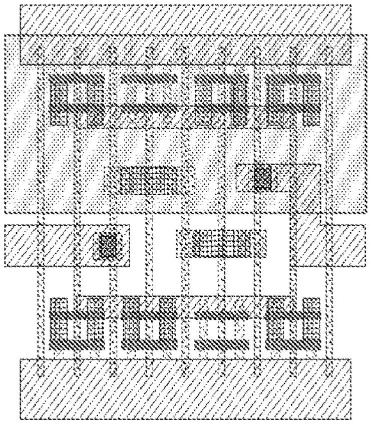
FIG. 1928A
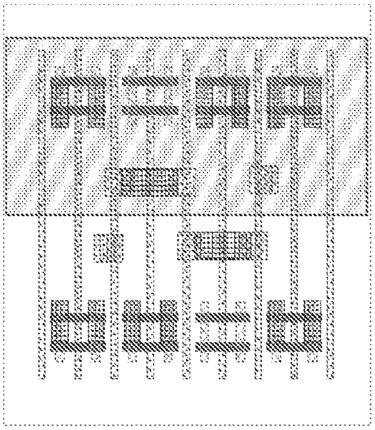
FIG. 1928B
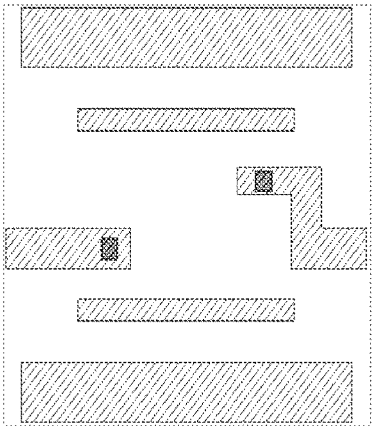
FIG. 1928C

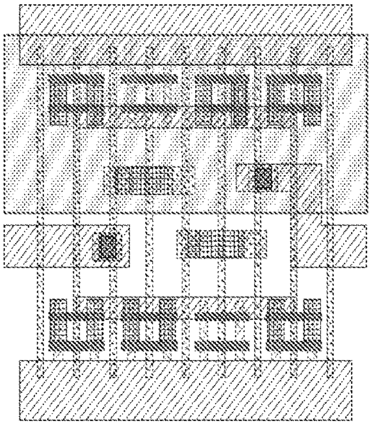
FIG. 1929A
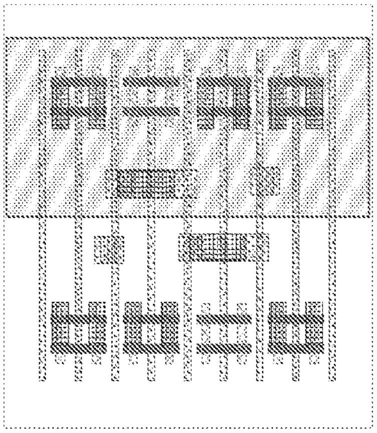
FIG. 1929B
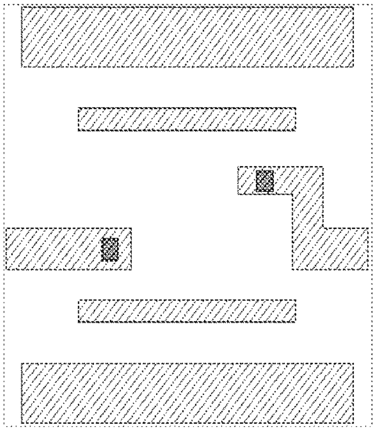
FIG. 1929C

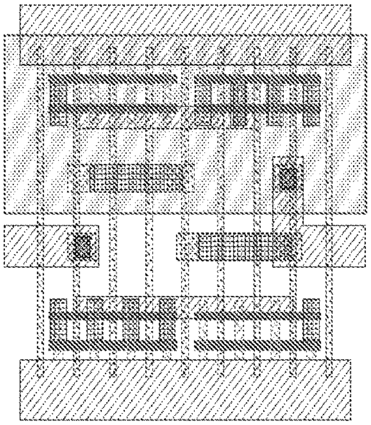
FIG. 1930A
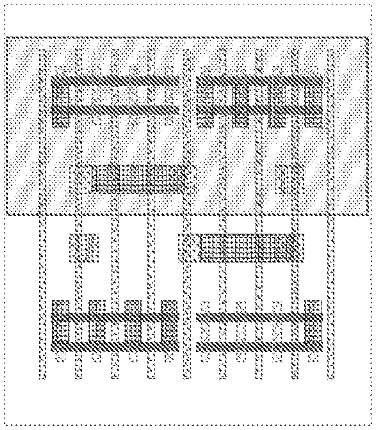
FIG. 1930B
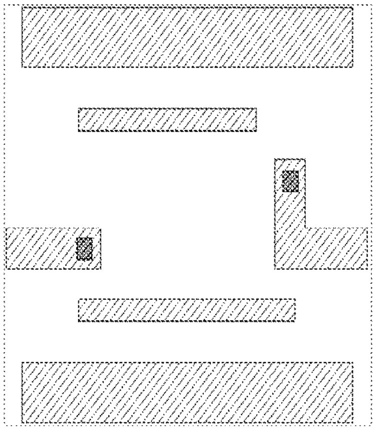
FIG. 1930C

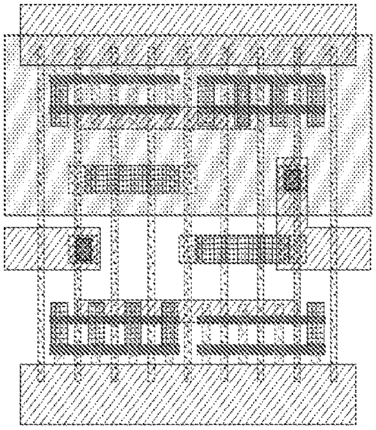
FIG. 1931A
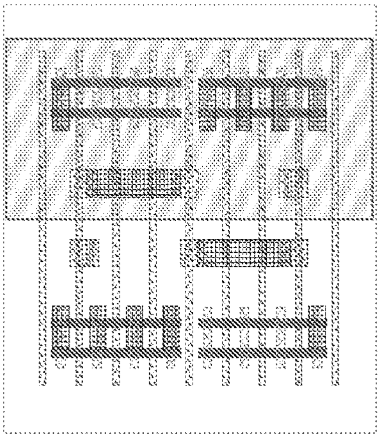
FIG. 1931B
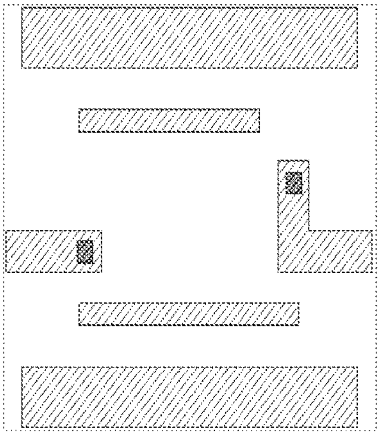
FIG. 1931C
*M* PDF Solutions, Inc.

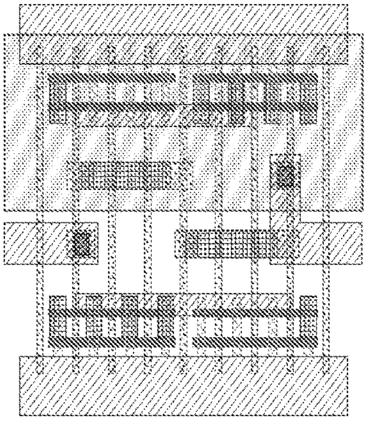
FIG. 1932A
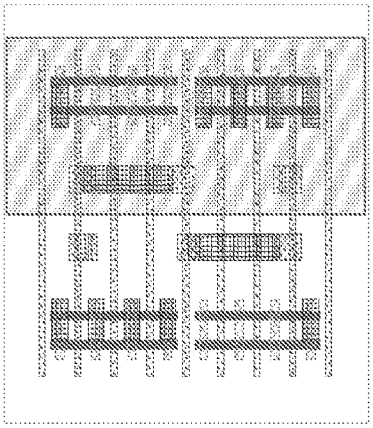
FIG. 1932B
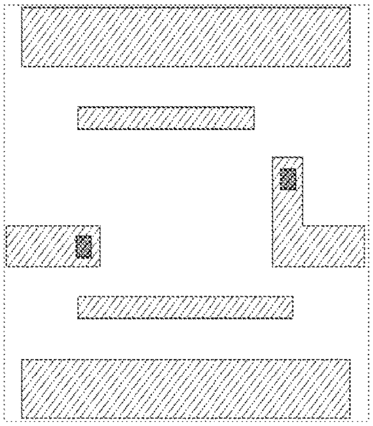
FIG. 1932C

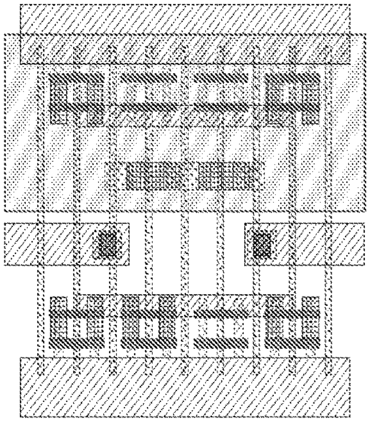
FIG. 1933A
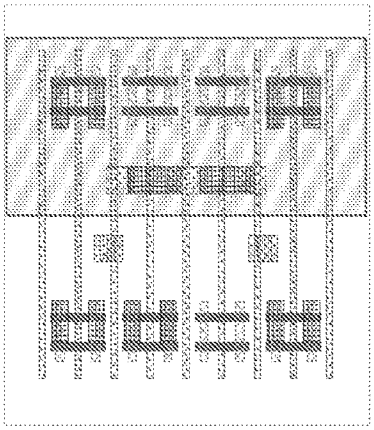
FIG. 1933B
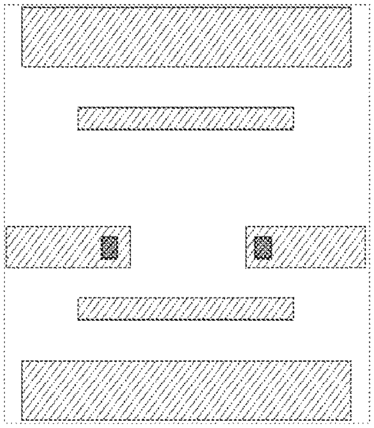
FIG. 1933C

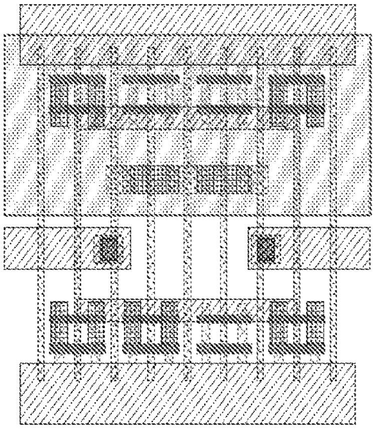
FIG. 1934A
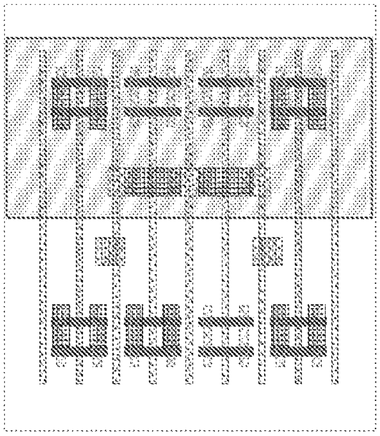
FIG. 1934B
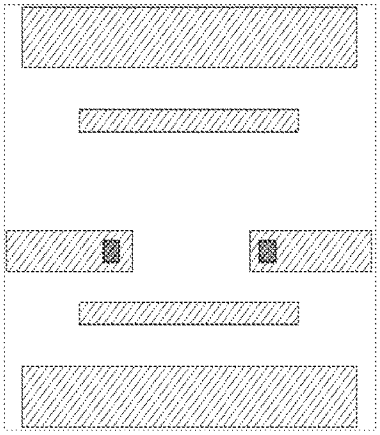
FIG. 1934C
*M* PDF Solutions, Inc.

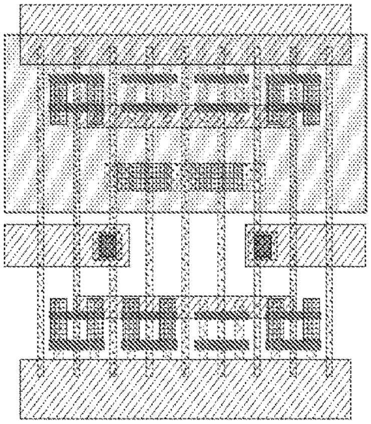
FIG. 1935A
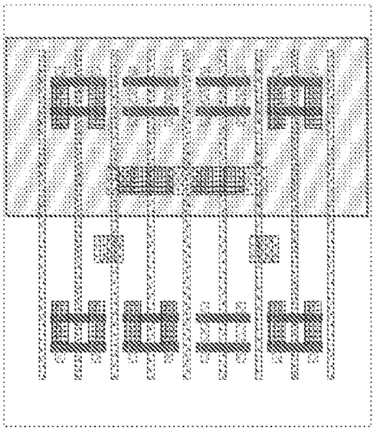
FIG. 1935B
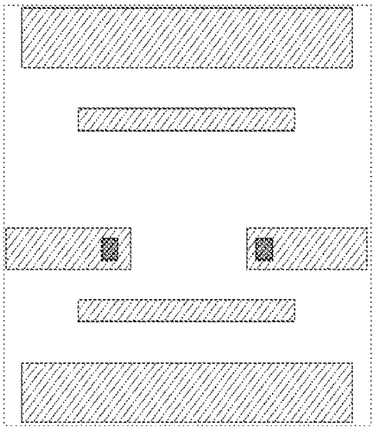
FIG. 1935C

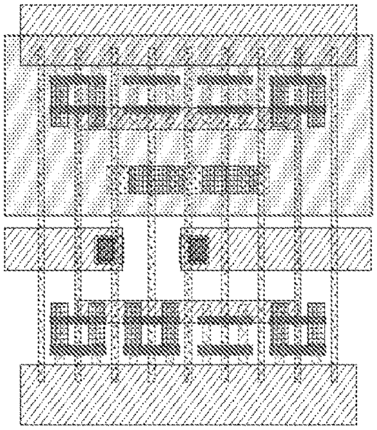
FIG. 1936A
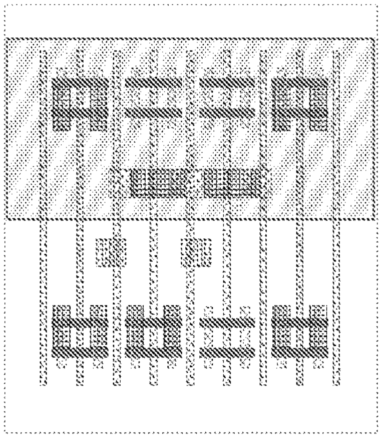
FIG. 1936B
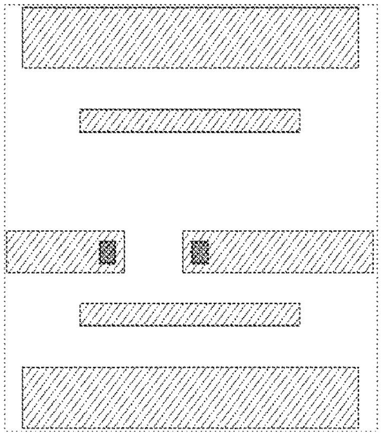
FIG. 1936C
*M* PDF Solutions, Inc.

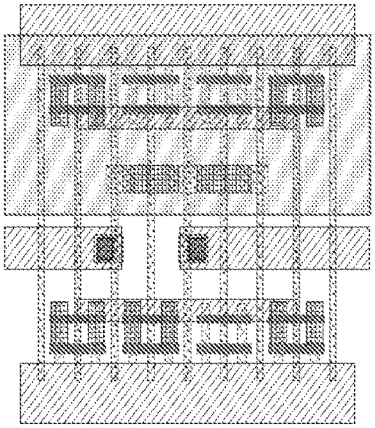
FIG. 1937A
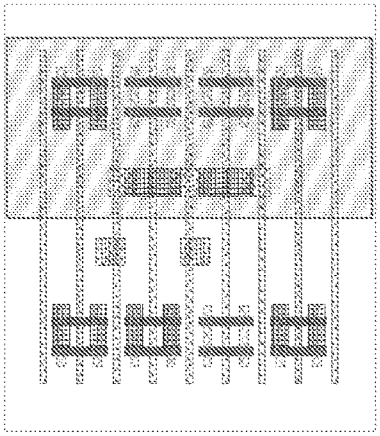
FIG. 1937B
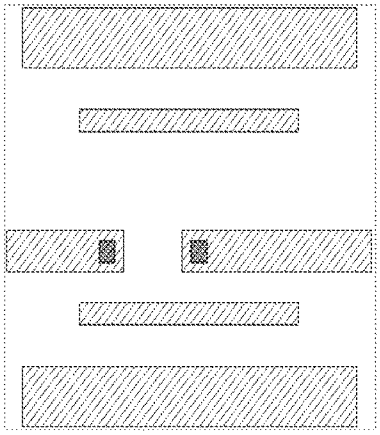
FIG. 1937C

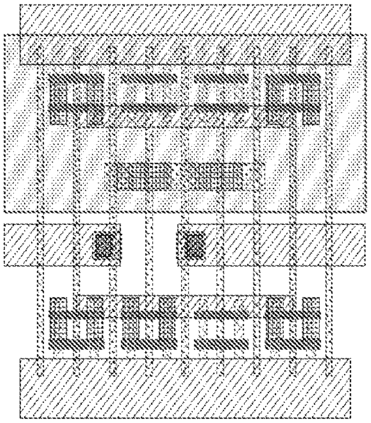
FIG. 1938A
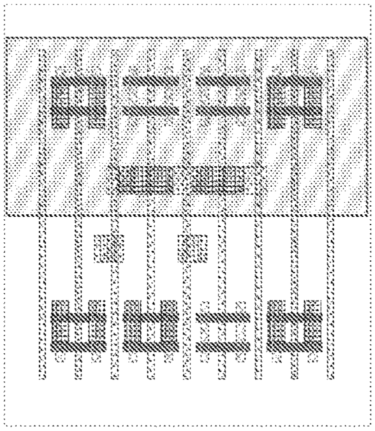
FIG. 1938B
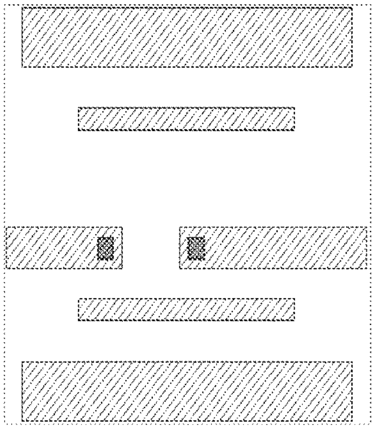
FIG. 1938C

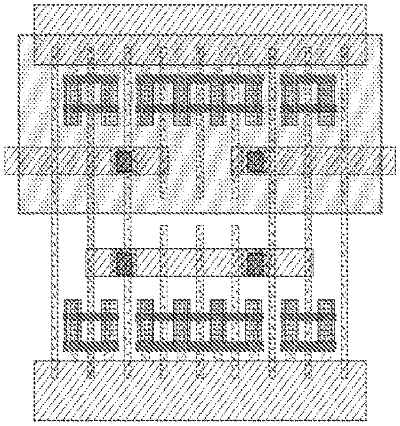
FIG. 1939A
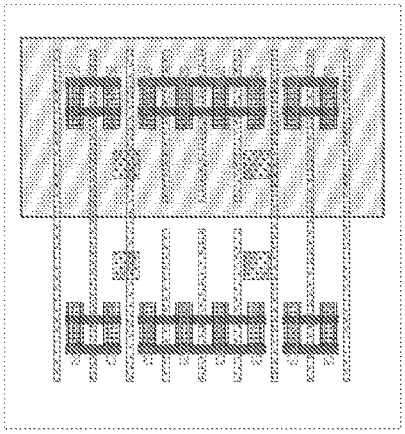
FIG. 1939B
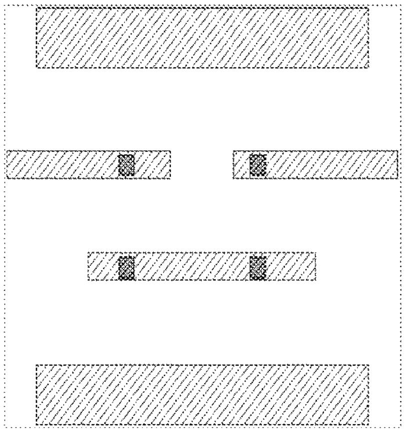
FIG. 1939C

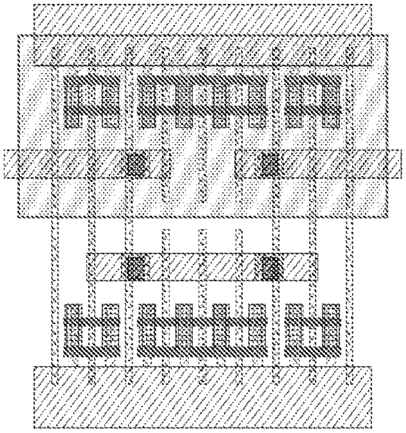
FIG. 1940A
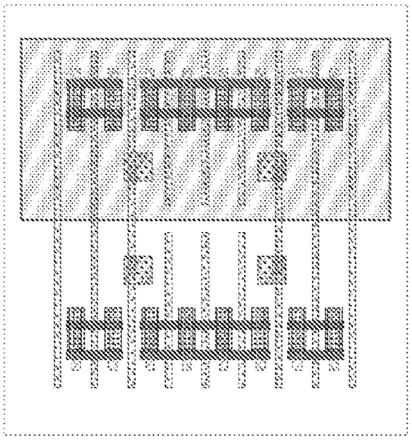
FIG. 1940B
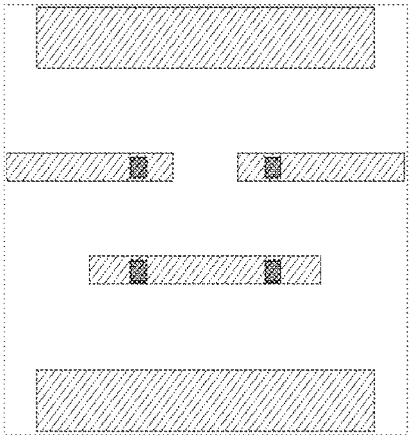
FIG. 1940C
*M* PDF Solutions, Inc.

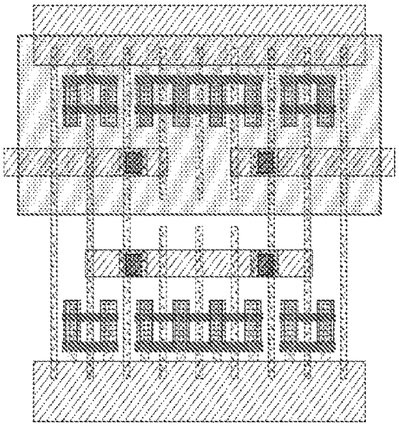
FIG. 1941A
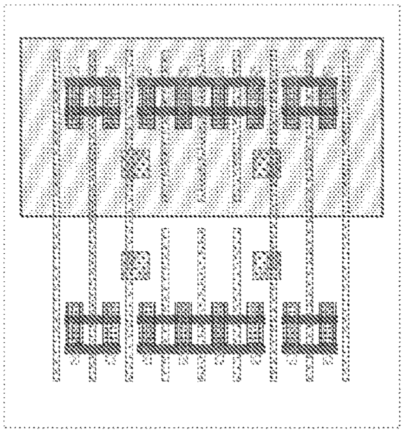
FIG. 1941B
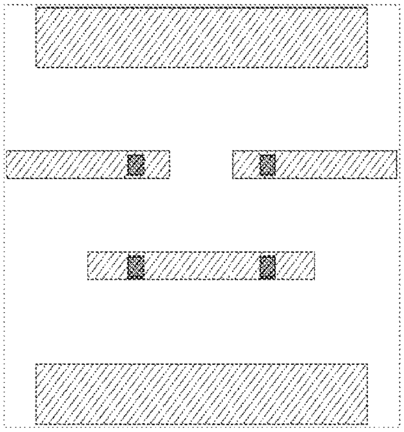
FIG. 1941C

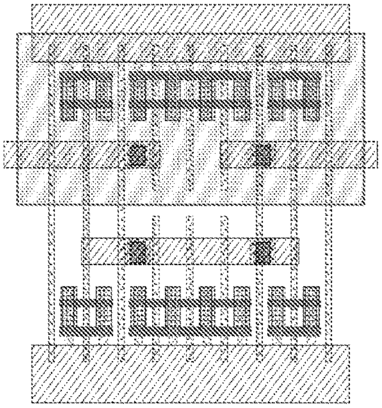
FIG. 1942A
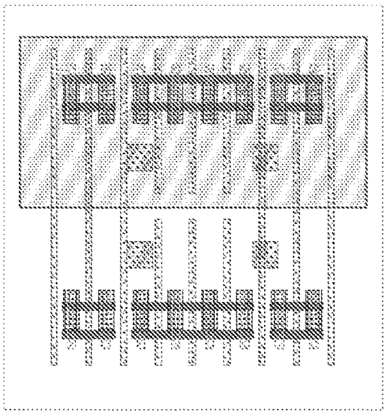
FIG. 1942B
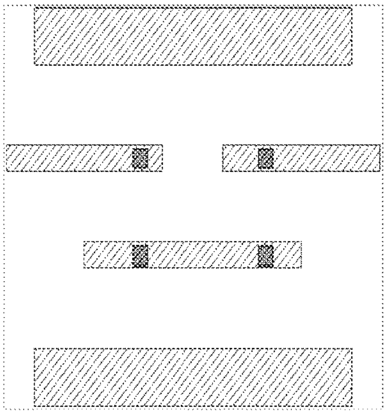
FIG. 1942C
*M* PDF Solutions, Inc.

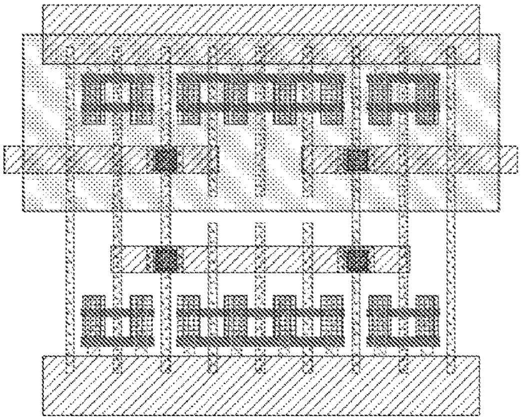
FIG. 1943A
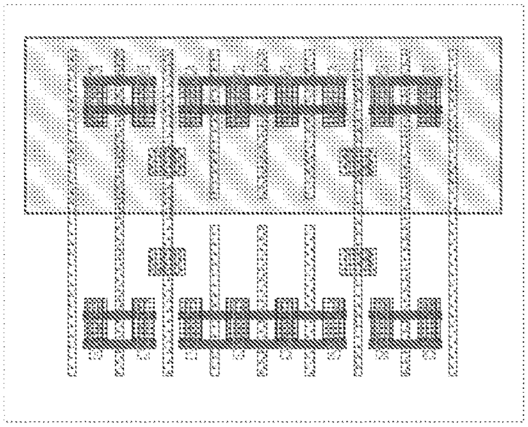
FIG. 1943B
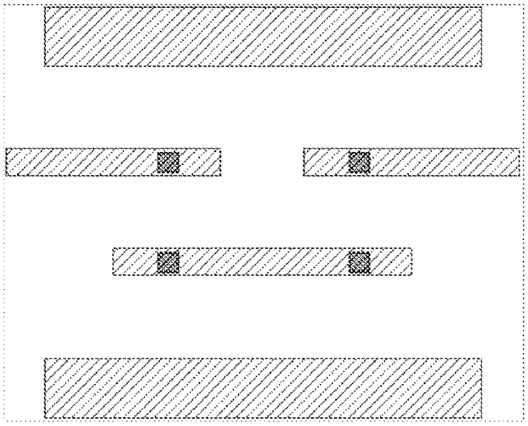
FIG. 1943C

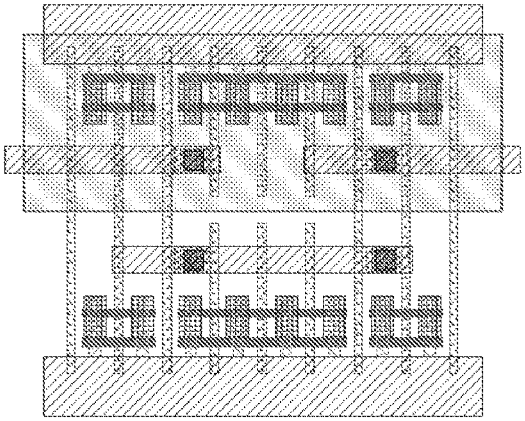
FIG. 1944A
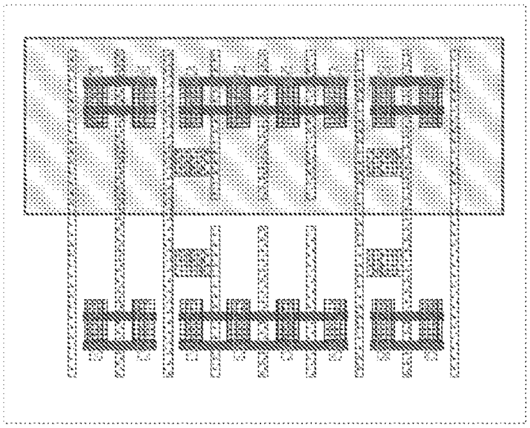
FIG. 1944B
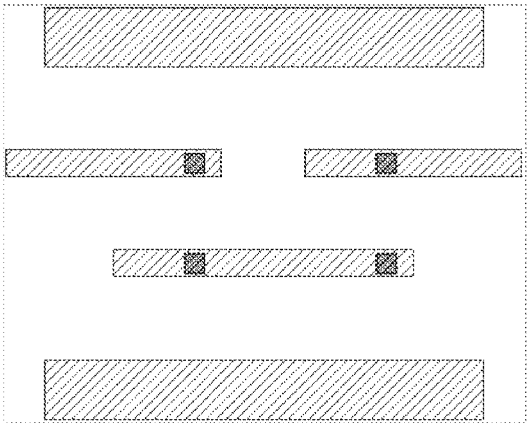
FIG. 1944C

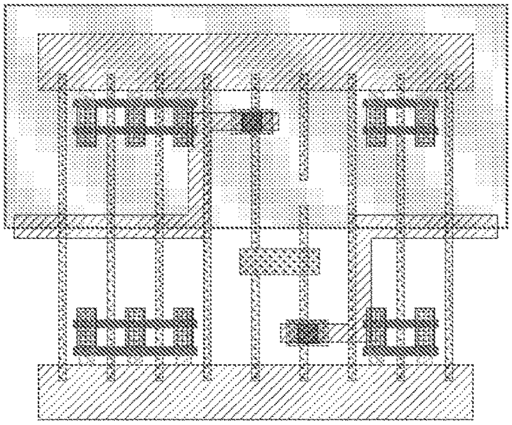
FIG. 1945A
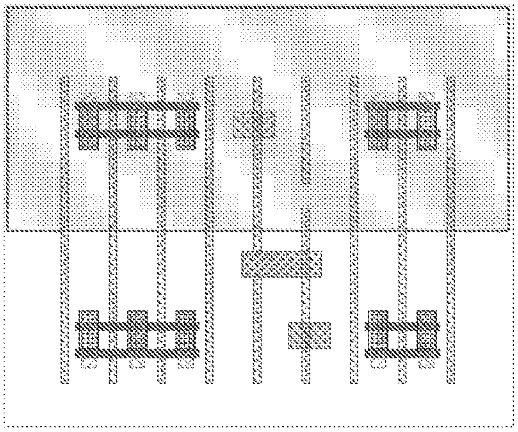
FIG. 1945B
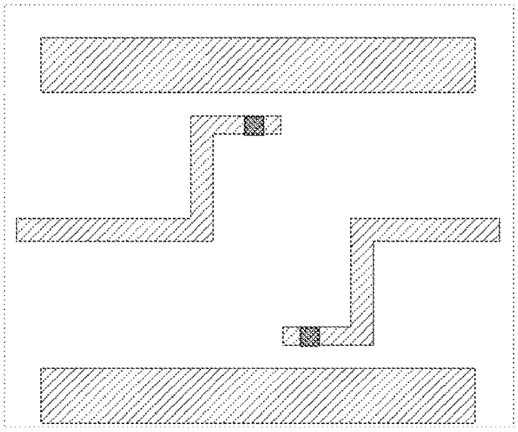
FIG. 1945C

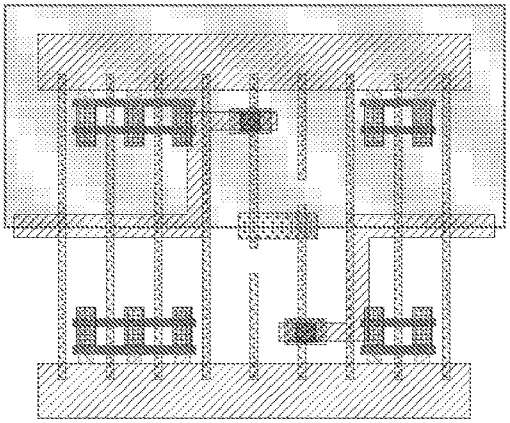
FIG. 1946A
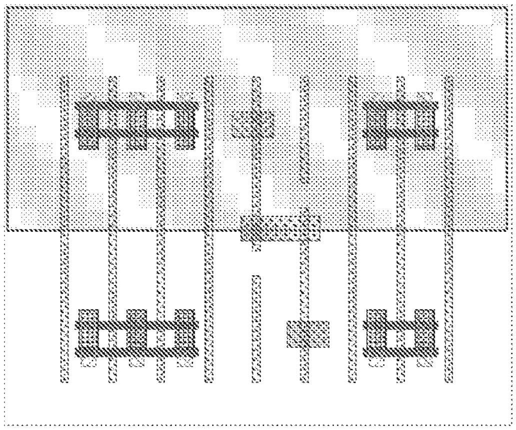
FIG. 1946B
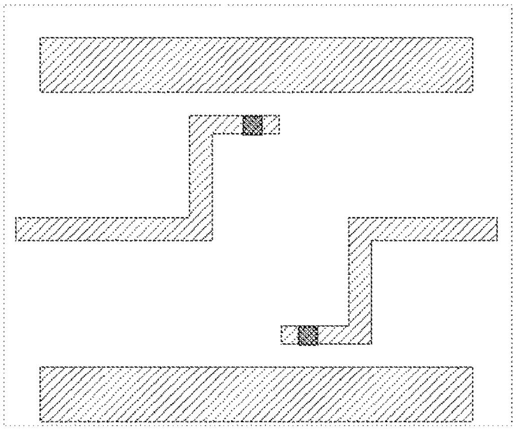
FIG. 1946C
*M* PDF Solutions, Inc.

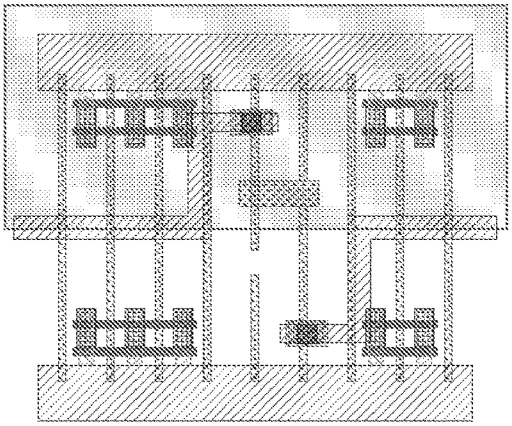
FIG. 1947A
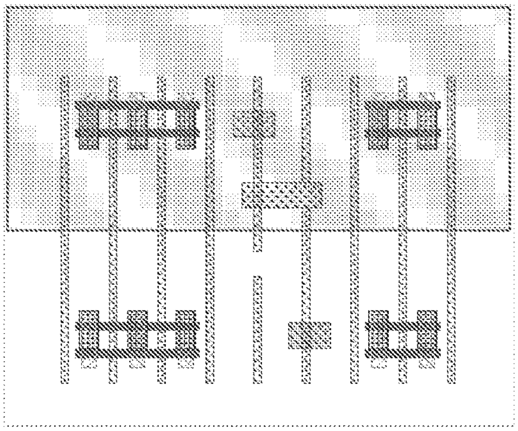
FIG. 1947B
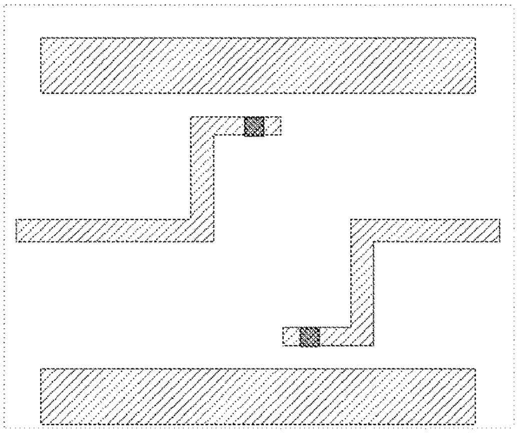
FIG. 1947C

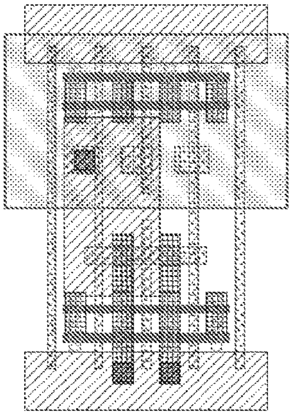
FIG. 1948A
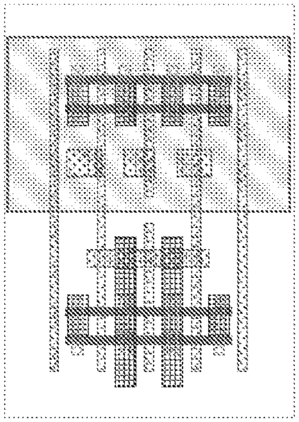
FIG. 1948B
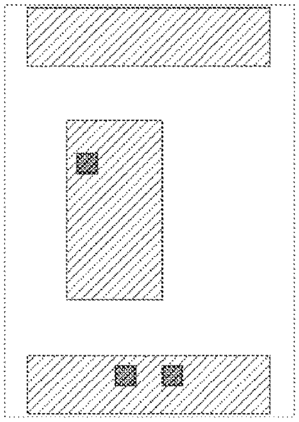
FIG. 1948C
*M* PDF Solutions, Inc.

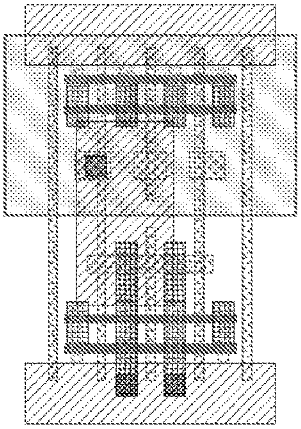
FIG. 1949A
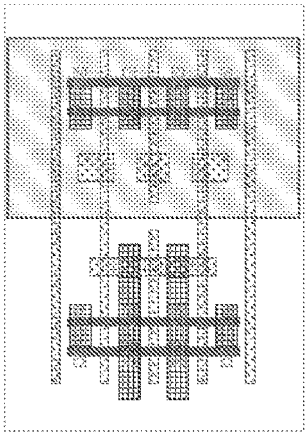
FIG. 1949B
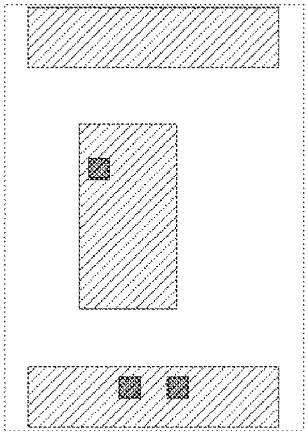
FIG. 1949C

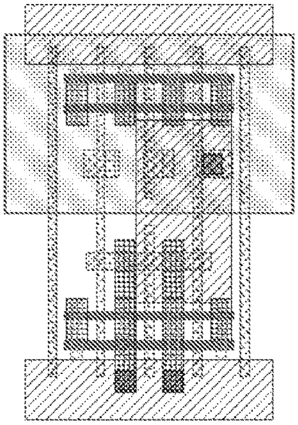
FIG. 1950A
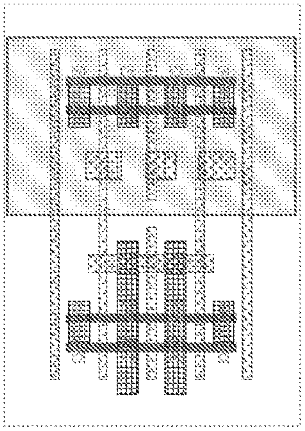
FIG. 1950B
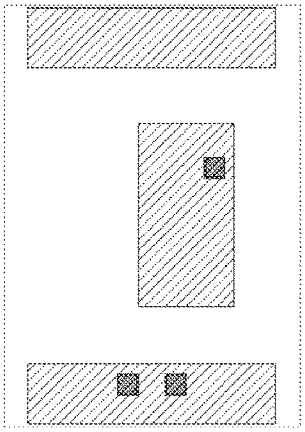
FIG. 1950C

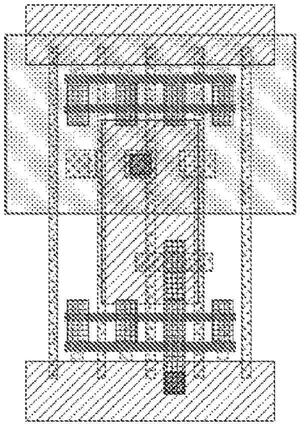
FIG. 1951A
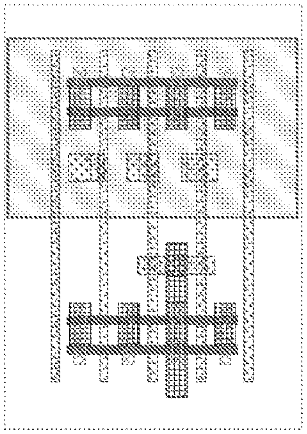
FIG. 1951B
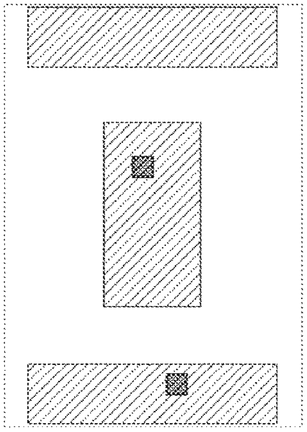
FIG. 1951C

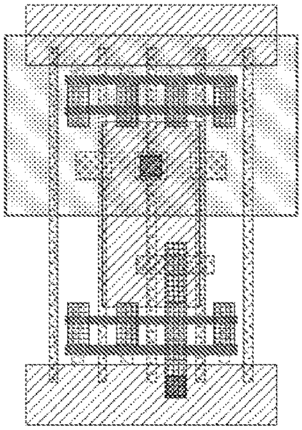
FIG. 1952A
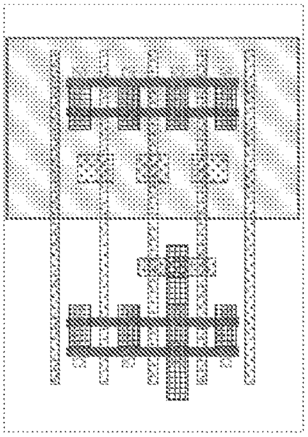
FIG. 1952B
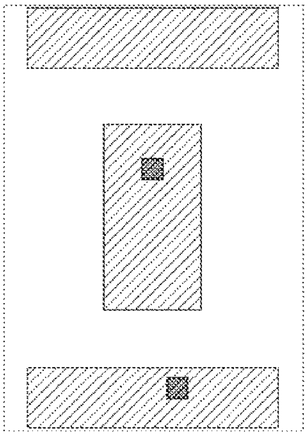
FIG. 1952C
*M* PDF Solutions, Inc.

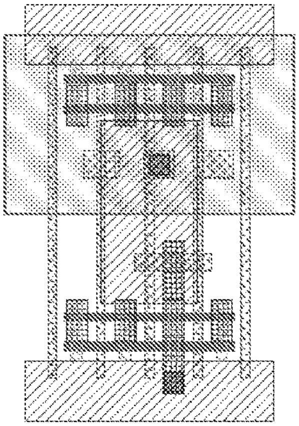
FIG. 1953A
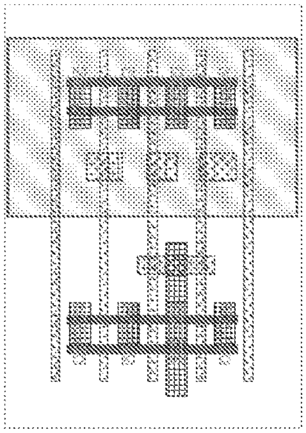
FIG. 1953B
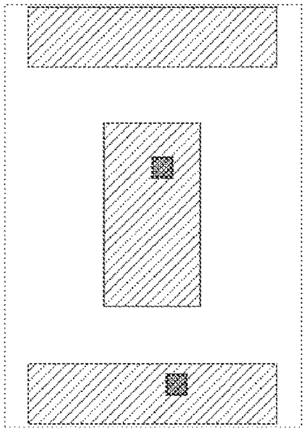
FIG. 1953C

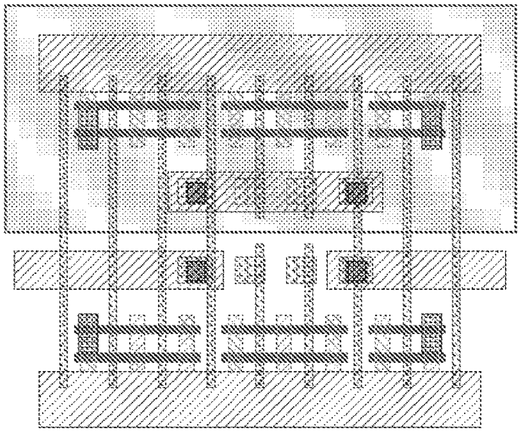
FIG. 1954A
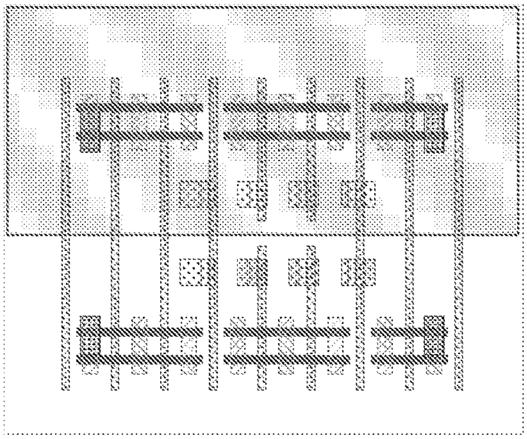
FIG. 1954B
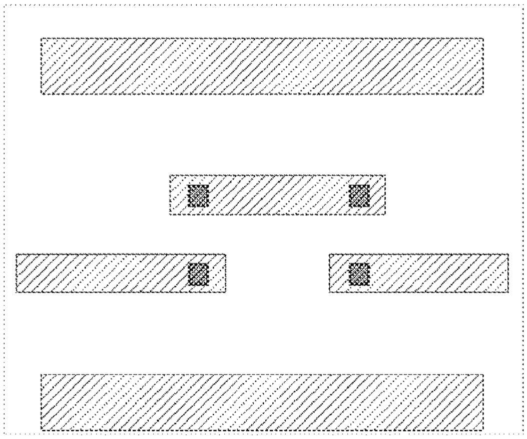
FIG. 1954C

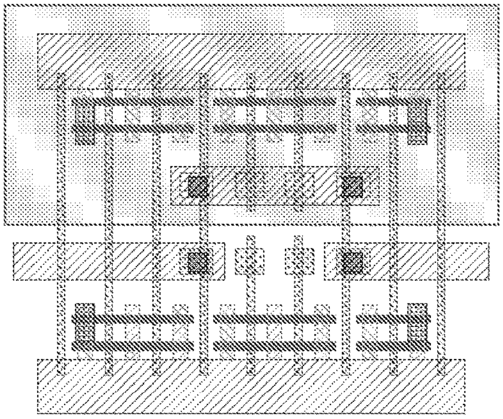
FIG. 1955A
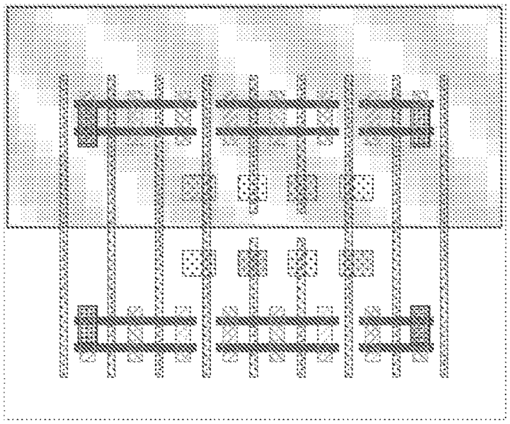
FIG. 1955B
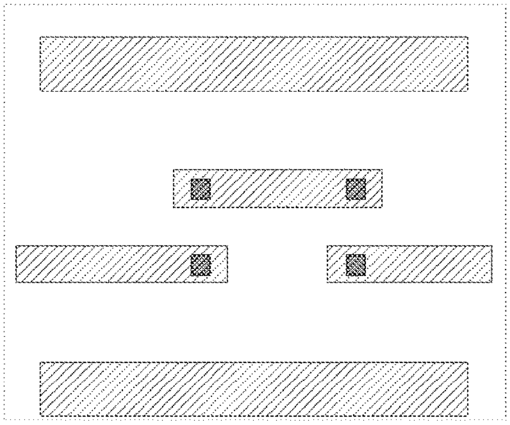
FIG. 1955C
*M* PDF Solutions, Inc.

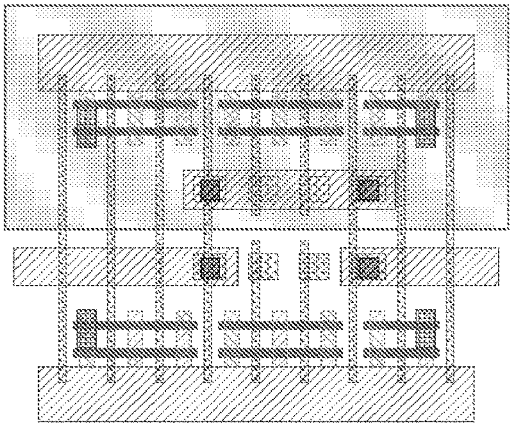
FIG. 1956A
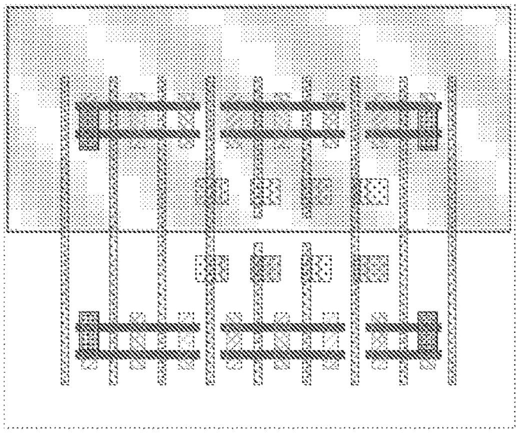
FIG. 1956B
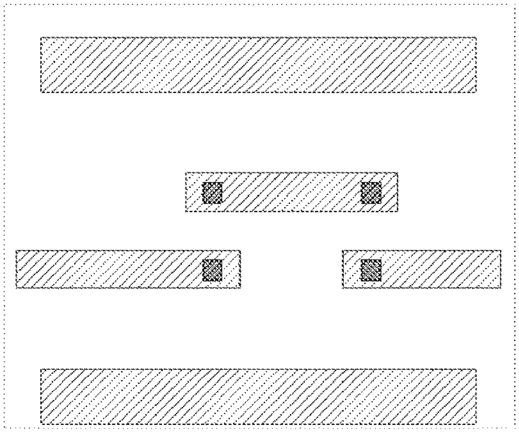
FIG. 1956C

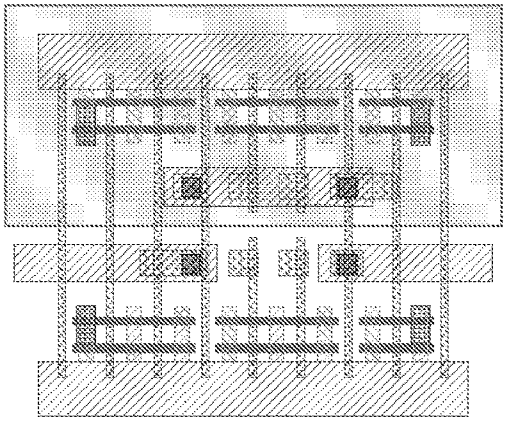
FIG. 1957A
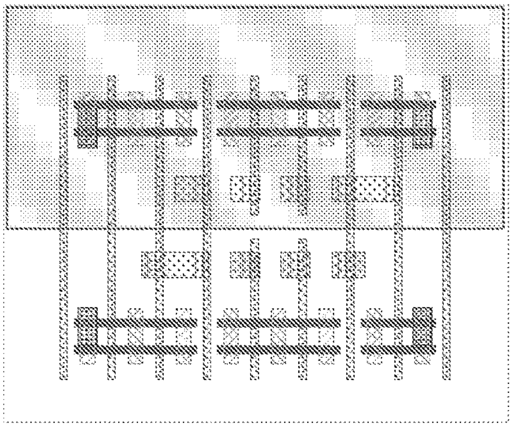
FIG. 1957B
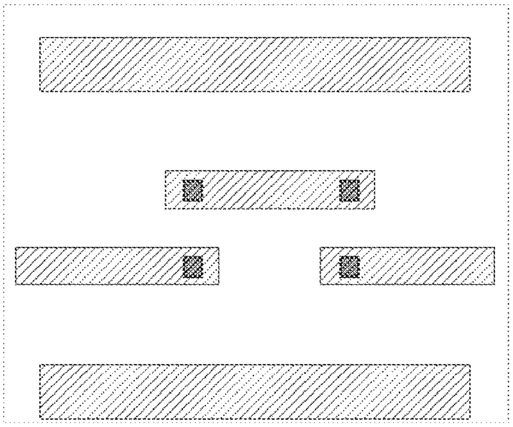
FIG. 1957C

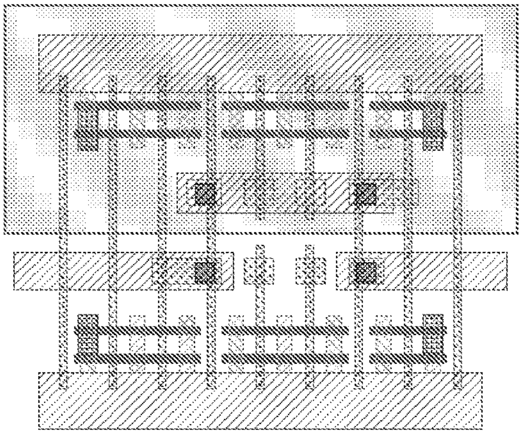
FIG. 1958A
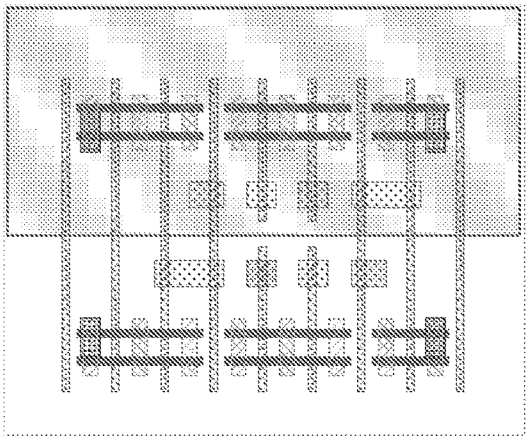
FIG. 1958B
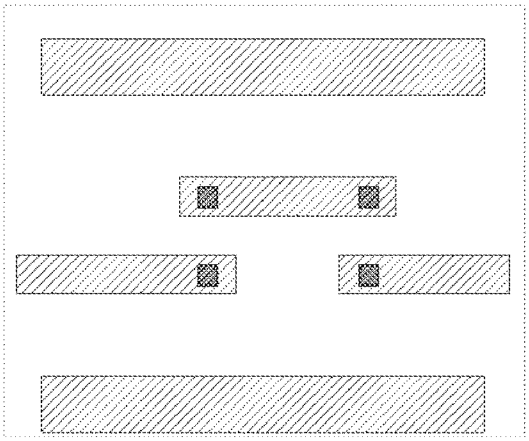
FIG. 1958C

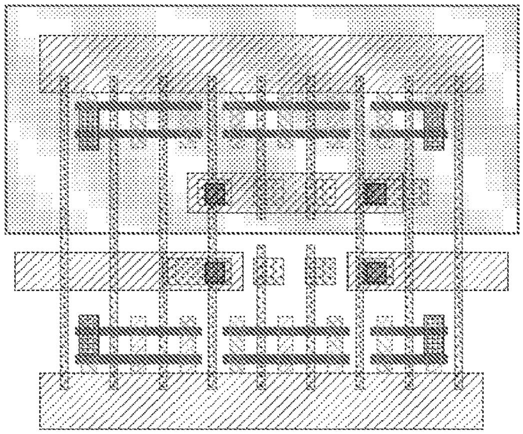
FIG. 1959A
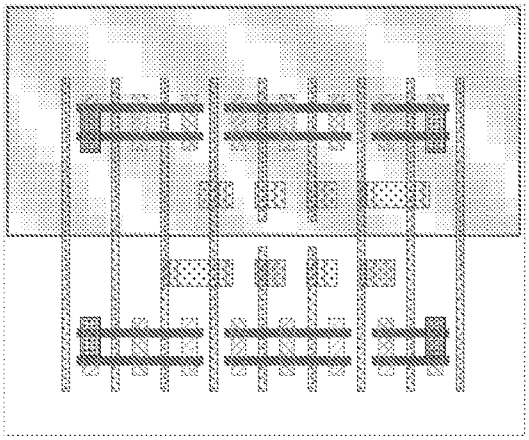
FIG. 1959B
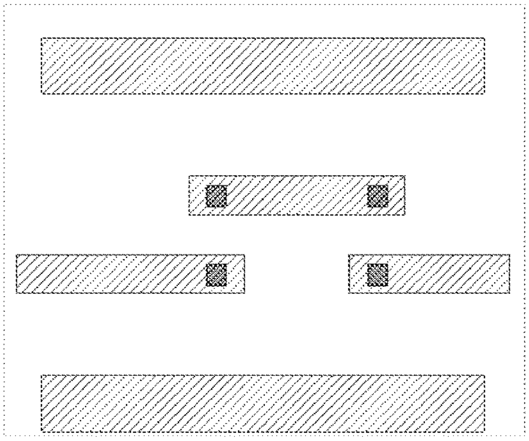
FIG. 1959C

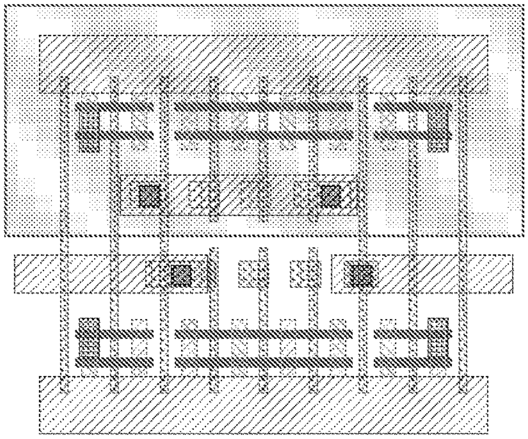
FIG. 1960A
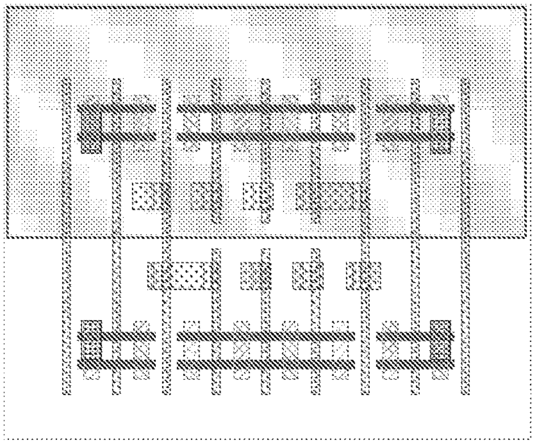
FIG. 1960B
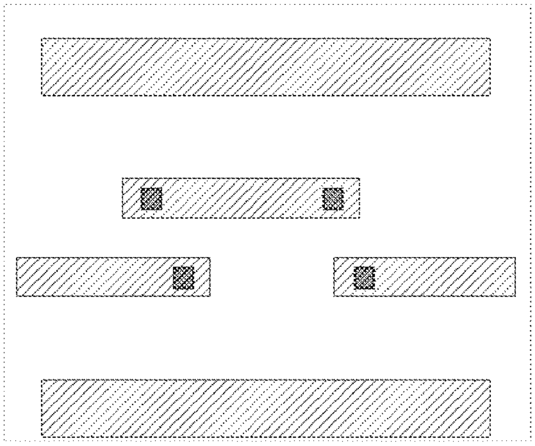
FIG. 1960C

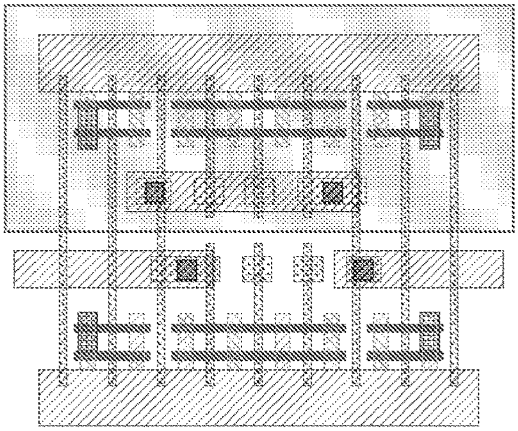
FIG. 1961A
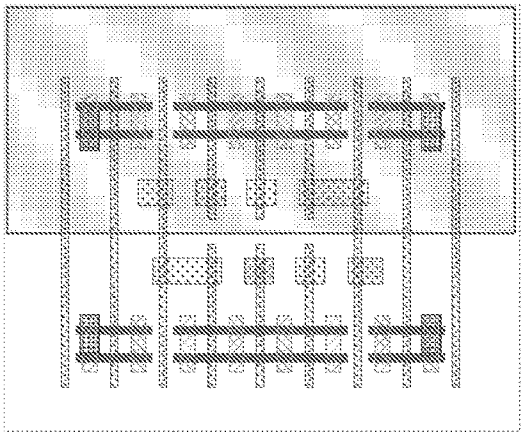
FIG. 1961B
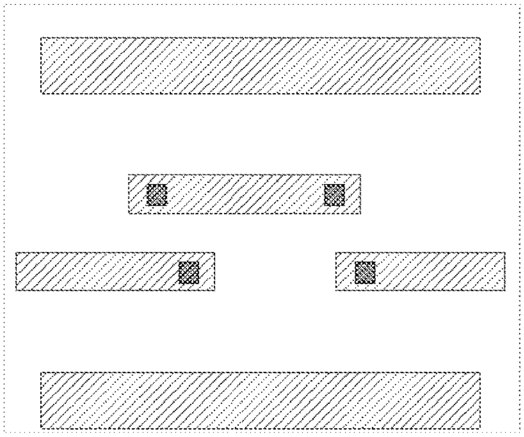
FIG. 1961C
*M* PDF Solutions, Inc.

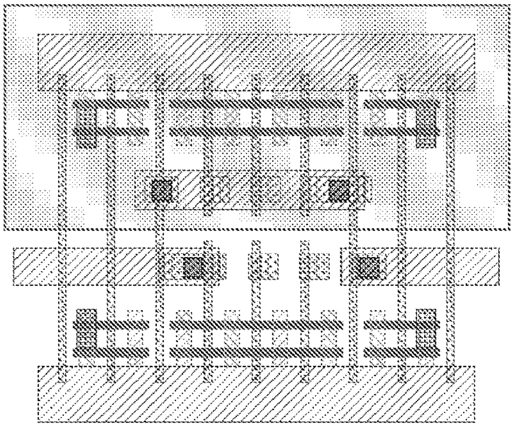
FIG. 1962A
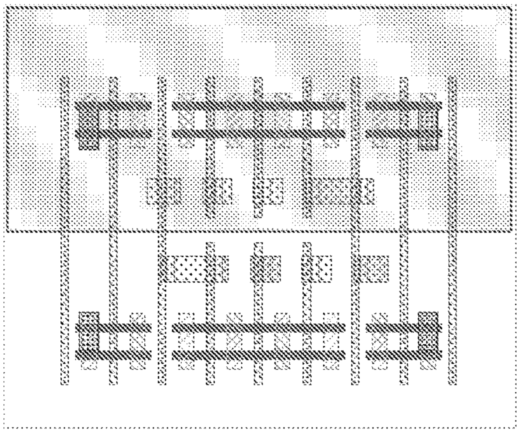
FIG. 1962B
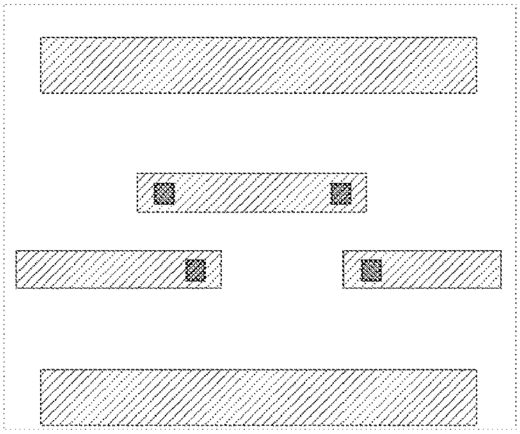
FIG. 1962C
*M* PDF Solutions, Inc.

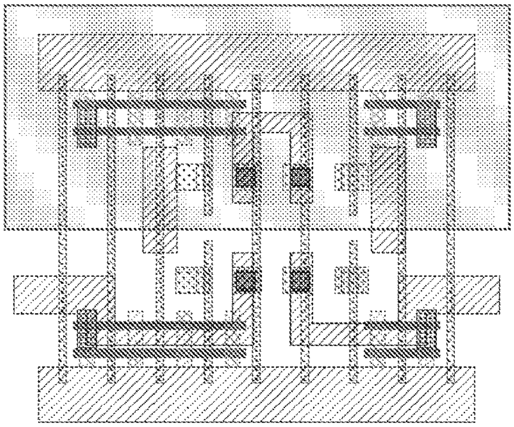
FIG. 1963A
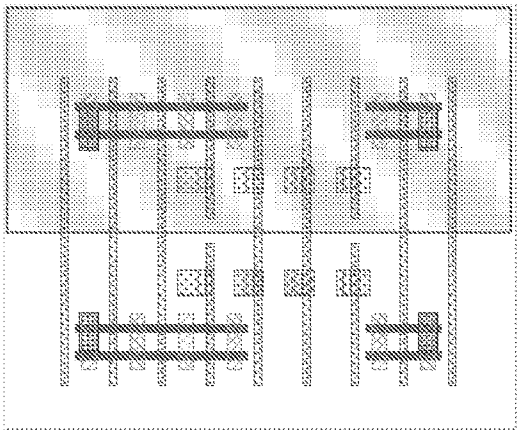
FIG. 1963B
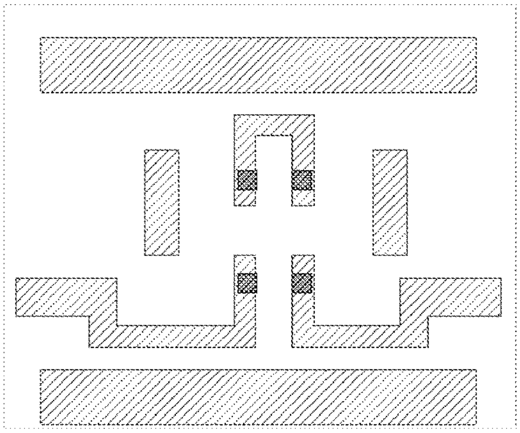
FIG. 1963C

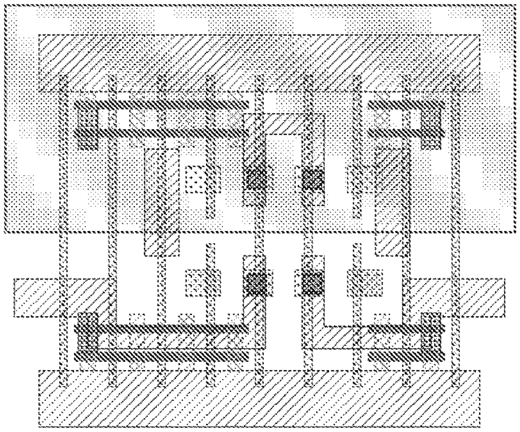
FIG. 1964A
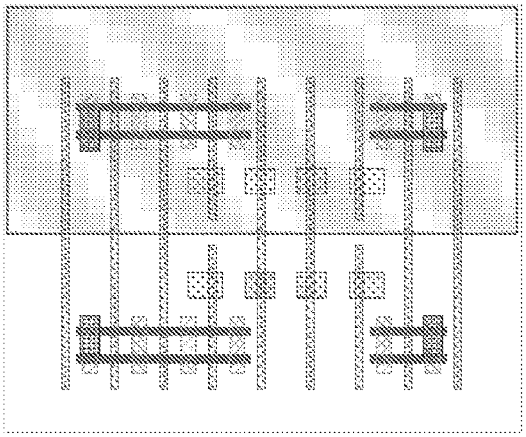
FIG. 1964B
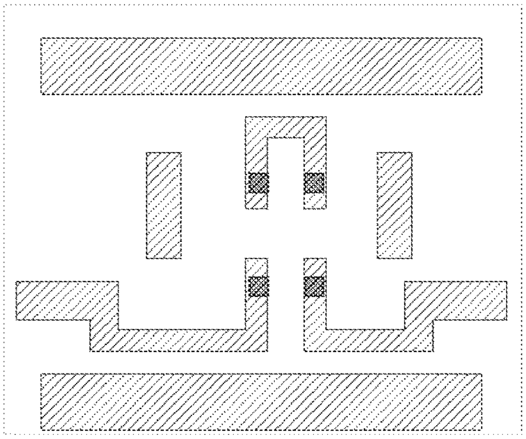
FIG. 1964C

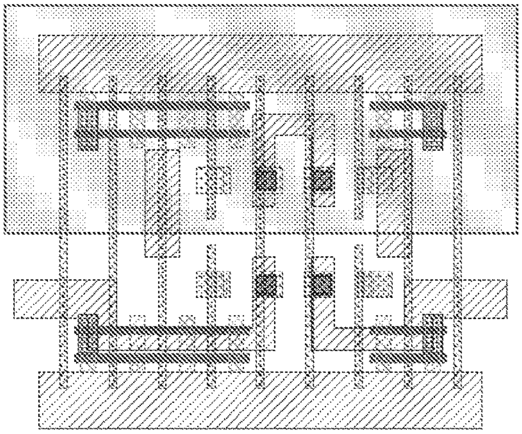
FIG. 1965A
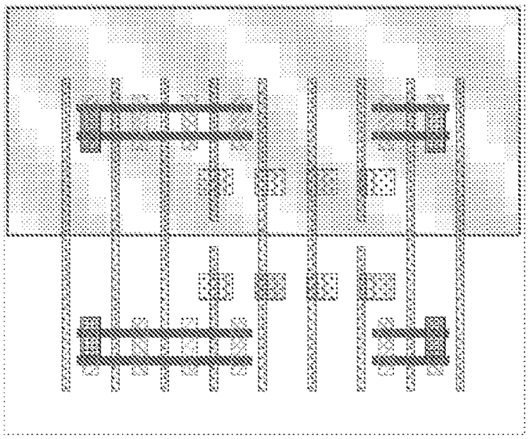
FIG. 1965B
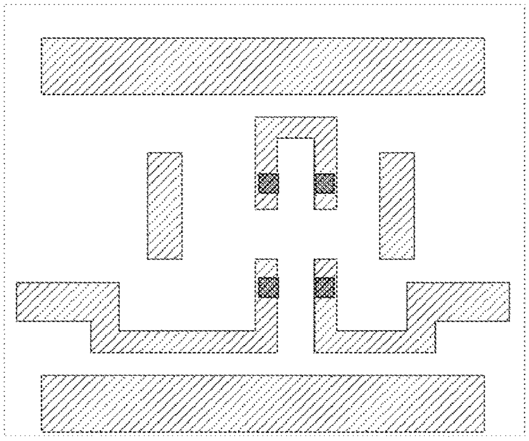
FIG. 1965C

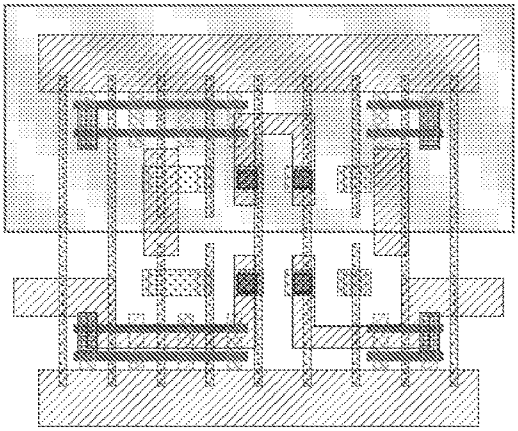
FIG. 1966A
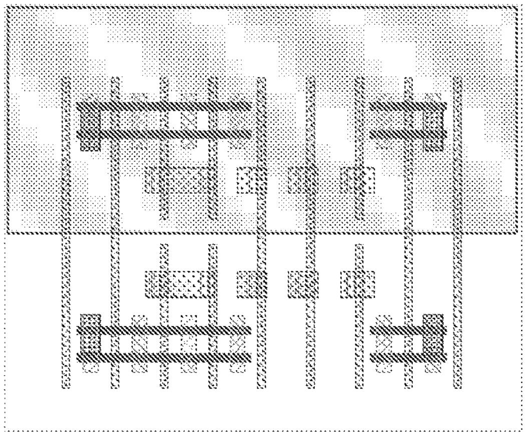
FIG. 1966B
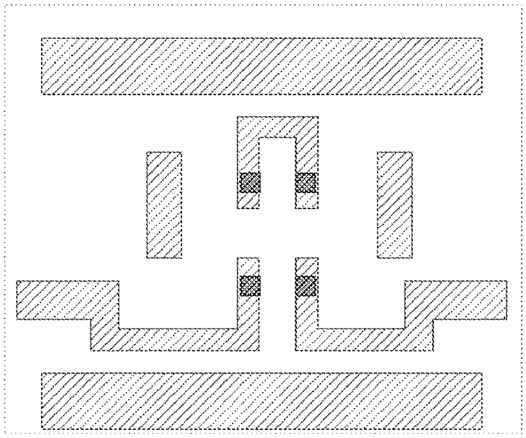
FIG. 1966C

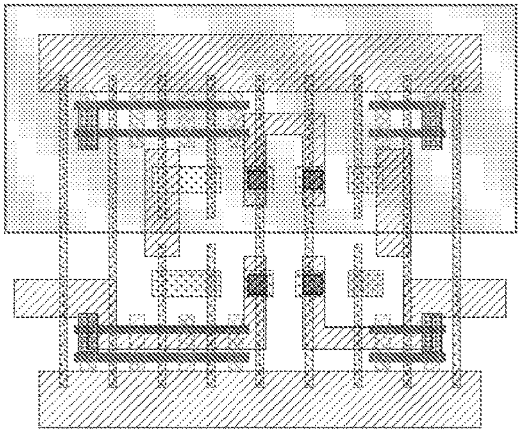
FIG. 1967A
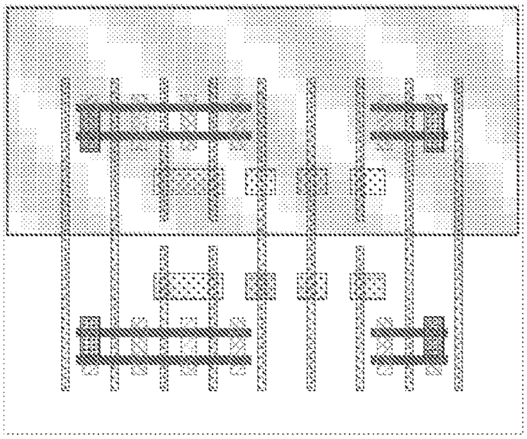
FIG. 1967B
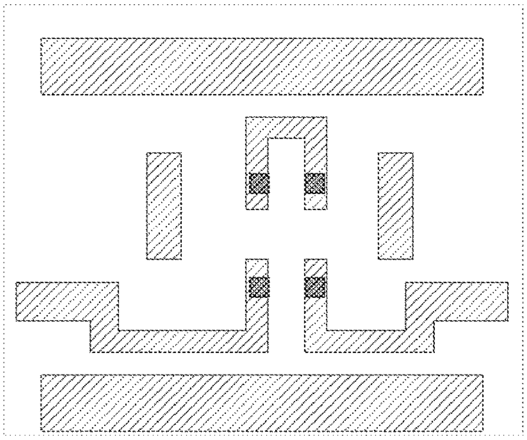
FIG. 1967C

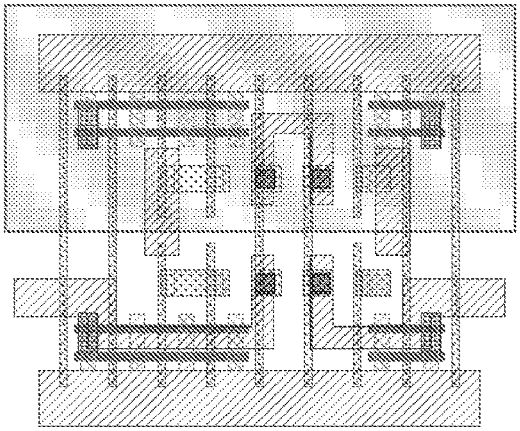
FIG. 1968A
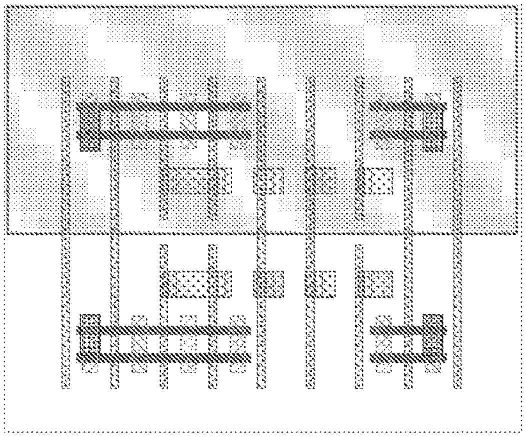
FIG. 1968B
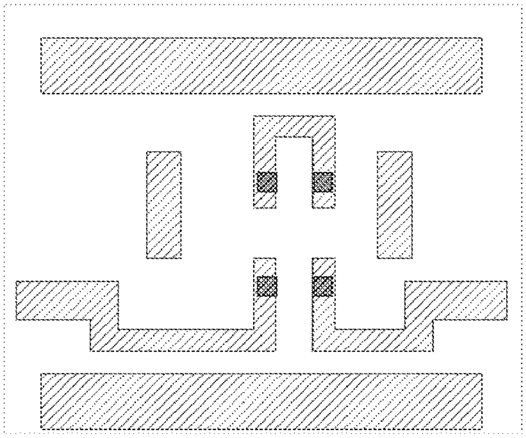
FIG. 1968C
*M* PDF Solutions, Inc.

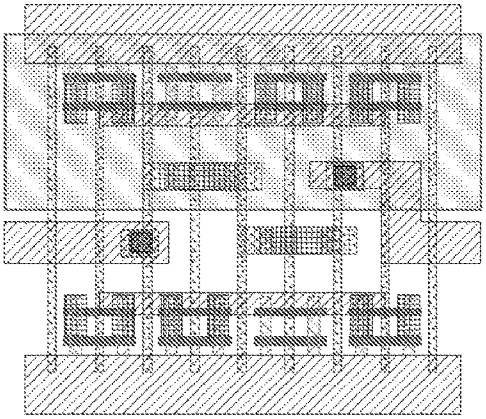
FIG. 1969A
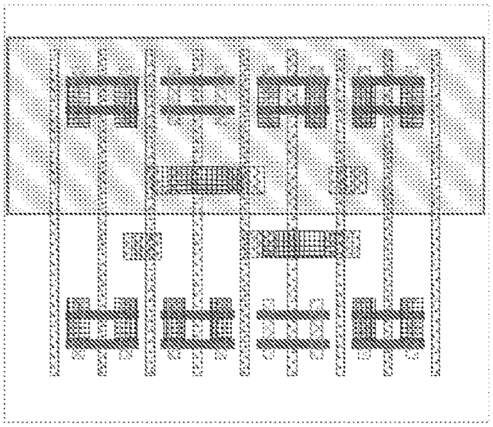
FIG. 1969B
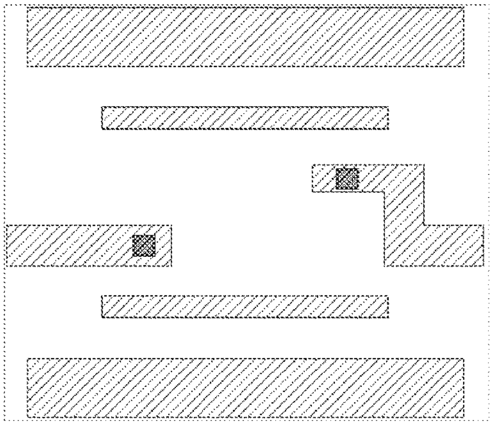
FIG. 1969C
*M* PDF Solutions, Inc.

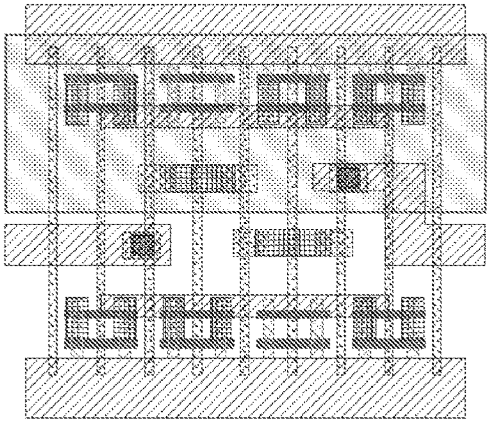
FIG. 1970A
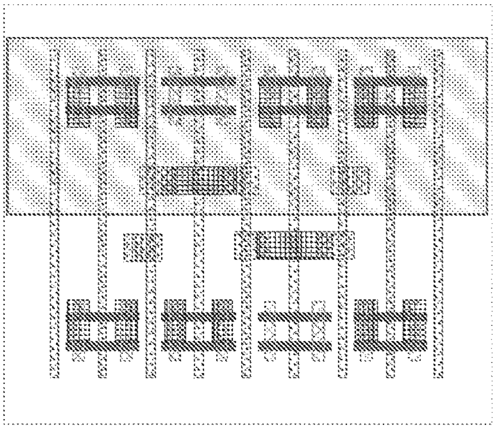
FIG. 1970B
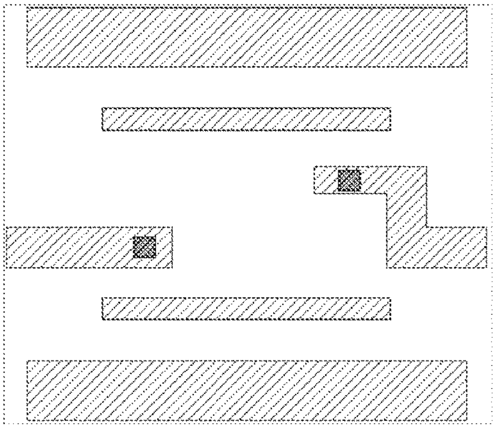
FIG. 1970C

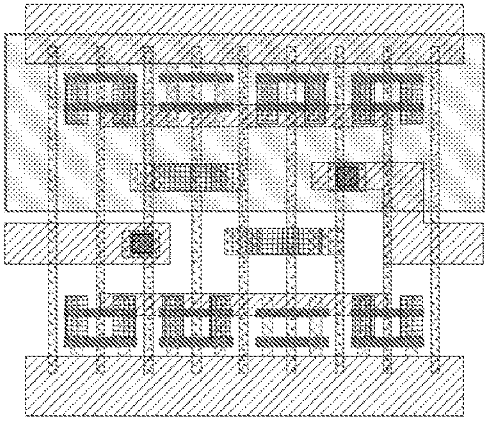
FIG. 1971A
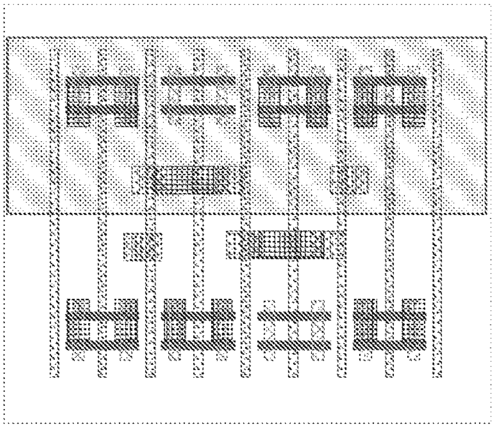
FIG. 1971B
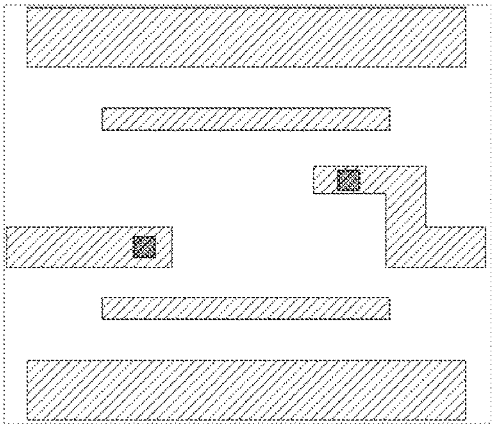
FIG. 1971C

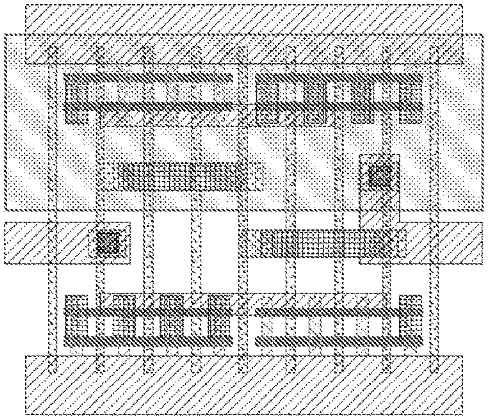
FIG. 1972A
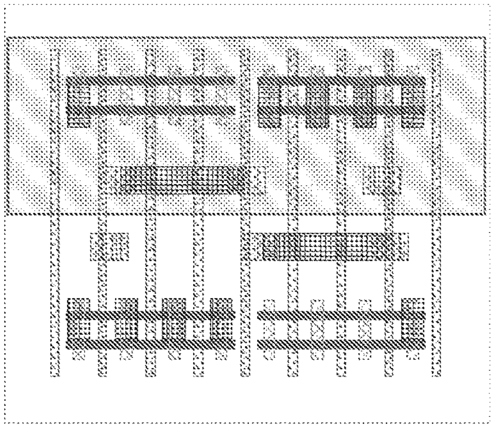
FIG. 1972B
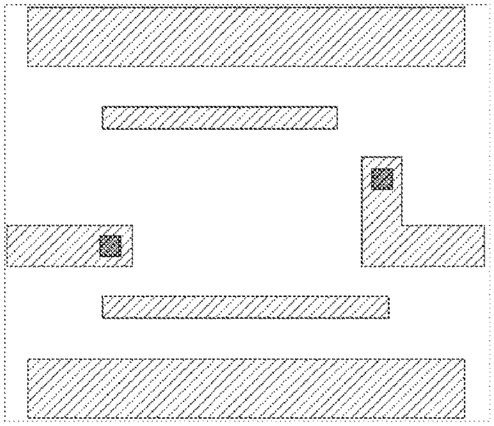
FIG. 1972C
*M* PDF Solutions, Inc.

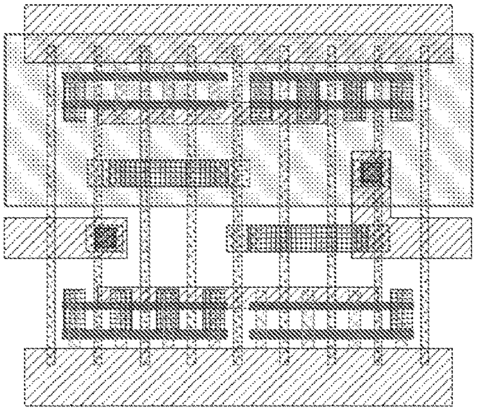
FIG. 1973A
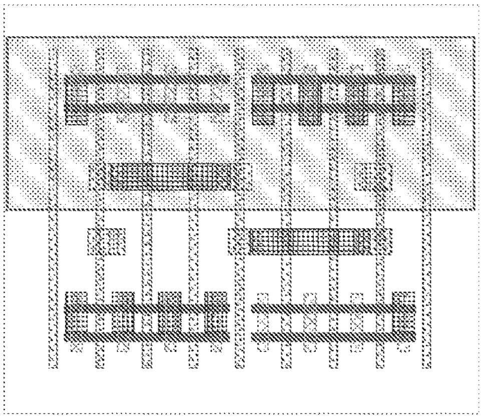
FIG. 1973B
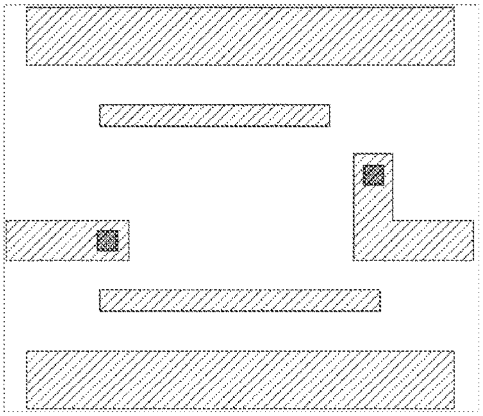
FIG. 1973C

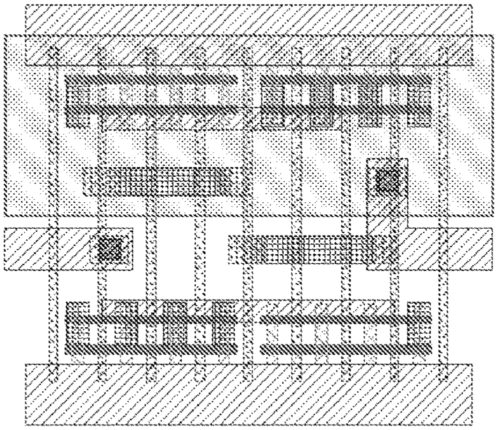
FIG. 1974A
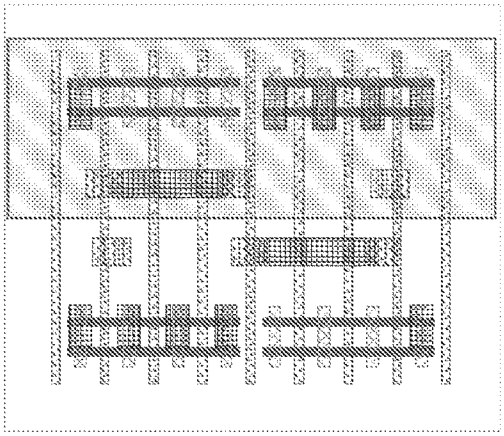
FIG. 1974B
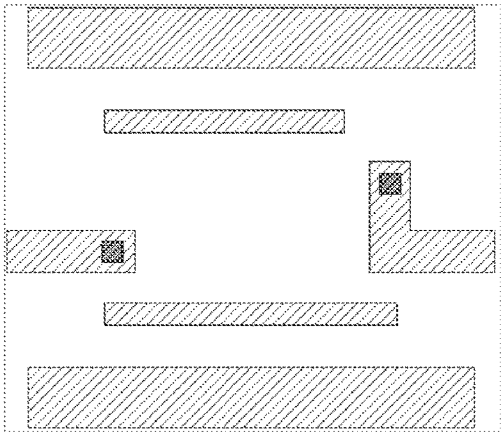
FIG. 1974C

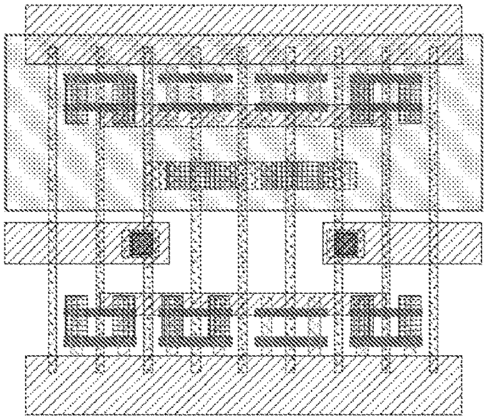
FIG. 1975A
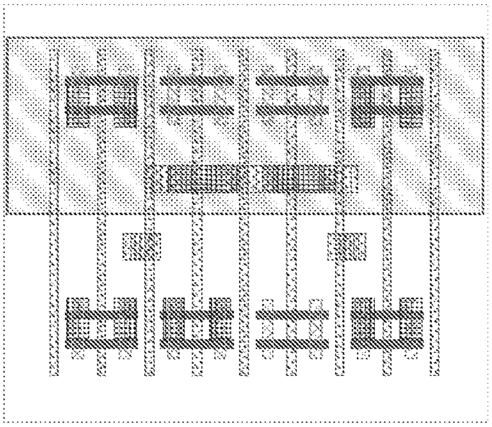
FIG. 1975B
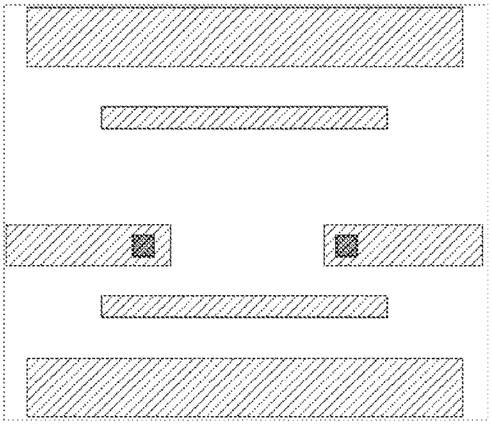
FIG. 1975C
*M* PDF Solutions, Inc.

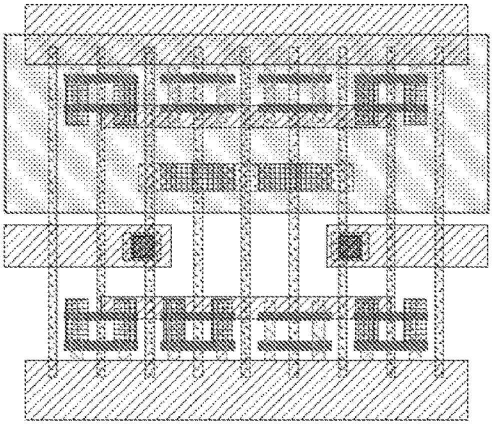
FIG. 1976A
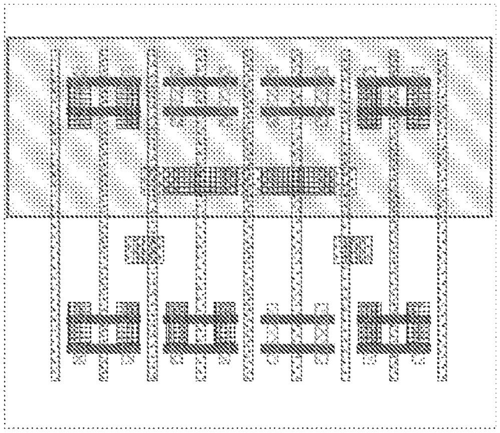
FIG. 1976B
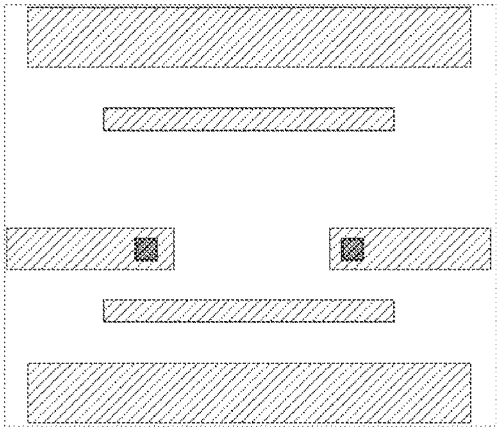
FIG. 1976C

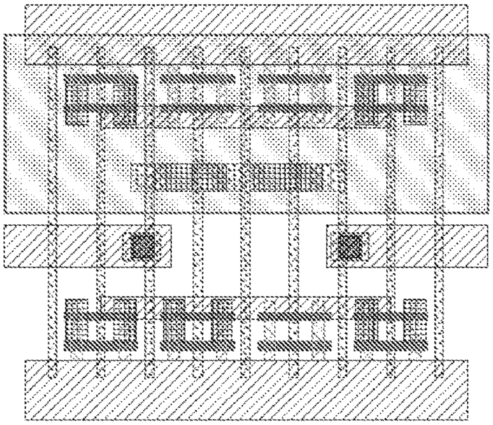
FIG. 1977A
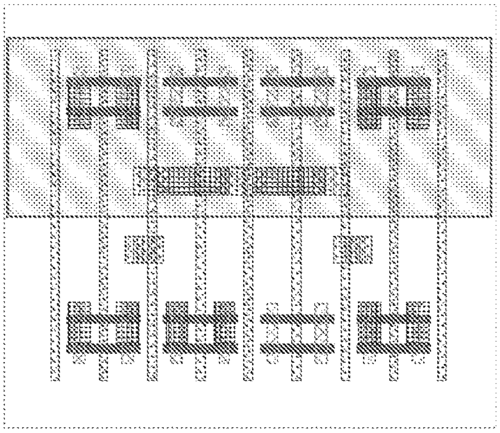
FIG. 1977B
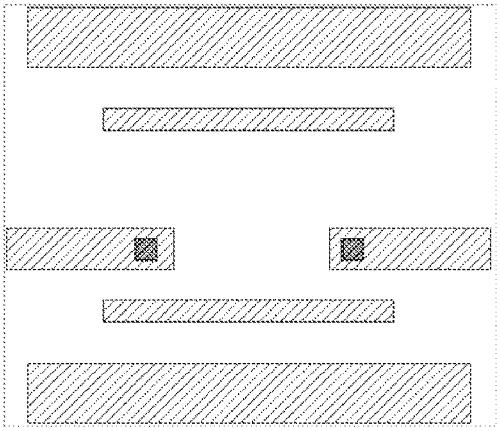
FIG. 1977C

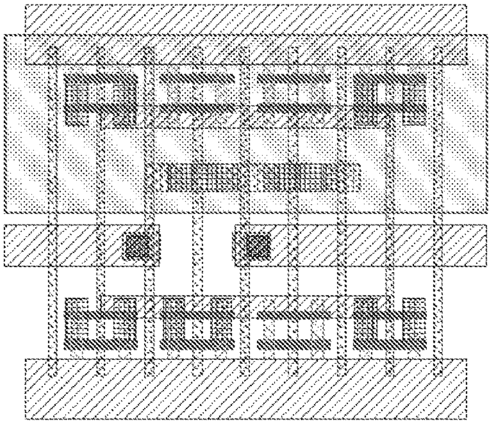
FIG. 1978A
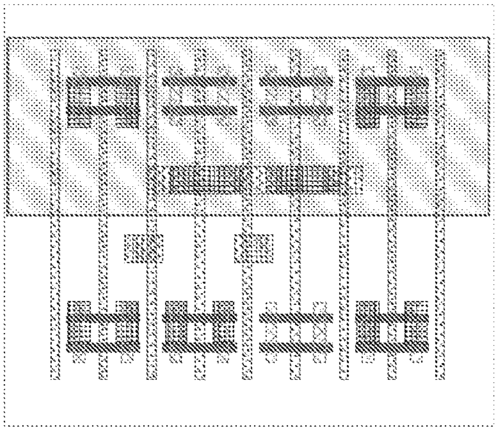
FIG. 1978B
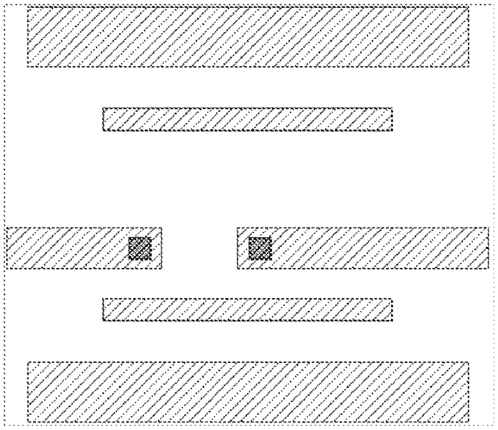
FIG. 1978C

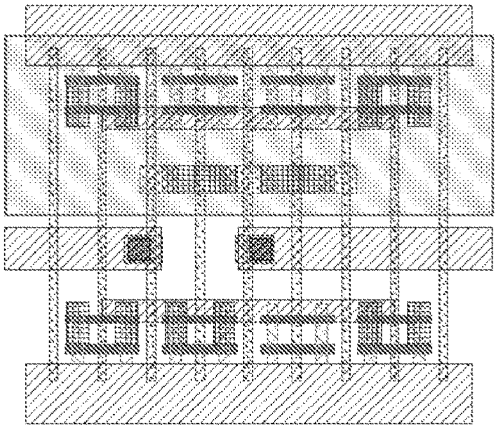
FIG. 1979A
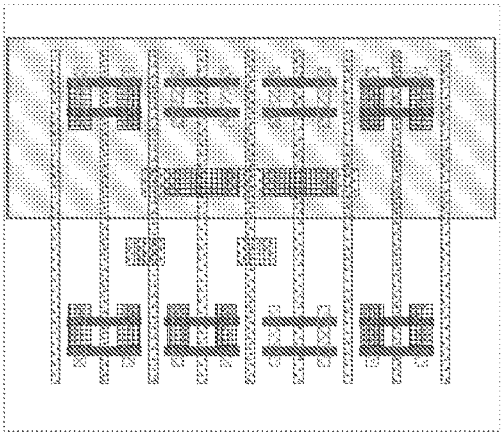
FIG. 1979B
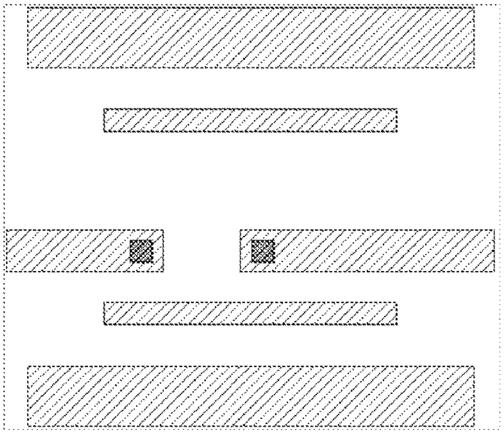
FIG. 1979C

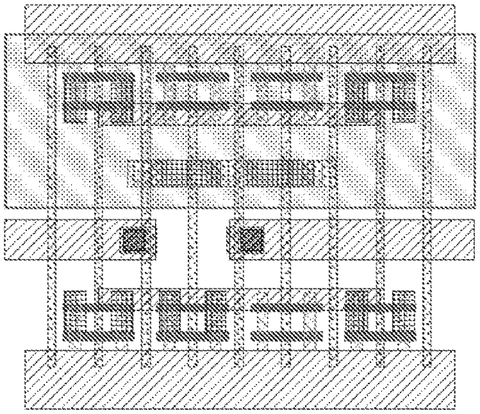
FIG. 1980A
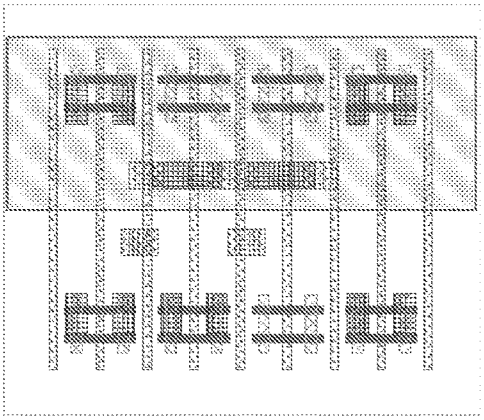
FIG. 1980B
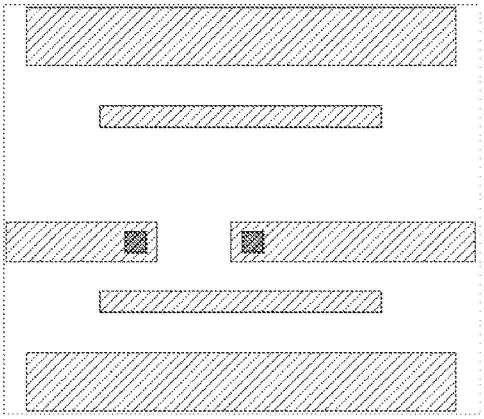
FIG. 1980C
*M* PDF Solutions, Inc.

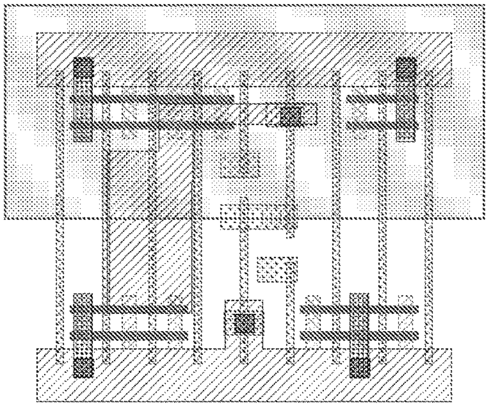
FIG. 1981A
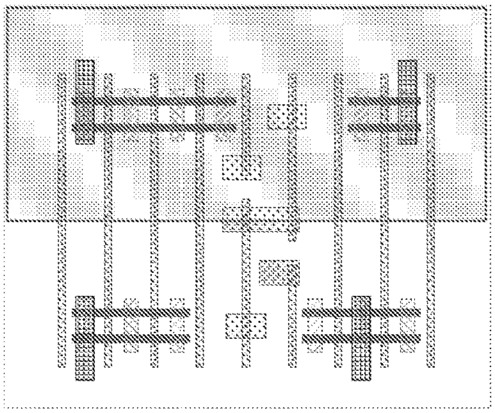
FIG. 1981B
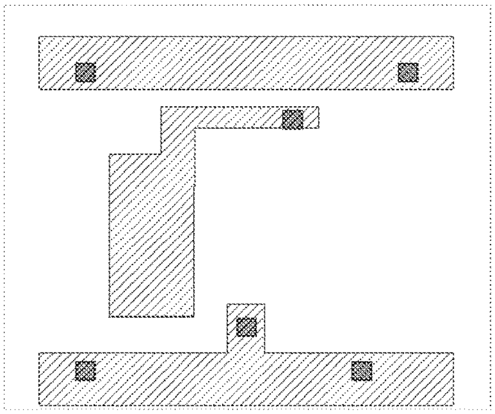
FIG. 1981C

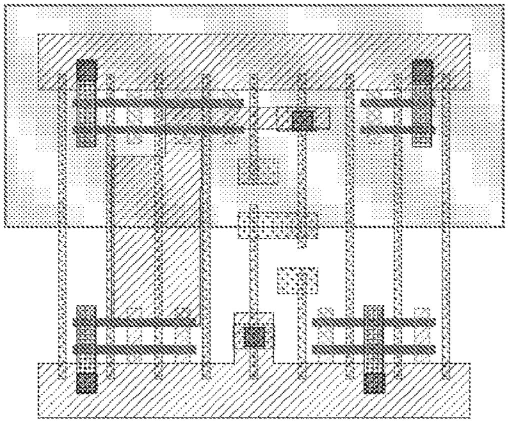
FIG. 1982A
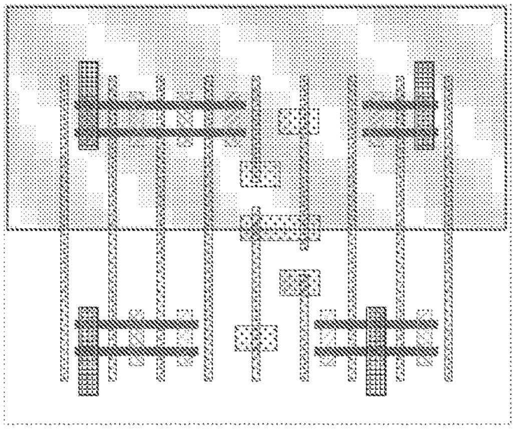
FIG. 1982B
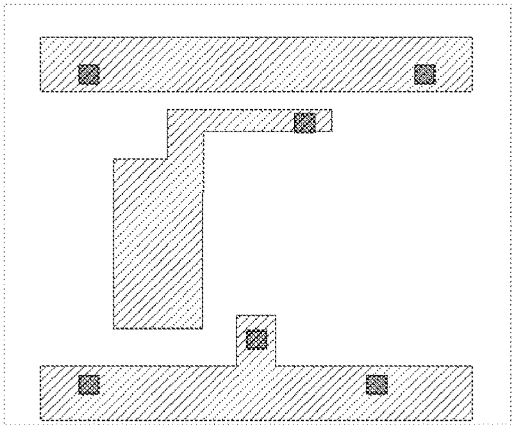
FIG. 1982C

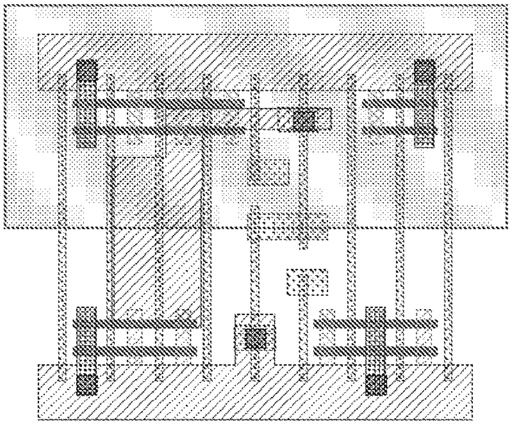
FIG. 1983A
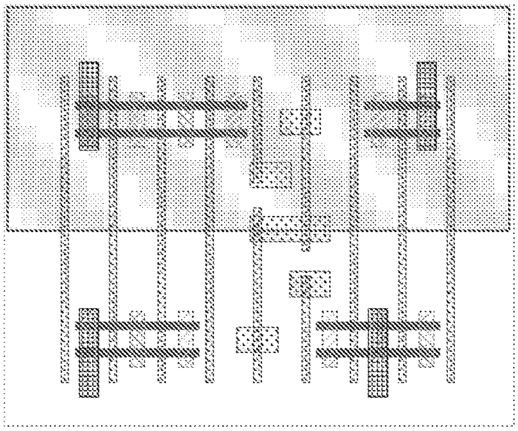
FIG. 1983B
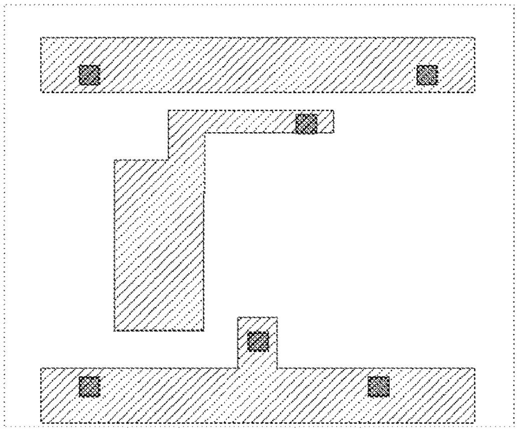
FIG. 1983C
*M* PDF Solutions, Inc.

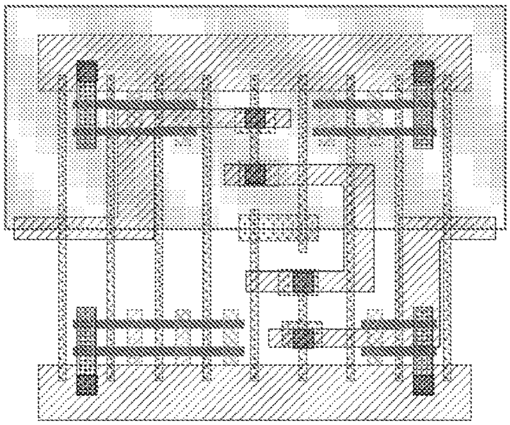
FIG. 1984A
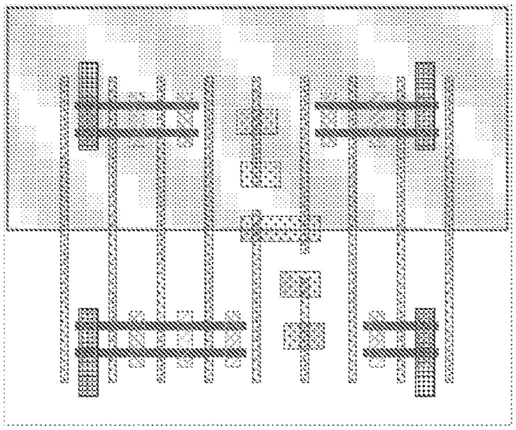
FIG. 1984B
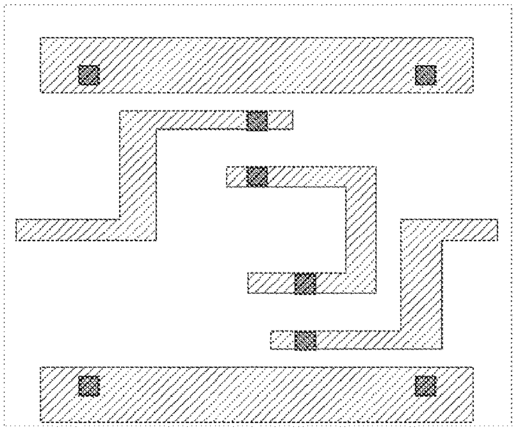
FIG. 1984C

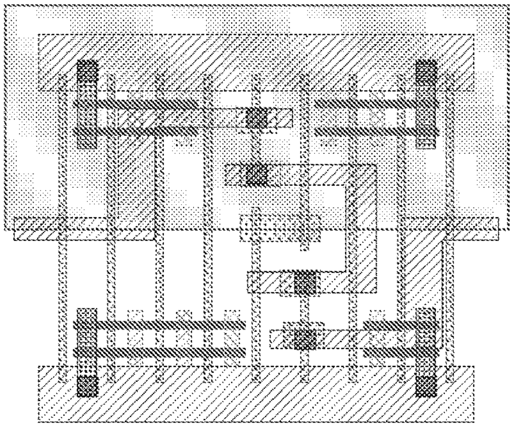
FIG. 1985A
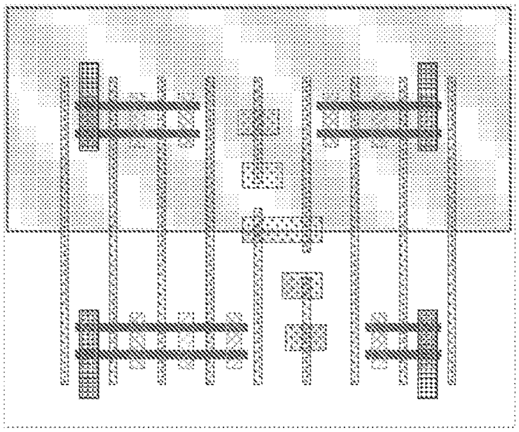
FIG. 1985B
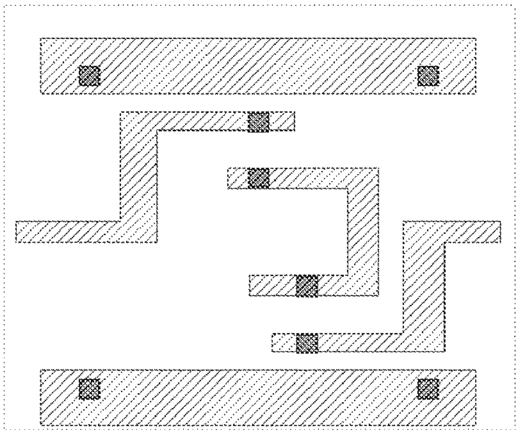
FIG. 1985C

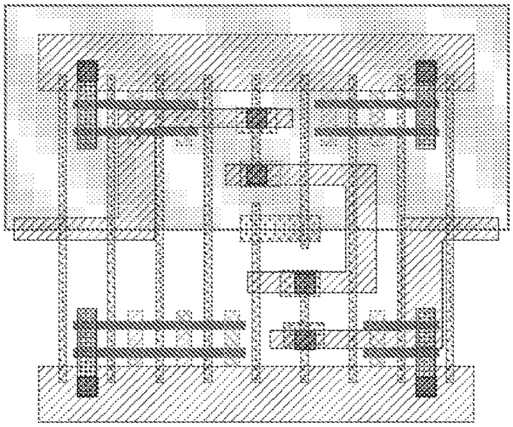
FIG. 1986A
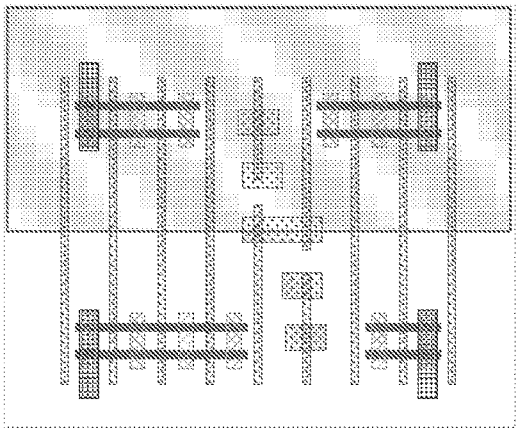
FIG. 1986B
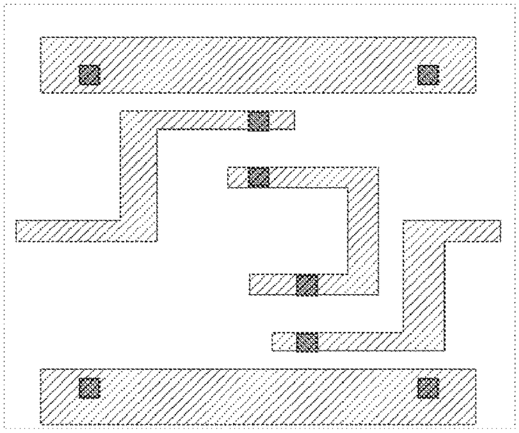
FIG. 1986C

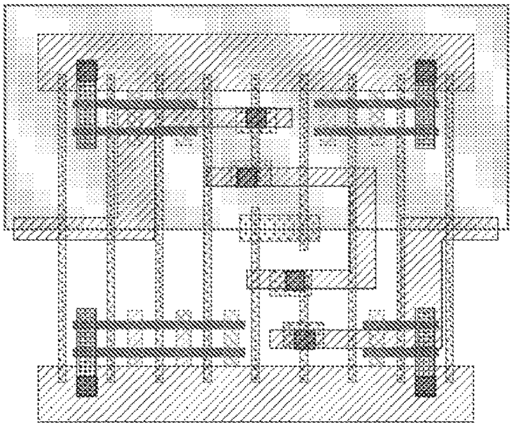
FIG. 1987A
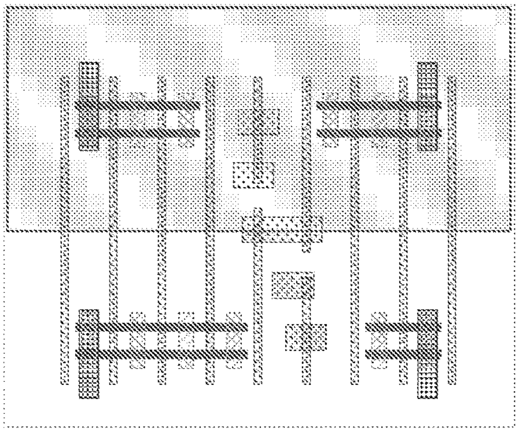
FIG. 1987B
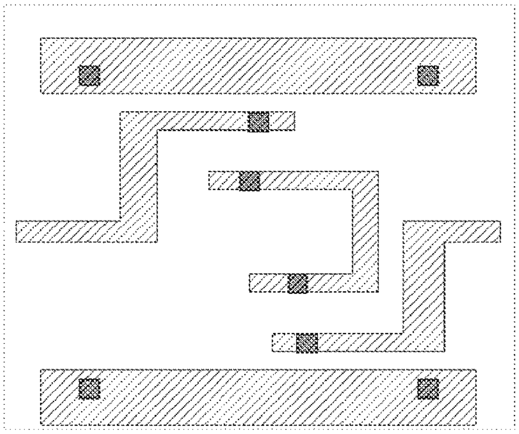
FIG. 1987C
*M* PDF Solutions, Inc.

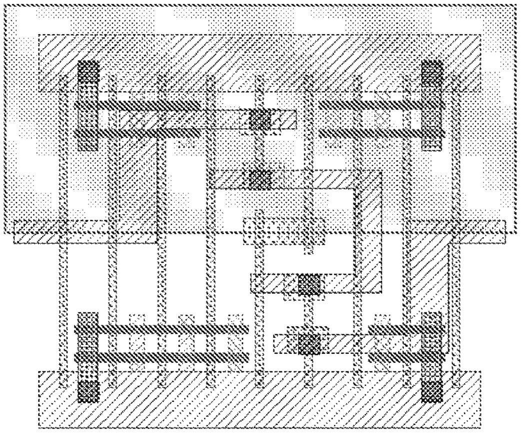
FIG. 1988A
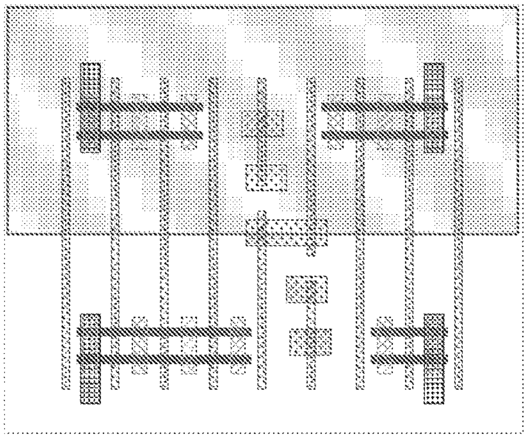
FIG. 1988B
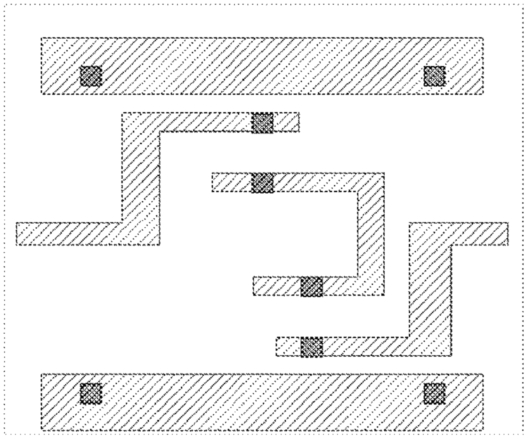
FIG. 1988C
*M* PDF Solutions, Inc.

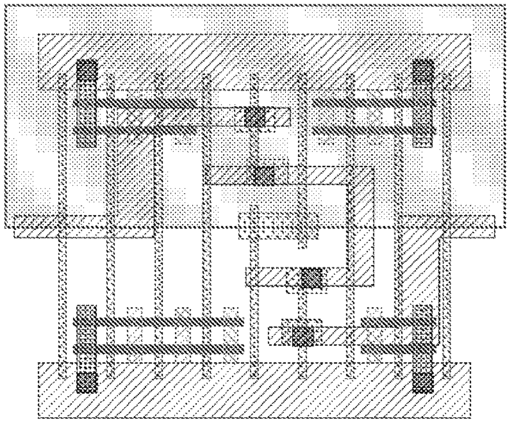
FIG. 1989A
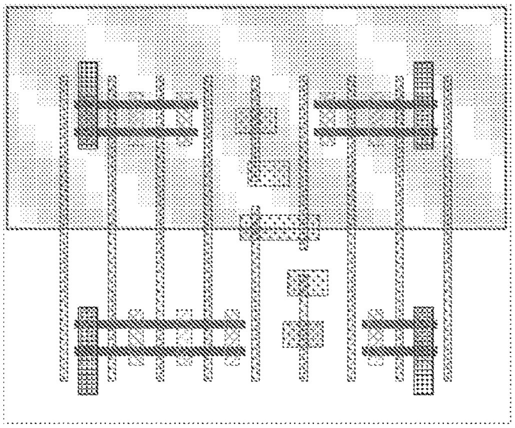
FIG. 1989B
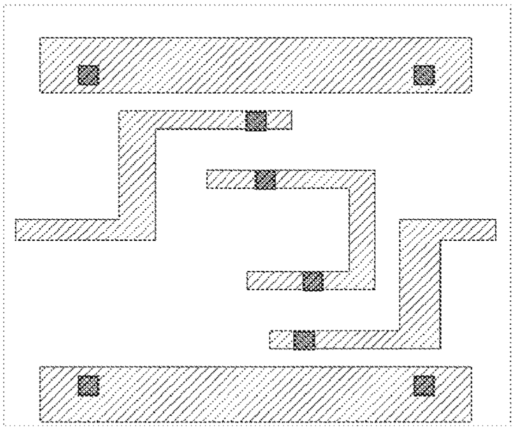
FIG. 1989C

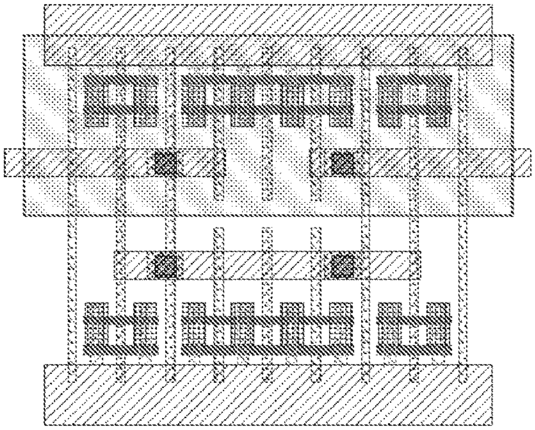
FIG. 1990A
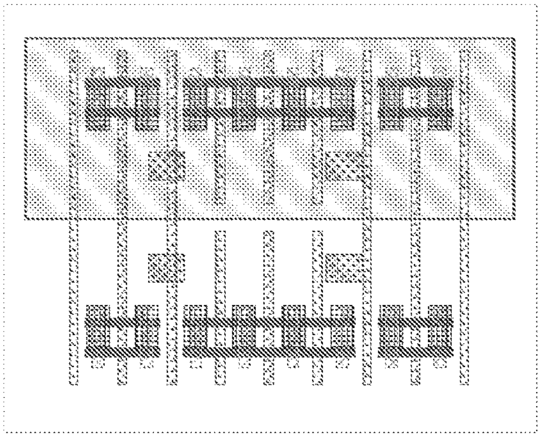
FIG. 1990B
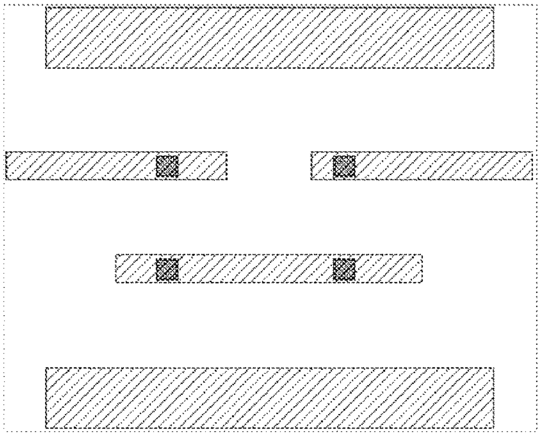
FIG. 1990C

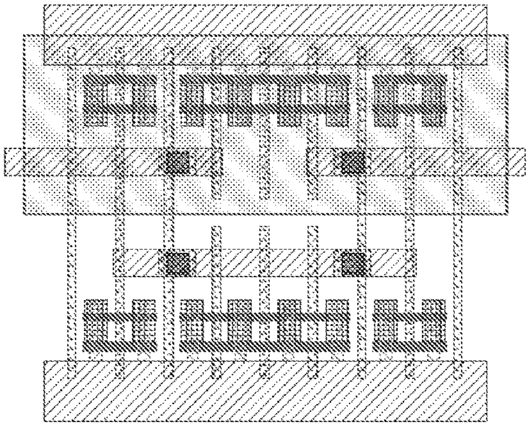
FIG. 1991A
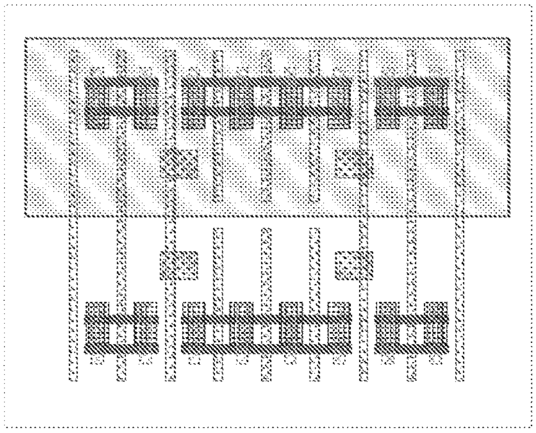
FIG. 1991B
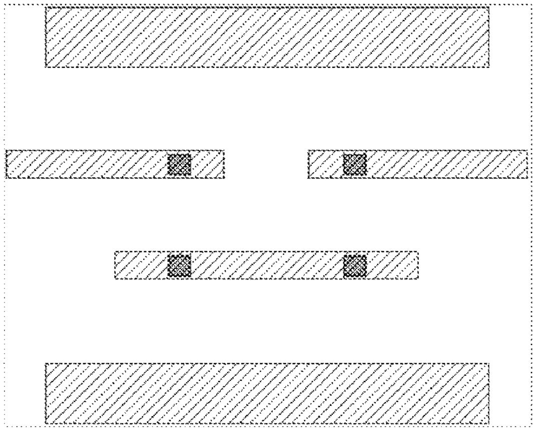
FIG. 1991C

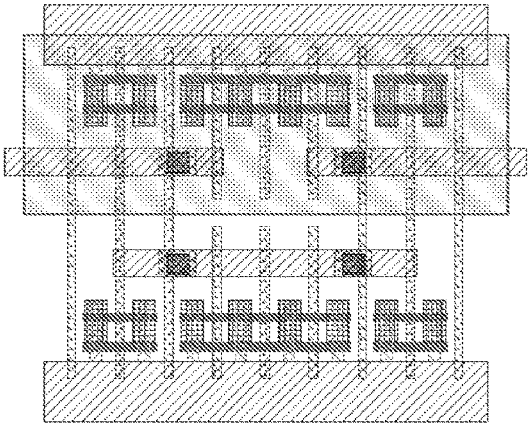
FIG. 1992A
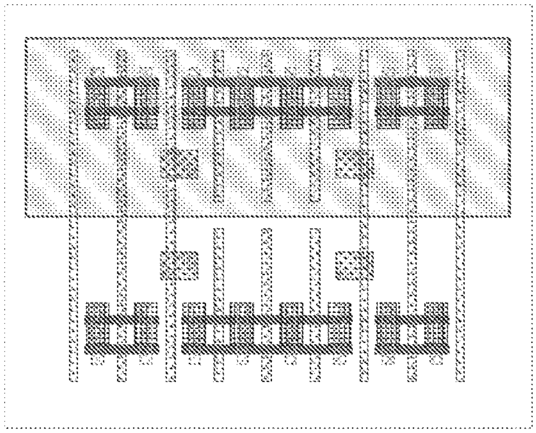
FIG. 1992B
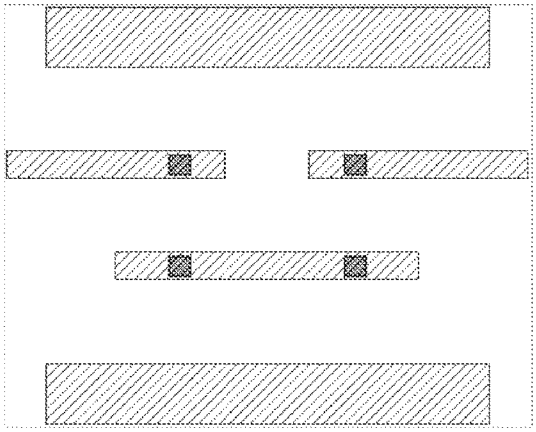
FIG. 1992C

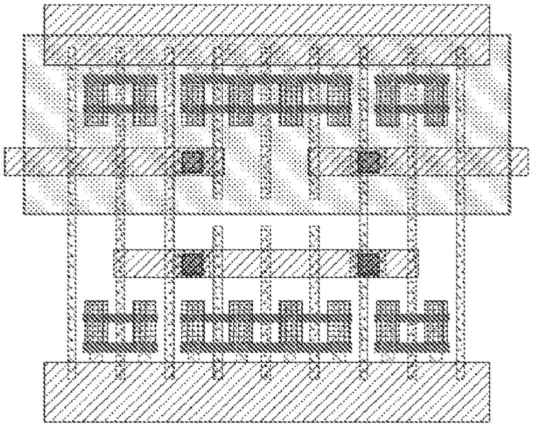
FIG. 1993A
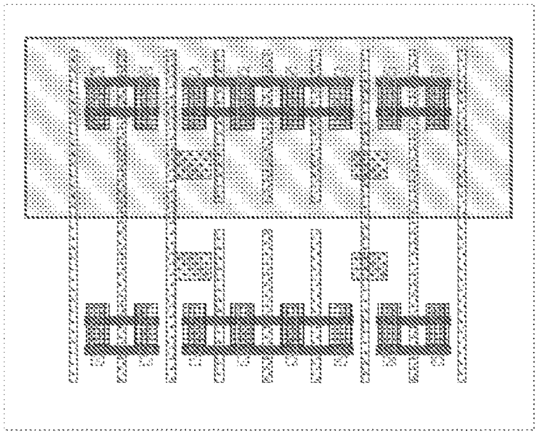
FIG. 1993B
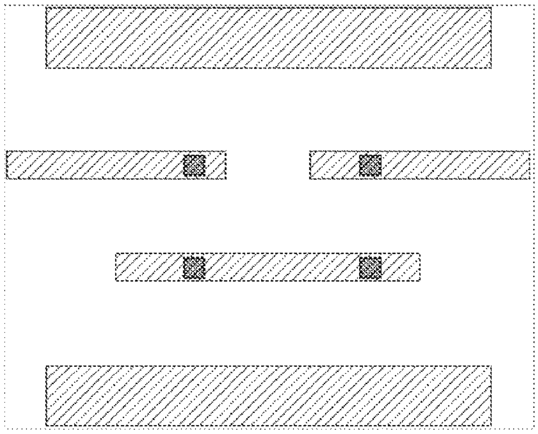
FIG. 1993C

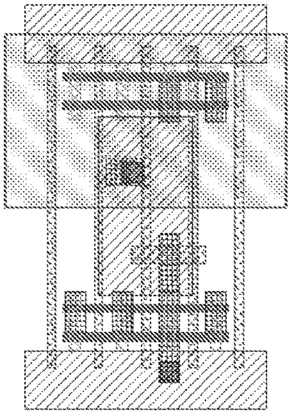
FIG. 1994A
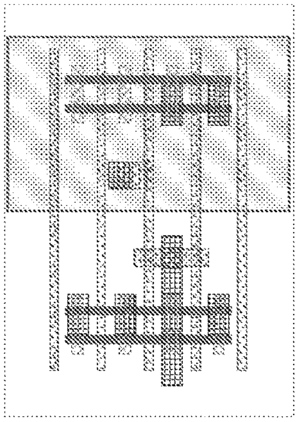
FIG. 1994B
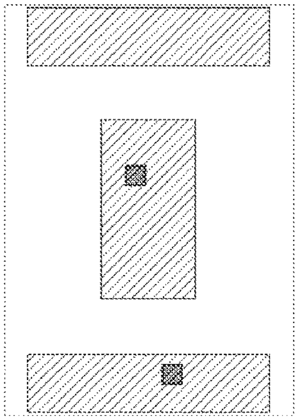
FIG. 1994C

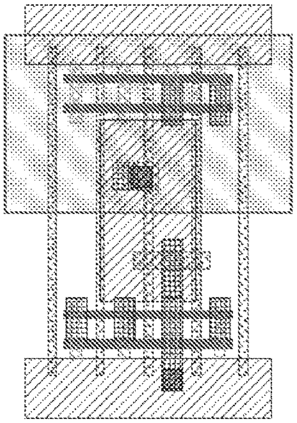
FIG. 1995A
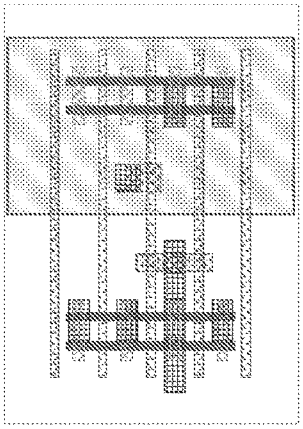
FIG. 1995B
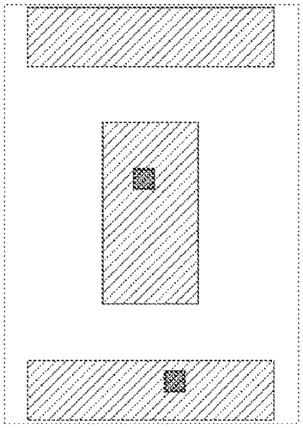
FIG. 1995C

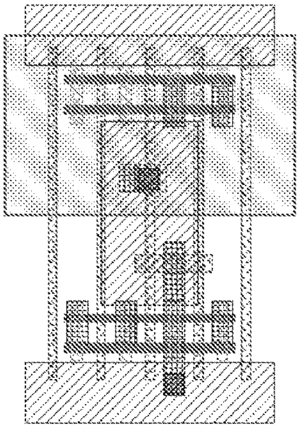
FIG. 1996A
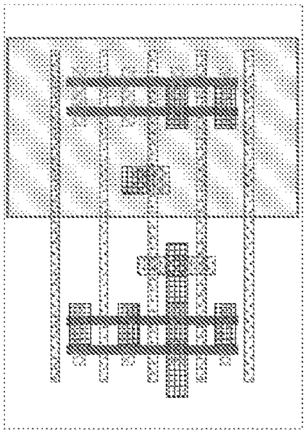
FIG. 1996B
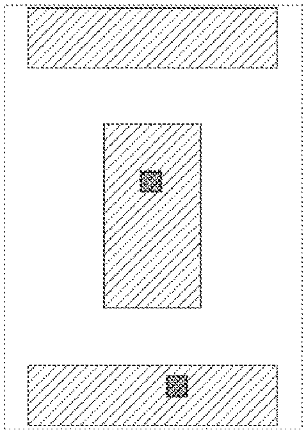
FIG. 1996C

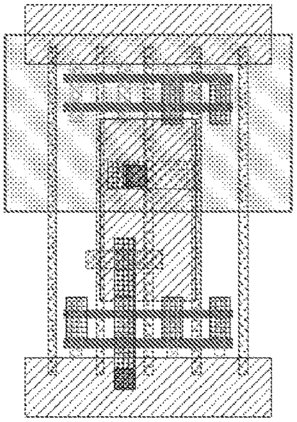
FIG. 1997A
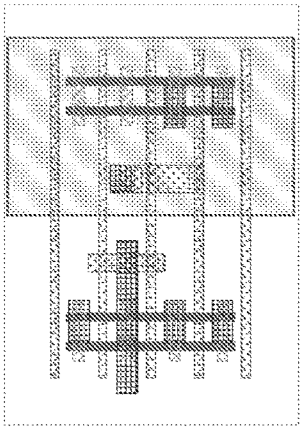
FIG. 1997B
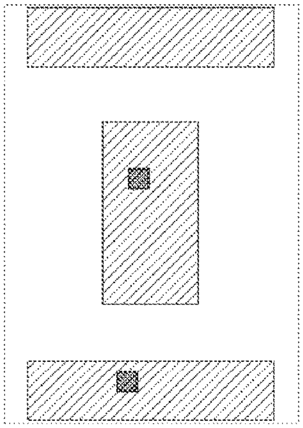
FIG. 1997C

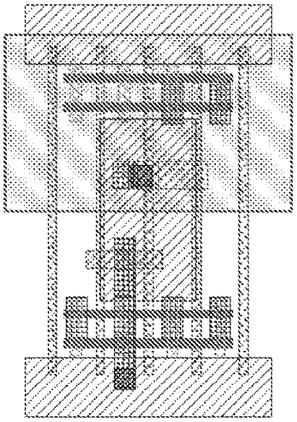
FIG. 1998A
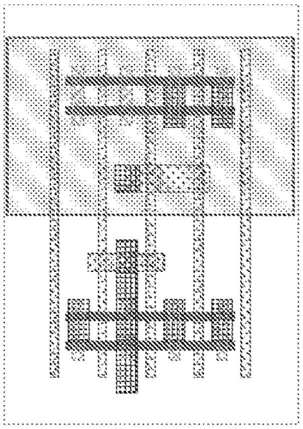
FIG. 1998B
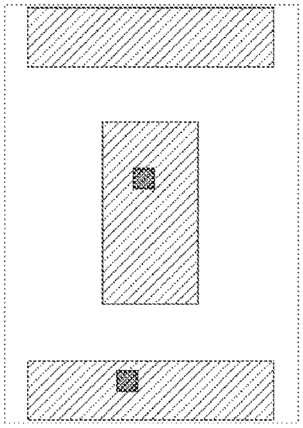
FIG. 1998C

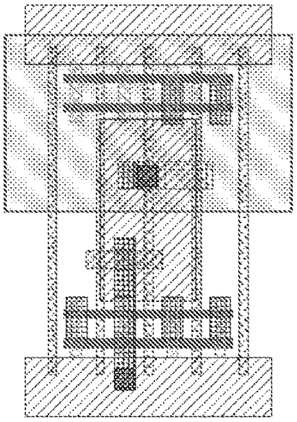
FIG. 1999A
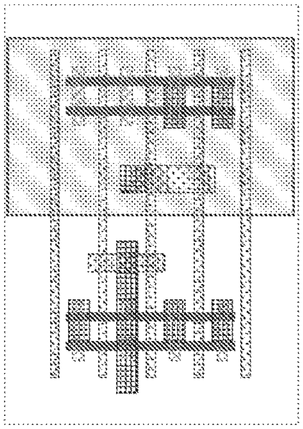
FIG. 1999B
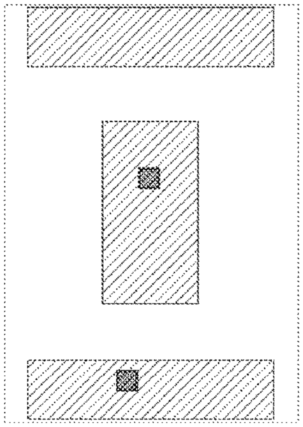
FIG. 1999C
*M* PDF Solutions, Inc.

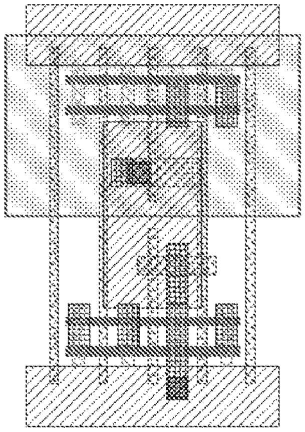
FIG. 2000A
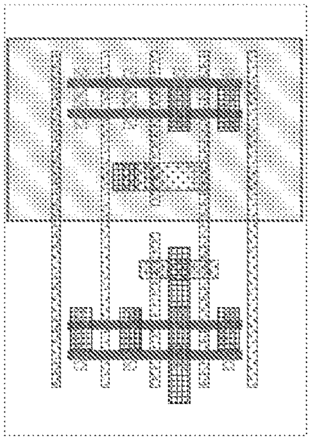
FIG. 2000B
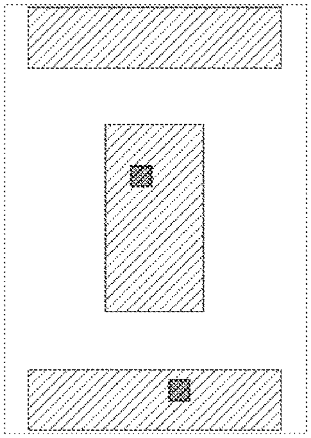
FIG. 2000C

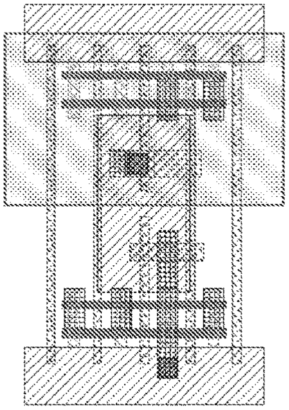
FIG. 2001A
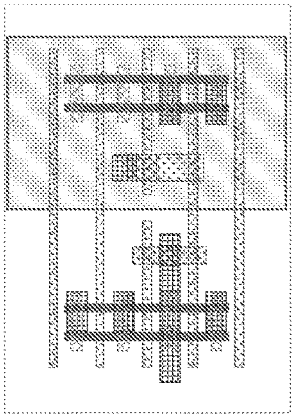
FIG. 2001B
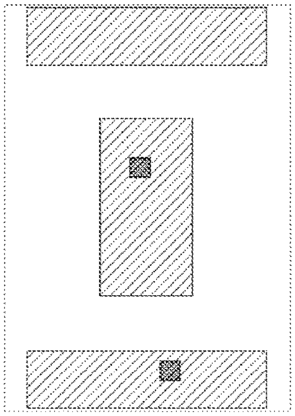
FIG. 2001C
*M* PDF Solutions, Inc.

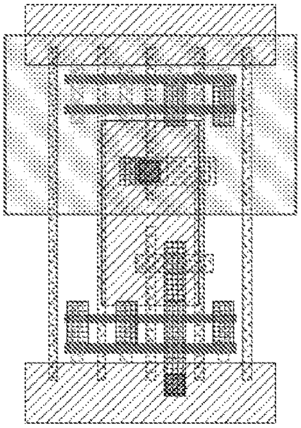
FIG. 2002A
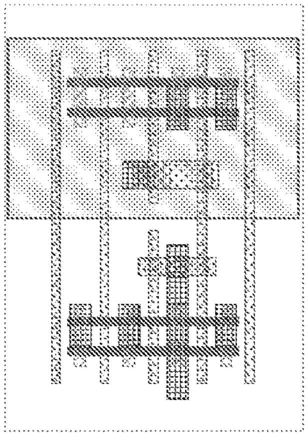
FIG. 2002B
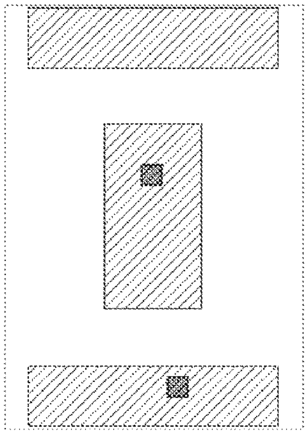
FIG. 2002C

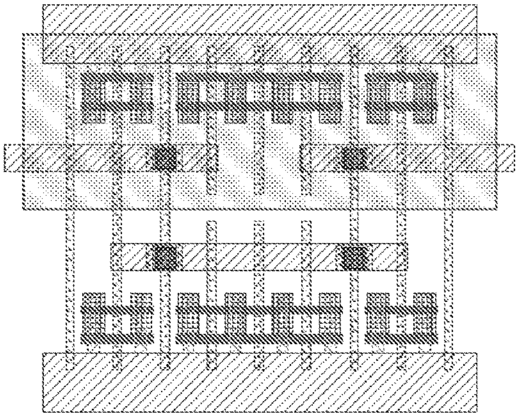
FIG. 2003A
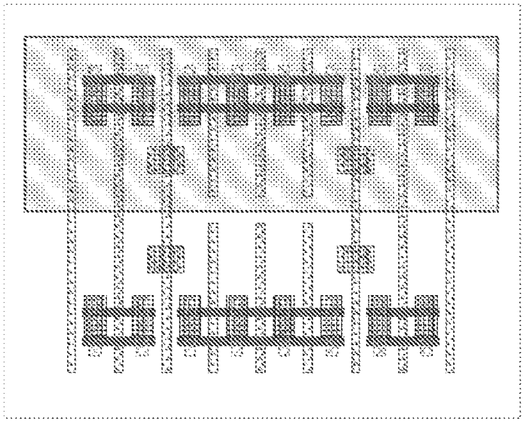
FIG. 2003B
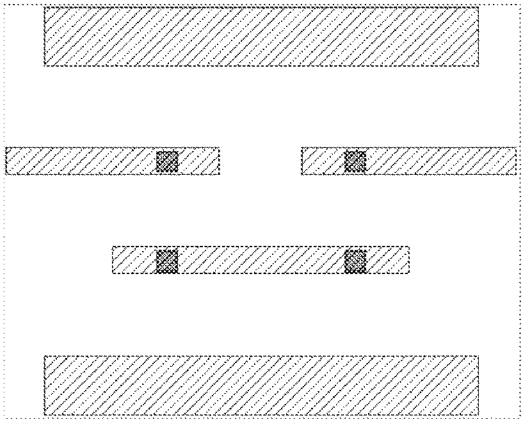
FIG. 2003C

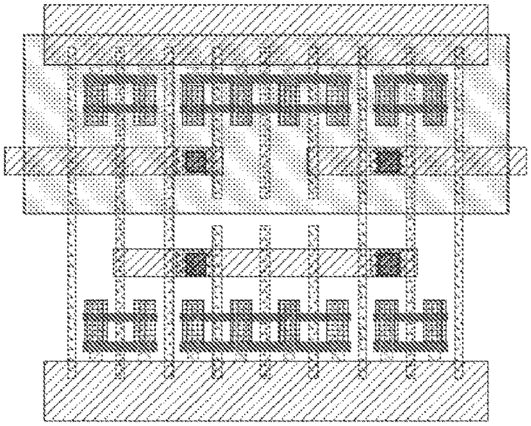
FIG. 2004A
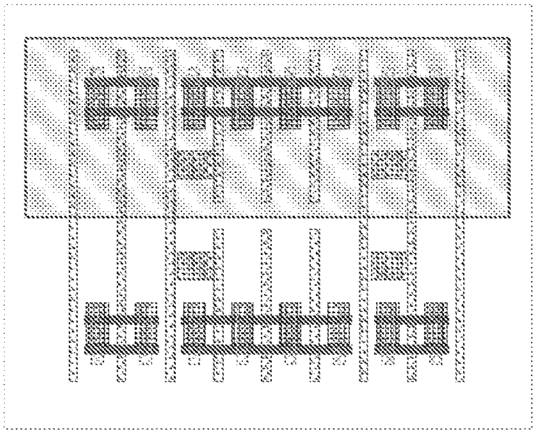
FIG. 2004B
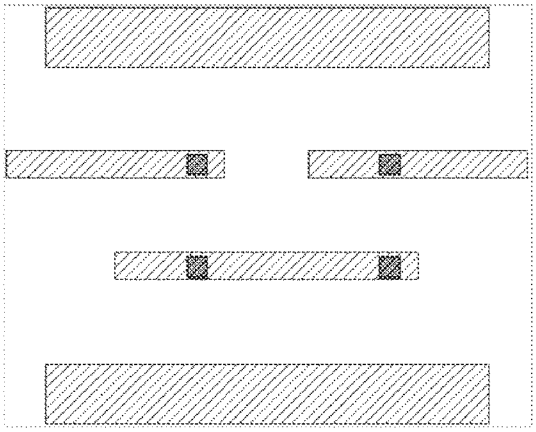
FIG. 2004C
*M* PDF Solutions, Inc.

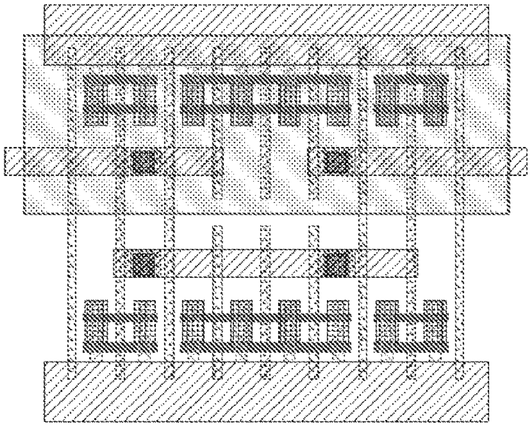
FIG. 2005A
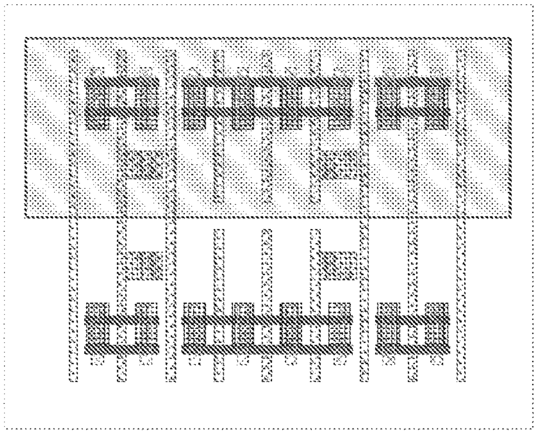
FIG. 2005B
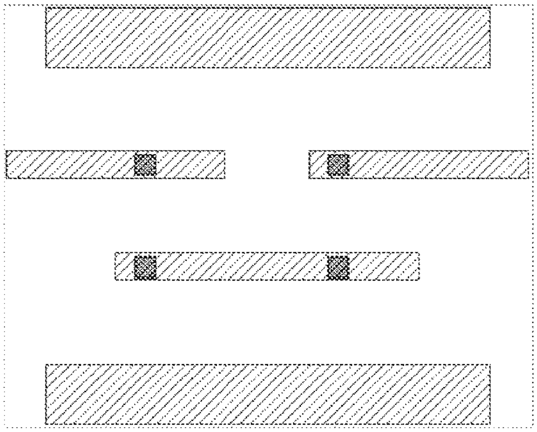
FIG. 2005C

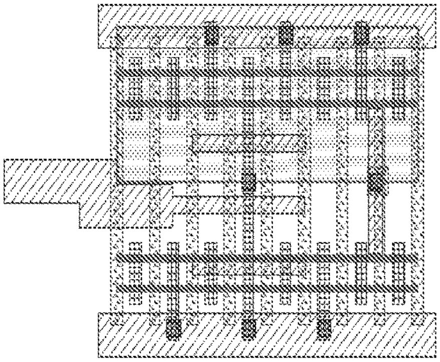
FIG. 2006A
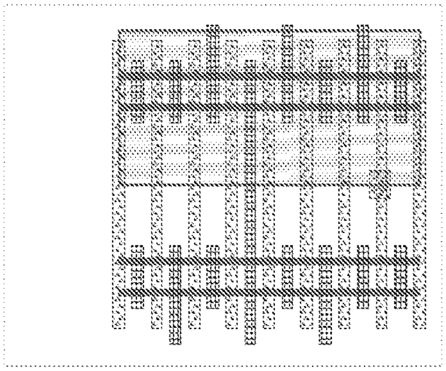
FIG. 2006B
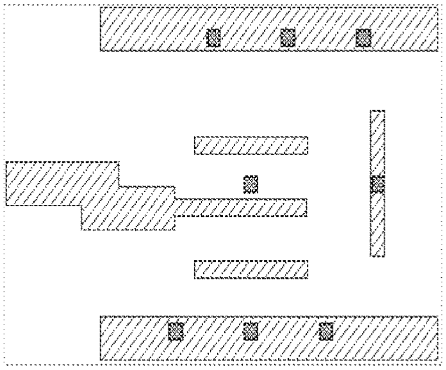
FIG. 2006C
*M* PDF Solutions, Inc.

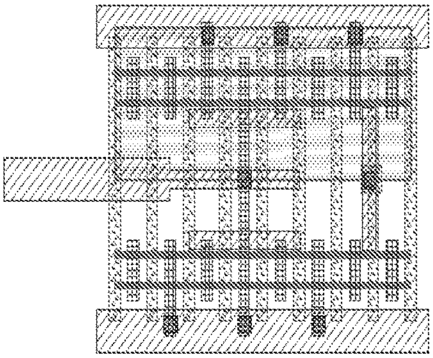
FIG. 2007A
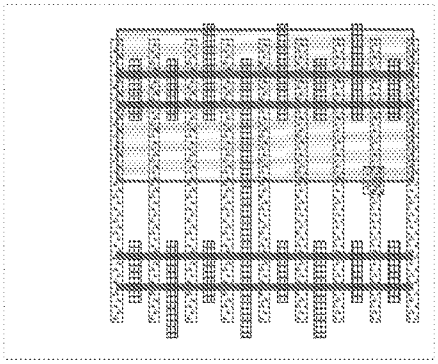
FIG. 2007B
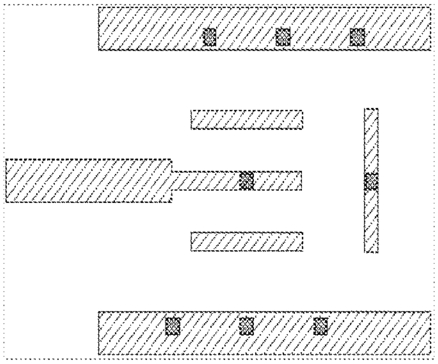
FIG. 2007C

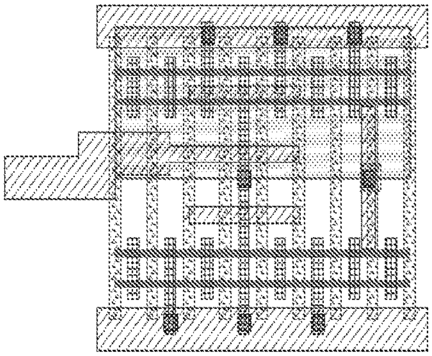
FIG. 2008A
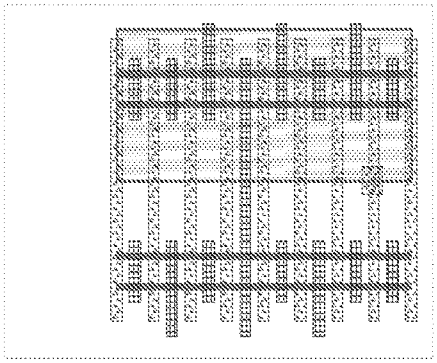
FIG. 2008B
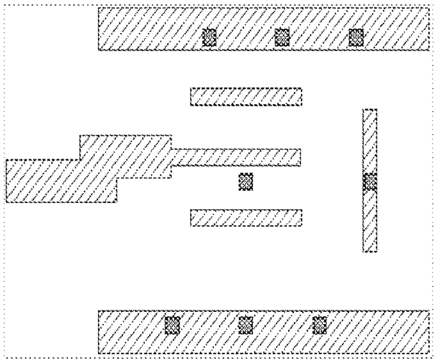
FIG. 2008C
*M* PDF Solutions, Inc.

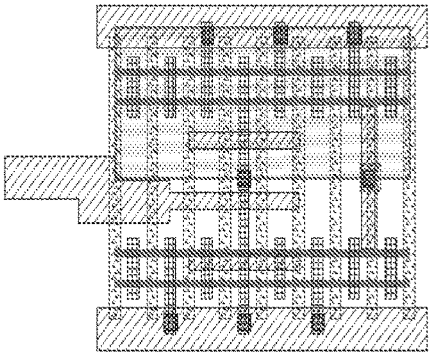
FIG. 2009A
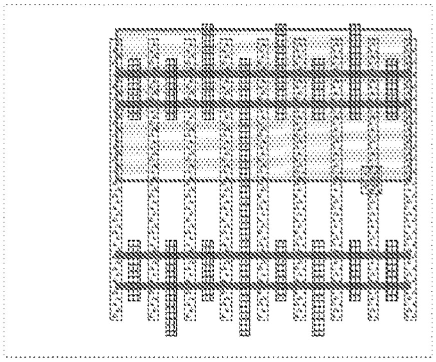
FIG. 2009B
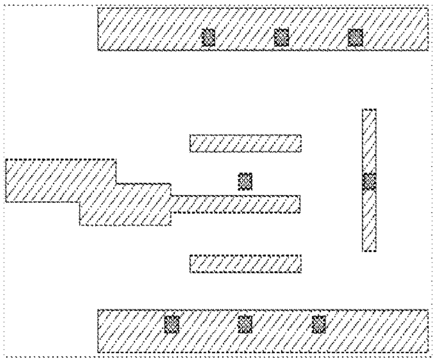
FIG. 2009C

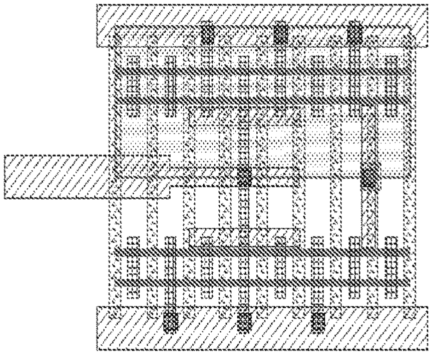
FIG. 2010A
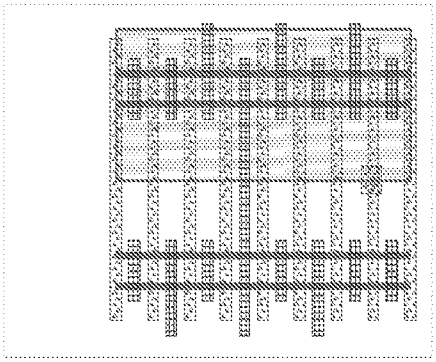
FIG. 2010B
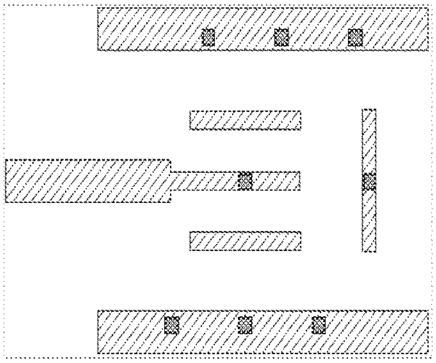
FIG. 2010C
*M* PDF Solutions, Inc.

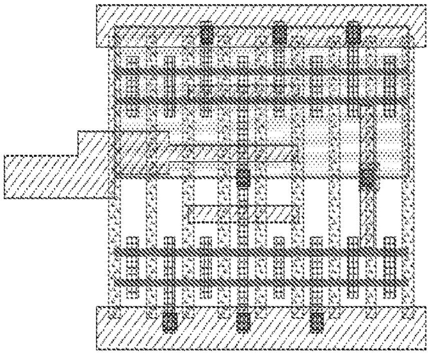
FIG. 2011A
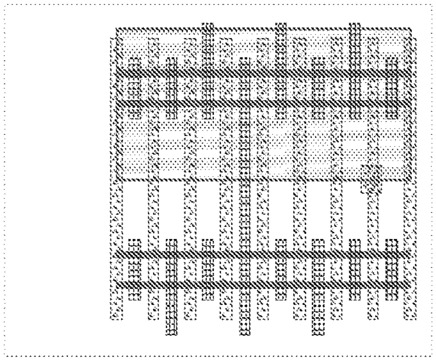
FIG. 2011B
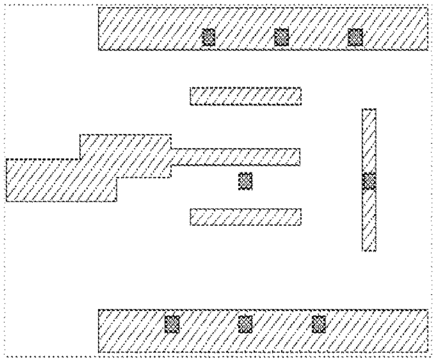
FIG. 2011C
*M* PDF Solutions, Inc.

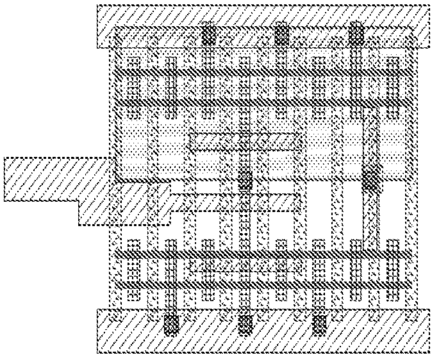
FIG. 2012A
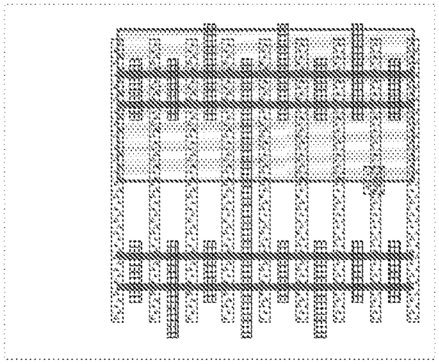
FIG. 2012B
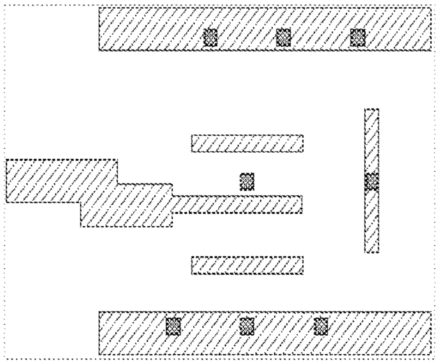
FIG. 2012C

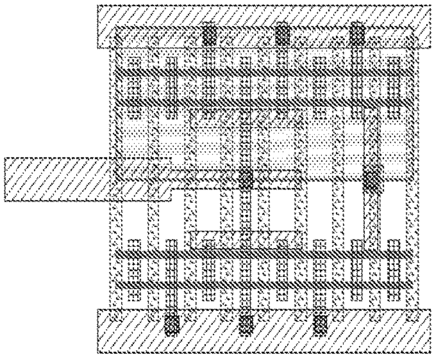
FIG. 2013A
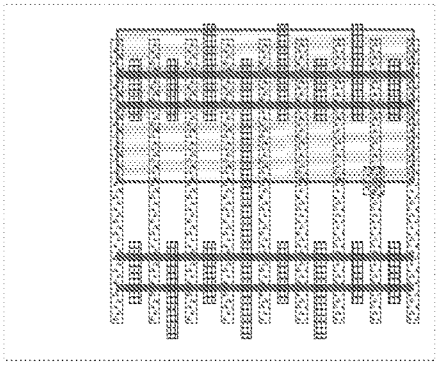
FIG. 2013B
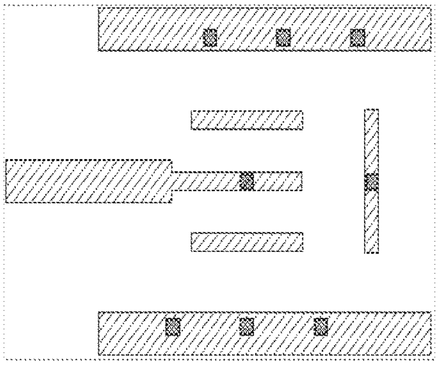
FIG. 2013C

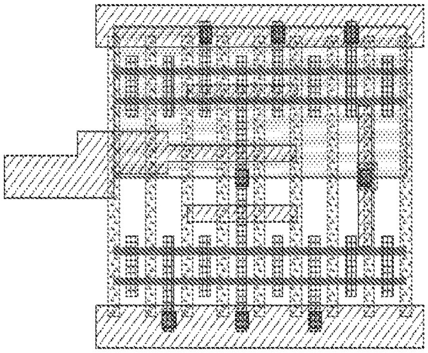
FIG. 2014A
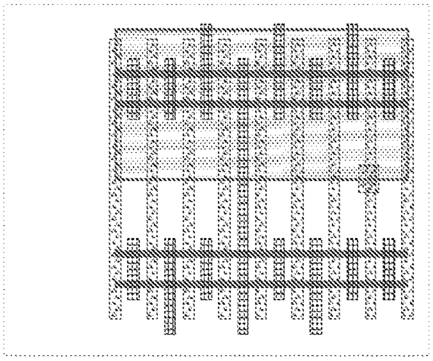
FIG. 2014B
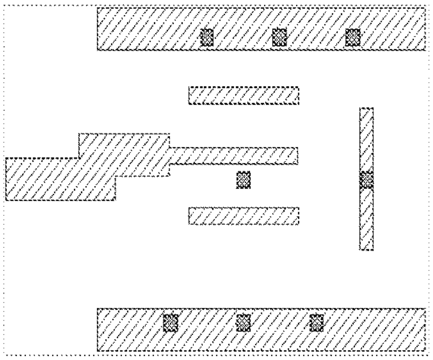
FIG. 2014C

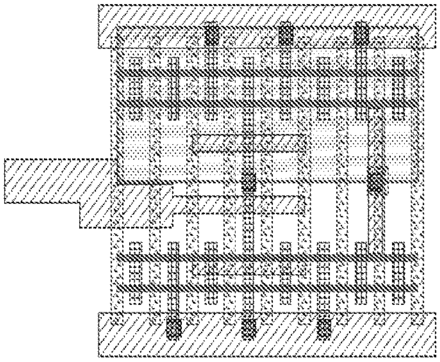
FIG. 2015A
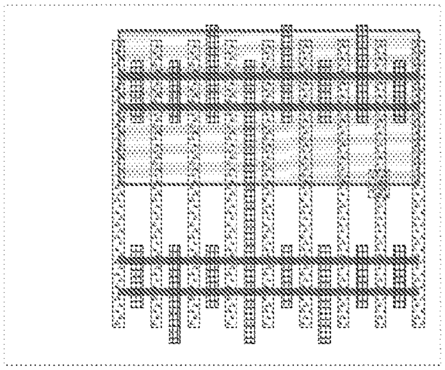
FIG. 2015B
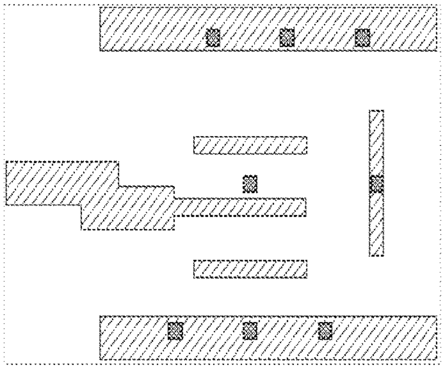
FIG. 2015C

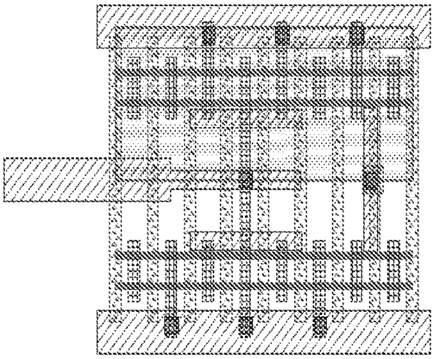
FIG. 2016A
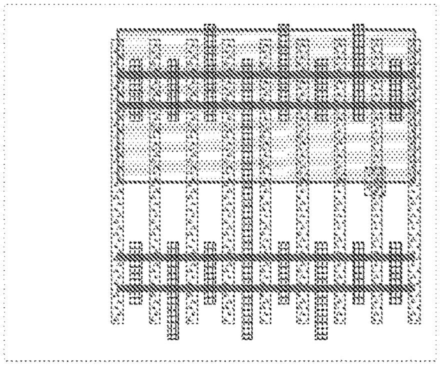
FIG. 2016B
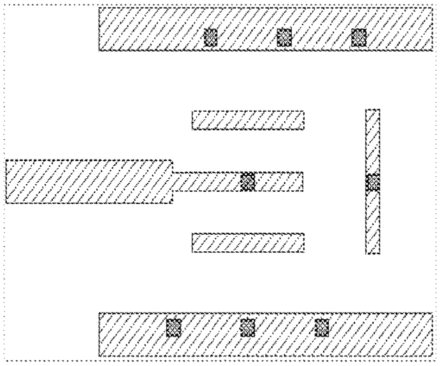
FIG. 2016C

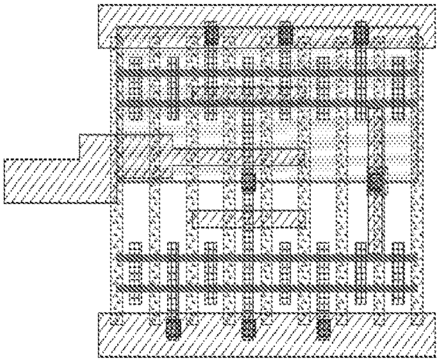
FIG. 2017A
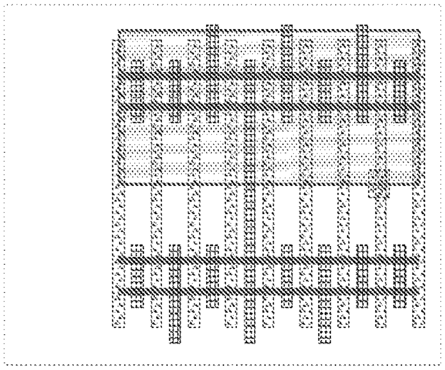
FIG. 2017B
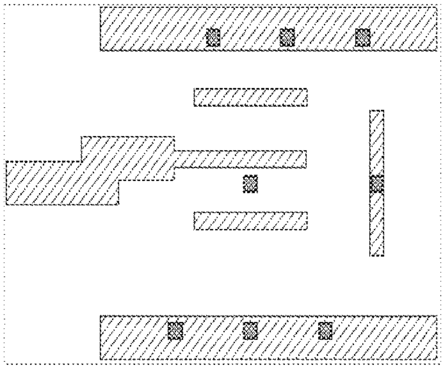
FIG. 2017C
*M* PDF Solutions, Inc.

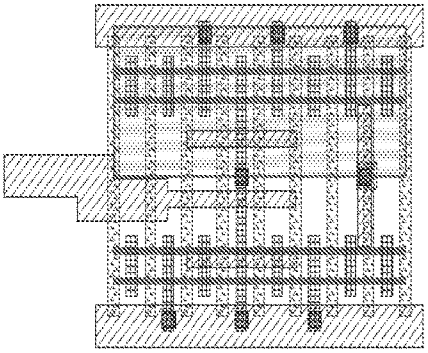
FIG. 2018A
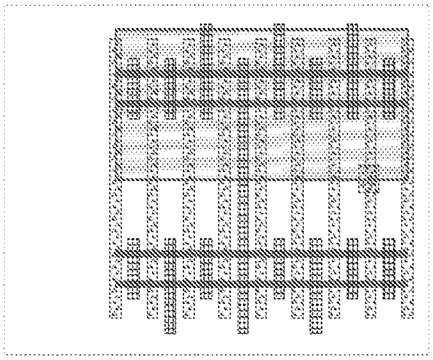
FIG. 2018B
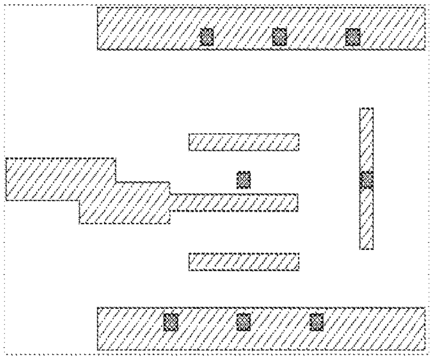
FIG. 2018C

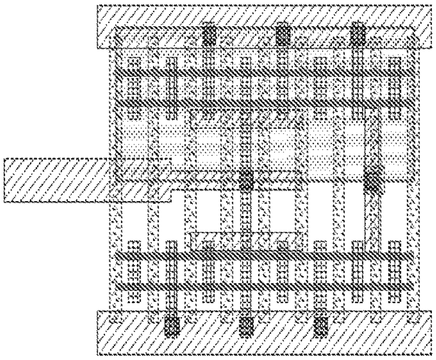
FIG. 2019A
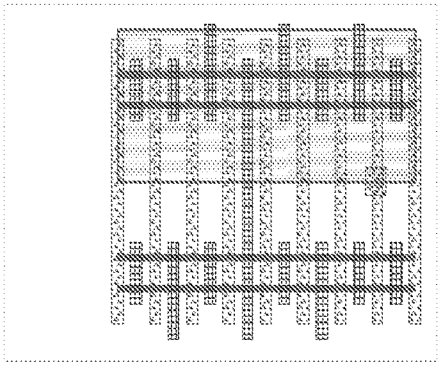
FIG. 2019B
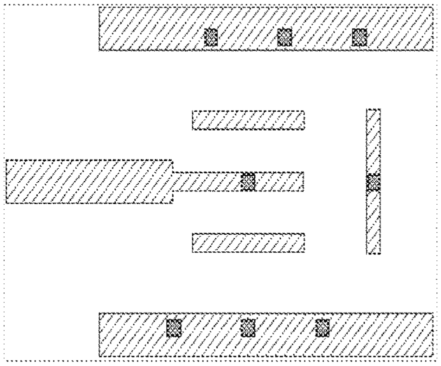
FIG. 2019C

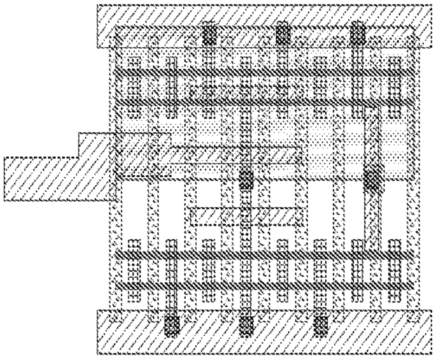
FIG. 2020A
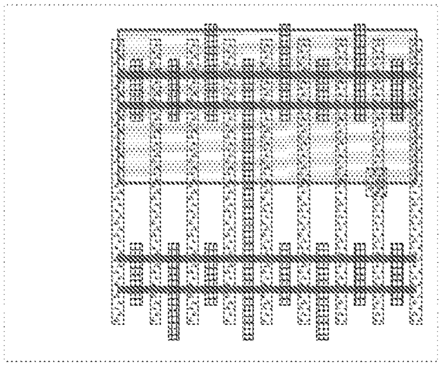
FIG. 2020B
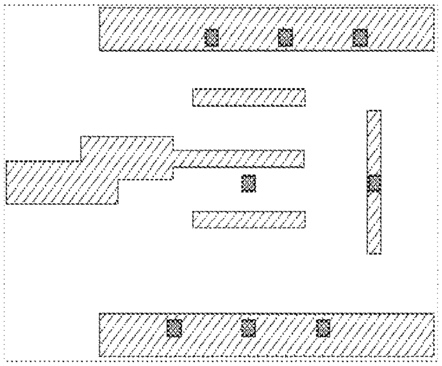
FIG. 2020C

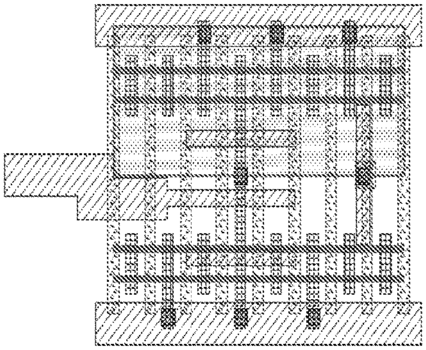
FIG. 2021A
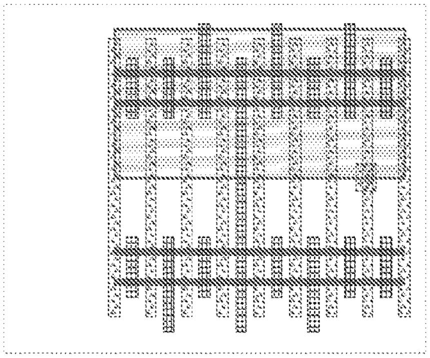
FIG. 2021B
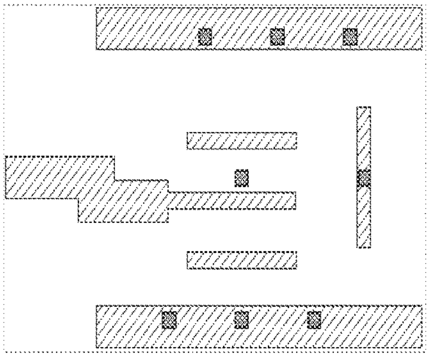
FIG. 2021C

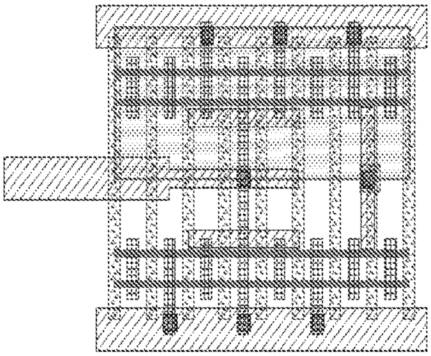
FIG. 2022A
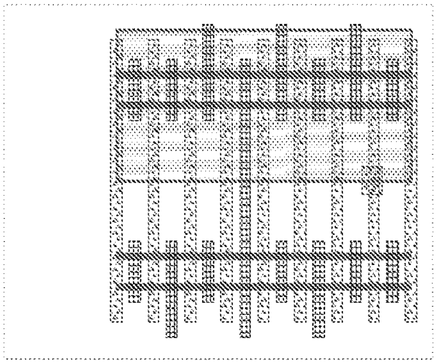
FIG. 2022B
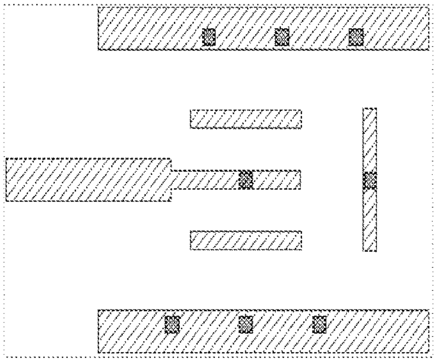
FIG. 2022C
*M* PDF Solutions, Inc.

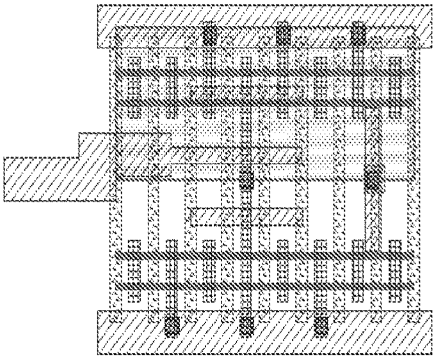
FIG. 2023A
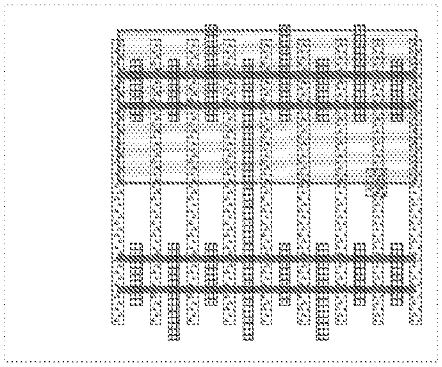
FIG. 2023B
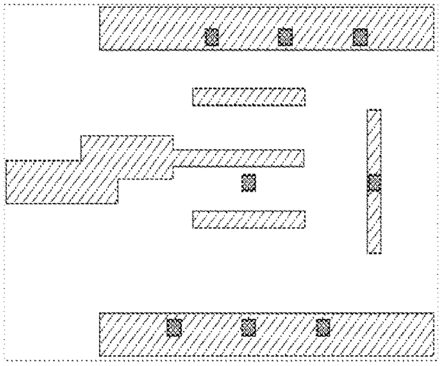
FIG. 2023C

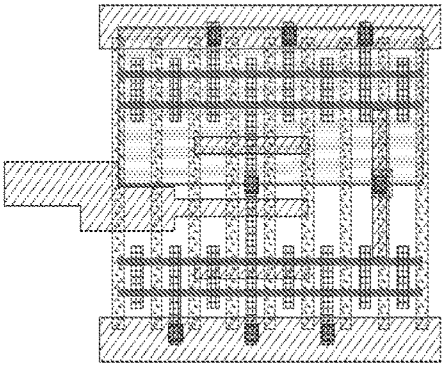
FIG. 2024A
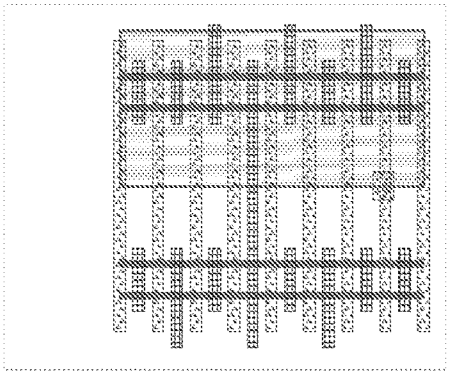
FIG. 2024B
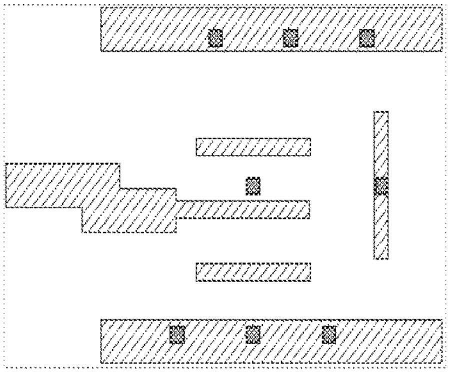
FIG. 2024C
*M* PDF Solutions, Inc.

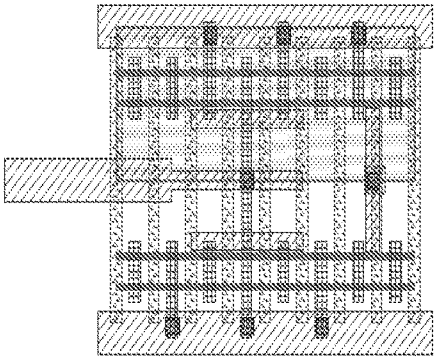
FIG. 2025A
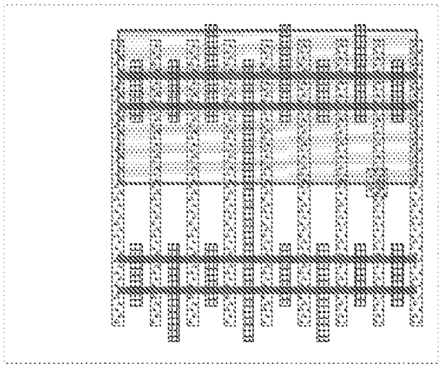
FIG. 2025B
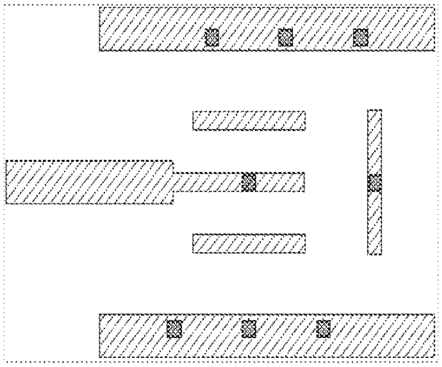
FIG. 2025C
*M* PDF Solutions, Inc.

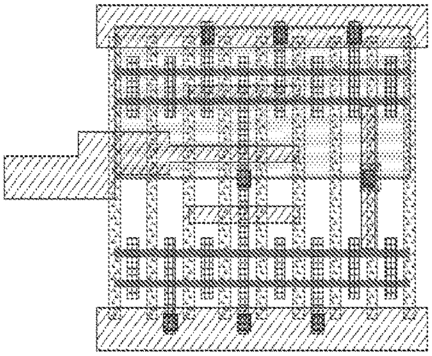
FIG. 2026A
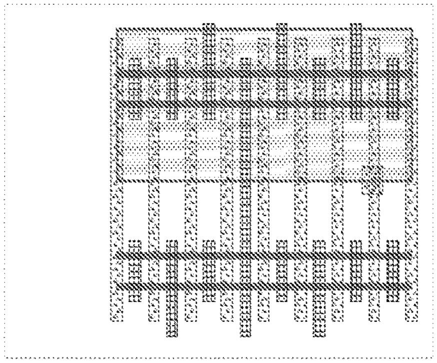
FIG. 2026B
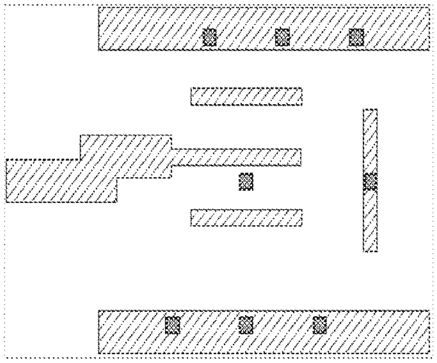
FIG. 2026C
*M* PDF Solutions, Inc.

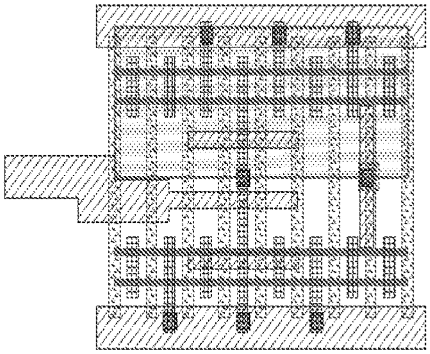
FIG. 2027A
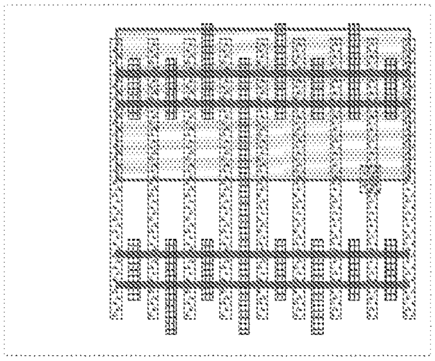
FIG. 2027B
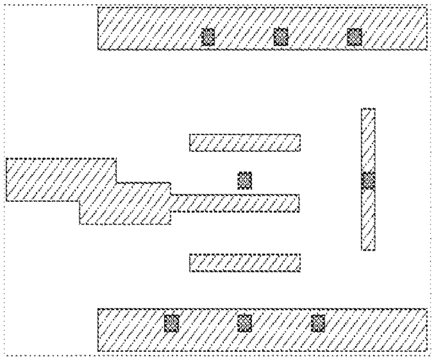
FIG. 2027C

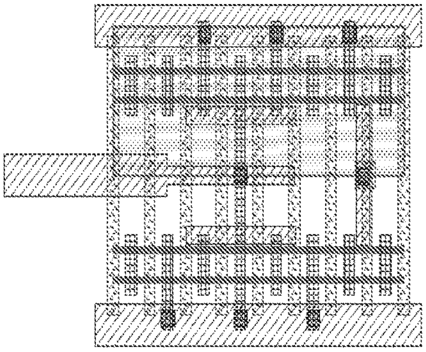
FIG. 2028A
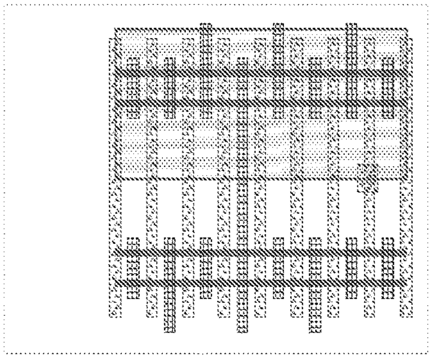
FIG. 2028B
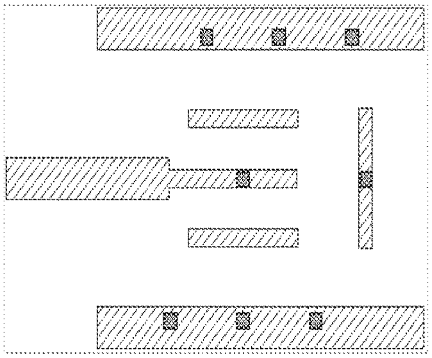
FIG. 2028C
*M* PDF Solutions, Inc.

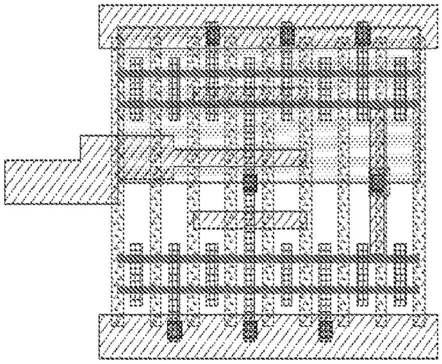
FIG. 2029A
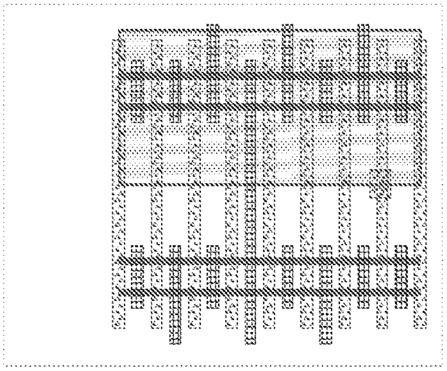
FIG. 2029B
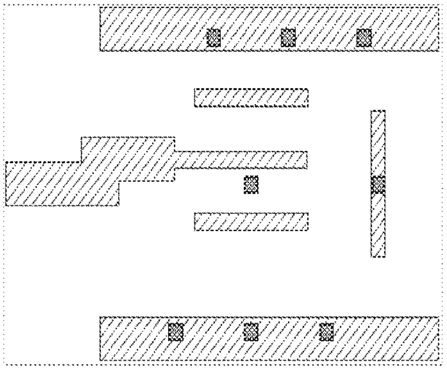
FIG. 2029C

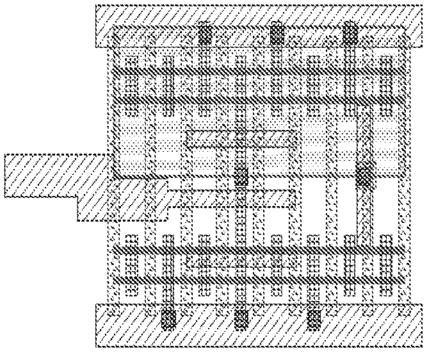
FIG. 2030A
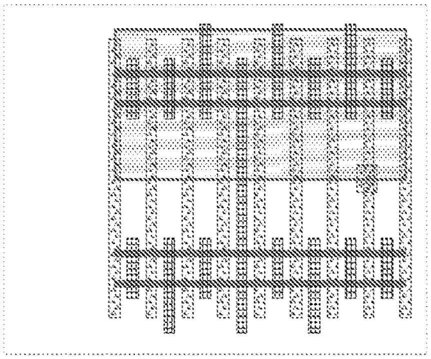
FIG. 2030B
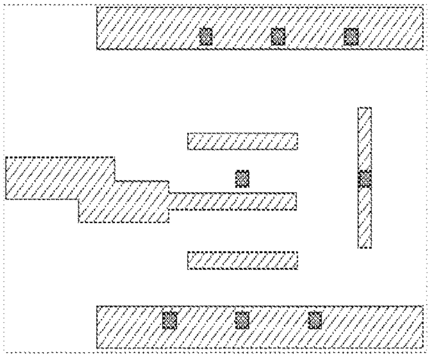
FIG. 2030C

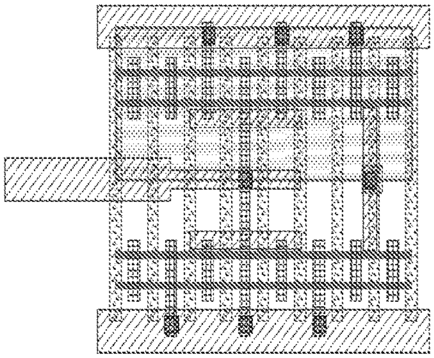
FIG. 2031A
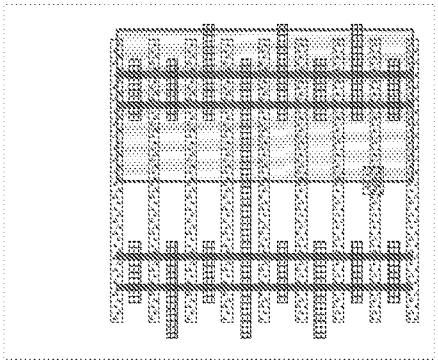
FIG. 2031B
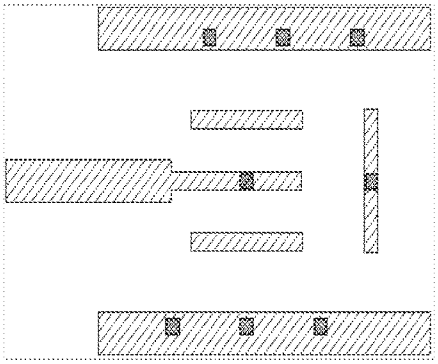
FIG. 2031C

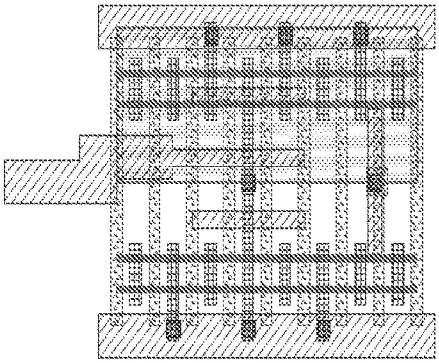
FIG. 2032A
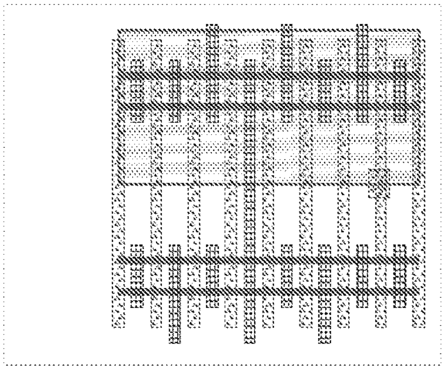
FIG. 2032B
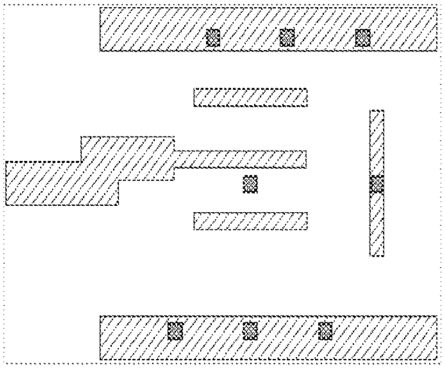
FIG. 2032C
*M* PDF Solutions, Inc.

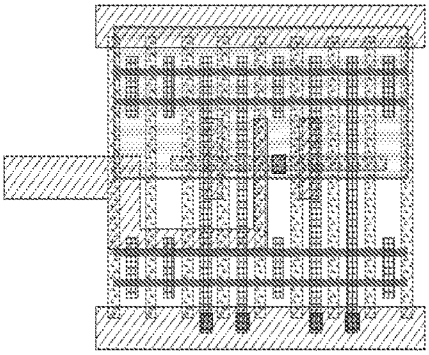
FIG. 2033A
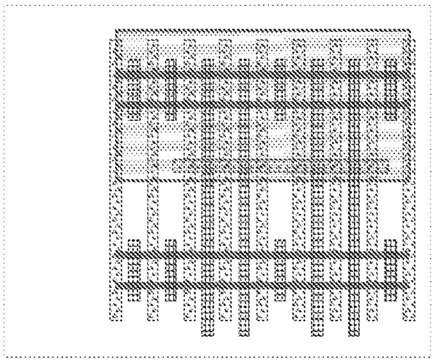
FIG. 2033B
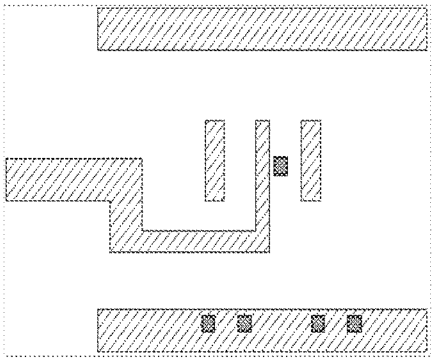
FIG. 2033C

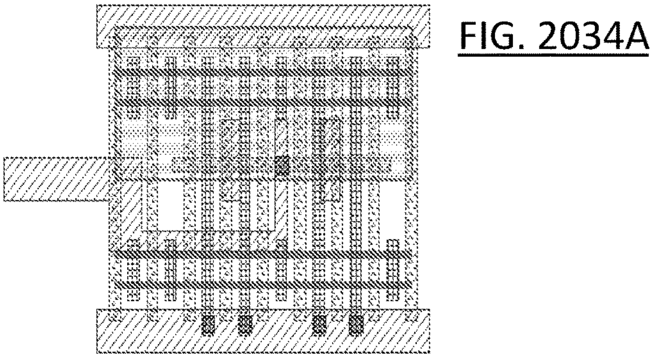
FIG. 2034A
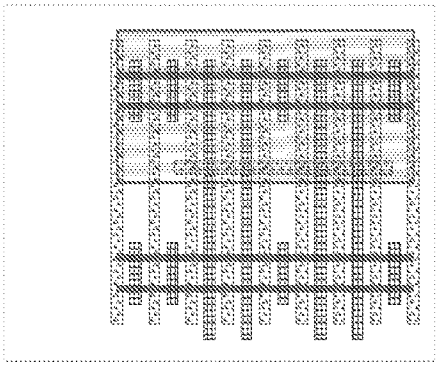
FIG. 2034B
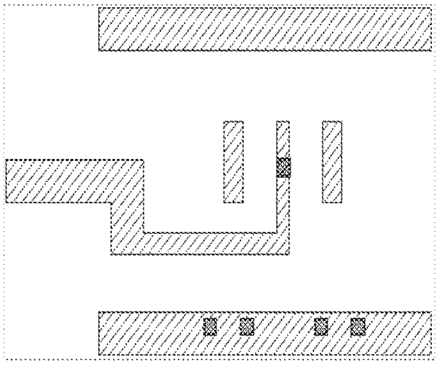
FIG. 2034C

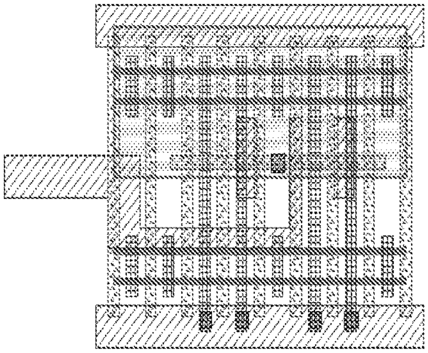
FIG. 2035A
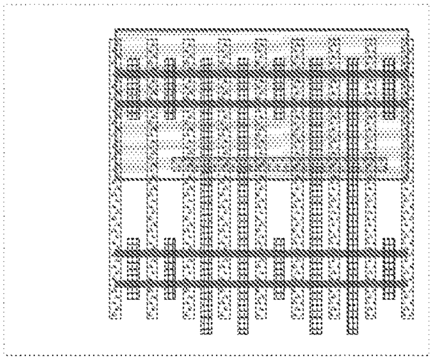
FIG. 2035B
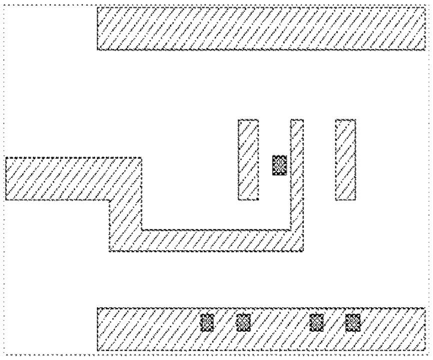
FIG. 2035C
*M* PDF Solutions, Inc.

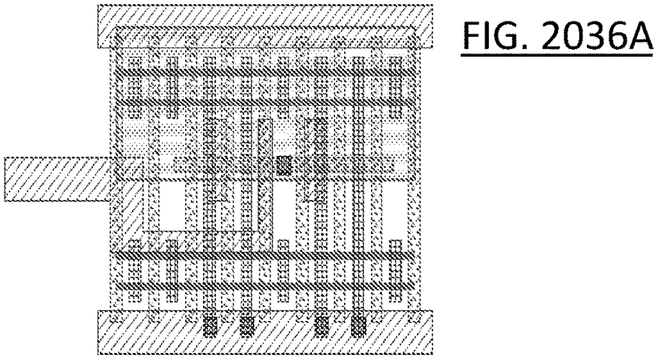
FIG. 2036A
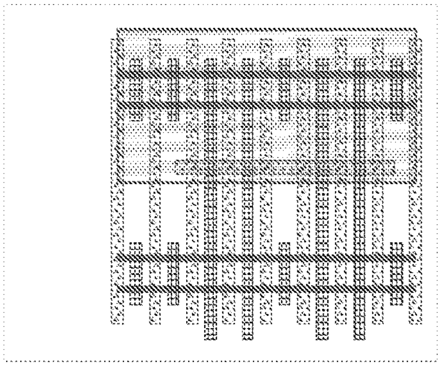
FIG. 2036B
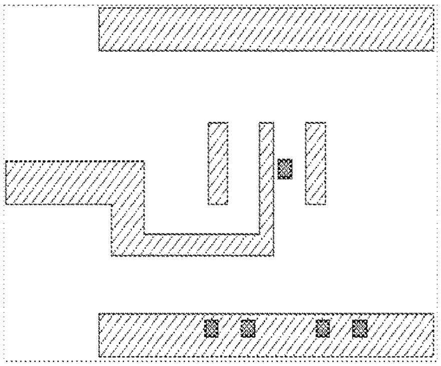
FIG. 2036C

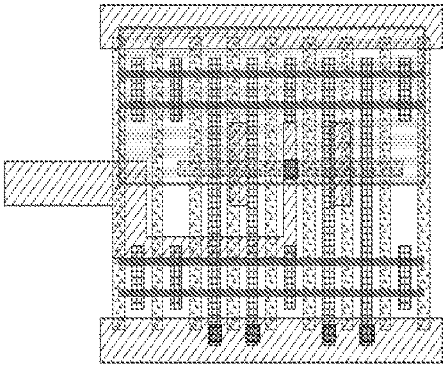
FIG. 2037A
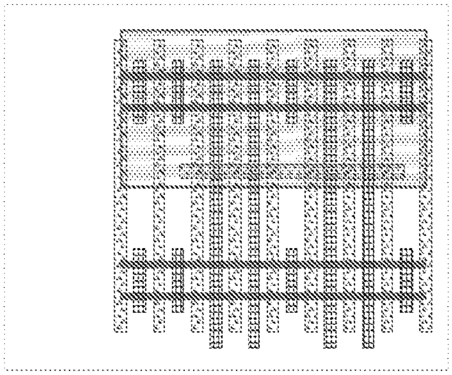
FIG. 2037B
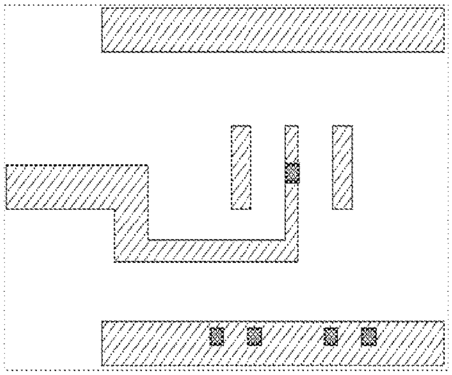
FIG. 2037C

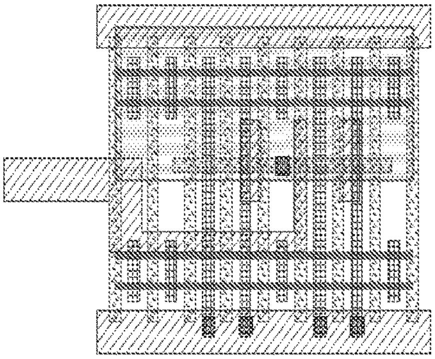
FIG. 2038A
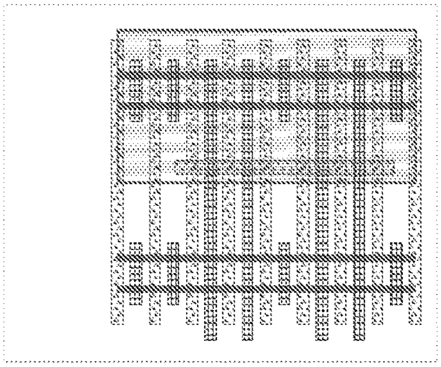
FIG. 2038B
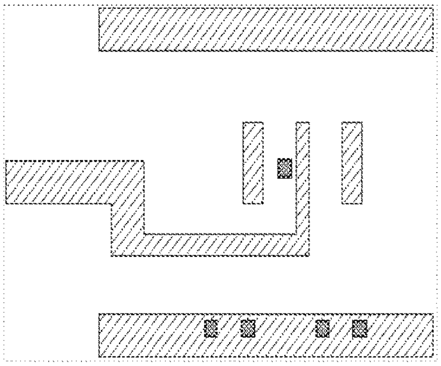
FIG. 2038C

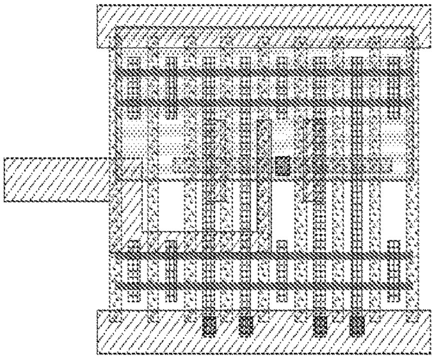
FIG. 2039A
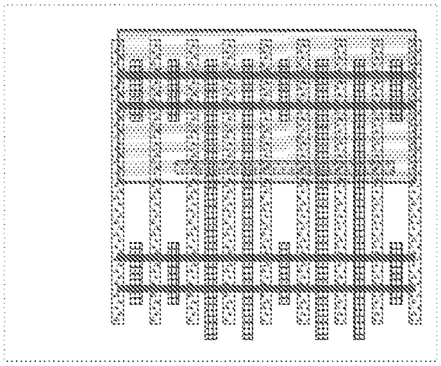
FIG. 2039B
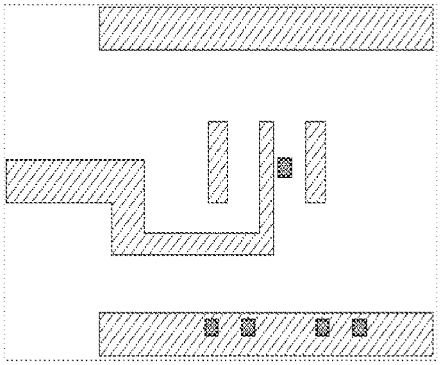
FIG. 2039C
*M* PDF Solutions, Inc.

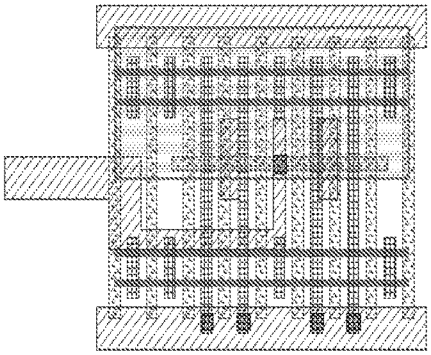
FIG. 2040A
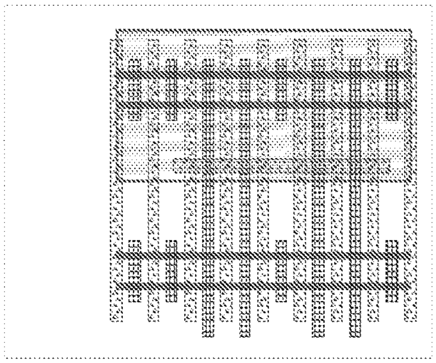
FIG. 2040B
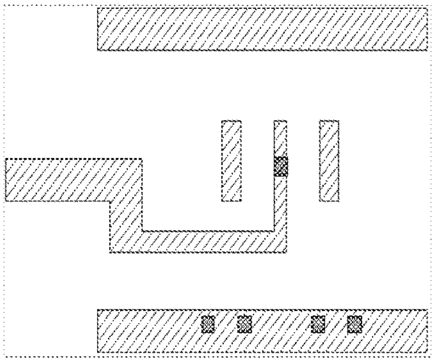
FIG. 2040C

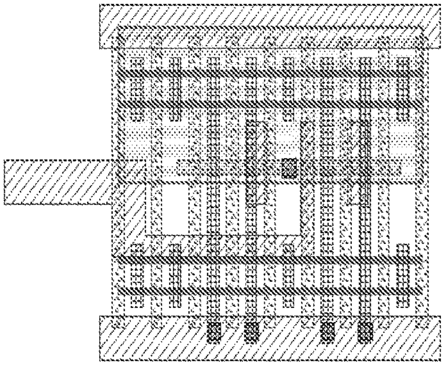
FIG. 2041A
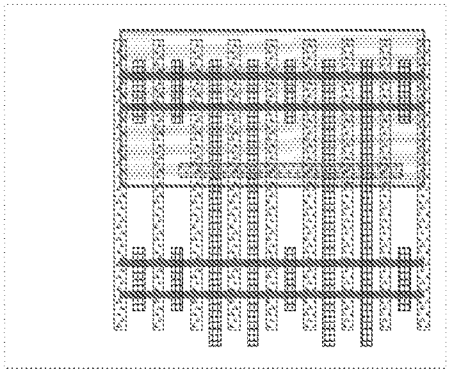
FIG. 2041B
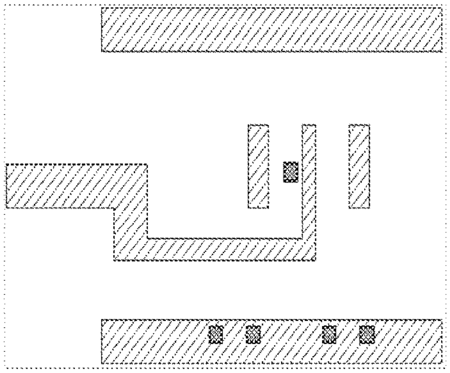
FIG. 2041C

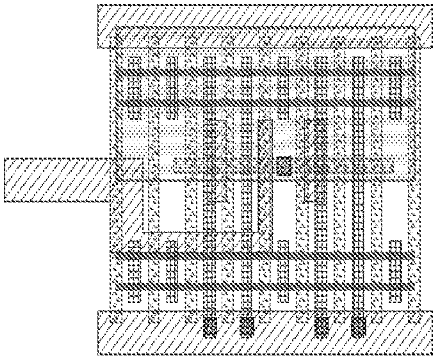
FIG. 2042A
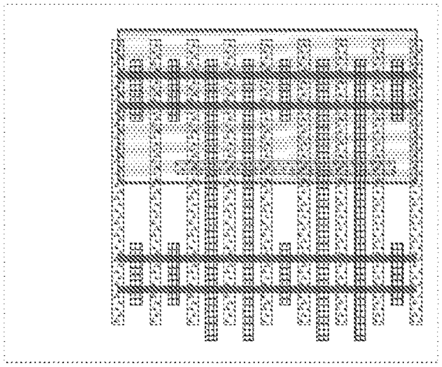
FIG. 2042B
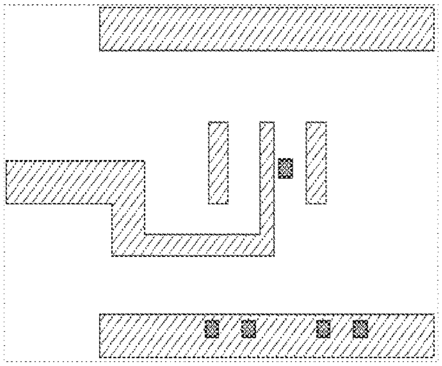
FIG. 2042C

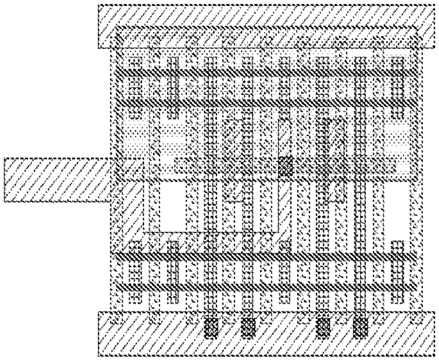
FIG. 2043A
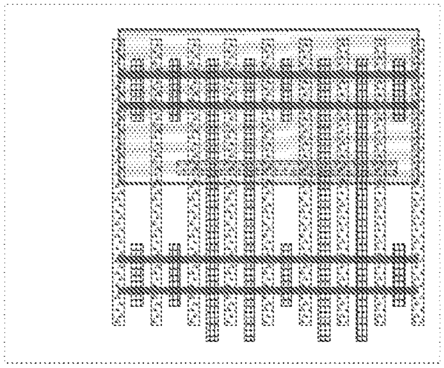
FIG. 2043B
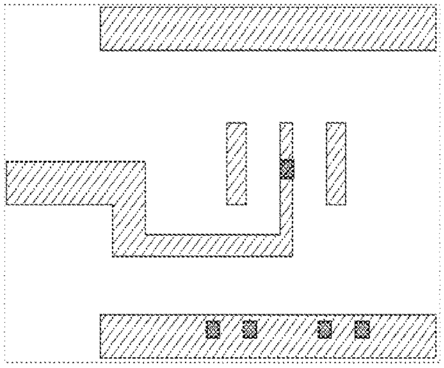
FIG. 2043C
*M* PDF Solutions, Inc.

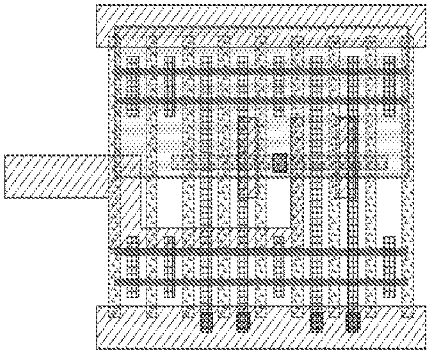
FIG. 2044A
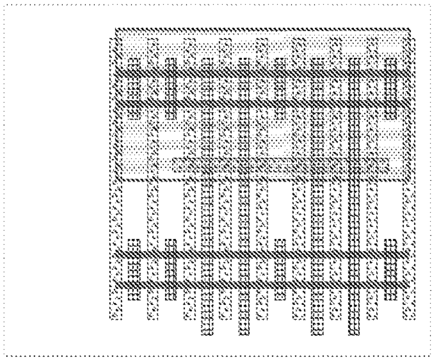
FIG. 2044B
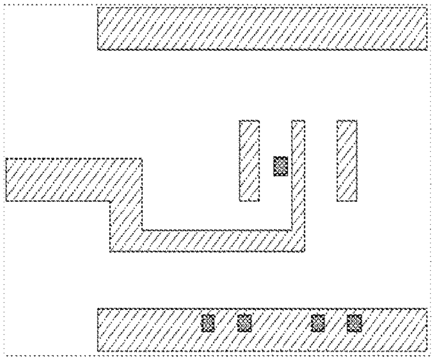
FIG. 2044C

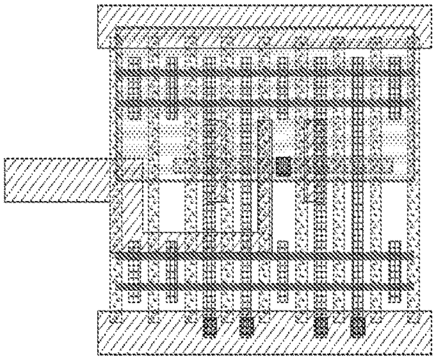
FIG. 2045A
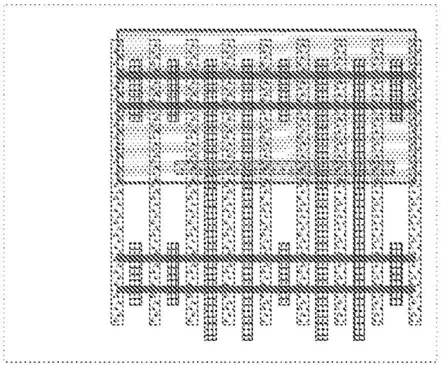
FIG. 2045B
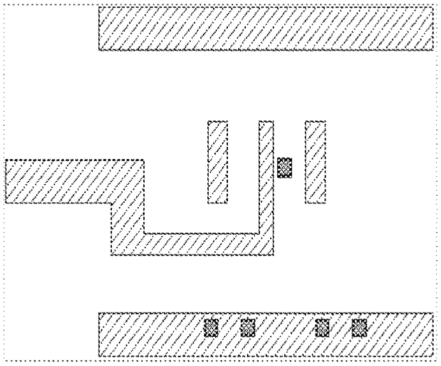
FIG. 2045C

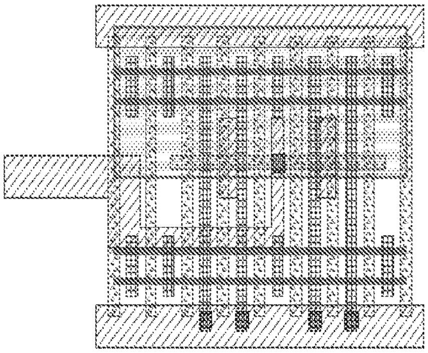
FIG. 2046A
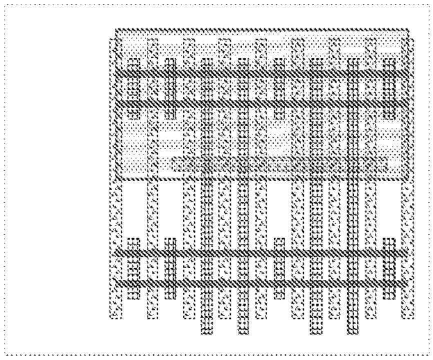
FIG. 2046B
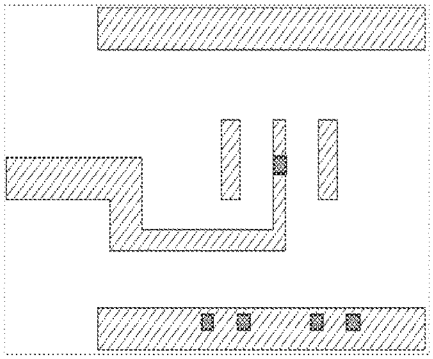
FIG. 2046C
*M* PDF Solutions, Inc.

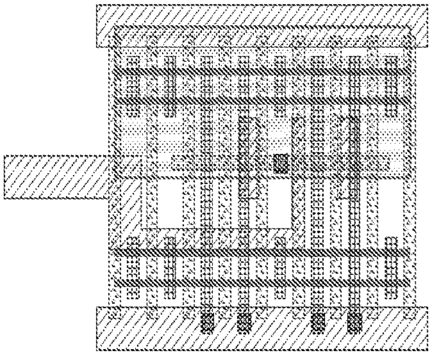
FIG. 2047A
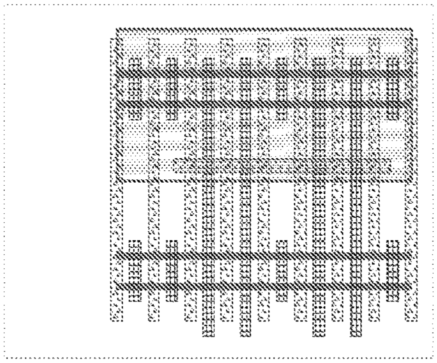
FIG. 2047B
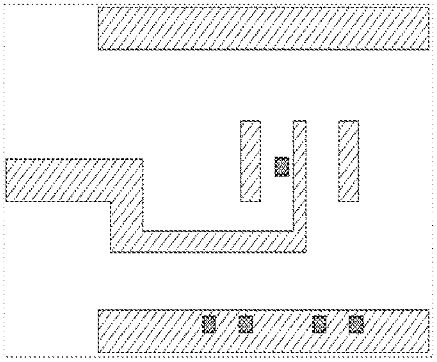
FIG. 2047C

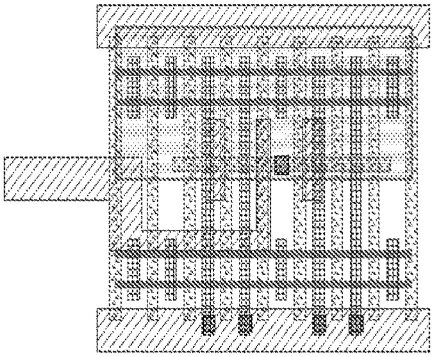
FIG. 2048A
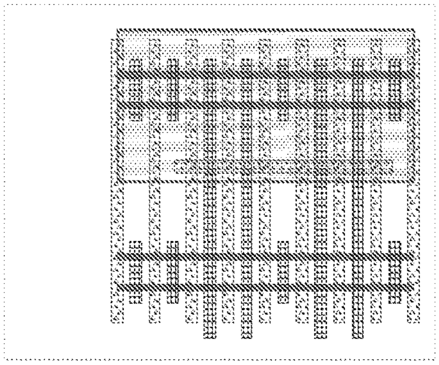
FIG. 2048B
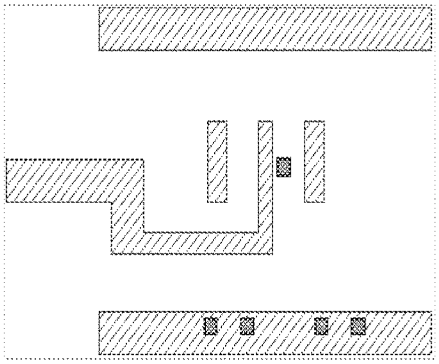
FIG. 2048C

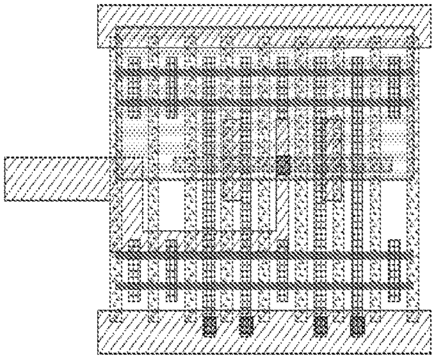
FIG. 2049A
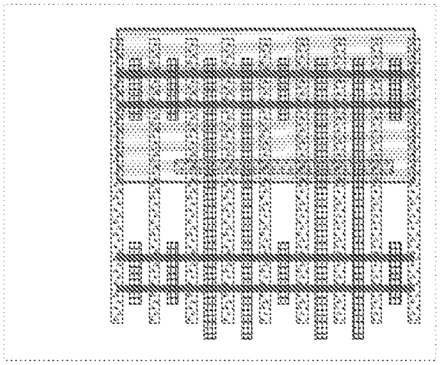
FIG. 2049B
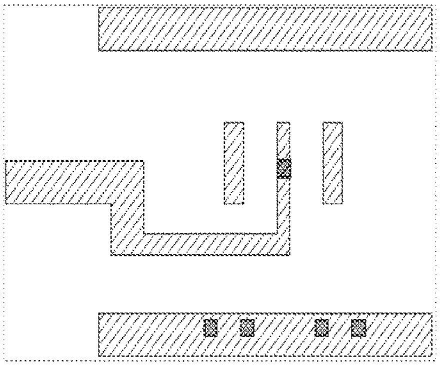
FIG. 2049C

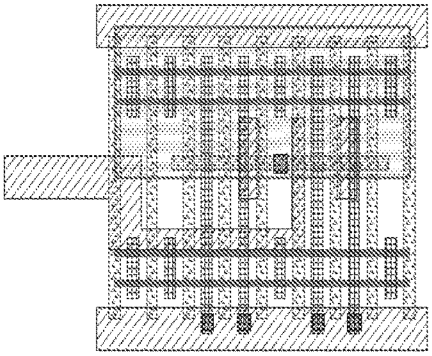
FIG. 2050A
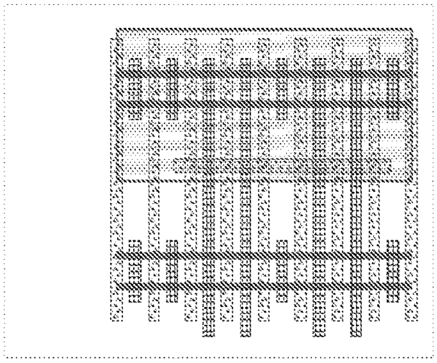
FIG. 2050B
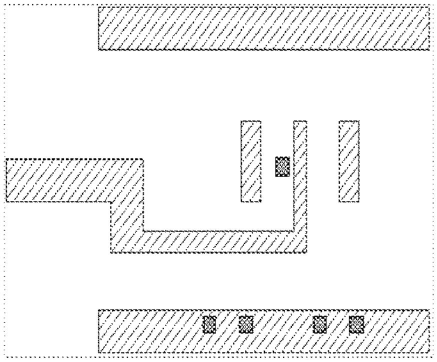
FIG. 2050C

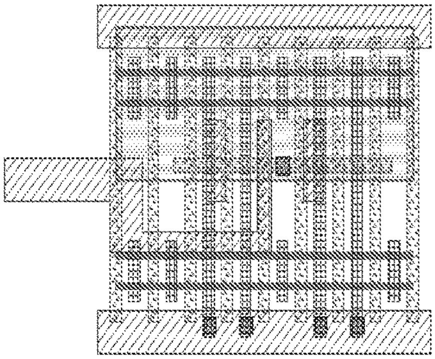
FIG. 2051A
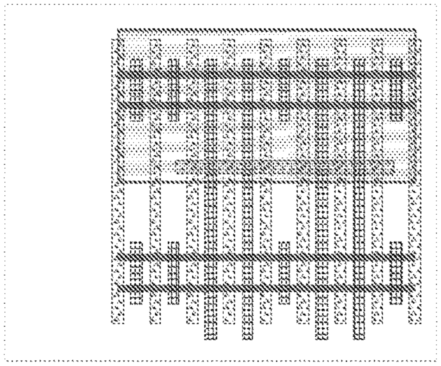
FIG. 2051B
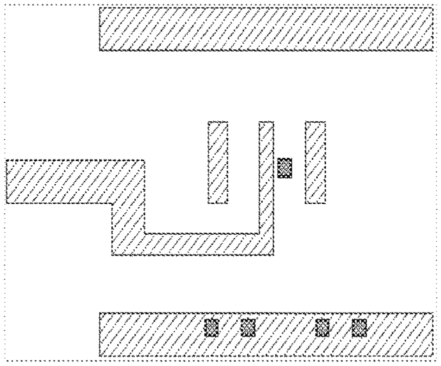
FIG. 2051C
*M* PDF Solutions, Inc.

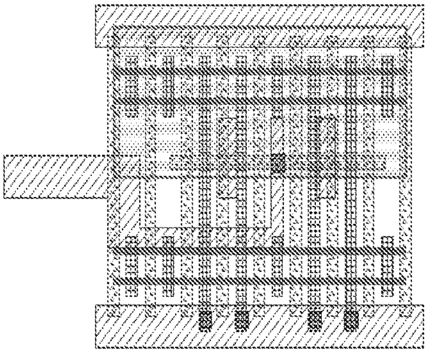
FIG. 2052A
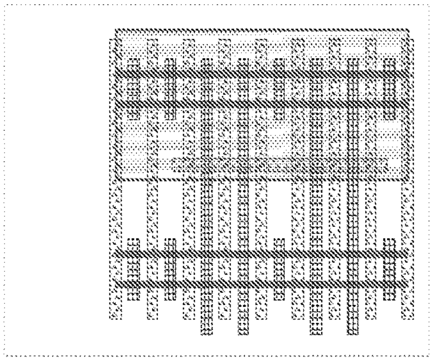
FIG. 2052B
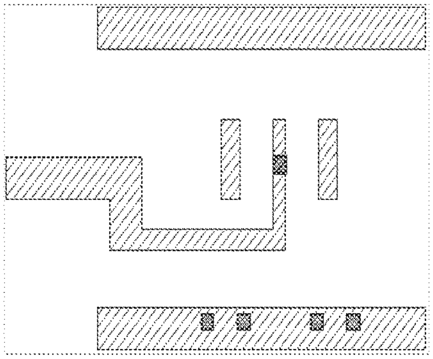
FIG. 2052C

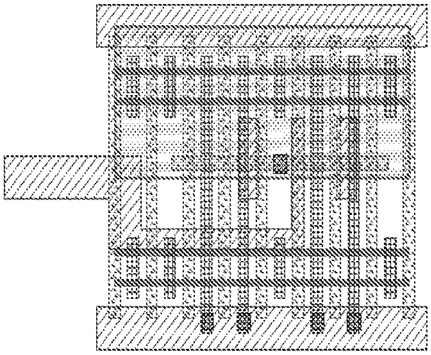
FIG. 2053A
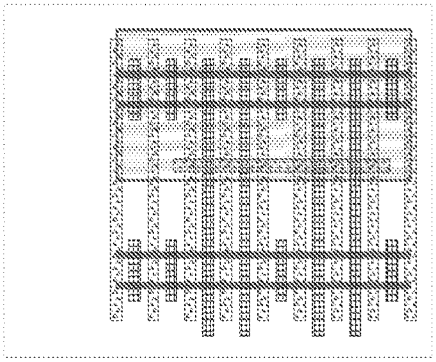
FIG. 2053B
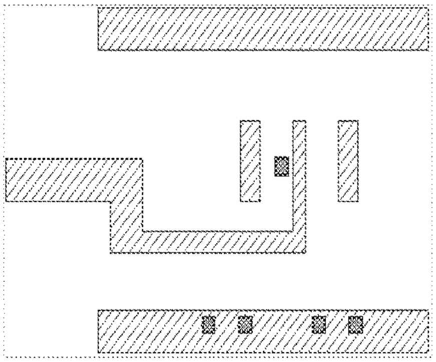
FIG. 2053C

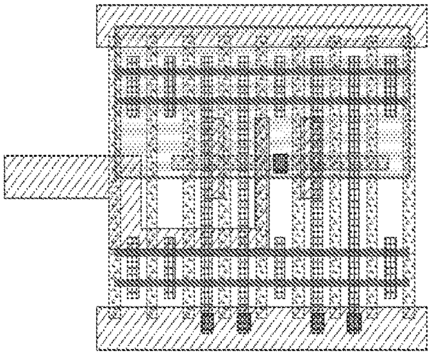
FIG. 2054A
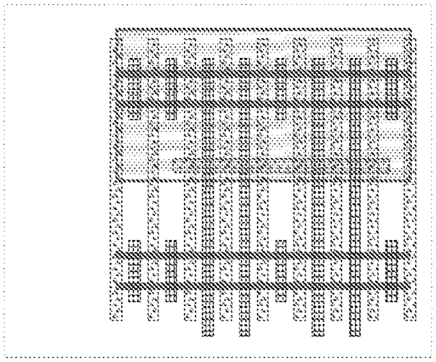
FIG. 2054B
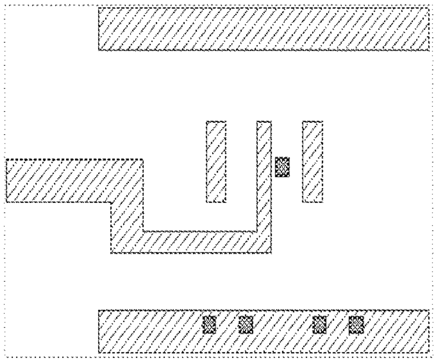
FIG. 2054C
*M* PDF Solutions, Inc.

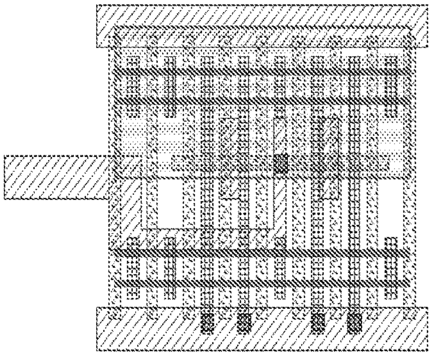
FIG. 2055A
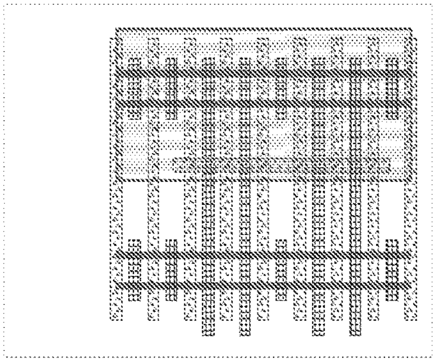
FIG. 2055B
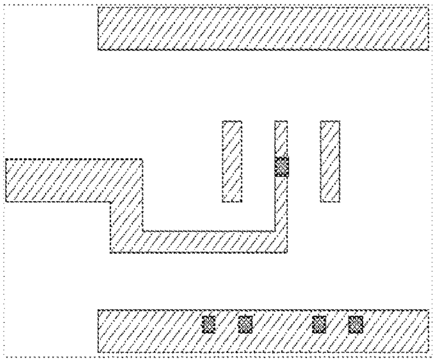
FIG. 2055C
*M* PDF Solutions, Inc.

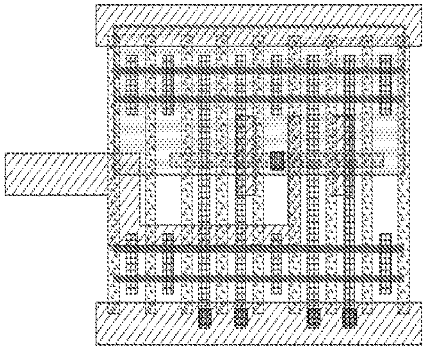
FIG. 2056A
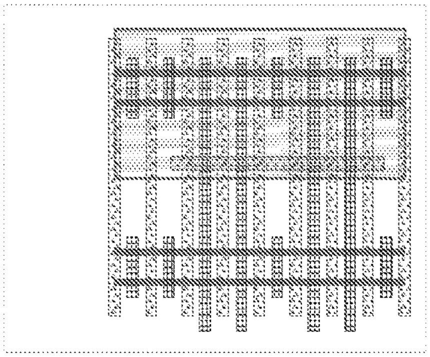
FIG. 2056B
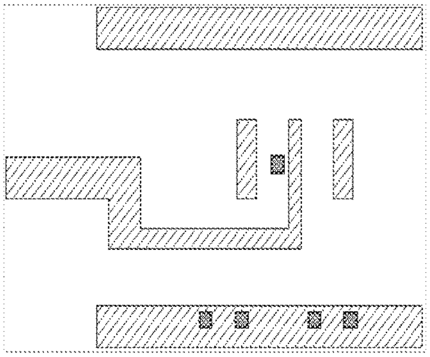
FIG. 2056C

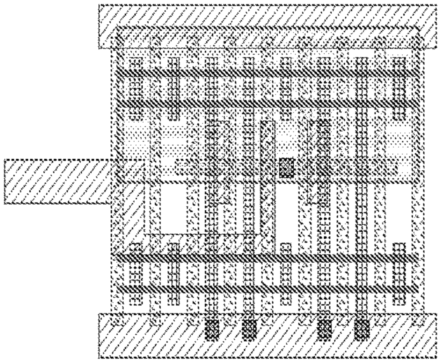
FIG. 2057A
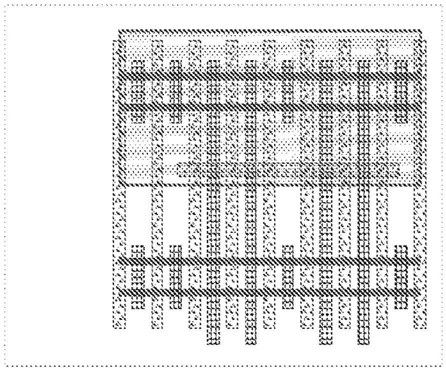
FIG. 2057B
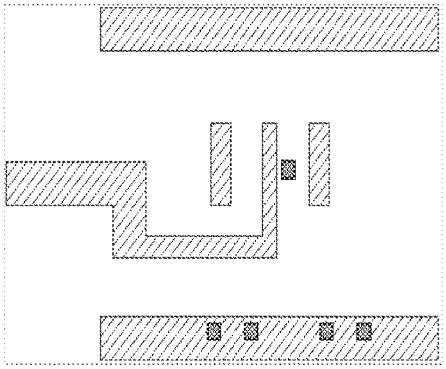
FIG. 2057C

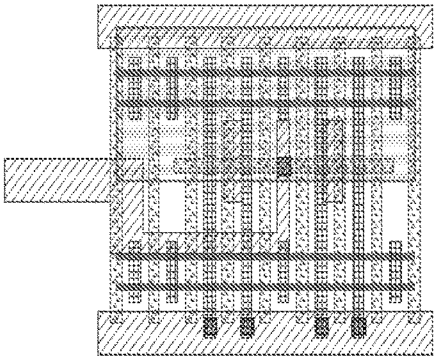
FIG. 2058A
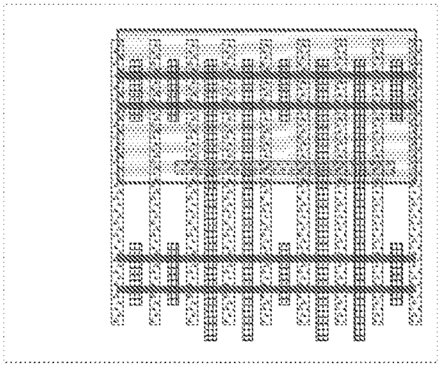
FIG. 2058B
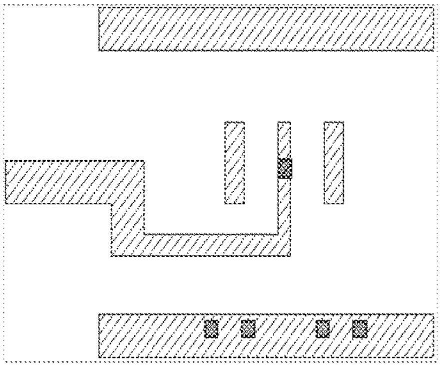
FIG. 2058C
*M* PDF Solutions, Inc.

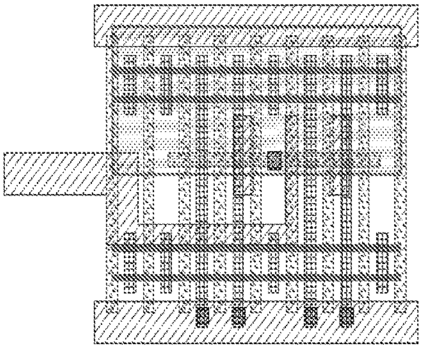
FIG. 2059A
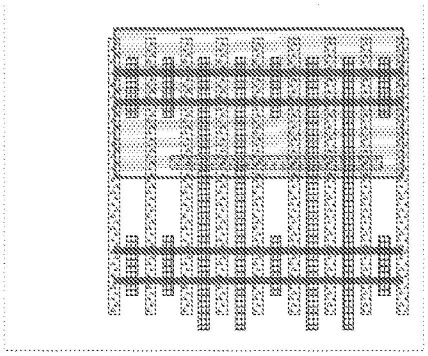
FIG. 2059B
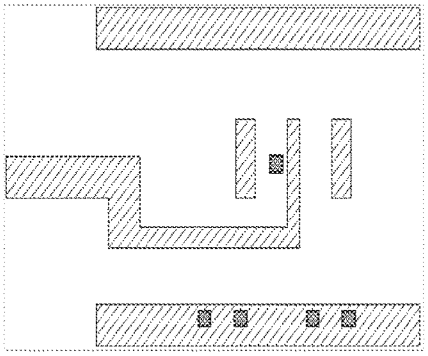
FIG. 2059C
*M* PDF Solutions, Inc.

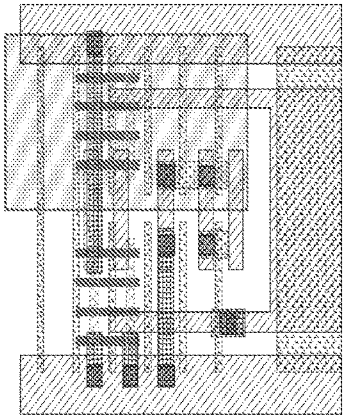
FIG. 2060A
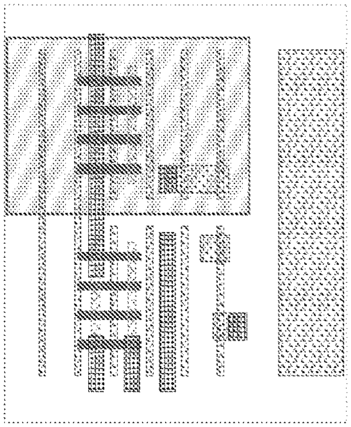
FIG. 2060B
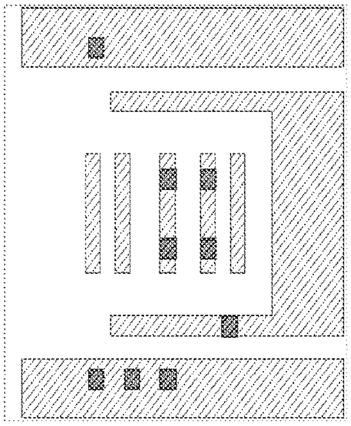
FIG. 2060C

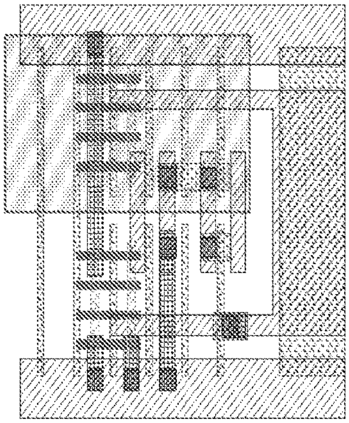
FIG. 2061A
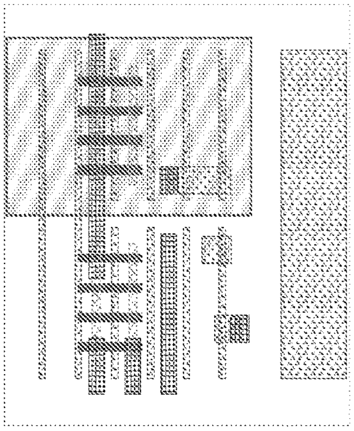
FIG. 2061B
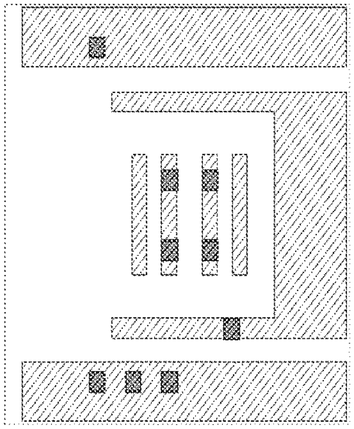
FIG. 2061C

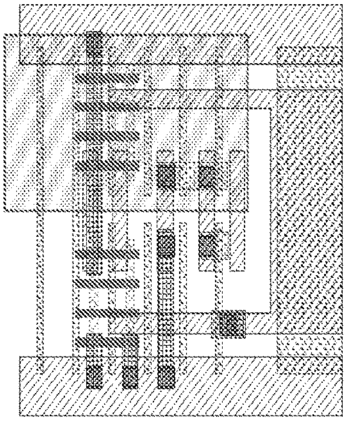
FIG. 2062A
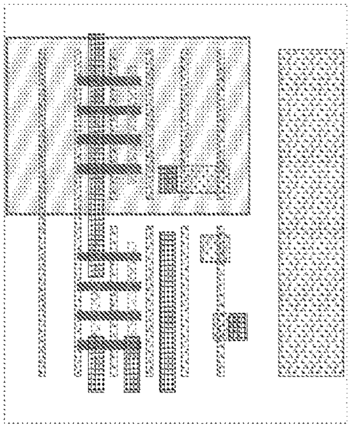
FIG. 2062B
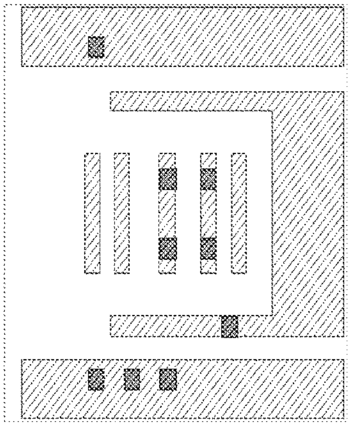
FIG. 2062C

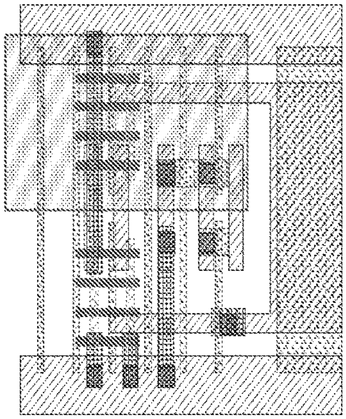
FIG. 2063A
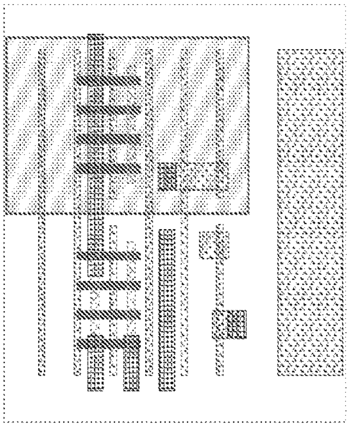
FIG. 2063B
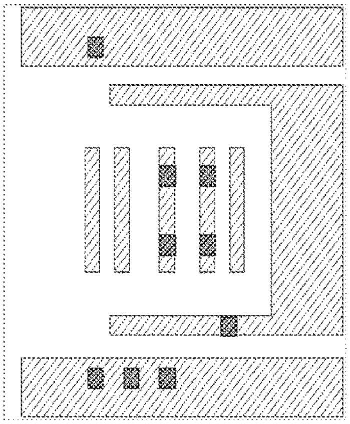
FIG. 2063C

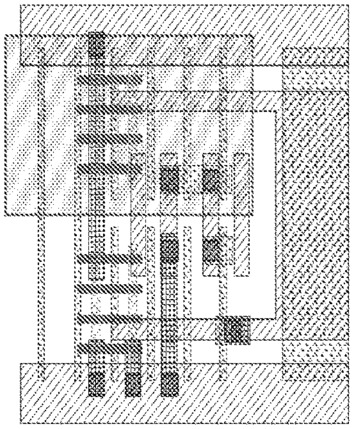
FIG. 2064A
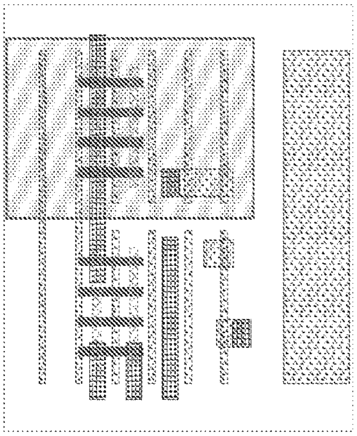
FIG. 2064B
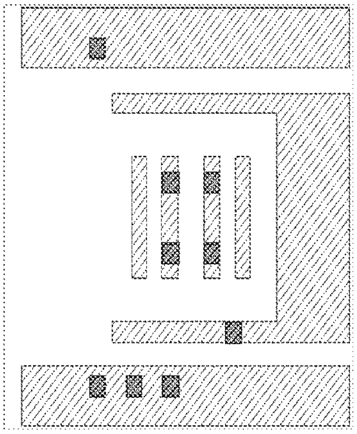
FIG. 2064C

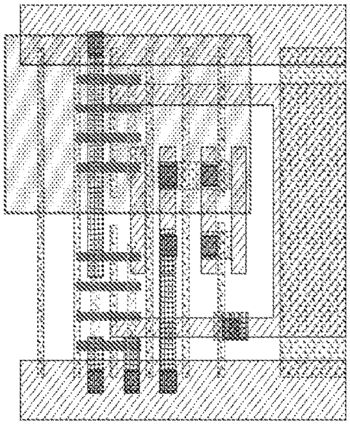
FIG. 2065A
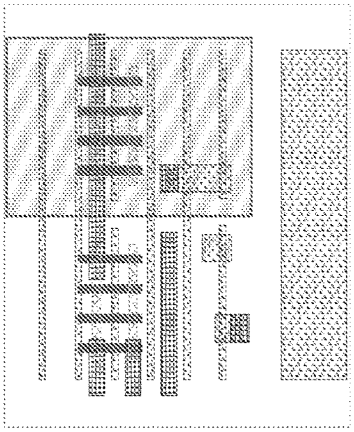
FIG. 2065B
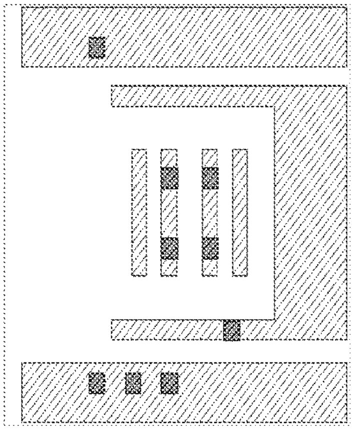
FIG. 2065C

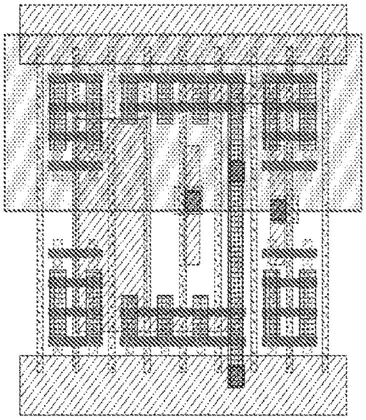
FIG. 2066A
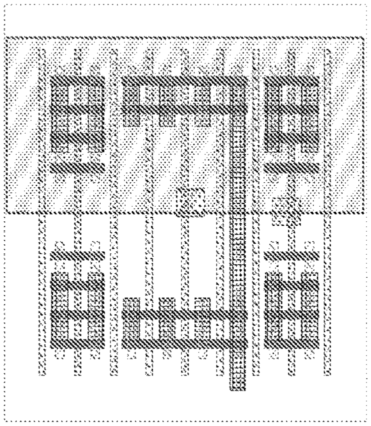
FIG. 2066B
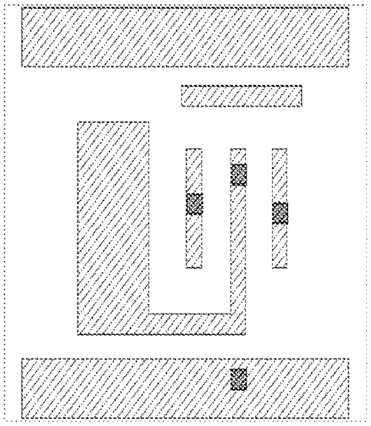
FIG. 2066C

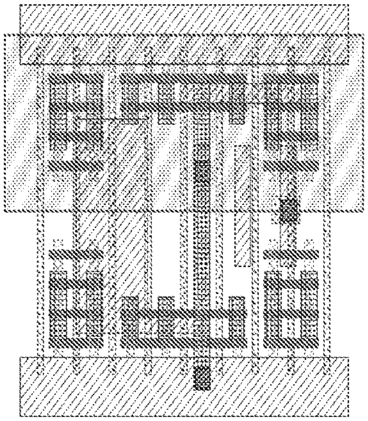
FIG. 2067A
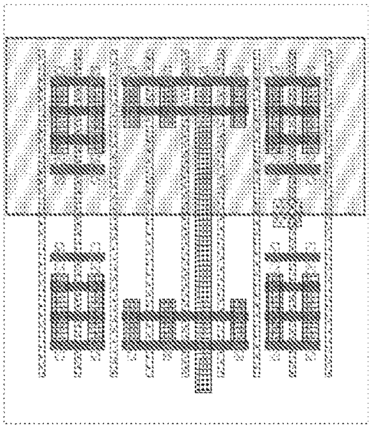
FIG. 2067B
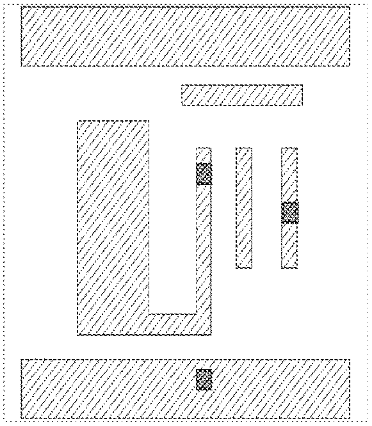
FIG. 2067C

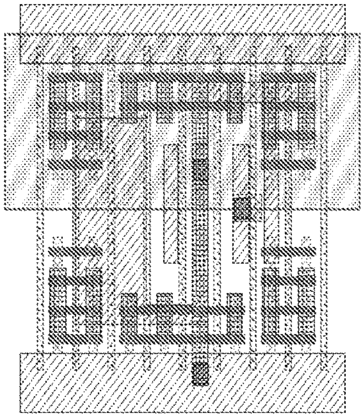
FIG. 2068A
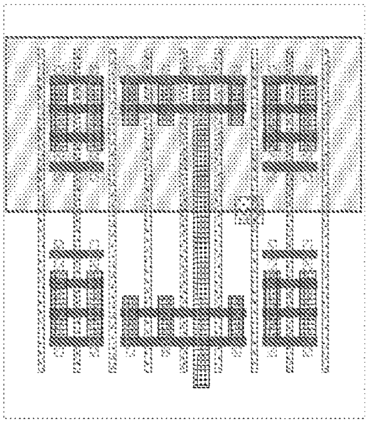
FIG. 2068B
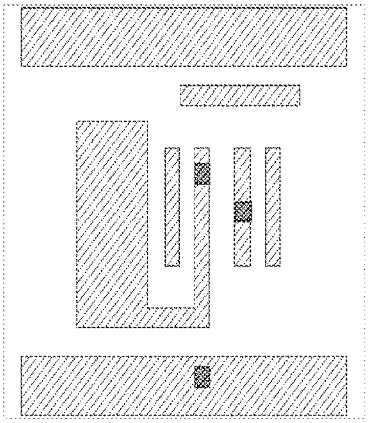
FIG. 2068C

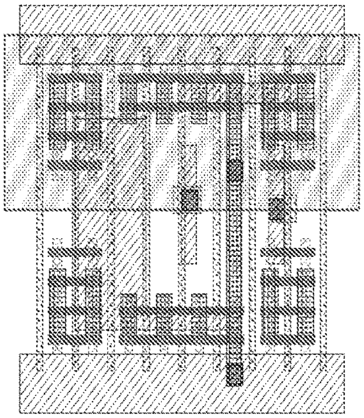
FIG. 2069A
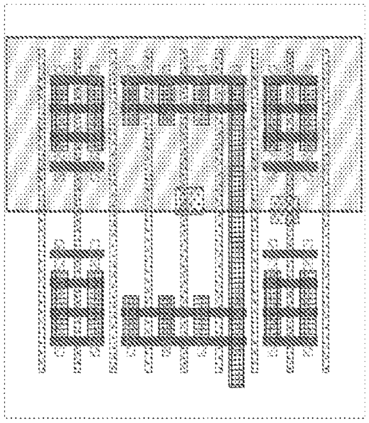
FIG. 2069B
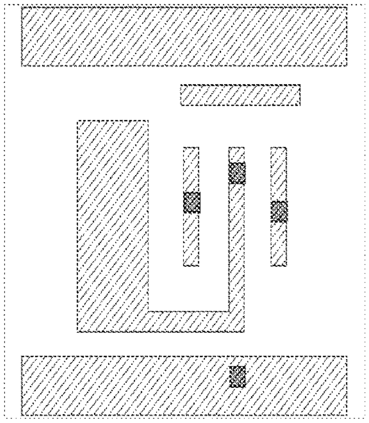
FIG. 2069C

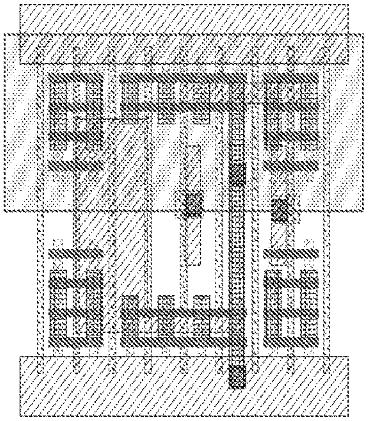
FIG. 2070A
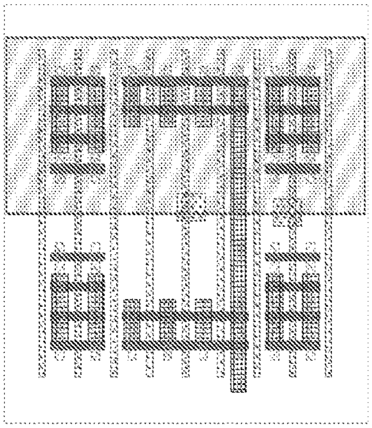
FIG. 2070B
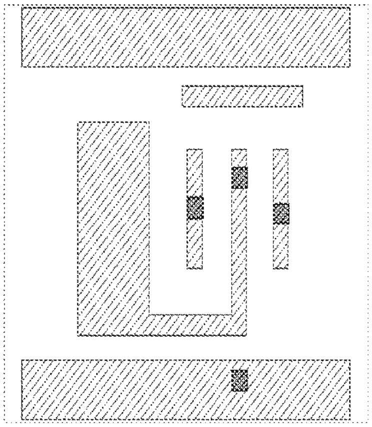
FIG. 2070C

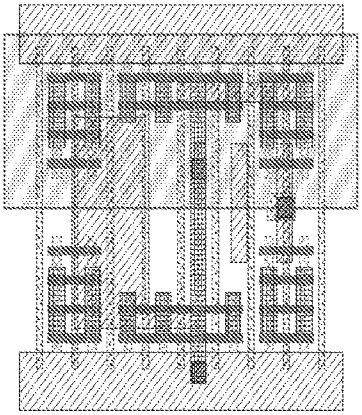
FIG. 2071A
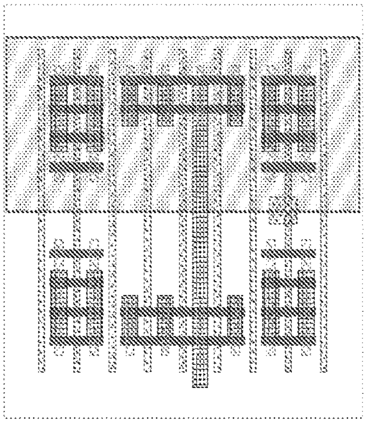
FIG. 2071B
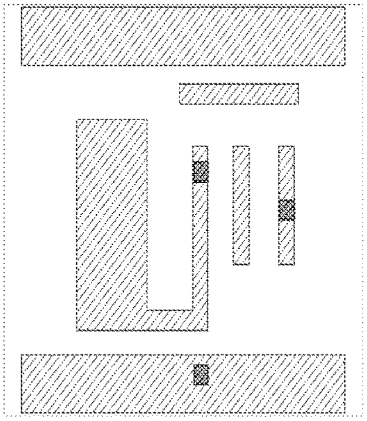
FIG. 2071C

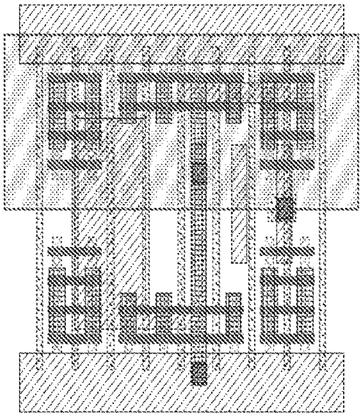
FIG. 2072A
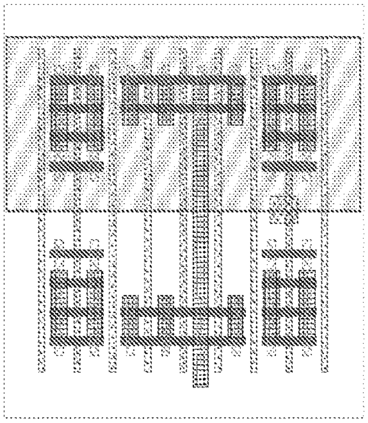
FIG. 2072B
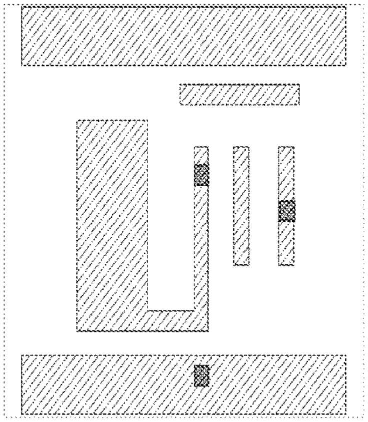
FIG. 2072C

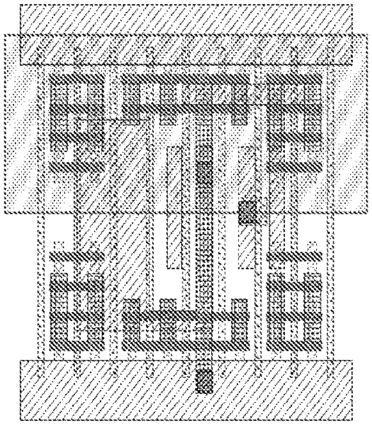
FIG. 2073A
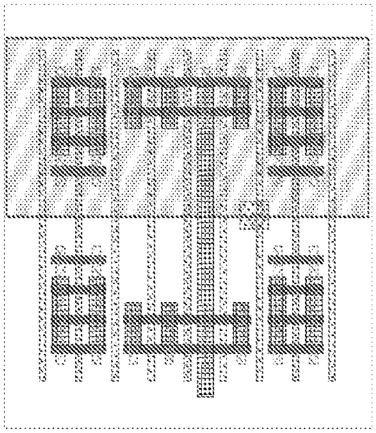
FIG. 2073B
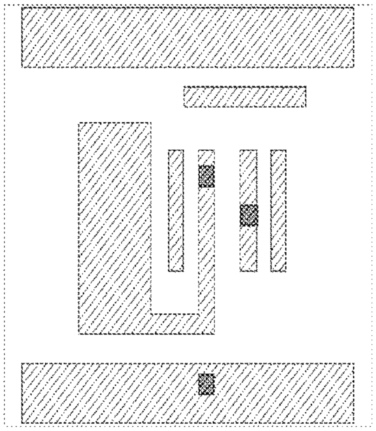
FIG. 2073C

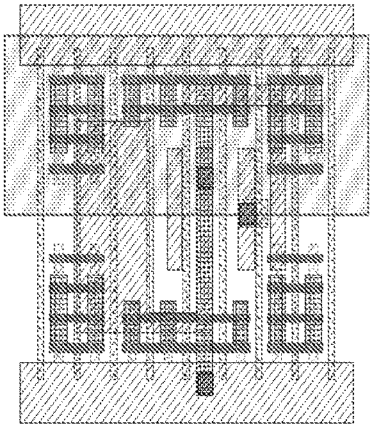
FIG. 2074A
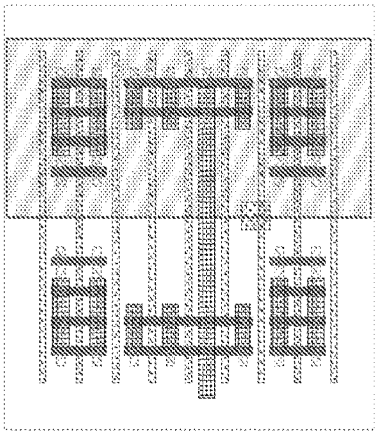
FIG. 2074B
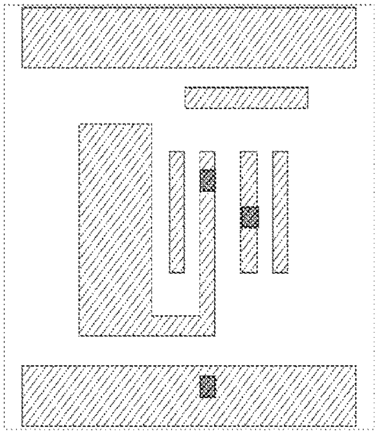
FIG. 2074C

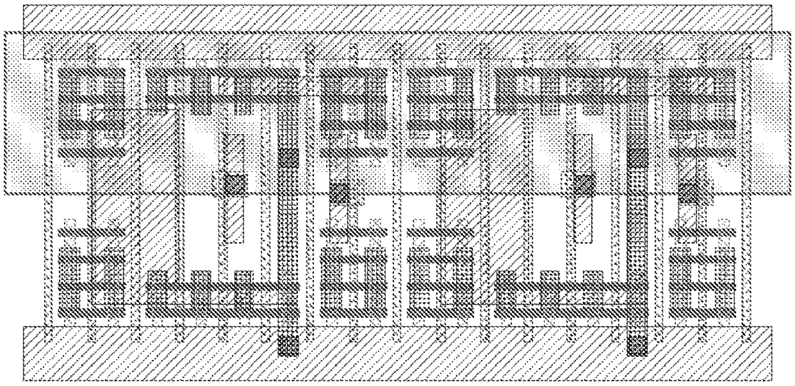
FIG. 2075A
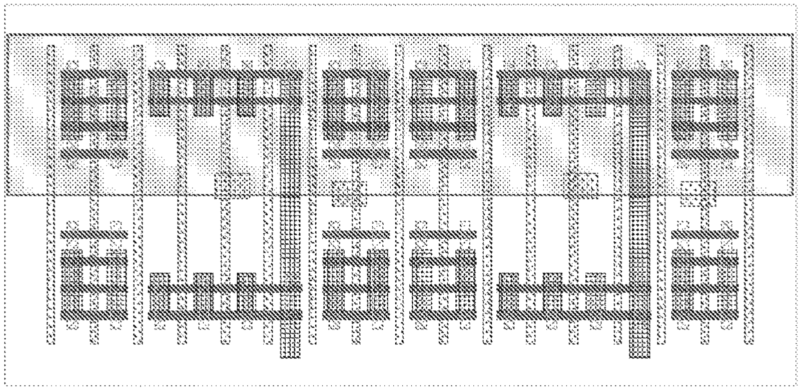
FIG. 2075B
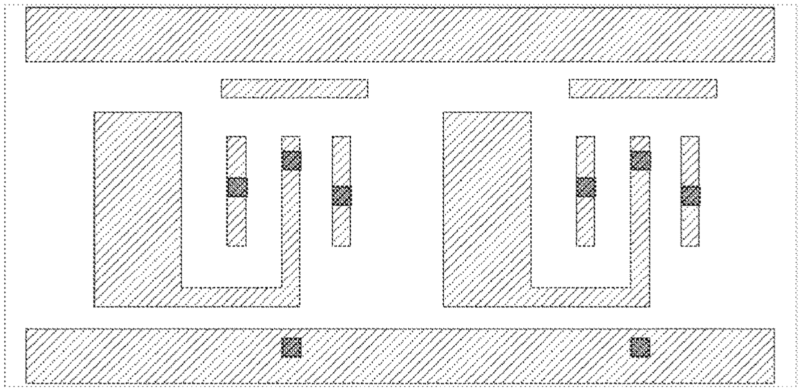
FIG. 2075C

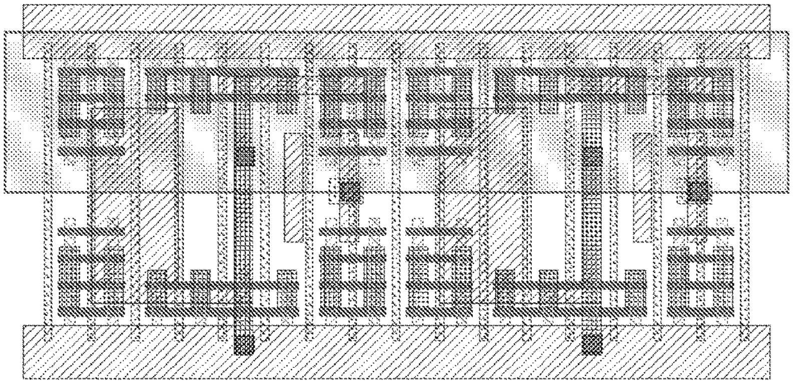
FIG. 2076A
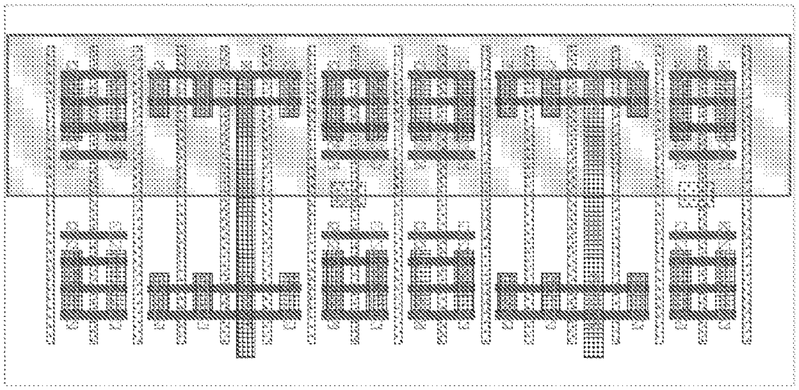
FIG. 2076B
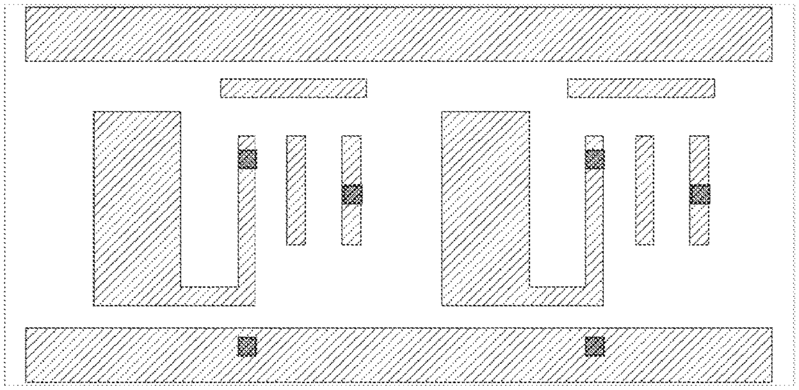
FIG. 2076C
*M* PDF Solutions, Inc.

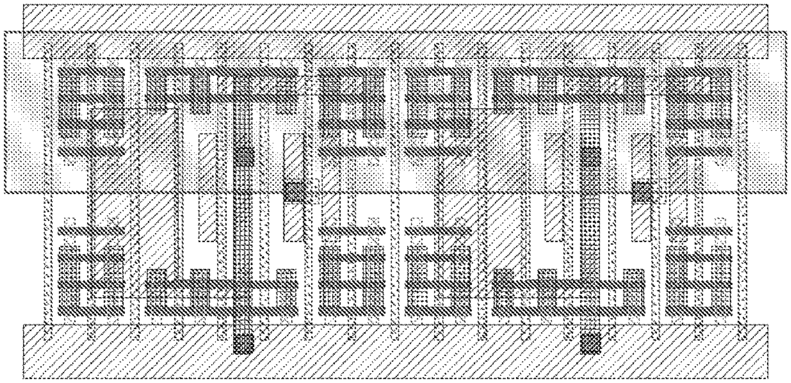
FIG. 2077A
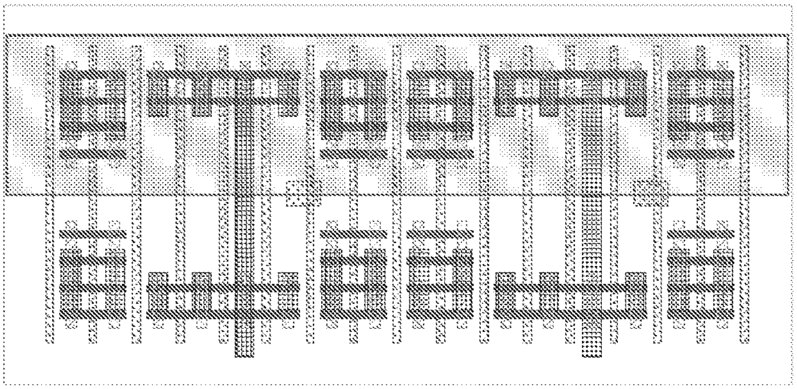
FIG. 2077B
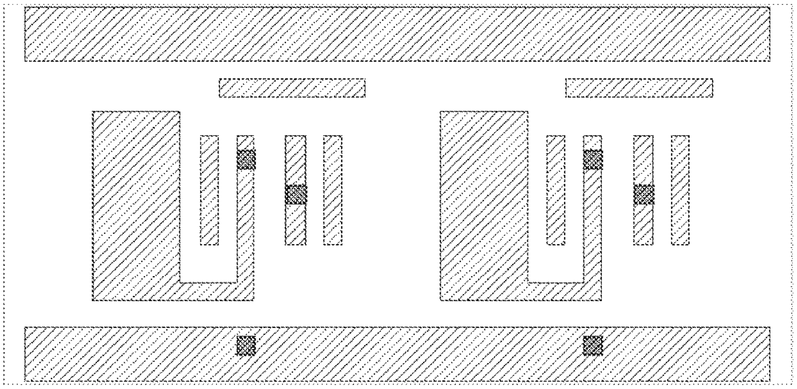
FIG. 2077C

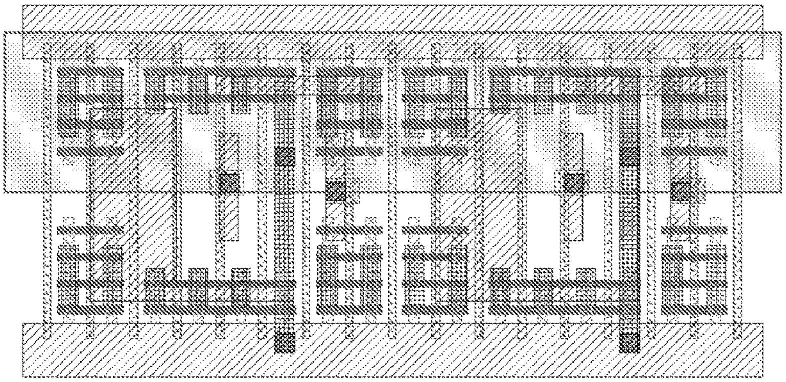
FIG. 2078A
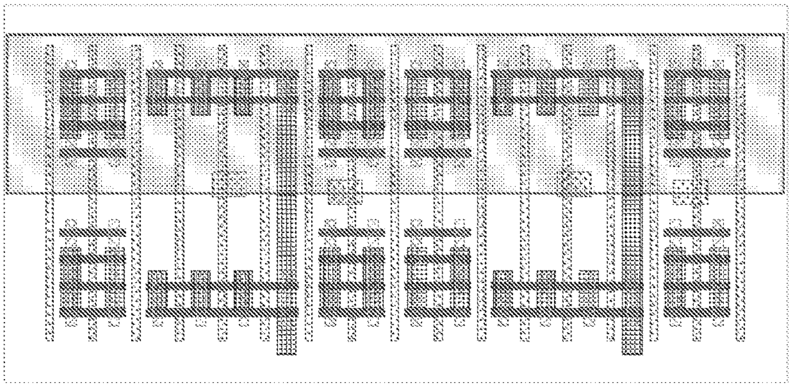
FIG. 2078B
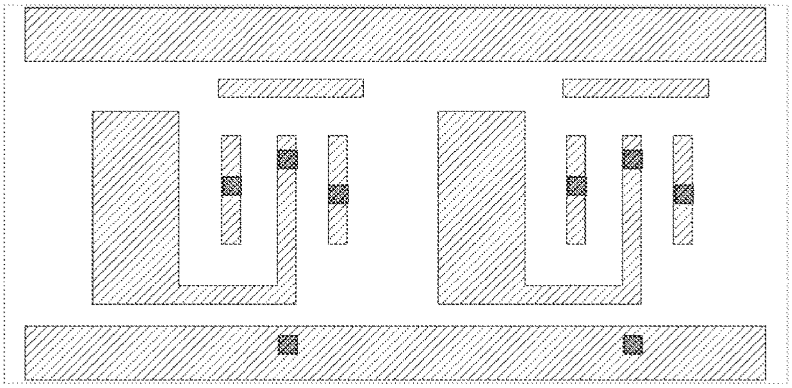
FIG. 2078C
*M* PDF Solutions, Inc.

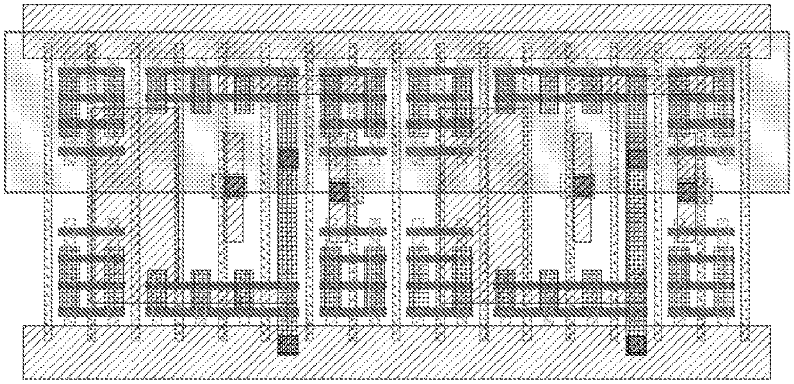
FIG. 2079A
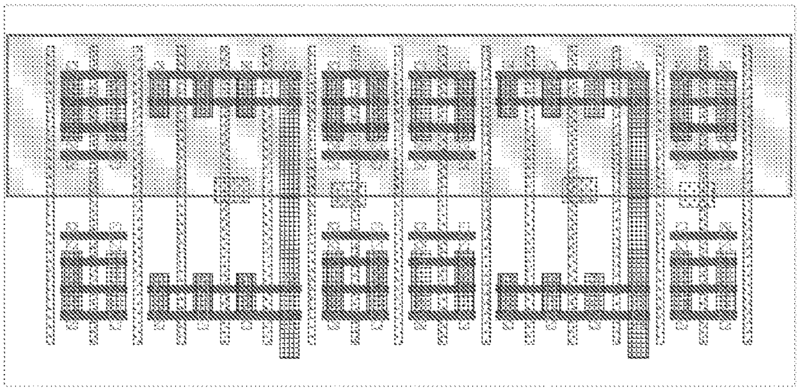
FIG. 2079B
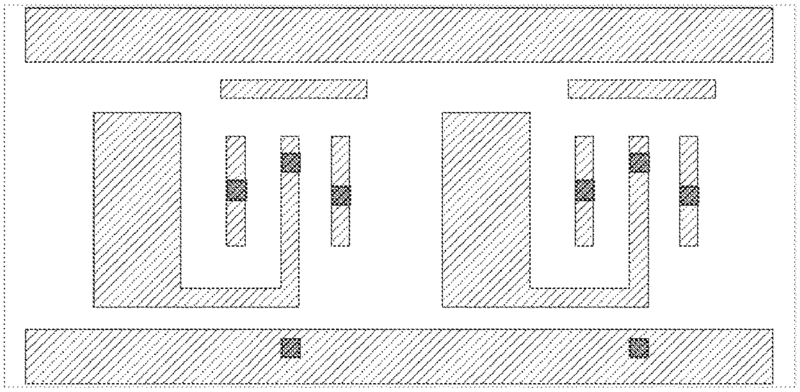
FIG. 2079C

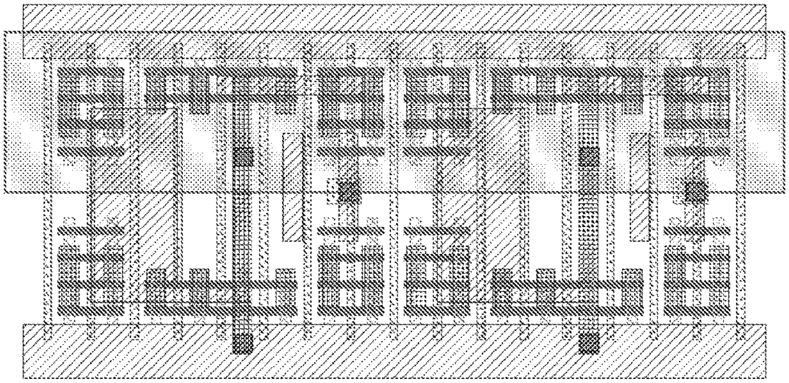
FIG. 2080A
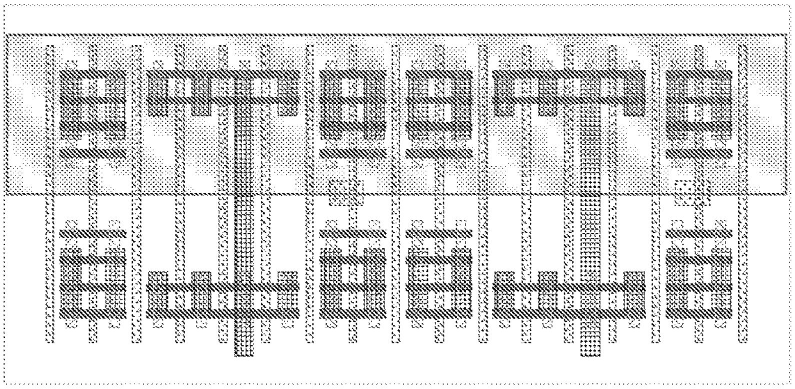
FIG. 2080B
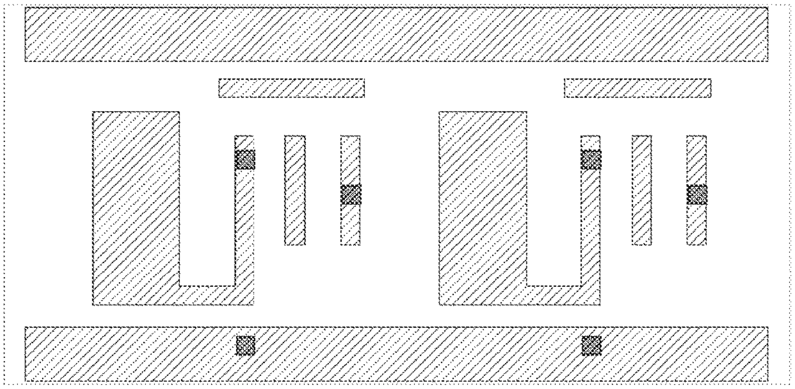
FIG. 2080C

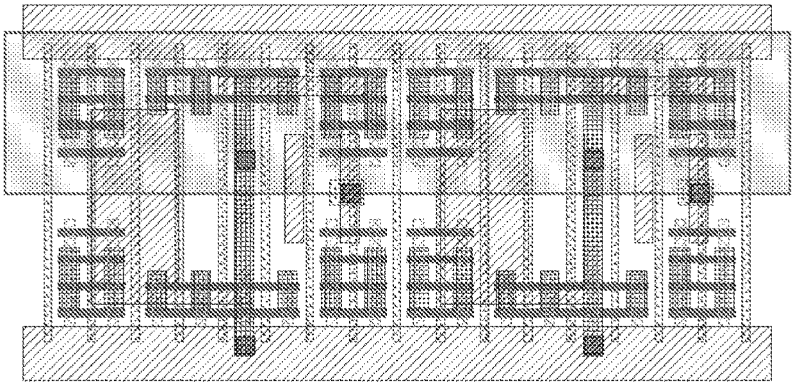
FIG. 2081A
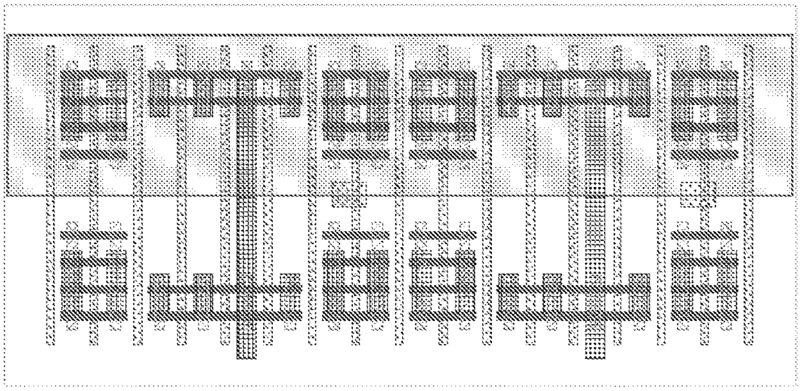
FIG. 2081B
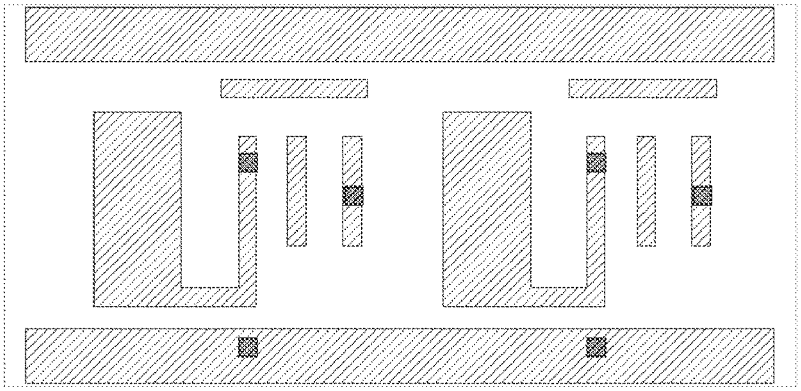
FIG. 2081C
*M* PDF Solutions, Inc.

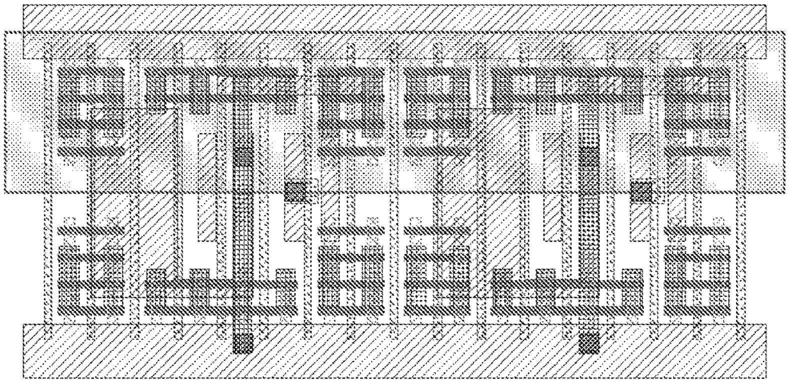
FIG. 2082A
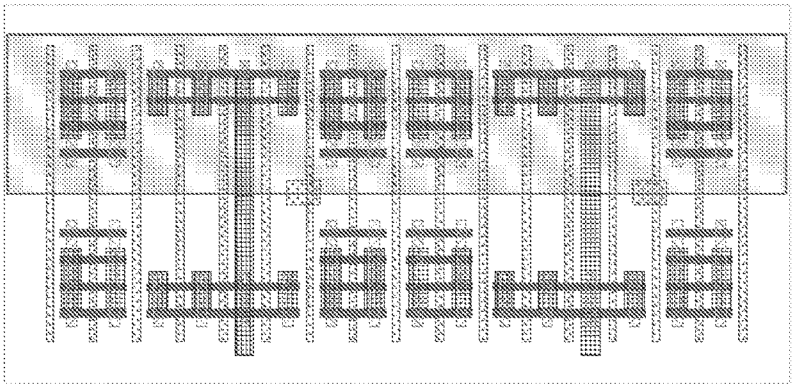
FIG. 2082B
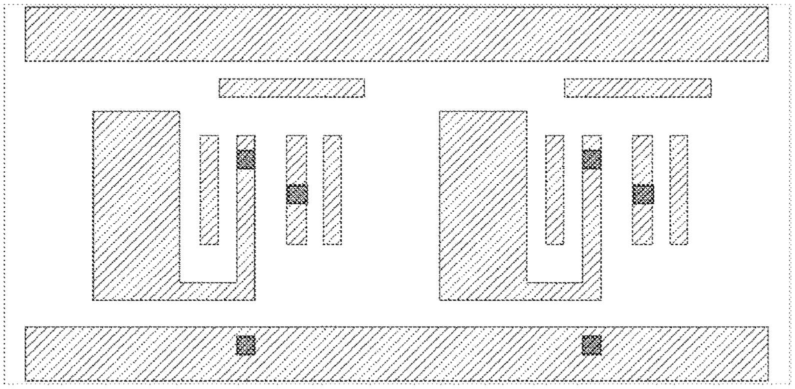
FIG. 2082C
*M* PDF Solutions, Inc.

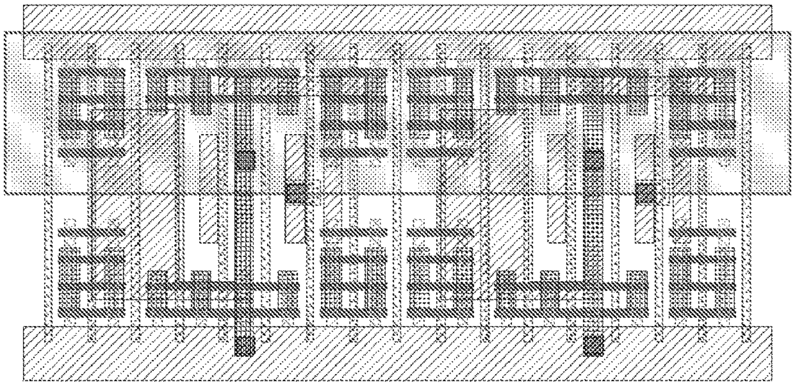
FIG. 2083A
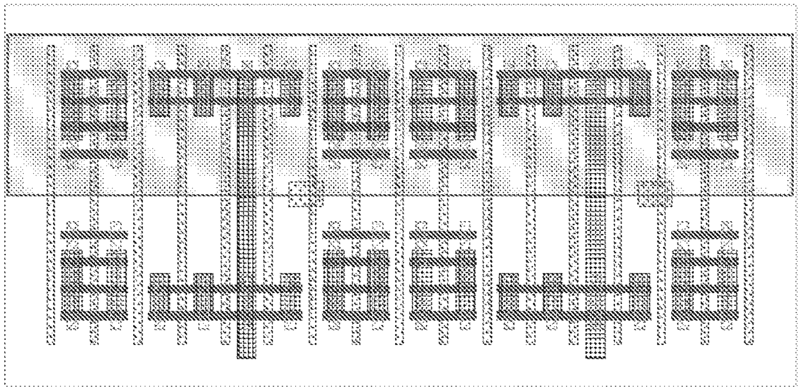
FIG. 2083B
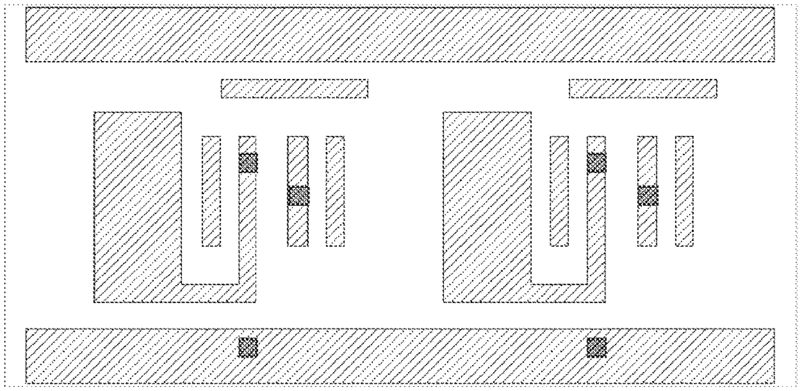
FIG. 2083C
*M* PDF Solutions, Inc.

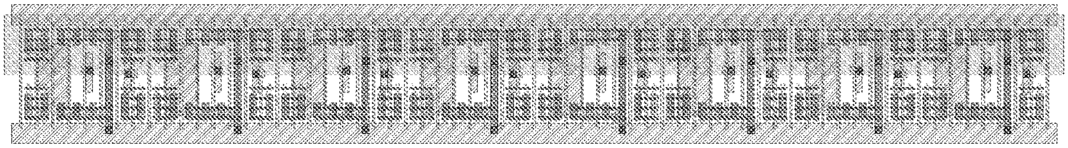
FIG. 2084A
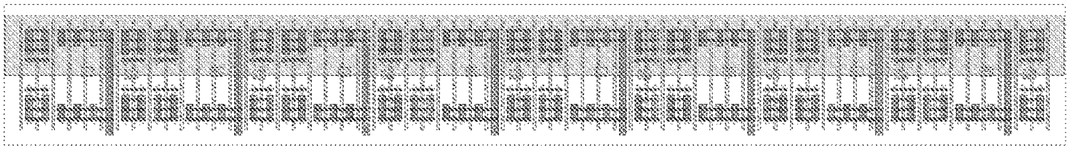
FIG. 2084B
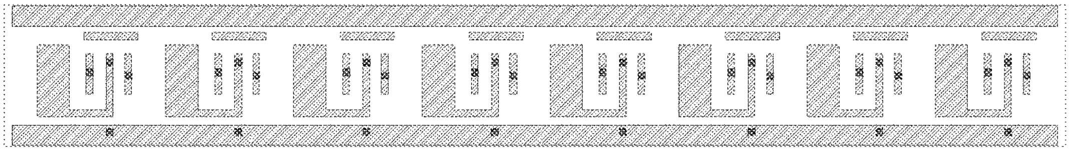
FIG. 2084C

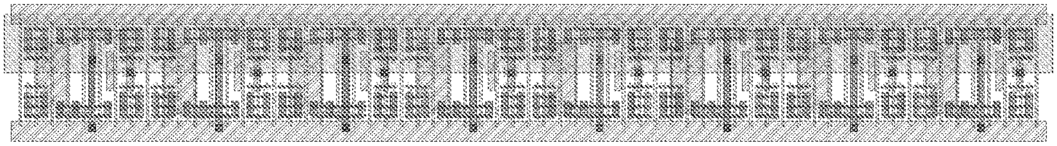
FIG. 2085A
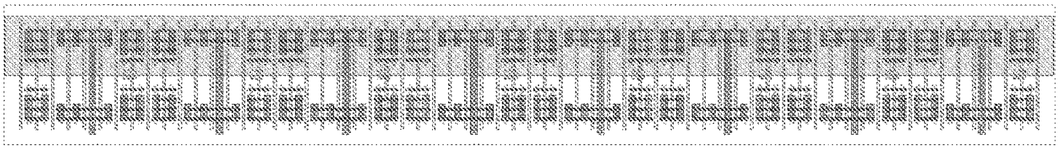
FIG. 2085B
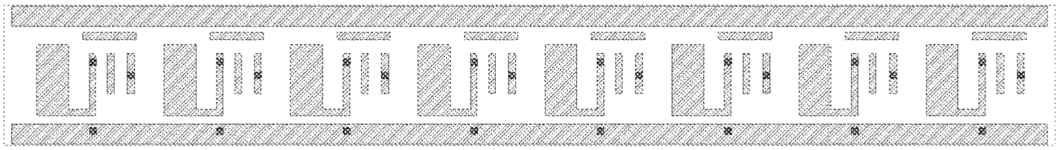
FIG. 2085C

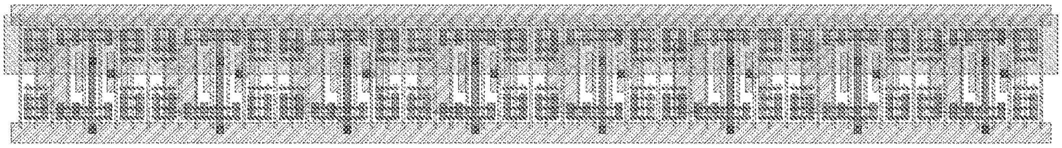
FIG. 2086A
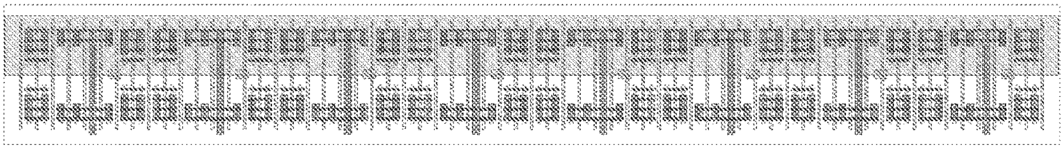
FIG. 2086B
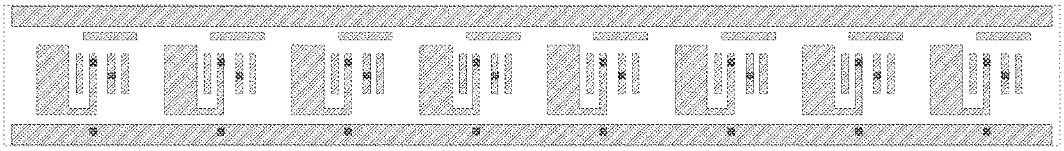
FIG. 2086C

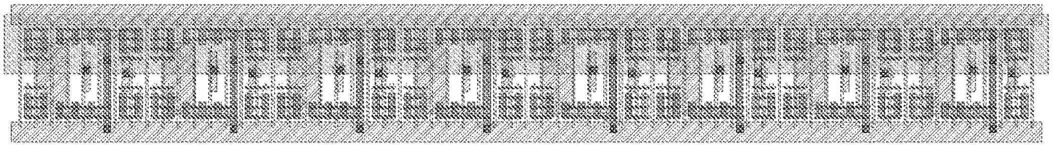
FIG. 2087A
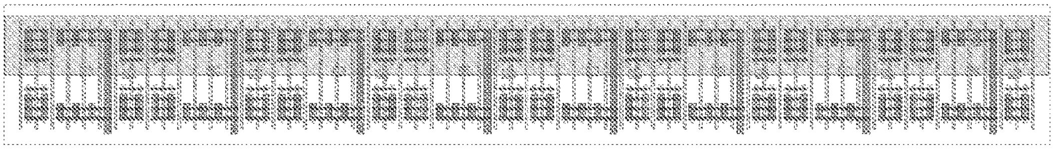
FIG. 2087B
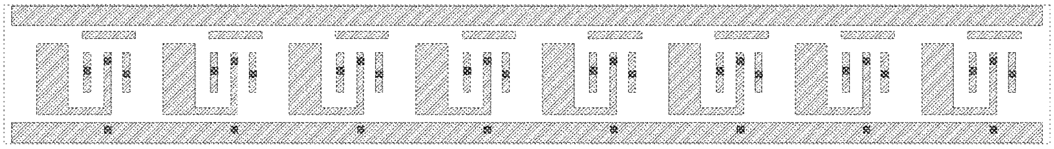
FIG. 2087C

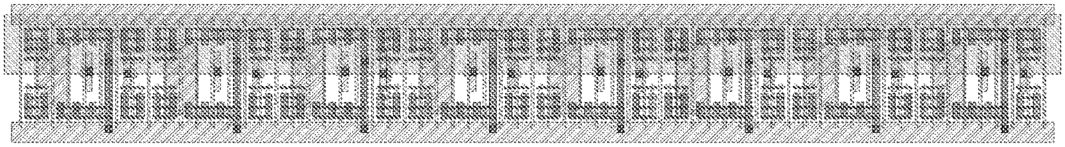
FIG. 2088A
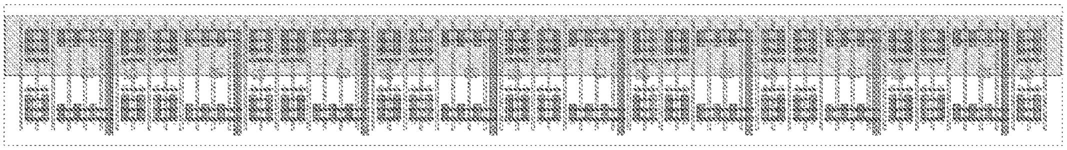
FIG. 2088B
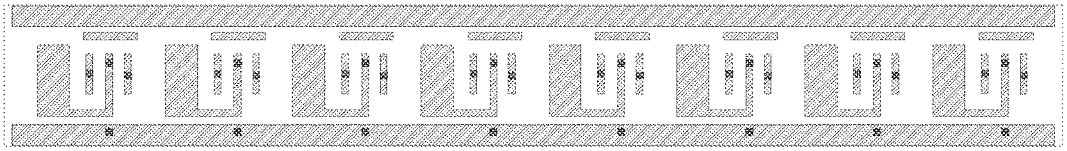
FIG. 2088C
*M* PDF Solutions, Inc.

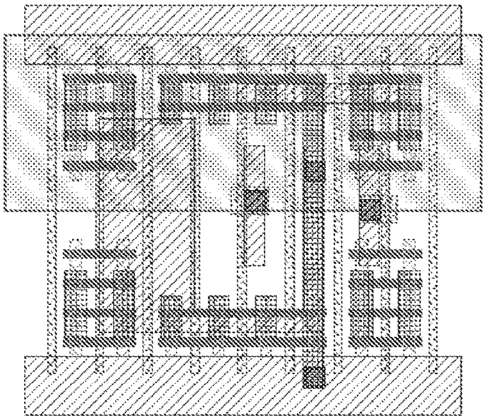
FIG. 2089A
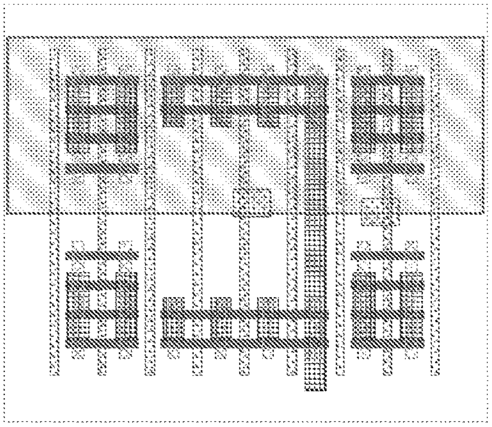
FIG. 2089B
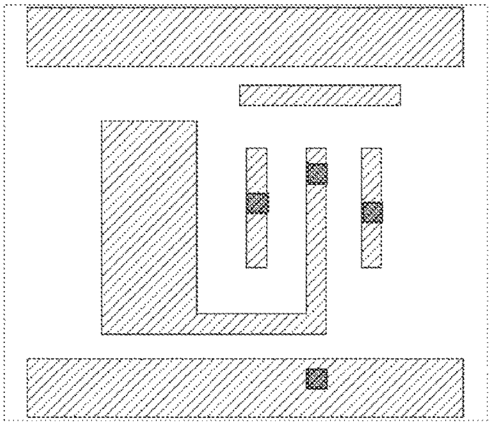
FIG. 2089C

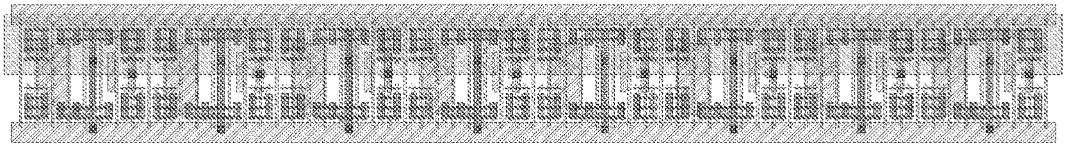
FIG. 2090A
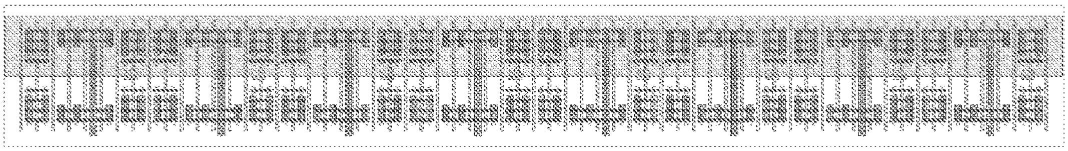
FIG. 2090B
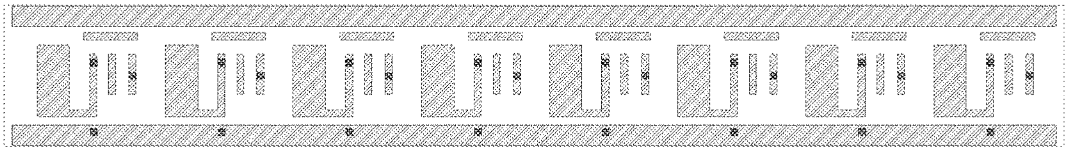
FIG. 2090C

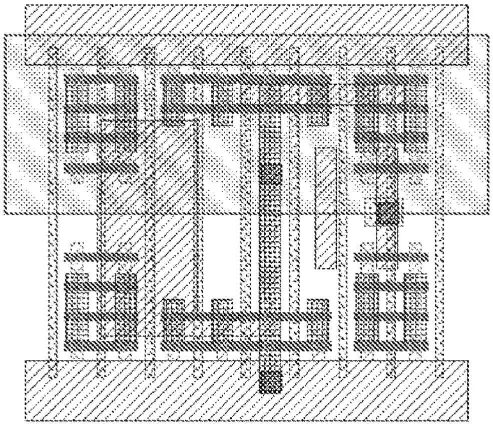
FIG. 2091A
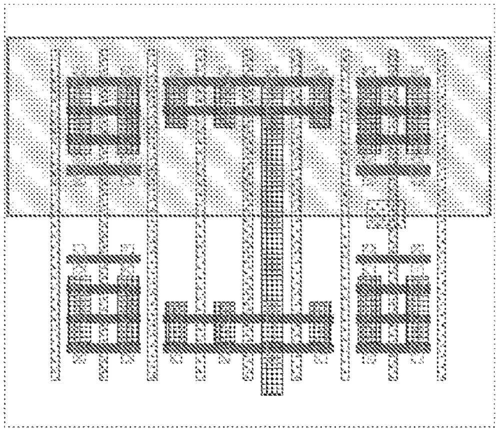
FIG. 2091B
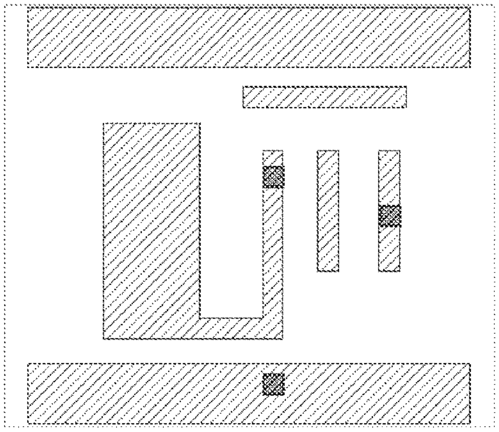
FIG. 2091C
*M* PDF Solutions, Inc.

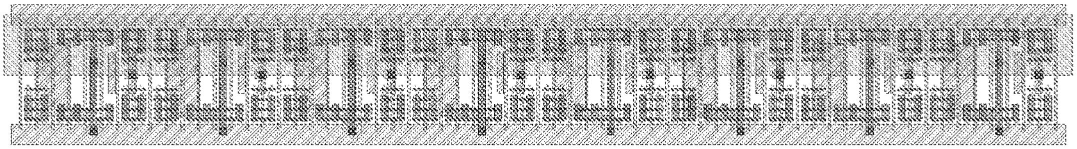
FIG. 2092A
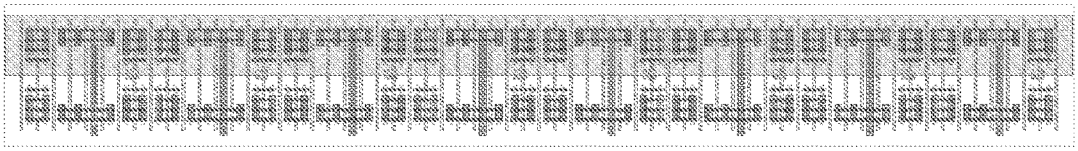
FIG. 2092B
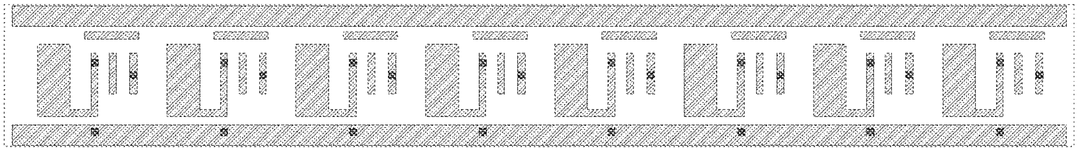
FIG. 2092C

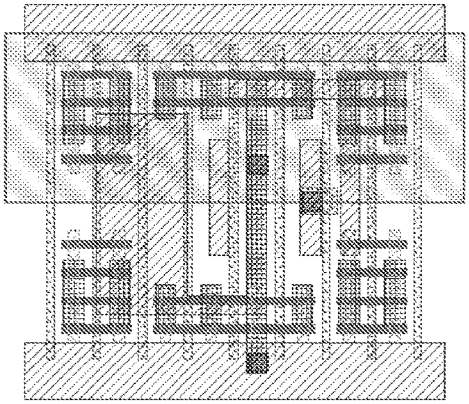
FIG. 2093A
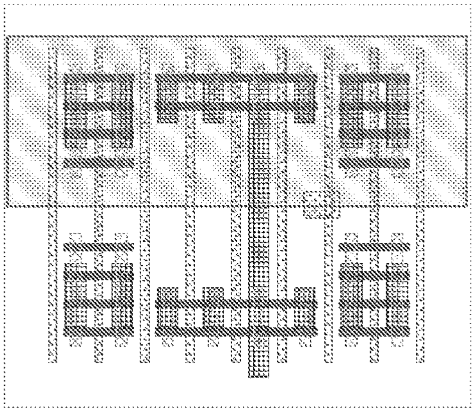
FIG. 2093B
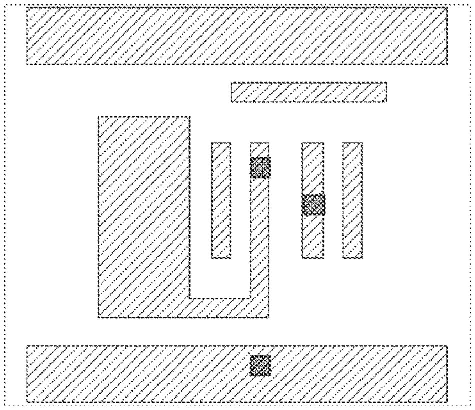
FIG. 2093C
*M* PDF Solutions, Inc.

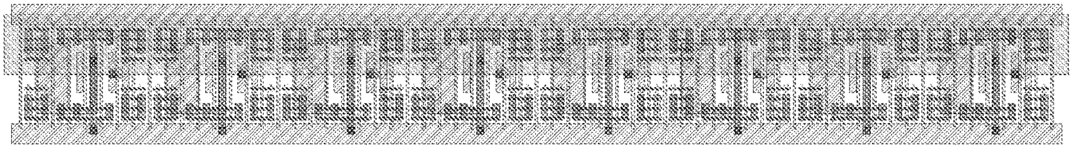
FIG. 2094A
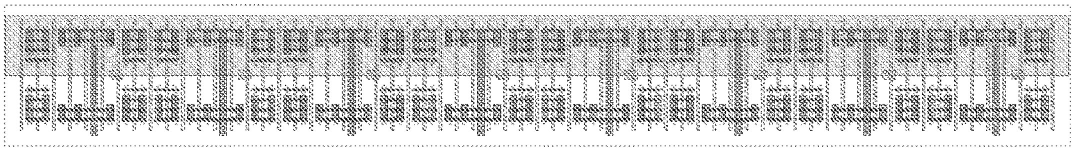
FIG. 2094B
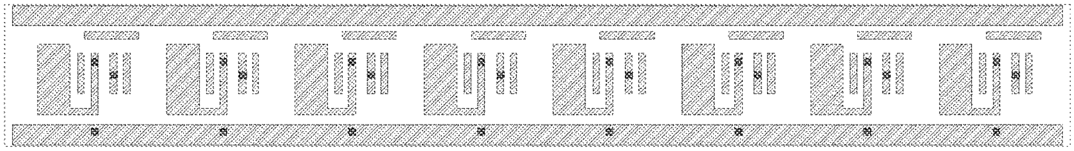
FIG. 2094C

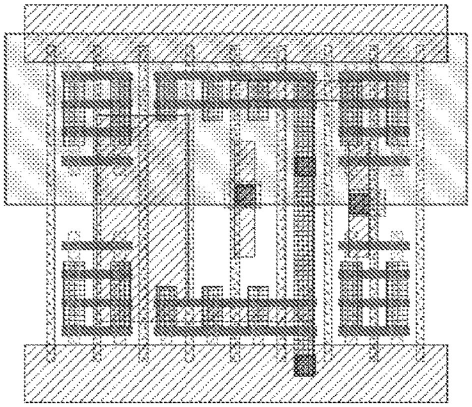
FIG. 2095A
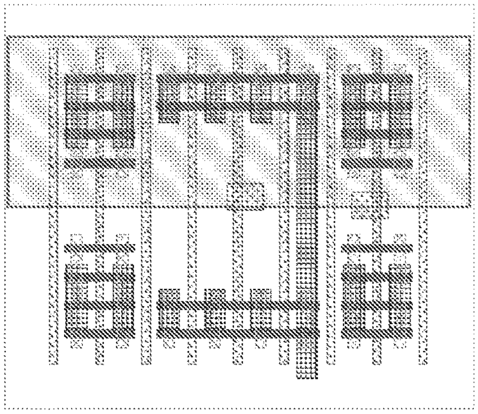
FIG. 2095B
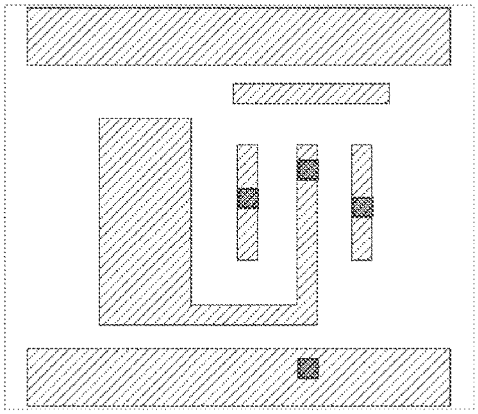
FIG. 2095C

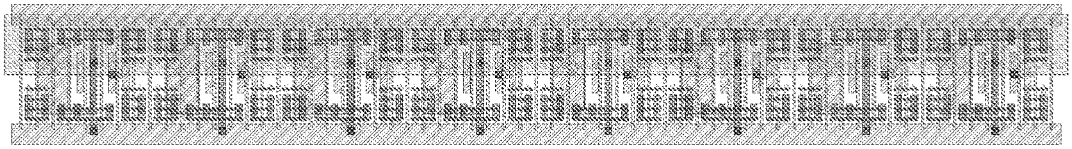
FIG. 2096A
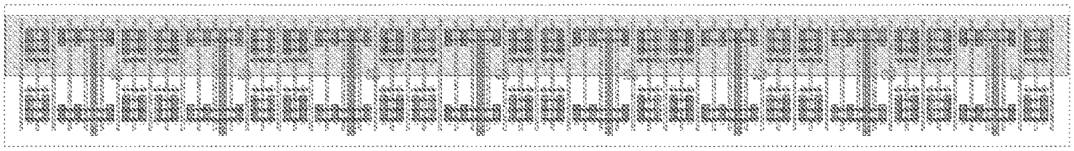
FIG. 2096B
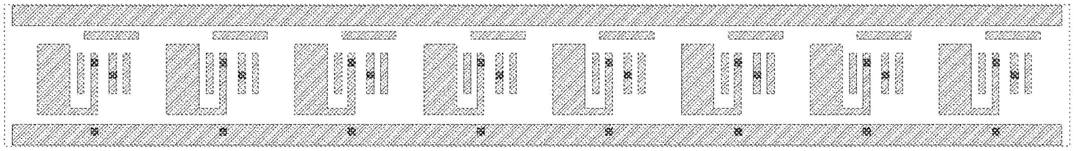
FIG. 2096C

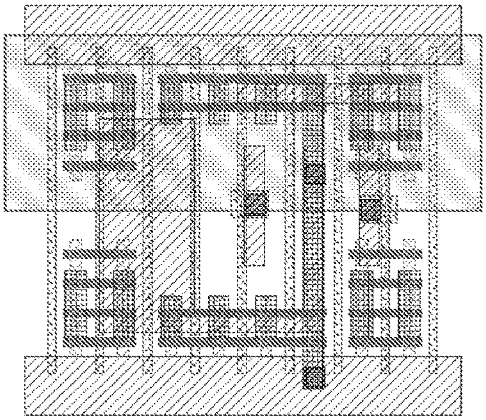
FIG. 2097A
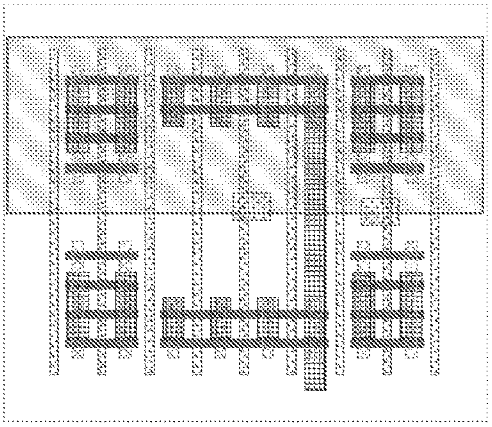
FIG. 2097B
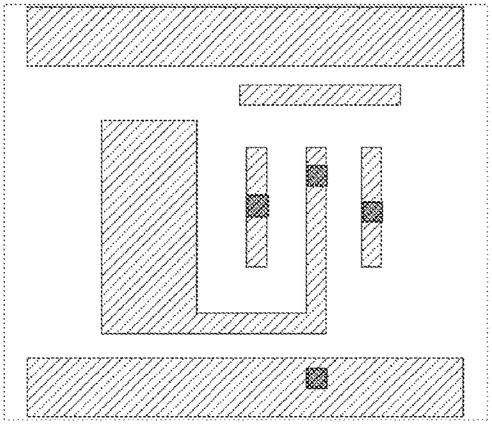
FIG. 2097C

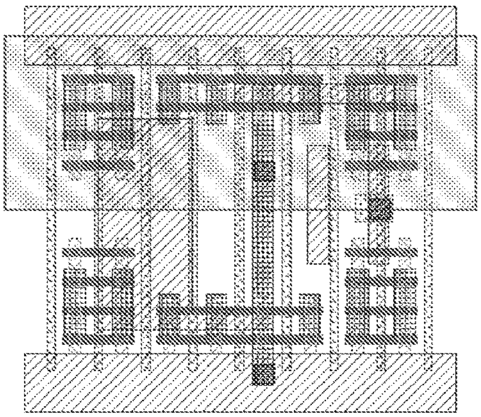
FIG. 2098A
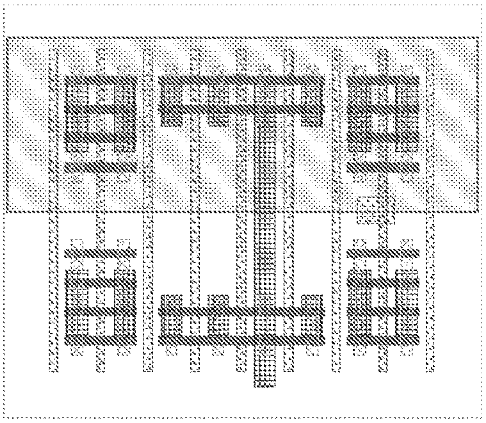
FIG. 2098B
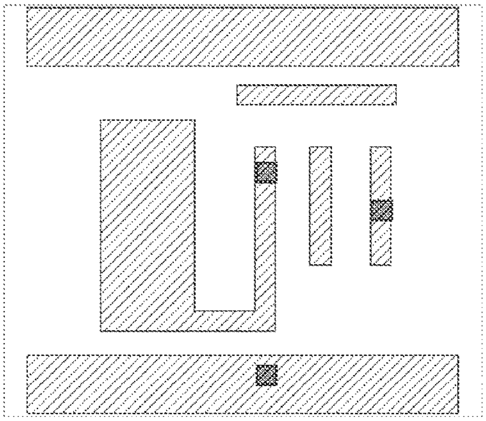
FIG. 2098C

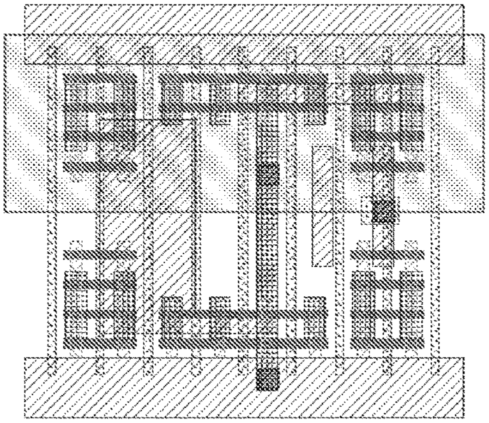
FIG. 2099A
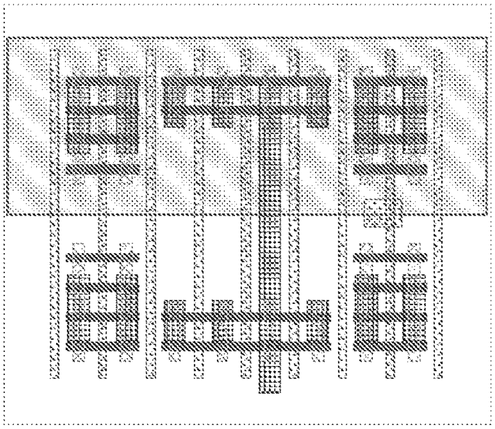
FIG. 2099B
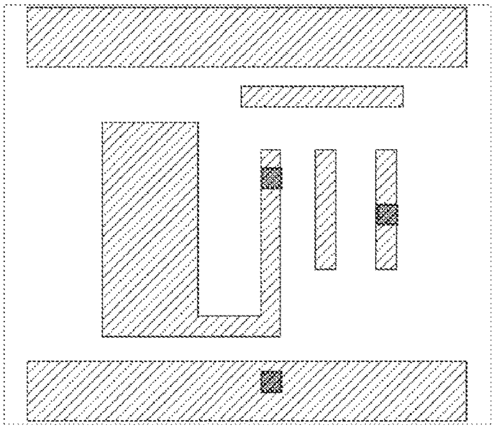
FIG. 2099C

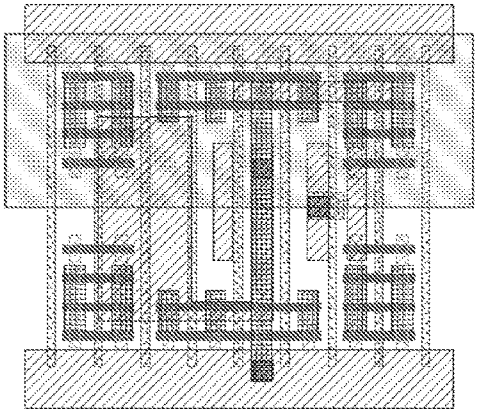
FIG. 2100A
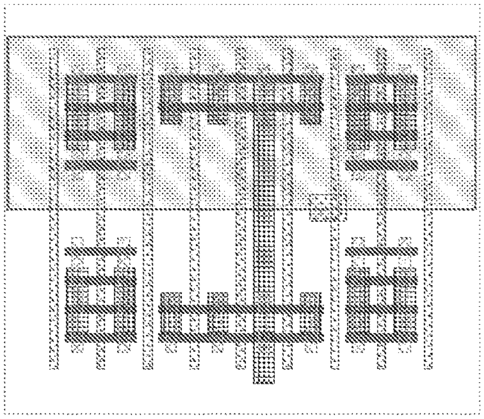
FIG. 2100B
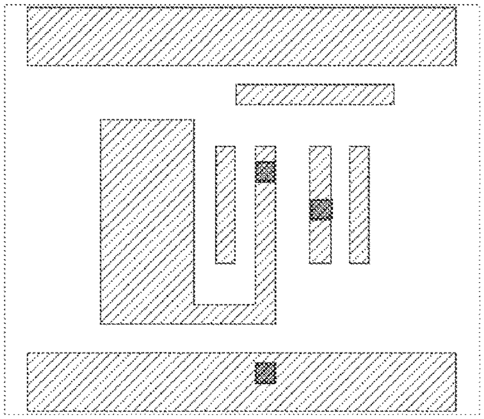
FIG. 2100C
*M* PDF Solutions, Inc.

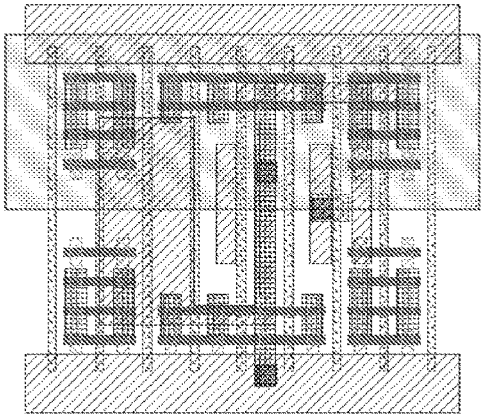
FIG. 2101A
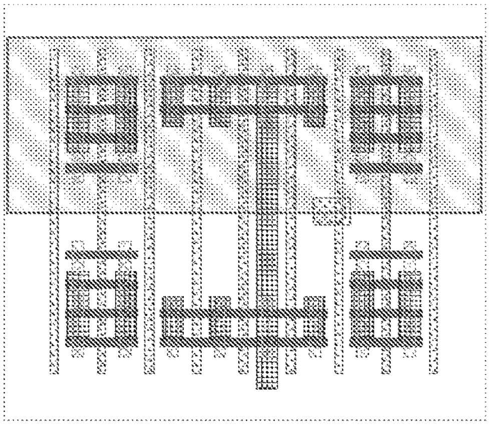
FIG. 2101B
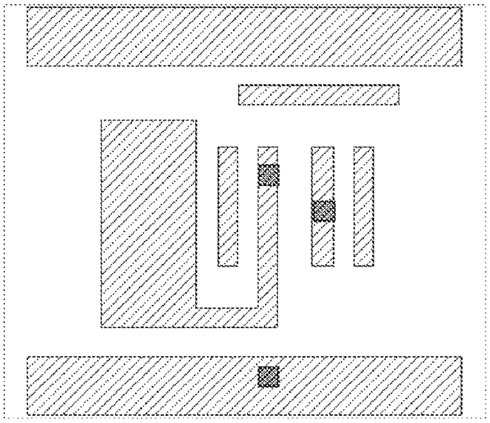
FIG. 2101C

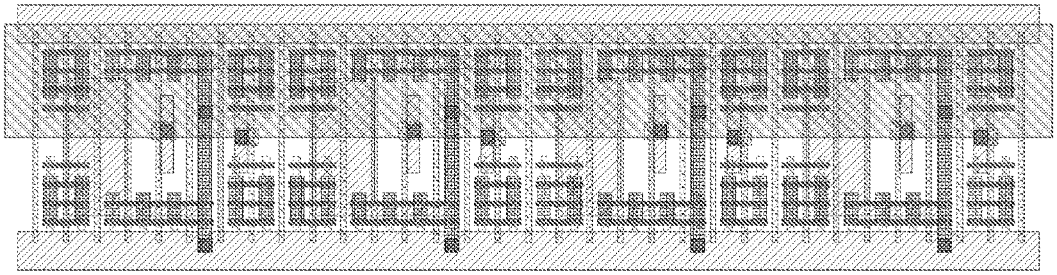
FIG. 2102A
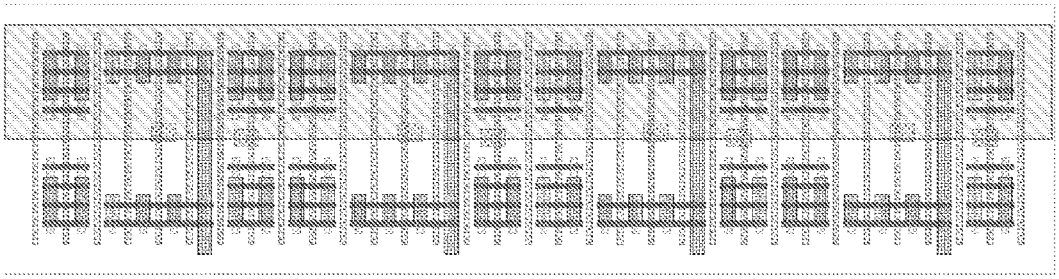
FIG. 2102B
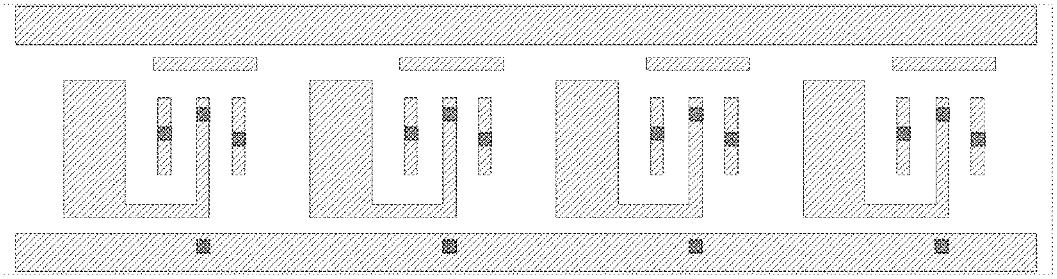
FIG. 2102C

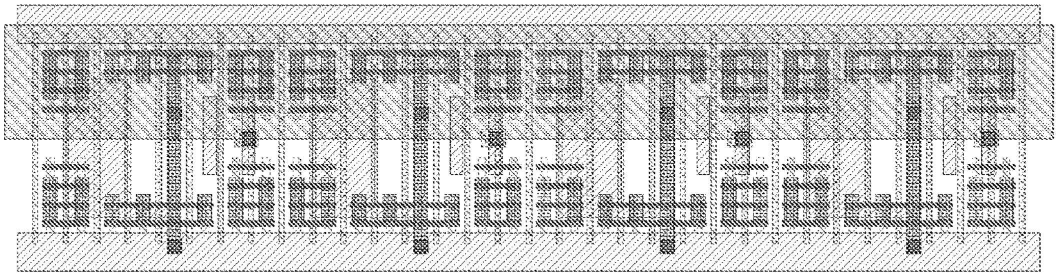
FIG. 2103A
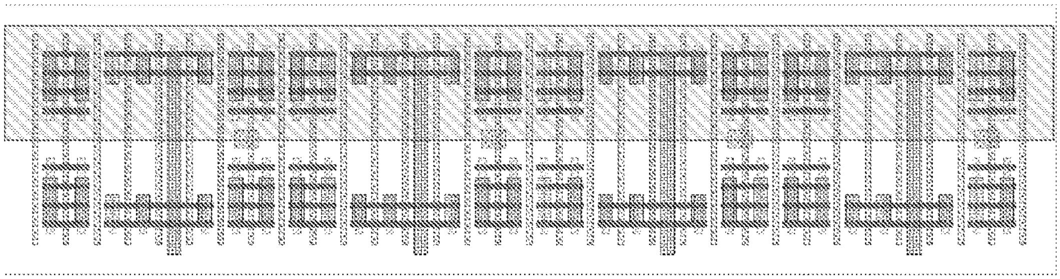
FIG. 2103B
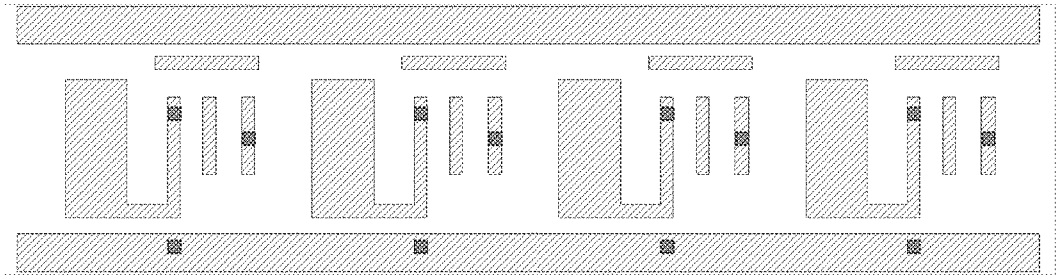
FIG. 2103C
*M* PDF Solutions, Inc.

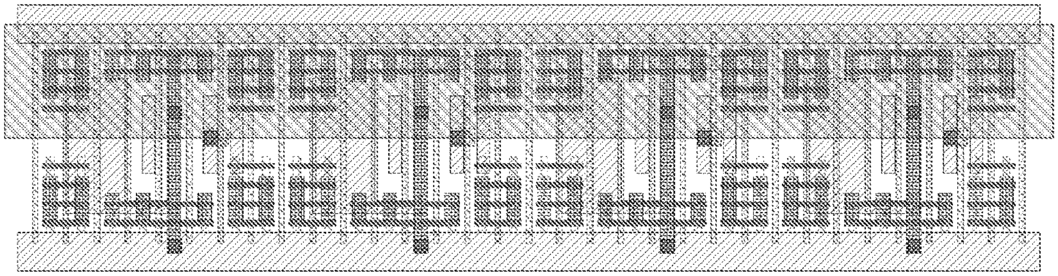
FIG. 2104A
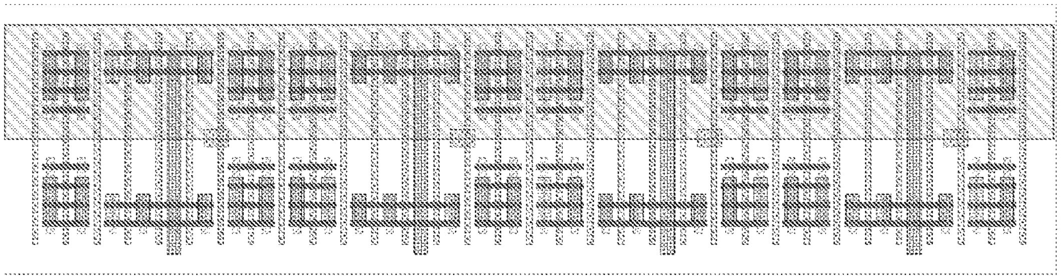
FIG. 2104B
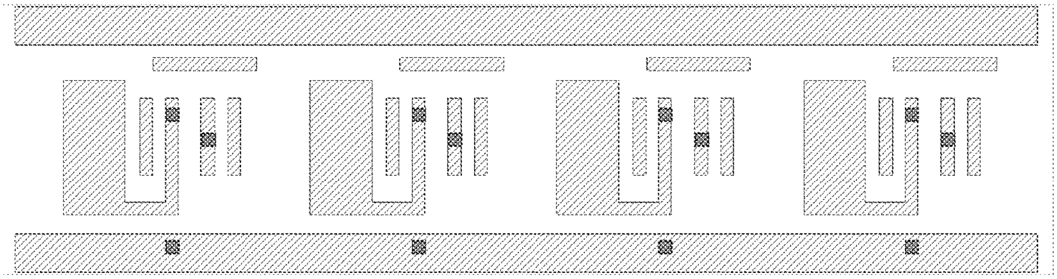
FIG. 2104C

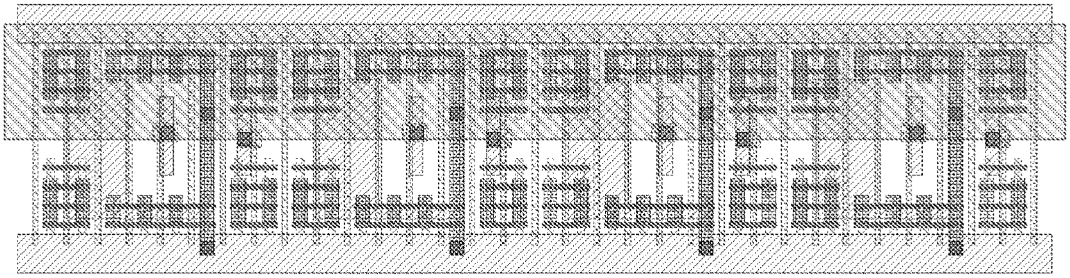
FIG. 2105A
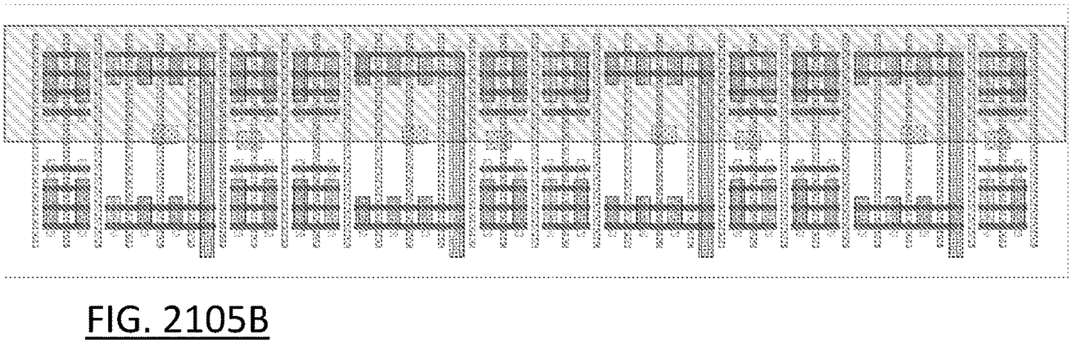
FIG. 2105B
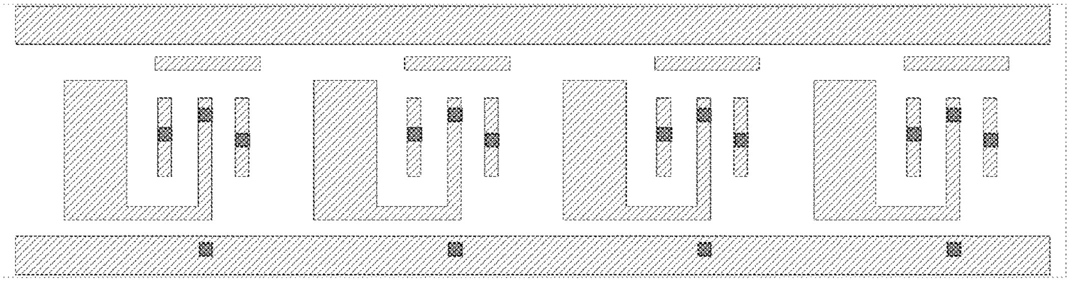
FIG. 2105C

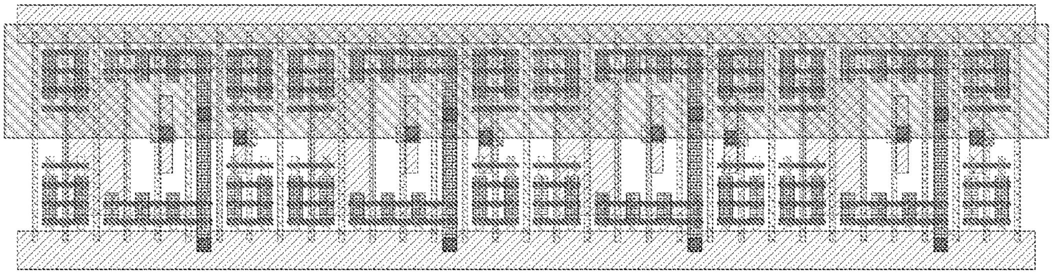
FIG. 2106A
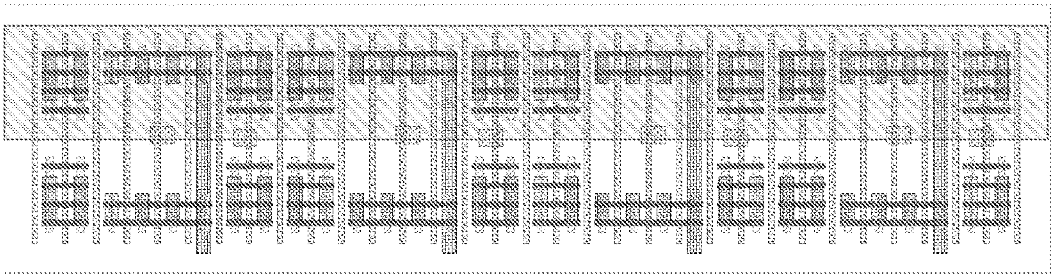
FIG. 2106B
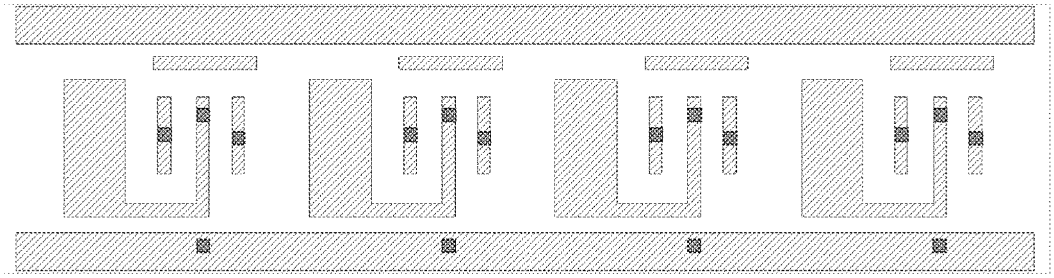
FIG. 2106C

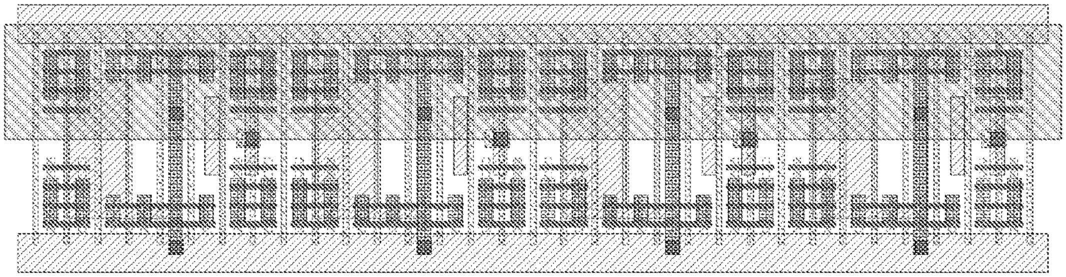
FIG. 2107A
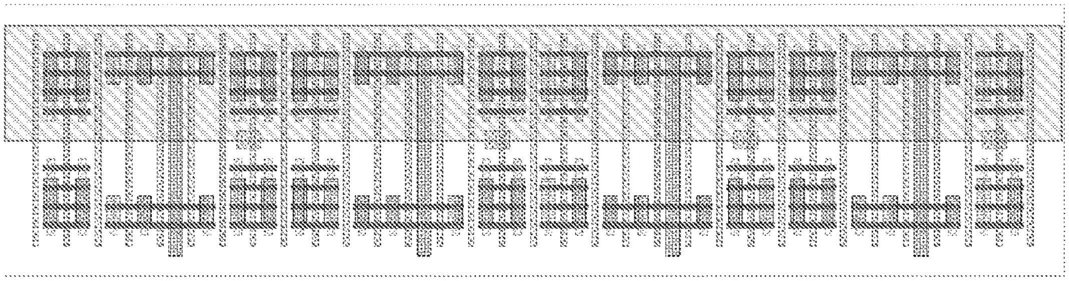
FIG. 2107B
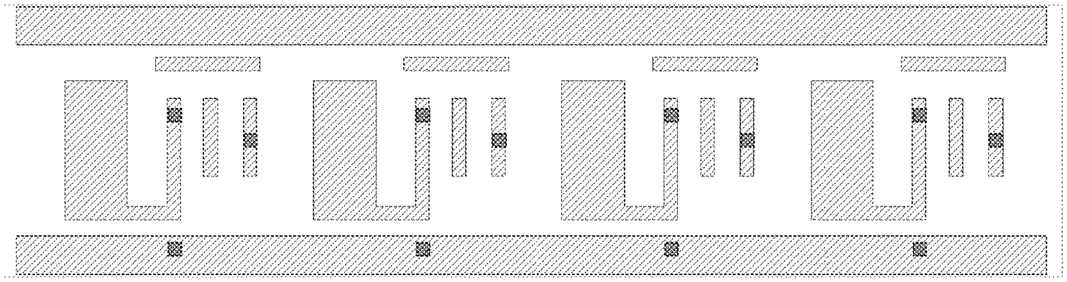
FIG. 2107C

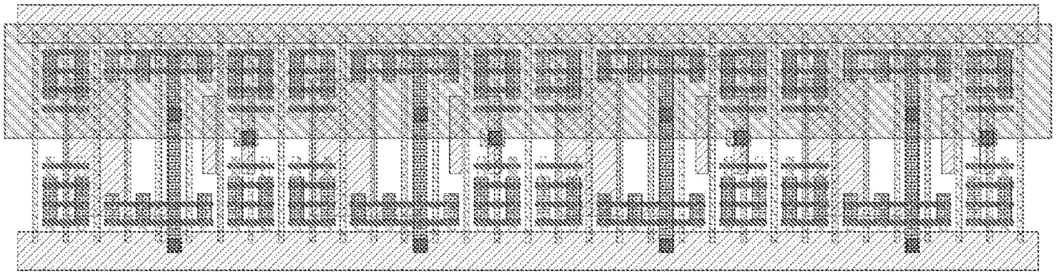
FIG. 2108A
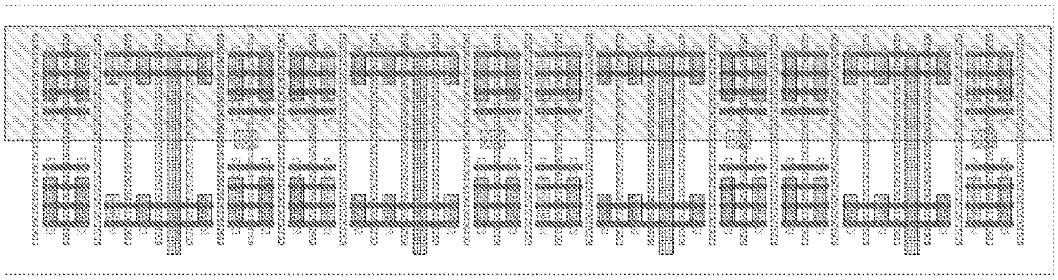
FIG. 2108B
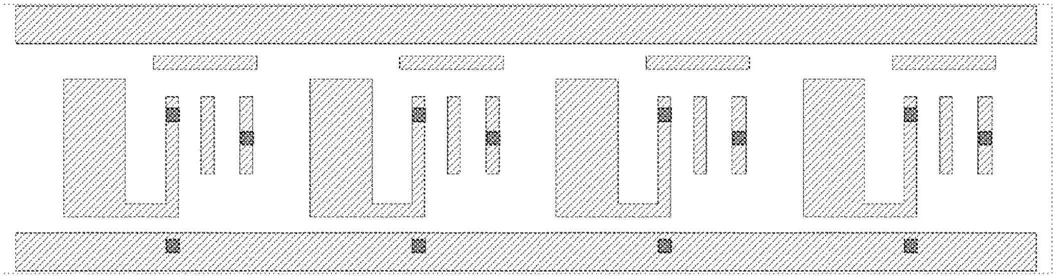
FIG. 2108C
*M* PDF Solutions, Inc.

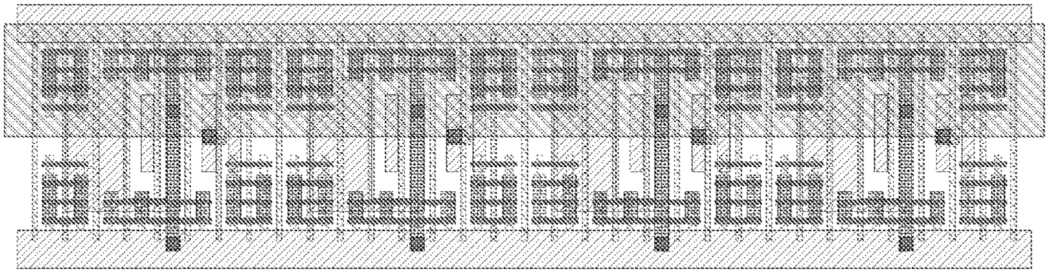
FIG. 2109A
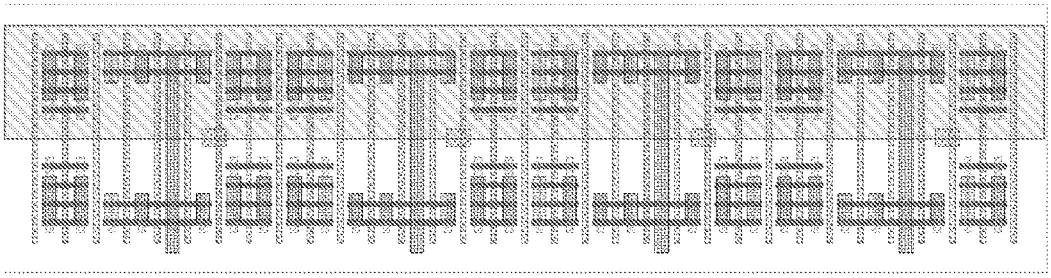
FIG. 2109B
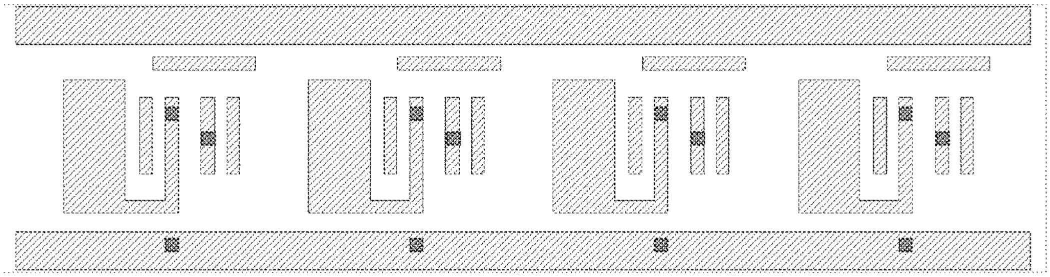
FIG. 2109C

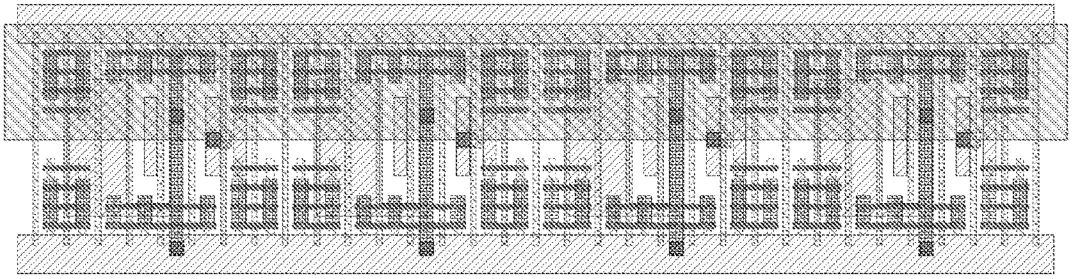
FIG. 2110A
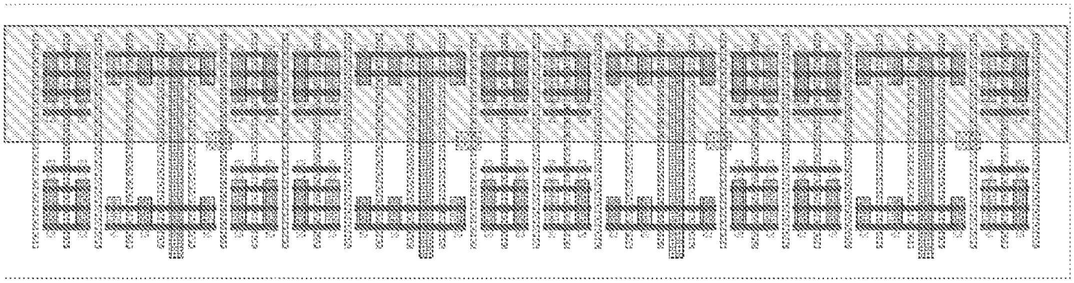
FIG. 2110B
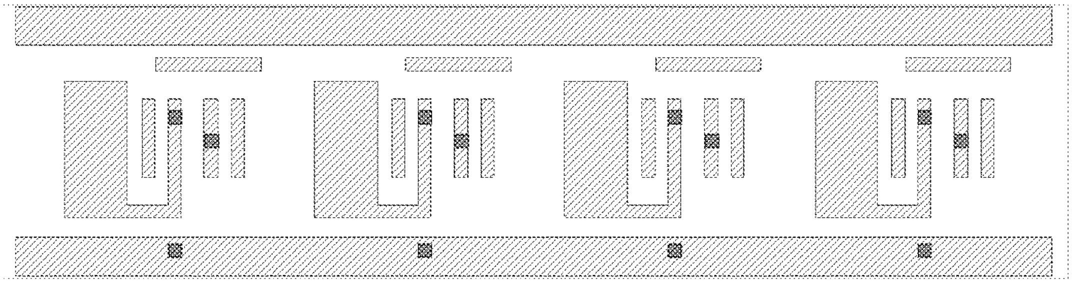
FIG. 2110C
*M* PDF Solutions, Inc.

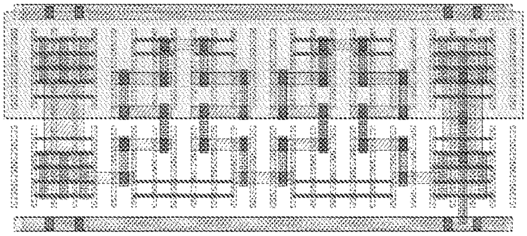
FIG. 2111A
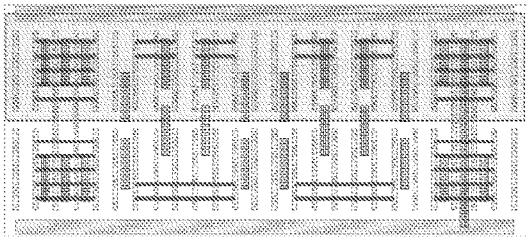
FIG. 2111B
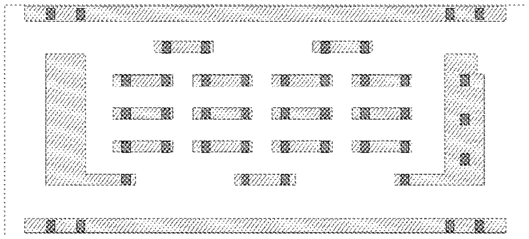
FIG. 2111C

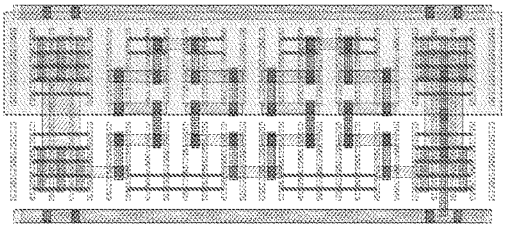
FIG. 2112A
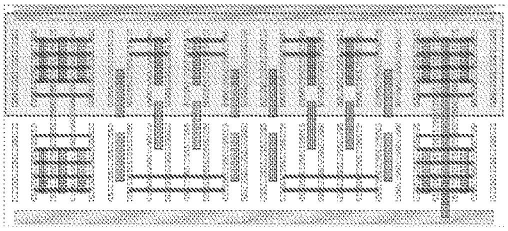
FIG. 2112B
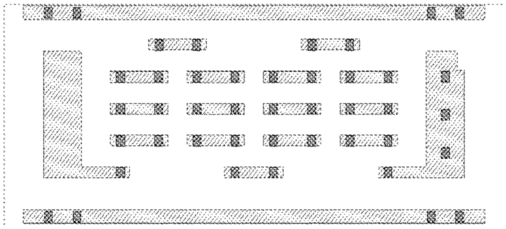
FIG. 2112C

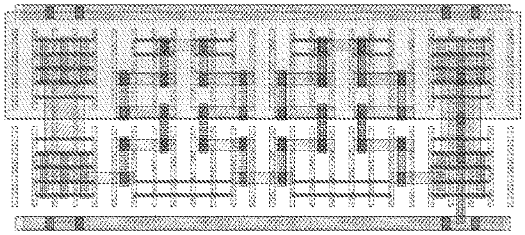
FIG. 2113A
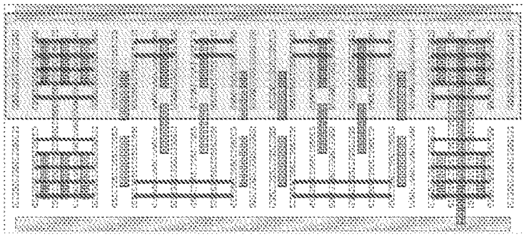
FIG. 2113B
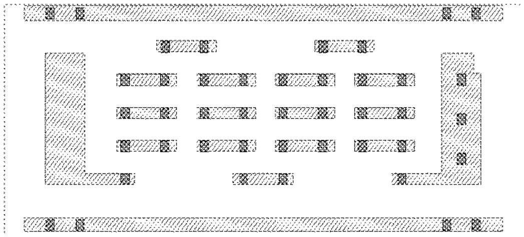
FIG. 2113C

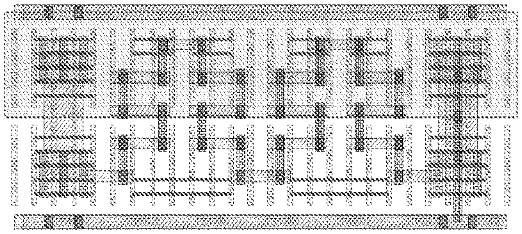
FIG. 2114A
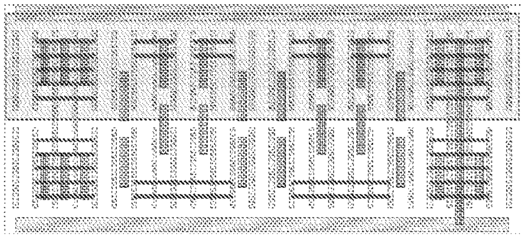
FIG. 2114B
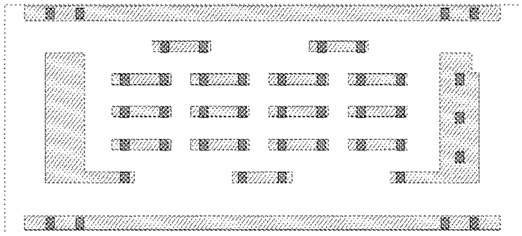
FIG. 2114C

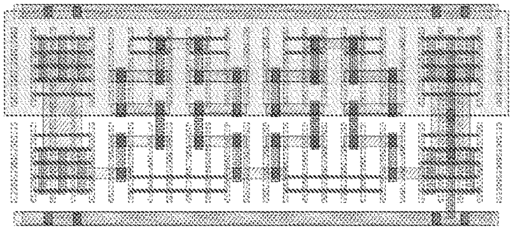
FIG. 2115A
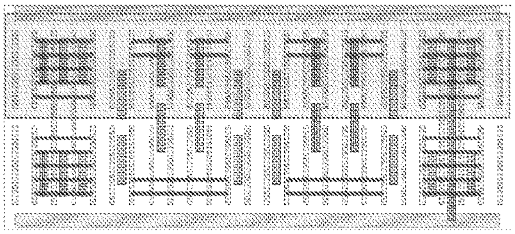
FIG. 2115B
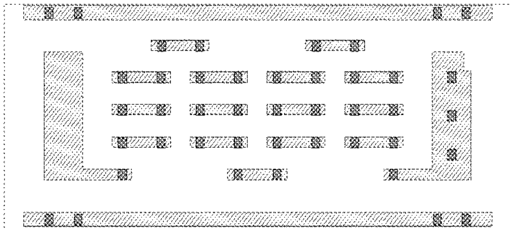
FIG. 2115C
*M* PDF Solutions, Inc.

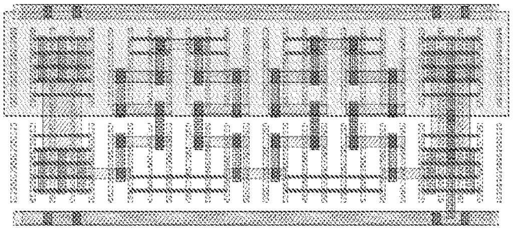
FIG. 2116A
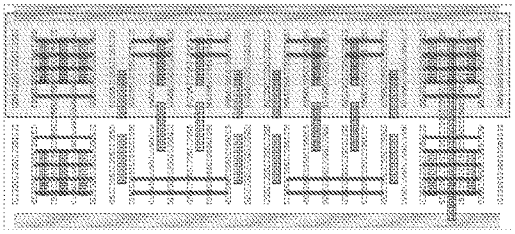
FIG. 2116B
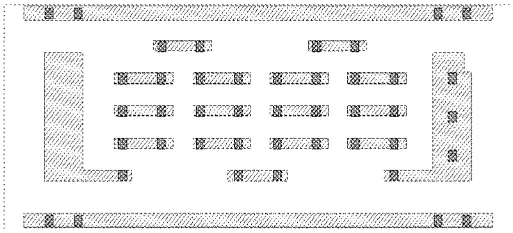
FIG. 2116C
*M* PDF Solutions, Inc.

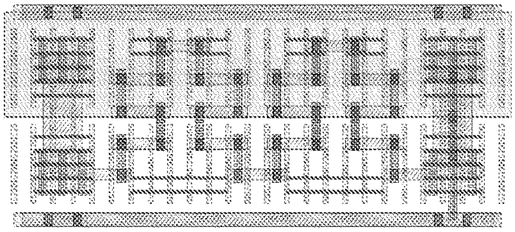
FIG. 2117A
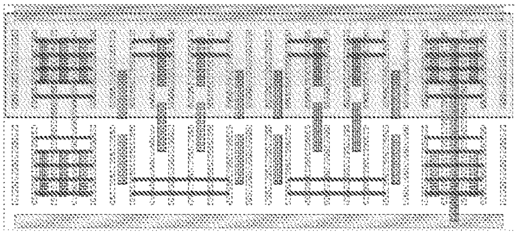
FIG. 2117B
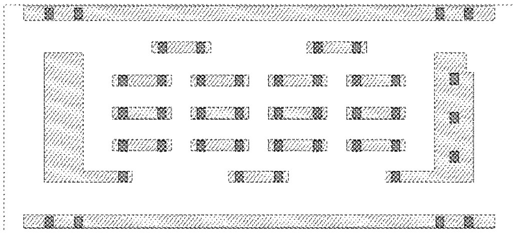
FIG. 2117C

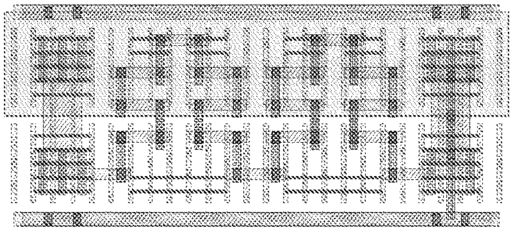
FIG. 2118A
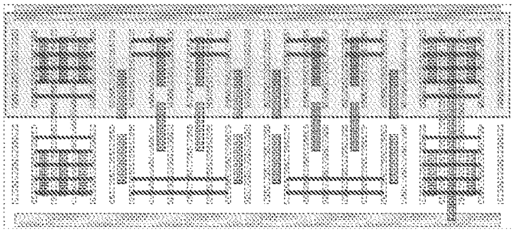
FIG. 2118B
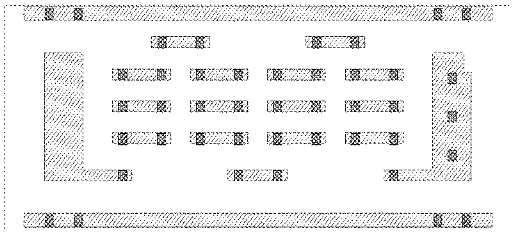
FIG. 2118C

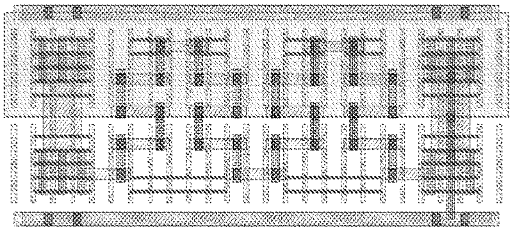
FIG. 2119A
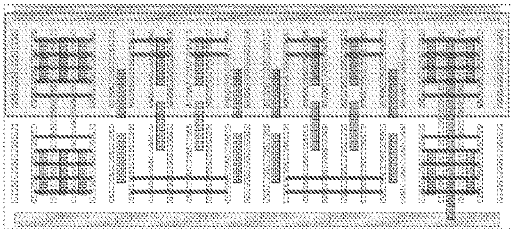
FIG. 2119B
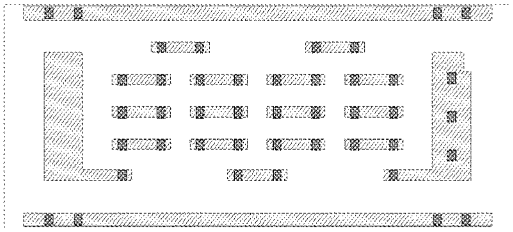
FIG. 2119C

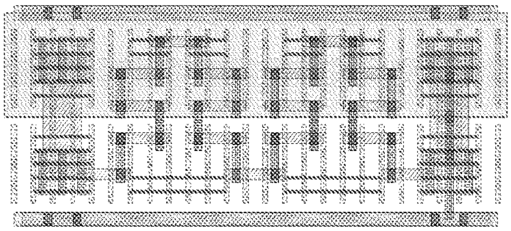
FIG. 2120A
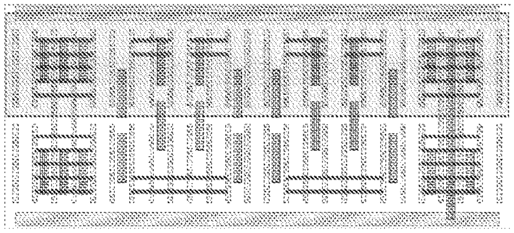
FIG. 2120B
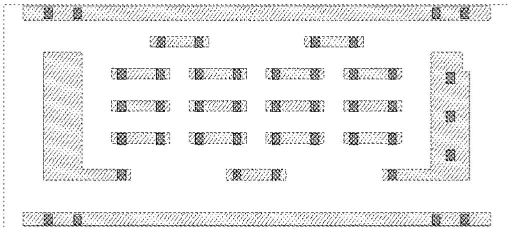
FIG. 2120C

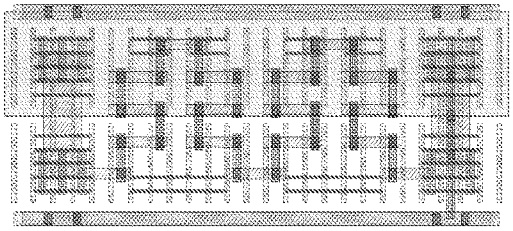
FIG. 2121A
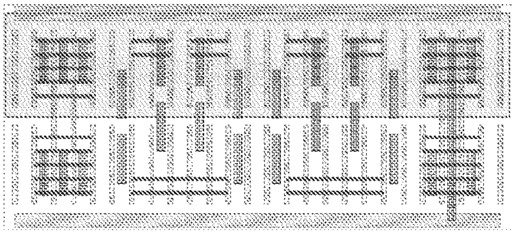
FIG. 2121B
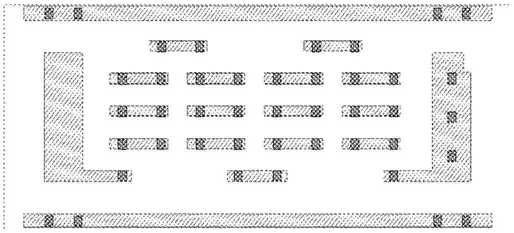
FIG. 2121C

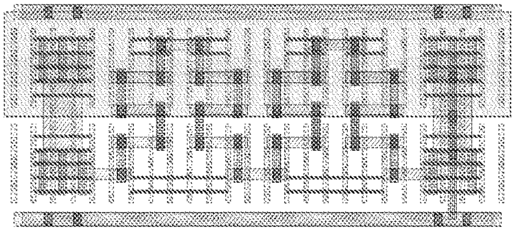
FIG. 2122A
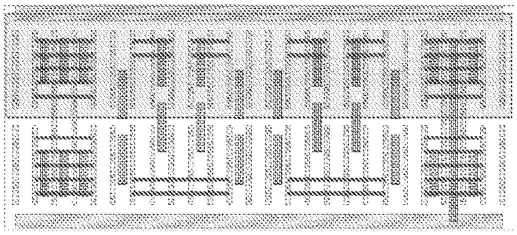
FIG. 2122B
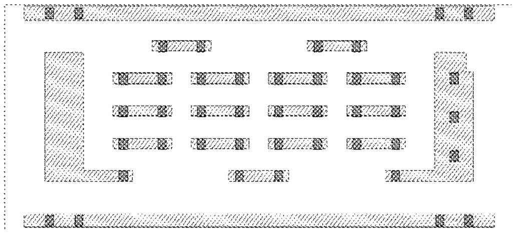
FIG. 2122C

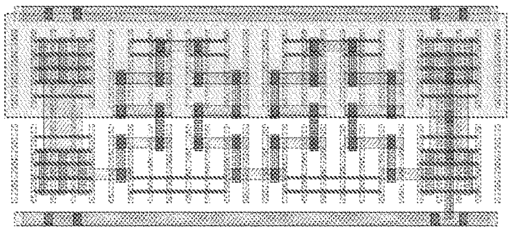
FIG. 2123A
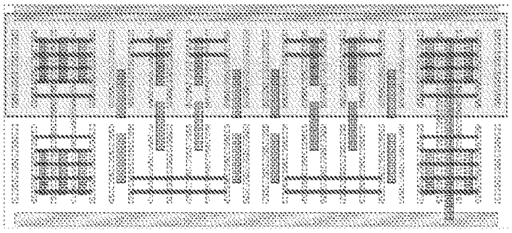
FIG. 2123B
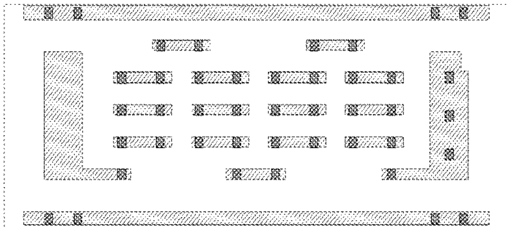
FIG. 2123C

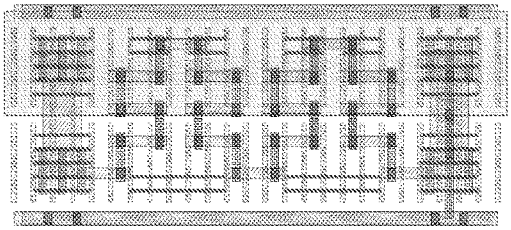
FIG. 2124A
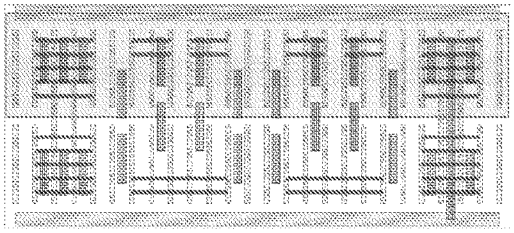
FIG. 2124B
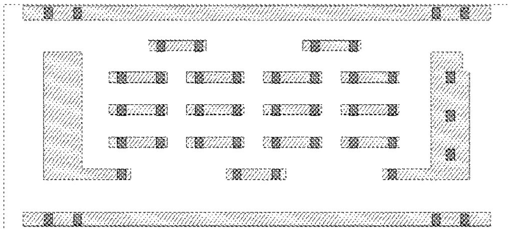
FIG. 2124C

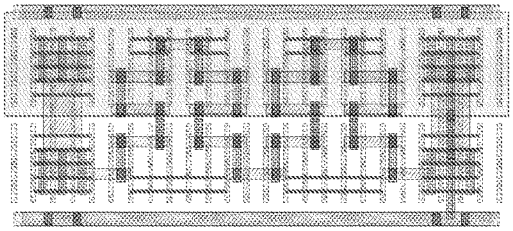
FIG. 2125A
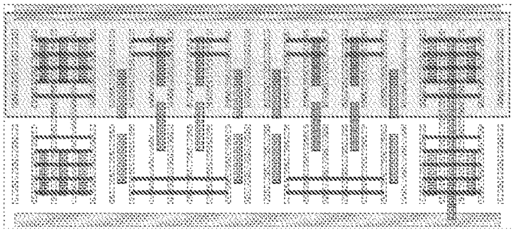
FIG. 2125B
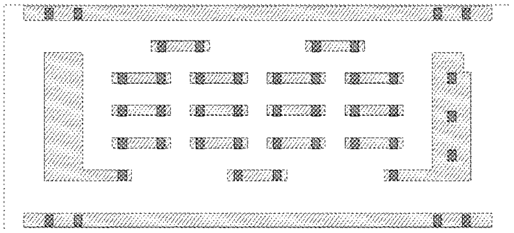
FIG. 2125C

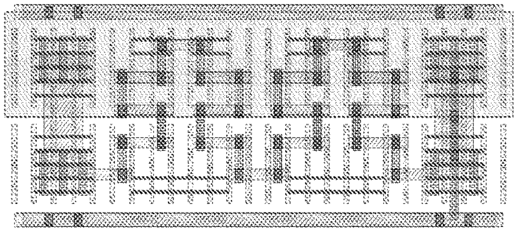
FIG. 2126A
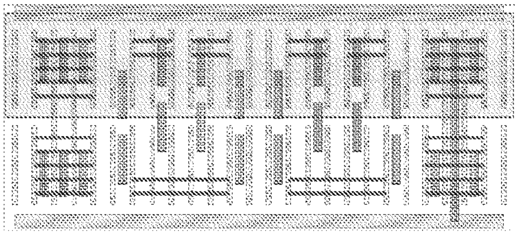
FIG. 2126B
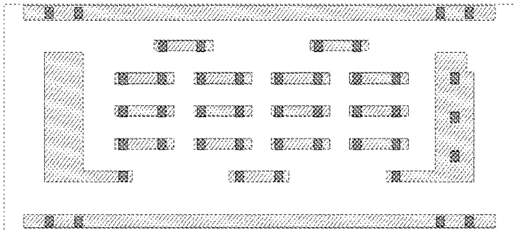
FIG. 2126C

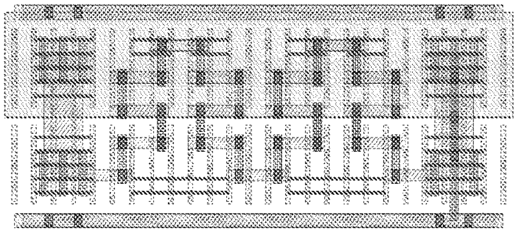
FIG. 2127A
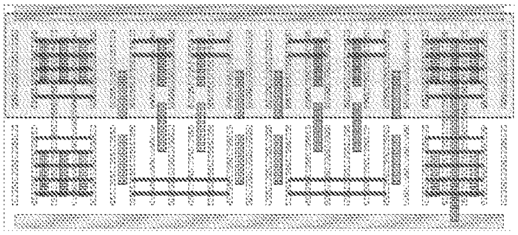
FIG. 2127B
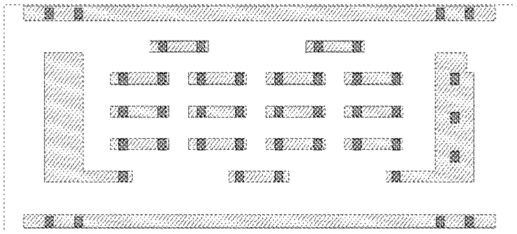
FIG. 2127C

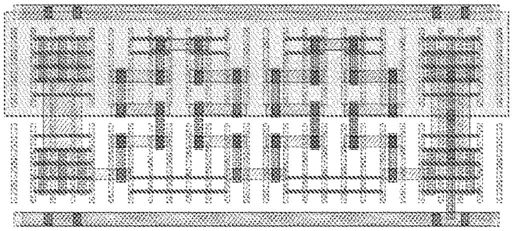
FIG. 2128A
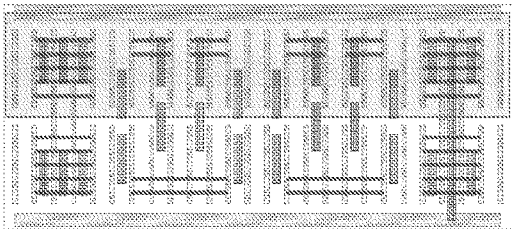
FIG. 2128B
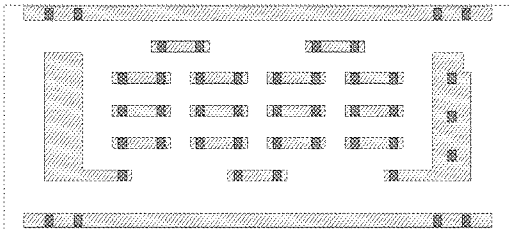
FIG. 2128C
*M* PDF Solutions, Inc.

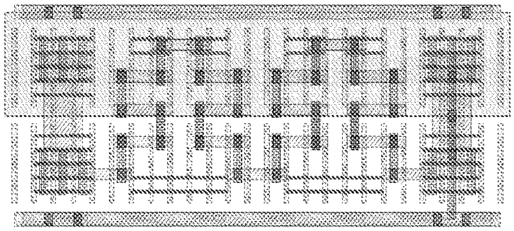
FIG. 2129A
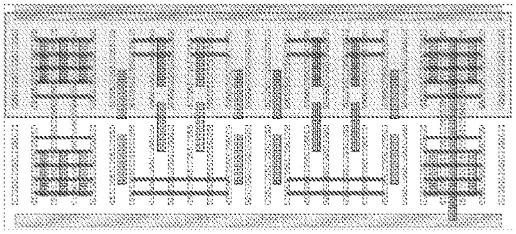
FIG. 2129B
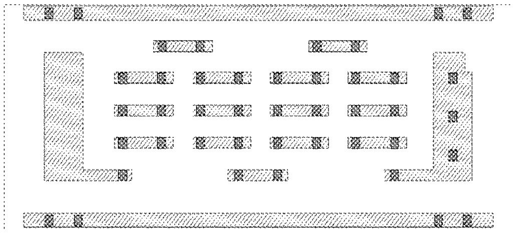
FIG. 2129C

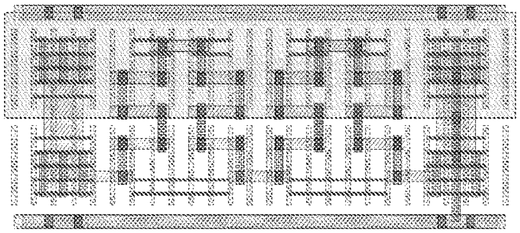
FIG. 2130A
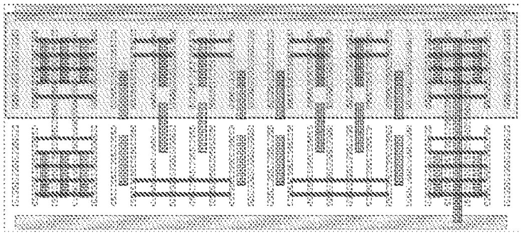
FIG. 2130B
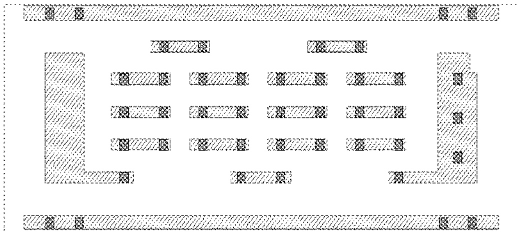
FIG. 2130C

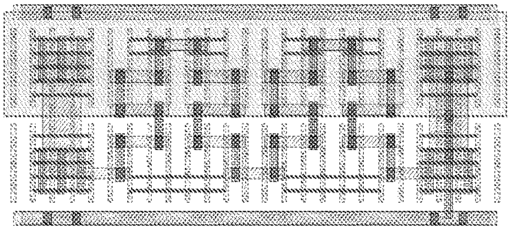
FIG. 2131A
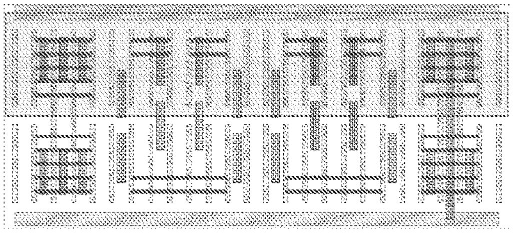
FIG. 2131B
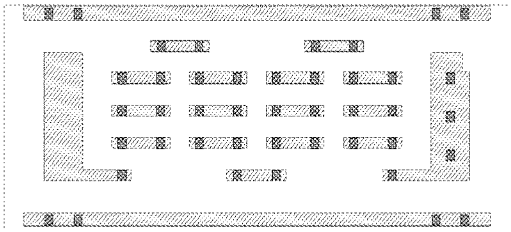
FIG. 2131C

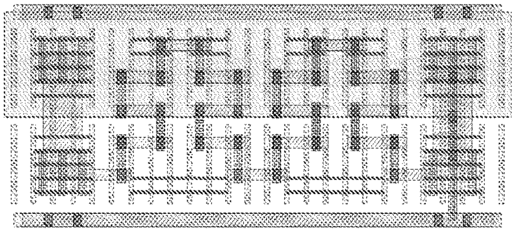
FIG. 2132A
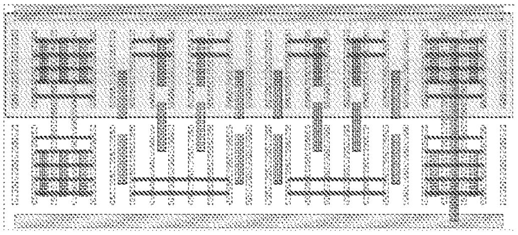
FIG. 2132B
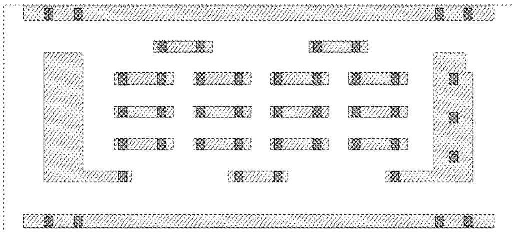
FIG. 2132C

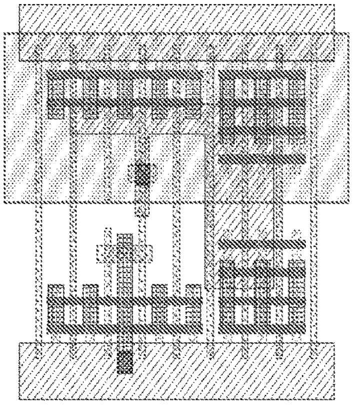
FIG. 2133A
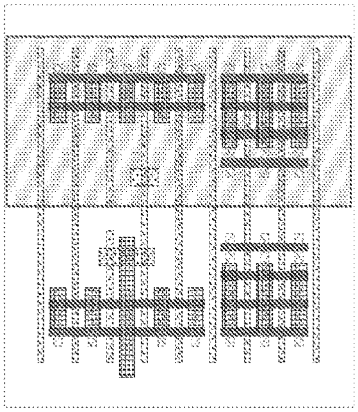
FIG. 2133B
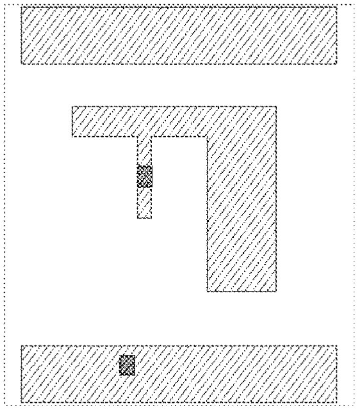
FIG. 2133C

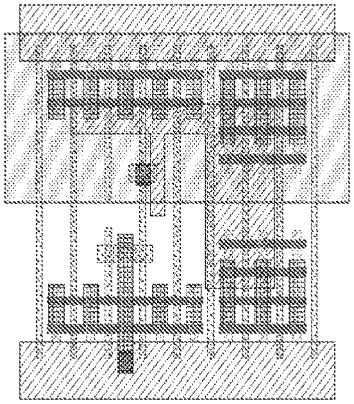
FIG. 2134A
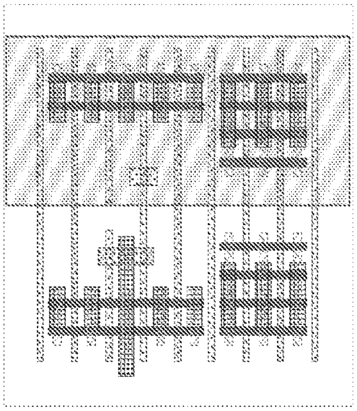
FIG. 2134B
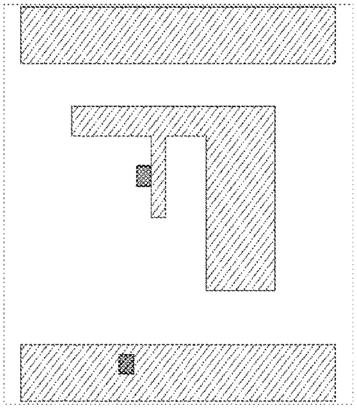
FIG. 2134C

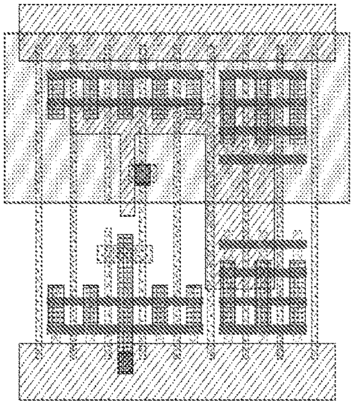
FIG. 2135A
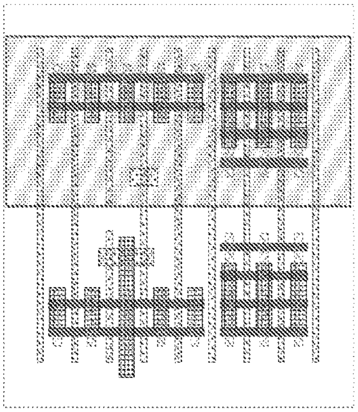
FIG. 2135B
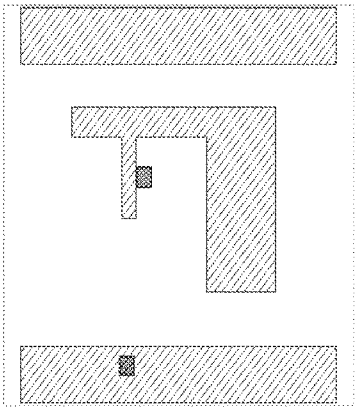
FIG. 2135C
*M* PDF Solutions, Inc.

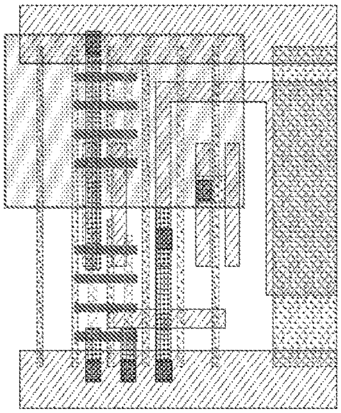
FIG. 2136A
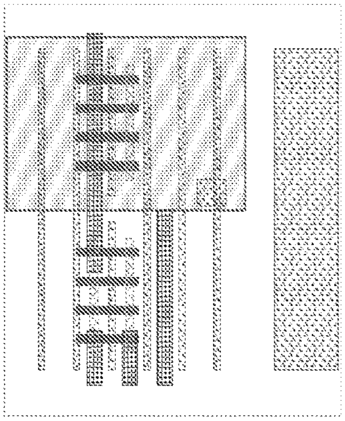
FIG. 2136B
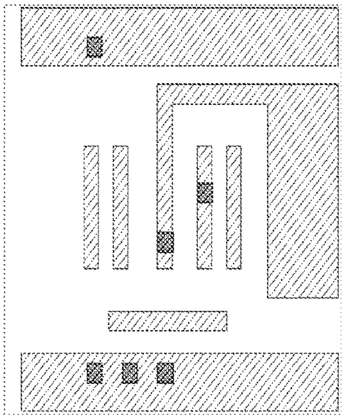
FIG. 2136C

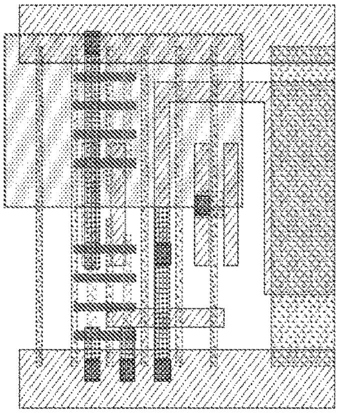
FIG. 2137A
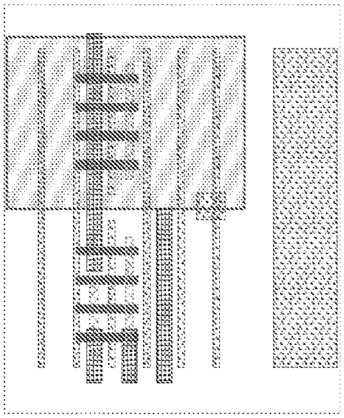
FIG. 2137B
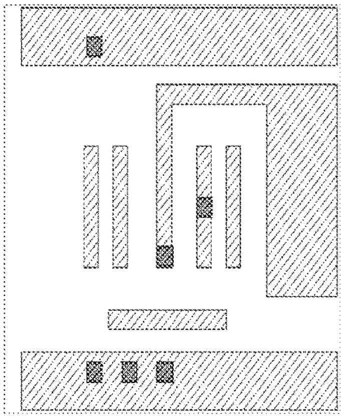
FIG. 2137C

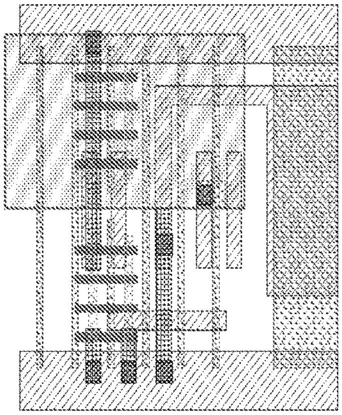
FIG. 2138A
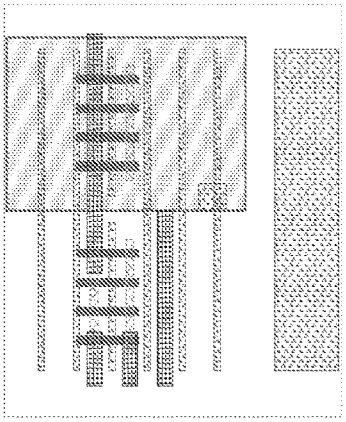
FIG. 2138B
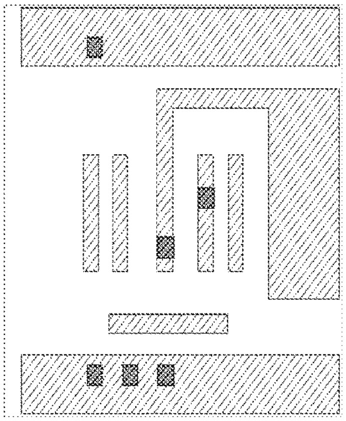
FIG. 2138C

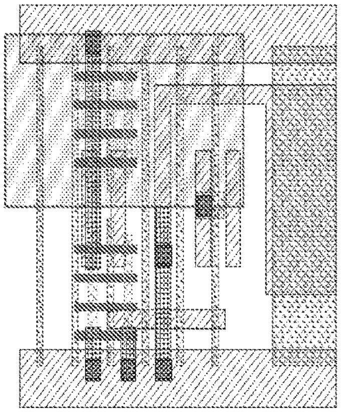
FIG. 2139A
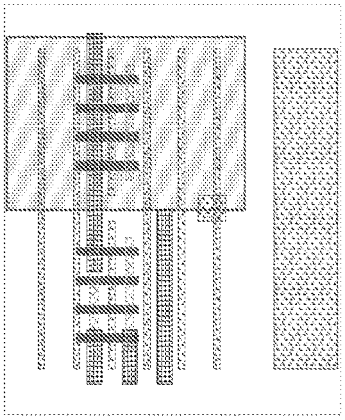
FIG. 2139B
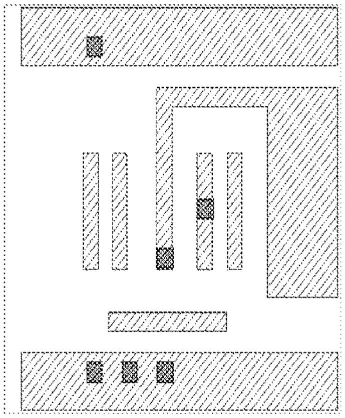
FIG. 2139C

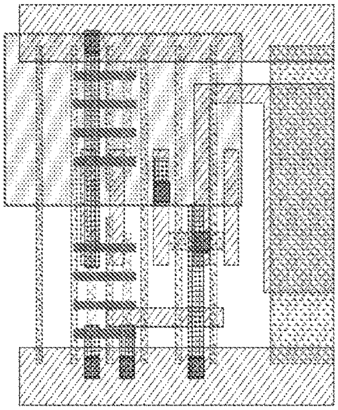
FIG. 2140A
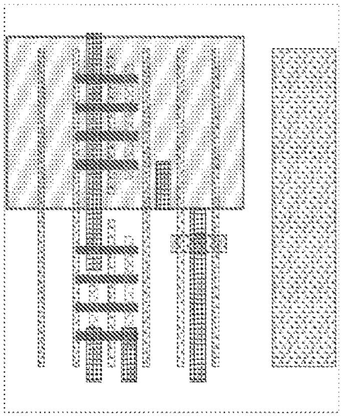
FIG. 2140B
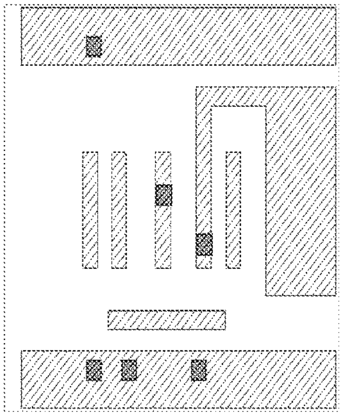
FIG. 2140C
*M* PDF Solutions, Inc.

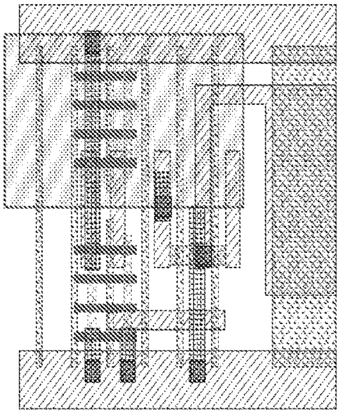
FIG. 2141A
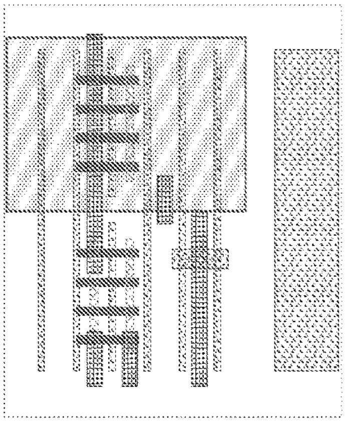
FIG. 2141B
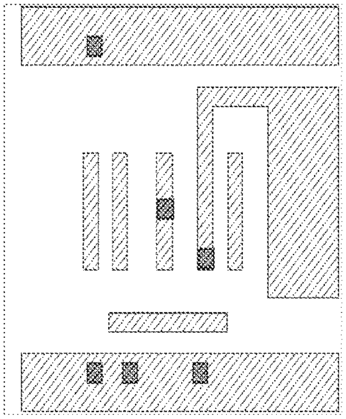
FIG. 2141C

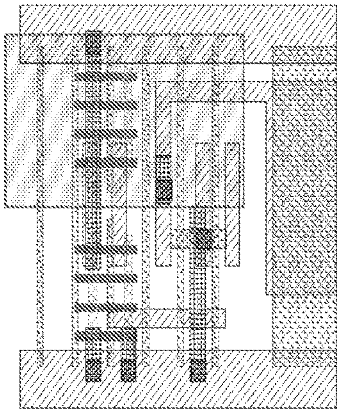
FIG. 2142A
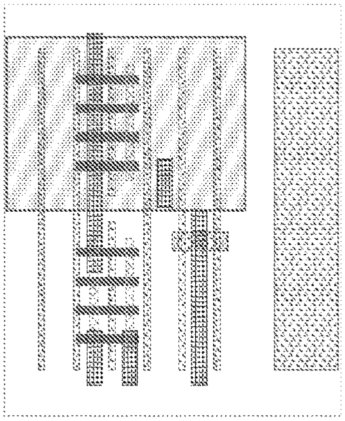
FIG. 2142B
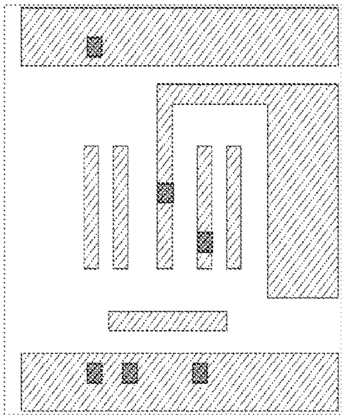
FIG. 2142C

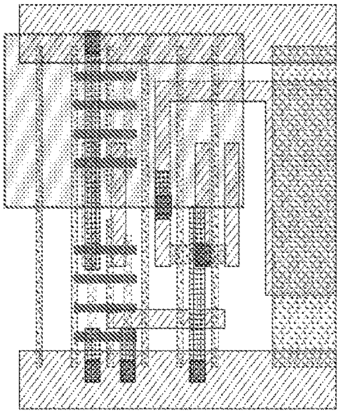
FIG. 2143A
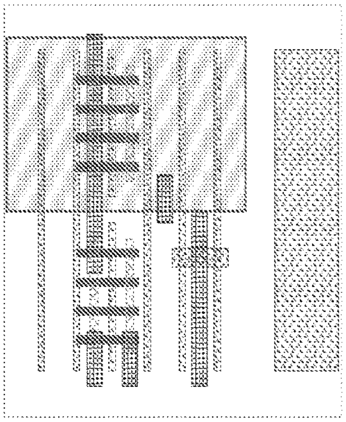
FIG. 2143B
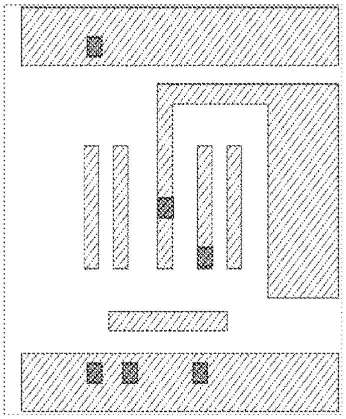
FIG. 2143C

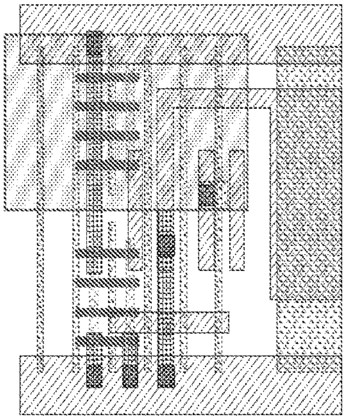
FIG. 2144A
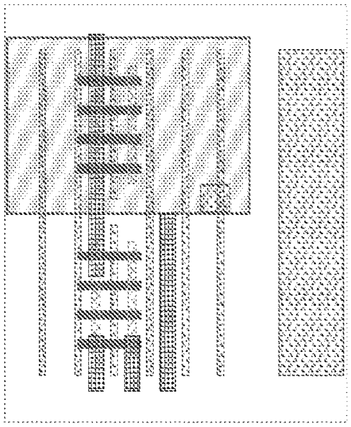
FIG. 2144B
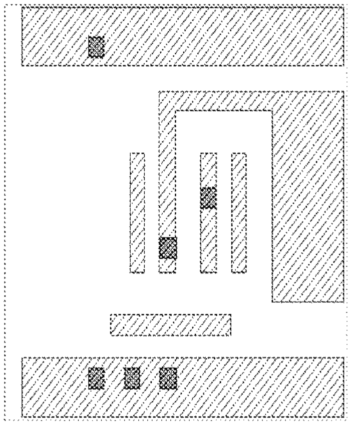
FIG. 2144C

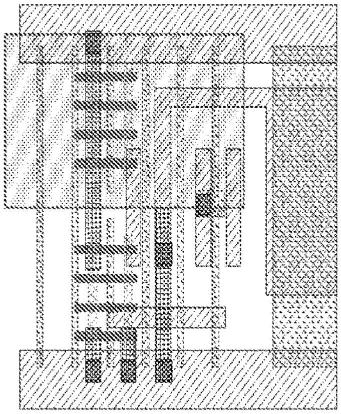
FIG. 2145A
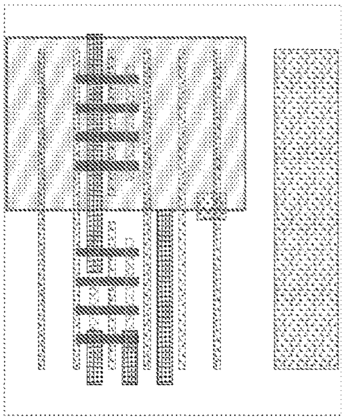
FIG. 2145B
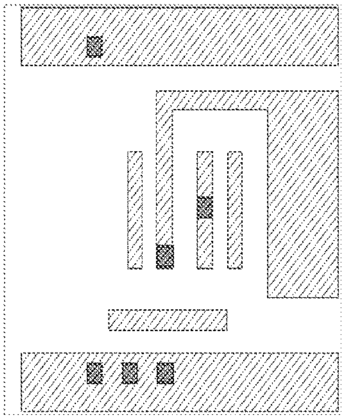
FIG. 2145C

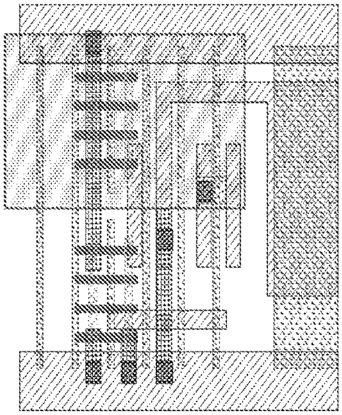
FIG. 2146A
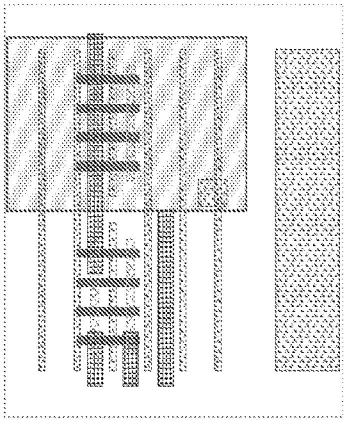
FIG. 2146B
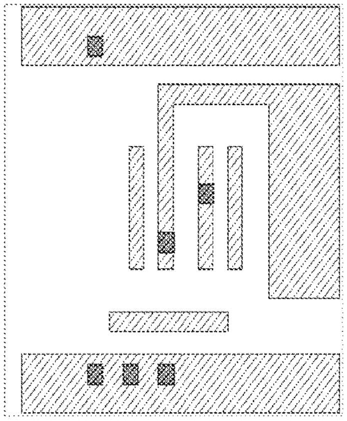
FIG. 2146C

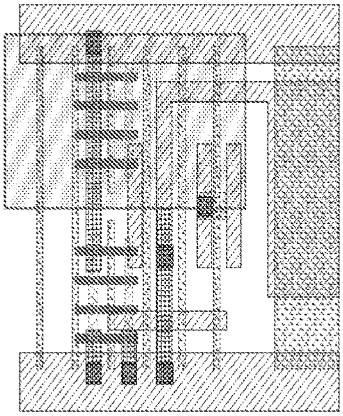
FIG. 2147A
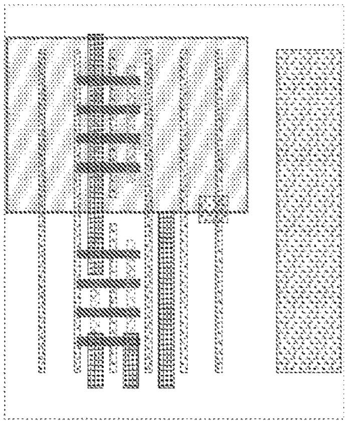
FIG. 2147B
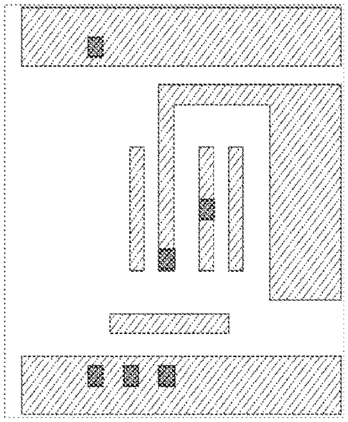
FIG. 2147C
*M* PDF Solutions, Inc.

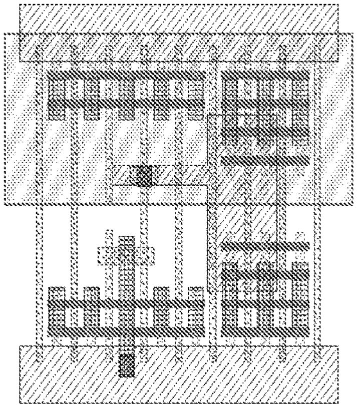
FIG. 2148A
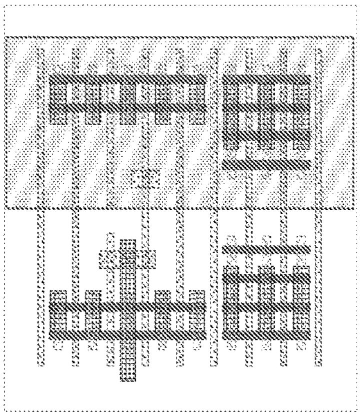
FIG. 2148B
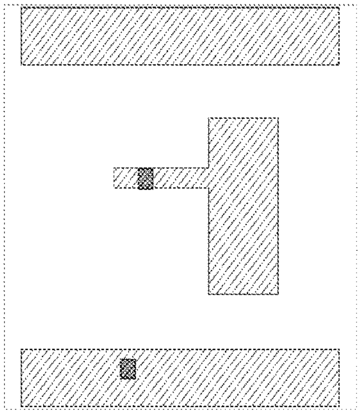
FIG. 2148C

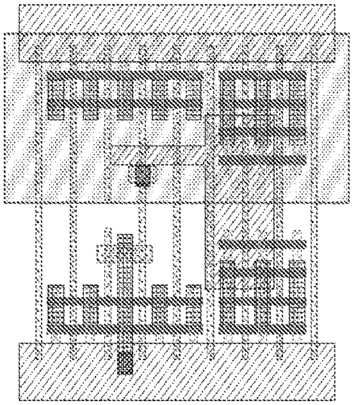
FIG. 2149A
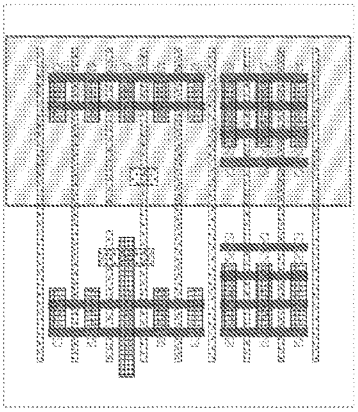
FIG. 2149B
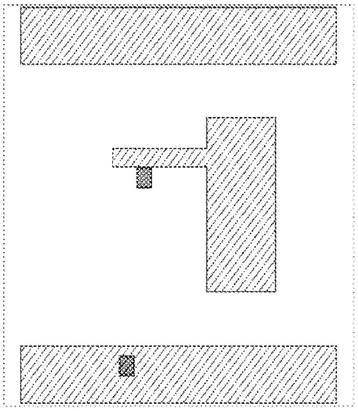
FIG. 2149C

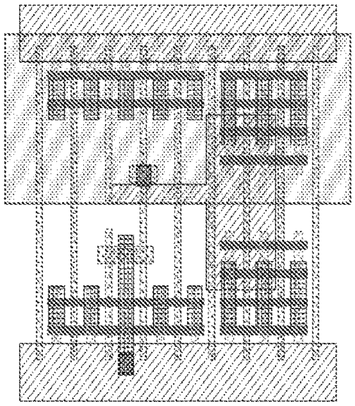
FIG. 2150A
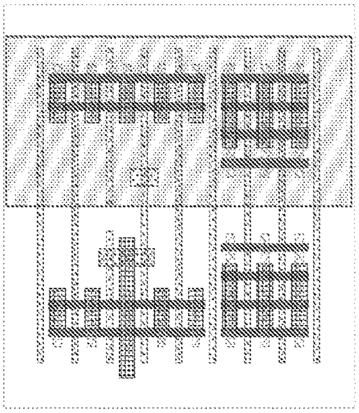
FIG. 2150B
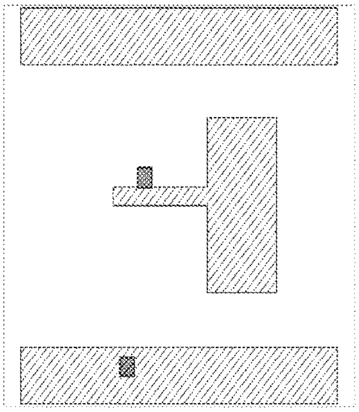
FIG. 2150C

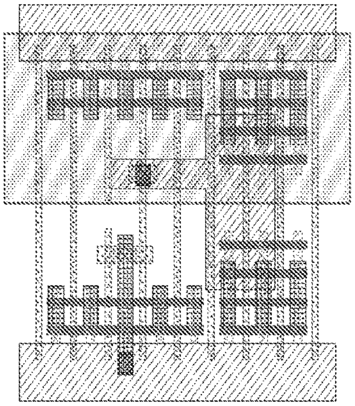
FIG. 2151A
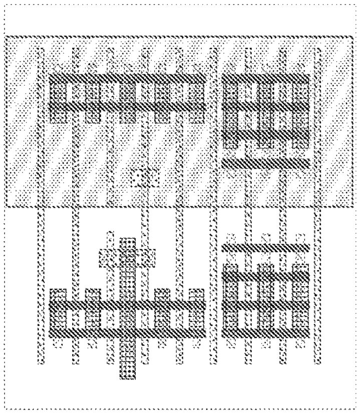
FIG. 2151B
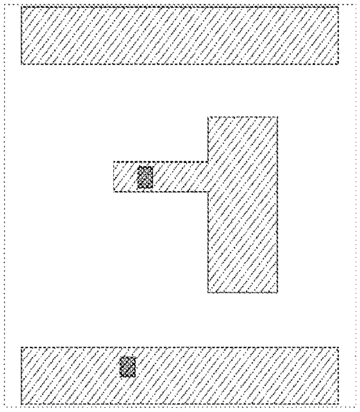
FIG. 2151C

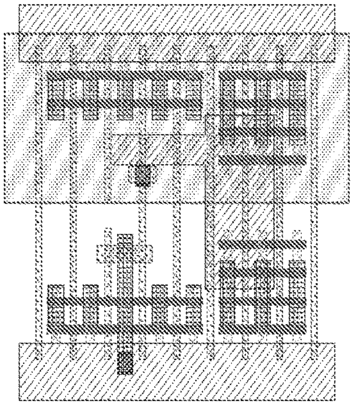
FIG. 2152A
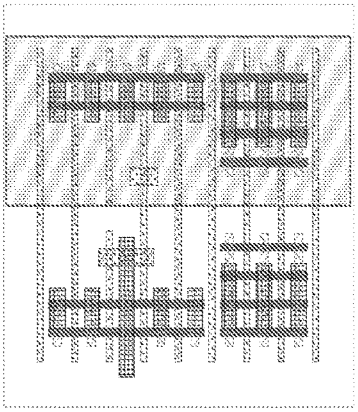
FIG. 2152B
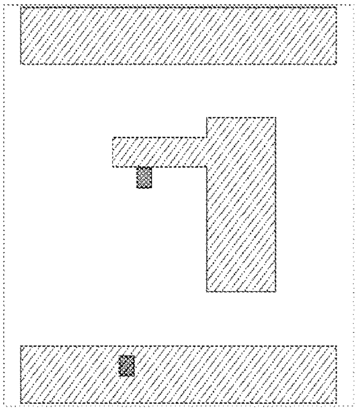
FIG. 2152C

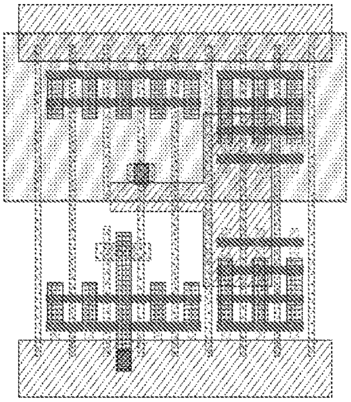
FIG. 2153A
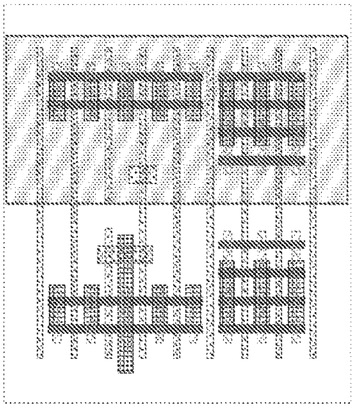
FIG. 2153B
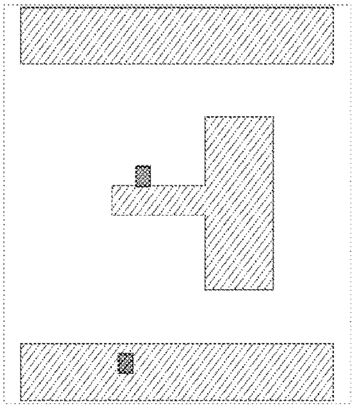
FIG. 2153C

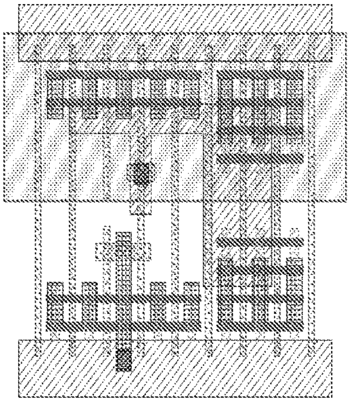
FIG. 2154A
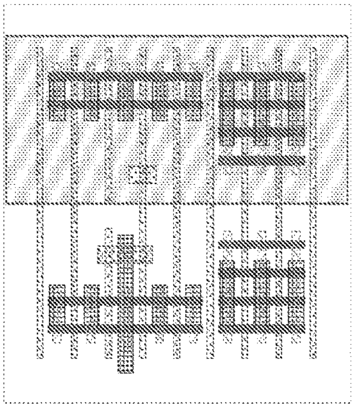
FIG. 2154B
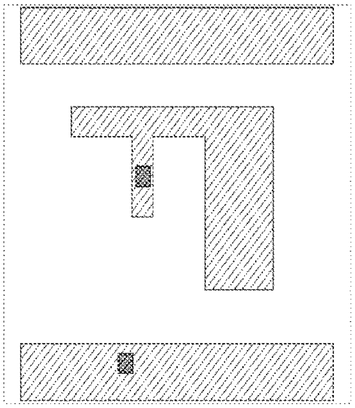
FIG. 2154C
*M* PDF Solutions, Inc.

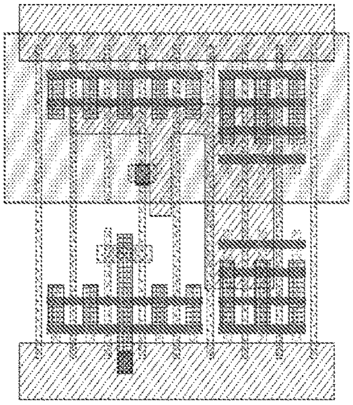
FIG. 2155A
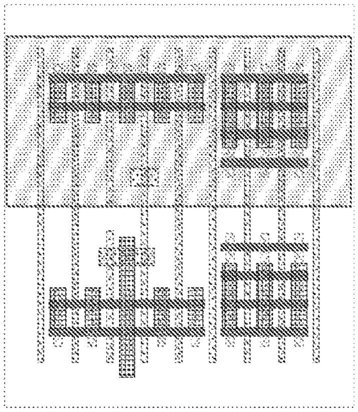
FIG. 2155B
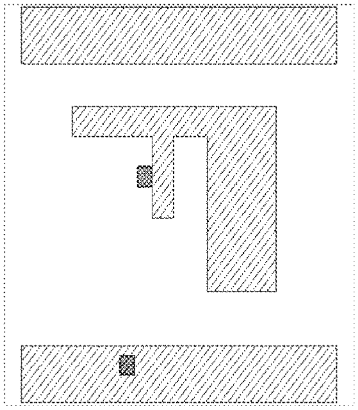
FIG. 2155C
*M* PDF Solutions, Inc.

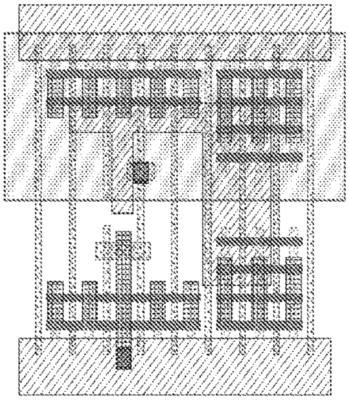
FIG. 2156A
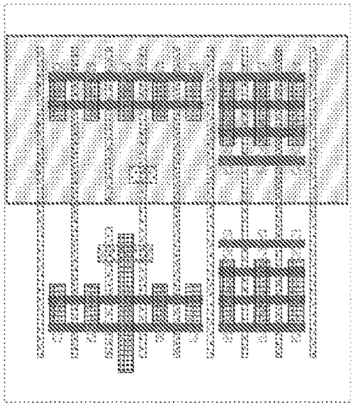
FIG. 2156B
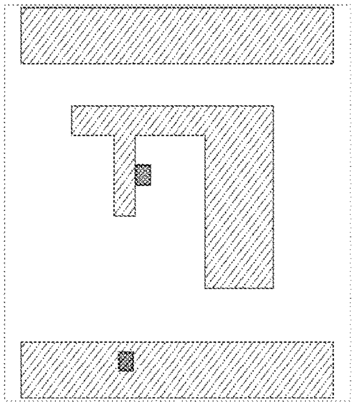
FIG. 2156C
*M* PDF Solutions, Inc.

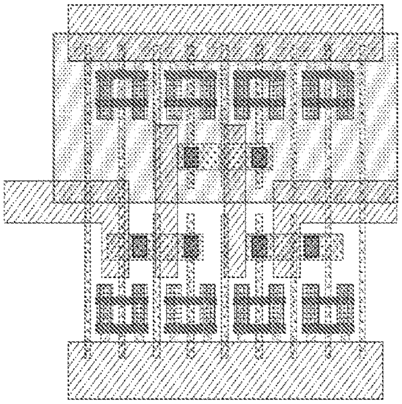
FIG. 2157A
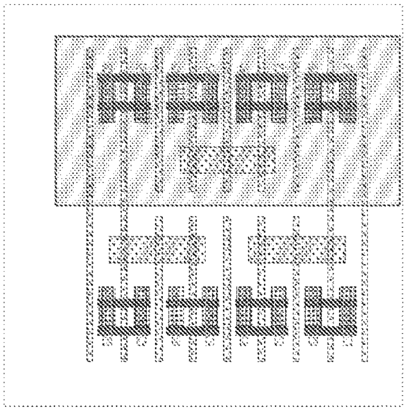
FIG. 2157B
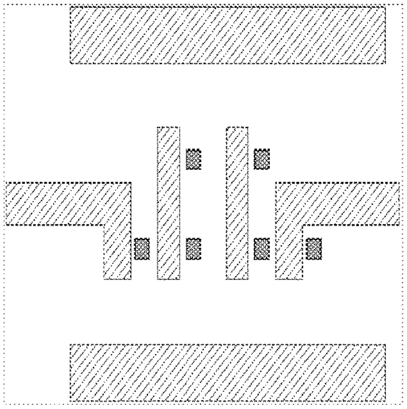
FIG. 2157C
*M* PDF Solutions, Inc.

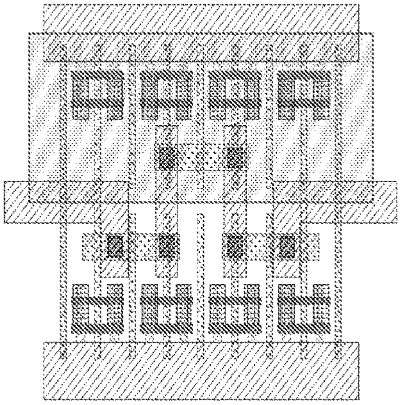
FIG. 2158A
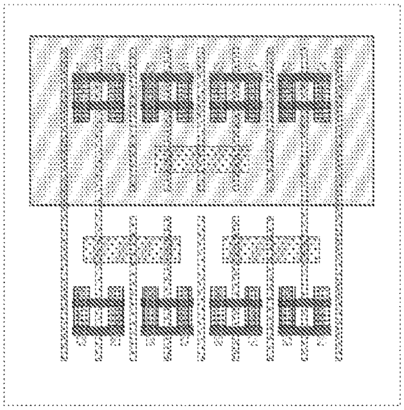
FIG. 2158B
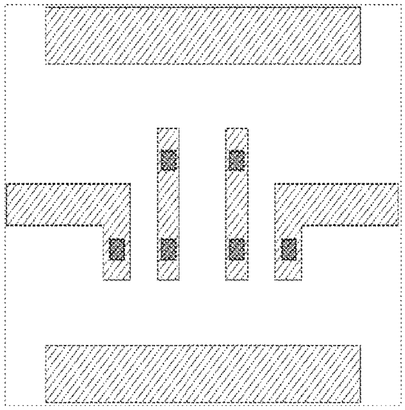
FIG. 2158C

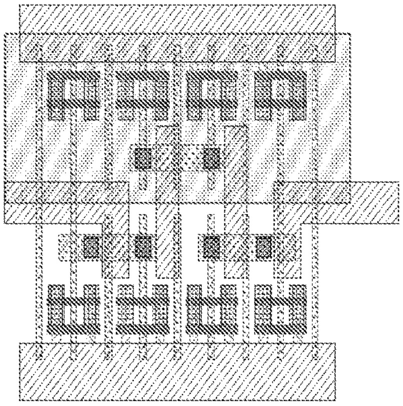
FIG. 2159A
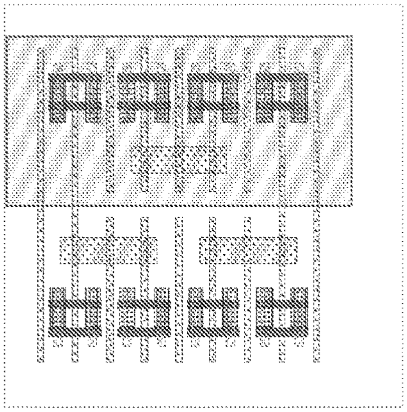
FIG. 2159B
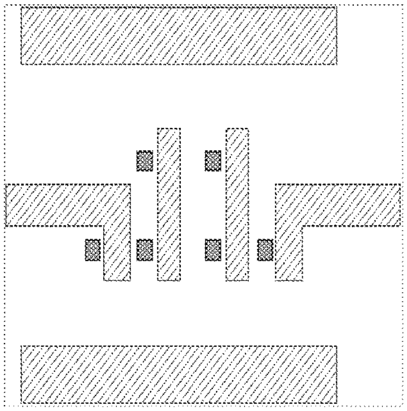
FIG. 2159C

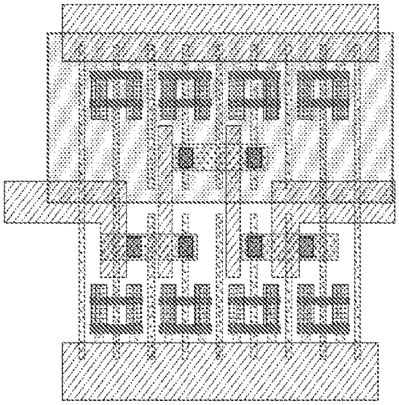
FIG. 2160A
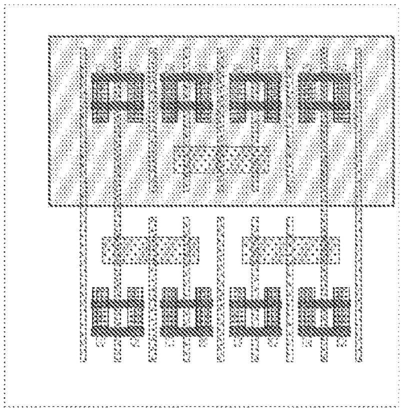
FIG. 2160B
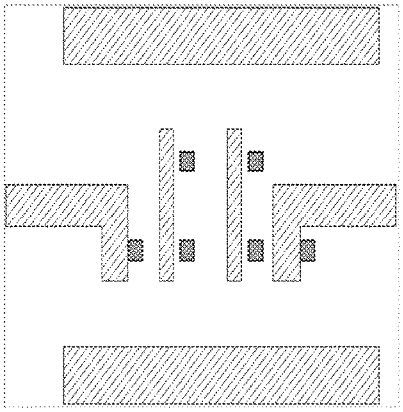
FIG. 2160C
*M* PDF Solutions, Inc.

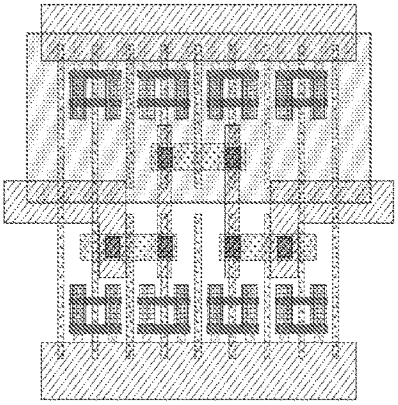
FIG. 2161A
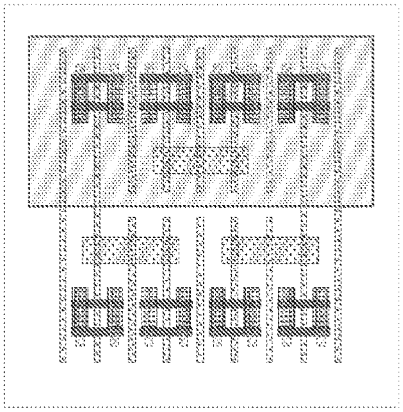
FIG. 2161B
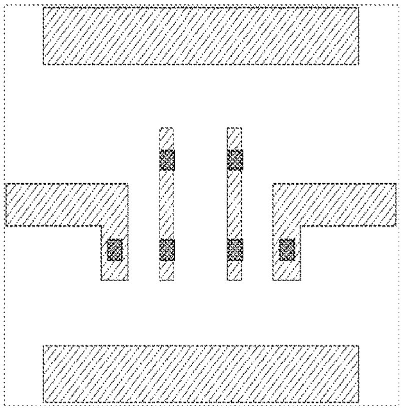
FIG. 2161C
*M* PDF Solutions, Inc.

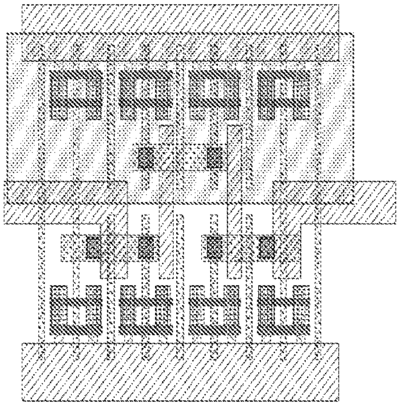
FIG. 2162A
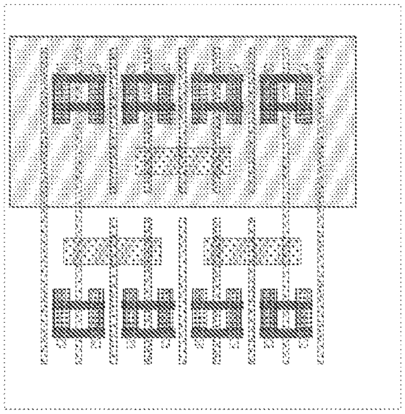
FIG. 2162B
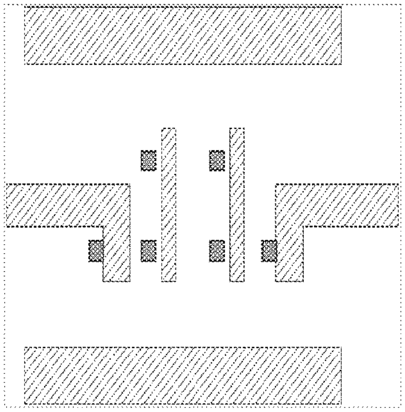
FIG. 2162C

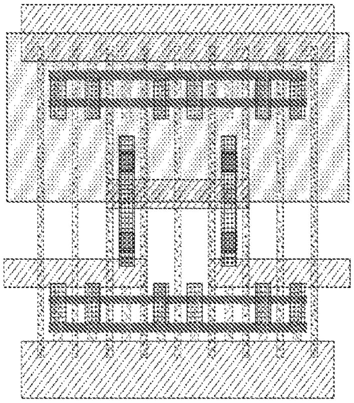
FIG. 2163A
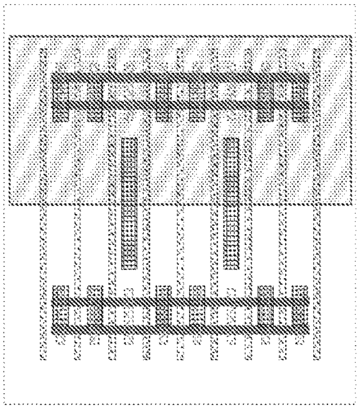
FIG. 2163B
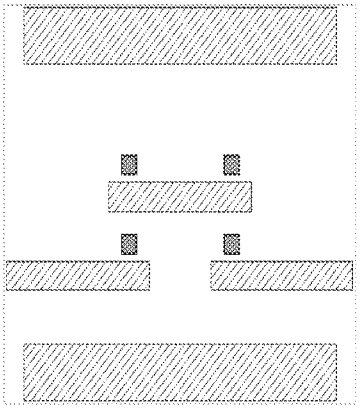
FIG. 2163C

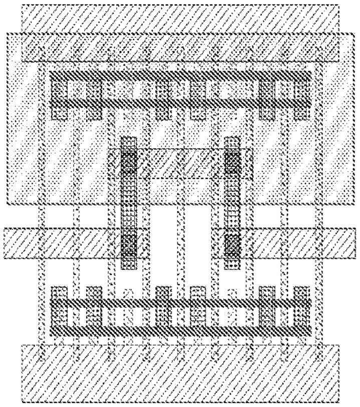
FIG. 2164A
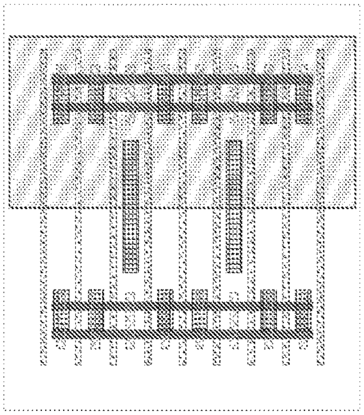
FIG. 2164B
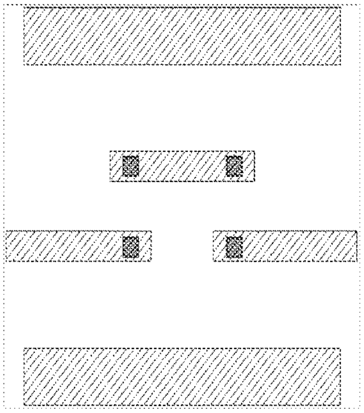
FIG. 2164C

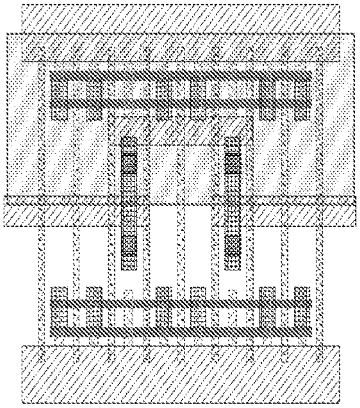
FIG. 2165A
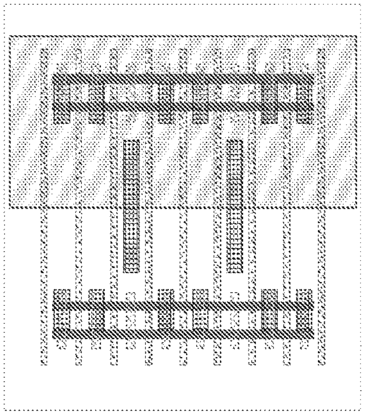
FIG. 2165B
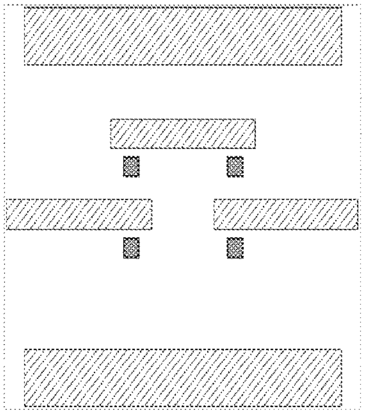
FIG. 2165C

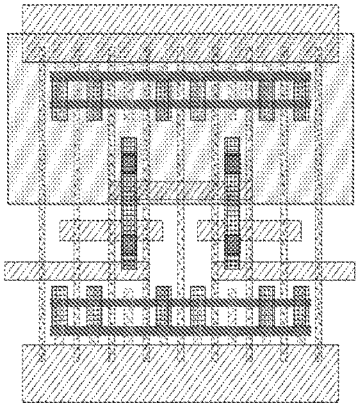
FIG. 2166A
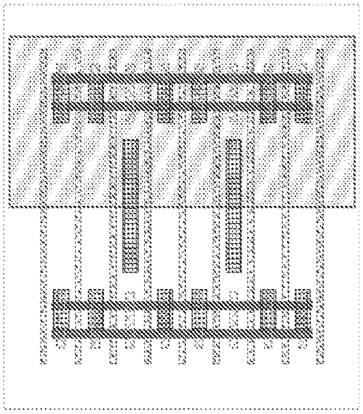
FIG. 2166B
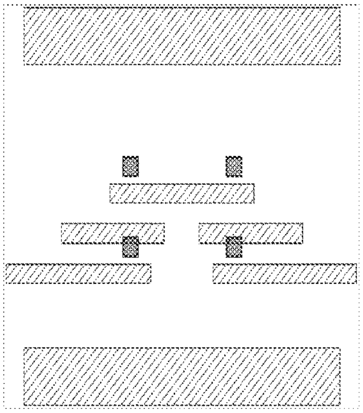
FIG. 2166C

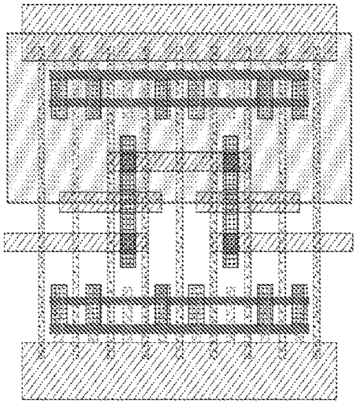
FIG. 2167A
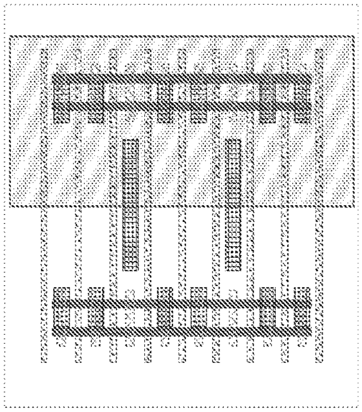
FIG. 2167B
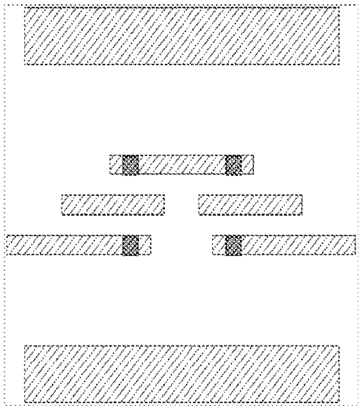
FIG. 2167C
*M* PDF Solutions, Inc.

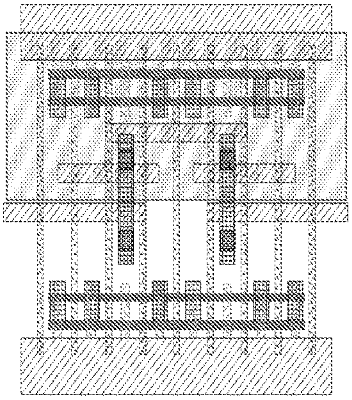
FIG. 2168A
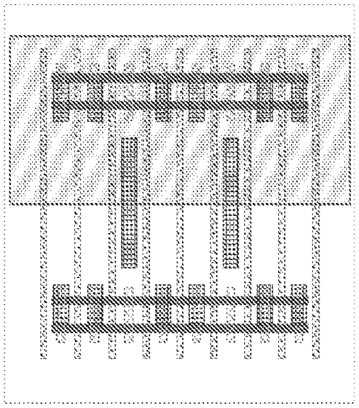
FIG. 2168B
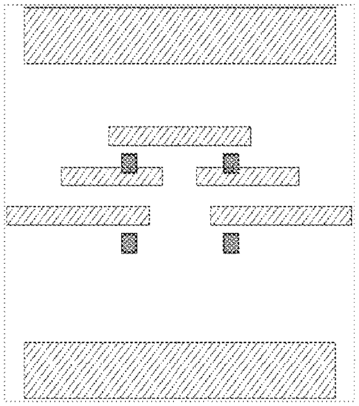
FIG. 2168C

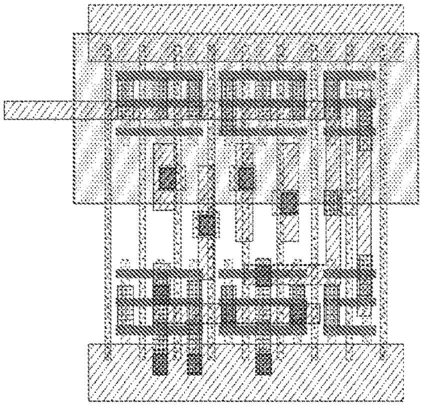
FIG. 2169A
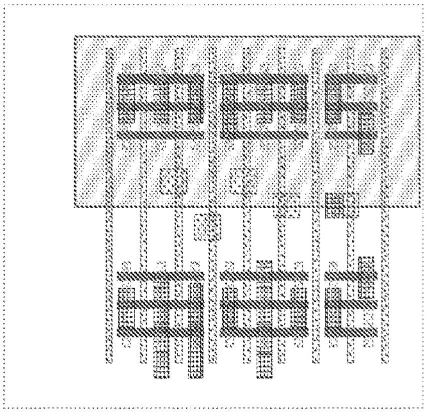
FIG. 2169B
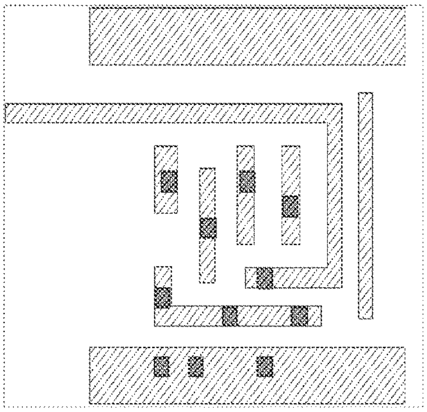
FIG. 2169C

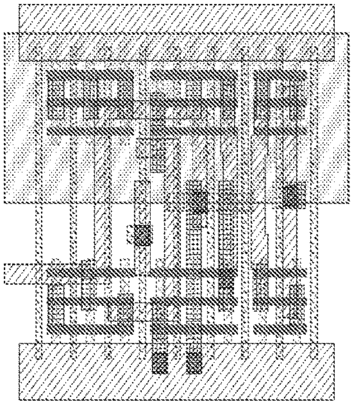
FIG. 2170A
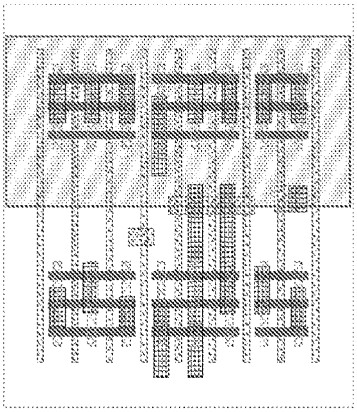
FIG. 2170B
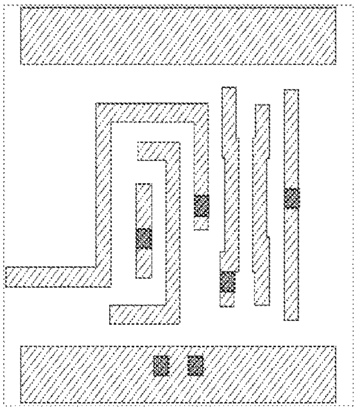
FIG. 2170C
*M* PDF Solutions, Inc.

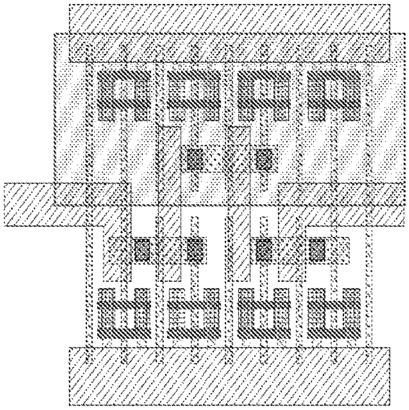
FIG. 2171A
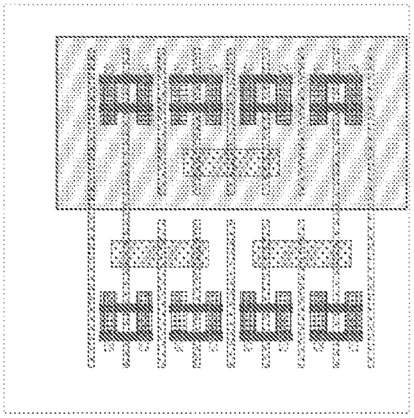
FIG. 2171B
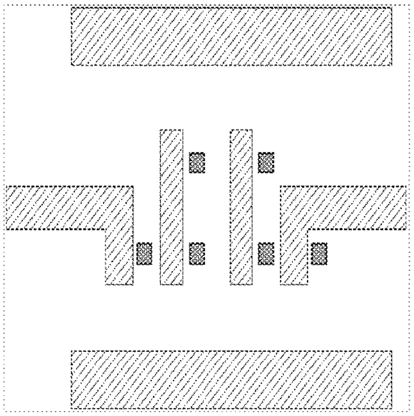
FIG. 2171C

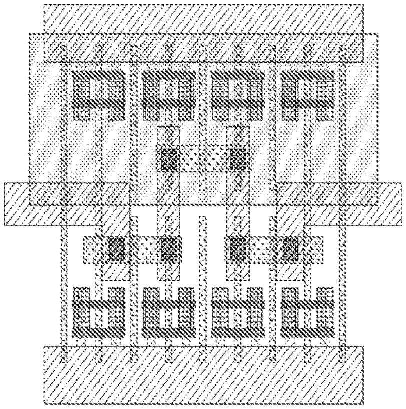
FIG. 2172A
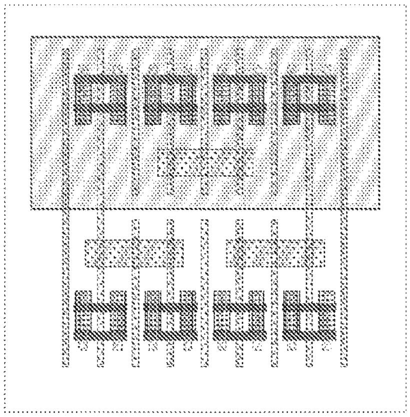
FIG. 2172B
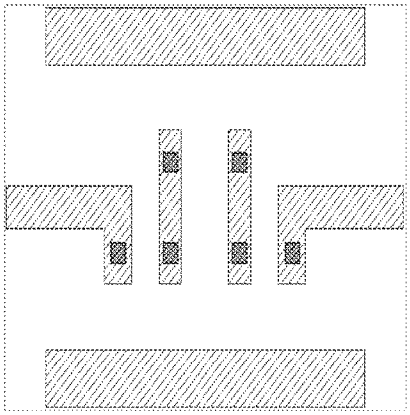
FIG. 2172C

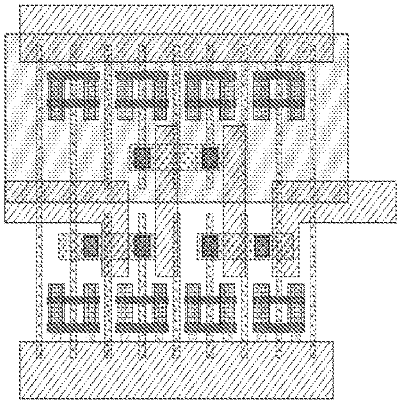
FIG. 2173A
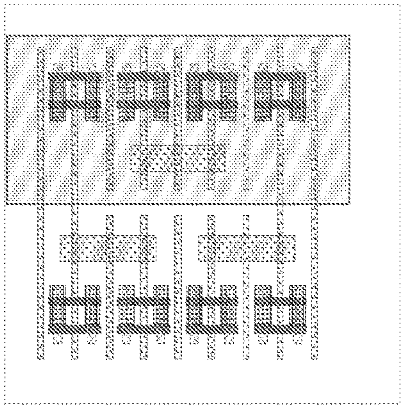
FIG. 2173B
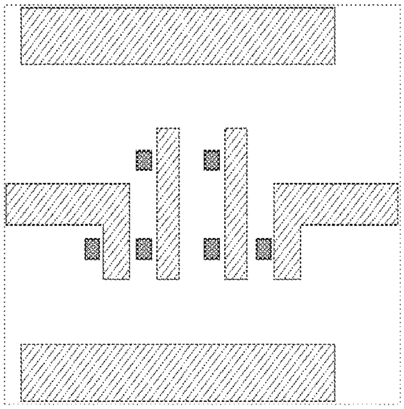
FIG. 2173C

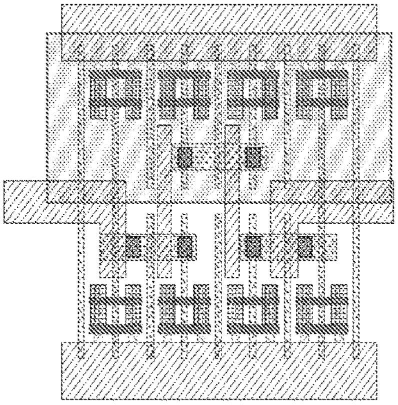
FIG. 2174A
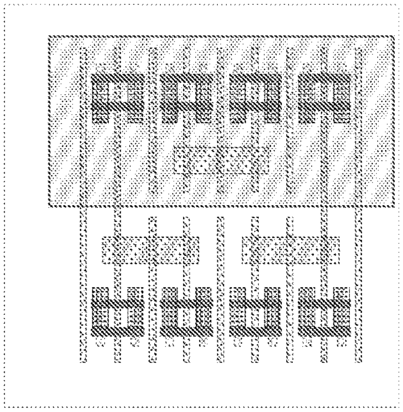
FIG. 2174B
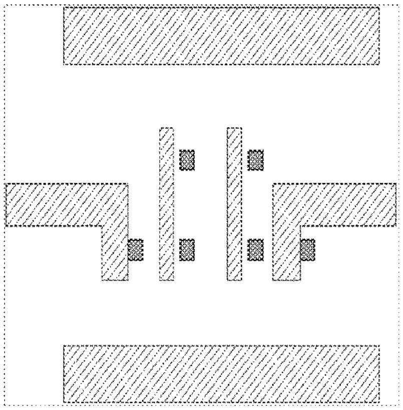
FIG. 2174C

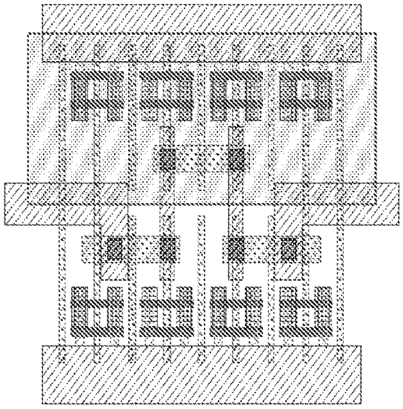
FIG. 2175A
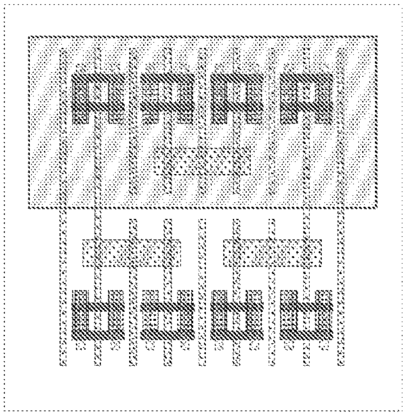
FIG. 2175B
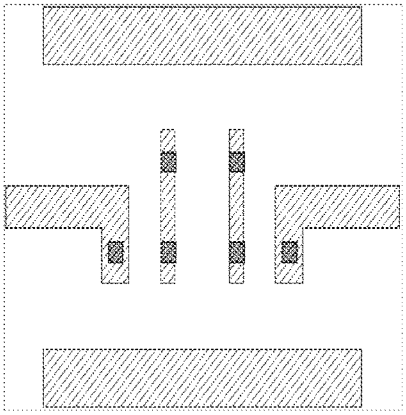
FIG. 2175C

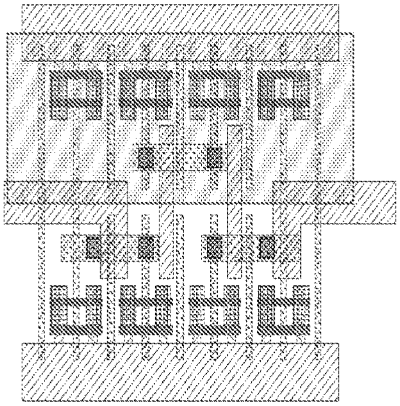
FIG. 2176A
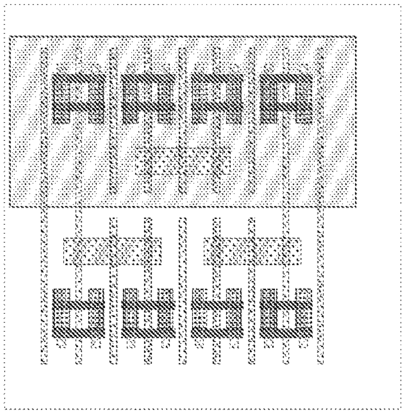
FIG. 2176B
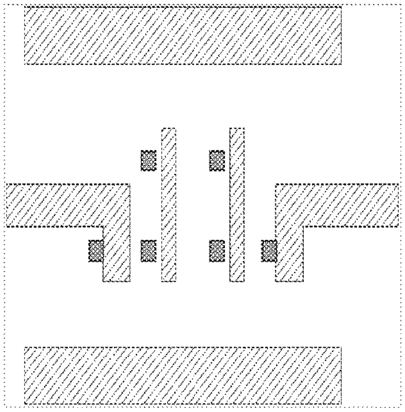
FIG. 2176C

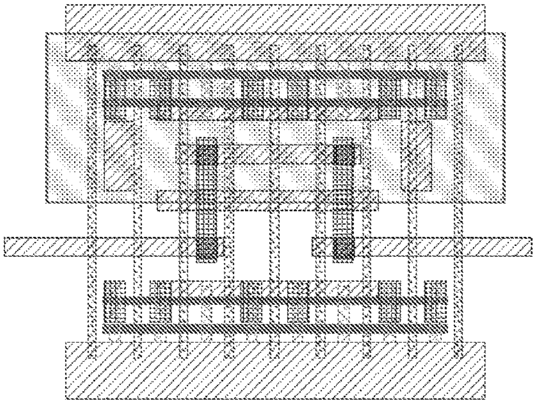
FIG. 2177A
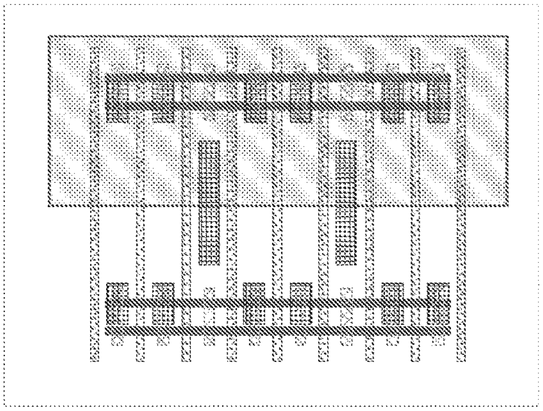
FIG. 2177B
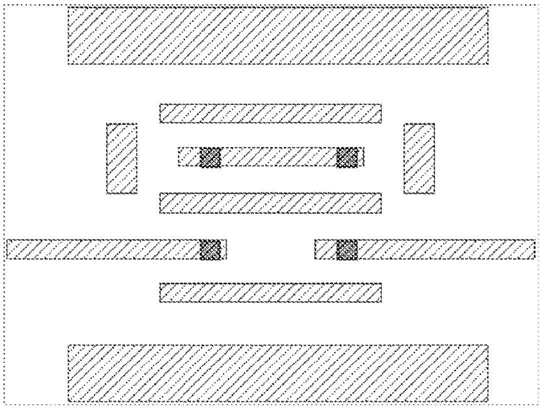
FIG. 2177C

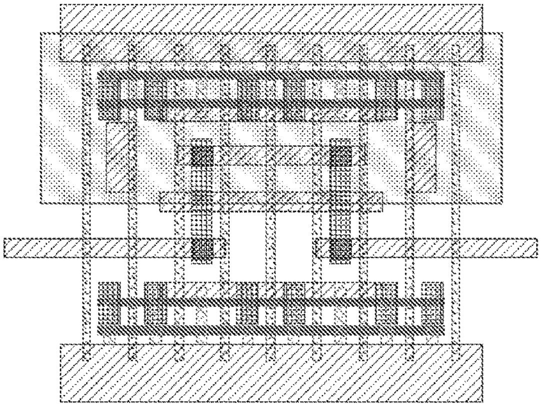
FIG. 2178A
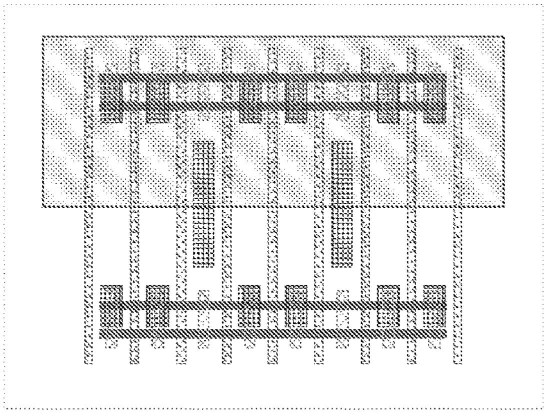
FIG. 2178B
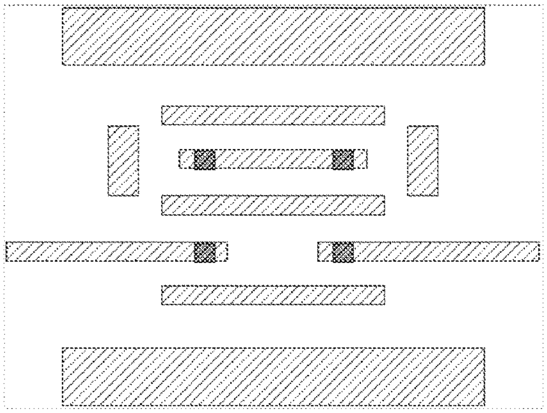
FIG. 2178C

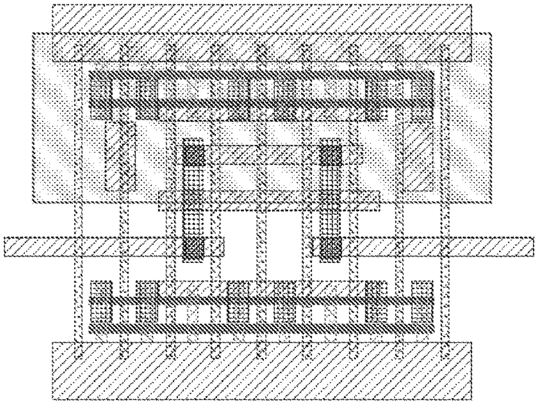
FIG. 2179A
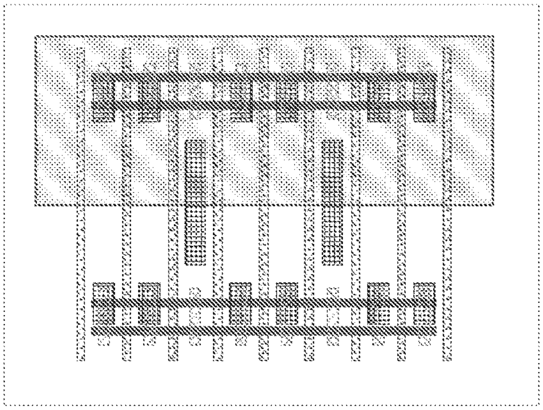
FIG. 2179B
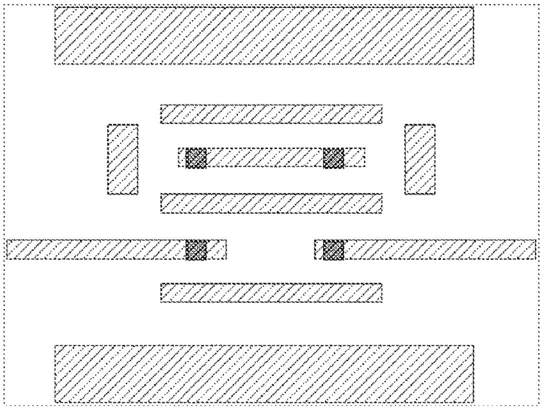
FIG. 2179C
*M* PDF Solutions, Inc.

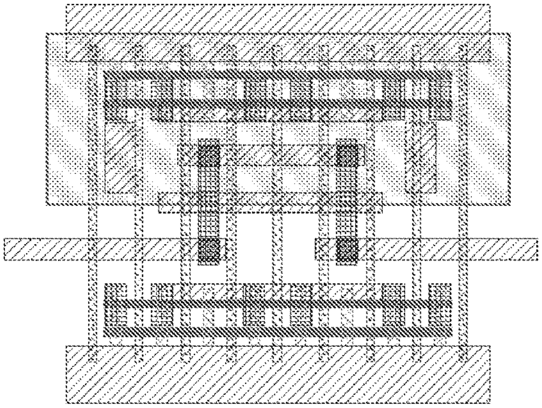
FIG. 2180A
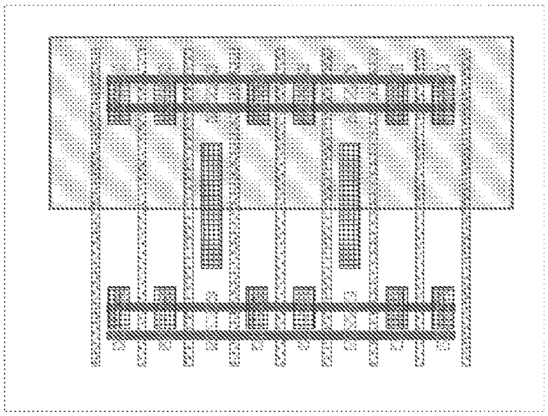
FIG. 2180B
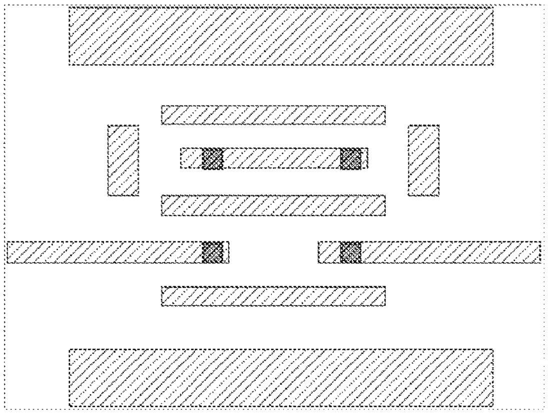
FIG. 2180C

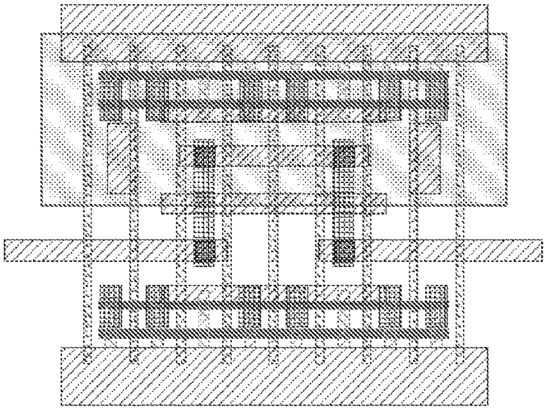
FIG. 2181A
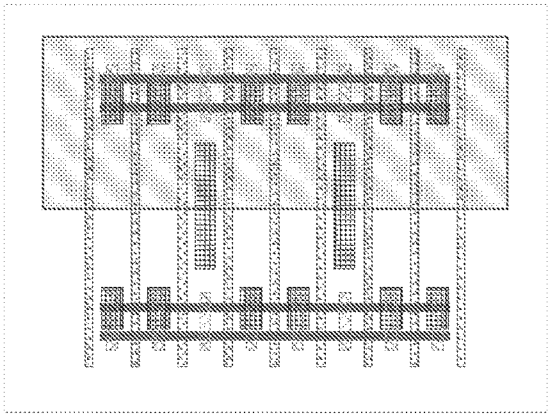
FIG. 2181B
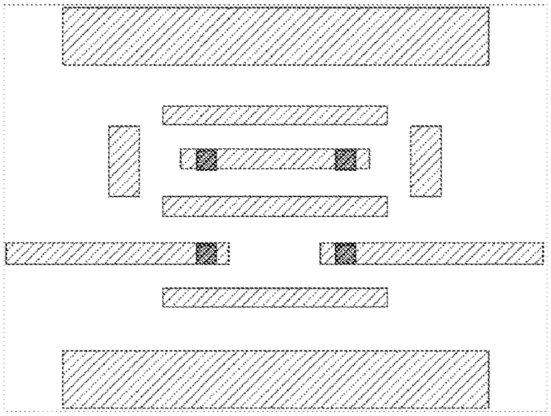
FIG. 2181C
*M* PDF Solutions, Inc.

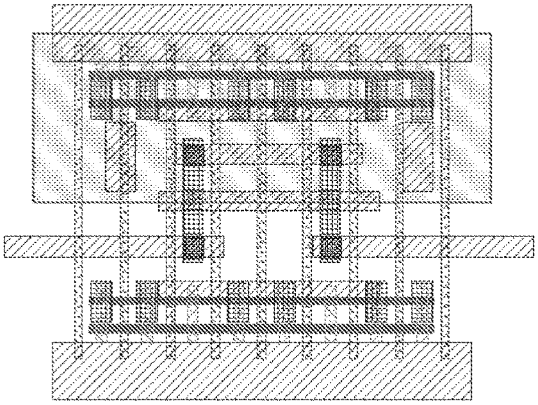
FIG. 2182A
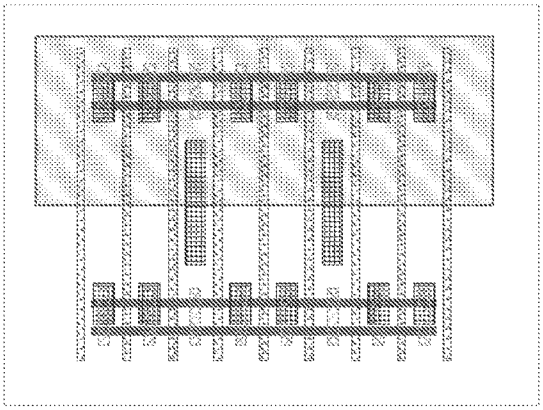
FIG. 2182B
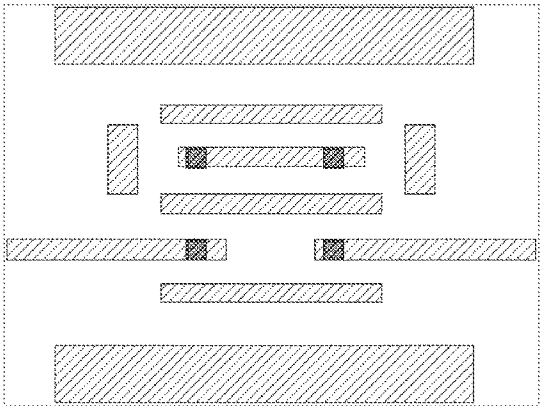
FIG. 2182C

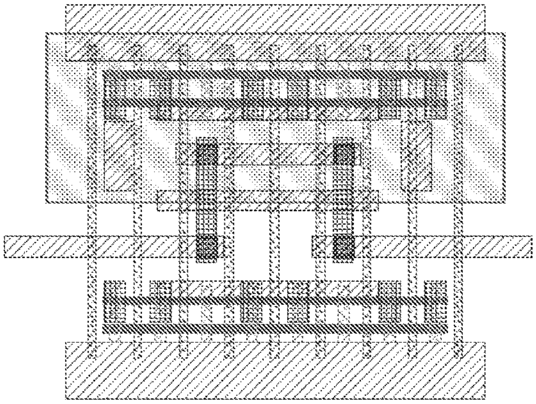
FIG. 2183A
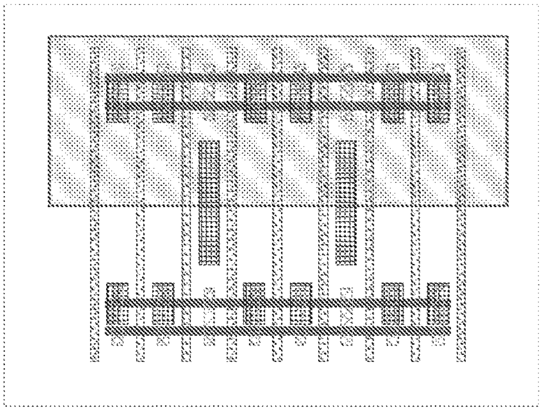
FIG. 2183B
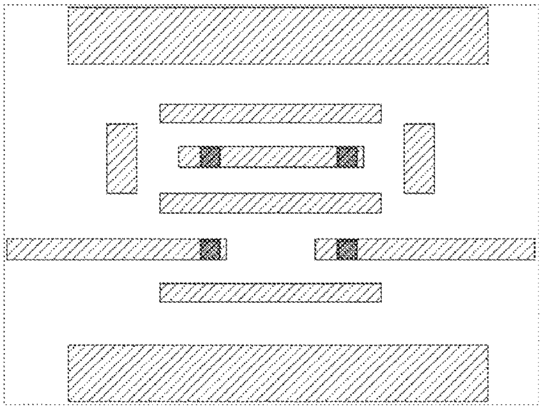
FIG. 2183C
*M* PDF Solutions, Inc.

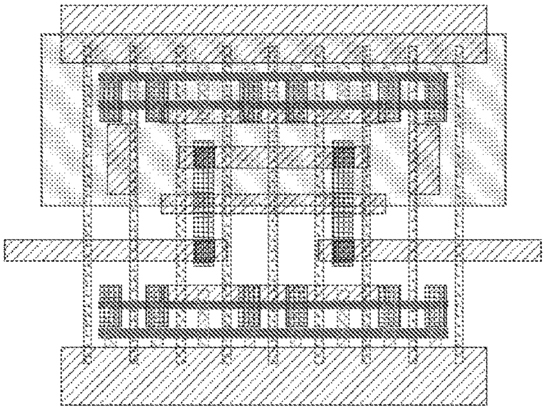
FIG. 2184A
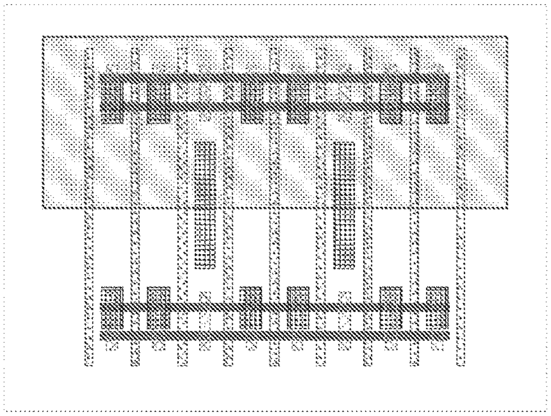
FIG. 2184B
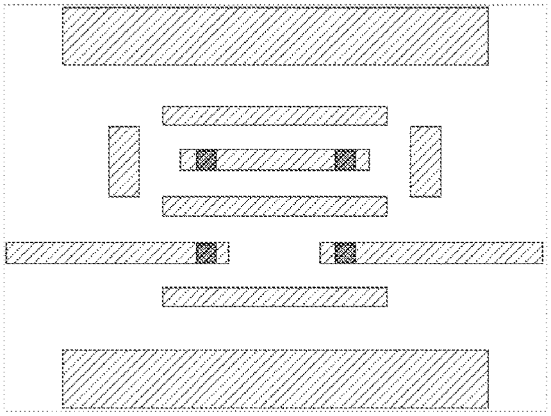
FIG. 2184C

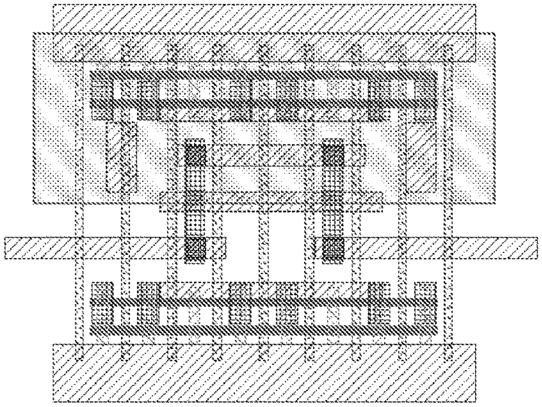
FIG. 2185A
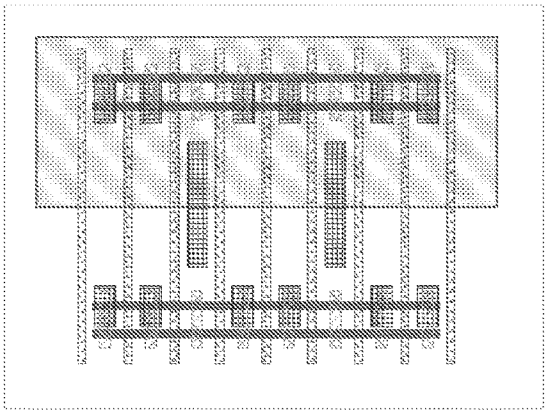
FIG. 2185B
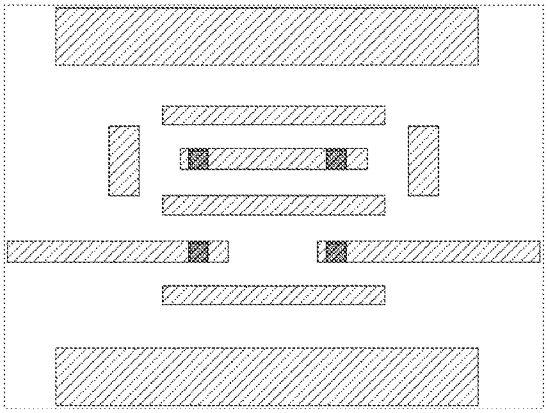
FIG. 2185C

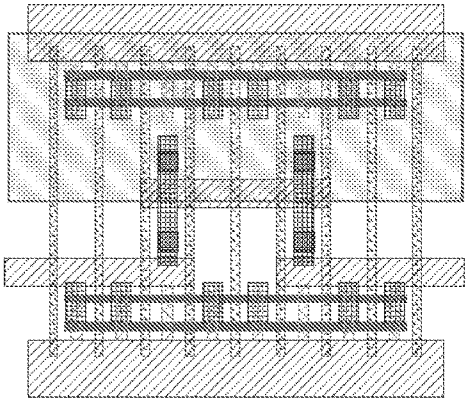
FIG. 2186A
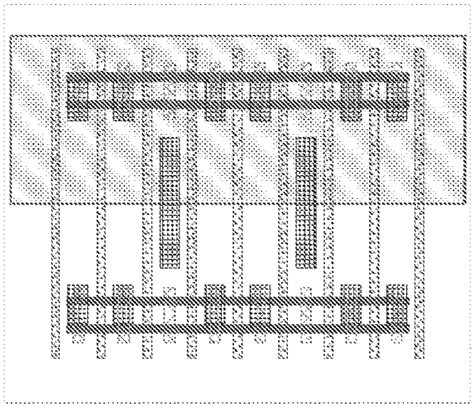
FIG. 2186B
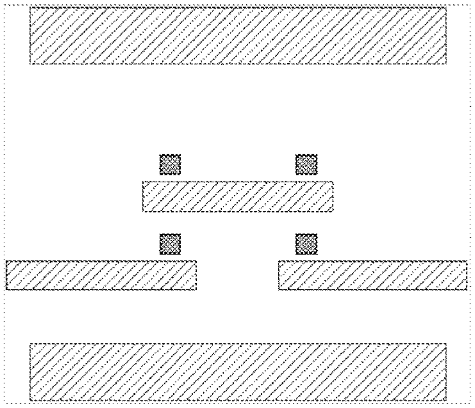
FIG. 2186C
*M* PDF Solutions, Inc.

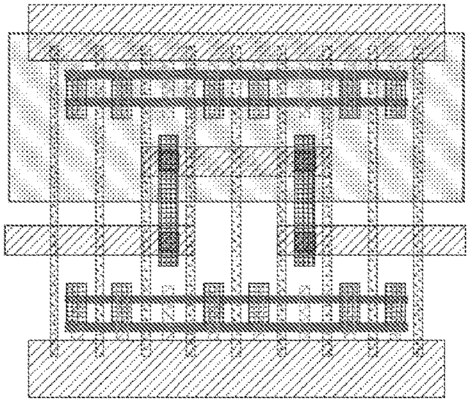
FIG. 2187A
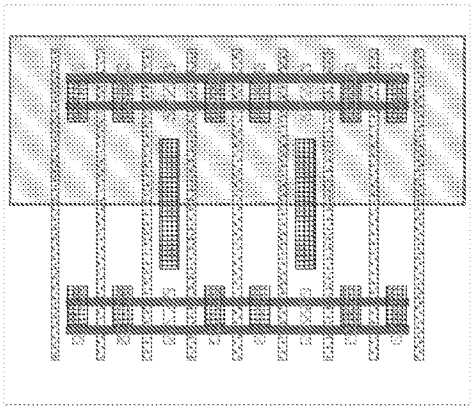
FIG. 2187B
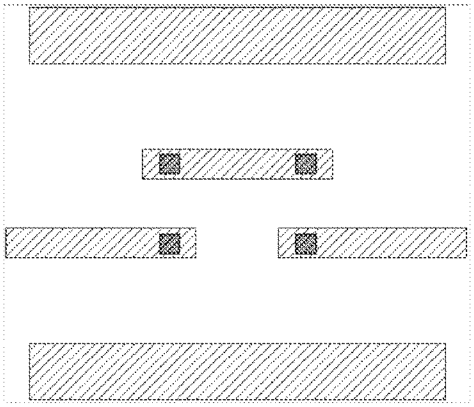
FIG. 2187C

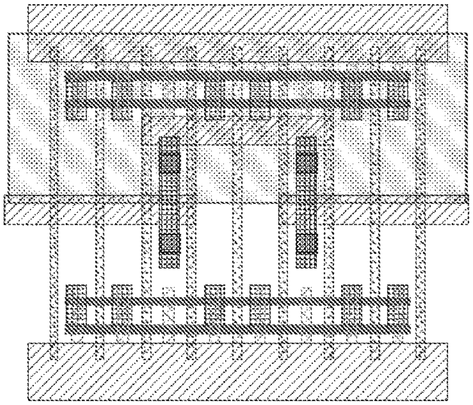
FIG. 2188A
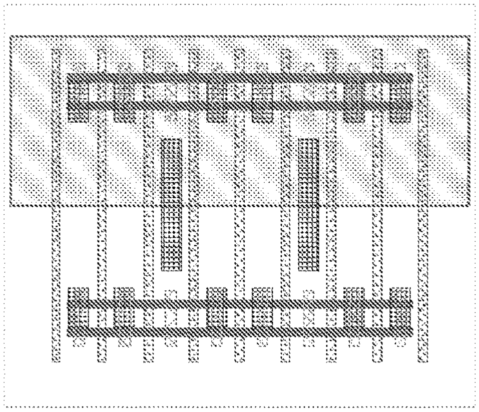
FIG. 2188B
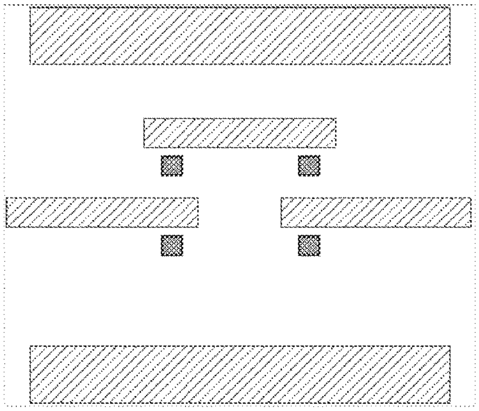
FIG. 2188C

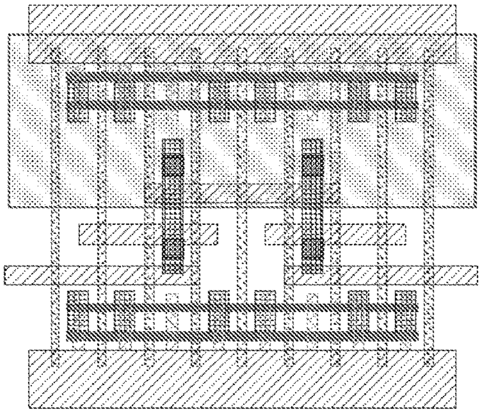
FIG. 2189A
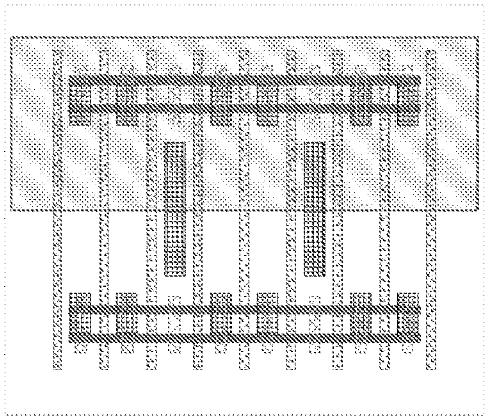
FIG. 2189B
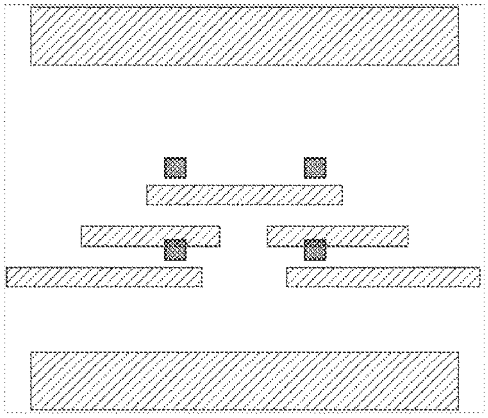
FIG. 2189C

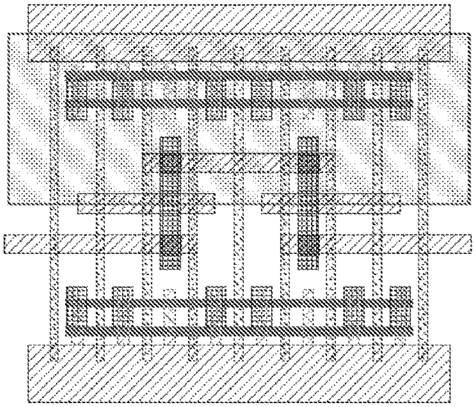
FIG. 2190A
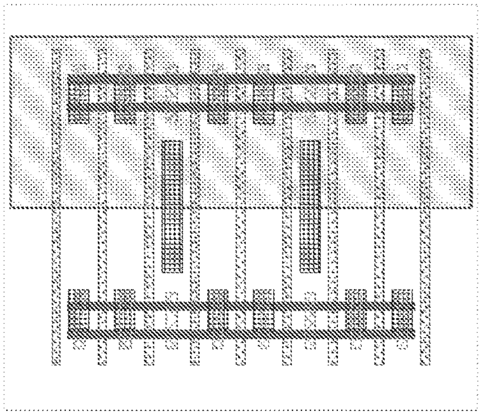
FIG. 2190B
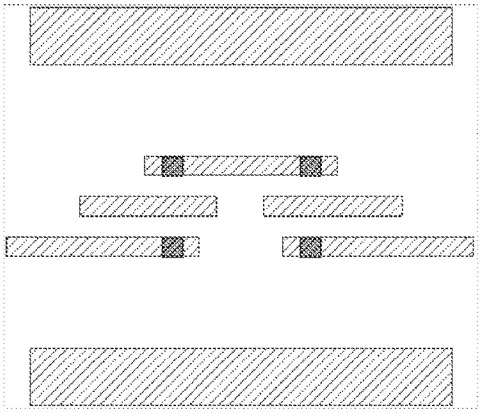
FIG. 2190C

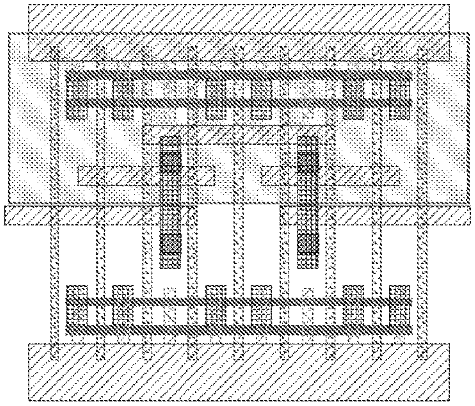
FIG. 2191A
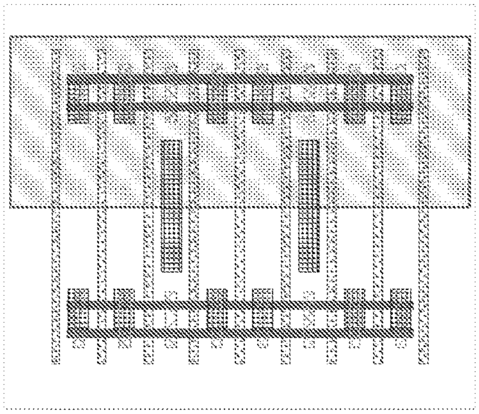
FIG. 2191B
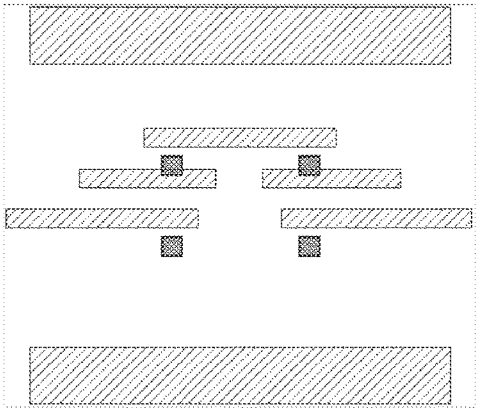
FIG. 2191C

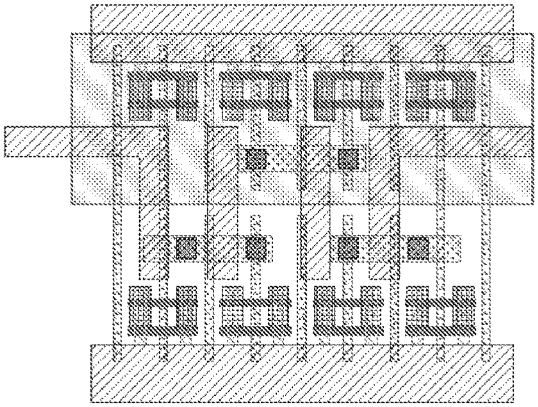
FIG. 2192A
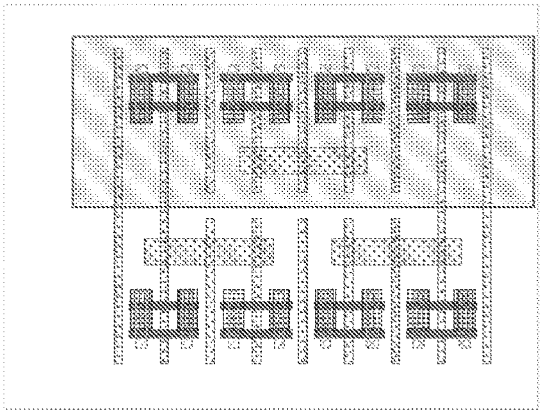
FIG. 2192B
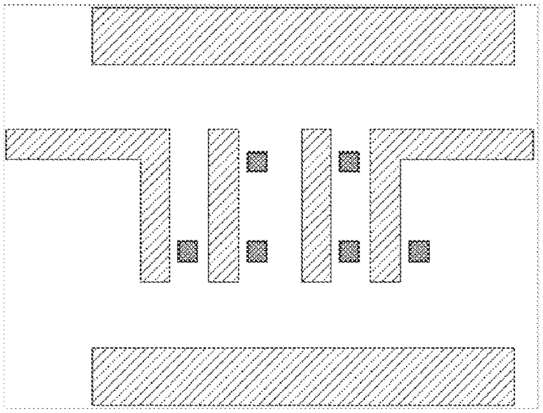
FIG. 2192C

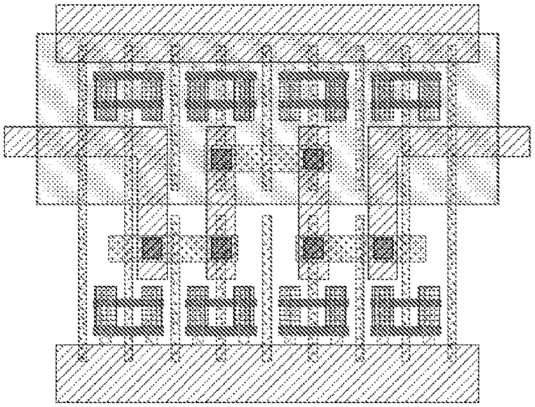
FIG. 2193A
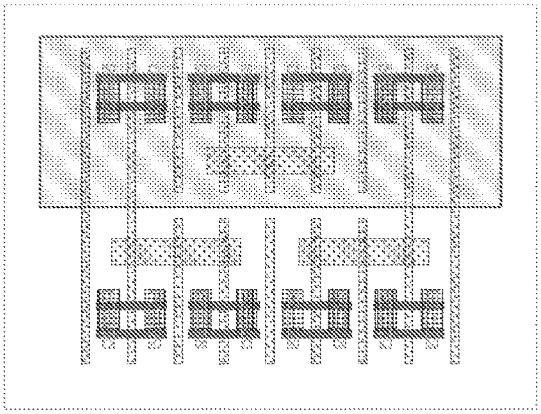
FIG. 2193B
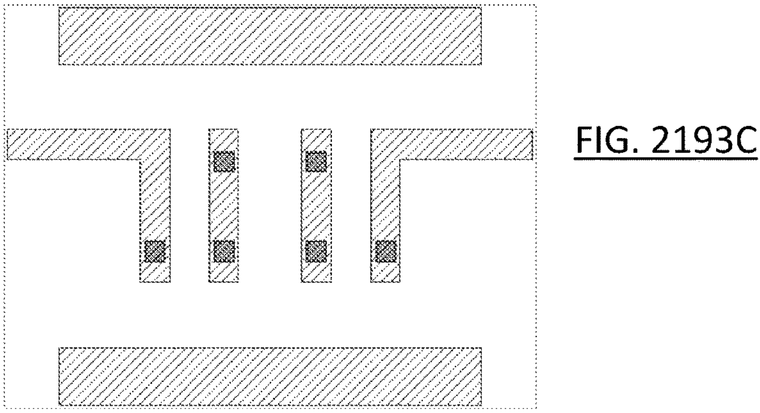
FIG. 2193C

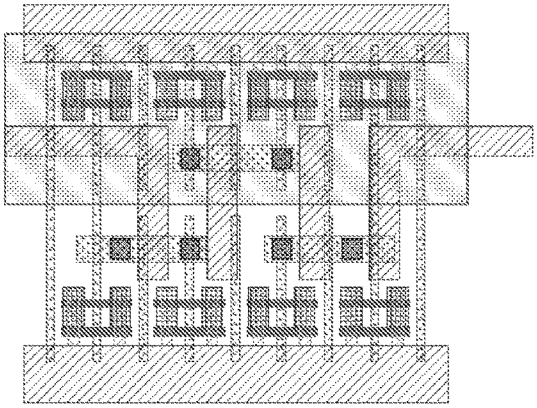
FIG. 2194A
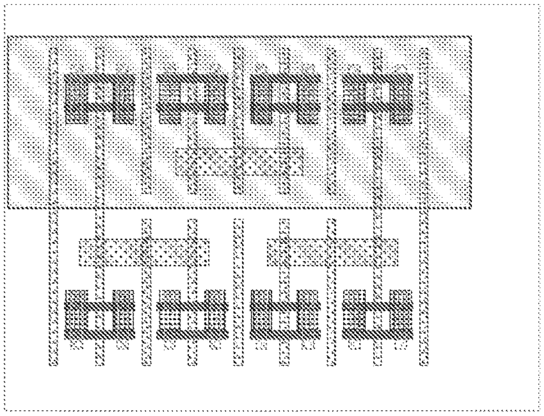
FIG. 2194B
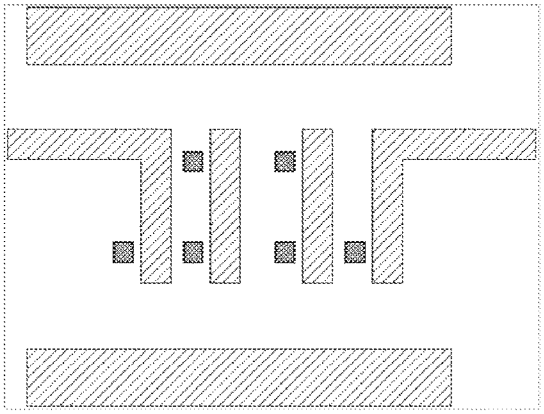
FIG. 2194C

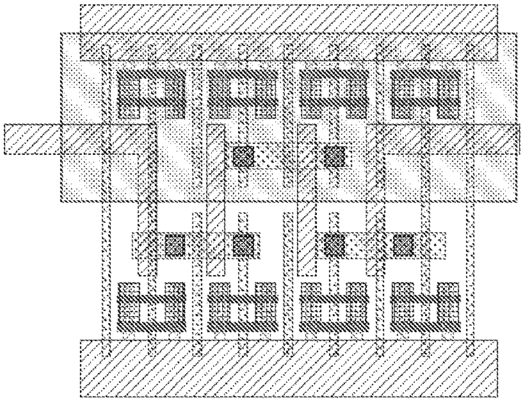
FIG. 2195A
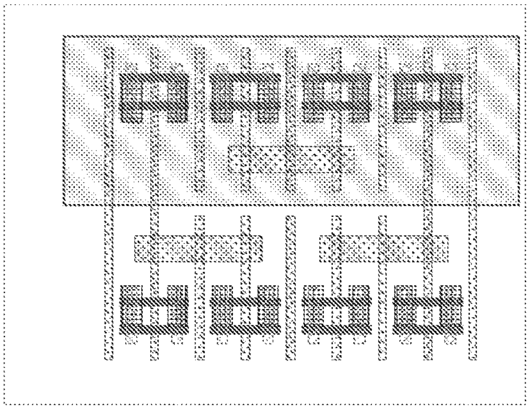
FIG. 2195B
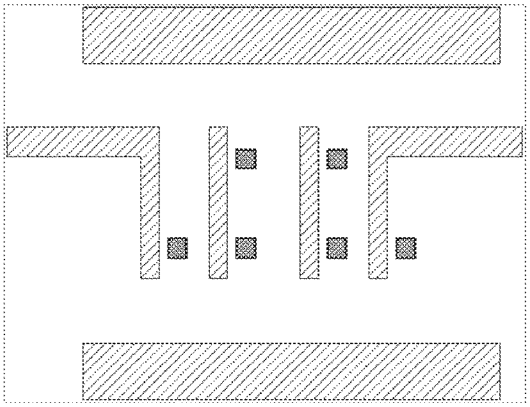
FIG. 2195C

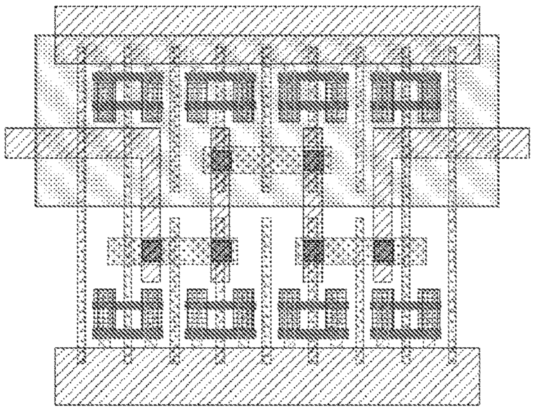
FIG. 2196A
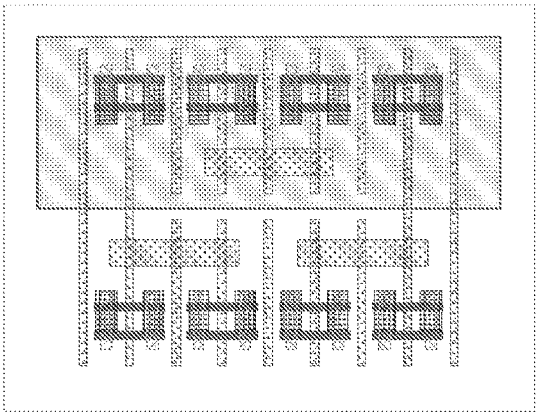
FIG. 2196B
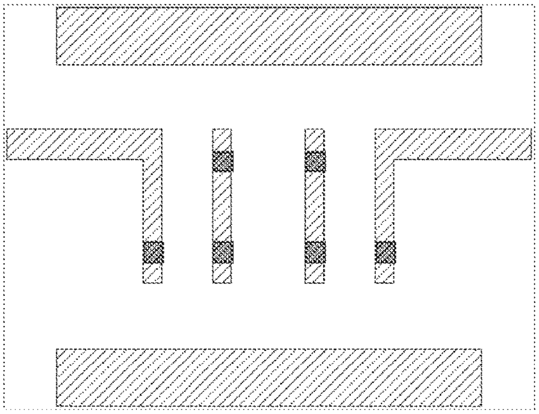
FIG. 2196C

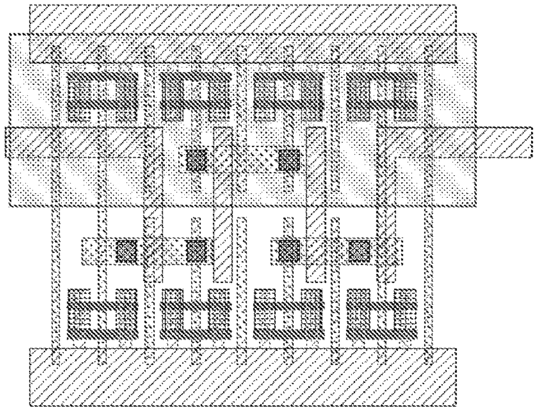
FIG. 2197A
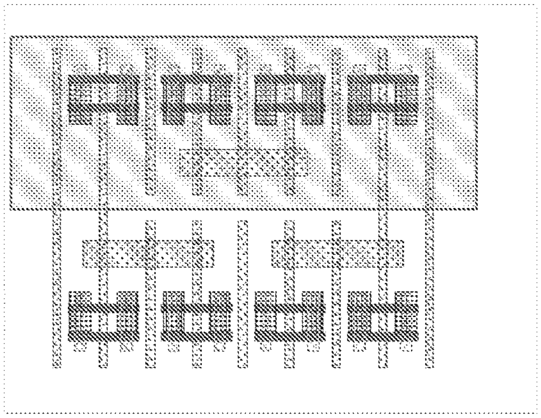
FIG. 2197B
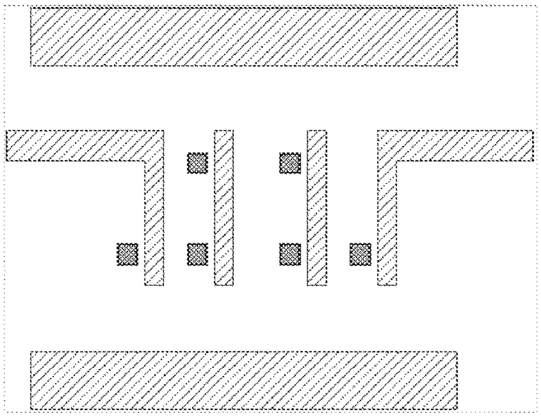
FIG. 2197C

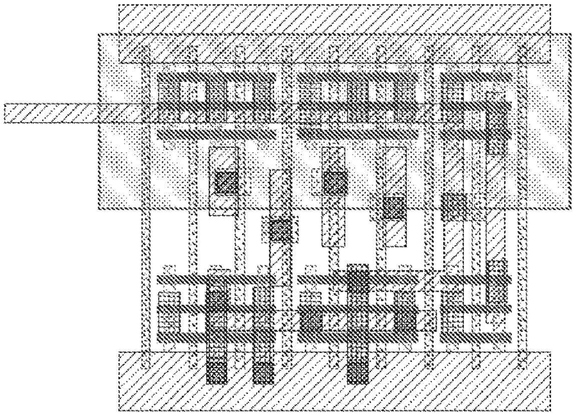
FIG. 2198A
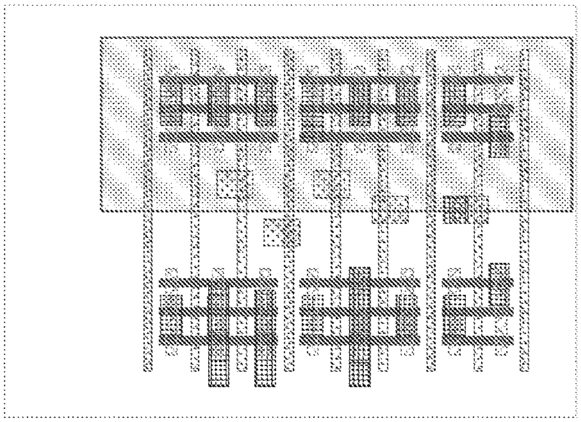
FIG. 2198B
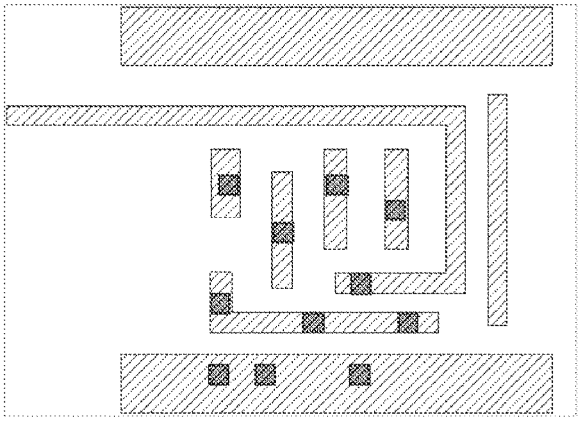
FIG. 2198C

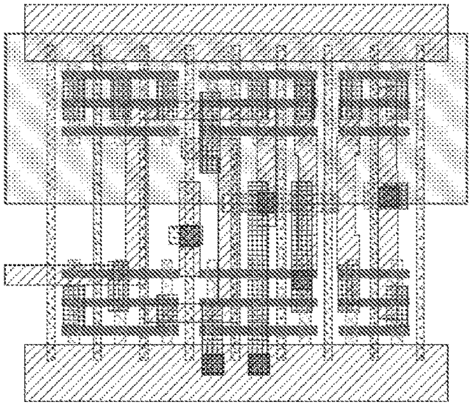
FIG. 2199A
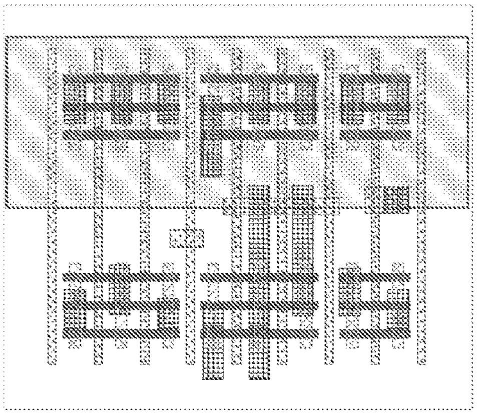
FIG. 2199B
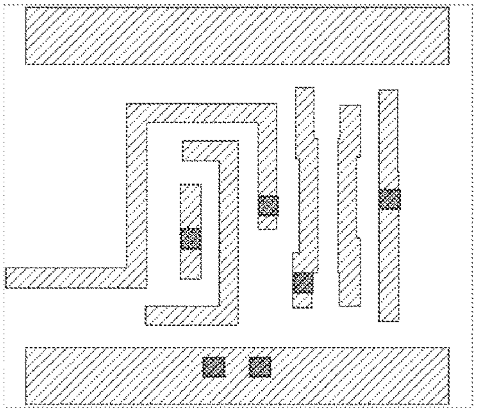
FIG. 2199C

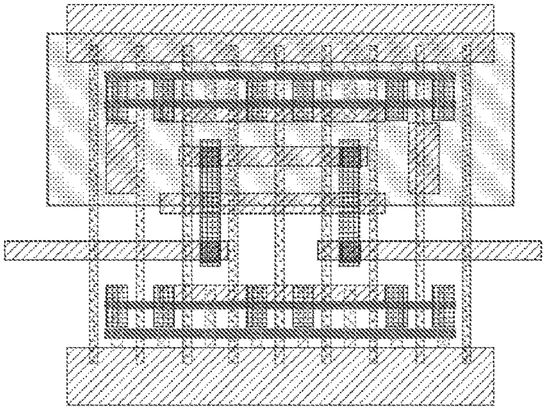
FIG. 2200A
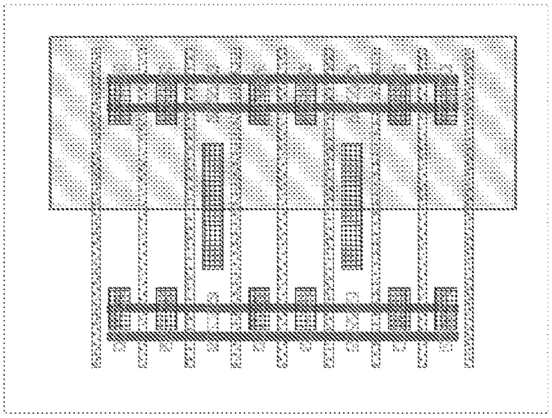
FIG. 2200B
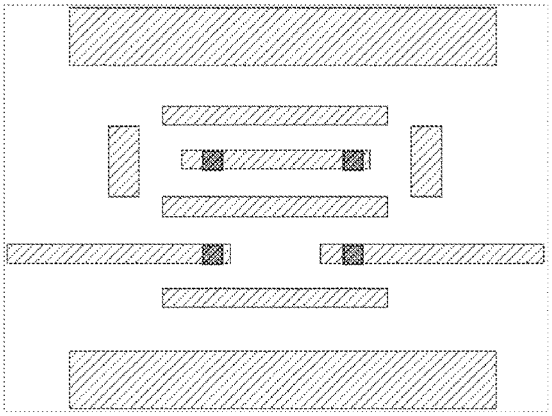
FIG. 2200C

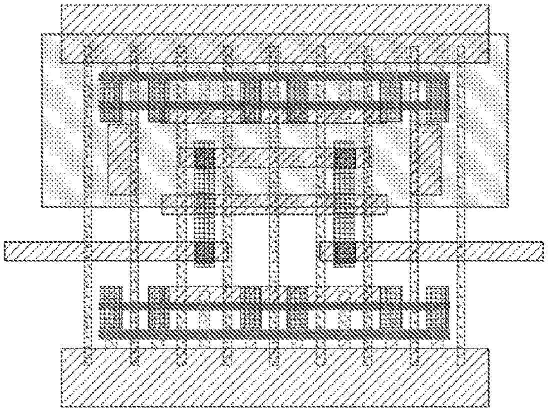
FIG. 2201A
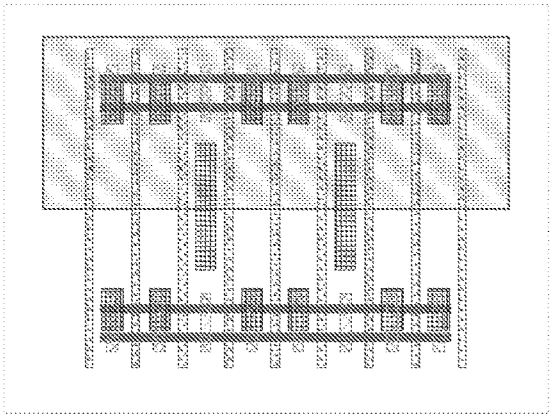
FIG. 2201B
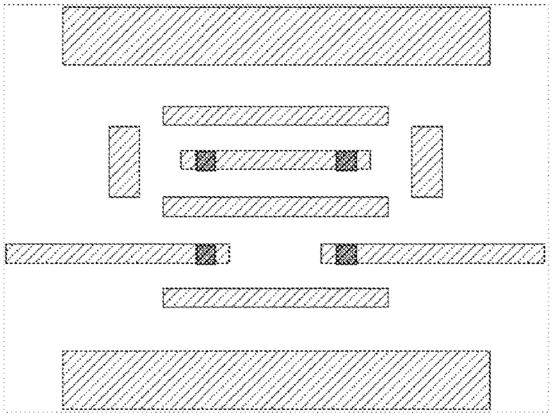
FIG. 2201C
*M* PDF Solutions, Inc.

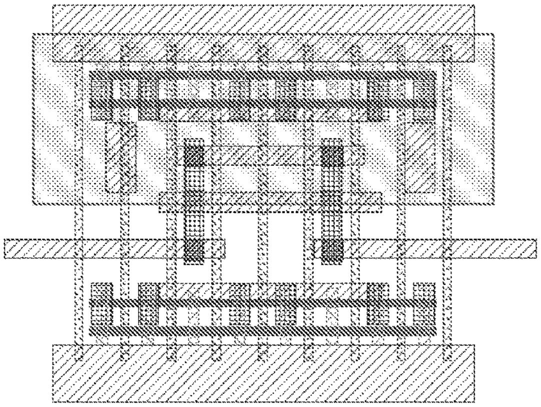
FIG. 2202A
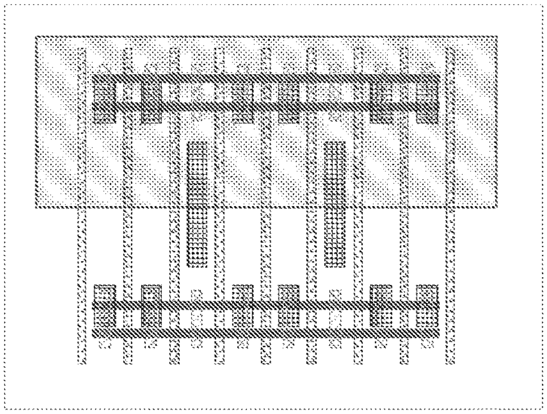
FIG. 2202B
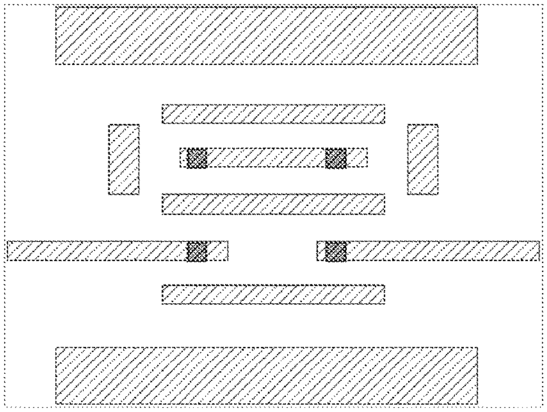
FIG. 2202C
*M* PDF Solutions, Inc.

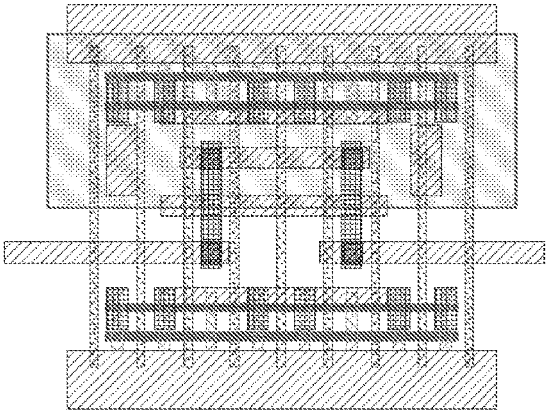
FIG. 2203A
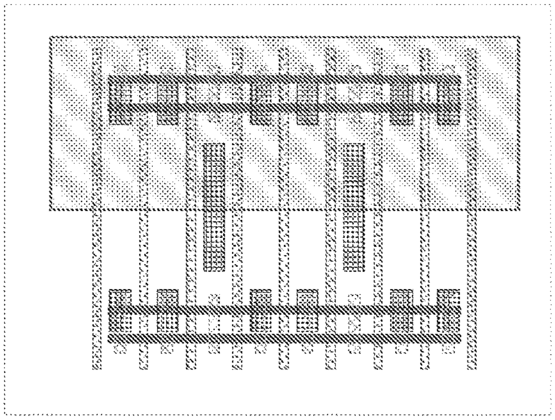
FIG. 2203B
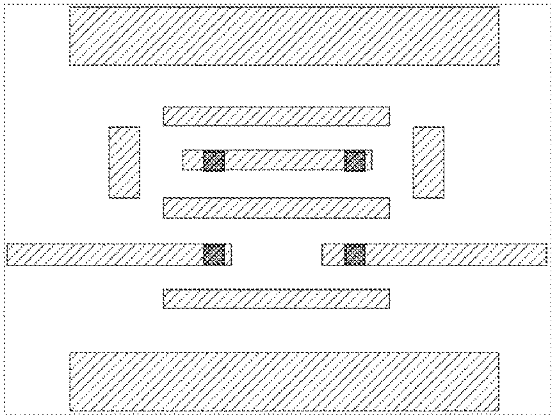
FIG. 2203C
*M* PDF Solutions, Inc.

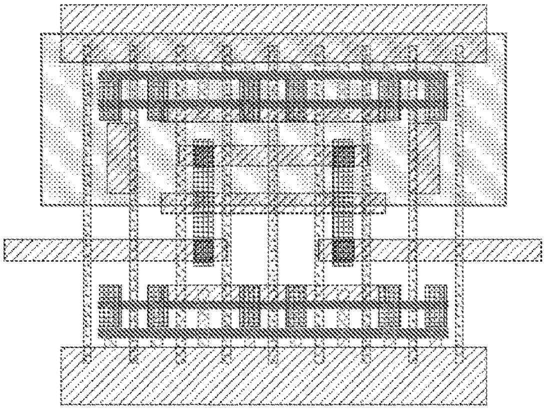
FIG. 2204A
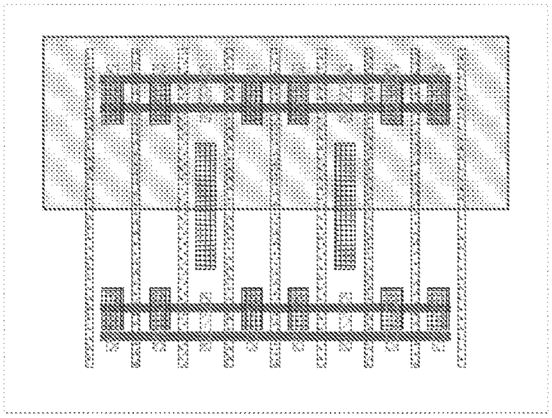
FIG. 2204B
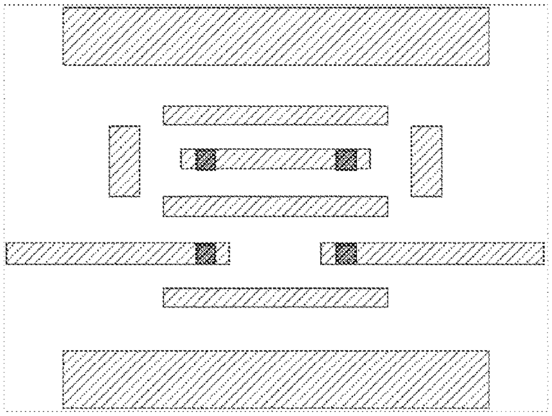
FIG. 2204C
*M* PDF Solutions, Inc.

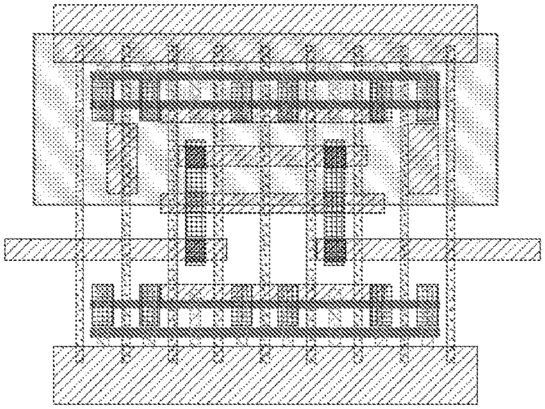
FIG. 2205A
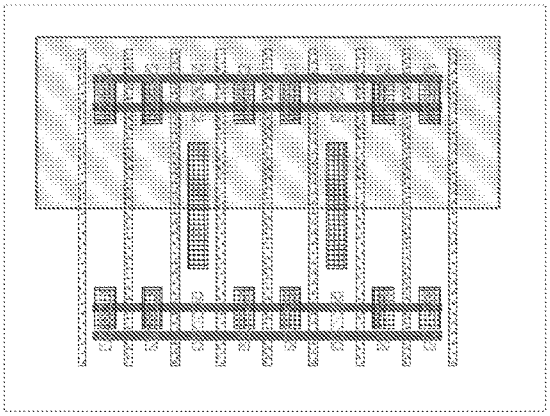
FIG. 2205B
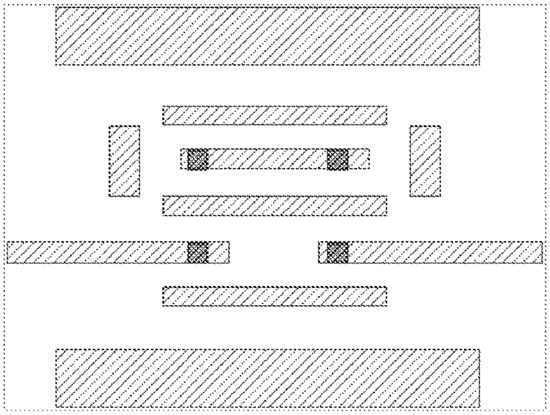
FIG. 2205C
*M* PDF Solutions, Inc.

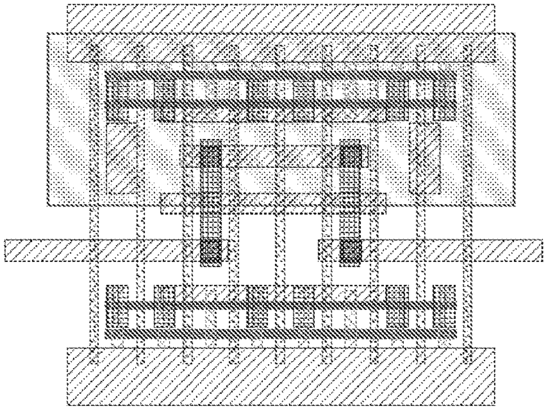
FIG. 2206A
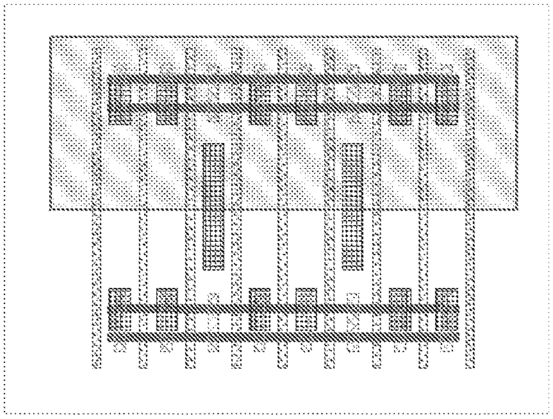
FIG. 2206B
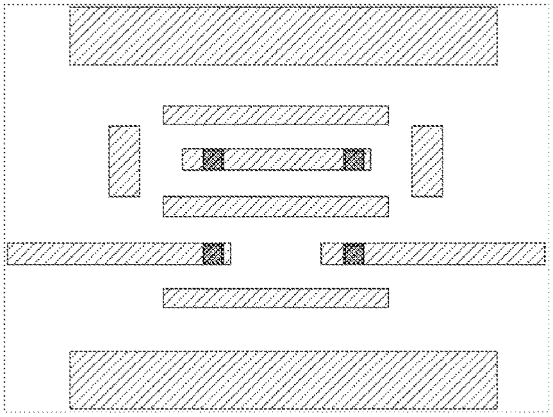
FIG. 2206C
*M* PDF Solutions, Inc.

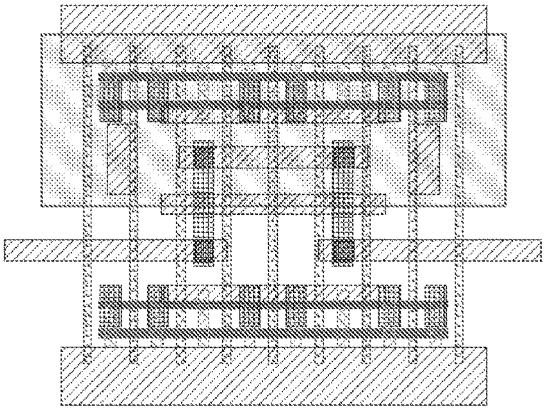
FIG. 2207A
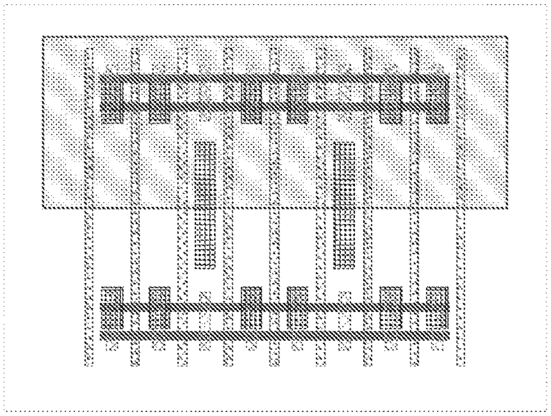
FIG. 2207B
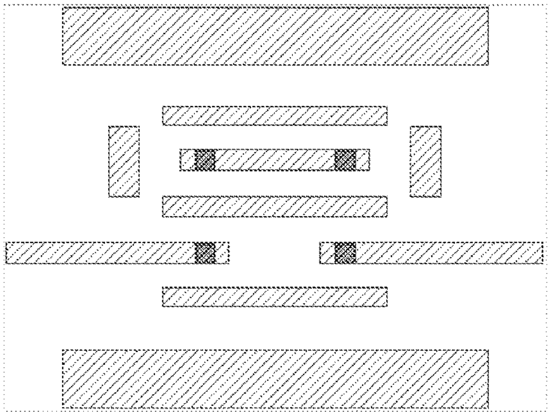
FIG. 2207C

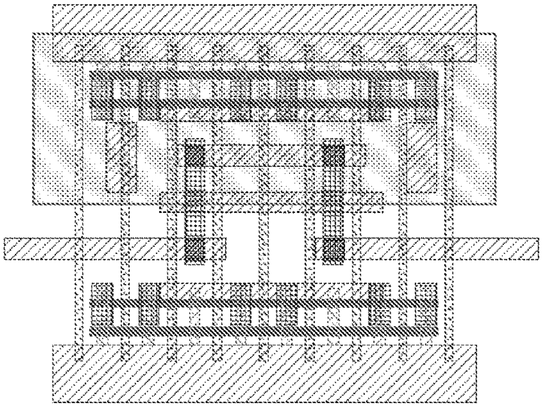
FIG. 2208A
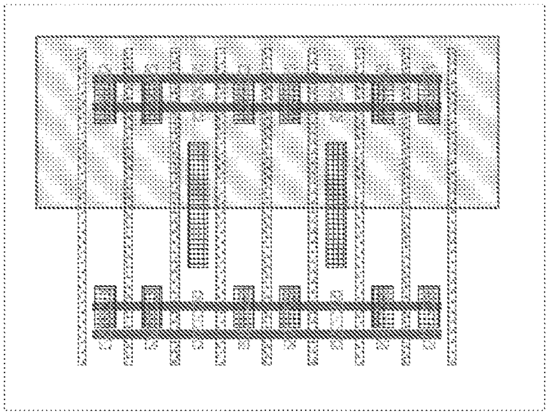
FIG. 2208B
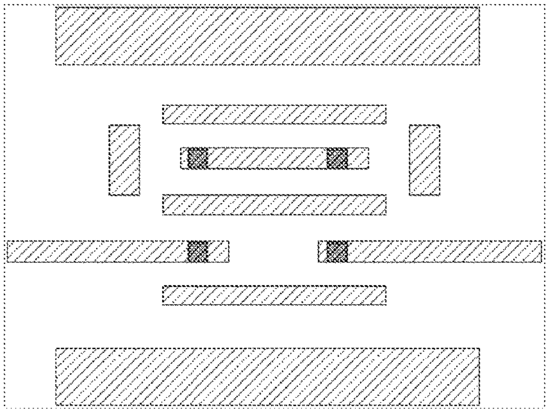
FIG. 2208C
*M* PDF Solutions, Inc.

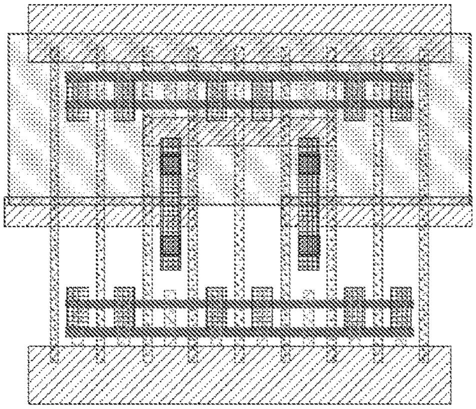
FIG. 2209A
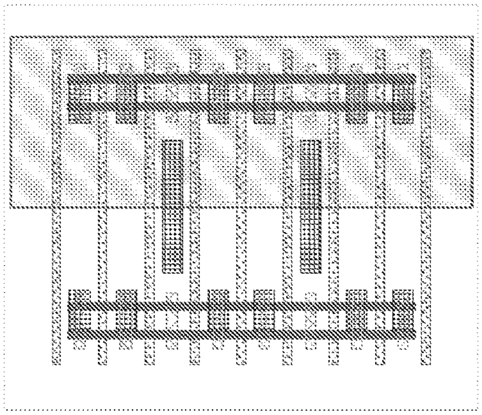
FIG. 2209B
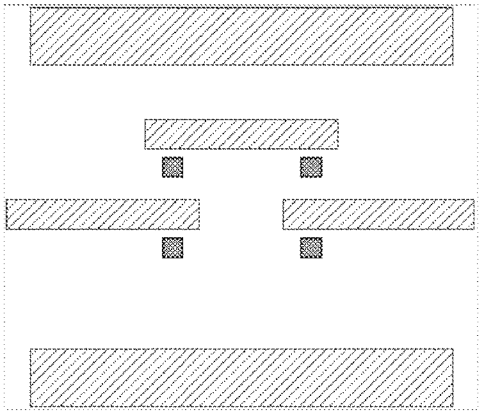
FIG. 2209C

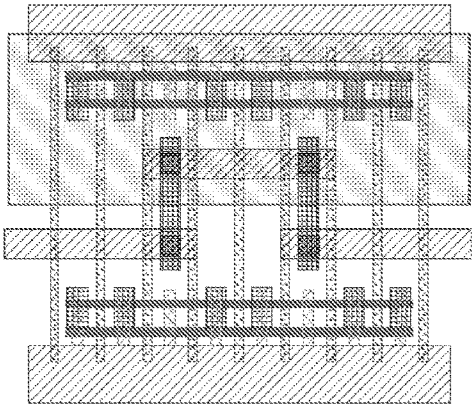
FIG. 2210A
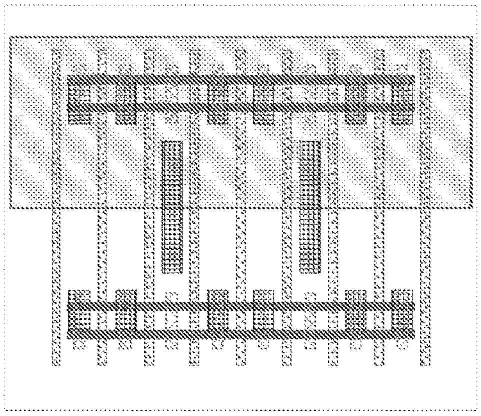
FIG. 2210B
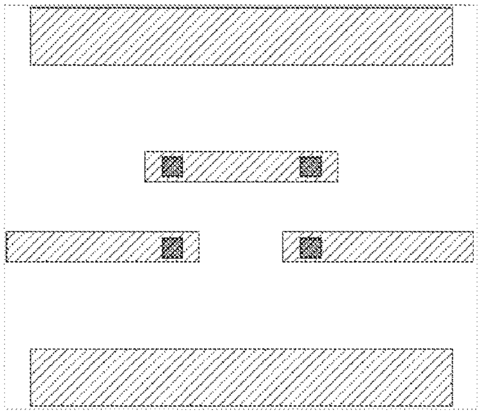
FIG. 2210C
*M* PDF Solutions, Inc.

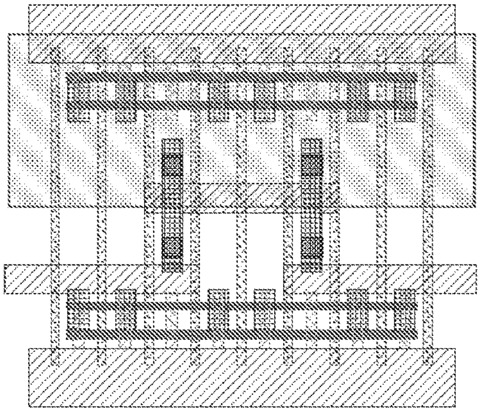
FIG. 2211A
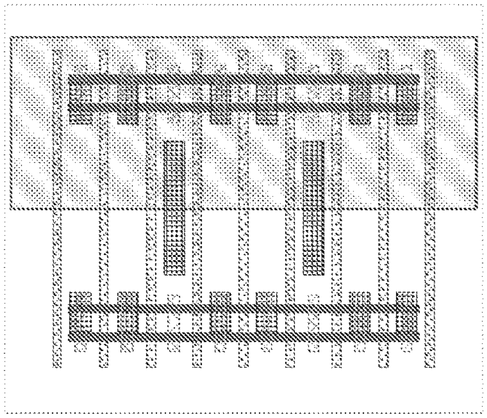
FIG. 2211B
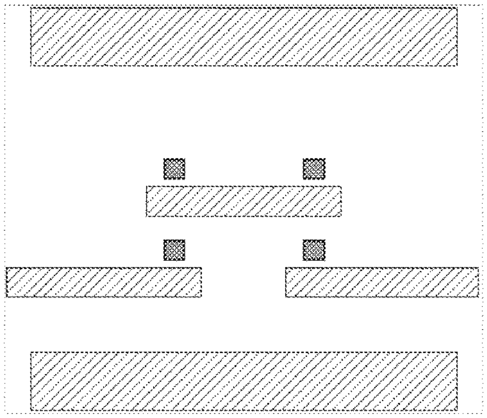
FIG. 2211C

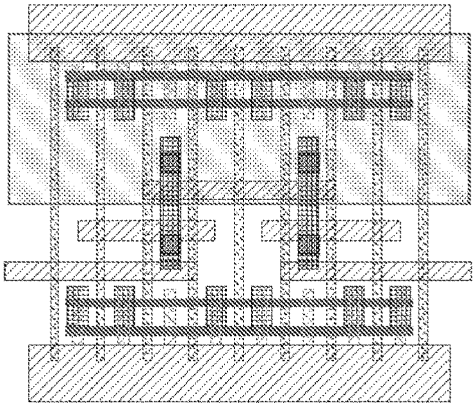
FIG. 2212A
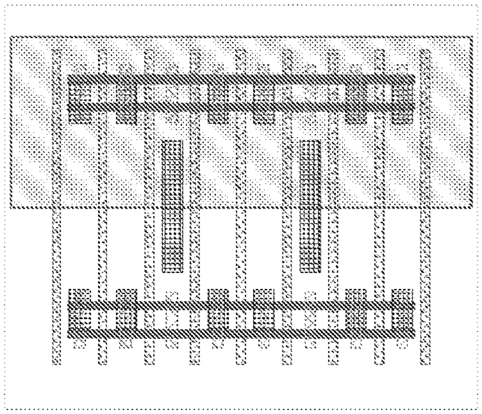
FIG. 2212B
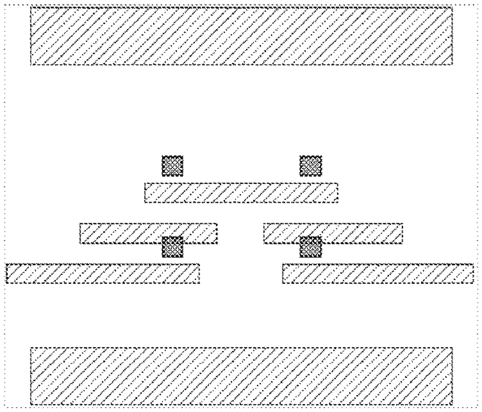
FIG. 2212C

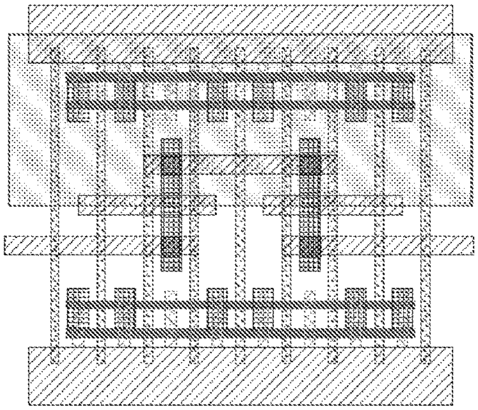
FIG. 2213A
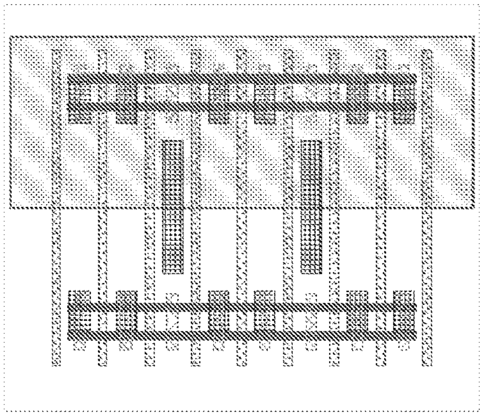
FIG. 2213B
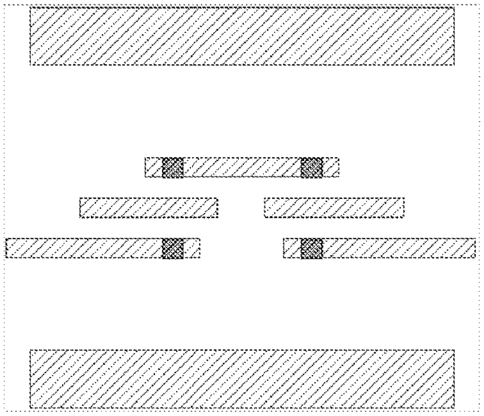
FIG. 2213C

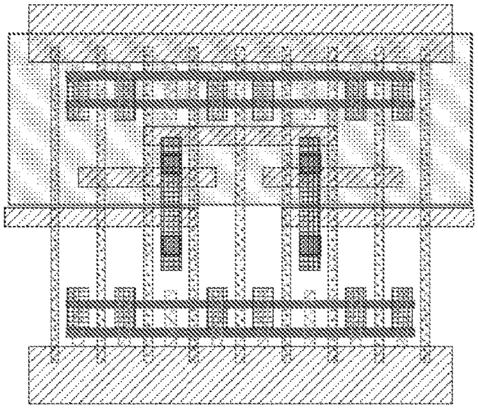
FIG. 2214A
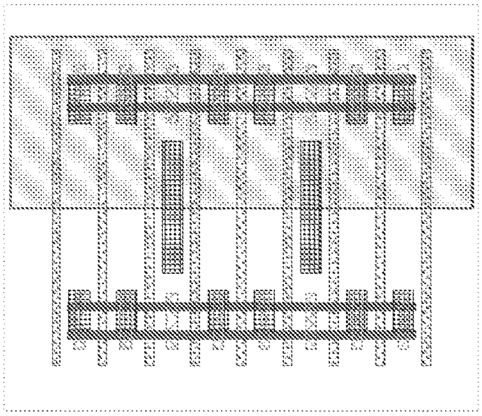
FIG. 2214B
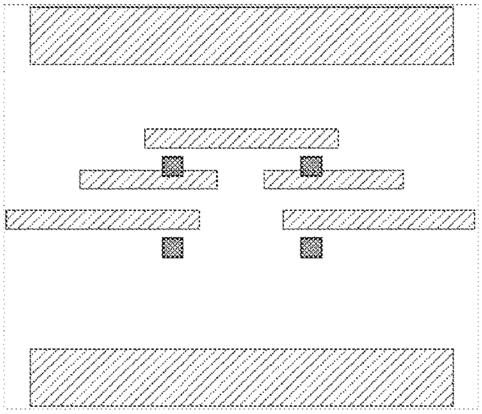
FIG. 2214C

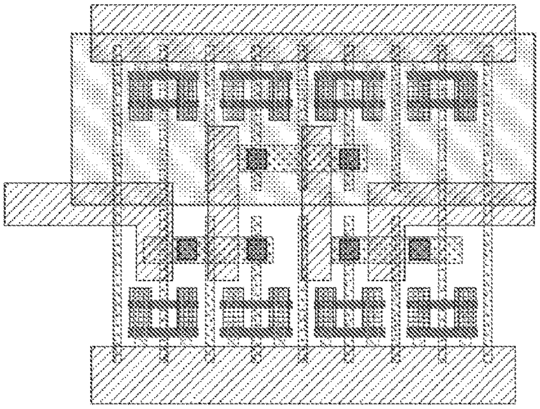
FIG. 2215A
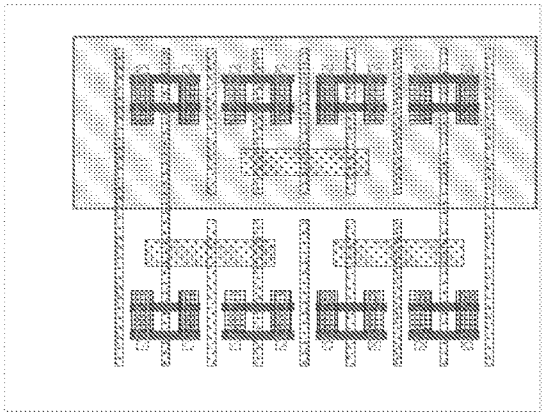
FIG. 2215B
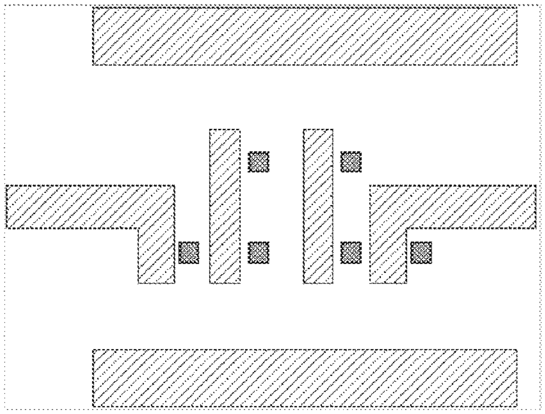
FIG. 2215C

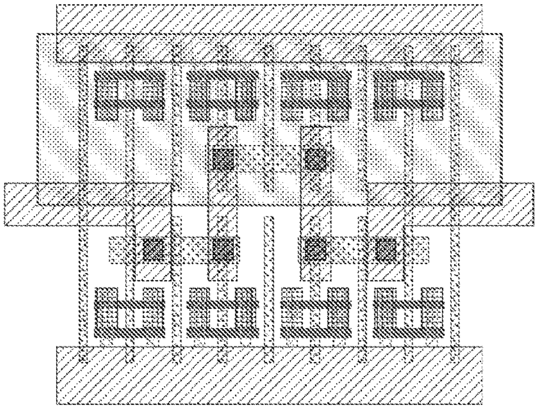
FIG. 2216A
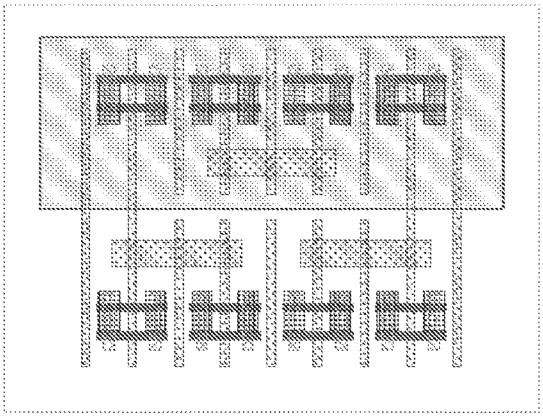
FIG. 2216B
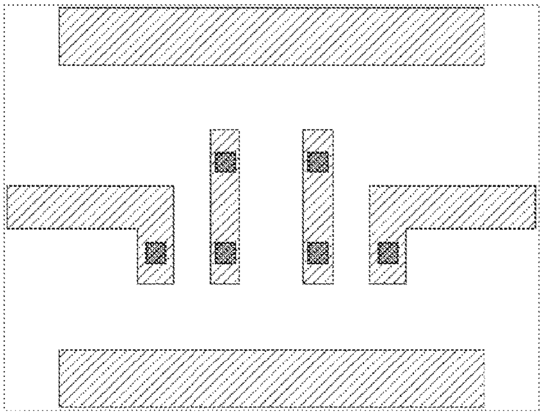
FIG. 2216C

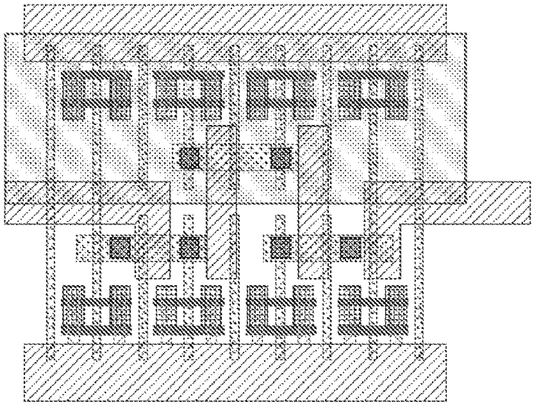
FIG. 2217A
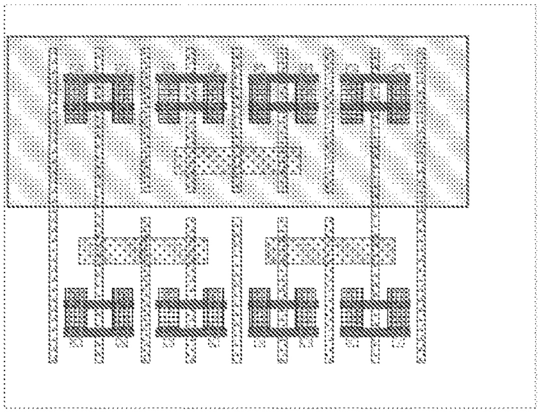
FIG. 2217B
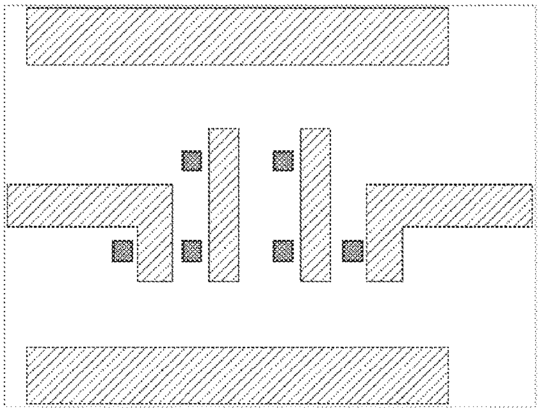
FIG. 2217C

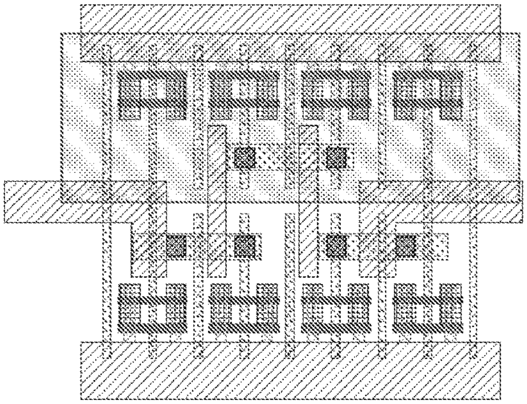
FIG. 2218A
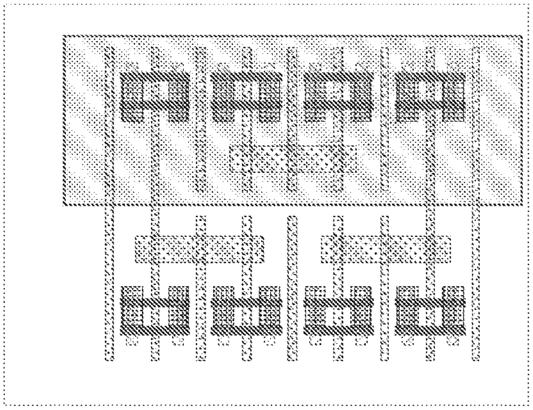
FIG. 2218B
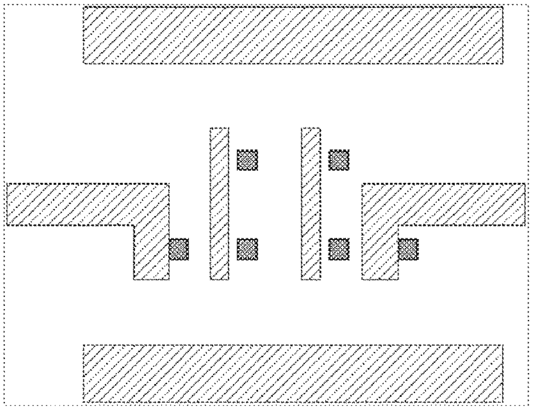
FIG. 2218C
*M* PDF Solutions, Inc.

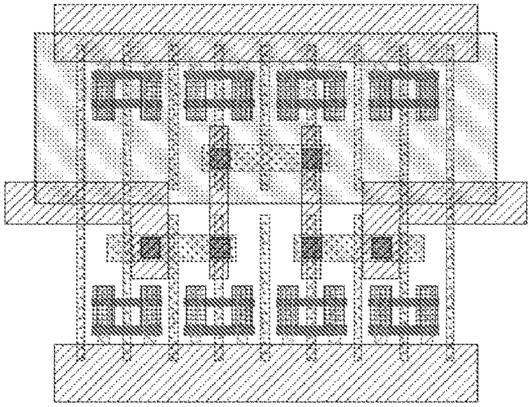
FIG. 2219A
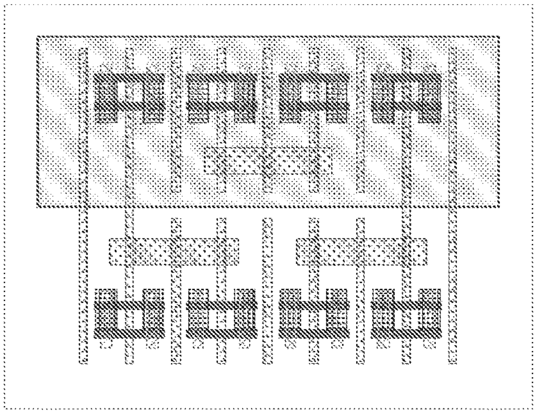
FIG. 2219B
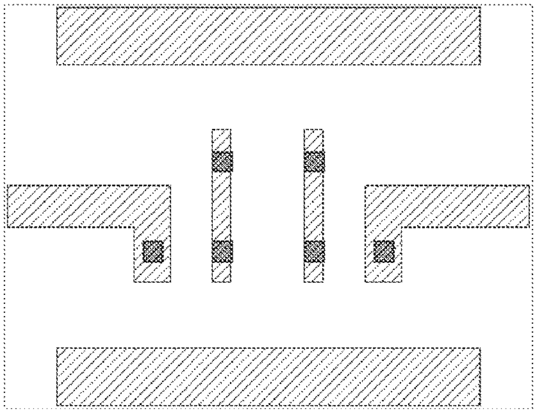
FIG. 2219C

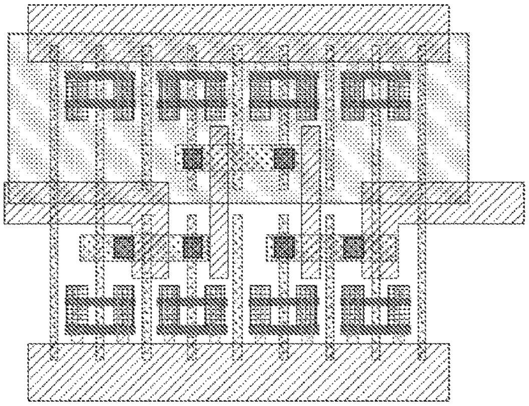
FIG. 2220A
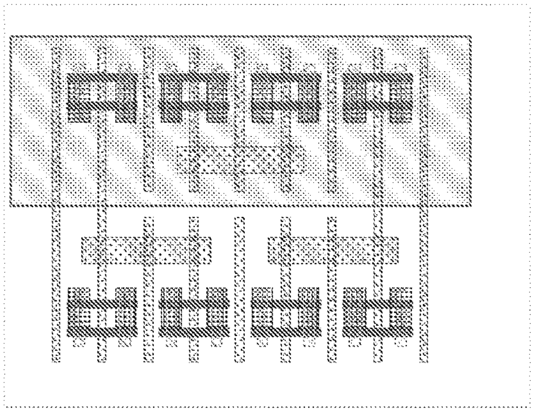
FIG. 2220B
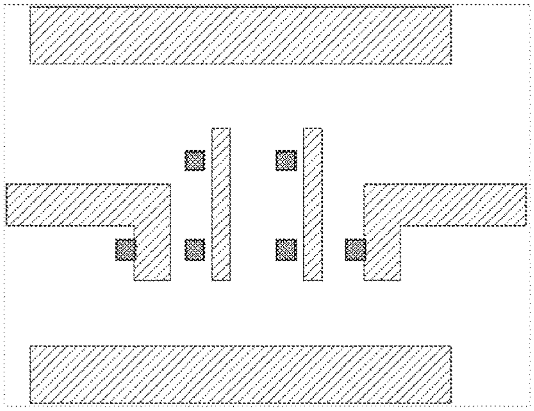
FIG. 2220C
*M* PDF Solutions, Inc.

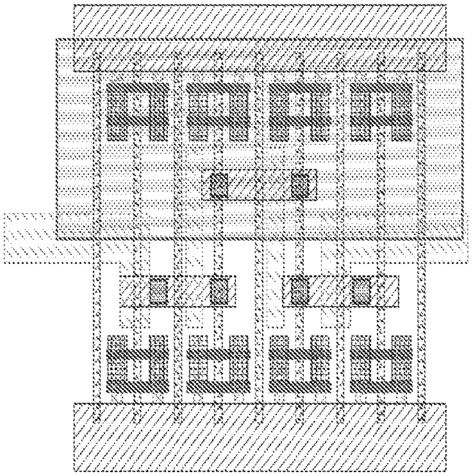
FIG. 2221A
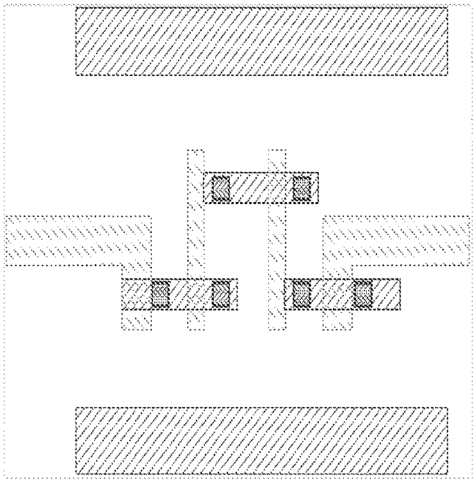
FIG. 2221B
*M* PDF Solutions, Inc.

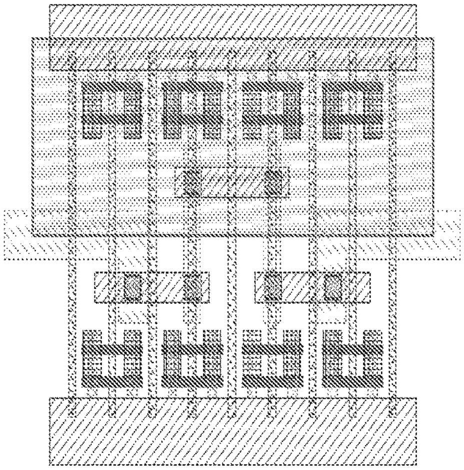
FIG. 2222A
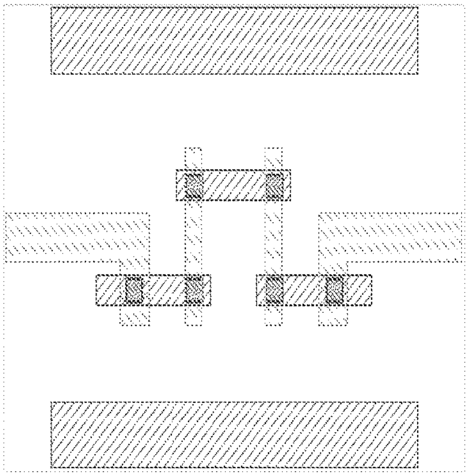
FIG. 2222B

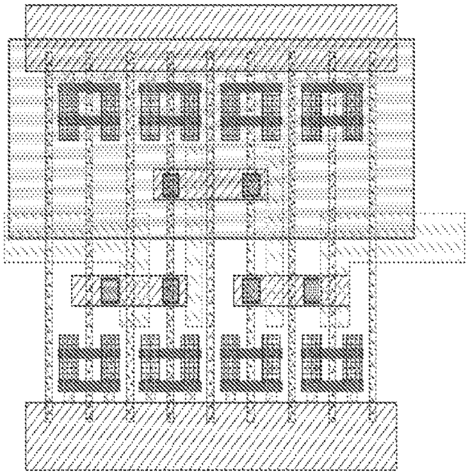
FIG. 2223A
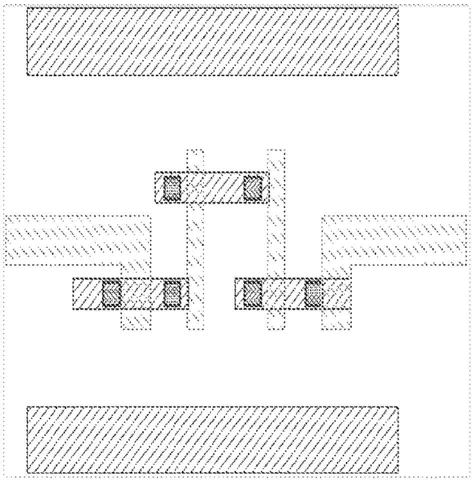
FIG. 2223B

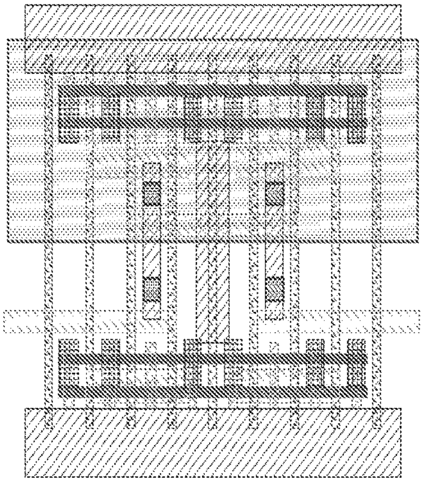
FIG. 2224A
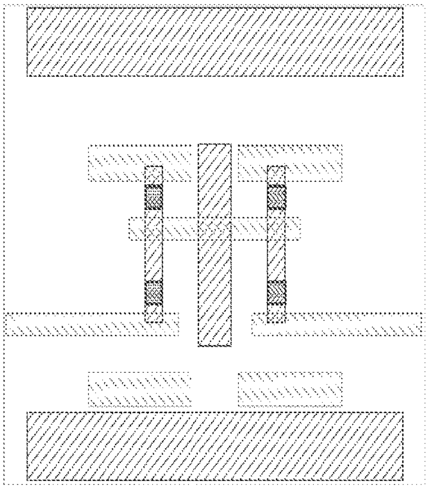
FIG. 2224B

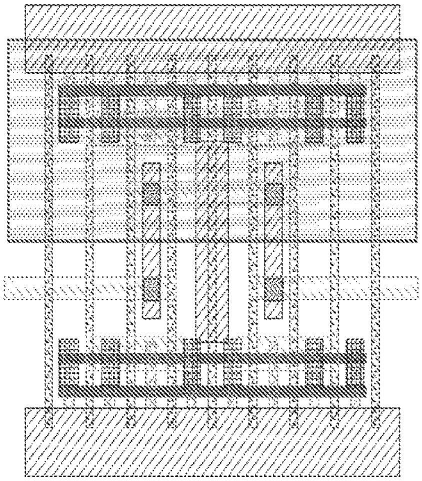
FIG. 2225A
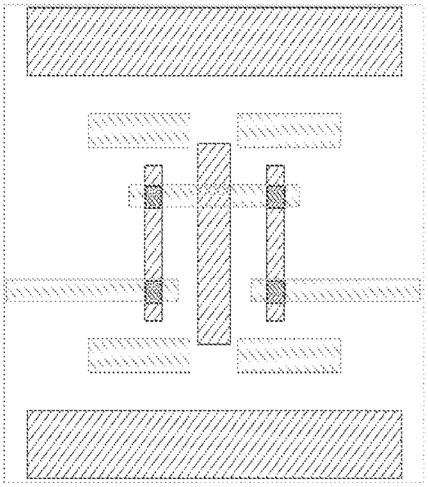
FIG. 2225B

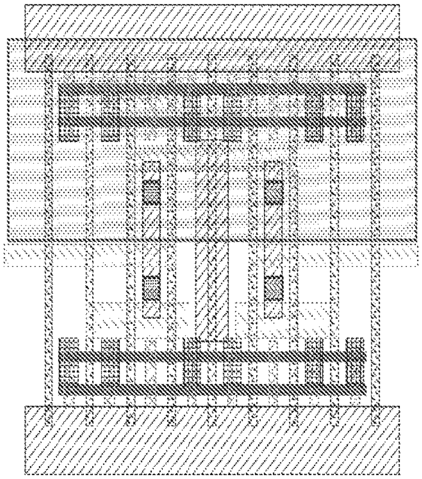
FIG. 2226A
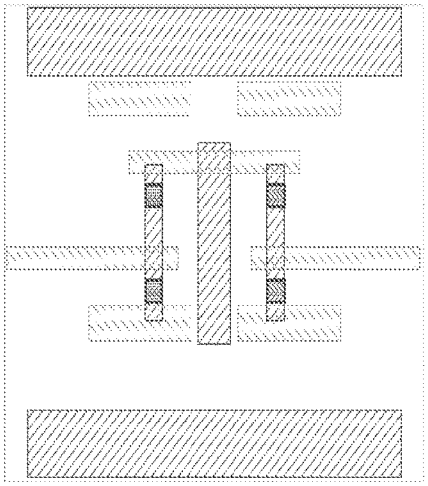
FIG. 2226B

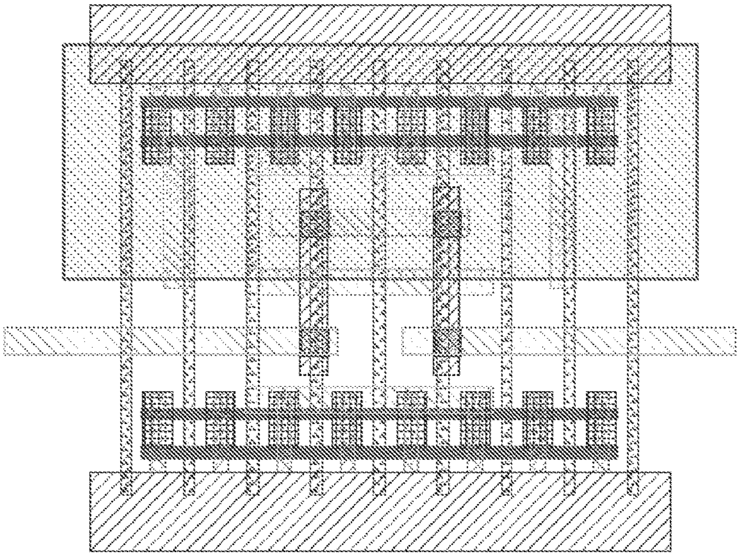
FIG. 2227A
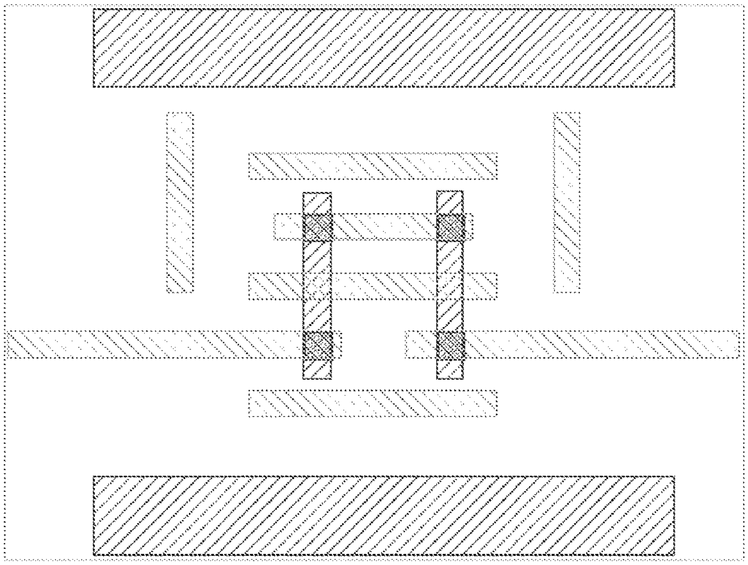
FIG. 2227B

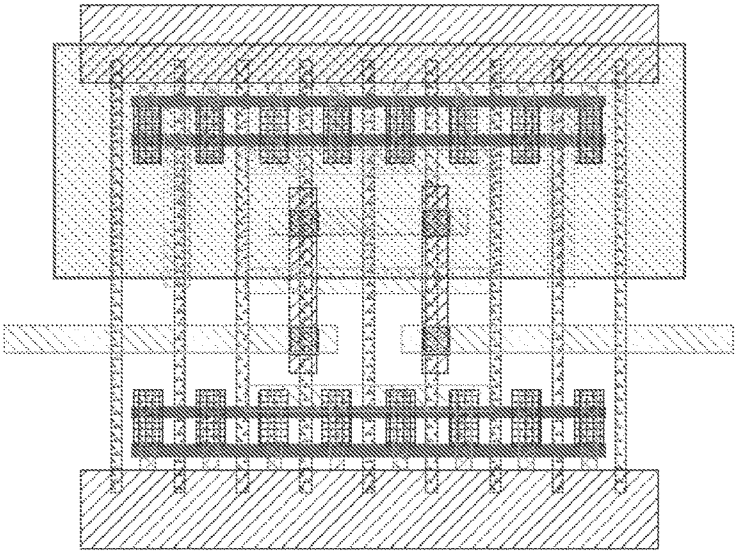
FIG. 2228A
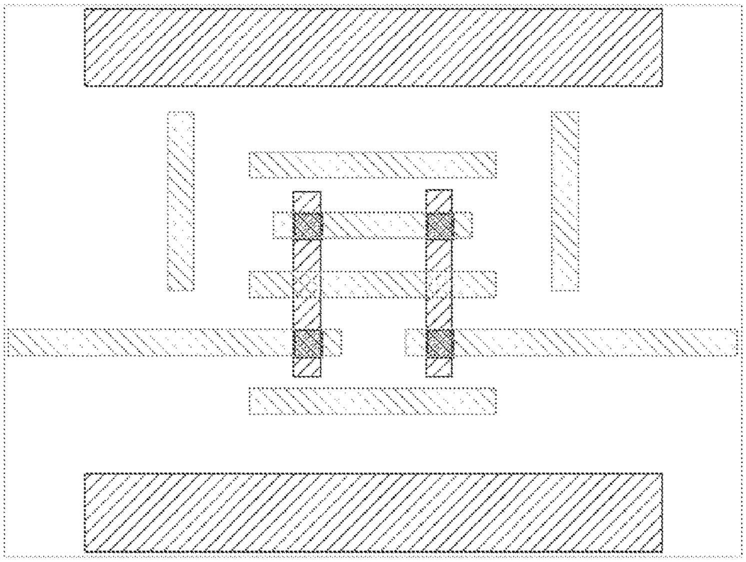
FIG. 2228B
*M* PDF Solutions, Inc.

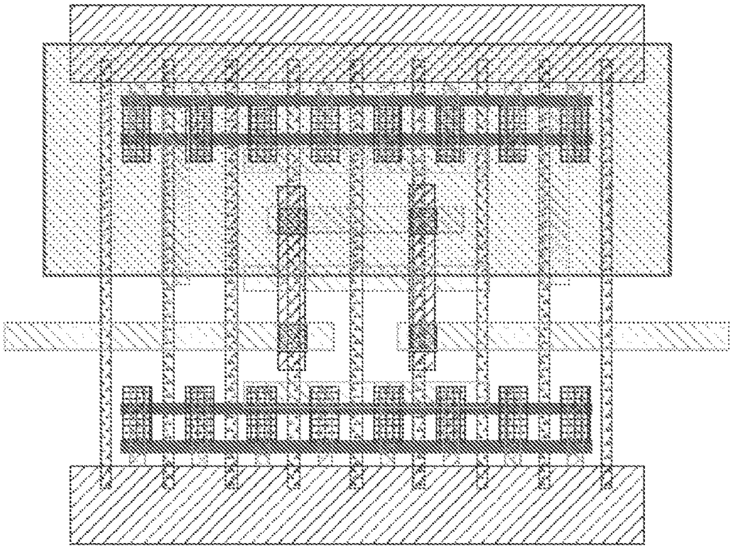
FIG. 2229A
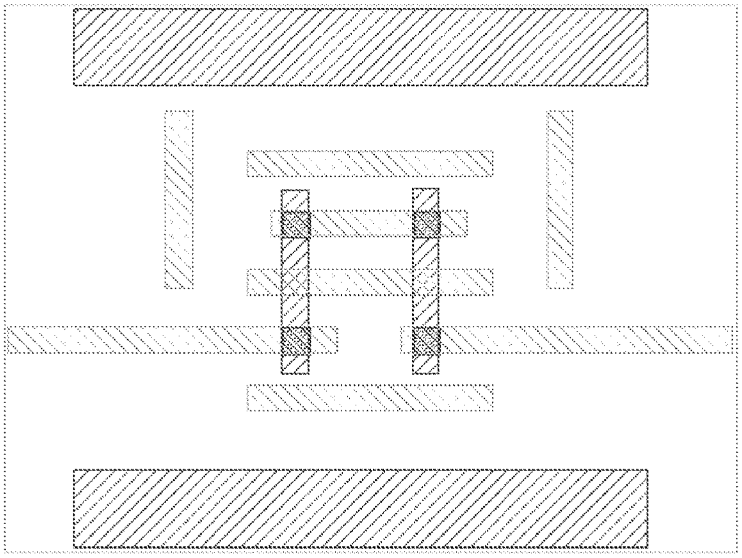
FIG. 2229B
*M* PDF Solutions, Inc.

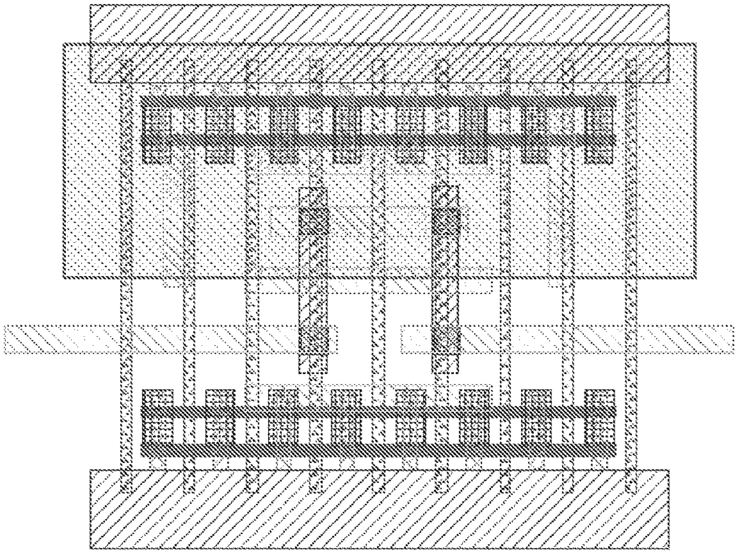
FIG. 2230A
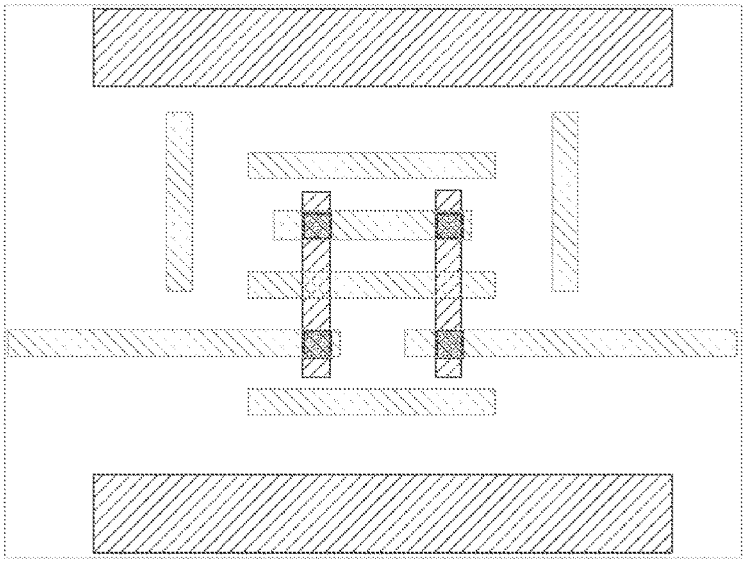
FIG. 2230B
*M* PDF Solutions, Inc.

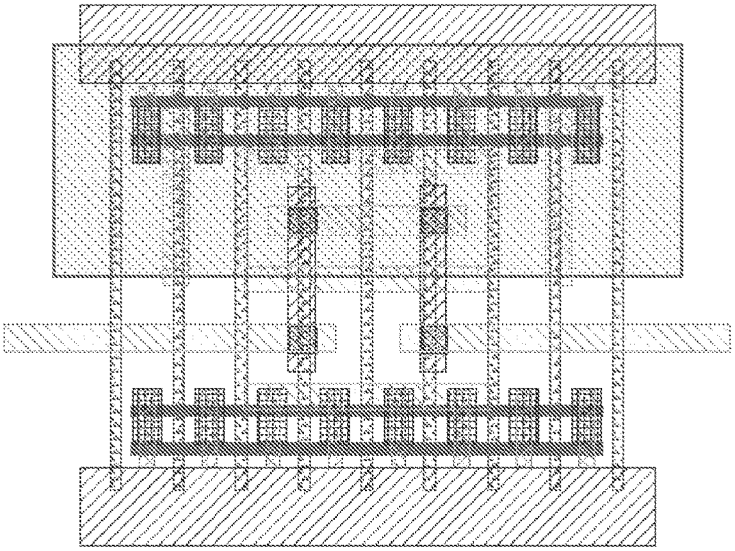
FIG. 2231A
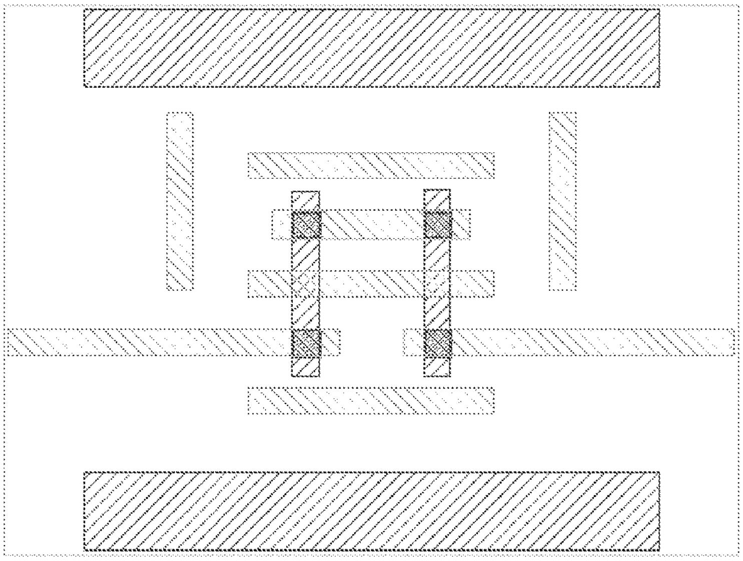
FIG. 2231B
*M* PDF Solutions, Inc.

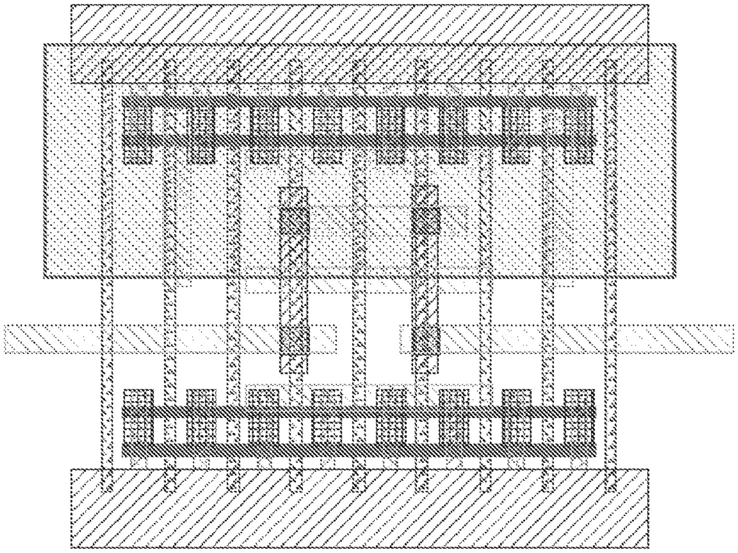
FIG. 2232A
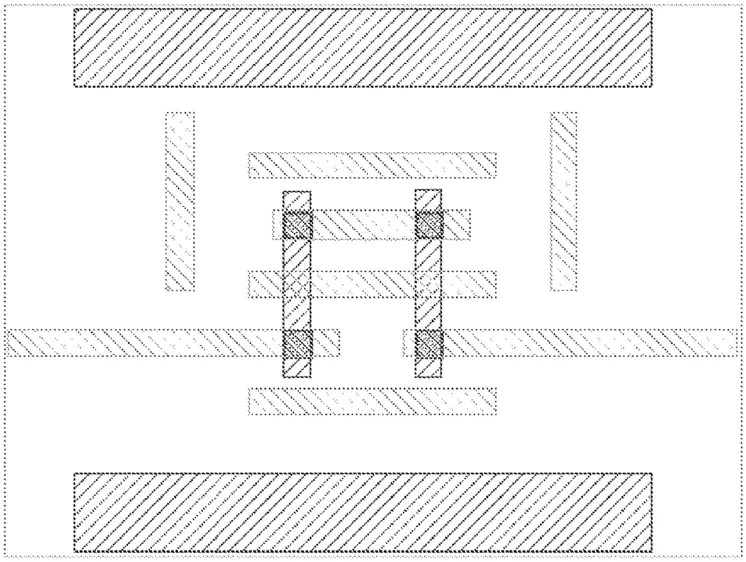
FIG. 2232B
*M* PDF Solutions, Inc.

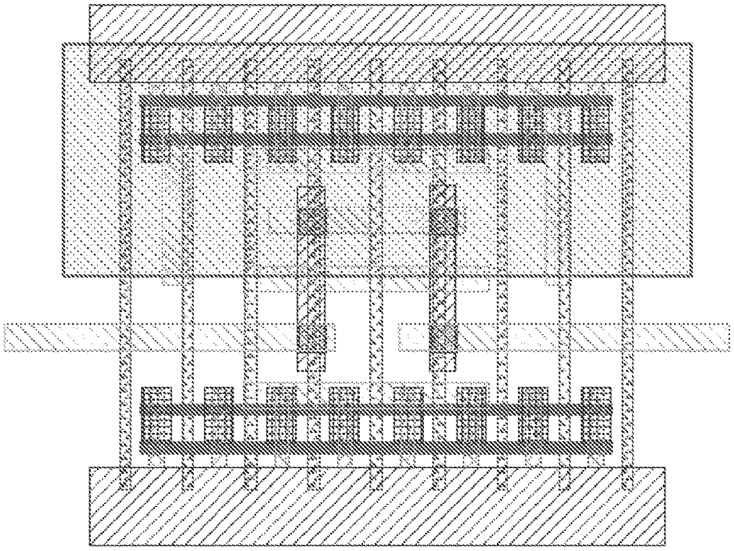
FIG. 2233A
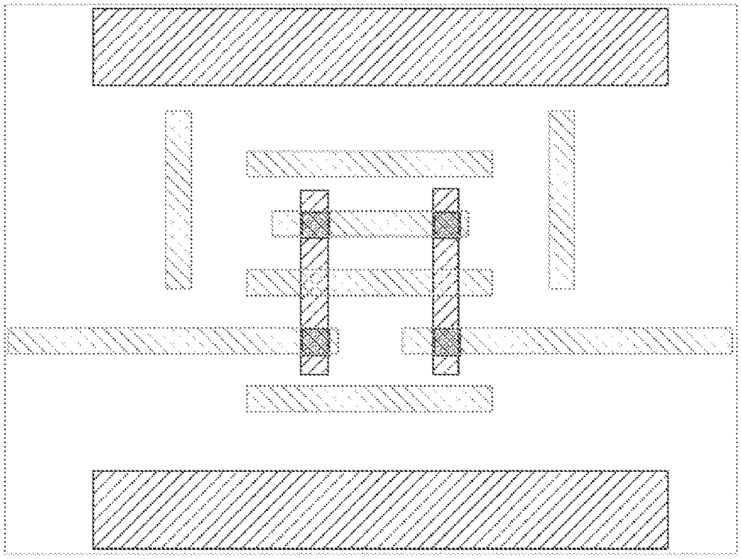
FIG. 2233B
*M* PDF Solutions, Inc.

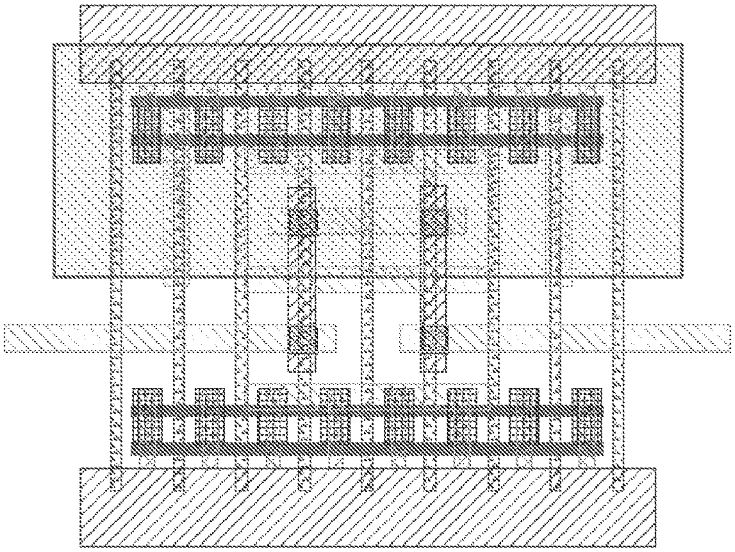
FIG. 2234A
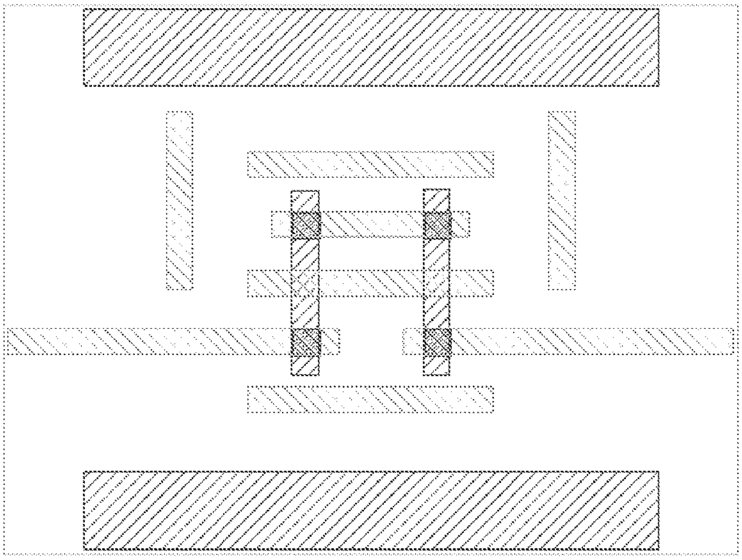
FIG. 2234B
*M* PDF Solutions, Inc.

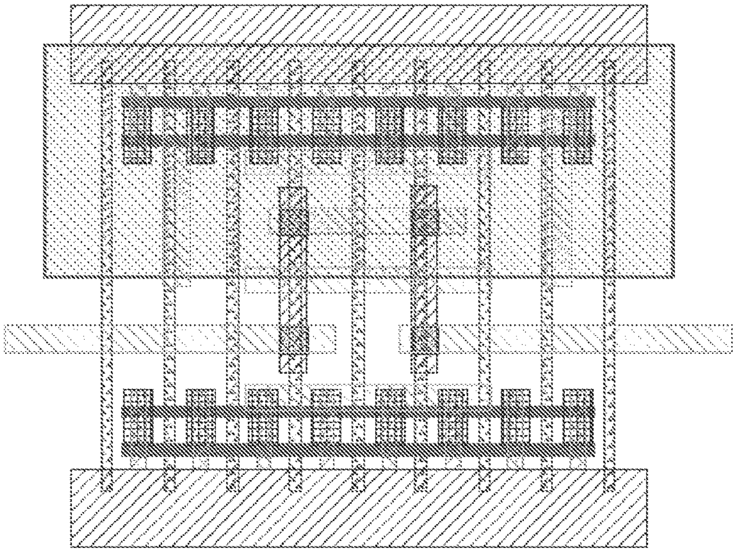
FIG. 2235A
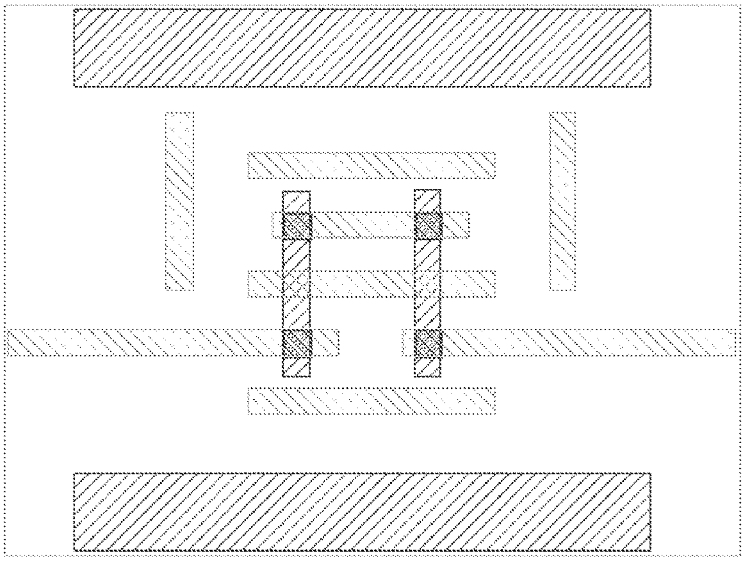
FIG. 2235B
*M* PDF Solutions, Inc.

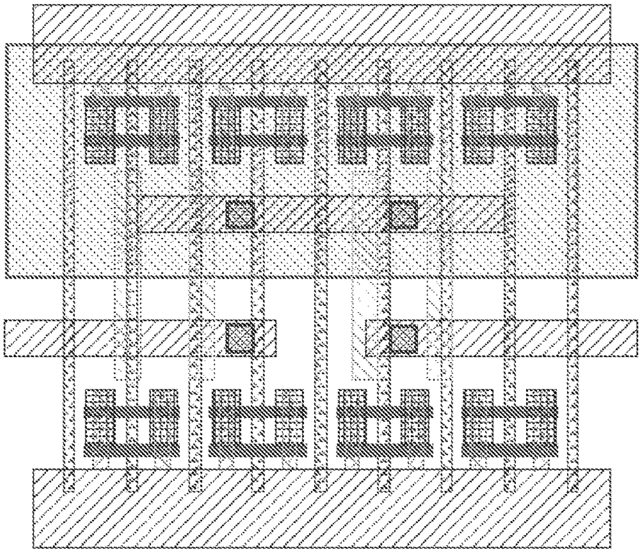
FIG. 2236A
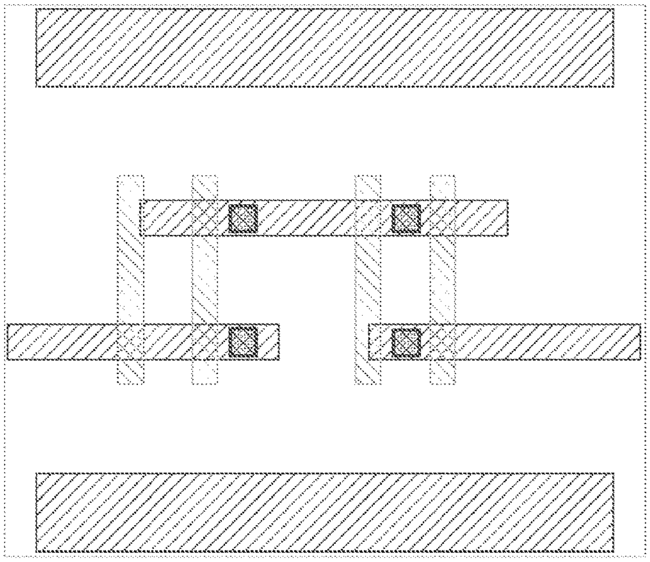
FIG. 2236B
*M* PDF Solutions, Inc.

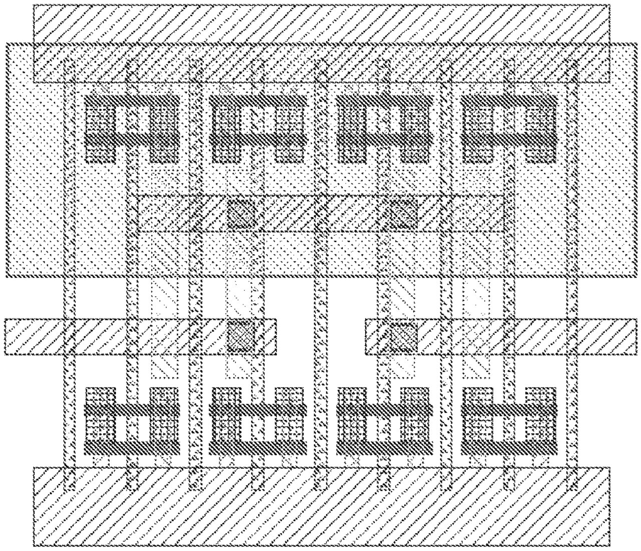
FIG. 2237A
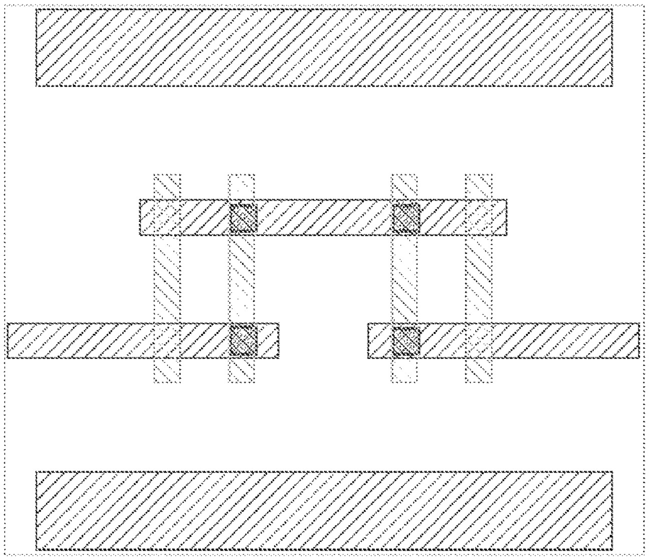
FIG. 2237B
*M* PDF Solutions, Inc.

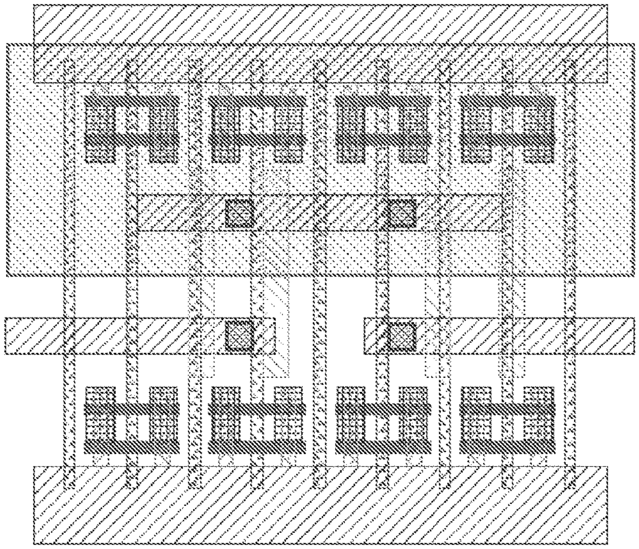
FIG. 2238A
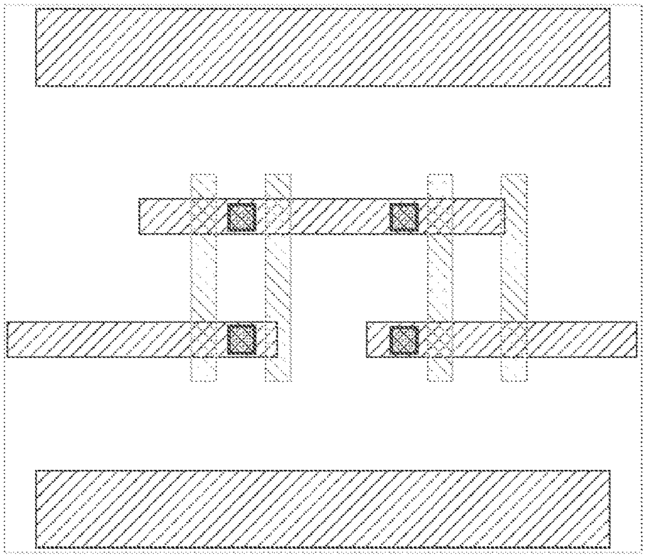
FIG. 2238B
*M* PDF Solutions, Inc.

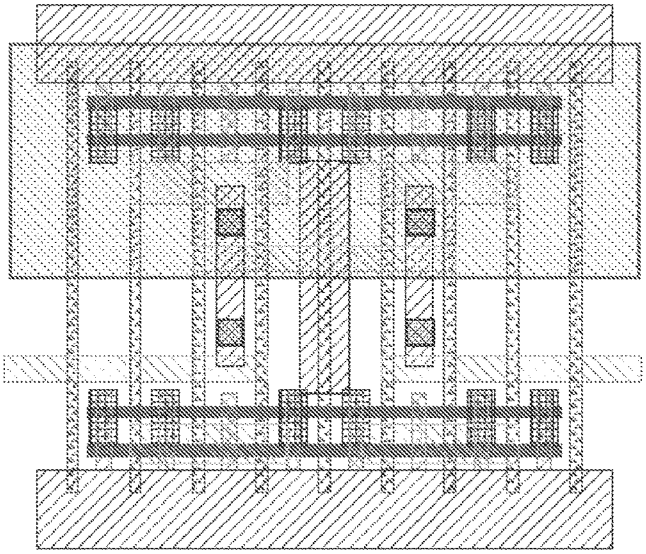
FIG. 2239A
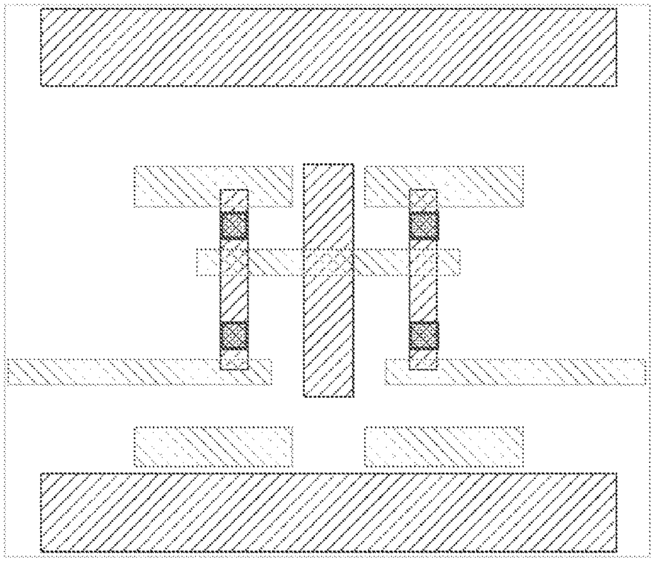
FIG. 2239B

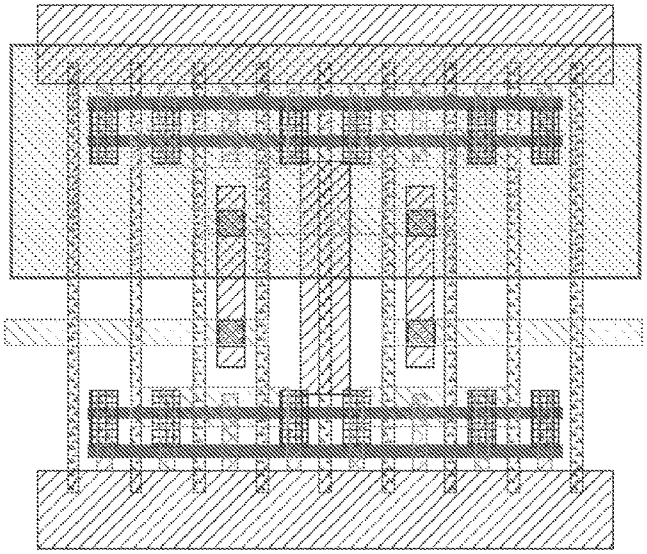
FIG. 2240A
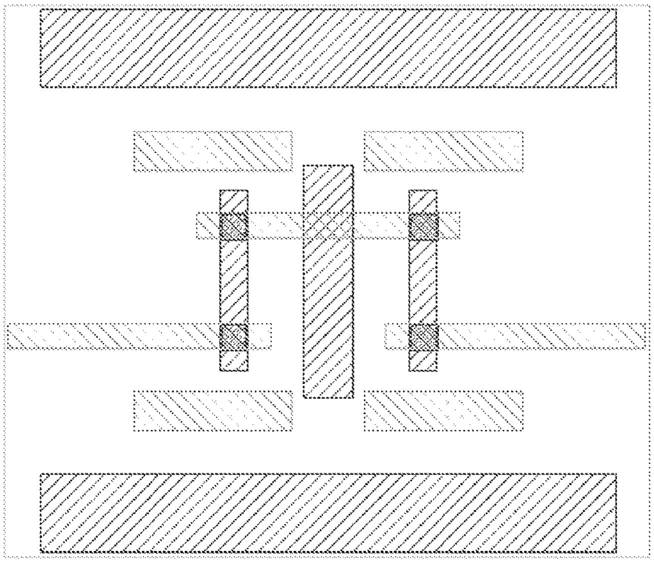
FIG. 2240B

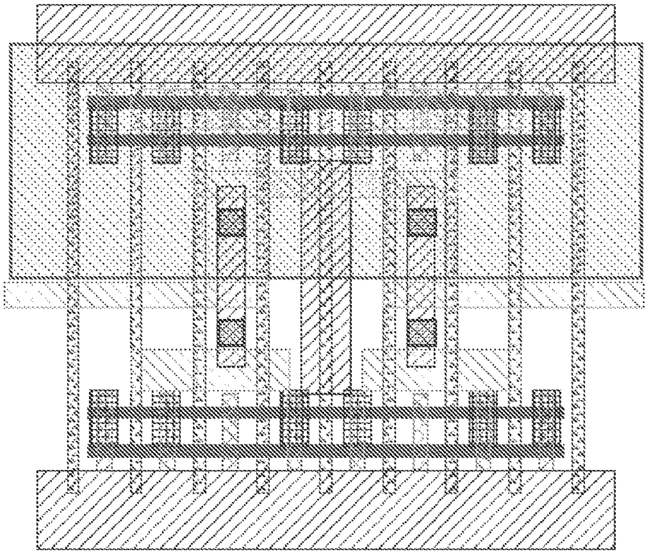
FIG. 2241A
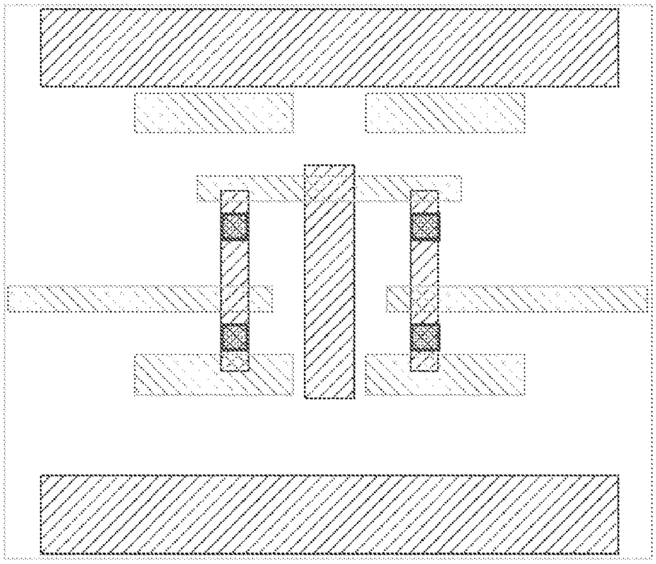
FIG. 2241B
*M* PDF Solutions, Inc.

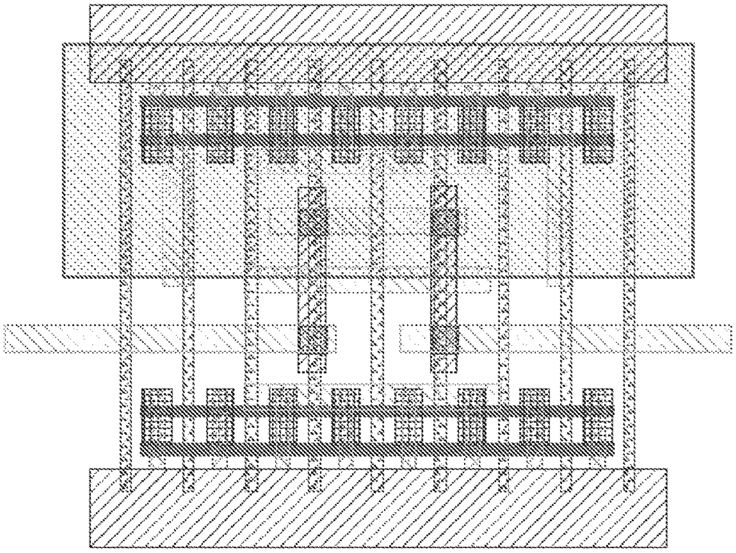
FIG. 2242A
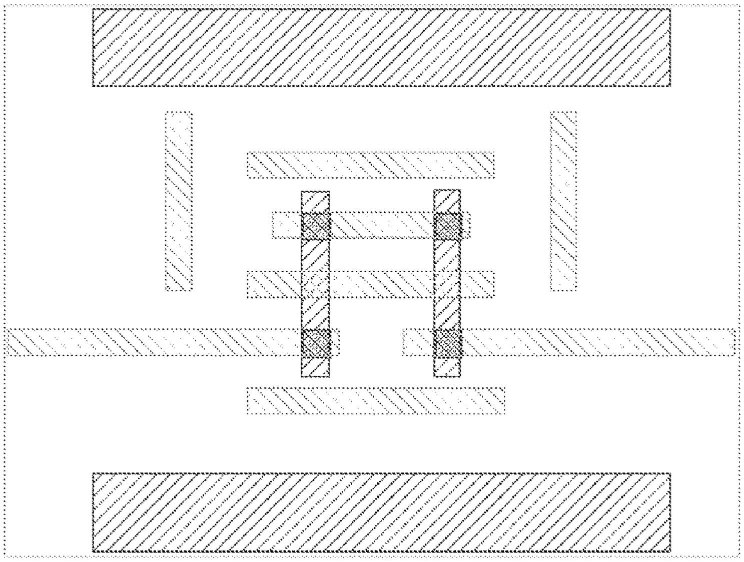
FIG. 2242B
*M* PDF Solutions, Inc.

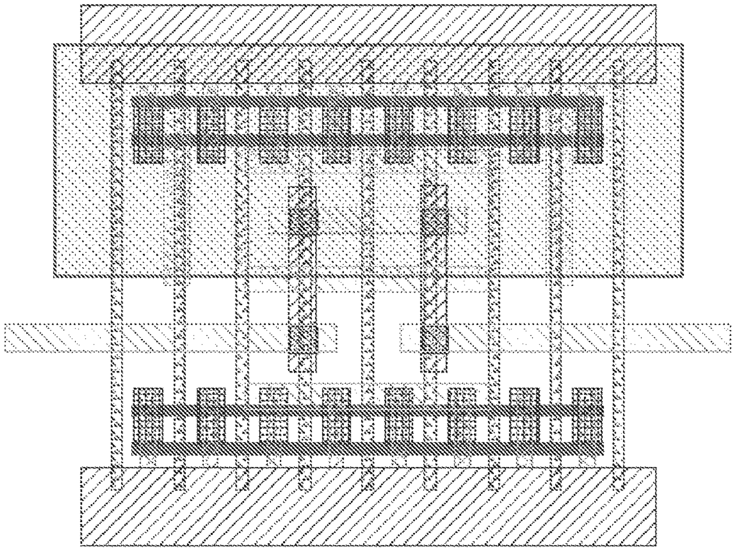
FIG. 2243A
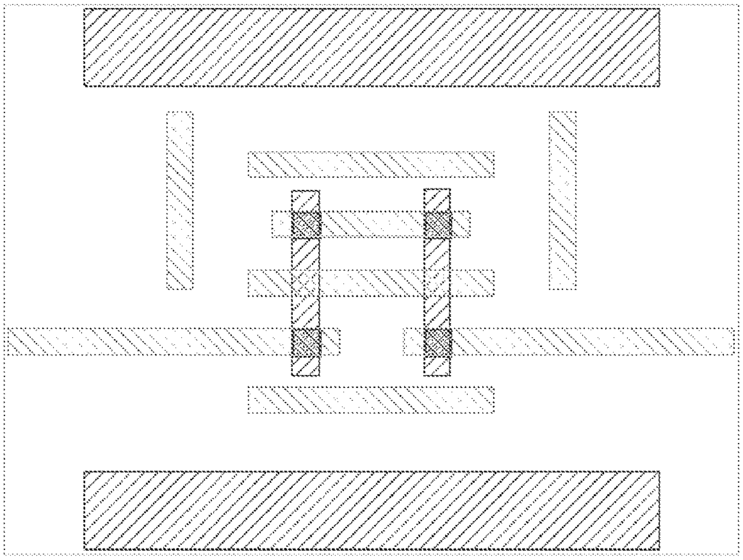
FIG. 2243B

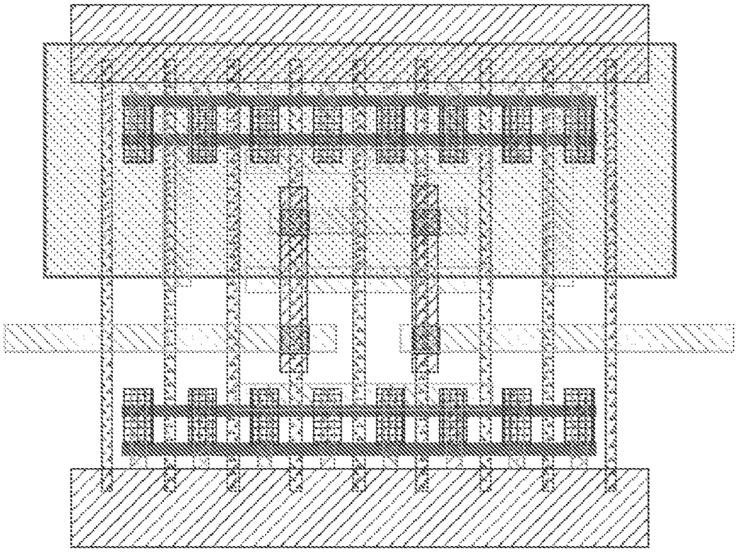
FIG. 2244A
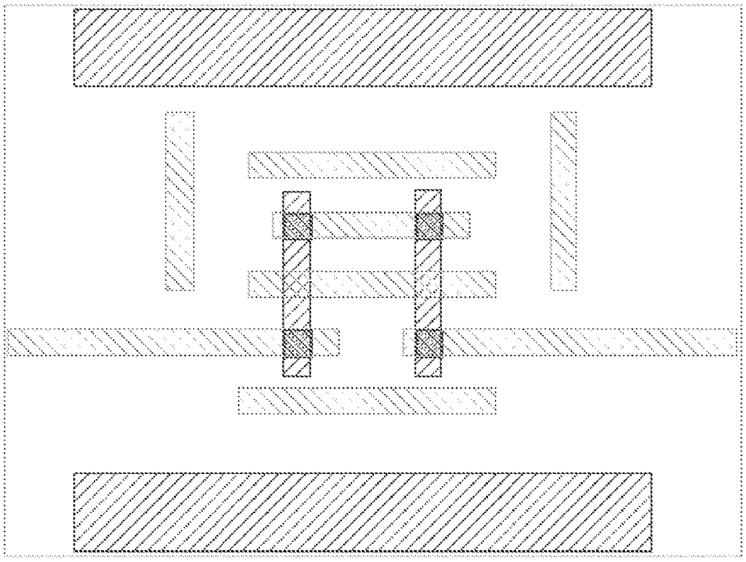
FIG. 2244B
*M* PDF Solutions, Inc.

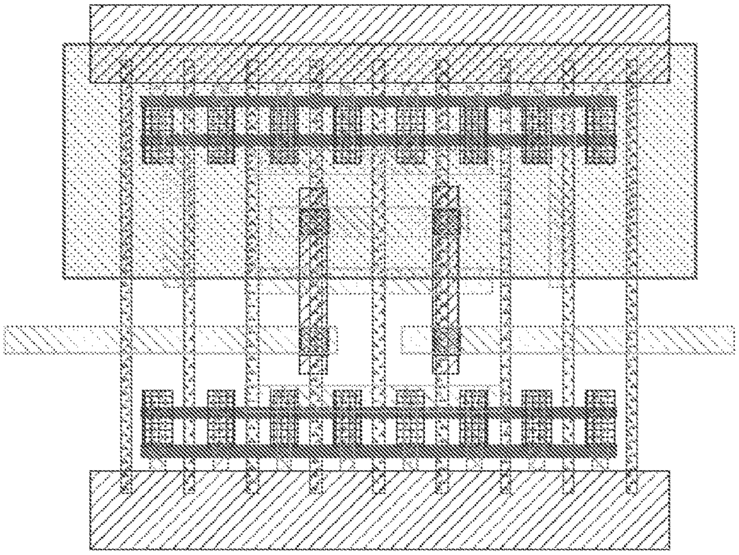
FIG. 2245A
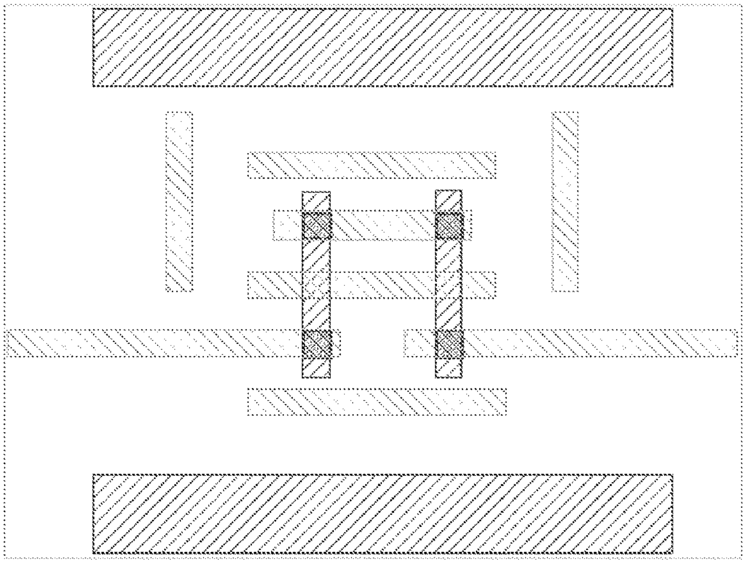
FIG. 2245B
*M* PDF Solutions, Inc.

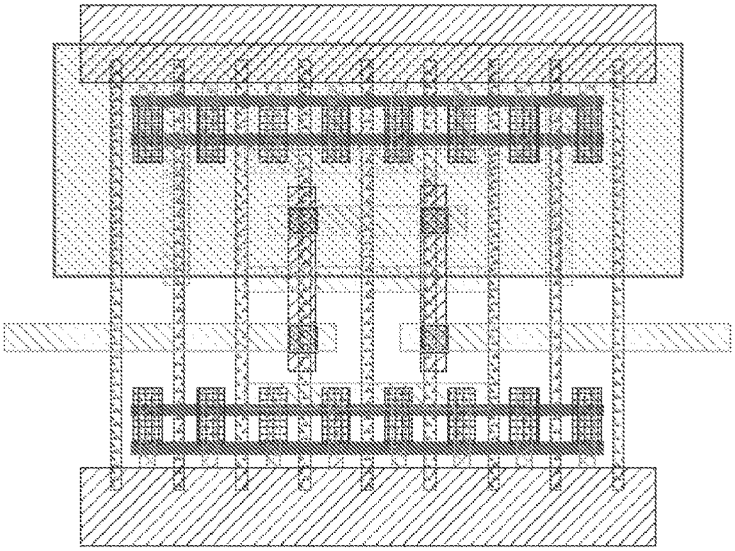
FIG. 2246A
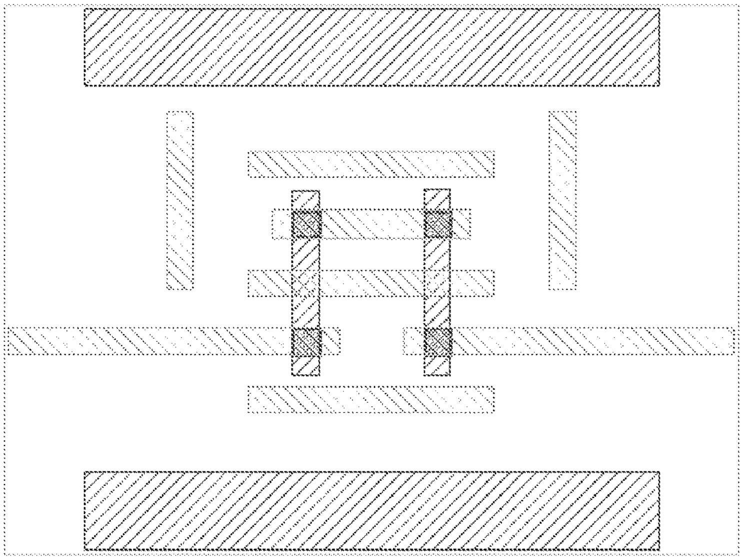
FIG. 2246B
*M* PDF Solutions, Inc.

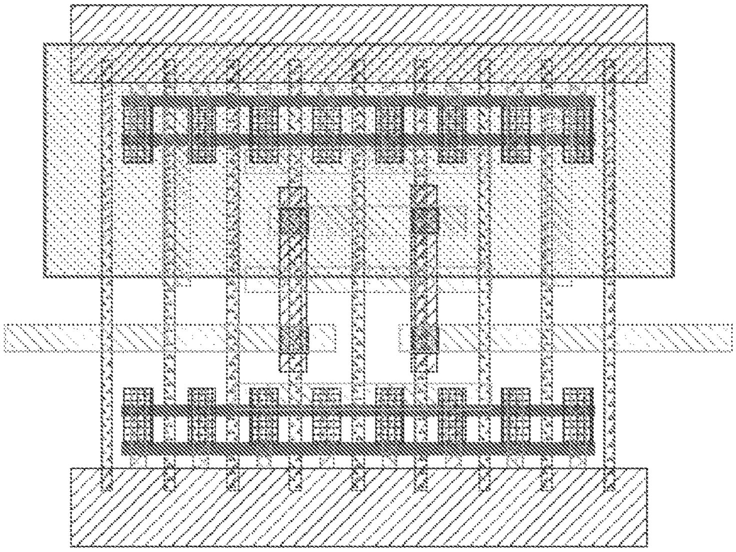
FIG. 2247A
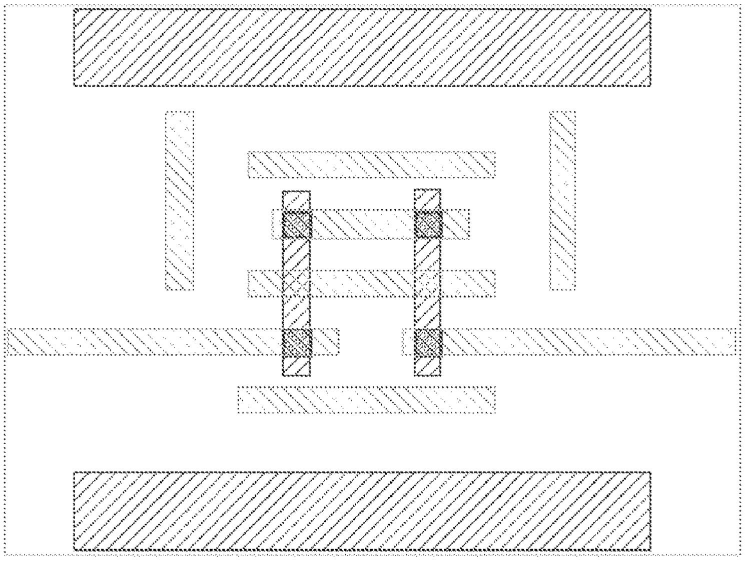
FIG. 2247B

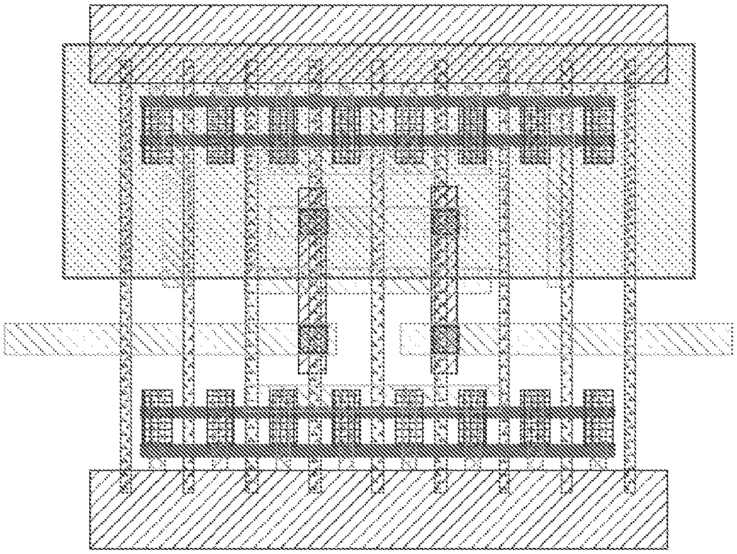
FIG. 2248A
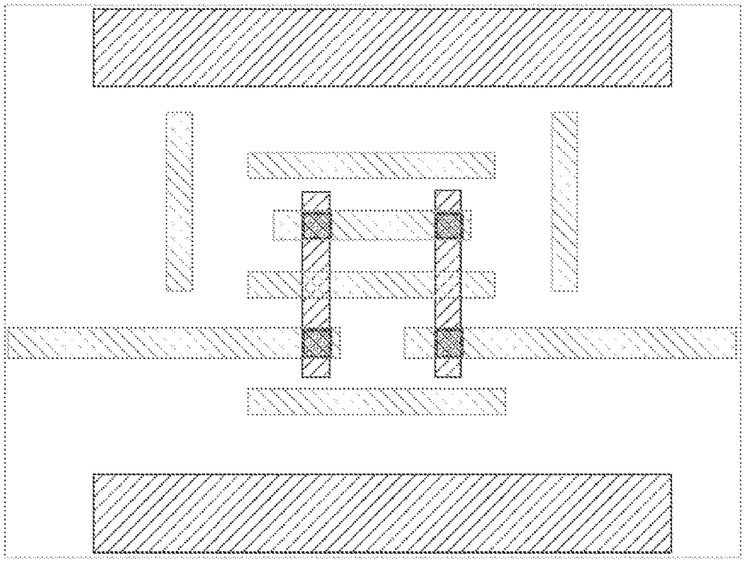
FIG. 2248B
*M* PDF Solutions, Inc.

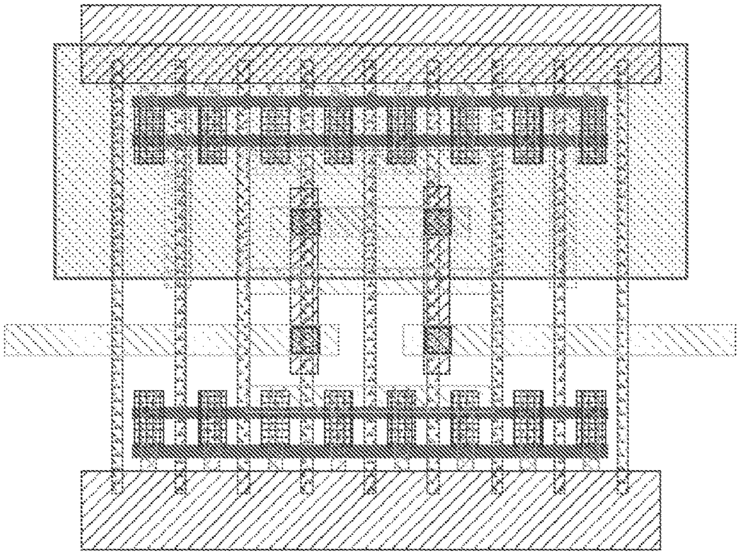
FIG. 2249A
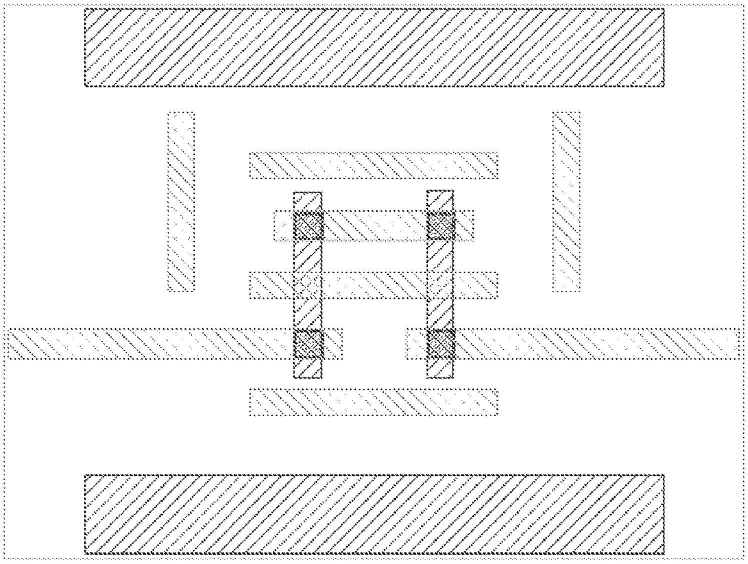
FIG. 2249B
*M* PDF Solutions, Inc.

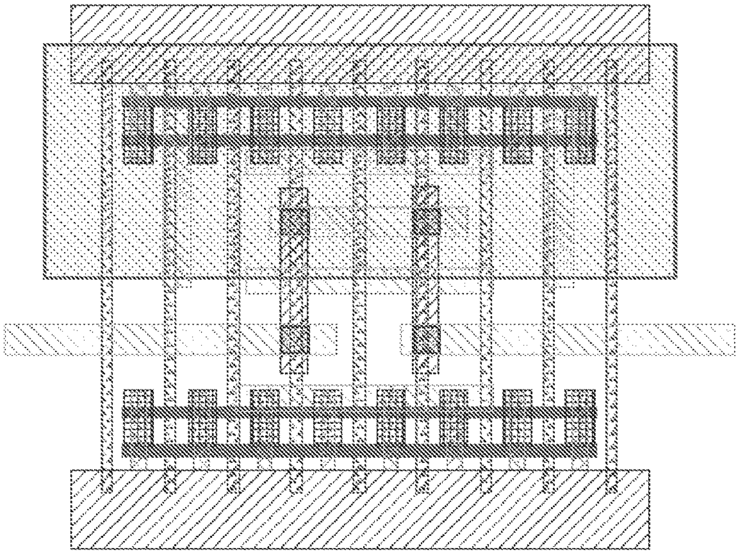
FIG. 2250A
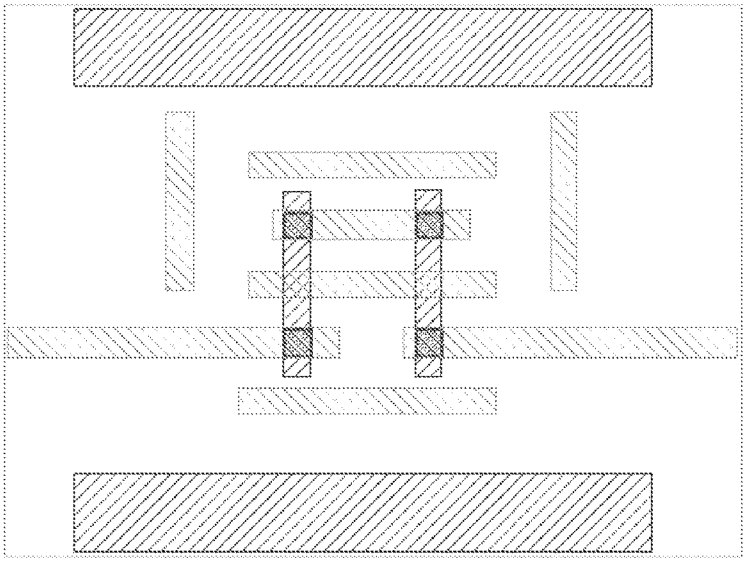
FIG. 2250B

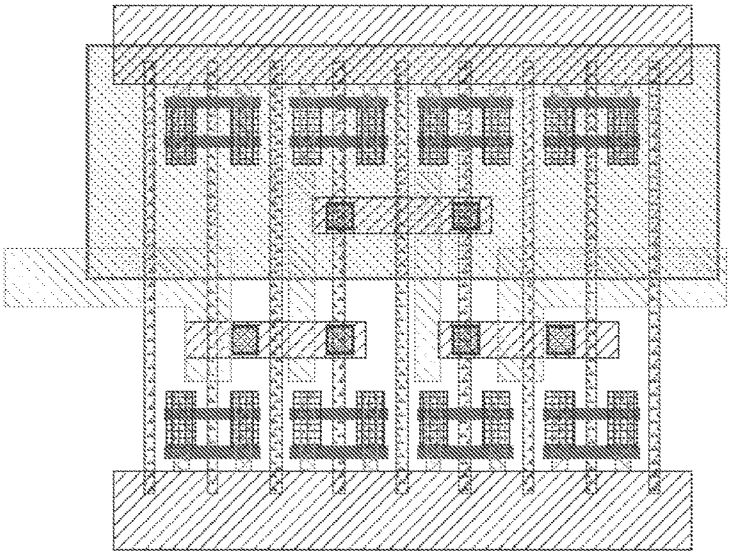
FIG. 2251A
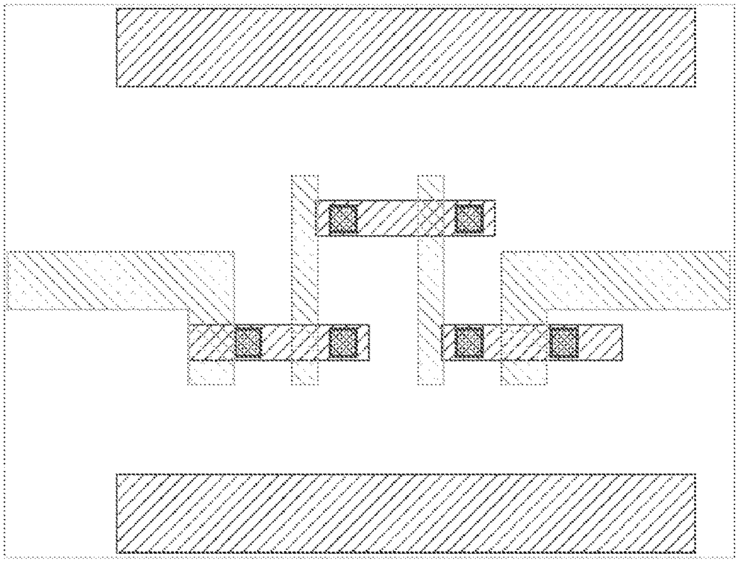
FIG. 2251B
*M* PDF Solutions, Inc.

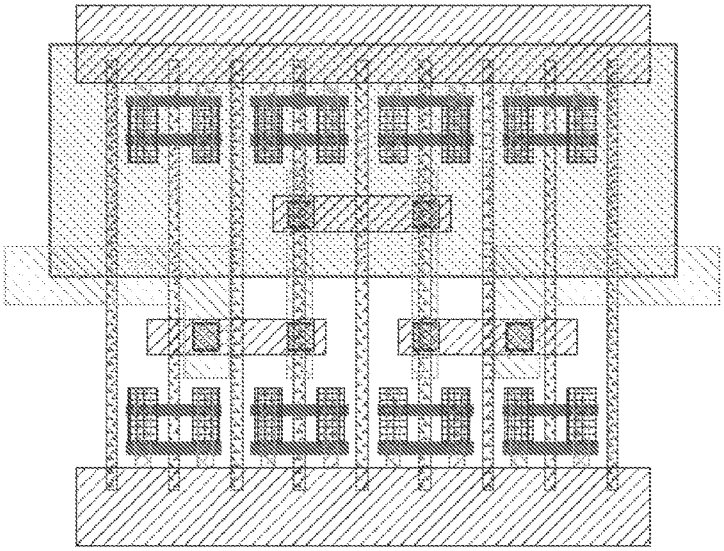
FIG. 2252A
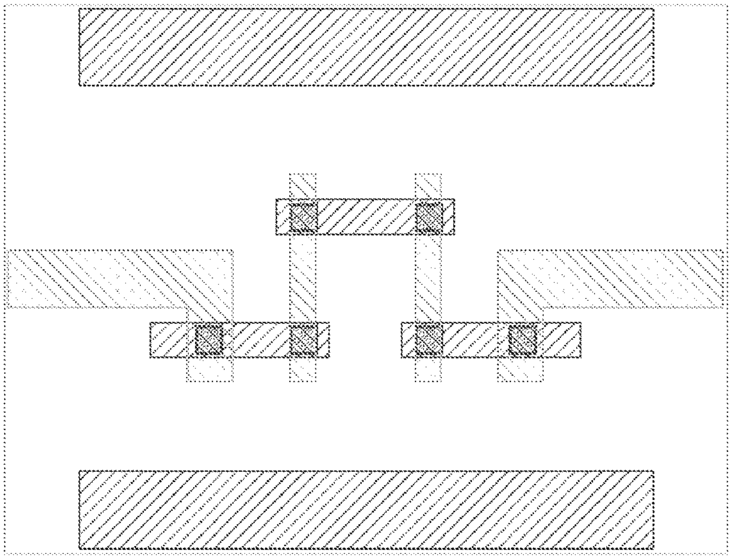
FIG. 2252B

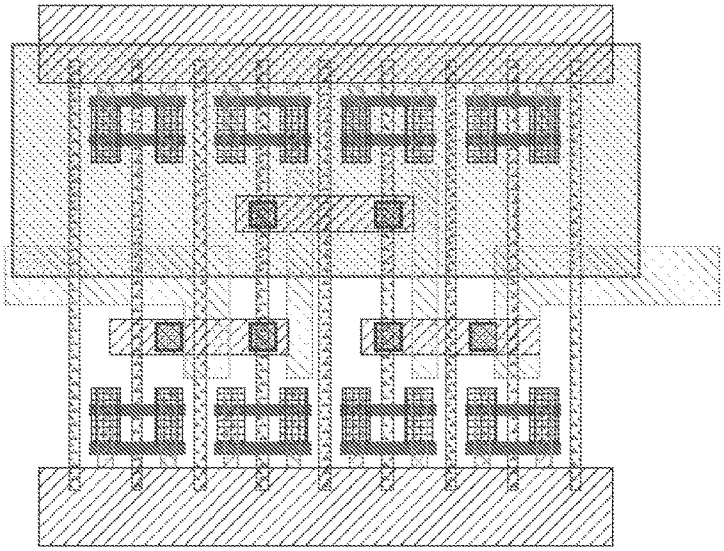
FIG. 2253A
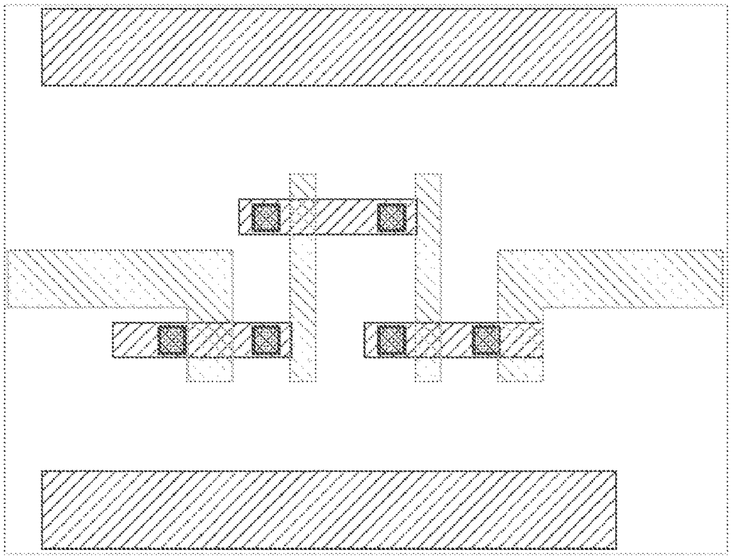
FIG. 2253B
*M* PDF Solutions, Inc.

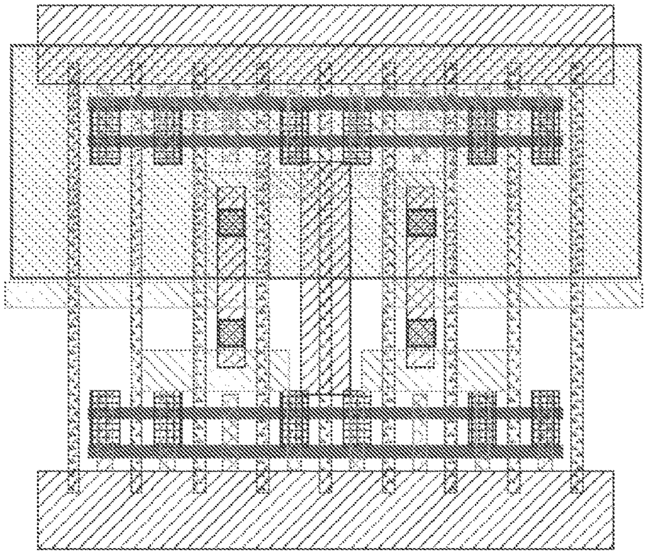
FIG. 2254A
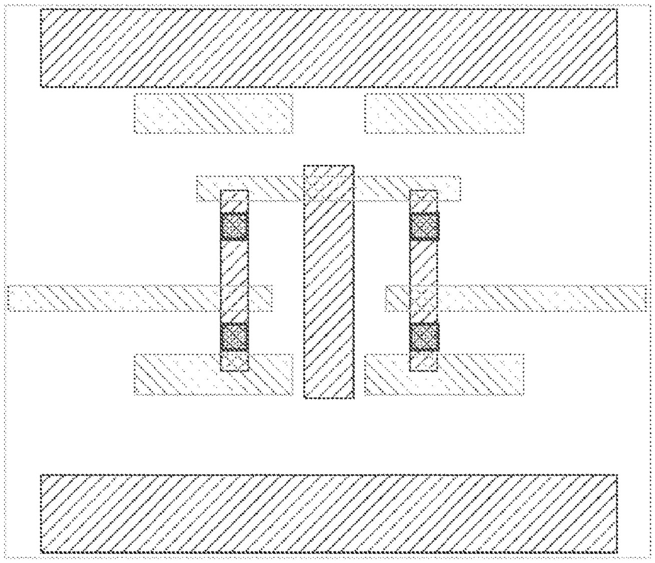
FIG. 2254B
*M* PDF Solutions, Inc.

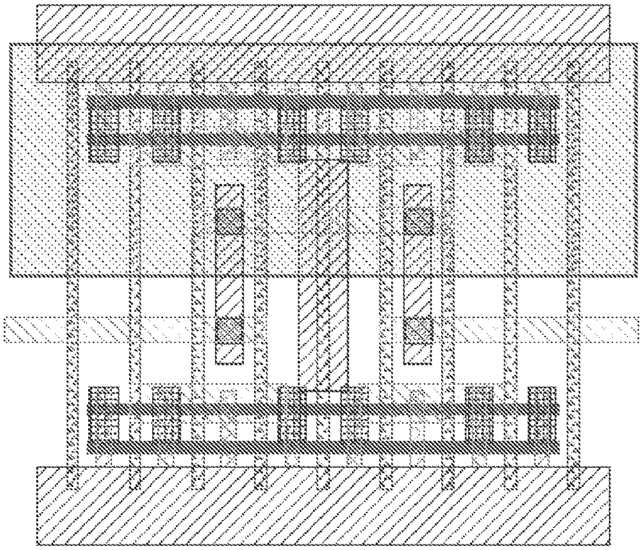
FIG. 2255A
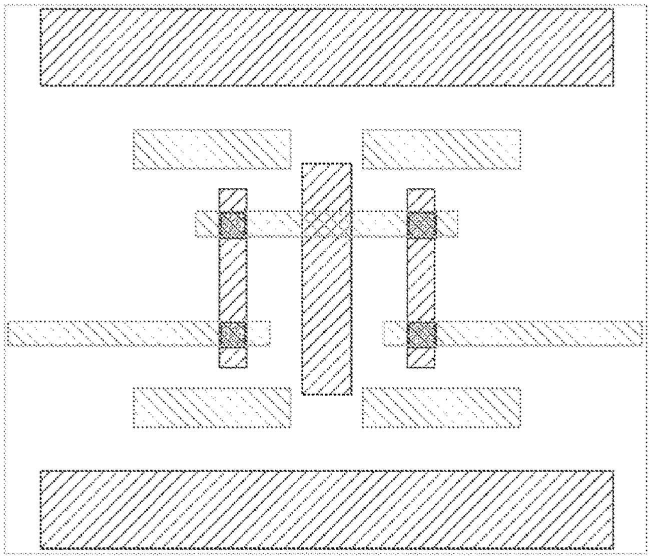
FIG. 2255B

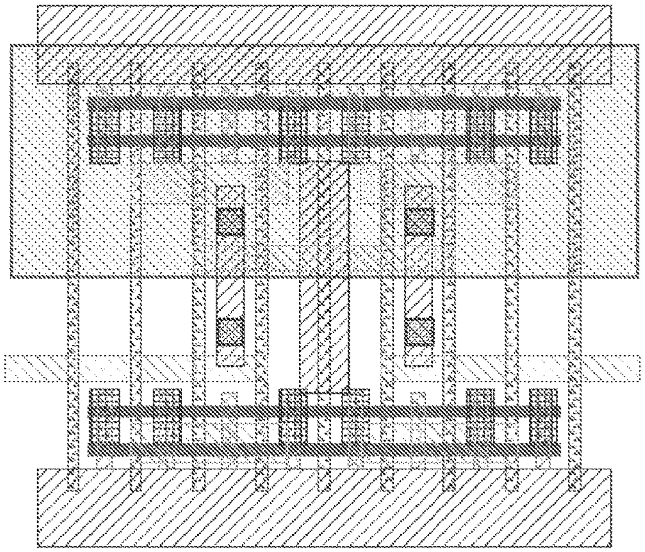
FIG. 2256A
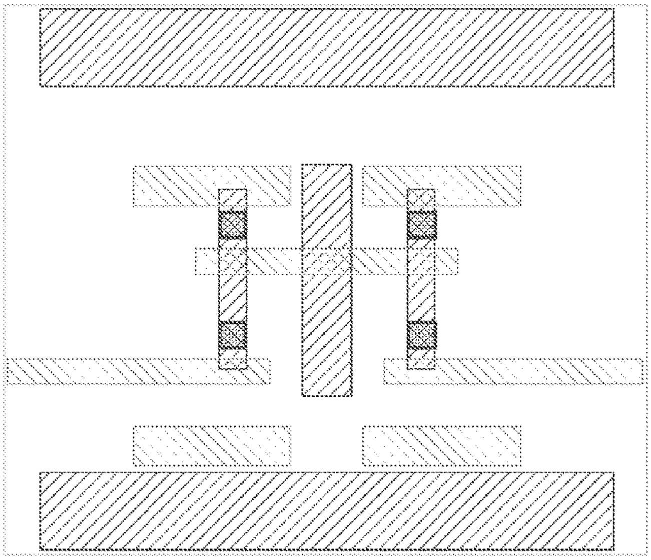
FIG. 2256B

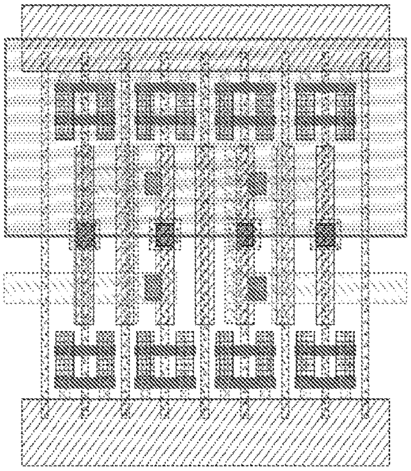
FIG. 2257A
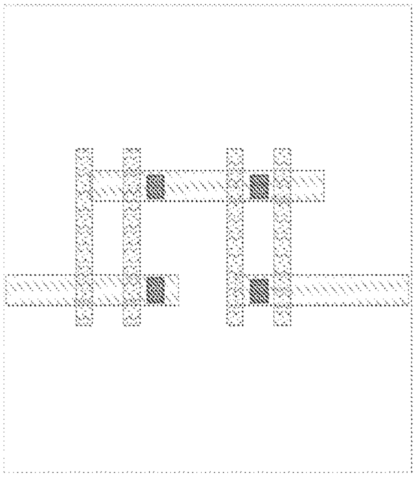
FIG. 2257B

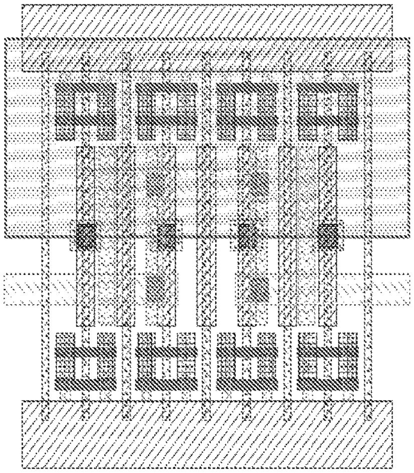
FIG. 2258A
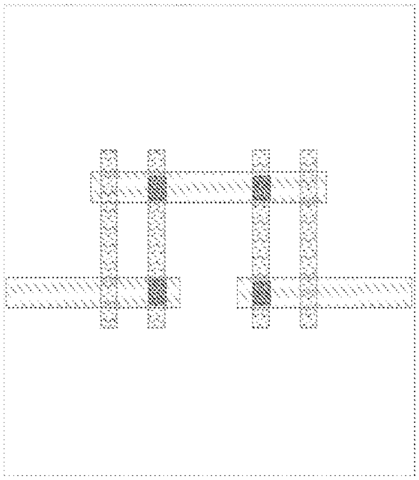
FIG. 2258B

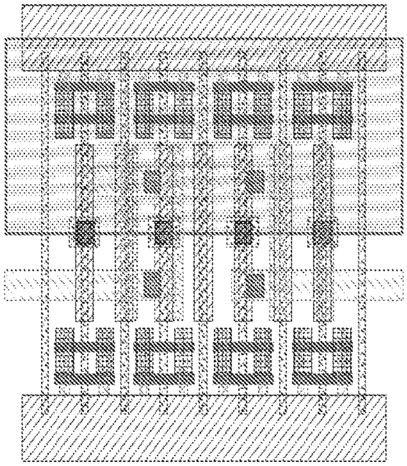
FIG. 2259A
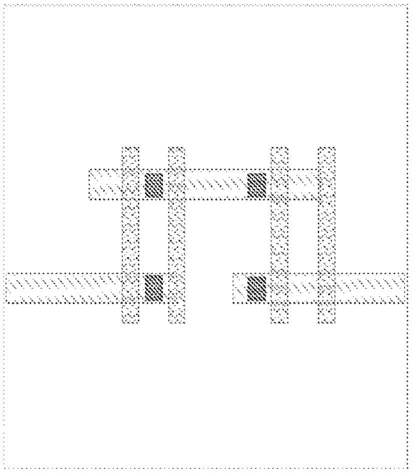
FIG. 2259B

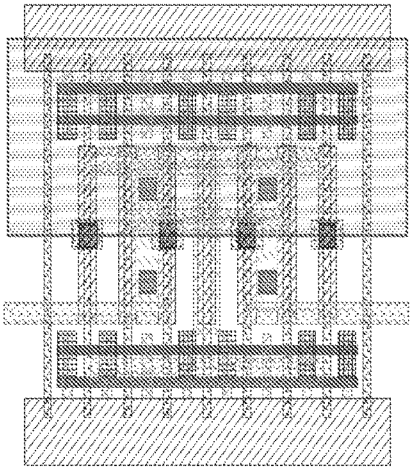
FIG. 2260A
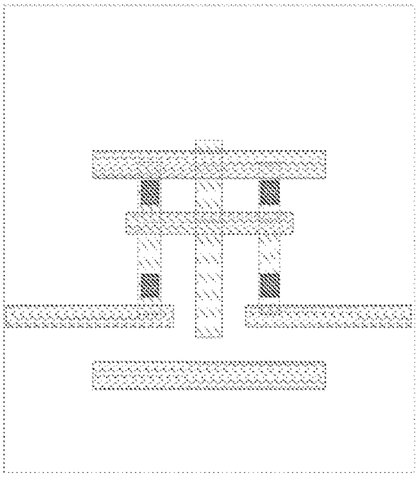
FIG. 2260B

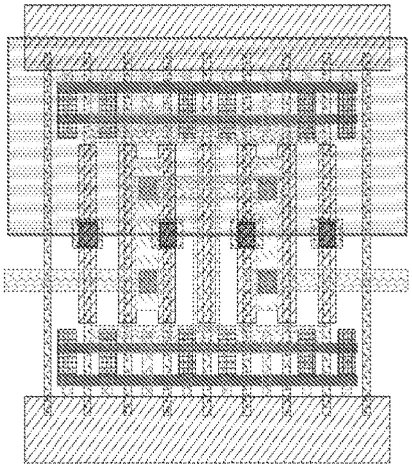
FIG. 2261A
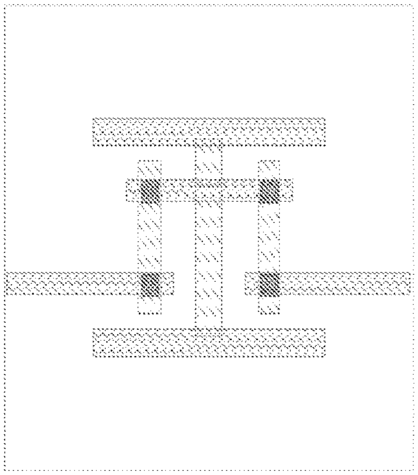
FIG. 2261B
*M* PDF Solutions, Inc.

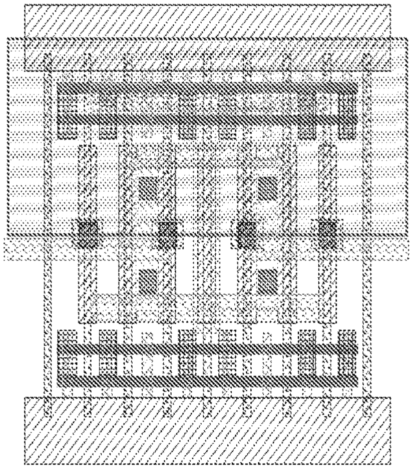
FIG. 2262A
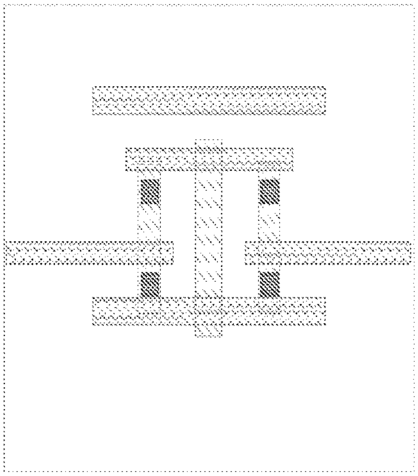
FIG. 2262B
*M* PDF Solutions, Inc.

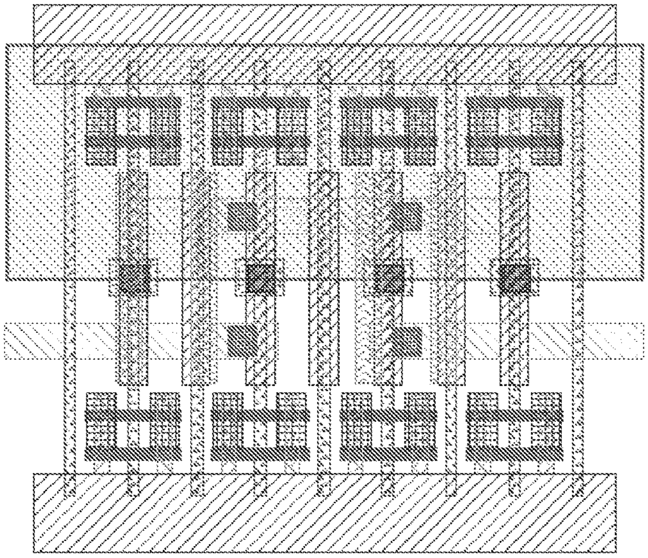
FIG. 2263A
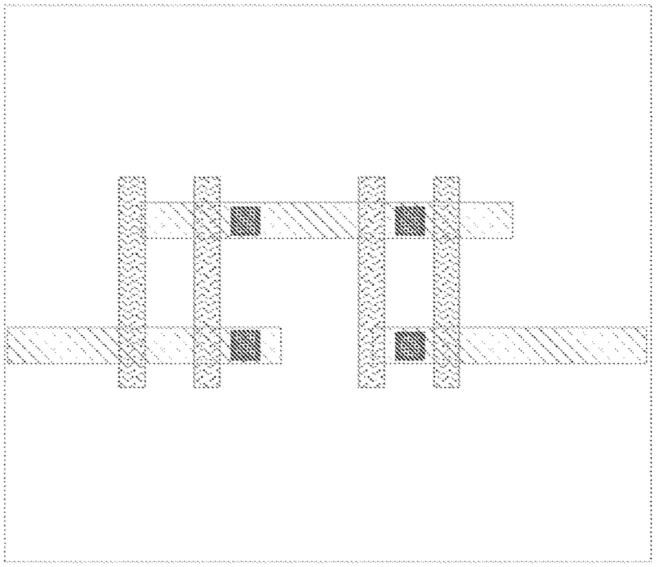
FIG. 2263B

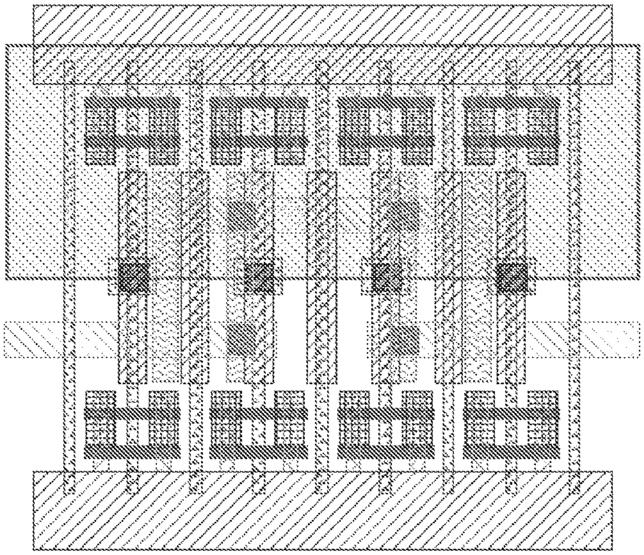
FIG. 2264A
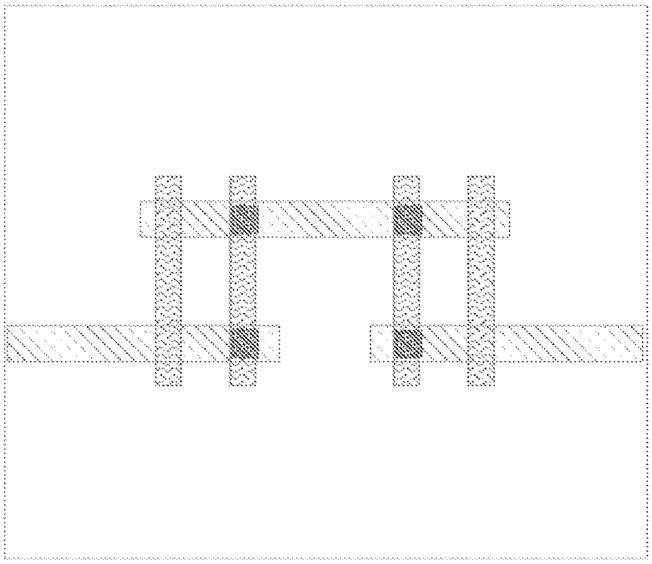
FIG. 2264B
*M* PDF Solutions, Inc.

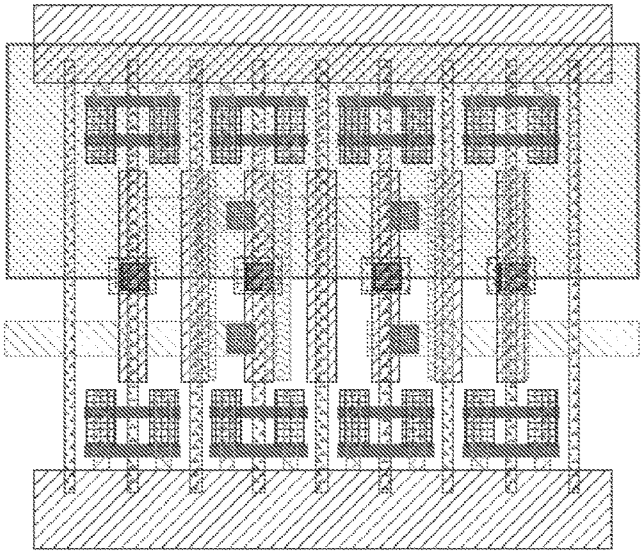
FIG. 2265A
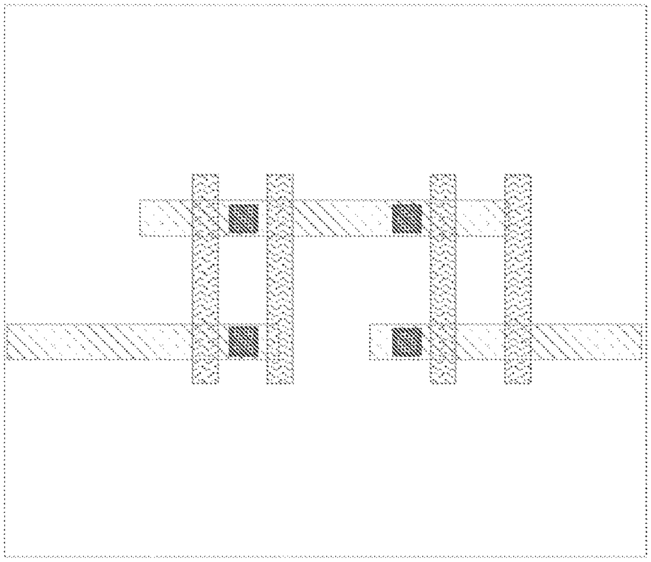
FIG. 2265B

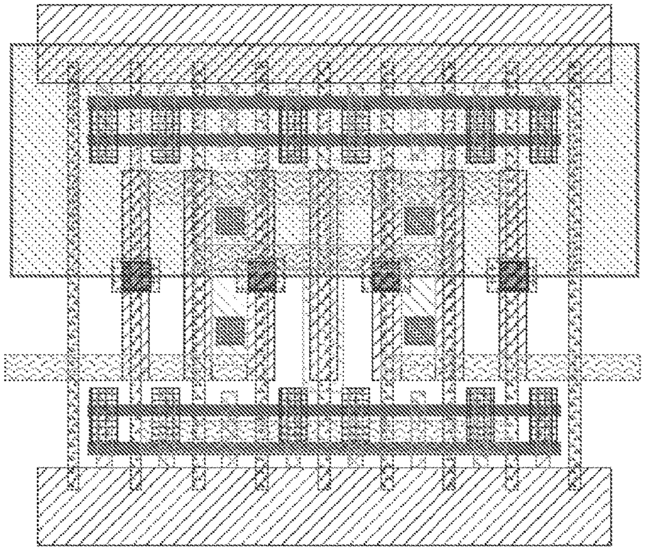
FIG. 2266A
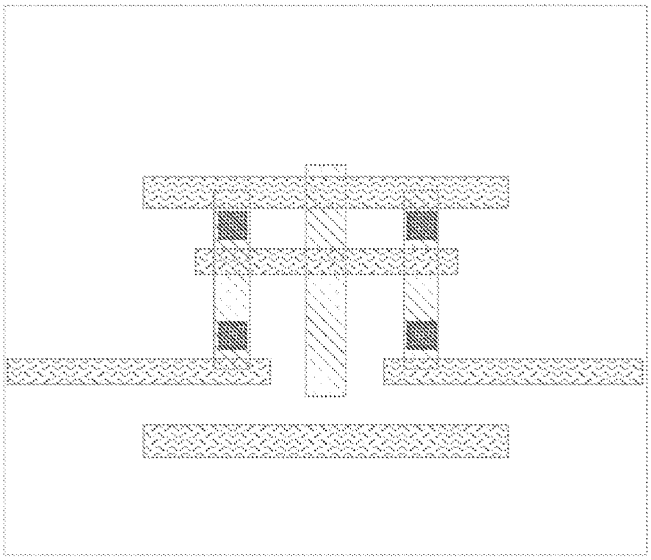
FIG. 2266B

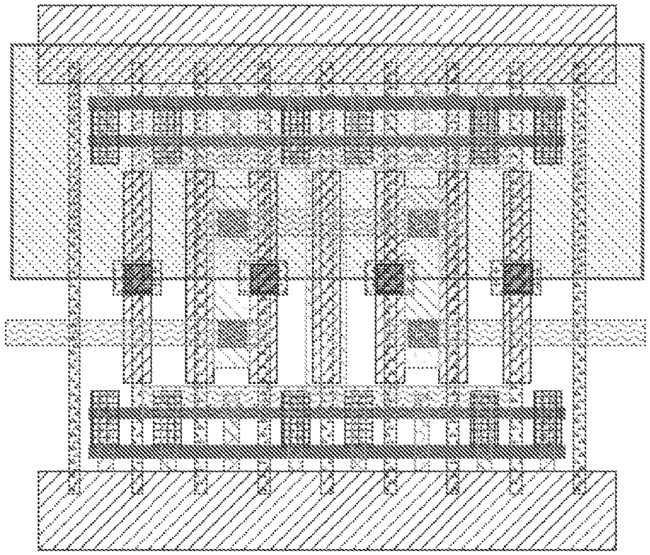
FIG. 2267A
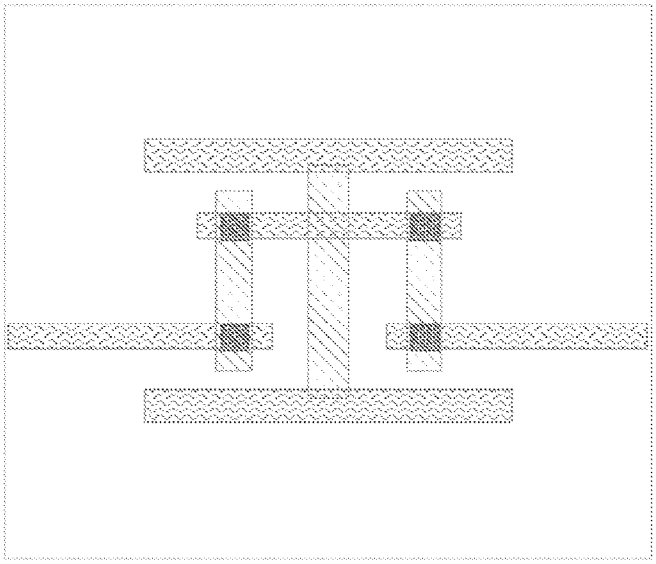
FIG. 2267B
*M* PDF Solutions, Inc.

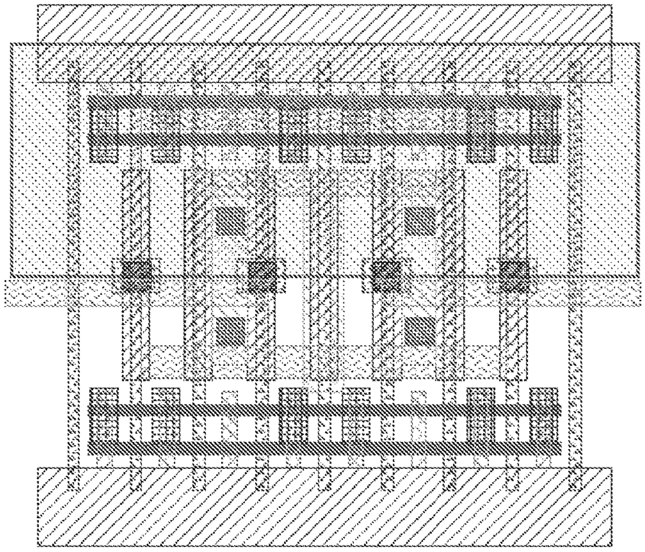
FIG. 2268A
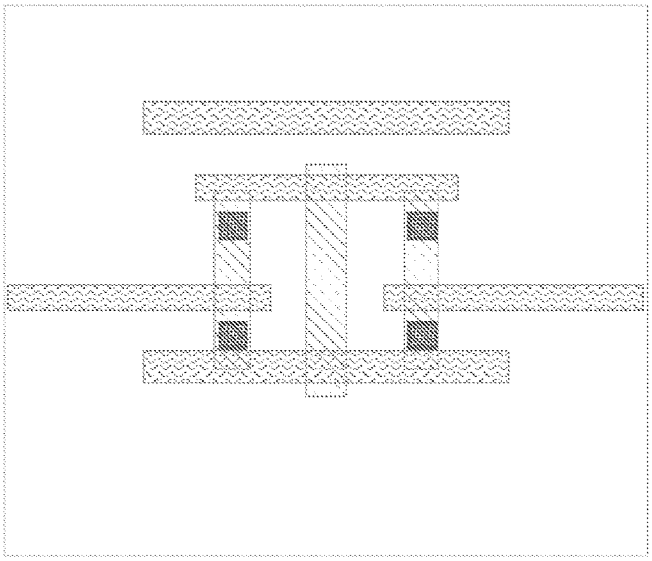
FIG. 2268B
*M* PDF Solutions, Inc.

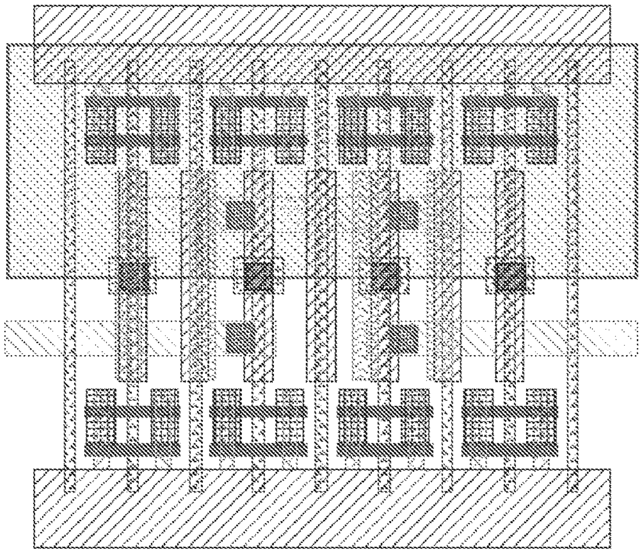
FIG. 2269A
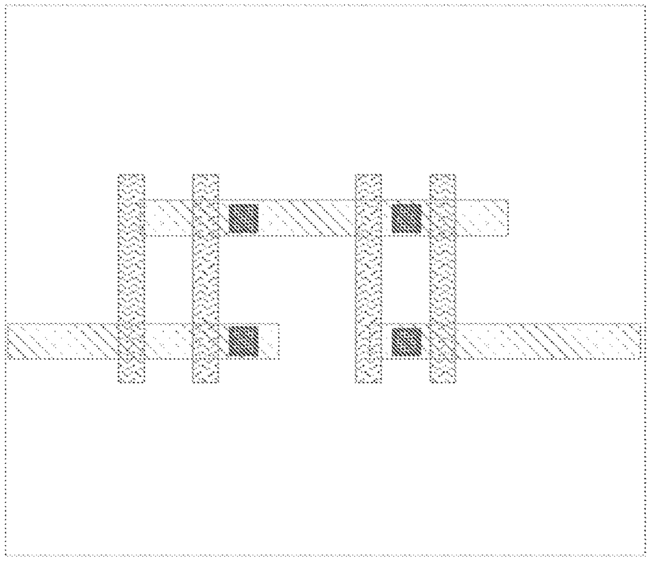
FIG. 2269B

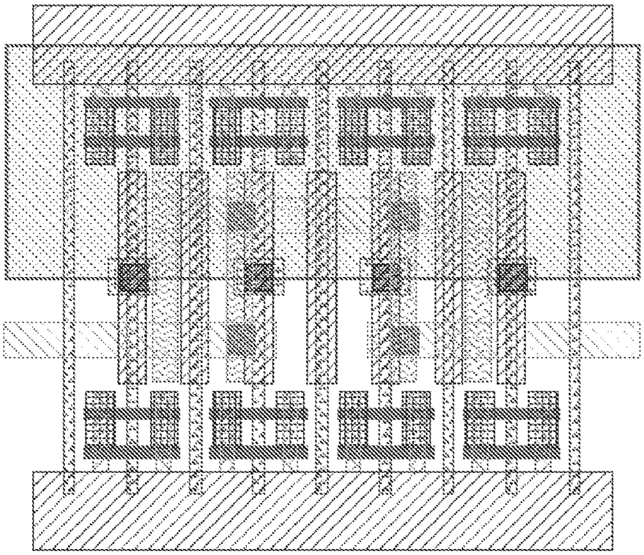
FIG. 2270A
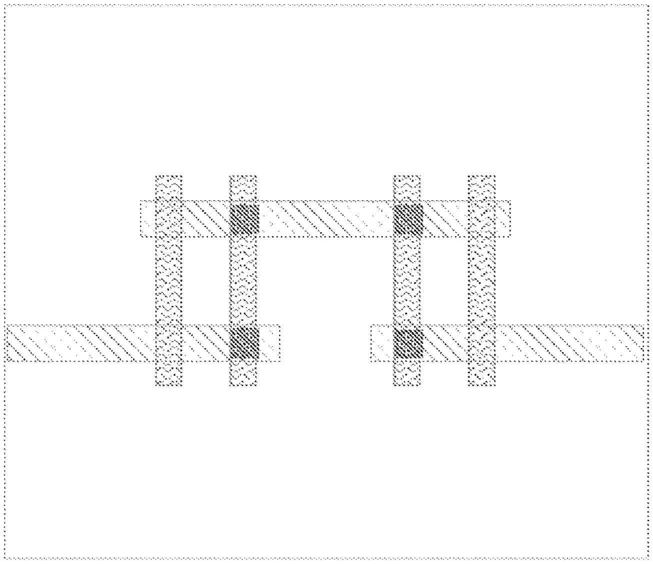
FIG. 2270B
*M* PDF Solutions, Inc.

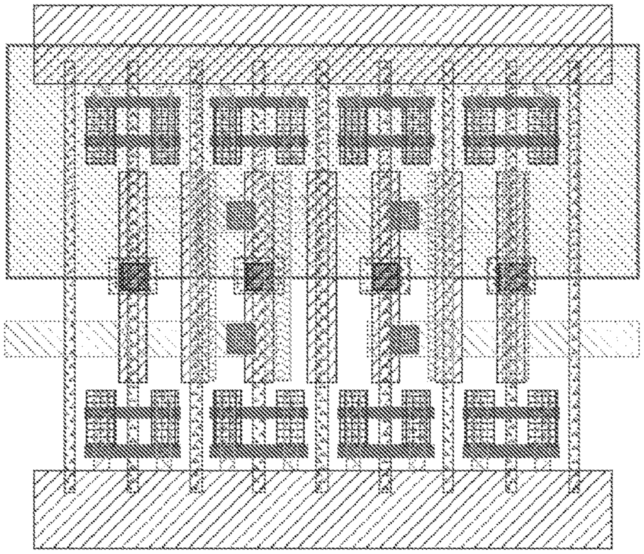
FIG. 2271A
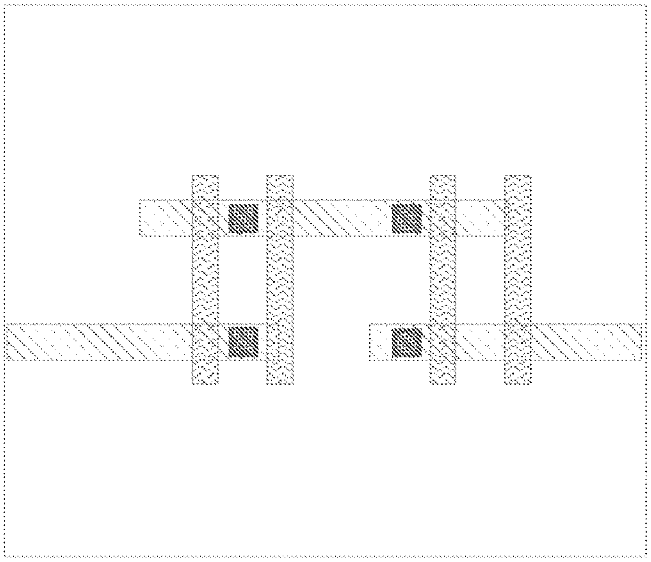
FIG. 2271B
*M* PDF Solutions, Inc.

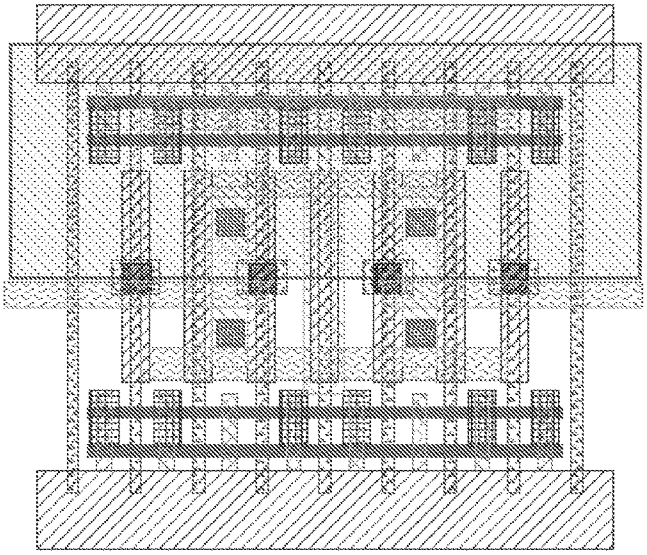
FIG. 2272A
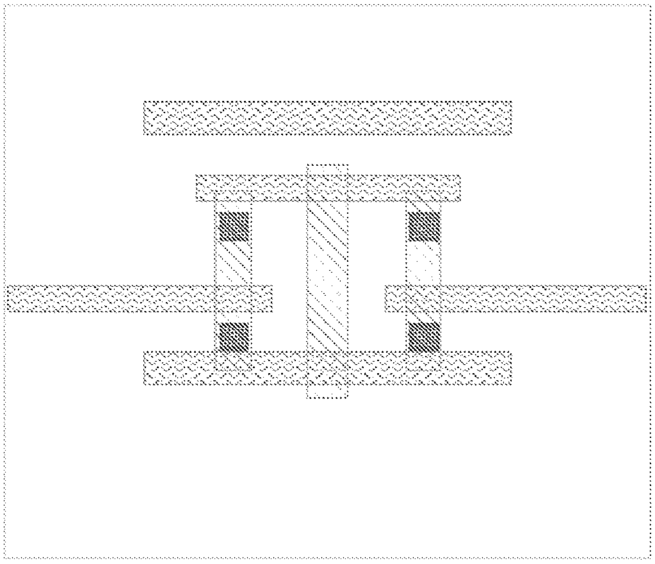
FIG. 2272B

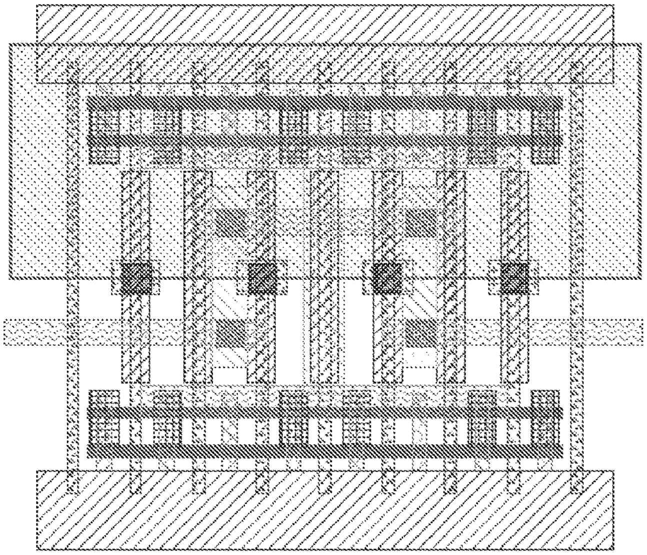
FIG. 2273A
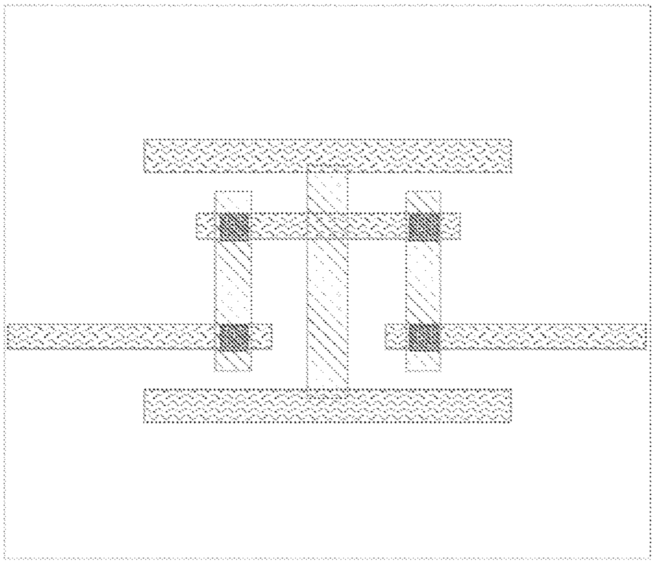
FIG. 2273B

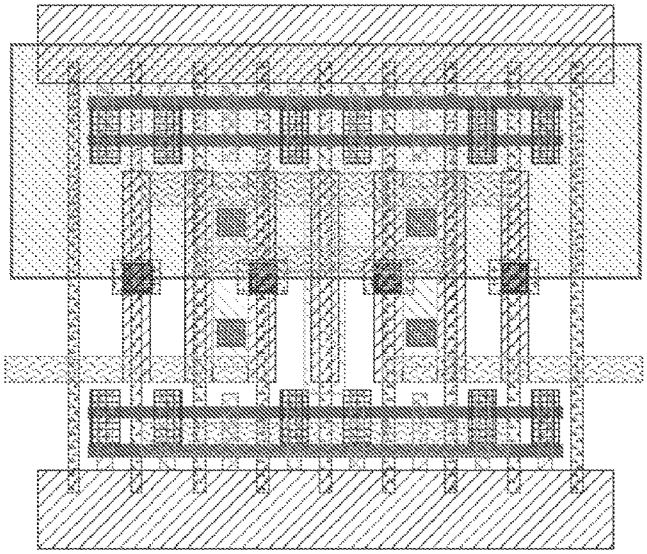
FIG. 2274A
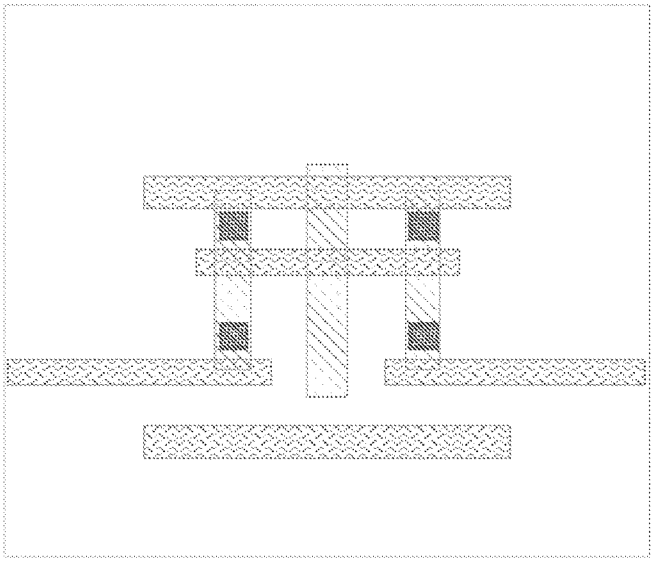
FIG. 2274B

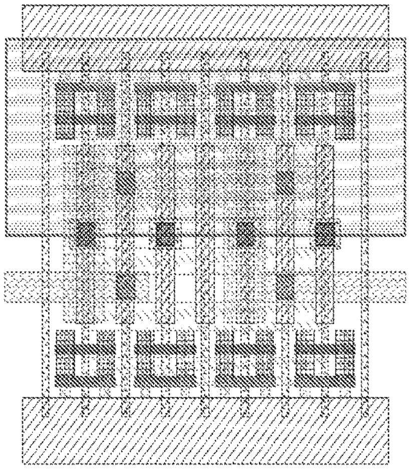
FIG. 2275A
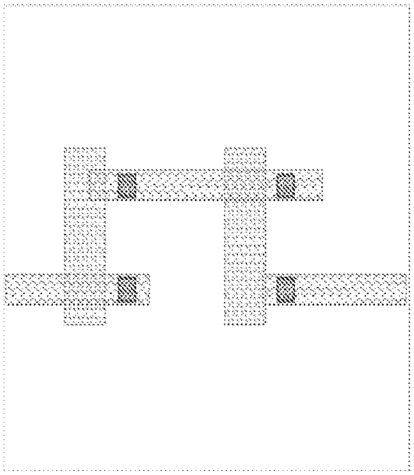
FIG. 2275B

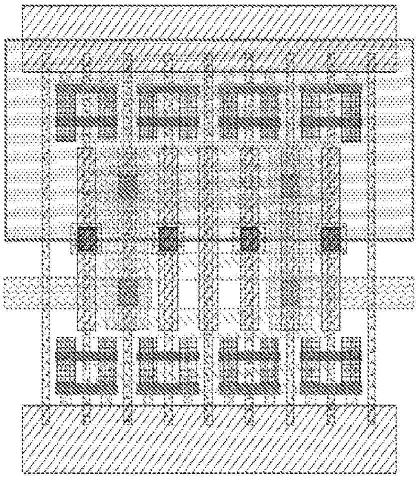
FIG. 2276A
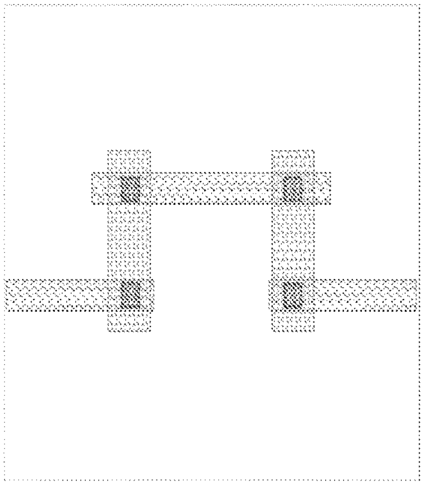
FIG. 2276B

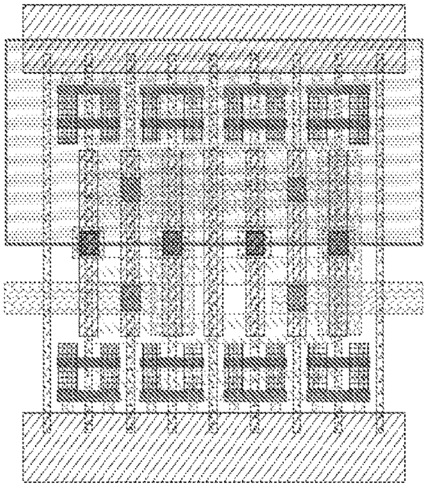
FIG. 2277A
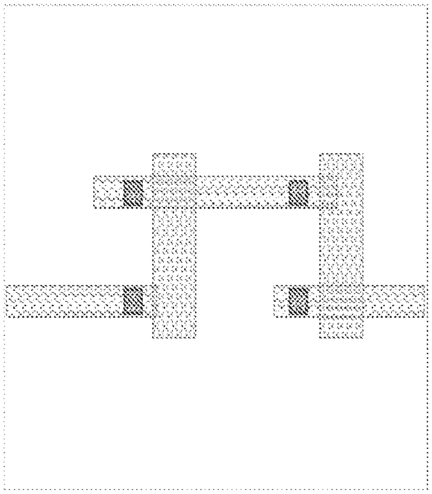
FIG. 2277B

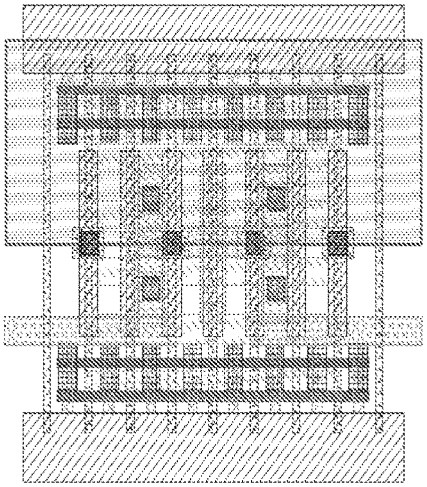
FIG. 2278A
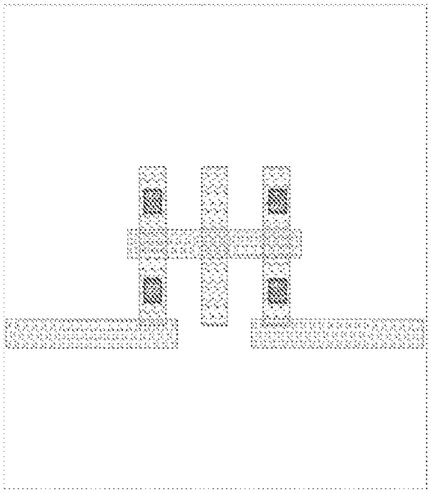
FIG. 2278B

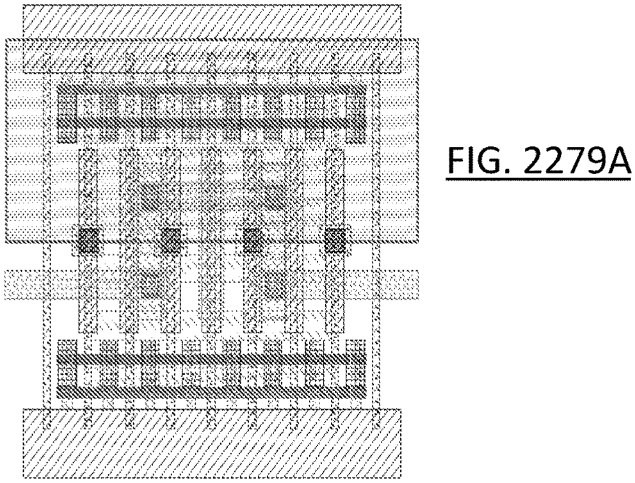
FIG. 2279A
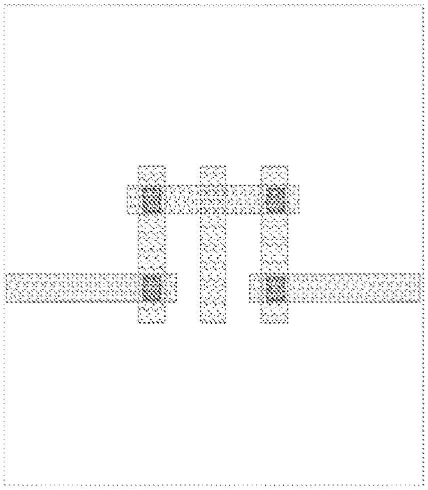
FIG. 2279B
*M* PDF Solutions, Inc.

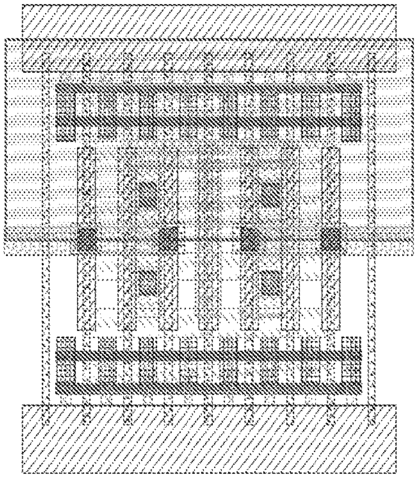
FIG. 2280A
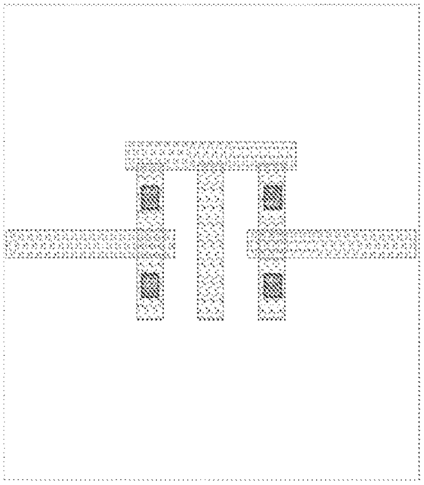
FIG. 2280B

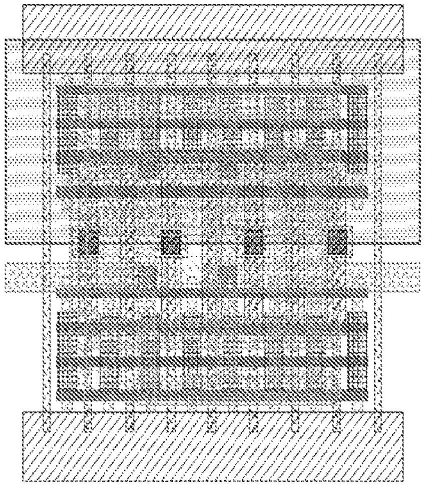
FIG. 2281A
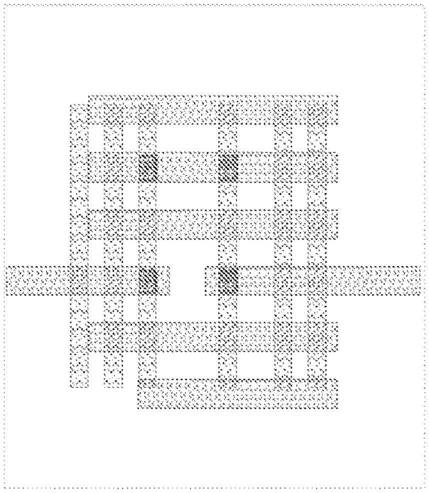
FIG. 2281B

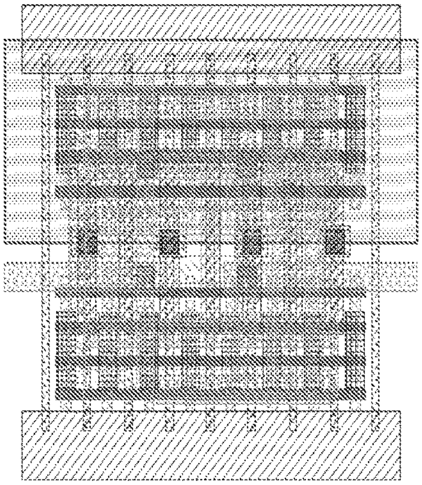
FIG. 2282A
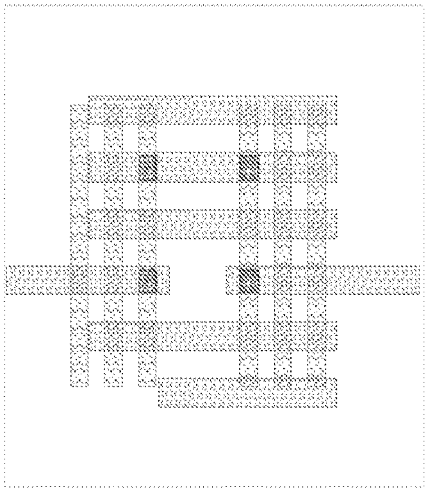
FIG. 2282B

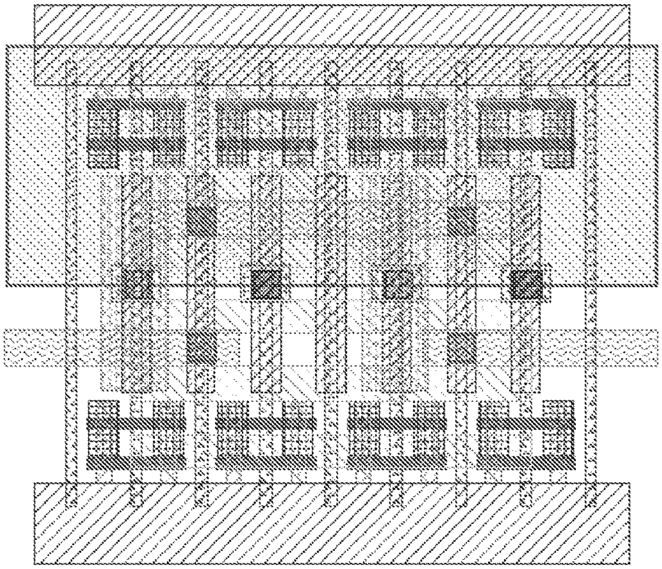
FIG. 2283A
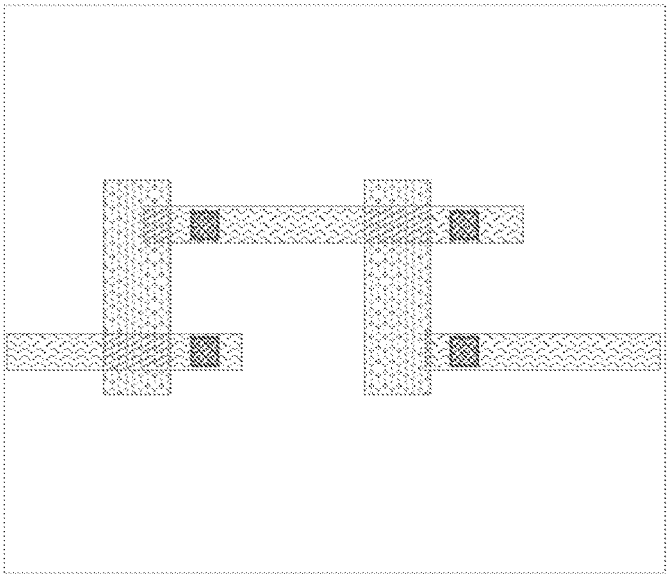
FIG. 2283B

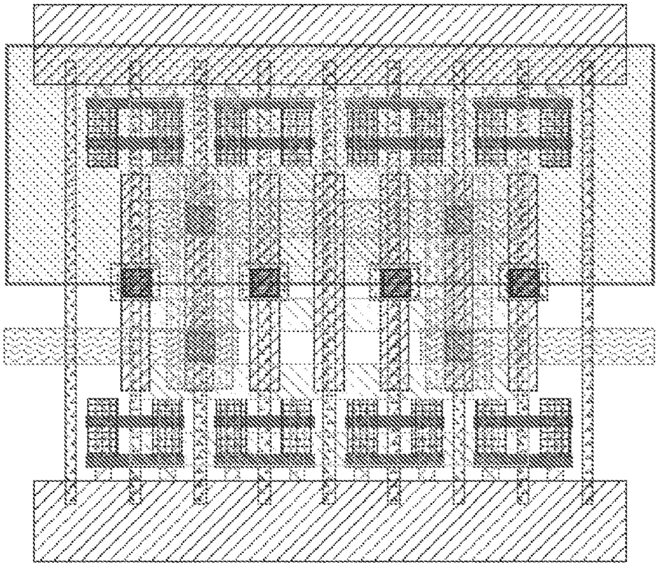
FIG. 2284A
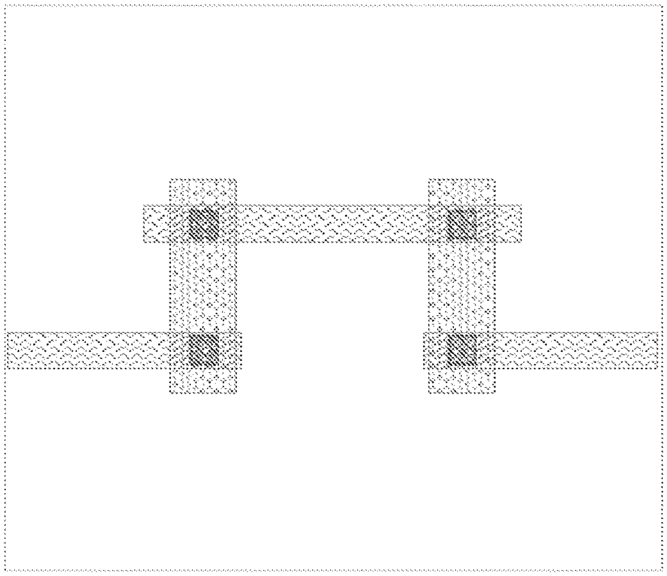
FIG. 2284B
*M* PDF Solutions, Inc.

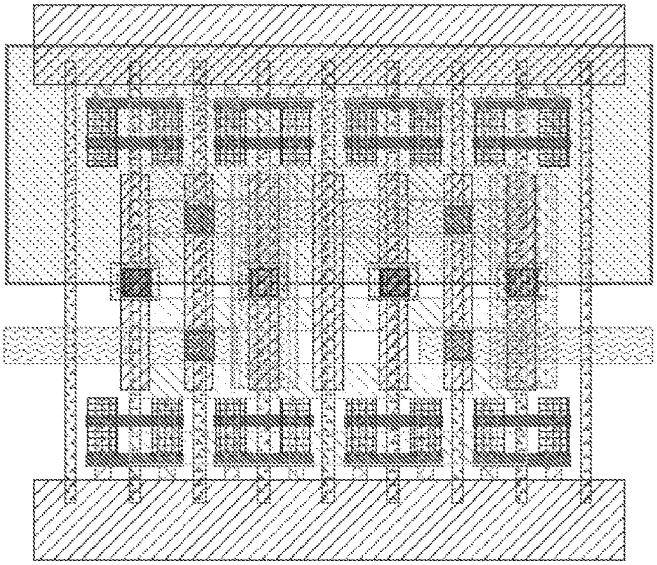
FIG. 2285A
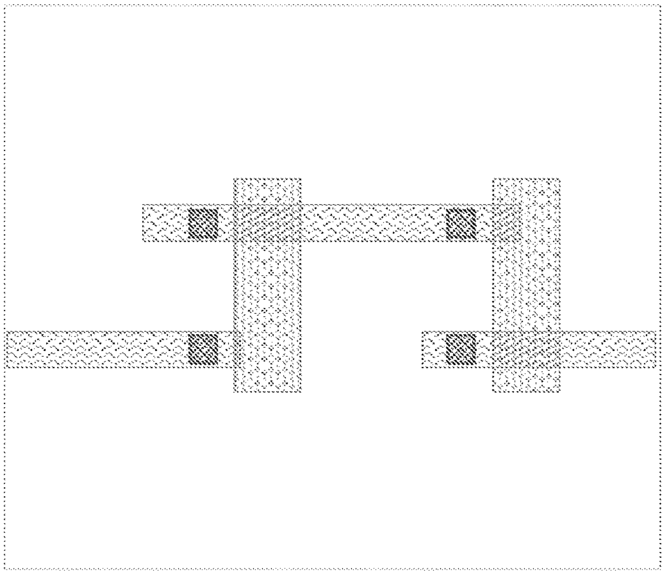
FIG. 2285B
*M* PDF Solutions, Inc.

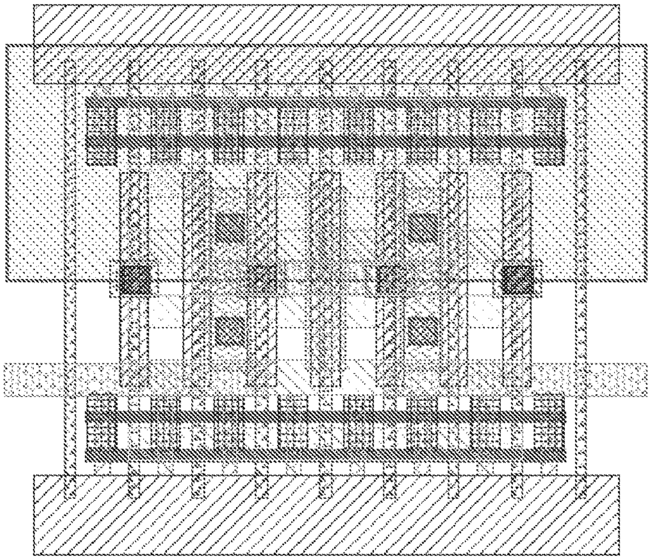
FIG. 2286A
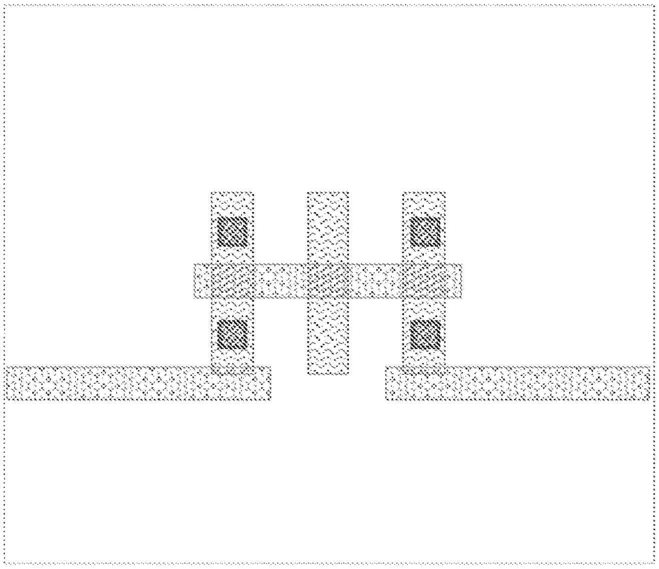
FIG. 2286B
*M* PDF Solutions, Inc.

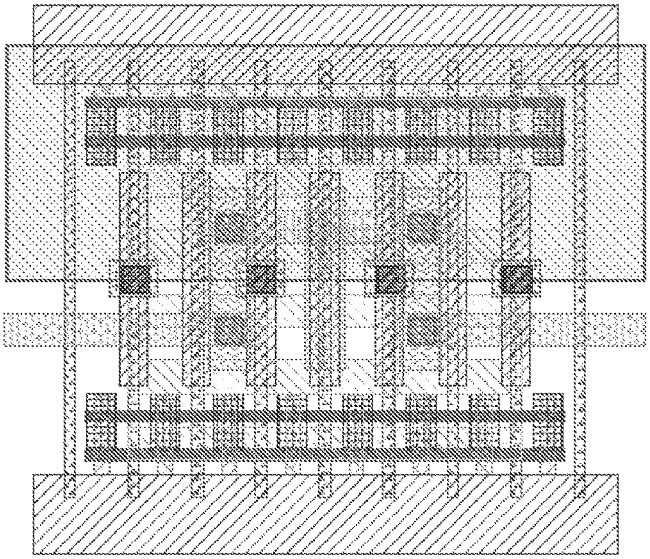
FIG. 2287A
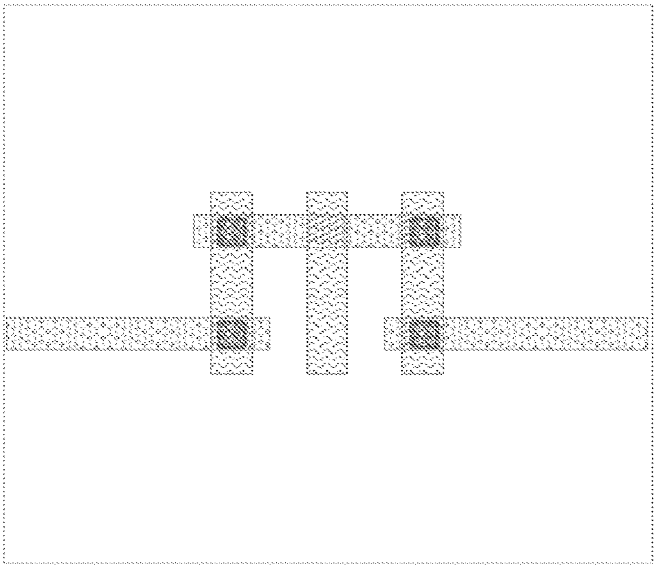
FIG. 2287B
*M* PDF Solutions, Inc.

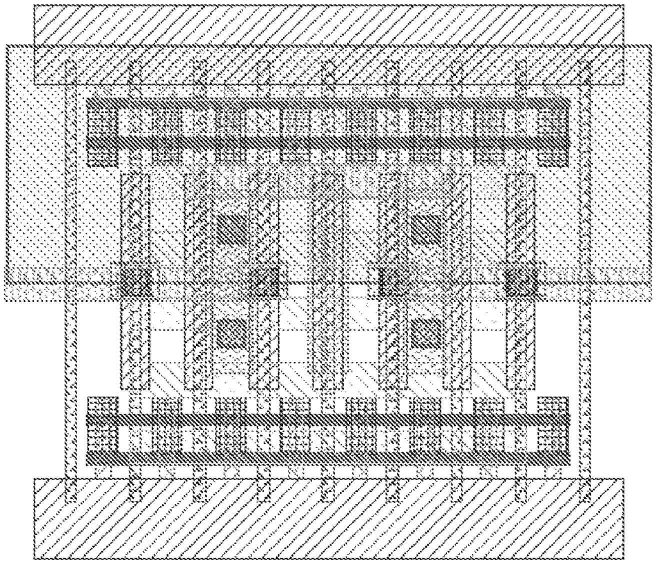
FIG. 2288A
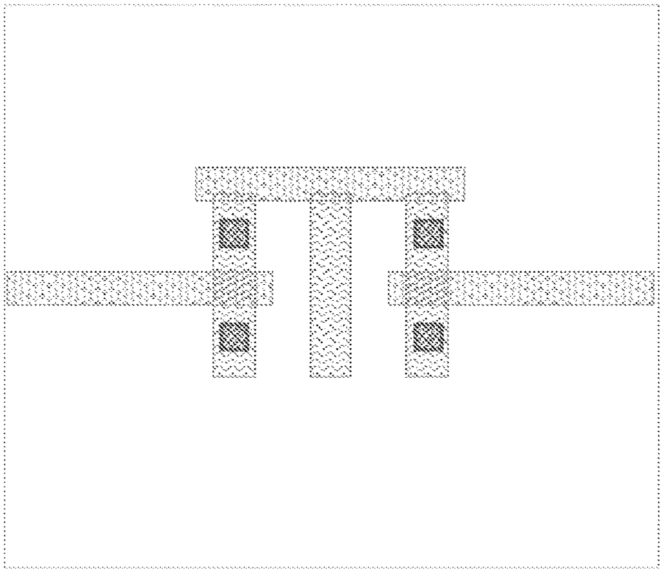
FIG. 2288B

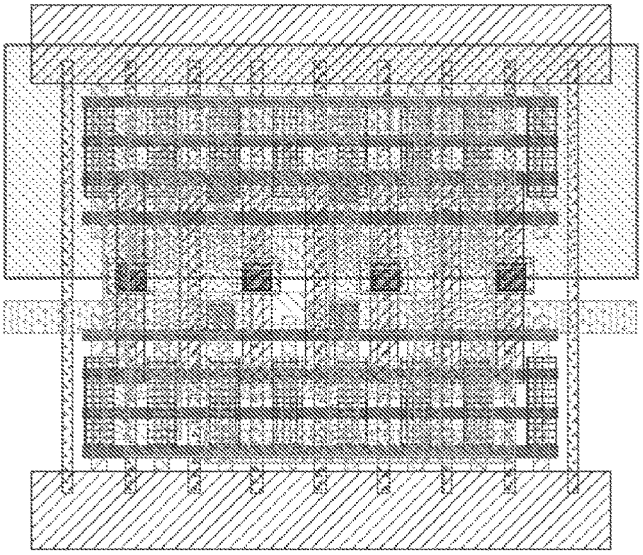
FIG. 2289A
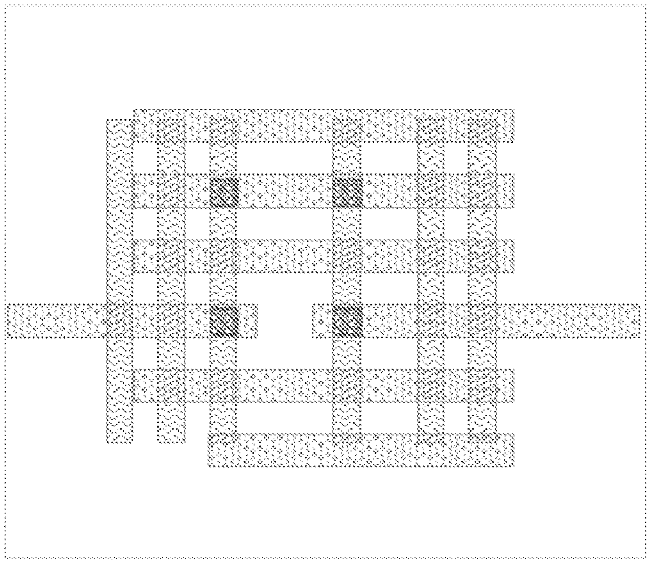
FIG. 2289B

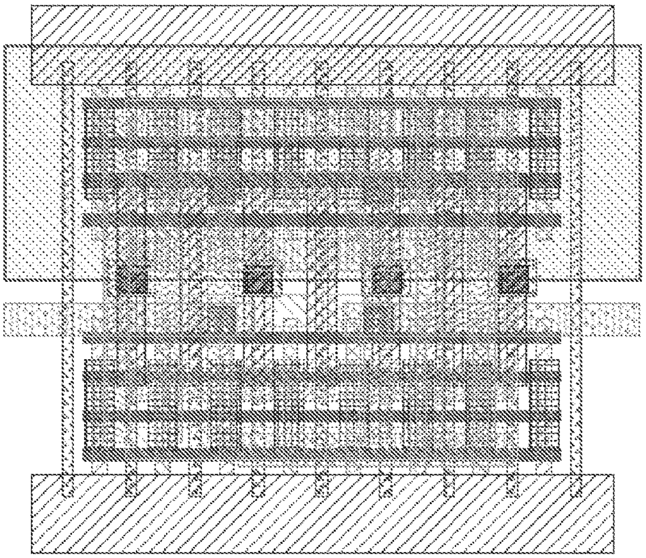
FIG. 2290A
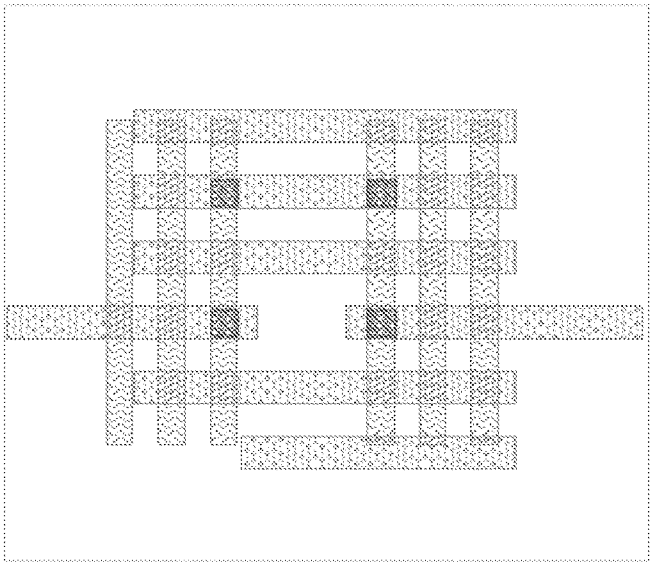
FIG. 2290B
*M* PDF Solutions, Inc.

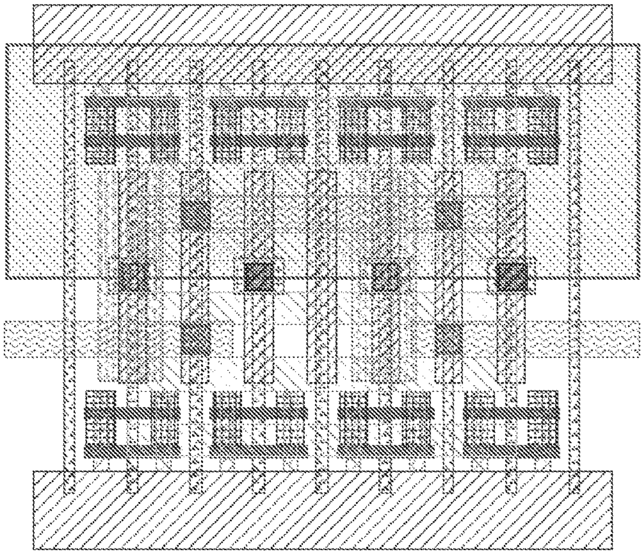
FIG. 2291A
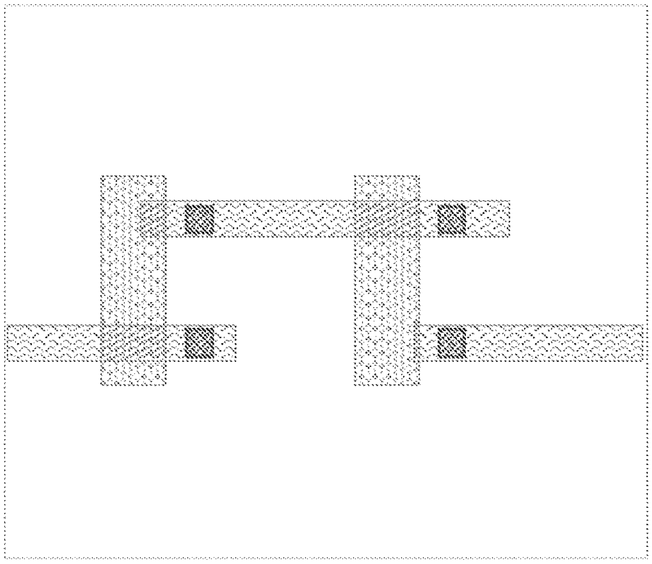
FIG. 2291B

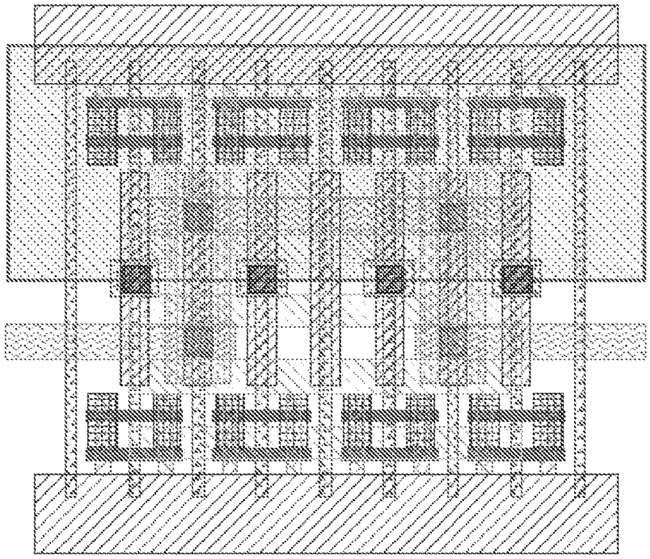
FIG. 2292A
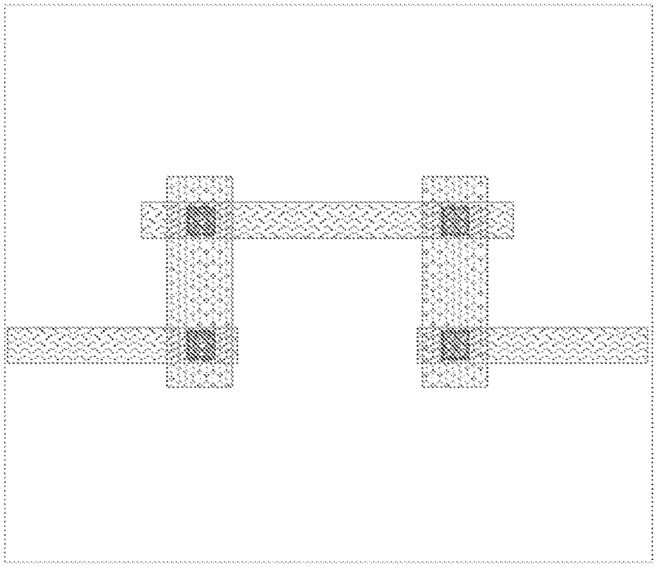
FIG. 2292B

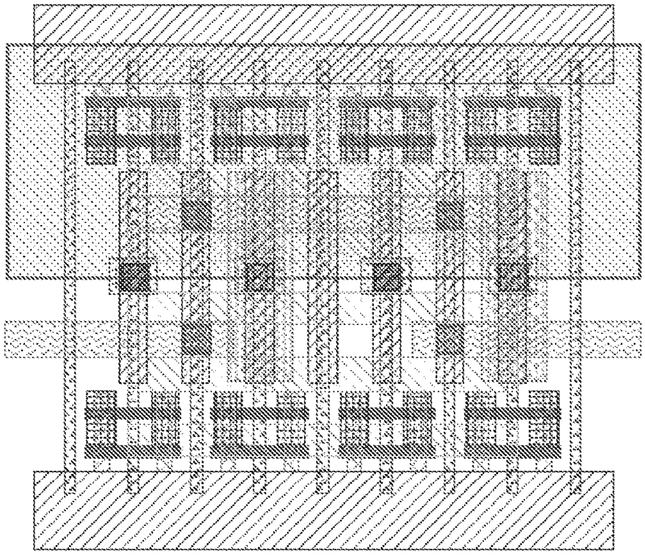
FIG. 2293A
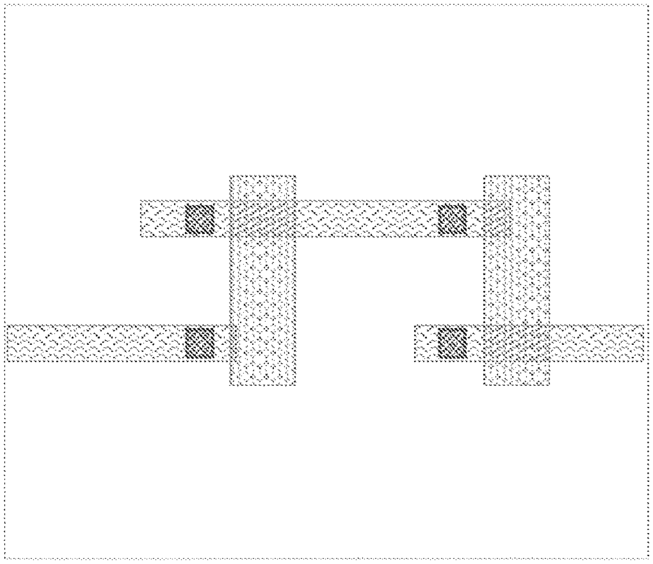
FIG. 2293B
*M* PDF Solutions, Inc.

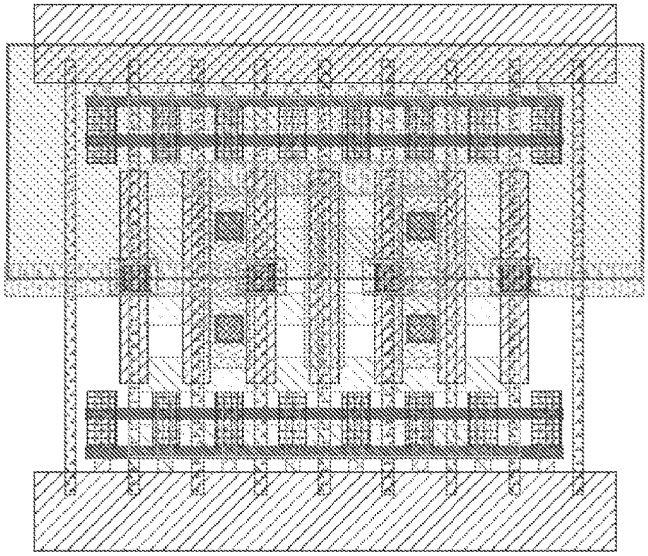
FIG. 2294A
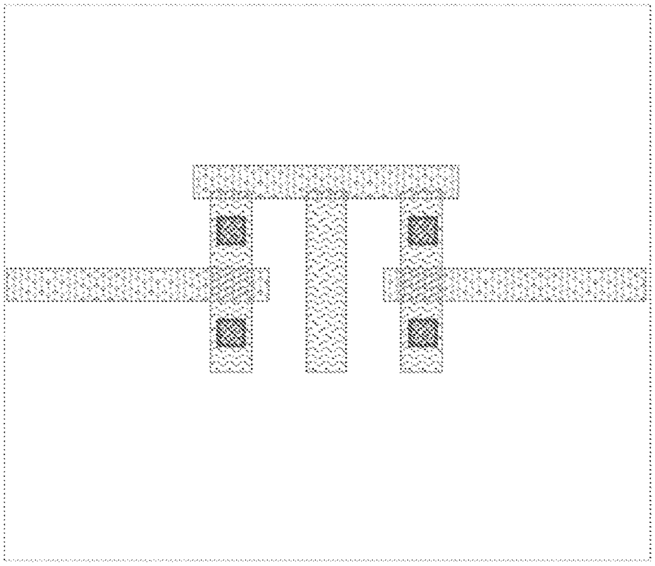
FIG. 2294B
*M* PDF Solutions, Inc.

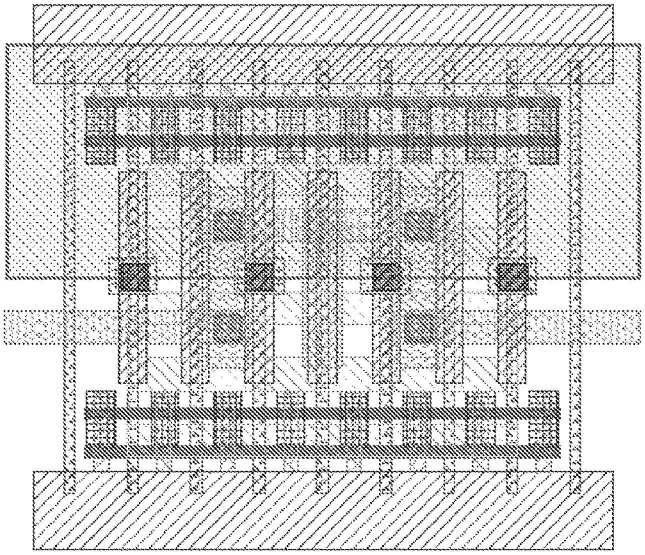
FIG. 2295A
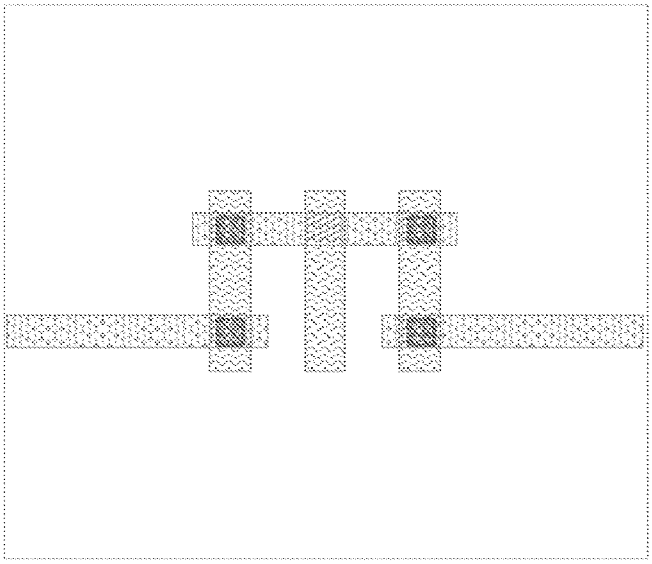
FIG. 2295B
*M* PDF Solutions, Inc.

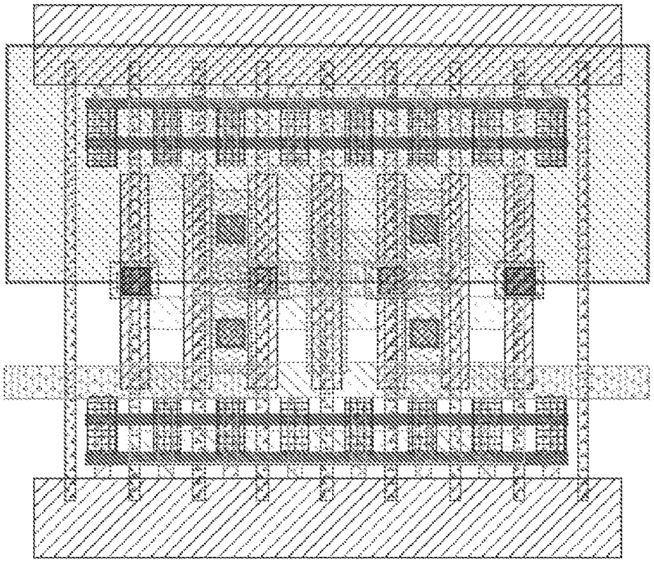
FIG. 2296A
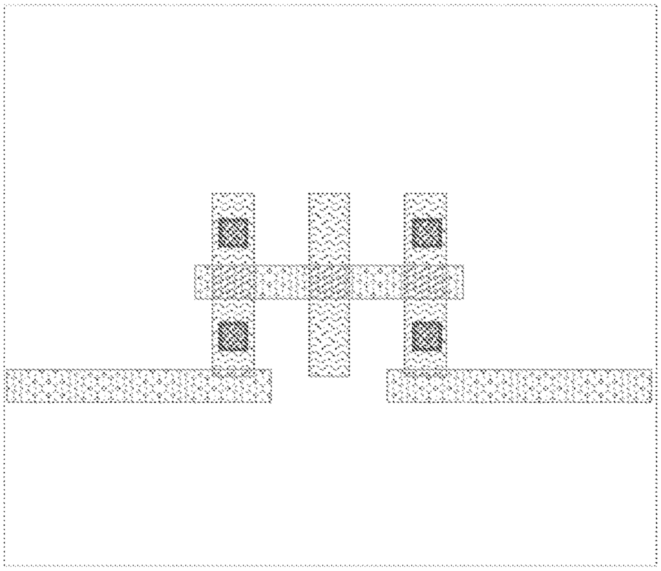
FIG. 2296B
*M* PDF Solutions, Inc.

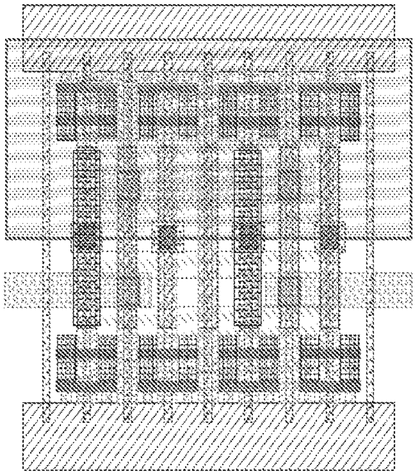
FIG. 2297A
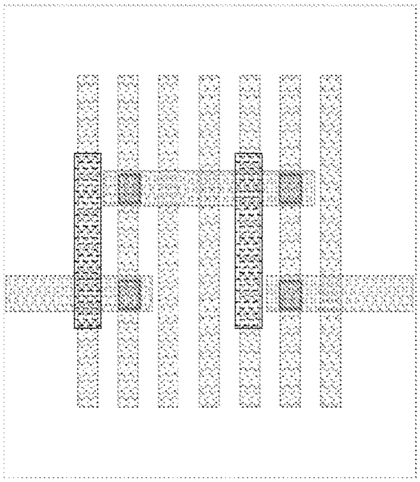
FIG. 2297B
*M* PDF Solutions, Inc.

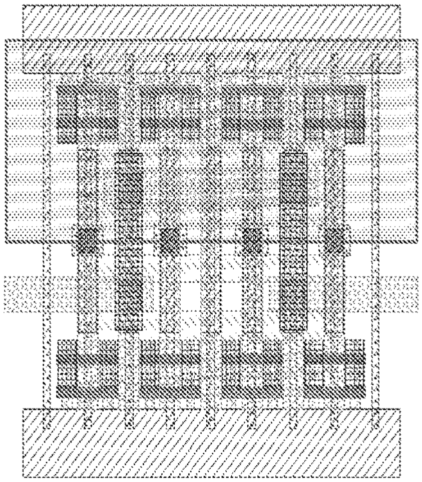
FIG. 2298A
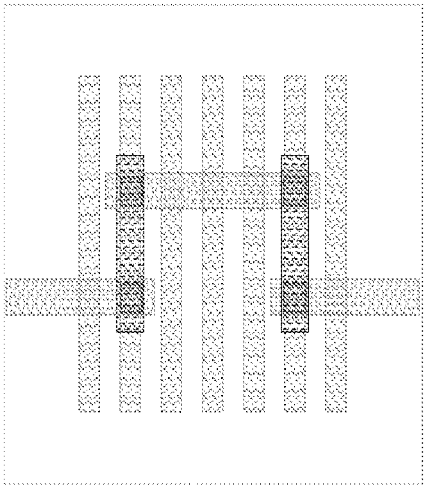
FIG. 2298B
*M* PDF Solutions, Inc.

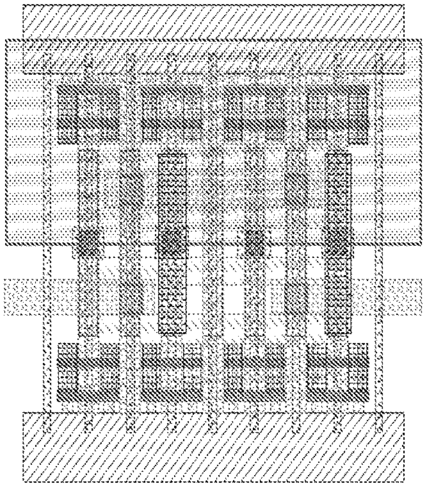
FIG. 2299A
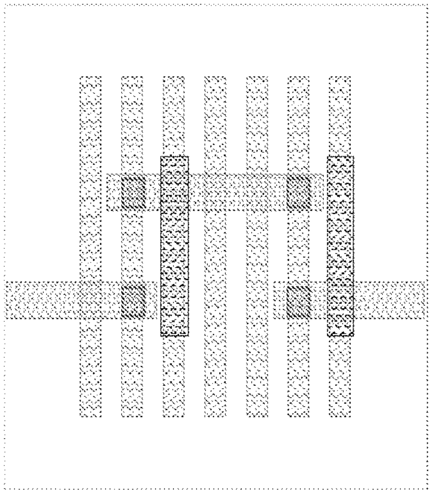
FIG. 2299B

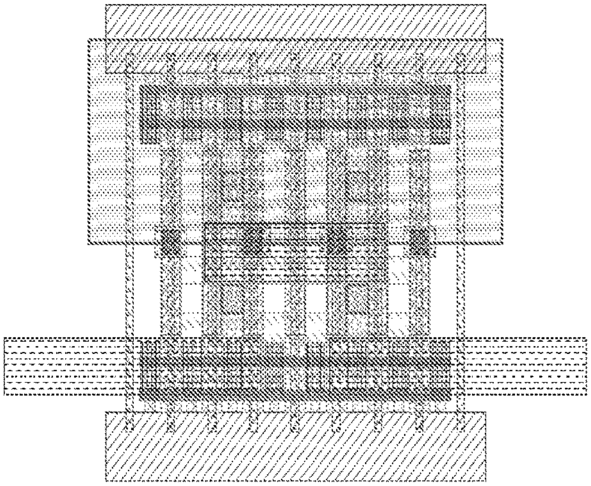
FIG. 2300A
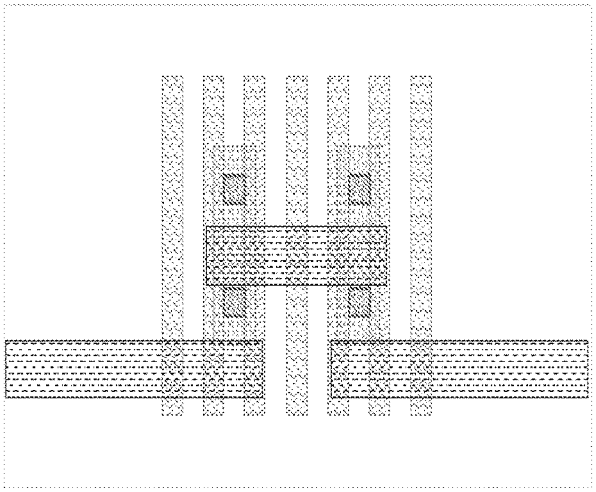
FIG. 2300B
*M* PDF Solutions, Inc.

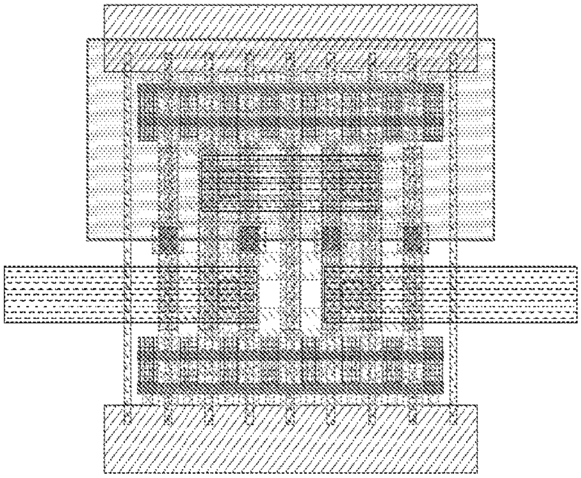
FIG. 2301A
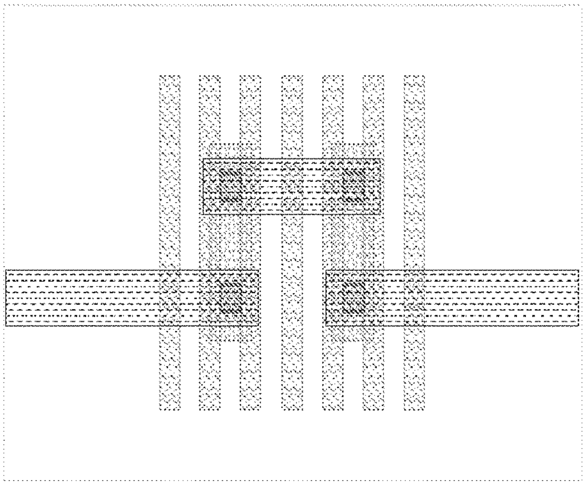
FIG. 2301B

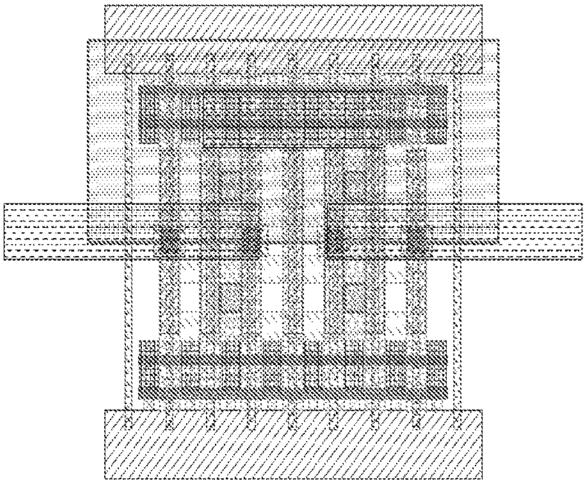
FIG. 2302A
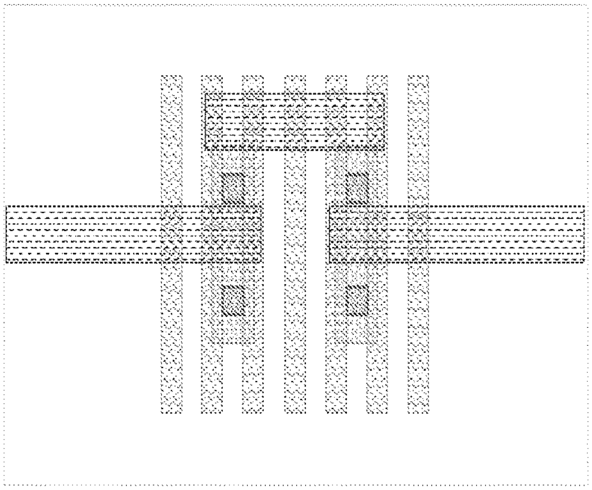
FIG. 2302B

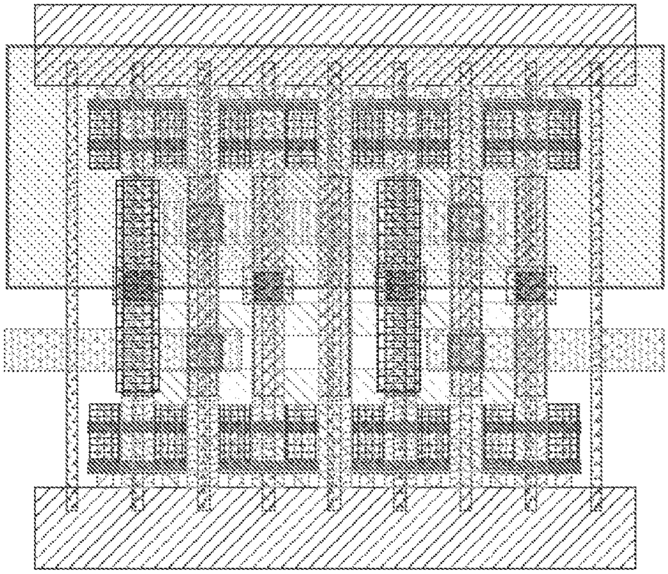
FIG. 2303A
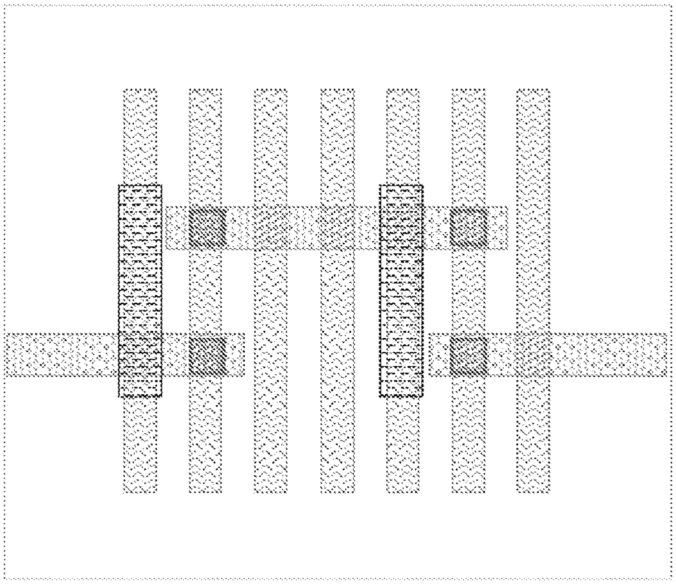
FIG. 2303B

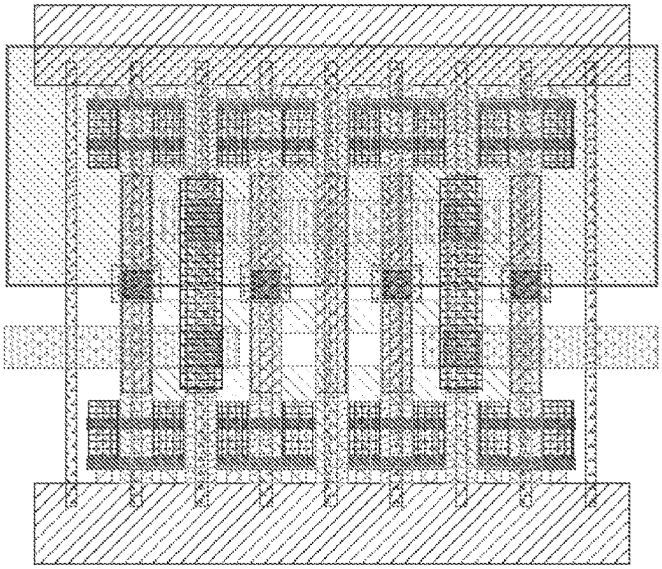
FIG. 2304A
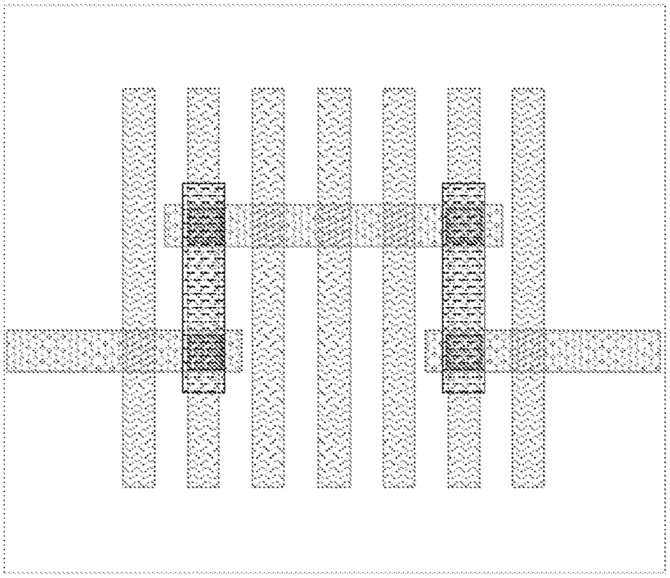
FIG. 2304B
*M* PDF Solutions, Inc.

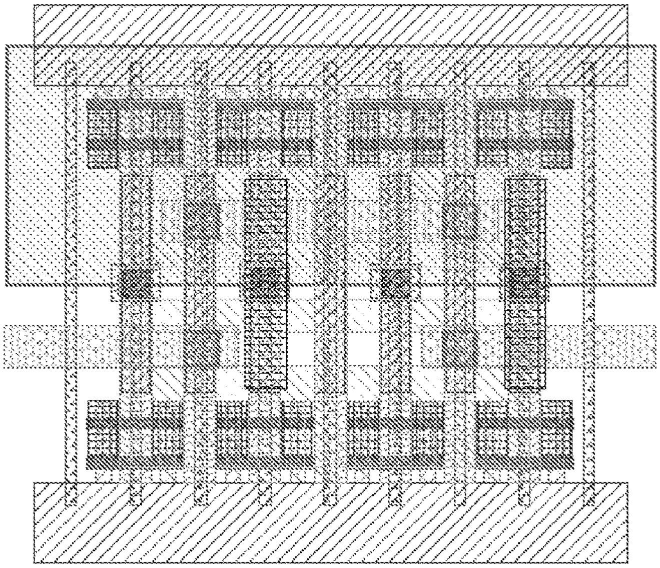
FIG. 2305A
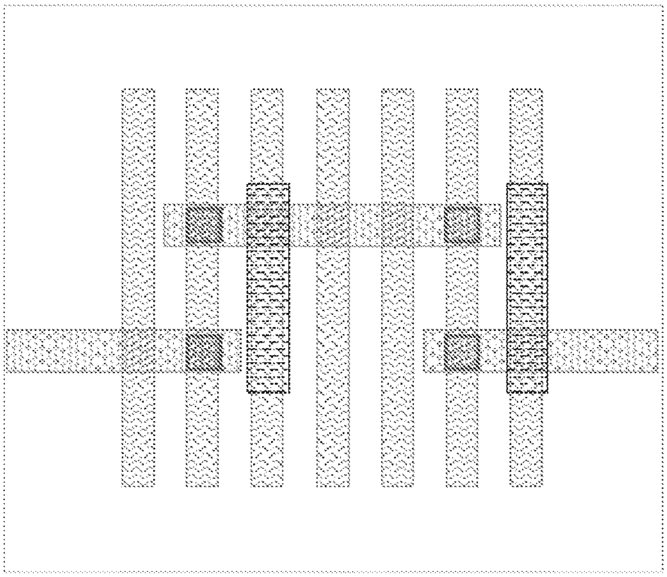
FIG. 2305B
*M* PDF Solutions, Inc.

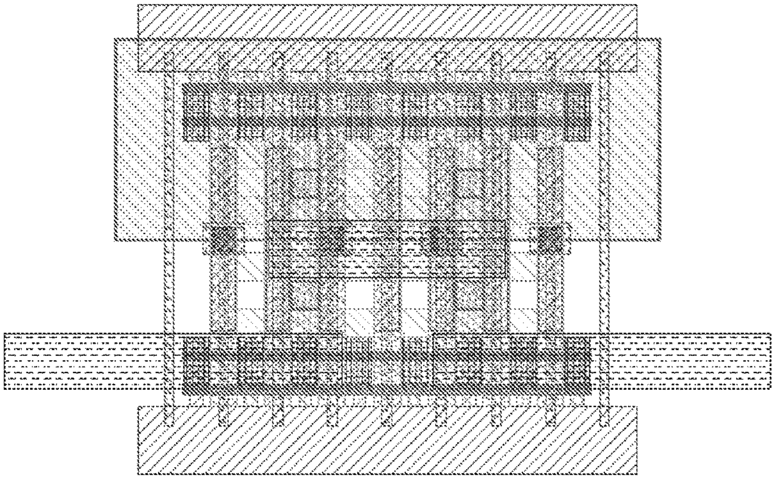
FIG. 2306A
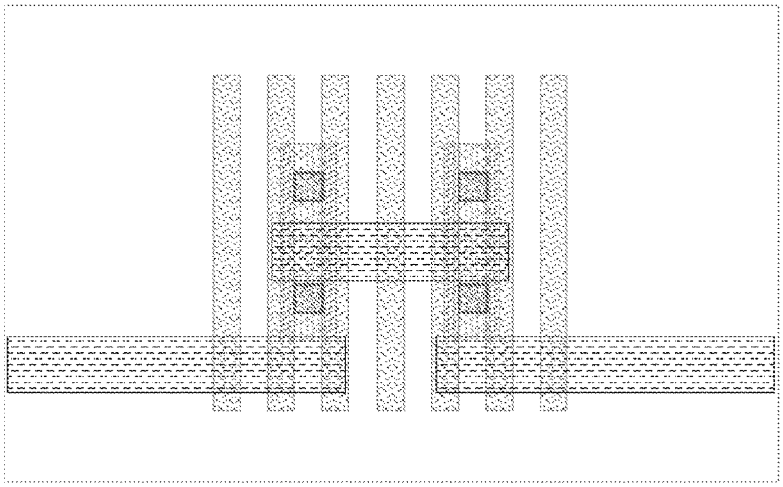
FIG. 2306B

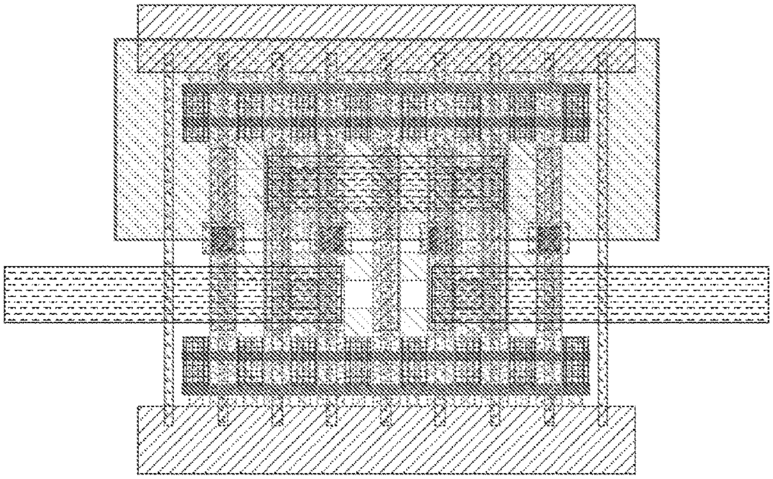
FIG. 2307A
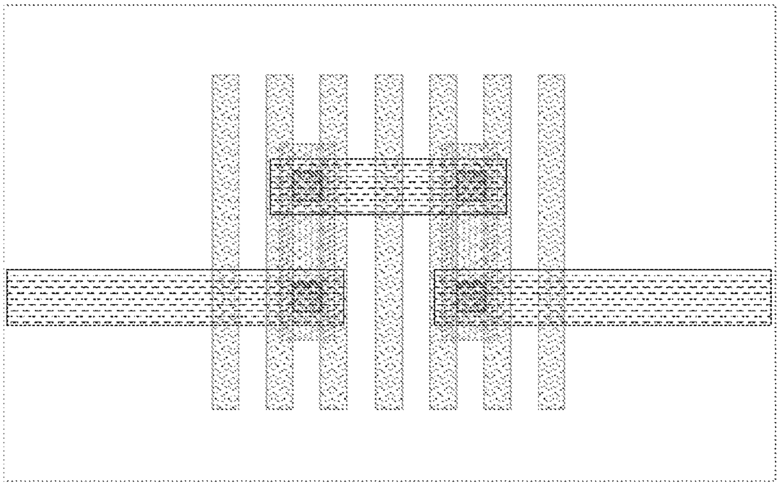
FIG. 2307B

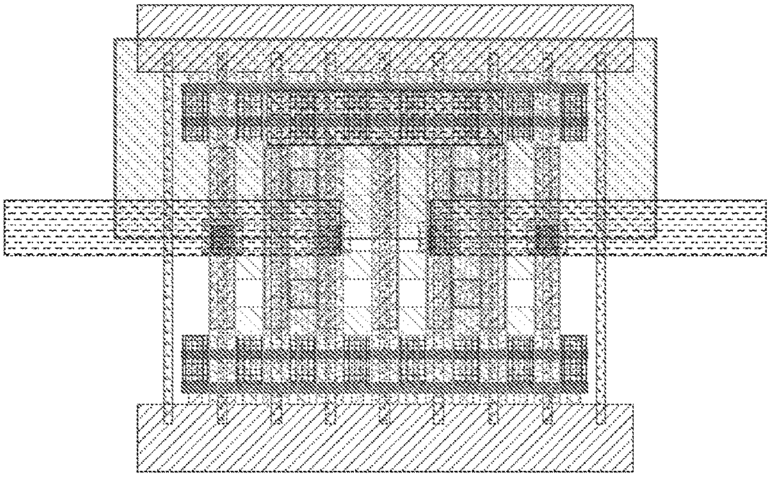
FIG. 2308A
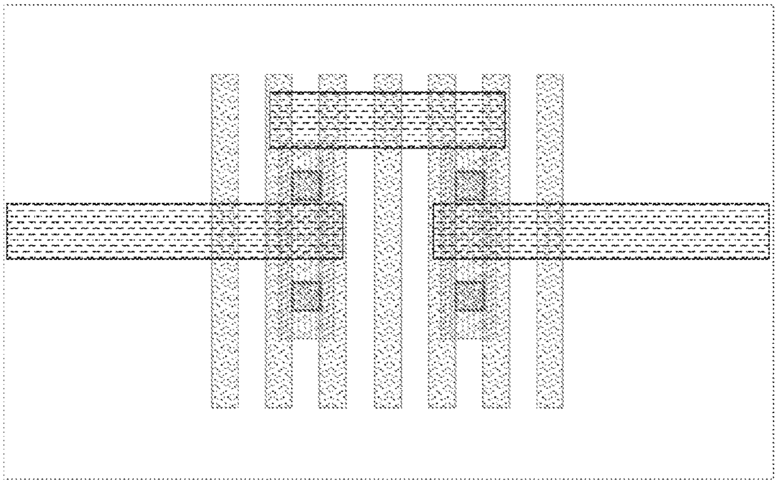
FIG. 2308B
*M* PDF Solutions, Inc.

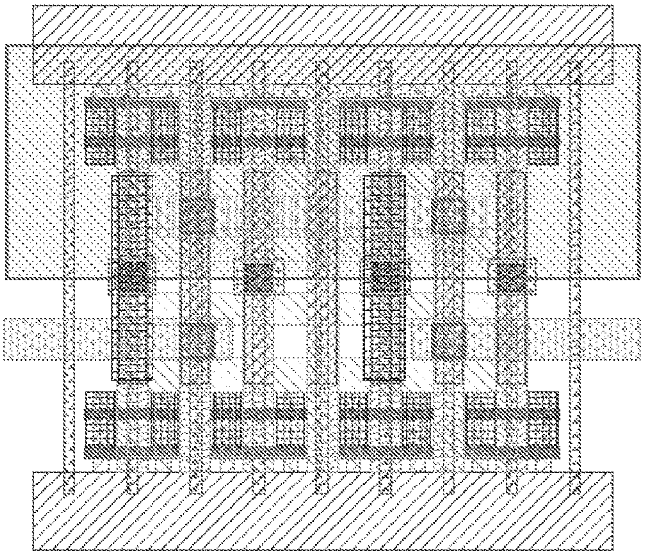
FIG. 2309A
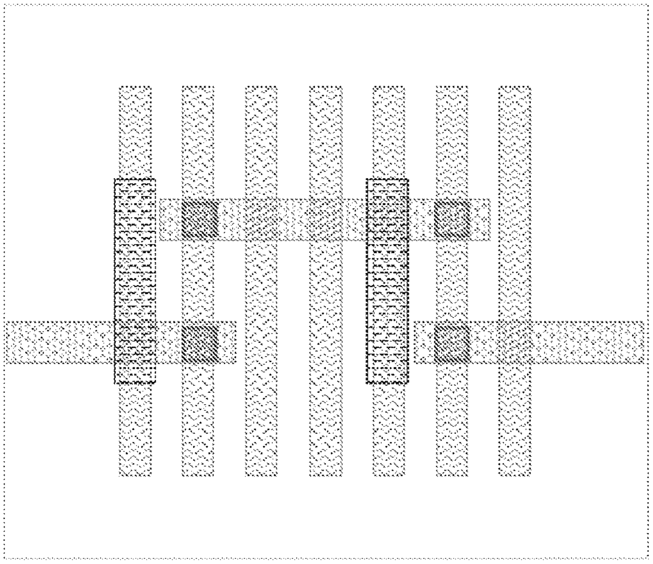
FIG. 2309B
*M* PDF Solutions, Inc.

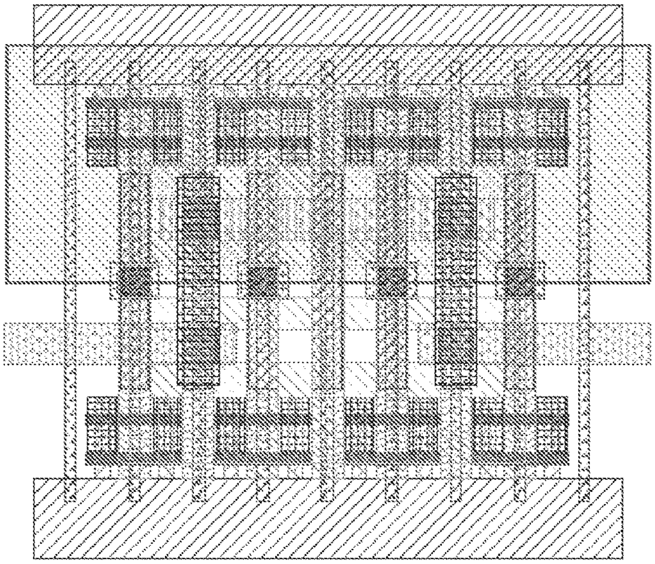
FIG. 2310A
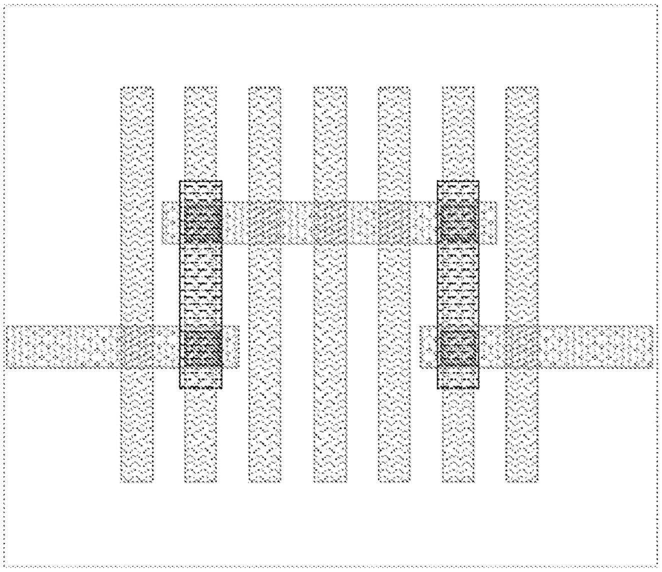
FIG. 2310B

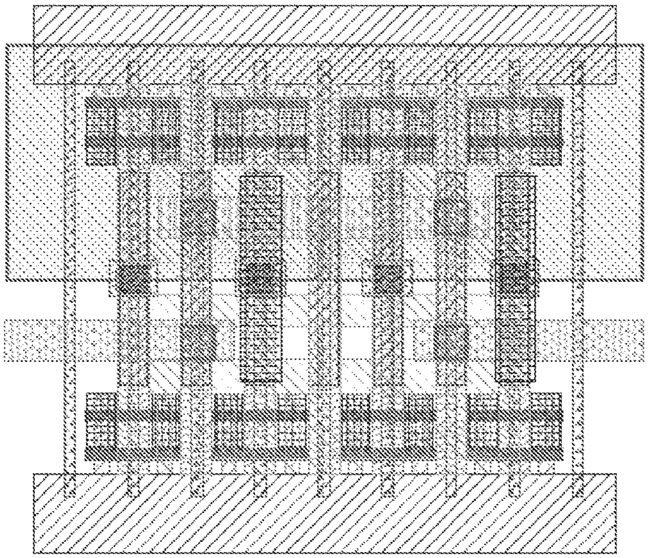
FIG. 2311A
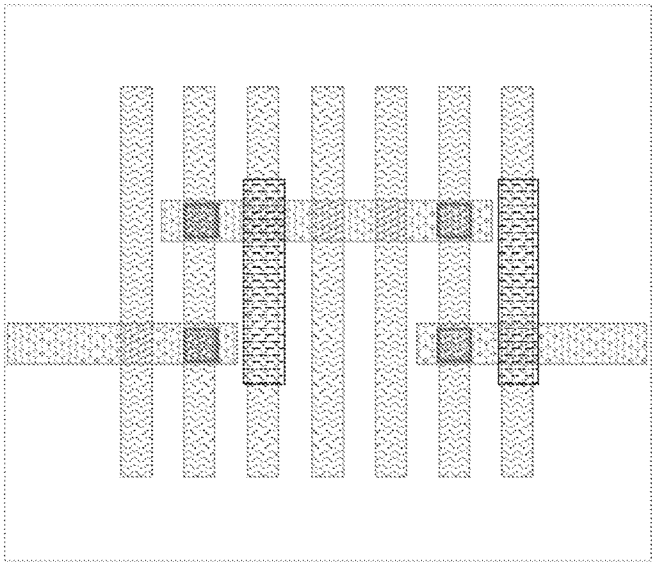
FIG. 2311B

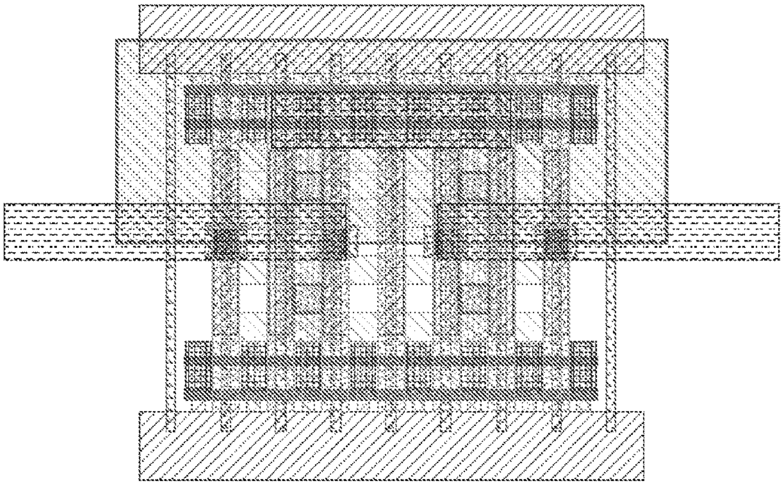
FIG. 2312A
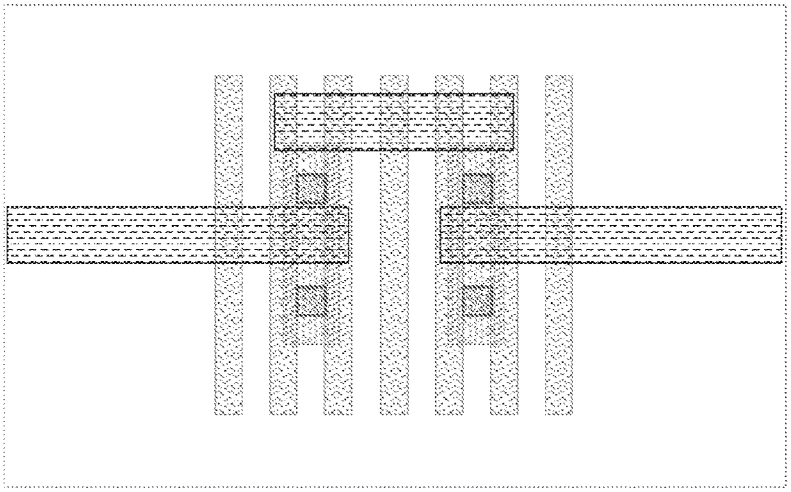
FIG. 2312B

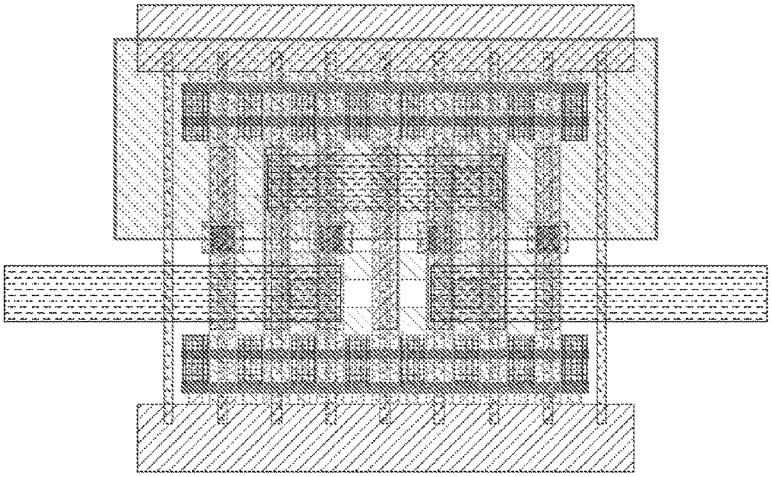
FIG. 2313A
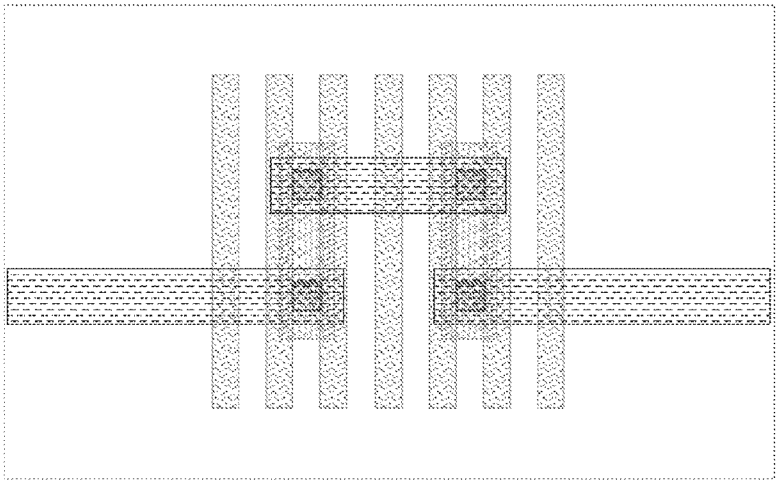
FIG. 2313B
*M* PDF Solutions, Inc.

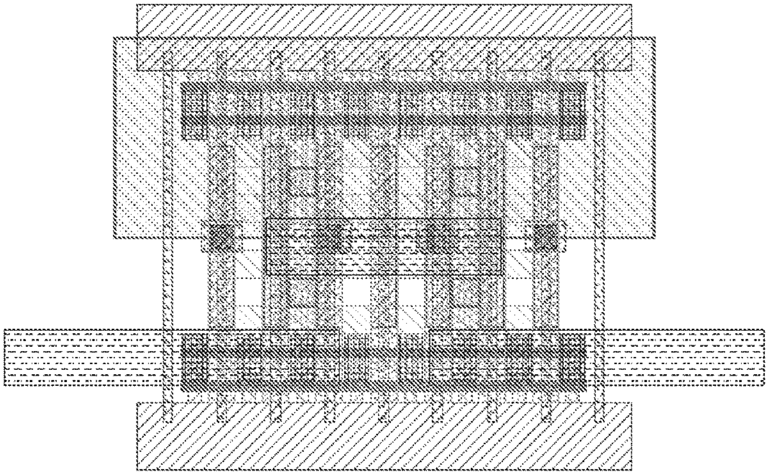
FIG. 2314A
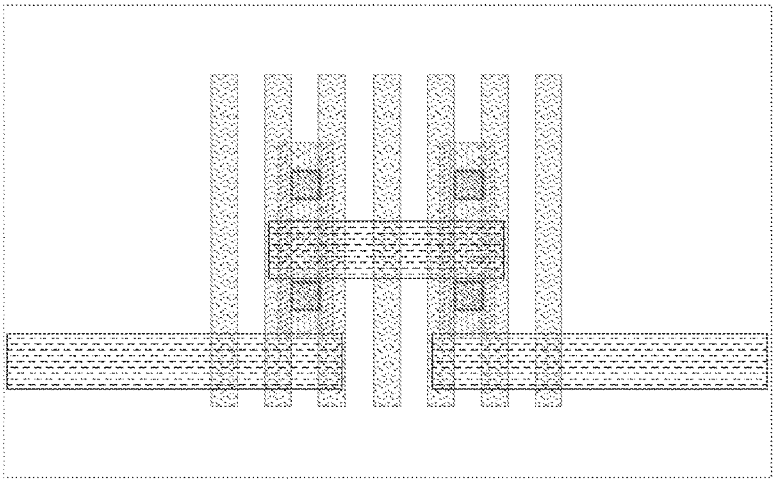
FIG. 2314B
*M* PDF Solutions, Inc.

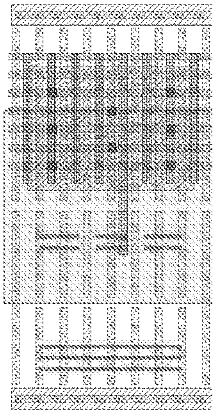
FIG. 2315A
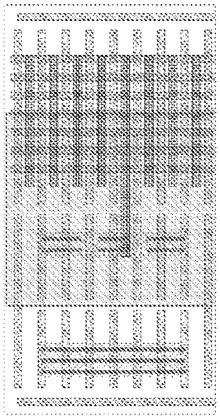
FIG. 2315B
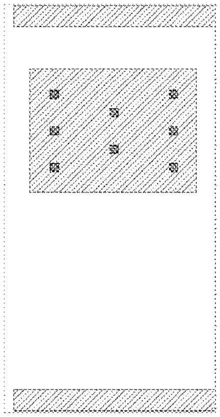
FIG. 2315C

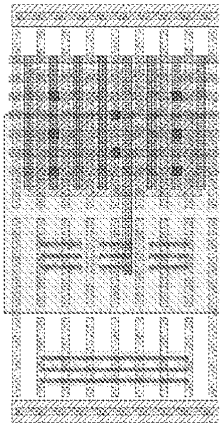
FIG. 2316A
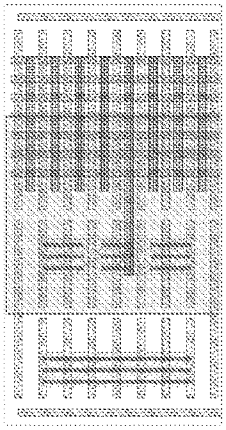
FIG. 2316B
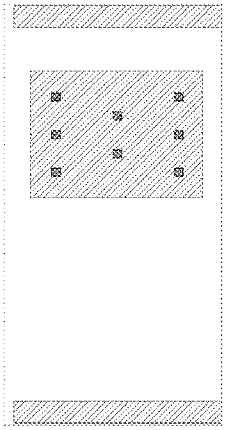
FIG. 2316C
*M* PDF Solutions, Inc.

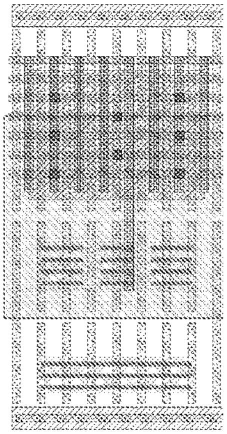
FIG. 2317A
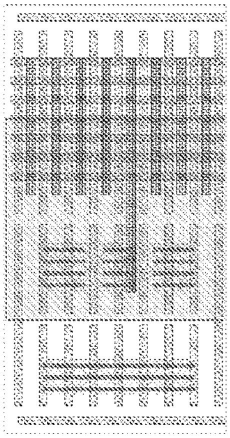
FIG. 2317B
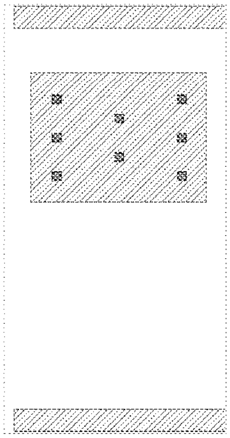
FIG. 2317C

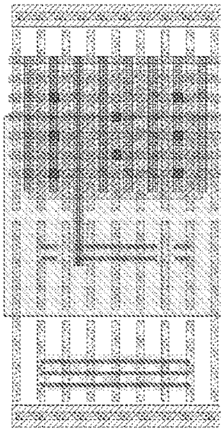
FIG. 2318A
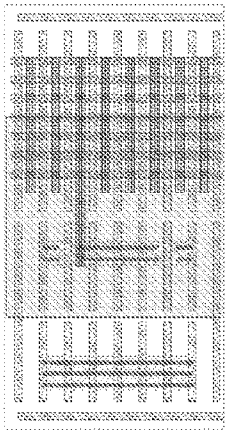
FIG. 2318B
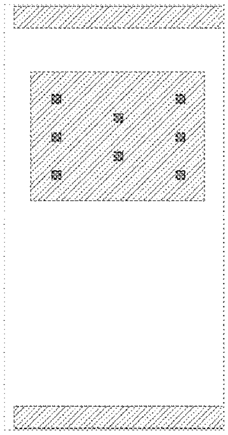
FIG. 2318C

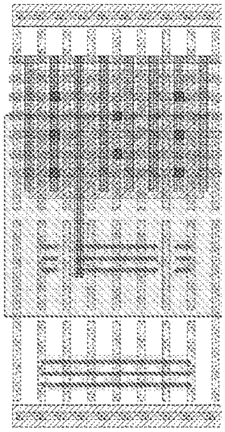
FIG. 2319A
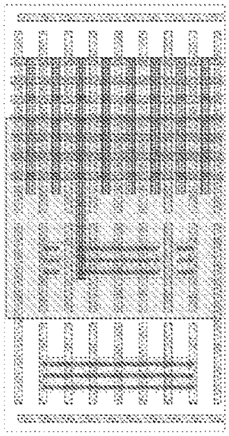
FIG. 2319B
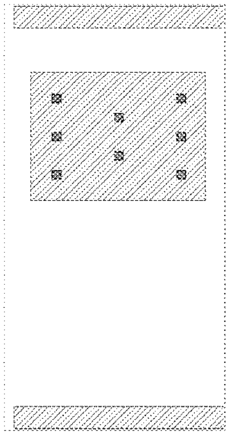
FIG. 2319C

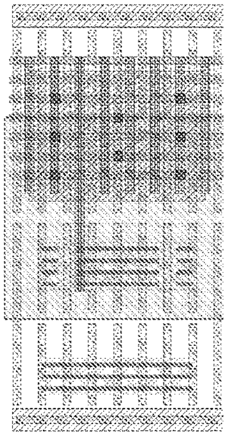
FIG. 2320A
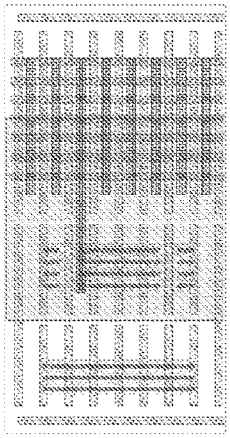
FIG. 2320B
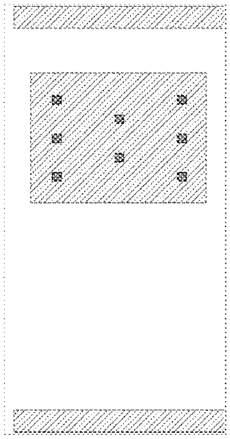
FIG. 2320C

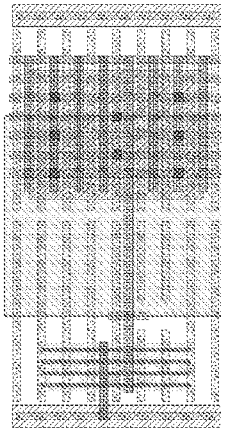
FIG. 2321A
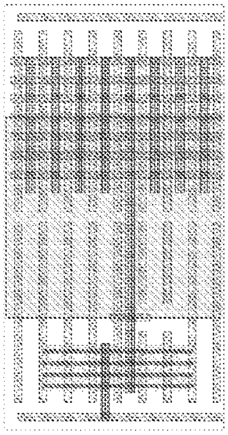
FIG. 2321B
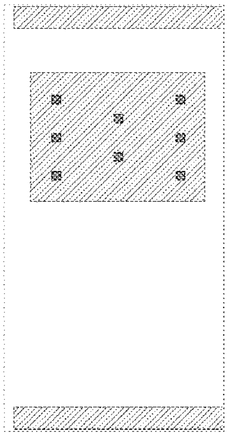
FIG. 2321C

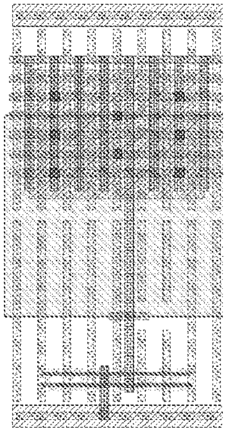
FIG. 2322A
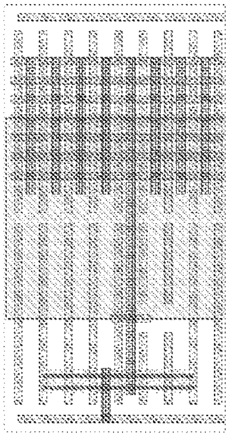
FIG. 2322B
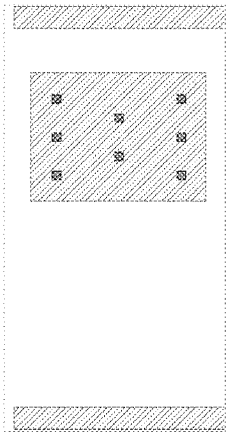
FIG. 2322C

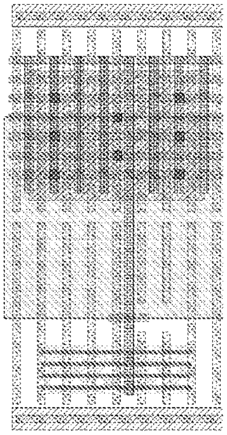
FIG. 2323A
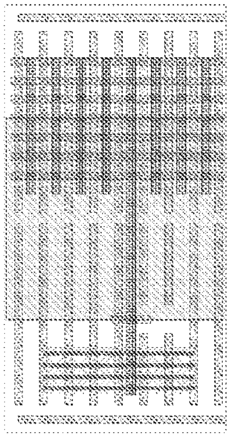
FIG. 2323B
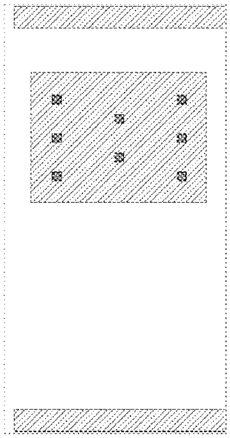
FIG. 2323C

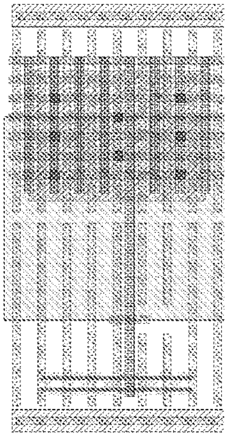
FIG. 2324A
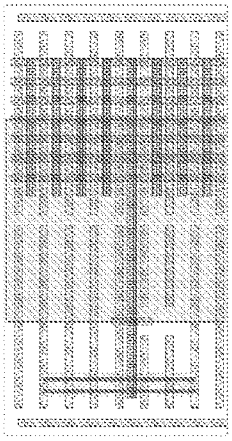
FIG. 2324B
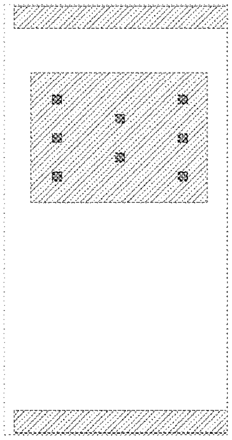
FIG. 2324C

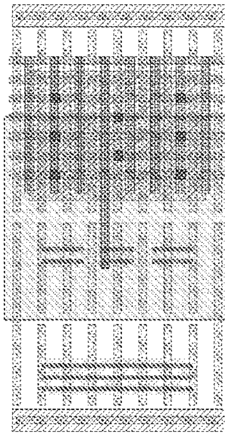
FIG. 2325A
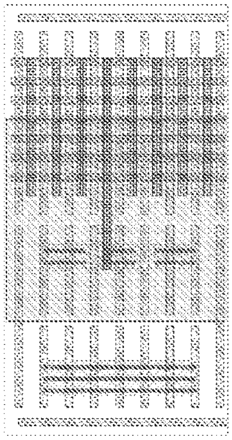
FIG. 2325B
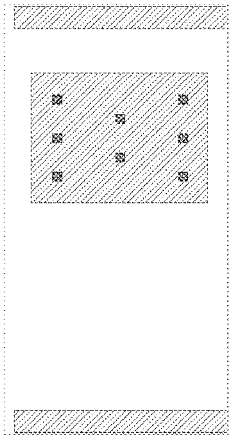
FIG. 2325C

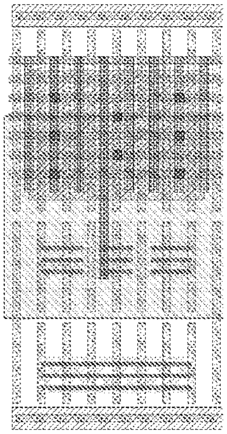
FIG. 2326A
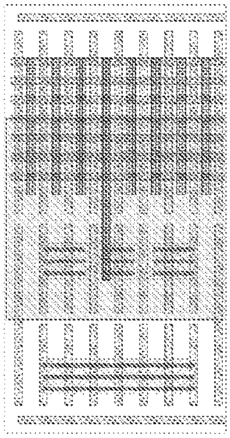
FIG. 2326B
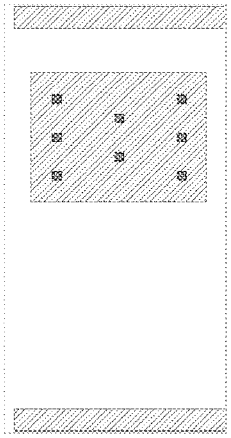
FIG. 2326C

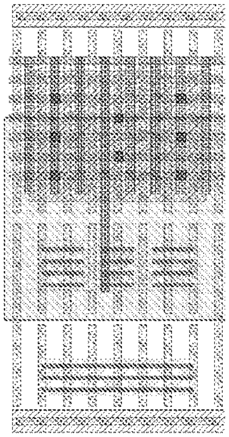
FIG. 2327A
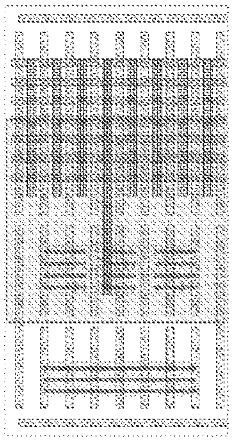
FIG. 2327B
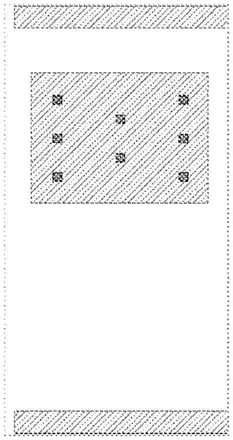
FIG. 2327C

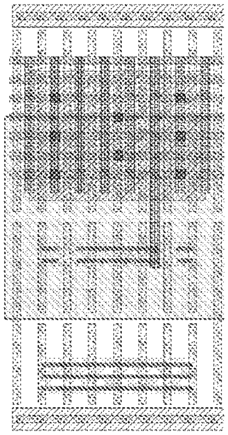
FIG. 2328A
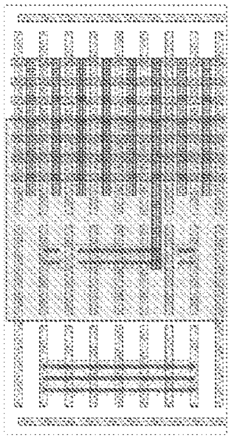
FIG. 2328B
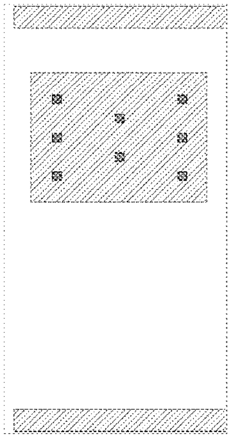
FIG. 2328C
*M* PDF Solutions, Inc.

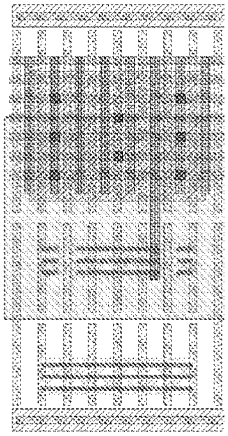
FIG. 2329A
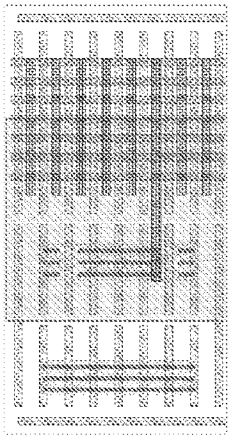
FIG. 2329B
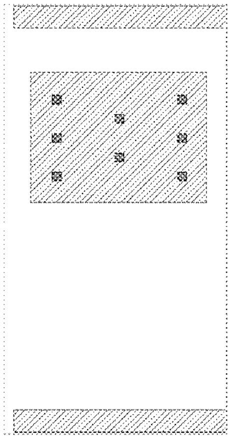
FIG. 2329C

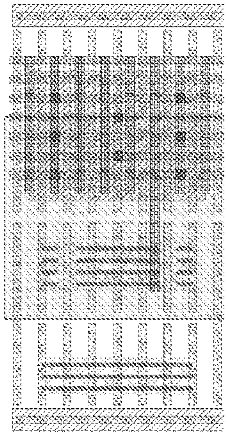
FIG. 2330A
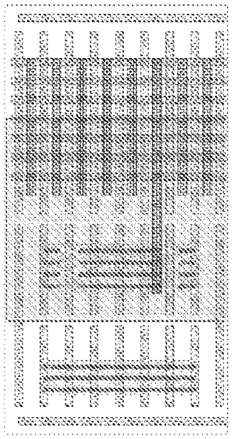
FIG. 2330B
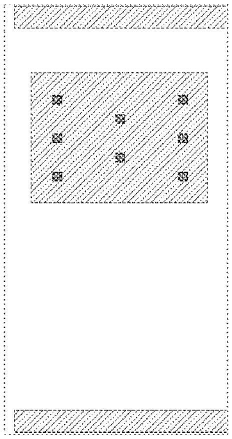
FIG. 2330C
*M* PDF Solutions, Inc.

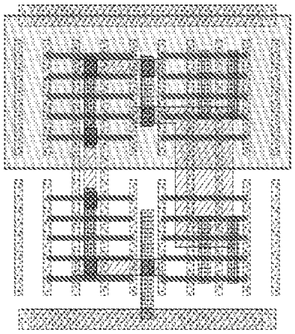
FIG. 2331A
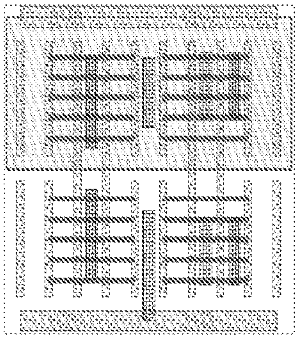
FIG. 2331B
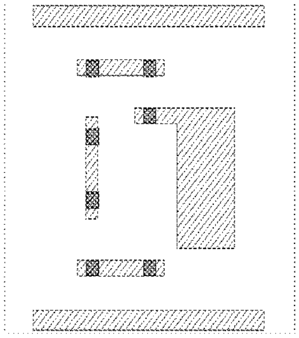
FIG. 2331C

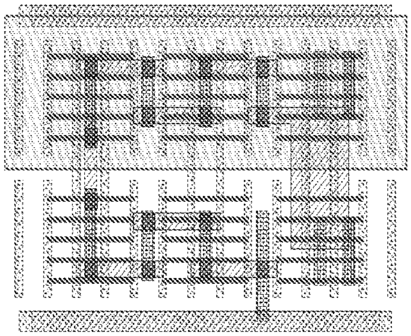
FIG. 2332A
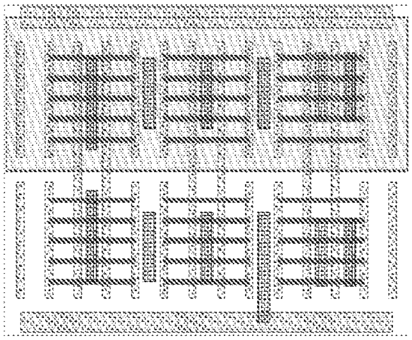
FIG. 2332B
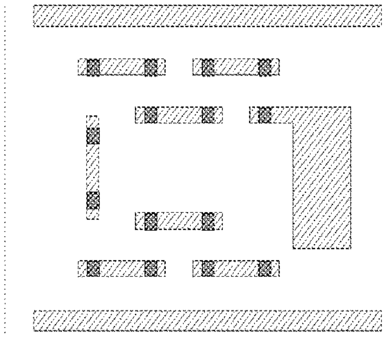
FIG. 2332C

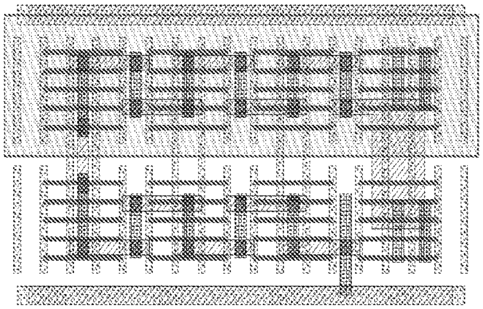
FIG. 2333A
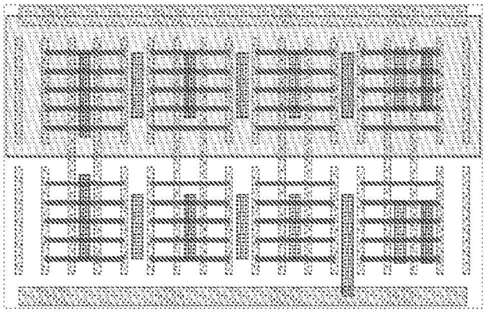
FIG. 2333B
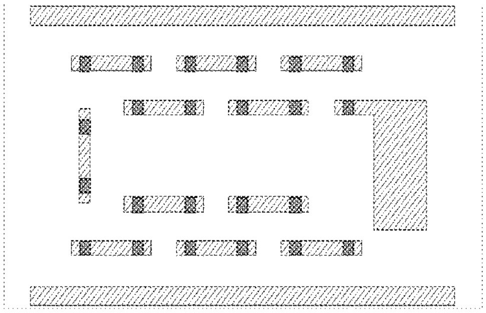
FIG. 2333C
*M* PDF Solutions, Inc.

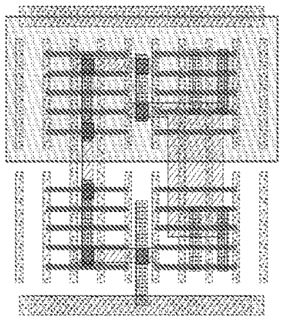
FIG. 2334A
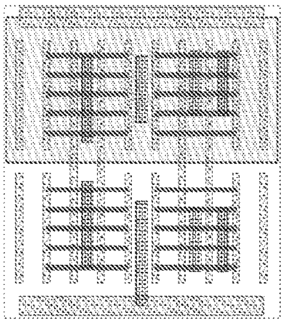
FIG. 2334B
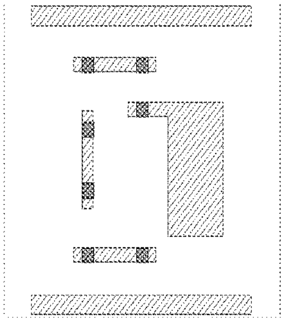
FIG. 2334C

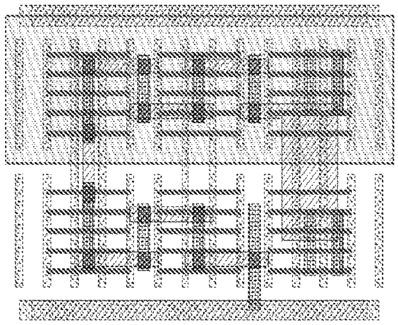
FIG. 2335A
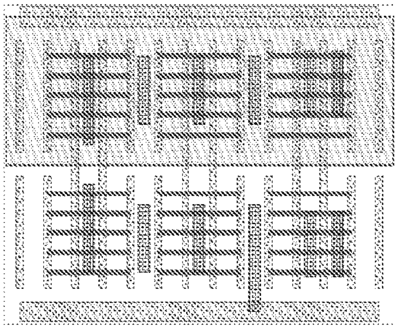
FIG. 2335B
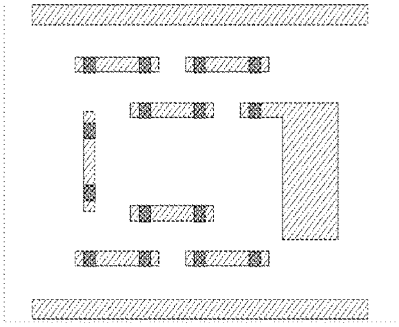
FIG. 2335C

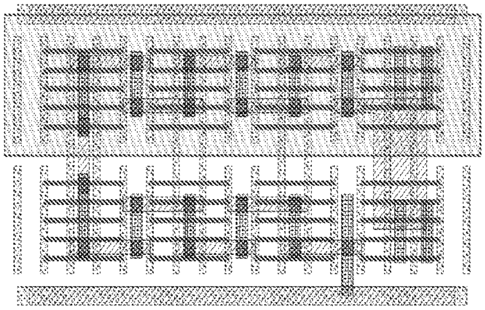
FIG. 2336A
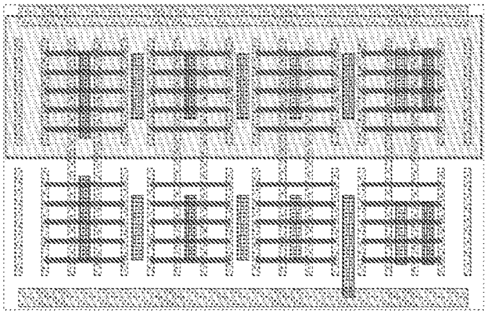
FIG. 2336B
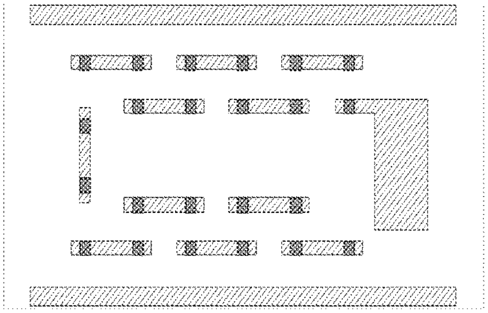
FIG. 2336C

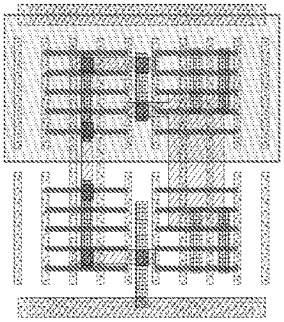
FIG. 2337A
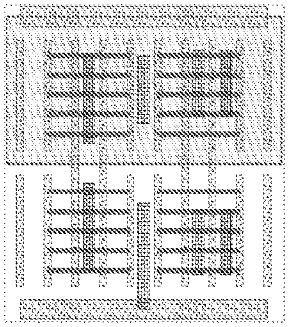
FIG. 2337B
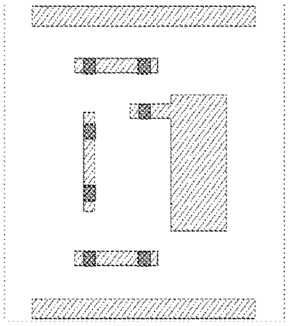
FIG. 2337C
*M* PDF Solutions, Inc.

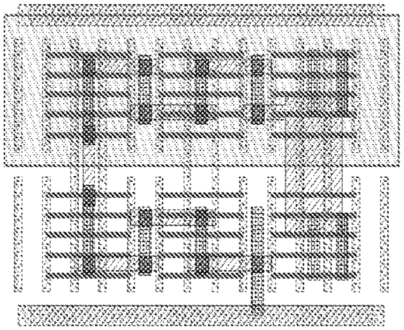
FIG. 2338A
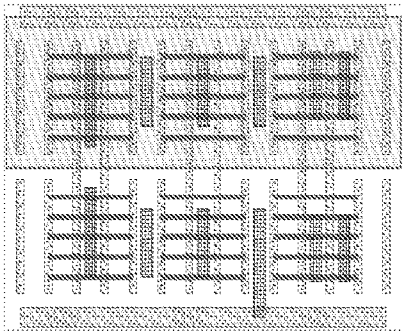
FIG. 2338B
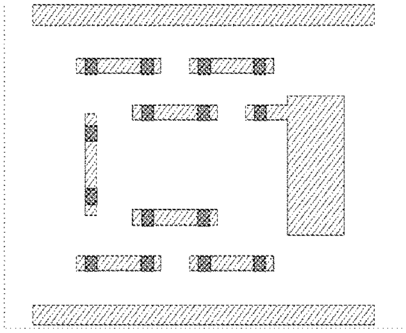
FIG. 2338C

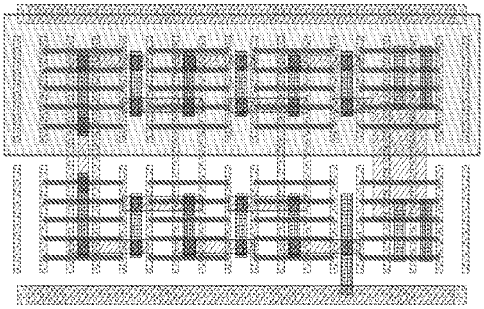
FIG. 2339A
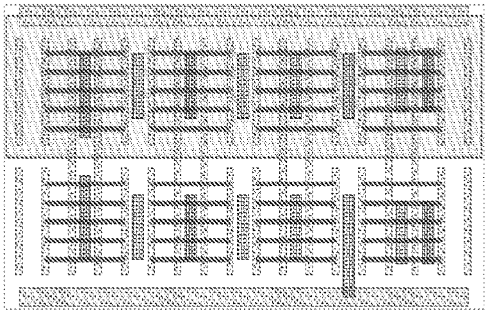
FIG. 2339B
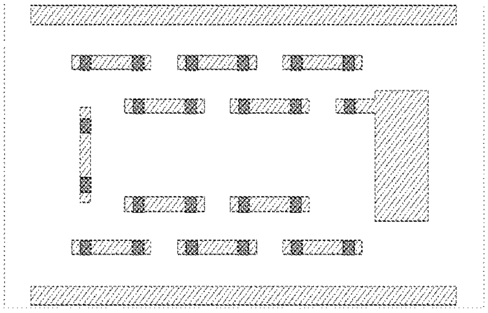
FIG. 2339C

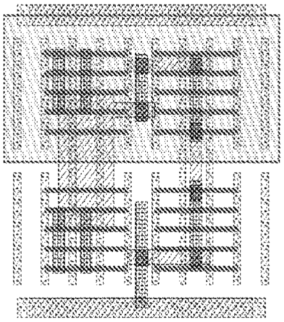
FIG. 2340A
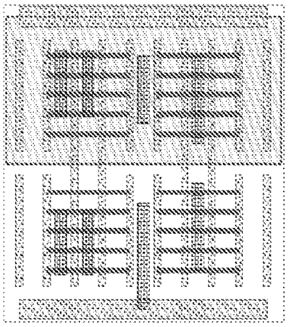
FIG. 2340B
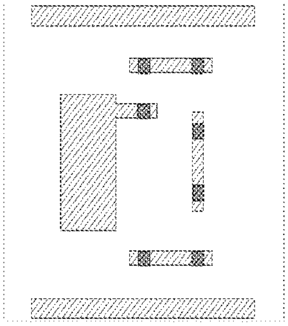
FIG. 2340C

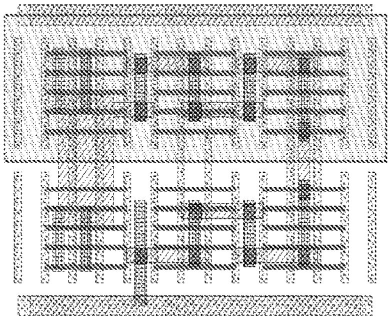
FIG. 2341A
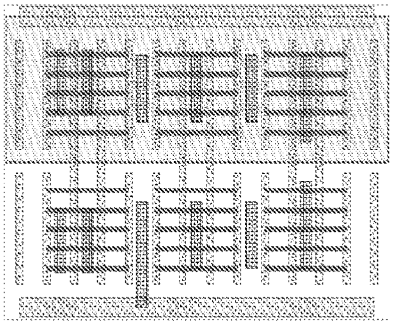
FIG. 2341B
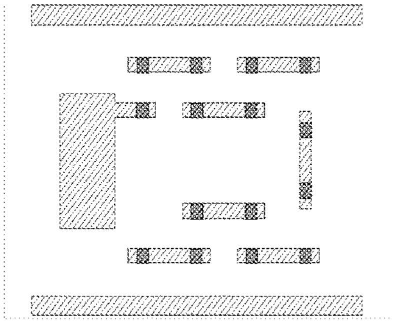
FIG. 2341C

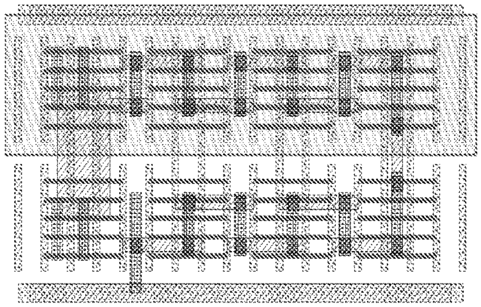
FIG. 2342A
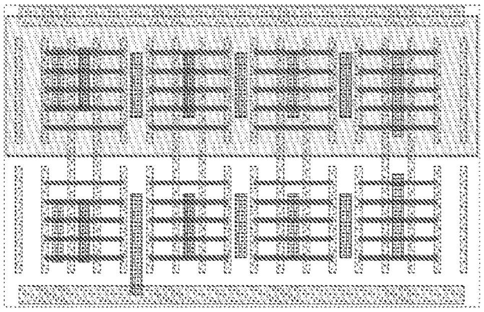
FIG. 2342B
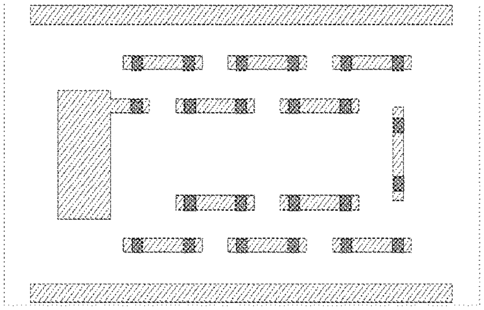
FIG. 2342C

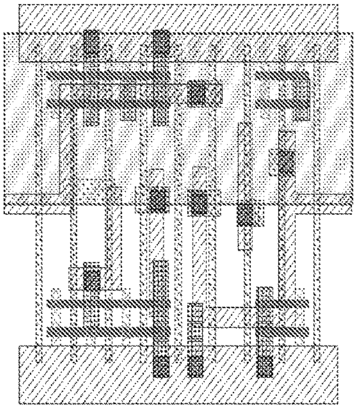
FIG. 2343A
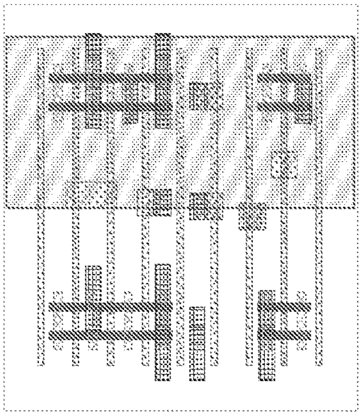
FIG. 2343B
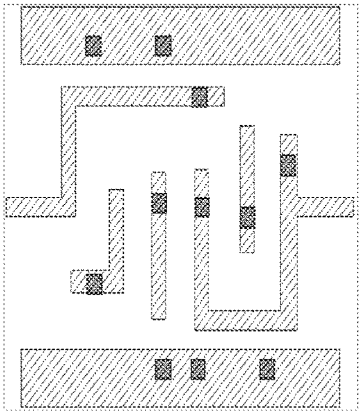
FIG. 2343C

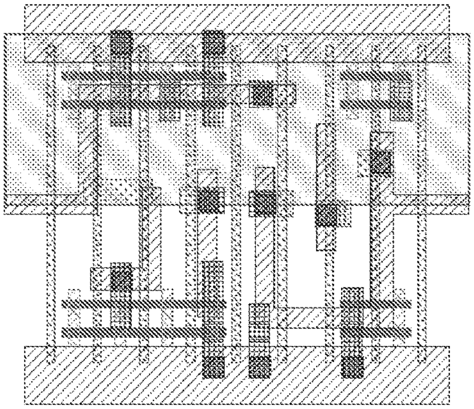
FIG. 2344A
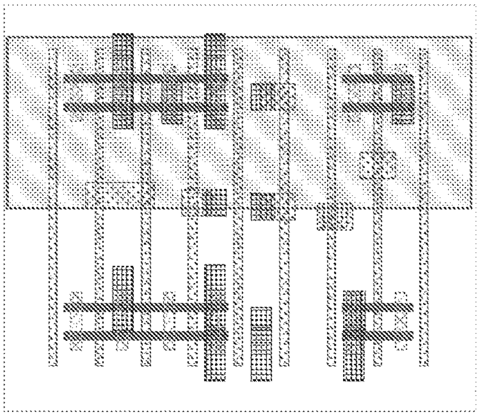
FIG. 2344B
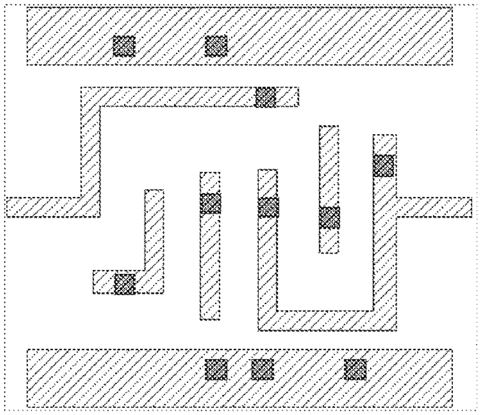
FIG. 2344C

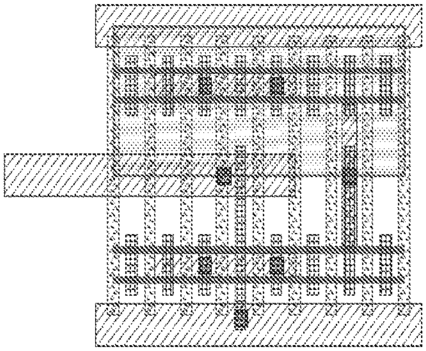
FIG. 2345A
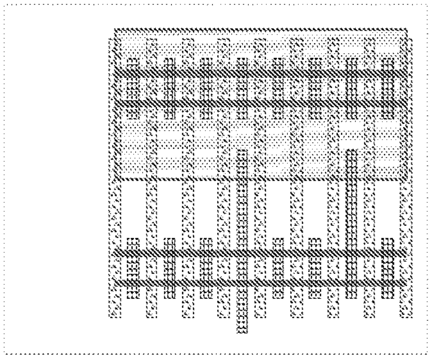
FIG. 2345B
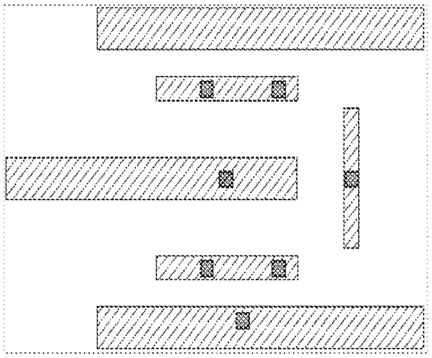
FIG. 2345C

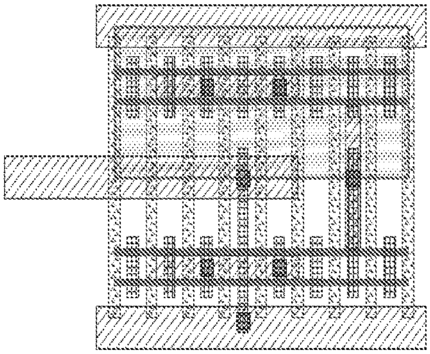
FIG. 2346A
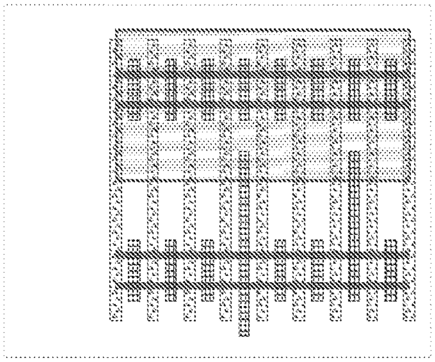
FIG. 2346B
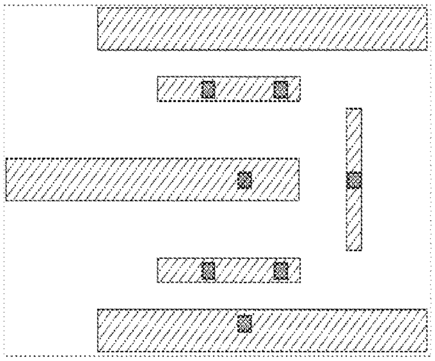
FIG. 2346C

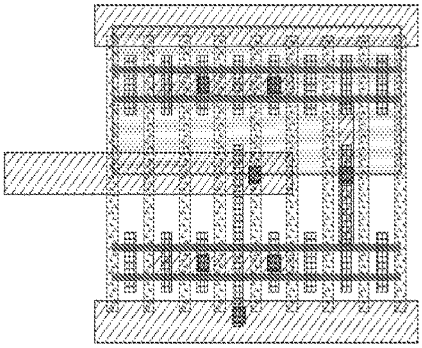
FIG. 2347A
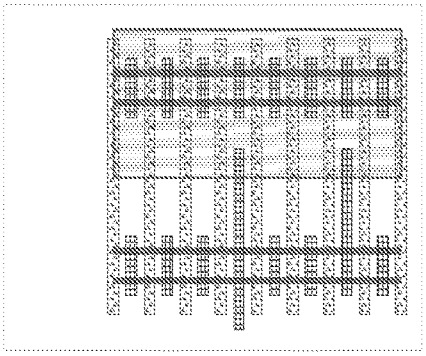
FIG. 2347B
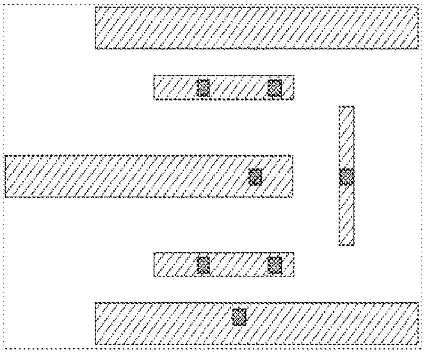
FIG. 2347C
*M* PDF Solutions, Inc.

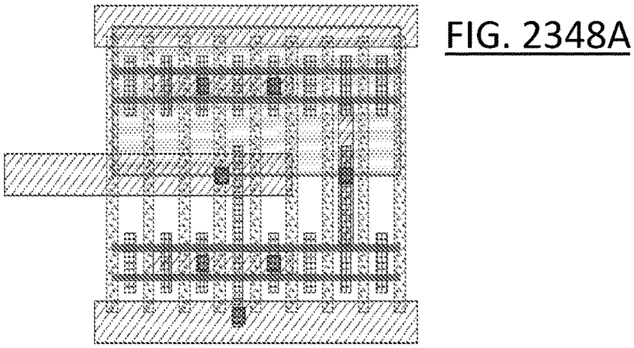
FIG. 2348A
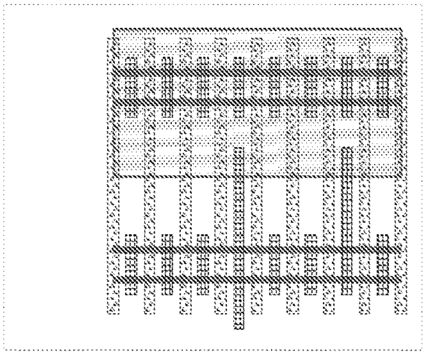
FIG. 2348B
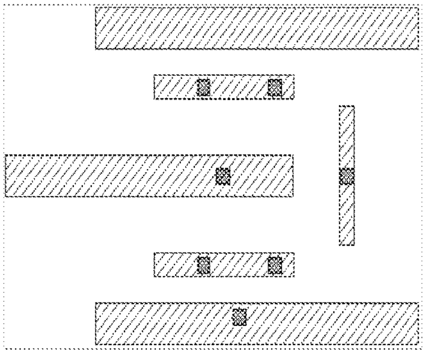
FIG. 2348C

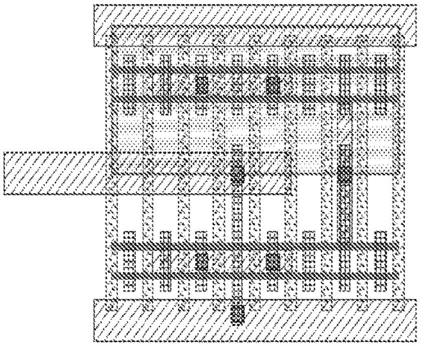
FIG. 2349A
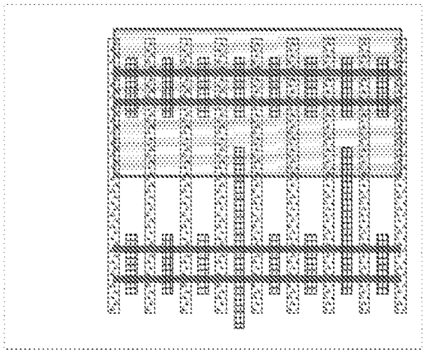
FIG. 2349B
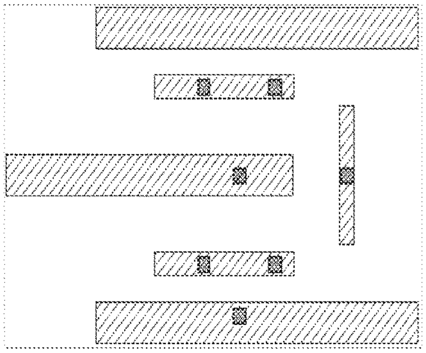
FIG. 2349C
*M* PDF Solutions, Inc.

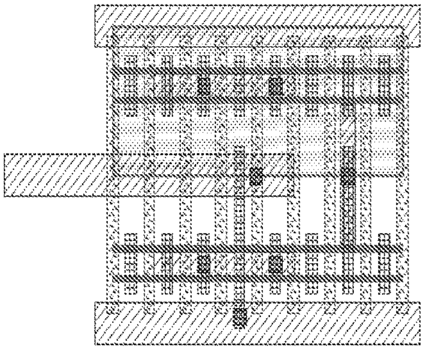
FIG. 2350A
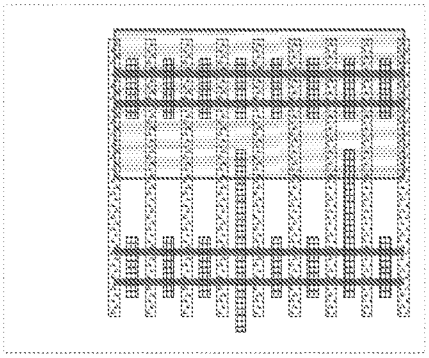
FIG. 2350B
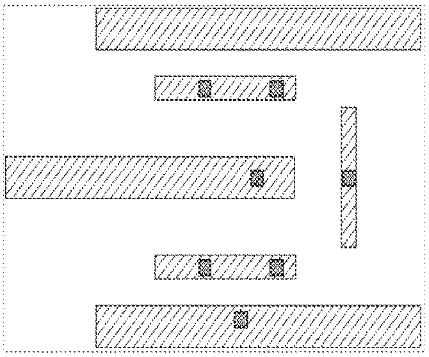
FIG. 2350C

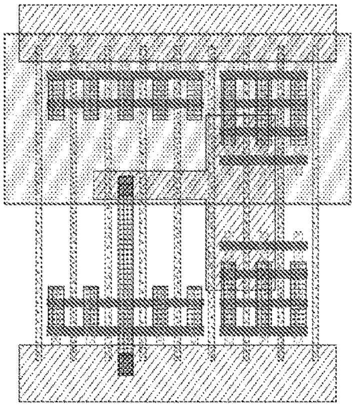
FIG. 2351A
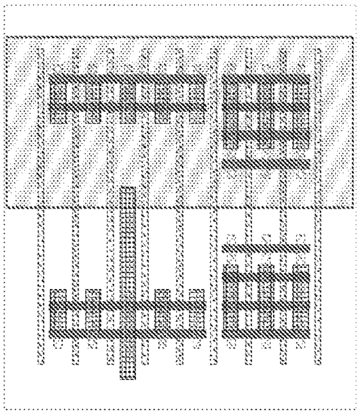
FIG. 2351B
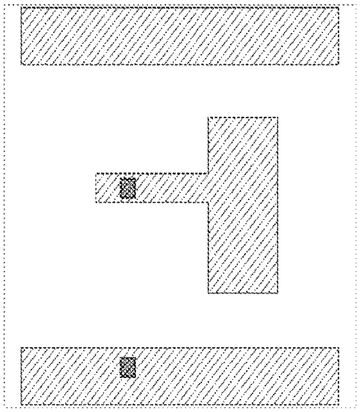
FIG. 2351C

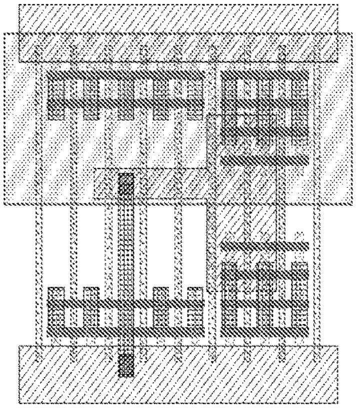
FIG. 2352A
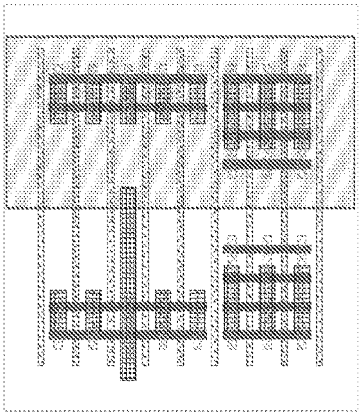
FIG. 2352B
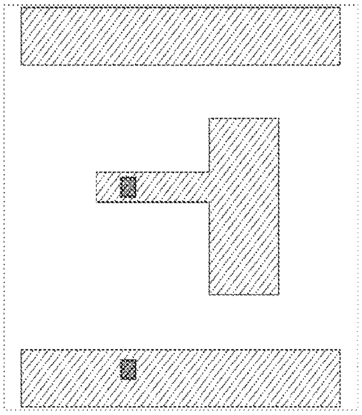
FIG. 2352C

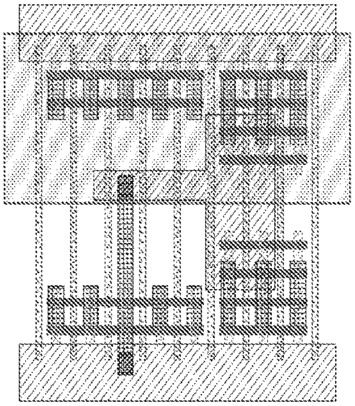
FIG. 2353A
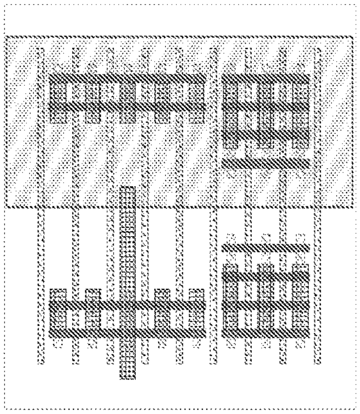
FIG. 2353B
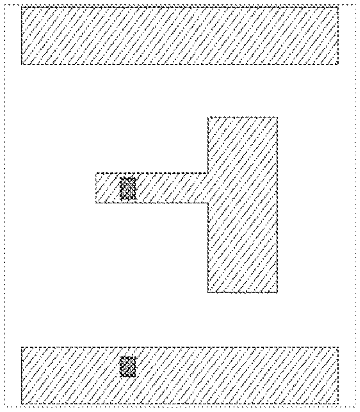
FIG. 2353C

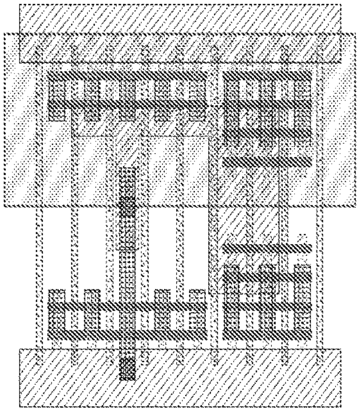
FIG. 2354A
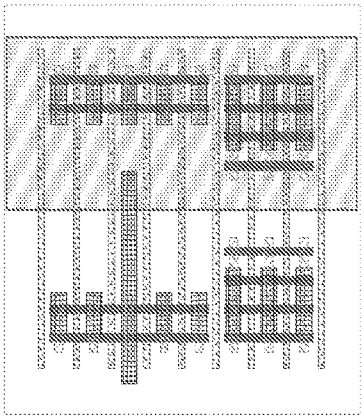
FIG. 2354B
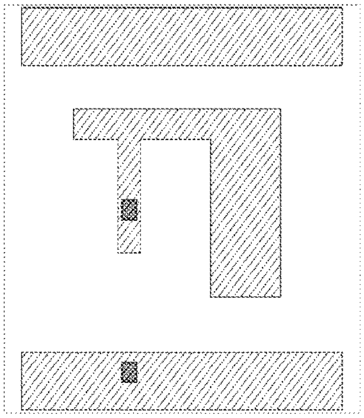
FIG. 2354C

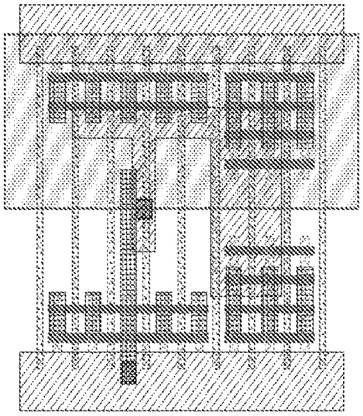
FIG. 2355A
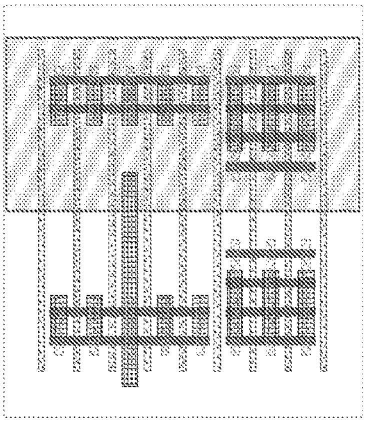
FIG. 2355B
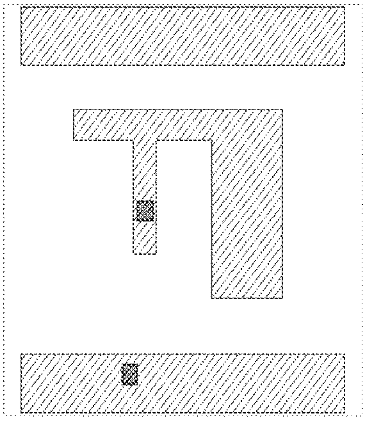
FIG. 2355C

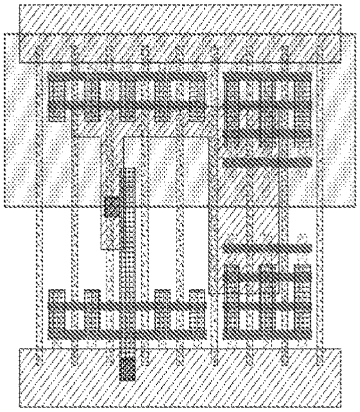
FIG. 2356A
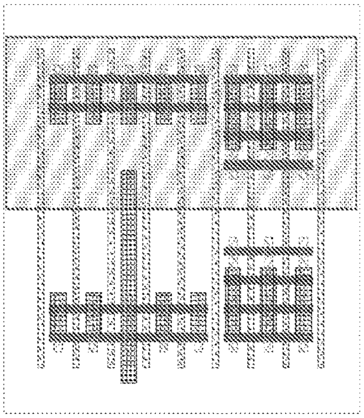
FIG. 2356B
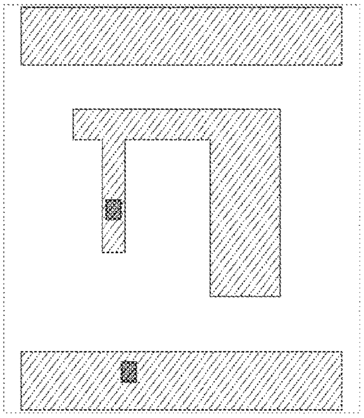
FIG. 2356C

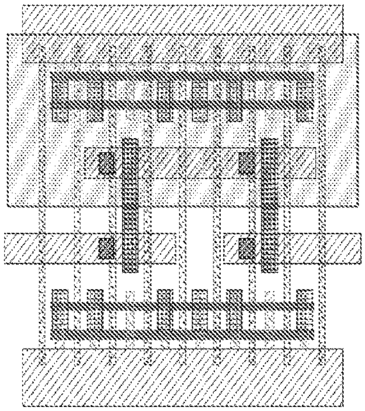
FIG. 2357A
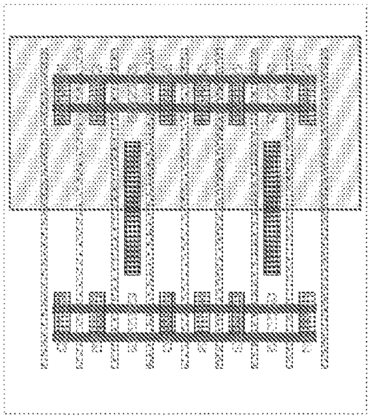
FIG. 2357B
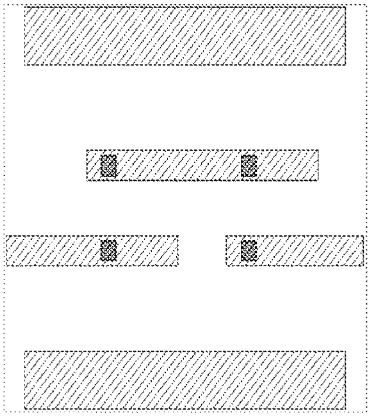
FIG. 2357C
*M* PDF Solutions, Inc.

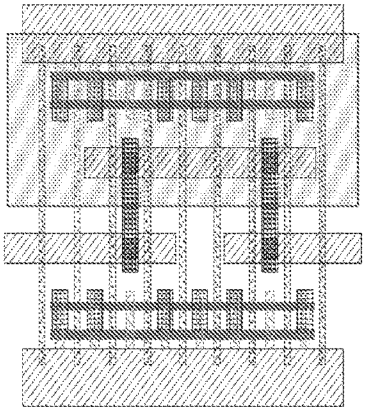
FIG. 2358A
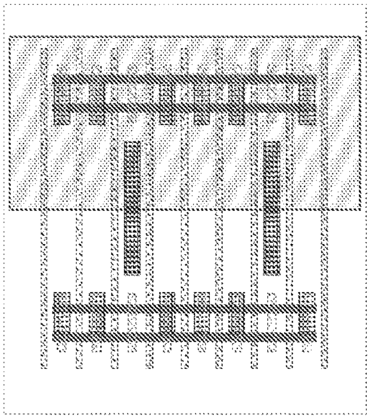
FIG. 2358B
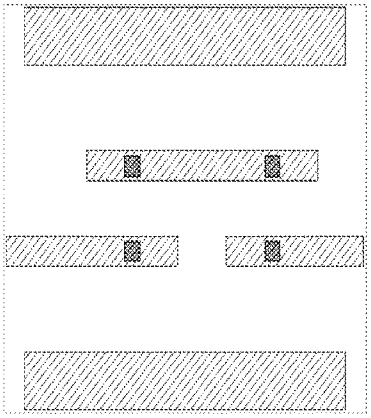
FIG. 2358C

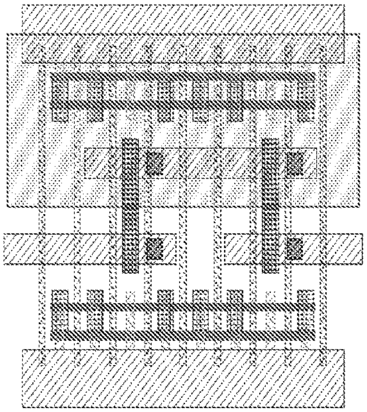
FIG. 2359A
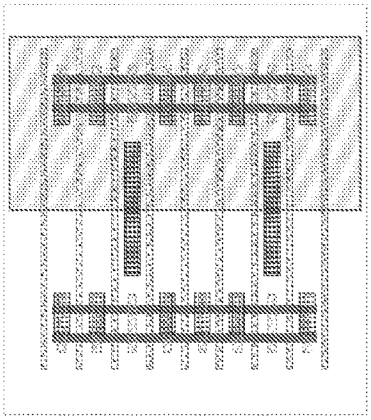
FIG. 2359B
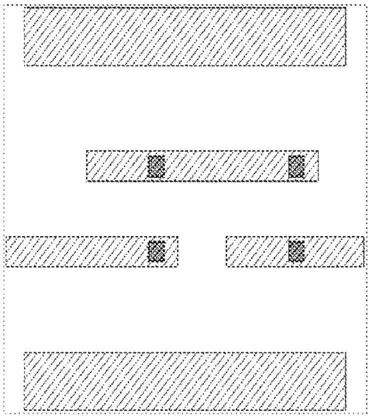
FIG. 2359C
*M* PDF Solutions, Inc.

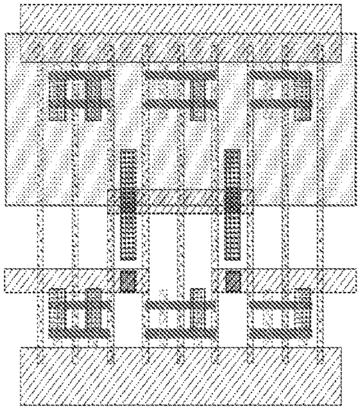
FIG. 2360A
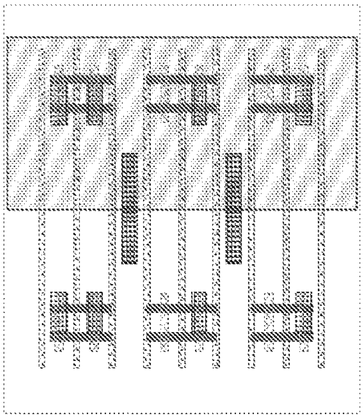
FIG. 2360B
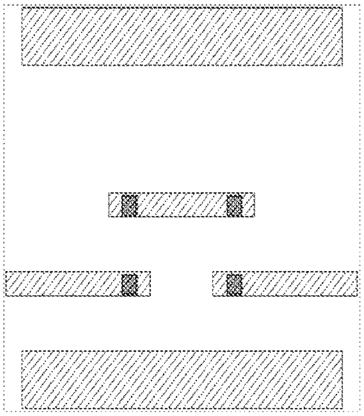
FIG. 2360C

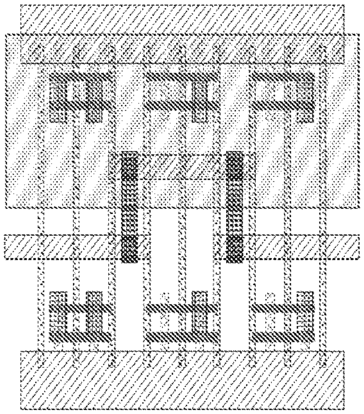
FIG. 2361A
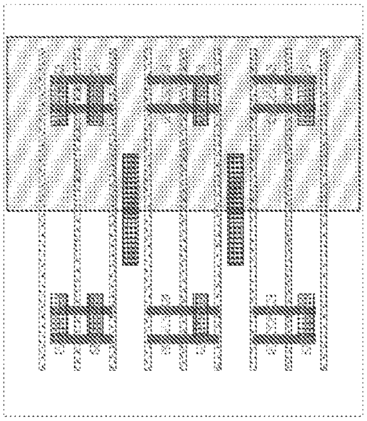
FIG. 2361B
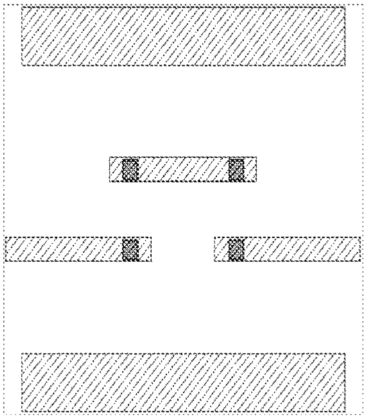
FIG. 2361C

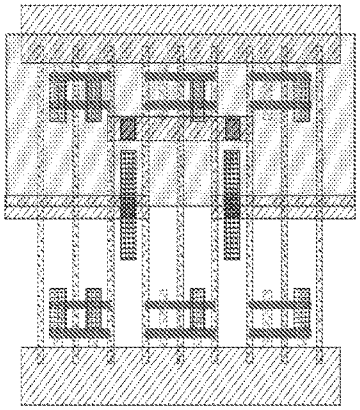
FIG. 2362A
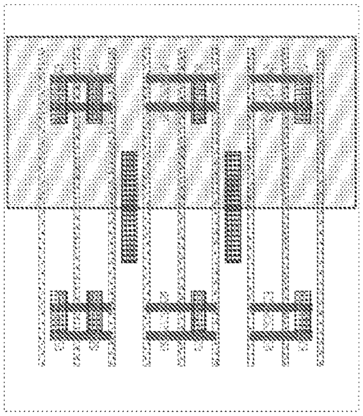
FIG. 2362B
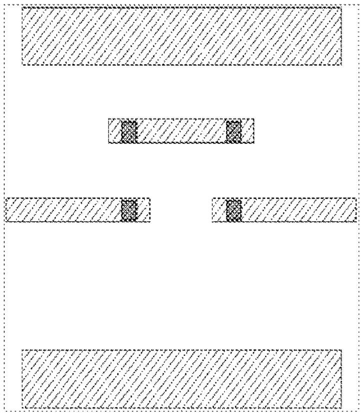
FIG. 2362C

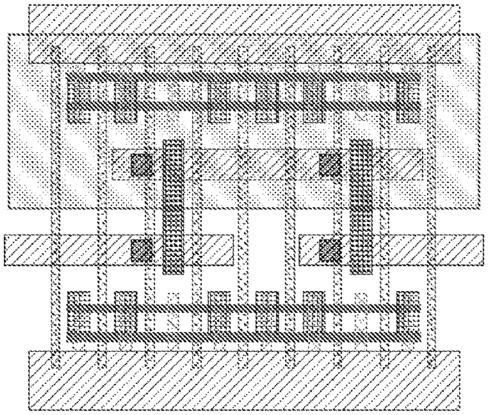
FIG. 2363A
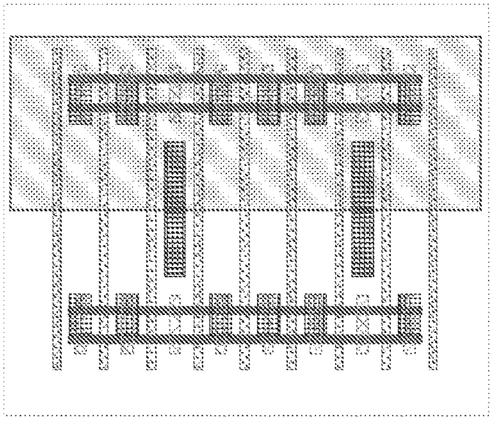
FIG. 2363B
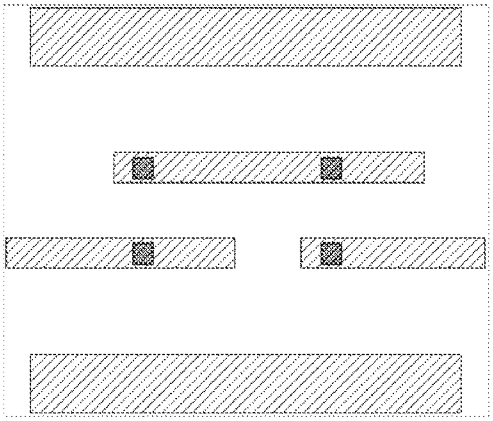
FIG. 2363C

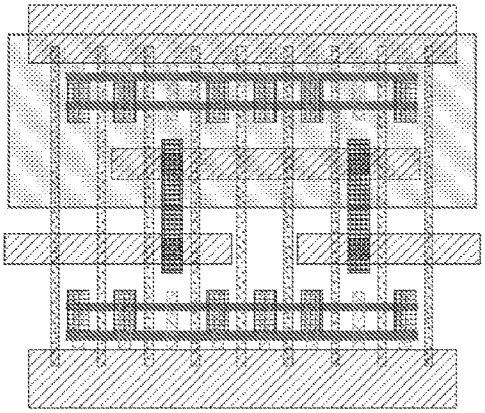
FIG. 2364A
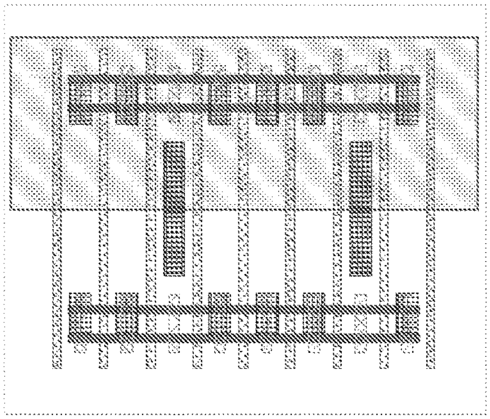
FIG. 2364B
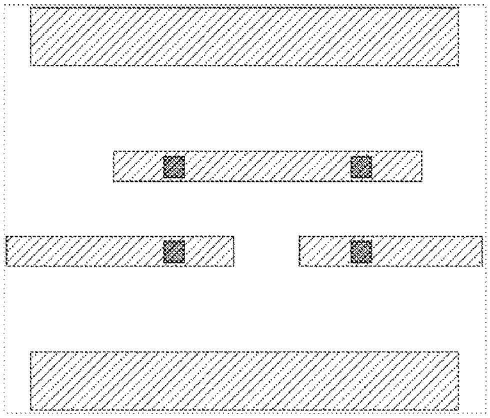
FIG. 2364C

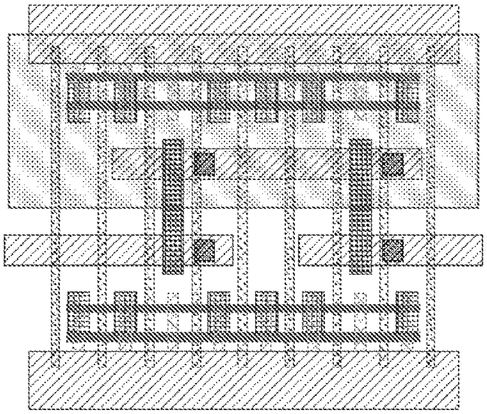
FIG. 2365A
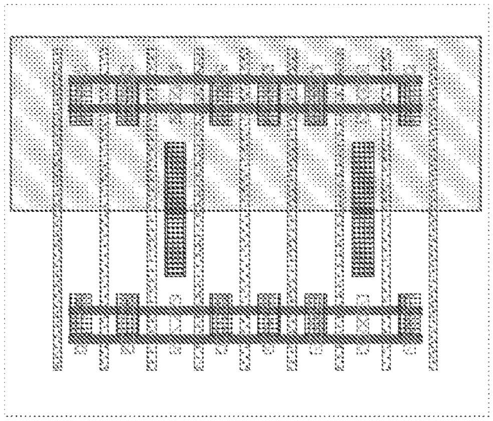
FIG. 2365B
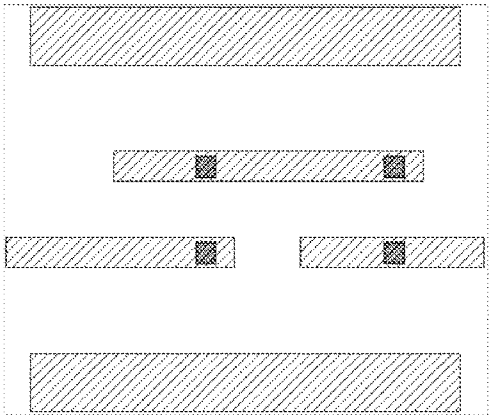
FIG. 2365C
*M* PDF Solutions, Inc.

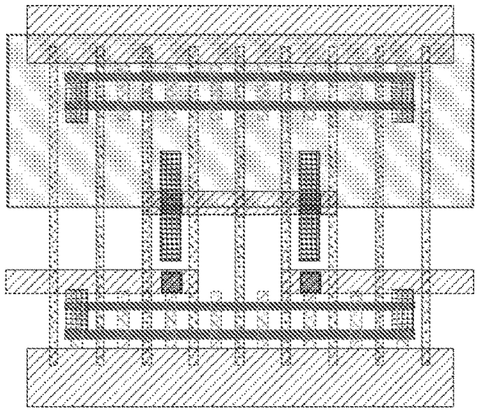
FIG. 2366A
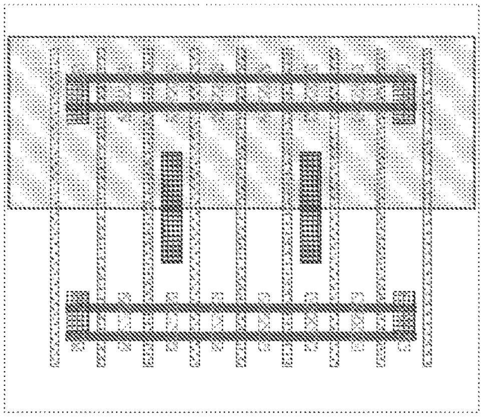
FIG. 2366B
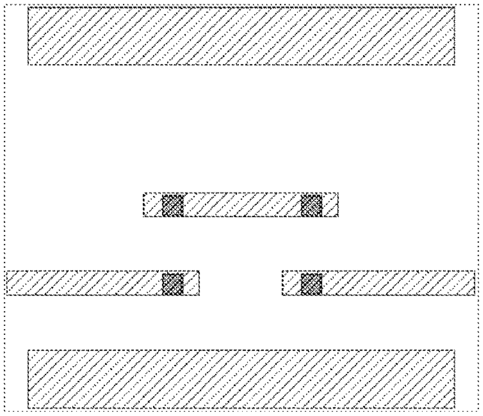
FIG. 2366C

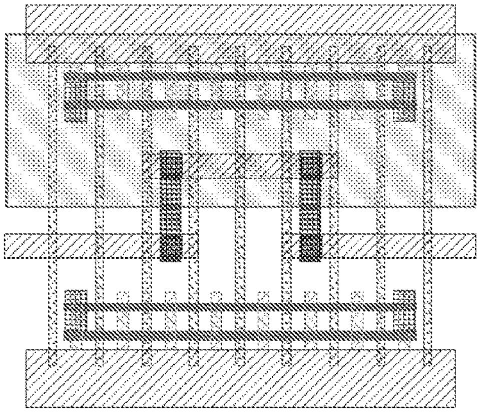
FIG. 2367A
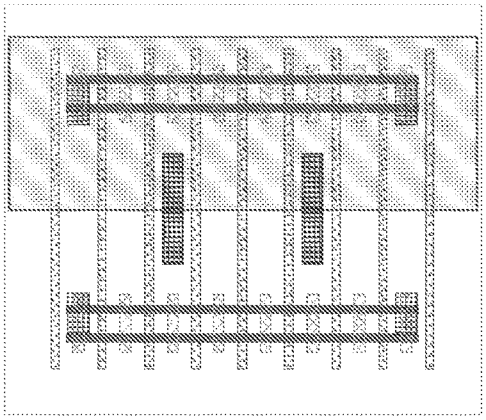
FIG. 2367B
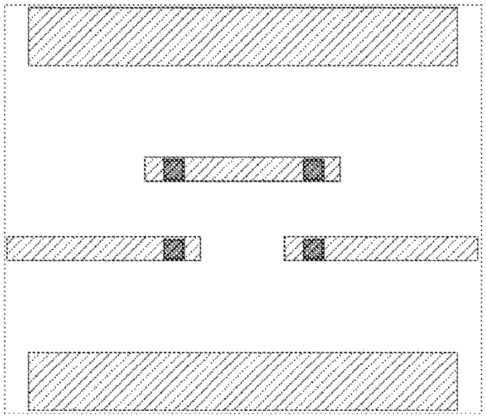
FIG. 2367C
*M* PDF Solutions, Inc.

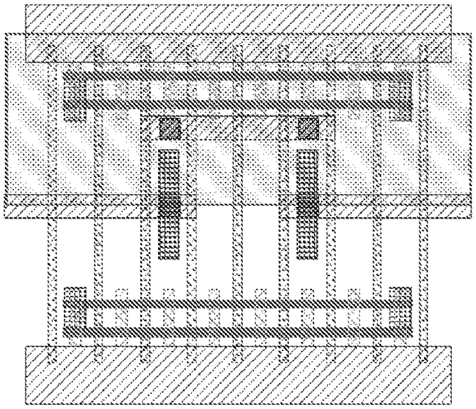
FIG. 2368A
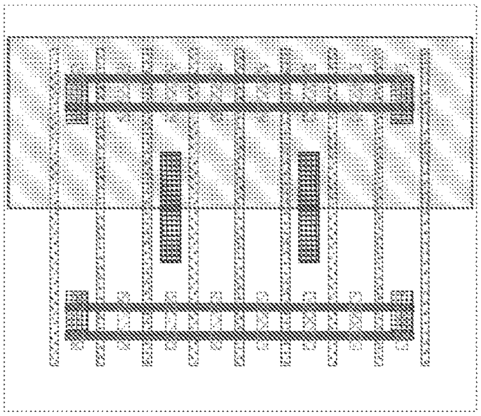
FIG. 2368B
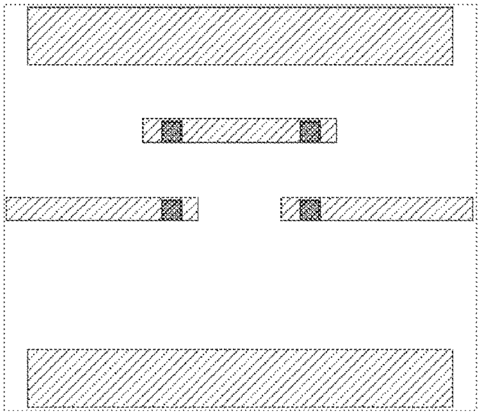
FIG. 2368C

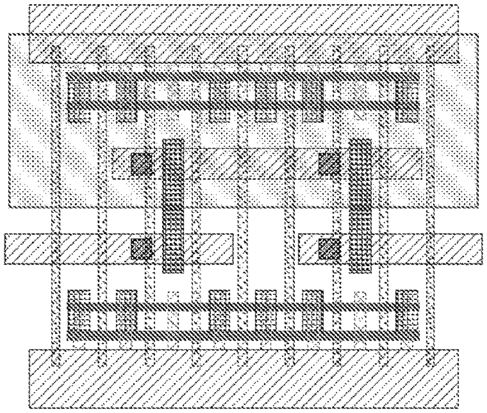
FIG. 2369A
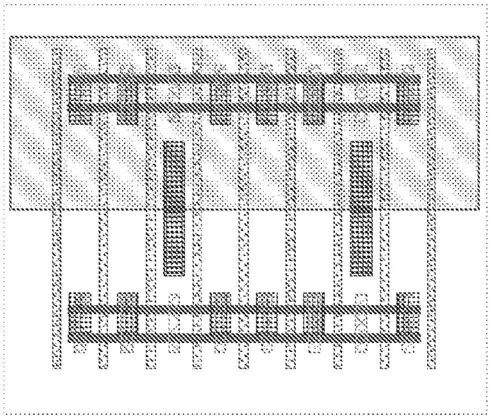
FIG. 2369B
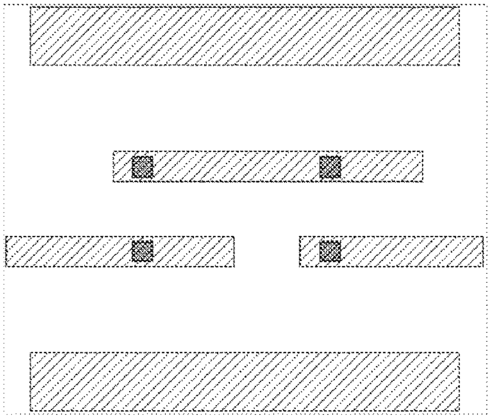
FIG. 2369C

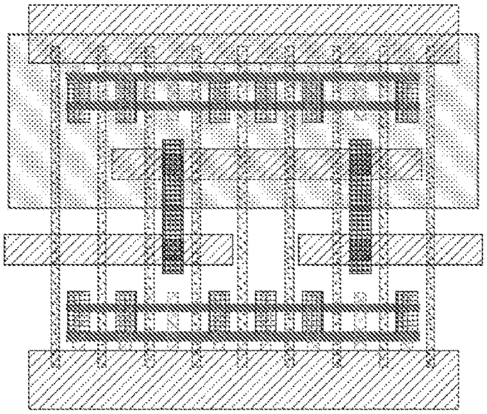
FIG. 2370A
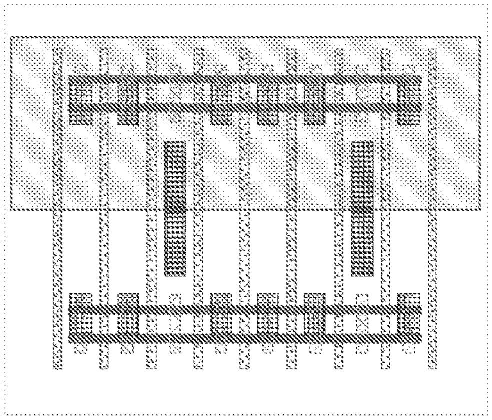
FIG. 2370B
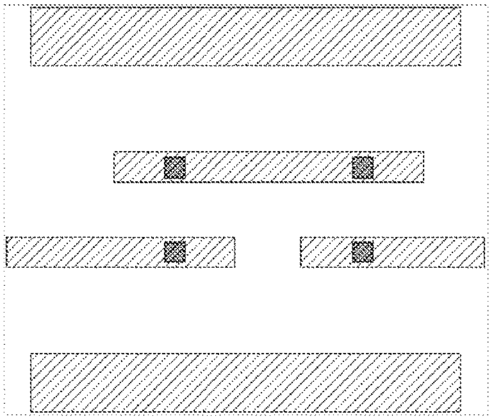
FIG. 2370C

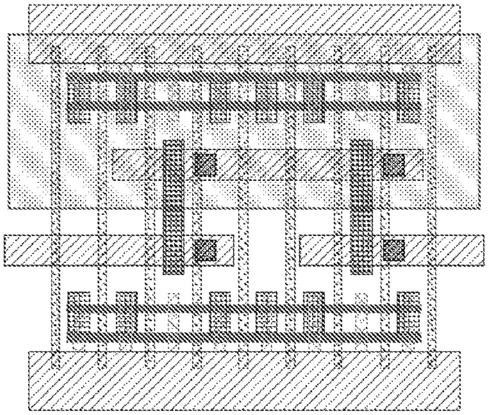
FIG. 2371A
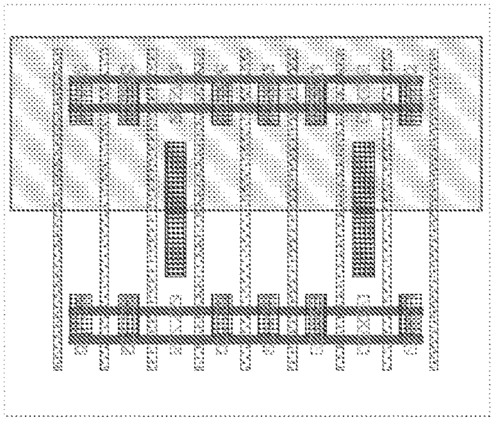
FIG. 2371B
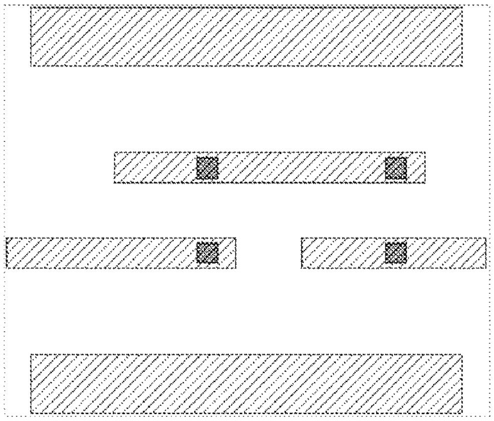
FIG. 2371C
*M* PDF Solutions, Inc.

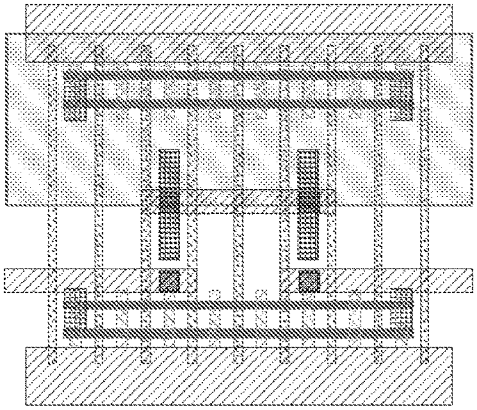
FIG. 2372A
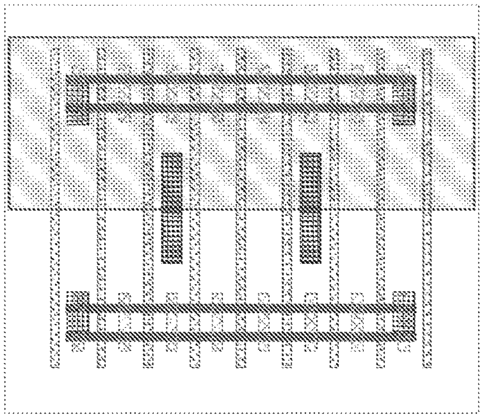
FIG. 2372B
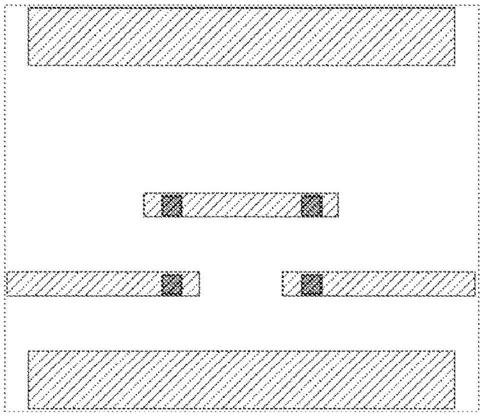
FIG. 2372C

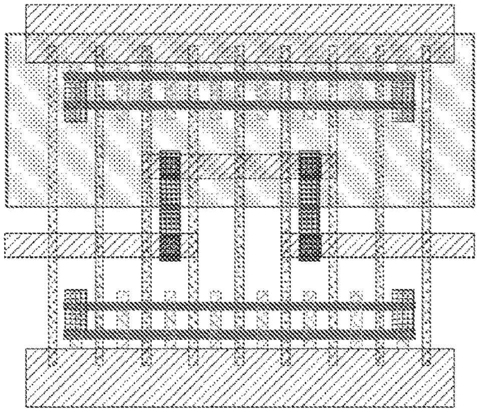
FIG. 2373A
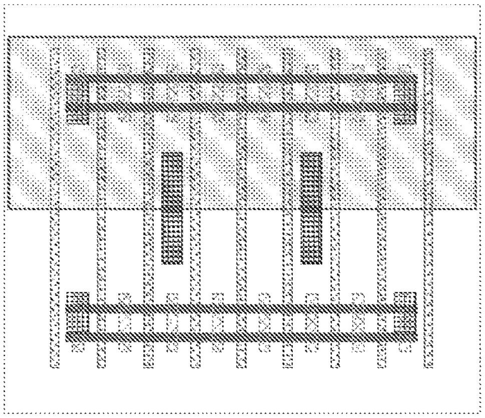
FIG. 2373B
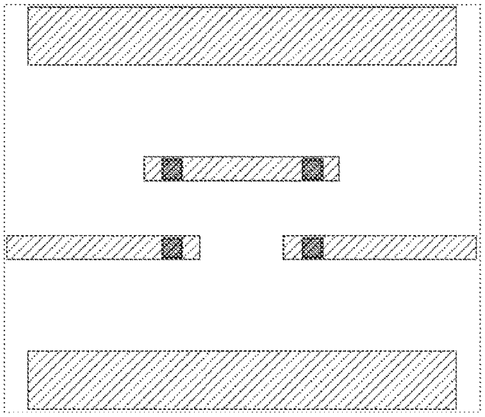
FIG. 2373C
*M* PDF Solutions, Inc.

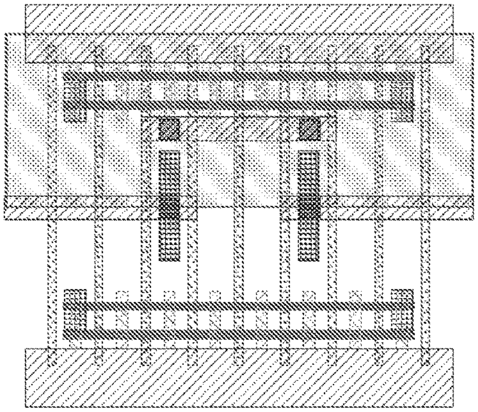
FIG. 2374A
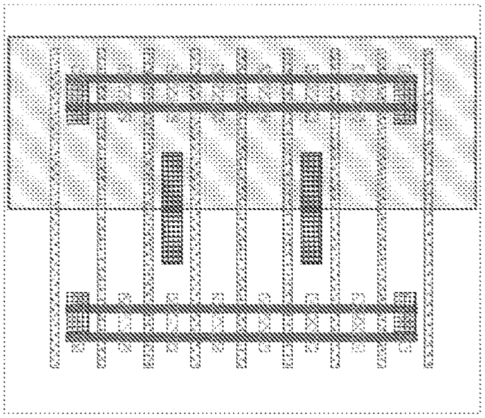
FIG. 2374B
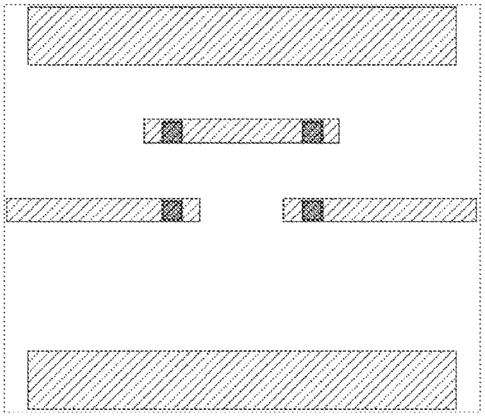
FIG. 2374C

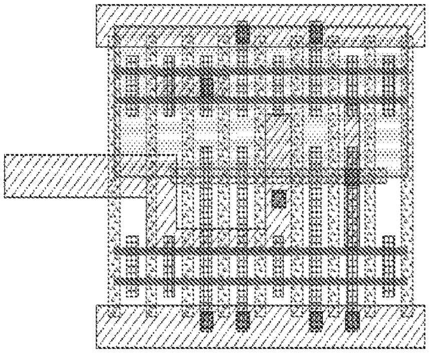
FIG. 2375A
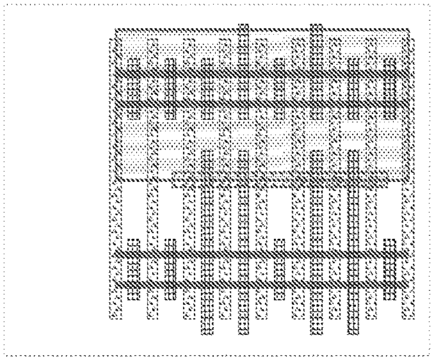
FIG. 2375B
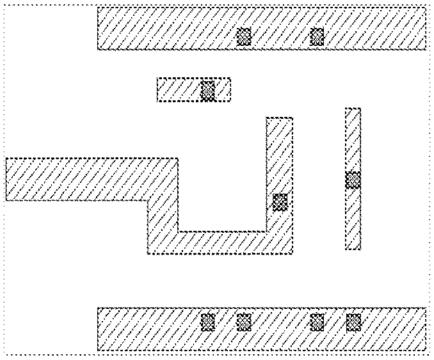
FIG. 2375C

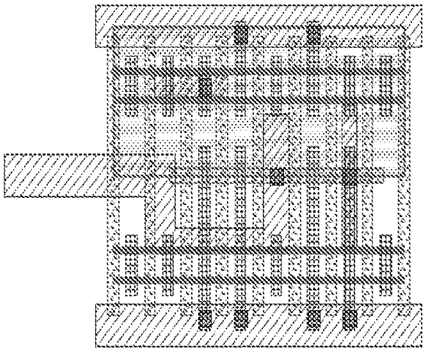
FIG. 2376A
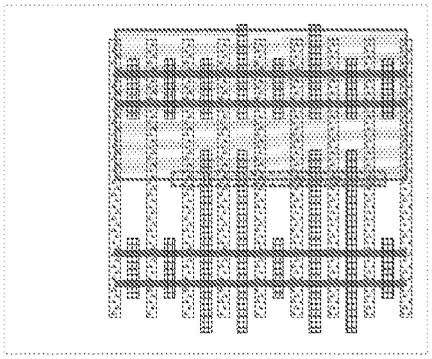
FIG. 2376B
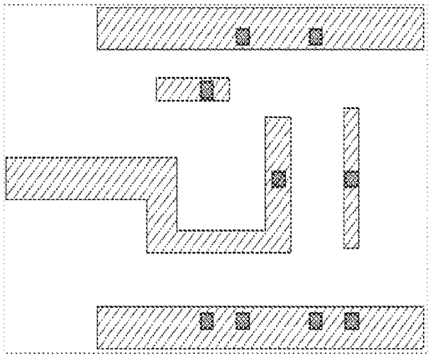
FIG. 2376C
*M* PDF Solutions, Inc.

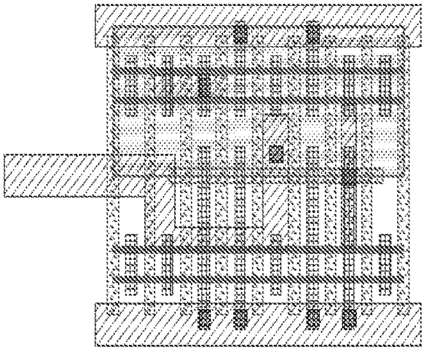
FIG. 2377A
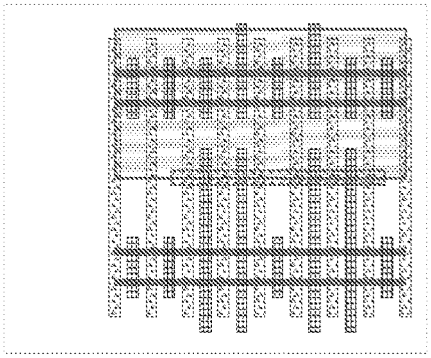
FIG. 2377B
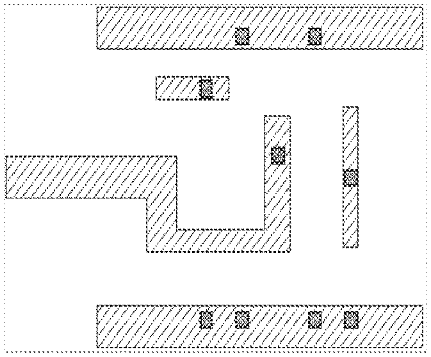
FIG. 2377C
*M* PDF Solutions, Inc.

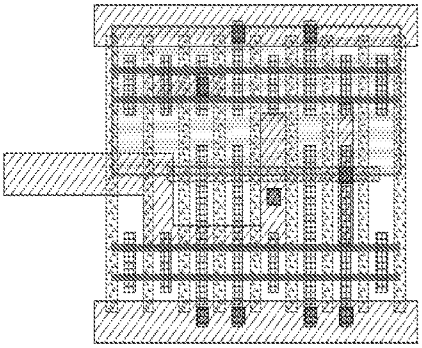
FIG. 2378A
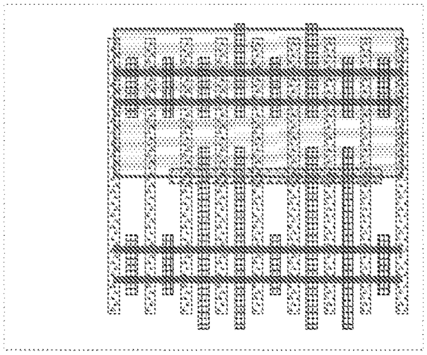
FIG. 2378B
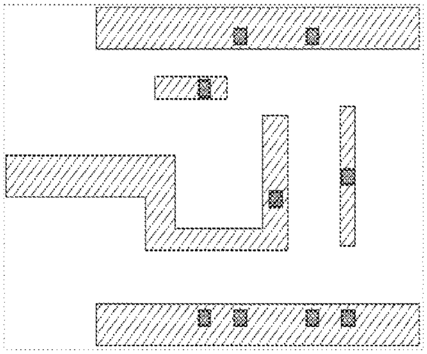
FIG. 2378C
*M* PDF Solutions, Inc.

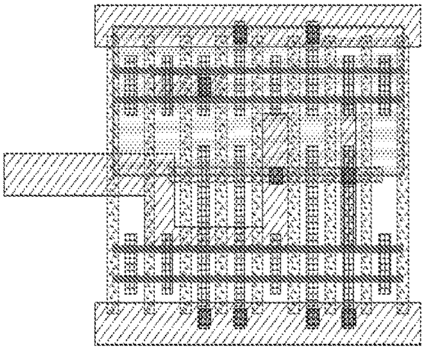
FIG. 2379A
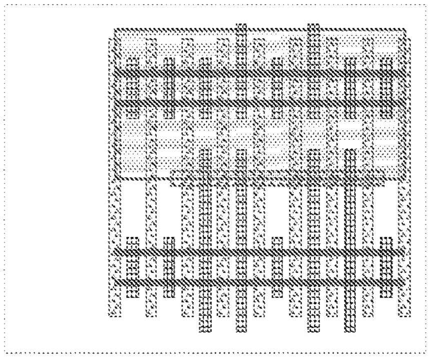
FIG. 2379B
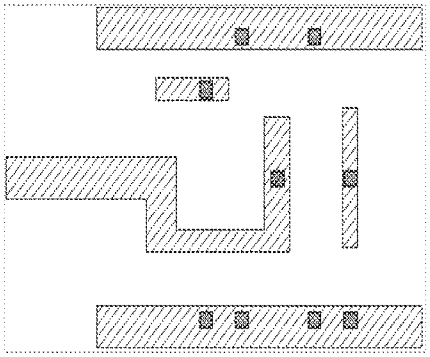
FIG. 2379C

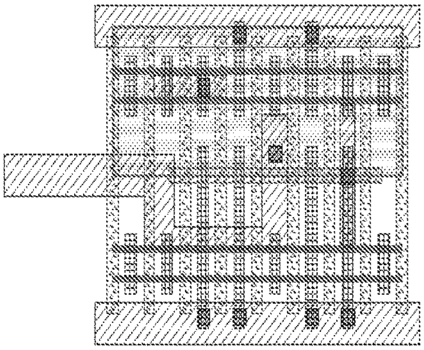
FIG. 2380A
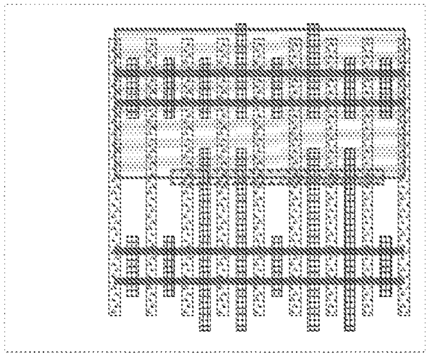
FIG. 2380B
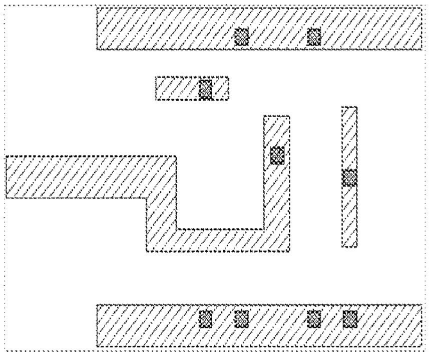
FIG. 2380C
*M* PDF Solutions, Inc.

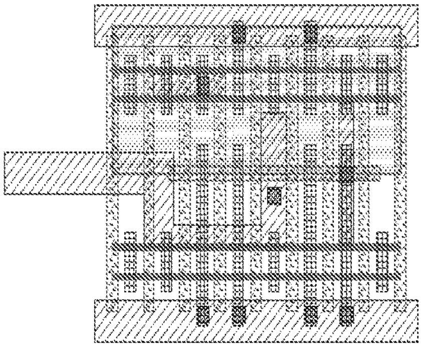
FIG. 2381A
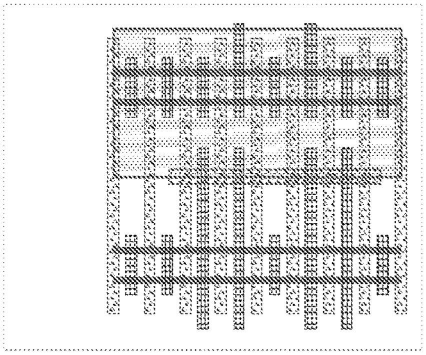
FIG. 2381B
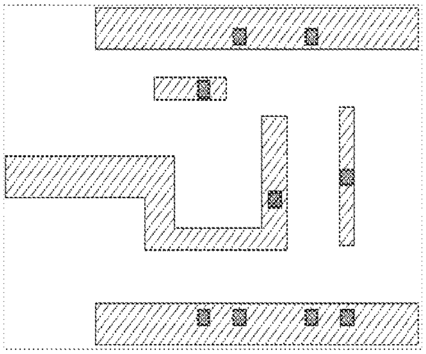
FIG. 2381C

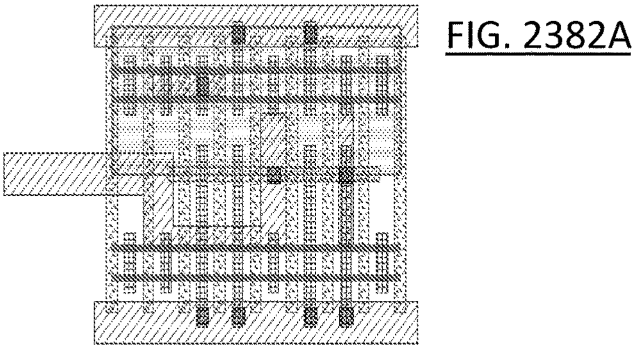
FIG. 2382A
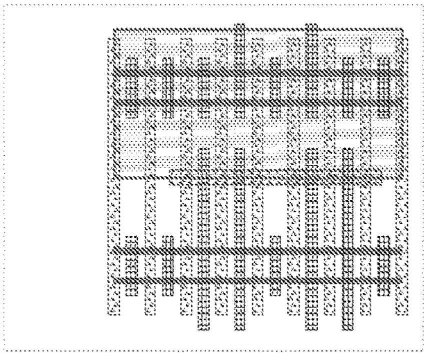
FIG. 2382B
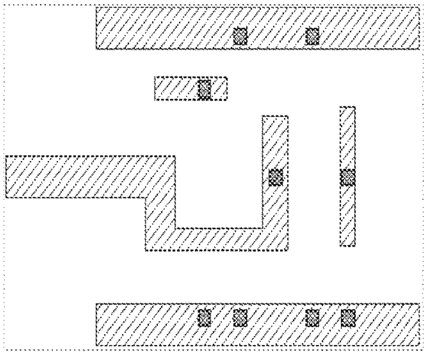
FIG. 2382C

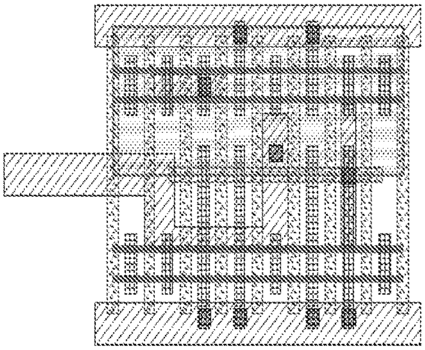
FIG. 2383A
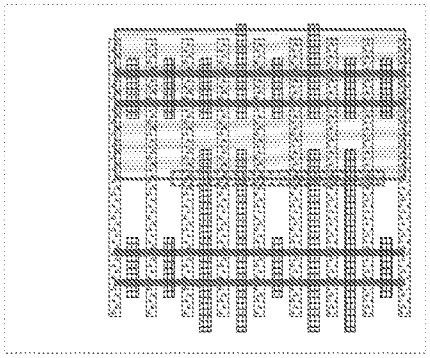
FIG. 2383B
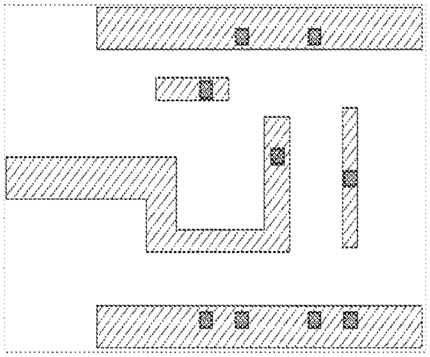
FIG. 2383C

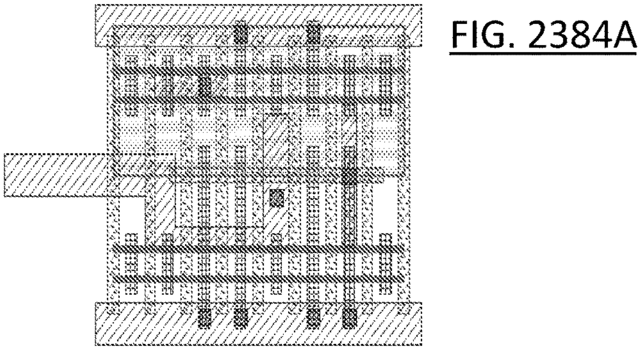
FIG. 2384A
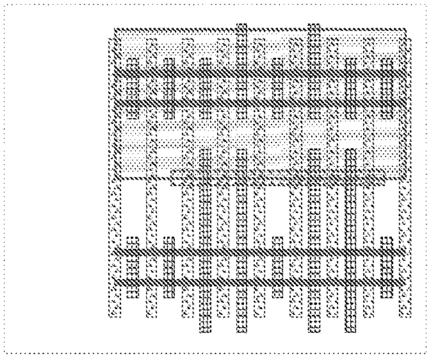
FIG. 2384B
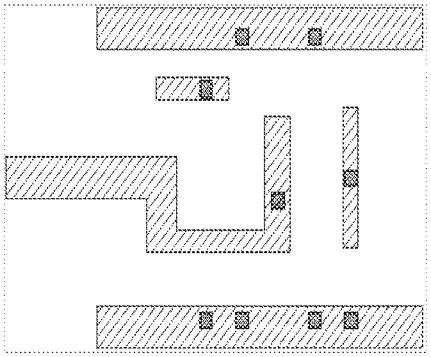
FIG. 2384C

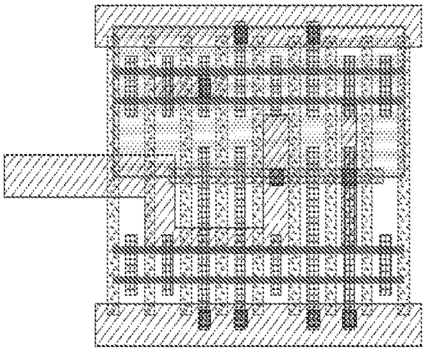
FIG. 2385A
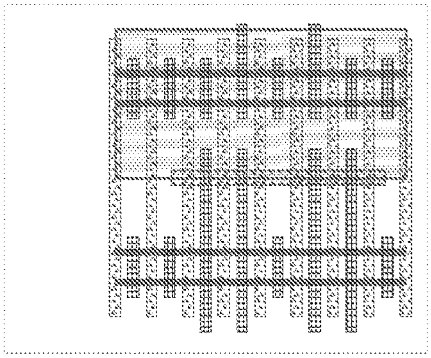
FIG. 2385B
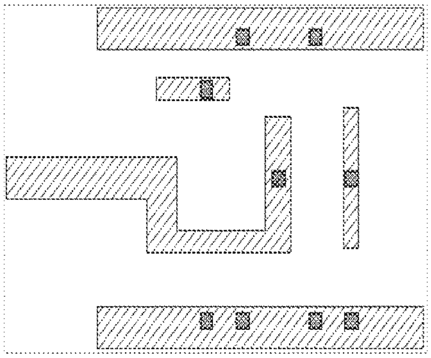
FIG. 2385C

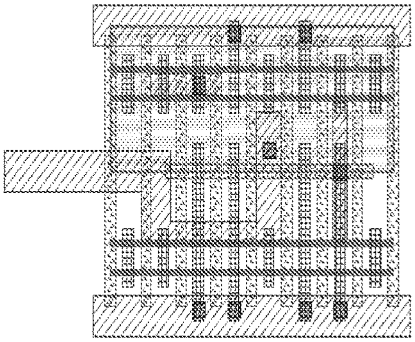
FIG. 2386A
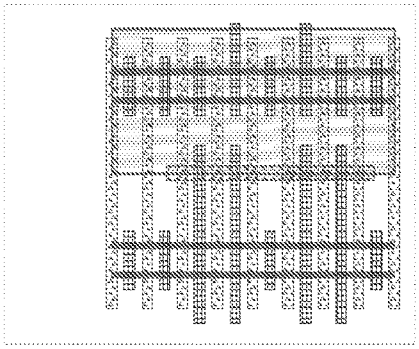
FIG. 2386B
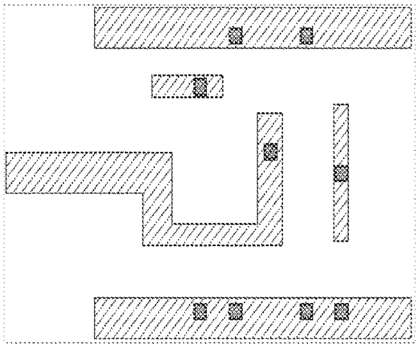
FIG. 2386C
*M* PDF Solutions, Inc.

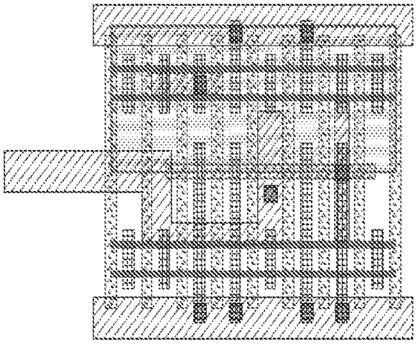
FIG. 2387A
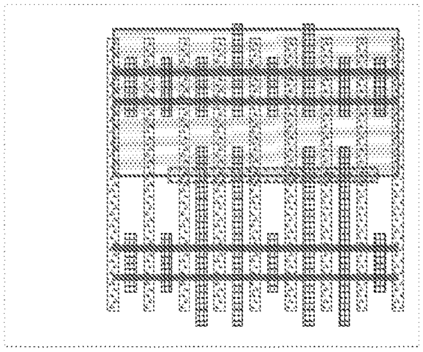
FIG. 2387B
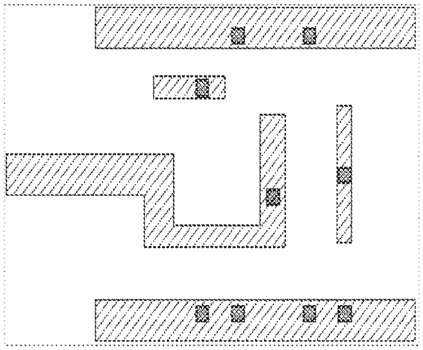
FIG. 2387C

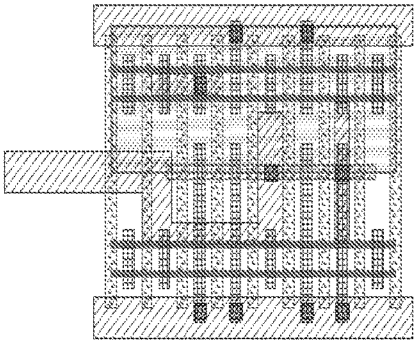
FIG. 2388A
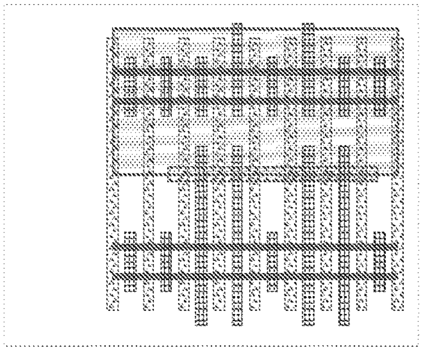
FIG. 2388B
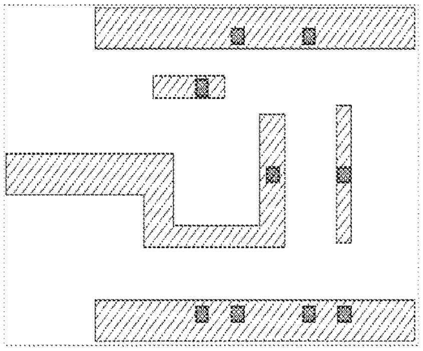
FIG. 2388C

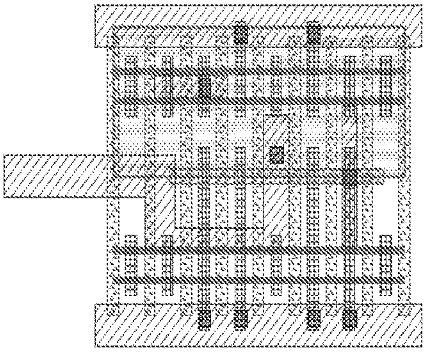
FIG. 2389A
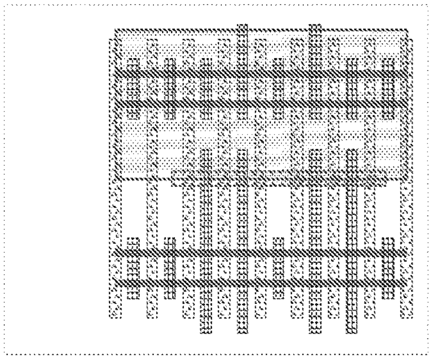
FIG. 2389B
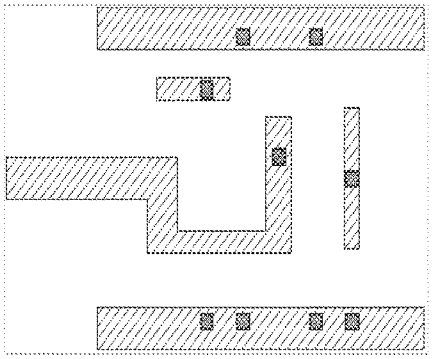
FIG. 2389C

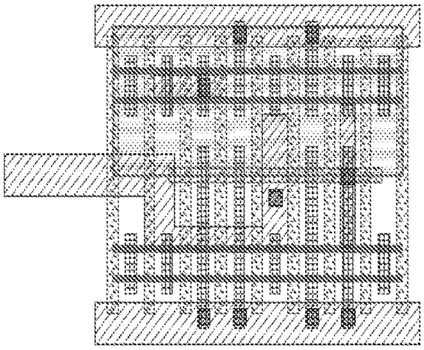
FIG. 2390A
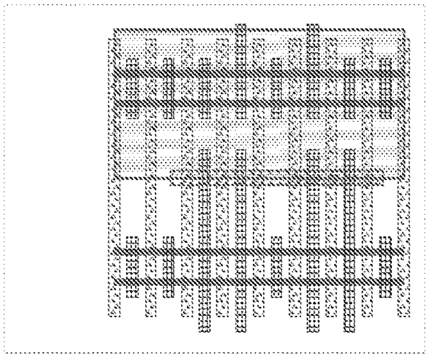
FIG. 2390B
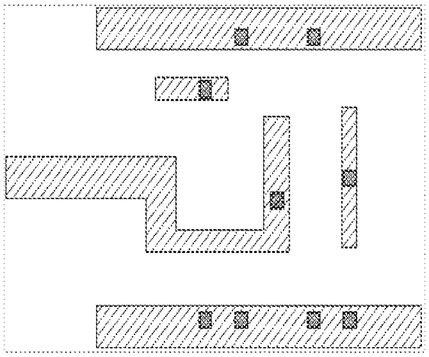
FIG. 2390C

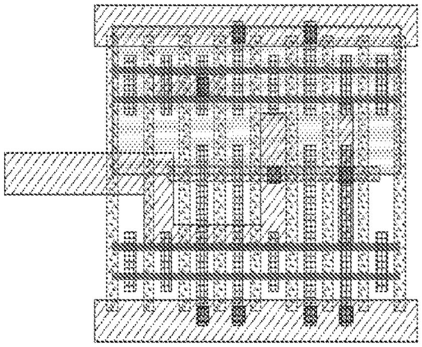
FIG. 2391A
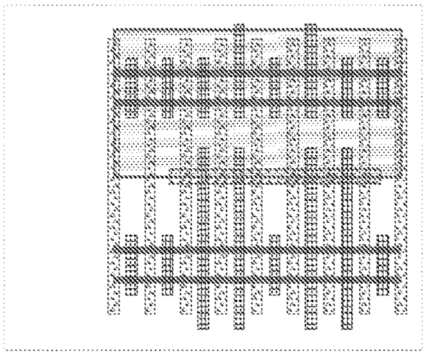
FIG. 2391B
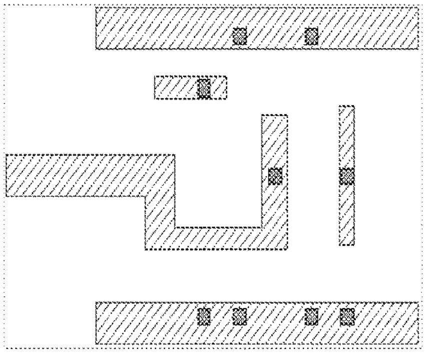
FIG. 2391C

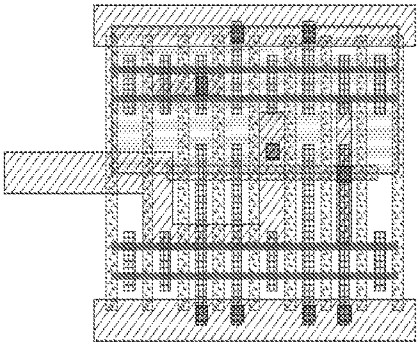
FIG. 2392A
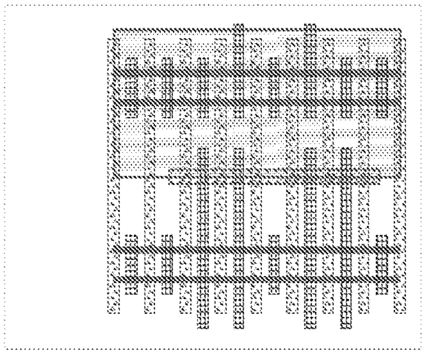
FIG. 2392B
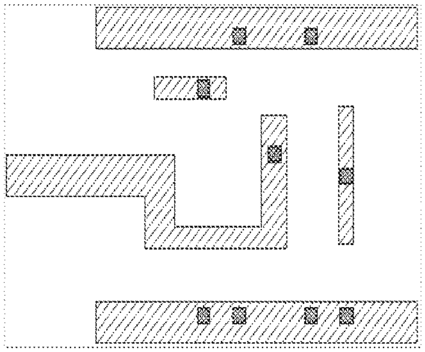
FIG. 2392C
*M* PDF Solutions, Inc.

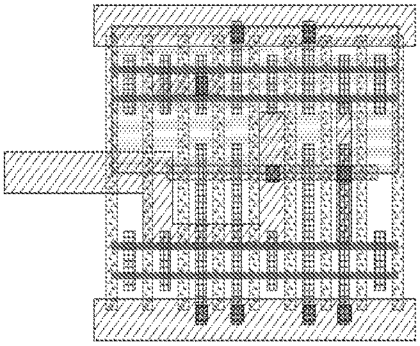
FIG. 2393A
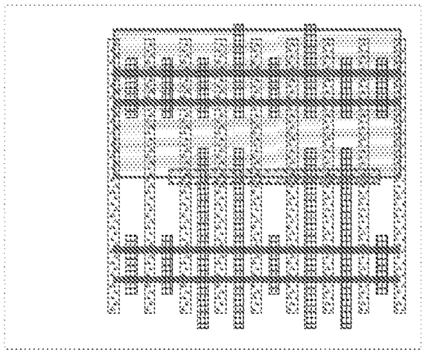
FIG. 2393B
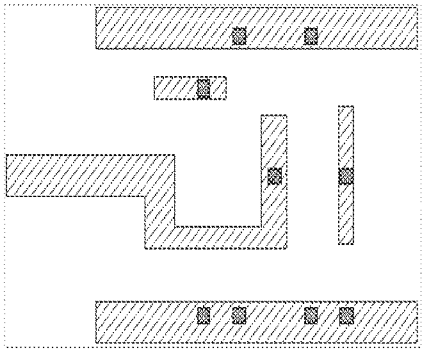
FIG. 2393C

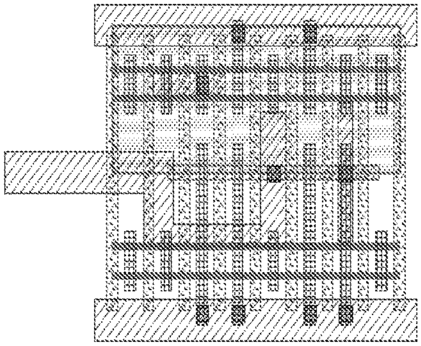
FIG. 2394A
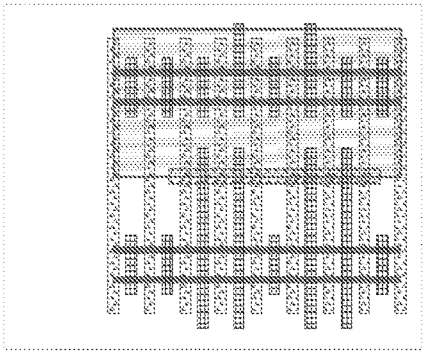
FIG. 2394B
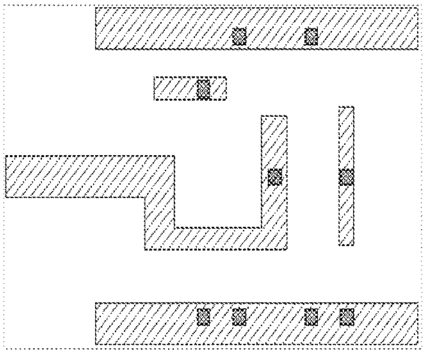
FIG. 2394C

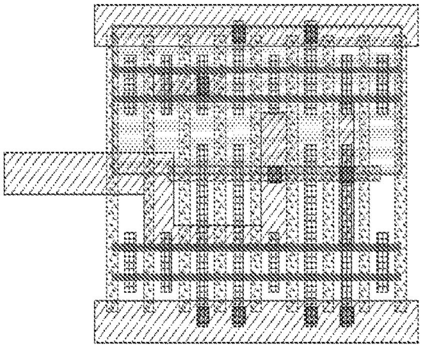
FIG. 2395A
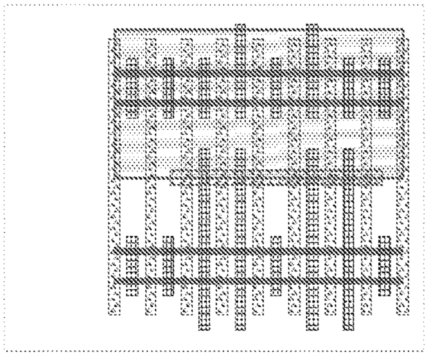
FIG. 2395B
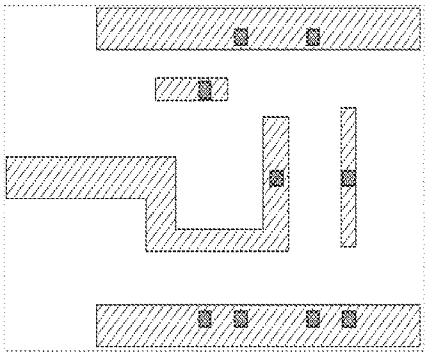
FIG. 2395C
*M* PDF Solutions, Inc.

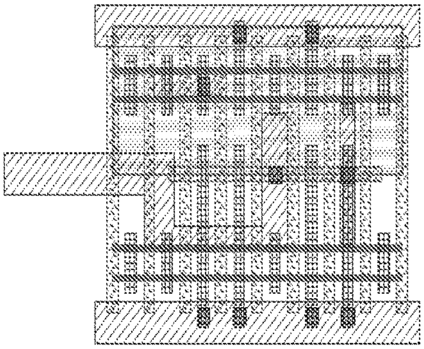
FIG. 2396A
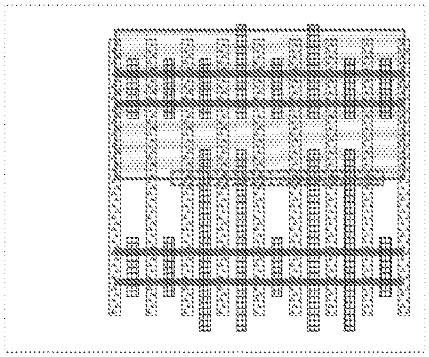
FIG. 2396B
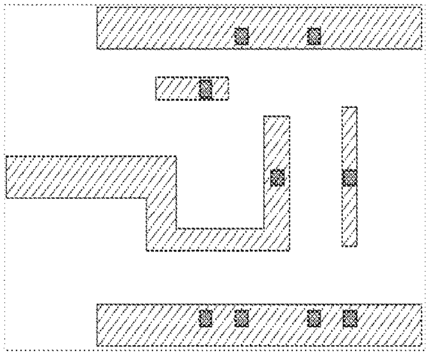
FIG. 2396C
*M* PDF Solutions, Inc.

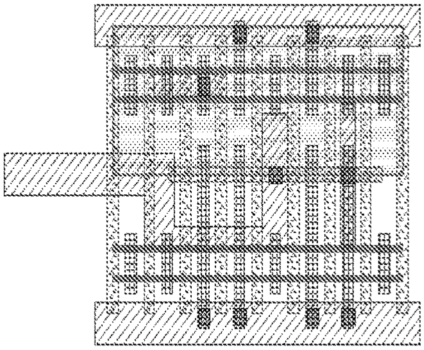
FIG. 2397A
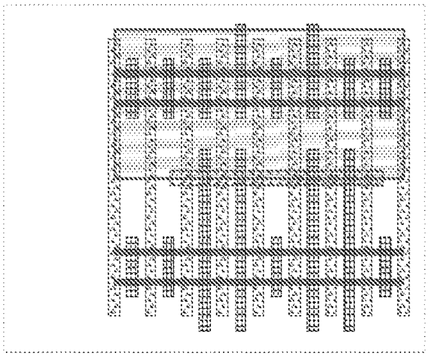
FIG. 2397B
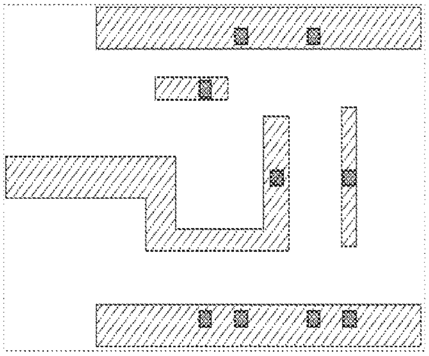
FIG. 2397C
*M* PDF Solutions, Inc.

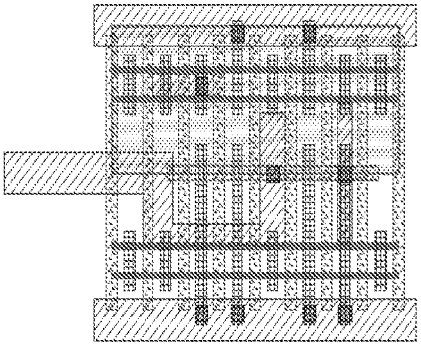
FIG. 2398A
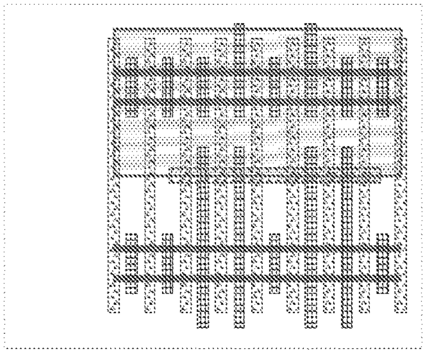
FIG. 2398B
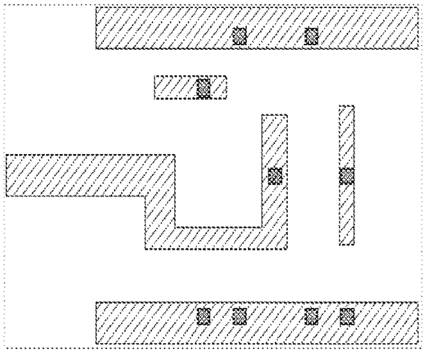
FIG. 2398C
*M* PDF Solutions, Inc.

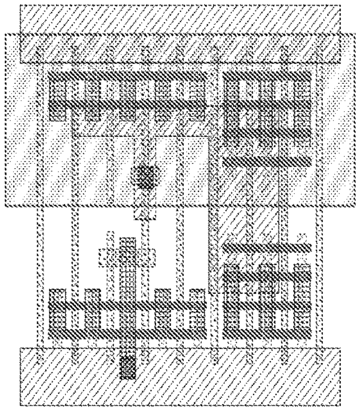
FIG. 2399A
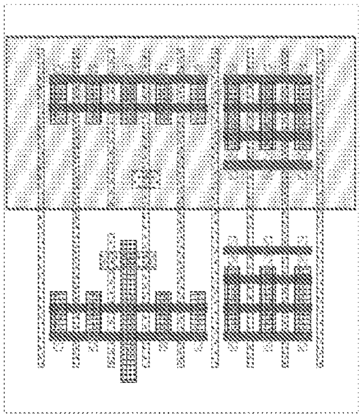
FIG. 2399B
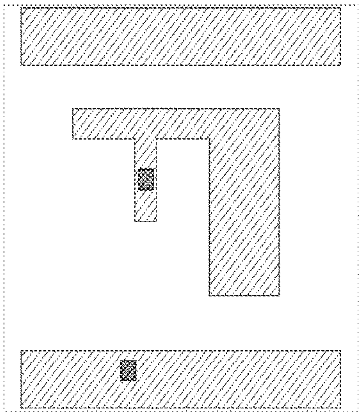
FIG. 2399C

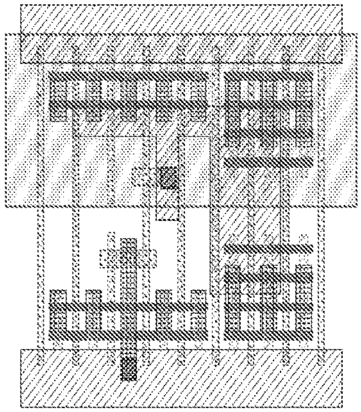
FIG. 2400A
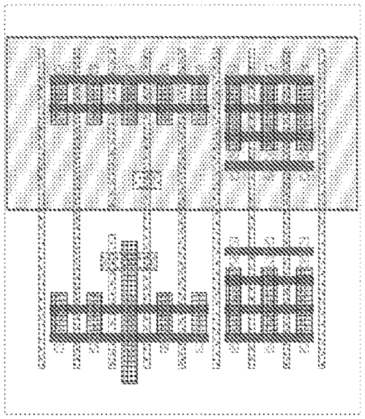
FIG. 2400B
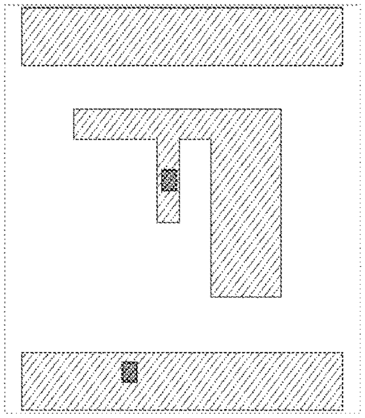
FIG. 2400C

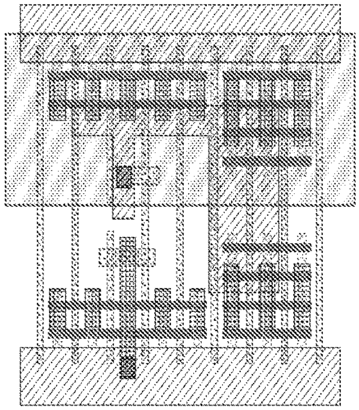
FIG. 2401A
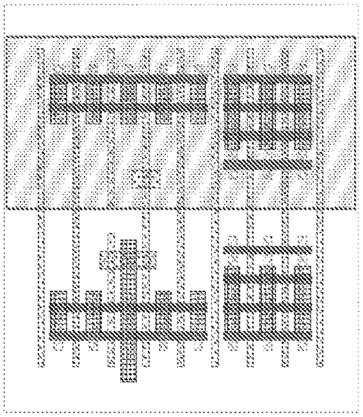
FIG. 2401B
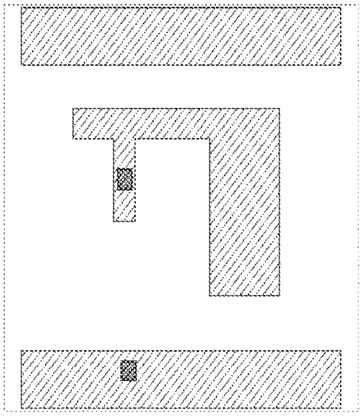
FIG. 2401C

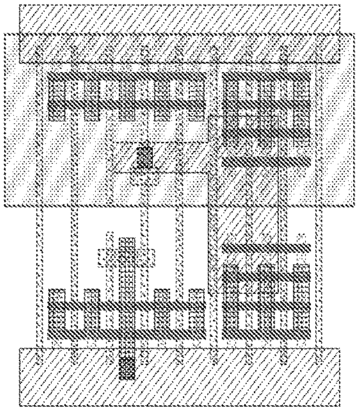
FIG. 2402A
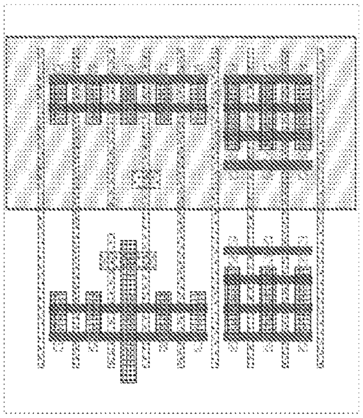
FIG. 2402B
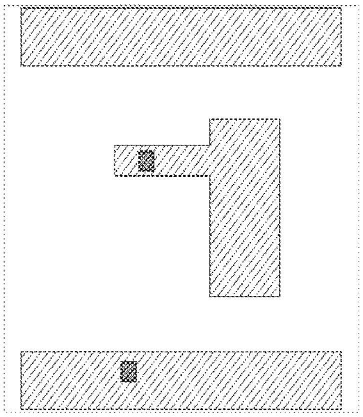
FIG. 2402C

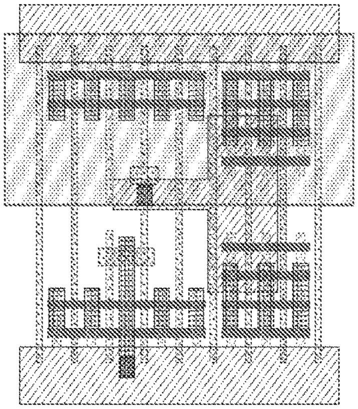
FIG. 2403A
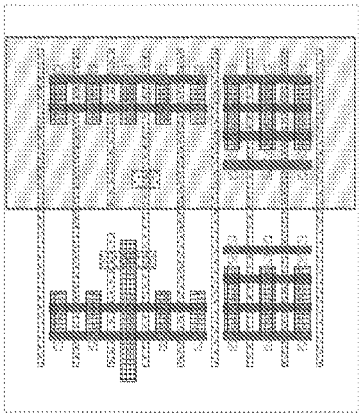
FIG. 2403B
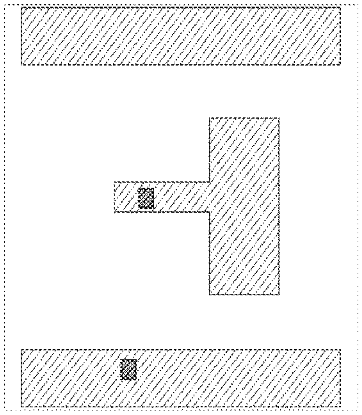
FIG. 2403C

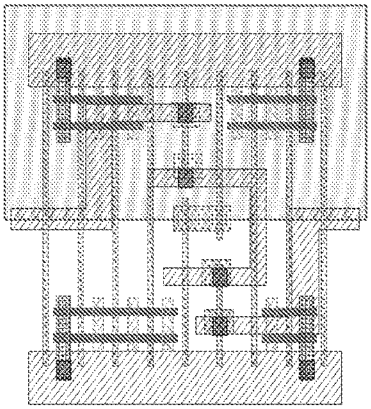
FIG. 2404A
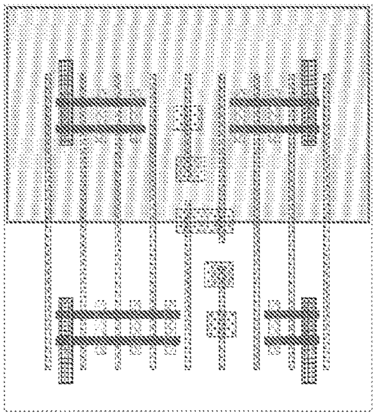
FIG. 2404B
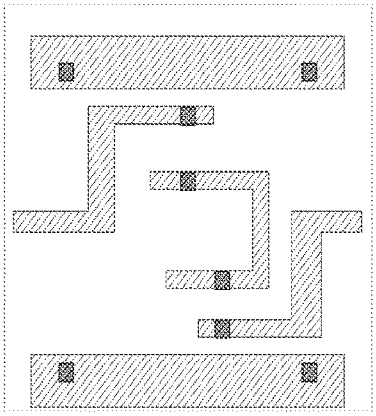
FIG. 2404C

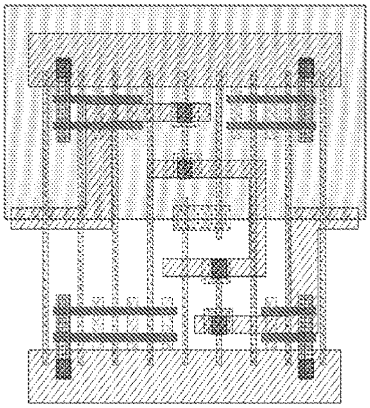
FIG. 2405A
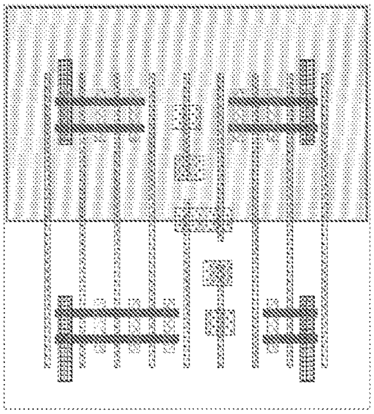
FIG. 2405B
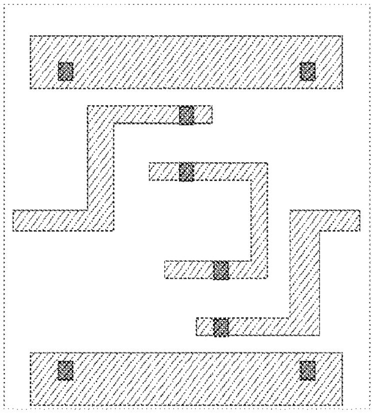
FIG. 2405C

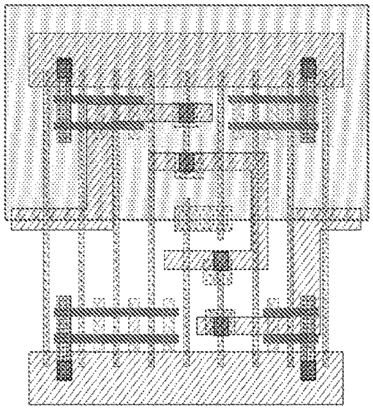
FIG. 2406A
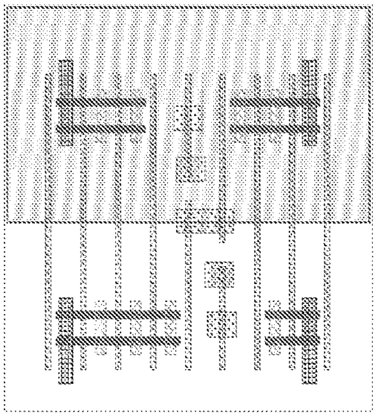
FIG. 2406B
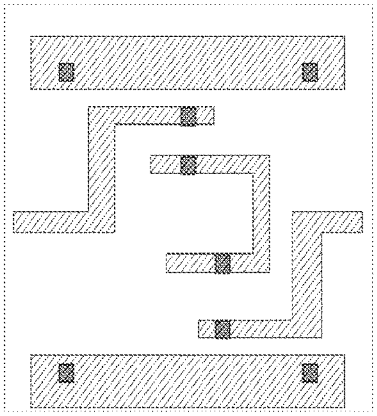
FIG. 2406C

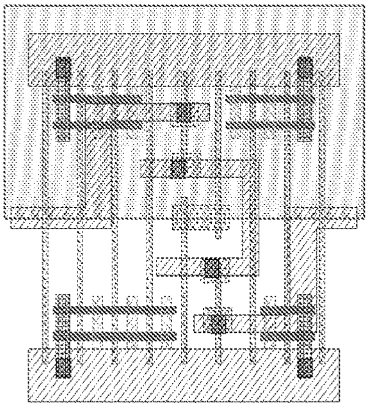
FIG. 2407A
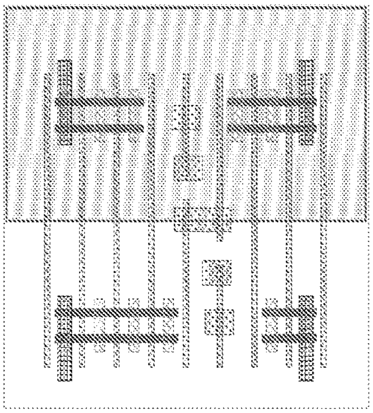
FIG. 2407B
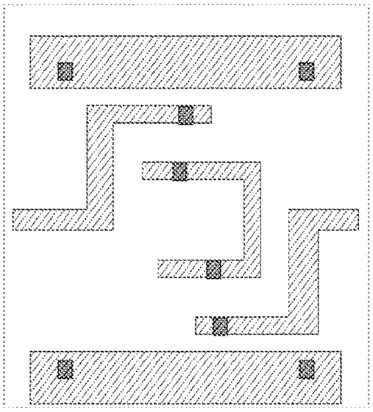
FIG. 2407C

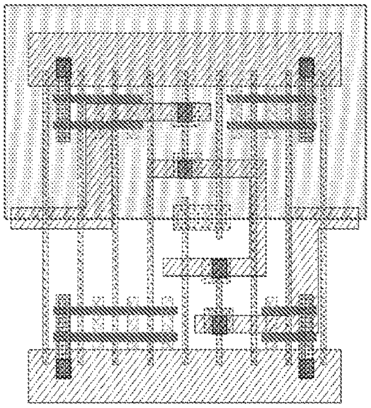
FIG. 2408A
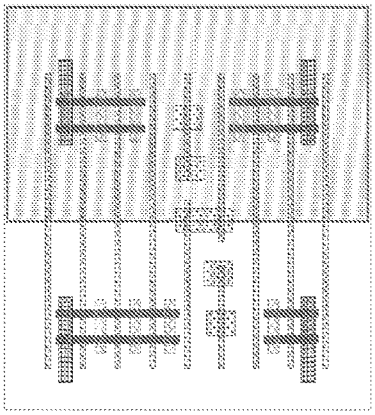
FIG. 2408B
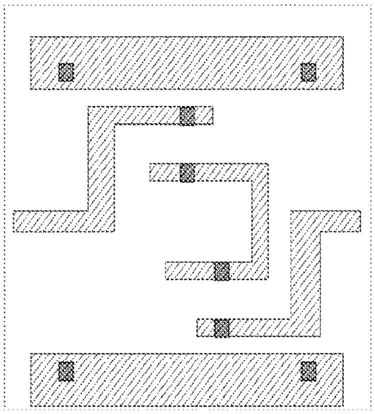
FIG. 2408C

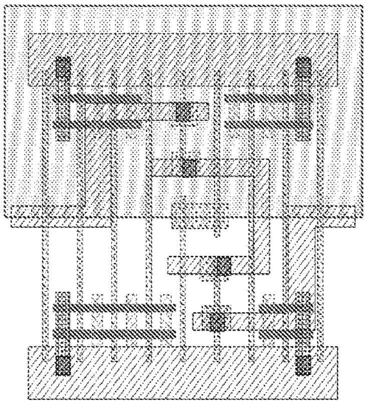
FIG. 2409A
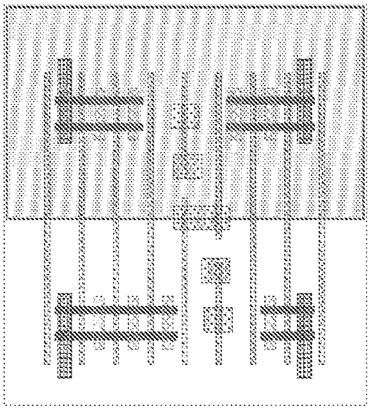
FIG. 2409B
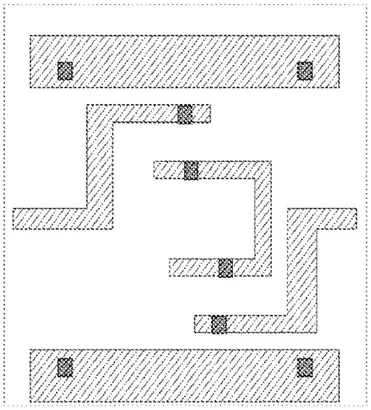
FIG. 2409C

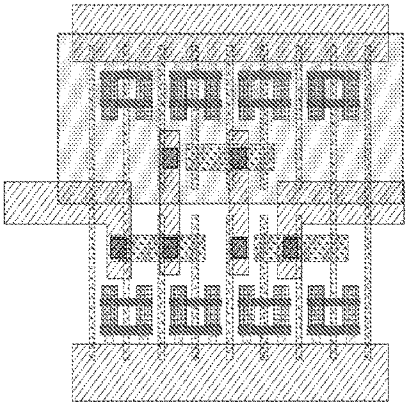
FIG. 2410A
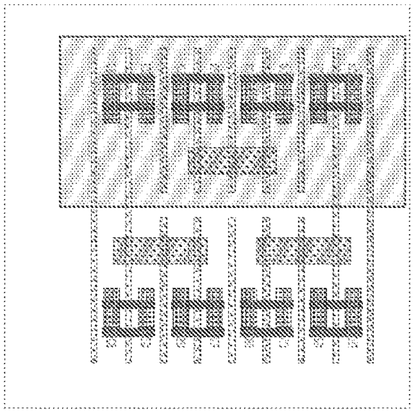
FIG. 2410B
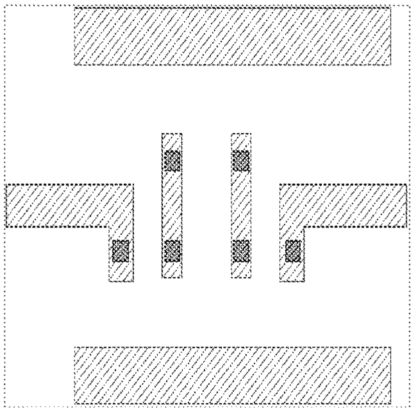
FIG. 2410C
*M* PDF Solutions, Inc.

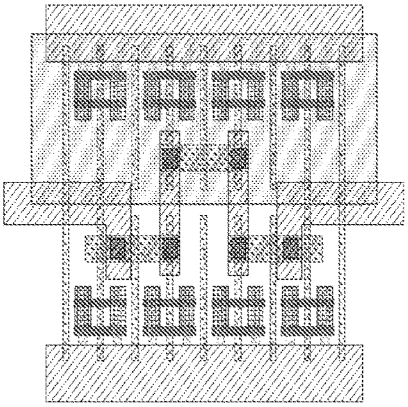
FIG. 2411A
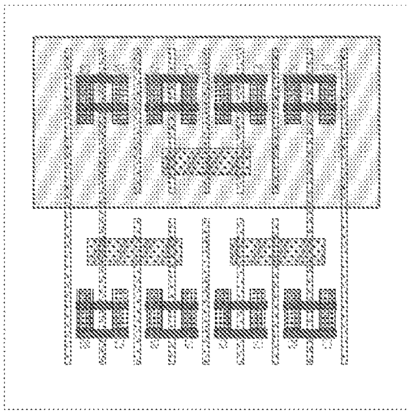
FIG. 2411B
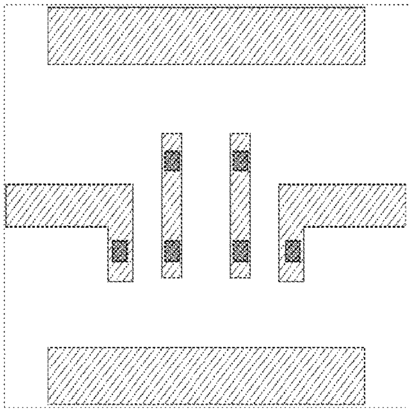
FIG. 2411C

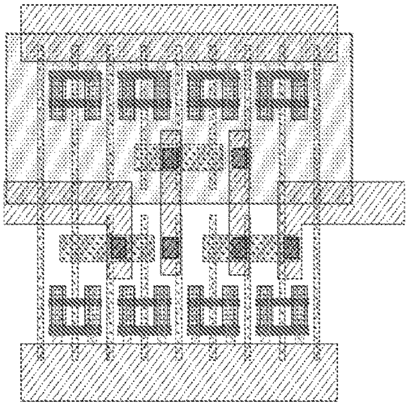
FIG. 2412A
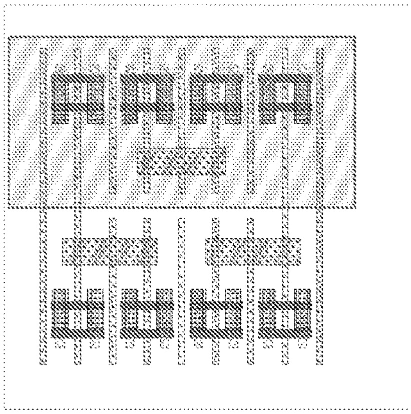
FIG. 2412B
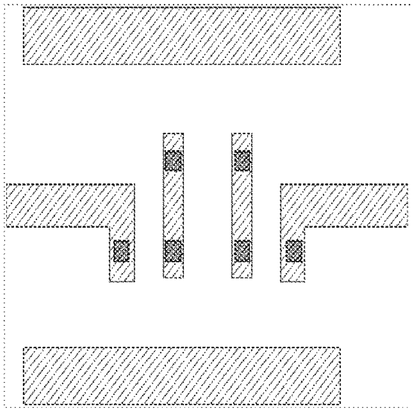
FIG. 2412C
*M* PDF Solutions, Inc.

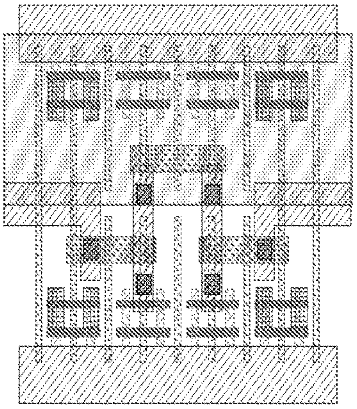
FIG. 2413A
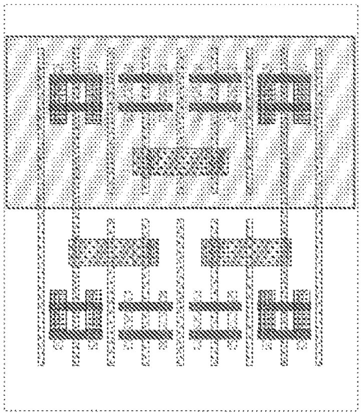
FIG. 2413B
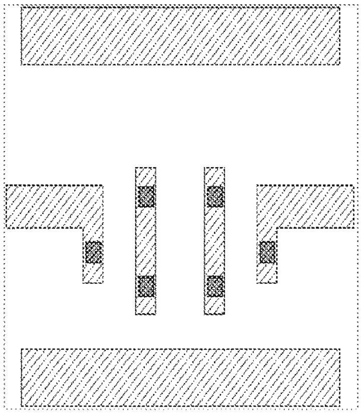
FIG. 2413C

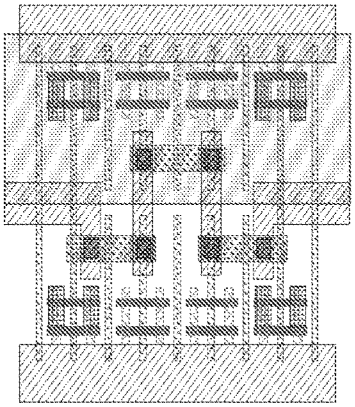
FIG. 2414A
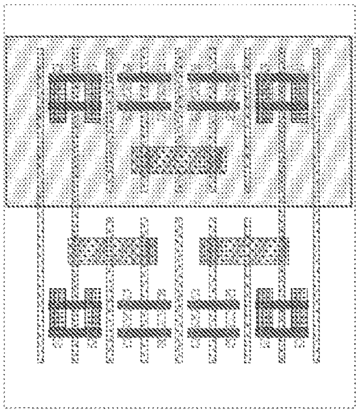
FIG. 2414B
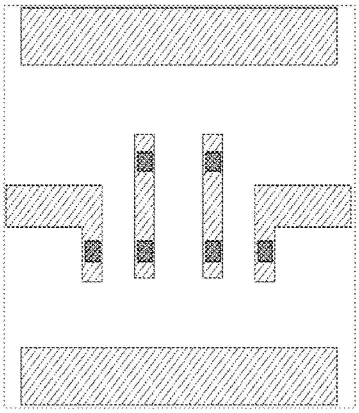
FIG. 2414C

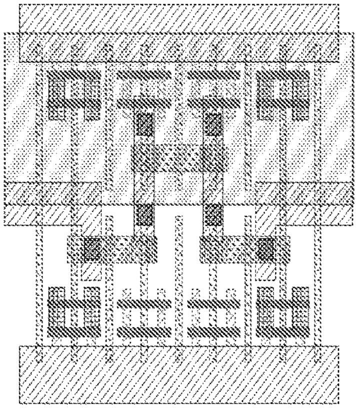
FIG. 2415A
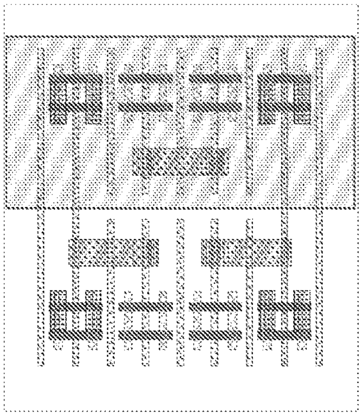
FIG. 2415B
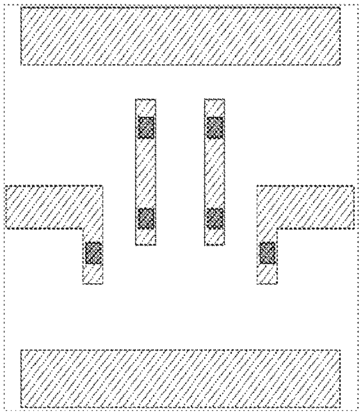
FIG. 2415C

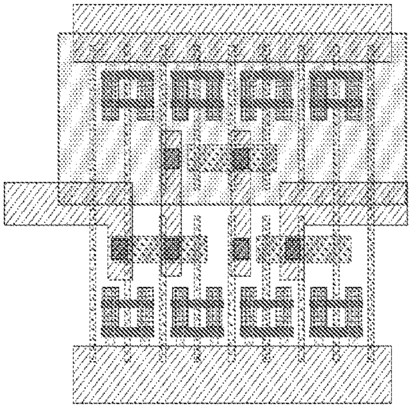
FIG. 2416A
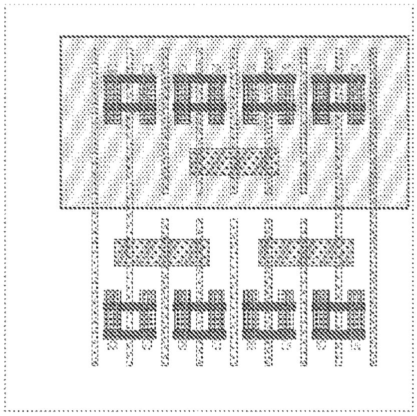
FIG. 2416B
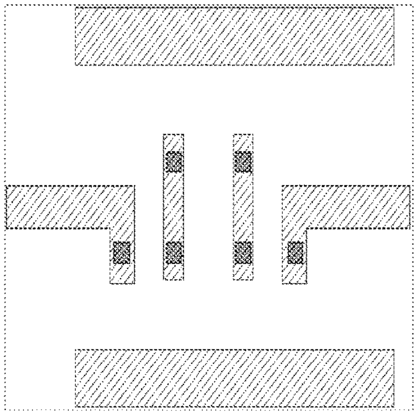
FIG. 2416C

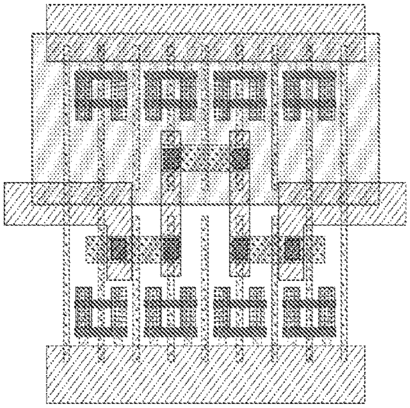
FIG. 2417A
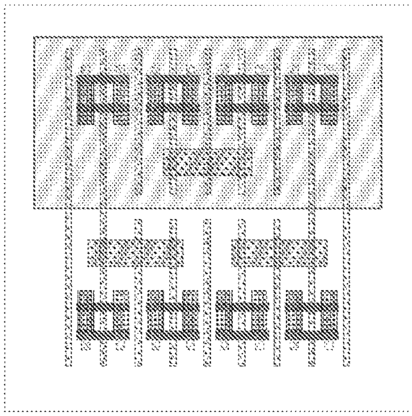
FIG. 2417B
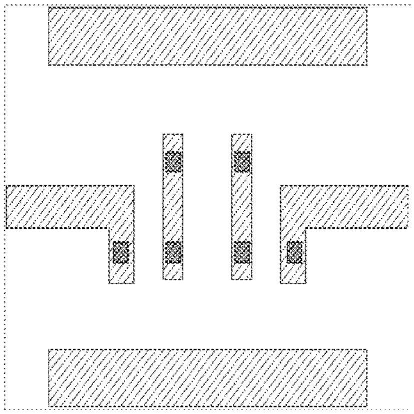
FIG. 2417C
*M* PDF Solutions, Inc.

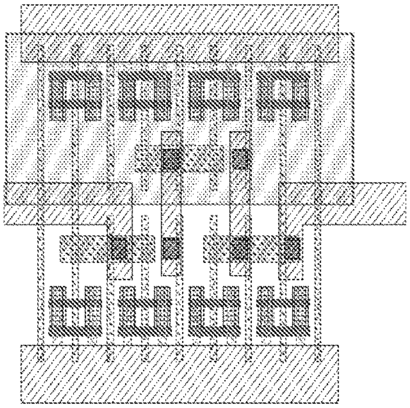
FIG. 2418A
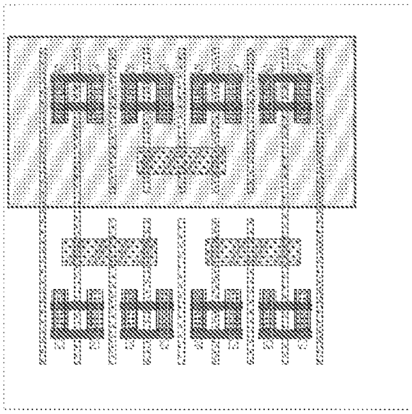
FIG. 2418B
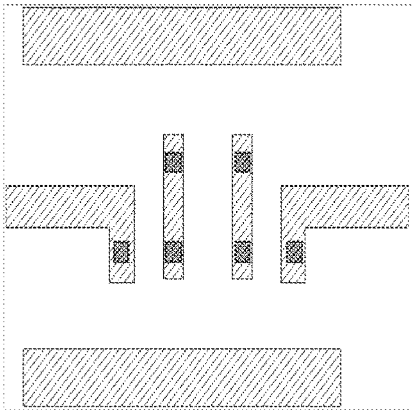
FIG. 2418C

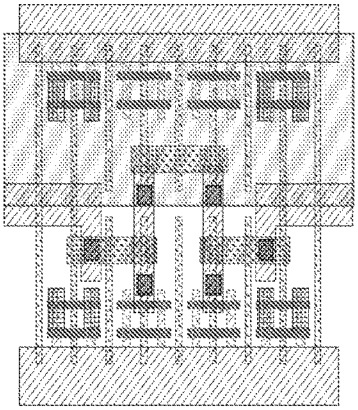
FIG. 2419A
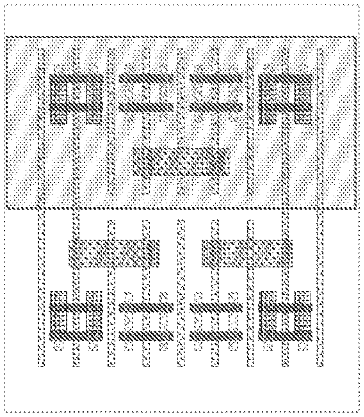
FIG. 2419B
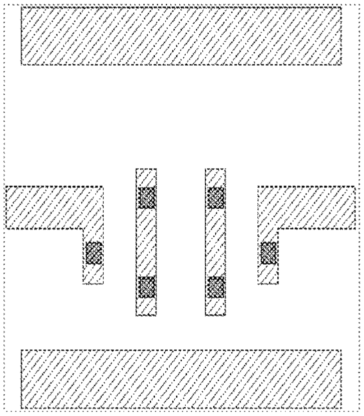
FIG. 2419C

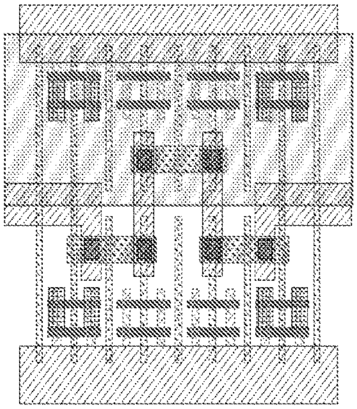
FIG. 2420A
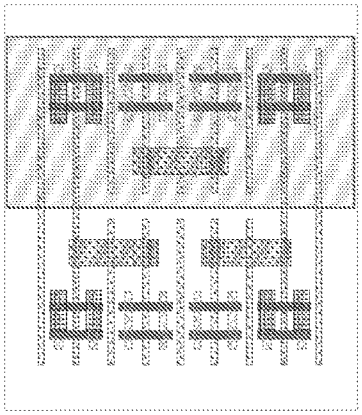
FIG. 2420B
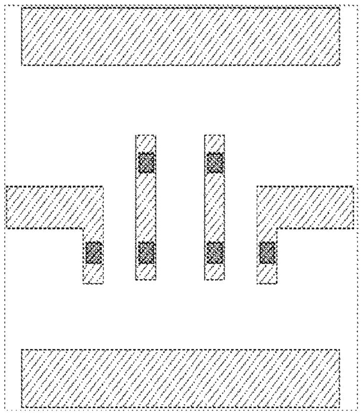
FIG. 2420C

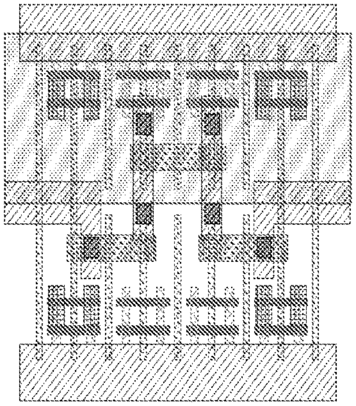
FIG. 2421A
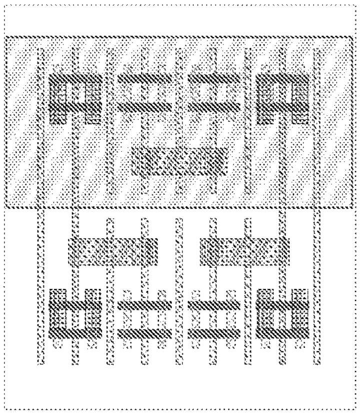
FIG. 2421B
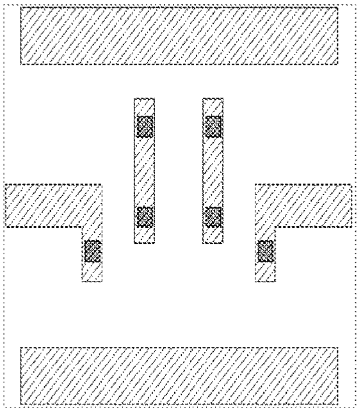
FIG. 2421C
*M* PDF Solutions, Inc.

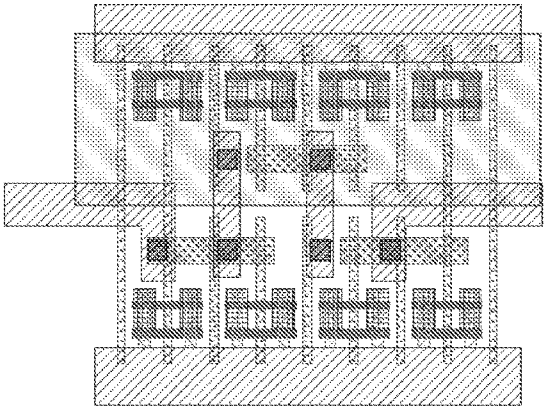
FIG. 2422A
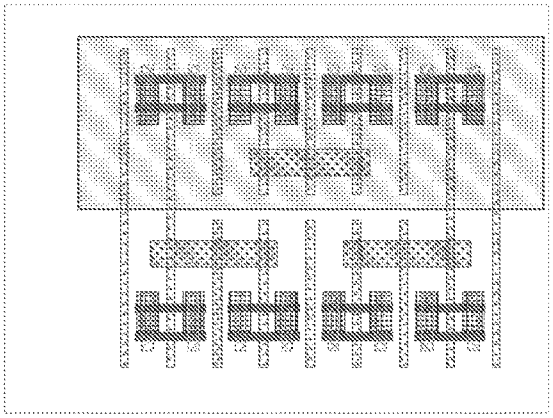
FIG. 2422B
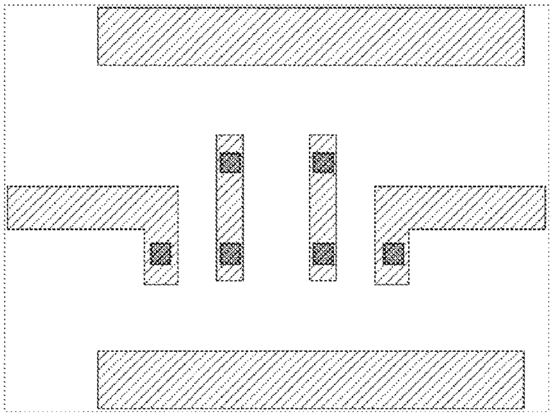
FIG. 2422C
*M* PDF Solutions, Inc.

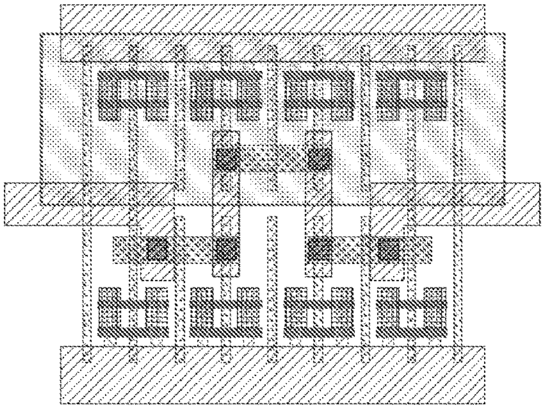
FIG. 2423A
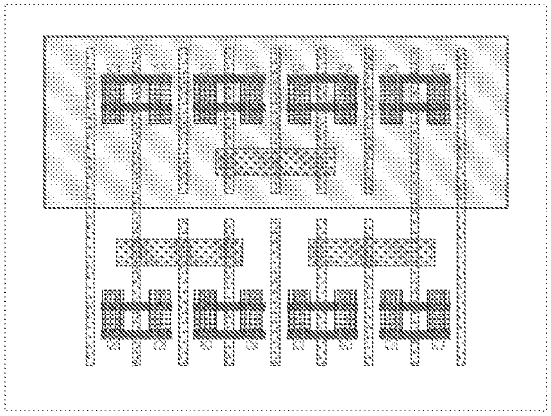
FIG. 2423B
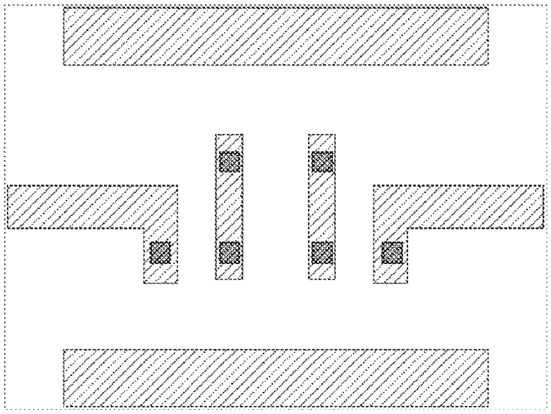
FIG. 2423C
*M* PDF Solutions, Inc.

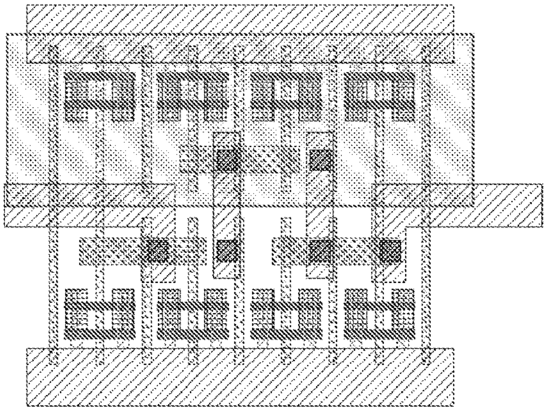
FIG. 2424A
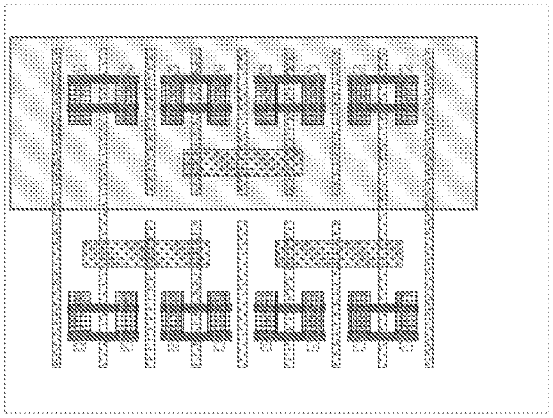
FIG. 2424B
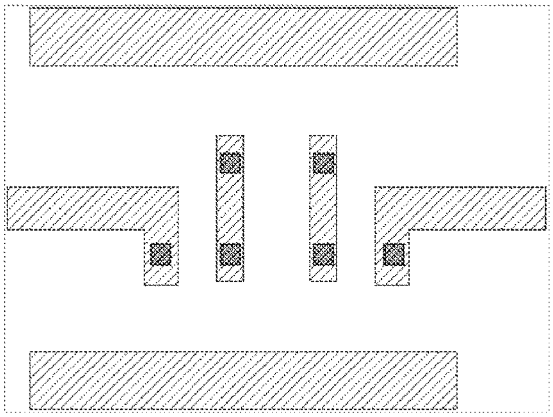
FIG. 2424C

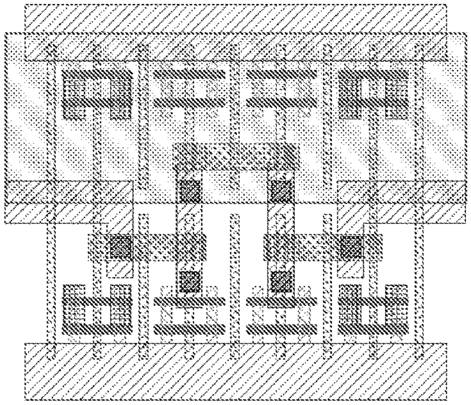
FIG. 2425A
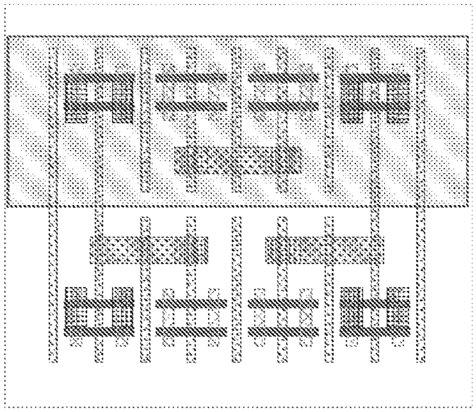
FIG. 2425B
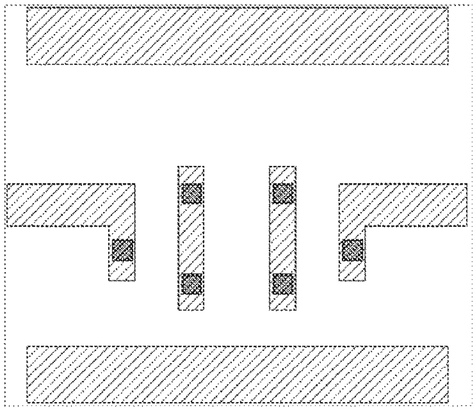
FIG. 2425C

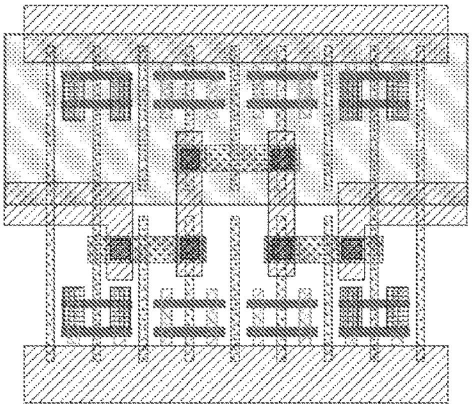
FIG. 2426A
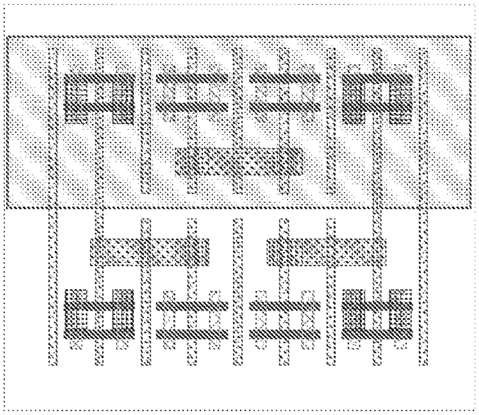
FIG. 2426B
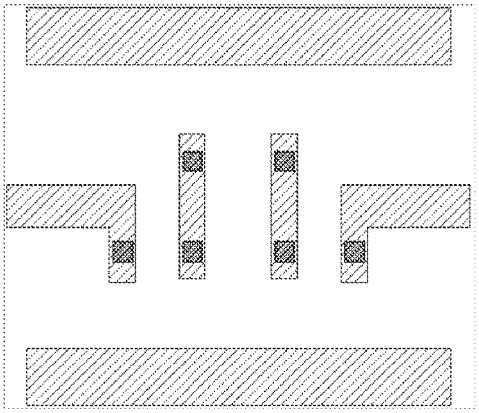
FIG. 2426C

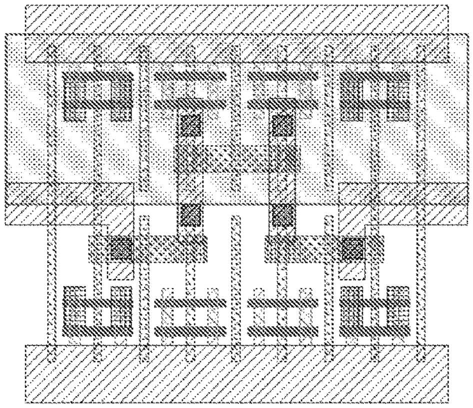
FIG. 2427A
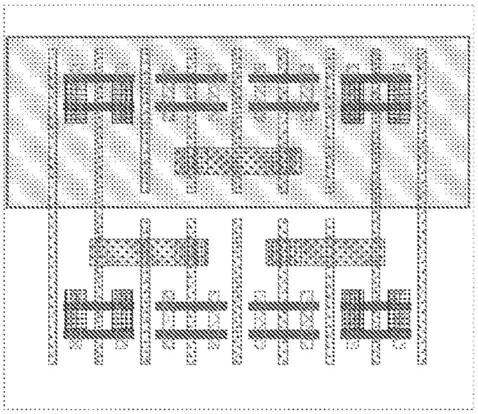
FIG. 2427B
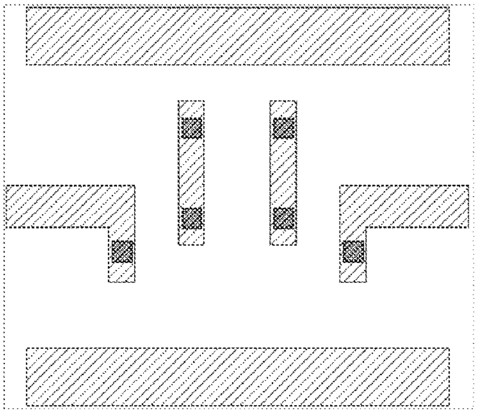
FIG. 2427C
*M* PDF Solutions, Inc.

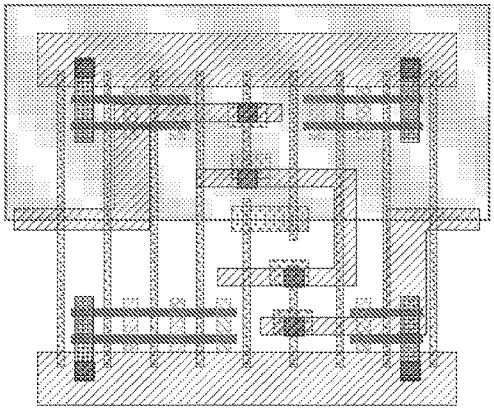
FIG. 2428A
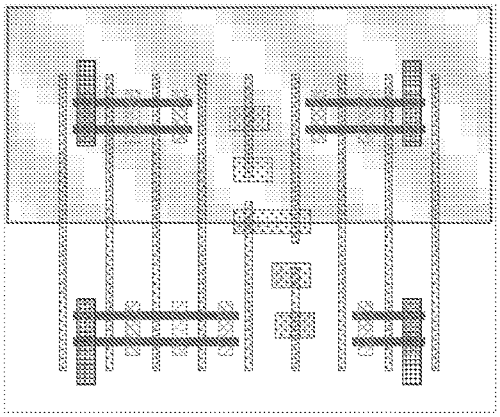
FIG. 2428B
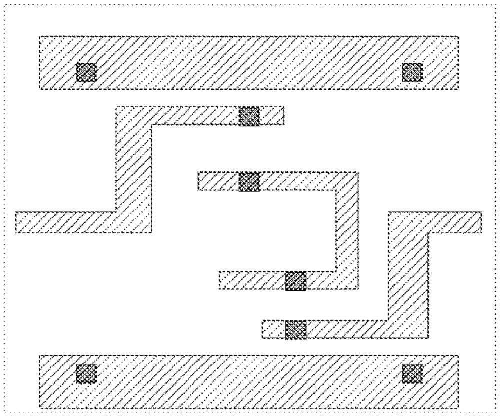
FIG. 2428C
*M* PDF Solutions, Inc.

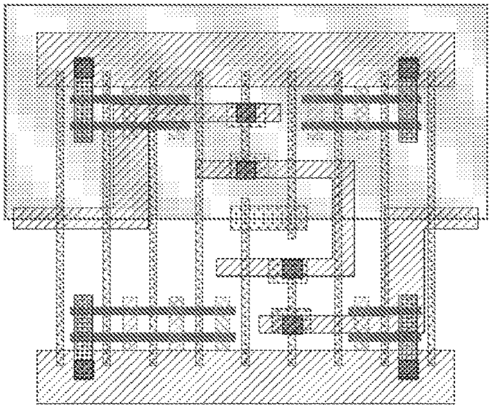
FIG. 2429A
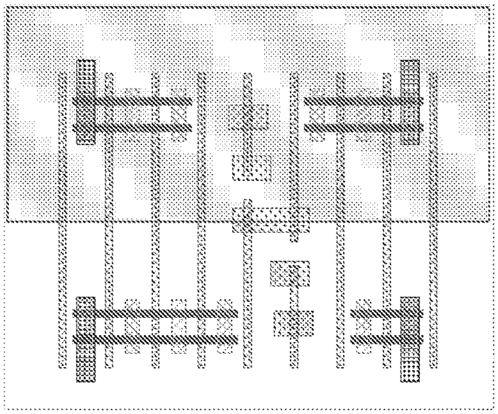
FIG. 2429B
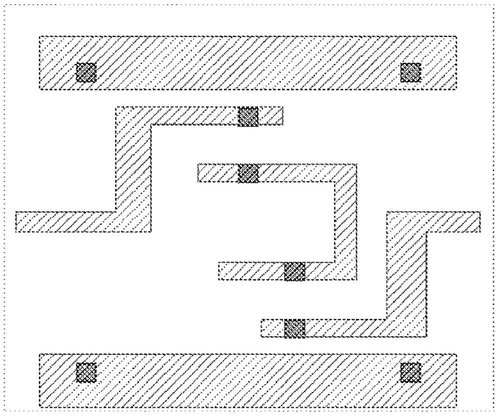
FIG. 2429C
*M* PDF Solutions, Inc.

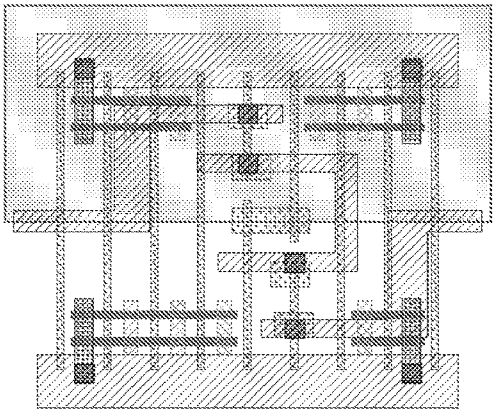
FIG. 2430A
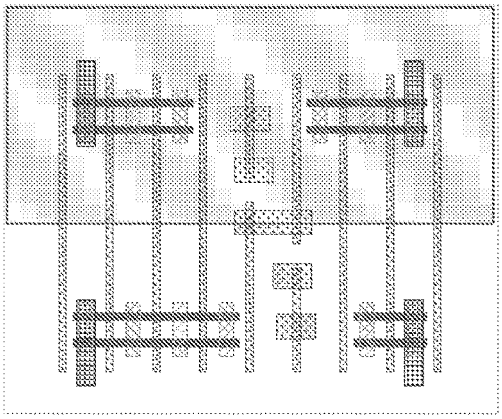
FIG. 2430B
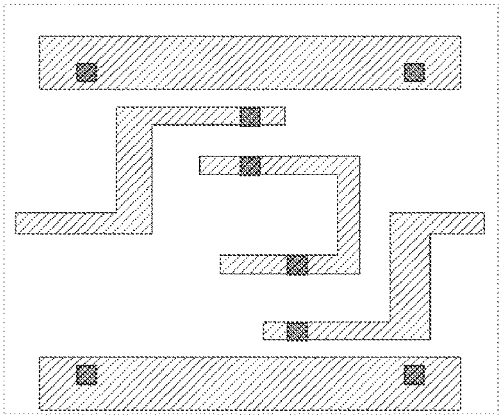
FIG. 2430C
*M* PDF Solutions, Inc.

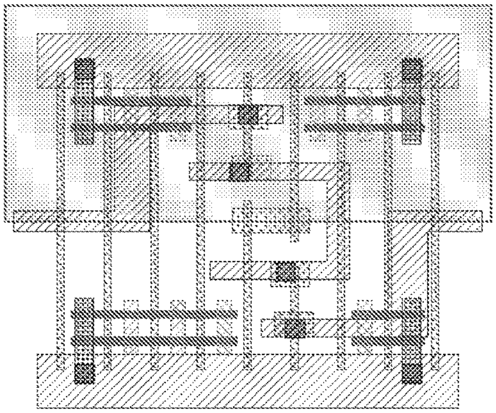
FIG. 2431A
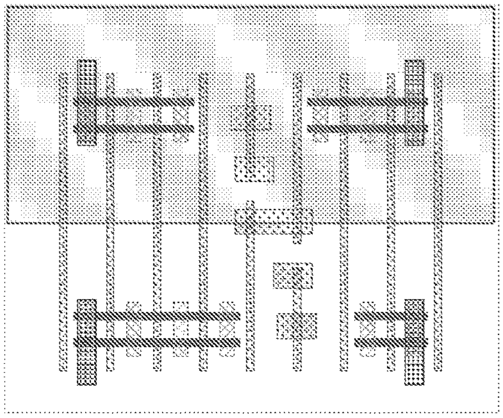
FIG. 2431B
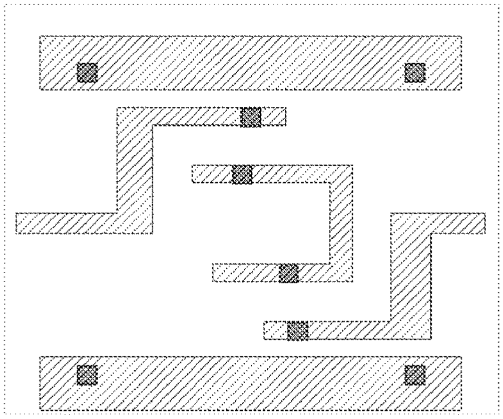
FIG. 2431C
*M* PDF Solutions, Inc.

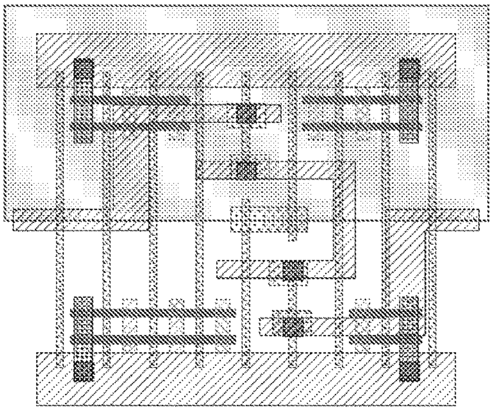
FIG. 2432A
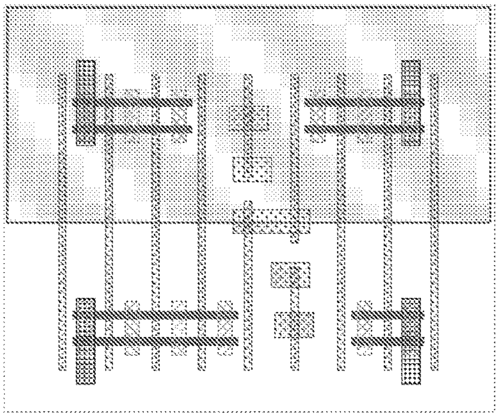
FIG. 2432B
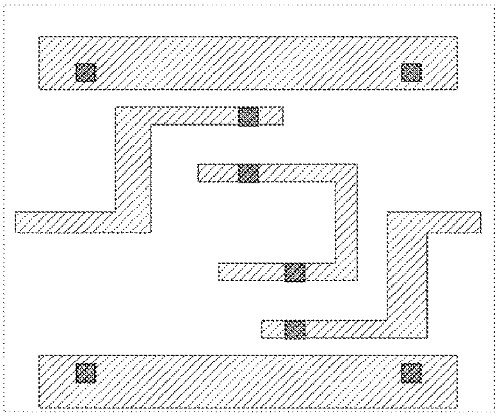
FIG. 2432C

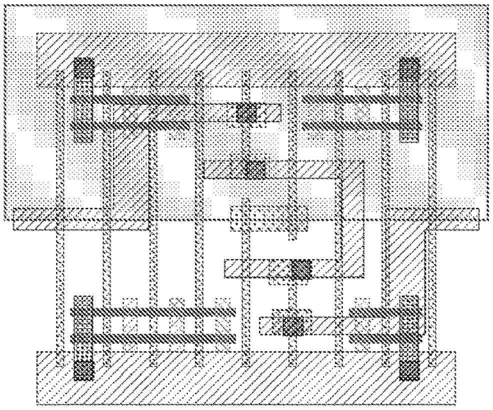
FIG. 2433A
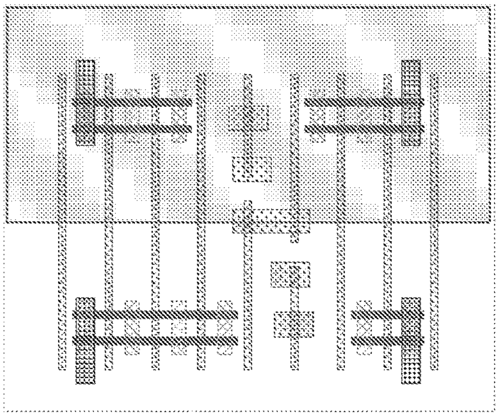
FIG. 2433B
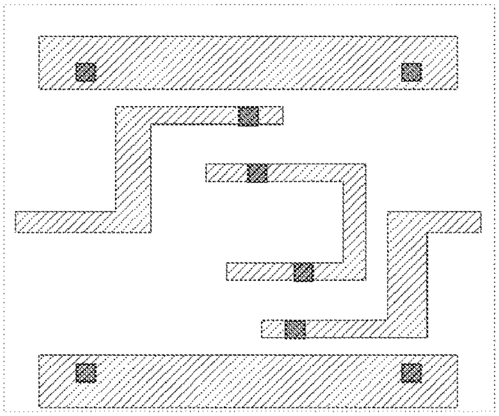
FIG. 2433C

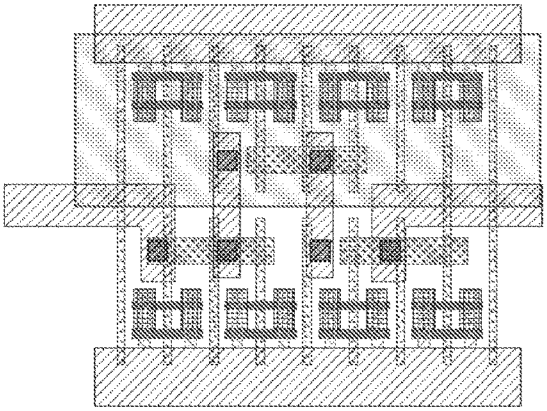
FIG. 2434A
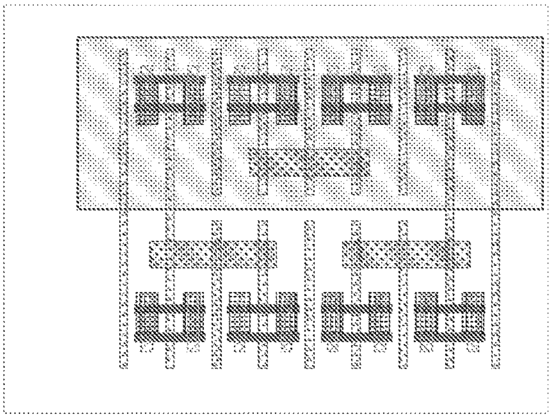
FIG. 2434B
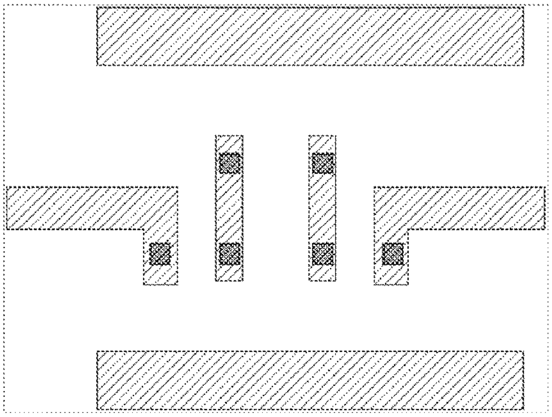
FIG. 2434C

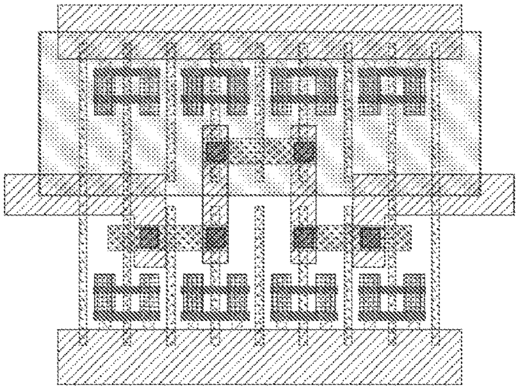
FIG. 2435A
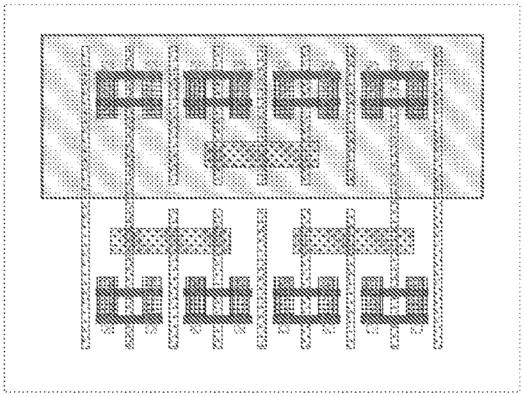
FIG. 2435B
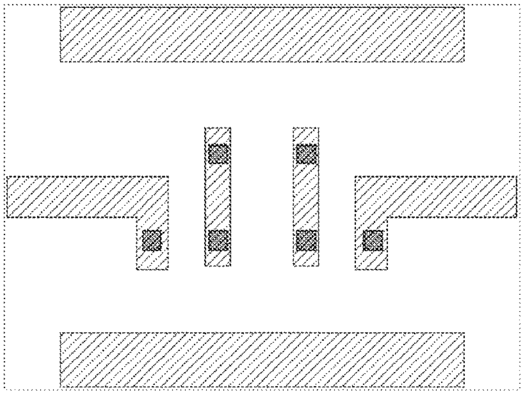
FIG. 2435C

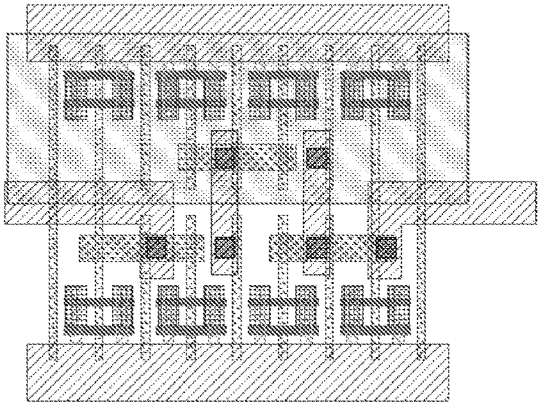
FIG. 2436A
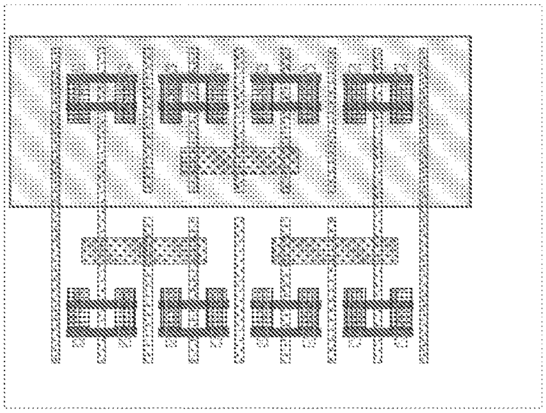
FIG. 2436B
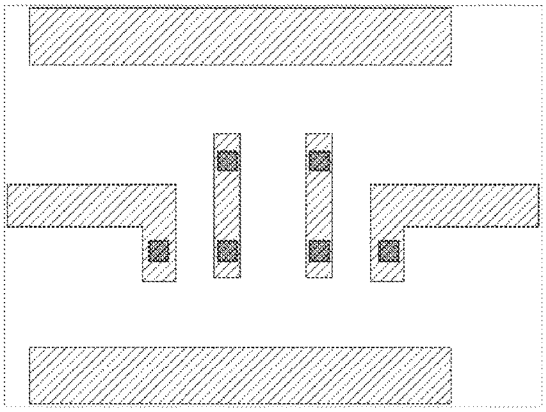
FIG. 2436C

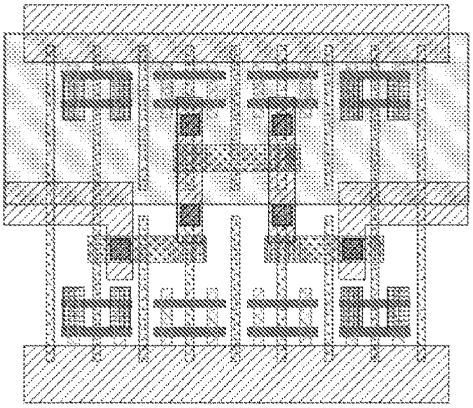
FIG. 2437A
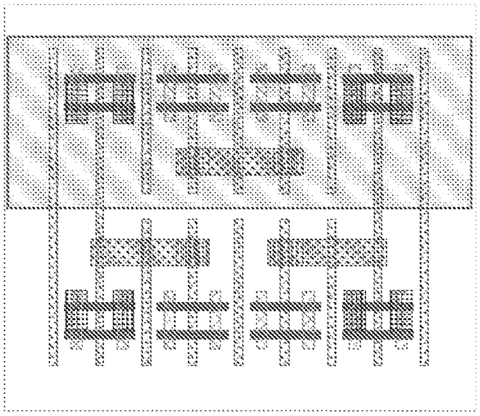
FIG. 2437B
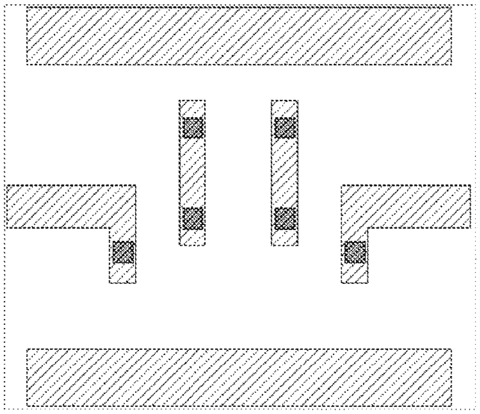
FIG. 2437C

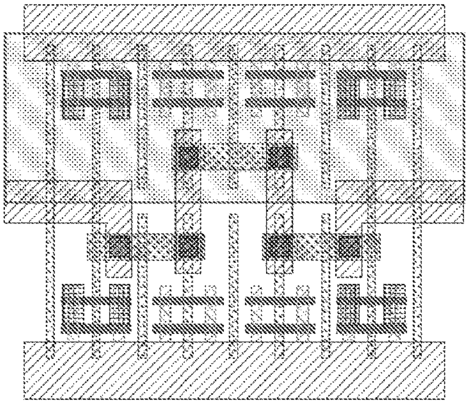
FIG. 2438A
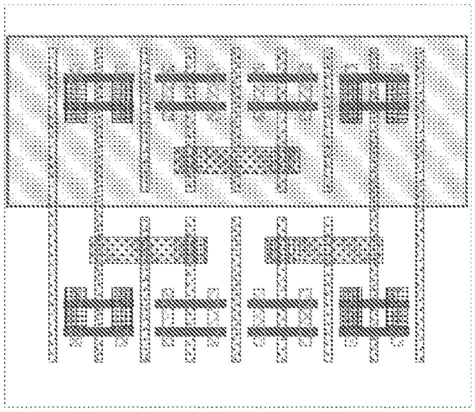
FIG. 2438B
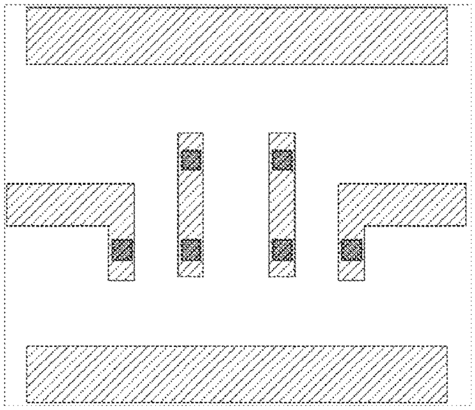
FIG. 2438C

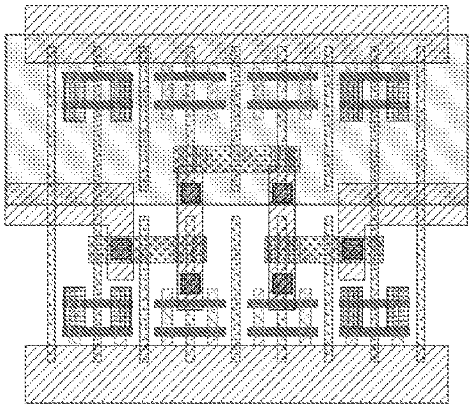
FIG. 2439A
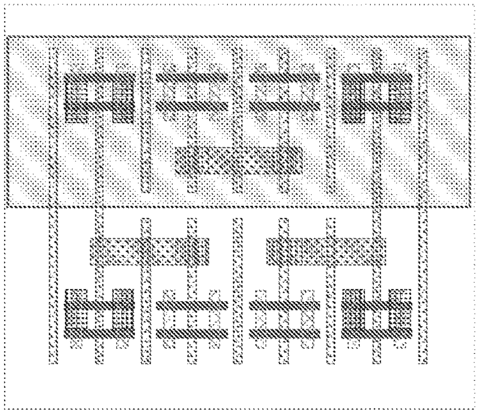
FIG. 2439B
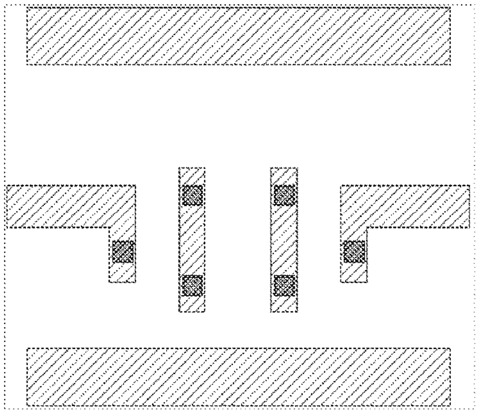
FIG. 2439C

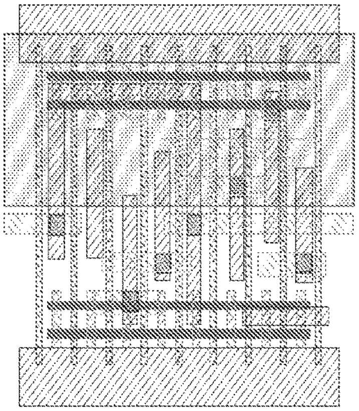
FIG. 2440A
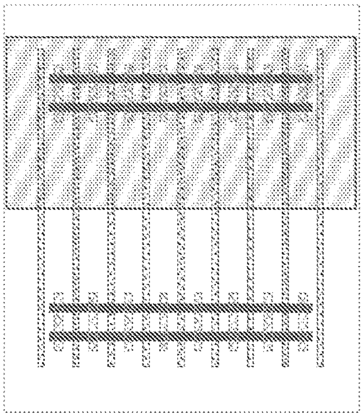
FIG. 2440B
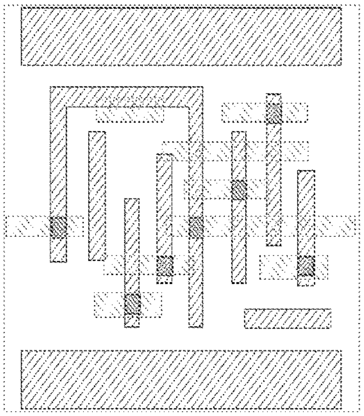
FIG. 2440C

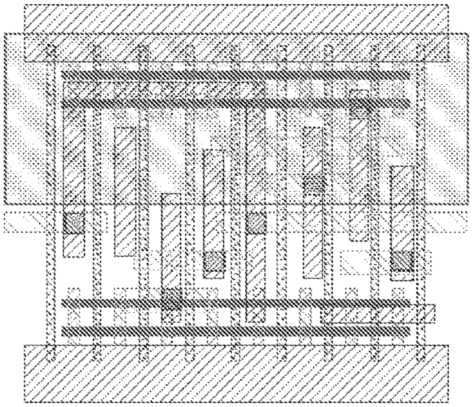
FIG. 2441A
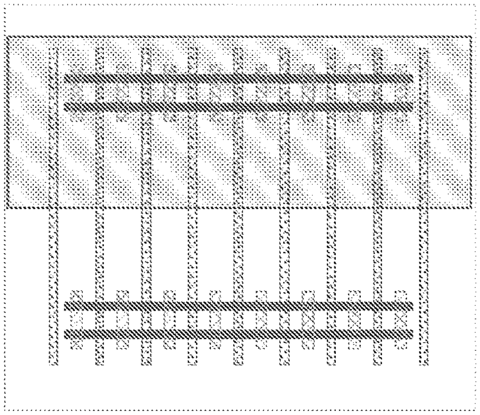
FIG. 2441B
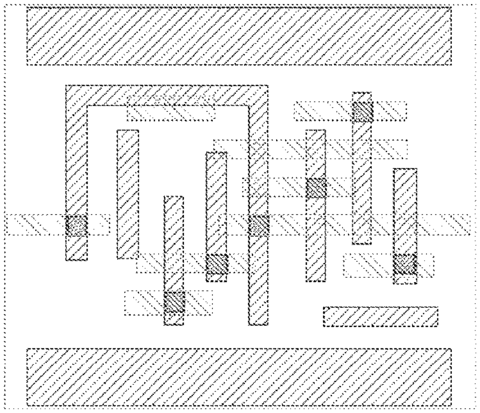
FIG. 2441C
*M* PDF Solutions, Inc.

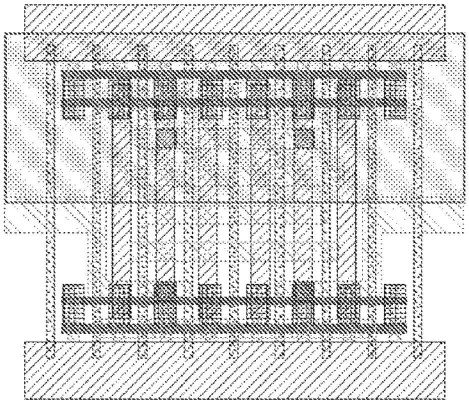
FIG. 2442A
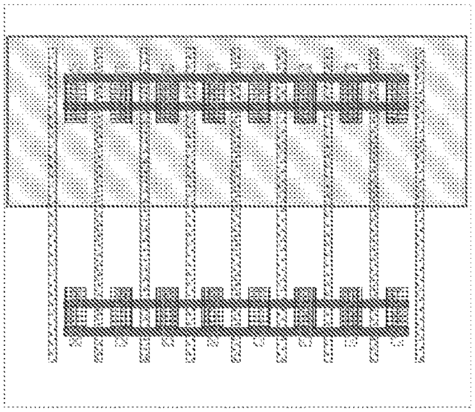
FIG. 2442B
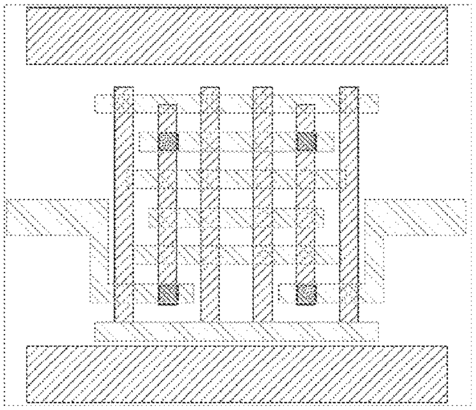
FIG. 2442C

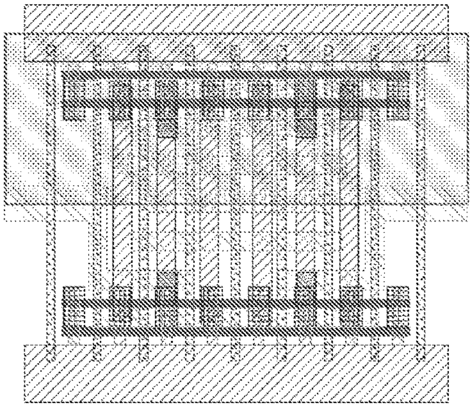
FIG. 2443A
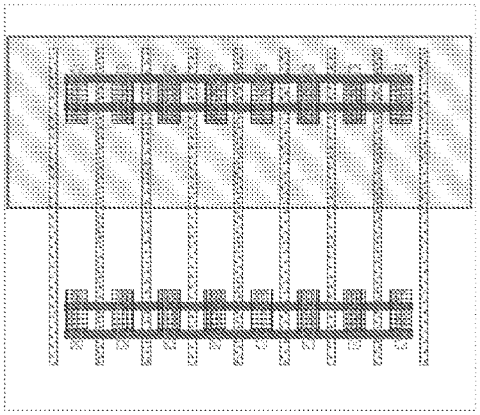
FIG. 2443B
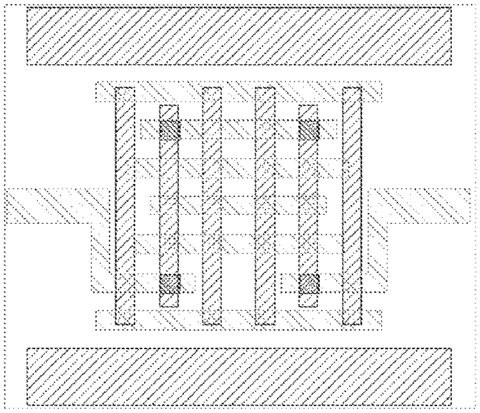
FIG. 2443C

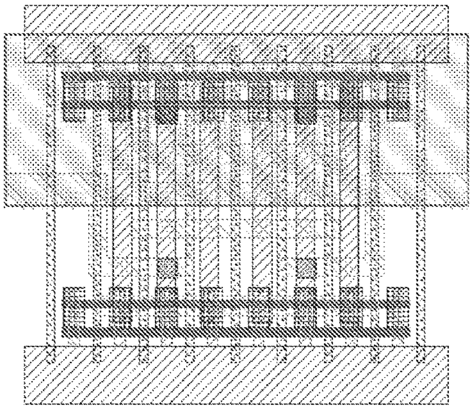
FIG. 2444A
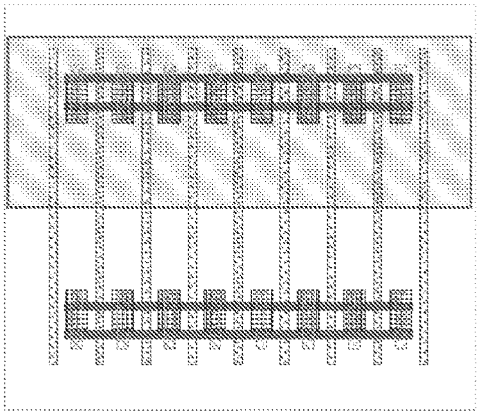
FIG. 2444B
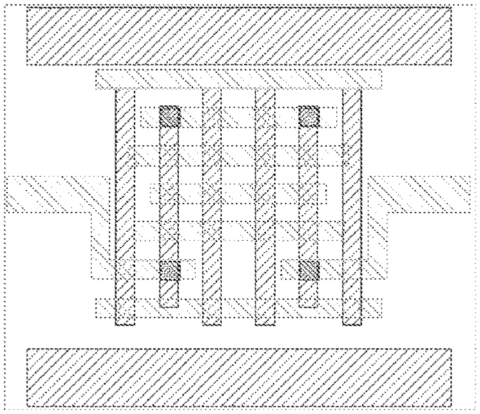
FIG. 2444C

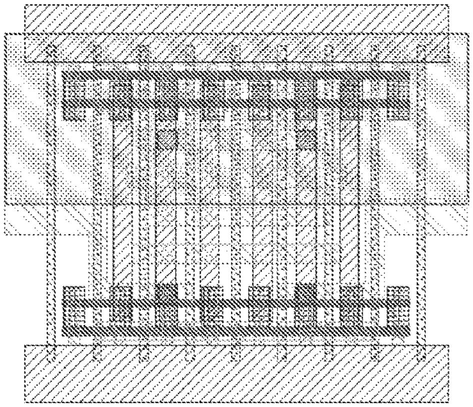
FIG. 2445A
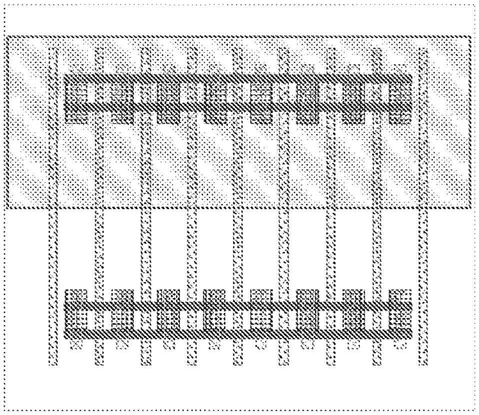
FIG. 2445B
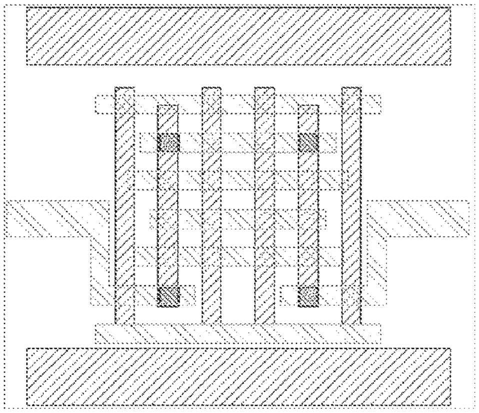
FIG. 2445C

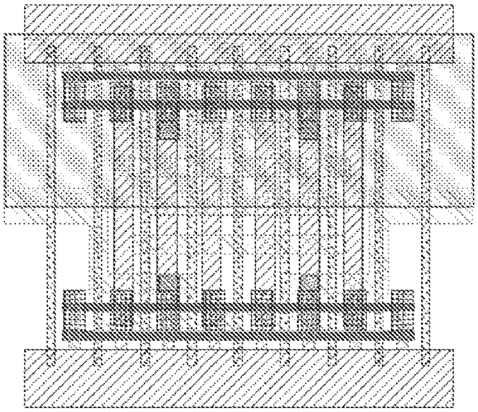
FIG. 2446A
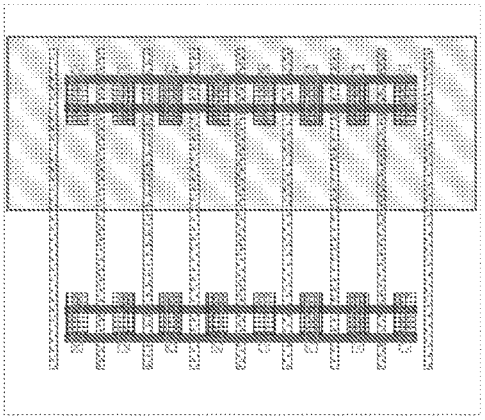
FIG. 2446B
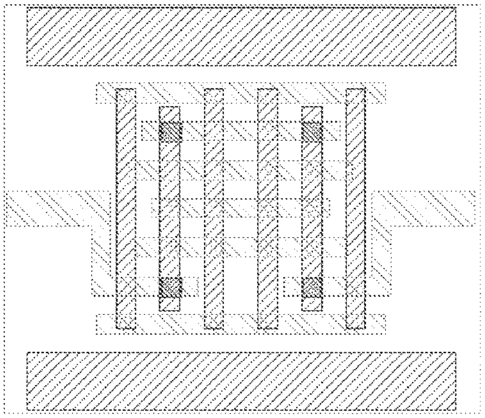
FIG. 2446C
*M* PDF Solutions, Inc.

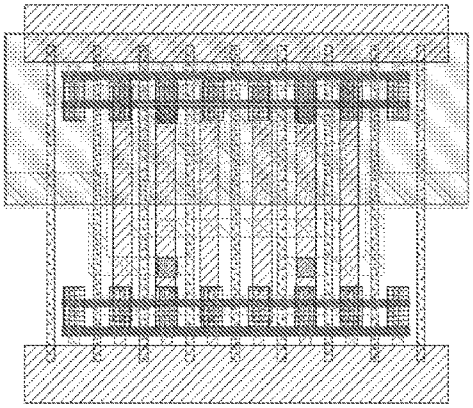
FIG. 2447A
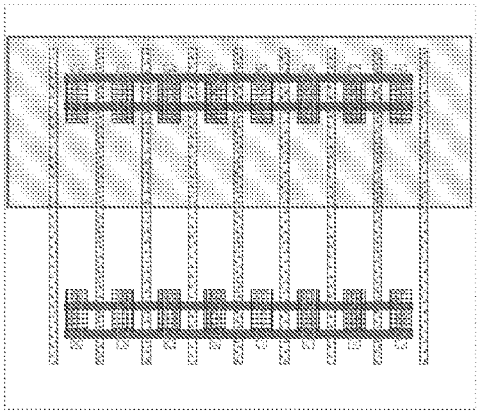
FIG. 2447B
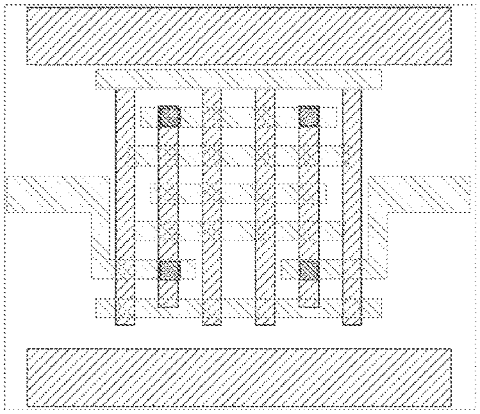
FIG. 2447C

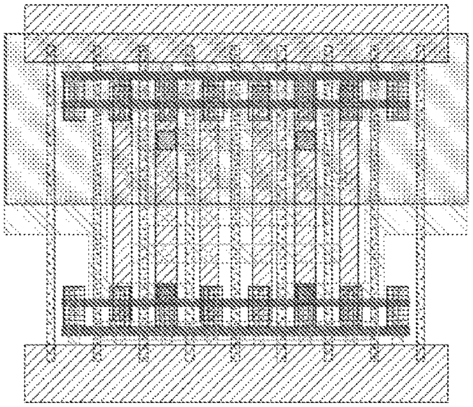
FIG. 2448A
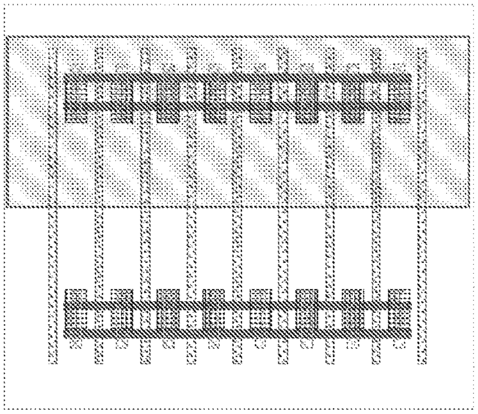
FIG. 2448B
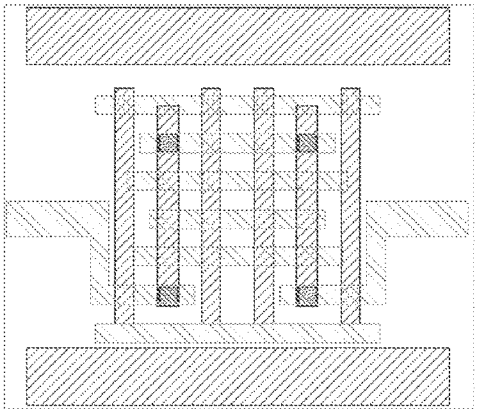
FIG. 2448C
*M* PDF Solutions, Inc.

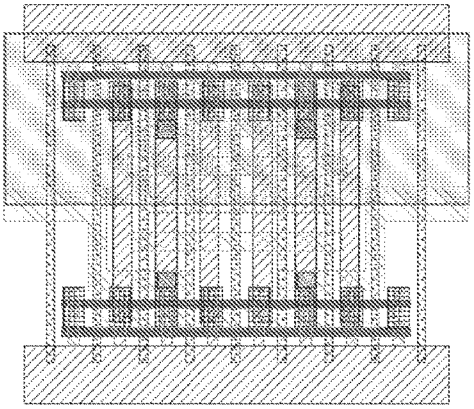
FIG. 2449A
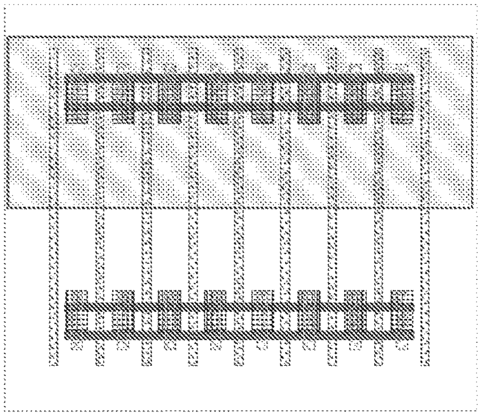
FIG. 2449B
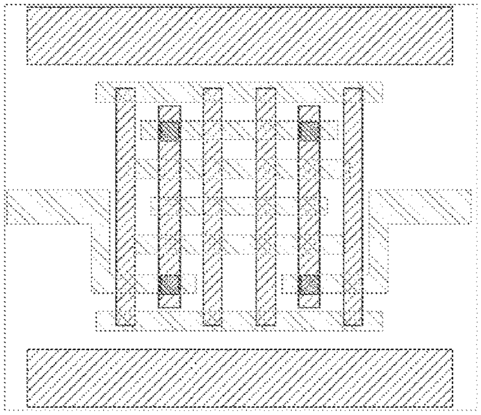
FIG. 2449C

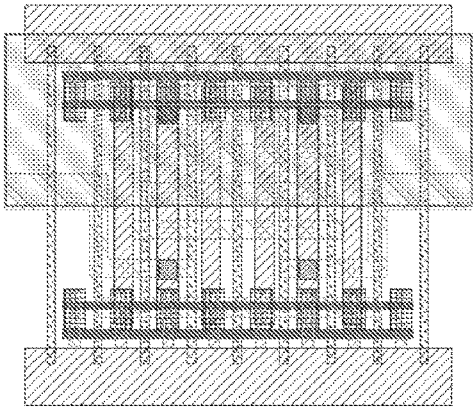
FIG. 2450A
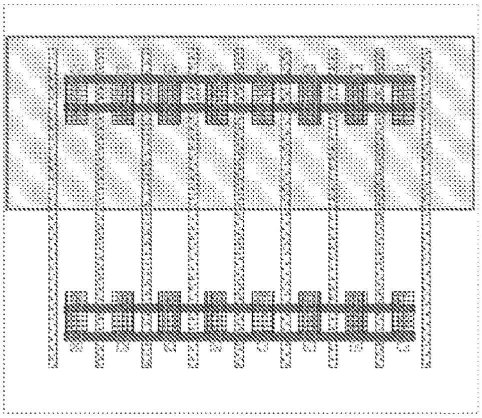
FIG. 2450B
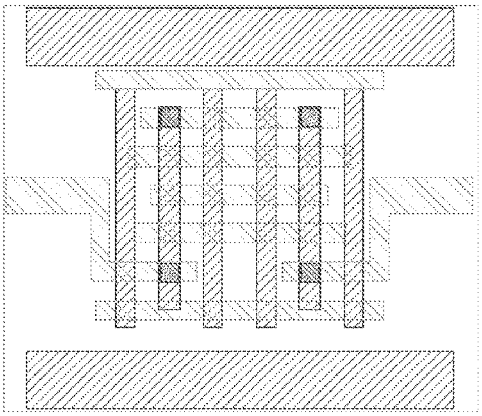
FIG. 2450C

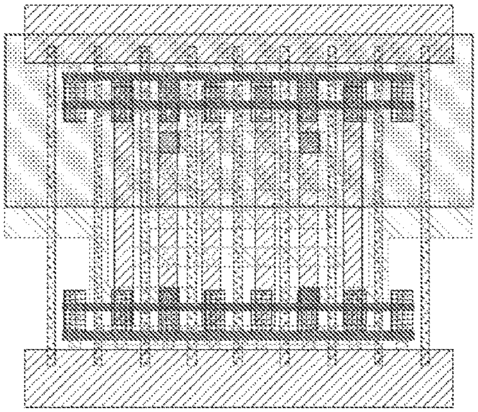
FIG. 2451A
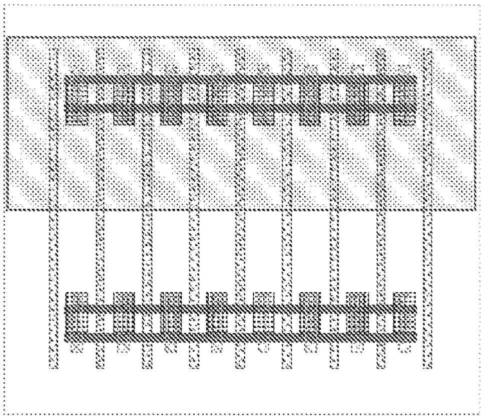
FIG. 2451B
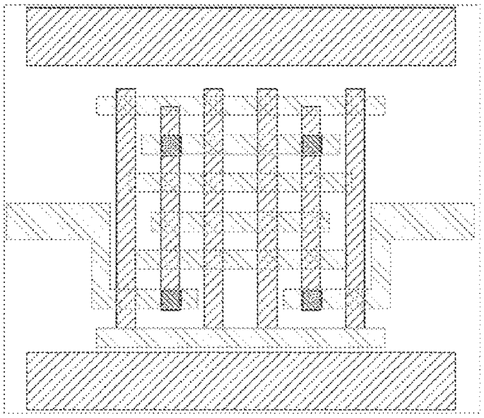
FIG. 2451C

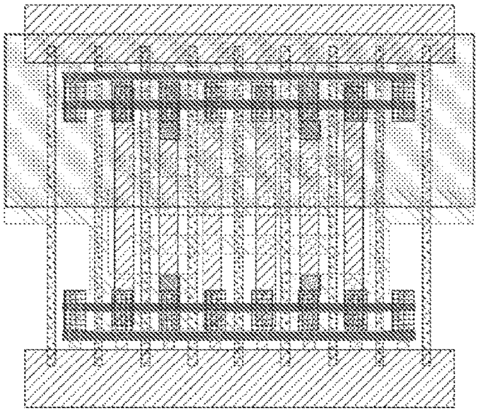
FIG. 2452A
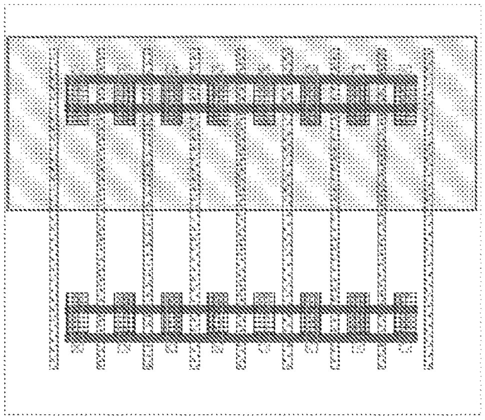
FIG. 2452B
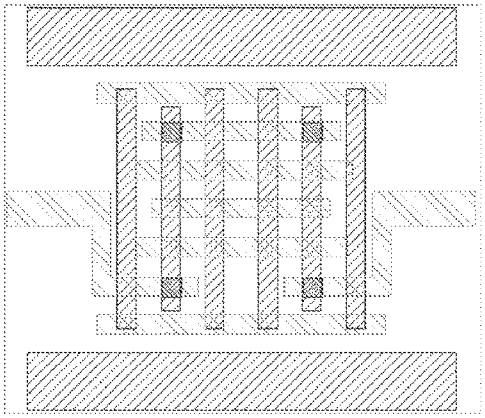
FIG. 2452C

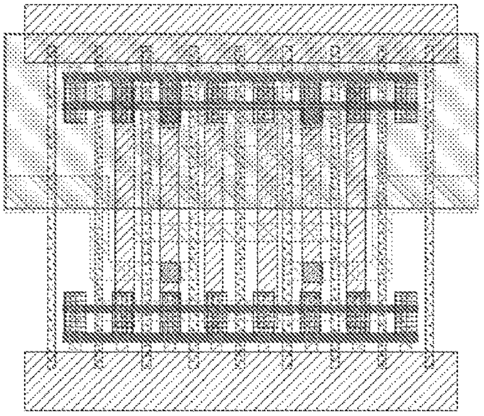
FIG. 2453A
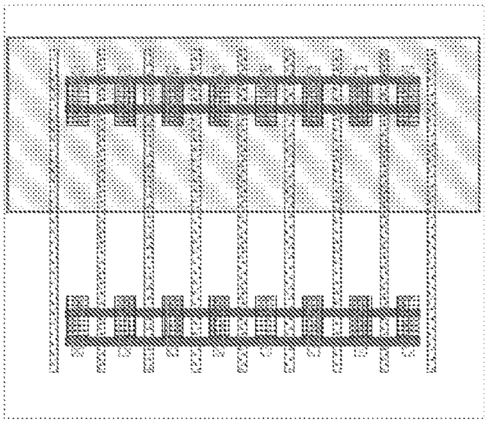
FIG. 2453B
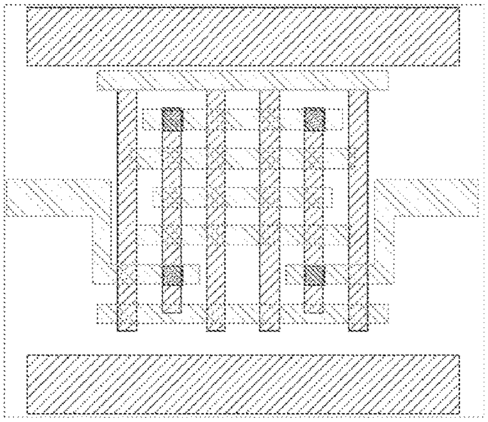
FIG. 2453C

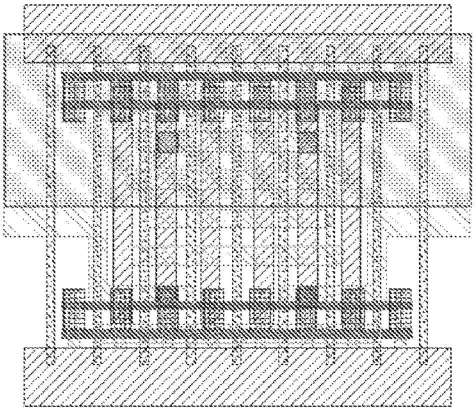
FIG. 2454A
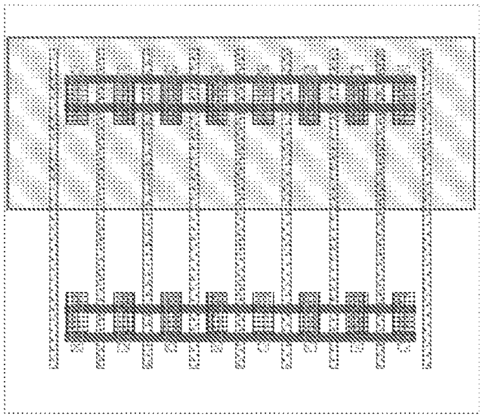
FIG. 2454B
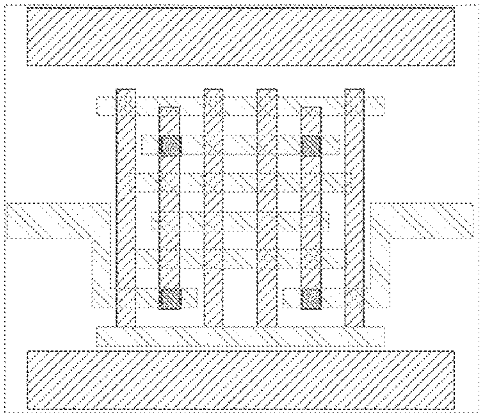
FIG. 2454C

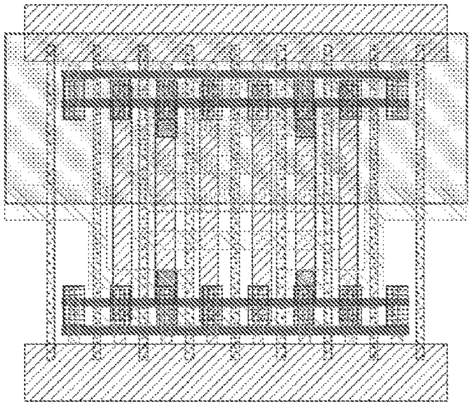
FIG. 2455A
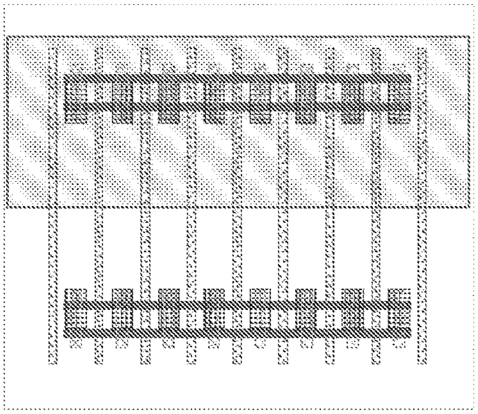
FIG. 2455B
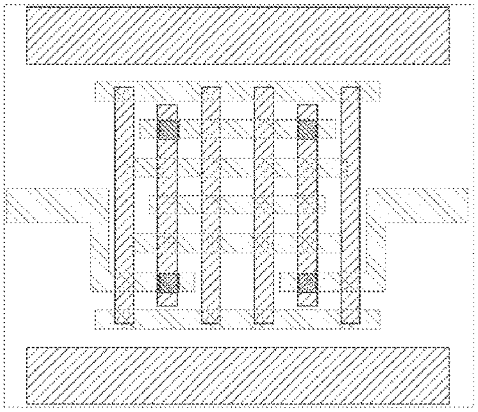
FIG. 2455C

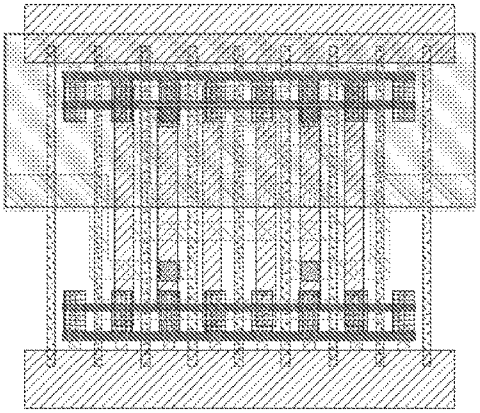
FIG. 2456A
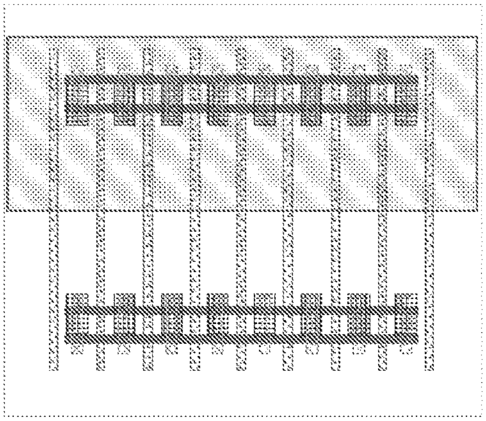
FIG. 2456B
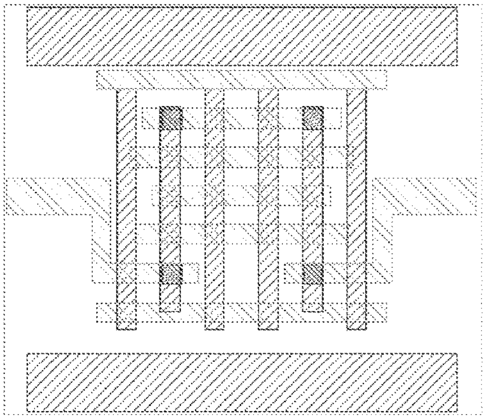
FIG. 2456C

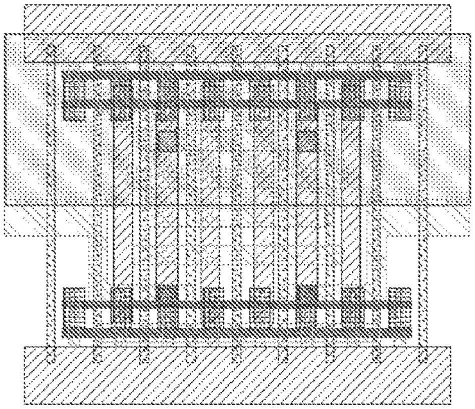
FIG. 2457A
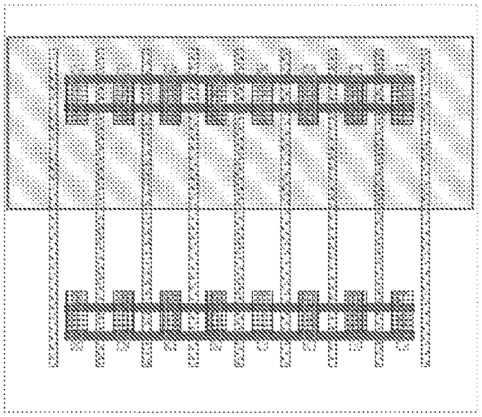
FIG. 2457B
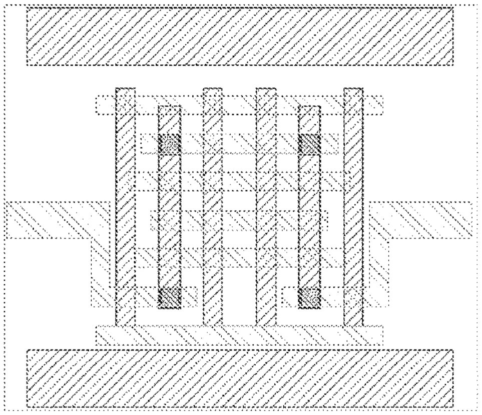
FIG. 2457C

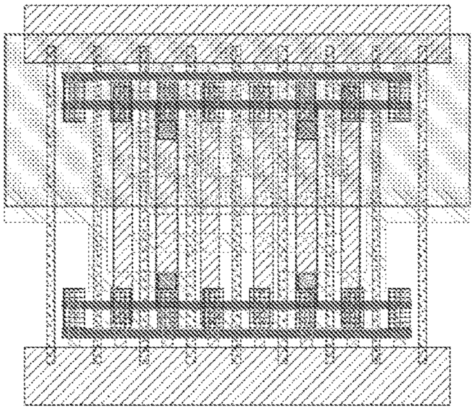
FIG. 2458A
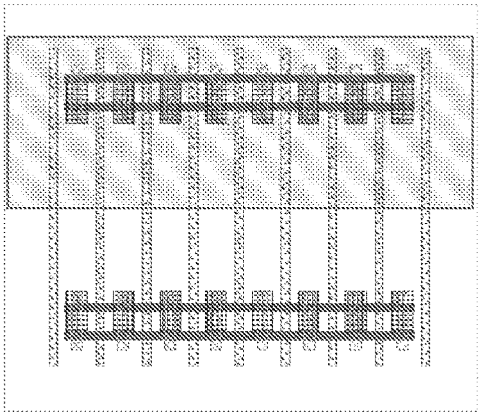
FIG. 2458B
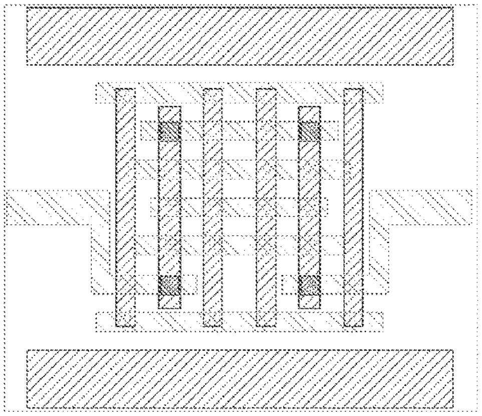
FIG. 2458C

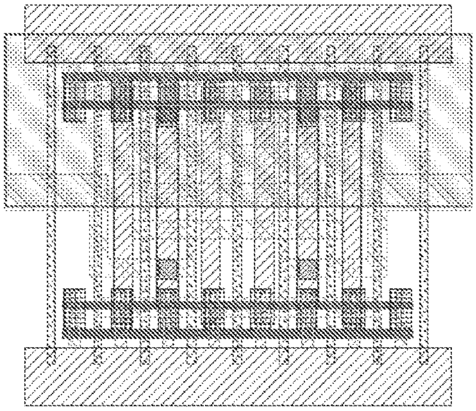
FIG. 2459A
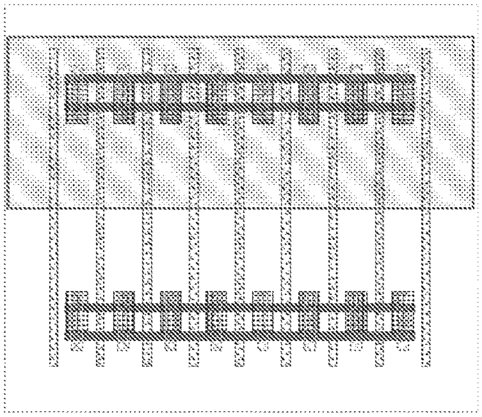
FIG. 2459B
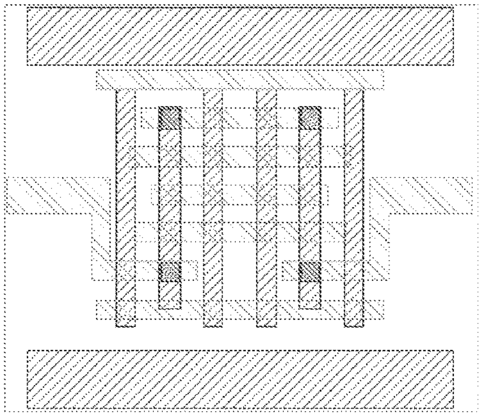
FIG. 2459C
*M* PDF Solutions, Inc.

MESH-STYLE NCEM PADS, AND PROCESS FOR MAKING SEMICONDUCTOR DIES, CHIPS, AND WAFERS USING IN-LINE MEASUREMENTS FROM SUCH PADS

CROSS-REFERENCE TO RELATED APPLICATIONS

This application claims priority from U.S. Pat. Applic. Ser. 62/268,463, entitled "Integrated Circuit Containing DOEs of NCEM-enabled Fill Cells+Process for Making Semiconductor Dies, Chips, and Wafers Using In-Line Measurements Obtained From DOEs of NCEM-enabled Fill Cells," filed Dec. 16, 2015, which '463 application is incorporated by reference herein. This application is also a continuation-in-part of U.S. patent application Ser. No. 14/612,841, filed Feb. 3, 2015, which '841 application is also incorporated by reference herein.

MASK WORK NOTICE

A portion of the disclosure of this patent document (including its incorporated documents) contains material which is subject to mask work protection, *M*, PDF Solutions, Inc. The mask work owner (PDF Solutions, Inc.) has no objection to the facsimile reproduction by anyone of the patent document (including its incorporated documents) or the patent disclosure, as it appears in the Patent and Trademark Office patent file or records, but otherwise reserves all mask work rights whatsoever.

FIELD OF THE INVENTION

This invention relates generally to improved processes for manufacturing semiconductor wafers and chips through use of in-line measurements obtained via non-contact electrical measurements ("NCEM"), to on-chip structures configured to provide useful information via NCEM, and to implementation of NCEM structures in library compatible fill cells.

BACKGROUND OF THE INVENTION

U.S. Pat. No. 5,008,727 ("Standard cell having test pad for probing and semiconductor integrated circuit device containing the standard cells") to Katsura et al., incorporated by reference herein, discloses placement of a testing pad in a standard cell.

U.S. Pat. No. 6,091,249 A ("Method and apparatus for detecting defects in wafers") to Graham et al., incorporated by reference herein, discloses structures and methods for testing certain defects using a non-contact ("NC") technique.

U.S. Pat. No. 6,452,412 B1 ("Drop-in test structure and methodology for characterizing an integrated circuit process flow and topography") to Jarvis et al., incorporated by reference herein, discloses structures and methods for testing certain defects using an NC technique.

U.S. Pat. No. 6,949,765 B2 ("Padless structure design for easy identification of bridging defects in lines by passive voltage contrast") to Song et al., incorporated by reference herein, discloses structures and methods for testing certain defects using an NC technique.

U.S. Pat. No. 7,101,722 B1 ("In-line voltage contrast determination of tunnel oxide weakness in integrated circuit technology development") to Wang et al., incorporated by reference herein, discloses structures and methods for testing certain defects using an NC technique.

U.S. Pat. No. 7,105,436 B2 ("Method for in-line monitoring of via/contact holes etch process based on test structures in semiconductor wafer manufacturing") to Zhao et al., incorporated by reference herein, discloses structures and methods for testing certain defects using an NC technique.

U.S. Pat. No. 7,518,190 B2 ("Grounding front-end-of-line structures on a SOI substrate") to Cote et al., incorporated by reference herein, discloses structures and methods for testing certain defects using an NC technique.

U.S. Pat. No. 7,930,660 B2 ("Measurement structure in a standard cell for controlling process parameters during manufacturing of an integrated circuit"), to Ruderer et al., incorporated by reference herein, describes the use of test structures in fill cells for manufacturing optimization.

U.S. Pat. No. 7,939,348 B2 ("E-beam inspection structure for leakage analysis"), to Seng et al., incorporated by reference herein, discloses structures and methods for testing certain defects using an NC technique.

U.S. Pat. No. 8,039,837 B2 ("In-line voltage contrast detection of PFET silicide encroachment") to Patterson et al., incorporated by reference herein, discloses structures and methods for testing certain defects using an NC technique.

U.S. Pat. No. 8,339,449 B2 ("Defect monitoring in semiconductor device fabrication"), to Fong et al., incorporated by reference herein, discloses structures and methods for testing certain defects using an NC technique.

U.S. Pat. No. 8,399,266 B2 ("Test structure for detection of gap in conductive layer of multilayer gate stack") to Mo et al., incorporated by reference herein, discloses structures and methods for testing certain defects using an NC technique.

U.S. Pat. No. 8,421,009 B2 ("Test structure for charged particle beam inspection and method for defect determination using the same") to Xiao, incorporated by reference herein, discloses structures and methods for testing certain defects using an NC technique.

U.S. Pat. No. 8,575,955 B1 ("Apparatus and method for electrical detection and localization of shorts in metal interconnect lines") to Brozek, incorporated by reference herein, discloses structures and methods for testing certain defects using an NC technique.

U.S. Patent Publication 20090102501 A1 ("Test structures for e-beam testing of systematic and random defects in integrated circuits") to Guldi et al., incorporated by reference herein, discloses structures and methods for testing certain defects using an NC technique.

SUMMARY OF THE INVENTION

The invention generally involves the placement of NC-testable structures, and DOEs (Designs of Experiments) based on such structures, preferably within the "fill cells" typically used in standard cell logic regions. As used in this application, "fill cells" (or "filler cells") refer to cells configured for placement in standard cell rows, but not configured to perform any logical or information storage function(s). Modern, standard-cell layouts commonly use such fill cells to relieve routing congestion. See, e.g., Cong, J., et al. "Optimizing routability in large-scale mixed-size placement," ASP-DAC, 2013; and Menezes, C., et al. "Design of regular layouts to improve predictability," Proceedings of the 6th IEEE International Caribbean Conference on Devices, Circuits and Systems, 2006. See also U.S. Pat. No. 8,504,969 ("Filler Cells for Design Optimization in a Place-and-Route System") to Lin et al., incorporated by reference herein. As used herein "fill cells" may include structures designed to perform ancillary (i.e., not logical or storage) functions, for example, well ties and/or decoupling capacitors.

One NC measurement technique, useful in connection with certain embodiments of the invention, involves measuring or inspecting the surface of a partially processed wafer (in-line) with a scanning electron microscope ("SEM") or other charged particle-based scanning/imaging device. As the measuring/inspecting proceeds, the SEM (or other device) induces charge on all electrically floating elements, whereas any grounded elements remain at zero potential. This voltage contrast becomes visible to the scanning/imaging device as a NCEM.

This NC measurement technique, commonly known as "voltage contrast inspection," has been used in the semiconductor industry for many years, see, e.g., U.S. Pat. No. 6,344,750 B1 ("Voltage contrast method for semiconductor inspection using low voltage particle beam"), and exists in many different flavors—as demonstrated by the dozens of subsequent patents that cite the '750 patent as prior art.

U.S. patent application Ser. No. 14/612,841 ("Opportunistic placement of IC test structures and/or e-beam target pads in areas otherwise used for filler cells, tap cells, decap cells, scribe lines, and/or dummy fill, as well as product IC chips containing same"), filed Feb. 3, 2015, by inventors De et al., incorporated by reference herein, and owned by the assignee of the present application, discloses a number of highly efficient—and herein preferred—methods for obtaining NCEMs from the NCEM-enabled test structures utilized in the present invention. While these '841 methods represent the applicant's preferred NC measurement methods, it is applicant's intent that usage of the terms "NC measurement" or "NCEM" in this application should not be limited to these preferred methods in the absence of specific language (e.g., "selectively targeting . . . ", " . . . fewer than 10 pixels") that indicates an intent to so limit a claim.

In general usage, the term Design of Experiments (DOE) or Experimental Design refers to the design of any information-gathering exercise where variation is present, whether under the full control of the experimenter or not.

Experimental Design is an established field, well known to persons skilled in the art. See NIST/SEMATECH e-Handbook of Statistical Methods, http://www.itl.nist.gov/div898/handbook/, updated Oct. 30, 2013, incorporated by reference herein.

As will be apparent to the skilled reader, the typical DOE herein relates to an experiment involving one or more semiconductor die(s) and/or wafer(s), wherein said one or more die(s) and/or wafer(s) contain multiple instances of a substantially similar test structure, at least some of which vary in terms of one or more layout-related parameters (including, but not limited to, size, spacing, offset, overlap, width, extension, run length, periodicity, density, neighborhood patterning, including underlayers) or process related parameters (including, but not limited to, dose, rate, exposure, processing time, temperature, or any tool-specifiable setting). As the person skilled in the art knows, the selection of specific parameter(s) to vary, the amount/distribution of their variation, and the number and location of test structures that express such variation will be selected based upon the goals of the experiment, the involved process, and the availability of appropriate places (e.g., fill cell locations, tap cell locations, decap cell locations, scribe line areas, etc.) to instantiate the test structures.

Preferred embodiments of the invention utilize DOEs constructed from NCEM-enabled fill cells. In accordance with certain preferred embodiments of the invention, NCEM-enabled fill cells all have some common elements (e.g., height, supply rail configuration, and gate patterning that is consistent with standard cells in the library), then vary according to the measurement type (e.g., short, open, leakage, or resistance), layer(s) involved, and/or structure(s) to be evaluated/tested. Such NCEM-enabled fill cells also generally include a pad, configured to accelerate targeted NC evaluation by, for example, determining an associated NCEM from a small number of enlarged pixels (e.g., 10 or fewer), or without creating any image at all. Such pads can be formed from a variety of low-resistance materials and configured in a variety of shapes.

In certain preferred embodiments, such NCEM-enabled fill cells may additionally include two or more mask-patterned features that define a rectangular test area, such test area being characterized by two parameters (e.g., X/Y or r/θ dimensions). Additionally, for such NCEM-enabled fill cells, an expanded test area surrounds the cell's test area, the expanded test area being defined by a predetermined expansion of each boundary of the test area, or by predetermined proportionate expansion of the test area's area. Alternatively, in the case of cells designed to measure or characterize inter-layer effects, such test areas may be characterized as "test volumes," with one or more additional parameter(s) characterizing the layers of the defining, mask-patterned features.

For fill cells designed to measure, detect, or characterize electrical short circuit behavior (so-called, "short-configured, NCEM-enabled fill cells"), the test area may represent an intended gap between two pattern-defined features that, in the absence of a manufacturing anomaly, would be electrically isolated. Alternatively, in such short-configured, NCEM-enabled fill cells, the test area may represent an overlap between two pattern-defined features that, in the absence of a manufacturing anomaly, would be electrically isolated. A single short-configured, NCEM-enabled fill cell may contain one or multiple test areas. In the case of a NCEM-enabled fill cell with multiple test areas, each of the cell's test areas is preferably wired in parallel, and each of the cell's test areas (and preferably each of its extended test areas, too) is identically or nearly identically configured.

Fill cells designed to measure, detect, or characterize electrical leakage behavior (so-called, "leakage-configured, NCEM-enabled fill cells") typically resemble short-configured cells. Like the short-configured cells, such leakage-configured cells may include a test area that represents an intended gap between two pattern-defined features that, in ideality, should be electrically isolated, but in reality, inevitably exhibit some amount of leakage. Alternatively, in such leakage-configured, NCEM-enabled fill cells, the test area may represent an overlap between two pattern-defined features that, in ideality, would be electrically isolated, but in reality, inevitably exhibit some amount of leakage. A single leakage-configured, NCEM-enabled fill cell may contain one, but preferably contains multiple test areas. In the case of a cell with multiple test areas, each of the cell's test areas is preferably wired in parallel, and each of the cell's test areas (and preferably each of its extended test areas, too) is identically or nearly identically configured.

For fill cells designed to measure, detect, or characterize electrical open circuit behavior (so-called, "open-configured, NCEM-enabled fill cells"), the test area typically represents an intended overlap, or extension, between two pattern-defined features that, in the absence of a manufacturing anomaly, would be electrically connected. (It may also represent a single-layer pattern, such as a snake.) A single open-configured, NCEM-enabled fill cell may contain one or multiple test areas. In the case of multiple test areas, each of the cell's test areas is preferably connected in series, and each of the cell's test areas (and preferably each of the extended test areas, too) is identically or nearly identically configured.

Fill cells designed to measure, detect, or characterize electrical resistance behavior (so-called, "resistance-configured, NCEM-enabled fill cells") typically resemble open-configured cells. Like the open-configured cells, such resistance-configured cells may include a test area that represents an intended overlap, or extension, between two pattern-defined features that, in ideality, would be connected by a nearly zero-resistance path, but in reality, inevitably produce a measurable level of resistance. (Such test area may also represent a single-layer pattern, such as a snake.) A single resistance-configured, NCEM-enabled fill cell may contain one, but preferably contains multiple test areas. In the case of multiple test areas, each of the cell's test areas is preferably connected in series, and each of the cell's test areas (and preferably each of the extended test areas, too) is identically or nearly identically configured.

DOEs, in accordance with such preferred embodiments, comprise a collection of substantially similarly configured NCEM-enabled fill cells, in a plurality of variants. Within a given DOE, such similarly configured fill cells would typically all be configured to measure, detect, or characterize the same behavior (e.g., gate-to-gate, or control-element-to-control-element, shorts, for example), in the same structural configuration (e.g., tip-to-tip, as per FIG. 14, for example). In single-parameter DOEs, the differences between variants may be limited to differences in the size, shape, or position of one of the features that defines the cells' test area. In multi-parameter DOEs, the differences between variants may involve differences in two or more such parameters. And in more complex DOEs, the differences may involve other non-incremental changes (e.g., the presence or absence of certain features, or changes in nearby or underlying patterning), either alone or in combination with additional to single- or multi-parameter variations.

In the case of DOEs involving complex changes to nearby patterning, changes that lie within an expanded test area (an area that encompasses a predetermined expansion of the test area by, for example 50-200%, or more) and involve either the test area-defining layer(s) or any layers that overlap or lie immediately above or below the test area-defining layers, are preferably limited in number. Limiting the number of such changes to fewer than three, five, ten, twenty, or thirty "background pattern variants" facilitates analysis of data that the experiment produces.

Another way to characterize the degree of relevant patterning variation between DOE variants—in certain embodiments of the invention—involves the concept of a pattern similarity ratio ("PSR"), whose computation is pictorially depicted in FIGS. 37-40 (and described later herein). In accordance with this aspect of the invention, for each variant in a DOE, there should exist another variant in the DOE that has a PSR of at least 0.90 (or preferably 0.95, or more preferably 0.97) for every test-area defining layer, and at least 0.75 (or preferably 0.85, or more preferably 0.90) for each layer that lies immediately below any of the test-area defining layer(s), when the expanded test areas are defined to be at least 150-200% of the corresponding test area sizes.

Another aspect of DOEs, in accordance with the preferred embodiments, is that they include multiple instances (e.g., 3, 5, 10, 20, 500, 100, 200, or 500+) of each NCEM-enabled fill cell variant. Furthermore, such variants are preferably distributed, either regularly or irregularly, throughout the space available for instantiation of fill cells.

Accordingly, generally speaking, and without intending to be limiting, one aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the integrated circuit includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the first DOE is configured to render a first selected manufacturing failure observable as an abnormal pad-to-ground leakage or conductance, detected by VC inspection of the pad; and, wherein the similarly-configured, NCEM-enabled fill cells of the first DOE include a plurality of variants, where the variants differ in terms of their respective probability of presenting an abnormal pad-to-ground leakage or resistance as a result of the first selected manufacturing failure. Such ICs may further include: a second DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the second DOE is configured to render a second selected manufacturing failure observable as an abnormal pad-to-ground leakage or conductance, detected by VC inspection of the pad, and wherein the second selected manufacturing failure is different than the first selected manufacturing failure; and, wherein the similarly-configured, NCEM-enabled fill cells of the second DOE include a plurality of variants, where the variants differ in terms of their respective probability of presenting an abnormal pad-to-ground leakage or conductance as a result of the second selected manufacturing failure. The first selected manufacturing failure may involve short or leakage defects that present as abnormally high pad-to-ground conductance or leakage, and the second selected manufacturing failure may involve open or resistance defects that present as abnormally low pad-to-ground conductance or abnormally high pad-to-ground resistance. Both the first and second selected manufacturing failures may involve layers in a connector stack region of the IC. Such ICs may further include: a third DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured NCEM-enabled fill cells in the third DOE is configured to render a third selected manufacturing failure observable as an abnormal pad-to-ground leakage, conductance or resistance, detected by VC inspection of the pad, and wherein the third selected manufacturing failure is different than the first selected manufacturing failure, and is different than the second selected manufacturing failure; and, wherein the similarly-configured NCEM-enabled fill cells of the third DOE include a plurality of variants, where the variants differ in terms of their respective probability of presenting an abnormal pad-to-ground leakage, conductance or resistance as a result of the third selected manufacturing failure. Each of the first, second, and third DOEs preferably include NCEM-enabled fill cells in at least three, five, seven, or ten variants. The NCEM-enabled fill cells of the first, second, and third DOEs are preferably irregularly distributed within the standard cell area of the IC. Each variant may differ from the other(s) only in the position, size, or shape of its first or second mask-patterned feature, or only by a single dimensional parameter that characterizes their respective test areas.

Again, generally speaking, and without intending to be limiting, another aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the IC includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of first and second distinct, mask-patterned features, the test area characterized by two dimensional parameters, the test area configured to provide electrical isolation between the first and second mask-patterned features in the absence of a first selected manufacturing failure; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the first DOE is configured to render a first selected manufacturing failure observable as an abnormally high pad-to-ground conductance or leakage, detected by VC inspection of the pad; and, wherein the similarly-configured, NCEM-enabled fill cells of the first DOE include a plurality of variants, where the variants differ in terms of their respective probability of presenting an abnormally high pad-to-ground conductance or leakage as a result of the first selected manufacturing failure. In each of the NCEM-enabled fill cells of the first DOE, the first and/or second distinct, mask-patterned features may each represent either a control element, or a portion thereof, and/or a portion of a control element connector or a substrate connector, and/or a portion of a control element jumper, substrate jumper, or interconnect jumper. In each of the NCEM-enabled fill cells of the first and/or second DOE(s), the first and second distinct, mask-patterned features may appear in a tip-to-tip configuration, a tip-to-side configuration, a side-to-side configuration, a diagonal configuration, or an inter-layer overlap configuration.

Again, generally speaking, and without intending to be limiting, another aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the IC includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in one or more conductive layer(s), the pad being at least two times larger, in at least one dimension, than a minimum size permitted by design rules; a rectangular test area defined by selected boundaries of a plurality of mask-patterned features, the test area characterized by two dimensional parameters, the plurality of mask-patterned features including at least first and second features that are electrically connected in the absence of a first manufacturing failure; a first conductive pathway that electrically connects the first mask-patterned feature to the pad; and, a second conductive pathway that electrically connects the second mask-patterned feature to a permanently or virtually grounded structure; wherein each of the similarly-configured NCEM-enabled fill cells in the first DOE is configured to render a first selected manufacturing failure observable as an abnormally high pad-to-ground conductance or leakage, detected by VC inspection of the pad; wherein the similarly-configured NCEM-enabled fill cells of the first DOE include a plurality of variants, where the variants differ in terms of their respective probability of presenting an abnormally high pad-to-ground conductance or leakage as a result of the first selected manufacturing failure; and, wherein the similarly-configured NCEM-enabled fill cells of the first DOE are selected from the list consisting of: source/drain (AA)-tip-to-tip-short-configured, NCEM-enabled fill cells; source/drain contact (AACNT)-tip-to-tip-short-configured, NCEM-enabled fill cells; AACNT-AA-tip-to-tip-short-configured, NCEM-enabled fill cells; source/drain silicide (TS)-tip-to-tip-short-configured, NCEM-enabled fill cells; gate (GATE)-tip-to-tip-short-configured, NCEM-enabled fill cells; gate contact (GATECNT)-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; first wiring layer (M1)-tip-to-tip-short-configured, NCEM-enabled fill cells; via to interconnect stack (V0)-tip-to-tip-short-configured, NCEM-enabled fill cells; M1-V0-tip-to-tip-short-configured, NCEM-enabled fill cells; first interconnect via layer (V1)-M1-tip-to-tip-short-configured, NCEM-enabled fill cells; V1-tip-to-tip-short-configured, NCEM-enabled fill cells; second wiring layer (M2)-tip-to-tip-short-configured, NCEM-enabled fill cells; M2-V1-tip-to-tip-short-configured, NCEM-enabled fill cells; second interconnect via layer (V2)-M2-tip-to-tip-short-configured, NCEM-enabled fill cells; third wiring layer (M3)-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-side-short-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AACNT-corner-short-configured, NCEM-enabled fill cells; M1-corner-short-configured, NCEM-enabled fill cells; V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-shortconfigured, NCEM-enabled fill cells; M3-V2-corner-short-configured, NCEM-enabled fill cells; GATE-AA-interlayer-overlap-short-configured, NCEM-enabled fill cells; GATE-TS-interlayer-overlap-short-configured, NCEM-enabled fill cells; GATE-AACNT-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V0-merged-via-short-configured, NCEM-enabled fill cells; V1-merged-via-short-configured, NCEM-enabled fill cells; and, V2-merged-via-short-configured, NCEM-enabled fill cells; a second DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the second DOE is configured to render a second selected manufacturing failure observable as an abnormally low pad-to-ground conductance or abnormally high pad-to-ground resistance, detected by VC inspection of the pad; and, wherein the similarly-configured, NCEM-enabled fill cells of the second DOE include a plurality of variants, where the variants differ in terms of their respective probability of presenting an abnormally low pad-to-ground conductance or abnormally high pad-to-ground resistance as a result of the second selected manufacturing failure; and, wherein the similarly-configured NCEM-enabled fill cells of the second DOE are selected from the list consisting of: AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells; GATECNT-snake-open-configured, NCEM-enabled fill cells; V0-snake-open-configured, NCEM-enabled fill cells; M1-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-M1-via-open-configured, NCEM-enabled fill cells; V1-M2-via-open-configured, NCEM-enabled fill cells; M1-GATECNT-via-open-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; V2-M2-merged-via-open-configured, NCEM-enabled fill cells.

Again, generally speaking, and without intending to be limiting, another aspect of the invention relates methods for making ICs that include, for example: (a) performing initial processing steps on a semiconductor wafer, the initial processing steps including: patterning a standard cell area that includes a mix of at least one thousand logic cells and fill cells of different widths and uniform heights, placed into at least twenty adjacent rows, with at least twenty cells placed side-by-side in each row; and, patterning a first DOE by instantiating a plurality of similarly-configured, NCEM-enabled fill cells in at least two variants, the NCEM-enabled fill cells configured for compatibility with logic cells in the standard cell area, each of the cells in the first DOE configured to enable evaluation of a first manufacturing failure by voltage contrast examination of a NCEM of a pad contained in the cell, the variants exhibiting different NCEM sensitivity to the first manufacturing failure; (b) determining a presence or absence of the first manufacturing failure by: performing a voltage contrast examination of NCEM-enabled fill cells in the first DOE; and, determining whether NCEMs of pads contained in the NCEM-enabled fill cells of the first DOE represent instance(s) of the first manufacturing failure and, if so, determining whether different cell variants exhibit a different prevalence of the first manufacturing failure; and, (c) based, at least in part, on results from step (b), selectively performing additional processing, metrology or inspection steps on the wafer, and/or on other wafer(s) currently being manufactured using a process flow(s) relevant to the observed first manufacturing failure. Step (a) may further involve: patterning a second DOE by instantiating a plurality of similarly-configured NCEM-enabled fill cells in at least two variants, the NCEM-enabled fill cells configured for compatibility with logic cells in the standard cell area and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and wherein step (b) further comprises: performing a voltage contrast examination of NCEM-enabled fill cells in the second DOE; and, determining whether NCEMs of pads contained in the NCEM-enabled fill cells of the second DOE represent instance(s) of the second manufacturing failure and, if so, determining whether different cell variants exhibit a different prevalence of the second manufacturing failure. Step (a) may further involve: patterning a third DOE by instantiating a plurality of similarly-configured NCEM-enabled fill cells in at least two variants, the NCEM-enabled fill cells configured for compatibility with logic cells in the standard cell area and fill cells in the first and second DOEs, each of the cells in the third DOE configured to enable evaluation of a third manufacturing failure, different from the first and second manufacturing failures, by voltage contrast examination of a NCEM of a pad contained in the cell, the variants exhibiting different NCEM sensitivity to the third manufacturing failure; and wherein step (b) further comprises: performing a voltage contrast examination of NCEM-enabled fill cells in the third DOE; and, determining whether NCEMs of pads contained in the NCEM-enabled fill cells of the third DOE represent instance(s) of the third manufacturing failure and, if so, determining whether different cell variants exhibit a different prevalence of the third manufacturing failure. At least one of the first, second, or third manufacturing failures preferably involves unintended shorts or leakages, and at least one of the first, second, or third manufacturing failures preferably involves unintended opens or excessive resistances. Instantiating the NCEM-enabled fill cells preferably comprises distributing the cells irregularly within the standard cell area. Within each of the DOEs, each variant may differ from the other(s) only in the position, size, or shape of a single mask-patterned feature. At least one of the first, second, or third manufacturing failures may involve unintended shorts between structures in a tip-to-tip configuration, or unintended shorts between structures in a tip-to-side configuration, or unintended shorts between structures in a side-to-side configuration, or unintended shorts between structures in a diagonal configuration, or unintended shorts between structures in an interlayer overlap configuration, or unintended interlayer shorts or leakages between structures in a corner configuration, unintended opens in snake-shaped structures, unintended opens in stitched structures, unintended opens in via-connected structures. Each of the first, second, and third DOEs preferably includes NCEM-enabled fill cells in at least three, five, seven, 11, 21, or more variants. Each of the first, second, and third DOEs may consist of cells selected from the list of: AA-tip-to-tip-short-configured, NCEM-enabled fill cells; AACNT-tip-to-tip-short-configured, NCEM-enabled fill cells; AACNT-AA-tip-to-tip-short-configured, NCEM-enabled fill cells; TS-tip-to-tip-short-configured, NCEM-enabled fill cells; GATE-tip-to-tip-short-configured, NCEM-enabled fill cells; GATECNT-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; M1-tip-to-tip-short-configured, NCEM-enabled fill cells; V0-tip-to-tip-short-configured, NCEM-enabled fill cells; M1-V0-tip-to-tip-short-configured, NCEM-enabled fill cells; V1-M1-tip-to-tip-short-configured, NCEM-enabled fill cells; V1-tip-to-tip-short-configured, NCEM-enabled fill cells; M2-tip-to-tip-short-configured, NCEM-enabled fill cells; M2-V1-tip-to-tip-short-configured, NCEM-enabled fill cells; V2-M2-tip-to-tip-short-configured, NCEM-enabled fill cells; M3-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-side-short-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AACNT-corner-short-configured, NCEM-enabled fill cells; M1-corner-short-configured, NCEM-enabled fill cells; V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-short-configured, NCEM-enabled fill cells; M3-V2-corner-short-configured, NCEM-enabled fill cells; GATE-AA-interlayer-overlap-short-configured, NCEM-enabled fill cells; GATE-AACNT-interlayer-overlap-short-configured, NCEM-enabled fill cells; GATE-TS-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V0-merged-via-short-configured, NCEM-enabled fill cells; V1-merged-via-short-configured, NCEM-enabled fill cells; V2-merged-via-short-configured, NCEM-enabled fill cells; AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells; GATECNT-snake-open-configured, NCEM-enabled fill cells; V0-snake-open-configured, NCEM-enabled fill cells; M1-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-M1-via-open-configured, NCEM-enabled fill cells; V1-M2-via-open-configured, NCEM-enabled fill cells; M1-GATECNT-via-open-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; V2-M2-merged-via-open-configured, NCEM-enabled fill cells.

Again, generally speaking, and without intending to be limiting, another aspect of the invention relates to methods for making ICs that include, for example: (a) performing initial processing steps on a first semiconductor wafer, the initial processing steps including, at least: patterning a first DOE by instantiating a plurality of similarly-configured NCEM-enabled fill cells in at least two variants, the NCEM-enabled fill cells configured for compatibility with logic cells in the standard cell library, each of the cells in the first DOE configured to enable evaluation of a first manufacturing failure by voltage contrast examination of a NCEM of a pad contained in the cell, the variants exhibiting different NCEM sensitivity to the first manufacturing failure; patterning a second DOE by instantiating a plurality of similarly-configured NCEM-enabled fill cells in at least two variants, the NCEM-enabled fill cells configured for compatibility with logic cells in the standard cell library and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and, patterning a third DOE by instantiating a plurality of similarly-configured NCEM-enabled fill cells in at least two variants, the NCEM-enabled fill cells configured for compatibility with logic cells in the standard cell library and fill cells in the first and second DOEs, each of the cells in the third DOE configured to enable evaluation of a third manufacturing failure, different from the first and second manufacturing failures, by voltage contrast examination of a NCEM of a pad contained in the cell, the variants exhibiting different NCEM sensitivity to the third manufacturing failure; and, (b) determining a presence or absence of the first, second, and third manufacturing failures by: performing a voltage contrast examination of NCEM-enabled fill cells in the first DOE; determining whether NCEMs of pads contained in the NCEM-enabled fill cells of the first DOE represent instance(s) of the first manufacturing failure and, if so, determining whether different cell variants exhibit a different prevalence of the first manufacturing failure; performing a voltage contrast examination of NCEM-enabled fill cells in the second DOE; determining whether NCEMs of pads contained in the NCEM-enabled fill cells of the second DOE represent instance(s) of the second manufacturing failure and, if so, determining whether different cell variants exhibit a different prevalence of the second manufacturing failure; performing a voltage contrast examination of NCEM-enabled fill cells in the third DOE; and, determining whether NCEMs of pads contained in the NCEM-enabled fill cells of the third DOE represent instance(s) of the third manufacturing failure and, if so, determining whether different cell variants exhibit a different prevalence of the third manufacturing failure; and, (c) based, at least in part, on results from step (b), fabricating product masks that include: a standard cell area that includes a mix of at least one thousand logic cells, from the standard cell library, and fill cells of different widths and uniform heights, placed into at least twenty adjacent rows, with at least twenty cells placed side-by-side in each row; and, a fourth DOE that includes a plurality of similarly-configured NCEM-enabled fill cells in at least two variants, the NCEM-enabled fill cells configured for compatibility with logic cells in the standard cell area, each of the cells in the fourth DOE configured to enable evaluation of the first manufacturing failure by voltage contrast examination of a NCEM of a pad contained in the cell, the variants exhibiting different NCEM sensitivity to the first manufacturing failure; and, the product masks not including any DOEs configured to enable evaluation of the second or third manufacturing failures; and, (d) using the product masks, performing initial processing steps on a product wafer, the initial processing steps including: patterning the standard cell area; and, patterning the fourth DOE; (e) determining a presence or absence of the first manufacturing failure on the product wafer by: performing a voltage contrast examination of NCEM-enabled fill cells in the fourth DOE; and, determining whether NCEMs of pads contained in the NCEM-enabled fill cells of the fourth DOE represent instance(s) of the first manufacturing failure and, if so, determining whether different cell variants exhibit a different prevalence of the first manufacturing failure; and, (f) based, at least in part, on results from step (e), selectively performing additional processing, metrology or inspection steps on the product wafer, and/or on other product wafer(s) currently being manufactured using a process flow(s) relevant to the observed first manufacturing failure.

Again, generally speaking, and without intending to be limiting, another aspect of the invention relates to methods for making ICs that include, for example: (a) performing initial processing steps on an initial product wafer, the initial processing steps including, at least: patterning a standard cell area that includes a mix of at least one thousand logic cells and fill cells of different widths and uniform heights, placed into at least twenty adjacent rows, with at least twenty cells placed side-by-side in each row; and, patterning, within the standard cell area, a first DOE by instantiating a plurality of similarly-configured NCEM-enabled fill cells in at least two variants, the NCEM-enabled fill cells configured for compatibility with logic cells in the standard cell area, each of the cells in the first DOE configured to enable evaluation of a first manufacturing failure by voltage contrast examination of a NCEM of a pad contained in the cell, the variants exhibiting different NCEM sensitivity to the first manufacturing failure; patterning a second DOE by instantiating a plurality of similarly-configured NCEM-enabled fill cells in at least two variants, the NCEM-enabled fill cells configured for compatibility with logic cells in the standard cell area and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and, (b) determining a presence or absence of the first and second manufacturing failures on the initial product wafer by: performing a voltage contrast examination of NCEM-enabled fill cells in the first DOE; determining whether NCEMs of pads contained in the NCEM-enabled fill cells of the first DOE represent instance(s) of the first manufacturing failure and, if so, determining whether different cell variants exhibit a different prevalence of the first manufacturing failure; performing a voltage contrast examination of NCEM-enabled fill cells in the second DOE; and, determining whether NCEMs of pads contained in the NCEM-enabled fill cells of the second DOE represent instance(s) of the second manufacturing failure and, if so, determining whether different cell variants exhibit a different prevalence of the second manufacturing failure; and, (c)

based, at least in part, on results from step (b), fabricating final product masks that include: a standard cell area that includes a mix of at least one thousand logic cells and fill cells of different widths and uniform heights, placed into at least twenty adjacent rows, with at least twenty cells placed side-by-side in each row; and, a third DOE that includes a plurality of similarly-configured NCEM-enabled fill cells in at least two variants, the NCEM-enabled fill cells configured for compatibility with logic cells in the standard cell area, each of the cells in the third DOE configured to enable evaluation of the first manufacturing failure by voltage contrast examination of a NCEM of a pad contained in the cell, the variants exhibiting different NCEM sensitivity to the first manufacturing failure; the final product masks not including any DOEs configured to enable evaluation of the second manufacturing failure; and, (d) using the final product masks, performing initial processing steps on a final product wafer, the initial processing steps including: patterning the standard cell area; and, patterning the third DOE; and, (e) determining a presence or absence of the first manufacturing failure on the final product wafer by: performing a voltage contrast examination of NCEM-enabled fill cells in the third DOE; and, determining whether NCEMs of pads contained in the NCEM-enabled fill cells of the third DOE represent instance(s) of the first manufacturing failure and, if so, determining whether different cell variants exhibit a different prevalence of the first manufacturing failure; and, (f) based, at least in part, on results from step (e), selectively performing additional processing, metrology or inspection steps on the final product wafer, and/or on other product wafer(s) currently being manufactured using a process flow(s) relevant to the observed first manufacturing failure.

Still further aspects of the invention relate to wafers, chips, and processes for making them that include/utilize DOEs based on means/steps for enabling NC detection of tip-to-tip shorts, including but not limited to:

- means/steps for enabling NC detection of AA tip-to-tip shorts [see FIGS. 10-11, 14-15, 41, 43, and 1298-1326 for corresponding §112(f) structure/acts];
- means/steps for enabling NC detection of AACNT tip-to-tip shorts [see FIGS. 10-11, 14-15, 41, 43, and 1327-1405 for corresponding §112(f) structure/acts];
- means/steps for enabling NC detection of TS tip-to-tip shorts [see FIGS. 10-11, 14-15, 41, and 43 for corresponding §112(f) structure/acts];
- means/steps for enabling NC detection of AACNT-AA tip-to-tip shorts [see FIGS. 10-11, 14-15, 41, and 43 for corresponding §112(f) structure/acts];
- means/steps for enabling NC detection of GATE tip-to-tip shorts [see FIGS. 10-11, 14-15, 41, 43, and 1413-1461 for corresponding §112(f) structure/acts];
- means/steps for enabling NC detection of GATECNT-GATE tip-to-tip shorts [see FIGS. 10-11, 14-15, 41, and 43 for corresponding §112(f) structure/acts];
- means/steps for enabling NC detection of GATECNT tip-to-tip shorts [see FIGS. 10-11, 14-15, 41, 43, and 1462-1548 for corresponding §112(f) structure/acts];
- means/steps for enabling NC detection of GATECNT-AACNT tip-to-tip shorts [see FIGS. 10-11, 14-15, 41, and 43 for corresponding §112(f) structure/acts];
- means/steps for enabling NC detection of M1 tip-to-tip shorts [see FIGS. 10-11, 14-15, 41, 43, and 1549-1556 for corresponding §112(f) structure/acts];
- means/steps for enabling NC detection of V0 tip-to-tip shorts [see FIGS. 10-11, 14-15, 41, and 43 for corresponding §112(f) structure/acts];
- means/steps for enabling NC detection of M1-V0 tip-to-tip shorts [see FIGS. 10-11, 14-15, 41, and 43 for corresponding §112(f) structure/acts];
- means/steps for enabling NC detection of V1-M1 tip-to-tip shorts [see FIGS. 10-11, 14-15, 41, and 43 for corresponding §112(f) structure/acts];
- means/steps for enabling NC detection of V1 tip-to-tip shorts [see FIGS. 10-11, 14-15, 41, and 43 for corresponding §112(f) structure/acts];
- means/steps for enabling NC detection of M2 tip-to-tip shorts [see FIGS. 10-11, 14-15, 41, and 43 for corresponding §112(f) structure/acts];
- means/steps for enabling NC detection of V2-M2 tip-to-tip shorts [see FIGS. 10-11, 14-15, 41, and 43 for corresponding §112(f) structure/acts];
- means/steps for enabling NC detection of M2-V1 tip-to-tip shorts [see FIGS. 10-11, 14-15, 41, and 43 for corresponding §112(f) structure/acts];
- means/steps for enabling NC detection of M3 tip-to-tip shorts [see FIGS. 10-11, 14-15, 41, and 43 for corresponding §112(f) structure/acts];
- means/steps for enabling NC detection of V2 tip-to-tip shorts [see FIGS. 10-11, 14-15, 41, and 43 for corresponding §112(f) structure/acts]; and,
- means/steps for enabling NC detection of M3-V2 tip-to-tip shorts [see FIGS. 10-11, 14-15, 41, and 43 for corresponding §112(f) structure/acts].

Still further aspects of the invention relate to wafers, chips, and processes for making them that include/utilize DOEs based on means/steps for enabling NC detection of tip-to-side shorts, including but not limited to:

- means/steps for enabling NC detection of AA tip-to-side shorts [see FIGS. 10-11, 16, 41, and 43 for corresponding §112(f) structure/acts];
- means/steps for enabling NC detection of AACNT tip-to-side shorts [see FIGS. 10-11, 16, 41, 43, and 45 for corresponding §112(f) structure/acts];
- means/steps for enabling NC detection of AACNT-AA tip-to-side shorts [see FIGS. 10-11, 16, 41, and 43 for corresponding §112(f) structure/acts];
- means/steps for enabling NC detection of GATE-AA tip-to-side shorts [see FIGS. 10-11, 16, 41, 43, 49, 50, and 1084-1119 for corresponding §112(f) structure/acts];
- means/steps for enabling NC detection of TS-GATECNT tip-to-side shorts [see FIGS. 10-11, 16, 41, 43, and 1239-1263 for corresponding §112(f) structure/acts];
- means/steps for enabling NC detection of GATECNT-GATE tip-to-side shorts [see FIGS. 10-11, 16, 41, 43, and 1201-1238 for corresponding §112(f) structure/acts];
- means/steps for enabling NC detection of GATECNT tip-to-side shorts [see FIGS. 10-11, 16, 41, 43, and 1120-1149 for corresponding §112(f) structure/acts];
- means/steps for enabling NC detection of GATECNT-AACNT tip-to-side shorts [see FIGS. 10-11, 16, 41, 43, 1150-1188 for corresponding §112(f) structure/acts];
- means/steps for enabling NC detection of M1 tip-to-side shorts [see FIGS. 10-11, 16, 41, 43, and 1264-1297 for corresponding §112(f) structure/acts];
- means/steps for enabling NC detection of V0 tip-to-side shorts [see FIGS. 10-11, 16, 41, and 43 for corresponding §112(f) structure/acts];
- means/steps for enabling NC detection of M1-V0 tip-to-side shorts [see FIGS. 10-11, 16, 41, and 43 for corresponding §112(f) structure/acts];

means/steps for enabling NC detection of V1-M1 tip-to-side shorts [see FIGS. 10-11, 16, 41, and 43 for corresponding §112(f) structure/acts];

means/steps for enabling NC detection of V1 tip-to-side shorts [see FIGS. 10-11, 16, 41, and 43 for corresponding §112(f) structure/acts];

means/steps for enabling NC detection of M2-V1 tip-to-side shorts [see FIGS. 10-11, 16, 41, and 43 for corresponding §112(f) structure/acts];

means/steps for enabling NC detection of M2 tip-to-side shorts [see FIGS. 10-11, 16, 41, and 43 for corresponding §112(f) structure/acts];

means/steps for enabling NC detection of V2-M2 tip-to-side shorts [see FIGS. 10-11, 16, 41, and 43 for corresponding §112(f) structure/acts];

means/steps for enabling NC detection of M3 tip-to-side shorts [see FIGS. 10-11, 16, 41, and 43 for corresponding §112(f) structure/acts];

means/steps for enabling NC detection of V2 tip-to-side shorts [see FIGS. 10-11, 16, 41, and 43 for corresponding §112(f) structure/acts]; and, means/steps for enabling NC detection of M3-V2 tip-to-side shorts [see FIGS. 10-11, 16, 41, and 43 for corresponding §112(f) structure/acts].

Still further aspects of the invention relate to wafers, chips, and processes for making them that include/utilize DOEs based on means/steps for enabling NC detection of side-to-side shorts, including but not limited to:

means/steps for enabling NC detection of AA side-to-side shorts [see FIGS. 10-11, 17, 41, and 43 for corresponding §112(f) structure/acts];

means/steps for enabling NC detection of AACNT side-to-side shorts [see FIGS. 10-11, 17, 41, 43, and 786-804 for corresponding §112(f) structure/acts];

means/steps for enabling NC detection of AACNT-AA side-to-side shorts [see FIGS. 10-11, 17, 41, and 43 for corresponding §112(f) structure/acts];

means/steps for enabling NC detection of GATE side-to-side shorts [see FIGS. 10-11, 17, 41, 43, and 833-859 for corresponding §112(f) structure/acts];

means/steps for enabling NC detection of GATECNT-GATE side-to-side shorts [see FIGS. 10-11, 17, 41, 43, and 886-903 for corresponding §112(f) structure/acts];

means/steps for enabling NC detection of GATECNT side-to-side shorts [see FIGS. 10-11, 17, 41, 43, and 860-872 for corresponding §112(f) structure/acts];

means/steps for enabling NC detection of GATECNT-AACNT side-to-side shorts [see FIGS. 10-11, 17, 41, 43, 47A-C, and 873-885 for corresponding §112(f) structure/acts];

means/steps for enabling NC detection of M1 side-to-side shorts [see FIGS. 10-11, 17, 41, 43, and 904-928 for corresponding §112(f) structure/acts];

means/steps for enabling NC detection of V0 side-to-side shorts [see FIGS. 10-11, 17, 41, and 43 for corresponding §112(f) structure/acts];

means/steps for enabling NC detection of M1-V0 side-to-side shorts [see FIGS. 10-11, 17, 41, 43, and 929-936 for corresponding §112(f) structure/acts];

means/steps for enabling NC detection of V1-M1 side-to-side shorts [see FIGS. 10-11, 17, 41, and 43 for corresponding §112(f) structure/acts];

means/steps for enabling NC detection of V1 side-to-side shorts [see FIGS. 10-11, 17, 41, and 43 for corresponding §112(f) structure/acts];

means/steps for enabling NC detection of M2-V1 side-to-side shorts [see FIGS. 10-11, 17, 41, and 43 for corresponding §112(f) structure/acts];

means/steps for enabling NC detection of M2 side-to-side shorts [see FIGS. 10-11, 17, 41, and 43 for corresponding §112(f) structure/acts];

means/steps for enabling NC detection of V2-M2 side-to-side shorts [see FIGS. 10-11, 17, 41, and 43 for corresponding §112(f) structure/acts];

means/steps for enabling NC detection of M3 side-to-side shorts [see FIGS. 10-11, 17, 41, and 43 for corresponding §112(f) structure/acts];

means/steps for enabling NC detection of V2 side-to-side shorts [see FIGS. 10-11, 17, 41, and 43 for corresponding §112(f) structure/acts]; and, means/steps for enabling NC detection of M3-V2 side-to-side shorts [see FIGS. 10-11, 17, 41, and 43 for corresponding §112(f) structure/acts].

Still further aspects of the invention relate to wafers, chips, and processes for making them that include/utilize DOEs based on means/steps for enabling NC detection of L-shape interlayer shorts, including but not limited to:

means/steps for enabling NC detection of AA L-shape interlayer shorts [see FIGS. 10-11, 18-22, 41, and 43 for corresponding §112(f) structure/acts];

means/steps for enabling NC detection of AACNT-L-shape interlayer shorts [see FIGS. 10-11, 18-22, 41, and 43 for corresponding §112(f) structure/acts];

means/steps for enabling NC detection of AACNT-AA-L-shape interlayer shorts [see FIGS. 10-11, 18-22, 41, and 43 for corresponding §112(f) structure/acts];

means/steps for enabling NC detection of GATE-AA-L-shape interlayer shorts [see FIGS. 10-11, 18-22, 41, and 43 for corresponding §112(f) structure/acts];

means/steps for enabling NC detection of GATE-TS L-shape interlayer shorts [see FIGS. 10-11, 18-22, 41, and 43 for corresponding §112(f) structure/acts];

means/steps for enabling NC detection of GATECNT-GATE-L-shape interlayer shorts [see FIGS. 10-11, 18-22, 41, and 43 for corresponding §112(f) structure/acts];

means/steps for enabling NC detection of GATECNT-AA L-shape interlayer shorts [see FIGS. 10-11, 18-22, 41, and 43 for corresponding §112(f) structure/acts];

means/steps for enabling NC detection of GATE-TS L-shape interlayer shorts [see FIGS. 10-11, 18-22, 41, and 43 for corresponding §112(f) structure/acts];

means/steps for enabling NC detection of GATECNT-AACNT-L-shape interlayer shorts [see FIGS. 10-11, 18-22, 41, and 43 for corresponding §112(f) structure/acts];

means/steps for enabling NC detection of V0-AA L-shape interlayer shorts [see FIGS. 10-11, 18-22, 41, and 43 for corresponding §112(f) structure/acts];

means/steps for enabling NC detection of V0-TS L-shape interlayer shorts [see FIGS. 10-11, 18-22, 41, and 43 for corresponding §112(f) structure/acts];

means/steps for enabling NC detection of V0-AACNT L-shape interlayer shorts [see FIGS. 10-11, 18-22, 41, and 43 for corresponding §112(f) structure/acts];

means/steps for enabling NC detection of V0-GATE L-shape interlayer shorts [see FIGS. 10-11, 18-22, 41, and 43 for corresponding §112(f) structure/acts];

means/steps for enabling NC detection of V0-GATECNT L-shape interlayer shorts [see FIGS. 10-11, 18-22, 41, and 43 for corresponding §112(f) structure/acts];

means/steps for enabling NC detection of M1-AACNT L-shape interlayer shorts [see FIGS. 10-11, 18-22, 41, and 43 for corresponding §112(f) structure/acts];

means/steps for enabling NC detection of M1-GATECNT L-shape interlayer shorts [see FIGS. 10-11, 18-22, 41, and 43 for corresponding §112(f) structure/acts];

means/steps for enabling NC detection of M1-V0-L-shape interlayer shorts [see FIGS. 10-11, 18-22, 41, and 43 for corresponding §112(f) structure/acts];

means/steps for enabling NC detection of V1-M1-L-shape interlayer shorts [see FIGS. 10-11, 18-22, 41, and 43 for corresponding §112(f) structure/acts];

means/steps for enabling NC detection of V1-V0 L-shape interlayer shorts [see FIGS. 10-11, 18-22, 41, and 43 for corresponding §112(f) structure/acts];

means/steps for enabling NC detection of M2-V1-L-shape interlayer shorts [see FIGS. 10-11, 18-22, 41, and 43 for corresponding §112(f) structure/acts];

means/steps for enabling NC detection of V2-V1 L-shape interlayer shorts [see FIGS. 10-11, 18-22, 41, and 43 for corresponding §112(f) structure/acts];

means/steps for enabling NC detection of V2-M2 L-shape interlayer shorts [see FIGS. 10-11, 18-22, 41, and 43 for corresponding §112(f) structure/acts];

means/steps for enabling NC detection of M3-M2 L-shape interlayer shorts [see FIGS. 10-11, 18-22, 41, and 43 for corresponding §112(f) structure/acts];

means/steps for enabling NC detection of M3-V2 L-shape interlayer shorts [see FIGS. 10-11, 18-22, 41, and 43 for corresponding §112(f) structure/acts].

Still further aspects of the invention relate to wafers, chips, and processes for making them that include/utilize DOEs based on means/steps for enabling NC detection of diagonal shorts, including but not limited to:

means/steps for enabling NC detection of AA diagonal shorts [see FIGS. 10-11, 23, 41, and 43 for corresponding §112(f) structure/acts];

means/steps for enabling NC detection of TS diagonal shorts [see FIGS. 10-11, 23, 41, and 43 for corresponding §112(f) structure/acts];

means/steps for enabling NC detection of AACNT diagonal shorts [see FIGS. 10-11, 23, 41, and 43 for corresponding §112(f) structure/acts];

means/steps for enabling NC detection of AACNT-AA diagonal shorts [see FIGS. 10-11, 23, 41, and 43 for corresponding §112(f) structure/acts];

means/steps for enabling NC detection of GATE diagonal shorts [see FIGS. 10-11, 23, 41, and 43 for corresponding §112(f) structure/acts];

means/steps for enabling NC detection of GATE-AACNT diagonal shorts [see FIGS. 10-11, 23, 41, and 43 for corresponding §112(f) structure/acts];

means/steps for enabling NC detection of GATECNT-GATE diagonal shorts [see FIGS. 10-11, 23, 41, and 43 for corresponding §112(f) structure/acts];

means/steps for enabling NC detection of GATECNT diagonal shorts [see FIGS. 10-11, 23, 41, 43, and 495-554 for corresponding §112(f) structure/acts];

means/steps for enabling NC detection of GATECNT-AACNT diagonal shorts [see FIGS. 10-11, 23, 41, 43, and 555-632 for corresponding §112(f) structure/acts];

means/steps for enabling NC detection of M1 diagonal shorts [see FIGS. 10-11, 23, 41, and 43 for corresponding §112(f) structure/acts];

means/steps for enabling NC detection of V0 diagonal shorts [see FIGS. 10-11, 23, 41, and 43 for corresponding §112(f) structure/acts];

means/steps for enabling NC detection of M1-V0 diagonal shorts [see FIGS. 10-11, 23, 41, and 43 for corresponding §112(f) structure/acts];

means/steps for enabling NC detection of V1-M1 diagonal shorts [see FIGS. 10-11, 23, 41, and 43 for corresponding §112(f) structure/acts];

means/steps for enabling NC detection of V1 diagonal shorts [see FIGS. 10-11, 23, 41, and 43 for corresponding §112(f) structure/acts];

means/steps for enabling NC detection of M2 diagonal shorts [see FIGS. 10-11, 23, 41, and 43 for corresponding §112(f) structure/acts];

means/steps for enabling NC detection of M2-V1 diagonal shorts [see FIGS. 10-11, 23, 41, and 43 for corresponding §112(f) structure/acts];

means/steps for enabling NC detection of M3 diagonal shorts [see FIGS. 10-11, 23, 41, and 43 for corresponding §112(f) structure/acts];

means/steps for enabling NC detection of V2-M2 diagonal shorts [see FIGS. 10-11, 23, 41, and 43 for corresponding §112(f) structure/acts];

means/steps for enabling NC detection of V2 diagonal shorts [see FIGS. 10-11, 23, 41, and 43 for corresponding §112(f) structure/acts]; and, means/steps for enabling NC detection of M3-V2 diagonal shorts [see FIGS. 10-11, 23, 41, and 43 for corresponding §112(f) structure/acts].

Still further aspects of the invention relate to wafers, chips, and processes for making them that include/utilize DOEs based on means/steps for enabling NC detection of corner shorts, including but not limited to:

means/steps for enabling NC detection of AA corner shorts [see FIGS. 10-11, 24-26, 41, and 43 for corresponding §112(f) structure/acts];

means/steps for enabling NC detection of AACNT corner shorts [see FIGS. 10-11, 24-26, 41, and 43 for corresponding §112(f) structure/acts];

means/steps for enabling NC detection of AACNT-AA corner shorts [see FIGS. 10-11, 24-26, 41, and 43 for corresponding §112(f) structure/acts];

means/steps for enabling NC detection of GATE corner shorts [see FIGS. 10-11, 24-26, 41, and 43 for corresponding §112(f) structure/acts];

means/steps for enabling NC detection of GATECNT-GATE corner shorts [see FIGS. 10-11, 24-26, 41, and 43 for corresponding §112(f) structure/acts];

means/steps for enabling NC detection of GATECNT-TS corner shorts [see FIGS. 10-11, 24-26, 41, and 43 for corresponding §112(f) structure/acts];

means/steps for enabling NC detection of GATECNT corner shorts [see FIGS. 10-11, 24-26, 41, and 43 for corresponding §112(f) structure/acts];

means/steps for enabling NC detection of GATECNT-AA corner shorts [see FIGS. 10-11, 24-26, 41, 43, and 263-286 for corresponding §112(f) structure/acts];

means/steps for enabling NC detection of GATECNT-AACNT corner shorts [see FIGS. 10-11, 24-26, 41, and 43 for corresponding §112(f) structure/acts];

means/steps for enabling NC detection of M1 corner shorts [see FIGS. 10-11, 24-26, 41, 43, and 416-494 for corresponding §112(f) structure/acts];

means/steps for enabling NC detection of V0 corner shorts [see FIGS. 10-11, 24-26, 41, and 43 for corresponding §112(f) structure/acts];

means/steps for enabling NC detection of M1-V0 corner shorts [see FIGS. 10-11, 24-26, 41, and 43 for corresponding §112(f) structure/acts];

means/steps for enabling NC detection of V1-M1 corner shorts [see FIGS. 10-11, 24-26, 41, and 43 for corresponding §112(f) structure/acts];

means/steps for enabling NC detection of V1 corner shorts [see FIGS. 10-11, 24-26, 41, and 43 for corresponding §112(f) structure/acts];

means/steps for enabling NC detection of M2 corner shorts [see FIGS. 10-11, 24-26, 41, and 43 for corresponding §112(f) structure/acts];

means/steps for enabling NC detection of M2-V1 corner shorts [see FIGS. 10-11, 24-26, 41, and 43 for corresponding §112(f) structure/acts];

means/steps for enabling NC detection of M3 corner shorts [see FIGS. 10-11, 24-26, 41, and 43 for corresponding §112(f) structure/acts];

means/steps for enabling NC detection of V2-M2 corner shorts [see FIGS. 10-11, 24-26, 41, and 43 for corresponding §112(f) structure/acts];

means/steps for enabling NC detection of V2 corner shorts [see FIGS. 10-11, 24-26, 41, and 43 for corresponding §112(f) structure/acts]; and, means/steps for enabling NC detection of M3-V2 corner shorts [see FIGS. 10-11, 24-26, 41, and 43 for corresponding §112(f) structure/acts].

Still further aspects of the invention relate to wafers, chips, and processes for making them that include/utilize DOEs based on means/steps for enabling NC detection of interlayer-overlap shorts, including but not limited to:

means/steps for enabling NC detection of GATE-AA interlayer overlap shorts [see FIGS. 10-11, 27, 41, 43, and 692-734 for corresponding §112(f) structure/acts];

means/steps for enabling NC detection of GATE-AACNT interlayer overlap shorts [see FIGS. 10-11, 27, 41, 43, and 633-691 for corresponding §112(f) structure/acts];

means/steps for enabling NC detection of GATE-TS interlayer overlap shorts [see FIGS. 10-11, 27, 41, and 43 for corresponding §112(f) structure/acts];

means/steps for enabling NC detection of GATECNT-TS interlayer overlap shorts [see FIGS. 10-11, 27, 41, and 43 for corresponding §112(f) structure/acts];

means/steps for enabling NC detection of GATECNT-AA interlayer overlap shorts [see FIGS. 10-11, 27, 41, and 43 for corresponding §112(f) structure/acts];

means/steps for enabling NC detection of V0-AA interlayer overlap shorts [see FIGS. 10-11, 27, 41, and 43 for corresponding §112(f) structure/acts];

means/steps for enabling NC detection of V0-AACNT interlayer overlap shorts [see FIGS. 10-11, 27, 41, and 43 for corresponding §112(f) structure/acts];

means/steps for enabling NC detection of V0-TS interlayer overlap shorts [see FIGS. 10-11, 27, 41, and 43 for corresponding §112(f) structure/acts];

means/steps for enabling NC detection of V0-GATE interlayer overlap shorts [see FIGS. 10-11, 27, 41, and 43 for corresponding §112(f) structure/acts];

means/steps for enabling NC detection of M1-GATECNT interlayer overlap shorts [see FIGS. 10-11, 27, 41, and 43 for corresponding §112(f) structure/acts];

means/steps for enabling NC detection of M1-AACNT interlayer overlap shorts [see FIGS. 10-11, 27, 41, and 43 for corresponding §112(f) structure/acts];

means/steps for enabling NC detection of V1-V0 interlayer overlap shorts [see FIGS. 10-11, 27, 41, and 43 for corresponding §112(f) structure/acts];

means/steps for enabling NC detection of M2-M1-interlayer-overlap shorts [see FIGS. 10-11, 27, 41, and 43 for corresponding §112(f) structure/acts];

means/steps for enabling NC detection of V2-V1-interlayer-overlap shorts [see FIGS. 10-11, 27, 41, and 43 for corresponding §112(f) structure/acts]; and, means/steps for enabling NC detection of M3-M2-interlayer-overlap shorts [see FIGS. 10-11, 27, 41, and 43 for corresponding §112(f) structure/acts].

Still further aspects of the invention relate to wafers, chips, and processes for making them that include/utilize DOEs based on means/steps for enabling NC detection of via-chamfer shorts, including but not limited to:

means/steps for enabling NC detection of V0-GATECNT via chamfer shorts [see FIGS. 10-11, 28, 41, and 43 for corresponding §112(f) structure/acts];

means/steps for enabling NC detection of V0-AACNT via chamfer shorts [see FIGS. 10-11, 28, 41, 43, and 52-256 for corresponding §112(f) structure/acts];

means/steps for enabling NC detection of V1-M1 via chamfer shorts [see FIGS. 10-11, 28, 41, and 43 for corresponding §112(f) structure/acts];

means/steps for enabling NC detection of V2-M2 via chamfer shorts [see FIGS. 10-11, 28, 41, and 43 for corresponding §112(f) structure/acts]; and, means/step for enabling NC detection of V3-M3 via chamfer shorts [see FIGS. 10-11, 28, 41, 43, and 257-262 for corresponding §112(f) structure/acts].

Still further aspects of the invention relate to wafers, chips, and processes for making them that include/utilize DOEs based on means/steps for enabling NC detection of merged-via shorts, including but not limited to:

means/steps for enabling NC detection of V0 merged via shorts [see FIGS. 10-11, 29, 41, and 43 for corresponding §112(f) structure/acts];

means/steps for enabling NC detection of V1 merged via shorts [see FIGS. 10-11, 29, 41, and 43 for corresponding §112(f) structure/acts]; and, means/steps for enabling NC detection of V2 merged via shorts [see FIGS. 10-11, 29, 41, and 43 for corresponding §112(f) structure/acts].

Still further aspects of the invention relate to wafers, chips, and processes for making them that include/utilize DOEs based on means/steps for enabling NC detection of snake opens, including but not limited to:

means/steps for enabling NC detection of AA snake opens [see FIGS. 12-13, 30, 41, and 43 for corresponding §112(f) structure/acts];

means/steps for enabling NC detection of TS snake opens [see FIGS. 12-13, 30, 41, and 43 for corresponding §112(f) structure/acts];

means/steps for enabling NC detection of AACNT snake opens [see FIGS. 12-13, 30, 41, and 43 for corresponding §112(f) structure/acts];

means/steps for enabling NC detection of GATE snake opens [see FIGS. 12-13, 30, 41, 43, and 1041-1048 for corresponding §112(f) structure/acts];

means/steps for enabling NC detection of GATECNT snake opens [see FIGS. 12-13, 30, 41, and 43 for corresponding §112(f) structure/acts];

means/steps for enabling NC detection of V0 snake opens [see FIGS. 12-13, 30, 41, and 43 for corresponding §112(f) structure/acts];

means/steps for enabling NC detection of M1 snake opens [see FIGS. 12-13, 30, 41, 43, 44, and 1049-1066 for corresponding §112(f) structure/acts];

means/steps for enabling NC detection of M1-V0-AACNT snake opens [see FIGS. 12-13, 30, 41, 43, and 1067-1071 for corresponding §112(f) structure/acts];

means/steps for enabling NC detection of V1 snake opens [see FIGS. 12-13, 30, 41, and 43 for corresponding §112(f) structure/acts];

means/steps for enabling NC detection of M2 snake opens [see FIGS. 12-13, 30, 41, and 43 for corresponding §112(f) structure/acts];

means/steps for enabling NC detection of V2 snake opens [see FIGS. 12-13, 30, 41, and 43 for corresponding §112(f) structure/acts]; and, means/steps for enabling NC detection of M3 snake opens [see FIGS. 12-13, 30, 41, and 43 for corresponding §112(f) structure/acts].

Still further aspects of the invention relate to wafers, chips, and processes for making them that include/utilize DOEs based on means/steps for enabling NC detection of stitch opens, including but not limited to:

means/steps for enabling NC detection of AA stitch opens [see FIGS. 12-13, 31-32, 41, and 43 for corresponding §112(f) structure/acts];

means/steps for enabling NC detection of TS stitch opens [see FIGS. 12-13, 31-32, 41, and 43 for corresponding §112(f) structure/acts];

means/steps for enabling NC detection of AACNT stitch opens [see FIGS. 12-13, 31-32, 41, and 43 for corresponding §112(f) structure/acts];

means/steps for enabling NC detection of GATECNT stitch opens [see FIGS. 12-13, 31-32, 41, and 43 for corresponding §112(f) structure/acts];

means/steps for enabling NC detection of V0 stitch opens [see FIGS. 12-13, 31-32, 41, and 43 for corresponding §112(f) structure/acts];

means/steps for enabling NC detection of M1 stitch opens [see FIGS. 12-13, 31-32, 41, 43, and 1072-1083 for corresponding §112(f) structure/acts];

means/steps for enabling NC detection of V1 stitch opens [see FIGS. 12-13, 31-32, 41, and 43 for corresponding §112(f) structure/acts];

means/steps for enabling NC detection of M2 stitch opens [see FIGS. 12-13, 31-32, 41, and 43 for corresponding §112(f) structure/acts];

means/steps for enabling NC detection of V2 stitch opens [see FIGS. 12-13, 31-32, 41, and 43 for corresponding §112(f) structure/acts]; and, means/steps for enabling NC detection of M3 stitch opens [see FIGS. 12-13, 31-32, 41, and 43 for corresponding §112(f) structure/acts].

Still further aspects of the invention relate to wafers, chips, and processes for making them that include/utilize DOEs based on means/steps for enabling NC detection of via opens, including but not limited to:

means/steps for enabling NC detection of AACNT-TS via opens [see FIGS. 12-13, 33, 41, 43, and 1629-1673 for corresponding §112(f) structure/acts];

means/steps for enabling NC detection of AACNT-AA via opens [see FIGS. 12-13, 33, 41, 43, and 1557-1628 for corresponding §112(f) structure/acts];

means/steps for enabling NC detection of TS-AA via opens [see FIGS. 12-13, 33, 41, 43, and 2315-2330 for corresponding §112(f) structure/acts];

means/steps for enabling NC detection of GATECNT-GATE via opens [see FIGS. 12-13, 33, 41, 43, 48, and 1699-2005 for corresponding §112(f) structure/acts];

means/steps for enabling NC detection of GATECNT-AACNT via opens [see FIGS. 12-13, 33, 41, 43, and 1674-1682 for corresponding §112(f) structure/acts];

means/steps for enabling NC detection of GATECNT-AACNT-GATE via opens [see FIGS. 12-13, 33, 41, 43, and 1683-1698 for corresponding §112(f) structure/acts];

means/steps for enabling NC detection of V0-GATECNT via opens [see FIGS. 12-13, 33, 41, 43, and 2375-2439 for corresponding §112(f) structure/acts];

means/steps for enabling NC detection of V0-AA via opens [see FIGS. 12-13, 33, 41, and 43 for corresponding §112(f) structure/acts];

means/steps for enabling NC detection of V0 via opens [see FIGS. 12-13, 33, 41, 43, and 2331-2344 for corresponding §112(f) structure/acts];

means/steps for enabling NC detection of V0-TS via opens [see FIGS. 12-13, 33, 41, and 43 for corresponding §112(f) structure/acts];

means/steps for enabling NC detection of V0-AACNT via opens [see FIGS. 12-13, 33, 41, 43, and 2345-2374 for corresponding §112(f) structure/acts];

means/steps for enabling NC detection of V0-GATE via opens [see FIGS. 12-13, 33, 41, and 43 for corresponding §112(f) structure/acts];

means/steps for enabling NC detection of V1 via opens [see FIGS. 12-13, 33, 41, 43, and 2440-2441 for corresponding §112(f) structure/acts];

means/steps for enabling NC detection of M1-V0 via opens [see FIGS. 12-13, 33, 41, 43, and 2006-2220 for corresponding §112(f) structure/acts];

means/steps for enabling NC detection of V1-M1 via opens [see FIGS. 12-13, 33, 41, 43, and 2442-2459 for corresponding §112(f) structure/acts];

means/steps for enabling NC detection of V1-M2 via opens [see FIGS. 12-13, 33, 41, 43, and 2221-2256 for corresponding §112(f) structure/acts];

means/steps for enabling NC detection of M1-GATECNT via opens [see FIGS. 12-13, 33, 41, and 43 for corresponding §112(f) structure/acts];

means/steps for enabling NC detection of V2-M3 via opens [see FIGS. 12-13, 33, 41, 43, and 2257-2274 for corresponding §112(f) structure/acts];

means/steps for enabling NC detection of M1-AANCT via opens [see FIGS. 12-13, 33, 41, and 43 for corresponding §112(f) structure/acts];

means/steps for enabling NC detection of V2-M2 via opens [see FIGS. 12-13, 33, 41, and 43 for corresponding §112(f) structure/acts];

means/steps for enabling NC detection V3 via opens [see FIGS. 12-13, 33, 41, 43, and 2460-2461 for corresponding §112(f) structure/acts];

means/steps for enabling NC detection of M4-V3 via opens [see FIGS. 12-13, 33, 41, 43, and 2275-2296 for corresponding §112(f) structure/acts]; and, means/steps for enabling NC detection of M5-V4 via opens [see FIGS. 12-13, 33, 41, 43, and 2297-2314 for corresponding §112(f) structure/acts].

Still further aspects of the invention relate to wafers, chips, and processes for making them that include/utilize DOEs based on means/steps for enabling NC detection of metal island opens, including but not limited to:

means/steps for enabling NC detection of M1 metal island opens [see FIGS. 12-13, 34-35, 41, and 43 for corresponding §112(f) structure/acts];

means/steps for enabling NC detection of M2 metal island opens [see FIGS. 12-13, 34-35, 41, and 43 for corresponding §112(f) structure/acts];

means/steps for enabling NC detection of M3 metal island opens [see FIGS. 12-13, 34-35, 41, and 43 for corresponding §112(f) structure/acts];

Still further aspects of the invention relate to wafers, chips, and processes for making them that include/utilize DOEs based on means/steps for enabling NC detection of merged-via opens, including but not limited to:

means/steps for enabling NC detection of V0-GATECNT merged via opens [see FIGS. 12-13, 36, 41, and 43 for corresponding §112(f) structure/acts];

means/steps for enabling NC detection of V0 merged via opens [see FIGS. 12-13, 36, 41, 43, and 735-785 for corresponding §112(f) structure/acts];

means/steps for enabling NC detection of V0-AACNT merged via opens [see FIGS. 12-13, 36, 41, and 43 for corresponding §112(f) structure/acts];

means/steps for enabling NC detection of V1 merged via opens [see FIGS. 12-13, 36, 41, and 43 for corresponding §112(f) structure/acts];

means/steps for enabling NC detection of V2 merged via opens [see FIGS. 12-13, 36, 41, and 43 for corresponding §112(f) structure/acts];

means/steps for enabling NC detection of V1-M1 merged via opens [see FIGS. 12-13, 36, 41, and 43 for corresponding §112(f) structure/acts]; and, means/steps for enabling NC detection of V2-M2 merged via opens [see FIGS. 12-13, 36, 41, and 43 for corresponding §112(f) structure/acts].

Still further aspects of the invention relate to wafers, chips, and processes for making them that include/utilize DOEs based on means/steps for enabling NC detection of tip-to-tip leakages, including but not limited to:

means/steps for enabling NC detection of AA tip-to-tip leakages [see FIGS. 10-11, 14-15, 41, 43, and 1298-1326 for corresponding §112(f) structure/acts];

means/steps for enabling NC detection of AACNT tip-to-tip leakages [see FIGS. 10-11, 14-15, 41, 43, and 1327-1405 for corresponding §112(f) structure/acts];

means/steps for enabling NC detection of TS tip-to-tip leakages [see FIGS. 10-11, 14-15, 41, and 43 for corresponding §112(f) structure/acts];

means/steps for enabling NC detection of AACNT-AA tip-to-tip leakages [see FIGS. 10-11, 14-15, 41, and 43 for corresponding §112(f) structure/acts];

means/steps for enabling NC detection of GATE tip-to-tip leakages [see FIGS. 10-11, 14-15, 41, 43, and 1413-1461 for corresponding §112(f) structure/acts];

means/steps for enabling NC detection of GATECNT-GATE tip-to-tip leakages [see FIGS. 10-11, 14-15, 41, and 43 for corresponding §112(f) structure/acts];

means/steps for enabling NC detection of GATECNT tip-to-tip leakages [see FIGS. 10-11, 14-15, 41, 43, and 1462-1548 for corresponding §112(f) structure/acts];

means/steps for enabling NC detection of GATECNT-AACNT tip-to-tip leakages [see FIGS. 10-11, 14-15, 41, and 43 for corresponding §112(f) structure/acts];

means/steps for enabling NC detection of M1 tip-to-tip leakages [see FIGS. 10-11, 14-15, 41, 43, and 1549-1556 for corresponding §112(f) structure/acts];

means/steps for enabling NC detection of V0 tip-to-tip leakages [see FIGS. 10-11, 14-15, 41, and 43 for corresponding §112(f) structure/acts];

means/steps for enabling NC detection of M1-V0 tip-to-tip leakages [see FIGS. 10-11, 14-15, 41, and 43 for corresponding §112(f) structure/acts];

means/steps for enabling NC detection of V1-M1 tip-to-tip leakages [see FIGS. 10-11, 14-15, 41, and 43 for corresponding §112(f) structure/acts];

means/steps for enabling NC detection of V1 tip-to-tip leakages [see FIGS. 10-11, 14-15, 41, and 43 for corresponding §112(f) structure/acts];

means/steps for enabling NC detection of M2 tip-to-tip leakages [see FIGS. 10-11, 14-15, 41, and 43 for corresponding §112(f) structure/acts];

means/steps for enabling NC detection of V2-M2 tip-to-tip leakages [see FIGS. 10-11, 14-15, 41, and 43 for corresponding §112(f) structure/acts];

means/steps for enabling NC detection of M2-V1 tip-to-tip leakages [see FIGS. 10-11, 14-15, 41, and 43 for corresponding §112(f) structure/acts];

means/steps for enabling NC detection of M3 tip-to-tip leakages [see FIGS. 10-11, 14-15, 41, and 43 for corresponding §112(f) structure/acts];

means/steps for enabling NC detection of V2 tip-to-tip leakages [see FIGS. 10-11, 14-15, 41, and 43 for corresponding §112(f) structure/acts]; and, means/steps for enabling NC detection of M3-V2 tip-to-tip leakages [see FIGS. 10-11, 14-15, 41, and 43 for corresponding §112(f) structure/acts].

Still further aspects of the invention relate to wafers, chips, and processes for making them that include/utilize DOEs based on means/steps for enabling NC detection of tip-to-side leakages, including but not limited to:

means/steps for enabling NC detection of AA tip-to-side leakages [see FIGS. 10-11, 16, 41, and 43 for corresponding §112(f) structure/acts];

means/steps for enabling NC detection of AACNT tip-to-side leakages [see FIGS. 10-11, 16, 41, 43, and 45 for corresponding §112(f) structure/acts];

means/steps for enabling NC detection of AACNT-AA tip-to-side leakages [see FIGS. 10-11, 16, 41, and 43 for corresponding §112(f) structure/acts];

means/steps for enabling NC detection of GATE-AA tip-to-side leakages [see FIGS. 10-11, 16, 41, 43, 49, 50, and 1084-1119 for corresponding §112(f) structure/acts];

means/steps for enabling NC detection of TS-GATECNT tip-to-side leakages [see FIGS. 10-11, 16, 41, 43, and 1239-1263 for corresponding §112(f) structure/acts];

means/steps for enabling NC detection of GATECNT-GATE tip-to-side leakages [see FIGS. 10-11, 16, 41, 43, and 1201-1238 for corresponding §112(f) structure/acts];

means/steps for enabling NC detection of GATECNT tip-to-side leakages [see FIGS. 10-11, 16, 41, 43, and 1120-1149 for corresponding §112(f) structure/acts];

means/steps for enabling NC detection of GATECNT-AACNT tip-to-side leakages [see FIGS. 10-11, 16, 41, 43, 1150-1188 for corresponding §112(f) structure/acts];

means/steps for enabling NC detection of M1 tip-to-side leakages [see FIGS. 10-11, 16, 41, 43, and 1264-1297 for corresponding §112(f) structure/acts];

means/steps for enabling NC detection of V0 tip-to-side leakages [see FIGS. 10-11, 16, 41, and 43 for corresponding §112(f) structure/acts];

means/steps for enabling NC detection of M1-V0 tip-to-side leakages [see FIGS. 10-11, 16, 41, and 43 for corresponding §112(f) structure/acts];

means/steps for enabling NC detection of V1-M1 tip-to-side leakages [see FIGS. 10-11, 16, 41, and 43 for corresponding §112(f) structure/acts];

- means/steps for enabling NC detection of V1 tip-to-side leakages [see FIGS. 10-11, 16, 41, and 43 for corresponding §112(f) structure/acts];
- means/steps for enabling NC detection of M2-V1 tip-to-side leakages [see FIGS. 10-11, 16, 41, and 43 for corresponding §112(f) structure/acts];
- means/steps for enabling NC detection of M2 tip-to-side leakages [see FIGS. 10-11, 16, 41, and 43 for corresponding §112(f) structure/acts];
- means/steps for enabling NC detection of V2-M2 tip-to-side leakages [see FIGS. 10-11, 16, 41, and 43 for corresponding §112(f) structure/acts];
- means/steps for enabling NC detection of M3 tip-to-side leakages [see FIGS. 10-11, 16, 41, and 43 for corresponding §112(f) structure/acts];
- means/steps for enabling NC detection of V2 tip-to-side leakages [see FIGS. 10-11, 16, 41, and 43 for corresponding §112(f) structure/acts]; and,
- means/steps for enabling NC detection of M3-V2 tip-to-side leakages [see FIGS. 10-11, 16, 41, and 43 for corresponding §112(f) structure/acts].

Still further aspects of the invention relate to wafers, chips, and processes for making them that include/utilize DOEs based on means/steps for enabling NC detection of side-to-side leakages, including but not limited to:

- means/steps for enabling NC detection of AA side-to-side leakages [see FIGS. 10-11, 17, 41, and 43 for corresponding §112(f) structure/acts];
- means/steps for enabling NC detection of AACNT side-to-side leakages [see FIGS. 10-11, 17, 41, 43, and 786-804 for corresponding §112(f) structure/acts];
- means/steps for enabling NC detection of AACNT-AA side-to-side leakages [see FIGS. 10-11, 17, 41, and 43 for corresponding §112(f) structure/acts];
- means/steps for enabling NC detection of GATE side-to-side leakages [see FIGS. 10-11, 17, 41, 43, and 833-859 for corresponding §112(f) structure/acts];
- means/steps for enabling NC detection of GATECNT-GATE side-to-side leakages [see FIGS. 10-11, 17, 41, 43, and 886-903 for corresponding §112(f) structure/acts];
- means/steps for enabling NC detection of GATECNT side-to-side leakages [see FIGS. 10-11, 17, 41, 43, and 860-872 for corresponding §112(f) structure/acts];
- means/steps for enabling NC detection of GATECNT-AACNT side-to-side leakages [see FIGS. 10-11, 17, 41, 43, 47A-C, and 873-885 for corresponding §112(f) structure/acts];
- means/steps for enabling NC detection of M1 side-to-side leakages [see FIGS. 10-11, 17, 41, 43, and 904-928 for corresponding §112(f) structure/acts];
- means/steps for enabling NC detection of V0 side-to-side leakages [see FIGS. 10-11, 17, 41, and 43 for corresponding §112(f) structure/acts];
- means/steps for enabling NC detection of M1-V0 side-to-side leakages [see FIGS. 10-11, 17, 41, 43, and 929-936 for corresponding §112(f) structure/acts];
- means/steps for enabling NC detection of V1-M1 side-to-side leakages [see FIGS. 10-11, 17, 41, and 43 for corresponding §112(f) structure/acts];
- means/steps for enabling NC detection of V1 side-to-side leakages [see FIGS. 10-11, 17, 41, and 43 for corresponding §112(f) structure/acts];
- means/steps for enabling NC detection of M2-V1 side-to-side leakages [see FIGS. 10-11, 17, 41, and 43 for corresponding §112(f) structure/acts];
- means/steps for enabling NC detection of M2 side-to-side leakages [see FIGS. 10-11, 17, 41, and 43 for corresponding §112(f) structure/acts];
- means/steps for enabling NC detection of V2-M2 side-to-side leakages [see FIGS. 10-11, 17, 41, and 43 for corresponding §112(f) structure/acts];
- means/steps for enabling NC detection of M3 side-to-side leakages [see FIGS. 10-11, 17, 41, and 43 for corresponding §112(f) structure/acts];
- means/steps for enabling NC detection of V2 side-to-side leakages [see FIGS. 10-11, 17, 41, and 43 for corresponding §112(f) structure/acts]; and,
- means/steps for enabling NC detection of M3-V2 side-to-side leakages [see FIGS. 10-11, 17, 41, and 43 for corresponding §112(f) structure/acts].

Still further aspects of the invention relate to wafers, chips, and processes for making them that include/utilize DOEs based on means/steps for enabling NC detection of L-shape interlayer leakages, including but not limited to:

- means/steps for enabling NC detection of AA L-shape interlayer leakages [see FIGS. 10-11, 18-22, 41, and 43 for corresponding §112(f) structure/acts];
- means/steps for enabling NC detection of AACNT-L-shape interlayer leakages [see FIGS. 10-11, 18-22, 41, and 43 for corresponding §112(f) structure/acts];
- means/steps for enabling NC detection of AACNT-AA-L-shape interlayer leakages [see FIGS. 10-11, 18-22, 41, and 43 for corresponding §112(f) structure/acts];
- means/steps for enabling NC detection of GATE-AA-L-shape interlayer leakages [see FIGS. 10-11, 18-22, 41, and 43 for corresponding §112(f) structure/acts];
- means/steps for enabling NC detection of GATE-TS L-shape interlayer leakages [see FIGS. 10-11, 18-22, 41, and 43 for corresponding §112(f) structure/acts];
- means/steps for enabling NC detection of GATECNT-GATE-L-shape interlayer leakages [see FIGS. 10-11, 18-22, 41, and 43 for corresponding §112(f) structure/acts];
- means/steps for enabling NC detection of GATECNT-AA L-shape interlayer leakages [see FIGS. 10-11, 18-22, 41, and 43 for corresponding §112(f) structure/acts];
- means/steps for enabling NC detection of GATE-TS L-shape interlayer leakages [see FIGS. 10-11, 18-22, 41, and 43 for corresponding §112(f) structure/acts];
- means/steps for enabling NC detection of GATECNT-AACNT-L-shape interlayer leakages [see FIGS. 10-11, 18-22, 41, and 43 for corresponding §112(f) structure/acts];
- means/steps for enabling NC detection of V0-AA L-shape interlayer leakages [see FIGS. 10-11, 18-22, 41, and 43 for corresponding §112(f) structure/acts];
- means/steps for enabling NC detection of V0-TS L-shape interlayer leakages [see FIGS. 10-11, 18-22, 41, and 43 for corresponding §112(f) structure/acts];
- means/steps for enabling NC detection of V0-AACNT L-shape interlayer leakages [see FIGS. 10-11, 18-22, 41, and 43 for corresponding §112(f) structure/acts];
- means/steps for enabling NC detection of V0-GATE L-shape interlayer leakages [see FIGS. 10-11, 18-22, 41, and 43 for corresponding §112(f) structure/acts];
- means/steps for enabling NC detection of V0-GATECNT L-shape interlayer leakages [see FIGS. 10-11, 18-22, 41, and 43 for corresponding §112(f) structure/acts];
- means/steps for enabling NC detection of M1-AACNT L-shape interlayer leakages [see FIGS. 10-11, 18-22, 41, and 43 for corresponding §112(f) structure/acts];

means/steps for enabling NC detection of M1-GATECNT L-shape interlayer leakages [see FIGS. 10-11, 18-22, 41, and 43 for corresponding §112(f) structure/acts];

means/steps for enabling NC detection of M1-V0-L-shape interlayer leakages [see FIGS. 10-11, 18-22, 41, and 43 for corresponding §112(f) structure/acts];

means/steps for enabling NC detection of V1-M1-L-shape interlayer leakages [see FIGS. 10-11, 18-22, 41, and 43 for corresponding §112(f) structure/acts];

means/steps for enabling NC detection of V1-V0 L-shape interlayer leakages [see FIGS. 10-11, 18-22, 41, and 43 for corresponding §112(f) structure/acts];

means/steps for enabling NC detection of M2-V1-L-shape interlayer leakages [see FIGS. 10-11, 18-22, 41, and 43 for corresponding §112(f) structure/acts];

means/steps for enabling NC detection of V2-V1 L-shape interlayer leakages [see FIGS. 10-11, 18-22, 41, and 43 for corresponding §112(f) structure/acts];

means/steps for enabling NC detection of V2-M2 L-shape interlayer leakages [see FIGS. 10-11, 18-22, 41, and 43 for corresponding §112(f) structure/acts];

means/steps for enabling NC detection of M3-M2 L-shape interlayer leakages [see FIGS. 10-11, 18-22, 41, and 43 for corresponding §112(f) structure/acts];

means/steps for enabling NC detection of M3-V2 L-shape interlayer leakages [see FIGS. 10-11, 18-22, 41, and 43 for corresponding §112(f) structure/acts].

Still further aspects of the invention relate to wafers, chips, and processes for making them that include/utilize DOEs based on means/steps for enabling NC detection of diagonal leakages, including but not limited to:

means/steps for enabling NC detection of AA diagonal leakages [see FIGS. 10-11, 23, 41, and 43 for corresponding §112(f) structure/acts];

means/steps for enabling NC detection of TS diagonal leakages [see FIGS. 10-11, 23, 41, and 43 for corresponding §112(f) structure/acts];

means/steps for enabling NC detection of AACNT diagonal leakages [see FIGS. 10-11, 23, 41, and 43 for corresponding §112(f) structure/acts];

means/steps for enabling NC detection of AACNT-AA diagonal leakages [see FIGS. 10-11, 23, 41, and 43 for corresponding §112(f) structure/acts];

means/steps for enabling NC detection of GATE diagonal leakages [see FIGS. 10-11, 23, 41, and 43 for corresponding §112(f) structure/acts];

means/steps for enabling NC detection of GATE-AACNT diagonal leakages [see FIGS. 10-11, 23, 41, and 43 for corresponding §112(f) structure/acts];

means/steps for enabling NC detection of GATECNT-GATE diagonal leakages [see FIGS. 10-11, 23, 41, and 43 for corresponding §112(f) structure/acts];

means/steps for enabling NC detection of GATECNT diagonal leakages [see FIGS. 10-11, 23, 41, 43, and 495-554 for corresponding §112(f) structure/acts];

means/steps for enabling NC detection of GATECNT-AACNT diagonal leakages [see FIGS. 10-11, 23, 41, 43, and 555-632 for corresponding §112(f) structure/acts];

means/steps for enabling NC detection of M1 diagonal leakages [see FIGS. 10-11, 23, 41, and 43 for corresponding §112(f) structure/acts];

means/steps for enabling NC detection of V0 diagonal leakages [see FIGS. 10-11, 23, 41, and 43 for corresponding §112(f) structure/acts];

means/steps for enabling NC detection of M1-V0 diagonal leakages [see FIGS. 10-11, 23, 41, and 43 for corresponding §112(f) structure/acts];

means/steps for enabling NC detection of V1-M1 diagonal leakages [see FIGS. 10-11, 23, 41, and 43 for corresponding §112(f) structure/acts];

means/steps for enabling NC detection of V1 diagonal leakages [see FIGS. 10-11, 23, 41, and 43 for corresponding §112(f) structure/acts];

means/steps for enabling NC detection of M2 diagonal leakages [see FIGS. 10-11, 23, 41, and 43 for corresponding §112(f) structure/acts];

means/steps for enabling NC detection of M2-V1 diagonal leakages [see FIGS. 10-11, 23, 41, and 43 for corresponding §112(f) structure/acts];

means/steps for enabling NC detection of M3 diagonal leakages [see FIGS. 10-11, 23, 41, and 43 for corresponding §112(f) structure/acts];

means/steps for enabling NC detection of V2-M2 diagonal leakages [see FIGS. 10-11, 23, 41, and 43 for corresponding §112(f) structure/acts];

means/steps for enabling NC detection of V2 diagonal leakages [see FIGS. 10-11, 23, 41, and 43 for corresponding §112(f) structure/acts]; and, means/steps for enabling NC detection of M3-V2 diagonal leakages [see FIGS. 10-11, 23, 41, and 43 for corresponding §112(f) structure/acts].

Still further aspects of the invention relate to wafers, chips, and processes for making them that include/utilize DOEs based on means/steps for enabling NC detection of corner leakages, including but not limited to:

means/steps for enabling NC detection of AA corner leakages [see FIGS. 10-11, 24-26, 41, and 43 for corresponding §112(f) structure/acts];

means/steps for enabling NC detection of AACNT corner leakages [see FIGS. 10-11, 24-26, 41, and 43 for corresponding §112(f) structure/acts];

means/steps for enabling NC detection of AACNT-AA corner leakages [see FIGS. 10-11, 24-26, 41, and 43 for corresponding §112(f) structure/acts];

means/steps for enabling NC detection of GATE corner leakages [see FIGS. 10-11, 24-26, 41, and 43 for corresponding §112(f) structure/acts];

means/steps for enabling NC detection of GATECNT-GATE corner leakages [see FIGS. 10-11, 24-26, 41, and 43 for corresponding §112(f) structure/acts];

means/steps for enabling NC detection of GATECNT-TS corner leakages [see FIGS. 10-11, 24-26, 41, and 43 for corresponding §112(f) structure/acts];

means/steps for enabling NC detection of GATECNT corner leakages [see FIGS. 10-11, 24-26, 41, and 43 for corresponding §112(f) structure/acts];

means/steps for enabling NC detection of GATECNT-AA corner leakages [see FIGS. 10-11, 24-26, 41, 43, and 263-286 for corresponding §112(f) structure/acts];

means/steps for enabling NC detection of GATECNT-AACNT corner leakages [see FIGS. 10-11, 24-26, 41, and 43 for corresponding §112(f) structure/acts];

means/steps for enabling NC detection of M1 corner leakages [see FIGS. 10-11, 24-26, 41, 43, and 416-494 for corresponding §112(f) structure/acts];

means/steps for enabling NC detection of V0 corner leakages [see FIGS. 10-11, 24-26, 41, and 43 for corresponding §112(f) structure/acts];

means/steps for enabling NC detection of M1-V0 corner leakages [see FIGS. 10-11, 24-26, 41, and 43 for corresponding §112(f) structure/acts];

means/steps for enabling NC detection of V1-M1 corner leakages [see FIGS. 10-11, 24-26, 41, and 43 for corresponding §112(f) structure/acts];

means/steps for enabling NC detection of V1 corner leakages [see FIGS. 10-11, 24-26, 41, and 43 for corresponding §112(f) structure/acts];

means/steps for enabling NC detection of M2 corner leakages [see FIGS. 10-11, 24-26, 41, and 43 for corresponding §112(f) structure/acts];

means/steps for enabling NC detection of M2-V1 corner leakages [see FIGS. 10-11, 24-26, 41, and 43 for corresponding §112(f) structure/acts];

means/steps for enabling NC detection of M3 corner leakages [see FIGS. 10-11, 24-26, 41, and 43 for corresponding §112(f) structure/acts];

means/steps for enabling NC detection of V2-M2 corner leakages [see FIGS. 10-11, 24-26, 41, and 43 for corresponding §112(f) structure/acts];

means/steps for enabling NC detection of V2 corner leakages [see FIGS. 10-11, 24-26, 41, and 43 for corresponding §112(f) structure/acts]; and, means/steps for enabling NC detection of M3-V2 corner leakages [see FIGS. 10-11, 24-26, 41, and 43 for corresponding §112(f) structure/acts];

Still further aspects of the invention relate to wafers, chips, and processes for making them that include/utilize DOEs based on means/steps for enabling NC detection of interlayer-overlap leakages, including but not limited to:

means/steps for enabling NC detection of GATE-AA interlayer overlap leakages [see FIGS. 10-11, 27, 41, 43, and 692-734 for corresponding §112(f) structure/acts];

means/steps for enabling NC detection of GATE-AACNT interlayer overlap leakages [see FIGS. 10-11, 27, 41, 43, and 633-691 for corresponding §112(f) structure/acts];

means/steps for enabling NC detection of GATE-TS interlayer overlap leakages [see FIGS. 10-11, 27, 41, and 43 for corresponding §112(f) structure/acts];

means/steps for enabling NC detection of GATECNT-TS interlayer overlap leakages [see FIGS. 10-11, 27, 41, and 43 for corresponding §112(f) structure/acts];

means/steps for enabling NC detection of GATECNT-AA interlayer overlap leakages [see FIGS. 10-11, 27, 41, and 43 for corresponding §112(f) structure/acts];

means/steps for enabling NC detection of V0-AA interlayer overlap leakages [see FIGS. 10-11, 27, 41, and 43 for corresponding §112(f) structure/acts];

means/steps for enabling NC detection of V0-AACNT interlayer overlap leakages [see FIGS. 10-11, 27, 41, and 43 for corresponding §112(f) structure/acts];

means/steps for enabling NC detection of V0-TS interlayer overlap leakages [see FIGS. 10-11, 27, 41, and 43 for corresponding §112(f) structure/acts];

means/steps for enabling NC detection of V0-GATE interlayer overlap leakages [see FIGS. 10-11, 27, 41, and 43 for corresponding §112(f) structure/acts];

means/steps for enabling NC detection of M1-GATECNT interlayer overlap leakages see FIGS. 10-11, 27, 41, and 43 for corresponding §112(f) structure/acts];

means/steps for enabling NC detection of M1-AACNT interlayer overlap leakages [see FIGS. 10-11, 27, 41, and 43 for corresponding §112(f) structure/acts];

means/steps for enabling NC detection of V1-V0 interlayer overlap leakages [see FIGS. 10-11, 27, 41, and 43 for corresponding §112(f) structure/acts];

means/steps for enabling NC detection of M2-M1-interlayer-overlap leakages [see FIGS. 10-11, 27, 41, and 43 for corresponding §112(f) structure/acts];

means/steps for enabling NC detection of V2-V1-interlayer-overlap leakages [see FIGS. 10-11, 27, 41, and 43 for corresponding §112(f) structure/acts]; and, means/steps for enabling NC detection of M3-M2-interlayer-overlap leakages [see FIGS. 10-11, 27, 41, and 43 for corresponding §112(f) structure/acts].

Still further aspects of the invention relate to wafers, chips, and processes for making them that include/utilize DOEs based on means/steps for enabling NC detection of via-chamfer leakages, including but not limited to:

means/steps for enabling NC detection of V0-GATECNT via chamfer leakages [see FIGS. 10-11, 28, 41, and 43 for corresponding §112(f) structure/acts];

means/steps for enabling NC detection of V0-AACNT via chamfer leakages [see FIGS. 10-11, 28, 41, 43, and 52-256 for corresponding §112(f) structure/acts];

means/steps for enabling NC detection of V1-M1 via chamfer leakages [see FIGS. 10-11, 28, 41, and 43 for corresponding §112(f) structure/acts];

means/steps for enabling NC detection of V2-M2 via chamfer leakages [see FIGS. 10-11, 28, 41, and 43 for corresponding §112(f) structure/acts]; and, means/steps for enabling NC detection of V3-M3 via chamfer leakages [see FIGS. 10-11, 28, 41, 43, and 257-262 for corresponding §112(f) structure/acts].

Still further aspects of the invention relate to wafers, chips, and processes for making them that include/utilize DOEs based on means/steps for enabling NC detection of merged-via leakages, including but not limited to:

means/steps for enabling NC detection of V0 merged via leakages [see FIGS. 10-11, 29, 41, and 43 for corresponding §112(f) structure/acts];

means/steps for enabling NC detection of V1 merged via leakages [see FIGS. 10-11, 29, 41, and 43 for corresponding §112(f) structure/acts]; and, means/steps for enabling NC detection of V2 merged via leakages [see FIGS. 10-11, 29, 41, and 43 for corresponding §112(f) structure/acts].

Still further aspects of the invention relate to wafers, chips, and processes for making them that include/utilize DOEs based on means/steps for enabling NC detection of snake resistances, including but not limited to:

means/steps for enabling NC detection of AA snake resistances [see FIGS. 12-13, 30, 41, and 43 for corresponding §112(f) structure/acts];

means/steps for enabling NC detection of TS snake resistances [see FIGS. 12-13, 30, 41, and 43 for corresponding §112(f) structure/acts];

means/steps for enabling NC detection of AACNT snake resistances [see FIGS. 12-13, 30, 41, and 43 for corresponding §112(f) structure/acts];

means/steps for enabling NC detection of GATE snake resistances [see FIGS. 12-13, 30, 41, 43, and 1041-1048 for corresponding §112(f) structure/acts];

means/steps for enabling NC detection of GATECNT snake resistances [see FIGS. 12-13, 30, 41, and 43 for corresponding §112(f) structure/acts];

means/steps for enabling NC detection of V0 snake resistances [see FIGS. 12-13, 30, 41, and 43 for corresponding §112(f) structure/acts];

means/steps for enabling NC detection of M1 snake resistances [see FIGS. 12-13, 30, 41, 43, 44, and 1049-1066 for corresponding §112(f) structure/acts];

- means/steps for enabling NC detection of M1-V0-AACNT snake resistances [see FIGS. 12-13, 30, 41, 43, and 1067-1071 for corresponding §112(f) structure/acts];
- means/steps for enabling NC detection of V1 snake resistances [see FIGS. 12-13, 30, 41, and 43 for corresponding §112(f) structure/acts];
- means/steps for enabling NC detection of M2 snake resistances [see FIGS. 12-13, 30, 41, and 43 for corresponding §112(f) structure/acts];
- means/steps for enabling NC detection of V2 snake resistances [see FIGS. 12-13, 30, 41, and 43 for corresponding §112(f) structure/acts]; and,
- means/steps for enabling NC detection of M3 snake resistances [see FIGS. 12-13, 30, 41, and 43 for corresponding §112(f) structure/acts].

Still further aspects of the invention relate to wafers, chips, and processes for making them that include/utilize DOEs based on means/steps for enabling NC detection of stitch resistances, including but not limited to:

- means/steps for enabling NC detection of AA stitch resistances [see FIGS. 12-13, 31-32, 41, and 43 for corresponding §112(f) structure/acts];
- means/steps for enabling NC detection of TS stitch resistances [see FIGS. 12-13, 31-32, 41, and 43 for corresponding §112(f) structure/acts];
- means/steps for enabling NC detection of AACNT stitch resistances [see FIGS. 12-13, 31-32, 41, and 43 for corresponding §112(f) structure/acts];
- means/steps for enabling NC detection of GATECNT stitch resistances [see FIGS. 12-13, 31-32, 41, and 43 for corresponding §112(f) structure/acts];
- means/steps for enabling NC detection of V0 stitch resistances [see FIGS. 12-13, 31-32, 41, and 43 for corresponding §112(f) structure/acts];
- means/steps for enabling NC detection of M1 stitch resistances [see FIGS. 12-13, 31-32, 41, 43, and 1072-1083 for corresponding §112(f) structure/acts];
- means/steps for enabling NC detection of V1 stitch resistances [see FIGS. 12-13, 31-32, 41, and 43 for corresponding §112(f) structure/acts];
- means/steps for enabling NC detection of M2 stitch resistances [see FIGS. 12-13, 31-32, 41, and 43 for corresponding §112(f) structure/acts];
- means/steps for enabling NC detection of V2 stitch resistances [see FIGS. 12-13, 31-32, 41, and 43 for corresponding §112(f) structure/acts]; and,
- means/steps for enabling NC detection of M3 stitch resistances [see FIGS. 12-13, 31-32, 41, and 43 for corresponding §112(f) structure/acts].

Still further aspects of the invention relate to wafers, chips, and processes for making them that include/utilize DOEs based on means/steps for enabling NC detection of via resistances, including but not limited to:

- means/steps for enabling NC detection of AACNT-TS via resistances [see FIGS. 12-13, 33, 41, 43, and 1629-1673 for corresponding §112(f) structure/acts];
- means/steps for enabling NC detection of AACNT-AA via resistances [see FIGS. 12-13, 33, 41, 43, and 1557-1628 for corresponding §112(f) structure/acts];
- means/steps for enabling NC detection of TS-AA via resistances [see FIGS. 12-13, 33, 41, 43, and 2315-2330 for corresponding §112(f) structure/acts];
- means/steps for enabling NC detection of GATECNT-GATE via resistances [see FIGS. 12-13, 33, 41, 43, 48, and 1699-2005 for corresponding §112(f) structure/acts];
- means/steps for enabling NC detection of GATECNT-AACNT via resistances [see FIGS. 12-13, 33, 41, 43, and 1674-1682 for corresponding §112(f) structure/acts];
- means/steps for enabling NC detection of GATECNT-AACNT-GATE via resistances [see FIGS. 12-13, 33, 41, 43, and 1683-1698 for corresponding §112(f) structure/acts];
- means/steps for enabling NC detection of V0-GATECNT via resistances [see FIGS. 12-13, 33, 41, 43, and 2375-2439 for corresponding §112(f) structure/acts];
- means/steps for enabling NC detection of V0-AA via resistances [see FIGS. 12-13, 33, 41, and 43 for corresponding §112(f) structure/acts];
- means/steps for enabling NC detection of V0 via resistances [see FIGS. 12-13, 33, 41, 43, and 2331-2344 for corresponding §112(f) structure/acts];
- means/steps for enabling NC detection of V0-TS via resistances [see FIGS. 12-13, 33, 41, and 43 for corresponding §112(f) structure/acts];
- means/steps for enabling NC detection of V0-AACNT via resistances [see FIGS. 12-13, 33, 41, 43, and 2345-2374 for corresponding §112(f) structure/acts];
- means/steps for enabling NC detection of V0-GATE via resistances [see FIGS. 12-13, 33, 41, and 43 for corresponding §112(f) structure/acts];
- means/steps for enabling NC detection of V1 via resistances [see FIGS. 12-13, 33, 41, 43, and 2440-2441 for corresponding §112(f) structure/acts];
- means/steps for enabling NC detection of M1-V0 resistances [see FIGS. 12-13, 33, 41, 43, and 2006-2220 for corresponding §112(f) structure/acts];
- means/steps for enabling NC detection of V1-M1 via resistances [see FIGS. 12-13, 33, 41, 43, and 2442-2459 for corresponding §112(f) structure/acts];
- means/steps for enabling NC detection of V1-M2 via resistances [see FIGS. 12-13, 33, 41, 43, and 2221-2256 for corresponding §112(f) structure/acts];
- means/steps for enabling NC detection of M1-GATECNT via resistances [see FIGS. 12-13, 33, 41, and 43 for corresponding §112(f) structure/acts];
- means/steps for enabling NC detection of V2-M3 via resistances [see FIGS. 12-13, 33, 41, 43, and 2257-2274 for corresponding §112(f) structure/acts];
- means/steps for enabling NC detection of M1-AANCT via resistances [see FIGS. 12-13, 33, 41, and 43 for corresponding §112(f) structure/acts];
- means/steps for enabling NC detection of V2-M2 via resistances [see FIGS. 12-13, 33, 41, and 43 for corresponding §112(f) structure/acts];
- means/steps for enabling NC detection V3 via resistances [see FIGS. 12-13, 33, 41, 43, and 2460-2461 for corresponding §112(f) structure/acts];
- means/steps for enabling NC detection of M4-V3 via resistances [see FIGS. 12-13, 33, 41, 43, and 2275-2296 for corresponding §112(f) structure/acts]; and,
- means/steps for enabling NC detection of M5-V4 via resistances [see FIGS. 12-13, 33, 41, 43, and 2297-2314 for corresponding §112(f) structure/acts].

Still further aspects of the invention relate to wafers, chips, and processes for making them that include/utilize DOEs based on means/steps for enabling NC detection of metal island resistances, including but not limited to:

- means/steps for enabling NC detection of M1 metal island resistances [see FIGS. 12-13, 34-35, 41, and 43 for corresponding §112(f) structure/acts];

means/steps for enabling NC detection of M2 metal island resistances [see FIGS. 12-13, 34-35, 41, and 43 for corresponding §112(f) structure/acts];

means/steps for enabling NC detection of M3 metal island resistances [see FIGS. 12-13, 34-35, 41, and 43 for corresponding §112(f) structure/acts];

Still further aspects of the invention relate to wafers, chips, and processes for making them that include/utilize DOEs based on means/steps for enabling NC detection of merged-via resistances, including but not limited to:

means/steps for enabling NC detection of V0-GATECNT merged via resistances [see FIGS. 12-13, 36, 41, and 43 for corresponding §112(f) structure/acts];

means/steps for enabling NC detection of V0 merged via resistances [see FIGS. 12-13, 36, 41, 43, and 735-785 for corresponding §112(f) structure/acts];

means/steps for enabling NC detection of V0-AACNT merged via resistances [see FIGS. 12-13, 36, 41, and 43 for corresponding §112(f) structure/acts];

means/steps for enabling NC detection of V1 merged via resistances [see FIGS. 12-13, 36, 41, and 43 for corresponding §112(f) structure/acts];

means/steps for enabling NC detection of V2 merged via resistances [see FIGS. 12-13, 36, 41, and 43 for corresponding §112(f) structure/acts];

means/steps for enabling NC detection of V1-M1 merged via resistances [see FIGS. 12-13, 36, 41, and 43 for corresponding §112(f) structure/acts]; and, means/steps for enabling NC detection of V2-M2 merged via resistances [see FIGS. 12-13, 36, 41, and 43 for corresponding §112(f) structure/acts].

Still further aspects of the invention relate to mesh-style NCEM pads, and their use with in-line process control/optimization, such pads comprising, for example: at least two parallel, elongated AACNT features, extending longitudinally in a first direction; at least two parallel, elongated GATECNT features, extending longitudinally in a second direction, perpendicular to the first direction; wherein the features are positioned such that each of the AANCT features intersects each of the GATECNT features. Such pads may include at least three (or four, or five, or six, etc.) parallel, elongated AACNT features that extend longitudinally in the first direction, and/or at least three (or four, or five, or six, etc.) parallel, elongated GATECNT features that extend longitudinally in the second direction. Such pads may be part of an assembly that includes: a mesh-style NCEM pad; and, an upper layer NCEM pad, overlying the mesh-style NCEM pad, said upper layer NCEM pad comprising: one or more mask-patterned features, in a first wiring layer (M1), that substantially cover the mesh-style NCEM pad; and, one or more mask-patterned features, in a via to interconnect stack (V0) layer, that provide electrical connection(s) between the M1 feature(s) and the mesh-style NCEM pad. Such V0 features may be positioned at the intersections of the underlying AACNT and GATECNT features, or may be positioned to avoid intersections of the underlying AACNT and GATECNT features. The one or more M1 features may include multiple, parallel, elongated M1 features. Any of the aforesaid features may be single-patterned, double-patterned, triple-patterned, etc. Such mesh-style NCEM pads may be used in NCEM-enabled fill cells, including but not limited to: AA-tip-to-tip-short-configured, NCEM-enabled fill cells; AACNT-tip-to-tip-short-configured, NCEM-enabled fill cells; AACNT-AA-tip-to-tip-short-configured, NCEM-enabled fill cells; AACNT-TS-tip-to-tip-short-configured, NCEM-enabled fill cells; TS-tip-to-tip-short-configured, NCEM-enabled fill cells; GATE-tip-to-tip-short-configured, NCEM-enabled fill cells; GATECNT-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; M1-tip-to-tip-short-configured, NCEM-enabled fill cells; V0-tip-to-tip-short-configured, NCEM-enabled fill cells; M1-V0-tip-to-tip-short-configured, NCEM-enabled fill cells; V1-M1-tip-to-tip-short-configured, NCEM-enabled fill cells; V1-tip-to-tip-short-configured, NCEM-enabled fill cells; M2-tip-to-tip-short-configured, NCEM-enabled fill cells; M2-V1-tip-to-tip-short-configured, NCEM-enabled fill cells; V2-M2-tip-to-tip-short-configured, NCEM-enabled fill cells; M3-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; GATECNT-AACNT-TS-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-side-short-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AA-corner-short-configured, NCEM-enabled fill cells; GATECNT-AACNT-corner-short-configured, NCEM-enabled fill cells; M1-corner-short-configured, NCEM-enabled fill cells; V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-short-configured, NCEM-enabled fill cells; M3-V2-corner-short-configured, NCEM-enabled fill cells; GATE-AA-interlayer-overlap-short-configured, NCEM-enabled fill cells; GATE-AACNT-interlayer-overlap-short-configured, NCEM-enabled fill cells; GATE-TS-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V3-M3-via-chamfer-short-configured, NCEM-enabled fill cells; V0-merged-via-short-configured, NCEM-enabled fill cells; V1-merged-via-short-configured, NCEM-enabled fill cells; V2-merged-via-short-configured, NCEM-enabled fill cells; AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells; GATECNT-snake-open-configured, NCEM-enabled fill cells; V0-snake-open-configured, NCEM-enabled fill cells; M1-snake-open-configured, NCEM-enabled fill cells; M1-V0-AACNT-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open-configured, NCEM-enabled fill cells; GATECNT-AACNT-via-open-configured, NCEM-enabled fill cells; GATECNT-AACNT-GATE-via-open-configured, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-via-open-configured, NCEM-enabled fill cells; V1-M1-viaopen-configured, NCEM-enabled fill cells; V1-M2-via-open-configured, NCEM-enabled fill cells; M1-GATECNT-via-open-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; V3-via-open-configured, NCEM-enabled fill cells; M4-V3-via-open-configured, NCEM-enabled fill cells; M5-V4-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; and/or V2-M2-merged-via-open-configured, NCEM-enabled fill cells. Using such mesh-style pads, a method for processing a semiconductor substrate may include: using a first mask to pattern a plurality of adjacent AACNT stripes on the substrate; using a second mask to pattern a plurality of adjacent GATECNT stripes on the substrate, where the GATECNT stripes perpendicularly overlap the AACNT stripes to form a mesh-style NCEM pad; and, obtaining in-line NCEM from the mesh-style NCEM pad. Such process may further include: using a third mask to pattern a plurality of V0 vias above at least some of the GATECNT and/or AACNT stripes of the mesh-style NCEM pad; and, using a fourth mask to pattern one or more M1 features above one or more of said V0 vias to form an M1 NCEM pad, and may further include: obtaining in-line NCEM from the M1 NCEM pad.

BRIEF DESCRIPTION OF THE FIGURES

To provide a more complete understanding of the present disclosure and features and advantages thereof, reference is made to the following set of figures, taken in conjunction with the accompanying description, in which:

[Note regarding the figures in this application, as well as in the '463 provisional application: Those figures numbered 52[A,B,C], 53[A,B,C], et seq. are to-scale layouts of the exemplified cells. While certain detail in these layouts may be difficult to see on the application or patent as published, persons skilled in the art will appreciate that the SCORE tab in USPTO's Public PAIR system provides access to the applicant's PDF drawings, as originally uploaded, which can be electronically downloaded and blown up to reveal any level of desired detail.]

FIG. 9AA depicts an exemplary mesh-style, NCEM-enabled pad, formed from a 10×9 grid of single-patterned GATECNT and double-patterned AACNT stripes, with an overlying, solid M1 pad, and a plurality of V0 vias positioned to avoid GATECNT-AACNT junction points;

FIG. 9BB depicts an exemplary mesh-style, NCEM-enabled pad, formed from a 10×9 grid of double-patterned GATECNT and double-patterned AACNT stripes, with an overlying, solid M1 pad, and a plurality of V0 vias positioned to avoid GATECNT-AACNT junction points;

FIG. 9CC depicts an exemplary mesh-style, NCEM-enabled pad, formed from a 10×9 grid of triple-patterned GATECNT and single-patterned AACNT stripes, with an overlying, solid M1 pad, and a plurality of V0 vias positioned to avoid GATECNT-AACNT junction points;

FIG. 9DD depicts an exemplary mesh-style, NCEM-enabled pad, formed from a 10×9 grid of triple-patterned GATECNT and double-patterned AACNT stripes, with an overlying, solid M1 pad, and a plurality of V0 vias positioned to avoid GATECNT-AACNT junction points;

FIG. 9EE depicts an exemplary mesh-style, NCEM-enabled pad, formed from a 10×9 grid of single-patterned GATECNT and triple-patterned AACNT stripes, with an overlying, solid M1 pad, and a plurality of V0 vias positioned to avoid GATECNT-AACNT junction points;

FIG. 9FF depicts an exemplary mesh-style, NCEM-enabled pad, formed from a 10×9 grid of double-patterned GATECNT and triple-patterned AACNT stripes, with an overlying, solid M1 pad, and a plurality of V0 vias positioned to avoid GATECNT-AACNT junction points, with an overlying, solid M1 pad, and a plurality of V0 vias positioned to avoid GATECNT-AACNT junction points;

FIG. 9GG depicts an exemplary mesh-style, NCEM-enabled pad, formed from a 10×9 grid of triple-patterned GATECNT and triple-patterned AACNT stripes, with an overlying, solid M1 pad, and a plurality of V0 vias positioned to avoid GATECNT-AACNT junction points;

FIG. 9HH depicts an exemplary mesh-style, NCEM-enabled pad, formed from a 10×9 grid of single-patterned GATECNT and single-patterned AACNT stripes, with an overlying, non-solid M1 pad, and a plurality of V0 vias positioned at GATECNT-AACNT junction points;

FIG. 9II depicts an exemplary mesh-style, NCEM-enabled pad, formed from a 10×9 grid of double-patterned GATECNT and single-patterned AACNT stripes, with an overlying, non-solid M1 pad, and a plurality of V0 vias positioned at GATECNT-AACNT junction points;

FIG. 9JJ depicts an exemplary mesh-style, NCEM-enabled pad, formed from a 10×9 grid of single-patterned GATECNT and double-patterned AACNT stripes, with an overlying, non-solid M1 pad, and a plurality of V0 vias positioned at GATECNT-AACNT junction points;

FIG. 9KK depicts an exemplary mesh-style, NCEM-enabled pad, formed from a 10×9 grid of double-patterned GATECNT and double-patterned AACNT stripes, with an overlying, non-solid M1 pad, and a plurality of V0 vias positioned at GATECNT-AACNT junction points;

FIG. 9LL depicts an exemplary mesh-style, NCEM-enabled pad, formed from a 10×9 grid of triple-patterned GATECNT and single-patterned AACNT stripes, with an overlying, non-solid M1 pad, and a plurality of V0 vias positioned at GATECNT-AACNT junction points;

FIG. 9MM depicts an exemplary mesh-style, NCEM-enabled pad, formed from a 10×9 grid of triple-patterned GATECNT and double-patterned AACNT stripes, with an overlying, non-solid M1 pad, and a plurality of V0 vias positioned at GATECNT-AACNT junction points;

FIG. 9NN depicts an exemplary mesh-style, NCEM-enabled pad, formed from a 10×9 grid of single-patterned GATECNT and triple-patterned AACNT stripes, with an overlying, non-solid M1 pad, and a plurality of V0 vias positioned at GATECNT-AACNT junction points;

FIG. 9OO depicts an exemplary mesh-style, NCEM-enabled pad, formed from a 10×9 grid of double-patterned GATECNT and triple-patterned AACNT stripes, with an overlying, non-solid M1 pad, and a plurality of V0 vias positioned at GATECNT-AACNT junction points;

FIG. 9PP depicts an exemplary mesh-style, NCEM-enabled pad, formed from a 10×9 grid of triple-patterned GATECNT and triple-patterned AACNT stripes, with an overlying, non-solid M1 pad, and a plurality of V0 vias positioned at GATECNT-AACNT junction points;

FIG. 9QQ depicts an exemplary mesh-style, NCEM-enabled pad, formed from a 10×9 grid of single-patterned GATECNT and single-patterned AACNT stripes, with an overlying, non-solid M1 pad, and a plurality of V0 vias positioned to avoid GATECNT-AACNT junction points;

FIG. 9RR depicts an exemplary mesh-style, NCEM-enabled pad, formed from a 10×9 grid of double-patterned GATECNT and single-patterned AACNT stripes, with an overlying, non-solid M1 pad, and a plurality of V0 vias positioned to avoid GATECNT-AACNT junction points;

FIG. 9SS depicts an exemplary mesh-style, NCEM-enabled pad, formed from a 10×9 grid of single-patterned GATECNT and double-patterned AACNT stripes, with an overlying, non-solid M1 pad, and a plurality of V0 vias positioned to avoid GATECNT-AACNT junction points;

FIG. 9TT depicts an exemplary mesh-style, NCEM-enabled pad, formed from a 10×9 grid of double-patterned GATECNT and double-patterned AACNT stripes, with an overlying, non-solid M1 pad, and a plurality of V0 vias positioned to avoid GATECNT-AACNT junction points;

FIG. 9UU depicts an exemplary mesh-style, NCEM-enabled pad, formed from a 10×9 grid of triple-patterned GATECNT and single-patterned AACNT stripes, with an overlying, non-solid M1 pad, and a plurality of V0 vias positioned to avoid GATECNT-AACNT junction points;

FIG. 9VV depicts an exemplary mesh-style, NCEM-enabled pad, formed from a 10×9 grid of triple-patterned GATECNT and double-patterned AACNT stripes, with an overlying, non-solid M1 pad, and a plurality of V0 vias positioned to avoid GATECNT-AACNT junction points;

FIG. 9WW depicts an exemplary mesh-style, NCEM-enabled pad, formed from a 10×9 grid of single-patterned GATECNT and triple-patterned AACNT stripes, with an overlying, non-solid M1 pad, and a plurality of V0 vias positioned to avoid GATECNT-AACNT junction points;

FIG. 9XX depicts an exemplary mesh-style, NCEM-enabled pad, formed from a 10×9 grid of double-patterned GATECNT and triple-patterned AACNT stripes, with an overlying, non-solid M1 pad, and a plurality of V0 vias positioned to avoid GATECNT-AACNT junction points;

FIG. 9YY depicts an exemplary mesh-style, NCEM-enabled pad, formed from a 10×9 grid of triple-patterned GATECNT and triple-patterned AACNT stripes, with an overlying, non-solid M1 pad, and a plurality of V0 vias positioned to avoid GATECNT-AACNT junction points;

FIG. 9ZZ depicts an exemplary mesh-style, NCEM-enabled pad, formed from a 10×9 grid of single-patterned GATECNT and single-patterned AACNT stripes, with an overlying, non-solid, double-patterned M1 pad, and a plurality of V0 vias positioned at GATECNT-AACNT junction points;

FIG. 9AAA depicts an exemplary mesh-style, NCEM-enabled pad, formed from a 10×9 grid of double-patterned GATECNT and single-patterned AACNT stripes, with an overlying, non-solid, double-patterned M1 pad, and a plurality of V0 vias positioned at GATECNT-AACNT junction points;

FIG. 9BBB depicts an exemplary mesh-style, NCEM-enabled pad, formed from a 10×9 grid of single-patterned GATECNT and double-patterned AACNT stripes, with an overlying, non-solid, double-patterned M1 pad, and a plurality of V0 vias positioned at GATECNT-AACNT junction points;

FIG. 9CCC depicts an exemplary mesh-style, NCEM-enabled pad, formed from a 10×9 grid of double-patterned GATECNT and double-patterned AACNT stripes, with an overlying, non-solid, double-patterned M1 pad, and a plurality of V0 vias positioned at GATECNT-AACNT junction points;

FIG. 9DDD depicts an exemplary mesh-style, NCEM-enabled pad, formed from a 10×9 grid of triple-patterned GATECNT and single-patterned AACNT stripes, with an overlying, non-solid, double-patterned M1 pad, and a plurality of V0 vias positioned at GATECNT-AACNT junction points;

FIG. 9EEE depicts an exemplary mesh-style, NCEM-enabled pad, formed from a 10×9 grid of triple-patterned GATECNT and double-patterned AACNT stripes, with an overlying, non-solid, double-patterned M1 pad, and a plurality of V0 vias positioned at GATECNT-AACNT junction points;

FIG. 9FFF depicts an exemplary mesh-style, NCEM-enabled pad, formed from a 10×9 grid of single-patterned GATECNT and triple-patterned AACNT stripes, with an overlying, non-solid, double-patterned M1 pad, and a plurality of V0 vias positioned at GATECNT-AACNT junction points;

FIG. 9GGG depicts an exemplary mesh-style, NCEM-enabled pad, formed from a 10×9 grid of double-patterned GATECNT and triple-patterned AACNT stripes, with an overlying, non-solid, double-patterned M1 pad, and a plurality of V0 vias positioned at GATECNT-AACNT junction points;

FIG. 9HHH depicts an exemplary mesh-style, NCEM-enabled pad, formed from a 10×9 grid of triple-patterned GATECNT and triple-patterned AACNT stripes, with an overlying, non-solid, double-patterned M1 pad, and a plurality of V0 vias positioned at GATECNT-AACNT junction points;

FIG. 9III depicts an exemplary mesh-style, NCEM-enabled pad, formed from a 10×9 grid of single-patterned GATECNT and single-patterned AACNT stripes, with an overlying, non-solid, double-patterned M1 pad, and a plurality of V0 vias positioned to avoid GATECNT-AACNT junction points;

FIG. 9JJJ depicts an exemplary mesh-style, NCEM-enabled pad, formed from a 10×9 grid of double-patterned GATECNT and single-patterned AACNT stripes, with an overlying, non-solid, double-patterned M1 pad, and a plurality of V0 vias positioned to avoid GATECNT-AACNT junction points;

FIG. 9KKK depicts an exemplary mesh-style, NCEM-enabled pad, formed from a 10×9 grid of single-patterned GATECNT and double-patterned AACNT stripes, with an overlying, non-solid, double-patterned M1 pad, and a plurality of V0 vias positioned to avoid GATECNT-AACNT junction points;

FIG. 9LLL depicts an exemplary mesh-style, NCEM-enabled pad, formed from a 10×9 grid of double-patterned GATECNT and double-patterned AACNT stripes, with an overlying, non-solid, double-patterned M1 pad, and a plurality of V0 vias positioned to avoid GATECNT-AACNT junction points;

FIG. 9MMM depicts an exemplary mesh-style, NCEM-enabled pad, formed from a 10×9 grid of triple-patterned GATECNT and single-patterned AACNT stripes, with an overlying, non-solid, double-patterned M1 pad, and a plurality of V0 vias positioned to avoid GATECNT-AACNT junction points;

FIG. 9NNN depicts an exemplary mesh-style, NCEM-enabled pad, formed from a 10×9 grid of triple-patterned GATECNT and double-patterned AACNT stripes, with an overlying, non-solid, double-patterned M1 pad, and a plurality of V0 vias positioned to avoid GATECNT-AACNT junction points;

FIG. 9000 depicts an exemplary mesh-style, NCEM-enabled pad, formed from a 10×9 grid of single-patterned GATECNT and triple-patterned AACNT stripes, with an overlying, non-solid, double-patterned M1 pad, and a plurality of V0 vias positioned to avoid GATECNT-AACNT junction points;

FIG. 9PPP depicts an exemplary mesh-style, NCEM-enabled pad, formed from a 10×9 grid of double-patterned GATECNT and triple-patterned AACNT stripes, with an overlying, non-solid, double-patterned M1 pad, and a plurality of V0 vias positioned to avoid GATECNT-AACNT junction points;

FIG. 9QQQ depicts an exemplary mesh-style, NCEM-enabled pad, formed from a 10×9 grid of triple-patterned GATECNT and triple-patterned AACNT stripes, with an overlying, non-solid, double-patterned M1 pad, and a plurality of V0 vias positioned to avoid GATECNT-AACNT junction points;

FIG. 9RRR depicts an exemplary mesh-style, NCEM-enabled pad, formed from a 10×9 grid of single-patterned GATECNT and single-patterned AACNT stripes, with an overlying, non-solid, triple-patterned M1 pad, and a plurality of V0 vias positioned at GATECNT-AACNT junction points;

FIG. 9SSS depicts an exemplary mesh-style, NCEM-enabled pad, formed from a 10×9 grid of double-patterned GATECNT and single-patterned AACNT stripes, with an overlying, non-solid, triple-patterned M1 pad, and a plurality of V0 vias positioned at GATECNT-AACNT junction points;

FIG. 9TTT depicts an exemplary mesh-style, NCEM-enabled pad, formed from a 10×9 grid of single-patterned GATECNT and double-patterned AACNT stripes, with an overlying, non-solid, triple-patterned M1 pad, and a plurality of V0 vias positioned at GATECNT-AACNT junction points;

FIG. 9000 depicts an exemplary mesh-style, NCEM-enabled pad, formed from a 10×9 grid of double-patterned GATECNT and double-patterned AACNT stripes, with an overlying, non-solid, triple-patterned M1 pad, and a plurality of V0 vias positioned at GATECNT-AACNT junction points;

FIG. 9VVV depicts an exemplary mesh-style, NCEM-enabled pad, formed from a 10×9 grid of triple-patterned GATECNT and single-patterned AACNT stripes, with an overlying, non-solid, triple-patterned M1 pad, and a plurality of V0 vias positioned at GATECNT-AACNT junction points;

FIG. 9WWW depicts an exemplary mesh-style, NCEM-enabled pad, formed from a 10×9 grid of triple-patterned GATECNT and double-patterned AACNT stripes, with an overlying, non-solid, triple-patterned M1 pad, and a plurality of V0 vias positioned at GATECNT-AACNT junction points;

FIG. 9XXX depicts an exemplary mesh-style, NCEM-enabled pad, formed from a 10×9 grid of single-patterned GATECNT and triple-patterned AACNT stripes, with an overlying, non-solid, triple-patterned M1 pad, and a plurality of V0 vias positioned at GATECNT-AACNT junction points;

FIG. 9YYY depicts an exemplary mesh-style, NCEM-enabled pad, formed from a 10×9 grid of double-patterned GATECNT and triple-patterned AACNT stripes, with an overlying, non-solid, triple-patterned M1 pad, and a plurality of V0 vias positioned at GATECNT-AACNT junction points;

FIG. 9ZZZ depicts an exemplary mesh-style, NCEM-enabled pad, formed from a 10×9 grid of triple-patterned GATECNT and triple-patterned AACNT stripes, with an overlying, non-solid, triple-patterned M1 pad, and a plurality of V0 vias positioned at GATECNT-AACNT junction points;

FIG. 9AAAA depicts an exemplary mesh-style, NCEM-enabled pad, formed from a 10×9 grid of single-patterned GATECNT and single-patterned AACNT stripes, with an overlying, non-solid, triple-patterned M1 pad, and a plurality of V0 vias positioned to avoid GATECNT-AACNT junction points;

FIG. 9BBBB depicts an exemplary mesh-style, NCEM-enabled pad, formed from a 10×9 grid of double-patterned GATECNT and single-patterned AACNT stripes, with an overlying, non-solid, triple-patterned M1 pad, and a plurality of V0 vias positioned to avoid GATECNT-AACNT junction points;

FIG. 9CCCC depicts an exemplary mesh-style, NCEM-enabled pad, formed from a 10×9 grid of single-patterned GATECNT and double-patterned AACNT stripes, with an overlying, non-solid, triple-patterned M1 pad, and a plurality of V0 vias positioned to avoid GATECNT-AACNT junction points;

FIG. 9DDDD depicts an exemplary mesh-style, NCEM-enabled pad, formed from a 10×9 grid of double-patterned GATECNT and double-patterned AACNT stripes, with an overlying, non-solid, triple-patterned M1 pad, and a plurality of V0 vias positioned to avoid GATECNT-AACNT junction points;

FIG. 9EEEE depicts an exemplary mesh-style, NCEM-enabled pad, formed from a 10×9 grid of triple-patterned GATECNT and single-patterned AACNT stripes, with an overlying, non-solid, triple-patterned M1 pad, and a plurality of V0 vias positioned to avoid GATECNT-AACNT junction points;

FIG. 9FFFF depicts an exemplary mesh-style, NCEM-enabled pad, formed from a 10×9 grid of triple-patterned GATECNT and double-patterned AACNT stripes, with an overlying, non-solid, triple-patterned M1 pad, and a plurality of V0 vias positioned to avoid GATECNT-AACNT junction points;

FIG. 9GGGG depicts an exemplary mesh-style, NCEM-enabled pad, formed from a 10×9 grid of single-patterned GATECNT and triple-patterned AACNT stripes, with an overlying, non-solid, triple-patterned M1 pad, and a plurality of V0 vias positioned to avoid GATECNT-AACNT junction points;

FIG. 9HHHH depicts an exemplary mesh-style, NCEM-enabled pad, formed from a 10×9 grid of double-patterned GATECNT and triple-patterned AACNT stripes, with an overlying, non-solid, triple-patterned M1 pad, and a plurality of V0 vias positioned to avoid GATECNT-AACNT junction points;

FIG. 9IIII depicts an exemplary mesh-style, NCEM-enabled pad, formed from a 10×9 grid of triple-patterned GATECNT and triple-patterned AACNT stripes, with an overlying, non-solid, triple-patterned M1 pad, and a plurality of V0 vias positioned to avoid GATECNT-AACNT junction points;

FIG. 39 shows the logical AND of patterning within both expanded test areas (of FIGS. 37 & 38);

FIG. 40 shows the logical OR of patterning within both expanded test areas (of FIGS. 37 & 38);

FIG. 41 depicts an exemplary process flow, suitable for use in connection with certain embodiments of the invention;

FIG. 42 depicts an exemplary process flow for obtaining and (optionally) using measurements from mesh-style NCEM pads;

FIG. 43 depicts another exemplary process flow, suitable for use in accordance with certain embodiments of the invention;

FIG. 44 depicts a plan view of an exemplary M1-snake-open-configured, NCEM-enabled fill cell;

FIG. 45 depicts a plan view of an exemplary AACNT-tip-to-side-short-configured, NCEM-enabled fill cell;

Figure 46A:
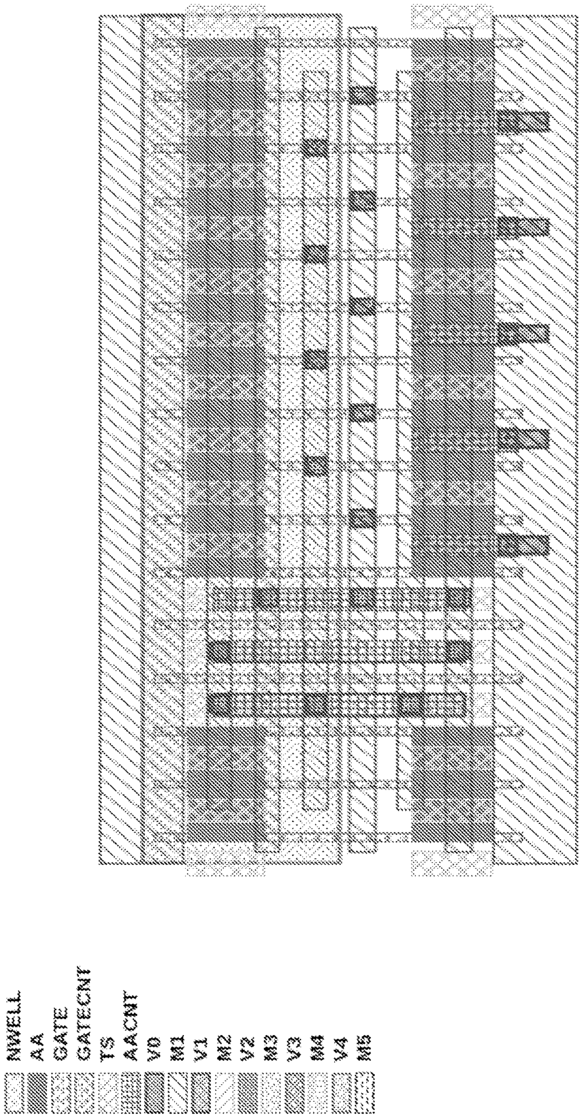
Figure 46B:
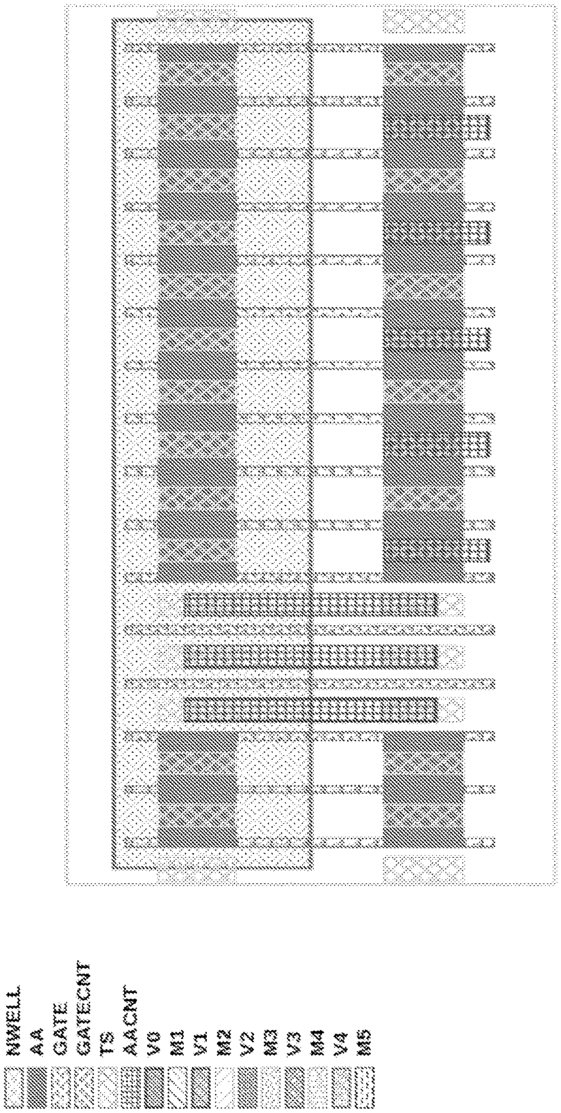
Figure 46C:
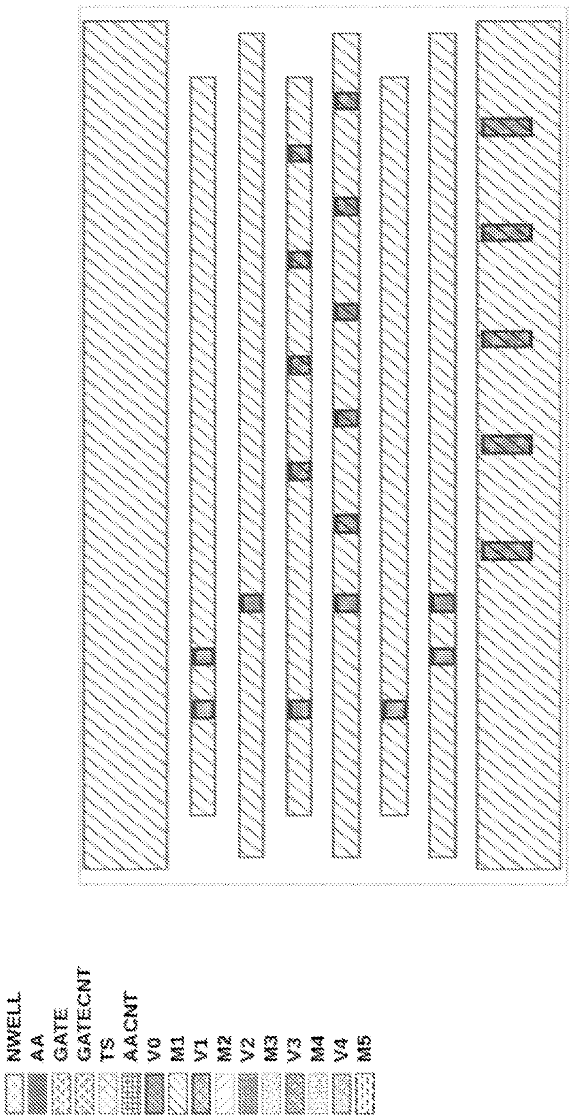
Figure 47A:
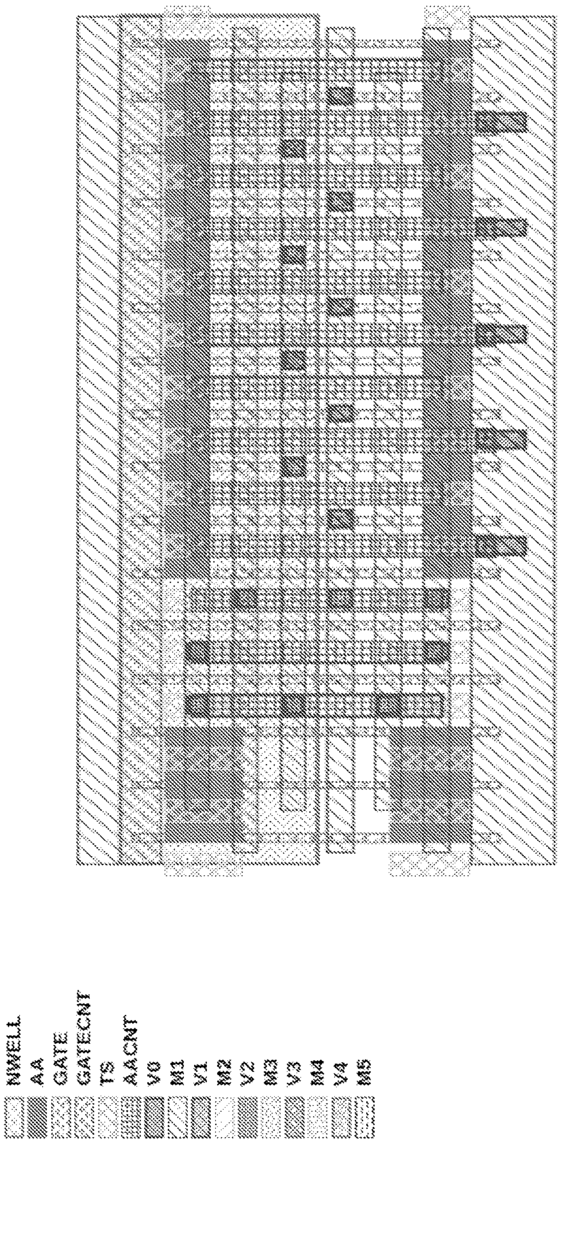
Figure 47B:
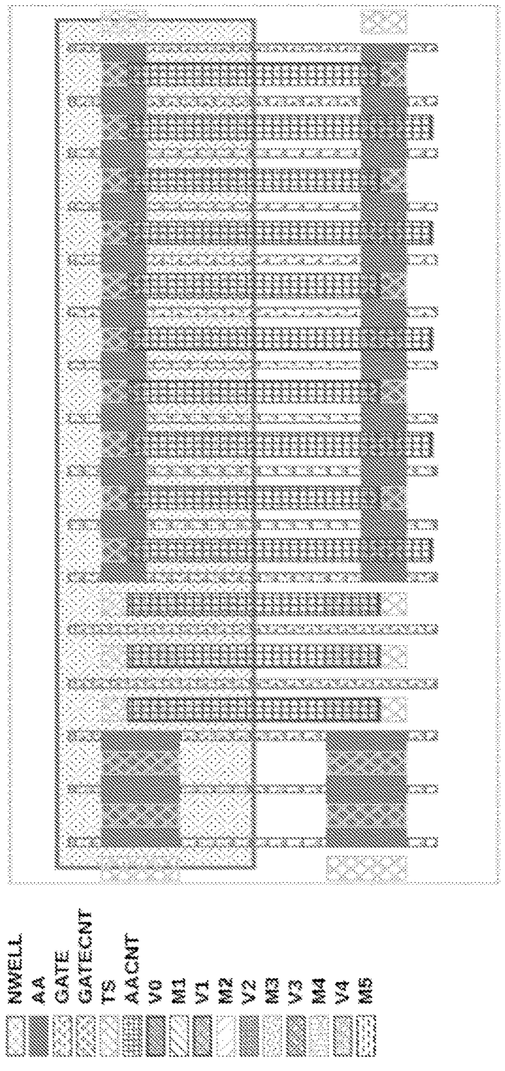
Figure 47C:
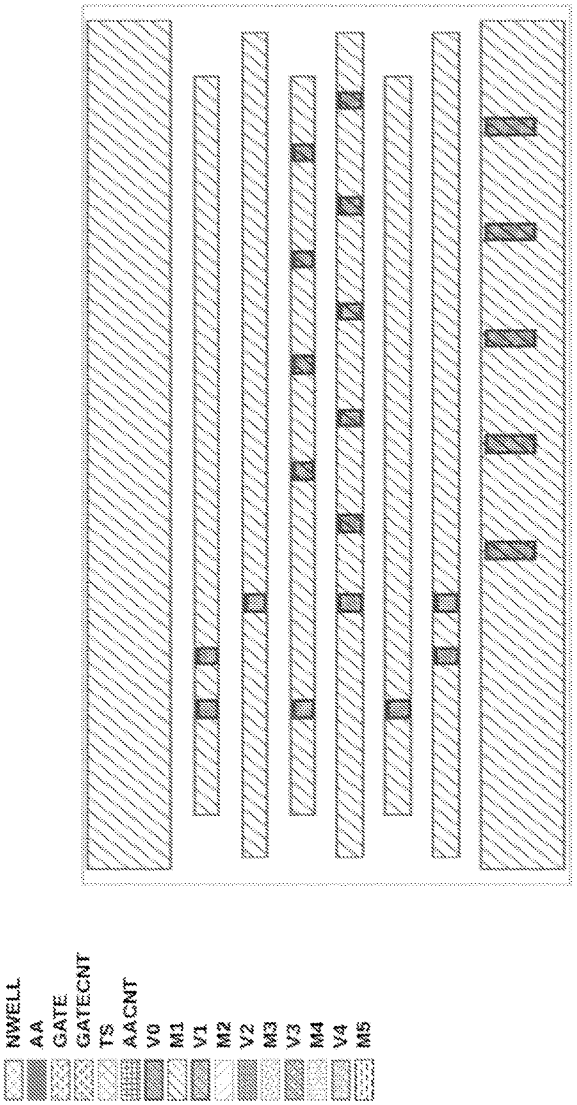
Figure 48A:
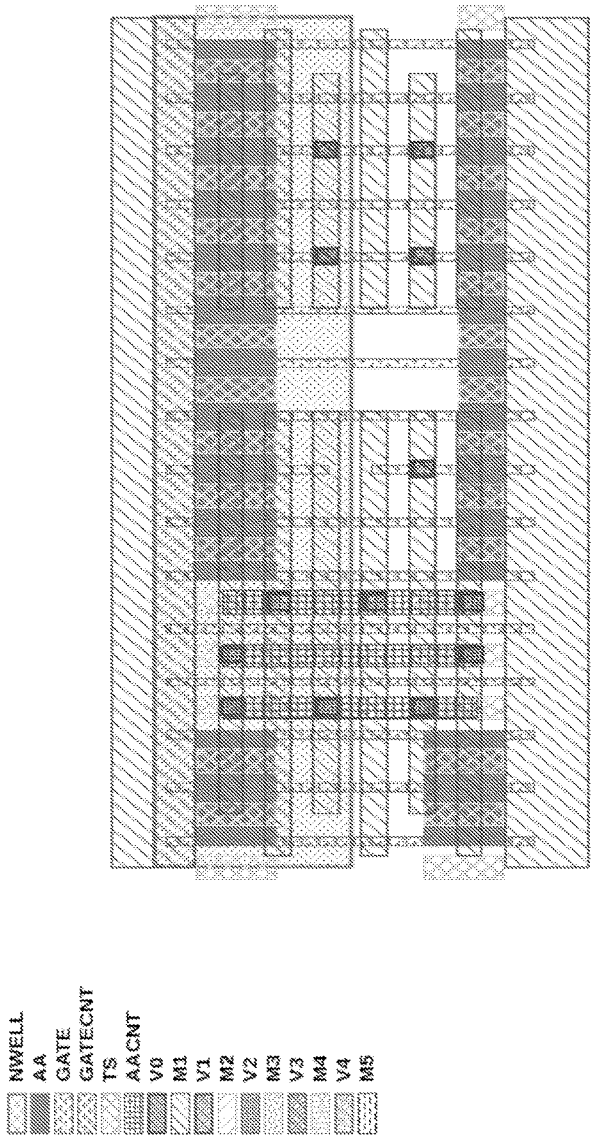
Figure 48B:
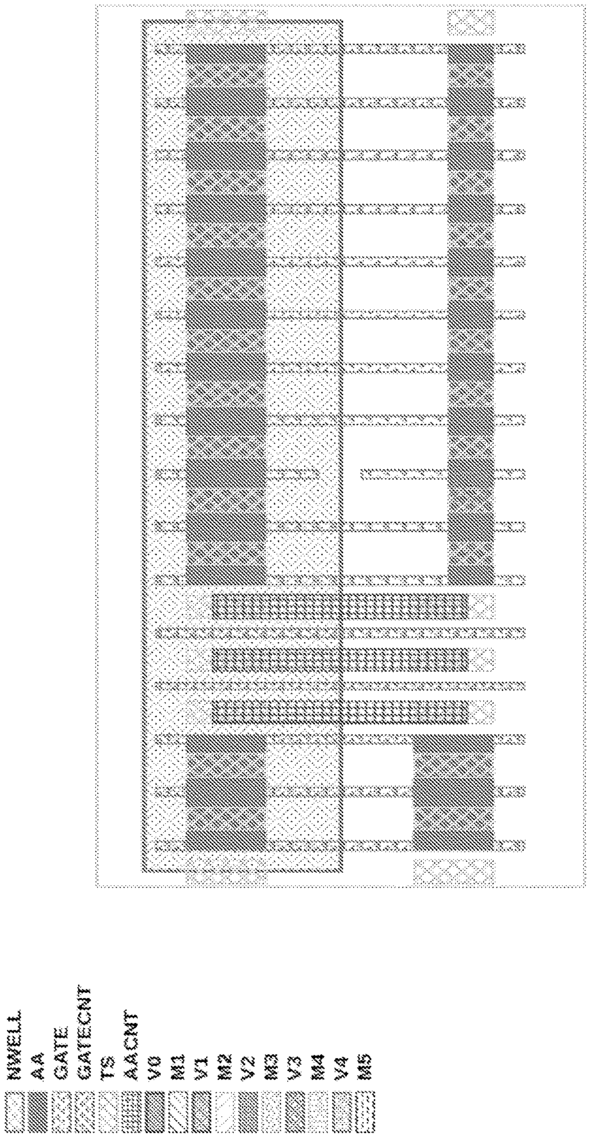
Figure 48C:
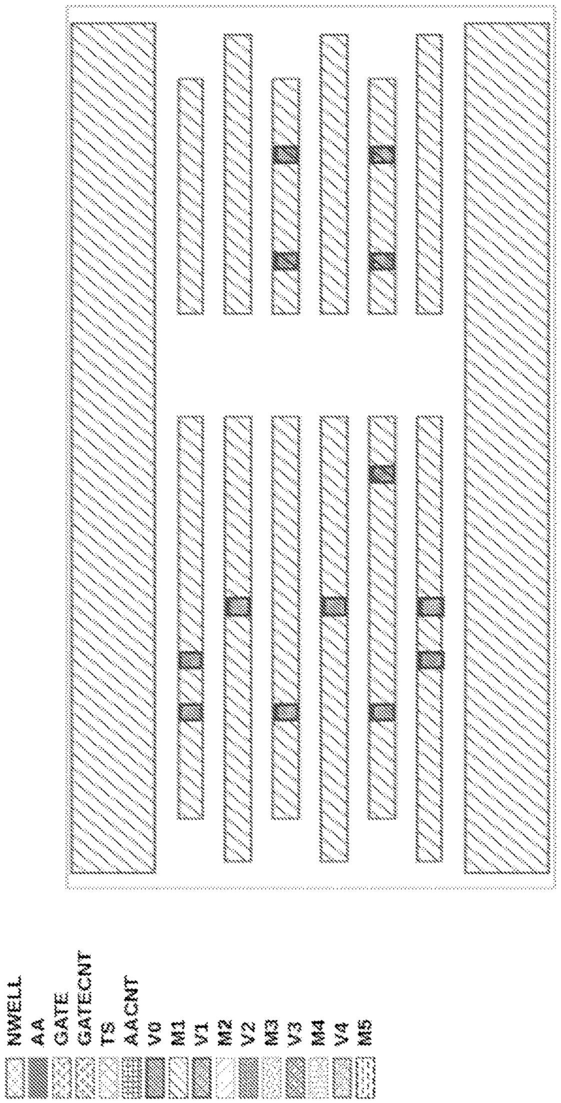
Figure 49A:
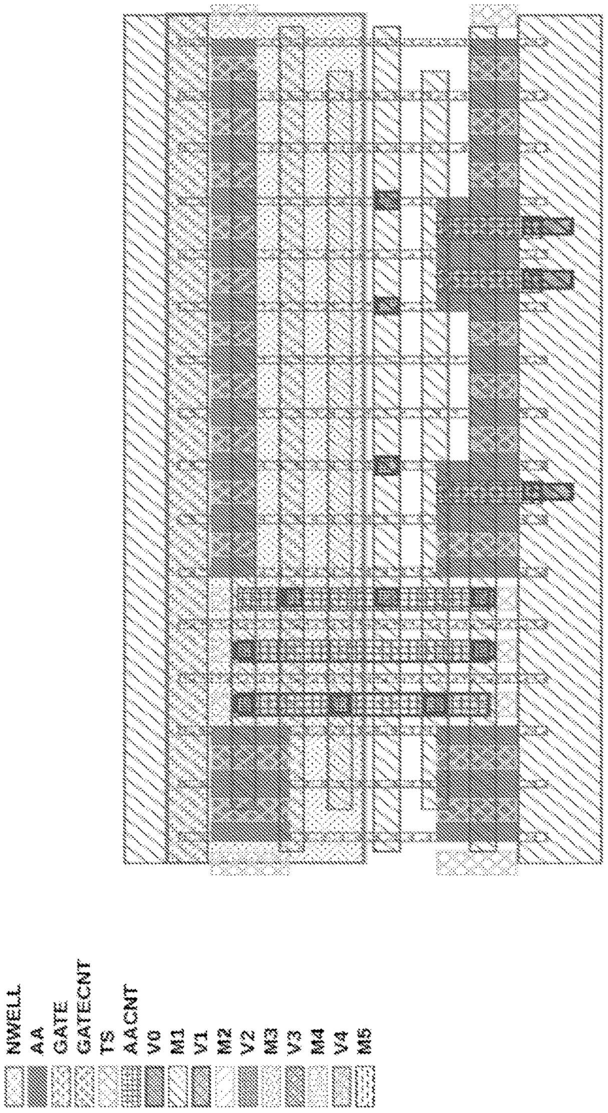
Figure 49B:
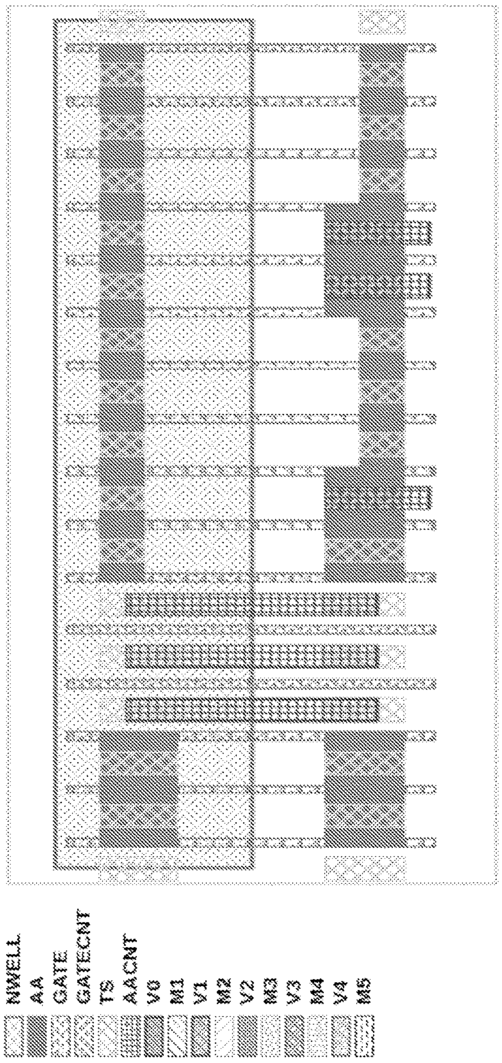
Figure 49C:
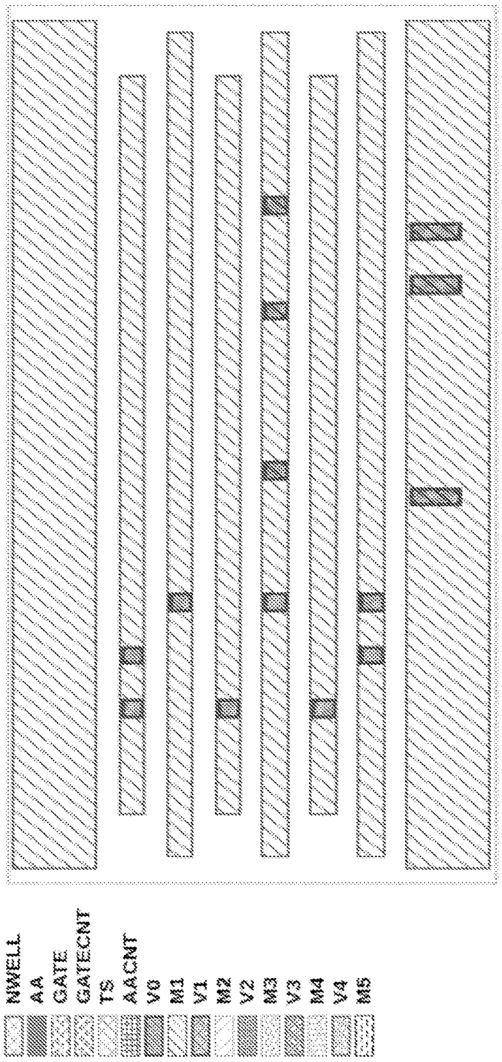
Figure 50A:
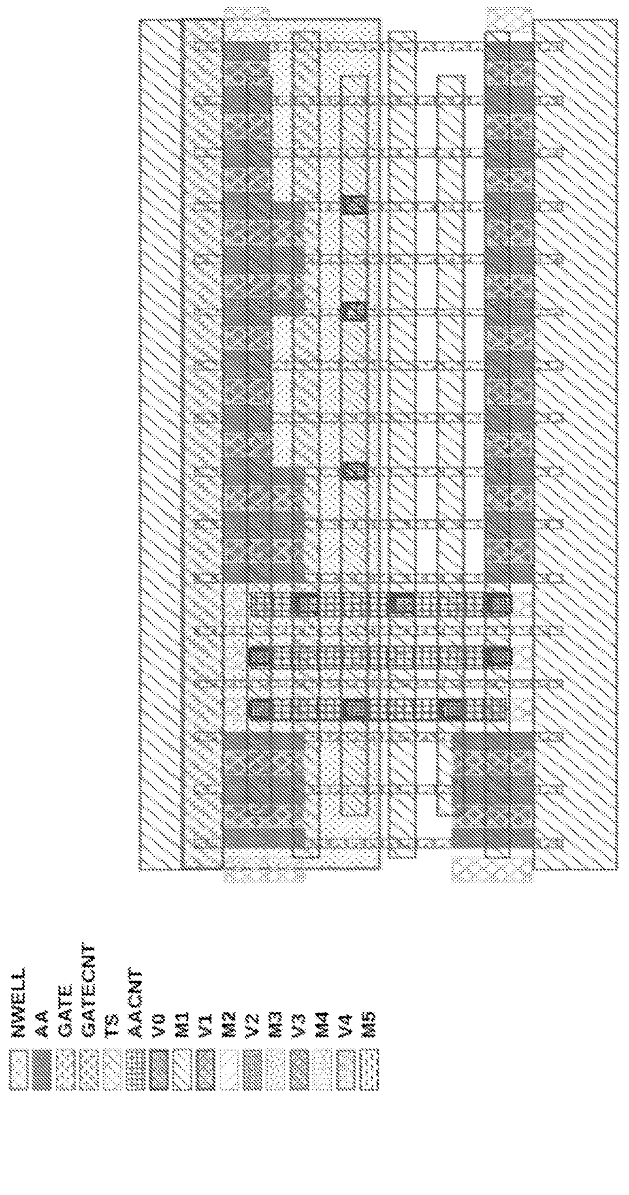
Figure 50B:
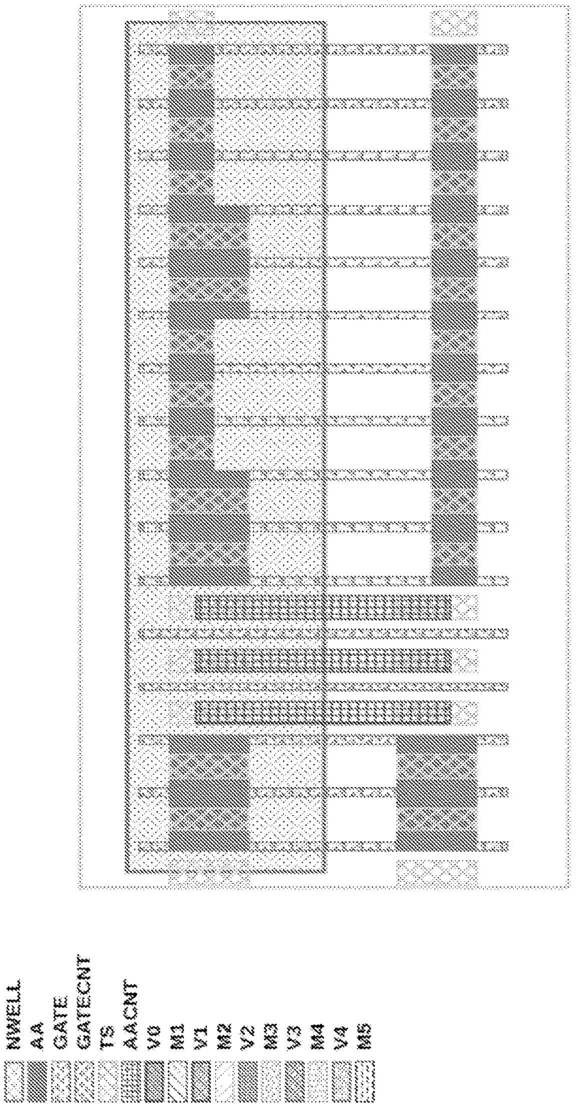
Figure 50C:
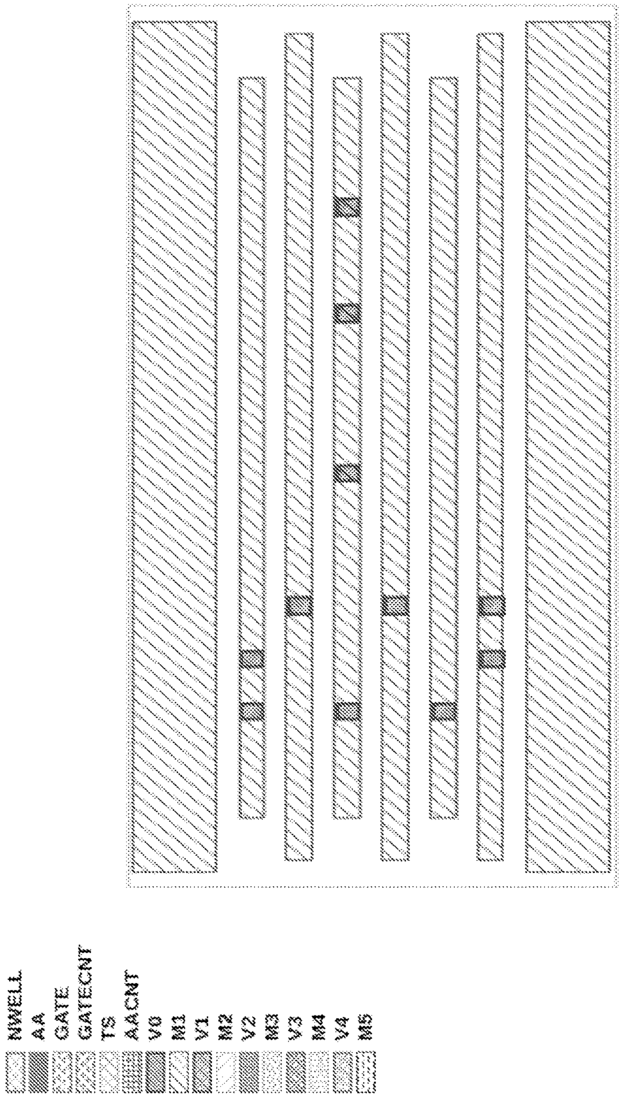
Figure 51:
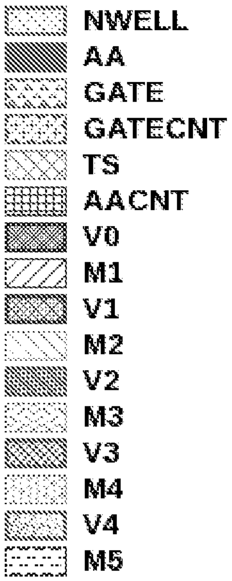
Figure 52A:
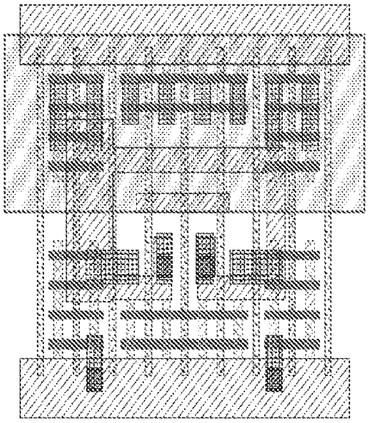
Figure 52B:
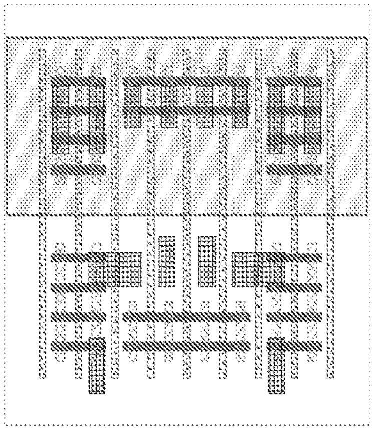
Figure 52C:
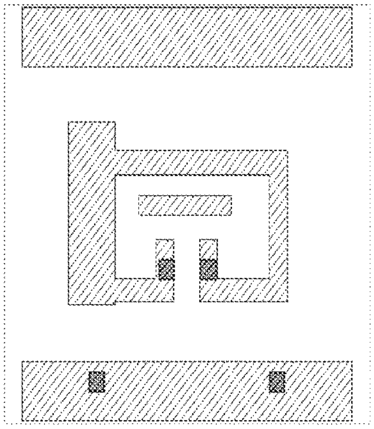
Figure 53A:
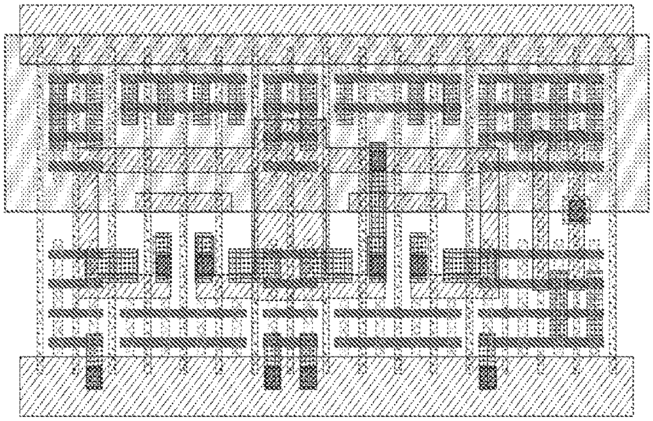
Figure 53B:
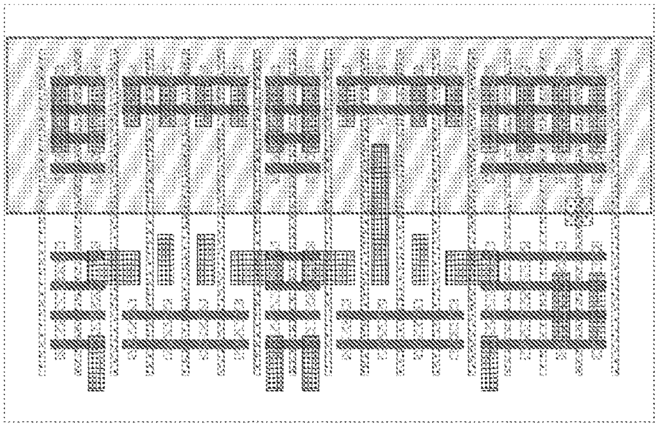
Figure 53C:
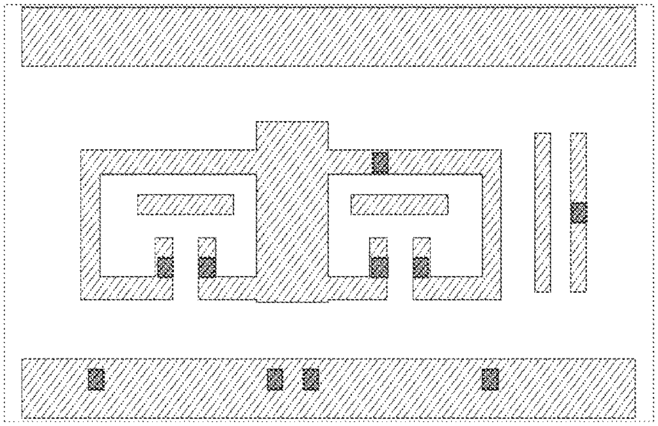
Figure 54A:
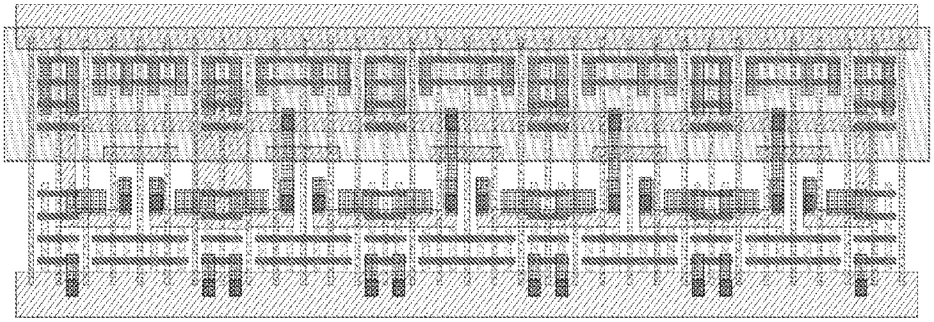
Figure 54B:
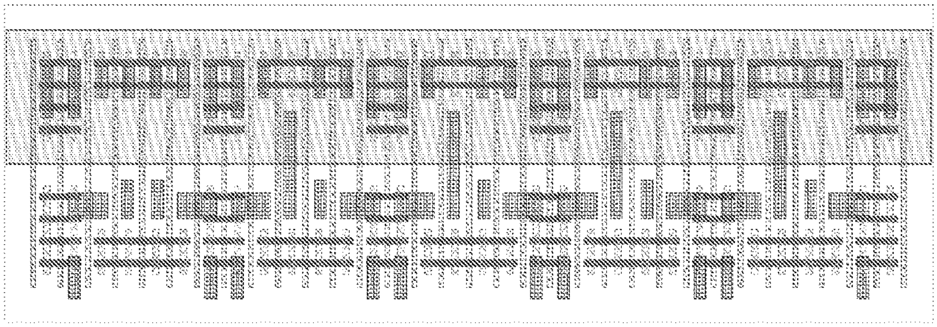
Figure 54C:
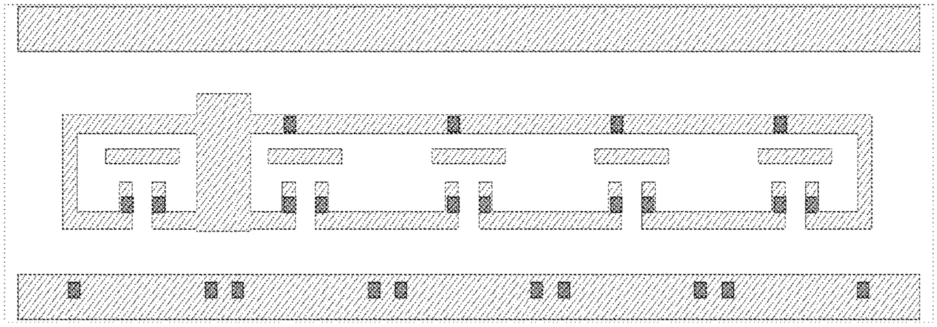
Figure 55A:
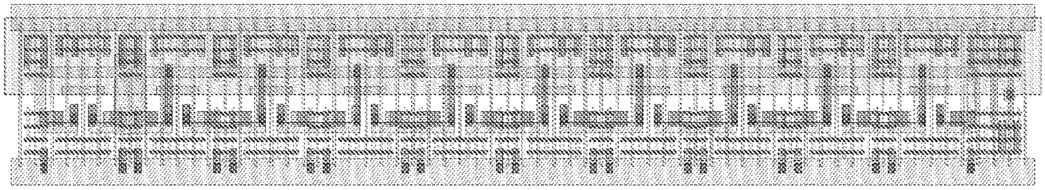
Figure 55B:
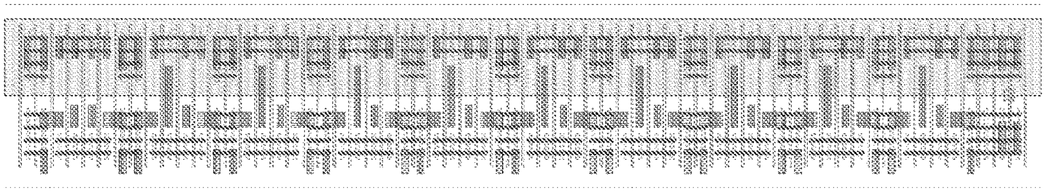
Figure 55C:
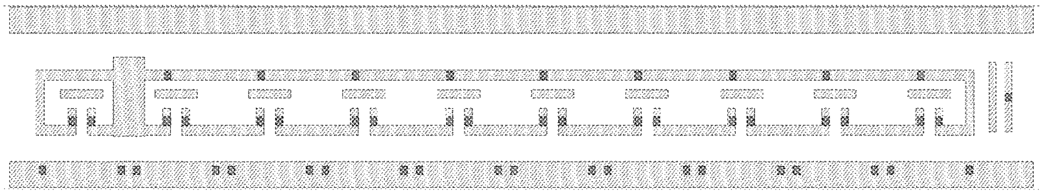
Figure 56A:
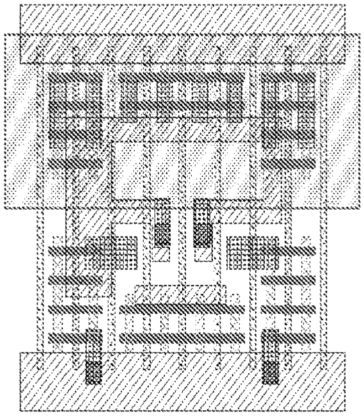
Figure 56B:
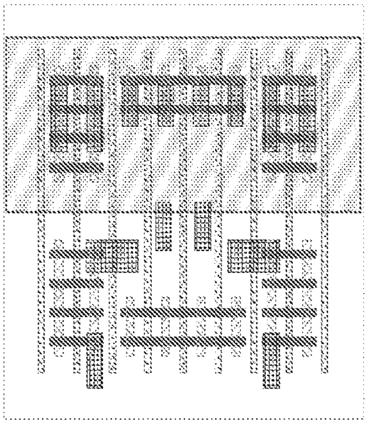
Figure 56C:
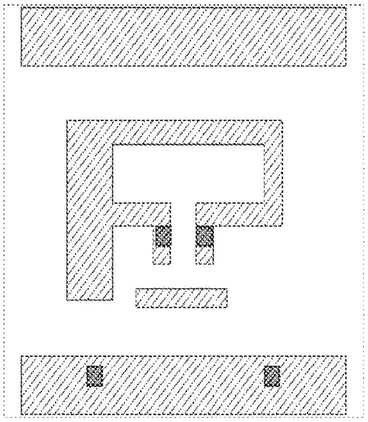
Figure 57A:
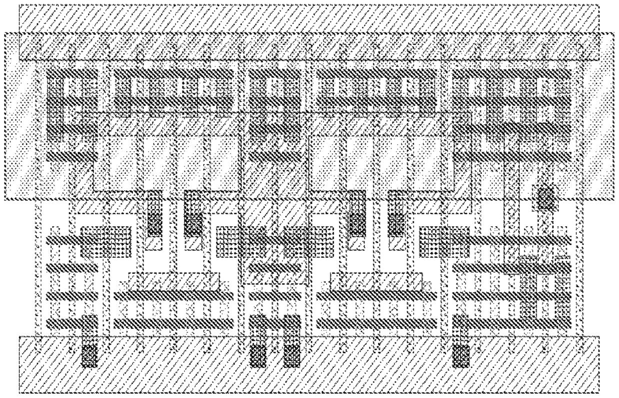
Figure 57B:
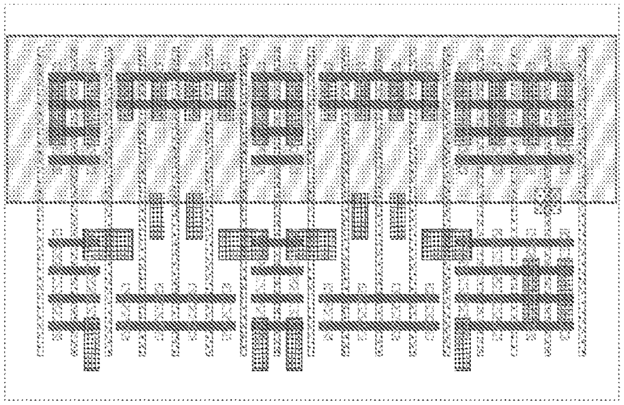
Figure 57C:
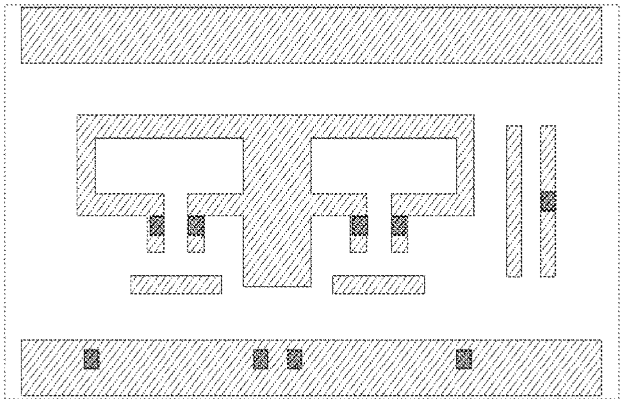
Figure 58A:
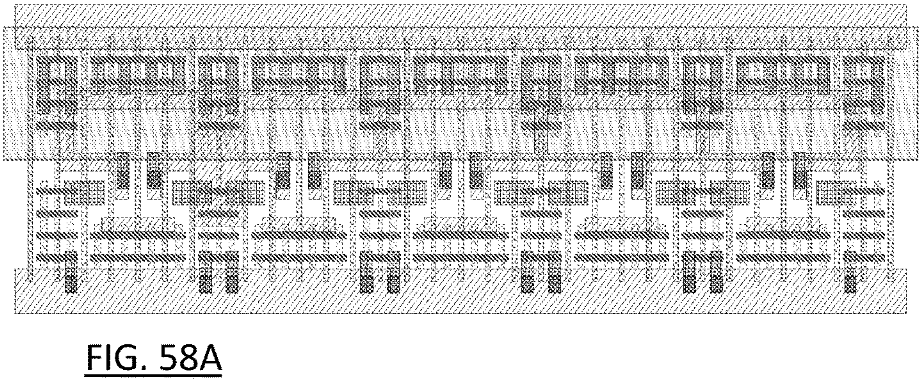
Figure 58B:
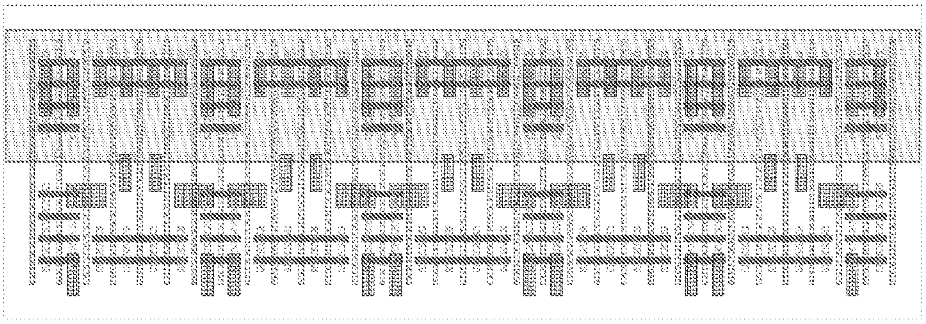
Figure 58C:
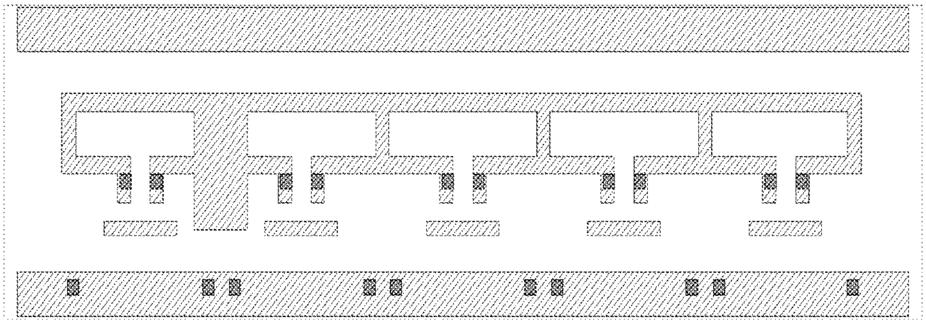
Figure 59A:
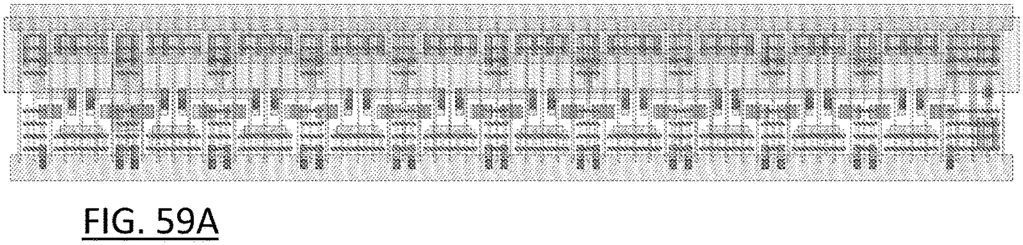
Figure 59B:
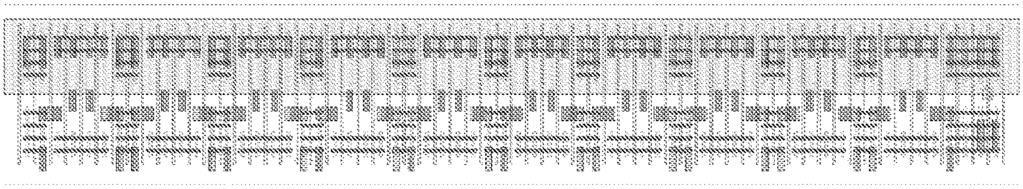
Figure 59C:
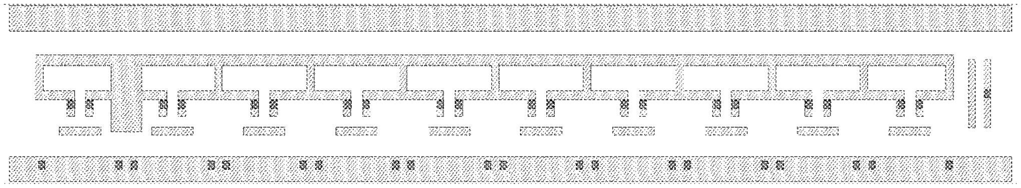
Figure 60A:
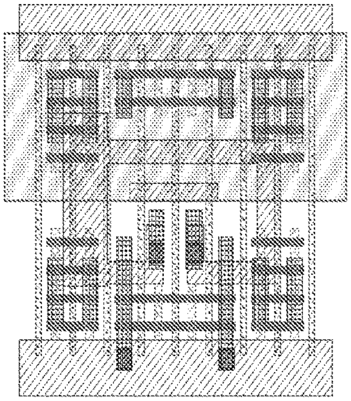
Figure 60B:
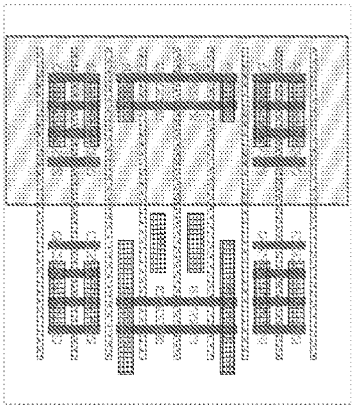
Figure 60C:
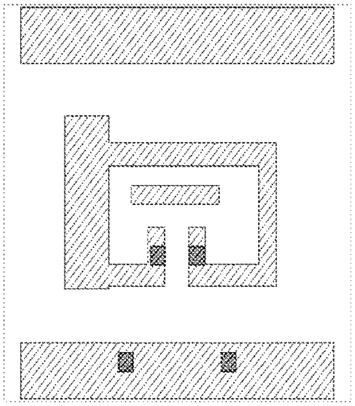
Figure 61A:
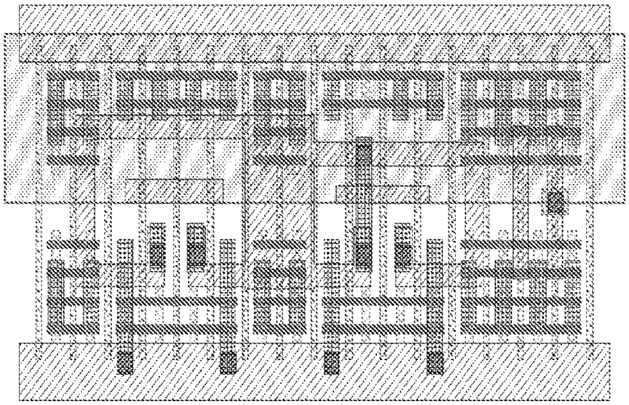
Figure 61B:
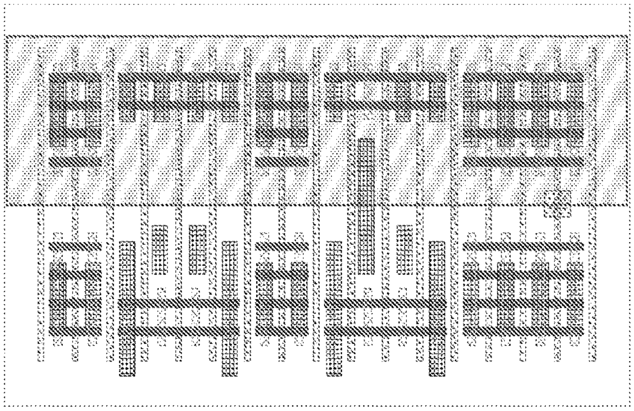
Figure 61C:
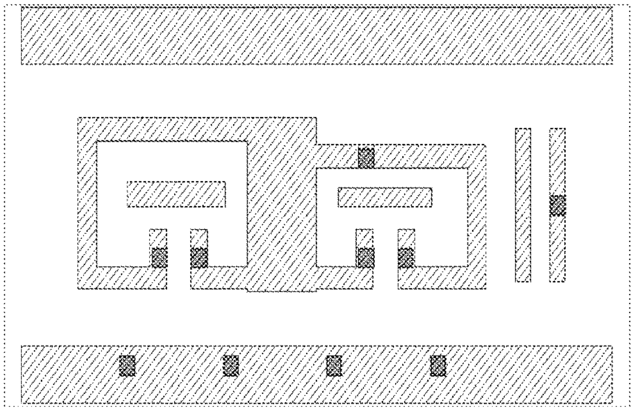
Figure 62A:
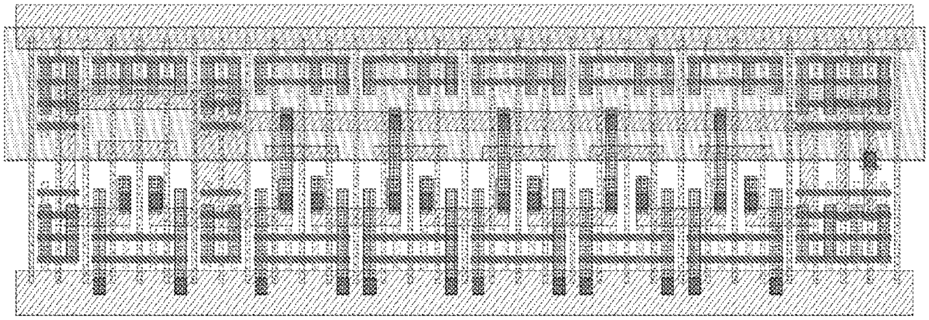
Figure 62B:
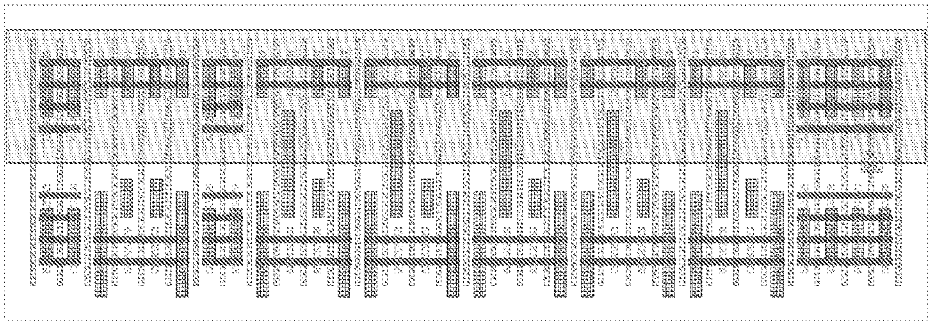
Figure 62C:
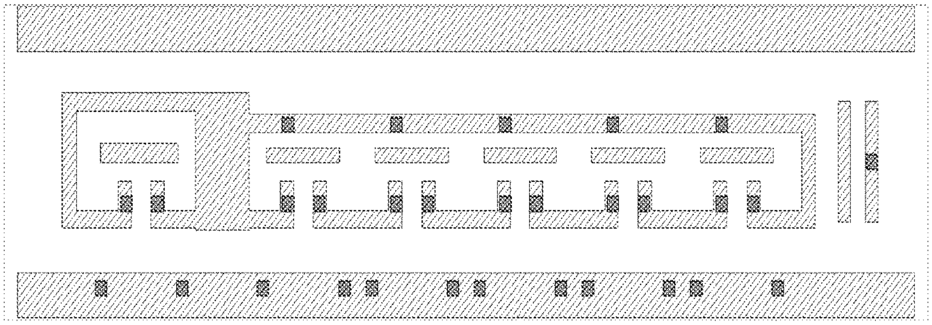
Figure 63A:
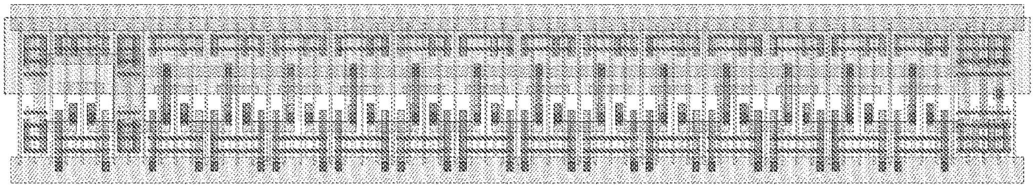
Figure 63B:
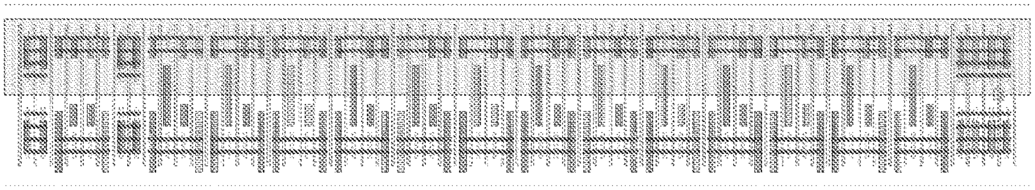
Figure 63C:
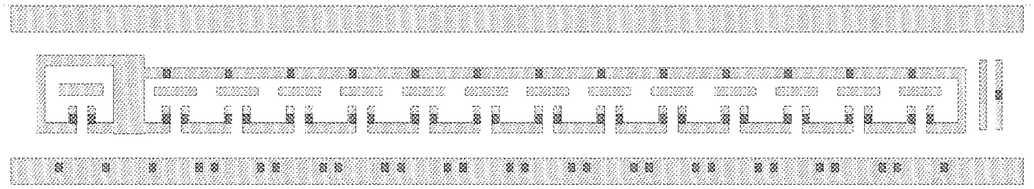
Figure 64A:
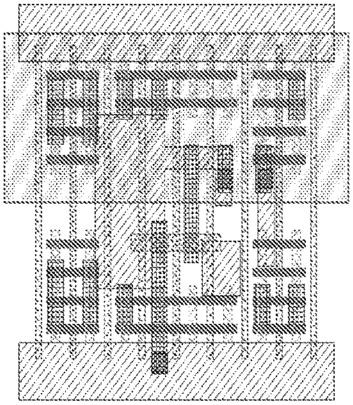
Figure 64B:
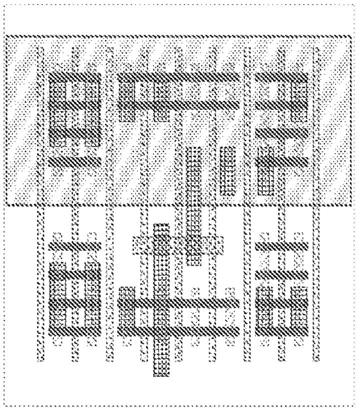
Figure 64C:
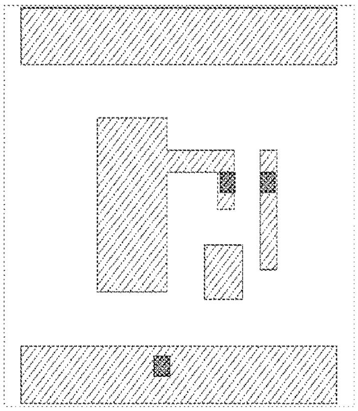
Figure 65A:
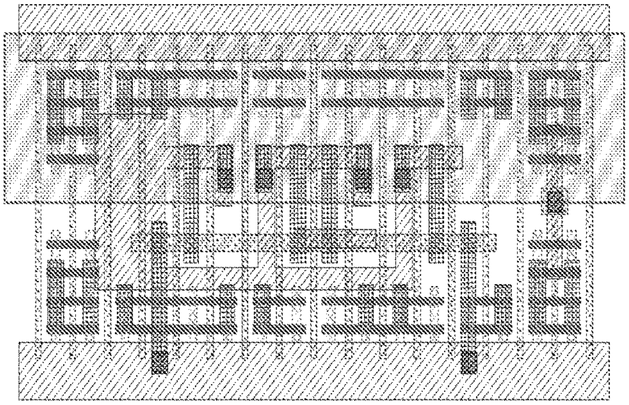
Figure 65B:
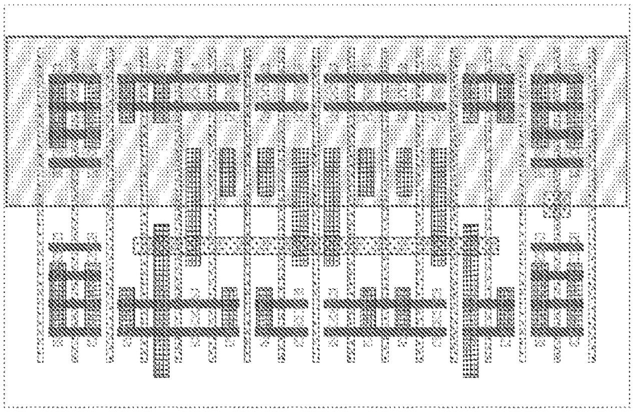
Figure 65C:
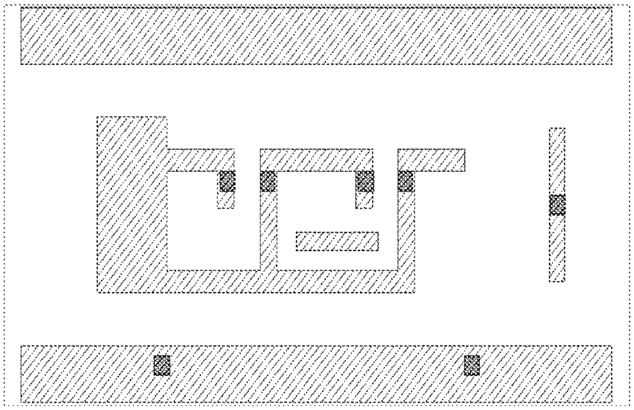
Figure 66A:
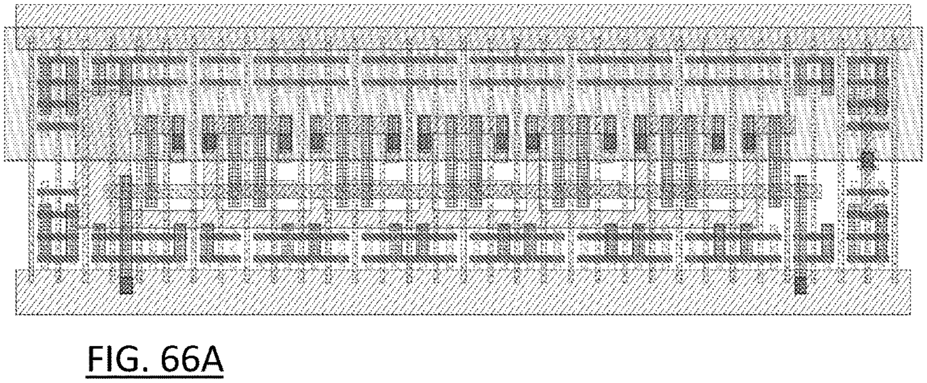
Figure 66B:
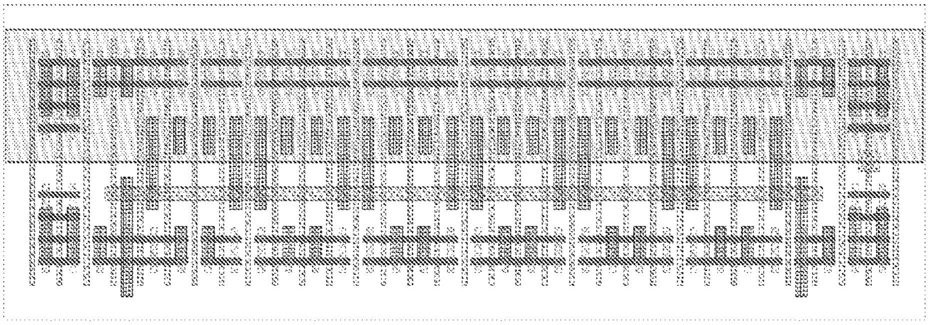
Figure 66C:
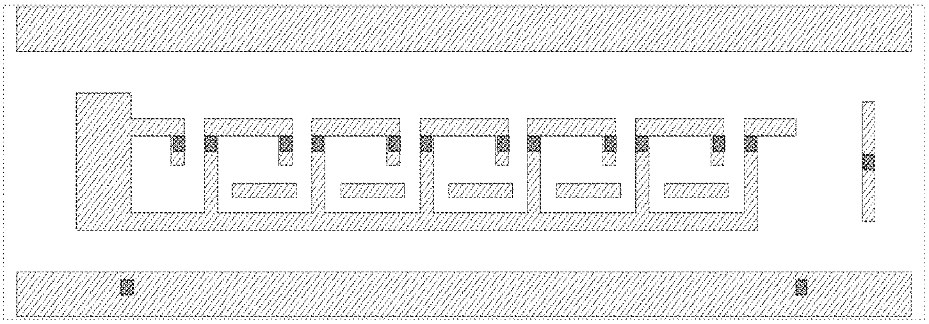
Figure 67A:
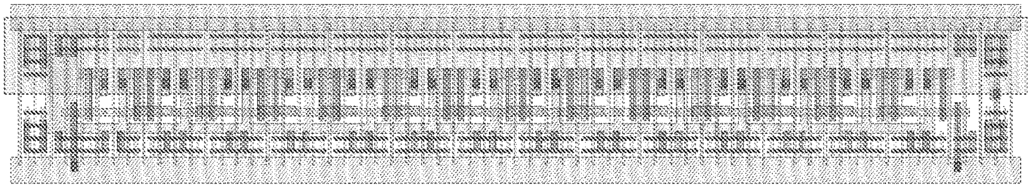
Figure 67B:
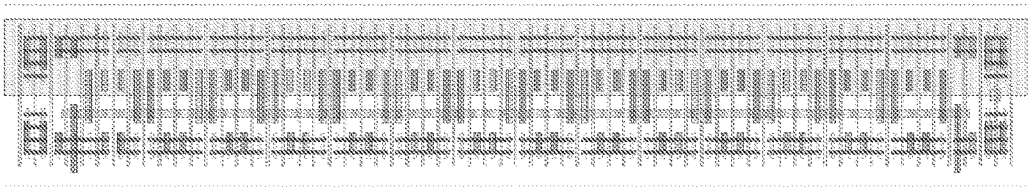
Figure 67C:
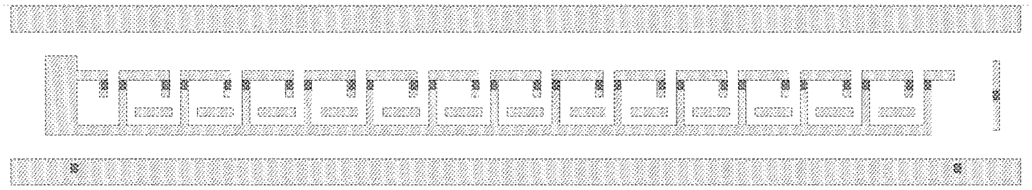
Figure 68A:
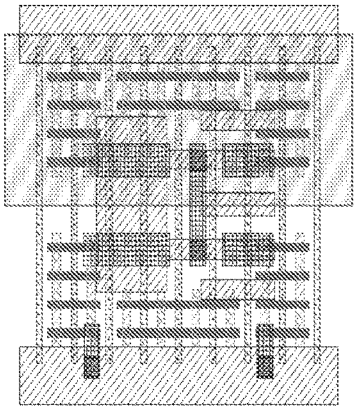
Figure 68B:
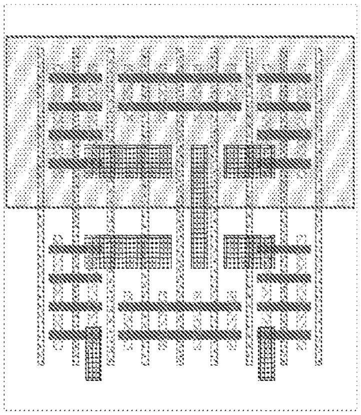
Figure 68C:
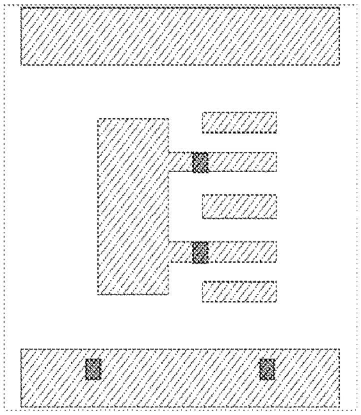
Figure 69A:
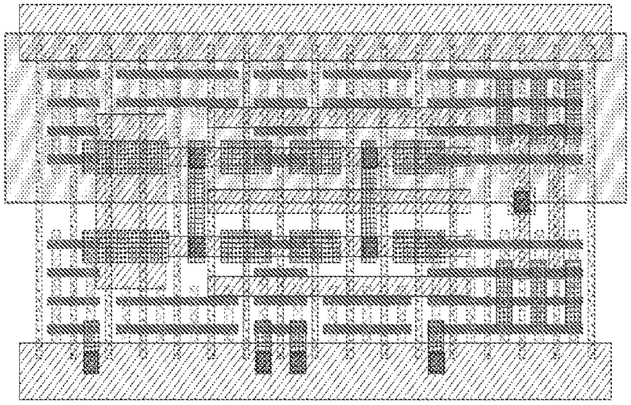
Figure 69B:
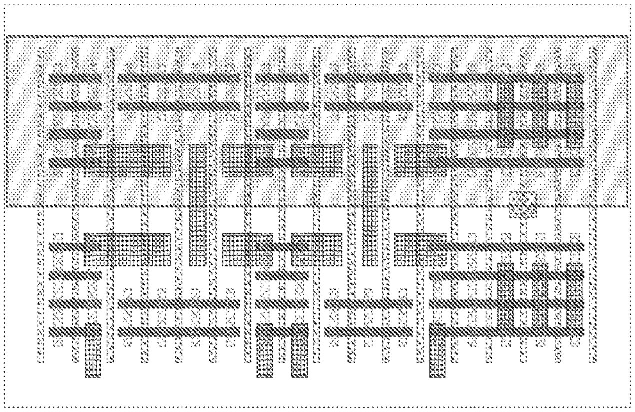
Figure 69C:
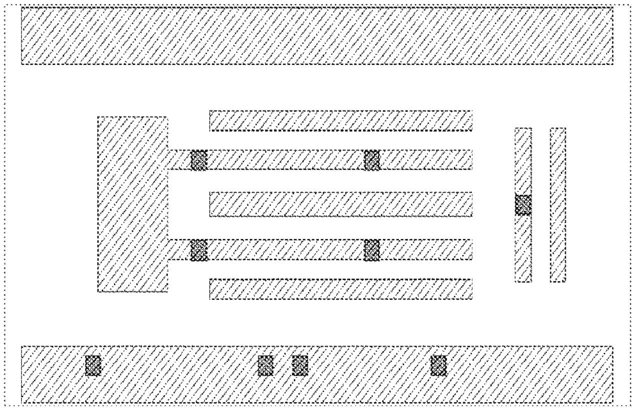
Figure 70A:
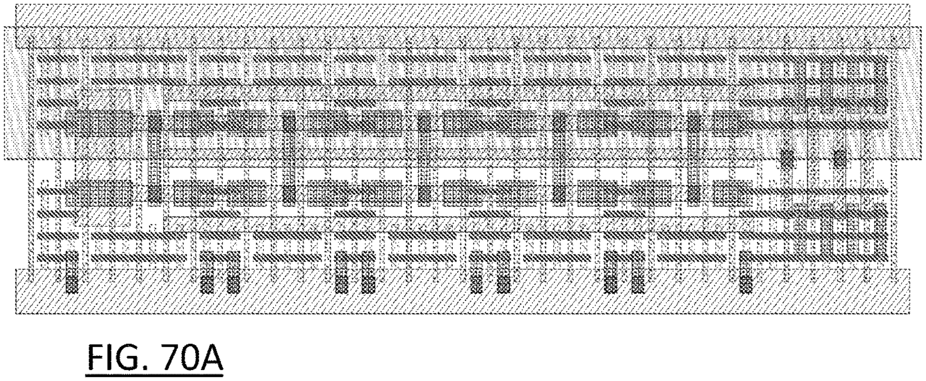
Figure 70B:
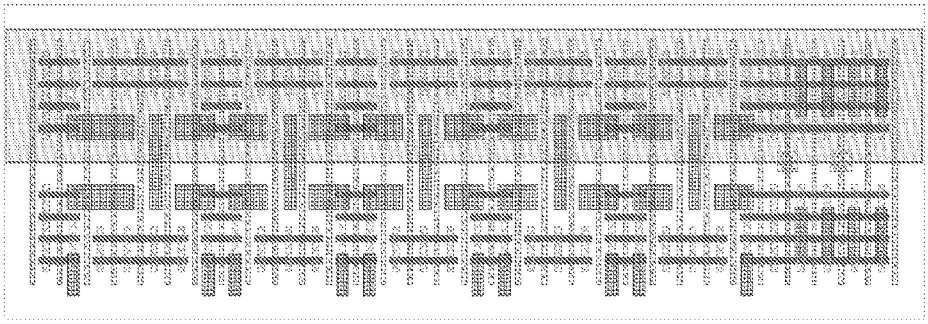
Figure 70C:
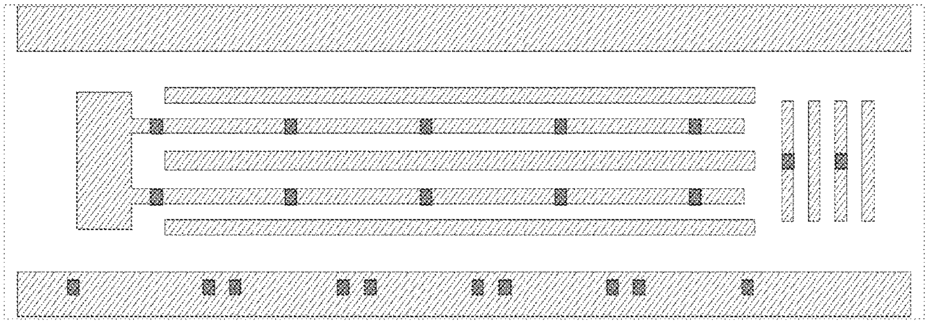
Figure 71A:
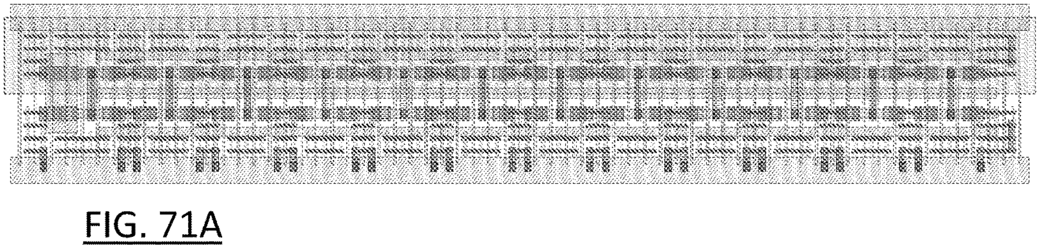
Figure 71B:
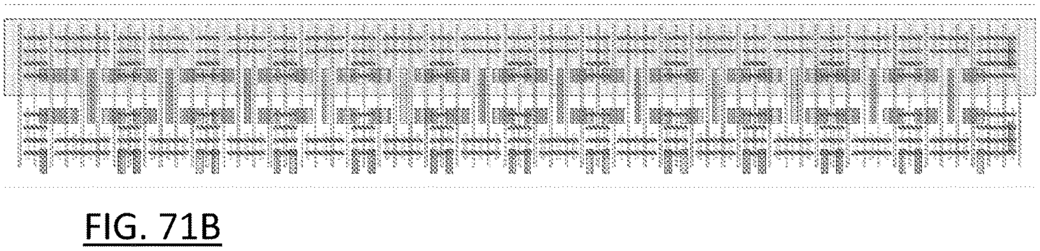
Figure 71C:
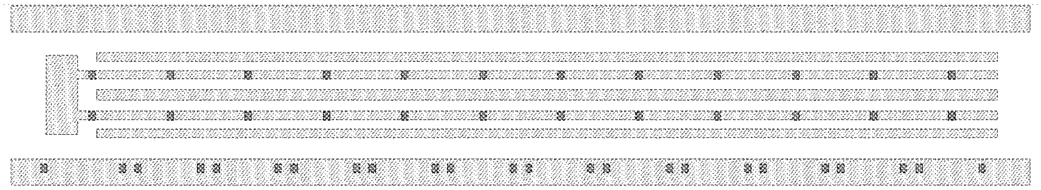
Figure 72A:
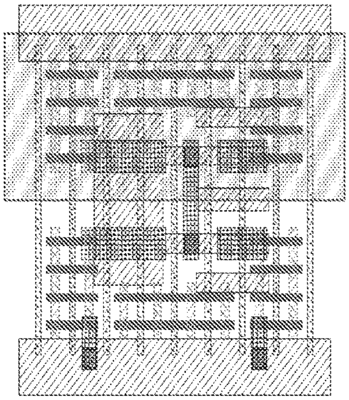
Figure 72B:
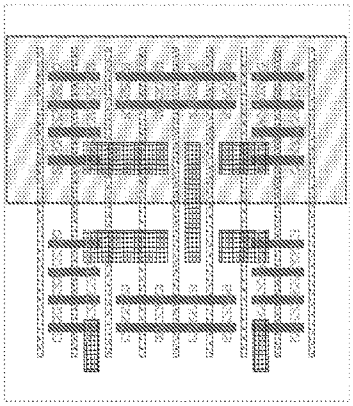
Figure 72C:
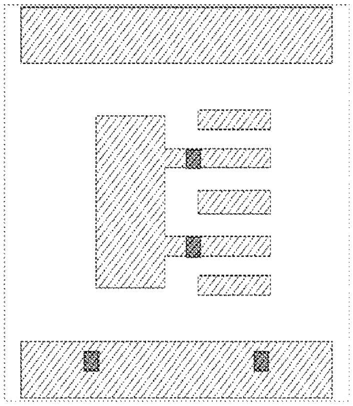
Figure 73A:
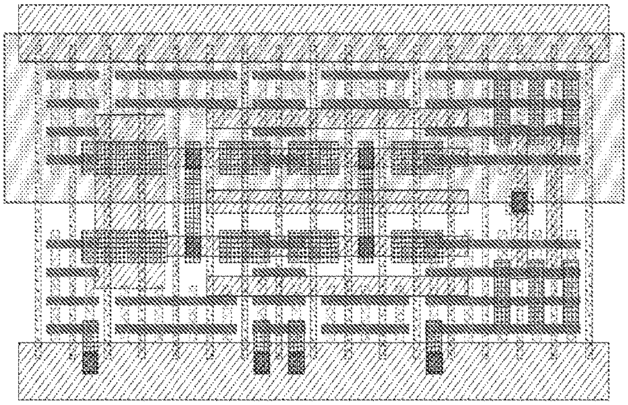
Figure 73B:
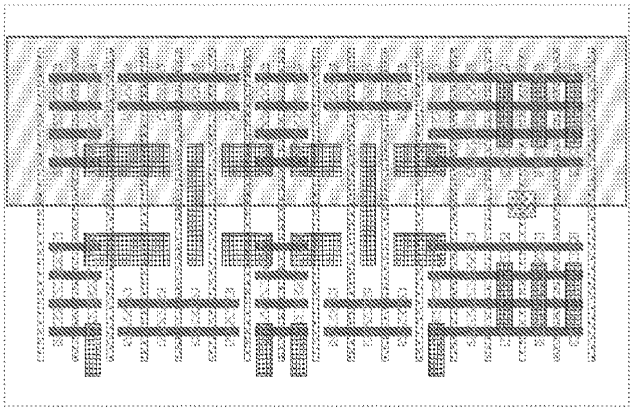
Figure 73C:
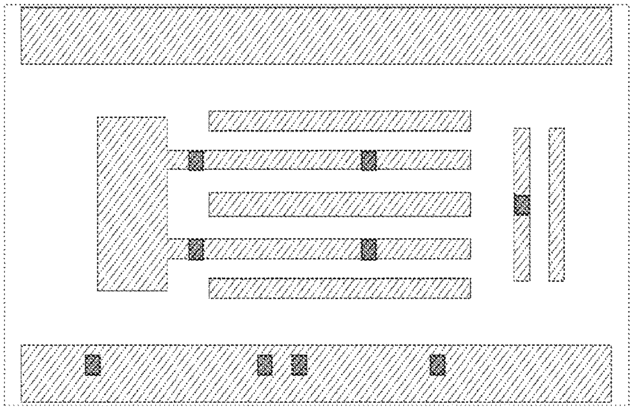
Figure 74A:
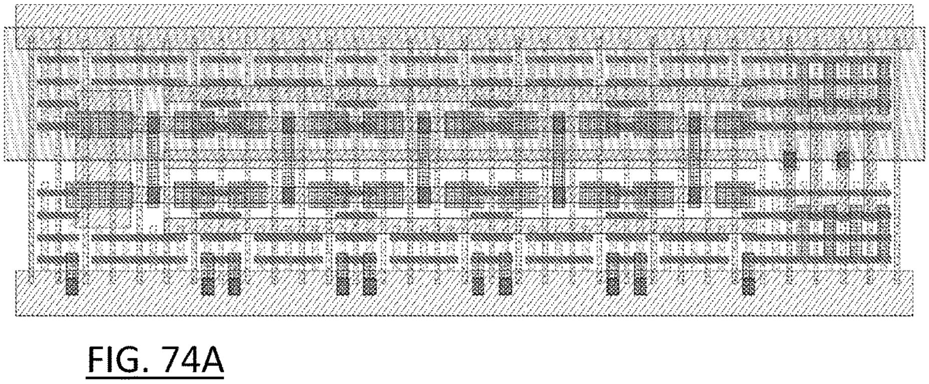
Figure 74B:
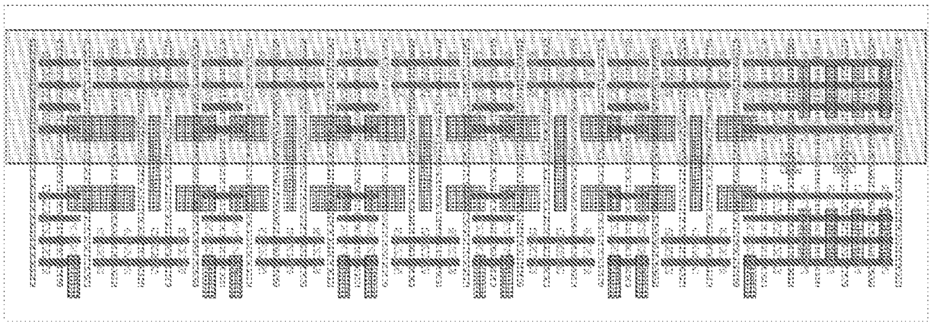
Figure 74C:
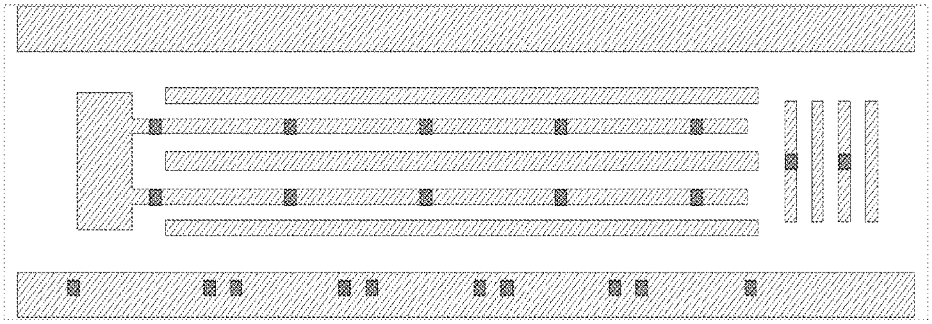
Figure 75A:
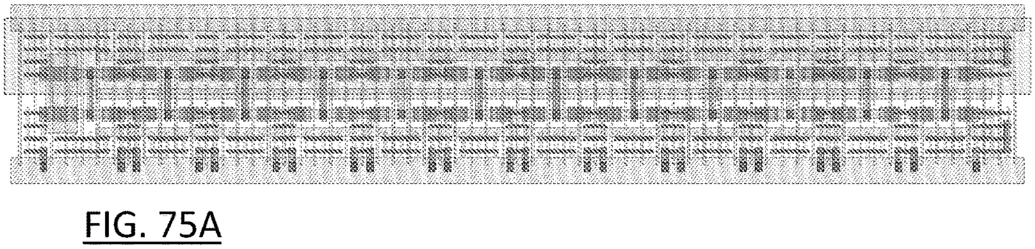
Figure 75B:
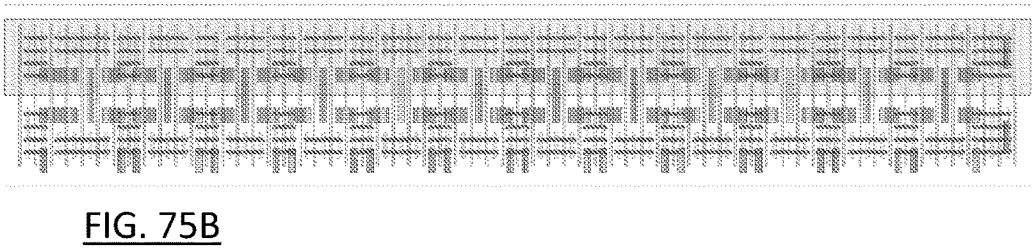
Figure 75C:
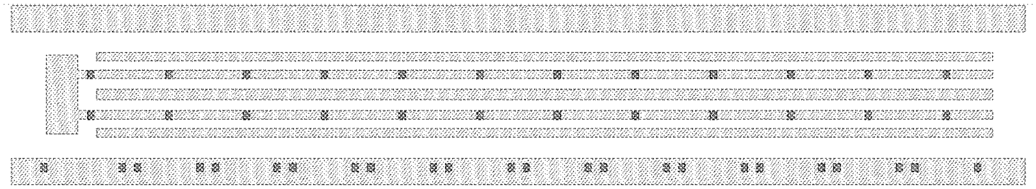
Figure 76A:
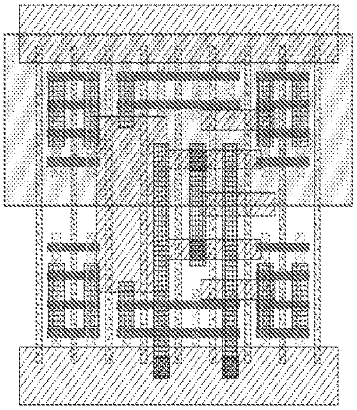
Figure 76B:
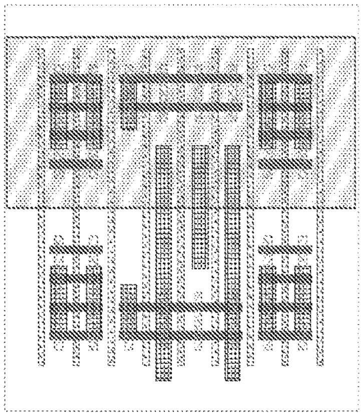
Figure 76C:
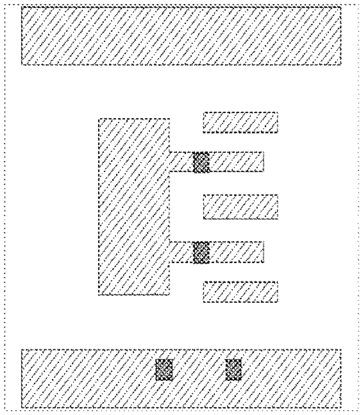
Figure 77A:
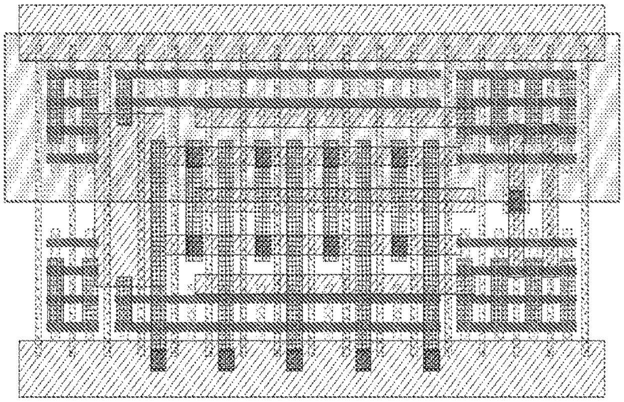
Figure 77B:
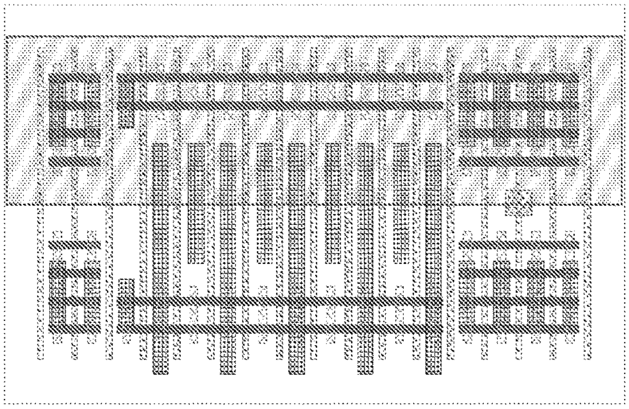
Figure 77C:
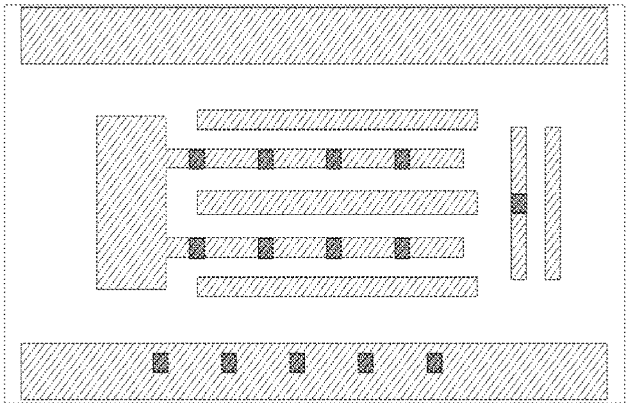
Figure 78A:
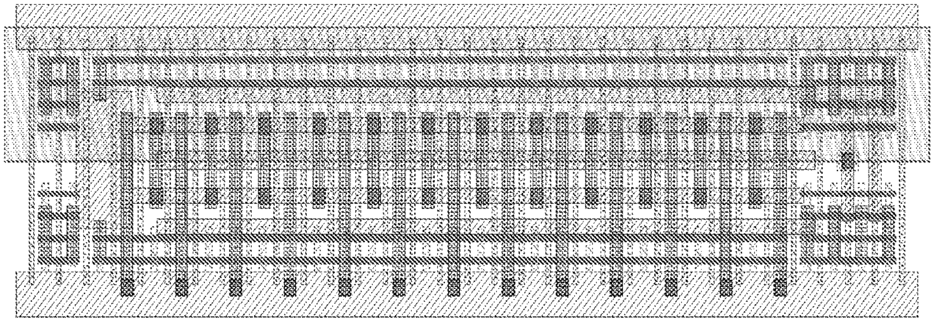
Figure 78B:
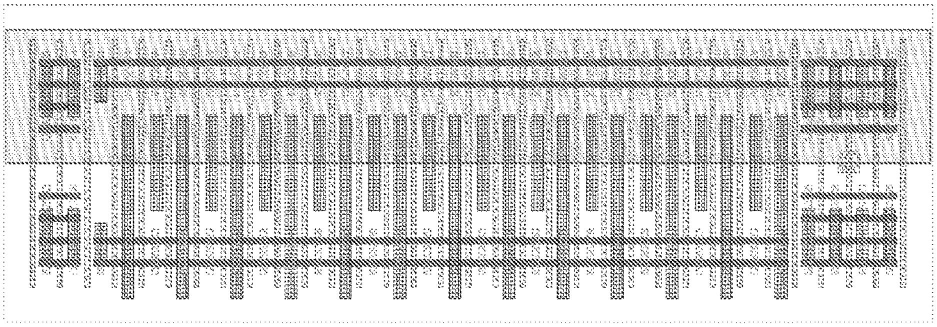
Figure 78C:
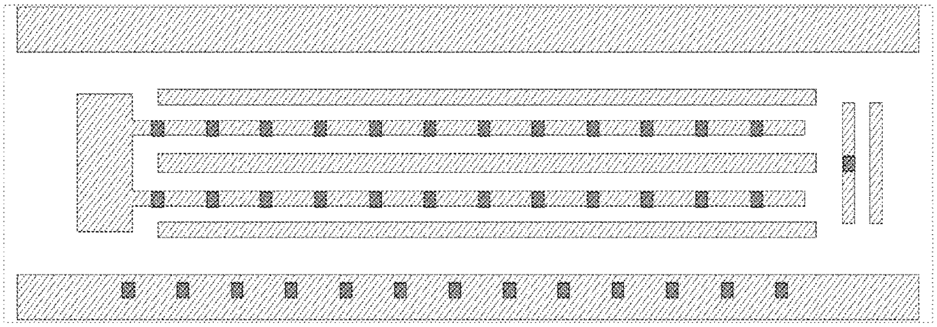
Figure 79A:
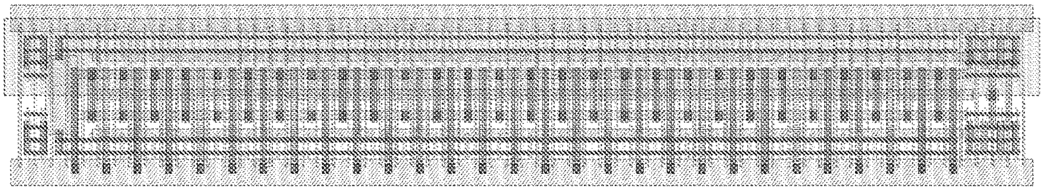
Figure 79B:
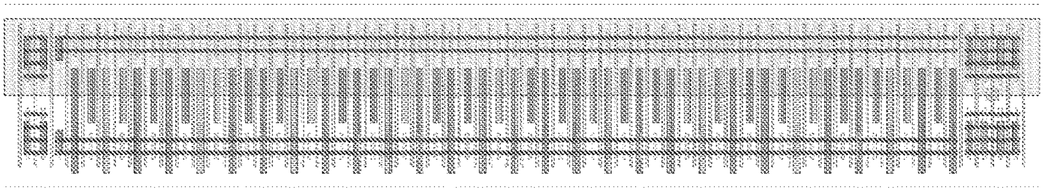
Figure 79C:
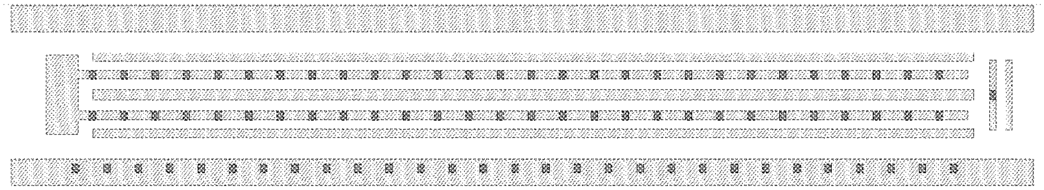
Figure 80A:
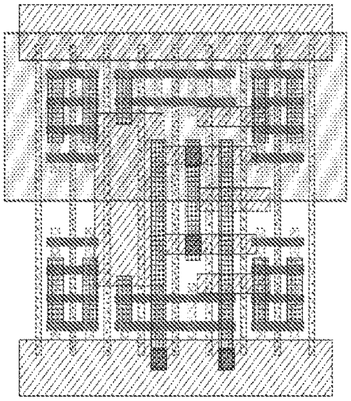
Figure 80B:
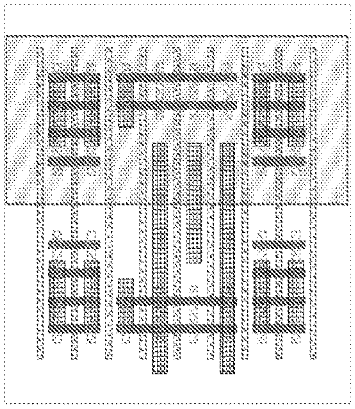
Figure 80C:
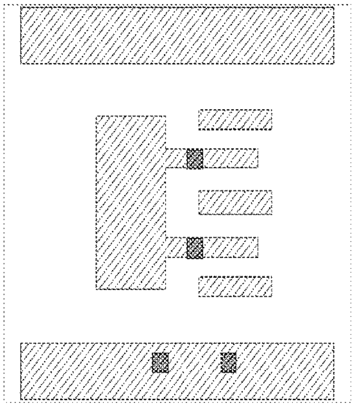
Figure 81A:
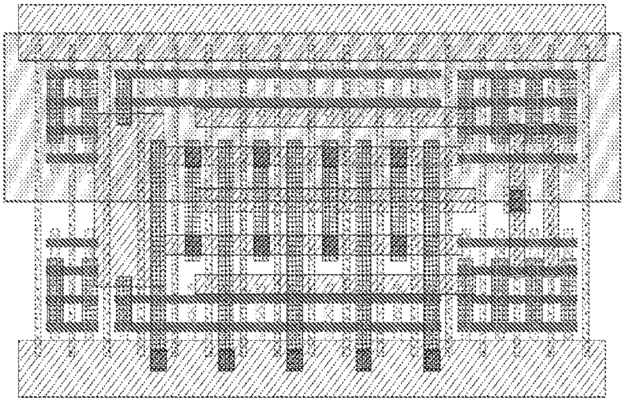
Figure 81B:
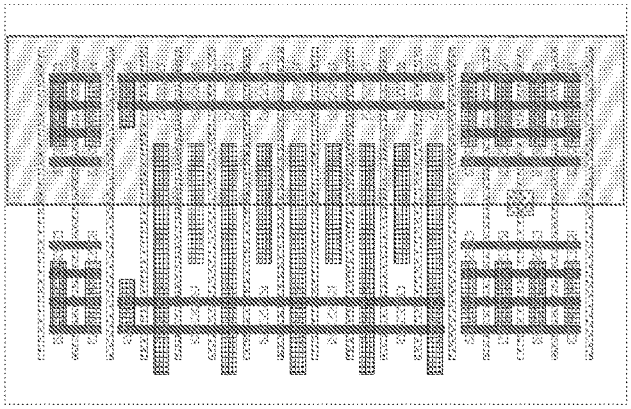
Figure 81C:
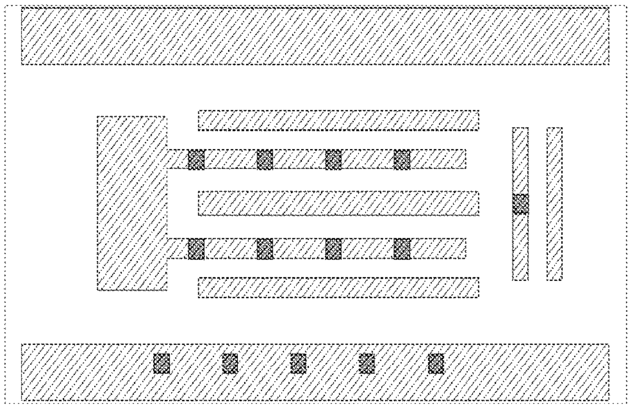
Figure 82A:
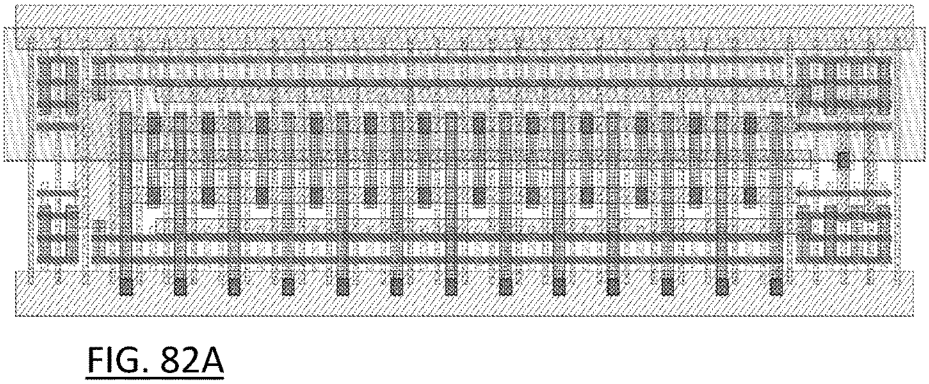
Figure 82B:
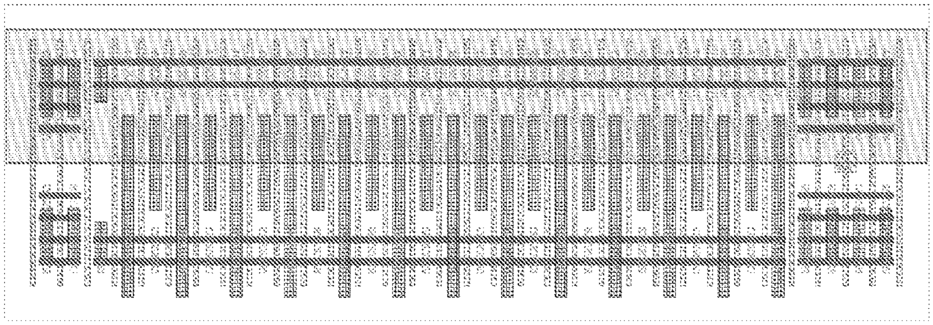
Figure 82C:
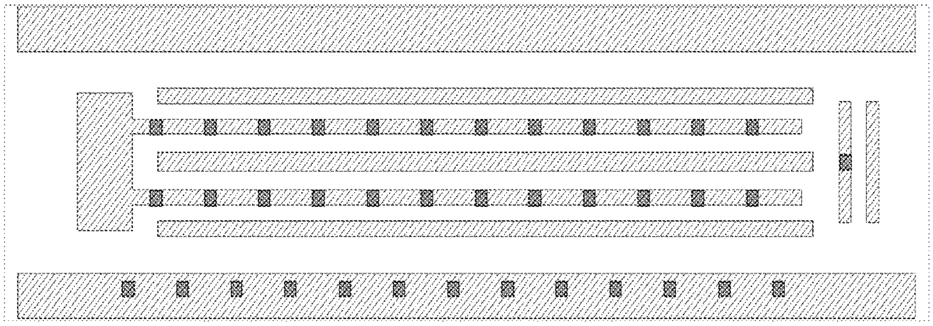
Figure 83A:
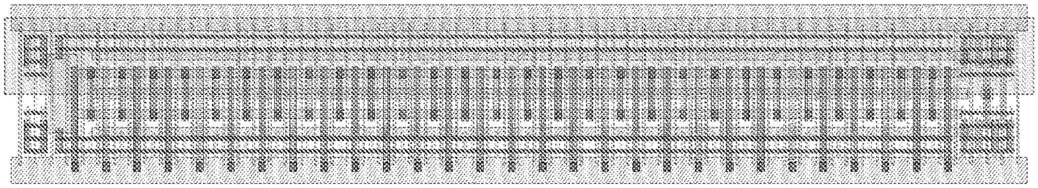
Figure 83B:
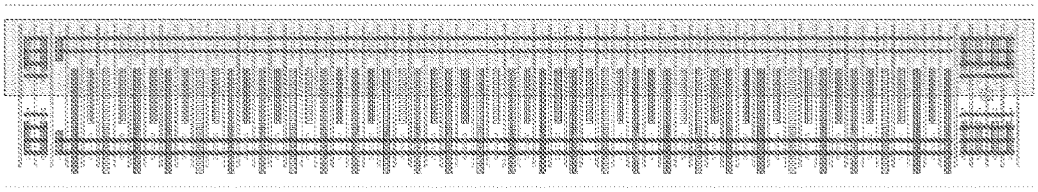
Figure 83C:
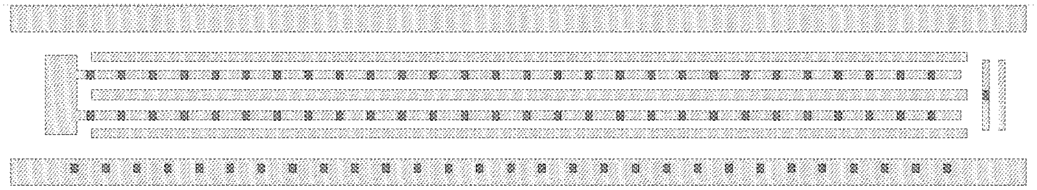
Figure 84A:
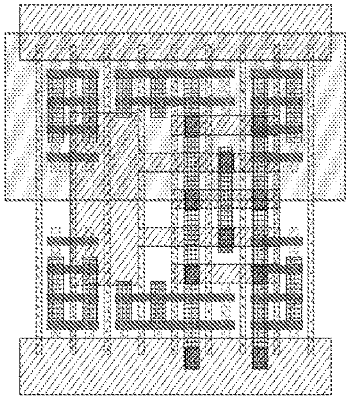
Figure 84B:
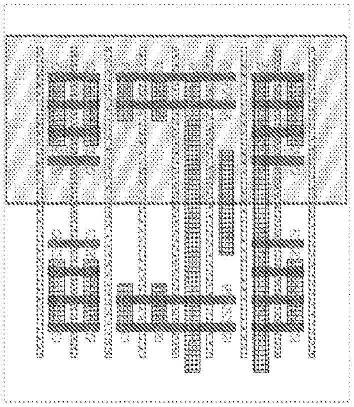
Figure 84C:
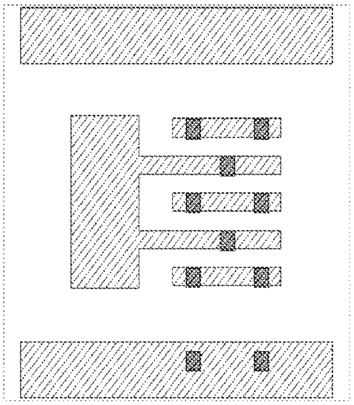
Figure 85A:
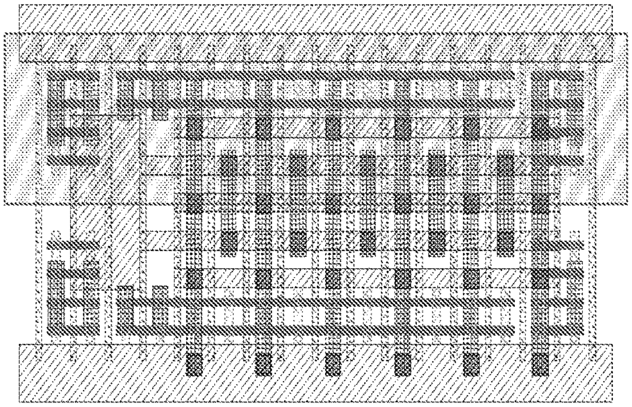
Figure 85B:
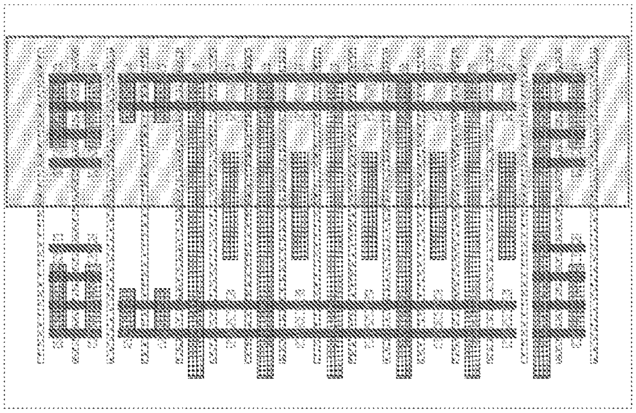
Figure 85C:
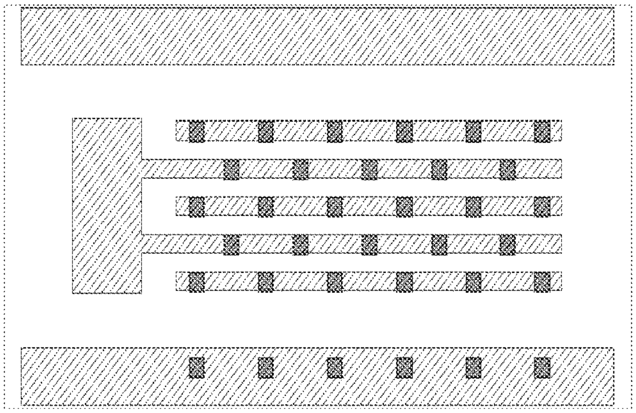
Figure 86A:
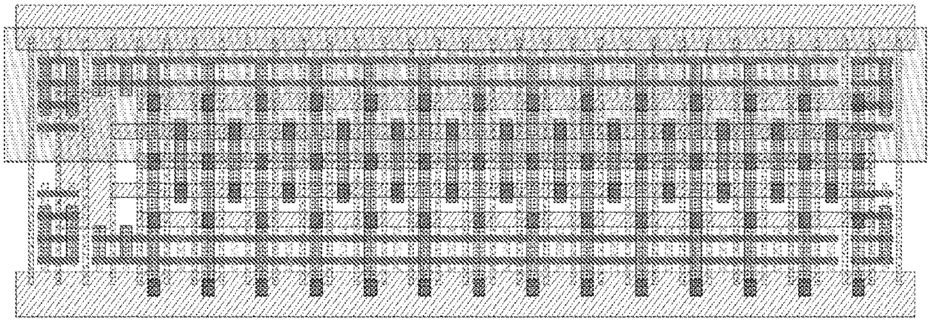
Figure 86B:
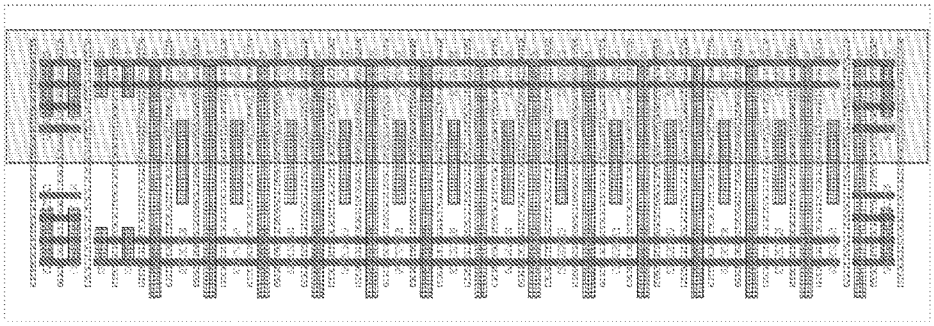
Figure 86C:
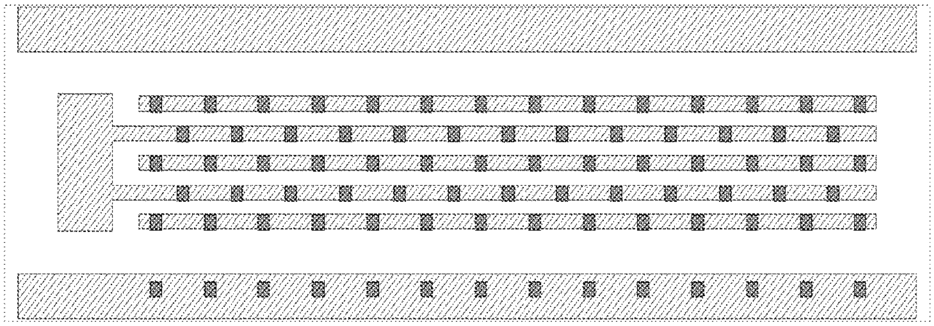
Figure 87A:
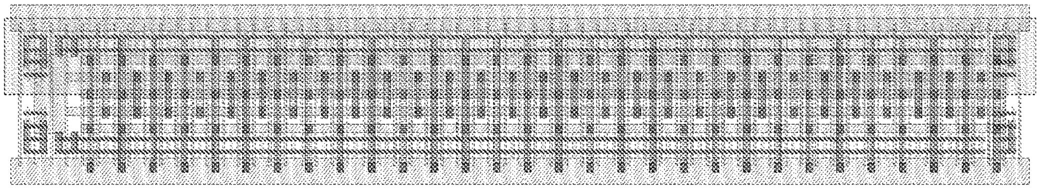
Figure 87B:
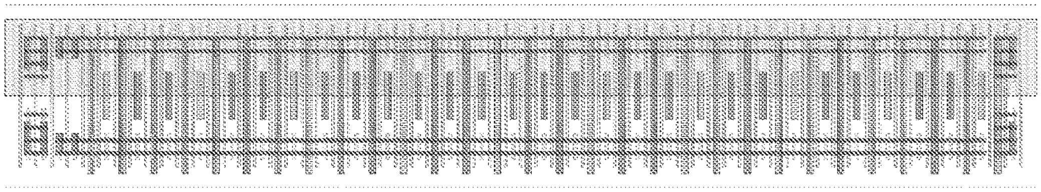
Figure 87C:
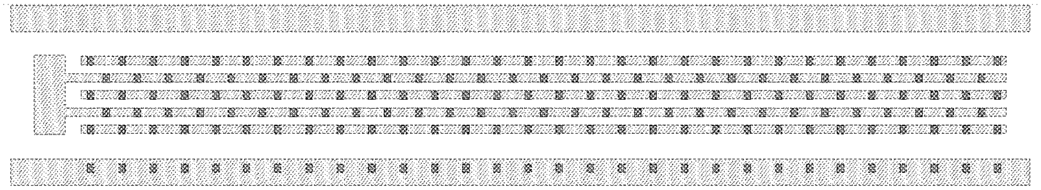
Figure 88A:
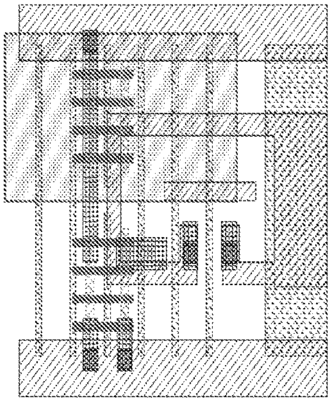
Figure 88B:
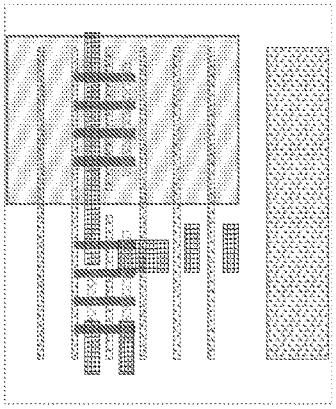
Figure 88C:
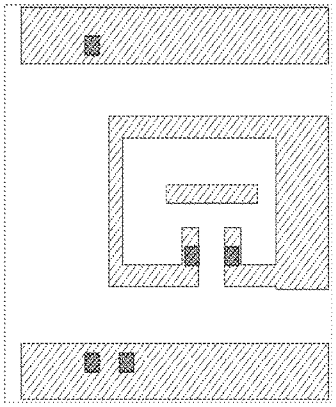
Figure 89A:
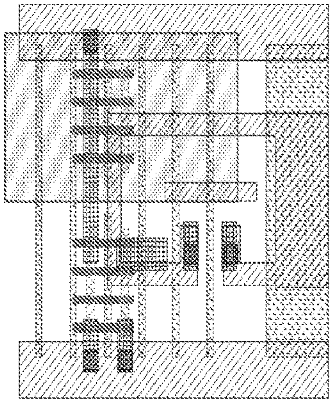
Figure 89B:
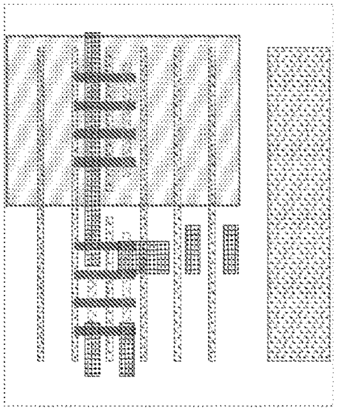
Figure 89C:
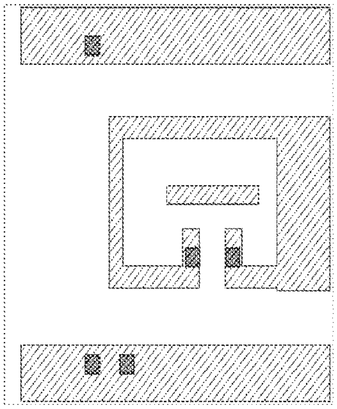
Figure 90A:
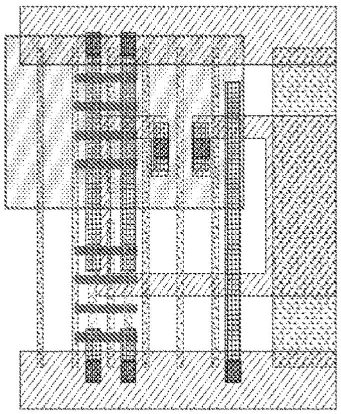
Figure 90B:
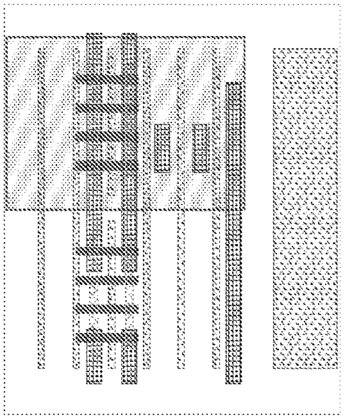
Figure 90C:
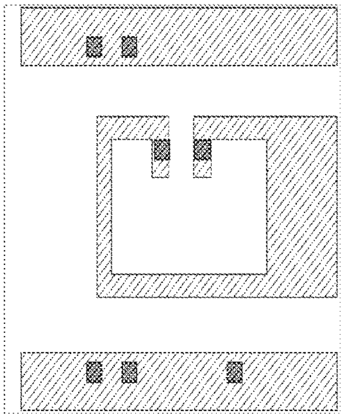
Figure 91A:
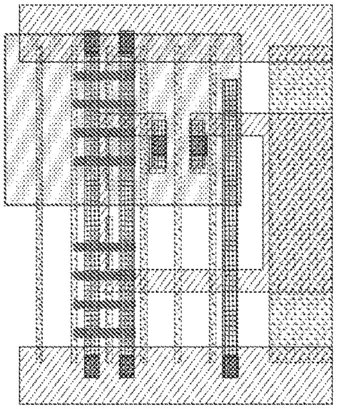
Figure 91B:
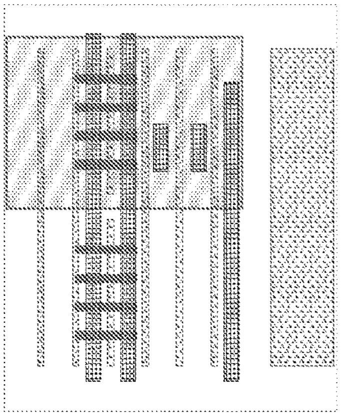
Figure 91C:
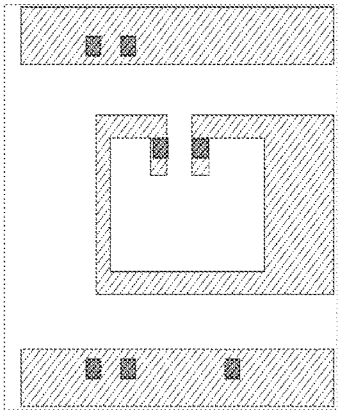
Figure 92A:
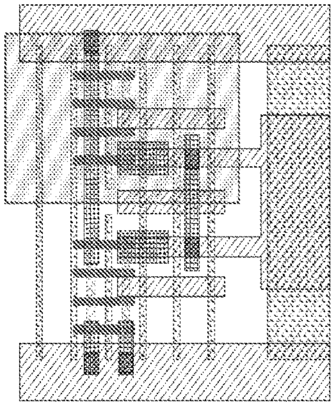
Figure 92B:
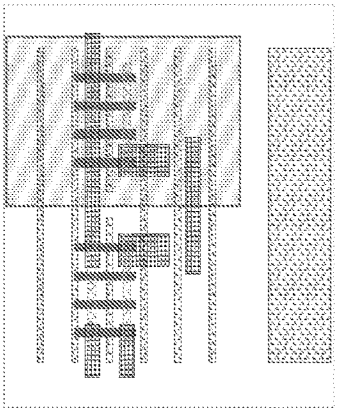
Figure 92C:
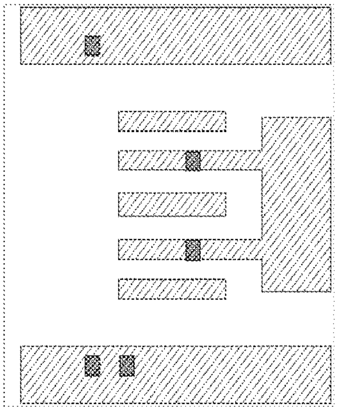
Figure 93A:
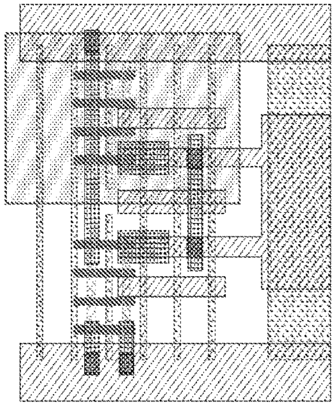
Figure 93B:
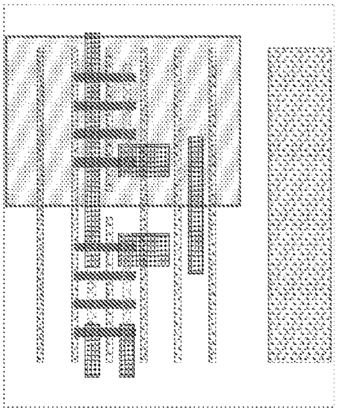
Figure 93C:
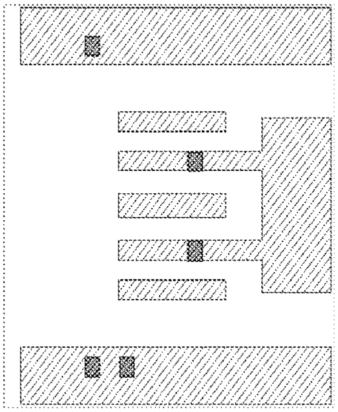
Figure 94A:
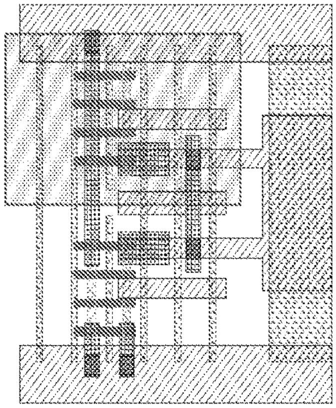
Figure 94B:
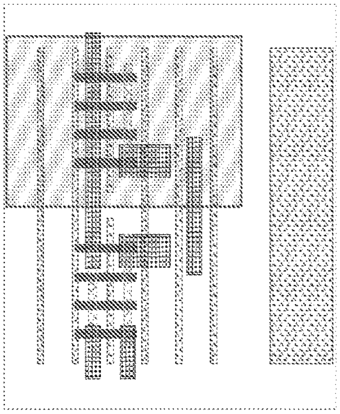
Figure 94C:
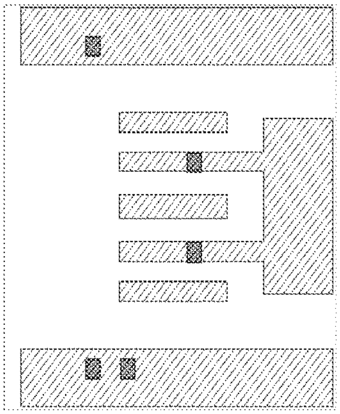
Figure 95A:
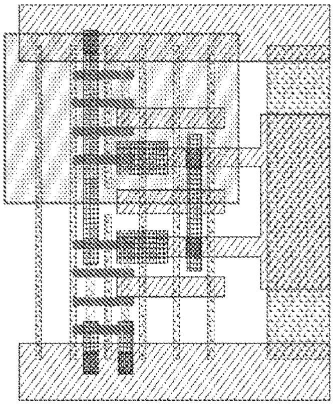
Figure 95B:
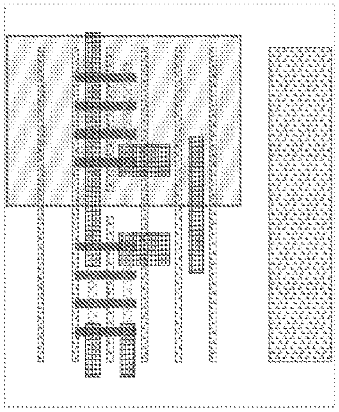
Figure 95C:
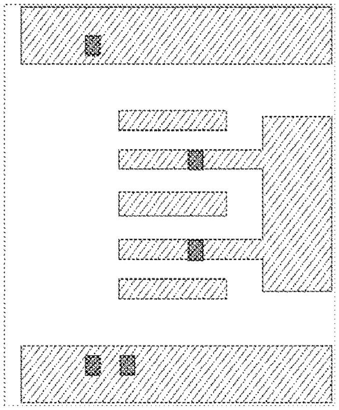
Figure 96A:
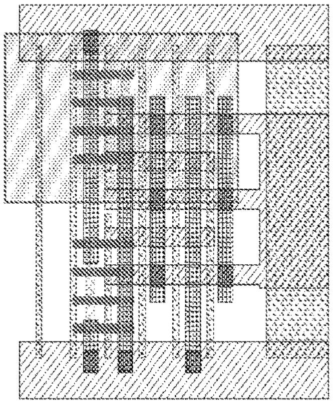
Figure 96B:
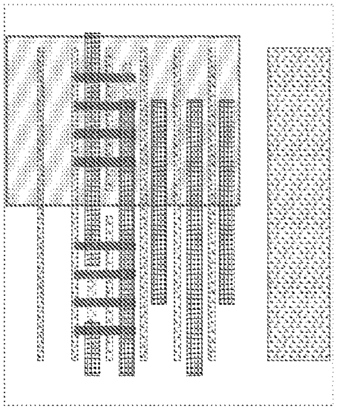
Figure 96C:
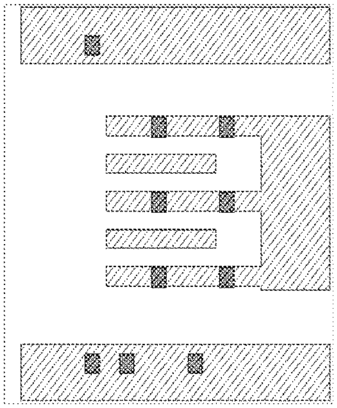
Figure 97A:
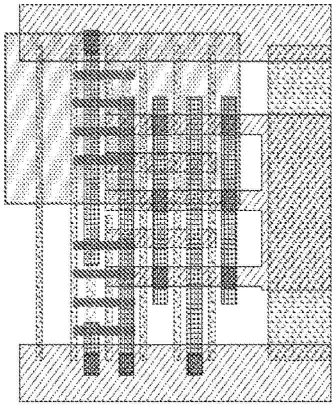
Figure 97B:
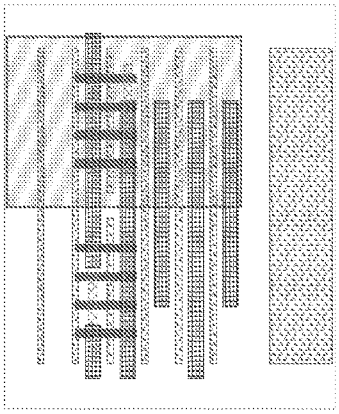
Figure 97C:
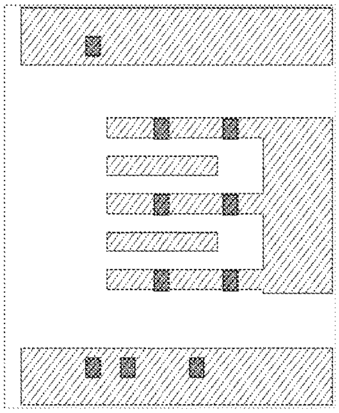
Figure 98A:
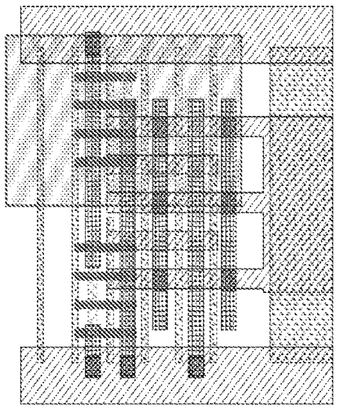
Figure 98B:
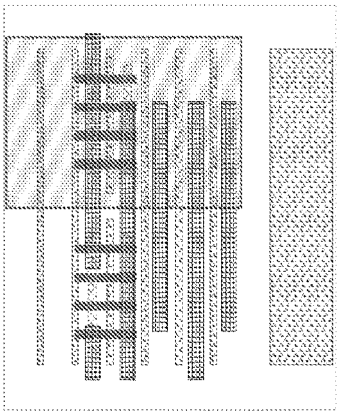
Figure 98C:
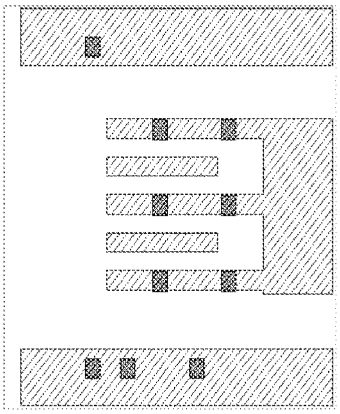
Figure 99A:
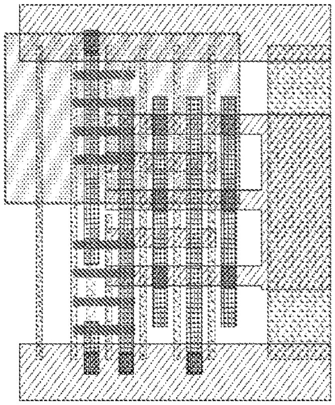
Figure 99B:
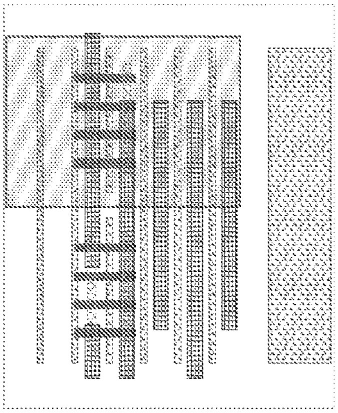
Figure 99C:
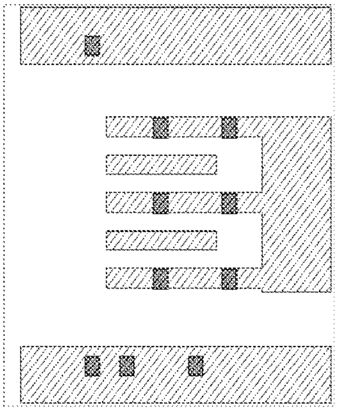
Figure 100A:
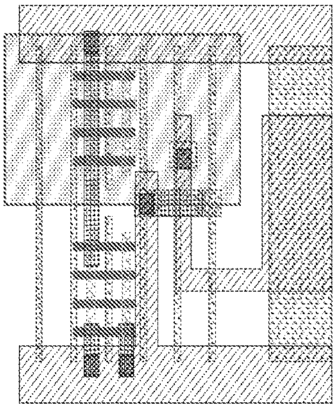
Figure 100B:
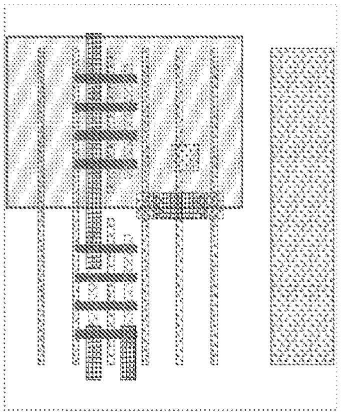
Figure 100C:
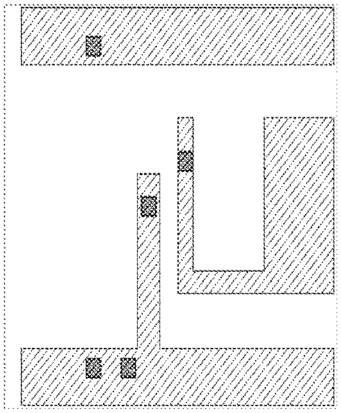
Figure 101A:
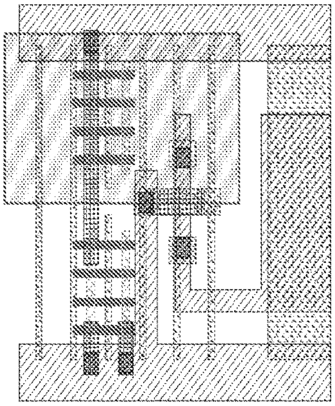
Figure 101B:
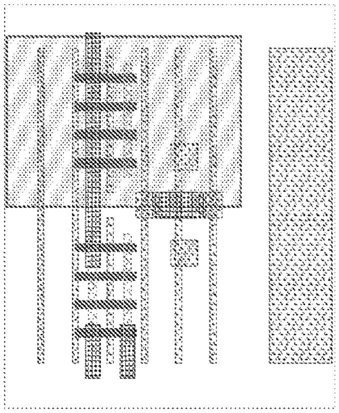
Figure 101C:
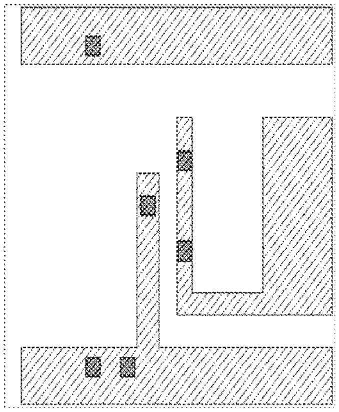
Figure 102A:
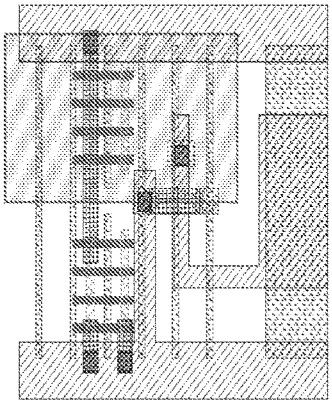
Figure 102B:
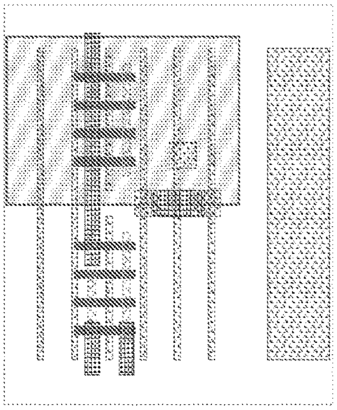
Figure 102C:
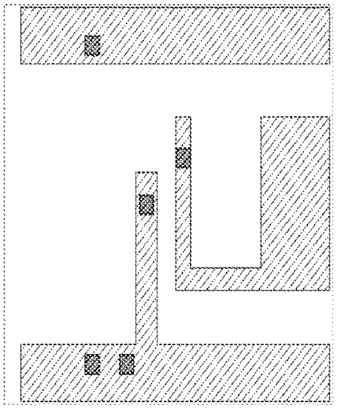
Figure 103A:
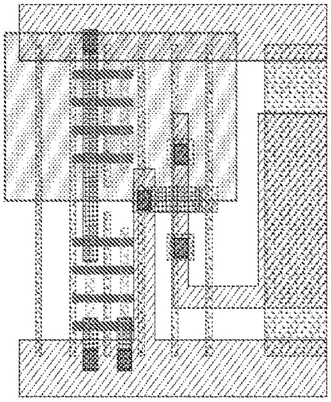
Figure 103B:
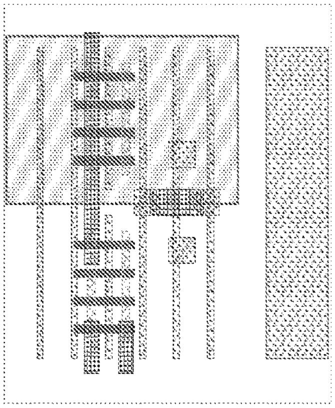
Figure 103C:
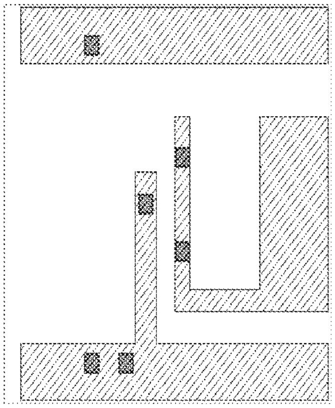
Figure 104A:
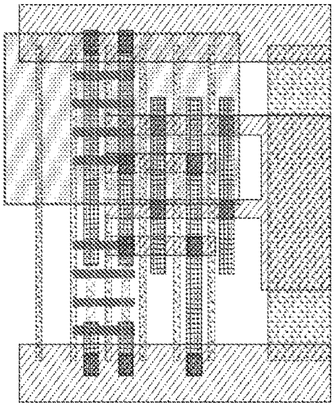
Figure 104B:
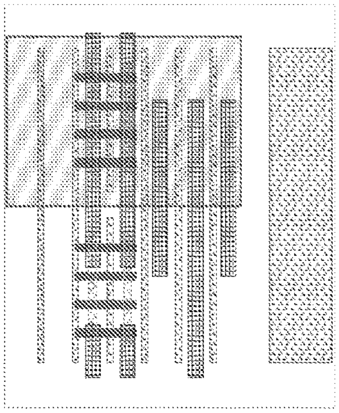
Figure 104C:
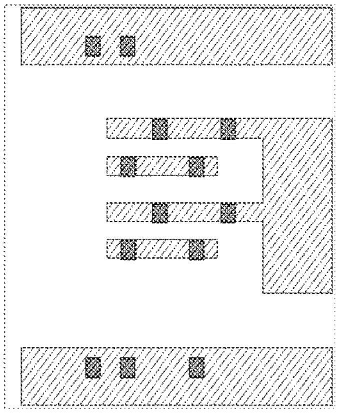
Figure 105A:
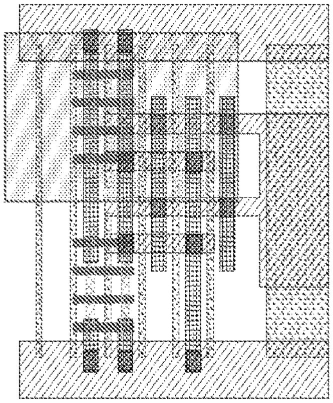
Figure 105B:
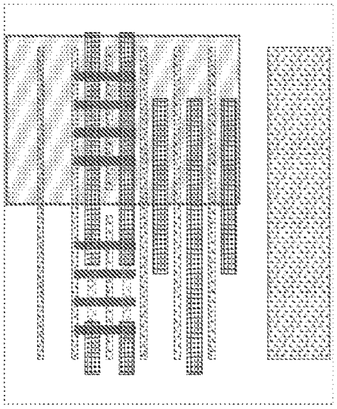
Figure 105C:
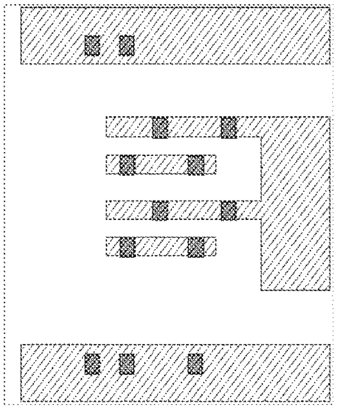
Figure 106A:
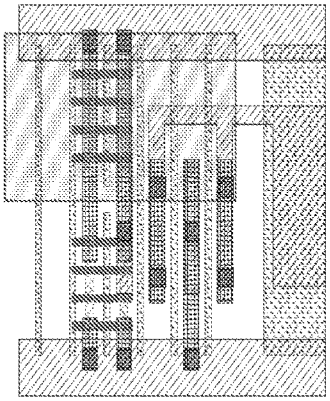
Figure 106B:
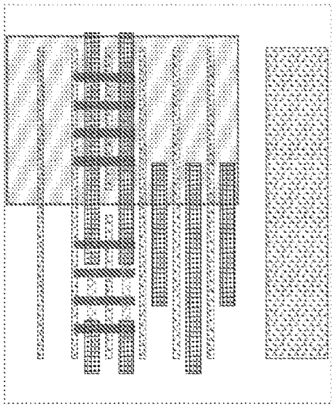
Figure 106C:
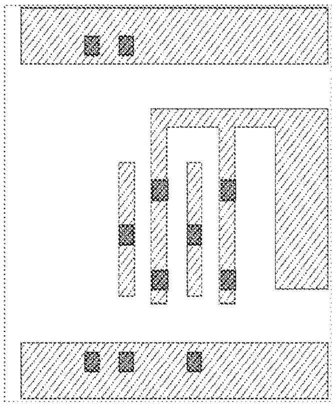
Figure 107A:
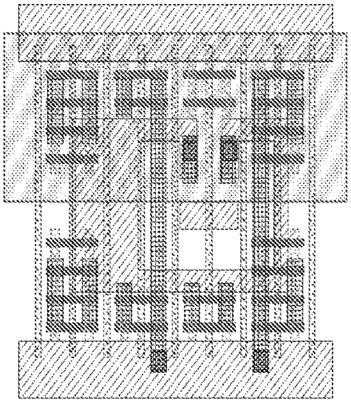
Figure 107B:
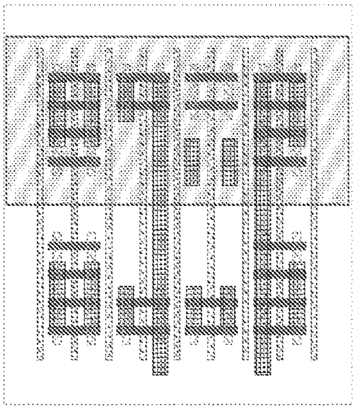
Figure 107C:
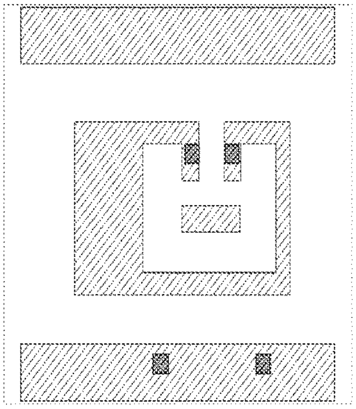
Figure 108A:
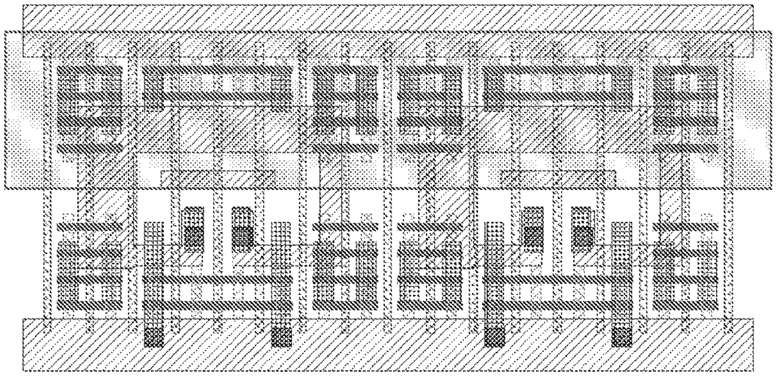
Figure 108B:
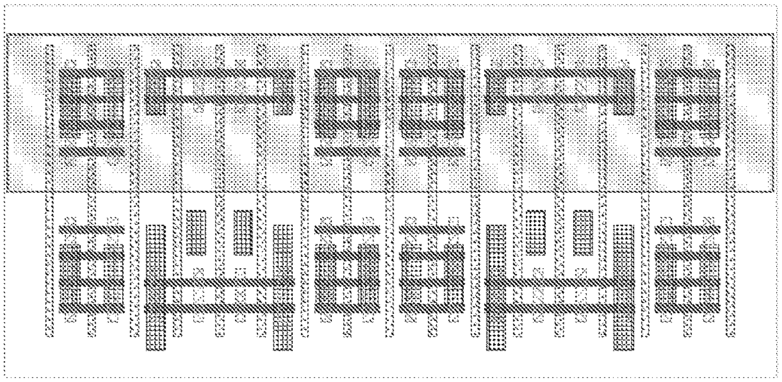
Figure 108C:
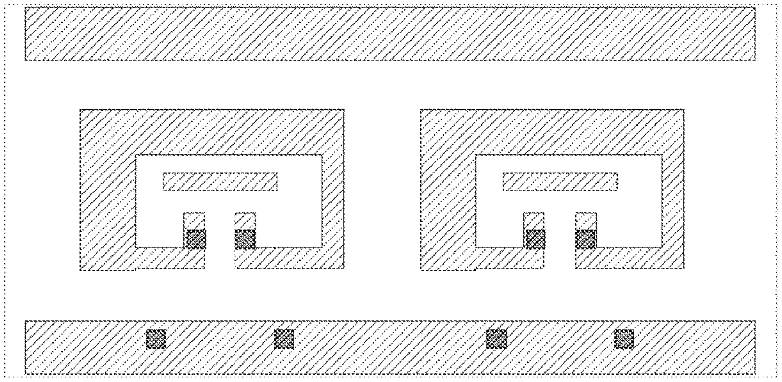
Figure 109A:
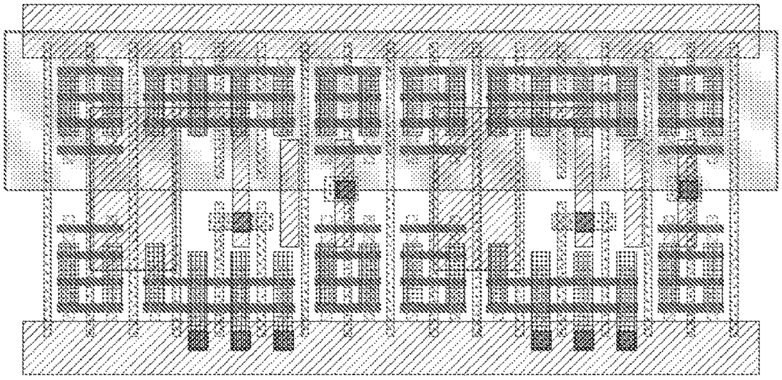
Figure 109B:
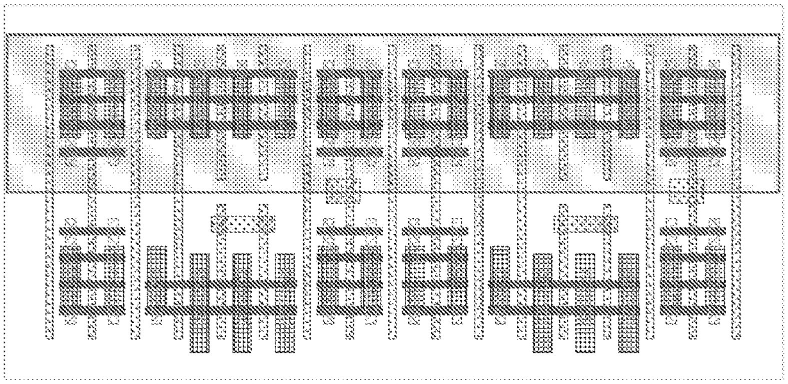
Figure 109C:
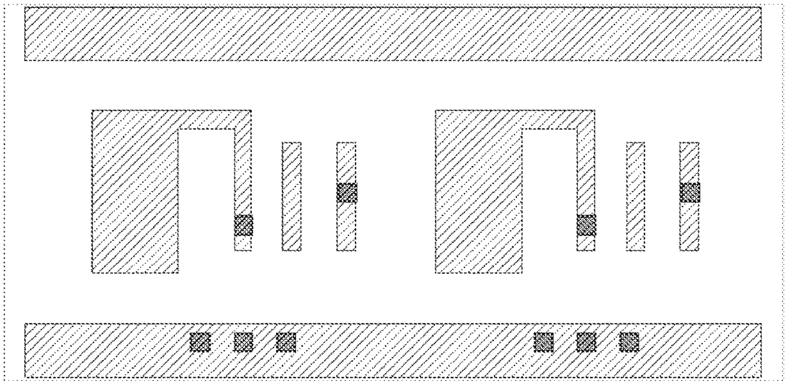
Figure 110A:
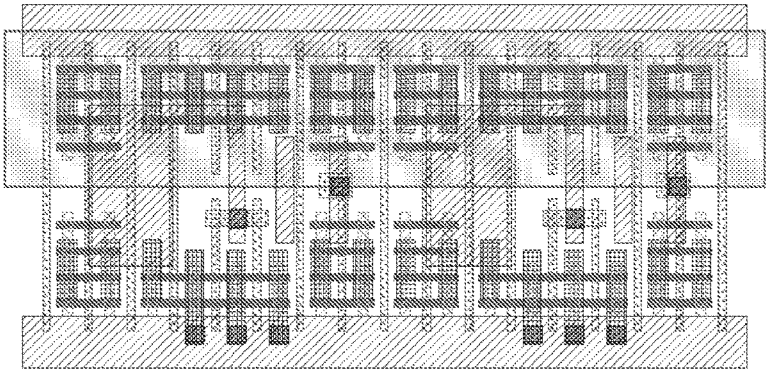
Figure 110B:
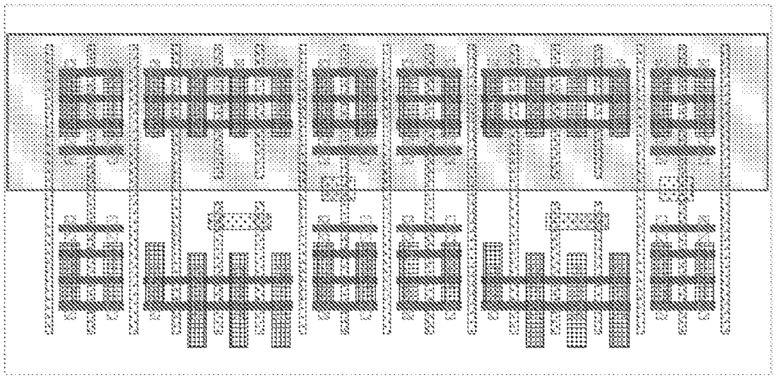
Figure 110C:
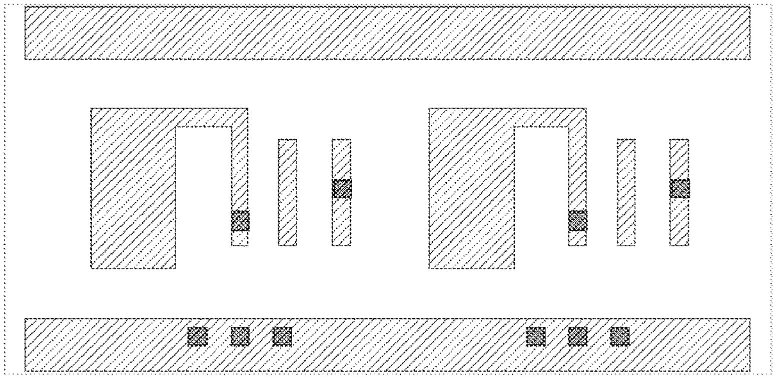
Figure 111A:
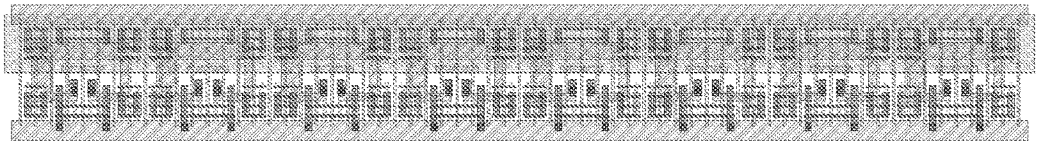
Figure 111B:
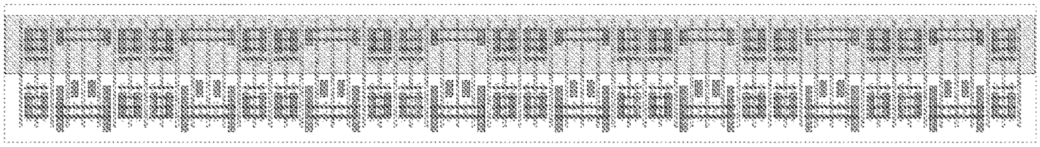
Figure 111C:
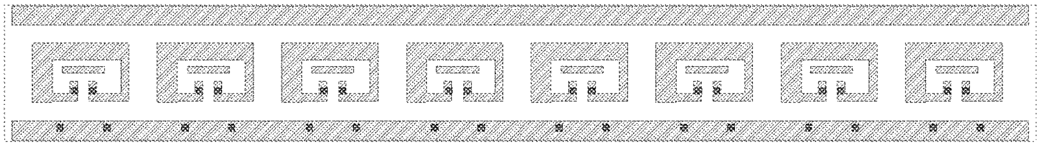
Figure 112A:
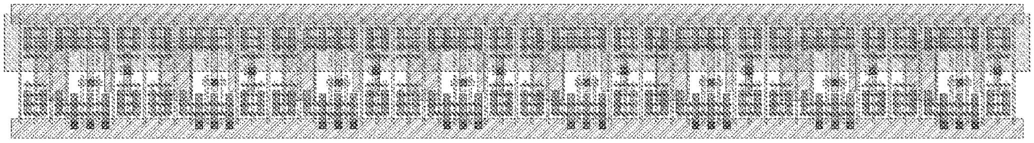
Figure 112B:
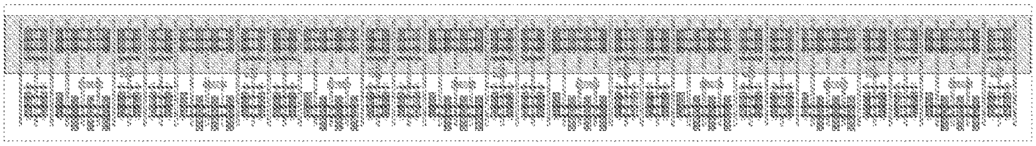
Figure 112C:
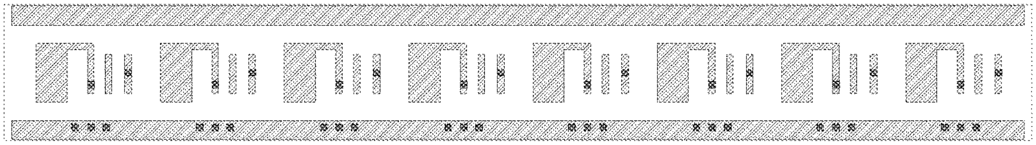
Figure 113A:
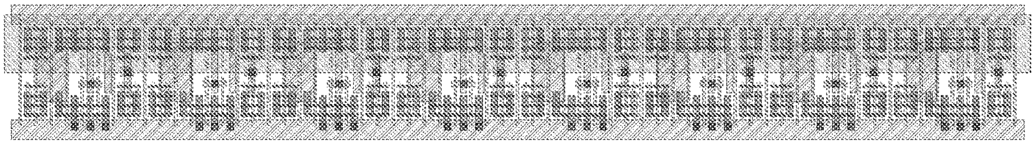
Figure 113B:
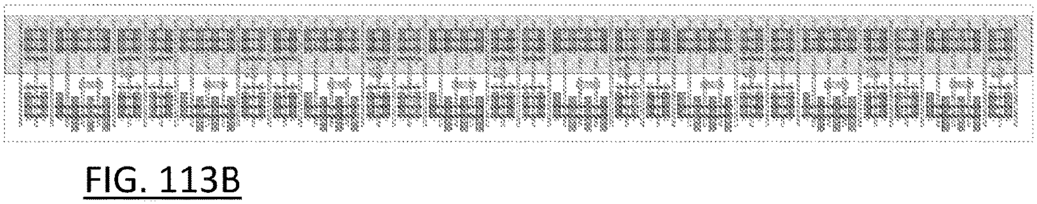
Figure 113C:
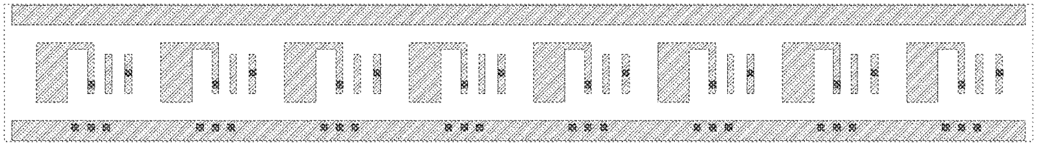
Figure 114A:
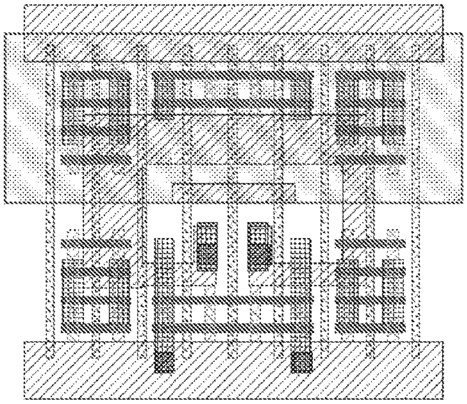
Figure 114B:
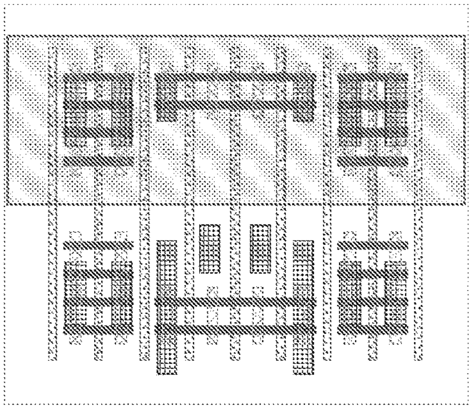
Figure 114C:
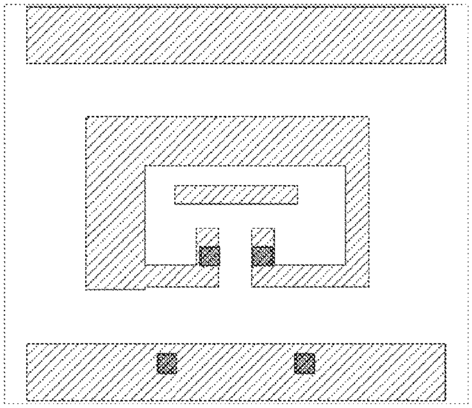
Figure 115A:
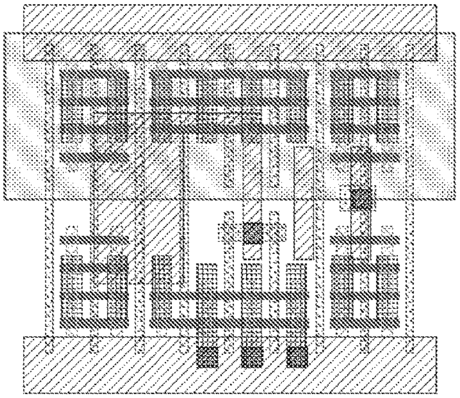
Figure 115B:
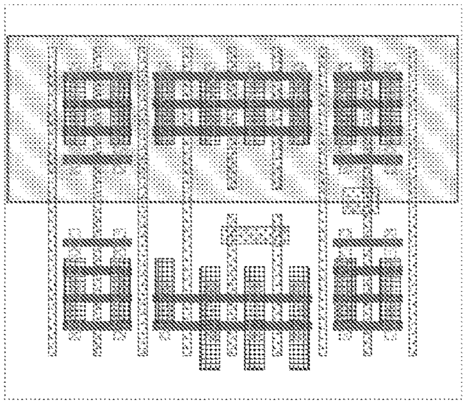
Figure 115C:
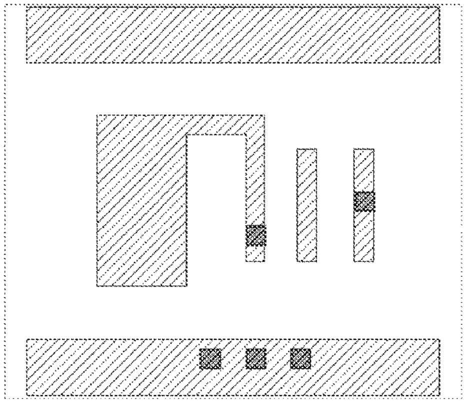
Figure 116A:
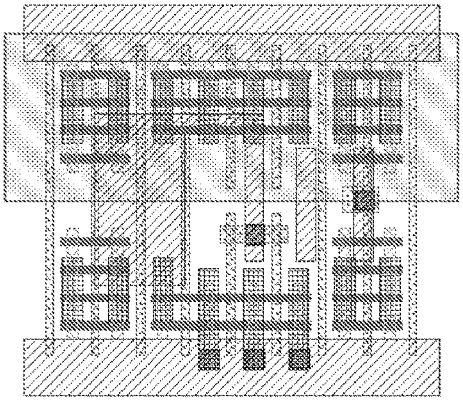
Figure 116B:
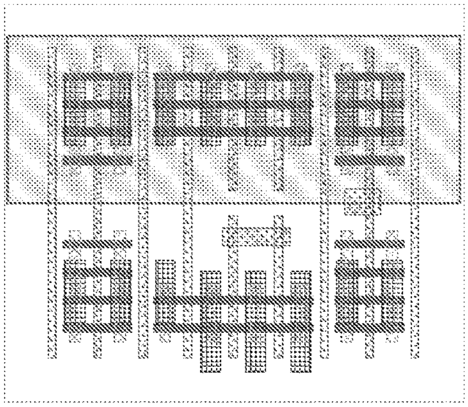
Figure 116C:
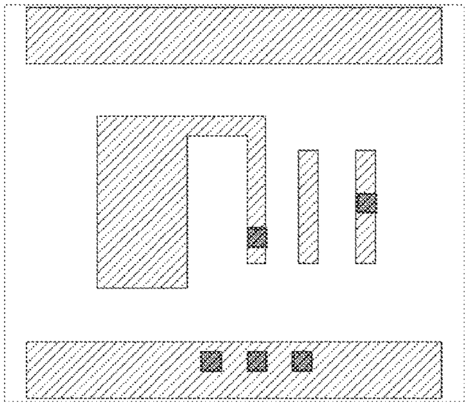
Figure 117A:
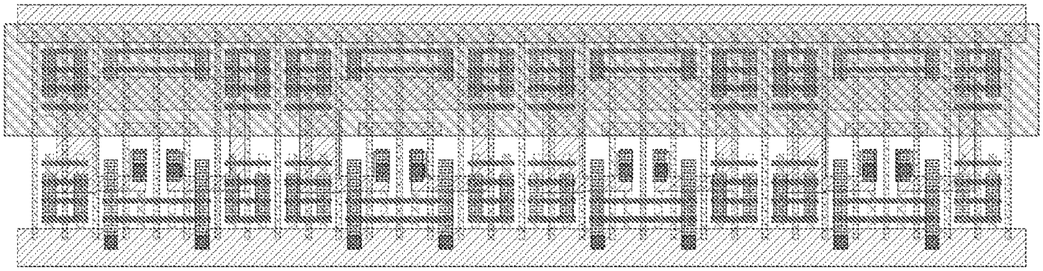
Figure 117B:
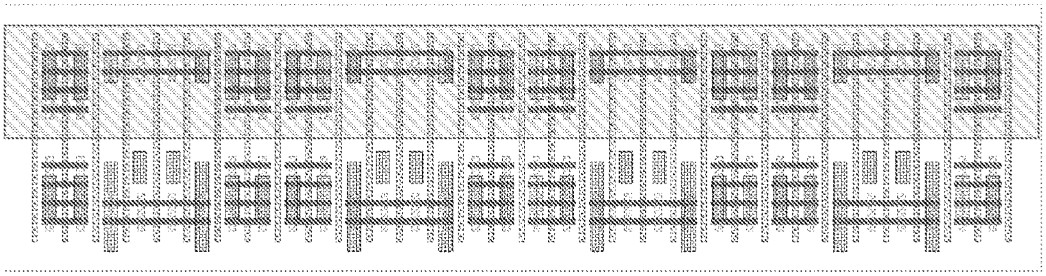
Figure 117C:
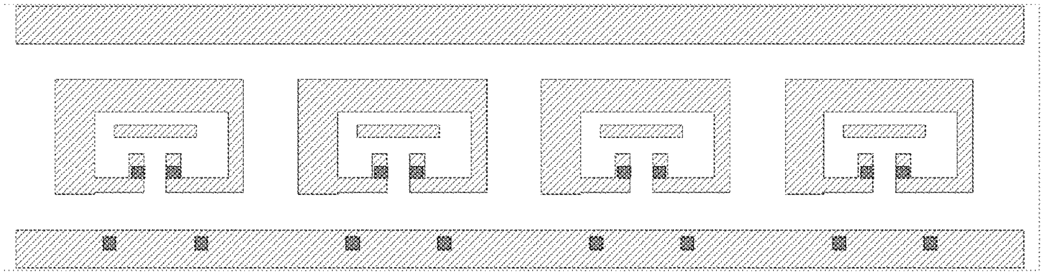
Figure 118A:
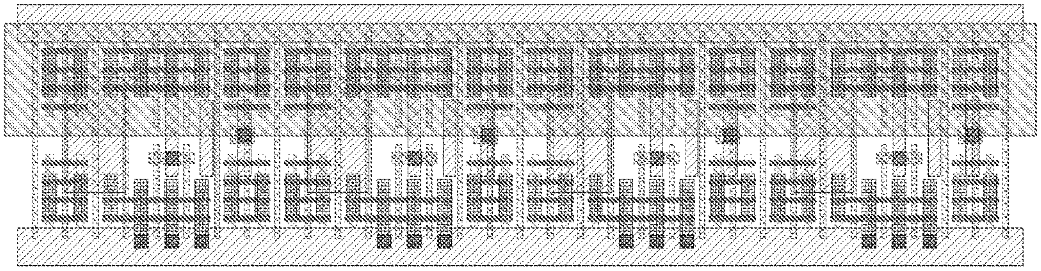
Figure 118B:
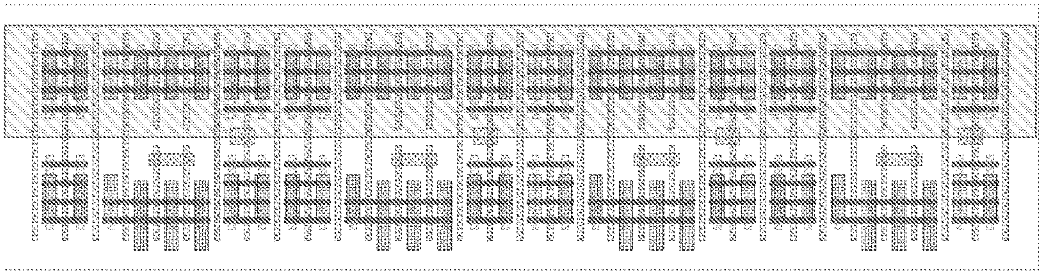
Figure 118C:
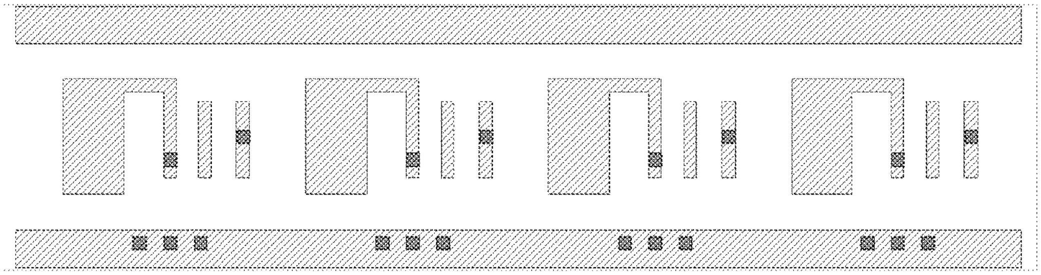
Figure 119A:
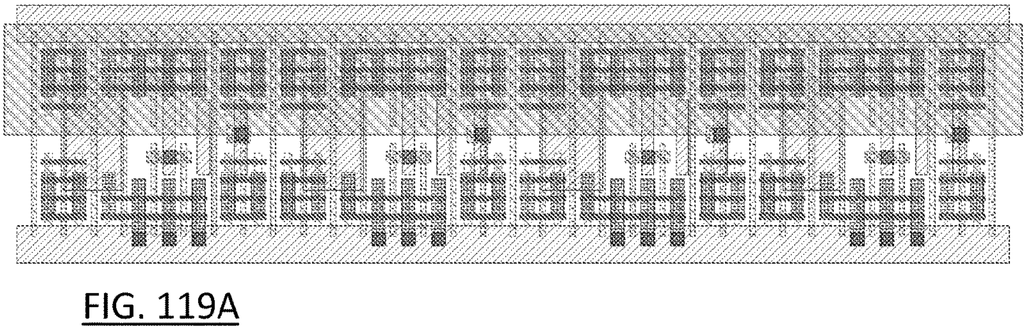
Figure 119B:
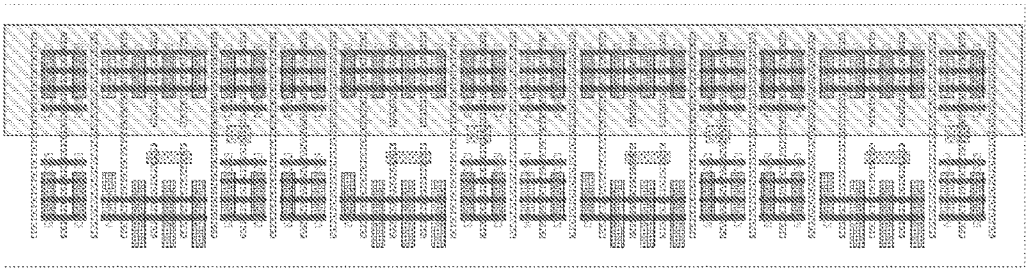
Figure 119C:
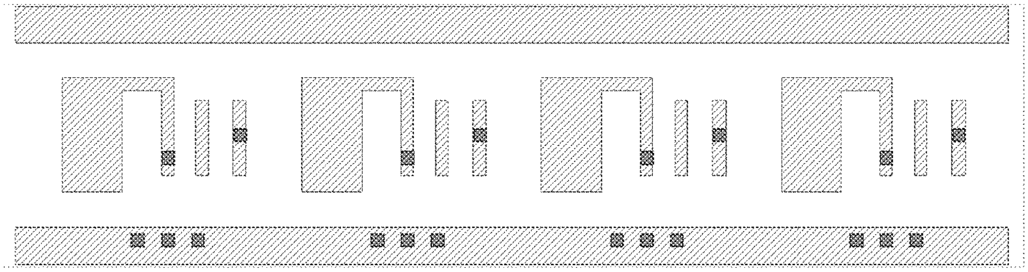
Figure 120A:
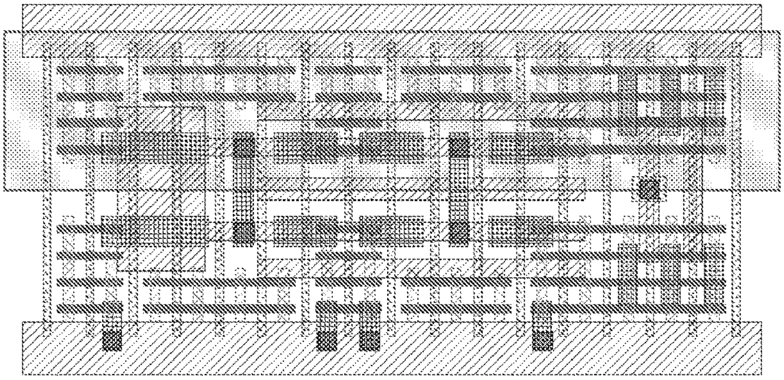
Figure 120B:
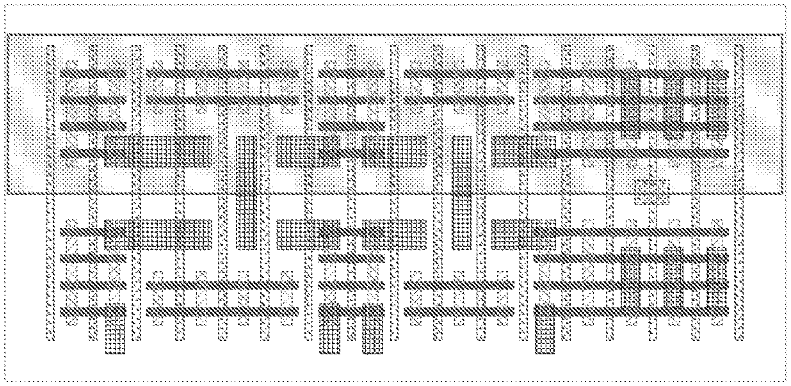
Figure 120C:
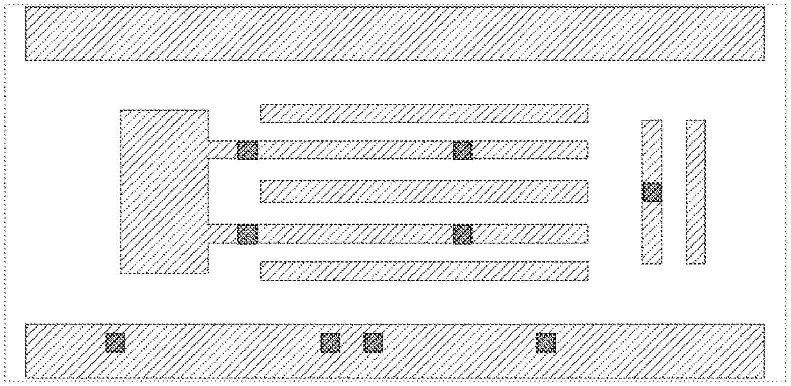
Figure 121A:
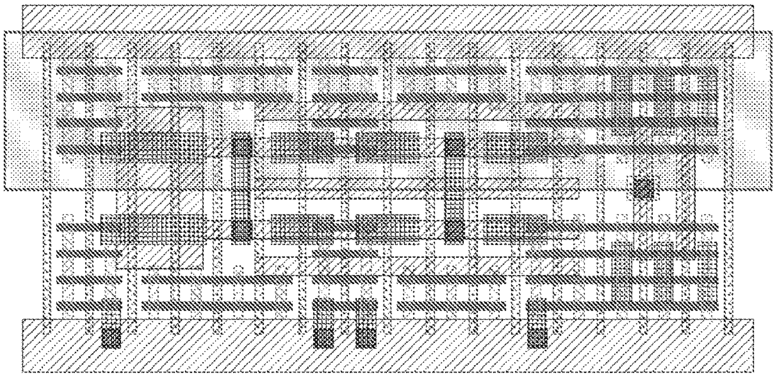
Figure 121B:
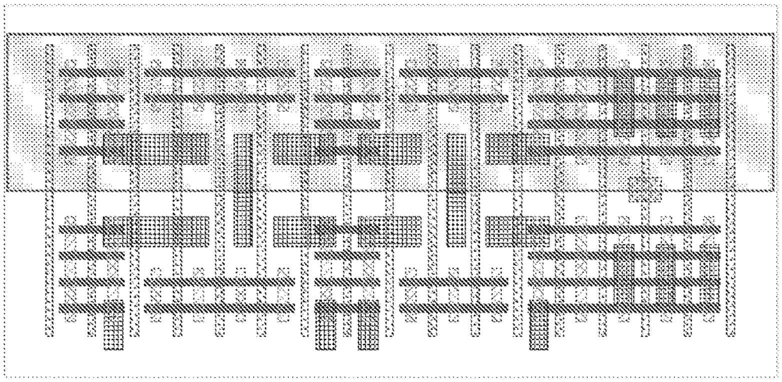
Figure 121C:
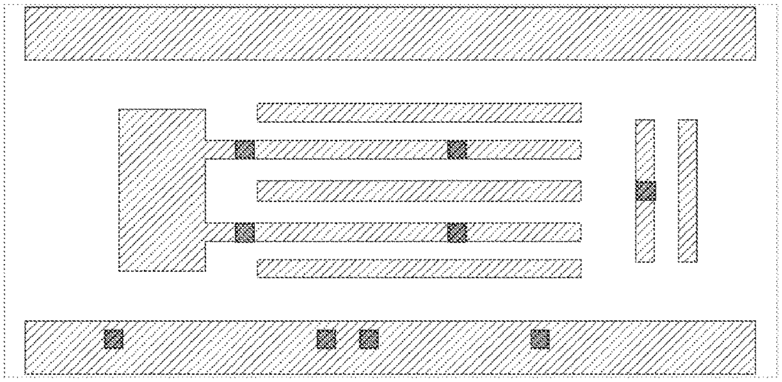
Figure 122A:
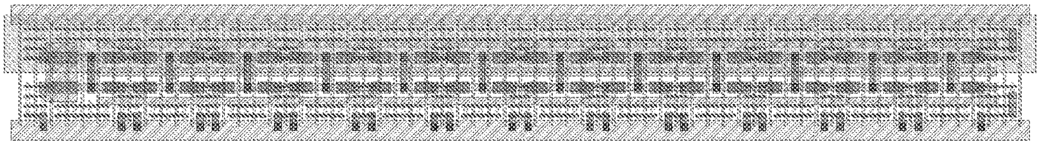
Figure 122B:
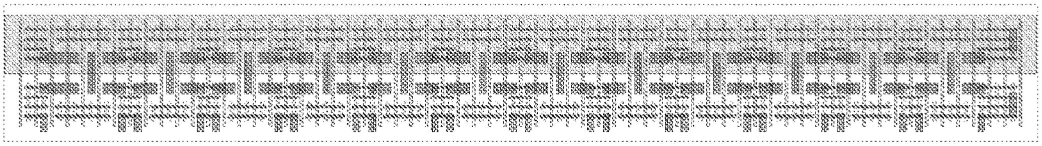
Figure 122C:
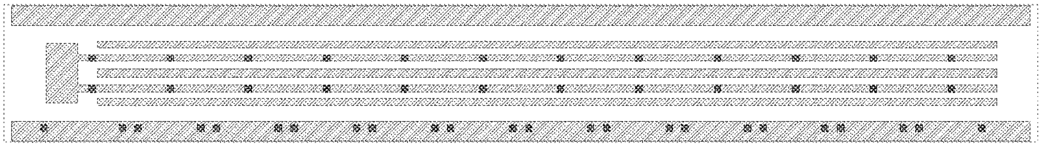
Figure 123A:
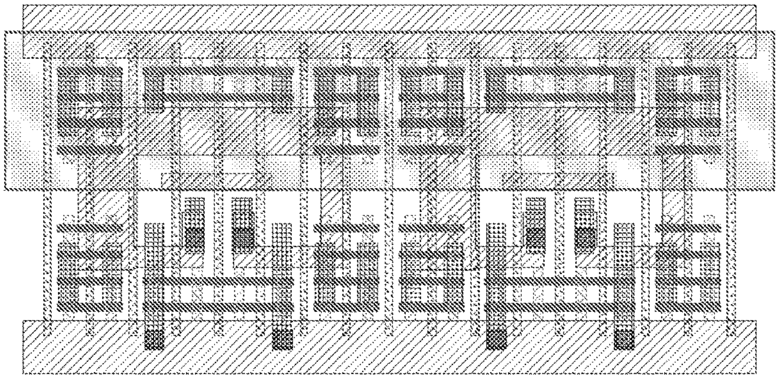
Figure 123B:
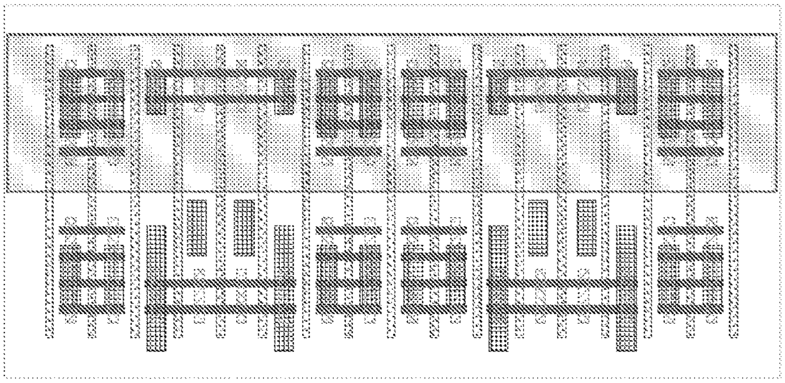
Figure 123C:
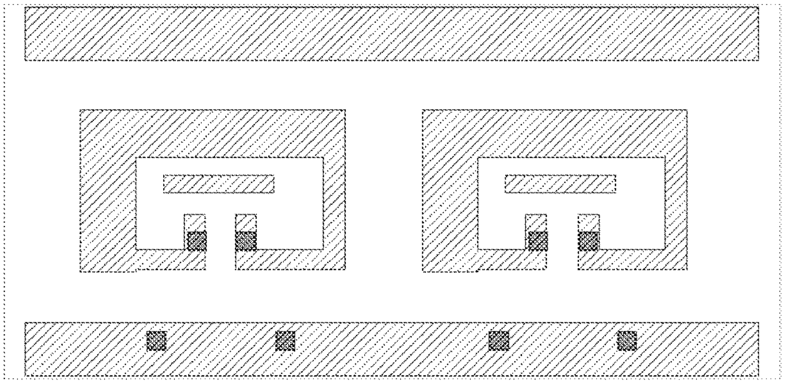
Figure 124A:
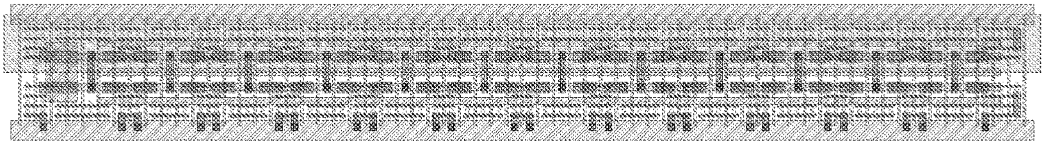
Figure 124B:
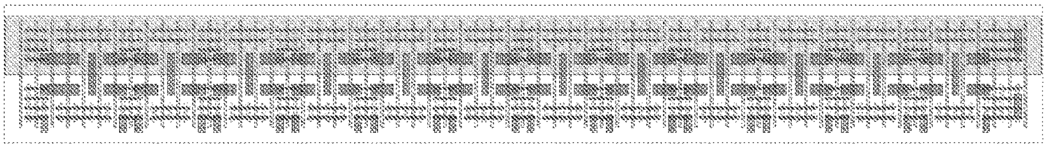
Figure 124C:
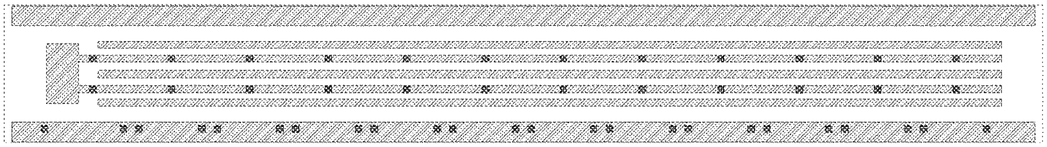
Figure 125A:
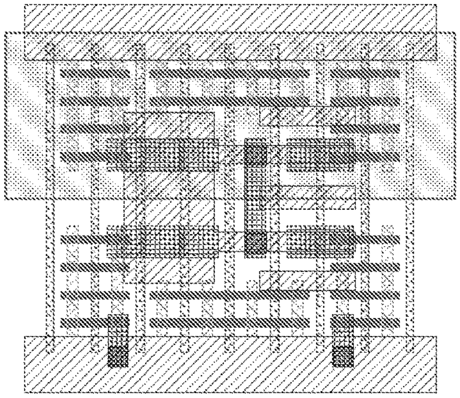
Figure 125B:
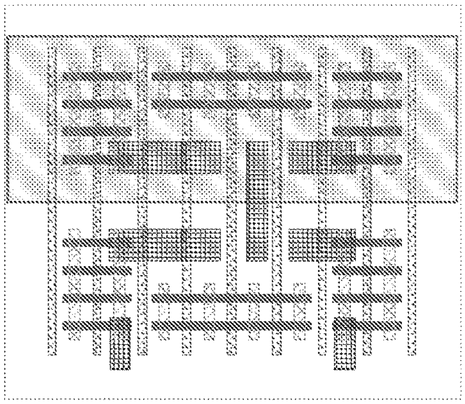
Figure 125C:
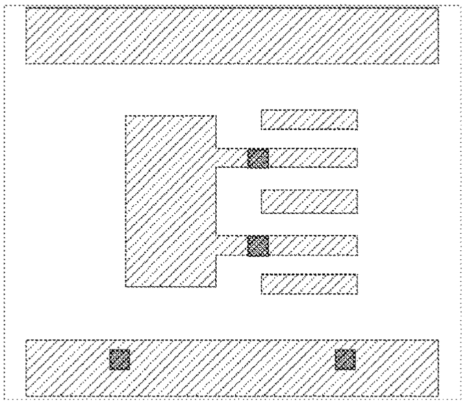
Figure 126A:
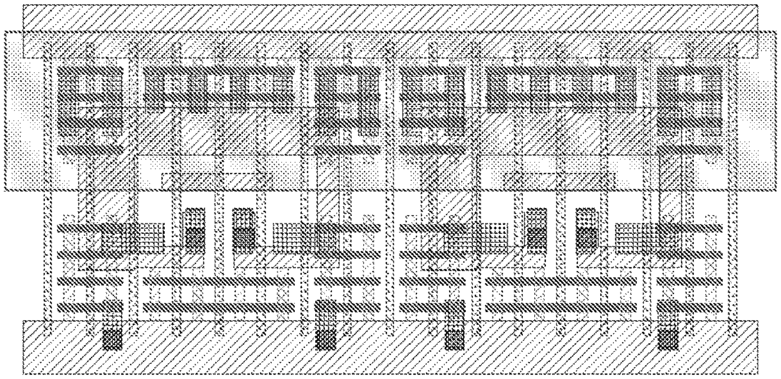
Figure 126B:
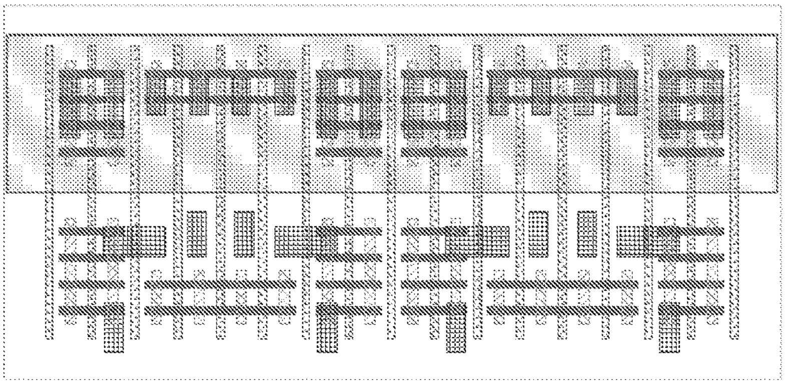
Figure 126C:
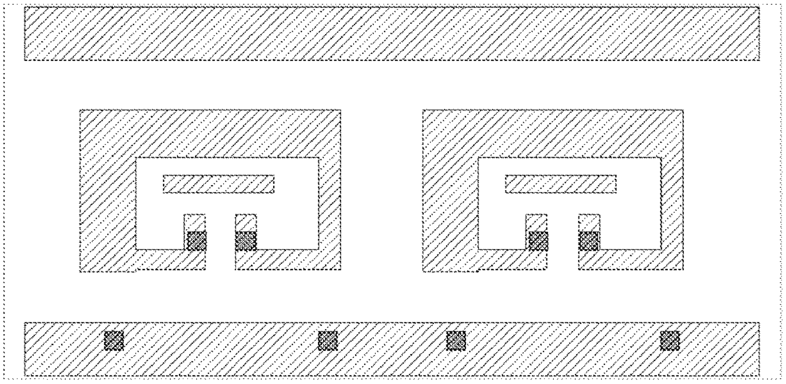
Figure 127A:
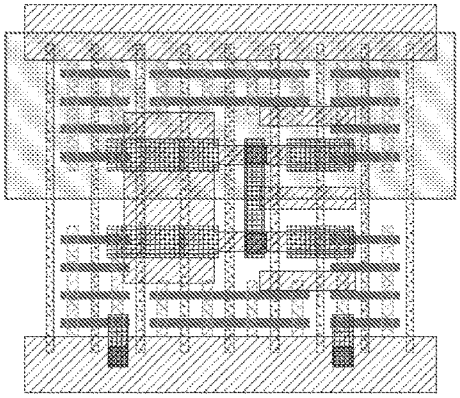
Figure 127B:
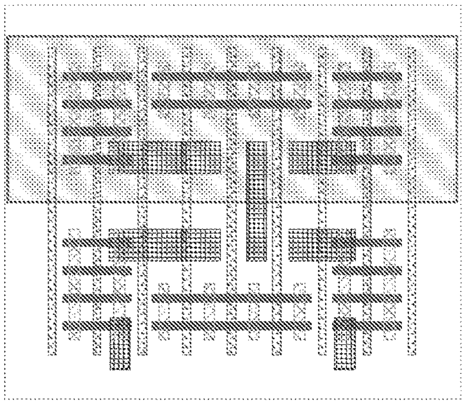
Figure 127C:
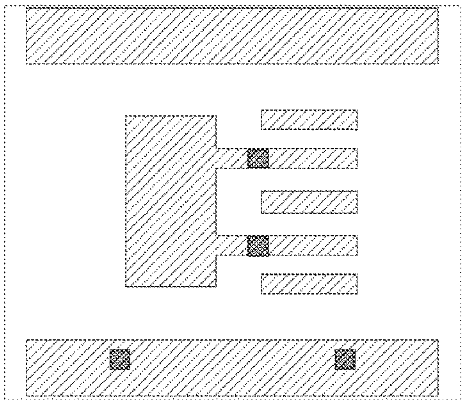
Figure 128A:
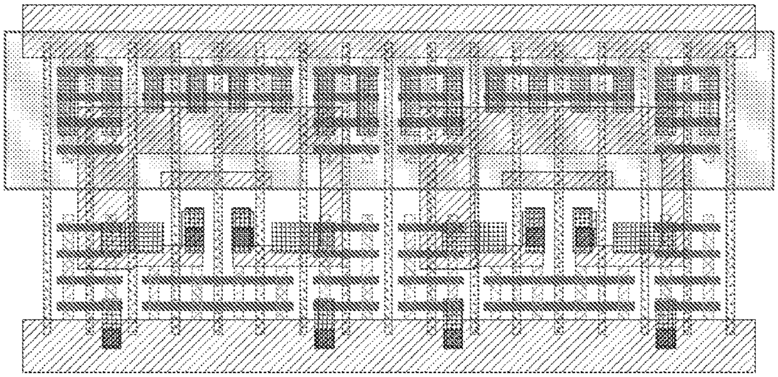
Figure 128B:
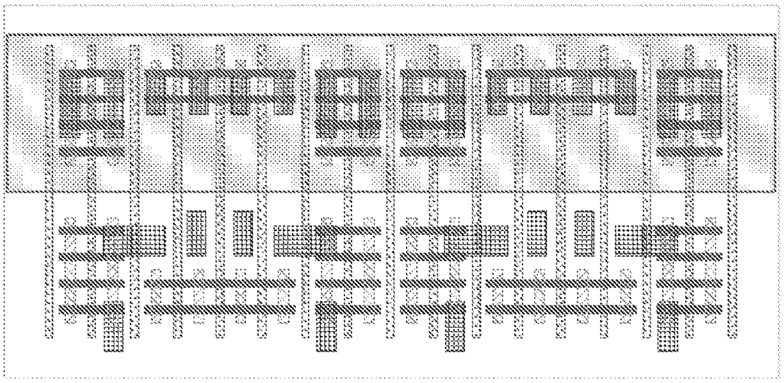
Figure 128C:
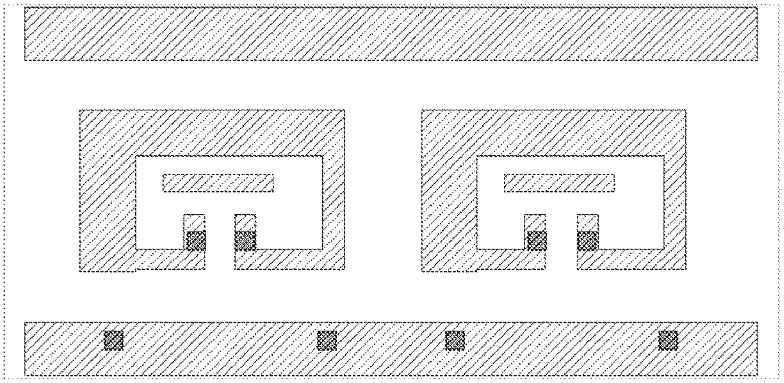
Figure 129A:
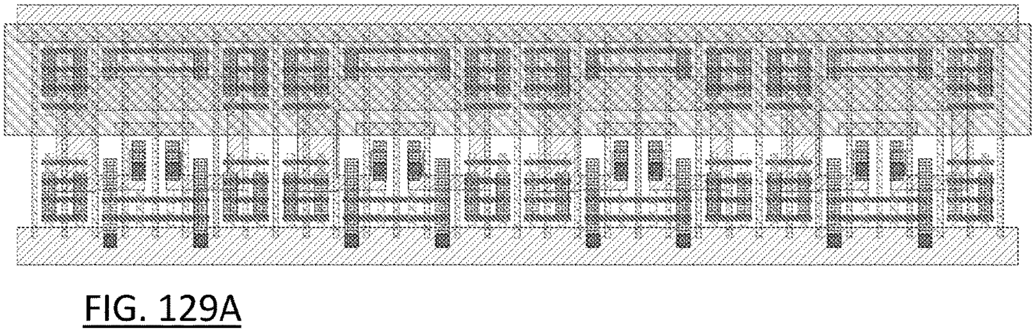
Figure 129B:
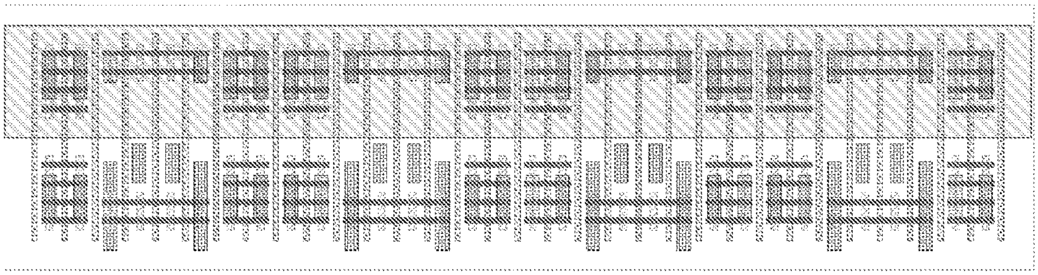
Figure 129C:
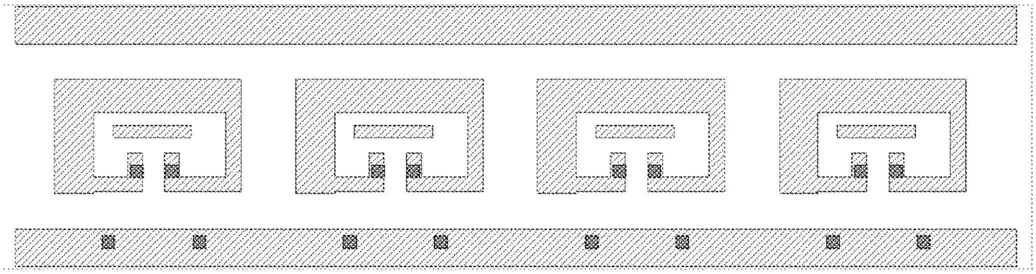
Figure 130A:
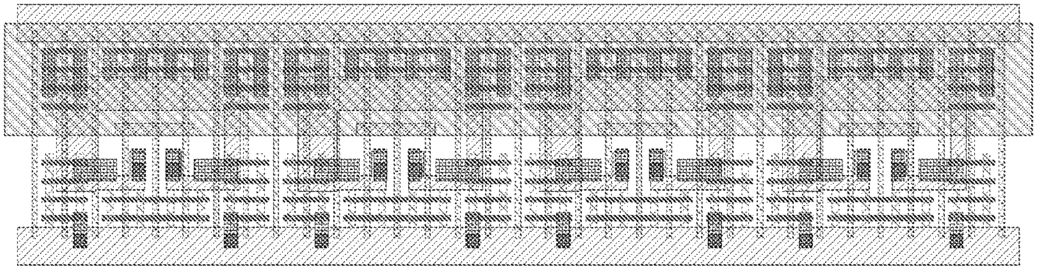
Figure 130B:
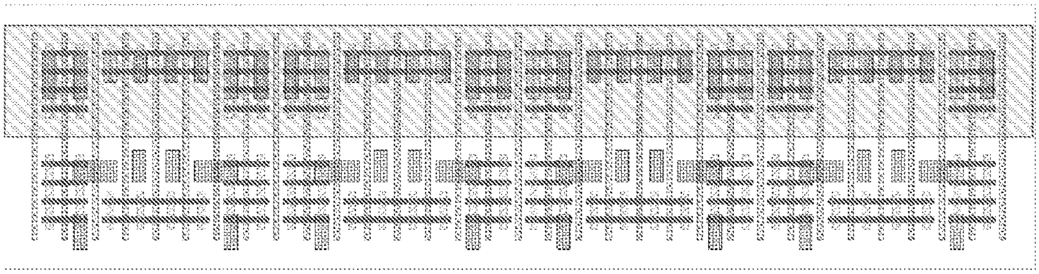
Figure 130C:
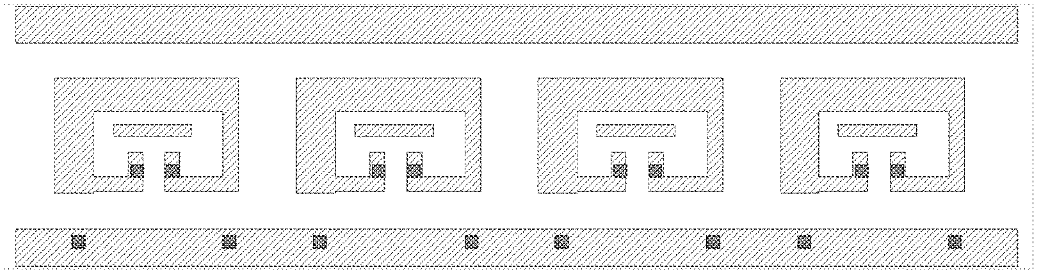
Figure 131A:
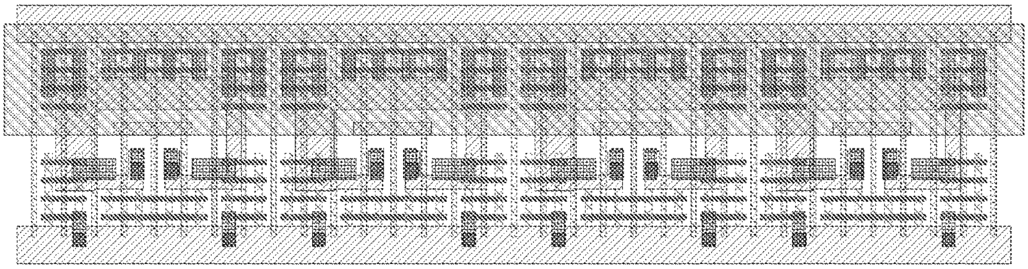
Figure 131B:
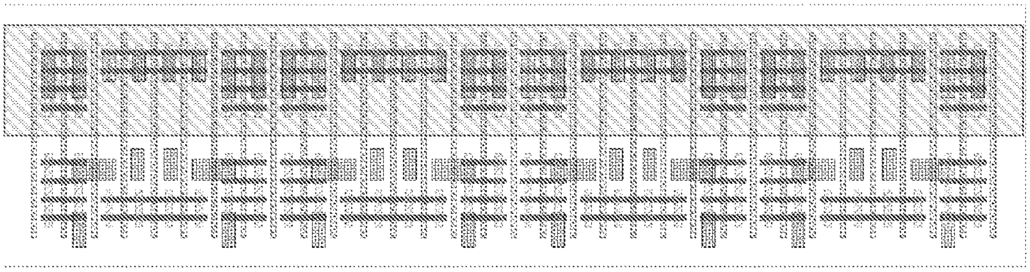
Figure 131C:
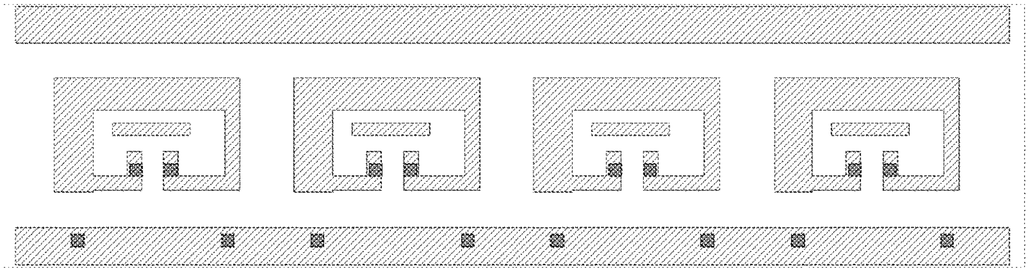
Figure 132A:
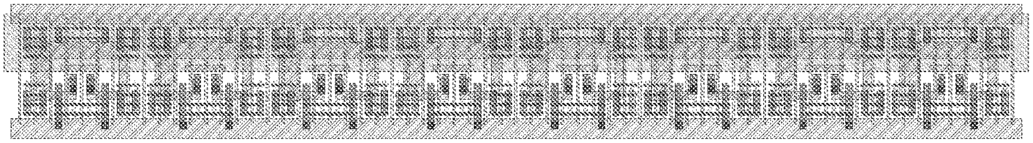
Figure 132B:
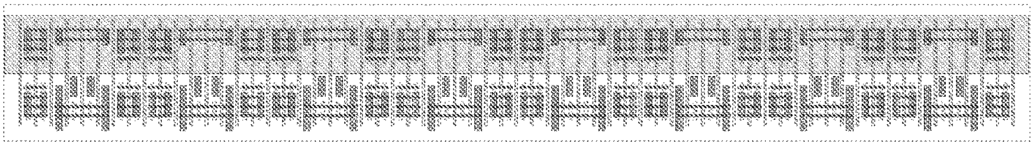
Figure 132C:
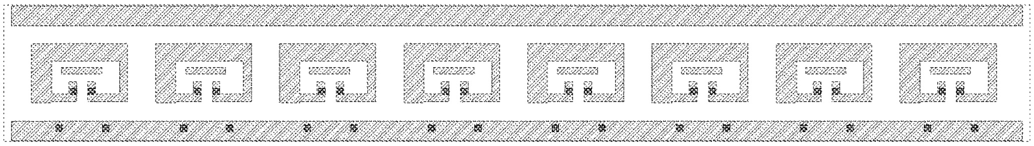
Figure 133A:
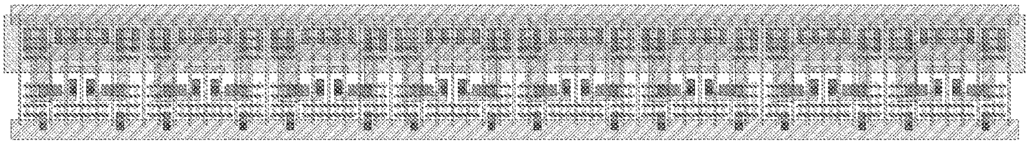
Figure 133B:
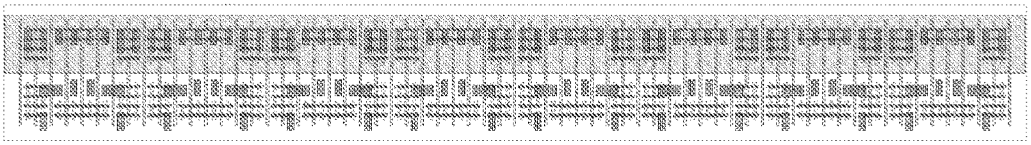
Figure 133C:
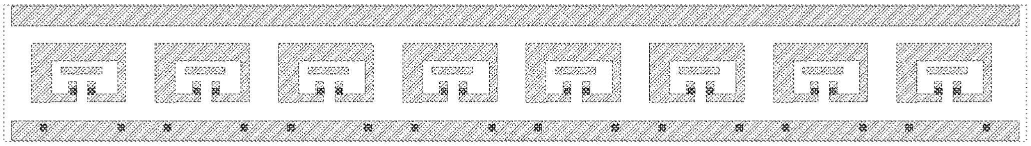
Figure 134A:
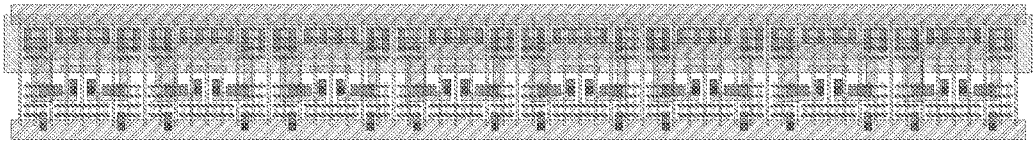
Figure 134B:
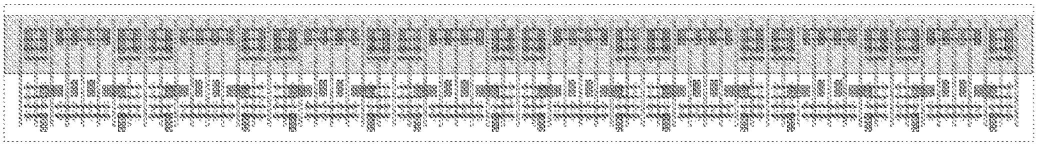
Figure 134C:
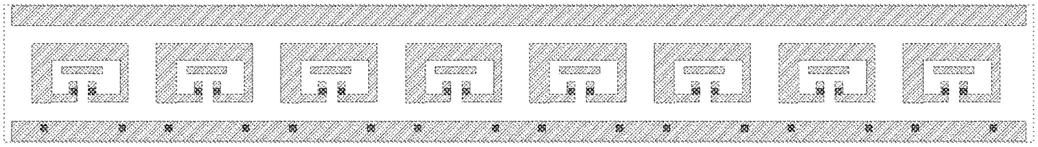
Figure 135A:
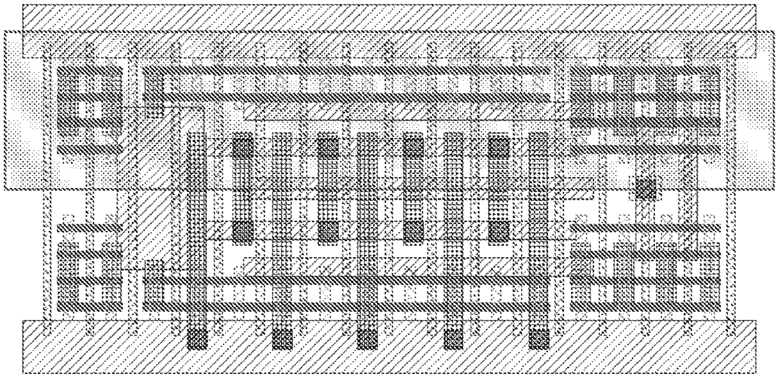
Figure 135B:
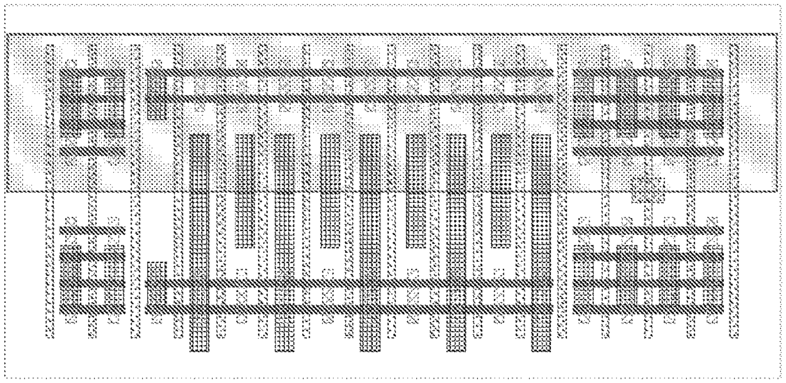
Figure 135C:
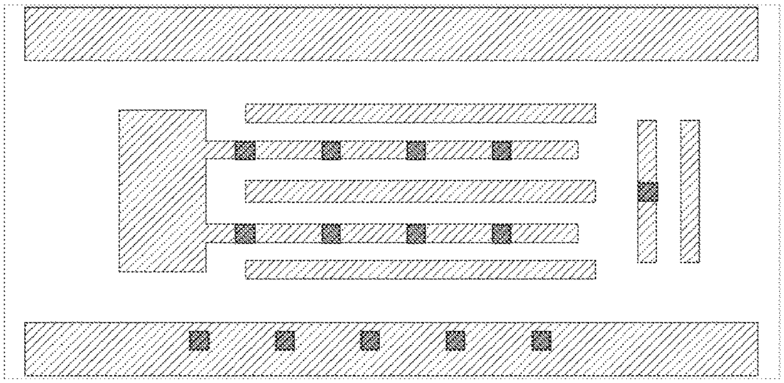
Figure 136A:
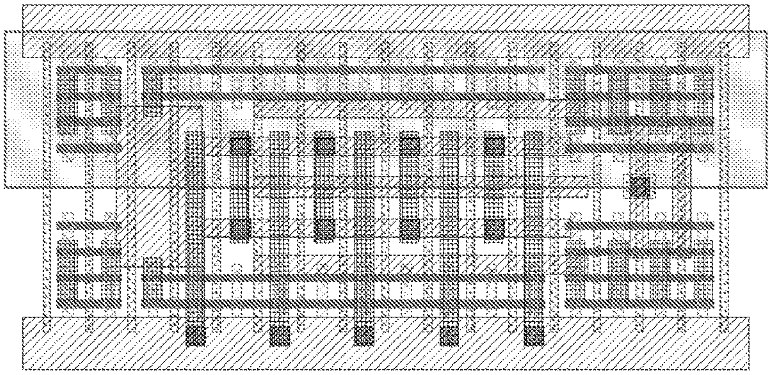
Figure 136B:
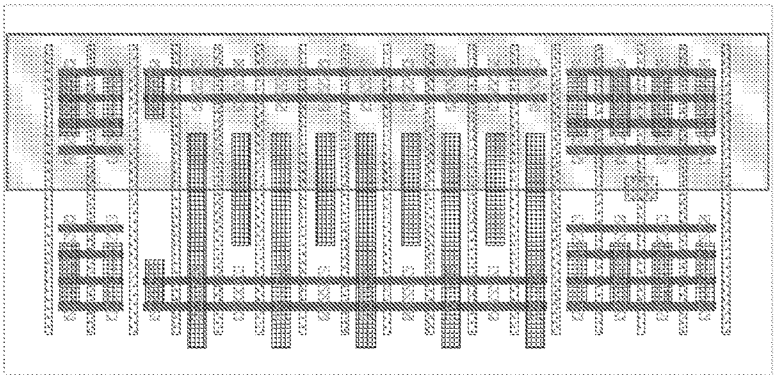
Figure 136C:
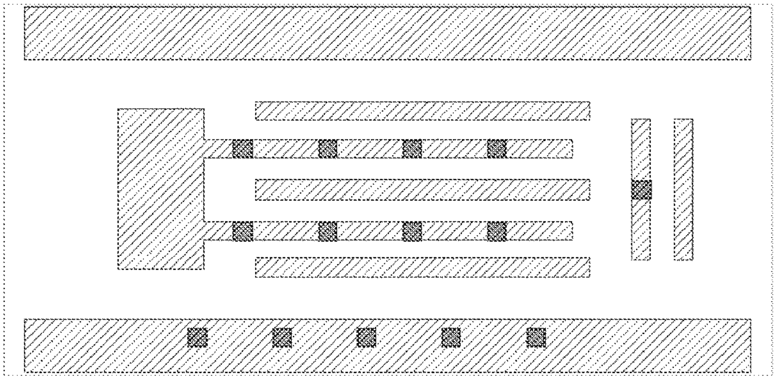
Figure 137A:
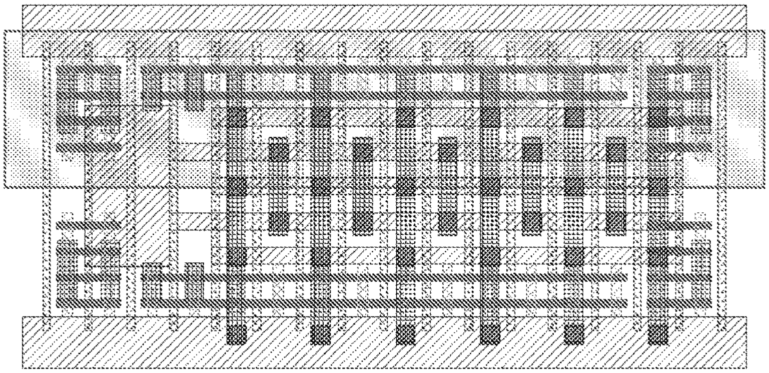
Figure 137B:
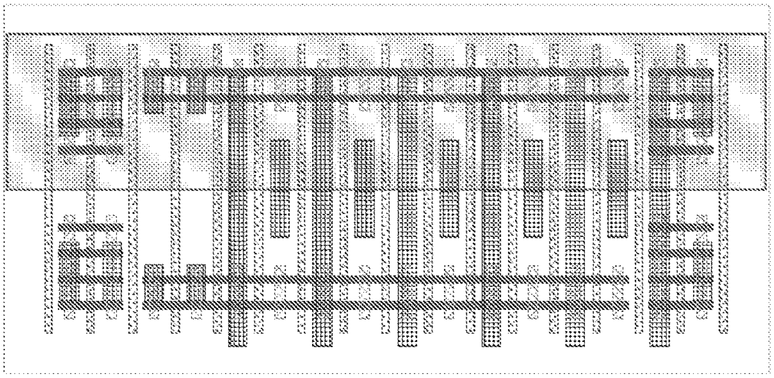
Figure 137C:
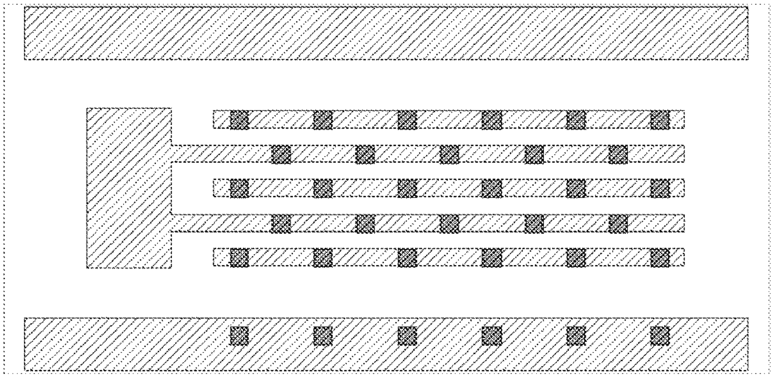
Figure 138A:
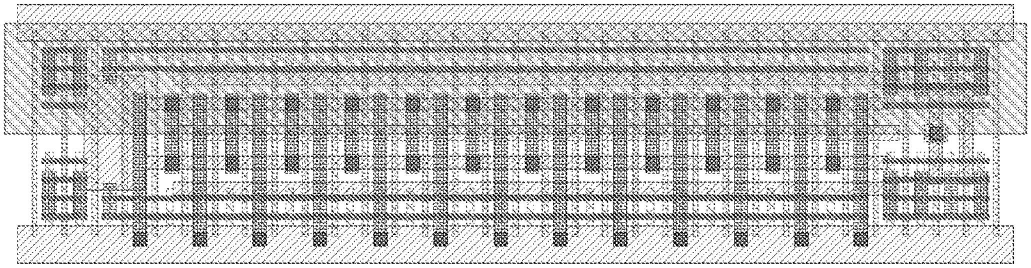
Figure 138B:
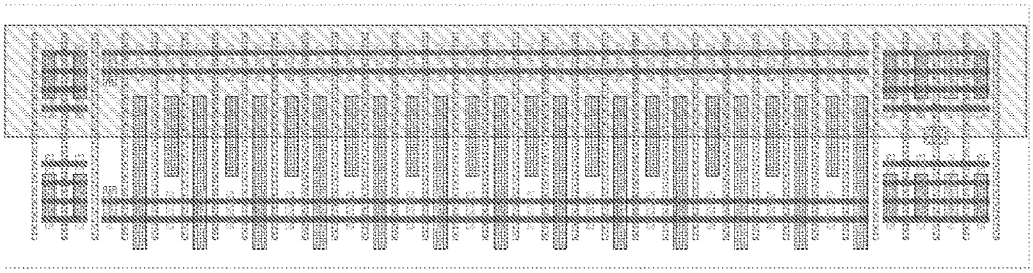
Figure 138C:
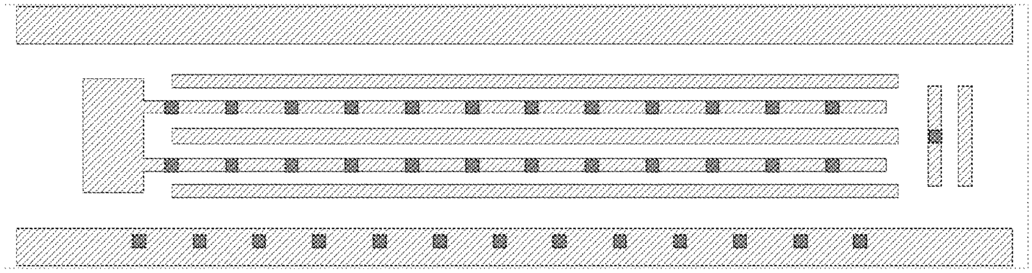
Figure 139A:
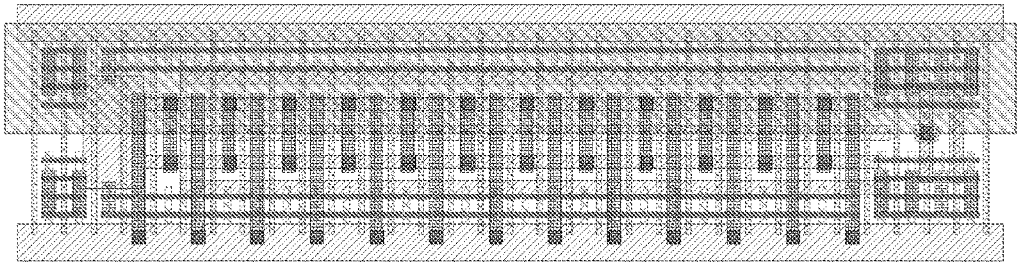
Figure 139B:
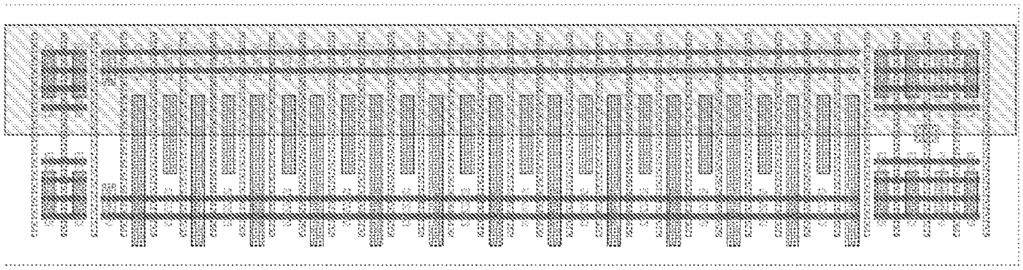
Figure 139C:
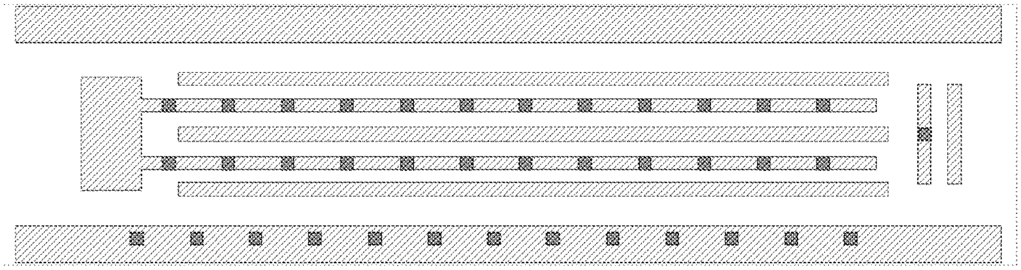
Figure 140A:
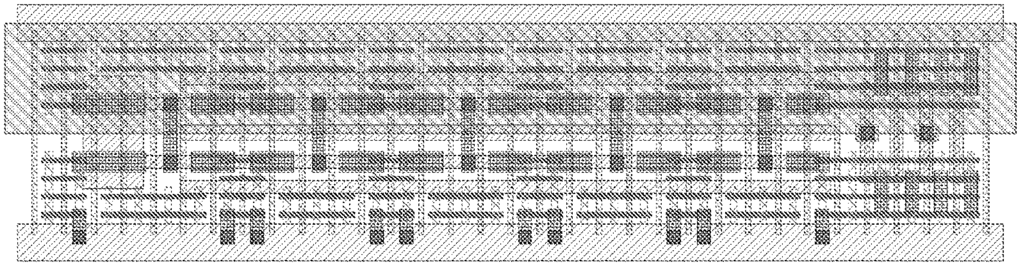
Figure 140B:
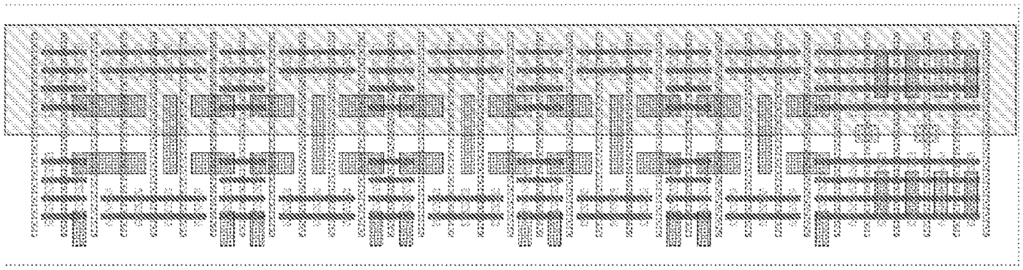
Figure 140C:
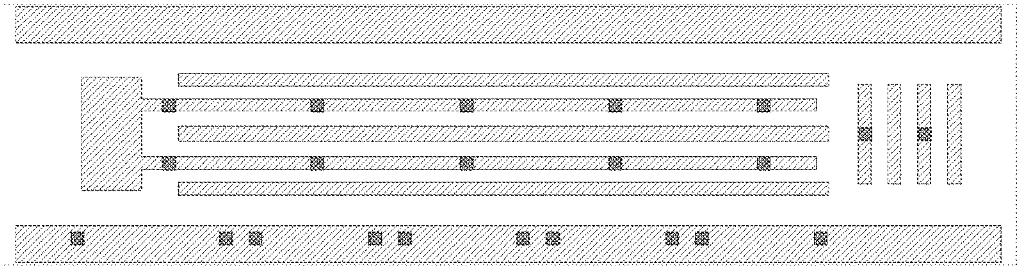
Figure 141A:
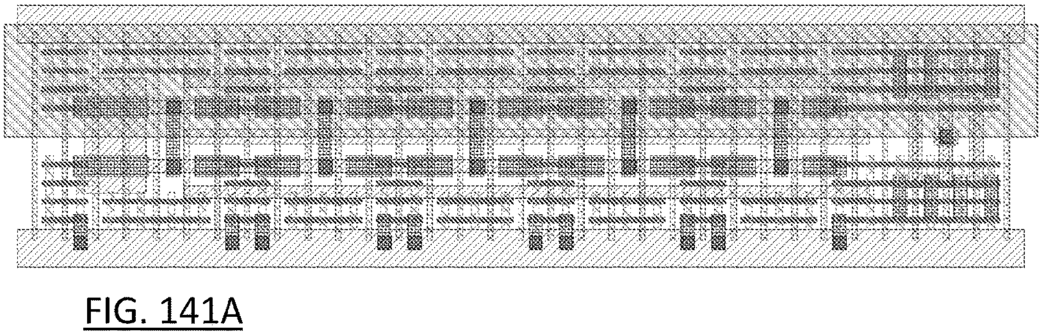
Figure 141B:
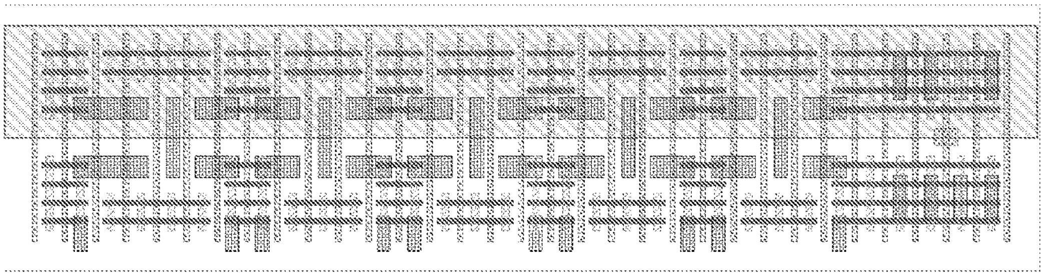
Figure 141C:
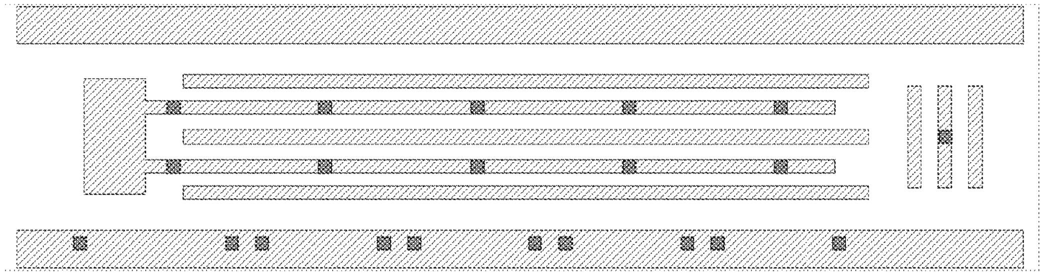
Figure 142A:
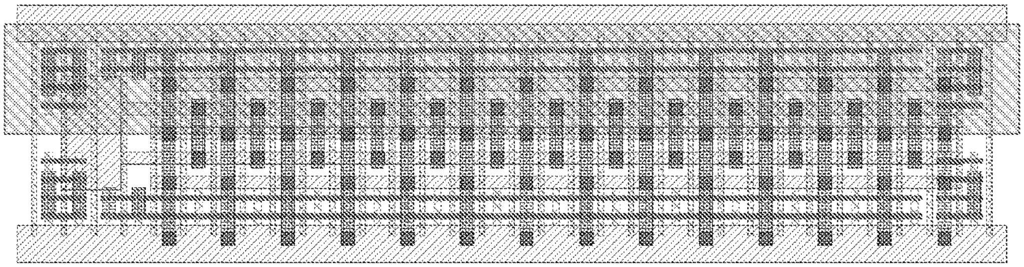
Figure 142B:
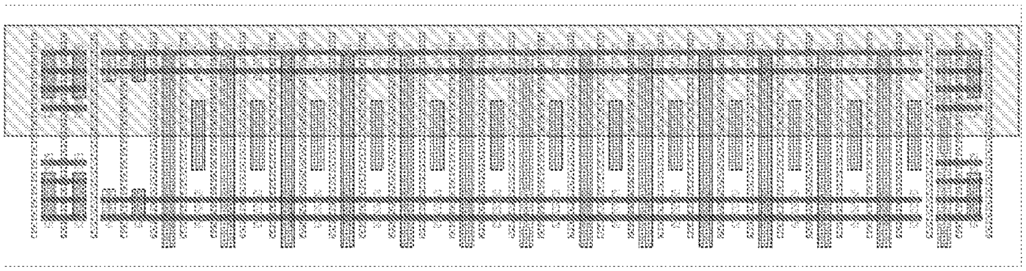
Figure 142C:
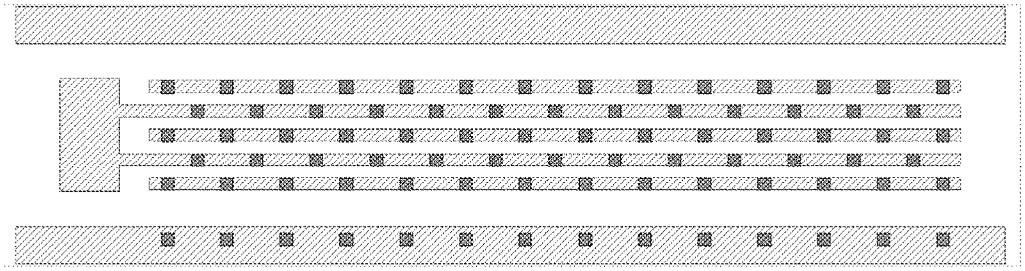
Figure 143A:
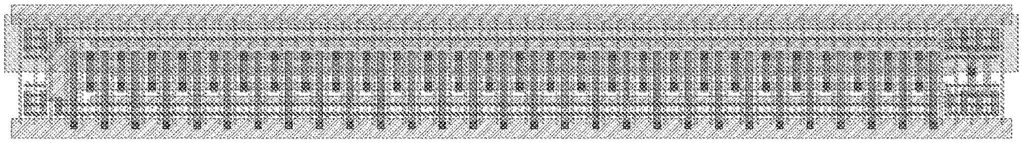
Figure 143B:
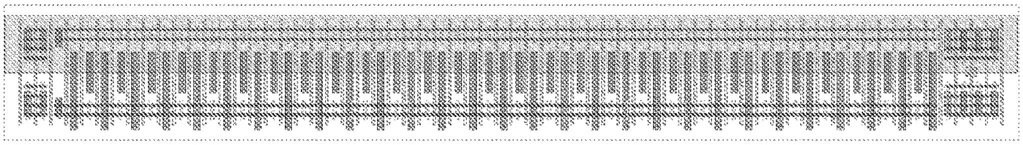
Figure 143C:
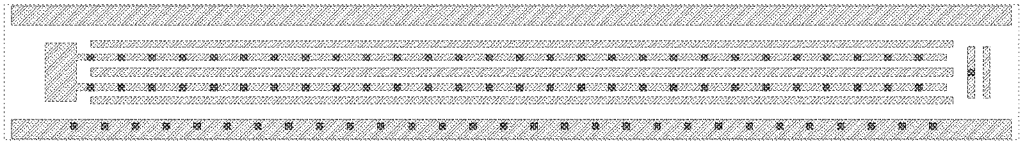
Figure 144A:
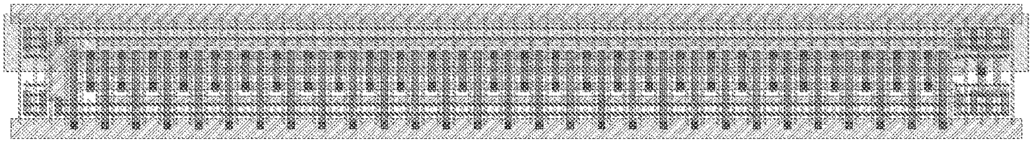
Figure 144B:
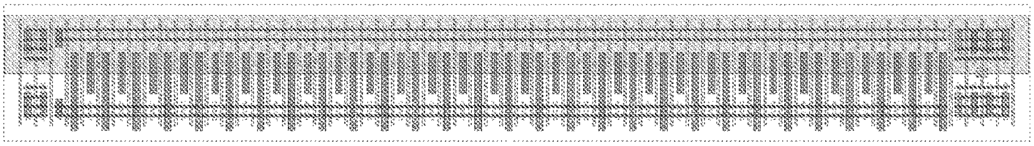
Figure 144C:
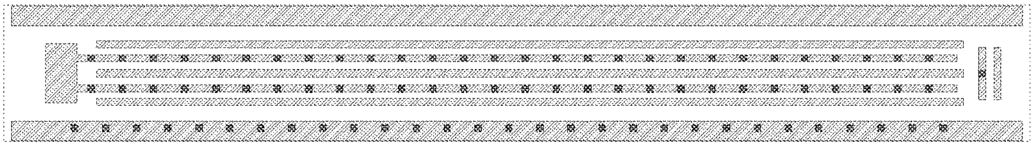
Figure 145A:
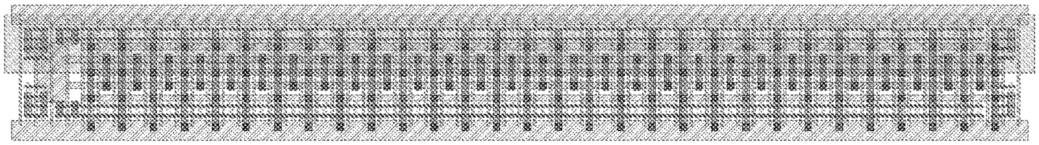
Figure 145B:
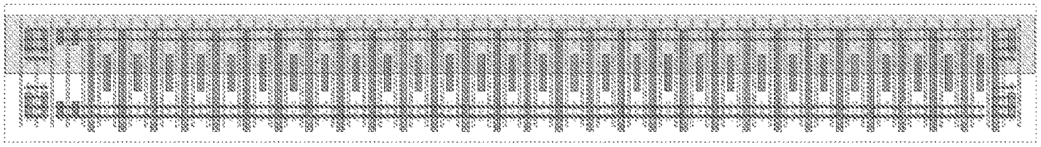
Figure 145C:
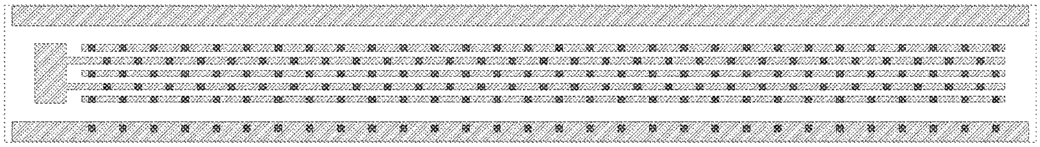
Figure 146A:
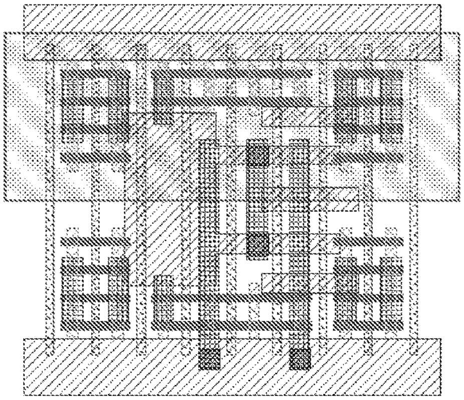
Figure 146B:
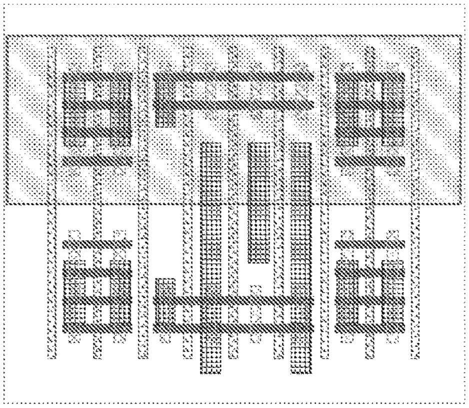
Figure 146C:
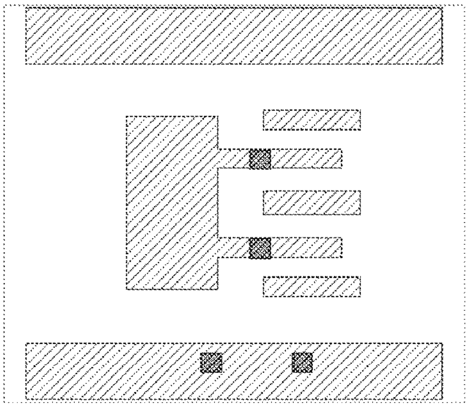
Figure 147A:
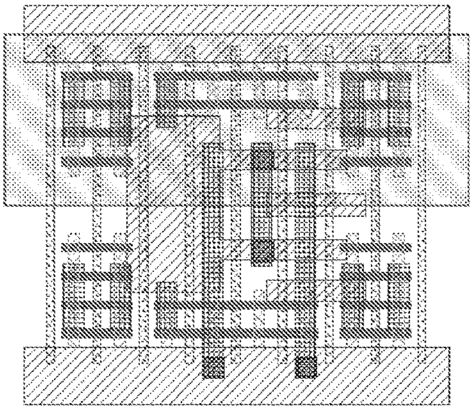
Figure 147B:
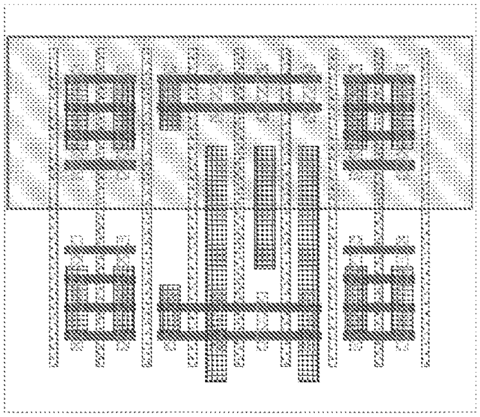
Figure 147C:
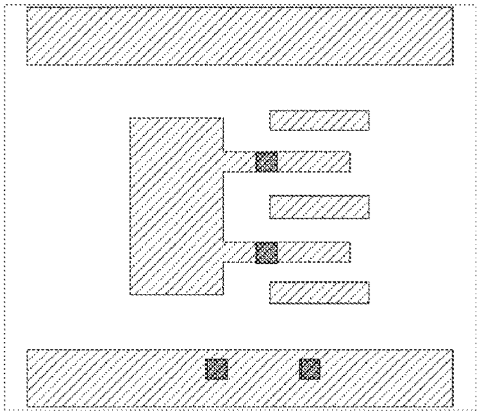
Figure 148A:
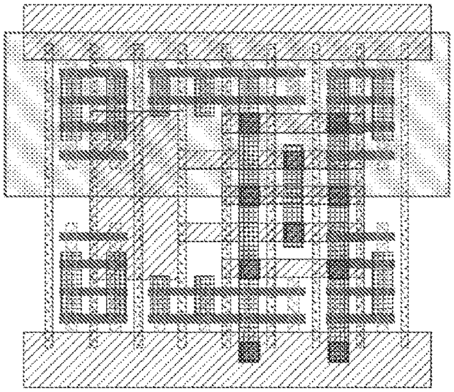
Figure 148B:
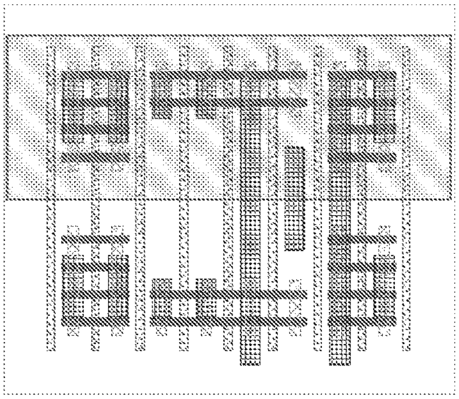
Figure 148C:
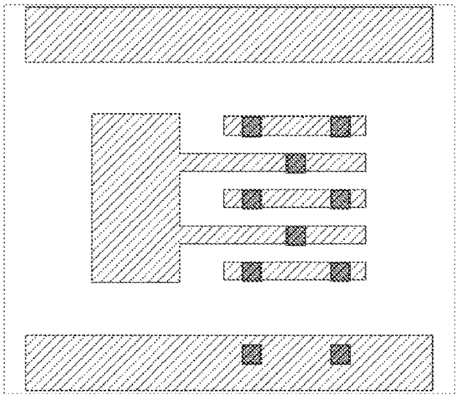
Figure 149A:
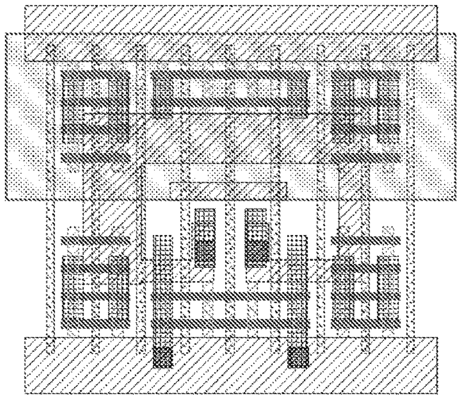
Figure 149B:
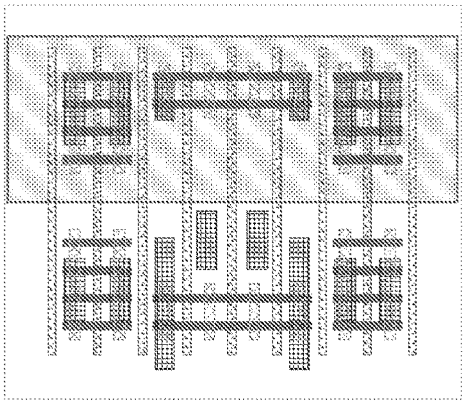
Figure 149C:
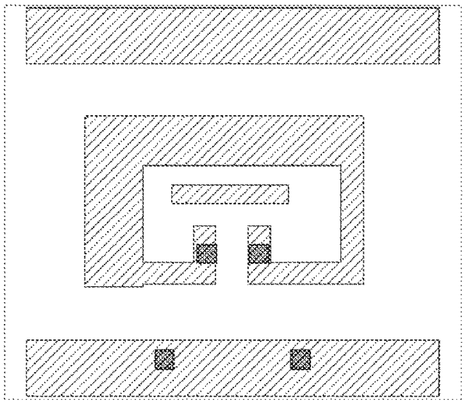
Figure 150A:
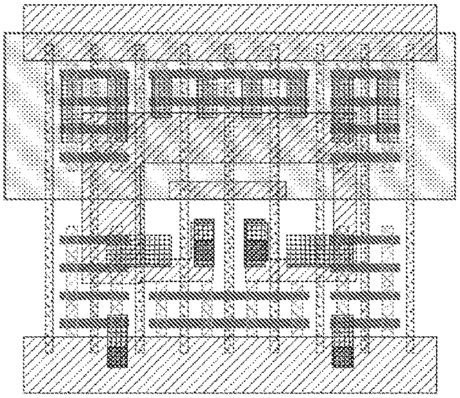
Figure 150B:
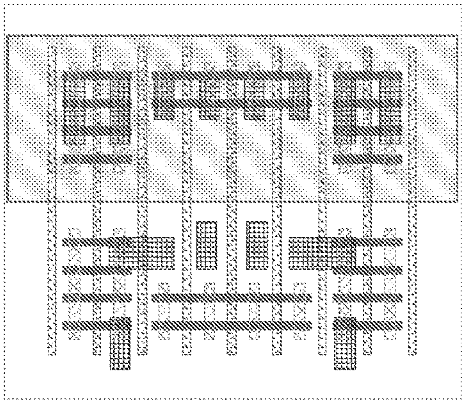
Figure 150C:
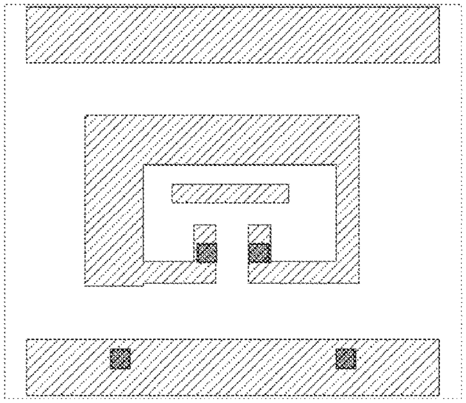
Figure 151A:
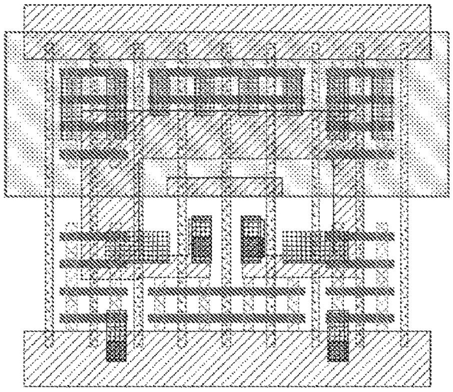
Figure 151B:
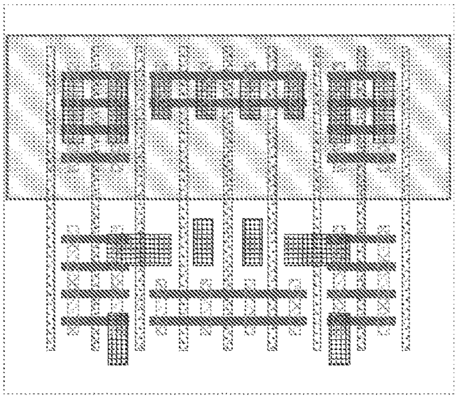
Figure 151C:
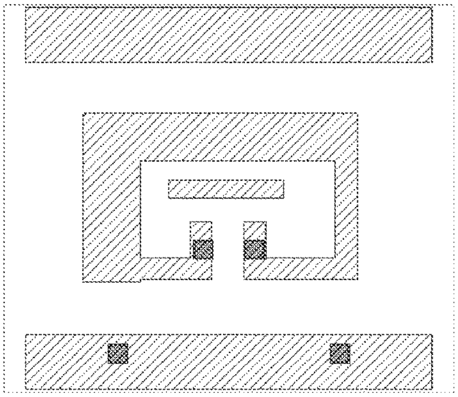
Figure 152A:
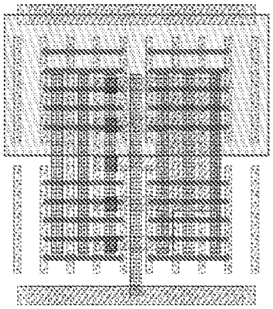
Figure 152B:
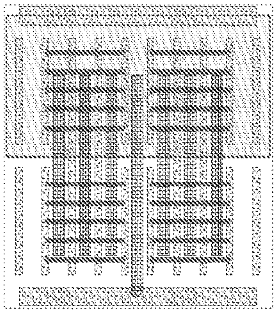
Figure 152C:
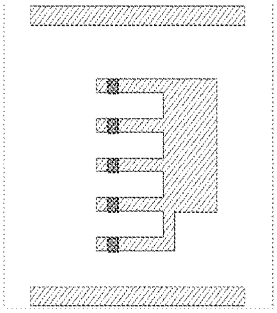
Figure 153A:
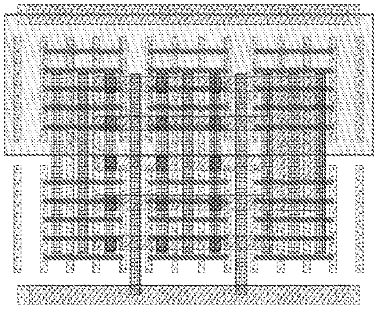
Figure 153B:
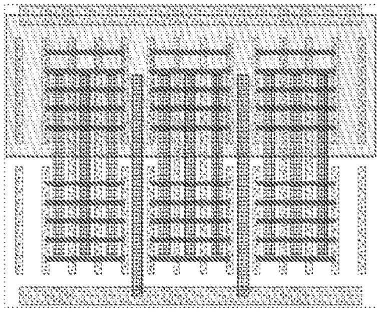
Figure 153C:
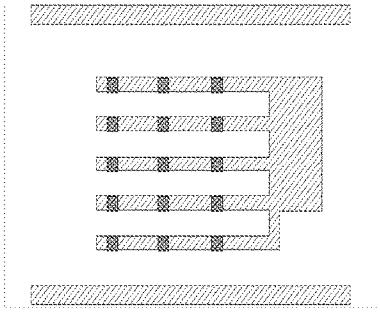
Figure 154A:
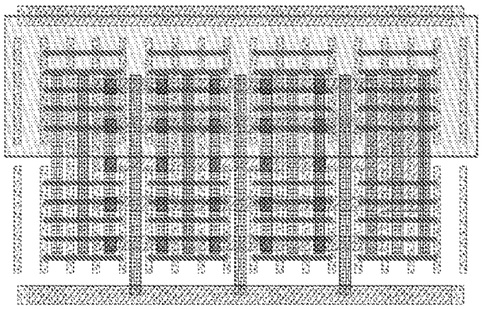
Figure 154B:
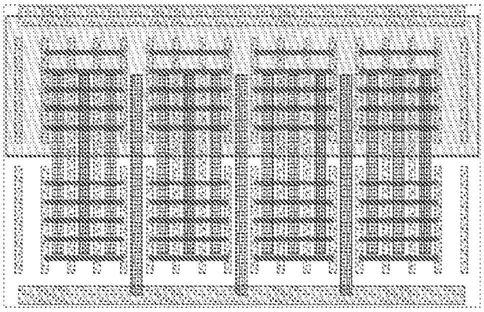
Figure 154C:
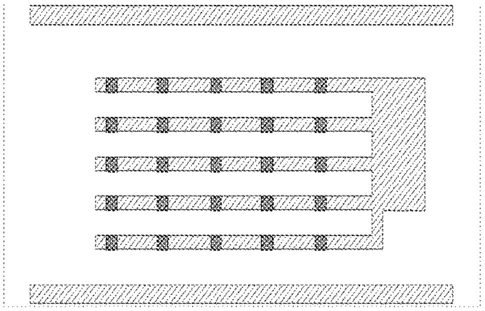
Figure 155A:
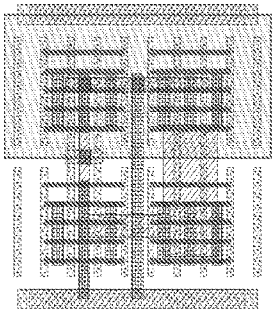
Figure 155B:
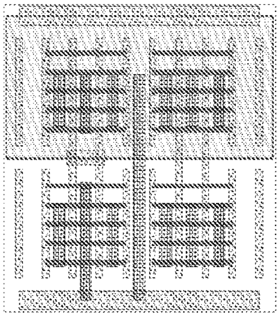
Figure 155C:
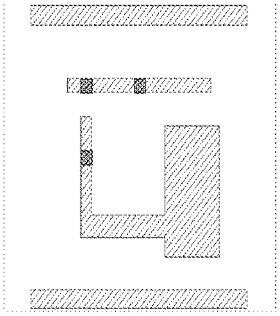
Figure 156A:
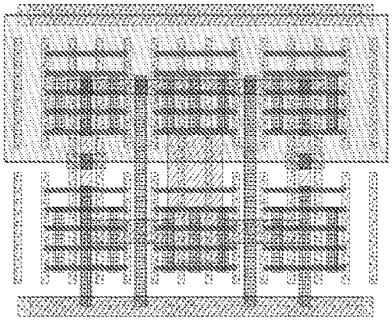
Figure 156B:
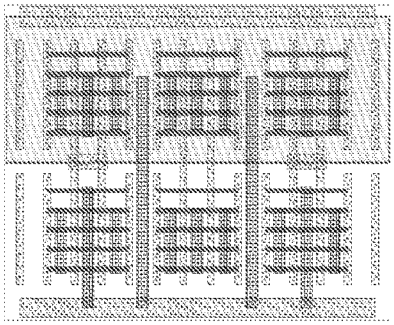
Figure 156C:
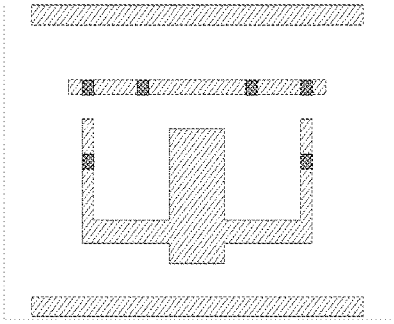
Figure 157A:
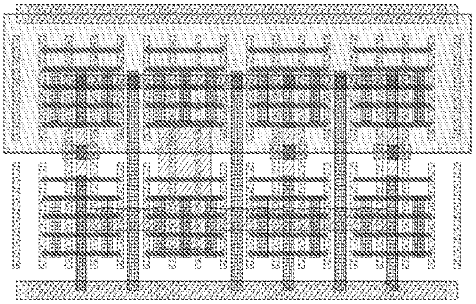
Figure 157B:
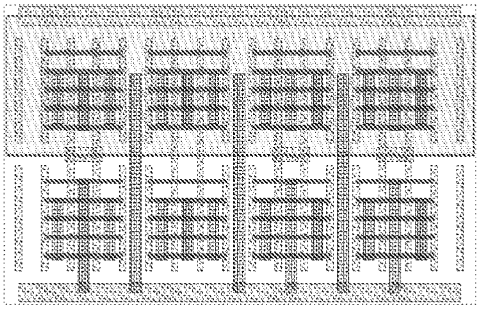
Figure 157C:
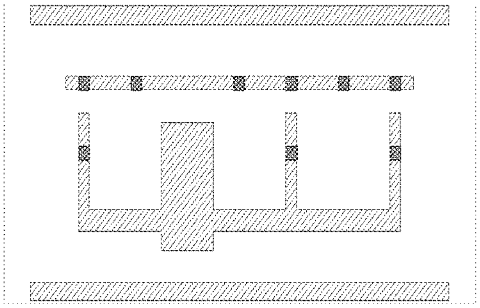
Figure 158A:
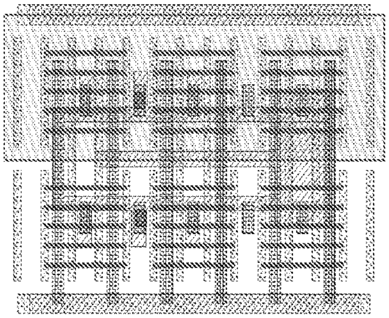
Figure 158B:
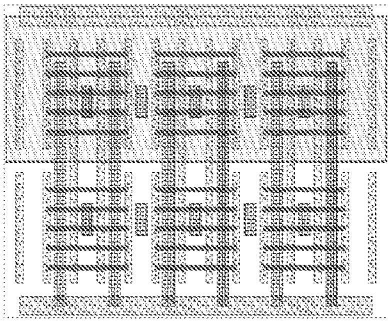
Figure 158C:
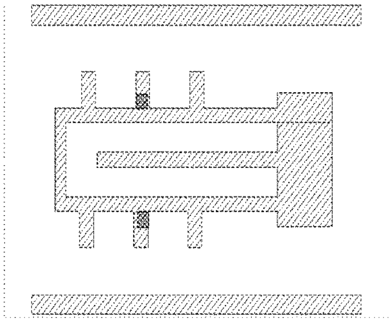
Figure 159A:
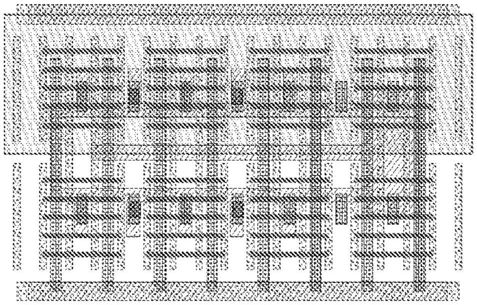
Figure 159B:
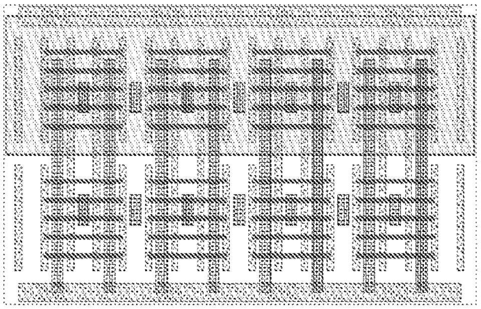
Figure 159C:
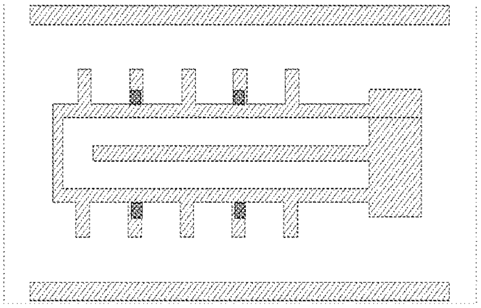
Figure 160A:
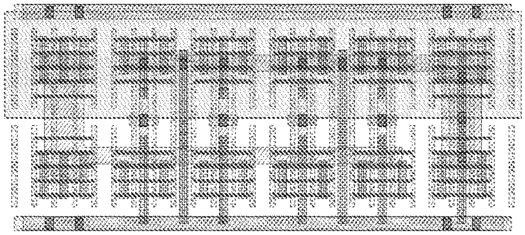
Figure 160B:
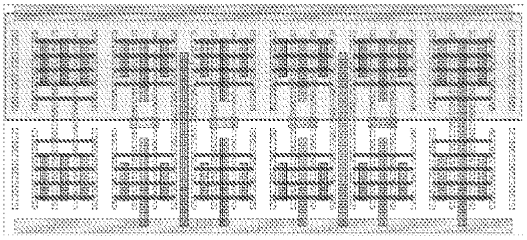
Figure 160C:
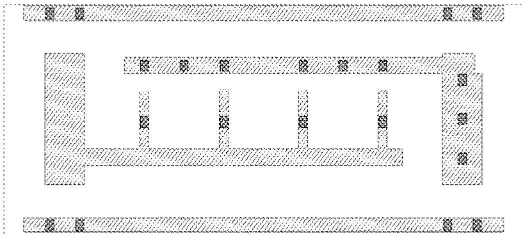
Figure 161A:
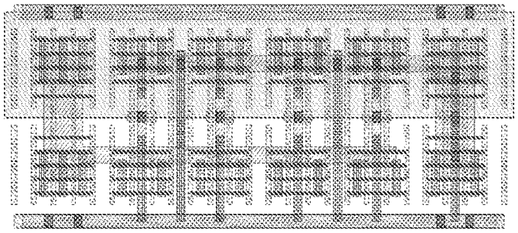
Figure 161B:
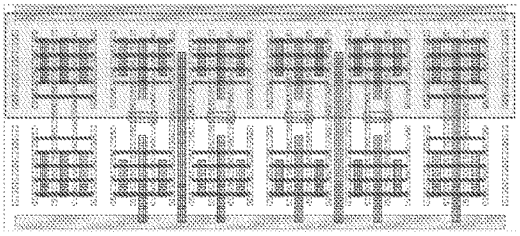
Figure 161C:
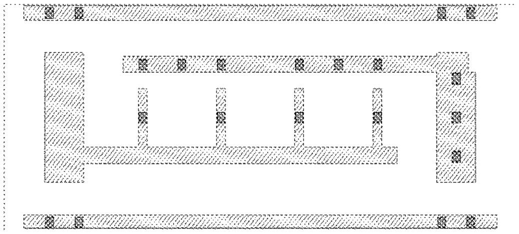
Figure 162A:
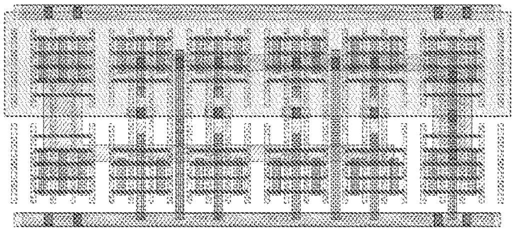
Figure 162B:
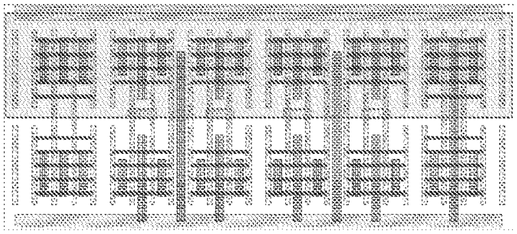
Figure 162C:
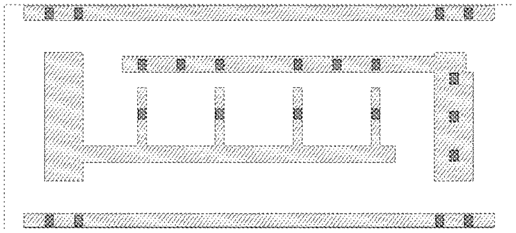
Figure 163A:
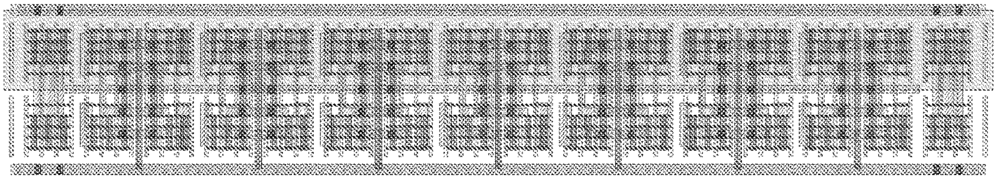
Figure 163B:
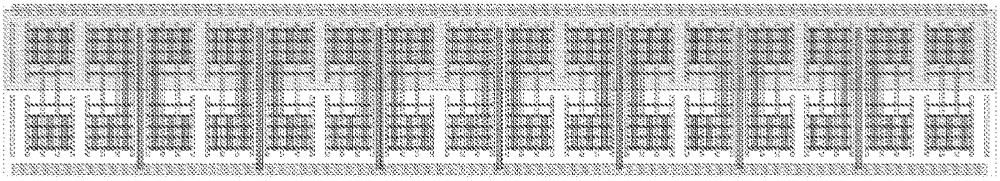
Figure 163C:
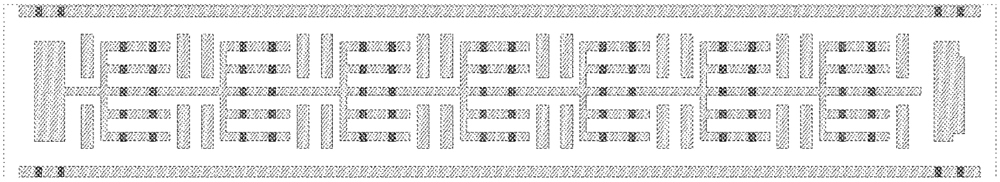
Figure 164A:
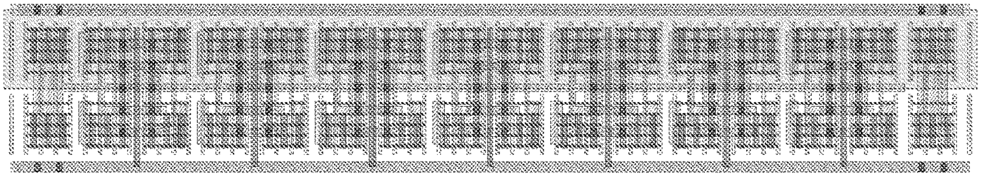
Figure 164B:
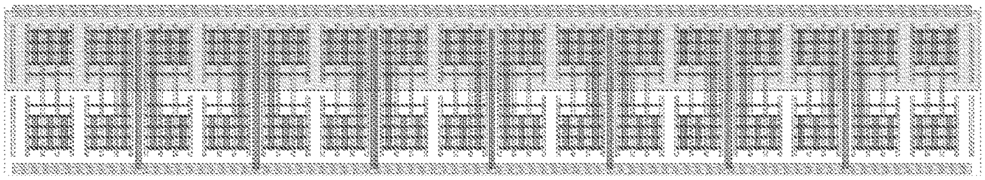
Figure 164C:
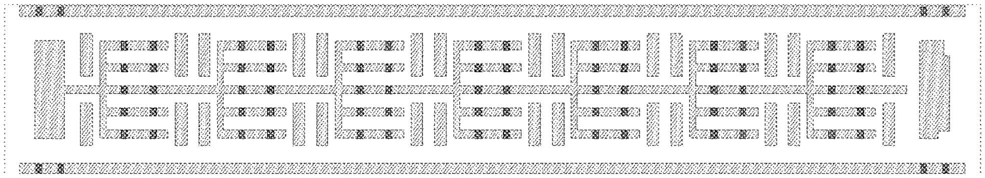
Figure 165A:
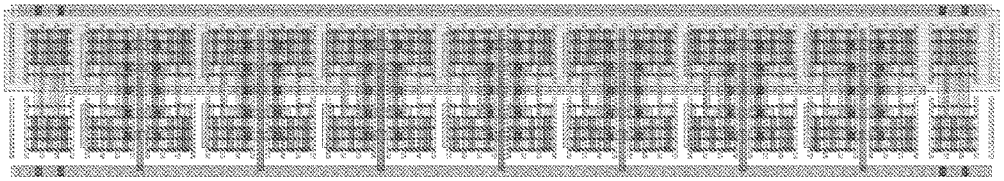
Figure 165B:
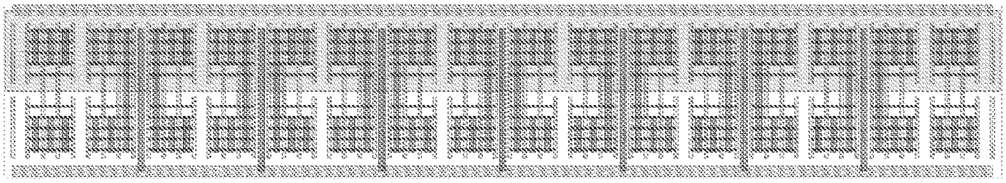
Figure 165C:
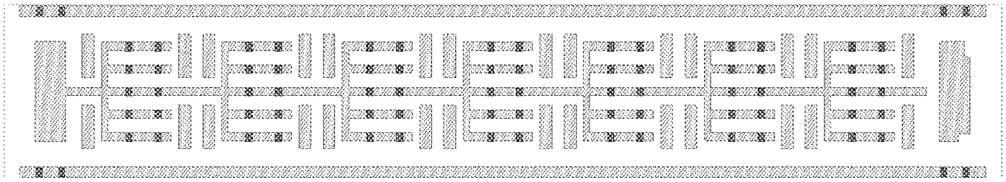
Figure 166A:
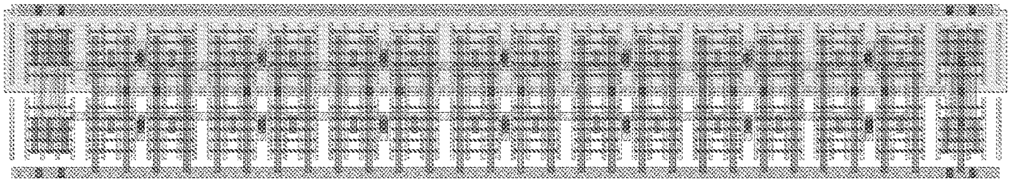
Figure 166B:
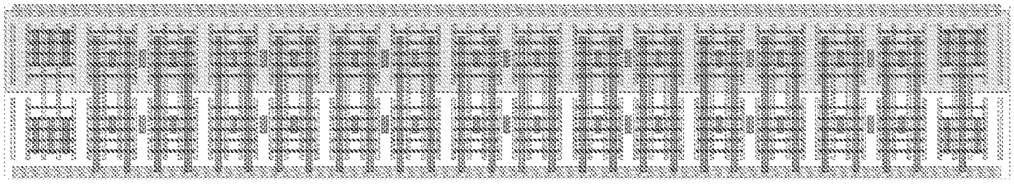
Figure 166C:
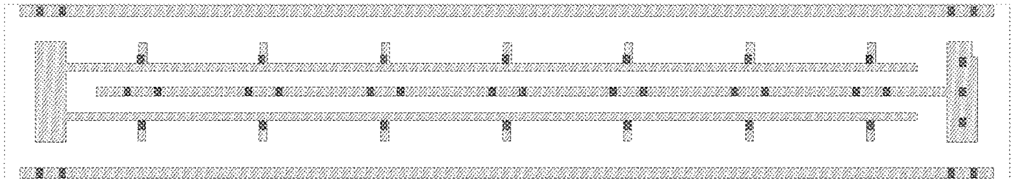
Figure 167A:
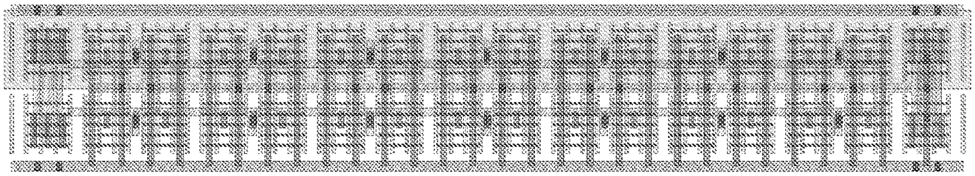
Figure 167B:
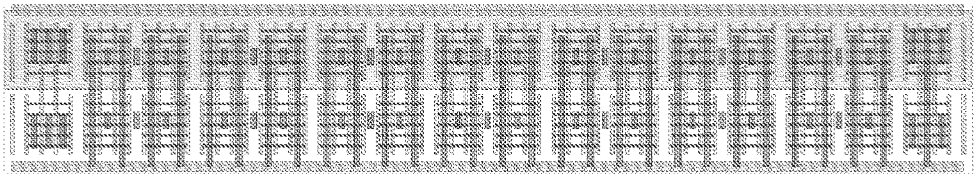
Figure 167C:
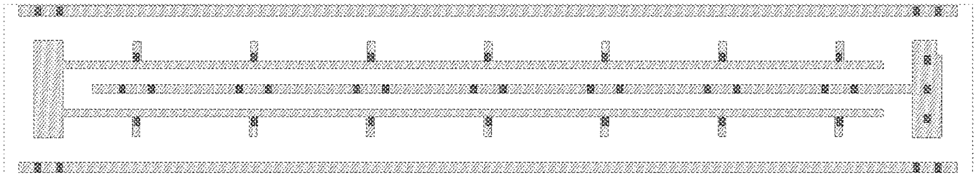
Figure 168A:
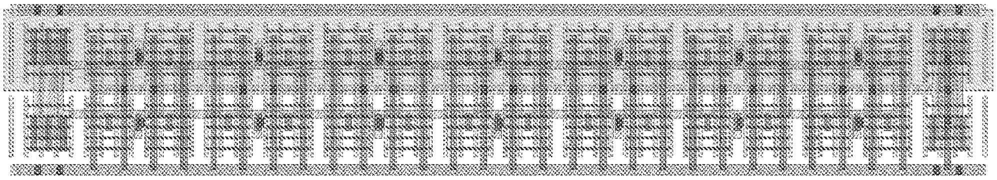
Figure 168B:
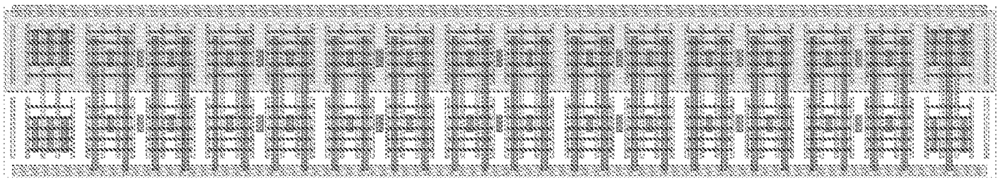
Figure 168C:
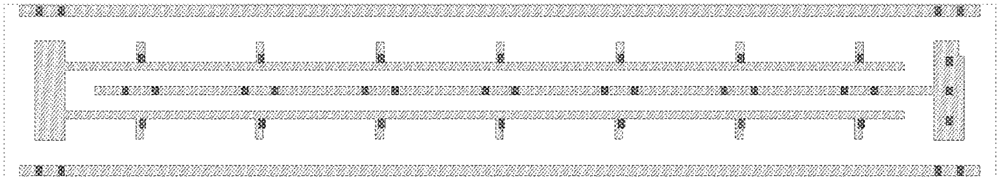
Figure 169A:
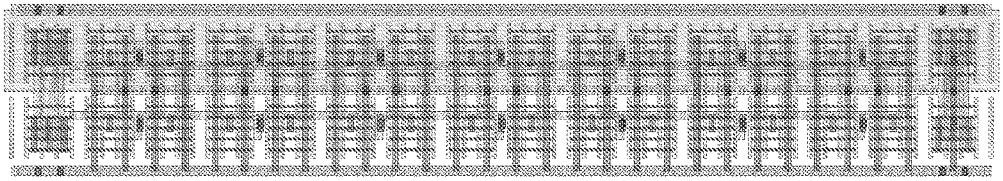
Figure 169B:
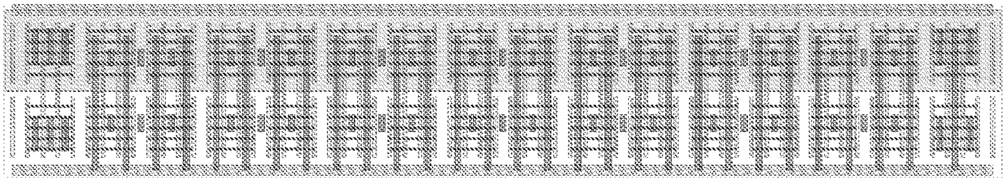
Figure 169C:
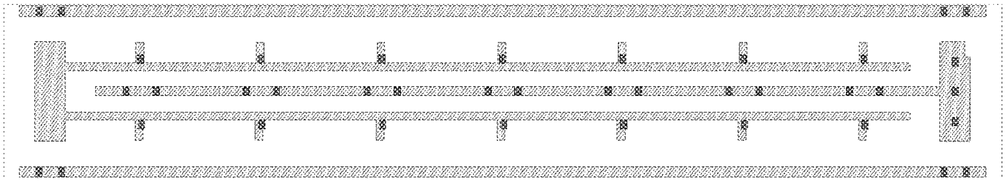
Figure 170A:
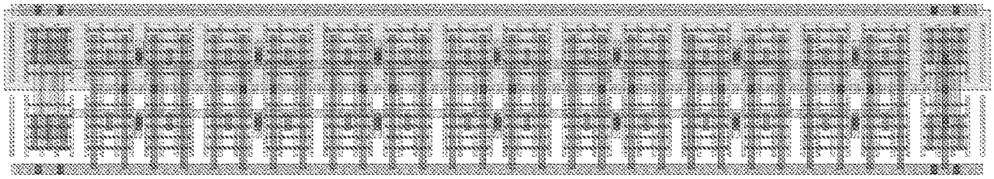
Figure 170B:
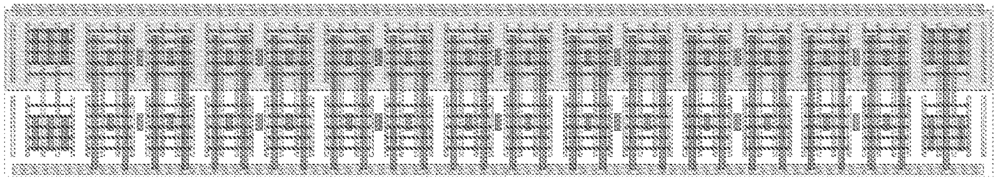
Figure 170C:
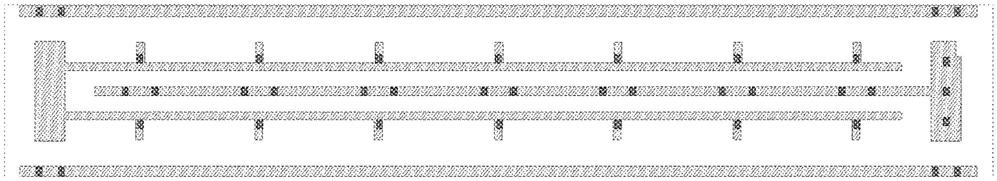
Figure 171A:
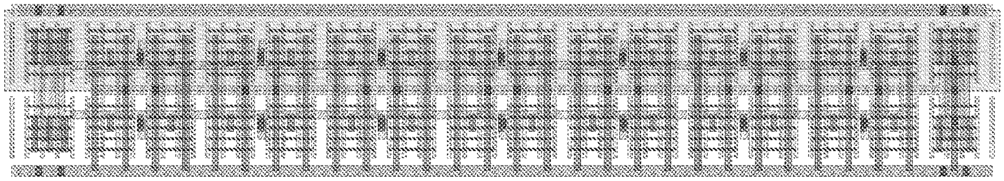
Figure 171B:
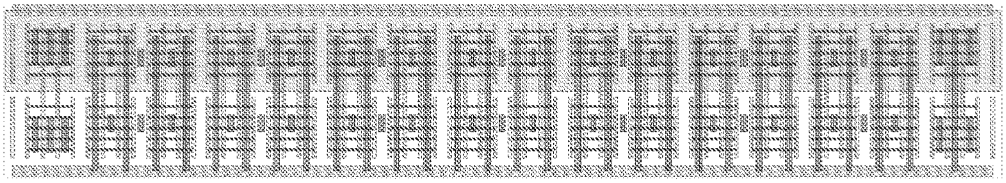
Figure 171C:
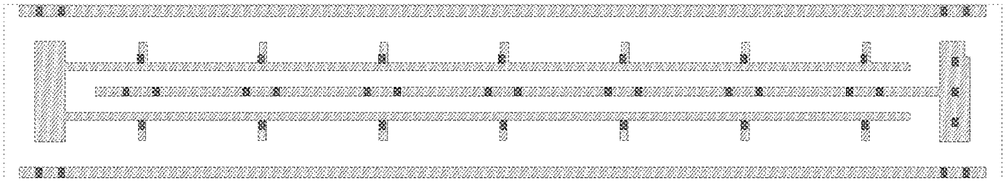
Figure 172A:
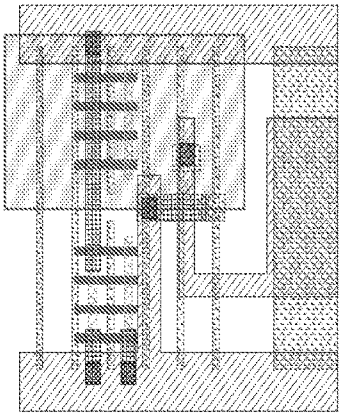
Figure 172B:
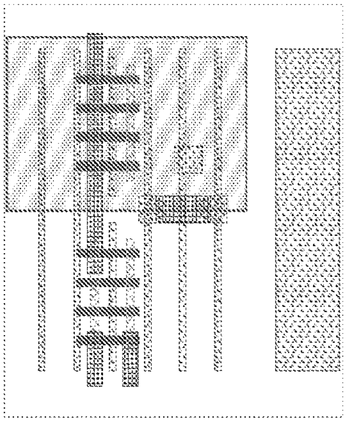
Figure 172C:
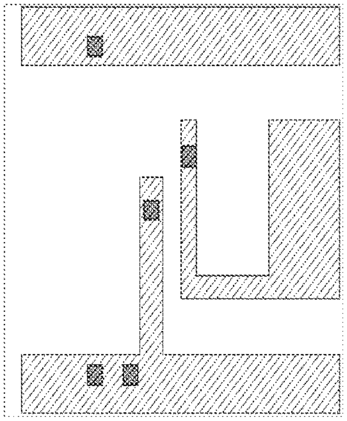
Figure 173A:
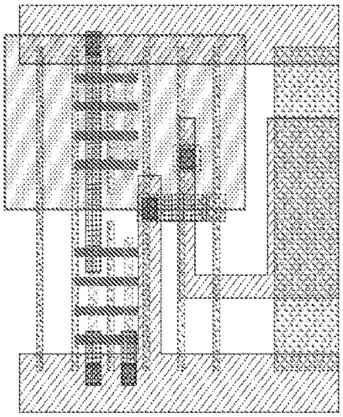
Figure 173B:
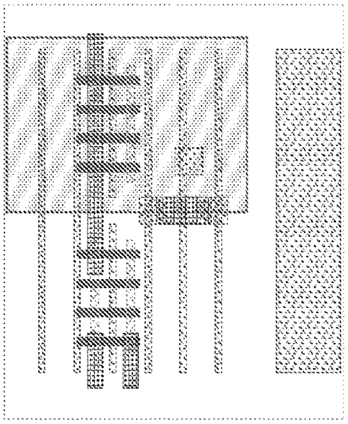
Figure 173C:
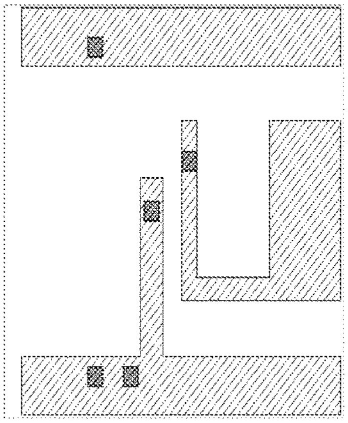
Figure 174A:
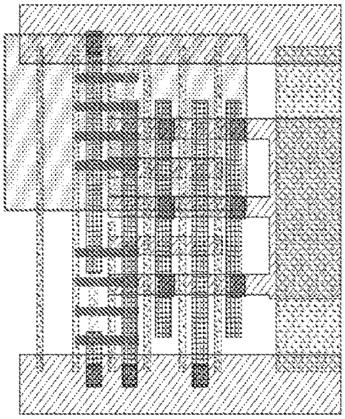
Figure 174B:
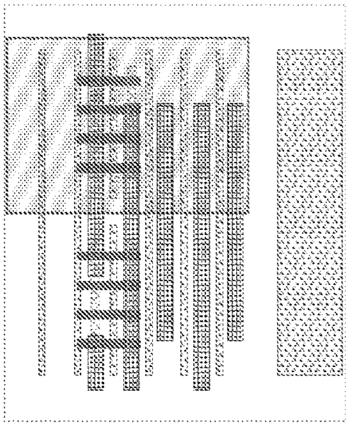
Figure 174C:
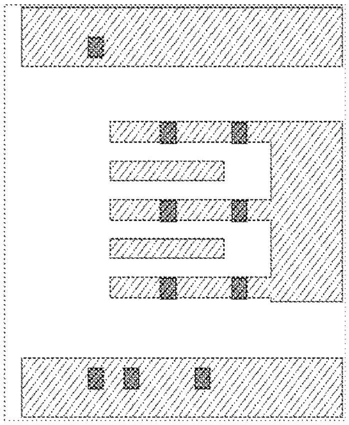
Figure 175A:
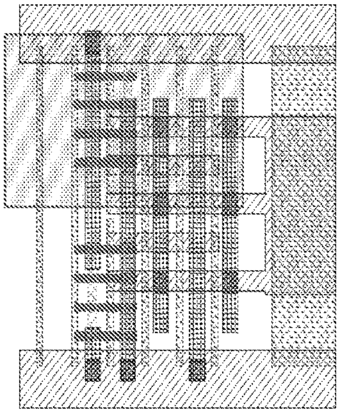
Figure 175B:
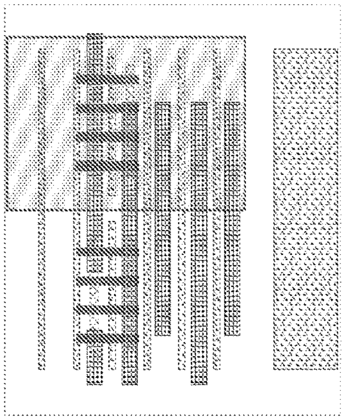
Figure 175C:
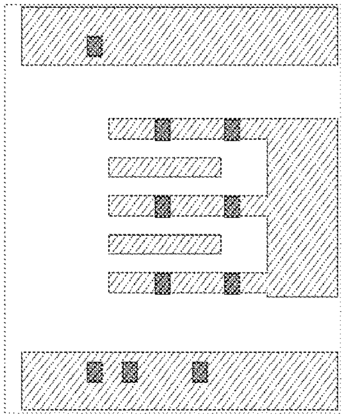
Figure 176A:
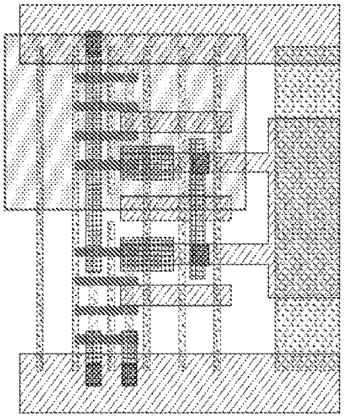
Figure 176B:
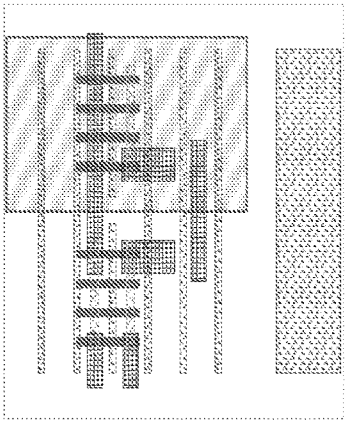
Figure 176C:
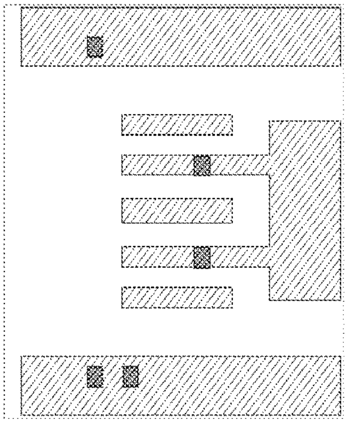
Figure 177A:
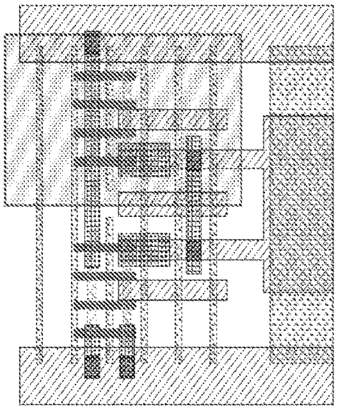
Figure 177B:
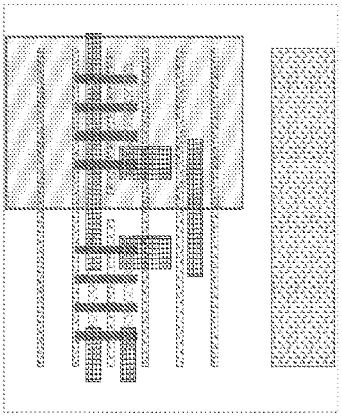
Figure 177C:
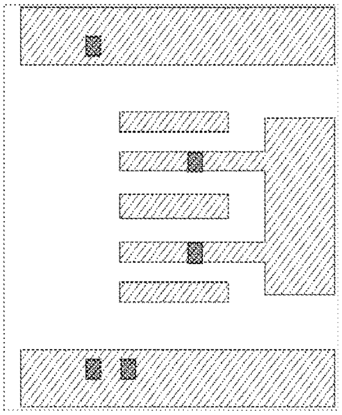
Figure 178A:
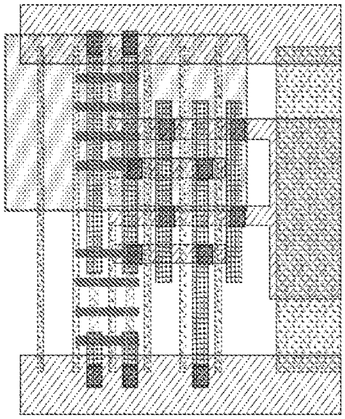
Figure 178B:
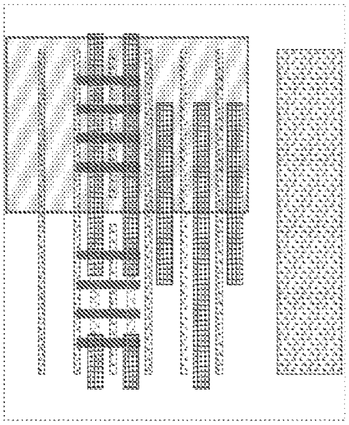
Figure 178C:
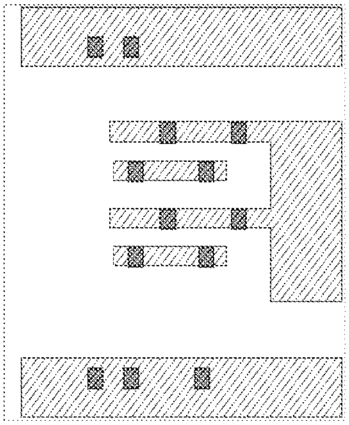
Figure 179A:
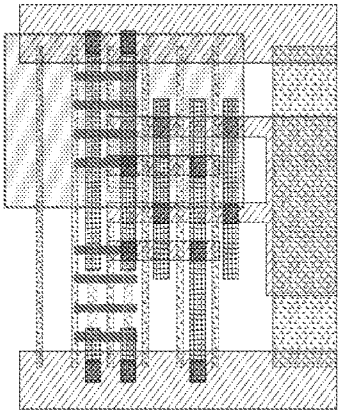
Figure 179B:
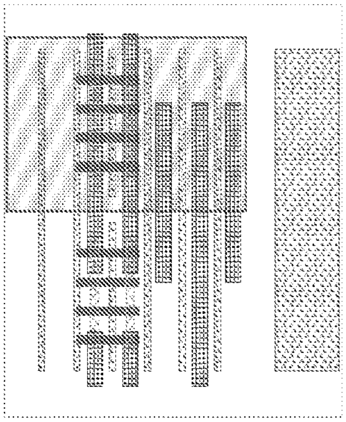
Figure 179C:
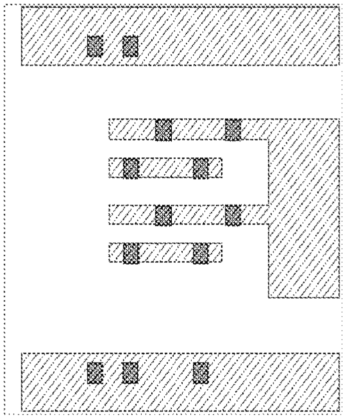
Figure 180A:
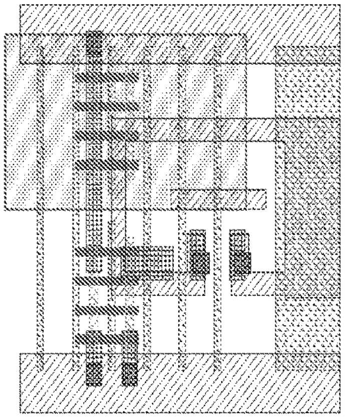
Figure 180B:
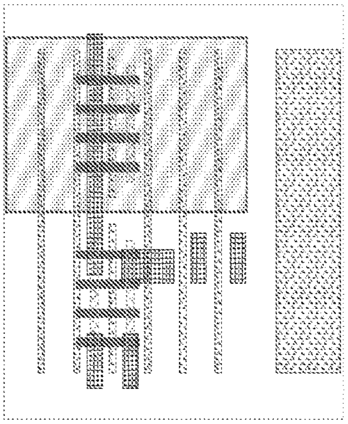
Figure 180C:
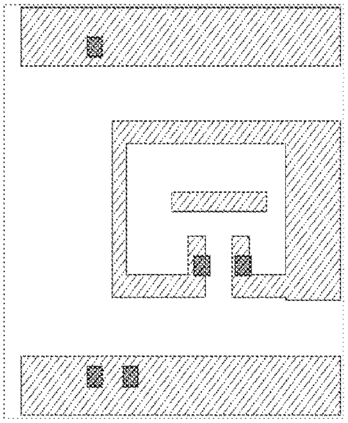
Figure 181A:
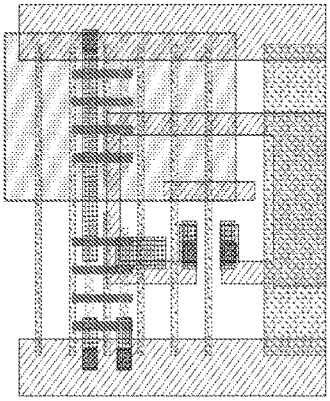
Figure 181B:
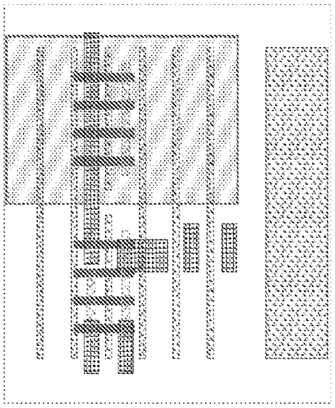
Figure 181C:
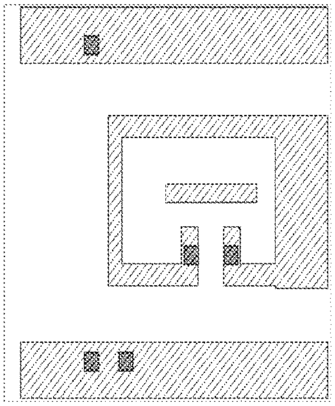
Figure 182A:
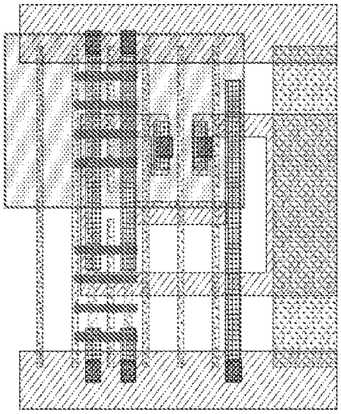
Figure 182B:
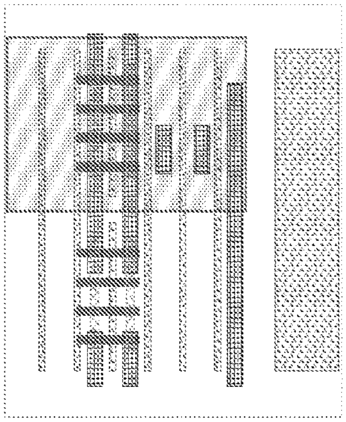
Figure 182C:
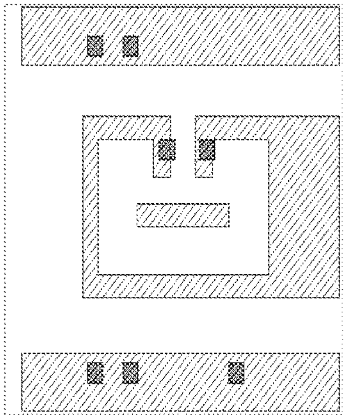
Figure 183A:
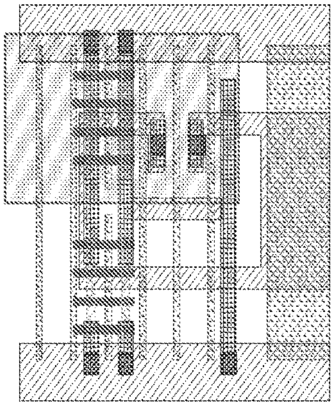
Figure 183B:
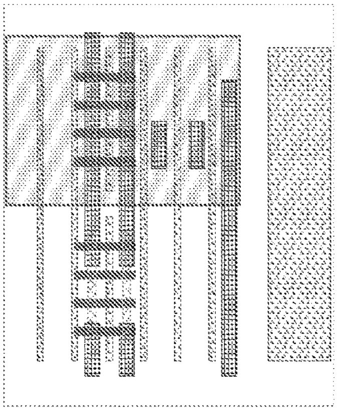
Figure 183C:
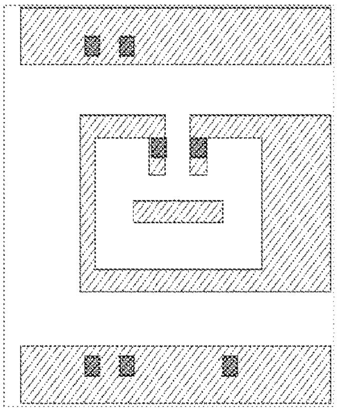
Figure 184A:
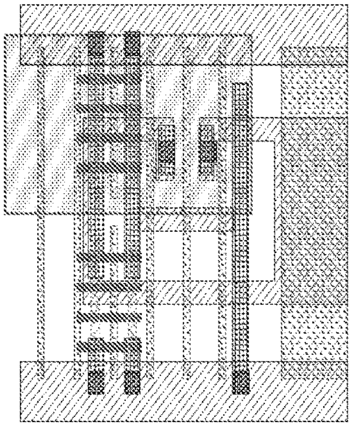
Figure 184B:
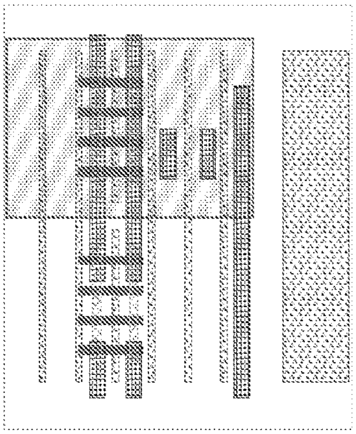
Figure 184C:
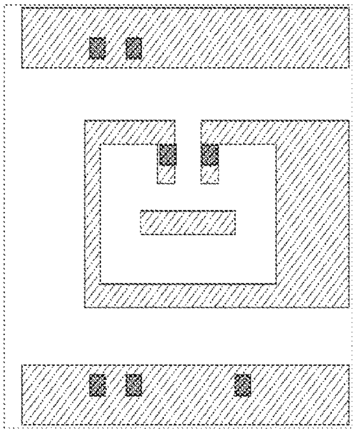
Figure 185A:
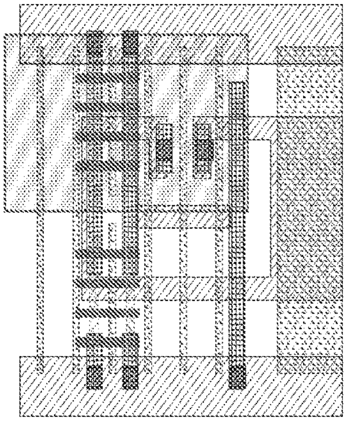
Figure 185B:
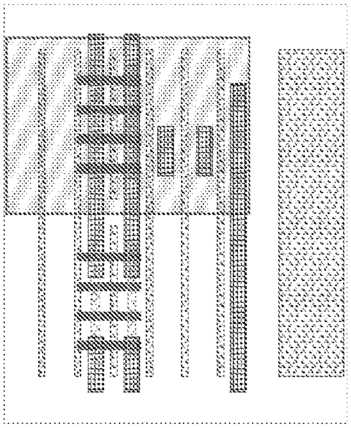
Figure 185C:
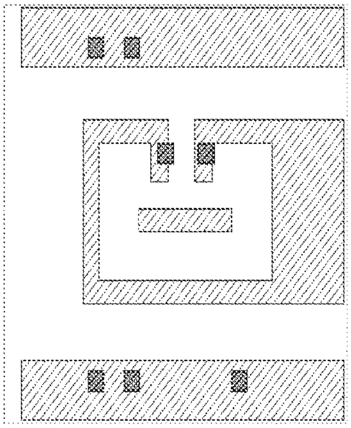
Figure 186A:
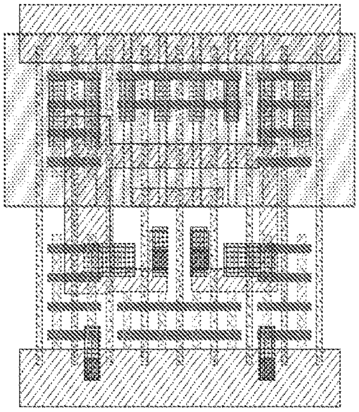
Figure 186B:
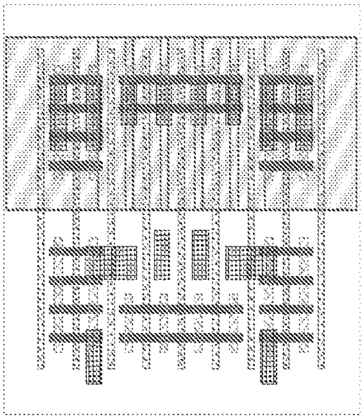
Figure 186C:
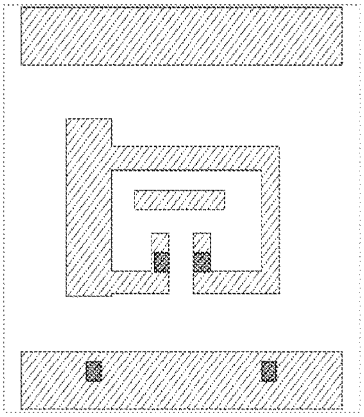
Figure 187A:
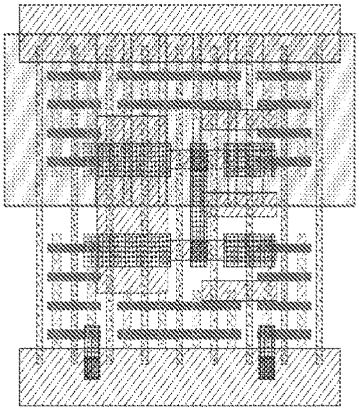
Figure 187B:
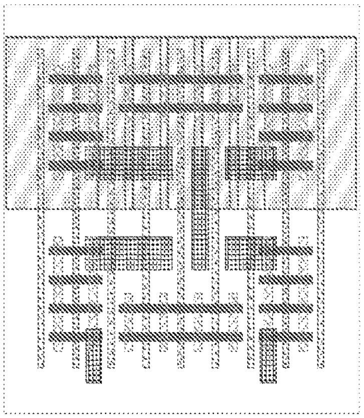
Figure 187C:
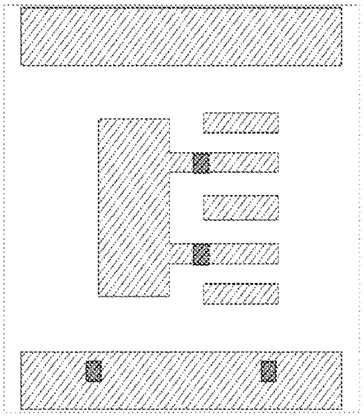
Figure 188A:
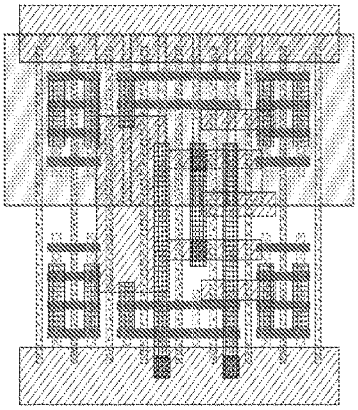
Figure 188B:
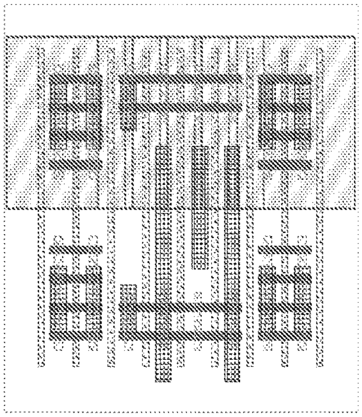
Figure 188C:
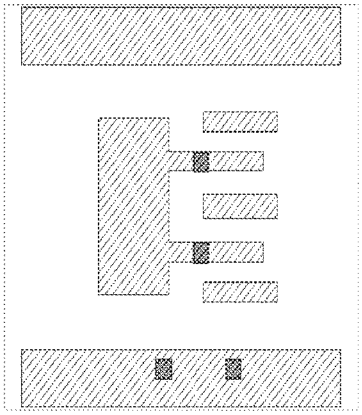
Figure 189A:
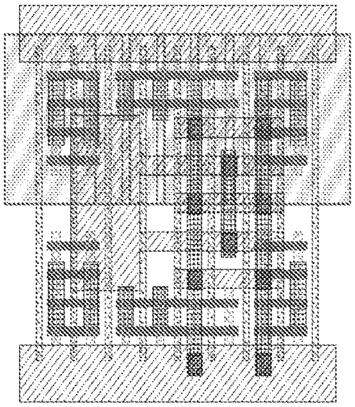
Figure 189B:
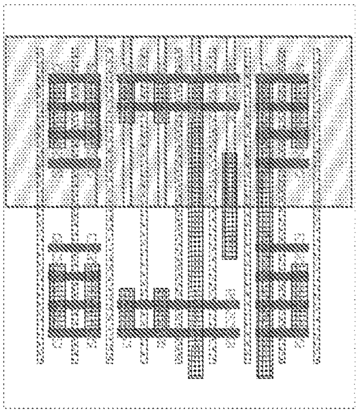
Figure 189C:
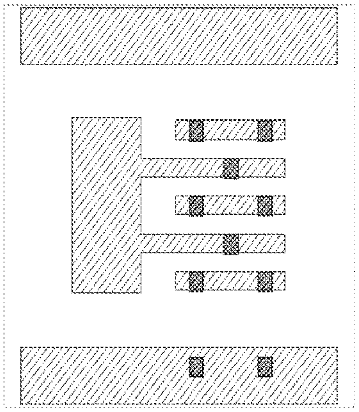
Figure 190A:
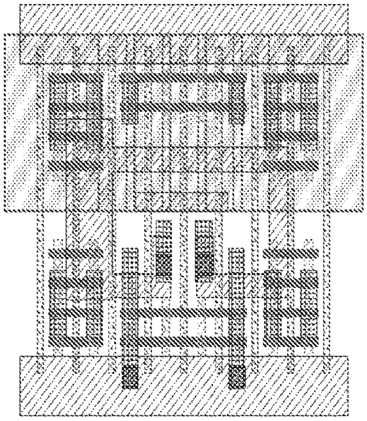
Figure 190B:
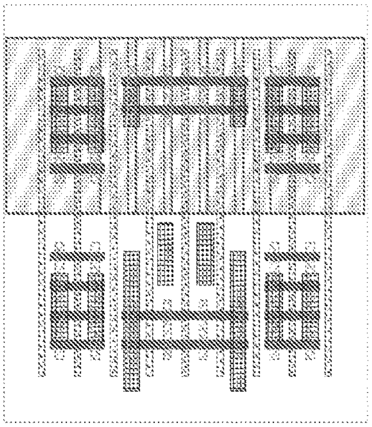
Figure 190C:
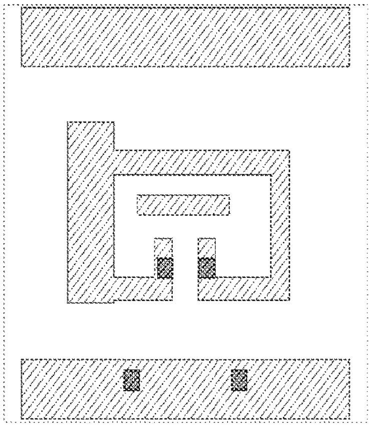
Figure 191A:
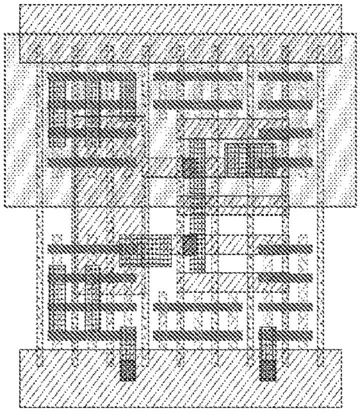
Figure 191B:
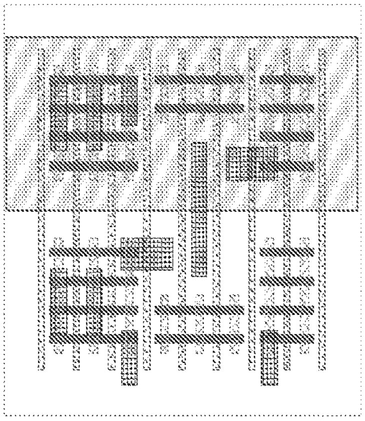
Figure 191C:
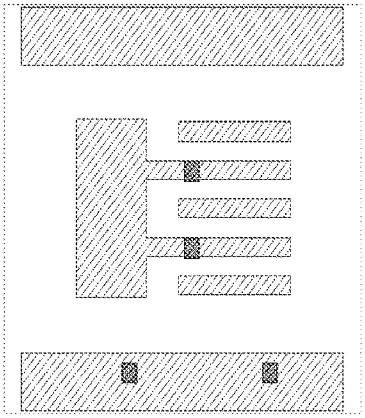
Figure 192A:
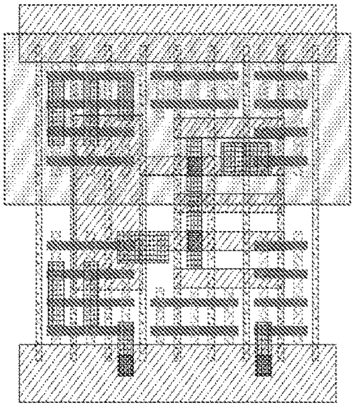
Figure 192B:
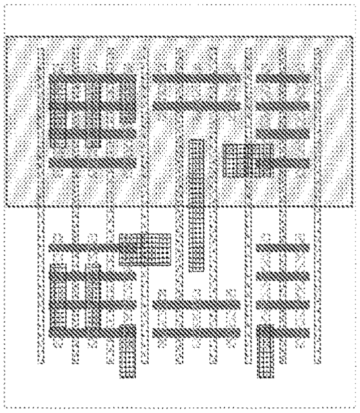
Figure 192C:
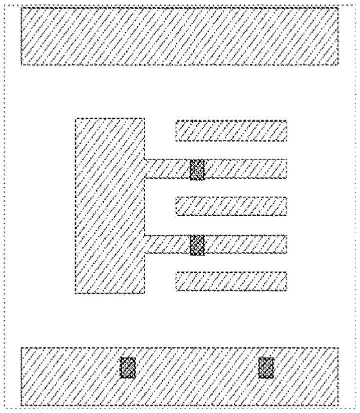
Figure 193A:
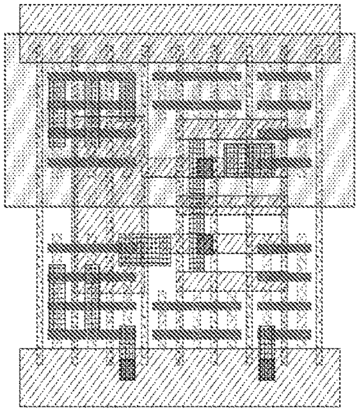
Figure 193B:
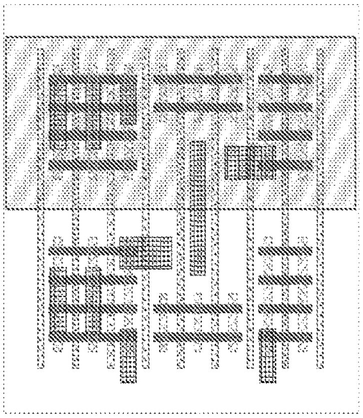
Figure 193C:
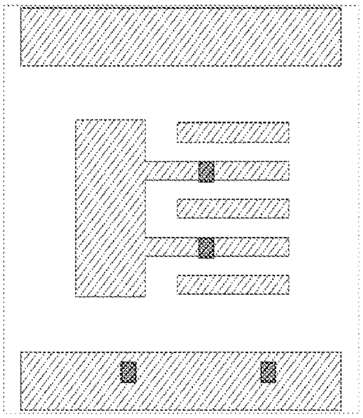
Figure 194A:
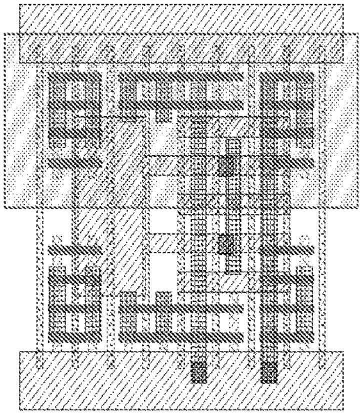
Figure 194B:
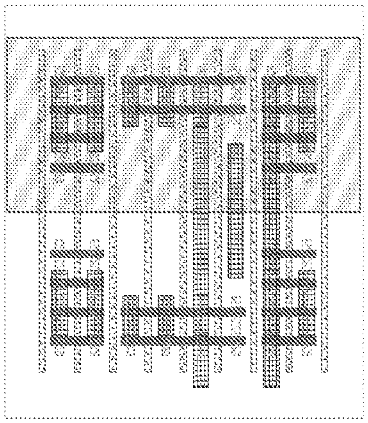
Figure 194C:
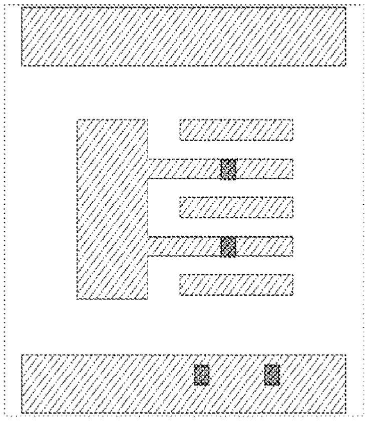
Figure 195A:
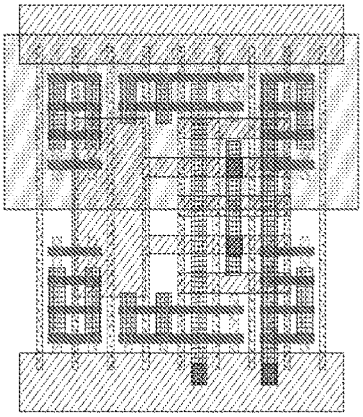
Figure 195B:
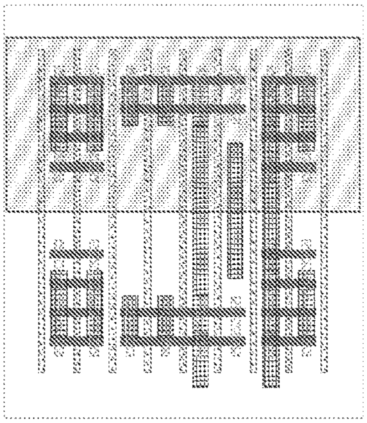
Figure 195C:
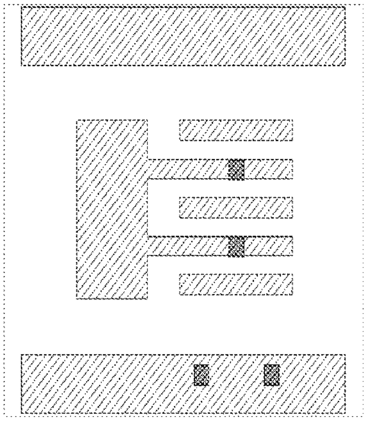
Figure 196A:
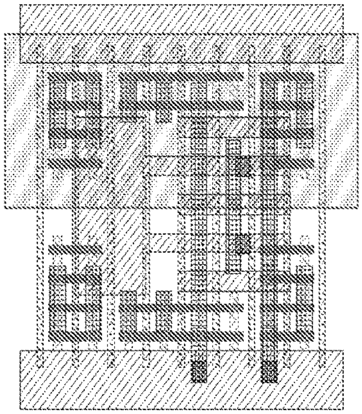
Figure 196B:
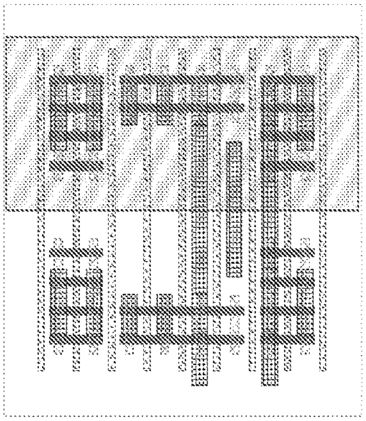
Figure 196C:
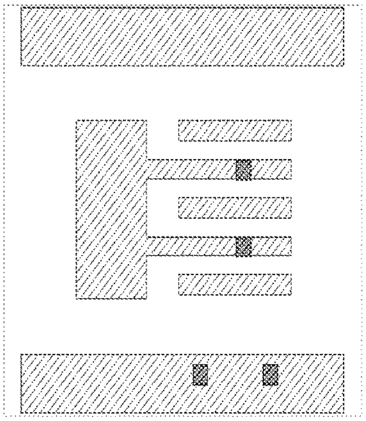
Figure 197A:
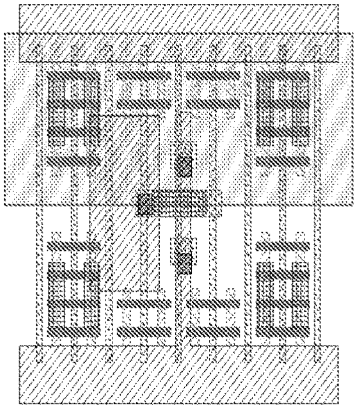
Figure 197B:
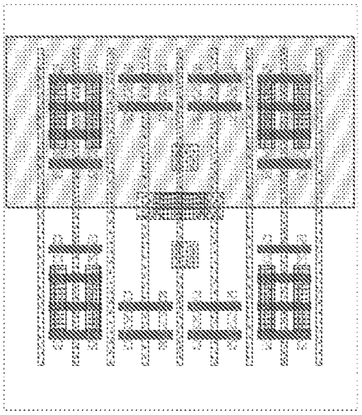
Figure 197C:
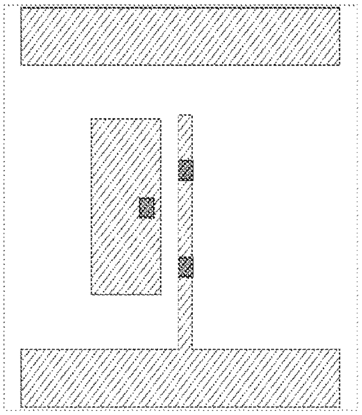
Figure 198A:
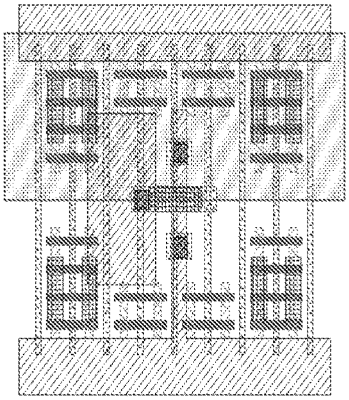
Figure 198B:
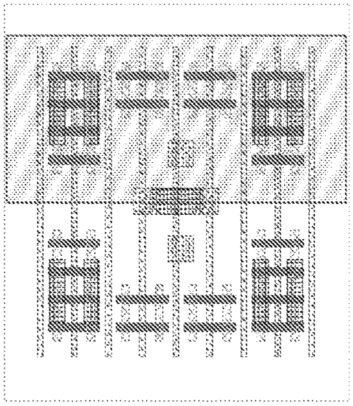
Figure 198C:
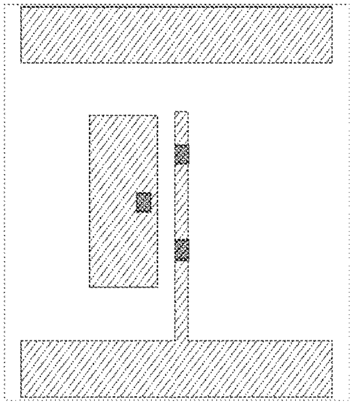
Figure 199A:
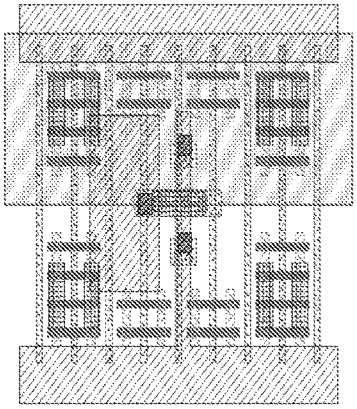
Figure 199B:
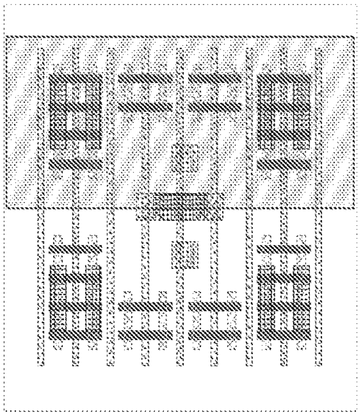
Figure 199C:
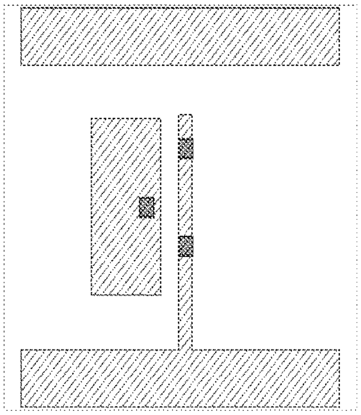
Figure 200A:
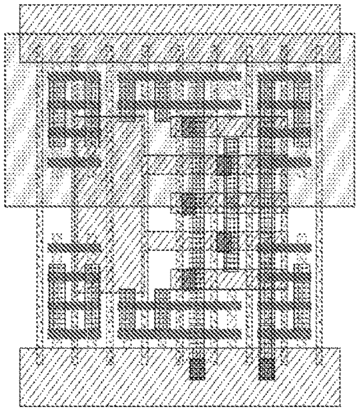
Figure 200B:
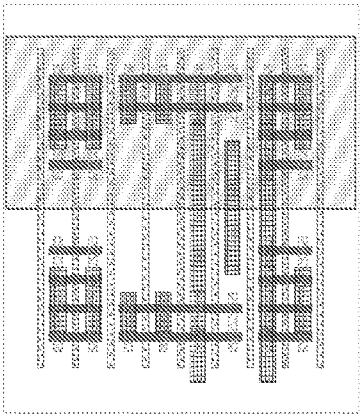
Figure 200C:
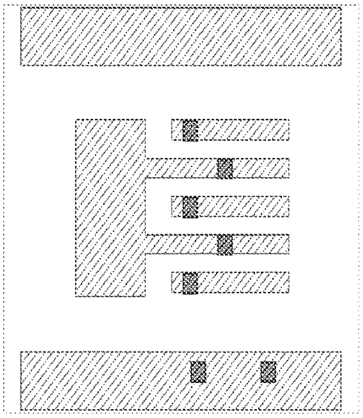
Figure 201A:
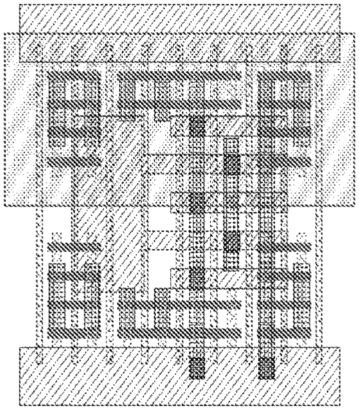
Figure 201B:
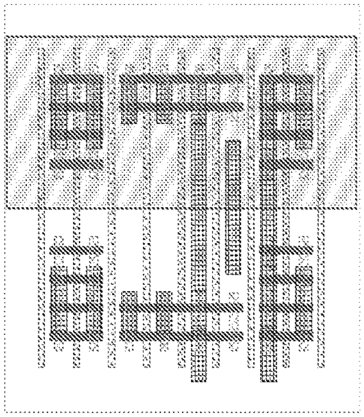
Figure 201C:
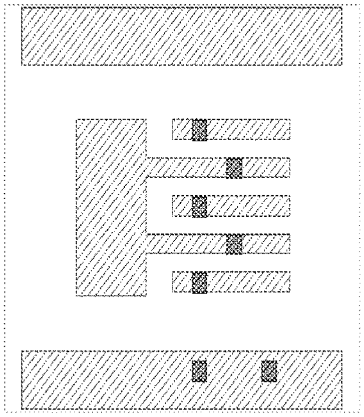
Figure 202A:
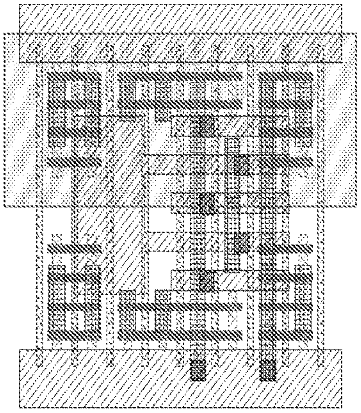
Figure 202B:
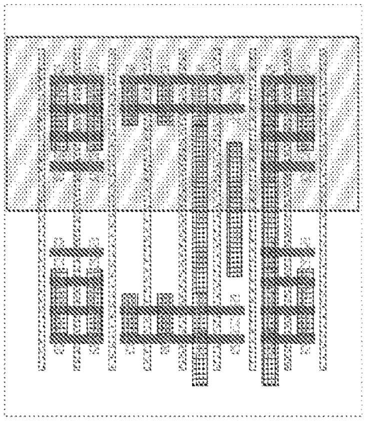
Figure 202C:
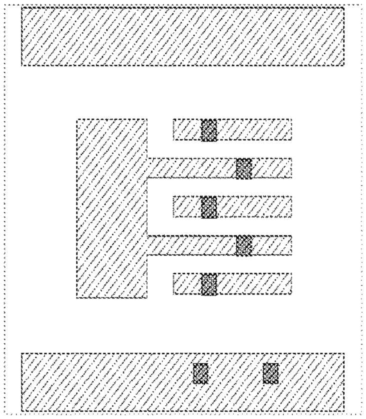
Figure 203A:
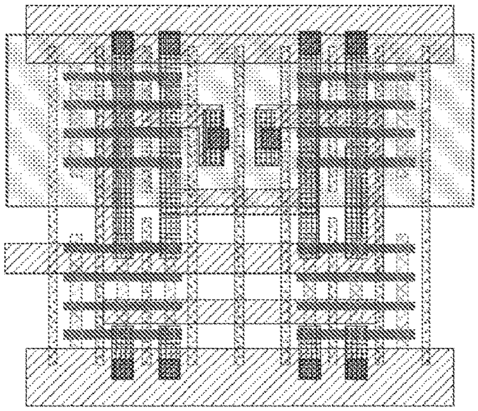
Figure 203B:
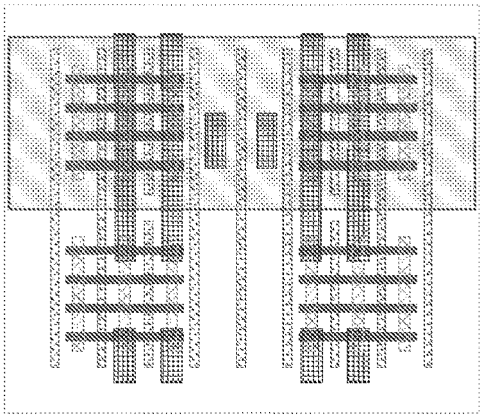
Figure 203C:
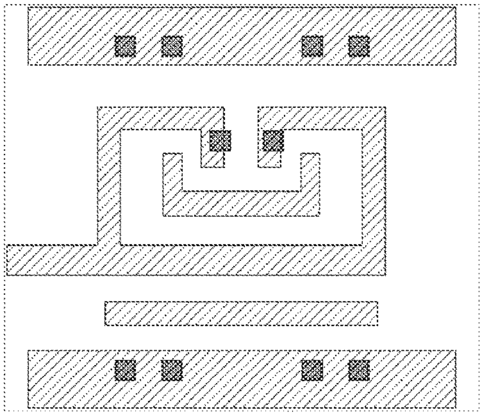
Figure 204A:
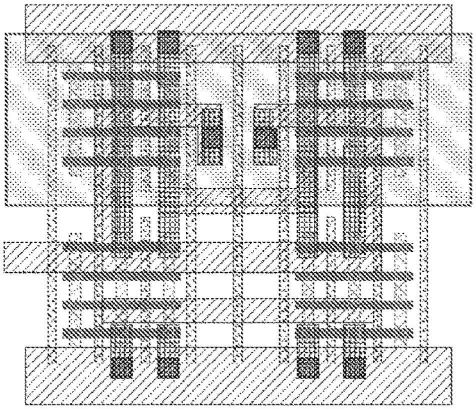
Figure 204B:
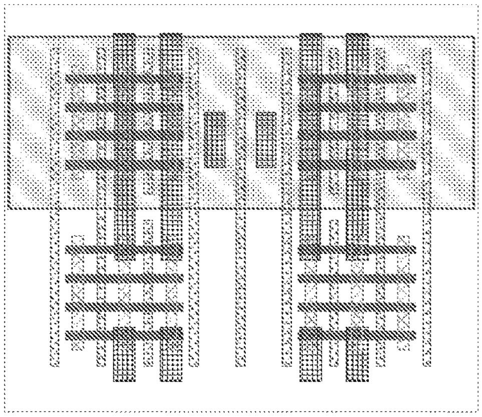
Figure 204C:
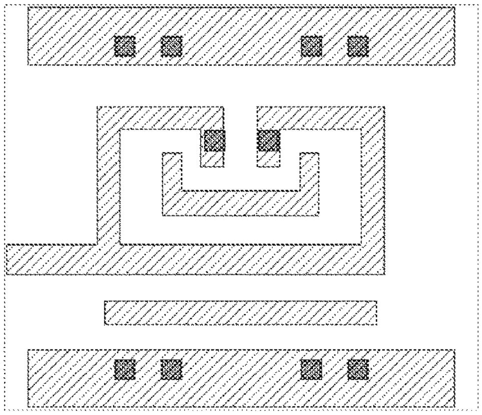
Figure 205A:
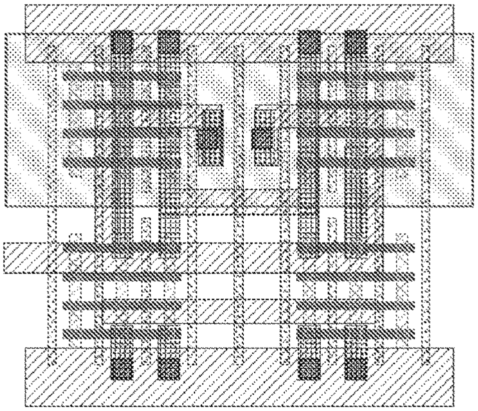
Figure 205B:
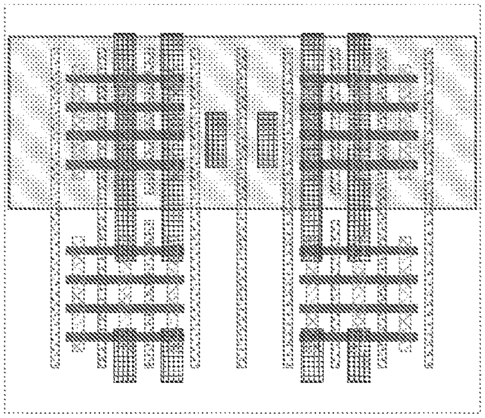
Figure 205C:
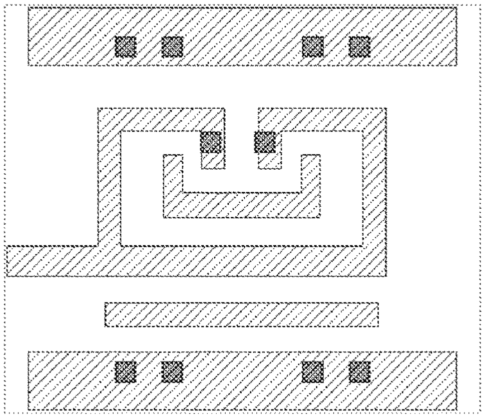
Figure 206A:
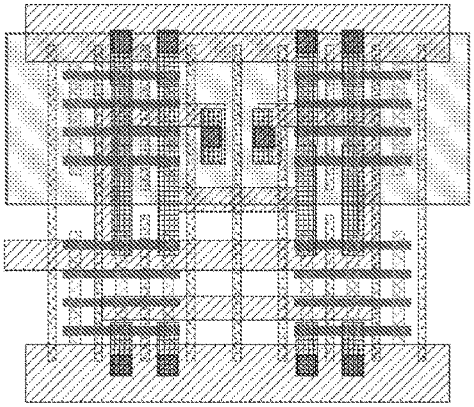
Figure 206B:
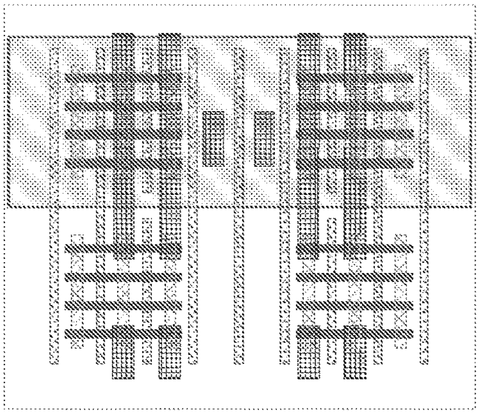
Figure 206C:
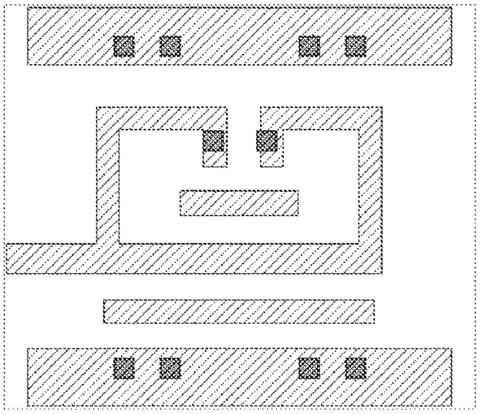
Figure 207A:
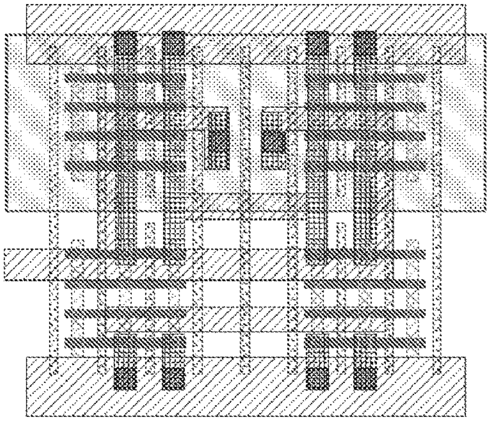
Figure 207B:
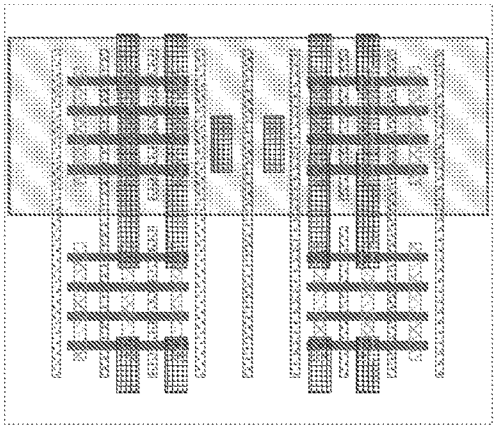
Figure 207C:
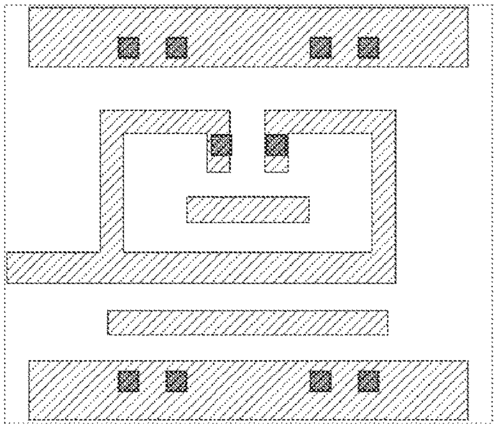
Figure 208A:
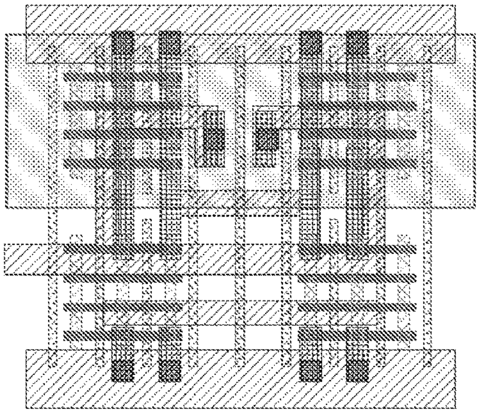
Figure 208B:
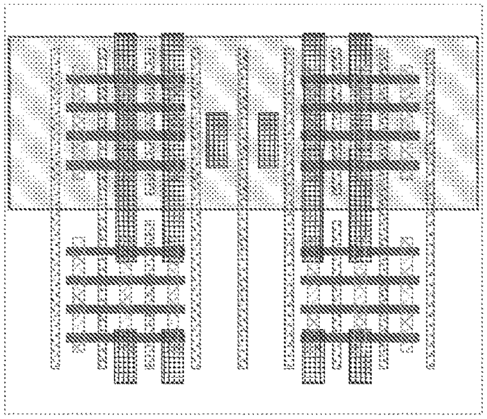
Figure 208C:
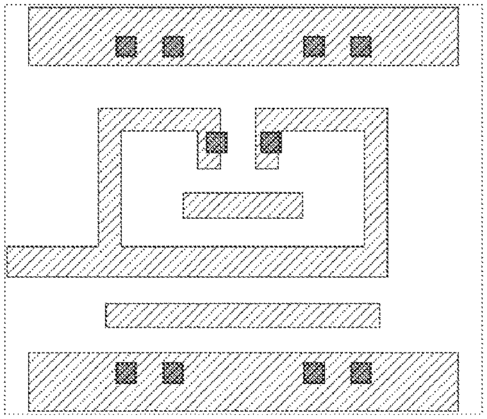
Figure 209A:
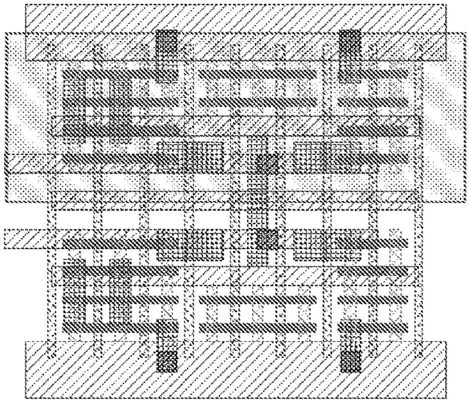
Figure 209B:
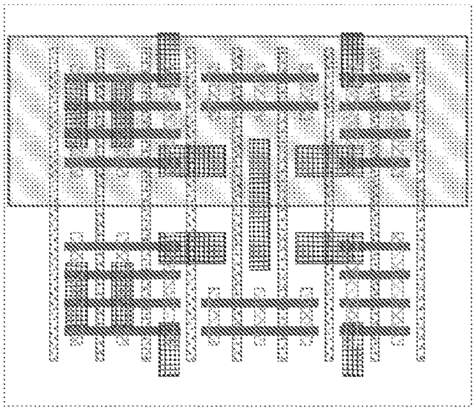
Figure 209C:
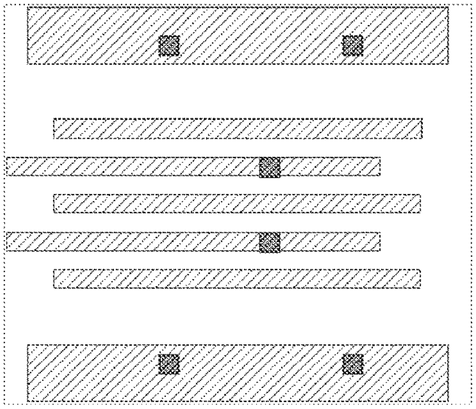
Figure 210A:
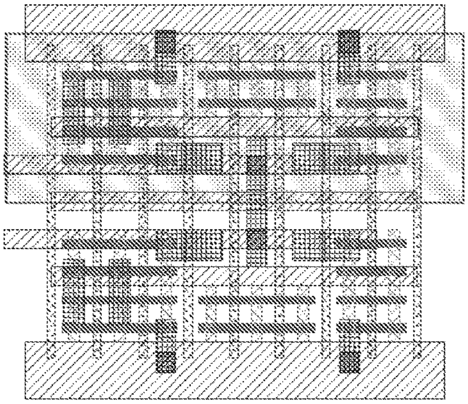
Figure 210B:
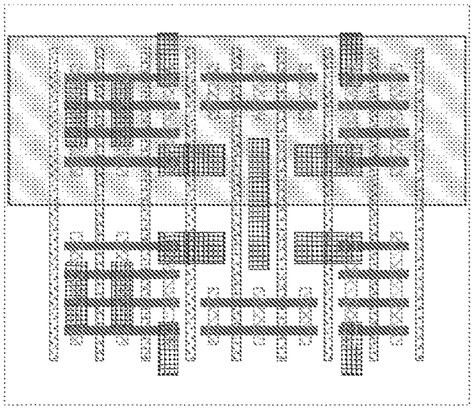
Figure 210C:
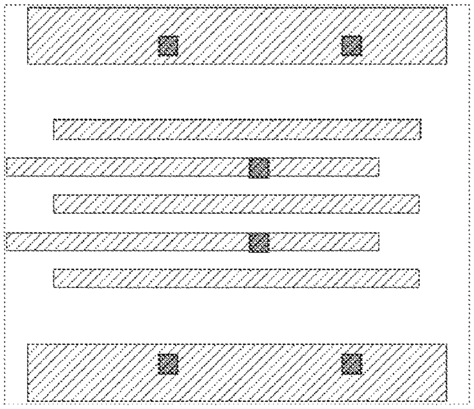
Figure 211A:
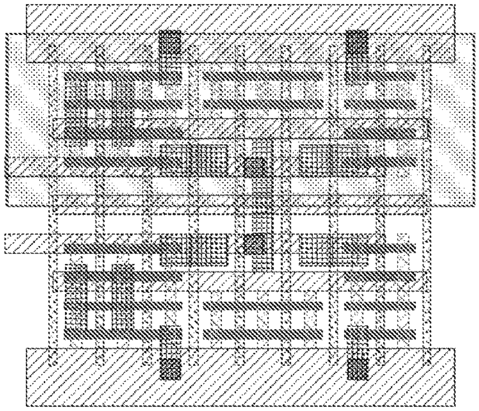
Figure 211B:
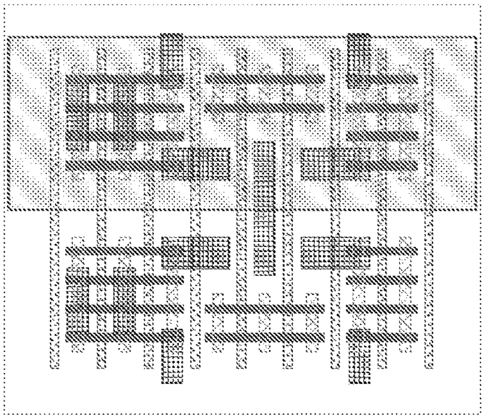
Figure 211C:
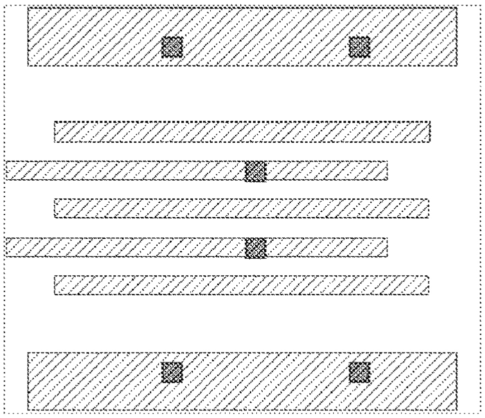
Figure 212A:
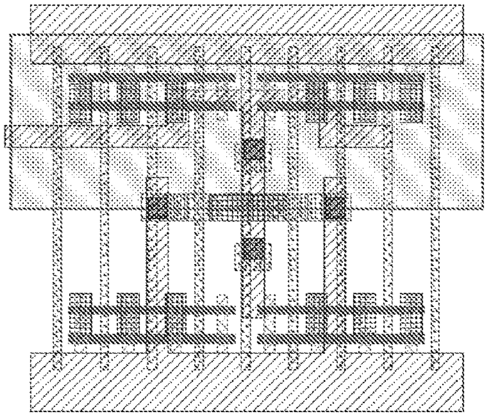
Figure 212B:
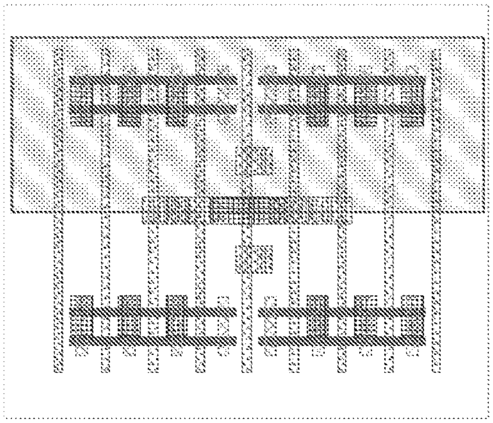
Figure 212C:
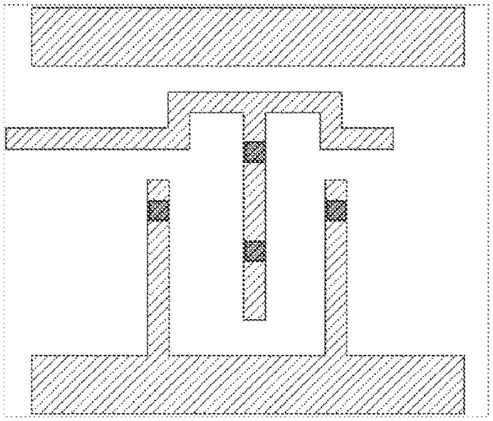
Figure 213A:
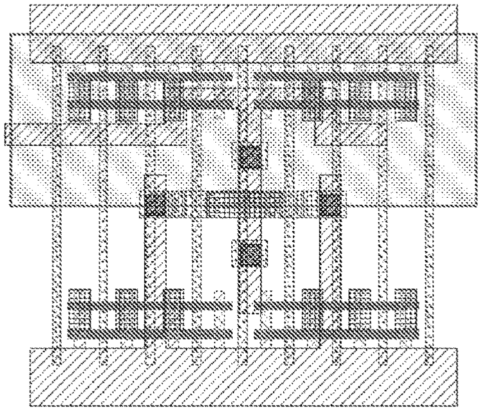
Figure 213B:
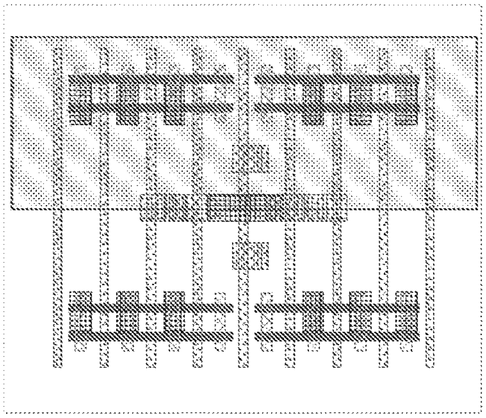
Figure 213C:
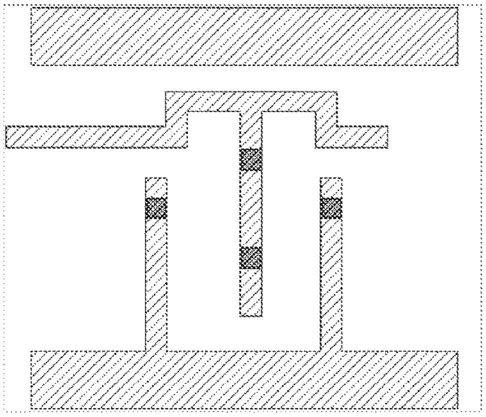
Figure 214A:
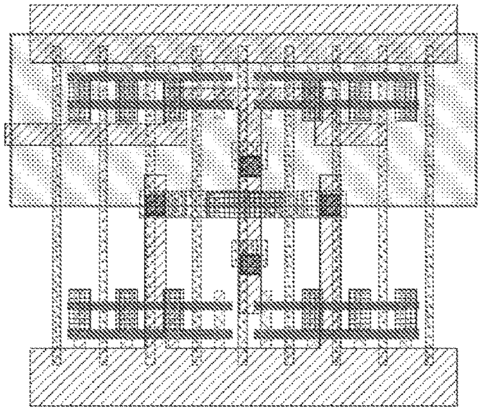
Figure 214B:
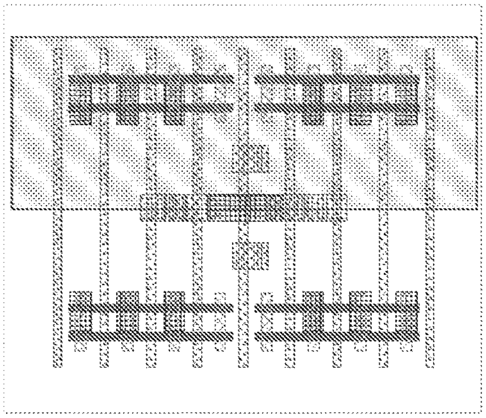
Figure 214C:
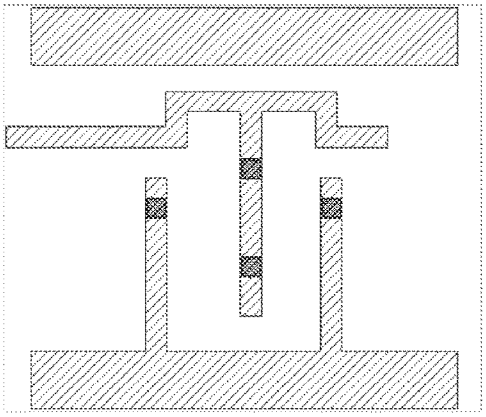
Figure 215A:
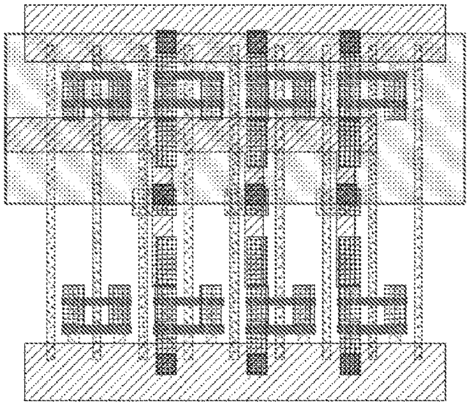
Figure 215B:
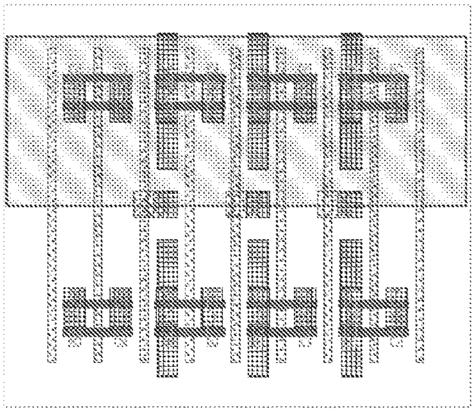
Figure 215C:
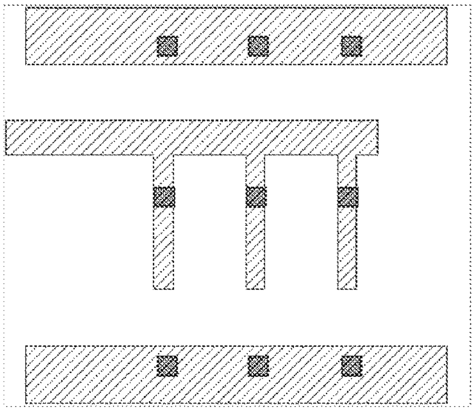
Figure 216A:
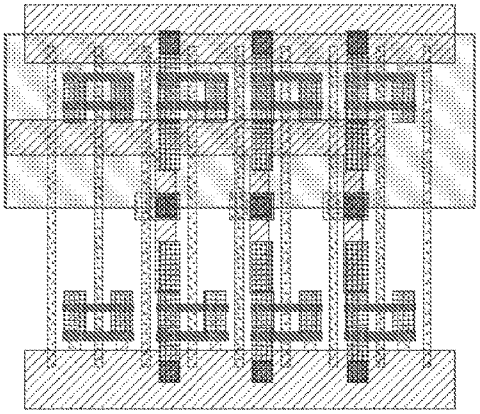
Figure 216B:
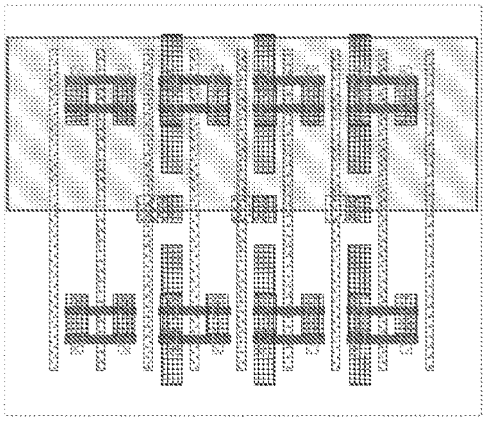
Figure 216C:
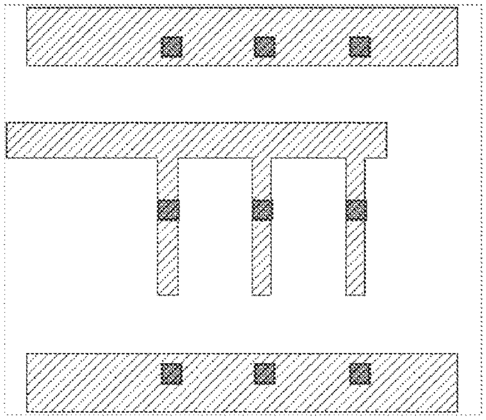
Figure 217A:
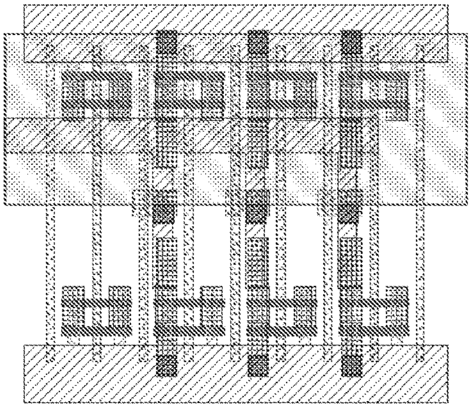
Figure 217B:
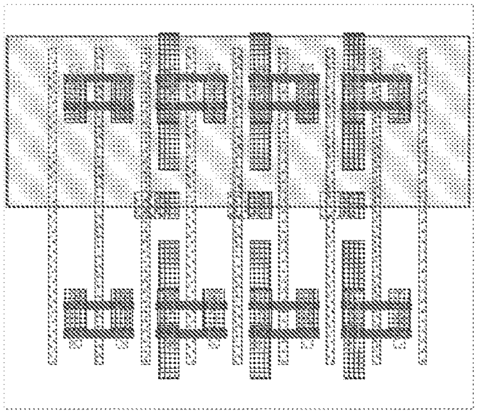
Figure 217C:
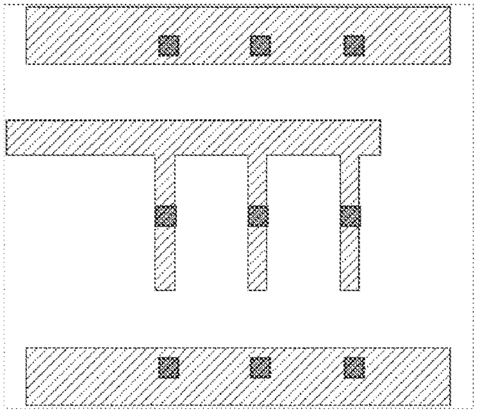
Figure 218A:
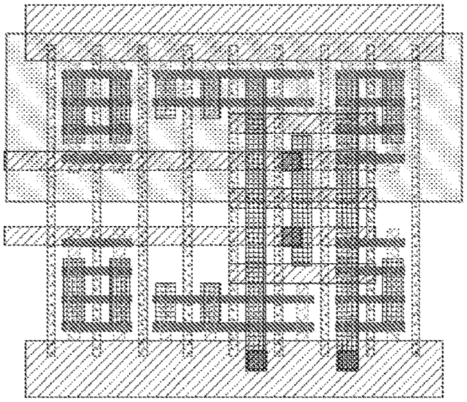
Figure 218B:
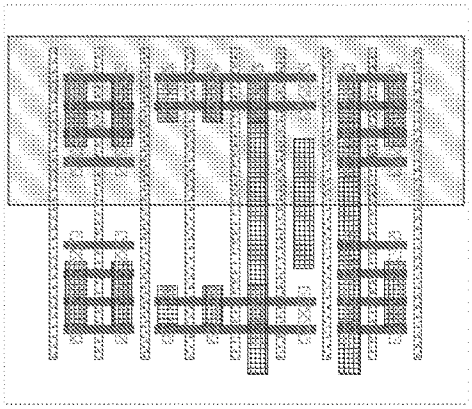
Figure 218C:
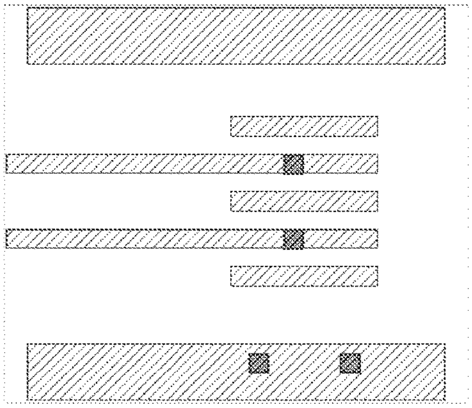
Figure 219A:
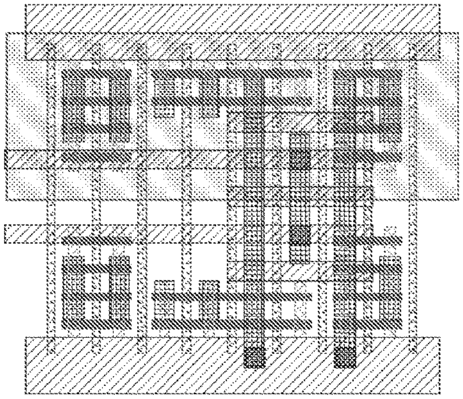
Figure 219B:
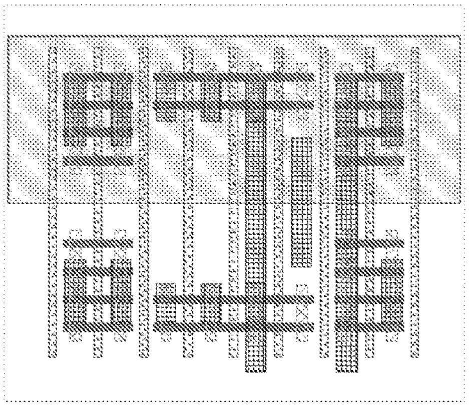
Figure 219C:
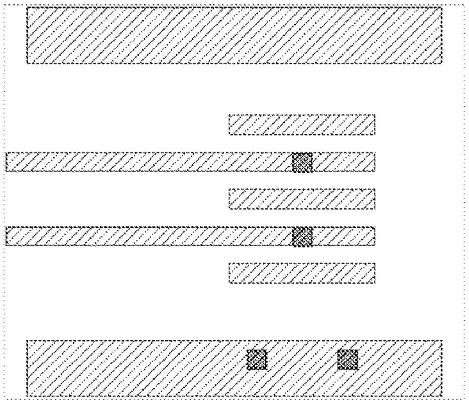
Figure 220A:
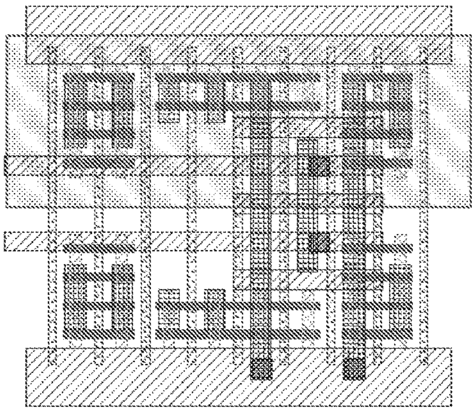
Figure 220B:
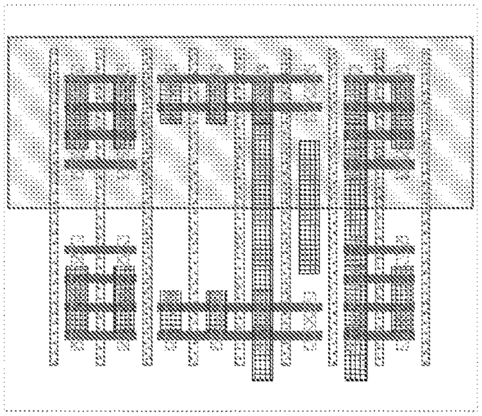
Figure 220C:
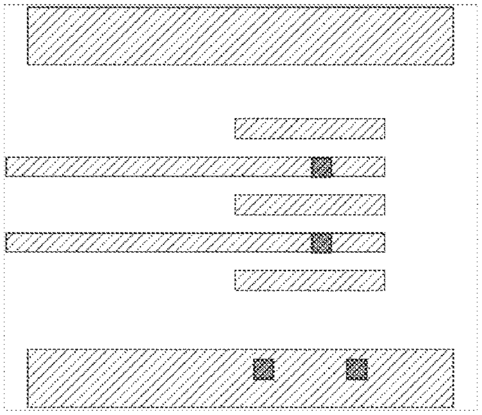
Figure 221A:
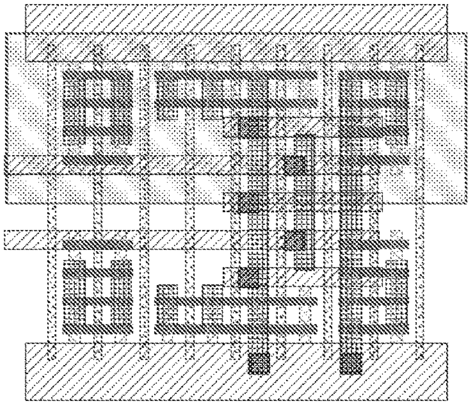
Figure 221B:
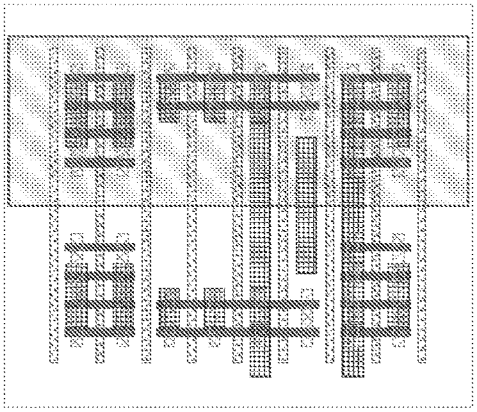
Figure 221C:
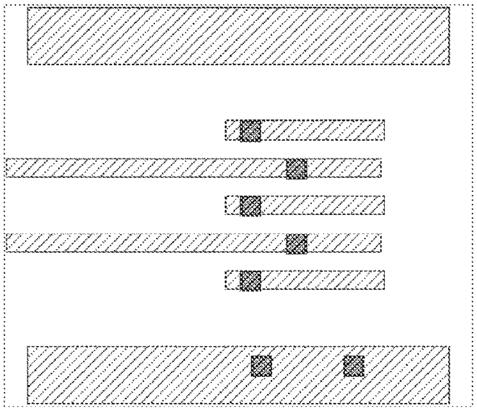
Figure 222A:
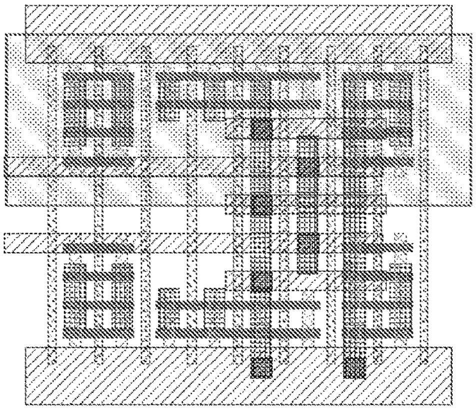
Figure 222B:
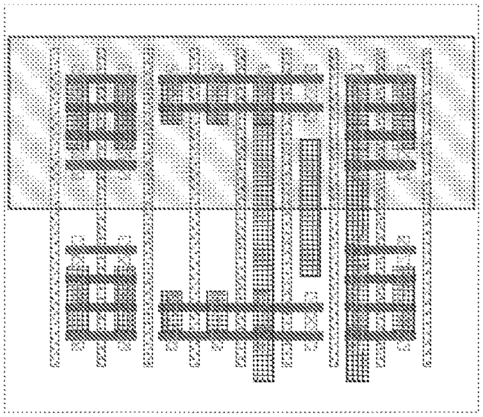
Figure 222C:
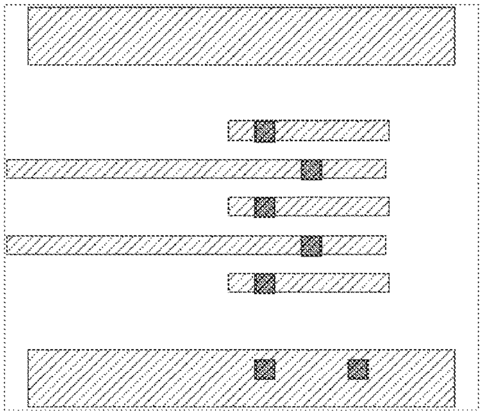
Figure 223A:
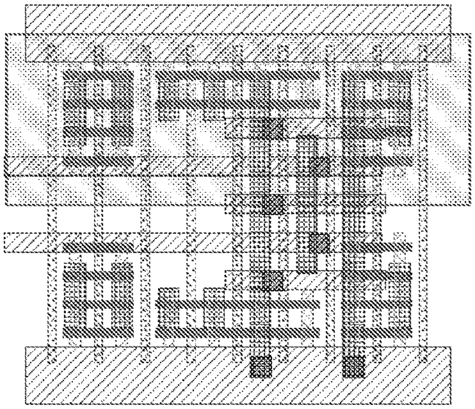
Figure 223B:
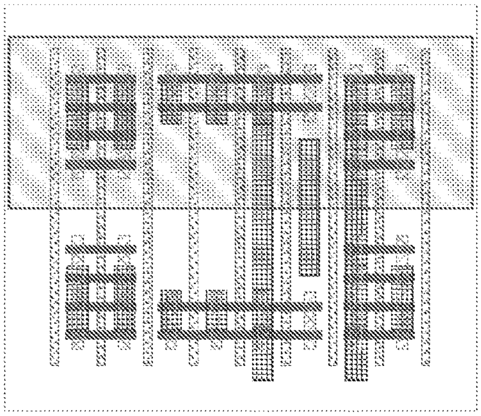
Figure 223C:
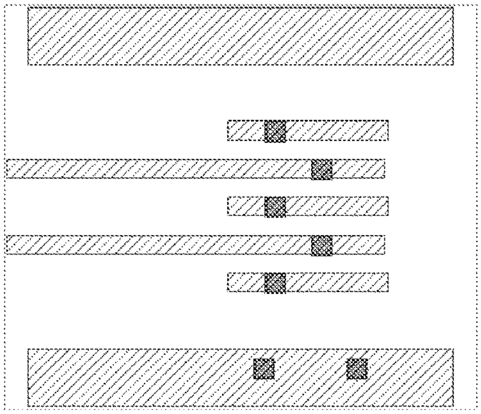
Figure 224A:
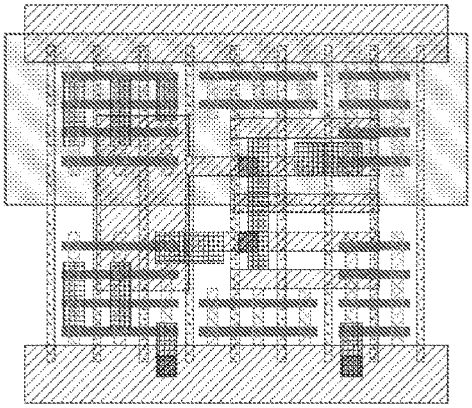
Figure 224B:
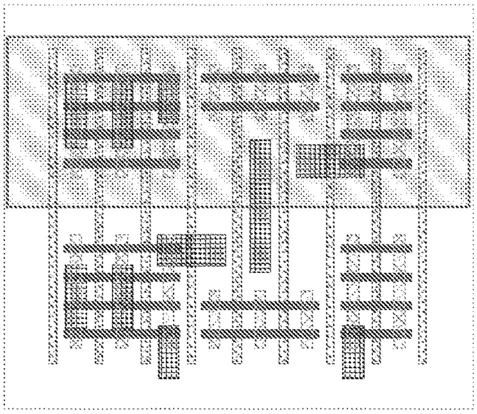
Figure 224C:
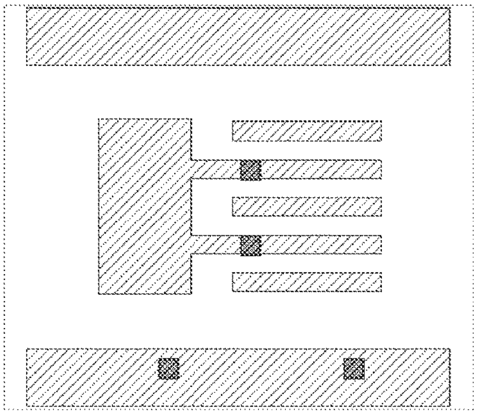
Figure 225A:
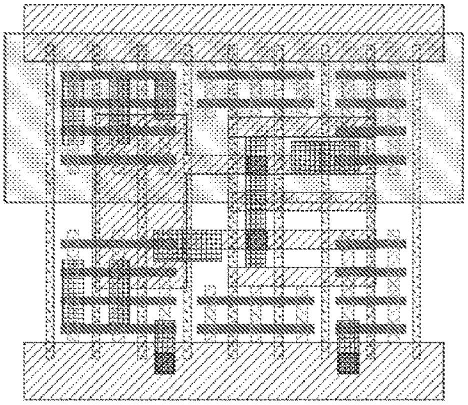
Figure 225B:
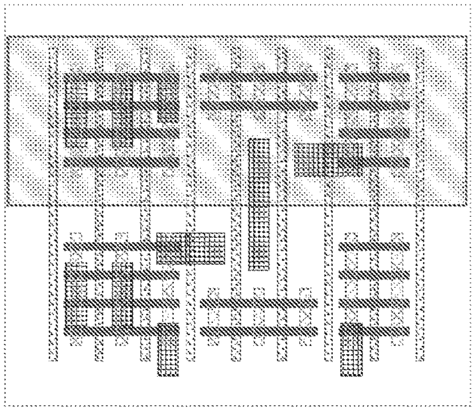
Figure 225C:
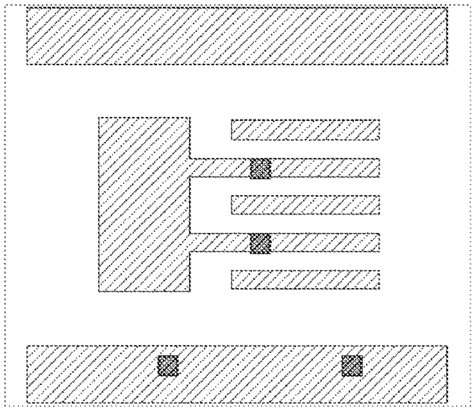
Figure 226A:
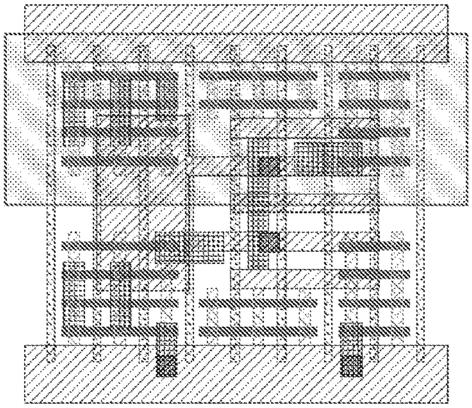
Figure 226B:
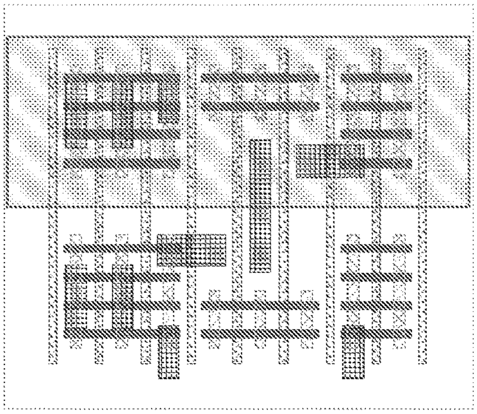
Figure 226C:
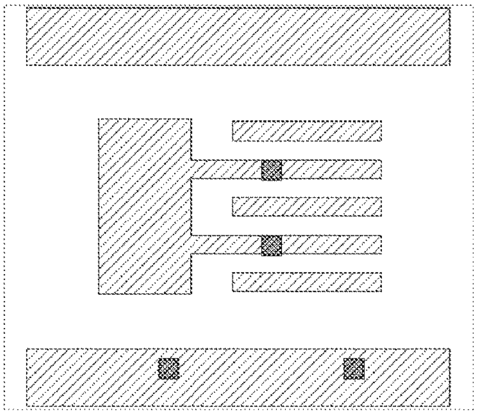
Figure 227A:
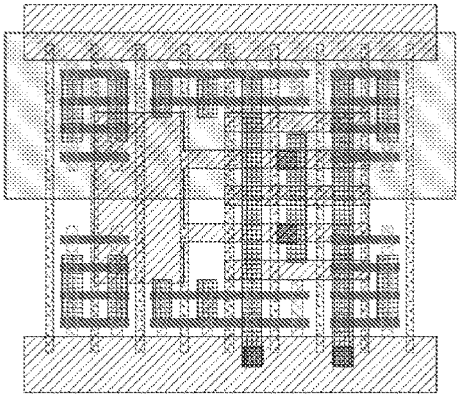
Figure 227B:
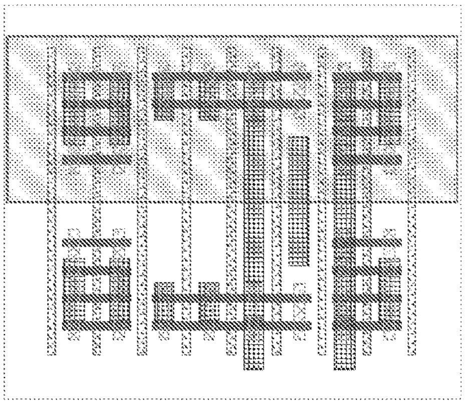
Figure 227C:
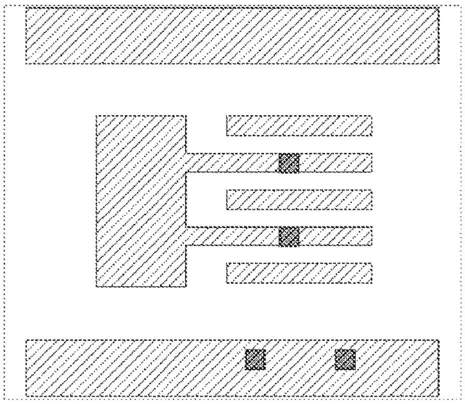
Figure 228A:
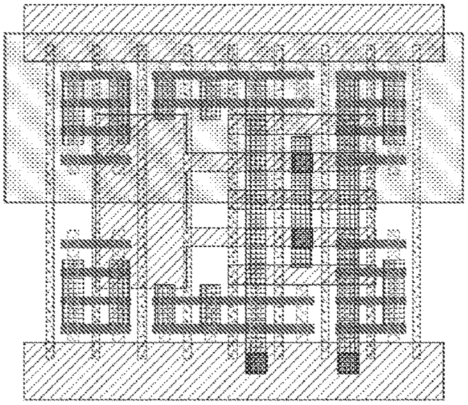
Figure 228B:
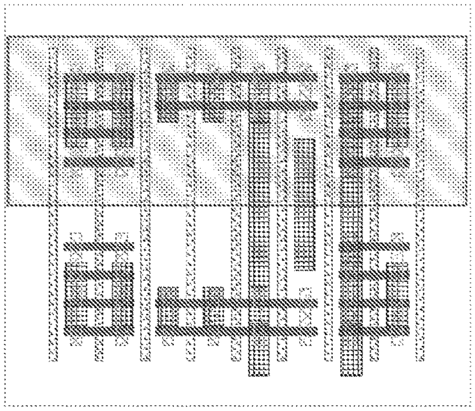
Figure 228C:
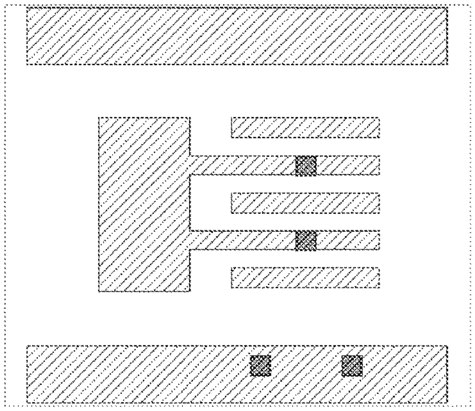
Figure 229A:
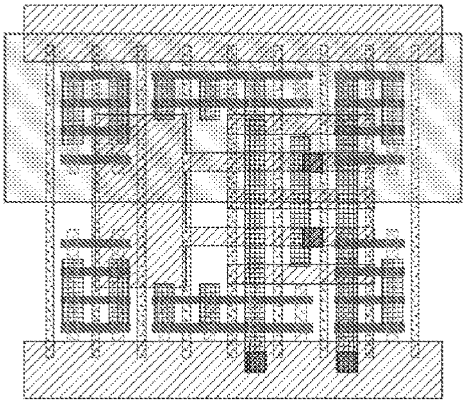
Figure 229B:
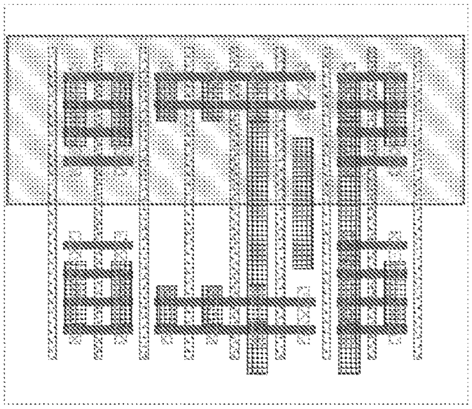
Figure 229C:
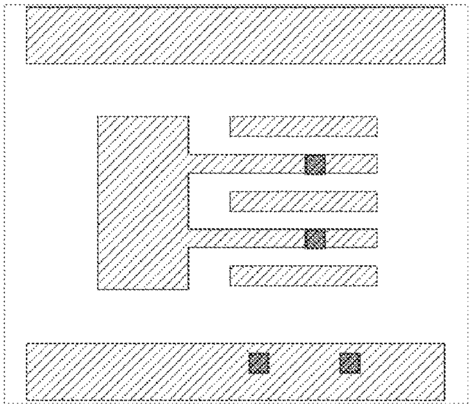
Figure 230A:
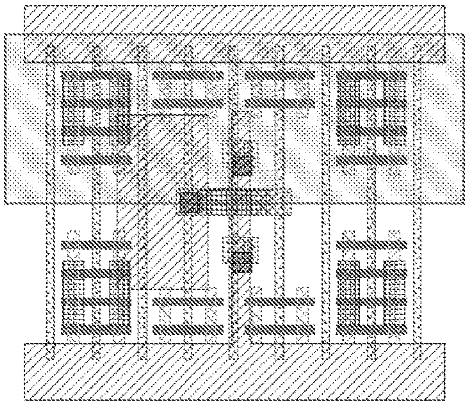
Figure 230B:
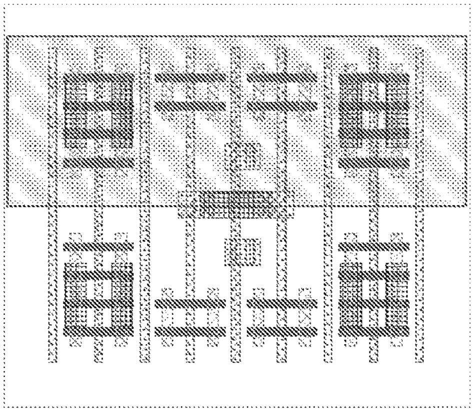
Figure 230C:
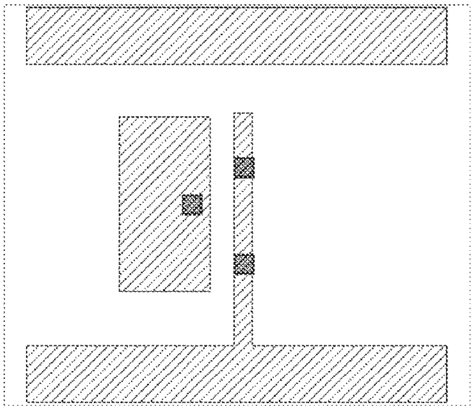
Figure 231A:
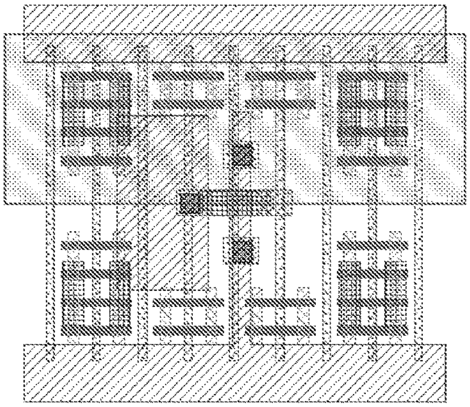
Figure 231B:
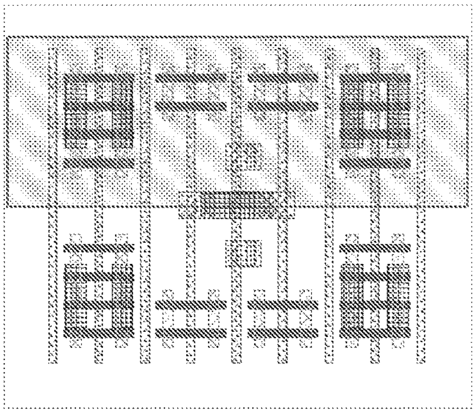
Figure 231C:
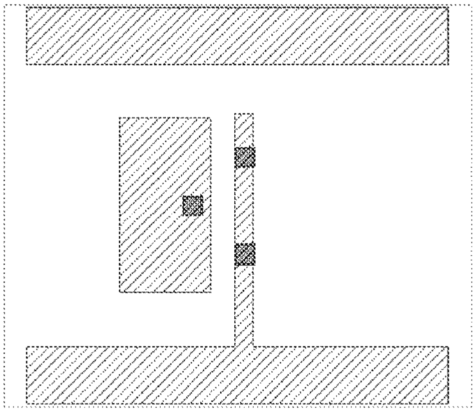
Figure 232A:
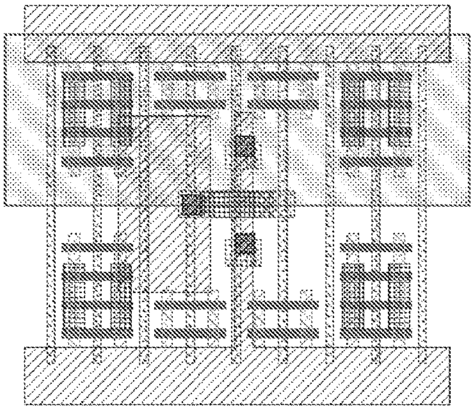
Figure 232B:
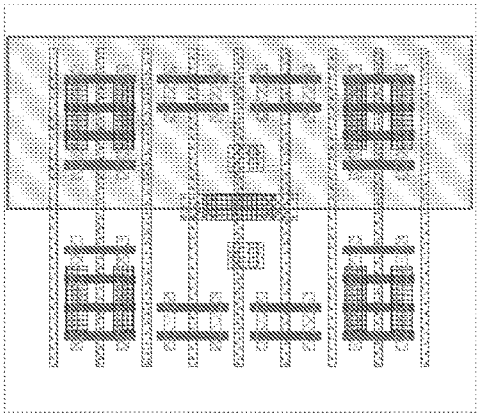
Figure 232C:
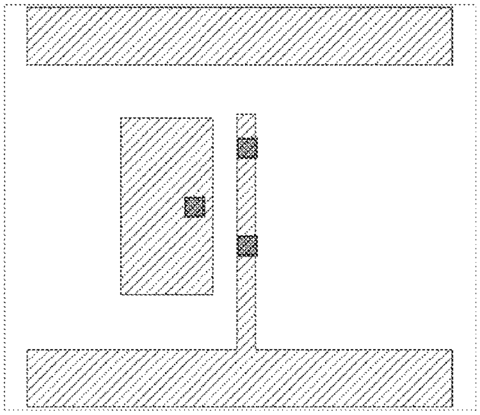
Figure 233A:
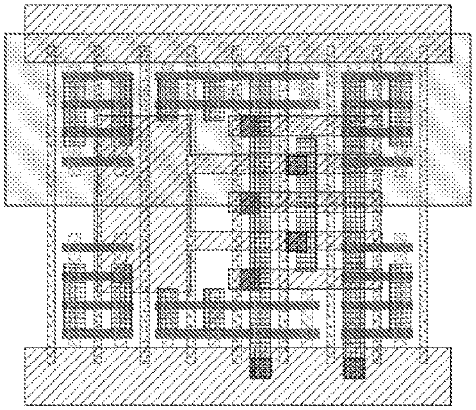
Figure 233B:
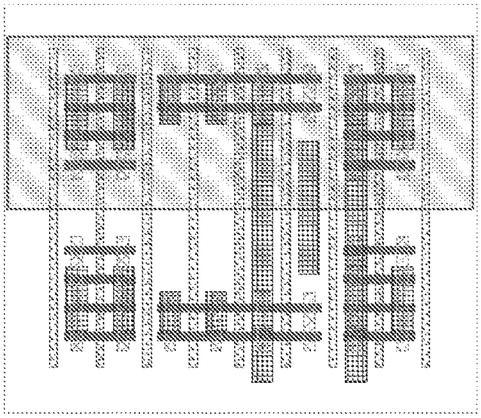
Figure 233C:
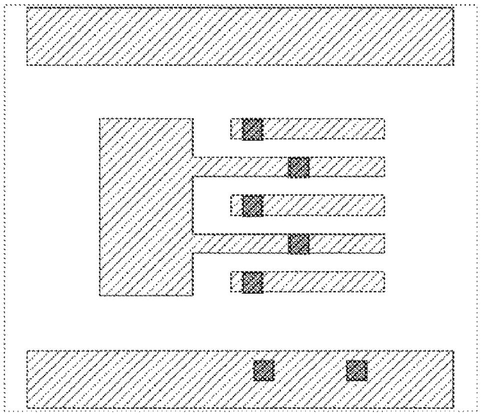
Figure 234A:
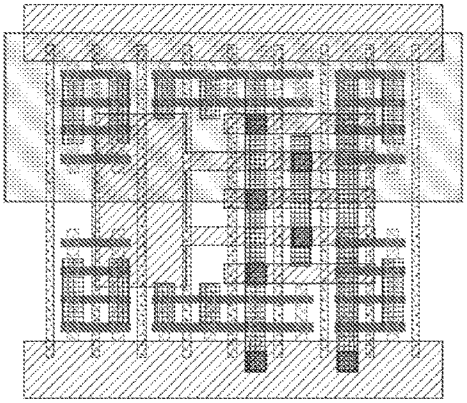
Figure 234B:
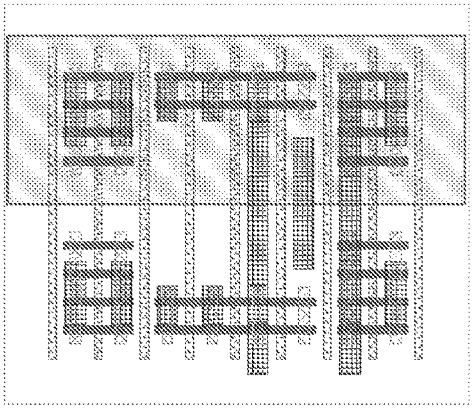
Figure 234C:
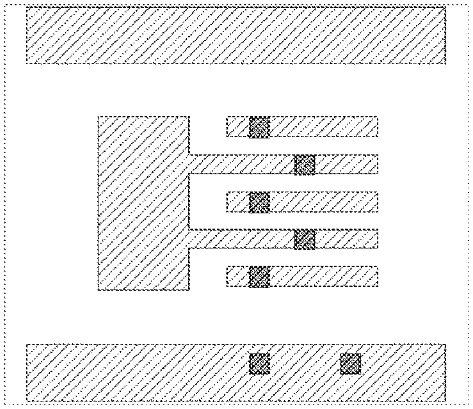
Figure 235A:
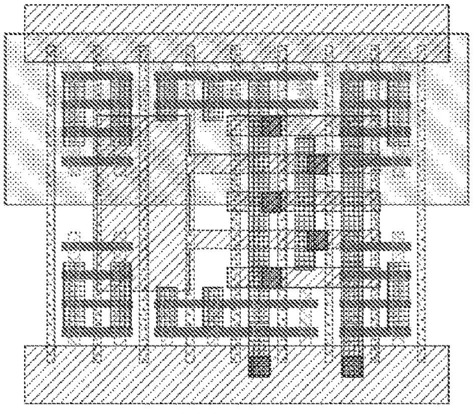
Figure 235B:
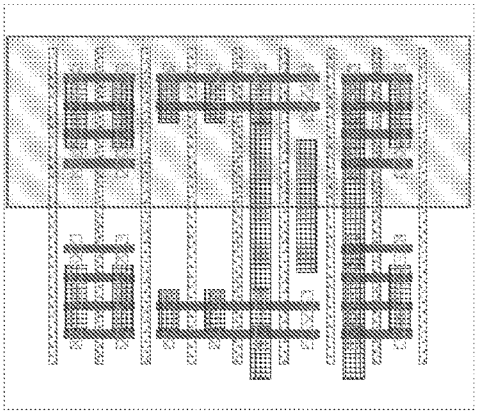
Figure 235C:
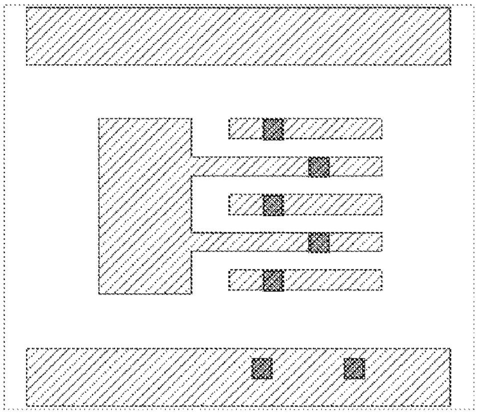
Figure 236A:
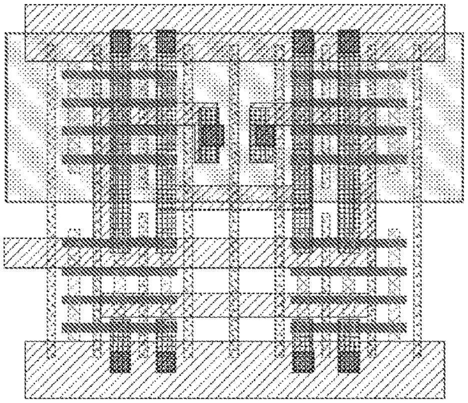
Figure 236B:
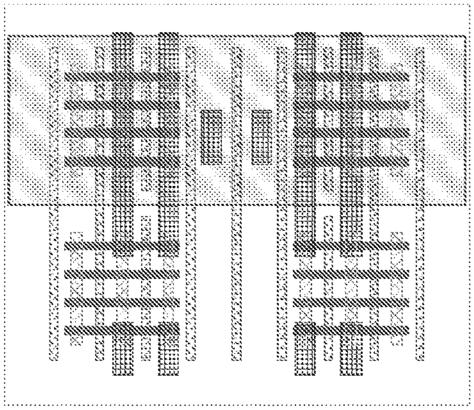
Figure 236C:
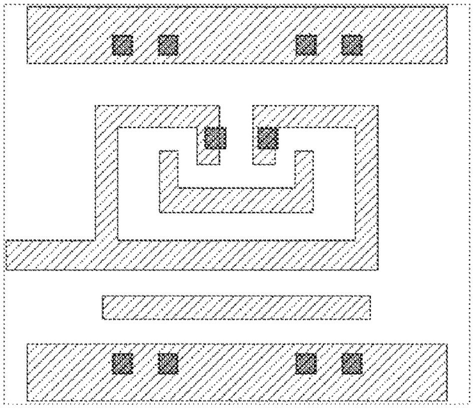
Figure 237A:
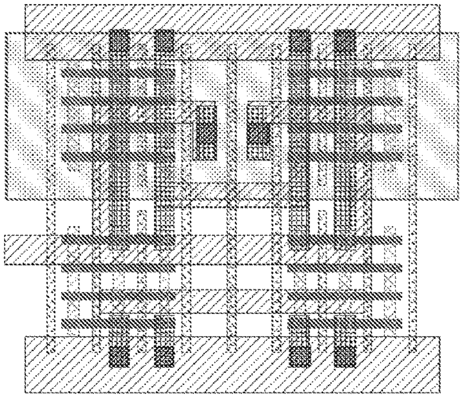
Figure 237B:
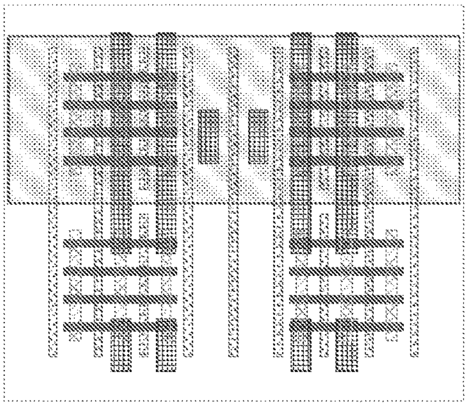
Figure 237C:
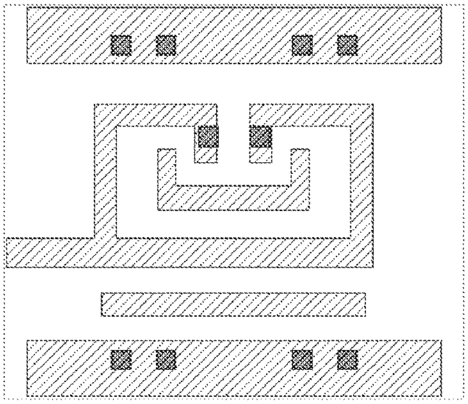
Figure 238A:
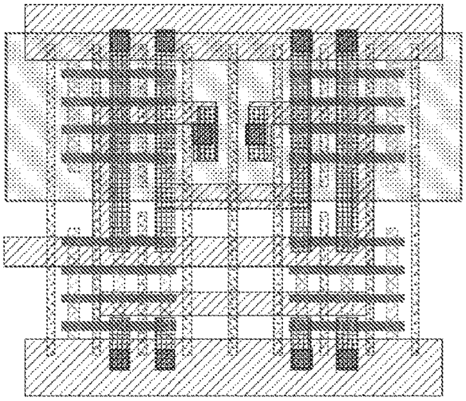
Figure 238B:
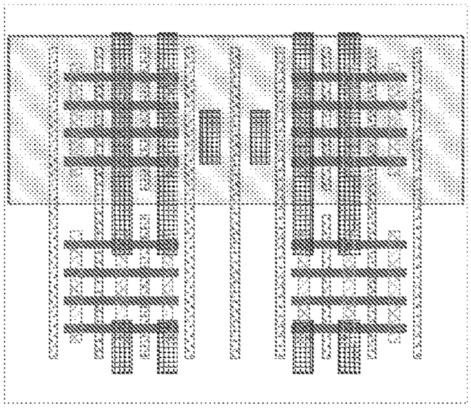
Figure 238C:
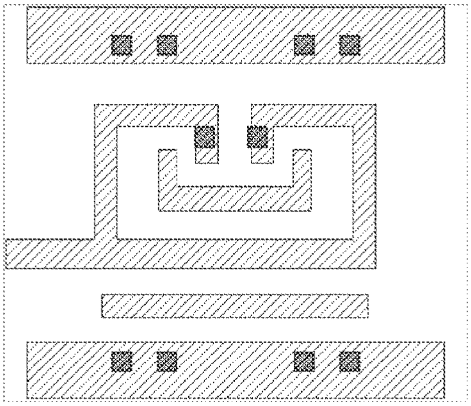
Figure 239A:
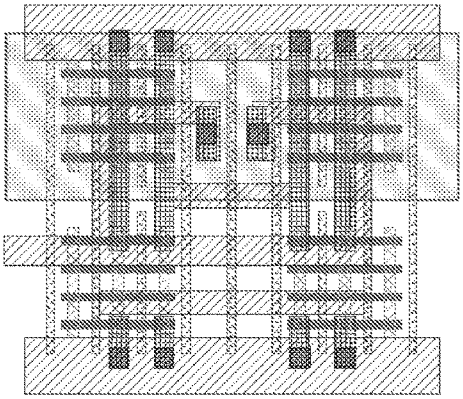
Figure 239B:
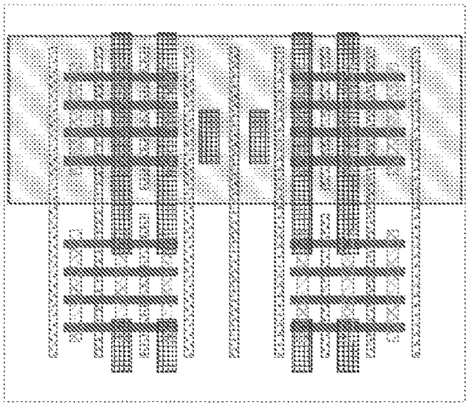
Figure 239C:
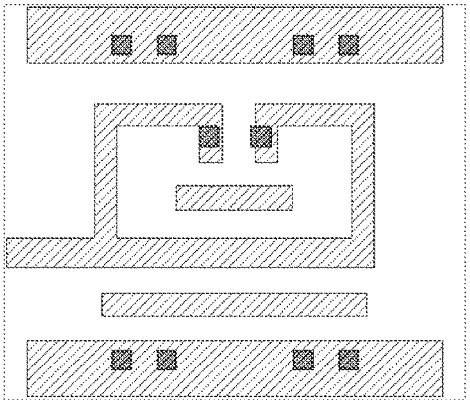
Figure 240A:
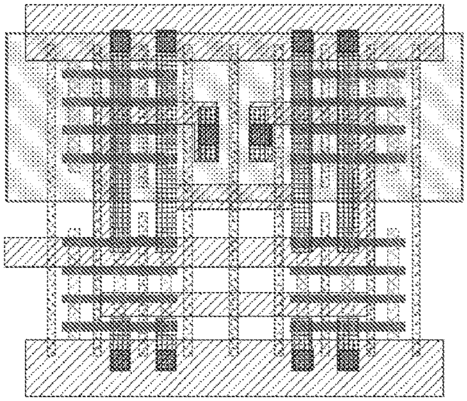
Figure 240B:
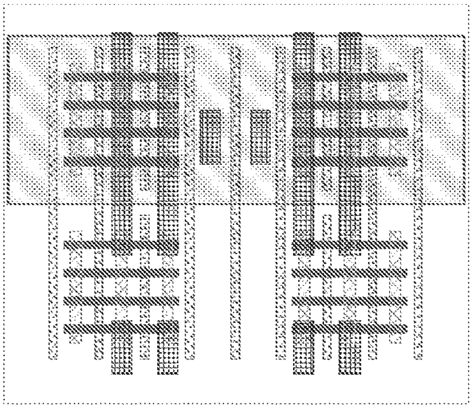
Figure 240C:
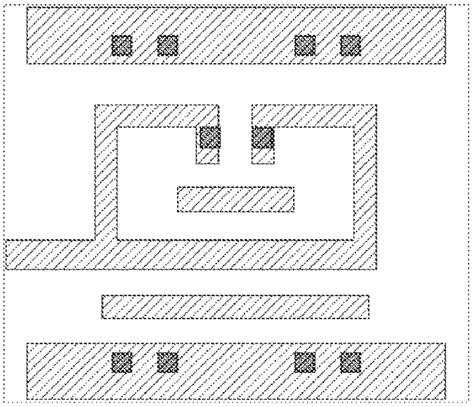
Figure 241A:
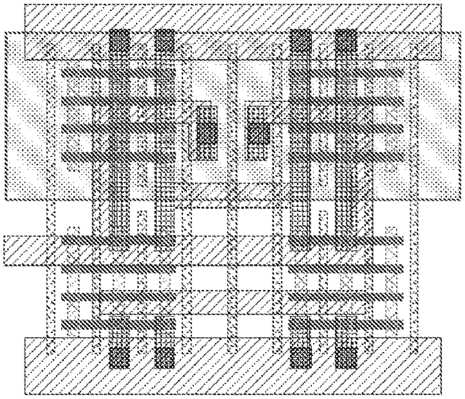
Figure 241B:
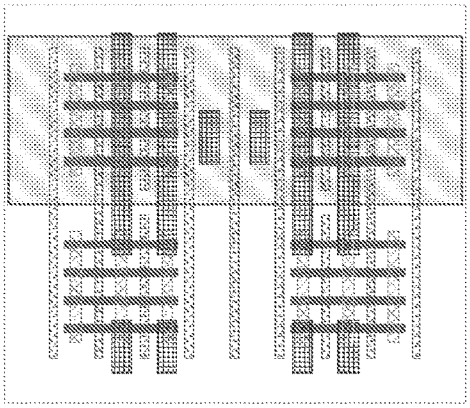
Figure 241C:
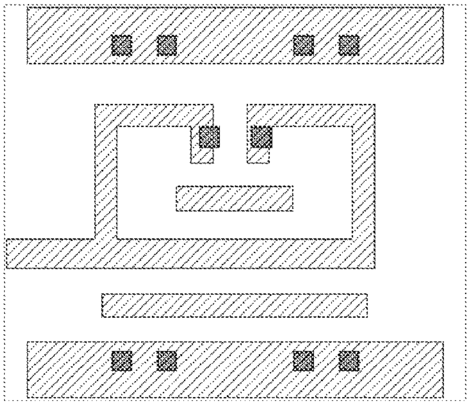
Figure 242A:
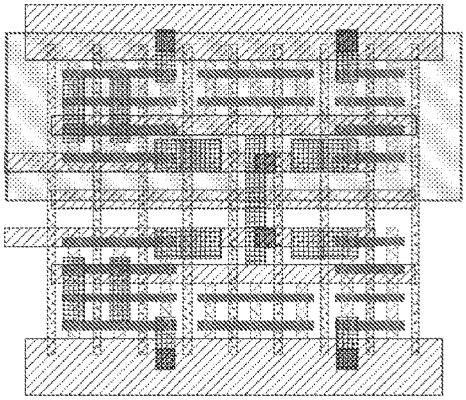
Figure 242B:
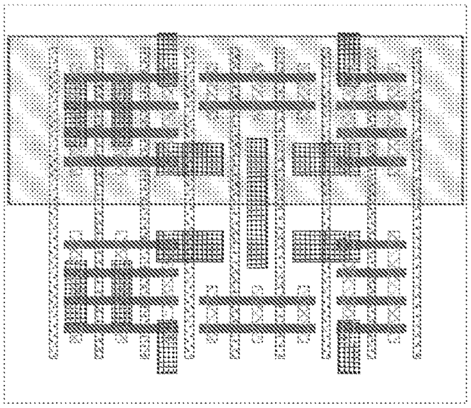
Figure 242C:
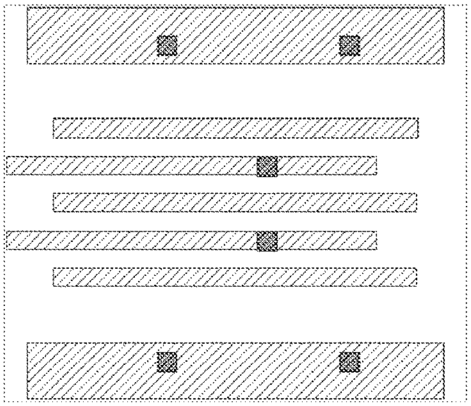
Figure 243A:
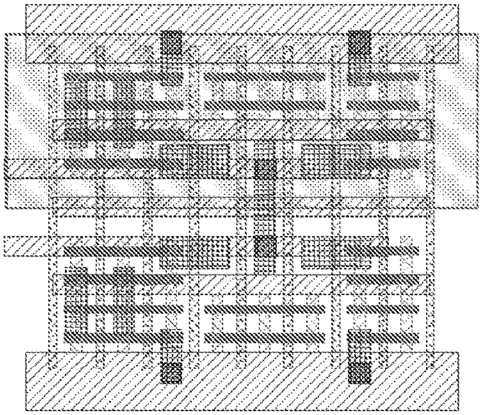
Figure 243B:
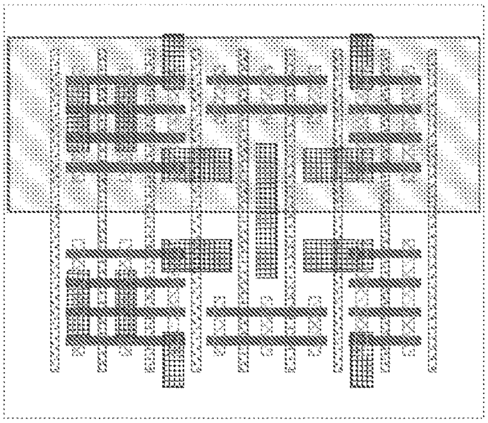
Figure 243C:
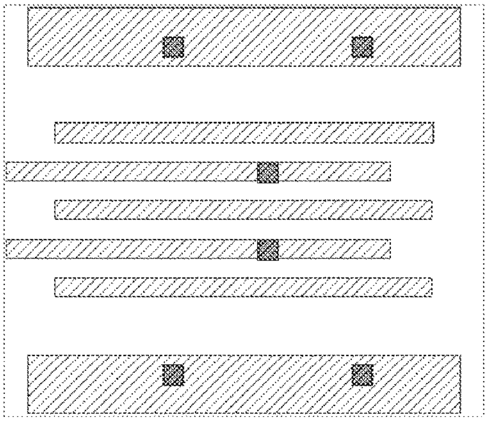
Figure 244A:
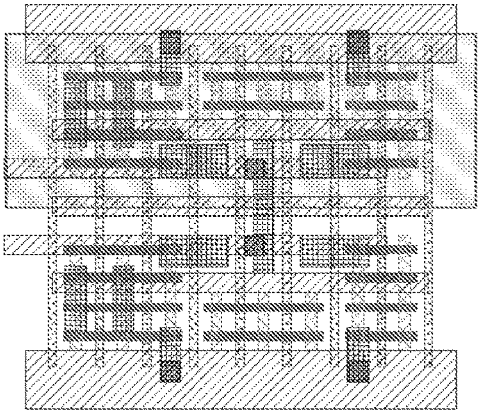
Figure 244B:
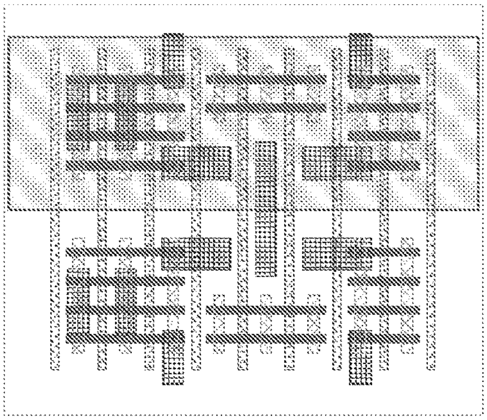
Figure 244C:
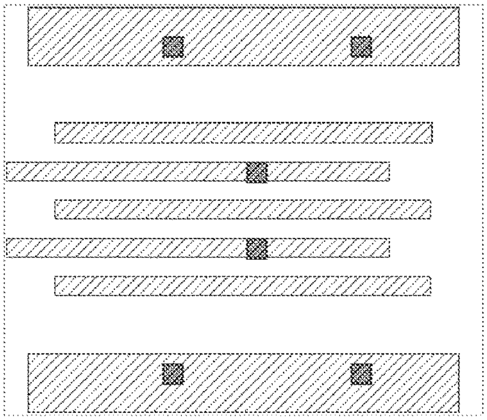
Figure 245A:
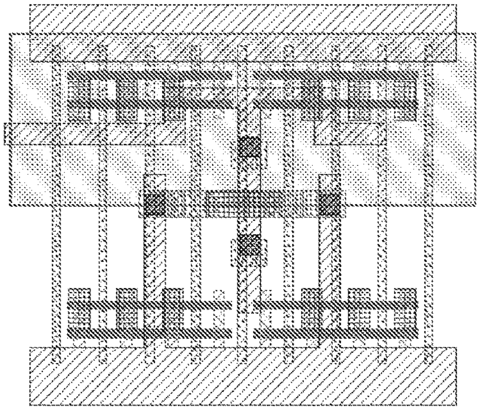
Figure 245B:
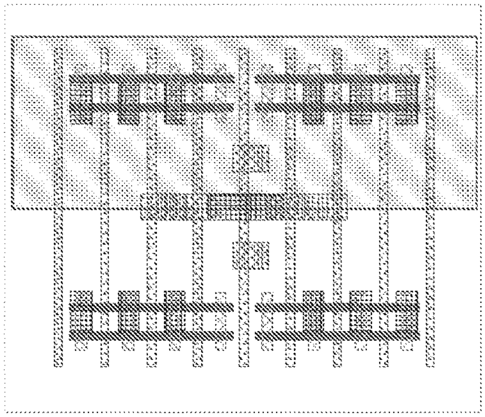
Figure 245C:
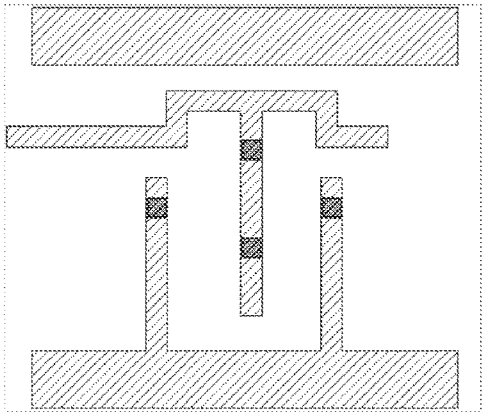
Figure 246A:
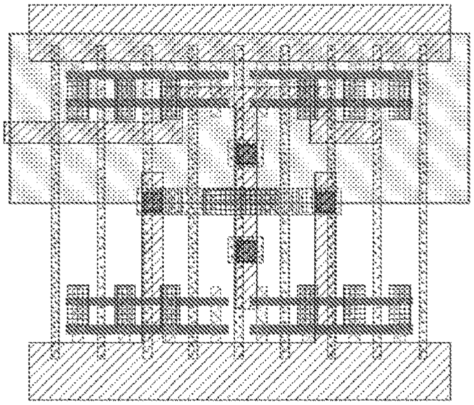
Figure 246B:
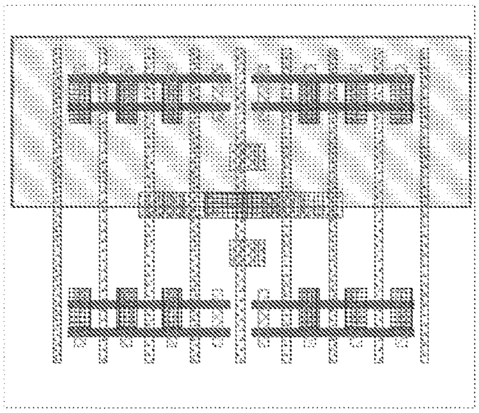
Figure 246C:
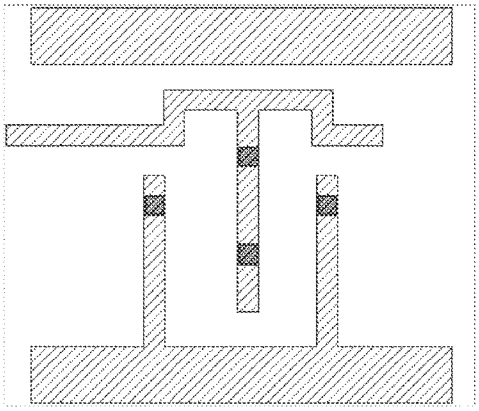
Figure 247A:
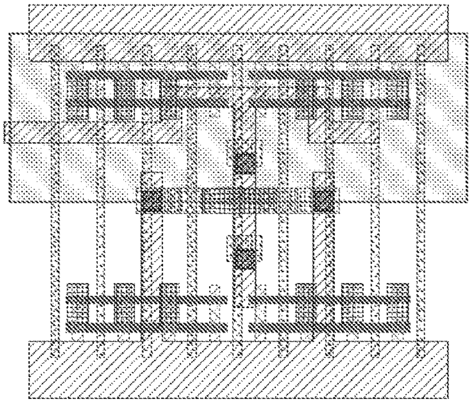
Figure 247B:
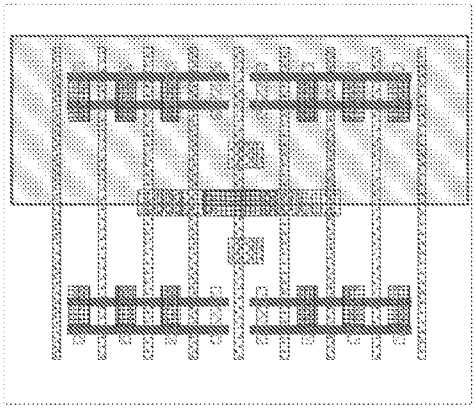
Figure 247C:
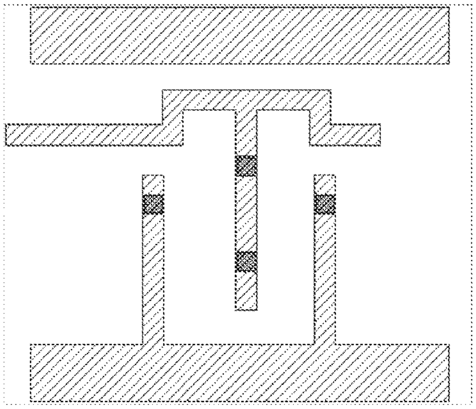
Figure 248A:
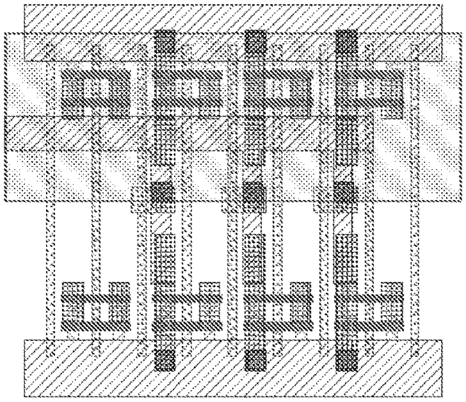
Figure 248B:
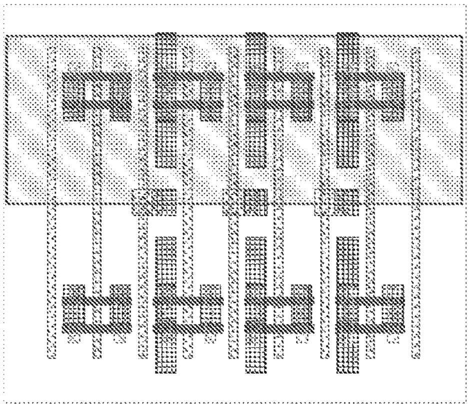
Figure 248C:
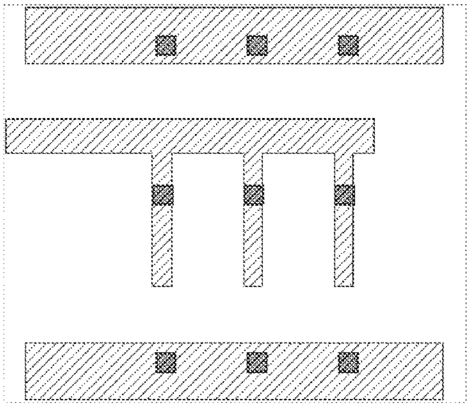
Figure 249A:
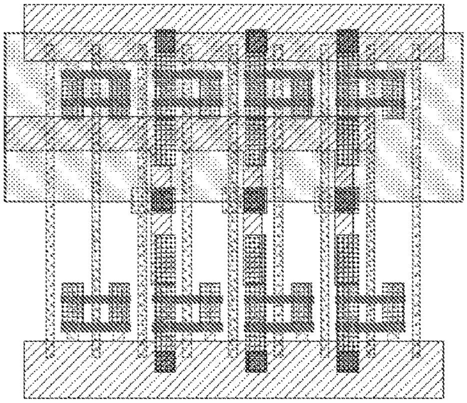
Figure 249B:
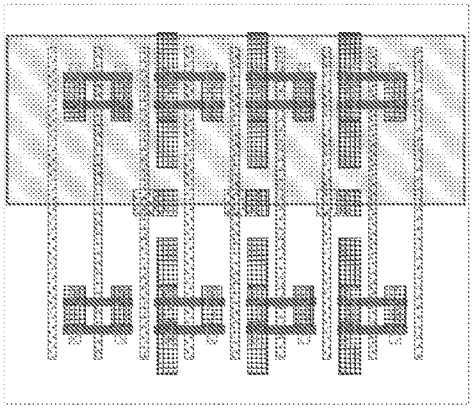
Figure 249C:
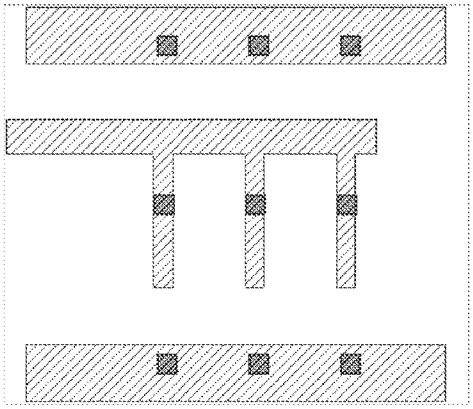
Figure 250A:
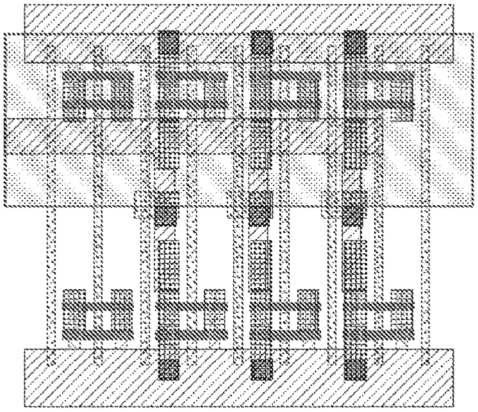
Figure 250B:
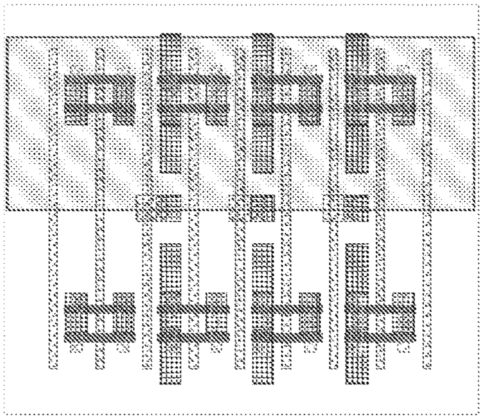
Figure 250C:
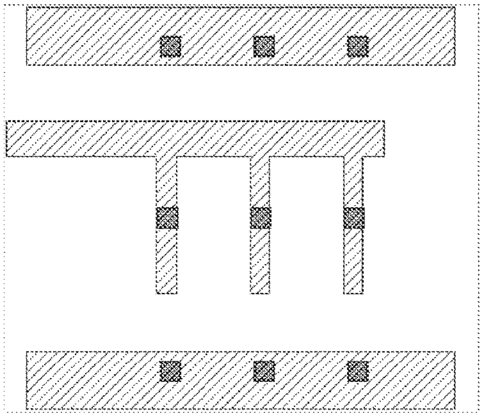
Figure 251A:
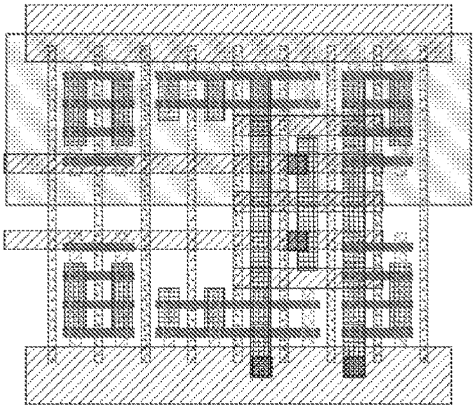
Figure 251B:
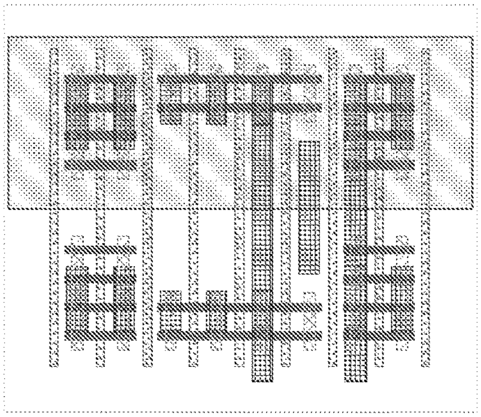
Figure 251C:
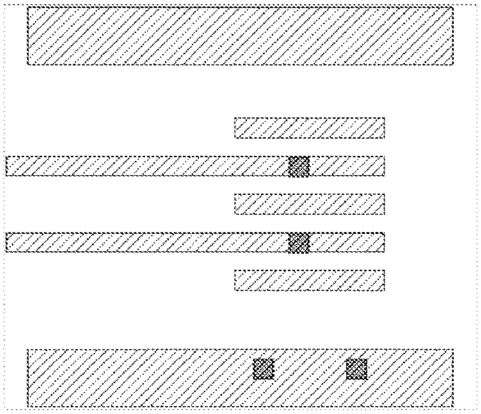
Figure 252A:
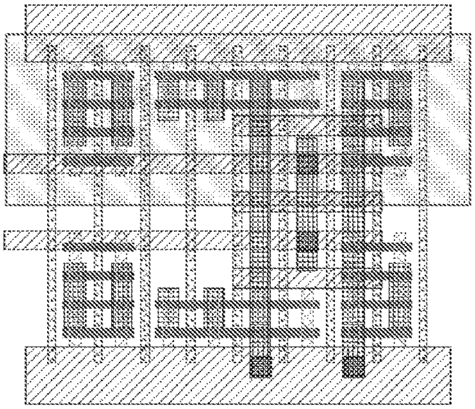
Figure 252B:
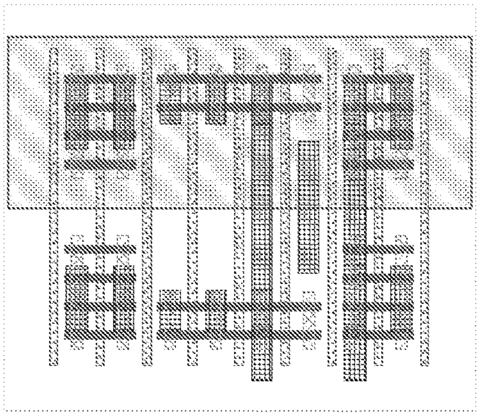
Figure 252C:
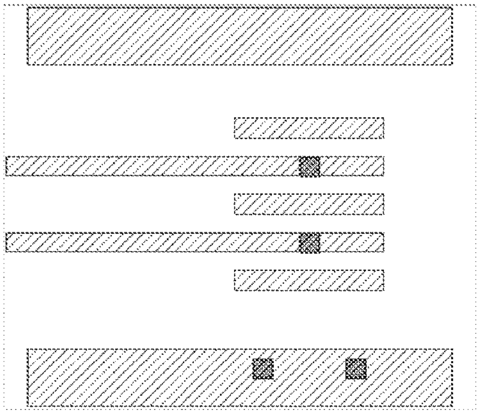
Figure 253A:
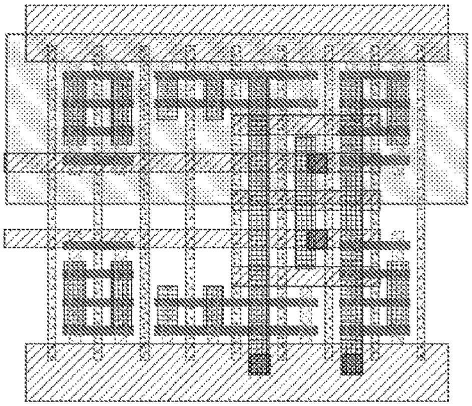
Figure 253B:
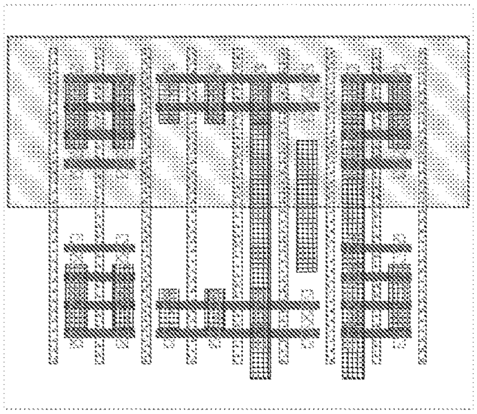
Figure 253C:
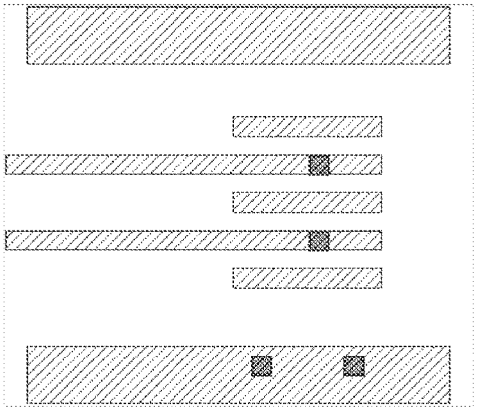
Figure 254A:
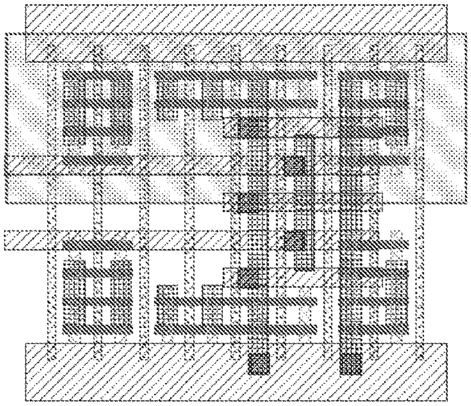
Figure 254B:
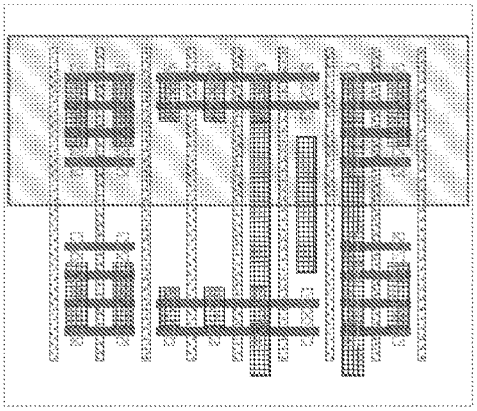
Figure 254C:
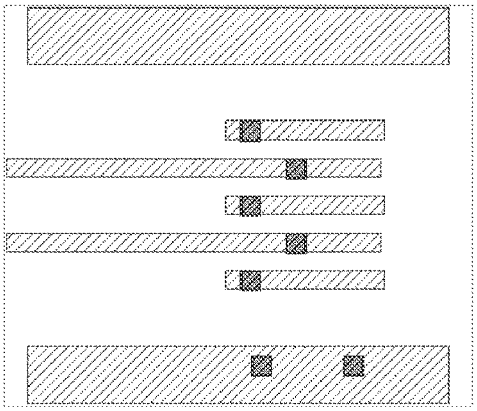
Figure 255A:
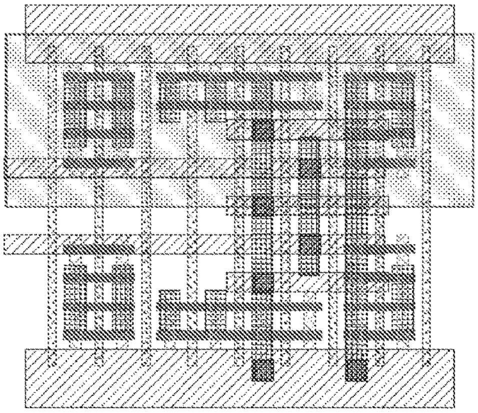
Figure 255B:
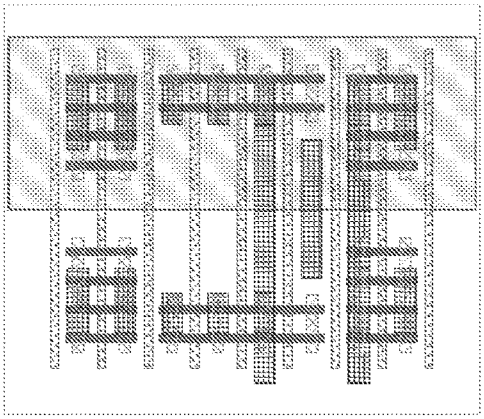
Figure 255C:
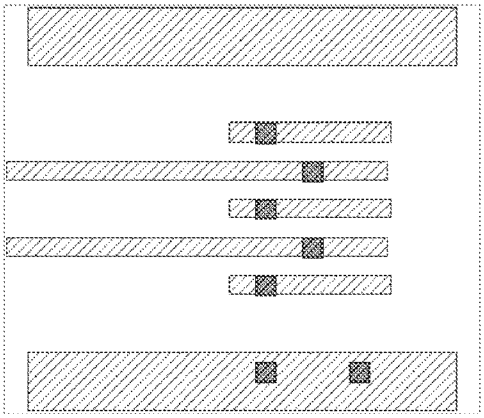
Figure 256A:
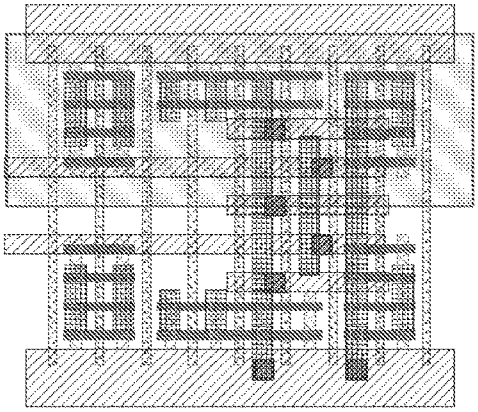
Figure 256B:
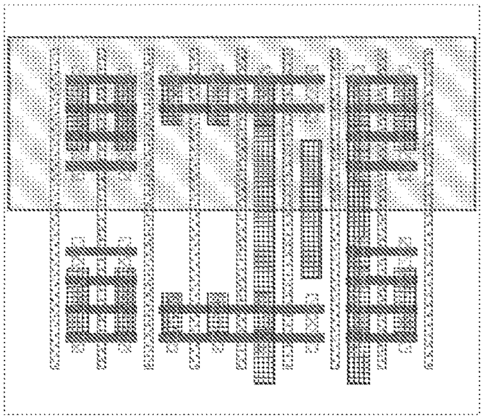
Figure 256C:
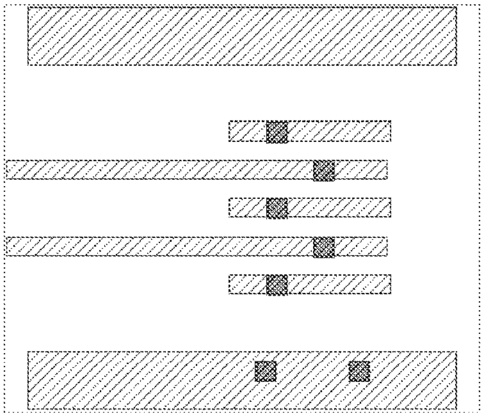
Figure 257A:
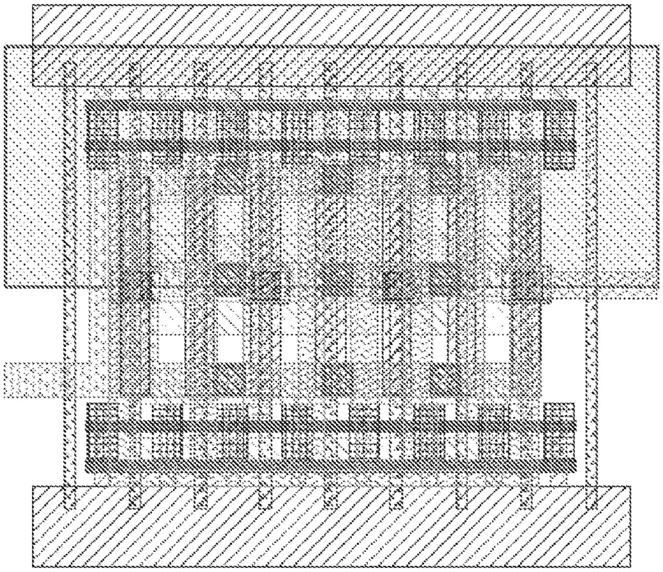
Figure 257B:
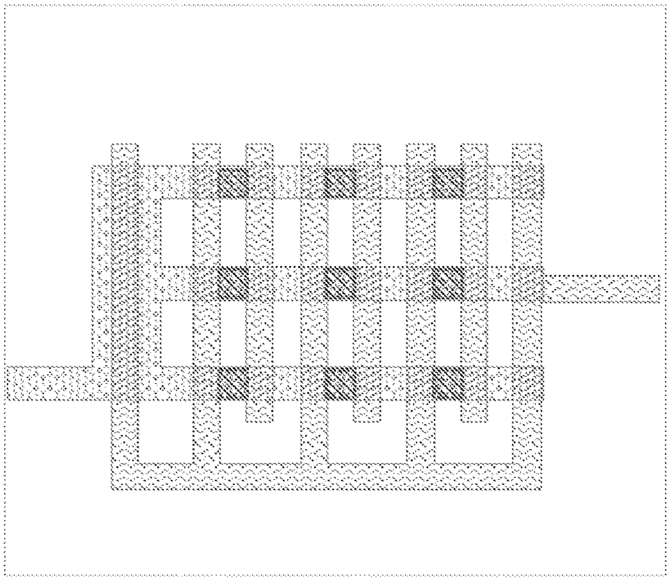
Figure 258A:
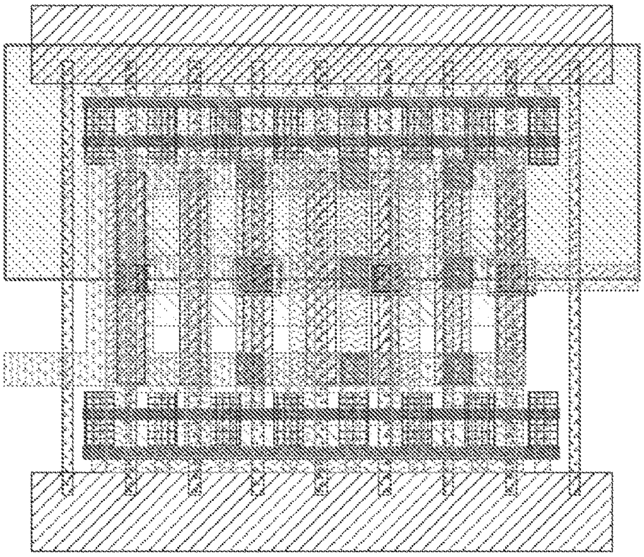
Figure 258B:
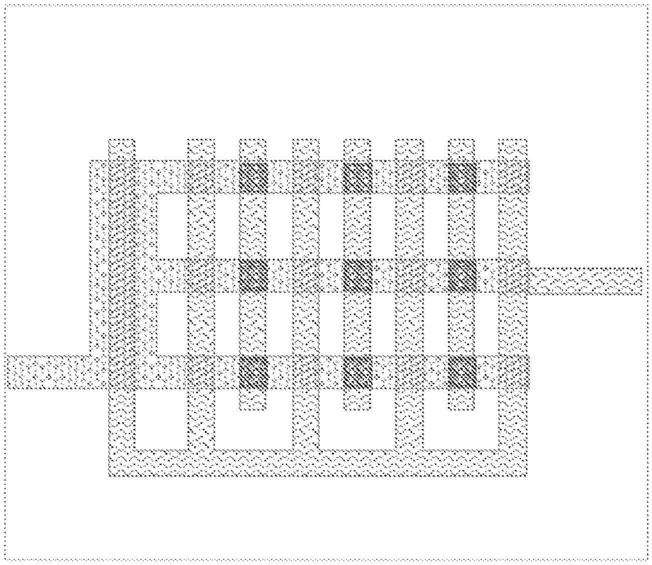
Figure 259A:
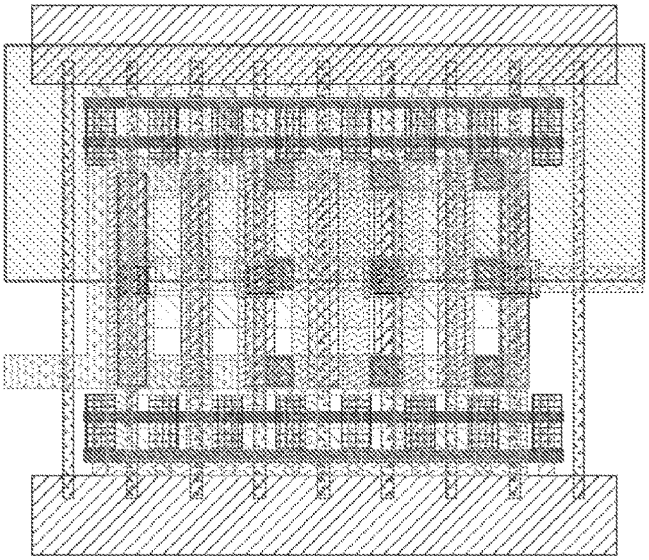
Figure 259B:
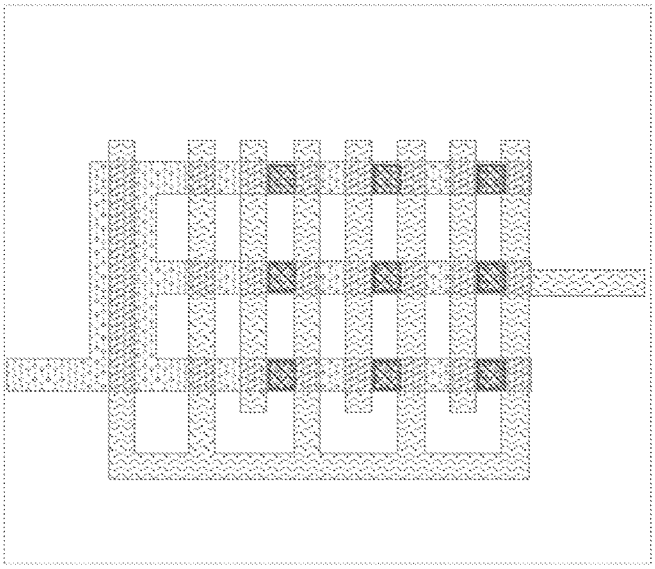
Figure 260A:
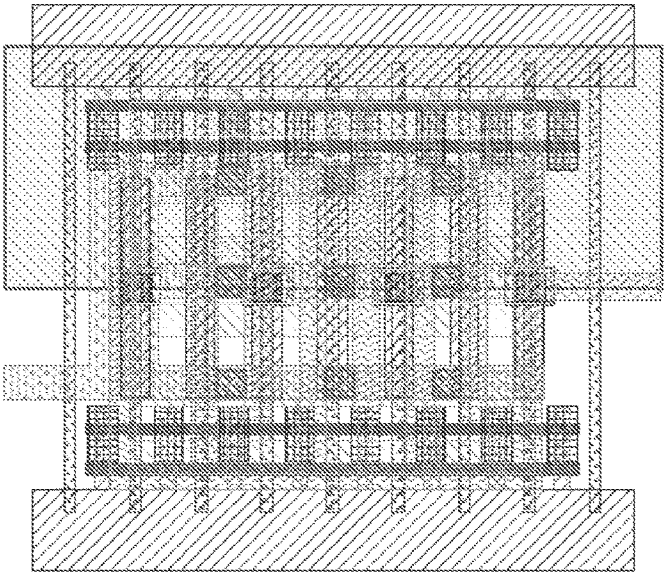
Figure 260B:
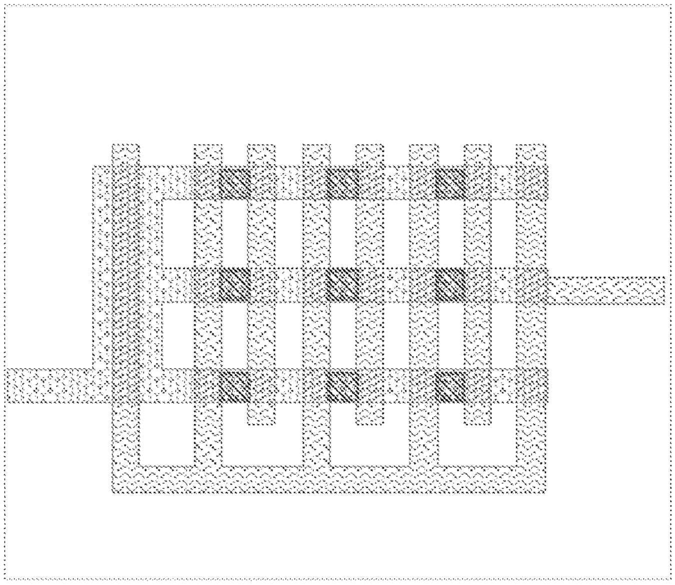
Figure 261A:
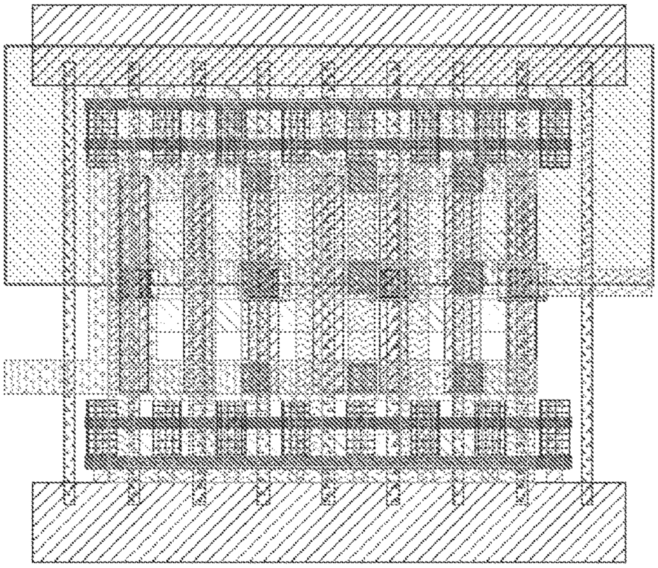
Figure 261B:
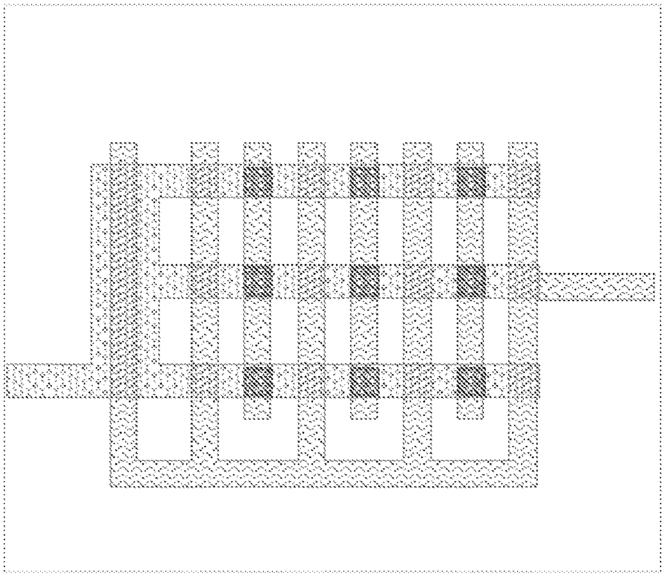
Figure 262A:
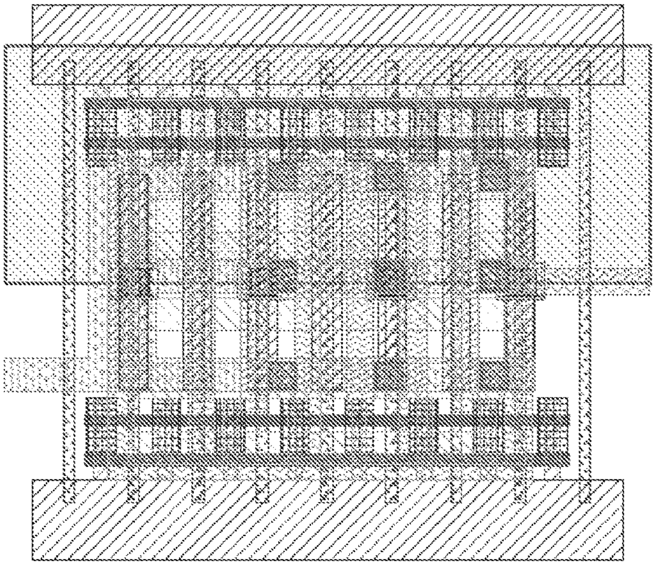
Figure 262B:
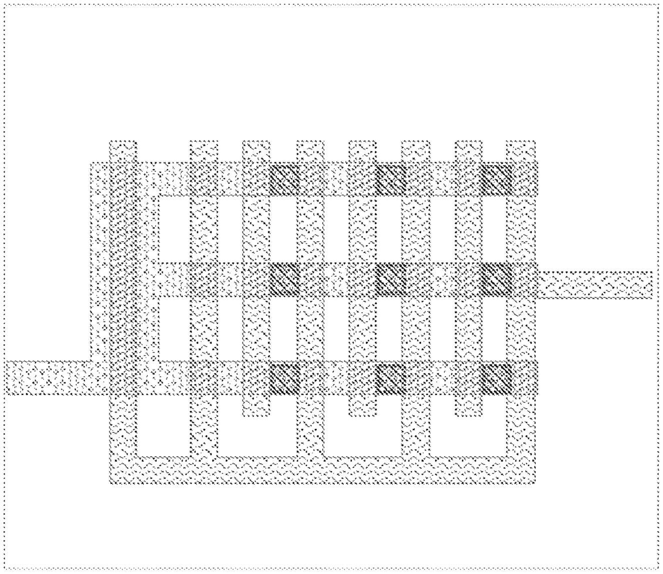
Figure 263A:
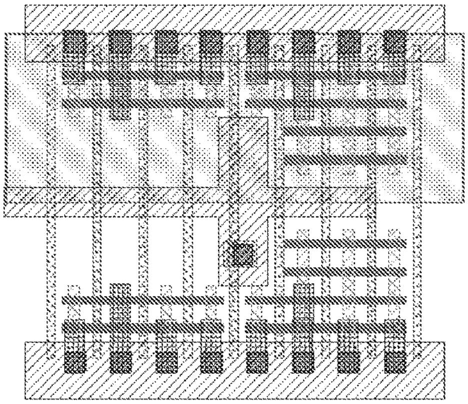
Figure 263B:
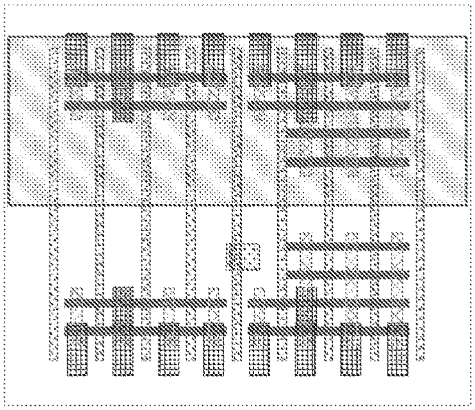
Figure 263C:
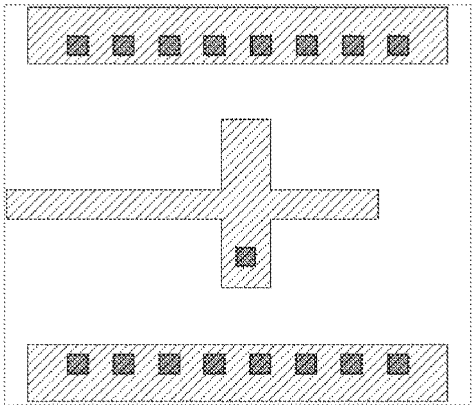
Figure 264A:
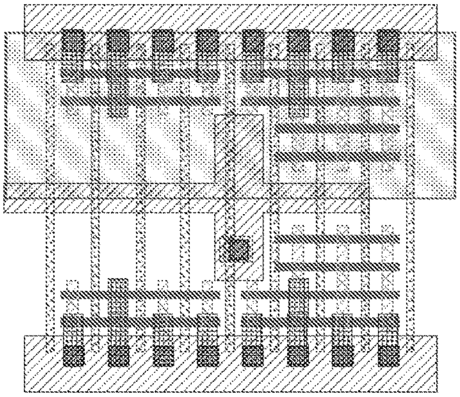
Figure 264B:
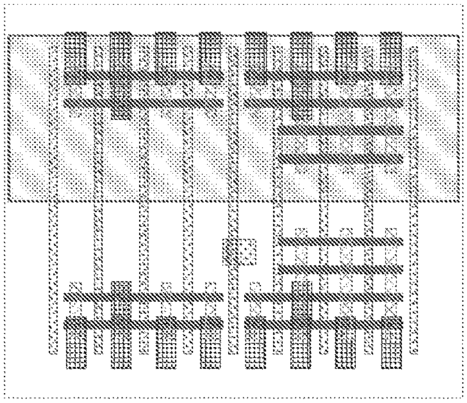
Figure 264C:
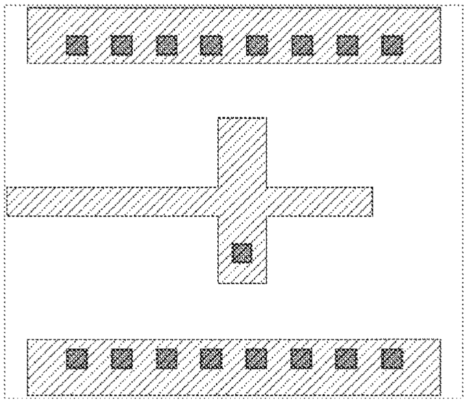
Figure 265A:
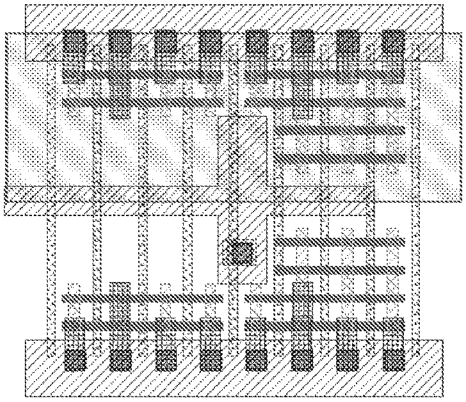
Figure 265B:
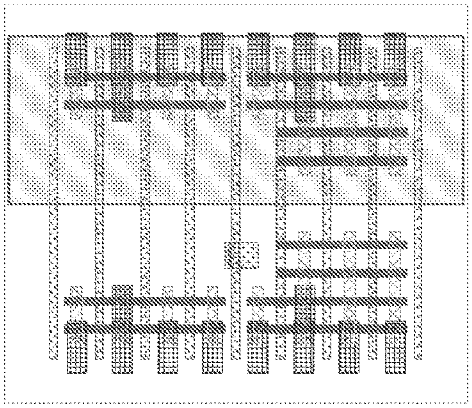
Figure 265C:
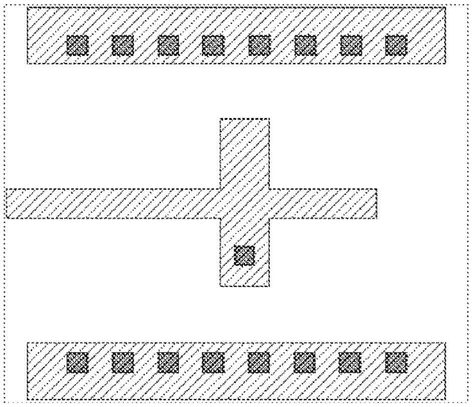
Figure 266A:
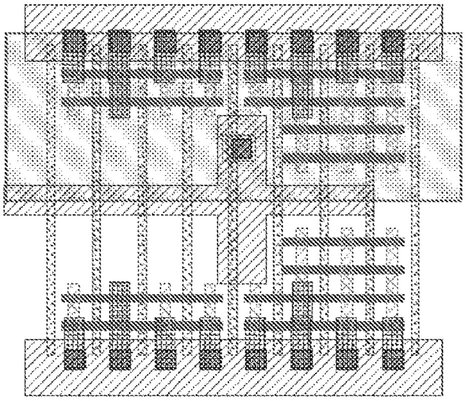
Figure 266B:
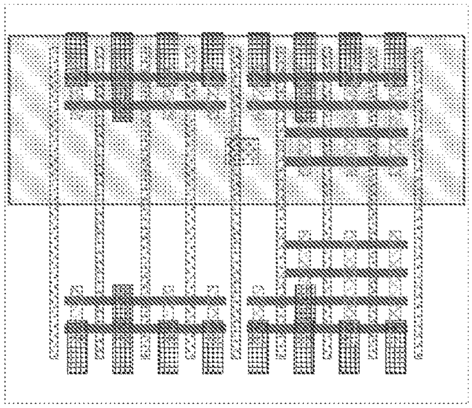
Figure 266C:
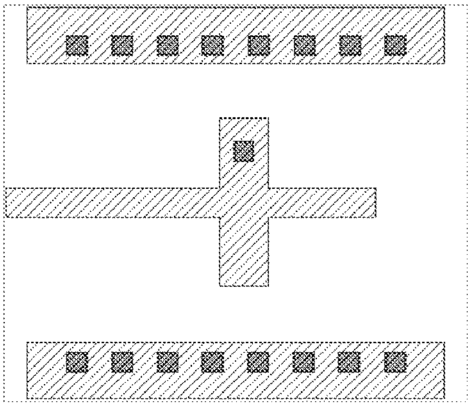
Figure 267A:
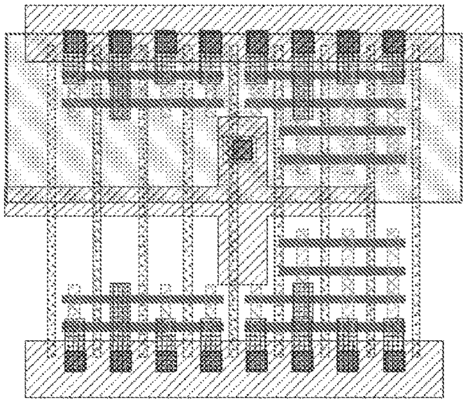
Figure 267B:
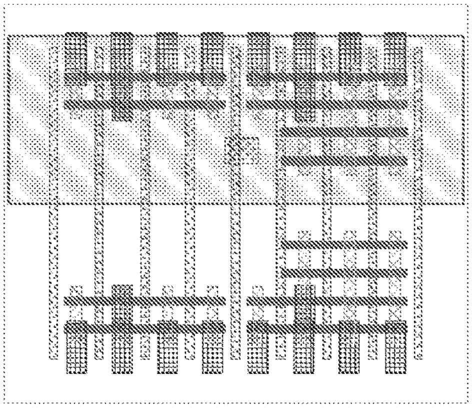
Figure 267C:
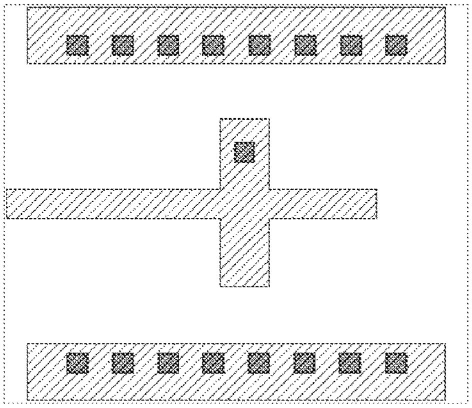
Figure 268A:
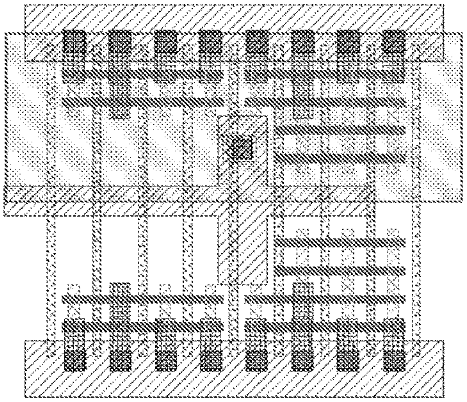
Figure 268B:
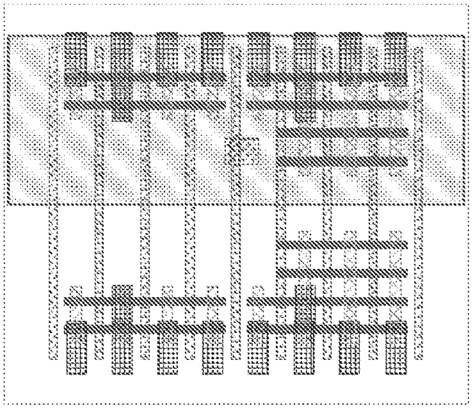
Figure 268C:
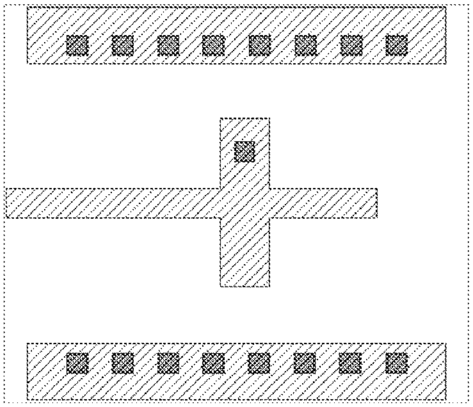
Figure 269A:
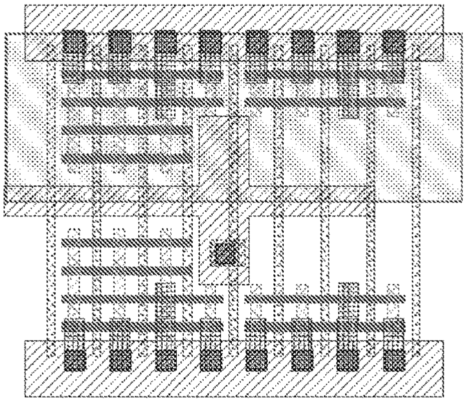
Figure 269B:
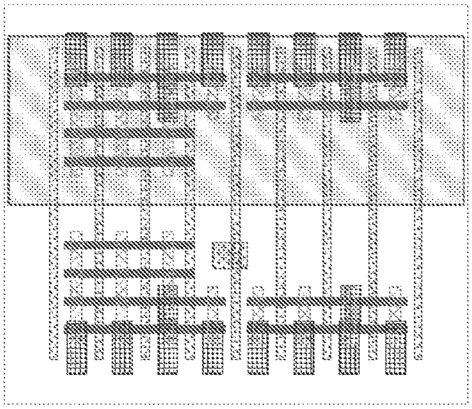
Figure 269C:
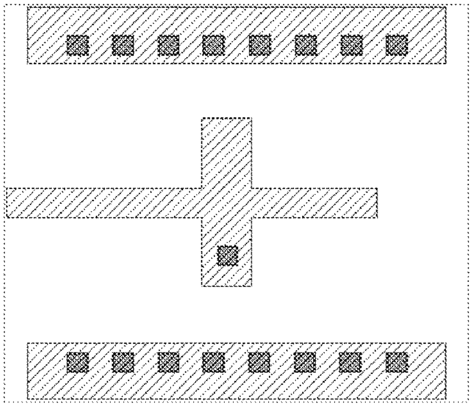
Figure 270A:
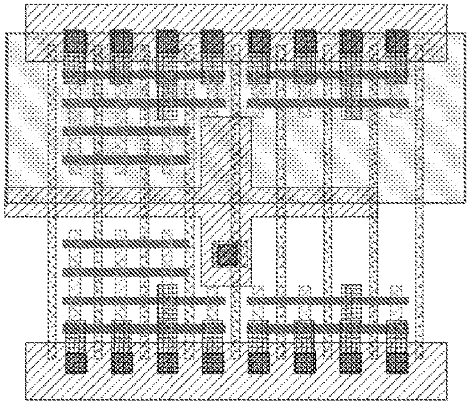
Figure 270B:
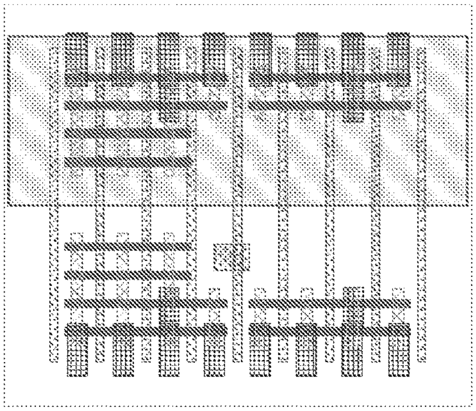
Figure 270C:
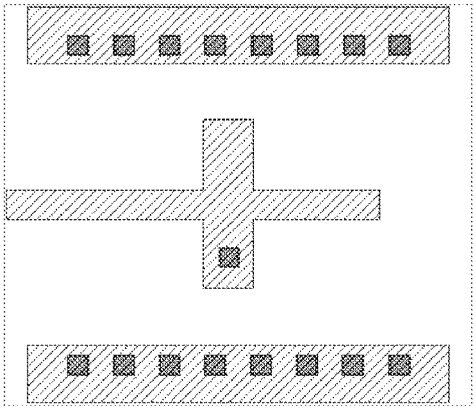
Figure 271A:
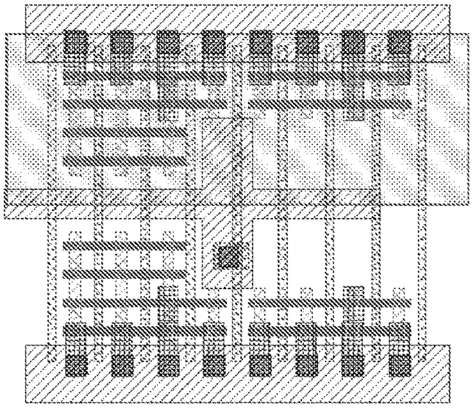
Figure 271B:
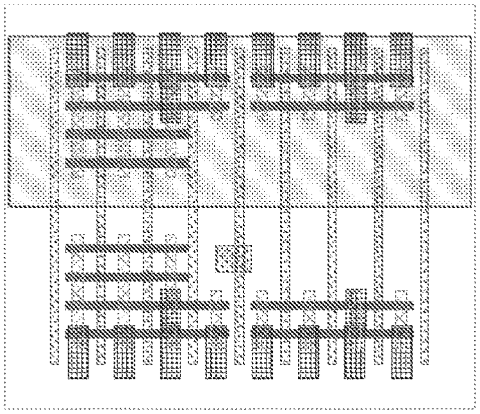
Figure 271C:
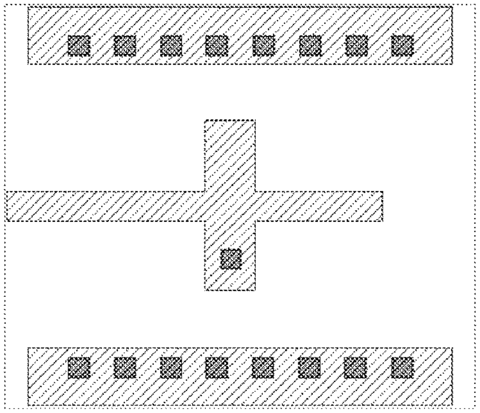
Figure 272A:
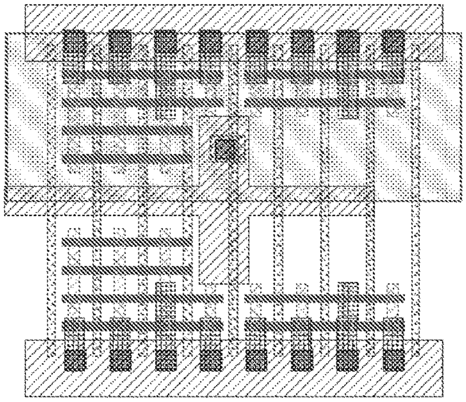
Figure 272B:
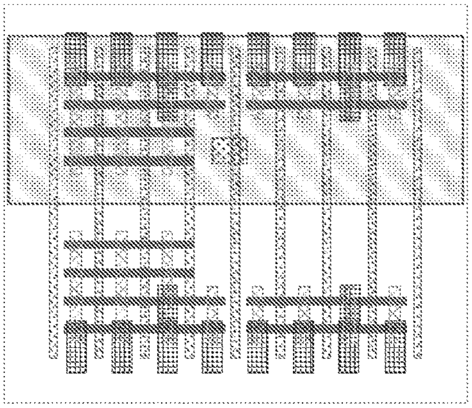
Figure 272C:
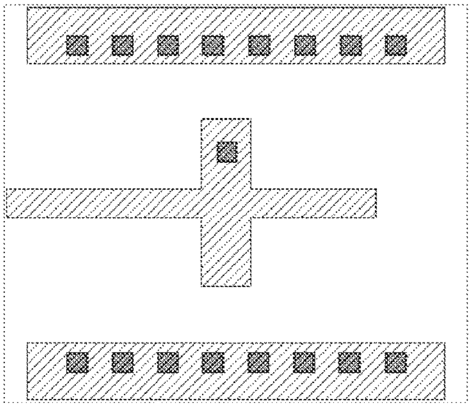
Figure 273A:
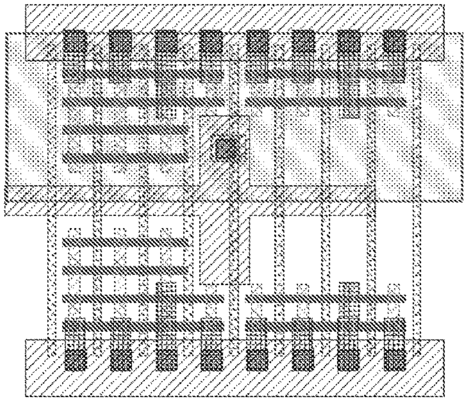
Figure 273B:
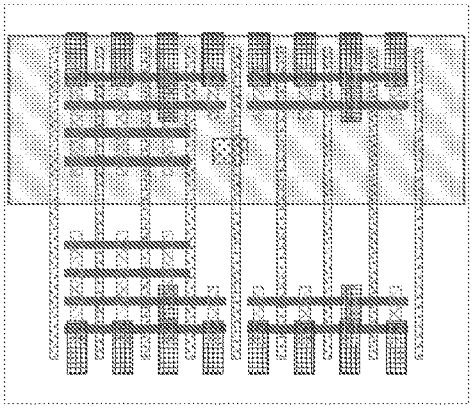
Figure 273C:
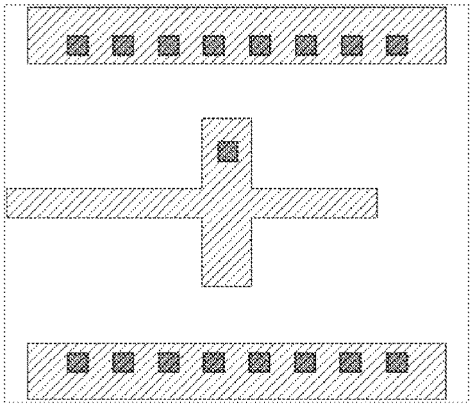
Figure 274A:
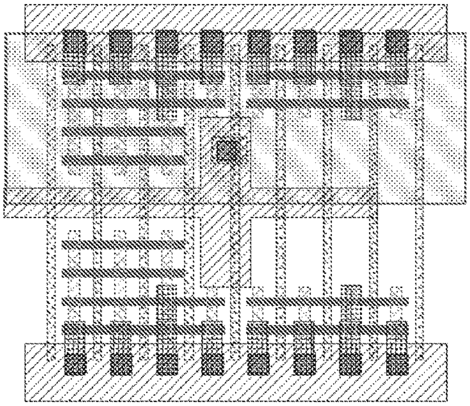
Figure 274B:
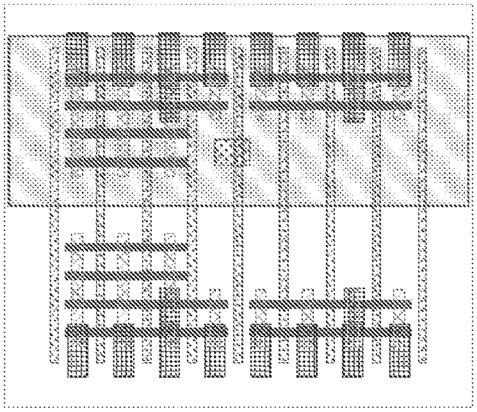
Figure 274C:
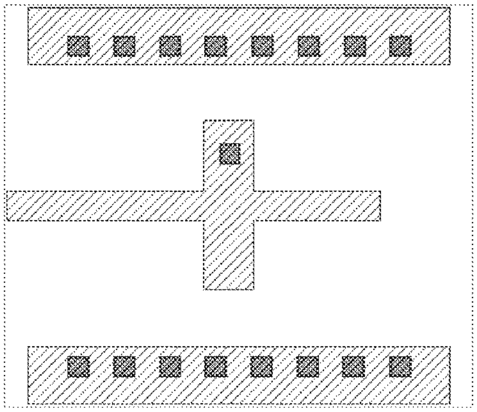
Figure 275A:
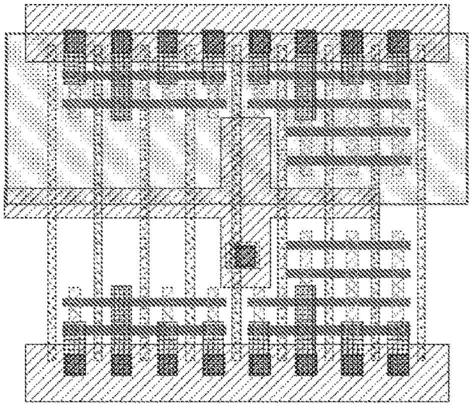
Figure 275B:
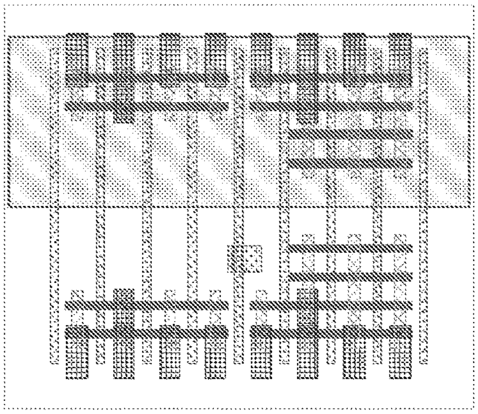
Figure 275C:
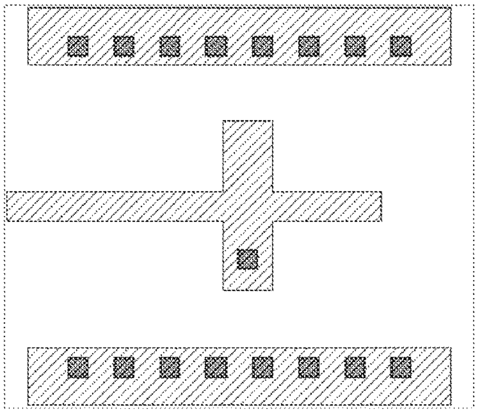
Figure 276A:
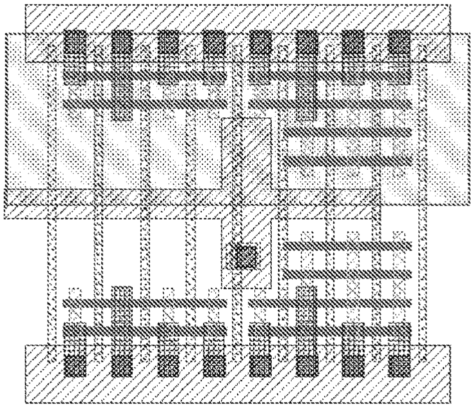
Figure 276B:
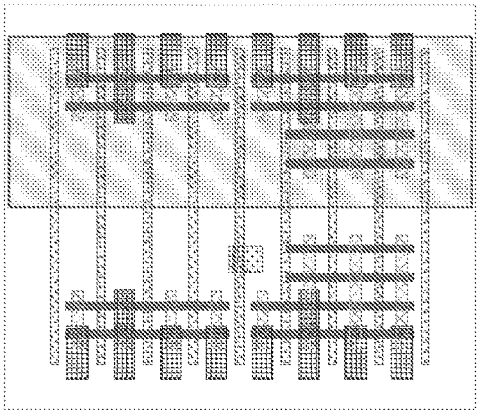
Figure 276C:
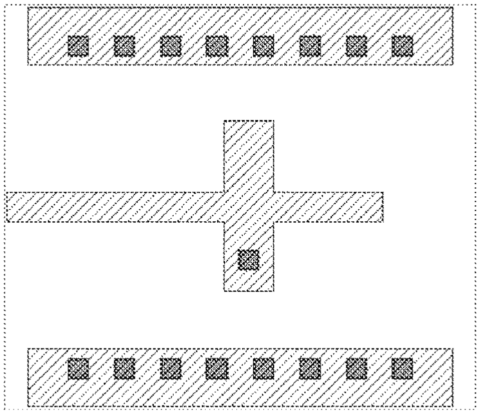
Figure 277A:
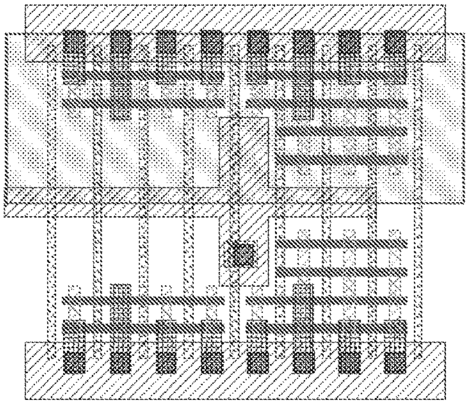
Figure 277B:
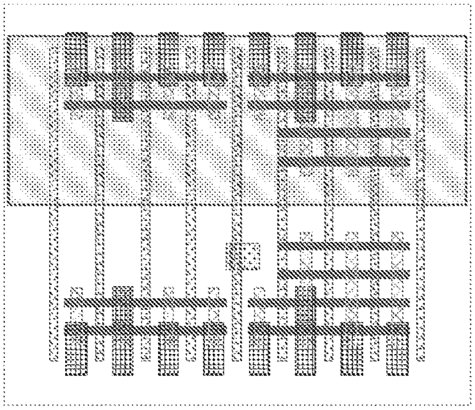
Figure 277C:
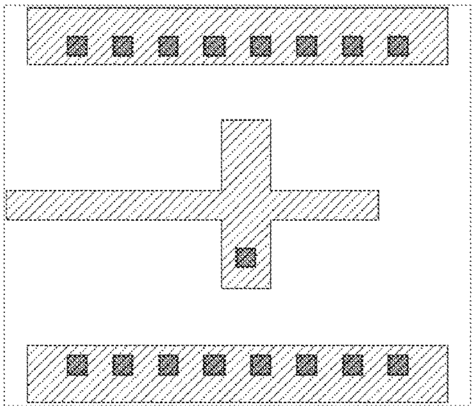
Figure 278A:
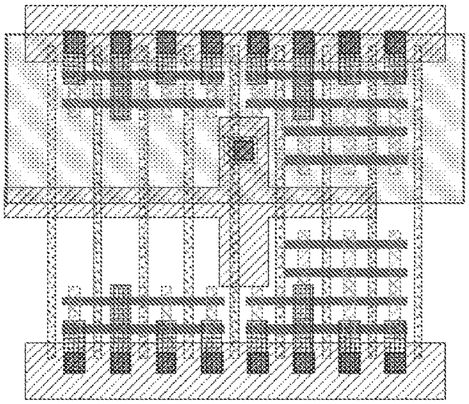
Figure 278B:
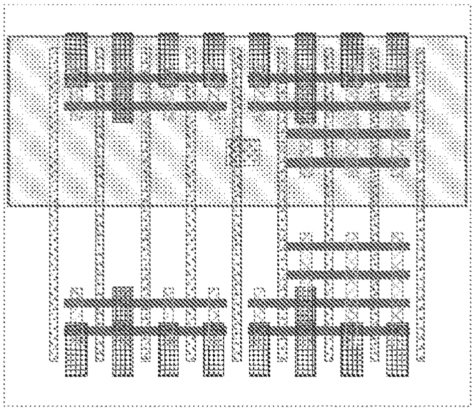
Figure 278C:
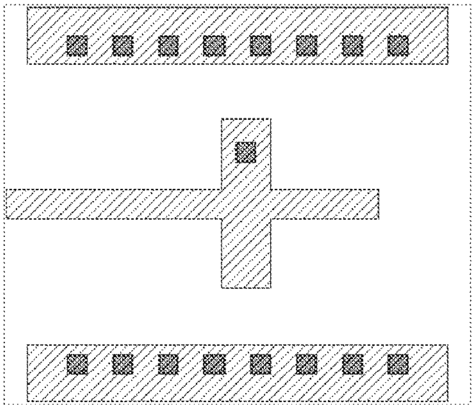
Figure 279A:
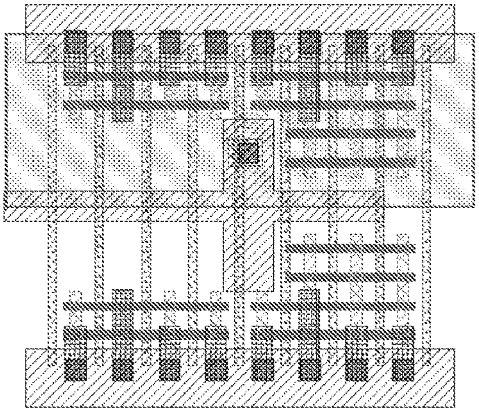
Figure 279B:
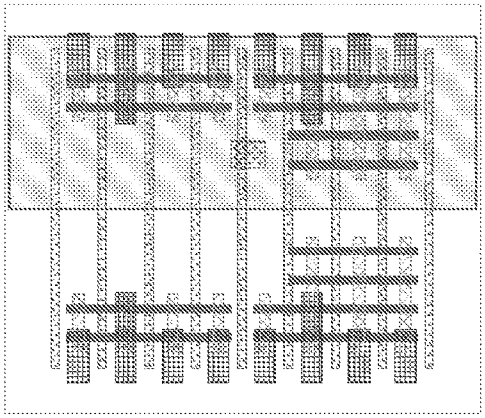
Figure 279C:
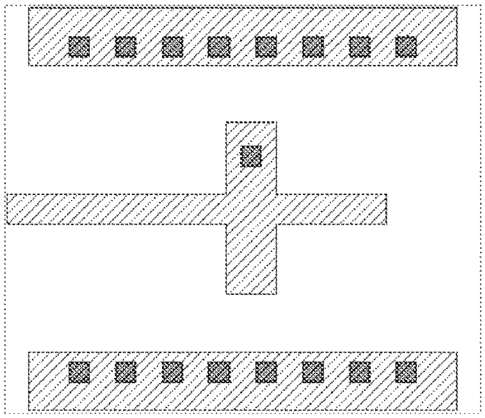
Figure 280A:
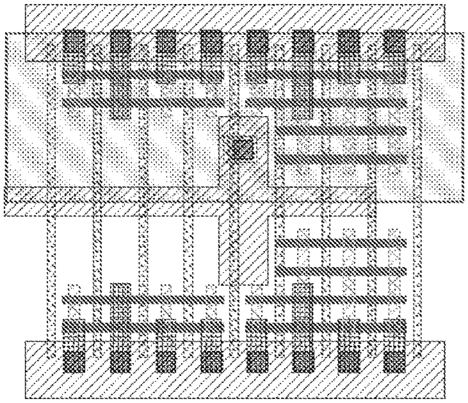
Figure 280B:
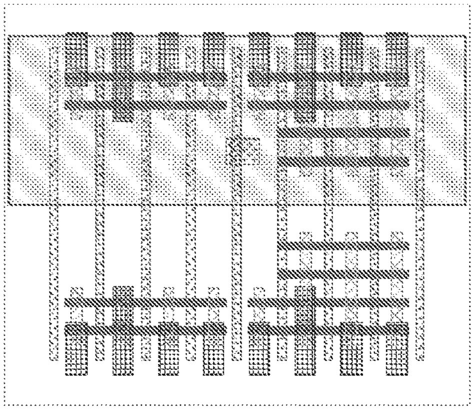
Figure 280C:
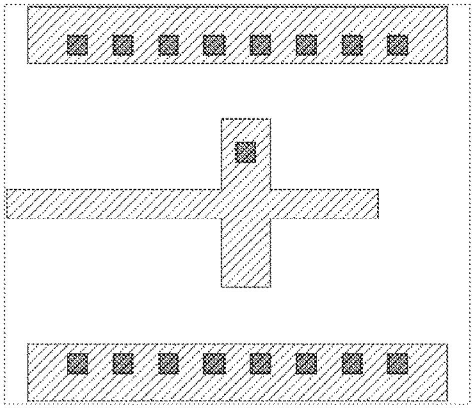
Figure 281A:
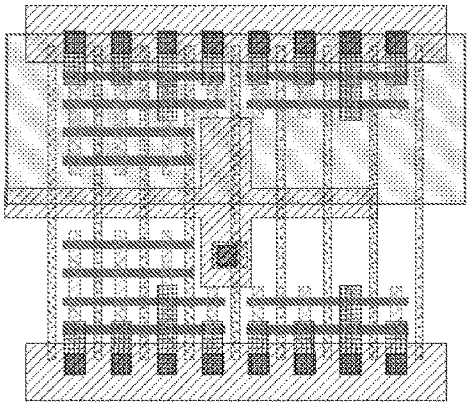
Figure 281B:
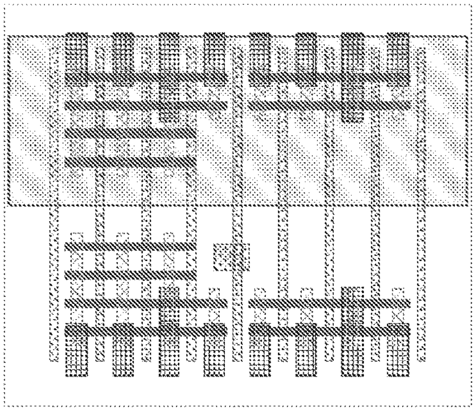
Figure 281C:
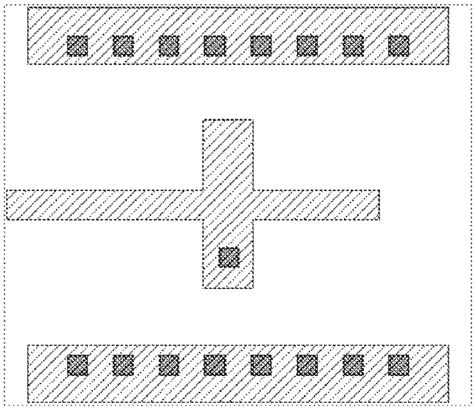
Figure 282A:
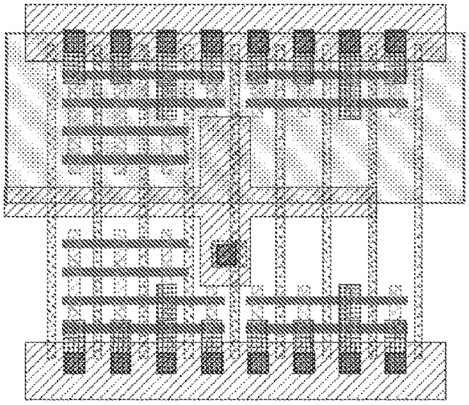
Figure 282B:
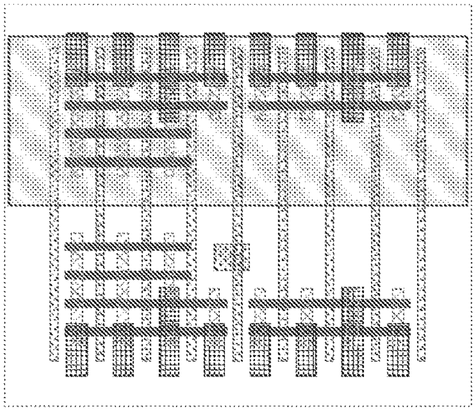
Figure 282C:
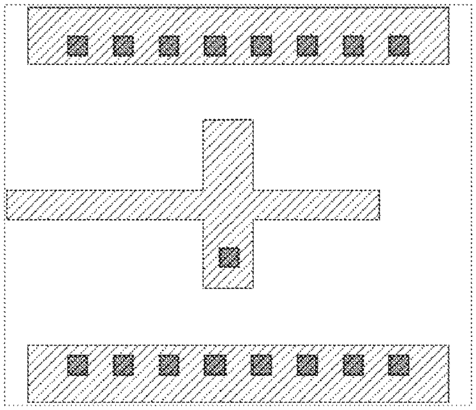
Figure 283A:
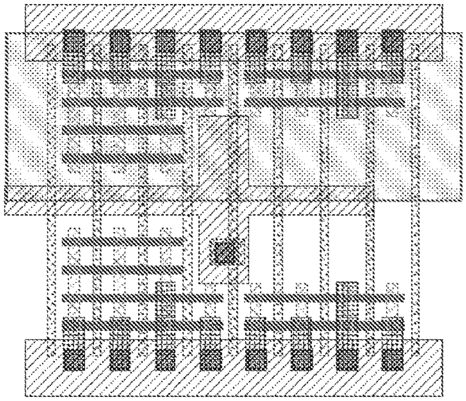
Figure 283B:
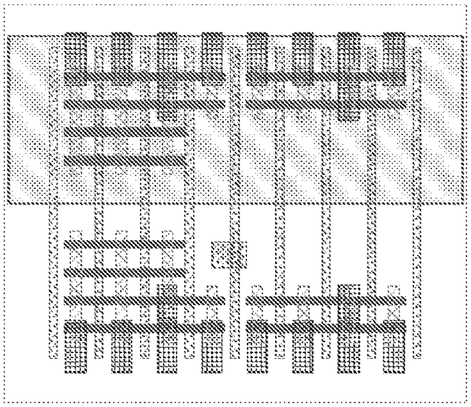
Figure 283C:
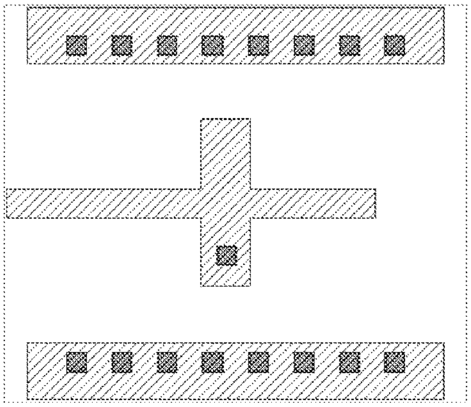
Figure 284A:
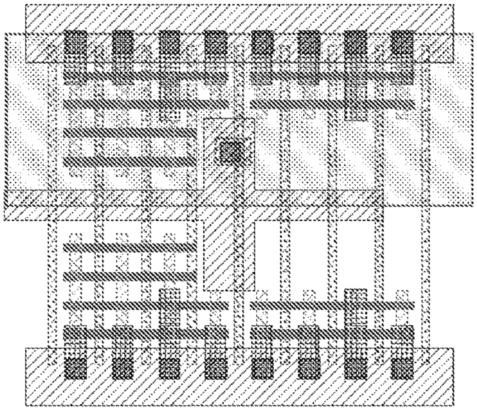
Figure 284B:
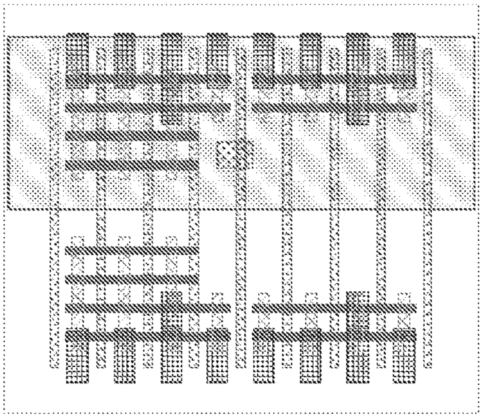
Figure 284C:
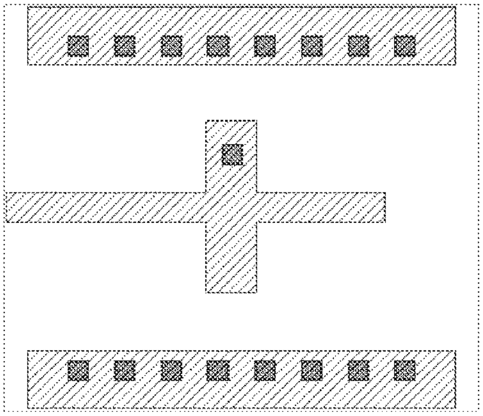
Figure 285A:
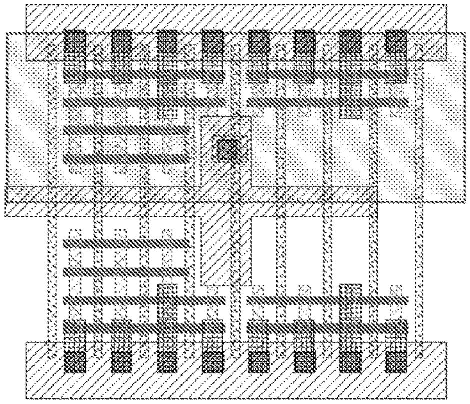
Figure 285B:
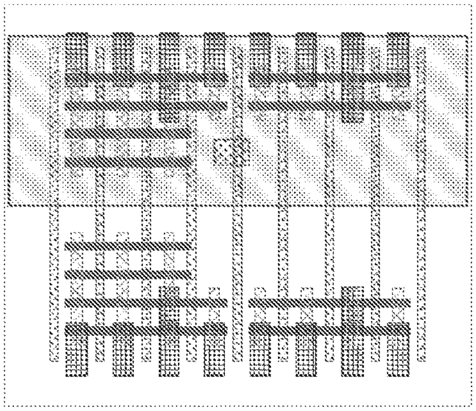
Figure 285C:
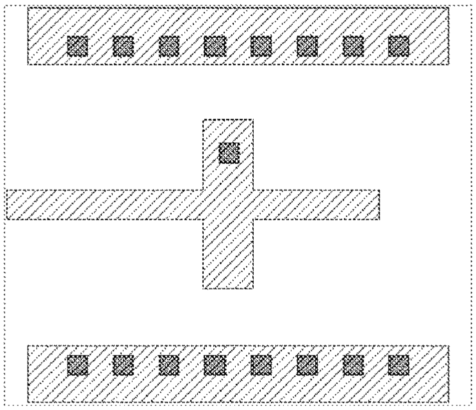
Figure 286A:
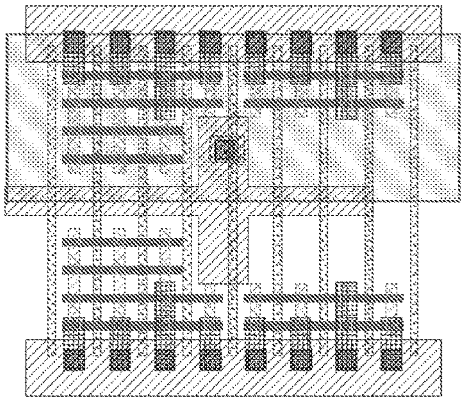
Figure 286B:
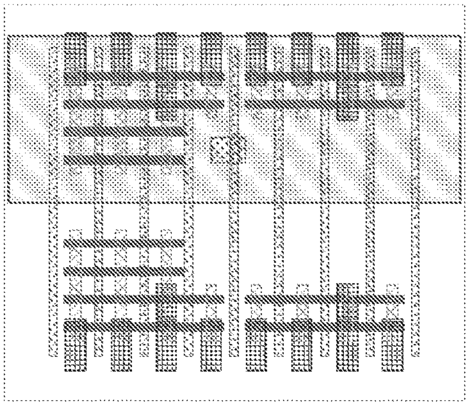
Figure 286C:
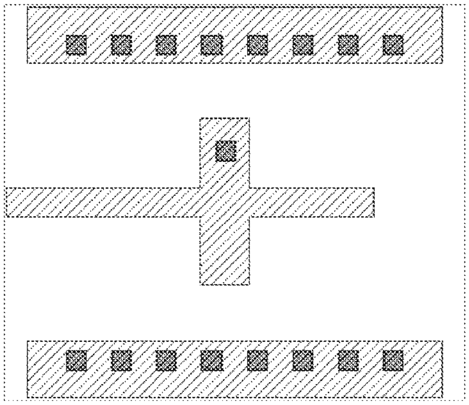
Figure 287A:
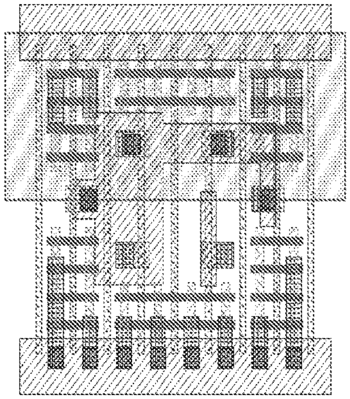
Figure 287B:
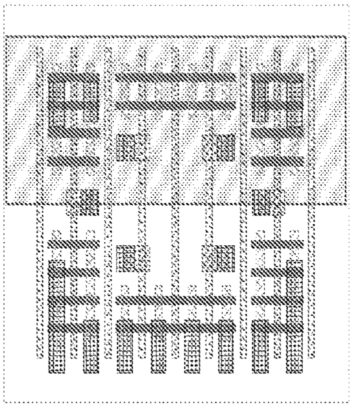
Figure 287C:
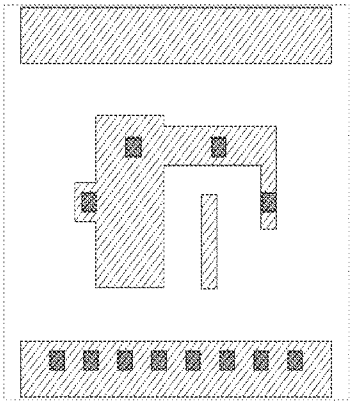
Figure 288A:
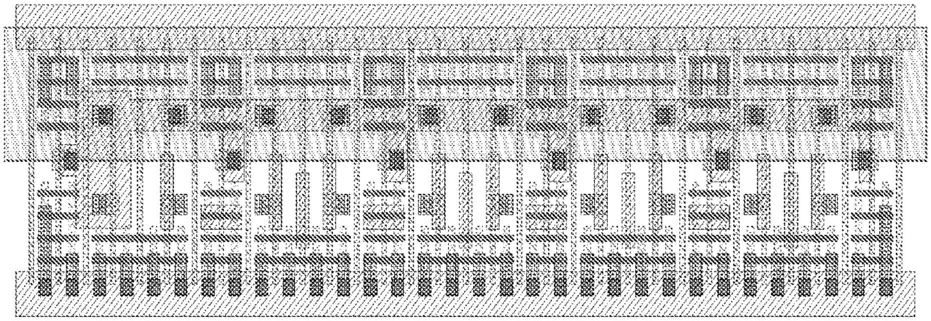
Figure 288B:
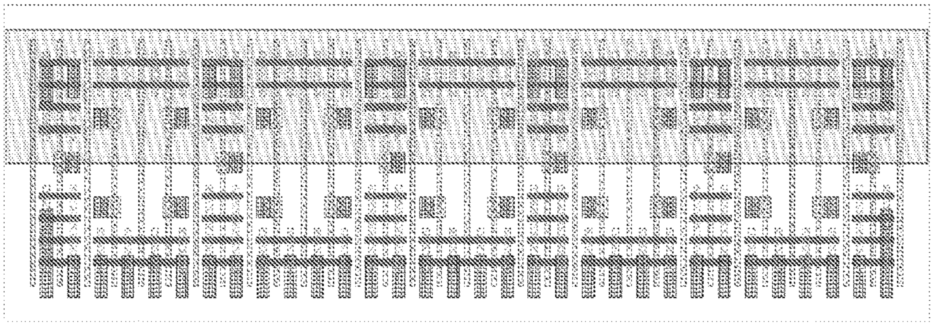
Figure 288C:
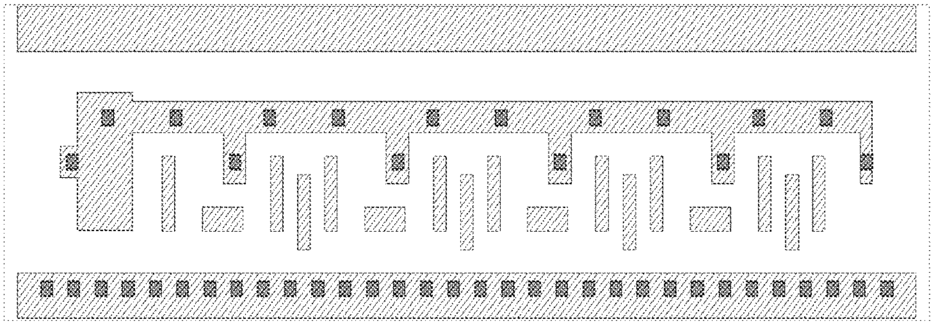
Figure 289A:
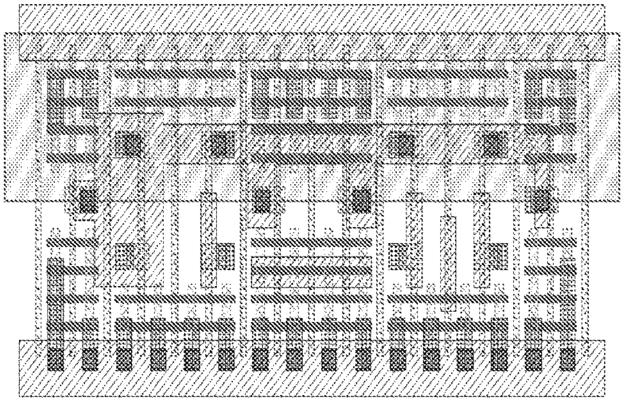
Figure 289B:
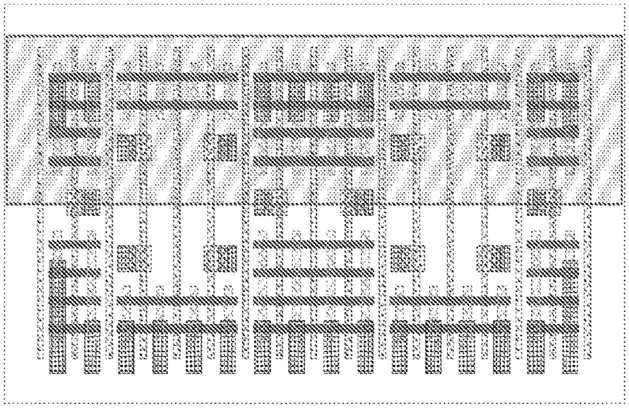
Figure 289C:
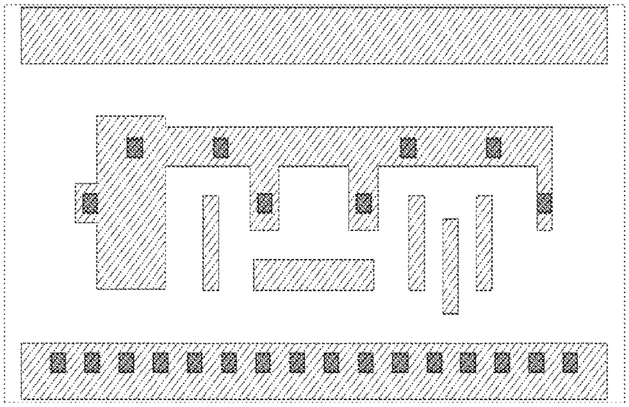
Figure 290A:
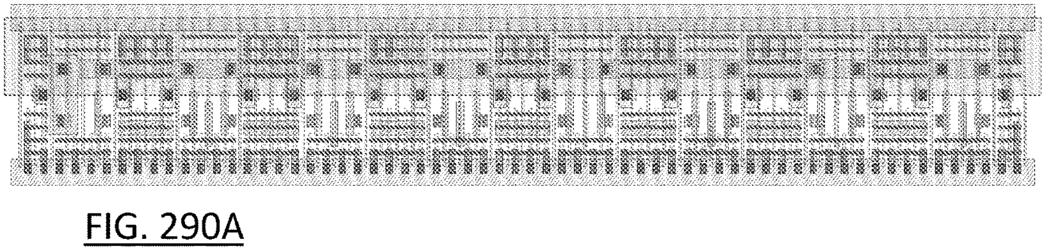
Figure 290B:
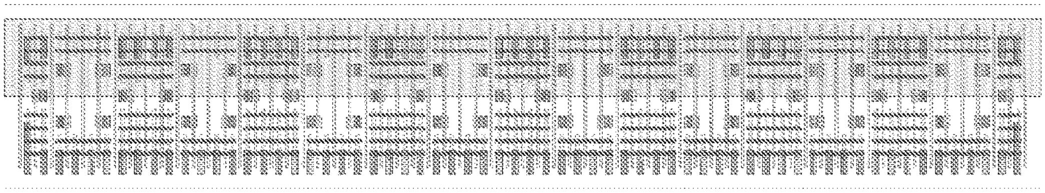
Figure 290C:
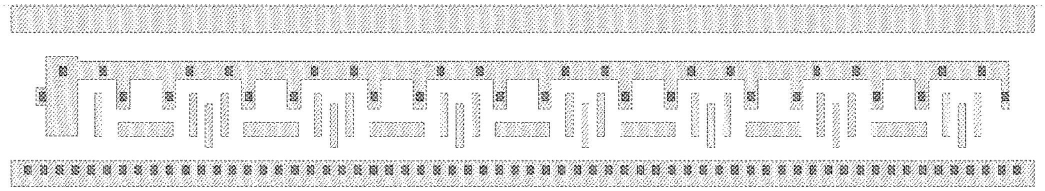
Figure 291A:
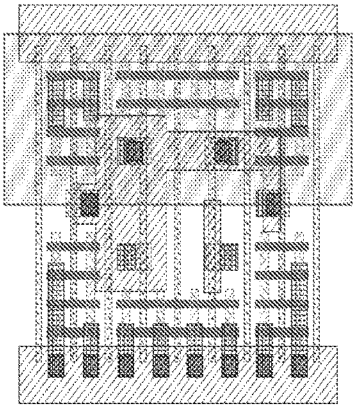
Figure 291B:
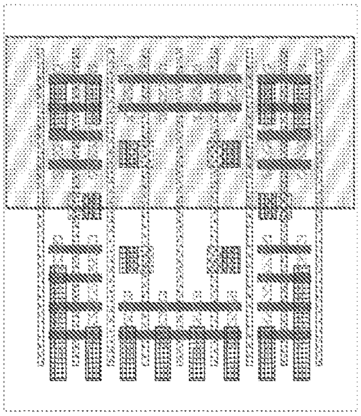
Figure 291C:
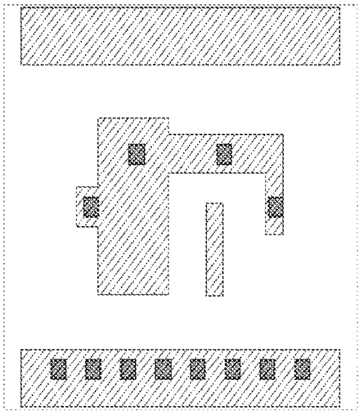
Figure 292A:
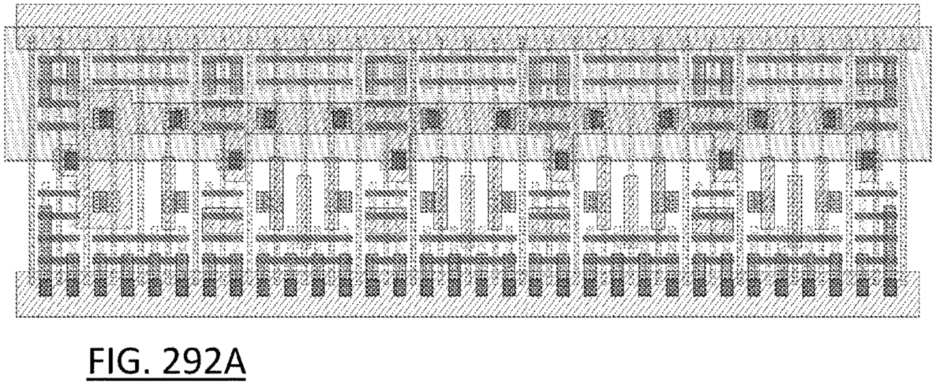
Figure 292B:
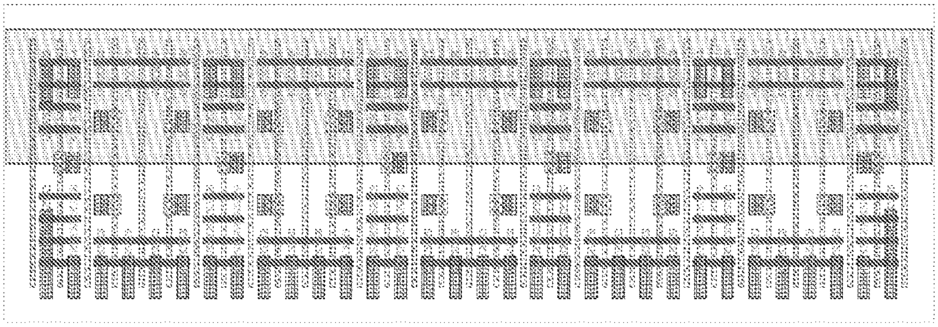
Figure 292C:
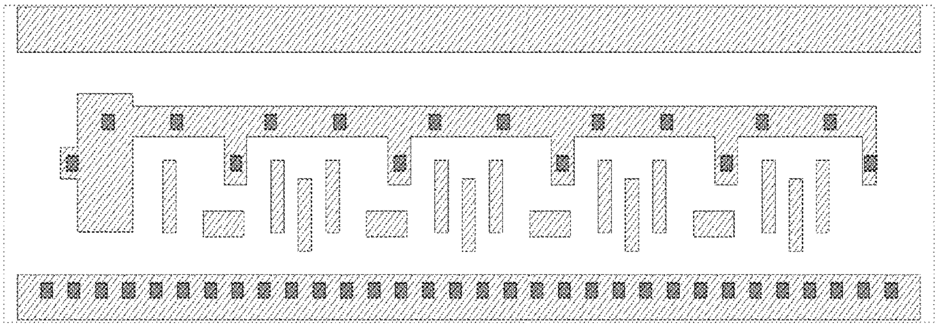
Figure 293A:
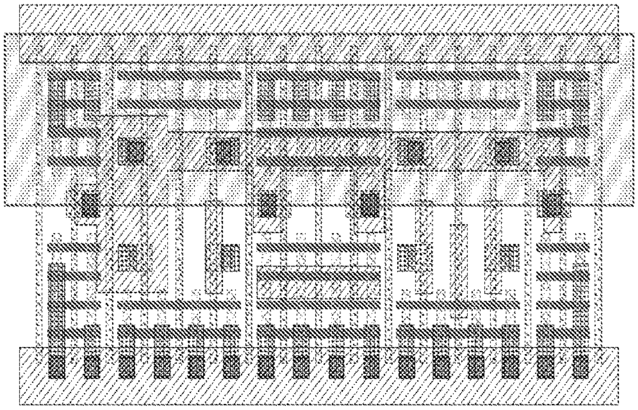
Figure 293B:
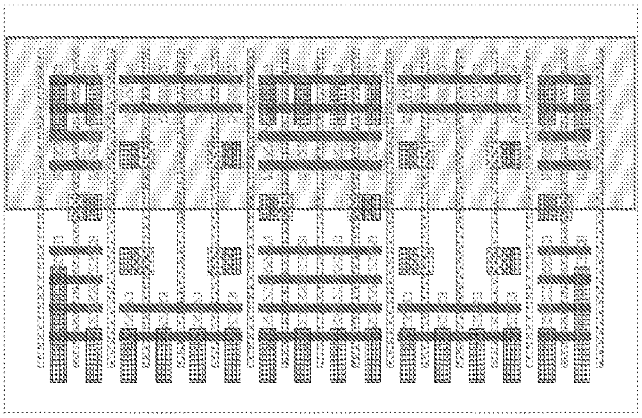
Figure 293C:
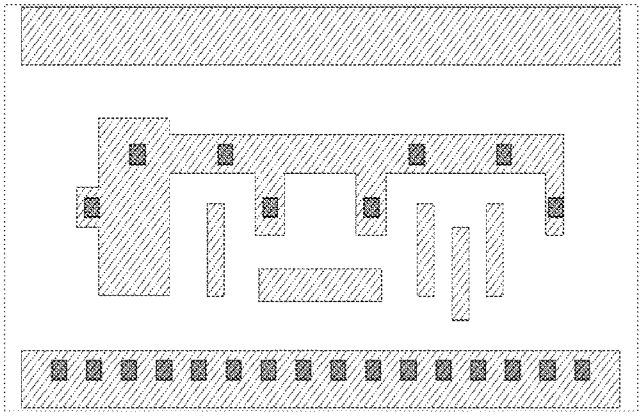
Figure 294A:
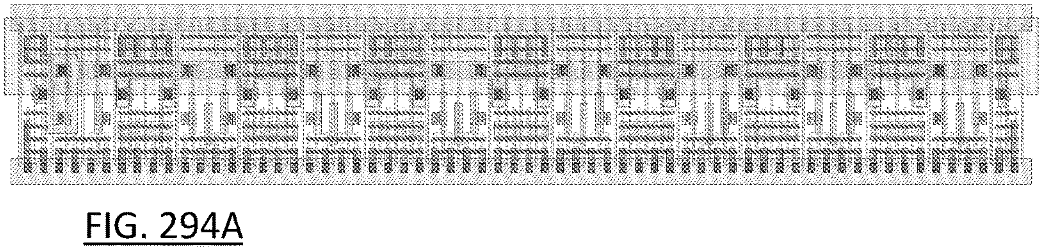
Figure 294B:
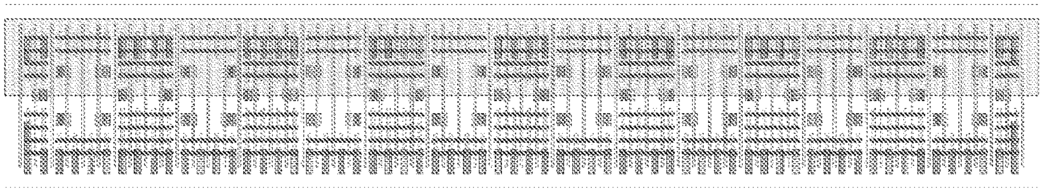
Figure 294C:
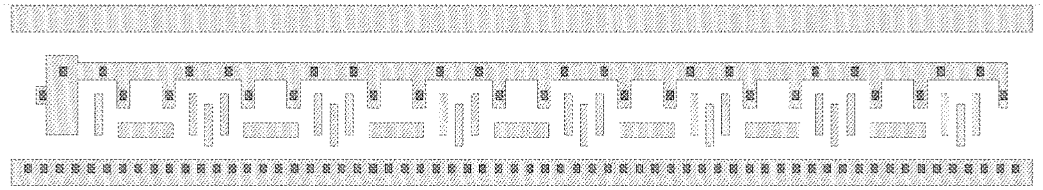
Figure 295A:
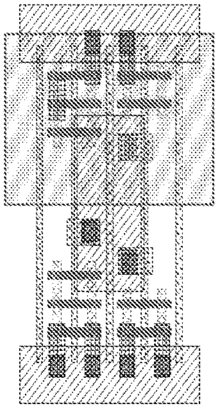
Figure 295B:
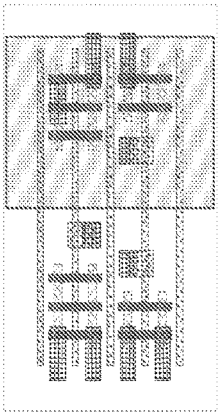
Figure 295C:
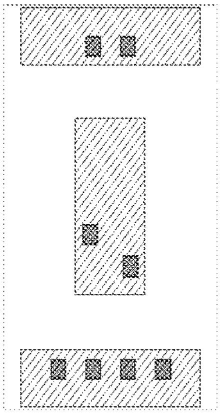
Figure 296A:
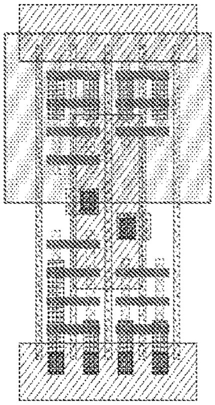
Figure 296B:
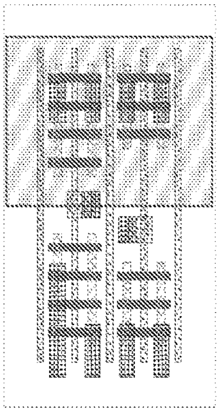
Figure 296C:
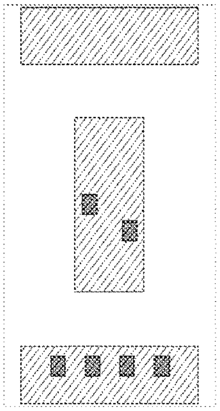
Figure 297A:
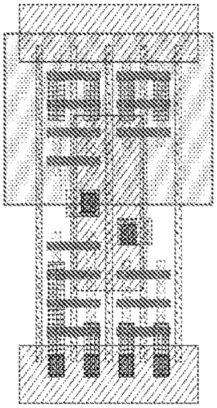
Figure 297B:
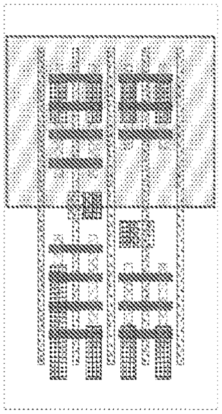
Figure 297C:
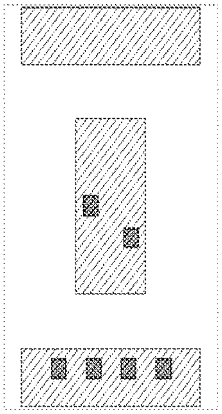
Figure 298A:
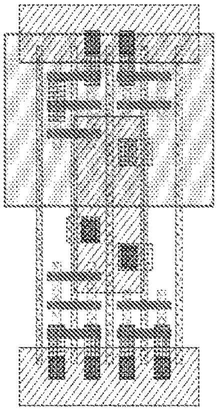
Figure 298B:
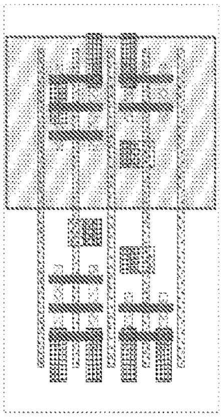
Figure 298C:
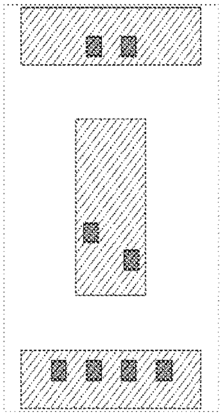
Figure 299A:
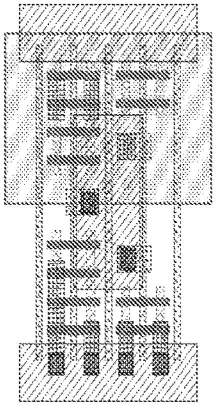
Figure 299B:
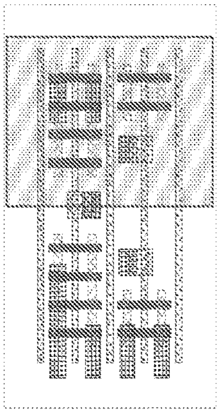
Figure 299C:
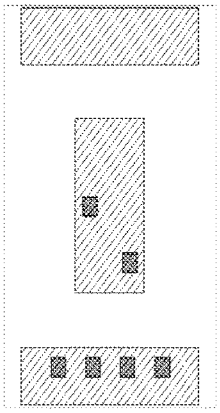
Figure 300A:
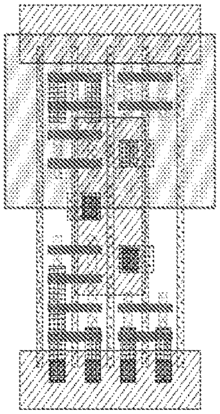
Figure 300B:
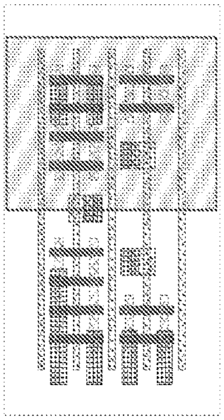
Figure 300C:
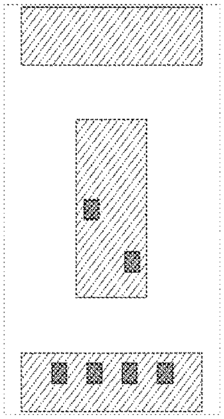
Figure 301A:
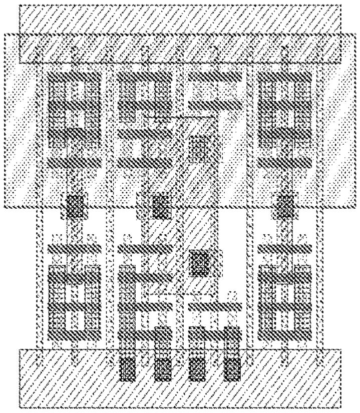
Figure 301B:
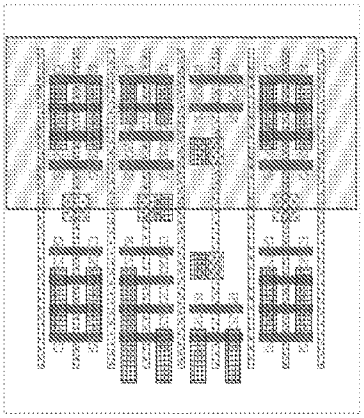
Figure 301C:
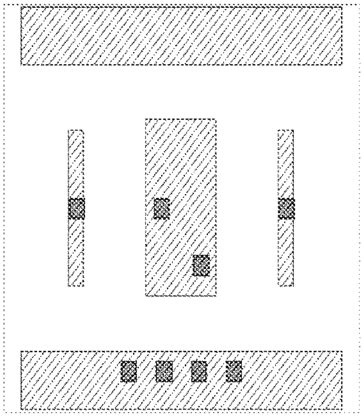
Figure 302A:
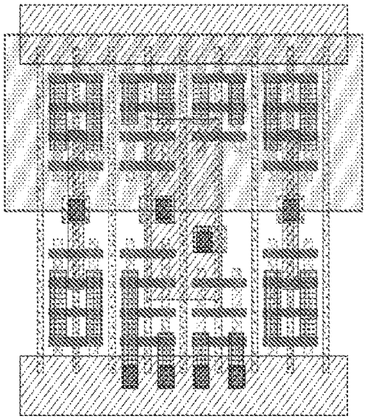
Figure 302B:
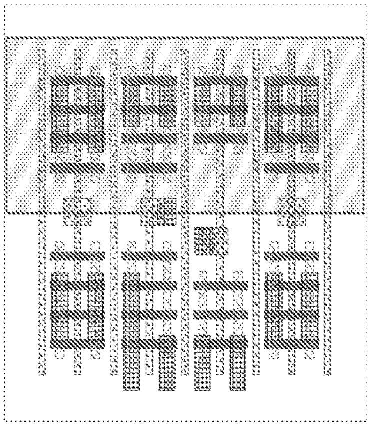
Figure 302C:
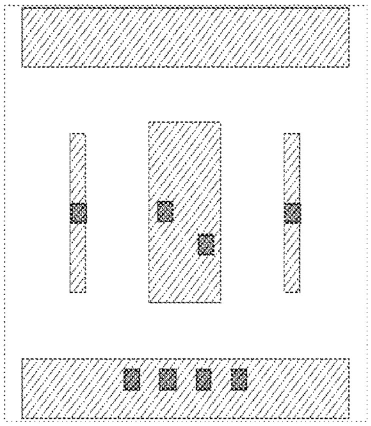
Figure 303A:
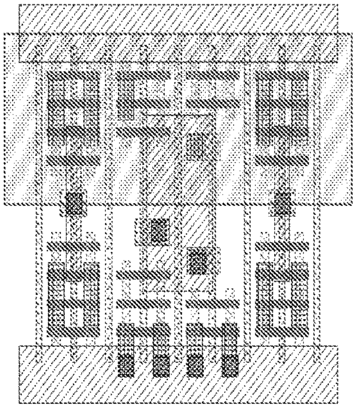
Figure 303B:
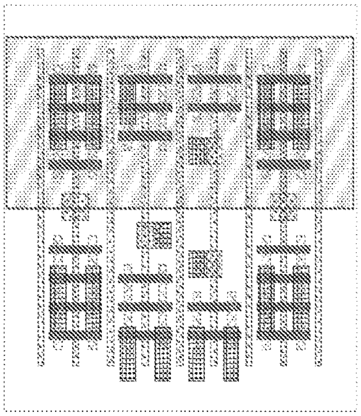
Figure 303C:
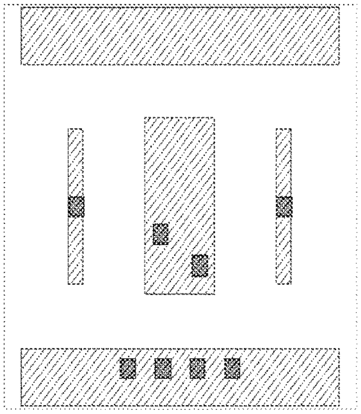
Figure 304A:
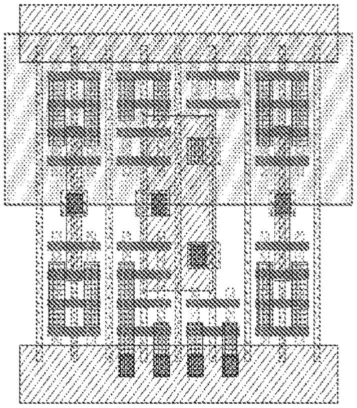
Figure 304B:
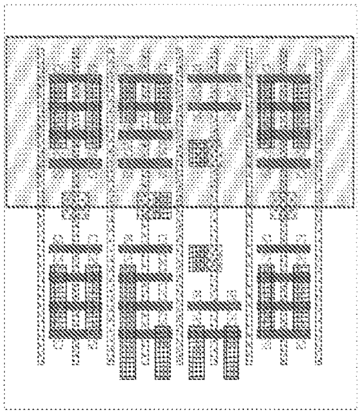
Figure 304C:
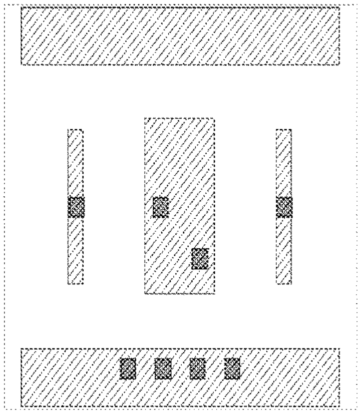
Figure 305A:
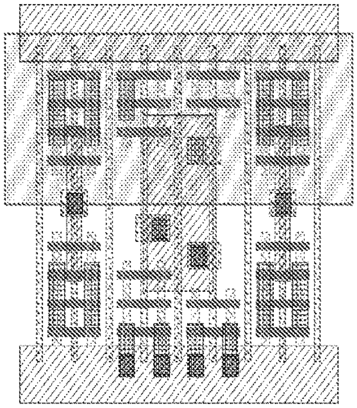
Figure 305B:
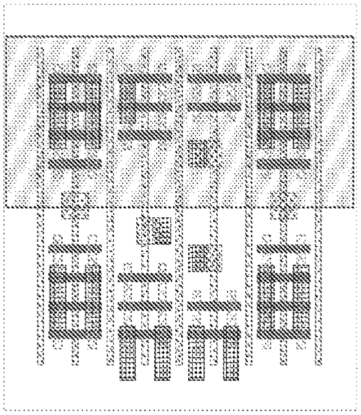
Figure 305C:
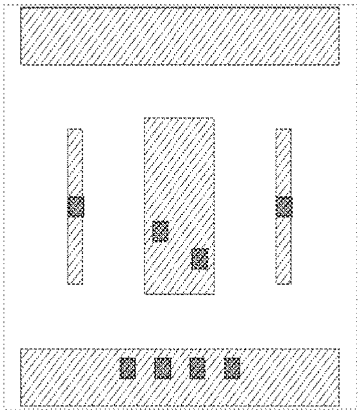
Figure 306A:
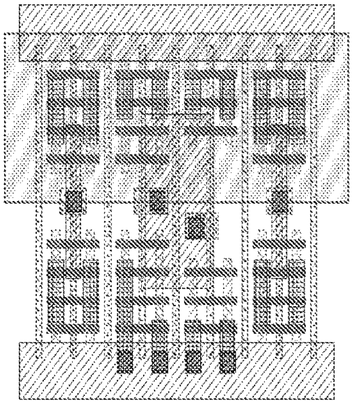
Figure 306B:
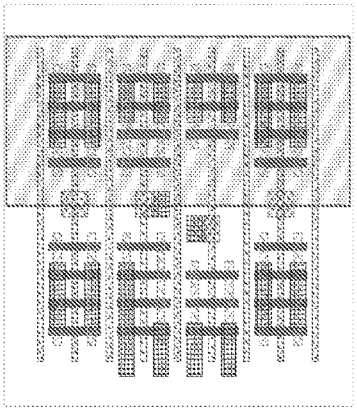
Figure 306C:
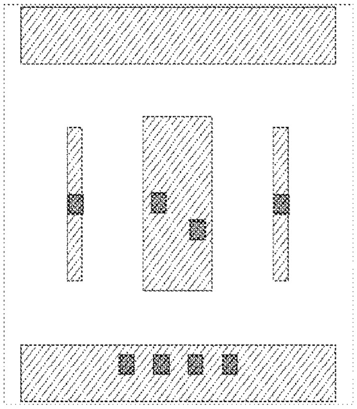
Figure 307A:
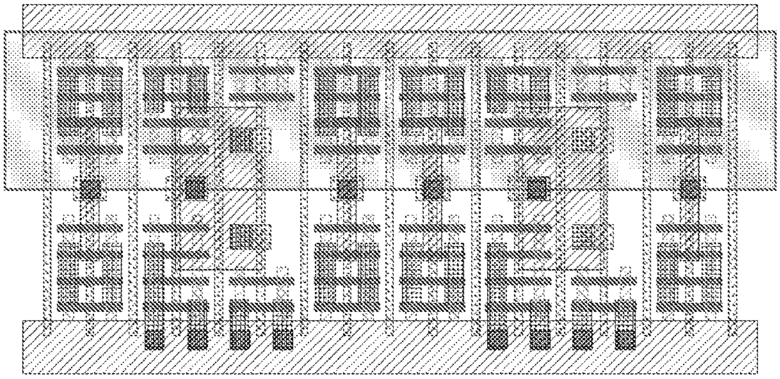
Figure 307B:
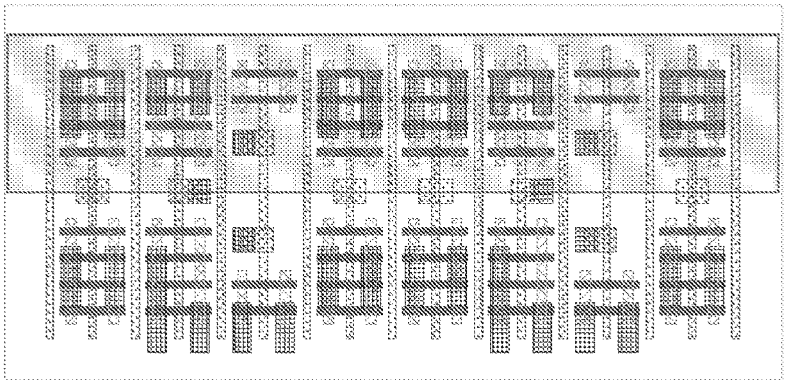
Figure 307C:
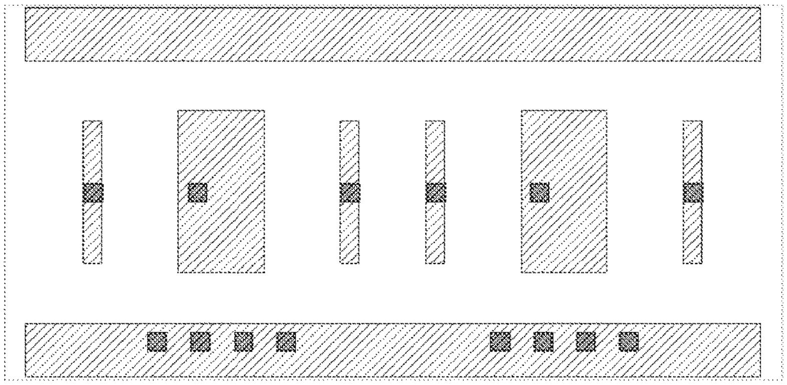
Figure 308A:
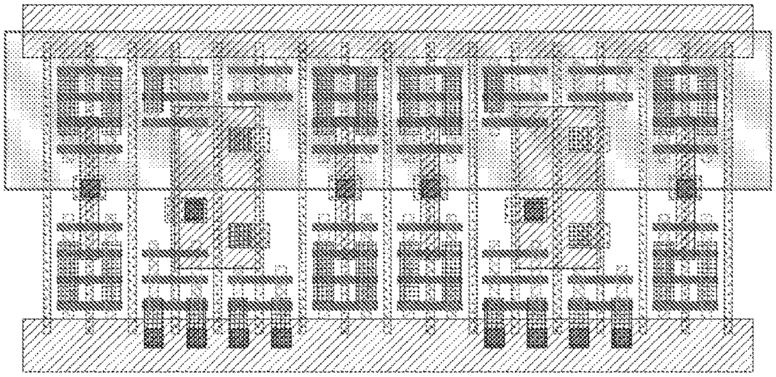
Figure 308B:
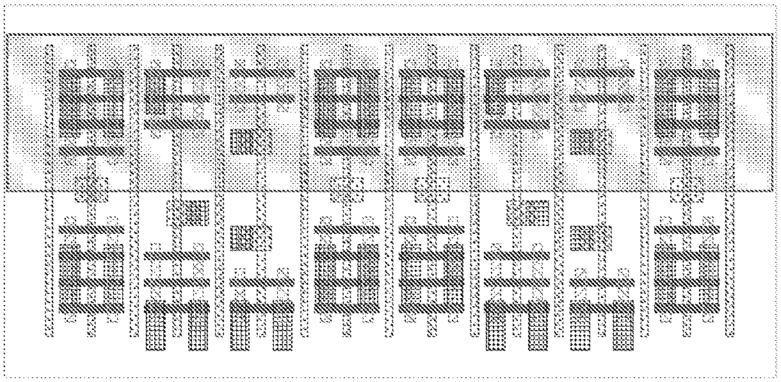
Figure 308C:
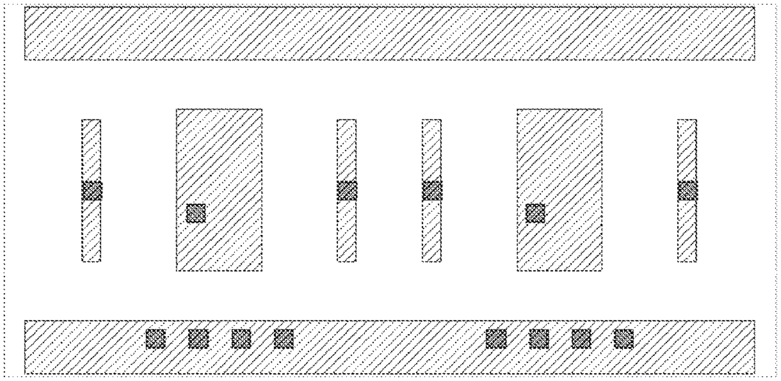
Figure 309A:
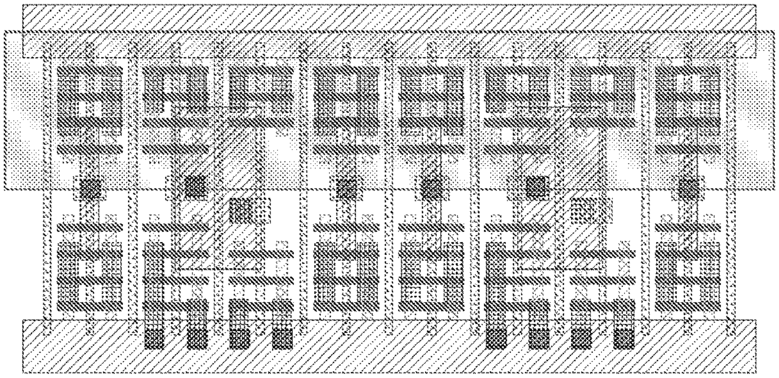
Figure 309B:
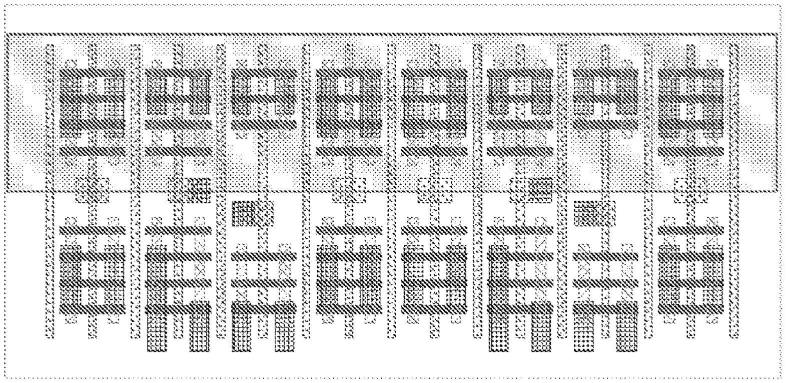
Figure 309C:
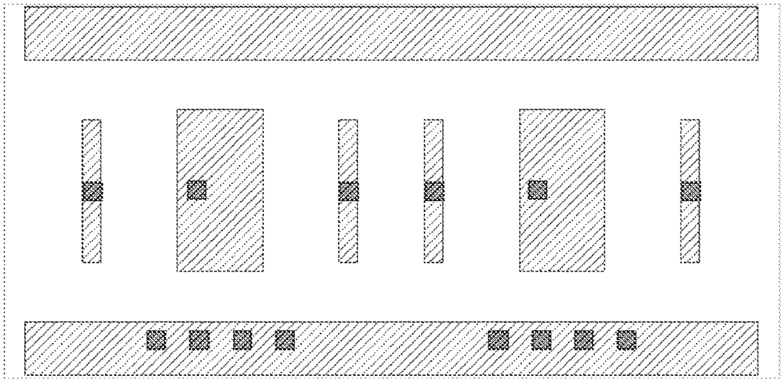
Figure 310A:
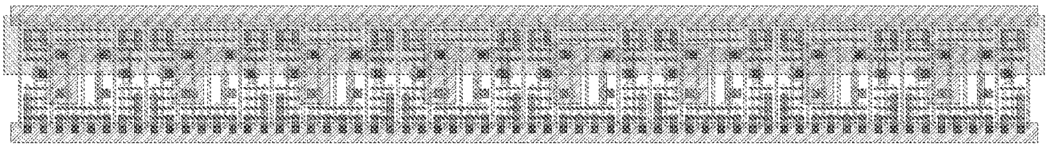
Figure 310B:
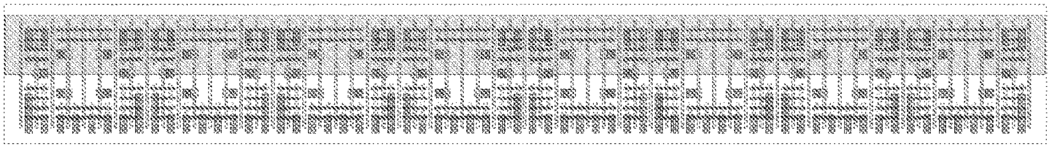
Figure 310C:
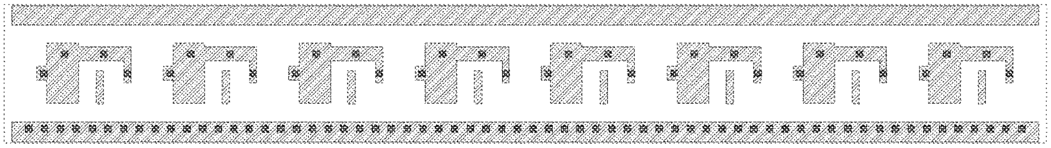
Figure 311A:
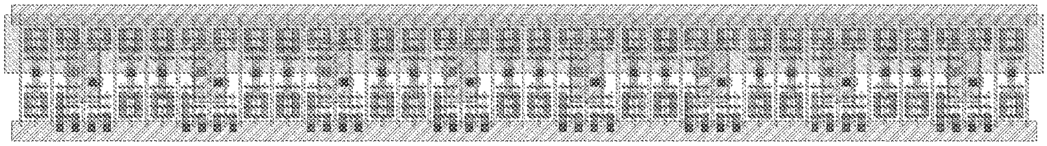
Figure 311B:
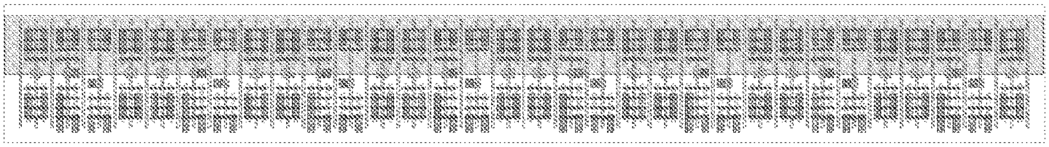
Figure 311C:
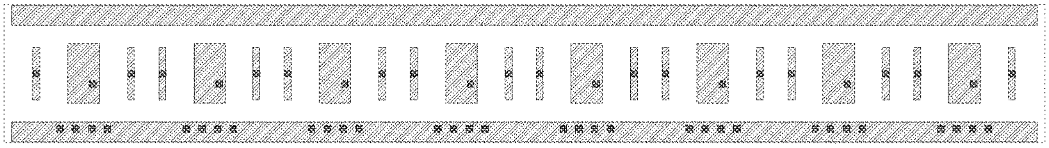
Figure 312A:
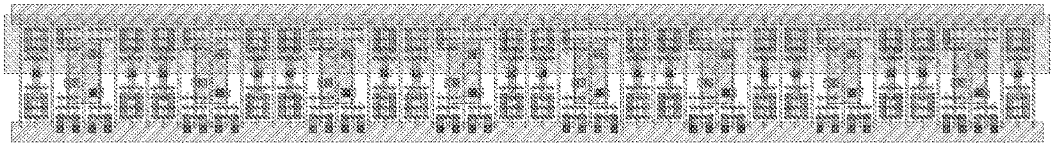
Figure 312B:
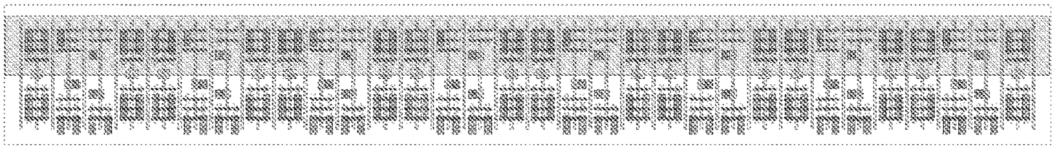
Figure 312C:
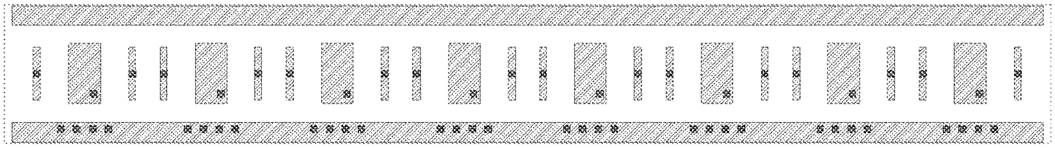
Figure 313A:
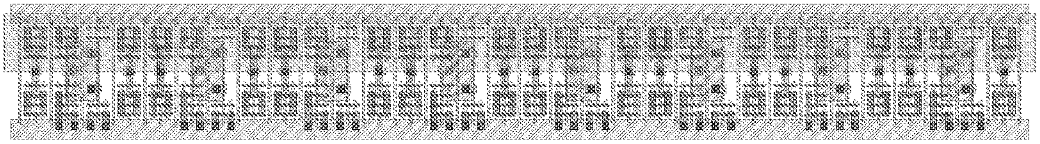
Figure 313B:
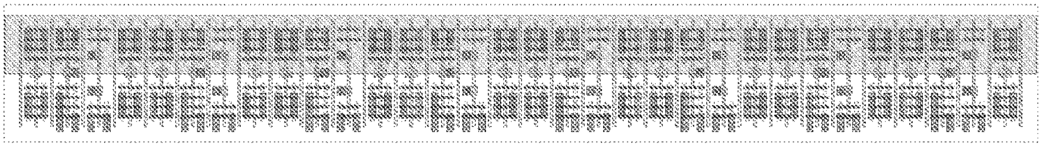
Figure 313C:
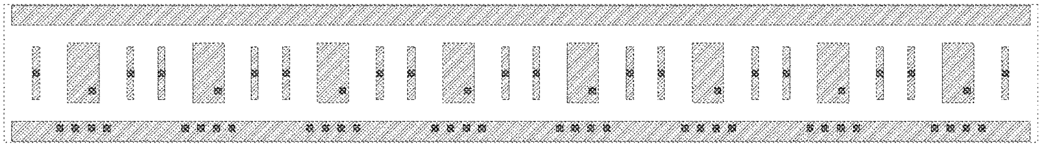
Figure 314A:
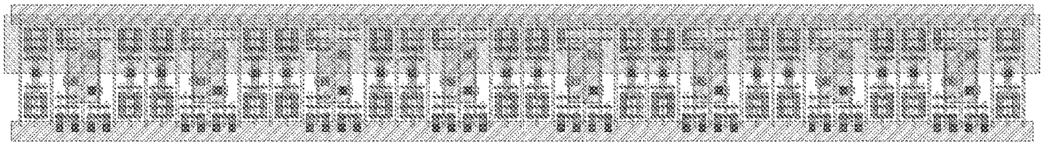
Figure 314B:
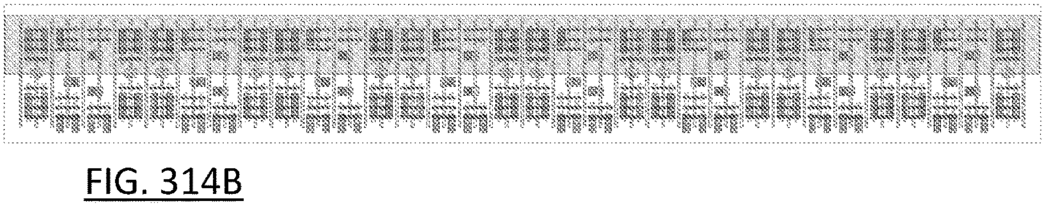
Figure 314C:
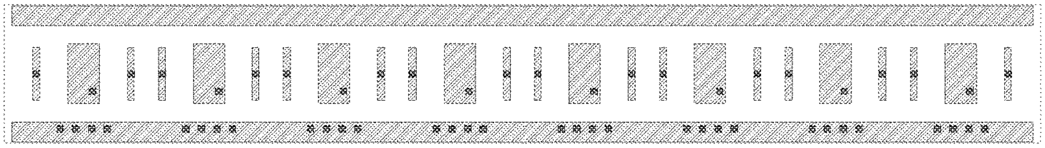
Figure 315A:
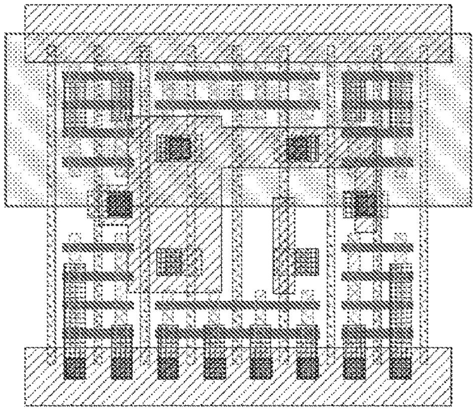
Figure 315B:
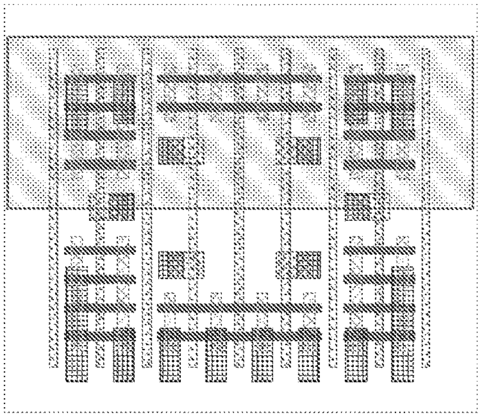
Figure 315C:
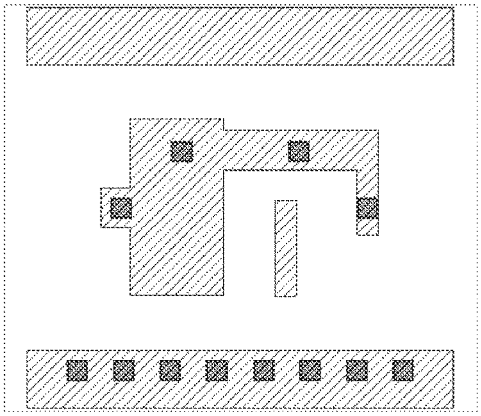
Figure 316A:
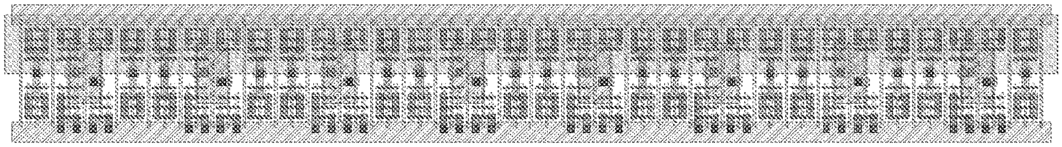
Figure 316B:
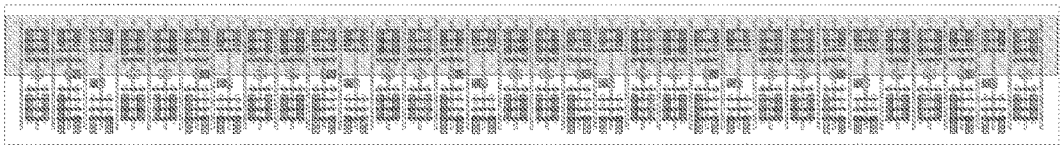
Figure 316C:
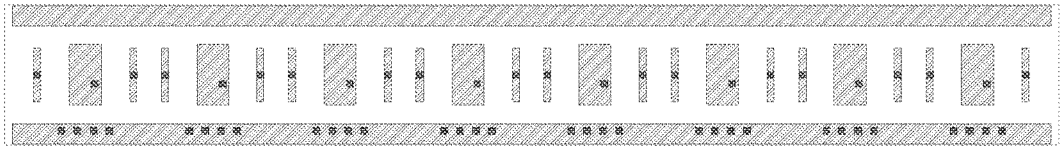
Figure 317A:
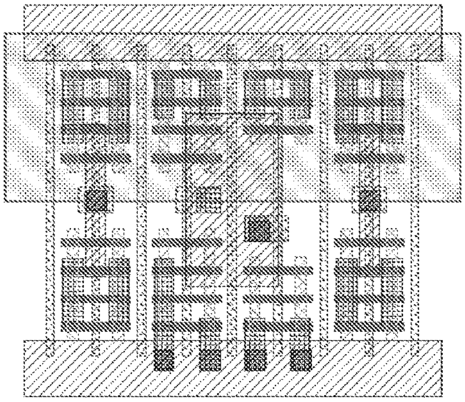
Figure 317B:
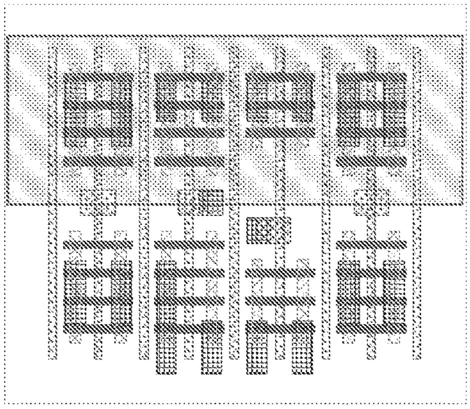
Figure 317C:
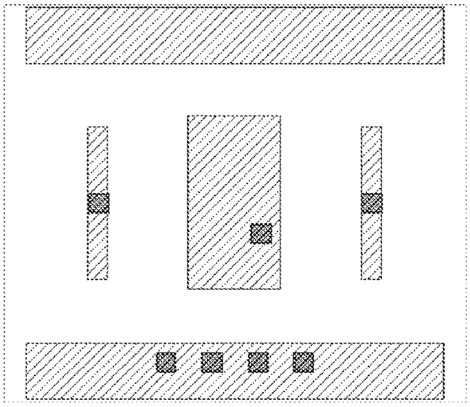
Figure 318A:
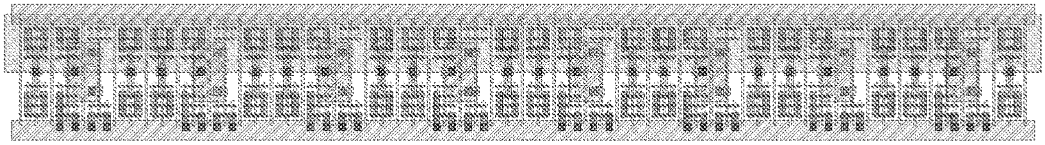
Figure 318B:
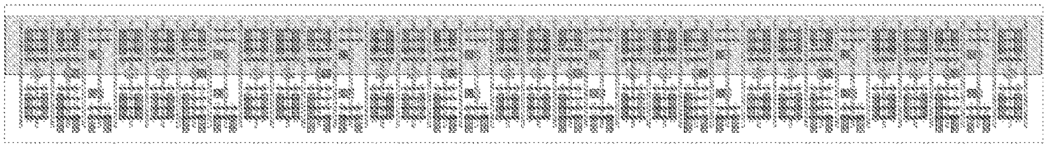
Figure 318C:
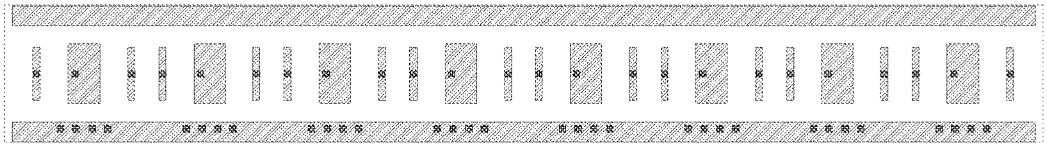
Figure 319A:
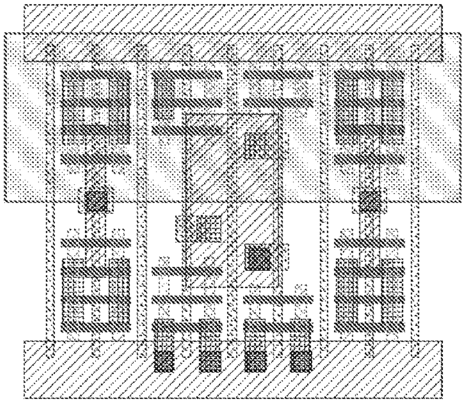
Figure 319B:
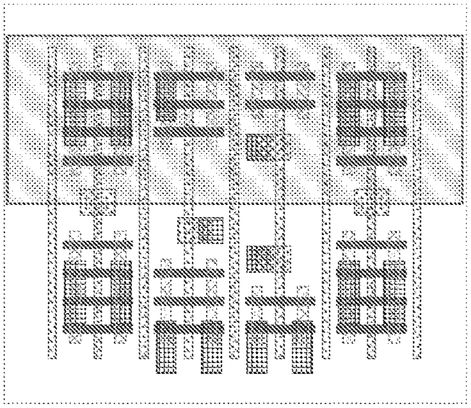
Figure 319C:
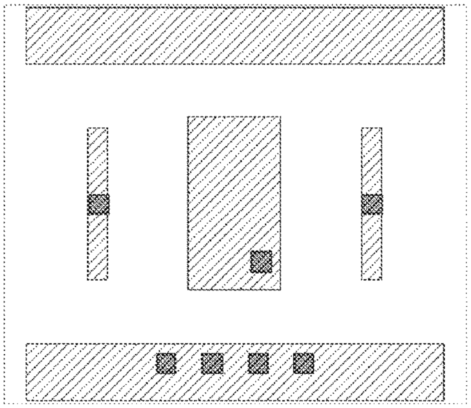
Figure 320A:
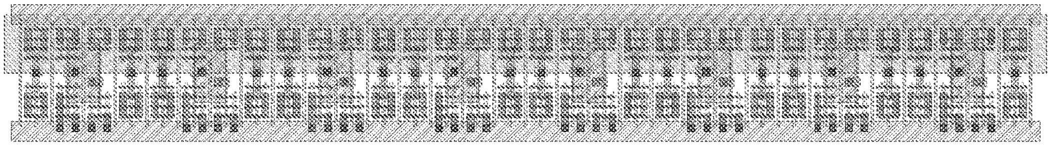
Figure 320B:
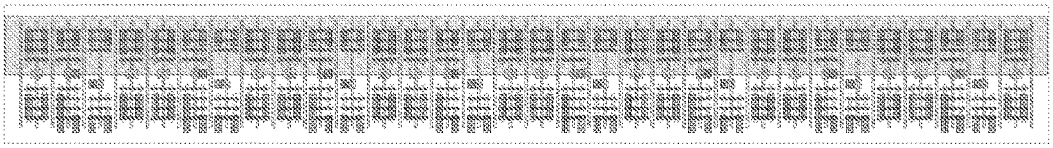
Figure 320C:
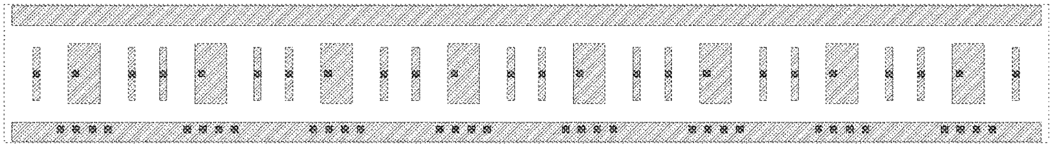
Figure 321A:
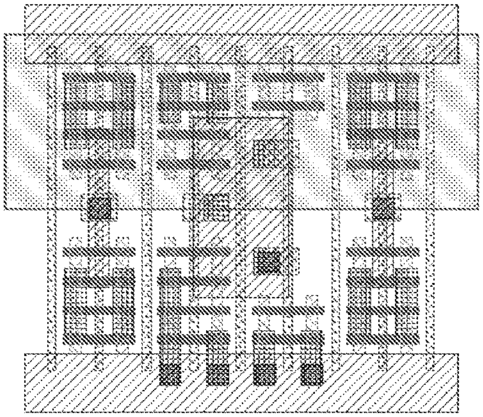
Figure 321B:
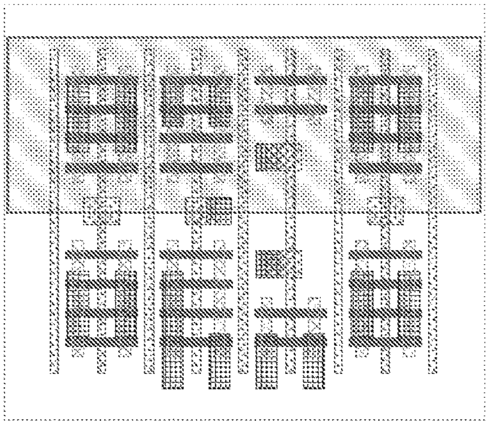
Figure 321C:
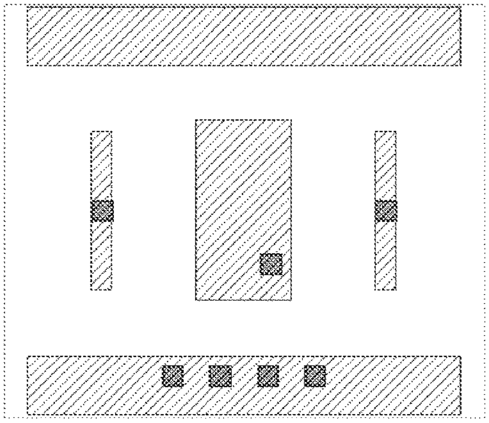
Figure 322A:
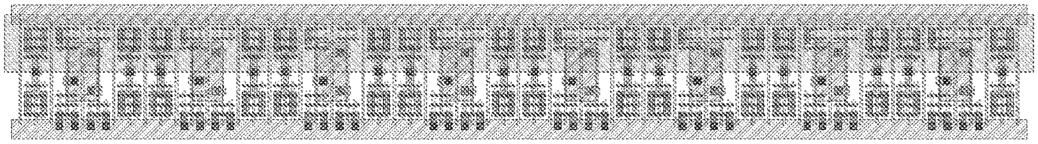
Figure 322B:
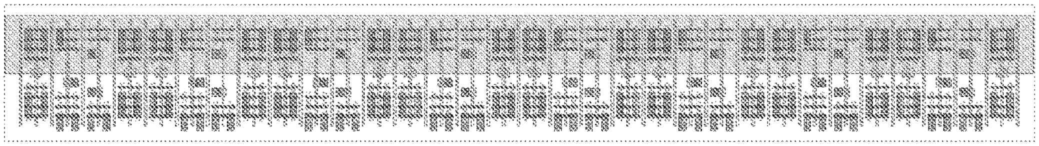
Figure 322C:
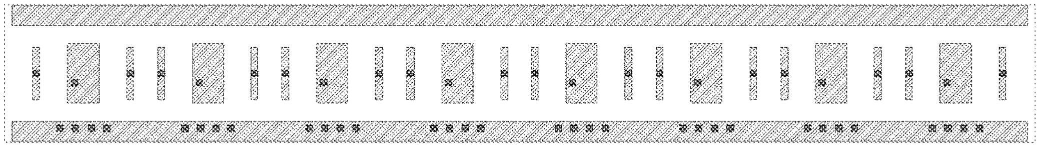
Figure 323A:
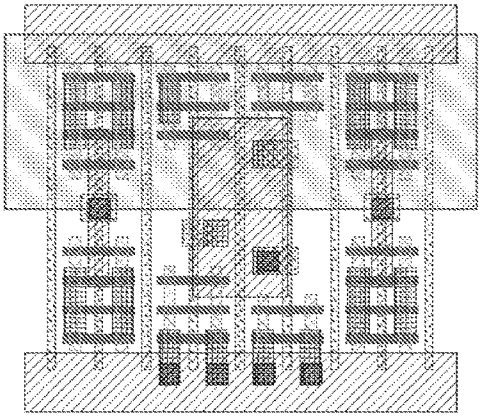
Figure 323B:
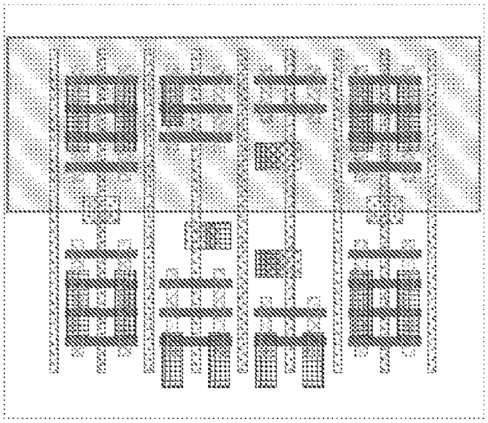
Figure 323C:
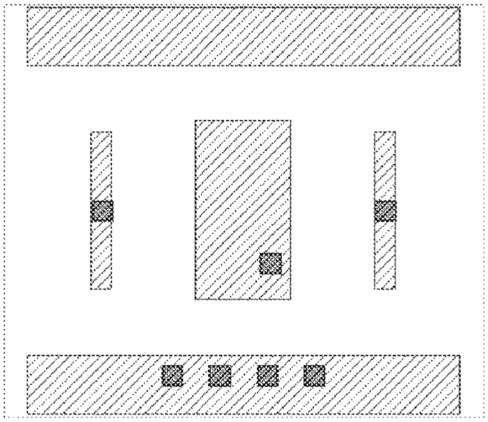
Figure 324A:
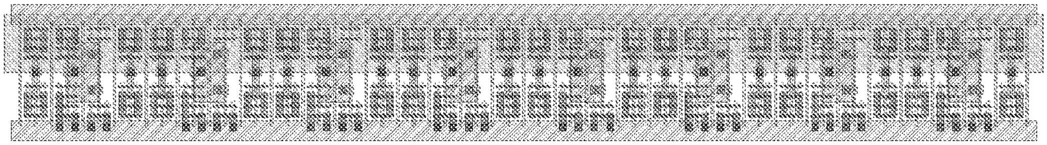
Figure 324B:
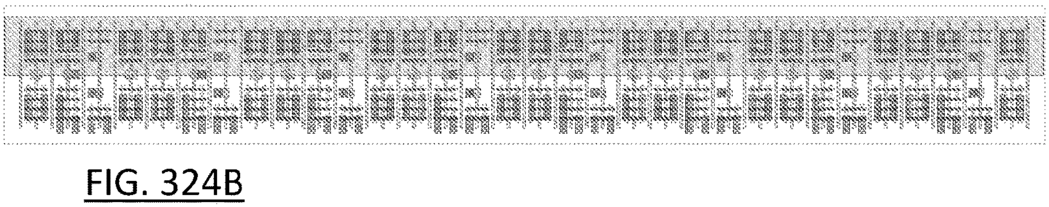
Figure 324C:
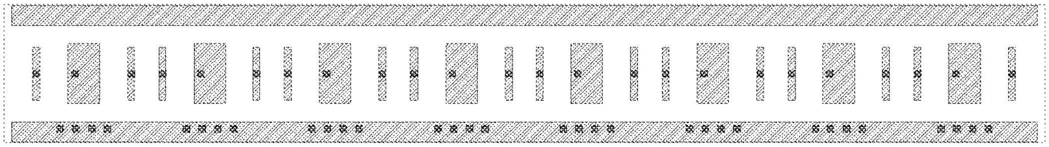
Figure 325A:
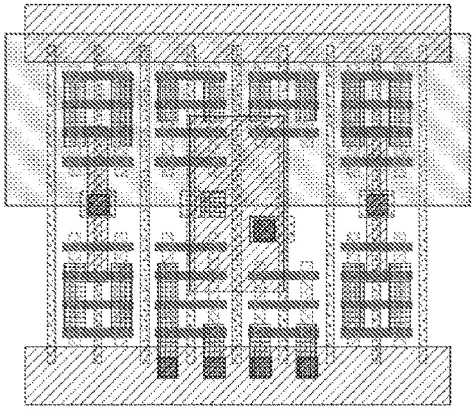
Figure 325B:
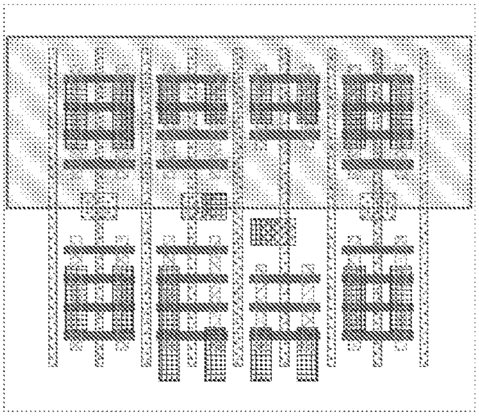
Figure 325C:
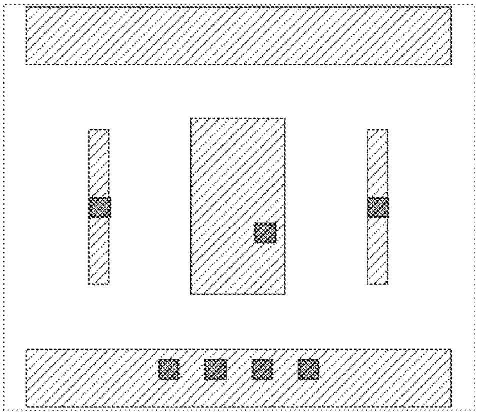
Figure 326A:
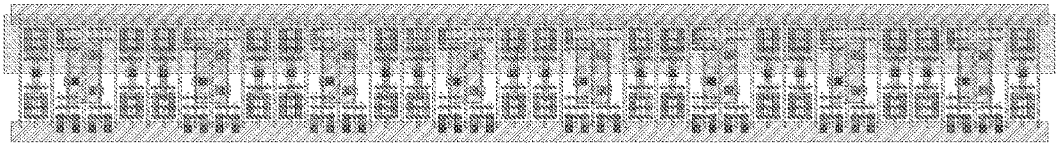
Figure 326B:
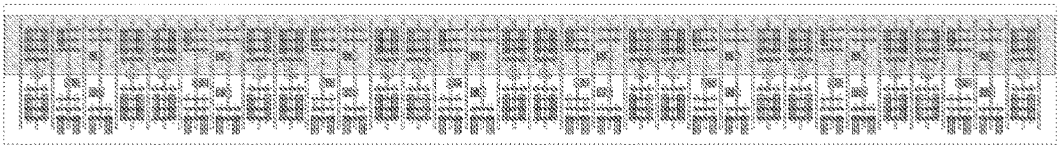
Figure 326C:
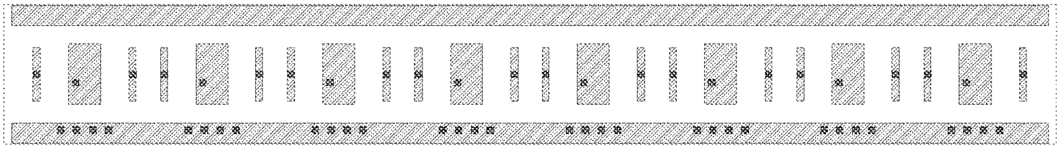
Figure 327A:
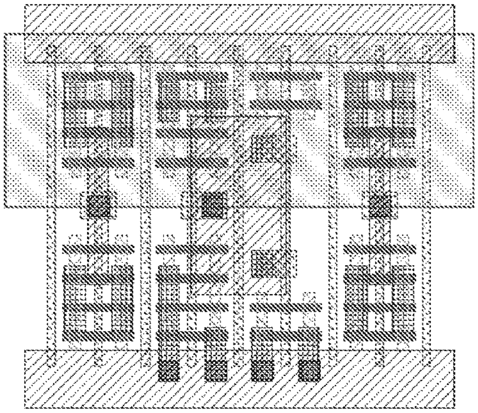
Figure 327B:
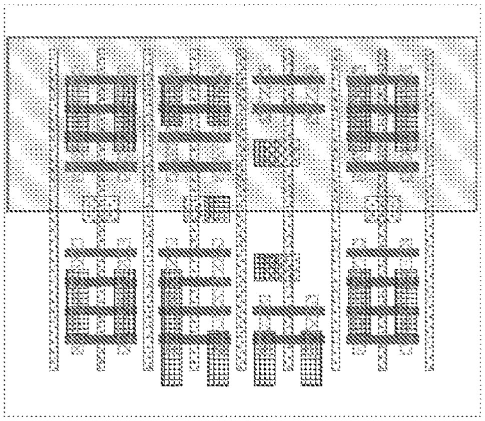
Figure 327C:
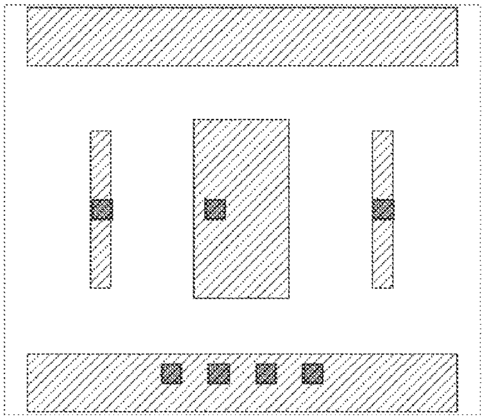
Figure 328A:
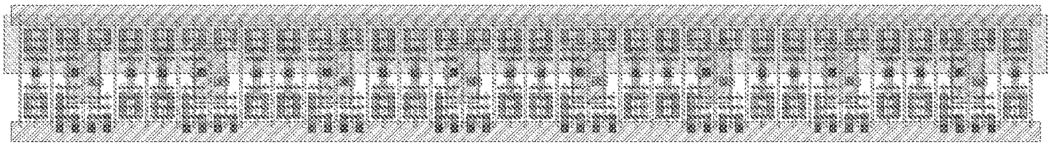
Figure 328B:
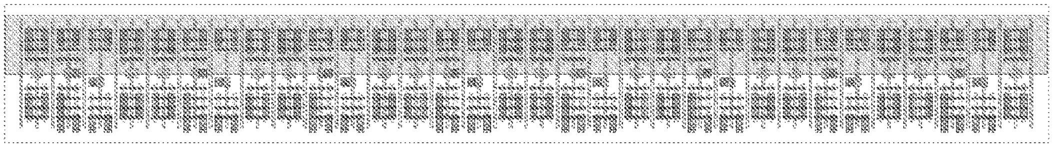
Figure 328C:
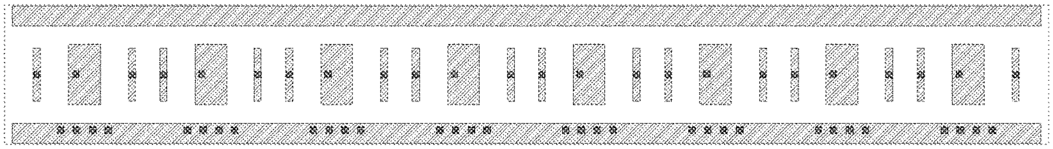
Figure 329A:
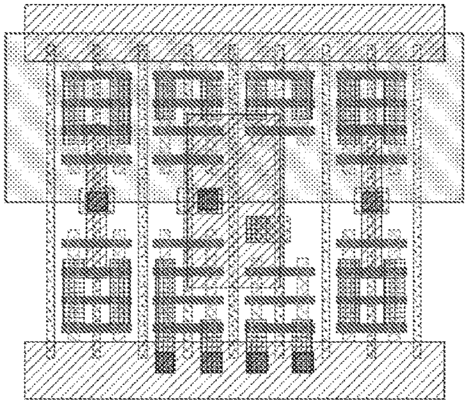
Figure 329B:
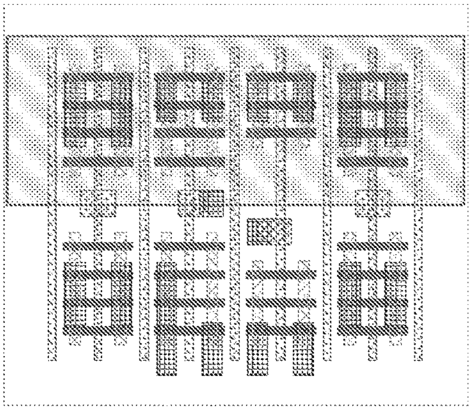
Figure 329C:
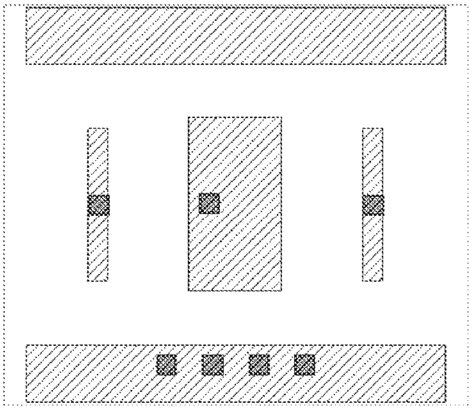
Figure 330A:
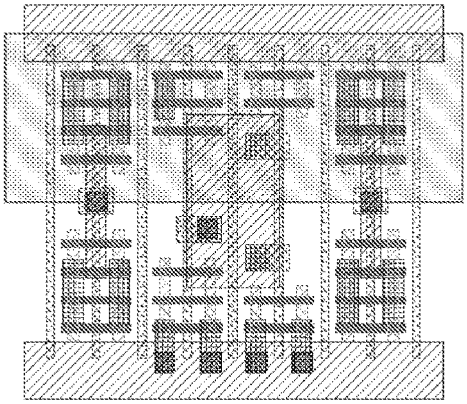
Figure 330B:
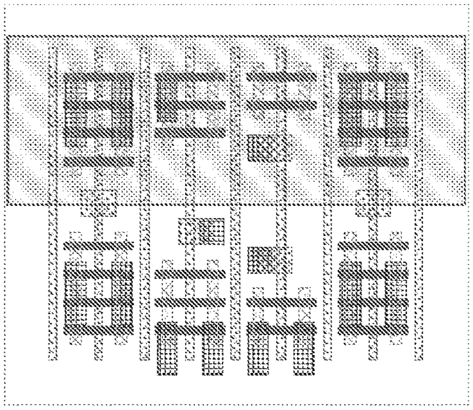
Figure 330C:
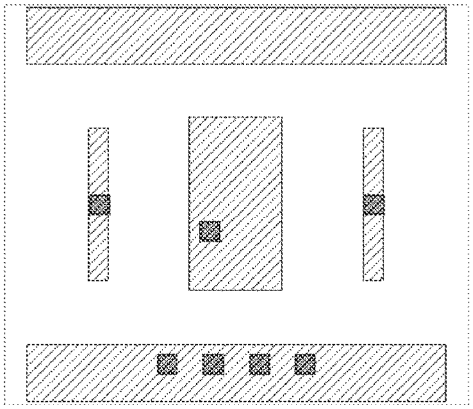
Figure 331A:
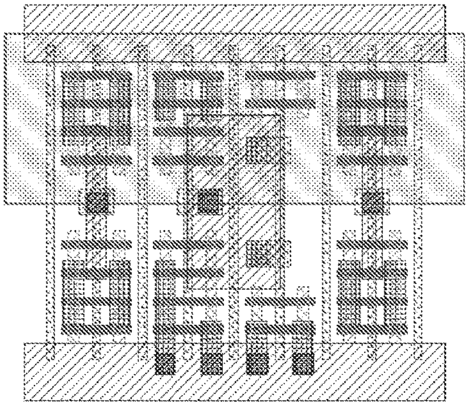
Figure 331B:
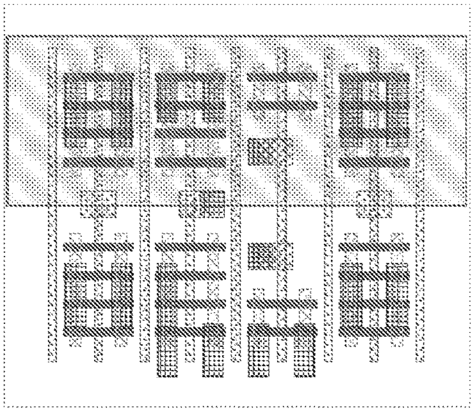
Figure 331C:
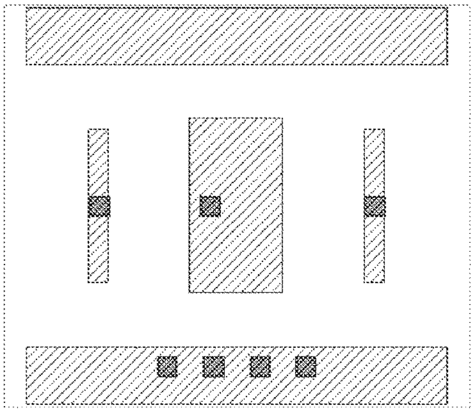
Figure 332A:
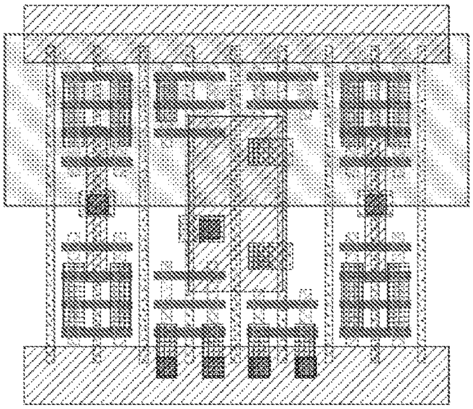
Figure 332B:
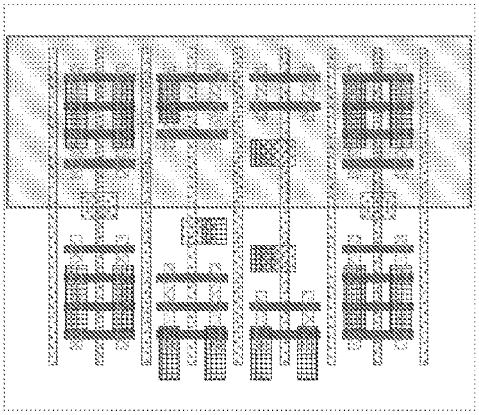
Figure 332C:
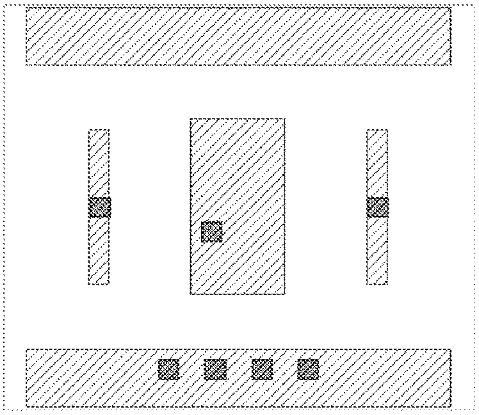
Figure 333A:
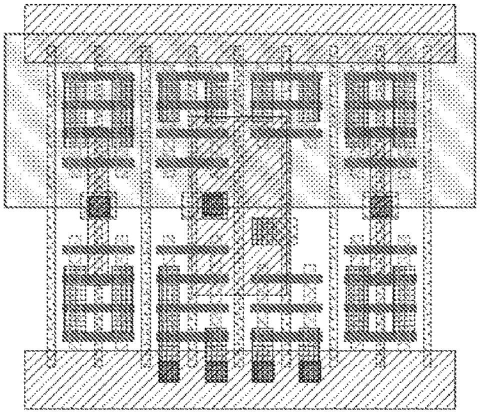
Figure 333B:
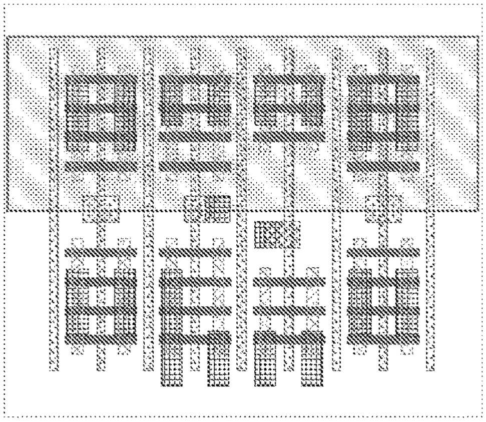
Figure 333C:
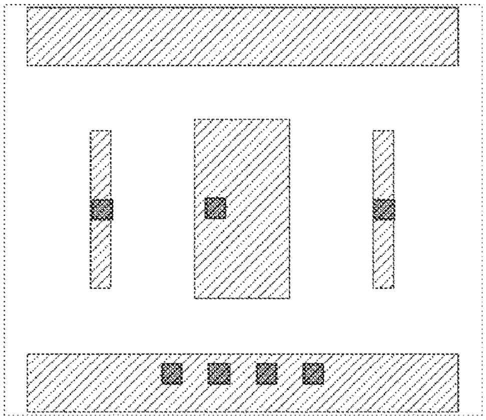
Figure 334A:
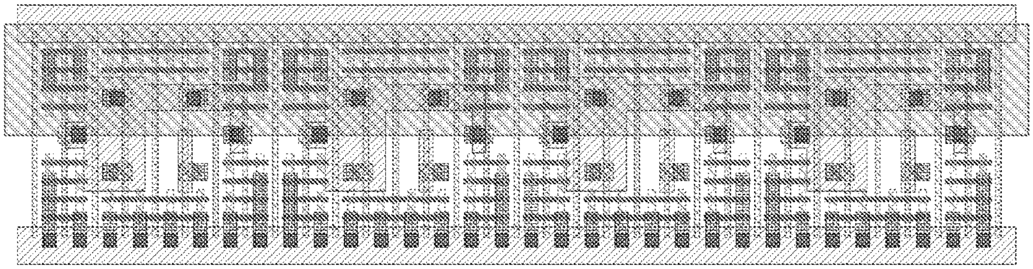
Figure 334B:
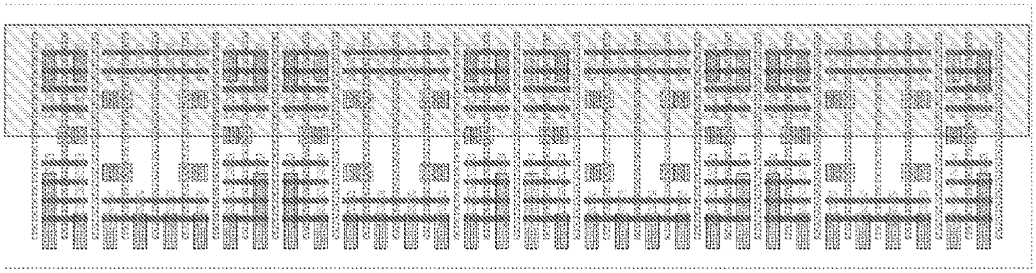
Figure 334C:
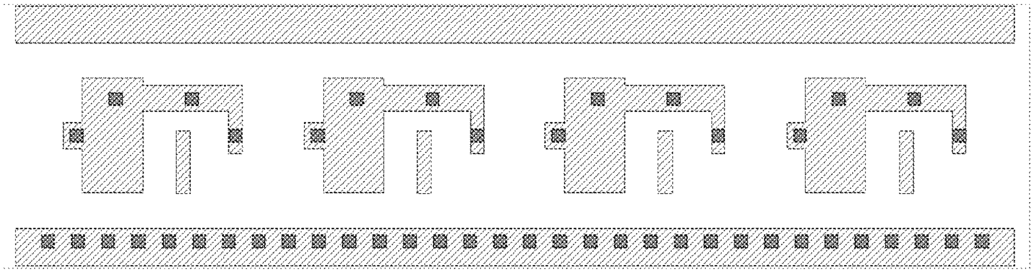
Figure 335A:
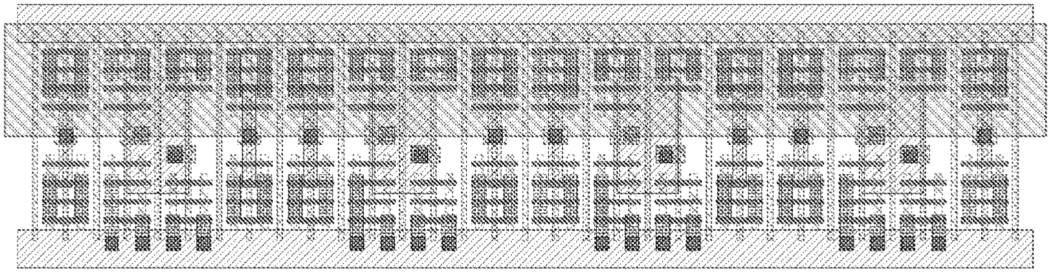
Figure 335B:
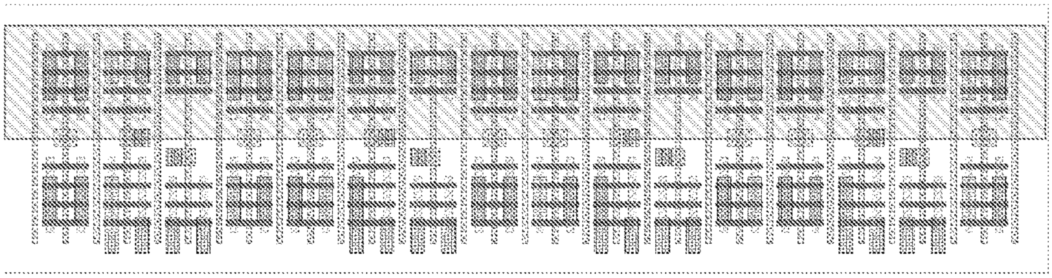
Figure 335C:
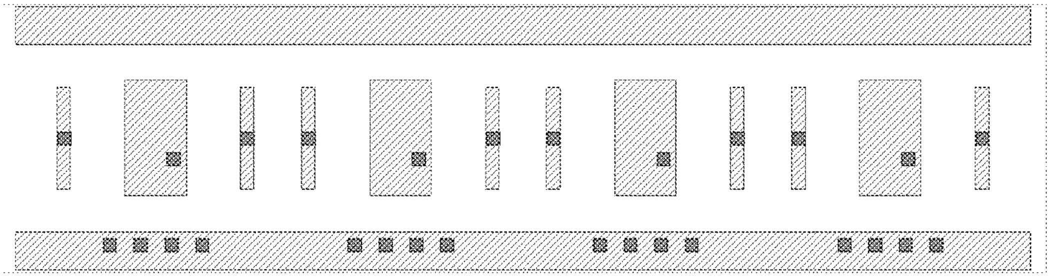
Figure 336A:
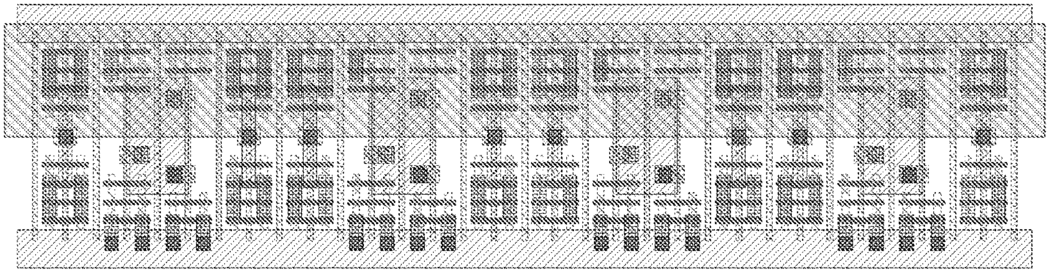
Figure 336B:
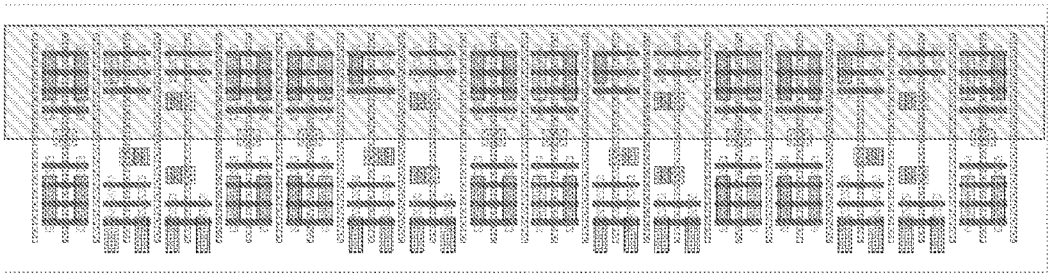
Figure 336C:
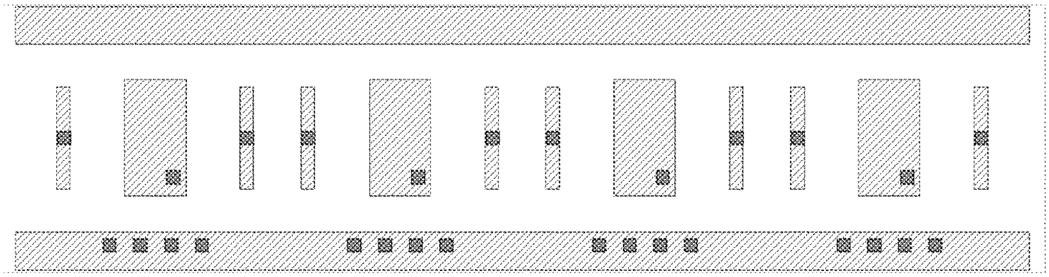
Figure 337A:
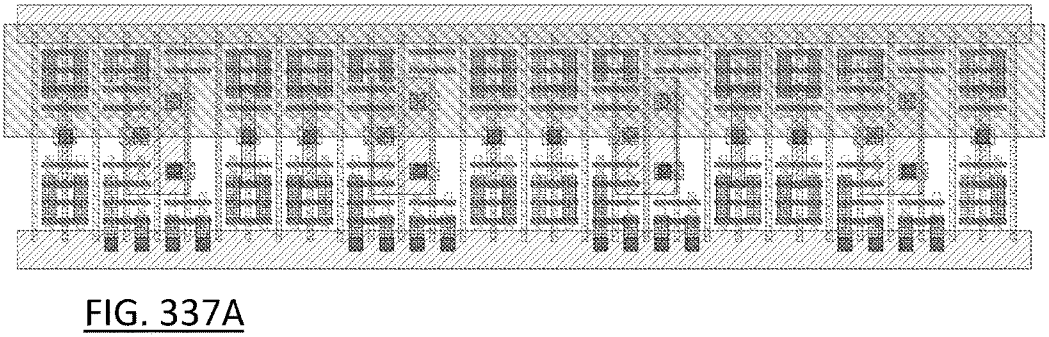
Figure 337B:
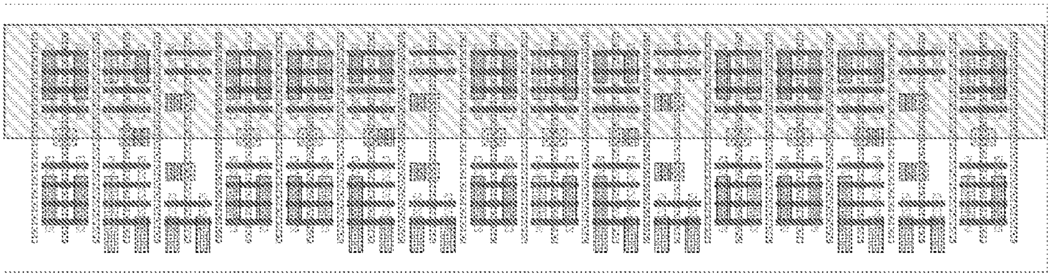
Figure 337C:
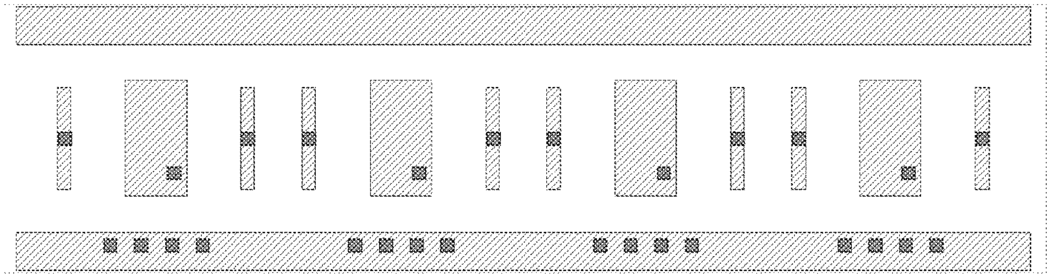
Figure 338A:
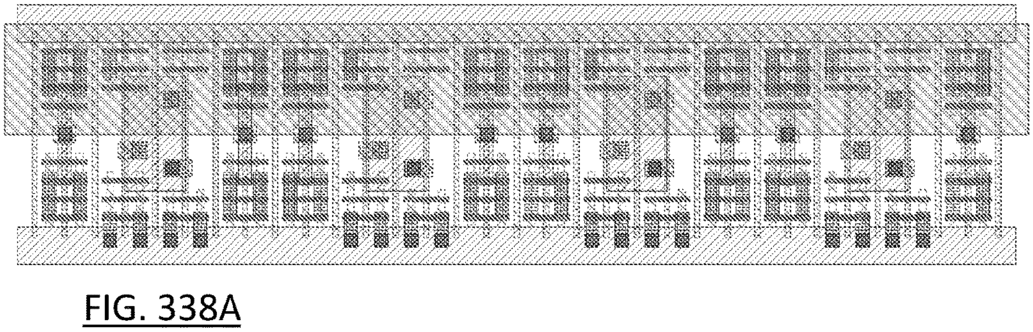
Figure 338B:
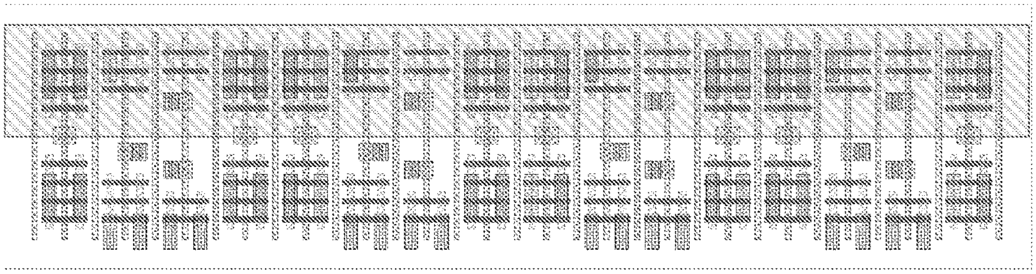
Figure 338C:
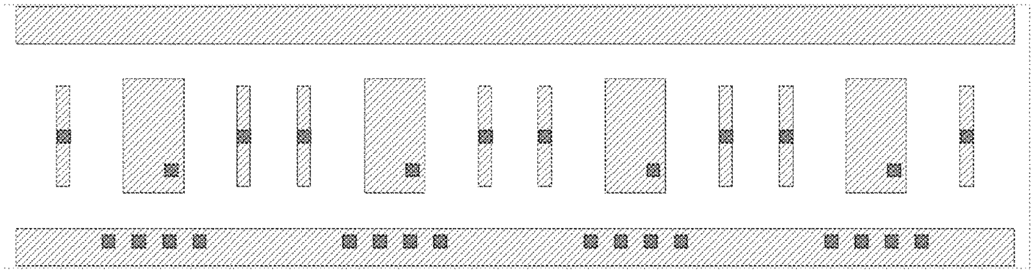
Figure 339A:
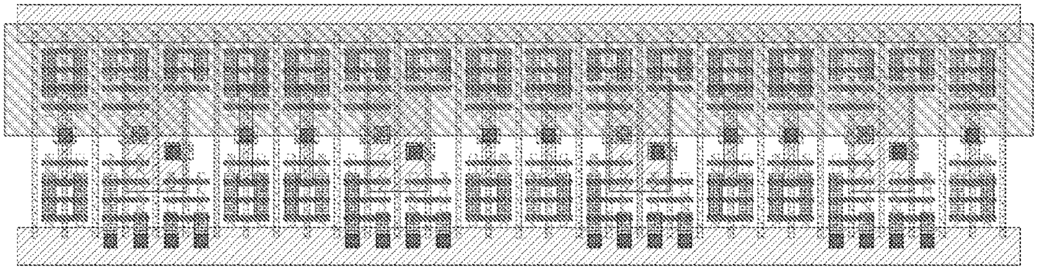
Figure 339B:
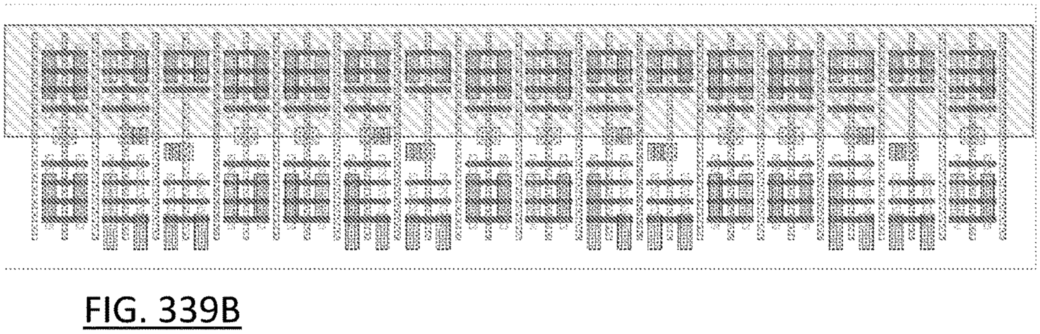
Figure 339C:
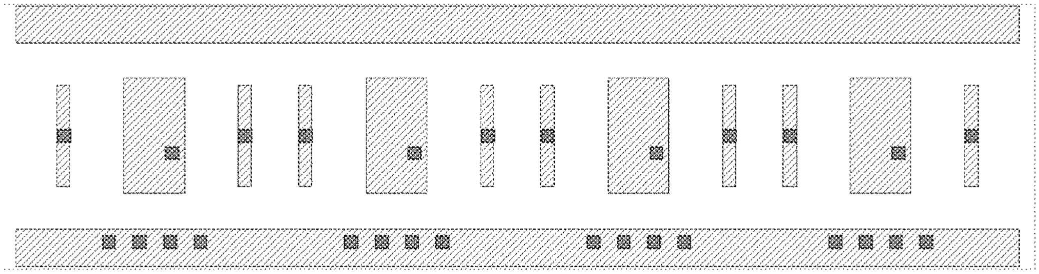
Figure 340A:
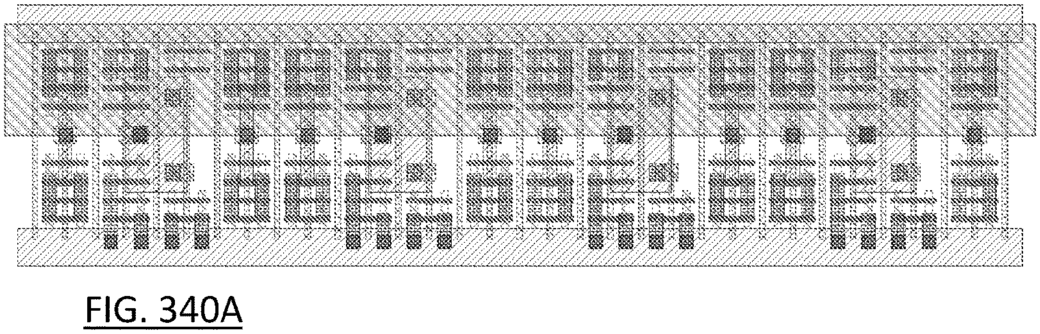
Figure 340B:
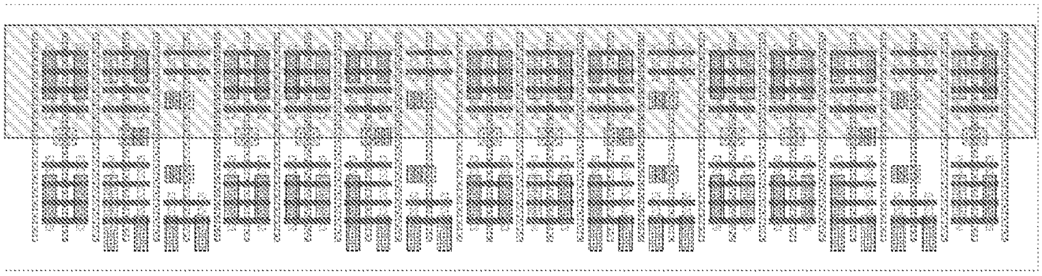
Figure 340C:
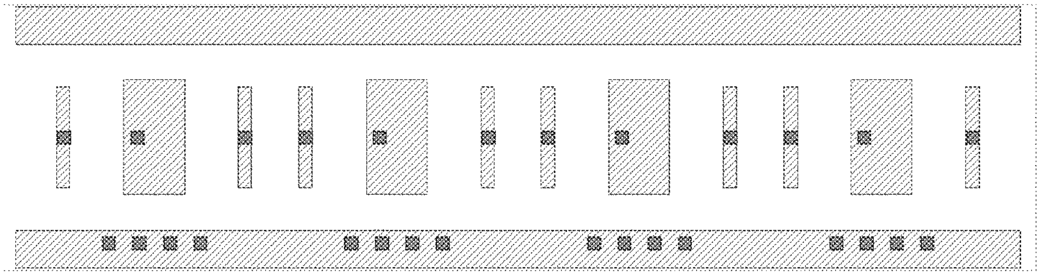
Figure 341A:
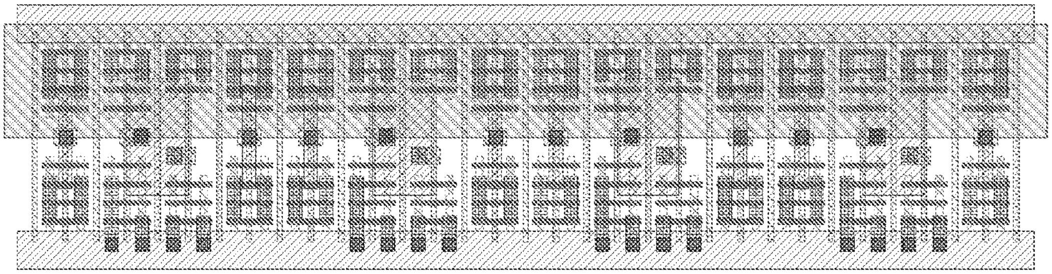
Figure 341B:
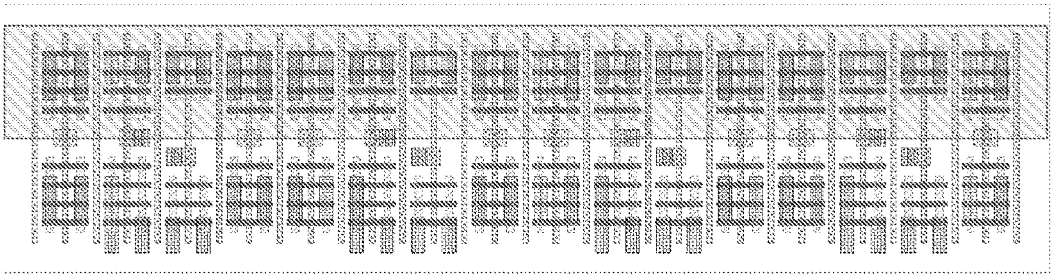
Figure 341C:
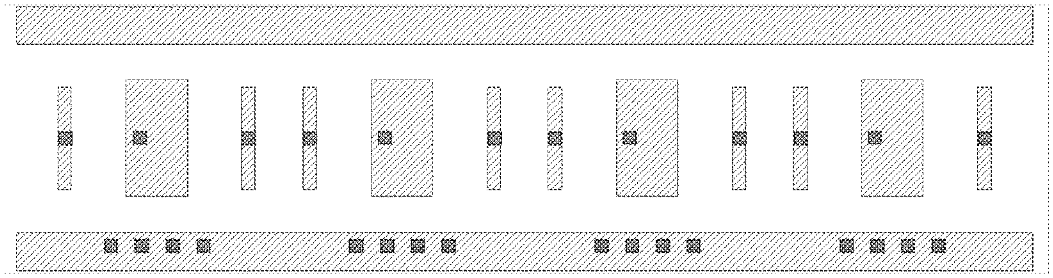
Figure 342A:
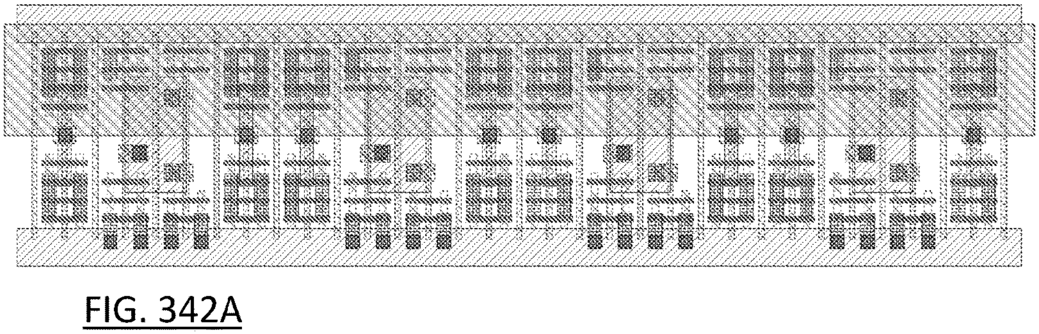
Figure 342B:
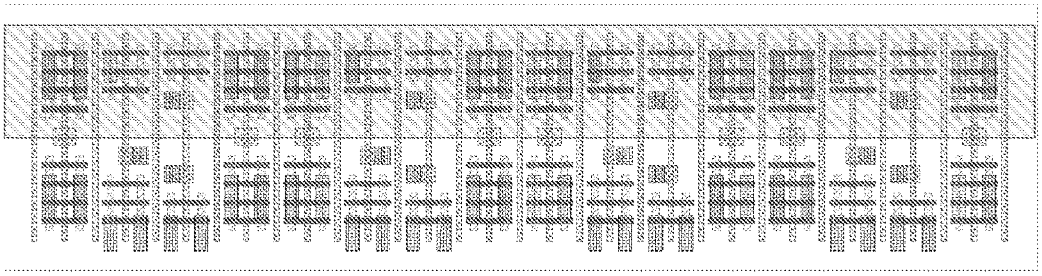
Figure 342C:
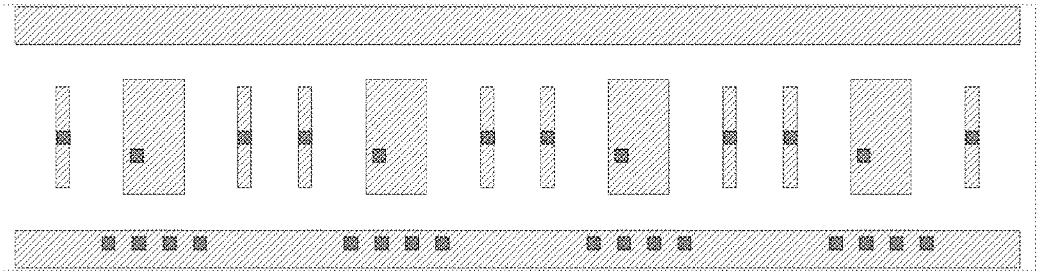
Figure 343A:
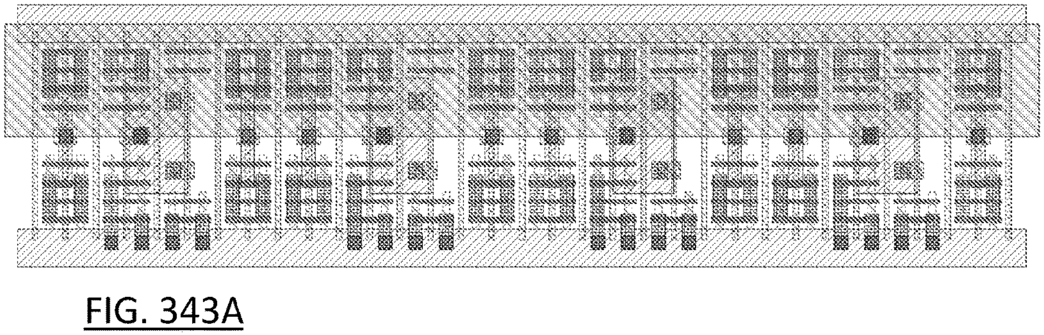
Figure 343B:
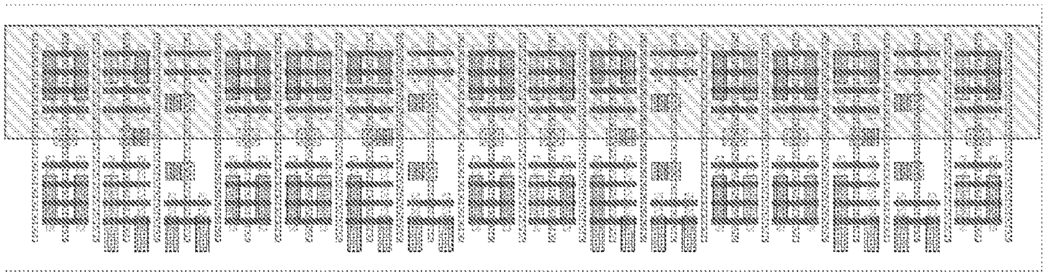
Figure 343C:
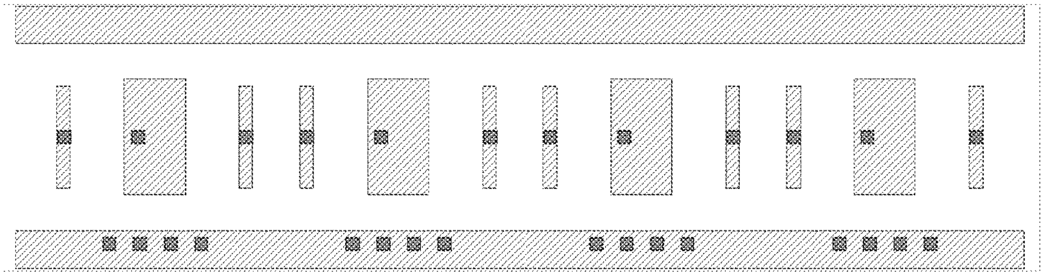
Figure 344A:
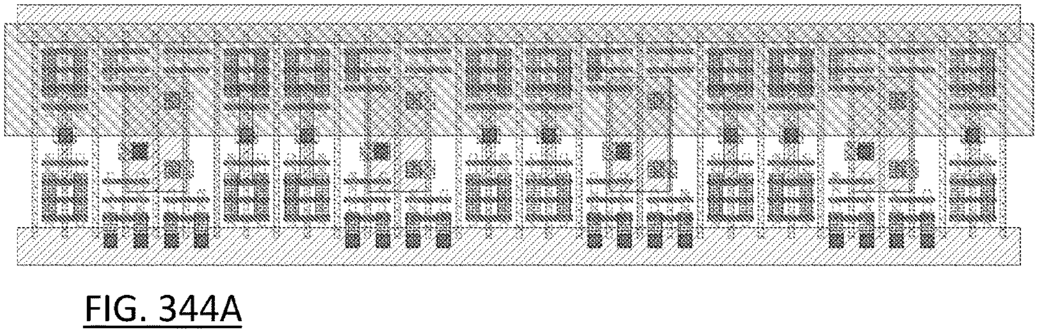
Figure 344B:
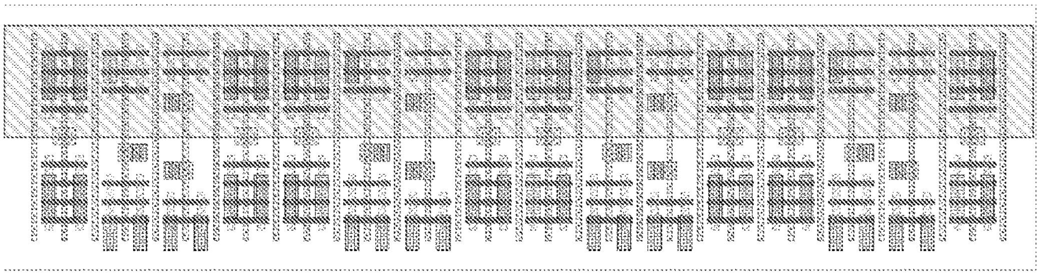
Figure 344C:
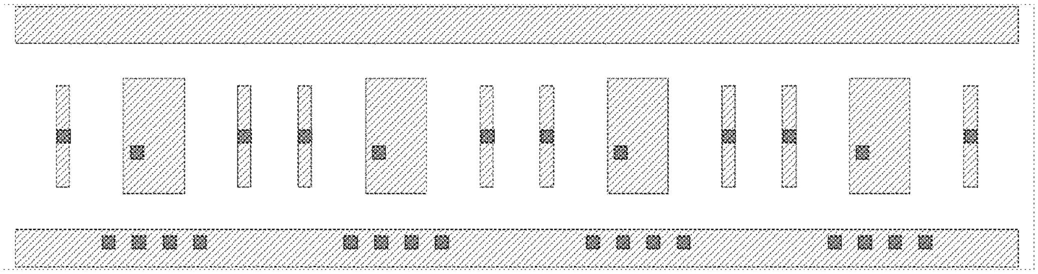
Figure 345A:
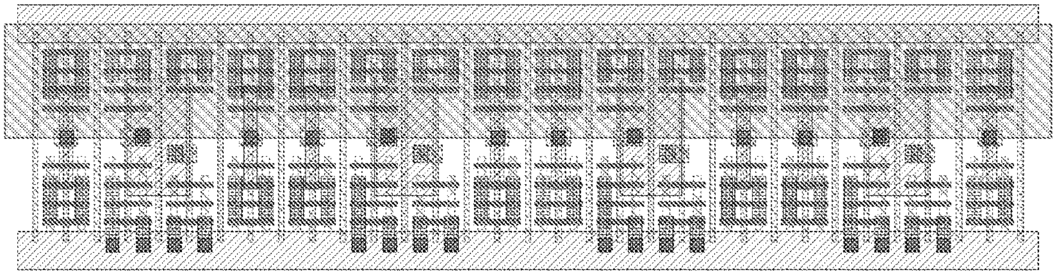
Figure 345B:
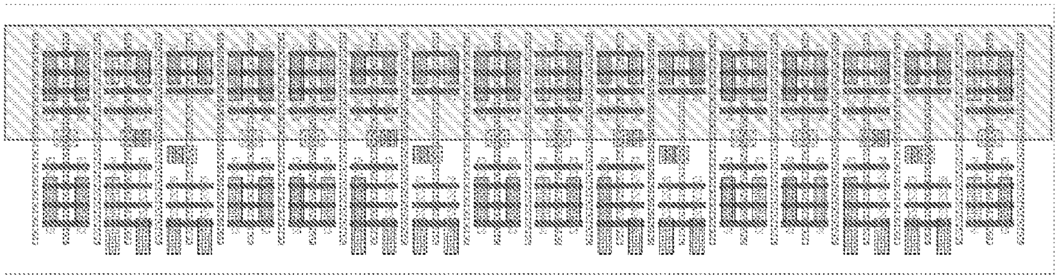
Figure 345C:
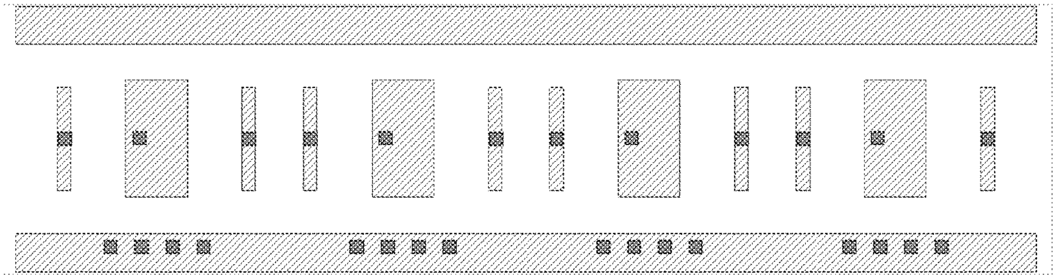
Figure 346A:
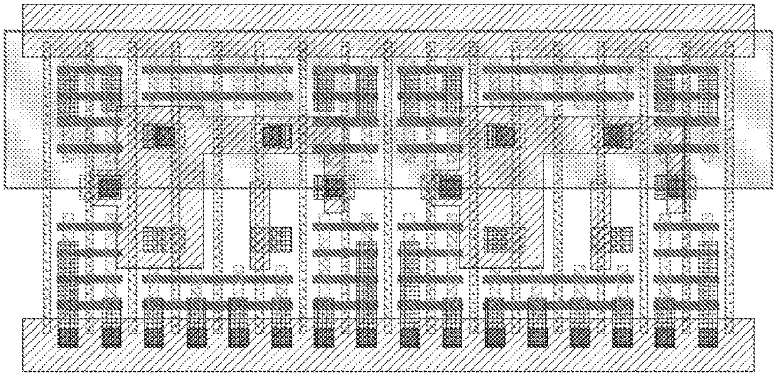
Figure 346B:
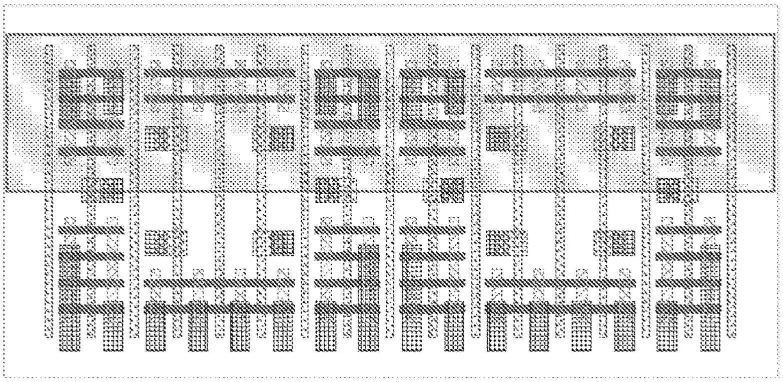
Figure 346C:
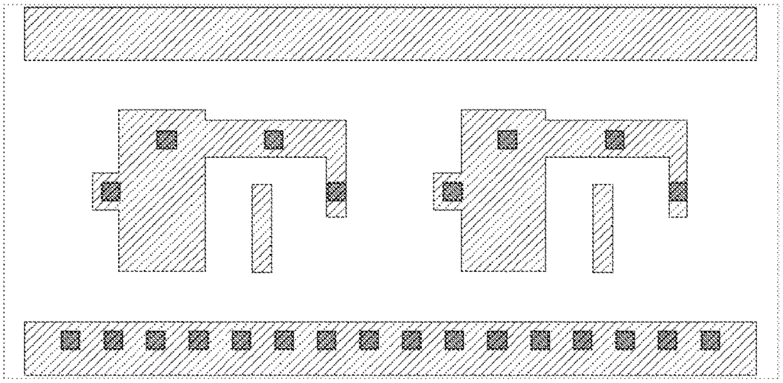
Figure 347A:
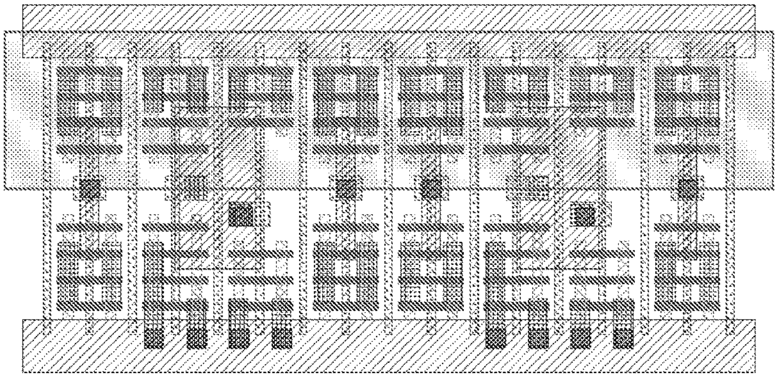
Figure 347B:
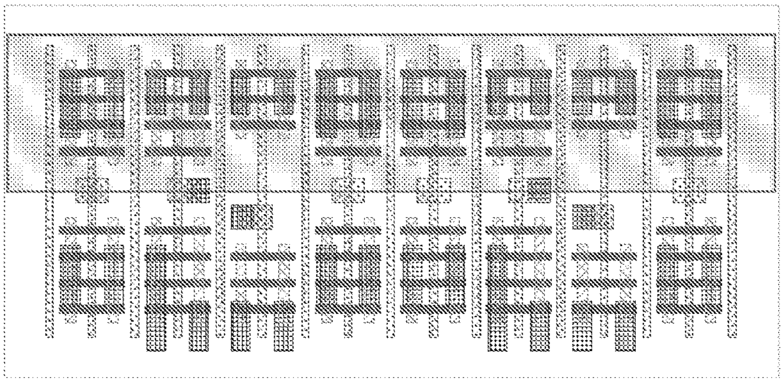
Figure 347C:
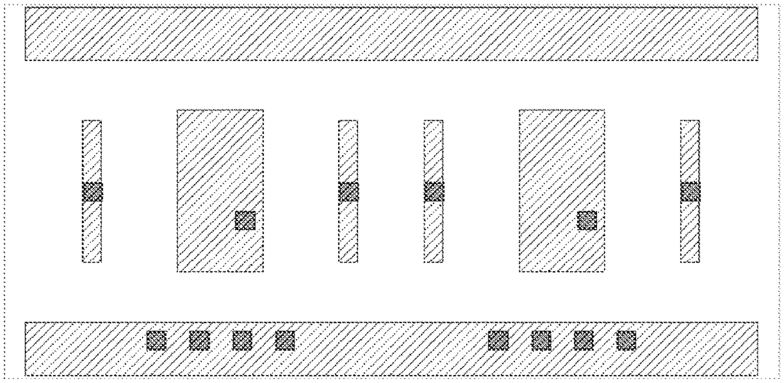
Figure 348A:
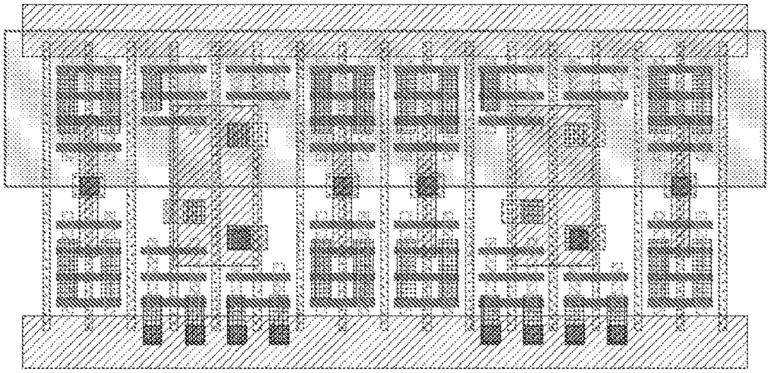
Figure 348B:
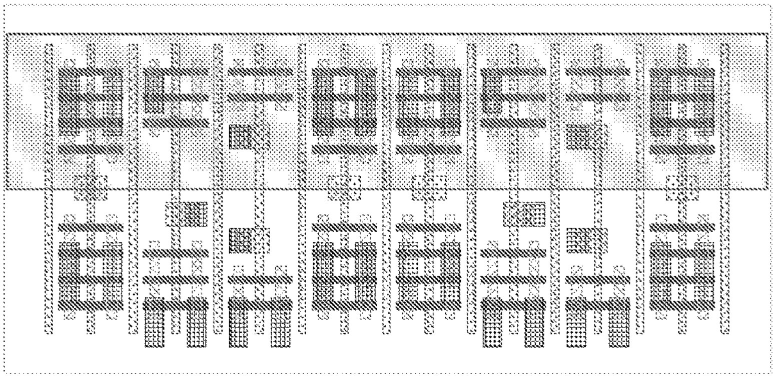
Figure 348C:
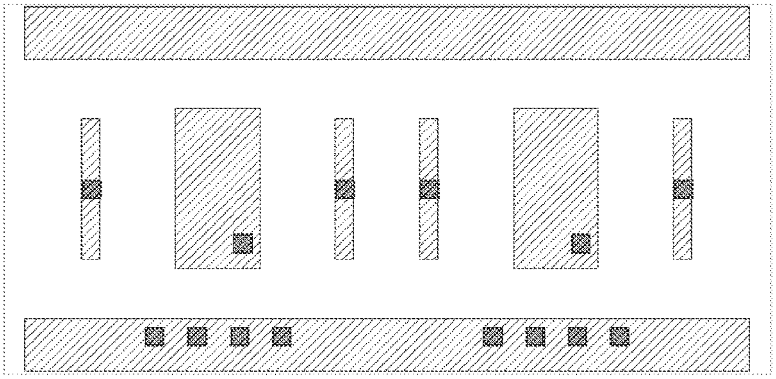
Figure 349A:
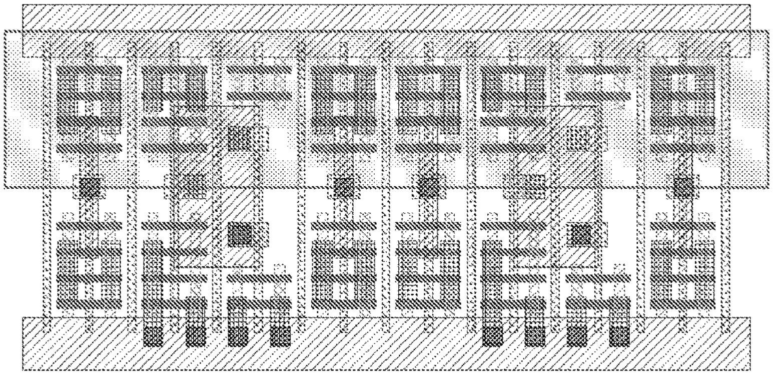
Figure 349B:
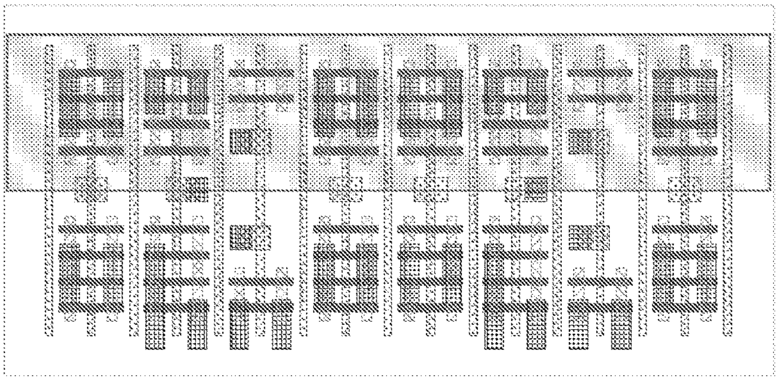
Figure 349C:
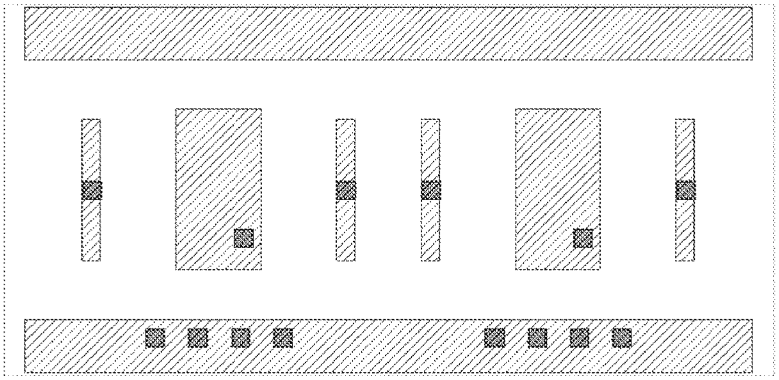
Figure 350A:
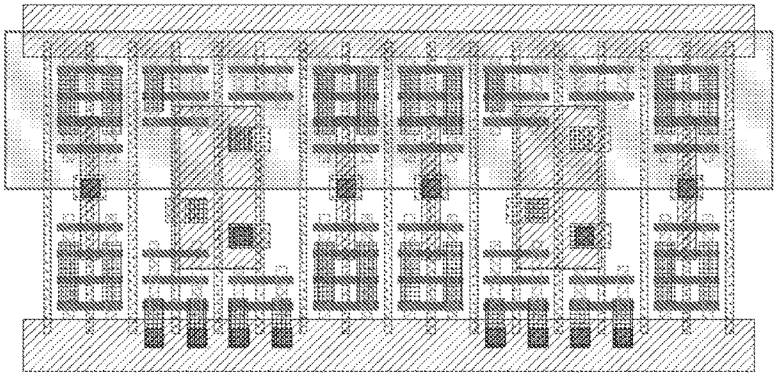
Figure 350B:
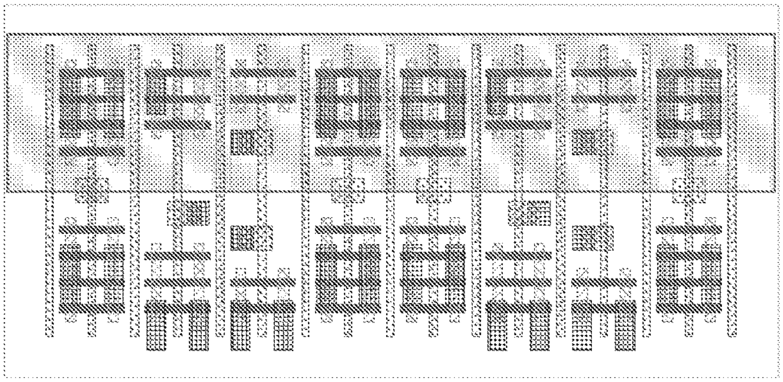
Figure 350C:
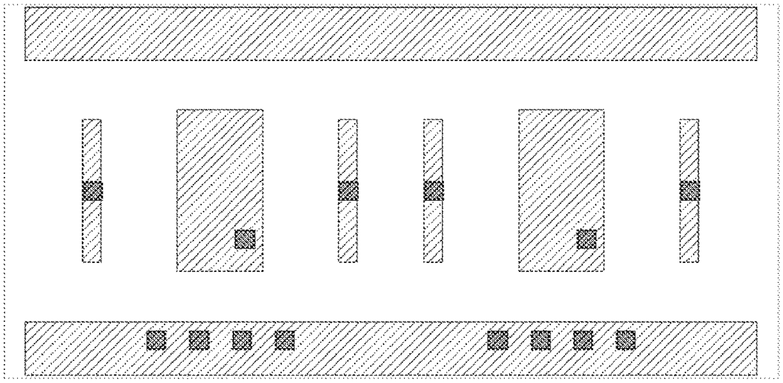
Figure 351A:
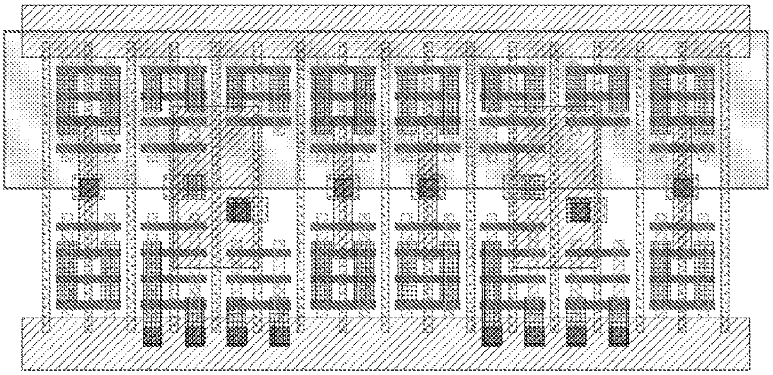
Figure 351B:
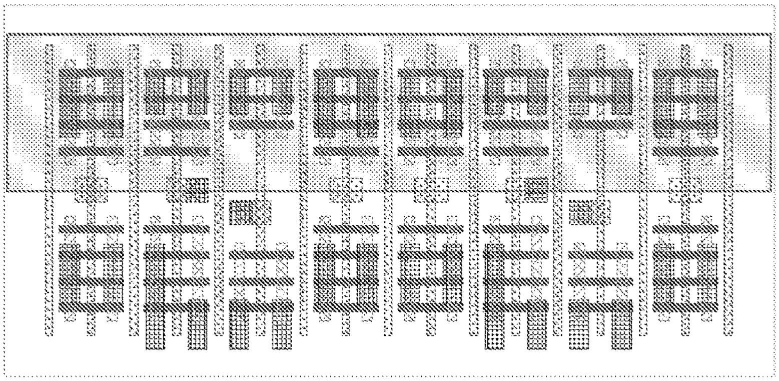
Figure 351C:
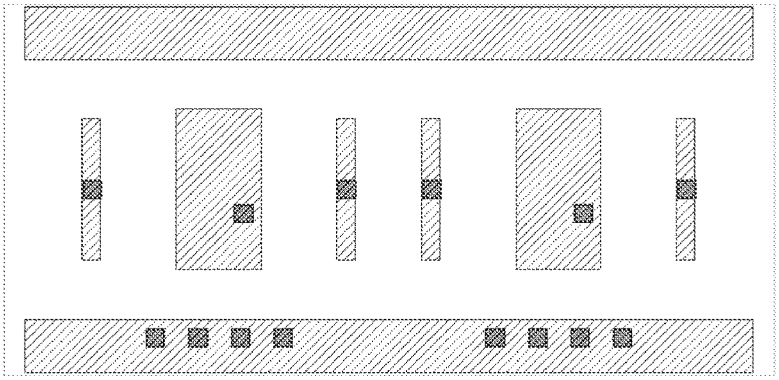
Figure 352A:
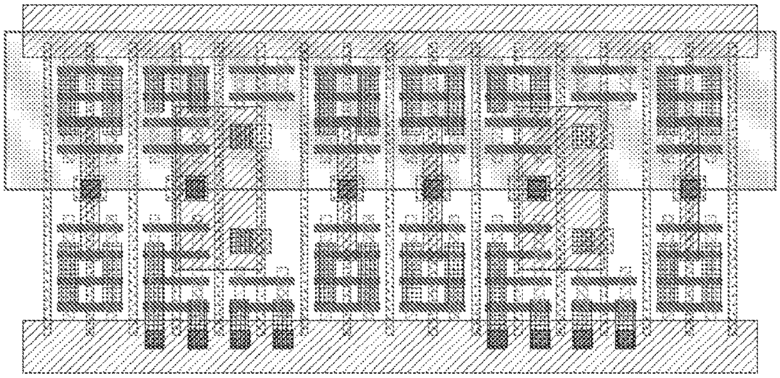
Figure 352B:
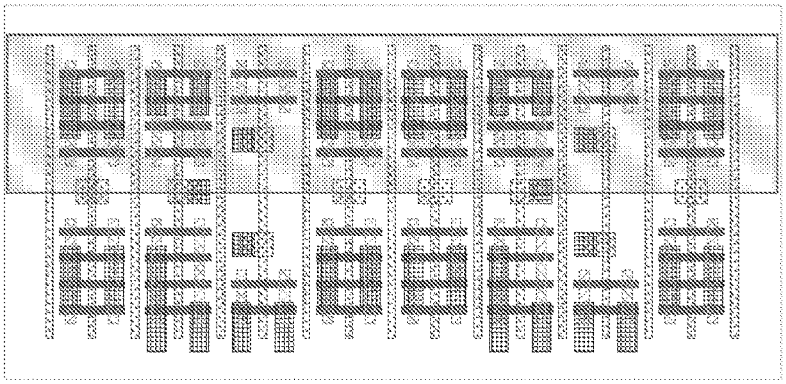
Figure 352C:
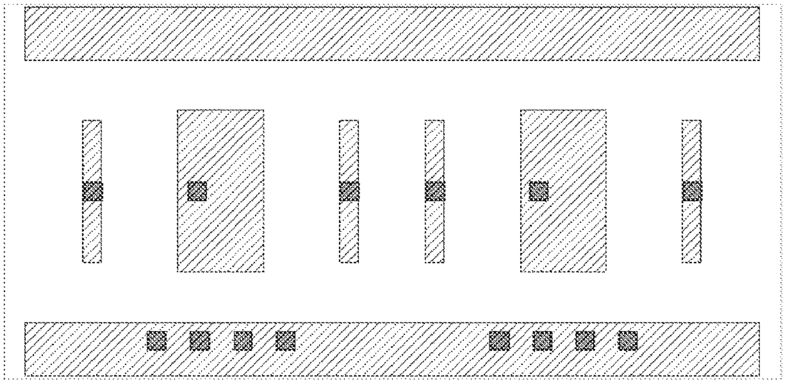
Figure 353A:
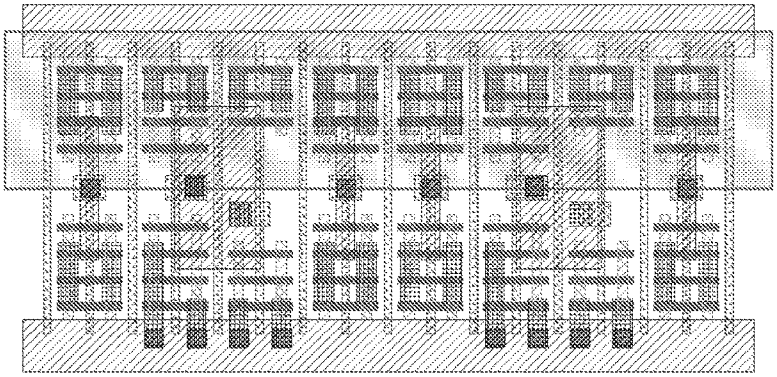
Figure 353B:
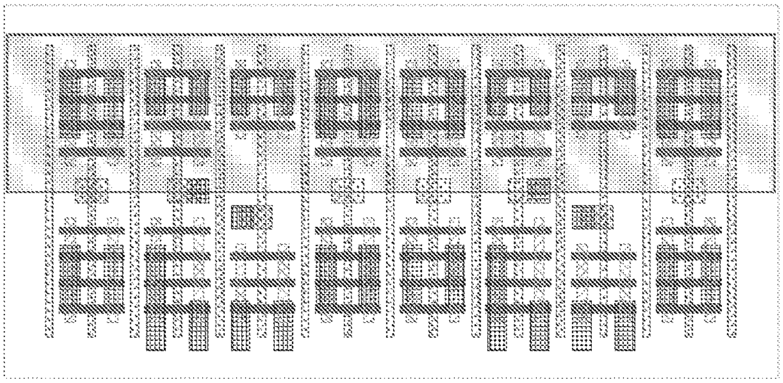
Figure 353C:
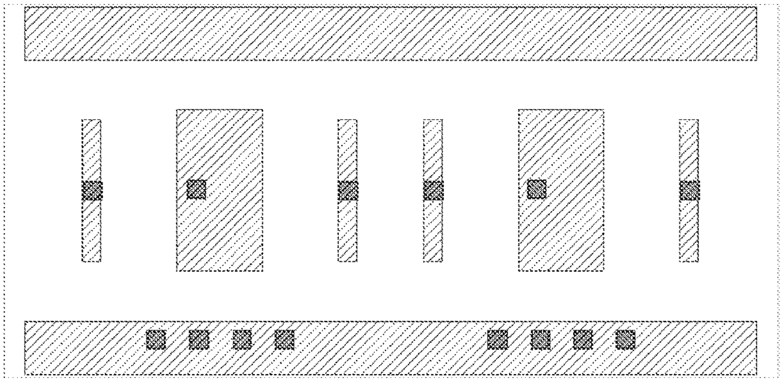
Figure 354A:
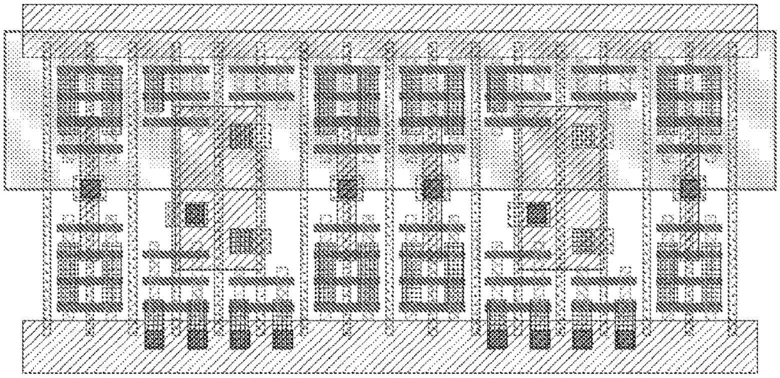
Figure 354B:
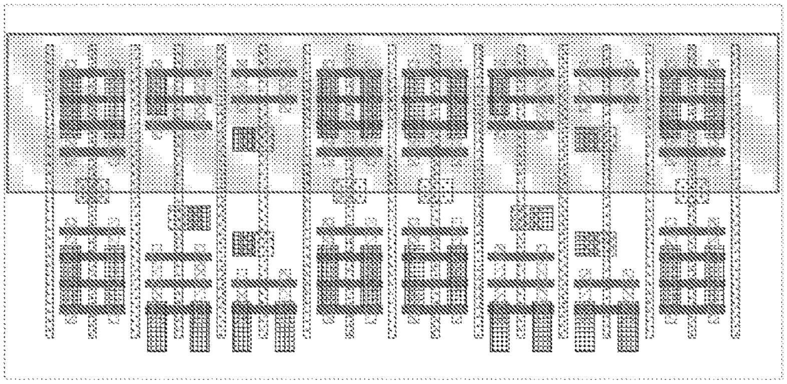
Figure 354C:
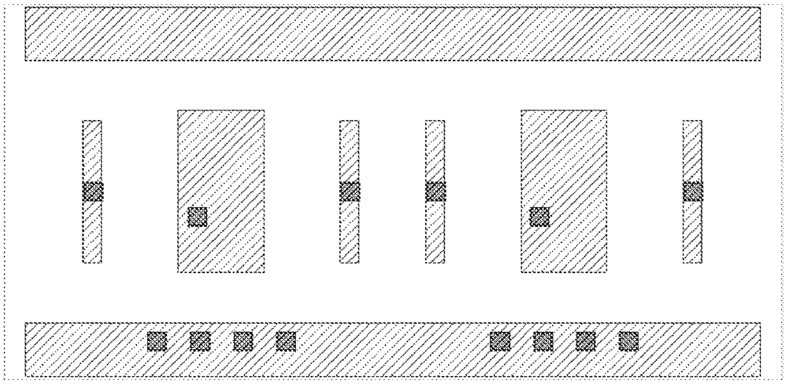
Figure 355A:
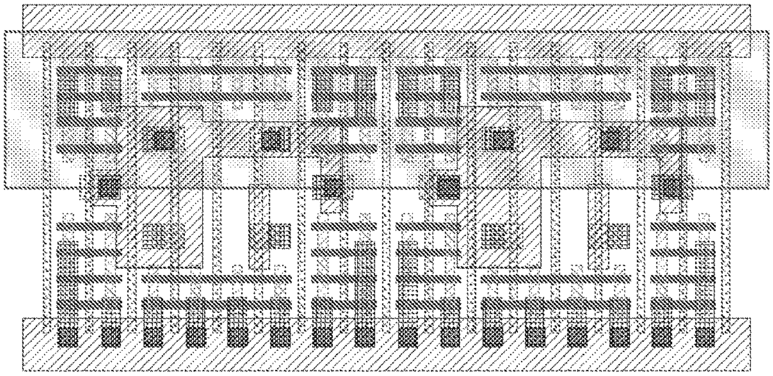
Figure 355B:
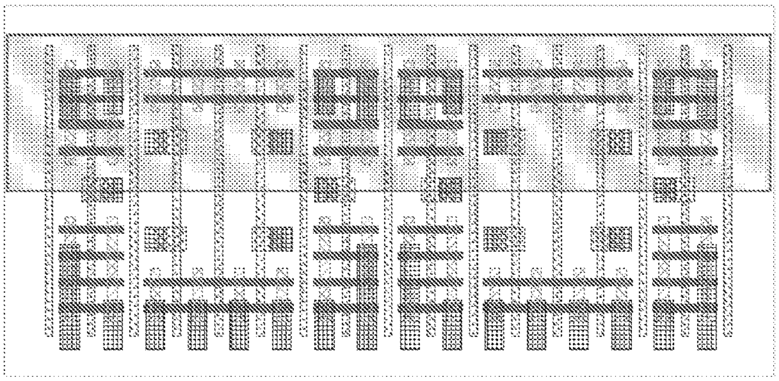
Figure 355C:
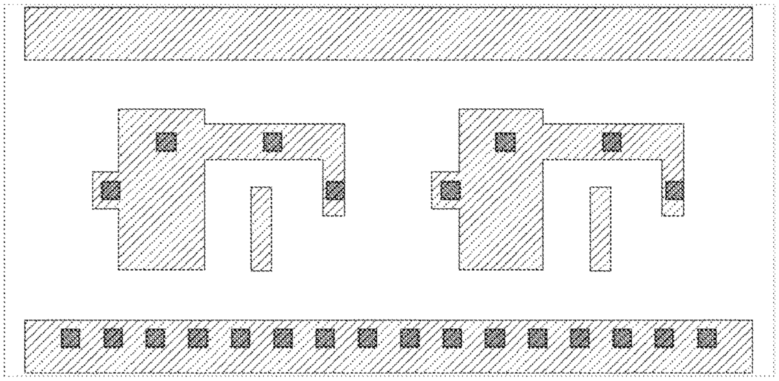
Figure 356A:
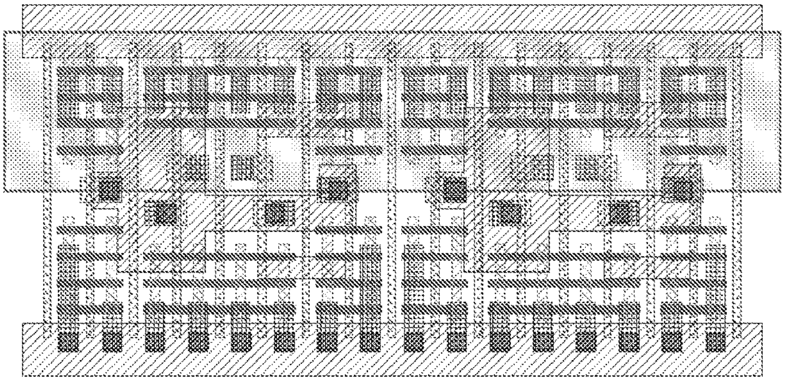
Figure 356B:
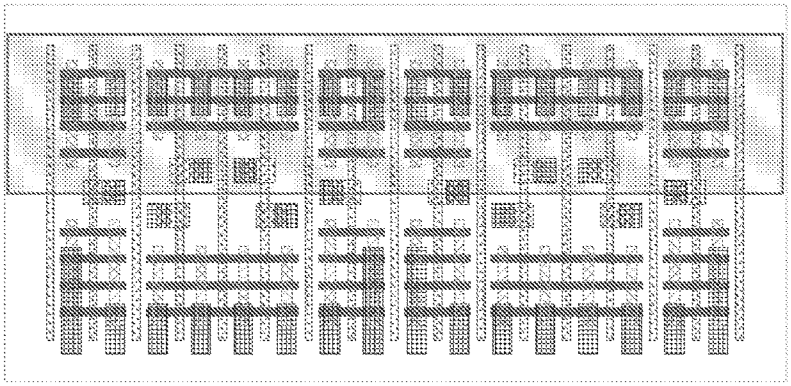
Figure 356C:
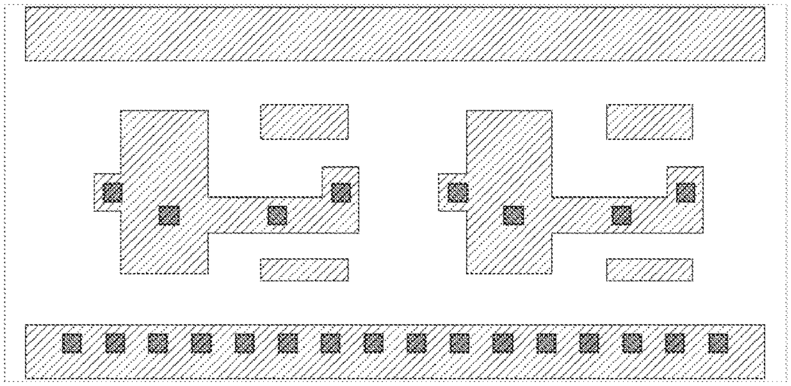
Figure 357A:
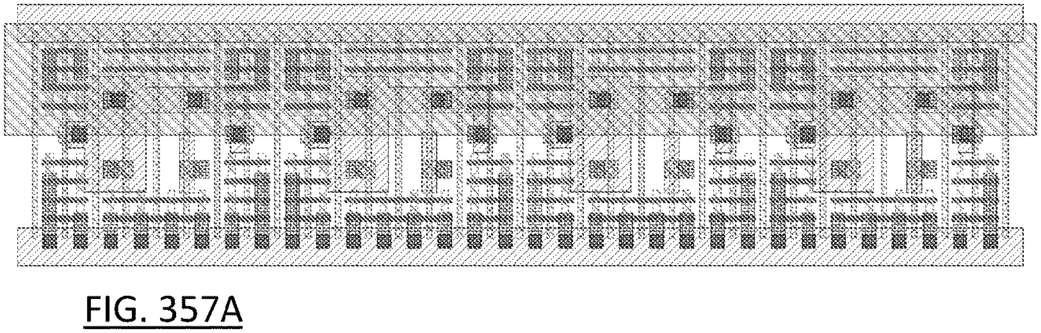
Figure 357B:
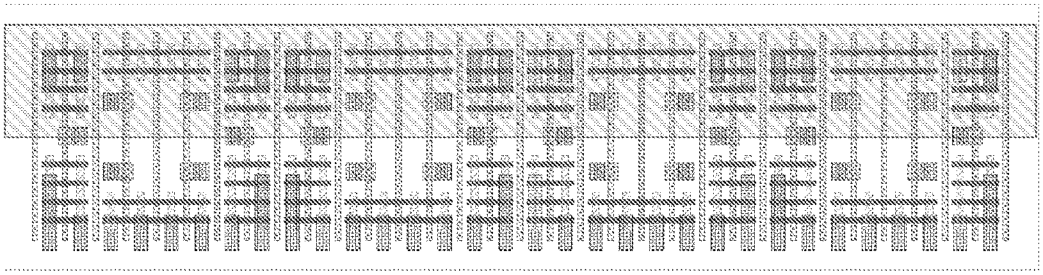
Figure 357C:
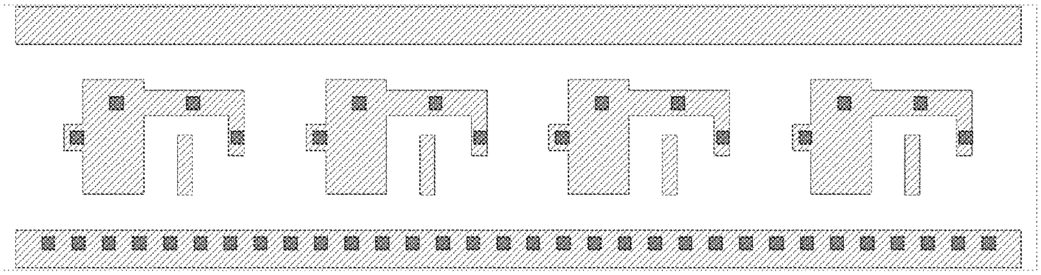
Figure 358A:
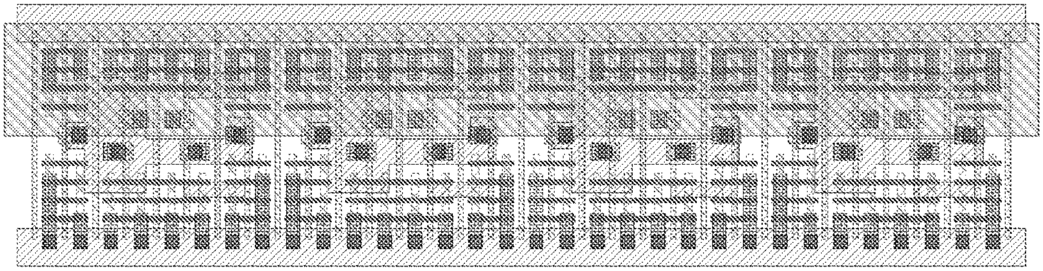
Figure 358B:
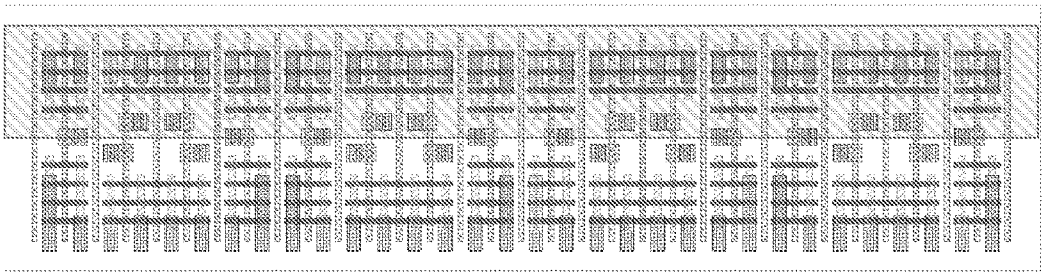
Figure 358C:
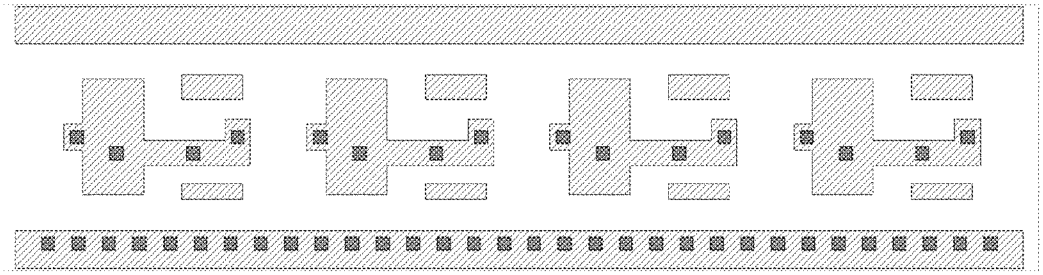
Figure 359A:
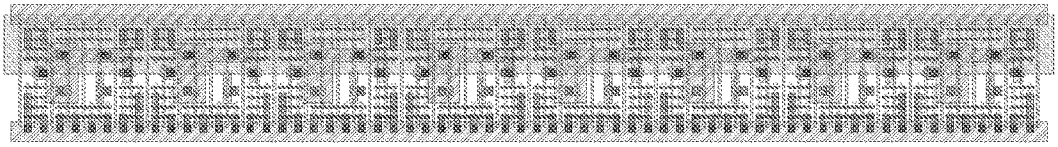
Figure 359B:
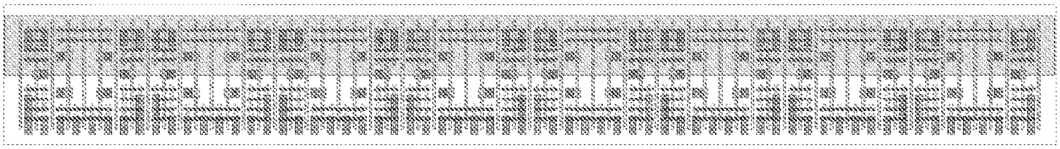
Figure 359C:
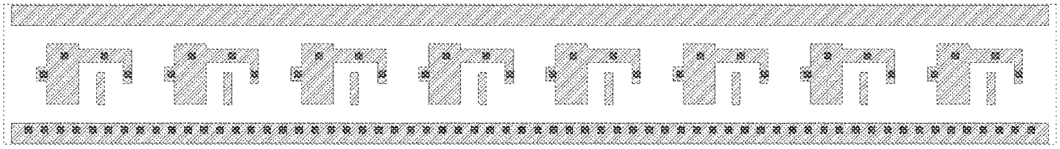
Figure 360A:
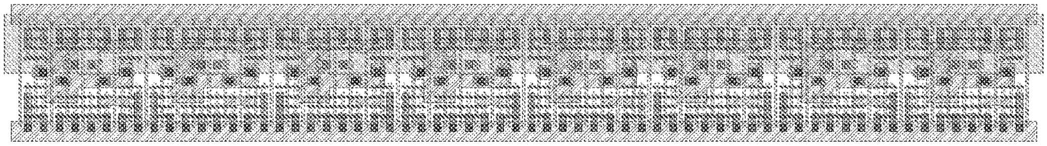
Figure 360B:
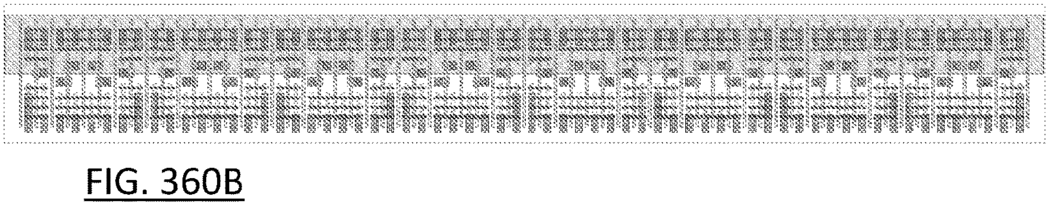
Figure 360C:
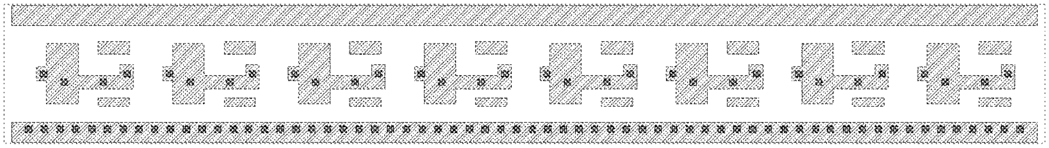
Figure 361A:
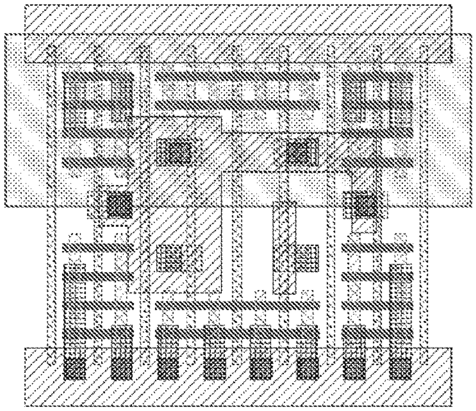
Figure 361B:
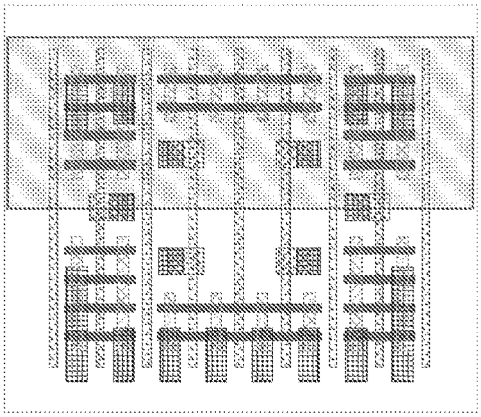
Figure 361C:
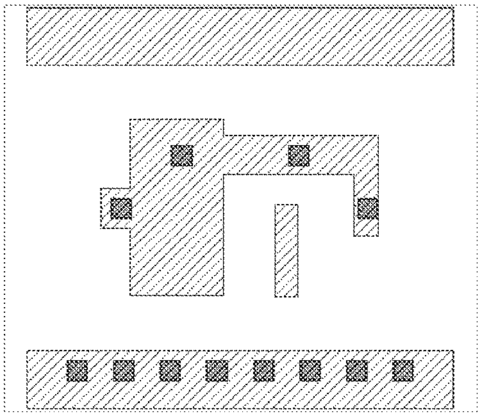
Figure 362A:
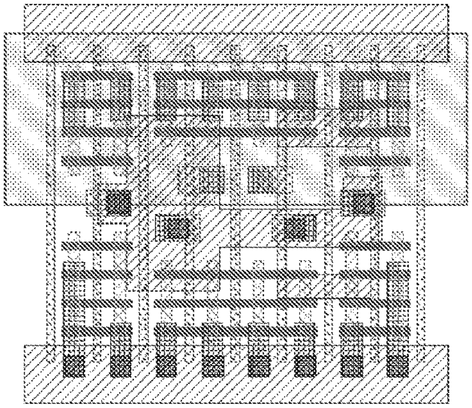
Figure 362B:
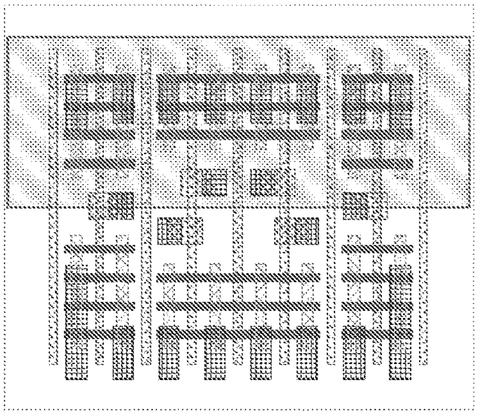
Figure 362C:
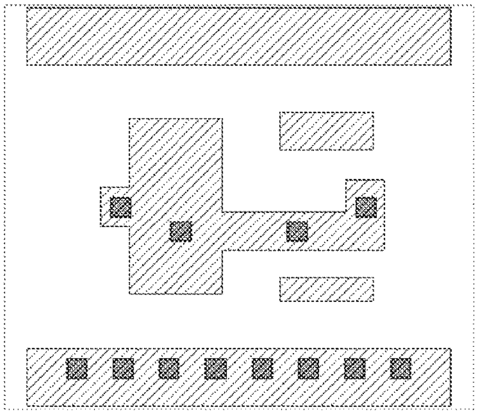
Figure 363A:
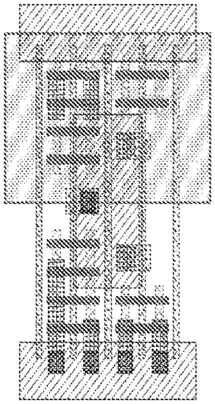
Figure 363B:
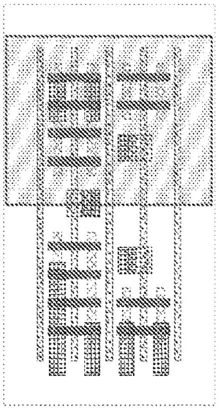
Figure 363C:
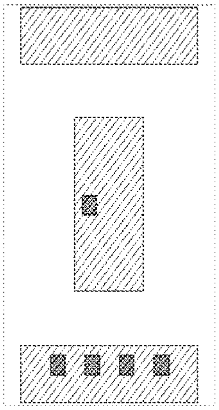
Figure 364A:
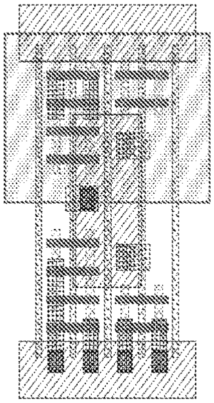
Figure 364B:
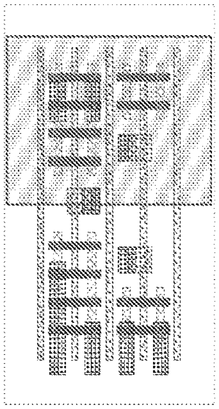
Figure 364C:
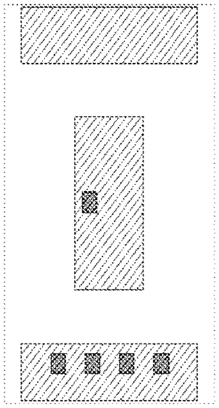
Figure 365A:
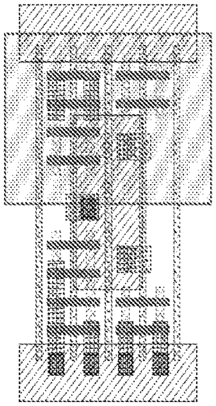
Figure 365B:
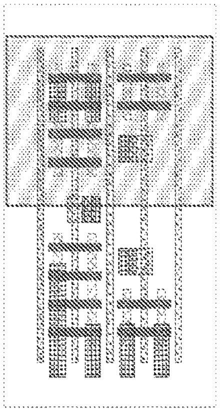
Figure 365C:
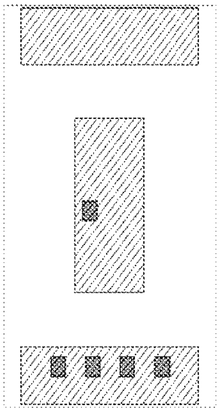
Figure 366A:
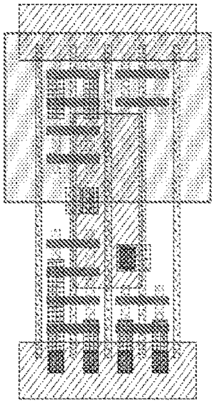
Figure 366B:
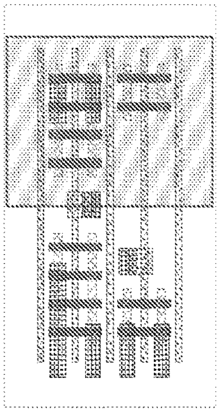
Figure 366C:
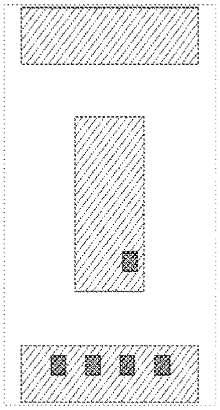
Figure 367A:
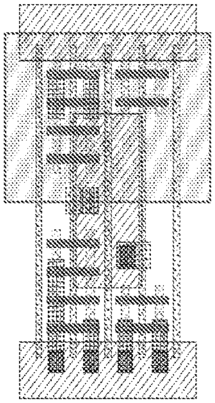
Figure 367B:
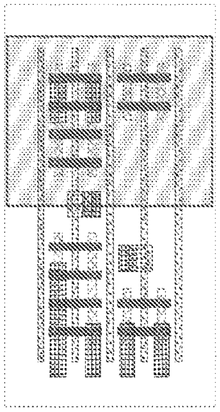
Figure 367C:
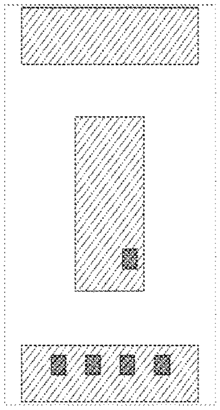
Figure 368A:
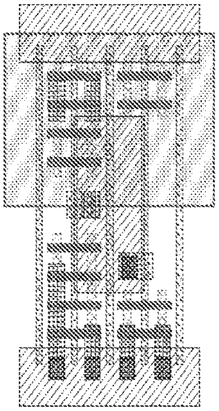
Figure 368B:
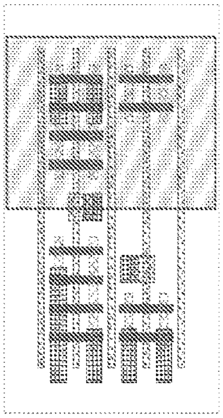
Figure 368C:
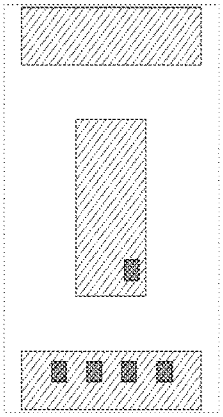
Figure 369A:
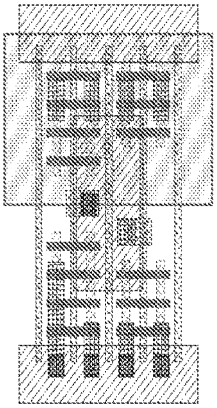
Figure 369B:
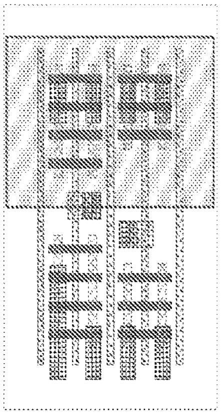
Figure 369C:
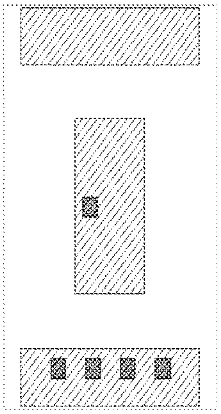
Figure 370A:
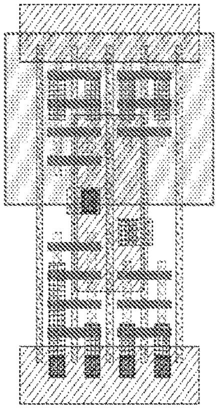
Figure 370B:
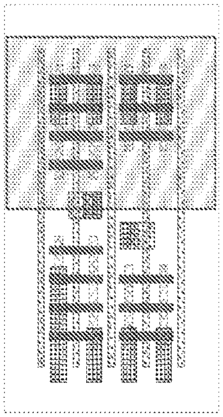
Figure 370C:
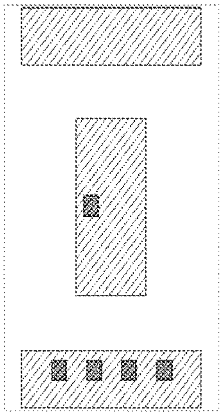
Figure 371A:
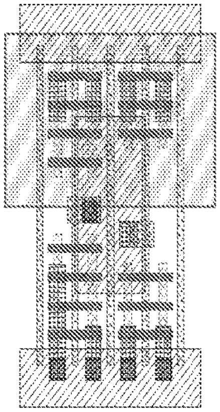
Figure 371B:
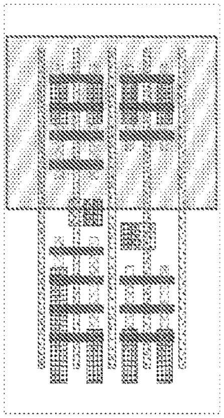
Figure 371C:
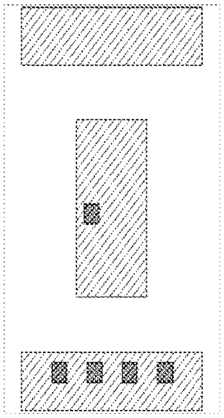
Figure 372A:
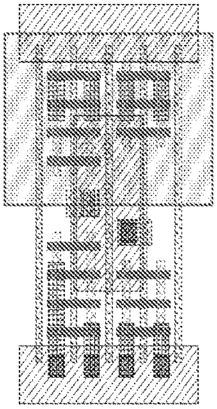
Figure 372B:
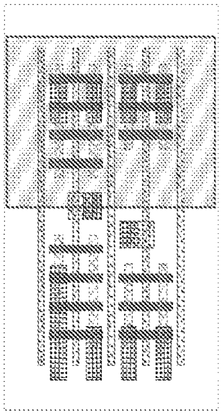
Figure 372C:
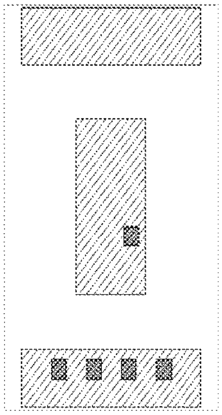
Figure 373A:
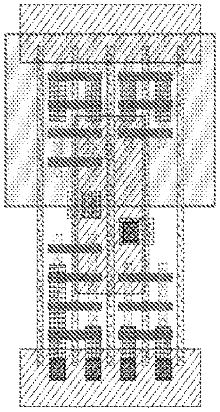
Figure 373B:
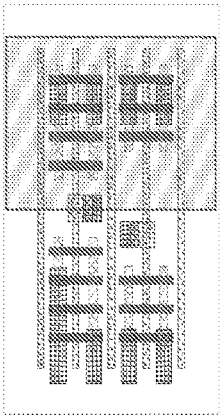
Figure 373C:
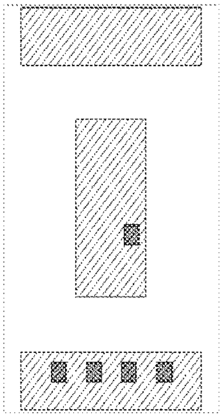
Figure 374A:
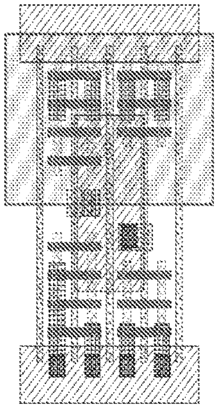
Figure 374B:
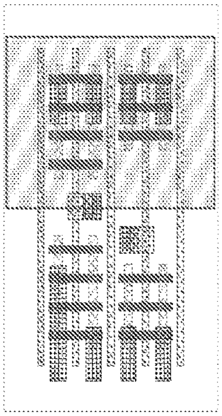
Figure 374C:
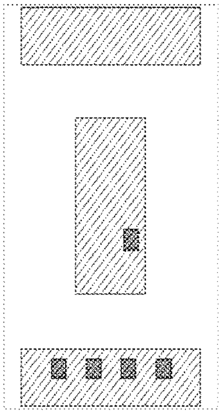
Figure 375A:
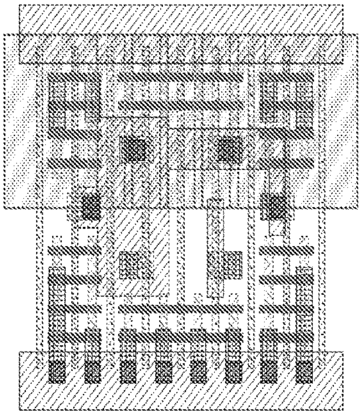
Figure 375B:
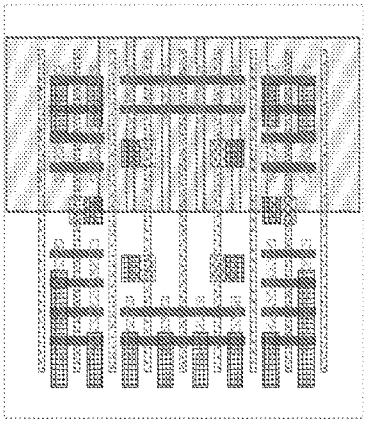
Figure 375C:
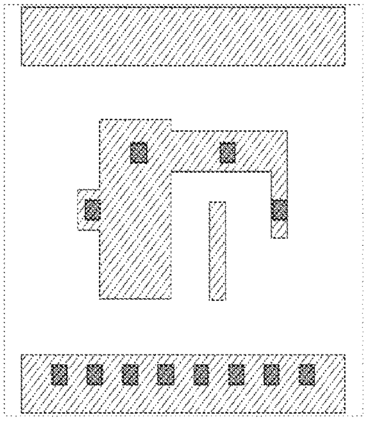
Figure 376A:
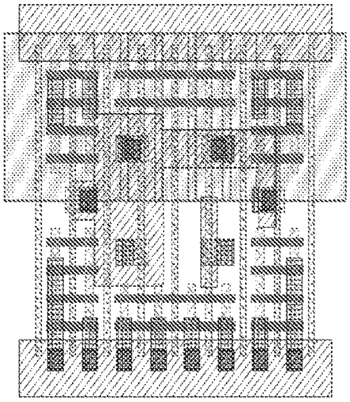
Figure 376B:
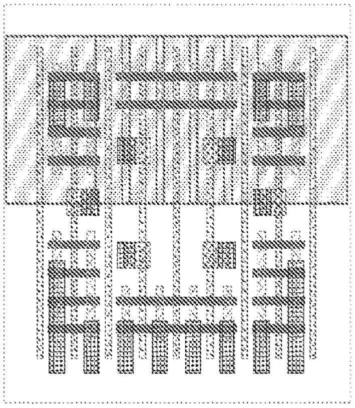
Figure 376C:
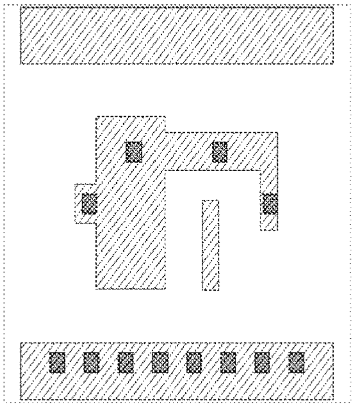
Figure 377A:
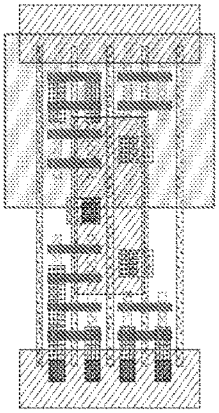
Figure 377B:
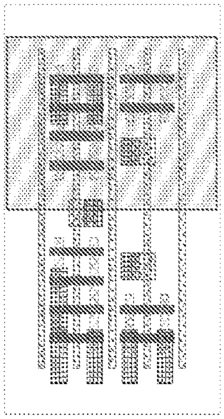
Figure 377C:
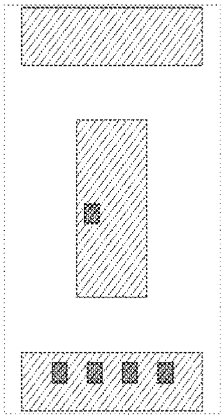
Figure 378A:
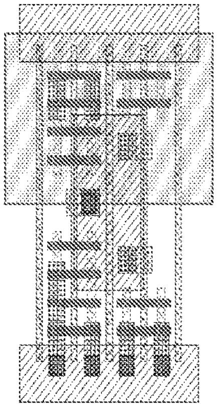
Figure 378B:
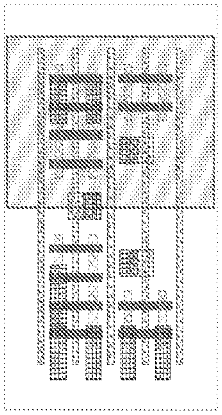
Figure 378C:
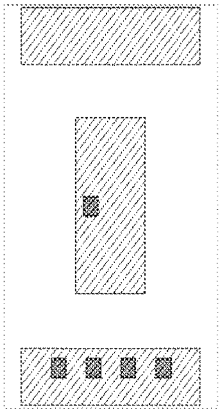
Figure 379A:
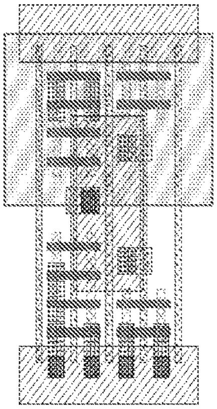
Figure 379B:
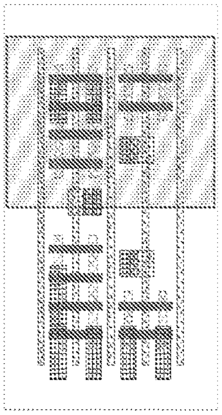
Figure 379C:
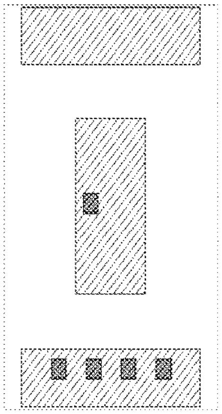
Figure 380A:
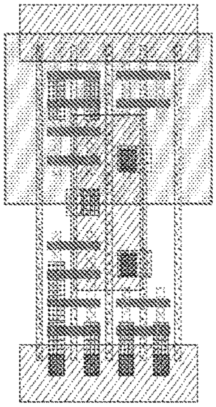
Figure 380B:
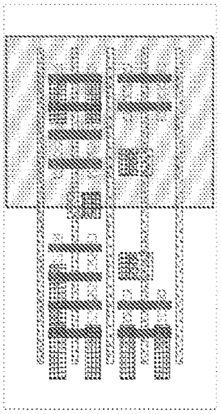
Figure 380C:
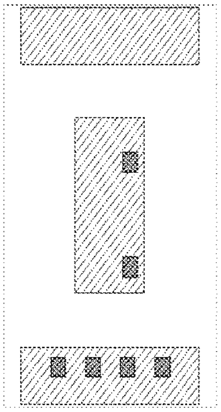
Figure 381A:
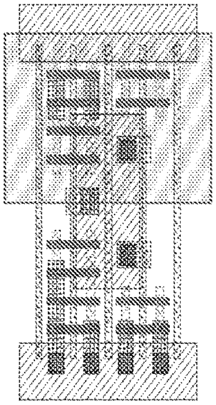
Figure 381B:
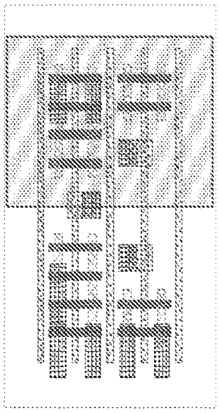
Figure 381C:
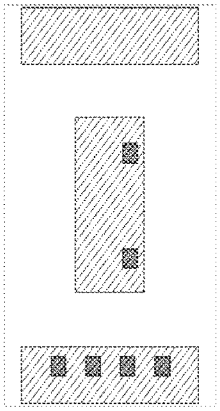
Figure 382A:
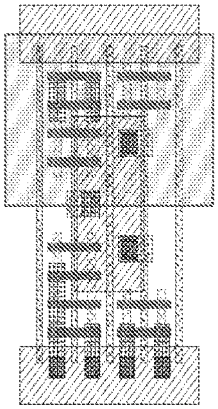
Figure 382B:
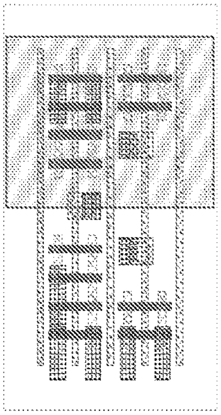
Figure 382C:
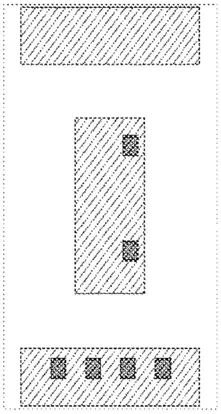
Figure 383A:
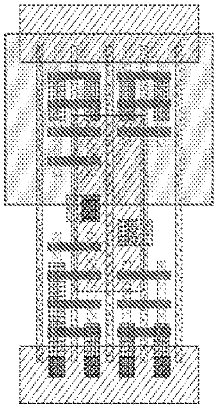
Figure 383B:
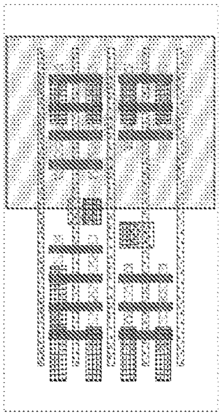
Figure 383C:
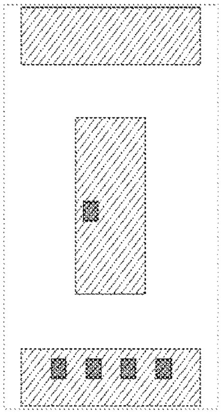
Figure 384A:
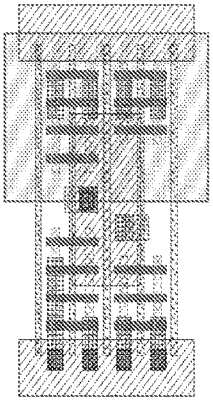
Figure 384B:
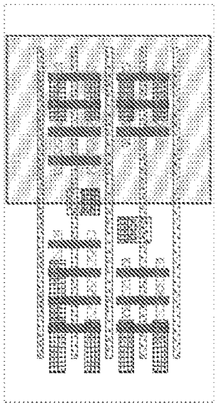
Figure 384C:
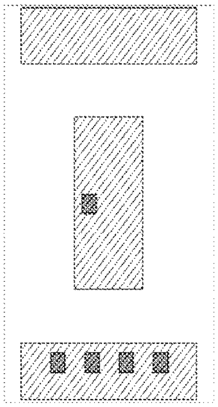
Figure 385A:
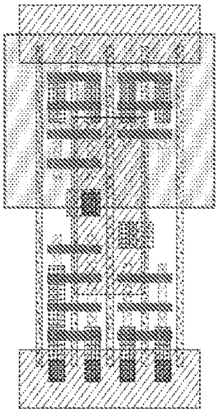
Figure 385B:
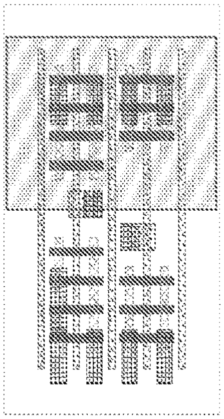
Figure 385C:
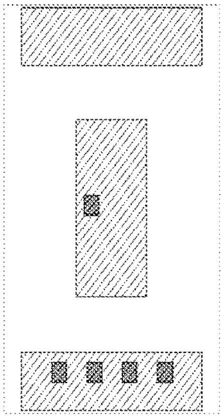
Figure 386A:
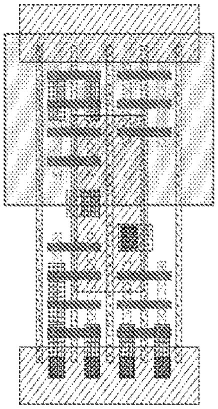
Figure 386B:
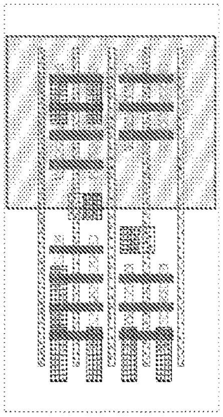
Figure 386C:
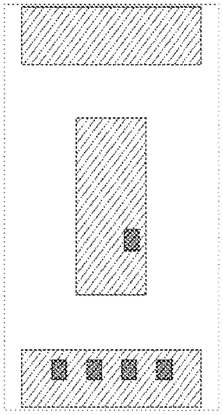
Figure 387A:
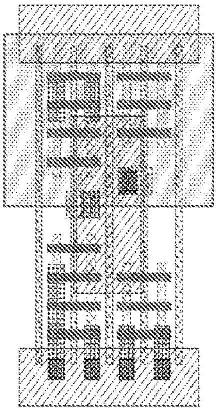
Figure 387B:
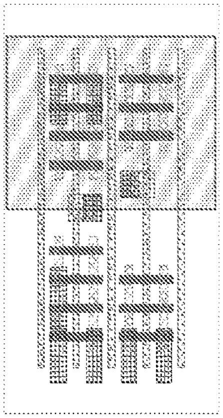
Figure 387C:
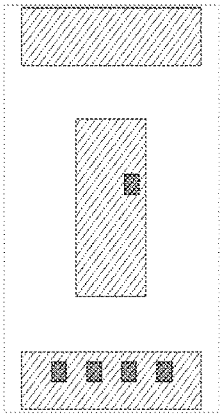
Figure 388A:
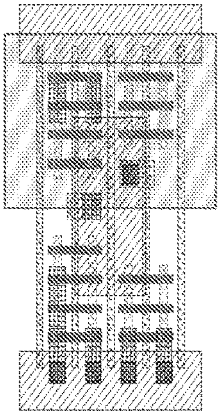
Figure 388B:
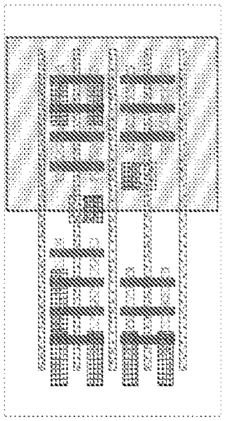
Figure 388C:
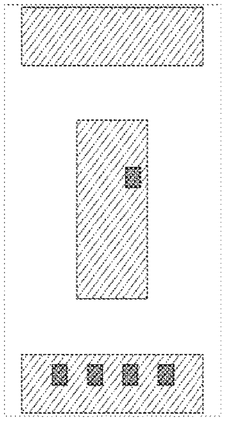
Figure 389A:
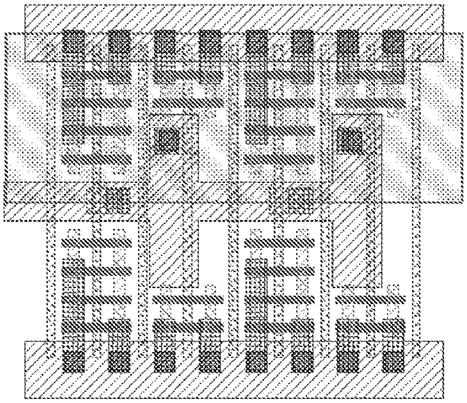
Figure 389B:
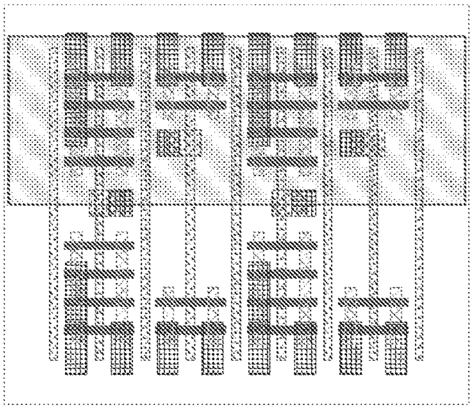
Figure 389C:
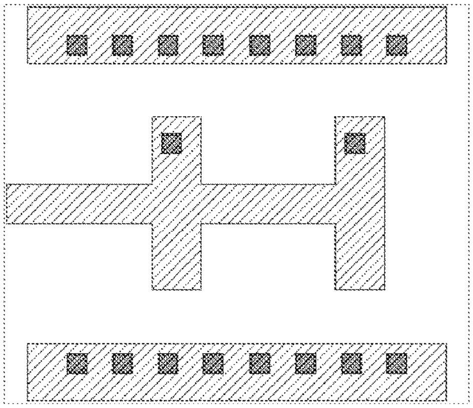
Figure 390A:
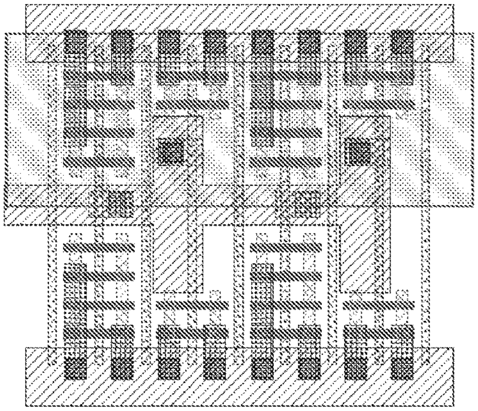
Figure 390B:
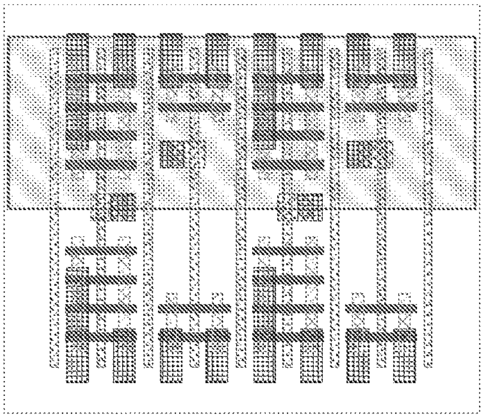
Figure 390C:
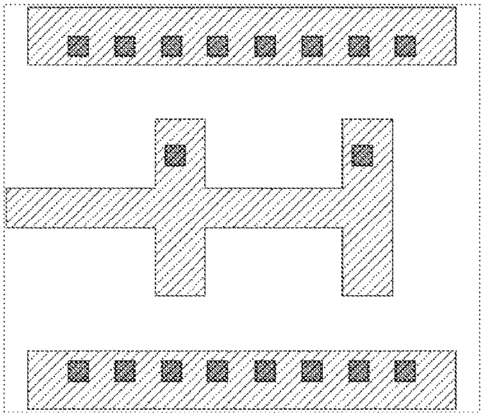
Figure 391A:
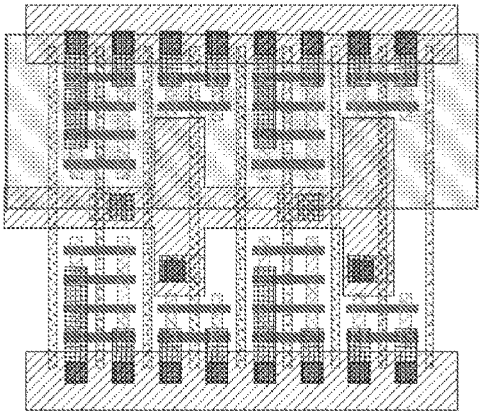
Figure 391B:
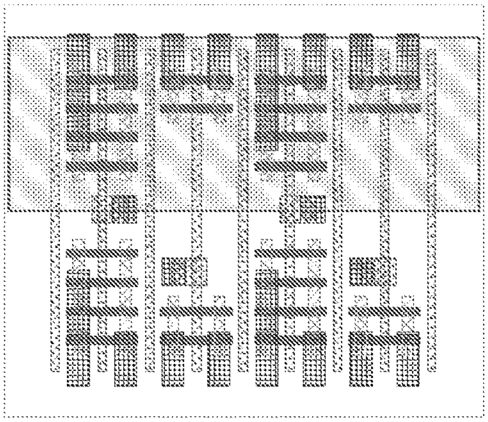
Figure 391C:
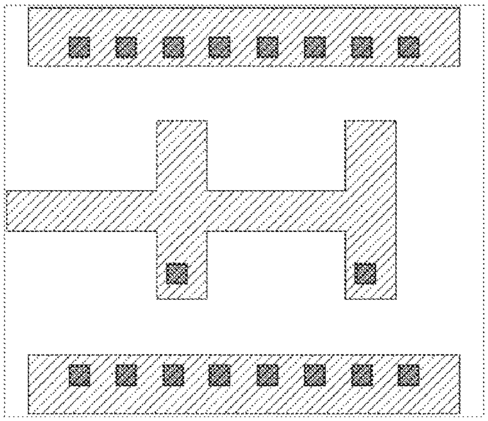
Figure 392A:
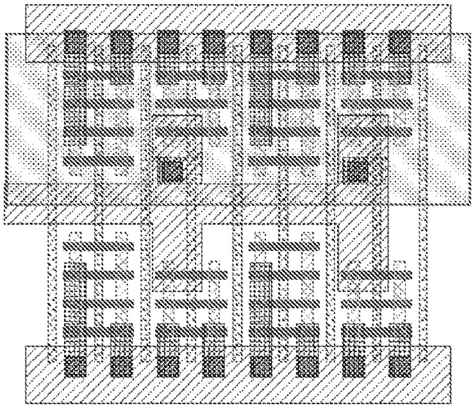
Figure 392B:
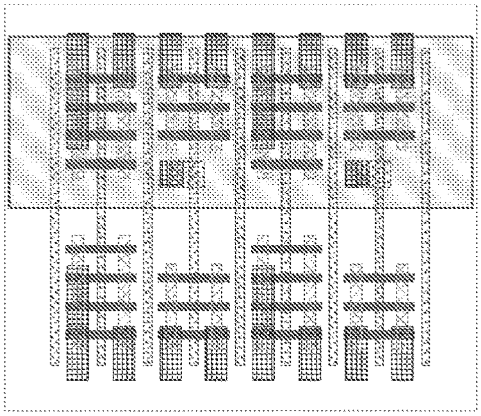
Figure 392C:
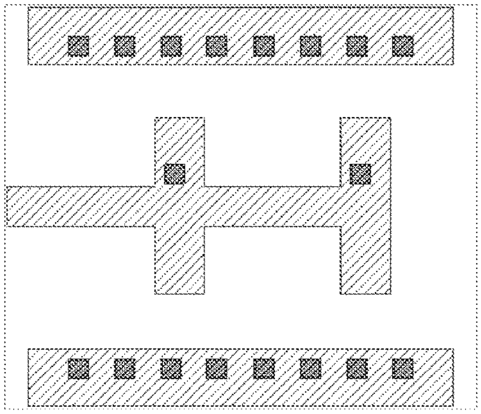
Figure 393A:
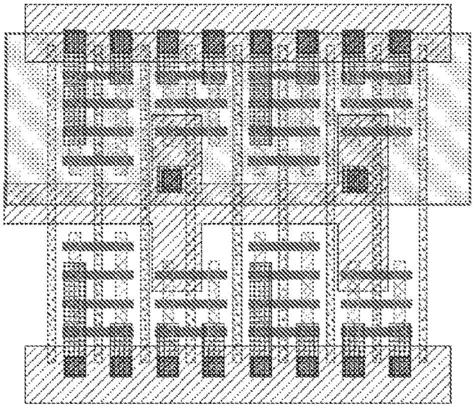
Figure 393B:
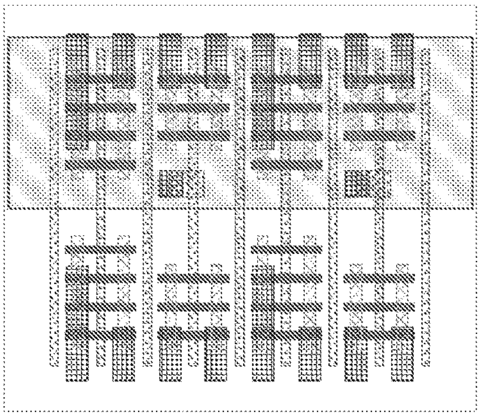
Figure 393C:
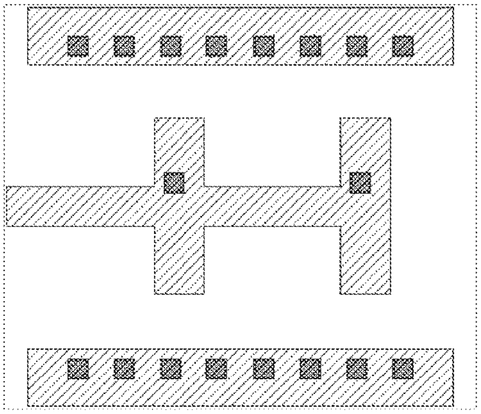
Figure 394A:
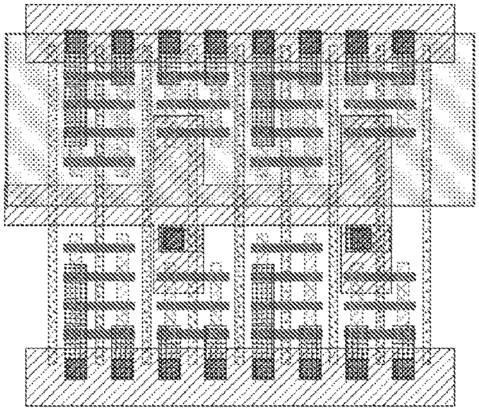
Figure 394B:
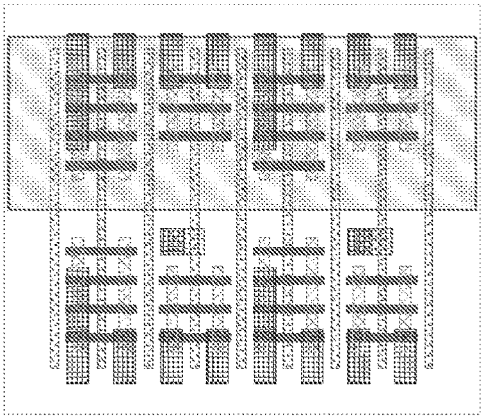
Figure 394C:
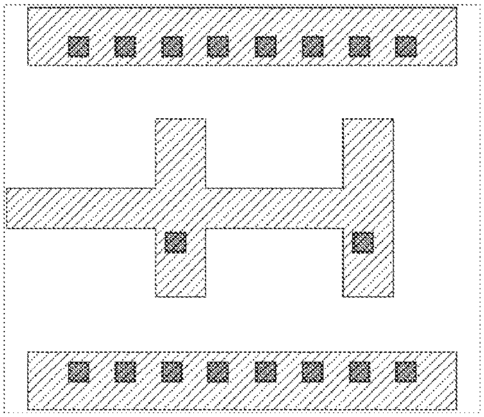
Figure 395A:
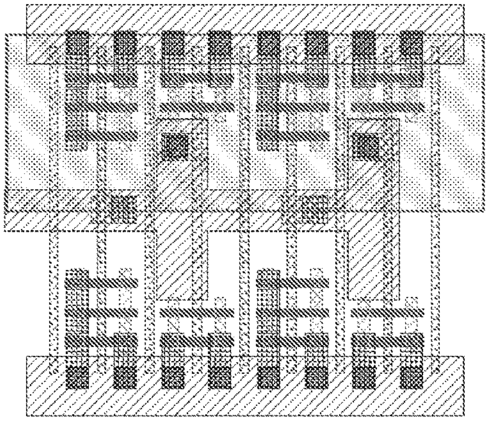
Figure 395B:
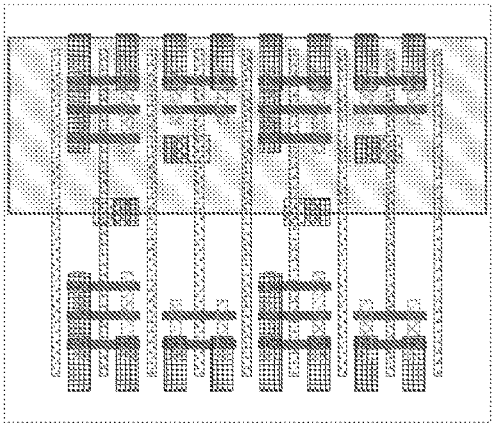
Figure 395C:
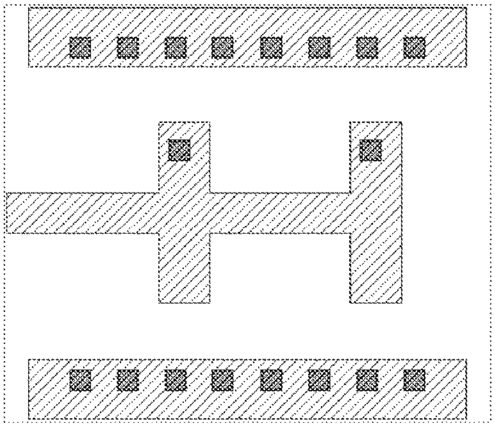
Figure 396A:
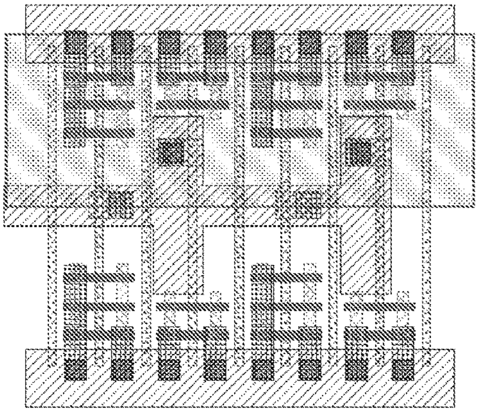
Figure 396B:
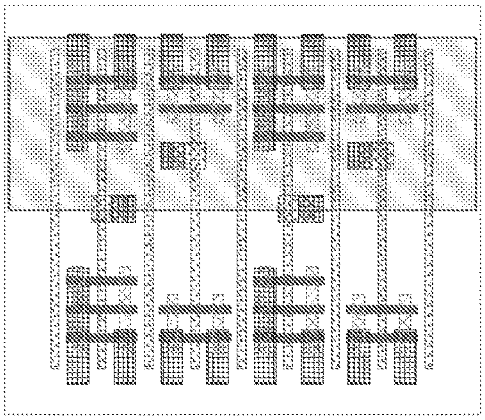
Figure 396C:
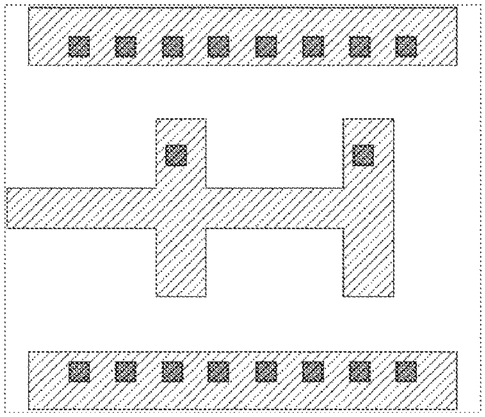
Figure 397A:
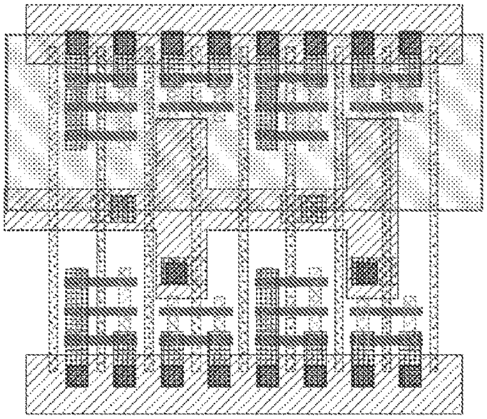
Figure 397B:
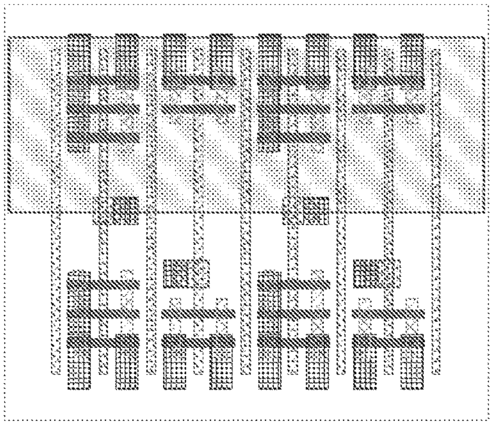
Figure 397C:
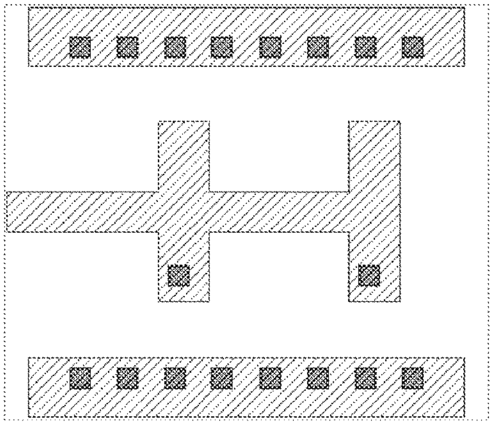
Figure 398A:
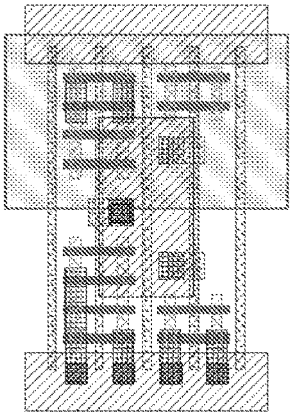
Figure 398B:
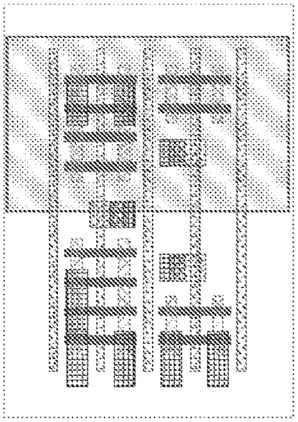
Figure 398C:
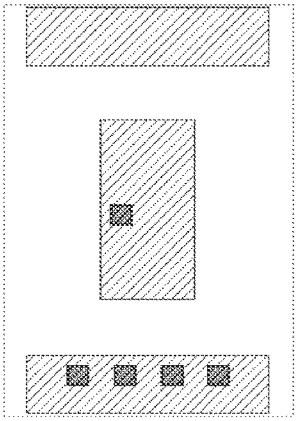
Figure 399A:
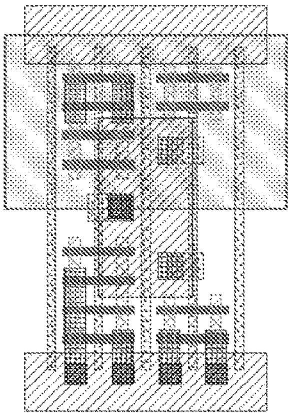
Figure 399B:
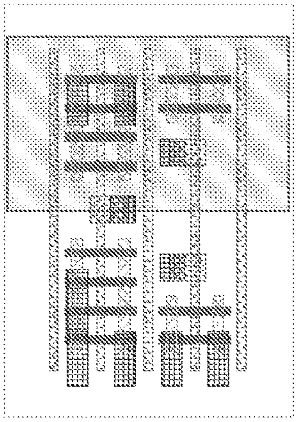
Figure 399C:
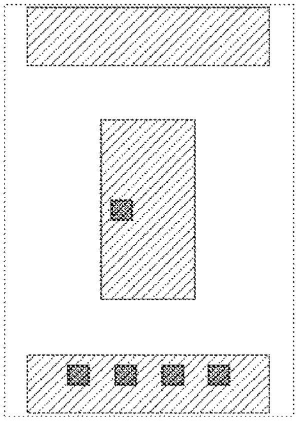
Figure 400A:
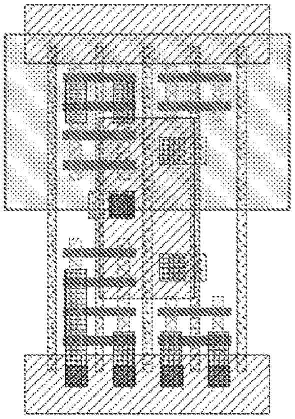
Figure 400B:
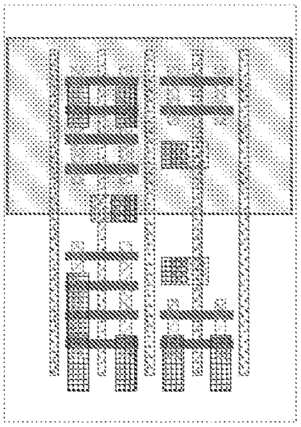
Figure 400C:
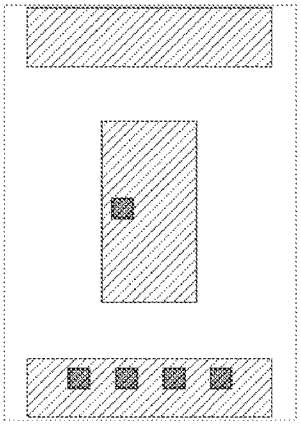
Figure 401A:
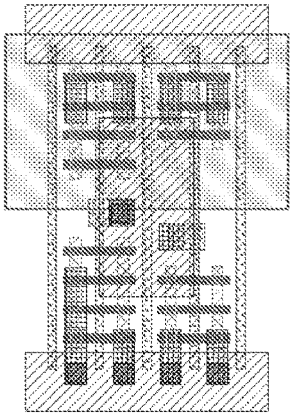
Figure 401B:
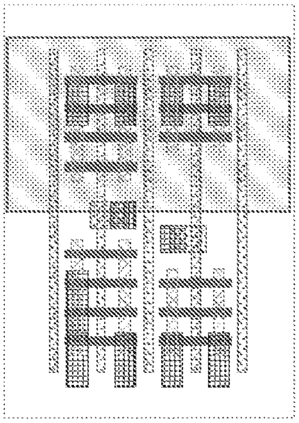
Figure 401C:
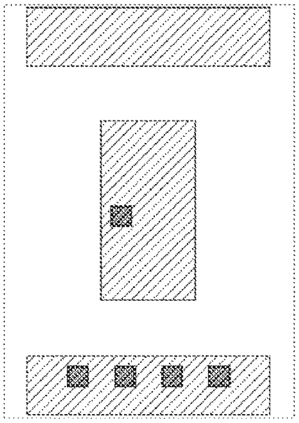
Figure 402A:
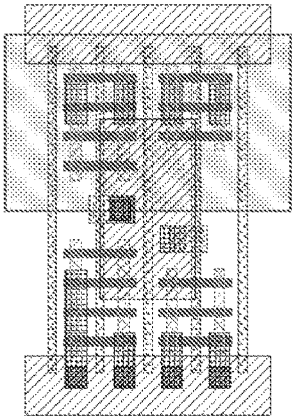
Figure 402B:
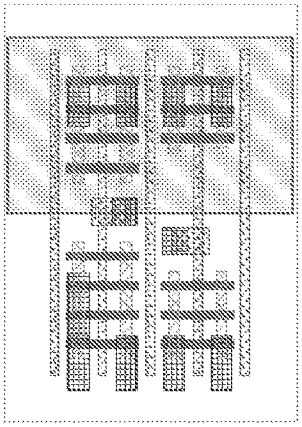
Figure 402C:
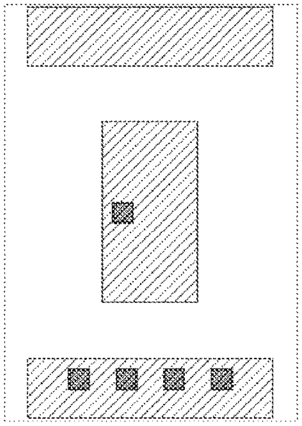
Figure 403A:
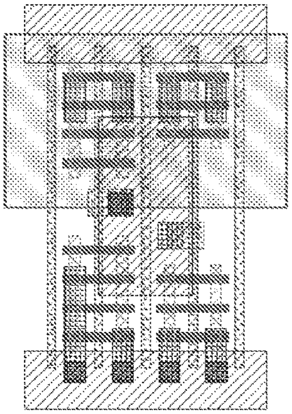
Figure 403B:
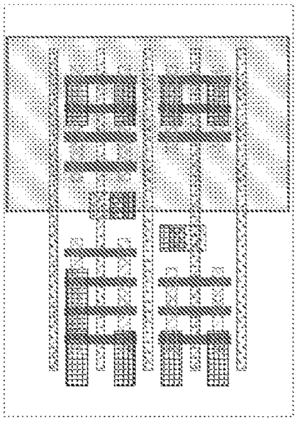
Figure 403C:
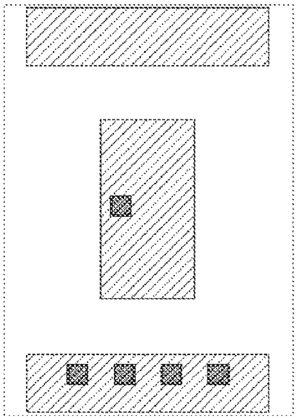
Figure 404A:
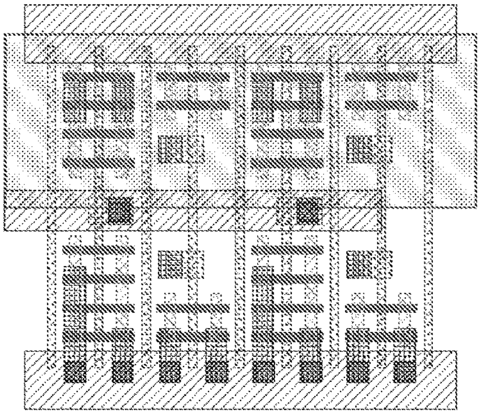
Figure 404B:
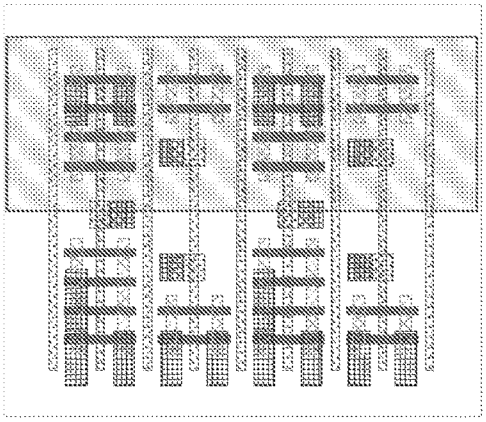
Figure 404C:
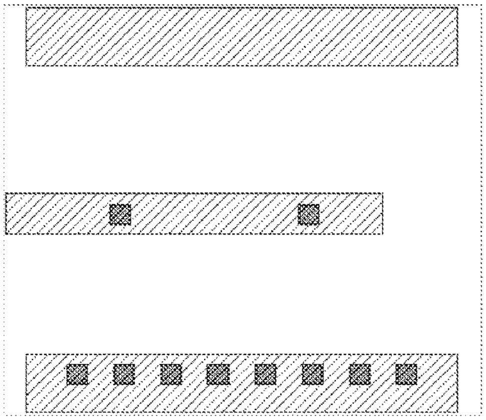
Figure 405A:
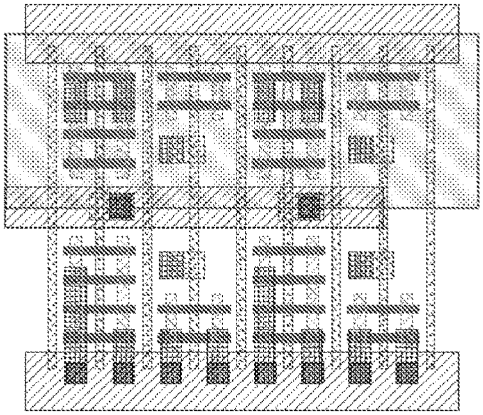
Figure 405B:
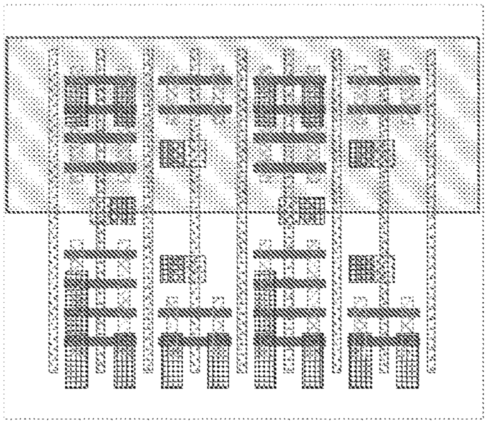
Figure 405C:
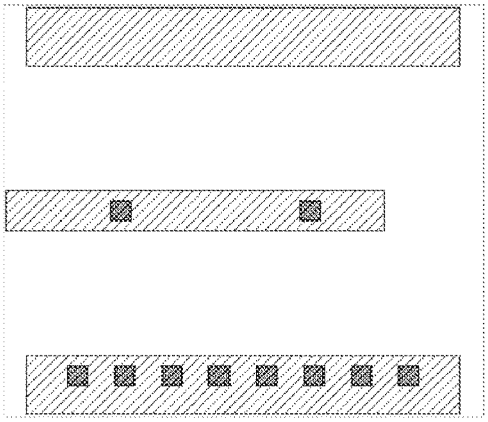
Figure 406A:
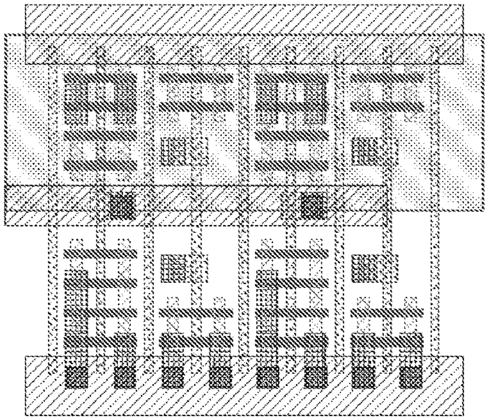
Figure 406B:
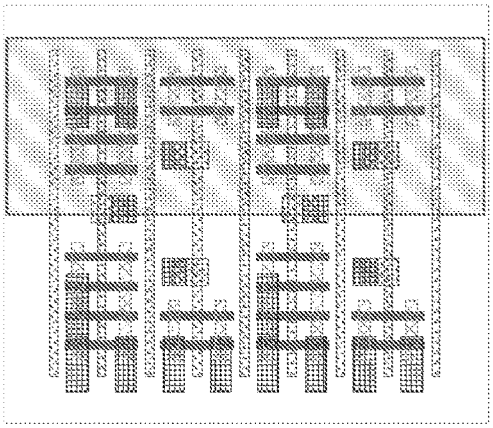
Figure 406C:
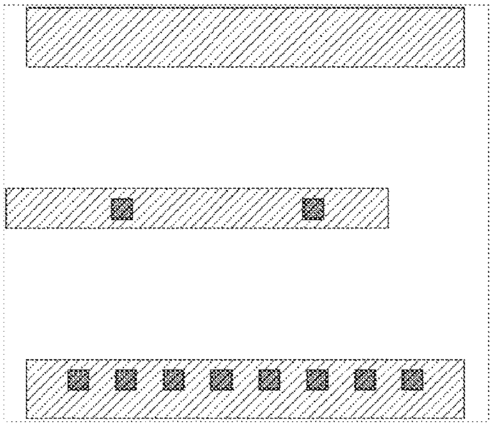
Figure 407A:
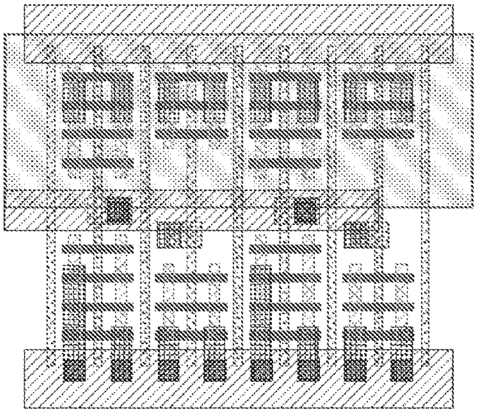
Figure 407B:
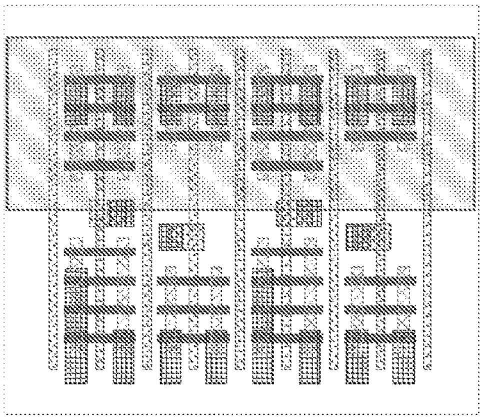
Figure 407C:
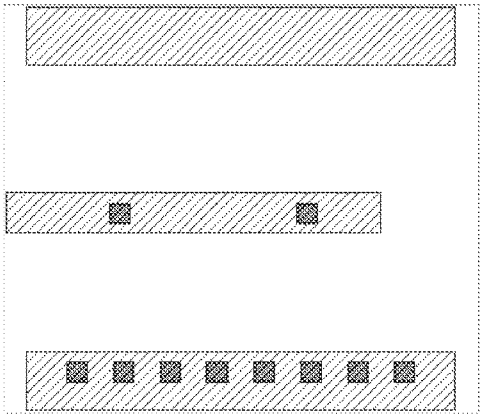
Figure 408A:
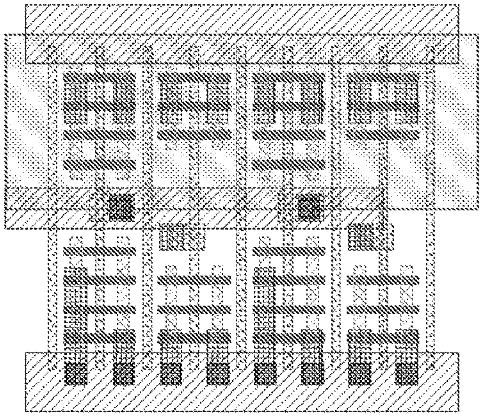
Figure 408B:
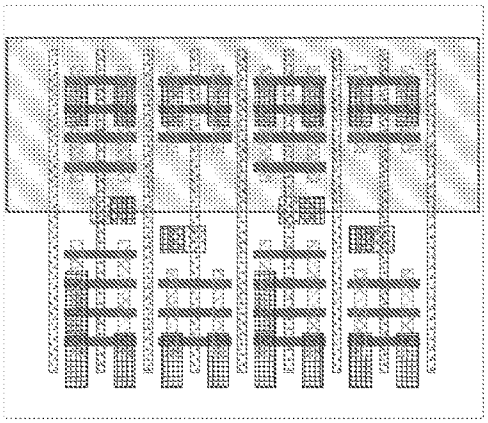
Figure 408C:
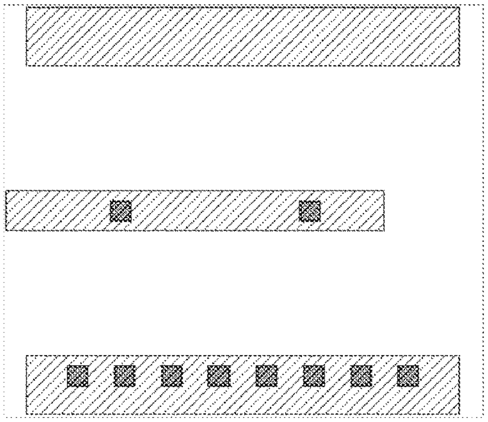
Figure 409A:
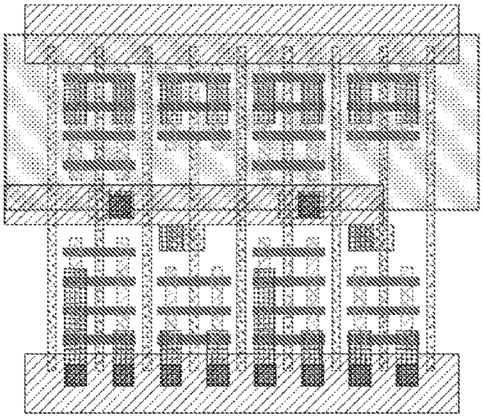
Figure 409B:
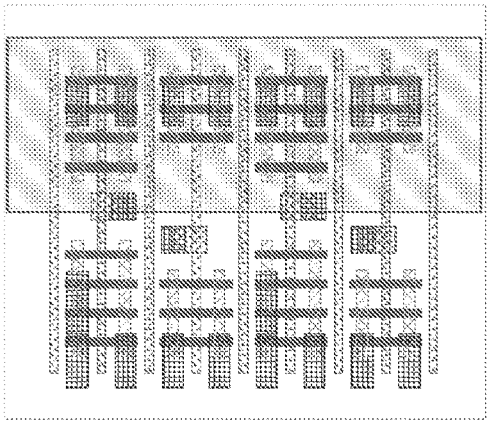
Figure 409C:
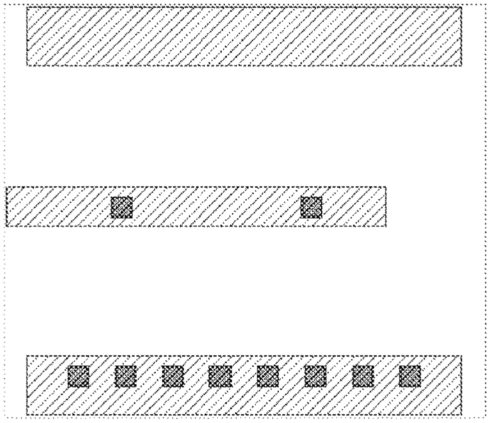
Figure 410A:
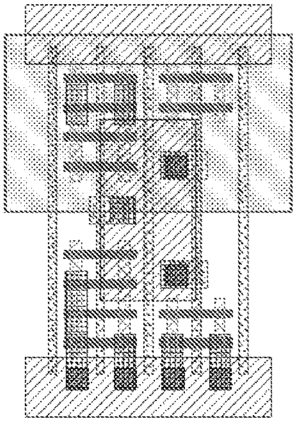
Figure 410B:
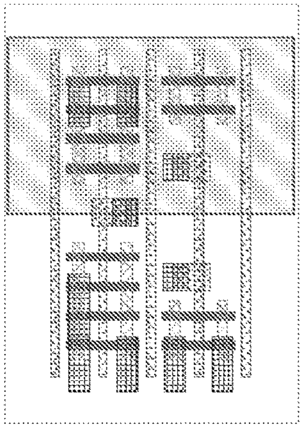
Figure 410C:
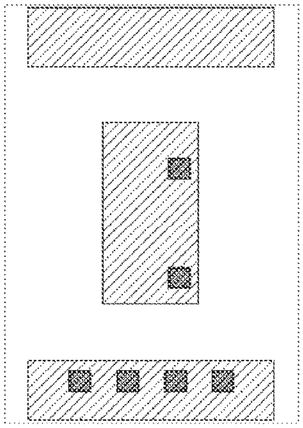
Figure 411A:
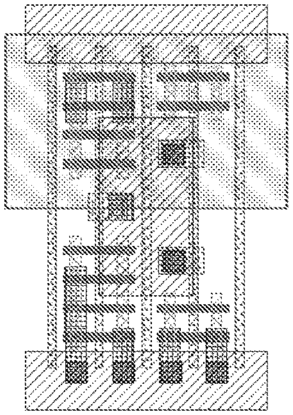
Figure 411B:
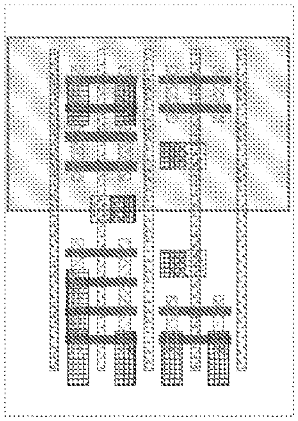
Figure 411C:
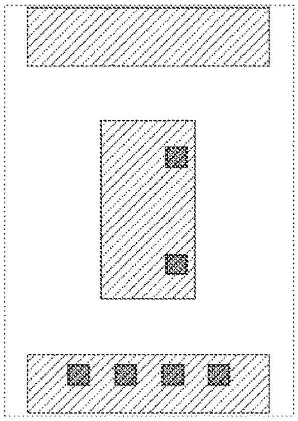
Figure 412A:
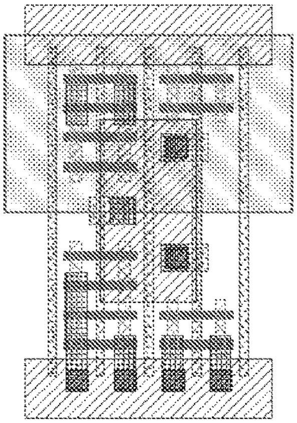
Figure 412B:
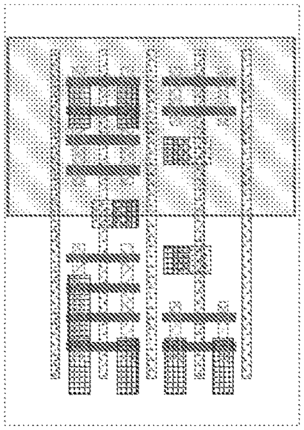
Figure 412C:
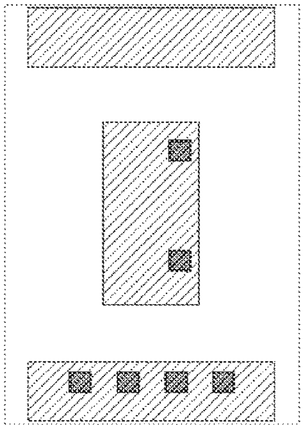
Figure 413A:
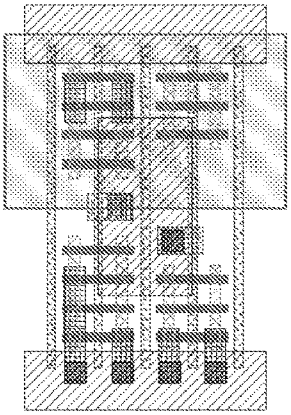
Figure 413B:
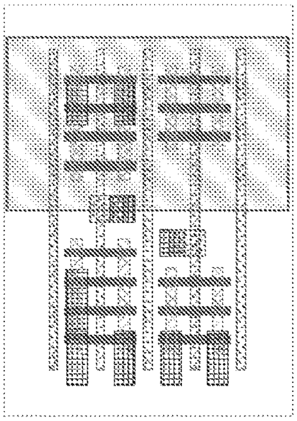
Figure 413C:
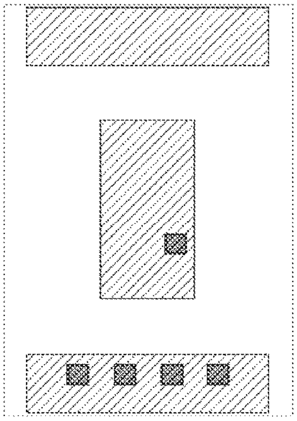
Figure 414A:
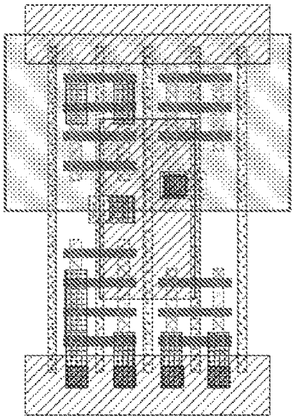
Figure 414B:
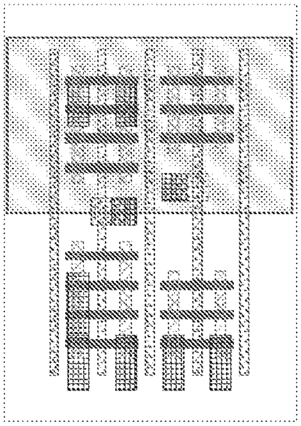
Figure 414C:
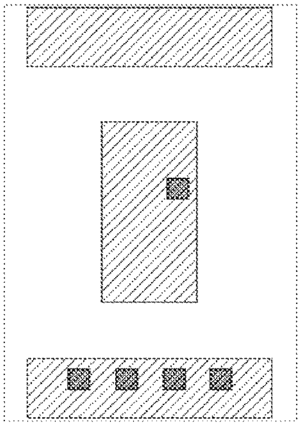
Figure 415A:
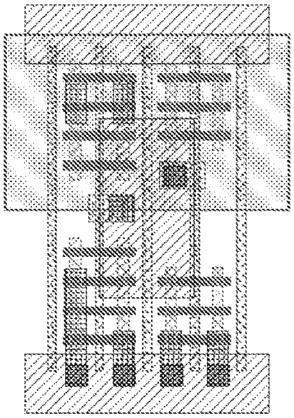
Figure 415B:
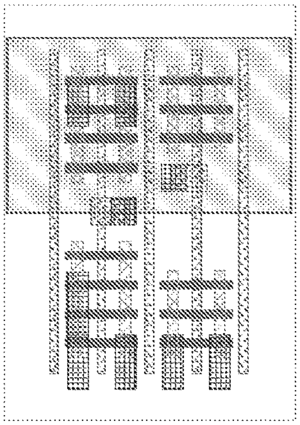
Figure 415C:
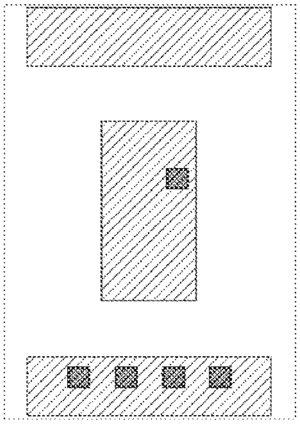
Figure 416A:
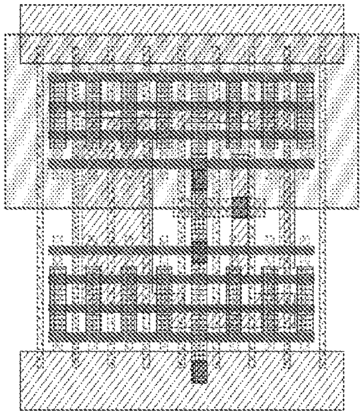
Figure 416B:
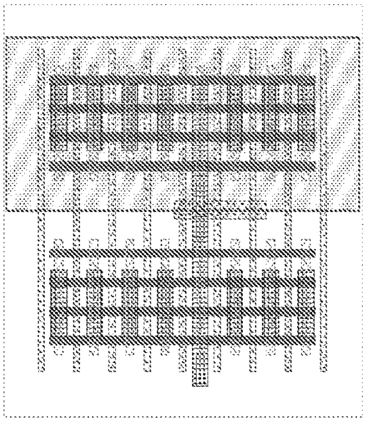
Figure 416C:
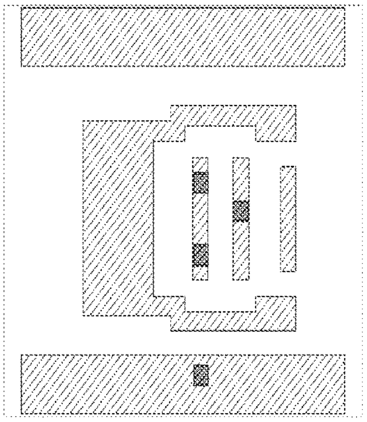
Figure 417A:
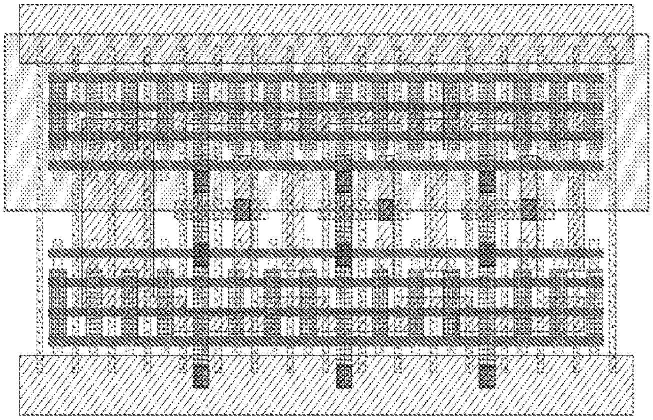
Figure 417B:
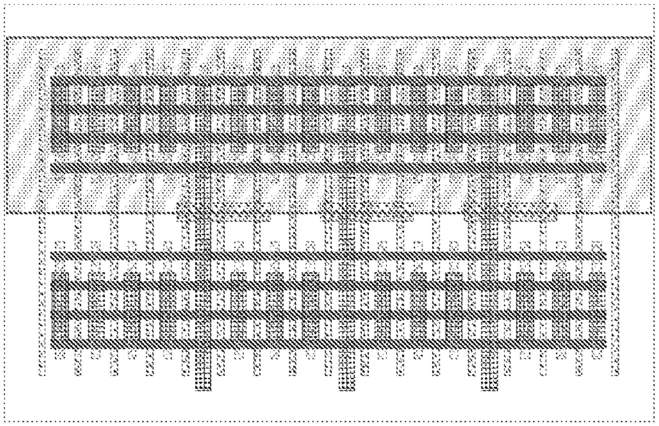
Figure 417C:
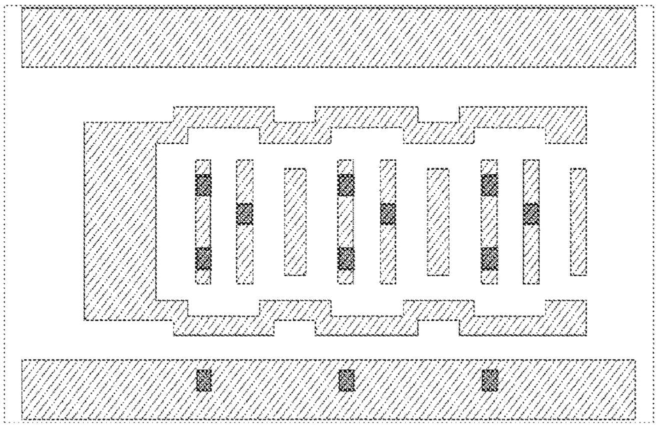
Figure 418A:
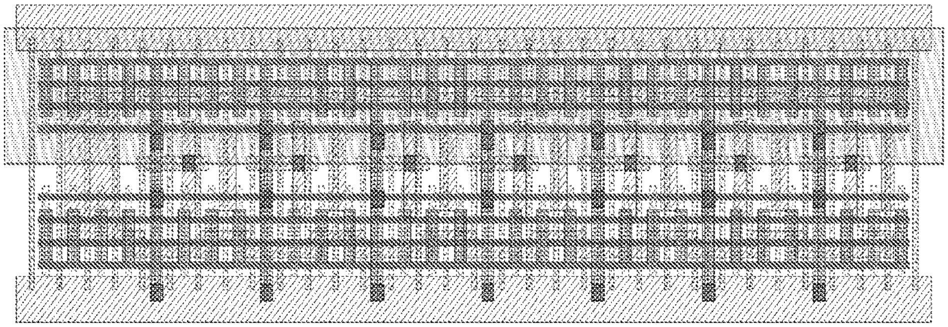
Figure 418B:
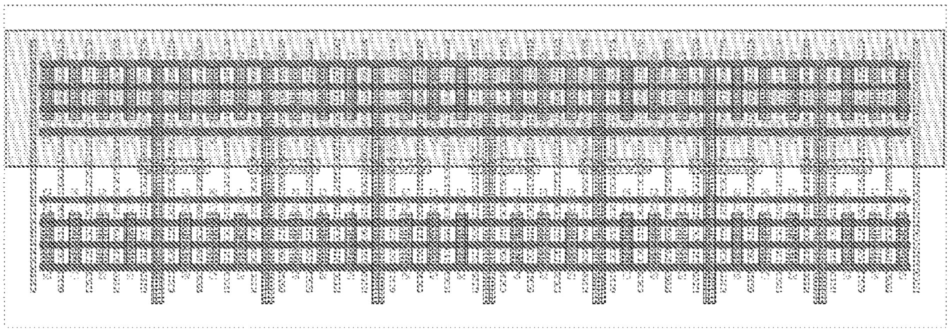
Figure 418C:
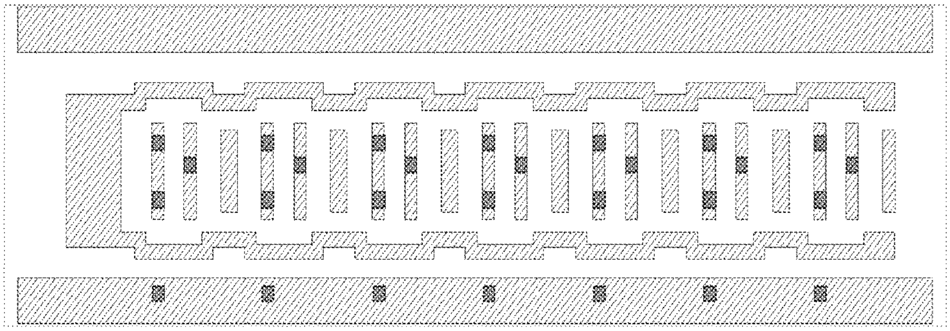
Figure 419A:
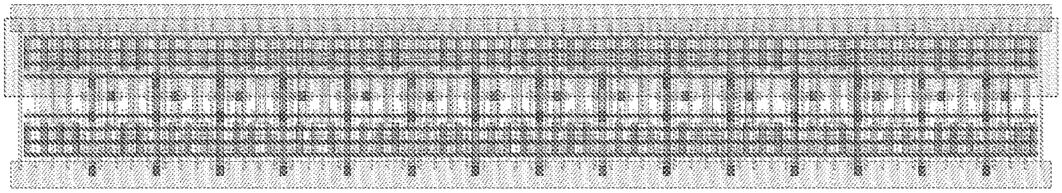
Figure 419B:
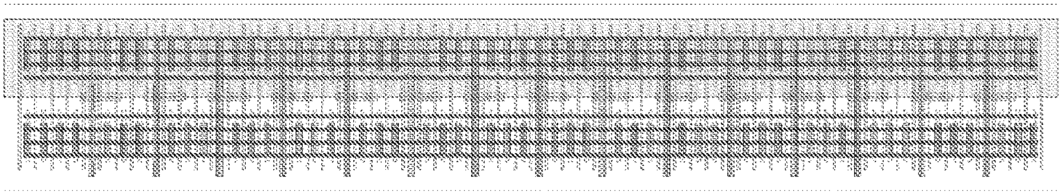
Figure 419C:
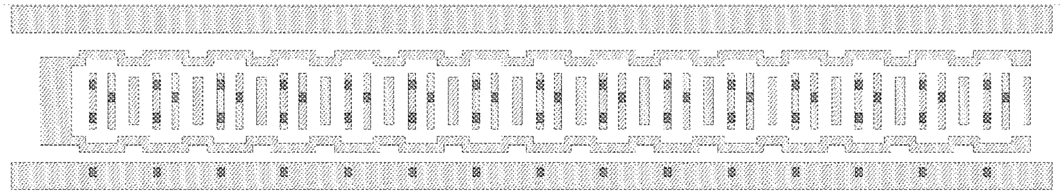
Figure 420A:
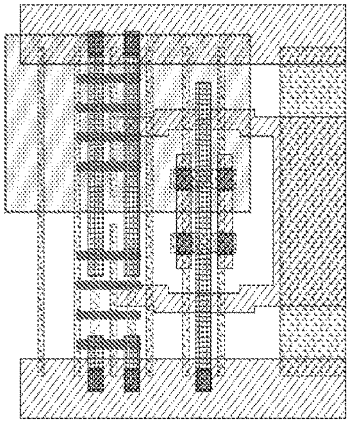
Figure 420B:
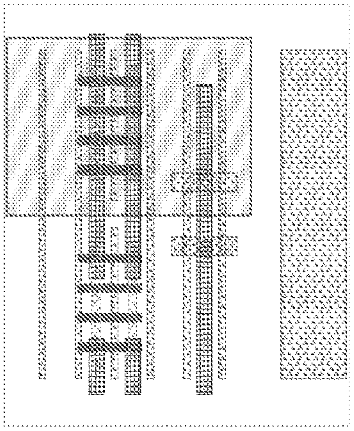
Figure 420C:
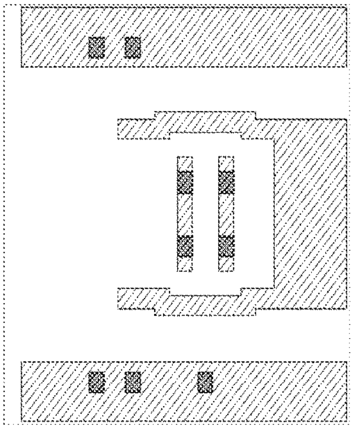
Figure 421A:
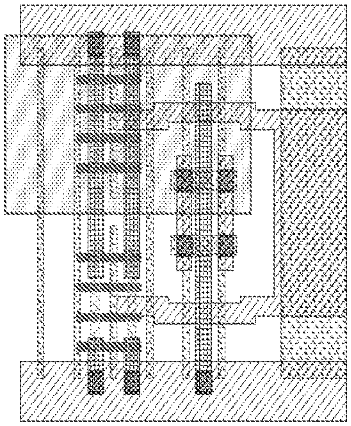
Figure 421B:
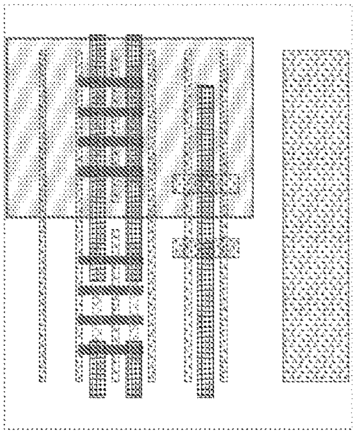
Figure 421C:
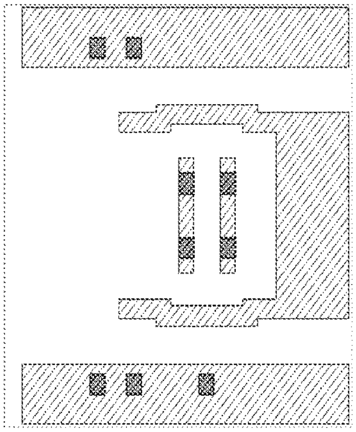
Figure 422A:
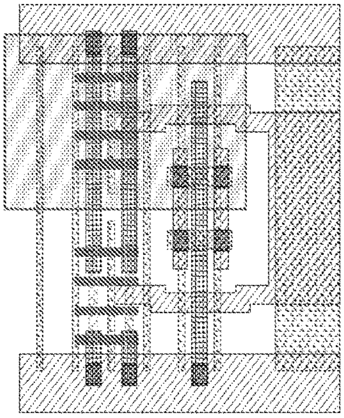
Figure 422B:
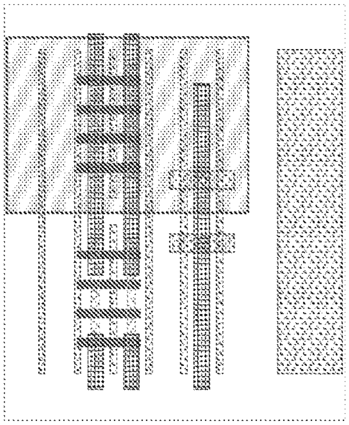
Figure 422C:
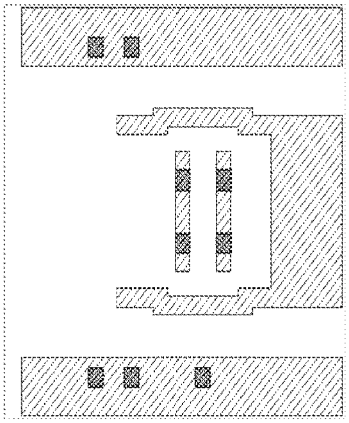
Figure 423A:
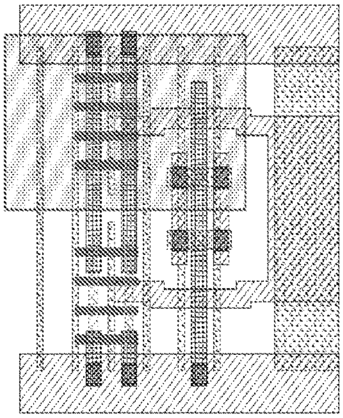
Figure 423B:
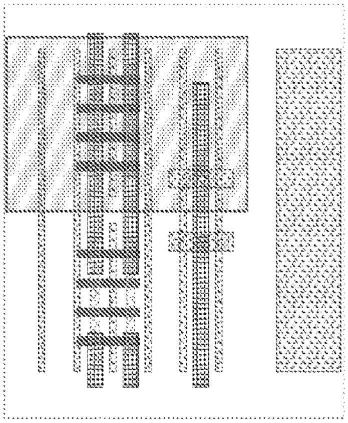
Figure 423C:
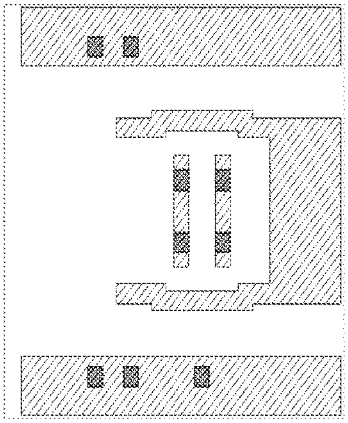
Figure 424A:
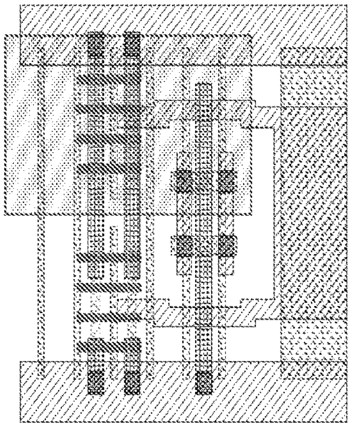
Figure 424B:
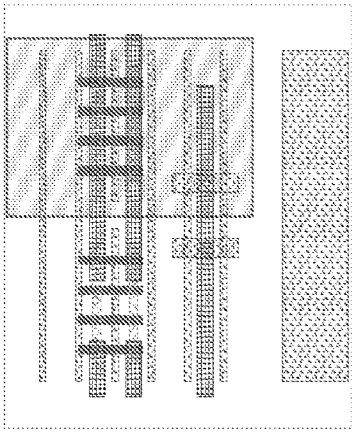
Figure 424C:
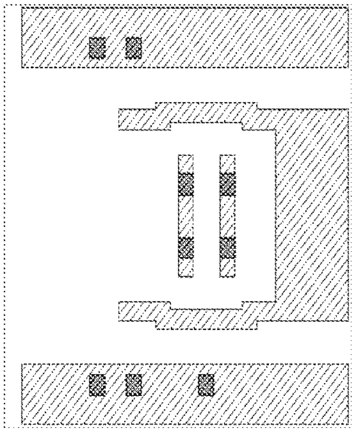
Figure 425A:
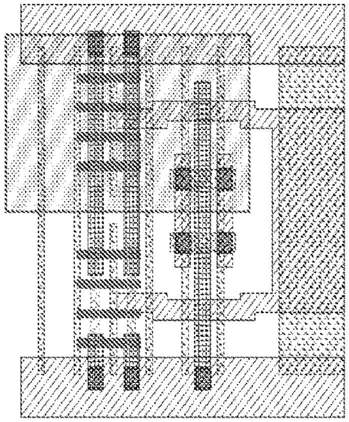
Figure 425B:
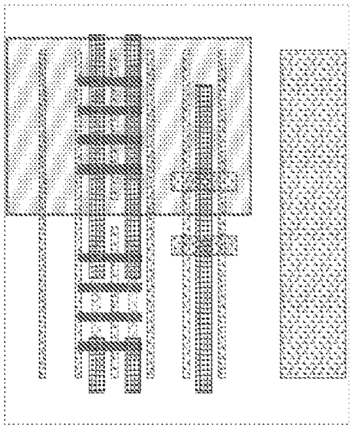
Figure 425C:
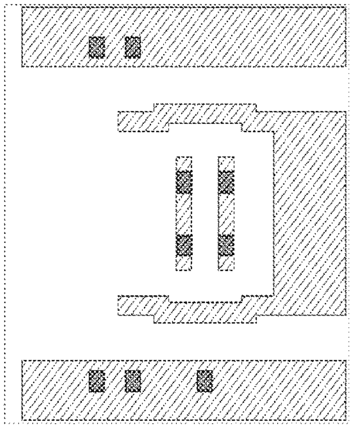
Figure 426A:
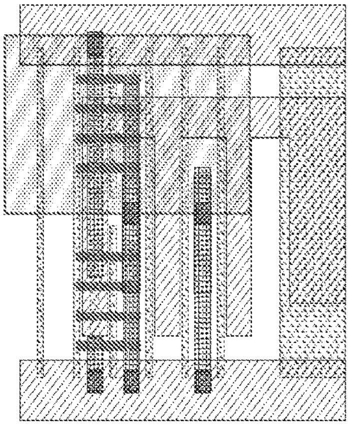
Figure 426B:
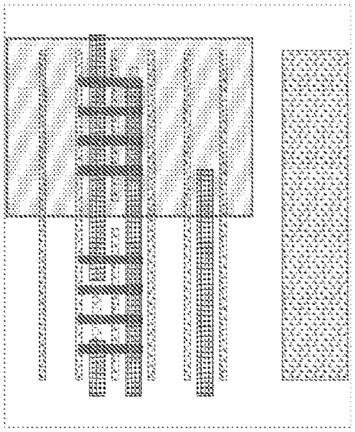
Figure 426C:
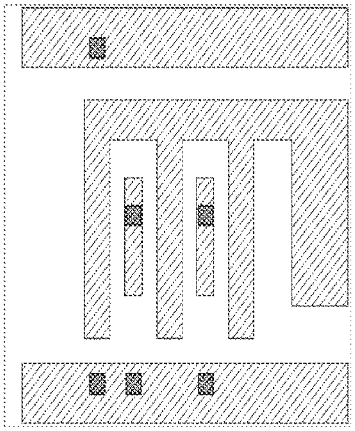
Figure 427A:
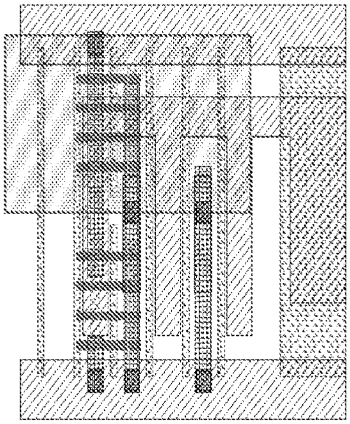
Figure 427B:
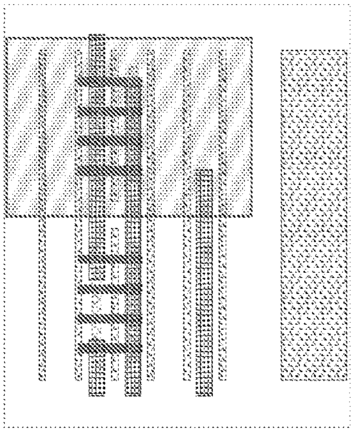
Figure 427C:
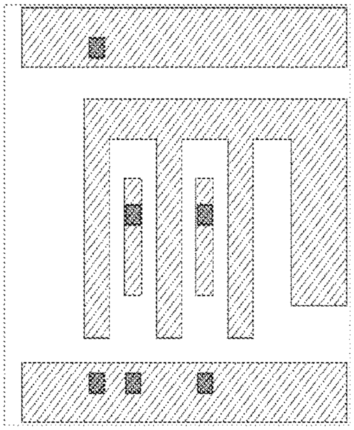
Figure 428A:
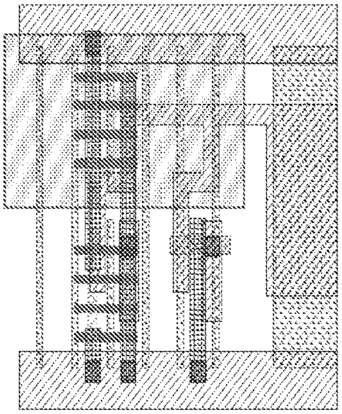
Figure 428B:
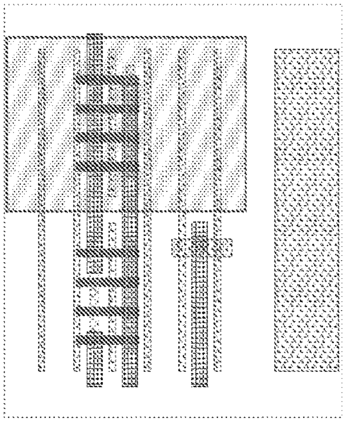
Figure 428C:
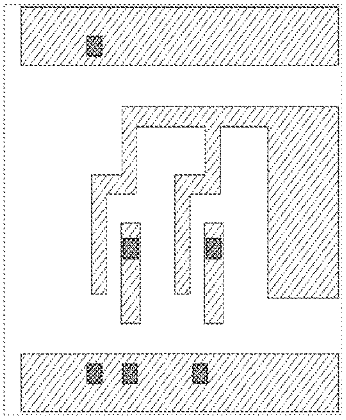
Figure 429A:
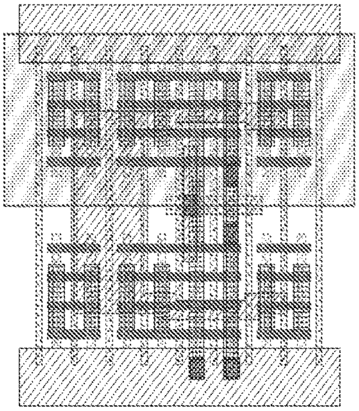
Figure 429B:
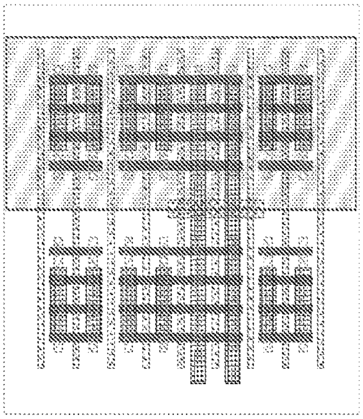
Figure 429C:
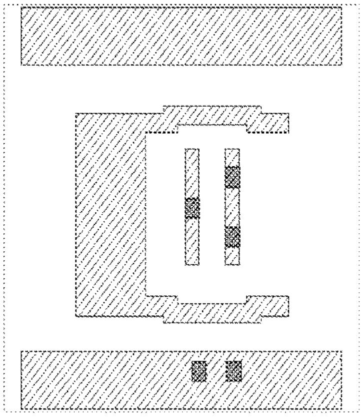
Figure 430A:
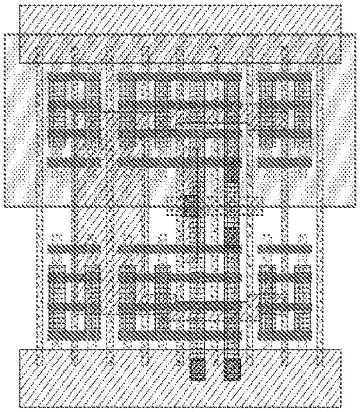
Figure 430B:
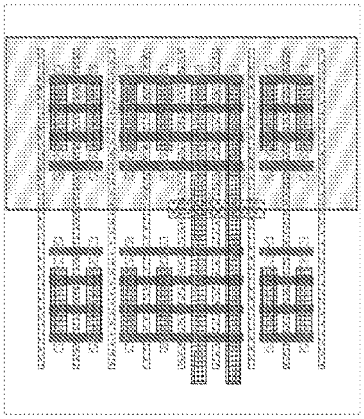
Figure 430C:
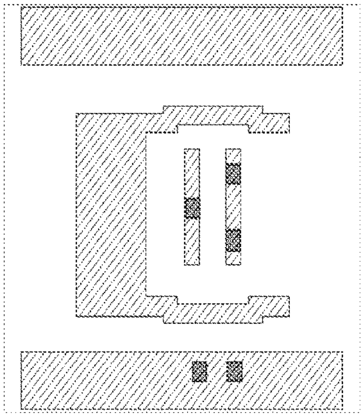
Figure 431A:
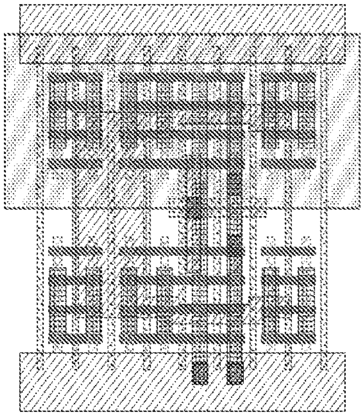
Figure 431B:
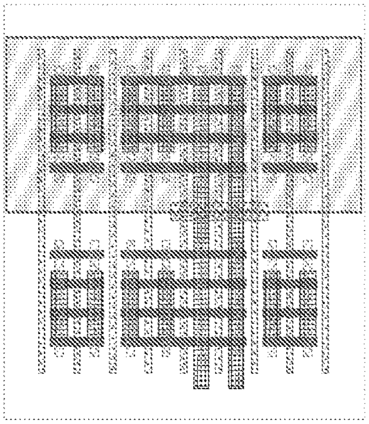
Figure 431C:
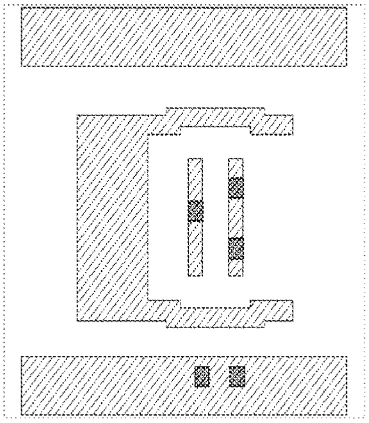
Figure 432A:
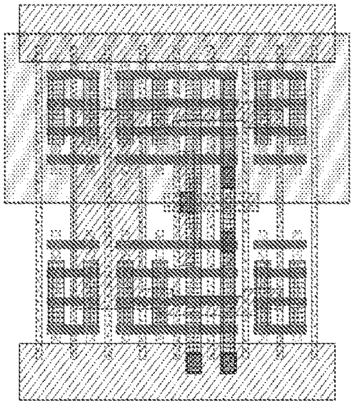
Figure 432B:
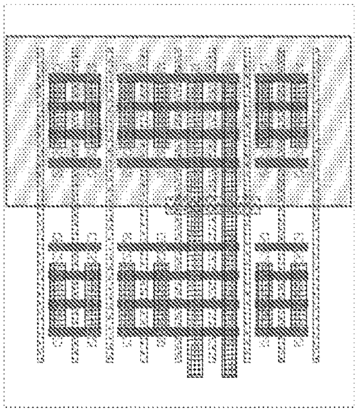
Figure 432C:
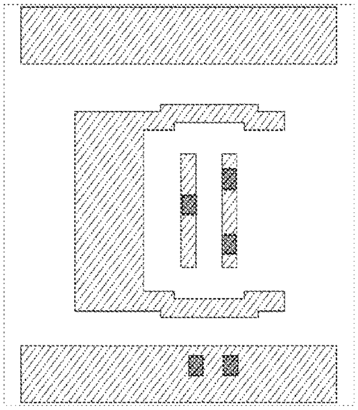
Figure 433A:
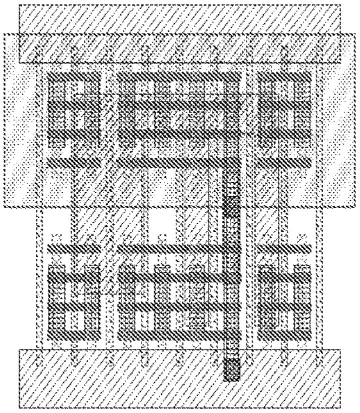
Figure 433B:
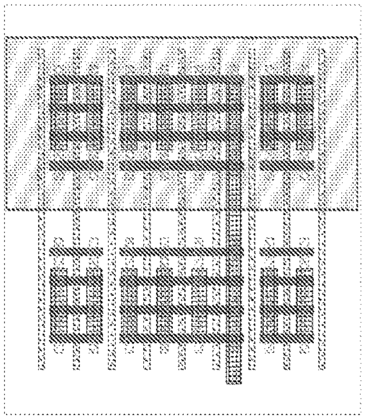
Figure 433C:
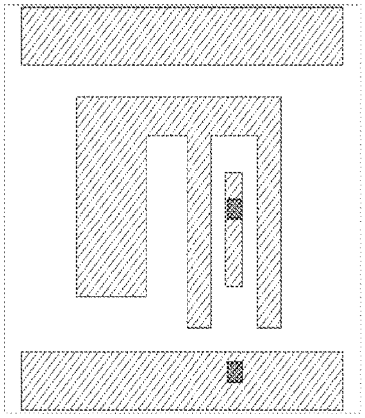
Figure 434A:
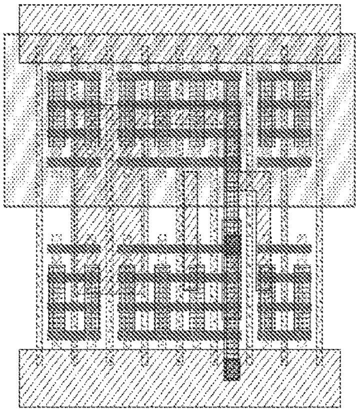
Figure 434B:
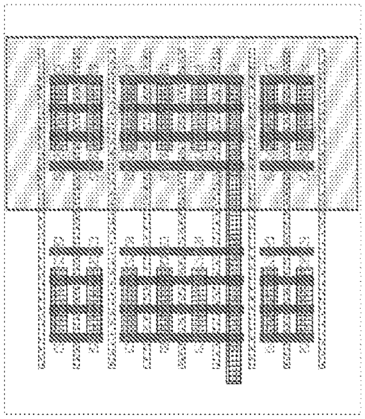
Figure 434C:
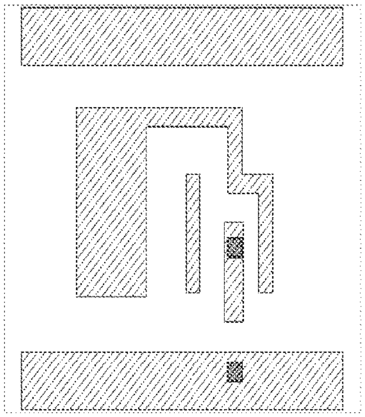
Figure 435A:
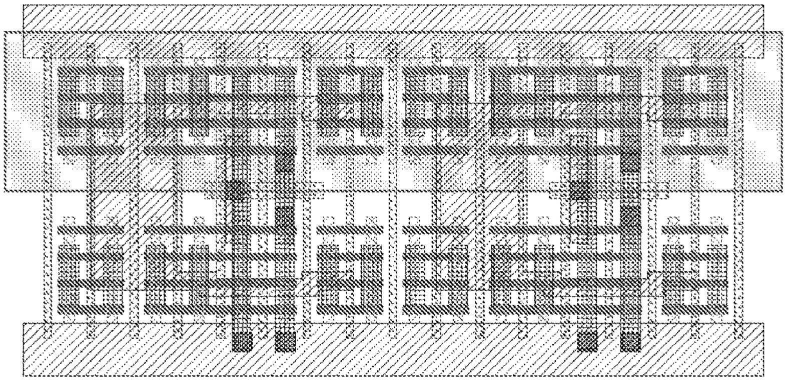
Figure 435B:
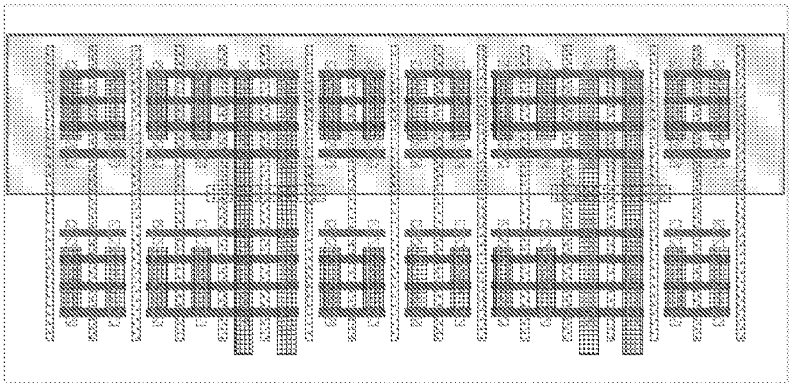
Figure 435C:
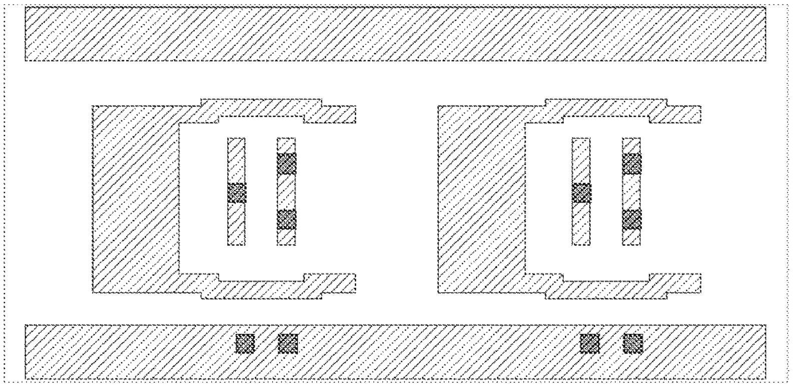
Figure 436A:
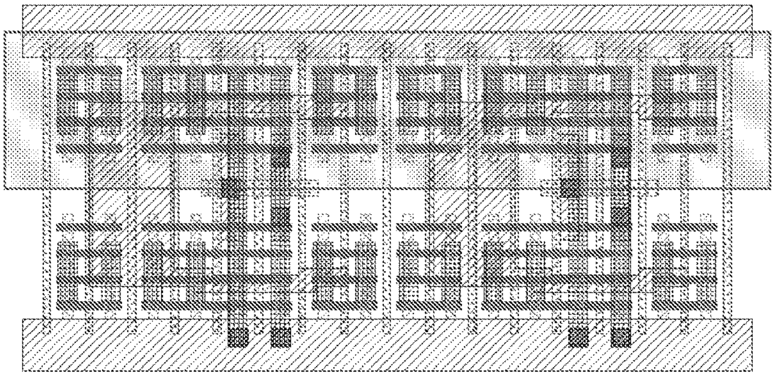
Figure 436B:
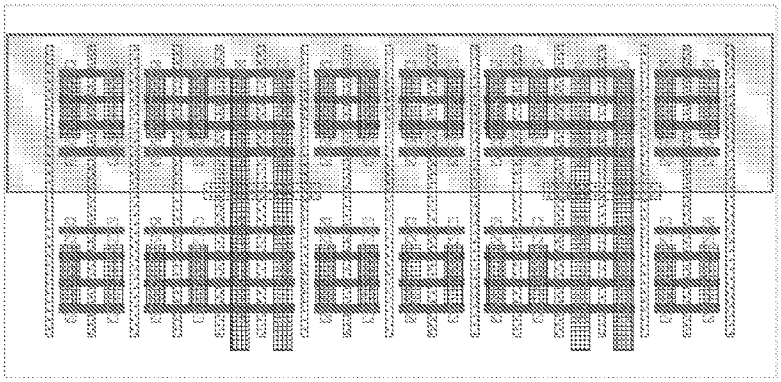
Figure 436C:
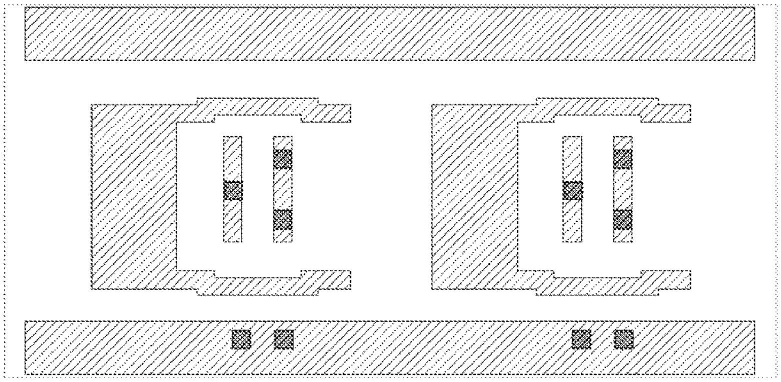
Figure 437A:
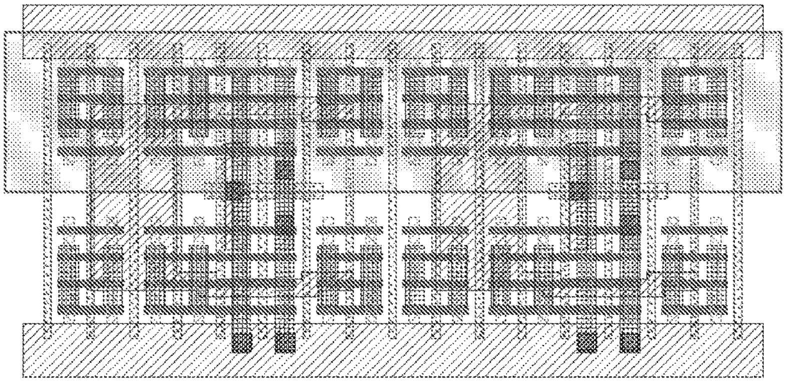
Figure 437B:
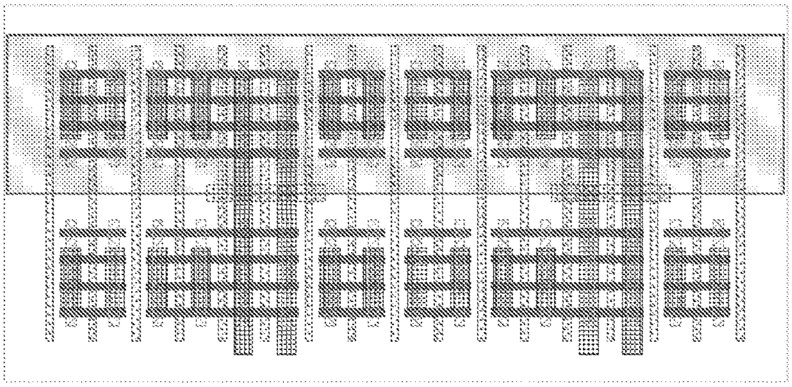
Figure 437C:
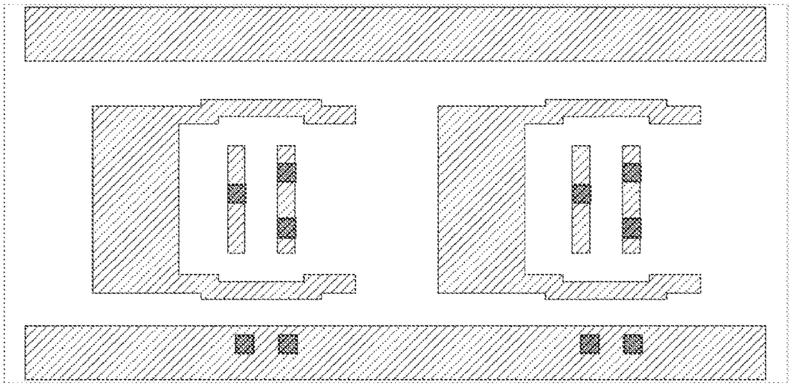
Figure 438A:
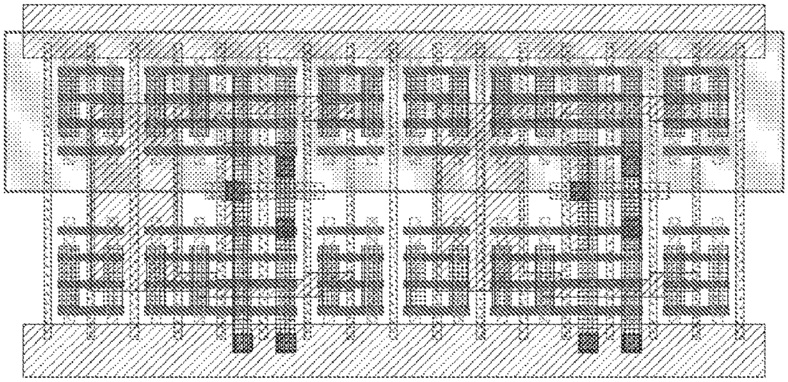
Figure 438B:
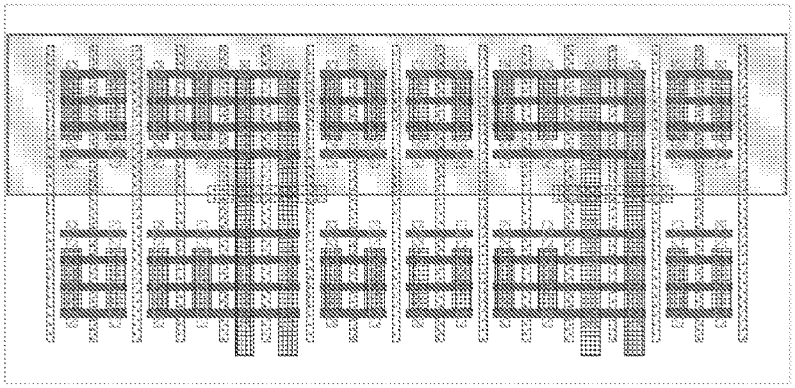
Figure 438C:
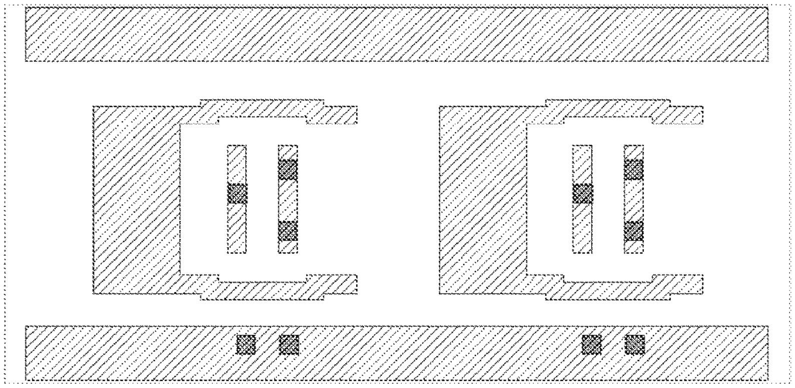
Figure 439A:
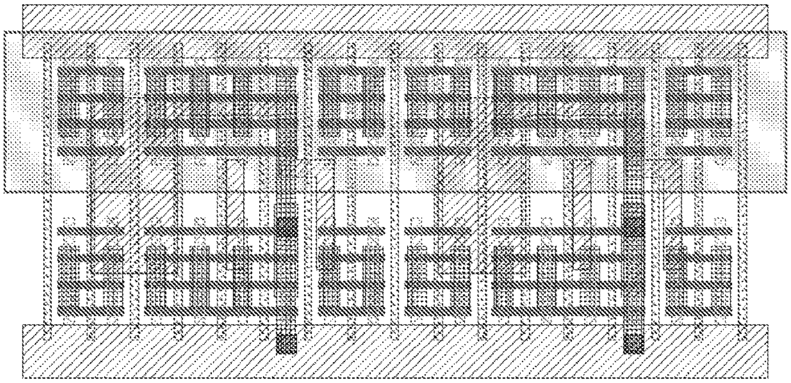
Figure 439B:
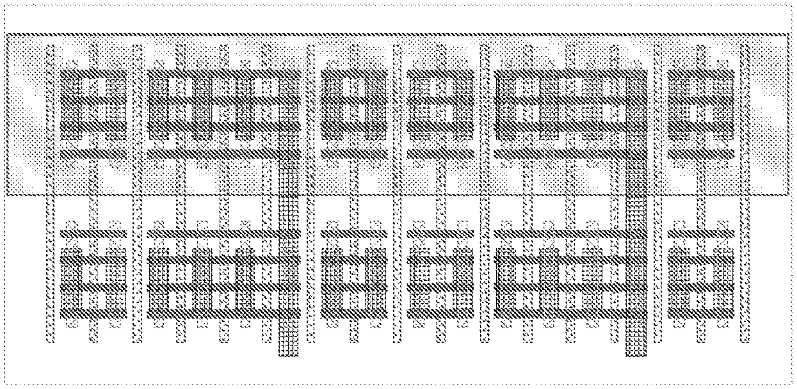
Figure 439C:
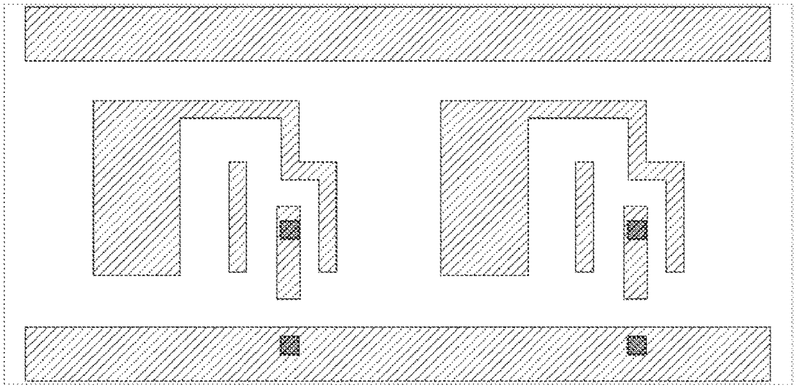
Figure 440A:
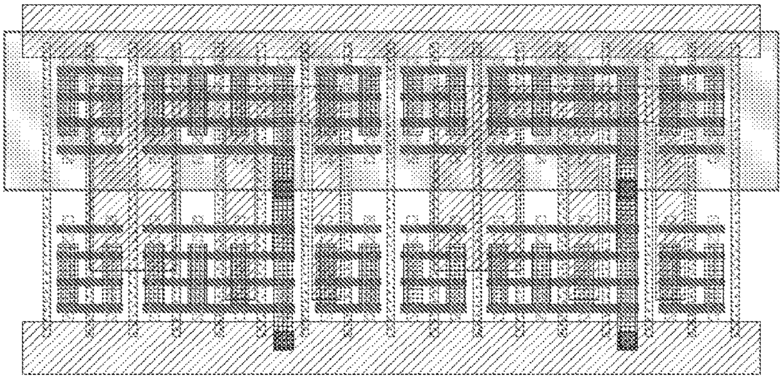
Figure 440B:
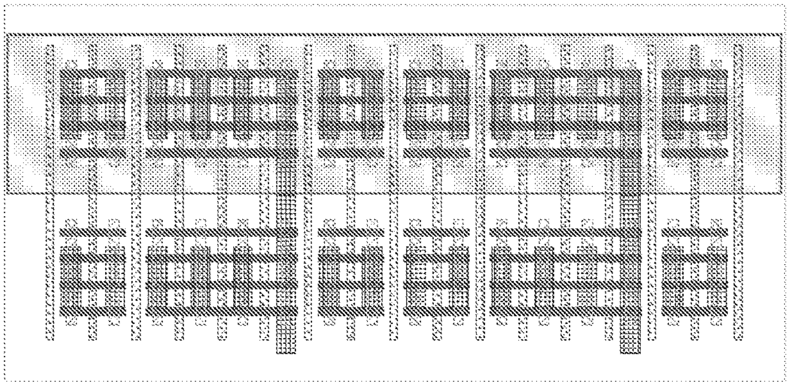
Figure 440C:
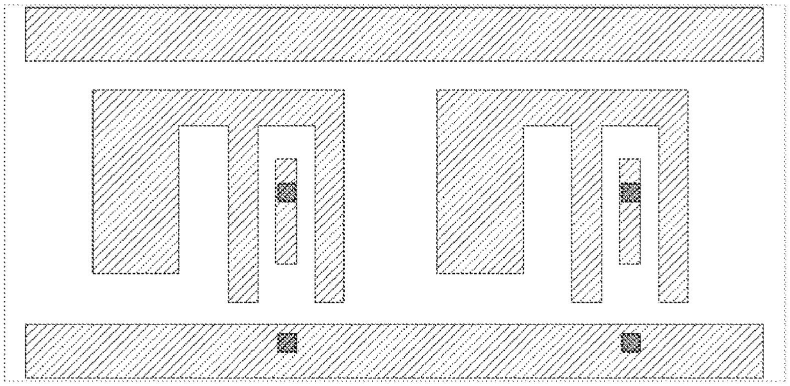
Figure 441A:
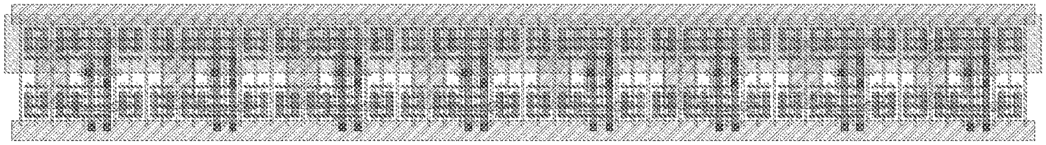
Figure 441B:
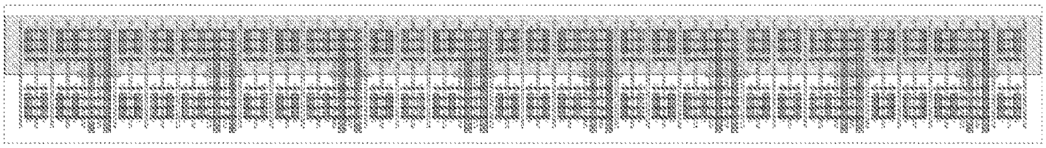
Figure 441C:
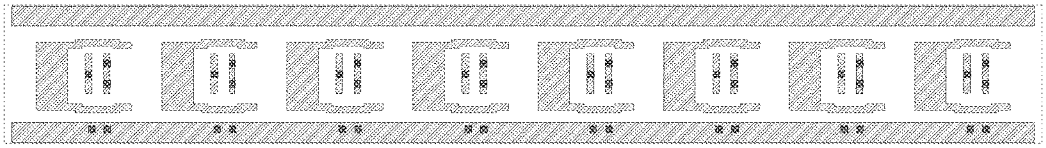
Figure 442A:
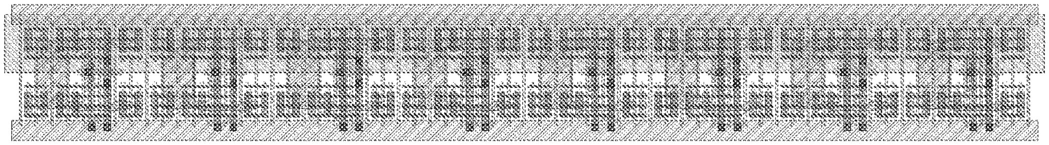
Figure 442B:
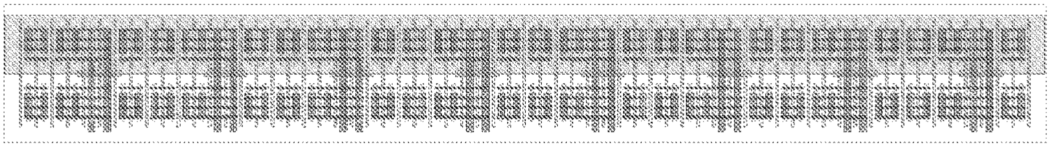
Figure 442C:
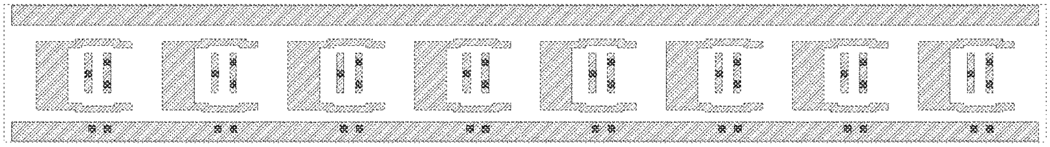
Figure 443A:
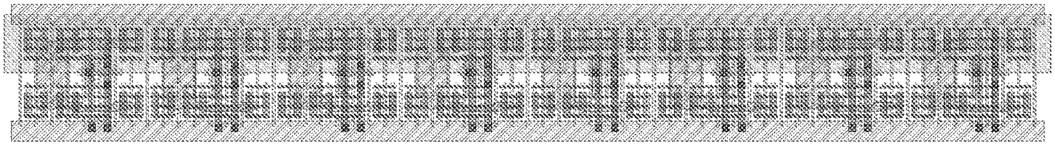
Figure 443B:
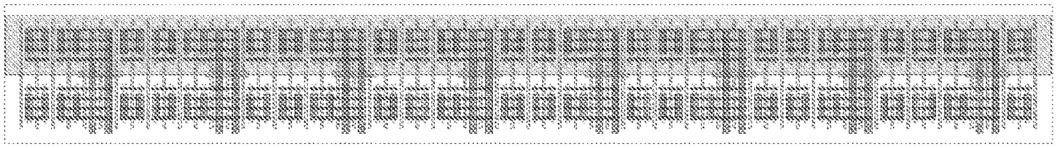
Figure 443C:
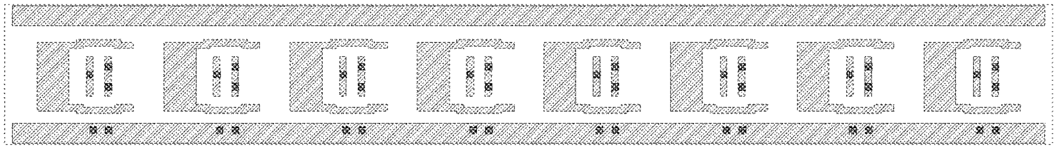
Figure 444A:
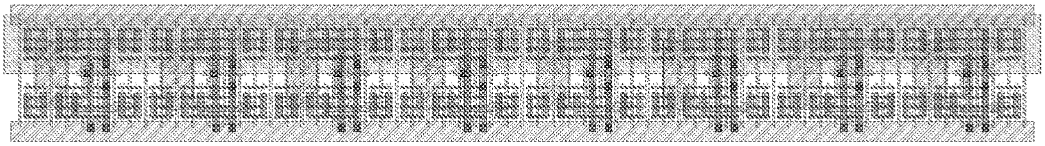
Figure 444B:
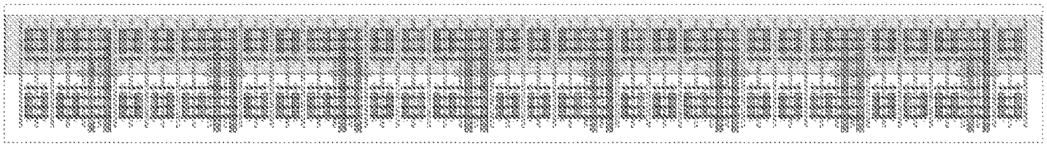
Figure 444C:
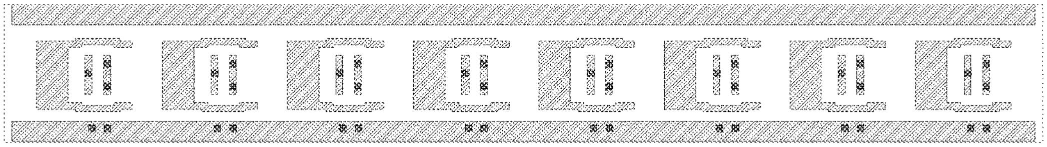
Figure 445A:
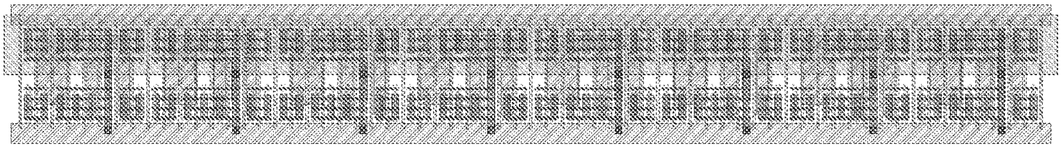
Figure 445B:
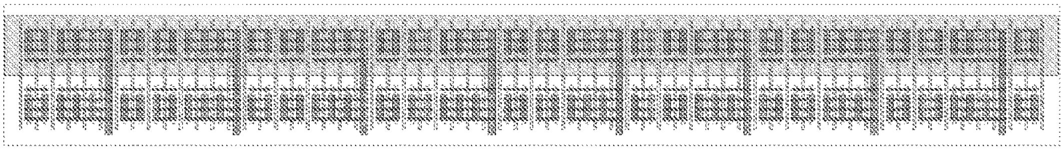
Figure 445C:
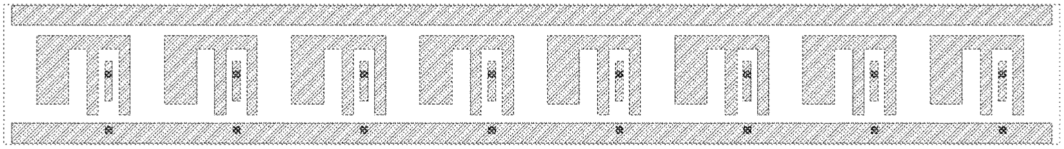
Figure 446A:
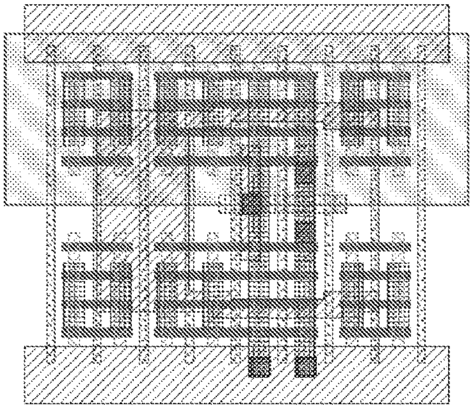
Figure 446B:
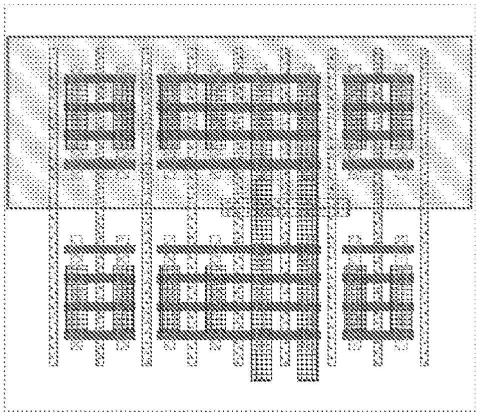
Figure 446C:
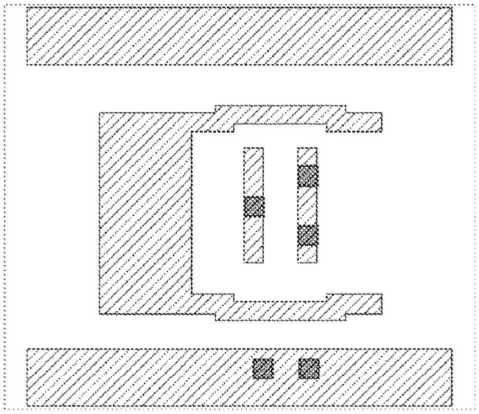
Figure 447A:
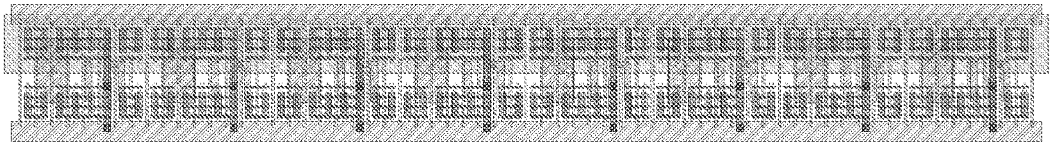
Figure 447B:
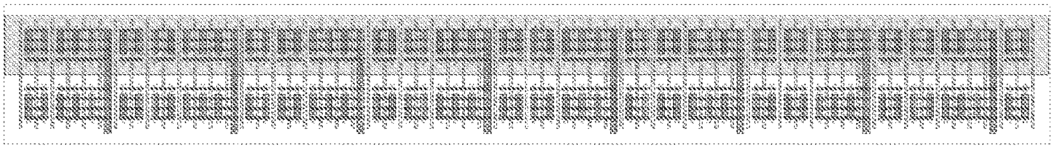
Figure 447C:
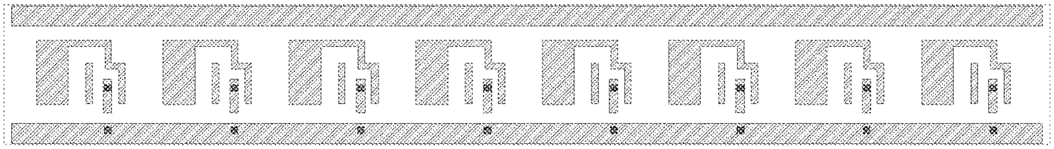
Figure 448A:
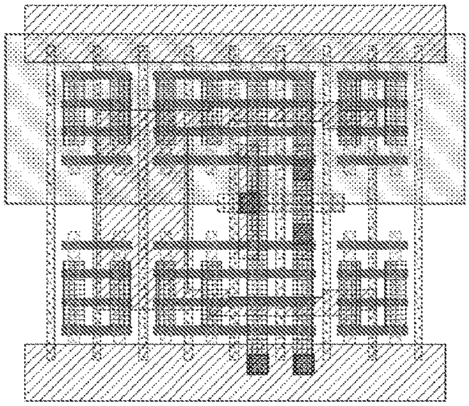
Figure 448B:
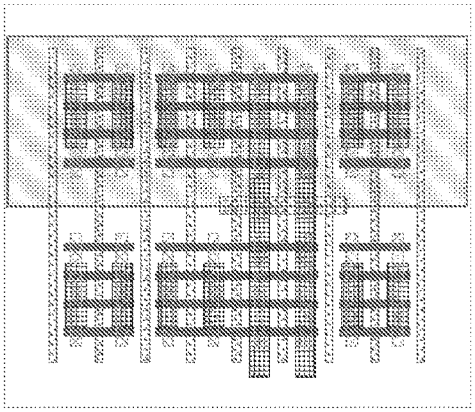
Figure 448C:
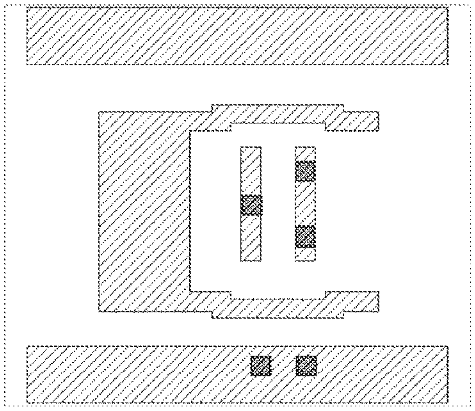
Figure 449A:
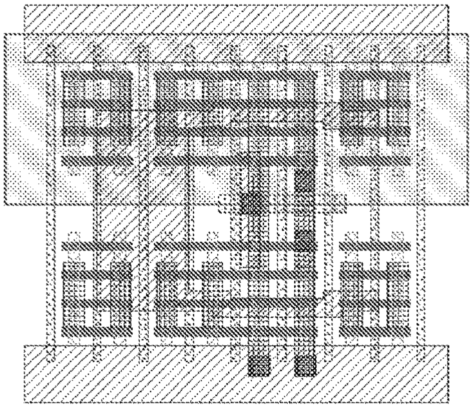
Figure 449B:
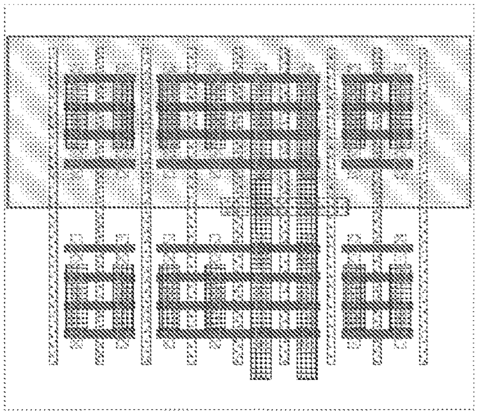
Figure 449C:
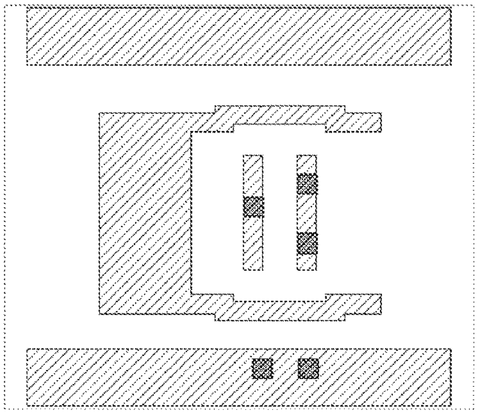
Figure 450A:
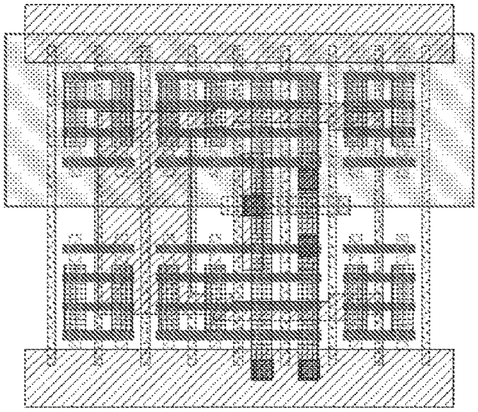
Figure 450B:
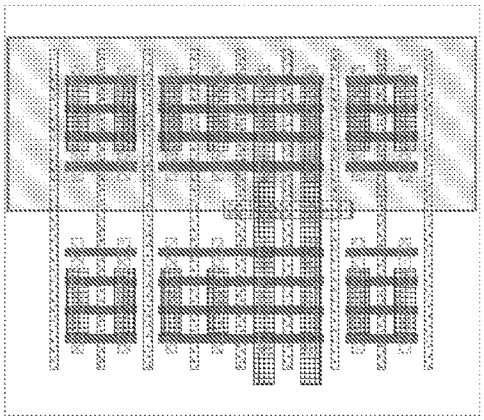
Figure 450C:
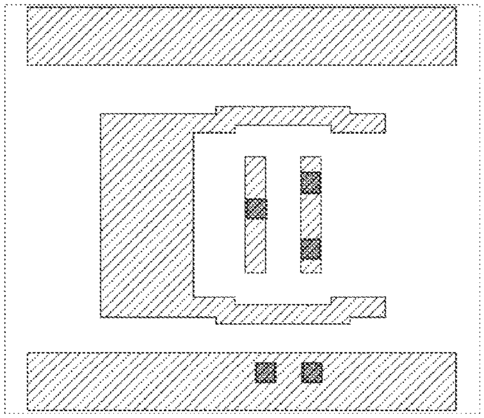
Figure 451A:
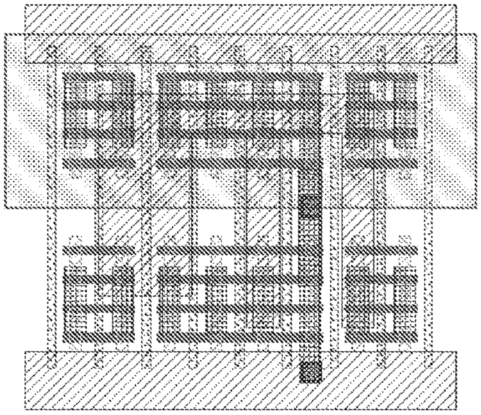
Figure 451B:
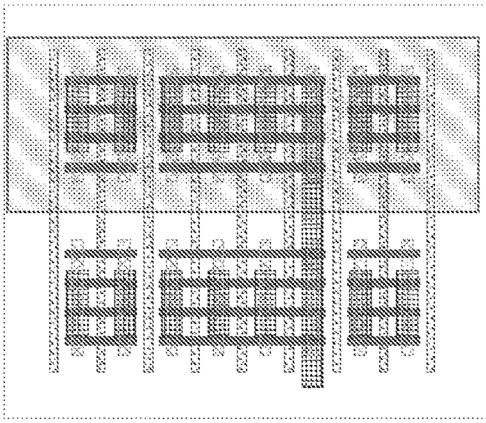
Figure 451C:
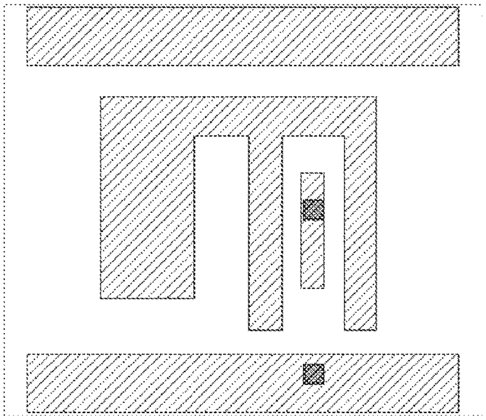
Figure 452A:
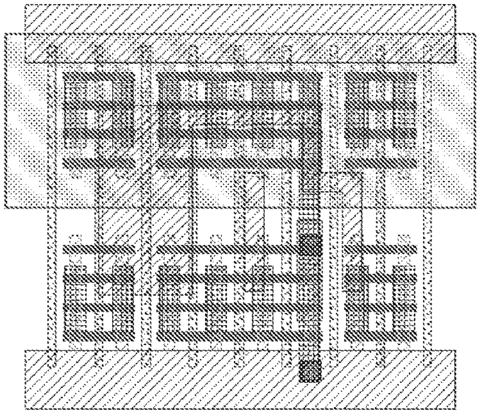
Figure 452B:
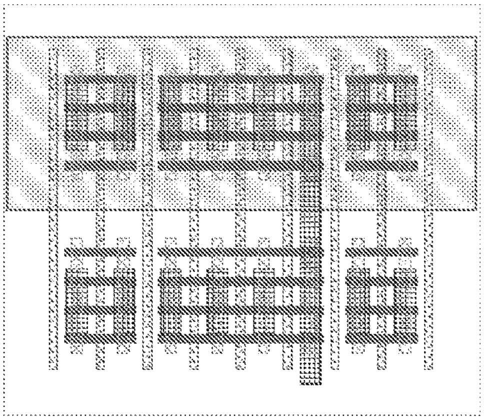
Figure 452C:
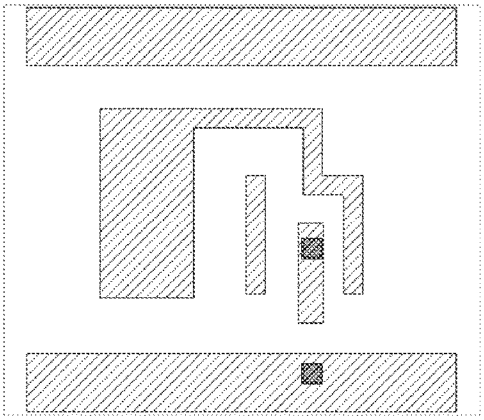
Figure 453A:
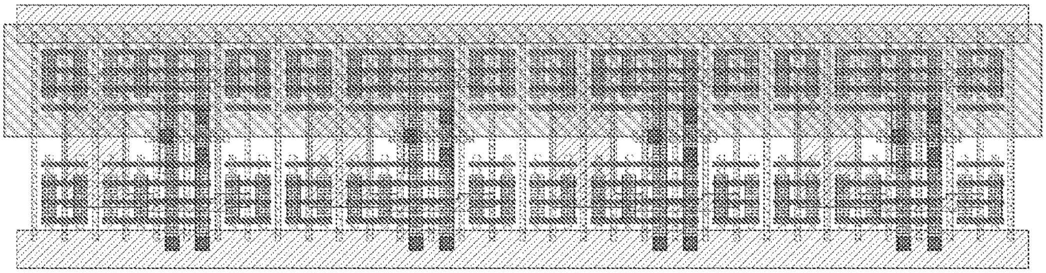
Figure 453B:
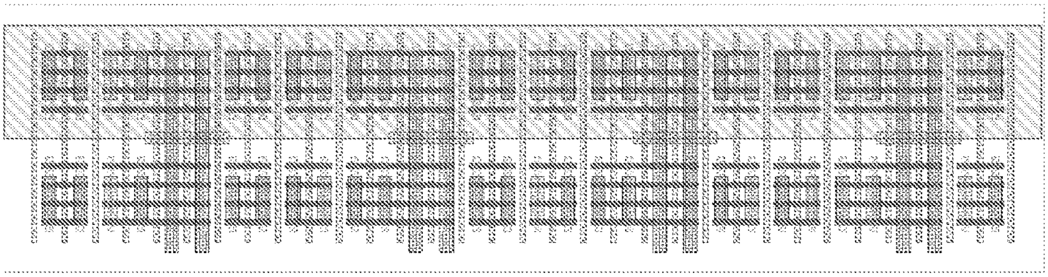
Figure 453C:
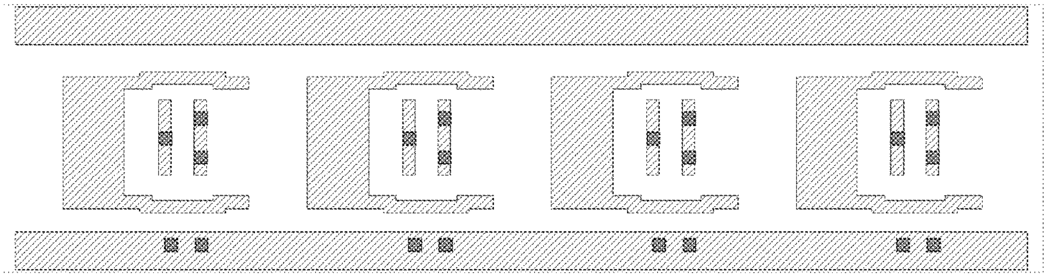
Figure 454A:
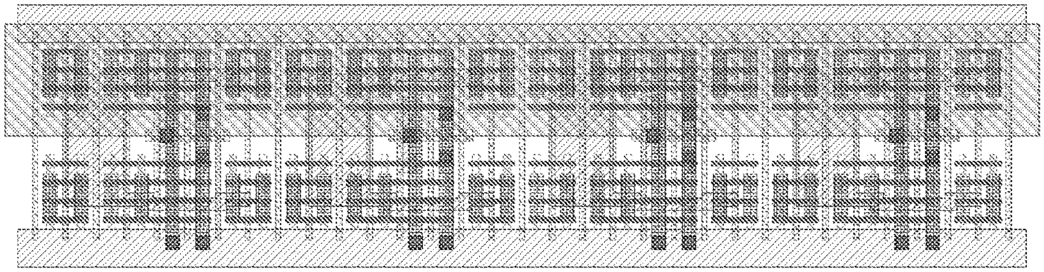
Figure 454B:
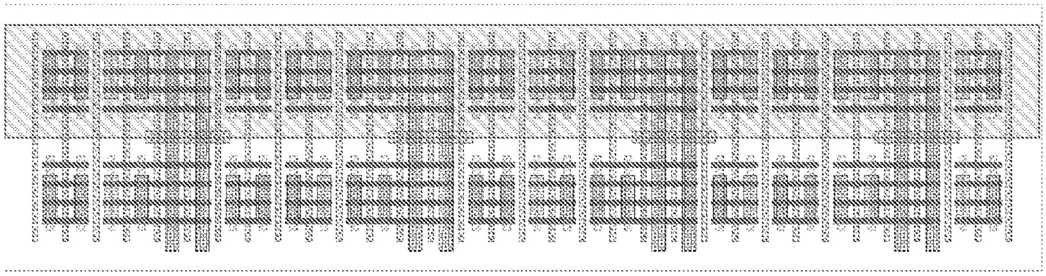
Figure 454C:
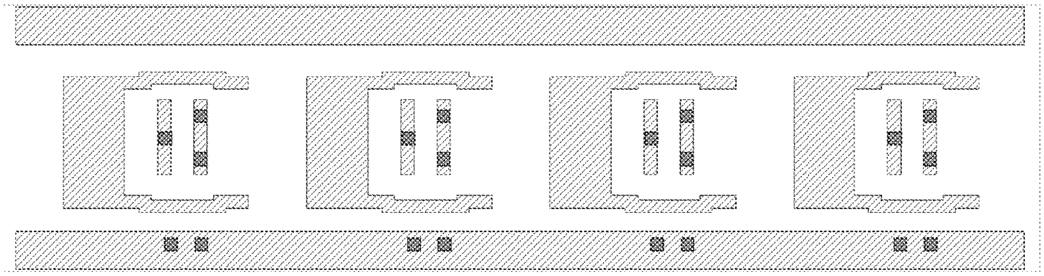
Figure 455A:
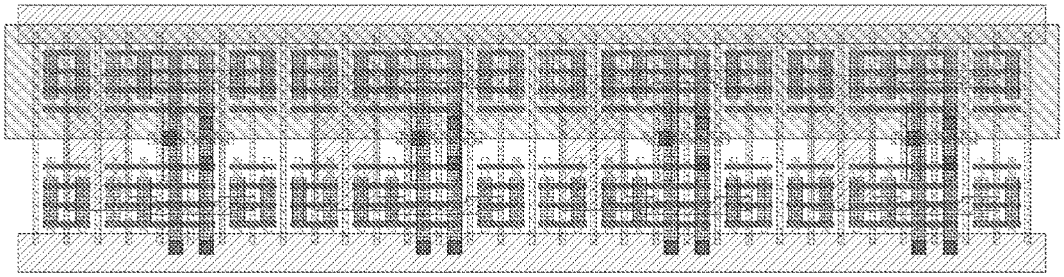
Figure 455B:
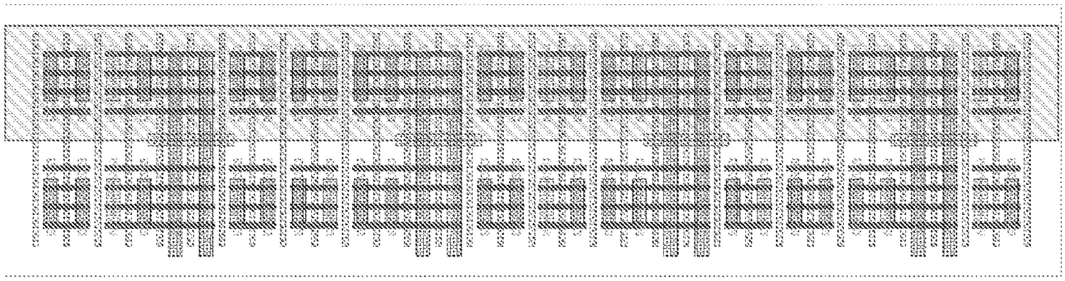
Figure 455C:
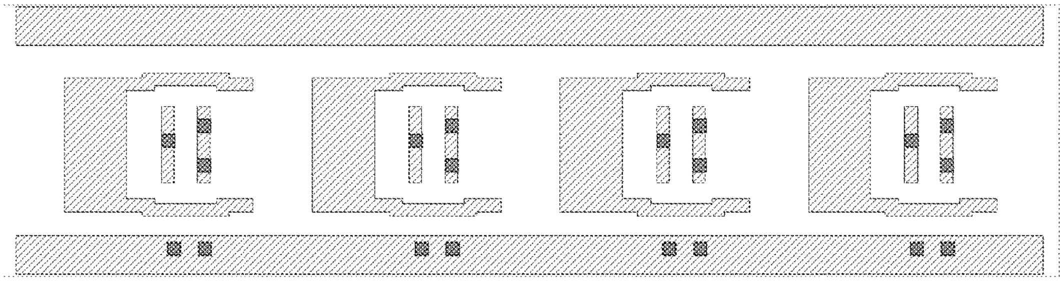
Figure 456A:
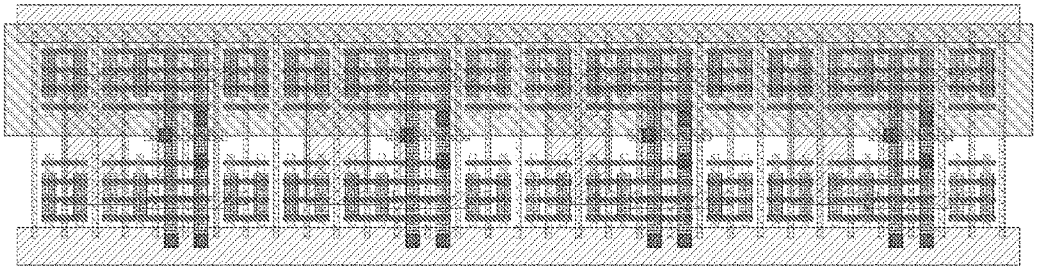
Figure 456B:
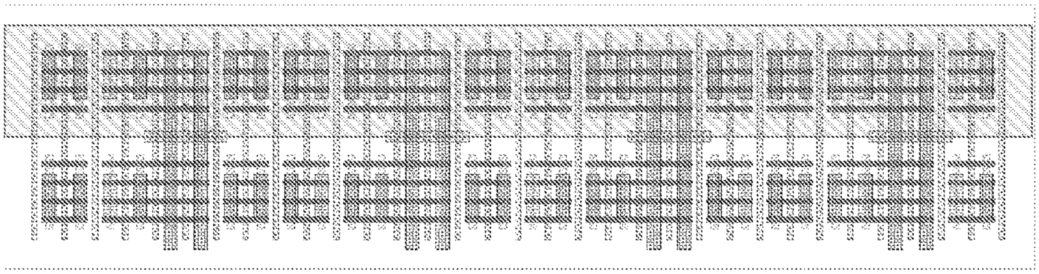
Figure 456C:
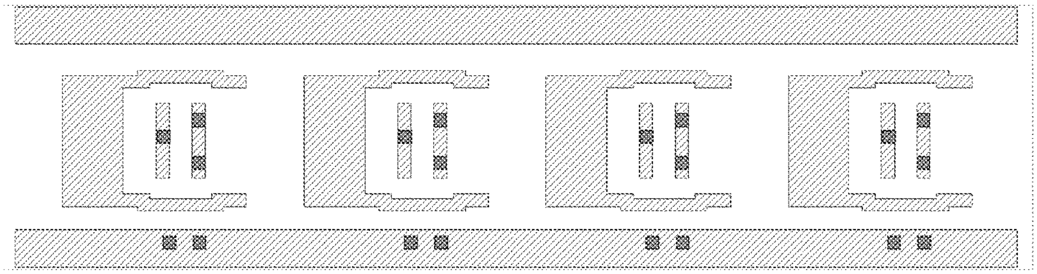
Figure 457A:
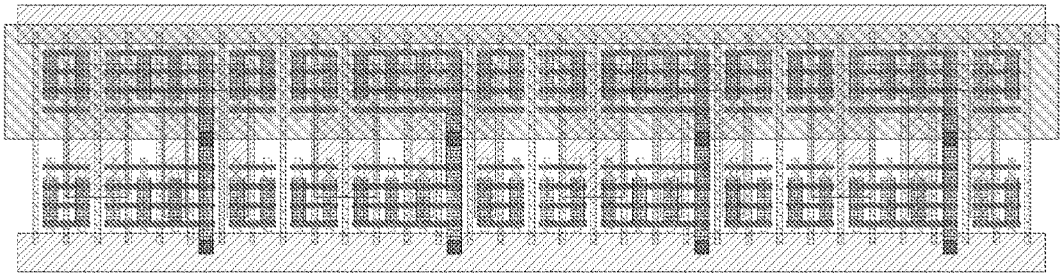
Figure 457B:
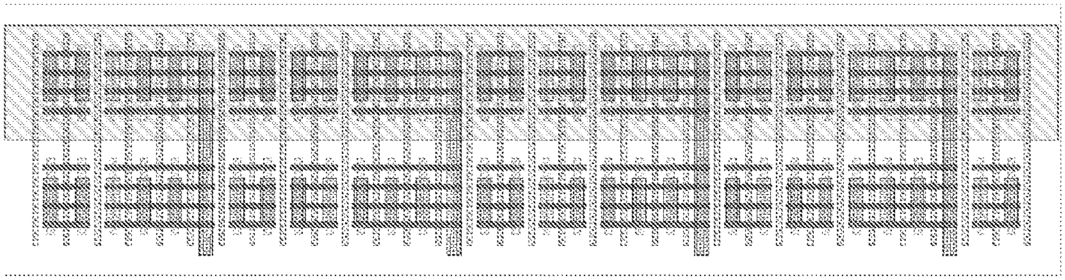
Figure 457C:
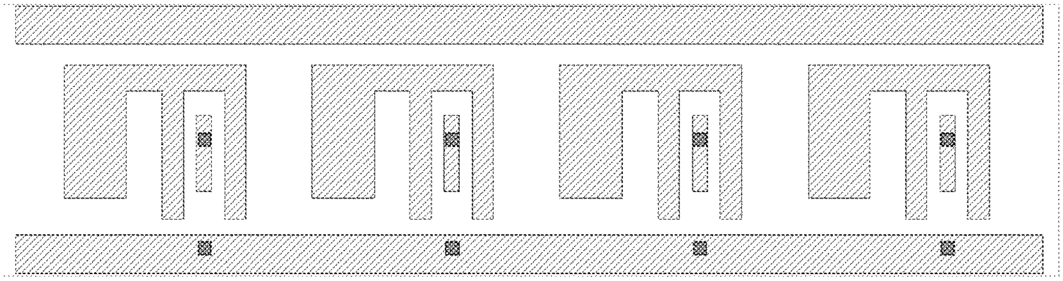
Figure 458A:
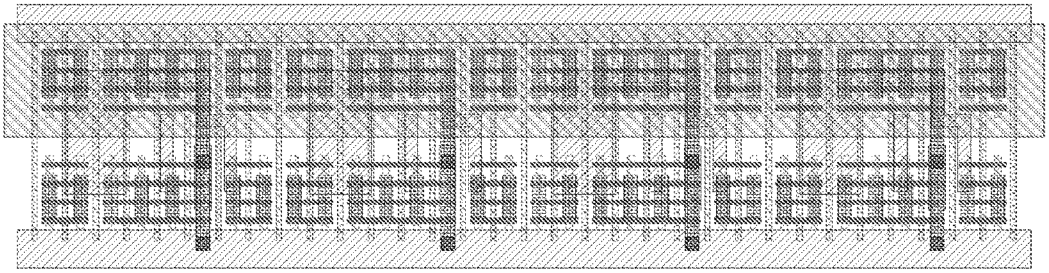
Figure 458B:
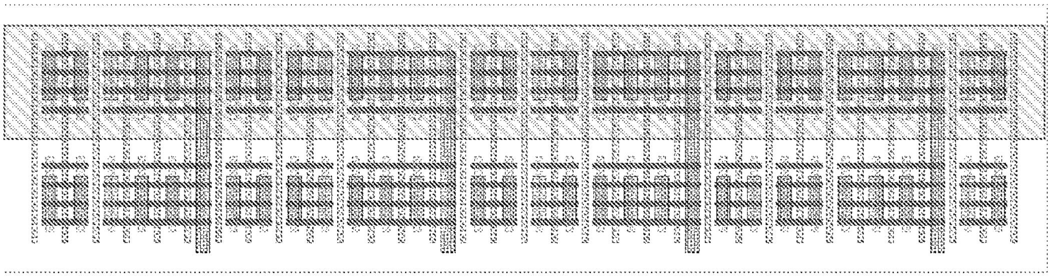
Figure 458C:
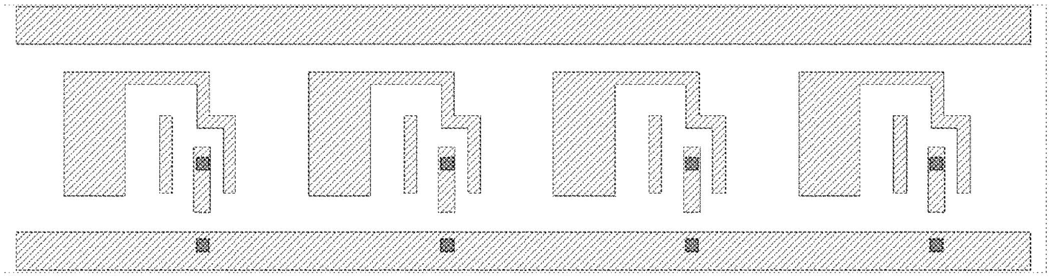
Figure 459A:
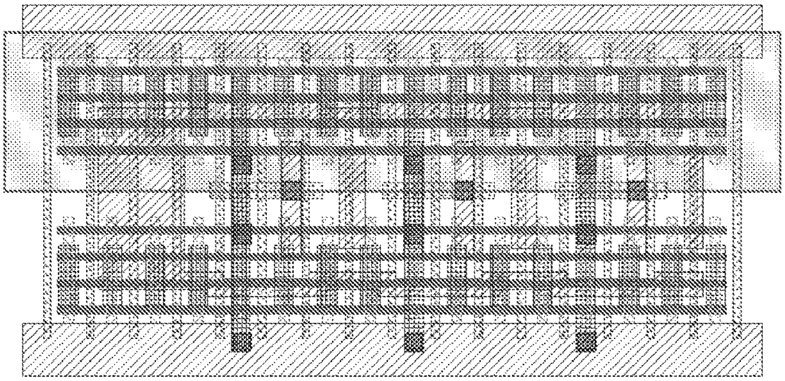
Figure 459B:
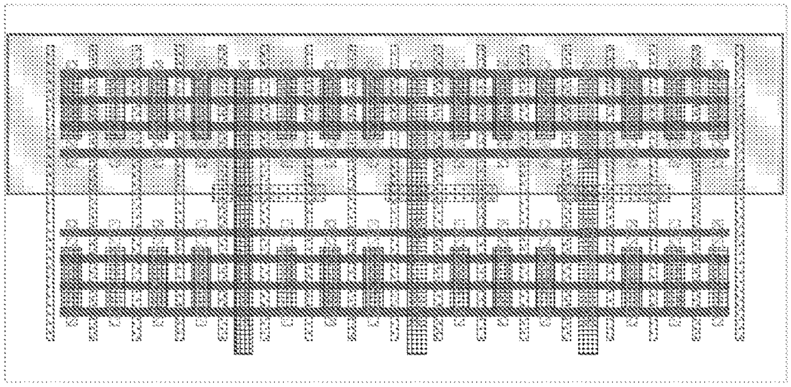
Figure 459C:
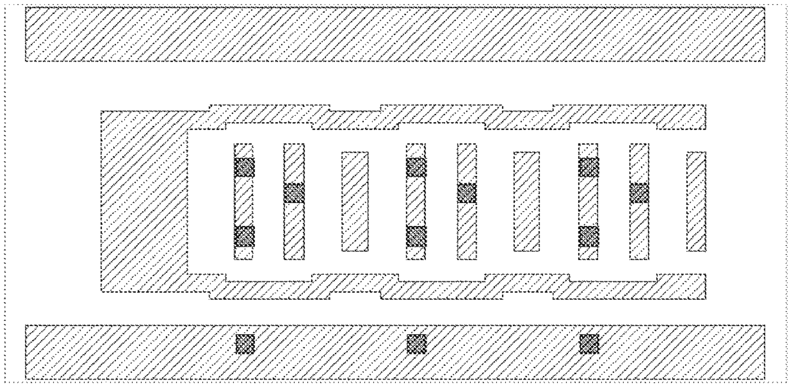
Figure 460A:
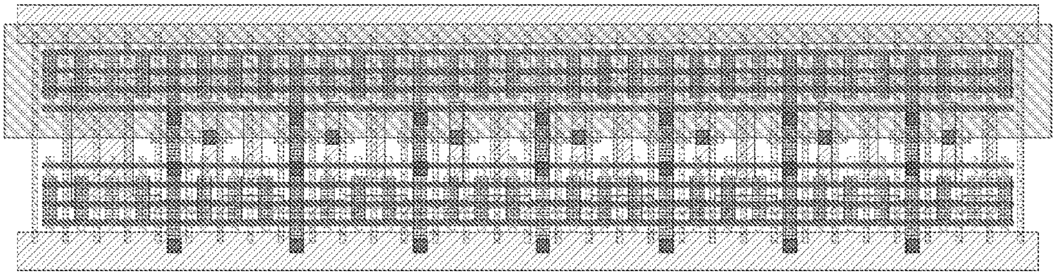
Figure 460B:
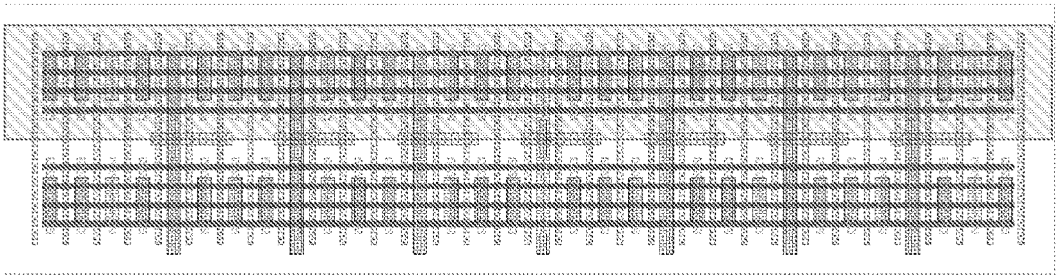
Figure 460C:
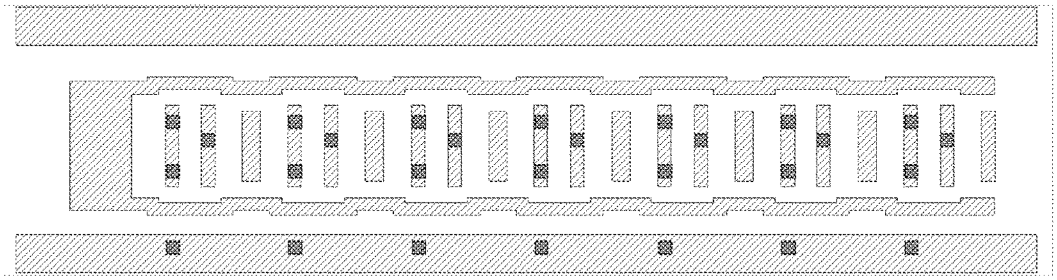
Figure 461A:
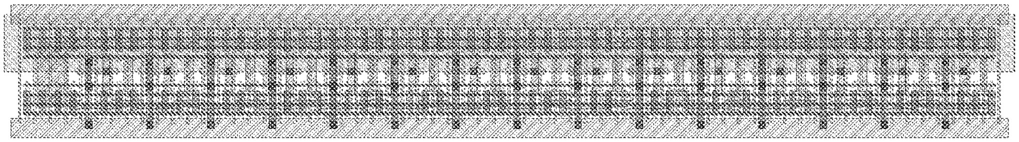
Figure 461B:
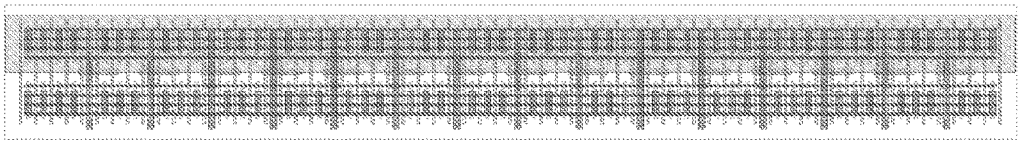
Figure 461C:
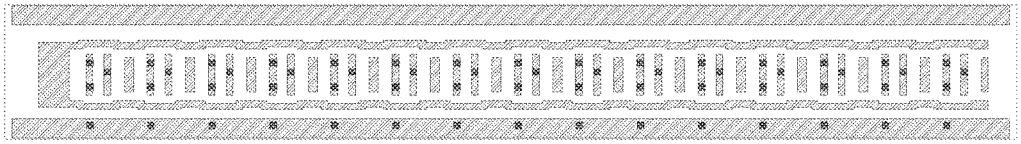
Figure 462A:
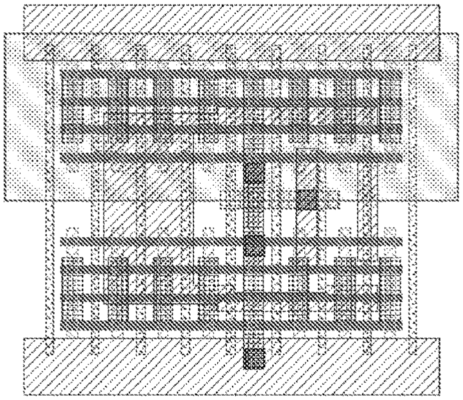
Figure 462B:
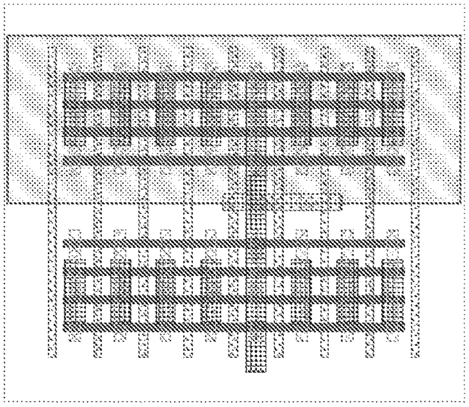
Figure 462C:
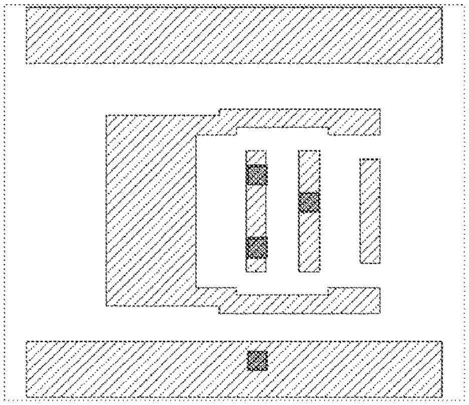
Figure 463A:
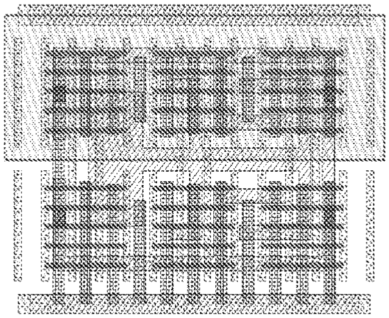
Figure 463B:
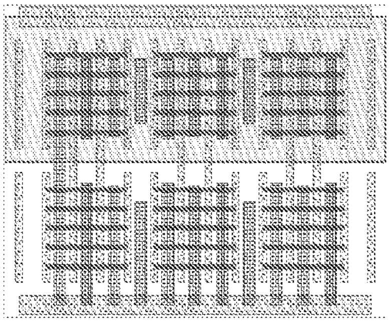
Figure 463C:
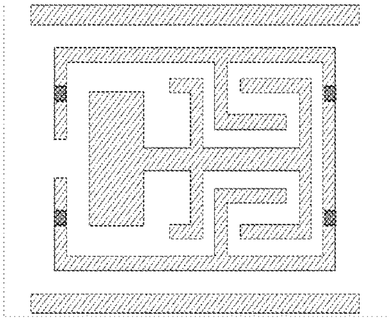
Figure 464A:
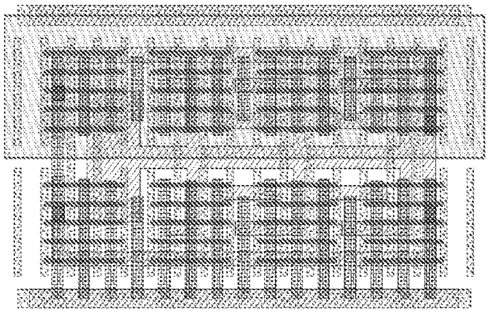
Figure 464B:
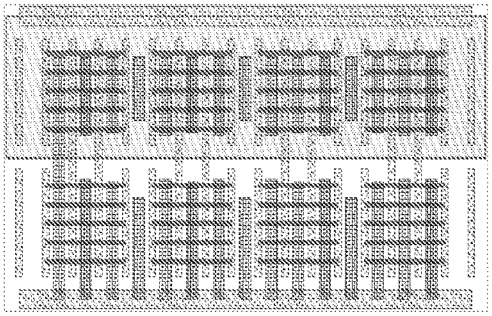
Figure 464C:
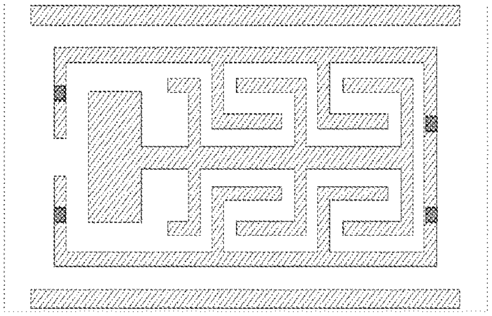
Figure 465A:
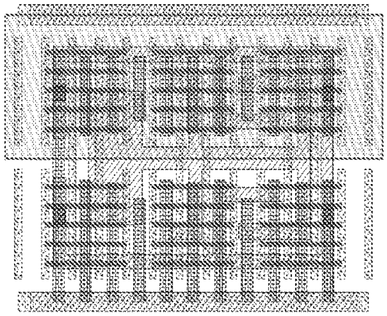
Figure 465B:
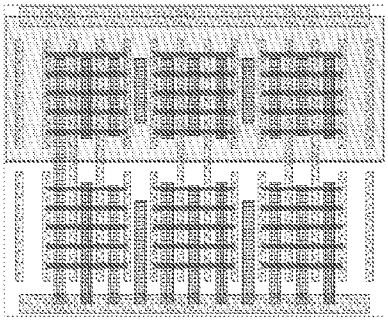
Figure 465C:
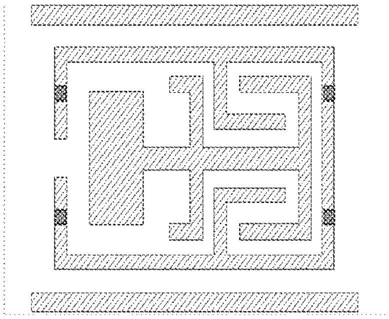
Figure 466A:
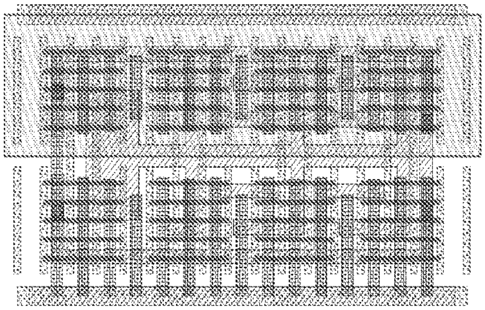
Figure 466B:
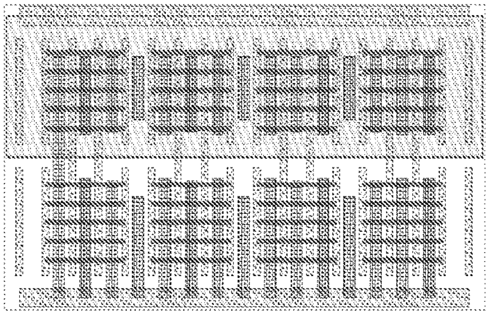
Figure 466C:
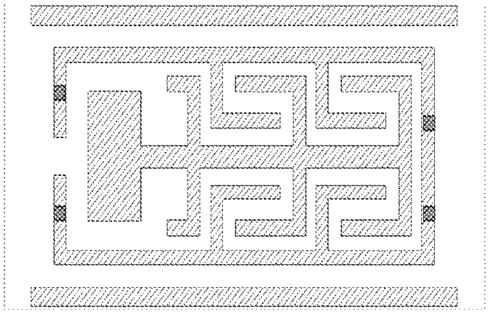
Figure 467A:
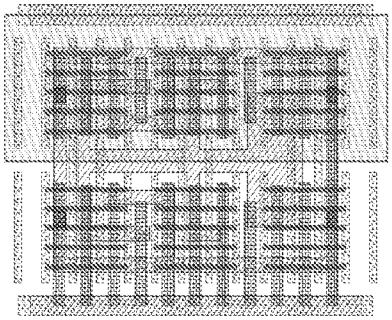
Figure 467B:
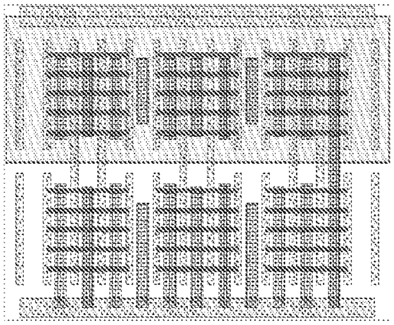
Figure 467C:
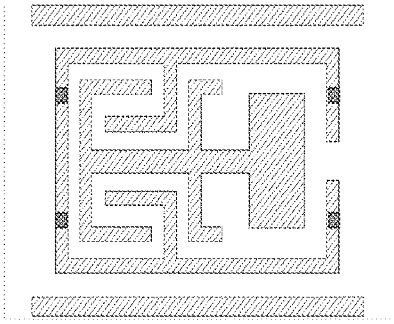
Figure 468A:
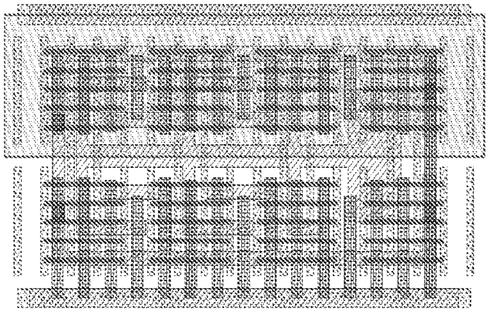
Figure 468B:
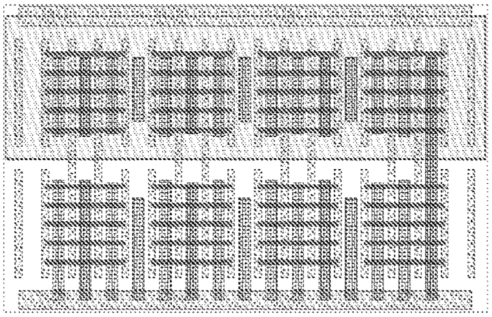
Figure 468C:
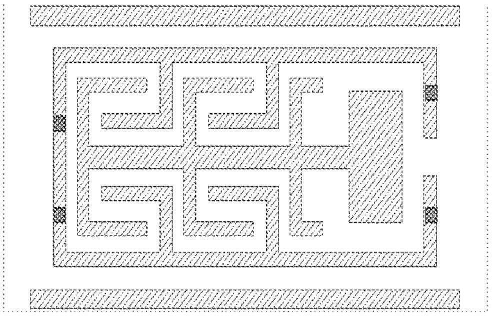
Figure 469A:
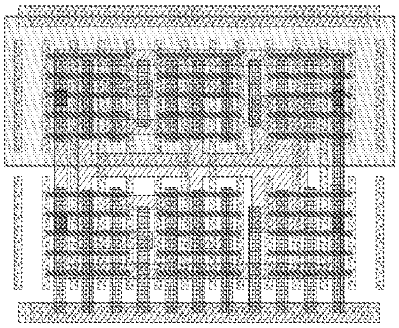
Figure 469B:
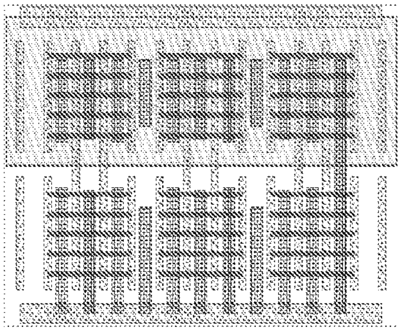
Figure 469C:
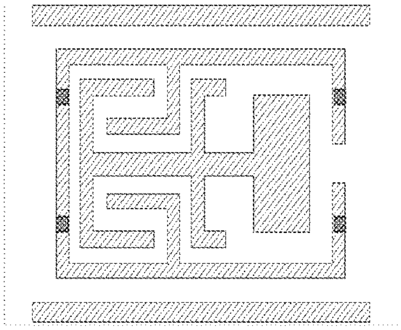
Figure 470A:
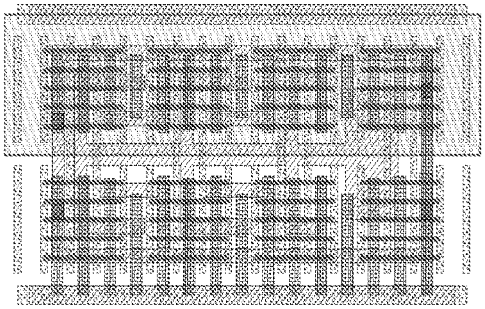
Figure 470B:
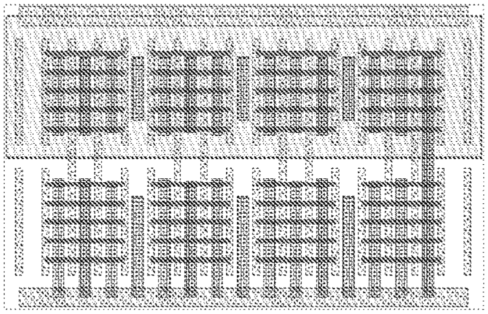
Figure 470C:
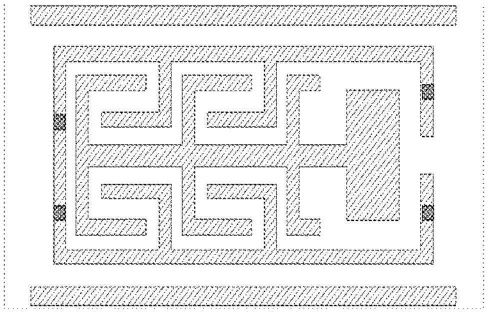
Figure 471A:
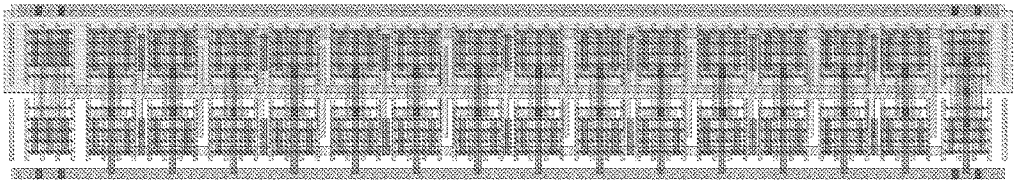
Figure 471B:
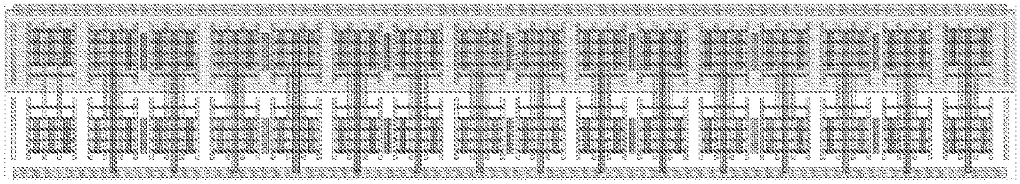
Figure 471C:
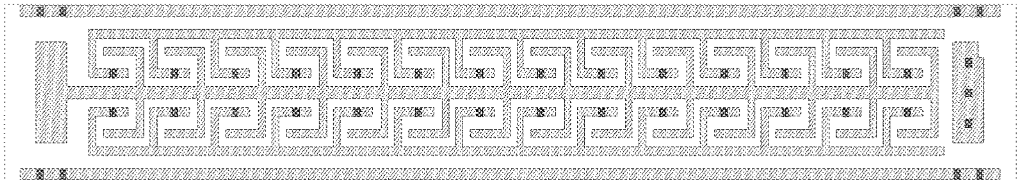
Figure 472A:
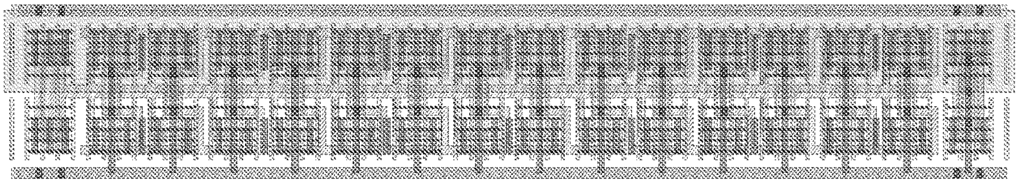
Figure 472B:
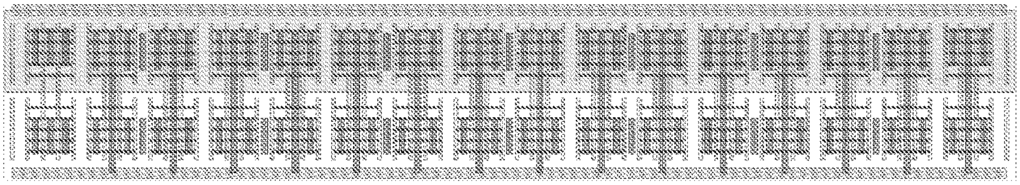
Figure 472C:
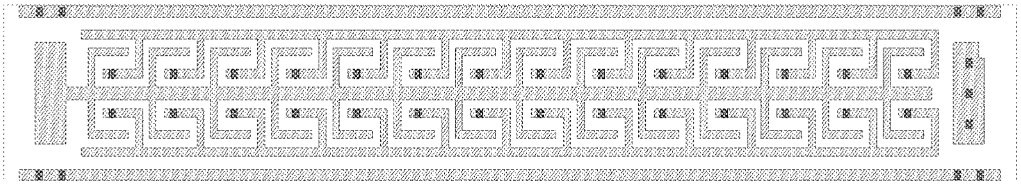
Figure 473A:
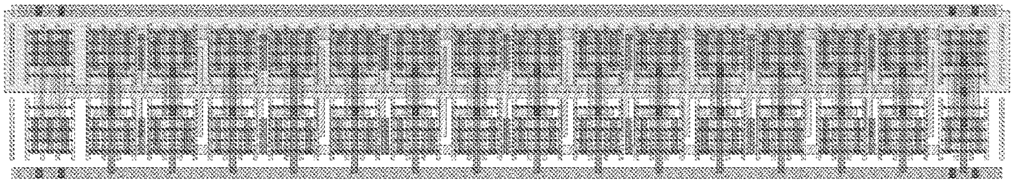
Figure 473B:
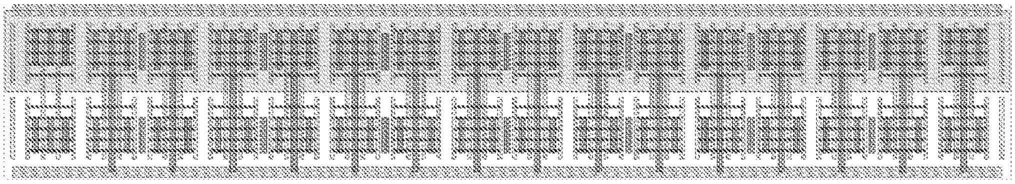
Figure 473C:
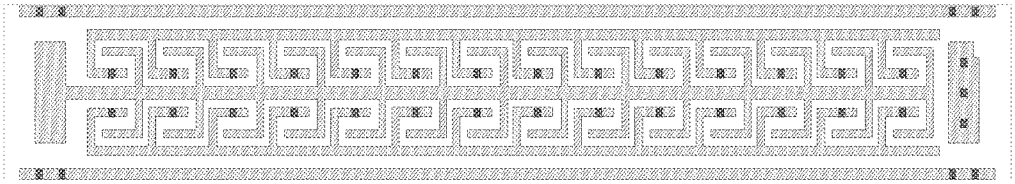
Figure 474A:
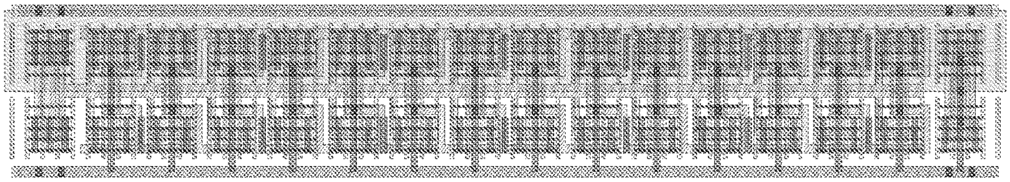
Figure 474B:
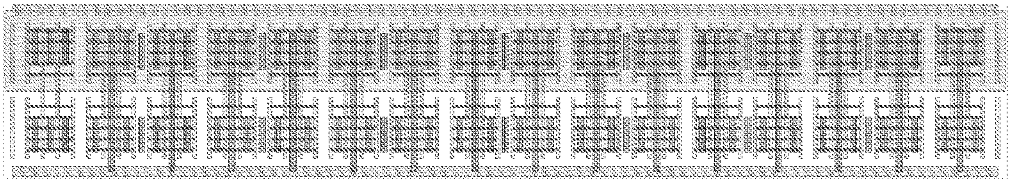
Figure 474C:
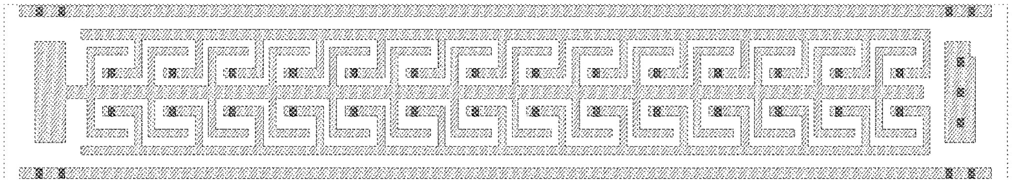
Figure 475A:
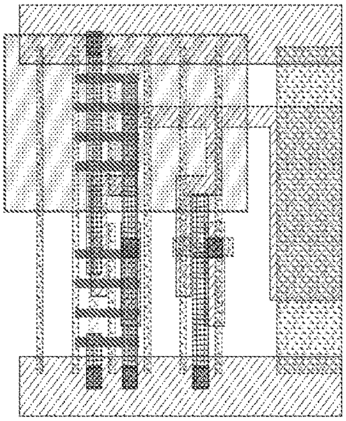
Figure 475B:
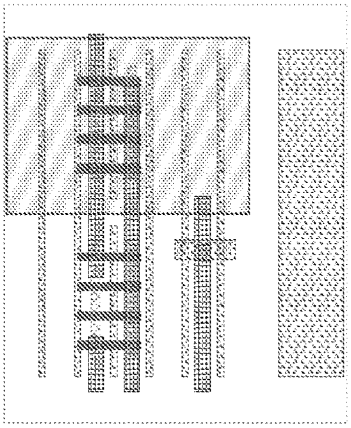
Figure 475C:
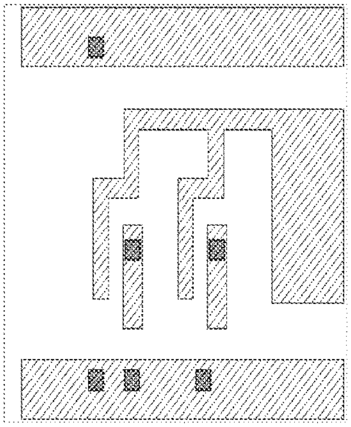
Figure 476A:
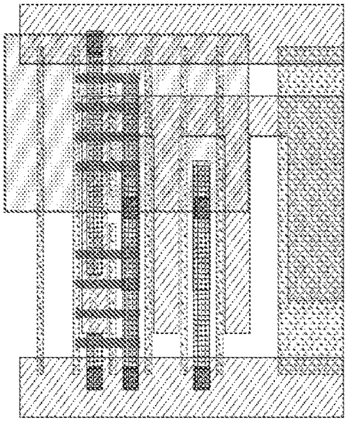
Figure 476B:
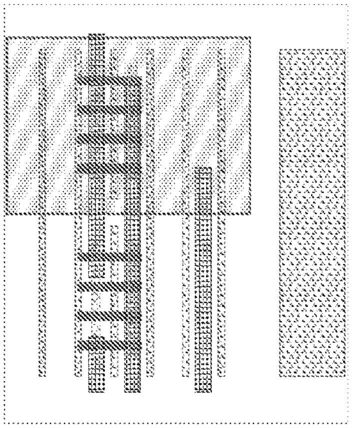
Figure 476C:
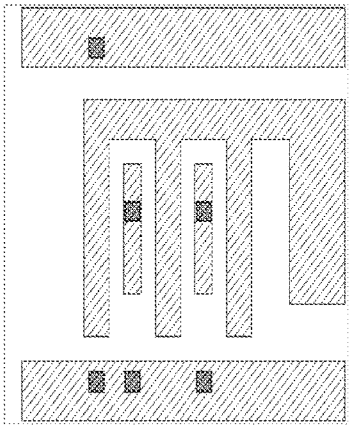
Figure 477A:
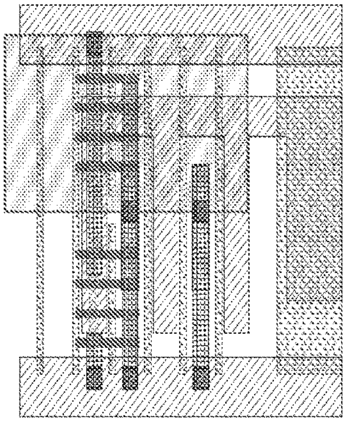
Figure 477B:
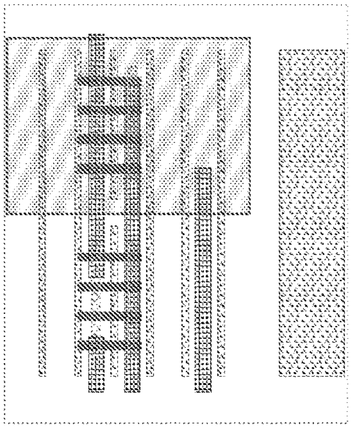
Figure 477C:
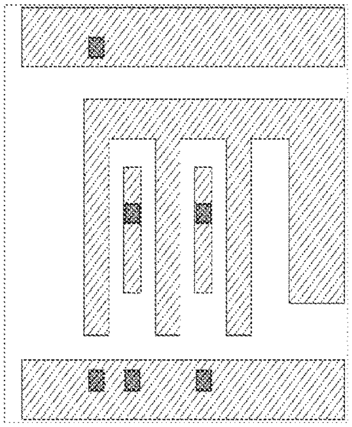
Figure 478A:
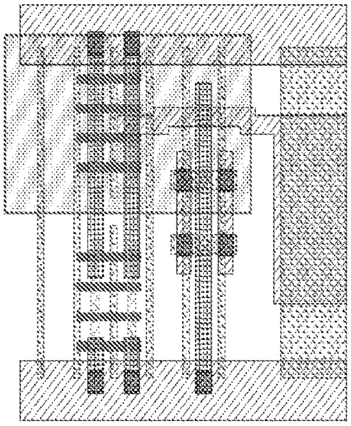
Figure 478B:
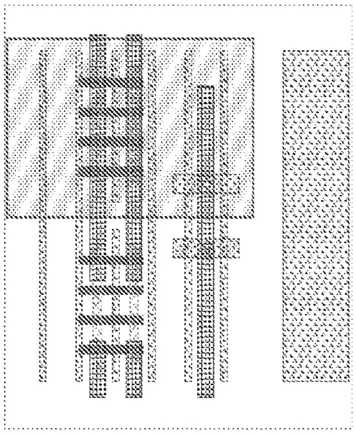
Figure 478C:
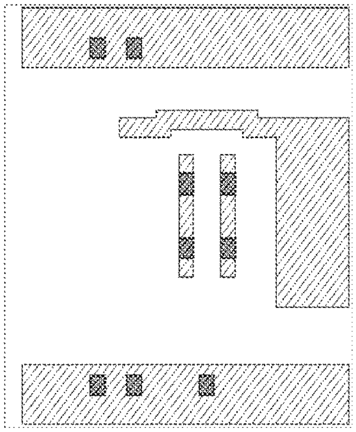
Figure 479A:
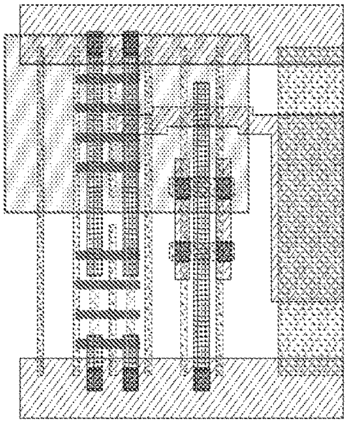
Figure 479B:
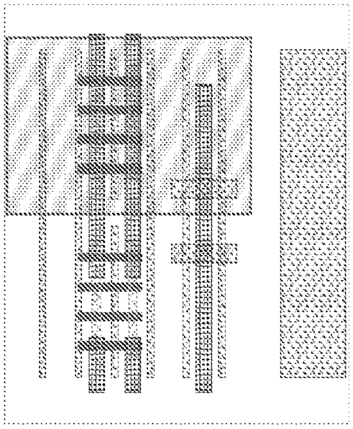
Figure 479C:
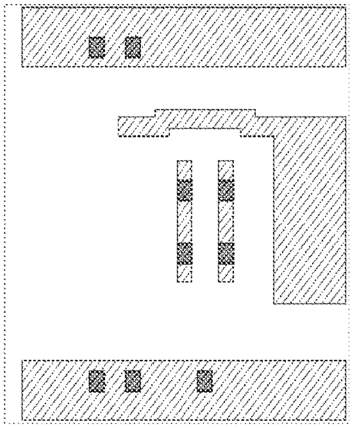
Figure 480A:
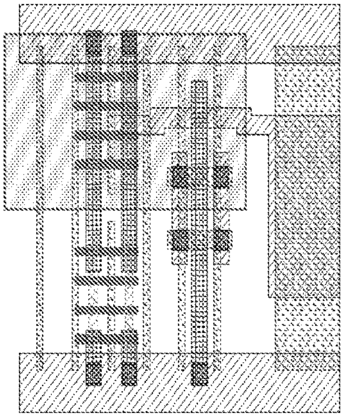
Figure 480B:
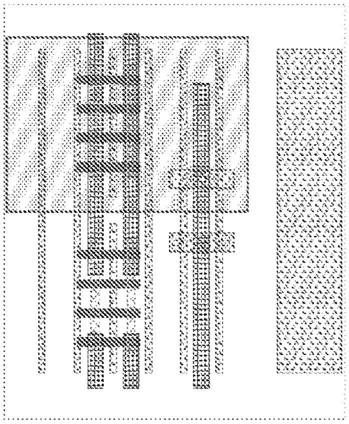
Figure 480C:
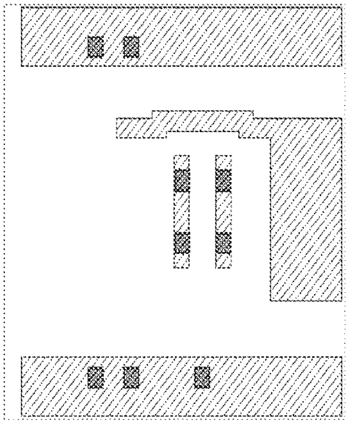
Figure 481A:
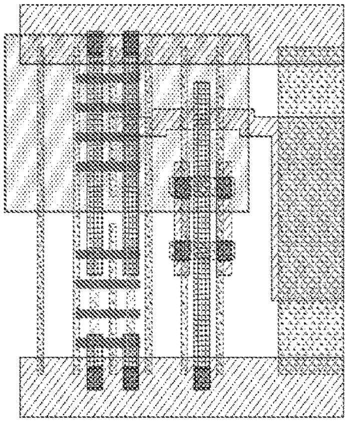
Figure 481B:
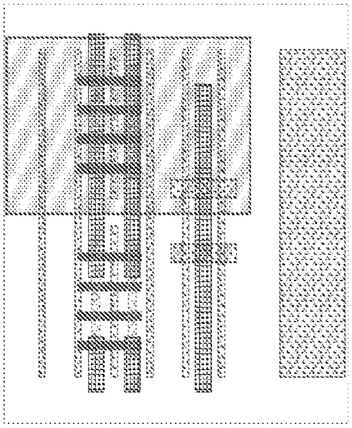
Figure 481C:
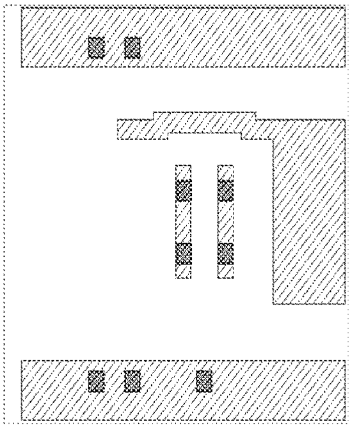
Figure 482A:
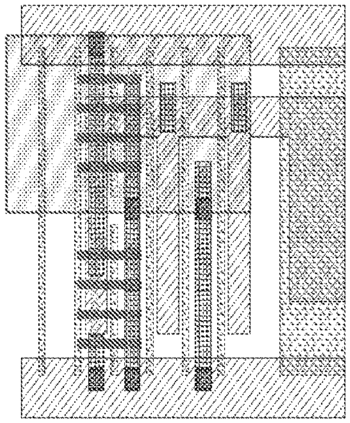
Figure 482B:
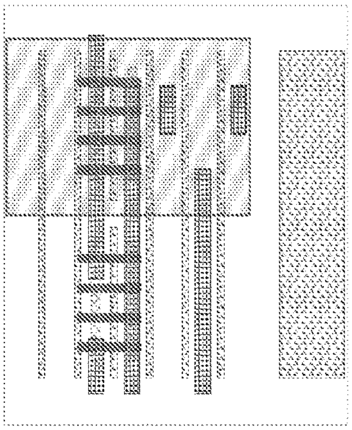
Figure 482C:
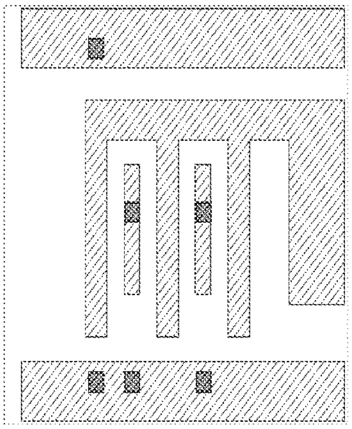
Figure 483A:
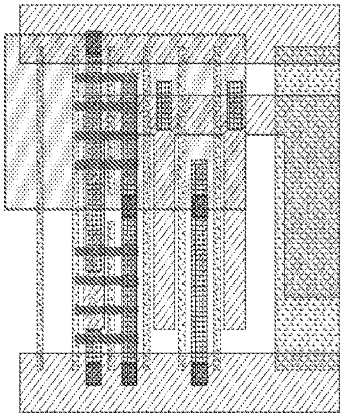
Figure 483B:
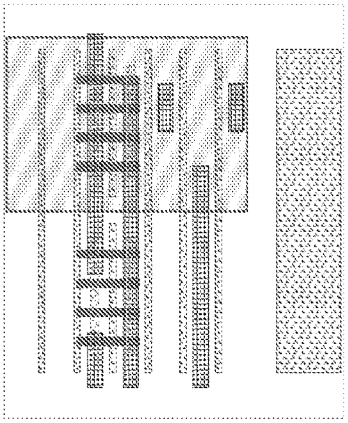
Figure 483C:
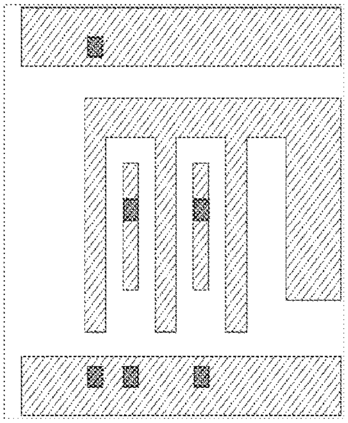
Figure 484A:
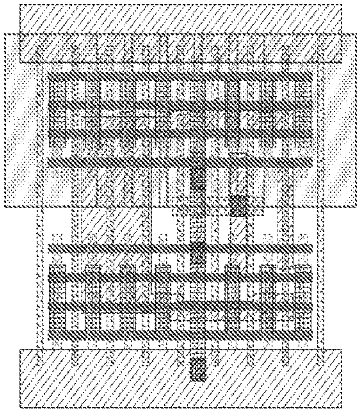
Figure 484B:
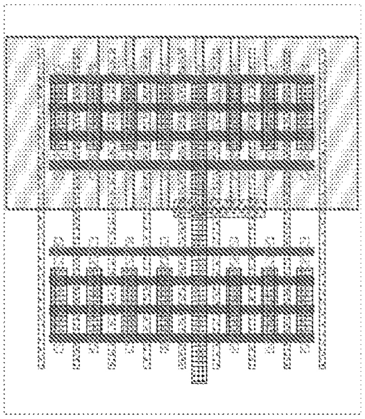
Figure 484C:
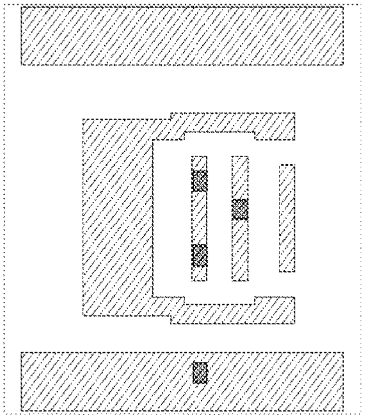
Figure 485A:
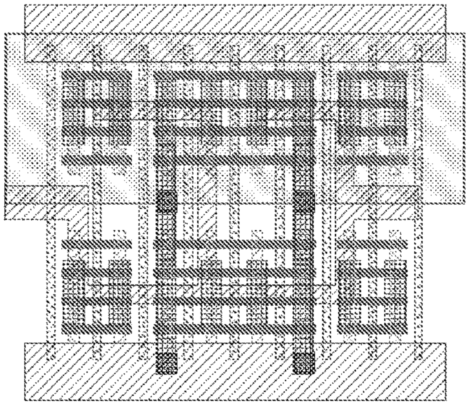
Figure 485B:
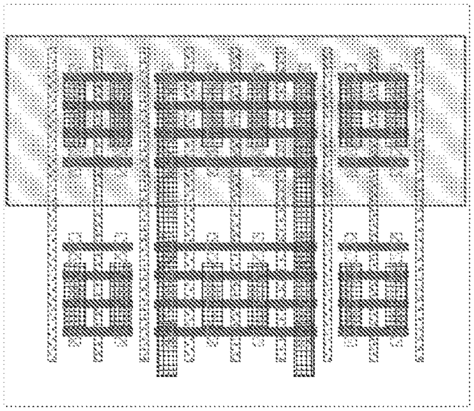
Figure 485C:
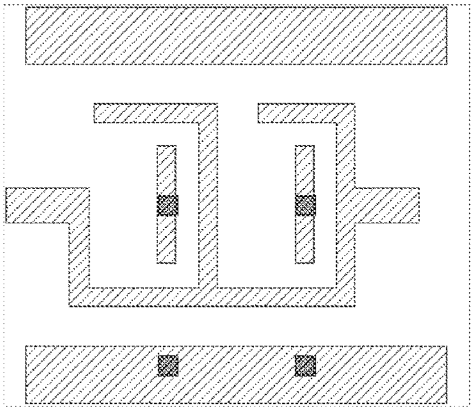
Figure 486A:
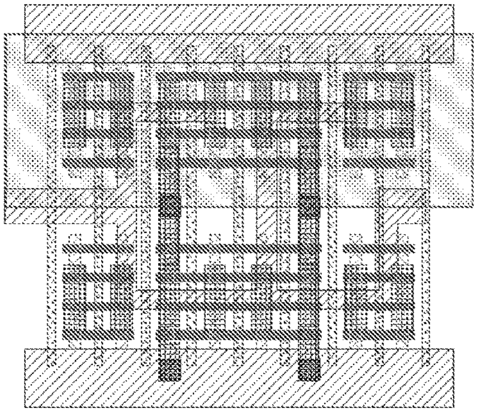
Figure 486B:
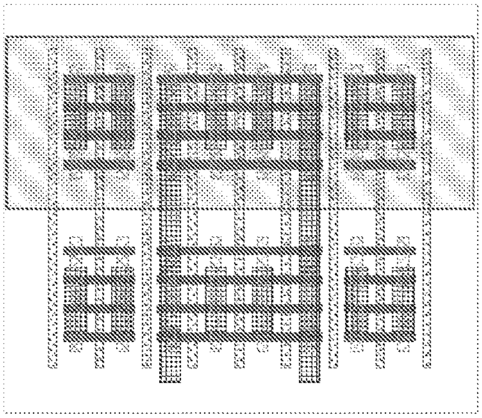
Figure 486C:
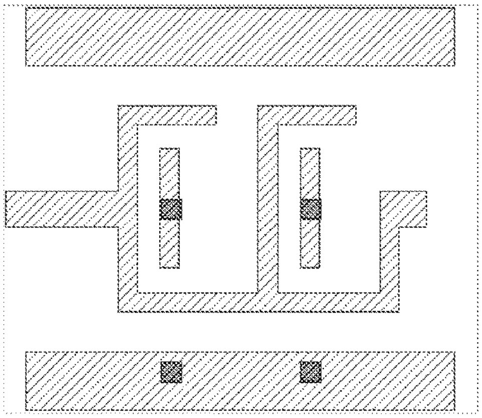
Figure 487A:
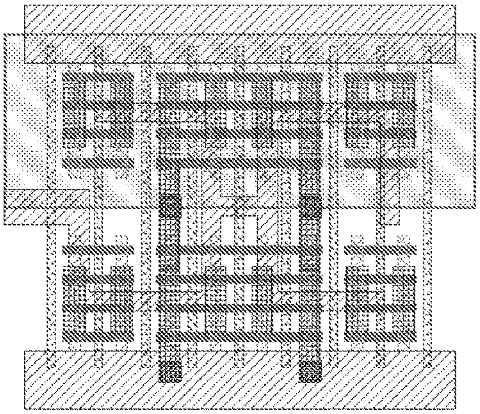
Figure 487B:
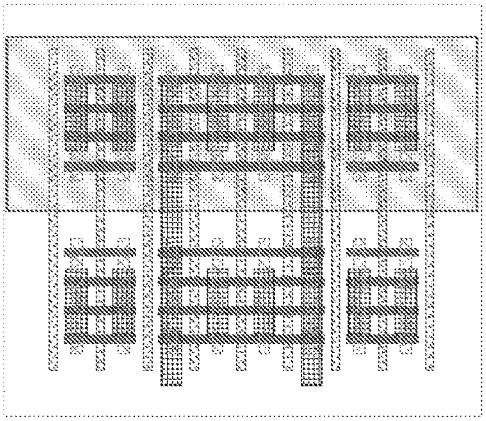
Figure 487C:
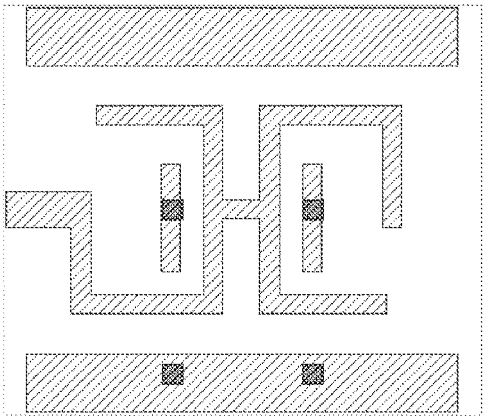
Figure 488A:
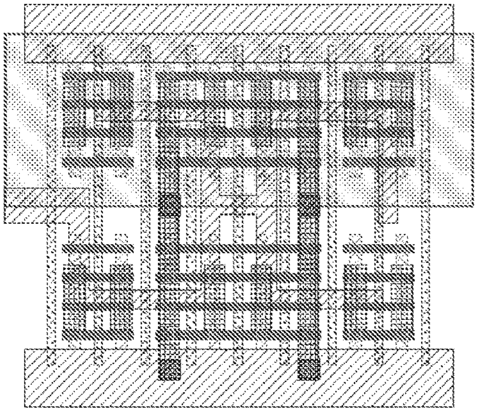
Figure 488B:
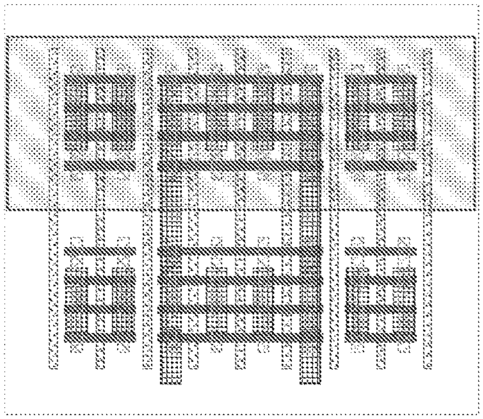
Figure 488C:
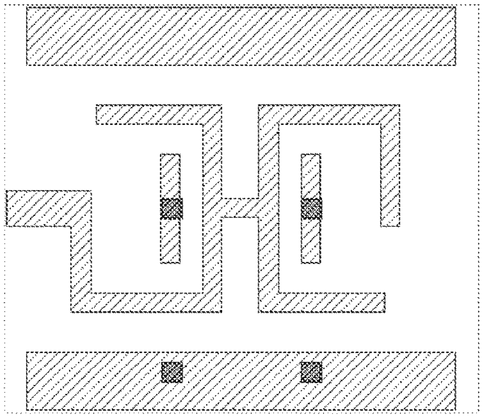
Figure 489A:
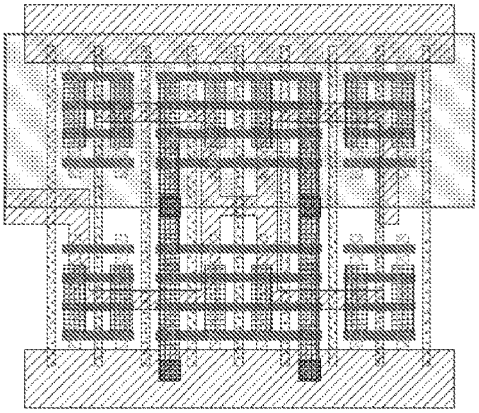
Figure 489B:
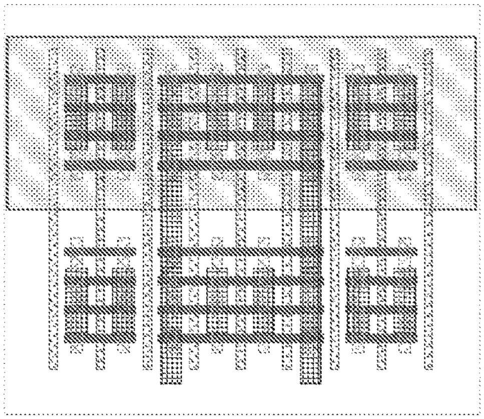
Figure 489C:
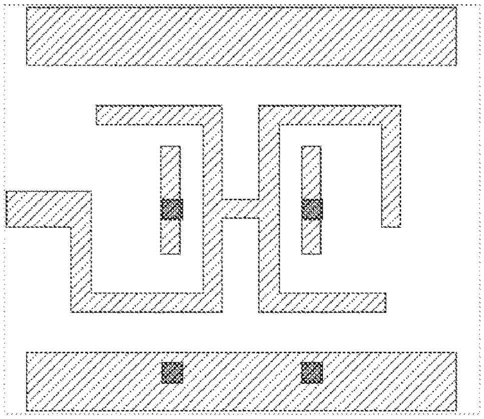
Figure 490A:
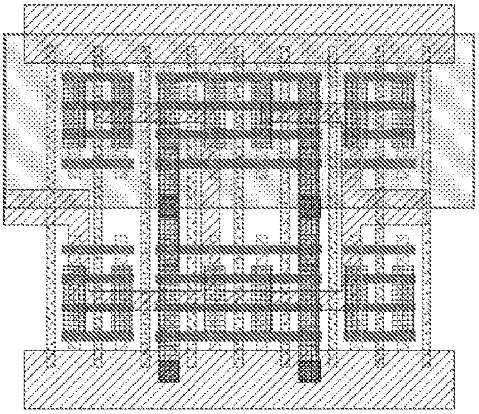
Figure 490B:
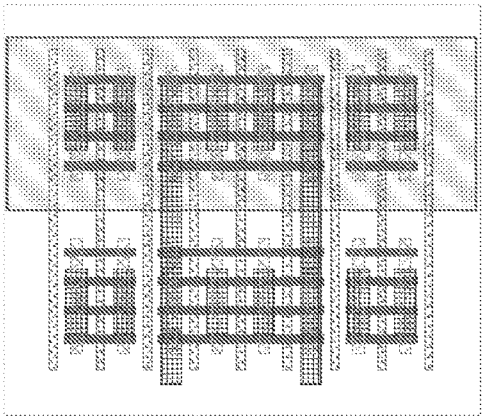
Figure 490C:
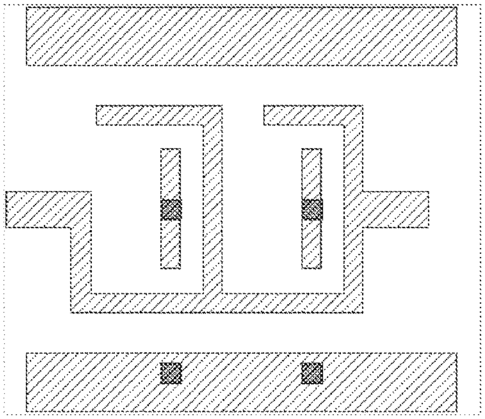
Figure 491A:
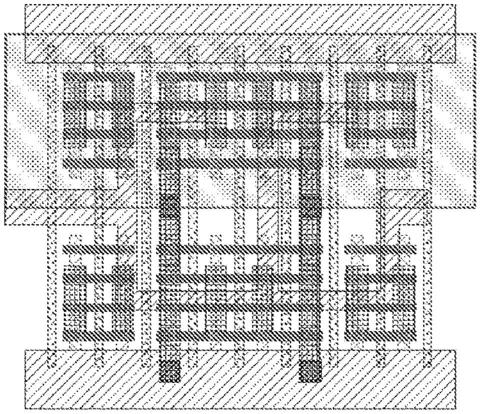
Figure 491B:
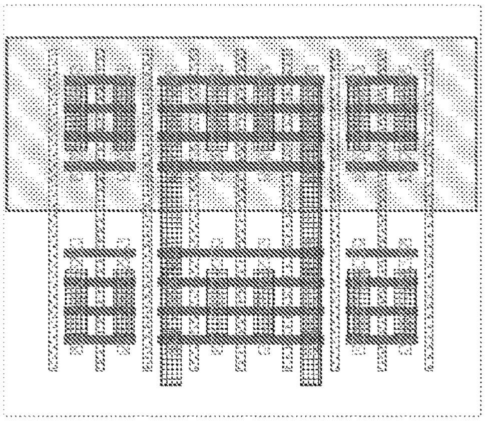
Figure 491C:
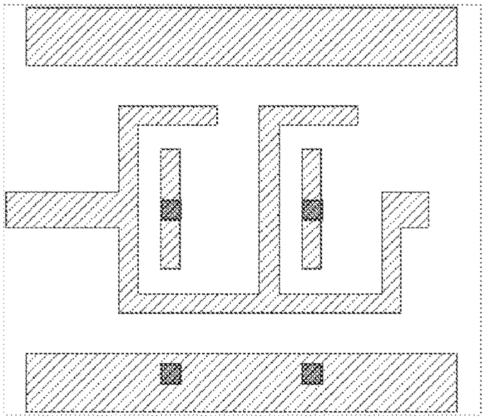
Figure 492A:
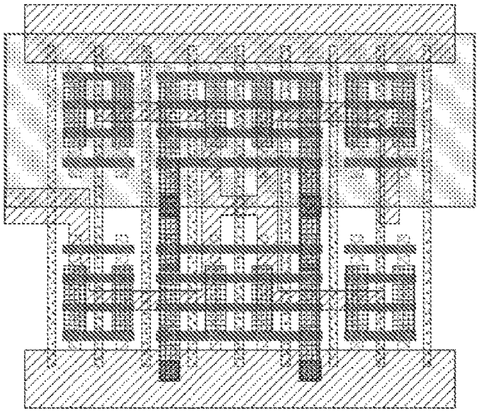
Figure 492B:
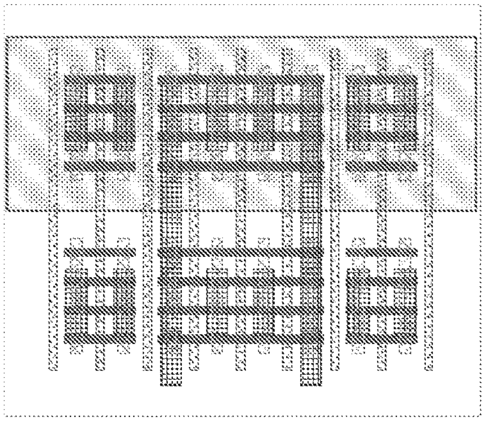
Figure 492C:
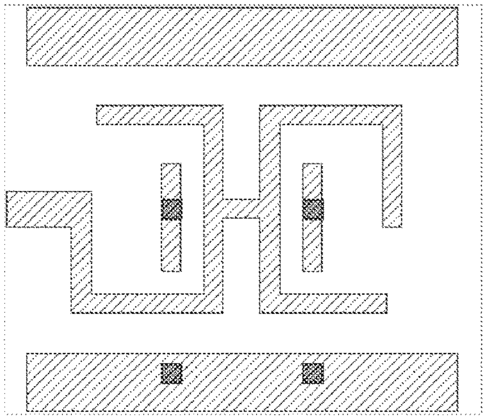
Figure 493A:
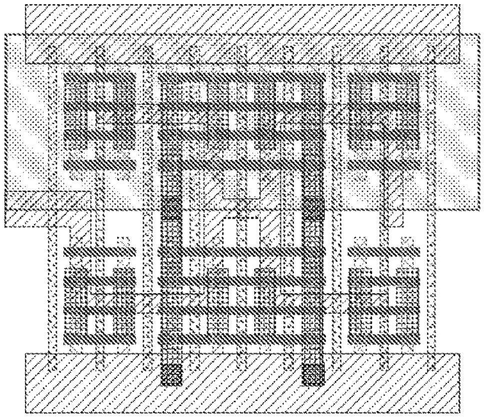
Figure 493B:
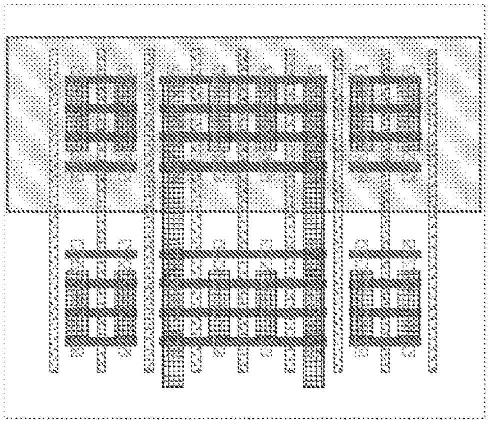
Figure 493C:
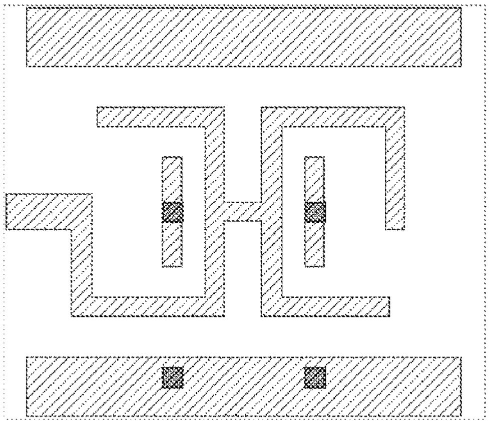
Figure 494A:
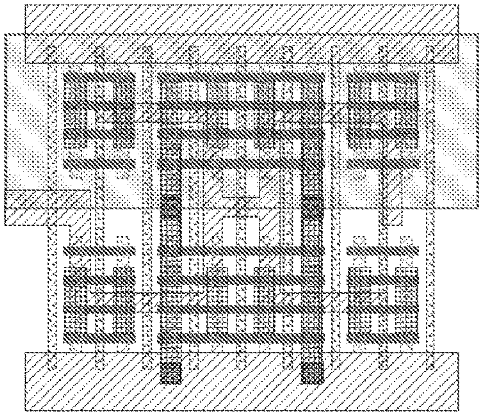
Figure 494B:
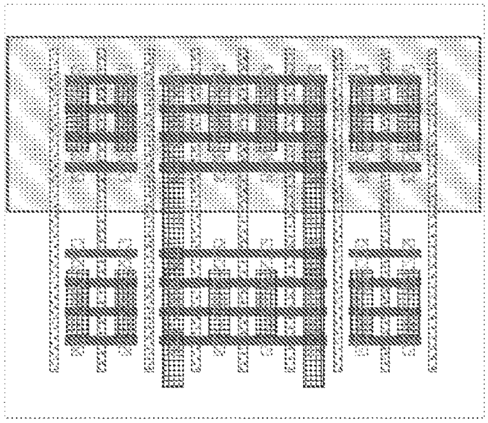
Figure 494C:
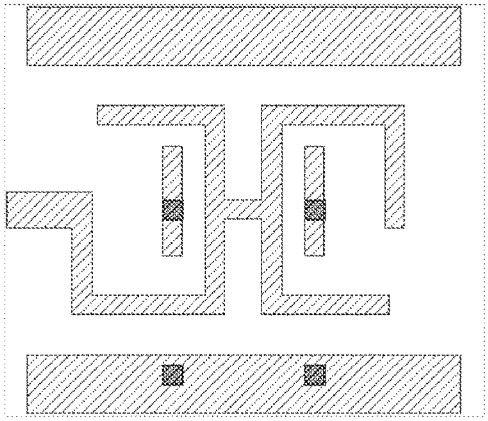
Figure 495A:
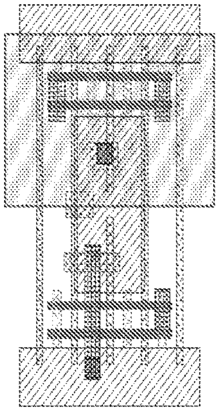
Figure 495B:
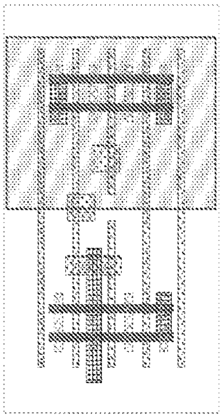
Figure 495C:
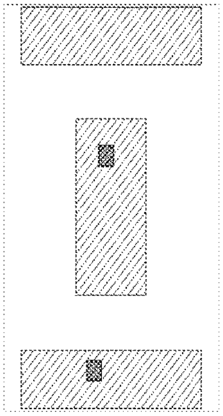
Figure 496A:
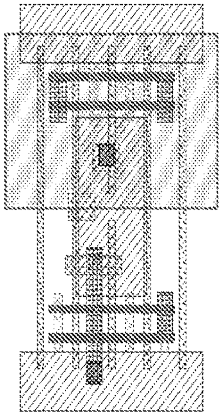
Figure 496B:
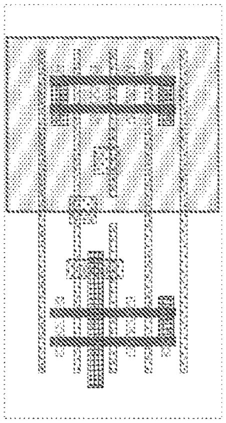
Figure 496C:
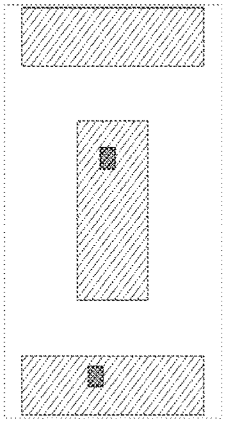
Figure 497A:
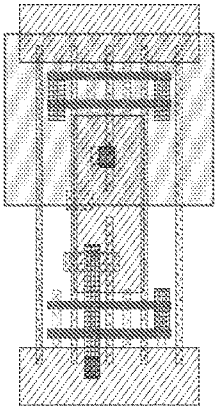
Figure 497B:
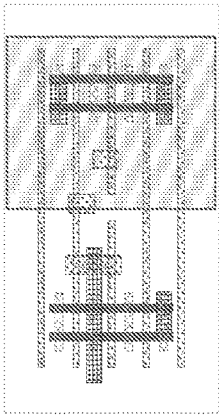
Figure 497C:
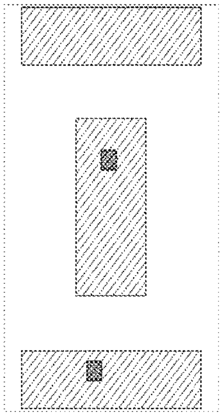
Figure 498A:
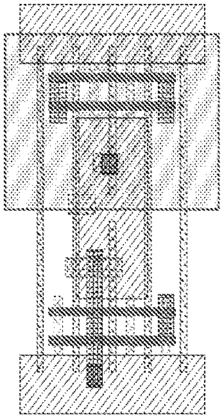
Figure 498B:
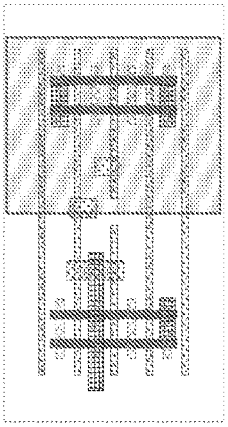
Figure 498C:
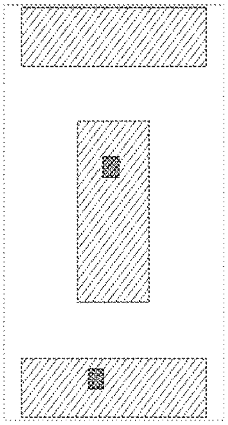
Figure 499A:
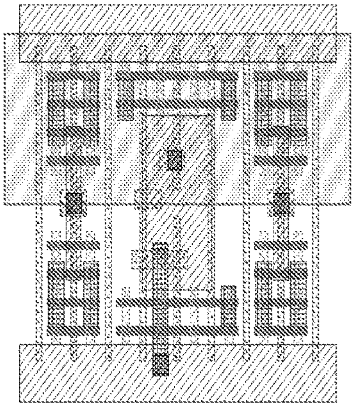
Figure 499B:
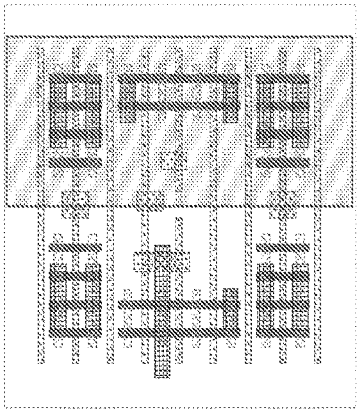
Figure 499C:
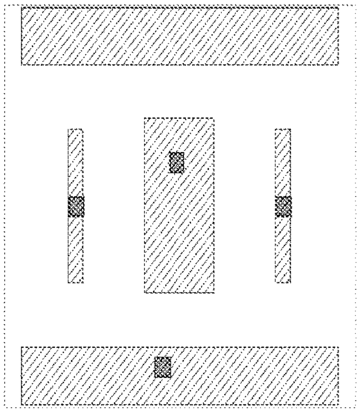
Figure 500A:
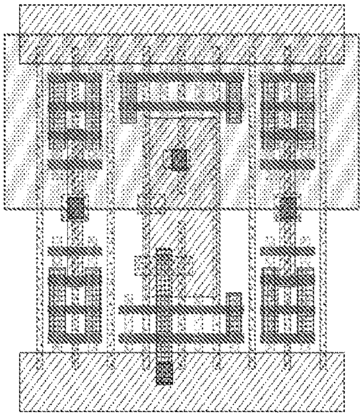
Figure 500B:
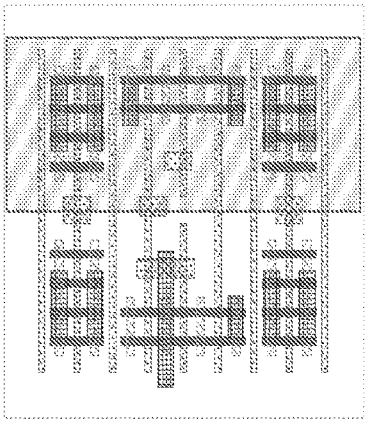
Figure 500C:
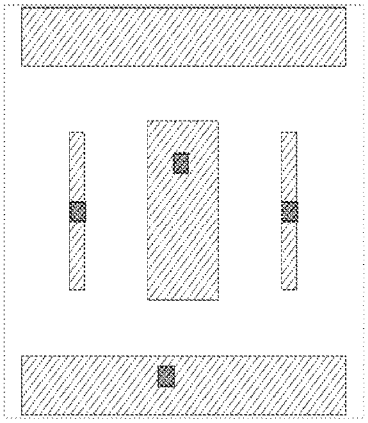
Figure 501A:
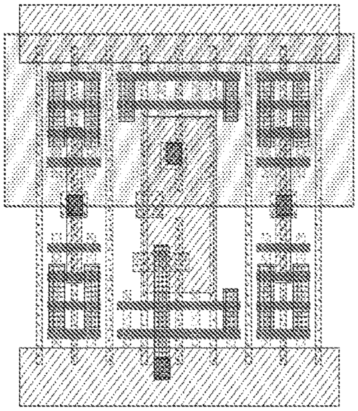
Figure 501B:
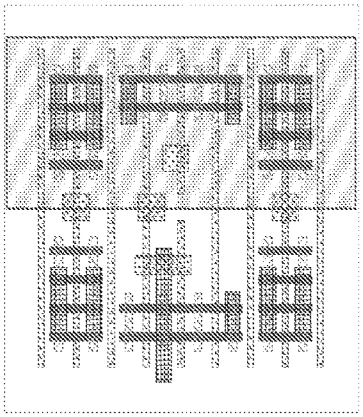
Figure 501C:
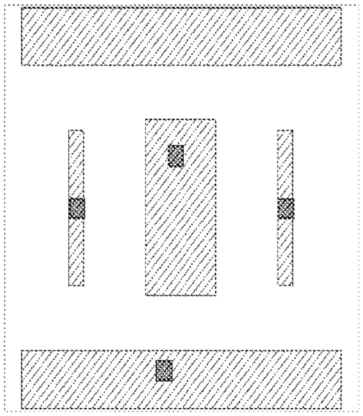
Figure 502A:
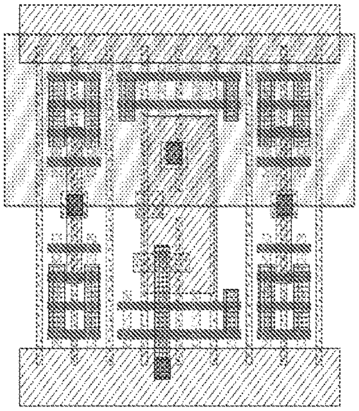
Figure 502B:
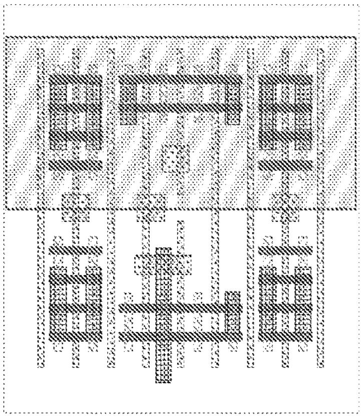
Figure 502C:
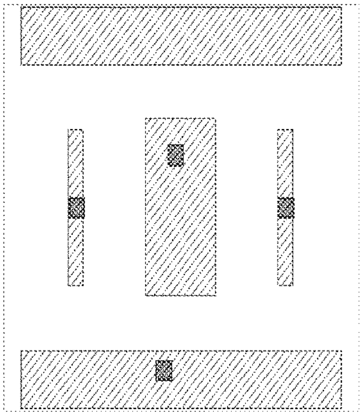
Figure 503A:
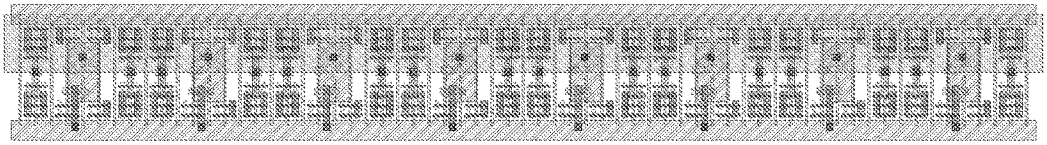
Figure 503B:
Figure 503C:
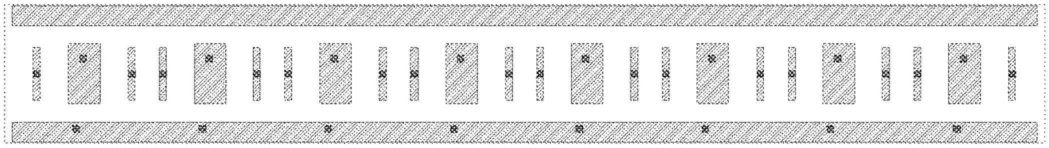
Figure 504A:
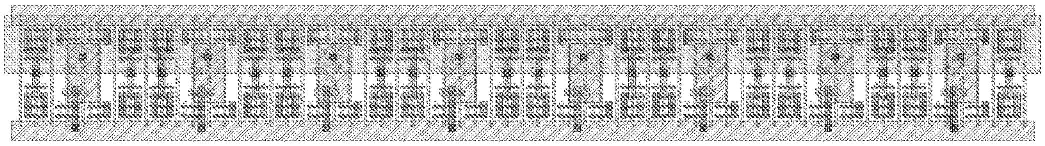
Figure 504B:
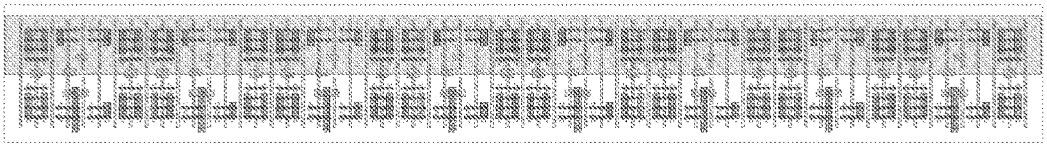
Figure 504C:
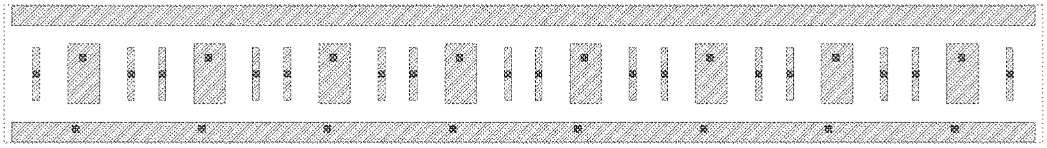
Figure 505A:
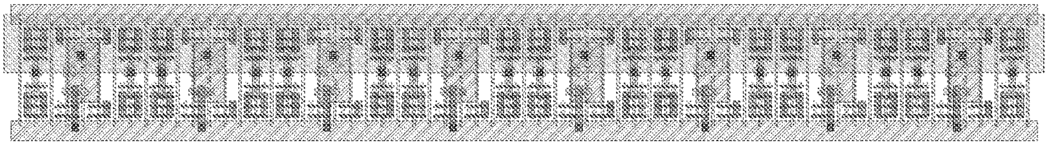
Figure 505B:
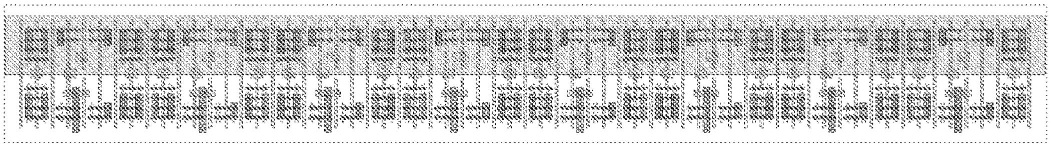
Figure 505C:
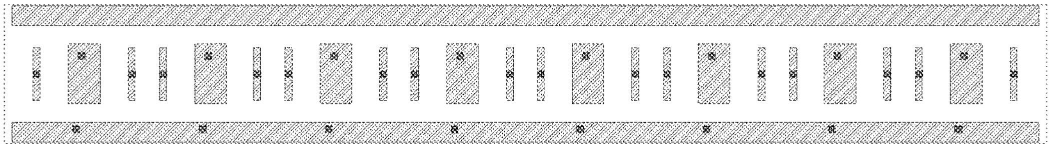
Figure 506A:
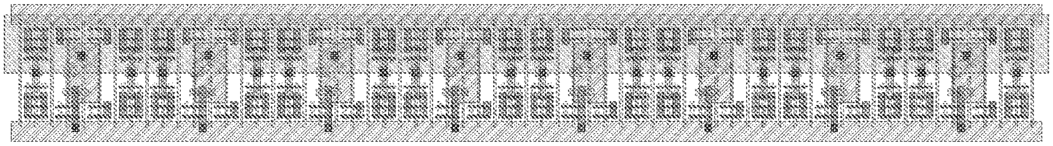
Figure 506B:
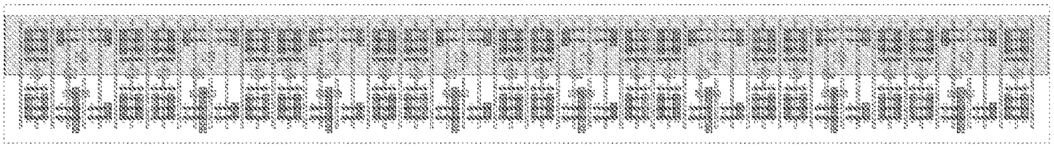
Figure 506C:
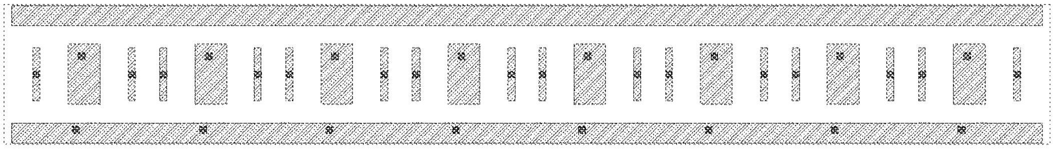
Figure 507A:
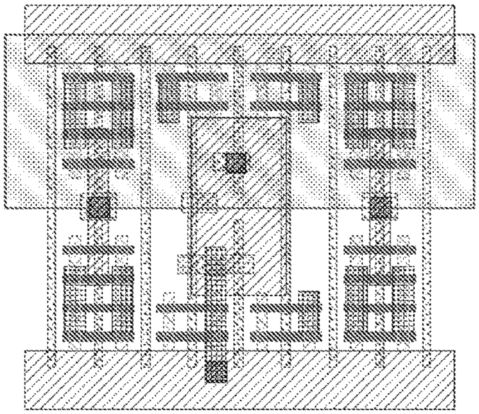
Figure 507B:
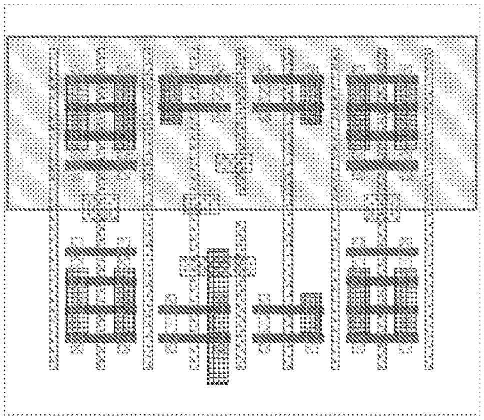
Figure 507C:
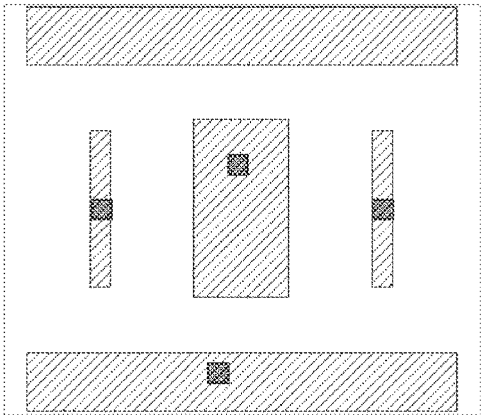
Figure 508A:
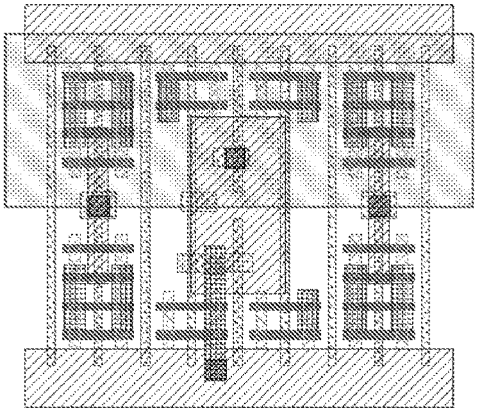
Figure 508B:
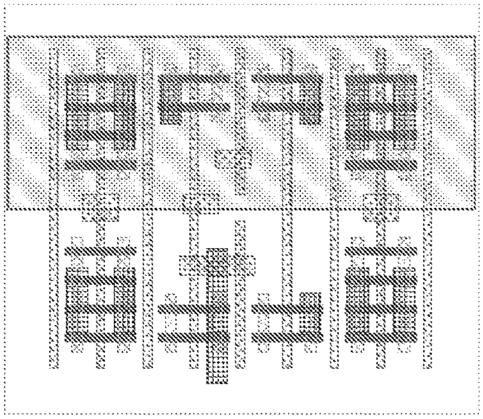
Figure 508C:
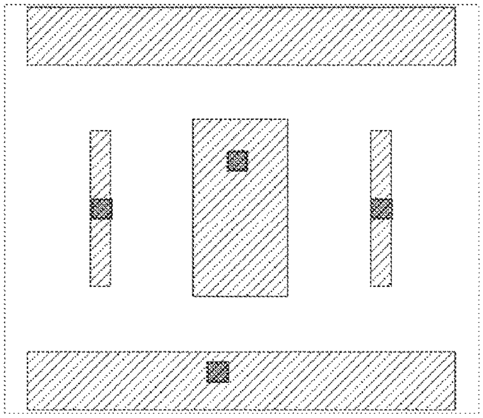
Figure 509A:
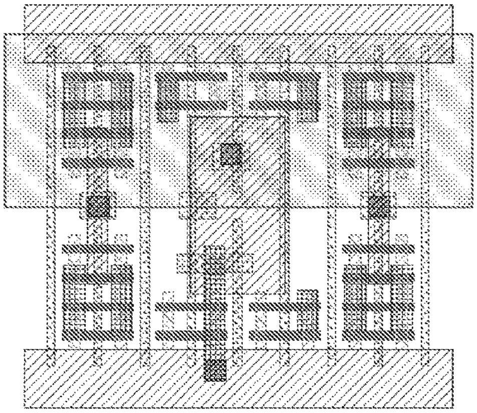
Figure 509B:
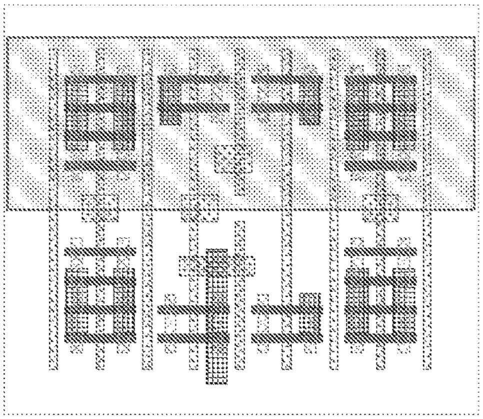
Figure 509C:
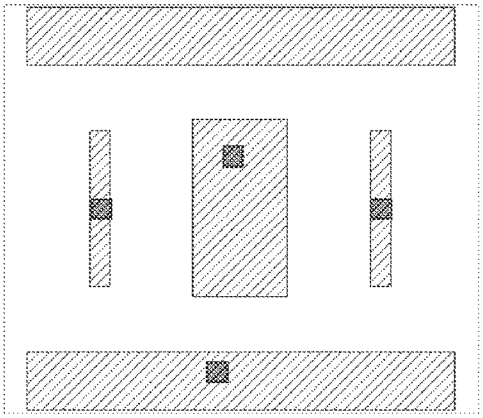
Figure 510A:
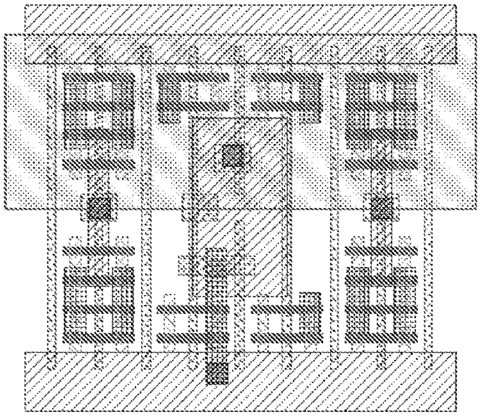
Figure 510B:
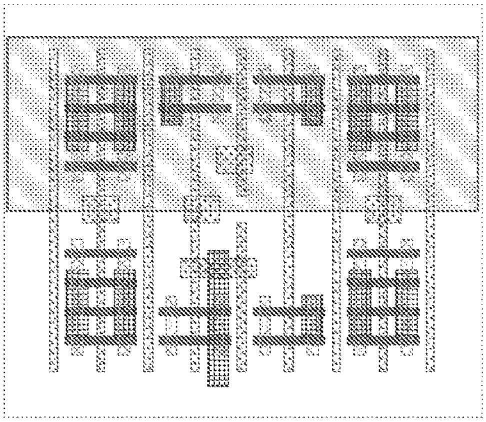
Figure 510C:
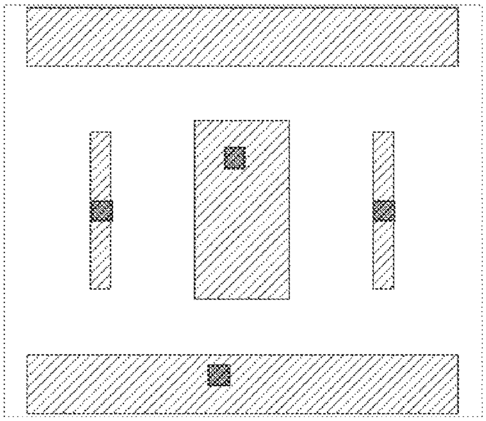
Figure 511A:
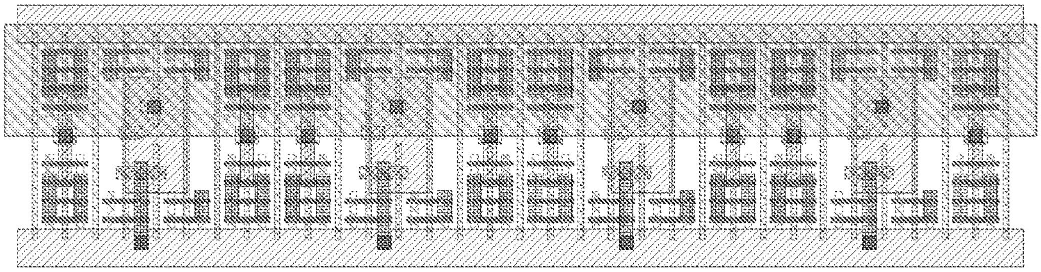
Figure 511B:
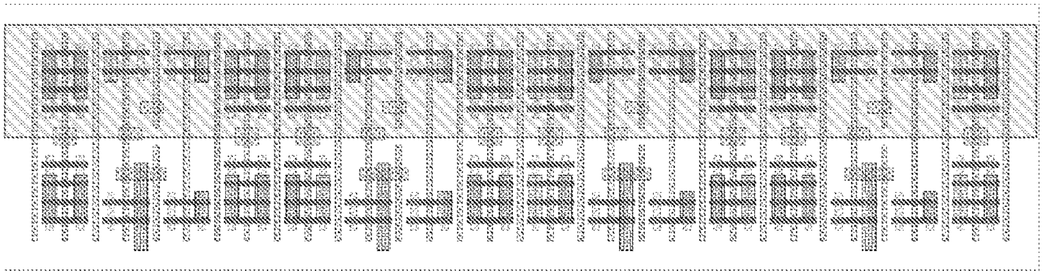
Figure 511C:
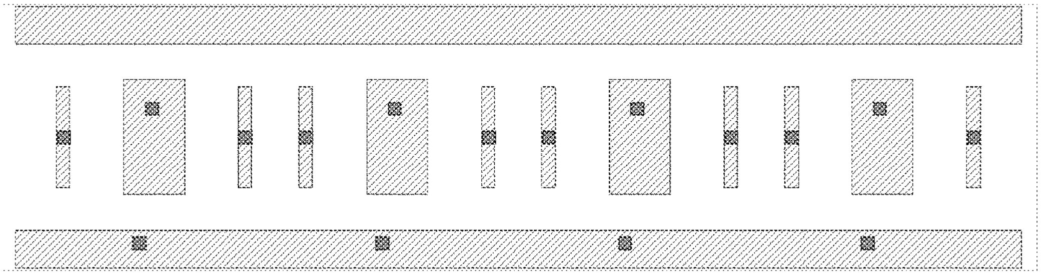
Figure 512A:
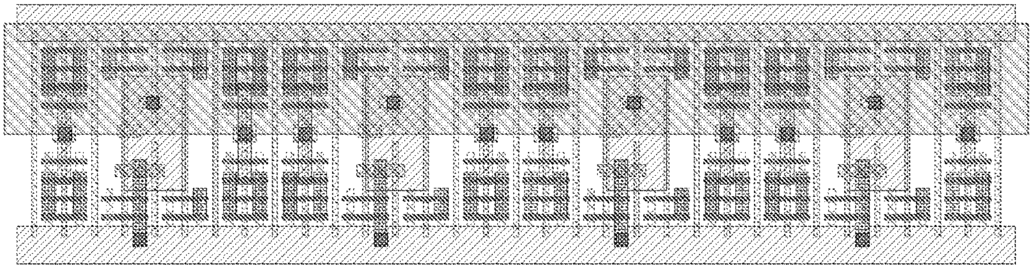
Figure 512B:
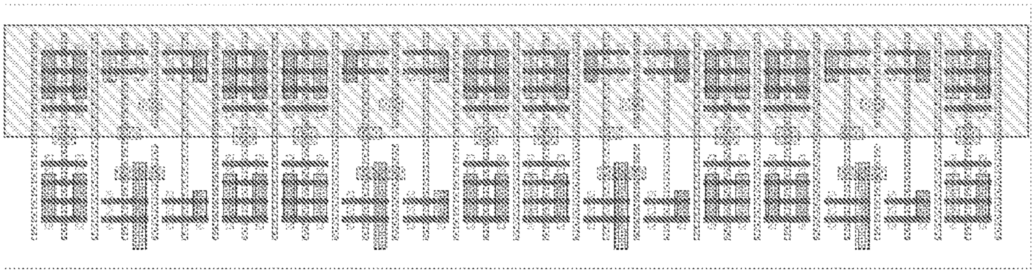
Figure 512C:
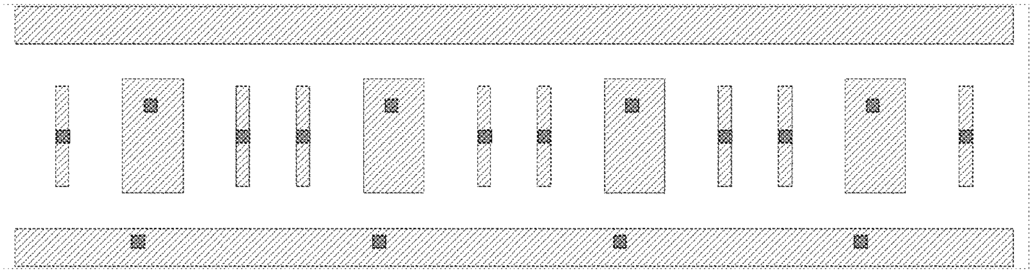
Figure 513A:
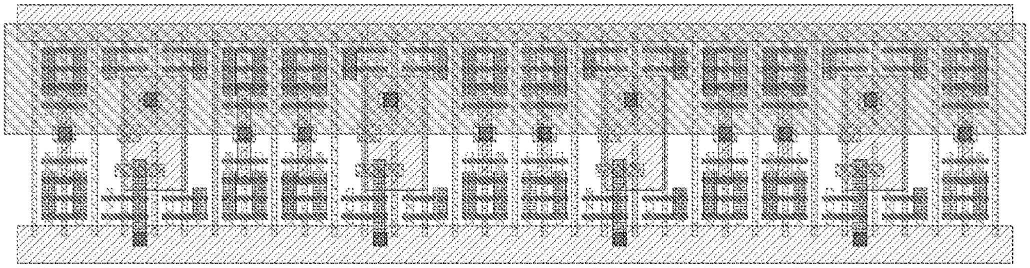
Figure 513B:
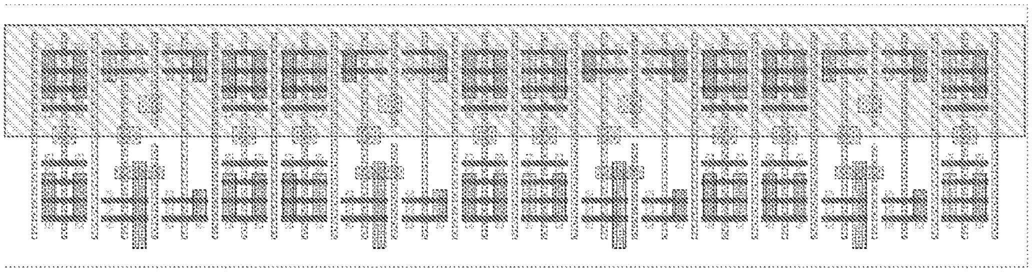
Figure 513C:
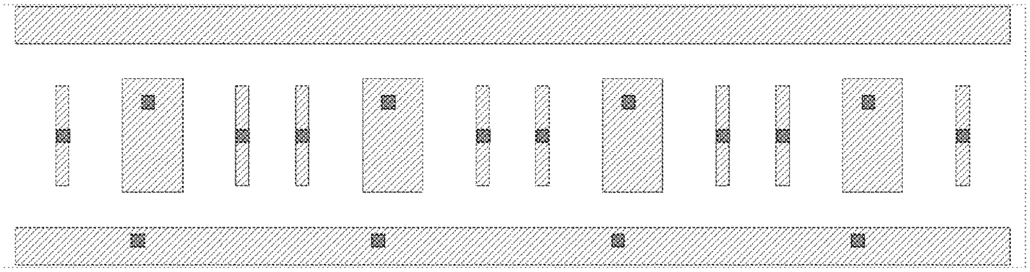
Figure 514A:
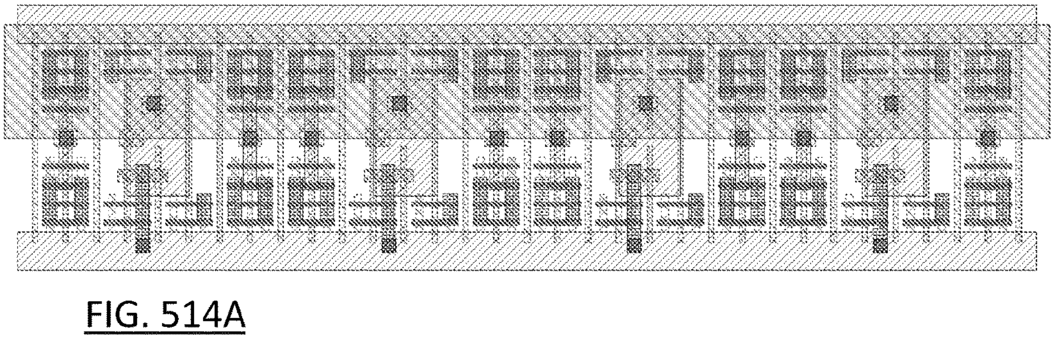
Figure 514B:
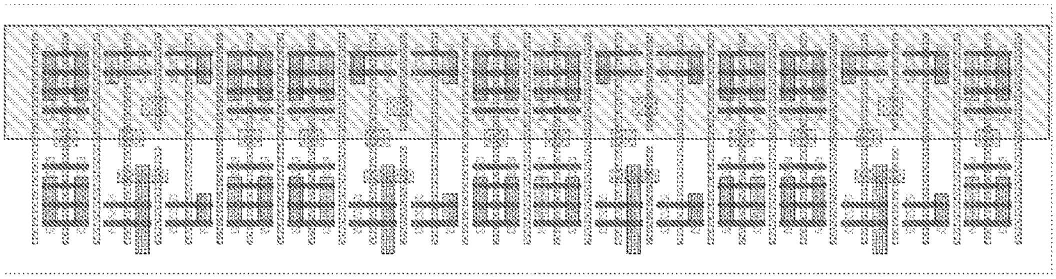
Figure 514C:
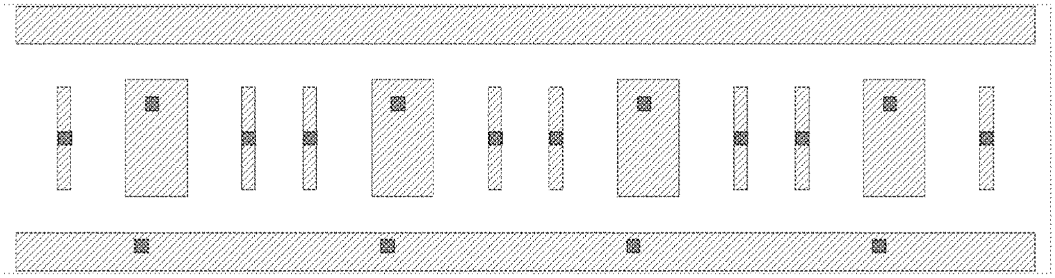
Figure 515A:
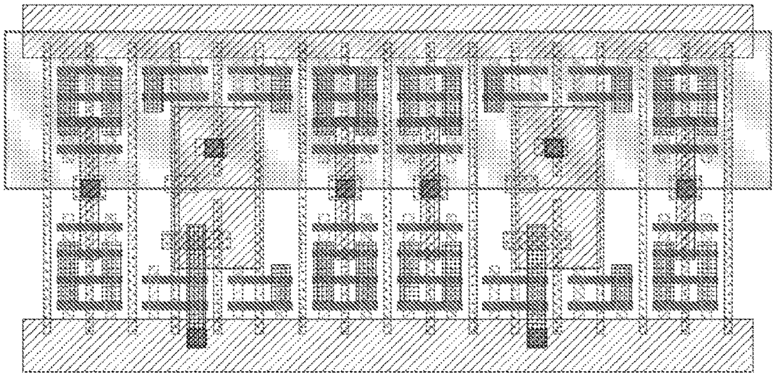
Figure 515B:
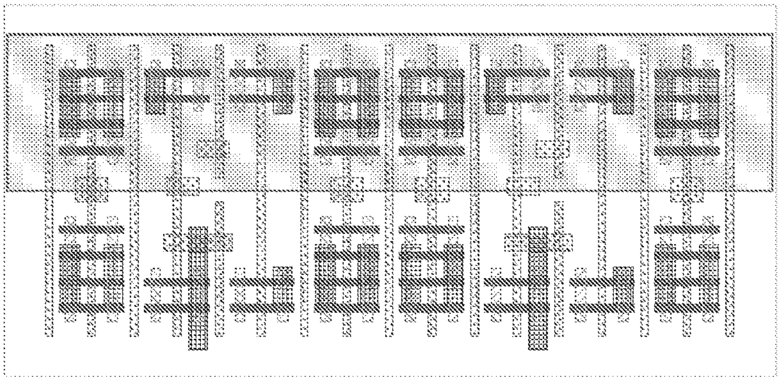
Figure 515C:
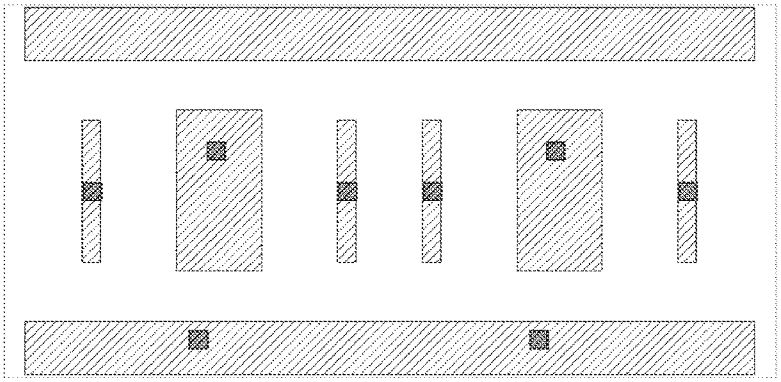
Figure 516A:
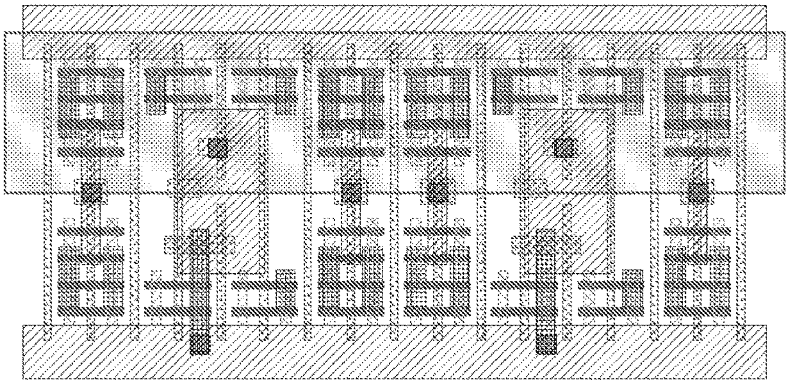
Figure 516B:
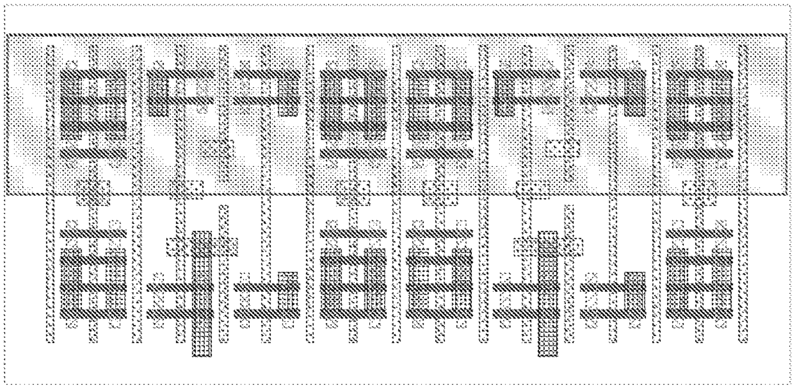
Figure 516C:
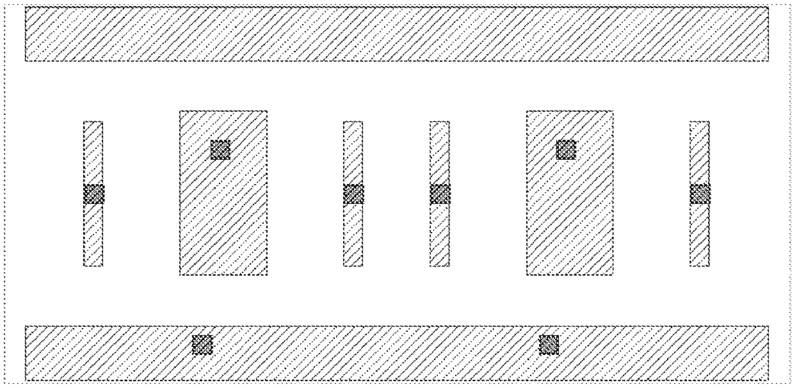
Figure 517A:
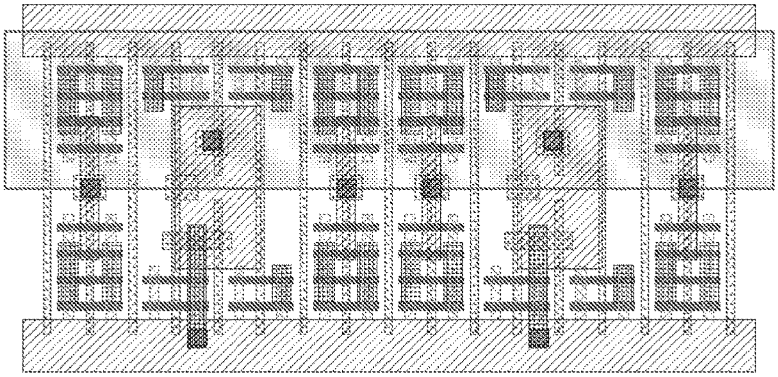
Figure 517B:
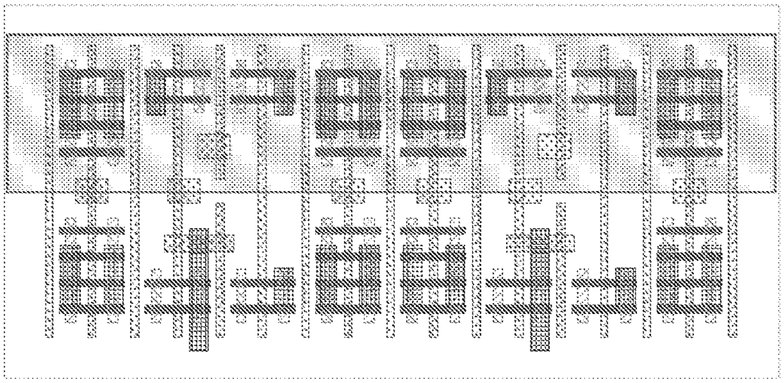
Figure 517C:
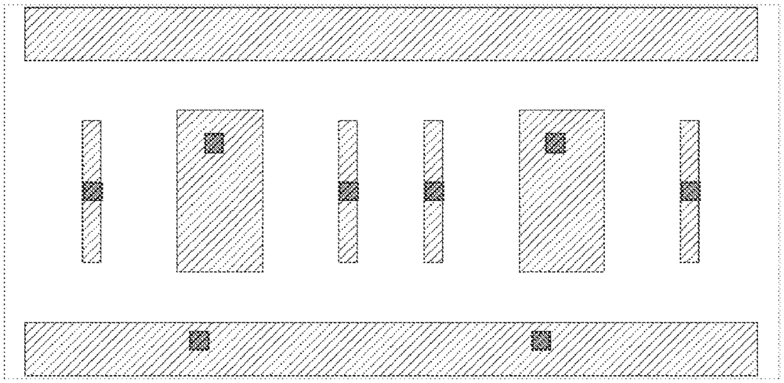
Figure 518A:
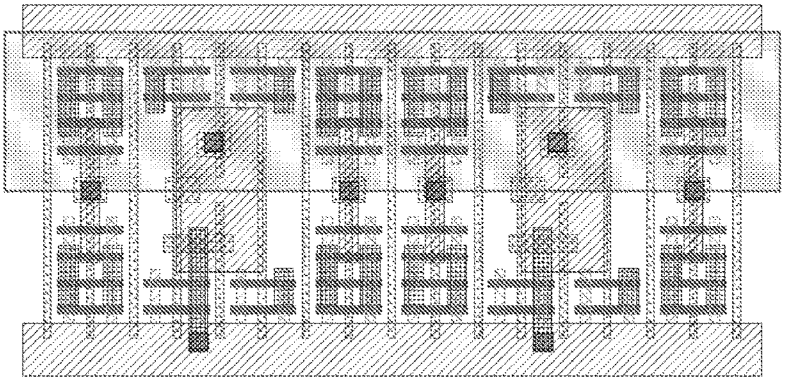
Figure 518B:
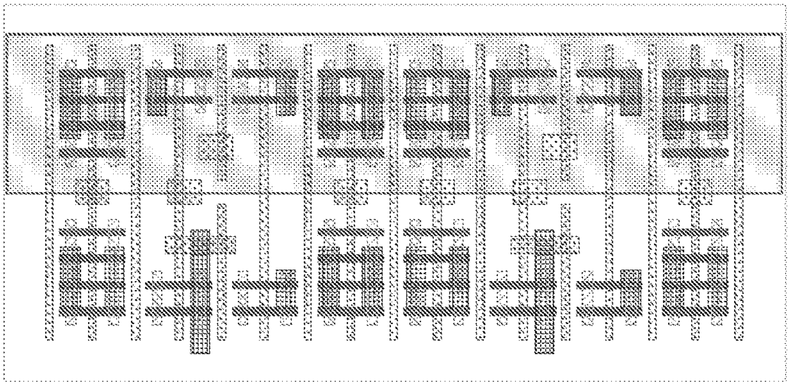
Figure 518C:
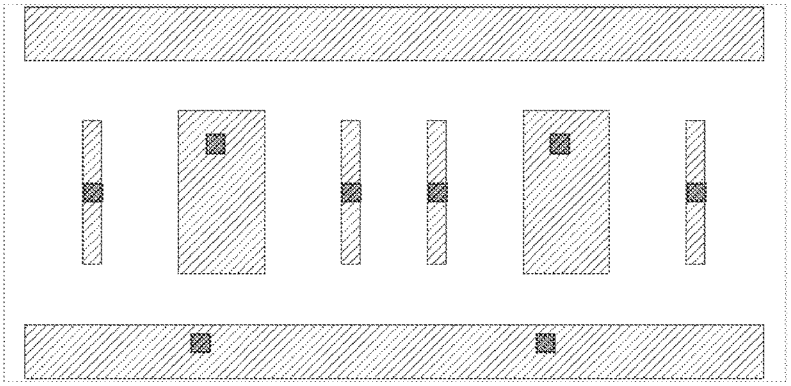
Figure 519A:
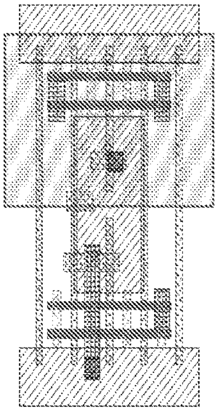
Figure 519B:
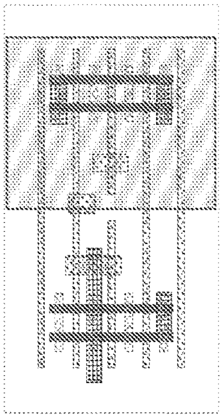
Figure 519C:
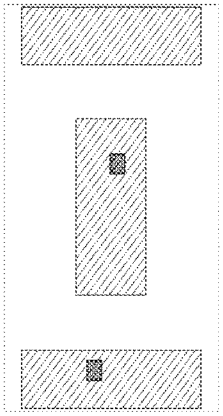
Figure 520A:
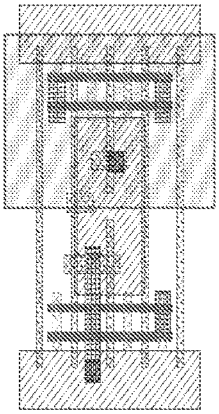
Figure 520B:
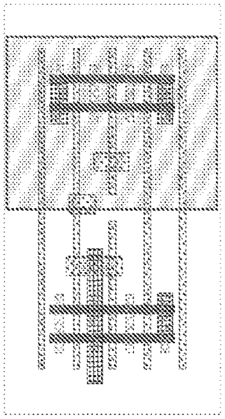
Figure 520C:
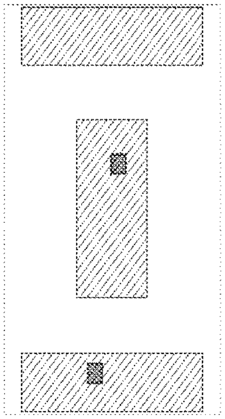
Figure 521A:
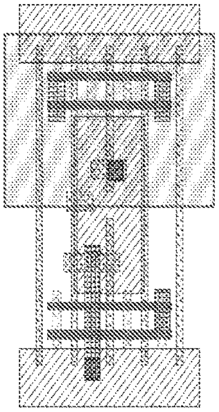
Figure 521B:
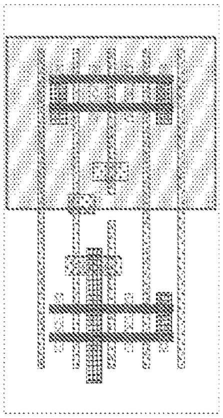
Figure 521C:
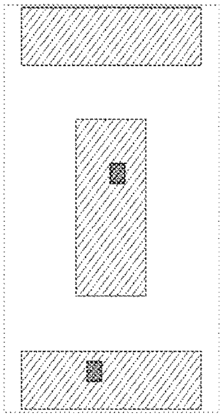
Figure 522A:
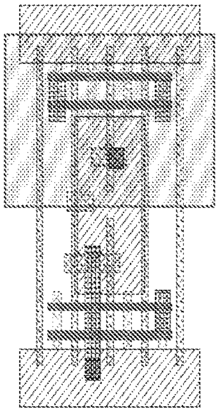
Figure 522B:
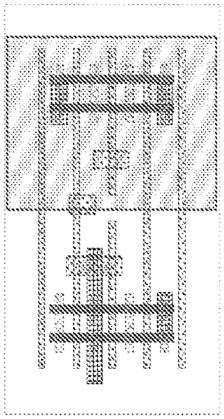
Figure 522C:
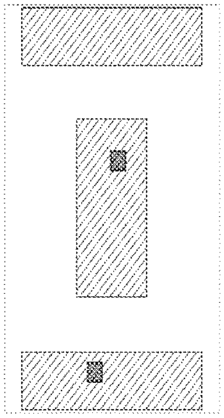
Figure 523A:
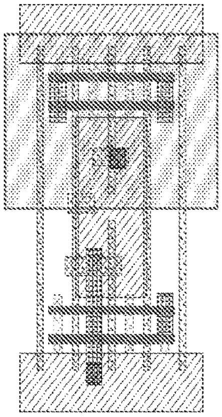
Figure 523B:
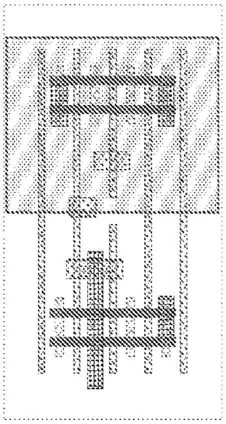
Figure 523C:
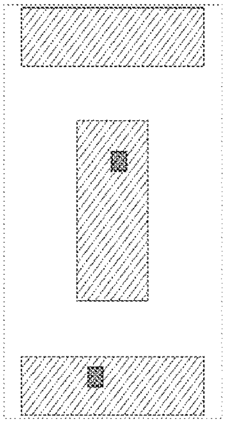
Figure 524A:
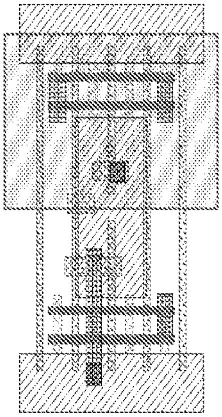
Figure 524B:
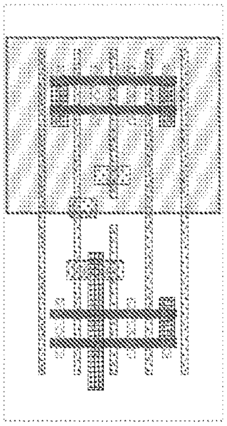
Figure 524C:
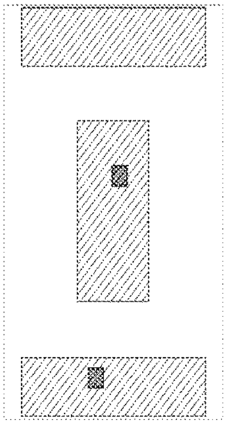
Figure 525A:
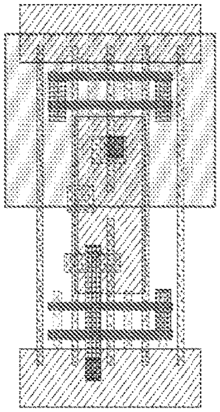
Figure 525B:
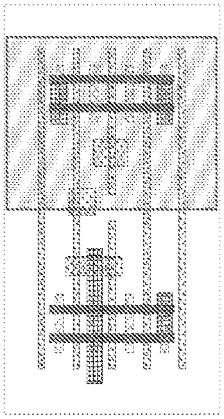
Figure 525C:
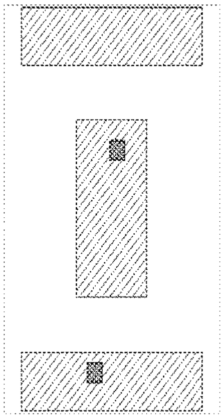
Figure 526A:
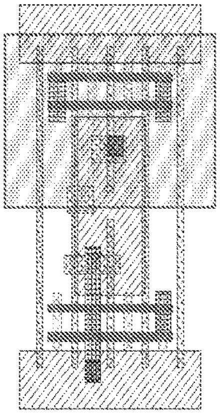
Figure 526B:
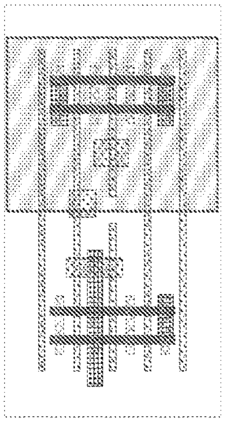
Figure 526C:
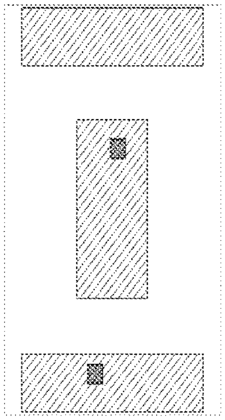
Figure 527A:
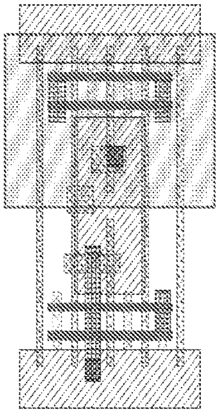
Figure 527B:
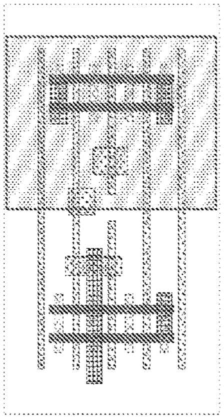
Figure 527C:
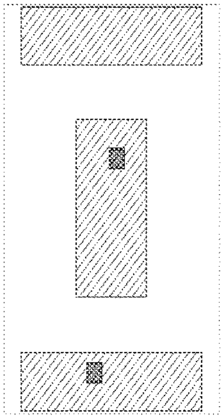
Figure 528A:
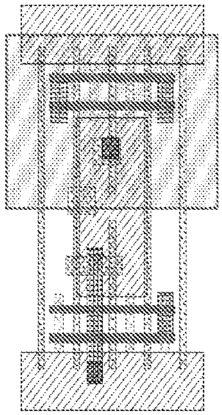
Figure 528B:
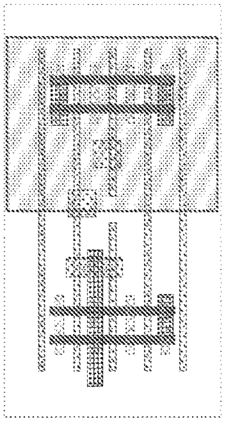
Figure 528C:
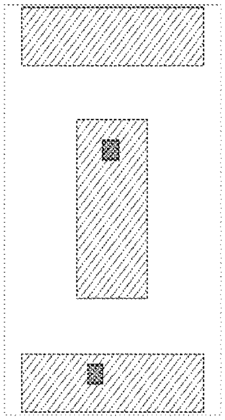
Figure 529A:
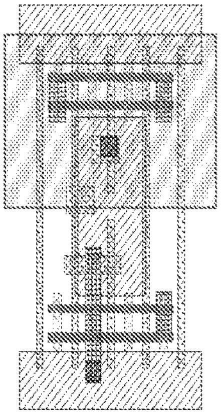
Figure 529B:
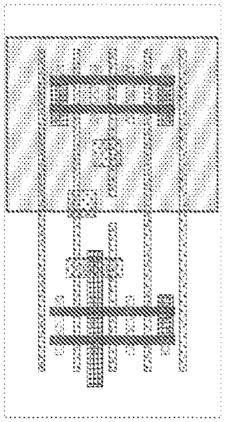
Figure 529C:
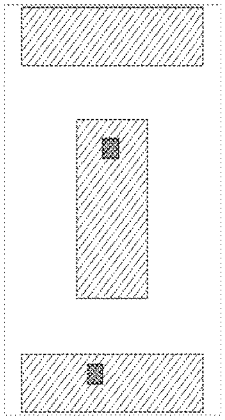
Figure 530A:
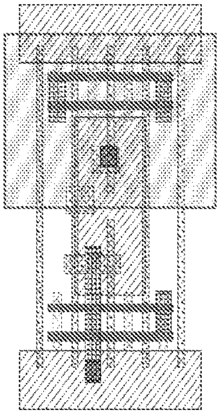
Figure 530B:
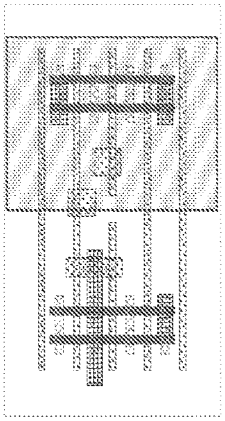
Figure 530C:
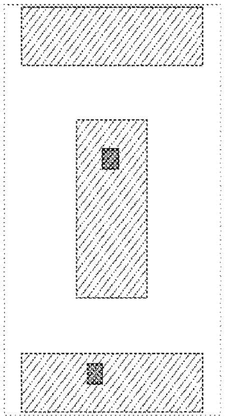
Figure 531A:
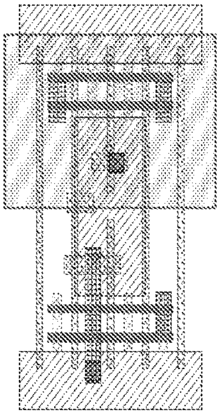
Figure 531B:
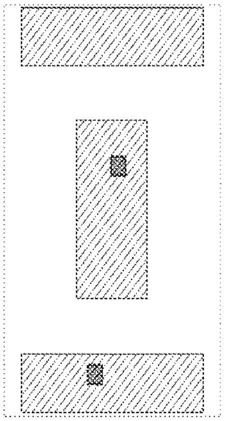
Figure 531C:
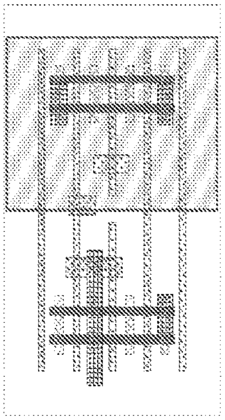
Figure 532A:
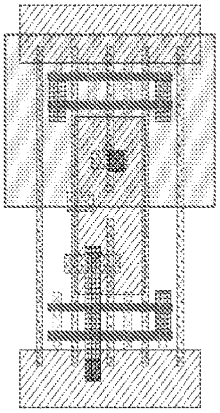
Figure 532B:
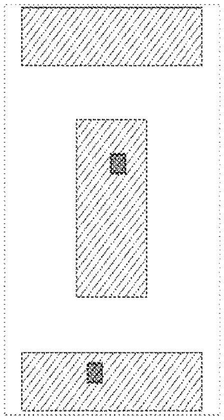
Figure 532C:
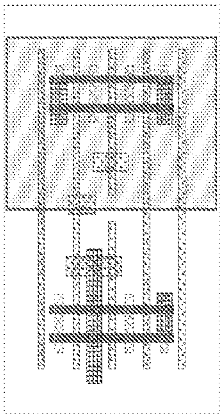
Figure 533A:
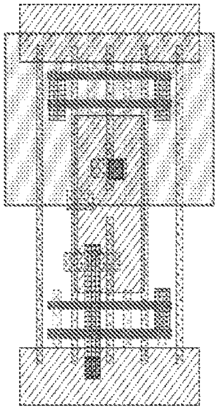
Figure 533B:
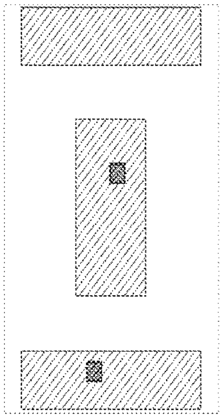
Figure 533C:
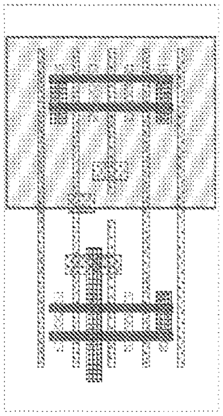
Figure 534A:
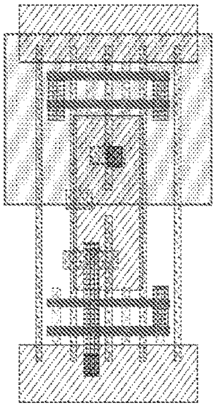
Figure 534B:
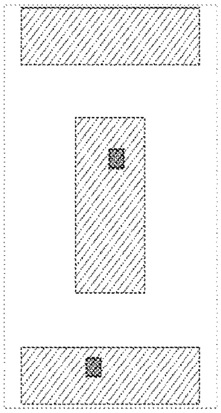
Figure 534C:
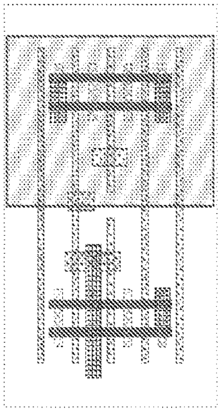
Figure 535A:
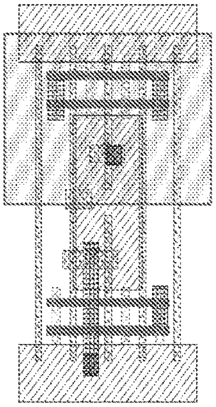
Figure 535B:
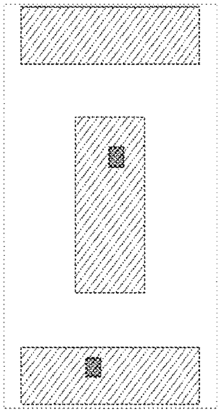
Figure 535C:
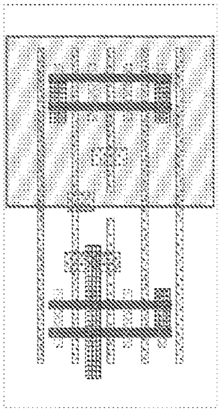
Figure 536A:
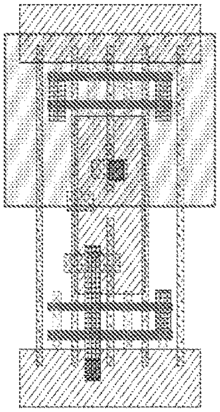
Figure 536B:
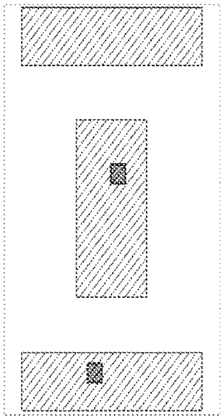
Figure 536C:
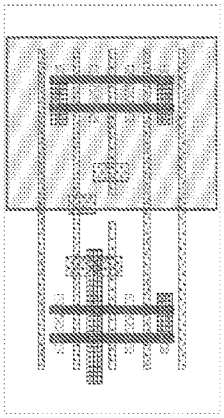
Figure 537A:
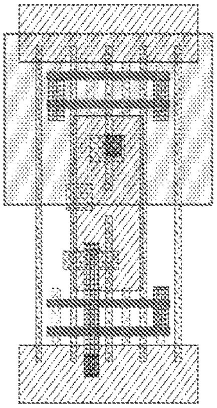
Figure 537B:
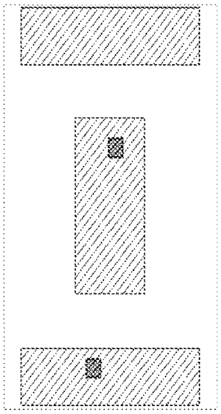
Figure 537C:
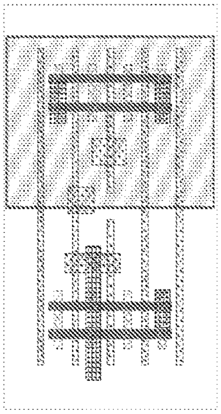
Figure 538A:
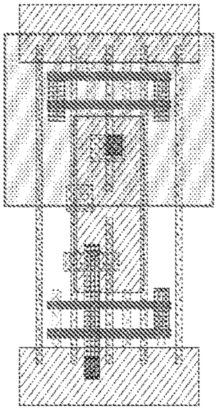
Figure 538B:
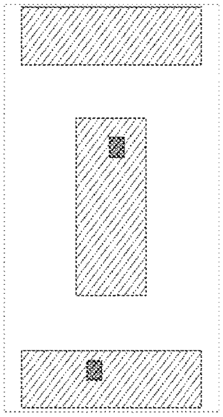
Figure 538C:
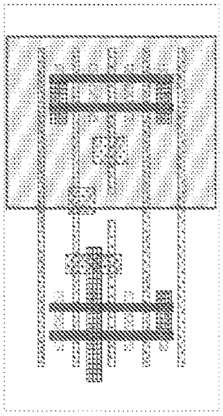
Figure 539A:
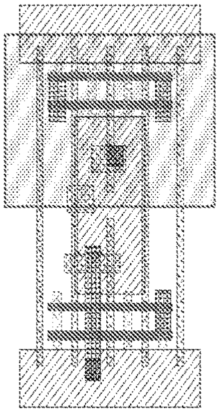
Figure 539B:
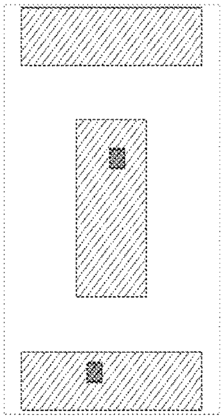
Figure 539C:
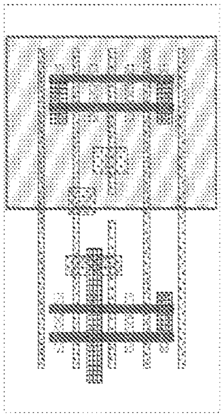
Figure 540A:
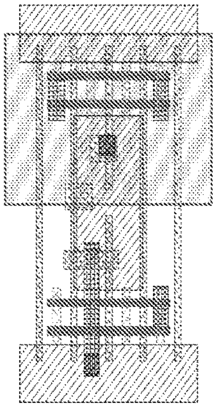
Figure 540B:
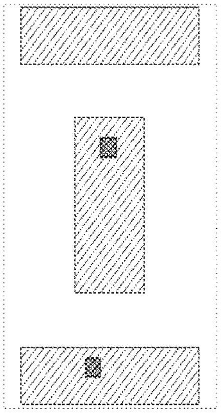
Figure 540C:
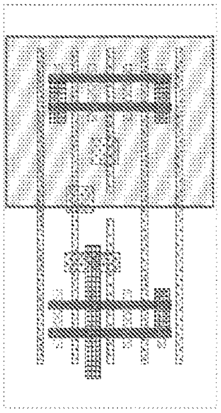
Figure 541A:
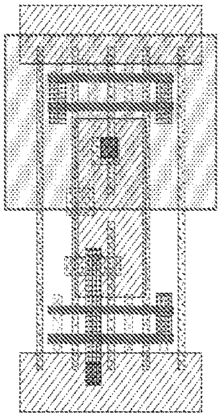
Figure 541B:
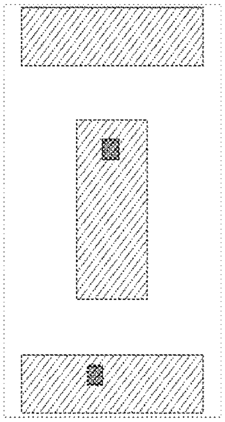
Figure 541C:
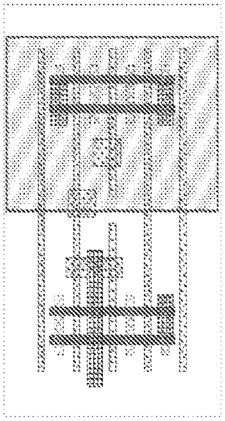
Figure 542A:
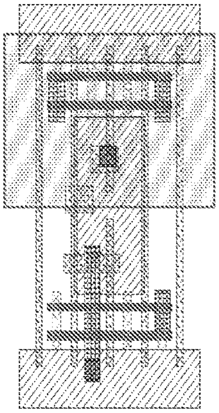
Figure 542B:
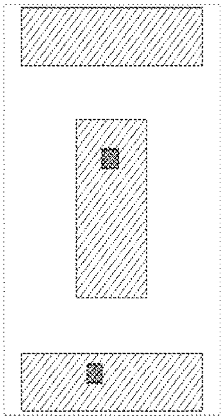
Figure 542C:
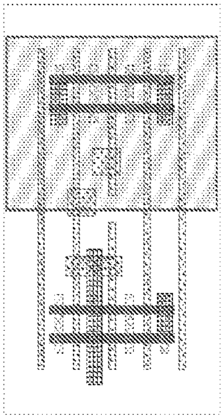
Figure 543A:
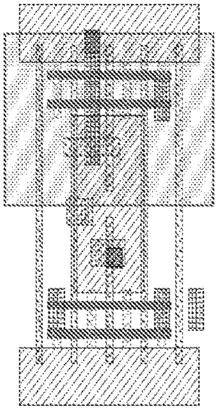
Figure 543B:
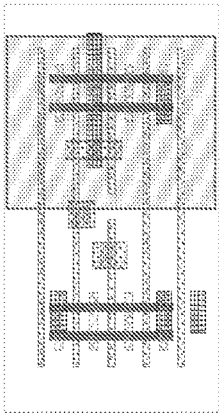
Figure 543C:
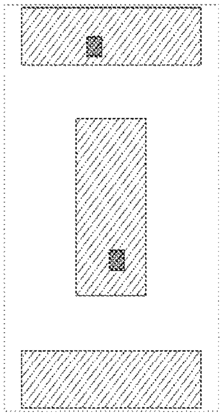
Figure 544A:
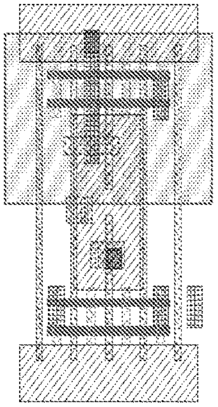
Figure 544B:
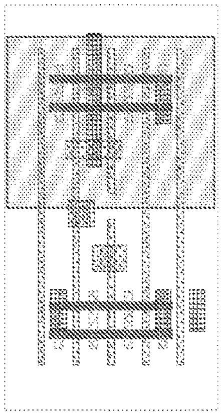
Figure 544C:
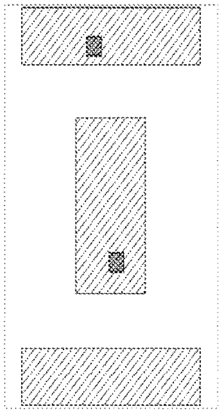
Figure 545A:
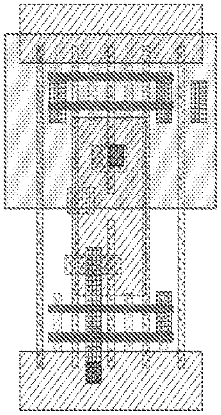
Figure 545B:
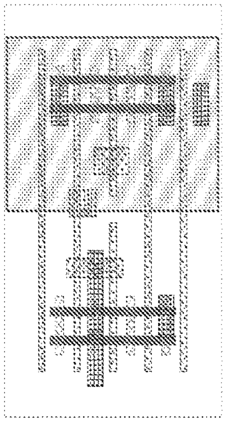
Figure 545C:
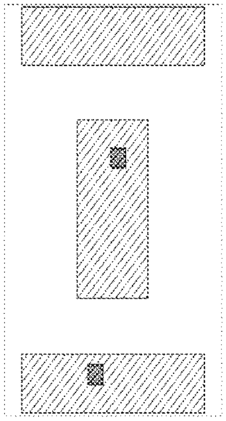
Figure 546A:
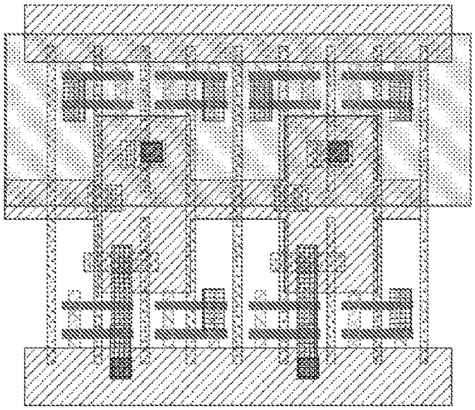
Figure 546B:
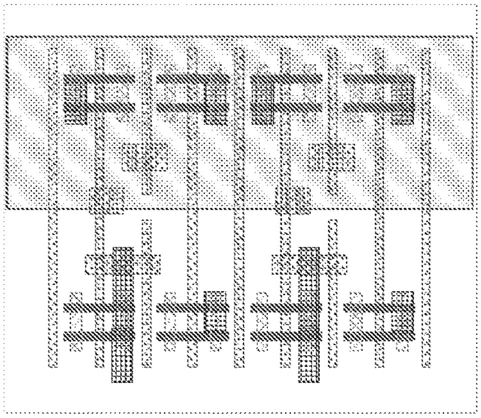
Figure 546C:
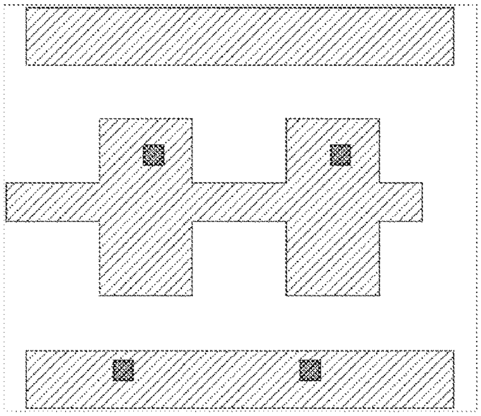
Figure 547A:
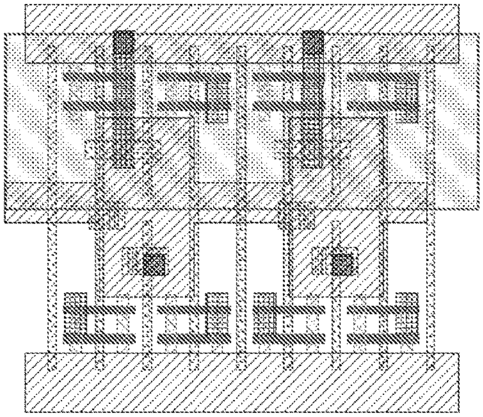
Figure 547B:
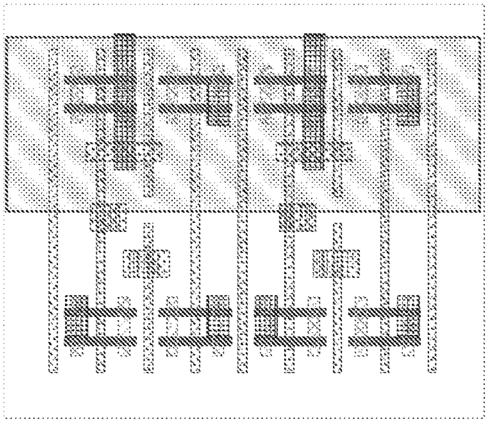
Figure 547C:
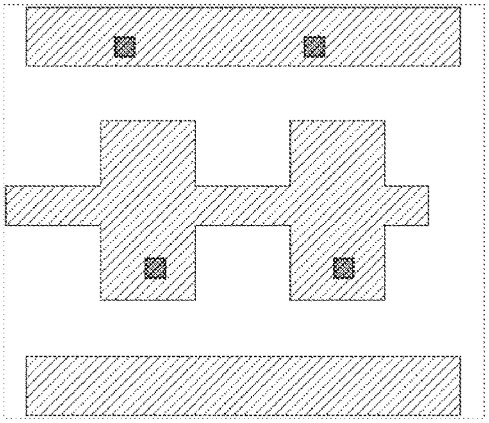
Figure 548A:
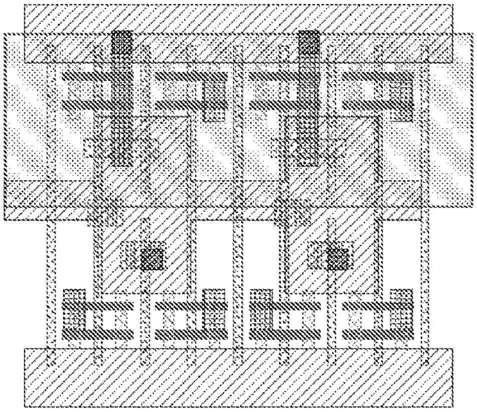
Figure 548B:
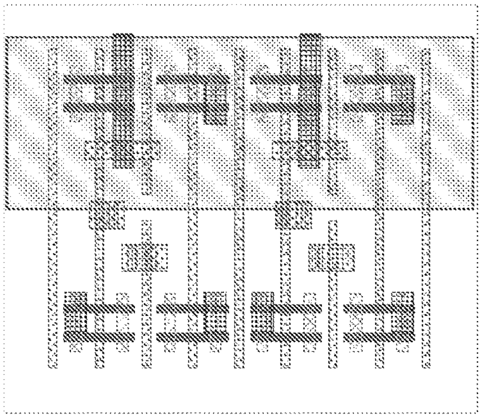
Figure 548C:
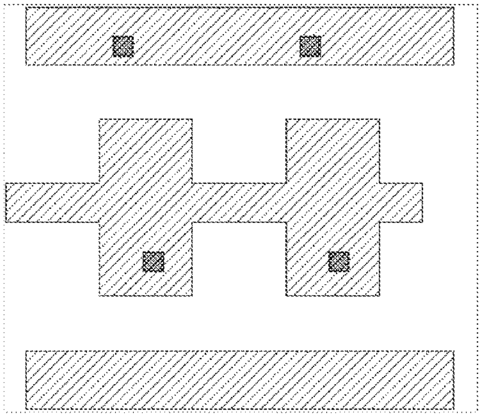
Figure 549A:
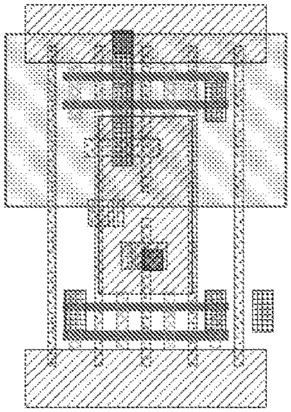
Figure 549B:
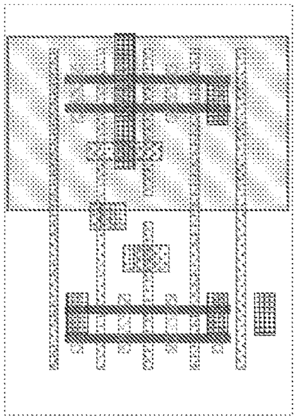
Figure 549C:
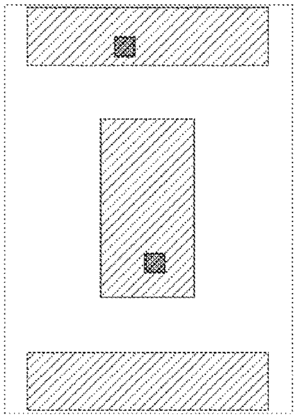
Figure 550A:
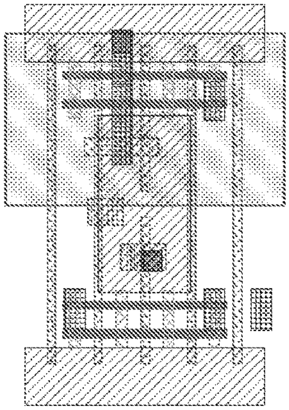
Figure 550B:
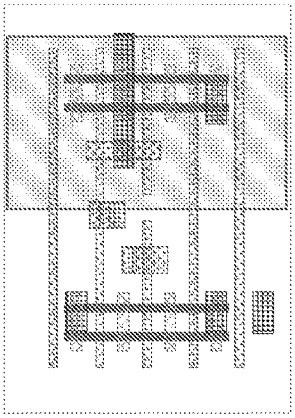
Figure 550C:
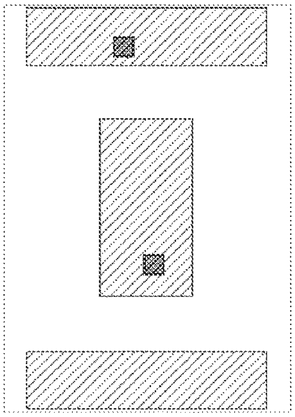
Figure 551A:
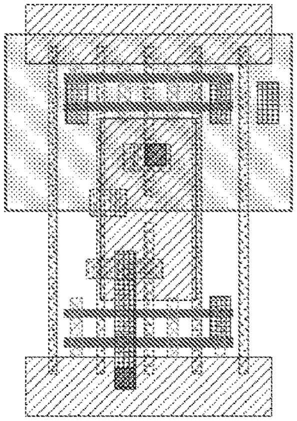
Figure 551B:
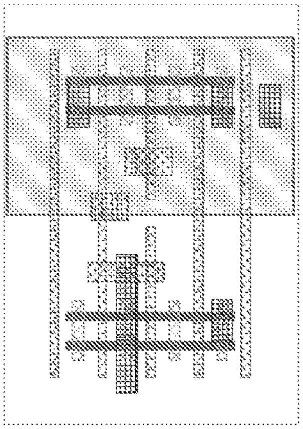
Figure 551C:
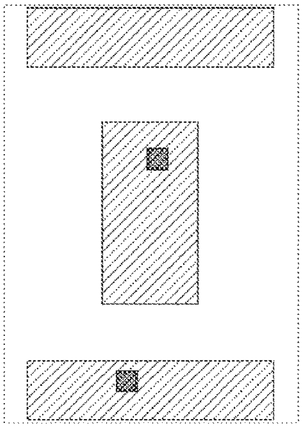
Figure 552A:
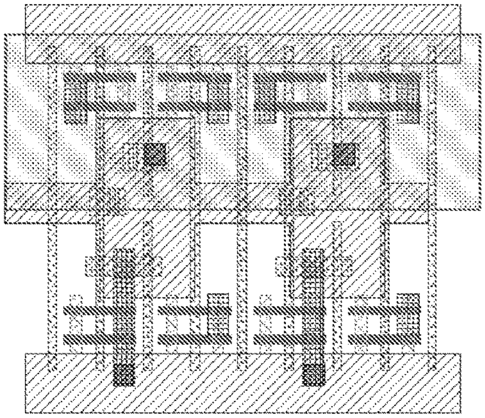
Figure 552B:
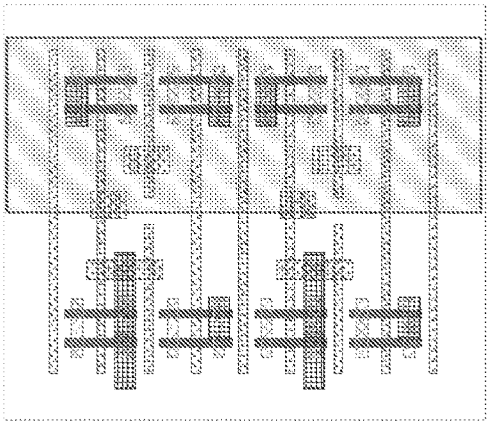
Figure 552C:
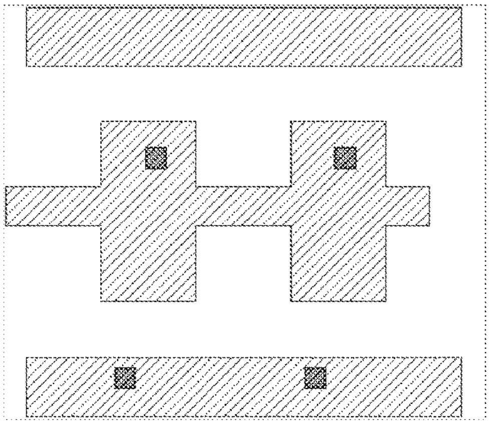
Figure 553A:
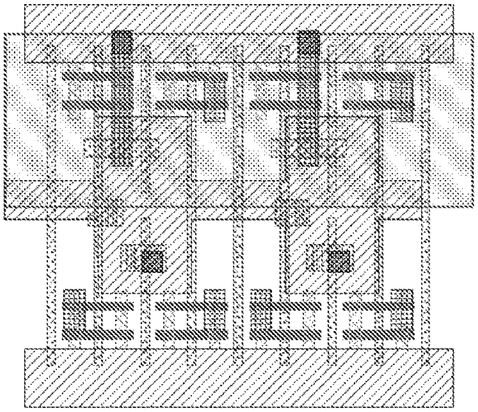
Figure 553B:
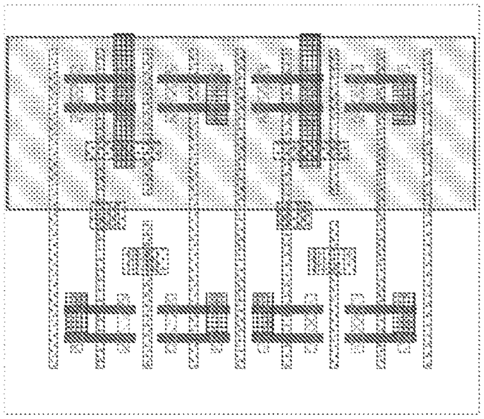
Figure 553C:
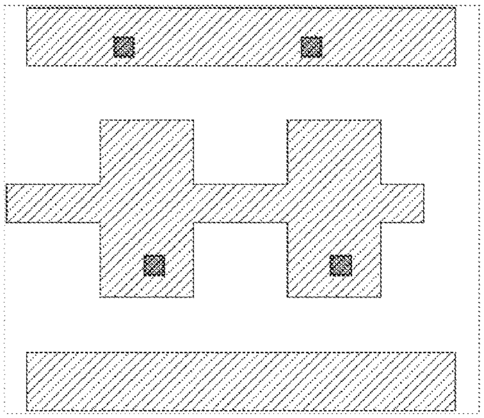
Figure 554A:
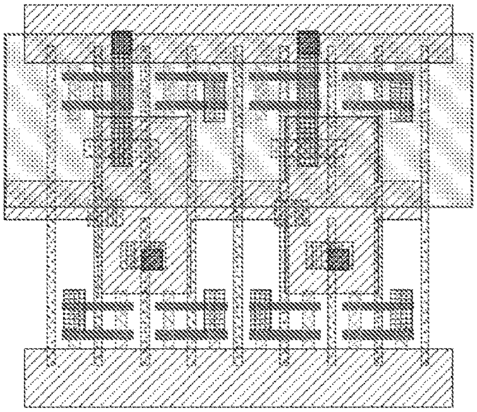
Figure 554B:
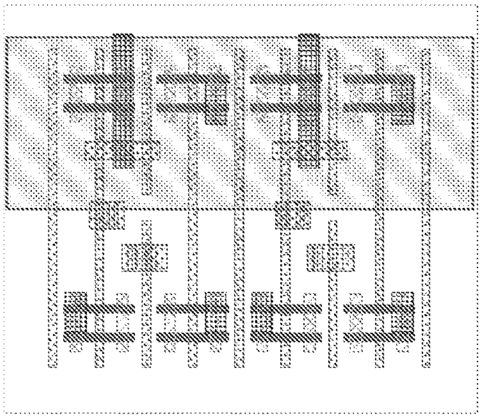
Figure 554C:
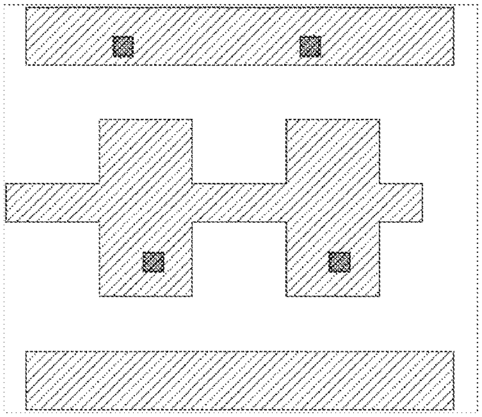
Figure 555A:
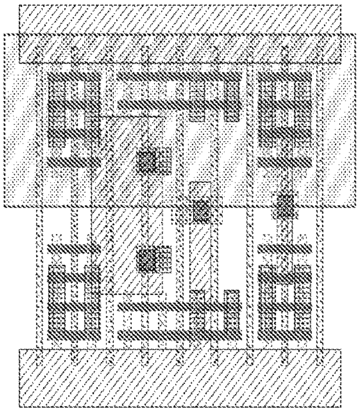
Figure 555B:
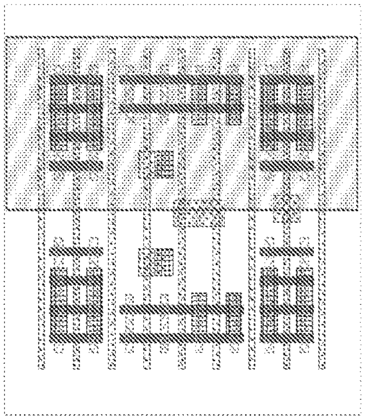
Figure 555C:
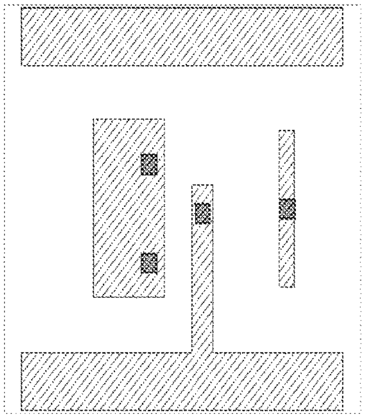
Figure 556A:
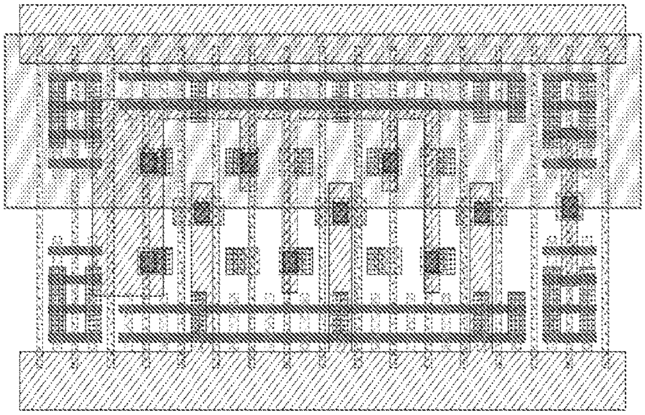
Figure 556B:
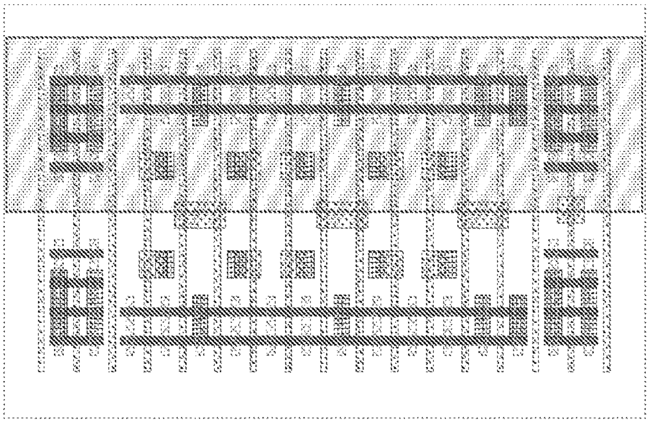
Figure 556C:
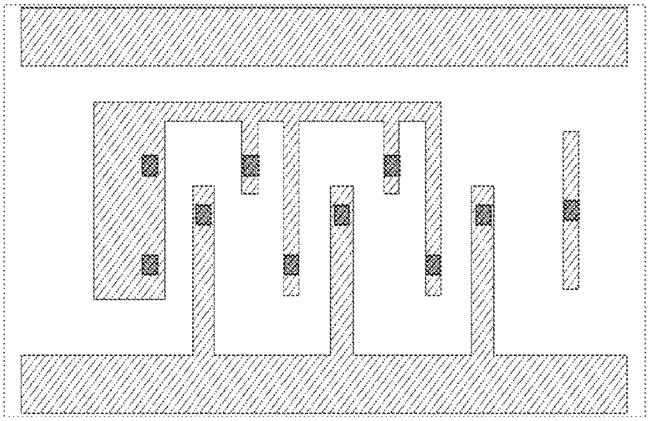
Figure 557A:
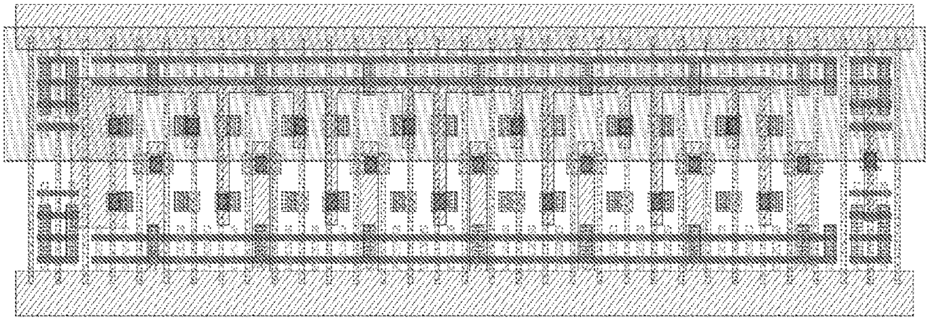
Figure 557B:
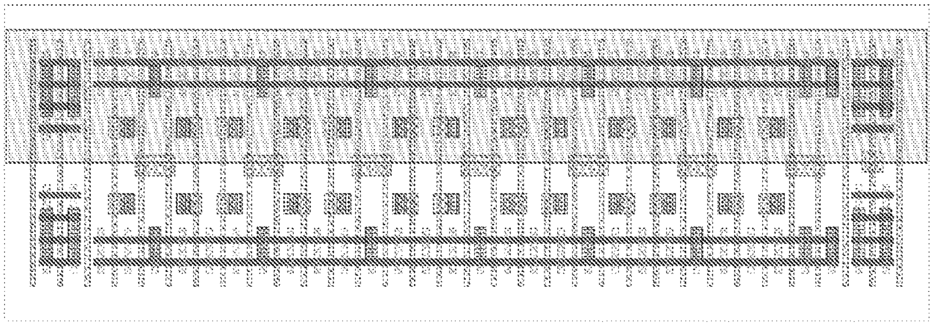
Figure 557C:
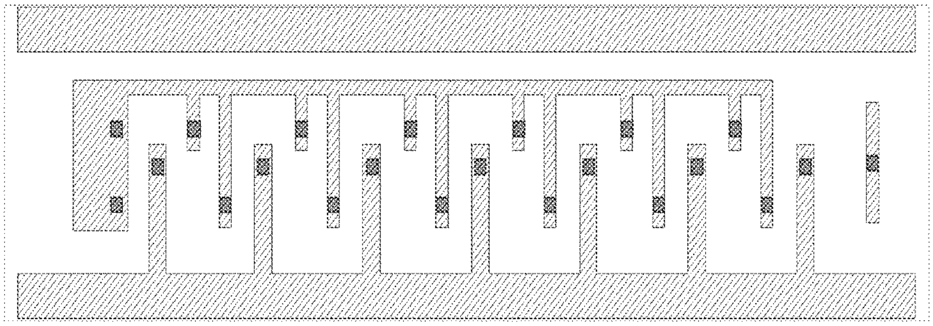
Figure 558A:
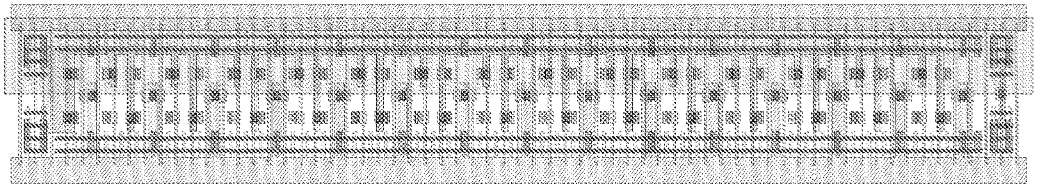
Figure 558B:
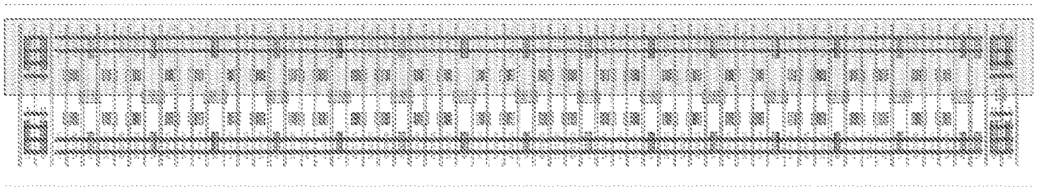
Figure 558C:
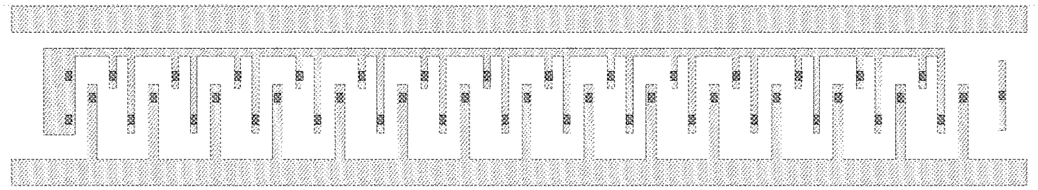
Figure 559A:
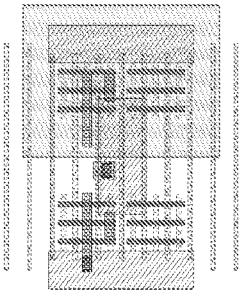
Figure 559B:
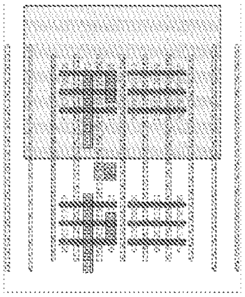
Figure 559C:
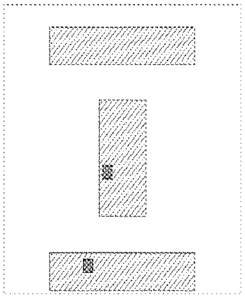
Figure 560A:
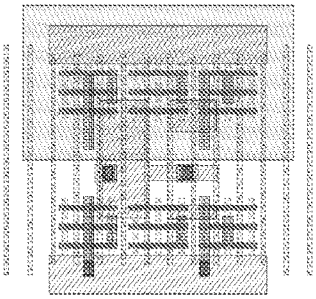
Figure 560B:
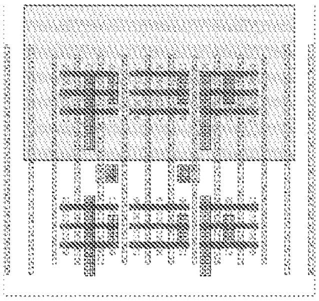
Figure 560C:
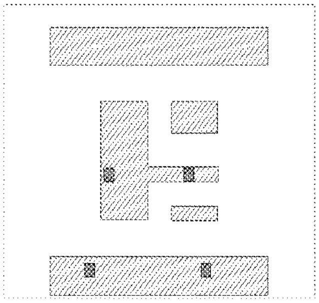
Figure 561A:
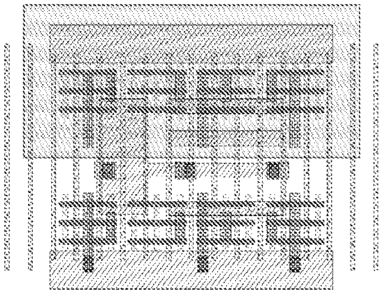
Figure 561B:
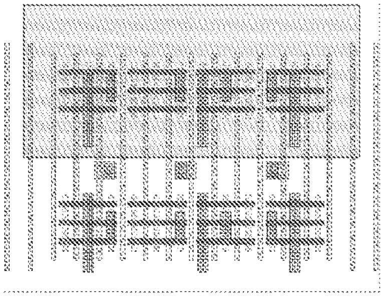
Figure 561C:
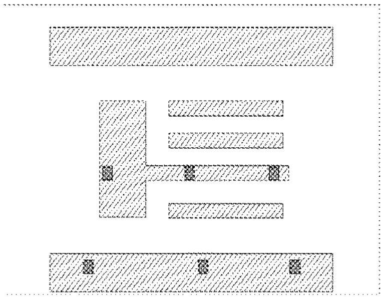
Figure 562A:
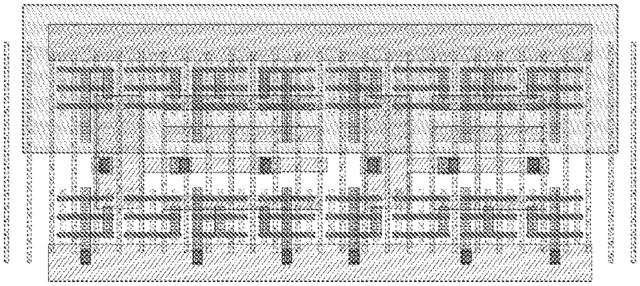
Figure 562B:
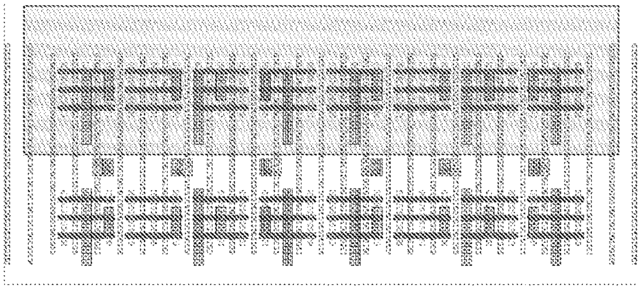
Figure 562C:
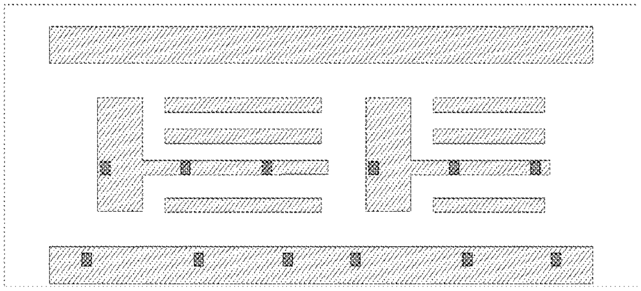
Figure 563A:
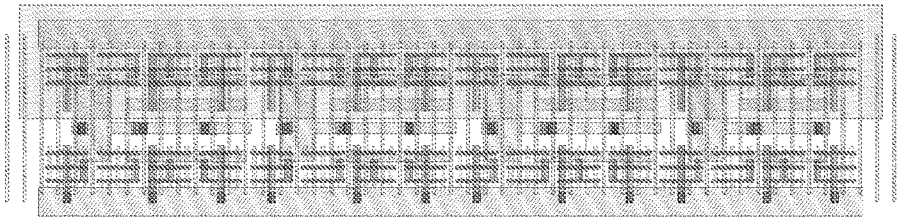
Figure 563B:
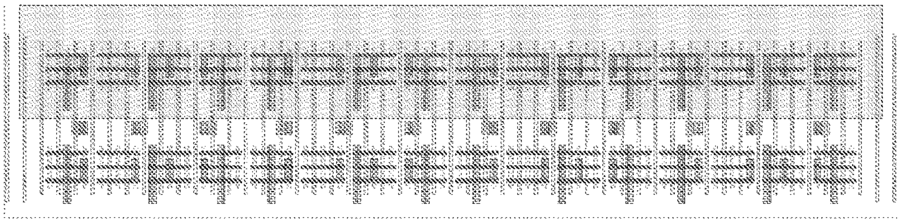
Figure 563C:
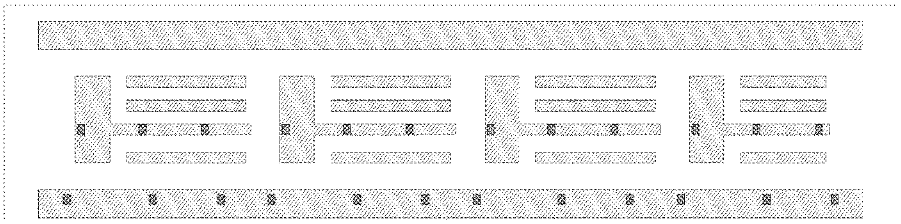
Figure 564A:
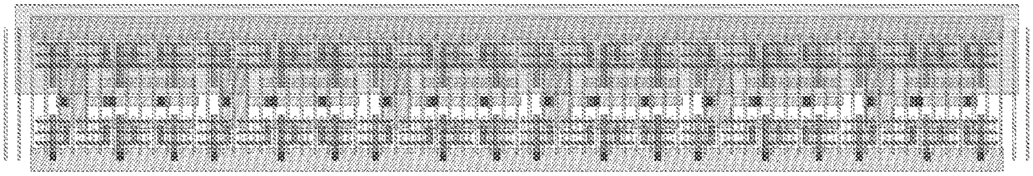
Figure 564B:
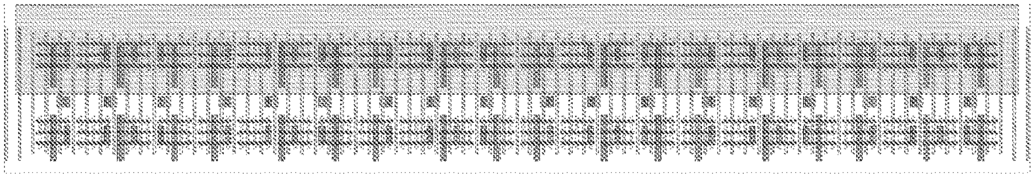
Figure 564C:
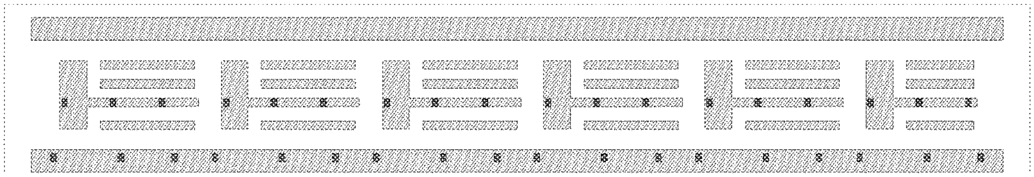
Figure 565A:
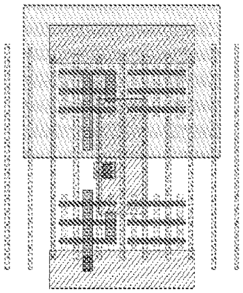
Figure 565B:
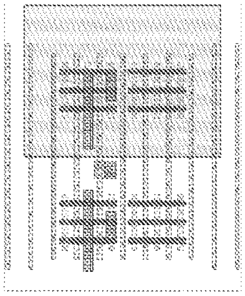
Figure 565C:
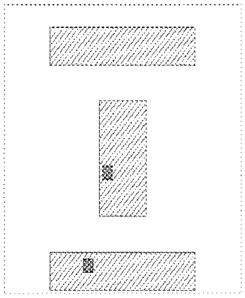
Figure 566A:
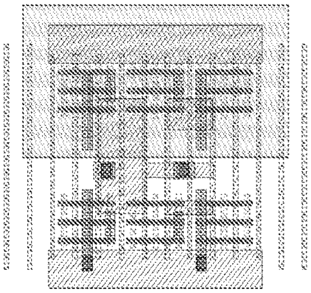
Figure 566B:
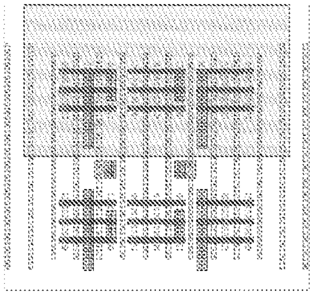
Figure 566C:
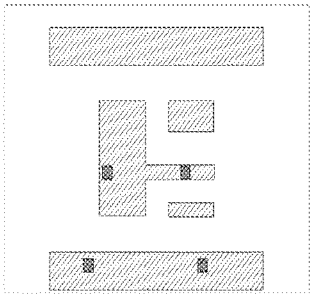
Figure 567A:
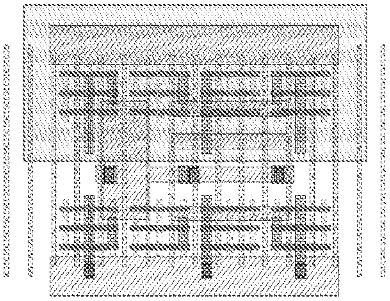
Figure 567B:
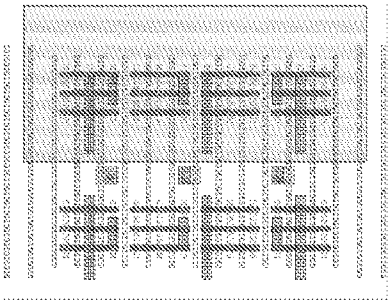
Figure 567C:
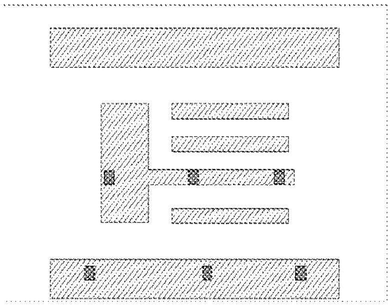
Figure 568A:
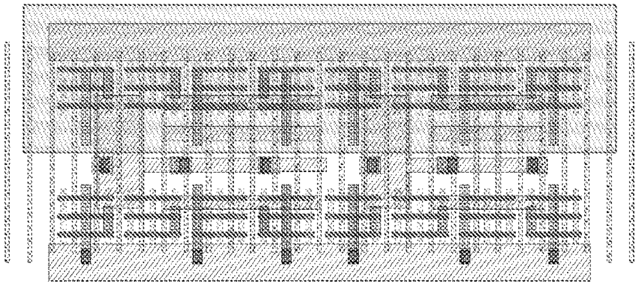
Figure 568B:
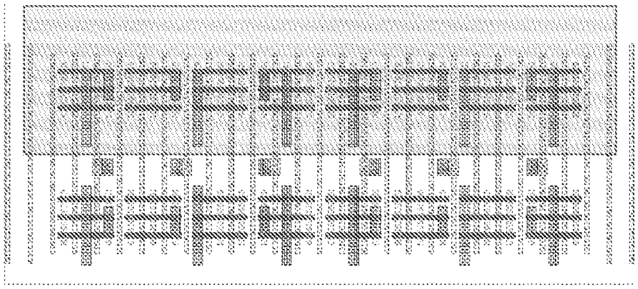
Figure 568C:
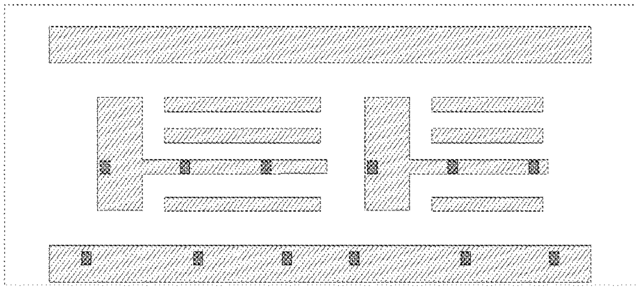
Figure 569A:
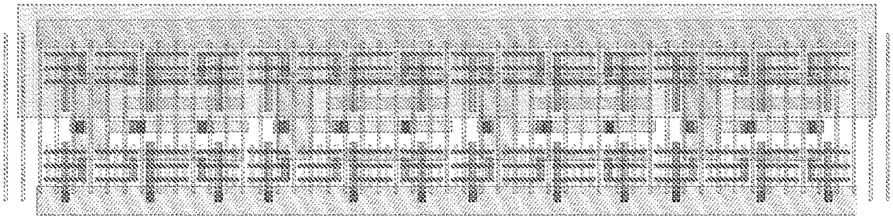
Figure 569B:
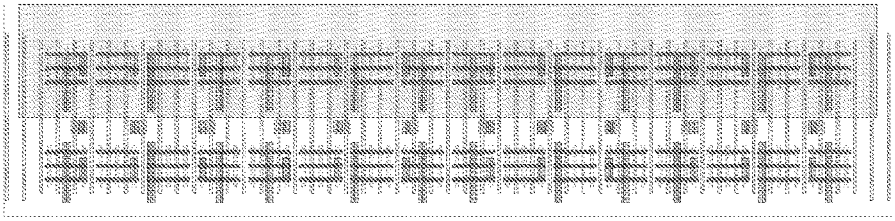
Figure 569C:
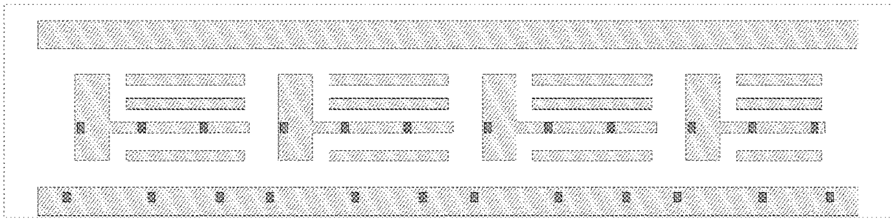
Figure 570A:
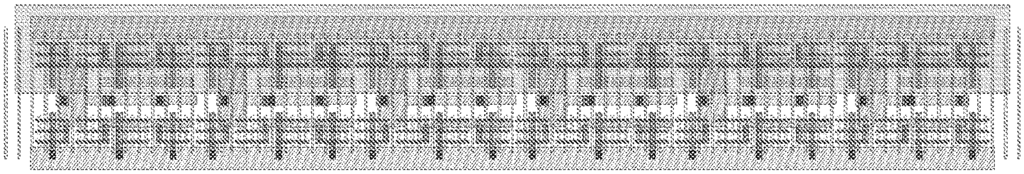
Figure 570B:
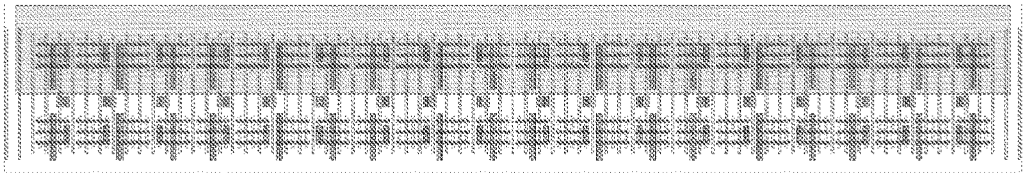
Figure 570C:
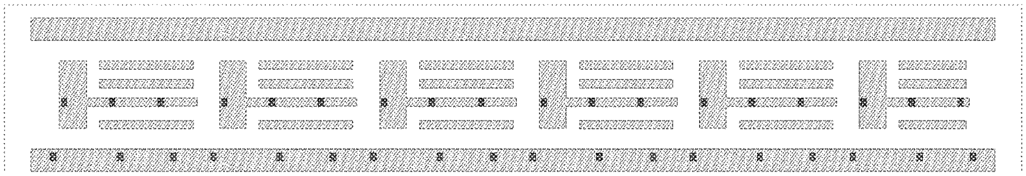
Figure 571A:
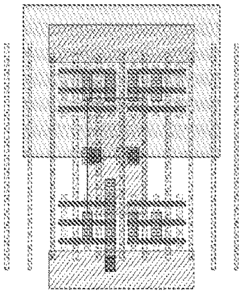
Figure 571B:
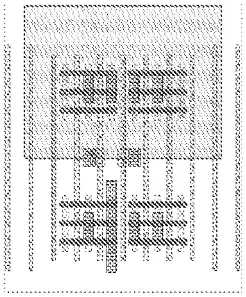
Figure 571C:
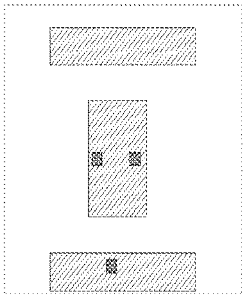
Figure 572A:
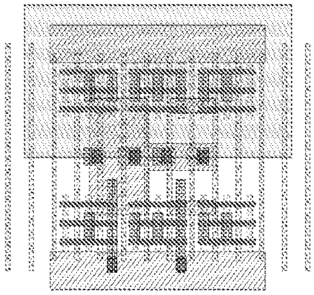
Figure 572B:
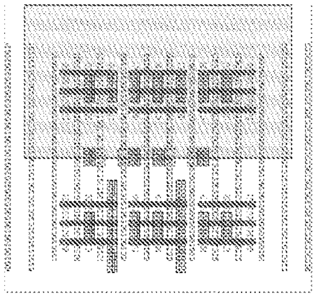
Figure 572C:
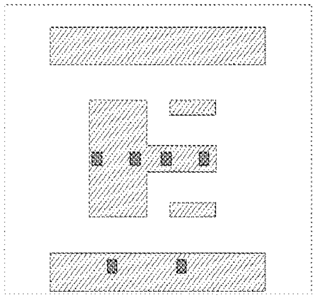
Figure 573A:
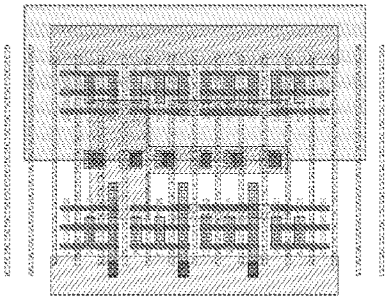
Figure 573B:
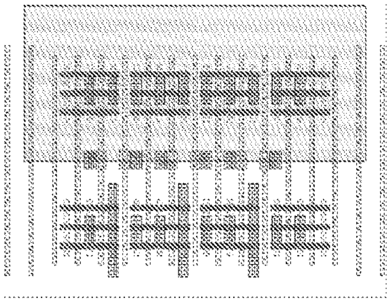
Figure 573C:
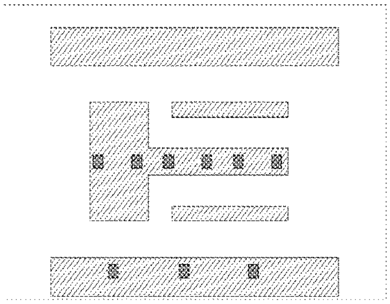
Figure 574A:
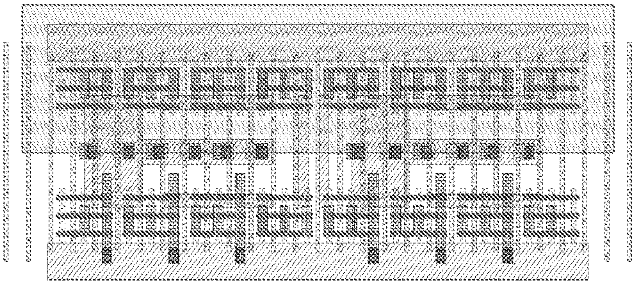
Figure 574B:
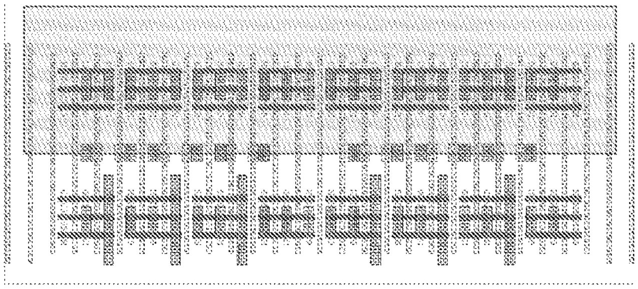
Figure 574C:
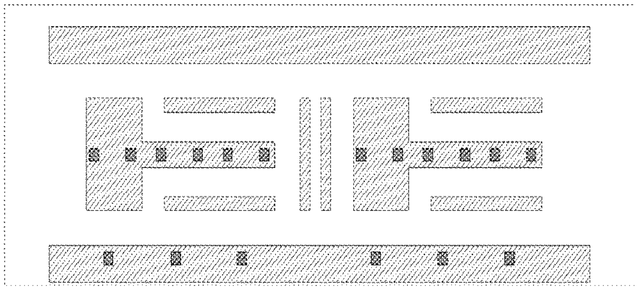
Figure 575A:
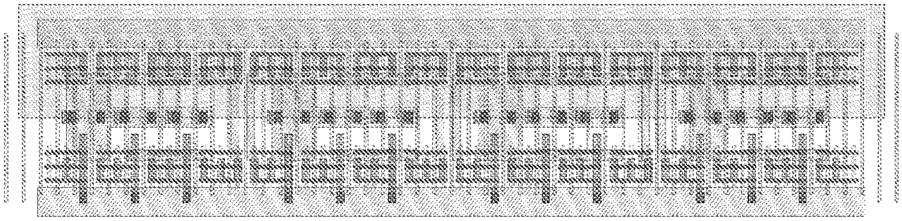
Figure 575B:
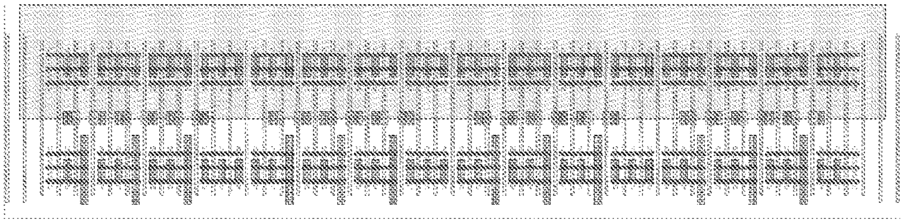
Figure 575C:
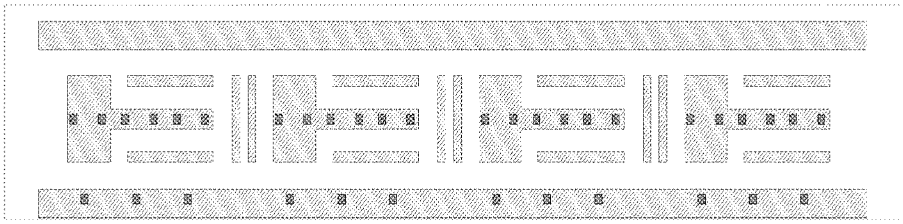
Figure 576A:
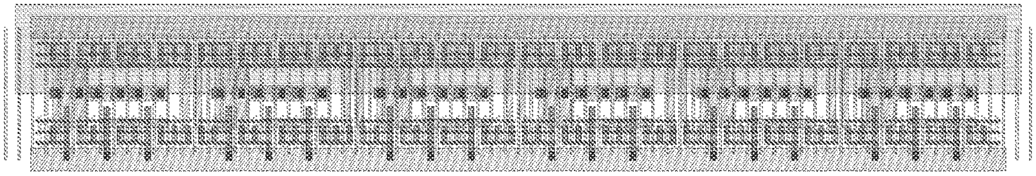
Figure 576B:
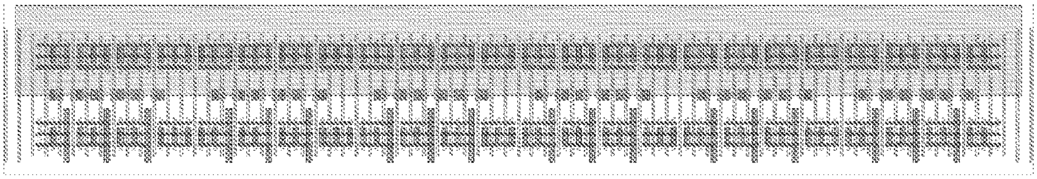
Figure 576C:
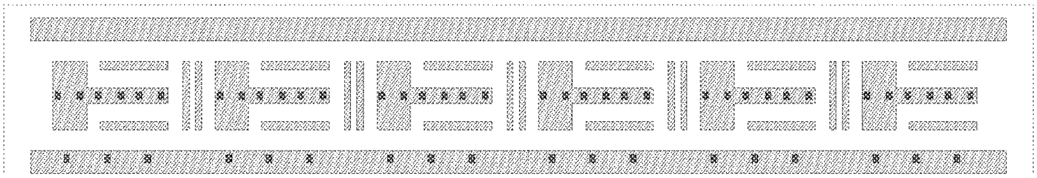
Figure 577A:
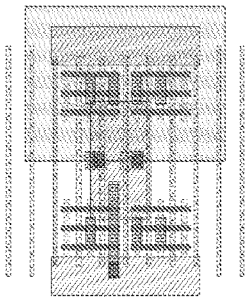
Figure 577B:
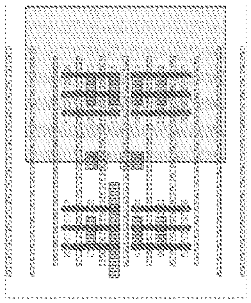
Figure 577C:
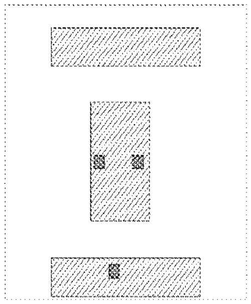
Figure 578A:
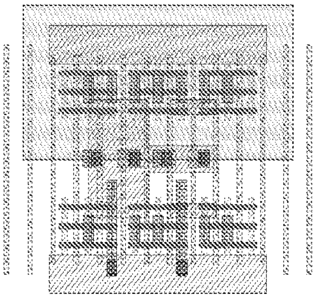
Figure 578B:
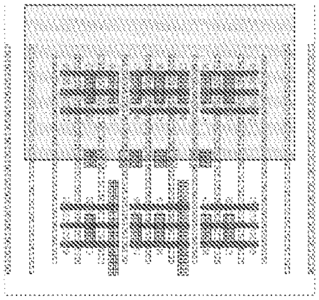
Figure 578C:
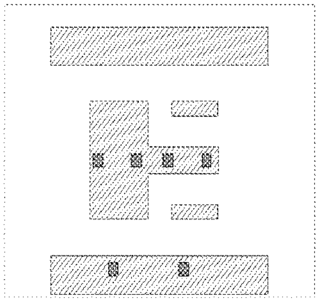
Figure 579A:
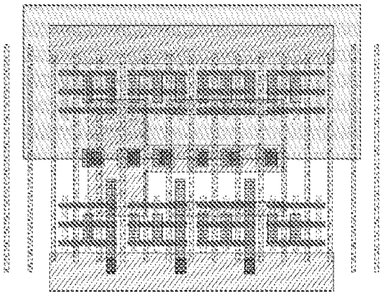
Figure 579B:
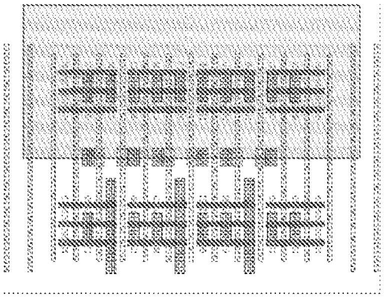
Figure 579C:
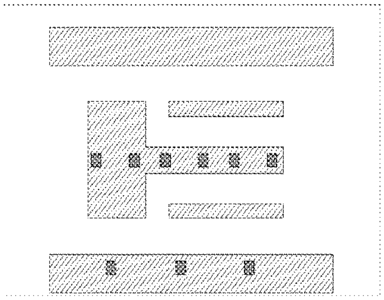
Figure 580A:
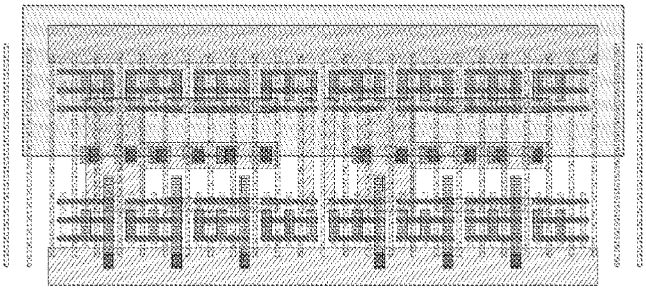
Figure 580B:
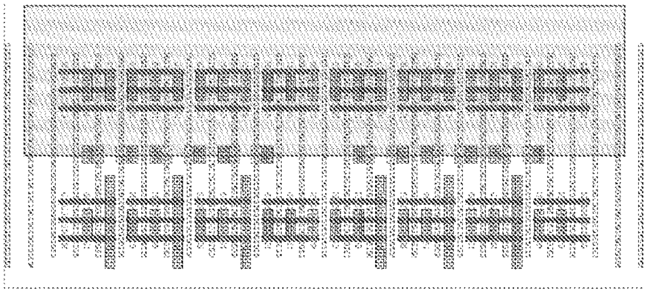
Figure 580C:
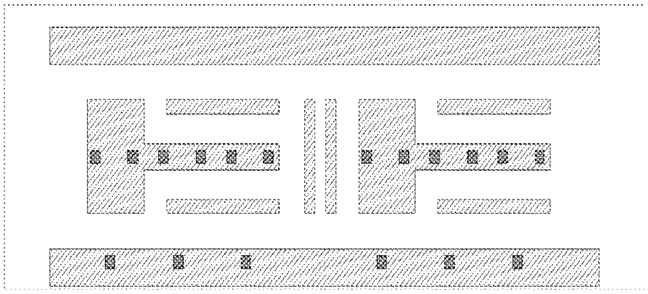
Figure 581A:
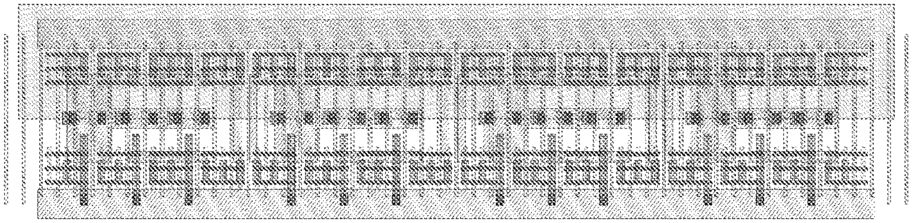
Figure 581B:
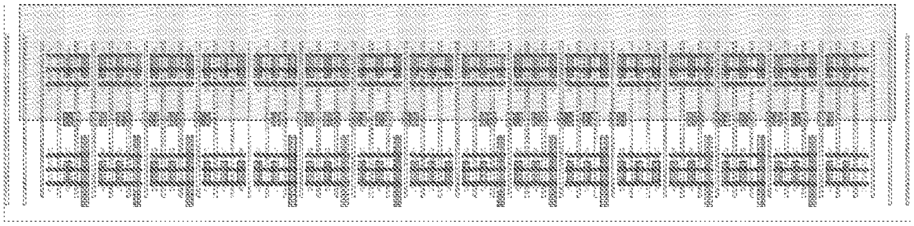
Figure 581C:
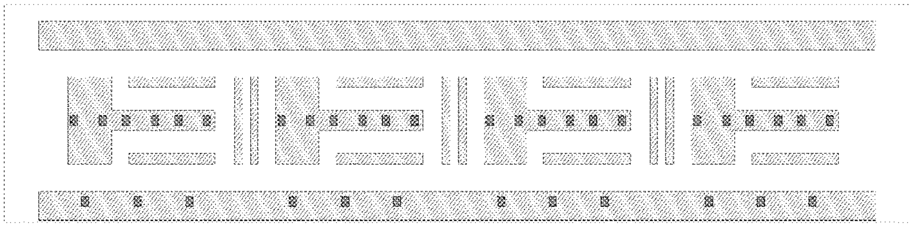
Figure 582A:
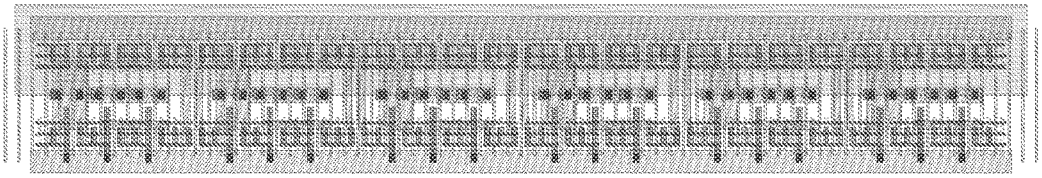
Figure 582B:
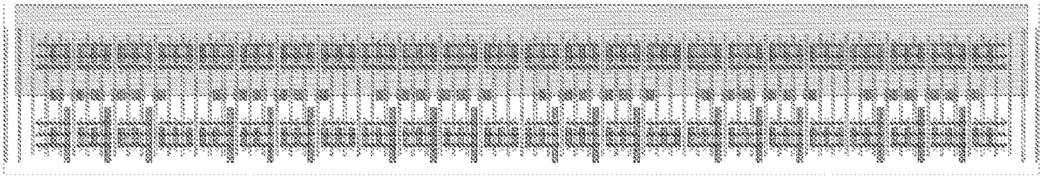
Figure 582C:
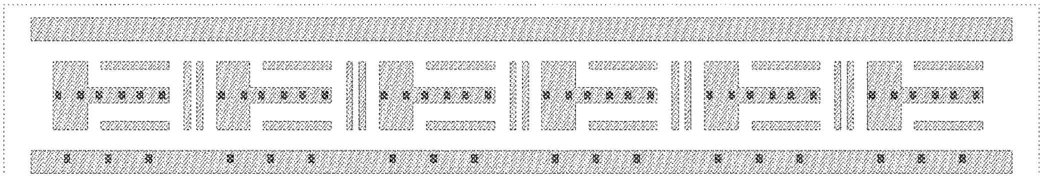
Figure 583A:
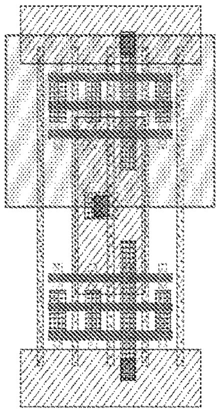
Figure 583B:
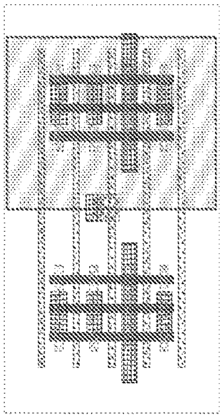
Figure 583C:
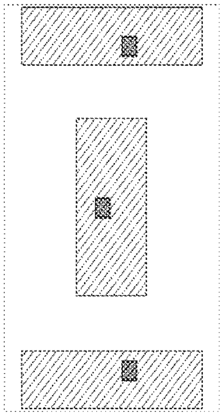
Figure 584A:
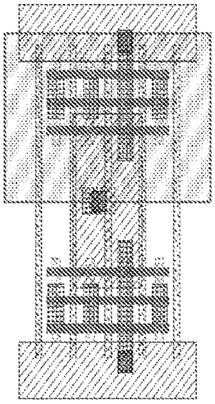
Figure 584B:
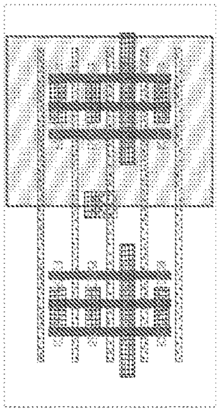
Figure 584C:
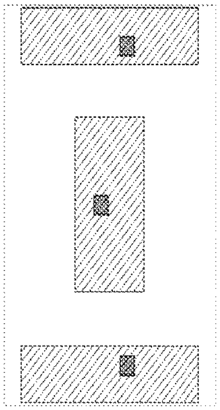
Figure 585A:
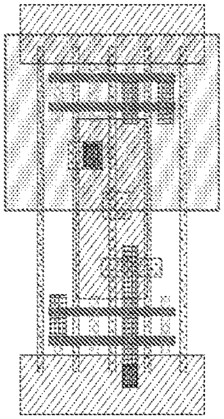
Figure 585B:
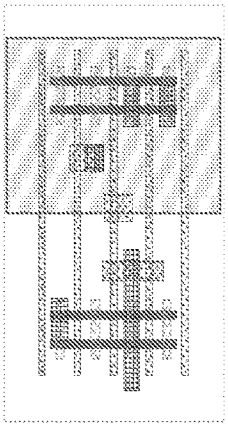
Figure 585C:
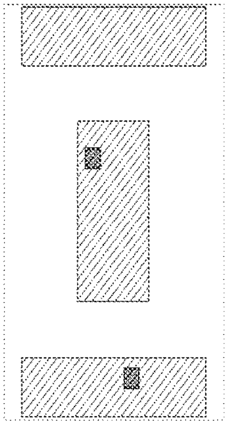
Figure 586A:
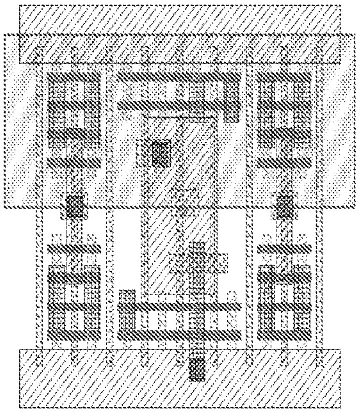
Figure 586B:
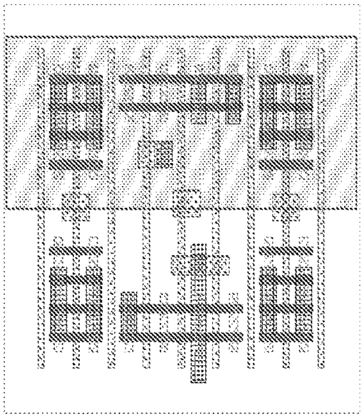
Figure 586C:
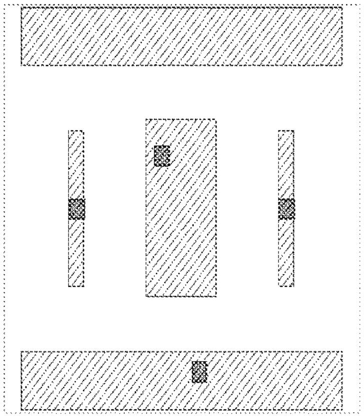
Figure 587A:
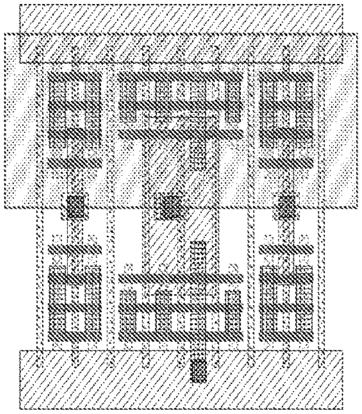
Figure 587B:
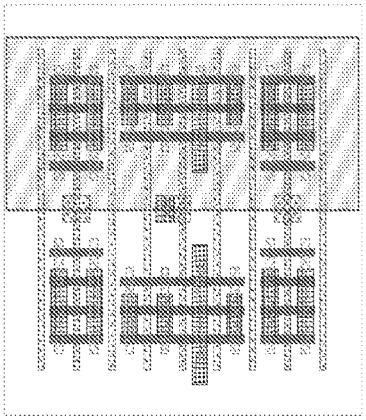
Figure 587C:
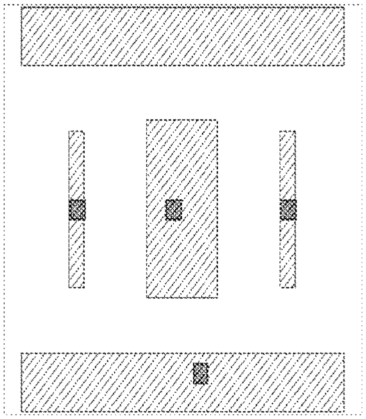
Figure 588A:
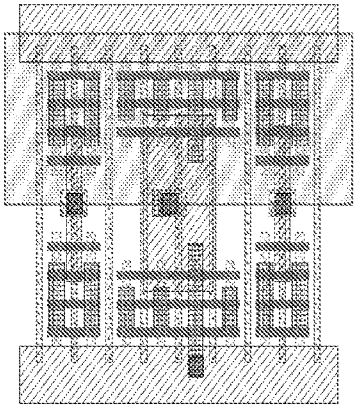
Figure 588B:
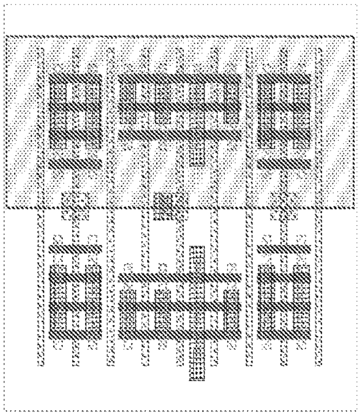
Figure 588C:
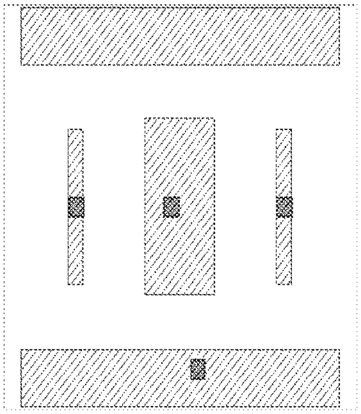
Figure 589A:
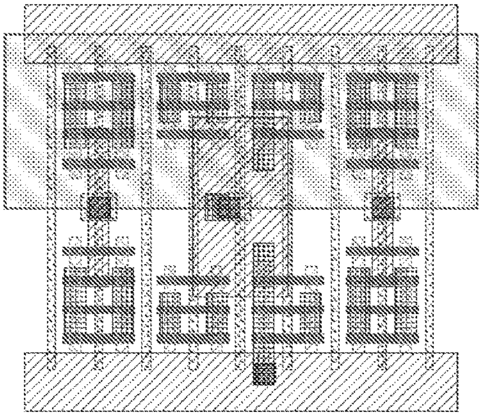
Figure 589B:
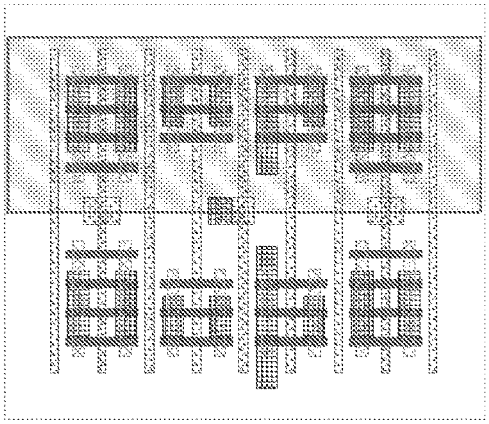
Figure 589C:
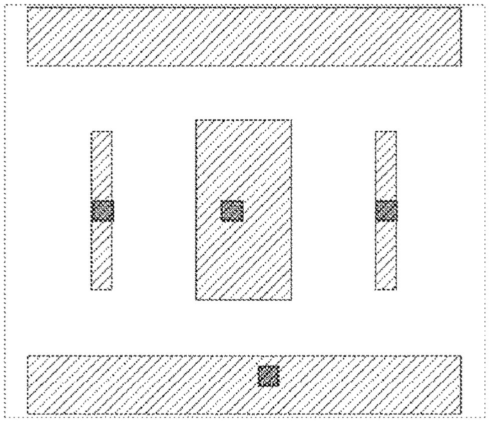
Figure 590A:
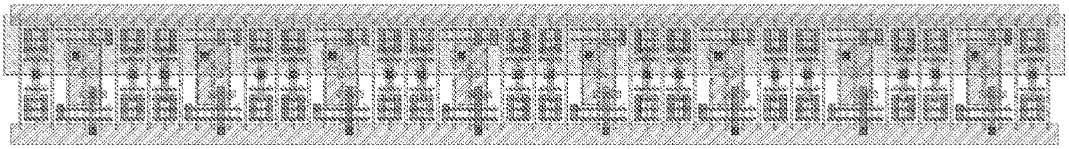
Figure 590B:
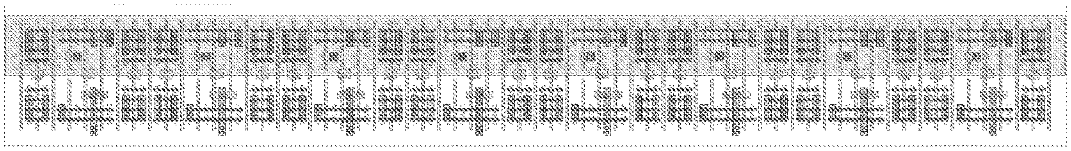
Figure 590C:
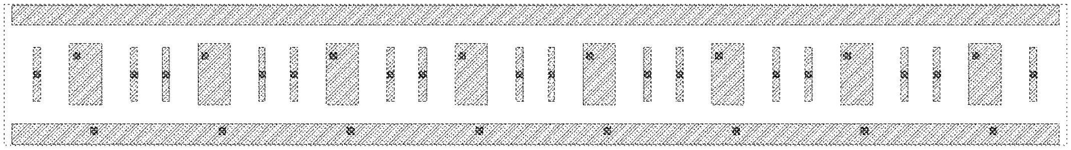
Figure 591A:
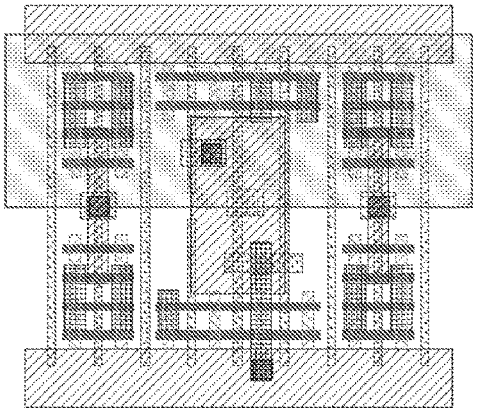
Figure 591B:
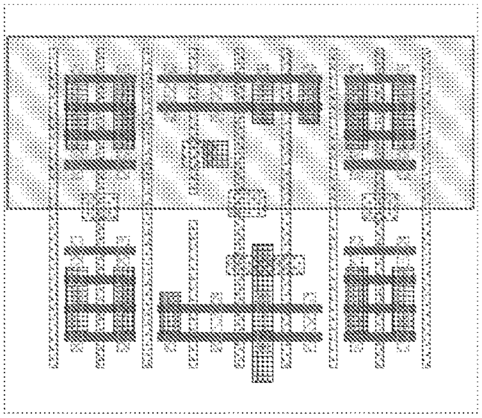
Figure 591C:
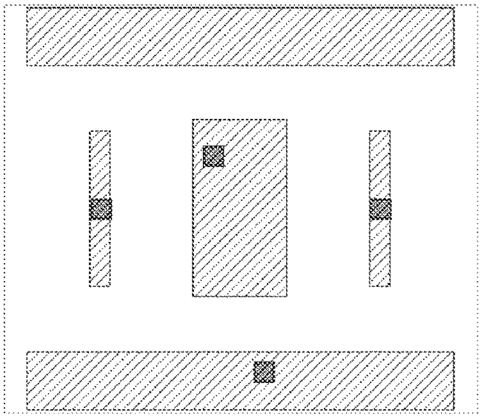
Figure 592A:
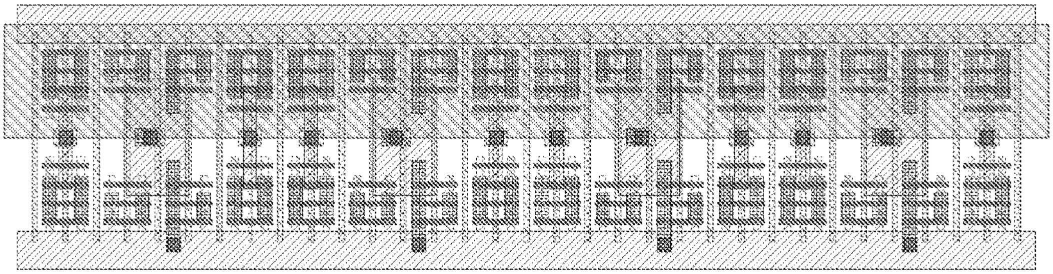
Figure 592B:
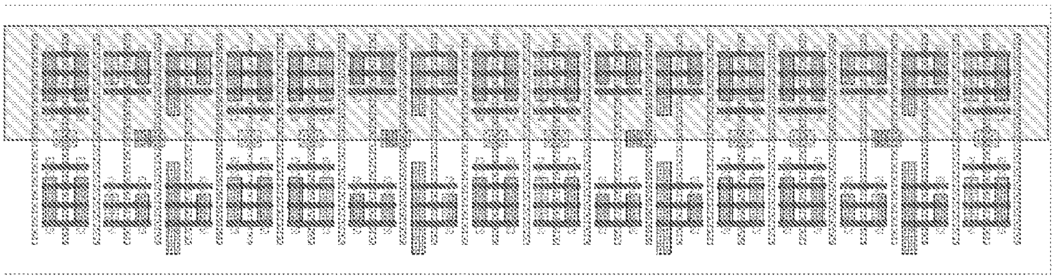
Figure 592C:
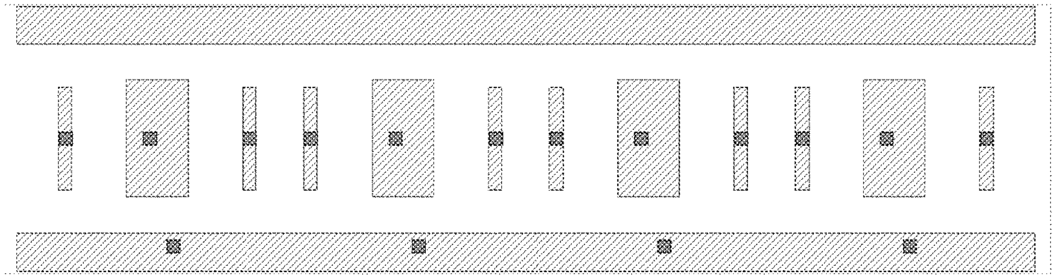
Figure 593A:
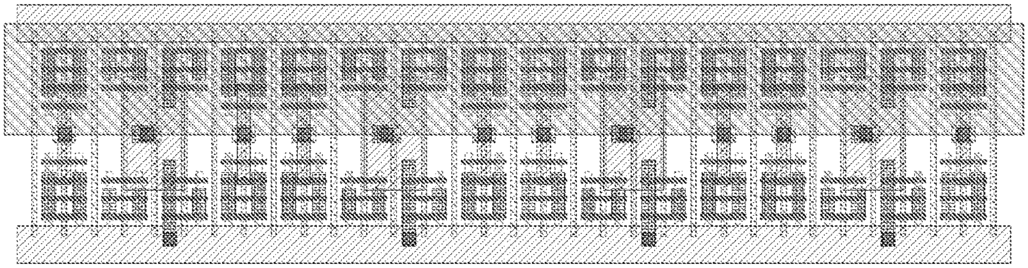
Figure 593B:
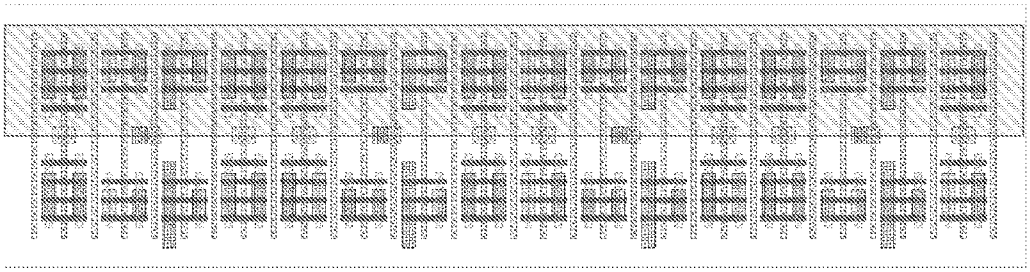
Figure 593C:
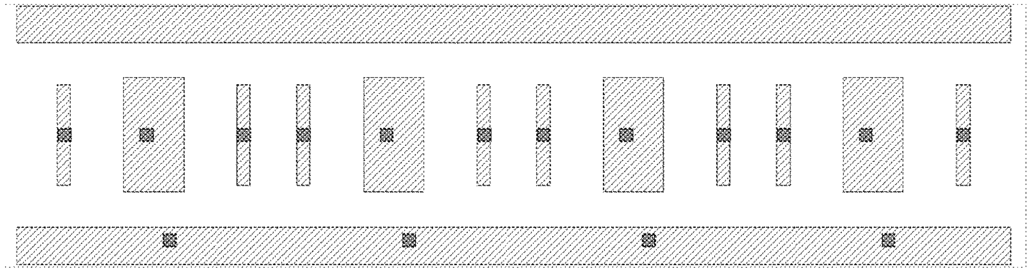
Figure 594A:
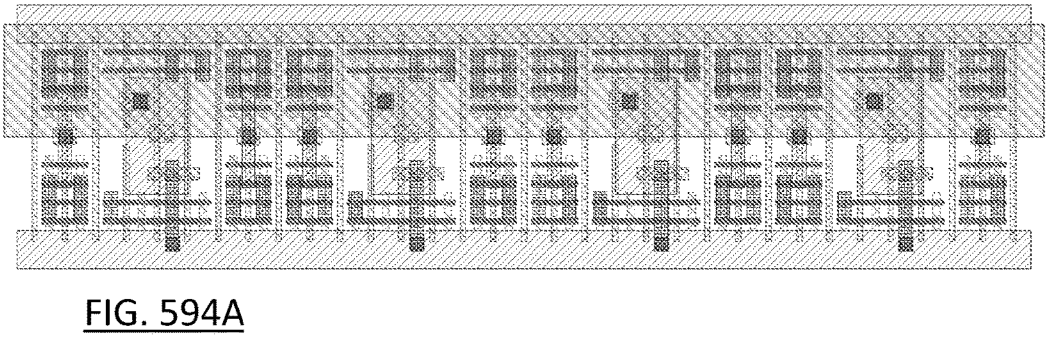
Figure 594B:
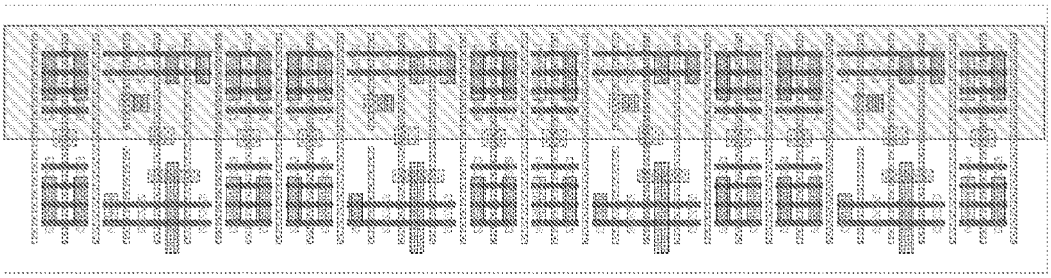
Figure 594C:
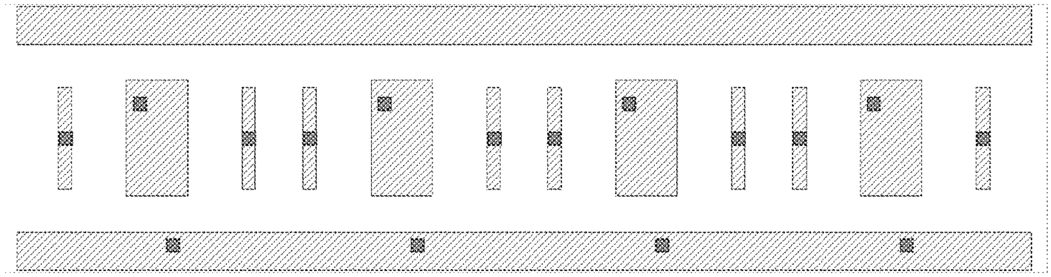
Figure 595A:
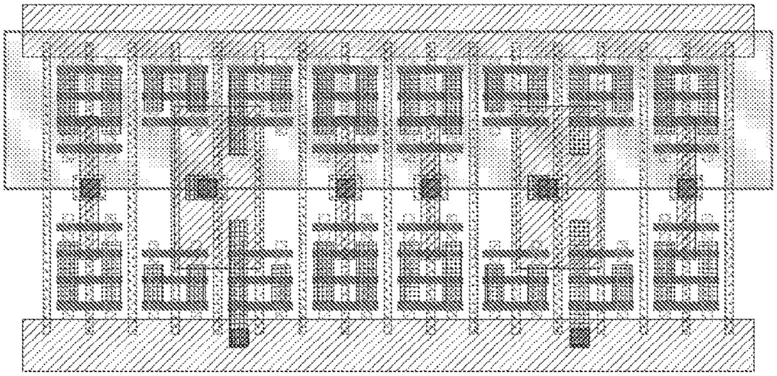
Figure 595B:
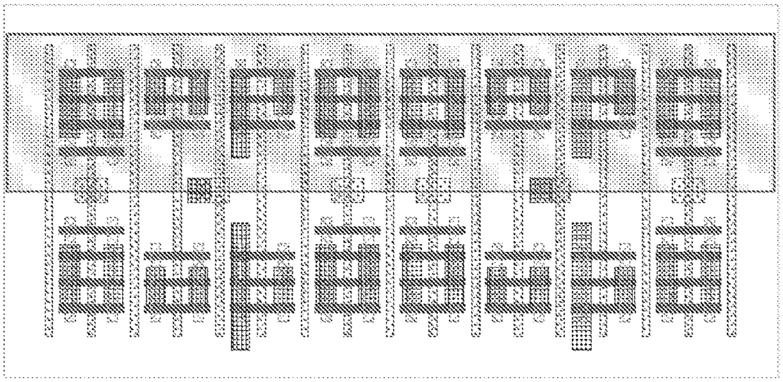
Figure 595C:
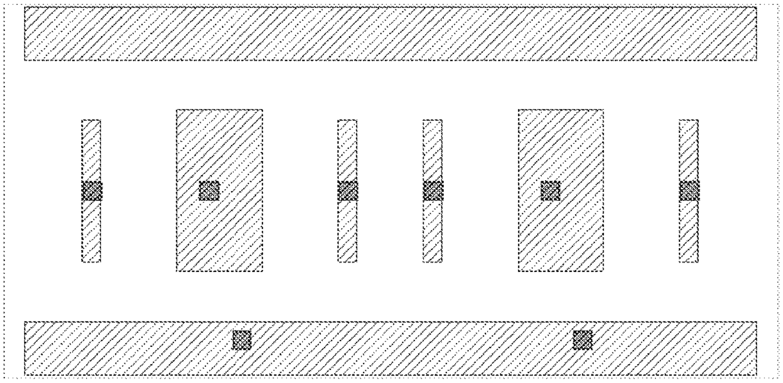
Figure 596A:
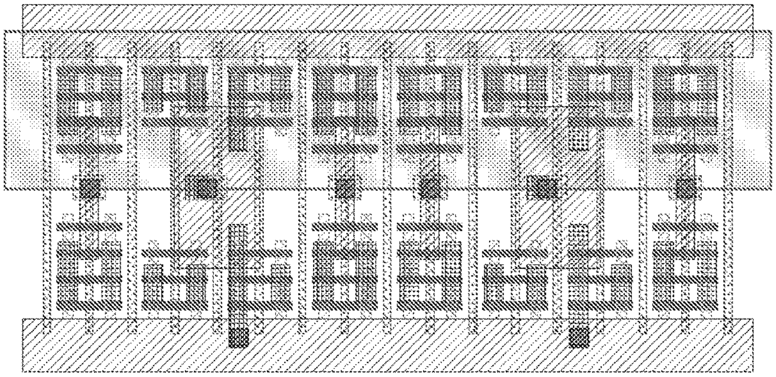
Figure 596B:
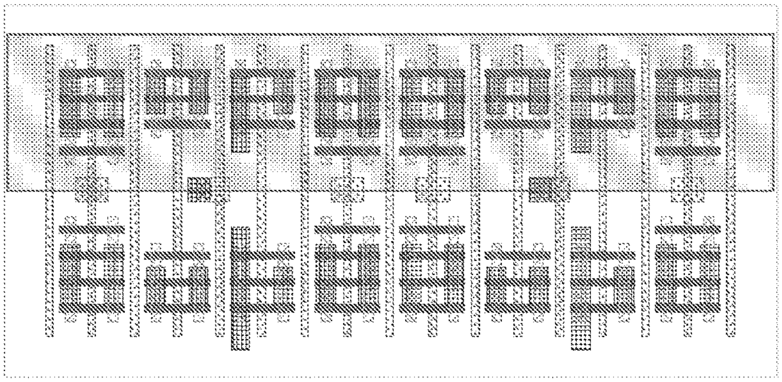
Figure 596C:
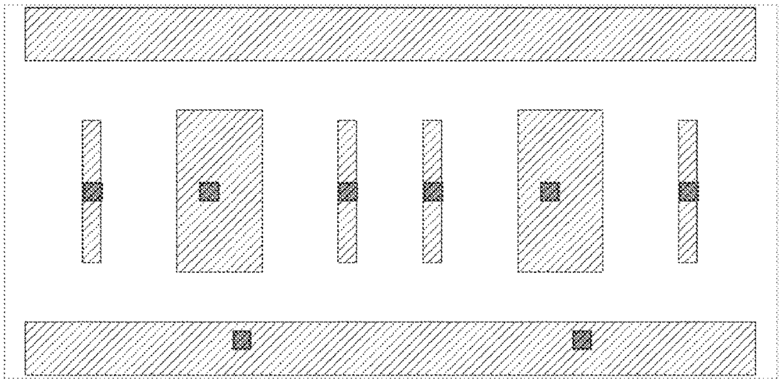
Figure 597A:
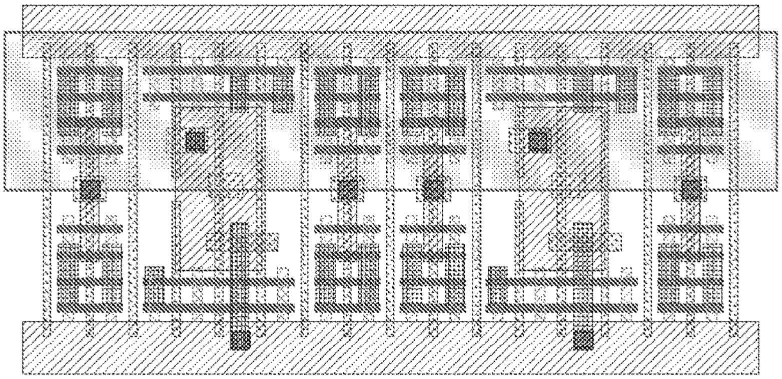
Figure 597B:
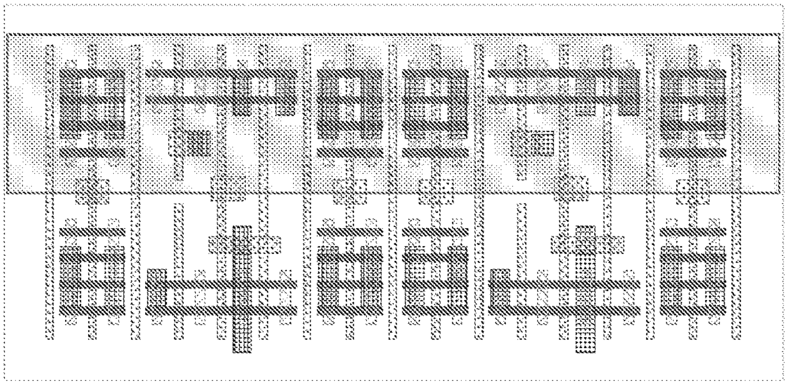
Figure 597C:
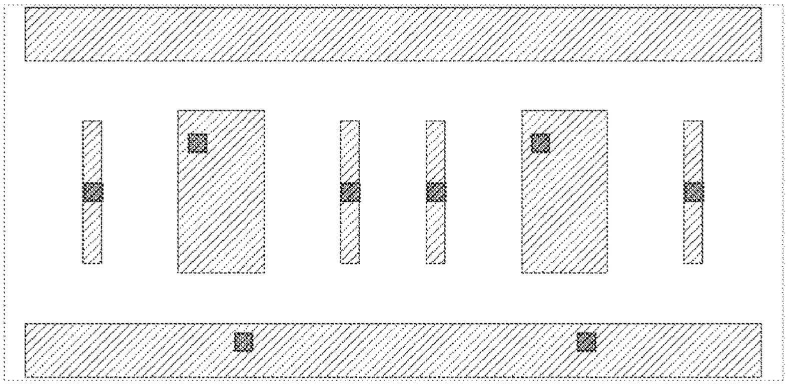
Figure 598A:
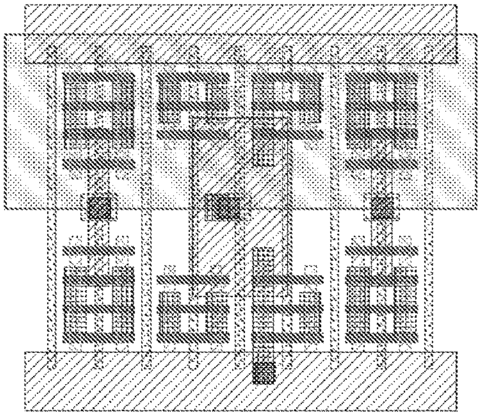
Figure 598B:
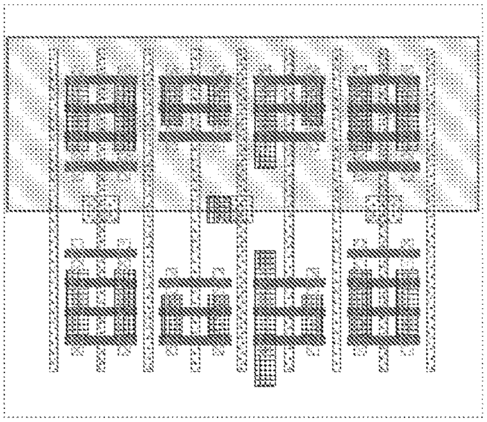
Figure 598C:
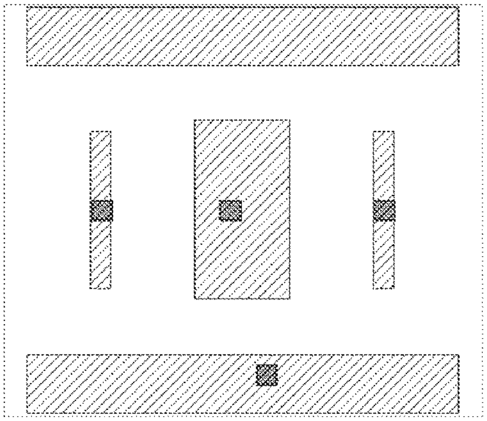
Figure 599A:
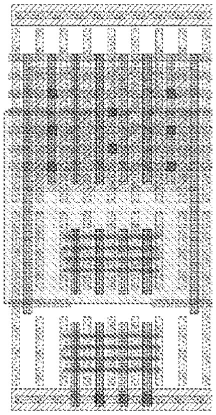
Figure 599B:
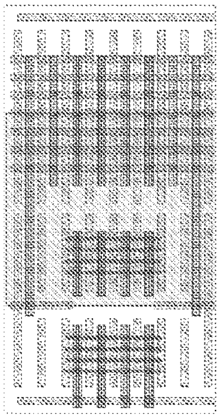
Figure 599C:
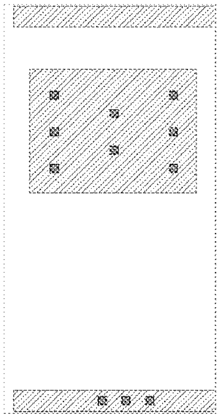
Figure 600A:
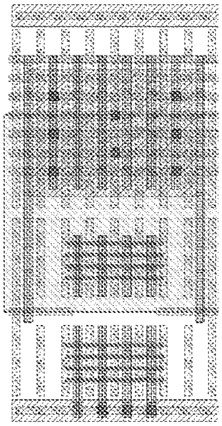
Figure 600B:
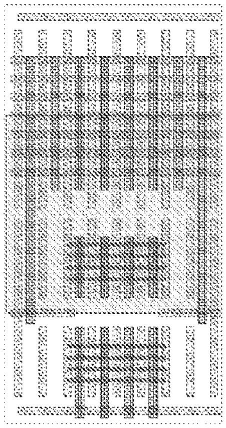
Figure 600C:
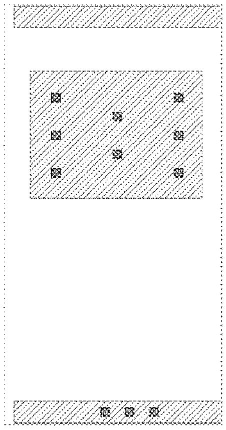
Figure 601A:
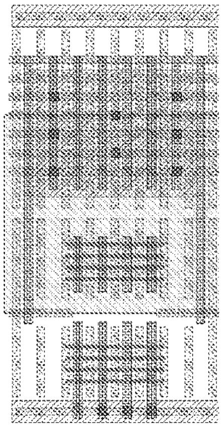
Figure 601B:
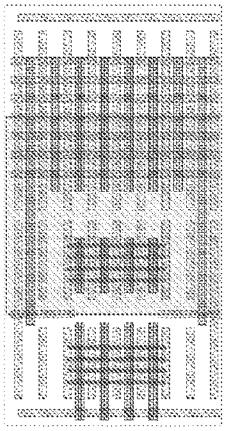
Figure 601C:
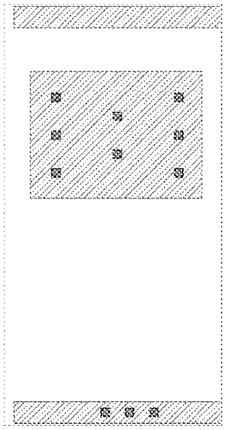
Figure 602A:
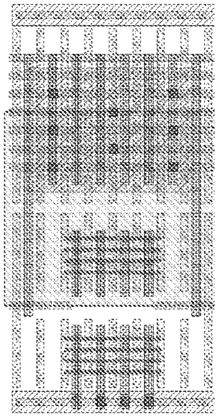
Figure 602B:
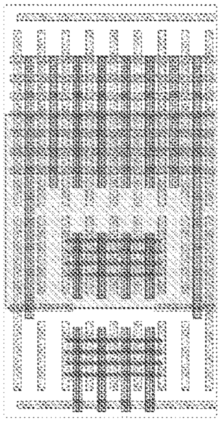
Figure 602C:
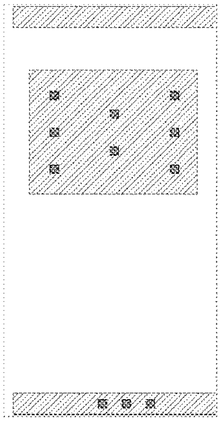
Figure 603A:
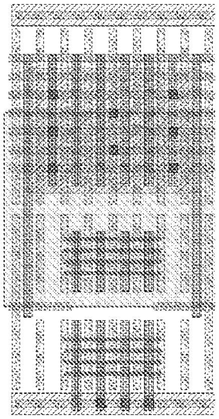
Figure 603B:
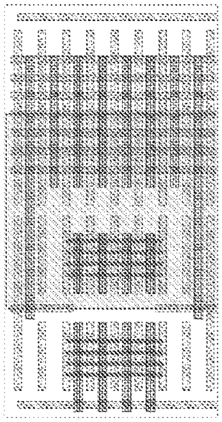
Figure 603C:
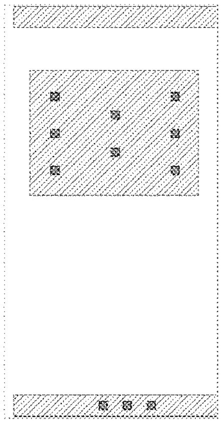
Figure 604A:
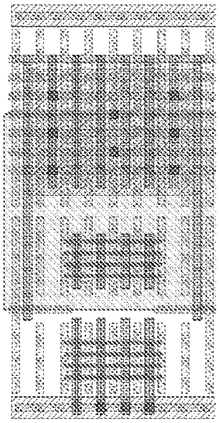
Figure 604B:
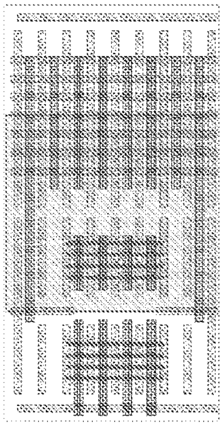
Figure 604C:
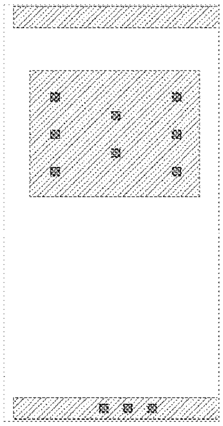
Figure 605A:
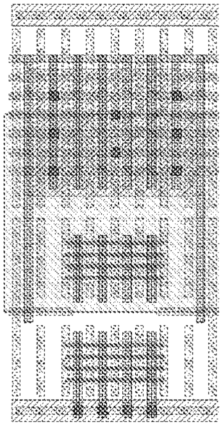
Figure 605B:
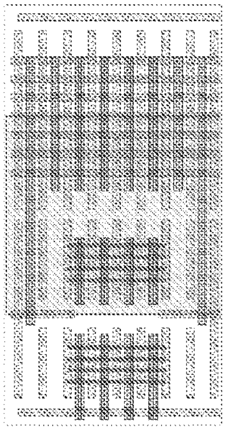
Figure 605C:
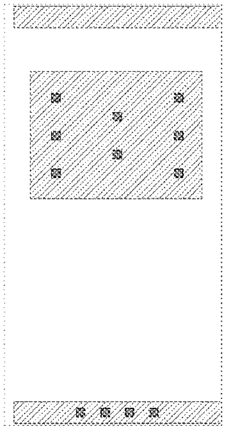
Figure 606A:
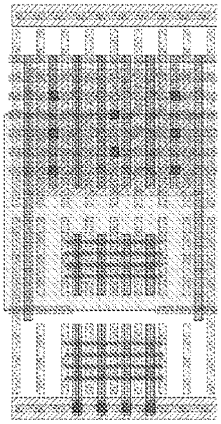
Figure 606B:
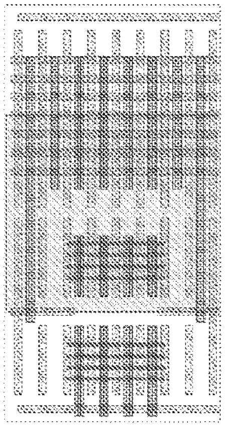
Figure 606C:
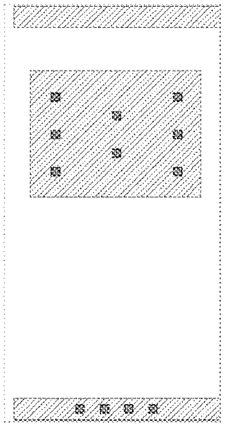
Figure 607A:
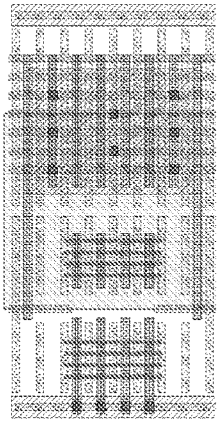
Figure 607B:
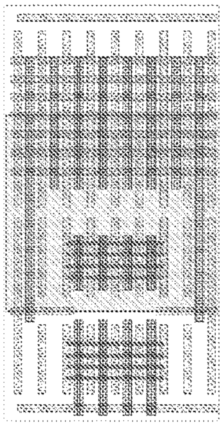
Figure 607C:
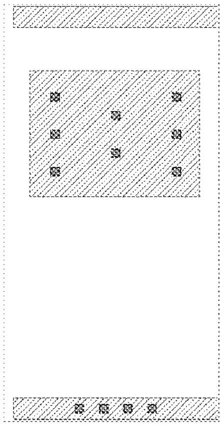
Figure 608A:
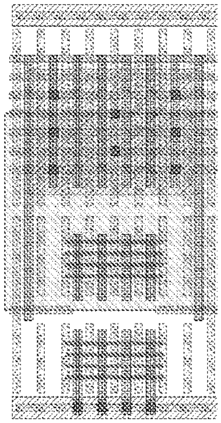
Figure 608B:
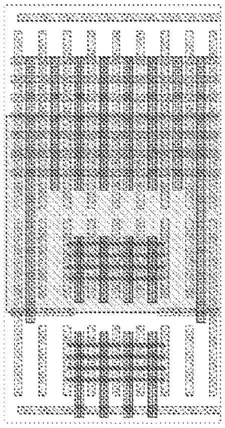
Figure 608C:
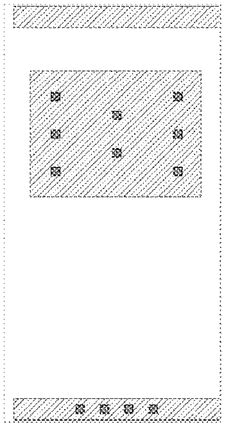
Figure 609A:
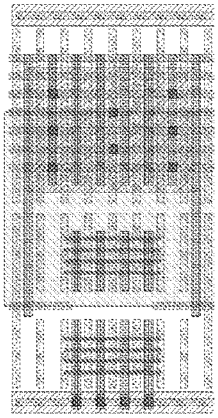
Figure 609B:
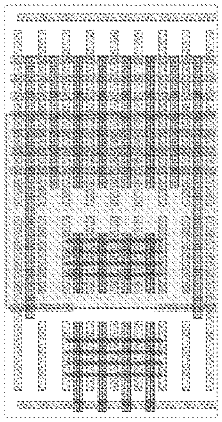
Figure 609C:
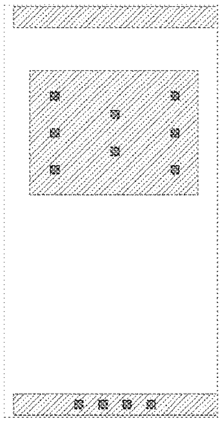
Figure 610A:
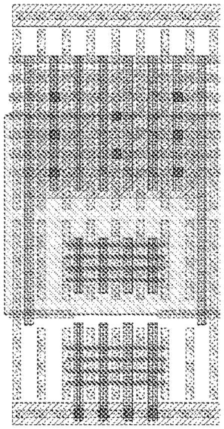
Figure 610B:
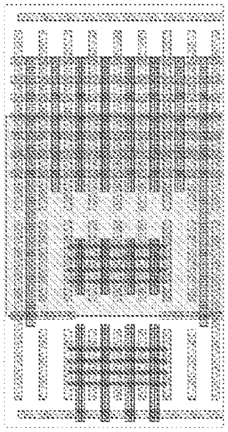
Figure 610C:
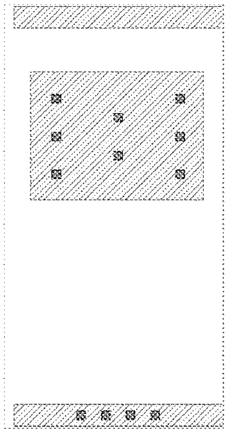
Figure 611A:
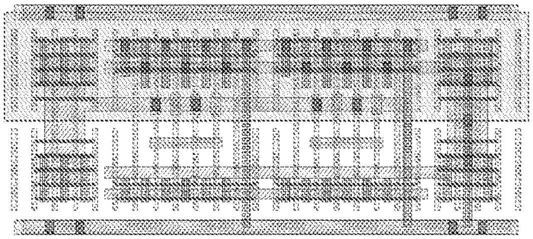
Figure 611B:
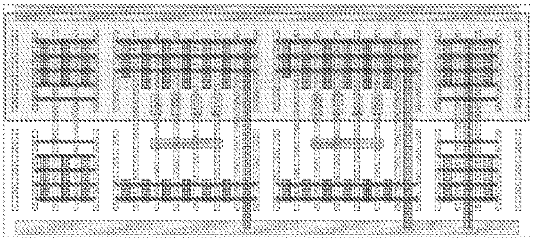
Figure 611C:
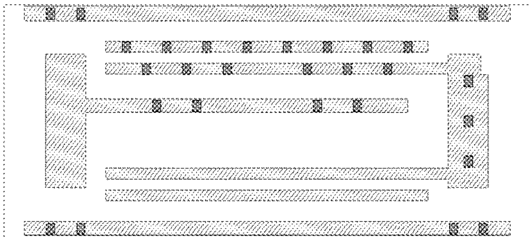
Figure 612A:
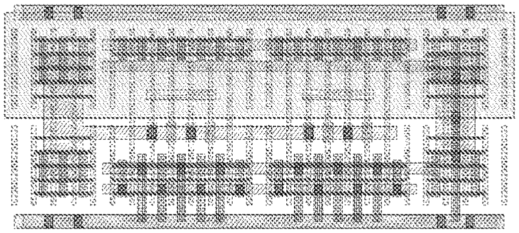
Figure 612B:
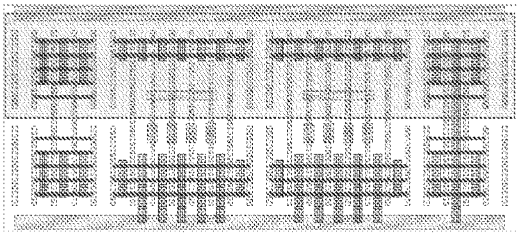
Figure 612C:
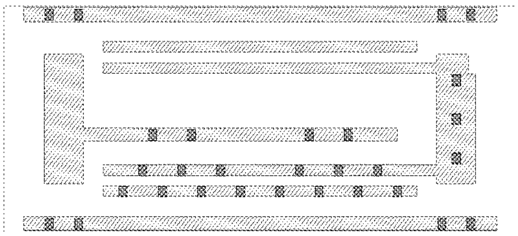
Figure 613A:
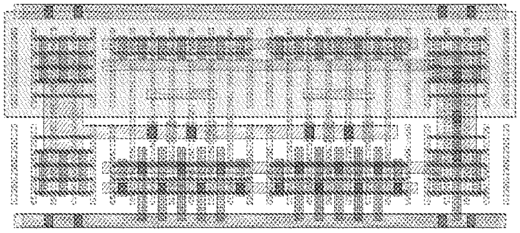
Figure 613B:
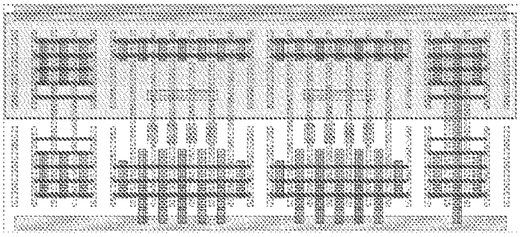
Figure 613C:
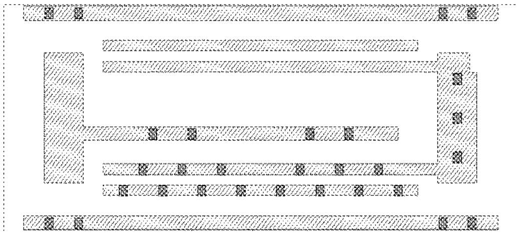
Figure 614A:
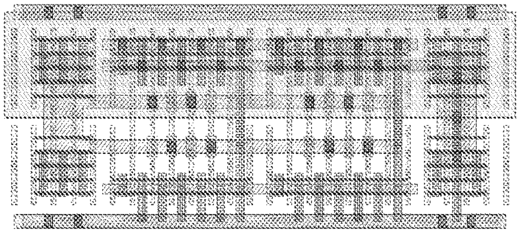
Figure 614B:
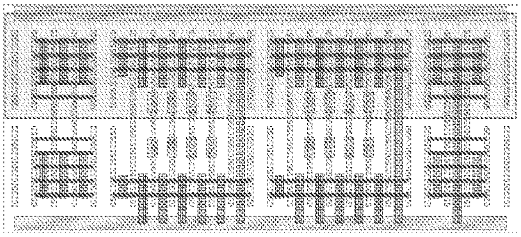
Figure 614C:
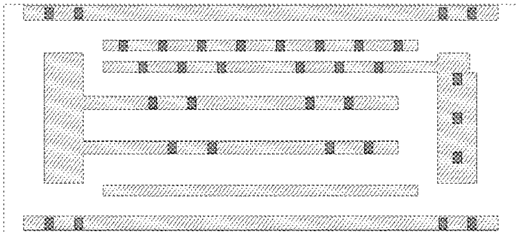
Figure 615A:
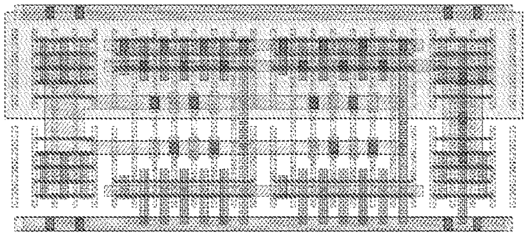
Figure 615B:
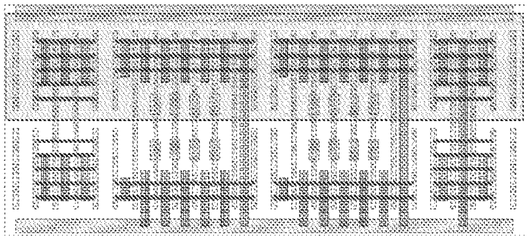
Figure 615C:
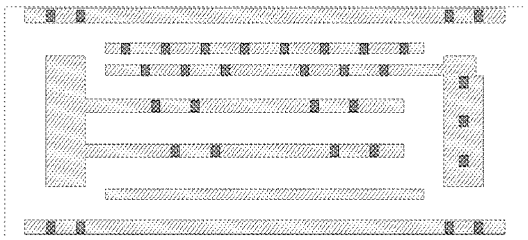
Figure 616A:
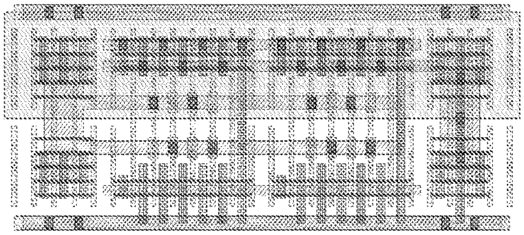
Figure 616B:
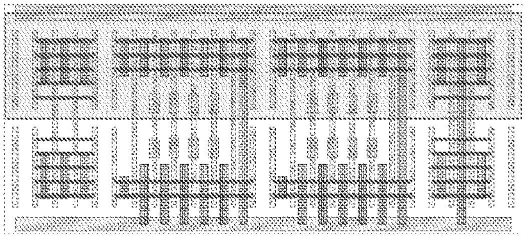
Figure 616C:
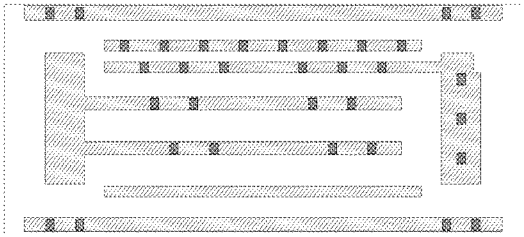
Figure 617A:
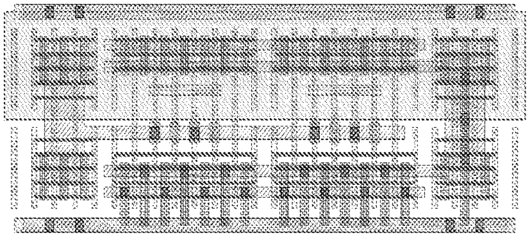
Figure 617B:
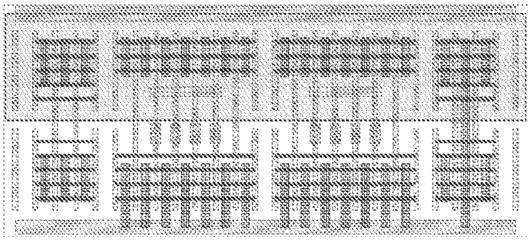
Figure 617C:
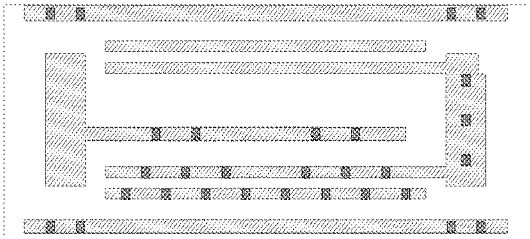
Figure 618A:
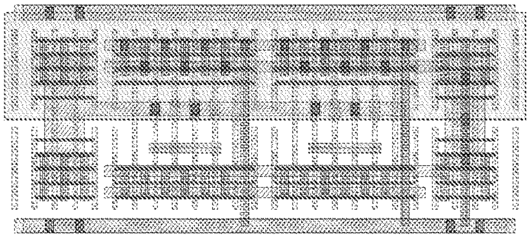
Figure 618B:
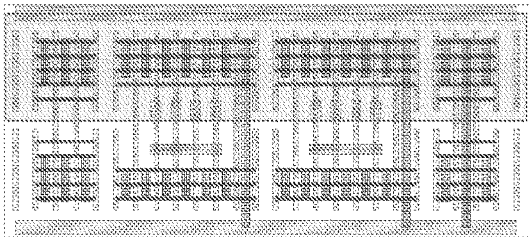
Figure 618C:
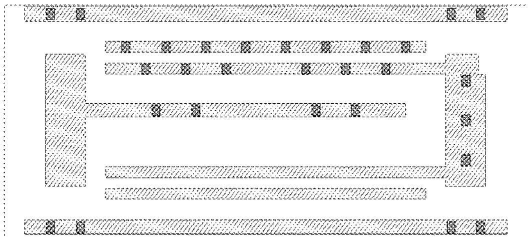
Figure 619A:
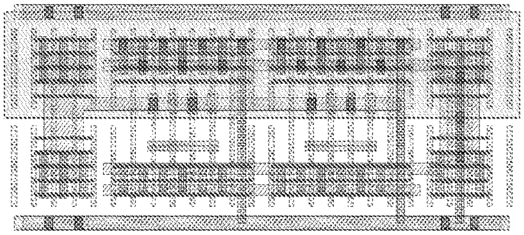
Figure 619B:
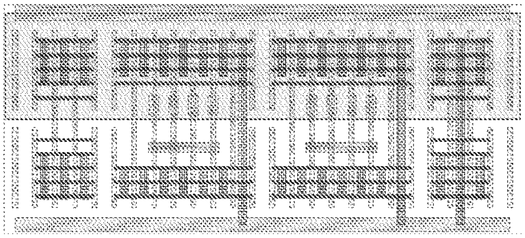
Figure 619C:
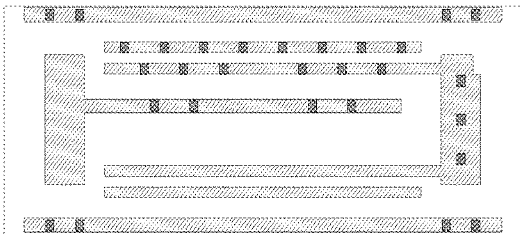
Figure 620A:
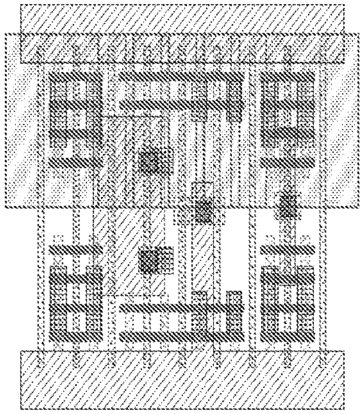
Figure 620B:
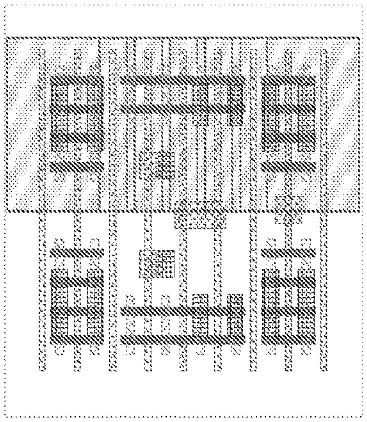
Figure 620C:
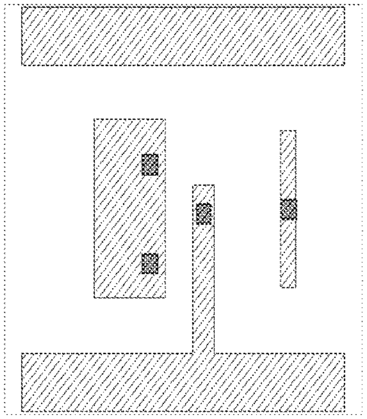
Figure 621A:
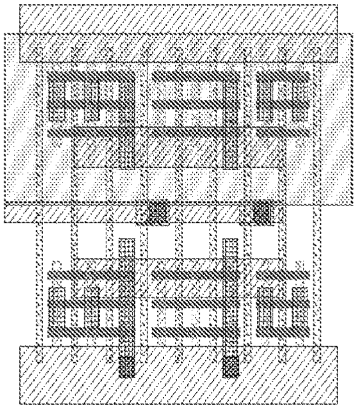
Figure 621B:
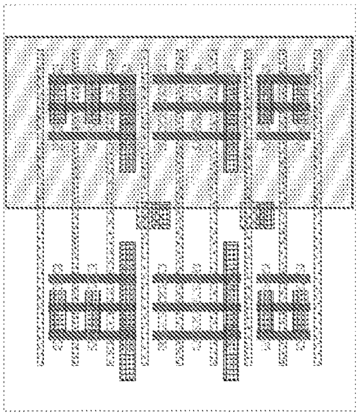
Figure 621C:
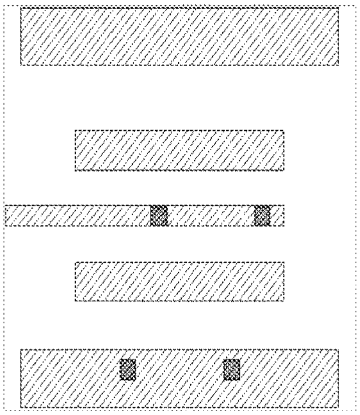
Figure 622A:
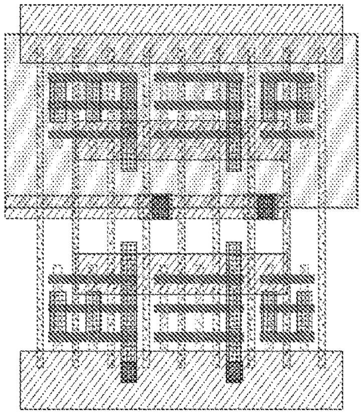
Figure 622B:
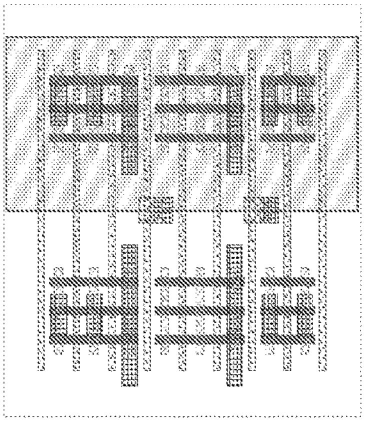
Figure 622C:
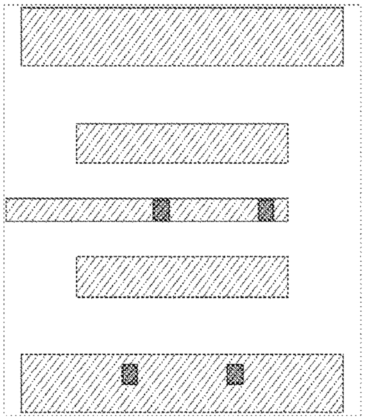
Figure 623A:
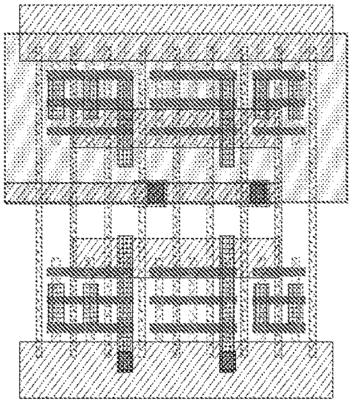
Figure 623B:
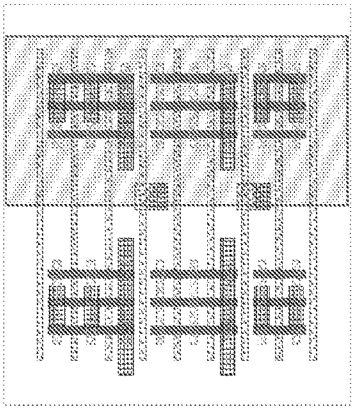
Figure 623C:
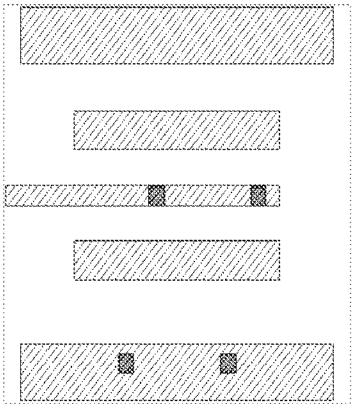
Figure 624A:
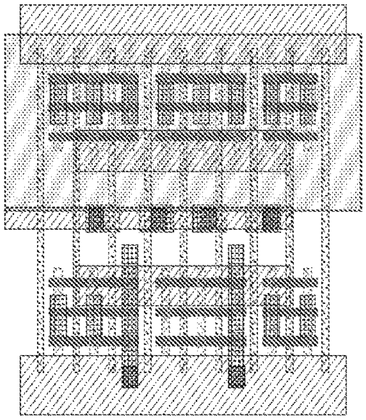
Figure 624B:
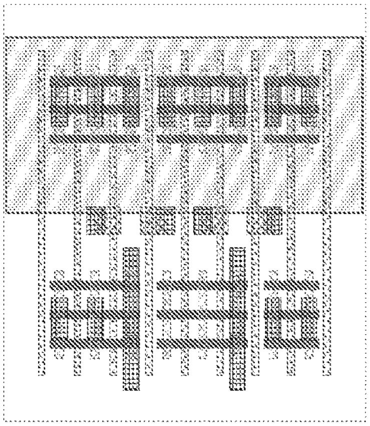
Figure 624C:
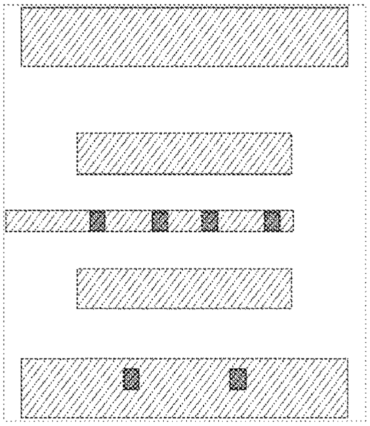
Figure 625A:
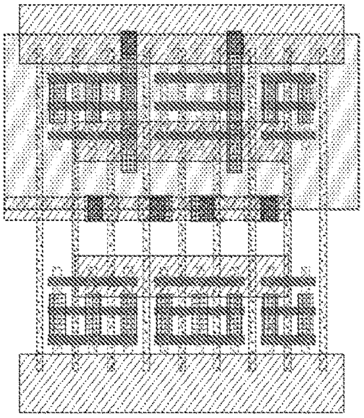
Figure 625B:
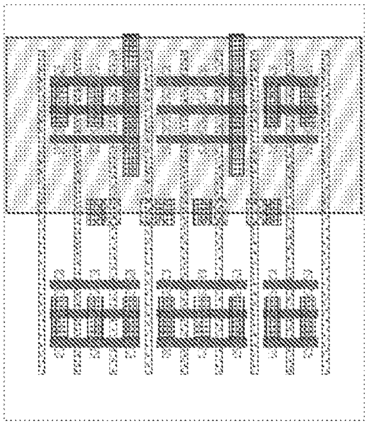
Figure 625C:
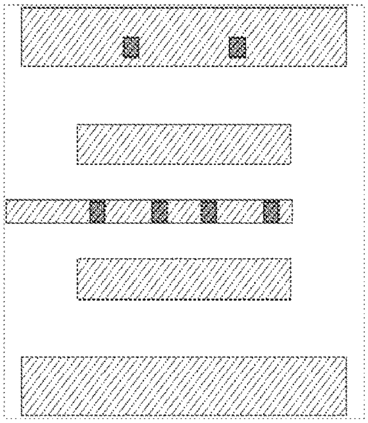
Figure 626A:
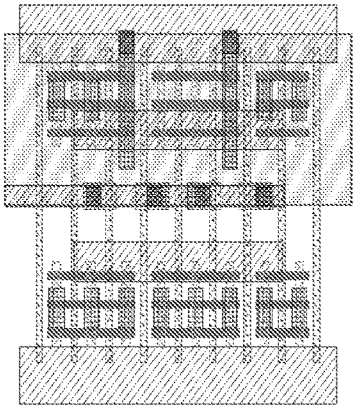
Figure 626B:
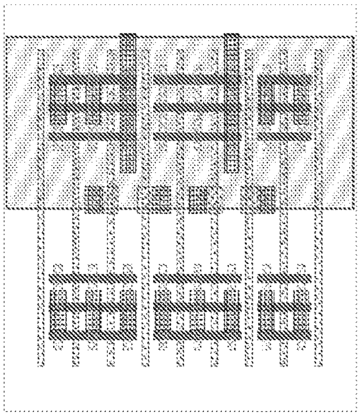
Figure 626C:
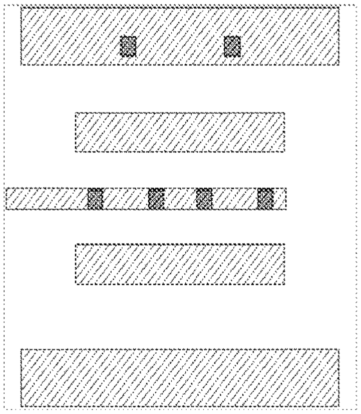
Figure 627A:
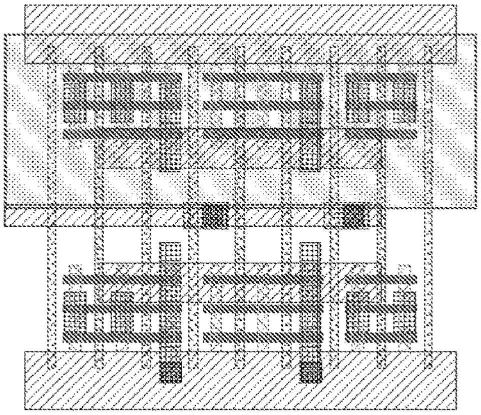
Figure 627B:
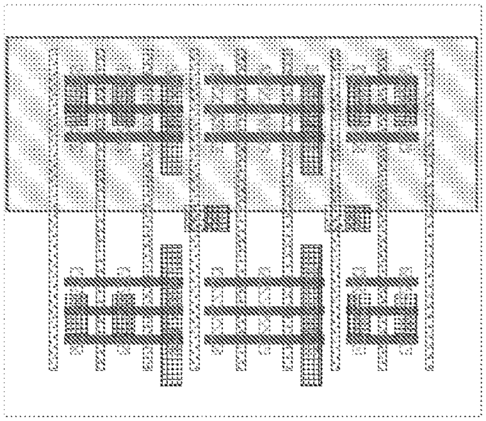
Figure 627C:
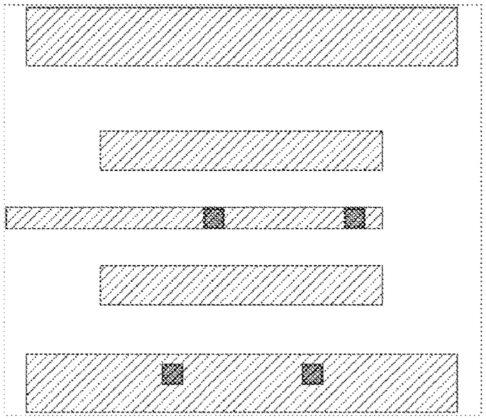
Figure 628A:
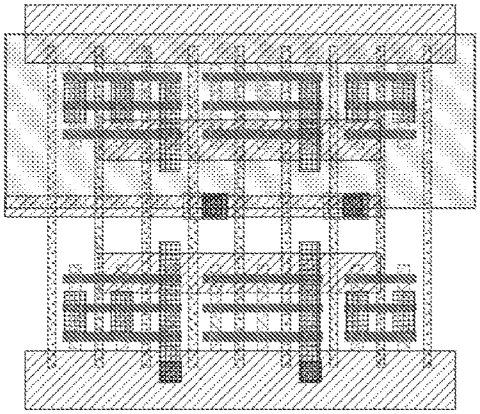
Figure 628B:
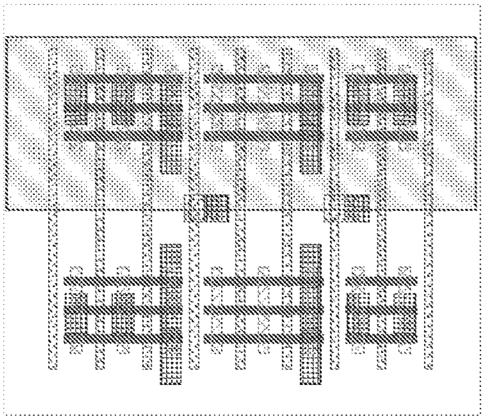
Figure 628C:
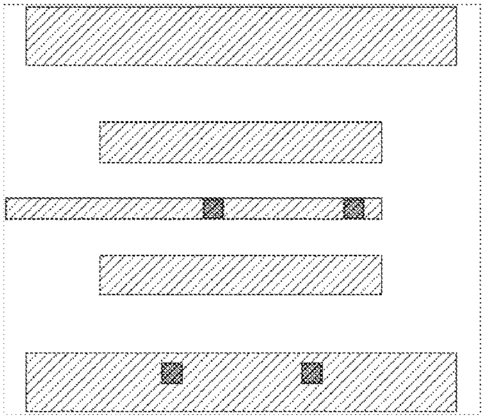
Figure 629A:
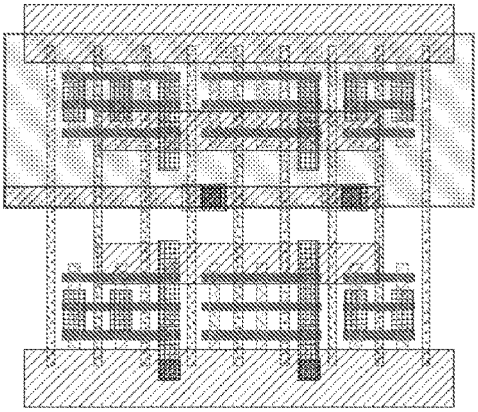
Figure 629B:
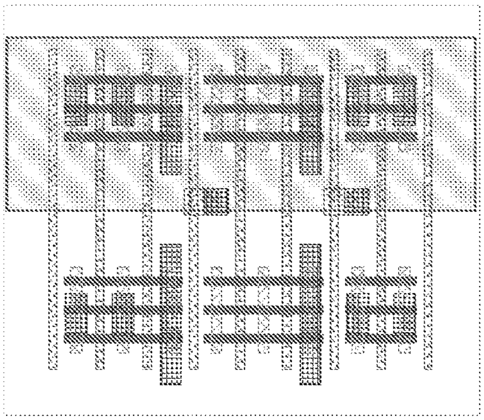
Figure 629C:
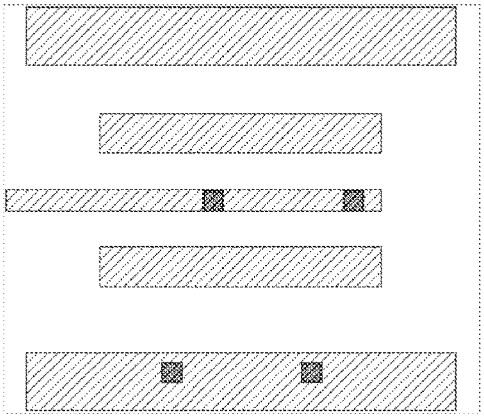
Figure 630A:
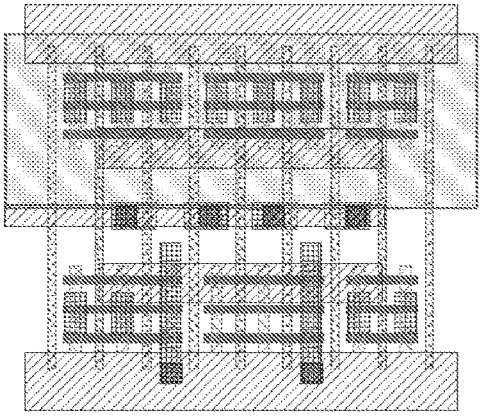
Figure 630B:
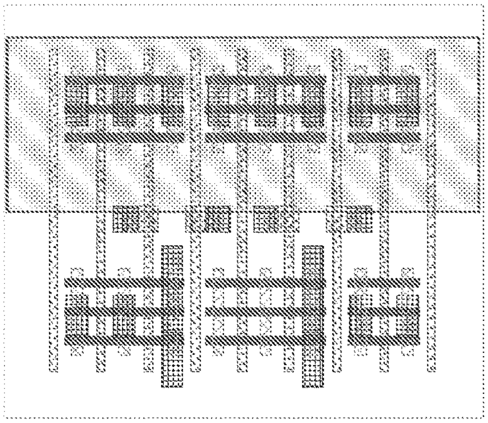
Figure 630C:
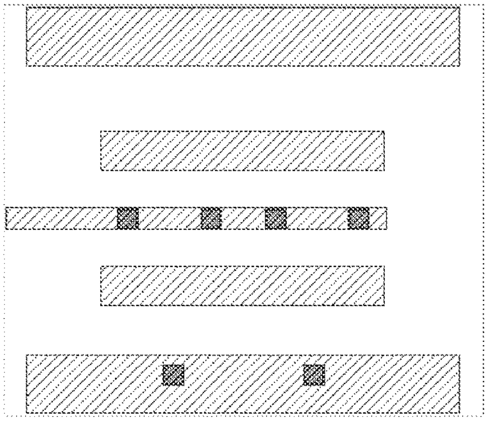
Figure 631A:
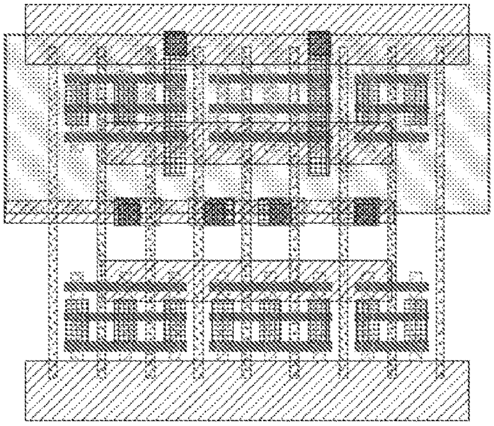
Figure 631B:
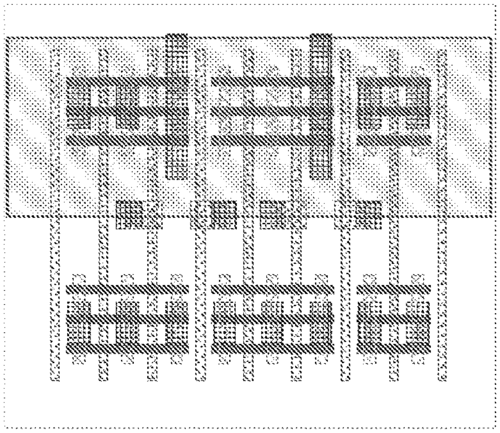
Figure 631C:
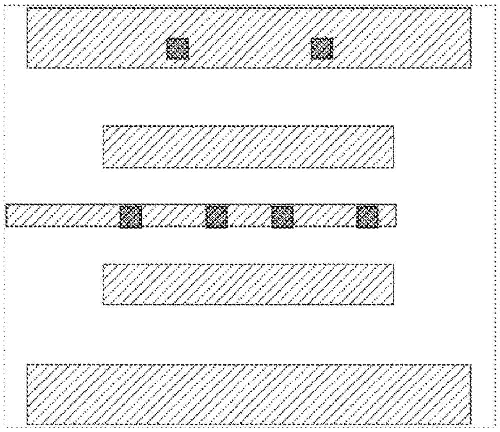
Figure 632A:
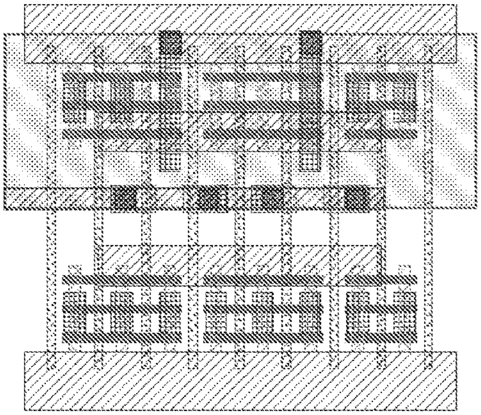
Figure 632B:
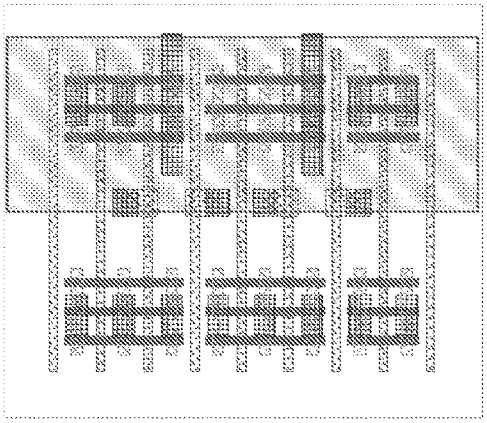
Figure 632C:
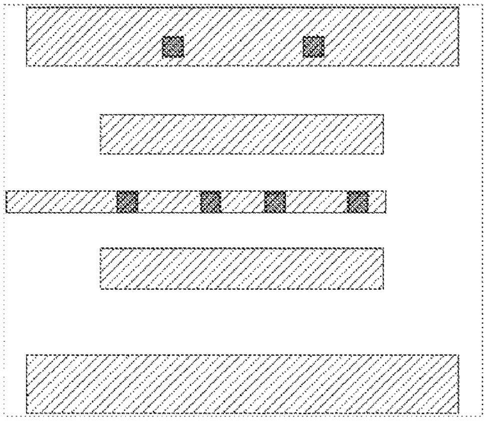
Figure 633A:
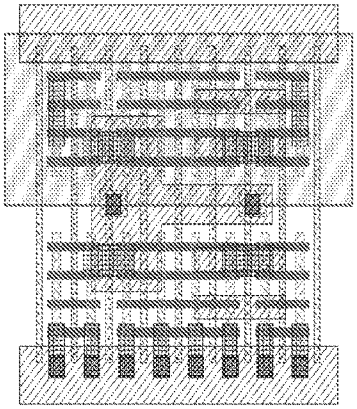
Figure 633B:
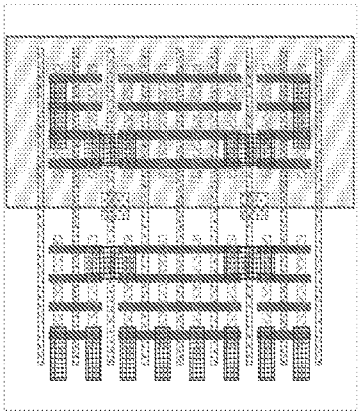
Figure 633C:
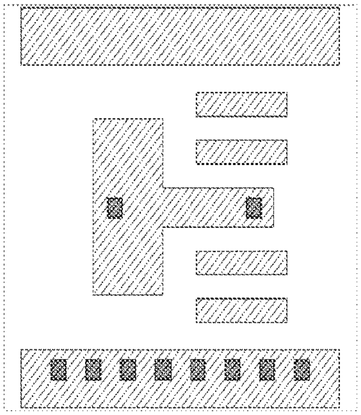
Figure 634A:
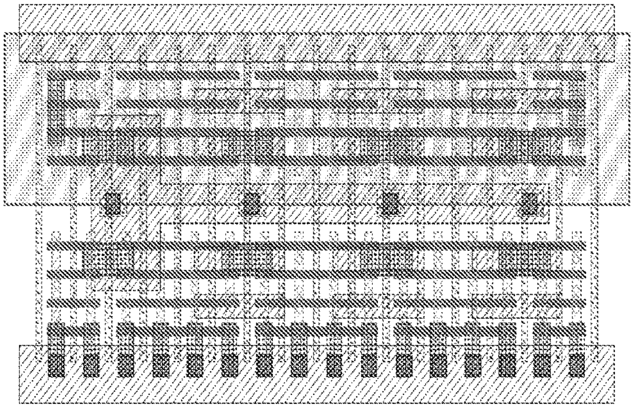
Figure 634B:
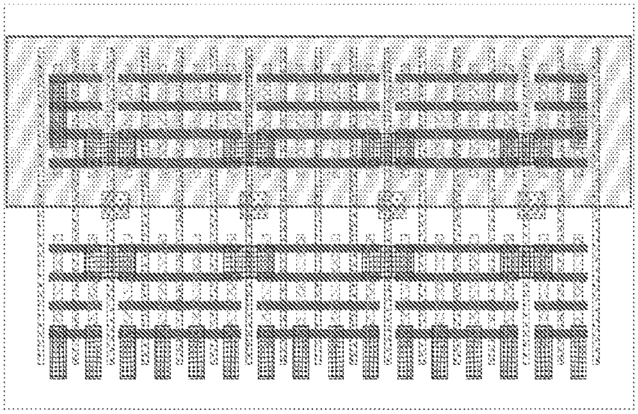
Figure 634C:
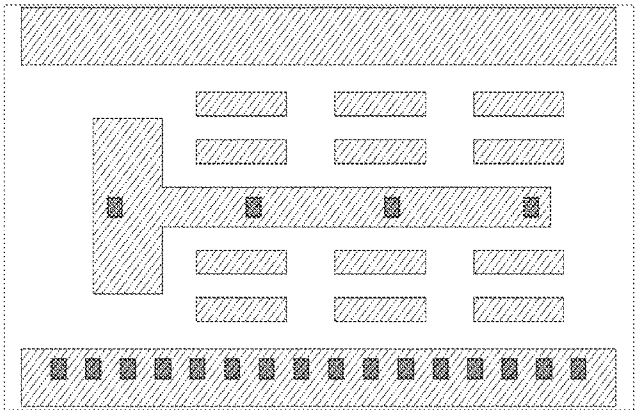
Figure 635A:
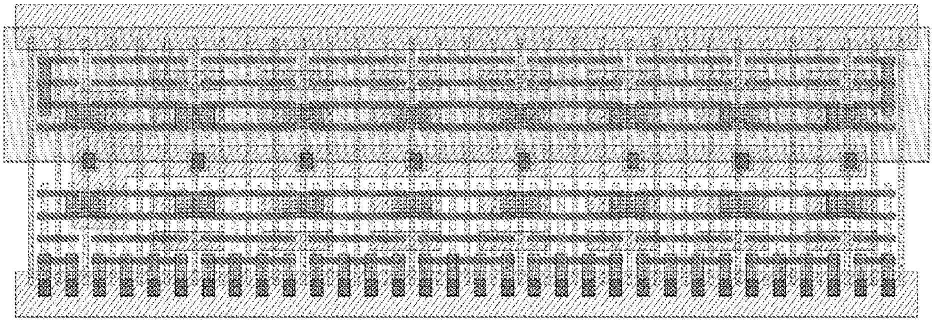
Figure 635B:
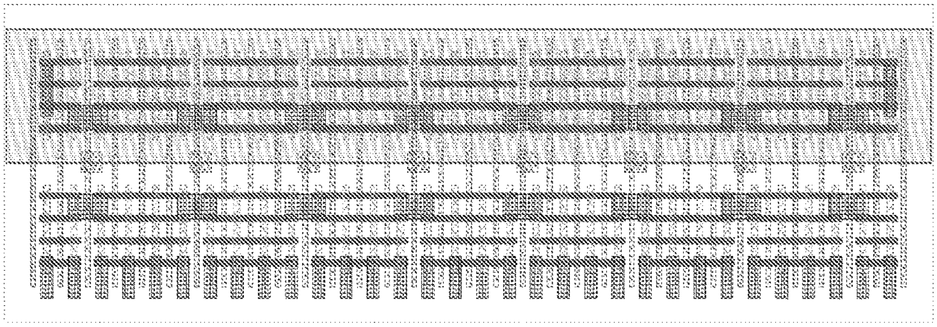
Figure 635C:
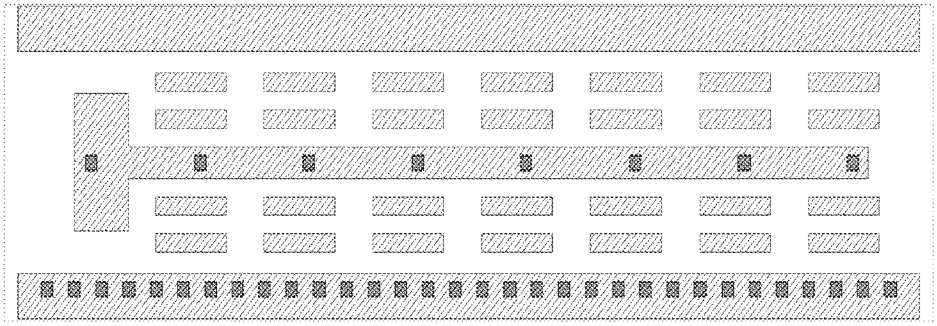
Figure 636A:
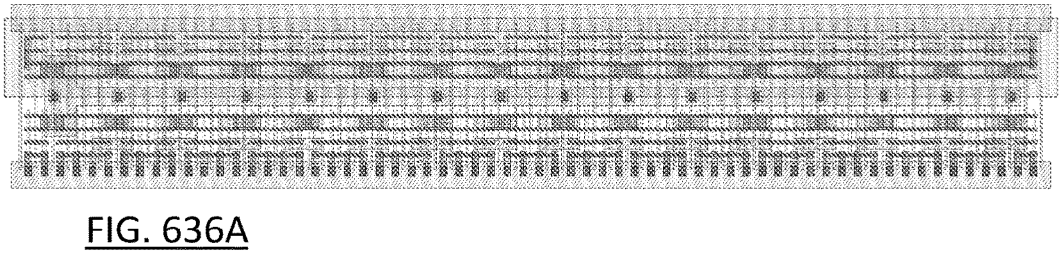
Figure 636B:
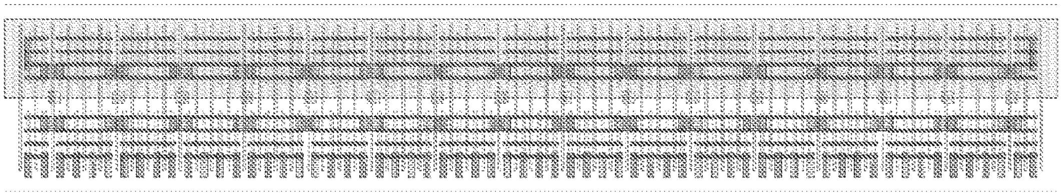
Figure 636C:
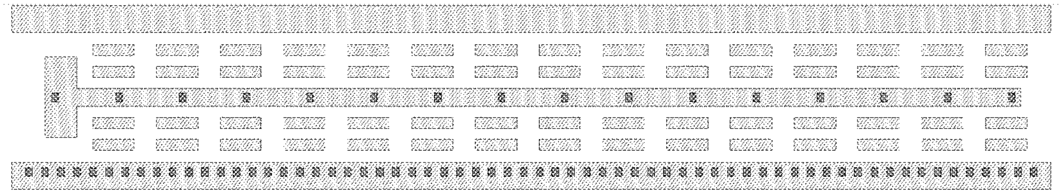
Figure 637A:
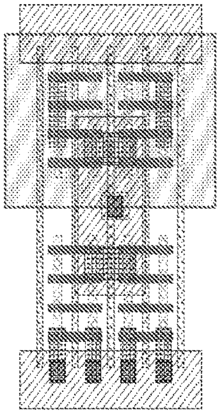
Figure 637B:
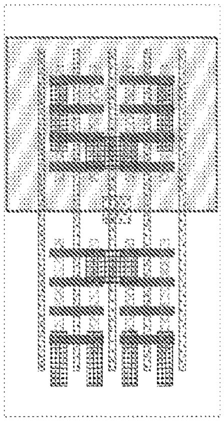
Figure 637C:
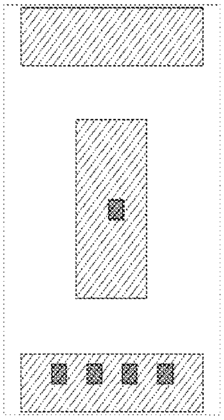
Figure 638A:
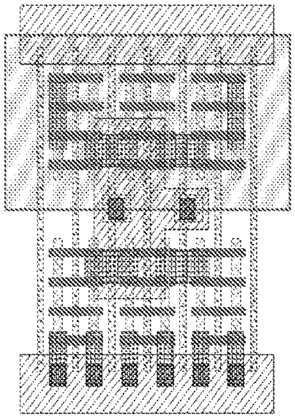
Figure 638B:
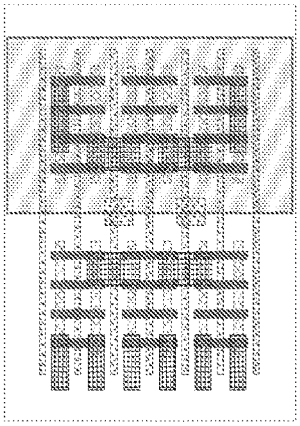
Figure 638C:
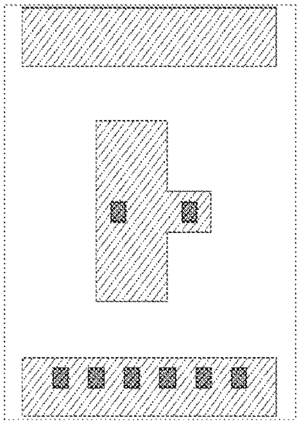
Figure 639A:
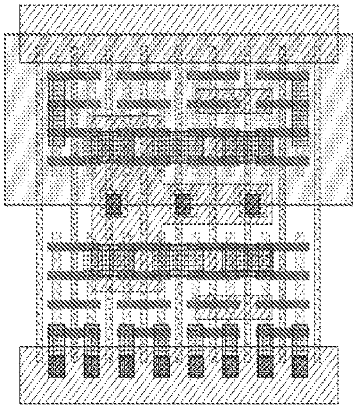
Figure 639B:
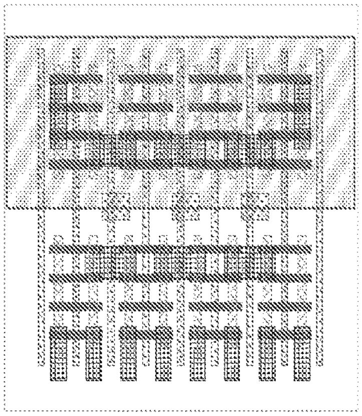
Figure 639C:
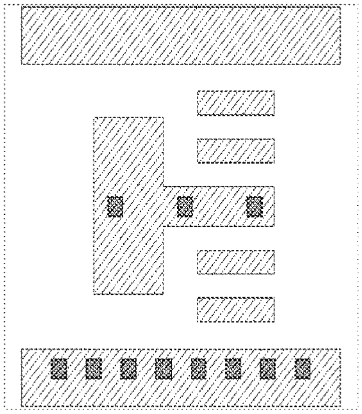
Figure 640A:
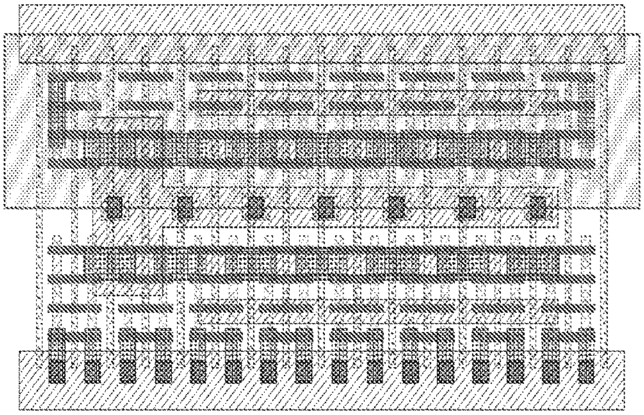
Figure 640B:
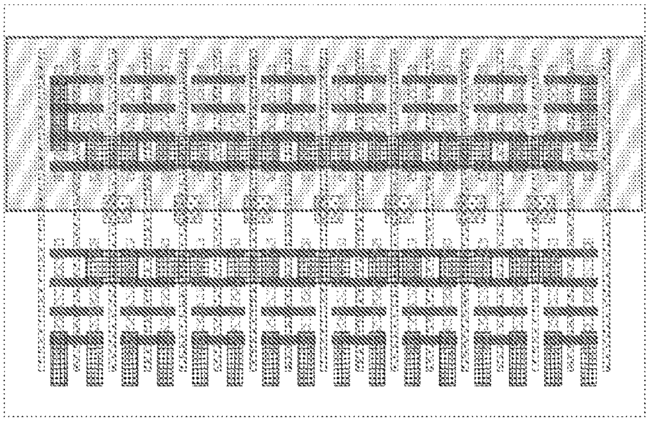
Figure 640C:
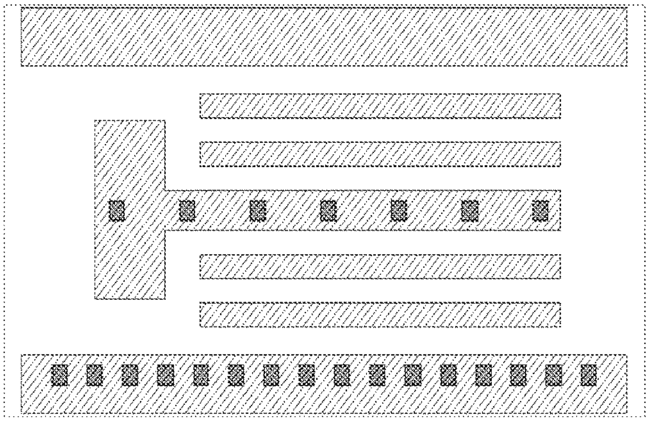
Figure 641A:
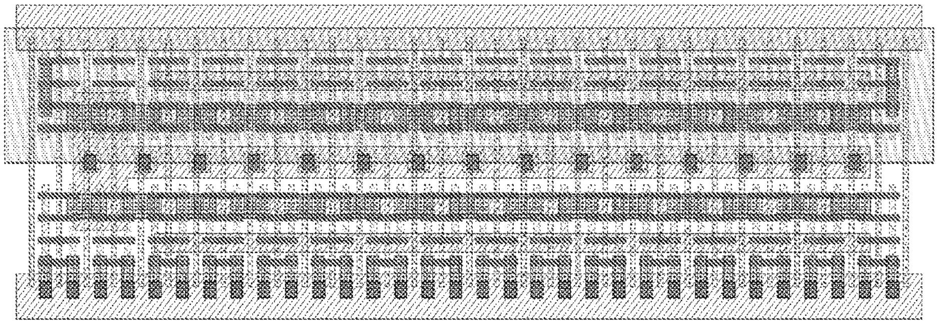
Figure 641B:
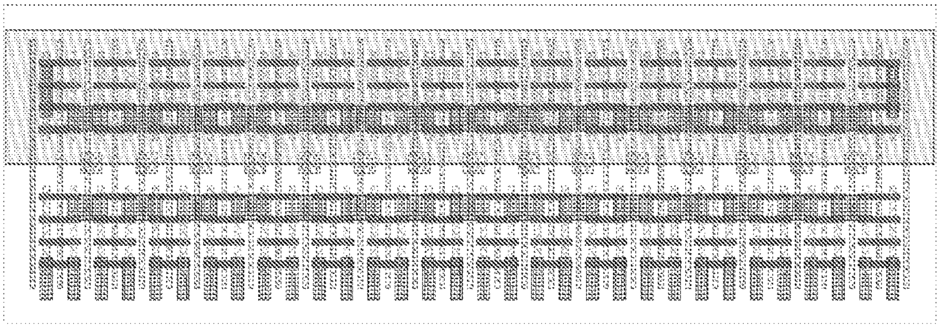
Figure 641C:
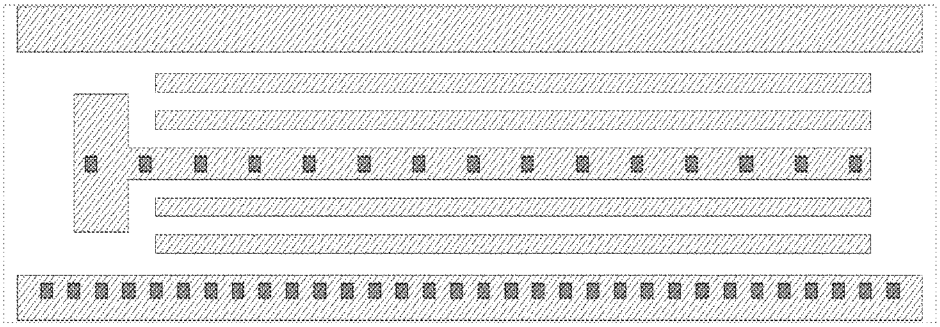
Figure 642A:
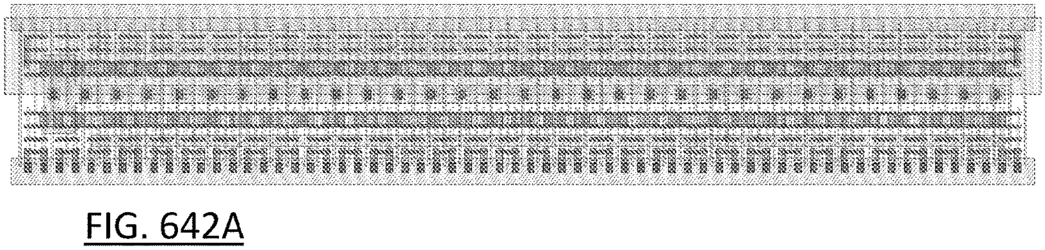
Figure 642B:
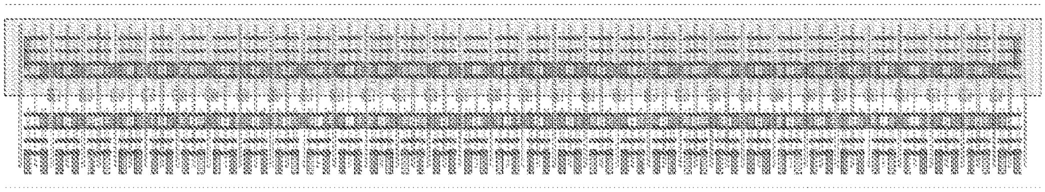
Figure 642C:
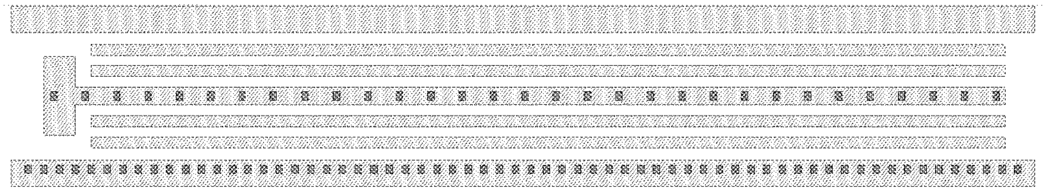
Figure 643A:
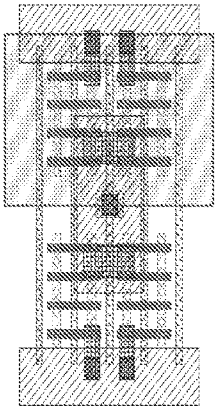
Figure 643B:
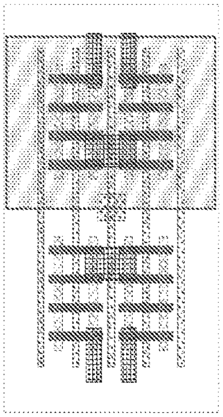
Figure 643C:
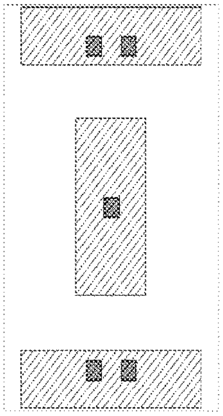
Figure 644A:
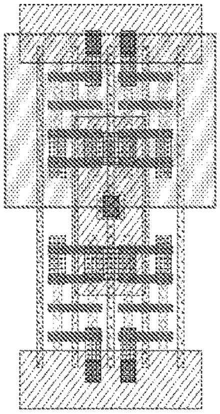
Figure 644B:
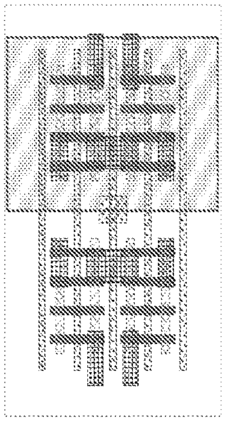
Figure 644C:
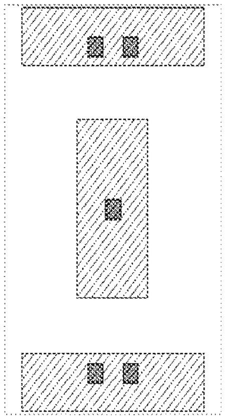
Figure 645A:
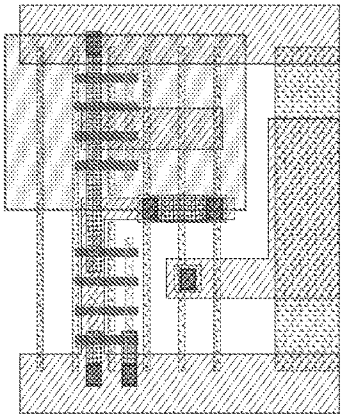
Figure 645B:
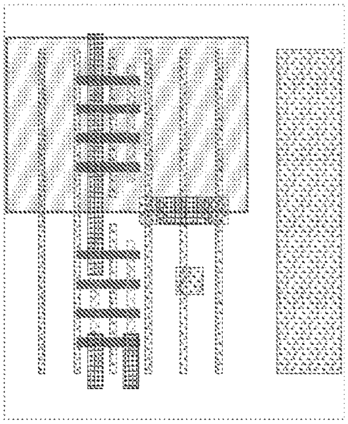
Figure 645C:
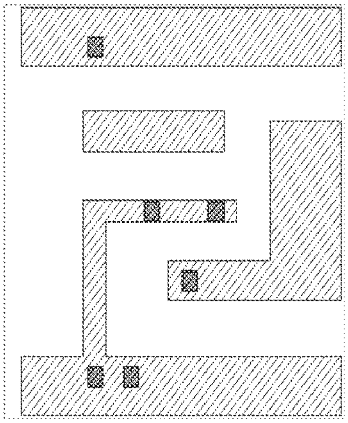
Figure 646A:
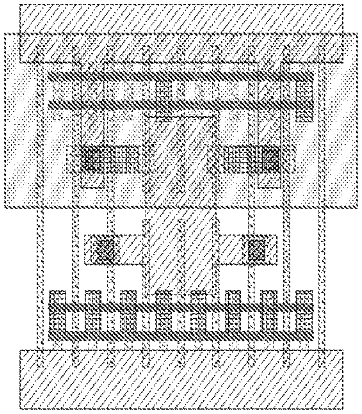
Figure 646B:
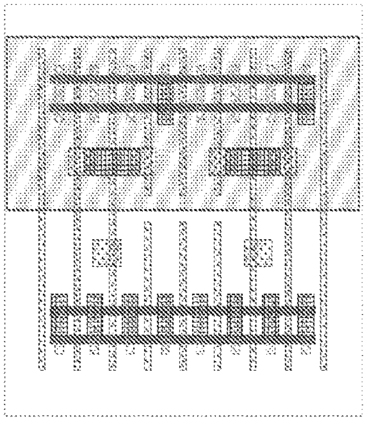
Figure 646C:
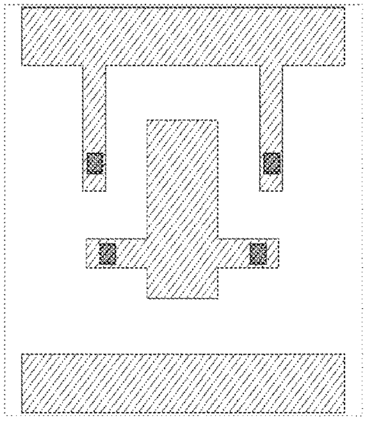
Figure 647A:
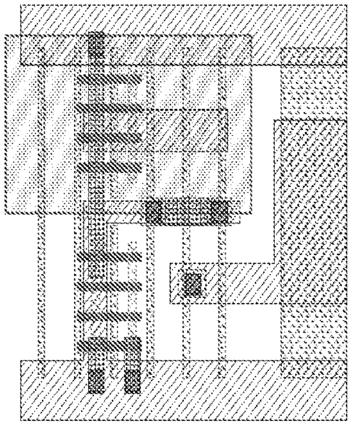
Figure 647B:
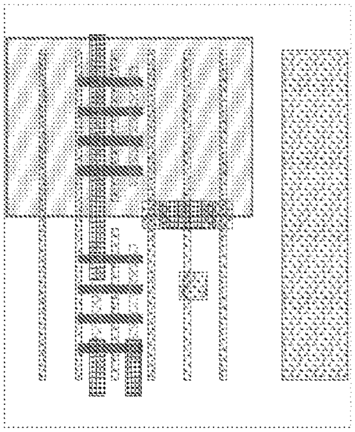
Figure 647C:
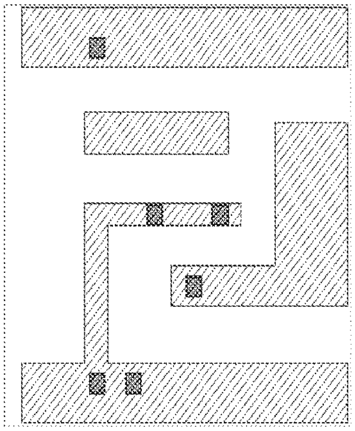
Figure 648A:
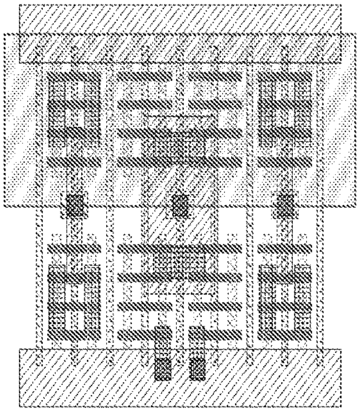
Figure 648B:
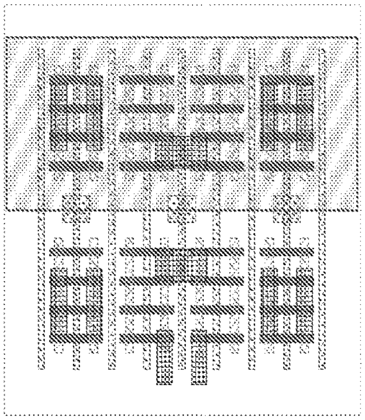
Figure 648C:
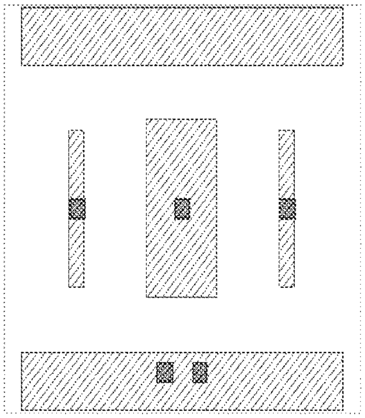
Figure 649A:
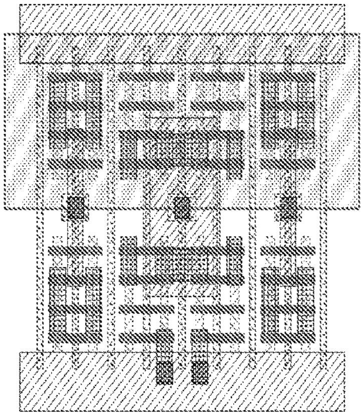
Figure 649B:
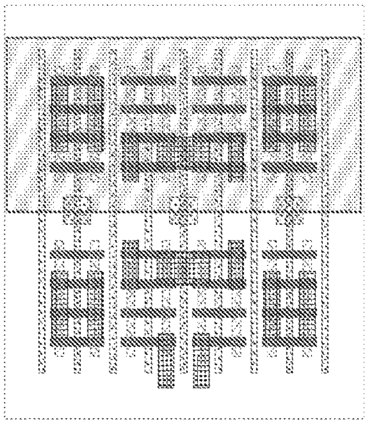
Figure 649C:
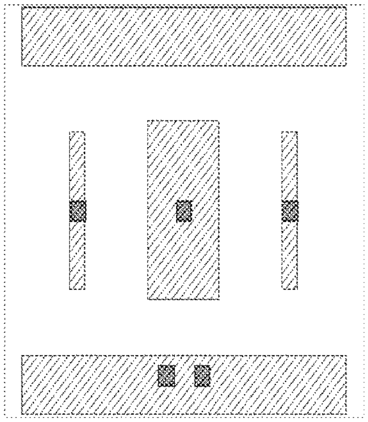
Figure 650A:
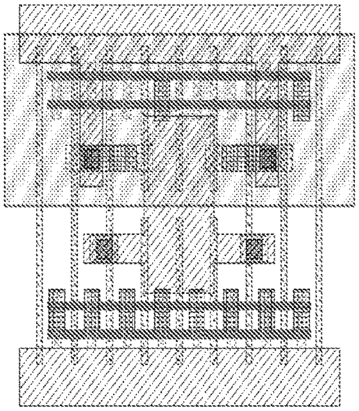
Figure 650B:
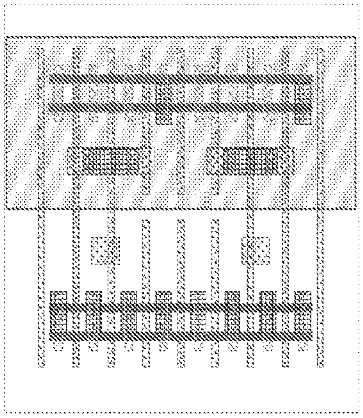
Figure 650C:
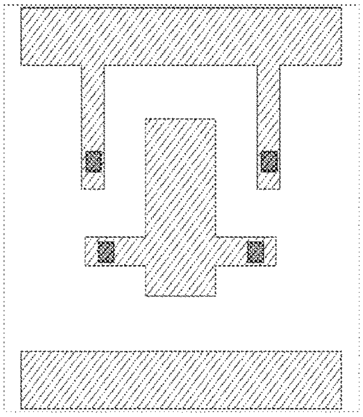
Figure 651A:
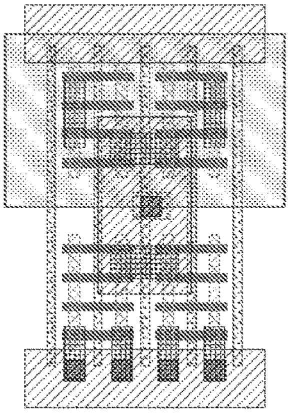
Figure 651B:
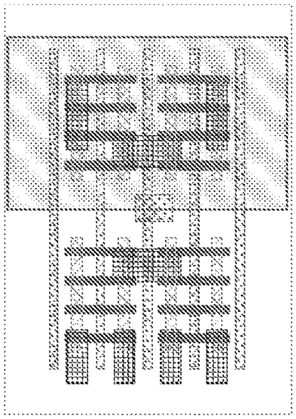
Figure 651C:
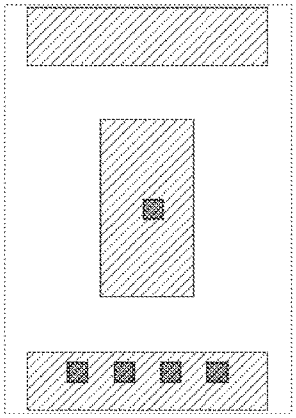
Figure 652A:
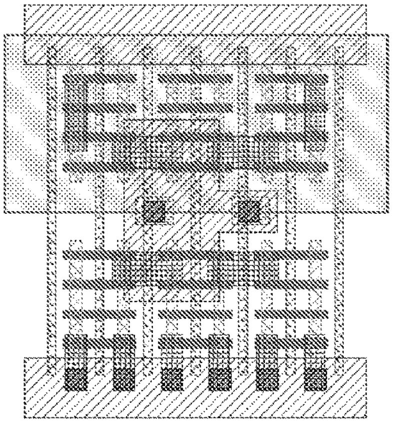
Figure 652B:
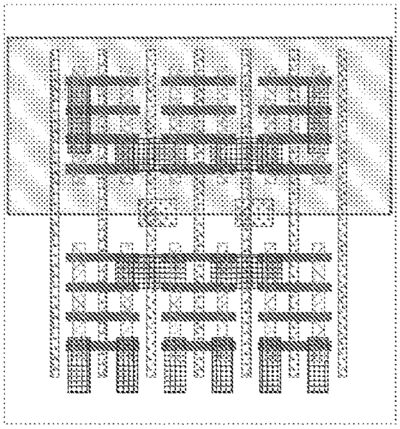
Figure 652C:
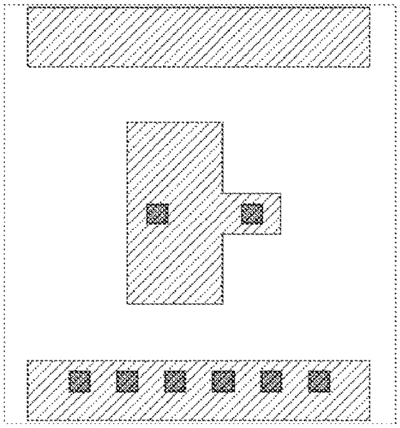
Figure 653A:
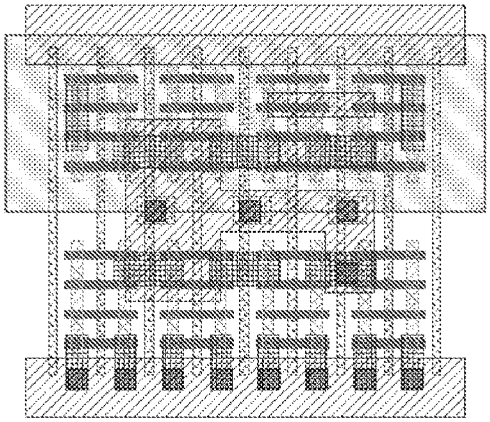
Figure 653B:
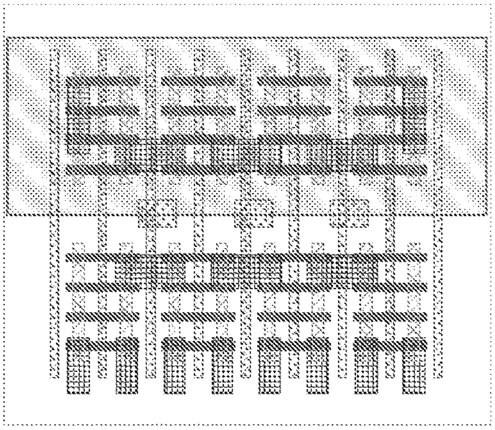
Figure 653C:
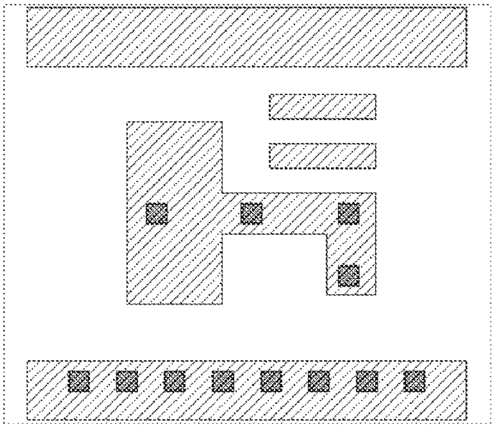
Figure 654A:
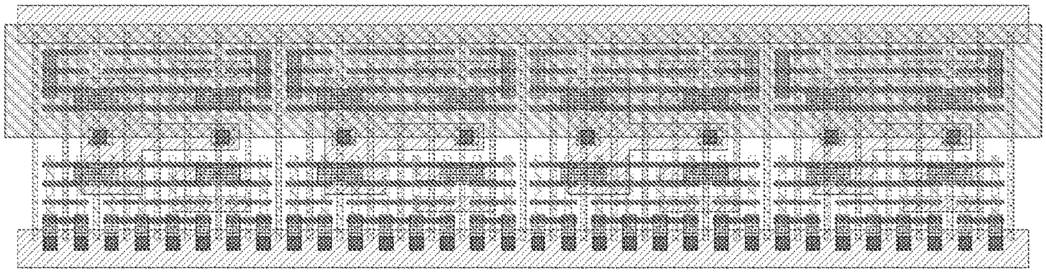
Figure 654B:
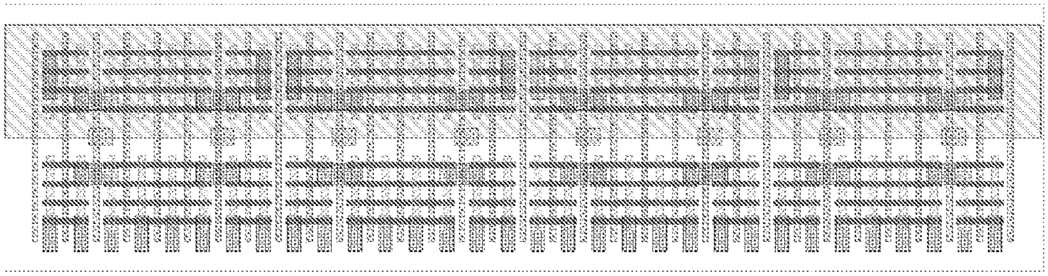
Figure 654C:
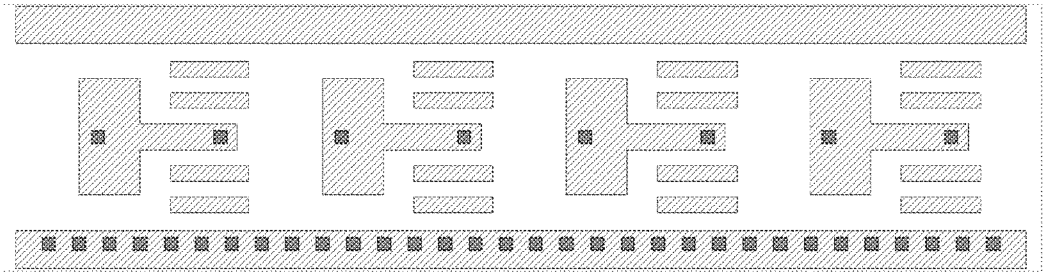
Figure 655A:
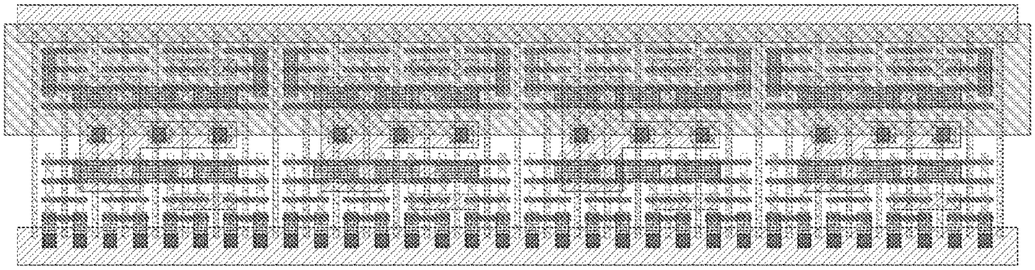
Figure 655B:
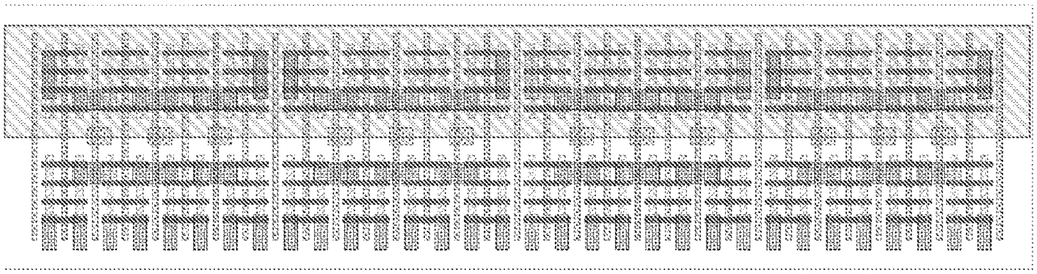
Figure 655C:
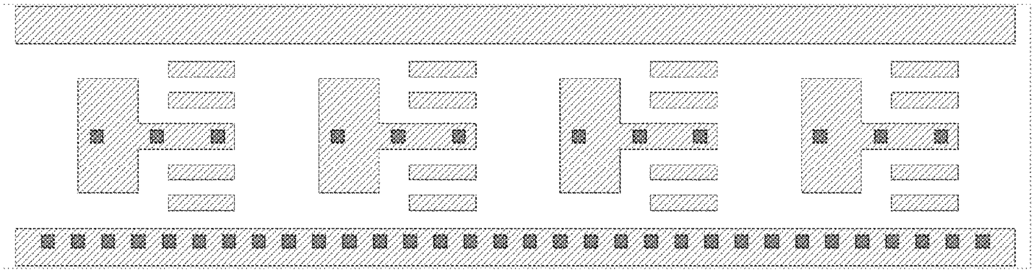
Figure 656A:
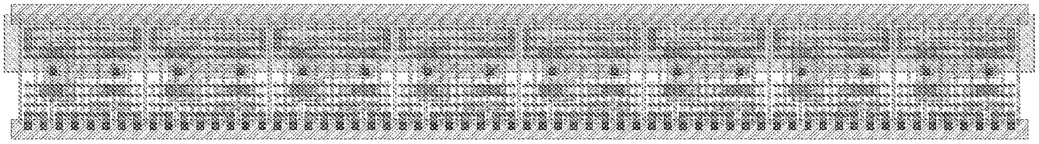
Figure 656B:
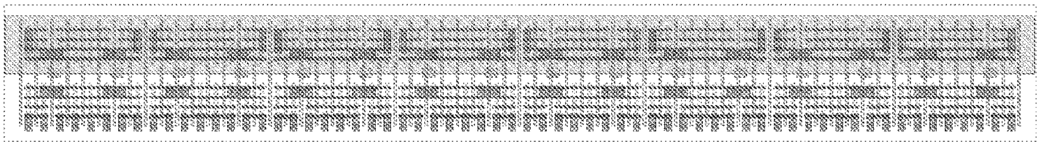
Figure 656C:
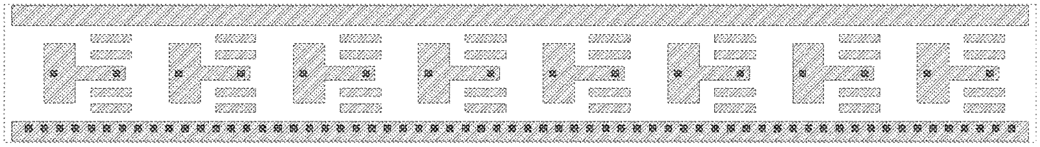
Figure 657A:
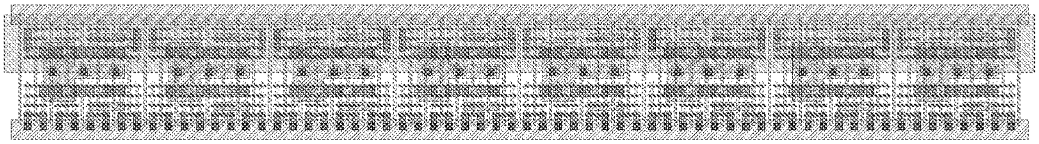
Figure 657B:
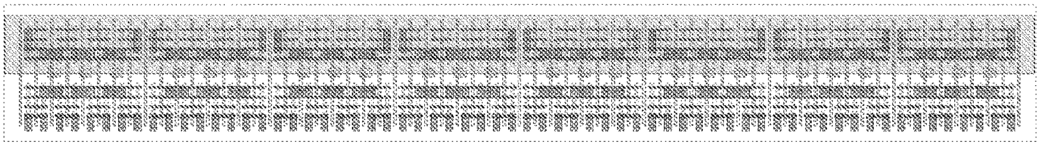
Figure 657C:
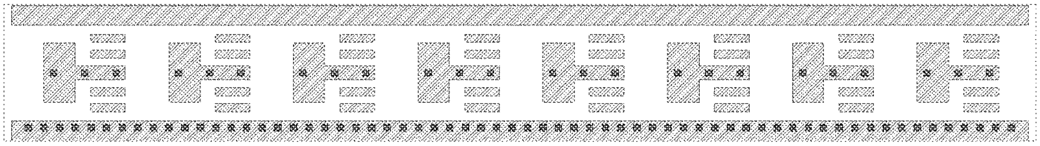
Figure 658A:
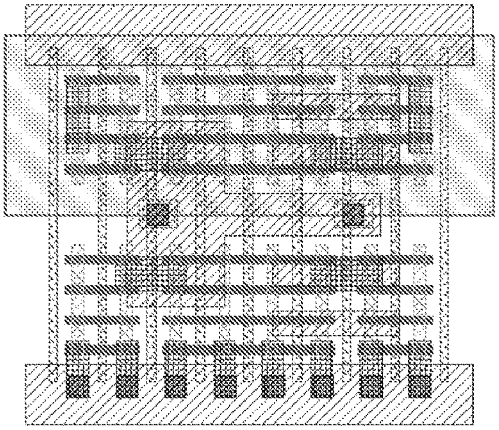
Figure 658B:
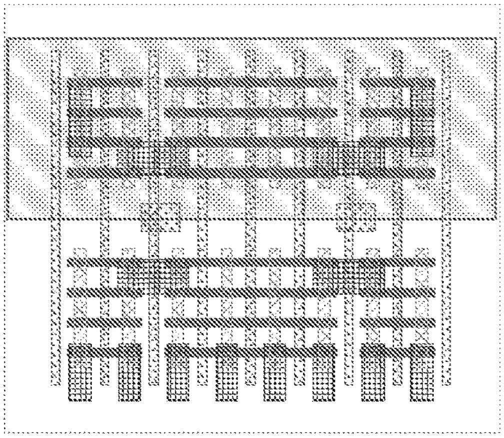
Figure 658C:
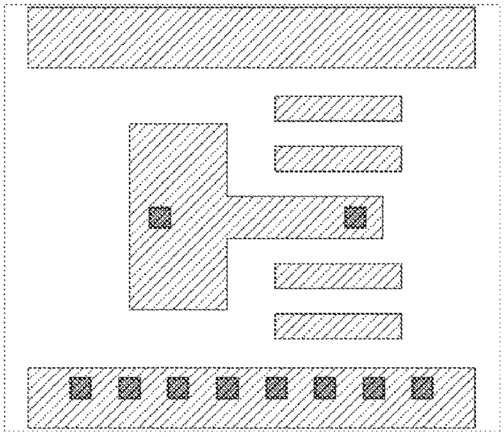
Figure 659A:
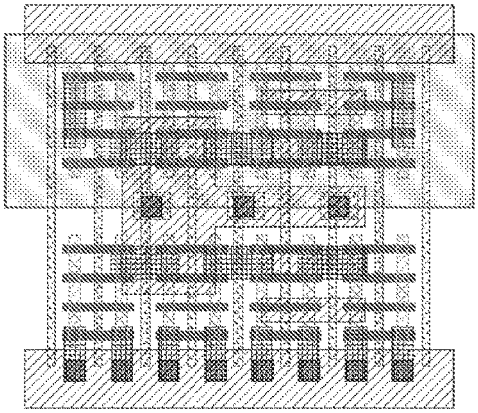
Figure 659B:
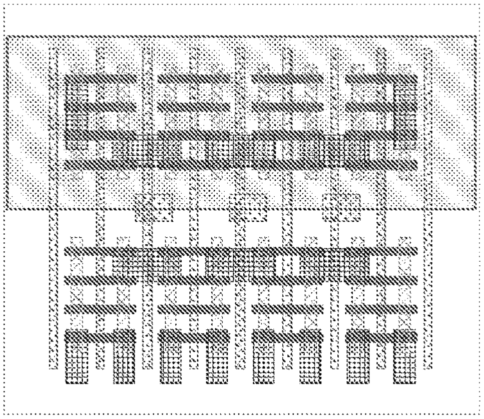
Figure 659C:
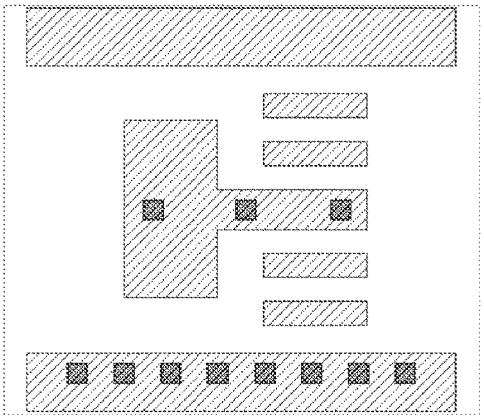
Figure 660A:
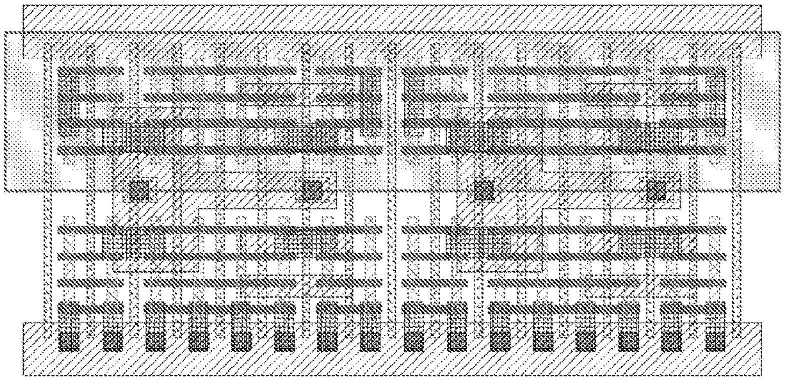
Figure 660B:
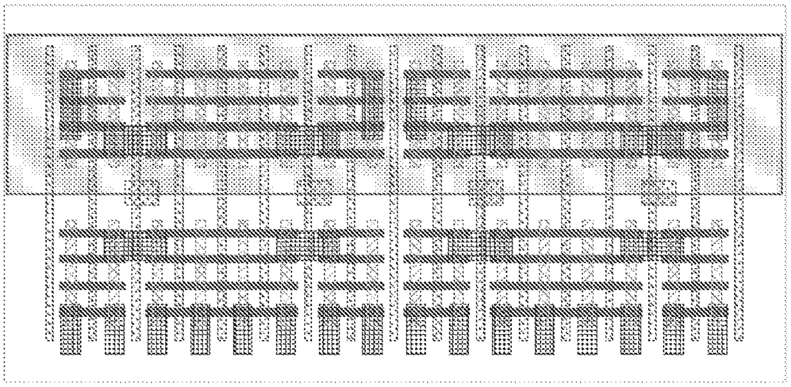
Figure 660C:
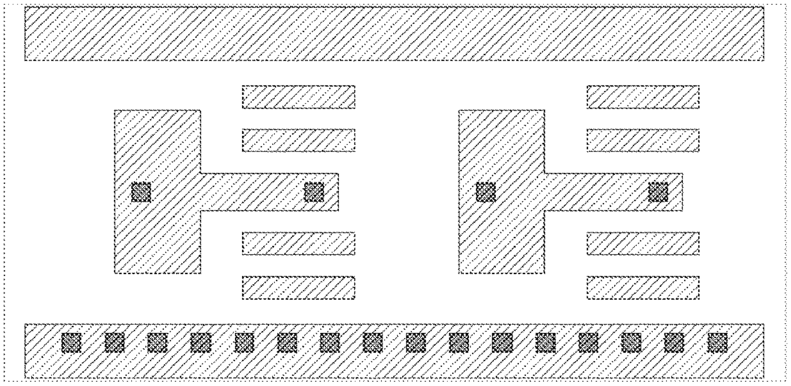
Figure 661A:
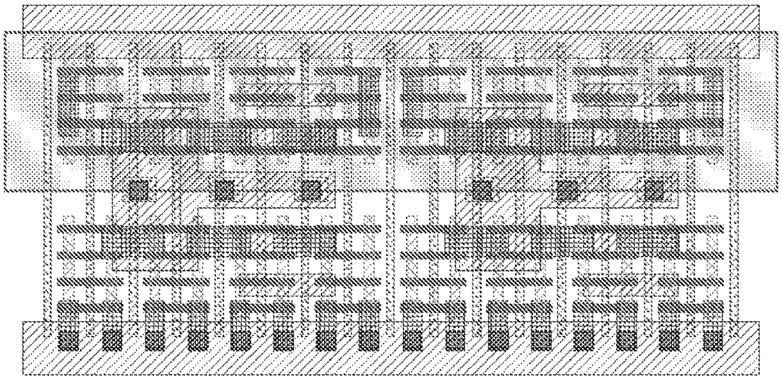
Figure 661B:
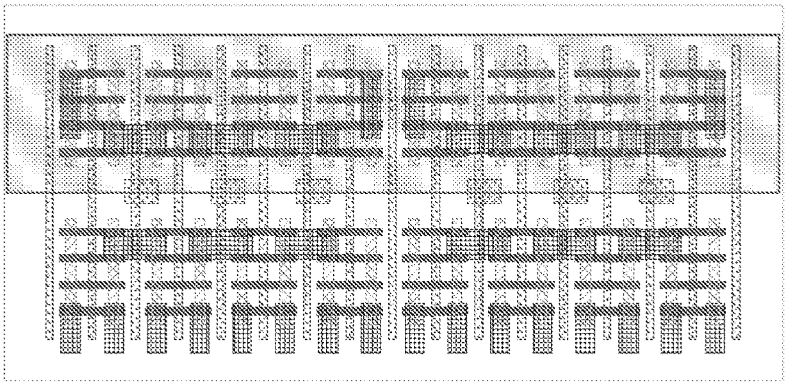
Figure 661C:
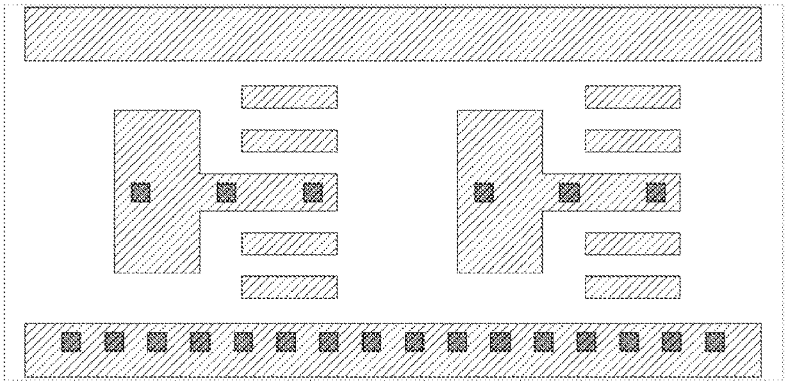
Figure 662A:
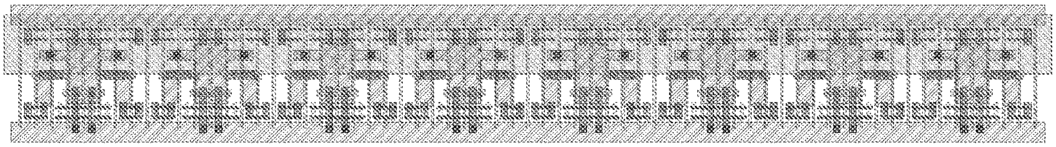
Figure 662B:
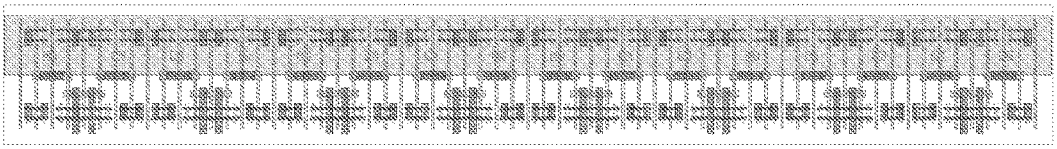
Figure 662C:
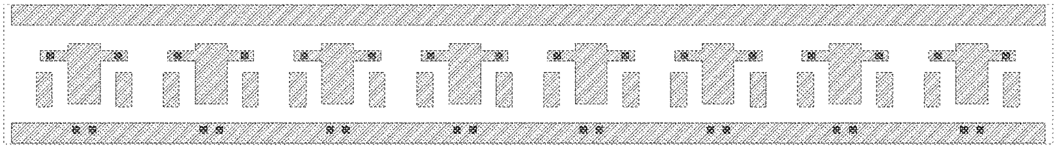
Figure 663A:
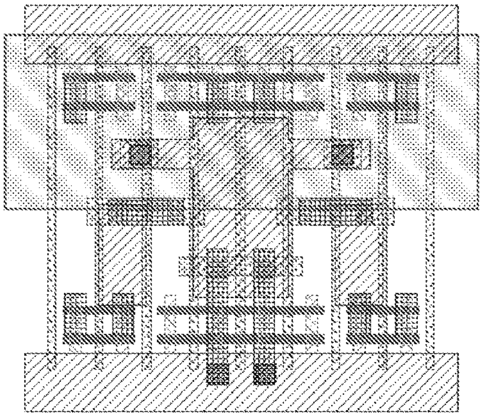
Figure 663B:
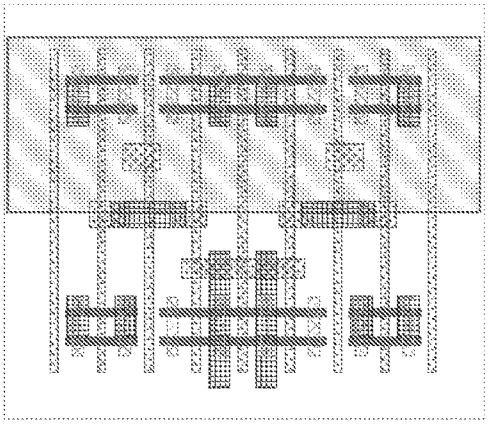
Figure 663C:
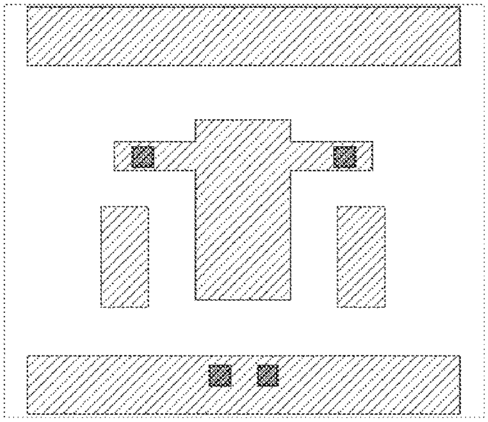
Figure 664A:
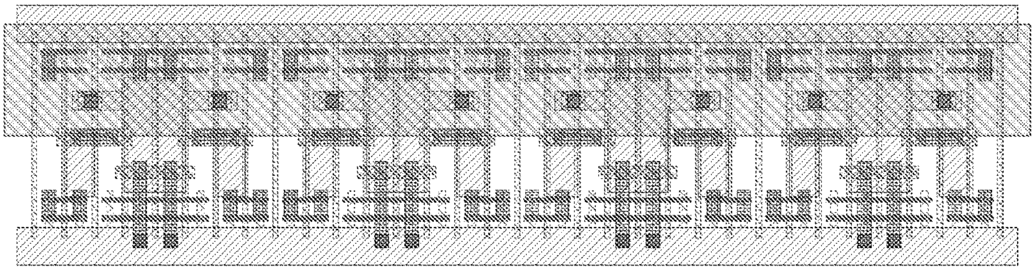
Figure 664B:
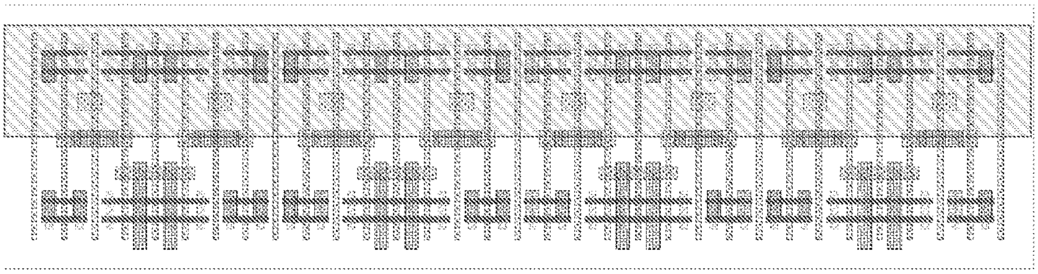
Figure 664C:
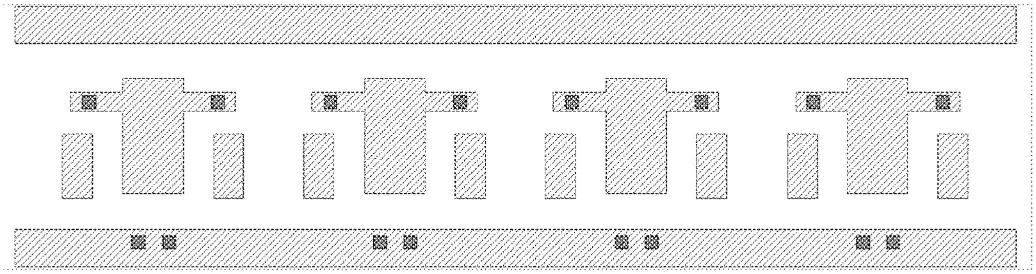
Figure 665A:
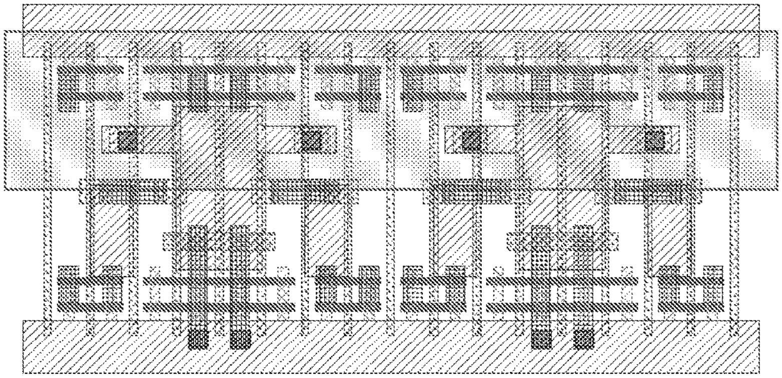
Figure 665B:
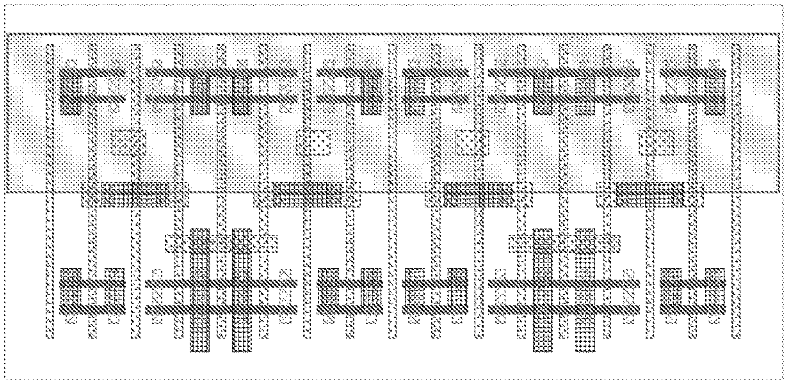
Figure 665C:
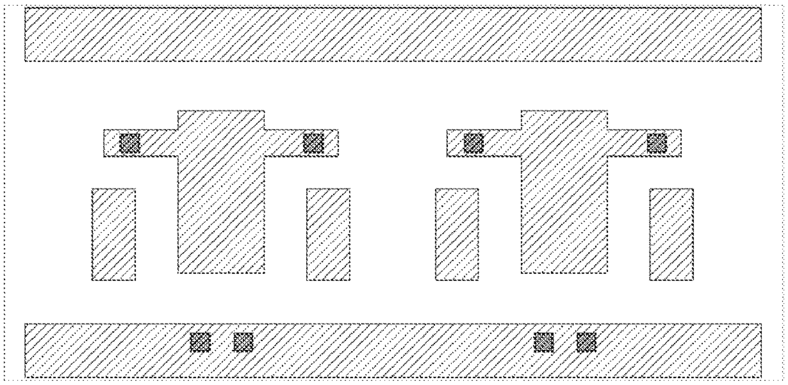
Figure 666A:
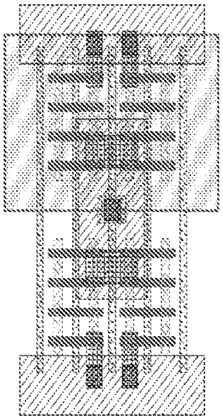
Figure 666B:
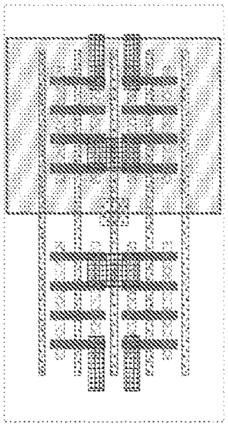
Figure 666C:
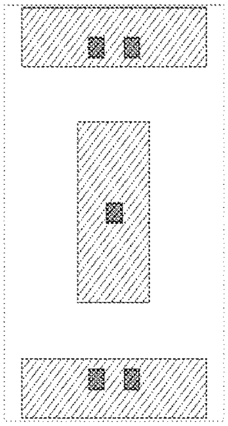
Figure 667A:
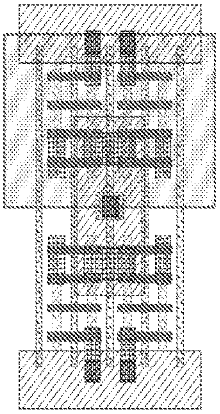
Figure 667B:
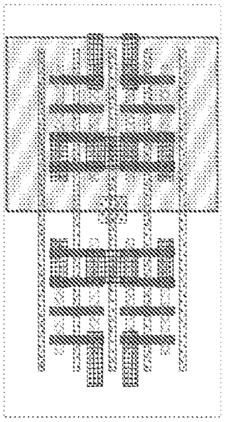
Figure 667C:
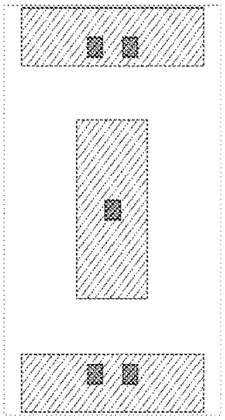
Figure 668A:
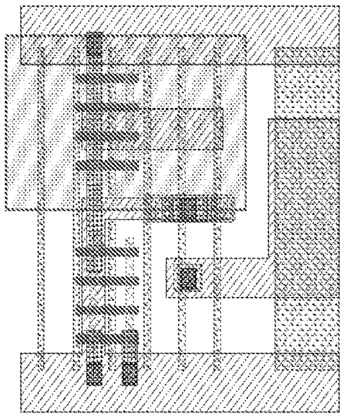
Figure 668B:
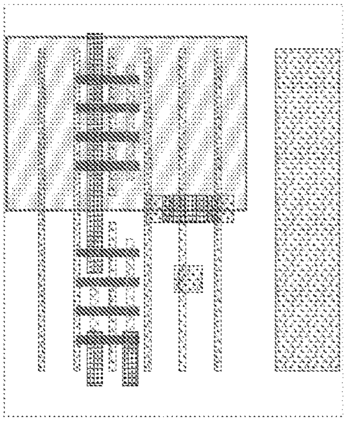
Figure 668C:
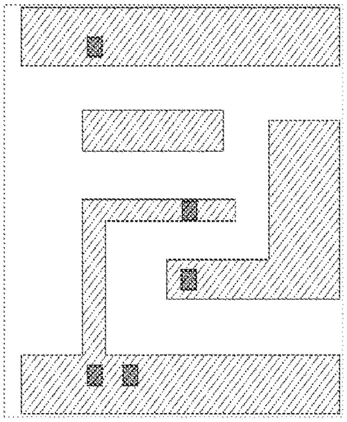
Figure 669A:
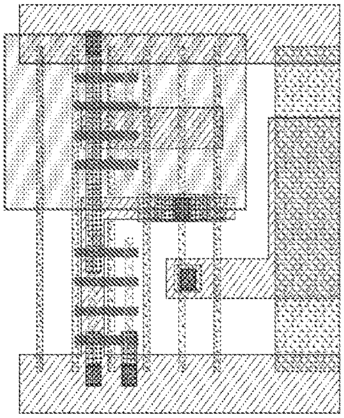
Figure 669B:
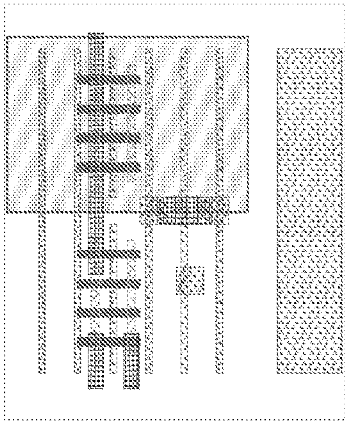
Figure 669C:
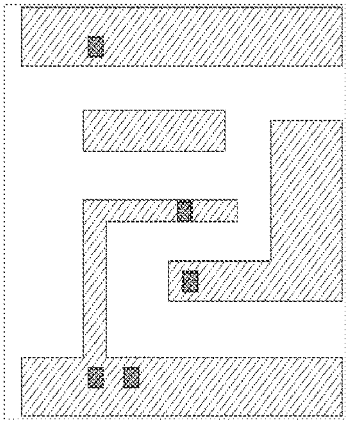
Figure 670A:
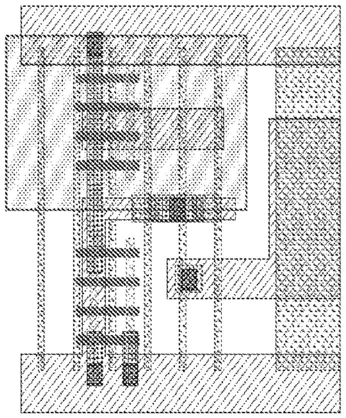
Figure 670B:
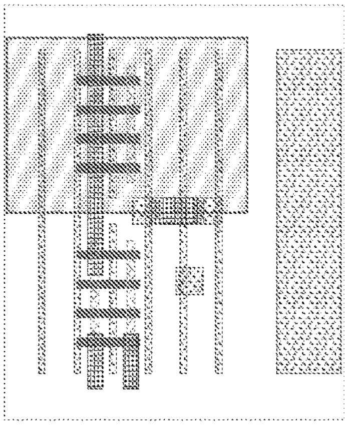
Figure 670C:
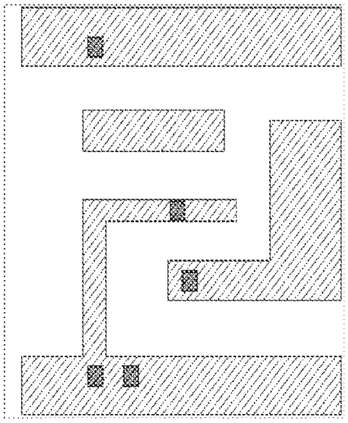
Figure 671A:
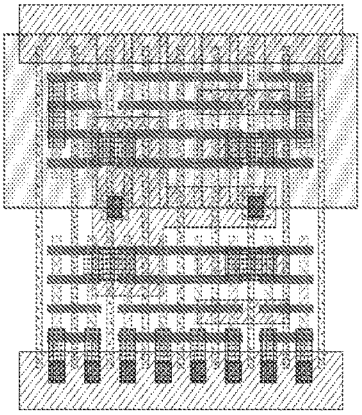
Figure 671B:
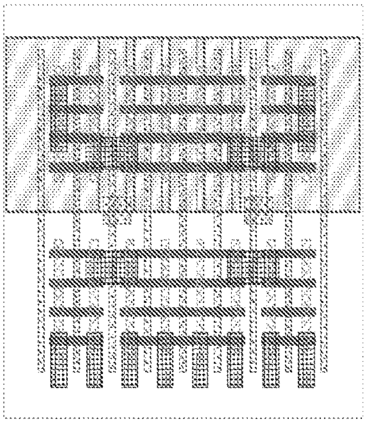
Figure 671C:
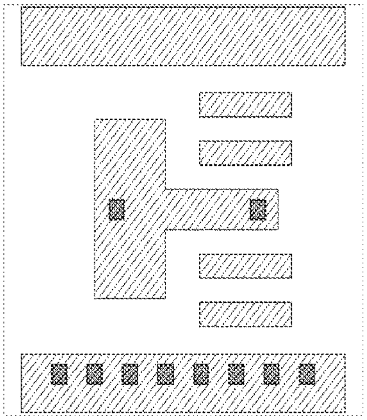
Figure 672A:
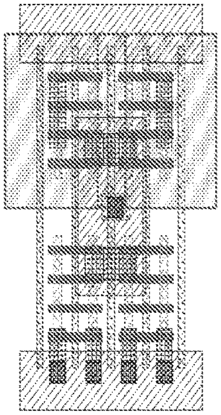
Figure 672B:
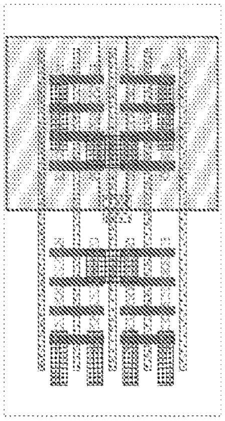
Figure 672C:
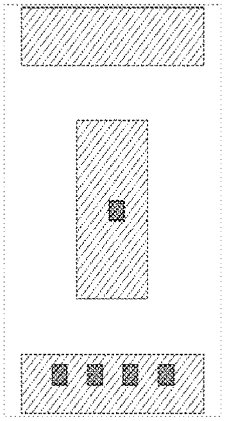
Figure 673A:
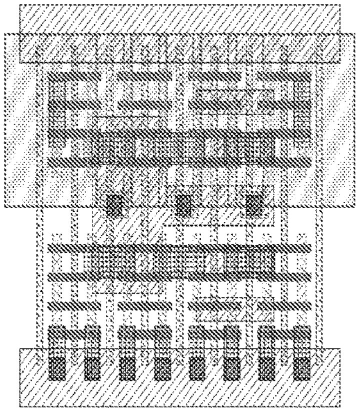
Figure 673B:
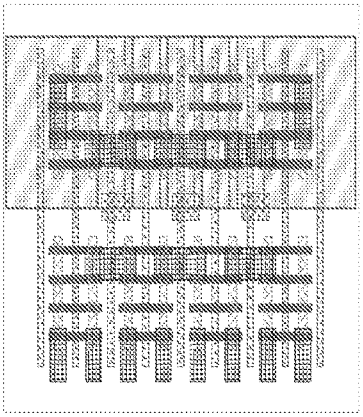
Figure 673C:
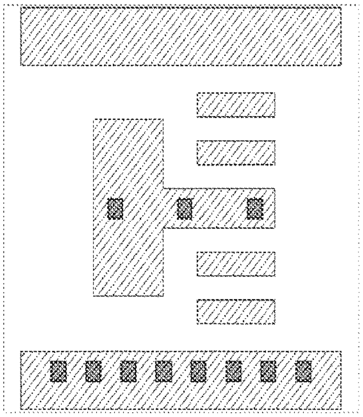
Figure 674A:
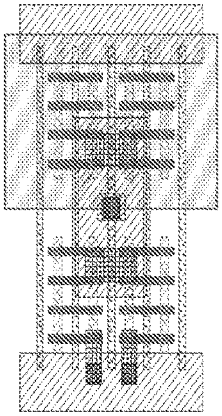
Figure 674B:
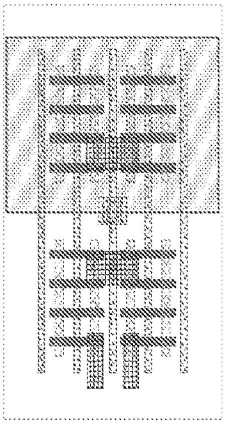
Figure 674C:
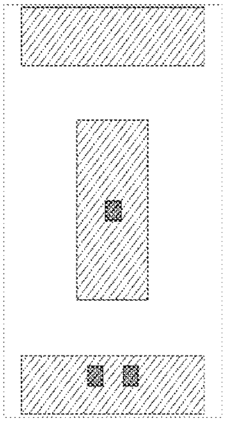
Figure 675A:
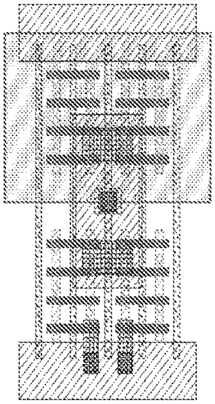
Figure 675B:
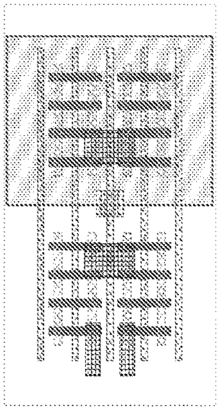
Figure 675C:
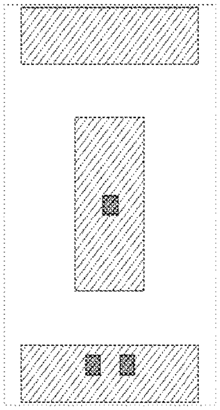
Figure 676A:
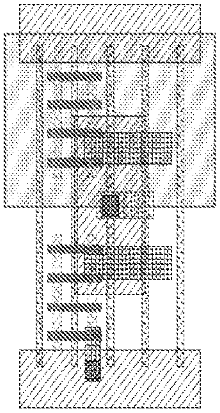
Figure 676B:
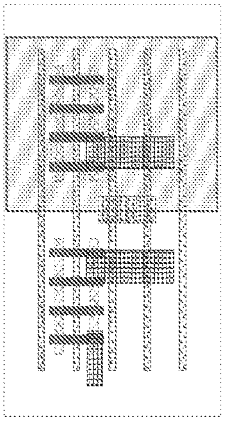
Figure 676C:
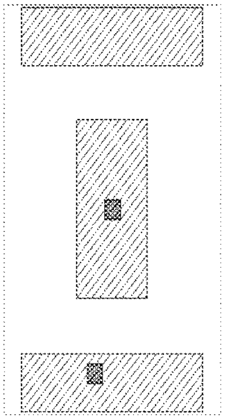
Figure 677A:
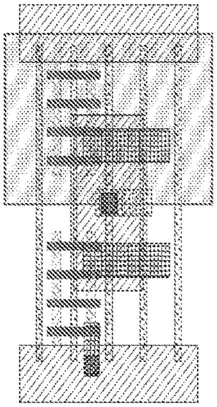
Figure 677B:
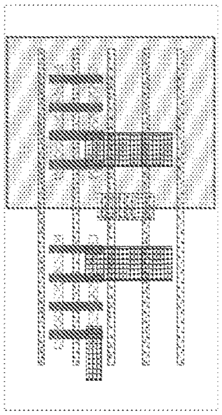
Figure 677C:
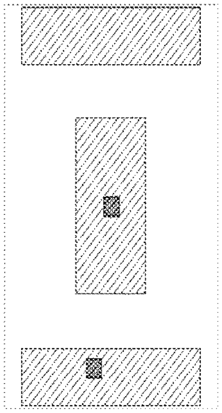
Figure 678A:
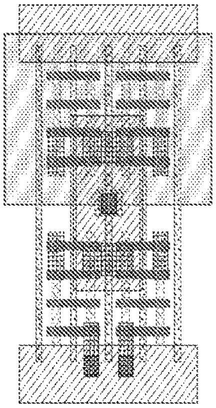
Figure 678B:
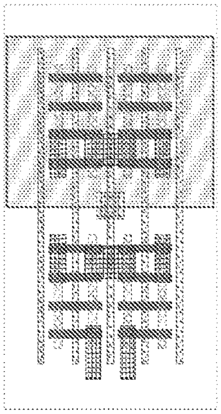
Figure 678C:
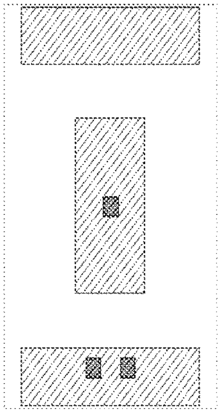
Figure 679A:
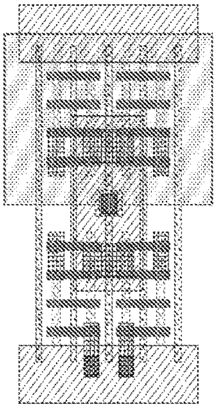
Figure 679B:
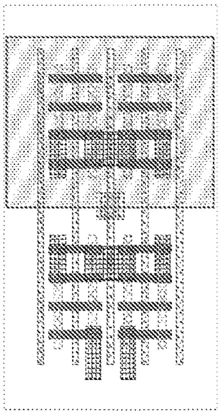
Figure 679C:
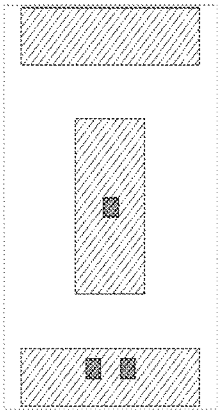
Figure 680A:
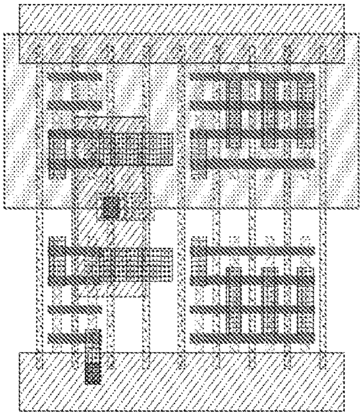
Figure 680B:
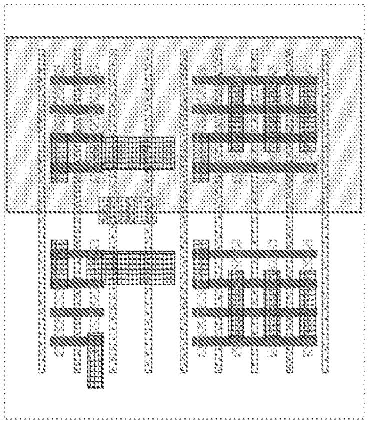
Figure 680C:
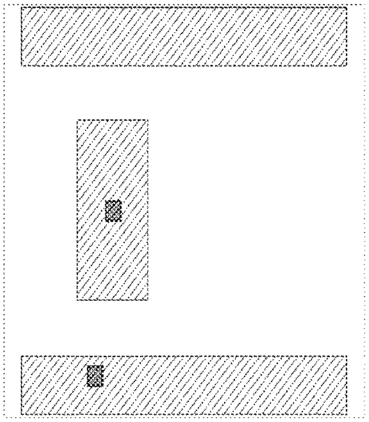
Figure 681A:
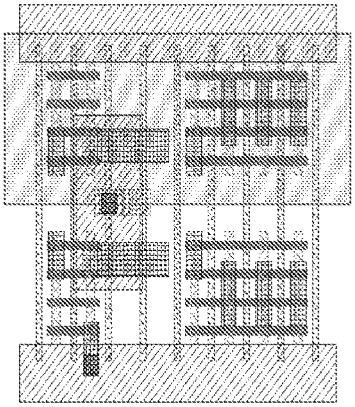
Figure 681B:
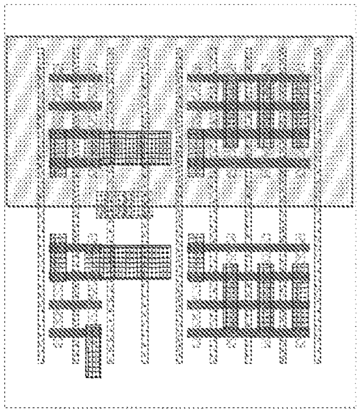
Figure 681C:
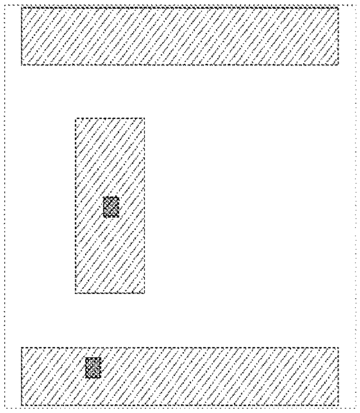
Figure 682A:
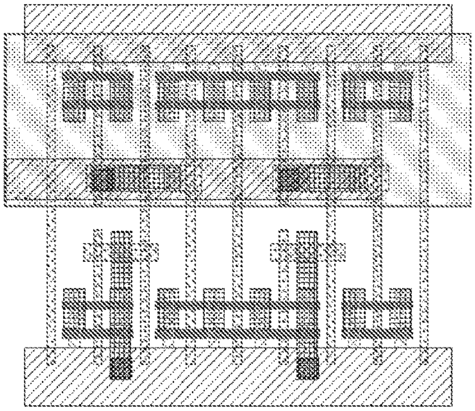
Figure 682B:
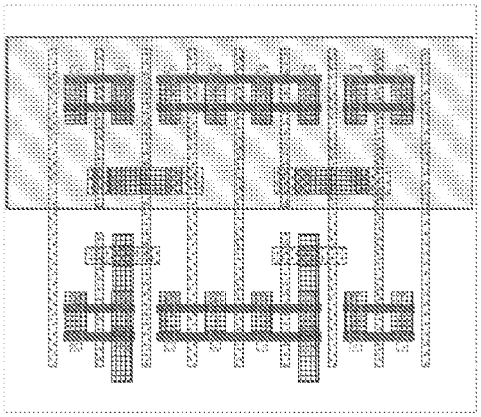
Figure 682C:
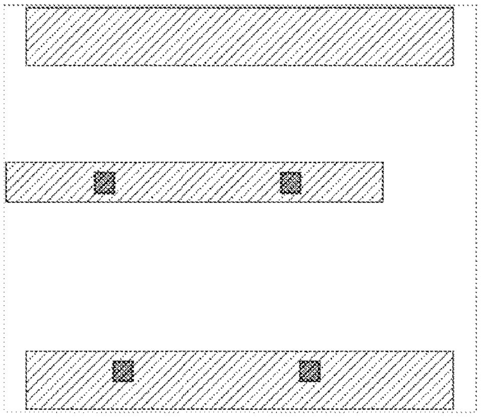
Figure 683A:
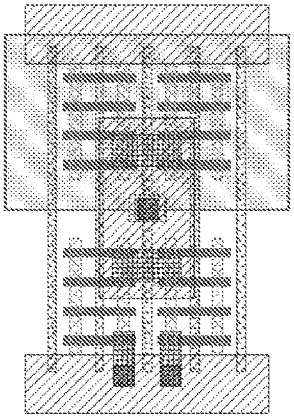
Figure 683B:
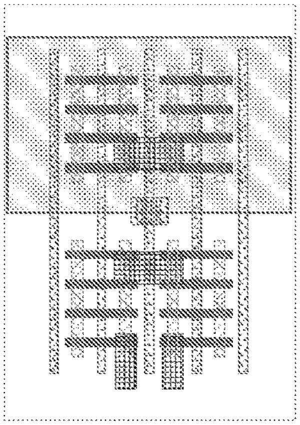
Figure 683C:
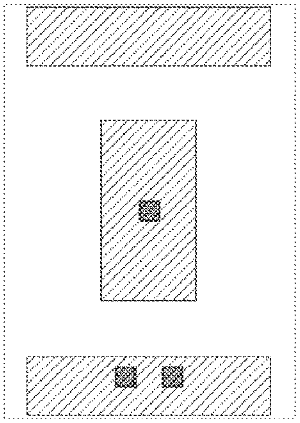
Figure 684A:
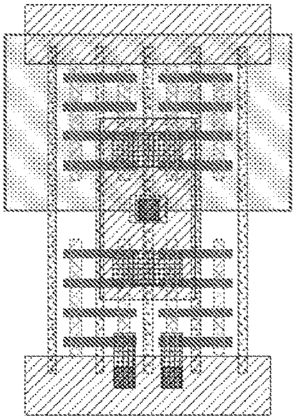
Figure 684B:
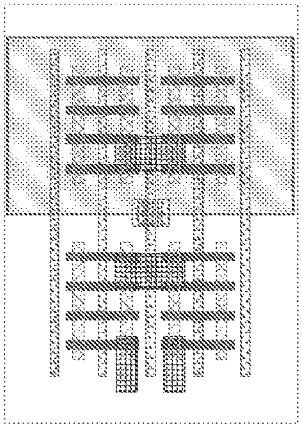
Figure 684C:
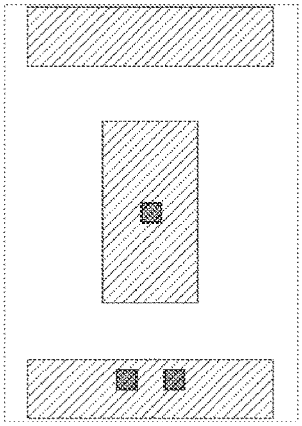
Figure 685A:
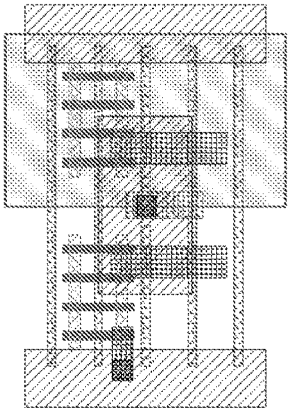
Figure 685B:
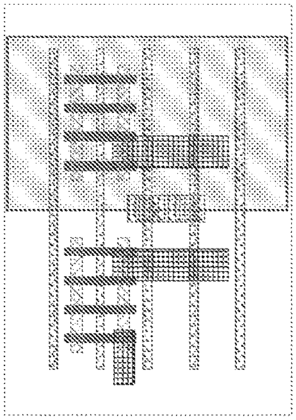
Figure 685C:
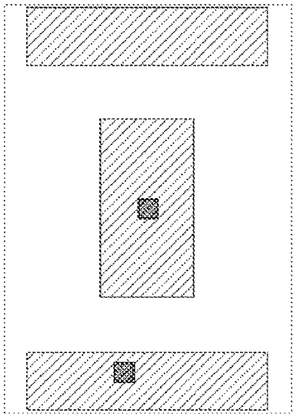
Figure 686A:
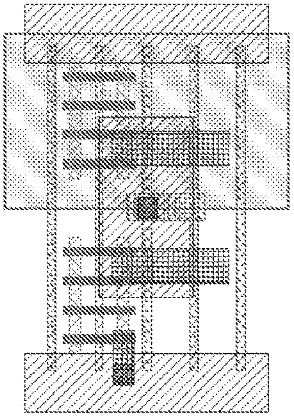
Figure 686B:
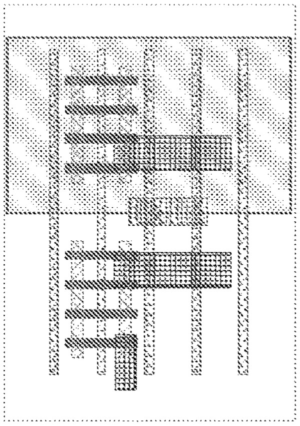
Figure 686C:
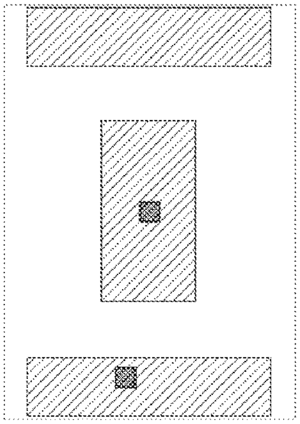
Figure 687A:
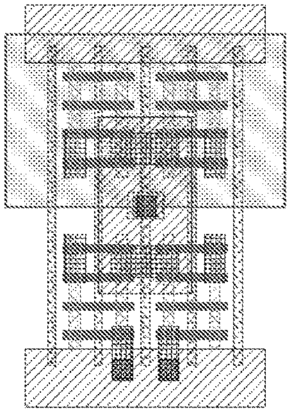
Figure 687B:
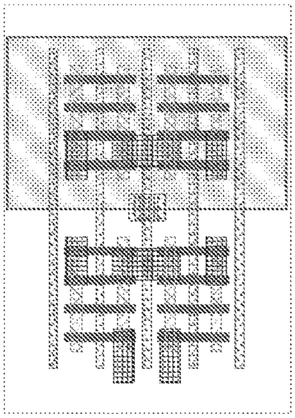
Figure 687C:
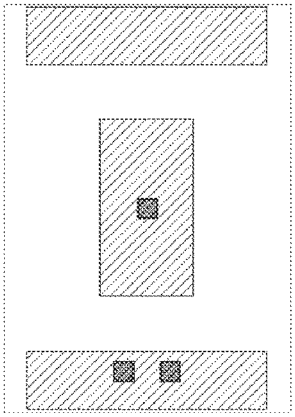
Figure 688A:
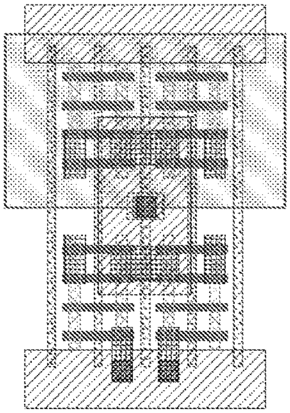
Figure 688B:
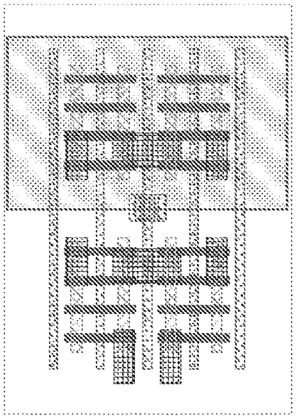
Figure 688C:
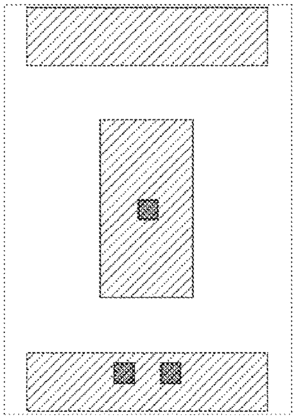
Figure 689A:
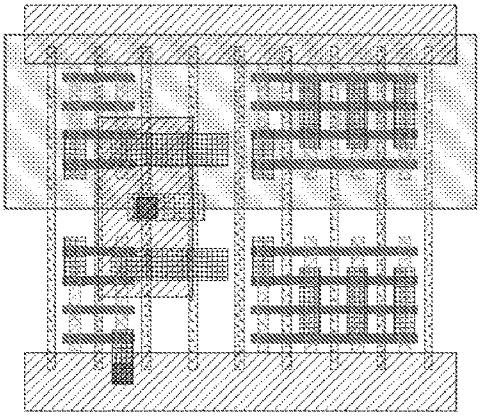
Figure 689B:
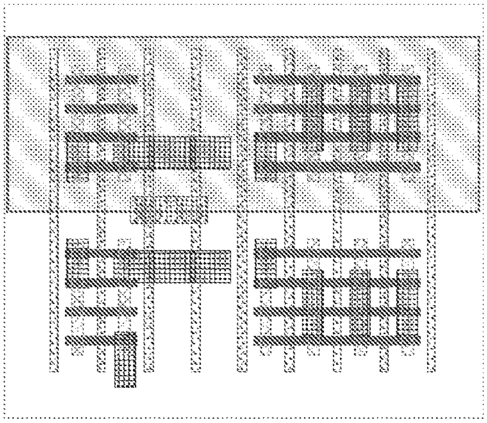
Figure 689C:
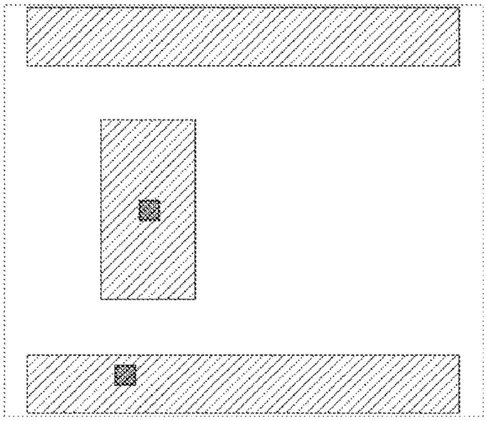
Figure 690A:
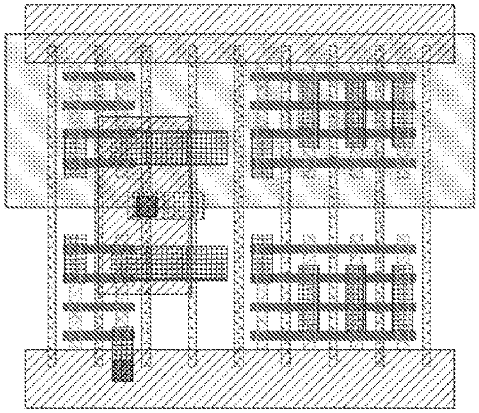
Figure 690B:
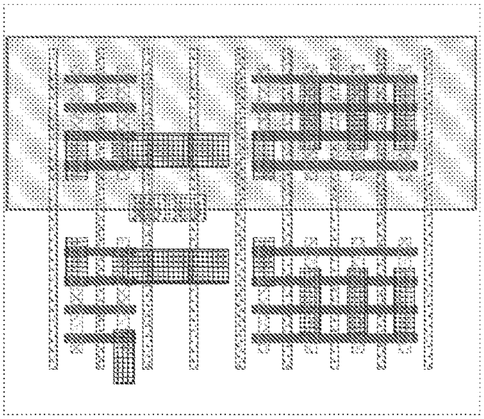
Figure 690C:
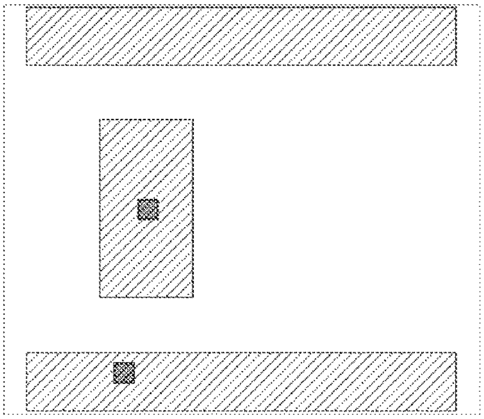
Figure 691A:
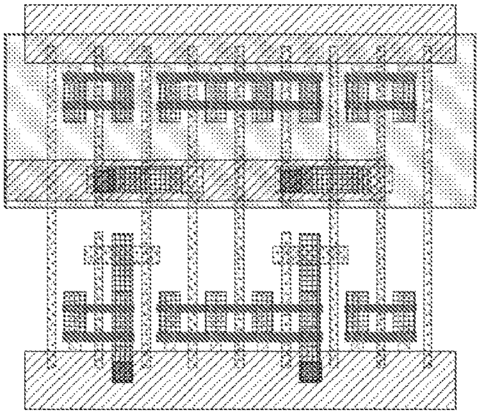
Figure 691B:
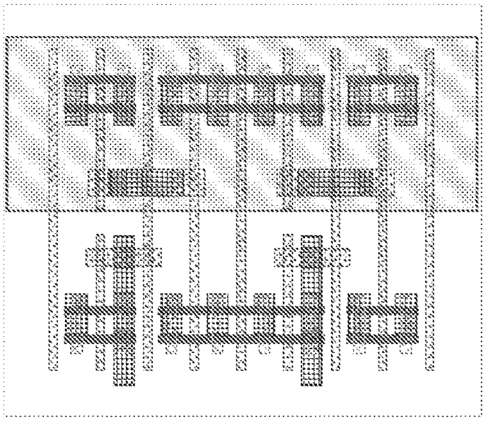
Figure 691C:
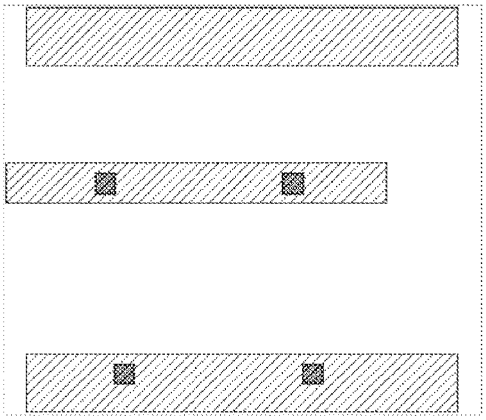
Figure 692A:
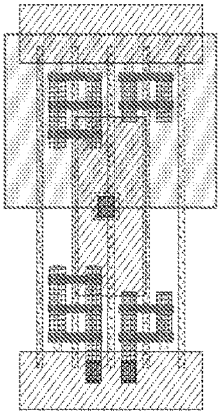
Figure 692B:
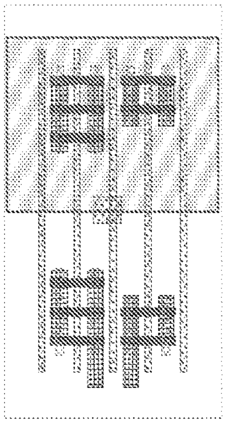
Figure 692C:
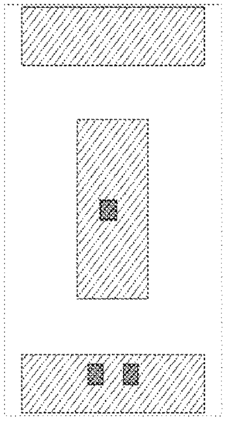
Figure 693A:
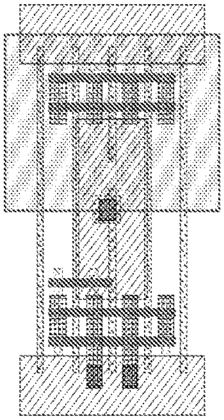
Figure 693B:
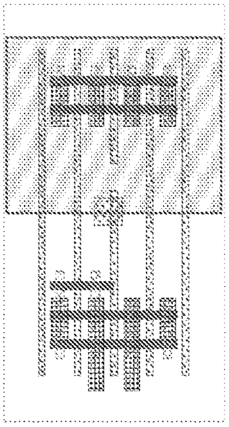
Figure 693C:
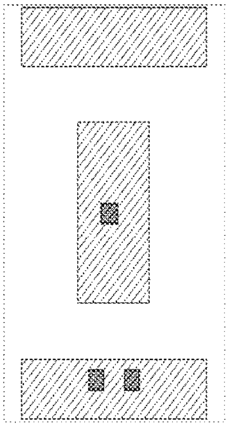
Figure 694A:
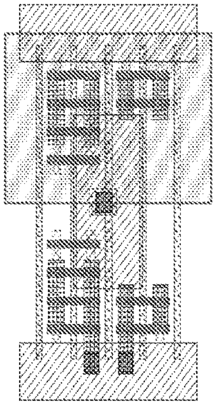
Figure 694B:
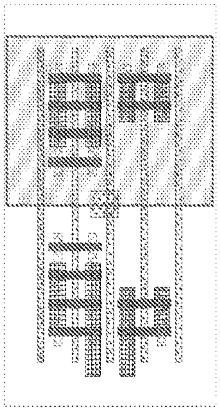
Figure 694C:
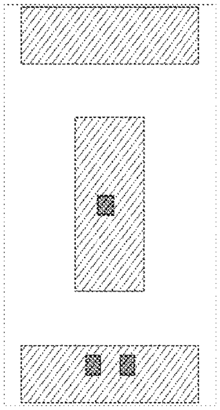
Figure 695A:
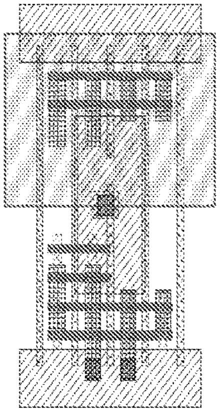
Figure 695B:
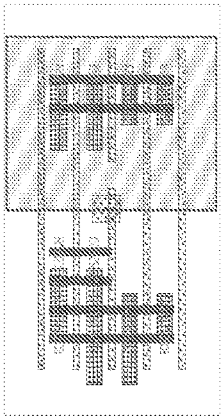
Figure 695C:
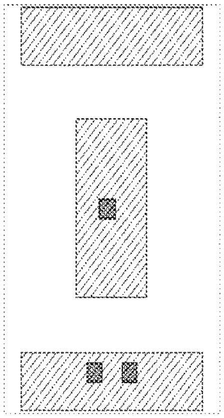
Figure 696A:
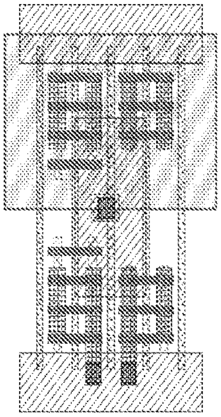
Figure 696B:
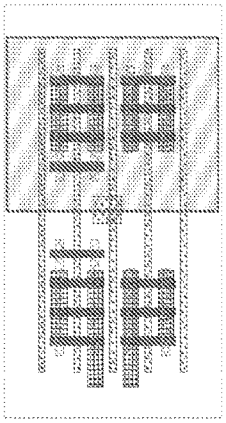
Figure 696C:
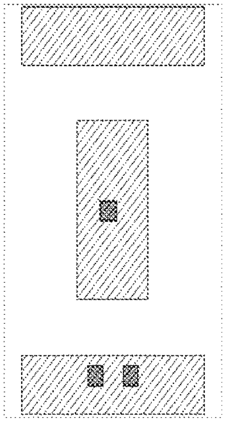
Figure 697A:
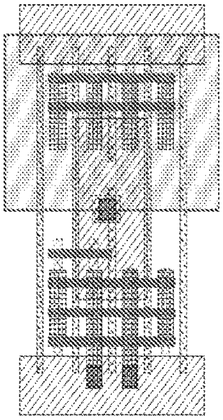
Figure 697B:
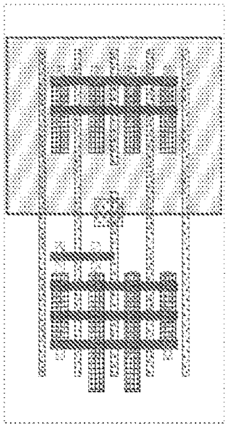
Figure 697C:
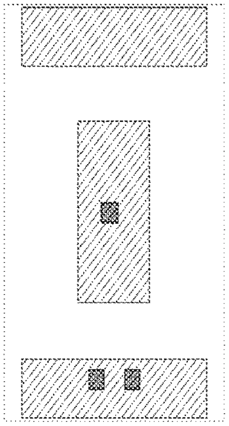
Figure 698A:
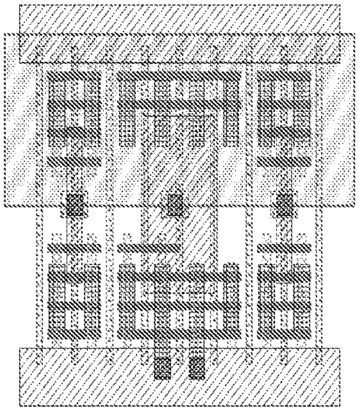
Figure 698B:
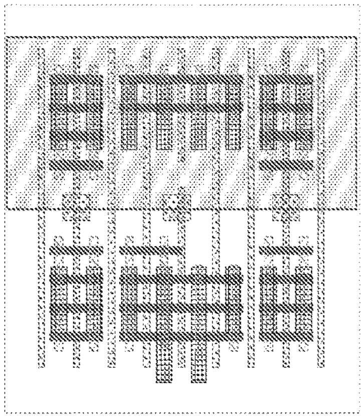
Figure 698C:
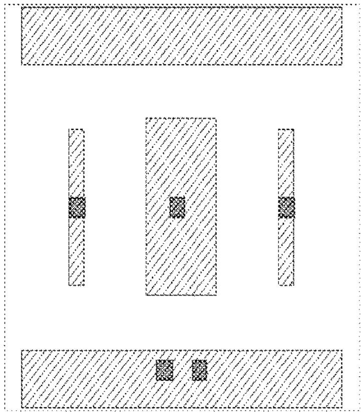
Figure 699A:
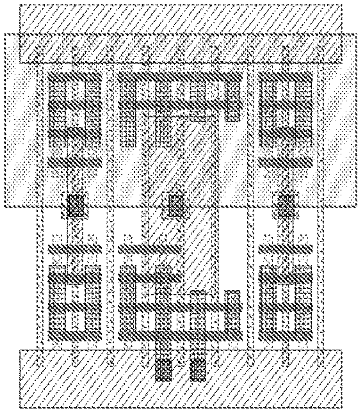
Figure 699B:
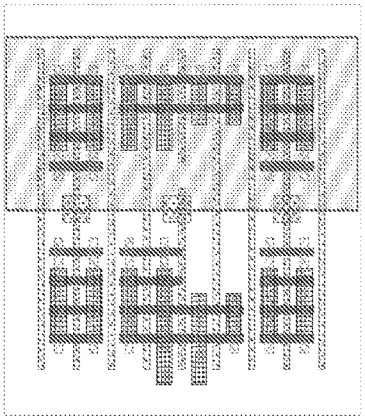
Figure 699C:
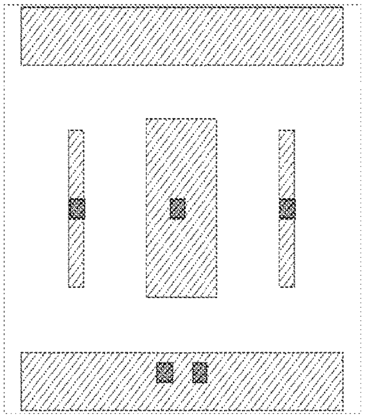
Figure 700A:
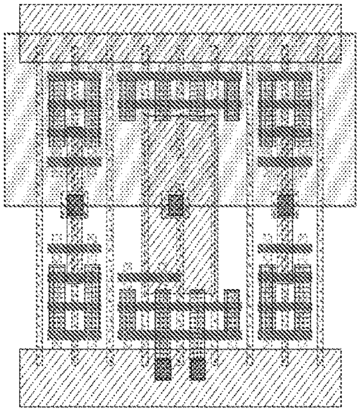
Figure 700B:
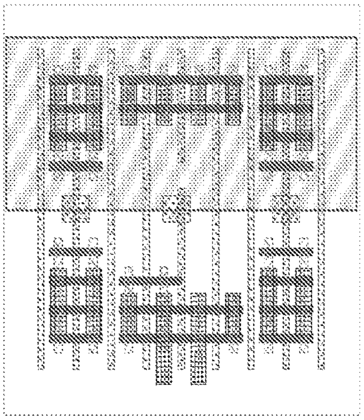
Figure 700C:
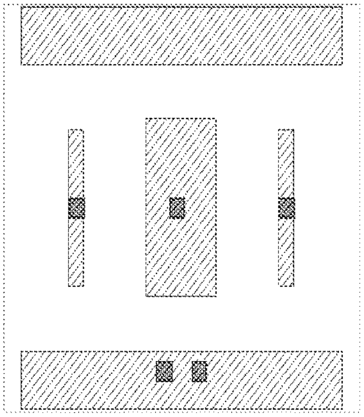
Figure 701A:
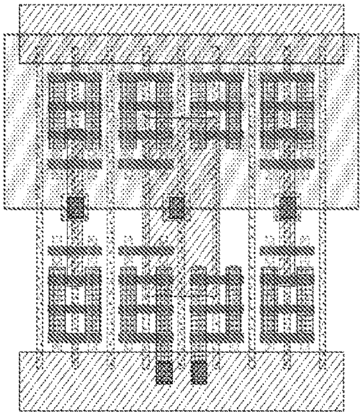
Figure 701B:
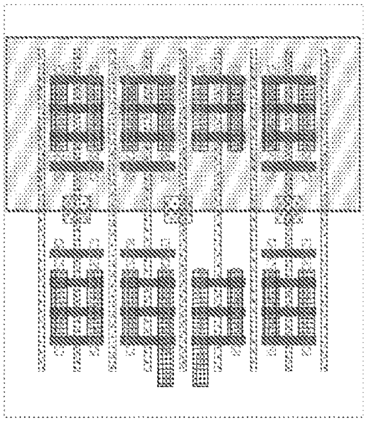
Figure 701C:
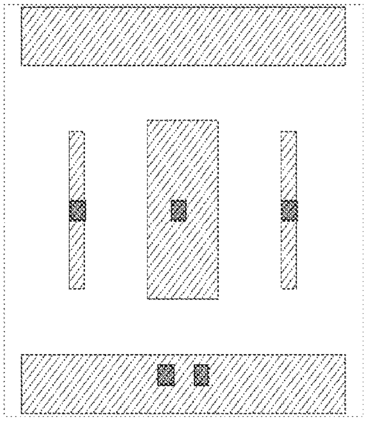
Figure 702A:
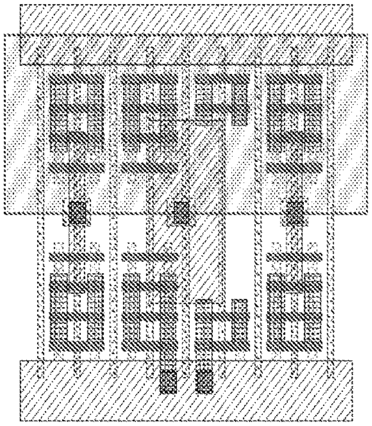
Figure 702B:
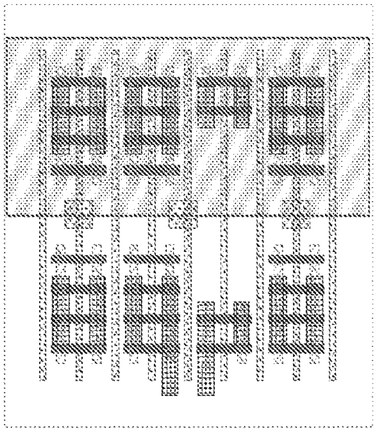
Figure 702C:
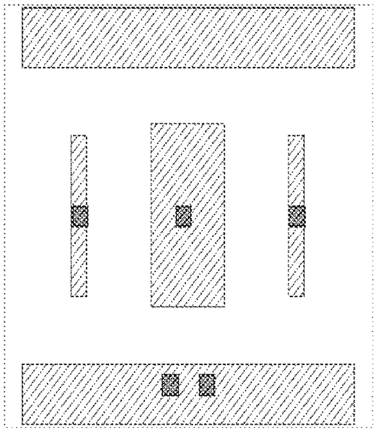
Figure 703A:
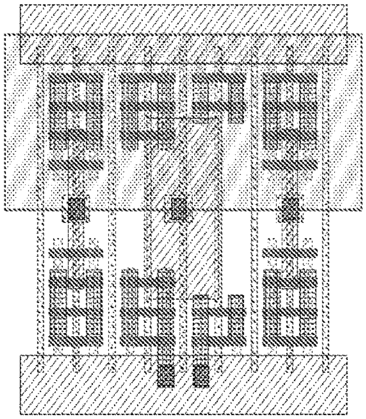
Figure 703B:
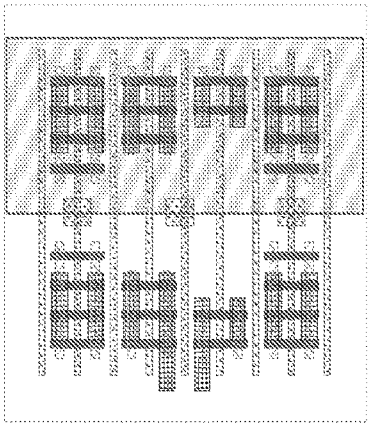
Figure 703C:
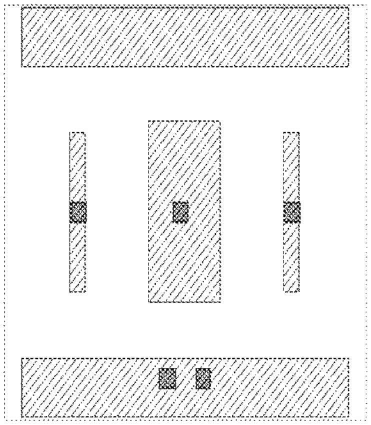
Figure 704A:
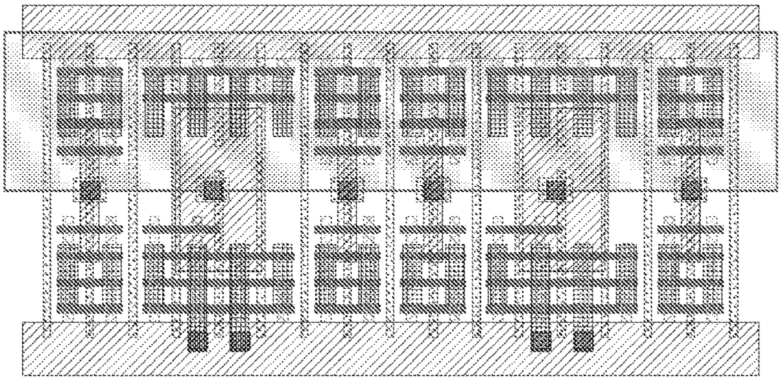
Figure 704B:
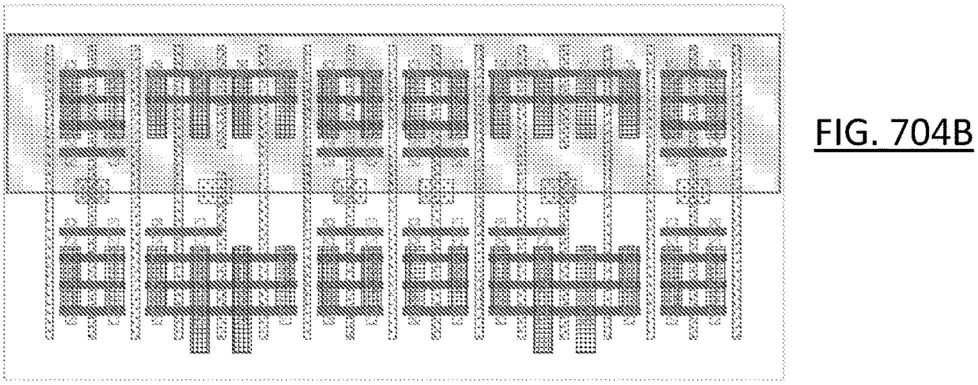
Figure 704C:
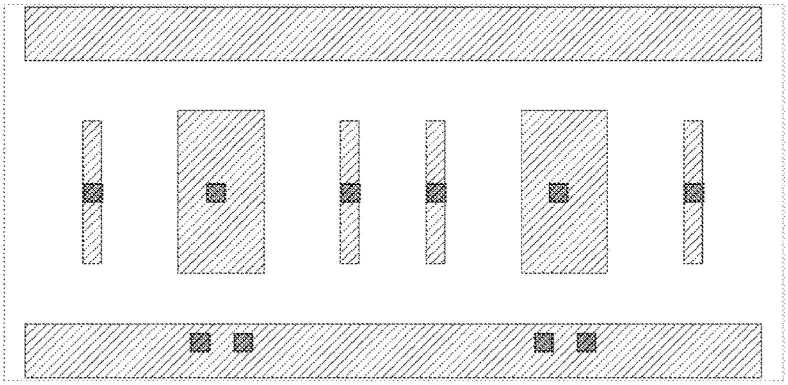
Figure 705A:
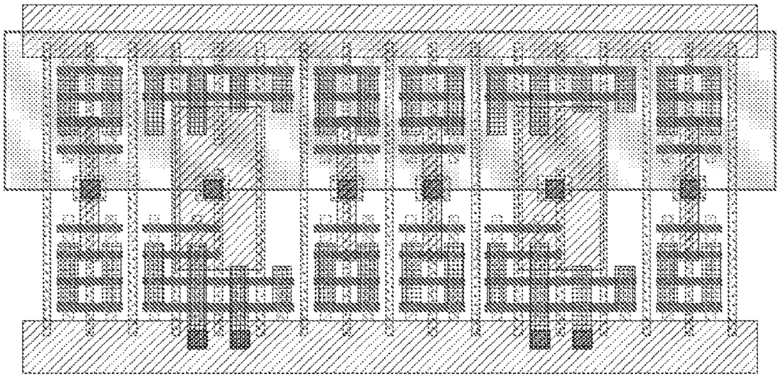
Figure 705B:
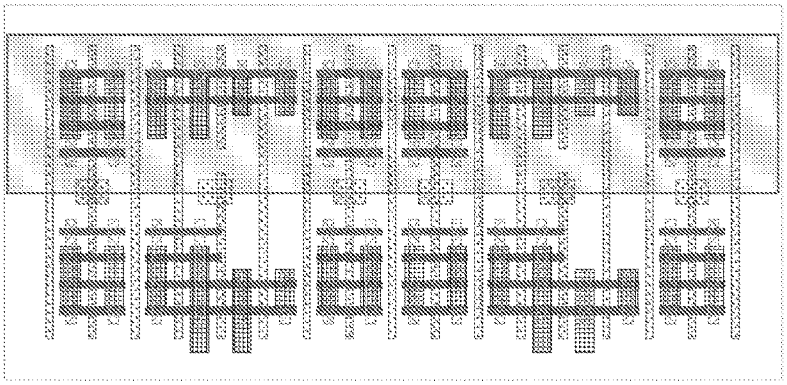
Figure 705C:
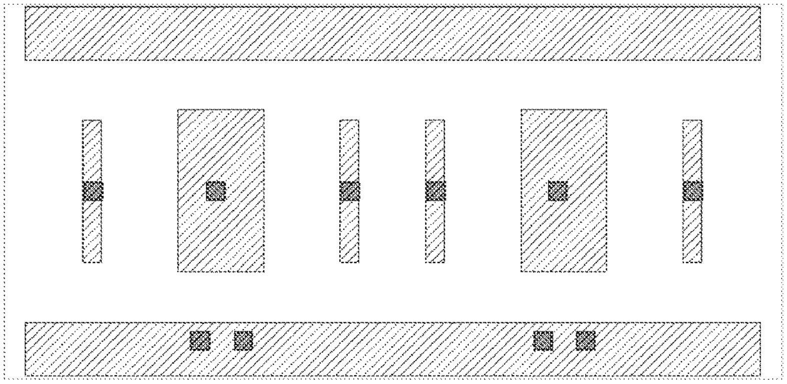
Figure 706A:
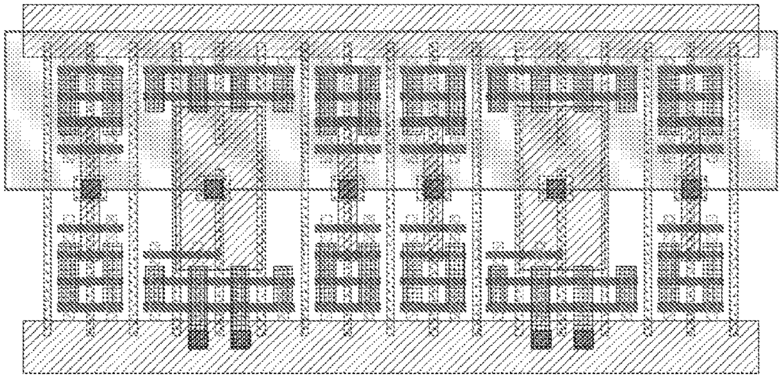
Figure 706B:
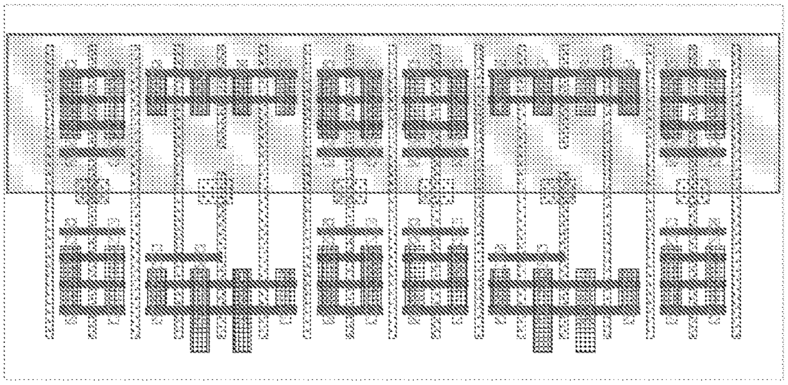
Figure 706C:
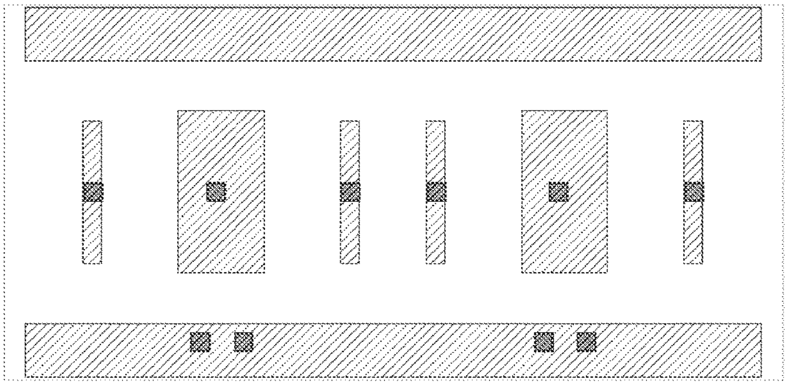
Figure 707A:
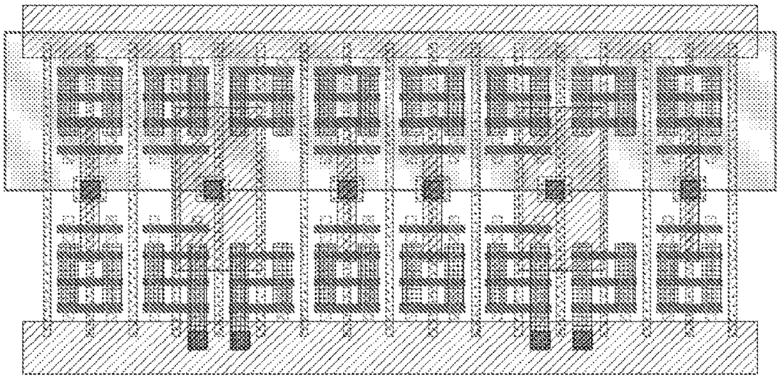
Figure 707B:
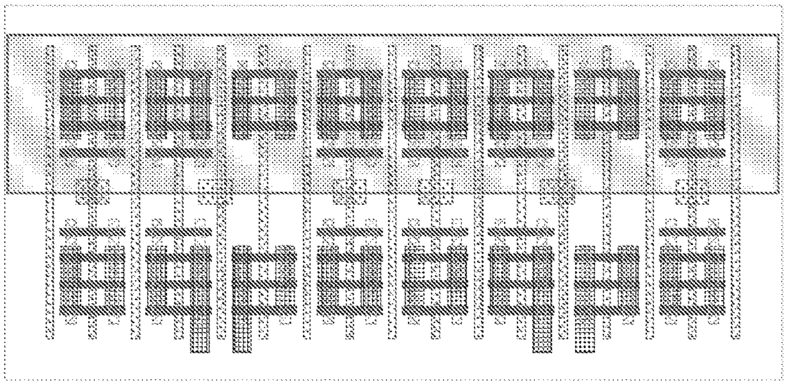
Figure 707C:
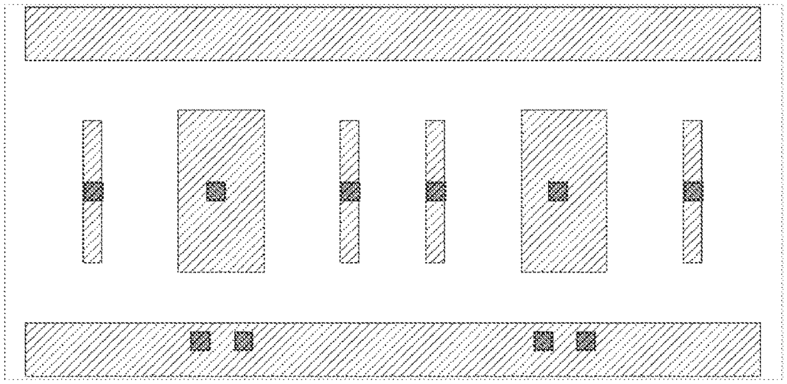
Figure 708A:
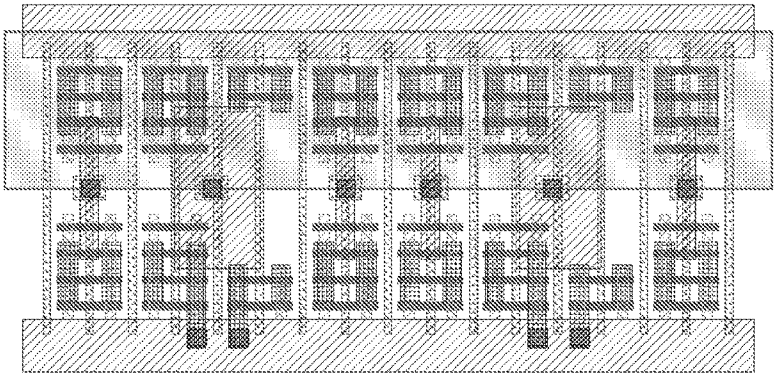
Figure 708B:
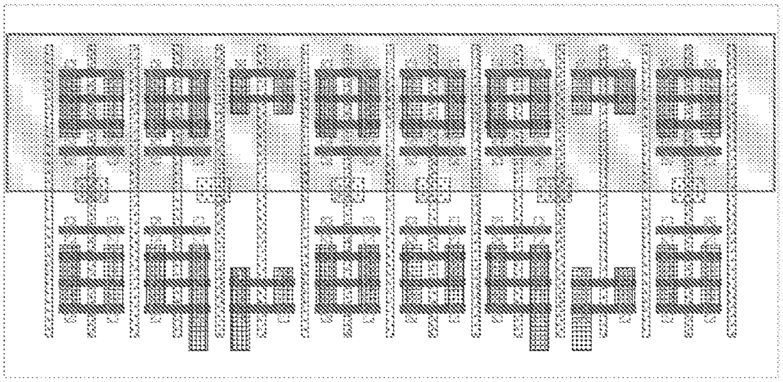
Figure 708C:
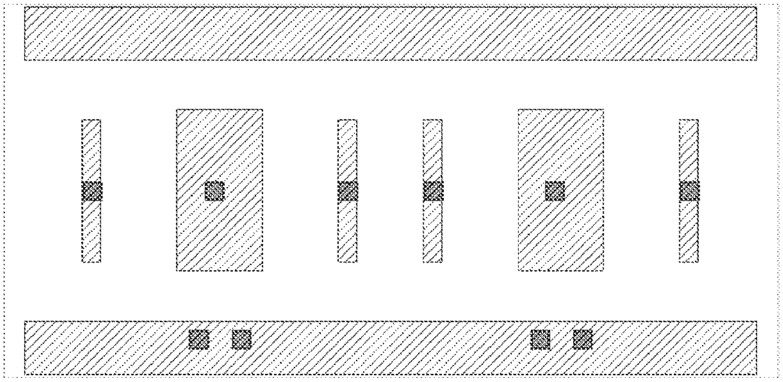
Figure 709A:
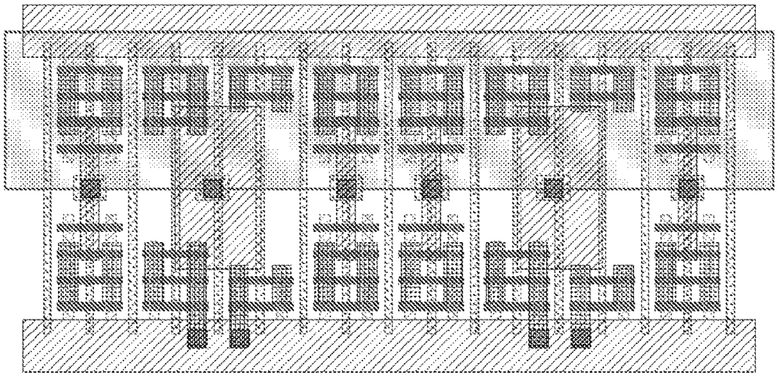
Figure 709B:
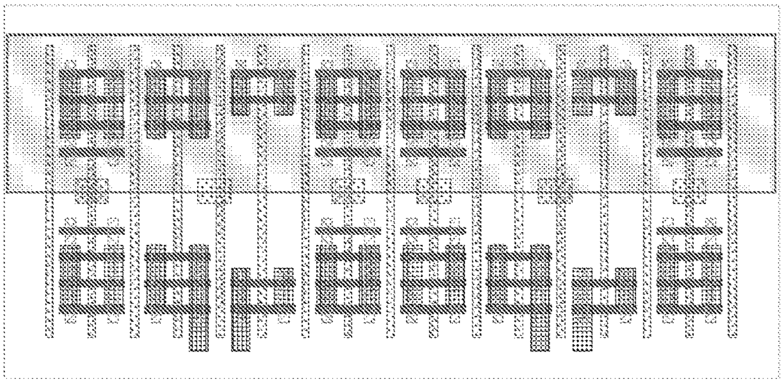
Figure 709C:
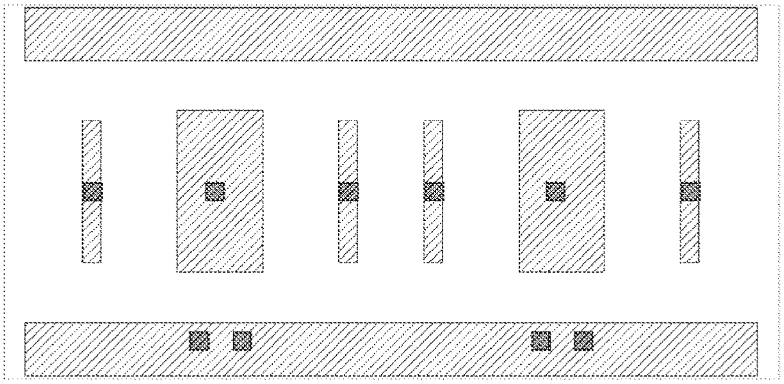
Figure 710A:
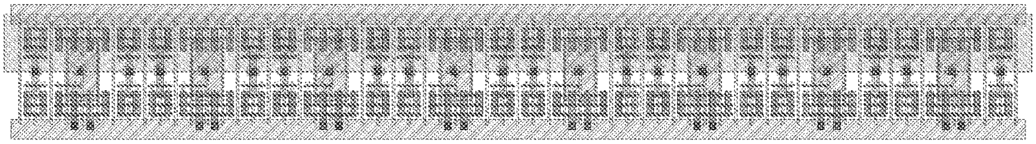
Figure 710B:
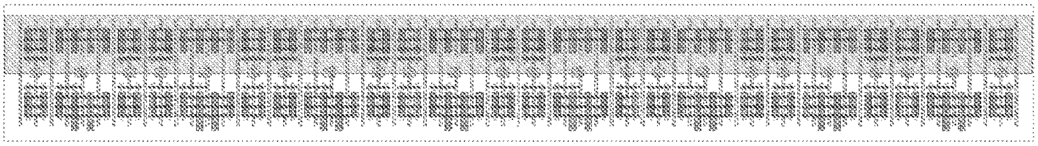
Figure 710C:
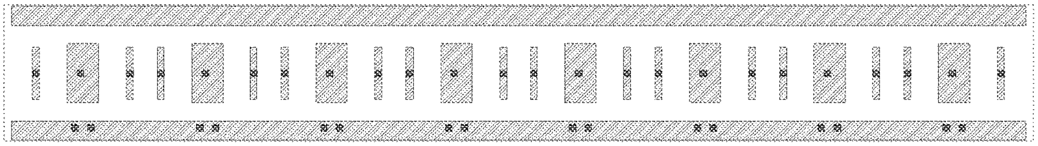
Figure 711A:
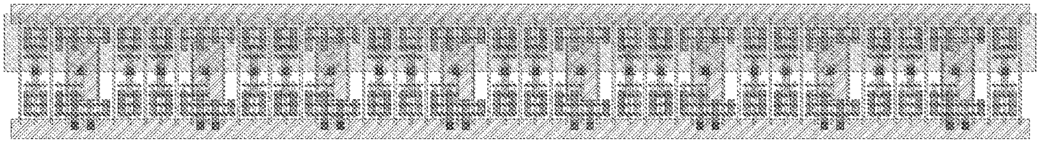
Figure 711B:
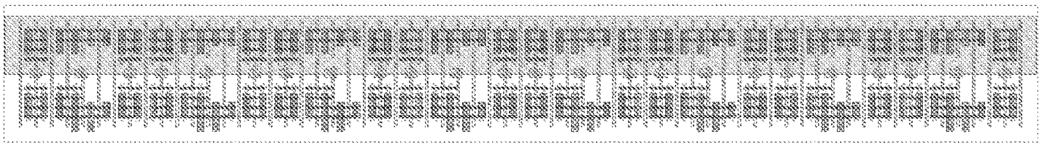
Figure 711C:
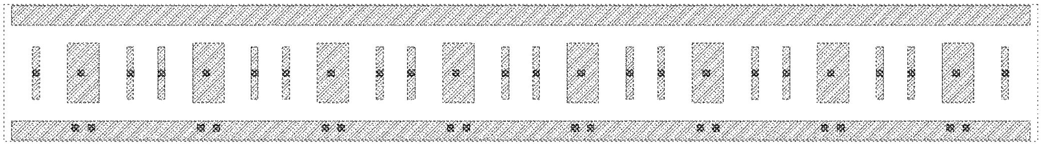
Figure 712A:
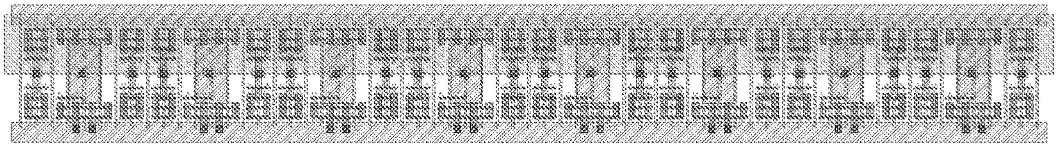
Figure 712B:
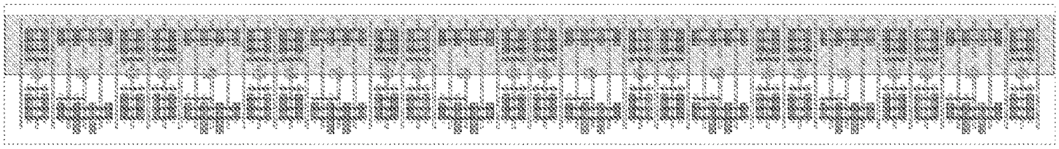
Figure 712C:
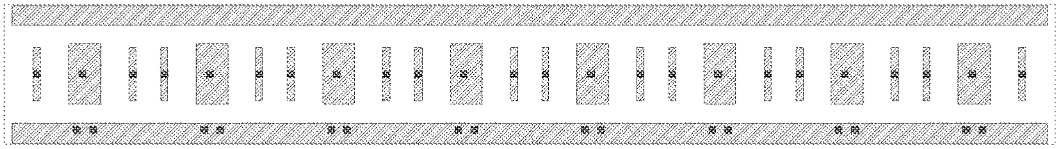
Figure 713A:
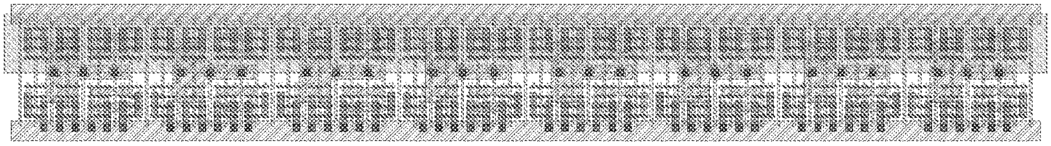
Figure 713B:
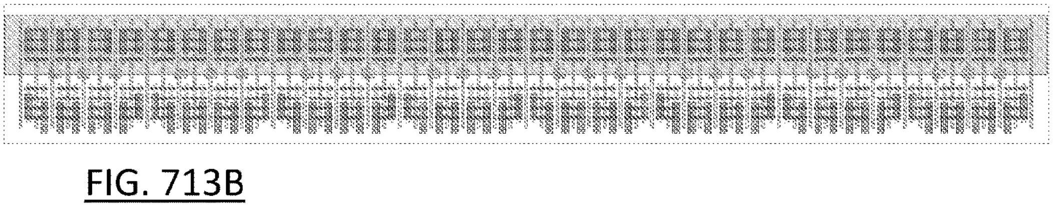
Figure 713C:
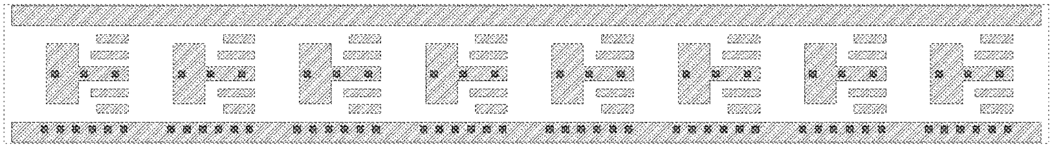
Figure 714A:
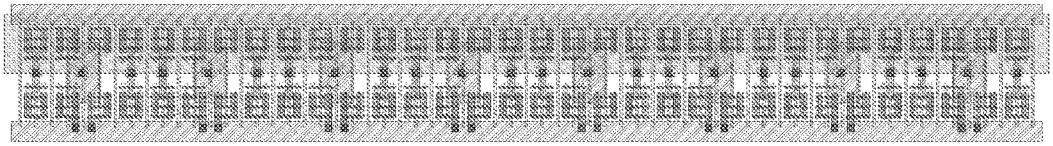
Figure 714B:
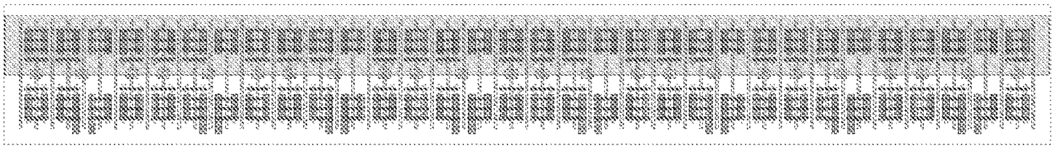
Figure 714C:
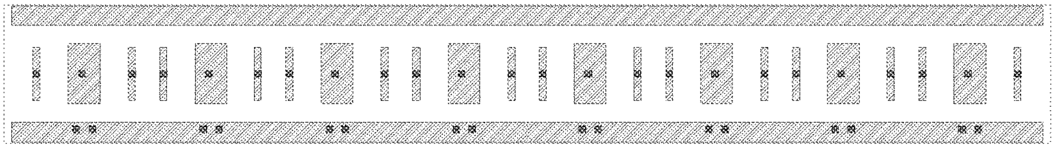
Figure 715A:
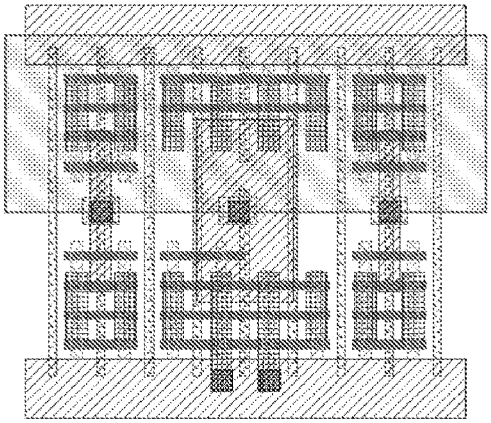
Figure 715B:
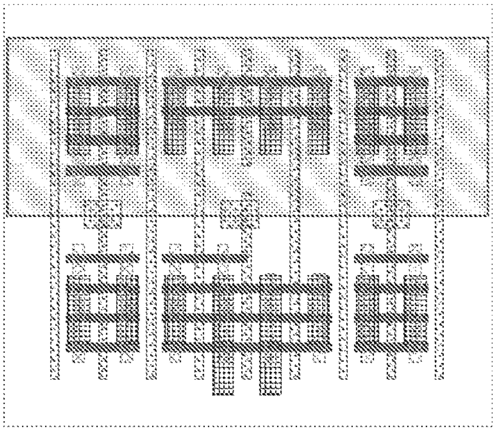
Figure 715C:
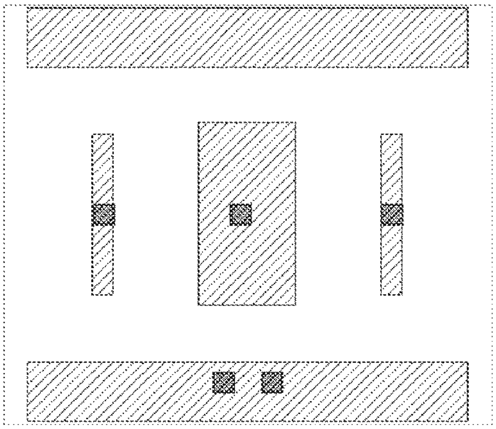
Figure 716A:
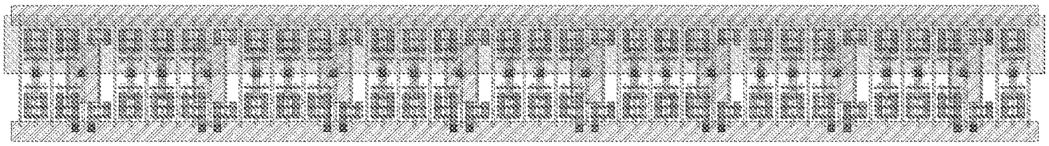
Figure 716B:
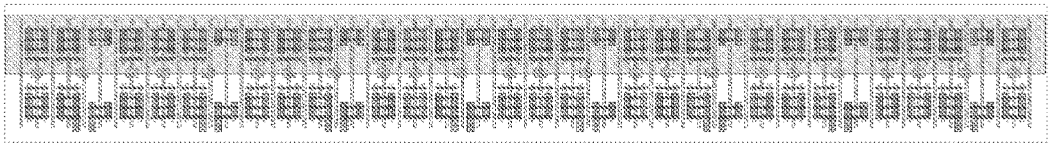
Figure 716C:
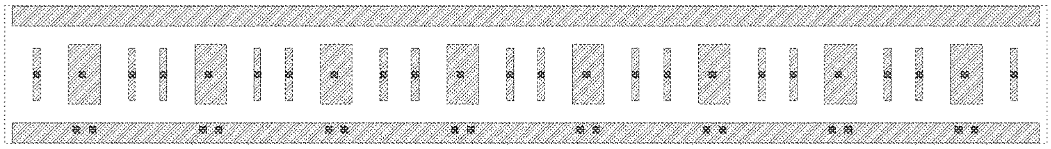
Figure 717A:
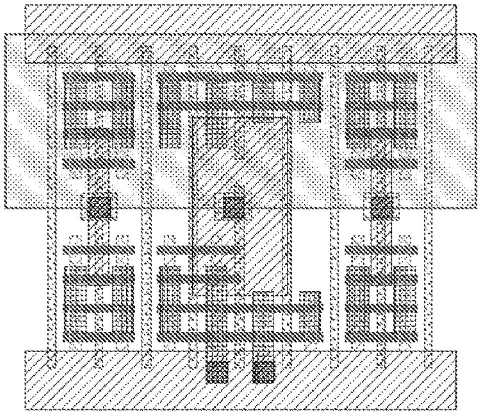
Figure 717B:
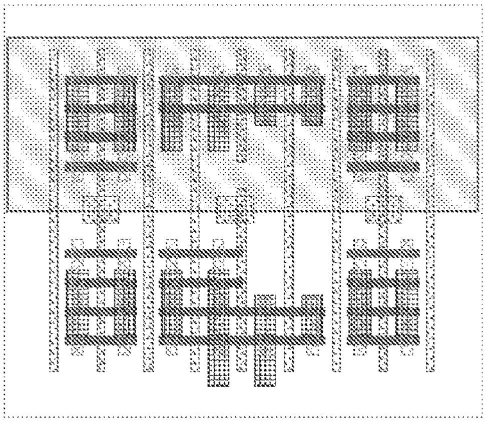
Figure 717C:
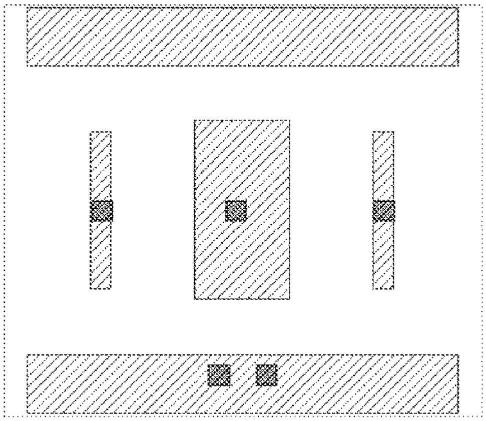
Figure 718A:
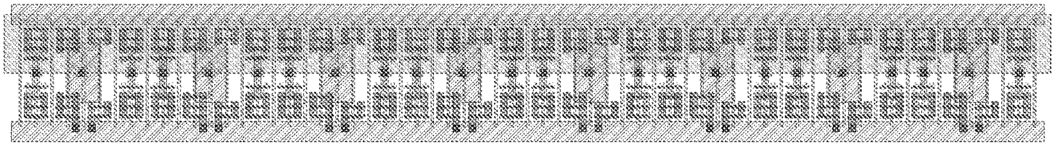
Figure 718B:
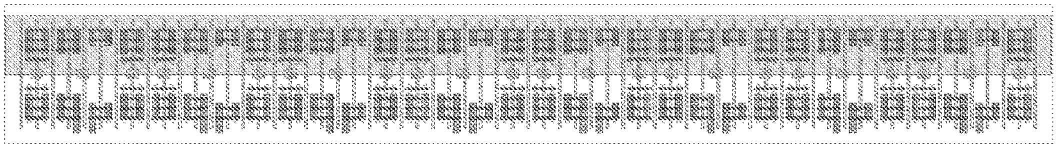
Figure 718C:
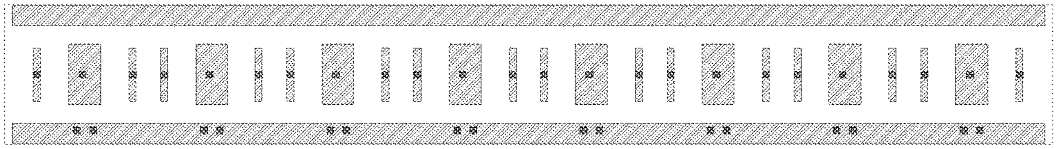
Figure 719A:
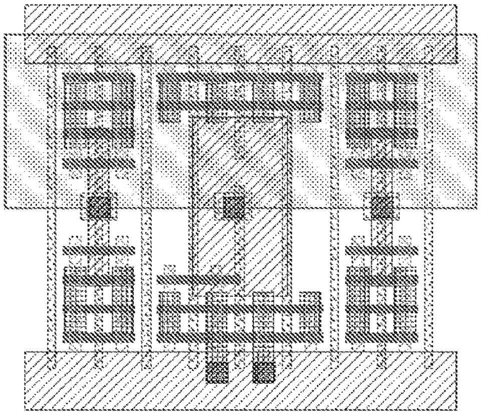
Figure 719B:
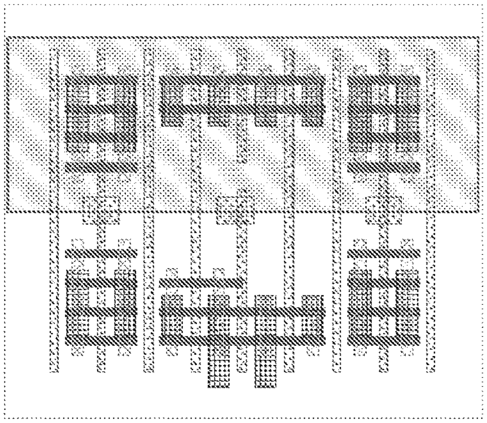
Figure 719C:
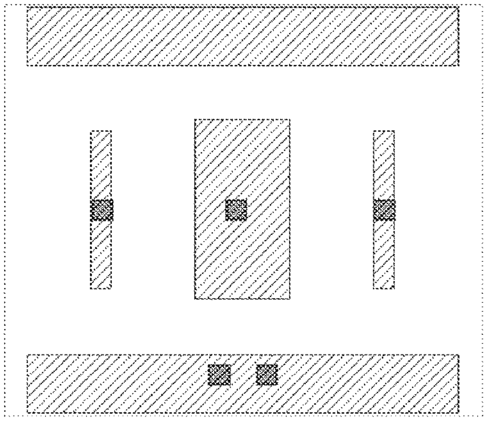
Figure 720A:
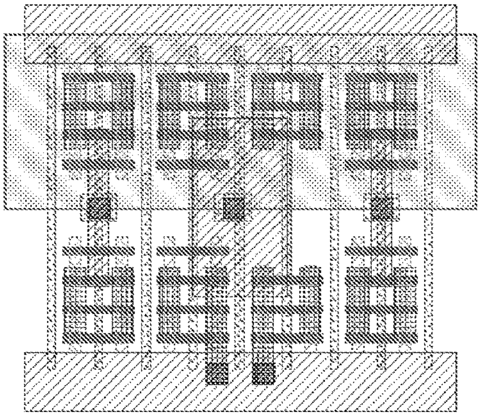
Figure 720B:
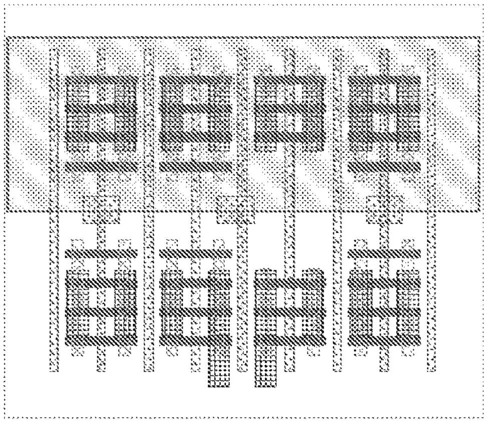
Figure 720C:
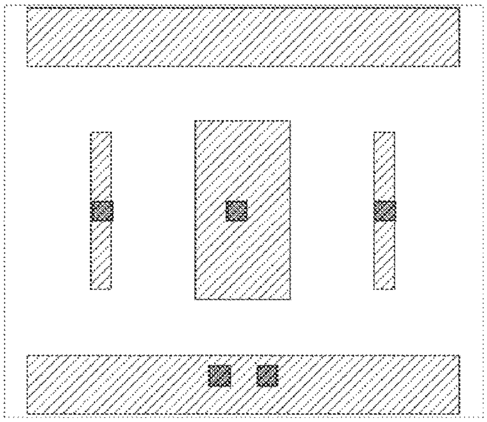
Figure 721A:
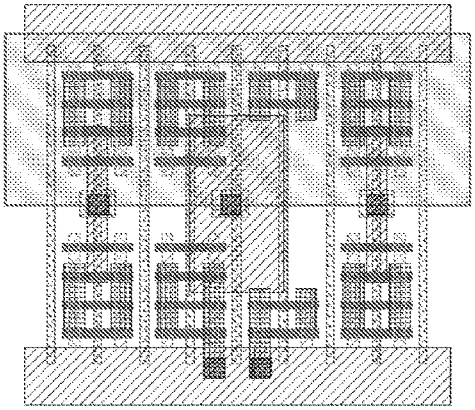
Figure 721B:
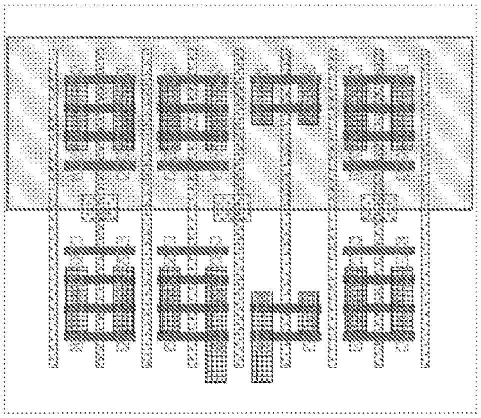
Figure 721C:
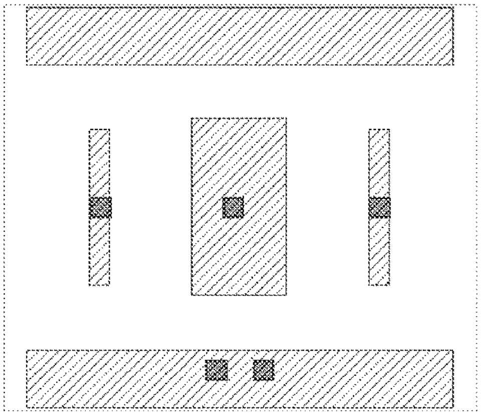
Figure 722A:
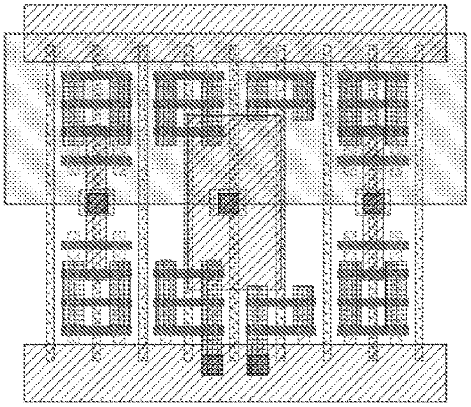
Figure 722B:
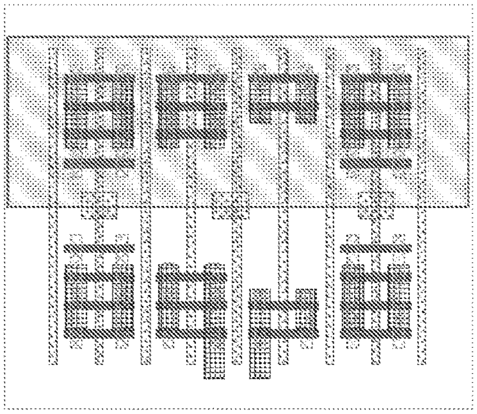
Figure 722C:
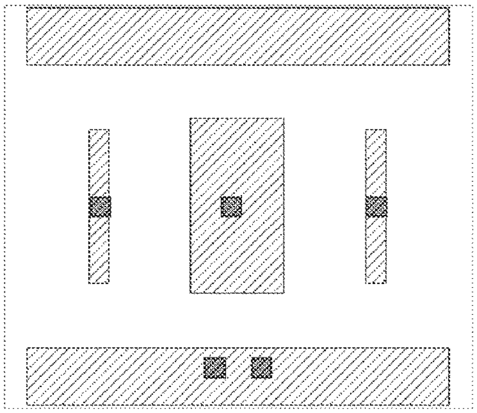
Figure 723A:
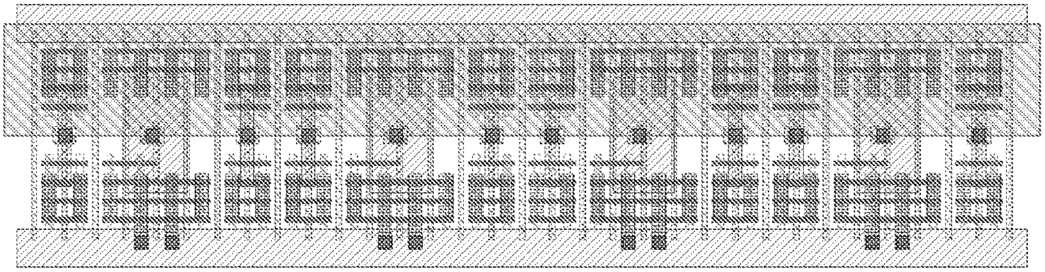
Figure 723B:
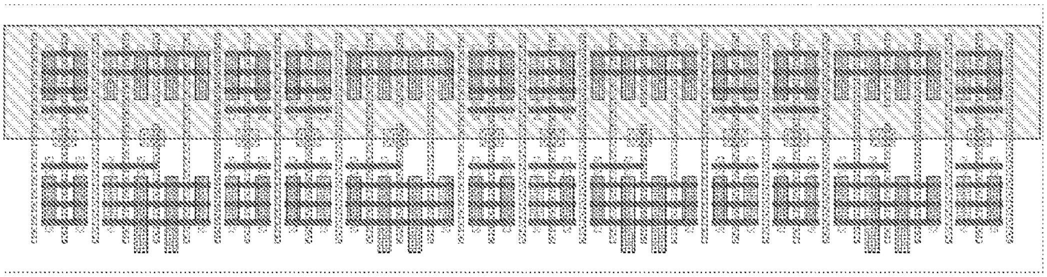
Figure 723C:
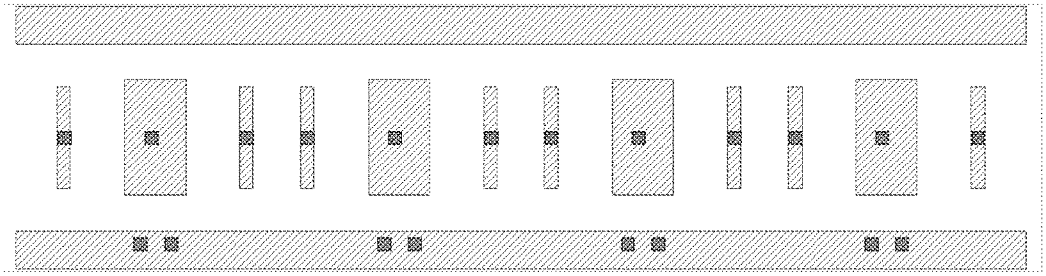
Figure 724A:
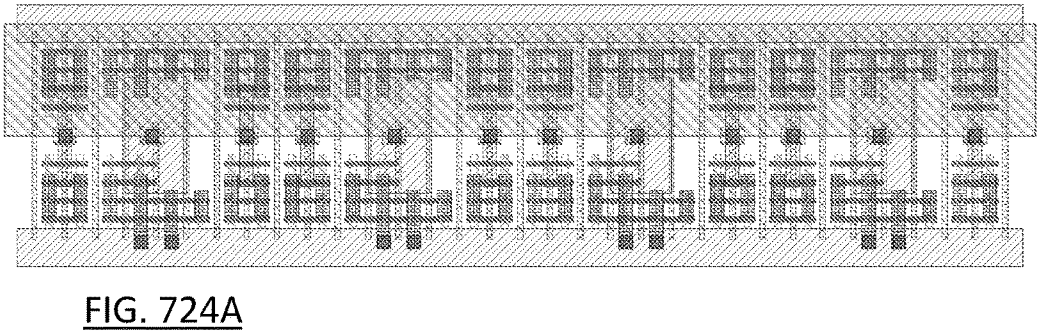
Figure 724B:
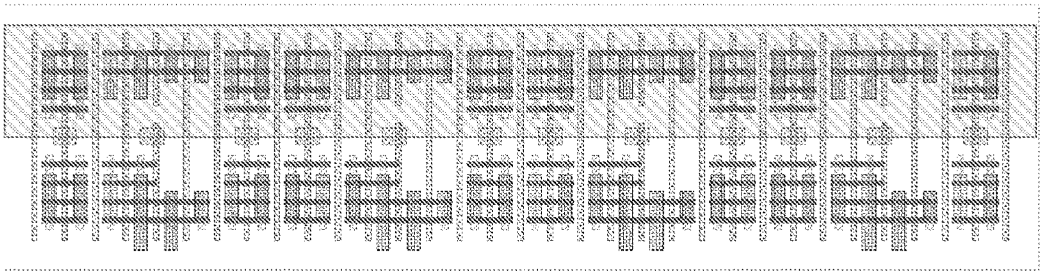
Figure 724C:
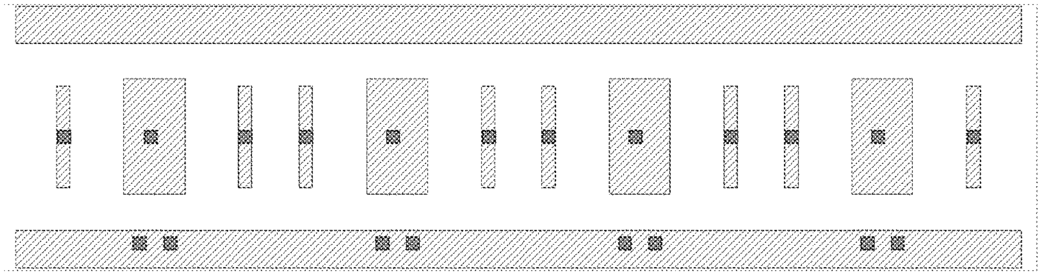
Figure 725A:
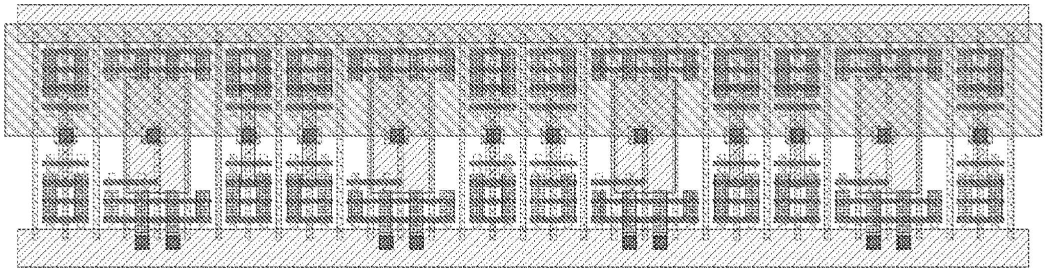
Figure 725B:
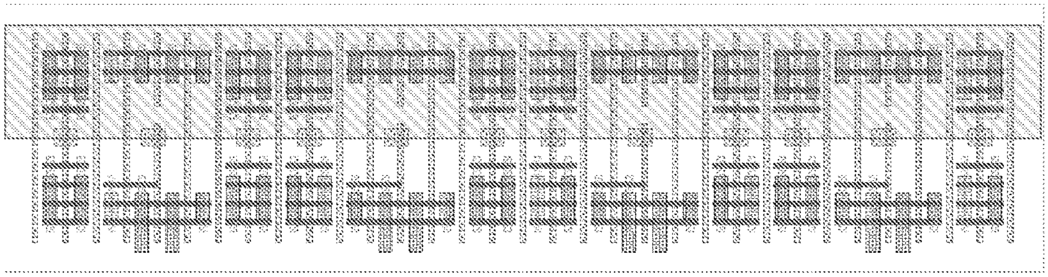
Figure 725C:
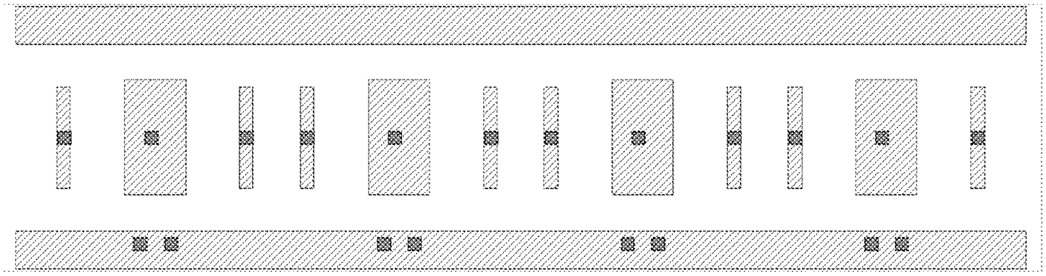
Figure 726A:
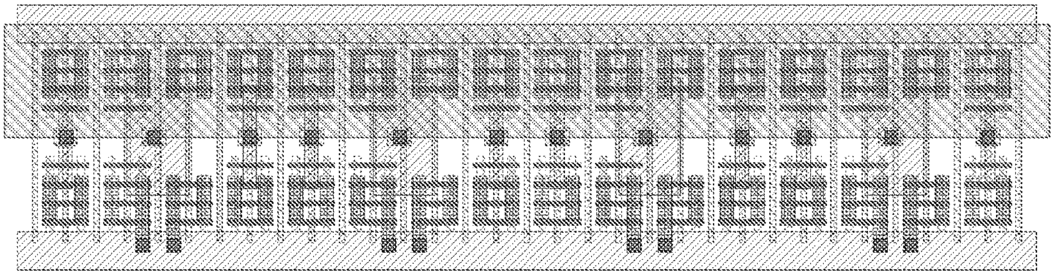
Figure 726B:
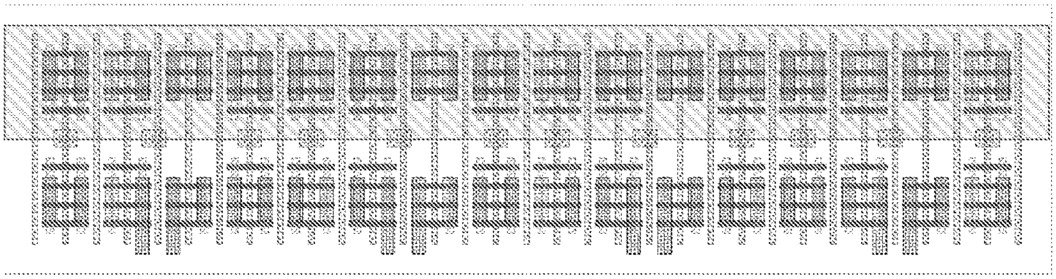
Figure 726C:
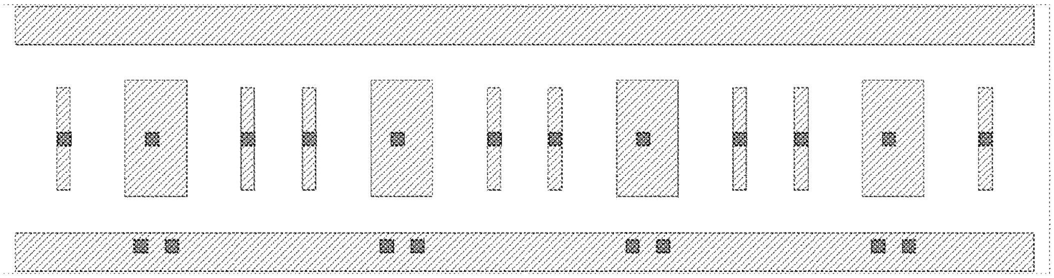
Figure 727A:
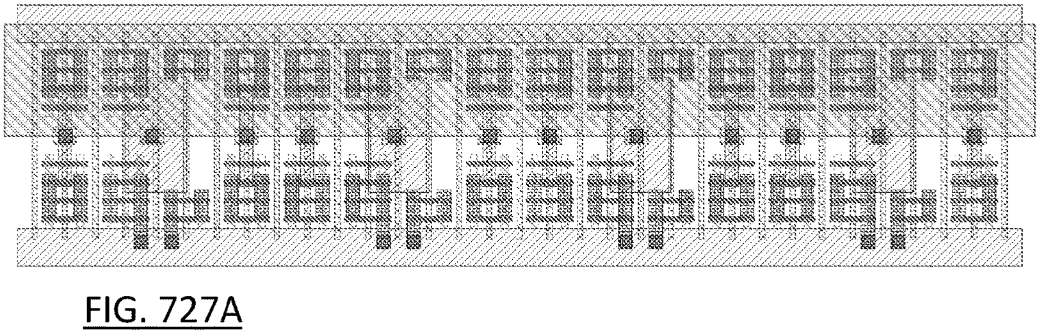
Figure 727B:
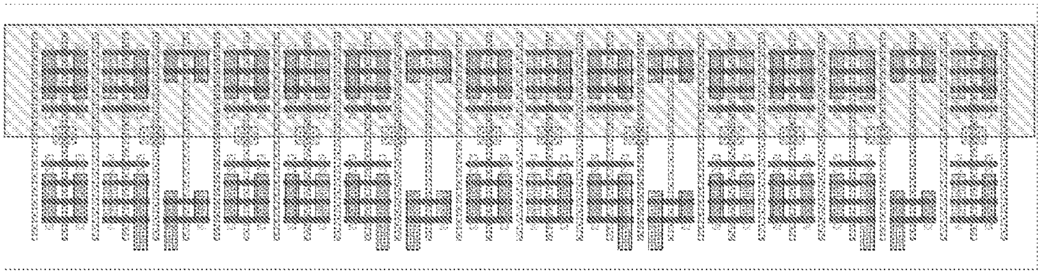
Figure 727C:
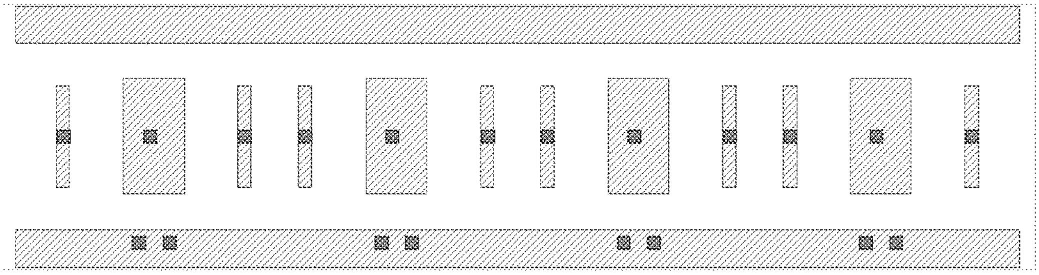
Figure 728A:
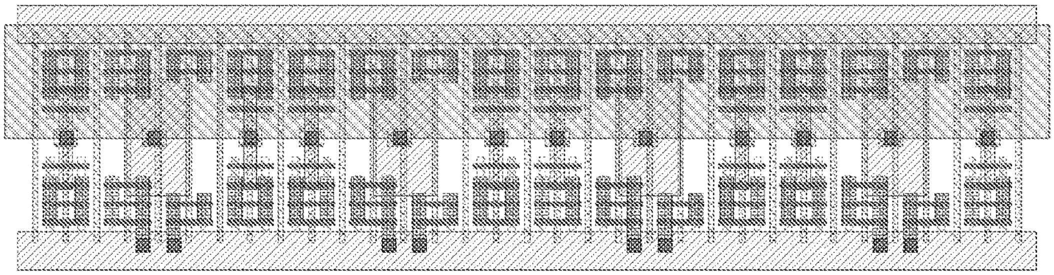
Figure 728B:
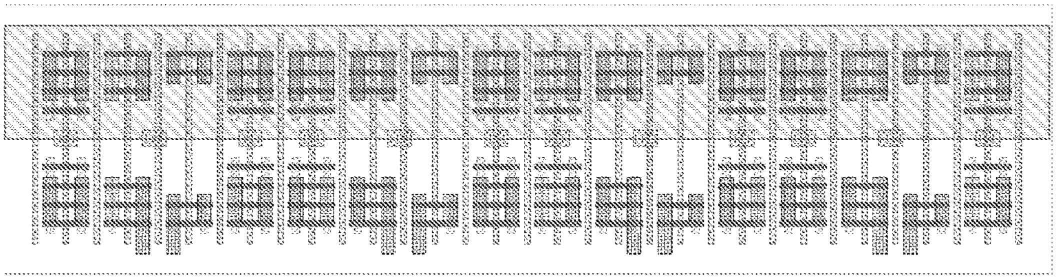
Figure 728C:
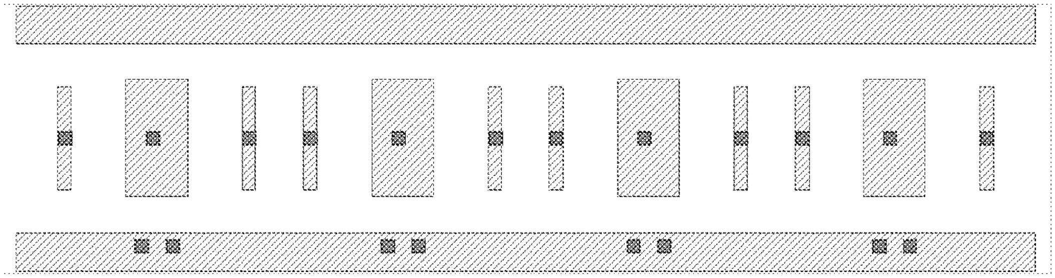
Figure 729A:
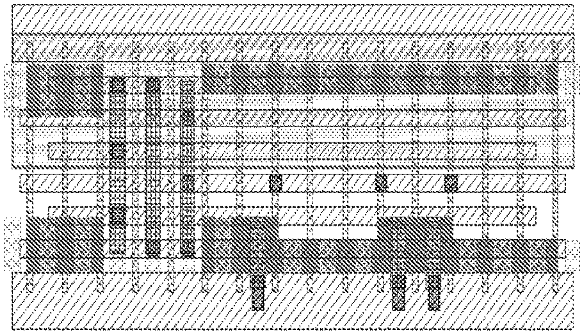
Figure 729B:
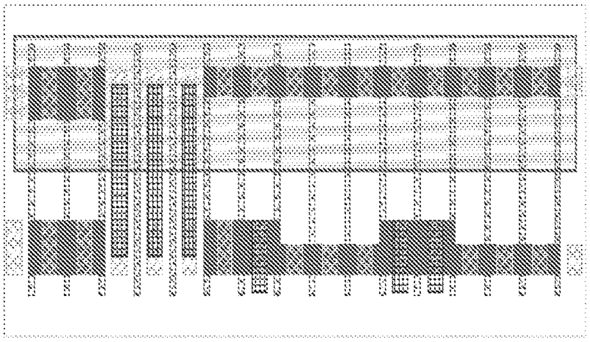
Figure 729C:
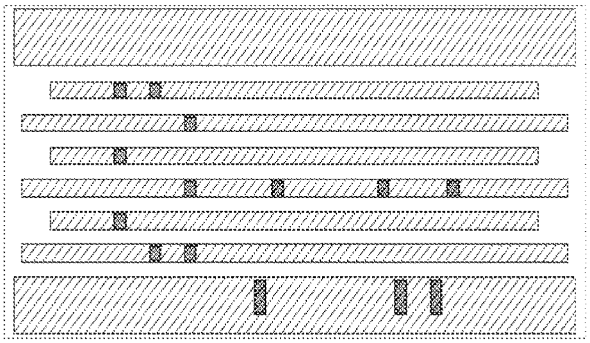
Figure 730A:
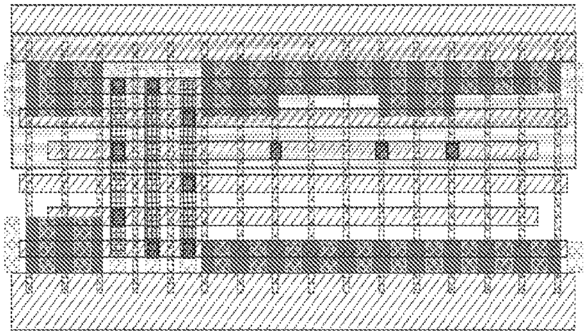
Figure 730B:
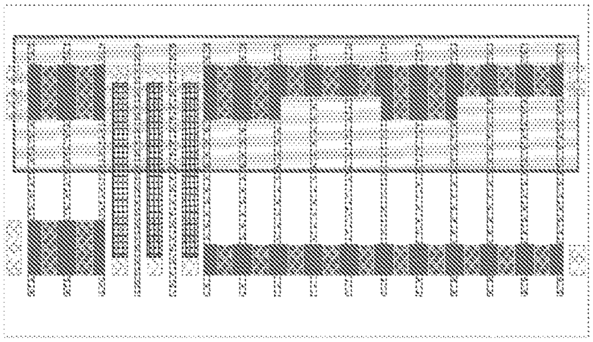
Figure 730C:
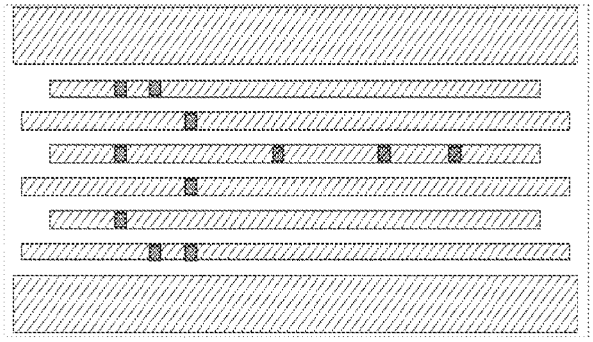
Figure 731A:
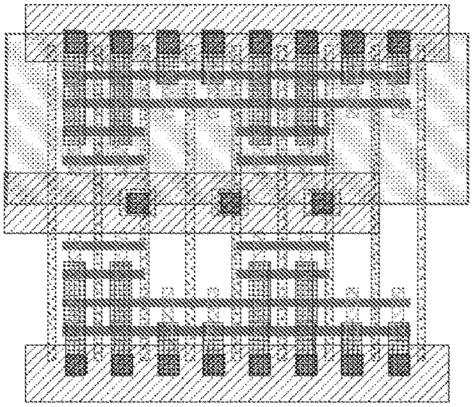
Figure 731B:
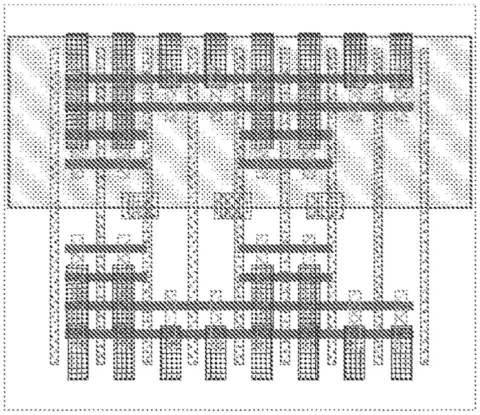
Figure 731C:
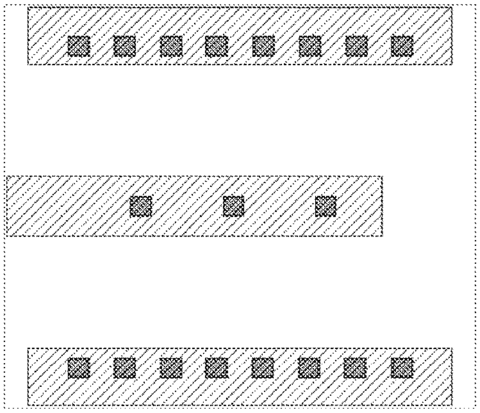
Figure 732A:
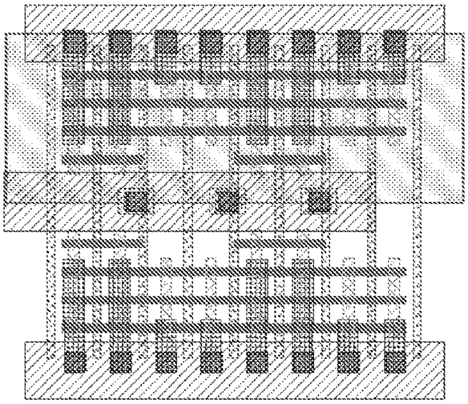
Figure 732B:
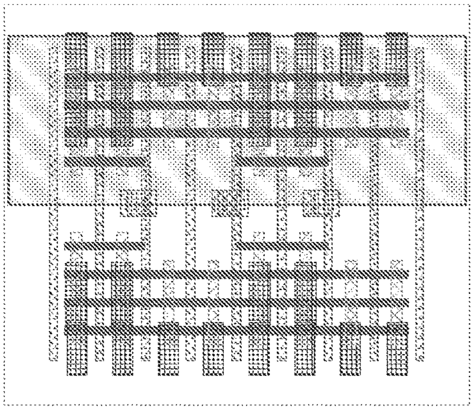
Figure 732C:
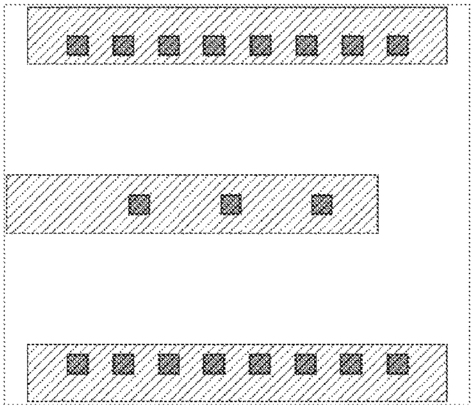
Figure 733A:
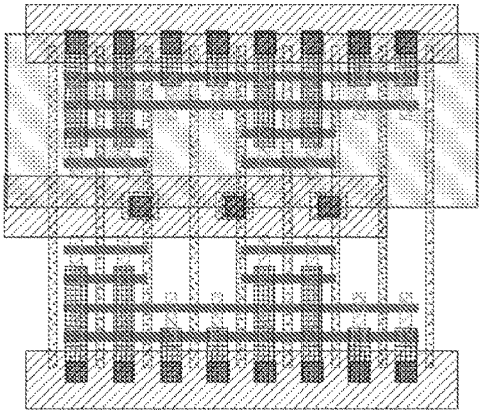
Figure 733B:
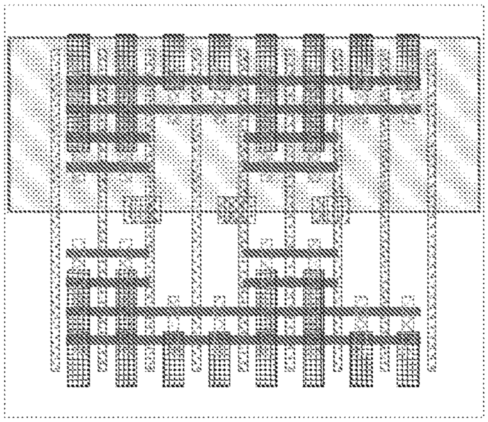
Figure 733C:
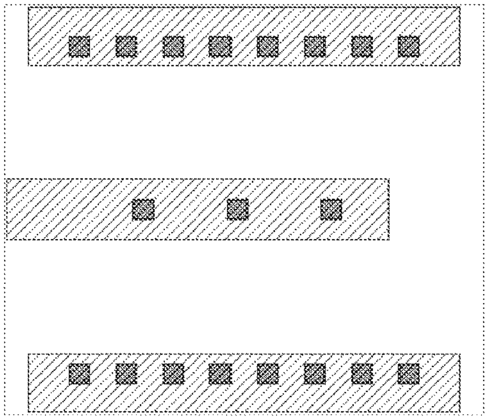
Figure 734A:
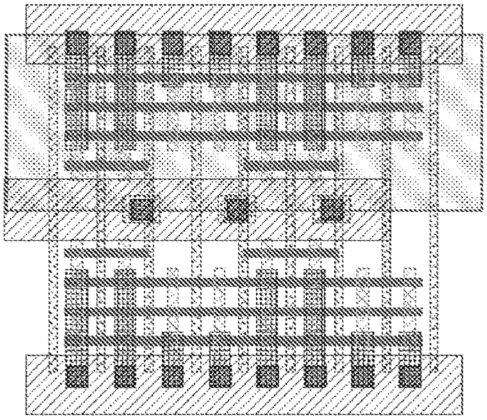
Figure 734B:
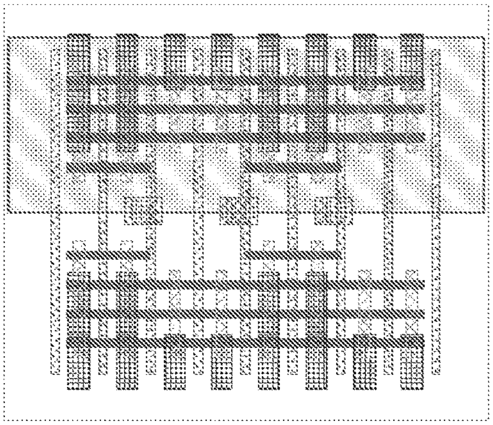
Figure 734C:
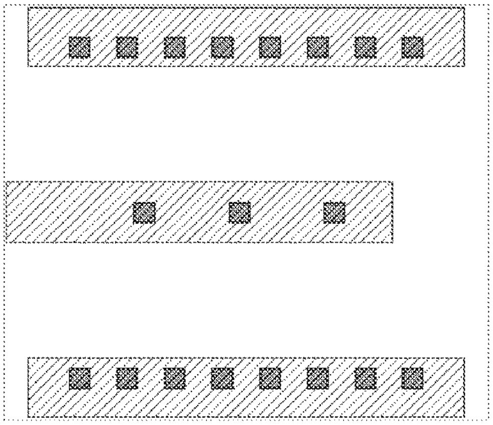
Figure 735A:
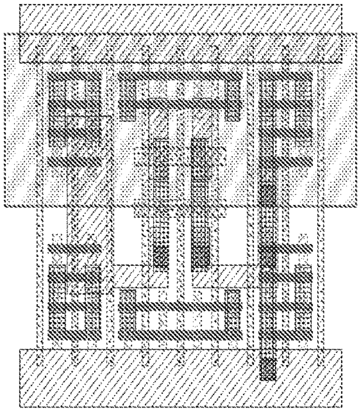
Figure 735B:
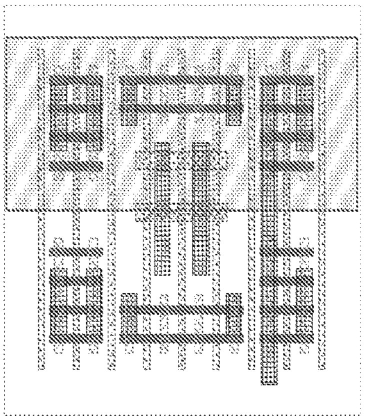
Figure 735C:
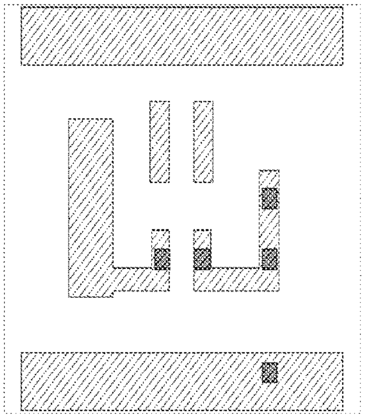
Figure 736A:
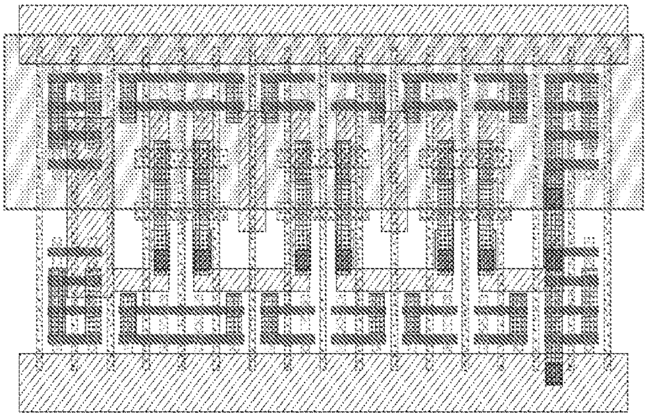
Figure 736B:
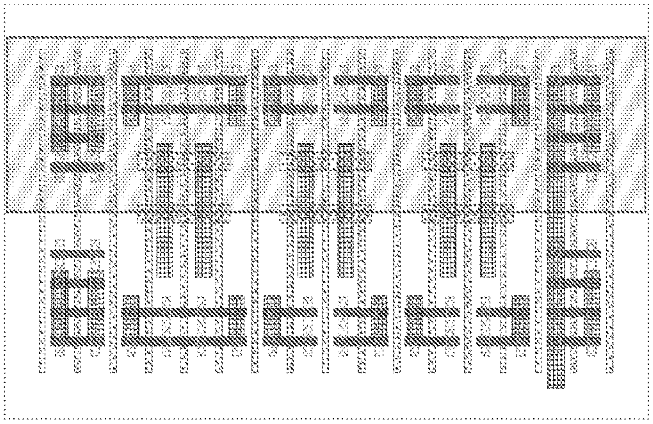
Figure 736C:
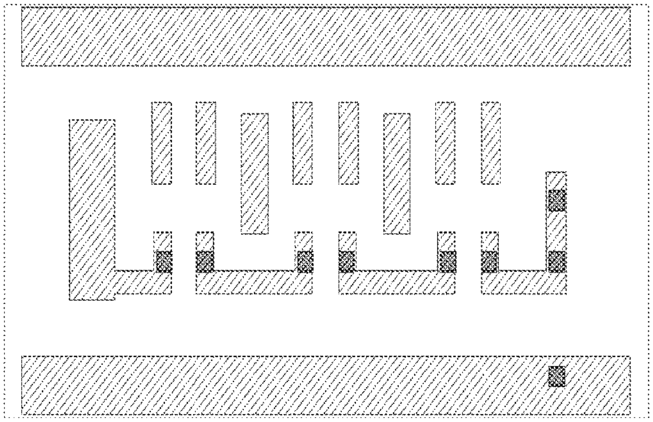
Figure 737A:
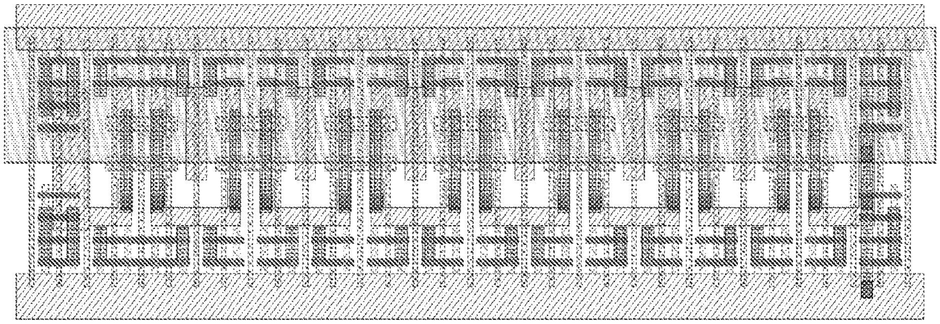
Figure 737B:
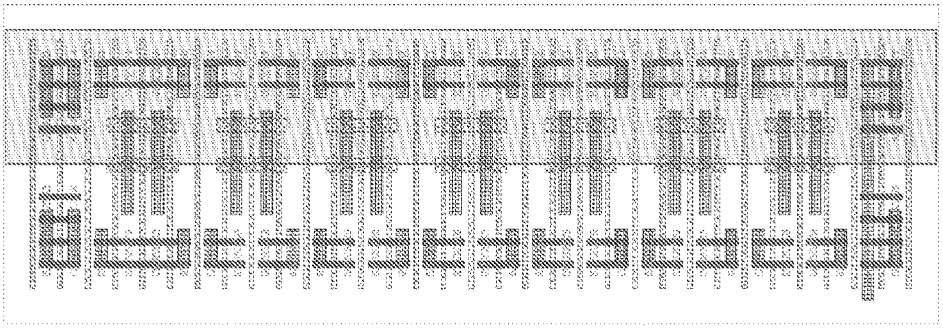
Figure 737C:
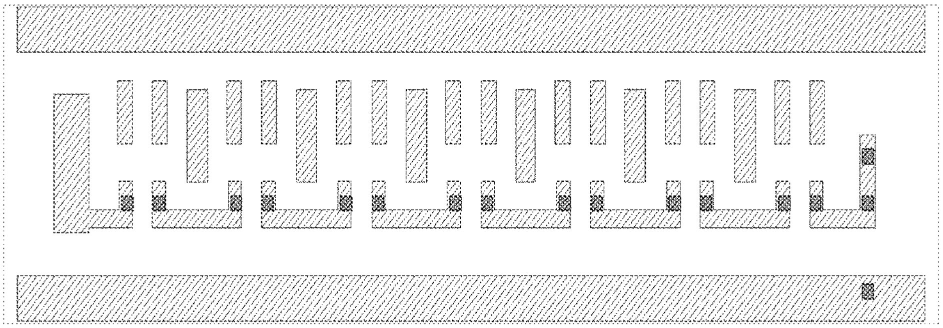
Figure 738A:
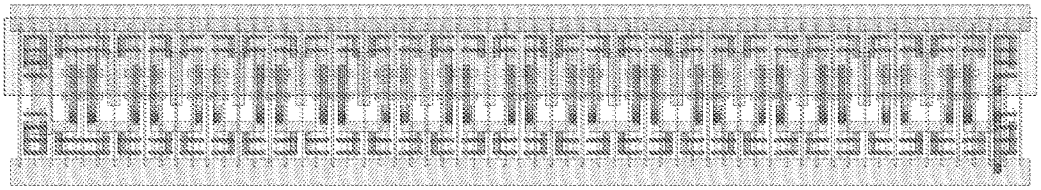
Figure 738B:
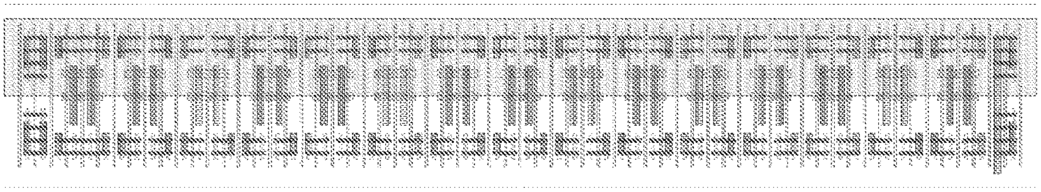
Figure 738C:
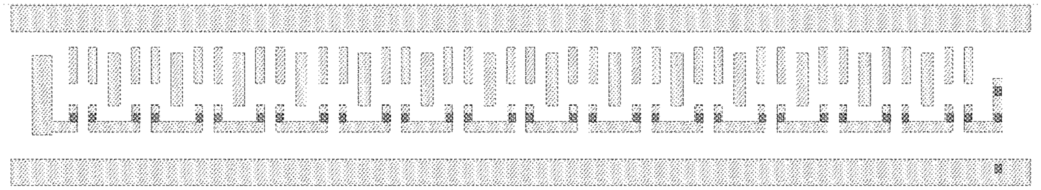
Figure 739A:
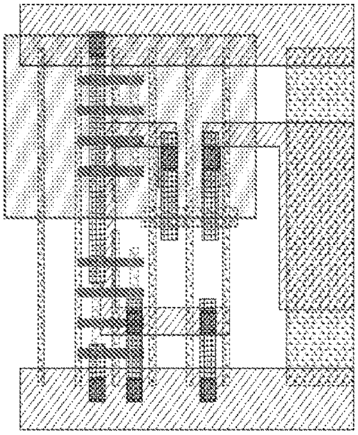
Figure 739B:
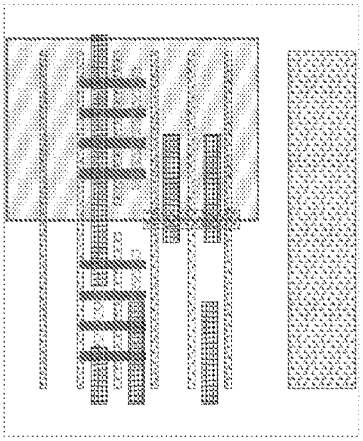
Figure 739C:
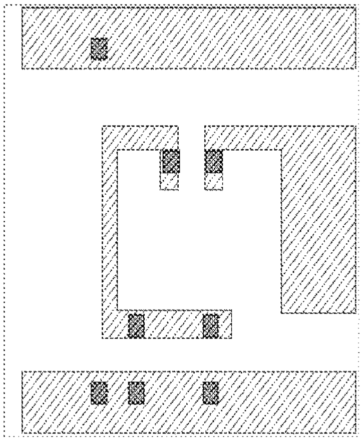
Figure 740A:
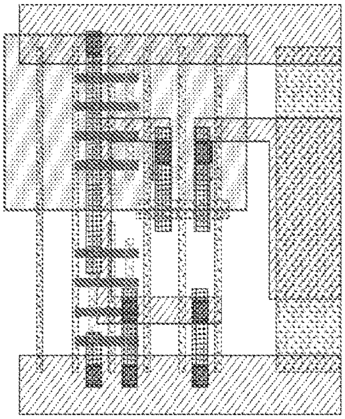
Figure 740B:
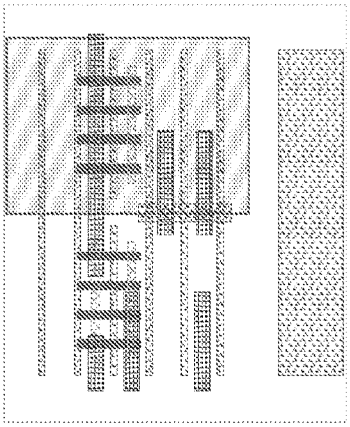
Figure 740C:
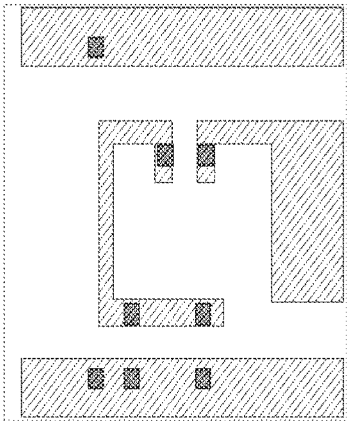
Figure 741A:
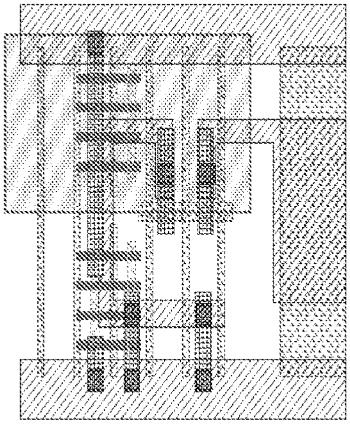
Figure 741B:
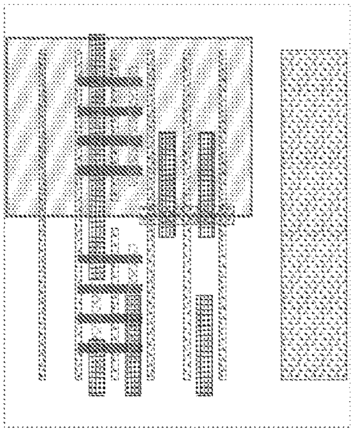
Figure 741C:
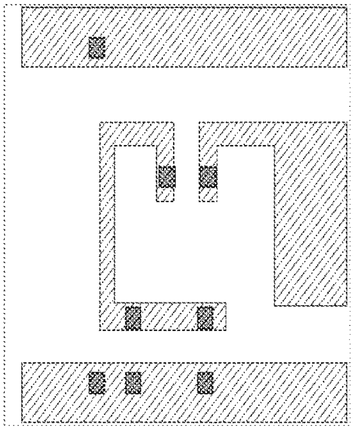
Figure 742A:
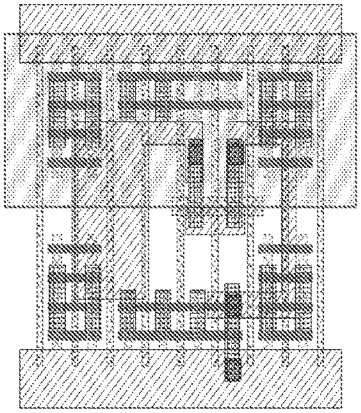
Figure 742B:
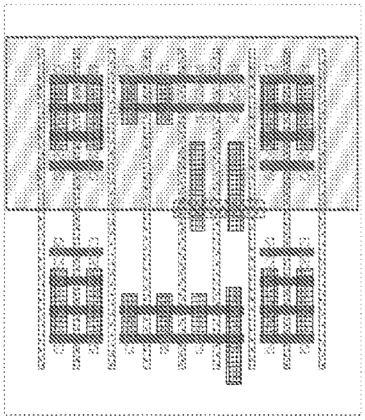
Figure 742C:
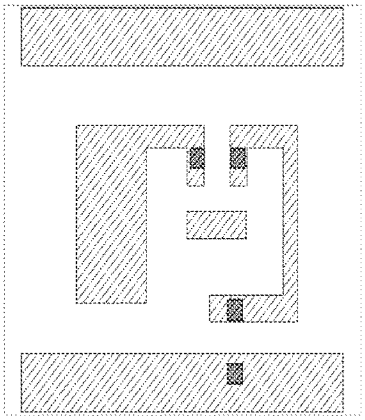
Figure 743A:
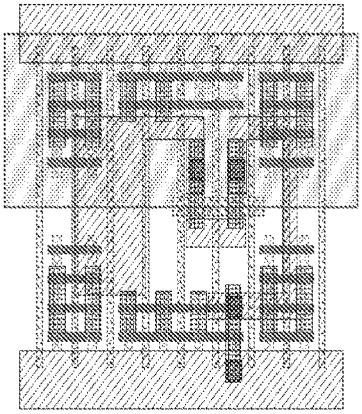
Figure 743B:
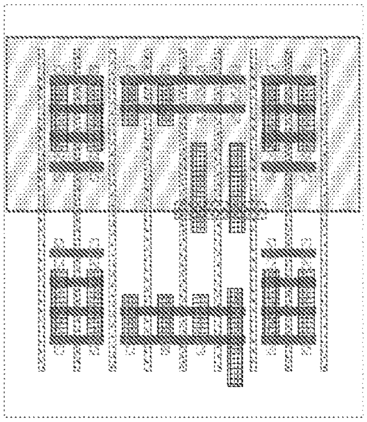
Figure 743C:
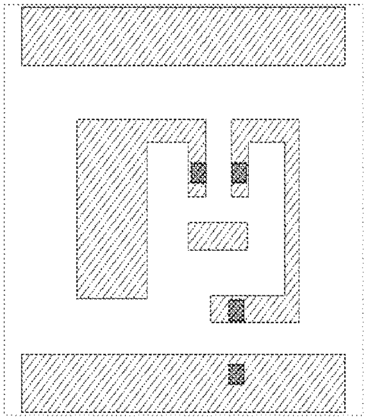
Figure 744A:
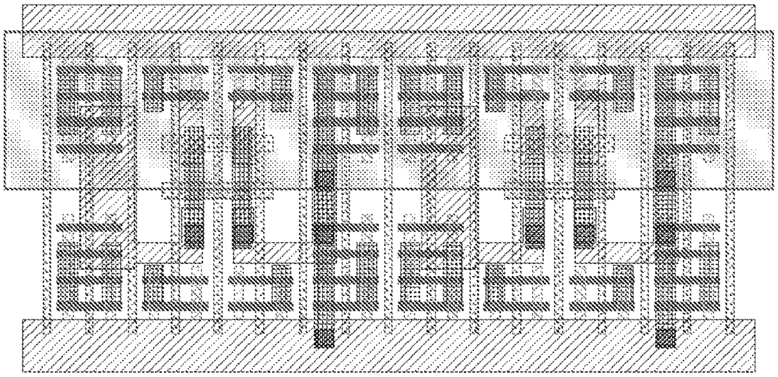
Figure 744B:
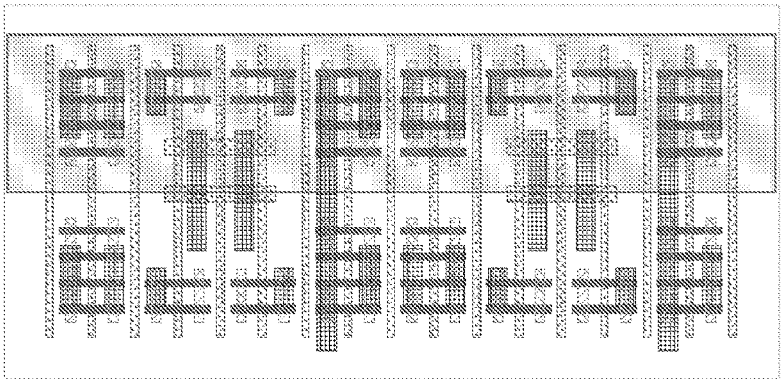
Figure 744C:
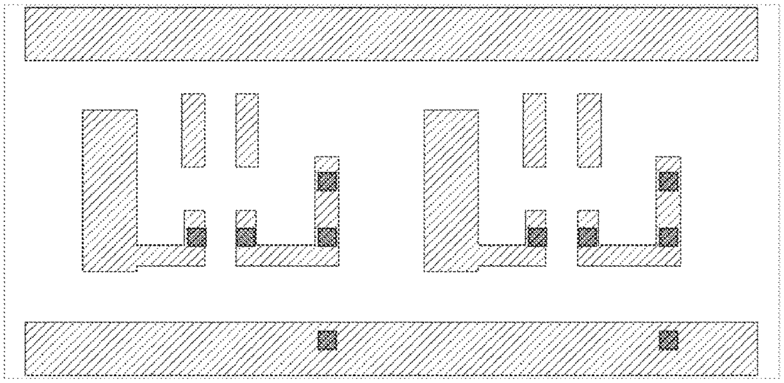
Figure 745A:
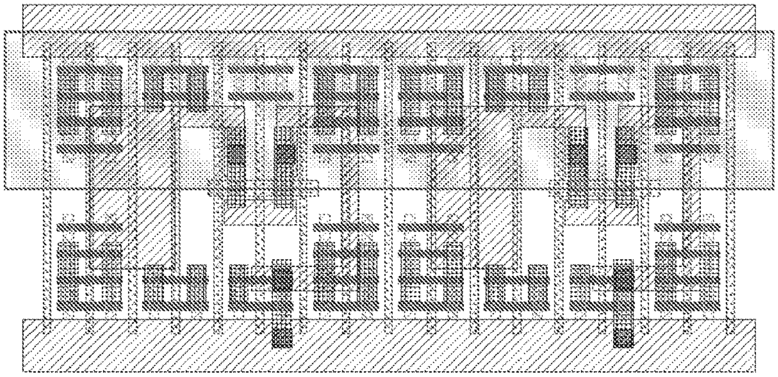
Figure 745B:
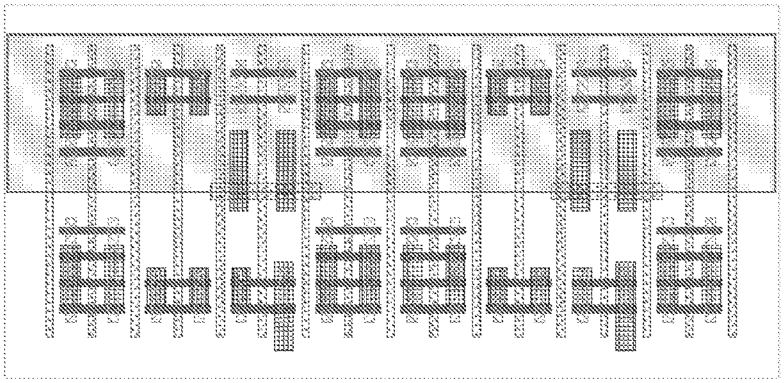
Figure 745C:
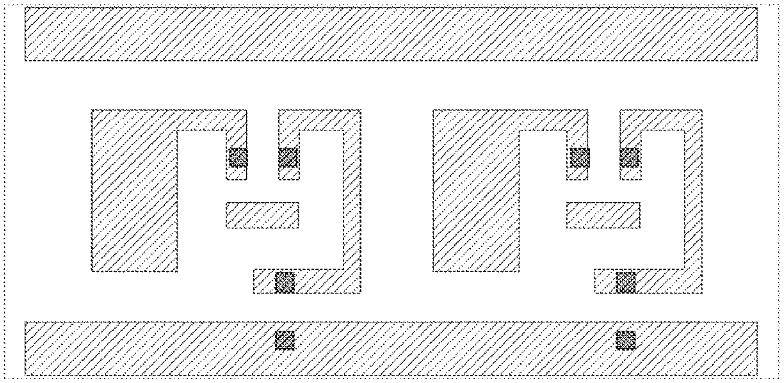
Figure 746A:
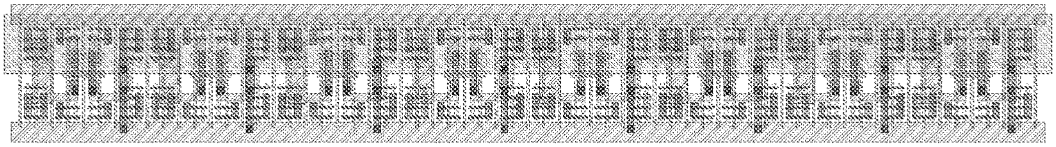
Figure 746B:
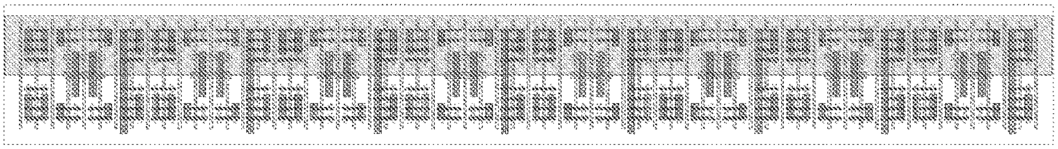
Figure 746C:
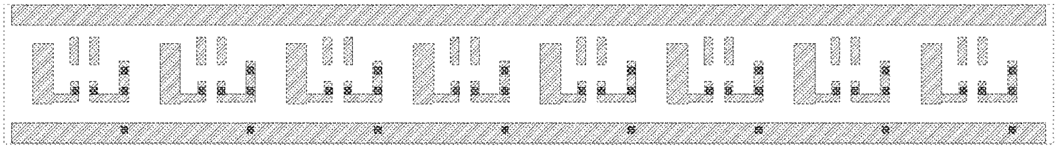
Figure 747A:
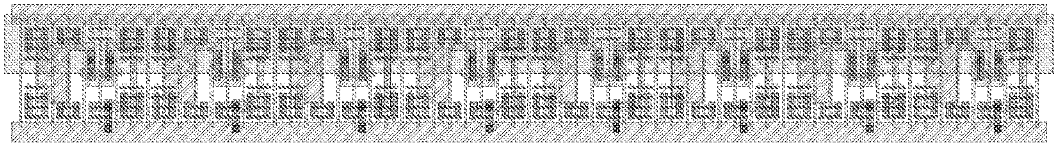
Figure 747B:
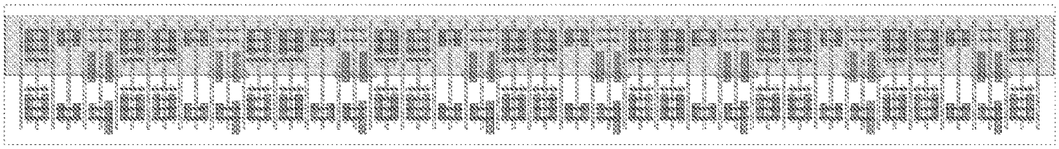
Figure 747C:
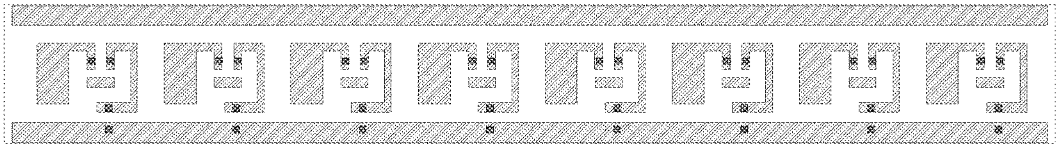
Figure 748A:
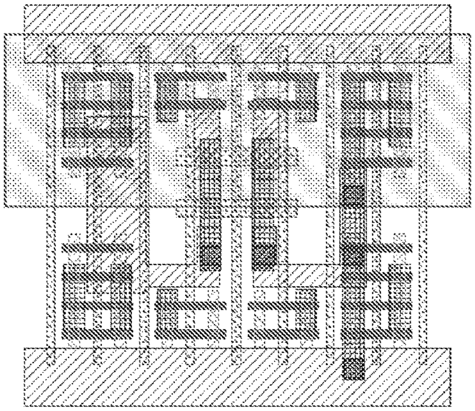
Figure 748B:
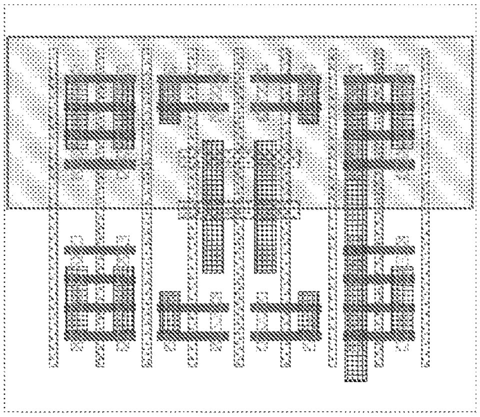
Figure 748C:
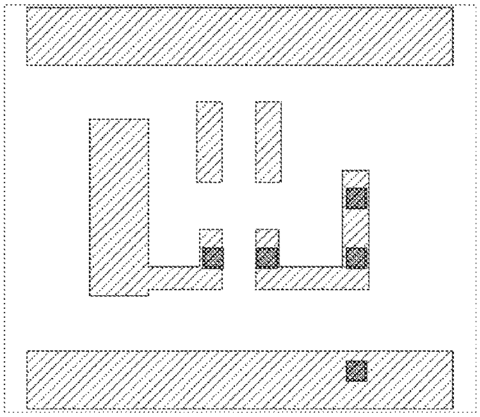
Figure 749A:
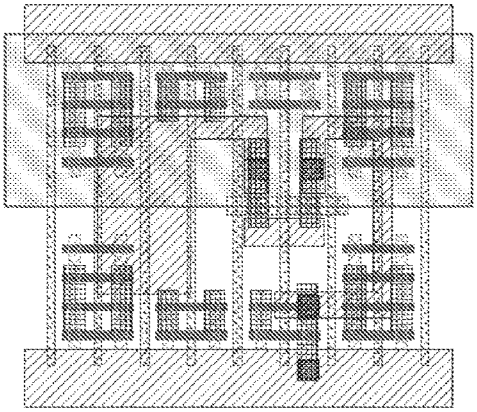
Figure 749B:
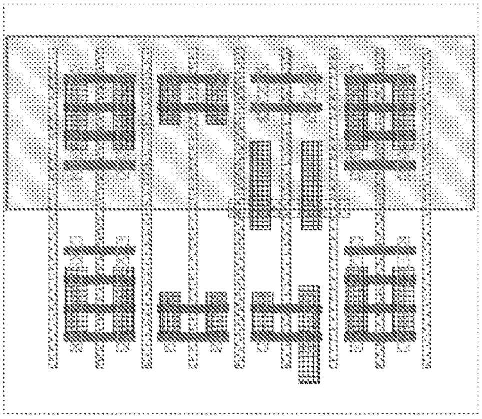
Figure 749C:
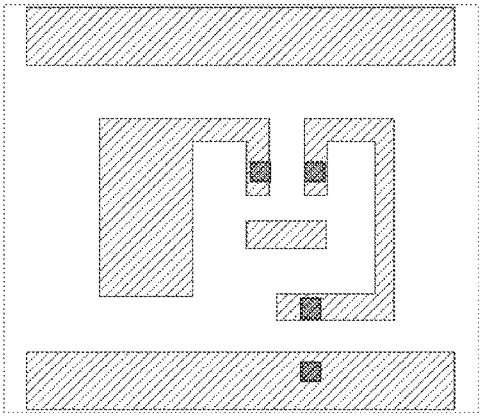
Figure 750A:
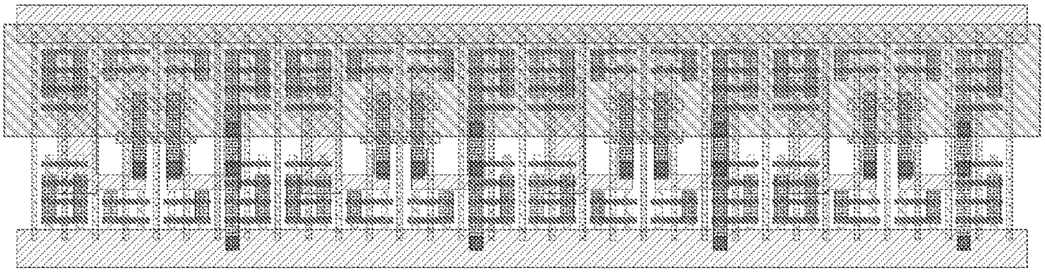
Figure 750B:
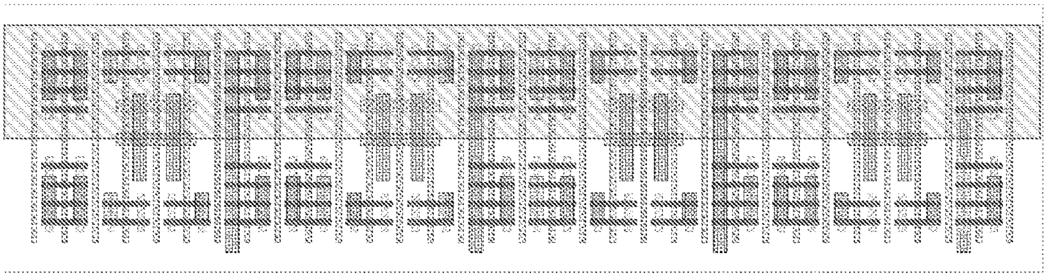
Figure 750C:
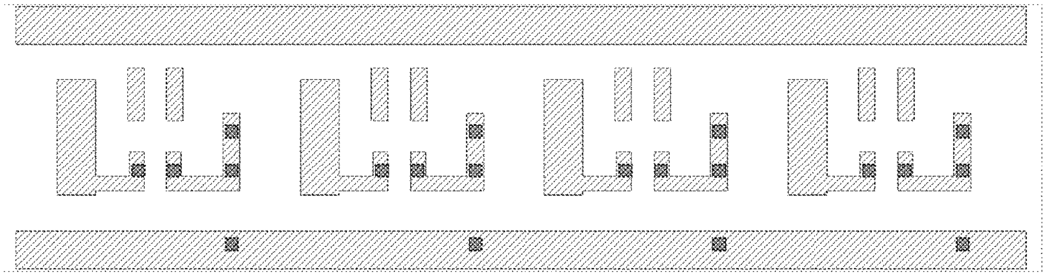
Figure 751A:
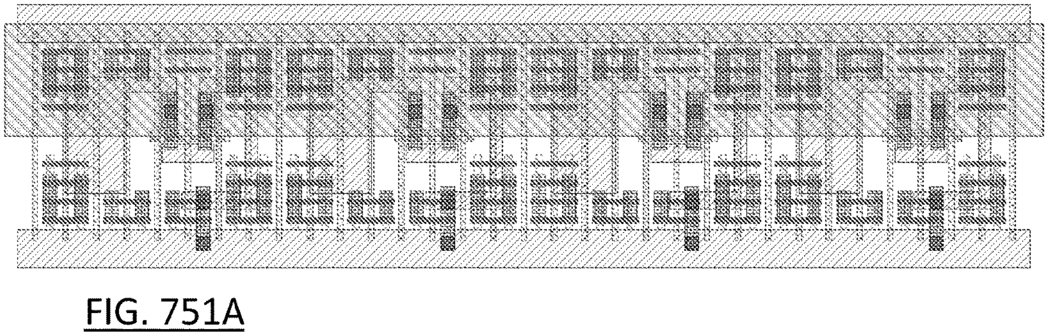
Figure 751B:
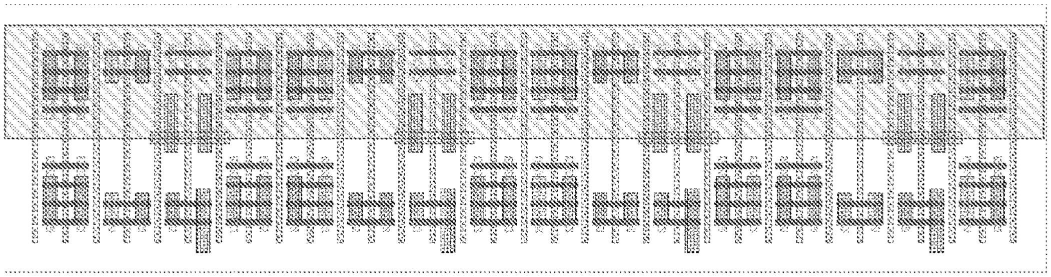
Figure 751C:
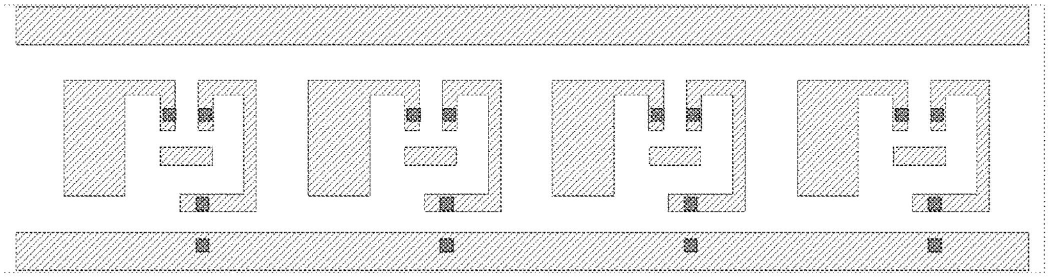
Figure 752A:
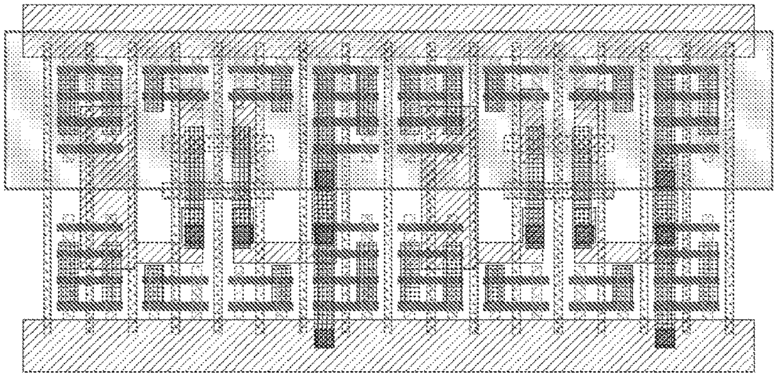
Figure 752B:
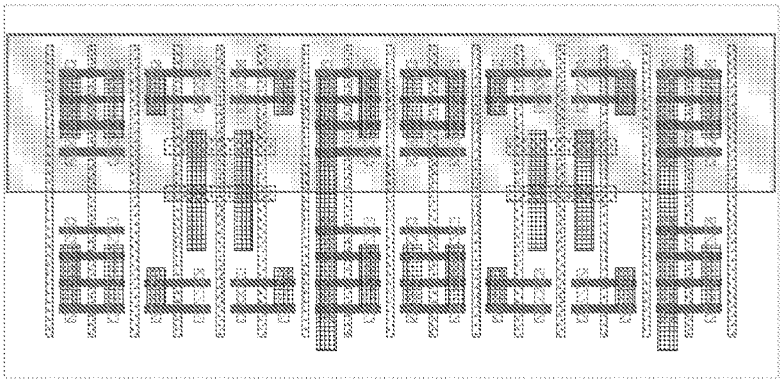
Figure 752C:
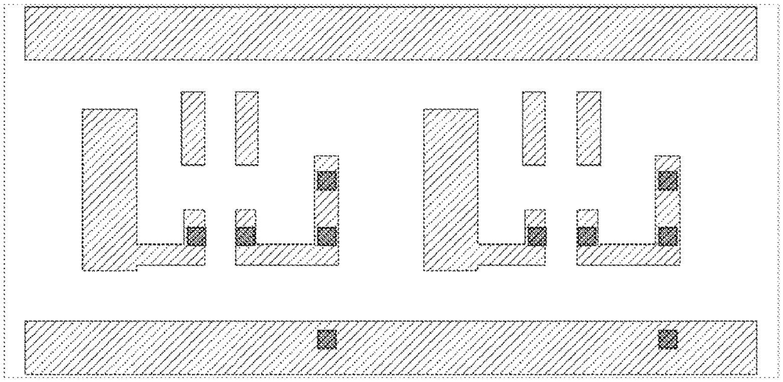
Figure 753A:
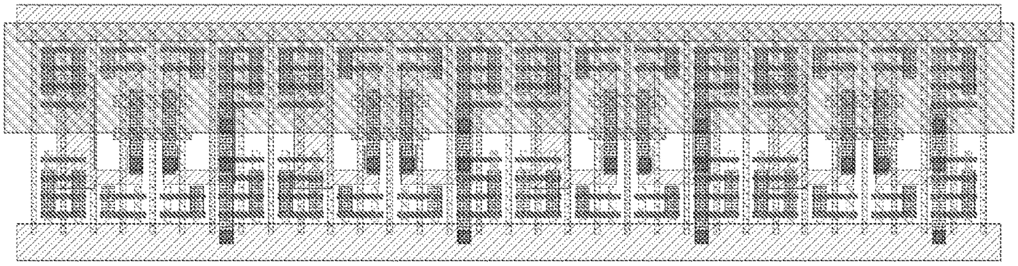
Figure 753B:
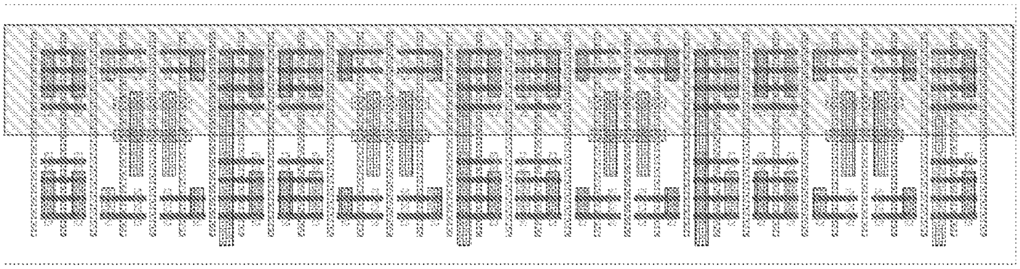
Figure 753C:
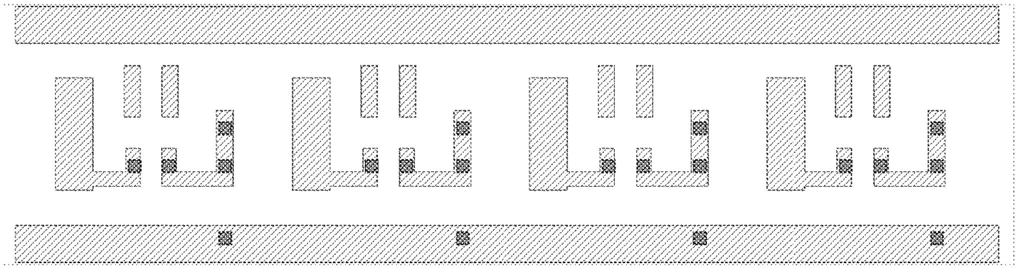
Figure 754A:
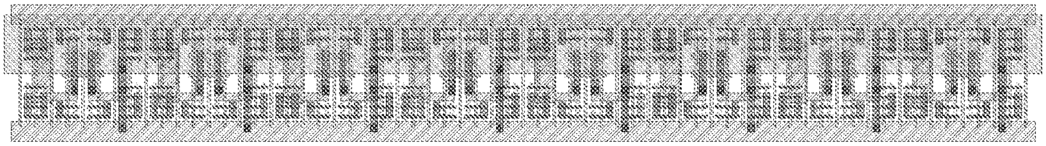
Figure 754B:
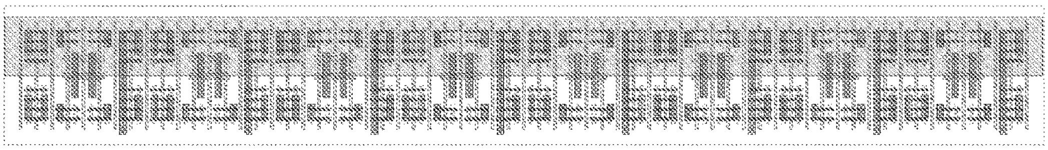
Figure 754C:
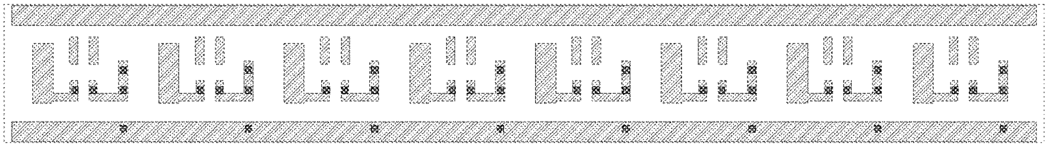
Figure 755A:
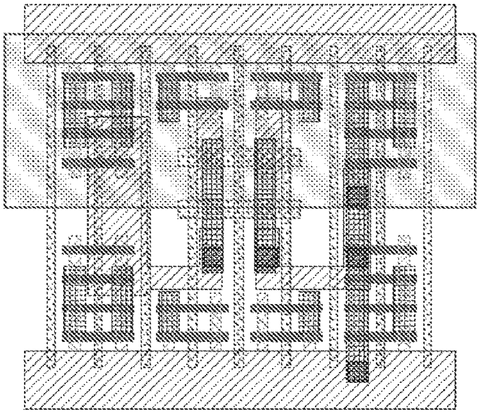
Figure 755B:
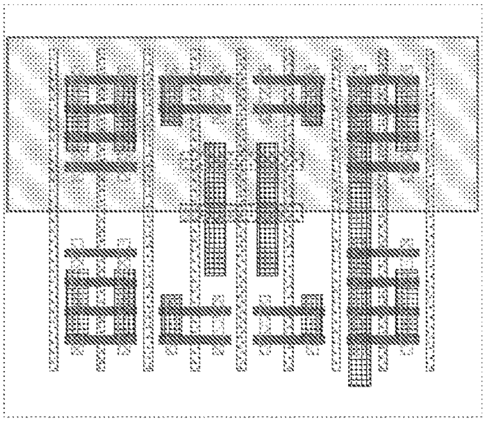
Figure 755C:
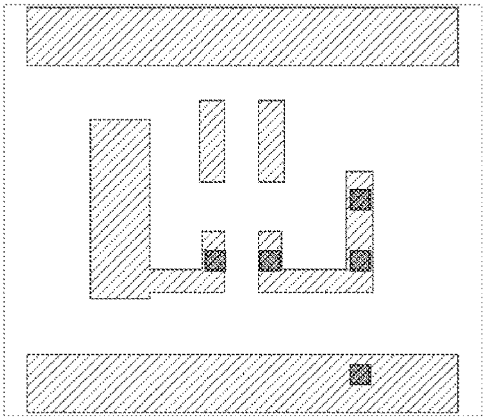
Figure 756A:
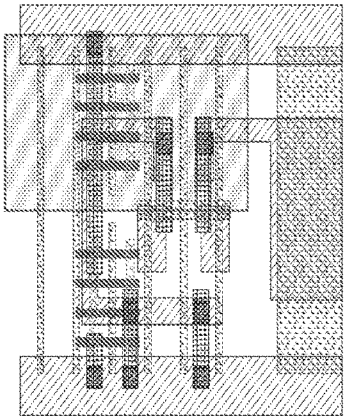
Figure 756B:
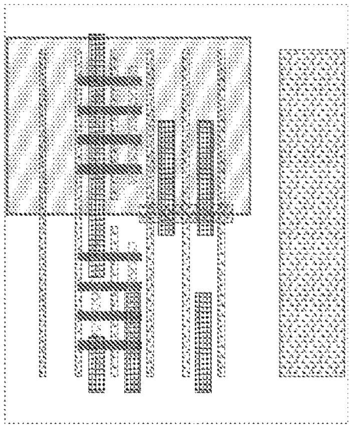
Figure 756C:
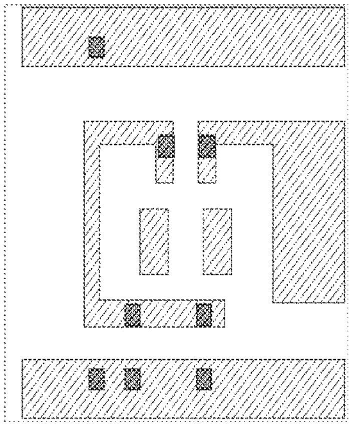
Figure 757A:
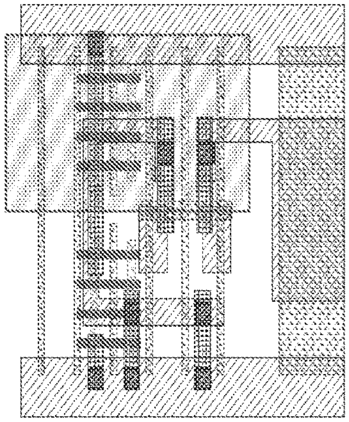
Figure 757B:
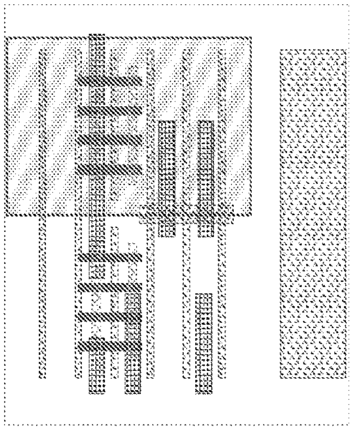
Figure 757C:
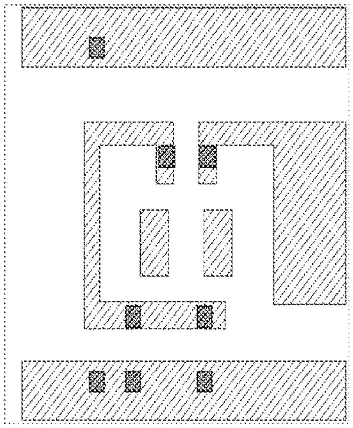
Figure 758A:
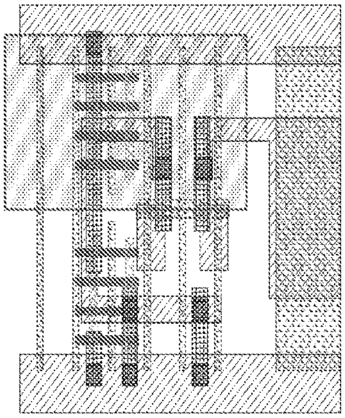
Figure 758B:
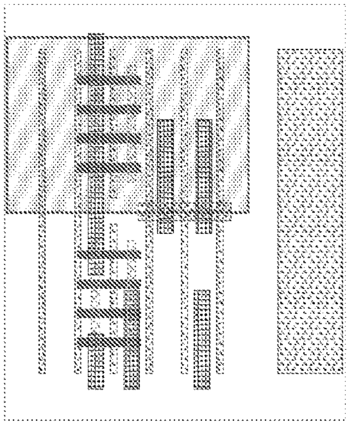
Figure 758C:
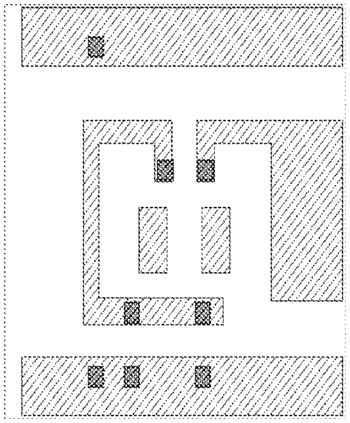
Figure 759A:
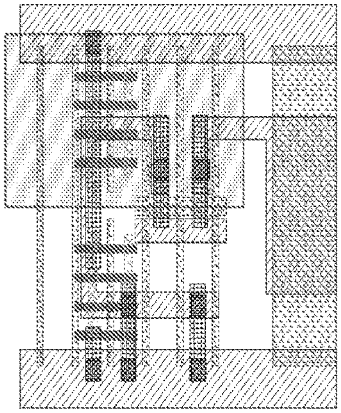
Figure 759B:
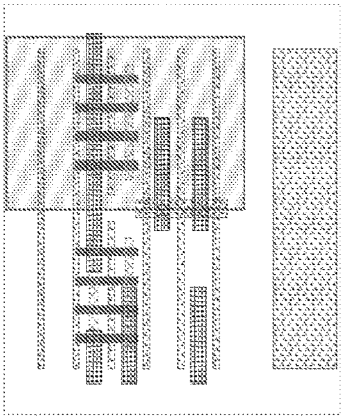
Figure 759C:
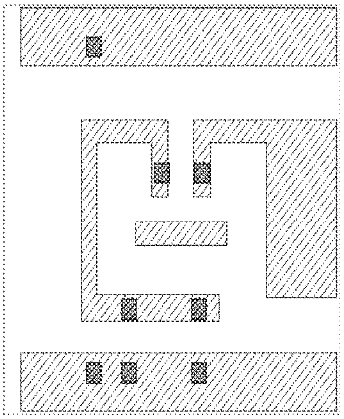
Figure 760A:
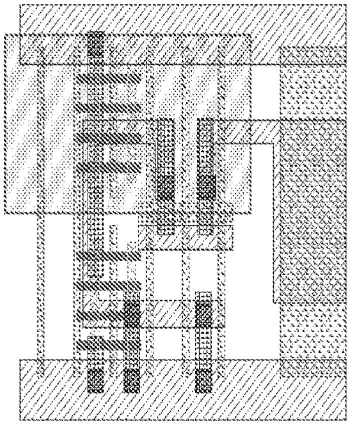
Figure 760B:
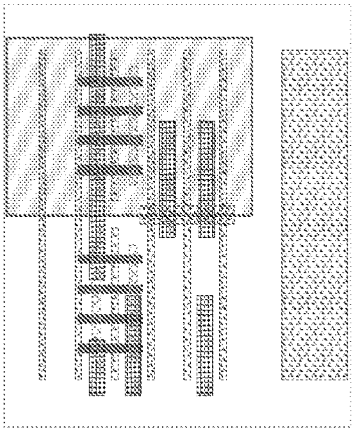
Figure 760C:
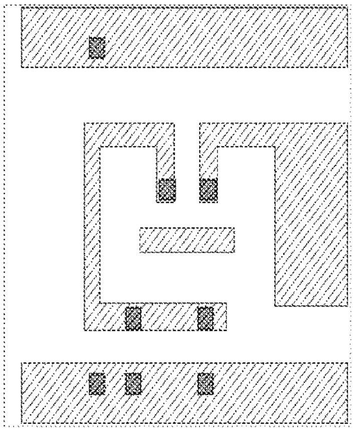
Figure 761A:
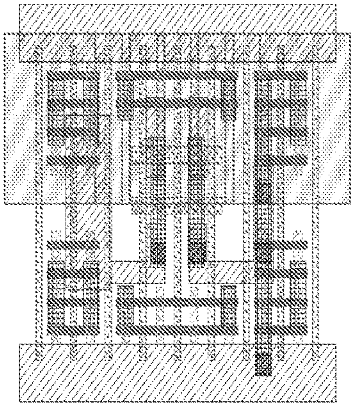
Figure 761B:
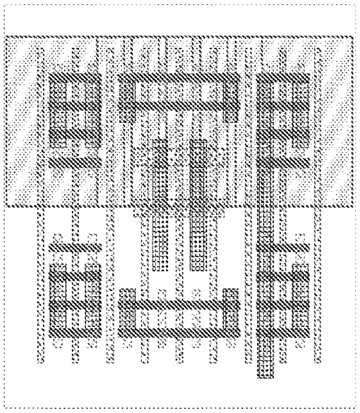
Figure 761C:
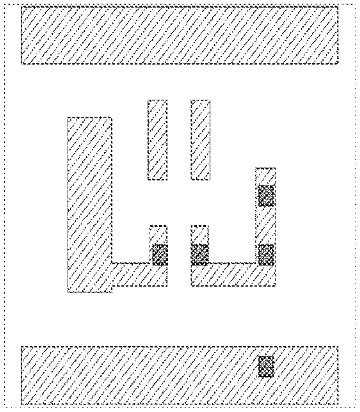
Figure 762A:
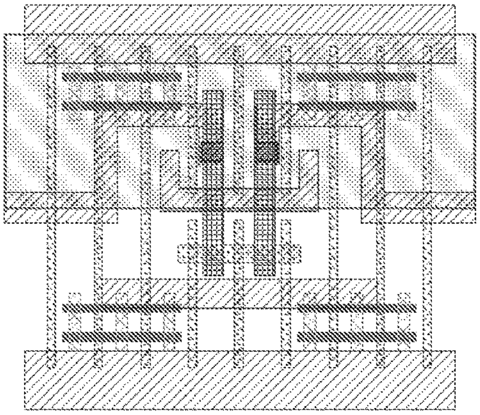
Figure 762B:
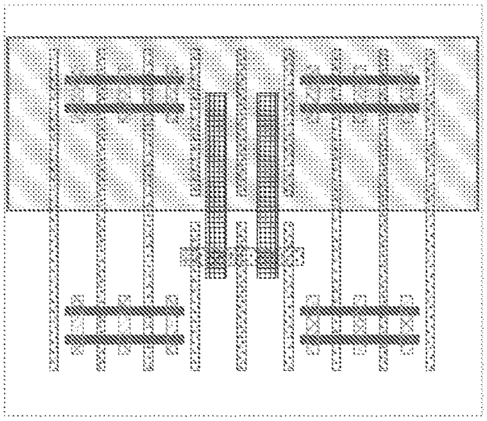
Figure 762C:
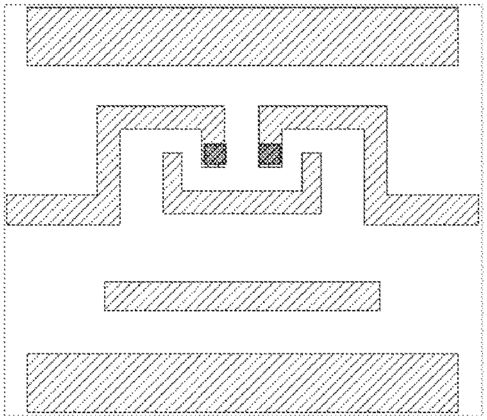
Figure 763A:
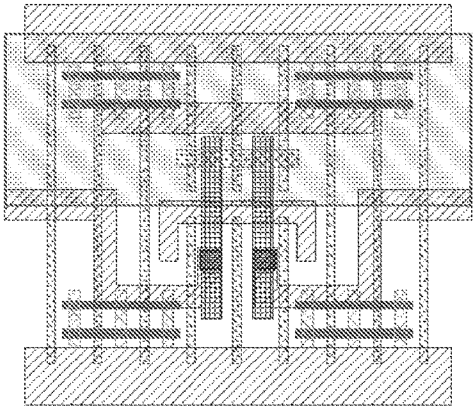
Figure 763B:
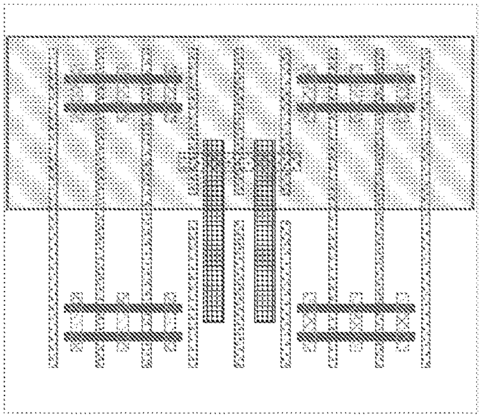
Figure 763C:
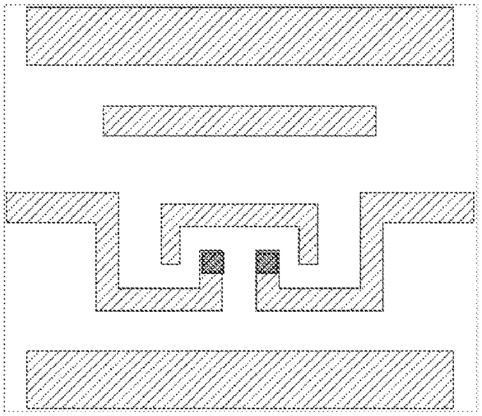
Figure 764A:
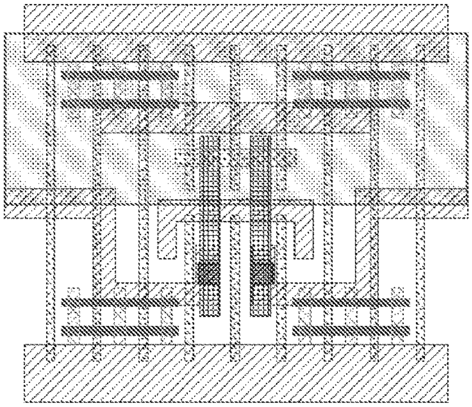
Figure 764B:
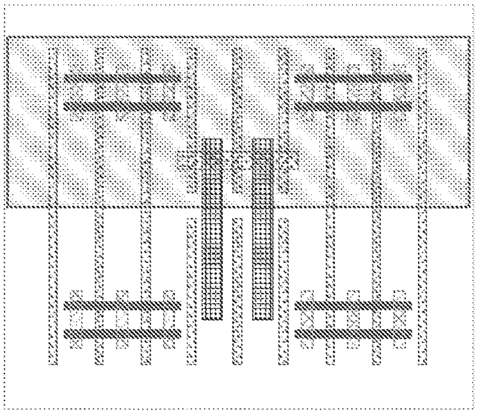
Figure 764C:
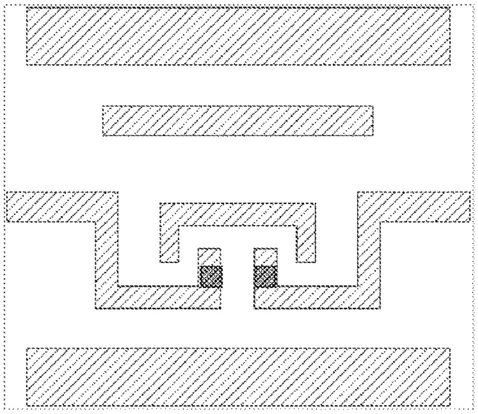
Figure 765A:
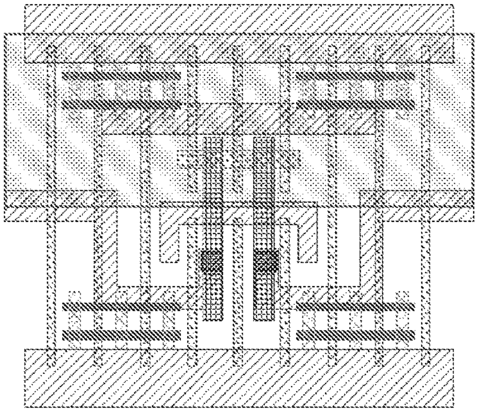
Figure 765B:
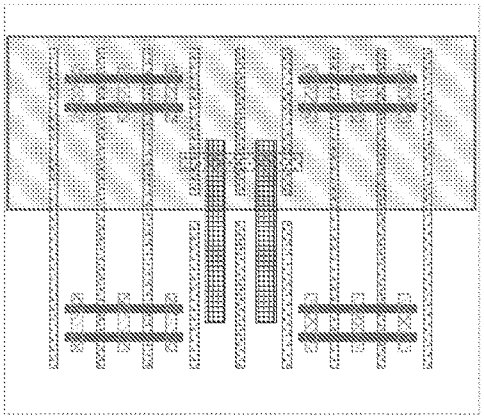
Figure 765C:
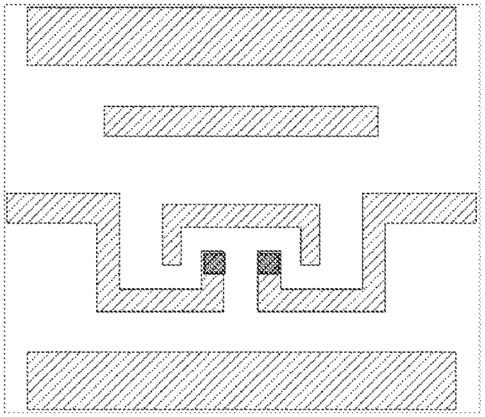
Figure 766A:
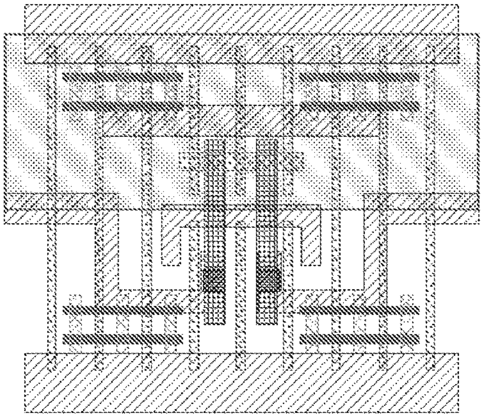
Figure 766B:
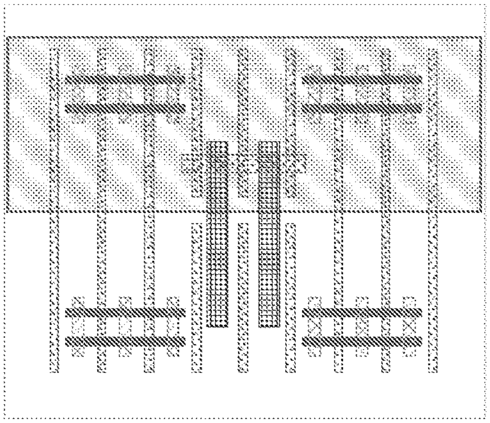
Figure 766C:
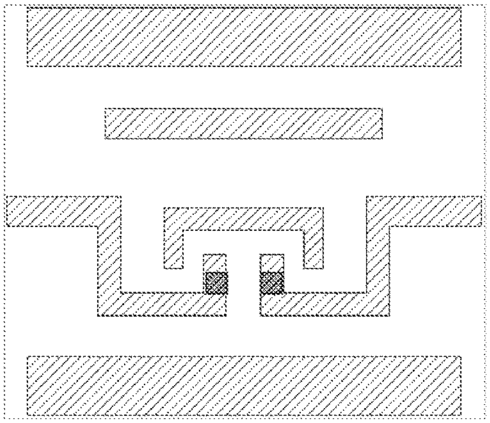
Figure 767A:
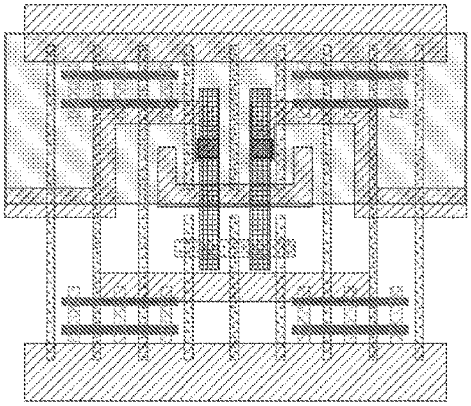
Figure 767B:
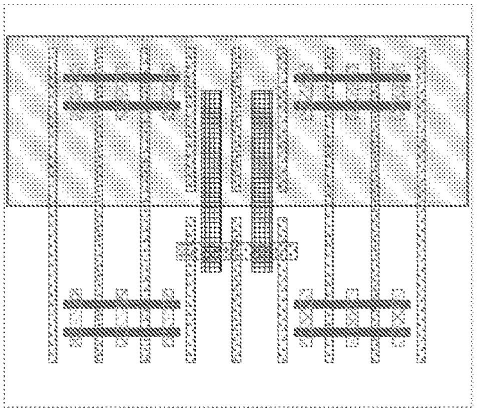
Figure 767C:
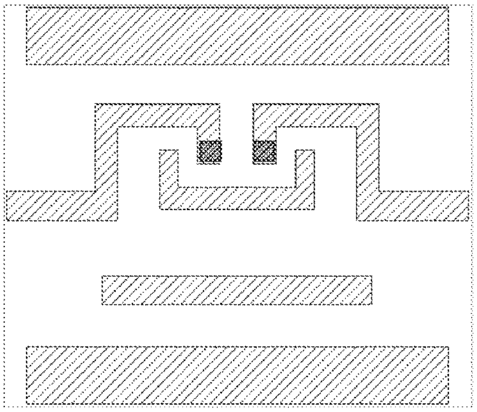
Figure 768A:
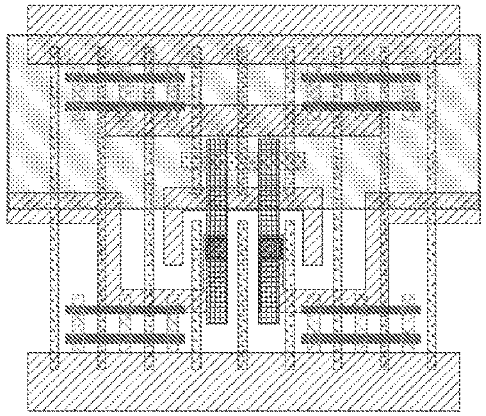
Figure 768B:
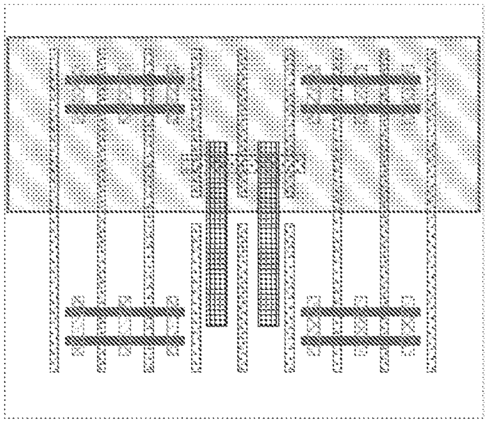
Figure 768C:
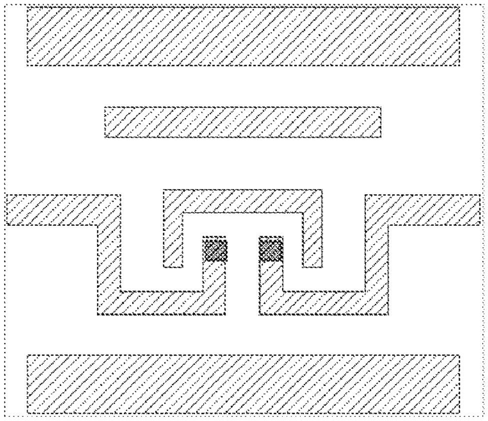
Figure 769A:
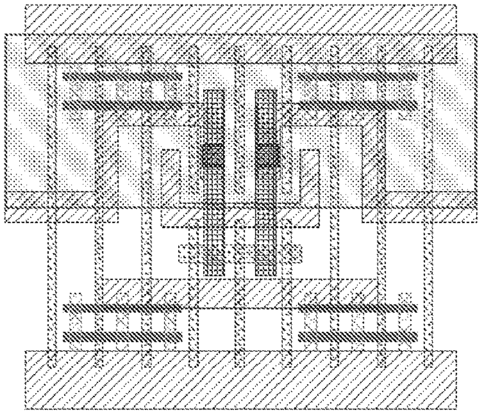
Figure 769B:
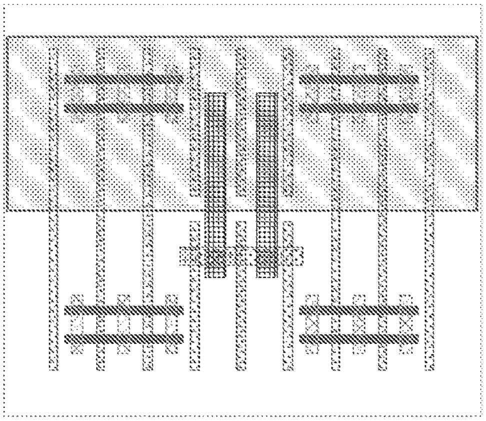
Figure 769C:
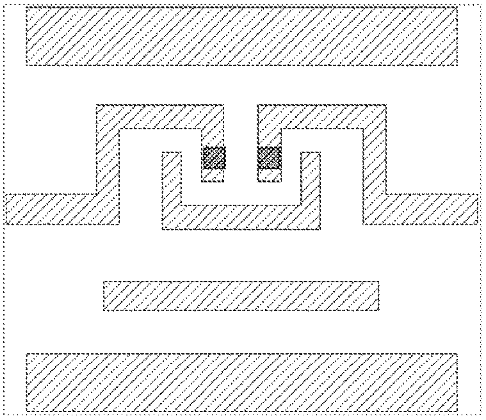
Figure 770A:
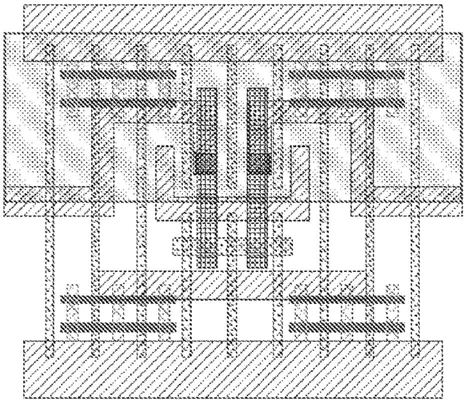
Figure 770B:
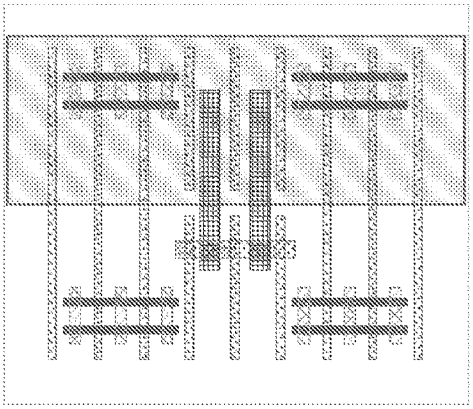
Figure 770C:
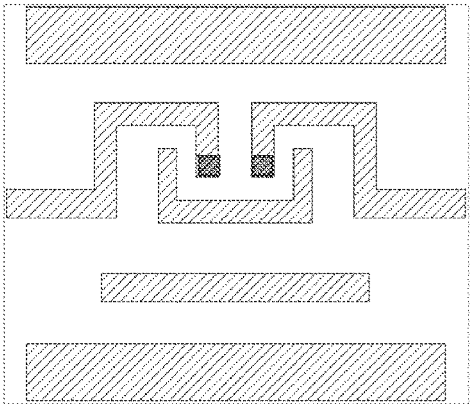
Figure 771A:
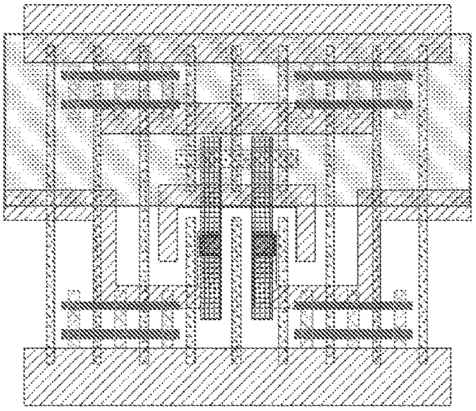
Figure 771B:
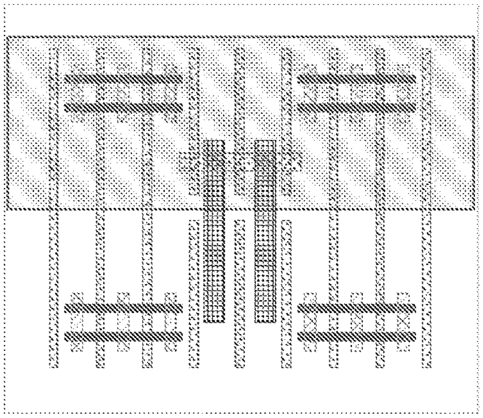
Figure 771C:
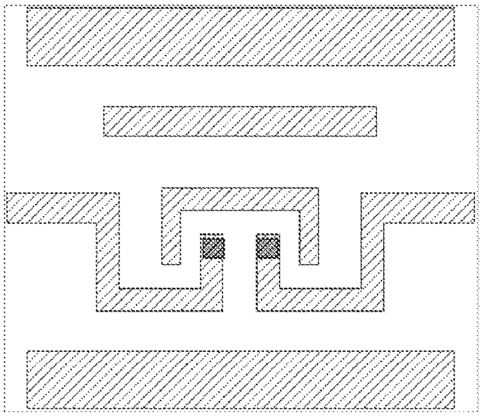
Figure 772A:
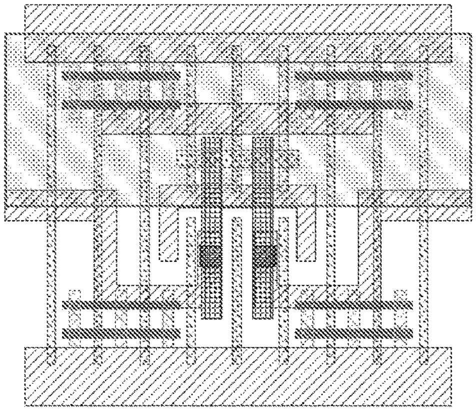
Figure 772B:
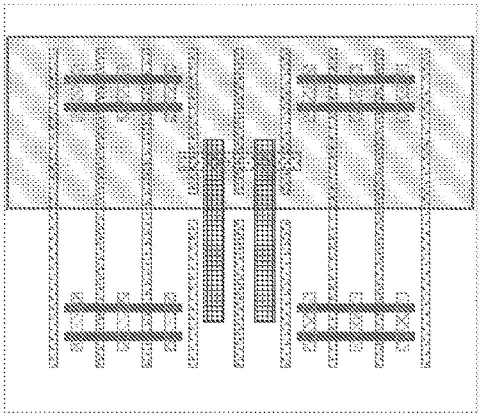
Figure 772C:
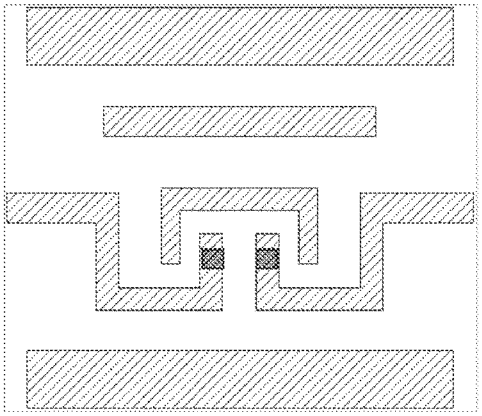
Figure 773A:
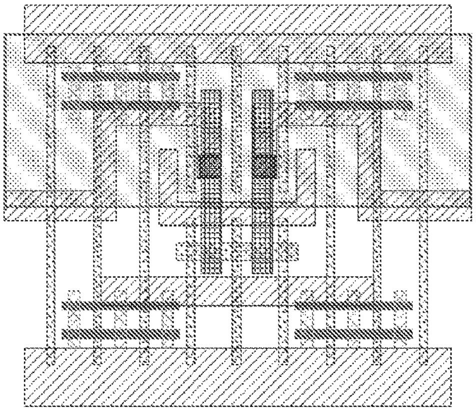
Figure 773B:
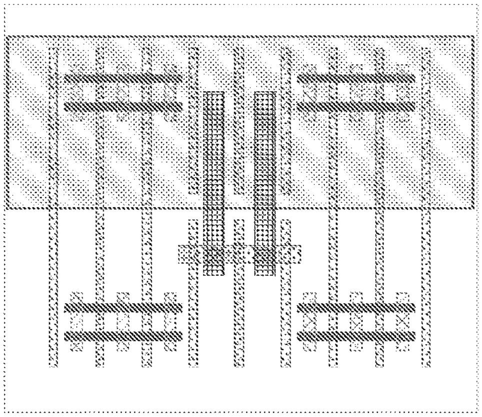
Figure 773C:
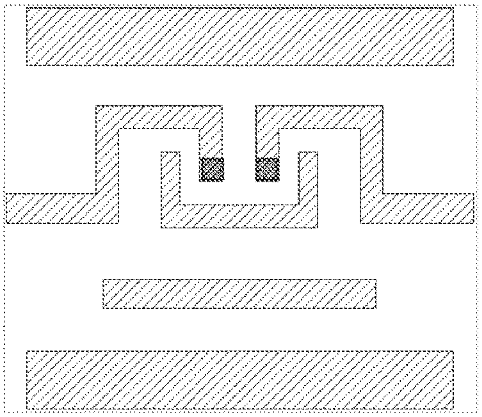
Figure 774A:
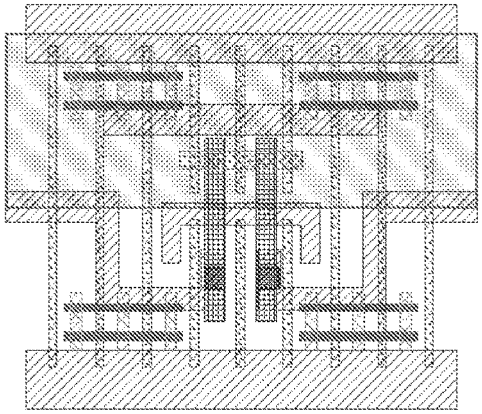
Figure 774B:
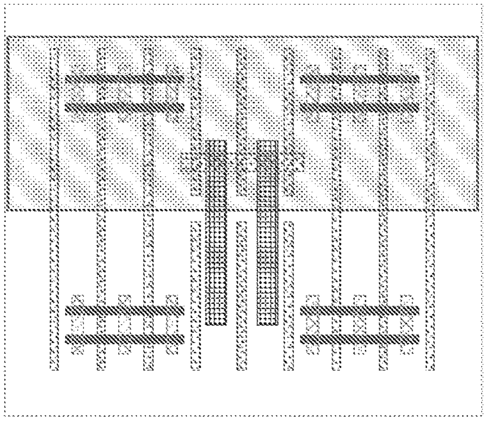
Figure 774C:
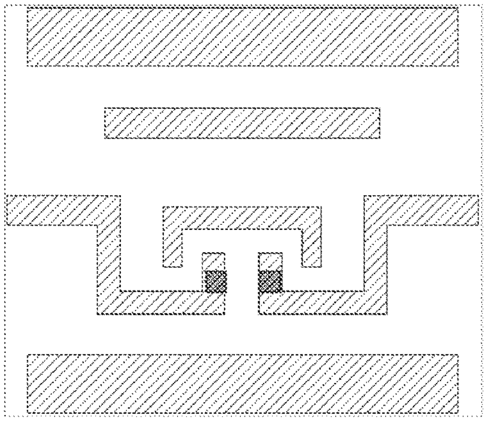
Figure 775A:
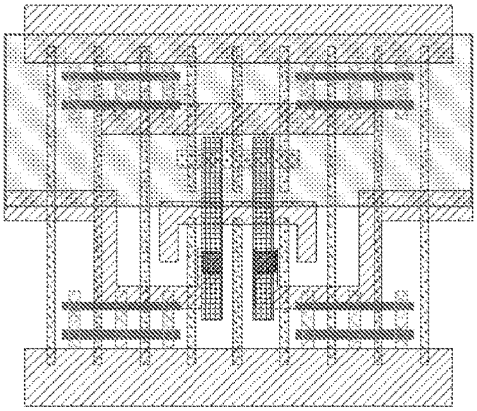
Figure 775B:
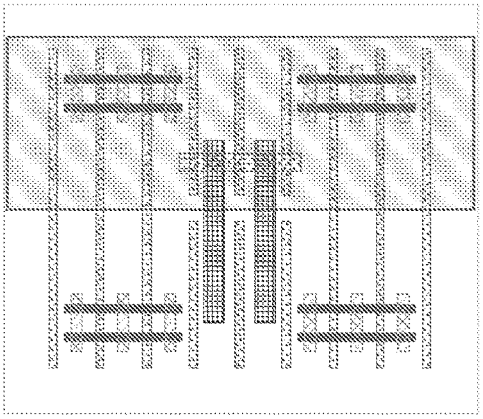
Figure 775C:
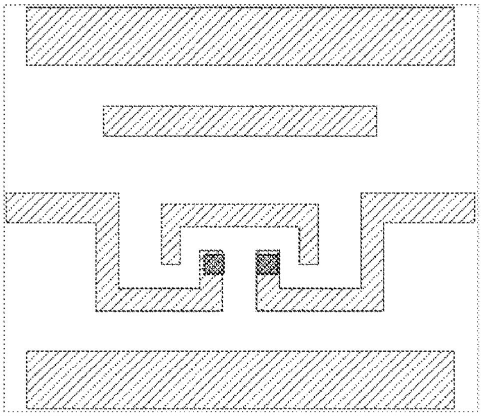
Figure 776A:
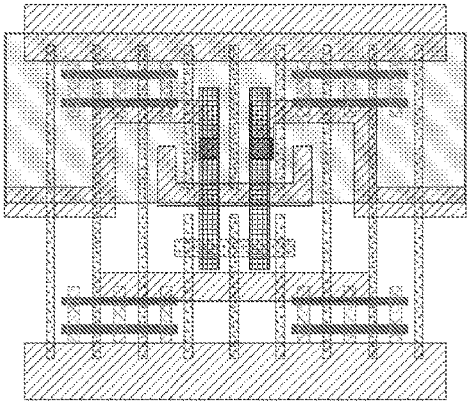
Figure 776B:
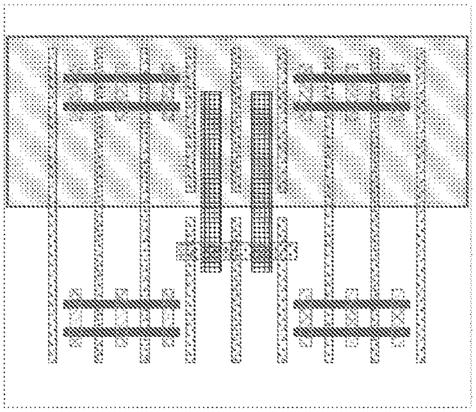
Figure 776C:
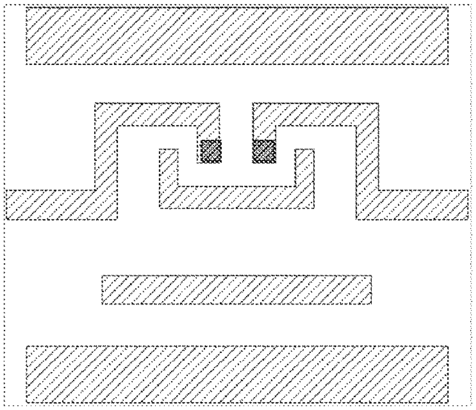
Figure 777A:
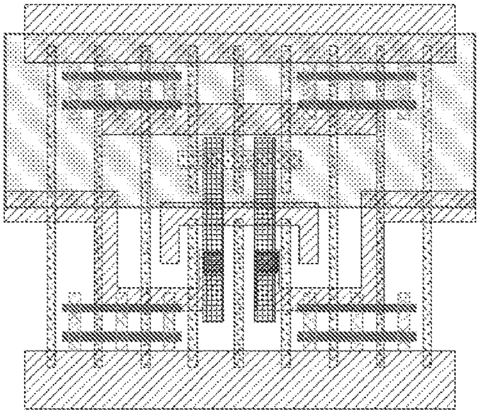
Figure 777B:
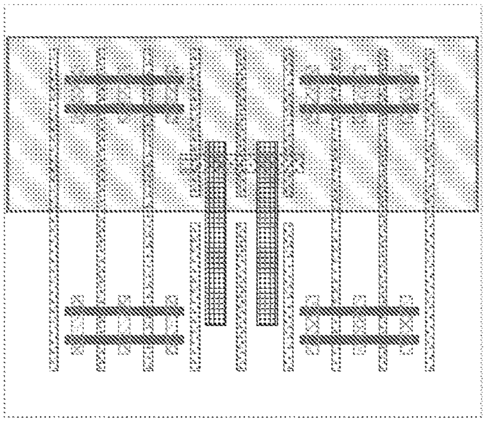
Figure 777C:
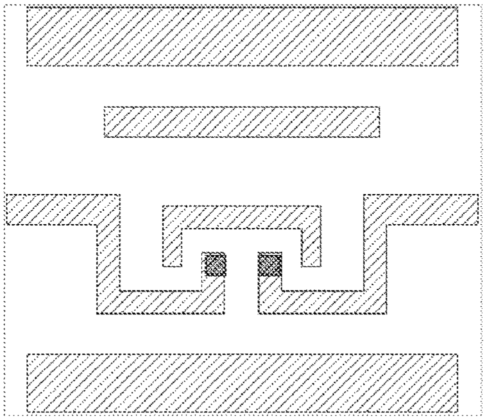
Figure 778A:
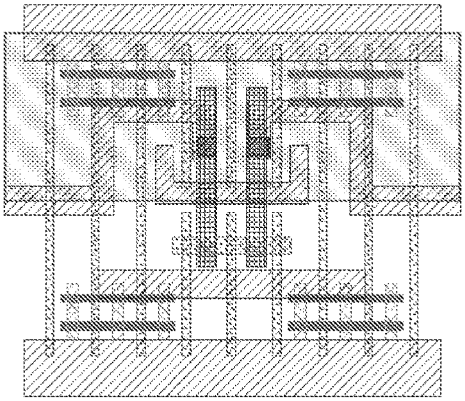
Figure 778B:
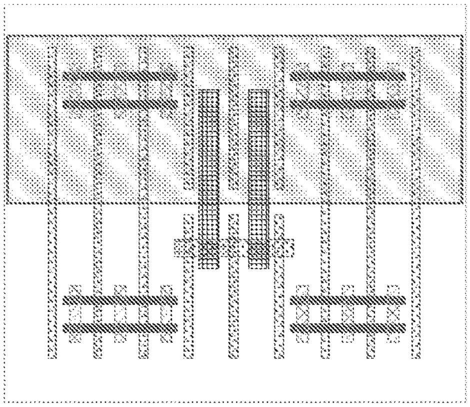
Figure 778C:
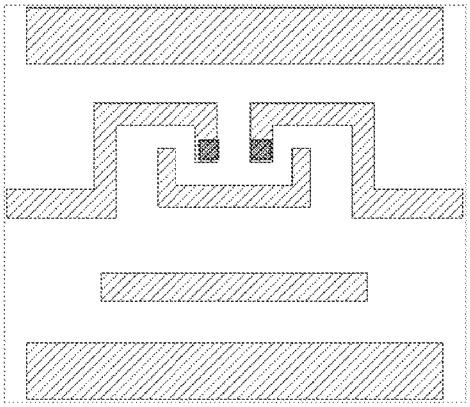
Figure 779A:
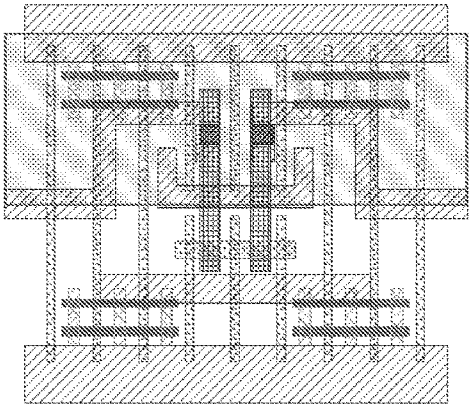
Figure 779B:
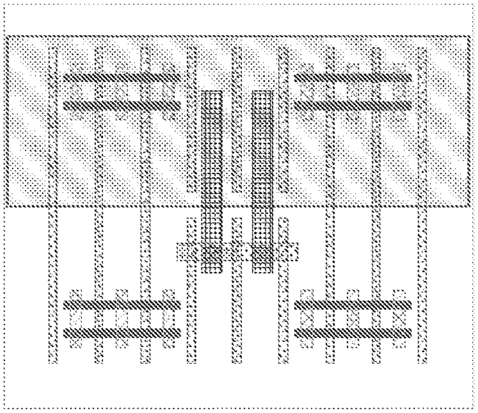
Figure 779C:
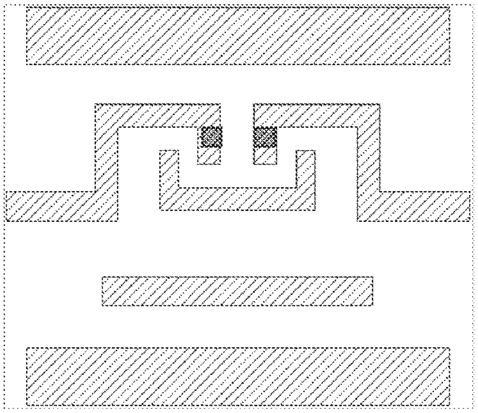
Figure 780A:
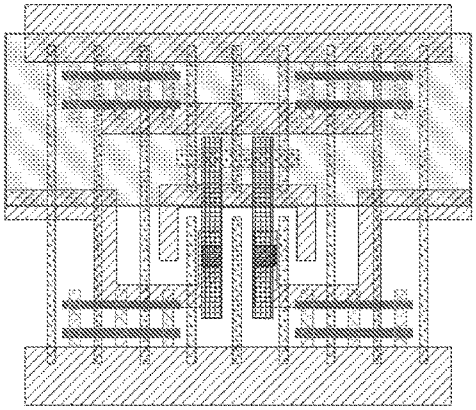
Figure 780B:
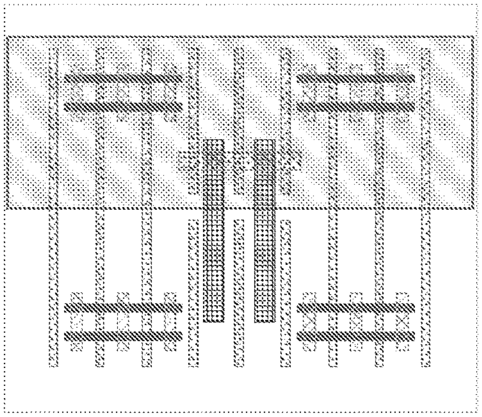
Figure 780C:
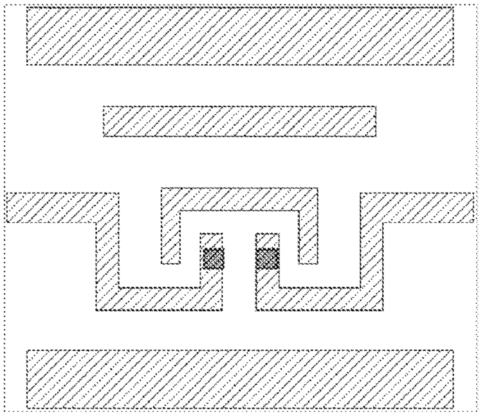
Figure 781A:
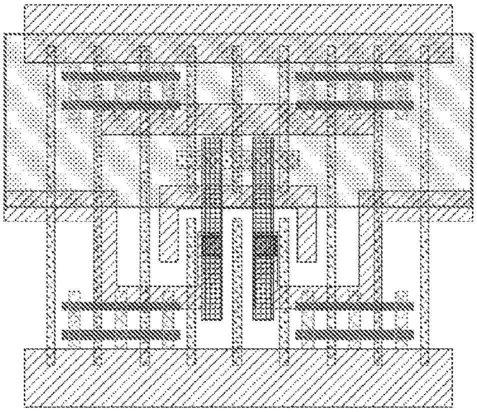
Figure 781B:
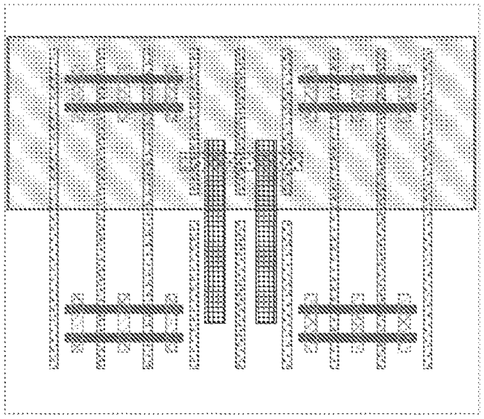
Figure 781C:
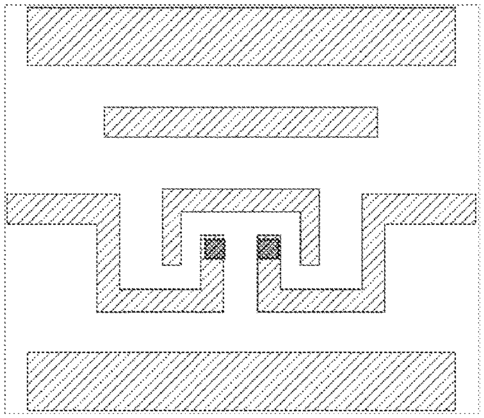
Figure 782A:
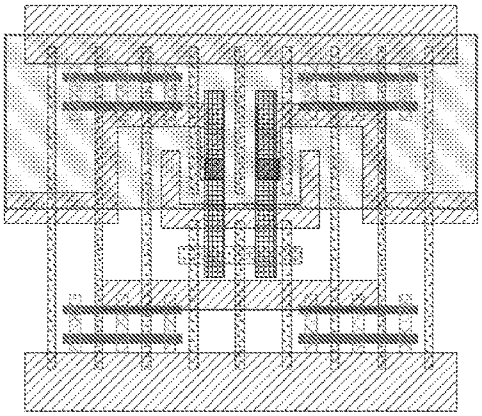
Figure 782B:
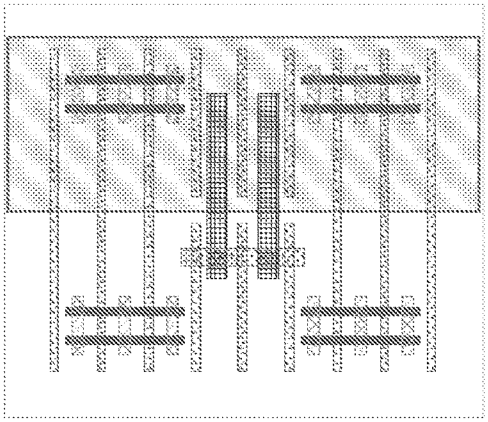
Figure 782C:
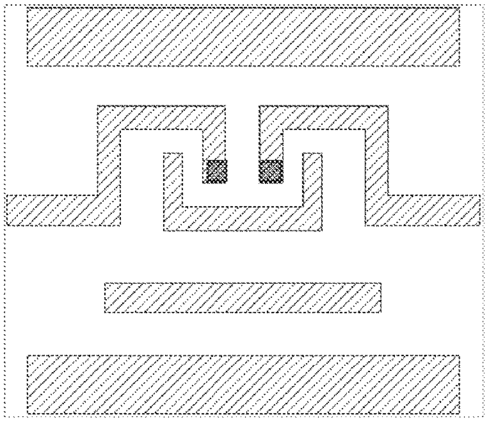
Figure 783A:
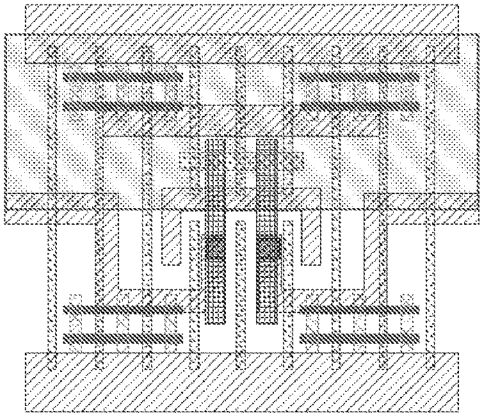
Figure 783B:
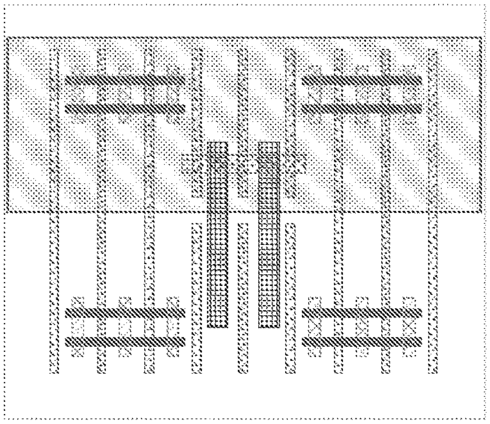
Figure 783C:
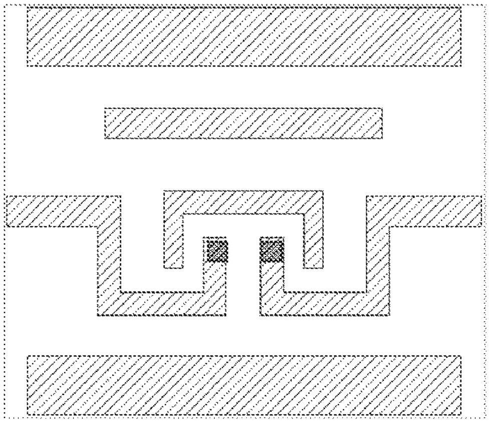
Figure 784A:
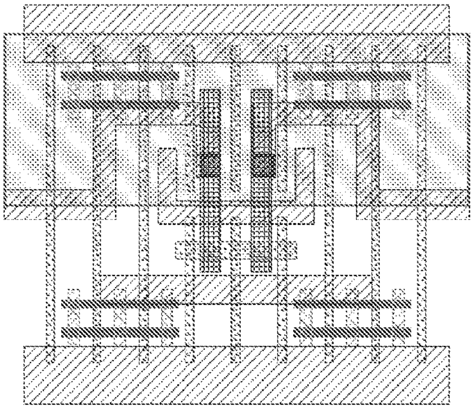
Figure 784B:
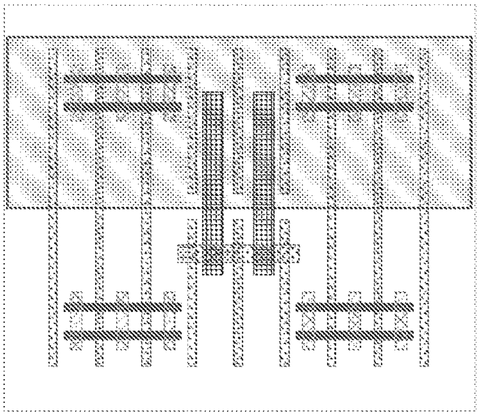
Figure 784C:
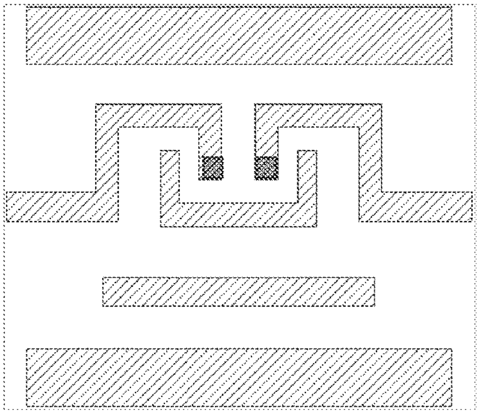
Figure 785A:
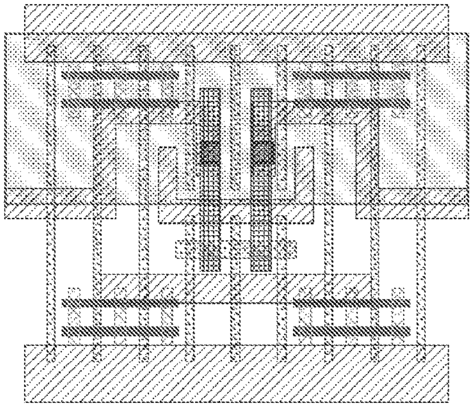
Figure 785B:
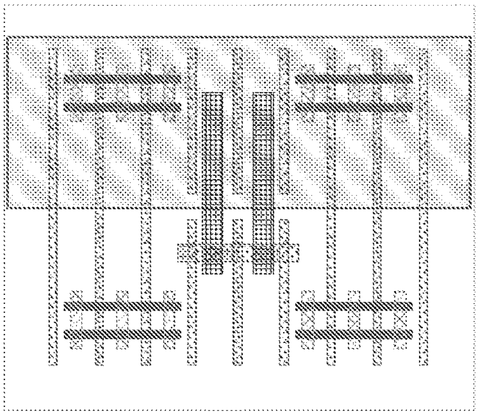
Figure 785C:
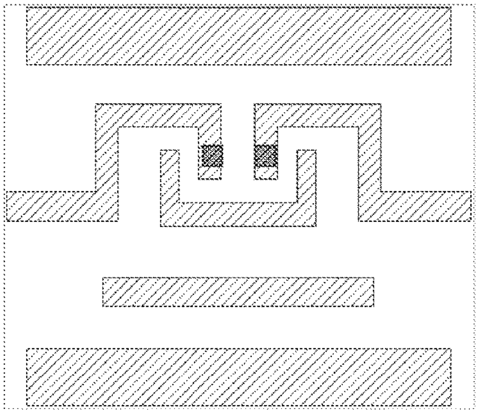
Figure 786A:
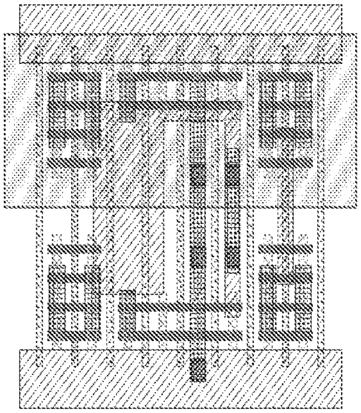
Figure 786B:
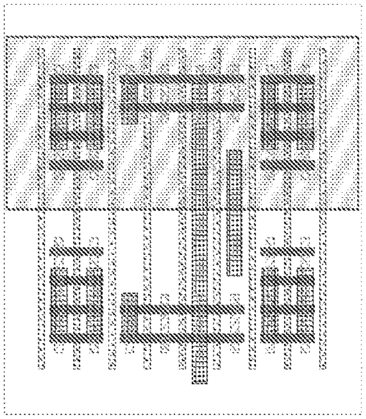
Figure 786C:
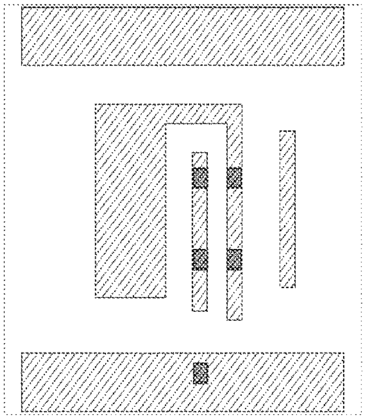
Figure 787A:
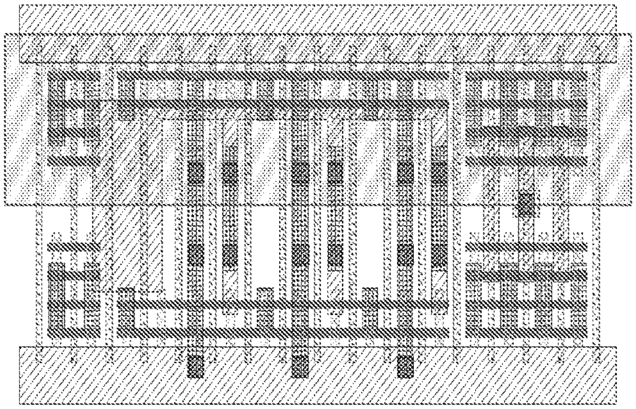
Figure 787B:
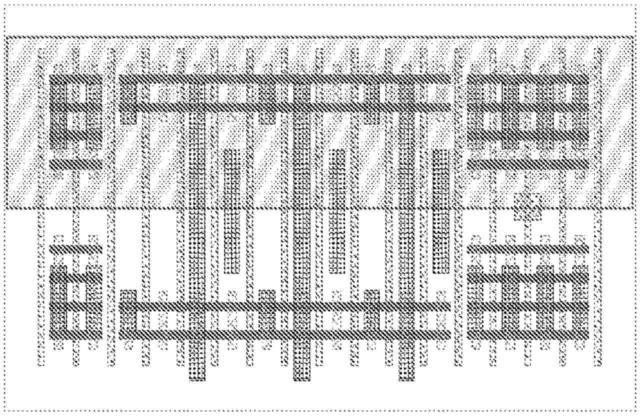
Figure 787C:
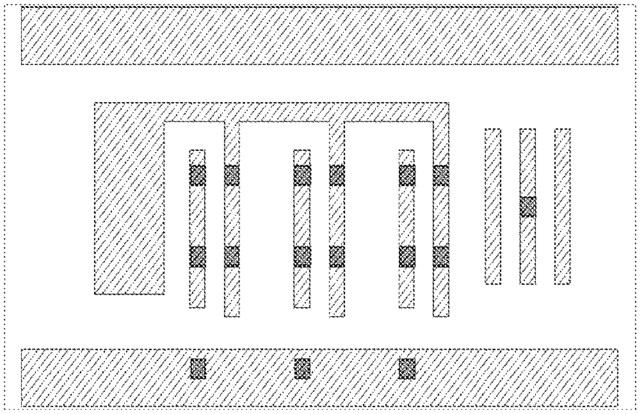
Figure 788A:
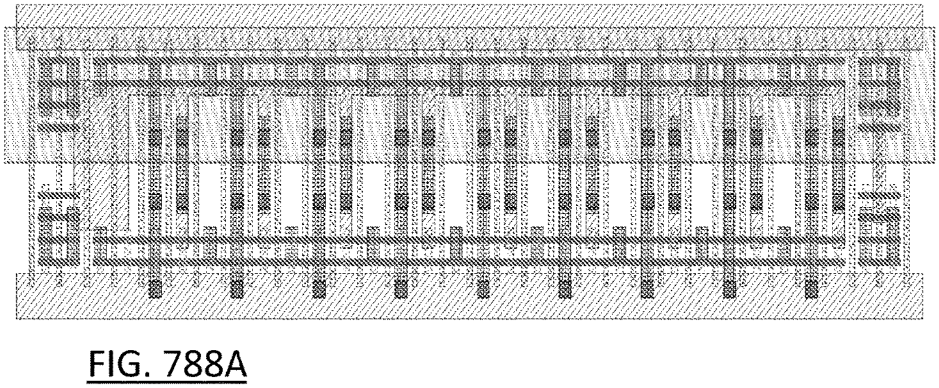
Figure 788B:
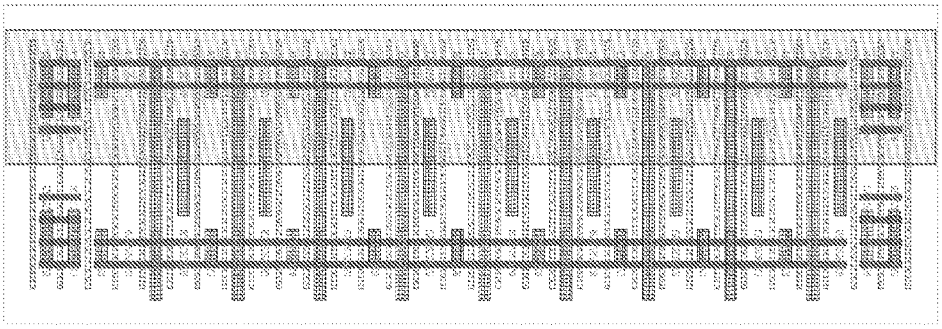
Figure 788C:
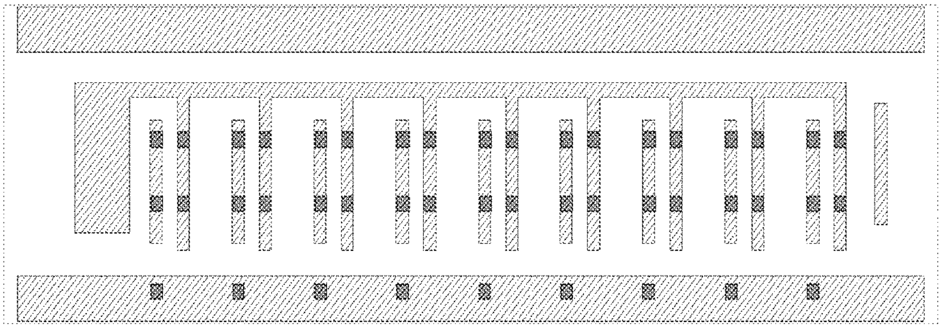
Figure 789A:
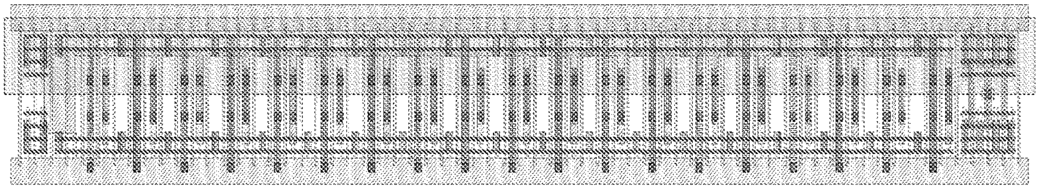
Figure 789B:
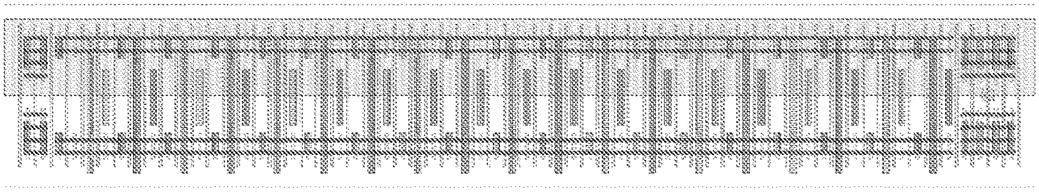
Figure 789C:
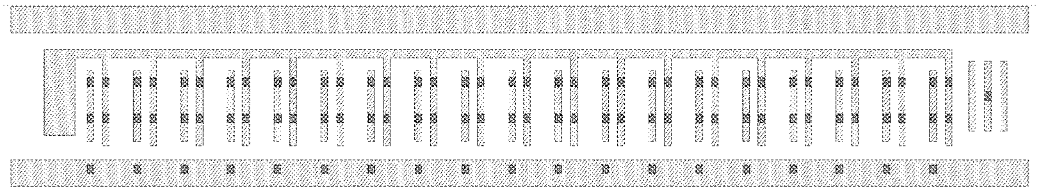
Figure 790A:
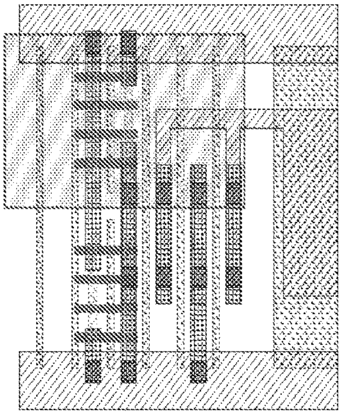
Figure 790B:
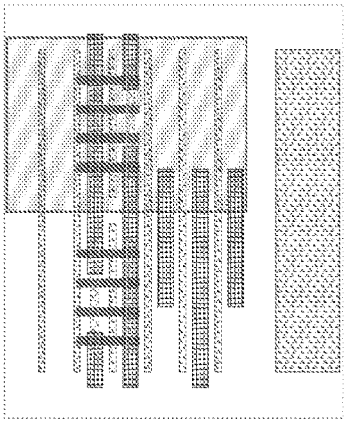
Figure 790C:
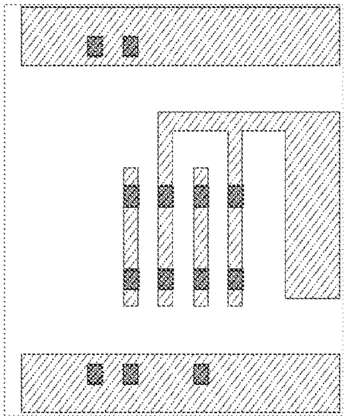
Figure 791A:
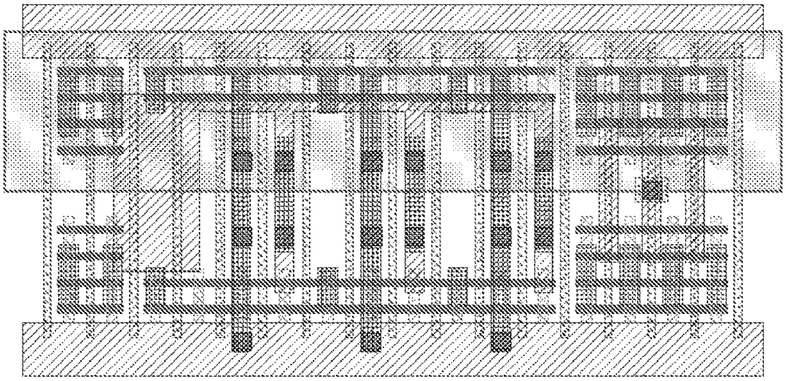
Figure 791B:
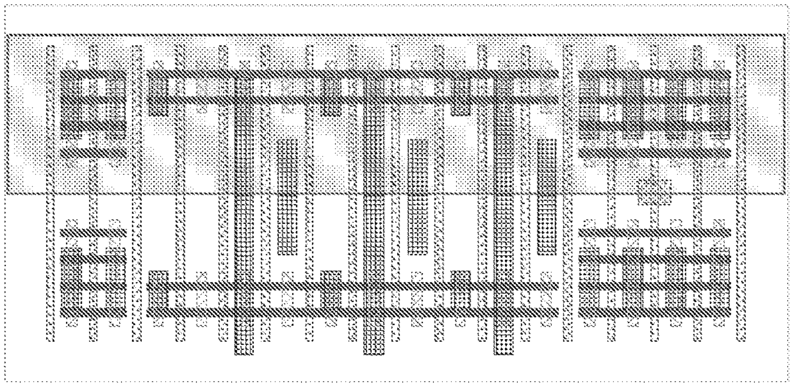
Figure 791C:
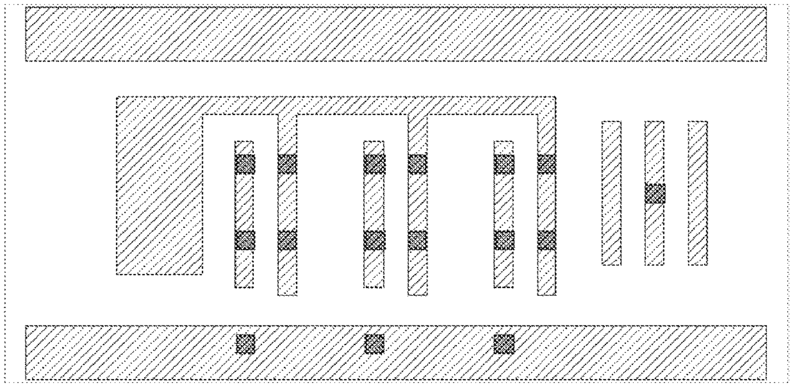
Figure 792A:
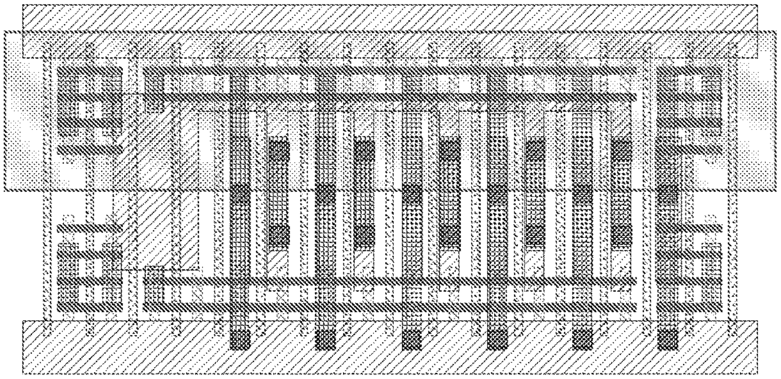
Figure 792B:
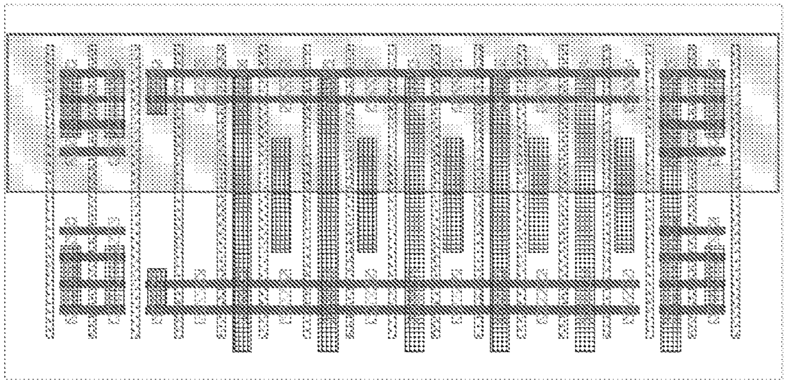
Figure 792C:
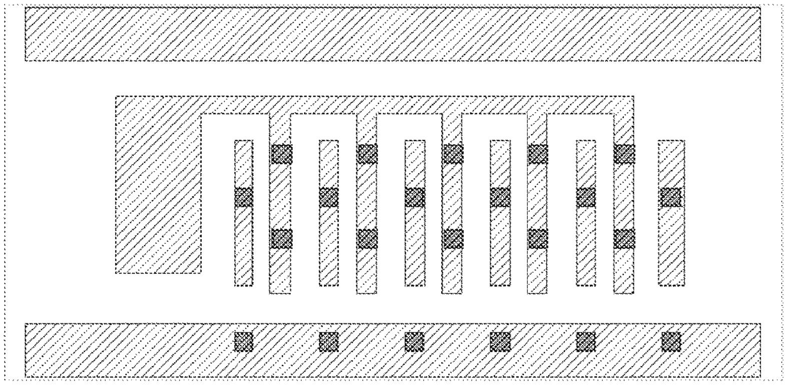
Figure 793A:
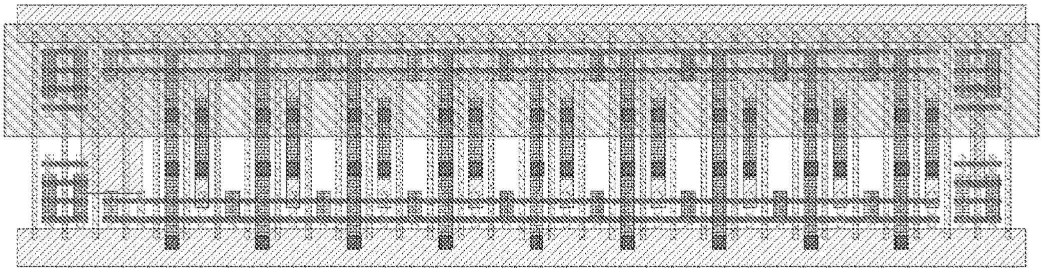
Figure 793B:
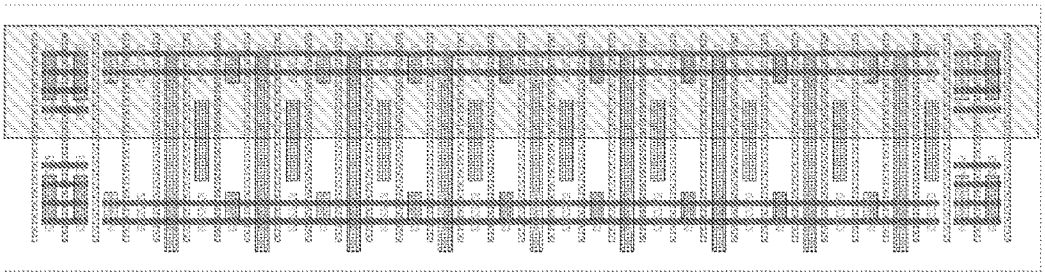
Figure 793C:
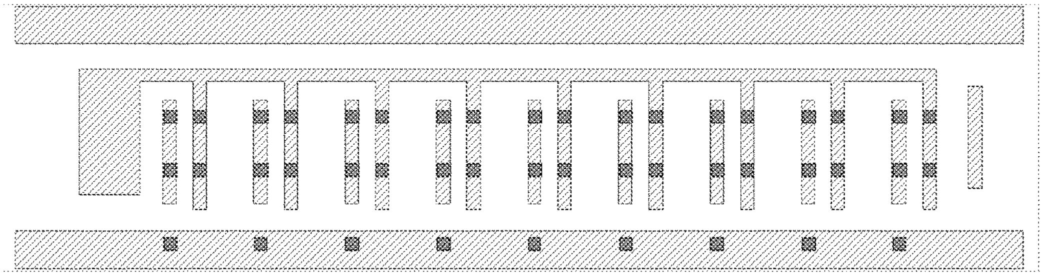
Figure 794A:
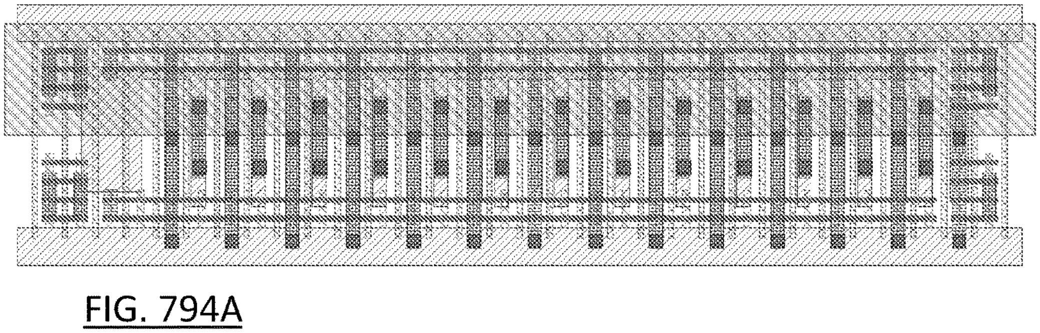
Figure 794B:
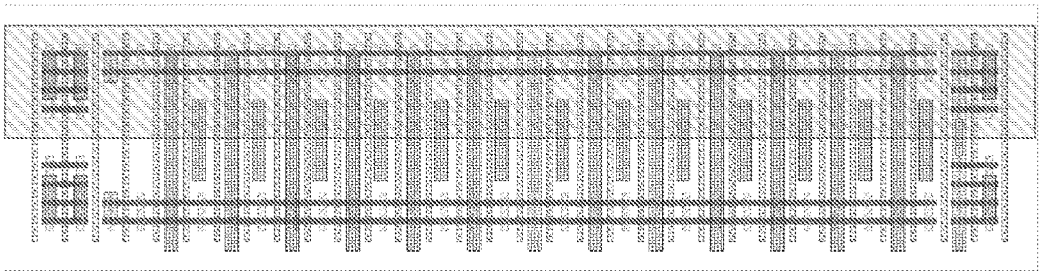
Figure 794C:
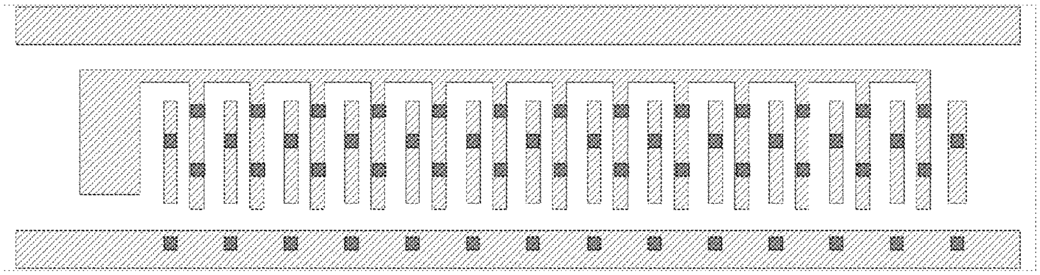
Figure 795A:
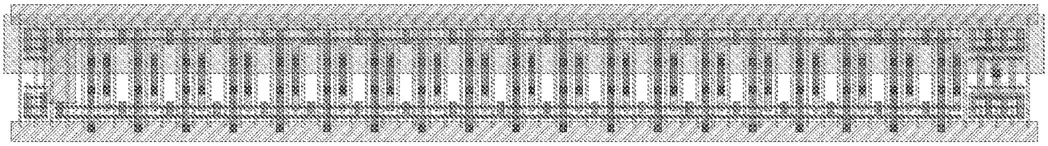
Figure 795B:
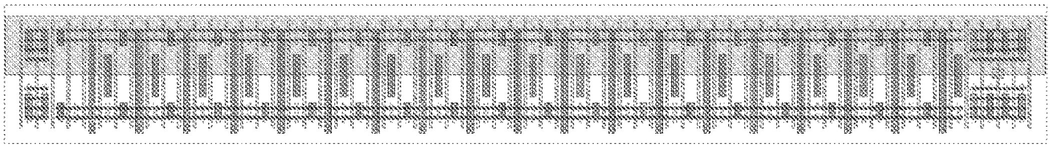
Figure 795C:
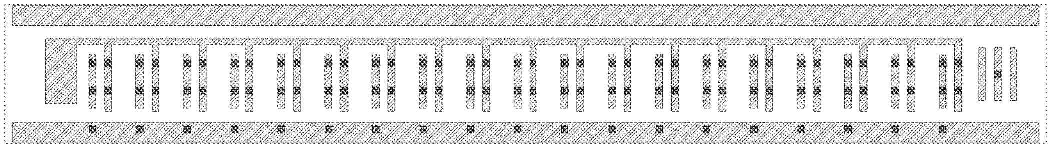
Figure 796A:
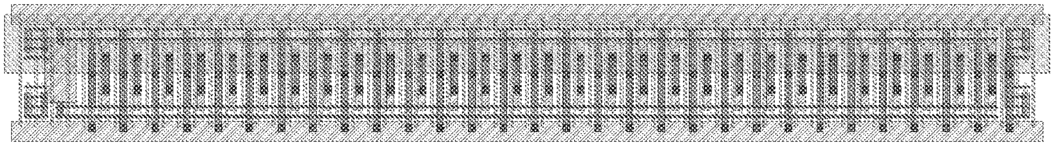
Figure 796B:
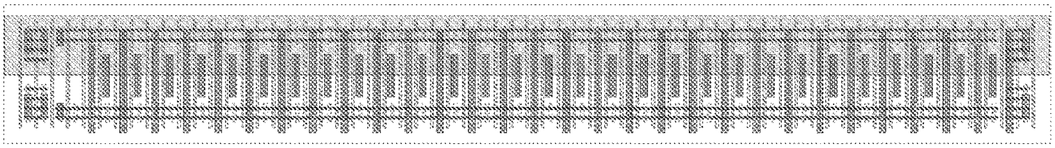
Figure 796C:
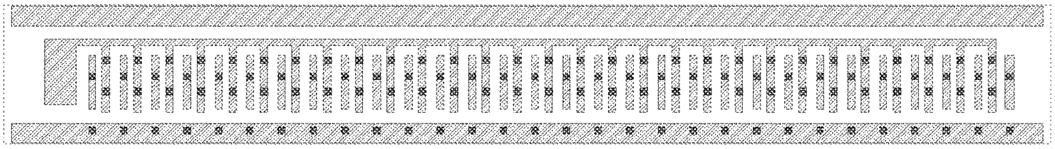
Figure 797A:
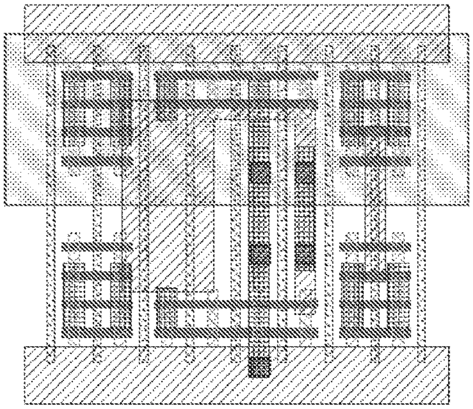
Figure 797B:
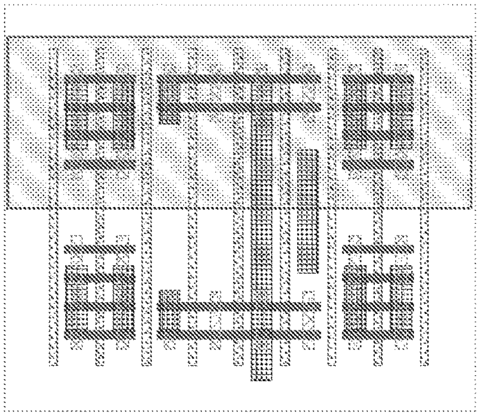
Figure 797C:
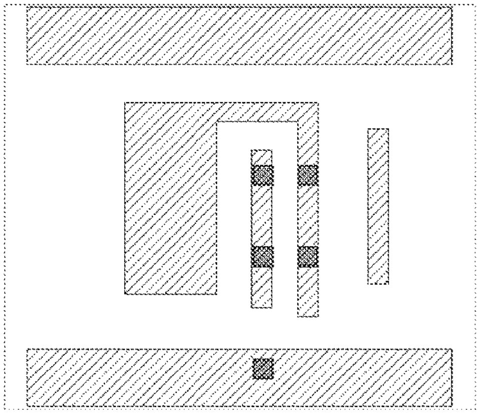
Figure 798A:
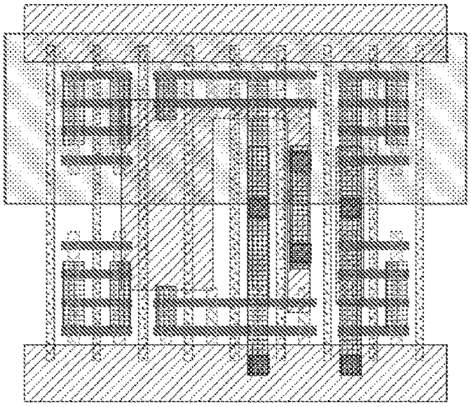
Figure 798B:
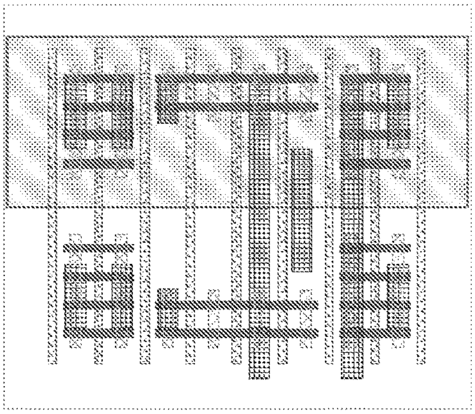
Figure 798C:
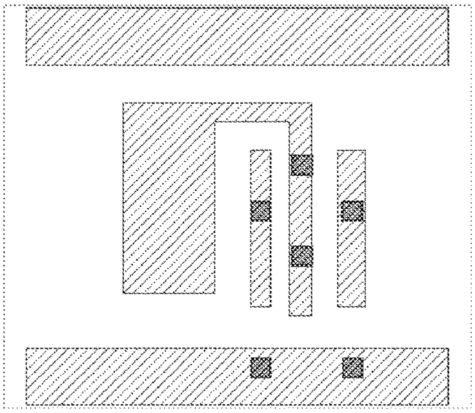
Figure 799A:
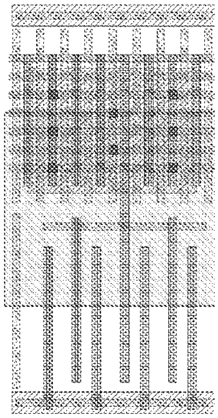
Figure 799B:
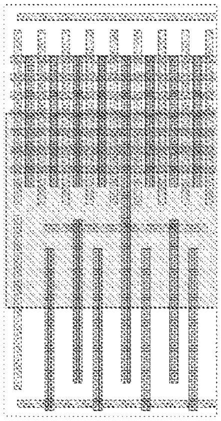
Figure 799C:
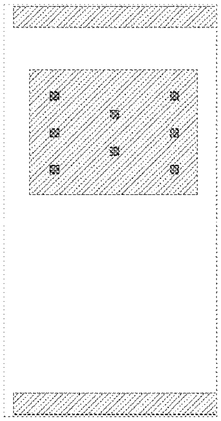
Figure 800A:
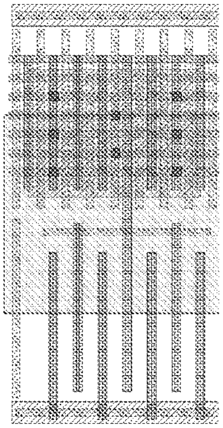
Figure 800B:
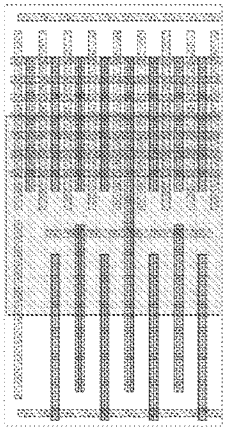
Figure 800C:
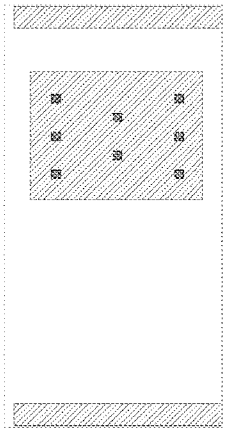
Figure 801A:
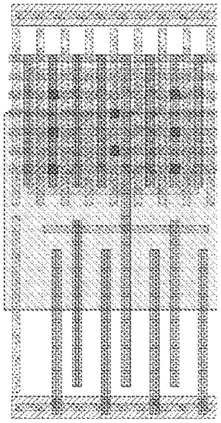
Figure 801B:
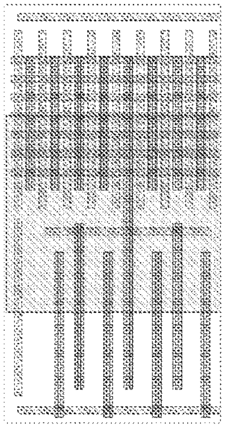
Figure 801C:
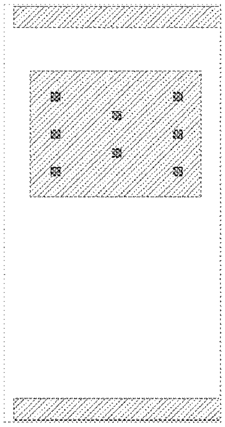
Figure 802A:
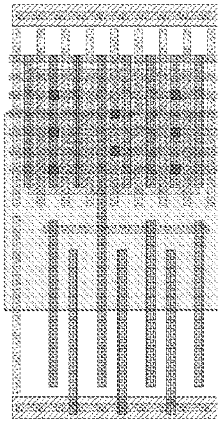
Figure 802B:
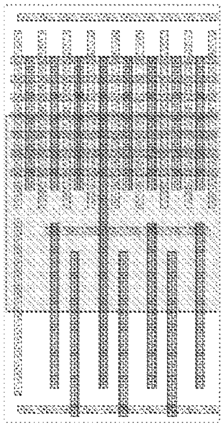
Figure 802C:
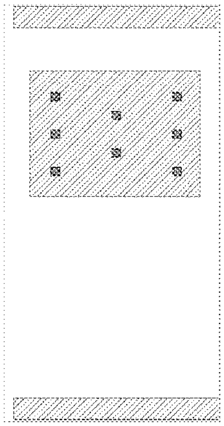
Figure 803A:
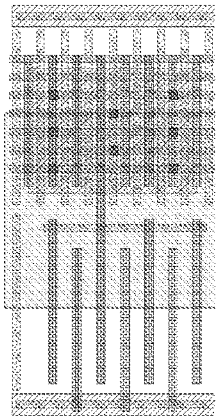
Figure 803B:
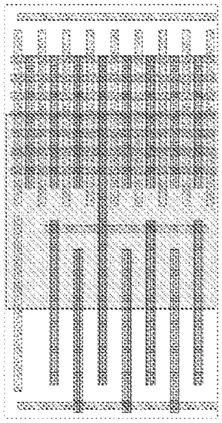
Figure 803C:
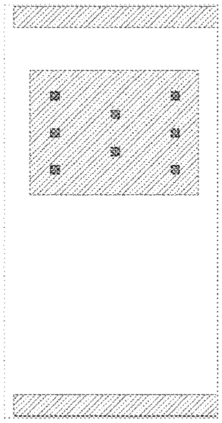
Figure 804A:
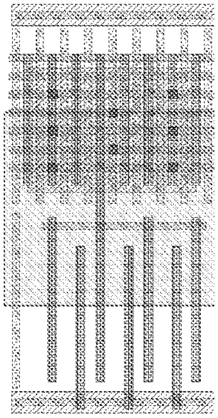
Figure 804B:
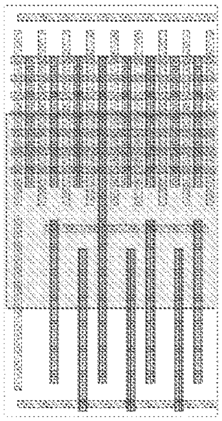
Figure 804C:
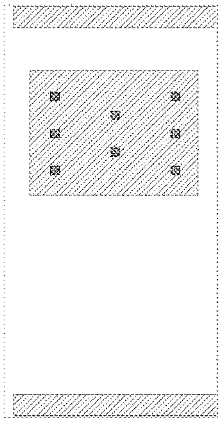
Figure 805A:
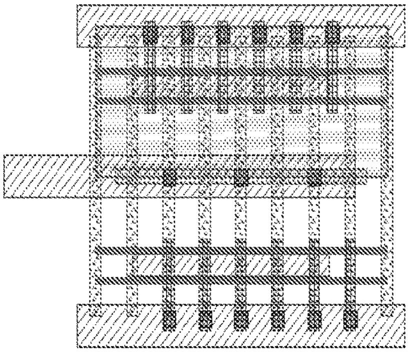
Figure 805B:
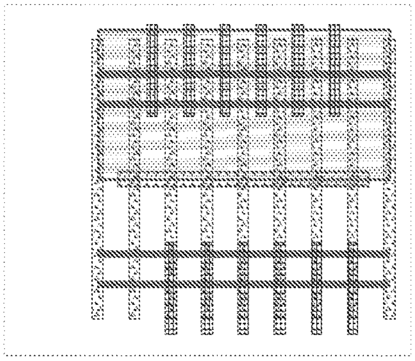
Figure 805C:
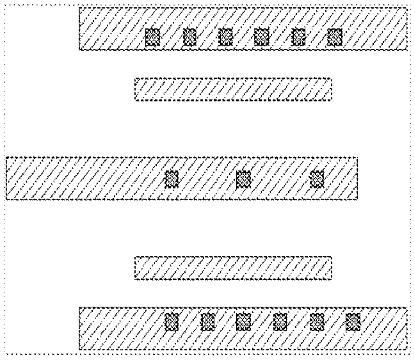
Figure 806A:
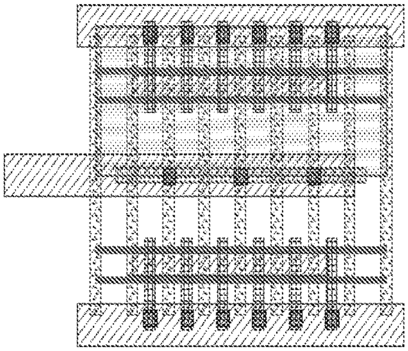
Figure 806B:
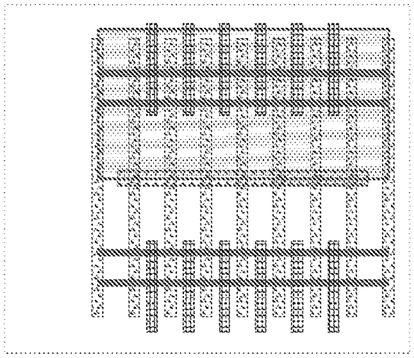
Figure 806C:
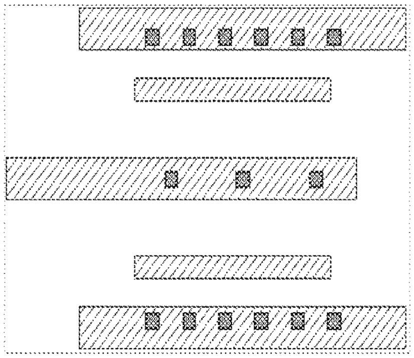
Figure 807A:
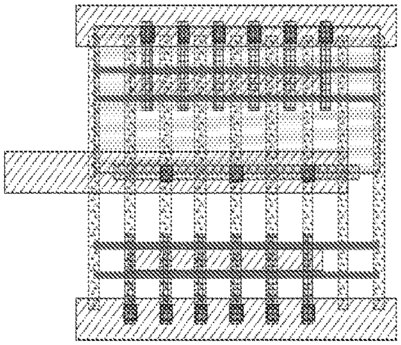
Figure 807B:
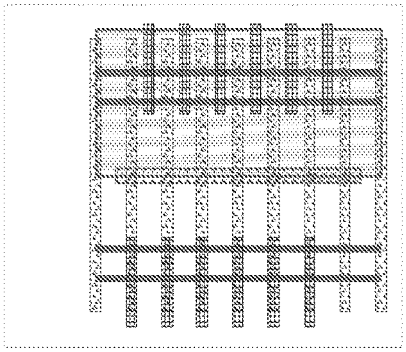
Figure 807C:
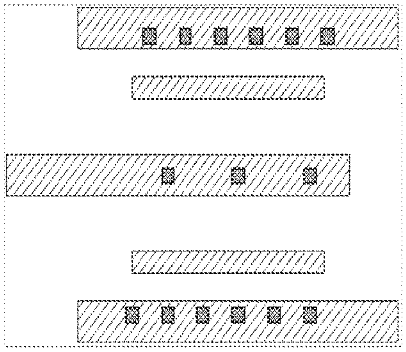
Figure 808A:
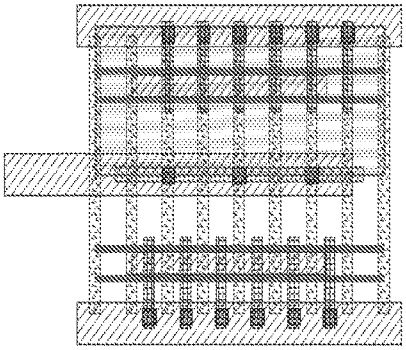
Figure 808B:
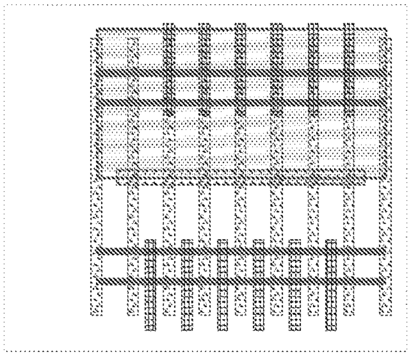
Figure 808C:
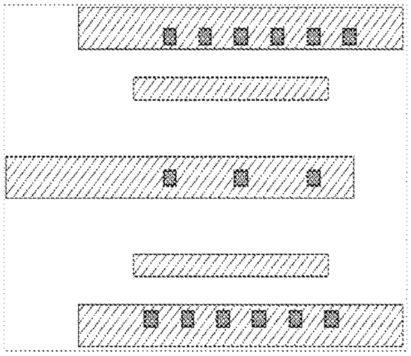
Figure 809A:
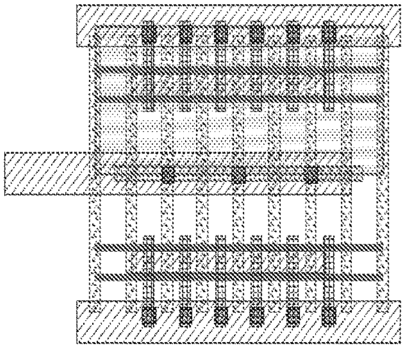
Figure 809B:
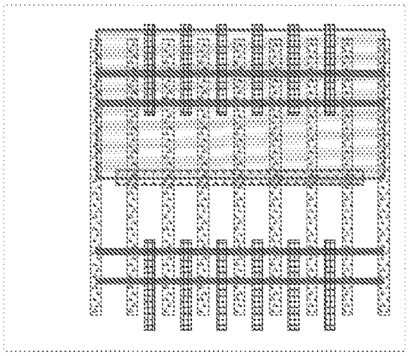
Figure 809C:
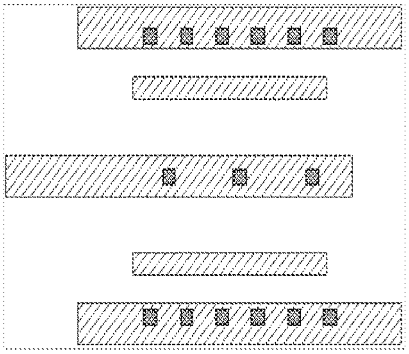
Figure 810A:
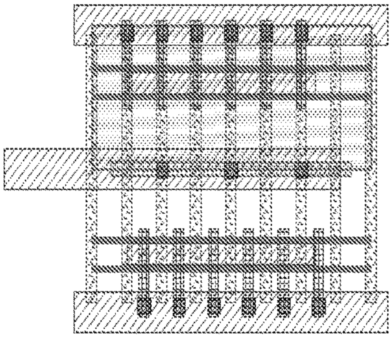
Figure 810B:
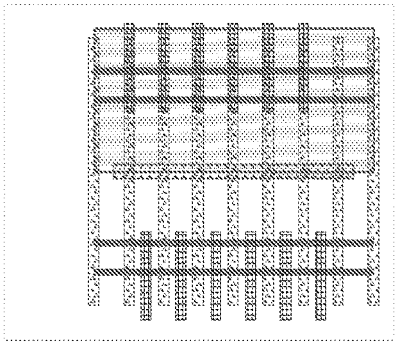
Figure 810C:
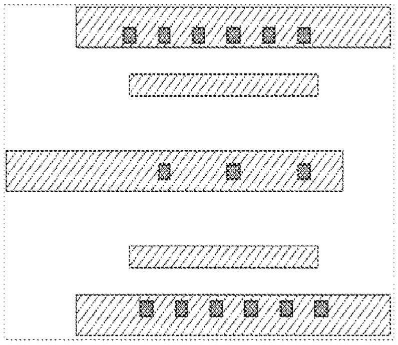
Figure 811A:
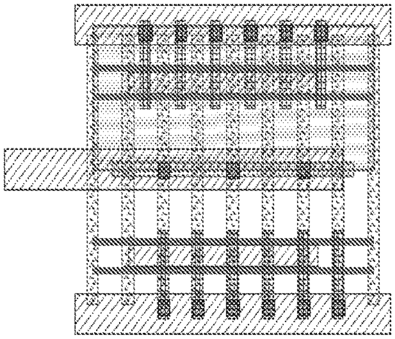
Figure 811B:
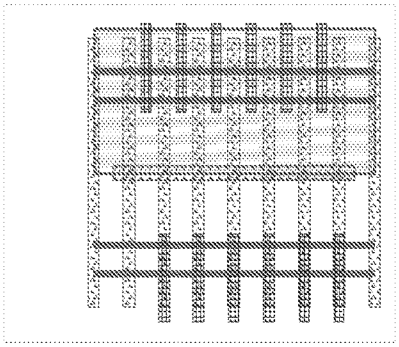
Figure 811C:
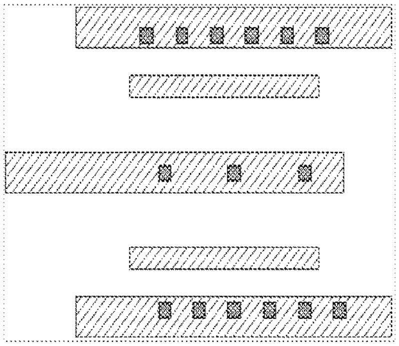
Figure 812A:
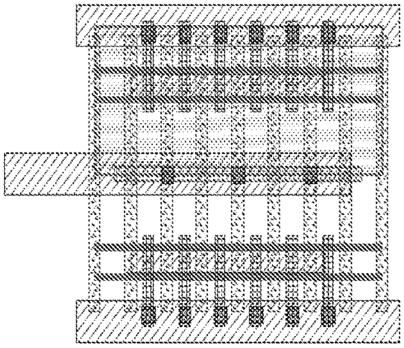
Figure 812B:
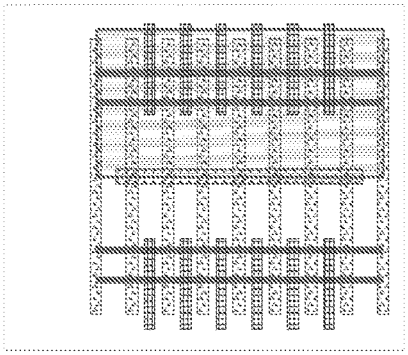
Figure 812C:
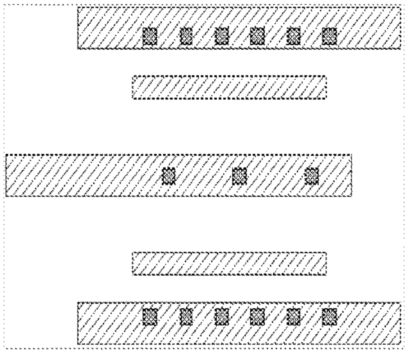
Figure 813A:
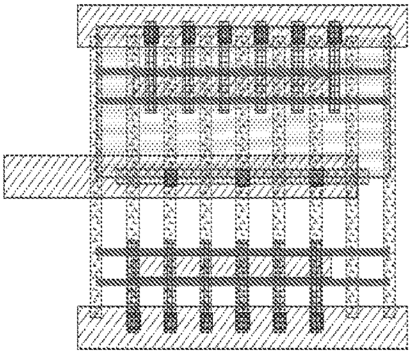
Figure 813B:
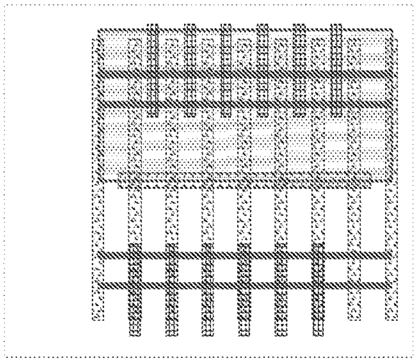
Figure 813C:
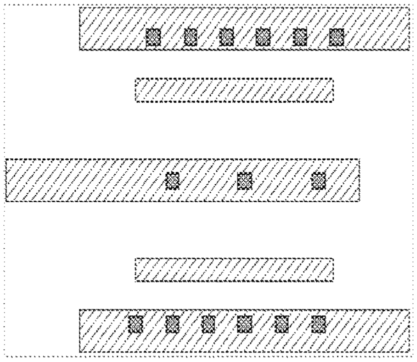
Figure 814A:
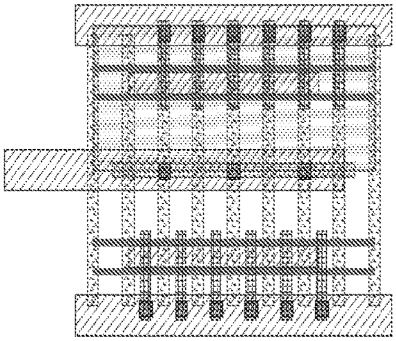
Figure 814B:
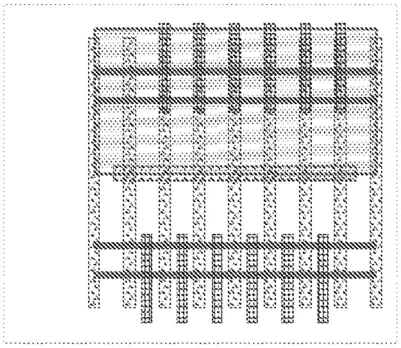
Figure 814C:
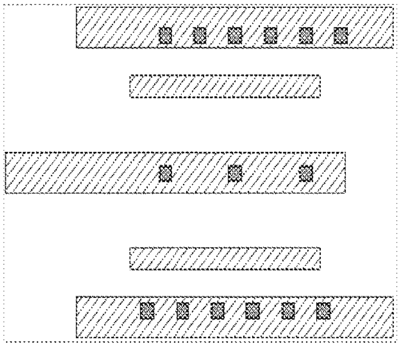
Figure 815A:
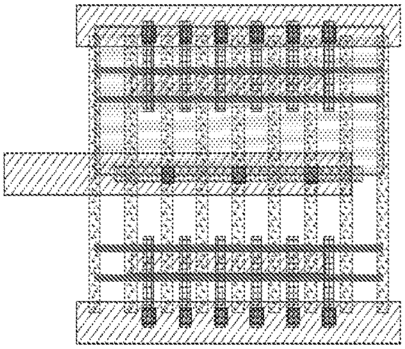
Figure 815B:
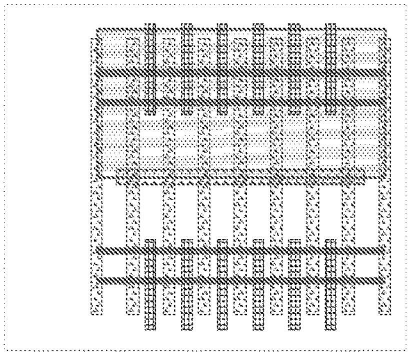
Figure 815C:
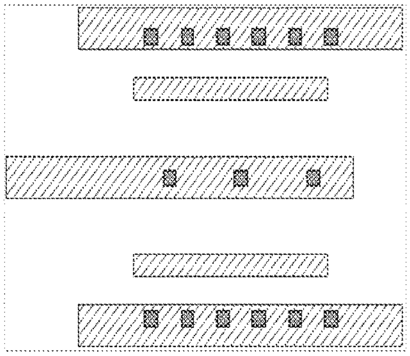
Figure 816A:
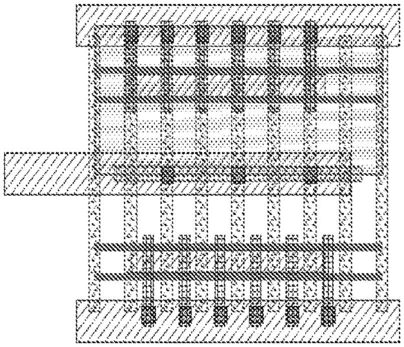
Figure 816B:
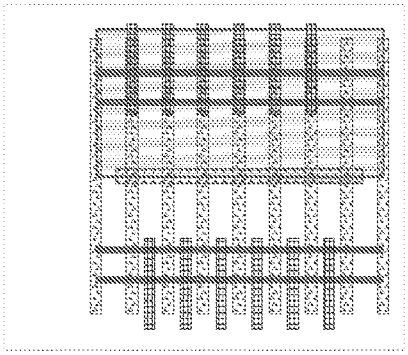
Figure 816C:
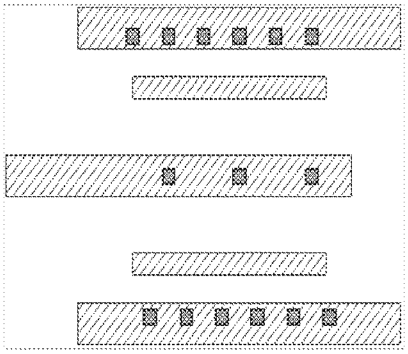
Figure 817A:
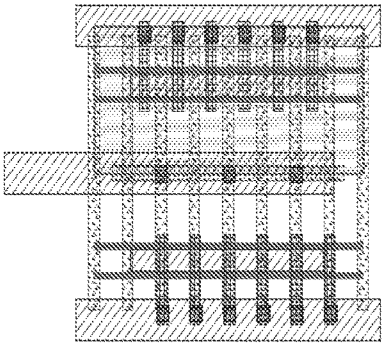
Figure 817B:
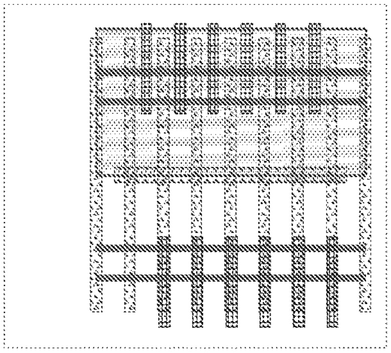
Figure 817C:
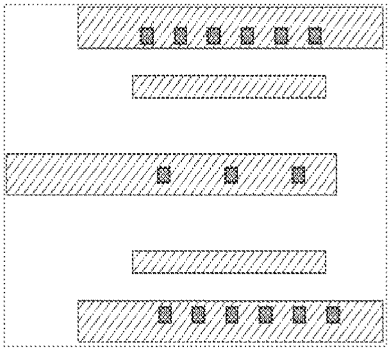
Figure 818A:
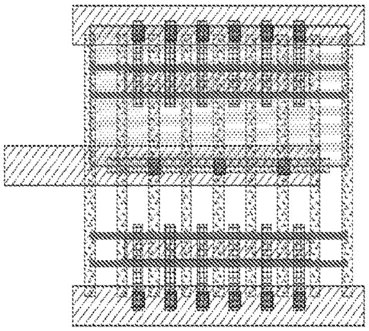
Figure 818B:
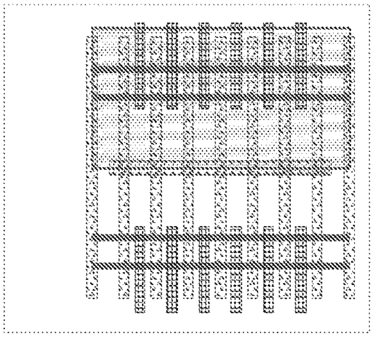
Figure 818C:
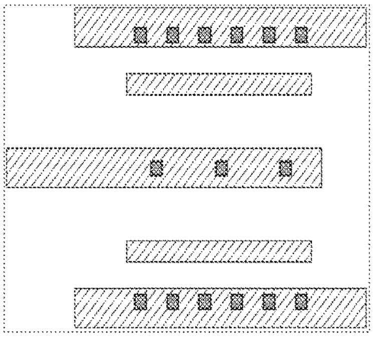
Figure 819A:
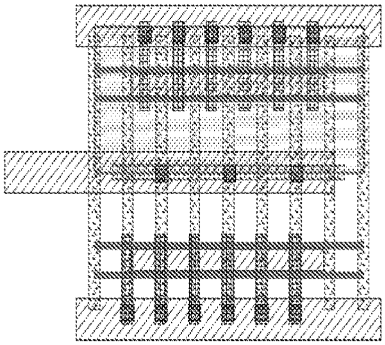
Figure 819B:
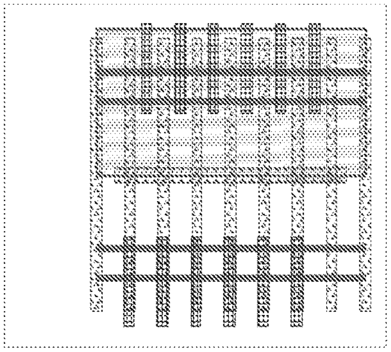
Figure 819C:
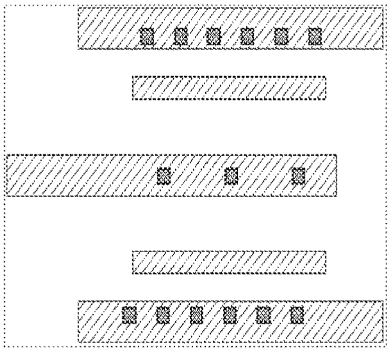
Figure 820A:
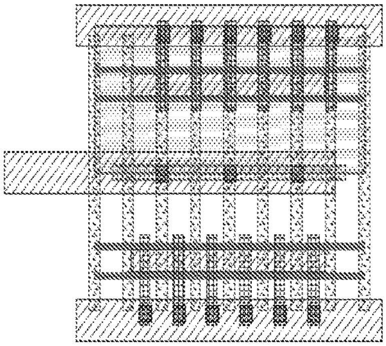
Figure 820B:
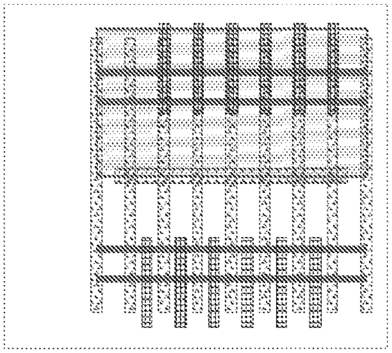
Figure 820C:
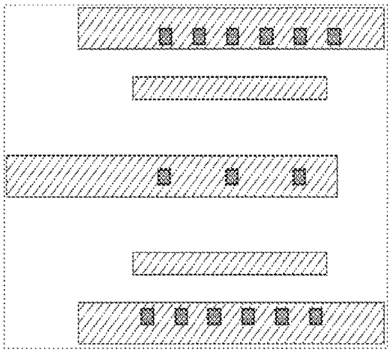
Figure 821A:
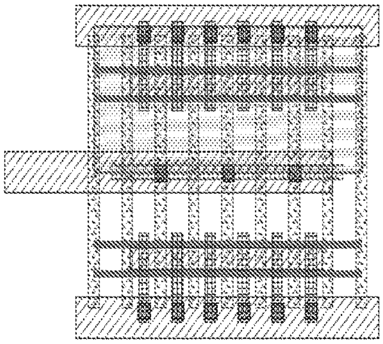
Figure 821B:
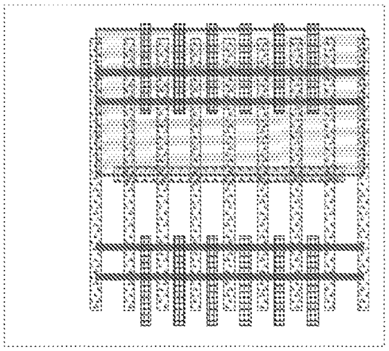
Figure 821C:
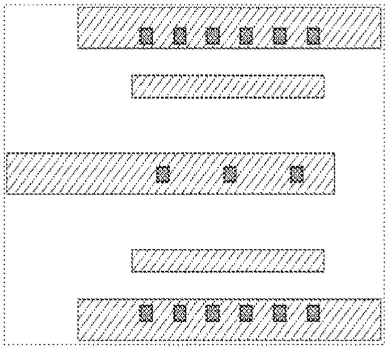
Figure 822A:
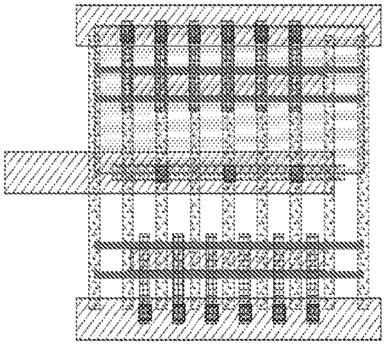
Figure 822B:
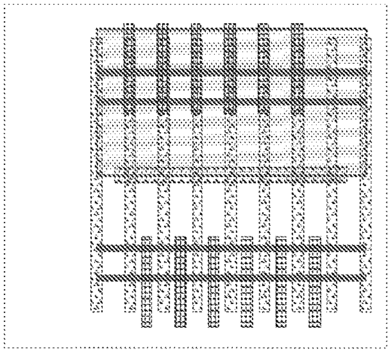
Figure 822C:
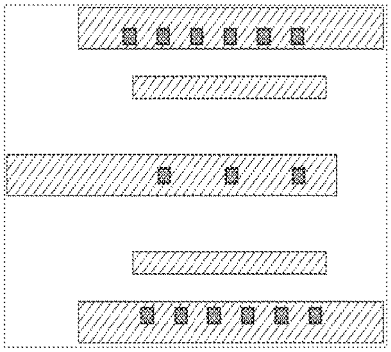
Figure 823A:
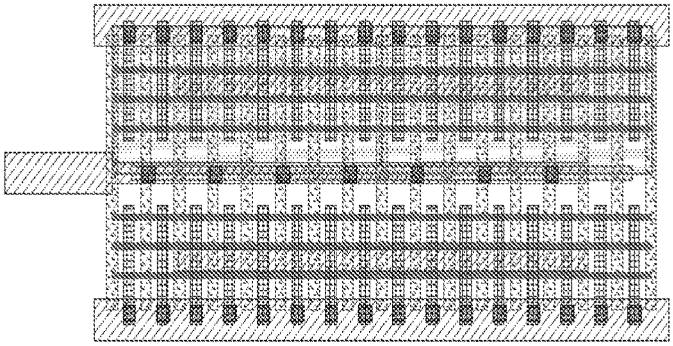
Figure 823B:
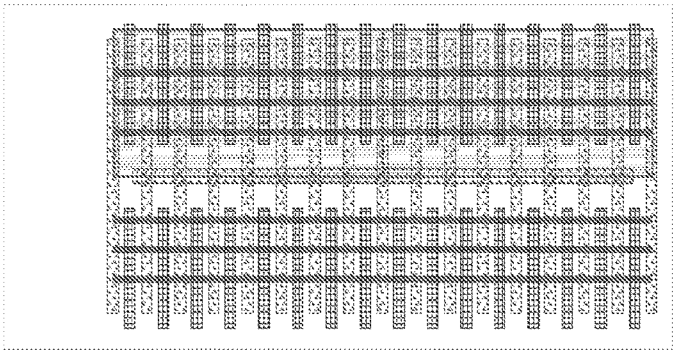
Figure 823C:
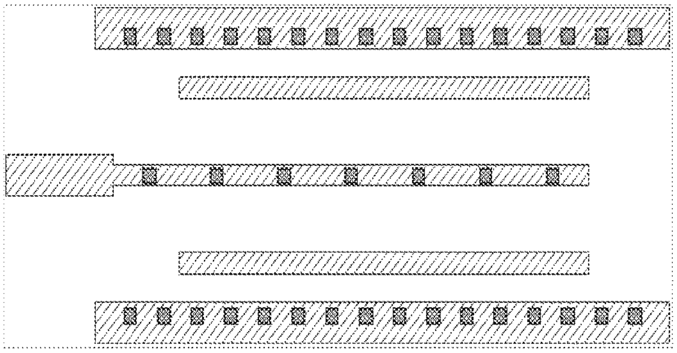
Figure 824A:
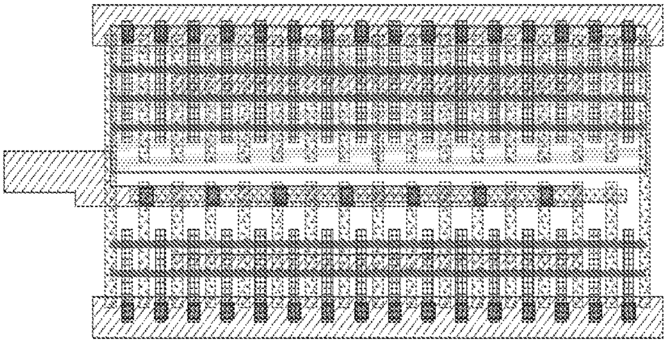
Figure 824B:
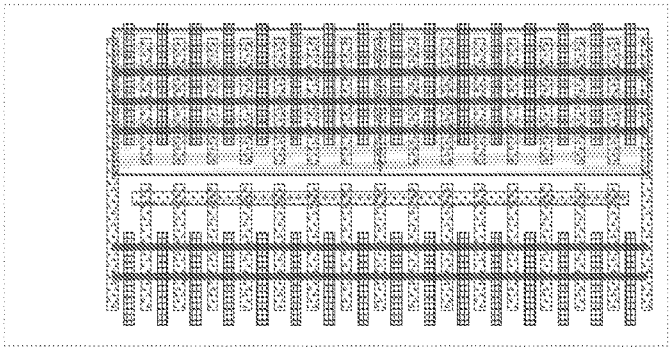
Figure 824C:
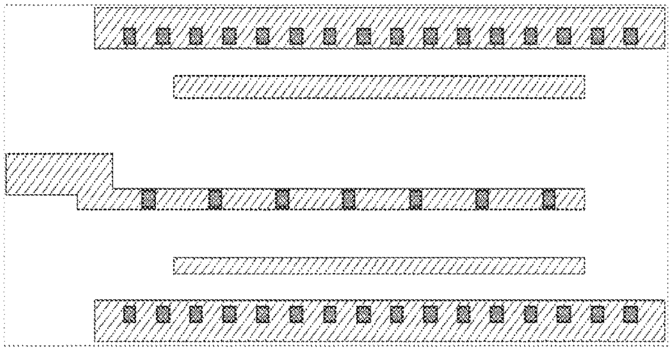
Figure 825A:
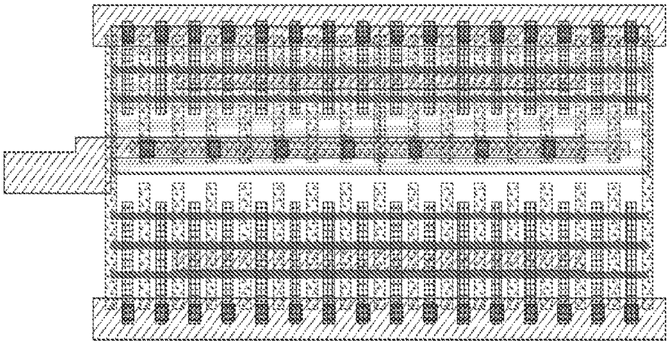
Figure 825B:
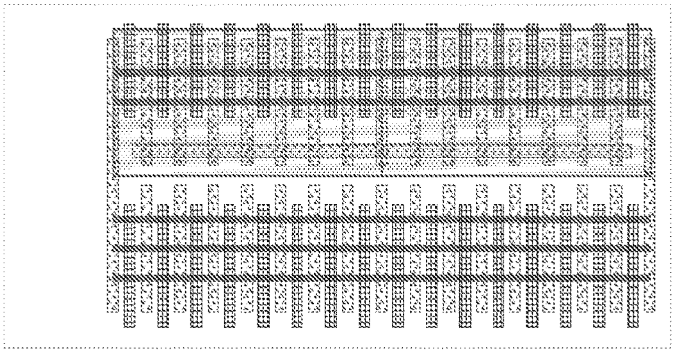
Figure 825C:
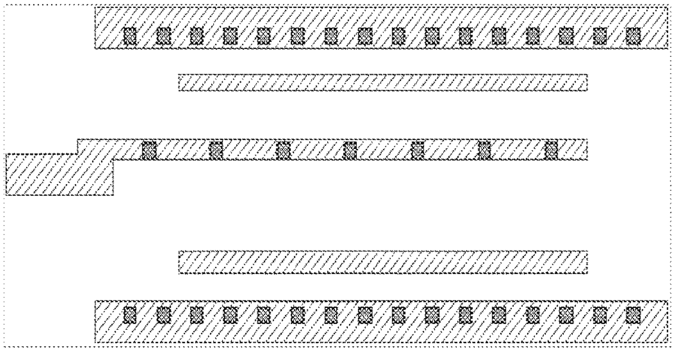
Figure 826A:
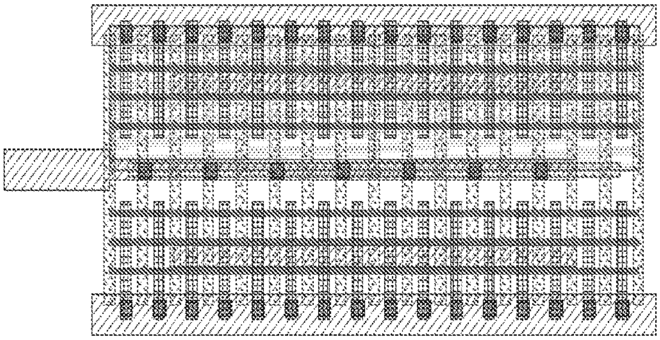
Figure 826B:
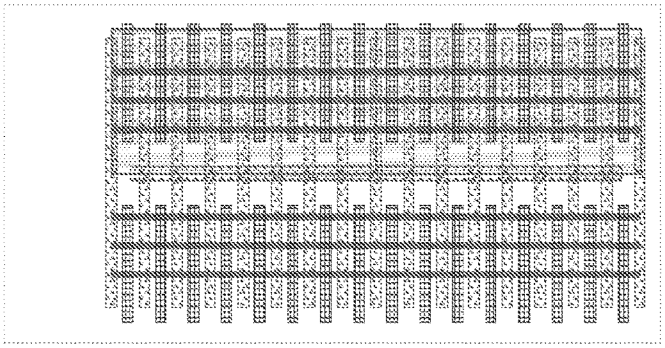
Figure 826C:
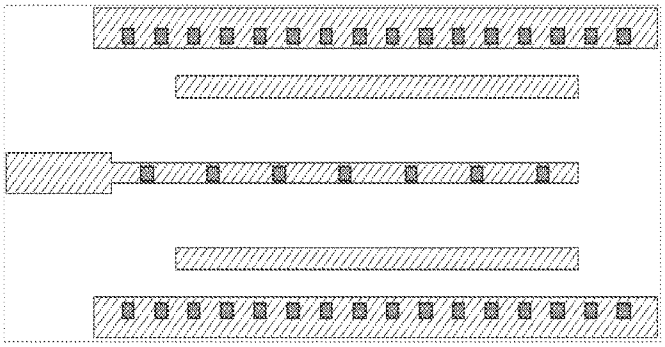
Figure 827A:
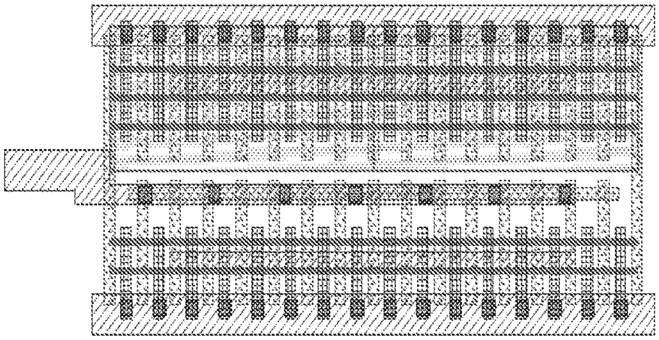
Figure 827B:
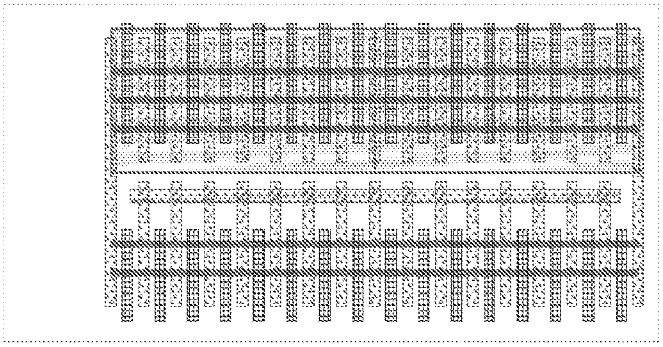
Figure 827C:
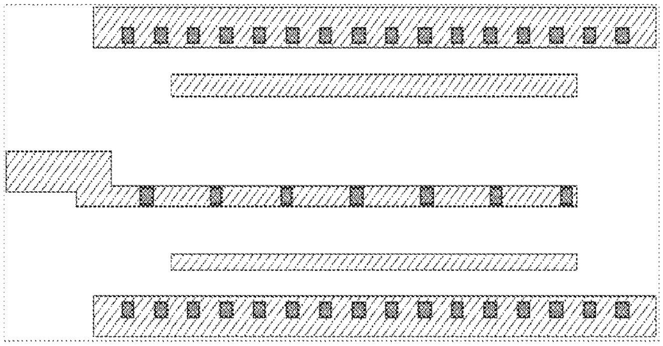
Figure 828A:
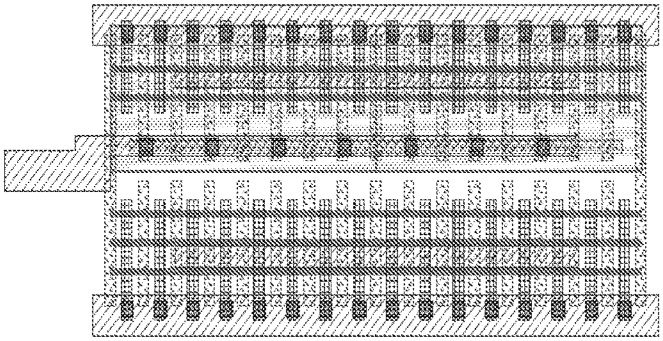
Figure 828B:
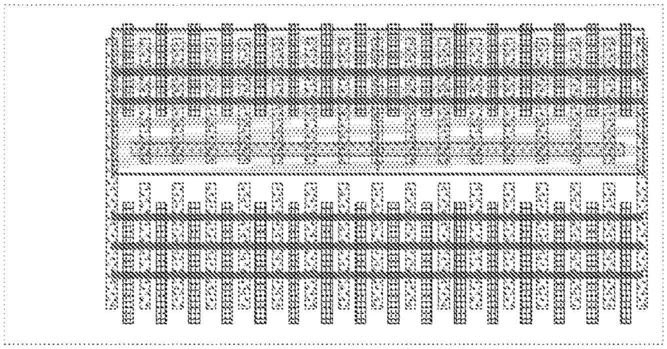
Figure 828C:
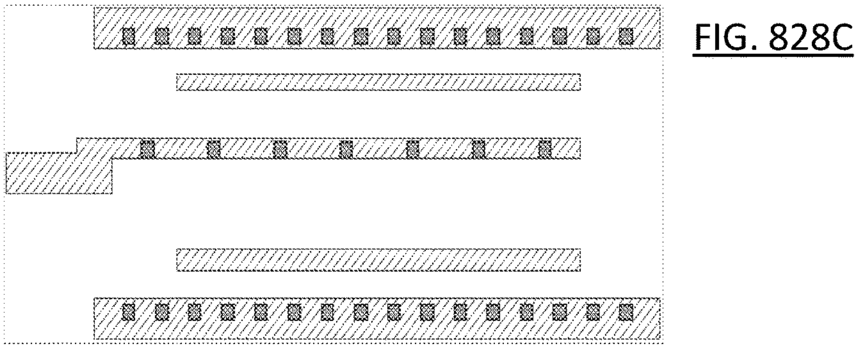
Figure 829A:
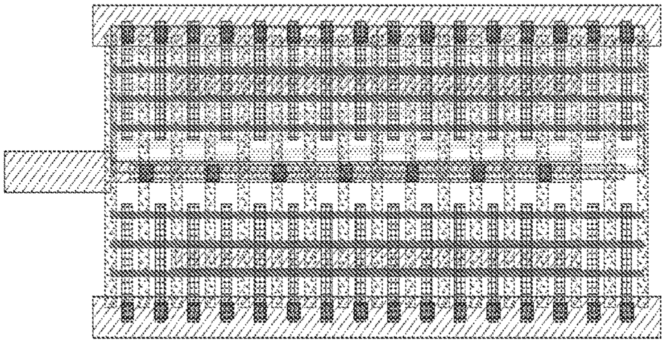
Figure 829B:
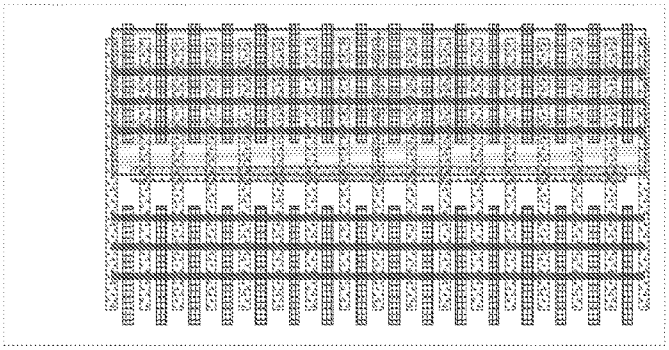
Figure 829C:
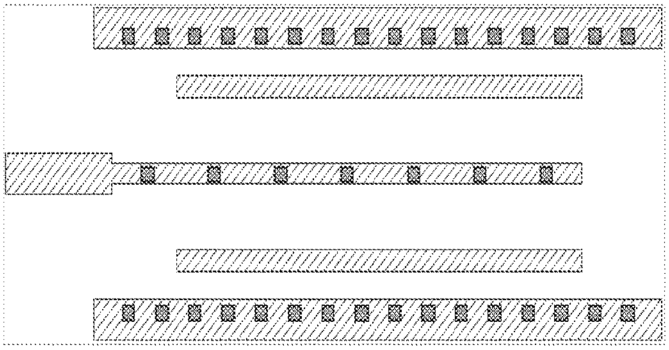
Figure 830A:
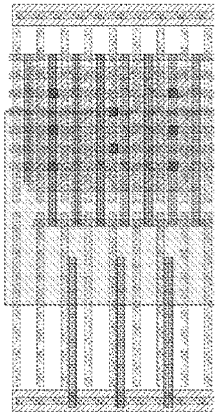
Figure 830B:
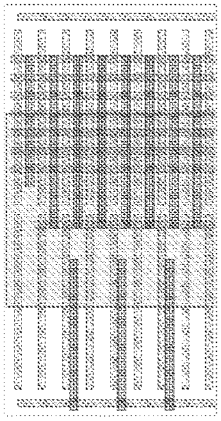
Figure 830C:
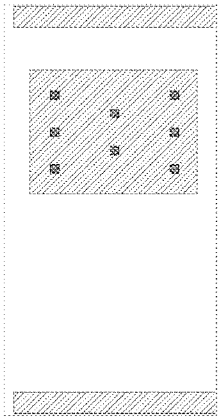
Figure 831A:
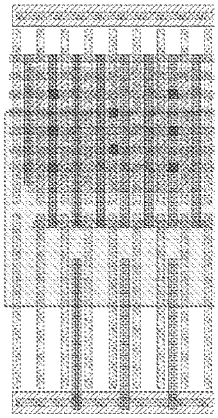
Figure 831B:
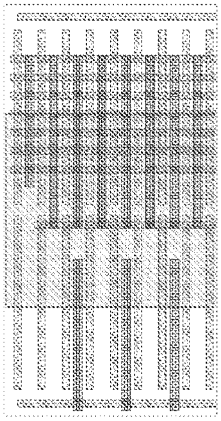
Figure 831C:
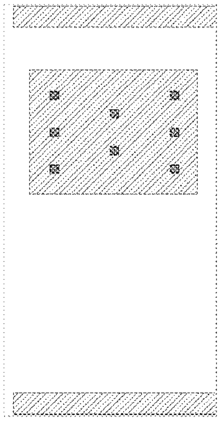
Figure 832A:
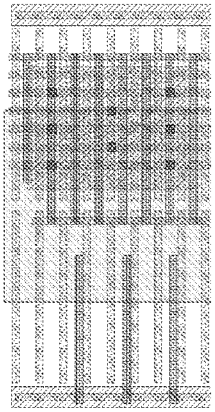
Figure 832B:
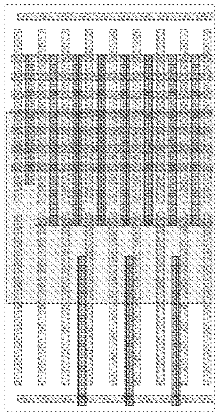
Figure 832C:
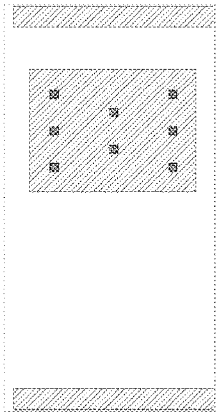
Figure 833A:
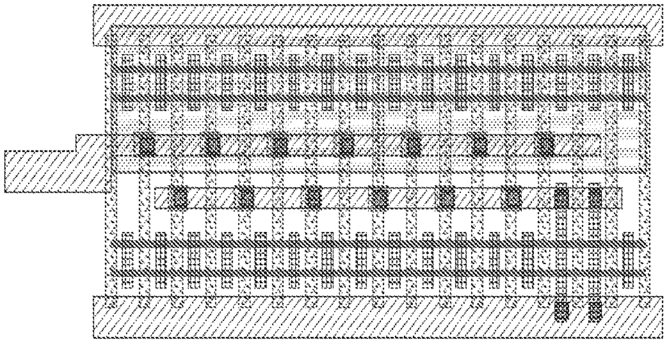
Figure 833B:
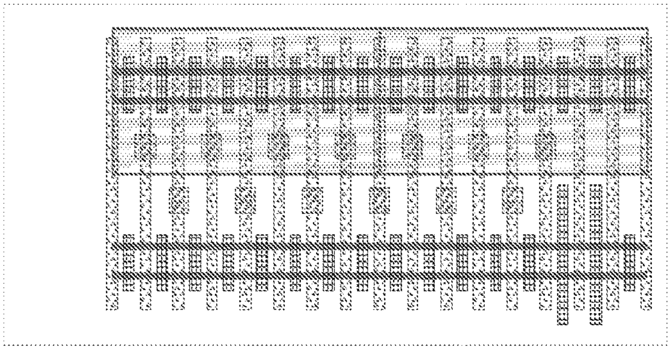
Figure 833C:
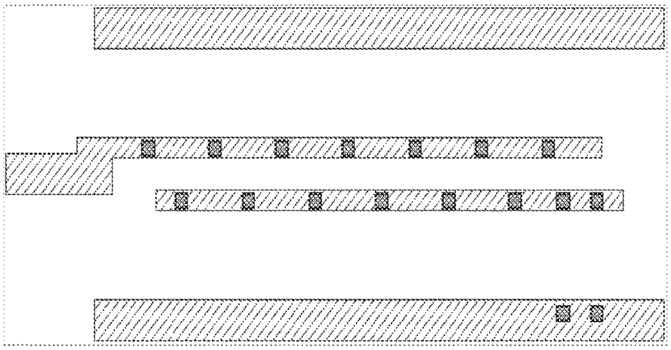
Figure 834A:
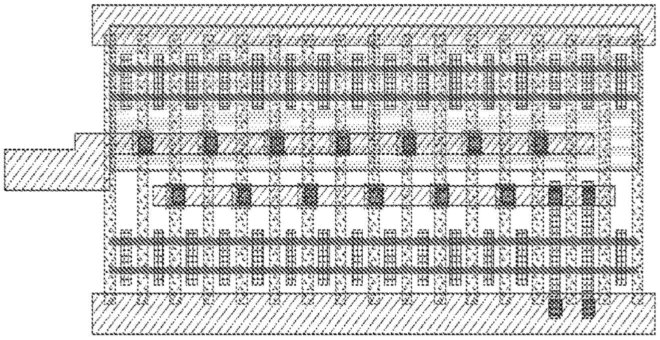
Figure 834B:
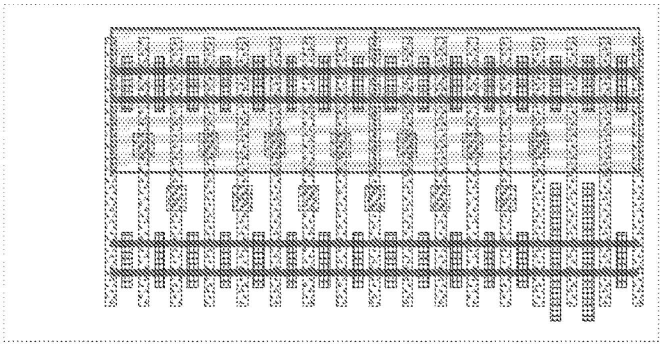
Figure 834C:
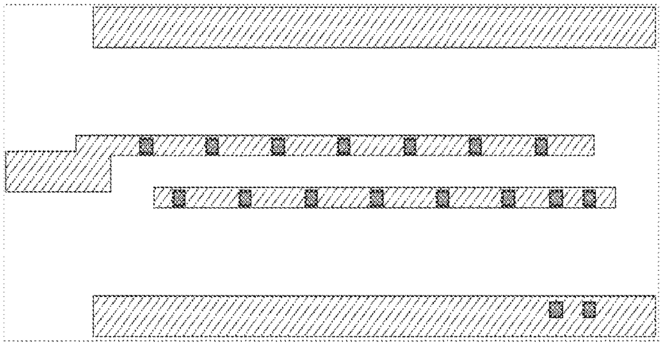
Figure 835A:
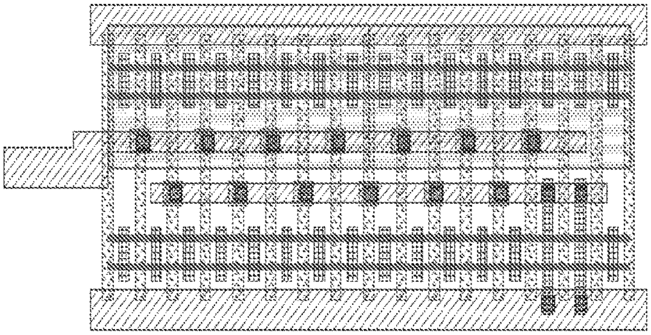
Figure 835B:
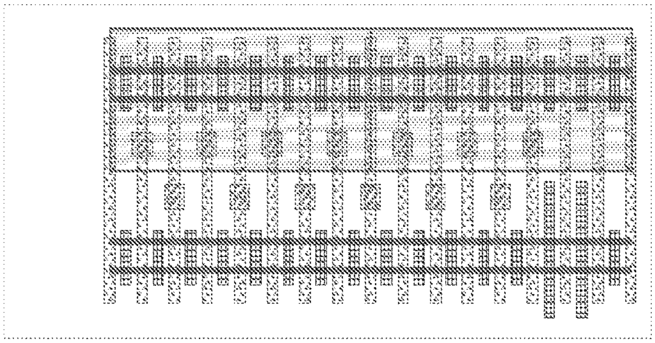
Figure 835C:
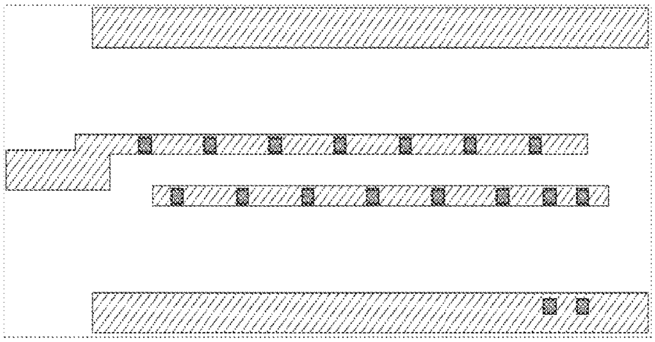
Figure 836A:
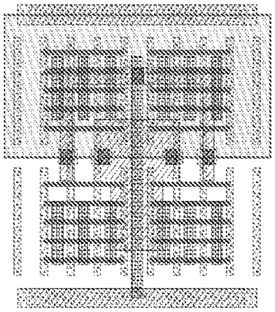
Figure 836B:
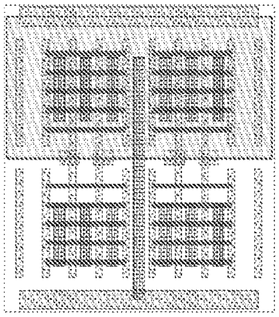
Figure 836C:
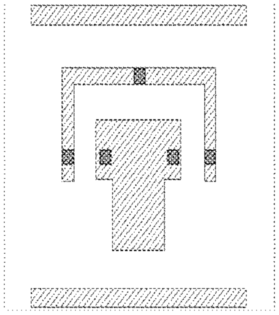
Figure 837A:
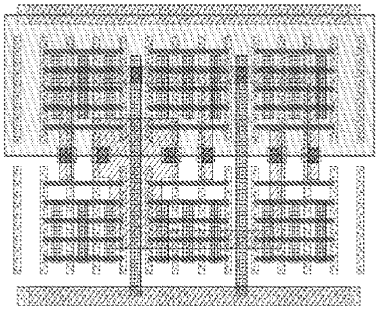
Figure 837B:
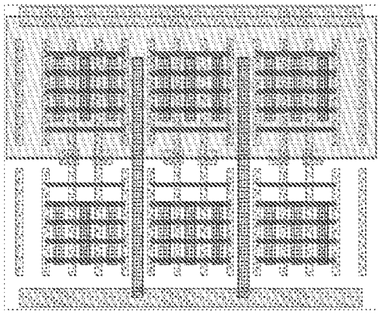
Figure 837C:
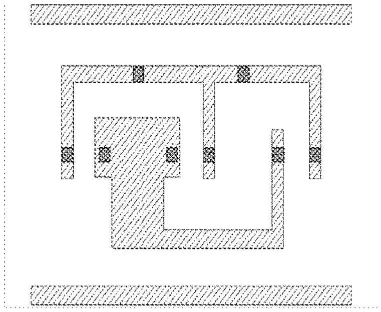
Figure 838A:
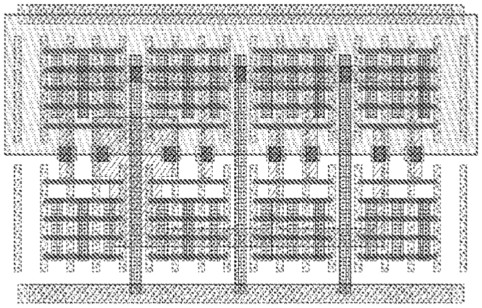
Figure 838B:
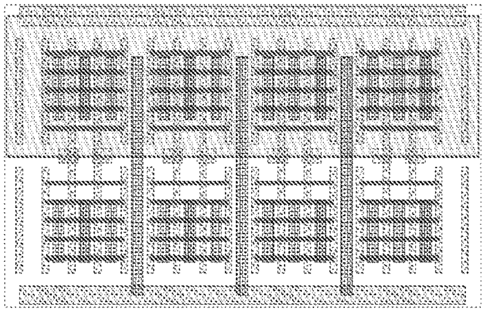
Figure 838C:
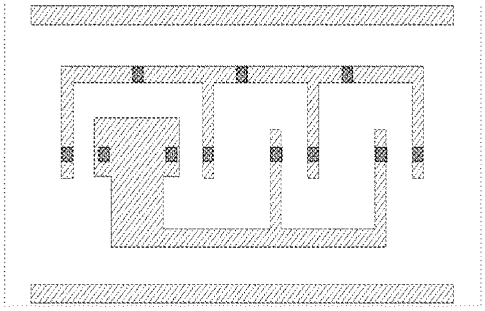
Figure 839A:
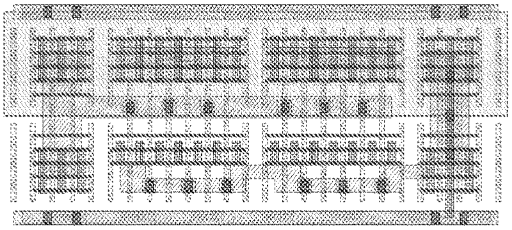
Figure 839B:
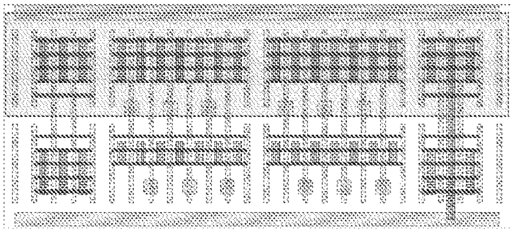
Figure 839C:
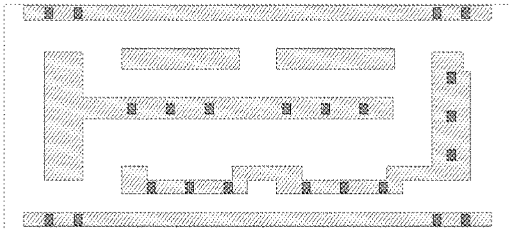
Figure 840A:
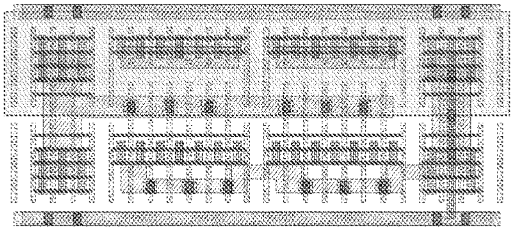
Figure 840B:
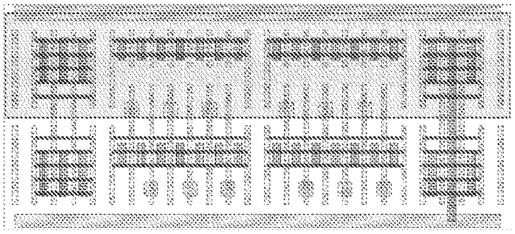
Figure 840C:
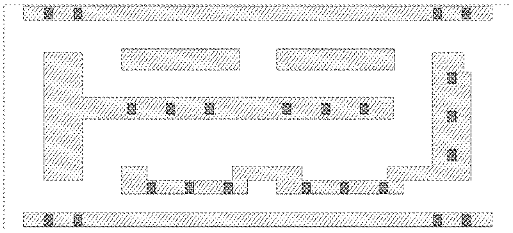
Figure 841A:
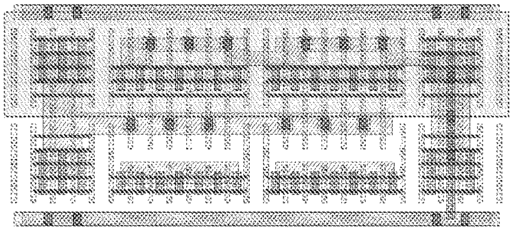
Figure 841B:
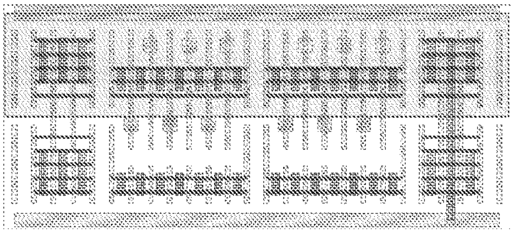
Figure 841C:
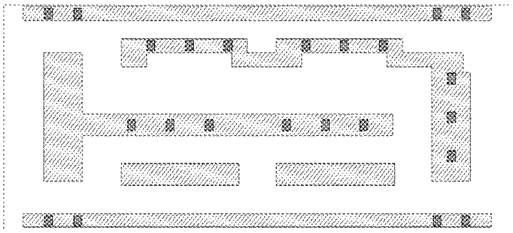
Figure 842A:
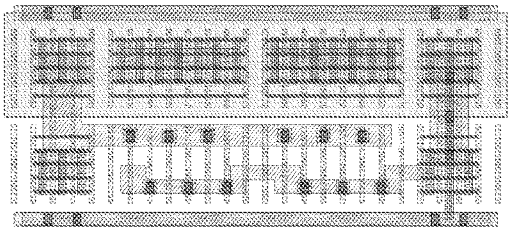
Figure 842B:
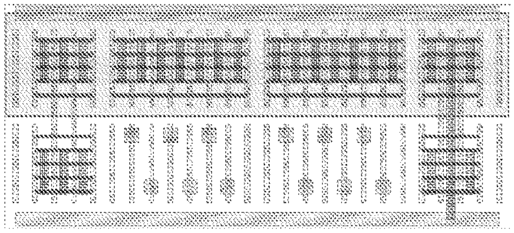
Figure 842C:
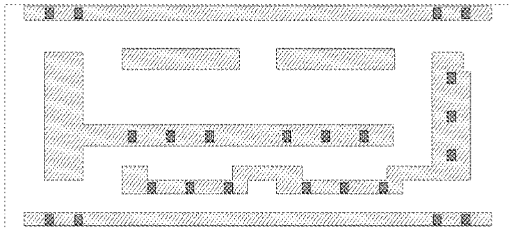
Figure 843A:
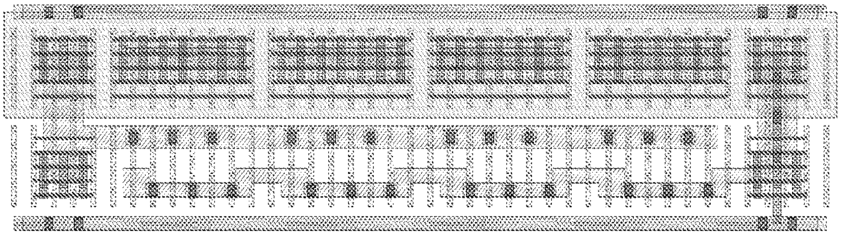
Figure 843B:
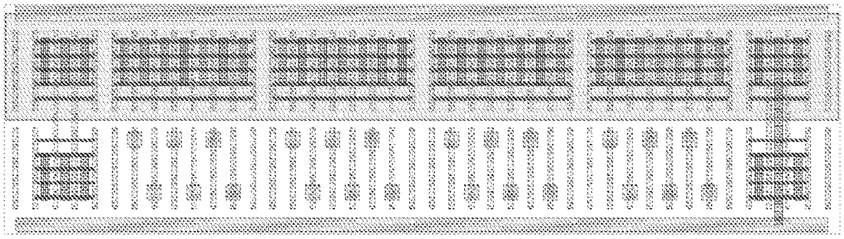
Figure 843C:
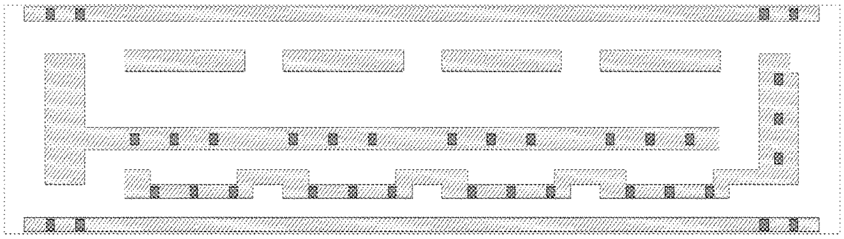
Figure 844A:
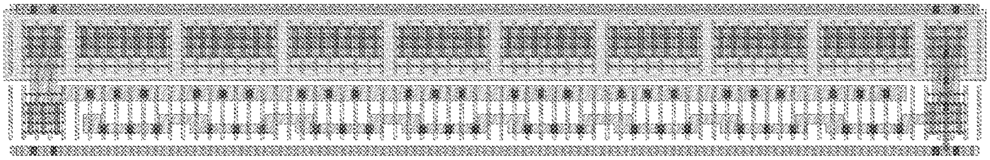
Figure 844B:
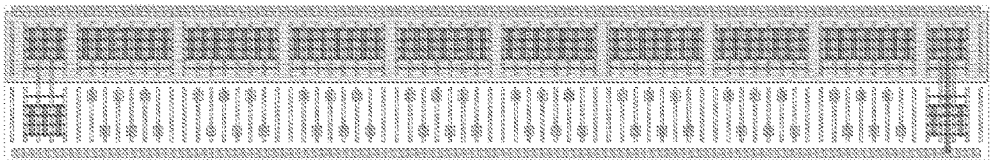
Figure 844C:
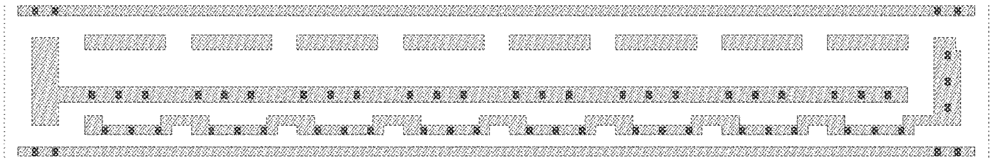
Figure 845A:
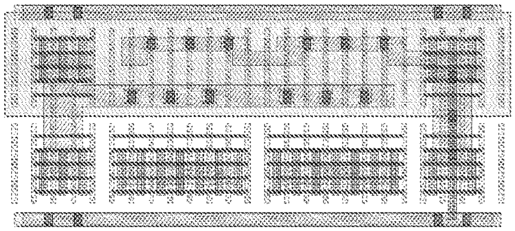
Figure 845B:
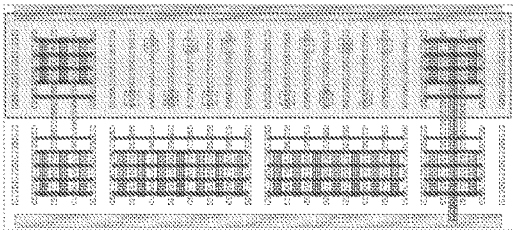
Figure 845C:
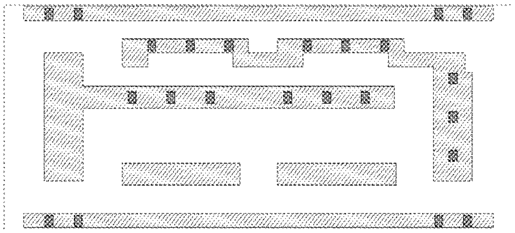
Figure 846A:
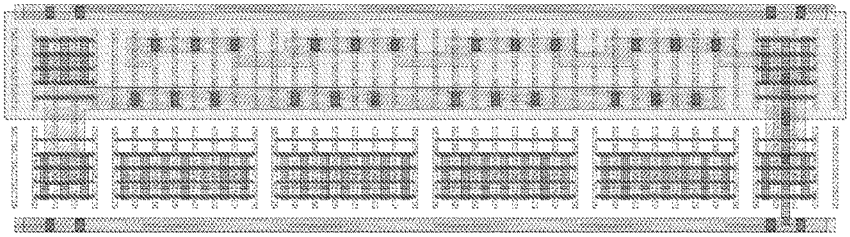
Figure 846B:
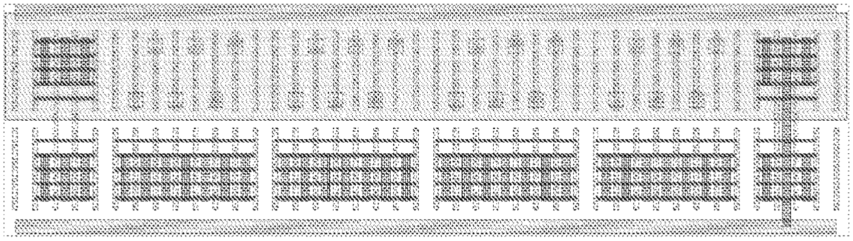
Figure 846C:
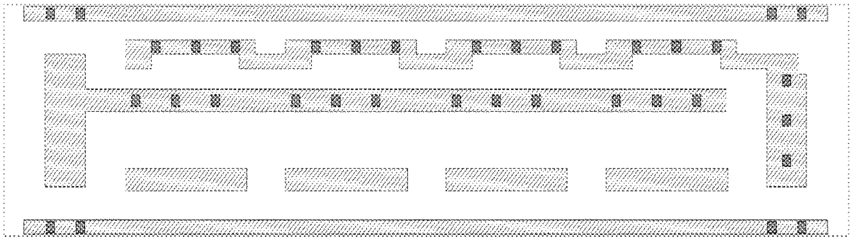
Figure 847A:
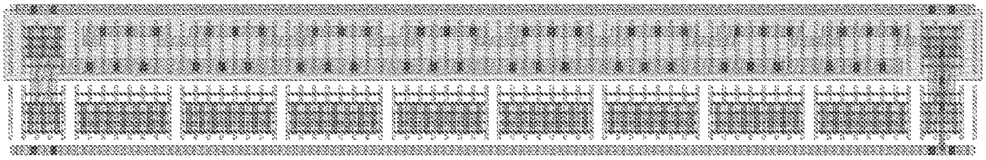
Figure 847B:
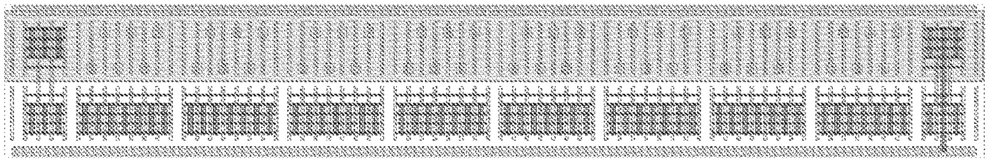
Figure 847C:
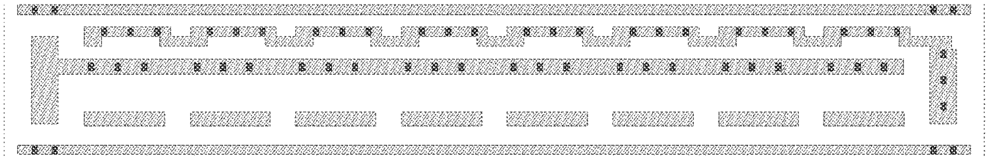
Figure 848A:
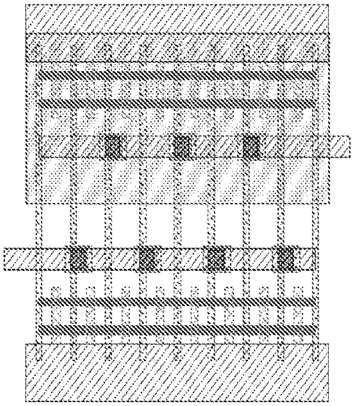
Figure 848B:
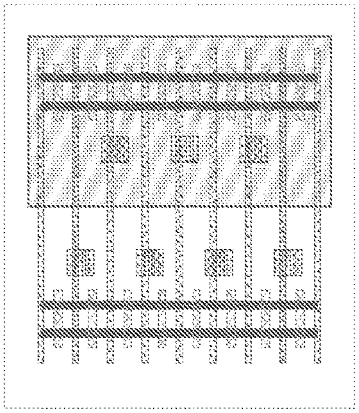
Figure 848C:
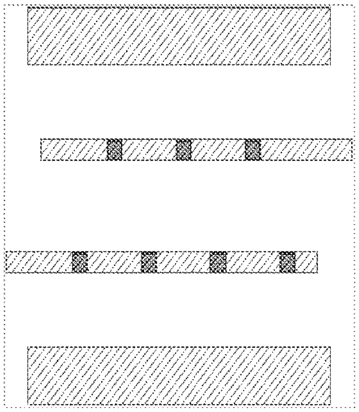
Figure 849A:
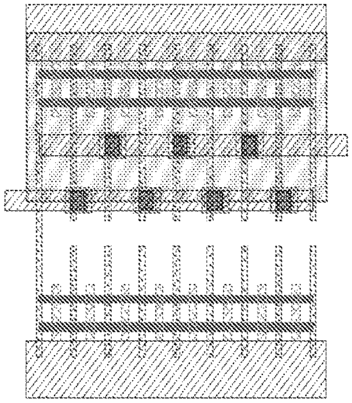
Figure 849B:
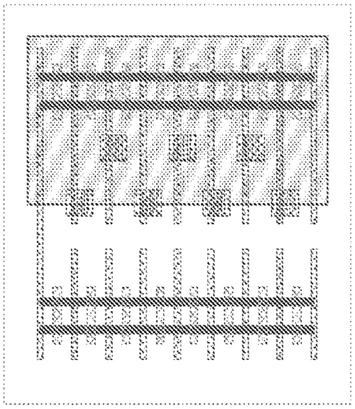
Figure 849C:
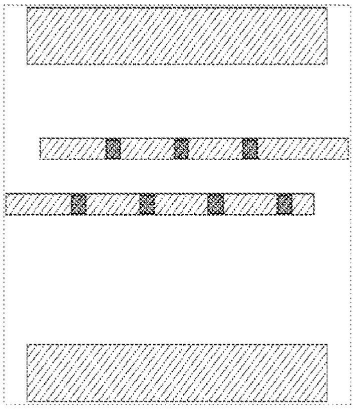
Figure 850A:
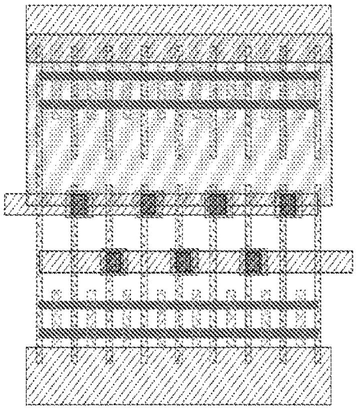
Figure 850B:
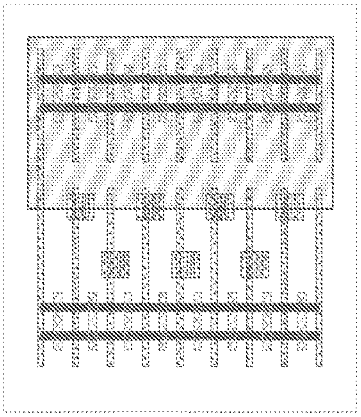
Figure 850C:
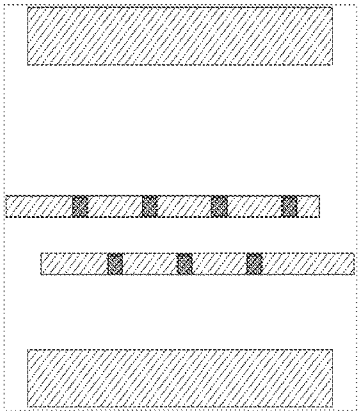
Figure 851A:
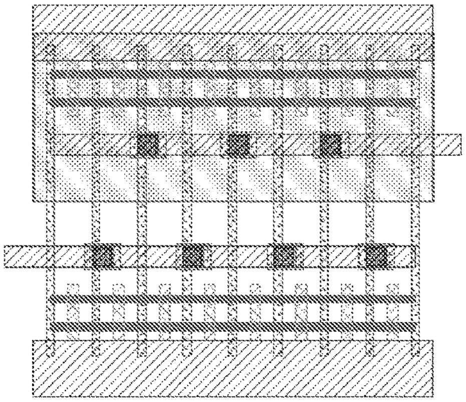
Figure 851B:
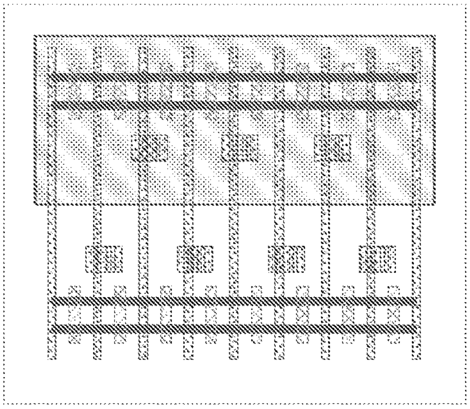
Figure 851C:
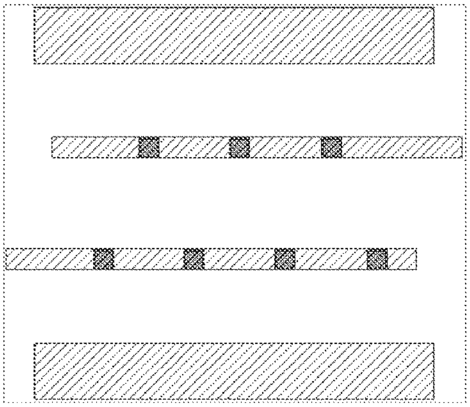
Figure 852A:
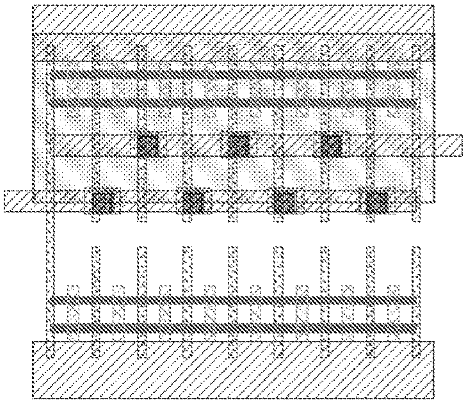
Figure 852B:
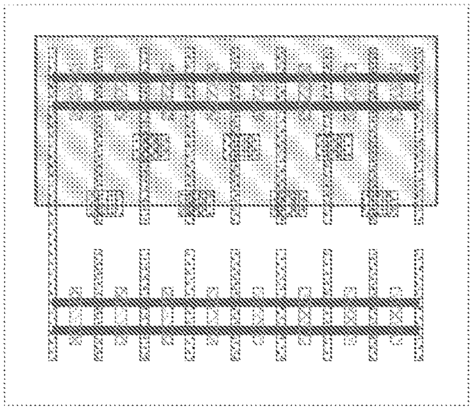
Figure 852C:
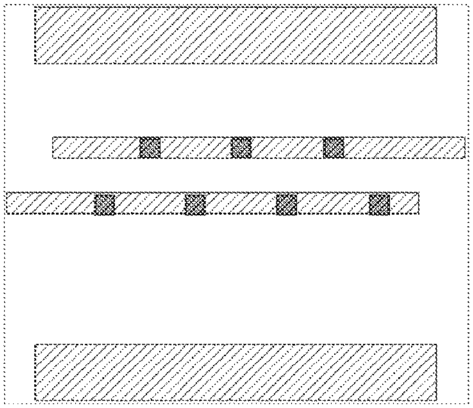
Figure 853A:
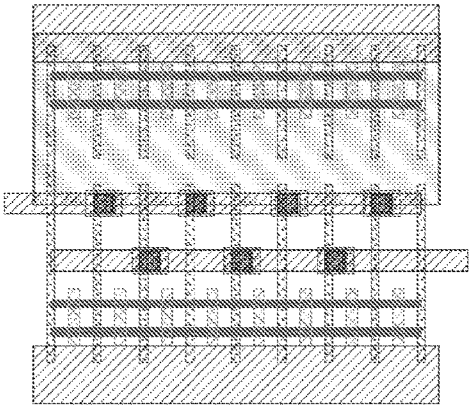
Figure 853B:
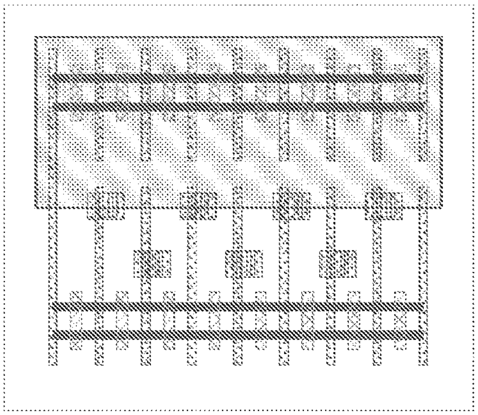
Figure 853C:
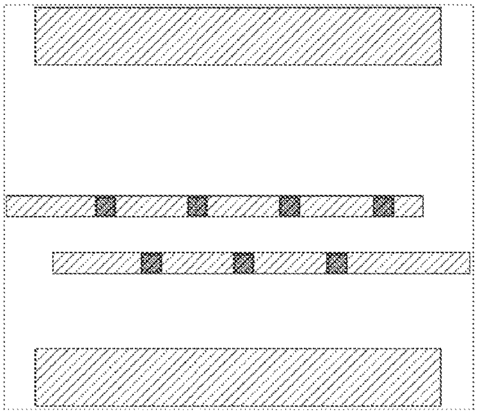
Figure 854A:
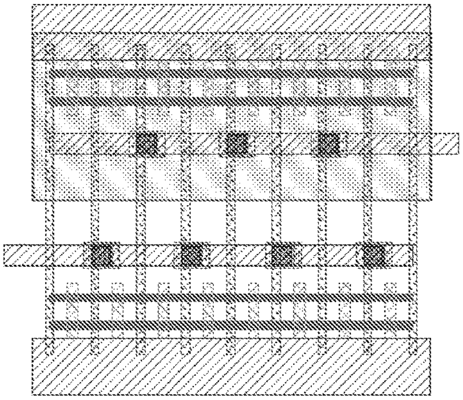
Figure 854B:
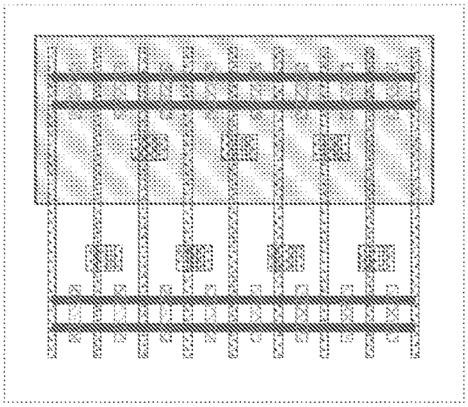
Figure 854C:
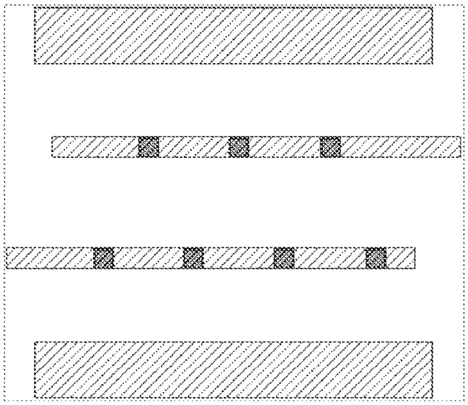
Figure 855A:
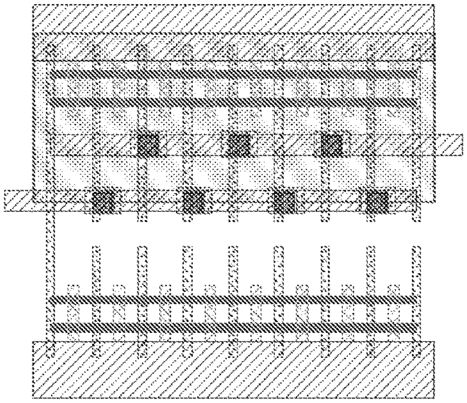
Figure 855B:
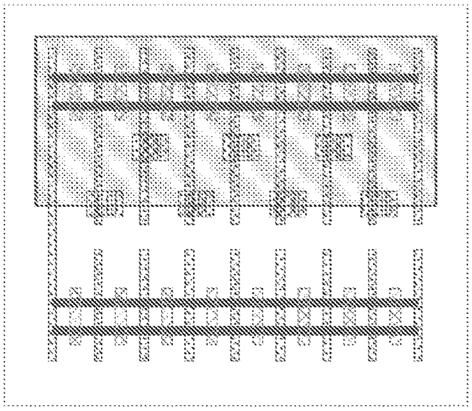
Figure 855C:
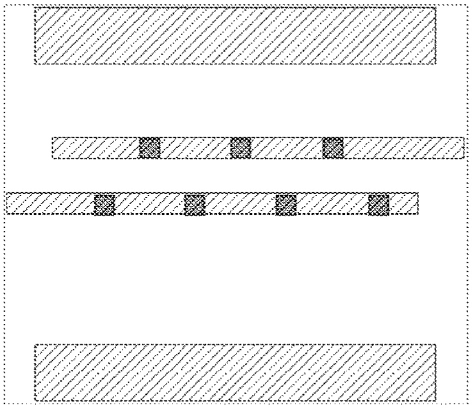
Figure 856A:
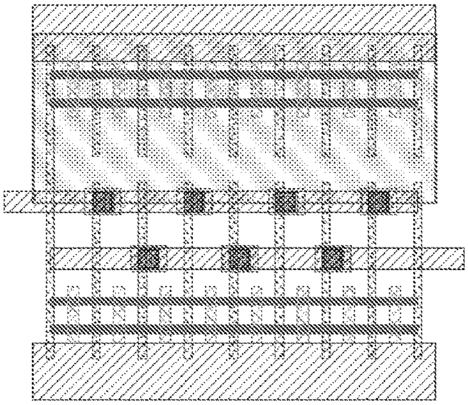
Figure 856B:
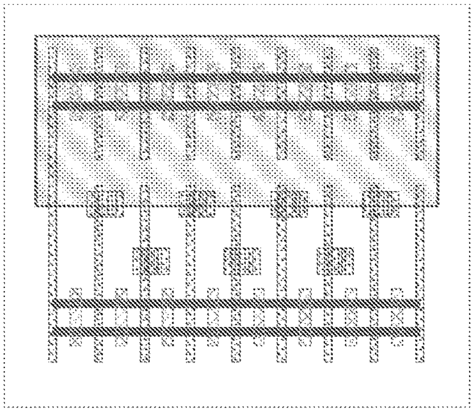
Figure 856C:
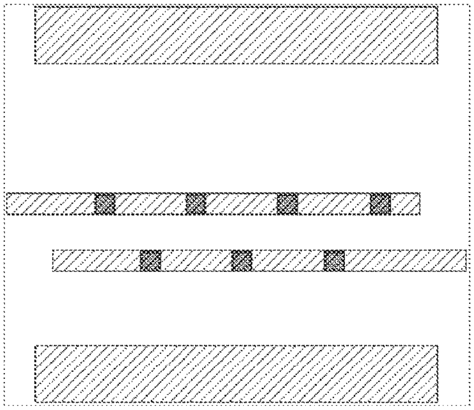
Figure 857A:
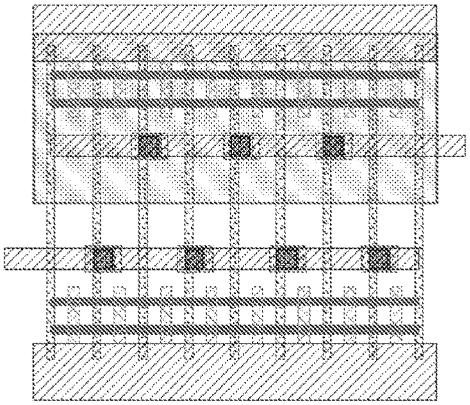
Figure 857B:
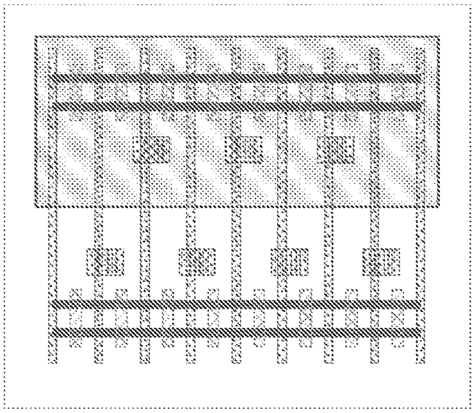
Figure 857C:
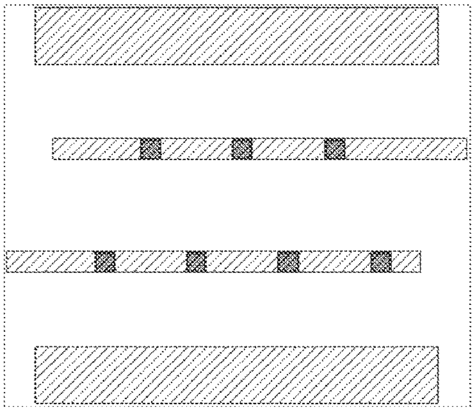
Figure 858A:
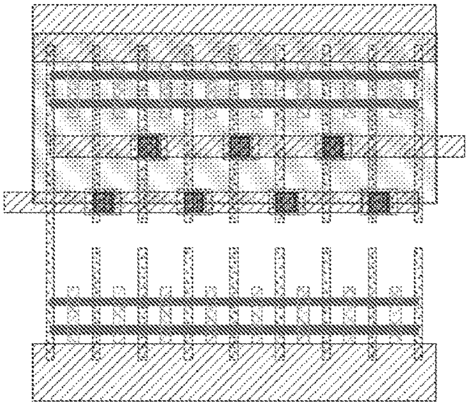
Figure 858B:
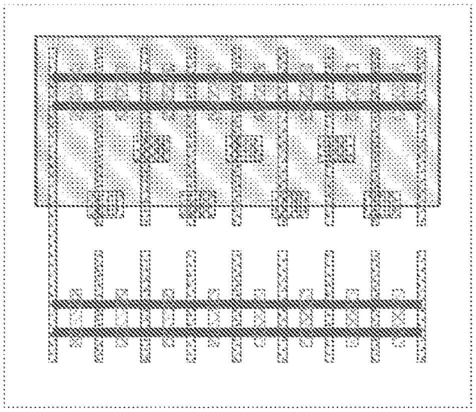
Figure 858C:
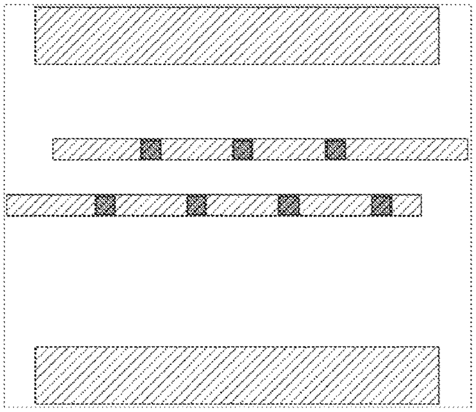
Figure 859A:
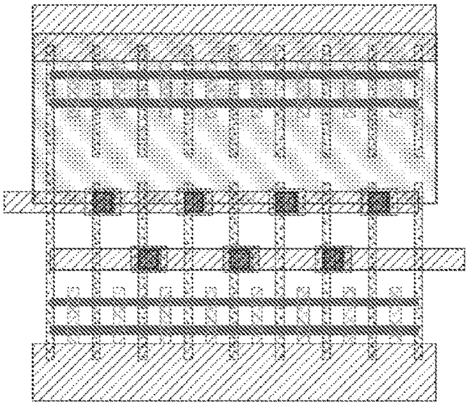
Figure 859B:
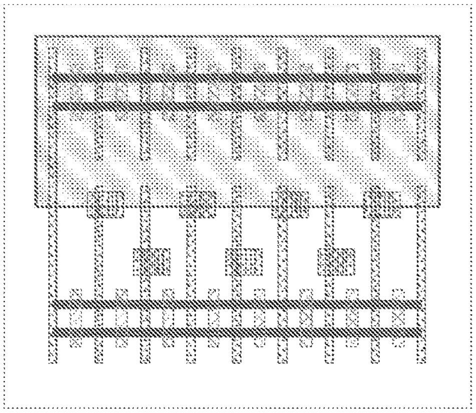
Figure 859C:
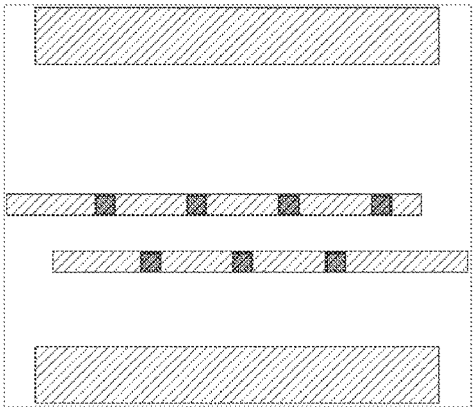
Figure 860A:
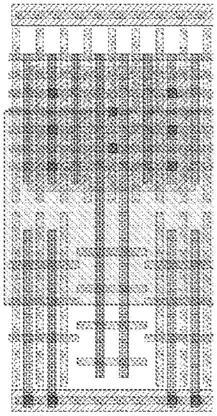
Figure 860B:
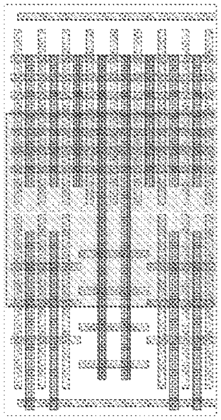
Figure 860C:
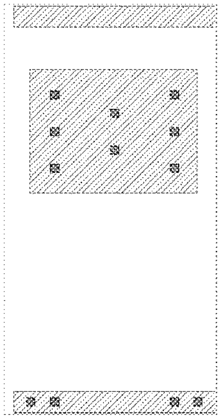
Figure 861A:
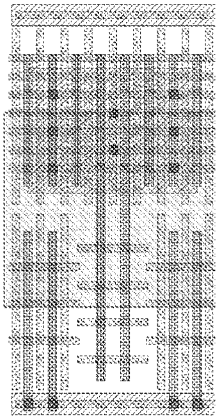
Figure 861B:
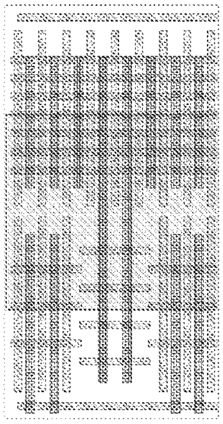
Figure 861C:
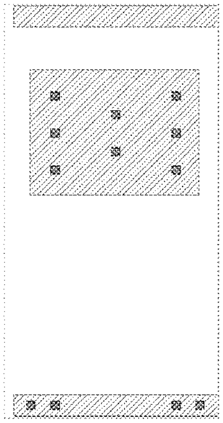
Figure 862A:
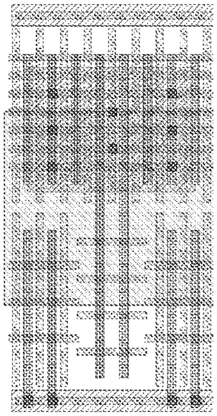
Figure 862B:
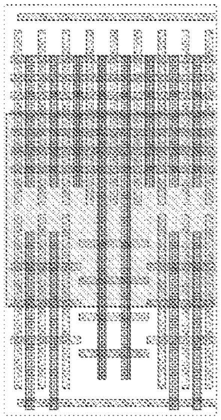
Figure 862C:
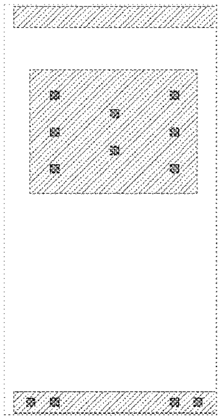
Figure 863A:
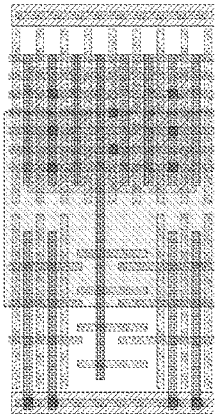
Figure 863B:
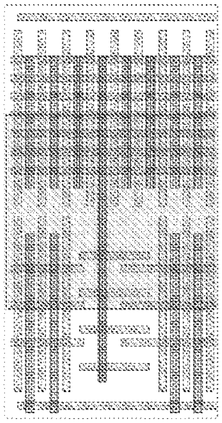
Figure 863C:
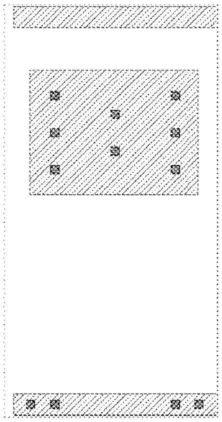
Figure 864A:
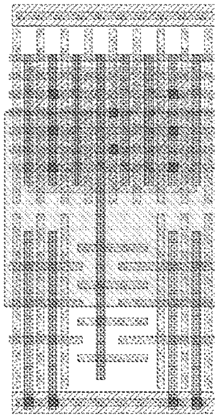
Figure 864B:
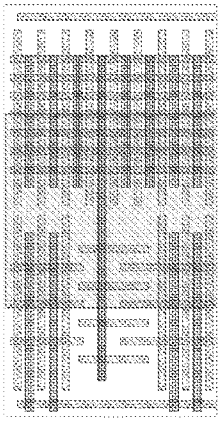
Figure 864C:
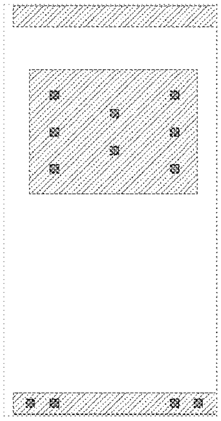
Figure 865A:
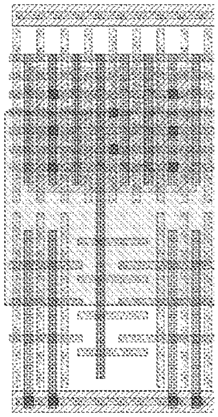
Figure 865B:
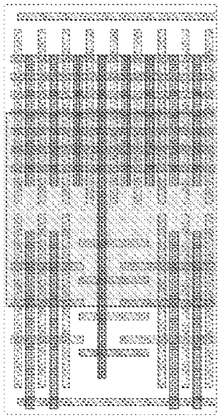
Figure 865C:
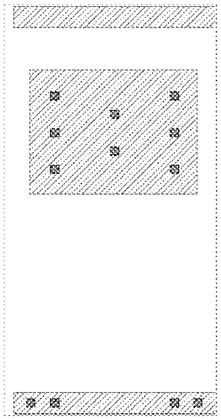
Figure 866A:
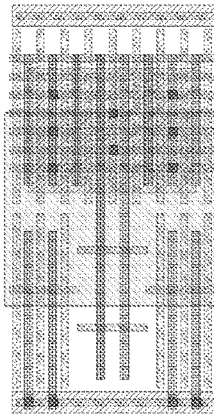
Figure 866B:
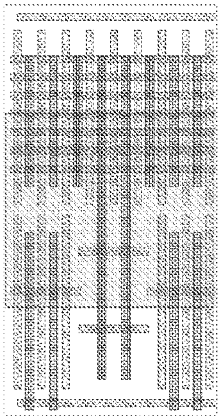
Figure 866C:
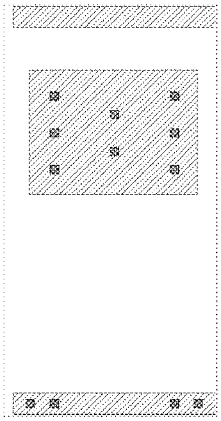
Figure 867A:
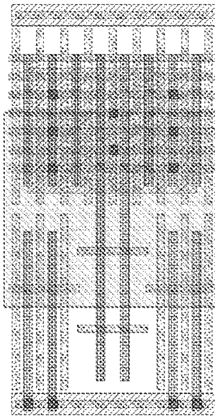
Figure 867B:
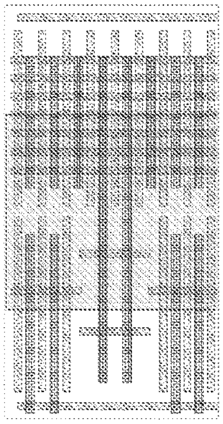
Figure 867C:
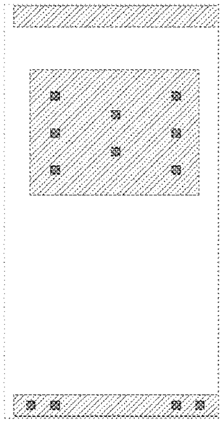
Figure 868A:
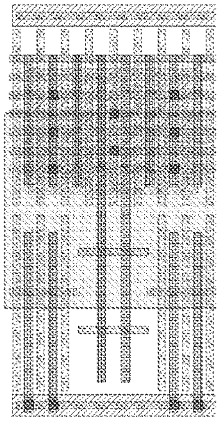
Figure 868B:
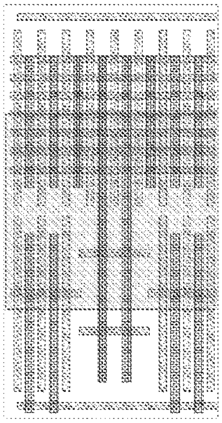
Figure 868C:
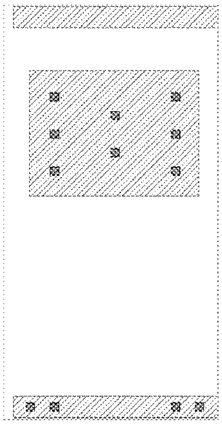
Figure 869A:
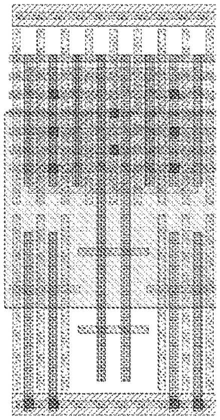
Figure 869B:
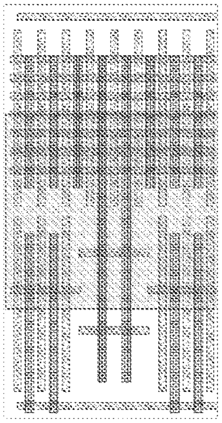
Figure 869C:
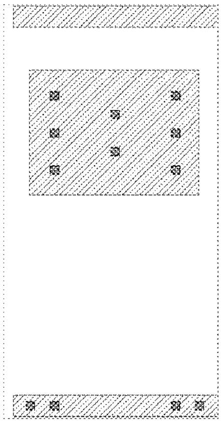
Figure 870A:
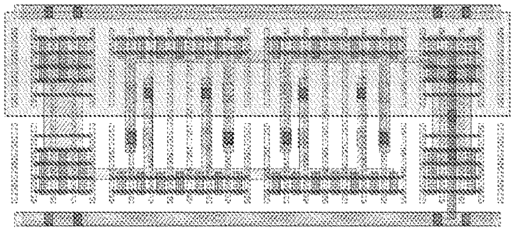
Figure 870B:
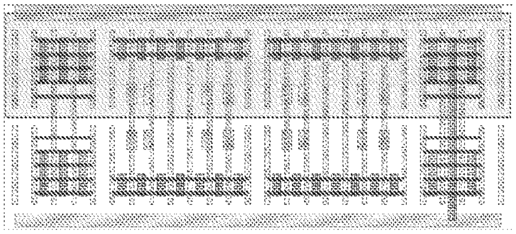
Figure 870C:
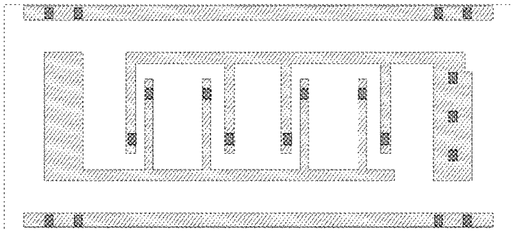
Figure 871A:
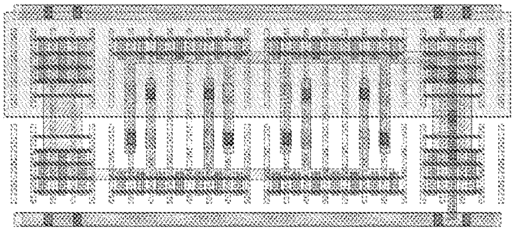
Figure 871B:
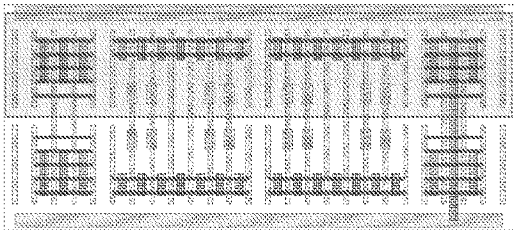
Figure 871C:
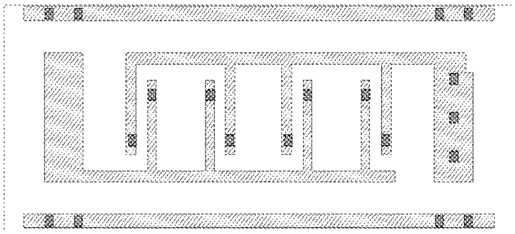
Figure 872A:
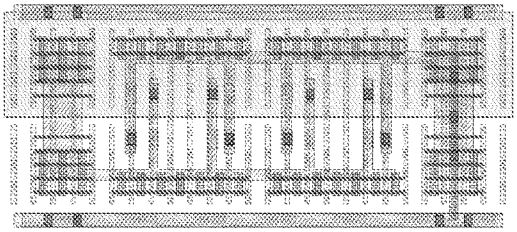
Figure 872B:
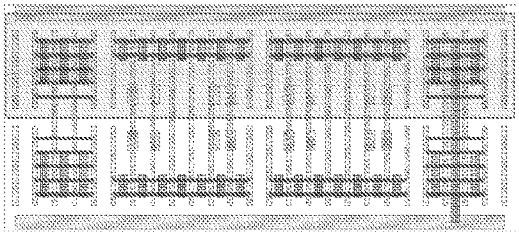
Figure 872C:
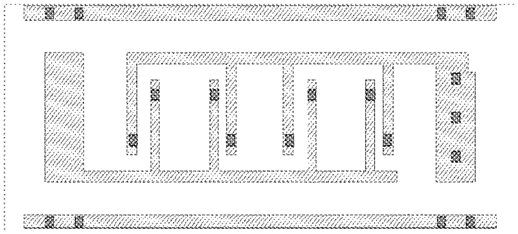
Figure 873A:
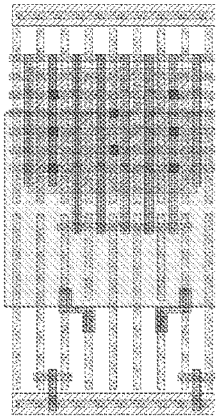
Figure 873B:
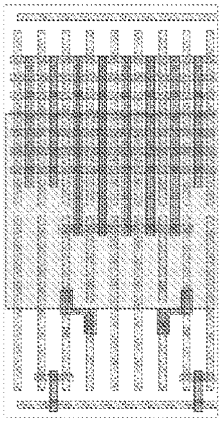
Figure 873C:
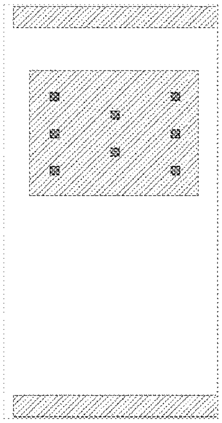
Figure 874A:
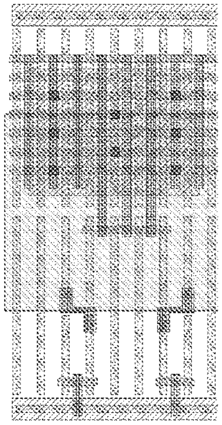
Figure 874B:
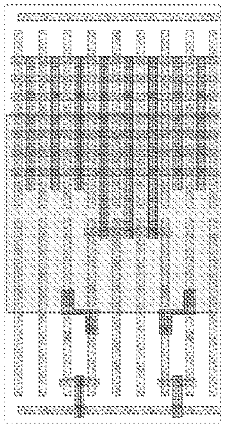
Figure 874C:
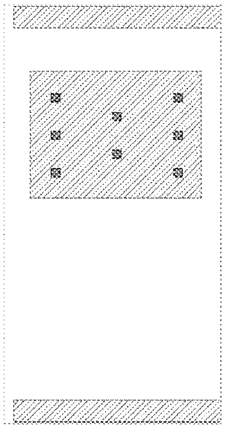
Figure 875A:
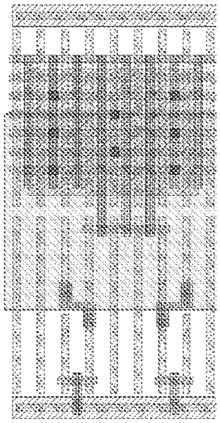
Figure 875B:
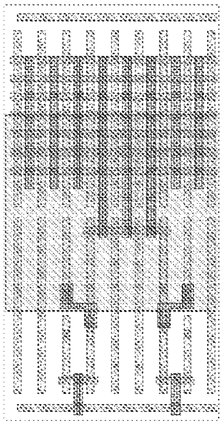
Figure 875C:
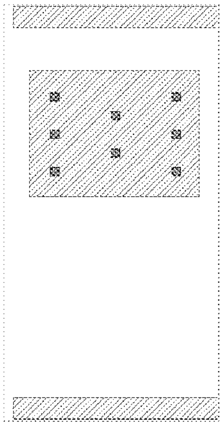
Figure 876A:
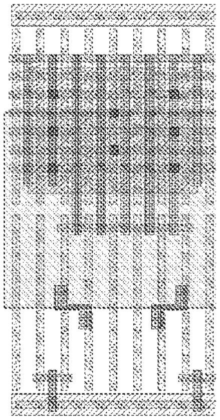
Figure 876B:
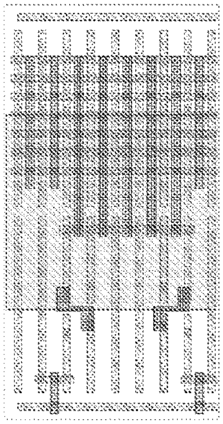
Figure 876C:
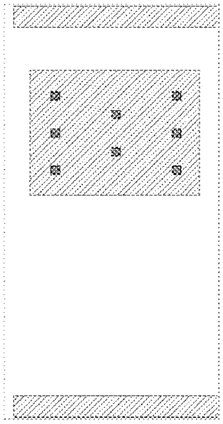
Figure 877A:
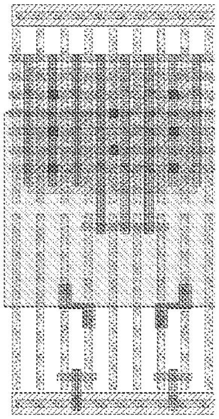
Figure 877B:
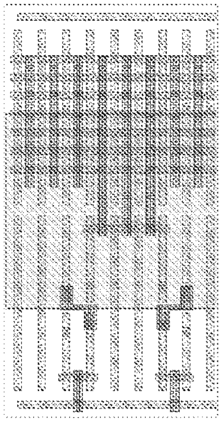
Figure 877C:
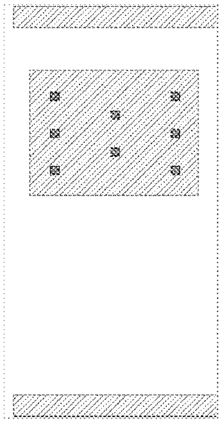
Figure 878A:
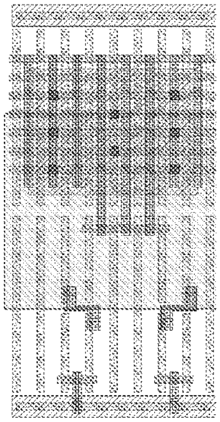
Figure 878B:
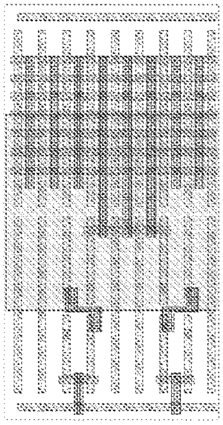
Figure 878C:
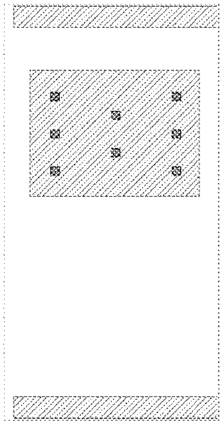
Figure 879A:
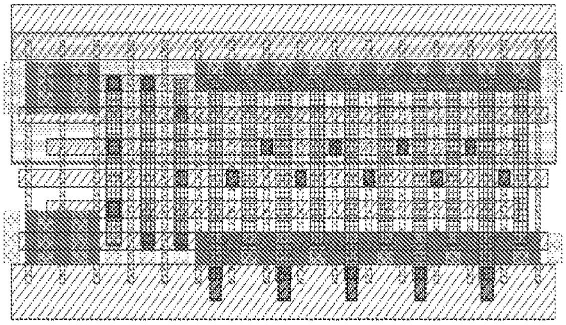
Figure 879B:
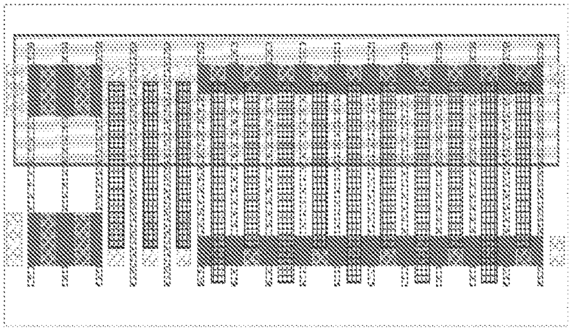
Figure 879C:
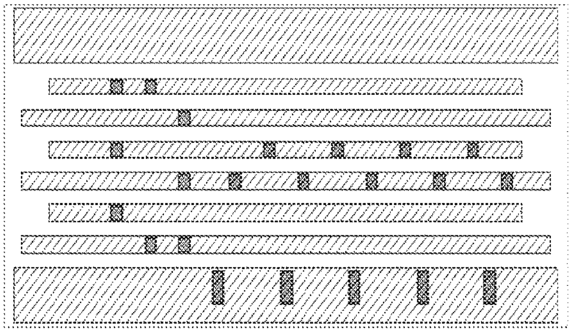
Figure 880A:
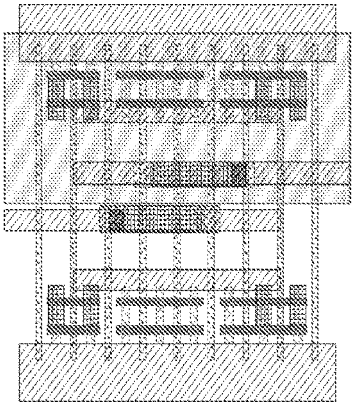
Figure 880B:
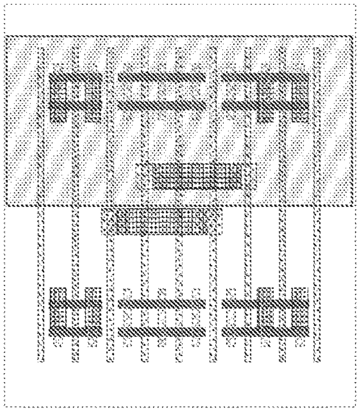
Figure 880C:
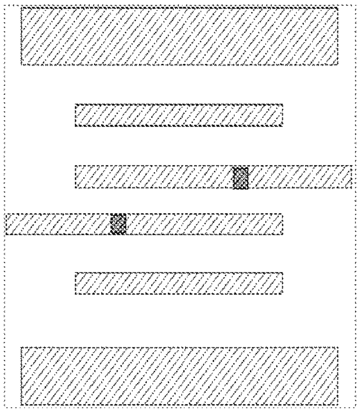
Figure 881A:
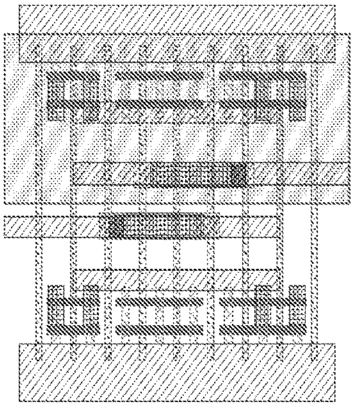
Figure 881B:
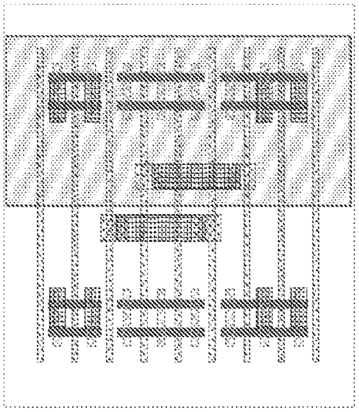
Figure 881C:
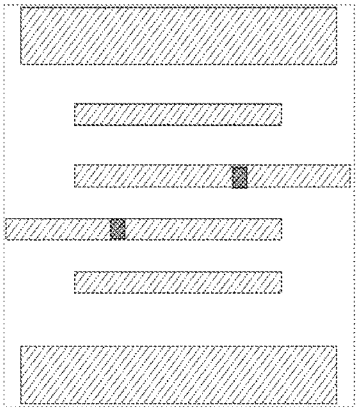
Figure 882A:
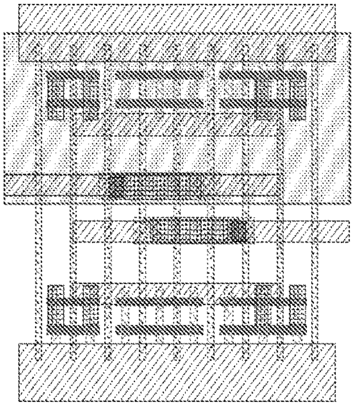
Figure 882B:
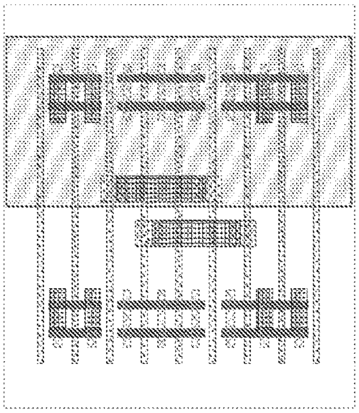
Figure 882C:
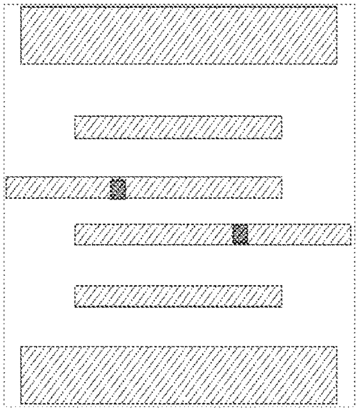
Figure 883A:
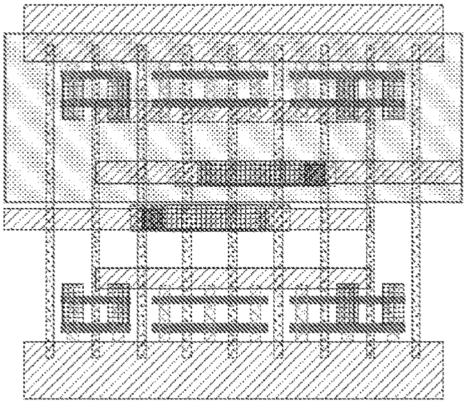
Figure 883B:
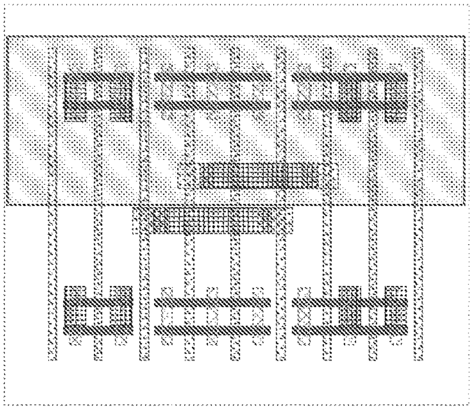
Figure 883C:
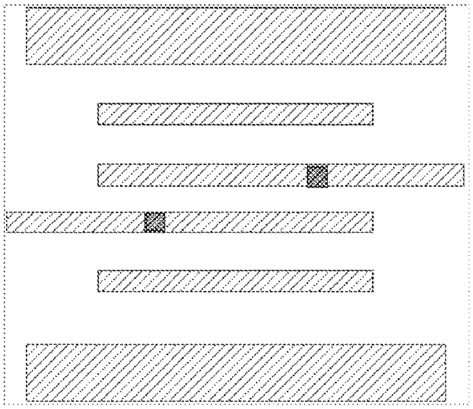
Figure 884A:
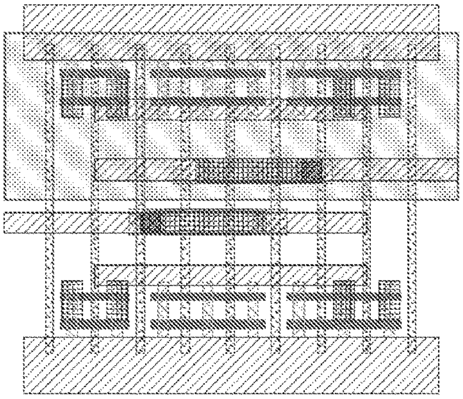
Figure 884B:
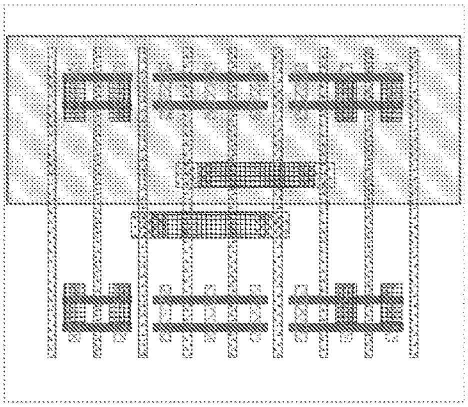
Figure 884C:
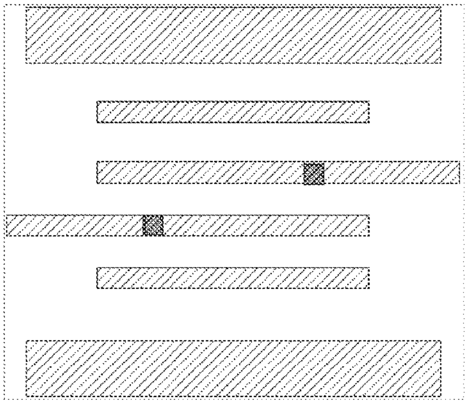
Figure 885A:
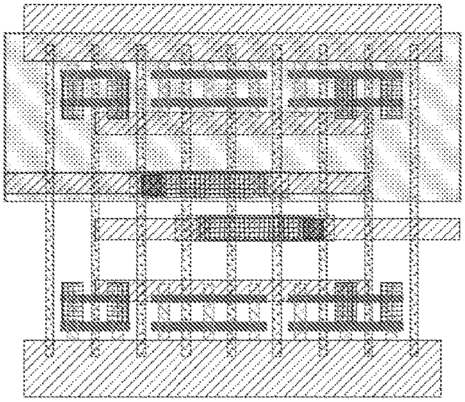
Figure 885B:
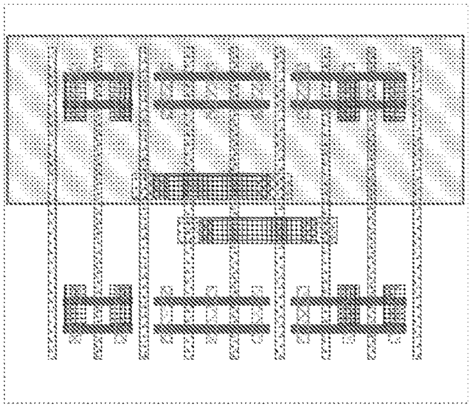
Figure 885C:
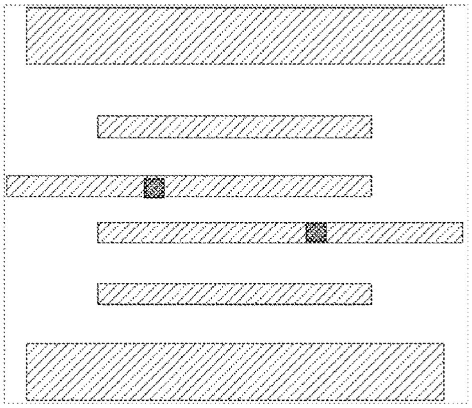
Figure 886A:
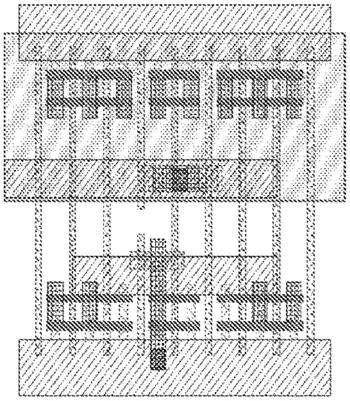
Figure 886B:
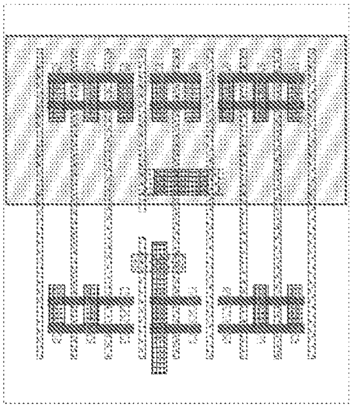
Figure 886C:
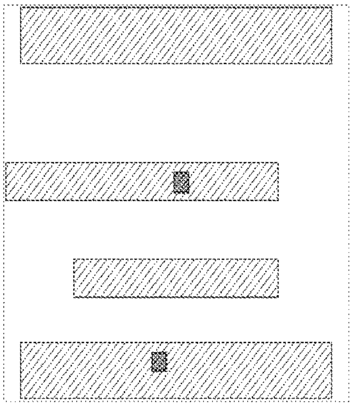
Figure 887A:
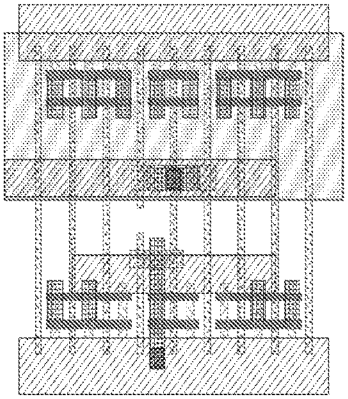
Figure 887B:
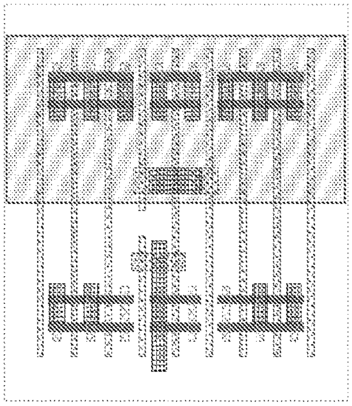
Figure 887C:
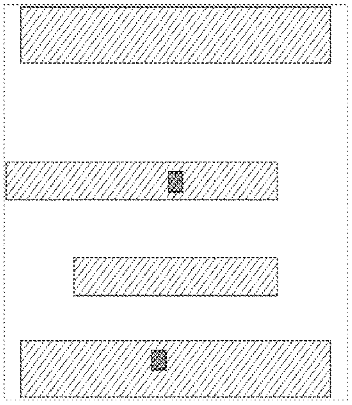
Figure 888A:
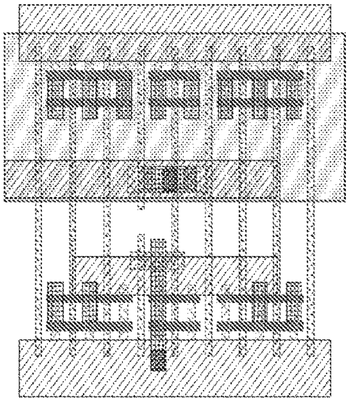
Figure 888B:
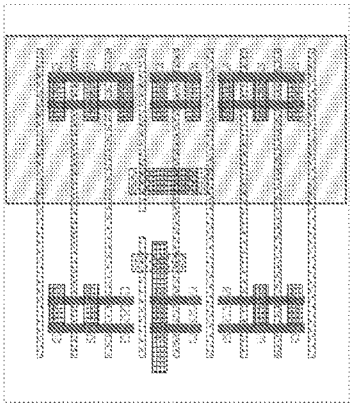
Figure 888C:
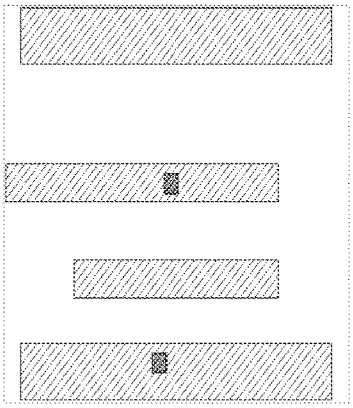
Figure 889A:
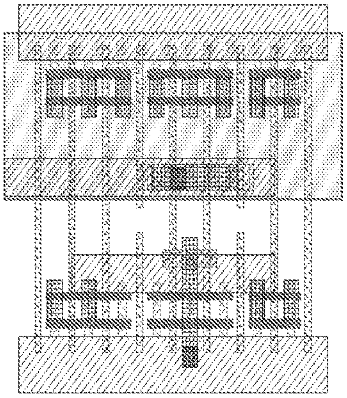
Figure 889B:
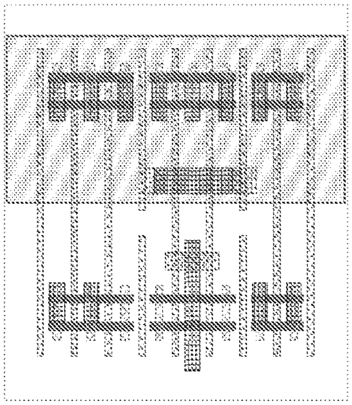
Figure 889C:
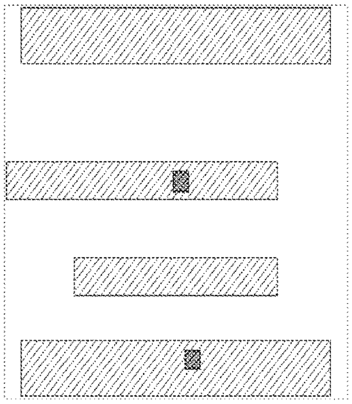
Figure 890A:
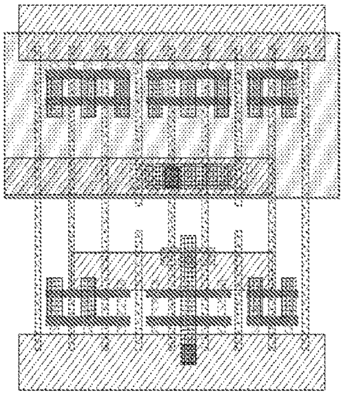
Figure 890B:
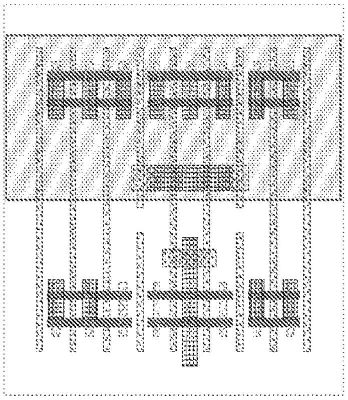
Figure 890C:
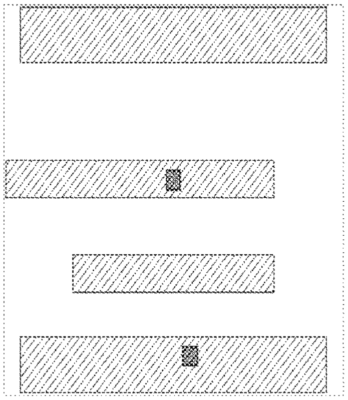
Figure 891A:
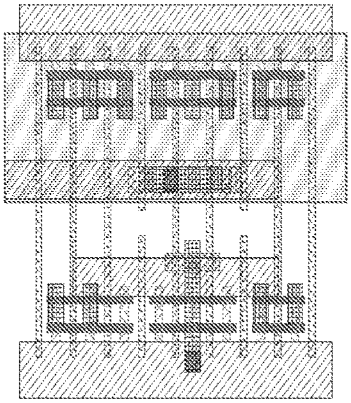
Figure 891B:
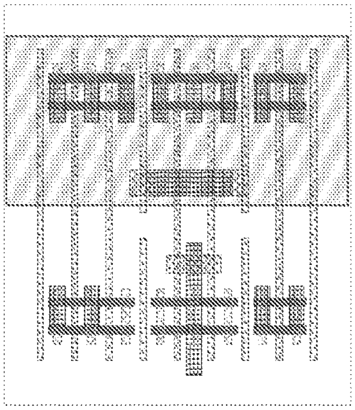
Figure 891C:
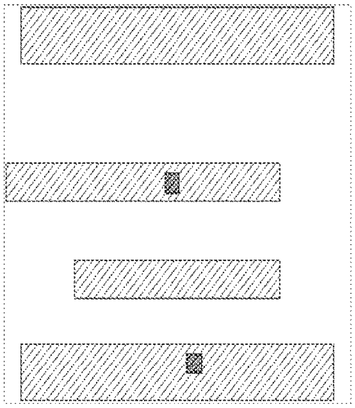
Figure 892A:
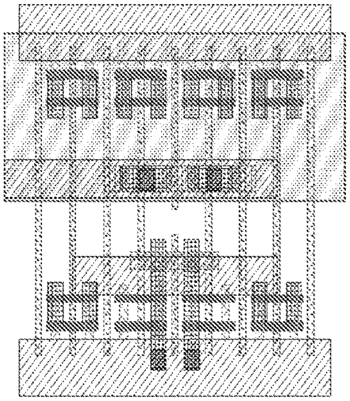
Figure 892B:
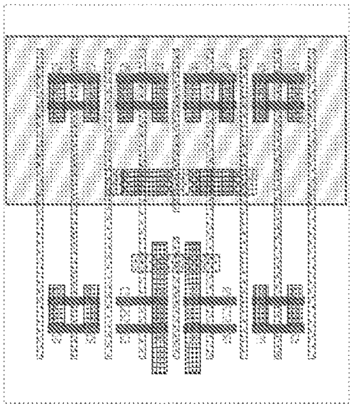
Figure 892C:
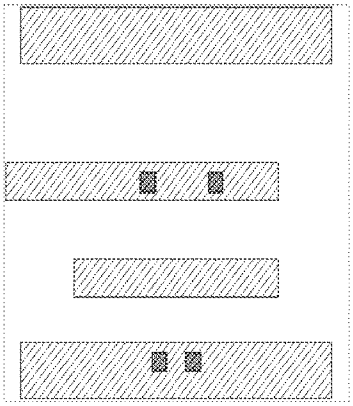
Figure 893A:
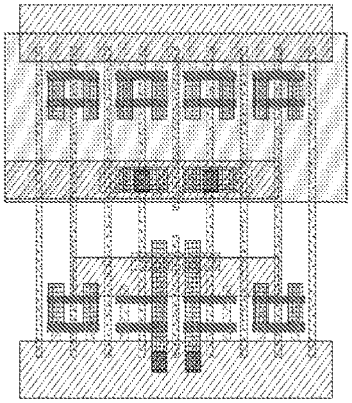
Figure 893B:
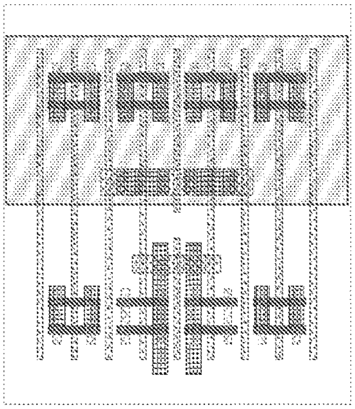
Figure 893C:
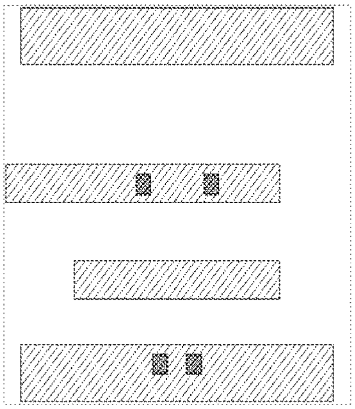
Figure 894A:
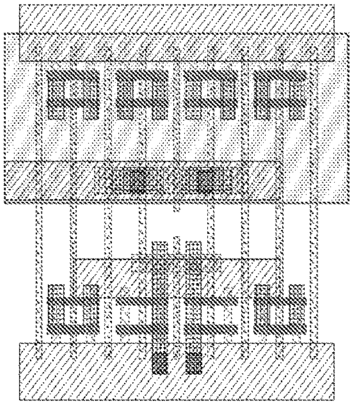
Figure 894B:
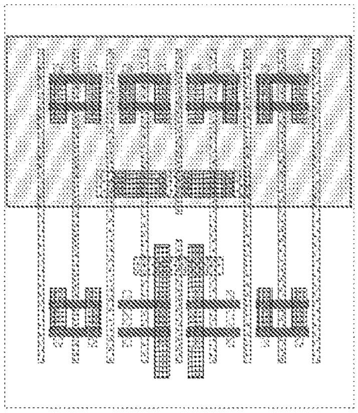
Figure 894C:
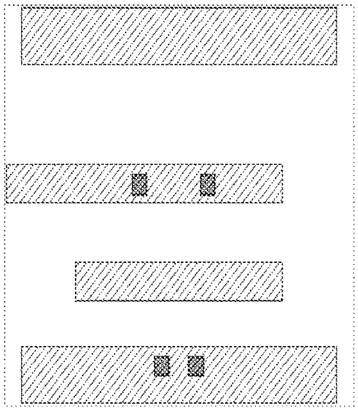
Figure 895A:
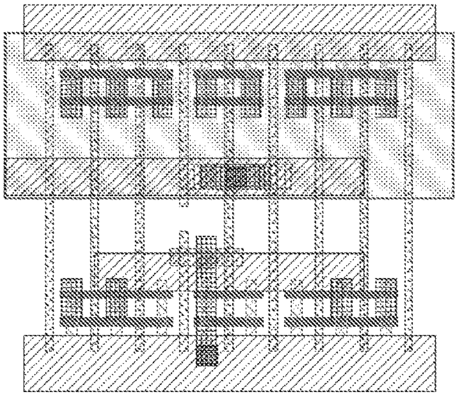
Figure 895B:
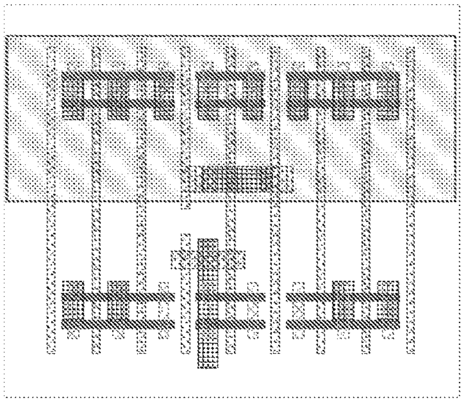
Figure 895C:
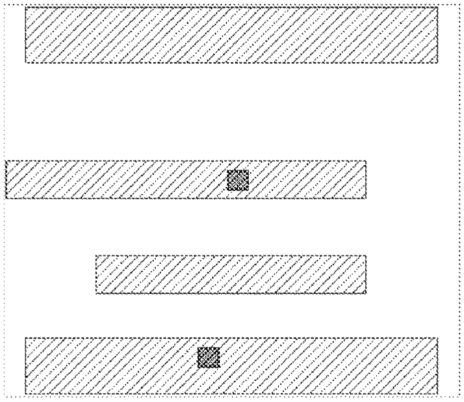
Figure 896A:
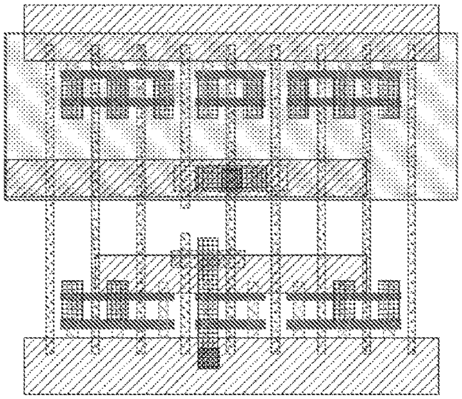
Figure 896B:
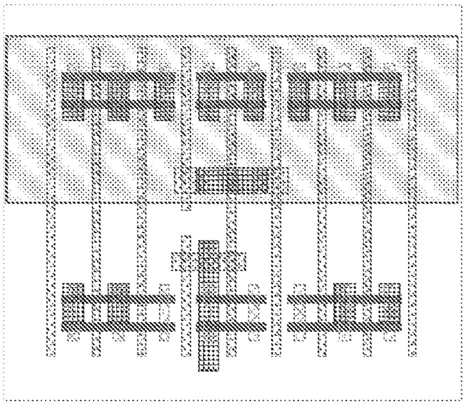
Figure 896C:
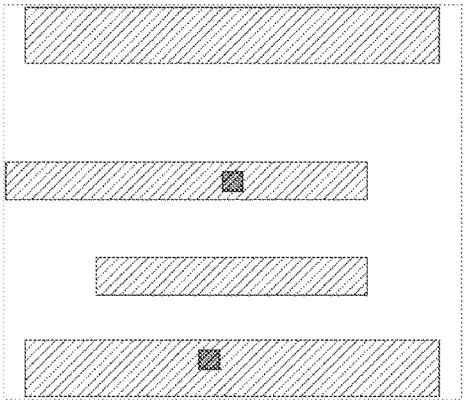
Figure 897A:
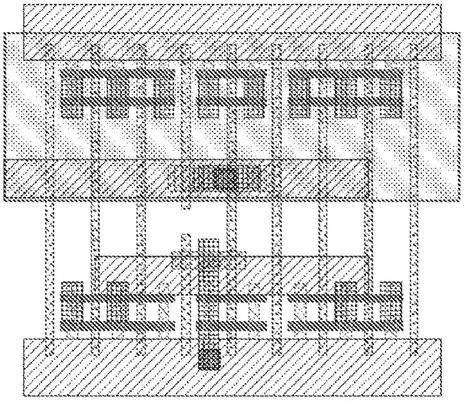
Figure 897B:
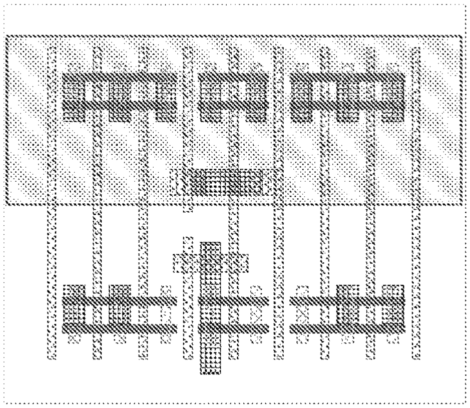
Figure 897C:
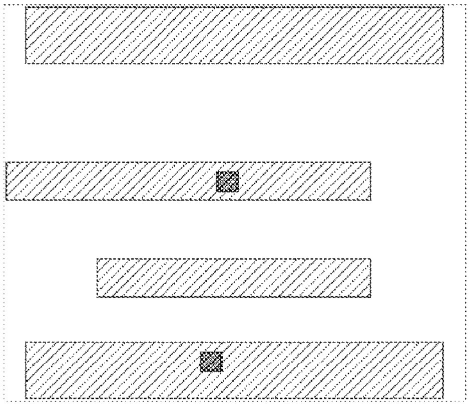
Figure 898A:
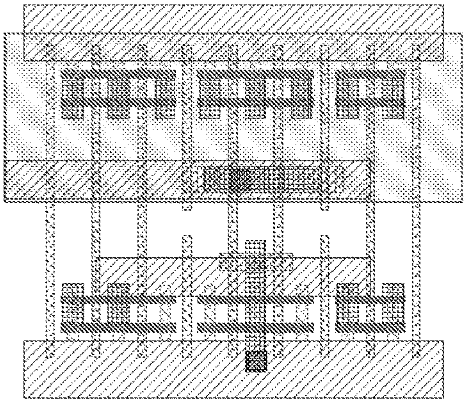
Figure 898B:
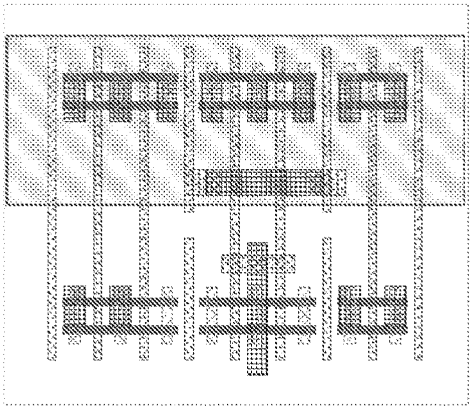
Figure 898C:
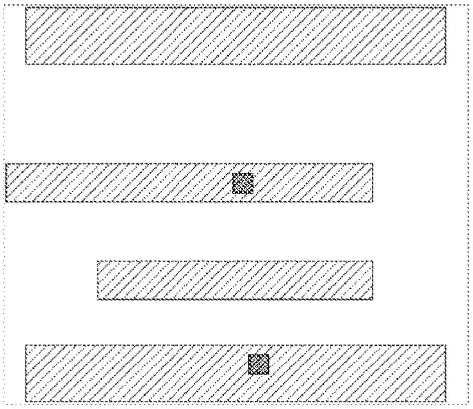
Figure 899A:
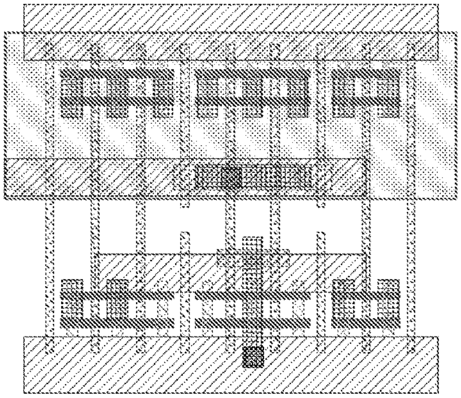
Figure 899B:
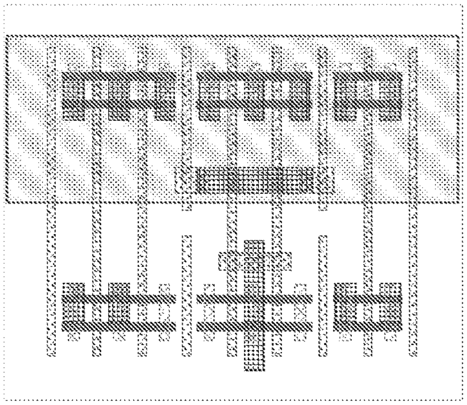
Figure 899C:
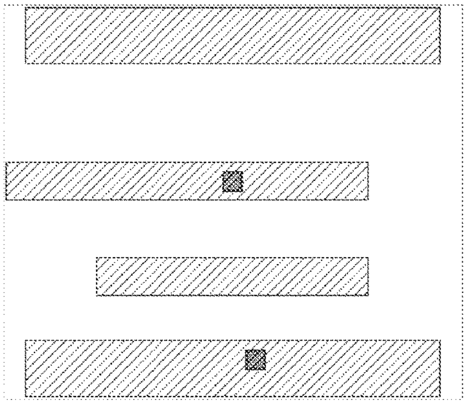
Figure 900A:
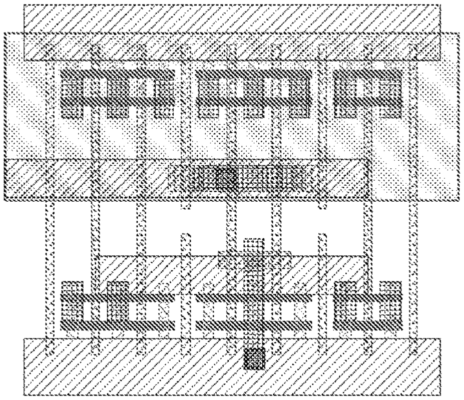
Figure 900B:
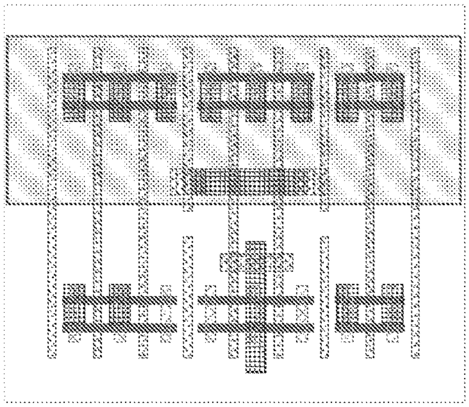
Figure 900C:
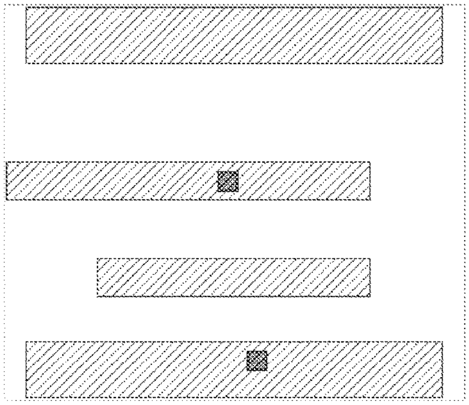
Figure 901A:
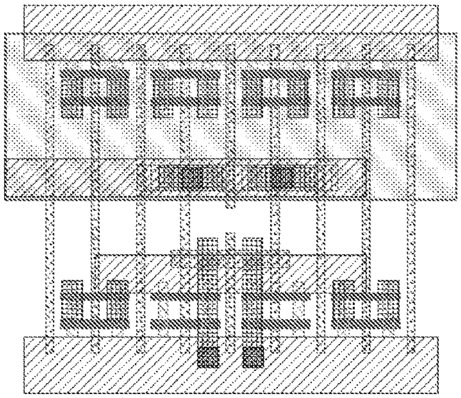
Figure 901B:
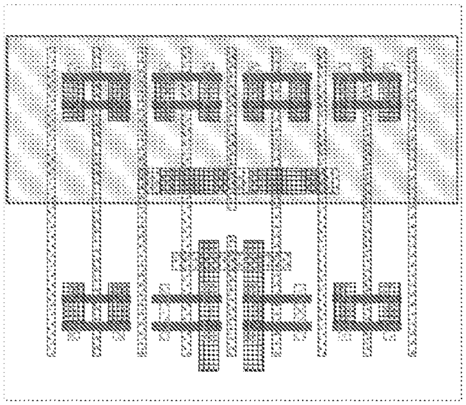
Figure 901C:
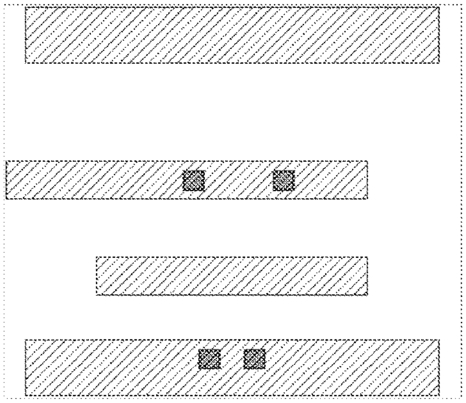
Figure 902A:
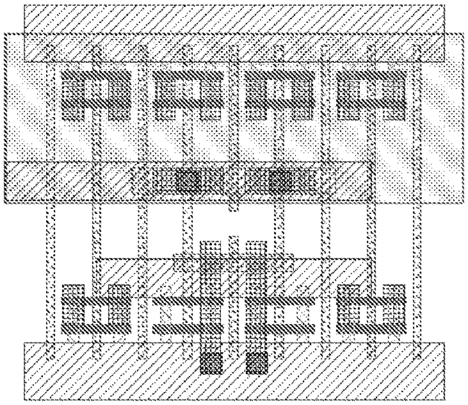
Figure 902B:
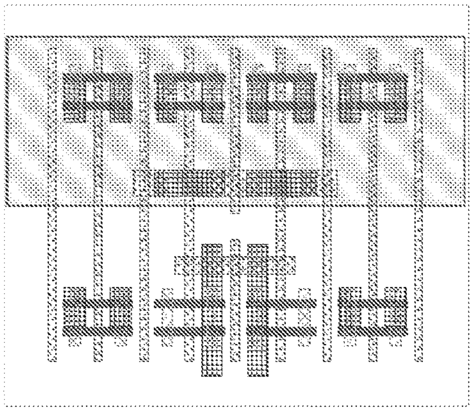
Figure 902C:
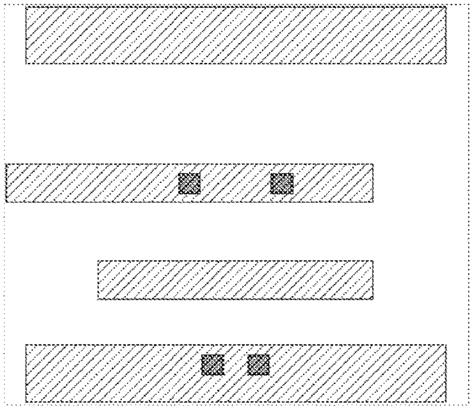
Figure 903A:
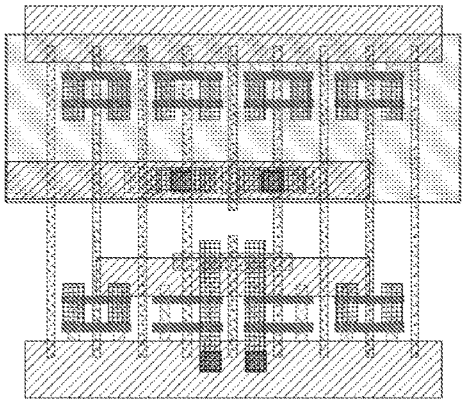
Figure 903B:
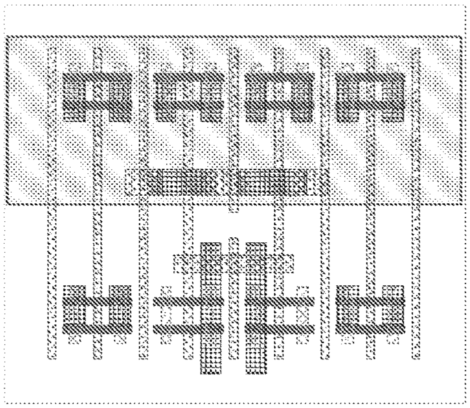
Figure 903C:
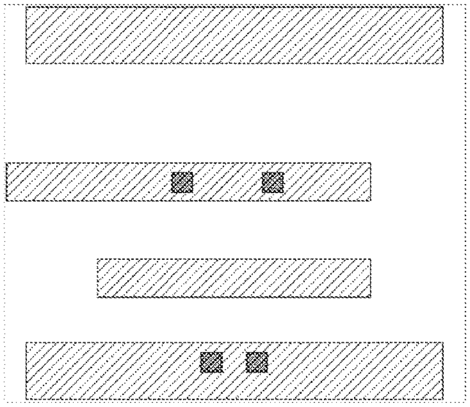
Figure 904A:
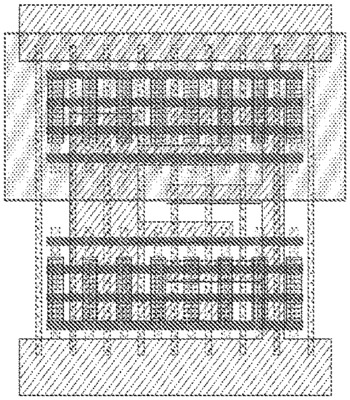
Figure 904B:
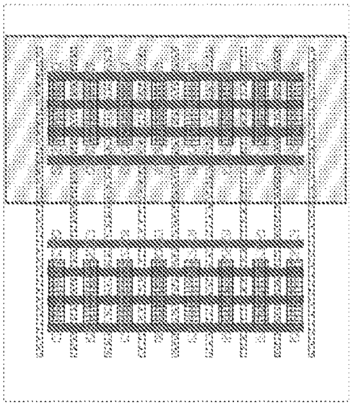
Figure 904C:
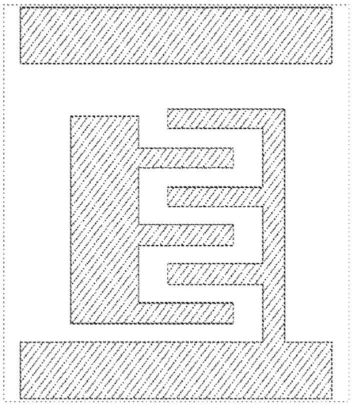
Figure 905A:
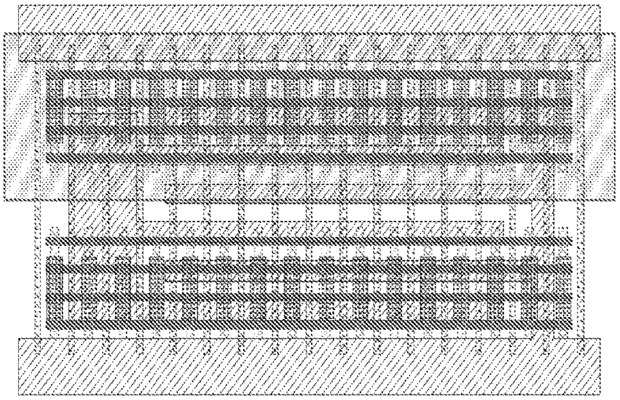
Figure 905B:
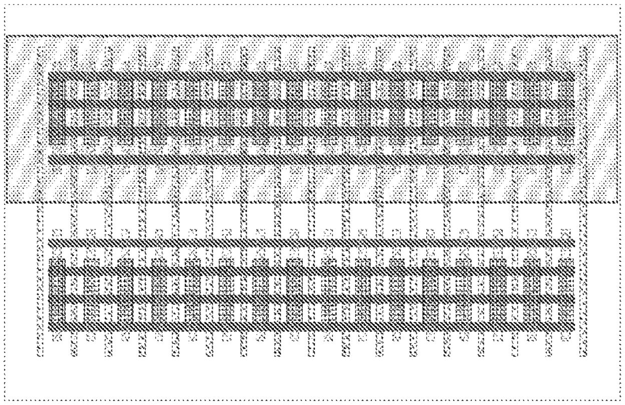
Figure 905C:
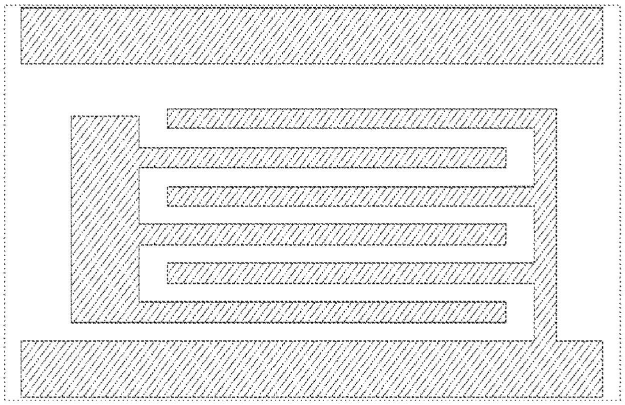
Figure 906A:
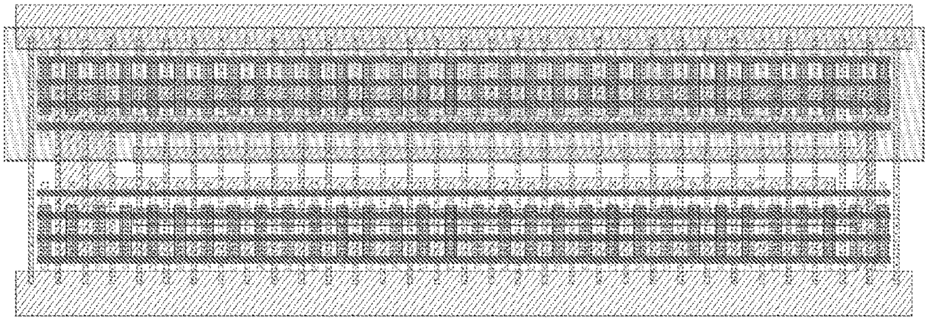
Figure 906B:
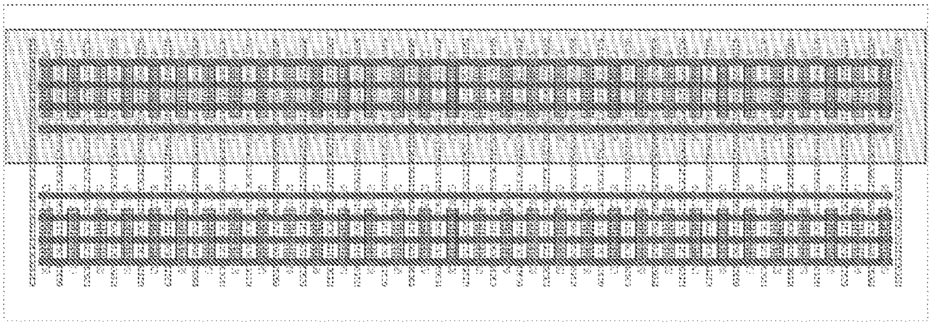
Figure 906C:
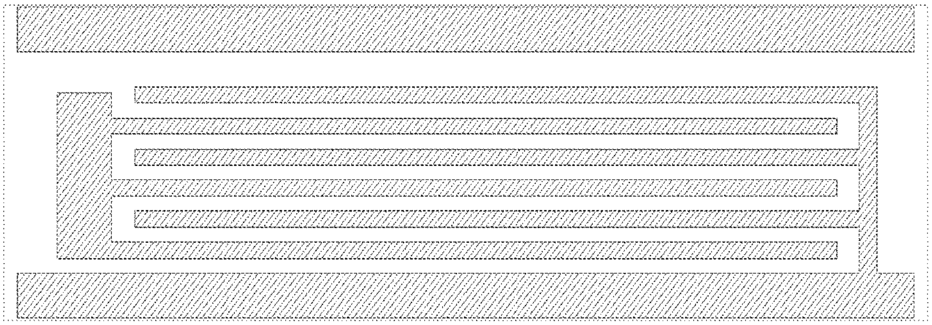
Figure 907A:
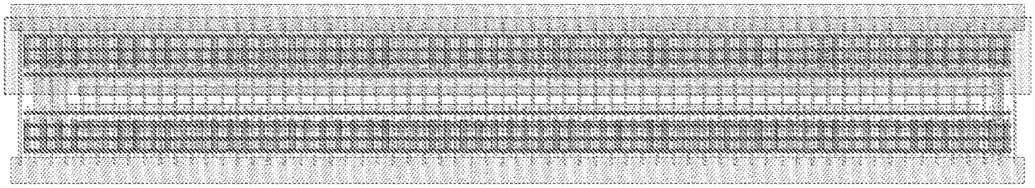
Figure 907B:
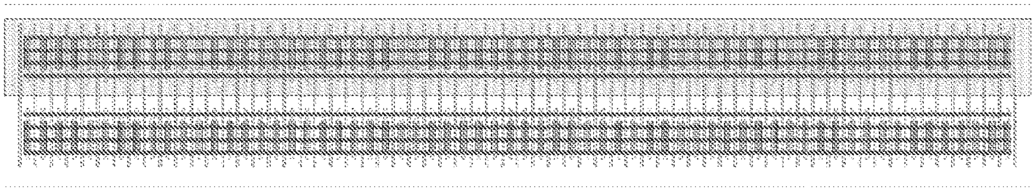
Figure 907C:
Figure 908A:
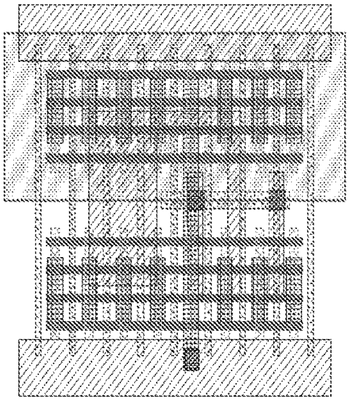
Figure 908B:
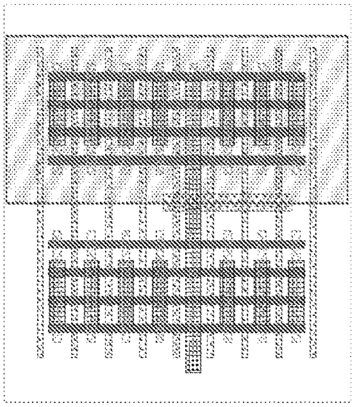
Figure 908C:
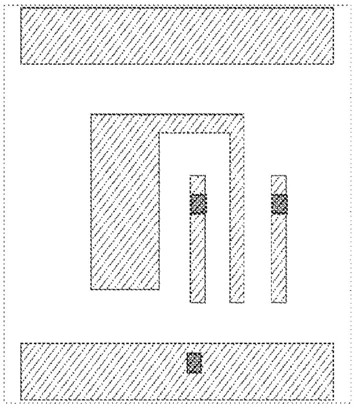
Figure 909A:
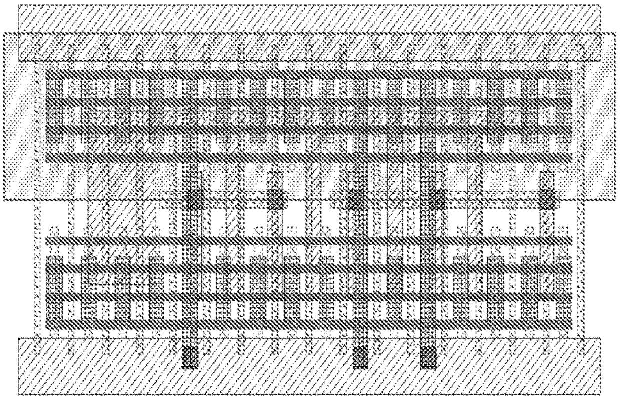
Figure 909B:
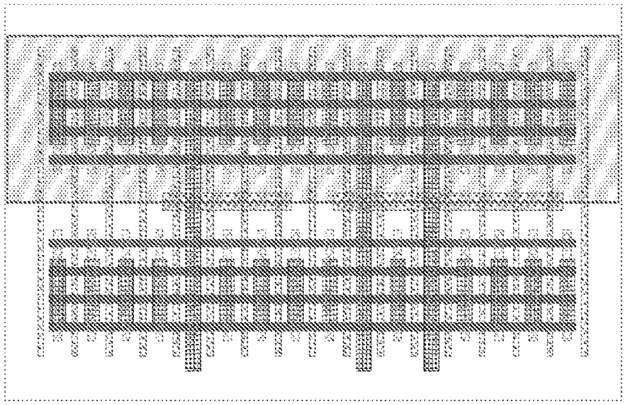
Figure 909C:
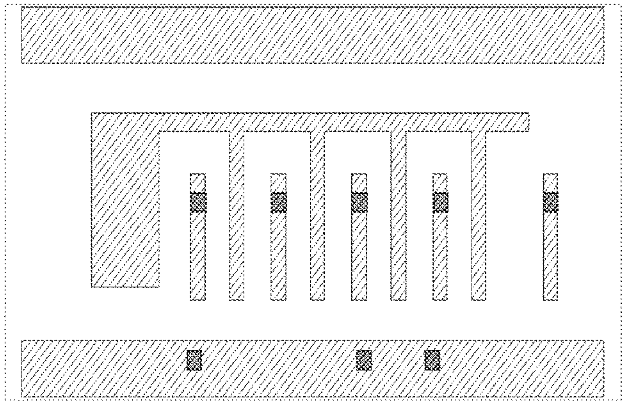
Figure 910A:
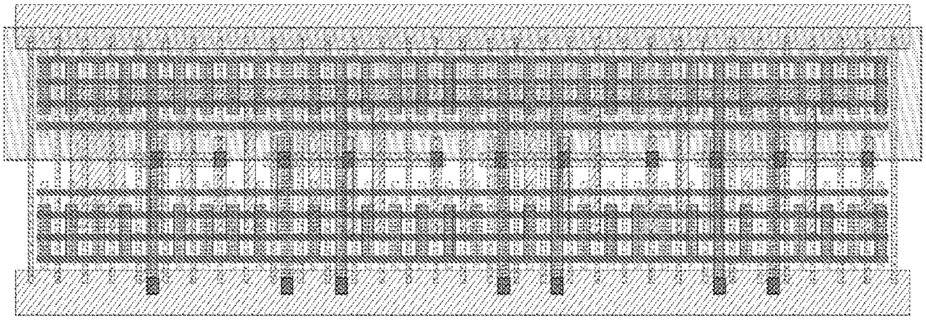
Figure 910B:
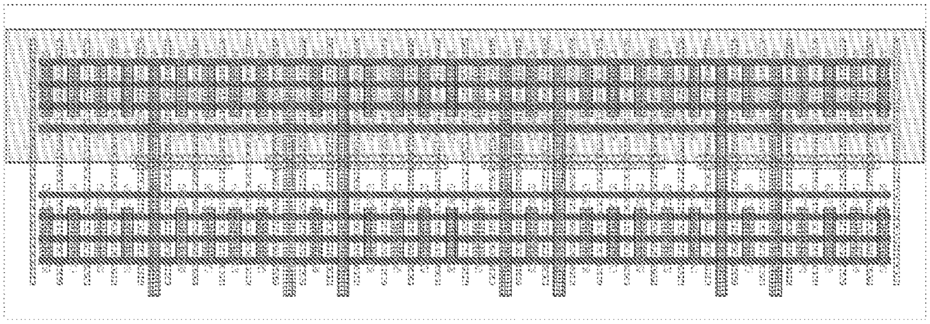
Figure 910C:
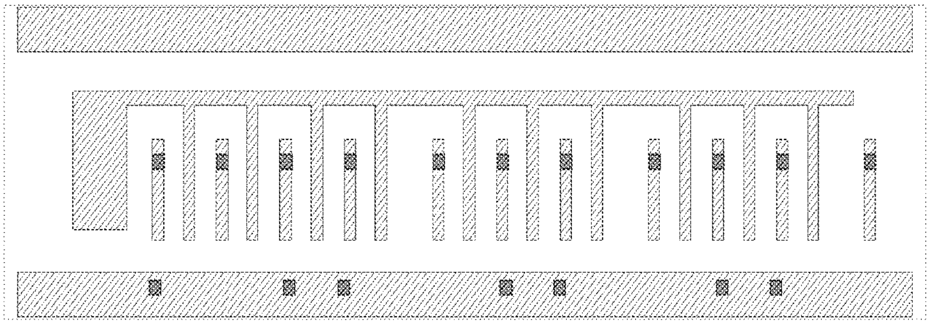
Figure 911A:
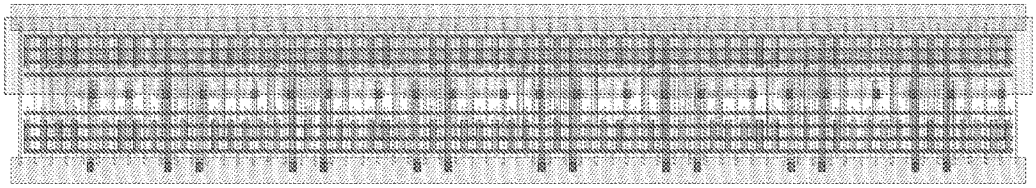
Figure 911B:
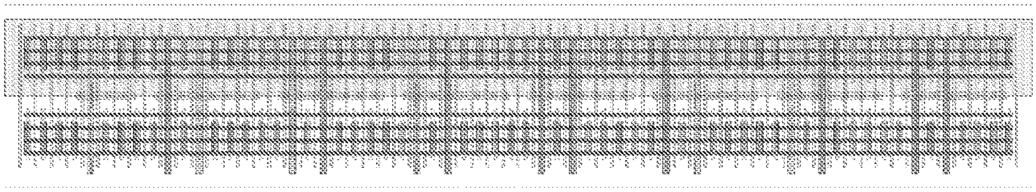
Figure 911C:
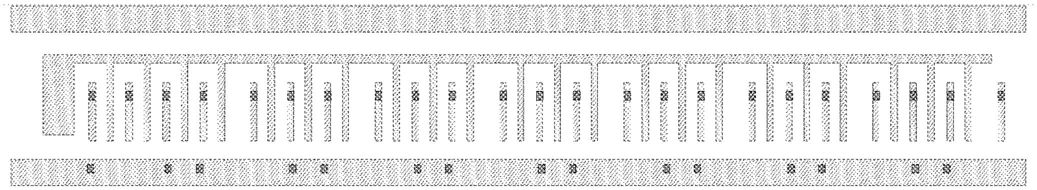
Figure 912A:
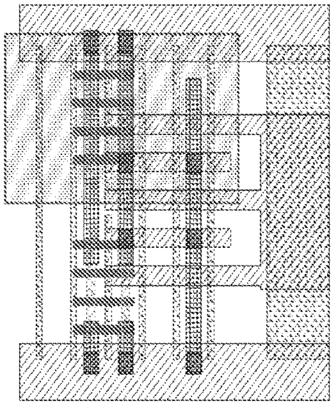
Figure 912B:
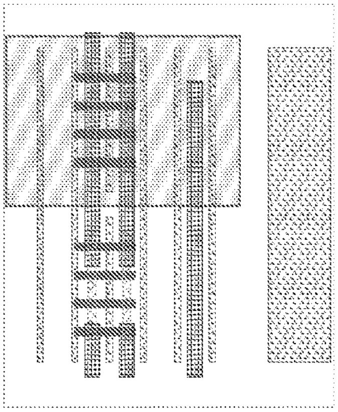
Figure 912C:
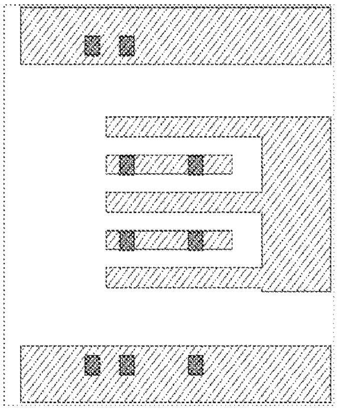
Figure 913A:
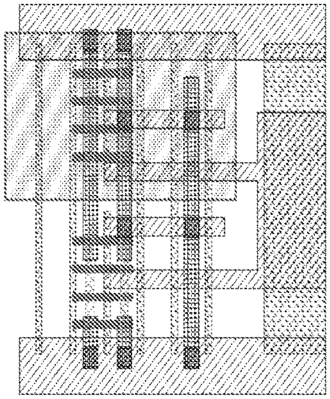
Figure 913B:
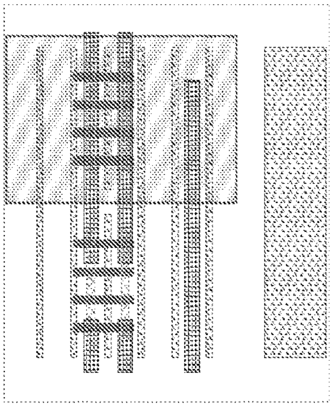
Figure 913C:
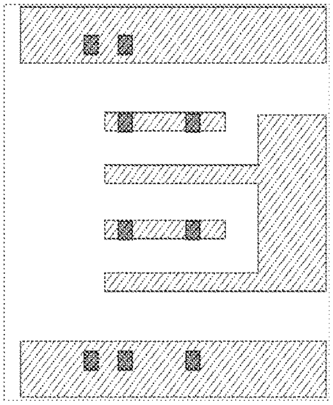
Figure 914A:
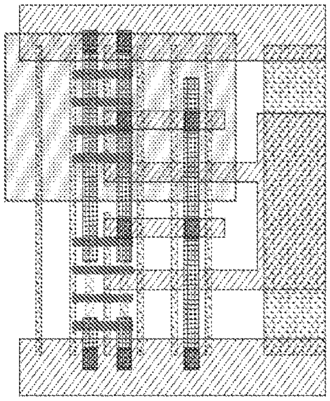
Figure 914B:
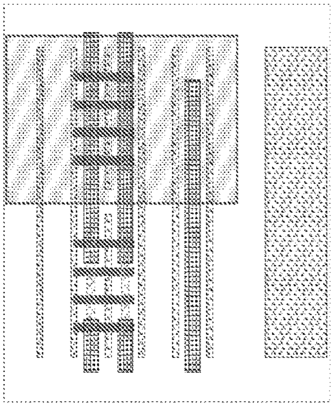
Figure 914C:
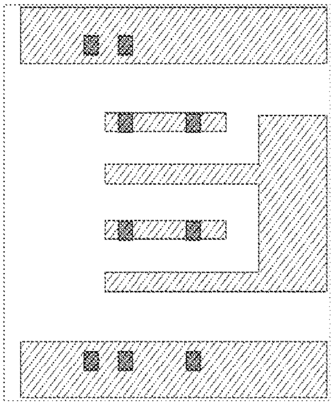
Figure 915A:
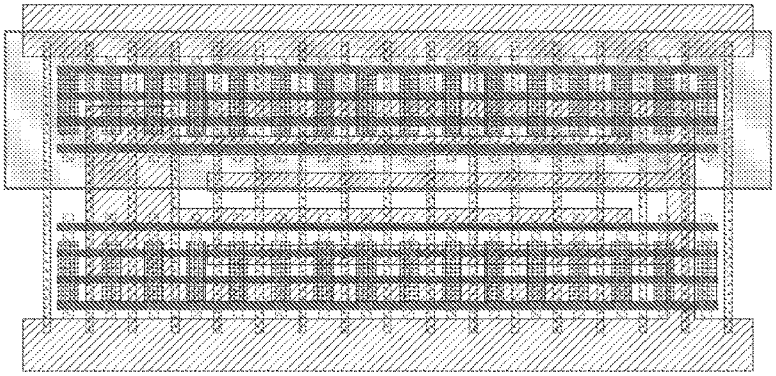
Figure 915B:
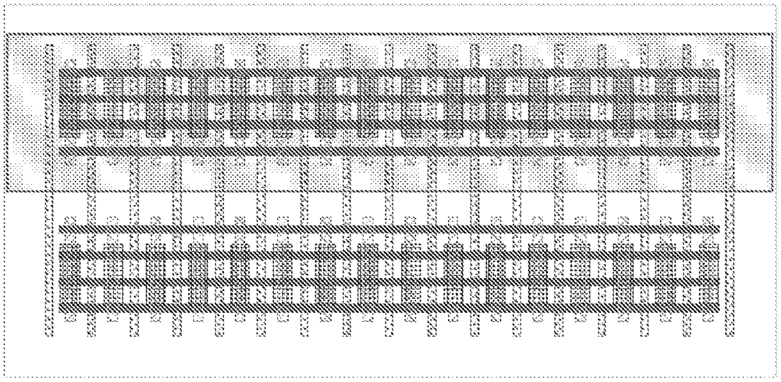
Figure 915C:
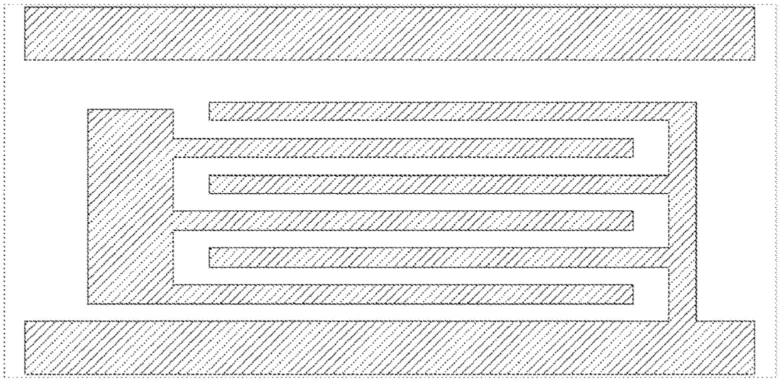
Figure 916A:
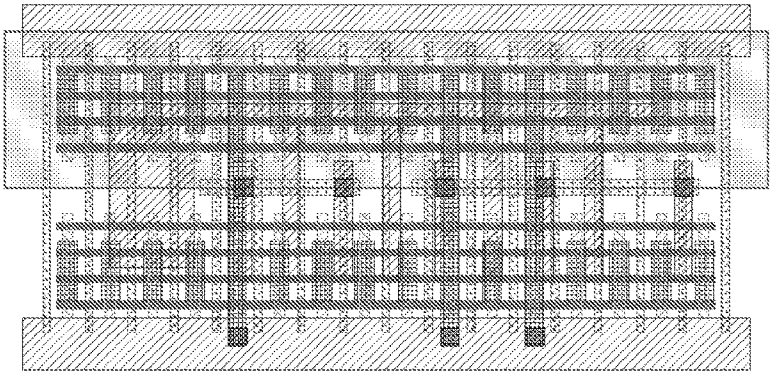
Figure 916B:
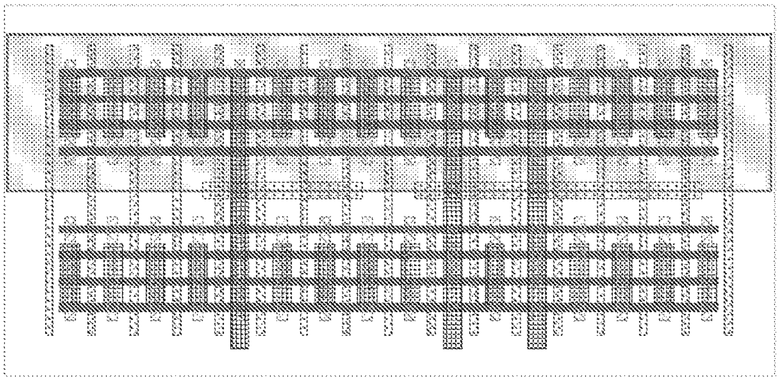
Figure 916C:
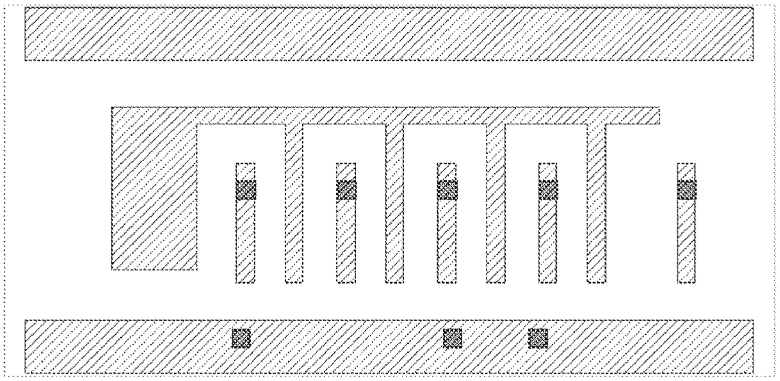
Figure 917A:
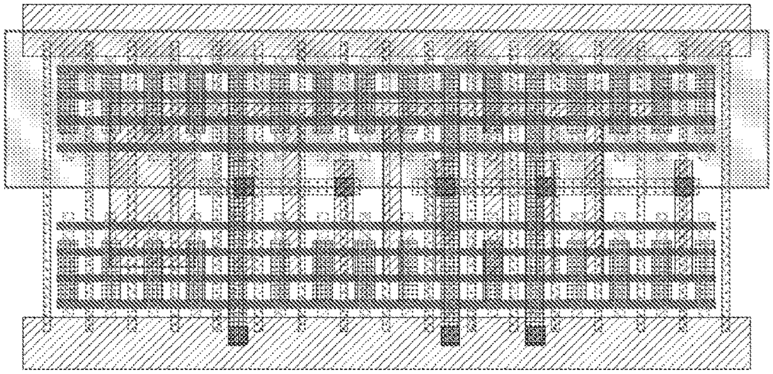
Figure 917B:
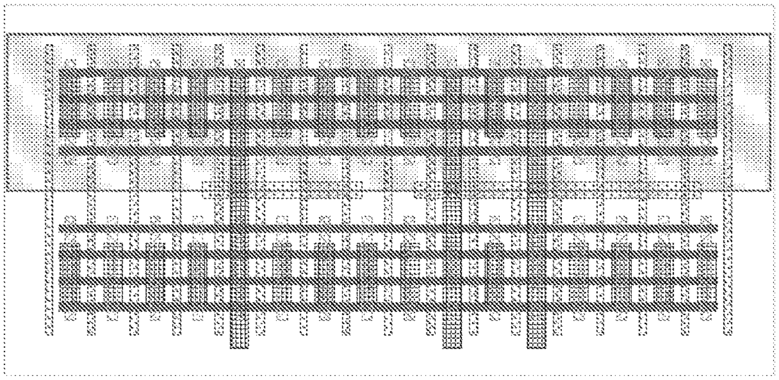
Figure 917C:
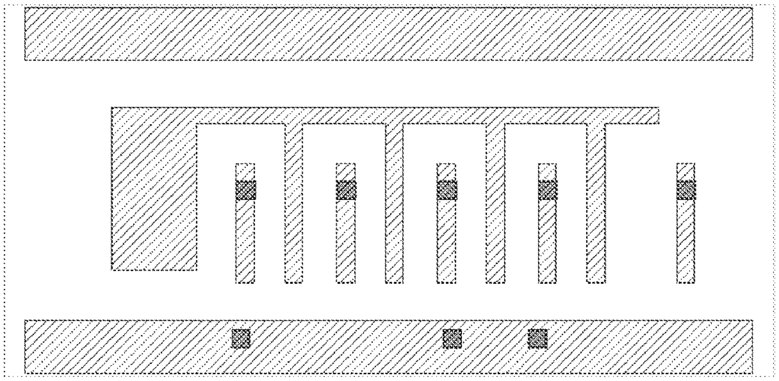
Figure 918A:
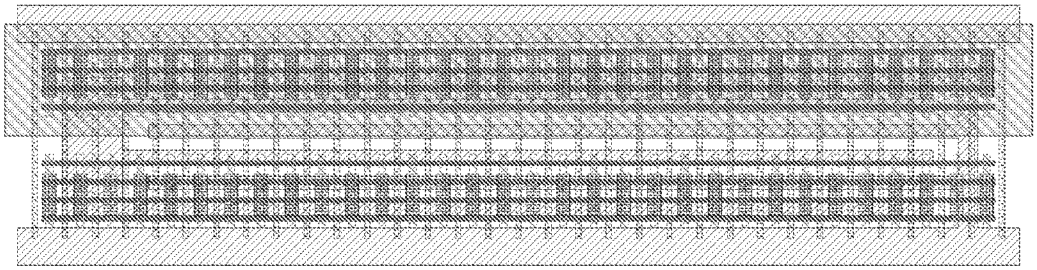
Figure 918B:
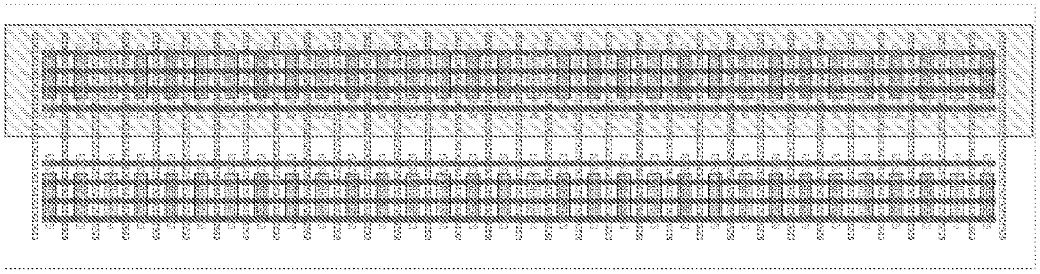
Figure 918C:
Figure 919A:
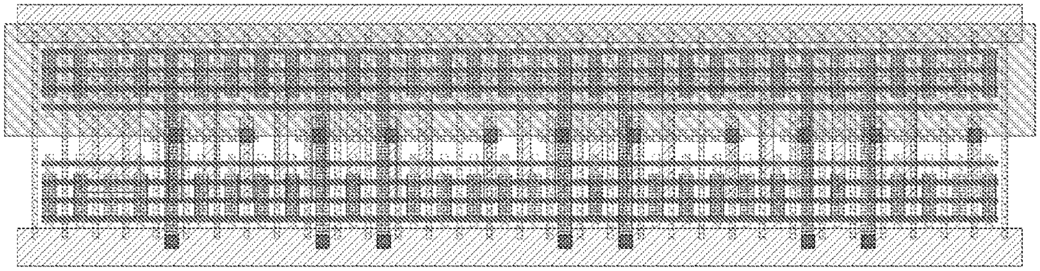
Figure 919B:
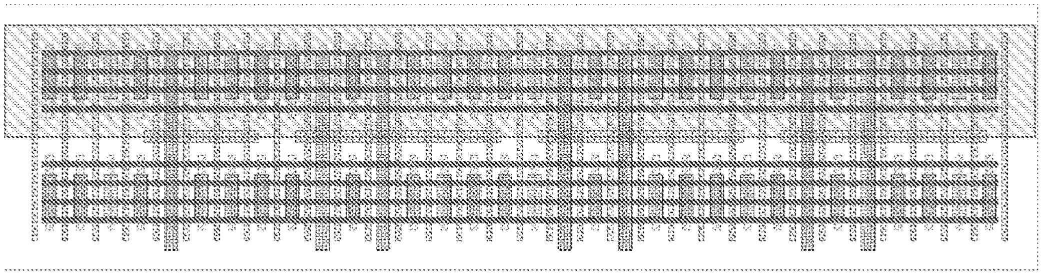
Figure 919C:
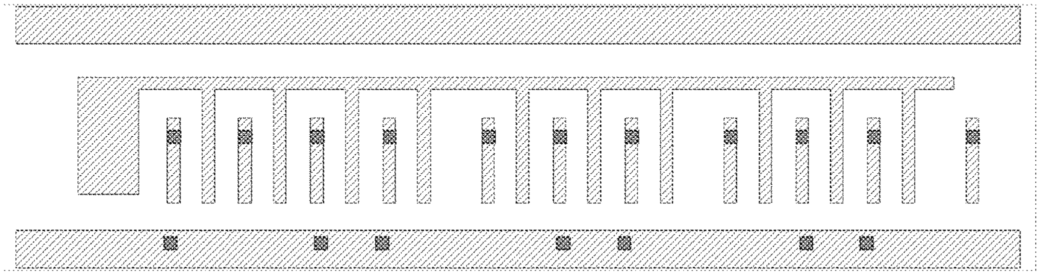
Figure 920A:
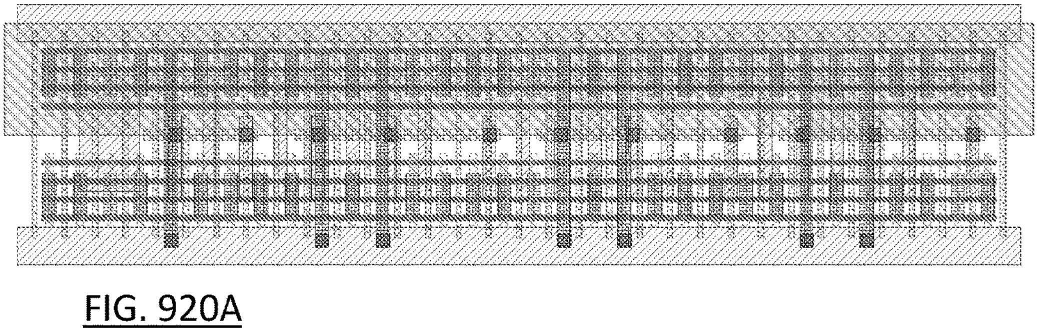
Figure 920B:
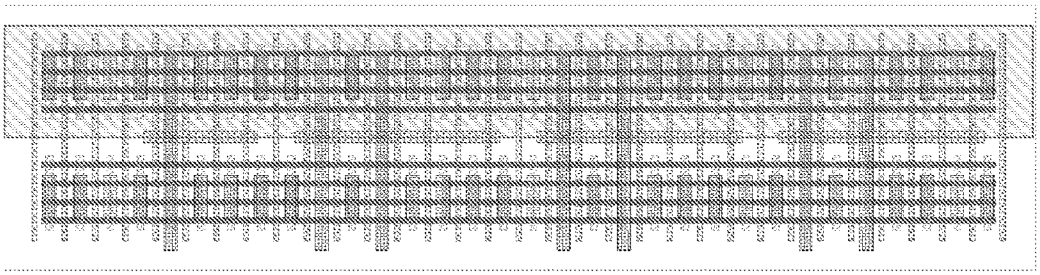
Figure 920C:
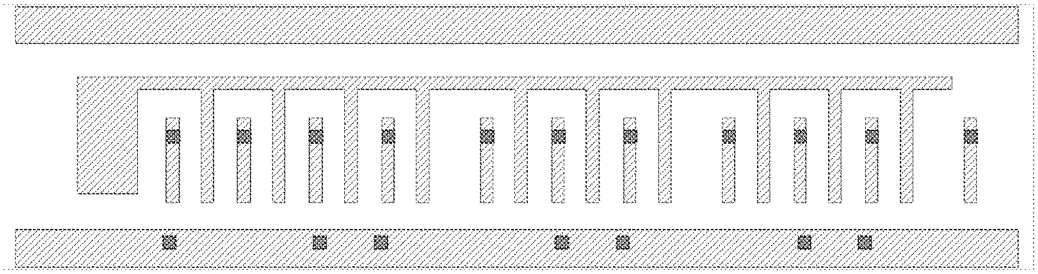
Figure 921A:
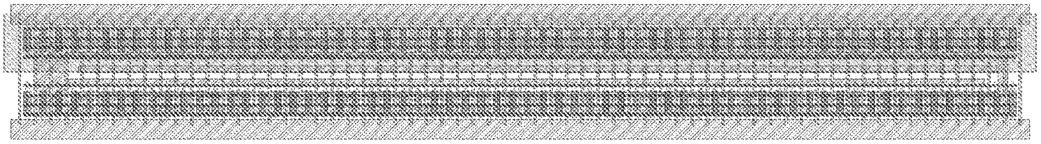
Figure 921B:
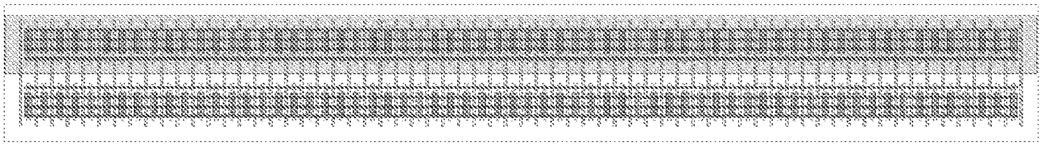
Figure 921C:
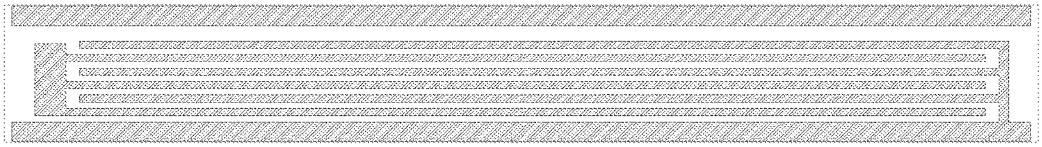
Figure 922A:
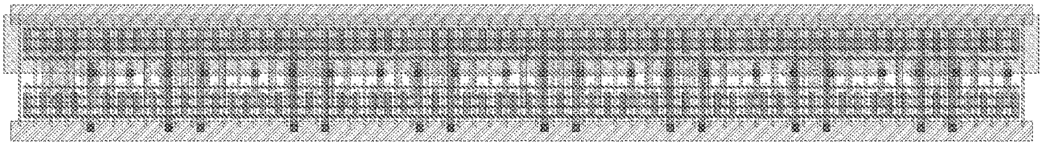
Figure 922B:
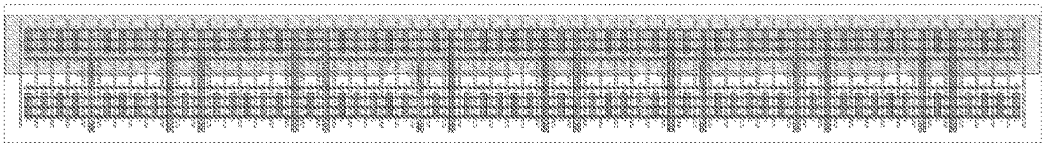
Figure 922C:
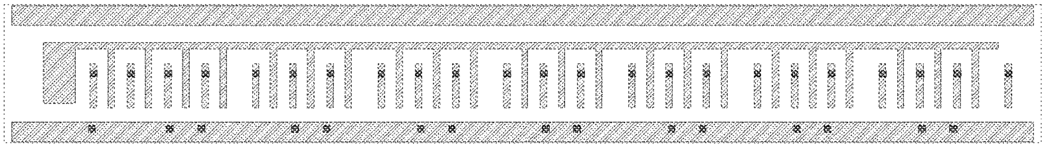
Figure 923A:
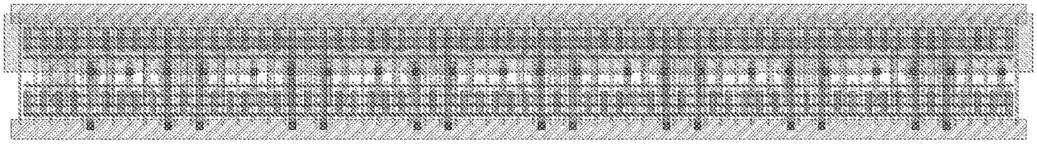
Figure 923B:
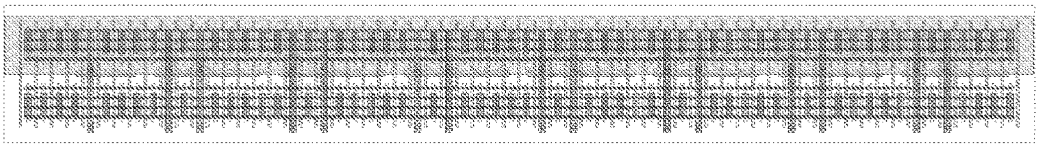
Figure 923C:
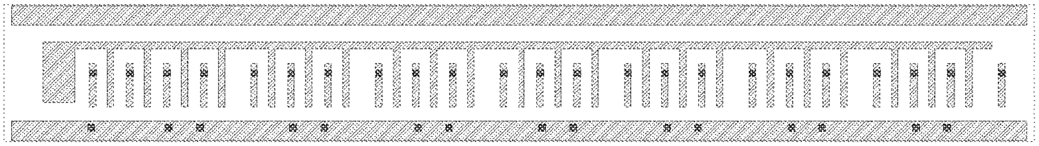
Figure 924A:
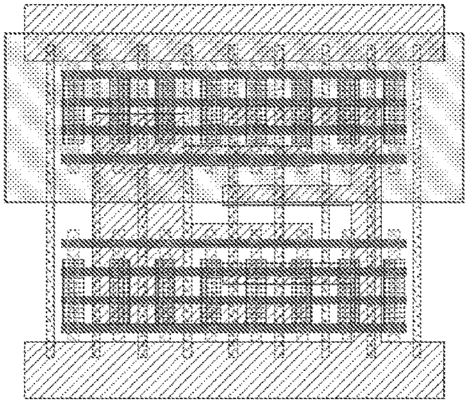
Figure 924B:
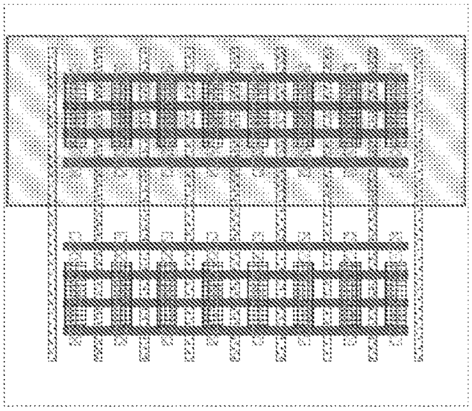
Figure 924C:
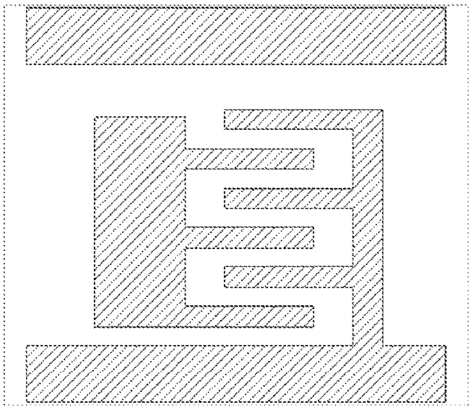
Figure 925A:
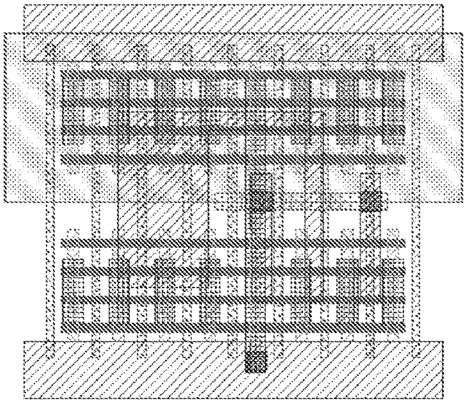
Figure 925B:
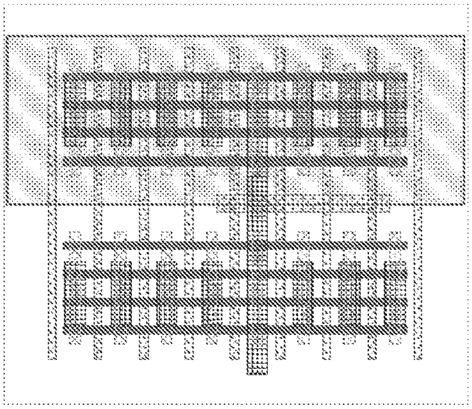
Figure 925C:
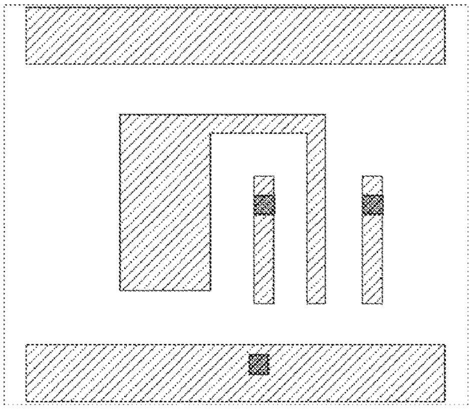
Figure 926A:
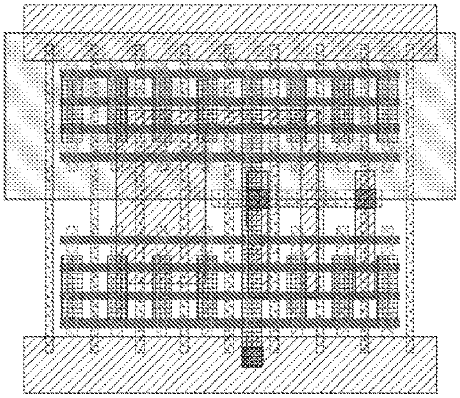
Figure 926B:
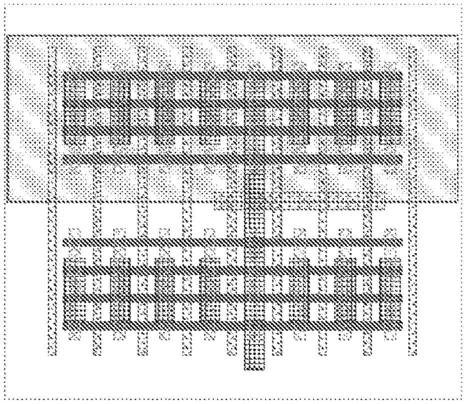
Figure 926C:
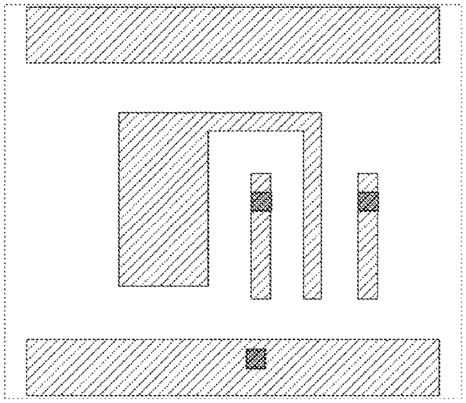
Figure 927A:
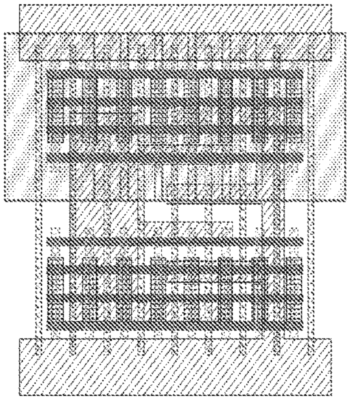
Figure 927B:
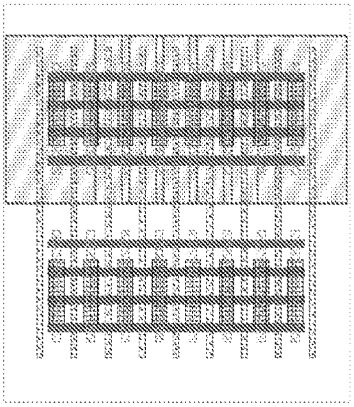
Figure 927C:
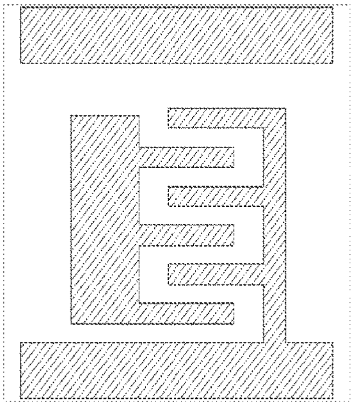
Figure 928A:
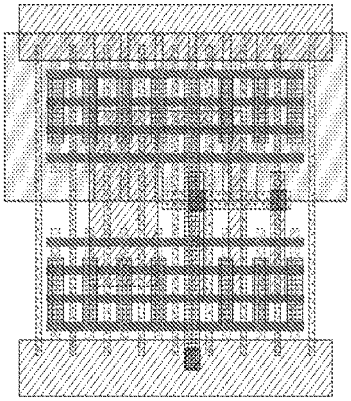
Figure 928B:
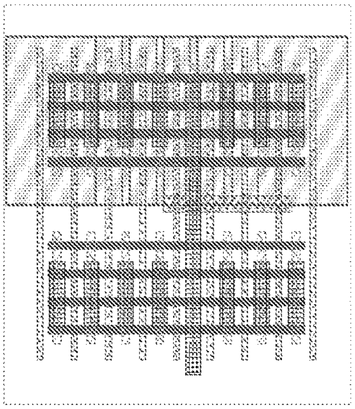
Figure 928C:
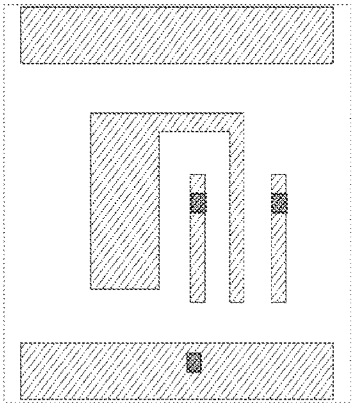
Figure 929A:
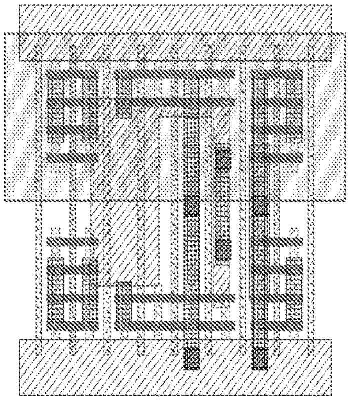
Figure 929B:
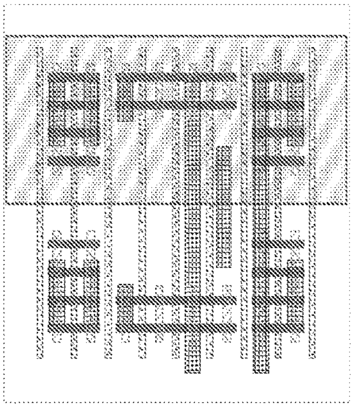
Figure 929C:
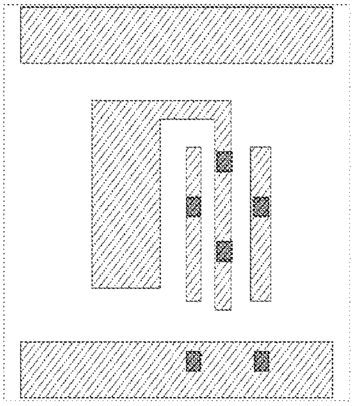
Figure 930A:
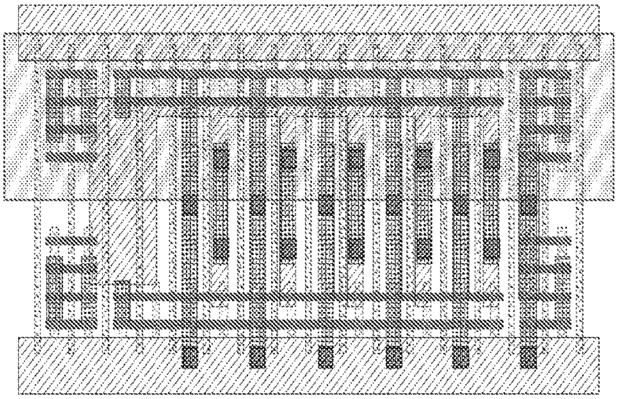
Figure 930B:
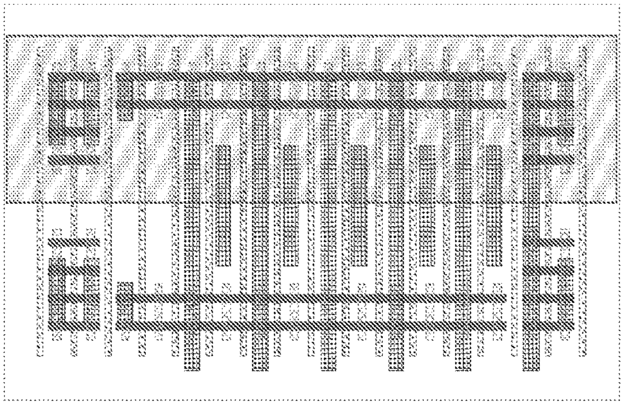
Figure 930C:
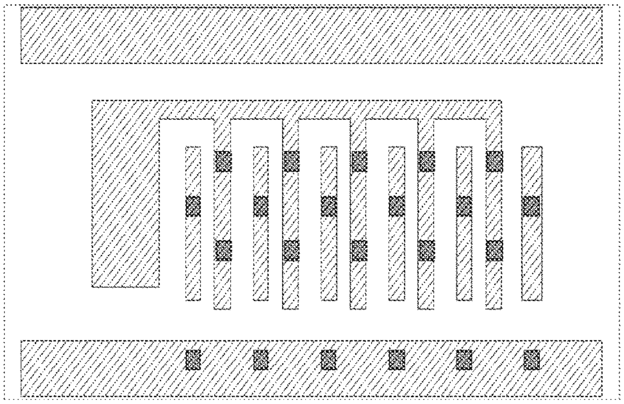
Figure 931A:
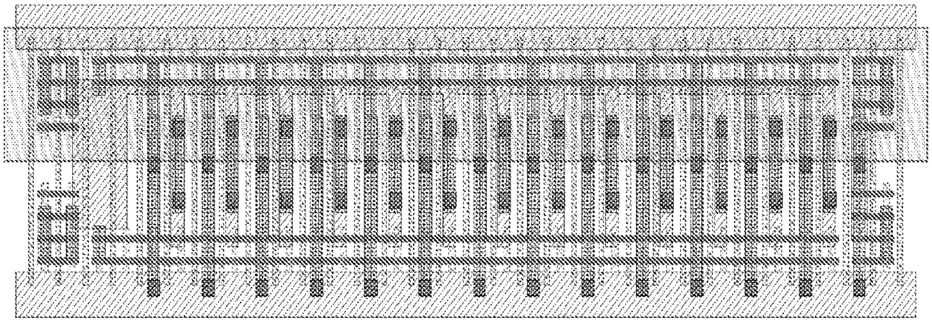
Figure 931B:
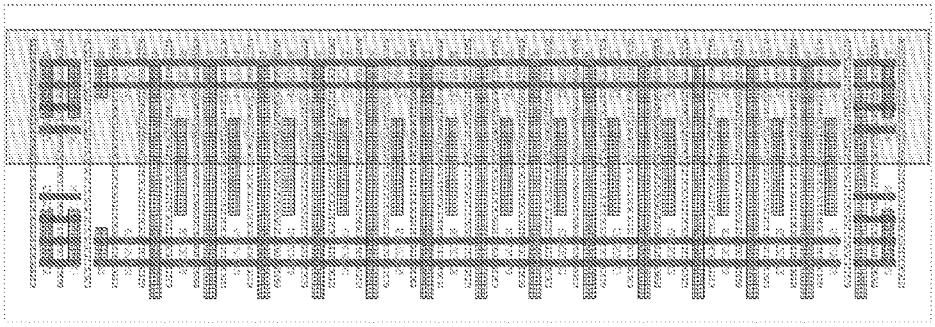
Figure 931C:
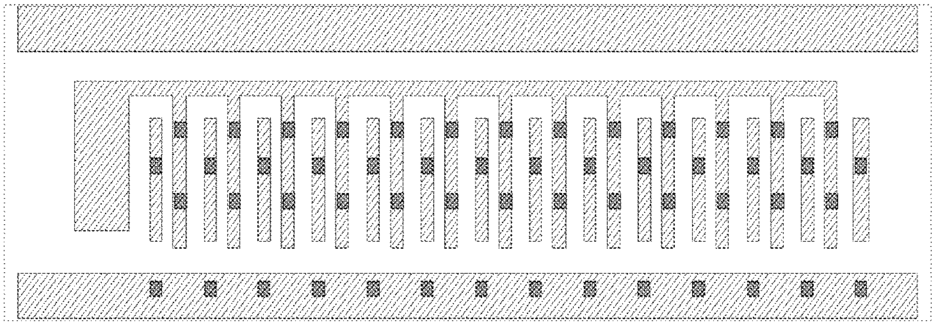
Figure 932A:
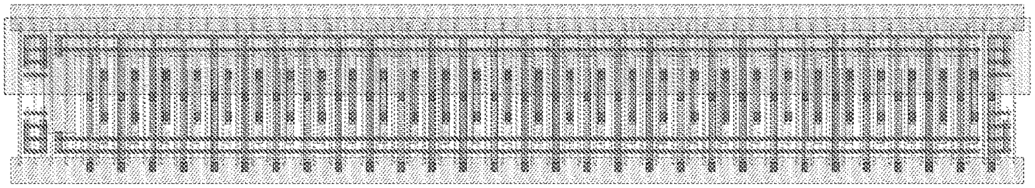
Figure 932B:
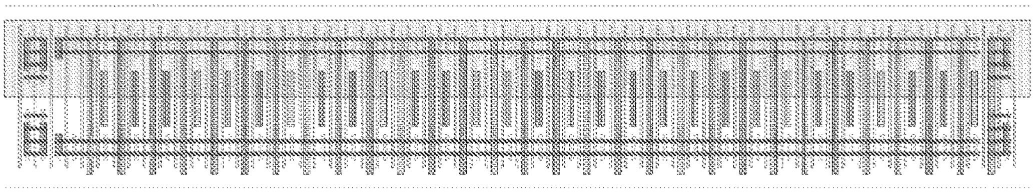
Figure 932C:
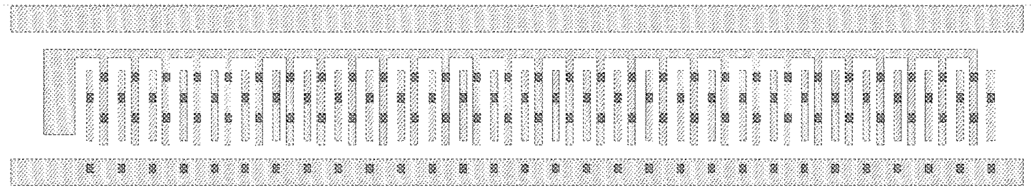
Figure 933A:
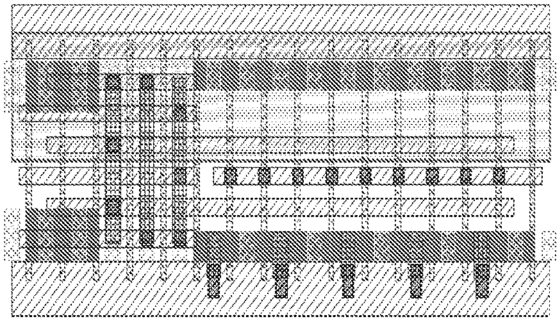
Figure 933B:
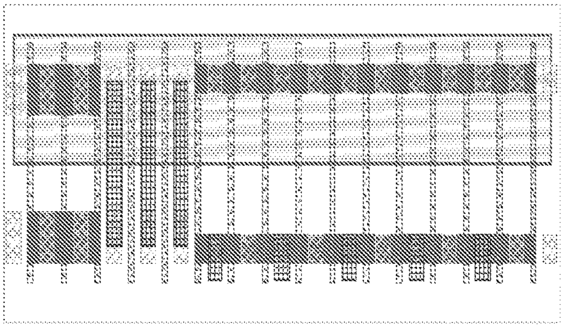
Figure 933C:
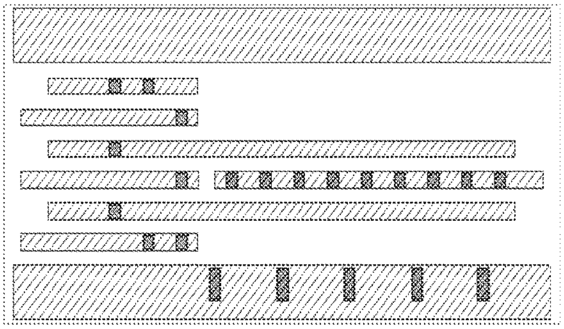
Figure 934A:
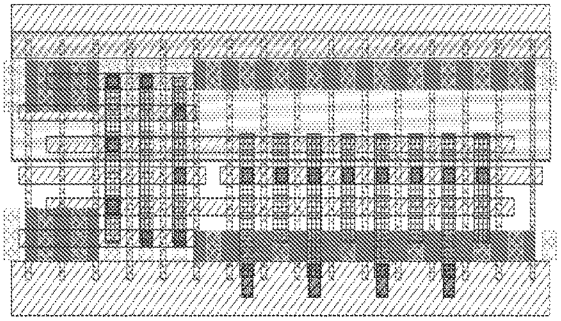
Figure 934B:
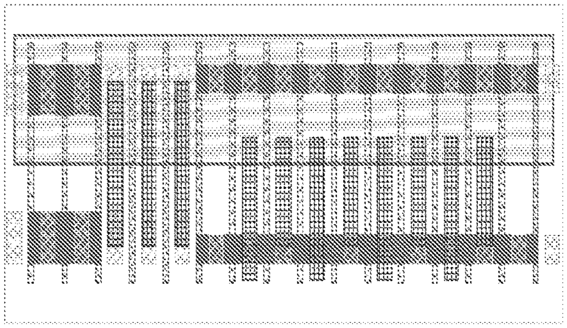
Figure 934C:
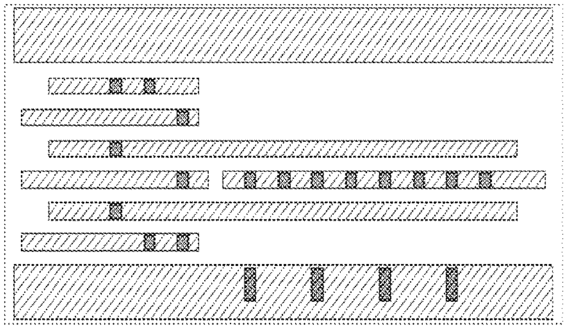
Figure 935A:
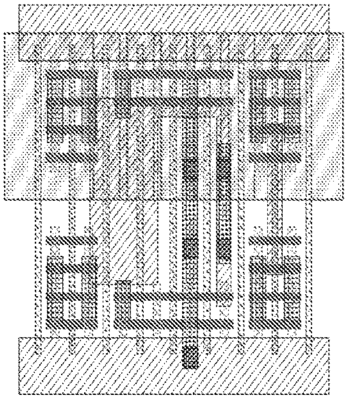
Figure 935B:
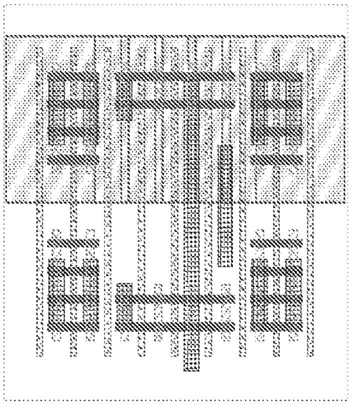
Figure 935C:
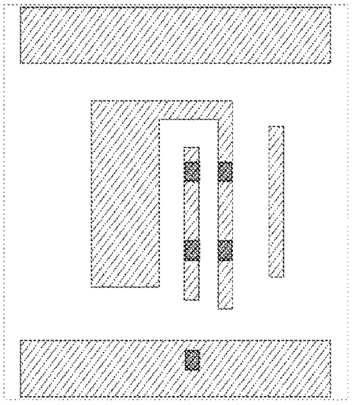
Figure 936A:
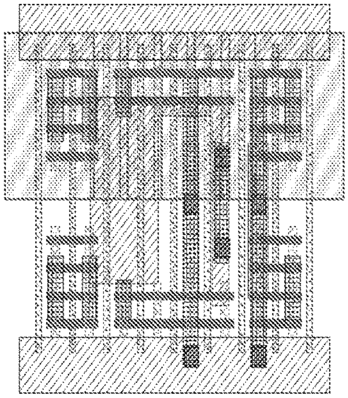
Figure 936B:
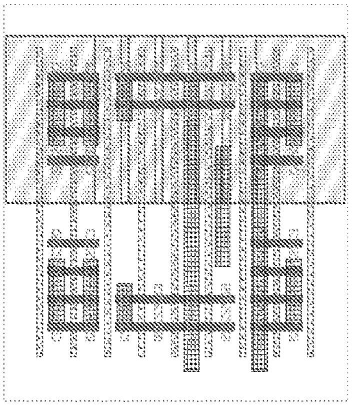
Figure 936C:
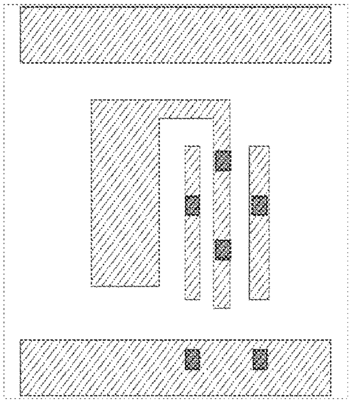
Figure 937A:
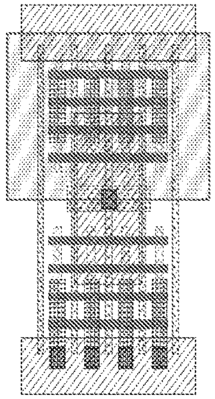
Figure 937B:
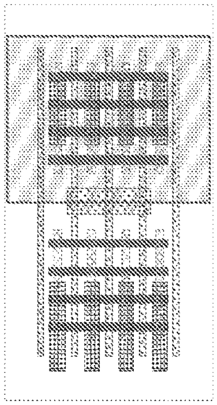
Figure 937C:
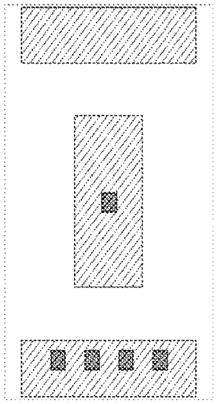
Figure 938A:
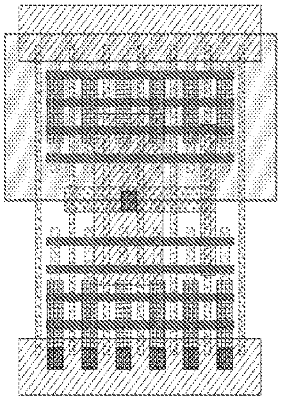
Figure 938B:
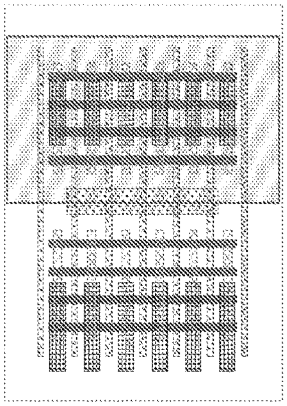
Figure 938C:
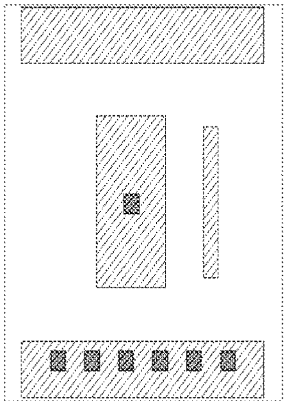
Figure 939A:
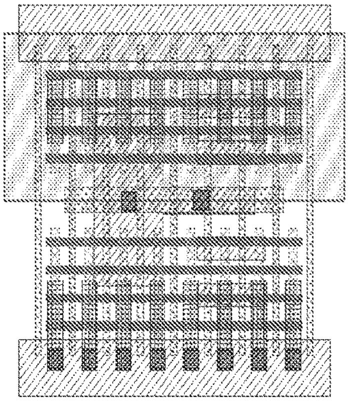
Figure 939B:
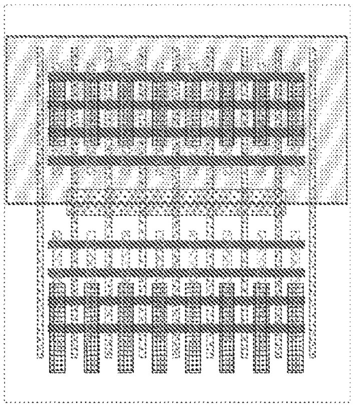
Figure 939C:
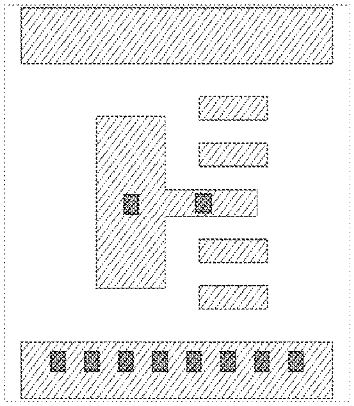
Figure 940A:
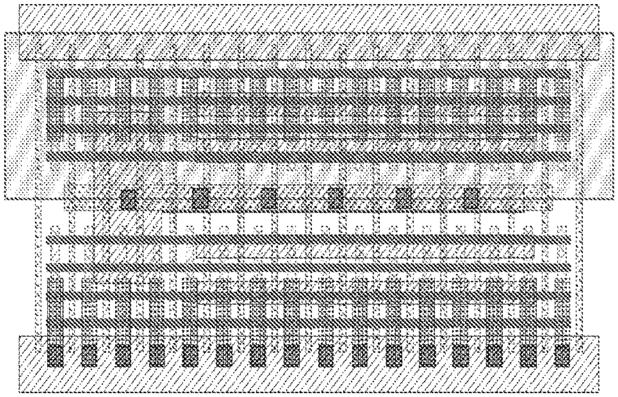
Figure 940B:
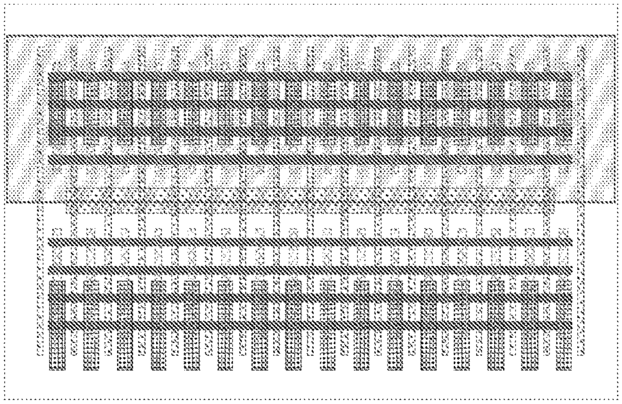
Figure 940C:
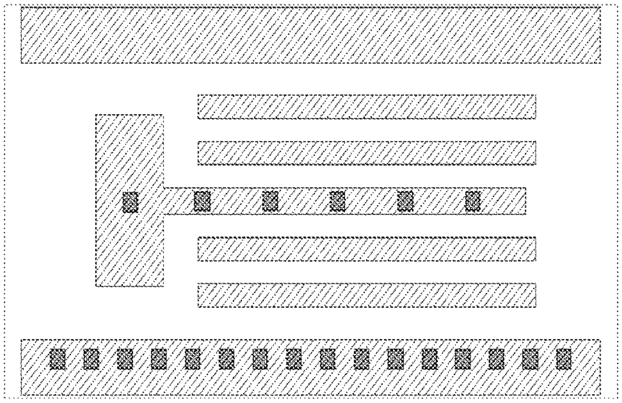
Figure 941A:
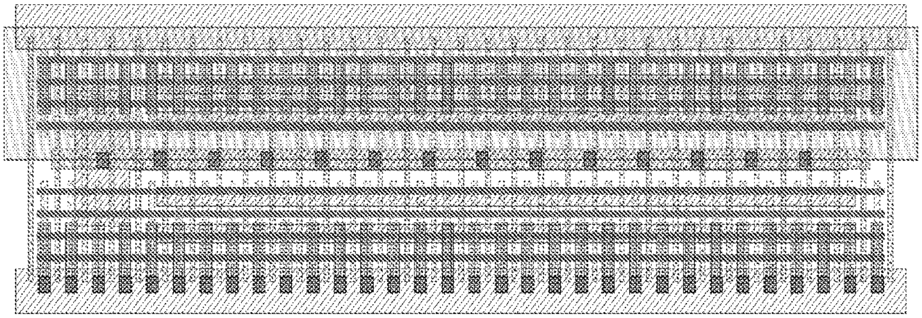
Figure 941B:
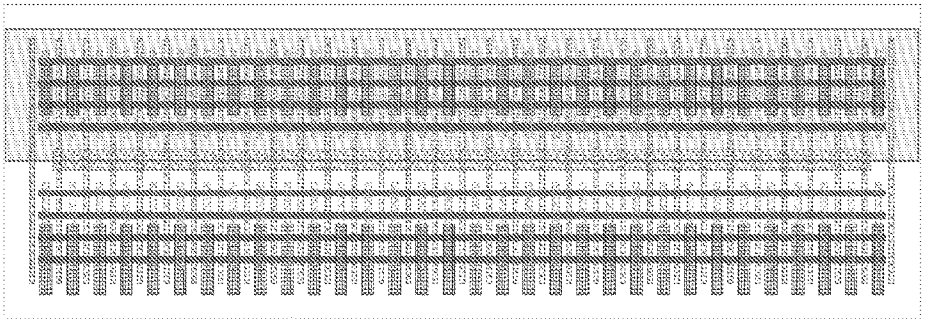
Figure 941C:
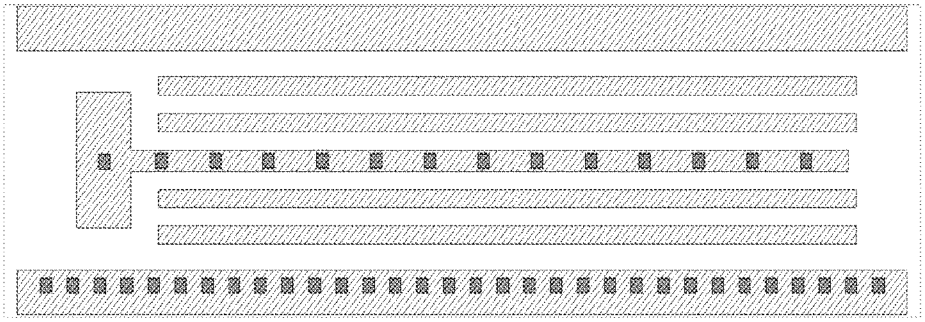
Figure 942A:
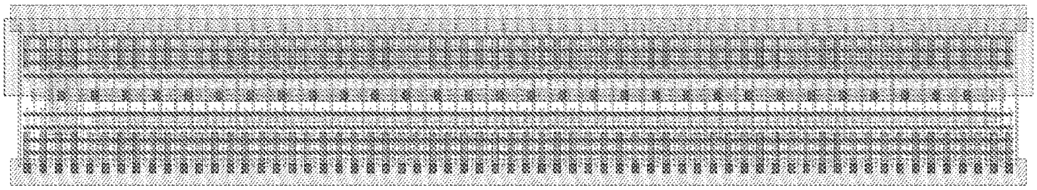
Figure 942B:
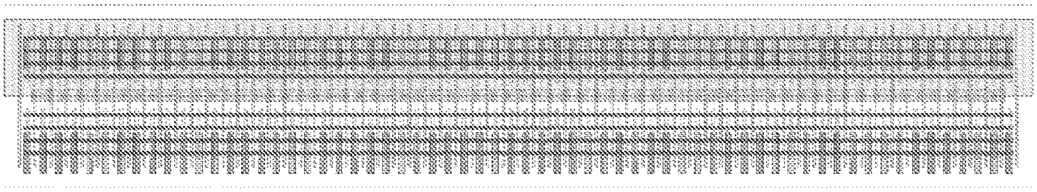
Figure 942C:
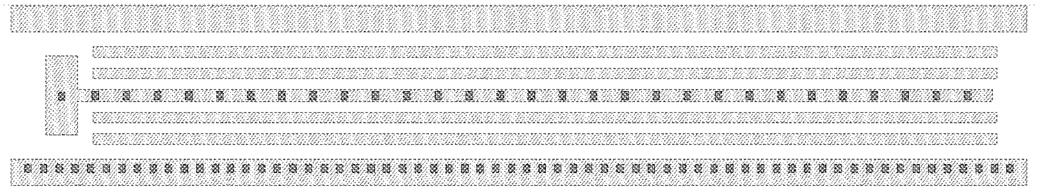
Figure 943A:
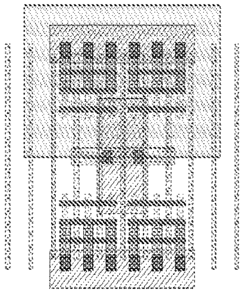
Figure 943B:
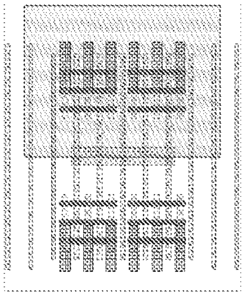
Figure 943C:
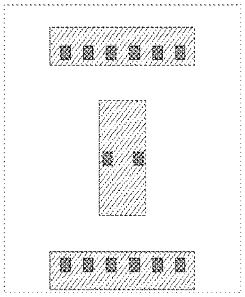
Figure 944A:
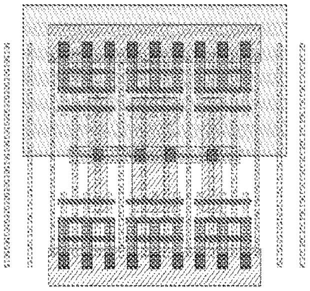
Figure 944B:
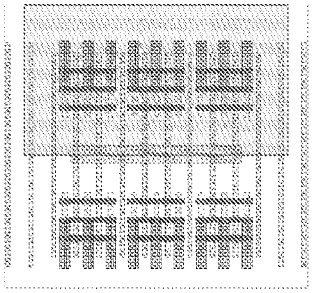
Figure 944C:
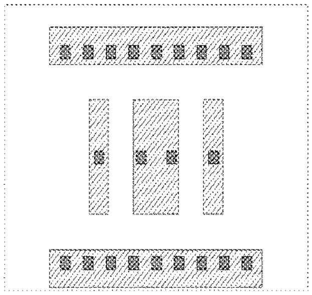
Figure 945A:
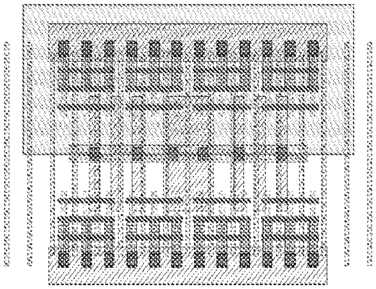
Figure 945B:
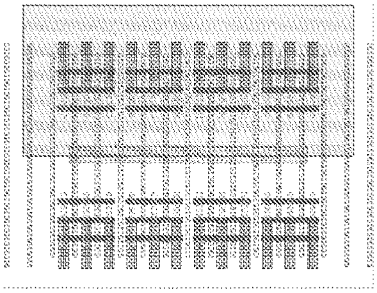
Figure 945C:
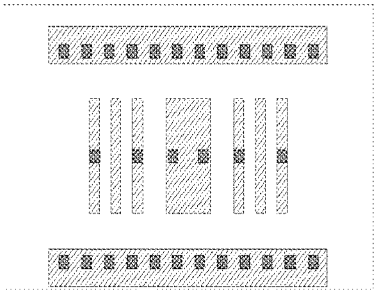
Figure 946A:
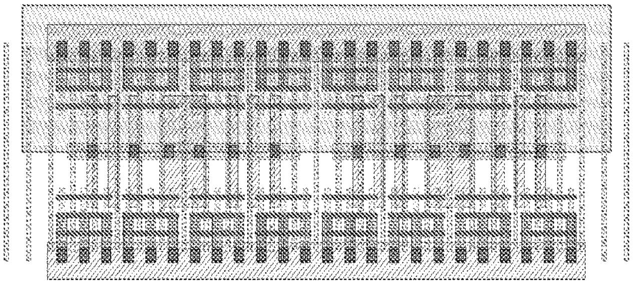
Figure 946B:
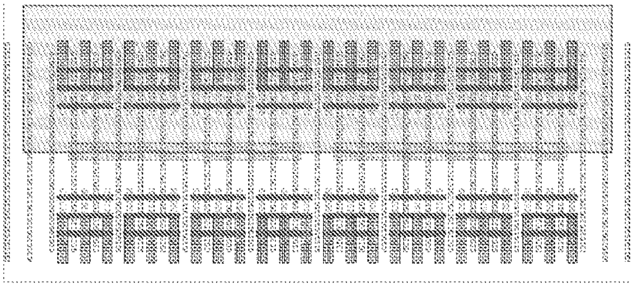
Figure 946C:
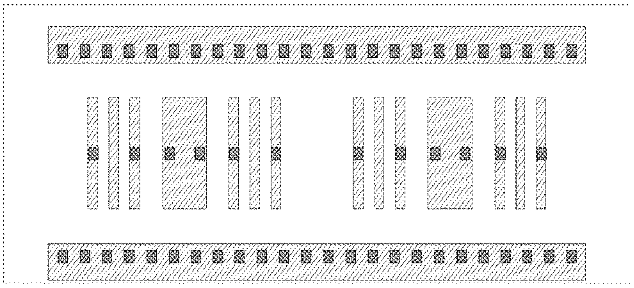
Figure 947A:
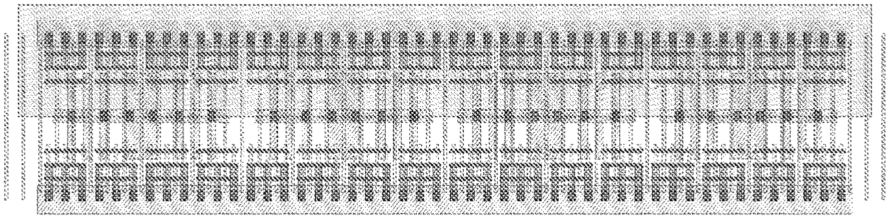
Figure 947B:
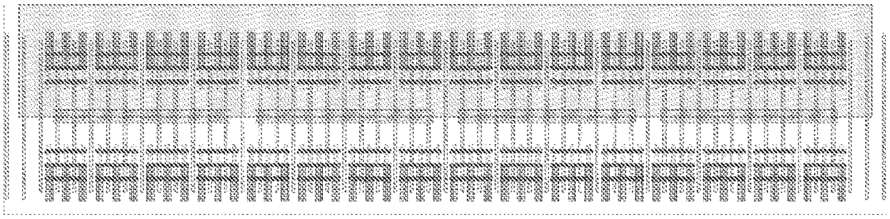
Figure 947C:
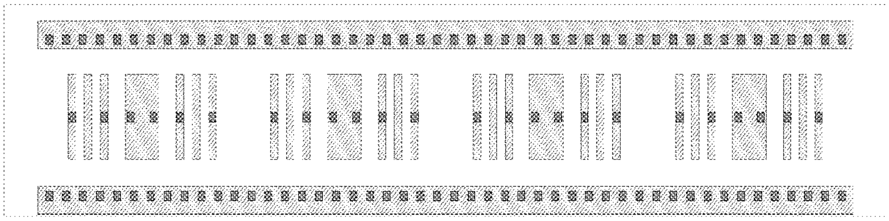
Figure 948A:
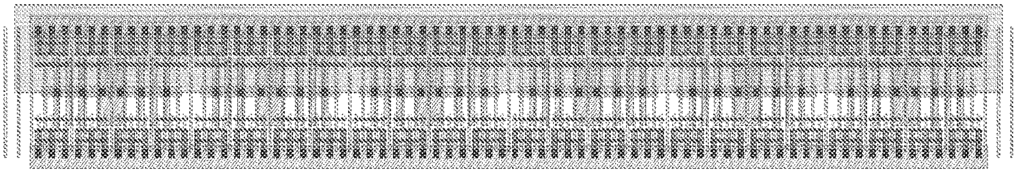
Figure 948B:
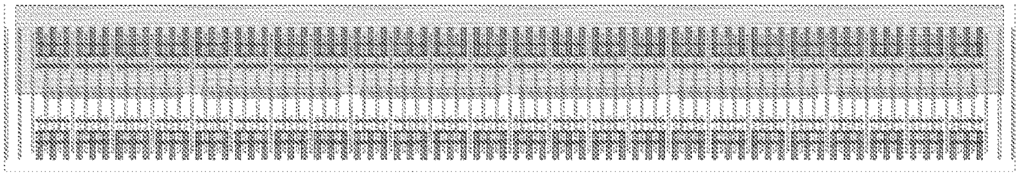
Figure 948C:
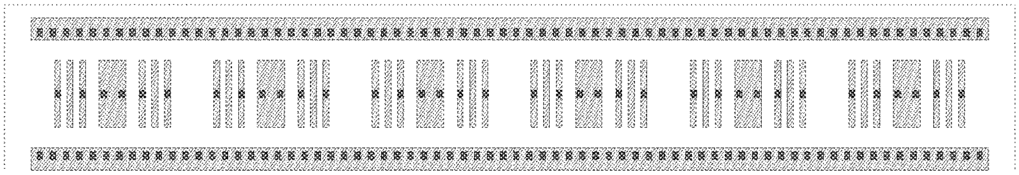
Figure 949A:
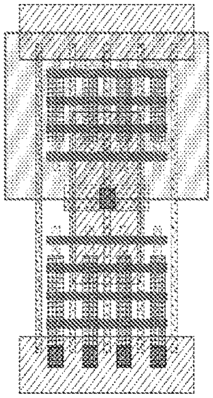
Figure 949B:
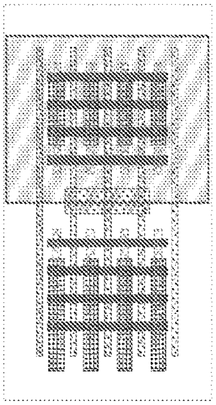
Figure 949C:
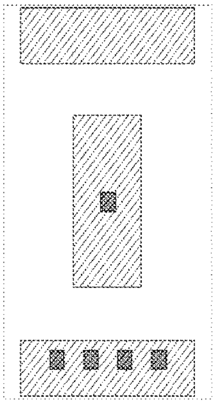
Figure 950A:
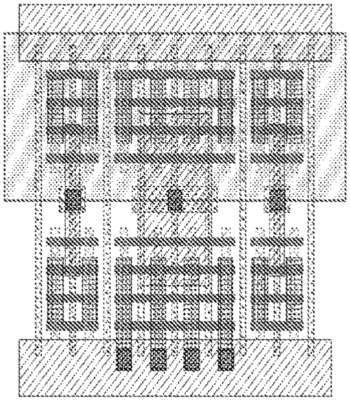
Figure 950B:
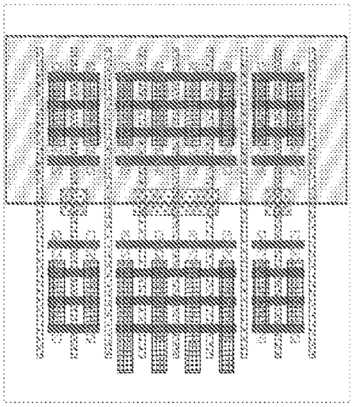
Figure 950C:
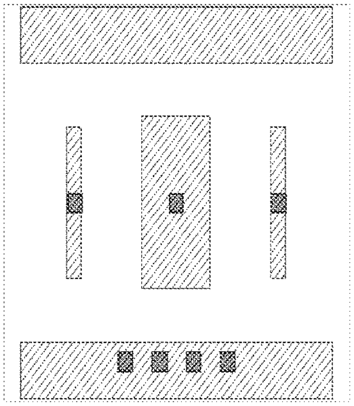
Figure 951A:
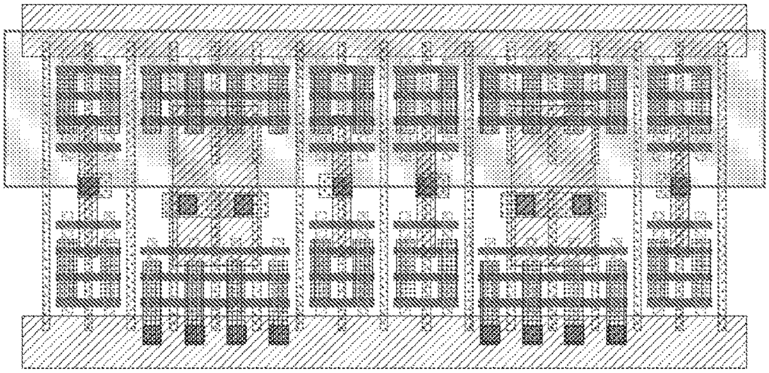
Figure 951B:
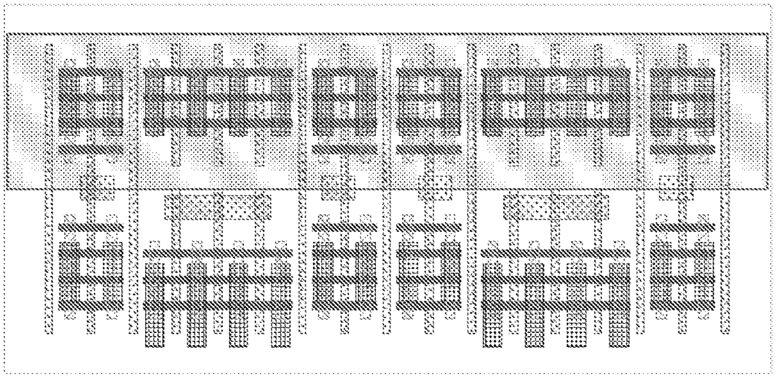
Figure 951C:
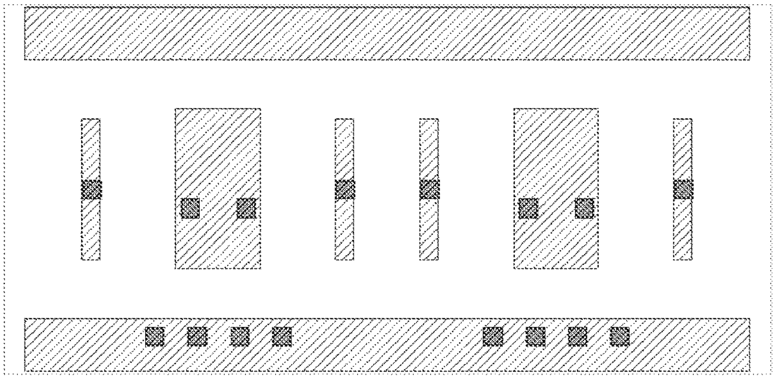
Figure 952A:
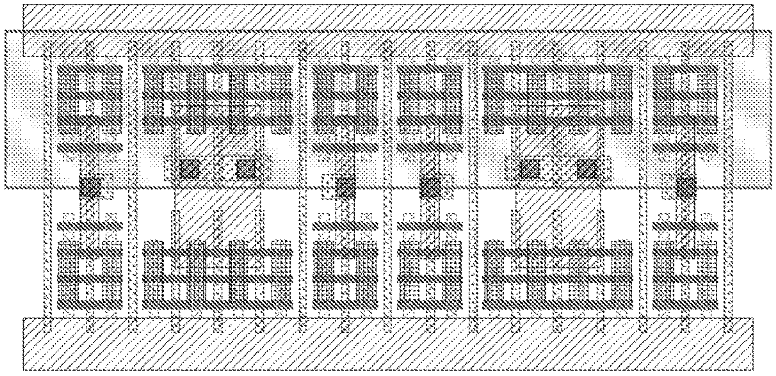
Figure 952B:
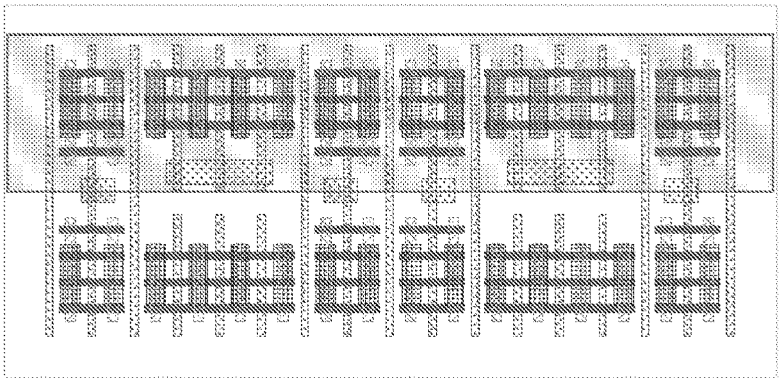
Figure 952C:
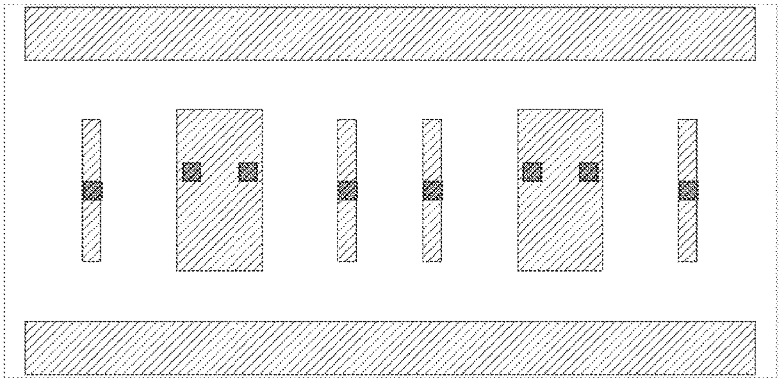
Figure 953A:
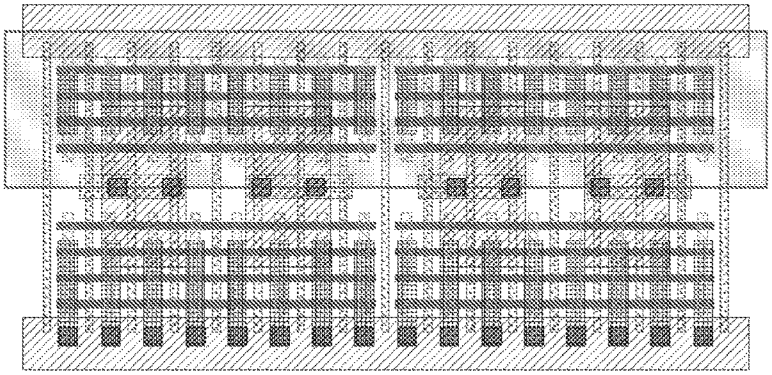
Figure 953B:
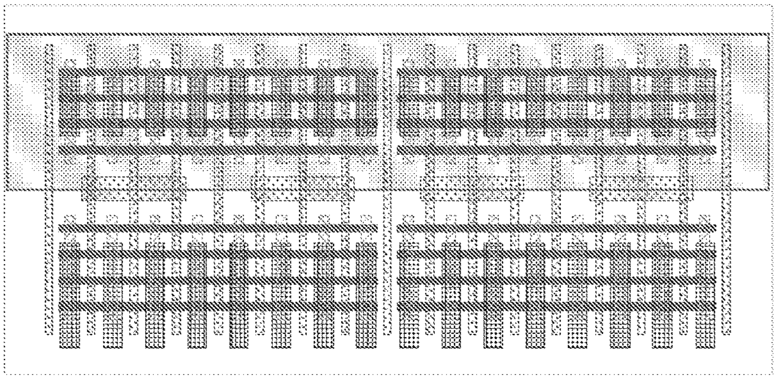
Figure 953C:
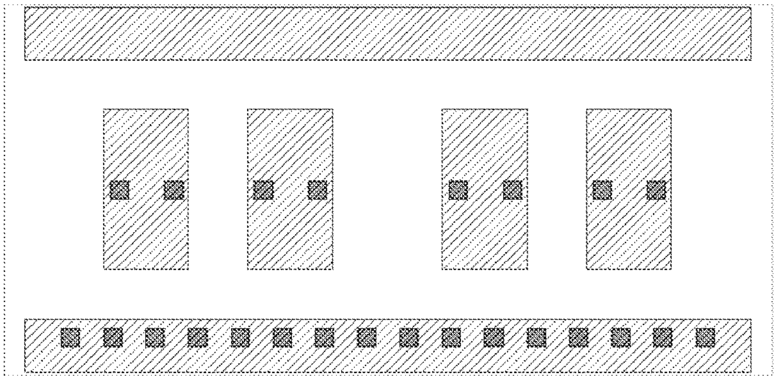
Figure 954A:
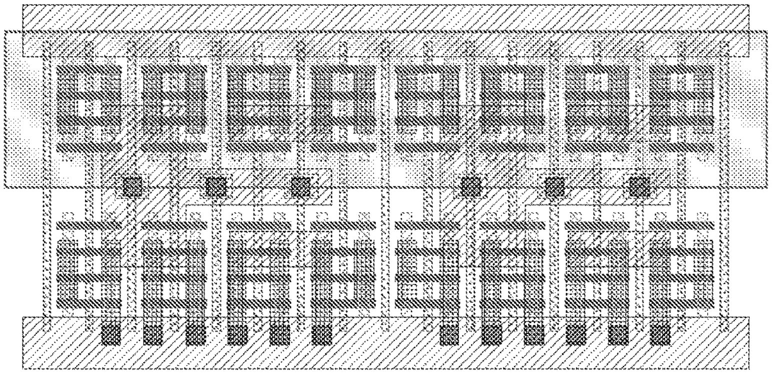
Figure 954B:
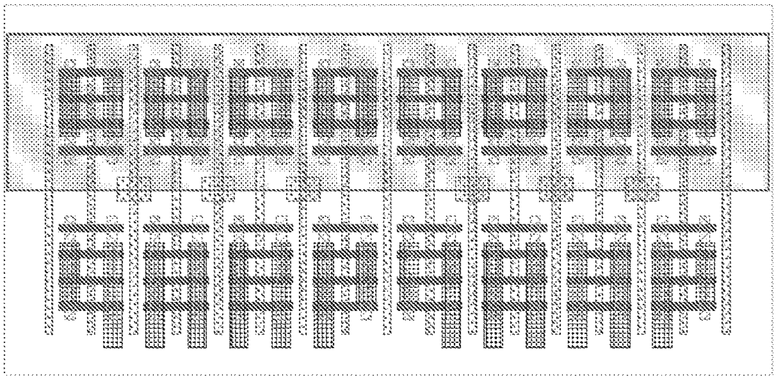
Figure 954C:
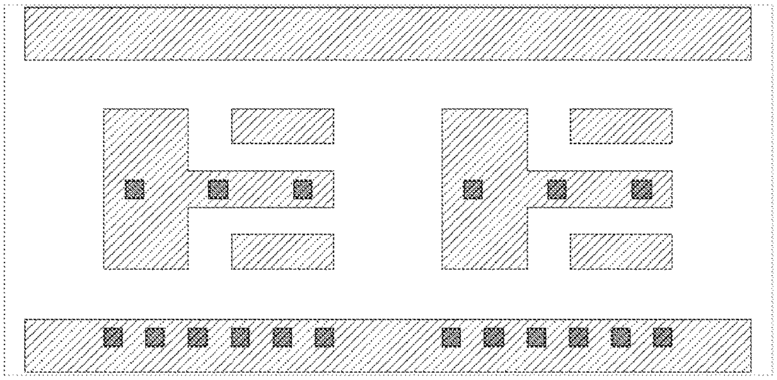
Figure 955A:
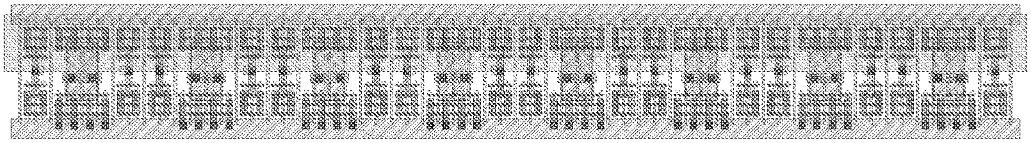
Figure 955B:
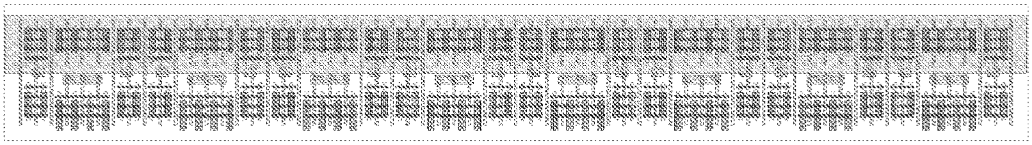
Figure 955C:
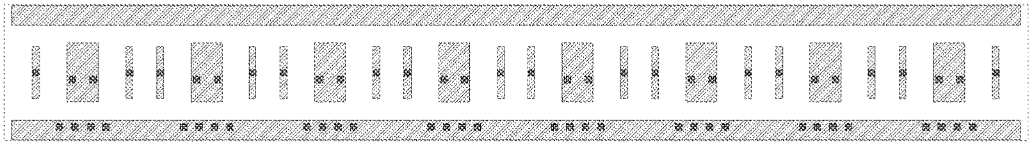
Figure 956A:
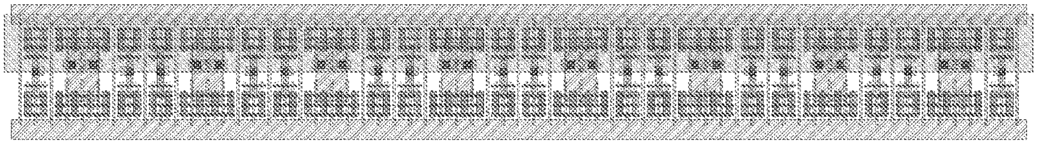
Figure 956B:
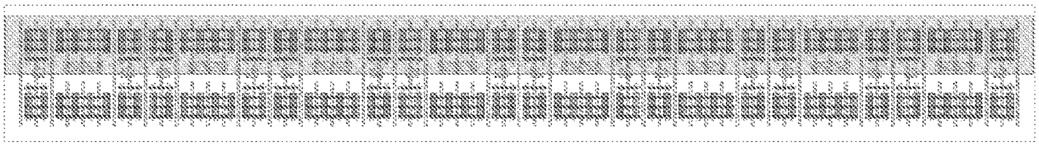
Figure 956C:
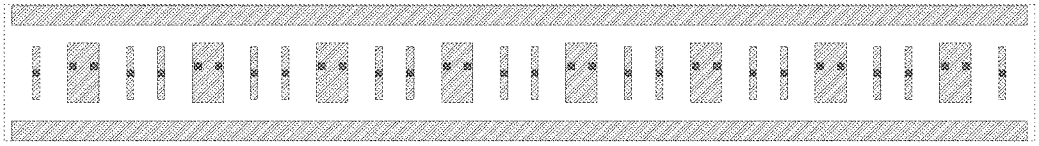
Figure 957A:
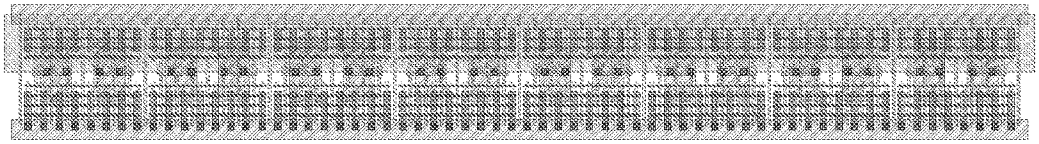
Figure 957B:
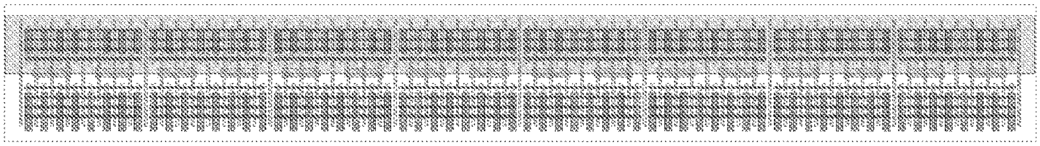
Figure 957C:
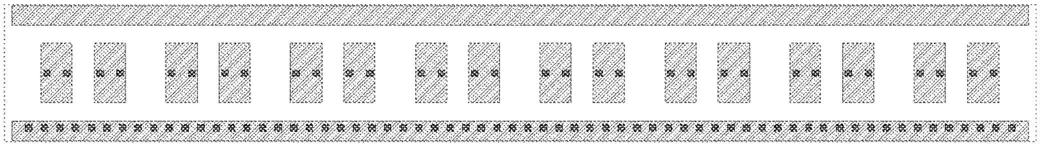
Figure 958A:
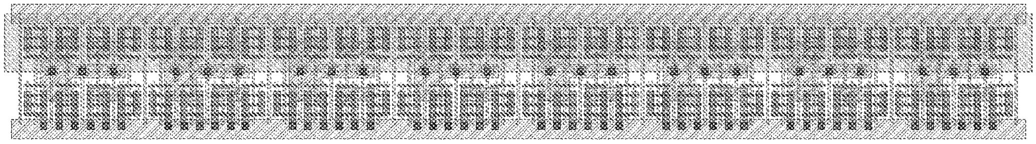
Figure 958B:
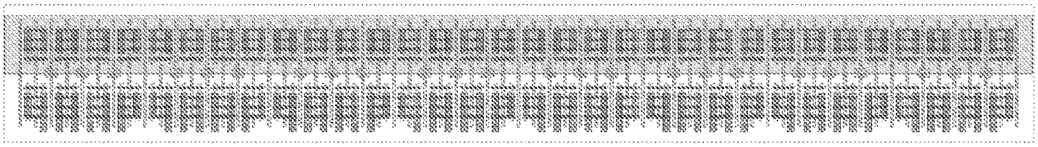
Figure 958C:
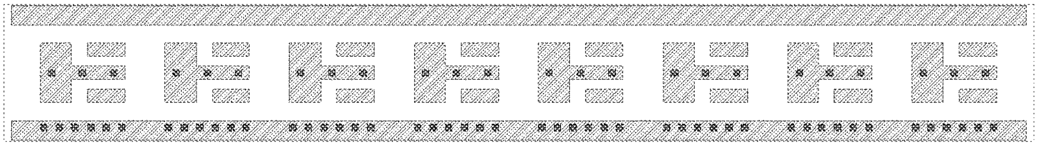
Figure 959A:
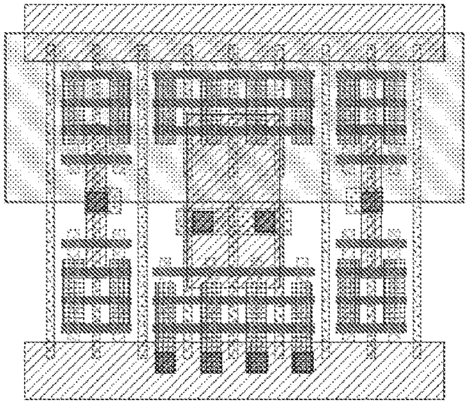
Figure 959B:
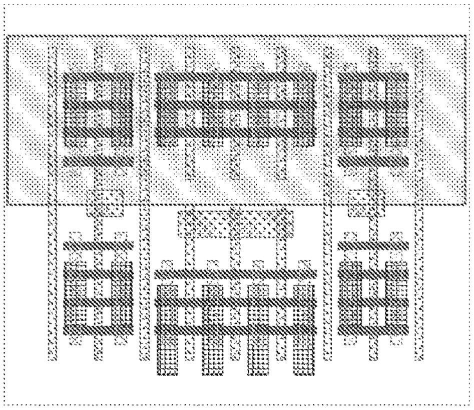
Figure 959C:
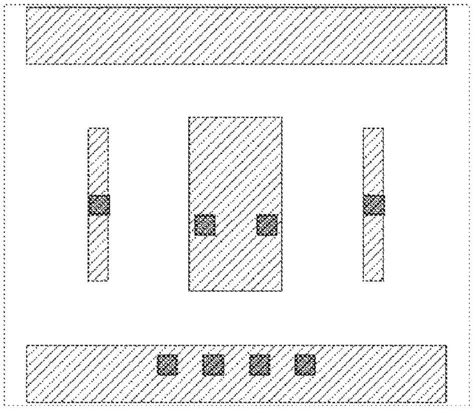
Figure 960A:
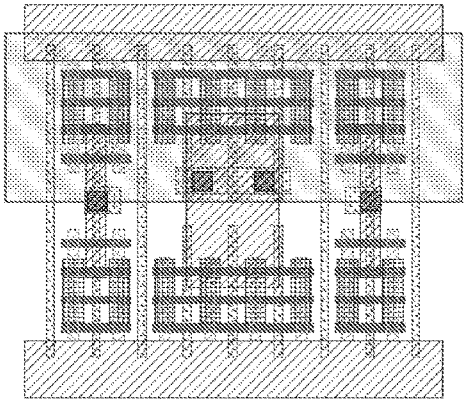
Figure 960B:
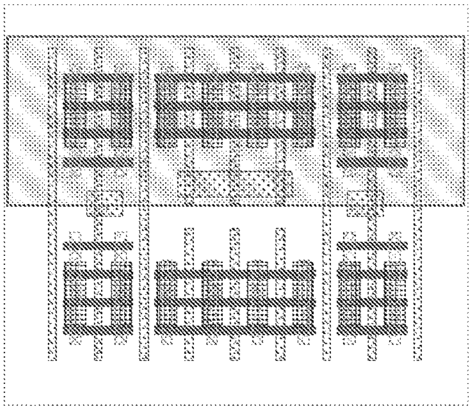
Figure 960C:
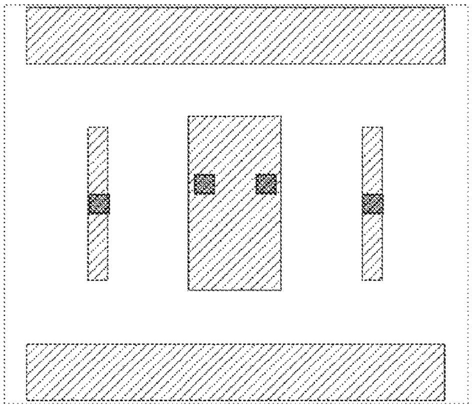
Figure 961A:
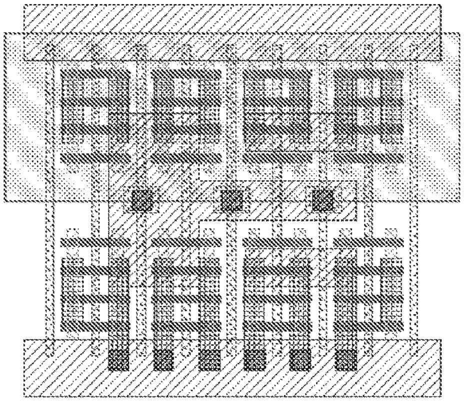
Figure 961B:
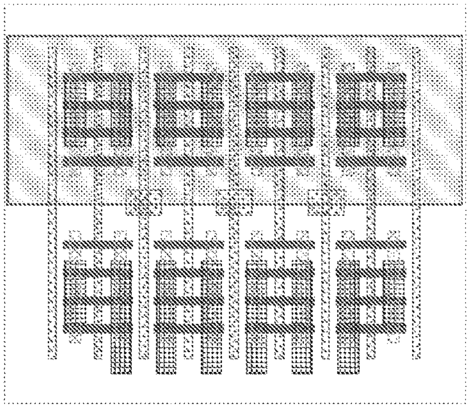
Figure 961C:
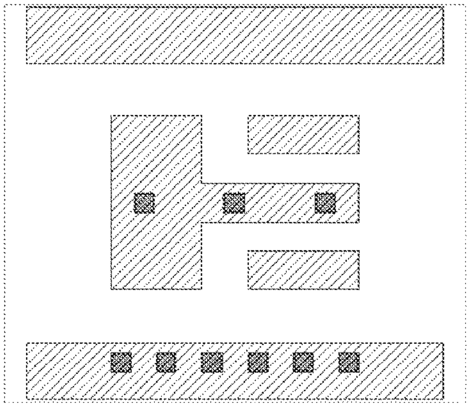
Figure 962A:
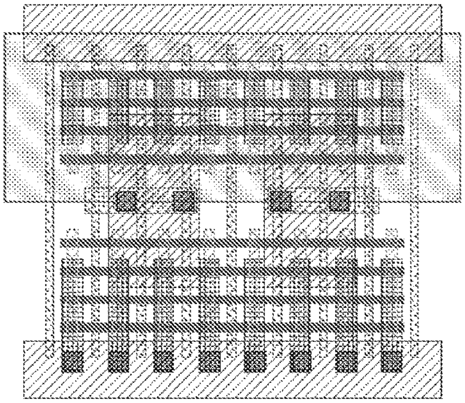
Figure 962B:
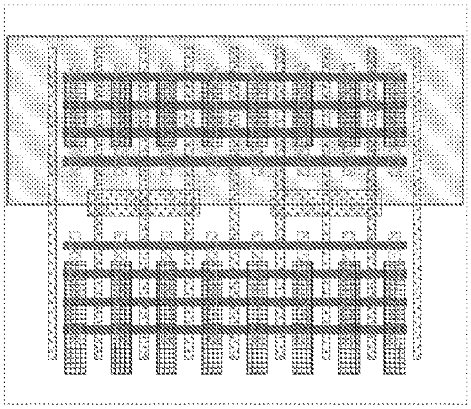
Figure 962C:
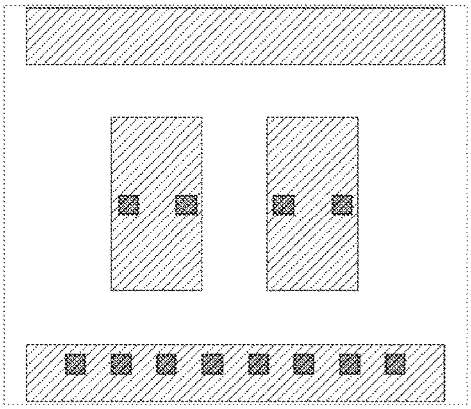
Figure 963A:
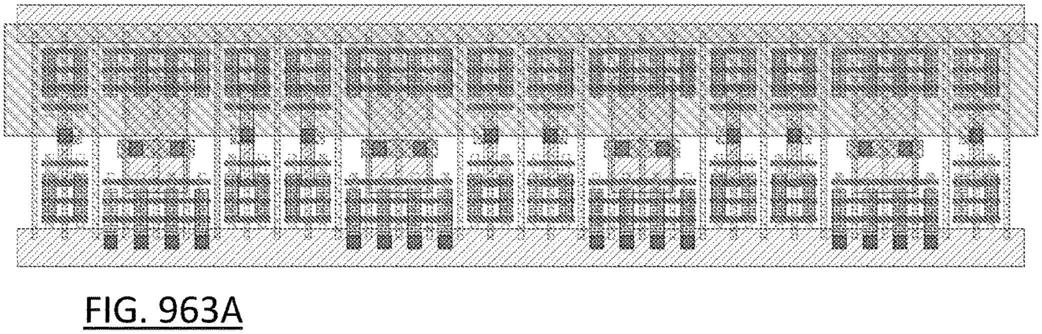
Figure 963B:
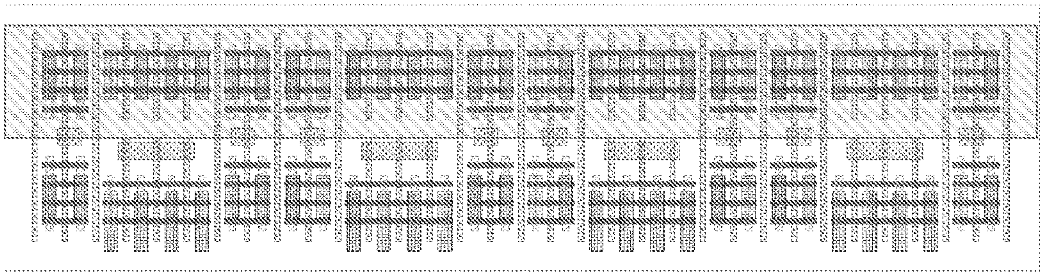
Figure 963C:
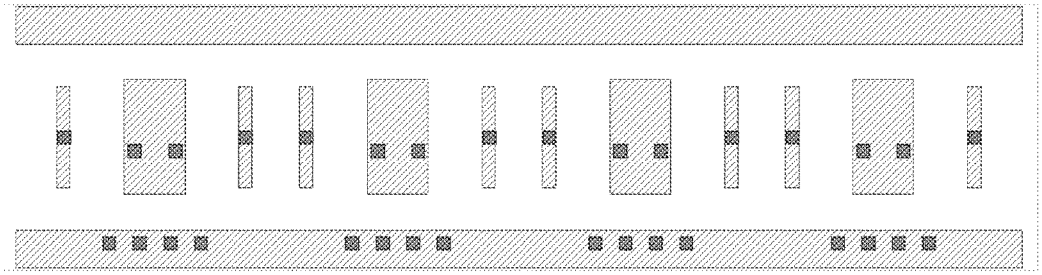
Figure 964A:
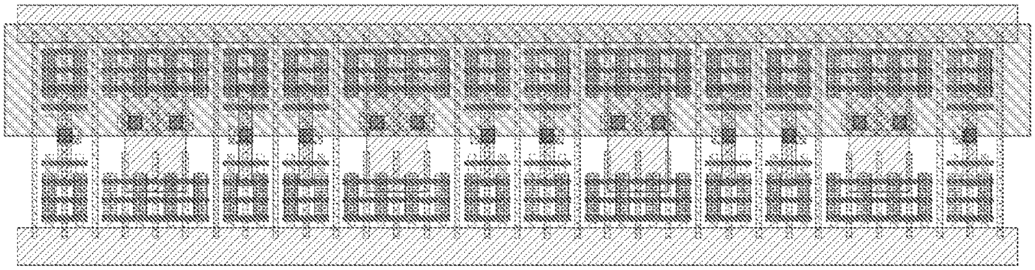
Figure 964B:
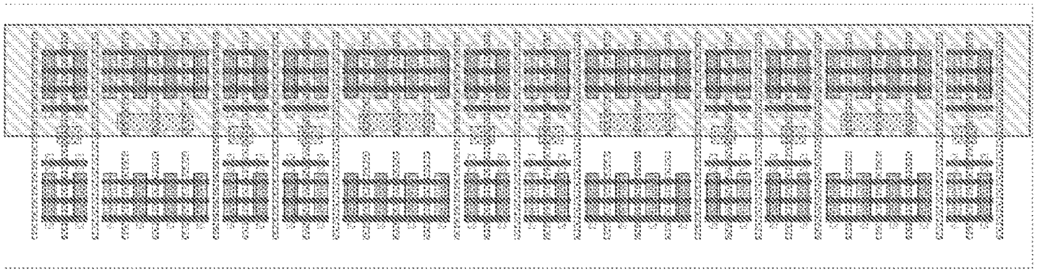
Figure 964C:
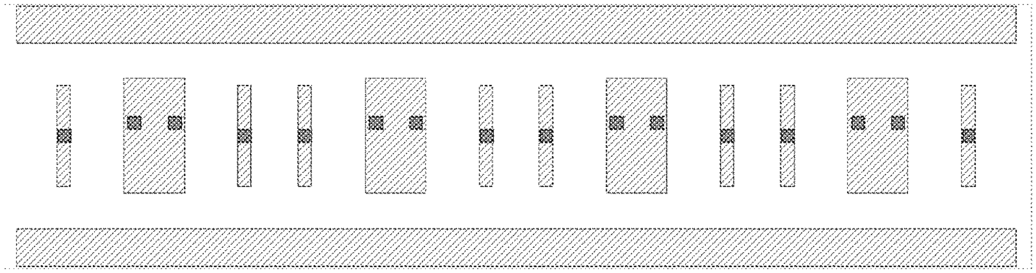
Figure 965A:
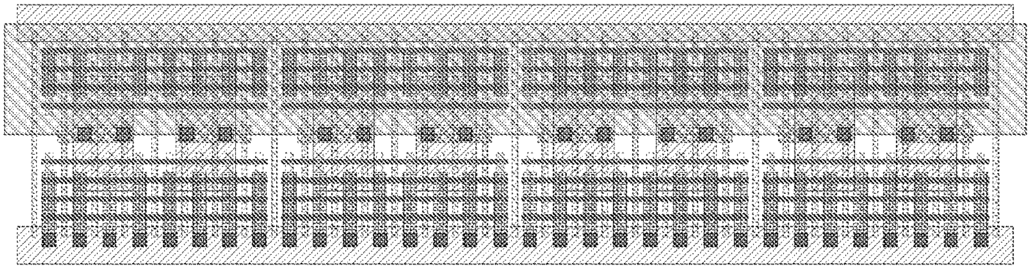
Figure 965B:
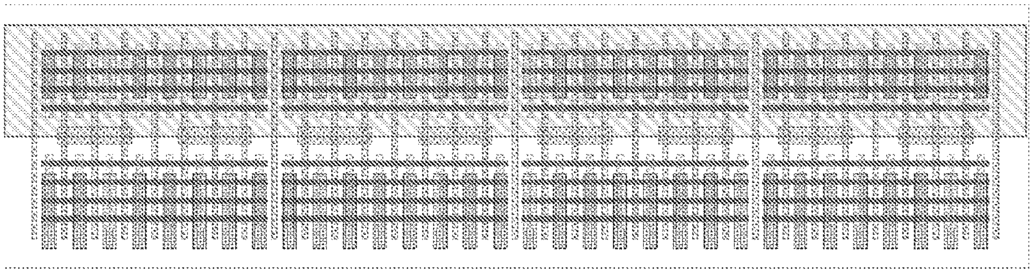
Figure 965C:
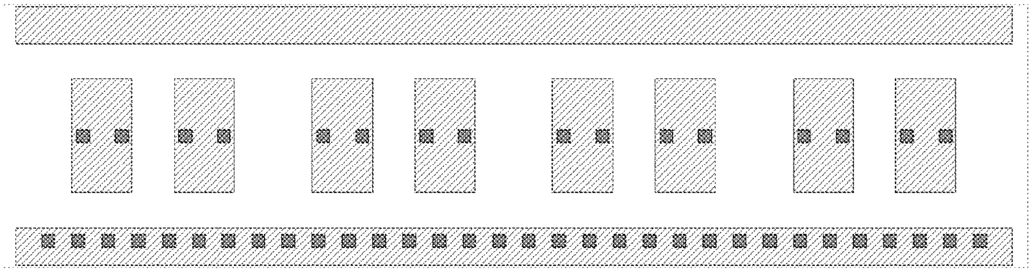
Figure 966A:
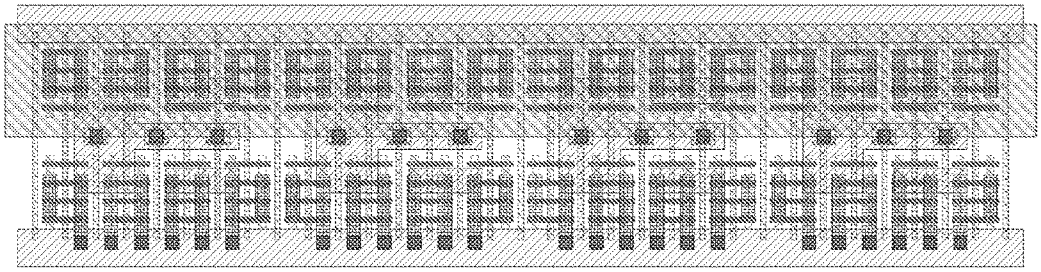
Figure 966B:
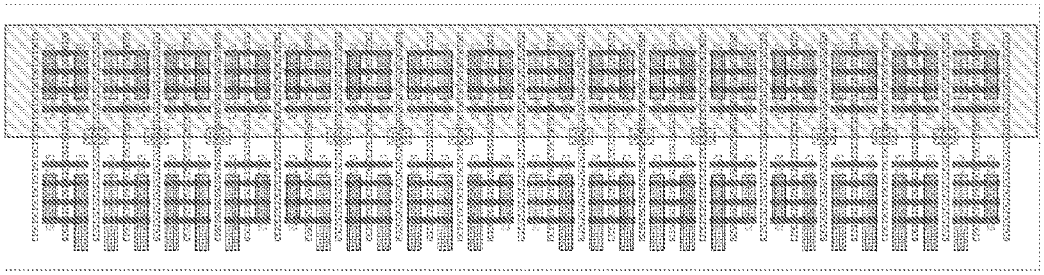
Figure 966C:
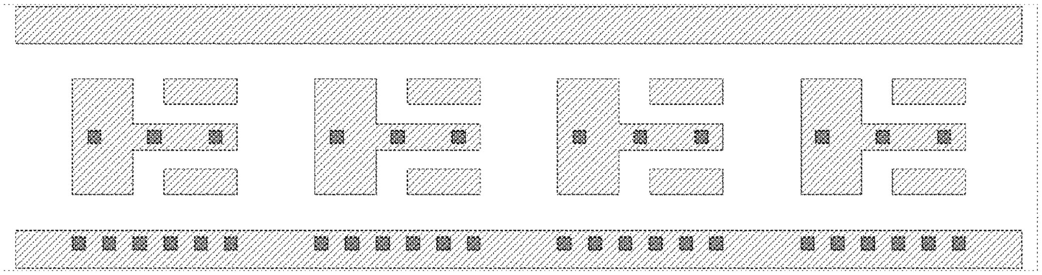
Figure 967A:
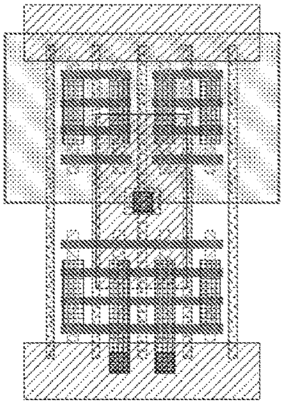
Figure 967B:
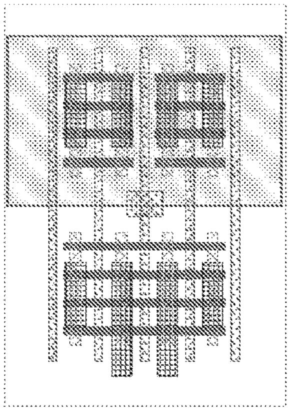
Figure 967C:
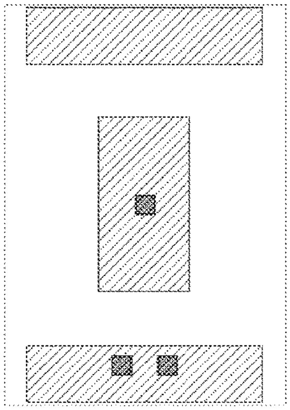
Figure 968A:
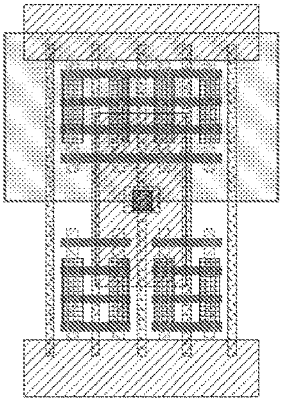
Figure 968B:
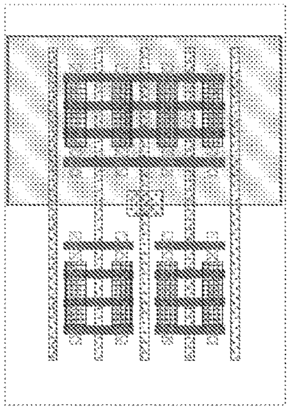
Figure 968C:
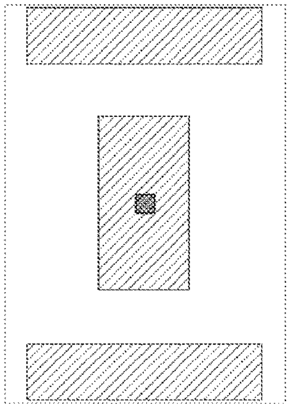
Figure 969A:
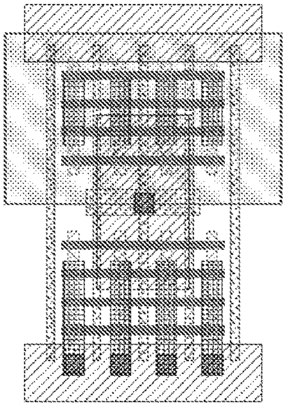
Figure 969B:
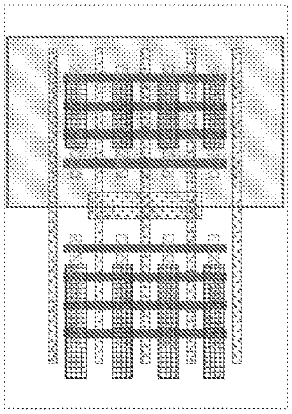
Figure 969C:
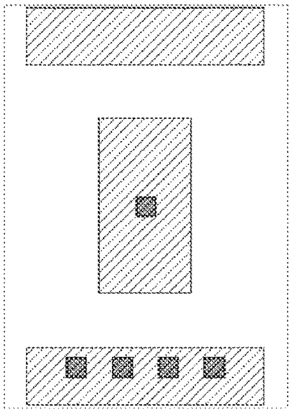
Figure 970A:
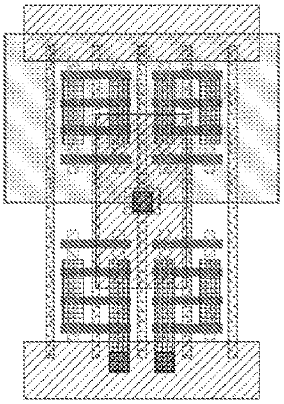
Figure 970B:
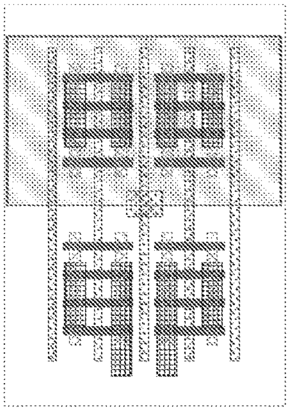
Figure 970C:
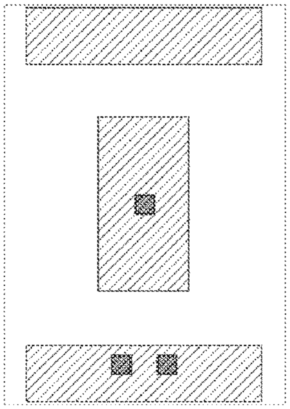
Figure 971A:
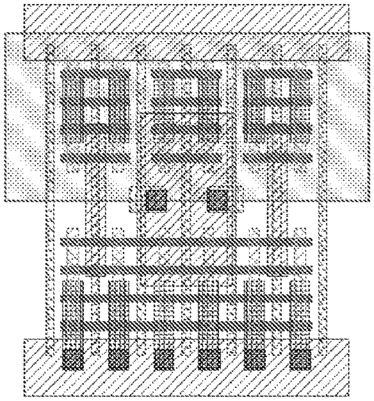
Figure 971B:
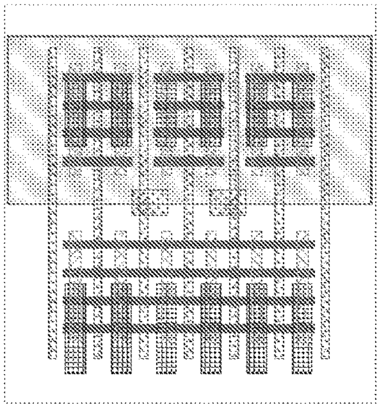
Figure 971C:
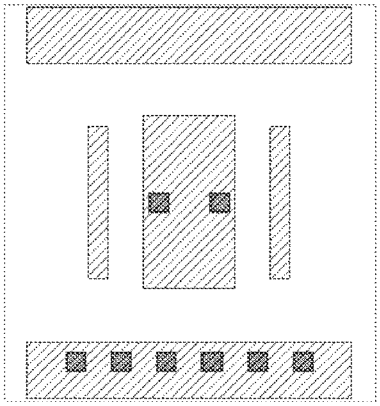
Figure 972A:
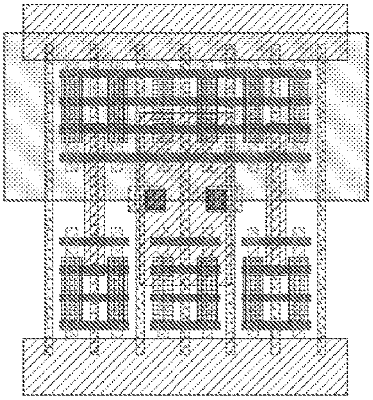
Figure 972B:
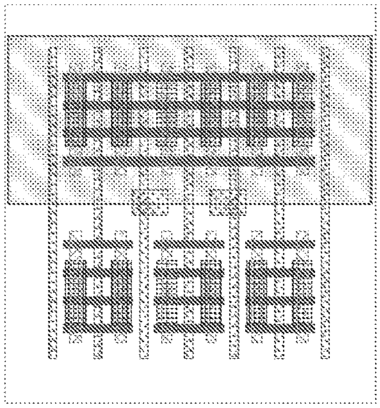
Figure 972C:
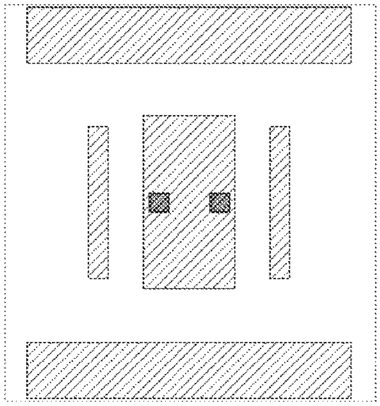
Figure 973A:
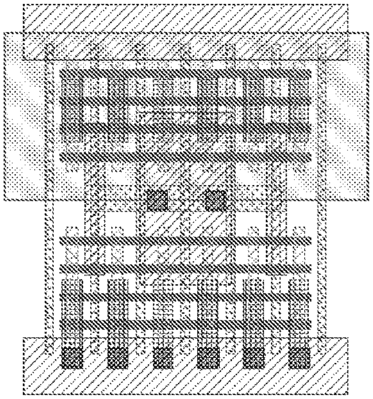
Figure 973B:
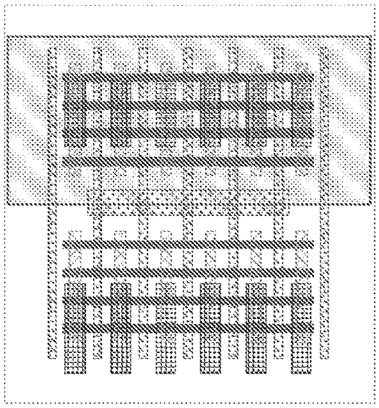
Figure 973C:
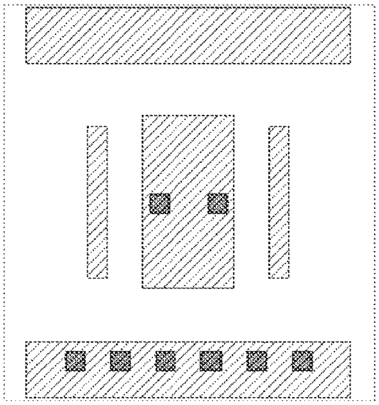
Figure 974A:
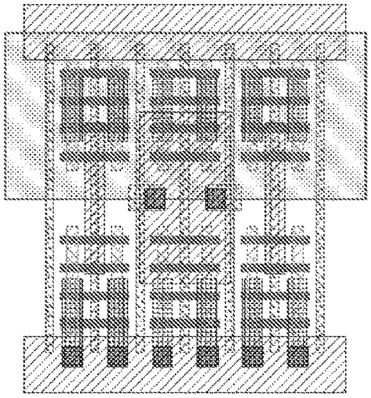
Figure 974B:
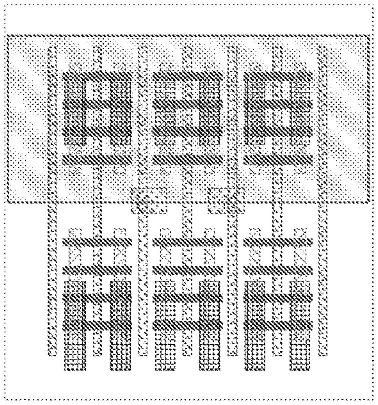
Figure 974C:
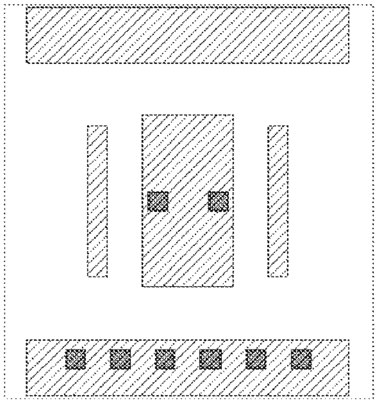
Figure 975A:
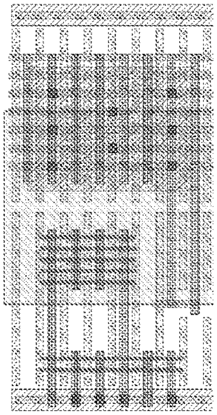
Figure 975B:
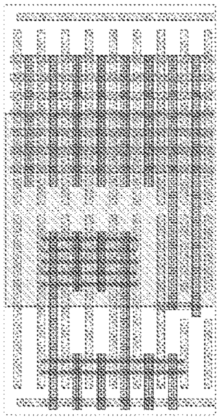
Figure 975C:
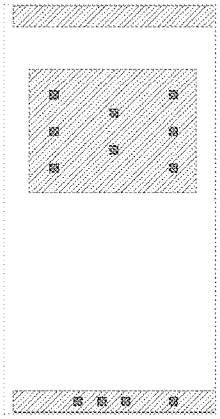
Figure 976A:
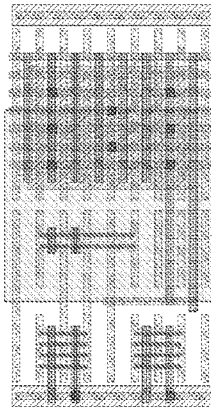
Figure 976B:
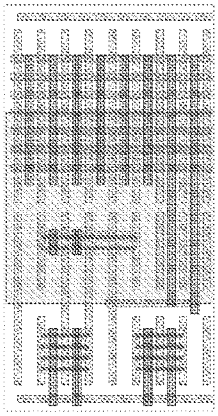
Figure 976C:
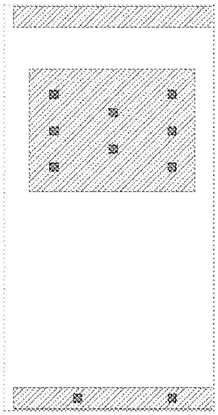
Figure 977A:
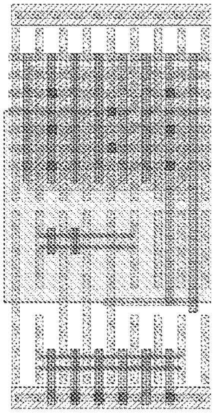
Figure 977B:
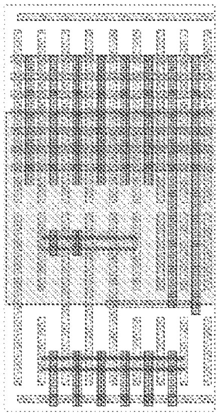
Figure 977C:
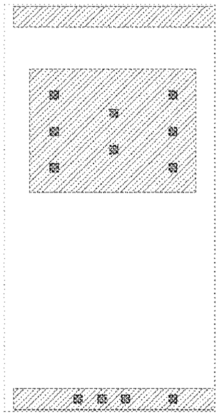
Figure 978A:
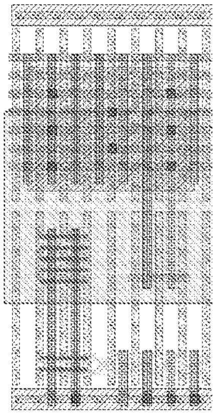
Figure 978B:
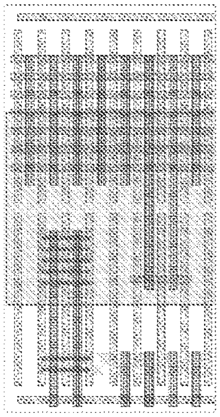
Figure 978C:
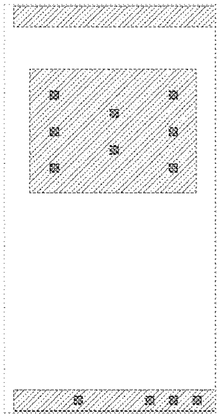
Figure 979A:
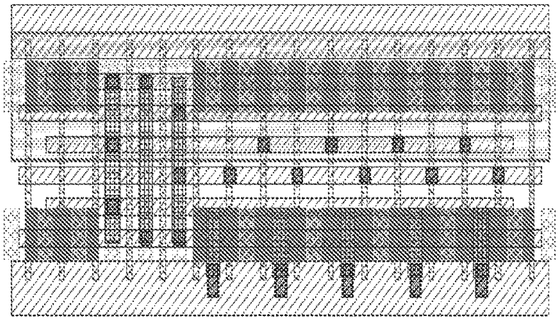
Figure 979B:
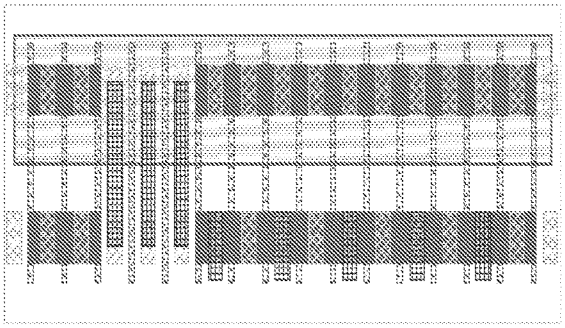
Figure 979C:
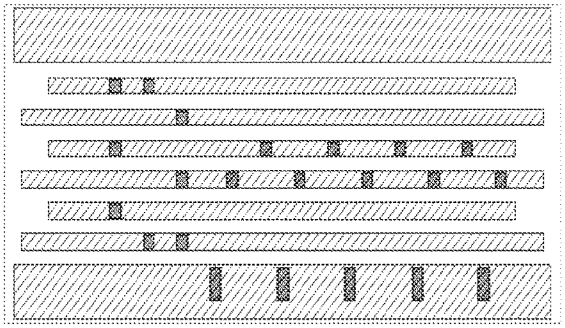
Figure 980A:
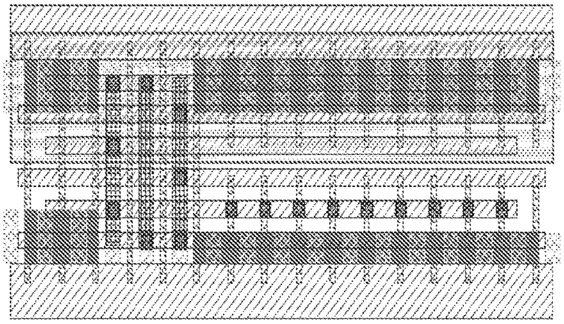
Figure 980B:
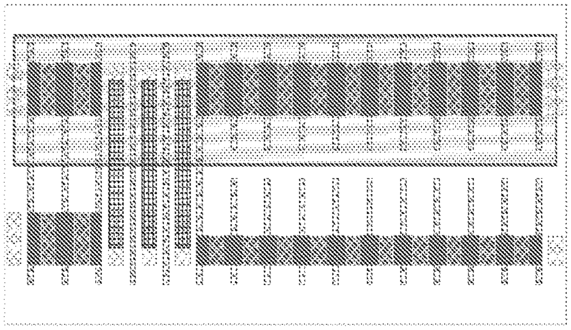
Figure 980C:
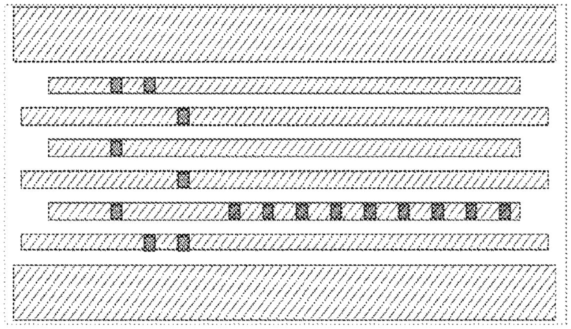
Figure 981A:
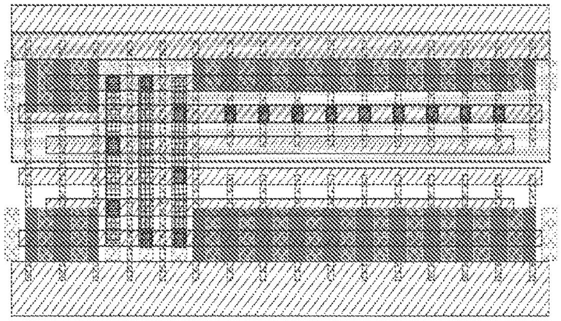
Figure 981B:
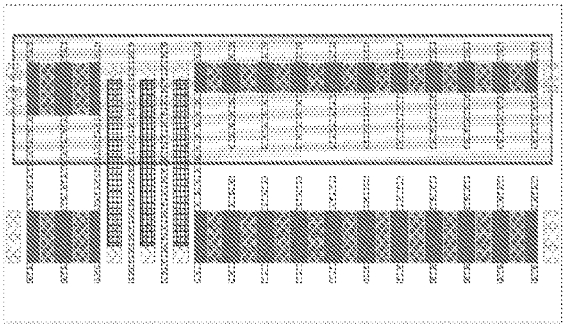
Figure 981C:
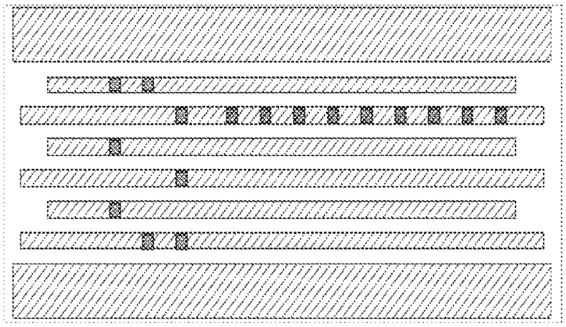
Figure 982A:
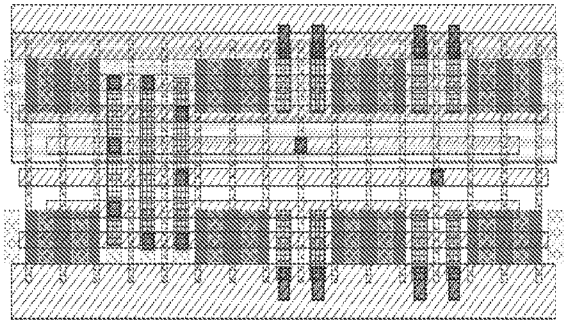
Figure 982B:
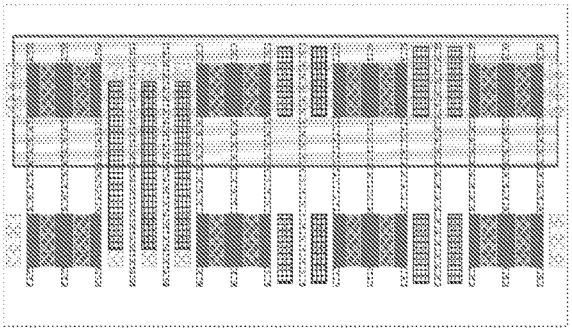
Figure 982C:
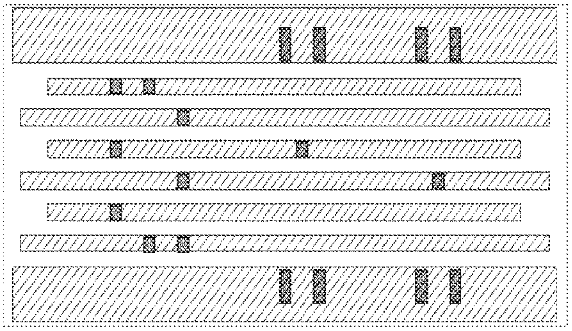
Figure 983A:
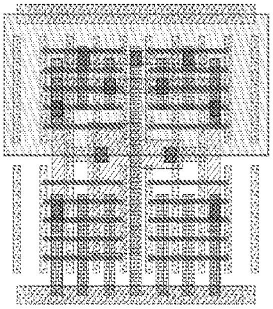
Figure 983B:
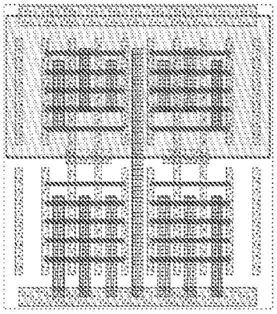
Figure 983C:
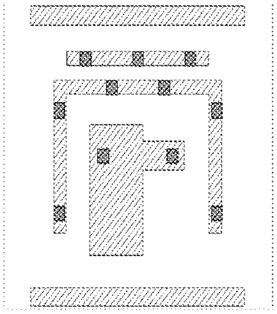
Figure 984A:
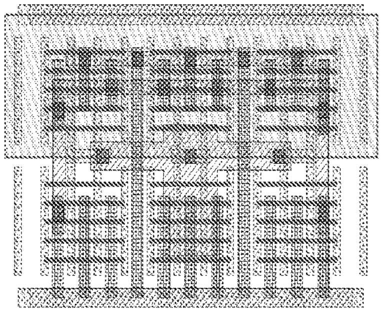
Figure 984B:
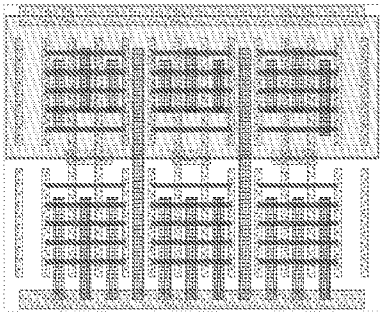
Figure 984C:
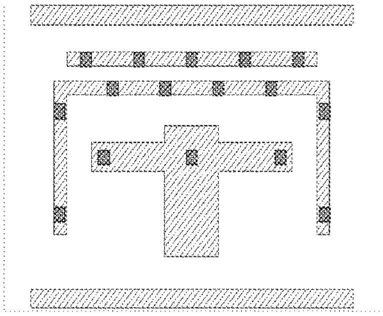
Figure 985A:
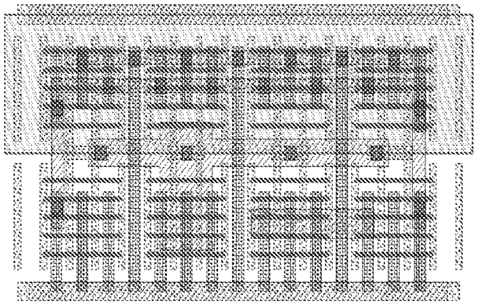
Figure 985B:
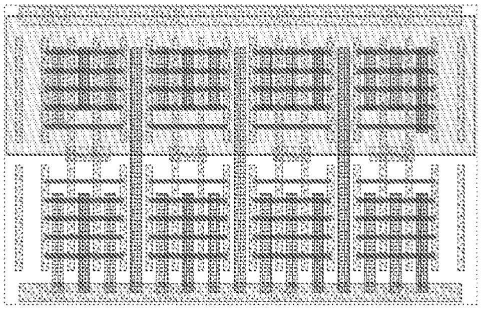
Figure 985C:
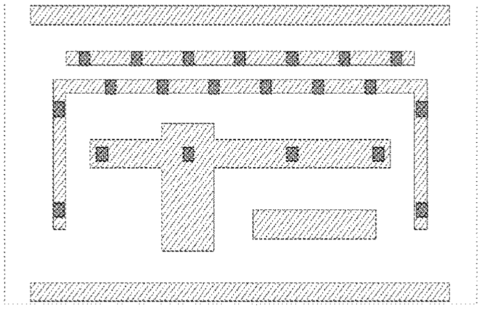
Figure 986A:
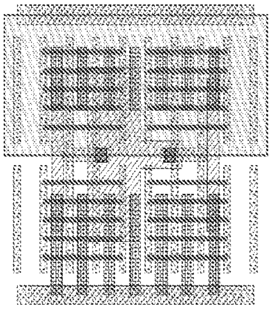
Figure 986B:
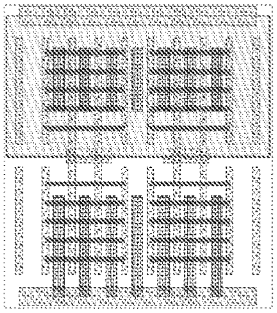
Figure 986C:
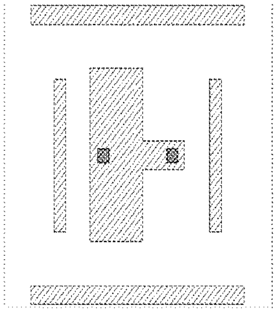
Figure 987A:
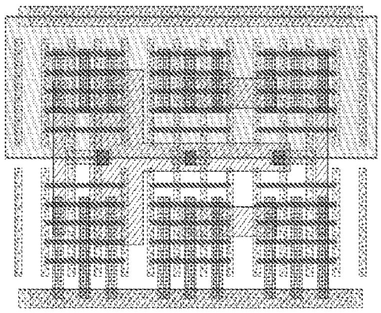
Figure 987B:
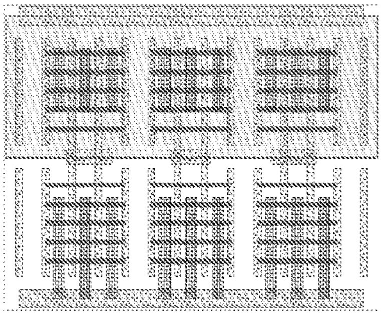
Figure 987C:
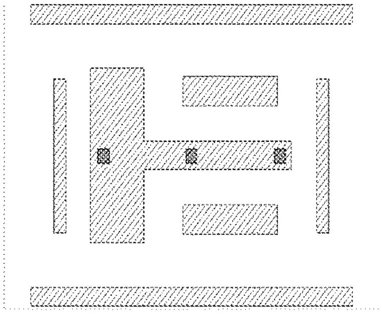
Figure 988A:
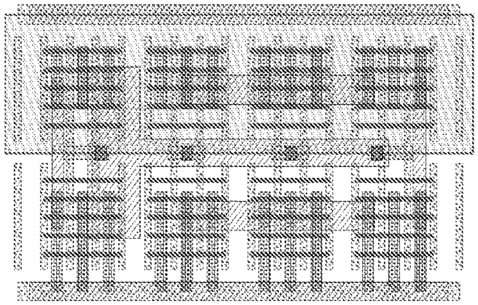
Figure 988B:
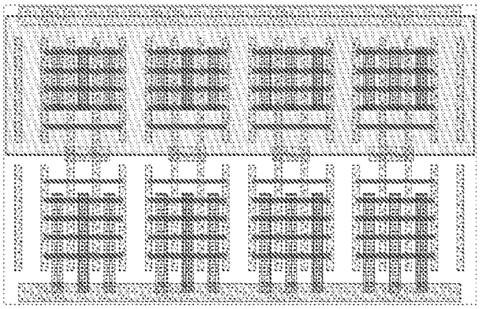
Figure 988C:
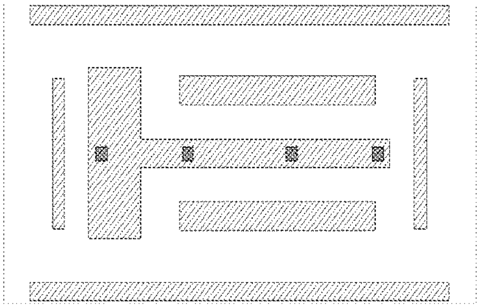
Figure 989A:
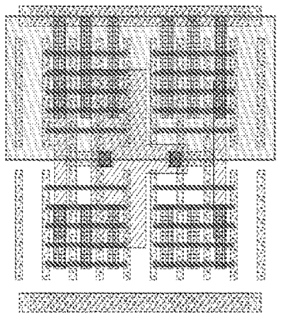
Figure 989B:
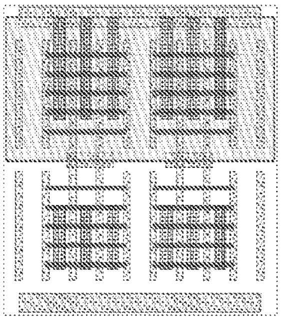
Figure 989C:
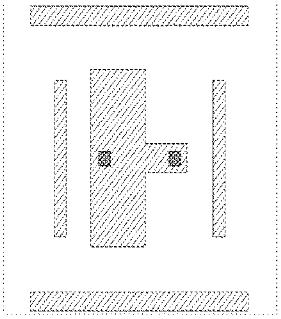
Figure 990A:
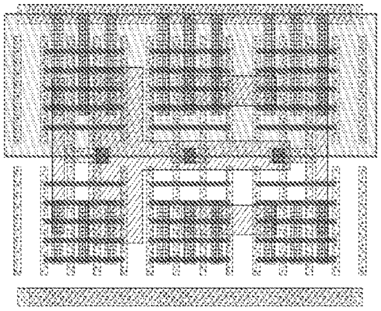
Figure 990B:
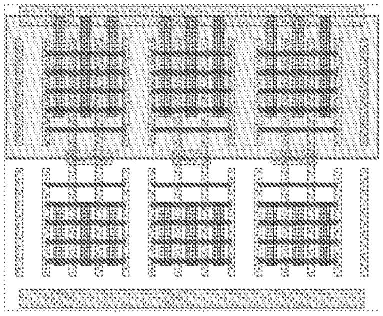
Figure 990C:
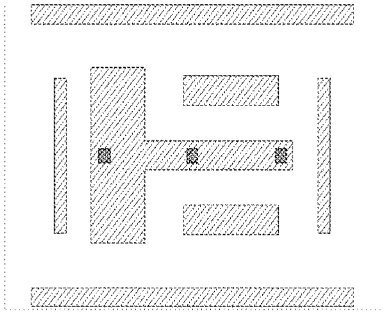
Figure 991A:
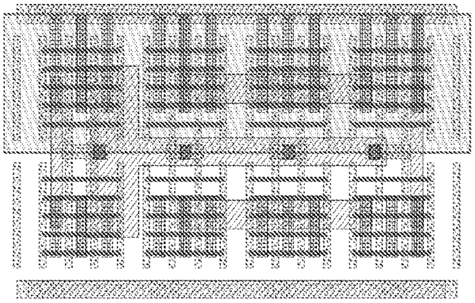
Figure 991B:
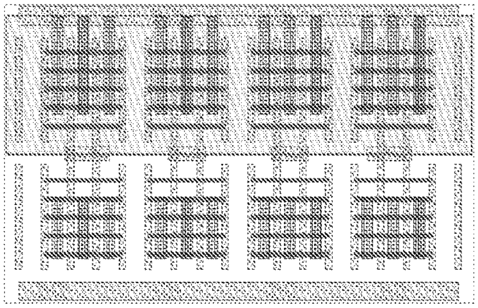
Figure 991C:
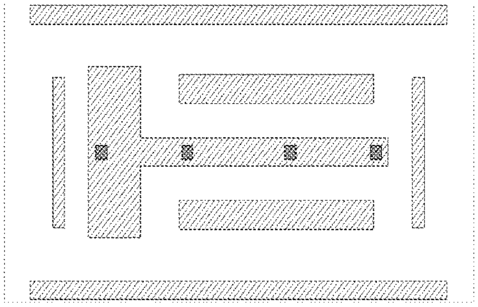
Figure 992A:
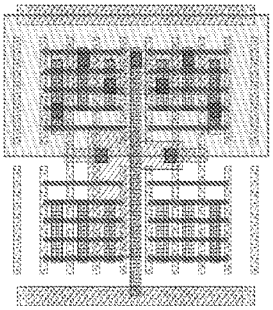
Figure 992B:
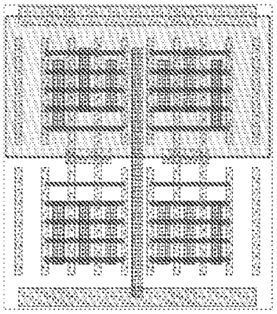
Figure 992C:
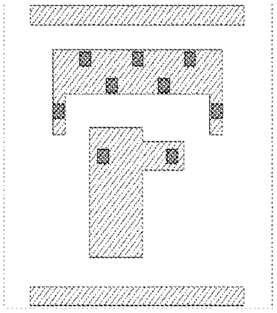
Figure 993A:
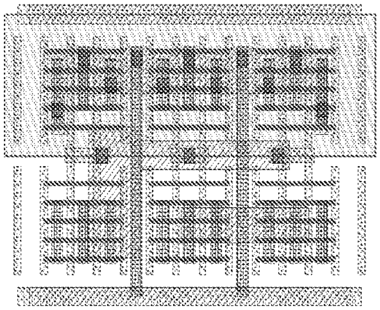
Figure 993B:
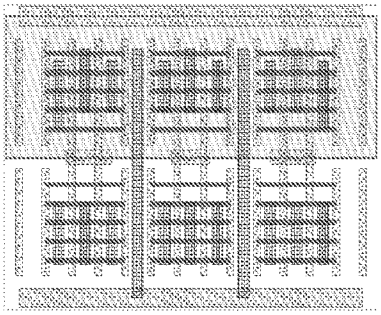
Figure 993C:
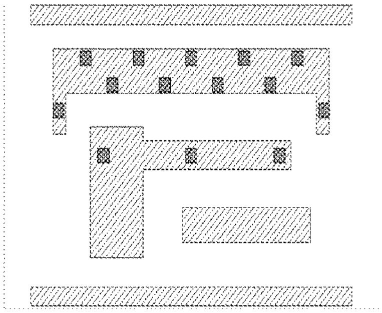
Figure 994A:
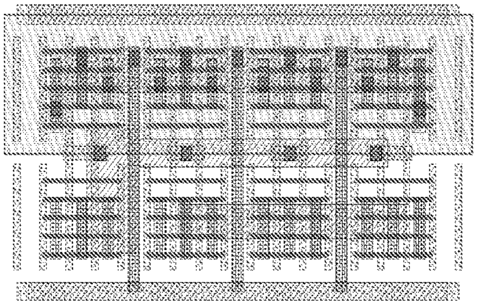
Figure 994B:
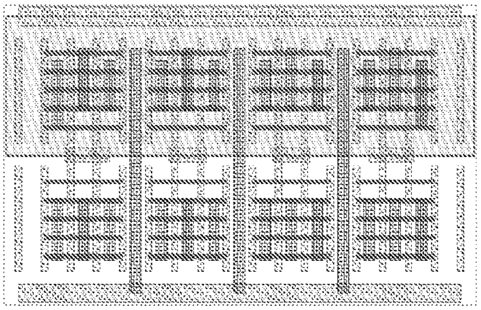
Figure 994C:
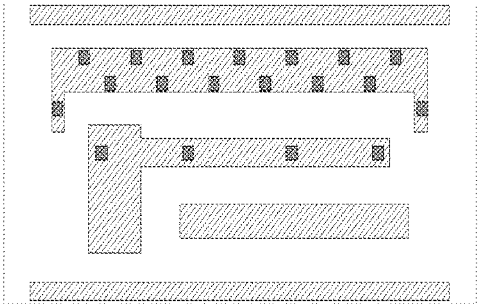
Figure 995A:
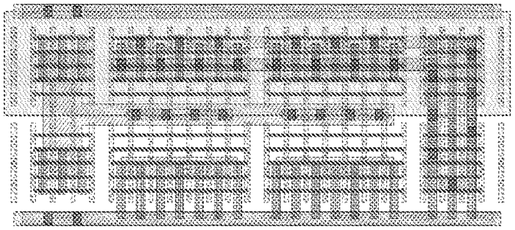
Figure 995B:
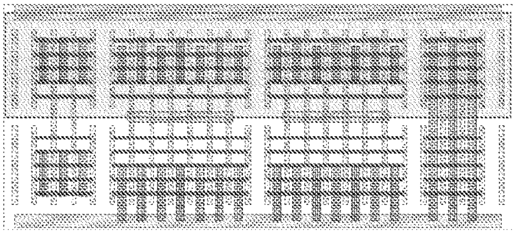
Figure 995C:
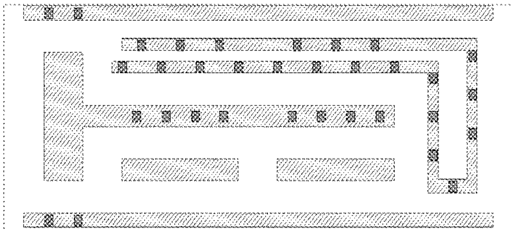
Figure 996A:
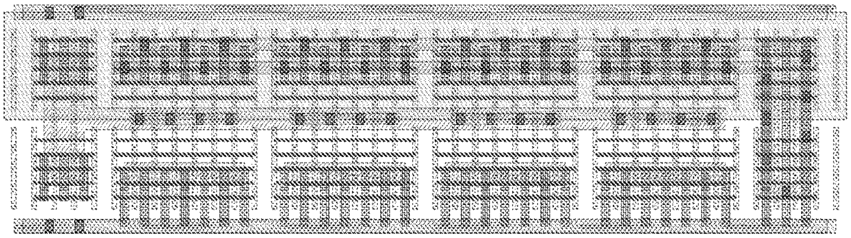
Figure 996B:
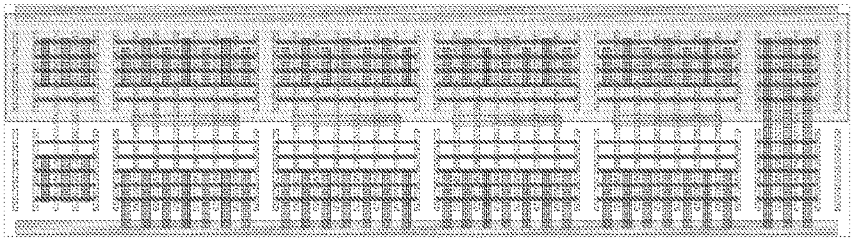
Figure 996C:
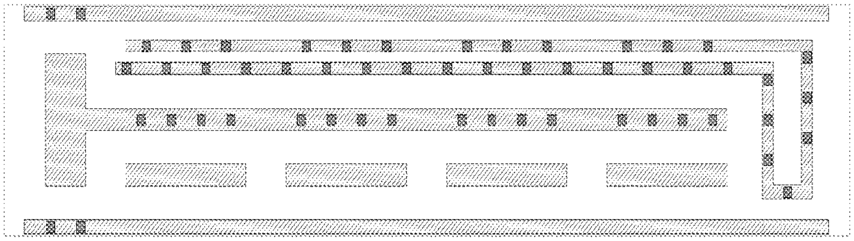
Figure 997A:
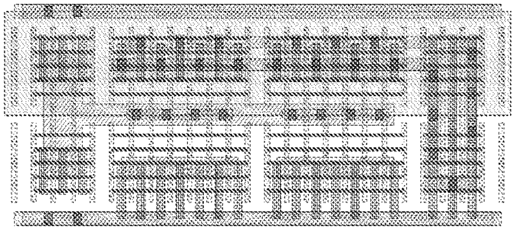
Figure 997B:
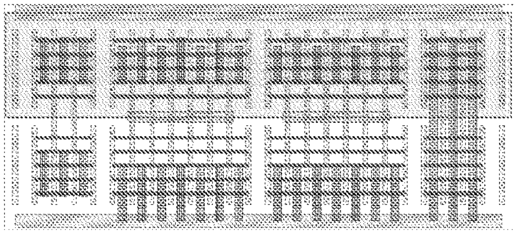
Figure 997C:
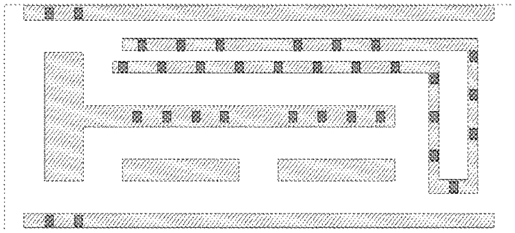
Figure 998A:
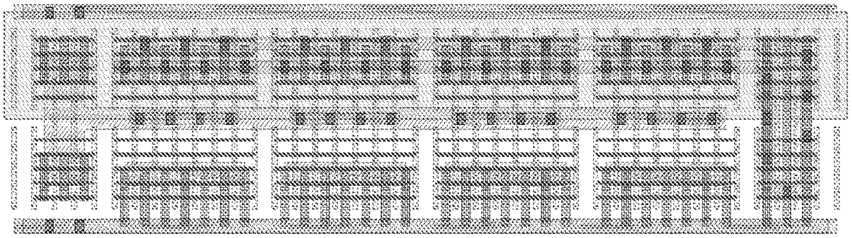
Figure 998B:
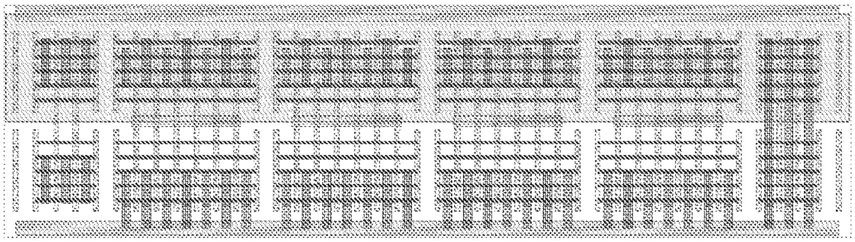
Figure 998C:
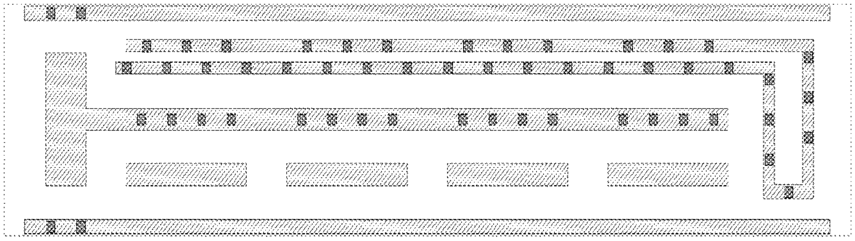
Figure 999A:
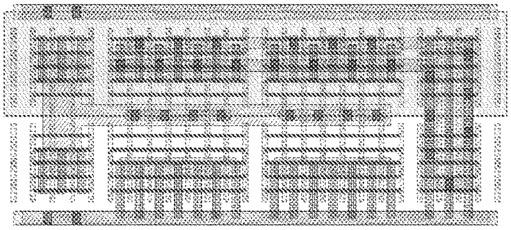
Figure 999B:
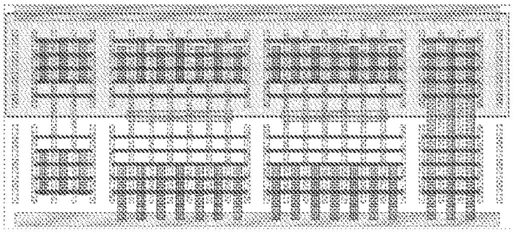
Figure 999C:
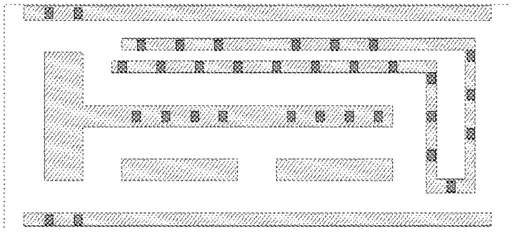

FIGS. 46A-C respectively depict plan views of—(A) all layers; (B) NWELL, AA, GATE, GATECNT, TS, and AACNT layers; (C) V0 and M1 layers—of an exemplary TS-GATE-side-to-side-short-configured, NCEM-enabled fill cell of type PDF_D_VCI_V16_14S1_01;

FIGS. 47A-C respectively depict plan views of—(A) all layers; (B) NWELL, AA, GATE, GATECNT, TS, and AACNT layers; (C) V0 and M1 layers—of an exemplary GATECNT-AACNT-side-to-side-short-configured, NCEM-enabled fill cell of type PDF_D_VCI_V16_14S1_05;

FIGS. 48A-C respectively depict plan views of—(A) all layers; (B) NWELL, AA, GATE, GATECNT, TS, and AACNT layers; (C) V0 and M1 layers—of an exemplary GATECNT-via-open-configured, NCEM-enabled fill cell of type PDF_D_VCI_V16_14S1_08;

FIGS. 49A-C respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_11;

FIGS. 50A-C respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_12;

FIG. 51 contains a layer legend for FIGS. 1A-C, 2A-C, 3A-C, etc., which follow;

FIGS. 52A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S117_0009_1;

FIGS. 53A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S117_0009_1;

FIGS. 54A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S117_0009_1;

FIGS. 55A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S117_0009_1;

FIGS. 56A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S117_0007_1;

FIGS. 57A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S117_0007_1;

FIGS. 58A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S117_0007_1;

FIGS. 59A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S117_0007_1;

FIGS. 60A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S117_0006_1;

FIGS. 61A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S117_0006_1;

FIGS. 62A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S117_0006_1;

FIGS. 63A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S117_0006_1;

FIGS. 64A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S117_0004_1;

FIGS. 65A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S117_0004_1;

FIGS. 66A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S117_0004_1;

FIGS. 67A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S117_0004_1;

FIGS. 68A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S121_0007_1;

FIGS. 69A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S121_0007_1;

FIGS. 70A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S121_0007_1;

FIGS. 71A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S121_0007_1;

FIGS. 72A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S121_0005_1;

FIGS. 73A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S121_0005_1;

FIGS. 74A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S121_0005_1;

FIGS. 75A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S121_0005_1;

FIGS. 76A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S121_0004_1;

FIGS. 77A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S121_0004_1;

FIGS. 78A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S121_0004_1;

FIGS. 79A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S121_0004_1;

FIGS. 80A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S121_0002_1;

FIGS. 81A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S121_0002_1;

FIGS. 82A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S121_0002_1;

FIGS. 83A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S121_0002_1;

FIGS. 84A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL8_9S121_0001_1;

FIGS. 85A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL16_9S121_0001_1;

FIGS. 86A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL32_9S121_0001_1;

FIGS. 87A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type A_PDF_VCI_FILL64_9S121_0001_1;

FIGS. 88A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0029_1;

FIGS. 89A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0028_1;

FIGS. 90A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0024_1;

FIGS. 91A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0023_1;

FIGS. 92A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0021_1;

FIGS. 93A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0020_1;

FIGS. 94A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0019_1;

FIGS. 95A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0018_1;

FIGS. 96A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0017_1;

FIGS. 97A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0016_1;

FIGS. 98A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0015_1;

FIGS. 99A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0014_1;

FIGS. 100A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0013_1;

FIGS. 101A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0012_1;

FIGS. 102A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0011_1;

FIGS. 103A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0010_1;

FIGS. 104A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0009_1;

FIGS. 105A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0008_1;

FIGS. 106A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type D_PDF_VCI_VFILLE_12S02_0001_1;

FIGS. 107A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type E_PDF_VCI_FILL8_17S2_0018_1;

FIGS. 108A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0022_1;

FIGS. 109A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S1_0045_1;

FIGS. 110A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S1_0044_1;

FIGS. 111A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0008_1;

FIGS. 112A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S1_0005_1;

FIGS. 113A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S1_0004_1;

FIGS. 114A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0005_1;

FIGS. 115A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S1_0002_1;

FIGS. 116A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S1_0001_1;

FIGS. 117A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0017_1;

FIGS. 118A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S1_0002_1;

FIGS. 119A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S1_0001_1;

FIGS. 120A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0027_1;

FIGS. 121A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0025_1;

FIGS. 122A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0044_1;

FIGS. 123A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0023_1;

FIGS. 124A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0043_1;

FIGS. 125A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0045_1;

FIGS. 126A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0021_1;

FIGS. 127A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0044_1;

FIGS. 128A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0020_1;

FIGS. 129A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0019_1;

FIGS. 130A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0015_1;

FIGS. 131A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0014_1;

FIGS. 132A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0010_1;

FIGS. 133A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0007_1;

FIGS. 134A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0006_1;

FIGS. 135A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0005_1;

FIGS. 136A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0004_1;

FIGS. 137A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL16_24S2_0003_1;

FIGS. 138A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0005_1;

FIGS. 139A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0004_1;

FIGS. 140A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0003_1;

FIGS. 141A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0002_1;

FIGS. 142A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL32_24S2_0001_1;

FIGS. 143A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0003_1;

FIGS. 144A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0002_1;

FIGS. 145A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL64_24S2_0001_1;

FIGS. 146A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0030_1;

FIGS. 147A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0029_1;

FIGS. 148A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0028_1;

FIGS. 149A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0006_1;

FIGS. 150A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0004_1;

FIGS. 151A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type F_PDF_VCI_FILL08_24S2_0003_1;

FIGS. 152A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL08_19S200016C;

FIGS. 153A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL12_19S200026C;

FIGS. 154A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL16_19S200036C;

FIGS. 155A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL08_19S2000176;

FIGS. 156A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL12_19S2000276;

FIGS. 157A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL16_19S2000376;

FIGS. 158A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL12_19S2000180;

FIGS. 159A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_PDF_VCI_FILL16_19S2000280;

FIGS. 160A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S10001F4_001;

FIGS. 161A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S1000AF4_010;

FIGS. 162A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S10013F4_019;

FIGS. 163A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S3000120_001;

FIGS. 164A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S3000D20_013;

FIGS. 165A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S3001920_025;

FIGS. 166A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S200010D_001;

FIGS. 167A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S200090D_009;

FIGS. 168A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S200110D_017;

FIGS. 169A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S2000112_001;

FIGS. 170A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S2000912_009;

FIGS. 171A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type I_V421_VCI_20S2001112_017;

FIGS. 172A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S160_216_1;

FIGS. 173A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S160_224_1;

FIGS. 174A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S159_197_1;

FIGS. 175A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S159_205_1;

FIGS. 176A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S158_178_1;

FIGS. 177A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S158_186_1;

FIGS. 178A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S161_235_1;

FIGS. 179A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S161_243_1;

FIGS. 180A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S294_0017_1;

FIGS. 181A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S294_0009_1;

FIGS. 182A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S292_0017_1;

FIGS. 183A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S292_0009_1;

FIGS. 184A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S293_0009_1;

FIGS. 185A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_VFILLCVE_7S293_0001_1;

FIGS. 186A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_FILL8_40_1;

FIGS. 187A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_FILL8_59_1;

FIGS. 188A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_FILL8_61_1;

FIGS. 189A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_FILL8_63_1;

FIGS. 190A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type J_PDF_VCI_FILL8_42_1;

FIGS. 191A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20001BF_01;

FIGS. 192A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20013BF_19;

FIGS. 193A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20025BF_37;

FIGS. 194A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20001BD_01;

FIGS. 195A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20014BD_20;

FIGS. 196A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20027BD_39;

FIGS. 197A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20001C0_01;

FIGS. 198A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20013C0_19;

FIGS. 199A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20025C0_37;

FIGS. 200A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20001BE_01;

FIGS. 201A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20014BE_20;

FIGS. 202A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type K_V549_PDF_VCI_20027BE_39;

FIGS. 203A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000164_01;

FIGS. 204A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000964_09;

FIGS. 205A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2001164_17;

FIGS. 206A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000166_01;

FIGS. 207A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000966_09;

FIGS. 208A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2001166_17;

FIGS. 209A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000194_01;

FIGS. 210A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2001194_17;

FIGS. 211A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2002194_33;

FIGS. 212A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000198_01;

FIGS. 213A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2001198_17;

FIGS. 214A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2002198_33;

FIGS. 215A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2000196_01;

FIGS. 216A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2001196_17;

FIGS. 217A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_E_PDF_VCI_2002196_33;

FIGS. 218A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20001BD_01;

FIGS. 219A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20014BD_20;

FIGS. 220A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20027BD_39;

FIGS. 221A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20001BE_01;

FIGS. 222A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20014BE_20;

FIGS. 223A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_B_PDF_VCI_20027BE_39;

FIGS. 224A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20001BF_01;

FIGS. 225A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20013BF_19;

FIGS. 226A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20025BF_37;

FIGS. 227A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20001BD_01;

FIGS. 228A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20014BD_20;

FIGS. 229A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20027BD_39;

FIGS. 230A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20001C0_01;

FIGS. 231A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20013C0_19;

FIGS. 232A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20025C0_37;

FIGS. 233A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20001BE_01;

FIGS. 234A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20014BE_20;

FIGS. 235A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type L_V54C_M_PDF_VCI_20027BE_39;

FIGS. 236A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000164_01;

FIGS. 237A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000964_09;

FIGS. 238A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2001164_17;

FIGS. 239A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000166_01;

FIGS. 240A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000966_09;

FIGS. 241A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2001166_17;

FIGS. 242A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000194_01;

FIGS. 243A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2001194_17;

FIGS. 244A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2002194_33;

FIGS. 245A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000198_01;

FIGS. 246A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2001198_17;

FIGS. 247A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2002198_33;

FIGS. 248A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2000196_01;

FIGS. 249A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2001196_17;

FIGS. 250A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54A_PDF_VCI_2002196_33;

FIGS. 251A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20001BD_01;

FIGS. 252A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20014BD_20;

FIGS. 253A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20027BD_39;

FIGS. 254A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20001BE_01;

FIGS. 255A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20014BE_20;

FIGS. 256A-C respectively depict plan views of—(A) all layers; (B) NWELL, AA, GATE, GATECNT, TS, and AACNT layers; (C) V0, and M1 layers—of an exemplary V0-AACNT-chamfer-short-configured, NCEM-enabled fill cell of type M_V54B_PDF_VCI_20027BE_39;

FIGS. 257A-B respectively depict plan views of—(A) all layers; (B) M3, V3, M4, V4, and M5 layers—of an exemplary V3-M3-chamfer-short-configured, NCEM-enabled fill cell of type L_V54C_B_PDF_VCI_10001F6_01;

FIGS. 258A-B respectively depict plan views of—(A) all layers; (B) M3, V3, M4, V4, and M5 layers—of an exemplary V3-M3-chamfer-short-configured, NCEM-enabled fill cell of type L_V54C_B_PDF_VCI_10022F6_34;

FIGS. 259A-B respectively depict plan views of—(A) all layers; (B) M3, V3, M4, V4, and M5 layers—of an exemplary V3-M3-chamfer-short-configured, NCEM-enabled fill cell of type L_V54C_B_PDF_VCI_10043F6_67;

FIGS. 260A-B respectively depict plan views of—(A) all layers; (B) M3, V3, M4, V4, and M5 layers—of an exemplary V3-M3-chamfer-short-configured, NCEM-enabled fill cell of type M_V54B_PDF_VCI_10001F6_01;

FIGS. 261A-B respectively depict plan views of—(A) all layers; (B) M3, V3, M4, V4, and M5 layers—of an exemplary V3-M3-chamfer-short-configured, NCEM-enabled fill cell of type M_V54B_PDF_VCI_10022F6_34;

FIGS. 262A-B respectively depict plan views of—(A) all layers; (B) M3, V3, M4, V4, and M5 layers—of an exemplary V3-M3-chamfer-short-configured, NCEM-enabled fill cell of type M_V54B_PDF_VCI_10043F6_67;

FIGS. 263A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2000180_01;

FIGS. 264A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2000880_08;

FIGS. 265A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2000F80_15;

FIGS. 266A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001080_16;

FIGS. 267A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001780_23;

FIGS. 268A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001E80_30;

FIGS. 269A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_20001B2_01;

FIGS. 270A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2000882_08;

FIGS. 271A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2000F82_15;

FIGS. 272A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001082_16;

FIGS. 273A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001782_23;

FIGS. 274A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type L_V54C_E_PDF_VCI_2001E82_30;

FIGS. 275A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2000180_01;

FIGS. 276A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2000880_08;

FIGS. 277A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2000F80_15;

FIGS. 278A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001080_16;

FIGS. 279A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001780_23;

FIGS. 280A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001E80_30;

FIGS. 281A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_20001B2_01;

FIGS. 282A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2000882_08;

FIGS. 283A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2000F82_15;

FIGS. 284A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001082_16;

FIGS. 285A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001782_23;

FIGS. 286A-C respectively depict plan views of—(A) all layers; (B) NWELL, AA, GATE, GATECNT, TS, and AACNT layers; (C) V0, and M1 layers—of an exemplary GATECNT-AA-corner-short-configured, NCEM-enabled fill cell of type M_V54A_PDF_VCI_2001E82_30;

FIGS. 287A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL8_9S108_0003_1;

FIGS. 288A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL32_9S108_0003_1;

FIGS. 289A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL16_9S108_0003_1;

FIGS. 290A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL64_9S108_0003_1;

FIGS. 291A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL8_9S108_0002_1;

FIGS. 292A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL32_9S108_0002_1;

FIGS. 293A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL16_9S108_0002_1;

FIGS. 294A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type A_PDF_VCI_FILL64_9S108_0002_1;

FIGS. 295A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0048_1;

FIGS. 296A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0102_1;

FIGS. 297A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0030_1;

FIGS. 298A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0084_1;

FIGS. 299A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0012_1;

FIGS. 300A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type D_PDF_VCI_VFILL4_12S01_0066_1;

FIGS. 301A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0055_1;

FIGS. 302A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0054_1;

FIGS. 303A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0052_1;

FIGS. 304A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0050_1;

FIGS. 305A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0048_1;

FIGS. 306A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type E_PDF_VCI_FILL8_17S1_0046_1;

FIGS. 307A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0084_1;

FIGS. 308A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0083_1;

FIGS. 309A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0082_1;

FIGS. 310A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S2_0021_1;

FIGS. 311A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0052_1;

FIGS. 312A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0051_1;

FIGS. 313A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0050_1;

FIGS. 314A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0049_1;

FIGS. 315A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S2_0015_1;

FIGS. 316A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0048_1;

FIGS. 317A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0049_1;

FIGS. 318A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0047_1;

FIGS. 319A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0048_1;

FIGS. 320A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0046_1;

FIGS. 321A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0047_1;

FIGS. 322A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0045_1;

FIGS. 323A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0046_1;

FIGS. 324A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0044_1;

FIGS. 325A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0045_1;

FIGS. 326A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0043_1;

FIGS. 327A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0044_1;

FIGS. 328A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S1_0042_1;

FIGS. 329A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0043_1;

FIGS. 330A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0042_1;

FIGS. 331A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0041_1;

FIGS. 332A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0040_1;

FIGS. 333A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S1_0039_1;

FIGS. 334A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S2_0029_1;

FIGS. 335A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0049_1;

FIGS. 336A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0048_1;

FIGS. 337A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0047_1;

FIGS. 338A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0046_1;

FIGS. 339A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0045_1;

FIGS. 340A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0044_1;

FIGS. 341A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0043_1;

FIGS. 342A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0042_1;

FIGS. 343A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0041_1;

FIGS. 344A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0040_1;

FIGS. 345A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S1_0039_1;

FIGS. 346A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S2_0034_1;

FIGS. 347A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0008_1;

FIGS. 348A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0007_1;

FIGS. 349A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0006_1;

FIGS. 350A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0005_1;

FIGS. 351A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0004_1;

FIGS. 352A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0003_1;

FIGS. 353A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0002_1;

FIGS. 354A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S1_0001_1;

FIGS. 355A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S2_0033_1;

FIGS. 356A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL16_24S2_0032_1;

FIGS. 357A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S2_0027_1;

FIGS. 358A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL32_24S2_0026_1;

FIGS. 359A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S2_0019_1;

FIGS. 360A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL64_24S2_0018_1;

FIGS. 361A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S2_0014_1;

FIGS. 362A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type F_PDF_VCI_FILL08_24S2_0013_1;

FIGS. 363A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S250_0012_1;

FIGS. 364A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S250_0005_1;

FIGS. 365A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S250_0001_1;

FIGS. 366A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S251_0012_1;

FIGS. 367A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S251_0005_1;

FIGS. 368A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S251_0001_1;

FIGS. 369A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S252_0012_1;

FIGS. 370A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S252_0005_1;

FIGS. 371A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S252_0001_1;

FIGS. 372A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S253_0012_1;

FIGS. 373A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S253_0005_1;

FIGS. 374A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_VFILLCV4_7S253_0001_1;

FIGS. 375A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_FILL8_22_1;

FIGS. 376A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type J_PDF_VCI_FILL8_23_1;

FIGS. 377A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000123_01;

FIGS. 378A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000823_08;

FIGS. 379A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000F23_15;

FIGS. 380A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000124_01;

FIGS. 381A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000F24_15;

FIGS. 382A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3001D24_29;

FIGS. 383A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000125_01;

FIGS. 384A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000825_08;

FIGS. 385A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000F25_15;

FIGS. 386A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000126_01;

FIGS. 387A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3000F26_15;

FIGS. 388A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type K_V549_PDF_VCI_3001D26_29;

FIGS. 389A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2000168_01;

FIGS. 390A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2000F68_15;

FIGS. 391A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2001D68_29;

FIGS. 392A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_200016A_01;

FIGS. 393A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2000F6A_15;

FIGS. 394A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2001D6A_29;

FIGS. 395A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_200016C_01;

FIGS. 396A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2000F6C_15;

FIGS. 397A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_E_PDF_VCI_2001D6C_29;

FIGS. 398A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000123_01;

FIGS. 399A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000823_08;

FIGS. 400A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000F23_15;

FIGS. 401A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000125_01;

FIGS. 402A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000825_08;

FIGS. 403A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000F25_15;

FIGS. 404A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_30001E9_01;

FIGS. 405A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_30008E9_08;

FIGS. 406A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000FE9_15;

FIGS. 407A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_30001EA_01;

FIGS. 408A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_30008EA_08;

FIGS. 409A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_B_PDF_VCI_3000FEA_15;

FIGS. 410A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3000124_01;

FIGS. 411A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3000F24_15;

FIGS. 412A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3001D24_29;

FIGS. 413A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3000126_01;

FIGS. 414A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3000F26_15;

FIGS. 415A-C respectively depict plan views of—(A) all layers; (B) NWELL, AA, GATE, GATECNT, TS, and AACNT layers; (C) V0, and M1 layers—of an exemplary GATECNT-TS-corner-short-configured, NCEM-enabled fill cell of type L_V54C_M_PDF_VCI_3001D26_29;

FIGS. 416A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type A_PDF_VCI_FILL8_9S113_0001_1;

FIGS. 417A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type A_PDF_VCI_FILL16_9S113_0001_1;

FIGS. 418A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type A_PDF_VCI_FILL32_9S113_0001_1;

FIGS. 419A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type A_PDF_VCI_FILL64_9S113_0001_1;

FIGS. 420A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0047_1;

FIGS. 421A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0046_1;

FIGS. 422A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0045_1;

FIGS. 423A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0044_1;

FIGS. 424A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0043_1;

FIGS. 425A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0042_1;

FIGS. 426A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0040_1;

FIGS. 427A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0039_1;

FIGS. 428A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type D_PDF_VCI_VFILLE_12S02_0038_1;

FIGS. 429A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0008_1;

FIGS. 430A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0007_1;

FIGS. 431A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0006_1;

FIGS. 432A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0005_1;

FIGS. 433A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0004_1;

FIGS. 434A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type E_PDF_VCI_FILL8_17S2_0003_1;

FIGS. 435A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0079_1;

FIGS. 436A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0078_1;

FIGS. 437A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0077_1;

FIGS. 438A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0076_1;

FIGS. 439A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0074_1;

FIGS. 440A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S1_0075_1;

FIGS. 441A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0039_1;

FIGS. 442A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0038_1;

FIGS. 443A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0037_1;

FIGS. 444A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0036_1;

FIGS. 445A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0035_1;

FIGS. 446A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0036_1;

FIGS. 447A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S1_0034_1;

FIGS. 448A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0035_1;

FIGS. 449A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0034_1;

FIGS. 450A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0033_1;

FIGS. 451A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0032_1;

FIGS. 452A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S1_0031_1;

FIGS. 453A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0036_1;

FIGS. 454A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0035_1;

FIGS. 455A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0034_1;

FIGS. 456A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0033_1;

FIGS. 457A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0032_1;

FIGS. 458A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S1_0031_1;

FIGS. 459A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL16_24S2_0017_1;

FIGS. 460A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL32_24S2_0039_1;

FIGS. 461A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL64_24S2_0042_1;

FIGS. 462A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type F_PDF_VCI_FILL08_24S2_0042_1;

FIGS. 463A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL12_19S2000162;

FIGS. 464A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL16_19S2000262;

FIGS. 465A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL12_19S2000362;

FIGS. 466A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL16_19S2000462;

FIGS. 467A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL12_19S2000562;

FIGS. 468A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL16_19S2000662;

FIGS. 469A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL12_19S2000762;

FIGS. 470A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_PDF_VCI_FILL16_19S2000862;

FIGS. 471A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_V421_VCI_20S2000103_001;

FIGS. 472A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_V421_VCI_20S2000203_002;

FIGS. 473A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_V421_VCI_20S2000108_001;

FIGS. 474A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type I_V421_VCI_20S2000208_002;

FIGS. 475A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S155_123_1;

FIGS. 476A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S153_65_1;

FIGS. 477A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S153_70_1;

FIGS. 478A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S151_1_1;

FIGS. 479A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S151_14_1;

FIGS. 480A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S152_33_1;

FIGS. 481A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S152_46_1;

FIGS. 482A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S154_92_1;

FIGS. 483A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_VFILLCVE_7S154_93_1;

FIGS. 484A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type J_PDF_VCI_FILL8_30_1;

FIGS. 485A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type L_V54C_E_PDF_VCI_2000705_07;

FIGS. 486A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type L_V54C_E_PDF_VCI_2000706_07;

FIGS. 487A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type L_V54C_E_PDF_VCI_2000102_01;

FIGS. 488A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type L_V54C_E_PDF_VCI_2000F02_15;

FIGS. 489A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type L_V54C_E_PDF_VCI_2001D02_29;

FIGS. 490A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type M_V54A_PDF_VCI_2000705_07;

FIGS. 491A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type M_V54A_PDF_VCI_2000706_07;

FIGS. 492A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type M_V54A_PDF_VCI_2000102_01;

FIGS. 493A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type M_V54A_PDF_VCI_2000F02_15;

FIGS. 494A-C respectively depict plan views of—(A) all layers; (B) NWELL, AA, GATE, GATECNT, TS, and AACNT layers; (C) V0, and M1 layers—of an exemplary M1-corner-short-configured, NCEM-enabled fill cell of type M_V54A_PDF_VCI_2001D02_29;

FIGS. 495A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type D_PDF_VCI_VFILL4_12S01_0109_1;

FIGS. 496A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type D_PDF_VCI_VFILL4_12S01_0091_1;

FIGS. 497A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type D_PDF_VCI_VFILL4_12S01_0073_1;

FIGS. 498A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type D_PDF_VCI_VFILL4_12S01_0055_1;

FIGS. 499A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type E_PDF_VCI_FILL8_17S1_0004_1;

FIGS. 500A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type E_PDF_VCI_FILL8_17S1_0003_1;

FIGS. 501A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type E_PDF_VCI_FILL8_17S1_0002_1;

FIGS. 502A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type E_PDF_VCI_FILL8_17S1_0001_1;

FIGS. 503A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL64_2451_0064_1;

FIGS. 504A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL64_2451_0063_1;

FIGS. 505A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL64_2451_0062_1;

FIGS. 506A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL64_2451_0061_1;

FIGS. 507A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL08_2451_0061_1;

FIGS. 508A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL08_2451_0060_1;

FIGS. 509A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL08_24S1_0058_1;

FIGS. 510A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL08_24S1_0059_1;

FIGS. 511A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL32_24S1_0061_1;

FIGS. 512A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL32_24S1_0060_1;

FIGS. 513A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL32_24S1_0059_1;

FIGS. 514A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL32_24S1_0058_1;

FIGS. 515A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL16_2451_0020_1;

FIGS. 516A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL16_2451_0019_1;

FIGS. 517A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL16_2451_0018_1;

FIGS. 518A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type F_PDF_VCI_FILL16_2451_0017_1;

FIGS. 519A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S115_98_1;

FIGS. 520A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S115_102_1;

FIGS. 521A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S115_115_1;

FIGS. 522A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S116_116_1;

FIGS. 523A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S116_120_1;

FIGS. 524A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S116_139_1;

FIGS. 525A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S117_172_1;

FIGS. 526A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S117_176_1;

FIGS. 527A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S117_189_1;

FIGS. 528A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S118_190_1;

FIGS. 529A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S118_194_1;

FIGS. 530A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type J_PDF_VCI_VFILLCV4_7S118_207_1;

FIGS. 531A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S245_0018_1;

FIGS. 532A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S245_0014_1;

FIGS. 533A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S245_0001_1;

FIGS. 534A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S246_0024_1;

FIGS. 535A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S246_0020_1;

FIGS. 536A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S246_0001_1;

FIGS. 537A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S247_0018_1;

FIGS. 538A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S247_0014_1;

FIGS. 539A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S247_0001_1;

FIGS. 540A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S248_0018_1;

FIGS. 541A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S248_0014_1;

FIGS. 542A-C respectively depict plan views of—(A) all layers; (B) V0, and M1 layers; (C) NWELL, AA, GATE, GATECNT, TS, and AACNT layers—of an exemplary GATECNT-diagonal-short-configured, NCEM-enabled fill cell of type J_PDF_VCI_VFILLCV4_7S248_0001_1;

FIGS. 543A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type K_V549_PDF_VCI_20001C9_01;

FIGS. 544A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type K_V549_PDF_VCI_20007C9_07;

FIGS. 545A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type K_V549_PDF_VCI_2000DC9_13;

FIG. 546A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_E_PDF_VCI_2000104_01;

FIGS. 547A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_E_PDF_VCI_2000404_04;

FIGS. 548A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_E_PDF_VCI_2000704_07;

FIGS. 549A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_M_PDF_VCI_20001C9_01;

FIGS. 550A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_M_PDF_VCI_20004C9_04;

FIGS. 551A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type L_V54C_M_PDF_VCI_20007C9_07;

FIGS. 552A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type M_V54A_PDF_VCI_2000104_01;

FIGS. 553A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type M_V54A_PDF_VCI_2000404_04;

FIGS. 554A-C respectively depict plan views of—(A) all layers; (B) NWELL, AA, GATE, GATECNT, TS, and AACNT layers; (C) V0, and M1 layers—of an exemplary GATECNT-diagonal-short-configured, NCEM-enabled fill cell of type M_V54A_PDF_VCI_2000704_07;

FIGS. 555A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type A_PDF_VCI_FILL8_9S102_0001_1;

FIGS. 556A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type A_PDF_VCI_FILL16_9S102_0001_1;

FIGS. 557A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type A_PDF_VCI_FILL32_9S102_0001_1;

FIGS. 558A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type A_PDF_VCI_FILL64_9S102_0001_1;

FIGS. 559A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL6_11S120_01_02_1;

FIGS. 560A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL9_11S120_01_02_2;

FIGS. 561A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL12_11S120_01_02_3;

FIGS. 562A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL24_11S120_01_02_4;

FIGS. 563A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL48_11S120_01_02_5;

FIGS. 564A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL72_11S120_01_02_6;

FIGS. 565A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL6_11S120_01_02_31;

FIGS. 566A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL9_11S120_01_02_32;

FIGS. 567A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL12_11S120_01_02_33;

FIGS. 568A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL24_11S120_01_02_34;

FIGS. 569A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL48_11S120_01_02_35;

FIGS. 570A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL72_11S120_01_02_36;

FIGS. 571A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL6_11S120_03_04_1;

FIGS. 572A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL9_11S120_03_04_2;

FIGS. 573A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL12_11S120_03_04_3;

FIGS. 574A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL24_11S120_03_04_4;

FIGS. 575A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL48_11S120_03_04_5;

FIGS. 576A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL72_11S120_03_04_6;

FIGS. 577A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL6_11S120_03_04_31;

FIGS. 578A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL9_11S120_03_04_32;

FIGS. 579A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL12_11S120_03_04_33;

FIGS. 580A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL24_11S120_03_04_34;

FIGS. 581A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL48_11S120_03_04_35;

FIGS. 582A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type B_PDF_VCI_FILL72_11S120_03_04_36;

FIGS. 583A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type D_PDF_VCI_VFILL4_12S01_0041_1;

FIGS. 584A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type D_PDF_VCI_VFILL4_12S01_0076_1;

FIGS. 585A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type D_PDF_VCI_VFILL4_12S01_0005_1;

FIGS. 586A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type E_PDF_VCI_FILL8_1751_0043_1;

FIGS. 587A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type E_PDF_VCI_FILL8_17S1_0039_1;

FIGS. 588A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type E_PDF_VCI_FILL8_17S1_0035_1;

FIGS. 589A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL08_24S1_0071_1;

FIGS. 590A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL64_24S1_0069_1;

FIGS. 591A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL08_24S1_0066_1;

FIGS. 592A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL32_24S1_0071_1;

FIGS. 593A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL32_2451_0069_1;

FIGS. 594A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL32_2451_0066_1;

FIGS. 595A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL16_2451_0030_1;

FIGS. 596A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL16_2451_0028_1;

FIGS. 597A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL16_2451_0025_1;

FIGS. 598A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type F_PDF_VCI_FILL08_2451_0069_1;

FIGS. 599A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3000152_01;

FIGS. 600A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3001152_17;

FIGS. 601A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3002152_33;

FIGS. 602A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3000154_01;

FIGS. 603A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3001154_17;

FIGS. 604A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3002154_33;

FIGS. 605A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3000156_01;

FIGS. 606A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3001156_17;

FIGS. 607A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3002156_33;

FIGS. 608A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3000158_01;

FIGS. 609A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3001158_17;

FIGS. 610A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type G_V931_PDF_VCI_3002158_33;

FIGS. 611A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2000117_001;

FIGS. 612A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2001117_017;

FIGS. 613A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2002117_033;

FIGS. 614A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2000118_001;

FIGS. 615A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2001118_017;

FIGS. 616A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2002118_033;

FIGS. 617A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2000121_001;

FIGS. 618A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2000D21_013;

FIGS. 619A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type I_V421_VCI_20S2001921_025;

FIGS. 620A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type J_PDF_VCI_FILL8_5_1;

FIGS. 621A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_300013E_01;

FIGS. 622A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_3000F3E_15;

FIGS. 623A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_3001D3E_29;

FIGS. 624A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_3001E3E_30;

FIGS. 625A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_3002C3E_44;

FIGS. 626A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type K_V549_PDF_VCI_3003A3E_58;

FIGS. 627A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_300013E_01;

FIGS. 628A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_3000F3E_15;

FIGS. 629A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_3001D3E_29;

FIGS. 630A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_3001E3E_30;

FIGS. 631A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_3002C3E_44;

FIGS. 632A-C respectively depict plan views of—(A) all layers; (B) NWELL, AA, GATE, GATECNT, TS, and AACNT layers; (C) V0, and M1 layers—of an exemplary GATECNT-AACNT-diagonal-short-configured, NCEM-enabled fill cell of type L_V54C_M_PDF_VCI_3003A3E_58;

FIGS. 633A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL8_9S104_0003_1;

FIGS. 634A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL16_9S104_0003_1;

FIGS. 635A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL32_9S104_0003_1;

FIGS. 636A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL64_9S104_0003_1;

FIGS. 637A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL4_9S104_0001_1;

FIGS. 638A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL6_9S104_0001_1;

FIGS. 639A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL8_9S104_0002_1;

FIGS. 640A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL16_9S104_0002_1;

FIGS. 641A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL32_9S104_0002_1;

FIGS. 642A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type A_PDF_VCI_FILL64_9S104_0002_1;

FIGS. 643A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type D_PDF_VCI_VFILL4_12S01_0112_1;

FIGS. 644A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type D_PDF_VCI_VFILL4_12S01_0033_1;

FIGS. 645A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type D_PDF_VCI_VFILLE_12S02_0049_1;

FIGS. 646A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type D_PDF_VCI_VFILL8_12S01_0012_1;

FIGS. 647A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type D_PDF_VCI_VFILLE_12S02_0048_1;

FIGS. 648A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type E_PDF_VCI_FILL8_17S1_0031_1;

FIGS. 649A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type E_PDF_VCI_FILL8_17S1_0027_1;

FIGS. 650A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type E_PDF_VCI_FILL8_17S1_0024_1;

FIGS. 651A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL04_24S2_0006_1;

FIGS. 652A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL06_24S2_0010_1;

FIGS. 653A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL08_24S2_0046_1;

FIGS. 654A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL32_24S2_0044_1;

FIGS. 655A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL32_24S2_0043_1;

FIGS. 656A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL64_24S2_0036_1;

FIGS. 657A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL64_24S2_0035_1;

FIGS. 658A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL08_24S2_0027_1;

FIGS. 659A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL08_24S2_0026_1;

FIGS. 660A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL16_24S2_0002_1;

FIGS. 661A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL16_24S2_0001_1;

FIGS. 662A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL64_24S1_0077_1;

FIGS. 663A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL08_24S1_0074_1;

FIGS. 664A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL32_24S1_0074_1;

FIGS. 665A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type F_PDF_VCI_FILL16_24S1_0033_1;

FIGS. 666A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_VFILLCV4_7S106_94_1;

FIGS. 667A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_VFILLCV4_7S107_96_1;

FIGS. 668A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_VFILLCVE_7S296_0031_1;

FIGS. 669A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_VFILLCVE_7S296_0016_1;

FIGS. 670A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_VFILLCVE_7S296_0001_1;

FIGS. 671A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_FILL8_8_1;

FIGS. 672A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_FILL4_1_1;

FIGS. 673A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type J_PDF_VCI_FILL8_9_1;

FIGS. 674A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300012A_01;

FIGS. 675A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300022A_02;

FIGS. 676A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300032A_03;

FIGS. 677A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300042A_04;

FIGS. 678A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300052A_05;

FIGS. 679A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300062A_06;

FIGS. 680A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300072A_07;

FIGS. 681A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type K_V549_PDF_VCI_300082A_08;

FIGS. 682A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_E_PDF_VCI_200019C_01;

FIGS. 683A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300012A_01;

FIGS. 684A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300022A_02;

FIGS. 685A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300032A_03;

FIGS. 686A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300042A_04;

FIGS. 687A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300052A_05;

FIGS. 688A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300062A_06;

FIGS. 689A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300072A_07;

FIGS. 690A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type L_V54C_M_PDF_VCI_300082A_08;

FIGS. 691A-C respectively depict plan views of—(A) all layers; (B) NWELL, AA, GATE, GATECNT, TS, and AACNT layers; (C) V0, and M1 layers—of an exemplary AACNT-GATE-interlayer-overlap-short-configured, NCEM-enabled fill cell of type M_V54A_PDF_VCI_200019C_01;

FIGS. 692A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0113_1;

FIGS. 693A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0042_1;

FIGS. 694A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0095_1;

FIGS. 695A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0024_1;

FIGS. 696A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0077_1;

FIGS. 697A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type D_PDF_VCI_VFILL4_12S01_0006_1;

FIGS. 698A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0044_1;

FIGS. 699A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0042_1;

FIGS. 700A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0040_1;

FIGS. 701A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0036_1;

FIGS. 702A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0034_1;

FIGS. 703A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type E_PDF_VCI_FILL8_17S1_0032_1;

FIGS. 704A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0059_1;

FIGS. 705A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0058_1;

FIGS. 706A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0057_1;

FIGS. 707A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0055_1;

FIGS. 708A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0054_1;

FIGS. 709A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL16_24S1_0053_1;

FIGS. 710A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0019_1;

FIGS. 711A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0018_1;

FIGS. 712A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0017_1;

FIGS. 713A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S2_0012_1;

FIGS. 714A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0015_1;

FIGS. 715A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0016_1;

FIGS. 716A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0014_1;

FIGS. 717A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0015_1;

FIGS. 718A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL64_24S1_0013_1;

FIGS. 719A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0014_1;

FIGS. 720A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0012_1;

FIGS. 721A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0011_1;

FIGS. 722A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL08_24S1_0010_1;

FIGS. 723A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0016_1;

FIGS. 724A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0015_1;

FIGS. 725A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0014_1;

FIGS. 726A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0012_1;

FIGS. 727A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0011_1;

FIGS. 728A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type F_PDF_VCI_FILL32_24S1_0010_1;

FIGS. 729A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type H_PDF_VCI_V16_14S1_11;

FIGS. 730A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type H_PDF_VCI_V16_14S1_12;

FIGS. 731A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type L_V54C_E_PDF_VCI_200018A_01;

FIGS. 732A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type L_V54C_E_PDF_VCI_200018C_01;

FIGS. 733A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type M_V54A_PDF_VCI_200018A_01;

FIGS. 734A-C respectively depict plan views of—(A) all layers; (B) NWELL, AA, GATE, GATECNT, TS, and AACNT layers; (C) V0, and M1 layers—of an exemplary GATE-AA-interlayer-overlap-short-configured, NCEM-enabled fill cell of type M_V54A_PDF_VCI_200018C_01;

FIGS. 735A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type A_PDF_VCI_FILL8_9S117_0003_1;

FIGS. 736A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type A_PDF_VCI_FILL16_9S117_0003_1;

FIGS. 737A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type A_PDF_VCI_FILL32_9S117_0003_1;

FIGS. 738A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type A_PDF_VCI_FILL64_9S117_0003_1;

FIGS. 739A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type D_PDF_VCI_VFILLE_12S02_0027_1;

FIGS. 740A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type D_PDF_VCI_VFILLE_12S02_0026_1;

FIGS. 741A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type D_PDF_VCI_VFILLE_12S02_0025_1;

FIGS. 742A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type E_PDF_VCI_FILL8_17S2_0020_1;

FIGS. 743A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type E_PDF_VCI_FILL8_17S2_0019_1;

FIGS. 744A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL16_24S2_0019_1;

FIGS. 745A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL16_24S1_0046_1;

FIGS. 746A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL64_24S2_0005_1;

FIGS. 747A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL64_24S1_0006_1;

FIGS. 748A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL08_24S2_0002_1;

FIGS. 749A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL08_24S1_0003_1;

FIGS. 750A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL32_24S2_0013_1;

FIGS. 751A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL32_2451_0003_1;

FIGS. 752A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL16_24S2_0018_1;

FIGS. 753A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL32_24S2_0012_1;

FIGS. 754A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL64_24S2_0004_1;

FIGS. 755A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type F_PDF_VCI_FILL08_24S2_0001_1;

FIGS. 756A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_VFILLCVE_7S290_0042_1;

FIGS. 757A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_VFILLCVE_7S290_0027_1;

FIGS. 758A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_VFILLCVE_7S290_0001_1;

FIGS. 759A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_VFILLCVE_7S291_0021_1;

FIGS. 760A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_VFILLCVE_7S291_0001_1;

FIGS. 761A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type J_PDF_VCI_FILL8_44_1;

FIGS. 762A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200155A_21;

FIGS. 763A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200165A_22;

FIGS. 764A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200235A_35;

FIGS. 765A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200015E_01;

FIGS. 766A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_2000E5E_14;

FIGS. 767A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_2002A5E_42;

FIGS. 768A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200025C_02;

FIGS. 769A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200155C_21;

FIGS. 770A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_200295C_41;

FIGS. 771A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_2000160_01;

FIGS. 772A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_2001560_21;

FIGS. 773A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type L_V54C_E_PDF_VCI_2002860_40;

FIGS. 774A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_200105A_16;

FIGS. 775A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_200115A_17;

FIGS. 776A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2002B5A_43;

FIGS. 777A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_200015E_01;

FIGS. 778A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2001A5E_26;

FIGS. 779A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2001B5E_27;

FIGS. 780A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_200155C_21;

FIGS. 781A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_200165C_22;

FIGS. 782A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2002A5C_42;

FIGS. 783A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2000160_01;

FIGS. 784A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2001460_20;

FIGS. 785A-C respectively depict plan views of—(A) all layers; (B) NWELL, AA, GATE, GATECNT, TS, and AACNT layers; (C) V0, and M1 layers—of an exemplary V0-merged-via-open-configured, NCEM-enabled fill cell of type M_V54A_PDF_VCI_2001560_21;

FIGS. 786A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type A_PDF_VCI_FILL8_9S117_0001_1;

FIGS. 787A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type A_PDF_VCI_FILL16_9S117_0001_1;

FIGS. 788A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type A_PDF_VCI_FILL32_9S117_0001_1;

FIGS. 789A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type A_PDF_VCI_FILL64_9S117_0001_1;

FIGS. 790A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type D_PDF_VCI_VFILLE_12S02_0022_1;

FIGS. 791A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL16_24S2_0007_1;

FIGS. 792A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL16_24S2_0006_1;

FIGS. 793A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL32_24S2_0007_1;

FIGS. 794A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL32_24S2_0006_1;

FIGS. 795A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL64_24S2_0011_1;

FIGS. 796A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL64_24S2_0009_1;

FIGS. 797A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL08_24S2_0032_1;

FIGS. 798A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type F_PDF_VCI_FILL08_24S2_0031_1;

FIGS. 799A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_20001A8_01;

FIGS. 800A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_2000DA8_13;

FIGS. 801A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_20019A8_25;

FIGS. 802A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_20001AA_01;

FIGS. 803A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_2000DAA_13;

FIGS. 804A-C respectively depict plan views of—(A) all layers; (B) NWELL, AA, GATE, GATECNT, TS, and AACNT layers; (C) V0, and M1 layers—of an exemplary AACNT-side-to-side-short-configured, NCEM-enabled fill cell of type G_V931_PDF_VCI_20019AA_25;

FIGS. 805A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2000171_01;

FIGS. 806A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2002371_35;

FIGS. 807A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2004571_69;

FIGS. 808A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2004671_70;

FIGS. 809A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2006871_104;

FIGS. 810A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2008A71_138;

FIGS. 811A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_200017D_01;

FIGS. 812A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_200237D_35;

FIGS. 813A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_200457D_69;

FIGS. 814A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_200467D_70;

FIGS. 815A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_200687D_104;

FIGS. 816A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2008A7D_138;

FIGS. 817A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2000189_01;

FIGS. 818A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2002389_35;

FIGS. 819A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2004589_69;

FIGS. 820A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2004689_70;

FIGS. 821A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2006889_104;

FIGS. 822A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_08_2008A89_138;

FIGS. 823A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_200032A_03;

FIGS. 824A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_2000192_01;

FIGS. 825A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_2000292_02;

FIGS. 826A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_2000392_03;

FIGS. 827A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_200019C_01;

FIGS. 828A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_200029C_02;

FIGS. 829A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type C_V682_PDF_VCI_16_200039C_03;

FIGS. 830A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type G_V931_PDF_VCI_20001B2_01;

FIGS. 831A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type G_V931_PDF_VCI_2000DB2_13;

FIGS. 832A-C respectively depict plan views of—(A) all layers; (B) NWELL, AA, GATE, GATECNT, TS, and AACNT layers; (C) V0, and M1 layers—of an exemplary AACNT-GATE-side-to-side-short-configured, NCEM-enabled fill cell of type G_V931_PDF_VCI_20019B2_25;

FIGS. 833A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type C_V682_PDF_VCI_16_2000106_01;

FIGS. 834A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type C_V682_PDF_VCI_16_2000178_01;

FIGS. 835A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type C_V682_PDF_VCI_16_2000184_01;

FIGS. 836A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_PDF_VCI_FILL08_19S20001DA;

FIGS. 837A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_PDF_VCI_FILL12_19S20002DA;

FIGS. 838A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_PDF_VCI_FILL16_19S20003DA;

FIGS. 839A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30001A7_001;

FIGS. 840A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30002A7_002;

FIGS. 841A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30003A7_003;

FIGS. 842A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30004A7_004;

FIGS. 843A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30005A7_005;

FIGS. 844A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30006A7_006;

FIGS. 845A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30007A7_007;

FIGS. 846A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30008A7_008;

FIGS. 847A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type I_V421_VCI_20S30009A7_009;

FIGS. 848A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type K_V549_PDF_VCI_20001C6_01;

FIGS. 849A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type K_V549_PDF_VCI_20001C7_01;

FIGS. 850A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type K_V549_PDF_VCI_20001C8_01;

FIGS. 851A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_B_PDF_VCI_20001C6_01;

FIGS. 852A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_B_PDF_VCI_20001C7_01;

FIGS. 853A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_B_PDF_VCI_20001C8_01;

FIGS. 854A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_M_PDF_VCI_20001C6_01;

FIGS. 855A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_M_PDF_VCI_20001C7_01;

FIGS. 856A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type L_V54C_M_PDF_VCI_20001C8_01;

FIGS. 857A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type M_V54B_PDF_VCI_20001C6_01;

FIGS. 858A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type M_V54B_PDF_VCI_20001C7_01;

FIGS. 859A-C respectively depict plan views of—(A) all layers; (B) NWELL, AA, GATE, GATECNT, TS, and AACNT layers; (C) V0, and M1 layers—of an exemplary GATE-side-to-side-short-configured, NCEM-enabled fill cell of type M_V54B_PDF_VCI_20001C8_01;

FIGS. 860A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3000134_01;

FIGS. 861A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3001034_16;

FIGS. 862A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3001F34_31;

FIGS. 863A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3000136_01;

FIGS. 864A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3001036_16;

FIGS. 865A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3001F36_31;

FIGS. 866A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3000A38_10;

FIGS. 867A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3001238_18;

FIGS. 868A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3002538_37;

FIGS. 869A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type G_V931_PDF_VCI_3002D38_45;

FIGS. 870A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type I_V421_VCI_20S2000130_001;

FIGS. 871A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type I_V421_VCI_20S2000C30_012;

FIGS. 872A-C respectively depict plan views of—(A) all layers; (B) NWELL, AA, GATE, GATECNT, TS, and AACNT layers; (C) V0, and M1 layers—of an exemplary GATECNT-side-to-side-short-configured, NCEM-enabled fill cell of type I_V421_VCI_20S2001730_023;

FIGS. 873A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4000160_01;

FIGS. 874A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4000D60_13;

FIGS. 875A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4001960_25;

FIGS. 876A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4001A60_26;

FIGS. 877A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4002660_38;

FIGS. 878A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type G_V931_PDF_VCI_4003260_50;

FIGS. 879A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type H_PDF_VCI_V16_14S1_05;

FIGS. 880A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type K_V549_PDF_VCI_3000135_01;

FIGS. 881A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type K_V549_PDF_VCI_3000D35_13;

FIGS. 882A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type K_V549_PDF_VCI_3001935_25;

FIGS. 883A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type L_V54C_M_PDF_VCI_3000135_01;

FIGS. 884A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type L_V54C_M_PDF_VCI_3000D35_13;

FIGS. 885A-C respectively depict plan views of—(A) all layers; (B) NWELL, AA, GATE, GATECNT, TS, and AACNT layers; (C) V0, and M1 layers—of an exemplary GATECNT-AACNT-side-to-side-short-configured, NCEM-enabled fill cell of type L_V54C_M_PDF_VCI_3001935_25;

FIGS. 886A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3000134_01;

FIGS. 887A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3000D34_13;

FIGS. 888A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3001934_25;

FIGS. 889A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3001A34_26;

FIGS. 890A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3002634_38;

FIGS. 891A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3003234_50;

FIGS. 892A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3003334_51;

FIGS. 893A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3003F34_63;

FIGS. 894A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type K_V549_PDF_VCI_3004B34_75;

FIGS. 895A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3000134_01;

FIGS. 896A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3000D34_13;

FIGS. 897A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3001934_25;

FIGS. 898A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3001A34_26;

FIGS. 899A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3002634_38;

FIGS. 900A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3003234_50;

FIGS. 901A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3003334_51;

FIGS. 902A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3003F34_63;

FIGS. 903A-C respectively depict plan views of—(A) all layers; (B) NWELL, AA, GATE, GATECNT, TS, and AACNT layers; (C) V0, and M1 layers—of an exemplary GATECNT-GATE-side-to-side-short-configured, NCEM-enabled fill cell of type L_V54C_M_PDF_VCI_3004B34_75;

FIGS. 904A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL8_9S114_0002_1;

FIGS. 905A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL16_9S114_0002_1;

FIGS. 906A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL32_9S114_0002_1;

FIGS. 907A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL64_9S114_0002_1;

FIGS. 908A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL8_9S114_0004_1;

FIGS. 909A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL16_9S114_0004_1;

FIGS. 910A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL32_9S114_0004_1;

FIGS. 911A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type A_PDF_VCI_FILL64_9S114_0004_1;

FIGS. 912A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type D_PDF_VCI_VFILLE_12S02_0041_1;

FIGS. 913A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type D_PDF_VCI_VFILLE_12S02_0036_1;

FIGS. 914A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type D_PDF_VCI_VFILLE_12S02_0034_1;

FIGS. 915A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL16_24S2_0016_1;

FIGS. 916A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL16_24S2_0015_1;

FIGS. 917A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL16_24S2_0014_1;

FIGS. 918A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL32_24S2_0032_1;

FIGS. 919A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL32_24S2_0030_1;

FIGS. 920A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL32_24S2_0028_1;

FIGS. 921A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL64_24S2_0041_1;

FIGS. 922A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL64_24S2_0040_1;

FIGS. 923A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL64_24S2_0039_1;

FIGS. 924A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL08_24S2_0041_1;

FIGS. 925A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL08_24S2_0040_1;

FIGS. 926A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type F_PDF_VCI_FILL08_24S2_0039_1;

FIGS. 927A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type J_PDF_VCI_FILL8_31_1;

FIGS. 928A-C respectively depict plan views of—(A) all layers; (B) NWELL, AA, GATE, GATECNT, TS, and AACNT layers; (C) V0, and M1 layers—of an exemplary M1-side-to-side-short-configured, NCEM-enabled fill cell of type J_PDF_VCI_FILL8_34_1;

FIGS. 929A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type A_PDF_VCI_FILL8_9S122_0001_1;

FIGS. 930A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type A_PDF_VCI_FILL16_9S122_0001_1;

FIGS. 931A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type A_PDF_VCI_FILL32_9S122_0001_1;

FIGS. 932A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type A_PDF_VCI_FILL64_9S122_0001_1;

FIGS. 933A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type H_PDF_VCI_V16_14S1_06;

FIGS. 934A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type H_PDF_VCI_V16_14S1_07;

FIGS. 935A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type J_PDF_VCI_FILL8_46_1;

FIGS. 936A-C respectively depict plan views of—(A) all layers; (B) NWELL, AA, GATE, GATECNT, TS, and AACNT layers; (C) V0, and M1 layers—of an exemplary M1-V0-side-to-side-short-configured, NCEM-enabled fill cell of type J_PDF_VCI_FILL8_64_1;

FIGS. 937A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL4_9S120_0001_1;

FIGS. 938A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL6_9S120_0001_1;

FIGS. 939A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL8_9S120_0001_1;

FIGS. 940A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL16_9S120_0001_1;

FIGS. 941A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL32_9S120_0001_1;

FIGS. 942A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type A_PDF_VCI_FILL64_9S120_0001_1;

FIGS. 943A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL6_11S100_01_1;

FIGS. 944A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL9_11S100_01_2;

FIGS. 945A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL12_11S100_01_3;

FIGS. 946A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL24_11S100_01_4;

FIGS. 947A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL48_11S100_01_5;

FIGS. 948A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type B_PDF_VCI_FILL72_11S100_01_6;

FIGS. 949A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type D_PDF_VCI_VFILL4_12S01_0038_1;

FIGS. 950A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type E_PDF_VCI_FILL8_17S1_0010_1;

FIGS. 951A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL16_24S1_0052_1;

FIGS. 952A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL16_24S1_0051_1;

FIGS. 953A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL16_24S1_0050_1;

FIGS. 954A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL16_24S1_0049_1;

FIGS. 955A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL64_24S1_0012_1;

FIGS. 956A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL64_24S1_0011_1;

FIGS. 957A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL64_24S1_0010_1;

FIGS. 958A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL64_24S1_0009_1;

FIGS. 959A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL08_24S1_0009_1;

FIGS. 960A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL08_24S1_0008_1;

FIGS. 961A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL08_24S1_0006_1;

FIGS. 962A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL08_24S1_0007_1;

FIGS. 963A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL32_24S1_0009_1;

FIGS. 964A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL32_24S1_0008_1;

FIGS. 965A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL32_24S1_0007_1;

FIGS. 966A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL32_24S1_0006_1;

FIGS. 967A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL04_24S2_0004_1;

FIGS. 968A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL04_24S2_0003_1;

FIGS. 969A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL04_24S2_0002_1;

FIGS. 970A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL04_24S2_0001_1;

FIGS. 971A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL06_24S2_0004_1;

FIGS. 972A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL06_24S2_0003_1;

FIGS. 973A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL06_24S2_0002_1;

FIGS. 974A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type F_PDF_VCI_FILL06_24S2_0001_1;

FIGS. 975A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type G_V931_PDF_VCI_300015C_01;

FIGS. 976A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type G_V931_PDF_VCI_300055C_05;

FIGS. 977A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type G_V931_PDF_VCI_300095C_09;

FIGS. 978A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type G_V931_PDF_VCI_3000D5C_13;

FIGS. 979A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type H_PDF_VCI_V16_14S1_01;

FIGS. 980A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type H_PDF_VCI_V16_14S1_02;

FIGS. 981A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type H_PDF_VCI_V16_14S1_03;

FIGS. 982A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type H_PDF_VCI_V16_14S1_04;

FIGS. 983A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL08_19S20001E4;

FIGS. 984A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL12_19S20002E4;

FIGS. 985A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL16_19S20003E4;

FIGS. 986A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL08_19S20004E4;

FIGS. 987A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL12_19S20005E4;

FIGS. 988A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL16_19S20006E4;

FIGS. 989A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL08_19S20007E4;

FIGS. 990A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL12_19S20008E4;

FIGS. 991A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL16_19S20009E4;

FIGS. 992A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL08_19S2000AE4;

FIGS. 993A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL12_19S2000BE4;

FIGS. 994A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_PDF_VCI_FILL16_19S2000CE4;

FIGS. 995A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30001B1_001;

FIGS. 996A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30005B1_005;

FIGS. 997A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30009B1_009;

FIGS. 998A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S3000DB1_013;

FIGS. 999A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30011B1_017;

FIGS. 1000A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30015B1_021;

FIGS. 1001A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30019B1_025;

FIGS. 1002A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S3001DB1_029;

FIGS. 1003A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30001AD_001;

FIGS. 1004A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30014AD_020;

FIGS. 1005A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30028AD_040;

FIGS. 1006A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30001AE_001;

FIGS. 1007A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30014AE_020;

FIGS. 1008A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30028AE_040;

FIGS. 1009A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30001AF_001;

FIGS. 1010A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30014AF_020;

FIGS. 1011A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type I_V421_VCI_20S30028AF_040;

FIGS. 1012A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type J_PDF_VCI_FILL4_3_1;

FIGS. 1013A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type J_PDF_VCI_FILL8_58_1;

FIGS. 1014A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000131_01;

FIGS. 1015A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000231_02;

FIGS. 1016A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000331_03;

FIGS. 1017A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000431_04;

FIGS. 1018A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000531_05;

FIGS. 1019A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000631_06;

FIGS. 1020A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000133_01;

FIGS. 1021A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3000933_09;

FIGS. 1022A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type K_V549_PDF_VCI_3001133_17;

FIGS. 1023A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000131_01;

FIGS. 1024A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000231_02;

FIGS. 1025A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000331_03;

FIGS. 1026A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000431_04;

FIGS. 1027A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000531_05;

FIGS. 1028A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000631_06;

FIGS. 1029A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000133_01;

FIGS. 1030A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3000933_09;

FIGS. 1031A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3001133_17;

FIGS. 1032A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3001933_25;

FIGS. 1033A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3001D33_29;

FIGS. 1034A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type L_V54C_M_PDF_VCI_3002133_33;

FIGS. 1035A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000131_01;

FIGS. 1036A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000231_02;

FIGS. 1037A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000331_03;

FIGS. 1038A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000431_04;

FIGS. 1039A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000531_05;

FIGS. 1040A-C respectively depict plan views of—(A) all layers; (B) NWELL, AA, GATE, GATECNT, TS, and AACNT layers; (C) V0, and M1 layers—of an exemplary TS-GATE-side-to-side-short-configured, NCEM-enabled fill cell of type M_V54B_PDF_VCI_3000631_06;

FIGS. 1041A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type C_V682_PDF_VCI_16_2000168_01;

FIGS. 1042A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type C_V682_PDF_VCI_16_2000468_04;

FIGS. 1043A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type C_V682_PDF_VCI_16_2000174_01;

FIGS. 1044A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type C_V682_PDF_VCI_16_2000474_04;

FIGS. 1045A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type G_V931_PDF_VCI_200016F_01;

FIGS. 1046A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type G_V931_PDF_VCI_2000171_01;

FIGS. 1047A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type G_V931_PDF_VCI_2000173_01;

FIGS. 1048A-C respectively depict plan views of—(A) all layers; (B) NWELL, AA, GATE, GATECNT, TS, and AACNT layers; (C) V0, and M1 layers—of an exemplary GATE-snake-open-configured, NCEM-enabled fill cell of type G_V931_PDF_VCI_2000175_01;

FIGS. 1049A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type A_PDF_VCI_FILL8_9S114_0001_1;

FIGS. 1050A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type A_PDF_VCI_FILL16_9S114_0001_1;

FIGS. 1051A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type A_PDF_VCI_FILL32_9S114_0001_1;

FIGS. 1052A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type A_PDF_VCI_FILL64_9S114_0001_1;

FIGS. 1053A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type D_PDF_VCI_VFILLE_12S02_0035_1;

FIGS. 1054A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type F_PDF_VCI_FILL16_24S2_0013_1;

FIGS. 1055A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type F_PDF_VCI_FILL32_24S2_0018_1;

FIGS. 1056A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type F_PDF_VCI_FILL64_24S2_0038_1;

FIGS. 1057A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type F_PDF_VCI_FILL08_24S2_0038_1;

FIGS. 1058A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type F_PDF_VCI_FILL08_24S2_0037_1;

FIGS. 1059A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL08_19S2000158;

FIGS. 1060A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL12_19S2000258;

FIGS. 1061A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL16_19S2000358;

FIGS. 1062A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL08_19S2000458;

FIGS. 1063A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL12_19S2000558;

FIGS. 1064A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_PDF_VCI_FILL16_19S2000658;

FIGS. 1065A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type I_V421_VCI_20S3000121_001;

FIGS. 1066A-C respectively depict plan views of—(A) all layers; (B) NWELL, AA, GATE, GATECNT, TS, and AACNT layers; (C) V0, and M1 layers—of an exemplary M1-snake-open-configured, NCEM-enabled fill cell of type J_PDF_VCI_FILL8_32_1;

FIGS. 1067A-C respectively depict plan views of—(A) all layers; (B) NWELL, AA, GATE, GATECNT, TS, and AACNT layers; (C) V0, and M1 layers—of an exemplary M1-V0-AACNT-snake-open-configured, NCEM-enabled fill cell of type I_V421_VCI_20S30001BB_001;

FIGS. 1068A-C respectively depict plan views of—(A) all layers; (B) NWELL, AA, GATE, GATECNT, TS, and AACNT layers; (C) V0, and M1 layers—of an exemplary M1-V0-AACNT-snake-open-configured, NCEM-enabled fill cell of type I_V421_VCI_20S30002BB_002;

FIGS. 1069A-C respectively depict plan views of—(A) all layers; (B) NWELL, AA, GATE, GATECNT, TS, and AACNT layers; (C) V0, and M1 layers—of an exemplary M1-V0-AACNT-snake-open-configured, NCEM-enabled fill cell of type I_PDF_VCI_FILL08_19S200018A;

FIGS. 1070A-C respectively depict plan views of—(A) all layers; (B) NWELL, AA, GATE, GATECNT, TS, and AACNT layers; (C) V0, and M1 layers—of an exemplary M1-V0-AACNT-snake-open-configured, NCEM-enabled fill cell of type I_PDF_VCI_FILL12_19S200028A;

FIGS. 1071A-C respectively depict plan views of—(A) all layers; (B) NWELL, AA, GATE, GATECNT, TS, and AACNT layers; (C) V0, and M1 layers—of an exemplary M1-V0-AACNT-snake-open-configured, NCEM-enabled fill cell of type I_PDF_VCI_FILL16_19S200038A;

FIGS. 1072A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type A_PDF_VCI_FILL8_9S116_0001_1;

FIGS. 1073A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type A_PDF_VCI_FILL16_9S116_0001_1;

FIGS. 1074A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type A_PDF_VCI_FILL32_9S116_0001_1;

FIGS. 1075A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type A_PDF_VCI_FILL64_9S116_0001_1;

FIGS. 1076A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type D_PDF_VCI_VFILLE_12S02_0030_1;

FIGS. 1077A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type F_PDF_VCI_FILL16_24S2_0011_1;

FIGS. 1078A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type F_PDF_VCI_FILL32_24S2_0011_1;

FIGS. 1079A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type F_PDF_VCI_FILL64_24S2_0033_1;

FIGS. 1080A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type F_PDF_VCI_FILL08_24S2_0036_1;

FIGS. 1081A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type J_PDF_VCI_VFILLCVE_7S295_0016_1;

FIGS. 1082A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type J_PDF_VCI_VFILLCVE_7S295_0001_1;

FIGS. 1083A-C respectively depict plan views of—(A) all layers; (B) NWELL, AA, GATE, GATECNT, TS, and AACNT layers; (C) V0, and M1 layers—of an exemplary M1-stitch-open-configured, NCEM-enabled fill cell of type J_PDF_VCI_FILL8_39_1;

FIGS. 1084A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type A_PDF_VCI_FILL6_9S109_0001_1;

FIGS. 1085A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type A_PDF_VCI_FILL8_9S109_0001_1;

FIGS. 1086A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type A_PDF_VCI_FILL16_9S109_0001_1;

FIGS. 1087A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type A_PDF_VCI_FILL32_9S109_0001_1;

FIGS. 1088A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type A_PDF_VCI_FILL64_9S109_0001_1;

FIGS. 1089A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type D_PDF_VCI_VFILL4_12S01_0059_1;

FIGS. 1090A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type E_PDF_VCI_FILL8_17S1_0038_1;

FIGS. 1091A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type F_PDF_VCI_FILL16_24S2_0024_1;

FIGS. 1092A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type F_PDF_VCI_FILL08_24S2_0007_1;

FIGS. 1093A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type F_PDF_VCI_FILL32_24S2_0020_1;

FIGS. 1094A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type F_PDF_VCI_FILL06_24S2_0005_1;

FIGS. 1095A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type J_PDF_VCI_FILL8_25_1;

FIGS. 1096A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20001CA_01;

FIGS. 1097A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20009CA_09;

FIGS. 1098A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20011CA_17;

FIGS. 1099A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20001CB_01;

FIGS. 1100A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20009CB_09;

FIGS. 1101A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type K_V549_PDF_VCI_20011CB_17;

FIGS. 1102A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20001CA_01;

FIGS. 1103A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20009CA_09;

FIGS. 1104A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20011CA_17;

FIGS. 1105A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20001CB_01;

FIGS. 1106A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20009CB_09;

FIGS. 1107A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_B_PDF_VCI_20011CB_17;

FIGS. 1108A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20001CA_01;

FIGS. 1109A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20009CA_09;

FIGS. 1110A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20011CA_17;

FIGS. 1111A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20001CB_01;

FIGS. 1112A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20009CB_09;

FIGS. 1113A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type L_V54C_M_PDF_VCI_20011CB_17;

FIGS. 1114A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20001CA_01;

FIGS. 1115A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20009CA_09;

FIGS. 1116A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20011CA_17;

FIGS. 1117A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20001CB_01;

FIGS. 1118A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20009CB_09;

FIGS. 1119A-C respectively depict plan views of—(A) all layers; (B) NWELL, AA, GATE, GATECNT, TS, and AACNT layers; (C) V0, and M1 layers—of an exemplary GATE-AA-tip-to-side-short-configured, NCEM-enabled fill cell of type M_V54B_PDF_VCI_20011CB_17;

FIGS. 1120A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type D_PDF_VCI_VFILL4_12S01_0101_1;

FIGS. 1121A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type D_PDF_VCI_VFILL8_12S01_0008_1;

FIGS. 1122A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type D_PDF_VCI_VFILL8_12S01_0006_1;

FIGS. 1123A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type E_PDF_VCI_FILL8_17S1_0049_1;

FIGS. 1124A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type E_PDF_VCI_FILL8_17S1_0047_1;

FIGS. 1125A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type E_PDF_VCI_FILL8_17S1_0045_1;

FIGS. 1126A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL64_24S1_0084_1;

FIGS. 1127A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL64_24S1_0083_1;

FIGS. 1128A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL08_24S1_0082_1;

FIGS. 1129A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL08_24S1_0081_1;

FIGS. 1130A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL08_24S1_0080_1;

FIGS. 1131A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL32_24S1_0082_1;

FIGS. 1132A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL32_24S1_0081_1;

FIGS. 1133A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL32_24S1_0080_1;

FIGS. 1134A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL16_24S1_0041_1;

FIGS. 1135A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL16_24S1_0040_1;

FIGS. 1136A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL16_24S1_0039_1;

FIGS. 1137A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type F_PDF_VCI_FILL64_24S1_0001_1;

FIGS. 1138A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300012A_01;

FIGS. 1139A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300122A_18;

FIGS. 1140A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300232A_35;

FIGS. 1141A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300012C_01;

FIGS. 1142A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300122C_18;

FIGS. 1143A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_300232C_35;

FIGS. 1144A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_4000110_01;

FIGS. 1145A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_4001710_23;

FIGS. 1146A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_4000112_01;

FIGS. 1147A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type G_V931_PDF_VCI_4001712_23;

FIGS. 1148A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type J_PDF_VCI_FILL8_3_1;

FIGS. 1149A-C respectively depict plan views of—(A) all layers; (B) NWELL, AA, GATE, GATECNT, TS, and AACNT layers; (C) V0, and M1 layers—of an exemplary GATECNT-tip-to-side-short-configured, NCEM-enabled fill cell of type J_PDF_VCI_FILL8_4_1;

FIGS. 1150A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300013E_01;

FIGS. 1151A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000D3E_13;

FIGS. 1152A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300193E_25;

FIGS. 1153A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000140_01;

FIGS. 1154A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000D40_13;

FIGS. 1155A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3001940_25;

FIGS. 1156A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000142_01;

FIGS. 1157A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000D42_13;

FIGS. 1158A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3001942_25;

FIGS. 1159A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000144_01;

FIGS. 1160A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000D44_13;

FIGS. 1161A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3001944_25;

FIGS. 1162A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3000148_01;

FIGS. 1163A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3001148_17;

FIGS. 1164A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_3002148_33;

FIGS. 1165A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300014A_01;

FIGS. 1166A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300114A_17;

FIGS. 1167A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300214A_33;

FIGS. 1168A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300014C_01;

FIGS. 1169A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300114C_17;

FIGS. 1170A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300214C_33;

FIGS. 1171A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300014E_01;

FIGS. 1172A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300114E_17;

FIGS. 1173A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_300214E_33;

FIGS. 1174A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_400011A_01;

FIGS. 1175A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_4000D1A_13;

FIGS. 1176A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_4007D1A_125;

FIGS. 1177A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_400011C_01;

FIGS. 1178A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_4000D1C_13;

FIGS. 1179A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type G_V931_PDF_VCI_4004B1C_75;

FIGS. 1180A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL12_19S20001A8;

FIGS. 1181A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL16_19S20002A8;

FIGS. 1182A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL12_19S20003A8;

FIGS. 1183A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL16_19S20004A8;

FIGS. 1184A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL12_19S20005A8;

FIGS. 1185A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_PDF_VCI_FILL16_19S20006A8;

FIGS. 1186A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_V421_VCI_20S10001F9_001;

FIGS. 1187A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_V421_VCI_20S1000DF9_013;

FIGS. 1188A-C respectively depict plan views of—(A) all layers; (B) NWELL, AA, GATE, GATECNT, TS, and AACNT layers; (C) V0, and M1 layers—of an exemplary GATECNT-AACNT-tip-to-side-short-configured, NCEM-enabled fill cell of type I_V421_VCI_20S10019F9_025;

FIGS. 1189A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2000104_01;

FIGS. 1190A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2001004_16;

FIGS. 1191A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2001F04_31;

FIGS. 1192A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2000105_01;

FIGS. 1193A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2001005_16;

FIGS. 1194A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type K_V549_PDF_VCI_2001F05_31;

FIGS. 1195A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2000104_01;

FIGS. 1196A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2001004_16;

FIGS. 1197A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2001F04_31;

FIGS. 1198A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2000105_01;

FIGS. 1199A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2001005_16;

FIGS. 1200A-C respectively depict plan views of—(A) all layers; (B) NWELL, AA, GATE, GATECNT, TS, and AACNT layers; (C) V0, and M1 layers—of an exemplary GATECNT-AACNT-TS-tip-to-side-short-configured, NCEM-enabled fill cell of type L_V54C_M_PDF_VCI_2001F05_31;

FIGS. 1201A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_2000181_01;

FIGS. 1202A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_2004581_69;

FIGS. 1203A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_2000183_01;

FIGS. 1204A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_4000106_01;

FIGS. 1205A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_4000D06_13;

FIGS. 1206A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type G_V931_PDF_VCI_4001906_25;

FIGS. 1207A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV4_7S103_32_1;

FIGS. 1208A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV4_7S103_61_1;

FIGS. 1209A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV4_7S103_62_1;

FIGS. 1210A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S104_1_1;

1211A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S104_30_1;

FIGS. 1212A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S104_31_1;

FIGS. 1213A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S105_32_1;

FIGS. 1214A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S105_61_1;

FIGS. 1215A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S105_62_1;

FIGS. 1216A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S272_0065_1;

FIGS. 1217A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S272_0002_1;

FIGS. 1218A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type J_PDF_VCI_VFILLCV8_7S272_0001_1;

FIGS. 1219A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_3000130_01;

FIGS. 1220A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_3001030_16;

FIGS. 1221A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_3001F30_31;

FIGS. 1222A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_2000106_01;

FIGS. 1223A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_2001006_16;

FIGS. 1224A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type K_V549_PDF_VCI_2001F06_31;

FIGS. 1225A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3000130_01;

FIGS. 1226A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3001030_16;

FIGS. 1227A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3001F30_31;

FIGS. 1228A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_300012D_01;

FIGS. 1229A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_300102D_16;

FIGS. 1230A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3001F2D_31;

FIGS. 1231A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_300012E_01;

FIGS. 1232A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_300102E_16;

FIGS. 1233A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3001F2E_31;

FIGS. 1234A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3000129_01;

FIGS. 1235A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_3000229_02;

FIGS. 1236A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_2000106_01;

FIGS. 1237A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_2001006_16;

FIGS. 1238A-C respectively depict plan views of—(A) all layers; (B) NWELL, AA, GATE, GATECNT, TS, and AACNT layers; (C) V0, and M1 layers—of an exemplary GATECNT-GATE-tip-to-side-short-configured, NCEM-enabled fill cell of type L_V54C_M_PDF_VCI_2001F06_31;

FIGS. 1239A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_V421_VCI_20S10001FE_001;

FIGS. 1240A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_V421_VCI_20S1000DFE_013;

FIGS. 2141A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_V421_VCI_20S10019FE_025;

FIGS. 1242A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_V421_VCI_20S1001AFE_026;

FIGS. 1243A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL12_19S20001D0;

FIGS. 1244A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL16_19S20002D0;

FIGS. 1245A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL12_19S20003D0;

FIGS. 1246A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL16_19S20004D0;

FIGS. 1247A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL12_19S20005D0;

FIGS. 1248A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type I_PDF_VCI_FILL16_19S20006D0;

FIGS. 1249A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2000168_01;

FIGS. 1250A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2000F68_15;

FIGS. 1251A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2001D68_29;

FIGS. 1252A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_200016A_01;

FIGS. 1253A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2000F6A_15;

FIGS. 1254A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2001D6A_29;

FIGS. 1255A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_200016C_01;

FIGS. 1256A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2000F6C_15;

FIGS. 1257A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54A_PDF_VCI_2001D6C_29;

FIGS. 1258A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000123_01;

FIGS. 1259A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000823_08;

FIGS. 1260A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000F23_15;

FIGS. 1261A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000125_01;

FIGS. 1262A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000825_08;

FIGS. 1263A-C respectively depict plan views of—(A) all layers; (B) NWELL, AA, GATE, GATECNT, TS, and AACNT layers; (C) V0, and M1 layers—of an exemplary GATECNT-TS-tip-to-side-short-configured, NCEM-enabled fill cell of type M_V54B_PDF_VCI_3000F25_15;

FIGS. 1264A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type A_PDF_VCI_FILL8_9S115_0003_1;

FIGS. 1265A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type A_PDF_VCI_FILL16_9S115_0003_1;

FIGS. 1266A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type A_PDF_VCI_FILL32_9S115_0003_1;

FIGS. 1267A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type A_PDF_VCI_FILL64_9S115_0003_1;

FIGS. 1268A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type D_PDF_VCI_VFILLE_12S02_0033_1;

FIGS. 1269A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type D_PDF_VCI_VFILLE_12S02_0032_1;

FIGS. 1270A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type D_PDF_VCI_VFILLE_12S02_0031_1;

FIGS. 1271A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type E_PDF_VCI_FILL8_17S2_0002_1;

FIGS. 1272A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type E_PDF_VCI_FILL8_17S2_0001_1;

FIGS. 1273A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL16_24S1_0073_1;

FIGS. 1274A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL16_24S1_0072_1;

FIGS. 1275A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL64_24S1_0033_1;

FIGS. 1276A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL64_24S1_0032_1;

FIGS. 1277A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL08_24S1_0030_1;

FIGS. 1278A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL08_24S1_0029_1;

FIGS. 1279A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL32_24S1_0030_1;

FIGS. 1280A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL32_24S1_0029_1;

FIGS. 1281A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL16_24S2_0010_1;

FIGS. 1282A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL16_24S2_0009_1;

FIGS. 1283A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL16_24S2_0008_1;

FIGS. 1284A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL32_24S2_0010_1;

FIGS. 1285A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL32_24S2_0009_1;

FIGS. 1286A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL32_24S2_0008_1;

FIGS. 1287A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL64_24S2_0024_1;

FIGS. 1288A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL64_24S2_0022_1;

FIGS. 1289A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL64_24S2_0020_1;

FIGS. 1290A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL08_24S2_0035_1;

FIGS. 1291A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL08_24S2_0034_1;

FIGS. 1292A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type F_PDF_VCI_FILL08_24S2_0033_1;

FIGS. 1293A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type J_PDF_VCI_VFILLCVE_7S156_136_1;

FIGS. 1294A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type J_PDF_VCI_VFILLCVE_7S156_146_1;

FIGS. 1295A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type J_PDF_VCI_VFILLCVE_7S157_157_1;

FIGS. 1296A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type J_PDF_VCI_VFILLCVE_7S157_167_1;

FIGS. 1297A-C respectively depict plan views of—(A) all layers; (B) NWELL, AA, GATE, GATECNT, TS, and AACNT layers; (C) V0, and M1 layers—of an exemplary M1-tip-to-side-short-configured, NCEM-enabled fill cell of type J_PDF_VCI_FILL8_36_1;

FIGS. 1298A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL4_9S110_0001_1;

FIGS. 1299A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL8_9S110_0002_1;

FIGS. 1300A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL16_9S110_0002_1;

FIGS. 1301A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL32_9S110_0002_1;

FIGS. 1302A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL64_9S110_0002_1;

FIGS. 1303A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL8_9S110_0001_1;

FIGS. 1304A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL16_9S110_0001_1;

FIGS. 1305A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL32_9S110_0001_1;

FIGS. 1306A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type A_PDF_VCI_FILL64_9S110_0001_1;

FIGS. 1307A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type D_PDF_VCI_VFILL8_12S01_0010_1;

FIGS. 1308A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type D_PDF_VCI_VFILL4_12S01_0016_1;

FIGS. 1309A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type E_PDF_VCI_FILL8_17S1_0030_1;

FIGS. 1310A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type E_PDF_VCI_FILL8_17S1_0028_1;

FIGS. 1311A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL16_24S2_0031_1;

FIGS. 1312A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL16_24S2_0030_1;

FIGS. 1313A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL64_24S2_0017_1;

FIGS. 1314A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL08_24S2_0012_1;

FIGS. 1315A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL08_24S2_0011_1;

FIGS. 1316A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL64_24S2_0016_1;

FIGS. 1317A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL32_24S2_0025_1;

FIGS. 1318A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL32_24S2_0024_1;

FIGS. 1319A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type F_PDF_VCI_FILL04_24S2_0005_1;

FIGS. 1320A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type G_V931_PDF_VCI_200015D_01;

FIGS. 1321A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type G_V931_PDF_VCI_200015E_01;

FIGS. 1322A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type G_V931_PDF_VCI_200015F_01;

FIGS. 1323A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type G_V931_PDF_VCI_2000161_01;

FIGS. 1324A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type J_PDF_VCI_FILL4_2_1;

FIGS. 1325A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type J_PDF_VCI_FILL8_26_1;

FIGS. 1326A-C respectively depict plan views of—(A) all layers; (B) NWELL, AA, GATE, GATECNT, TS, and AACNT layers; (C) V0, and M1 layers—of an exemplary AA-tip-to-tip-short-configured, NCEM-enabled fill cell of type J_PDF_VCI_FILL8_27_1;

FIGS. 1327A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL6_9S103_0002_1;

FIGS. 1328A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL8_9S103_0002_1;

FIGS. 1329A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL16_9S103_0002_1;

FIGS. 1330A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL32_9S103_0002_1;

FIGS. 1331A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL64_9S103_0002_1;

FIGS. 1332A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL6_9S105_0002_1;

FIGS. 1333A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL8_9S105_0002_1;

FIGS. 1334A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL16_9S105_0002_1;

FIGS. 1335A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL32_9S105_0002_1;

FIGS. 1336A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type A_PDF_VCI_FILL64_9S105_0002_1;

FIGS. 1337A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type D_PDF_VCI_VFILL4_12S01_0023_1;

FIGS. 1338A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type D_PDF_VCI_VFILL4_12S01_0069_1;

FIGS. 1339A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type D_PDF_VCI_VFILL4_12S01_0058_1;

FIGS. 1340A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type D_PDF_VCI_VFILL4_12S01_0051_1;

FIGS. 1341A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type E_PDF_VCI_FILL8_17S1_0041_1;

FIGS. 1342A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type E_PDF_VCI_FILL8_17S1_0037_1;

FIGS. 1343A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type E_PDF_VCI_FILL8_17S1_0025_1;

FIGS. 1344A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type E_PDF_VCI_FILL8_17S1_0023_1;

FIGS. 1345A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S2_0034_1;

FIGS. 1346A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S1_0074_1;

FIGS. 1347A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S2_0032_1;

FIGS. 1348A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S1_0072_1;

FIGS. 1349A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S2_0031_1;

FIGS. 1350A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL08_24S2_0025_1;

FIGS. 1351A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL64_24S2_0030_1;

FIGS. 1352A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL08_24S2_0024_1;

FIGS. 1353A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL08_24S2_0023_1;

FIGS. 1354A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL08_24S2_0022_1;

FIGS. 1355A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL32_24S2_0042_1;

FIGS. 1356A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL32_24S2_0041_1;

FIGS. 1357A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL32_24S2_0040_1;

FIGS. 1358A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL32_24S2_0038_1;

FIGS. 1359A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL16_24S2_0045_1;

FIGS. 1360A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL16_24S2_0044_1;

FIGS. 1361A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL16_24S2_0043_1;

FIGS. 1362A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL16_24S2_0042_1;

FIGS. 1363A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL06_24S2_0009_1;

FIGS. 1364A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL06_24S2_0008_1;

FIGS. 1365A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL06_24S2_0007_1;

FIGS. 1366A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type F_PDF_VCI_FILL06_24S2_0006_1;

FIGS. 1367A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200018D_01;

FIGS. 1368A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200098D_09;

FIGS. 1369A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200018F_01;

FIGS. 1370A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200098F_09;

FIGS. 1371A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_2000159_01;

FIGS. 1372A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_2000959_09;

FIGS. 1373A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200015B_01;

FIGS. 1374A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200095B_09;

FIGS. 1375A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200115B_17;

FIGS. 1376A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200017B_01;

FIGS. 1377A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_2000D7B_13;

FIGS. 1378A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_200017D_01;

FIGS. 1379A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type G_V931_PDF_VCI_2000D7D_13;

FIGS. 1380A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL08_19S20001B2;

FIGS. 1381A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL12_19S20002B2;

FIGS. 1382A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL16_19S20003B2;

FIGS. 1383A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL08_19S20004B2;

FIGS. 1384A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL12_19S20005B2;

FIGS. 1385A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_PDF_VCI_FILL16_19S20006B2;

FIGS. 1386A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S30001E3_001;

FIGS. 1387A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S30009E3_009;

FIGS. 1388A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S30012E3_018;

FIGS. 1389A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S3001AE3_026;

FIGS. 1390A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S30023E3_035;

FIGS. 1391A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type I_V421_VCI_20S3002BE3_043;

FIGS. 1392A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_VFILLCV4_7S200_0033_1;

FIGS. 1393A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_VFILLCV4_7S200_0002_1;

FIGS. 1394A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_VFILLCV4_7S200_0001_1;

FIGS. 1395A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_FILL8_6_1;

FIGS. 1396A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_FILL8_11_1;

FIGS. 1397A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type J_PDF_VCI_FILL8_13_1;

FIGS. 1398A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type K_V549_PDF_VCI_20009C2_09;

FIGS. 1399A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type K_V549_PDF_VCI_20001C1_01;

FIGS. 1400A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type K_V549_PDF_VCI_20009C1_09;

FIGS. 1401A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type K_V549_PDF_VCI_20011C1_17;

FIGS. 1402A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type L_V54C_M_PDF_VCI_20001C1_01;

FIGS. 1403A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type L_V54C_M_PDF_VCI_20009C1_09;

FIGS. 1404A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type L_V54C_M_PDF_VCI_20011C1_17;

FIGS. 1405A-C respectively depict plan views of—(A) all layers; (B) NWELL, AA, GATE, GATECNT, TS, and AACNT layers; (C) V0, and M1 layers—of an exemplary AACNT-tip-to-tip-short-configured, NCEM-enabled fill cell of type L_V54C_M_PDF_VCI_20009C2_09;

FIGS. 1406A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type G_V931_PDF_VCI_30001F2_01;

FIGS. 1407A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type G_V931_PDF_VCI_3000DF2_13;

FIGS. 1408A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type I_PDF_VCI_FILL12_19S20001BC;

FIGS. 1409A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type I_PDF_VCI_FILL16_19S20002BC;

FIGS. 1410A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type I_V421_VCI_20S200011C_001;

FIGS. 1411A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type I_V421_VCI_20S2000D1C_013;

FIGS. 1412A-C respectively depict plan views of—(A) all layers; (B) NWELL, AA, GATE, GATECNT, TS, and AACNT layers; (C) V0, and M1 layers—of an exemplary AACNT-TS-tip-to-tip-short-configured, NCEM-enabled fill cell of type I_V421_VCI_20S200191C_025;

FIGS. 1413A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL8_9S118_0003_1;

FIGS. 1414A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL16_9S118_0003_1;

FIGS. 1415A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL32_9S118_0003_1;

FIGS. 1416A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL64_9S118_0003_1;

FIGS. 1417A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL8_9S118_0002_1;

FIGS. 1418A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL16_9S118_0002_1;

FIGS. 1419A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL32_9S118_0002_1;

FIGS. 1420A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL64_9S118_0002_1;

FIGS. 1421A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL8_9S118_0001_1;

FIGS. 1422A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL16_9S118_0001_1;

FIGS. 1423A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL32_9S118_0001_1;

FIGS. 1424A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type A_PDF_VCI_FILL64_9S118_0001_1;

FIGS. 1425A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type D_PDF_VCI_VFILL4_12S01_0106_1;

FIGS. 1426A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type D_PDF_VCI_VFILL8_12S01_0004_1;

FIGS. 1427A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type D_PDF_VCI_VFILL8_12S01_0002_1;

FIGS. 1428A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type E_PDF_VCI_FILL8_17S1_0016_1;

FIGS. 1429A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type E_PDF_VCI_FILL8_17S1_0014_1;

FIGS. 1430A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type E_PDF_VCI_FILL8_17S1_0012_1;

FIGS. 1431A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL16_24S2_0029_1;

FIGS. 1432A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL16_24S1_0061_1;

FIGS. 1433A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL16_24S1_0060_1;

FIGS. 1434A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL64_24S2_0015_1;

FIGS. 1435A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL64_24S1_0021_1;

FIGS. 1436A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL64_24S1_0020_1;

FIGS. 1437A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL08_24S2_0010_1;

FIGS. 1438A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL08_24S1_0018_1;

FIGS. 1439A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL08_24S1_0017_1;

FIGS. 1440A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL32_24S2_0023_1;

FIGS. 1441A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL32_24S1_0018_1;

FIGS. 1442A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL32_24S1_0017_1;

FIGS. 1443A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL16_24S2_0028_1;

FIGS. 1444A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL16_24S2_0026_1;

FIGS. 1445A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL32_24S2_0022_1;

FIGS. 1446A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL32_24S2_0021_1;

FIGS. 1447A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL64_24S2_0014_1;

FIGS. 1448A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL64_24S2_0013_1;

FIGS. 1449A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL08_24S2_0009_1;

FIGS. 1450A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type F_PDF_VCI_FILL08_24S2_0008_1;

FIGS. 1451A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_2000168_01;

FIGS. 1452A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_2000568_05;

FIGS. 1453A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_2000167_01;

FIGS. 1454A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_2000169_01;

FIGS. 1455A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_200016B_01;

FIGS. 1456A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_400016A_01;

FIGS. 1457A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_4000D6A_13;

FIGS. 1458A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type G_V931_PDF_VCI_400196A_25;

FIGS. 1459A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type J_PDF_VCI_FILL8_47_1;

FIGS. 1460A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type J_PDF_VCI_FILL8_48_1;

FIGS. 1461A-C respectively depict plan views of—(A) all layers; (B) NWELL, AA, GATE, GATECNT, TS, and AACNT layers; (C) V0, and M1 layers—of an exemplary GATE-tip-to-tip-short-configured, NCEM-enabled fill cell of type J_PDF_VCI_FILL8_49_1;

FIGS. 1462A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL8_9S101_0002_1;

FIGS. 1463A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL16_9S101_0002_1;

FIGS. 1464A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL32_9S101_0002_1;

FIGS. 1465A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL64_9S101_0002_1;

FIGS. 1466A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL8_9S101_0001_1;

FIGS. 1467A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL16_9S101_0001_1;

FIGS. 1468A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL32_9S101_0001_1;

FIGS. 1469A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL64_9S101_0001_1;

FIGS. 1470A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL8_9S106_0004_1;

FIGS. 1471A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL16_9S106_0004_1;

FIGS. 1472A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL32_9S106_0004_1;

FIGS. 1473A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL64_9S106_0004_1;

FIGS. 1474A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL8_9S106_0003_1;

FIGS. 1475A-C respectively depict plan views of—(A) all layers; (B) NWELL, AA, GATE, GATECNT, TS, and AACNT layers;

AACNT layers; (C) V0, and M1 layers—of an exemplary GATECNT-tip-to-tip-short-configured, NCEM-enabled fill cell of type A_PDF_VCI_FILL16_9S106_0003_1;

FIGS. 1476A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL32_9S106_0003_1;

FIGS. 1477A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL64_9S106_0003_1;

FIGS. 1478A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL8_9S106_0002_1;

FIGS. 1479A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL16_9S106_0002_1;

FIGS. 1480A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL32_9S106_0002_1;

FIGS. 1481A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type A_PDF_VCI_FILL64_9S106_0002_1;

FIGS. 1482A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type D_PDF_VCI_VFILL4_12S01_0044_1;

FIGS. 1483A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type D_PDF_VCI_VFILL4_12S01_0026_1;

FIGS. 1484A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type D_PDF_VCI_VFILL4_12S01_0079_1;

FIGS. 1485A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type D_PDF_VCI_VFILL4_12S01_0061_1;

FIGS. 1486A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type E_PDF_VCI_FILL8_17S1_0015_1;

FIGS. 1487A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type E_PDF_VCI_FILL8_17S1_0013_1;

FIGS. 1488A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type E_PDF_VCI_FILL8_17S1_0011_1;

FIGS. 1489A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type E_PDF_VCI_FILL8_17S1_0009_1;

FIGS. 1490A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL64_24S2_0029_1;

FIGS. 1491A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL64_24S1_0067_1;

FIGS. 1492A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL64_24S2_0027_1;

FIGS. 1493A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL64_24S2_0026_1;

FIGS. 1494A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL08_24S2_0021_1;

FIGS. 1495A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL08_24S1_0064_1;

FIGS. 1496A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL08_24S2_0019_1;

FIGS. 1497A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL08_24S2_0018_1;

FIGS. 1498A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL32_24S2_0037_1;

FIGS. 1499A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL32_24S2_0035_1;

FIGS. 1500A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL32_24S2_0034_1;

FIGS. 1501A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL32_2451_0064_1;

FIGS. 1502A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL16_24S2_0041_1;

FIGS. 1503A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL16_2451_0023_1;

FIGS. 1504A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL16_24S2_0039_1;

FIGS. 1505A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL16_24S2_0038_1;

FIGS. 1506A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL16_24S2_0040_1;

FIGS. 1507A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL32_24S2_0036_1;

FIGS. 1508A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL64_24S2_0028_1;

FIGS. 1509A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type F_PDF_VCI_FILL08_24S2_0020_1;

FIGS. 1510A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3000120_01;

FIGS. 1511A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3001320_19;

FIGS. 1512A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3002520_37;

FIGS. 1513A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3000122_01;

FIGS. 1514A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3001122_17;

FIGS. 1515A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3002122_33;

FIGS. 1516A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3000124_01;

FIGS. 1517A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3001124_17;

FIGS. 1518A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type G_V931_PDF_VCI_3002124_33;

FIGS. 1519A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_PDF_VCI_FILL08_19S20001C6;

FIGS. 1520A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_PDF_VCI_FILL12_19S20002C6;

FIGS. 1521A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_PDF_VCI_FILL16_19S20003C6;

FIGS. 1522A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S2000126_001;

FIGS. 1523A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S2001026_016;

FIGS. 1524A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S2001F26_031;

FIGS. 1525A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S200012B_001;

FIGS. 1526A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S200102B_016;

FIGS. 1527A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type I_V421_VCI_20S2001F2B_031;

FIGS. 1528A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S240_0012_1;

FIGS. 1529A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S240_0008_1;

FIGS. 1530A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S240_0001_1;

FIGS. 1531A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S241_0018_1;

FIGS. 1532A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S241_0014_1;

FIGS. 1533A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S241_0001_1;

FIGS. 1534A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S242_0012_1;

FIGS. 1535A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S242_0009_1;

FIGS. 1536A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S242_0001_1;

FIGS. 1537A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S243_0014_1;

FIGS. 1538A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S243_0011_1;

FIGS. 1539A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_VFILLCV4_7S243_0001_1;

FIGS. 1540A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_FILL8_15_1;

FIGS. 1541A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_FILL8_16_1;

FIGS. 1542A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type J_PDF_VCI_FILL8_17_1;

FIGS. 1543A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type L_V54C_E_PDF_VCI_2000103_01;

FIGS. 1544A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type L_V54C_E_PDF_VCI_2000A03_10;

FIGS. 1545A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type L_V54C_E_PDF_VCI_2001303_19;

FIGS. 1546A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type M_V54A_PDF_VCI_2000103_01;

FIGS. 1547A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type M_V54A_PDF_VCI_2000A03_10;

FIGS. 1548A-C respectively depict plan views of—(A) all layers; (B) NWELL, AA, GATE, GATECNT, TS, and AACNT layers; (C) V0, and M1 layers—of an exemplary GATECNT-tip-to-tip-short-configured, NCEM-enabled fill cell of type M_V54A_PDF_VCI_2001303_19;

FIGS. 1549A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_PDF_VCI_FILL12_19S00019E;

FIGS. 1550A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_PDF_VCI_FILL16_19S00029E;

FIGS. 1551A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_PDF_VCI_FILL12_19S00039E;

FIGS. 1552A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_PDF_VCI_FILL16_19S00049E;

FIGS. 1553A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_V421_VCI_20S30001CF_001;

FIGS. 1554A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_V421_VCI_20S30005CF_005;

FIGS. 1555A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_V421_VCI_20S3000BCF_011;

FIGS. 1556A-C respectively depict plan views of—(A) all layers; (B) NWELL, AA, GATE, GATECNT, TS, and AACNT layers; (C) V0, and M1 layers—of an exemplary M1-tip-to-tip-short-configured, NCEM-enabled fill cell of type I_V421_VCI_20S3000FCF_015;

FIGS. 1557A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_10001F5_01;

FIGS. 1558A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_10023F5_35;

FIGS. 1559A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_10045F5_69;

FIGS. 1560A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_10161F5_353;

FIGS. 1561A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_10183F5_387;

FIGS. 1562A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_101A5F5_421;

FIGS. 1563A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200013F_01;

FIGS. 1564A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200233F_35;

FIGS. 1565A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200463F_70;

FIGS. 1566A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B13F_177;

FIGS. 1567A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D33F_211;

FIGS. 1568A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F63F_246;

FIGS. 1569A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000101_01;

FIGS. 1570A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002301_35;

FIGS. 1571A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004501_69;

FIGS. 1572A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2016101_353;

FIGS. 1573A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2018301_387;

FIGS. 1574A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201A501_421;

FIGS. 1575A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200010D_01;

FIGS. 1576A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200230D_35;

FIGS. 1577A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200450D_69;

FIGS. 1578A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201610D_353;

FIGS. 1579A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201830D_387;

FIGS. 1580A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201A50D_421;

FIGS. 1581A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000119_01;

FIGS. 1582A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002319_35;

FIGS. 1583A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004519_69;

FIGS. 1584A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2016119_353;

FIGS. 1585A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2018319_387;

FIGS. 1586A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201A519_421;

FIGS. 1587A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000125_01;

FIGS. 1588A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002325_35;

FIGS. 1589A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004525_69;

FIGS. 1590A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2016125_353;

FIGS. 1591A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2018325_387;

FIGS. 1592A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201A525_421;

FIGS. 1593A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000127_01;

FIGS. 1594A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002327_35;

FIGS. 1595A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004527_69;

FIGS. 1596A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2016127_353;

FIGS. 1597A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2018327_387;

FIGS. 1598A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_201A527_421;

FIGS. 1599A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000133_01;

FIGS. 1600A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002333_35;

FIGS. 1601A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004633_70;

FIGS. 1602A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B133_177;

FIGS. 1603A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D333_211;

FIGS. 1604A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F633_246;

FIGS. 1605A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200024B_02;

FIGS. 1606A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200234B_35;

FIGS. 1607A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200454B_69;

FIGS. 1608A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B24B_178;

FIGS. 1609A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D34B_211;

FIGS. 1610A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F54B_245;

FIGS. 1611A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000257_02;

FIGS. 1612A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002357_35;

FIGS. 1613A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004557_69;

FIGS. 1614A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B257_178;

FIGS. 1615A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D357_211;

FIGS. 1616A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F557_245;

FIGS. 1617A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000159_01;

FIGS. 1618A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002359_35;

FIGS. 1619A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004659_70;

FIGS. 1620A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B159_177;

FIGS. 1621A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D359_211;

FIGS. 1622A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F659_246;

FIGS. 1623A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2000165_01;

FIGS. 1624A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2002365_35;

FIGS. 1625A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_2004665_70;

FIGS. 1626A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200B165_177;

FIGS. 1627A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200D365_211;

FIGS. 1628A-C respectively depict plan views of—(A) all layers; (B) NWELL, AA, GATE, GATECNT, TS, and AACNT layers; (C) V0, and M1 layers—of an exemplary AACNT-AA-via-open-configured, NCEM-enabled fill cell of type C_V682_PDF_VCI_08_200F665_246;

FIGS. 1629A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILLE_12S02_0053_1;

FIGS. 1630A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILLE_12S02_0052_1;

FIGS. 1631A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILLE_12S02_0051_1;

FIGS. 1632A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILLE_12S02_0050_1;

FIGS. 1633A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILL4_12S01_0094_1;

FIGS. 1634A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type D_PDF_VCI_VFILL4_12S01_0015_1;

FIGS. 1635A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type E_PDF_VCI_FILL8_17S1_0033_1;

FIGS. 1636A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type E_PDF_VCI_FILL8_17S1_0029_1;

FIGS. 1637A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL64_24S1_0082_1;

FIGS. 1638A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL64_24S1_0081_1;

FIGS. 1639A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL08_24S1_0079_1;

FIGS. 1640A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL08_24S1_0078_1;

FIGS. 1641A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL32_24S1_0079_1;

FIGS. 1642A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL32_24S1_0078_1;

FIGS. 1643A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL16_24S1_0038_1;

FIGS. 1644A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type F_PDF_VCI_FILL16_24S1_0037_1;

FIGS. 1645A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type I_V421_VCI_20S3000122_001;

FIGS. 1646A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type J_PDF_VCI_VFILLCV4_7S210_0038_1;

FIGS. 1647A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type J_PDF_VCI_VFILLCV4_7S210_0020_1;

FIGS. 1648A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type J_PDF_VCI_VFILLCV4_7S210_0019_1;

FIGS. 1649A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type J_PDF_VCI_VFILLCV4_7S210_0001_1;

FIGS. 1650A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3000121_01;

FIGS. 1651A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3000D21_13;

FIGS. 1652A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3001921_25;

FIGS. 1653A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3001A21_26;

FIGS. 1654A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3002221_34;

FIGS. 1655A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3002A21_42;

FIGS. 1656A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3000122_01;

FIGS. 1657A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3000D22_13;

FIGS. 1658A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3001922_25;

FIGS. 1659A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3001A22_26;

FIGS. 1660A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3002222_34;

FIGS. 1661A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type K_V549_PDF_VCI_3002A22_42;

FIGS. 1662A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3000122_01;

FIGS. 1663A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3000D22_13;

FIGS. 1664A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3001922_25;

FIGS. 1665A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3001A22_26;

FIGS. 1666A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3002222_34;

FIGS. 1667A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3002A22_42;

FIGS. 1668A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3000121_01;

FIGS. 1669A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3000D21_13;

FIGS. 1670A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3001921_25;

FIGS. 1671A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3001A21_26;

FIGS. 1672A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3002221_34;

FIGS. 1673A-C respectively depict plan views of—(A) all layers; (B) NWELL, AA, GATE, GATECNT, TS, and AACNT layers; (C) V0, and M1 layers—of an exemplary AACNT-TS-via-open-configured, NCEM-enabled fill cell of type L_V54C_M_PDF_VCI_3002A21_42;

FIGS. 1674A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_30001FC_01;

FIGS. 1675A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_3000DFC_13;

FIGS. 1676A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_30019FC_25;

FIGS. 1677A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4000156_01;

FIGS. 1678A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4000D56_13;

FIGS. 1679A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4001956_25;

FIGS. 1680A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4001A56_26;

FIGS. 1681A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4002656_38;

FIGS. 1682A-C respectively depict plan views of—(A) all layers; (B) NWELL, AA, GATE, GATECNT, TS, and AACNT layers; (C) V0, and M1 layers—of an exemplary GATECNT-AACNT-via-open-configured, NCEM-enabled fill cell of type G_V931_PDF_VCI_4003256_50;

FIGS. 1683A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type A_PDF_VCI_FILL8_9S112_0001_1;

FIGS. 1684A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type A_PDF_VCI_FILL16_9S112_0001_1;

FIGS. 1685A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type A_PDF_VCI_FILL32_9S112_0001_1;

FIGS. 1686A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type A_PDF_VCI_FILL64_9S112_0001_1;

FIGS. 1687A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3000137_01;

FIGS. 1688A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3000D37_13;

FIGS. 1689A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3001937_25;

FIGS. 1690A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3001A37_26;

FIGS. 1691A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3002637_38;

FIGS. 1692A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3003237_50;

FIGS. 1693A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3003337_51;

FIGS. 1694A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3003F37_63;

FIGS. 1695A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3004B37_75;

FIGS. 1696A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3004C37_76;

FIGS. 1697A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3005837_88;

FIGS. 1698A-C respectively depict plan views of—(A) all layers; (B) NWELL, AA, GATE, GATECNT, TS, and AACNT layers; (C) V0, and M1 layers—of an exemplary GATECNT-AACNT-GATE-via-open-configured, NCEM-enabled fill cell of type L_V54C_M_PDF_VCI_3006437_100;

FIGS. 1699A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL8_9S101_0004_1;

FIGS. 1700A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL16_9S101_0004_1;

FIGS. 1701A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL32_9S101_0004_1;

FIGS. 1702A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL64_9S101_0004_1;

FIGS. 1703A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL8_9S101_0003_1;

FIGS. 1704A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL16_9S101_0003_1;

FIGS. 1705A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL32_9S101_0003_1;

FIGS. 1706A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL64_9S101_0003_1;

FIGS. 1707A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL8_9S107_0003_1;

FIGS. 1708A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL16_9S107_0002_1;

FIGS. 1709A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL32_9S107_0003_1;

FIGS. 1710A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL64_9S107_0003_1;

FIGS. 1711A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL8_9S111_0001_1;

FIGS. 1712A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL16_9S111_0001_1;

FIGS. 1713A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL32_9S111_0001_1;

FIGS. 1714A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type A_PDF_VCI_FILL64_9S111_0001_1;

FIGS. 1715A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2000140_01;

FIGS. 1716A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2002240_34;

FIGS. 1717A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2004340_67;

FIGS. 1718A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2000146_01;

FIGS. 1719A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2002246_34;

FIGS. 1720A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type C_V682_PDF_VCI_16_2004346_67;

FIGS. 1721A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0105_1;

FIGS. 1722A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0037_1;

FIGS. 1723A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0034_1;

FIGS. 1724A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0097_1;

FIGS. 1725A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0088_1;

FIGS. 1726A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0087_1;

FIGS. 1727A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0019_1;

FIGS. 1728A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0083_1;

FIGS. 1729A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0008_1;

FIGS. 1730A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0070_1;

FIGS. 1731A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0001_1;

FIGS. 1732A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0065_1;

FIGS. 1733A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type D_PDF_VCI_VFILL4_12S01_0052_1;

FIGS. 1734A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0053_1;

FIGS. 1735A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0051_1;

FIGS. 1736A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0026_1;

FIGS. 1737A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0022_1;

FIGS. 1738A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0021_1;

FIGS. 1739A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0020_1;

FIGS. 1740A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0019_1;

FIGS. 1741A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0018_1;

FIGS. 1742A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0017_1;

FIGS. 1743A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0008_1;

FIGS. 1744A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0007_1;

FIGS. 1745A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0006_1;

FIGS. 1746A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type E_PDF_VCI_FILL8_17S1_0005_1;

FIGS. 1747A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0084_1;

FIGS. 1748A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S2_0047_1;

FIGS. 1749A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0080_1;

FIGS. 1750A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0079_1;

FIGS. 1751A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0078_1;

FIGS. 1752A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_2451_0076_1;

FIGS. 1753A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_2451_0077_1;

FIGS. 1754A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_2451_0076_1;

FIGS. 1755A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_2451_0075_1;

FIGS. 1756A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_2451_0073_1;

FIGS. 1757A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_2451_0060_1;

FIGS. 1758A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0059_1;

FIGS. 1759A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0058_1;

FIGS. 1760A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S2_0025_1;

FIGS. 1761A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0056_1;

FIGS. 1762A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0057_1;

FIGS. 1763A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S2_0023_1;

FIGS. 1764A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0056_1;

FIGS. 1765A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0054_1;

FIGS. 1766A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0055_1;

FIGS. 1767A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S2_0017_1;

FIGS. 1768A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0053_1;

FIGS. 1769A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S2_0016_1;

FIGS. 1770A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S1_0051_1;

FIGS. 1771A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0084_1;

FIGS. 1772A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S2_0045_1;

FIGS. 1773A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0077_1;

FIGS. 1774A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0076_1;

FIGS. 1775A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0075_1;

FIGS. 1776A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0073_1;

FIGS. 1777A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0057_1;

FIGS. 1778A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0056_1;

FIGS. 1779A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0055_1;

FIGS. 1780A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S2_0033_1;

FIGS. 1781A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0053_1;

FIGS. 1782A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S2_0031_1;

FIGS. 1783A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL32_24S1_0051_1;

FIGS. 1784A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0043_1;

FIGS. 1785A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S2_0035_1;

FIGS. 1786A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0036_1;

FIGS. 1787A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0035_1;

FIGS. 1788A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0034_1;

FIGS. 1789A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0032_1;

FIGS. 1790A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0016_1;

FIGS. 1791A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0015_1;

FIGS. 1792A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0014_1;

FIGS. 1793A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S2_0037_1;

FIGS. 1794A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0012_1;

FIGS. 1795A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S2_0036_1;

FIGS. 1796A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL16_24S1_0010_1;

FIGS. 1797A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S1_0003_1;

FIGS. 1798A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL64_24S2_0045_1;

FIGS. 1799A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type F_PDF_VCI_FILL08_24S2_0043_1;

FIGS. 1800A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type G_V931_PDF_VCI_20001AC_01;

FIGS. 1801A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type G_V931_PDF_VCI_2000DAC_13;

FIGS. 1802A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type G_V931_PDF_VCI_20019AC_25;

FIGS. 1803A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type H_PDF_VCI_V16_14S1_08;

FIGS. 1804A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type H_PDF_VCI_V16_14S1_09;

FIGS. 1805A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type H_PDF_VCI_V16_14S1_10;

FIGS. 1806A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type H_PDF_VCI_V16_14S1_13;

FIGS. 1807A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000123_001;

FIGS. 1808A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000223_002;

FIGS. 1809A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000124_001;

FIGS. 1810A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000224_002;

FIGS. 1811A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000125_001;

FIGS. 1812A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000225_002;

FIGS. 1813A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000127_001;

FIGS. 1814A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3001227_018;

FIGS. 1815A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3002327_035;

FIGS. 1816A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3002427_036;

FIGS. 1817A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3003527_053;

FIGS. 1818A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3004627_070;

FIGS. 1819A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000128_001;

FIGS. 1820A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000D28_013;

FIGS. 1821A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3001928_025;

FIGS. 1822A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3001A28_026;

FIGS. 1823A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3002628_038;

FIGS. 1824A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3003228_050;

FIGS. 1825A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3000126_001;

FIGS. 1826A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3001226_018;

FIGS. 1827A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3002326_035;

FIGS. 1828A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3002426_036;

FIGS. 1829A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3003526_053;

FIGS. 1830A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type I_V421_VCI_20S3004626_070;

FIGS. 1831A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S101_1_1;

FIGS. 1832A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S101_31_1;

FIGS. 1833A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S102_63_1;

FIGS. 1834A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S102_92_1;

FIGS. 1835A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S102_93_1;

FIGS. 1836A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S111_282_1;

FIGS. 1837A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S111_311_1;

FIGS. 1838A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S111_312_1;

FIGS. 1839A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S112_313_1;

FIGS. 1840A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S112_342_1;

FIGS. 1841A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S112_343_1;

FIGS. 1842A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S113_344_1;

FIGS. 1843A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S113_373_1;

FIGS. 1844A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S113_374_1;

FIGS. 1845A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S114_375_1;

FIGS. 1846A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S114_404_1;

FIGS. 1847A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S114_405_1;

FIGS. 1848A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV8_7S270_0046_1;

FIGS. 1849A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV8_7S270_0001_1;

FIGS. 1850A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S108_140_1;

FIGS. 1851A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S108_142_1;

FIGS. 1852A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S108_171_1;

FIGS. 1853A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S109_208_1;

FIGS. 1854A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S109_210_1;

FIGS. 1855A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S109_244_1;

FIGS. 1856A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S110_245_1;

FIGS. 1857A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S110_247_1;

FIGS. 1858A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV4_7S110_281_1;

FIGS. 1859A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV8_7S271_0083_1;

FIGS. 1860A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV8_7S271_0002_1;

FIGS. 1861A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_VFILLCV8_7S271_0001_1;

FIGS. 1862A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_FILL8_1_1;

FIGS. 1863A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_FILL8_2_1;

FIGS. 1864A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_FILL8_19_1;

FIGS. 1865A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_FILL8_28_1;

FIGS. 1866A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type J_PDF_VCI_FILL8_29_1;

FIGS. 1867A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_300012B_01;

FIGS. 1868A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_300102B_16;

FIGS. 1869A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001F2B_31;

FIGS. 1870A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000158_01;

FIGS. 1871A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2002458_36;

FIGS. 1872A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2004758_71;

FIGS. 1873A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_300012C_01;

FIGS. 1874A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_300102C_16;

FIGS. 1875A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001F2C_31;

FIGS. 1876A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000128_01;

FIGS. 1877A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001028_16;

FIGS. 1878A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001F28_31;

FIGS. 1879A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002028_32;

FIGS. 1880A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002F28_47;

FIGS. 1881A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003E28_62;

FIGS. 1882A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000100_01;

FIGS. 1883A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001000_16;

FIGS. 1884A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001F00_31;

FIGS. 1885A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_200015A_01;

FIGS. 1886A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_200175A_23;

FIGS. 1887A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2002D5A_45;

FIGS. 1888A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000127_01;

FIGS. 1889A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001027_16;

FIGS. 1890A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001F27_31;

FIGS. 1891A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002027_32;

FIGS. 1892A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002F27_47;

FIGS. 1893A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003E27_62;

FIGS. 1894A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003F27_63;

FIGS. 1895A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3004E27_78;

FIGS. 1896A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3005D27_93;

FIGS. 1897A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000101_01;

FIGS. 1898A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001101_17;

FIGS. 1899A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2002101_33;

FIGS. 1900A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000103_01;

FIGS. 1901A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001003_16;

FIGS. 1902A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001F03_31;

FIGS. 1903A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20001C3_01;

FIGS. 1904A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000AC3_10;

FIGS. 1905A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20013C3_19;

FIGS. 1906A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20001C4_01;

FIGS. 1907A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000AC4_10;

FIGS. 1908A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20013C4_19;

FIGS. 1909A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20001C5_01;

FIGS. 1910A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000AC5_10;

FIGS. 1911A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20013C5_19;

FIGS. 1912A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2000194_01;

FIGS. 1913A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2001794_23;

FIGS. 1914A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2002D94_45;

FIGS. 1915A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000136_01;

FIGS. 1916A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000D36_13;

FIGS. 1917A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001936_25;

FIGS. 1918A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001A36_26;

FIGS. 1919A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002636_38;

FIGS. 1920A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003236_50;

FIGS. 1921A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003336_51;

FIGS. 1922A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003F36_63;

FIGS. 1923A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3004B36_75;

FIGS. 1924A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3004C36_76;

FIGS. 1925A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3005836_88;

FIGS. 1926A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3006436_100;

FIGS. 1927A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000137_01;

FIGS. 1928A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3000D37_13;

FIGS. 1929A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001937_25;

FIGS. 1930A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3001A37_26;

FIGS. 1931A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3002637_38;

FIGS. 1932A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003237_50;

FIGS. 1933A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003337_51;

FIGS. 1934A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3003F37_63;

FIGS. 1935A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3004B37_75;

FIGS. 1936A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3004C37_76;

FIGS. 1937A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3005837_88;

FIGS. 1938A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_3006437_100;

FIGS. 1939A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20001A8_01;

FIGS. 1940A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20017A8_23;

FIGS. 1941A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_20018A8_24;

FIGS. 1942A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type K_V549_PDF_VCI_2002EA8_46;

FIGS. 1943A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_B_PDF_VCI_100012E_01;

FIGS. 1944A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_B_PDF_VCI_100172E_23;

FIGS. 1945A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_B_PDF_VCI_100012C_01;

FIGS. 1946A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_B_PDF_VCI_100242C_36;

FIGS. 1947A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_B_PDF_VCI_100472C_71;

FIGS. 1948A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_300012B_01;

FIGS. 1949A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_300102B_16;

FIGS. 1950A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001F2B_31;

FIGS. 1951A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_300012C_01;

FIGS. 1952A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_300102C_16;

FIGS. 1953A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001F2C_31;

FIGS. 1954A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3000127_01;

FIGS. 1955A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001027_16;

FIGS. 1956A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001F27_31;

FIGS. 1957A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3002027_32;

FIGS. 1958A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3002F27_47;

FIGS. 1959A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003E27_62;

FIGS. 1960A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003F27_63;

FIGS. 1961A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3004E27_78;

FIGS. 1962A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3005D27_93;

FIGS. 1963A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3000128_01;

FIGS. 1964A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001028_16;

FIGS. 1965A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001F28_31;

FIGS. 1966A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3002028_32;

FIGS. 1967A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3002F28_47;

FIGS. 1968A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003E28_62;

FIGS. 1969A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3000136_01;

FIGS. 1970A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3000D36_13;

FIGS. 1971A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001936_25;

FIGS. 1972A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3001A36_26;

FIGS. 1973A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3002636_38;

FIGS. 1974A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003236_50;

FIGS. 1975A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003336_51;

FIGS. 1976A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3003F36_63;

FIGS. 1977A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3004B36_75;

FIGS. 1978A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3004C36_76;

FIGS. 1979A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3005836_88;

FIGS. 1980A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_3006436_100;

FIGS. 1981A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000100_01;

FIGS. 1982A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2001000_16;

FIGS. 1983A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2001F00_31;

FIGS. 1984A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000101_01;

FIGS. 1985A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000601_06;

FIGS. 1986A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000B01_11;

FIGS. 1987A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000103_01;

FIGS. 1988A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2001003_16;

FIGS. 1989A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2001F03_31;

FIGS. 1990A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20001A8_01;

FIGS. 1991A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20017A8_23;

FIGS. 1992A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20018A8_24;

FIGS. 1993A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2002EA8_46;

FIGS. 1994A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20001C3_01;

FIGS. 1995A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000AC3_10;

FIGS. 1996A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20013C3_19;

FIGS. 1997A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20001C4_01;

FIGS. 1998A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000AC4_10;

FIGS. 1999A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20013C4_19;

FIGS. 2000A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20001C5_01;

FIGS. 2001A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_2000AC5_10;

FIGS. 2002A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type L_V54C_M_PDF_VCI_20013C5_19;

FIGS. 2003A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type M_V54B_PDF_VCI_100012E_01;

FIGS. 2004A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type M_V54B_PDF_VCI_100172E_23;

FIGS. 2005A-C respectively depict plan views of—(A) all layers; (B) NWELL, AA, GATE, GATECNT, TS, and AACNT layers; (C) V0, and M1 layers—of an exemplary GATECNT-GATE-via-open-configured, NCEM-enabled fill cell of type M_V54B_PDF_VCI_100182E_24;

FIGS. 2006A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2000156_01;

FIGS. 2007A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2002256_34;

FIGS. 2008A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2004356_67;

FIGS. 2009A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2004456_68;

FIGS. 2010A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2006556_101;

FIGS. 2011A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2008656_134;

FIGS. 2012A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2008756_135;

FIGS. 2013A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200A856_168;

FIGS. 2014A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200C956_201;

FIGS. 2015A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200CA56_202;

FIGS. 2016A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200EB56_235;

FIGS. 2017A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2010C56_268;

FIGS. 2018A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2010D56_269;

FIGS. 2019A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2012E56_302;

FIGS. 2020A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2014F56_335;

FIGS. 2021A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2015056_336;

FIGS. 2022A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2017156_369;

FIGS. 2023A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2019256_402;

FIGS. 2024A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2019356_403;

FIGS. 2025A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201B456_436;

FIGS. 2026A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201D556_469;

FIGS. 2027A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201D656_470;

FIGS. 2028A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201F756_503;

FIGS. 2029A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2021856_536;

FIGS. 2030A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2021956_537;

FIGS. 2031A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2023A56_570;

FIGS. 2032A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2025B56_603;

FIGS. 2033A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200015C_01;

FIGS. 2034A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200225C_34;

FIGS. 2035A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200435C_67;

FIGS. 2036A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200445C_68;

FIGS. 2037A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200655C_101;

FIGS. 2038A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200865C_134;

FIGS. 2039A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200875C_135;

FIGS. 2040A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200A85C_168;

FIGS. 2041A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200C95C_201;

FIGS. 2042A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200CA5C_202;

FIGS. 2043A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_200EB5C_235;

FIGS. 2044A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2010C5C_268;

FIGS. 2045A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2010D5C_269;

FIGS. 2046A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2012E5C_302;

FIGS. 2047A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2014F5C_335;

FIGS. 2048A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201505C_336;

FIGS. 2049A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201715C_369;

FIGS. 2050A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201925C_402;

FIGS. 2051A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201935C_403;

FIGS. 2052A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201B45C_436;

FIGS. 2053A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201D55C_469;

FIGS. 2054A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201D65C_470;

FIGS. 2055A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_201F75C_503;

FIGS. 2056A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_202185C_536;

FIGS. 2057A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_202195C_537;

FIGS. 2058A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2023A5C_570;

FIGS. 2059A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type C_V682_PDF_VCI_08_2025B5C_603;

FIGS. 2060A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0007_1;

FIGS. 2061A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0006_1;

FIGS. 2062A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0005_1;

FIGS. 2063A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0004_1;

FIGS. 2064A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0003_1;

FIGS. 2065A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type D_PDF_VCI_VFILLE_12S02_0002_1;

FIGS. 2066A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0017_1;

FIGS. 2067A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0016_1;

FIGS. 2068A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0015_1;

FIGS. 2069A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0014_1;

FIGS. 2070A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0013_1;

FIGS. 2071A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0012_1;

FIGS. 2072A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0011_1;

FIGS. 2073A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0010_1;

FIGS. 2074A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type E_PDF_VCI_FILL8_17S2_0009_1;

FIGS. 2075A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0071_1;

FIGS. 2076A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0070_1;

FIGS. 2077A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0069_1;

FIGS. 2078A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0068_1;

FIGS. 2079A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0067_1;

FIGS. 2080A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0066_1;

FIGS. 2081A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0065_1;

FIGS. 2082A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0064_1;

FIGS. 2083A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL16_24S1_0063_1;

FIGS. 2084A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0031_1;

FIGS. 2085A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0030_1;

FIGS. 2086A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0029_1;

FIGS. 2087A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0028_1;

FIGS. 2088A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0027_1;

FIGS. 2089A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0028_1;

FIGS. 2090A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0026_1;

FIGS. 2091A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0027_1;

FIGS. 2092A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0025_1;

FIGS. 2093A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0026_1;

FIGS. 2094A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0024_1;

FIGS. 2095A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0025_1;

FIGS. 2096A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL64_24S1_0023_1;

FIGS. 2097A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0024_1;

FIGS. 2098A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0023_1;

FIGS. 2099A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0022_1;

FIGS. 2100A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0021_1;

FIGS. 2101A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL08_24S1_0020_1;

FIGS. 2102A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0028_1;

FIGS. 2103A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0027_1;

FIGS. 2104A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0026_1;

FIGS. 2105A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0025_1;

FIGS. 2106A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0024_1;

FIGS. 2107A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0023_1;

FIGS. 2108A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0022_1;

FIGS. 2109A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0021_1;

FIGS. 2110A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type F_PDF_VCI_FILL32_24S1_0020_1;

FIGS. 2111A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30001C2_001;

FIGS. 2112A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3000BC2_011;

FIGS. 2113A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30015C2_021;

FIGS. 2114A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30016C2_022;

FIGS. 2115A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30020C2_032;

FIGS. 2116A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3002AC2_042;

FIGS. 2117A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30001C4_001;

FIGS. 2118A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30013C4_019;

FIGS. 2119A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30014C4_020;

FIGS. 2120A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30026C4_038;

FIGS. 2121A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30001C6_001;

FIGS. 2122A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3000BC6_011;

FIGS. 2123A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30015C6_021;

FIGS. 2124A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30016C6_022;

FIGS. 2125A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30020C6_032;

FIGS. 2126A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3002AC6_042;

FIGS. 2127A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30001C8_001;

FIGS. 2128A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3000BC8_011;

FIGS. 2129A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30015C8_021;

FIGS. 2130A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30016C8_022;

FIGS. 2131A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S30020C8_032;

FIGS. 2132A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type I_V421_VCI_20S3002AC8_042;

FIGS. 2133A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S282_0134_1;

FIGS. 2134A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S282_0069_1;

FIGS. 2135A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S282_0068_1;

FIGS. 2136A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S163_300_1;

FIGS. 2137A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S163_325_1;

FIGS. 2138A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S162_269_1;

FIGS. 2139A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S162_289_1;

FIGS. 2140A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S164_341_1;

FIGS. 2141A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S164_361_1;

FIGS. 2142A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S165_372_1;

FIGS. 2143A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S165_397_1;

FIGS. 2144A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S166_413_1;

FIGS. 2145A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S166_433_1;

FIGS. 2146A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S167_444_1;

FIGS. 2147A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCVE_7S167_469_1;

FIGS. 2148A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S283_0134_1;

FIGS. 2149A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S283_0069_1;

FIGS. 2150A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S283_0068_1;

FIGS. 2151A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S281_0085_1;

FIGS. 2152A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S281_0002_1;

FIGS. 2153A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S281_0001_1;

FIGS. 2154A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S280_0170_1;

FIGS. 2155A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S280_0087_1;

FIGS. 2156A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type J_PDF_VCI_VFILLCV8_7S280_0086_1;

FIGS. 2157A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200016C_01;

FIGS. 2158A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200226C_34;

FIGS. 2159A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200436C_67;

FIGS. 2160A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2000170_01;

FIGS. 2161A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2002270_34;

FIGS. 2162A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2004370_67;

FIGS. 2163A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200016E_01;

FIGS. 2164A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200226E_34;

FIGS. 2165A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200436E_67;

FIGS. 2166A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2000172_01;

FIGS. 2167A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2002272_34;

FIGS. 2168A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_2004372_67;

FIGS. 2169A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_3000148_01;

FIGS. 2170A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_3000248_02;

FIGS. 2171A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200019E_01;

FIGS. 2172A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200229E_34;

FIGS. 2173A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_200439E_67;

FIGS. 2174A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_20001A0_01;

FIGS. 2175A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_20022A0_34;

FIGS. 2176A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type K_V549_PDF_VCI_20043A0_67;

FIGS. 2177A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10001F5_01;

FIGS. 2178A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_1000DF5_13;

FIGS. 2179A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10019F5_25;

FIGS. 2180A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10001F6_01;

FIGS. 2181A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_1000DF6_13;

FIGS. 2182A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10019F6_25;

FIGS. 2183A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10001F7_01;

FIGS. 2184A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_1000DF7_13;

FIGS. 2185A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_E_PDF_VCI_10019F7_25;

FIGS. 2186A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1000142_01;

FIGS. 2187A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1002242_34;

FIGS. 2188A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1004342_67;

FIGS. 2189A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1000146_01;

FIGS. 2190A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1002246_34;

FIGS. 2191A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1004346_67;

FIGS. 2192A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1000140_01;

FIGS. 2193A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1002240_34;

FIGS. 2194A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1004340_67;

FIGS. 2195A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1000144_01;

FIGS. 2196A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1002244_34;

FIGS. 2197A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_B_PDF_VCI_1004344_67;

FIGS. 2198A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_M_PDF_VCI_3000148_01;

FIGS. 2199A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type L_V54C_M_PDF_VCI_3000248_02;

FIGS. 2200A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10001F5_01;

FIGS. 2201A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_1000DF5_13;

FIGS. 2202A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10019F5_25;

FIGS. 2203A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10001F6_01;

FIGS. 2204A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_1000DF6_13;

FIGS. 2205A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10019F6_25;

FIGS. 2206A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10001F7_01;

FIGS. 2207A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_1000DF7_13;

FIGS. 2208A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54A_PDF_VCI_10019F7_25;

FIGS. 2209A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1002142_33;

FIGS. 2210A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1002242_34;

FIGS. 2211A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1002342_35;

FIGS. 2212A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1000146_01;

FIGS. 2213A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1001246_18;

FIGS. 2214A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1004346_67;

FIGS. 2215A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1000140_01;

FIGS. 2216A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1002240_34;

FIGS. 2217A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1004340_67;

FIGS. 2218A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1000144_01;

FIGS. 2219A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1002244_34;

FIGS. 2220A-C respectively depict plan views of—(A) all layers; (B) NWELL, AA, GATE, GATECNT, TS, and AACNT layers; (C) V0, and M1 layers—of an exemplary M1-V0-via-open-configured, NCEM-enabled fill cell of type M_V54B_PDF_VCI_1004344_67;

FIGS. 2221A-B respectively depict plan views of—(A) all layers; (B) V0, M1, V1, and M2 layers—of an exemplary M2-V1-via-open-configured, NCEM-enabled fill cell of type K_V549_PDF_VCI_2000176_01;

FIGS. 2222A-B respectively depict plan views of—(A) all layers; (B) V0, M1, V1, and M2 layers—of an exemplary M2-V1-via-open-configured, NCEM-enabled fill cell of type K_V549_PDF_VCI_2002276_34;

FIGS. 2223A-B respectively depict plan views of—(A) all layers; (B) V0, M1, V1, and M2 layers—of an exemplary M2-V1-via-open-configured, NCEM-enabled fill cell of type K_V549_PDF_VCI_2004376_67;

FIGS. 2224A-B respectively depict plan views of—(A) all layers; (B) V0, M1, V1, and M2 layers—of an exemplary M2-V1-via-open-configured, NCEM-enabled fill cell of type K_V549_PDF_VCI_2000178_01;

FIGS. 2225A-B respectively depict plan views of—(A) all layers; (B) V0, M1, V1, and M2 layers—of an exemplary M2-V1-via-open-configured, NCEM-enabled fill cell of type K_V549_PDF_VCI_2002278_34;

FIGS. 2226A-B respectively depict plan views of—(A) all layers; (B) V0, M1, V1, and M2 layers—of an exemplary M2-V1-via-open-configured, NCEM-enabled fill cell of type K_V549_PDF_VCI_2004378_67;

FIGS. 2227A-B respectively depict plan views of—(A) all layers; (B) V0, M1, V1, and M2 layers—of an exemplary M2-V1-via-open-configured, NCEM-enabled fill cell of type L_V54C_E_PDF_VCI_10001FD_01;

FIGS. 2228A-B respectively depict plan views of—(A) all layers; (B) V0, M1, V1, and M2 layers—of an exemplary M2-V1-via-open-configured, NCEM-enabled fill cell of type L_V54C_E_PDF_VCI_1000DFD_13;

FIGS. 2229A-B respectively depict plan views of—(A) all layers; (B) V0, M1, V1, and M2 layers—of an exemplary M2-V1-via-open-configured, NCEM-enabled fill cell of type L_V54C_E_PDF_VCI_10019FD_25;

FIGS. 2230A-B respectively depict plan views of—(A) all layers; (B) V0, M1, V1, and M2 layers—of an exemplary M2-V1-via-open-configured, NCEM-enabled fill cell of type L_V54C_E_PDF_VCI_10001FE_01;

FIGS. 2231A-B respectively depict plan views of—(A) all layers; (B) V0, M1, V1, and M2 layers—of an exemplary M2-V1-via-open-configured, NCEM-enabled fill cell of type L_V54C_E_PDF_VCI_1000DFE_13;

FIGS. 2232A-B respectively depict plan views of—(A) all layers; (B) V0, M1, V1, and M2 layers—of an exemplary M2-V1-via-open-configured, NCEM-enabled fill cell of type L_V54C_E_PDF_VCI_10019FE_25;

FIGS. 2233A-B respectively depict plan views of—(A) all layers; (B) V0, M1, V1, and M2 layers—of an exemplary M2-V1-via-open-configured, NCEM-enabled fill cell of type L_V54C_E_PDF_VCI_10001FF_01;

FIGS. 2234A-B respectively depict plan views of—(A) all layers; (B) V0, M1, V1, and M2 layers—of an exemplary M2-V1-via-open-configured, NCEM-enabled fill cell of type L_V54C_E_PDF_VCI_1000DFF_13;

FIGS. 2235A-B respectively depict plan views of—(A) all layers; (B) V0, M1, V1, and M2 layers—of an exemplary M2-V1-via-open-configured, NCEM-enabled fill cell of type L_V54C_E_PDF_VCI_10019FF_25;

FIGS. 2236A-B respectively depict plan views of—(A) all layers; (B) V0, M1, V1, and M2 layers—of an exemplary M2-V1-via-open-configured, NCEM-enabled fill cell of type L_V54C_B_PDF_VCI_100014A_01;

FIGS. 2237A-B respectively depict plan views of—(A) all layers; (B) V0, M1, V1, and M2 layers—of an exemplary M2-V1-via-open-configured, NCEM-enabled fill cell of type L_V54C_B_PDF_VCI_100224A_34;

FIGS. 2238A-B respectively depict plan views of—(A) all layers; (B) V0, M1, V1, and M2 layers—of an exemplary M2-V1-via-open-configured, NCEM-enabled fill cell of type L_V54C_B_PDF_VCI_100434A_67;

FIGS. 2239A-B respectively depict plan views of—(A) all layers; (B) V0, M1, V1, and M2 layers—of an exemplary M2-V1-via-open-configured, NCEM-enabled fill cell of type L_V54C_B_PDF_VCI_100014C_01;

FIGS. 2240A-B respectively depict plan views of—(A) all layers; (B) V0, M1, V1, and M2 layers—of an exemplary M2-V1-via-open-configured, NCEM-enabled fill cell of type L_V54C_B_PDF_VCI_100224C_34;

FIGS. 2241A-B respectively depict plan views of—(A) all layers; (B) V0, M1, V1, and M2 layers—of an exemplary M2-V1-via-open-configured, NCEM-enabled fill cell of type L_V54C_B_PDF_VCI_100434C_67;

FIGS. 2242A-B respectively depict plan views of—(A) all layers; (B) V0, M1, V1, and M2 layers—of an exemplary M2-V1-via-open-configured, NCEM-enabled fill cell of type M_V54A_PDF_VCI_10001FD_01;

FIGS. 2243A-B respectively depict plan views of—(A) all layers; (B) V0, M1, V1, and M2 layers—of an exemplary M2-V1-via-open-configured, NCEM-enabled fill cell of type M_V54A_PDF_VCI_1000DFD_13;

FIGS. 2244A-B respectively depict plan views of—(A) all layers; (B) V0, M1, V1, and M2 layers—of an exemplary M2-V1-via-open-configured, NCEM-enabled fill cell of type M_V54A_PDF_VCI_10019FD_25;

FIGS. 2245A-B respectively depict plan views of—(A) all layers; (B) V0, M1, V1, and M2 layers—of an exemplary M2-V1-via-open-configured, NCEM-enabled fill cell of type M_V54A_PDF_VCI_10001FE_01;

FIGS. 2246A-B respectively depict plan views of—(A) all layers; (B) V0, M1, V1, and M2 layers—of an exemplary M2-V1-via-open-configured, NCEM-enabled fill cell of type M_V54A_PDF_VCI_1000DFE_13;

FIGS. 2247A-B respectively depict plan views of—(A) all layers; (B) V0, M1, V1, and M2 layers—of an exemplary M2-V1-via-open-configured, NCEM-enabled fill cell of type M_V54A_PDF_VCI_10019FE_25;

FIGS. 2248A-B respectively depict plan views of—(A) all layers; (B) V0, M1, V1, and M2 layers—of an exemplary M2-V1-via-open-configured, NCEM-enabled fill cell of type M_V54A_PDF_VCI_10001FF_01;

FIGS. 2249A-B respectively depict plan views of—(A) all layers; (B) V0, M1, V1, and M2 layers—of an exemplary M2-V1-via-open-configured, NCEM-enabled fill cell of type M_V54A_PDF_VCI_1000DFF_13;

FIGS. 2250A-B respectively depict plan views of—(A) all layers; (B) V0, M1, V1, and M2 layers—of an exemplary M2-V1-via-open-configured, NCEM-enabled fill cell of type M_V54A_PDF_VCI_10019FF_25;

FIGS. 2251A-B respectively depict plan views of—(A) all layers; (B) V0, M1, V1, and M2 layers—of an exemplary M2-V1-via-open-configured, NCEM-enabled fill cell of type M_V54B_PDF_VCI_100014A_01;

FIGS. 2252A-B respectively depict plan views of—(A) all layers; (B) V0, M1, V1, and M2 layers—of an exemplary M2-V1-via-open-configured, NCEM-enabled fill cell of type M_V54B_PDF_VCI_100224A_34;

FIGS. 2253A-B respectively depict plan views of—(A) all layers; (B) V0, M1, V1, and M2 layers—of an exemplary M2-V1-via-open-configured, NCEM-enabled fill cell of type M_V54B_PDF_VCI_100434A_67;

FIGS. 2254A-B respectively depict plan views of—(A) all layers; (B) V0, M1, V1, and M2 layers—of an exemplary M2-V1-via-open-configured, NCEM-enabled fill cell of type M_V54B_PDF_VCI_100114C_17;

FIGS. 2255A-B respectively depict plan views of—(A) all layers; (B) V0, M1, V1, and M2 layers—of an exemplary M2-V1-via-open-configured, NCEM-enabled fill cell of type M_V54B_PDF_VCI_100224C_34;

FIGS. 2256A-B respectively depict plan views of—(A) all layers; (B) V0, M1, V1, and M2 layers—of an exemplary M2-V1-via-open-configured, NCEM-enabled fill cell of type M_V54B_PDF_VCI_100234C_35;

FIGS. 2257A-B respectively depict plan views of—(A) all layers; (B) V1, M2, V2, and M3 layers—of an exemplary M3-V2-via-open-configured, NCEM-enabled fill cell of type K_V549_PDF_VCI_200017C_01;

FIGS. 2258A-B respectively depict plan views of—(A) all layers; (B) V1, M2, V2, and M3 layers—of an exemplary M3-V2-via-open-configured, NCEM-enabled fill cell of type K_V549_PDF_VCI_200227C_34;

FIGS. 2259A-B respectively depict plan views of—(A) all layers; (B) V1, M2, V2, and M3 layers—of an exemplary M3-V2-via-open-configured, NCEM-enabled fill cell of type K_V549_PDF_VCI_200437C_67;

FIGS. 2260A-B respectively depict plan views of—(A) all layers; (B) V1, M2, V2, and M3 layers—of an exemplary M3-V2-via-open-configured, NCEM-enabled fill cell of type K_V549_PDF_VCI_200017E_01;

FIGS. 2261A-B respectively depict plan views of—(A) all layers; (B) V1, M2, V2, and M3 layers—of an exemplary M3-V2-via-open-configured, NCEM-enabled fill cell of type K_V549_PDF_VCI_200227E_34;

FIGS. 2262A-B respectively depict plan views of—(A) all layers; (B) V1, M2, V2, and M3 layers—of an exemplary M3-V2-via-open-configured, NCEM-enabled fill cell of type K_V549_PDF_VCI_200437E_67;

FIGS. 2263A-B respectively depict plan views of—(A) all layers; (B) V1, M2, V2, and M3 layers—of an exemplary M3-V2-via-open-configured, NCEM-enabled fill cell of type L_V54C_B_PDF_VCI_1000150_01;

FIGS. 2264A-B respectively depict plan views of—(A) all layers; (B) V1, M2, V2, and M3 layers—of an exemplary M3-V2-via-open-configured, NCEM-enabled fill cell of type L_V54C_B_PDF_VCI_1002250_34;

FIGS. 2265A-B respectively depict plan views of—(A) all layers; (B) V1, M2, V2, and M3 layers—of an exemplary M3-V2-via-open-configured, NCEM-enabled fill cell of type L_V54C_B_PDF_VCI_1004350_67;

FIGS. 2266A-B respectively depict plan views of—(A) all layers; (B) V1, M2, V2, and M3 layers—of an exemplary M3-V2-via-open-configured, NCEM-enabled fill cell of type L_V54C_B_PDF_VCI_1000152_01;

FIGS. 2267A-B respectively depict plan views of—(A) all layers; (B) V1, M2, V2, and M3 layers—of an exemplary M3-V2-via-open-configured, NCEM-enabled fill cell of type L_V54C_B_PDF_VCI_1002252_34;

FIGS. 2268A-B respectively depict plan views of—(A) all layers; (B) V1, M2, V2, and M3 layers—of an exemplary M3-V2-via-open-configured, NCEM-enabled fill cell of type L_V54C_B_PDF_VCI_1004352_67;

FIGS. 2269A-B respectively depict plan views of—(A) all layers; (B) V1, M2, V2, and M3 layers—of an exemplary M3-V2-via-open-configured, NCEM-enabled fill cell of type M_V54B_PDF_VCI_1000150_01;

FIGS. 2270A-B respectively depict plan views of—(A) all layers; (B) V1, M2, V2, and M3 layers—of an exemplary M3-V2-via-open-configured, NCEM-enabled fill cell of type M_V54B_PDF_VCI_1002250_34;

FIGS. 2271A-B respectively depict plan views of—(A) all layers; (B) V1, M2, V2, and M3 layers—of an exemplary M3-V2-via-open-configured, NCEM-enabled fill cell of type M_V54B_PDF_VCI_1004350_67;

FIGS. 2272A-B respectively depict plan views of—(A) all layers; (B) V1, M2, V2, and M3 layers—of an exemplary M3-V2-via-open-configured, NCEM-enabled fill cell of type M_V54B_PDF_VCI_1001152_17;

FIGS. 2273A-B respectively depict plan views of—(A) all layers; (B) V1, M2, V2, and M3 layers—of an exemplary M3-V2-via-open-configured, NCEM-enabled fill cell of type M_V54B_PDF_VCI_1002252_34;

FIGS. 2274A-B respectively depict plan views of—(A) all layers; (B) V1, M2, V2, and M3 layers—of an exemplary M3-V2-via-open-configured, NCEM-enabled fill cell of type M_V54B_PDF_VCI_1002352_35;

FIGS. 2275A-B respectively depict plan views of—(A) all layers; (B) M3, V3, M4, V4, and M5 layers—of an exemplary M4-V3-via-open-configured, NCEM-enabled fill cell of type K_V549_PDF_VCI_2000180_01;

FIGS. 2276A-B respectively depict plan views of—(A) all layers; (B) M3, V3, M4, V4, and M5 layers—of an exemplary M4-V3-via-open-configured, NCEM-enabled fill cell of type K_V549_PDF_VCI_2002C80_44;

FIGS. 2277A-B respectively depict plan views of—(A) all layers; (B) M3, V3, M4, V4, and M5 layers—of an exemplary M4-V3-via-open-configured, NCEM-enabled fill cell of type K_V549_PDF_VCI_2005780_87;

FIGS. 2278A-B respectively depict plan views of—(A) all layers; (B) M3, V3, M4, V4, and M5 layers—of an exemplary M4-V3-via-open-configured, NCEM-enabled fill cell of type K_V549_PDF_VCI_20001B2_01;

FIGS. 2279A-B respectively depict plan views of—(A) all layers; (B) M3, V3, M4, V4, and M5 layers—of an exemplary M4-V3-via-open-configured, NCEM-enabled fill cell of type K_V549_PDF_VCI_2002C82_44;

FIGS. 2280A-B respectively depict plan views of—(A) all layers; (B) M3, V3, M4, V4, and M5 layers—of an exemplary M4-V3-via-open-configured, NCEM-enabled fill cell of type K_V549_PDF_VCI_2005782_87;

FIGS. 2281A-B respectively depict plan views of—(A) all layers; (B) M3, V3, M4, V4, and M5 layers—of an exemplary M4-V3-via-open-configured, NCEM-enabled fill cell of type K_V549_PDF_VCI_3000155_01;

FIGS. 2282A-B respectively depict plan views of—(A) all layers; (B) M3, V3, M4, V4, and M5 layers—of an exemplary M4-V3-via-open-configured, NCEM-enabled fill cell of type K_V549_PDF_VCI_3002955_41;

FIGS. 2283A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1000154_01;

FIGS. 2284A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1002C54_44;

FIGS. 2285A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1005754_87;

FIGS. 2286A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1000156_01;

FIGS. 2287A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1002C56_44;

FIGS. 2288A-B respectively depict plan views of—(A) all layers; (B) M3, V3, M4, V4, and M5 layers—of an exemplary M4-V3-via-open-configured, NCEM-enabled fill cell of type L_V54C_B_PDF_VCI_1005756_87;

FIGS. 2289A-B respectively depict plan views of—(A) all layers; (B) M3, V3, M4, V4, and M5 layers—of an exemplary M4-V3-via-open-configured, NCEM-enabled fill cell of type L_V54C_M_PDF_VCI_3000155_01;

FIGS. 2290A-B respectively depict plan views of—(A) all layers; (B) M3, V3, M4, V4, and M5 layers—of an exemplary M4-V3-via-open-configured, NCEM-enabled fill cell of type L_V54C_M_PDF_VCI_3002955_41;

FIGS. 2291A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1000154_01;

FIGS. 2292A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1002C54_44;

FIGS. 2293A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1005754_87;

FIGS. 2294A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1001456_20;

FIGS. 2295A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1004E56_78;

FIGS. 2296A-B respectively depict plan views of—(A) all layers; (B) M3, V3, M4, V4, and M5 layers—of an exemplary M4-V3-via-open-configured, NCEM-enabled fill cell of type M_V54B_PDF_VCI_1004F56_79;

FIGS. 2297A-B respectively depict plan views of—(A) all layers; (B) M3, V3, M4, V4, and M5 layers—of an exemplary M5-V4-via-open-configured, NCEM-enabled fill cell of type K_V549_PDF_VCI_200018A_01;

FIGS. 2298A-B respectively depict plan views of—(A) all layers; (B) M3, V3, M4, V4, and M5 layers—of an exemplary M5-V4-via-open-configured, NCEM-enabled fill cell of type K_V549_PDF_VCI_2003A8A_58;

FIGS. 2299A-B respectively depict plan views of—(A) all layers; (B) M3, V3, M4, V4, and M5 layers—of an exemplary M5-V4-via-open-configured, NCEM-enabled fill cell of type K_V549_PDF_VCI_200738A_115;

FIGS. 2300A-B respectively depict plan views of—(A) all layers; (B) M3, V3, M4, V4, and M5 layers—of an exemplary M5-V4-via-open-configured, NCEM-enabled fill cell of type K_V549_PDF_VCI_200018C_01;

FIGS. 2301A-B respectively depict plan views of—(A) all layers; (B) M3, V3, M4, V4, and M5 layers—of an exemplary M5-V4-via-open-configured, NCEM-enabled fill cell of type K_V549_PDF_VCI_2003A8C_58;

FIGS. 2302A-B respectively depict plan views of—(A) all layers; (B) M3, V3, M4, V4, and M5 layers—of an exemplary M5-V4-via-open-configured, NCEM-enabled fill cell of type K_V549_PDF_VCI_200738C_115;

FIGS. 2303A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_100015E_01;

FIGS. 2304A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_1003A5E_58;

FIGS. 2305A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_100735E_115;

FIGS. 2306A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_1000160_01;

FIGS. 2307A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_1003A60_58;

FIGS. 2308A-B respectively depict plan views of—(A) all layers; (B) M3, V3, M4, V4, and M5 layers—of an exemplary M5-V4-via-open-configured, NCEM-enabled fill cell of type L_V54C_B_PDF_VCI_1007360_115;

FIGS. 2309A-B respectively depict plan views of—(A) all layers; (B) M3, V3, M4, V4, and M5 layers—of an exemplary M5-V4-via-open-configured, NCEM-enabled fill cell of type M_V54B_PDF_VCI_100015E_01;

FIGS. 2310A-B respectively depict plan views of—(A) all layers; (B) M3, V3, M4, V4, and M5 layers—of an exemplary M5-V4-via-open-configured, NCEM-enabled fill cell of type M_V54B_PDF_VCI_1003A5E_58;

FIGS. 2311A-B respectively depict plan views of—(A) all layers; (B) M3, V3, M4, V4, and M5 layers—of an exemplary M5-V4-via-open-configured, NCEM-enabled fill cell of type M_V54B_PDF_VCI_100735E_115;

FIGS. 2312A-B respectively depict plan views of—(A) all layers; (B) M3, V3, M4, V4, and M5 layers—of an exemplary M5-V4-via-open-configured, NCEM-enabled fill cell of type M_V54B_PDF_VCI_1001460_20;

FIGS. 2313A-B respectively depict plan views of—(A) all layers; (B) M3, V3, M4, V4, and M5 layers—of an exemplary M5-V4-via-open-configured, NCEM-enabled fill cell of type M_V54B_PDF_VCI_1004E60_78;

FIGS. 2314A-B respectively depict plan views of—(A) all layers; (B) M3, V3, M4, V4, and M5 layers—of an exemplary M5-V4-via-open-configured, NCEM-enabled fill cell of type M_V54B_PDF_VCI_1004F60_79;

FIGS. 2315A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000194_01;

FIGS. 2316A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000196_01;

FIGS. 2317A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000198_01;

FIGS. 2318A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019A_01;

FIGS. 2319A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019C_01;

FIGS. 2320A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019E_01;

FIGS. 2321A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_20001A0_01;

FIGS. 2322A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_20001A2_01;

FIGS. 2323A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_20001A4_01;

FIGS. 2324A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_20001A6_01;

FIGS. 2325A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000195_01;

FIGS. 2326A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000197_01;

FIGS. 2327A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_2000199_01;

FIGS. 2328A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019B_01;

FIGS. 2329A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019D_01;

FIGS. 2330A-C respectively depict plan views of—(A) all layers; (B) NWELL, AA, GATE, GATECNT, TS, and AACNT layers; (C) V0, and M1 layers—of an exemplary TS-AA-via-open-configured, NCEM-enabled fill cell of type G_V931_PDF_VCI_200019F_01;

FIGS. 2331A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL08_19S2000194;

FIGS. 2332A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL12_19S2000294;

FIGS. 2333A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL16_19S2000394;

FIGS. 2334A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL08_19S2000494;

FIGS. 2335A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL12_19S2000594;

FIGS. 2336A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL16_19S2000694;

FIGS. 2337A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL08_19S2000794;

FIGS. 2338A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL12_19S2000894;

FIGS. 2339A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL16_19S2000994;

FIGS. 2340A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL08_19S2000A94;

FIGS. 2341A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL12_19S2000B94;

FIGS. 2342A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type I_PDF_VCI_FILL16_19S2000C94;

FIGS. 2343A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type K_V549_PDF_VCI_3000153_01;

FIGS. 2344A-C respectively depict plan views of—(A) all layers; (B) NWELL, AA, GATE, GATECNT, TS, and AACNT layers; (C) V0, and M1 layers—of an exemplary V0-via-open-configured, NCEM-enabled fill cell of type L_V54C_M_PDF_VCI_3000153_01;

FIGS. 2345A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2000124_01;

FIGS. 2346A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2001624_22;

FIGS. 2347A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2002B24_43;

FIGS. 2348A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2002C24_44;

FIGS. 2349A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2004124_65;

FIGS. 2350A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type C_V682_PDF_VCI_08_2005624_86;

FIGS. 2351A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S285_0021_1;

FIGS. 2352A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S285_0017_1;

FIGS. 2353A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S285_0066_1;

FIGS. 2354A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S284_0138_1;

FIGS. 2355A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S284_0071_1;

FIGS. 2356A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type J_PDF_VCI_VFILLCV8_7S284_0070_1;

FIGS. 2357A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2000162_01;

FIGS. 2358A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2001862_24;

FIGS. 2359A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2002F62_47;

FIGS. 2360A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2000164_01;

FIGS. 2361A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2002264_34;

FIGS. 2362A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type K_V549_PDF_VCI_2004364_67;

FIGS. 2363A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1000136_01;

FIGS. 2364A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1001836_24;

FIGS. 2365A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1002F36_47;

FIGS. 2366A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1000138_01;

FIGS. 2367A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1002238_34;

FIGS. 2368A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type L_V54C_B_PDF_VCI_1004338_67;

FIGS. 2369A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1000136_01;

FIGS. 2370A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1001836_24;

FIGS. 2371A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1002F36_47;

FIGS. 2372A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1000138_01;

FIGS. 2373A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1001238_18;

FIGS. 2374A-C respectively depict plan views of—(A) all layers; (B) NWELL, AA, GATE, GATECNT, TS, and AACNT layers; (C) V0, and M1 layers—of an exemplary V0-AACNT-via-open-configured, NCEM-enabled fill cell of type M_V54B_PDF_VCI_1004338_67;

FIGS. 2375A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2000136_01;

FIGS. 2376A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2001636_22;

FIGS. 2377A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2002B36_43;

FIGS. 2378A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2002C36_44;

FIGS. 2379A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2004136_65;

FIGS. 2380A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2005636_86;

FIGS. 2381A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2005736_87;

FIGS. 2382A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2006C36_108;

FIGS. 2383A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2008136_129;

FIGS. 2384A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2008236_130;

FIGS. 2385A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2009736_151;

FIGS. 2386A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200AC36_172;

FIGS. 2387A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200AD36_173;

FIGS. 2388A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200C236_194;

FIGS. 2389A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200D736_215;

FIGS. 2390A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200D836_216;

FIGS. 2391A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_200ED36_237;

FIGS. 2392A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2010236_258;

FIGS. 2393A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2000BB0_11;

FIGS. 2394A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_20020B0_32;

FIGS. 2395A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_20035B0_53;

FIGS. 2396A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2004AB0_74;

FIGS. 2397A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_2005FB0_95;

FIGS. 2398A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type C_V682_PDF_VCI_08_20074B0_116;

FIGS. 2399A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type J_PDF_VCI_VFILLCV8_7S286_0194_1;

FIGS. 2400A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type J_PDF_VCI_VFILLCV8_7S286_0099_1;

FIGS. 2401A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type J_PDF_VCI_VFILLCV8_7S286_0098_1;

FIGS. 2402A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type J_PDF_VCI_VFILLCV8_7S287_0067_1;

FIGS. 2403A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type J_PDF_VCI_VFILLCV8_7S287_0066_1;

FIGS. 2404A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2000102_01;

FIGS. 2405A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2001002_16;

FIGS. 2406A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2001F02_31;

FIGS. 2407A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2002002_32;

FIGS. 2408A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2002F02_47;

FIGS. 2409A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2003E02_62;

FIGS. 2410A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2000168_01;

FIGS. 2411A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2002868_40;

FIGS. 2412A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2004F68_79;

FIGS. 2413A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_200016A_01;

FIGS. 2414A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_200286A_40;

FIGS. 2415A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2004F6A_79;

FIGS. 2416A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2000196_01;

FIGS. 2417A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2002896_40;

FIGS. 2418A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2004F96_79;

FIGS. 2419A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2000198_01;

FIGS. 2420A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2002898_40;

FIGS. 2421A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type K_V549_PDF_VCI_2004F98_79;

FIGS. 2422A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_100013C_01;

FIGS. 2423A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_100273C_39;

FIGS. 2424A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_1004D3C_77;

FIGS. 2425A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_100013E_01;

FIGS. 2426A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_100273E_39;

FIGS. 2427A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_B_PDF_VCI_1004D3E_77;

FIGS. 2428A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2000102_01;

FIGS. 2429A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2001002_16;

FIGS. 2430A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2001F02_31;

FIGS. 2431A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2002002_32;

FIGS. 2432A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2002F02_47;

FIGS. 2433A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type L_V54C_M_PDF_VCI_2003E02_62;

FIGS. 2434A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_100013C_01;

FIGS. 2435A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_100273C_39;

FIGS. 2436A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_1004D3C_77;

FIGS. 2437A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_100133E_19;

FIGS. 2438A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_100273E_39;

FIGS. 2439A-C respectively depict plan views of—(A) all layers; (B) NWELL, AA, GATE, GATECNT, TS, and AACNT layers; (C) V0, and M1 layers—of an exemplary V0-GATECNT-via-open-configured, NCEM-enabled fill cell of type M_V54B_PDF_VCI_100283E_40;

FIGS. 2440A-C respectively depict plan views of—(A) all layers; (B) NWELL, AA, GATE, GATECNT, TS, and AACNT layers; (C) V0, M1, V1, and M2 layers—of an exemplary V1-via-open-configured, NCEM-enabled fill cell of type K_V549_PDF_VCI_3000152_01;

FIGS. 2441A-C respectively depict plan views of—(A) all layers; (B) NWELL, AA, GATE, GATECNT, TS, and AACNT layers; (C) V0, M1, V1, and M2 layers—of an exemplary V1-via-open-configured, NCEM-enabled fill cell of type L_V54C_M_PDF_VCI_3000152_01;

FIGS. 2442A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10001F9_01;

FIGS. 2443A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10017F9_23;

FIGS. 2444A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_1002DF9_45;

FIGS. 2445A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10001FA_01;

FIGS. 2446A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10017FA_23;

FIGS. 2447A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_1002DFA_45;

FIGS. 2448A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10001FB_01;

FIGS. 2449A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_10017FB_23;

FIGS. 2450A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type L_V54C_E_PDF_VCI_1002DFB_45;

FIGS. 2451A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10001F9_01;

FIGS. 2452A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10017F9_23;

FIGS. 2453A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_1002DF9_45;

FIGS. 2454A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10001FA_01;

FIGS. 2455A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10017FA_23;

FIGS. 2456A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_1002DFA_45;

FIGS. 2457A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10001FB_01;

FIGS. 2458A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_10017FB_23;

FIGS. 2459A-C respectively depict plan views of—(A) all layers; (B) NWELL, AA, GATE, GATECNT, TS, and AACNT layers; (C) V0, M1, V1, and M2 layers—of an exemplary V1-M1-via-open-configured, NCEM-enabled fill cell of type M_V54A_PDF_VCI_1002DFB_45;

FIGS. 2460A-B respectively depict plan views of—(A) all layers; (B) M3, V3, M4, V4, and M5 layers—of an exemplary V3-via-open-configured, NCEM-enabled fill cell of type K_V549_PDF_VCI_3000154_01; and, FIGS. 2461A-B respectively depict plan views of—(A) all layers; (B) M3, V3, M4, V4, and M5 layers—of an exemplary V3-via-open-configured, NCEM-enabled fill cell of type L_V54C_M_PDF_VCI_3000154_01.

DESCRIPTION OF EXEMPLARY/PREFERRED EMBODIMENT(S)

Figure 1:
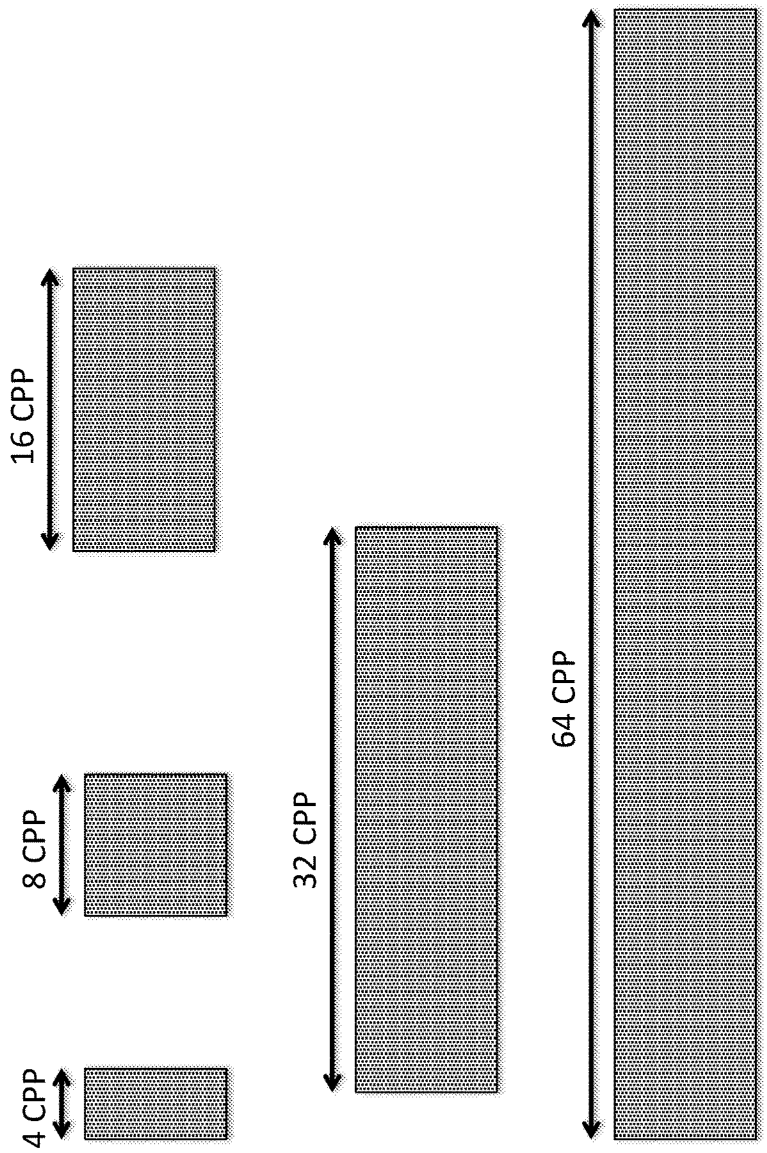
FIG. 1 depicts an outline of illustrative fill cells, suitable for use in connection certain embodiments of the invention.

Reference is now made to FIG. 1, which depicts an outline of illustrative fill cells suitable for use in connection certain embodiments of the invention, such fill cells are typically provided in a uniform height and various widths, traditionally multiples of the minimum contacted poly pitch (CPP) permitted by the fabrication process. FIG. 1 includes fill cells of width 4 CPP, 8 CPP, 16 CPP, 32 CPP, and 64 CPP, but any collection of widths—or just a single width—is possible. Furthermore, certain embodiments of the invention may include double or triple height fill cells, as well. As persons skilled in the art will appreciate, traditional fill cells include certain features necessary for compatibility with the logic cells used to form circuits on the chip. Such necessary features include a height that is consistent with logic cells in the library (or an integer multiple of that height), as well as power/ground rails that extend horizontally across the fill cells (traditionally, though not necessarily, at the top and bottom of each cell). Such necessary features are preferably maintained in the NCEM-enabled fill cells used in connection with the present invention.

Figure 2:
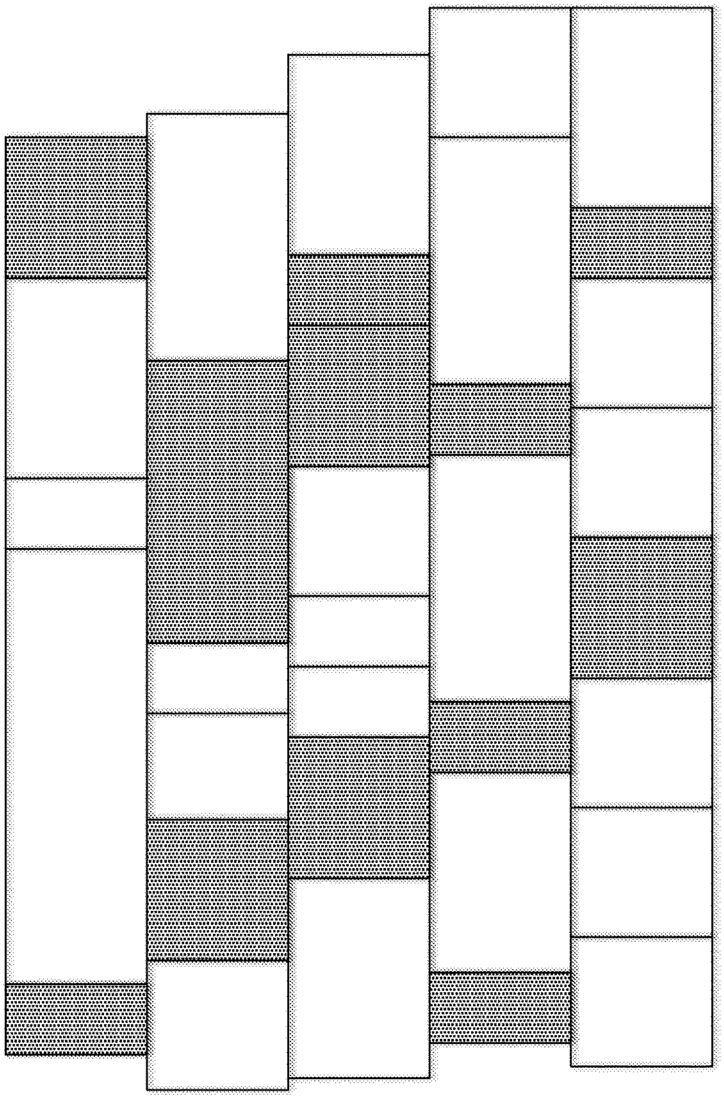
FIG. 2 depicts an exemplary standard cell logic section with (shaded) NCEM-enabled fill cells, of various widths.

Reference is now made to FIG. 2, which depicts an exemplary standard cell logic section with (shaded) NCEM-enabled fill cells, of various widths. As depicted, the NCEM-enabled fill cells are preferably instantiated wherever a traditional fill cell would otherwise be placed. However, the invention places no restriction on the distribution of such NCEM-enabled fill cells. While they would typically appear in each standard cell row, they need not. The fill cell placement can be regular, semi-regular (e.g., at least one fill cell every X nm, or every Y cells), or irregular. Two fill cells can be adjacent to each other. There may be some double height (or greater) fill cells. And the logic section may include both NCEM-enabled as well as other types of fill cells.

Figure 3:
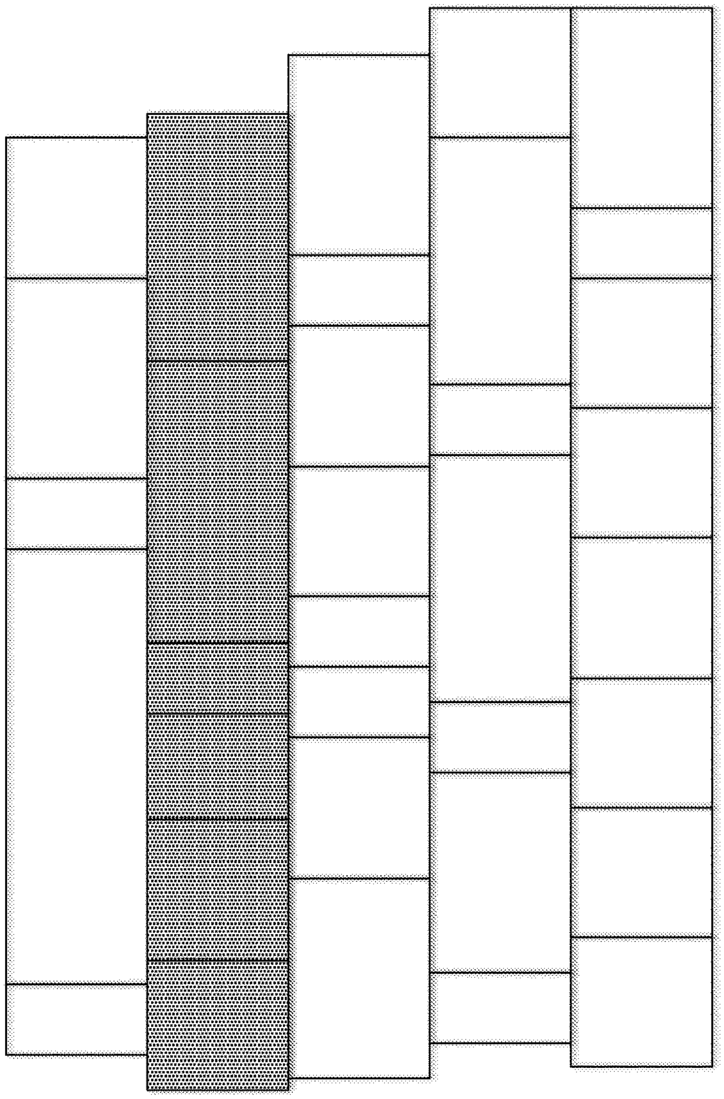
FIG. 3 depicts an exemplary standard cell logic section with a row (or portion thereof) that contains NCEM-enabled fill cells, of various widths.

Reference is now made to FIG. 3, which depicts an exemplary standard cell logic section with a row (or portion thereof) that contains NCEM-enabled fill cells, of various widths. As depicted, certain embodiments of the invention may include complete row(s), or contiguous portion(s) thereof, populated entirely with NCEM-enabled fill cells. Such row(s) may include fill cells of varying or fixed widths, and such row(s) may be adjacent or separated, and may be distributed regularly, semi-regularly or irregularly throughout the logic section.

Figure 4:
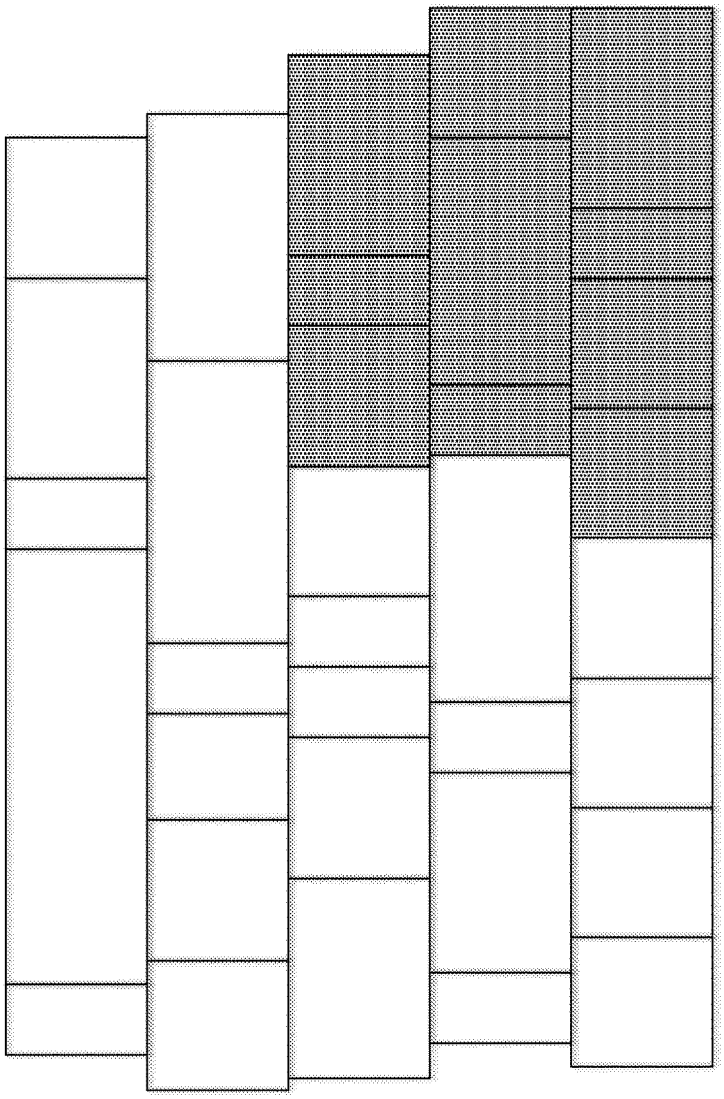
FIG. 4 depicts an exemplary standard cell logic section with a test block area (lower right portion) populated with NCEM-enabled fill cells, of various widths.

Reference is now made to FIG. 4, which depicts an exemplary standard cell logic section with a test block area (lower right portion) populated with NCEM-enabled fill cells, of various widths. Such test block section(s) need not be entirely contiguous, need not be generally rectangular or square, may include fill cells of a single width or multiple widths, and one or multiple heights.

Figure 5:
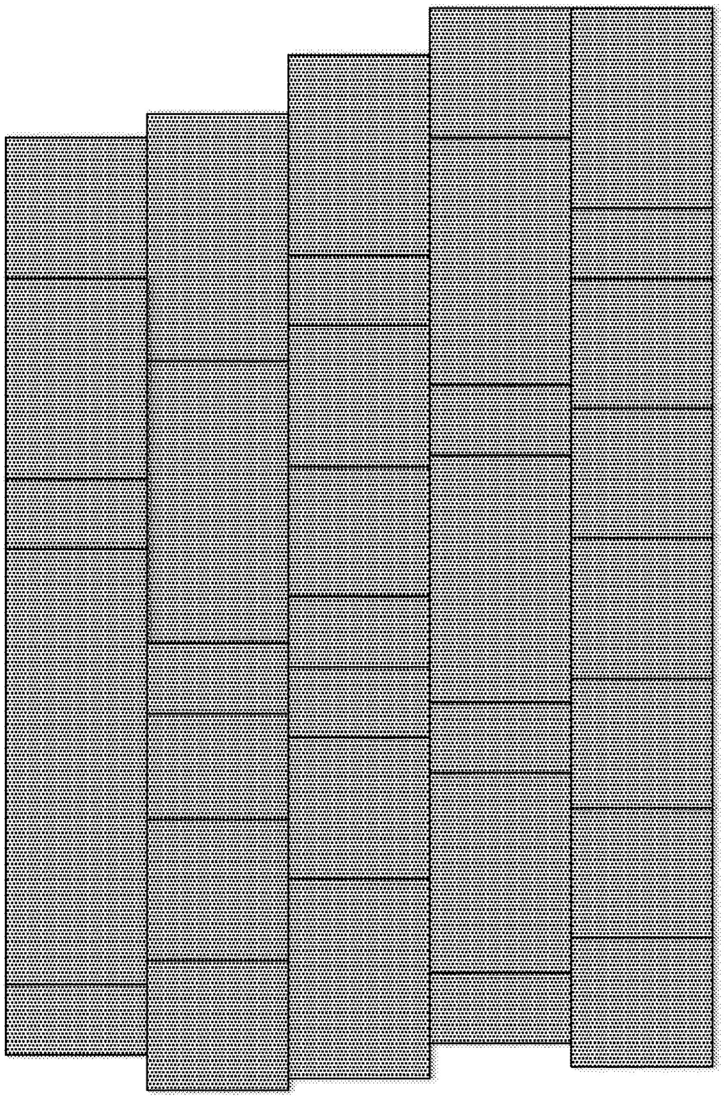
FIG. 5 depicts an exemplary portion of a test chip/wafer comprised of NCEM-enabled fill cells, of various widths.

Reference is now made to FIG. 5, which depicts an exemplary portion of a test chip/wafer comprised of NCEM-enabled fill cells, of various widths. Such test vehicles may comprise a die, a chip, a wafer, or a portion of any of these. Such test vehicles need not be entirely contiguous, may have any overall shape, and may include fill cells of a single width or multiple widths, and one or multiple heights.

Figure 6:
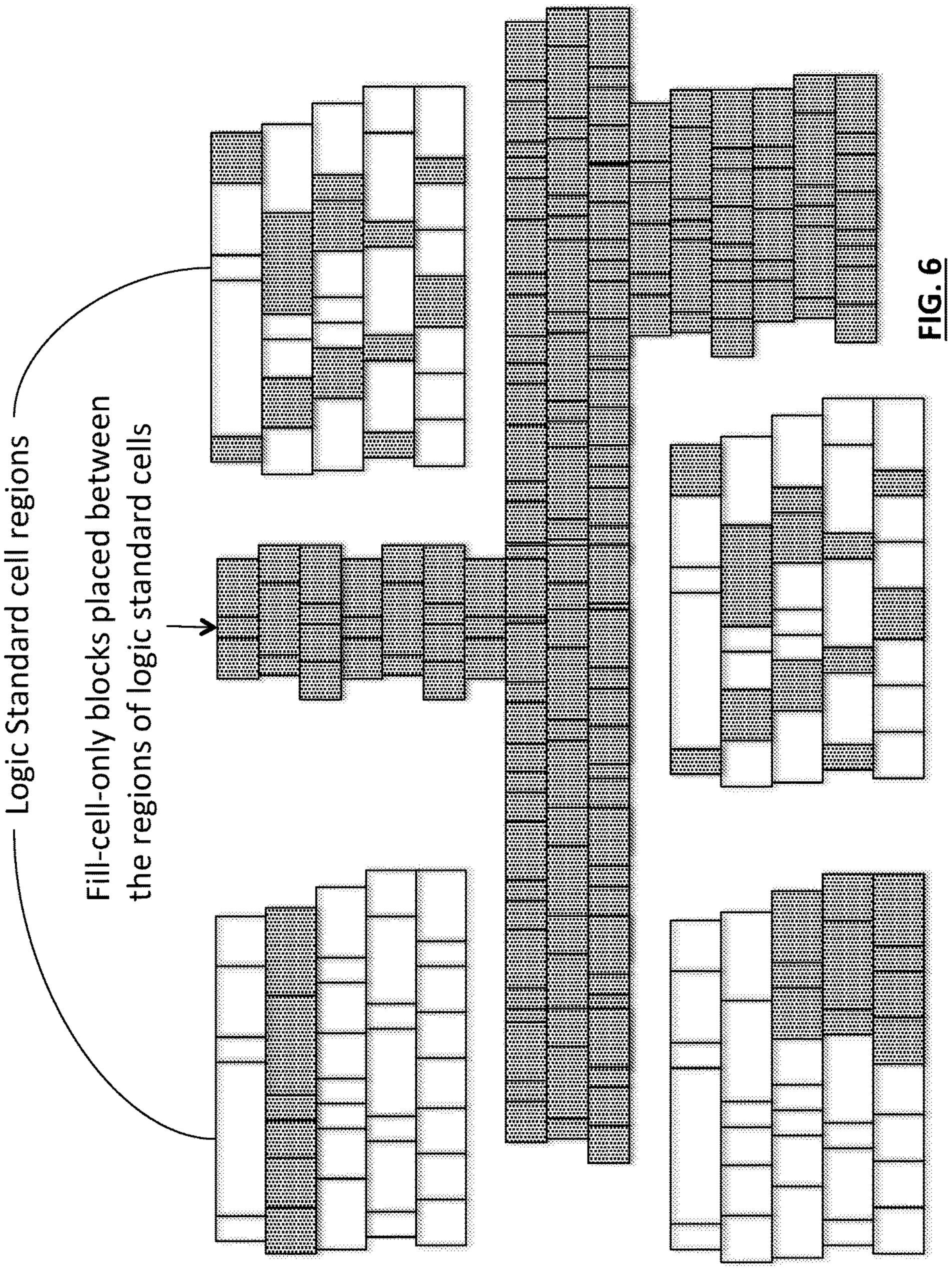
FIG. 6 conceptually depicts a portion of an exemplary chip/wafer in which a region comprised only (or almost only) of NCEM-enabled fill cells is positioned between two or more standard cell regions.

Reference is now made to FIG. 6, which conceptually depicts a portion of an exemplary chip/die/wafer with a region comprised only (or almost only) of NCEM-enabled fill cells positioned between two or more standard cell regions (such as those of FIGS. 2-5). As persons skilled in the art will appreciate, FIG. 6 illustrates how various embodiments of the invention may instantiate/distribute the inventive NCEM-enabled fill cells (and DOEs based on them) in any manner whatsoever, and that the distribution patterns—both regular and irregular—may vary throughout different regions of a chip or wafer.

As persons skilled in the art will appreciate, the configurations of FIGS. 2-5 and 6 are mere examples of many available possibilities, and are not intended to be limiting or exhaustive. Furthermore, such skilled persons will appreciate that any given die, chip or wafer may include a combination of these and/or other possible configurations.

Figure 7:
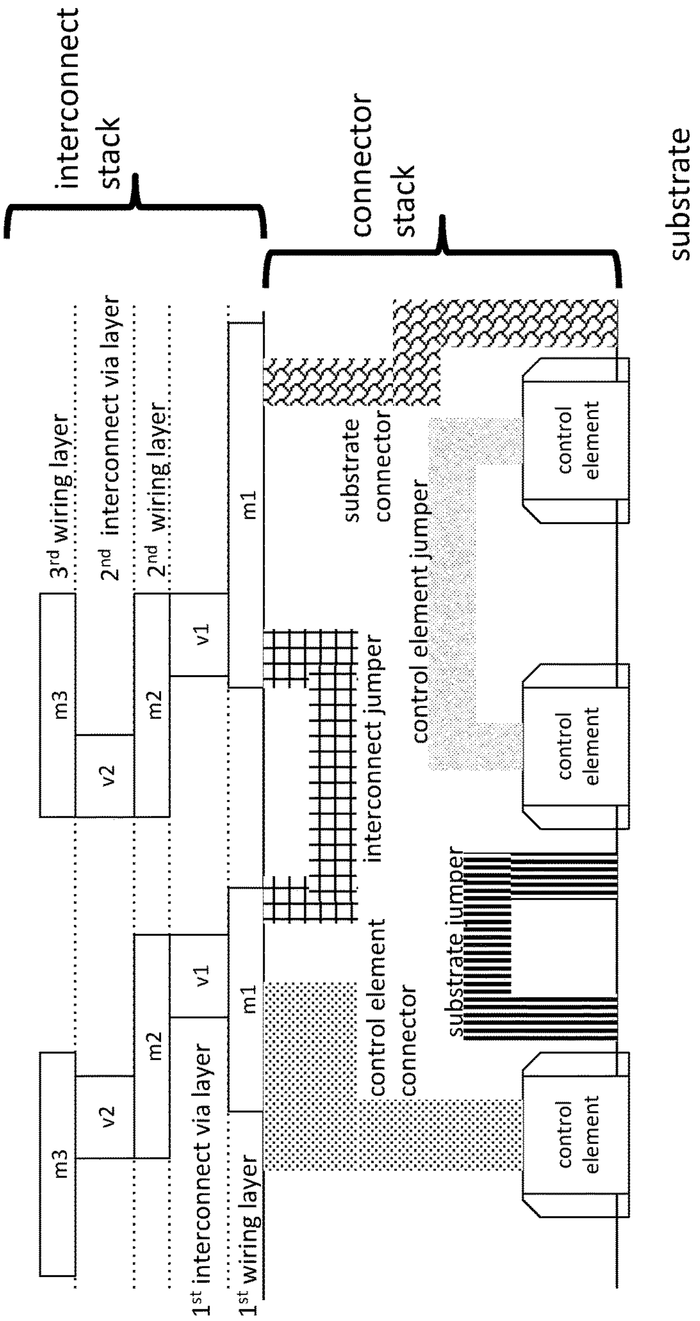
FIG. 7 depicts a cross-sectional, topological view of a monolithic IC structure.

Reference is now made to FIG. 7, which depicts cross-sectional, topological view of a monolithic IC structure to which the invention may be applied. This topological view depicts—from bottom to top—three vertically defined portions: (i) substrate; (ii) connector stack; and (iii) interconnect stack.

The substrate preferably comprises a wafer, die, or other portion of monocrystalline silicon, or another substrate suitable for forming semiconductor devices, such as silicon-on-insulator (SOI), Ge, C, GaAs, InP, GaInAs, AlAs, GaSb, (Ga,Mn)As, GaP, GaN, InAS, SiGe, SiSn, CdSe, CdTe, CdHgTe, ZnS, SiC, etc. Generally speaking, the substrate represents the object to which manufacturing steps (e.g., deposition, masking, etching, implantation) are initially applied, and is the object within which, or upon which, switching devices (e.g., FETs, bipolar transistors, photodiodes, magnetic devices, etc.) or storage devices (e.g., charged oxides, capacitors, phase change memories, etc.) are built.

Figure 8:
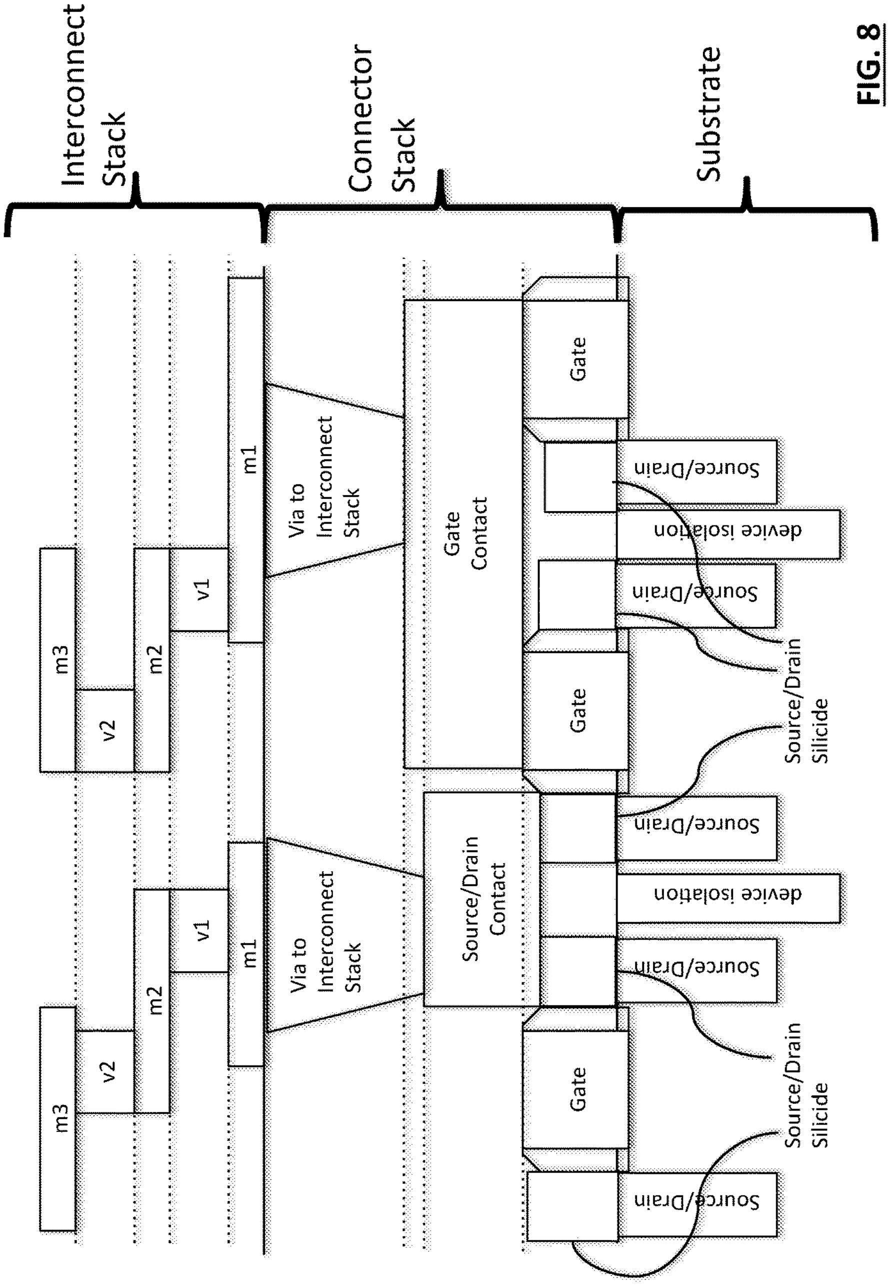
FIG. 8 depicts a physical layer stack for an exemplary CMOS process.

The connector stack is a collection of multiple layers, generally formed on top of the substrate, that supports localized connections between devices in, or on, the substrate, and/or connections to wires in an interconnect stack located above. The layers that make up the connector stack need not be strictly "stacked"; some can be partially or fully co-planar. For example, as illustrated in FIG. 8, which depicts a physical view of an exemplary CMOS layer stack, the source/drain contact and gate contact layers are partially co-planar because they share vertical extent, but on the bottom, the source/drain contact layer extends below the bottom of the gate contact layer, and on the top, the gate contact layer extends above the top of the source/drain contact layer. An example of full co-planarity would be where these two layers had identical vertical extent.

The connector stack supports various types of "connectors" and "jumpers," as illustrated in FIG. 7. These illustrative connectors and jumpers are not intended to represent individual physical layers, but rather conductive pathways that connect the identified elements. As persons skilled in the art will appreciate, each connector or jumper can be implemented using one or more manufactured "layers," where some layers may appear as parts of multiple types of connectors/jumpers.

FIG. 7. specifically illustrates the following connectors/jumpers:

Control element connector
: A conductive pathway between (i) one or more control elements and (ii) a wire in the first (e.g., m1) layer of the interconnect stack. Control element connectors will also contact any interconnect jumpers, substrate connectors, or control element jumpers that they cross.

Substrate connector
: A conductive pathway between (i) a portion of the substrate and (ii) a wire in the first layer of the interconnect stack. Substrate connectors will also contact any interconnect jumpers, substrate jumpers, control element connectors, or control element jumpers that they cross.

Substrate jumper
: A conductive pathway between two portions of the substrate that would not be connected without the substrate jumper. Substrate jumpers will also contact any substrate connectors—but not interconnect jumpers—that they cross.

Interconnect jumper
: A conductive pathway between two wires in the first interconnect layer that would not be connected without the interconnect jumper.

Interconnect jumpers will also contact any substrate connectors or control element connectors that they cross.

Control element jumper
: A conductive pathway between two control elements. Control element jumpers will also contact any control elements, control element connectors, or substrate connectors that they cross.

Non-adjacent control element jumper, not depicted in FIG. 7, but defined as follows:
: A conductive pathway between two control elements. Non-adjacent control element jumpers can pass over other control elements without contacting them. Non-adjacent control element jumpers will contact any control element connectors or substrate connectors that they cross.

Above the connector stack lies the interconnect stack. The interconnect stack is comprised of conductive wiring layers (labeled "m1," "m2," etc.—that need only be conductive, not necessarily metallic) with conductive vias (labeled "v1," "v2," etc.) that connect adjacent wiring layers. While three wiring layers are shown in FIGS. 7-8, it is understood that this number could vary from one to ten or more. Furthermore, while the vias and wiring layers in FIGS. 7-8 are shown as non-overlapping, it is possible for vias to extend into one or both of the wiring layers that they connect, or traverse more than two wiring layers.

Reference is now made to FIG. 8, which depicts a (simplified) layer stack for an exemplary CMOS process, with the correspondence between major regions—substrate, connector stack, interconnect stack—and process layers indicated on the drawing. As depicted in FIG. 8, the substrate hosts the source(s)/drain(s) of the FETs, the device isolation trenches (STI), and a lower portion of the gate(s). The connector stack implements the upper portions of the gate(s), the source/drain silicide(s), source/drain contact(s), gate contact(s), and via(s) to the interconnect stack. The interconnect stack contains multiple wiring (m1, m2, . . . ) layers, with vias (v1, v2, . . . ) between adjacent wiring layers.

The vendor-independent layers of FIG. 8 can be readily mapped to those of commercial CMOS processes, such as GlobalFoundries ("GF") (see U.S. Pat. Pub. Nos. US2014/0302660A1 and US2015/0170735A1 re the "GF layers") or Taiwan Semiconductor Manufacturing Co. ("TSMC") (see U.S. Pat. Pub. No. US2014/0210014A1 re the "TSMC layers"). Below is an exemplary mapping:

| FIG. 8 layer | GF layer | TSMC layer |
|---|---|---|
| gate (GATE) | PC | PO |
| source/drain (AA) | RX | OD |
| source/drain silicide (TS) | TS | M0_OD1 |
| gate contact (GATECNT) | CB | M0_PO |
| source/drain contact (AACNT) | CA | M0_OD2 |
| via to interconnect stack (V0) | V0 | Via0 |
| first wiring layer (M1) | M1 | M1 |

Figure 10:
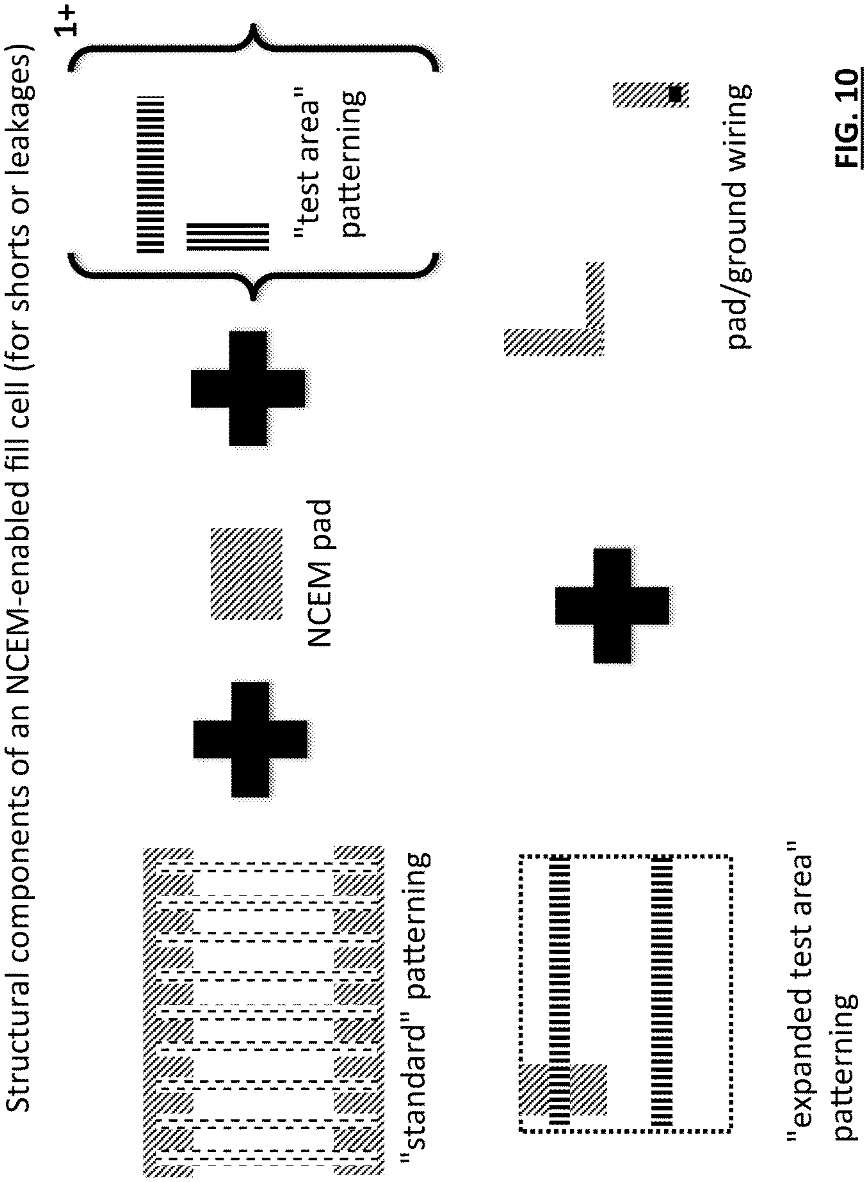
FIGS. 10-11, in conjunction with the description below, depict the overall physical structure and connectivity of short-configured (and/or leakage-configured), NCEM-enabled fill cells in accordance with certain aspects of the invention.
Figure 11:
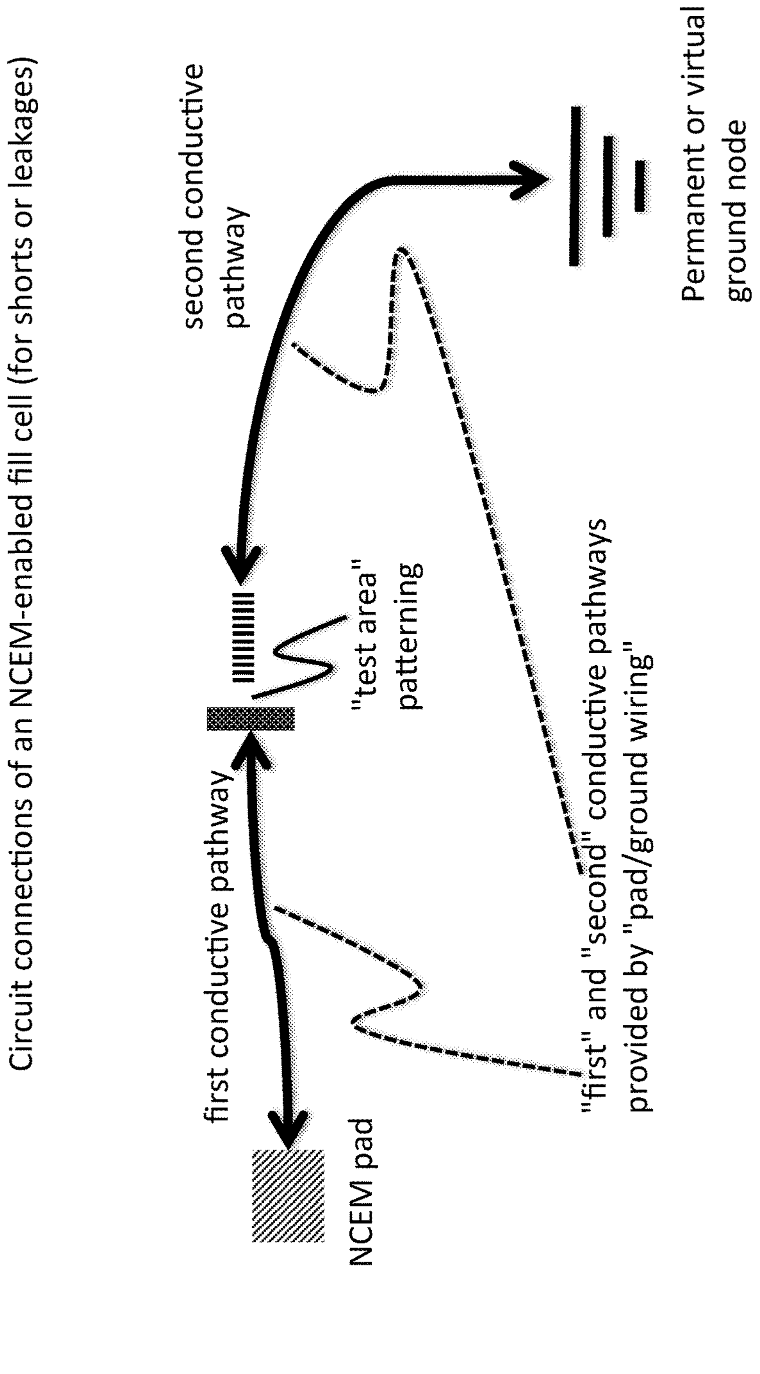

Indicated in parentheses are the names used to label these layers in FIGS. 10, 11, et seq. of this application. Persons skilled in the art will realize that these represent a minority of the many layers/masks/etc. used in the fabrication of modern devices. Nevertheless, these are believed to be the layers most relevant to enabling a skilled artisan to make and use the invention, and are the layers traditionally depicted in patent drawings of semiconductor structures (as shown, for example, by the cited GF and TSMC applications). In certain instances, additional layers may be added to depictions of selected NCEM-enabled fill cells.

Persons skilled in the art will also understand that most of the above layers can—and often are—rendered in multiple patterning steps. Typically, in this application, the drawings will combine all exposures into a single depicted layer (e.g., M1=M1E1+M1E2, or M1E1+M1E2+M1E3). In most cases, such details are irrelevant to the operation of the invention, and are determined largely by requirements of the fabrication process. In certain cases (e.g., an M1-M1-stitch-overlap-open-configured, NCEM-enabled fill cell), some potentially relevant detail(s) may be obscured by the exposure merging; however, such obscured detail(s) will nonetheless be readily apparent to the skilled artisan (by, for example, the fact that the named structure, e.g., M1-M1-stitch-overlap-open-configured, NCEM-enabled fill cell, must contain at least one overlap test region, as per FIG. 32, that is rendered in different exposures of M1, and located on the M1 path between the NCEM pad and ground).

Furthermore, short-configured cells can exist in both "same color" and "different color" varieties. For example, in a process that uses multi-patterned M1, the M1-tip-to-tip-configured, NCEM-enabled fill cells would come in two varieties: M1-tip-to-tip-same-color-short-configured cells, as well as M1-tip-to-tip-different-color-short-configured cells. The same applies to other short configurations, such as side-to-side, diagonal, etc.

Figure 9A:
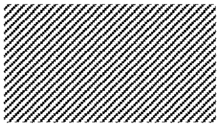
FIGS. 9A-9F depict several illustrative designs for a NCEM-enabled pad, suitable for use in connection with certain embodiments of the invention.
Figure 9B:
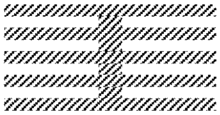
Figure 9C:
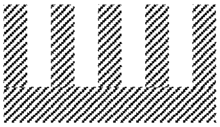
Figure 9D:
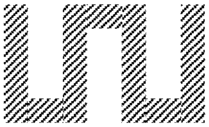
Figure 9E:
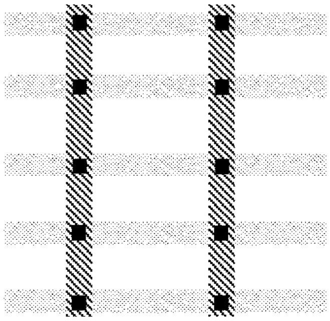
Figure 9F:
Figure 9G:
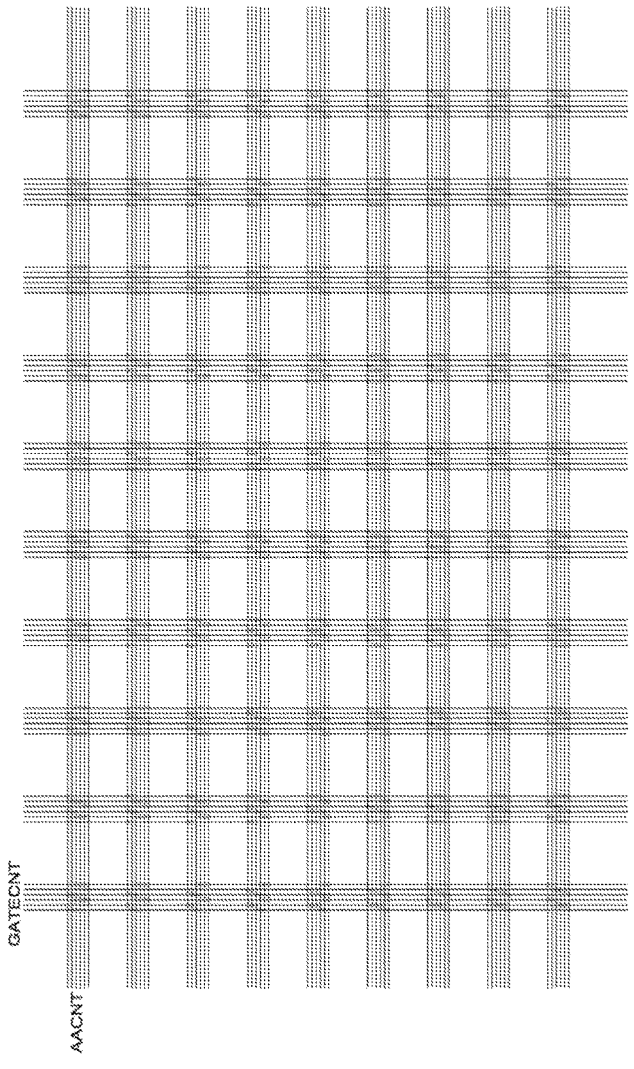
FIG. 9G depicts an exemplary mesh-style, NCEM-enabled pad, formed from a 10×9 grid of single-patterned GATECNT and single-patterned AACNT stripes.
Figure 9H:
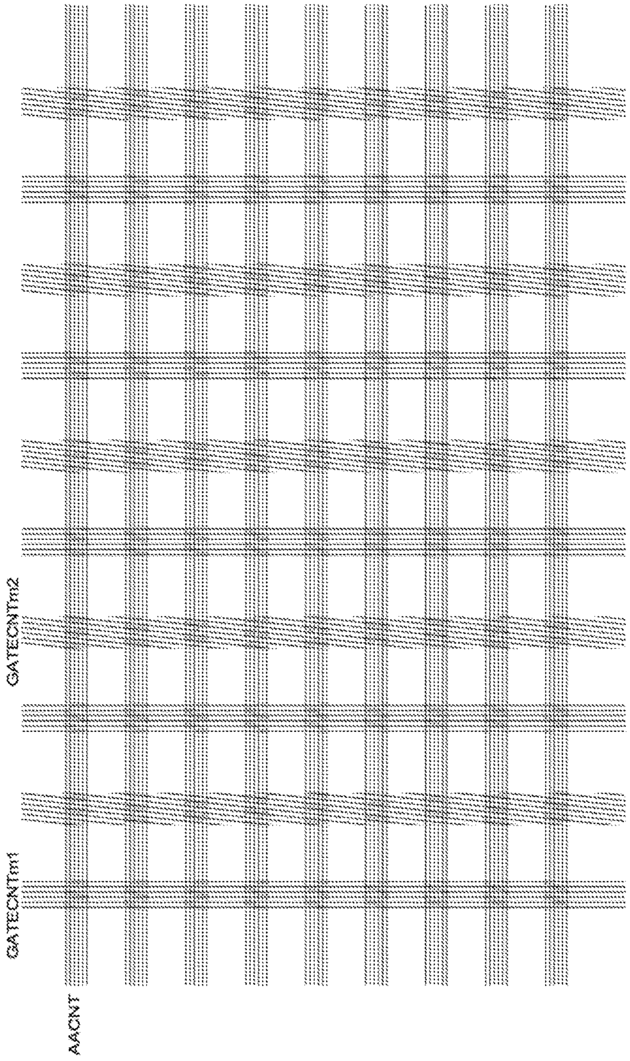
FIG. 9H depicts an exemplary mesh-style, NCEM-enabled pad, formed from a 10×9 grid of double-patterned GATECNT and single-patterned AACNT stripes.
Figure 9I:
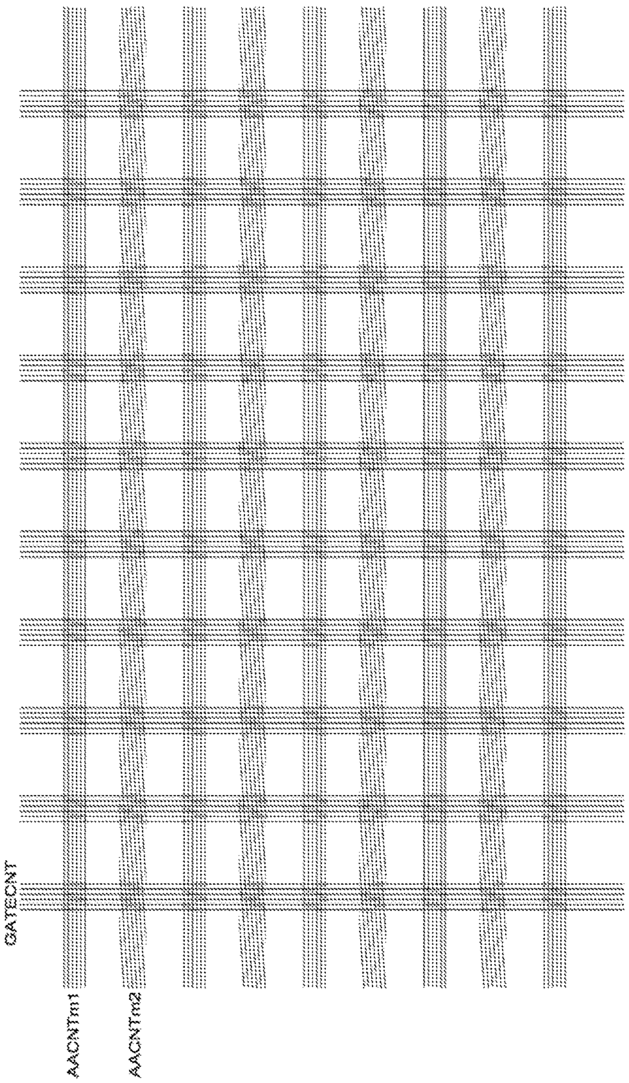
FIG. 9I depicts an exemplary mesh-style, NCEM-enabled pad, formed from a 10×9 grid of single-patterned GATECNT and double-patterned AACNT stripes.
Figure 9J:
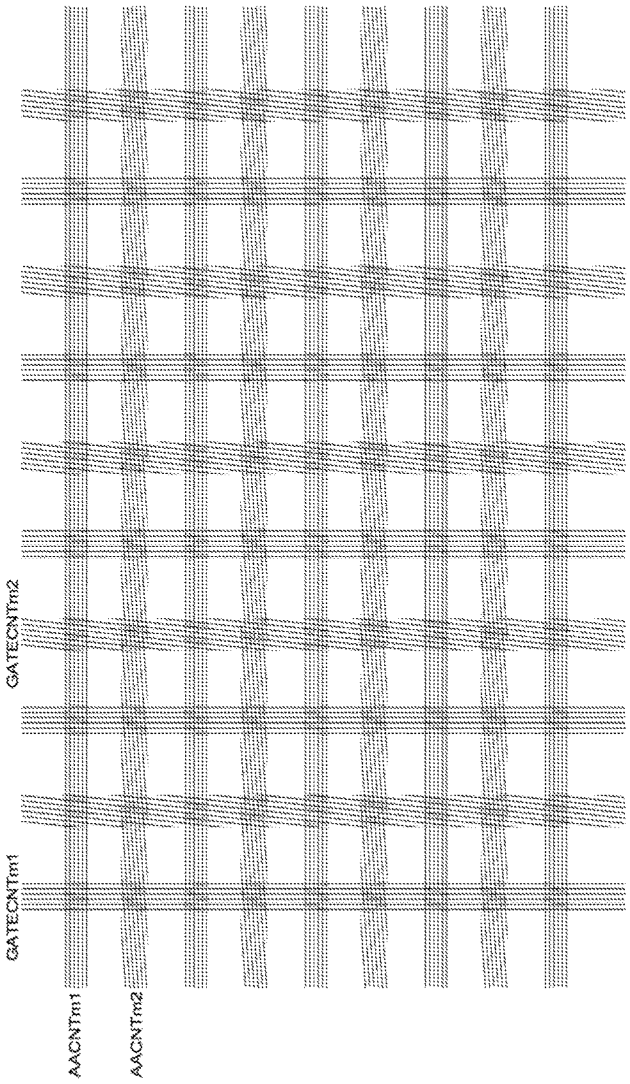
FIG. 9J depicts an exemplary mesh-style, NCEM-enabled pad, formed from a 10×9 grid of double-patterned GATECNT and double-patterned AACNT stripes.
Figure 9K:
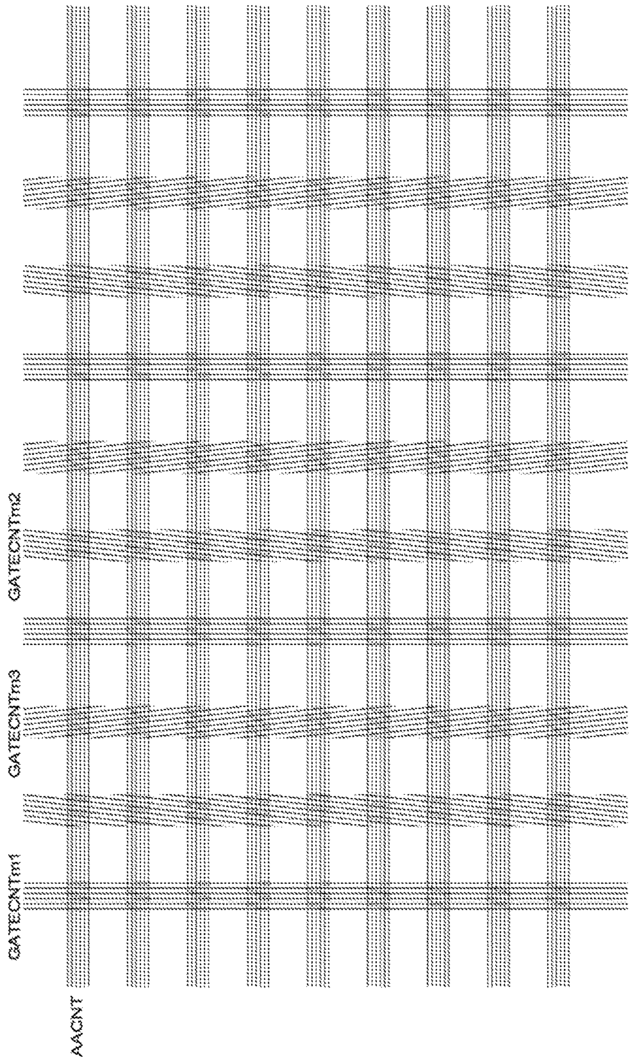
FIG. 9K depicts an exemplary mesh-style, NCEM-enabled pad, formed from a 10×9 grid of triple-patterned GATECNT and single-patterned AACNT stripes.
Figure 9L:
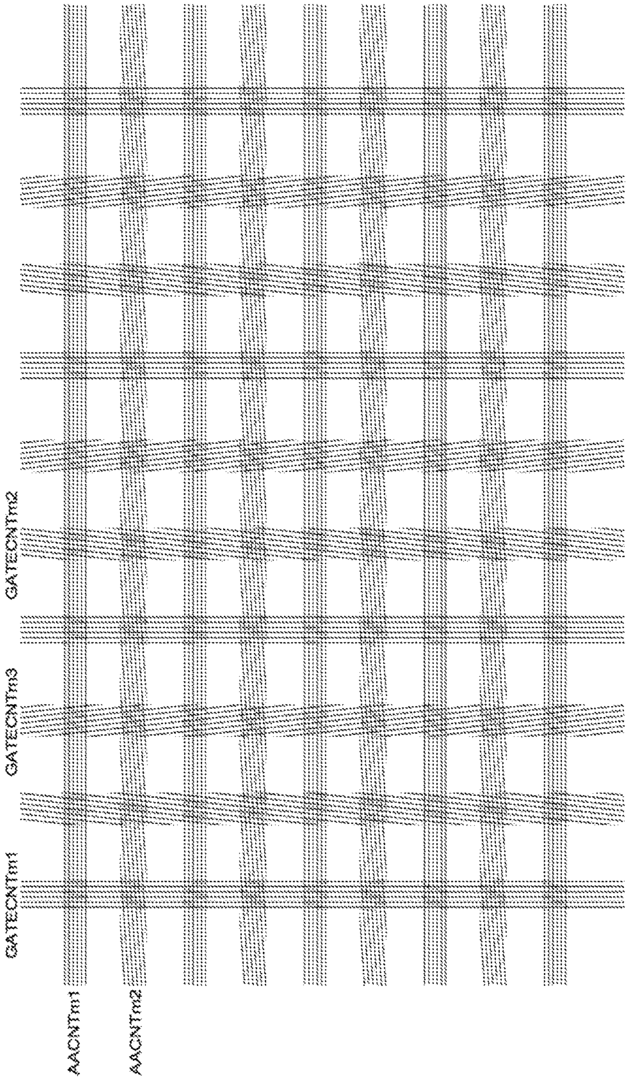
FIG. 9L depicts an exemplary mesh-style, NCEM-enabled pad, formed from a 10×9 grid of triple-patterned GATECNT and double-patterned AACNT stripes.
Figure 9M:
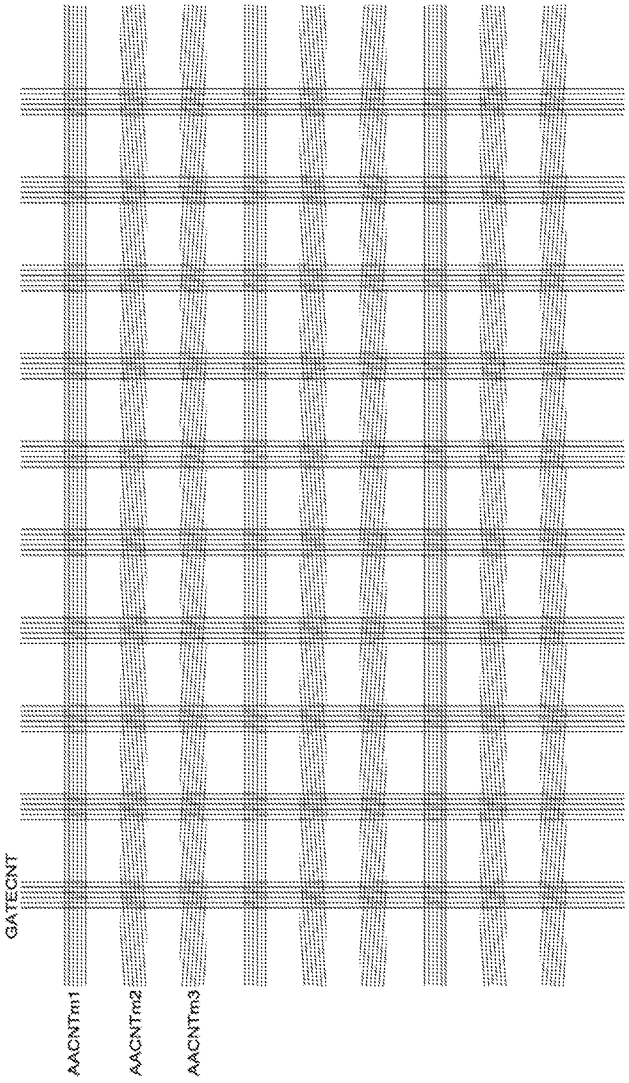
FIG. 9M depicts an exemplary mesh-style, NCEM-enabled pad, formed from a 10×9 grid of single-patterned GATECNT and triple-patterned AACNT stripes.
Figure 9N:
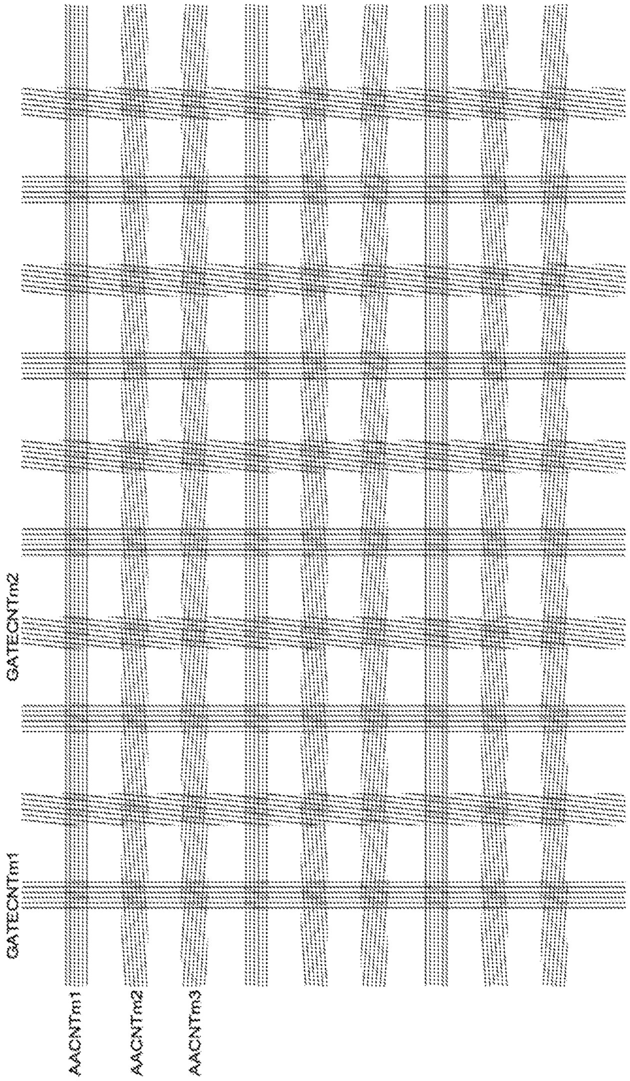
FIG. 9N depicts an exemplary mesh-style, NCEM-enabled pad, formed from a 10×9 grid of double-patterned GATECNT and triple-patterned AACNT stripes.
Figure 9O:
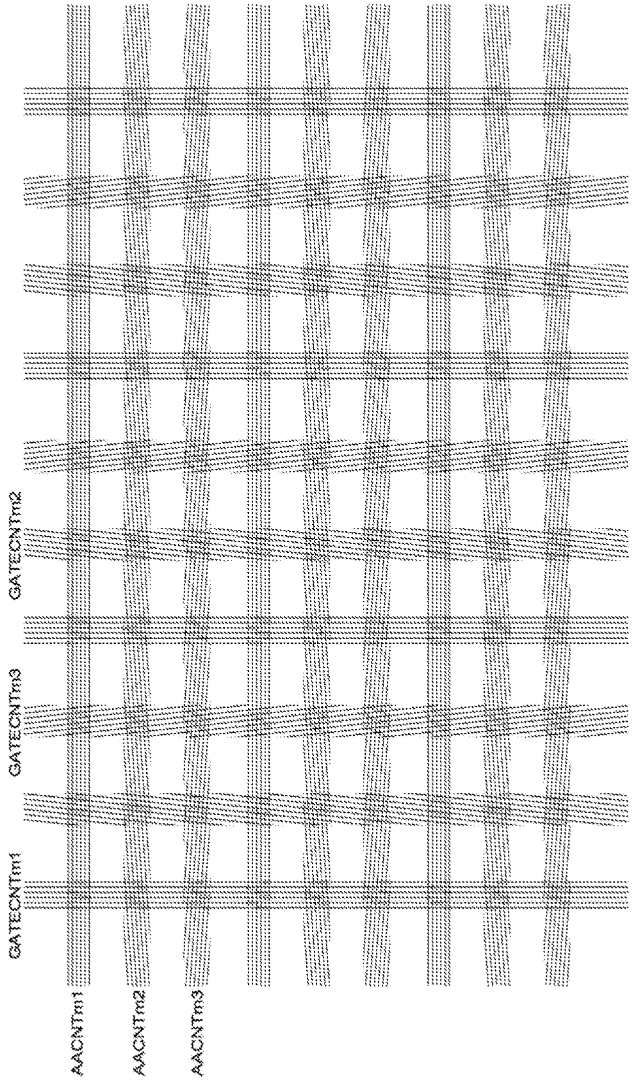
FIG. 9O depicts an exemplary mesh-style, NCEM-enabled pad, formed from a 10×9 grid of triple-patterned GATECNT and triple-patterned AACNT stripes.
Figure 9P:
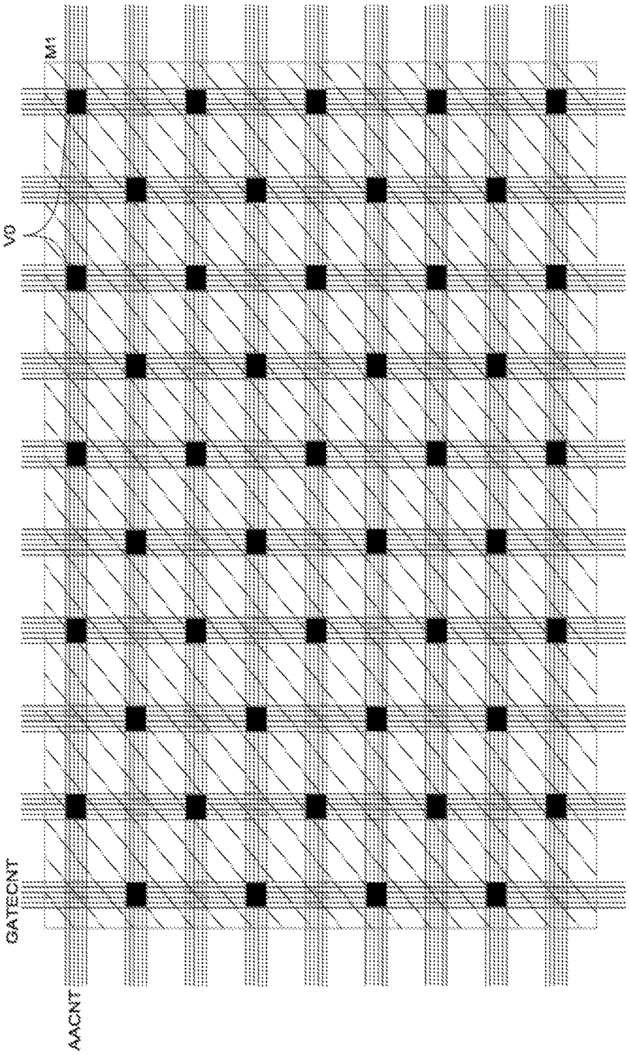
FIG. 9P depicts an exemplary mesh-style, NCEM-enabled pad, formed from a 10×9 grid of single-patterned GATECNT and single-patterned AACNT stripes, with an overlying, solid M1 pad, and a plurality of V0 vias positioned at GATECNT-AACNT junction points.
Figure 9Q:
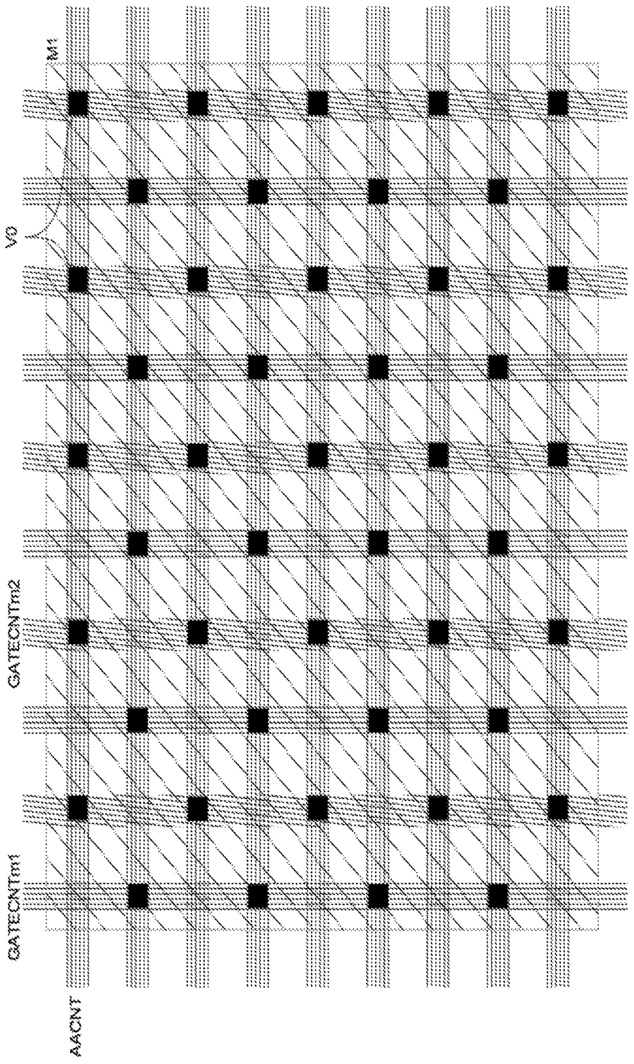
FIG. 9Q depicts an exemplary mesh-style, NCEM-enabled pad, formed from a 10×9 grid of double-patterned GATECNT and single-patterned AACNT stripes, with an overlying, solid M1 pad, and a plurality of V0 vias positioned at GATECNT-AACNT junction points.
Figure 9R:
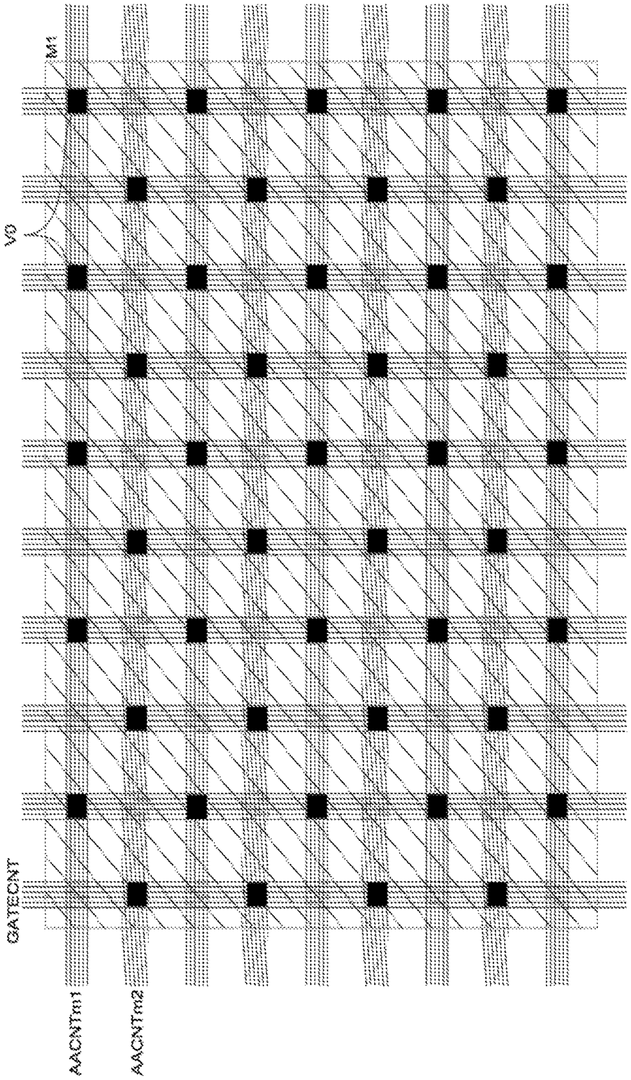
FIG. 9R depicts an exemplary mesh-style, NCEM-enabled pad, formed from a 10×9 grid of single-patterned GATECNT and double-patterned AACNT stripes, with an overlying, solid M1 pad, and a plurality of V0 vias positioned at GATECNT-AACNT junction points.
Figure 9S:
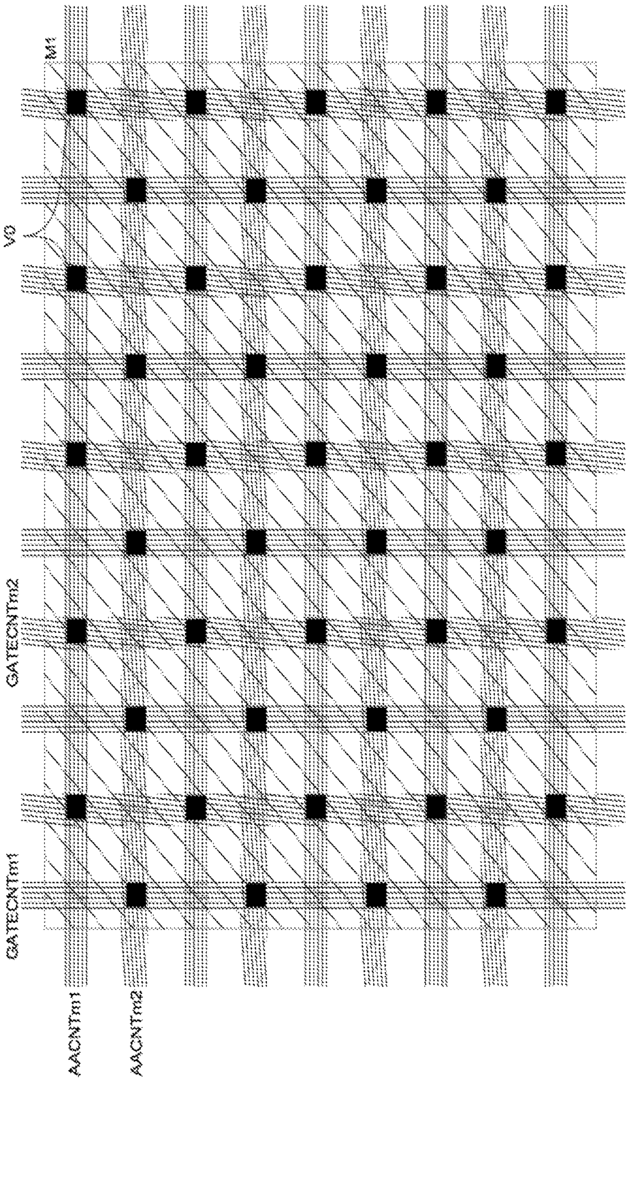
FIG. 9S depicts an exemplary mesh-style, NCEM-enabled pad, formed from a 10×9 grid of double-patterned GATECNT and double-patterned AACNT stripes, with an overlying, solid M1 pad, and a plurality of V0 vias positioned at GATECNT-AACNT junction points.
Figure 9T:
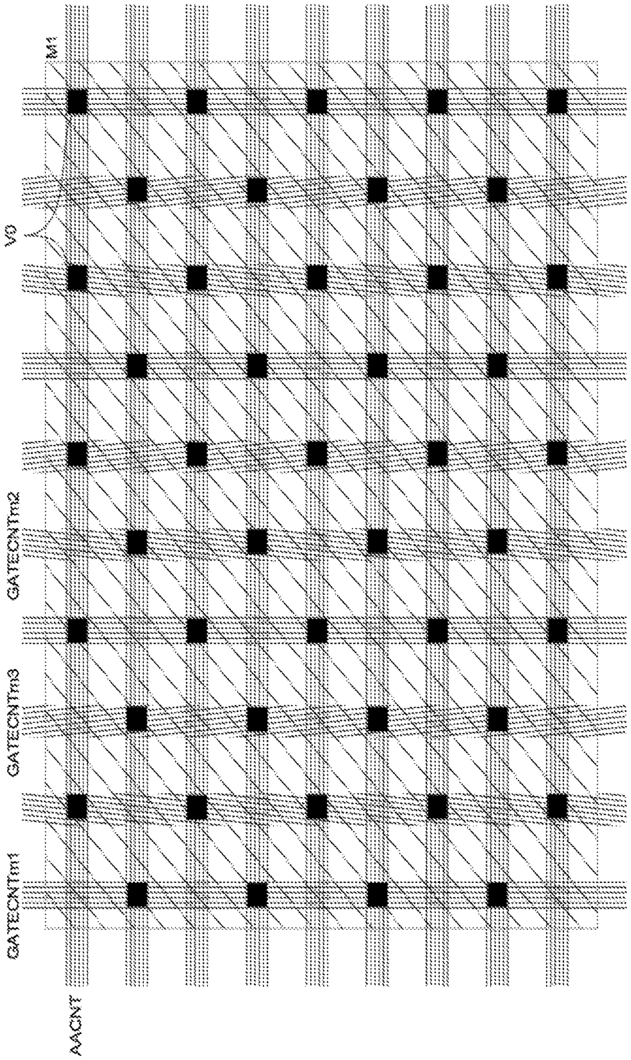
FIG. 9T depicts an exemplary mesh-style, NCEM-enabled pad, formed from a 10×9 grid of triple-patterned GATECNT and single-patterned AACNT stripes, with an overlying, solid M1 pad, and a plurality of V0 vias positioned at GATECNT-AACNT junction points.
Figure 9U:
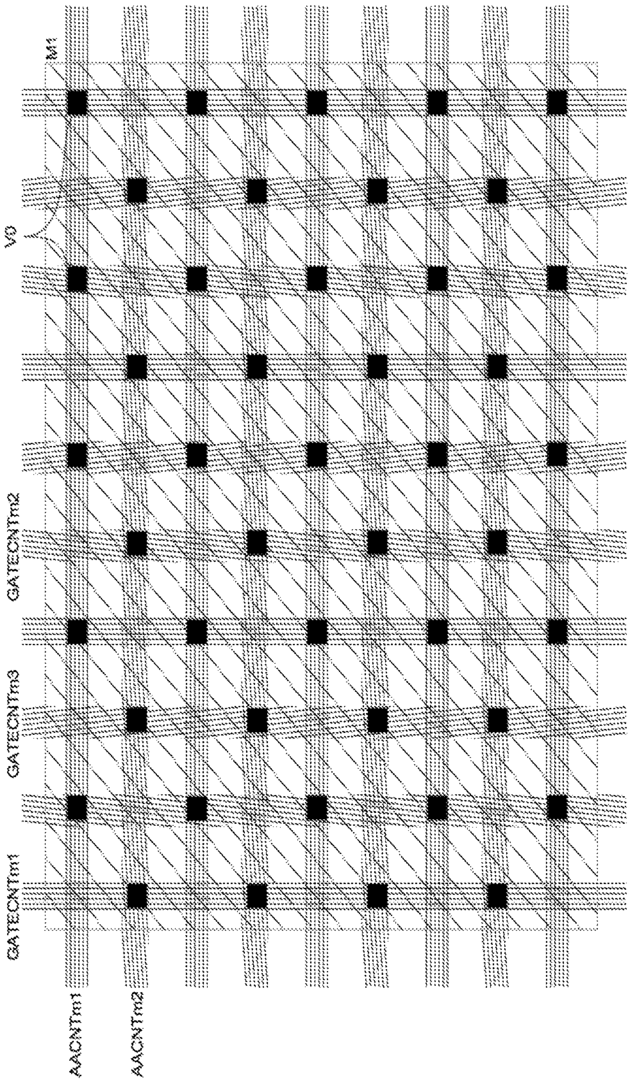
FIG. 9U depicts an exemplary mesh-style, NCEM-enabled pad, formed from a 10×9 grid of triple-patterned GATECNT and double-patterned AACNT stripes, with an overlying, solid M1 pad, and a plurality of V0 vias positioned at GATECNT-AACNT junction points.
Figure 9V:
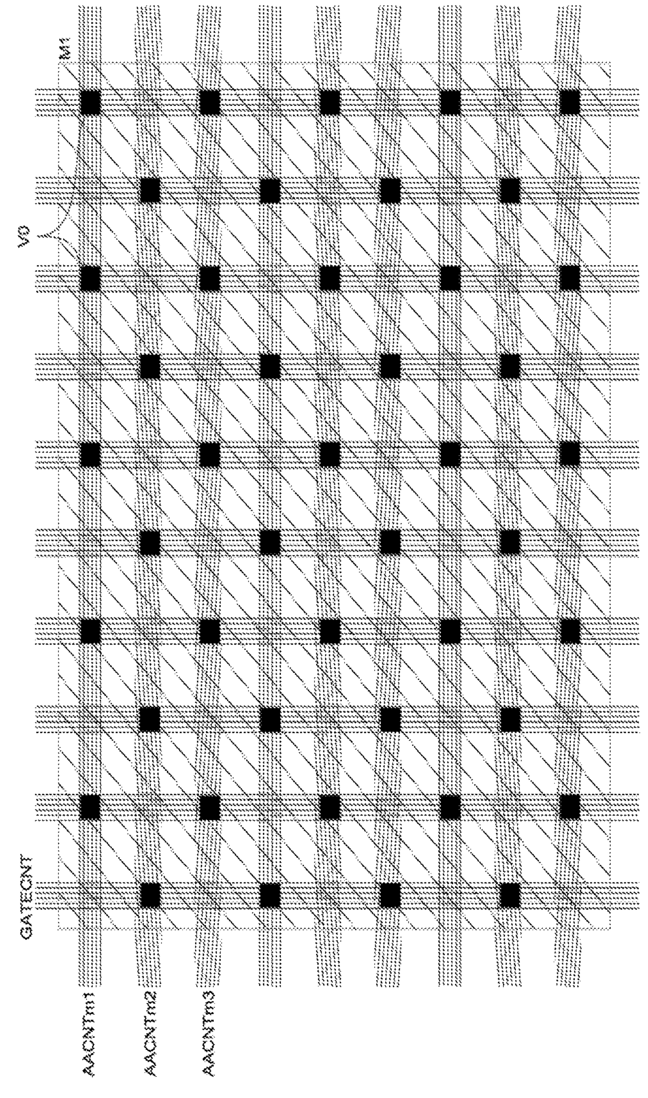
FIG. 9V depicts an exemplary mesh-style, NCEM-enabled pad, formed from a 10×9 grid of single-patterned GATECNT and triple-patterned AACNT stripes, with an overlying, solid M1 pad, and a plurality of V0 vias positioned at GATECNT-AACNT junction points.
Figure 9W:
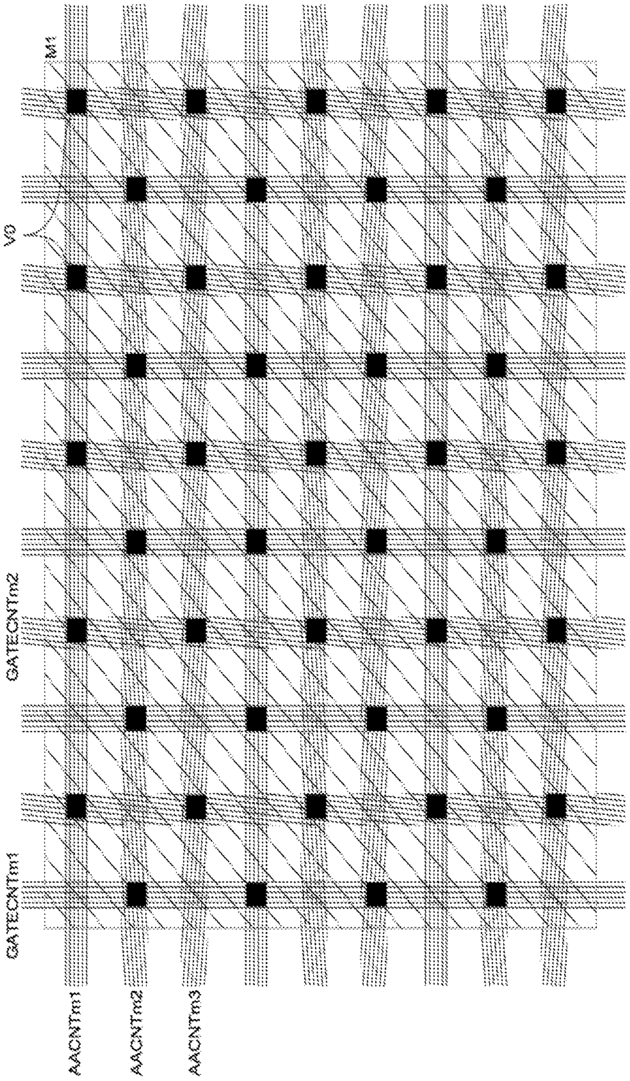
FIG. 9W depicts an exemplary mesh-style, NCEM-enabled pad, formed from a 10×9 grid of double-patterned GATECNT and triple-patterned AACNT stripes, with an overlying, solid M1 pad, and a plurality of V0 vias positioned at GATECNT-AACNT junction points.
Figure 9X:
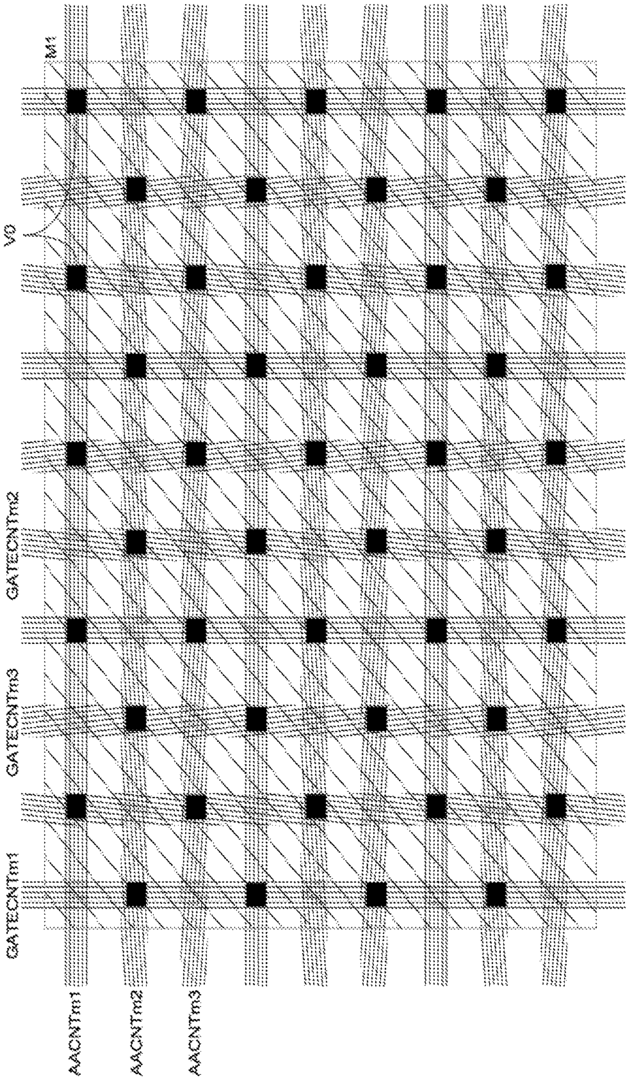
FIG. 9X depicts an exemplary mesh-style, NCEM-enabled pad, formed from a 10×9 grid of triple-patterned GATECNT and triple-patterned AACNT stripes, with an overlying, solid M1 pad, and a plurality of V0 vias positioned at GATECNT-AACNT junction points.
Figure 9Y:
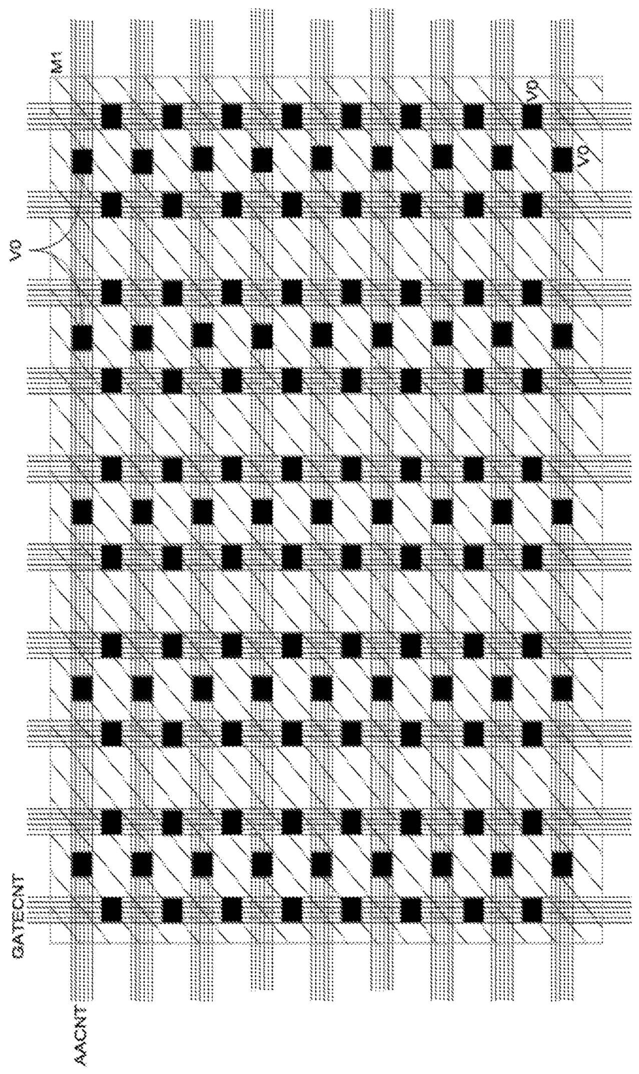
FIG. 9Y depicts an exemplary mesh-style, NCEM-enabled pad, formed from a 10×9 grid of single-patterned GATECNT and single-patterned AACNT stripes, with an overlying, solid M1 pad, and a plurality of V0 vias positioned to avoid GATECNT-AACNT junction points.
Figure 9Z:
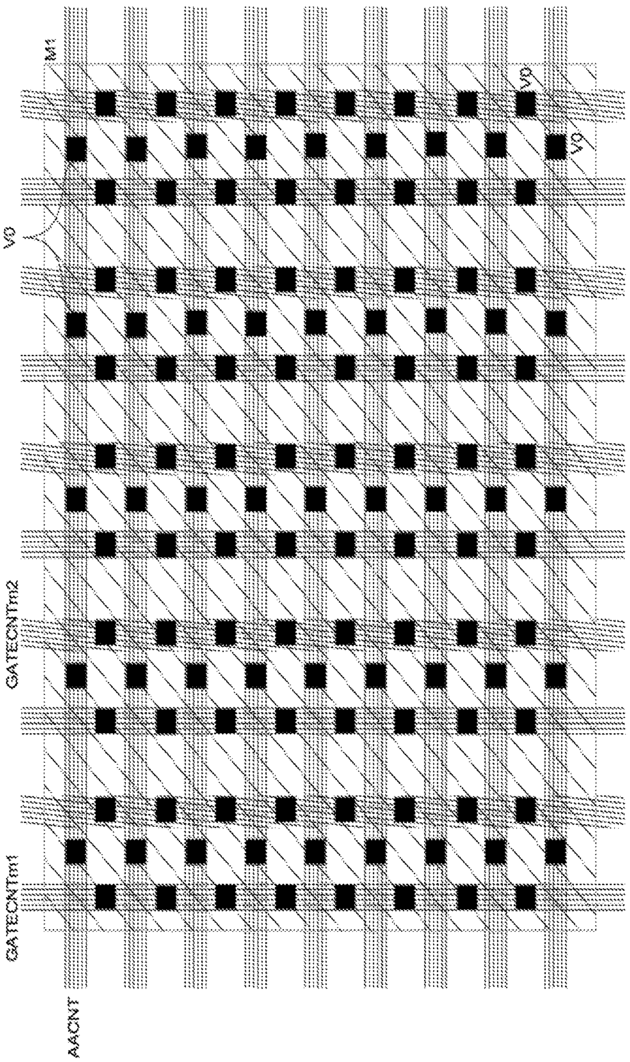
FIG. 9Z depicts an exemplary mesh-style, NCEM-enabled pad, formed from a 10×9 grid of double-patterned GATECNT and single-patterned AACNT stripes, with an overlying, solid M1 pad, and a plurality of V0 vias positioned to avoid GATECNT-AACNT junction points.
Figure 9A:
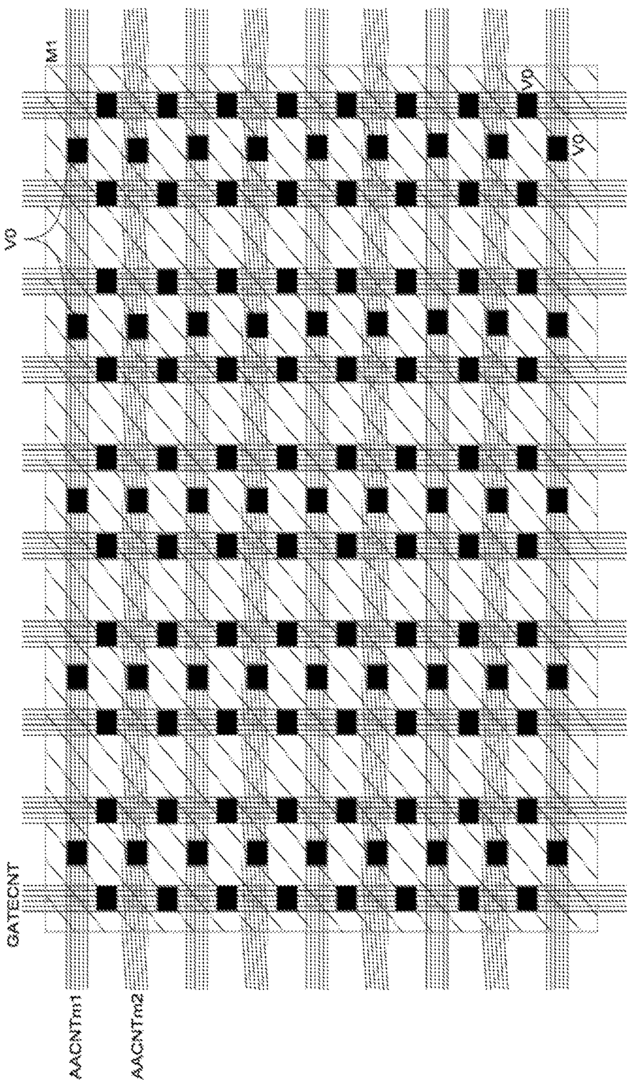
Figure 9B:
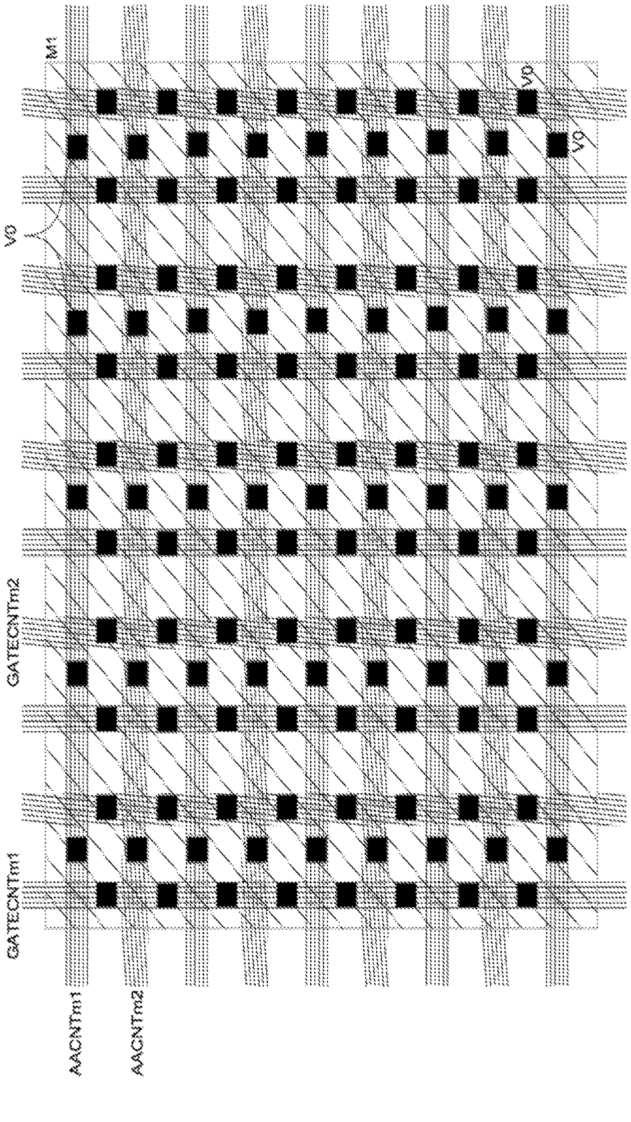
Figure 9C:
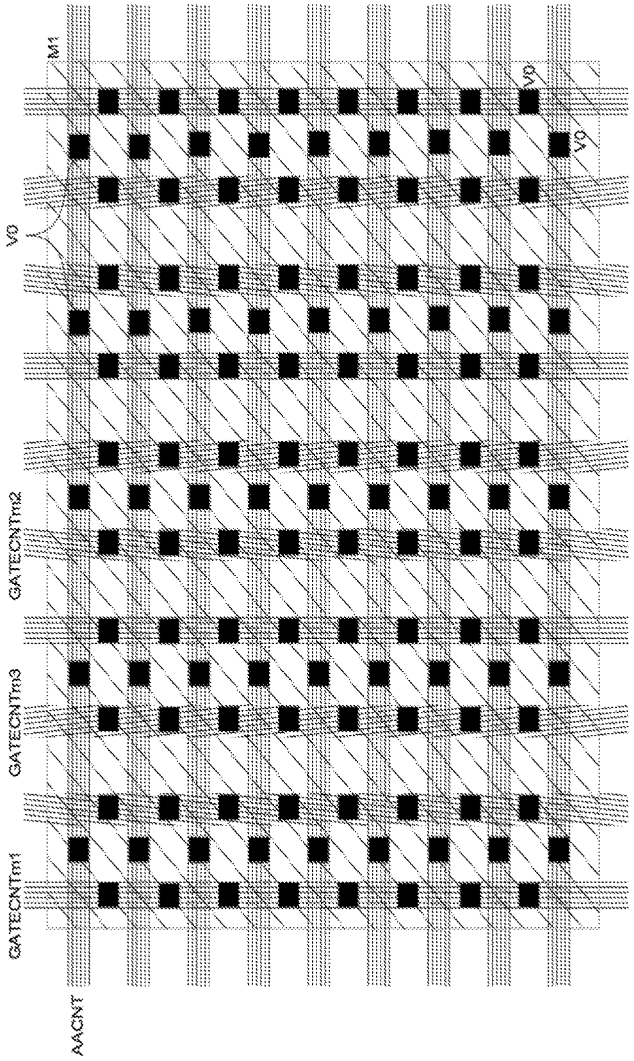
Figure 9D:
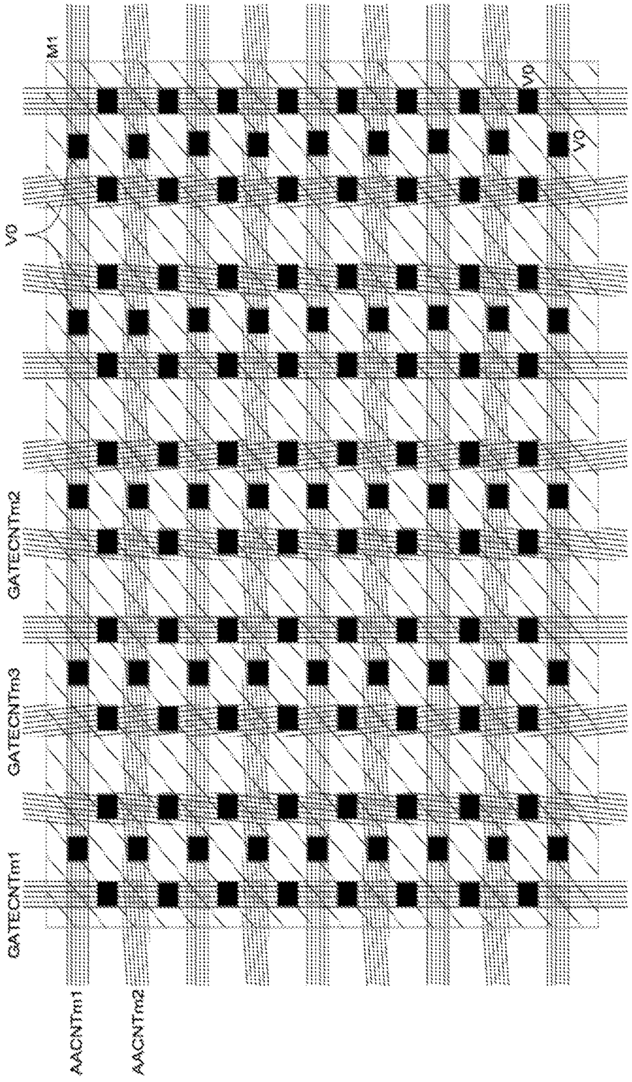
Figure 9E:
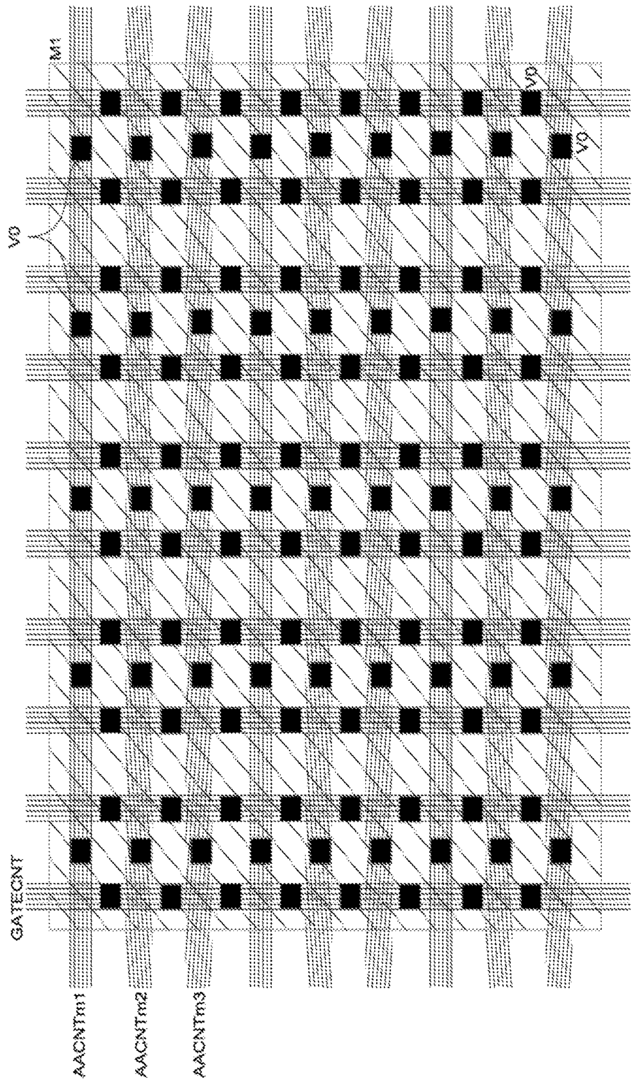
Figure 9F:
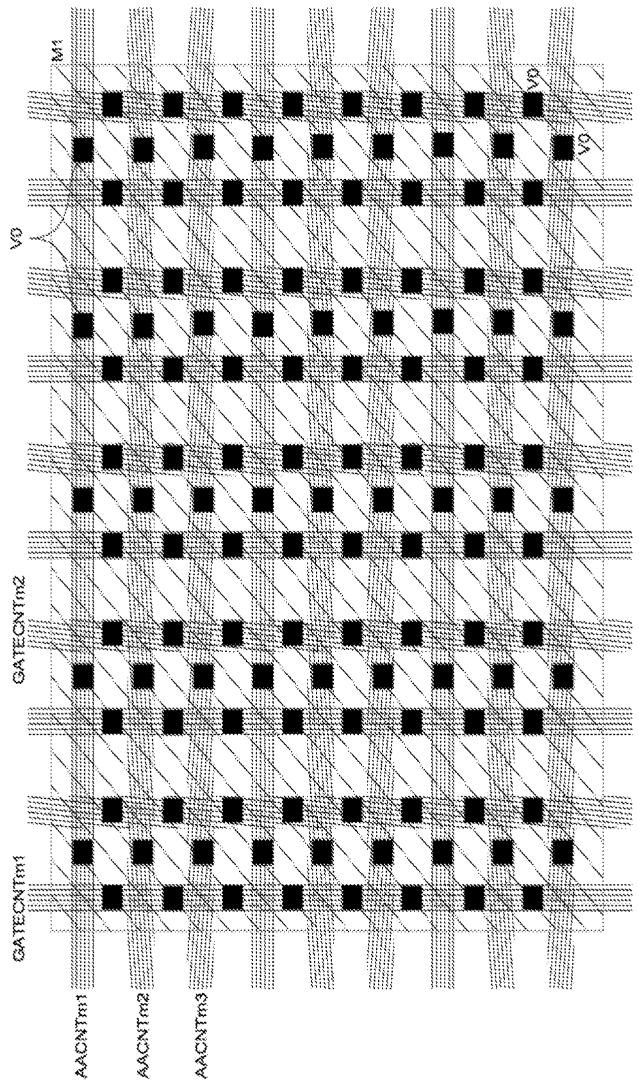
Figure 9G:
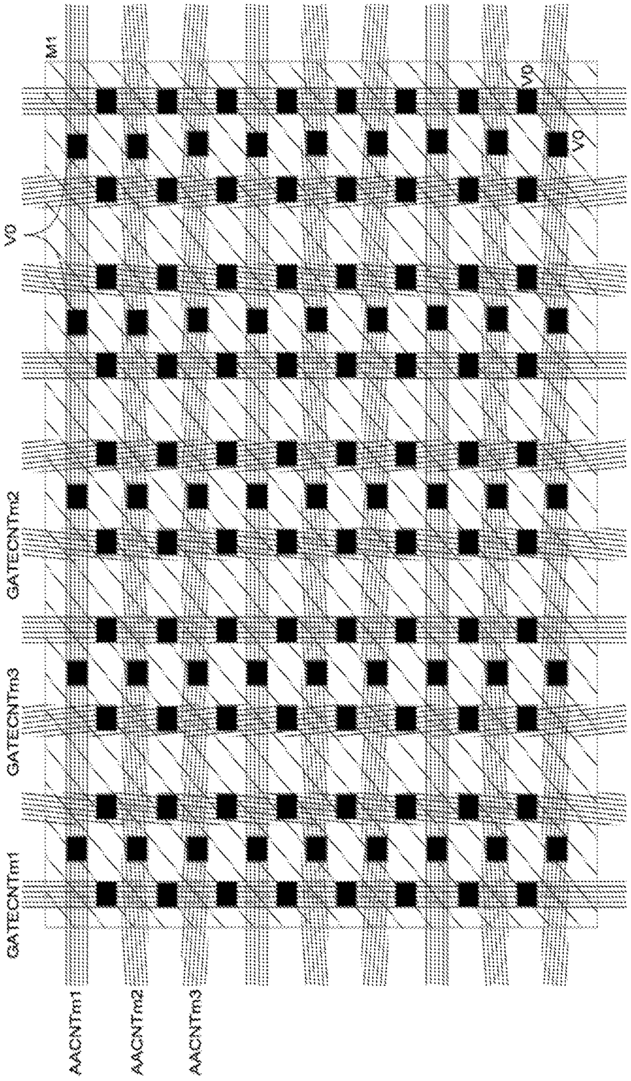
Figure 9H:
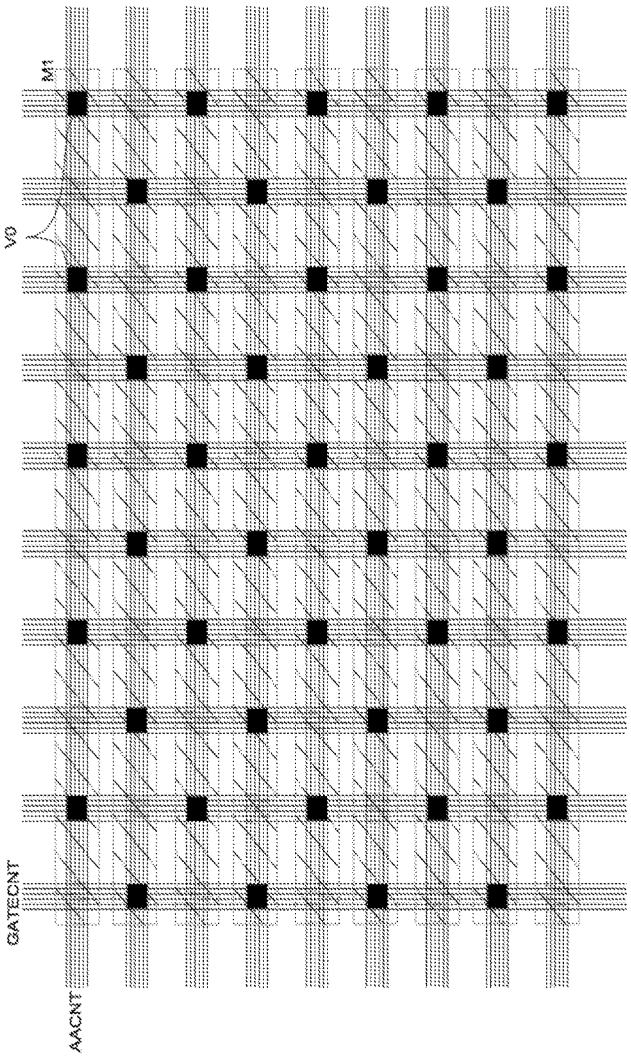
Figure 9I:
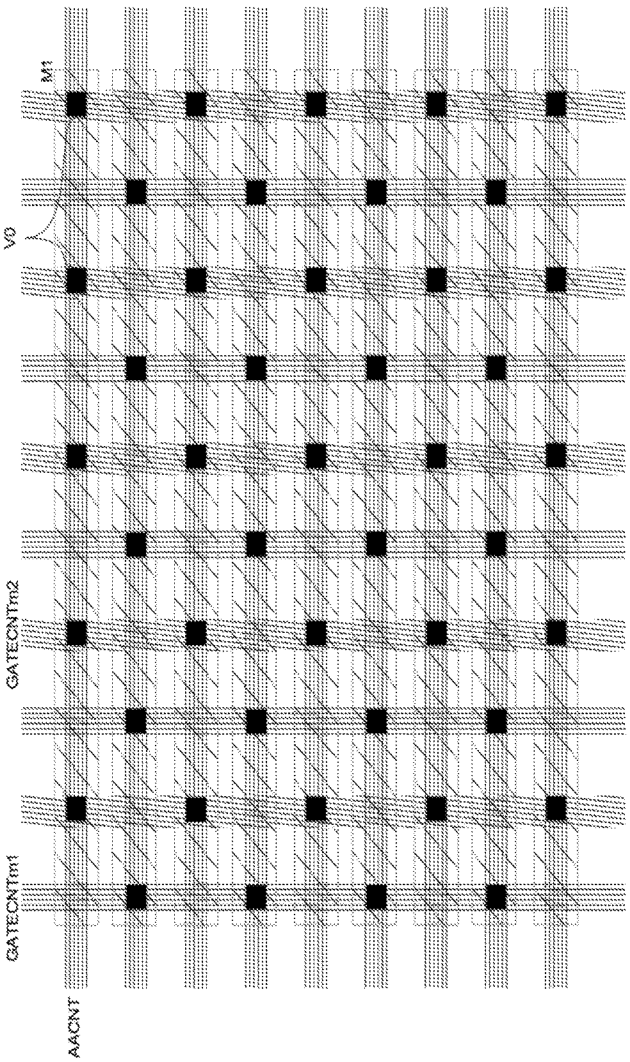
Figure 9J:
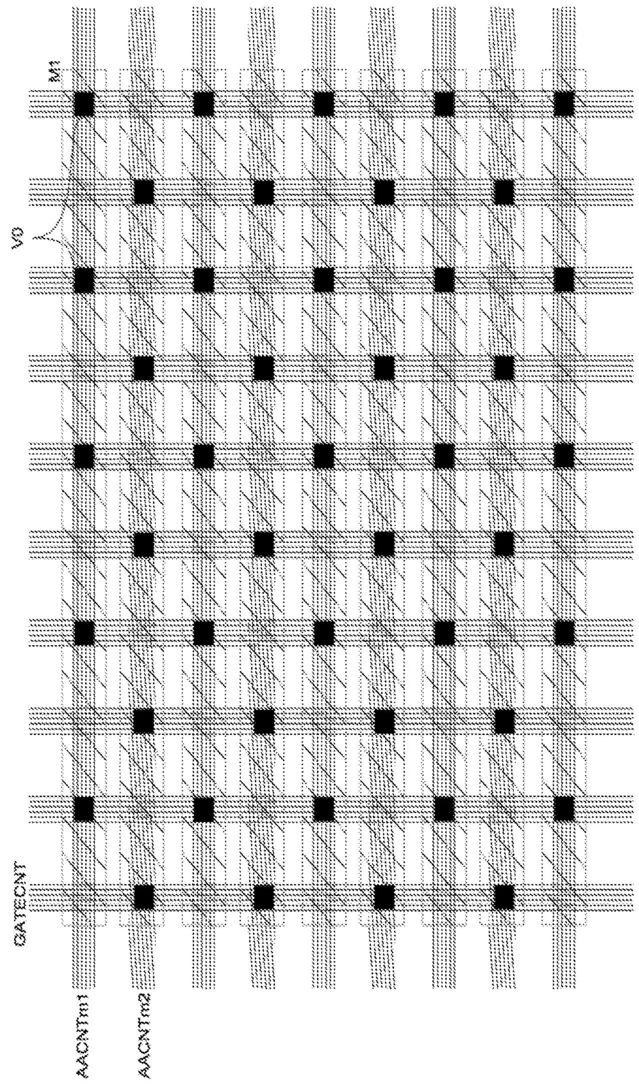
Figure 9K:
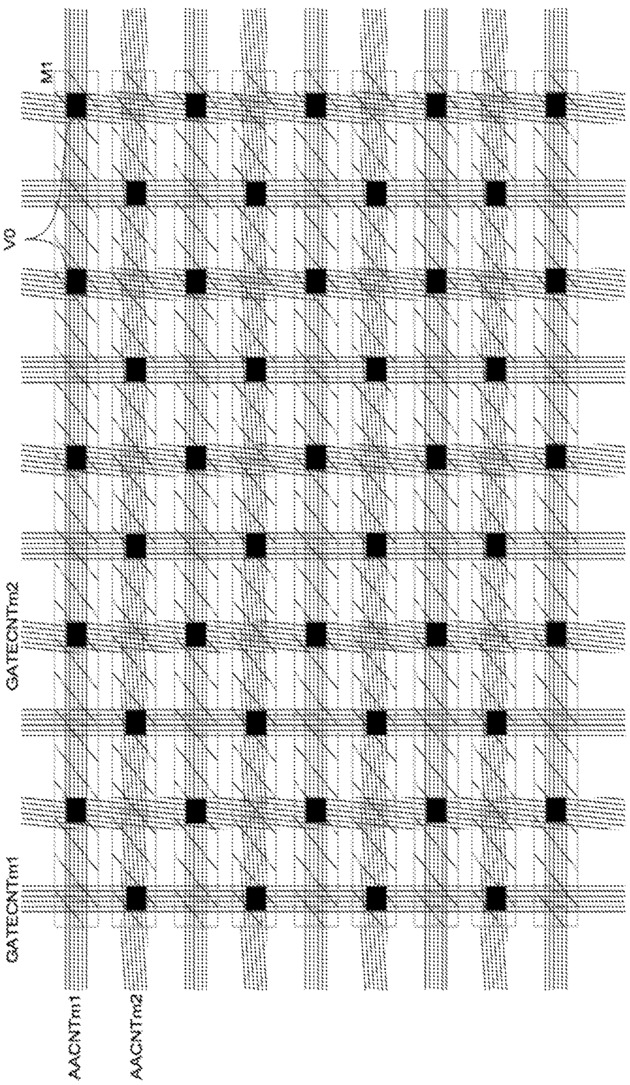
Figure 9L:
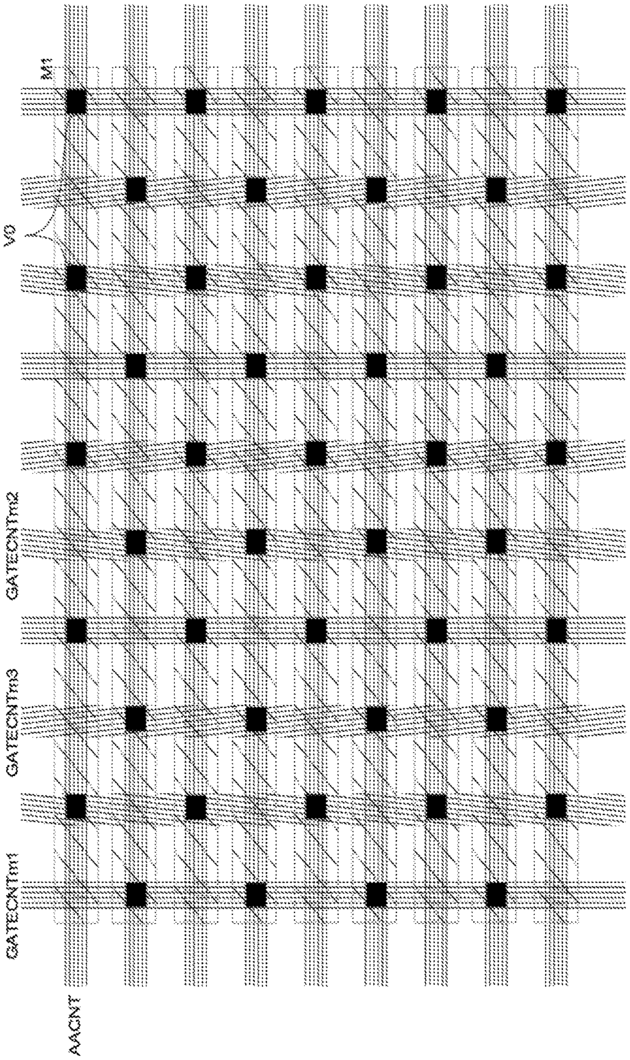
Figure 9M:
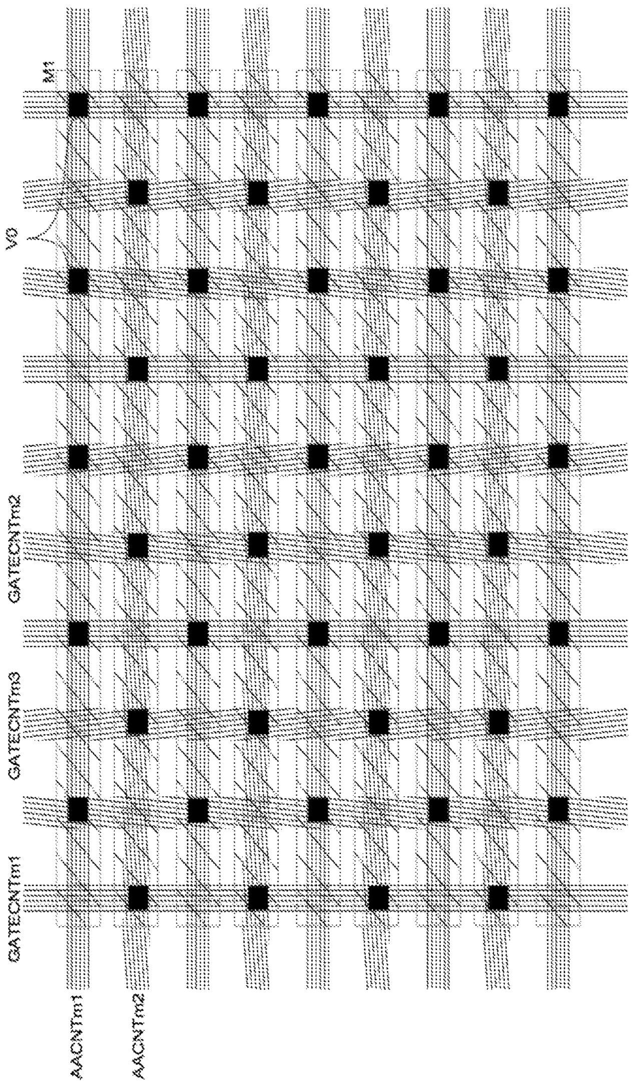
Figure 9N:
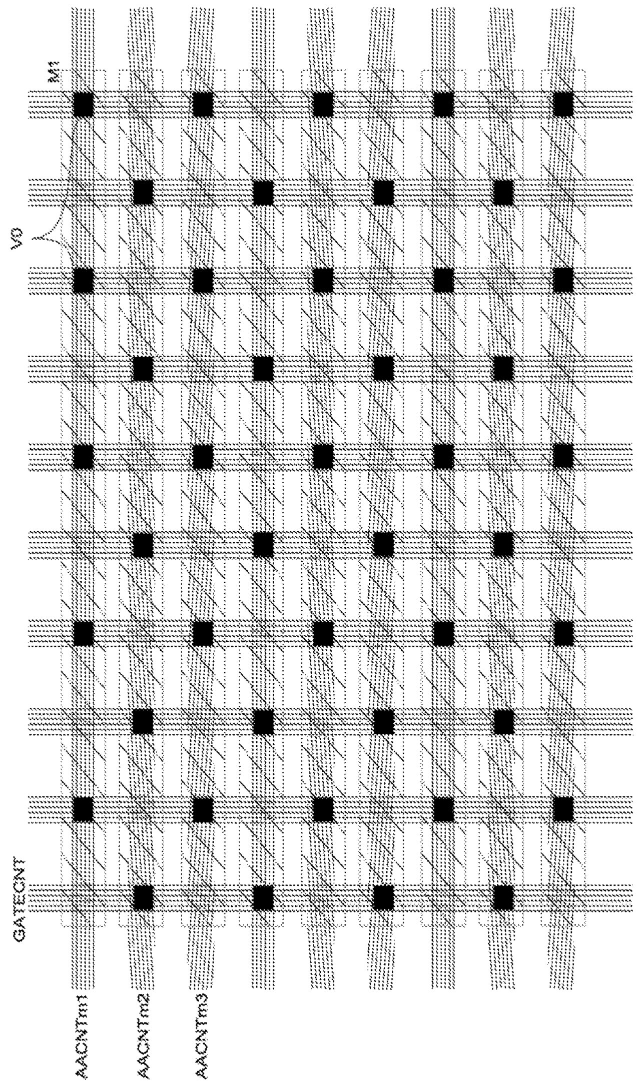
Figure 9O:
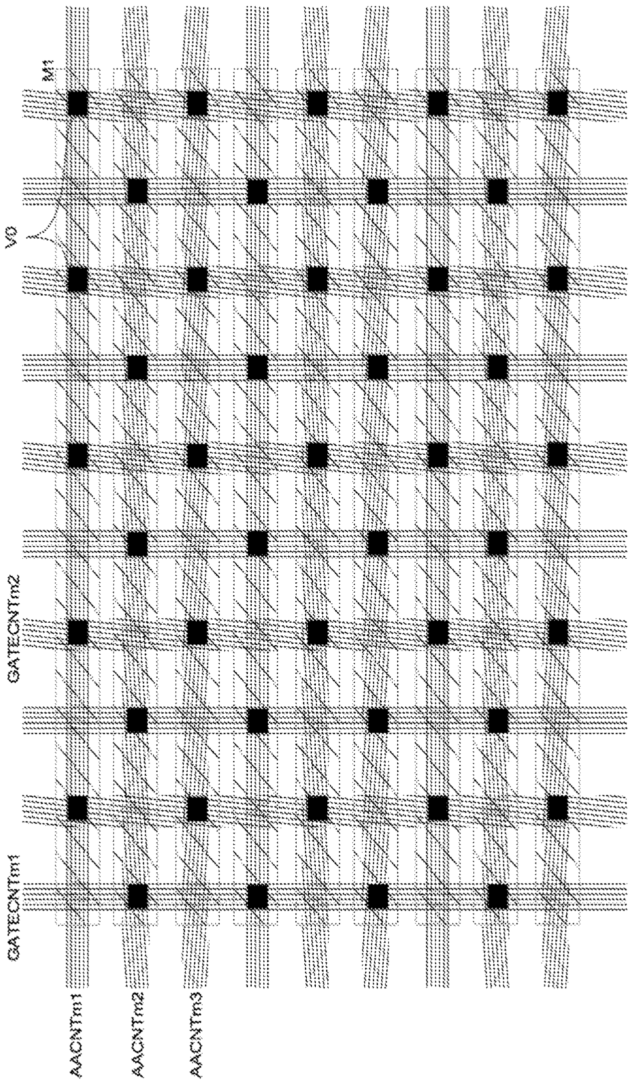
Figure 9P:
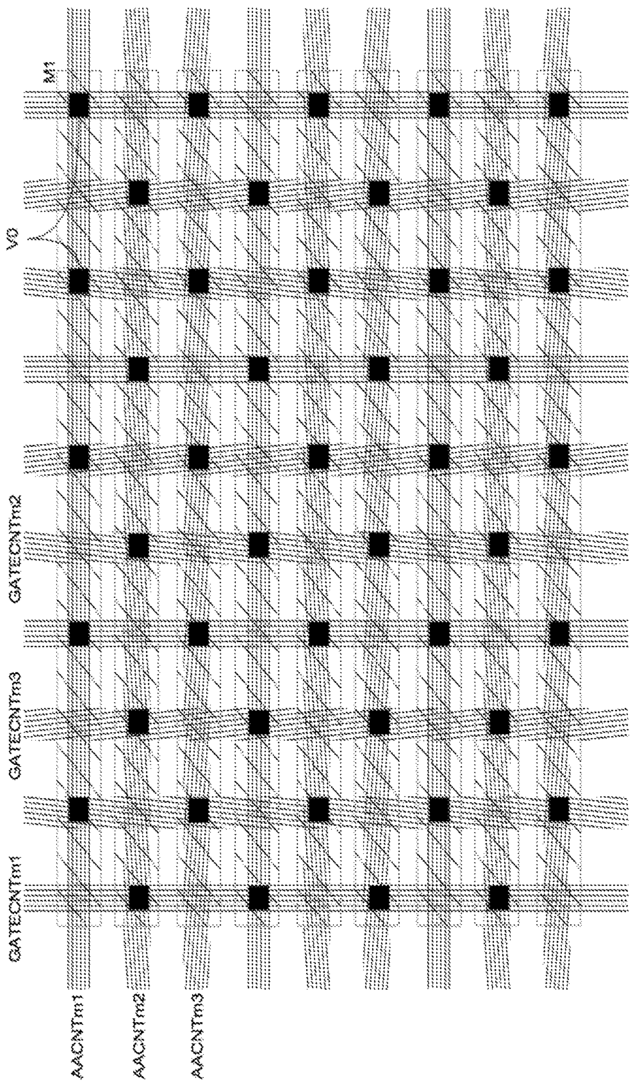
Figure 9Q:
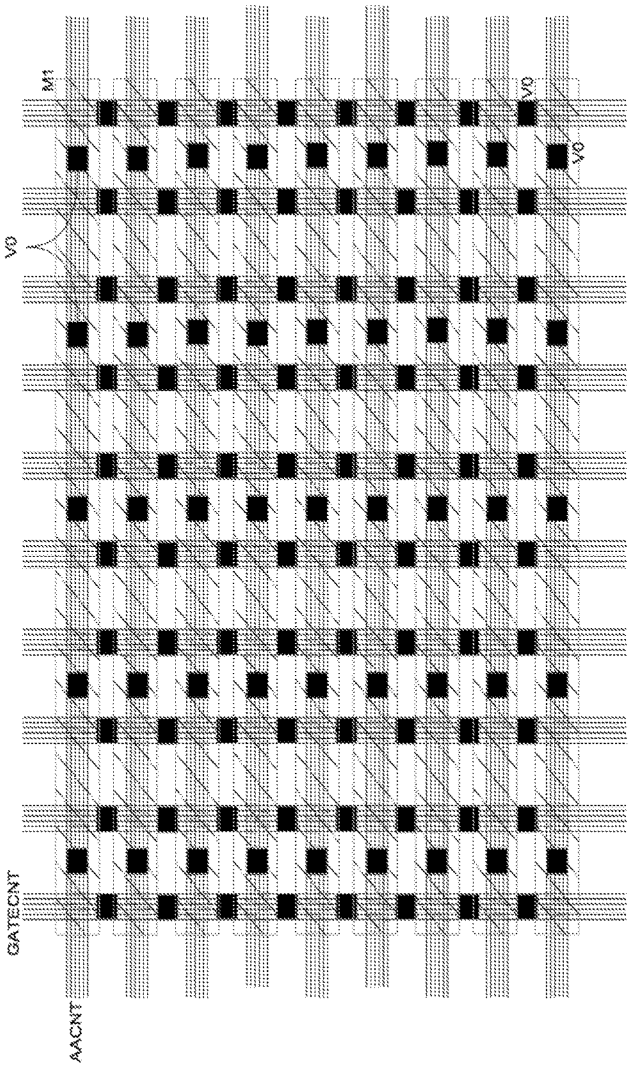
Figure 9R:
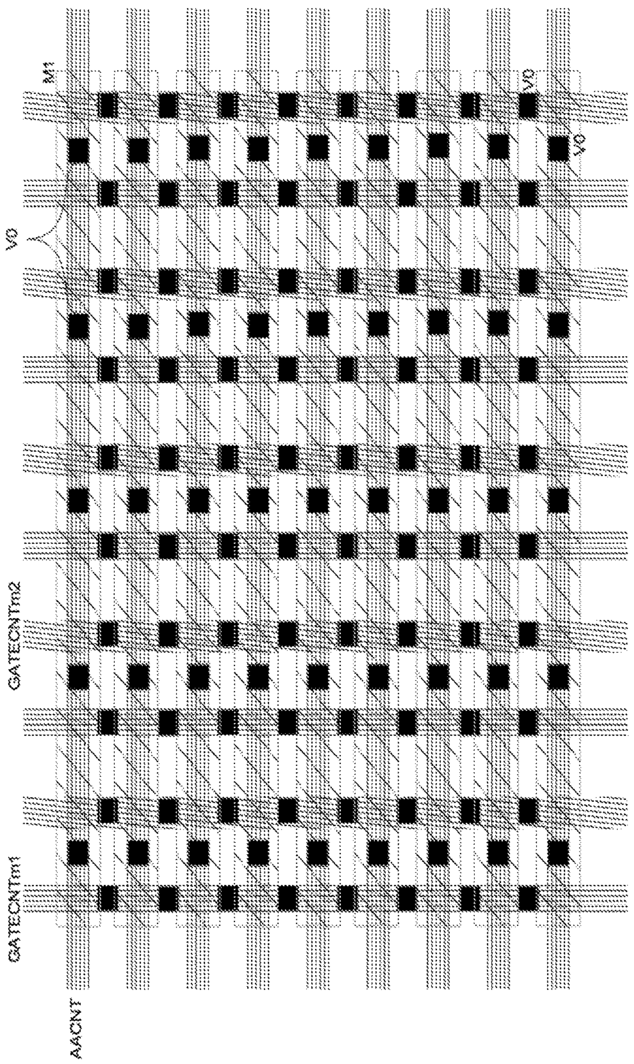
Figure 9S:
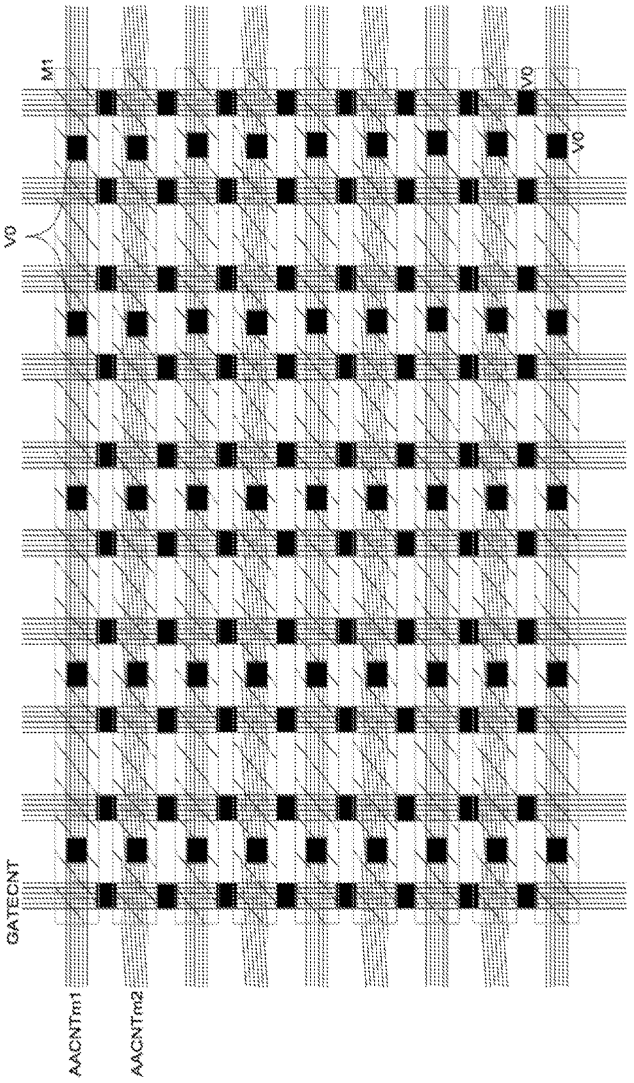
Figure 9T:
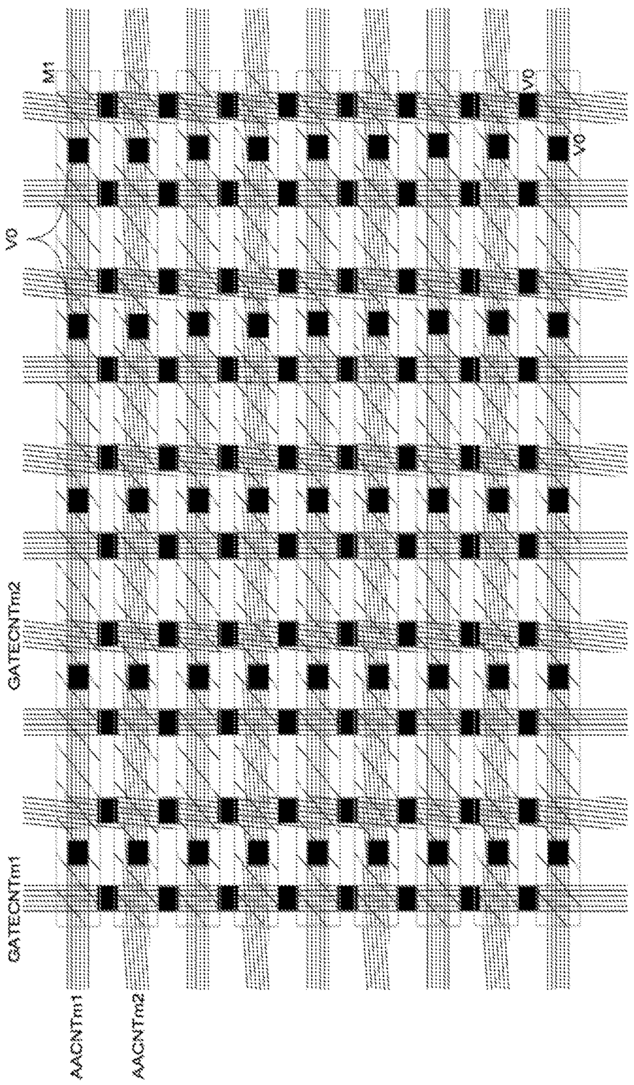
Figure 9U:
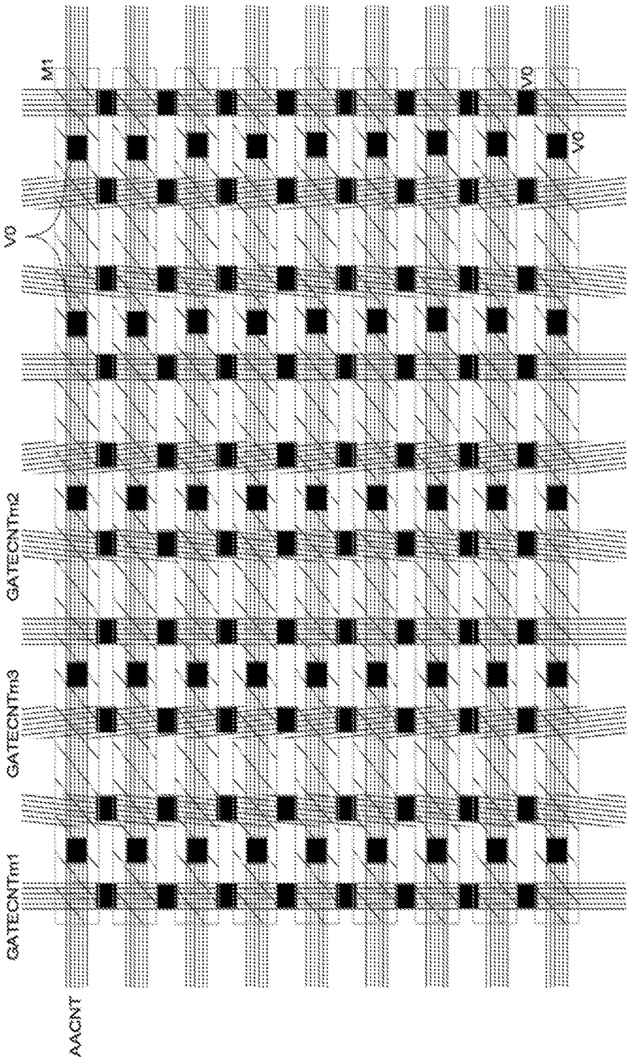
Figure 9V:
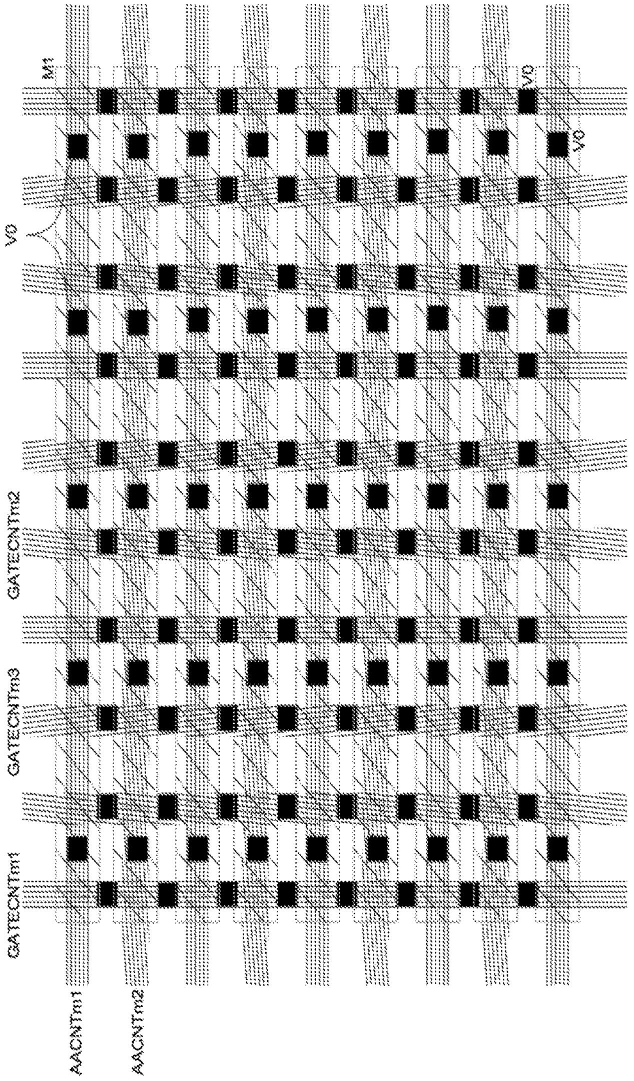
Figure 9W:
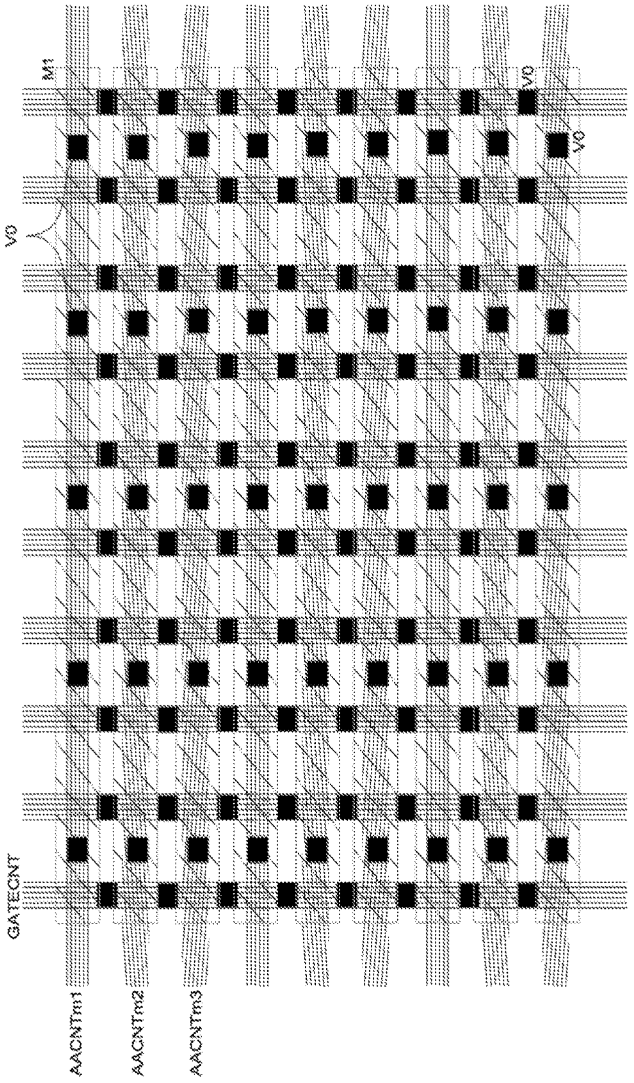
Figure 9X:
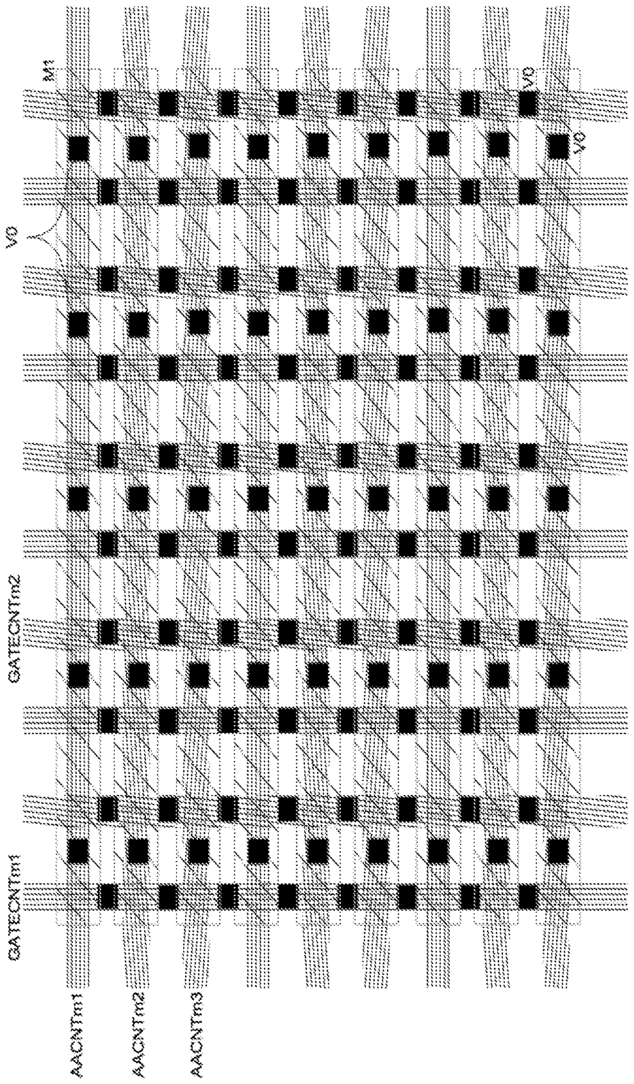
Figure 9Y:
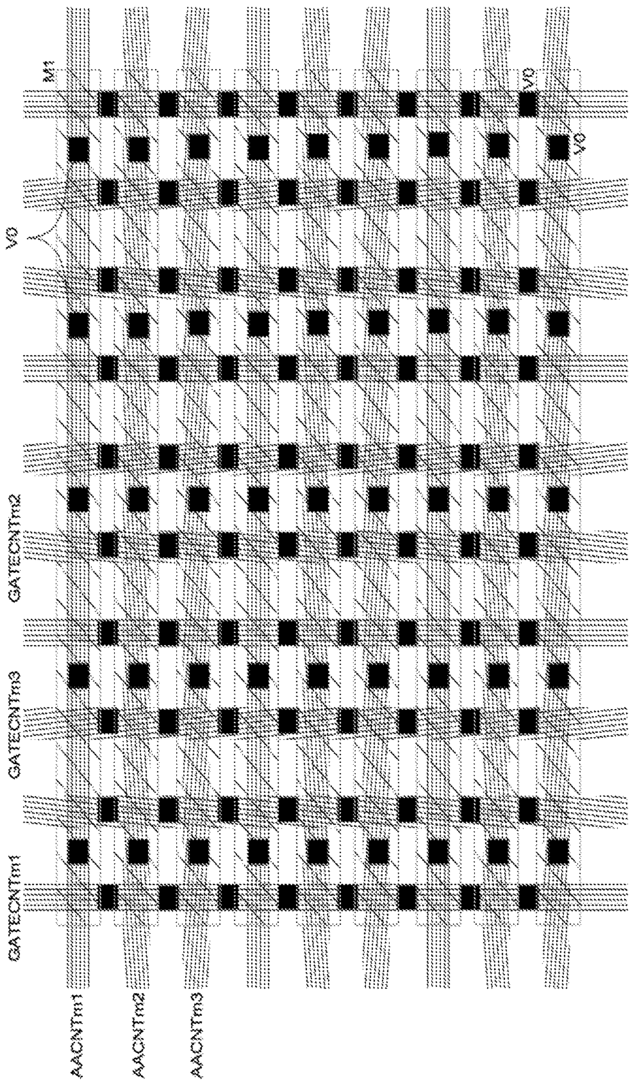
Figure 9Z:
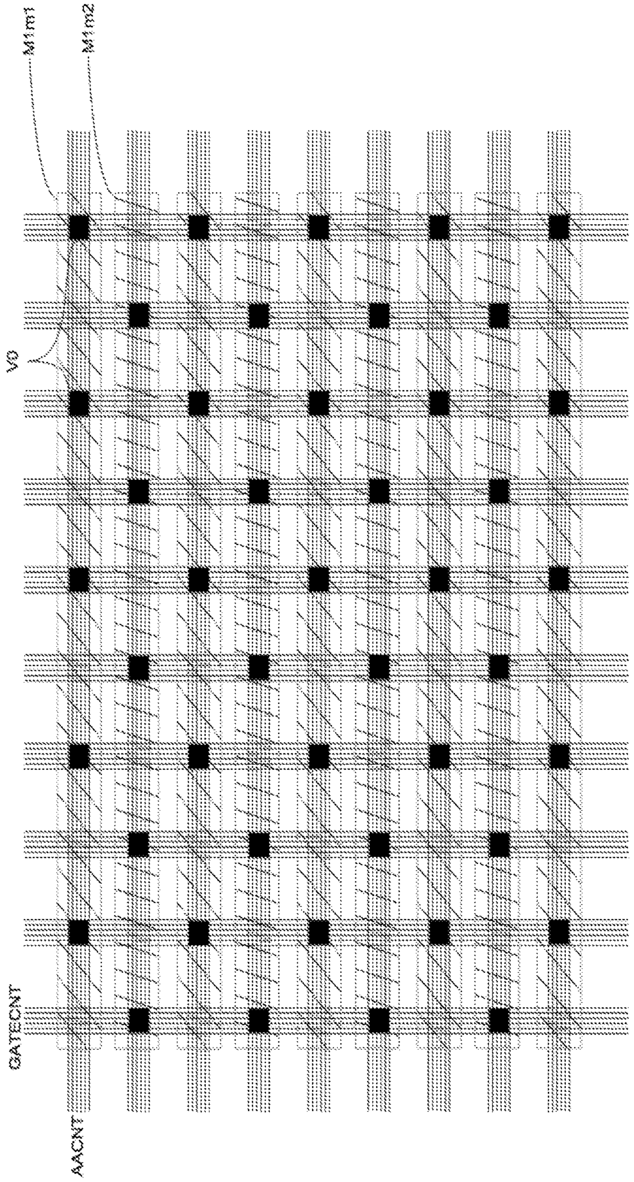

Reference is now made to FIGS. 9A-9E, which depict several illustrative designs for a NCEM pad, suitable for use in connection with embodiments of the invention. Additional NCEM pads are disclosed in the incorporated '841 application. FIG. 9A shows a simple, solid conductive pad, typically, though not necessarily, formed in M1. FIGS. 9B-9D depict several options for a non-solid, segmented, single-conductor pad. (As persons skilled in the art will appreciate, the variety of shapes for such pads is endless.) FIG. 9E depicts an example of a presently preferred, multi-conductor, mesh-style pad. Applicants' experimentation has revealed that these mesh-style pad designs—which are more space efficient and design rule friendly than single conductor pads—still produce a usable NCEM, particularly if sampled at low resolution, as taught in the incorporated '841 application. FIGS. 9F-9IIII depict additional embodiments of mesh pad structures. As persons skilled in the art will appreciate, these structures can be rendered in any size (e.g., 2×2, 2×3, 3×2, 3×3, etc.), and not just the specifically depicted 10×9 and 5×2 examples.

Design of the NCEM-enabled fill cells: Such fill cells preferably have certain common elements (e.g., height, supply rails, and GATE pitch (CPP) that is consistent with standard cells in the library), then vary according to the measurement type, layer(s) involved, and structure(s) to be evaluated/tested. NCEM-enabled fill cells come in two basic types: short[/leakage] and open[/resistance]. Relevant layers typically involve either a single process layer (e.g., GATE-to-GATE) or two process layers (e.g. GATECNT-to-GATE). Structural configurations are many, and include a set of standard structures (e.g., tip-to-tip, tip-to-side, side-to-side, etc.), as well as reference or ad hoc structures.

As depicted in FIGS. 10-11, the general structure of a short[/leakage]-configured, NCEM-enabled fill cell preferably includes four overlaid components: (i) "standard" patterning; (ii) a NCEM pad; (iii) "test gap" patterning; and (iv) pad/ground wiring. Standard patterning is that which appears in essentially all of the standard library cells, such as supply rails, and sometimes minimum contacted poly pitch (CPP) spaced rail-to-rail GATE stripes, etc. The NCEM pads can take a variety of shapes/patterns, as is non-exhaustively exemplified in FIGS. 9A-9IIII. The standard structures used for test gap patterning are depicted in FIGS. 14-30, and may include tip-to-tip, tip-to-side, side-to-side, etc. (Note that a single, short-configured NCEM-enabled fill cell may include more than one test gap, with all gaps preferably wired in parallel via the pad/ground wiring; an example with multiple test gaps appears in FIG. 45). The pad/ground wiring comprises low-resistance wiring from one side of the test gap(s) to the pad, and from the other side of the test gap(s) to a permanent or virtual ground. Points of effective ground include either supply rail, as well as any electrical structure that can conduct to the substrate under appropriate e-beam charging conditions (e.g., a p+ diode to NWELL that becomes positively charged during e-beam measurement). Virtual grounding can be accomplished by connecting to a node with sufficient capacitance to avoid discharge during e-beam measurement, and thus act as a source and/or sink for electrons during the measurement.

Figure 12:
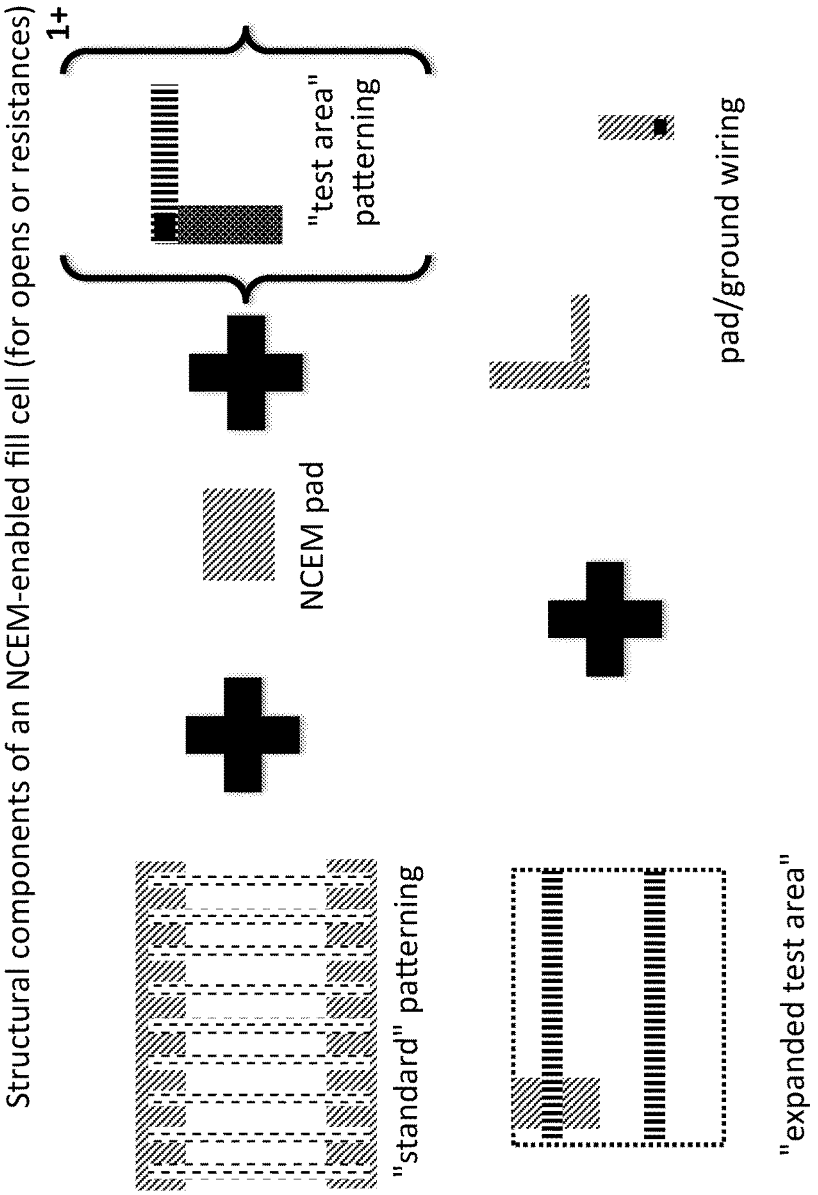
FIGS. 12-13, in conjunction with the description below, depict the overall physical structure and connectivity of open-configured (and/or resistance-configured), NCEM-enabled fill cells in accordance with certain aspects of the invention.
Figure 13:
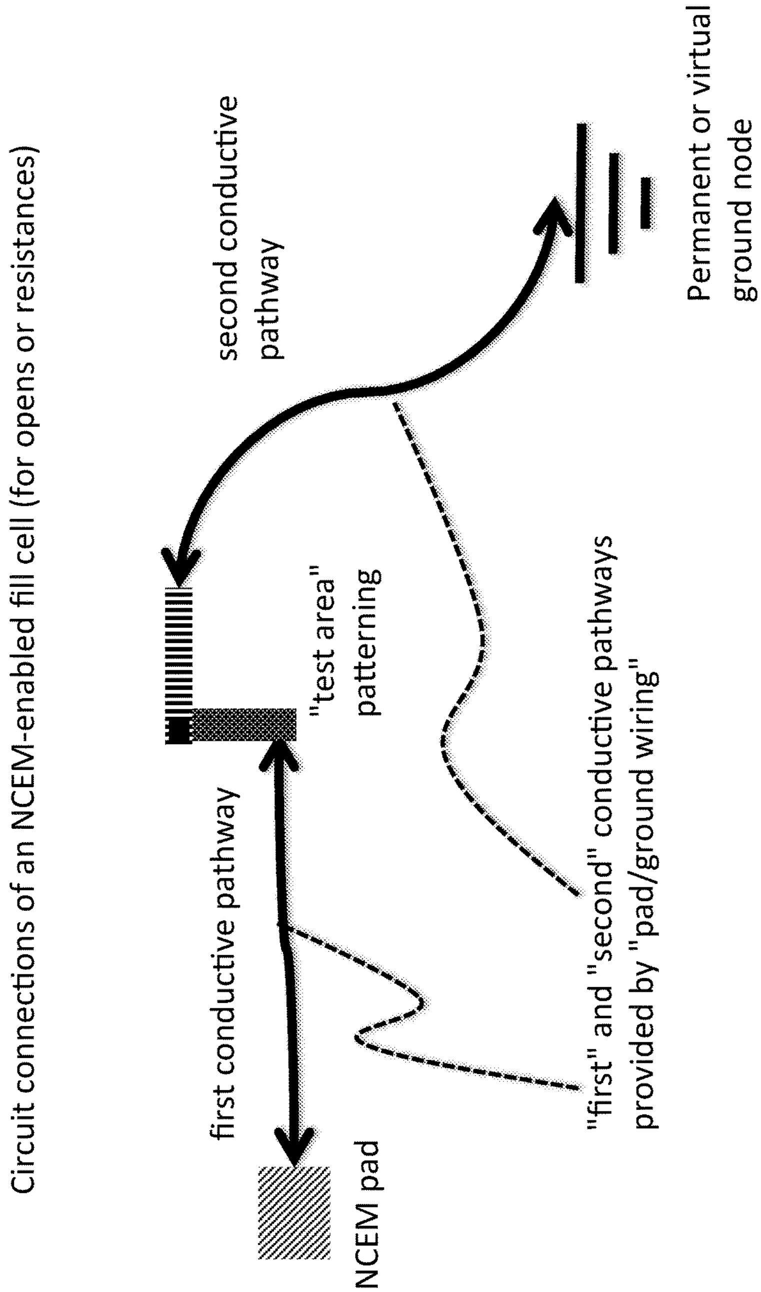

As depicted in FIGS. 12-13, the general structure of an open[/resistance]-configured, NCEM-enabled fill cell preferably includes four overlaid components: (i) "standard" patterning; (ii) a NCEM pad; (iii) "test area" patterning; and (iv) pad/ground wiring. As with the shorts, standard patterning is that which appears in essentially all of the standard library cells, such as supply rails, etc. Similarly, the NCEM pads can take a variety of shapes/patterns, as is non-exhaustively exemplified in FIGS. 9A-9IIII. Standard structures used for test structure patterning are depicted in FIGS. 28-36, and may include snake, overlap, stitch, etc. As with the shorts, the pad/ground wiring for opens comprises low-resistance wiring from one side of the test structure patterning to the pad, and from the other side of the test structure patterning to a permanent or virtual ground. Open-configured, NCEM-enabled fill cells can, and often do, include multiple test areas, in which case the pad/ground wiring connects all relevant test structures in a series-connected chain.

In cases where the NCEM-enabled fill cells will be used with a highly regular style cell library, an additional constraint on the NCEM-enabled fill cells is that they preferably conform, as closely as reasonably possible, to the regular patterns used for the library's functional cells. Preferred methods for measuring compliance with regular patterns, and/or constructing pattern-compliant cells, are described in U.S. Pat. Applic. Nos. 61/887,271 ("Template Based Design with LibAnalyzer") and 62/186,677 ("Template Based Design with LibAnalyzer"), both to Langnese et al., and both incorporated by reference herein. As those skilled in the art will appreciate, close, if not perfect, pattern compliance is feasible for those portions of the fill cell that do not affect the structure(s) or fail mode(s) to be evaluated. In general, however, perfect pattern compliance will prove infeasible for a several reasons. First, the structure to-be-evaluated may not, itself, be an "allowable" pattern (e.g., the pattern rules for the library may not allow any structure that spaces a GATE tip from a GATECNT side at minimum design rule dimensions, thus dictating that the "GATE-GATECNT-tip-to-side-short-configured, NCEM-enabled fill cell" will necessarily include at least one pattern violation). Second, DOEs typically involve several small variations in at least one minimum-spaced dimension, whereas regular patterning rules will typically only permit one of the variants. And third, the patterning used for the NCEM pad is preferably selected to match the operational capabilities of the scanner, but may well violate the library's pattern regularity constraints. Thus, ignoring these "necessary" pattern regularity violations, NCEM-enabled fill cells for use with highly regular libraries will preferably contain very few, if any, additional pattern regularity violations.

Figure 14:
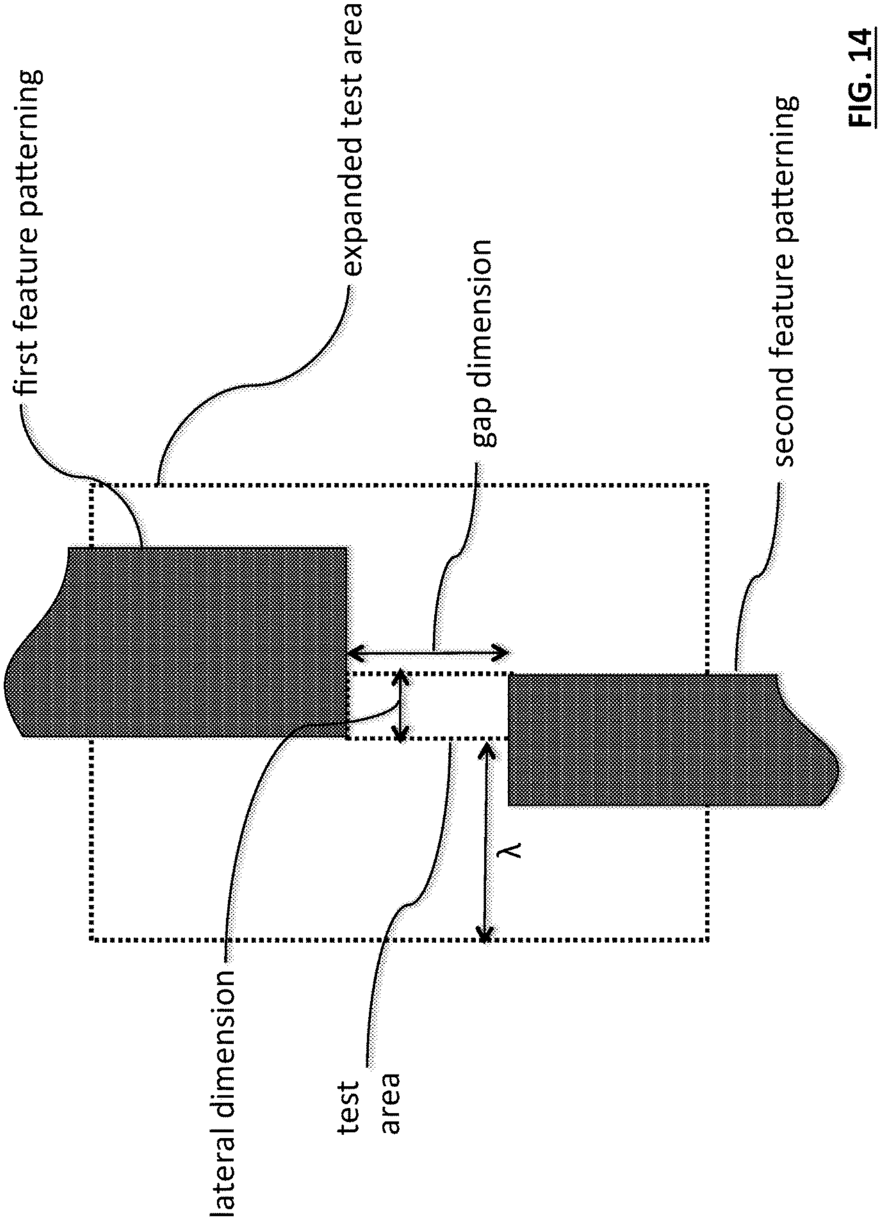
FIG. 14 depicts a plan view of exemplary test area geometry for an exemplary tip-to-tip-short-configured, NCEM-enabled fill cell.
Figure 15:
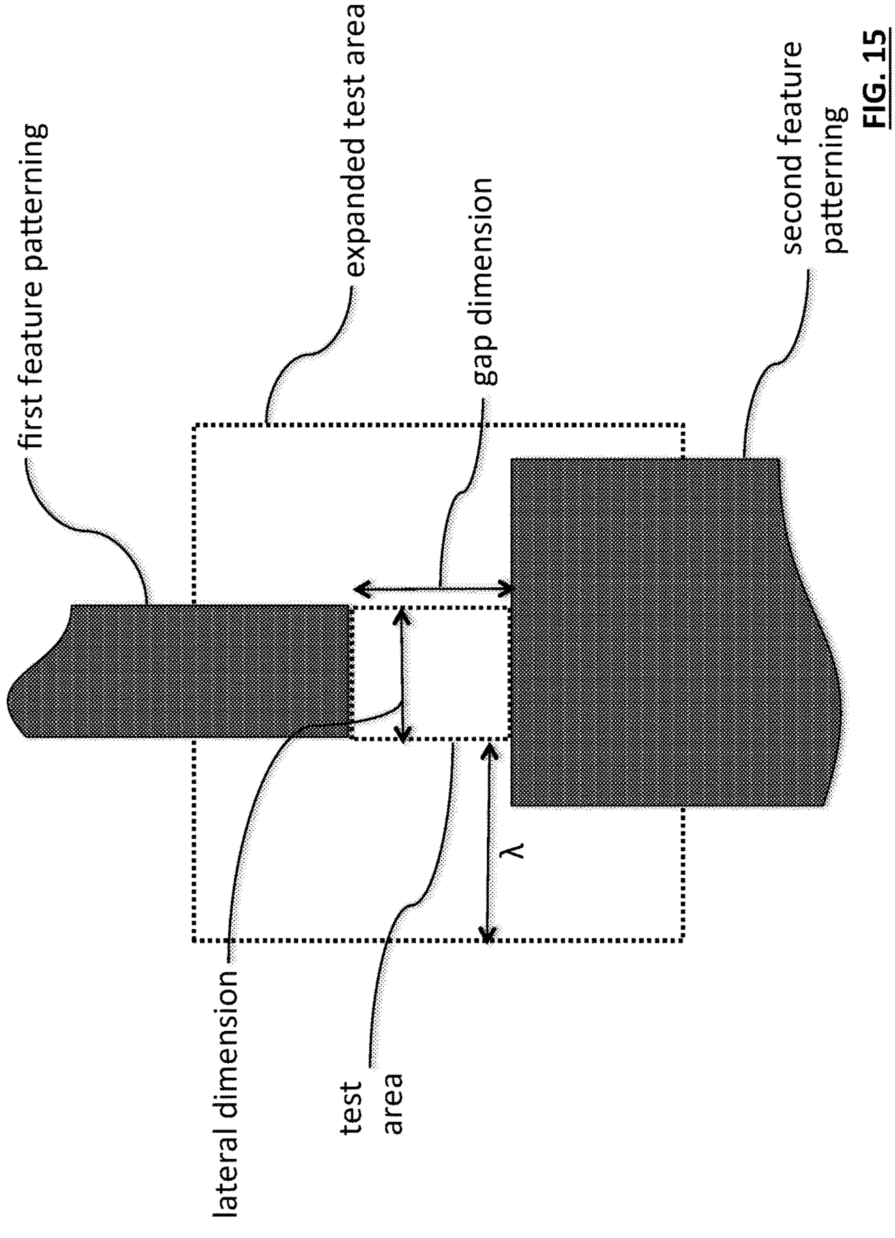
FIG. 15 depicts another plan view of exemplary test area geometry for an exemplary tip-to-tip-short-configured, NCEM-enabled fill cell.

Reference is now made to FIGS. 14-15, which depict plan views of two exemplary test area geometries for tip-to-tip-short-configured, NCEM-enabled fill cells. Cells that utilize these geometric configurations may include:

- AA-tip-to-tip-short-configured, NCEM-enabled fill cells [e.g., FIGS. 1298-1326];
- AACNT-tip-to-tip-short-configured, NCEM-enabled fill cells [e.g., FIGS. 1327-1405];
- AACNT-AA-tip-to-tip-short-configured, NCEM-enabled fill cells;
- AACNT-TS-tip-to-tip-short-configured, NCEM-enabled fill cells [e.g., FIGS. 1406-1412];
- TS-tip-to-tip-short-configured, NCEM-enabled fill cells;
- GATE-tip-to-tip-short-configured, NCEM-enabled fill cells [e.g., FIGS. 1413-1461];
- GATECNT-GATE-tip-to-tip-short-configured, NCEM-enabled fill cells;
- GATECNT-tip-to-tip-short-configured, NCEM-enabled fill cells [e.g., FIGS. 1462-1548];
- GATECNT-AACNT-tip-to-tip-short-configured, NCEM-enabled fill cells;
- M1-tip-to-tip-short-configured, NCEM-enabled fill cells [e.g., FIGS. 1549-1556];
- V0-tip-to-tip-short-configured, NCEM-enabled fill cells;
- M1-V0-tip-to-tip-short-configured, NCEM-enabled fill cells;
- V1-M1-tip-to-tip-short-configured, NCEM-enabled fill cells;
- V1-tip-to-tip-short-configured, NCEM-enabled fill cells;
- M2-tip-to-tip-short-configured, NCEM-enabled fill cells;
- M2-V1-tip-to-tip-short-configured, NCEM-enabled fill cells;
- V2-M2-tip-to-tip-short-configured, NCEM-enabled fill cells;
- M3-tip-to-tip-short-configured, NCEM-enabled fill cells;
- V2-tip-to-tip-short-configured, NCEM-enabled fill cells; and,
- M3-V2-tip-to-tip-short-configured, NCEM-enabled fill cells.
- [As persons skilled in the art will understand, for interconnect layers 2 and higher, any NCEM-enabled fill cell of type "$M_x$- . . . " can also be formed as a corresponding "$M_{(x+n)}$- . . . " cell, any "$V_x$- . . . " cell can also be formed as a corresponding "$V_{(x+n)}$- . . . " cell, any "$M_x$-$V_{(x+1)}$- . . . " cell can also be formed as a corresponding "$M_{(x+n)}$-$V_{(x+n+1)}$- . . . " cell, and any "$M_x$-$V_{(x-1)}$- . . . " cell can also be formed as a corresponding "$M_{(x+n)}$-$V_{(x+n-1)}$- . . . " cell, assuming that the process-in-question supports the referenced interconnect layers. The present description should be read as including all such possible higher interconnect layer, and layer combination, cells, in all available failure types and geometric configurations.]

DOEs of these structures are preferably constructed by varying the dimensional parameters that define the test area (e.g., lateral and/or gap dimension), or by varying other, same- or adjacent-layer patterning within the expanded test area.

Figure 16:
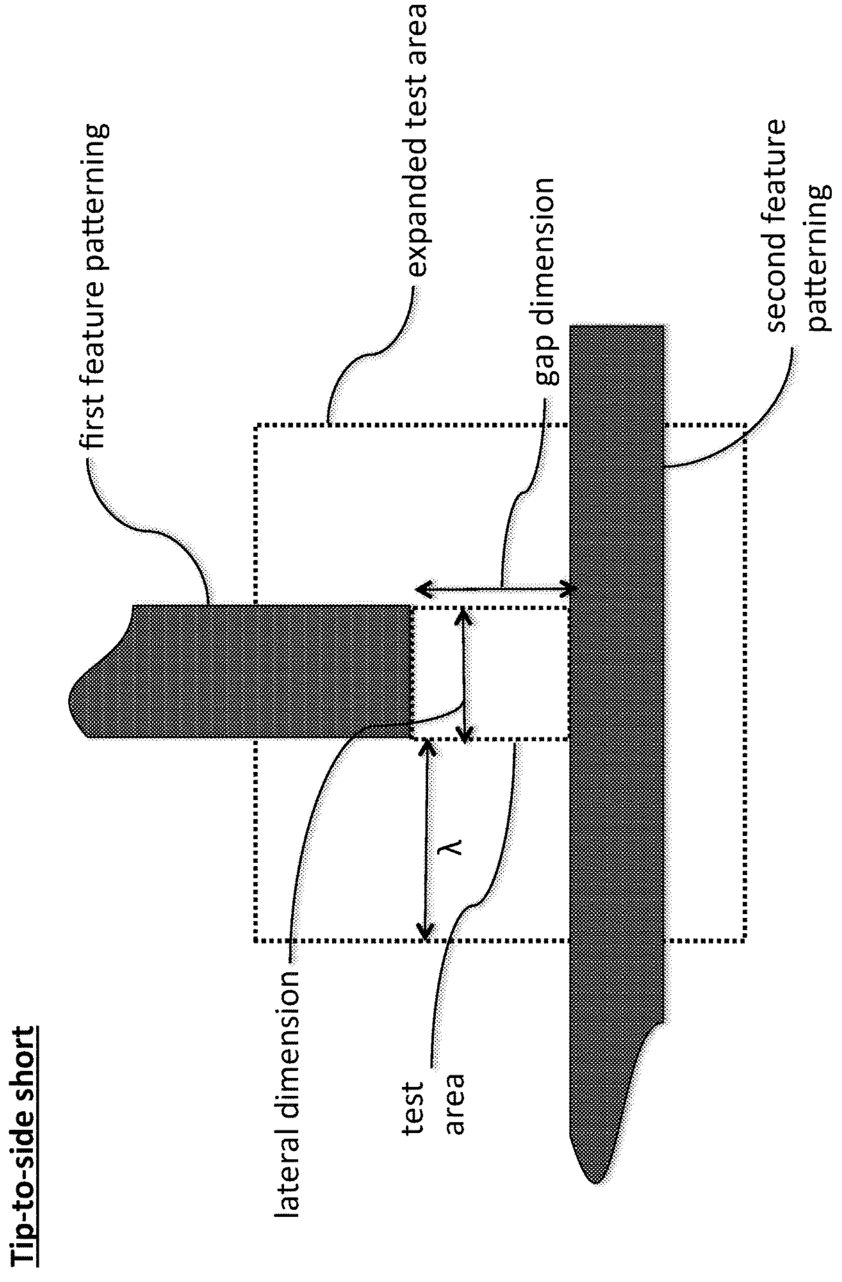
FIG. 16 depicts a plan view of exemplary test area geometry for an exemplary tip-to-side-short-configured, NCEM-enabled fill cell.
Figure 45:
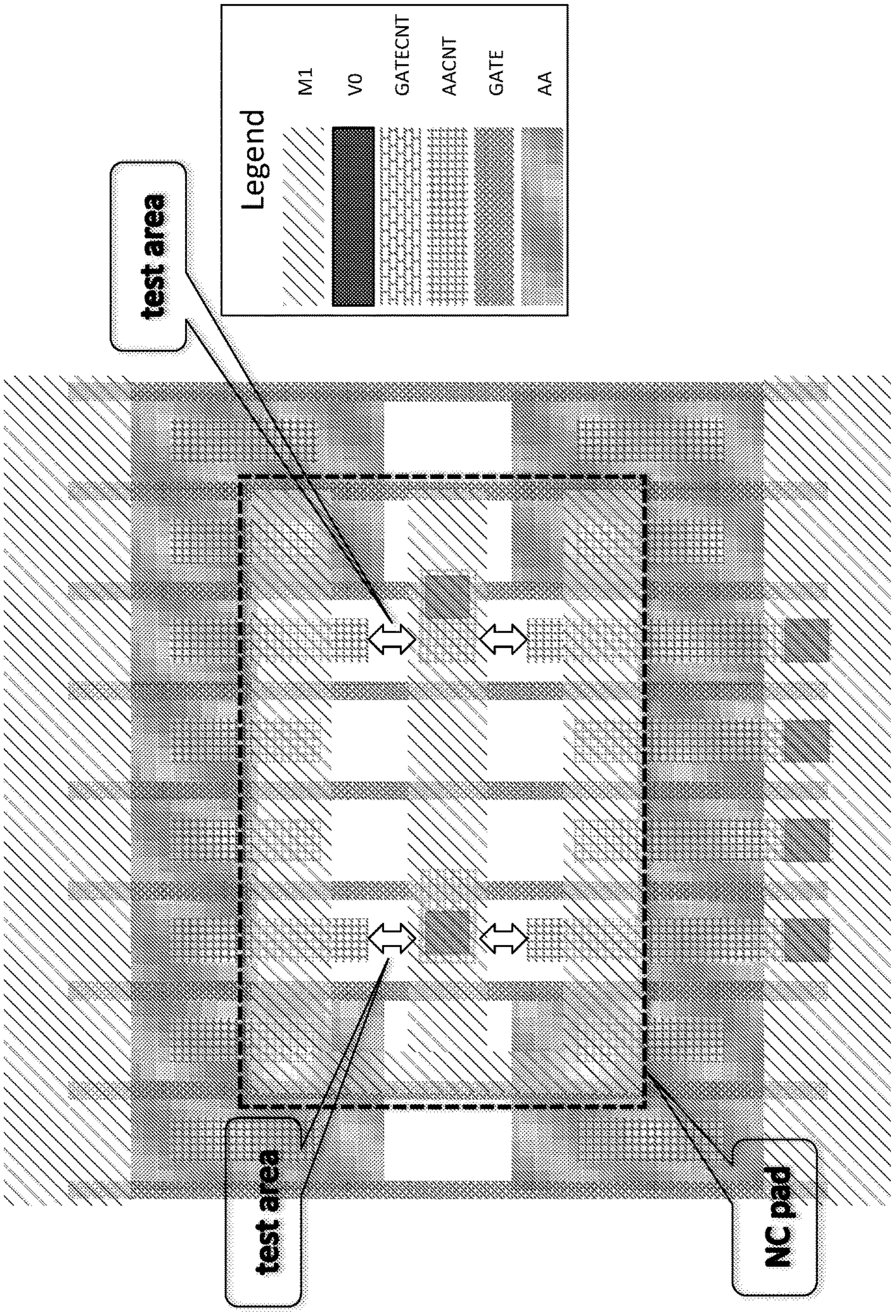

Reference is now made to FIG. 16, which depicts a plan view of exemplary test area geometry for tip-to-side-short-configured, NCEM-enabled fill cells. Cells that utilize this geometric configuration may include:

- AA-tip-to-side-short-configured, NCEM-enabled fill cells;
- AACNT-tip-to-side-short-configured, NCEM-enabled fill cells [e.g., FIG. 45];
- AACNT-AA-tip-to-side-short-configured, NCEM-enabled fill cells;
- GATE-AA-tip-to-side-short-configured, NCEM-enabled fill cells [e.g., FIGS. 49, 50, 1084-1119];
- GATECNT-GATE-tip-to-side-short-configured, NCEM-enabled fill cells [e.g., FIGS. 1201-1238];
- GATECNT-tip-to-side-short-configured, NCEM-enabled fill cells [e.g., FIGS. 1120-1149];
- TS-GATECNT-tip-to-side-short-configured, NCEM-enabled fill cells [e.g., FIGS. 1239-1263];
- GATECNT-AACNT-tip-to-side-short-configured, NCEM-enabled fill cells [FIGS. 1150-1188];
- GATECNT-AACNT-TS-tip-to-side-short-configured, NCEM-enabled fill cells [FIGS. 1189-1200];
- M1-tip-to-side-short-configured, NCEM-enabled fill cells [e.g., FIGS. 1264-1297];
- V0-tip-to-side-short-configured, NCEM-enabled fill cells;
- M1-V0-tip-to-side-short-configured, NCEM-enabled fill cells;
- V1-M1-tip-to-side-short-configured, NCEM-enabled fill cells;
- V1-tip-to-side-short-configured, NCEM-enabled fill cells;
- M2-tip-to-side-short-configured, NCEM-enabled fill cells;
- M2-V1-tip-to-side-short-configured, NCEM-enabled fill cells;
- V2-M2-tip-to-side-short-configured, NCEM-enabled fill cells;
- M3-tip-to-side-short-configured, NCEM-enabled fill cells;
- V2-tip-to-side-short-configured, NCEM-enabled fill cells; and,
- M3-V2-tip-to-side-short-configured, NCEM-enabled fill cells.

DOEs of these structures are preferably constructed by varying the dimensional parameters that define the test area (e.g., lateral and/or gap dimension), or by varying other, same- or adjacent-layer patterning within the expanded test area.

Figure 17:
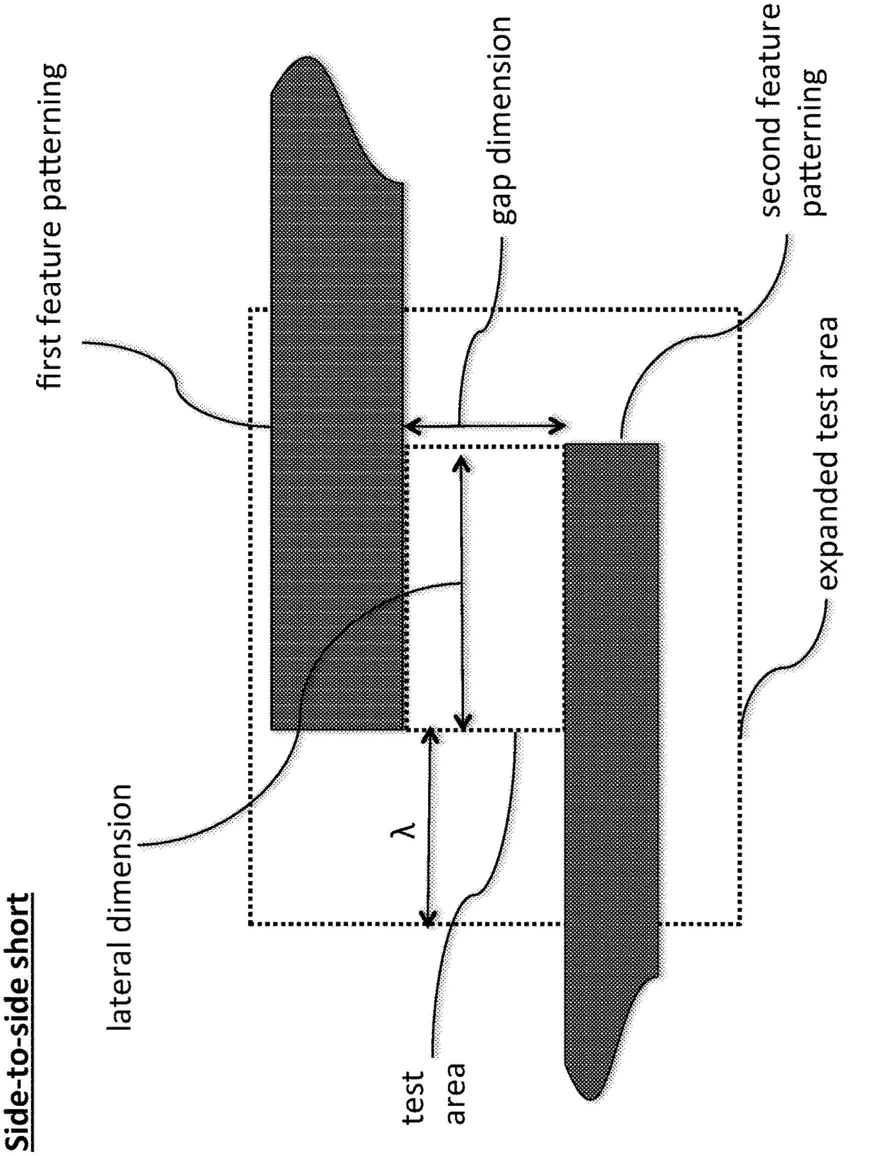
FIG. 17 depicts a plan view of exemplary test area geometry for an exemplary side-to-side-short-configured, NCEM-enabled fill cell.
Figure 18:
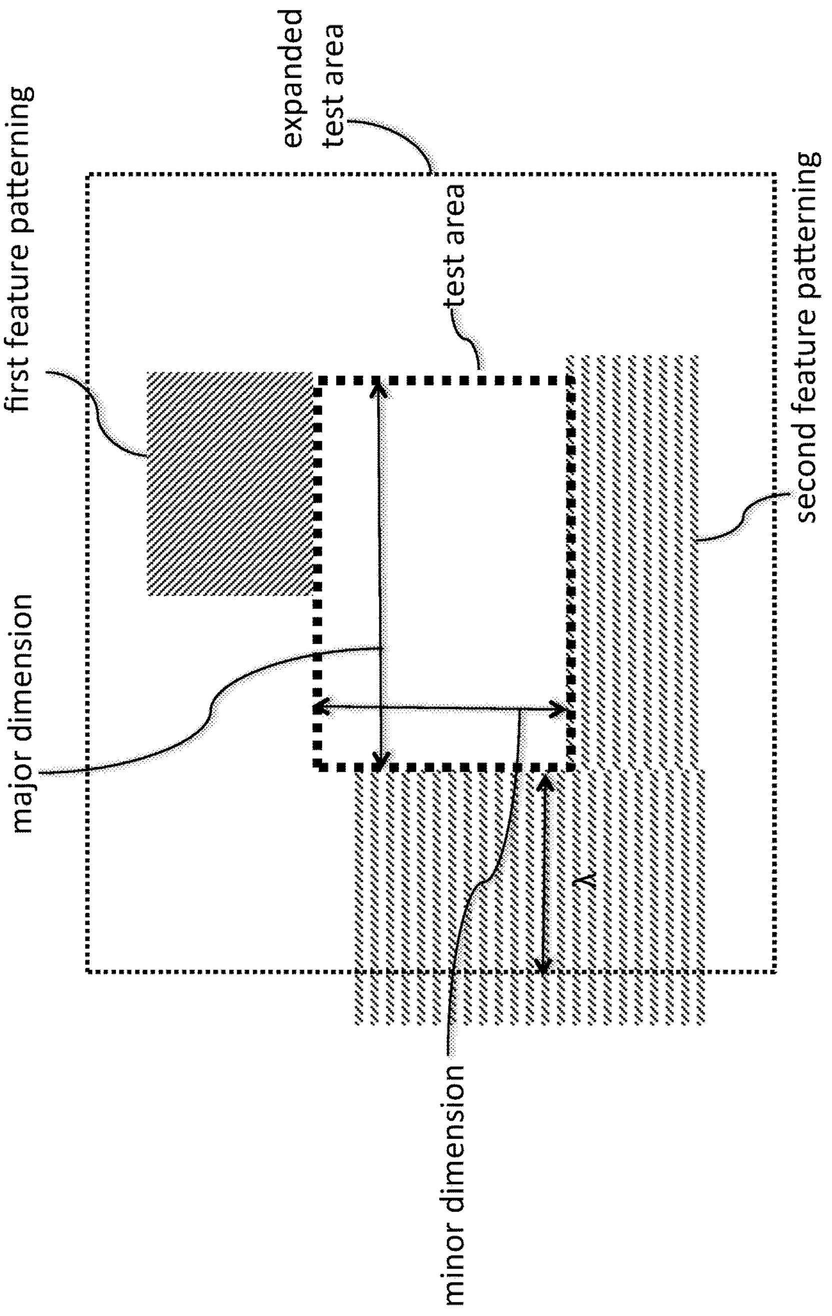
FIG. 18 depicts a plan view of exemplary test area geometry for an exemplary L-shape-interlayer-short-configured, NCEM-enabled fill cell.
Figure 19:
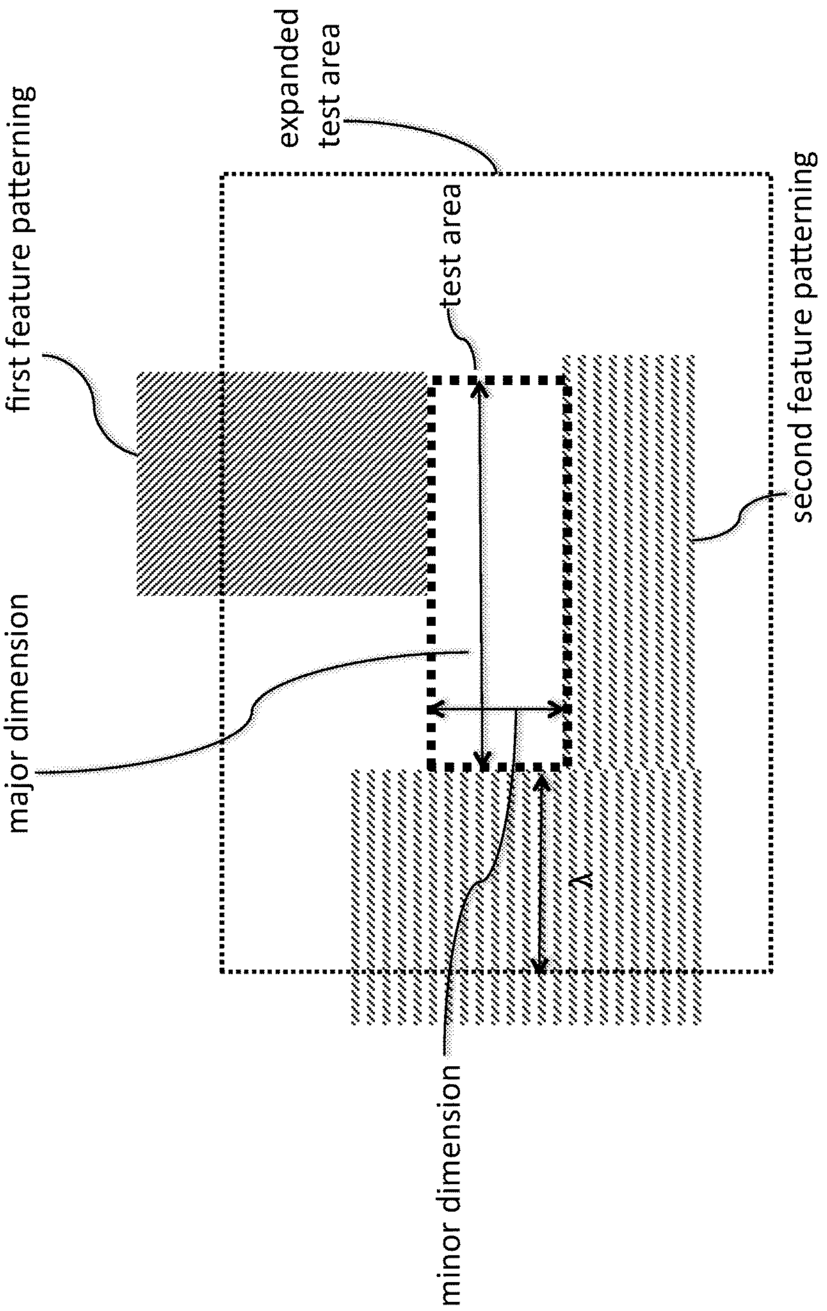
FIG. 19 depicts a plan view of exemplary test area geometry for another exemplary L-shape-interlayer-short-configured, NCEM-enabled fill cell.
Figure 20:
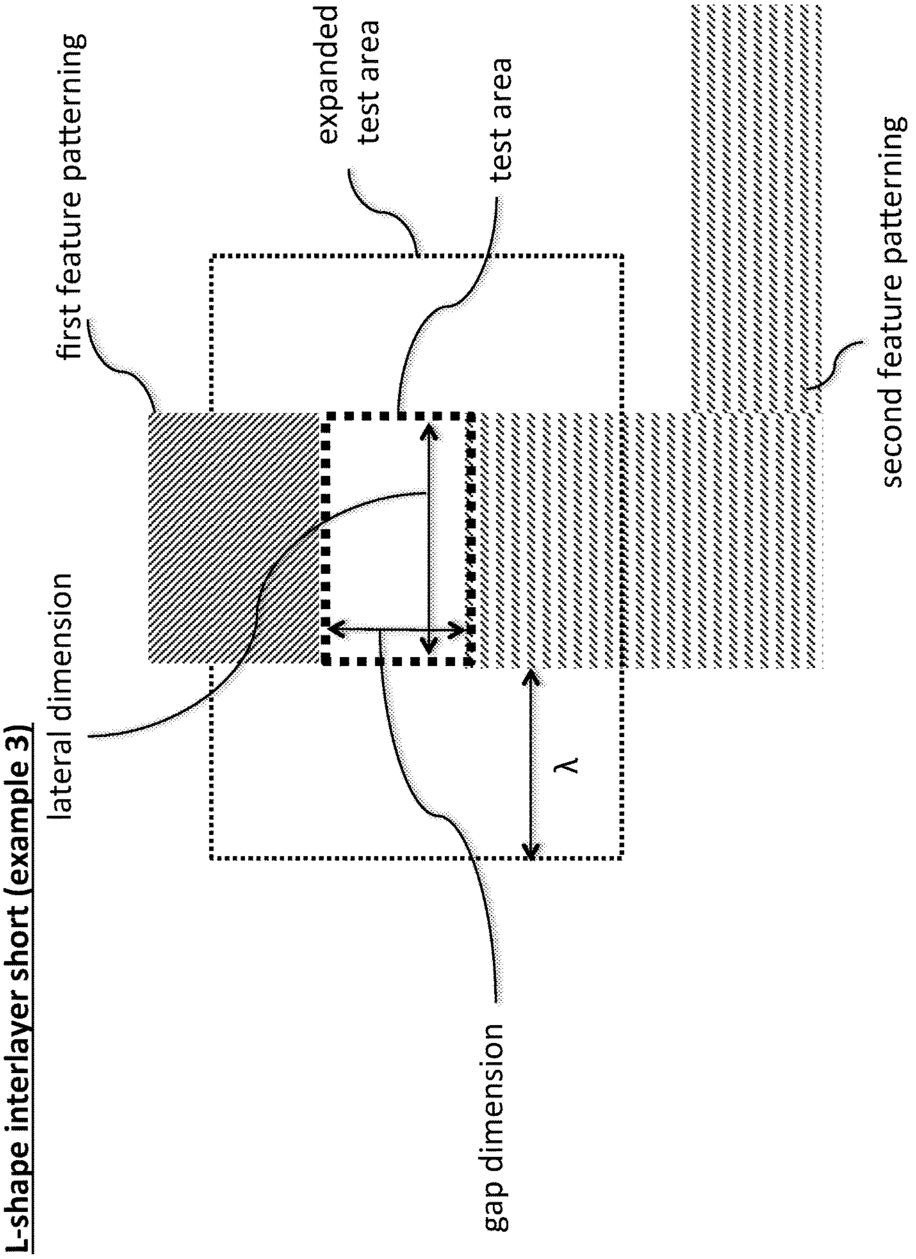
FIG. 20 depicts a plan view of exemplary test area geometry for another exemplary L-shape-interlayer-short-configured, NCEM-enabled fill cell.
Figure 21:
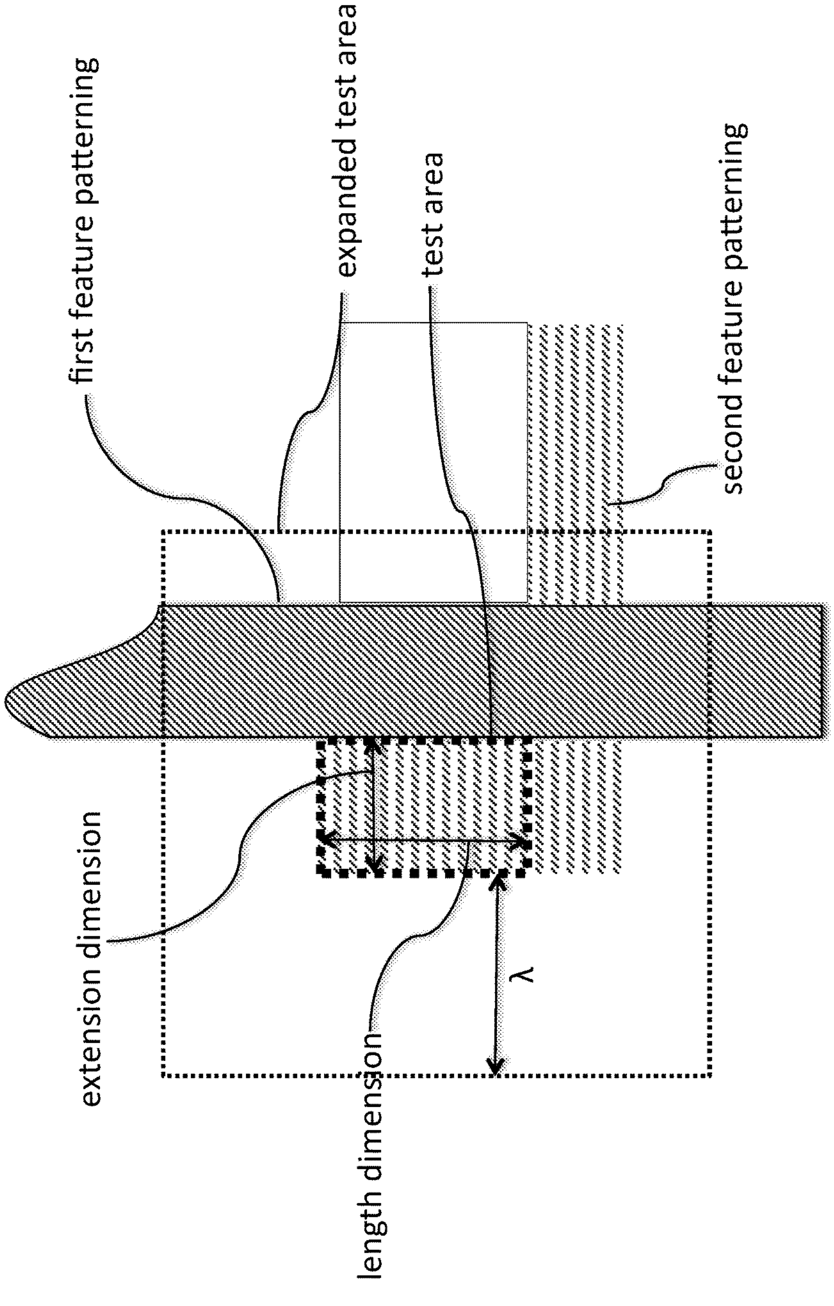
FIG. 21 depicts a plan view of exemplary test area geometry for another exemplary L-shape-interlayer-short-configured, NCEM-enabled fill cell.
Figure 22:
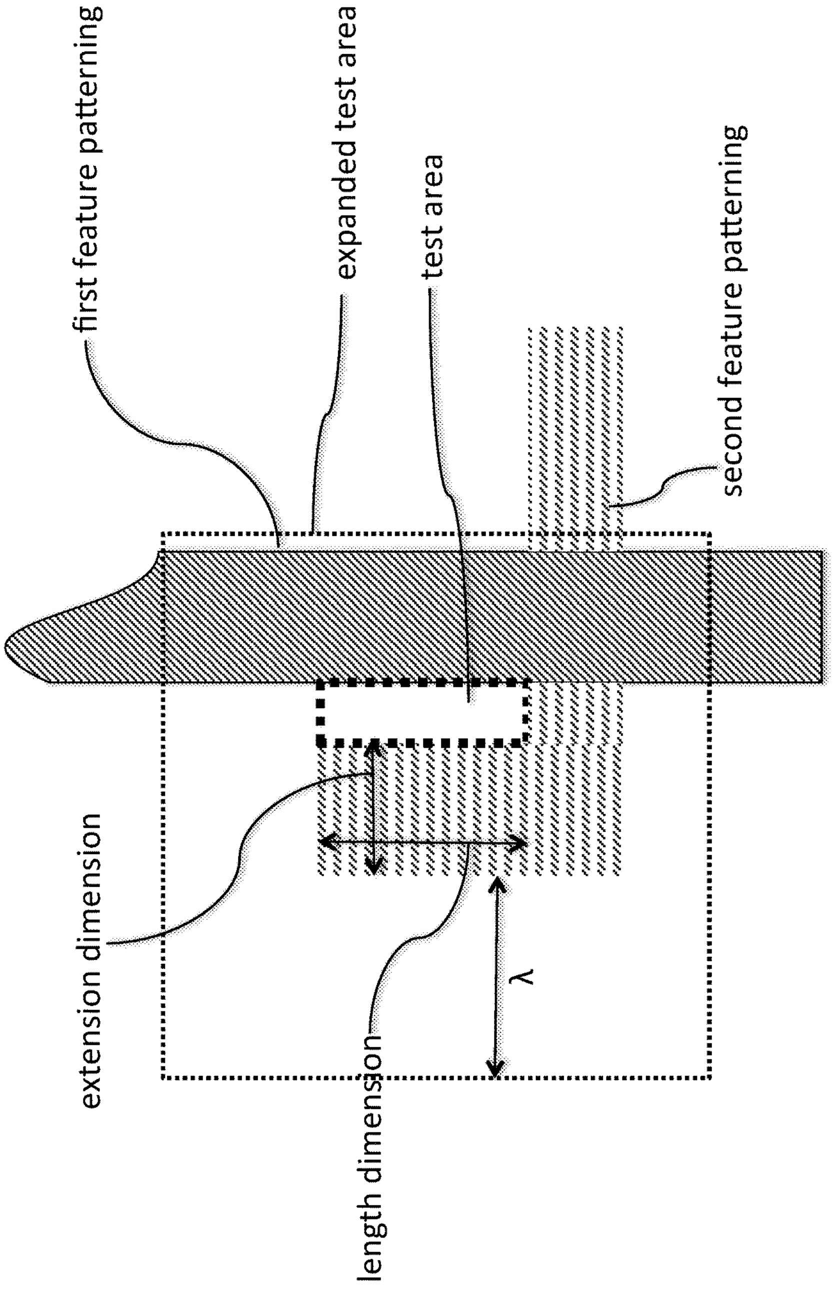
FIG. 22 depicts a plan view of exemplary test area geometry for another exemplary L-shape-interlayer-short-configured, NCEM-enabled fill cell.

Reference is now made to FIG. 17, which depicts a plan view of exemplary test area geometry for side-to-side-short-configured, NCEM-enabled fill cells. Cells that utilize this geometric configuration may include:

- AA-side-to-side-short-configured, NCEM-enabled fill cells;
- AACNT-side-to-side-short-configured, NCEM-enabled fill cells [e.g., FIGS. 786-804];
- AACNT-AA-side-to-side-short-configured, NCEM-enabled fill cells;
- AACNT-GATE-side-to-side-short-configured, NCEM-enabled fill cells [e.g., FIGS. 805-832];
- GATE-side-to-side-short-configured, NCEM-enabled fill cells [e.g., FIG. 833-859];
- GATECNT-GATE-side-to-side-short-configured, NCEM-enabled fill cells [e.g., FIGS. 886-903];
- TS-GATE-side-to-side-short-configured, NCEM-enabled fill cells [e.g., FIGS. 937-1040];

- GATECNT-side-to-side-short-configured, NCEM-enabled fill cells [e.g., FIGS. 860-872];
- GATECNT-AACNT-side-to-side-short-configured, NCEM-enabled fill cells [e.g., FIGS. 47(*a*)-(*c*), 873-885];
- M1-side-to-side-short-configured, NCEM-enabled fill cells [e.g., FIGS. 904-928];
- V0-side-to-side-short-configured, NCEM-enabled fill cells;
- M1-V0-side-to-side-short-configured, NCEM-enabled fill cells [e.g., FIGS. 929-936];
- V1-M1-side-to-side-short-configured, NCEM-enabled fill cells;
- V1-side-to-side-short-configured, NCEM-enabled fill cells;
- M2-side-to-side-short-configured, NCEM-enabled fill cells;
- M2-V1-side-to-side-short-configured, NCEM-enabled fill cells;
- V2-M2-side-to-side-short-configured, NCEM-enabled fill cells;
- M3-side-to-side-short-configured, NCEM-enabled fill cells;
- V2-side-to-side-short-configured, NCEM-enabled fill cells; and,
- M3-V2-side-to-side-short-configured, NCEM-enabled fill cells.

DOEs of these structures are preferably constructed by varying the dimensional parameters that define the test area (e.g., lateral and/or gap dimension), or by varying other, same- or adjacent-layer patterning within the expanded test area.

Reference is now made to FIGS. 18, 19, 20, 21, and 22, each of which depicts a plan view of exemplary test area geometry for L-shape-interlayer-short-configured, NCEM-enabled fill cells. Cells that utilize these geometric configurations may include:

- AA-L-shape-interlayer-short-configured, NCEM-enabled fill cells;
- AACNT-L-shape-interlayer-short-configured, NCEM-enabled fill cells;
- AACNT-AA-L-shape-interlayer-short-configured, NCEM-enabled fill cells;
- GATE-AA-L-shape-interlayer-short-configured, NCEM-enabled fill cells;
- GATE-TS-L-shape-interlayer-short-configured, NCEM-enabled fill cells;
- GATECNT-GATE-L-shape-interlayer-short-configured, NCEM-enabled fill cells;
- GATECNT-AA-L-shape-interlayer-short-configured, NCEM-enabled fill cells;
- GATECNT-TS-L-shape-interlayer-short-configured, NCEM-enabled fill cells;
- GATECNT-AACNT-L-shape-interlayer-short-configured, NCEM-enabled fill cells;
- V0-AA-L-shape-interlayer-short-configured, NCEM-enabled fill cells;
- V0-TS-L-shape-interlayer-short-configured, NCEM-enabled fill cells;
- V0-AACNT-L-shape-interlayer-short-configured, NCEM-enabled fill cells;
- V0-GATE-L-shape-interlayer-short-configured, NCEM-enabled fill cells;
- V0-GATECNT-L-shape-interlayer-short-configured, NCEM-enabled fill cells;
- M1-AACNT-L-shape-interlayer-short-configured, NCEM-enabled fill cells;
- M1-GATECNT-L-shape-interlayer-short-configured, NCEM-enabled fill cells;
- M1-V0-L-shape-interlayer-short-configured, NCEM-enabled fill cells;
- V1-M1-L-shape-interlayer-short-configured, NCEM-enabled fill cells;
- V1-V0-L-shape-interlayer-short-configured, NCEM-enabled fill cells;
- M2-M1-L-shape-interlayer-short-configured, NCEM-enabled fill cells;
- M2-V1-L-shape-interlayer-short-configured, NCEM-enabled fill cells;
- V2-V1-L-shape-interlayer-short-configured, NCEM-enabled fill cells;
- V2-M2-L-shape-interlayer-short-configured, NCEM-enabled fill cells;
- M3-M2-L-shape-interlayer-short-configured, NCEM-enabled fill cells; and,
- M3-V2-L-shape-interlayer-short-configured, NCEM-enabled fill cells.

DOEs of these structures are preferably constructed by varying the dimensional parameters that define the test area, or by varying other, same- or adjacent-layer patterning within the expanded test area.

Figure 23:
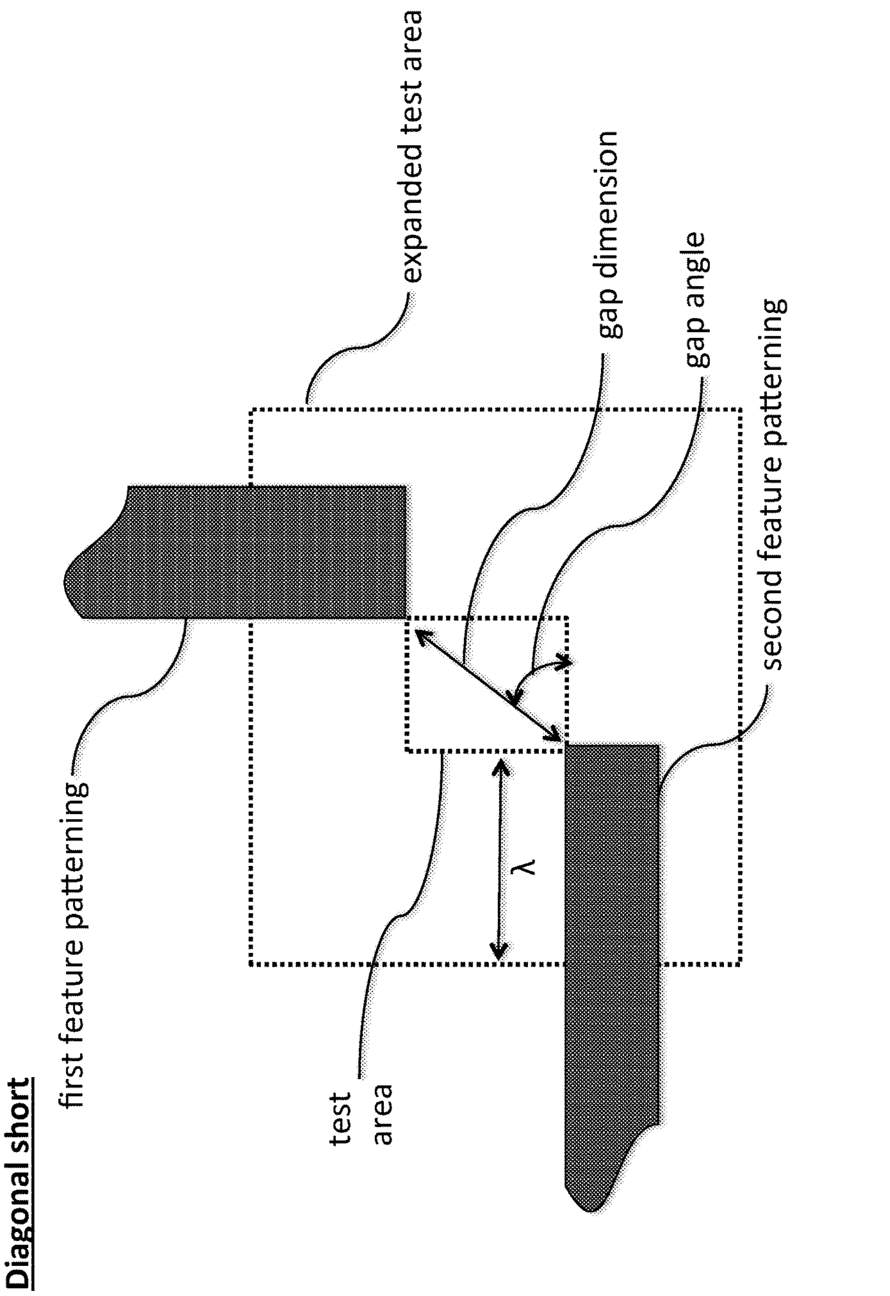
FIG. 23 depicts a plan view of exemplary test area geometry for an exemplary diagonal-short-configured, NCEM-enabled fill cell.

Reference is now made to FIG. 23, which depicts a plan view of exemplary test area geometry for diagonal-short-configured, NCEM-enabled fill cells. Cells that utilize this geometric configuration may include:

- AA-diagonal-short-configured, NCEM-enabled fill cells;
- TS-diagonal-short-configured, NCEM-enabled fill cells;
- AACNT-diagonal-short-configured, NCEM-enabled fill cells;
- AACNT-AA-diagonal-short-configured, NCEM-enabled fill cells;
- GATE-diagonal-short-configured, NCEM-enabled fill cells;
- GATE-AACNT-diagonal-short-configured, NCEM-enabled fill cells;
- GATECNT-GATE-diagonal-short-configured, NCEM-enabled fill cells;
- GATECNT-diagonal-short-configured, NCEM-enabled fill cells [e.g., FIGS. 495-554];
- GATECNT-AACNT-diagonal-short-configured, NCEM-enabled fill cells [e.g., FIGS. 555-632];
- M1-diagonal-short-configured, NCEM-enabled fill cells;
- V0-diagonal-short-configured, NCEM-enabled fill cells;
- M1-V0-diagonal-short-configured, NCEM-enabled fill cells;
- V1-M1-diagonal-short-configured, NCEM-enabled fill cells;
- V1-diagonal-short-configured, NCEM-enabled fill cells;
- M2-diagonal-short-configured, NCEM-enabled fill cells;
- M2-V1-diagonal-short-configured, NCEM-enabled fill cells;
- M3-diagonal-short-configured, NCEM-enabled fill cells;
- V2-M2-diagonal-short-configured, NCEM-enabled fill cells;
- V2-diagonal-short-configured, NCEM-enabled fill cells; and,
- M3-V2-diagonal-short-configured, NCEM-enabled fill cells.

DOEs of these structures are preferably constructed by varying the dimensional parameters that define the test area (e.g., gap dimension and/or gap angle), or by varying other, same- or adjacent-layer patterning within the expanded test area.

Figure 24:
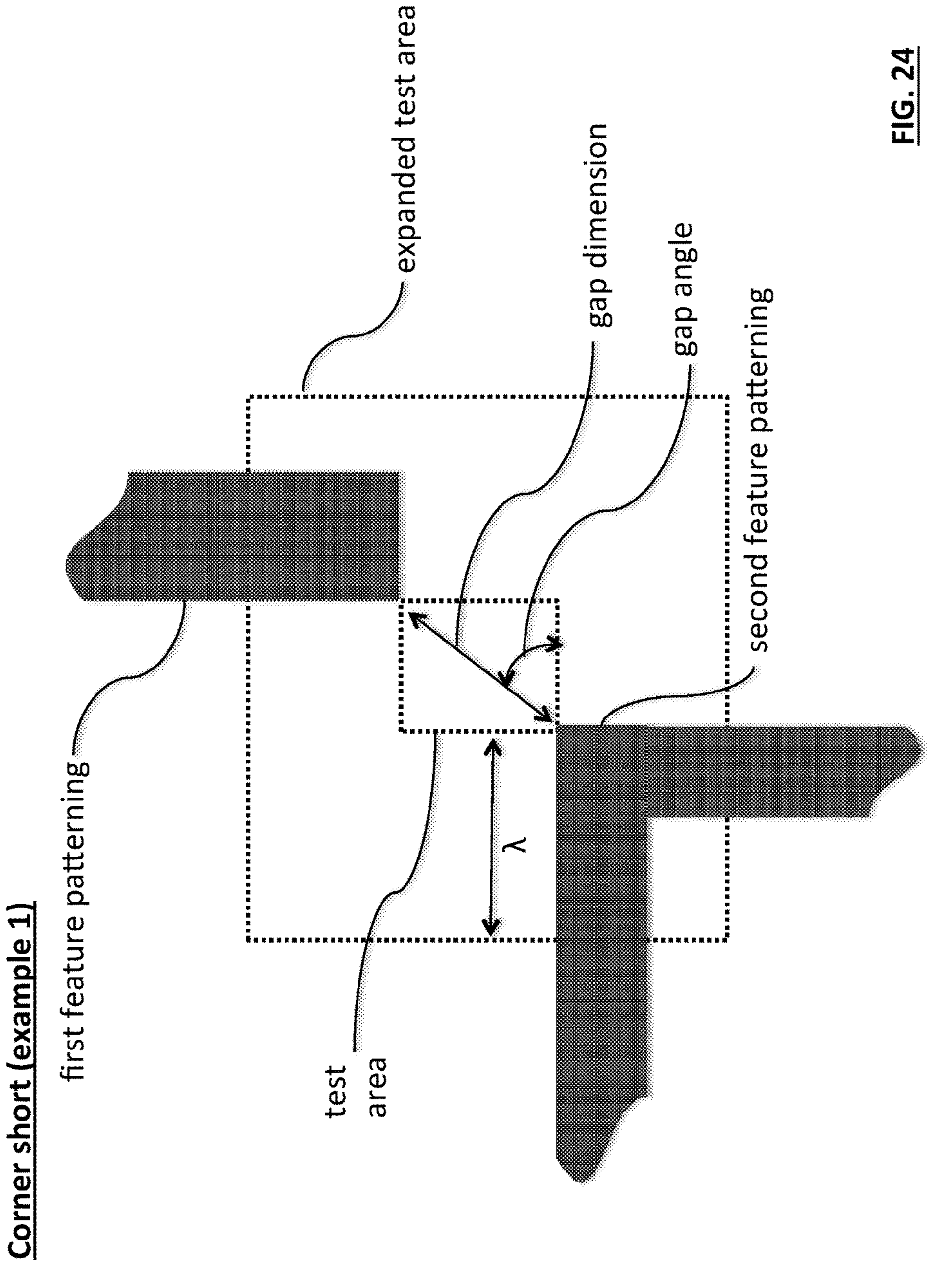
FIG. 24 depicts a plan view of exemplary test area geometry for an exemplary corner-short-configured, NCEM-enabled fill cell.
Figure 25:
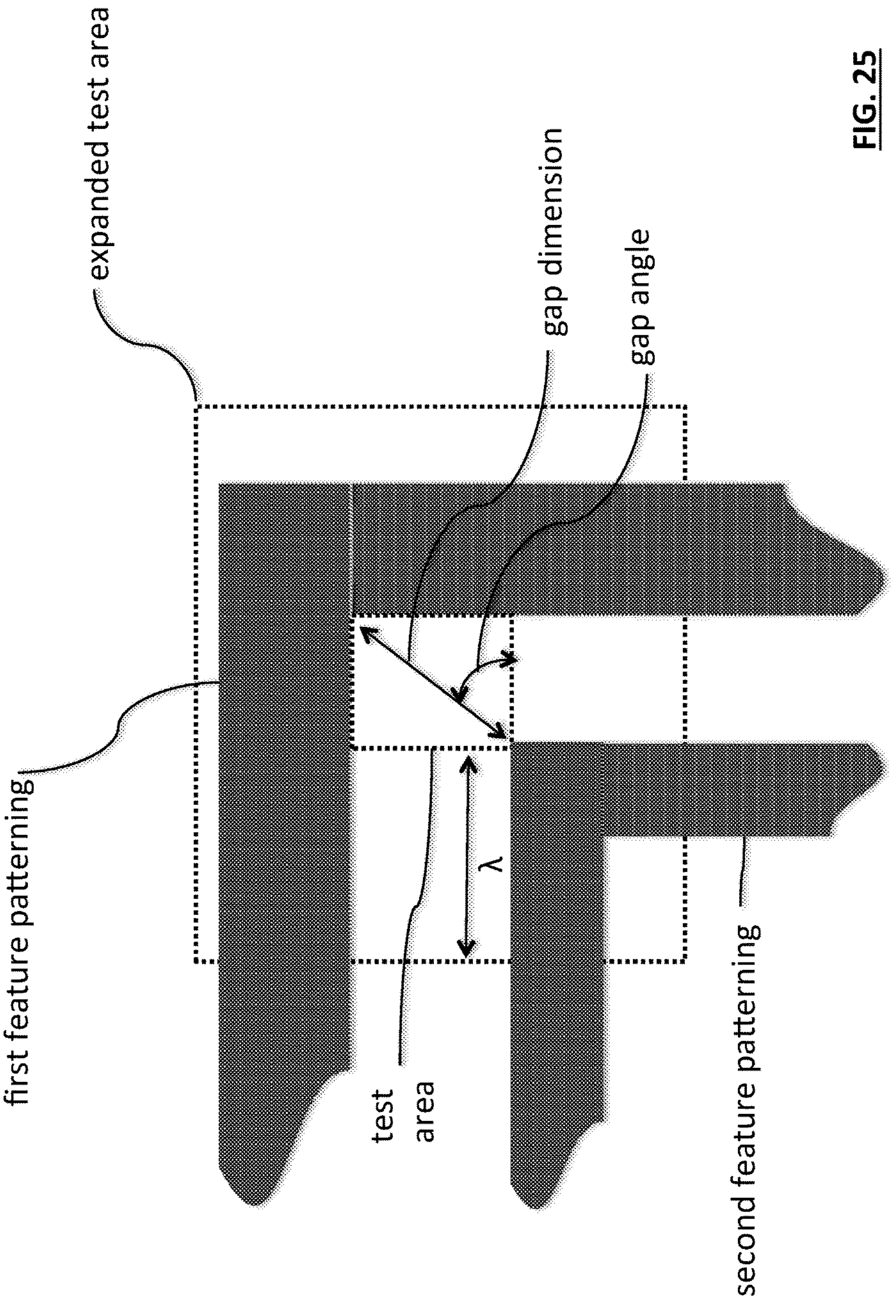
FIG. 25 depicts a plan view of exemplary test area geometry for another exemplary corner-short-configured, NCEM-enabled fill cell.
Figure 26:
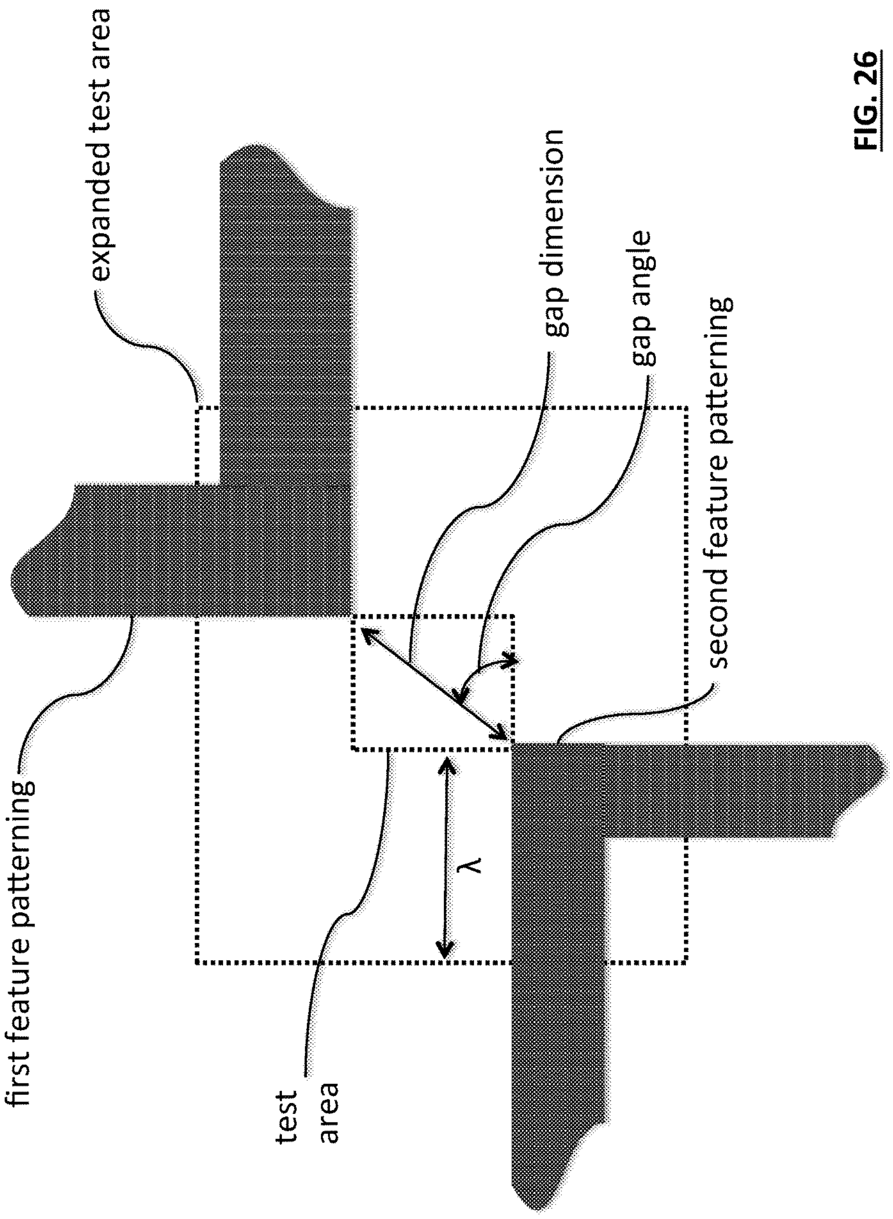
FIG. 26 depicts a plan view of exemplary test area geometry for another exemplary corner-short-configured, NCEM-enabled fill cell.

Reference is now made to FIGS. 24, 25, and 26, each of which depicts a plan view of exemplary test area geometry for corner-short-configured, NCEM-enabled fill cells. These configurations differ from the diagonal configuration because, in these corner configurations, at least one of the first and/or second features is non-rectangular. Cells that utilize these geometric configurations may include:

AA-corner-short-configured, NCEM-enabled fill cells;
AACNT-corner-short-configured, NCEM-enabled fill cells;
AACNT-AA-corner-short-configured, NCEM-enabled fill cells;
GATE-corner-short-configured, NCEM-enabled fill cells;
GATECNT-GATE-corner-short-configured, NCEM-enabled fill cells;
GATECNT-TS-corner-short-configured, NCEM-enabled fill cells [e.g., FIGS. 287-685];
GATECNT-corner-short-configured, NCEM-enabled fill cells;
GATECNT-AA-corner-short-configured, NCEM-enabled fill cells [e.g., FIGS. 263-286];
GATECNT-AACNT-corner-short-configured, NCEM-enabled fill cells;
M1-corner-short-configured, NCEM-enabled fill cells [e.g., FIGS. 416-494];
V0-corner-short-configured, NCEM-enabled fill cells;
M1-V0-corner-short-configured, NCEM-enabled fill cells;
V1-M1-corner-short-configured, NCEM-enabled fill cells;
V1-corner-short-configured, NCEM-enabled fill cells;
M2-corner-short-configured, NCEM-enabled fill cells;
M2-V1-corner-short-configured, NCEM-enabled fill cells;
M3-corner-short-configured, NCEM-enabled fill cells;
V2-M2-corner-short-configured, NCEM-enabled fill cells;
V2-corner-short-configured, NCEM-enabled fill cells; and,
M3-V2-corner-short-configured, NCEM-enabled fill cells.

DOEs of these structures are preferably constructed by varying the dimensional parameters that define the test area (e.g., gap dimension and/or gap angle), or by varying other, same- or adjacent-layer patterning within the expanded test area.

Figure 27:
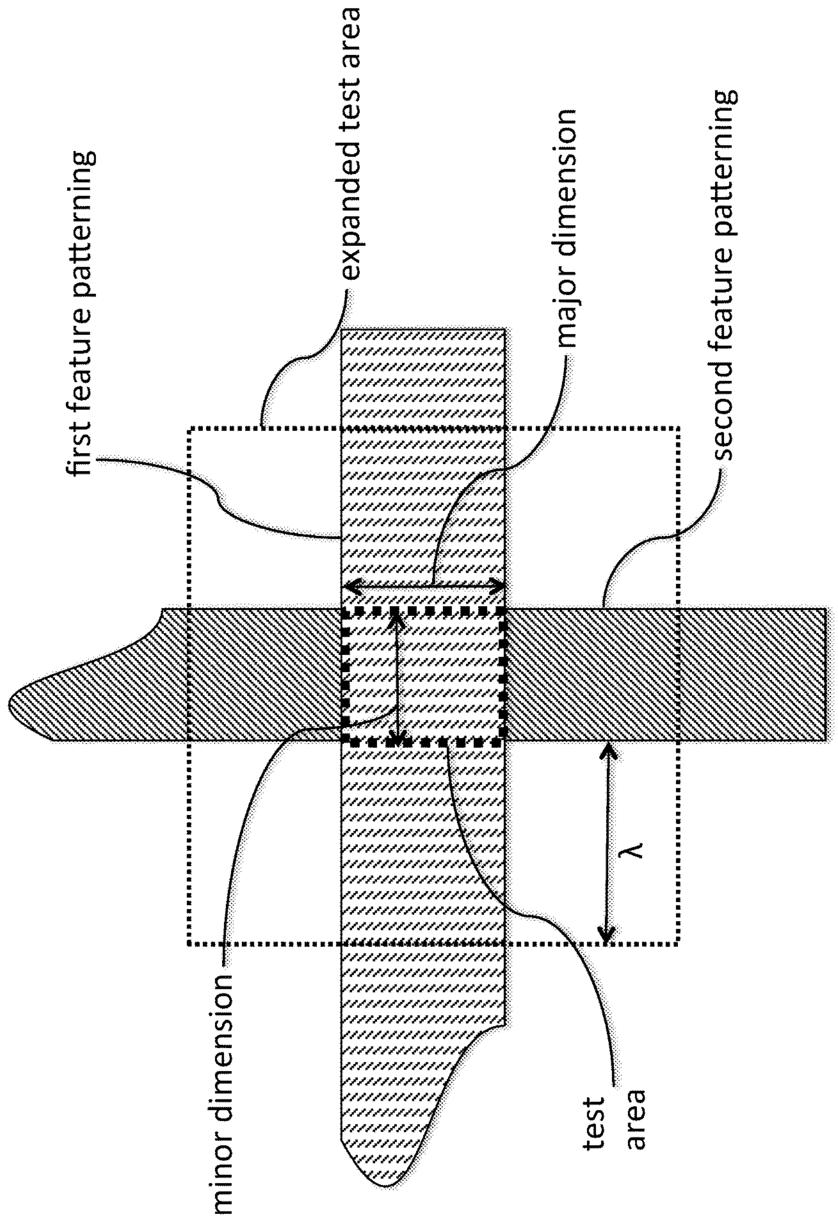
FIG. 27 depicts a plan view of exemplary test area geometry for an exemplary interlayer-overlap-short-configured, NCEM-enabled fill cell.

Reference is now made to FIG. 27, which depicts a plan view of exemplary test area geometry for interlayer-overlap-short-configured, NCEM-enabled fill cells. Cells that utilize this geometric configuration may include:

GATE-AA-interlayer-overlap-short-configured, NCEM-enabled fill cells [e.g., FIGS. 692-734];
GATE-AACNT-interlayer-overlap-short-configured, NCEM-enabled fill cells [e.g., FIGS. 633-691];
GATE-TS-interlayer-overlap-short-configured, NCEM-enabled fill cells;
GATECNT-TS-interlayer-overlap-short-configured, NCEM-enabled fill cells;
GATECNT-AA-interlayer-overlap-short-configured, NCEM-enabled fill cells;
V0-AA-interlayer-overlap-short-configured, NCEM-enabled fill cells;
V0-AACNT-interlayer-overlap-short-configured, NCEM-enabled fill cells;
V0-TS-interlayer-overlap-short-configured, NCEM-enabled fill cells;
V0-GATE-interlayer-overlap-short-configured, NCEM-enabled fill cells;
M1-GATECNT-interlayer-overlap-short-configured, NCEM-enabled fill cells;
M1-AACNT-interlayer-overlap-short-configured, NCEM-enabled fill cells;
V1-V0-interlayer-overlap-short-configured, NCEM-enabled fill cells;
M2-M1-interlayer-overlap-short-configured, NCEM-enabled fill cells;
V2-V1-interlayer-overlap-short-configured, NCEM-enabled fill cells; and,
M3-M2-interlayer-overlap-short-configured, NCEM-enabled fill cells.

DOEs of these structures are preferably constructed by varying the dimensional parameters that define the test area (e.g., major and/or minor dimension), or by varying other, same- or adjacent-layer patterning within the expanded test area.

Figure 28:
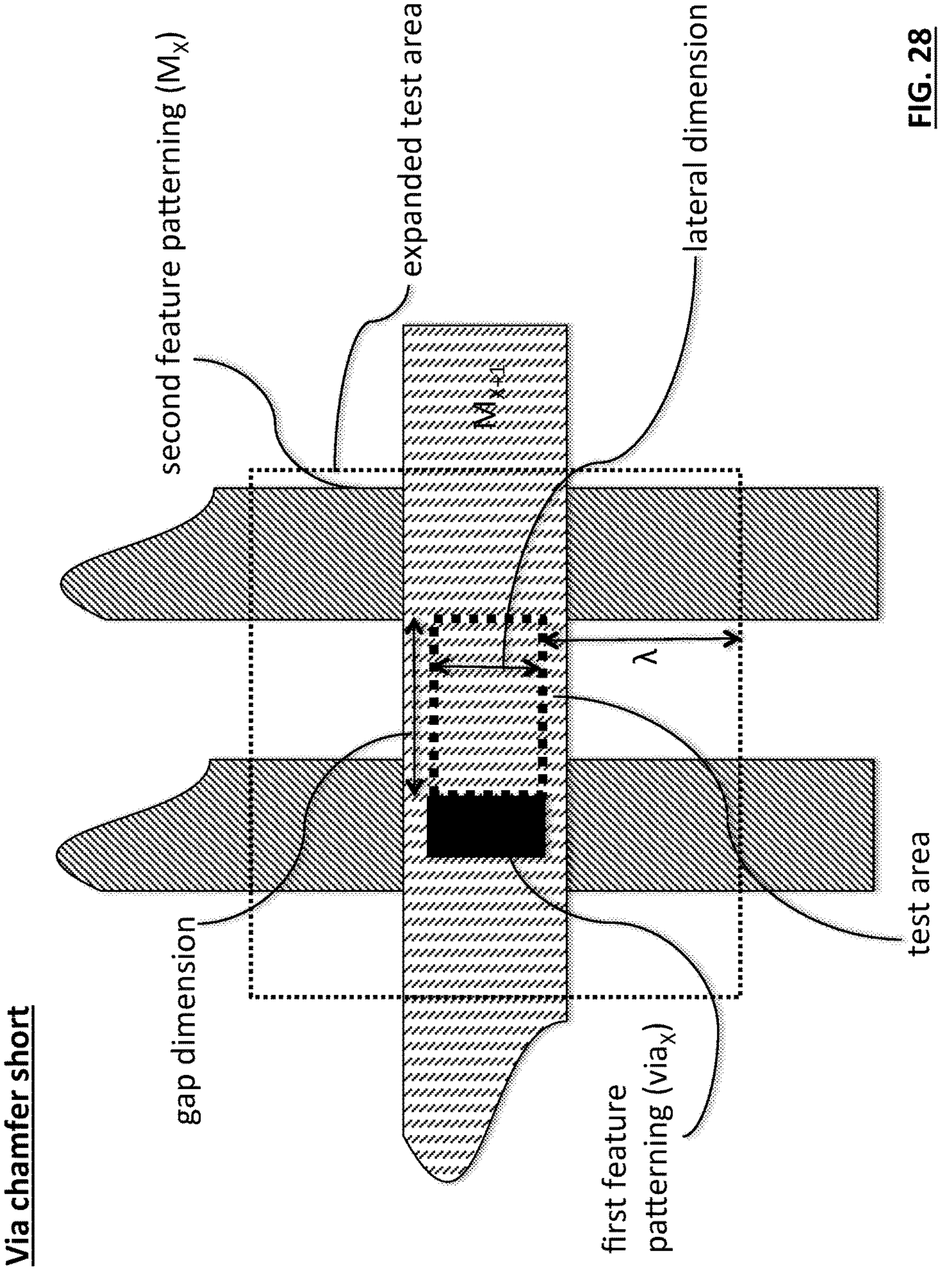
FIG. 28 depicts a plan view of exemplary test area geometry for an exemplary via-chamfer-short-configured, NCEM-enabled fill cell.

Reference is now made to FIG. 28, which depicts a plan view of exemplary test area geometry for via-chamfer-short-configured, NCEM-enabled fill cells. Cells that utilize this geometric configuration may include:

V0-GATECNT-via-chamfer-short-configured, NCEM-enabled fill cells;
V0-AACNT-via-chamfer-short-configured, NCEM-enabled fill cells [e.g., FIGS. 52-256];
V1-M1-via-chamfer-short-configured, NCEM-enabled fill cells;
V2-M2-via-chamfer-short-configured, NCEM-enabled fill cells; and,
V3-M3-via-chamfer-short-configured, NCEM-enabled fill cells [e.g., FIGS. 257-262].

DOEs of these structures are preferably constructed by varying the dimensional parameters that define the test area (e.g., gap and/or lateral dimension), or by varying other, same- or adjacent-layer patterning within the expanded test area.

Figure 29:
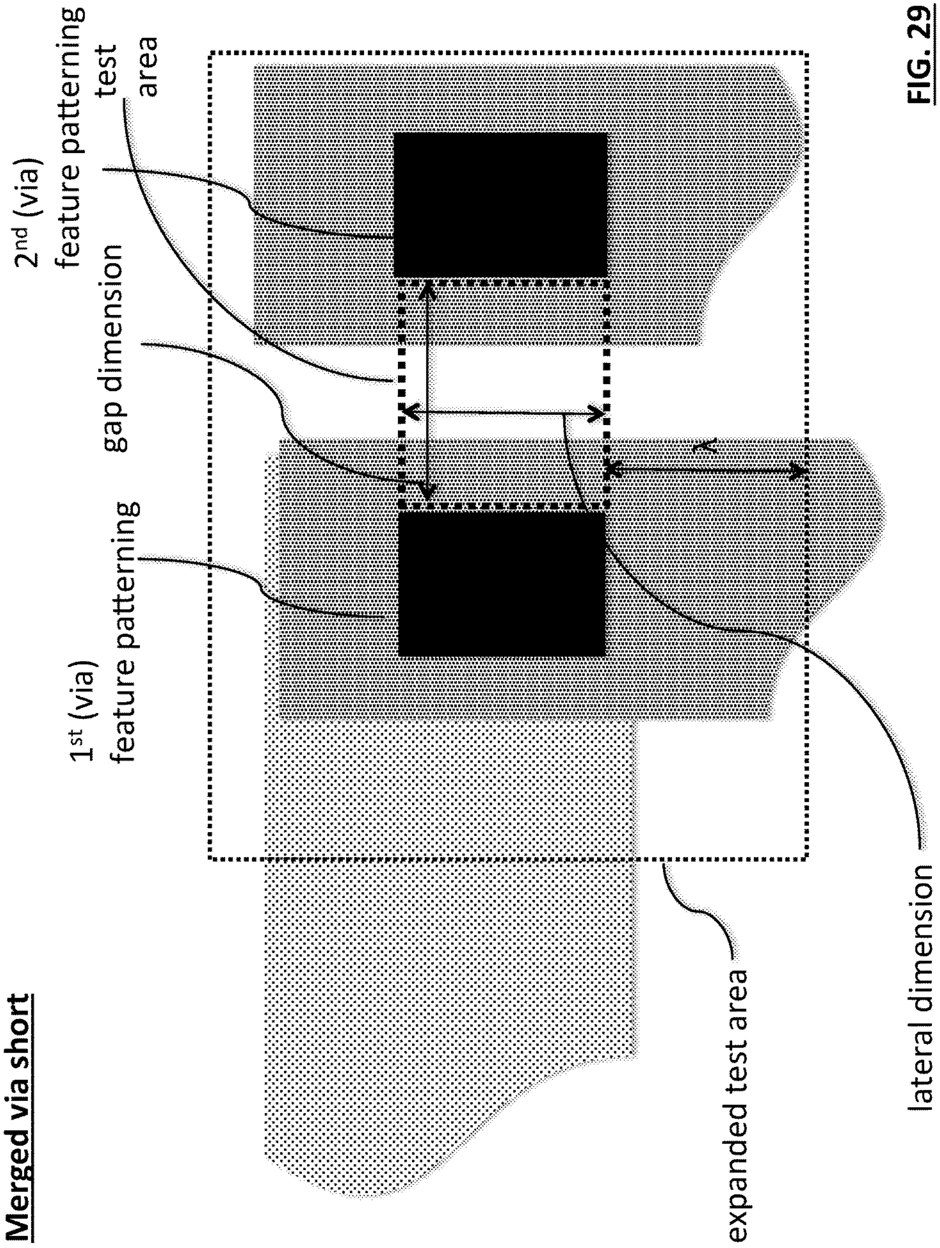
FIG. 29 depicts a plan view of exemplary test area geometry for an exemplary merged-via-short-configured, NCEM-enabled fill cell.

Reference is now made to FIG. 29, which depicts a plan view of exemplary test area geometry for merged-via-short-configured, NCEM-enabled fill cells. Cells that utilize this geometric configuration may include:

V0-merged-via-short-configured, NCEM-enabled fill cells;
V1-merged-via-short-configured, NCEM-enabled fill cells; and,
V2-merged-via-short-configured, NCEM-enabled fill cells.

DOEs of these structures are preferably constructed by varying the dimensional parameters that define the test area (e.g., gap and/or lateral dimension), or by varying other, same- or adjacent-layer patterning within the expanded test area.

Figure 30:
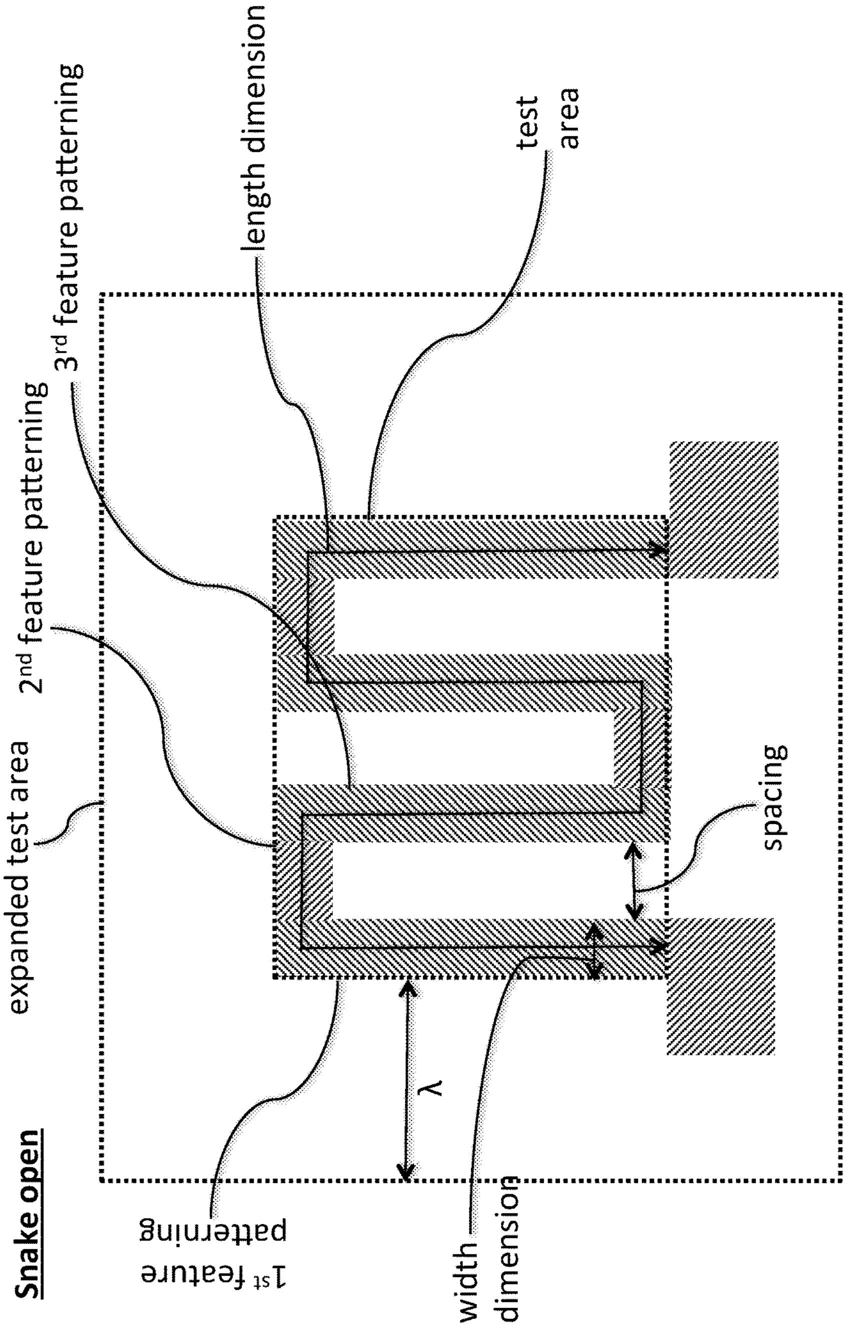
FIG. 30 depicts a plan view of exemplary test area geometry for an exemplary snake-open-configured, NCEM-enabled fill cell.

Reference is now made to FIG. 30, which depicts a plan view of exemplary test area geometry for snake-open-configured, NCEM-enabled fill cells. Cells that utilize this geometric configuration may include:

AA-snake-open-configured, NCEM-enabled fill cells;
TS-snake-open-configured, NCEM-enabled fill cells;
AACNT-snake-open-configured, NCEM-enabled fill cells;
GATE-snake-open-configured, NCEM-enabled fill cells [e.g., FIGS. 1041-1048];
GATECNT-snake-open-configured, NCEM-enabled fill cells;
V0-snake-open-configured, NCEM-enabled fill cells;

M1-snake-open-configured, NCEM-enabled fill cells [e.g., FIGS. 44, 1049-1066];

M1-V0-AACNT-snake-open-configured, NCEM-enabled fill cells [e.g., FIGS. 1067-1071];

V1-snake-open-configured, NCEM-enabled fill cells;

M2-snake-open-configured, NCEM-enabled fill cells;

V2-snake-open-configured, NCEM-enabled fill cells; and,

M3-snake-open-configured, NCEM-enabled fill cells.

DOEs of these structures are preferably constructed by varying the dimensional parameters that define the test area (e.g., length, width, spacing, etc.), or by varying other, same- or adjacent-layer patterning within the expanded test area.

Figure 31:
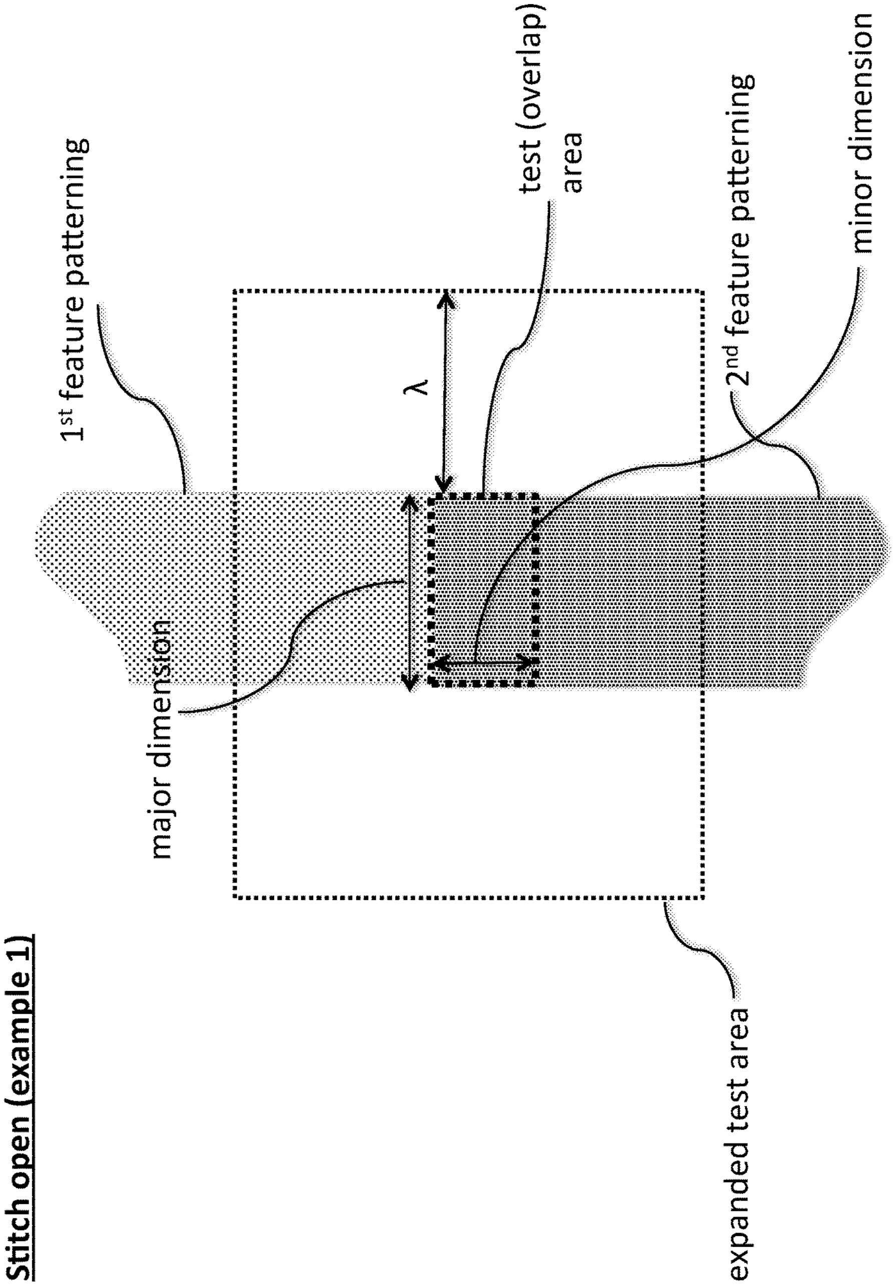
FIG. 31 depicts a plan view of exemplary test area geometry for an exemplary stitch-open-configured, NCEM-enabled fill cell.
Figure 32:
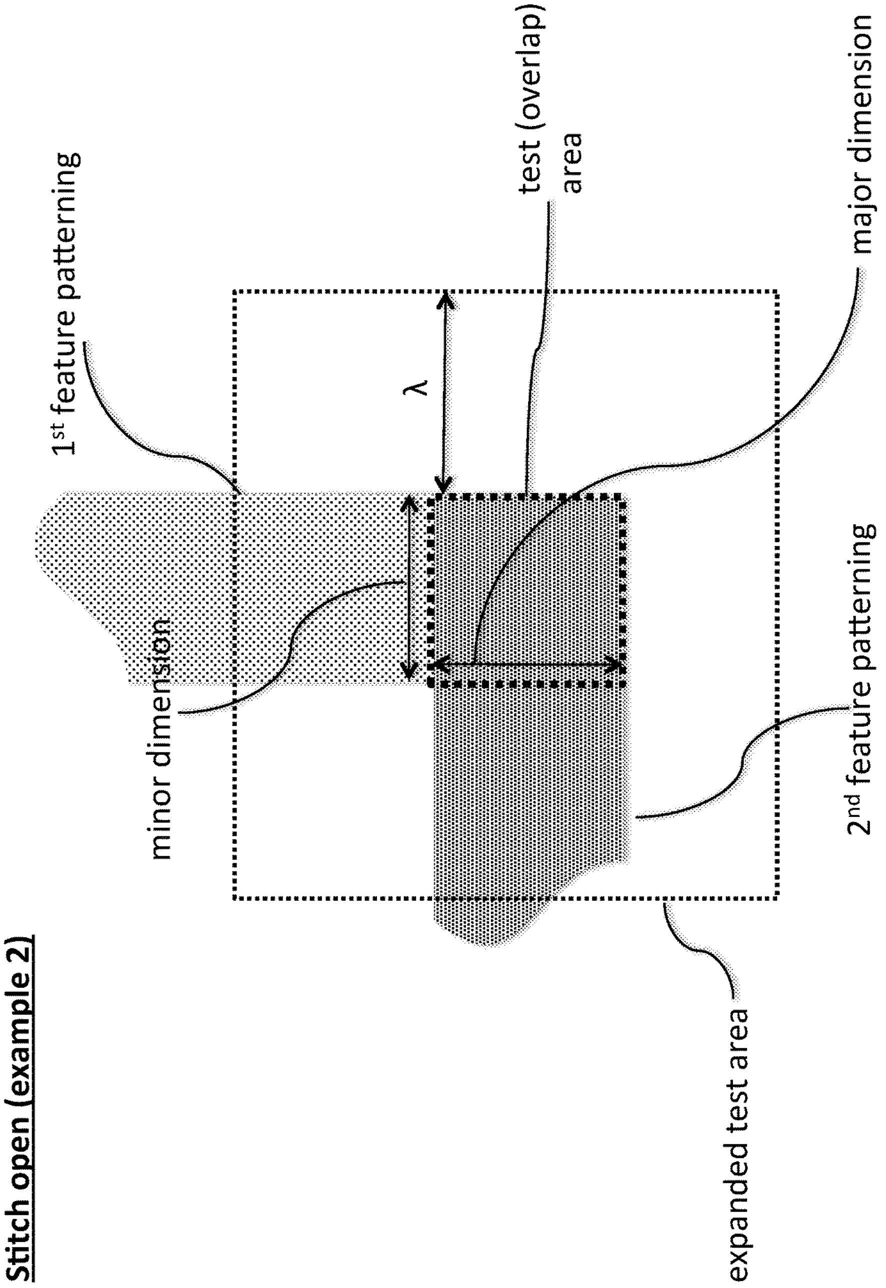
FIG. 32 depicts a plan view of exemplary test area geometry for another exemplary stitch-open-configured, NCEM-enabled fill cell.

Reference is now made to FIGS. 31-32, which each depict plan views of exemplary test area geometries for stitch-open-configured, NCEM-enabled fill cells. Cells that utilize these geometric configurations may include:

AA-stitch-open-configured, NCEM-enabled fill cells;

TS-stitch-open-configured, NCEM-enabled fill cells;

AACNT-stitch-open-configured, NCEM-enabled fill cells;

GATECNT-stitch-open-configured, NCEM-enabled fill cells;

V0-stitch-open-configured, NCEM-enabled fill cells;

M1-stitch-open-configured, NCEM-enabled fill cells [e.g., FIGS. 1072-1083];

V1-stitch-open-configured, NCEM-enabled fill cells;

M2-stitch-open-configured, NCEM-enabled fill cells;

V2-stitch-open-configured, NCEM-enabled fill cells; and,

M3-stitch-open-configured, NCEM-enabled fill cells.

DOEs of these structures are preferably constructed by varying the dimensional parameters that define the test area (e.g., major and/or minor dimension), or by varying other, same- or adjacent-layer patterning within the expanded test area.

Figure 33:
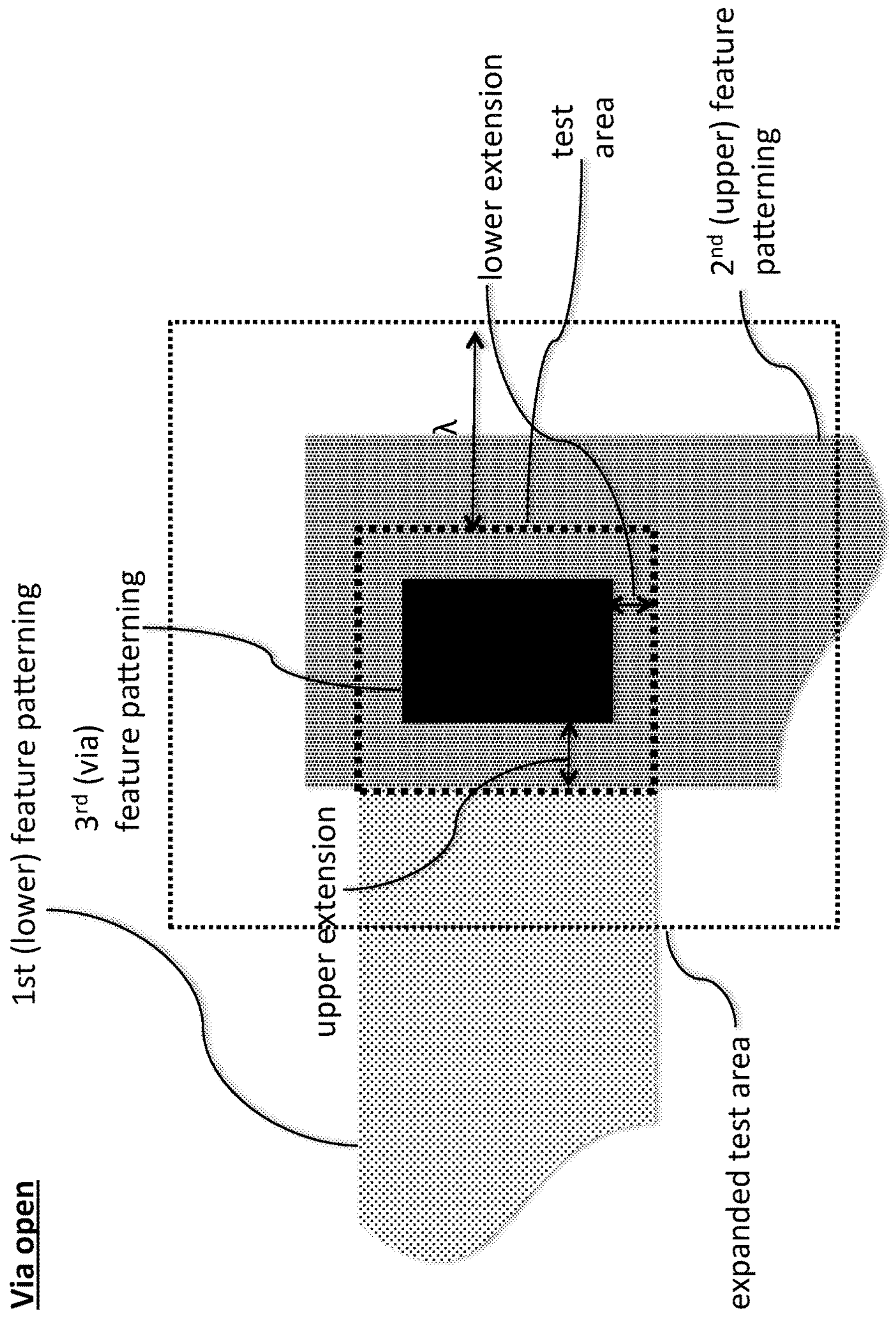
FIG. 33 depicts a plan view of exemplary test area geometry for an exemplary via-open-configured, NCEM-enabled fill cell.

Reference is now made to FIG. 33, which depicts a plan view of exemplary test area geometry for via-open-configured, NCEM-enabled fill cells. Cells that utilize this geometric configuration may include:

AACNT-TS-via-open-configured, NCEM-enabled fill cells [e.g., FIGS. 1629-1673];

AACNT-AA-via-open-configured, NCEM-enabled fill cells [FIGS. 1557-1628];

TS-AA-via-open-configured, NCEM-enabled fill cells [e.g., FIGS. 2315-2330];

GATECNT-GATE-via-open-configured, NCEM-enabled fill cells [e.g., FIGS. 48, 1699-2005];

GATECNT-AACNT-via-open-configured, NCEM-enabled fill cells [e.g., FIGS. 1674-1682];

GATECNT-AACNT-GATE-via-open-configured, NCEM-enabled fill cells [e.g., FIGS. 1683-1698];

V0-GATECNT-via-open-configured, NCEM-enabled fill cells [e.g., FIGS. 2375-2439];

V0-AA-via-open-configured, NCEM-enabled fill cells;

V0-TS-via-open-configured, NCEM-enabled fill cells;

V0-AACNT-via-open-configured, NCEM-enabled fill cells [e.g., FIGS. 2345-2374];

V0-GATE-via-open-configured, NCEM-enabled fill cells;

V0-via-open-configured, NCEM-enabled fill cells [e.g., FIGS. 2331-2344];

M1-V0-via-open-configured, NCEM-enabled fill cells [e.g., FIGS. 2006-2200];

V1-via-open-configured, NCEM-enabled fill cells [e.g., FIGS. 2440-2441];

V1-M1-via-open-configured, NCEM-enabled fill cells [e.g., FIGS. 2442-2459];

V1-M2-via-open-configured, NCEM-enabled fill cells [e.g., FIGS. 2221-2256];

M1-GATECNT-via-open-configured, NCEM-enabled fill cells;

M1-AANCT-via-open-configured, NCEM-enabled fill cells;

V2-M2-via-open-configured, NCEM-enabled fill cells;

V2-M3-via-open-configured, NCEM-enabled fill cells [e.g., FIGS. 2257-2274];

V3-via-open-configured, NCEM-enabled fill cells [e.g., FIGS. 2460-2461];

M4-V3-via-open-configured, NCEM-enabled fill cells [e.g., FIGS. 2275-2296]; and, M5-V4-via-open-configured, NCEM-enabled fill cells [e.g., FIGS. 2297-2314].

DOEs of these structures are preferably constructed by varying the dimensional parameters that define the test area (e.g., upper extension, lower extension, and/or via size/shape), or by varying other, same- or adjacent-layer patterning within the expanded test area.

Figure 34:
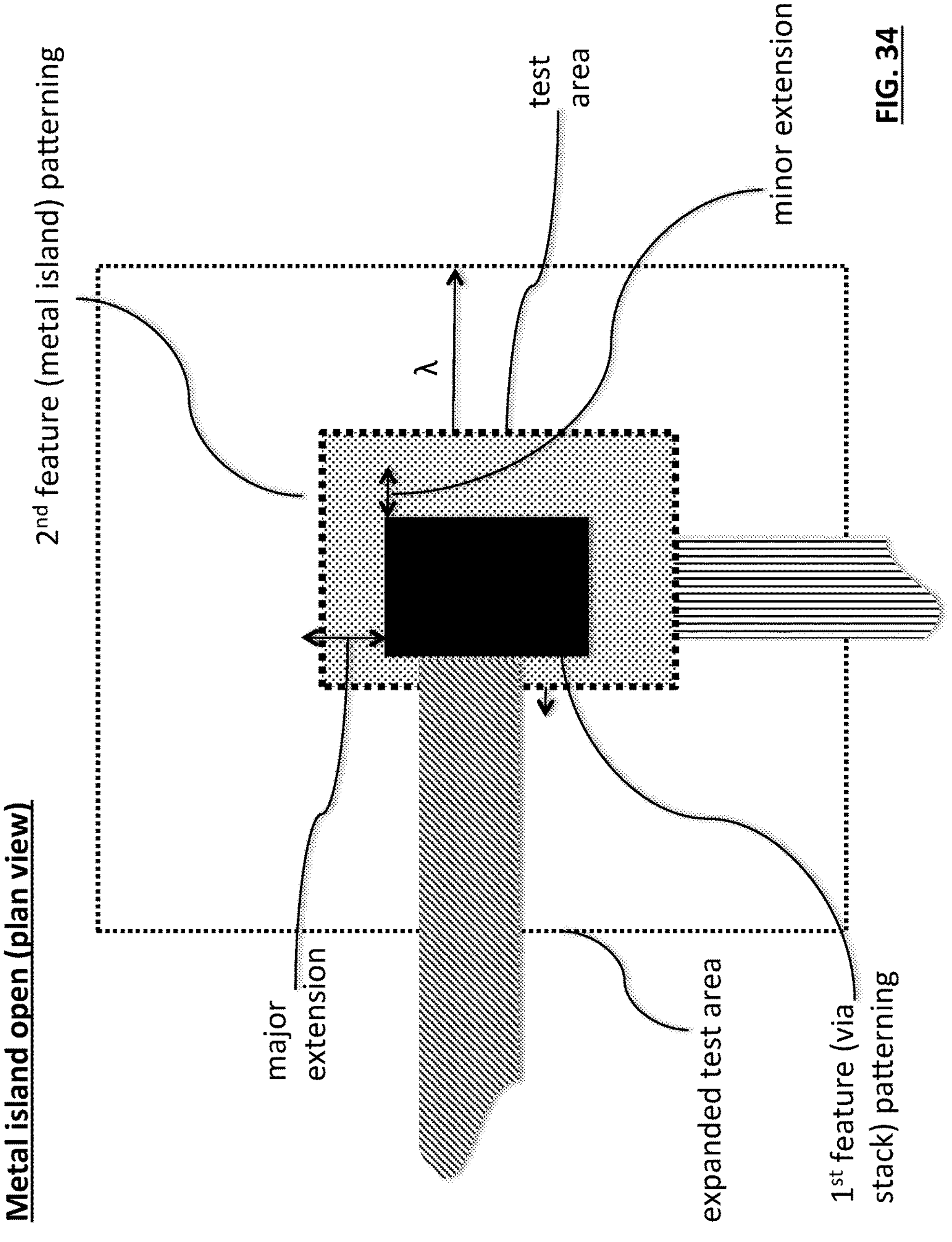
FIG. 34 depicts a plan view of exemplary test area geometry for an exemplary metal-island-open-configured, NCEM-enabled fill cell.
Figure 35:
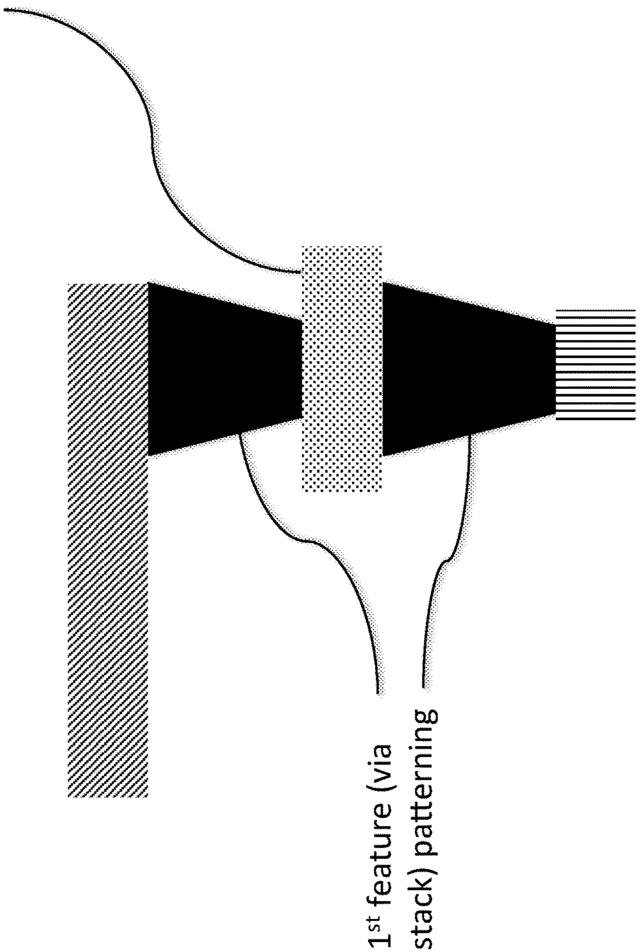
FIG. 35 depicts a cross-sectional view of exemplary test area geometry for the exemplary metal-island-open-configured, NCEM-enabled fill cell.

Reference is now made to FIGS. 34 and 35, which respectively depict plan and cross-sectional views of exemplary test area geometry for metal-island-open-configured, NCEM-enabled fill cells. Cells that utilize this geometric configuration may include:

M1-metal-island-open-configured, NCEM-enabled fill cells;

M2-metal-island-open-configured, NCEM-enabled fill cells; and,

M3-metal-island-open-configured, NCEM-enabled fill cells.

DOEs of these structures are preferably constructed by varying the dimensional parameters that define the test area (e.g., major extension, minor extension, and/or size(s)/shape(s) of lower and/or upper stacked vias), or by varying other, same- or adjacent-layer patterning within the expanded test area.

Figure 36:
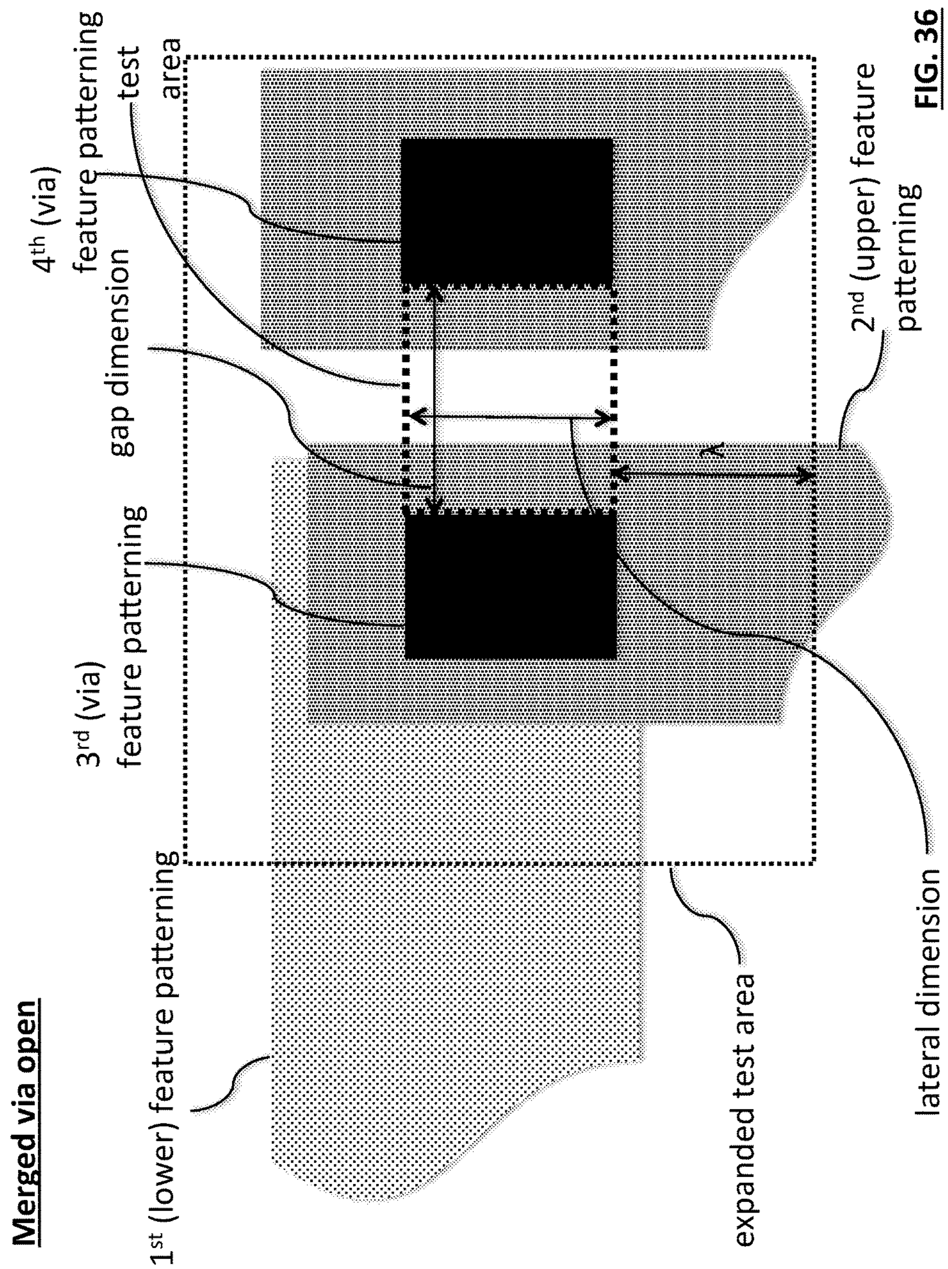
FIG. 36 depicts a plan view of exemplary test area geometry for an exemplary merged-via-open-configured, NCEM-enabled fill cell.

Reference is now made to FIG. 36, which depicts a plan view of exemplary test area geometry for merged-via-open-configured, NCEM-enabled fill cells. Cells that utilize this geometric configuration may include:

V0-merged-via-open-configured, NCEM-enabled fill cells [e.g., FIGS. 735-785];

V0-AACNT-merged-via-open-configured, NCEM-enabled fill cells;

V0-GATECNT-merged-via-open-configured, NCEM-enabled fill cells;

V1-merged-via-open-configured, NCEM-enabled fill cells;

V2-merged-via-open-configured, NCEM-enabled fill cells;

V1-M1-merged-via-open-configured, NCEM-enabled fill cells; and,

V2-M2-merged-via-open-configured, NCEM-enabled fill cells.

DOEs of these structures are preferably constructed by varying the dimensional parameters that define the test area (e.g., gap dimension, lateral dimension, and/or size/shape of one or both vias), or by varying other, same- or adjacent-layer patterning within the expanded test area.

Figure 37:
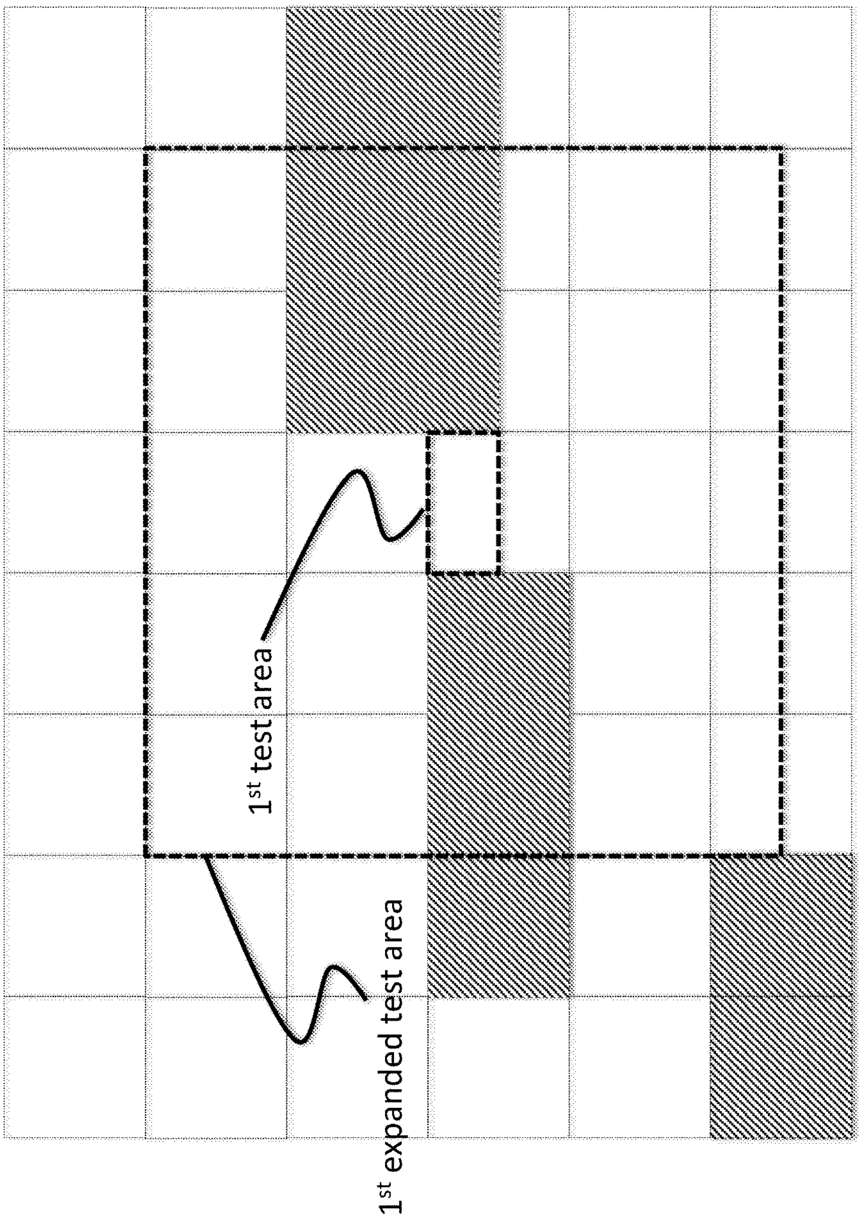
FIG. 37 shows exemplary expanded test area geometry from a $1^{st}$ variant of a NCEM-enabled fill cell.
Figure 38:
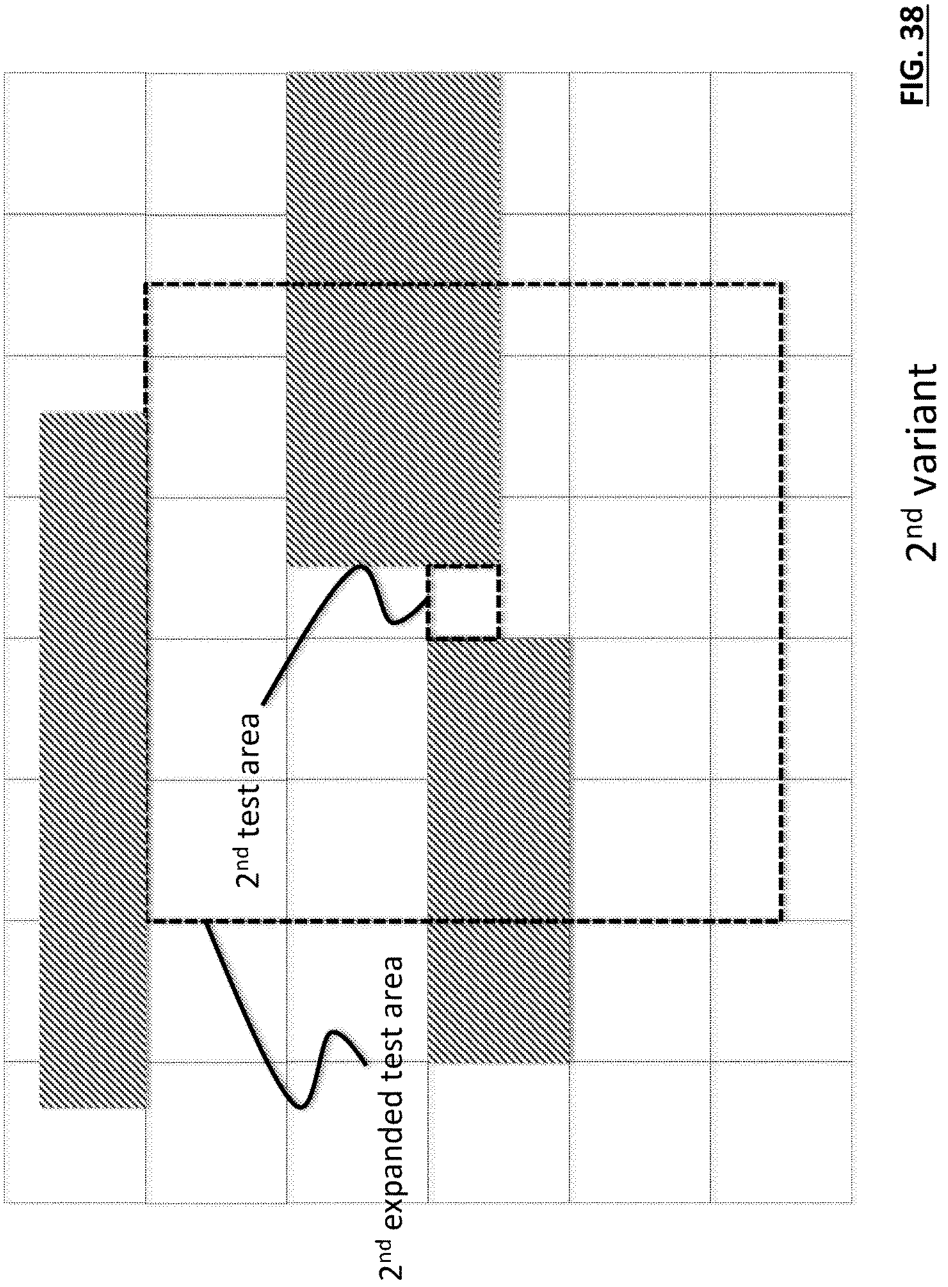
FIG. 38 shows exemplary expanded test area geometry from a $2^{nd}$ variant of a NCEM-enabled fill cell.
Figure 39:
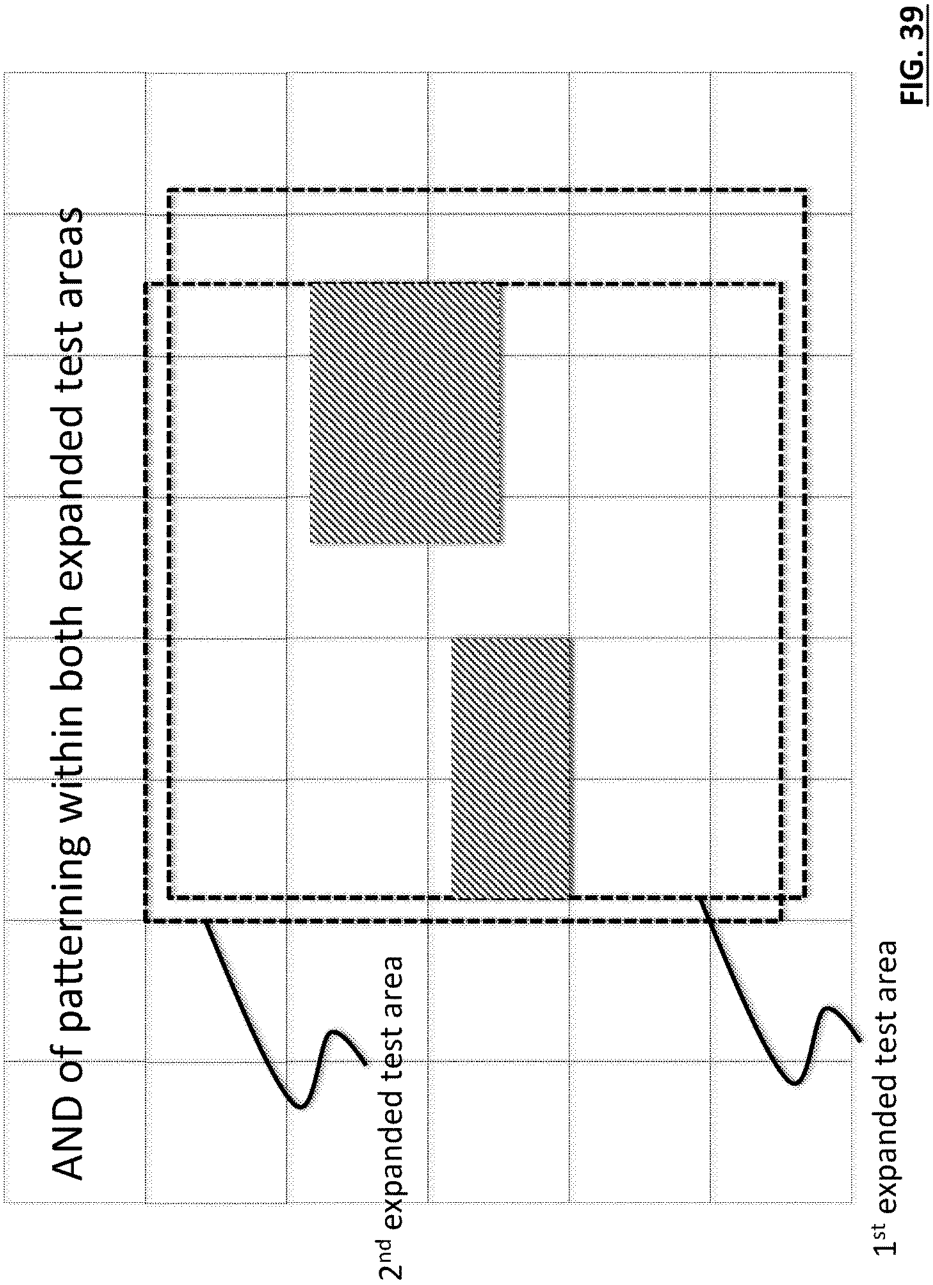
Figure 40:
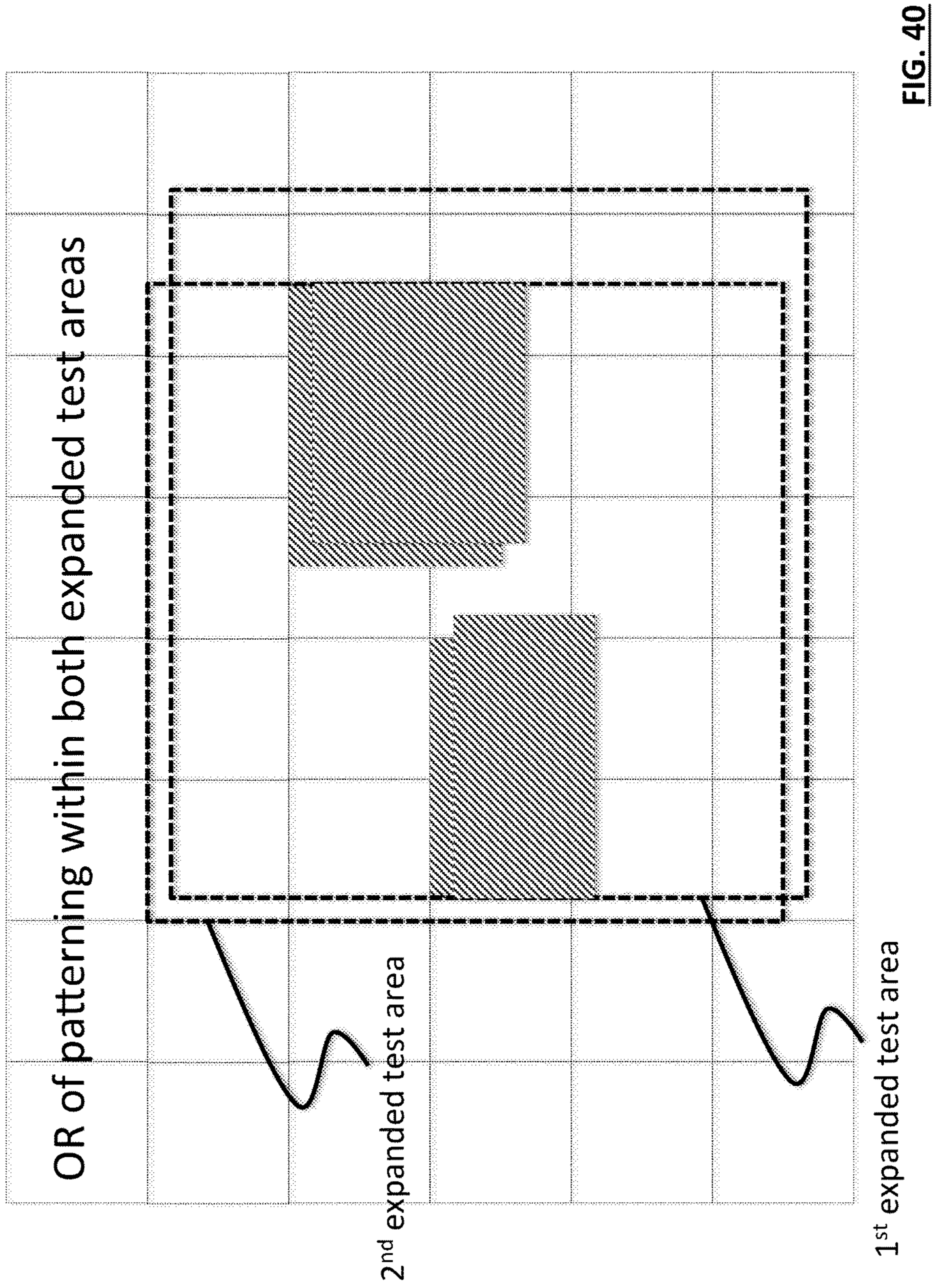

Reference is now made to FIG. 37, which shows exemplary expanded test area geometry from a $1^{st}$ variant of a NCEM-enabled fill cell, and to FIG. 38, which shows exemplary expanded test area geometry from a $2^{nd}$ variant of a NCEM-enabled fill cell. These figures, and the two that follow, illustrate the computation of the PSR between (the depicted layer, which could be any layer, of) the $1^{st}$ variant and the $2^{nd}$ variant. FIG. 39 shows the logical AND of (depicted layer) patterning within both expanded test areas (of FIGS. 37 & 38). FIG. 40 shows the logical OR of patterning within both expanded test areas (of FIGS. 37 & 38). The PSR (pattern similarity ratio) is then defined as the area ratio of the AND patterns to the OR patterns. Conceptually, PSR is a measure of how much of the patterning within the common expanded test areas is new. In other words, if the two cells are identical (within the layer(s)-at-issue, and within the common expanded test area), then the PSR will be 1.0. Conversely, if they share no common patterning (within the layer(s)-at-issue, and within the common expanded test area), then the AND patterns will be nil, and the PSR will be 0.0.

Figure 41:
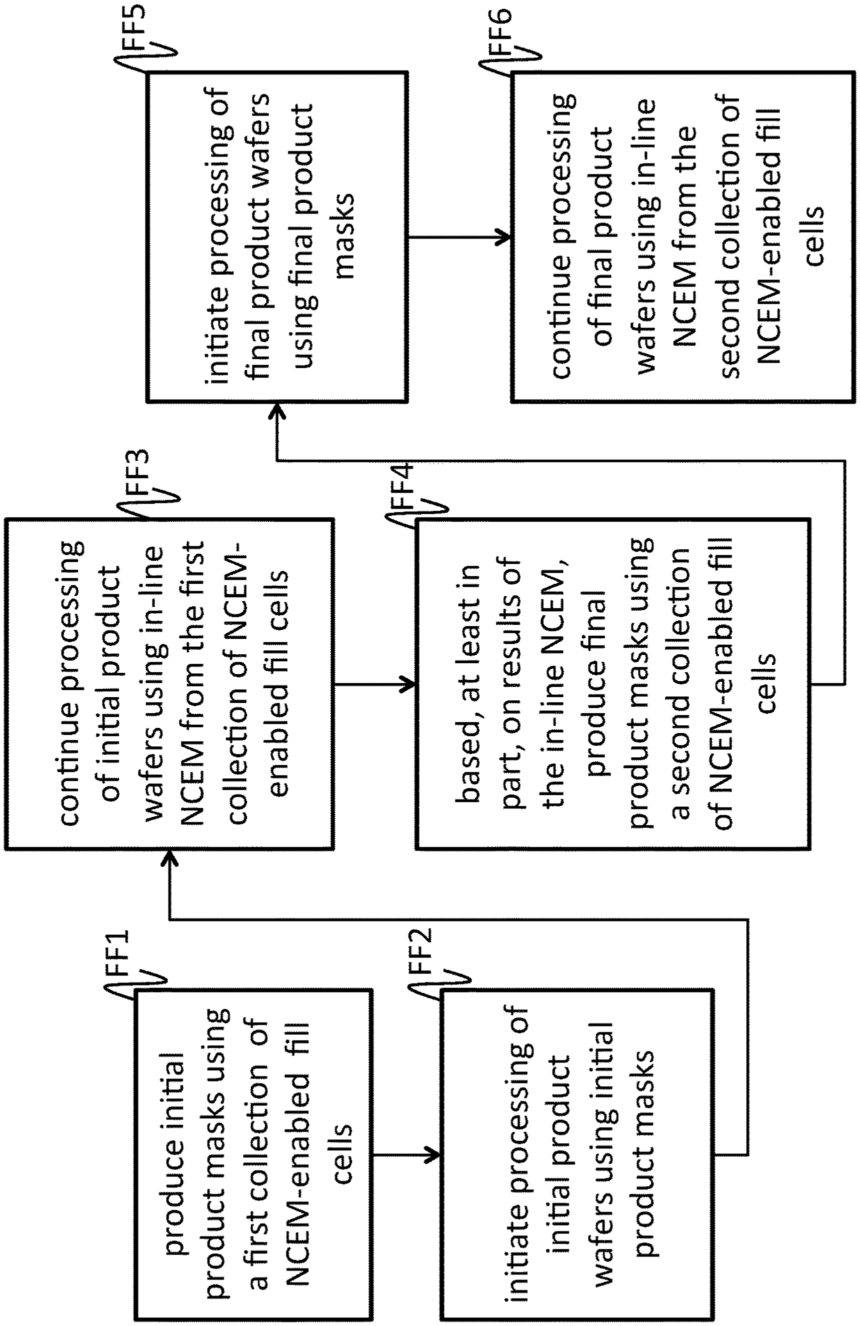

Reference is now made to FIG. 41, which depicts an exemplary process flow, suitable for use in connection with certain embodiments of the invention. At FF1, an initial set of product masks is produced (or otherwise obtained); these initial product masks include a first collection of NCEM-enabled fill cells.

At FF2, processing of wafers is initiated using the initial product masks. Such processing preferably includes at least FEOL and/or MOL processing, but may also include BEOL processing. Before FF3, NCEM measurements are preferably obtained from some or all of the NCEM-enabled fill cells on the partially-processed initial product wafers.

At FF3, some or all of the obtained NCEM measurements are "used" to continue processing of the initial product wafers. Such "use" may include determining whether to continue or abandon processing of one or more of the wafers, modifying one or more processing, inspection or metrology steps in the continued processing of one or more of the wafers (and/or other product wafers currently being manufactured using process flows relevant to observed manufacturing failures), and/or performing additional processing, metrology or inspection steps on one or more of the wafers (and/or other product wafers currently being manufactured using process flows relevant to observed manufacturing failures).

At FF4, final product masks are produced (or otherwise obtained) "using" at least some of the NCEM measurements obtained during the processing of initial product wafers. Here, such "use" preferably includes selecting and instantiating a second collection of NCEM-enabled fill cells that is better and/or optimally matched to failure modes observed during processing of the initial product wafers. For example, if the first collection of NCEM-enabled fill cells included GATE-side-to-side-short-configured cells, yet no GATE side-to-side shorts were observed during processing of the initial product wafers, then the second collection of NCEM-enabled fill cells would preferably omit GATE-side-to-side-short-configured cells, and instead replace them with other NCEM-enabled fill cells that are better matched to the observed or expected failure modes on the final product wafers.

At FF5, processing of wafers is initiated using the final product masks. Such processing preferably includes at least FEOL and/or MOL processing, but may also include BEOL processing. Before FF6, NCEM measurements are preferably obtained from some or all of the NCEM-enabled fill cells on the partially-processed final product wafers.

At FF6, some or all of the obtained NCEM measurements are "used" to continue processing of the final product wafers. Such "use" may include determining whether to continue or abandon processing of one or more of the wafers, modifying one or more processing, inspection or metrology steps in the continued processing of one or more of the wafers (and/or other product wafers currently being manufactured using process flows relevant to observed manufacturing failures), and/or performing additional processing, metrology or inspection steps on one or more of the wafers (and/or other product wafers currently being manufactured using process flows relevant to observed manufacturing failures).

Figure 42:
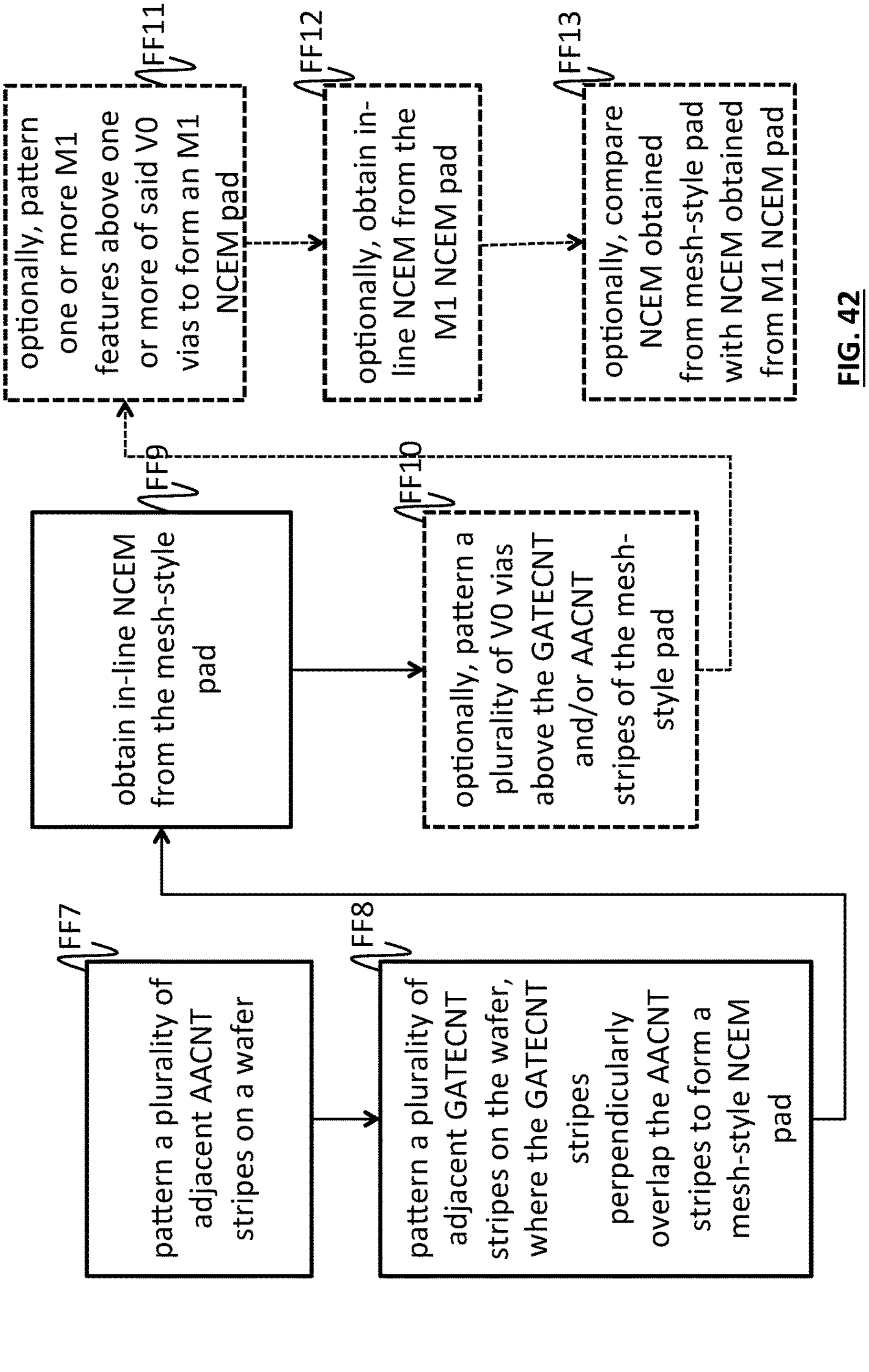

Reference is now made to FIG. 42, which depicts an exemplary process flow for obtaining and (optionally) using measurements from mesh-style NCEM pads. As persons skilled in the art will appreciate, this process can be utilized either with or without NCEM-enabled fill cells; in other words, the mesh-style NCEM pads can be instantiated within NCEM-enabled fill cells, but can also be instantiated anywhere on a chip, die, or wafer. Furthermore, as persons skilled in the art will also appreciate, the order of steps FF7 & FF8 can be reversed, or performed simultaneously, to accommodate processes where the order of AACNT & GATECNT patterning is different.

Figure 43:
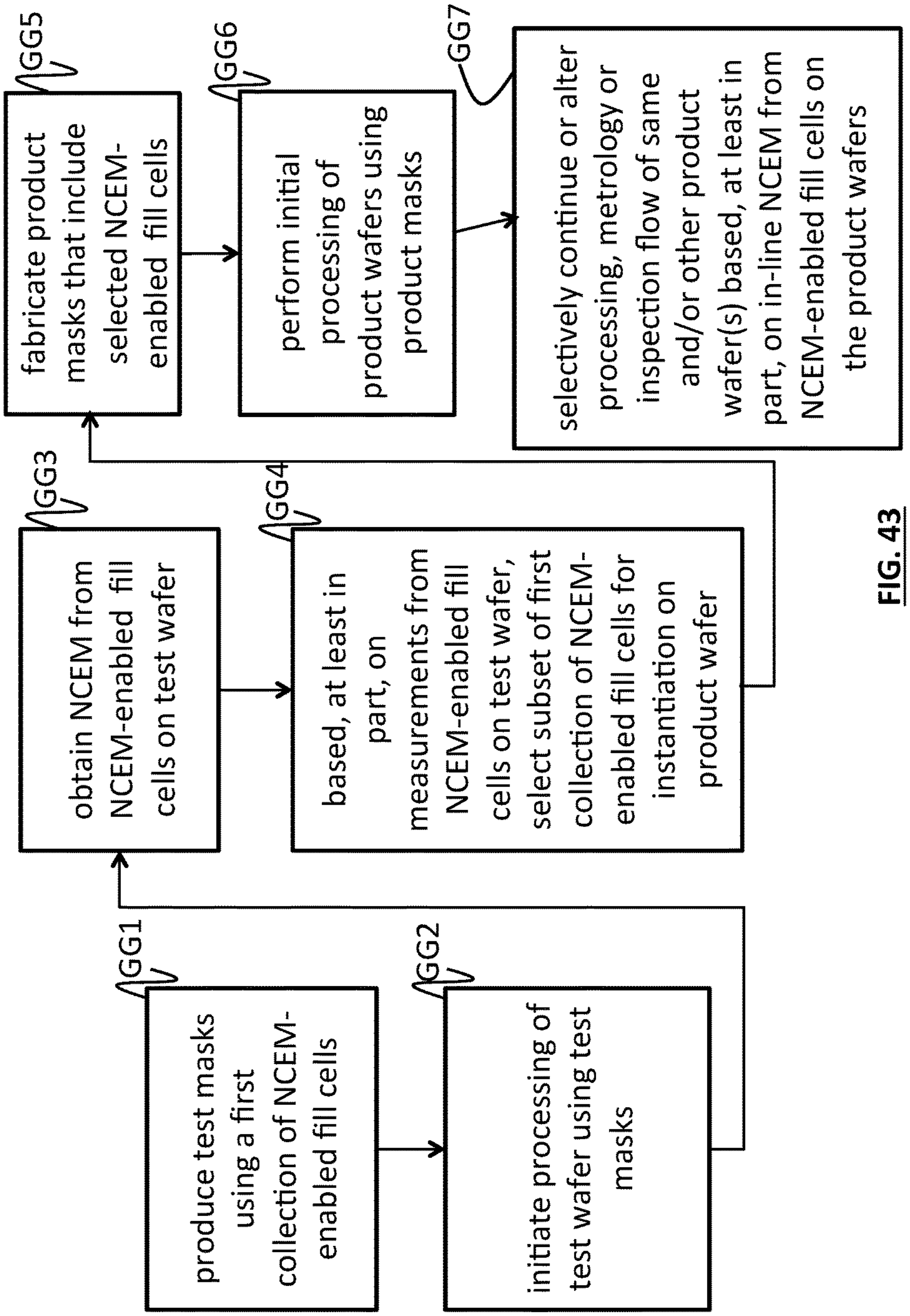

Reference is now made to FIG. 43, which depicts another exemplary process flow, suitable for use in accordance with certain embodiments of the invention. At GG1, test mask (e.g., masks to produce a "test" or "engineering" wafer) are produced or otherwise obtained; such test masks include a first collection of NCEM-enabled fill cells.

At GG2, processing of the test wafer(s) is initiated. Such processing preferably includes FEOL and/or MOL processing, but may also include BEOL processing.

At GG3, NCEM measurements are obtained from NCEM-enabled fill cells on the partially-processed test wafer(s).

At GG4, the obtained measurements are "used" to select a second collection of NCEM-enabled fill cells (preferably a subset of the first collection) for instantiation on product wafers. Here, such "use" preferably includes selecting a second collection of NCEM-enabled fill cells that, given the available fill cell space on the product wafers, is optimally matched to failure modes observed during processing of the test product wafers. For example, if the first collection of NCEM-enabled fill cells included GATE-side-to-side-short-configured cells, yet no GATE side-to-side shorts were observed during processing of test wafers, then the second collection of NCEM-enabled fill cells would preferably omit GATE-side-to-side-short-configured cells.

At GG5, product masks that include the second collection of NCEM-enabled fill cells are produced, or otherwise obtained.

At GG6, processing of the product wafer(s) is initiated. Such processing preferably includes at least FEOL and/or MOL processing, but may also include BEOL processing. Prior to GG7, NCEM measurements are obtained from at least some of the NCEM-enabled fill cells on the partially-processed product wafer(s).

At GG7, some or all of the obtained NCEM measurements are "used" to continue processing of the product wafer(s). Such "use" may include determining whether to continue or abandon processing of one or more of the product wafers, modifying one or more processing, inspection or metrology steps in the continued processing of one or more of the product wafers (and/or other product wafers currently being manufactured using process flows relevant to observed manufacturing failures), and/or performing additional processing, metrology or inspection steps on one or more of the product wafers (and/or other product wafers currently being manufactured using process flows relevant to observed manufacturing failures).

In certain embodiments, FF1-3 and/or GG5-7 could be practiced as stand-alone process flows.

Figure 44:
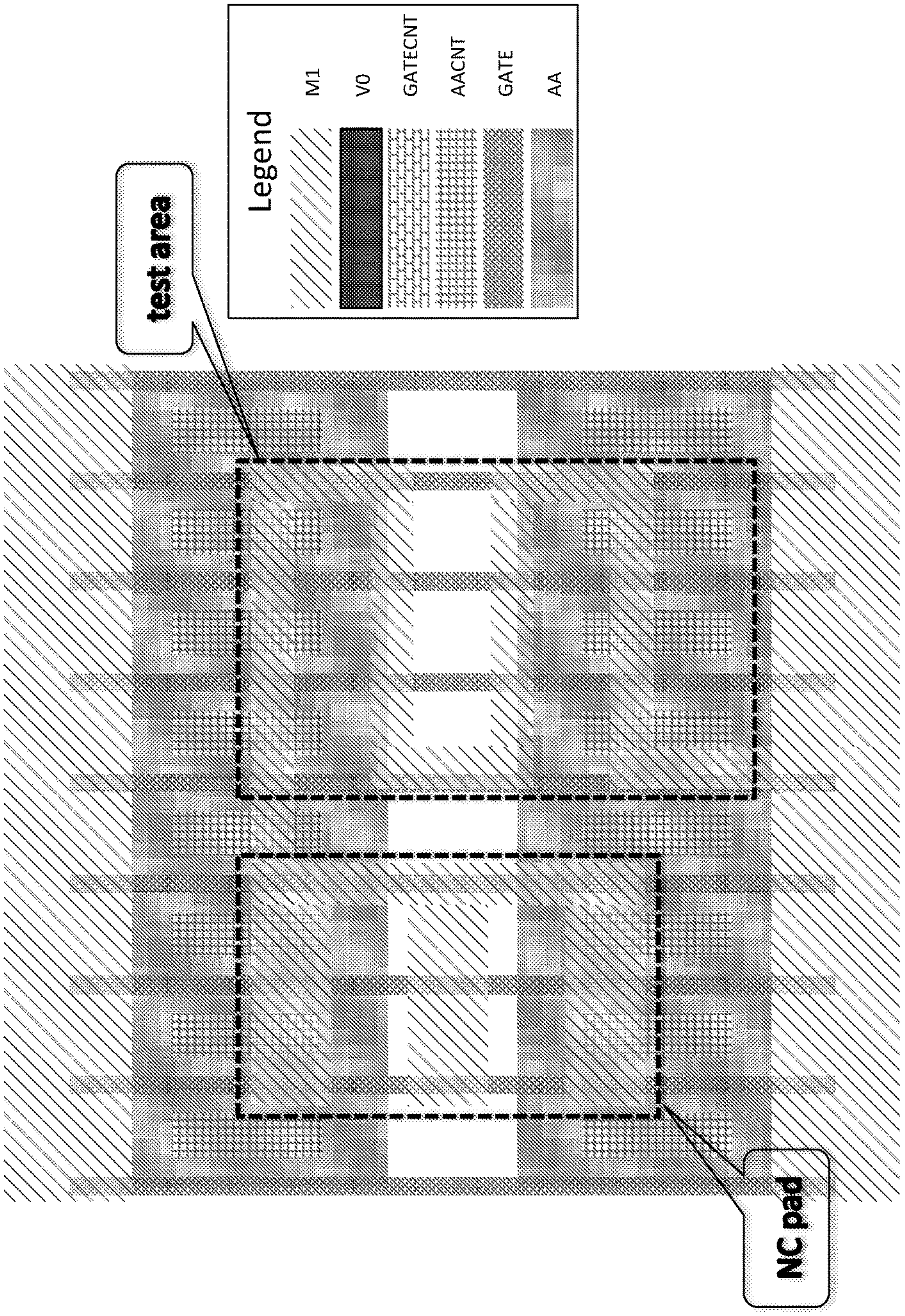

Reference is now made to FIG. 44, which depicts a plan view of an exemplary M1-snake-open-configured, NCEM-enabled fill cell. This cell contains a left-facing-E-shaped NCEM pad, a snake-open-configured test area, and is NCEM-enabled to detect the following failure mode: M1 snake open. In the depicted configuration, a passing response is grounded metal=bright NCEM, whereas a failing response is floating pad=dark NCEM.

Reference is now made to FIG. 45, which depicts a plan view of an exemplary AACNT-tip-to-side-short-configured, NCEM-enabled fill cell. This cell contains four test areas, and an E-shaped NCEM pad that overlies the test areas. It is NC-configured for inline measurement of the following failure mode: AACNT tip-to-side short. In the depicted configuration, a passing response is floating AA contacts=dark NCEM, whereas a failing response is a short to grounded contact layer=bright NCEM.

Reference is now made to FIGS. 46A-C, which respectively depict plan views of—(A) all layers; (B) NWELL, AA, GATE, GATECNT, TS, and AACNT layers; (C) V0 and M1 layers—of an exemplary TS-GATE-side-to-side-short-configured, NCEM-enabled fill cell of type PDF_D_VCI_V16_14S1_01. This cell utilizes a composite NCEM pad, as depicted in FIG. 9E.

Reference is now made to FIGS. 47A-C, which respectively depict plan views of—(A) all layers; (B) NWELL, AA, GATE, GATECNT, TS, and AACNT layers; (C) V0 and M1 layers—of an exemplary GATECNT-AACNT-side-to-side-short-configured, NCEM-enabled fill cell of type PDF_D_VCI_V16_14S1_05. This cell also utilizes a composite NCEM pad.

Reference is now made to FIGS. 48A-C, which respectively depict plan views of—(A) all layers; (B) NWELL, AA, GATE, GATECNT, TS, and AACNT layers; (C) V0 and M1 layers—of an exemplary GATECNT-GATE-via-open-configured, NCEM-enabled fill cell of type PDF_D_VCI_V16_14S1_08. This cell also utilizes a composite NCEM pad.

Reference is now made to FIGS. 49A-C, which respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_11. This cell also utilizes a composite NCEM pad.

Reference is now made to FIGS. 50(A)-(C), which respectively depict plan views of—(A) all layers; (B) NWELL, AA, GATE, GATECNT, TS, and AACNT layers; (C) V0 and M1 layers—of another exemplary GATE-AA-tip-to-side-short-configured, NCEM-enabled fill cell of type PDF_D_VCI_V16_14S1_12. This cell also utilizes a composite NCEM pad.

FIGS. 52A-C, 53A-C, 54A-C, et seq., which depict additional examples of NCEM-enabled fill cells, utilize the same layer shadings/patterns depicted in FIG. 51.

FIGS. 160-162 depict three variants of the same cell. FIGS. 161(A)-(C) show the nominal case, whereas the other figures represent intentionally misaligned conditions.

FIGS. 163-165 depict three variants of the same cell. FIGS. 164(A)-(C) show the nominal case, whereas the other figures represent intentionally misaligned conditions.

FIGS. 166-168 depict three variants of the same cell. FIGS. 167(A)-(C) show the nominal case, whereas the other figures represent intentionally misaligned conditions.

FIGS. 169-171 depict three variants of the same cell. FIGS. 170(A)-(C) show the nominal case, whereas the other figures represent intentionally misaligned conditions.

FIGS. 172-173 depict two variants of the same cell. FIGS. 173(A)-(C) show the nominal case, whereas the other figures represent intentionally misaligned conditions.

FIGS. 174-175 depict two variants of the same cell. FIGS. 175(A)-(C) show the nominal case, whereas the other figures represent intentionally misaligned conditions.

FIGS. 176-177 depict two variants of the same cell. FIGS. 177(A)-(C) show the nominal case, whereas the other figures represent intentionally misaligned conditions.

FIGS. 178-179 depict two variants of the same cell. FIGS. 179(A)-(C) show the nominal case, whereas the other figures represent intentionally misaligned conditions.

FIGS. 180-181 depict two variants of the same cell. FIGS. 181(A)-(C) show the nominal case, whereas the other figures represent intentionally misaligned conditions.

FIGS. 182-183 depict two variants of the same cell. FIGS. 183(A)-(C) show the nominal case, whereas the other figures represent intentionally misaligned conditions.

FIGS. 184-185 depict two variants of the same cell. FIGS. 184(A)-(C) show the nominal case, whereas the other figures represent intentionally misaligned conditions.

FIGS. 191-193 depict three variants of the same cell. FIGS. 192(A)-(C) show the nominal case, whereas the other figures represent intentionally misaligned conditions.

FIGS. 194-196 depict three variants of the same cell. FIGS. 195(A)-(C) show the nominal case, whereas the other figures represent intentionally misaligned conditions.

FIGS. 197-199 depict three variants of the same cell. FIGS. 198(A)-(C) show the nominal case, whereas the other figures represent intentionally misaligned conditions.

FIGS. 200-202 depict three variants of the same cell. FIGS. 201(A)-(C) show the nominal case, whereas the other figures represent intentionally misaligned conditions.

FIGS. 203-205 depict three variants of the same cell. FIGS. 204(A)-(C) show the nominal case, whereas the other figures represent intentionally misaligned conditions.

FIGS. 206-208 depict three variants of the same cell. FIGS. 207(A)-(C) show the nominal case, whereas the other figures represent intentionally misaligned conditions.

FIGS. 209-211 depict three variants of the same cell. FIGS. 210(A)-(C) show the nominal case, whereas the other figures represent intentionally misaligned conditions.

FIGS. 212-214 depict three variants of the same cell. FIGS. 213(A)-(C) show the nominal case, whereas the other figures represent intentionally misaligned conditions.

FIGS. 215-217 depict three variants of the same cell. FIGS. 216(A)-(C) show the nominal case, whereas the other figures represent intentionally misaligned conditions.

FIGS. 218-220 depict three variants of the same cell. FIGS. 219(A)-(C) show the nominal case, whereas the other figures represent intentionally misaligned conditions.

FIGS. 221-223 depict three variants of the same cell. FIGS. 222(A)-(C) show the nominal case, whereas the other figures represent intentionally misaligned conditions.

FIGS. 224-226 depict three variants of the same cell. FIGS. 225(A)-(C) show the nominal case, whereas the other figures represent intentionally misaligned conditions.

FIGS. 227-229 depict three variants of the same cell. FIGS. 228(A)-(C) show the nominal case, whereas the other figures represent intentionally misaligned conditions.

FIGS. 230-232 depict three variants of the same cell. FIGS. 231(A)-(C) show the nominal case, whereas the other figures represent intentionally misaligned conditions.

FIGS. 233-235 depict three variants of the same cell. FIGS. 234(A)-(C) show the nominal case, whereas the other figures represent intentionally misaligned conditions.

FIGS. 236-238 depict three variants of the same cell. FIGS. 237(A)-(C) show the nominal case, whereas the other figures represent intentionally misaligned conditions.

FIGS. 239-241 depict three variants of the same cell. FIGS. 240(A)-(C) show the nominal case, whereas the other figures represent intentionally misaligned conditions.

FIGS. 242-244 depict three variants of the same cell. FIGS. 243(A)-(C) show the nominal case, whereas the other figures represent intentionally misaligned conditions.

FIGS. 245-247 depict three variants of the same cell. FIGS. 246(A)-(C) show the nominal case, whereas the other figures represent intentionally misaligned conditions.

FIGS. 248-250 depict three variants of the same cell. FIGS. 249(A)-(C) show the nominal case, whereas the other figures represent intentionally misaligned conditions.

FIGS. 251-253 depict three variants of the same cell. FIGS. 252(A)-(C) show the nominal case, whereas the other figures represent intentionally misaligned conditions.

FIGS. 254-256 depict three variants of the same cell. FIGS. 255(A)-(C) show the nominal case, whereas the other figures represent intentionally misaligned conditions.

FIGS. 257-259 depict three variants of the same cell. FIGS. 258(A)-(B) show the nominal case, whereas the other figures represent intentionally misaligned conditions.

FIGS. 260-262 depict three variants of the same cell. FIGS. 261(A)-(B) show the nominal case, whereas the other figures represent intentionally misaligned conditions.

FIGS. 263-265 depict three variants of the same cell. FIGS. 264(A)-(C) show the nominal case, whereas the other figures represent intentionally misaligned conditions.

FIGS. 266-268 depict three variants of the same cell. FIGS. 267(A)-(C) show the nominal case, whereas the other figures represent intentionally misaligned conditions.

FIGS. 269-271 depict three variants of the same cell. FIGS. 219(A)-(C) show the nominal case, whereas the other figures represent intentionally misaligned conditions.

FIGS. 272-274 depict three variants of the same cell. FIGS. 273(A)-(C) show the nominal case, whereas the other figures represent intentionally misaligned conditions.

FIGS. 275-277 depict three variants of the same cell. FIGS. 276(A)-(C) show the nominal case, whereas the other figures represent intentionally misaligned conditions.

FIGS. 278-280 depict three variants of the same cell. FIGS. 279(A)-(C) show the nominal case, whereas the other figures represent intentionally misaligned conditions.

FIGS. 281-283 depict three variants of the same cell. FIGS. 2821(A)-(C) show the nominal case, whereas the other figures represent intentionally misaligned conditions.

FIGS. 284-286 depict three variants of the same cell. FIGS. 285(A)-(C) show the nominal case, whereas the other figures represent intentionally misaligned conditions.

FIGS. 363-365 depict three variants of the same cell. FIGS. 363(A)-(C) show the nominal case, whereas the other figures represent intentionally misaligned conditions.

FIGS. 366-368 depict three variants of the same cell. FIGS. 367(A)-(C) show the nominal case, whereas the other figures represent intentionally misaligned conditions.

FIGS. 369-371 depict three variants of the same cell. FIGS. 369(A)-(C) show the nominal case, whereas the other figures represent intentionally misaligned conditions.

FIGS. 372-374 depict three variants of the same cell. FIGS. 372(A)-(C) show the nominal case, whereas the other figures represent intentionally misaligned conditions.

FIGS. 377-379 depict three variants of the same cell. FIGS. 378(A)-(C) show the nominal case, whereas the other figures represent intentionally misaligned conditions.

FIGS. 380-382 depict three variants of the same cell. FIGS. 381(A)-(C) show the nominal case, whereas the other figures represent intentionally misaligned conditions.

FIGS. 383-385 depict three variants of the same cell. FIGS. 384(A)-(C) show the nominal case, whereas the other figures represent intentionally misaligned conditions.

FIGS. 386-388 depict three variants of the same cell. FIGS. 387(A)-(C) show the nominal case, whereas the other figures represent intentionally misaligned conditions.

FIGS. 389-391 depict three variants of the same cell. FIGS. 390(A)-(C) show the nominal case, whereas the other figures represent intentionally misaligned conditions.

FIGS. 392-394 depict three variants of the same cell. FIGS. 393(A)-(C) show the nominal case, whereas the other figures represent intentionally misaligned conditions.

FIGS. 395-397 depict three variants of the same cell. FIGS. 396(A)-(C) show the nominal case, whereas the other figures represent intentionally misaligned conditions.

FIGS. 398-400 depict three variants of the same cell. FIGS. 399(A)-(C) show the nominal case, whereas the other figures represent intentionally misaligned conditions.

FIGS. 401-403 depict three variants of the same cell. FIGS. 402(A)-(C) show the nominal case, whereas the other figures represent intentionally misaligned conditions.

FIGS. 404-406 depict three variants of the same cell. FIGS. 405(A)-(C) show the nominal case, whereas the other figures represent intentionally misaligned conditions.

FIGS. 407-409 depict three variants of the same cell. FIGS. 408(A)-(C) show the nominal case, whereas the other figures represent intentionally misaligned conditions.

FIGS. 410-412 depict three variants of the same cell. FIGS. 411(A)-(C) show the nominal case, whereas the other figures represent intentionally misaligned conditions.

FIGS. 413-415 depict three variants of the same cell. FIGS. 414(A)-(C) show the nominal case, whereas the other figures represent intentionally misaligned conditions.

FIGS. 476-477 depict two variants of the same cell. FIGS. 477(A)-(C) show the nominal case, whereas the other figures represent intentionally misaligned conditions.

FIGS. 478-479 depict two variants of the same cell. FIGS. 479(A)-(C) show the nominal case, whereas the other figures represent intentionally misaligned conditions.

FIGS. 480-481 depict two variants of the same cell. FIGS. 481(A)-(C) show the nominal case, whereas the other figures represent intentionally misaligned conditions.

FIGS. 482-483 depict two variants of the same cell. FIGS. 483(A)-(C) show the nominal case, whereas the other figures represent intentionally misaligned conditions.

FIGS. 487-489 depict three variants of the same cell. FIGS. 488(A)-(C) show the nominal case, whereas the other figures represent intentionally misaligned conditions.

FIGS. 492-494 depict three variants of the same cell. FIGS. 493(A)-(C) show the nominal case, whereas the other figures represent intentionally misaligned conditions.

FIGS. 519-533 depict variants of the same cell. FIGS. 519(A)-(C) show the nominal case, whereas the other figures represent intentionally misaligned conditions.

FIGS. 522-536 depict variants of the same cell. FIGS. 522(A)-(C) show the nominal case, whereas the other figures represent intentionally misaligned conditions.

FIGS. 525-539 depict variants of the same cell. FIGS. 525(A)-(C) show the nominal case, whereas the other figures represent intentionally misaligned conditions.

FIGS. 528-542 depict variants of the same cell. FIGS. 528(A)-(C) show the nominal case, whereas the other figures represent intentionally misaligned conditions.

FIGS. 543-545 depict three variants of the same cell. FIGS. 544(A)-(C) show the nominal case, whereas the other figures represent intentionally misaligned conditions.

FIGS. 546-548 depict three variants of the same cell. FIGS. 547(A)-(C) show the nominal case, whereas the other figures represent intentionally misaligned conditions.

FIGS. 549-551 depict three variants of the same cell. FIGS. 550(A)-(C) show the nominal case, whereas the other figures represent intentionally misaligned conditions.

FIGS. 552-554 depict three variants of the same cell. FIGS. 553(A)-(C) show the nominal case, whereas the other figures represent intentionally misaligned conditions.

FIGS. 599-601 depict three variants of the same cell. FIGS. 600(A)-(C) show the nominal case, whereas the other figures represent intentionally misaligned conditions.

FIGS. 602-604 depict three variants of the same cell. FIGS. 603(A)-(C) show the nominal case, whereas the other figures represent intentionally misaligned conditions.

FIGS. 605-607 depict three variants of the same cell. FIGS. 606(A)-(C) show the nominal case, whereas the other figures represent intentionally misaligned conditions.

FIGS. 608-610 depict three variants of the same cell. FIGS. 609(A)-(C) show the nominal case, whereas the other figures represent intentionally misaligned conditions.

FIGS. 611-613 depict three variants of the same cell. FIGS. 612(A)-(C) show the nominal case, whereas the other figures represent intentionally misaligned conditions.

FIGS. 614-616 depict three variants of the same cell. FIGS. 615(A)-(C) show the nominal case, whereas the other figures represent intentionally misaligned conditions.

FIGS. 617-619 depict three variants of the same cell. FIGS. 618(A)-(C) show the nominal case, whereas the other figures represent intentionally misaligned conditions.

FIGS. 621-623 depict three variants of the same cell. FIGS. 622(A)-(C) show the nominal case, whereas the other figures represent intentionally misaligned conditions.

FIGS. 624-626 depict three variants of the same cell. FIGS. 625(A)-(C) show the nominal case, whereas the other figures represent intentionally misaligned conditions.

FIGS. 627-629 depict three variants of the same cell. FIGS. 628(A)-(C) show the nominal case, whereas the other figures represent intentionally misaligned conditions.

FIGS. 630-632 depict three variants of the same cell. FIGS. 631(A)-(C) show the nominal case, whereas the other figures represent intentionally misaligned conditions.

FIGS. 668-670 depict three variants of the same cell. FIGS. 669(A)-(C) show the nominal case, whereas the other figures represent intentionally misaligned conditions.

FIGS. 756-758 depict three variants of the same cell. FIGS. 757(A)-(C) show the nominal case, whereas the other figures represent intentionally misaligned conditions.

FIGS. 759-760 depict two variants of the same cell. FIGS. 759(A)-(C) show the nominal case, whereas the other figures represent intentionally misaligned conditions.

FIGS. 762-764 depict three variants of the same cell. FIGS. 764(A)-(C) show the nominal case, whereas the other figures represent intentionally misaligned conditions.

FIGS. 765-767 depict three variants of the same cell. FIGS. 766(A)-(C) show the nominal case, whereas the other figures represent intentionally misaligned conditions.

FIGS. 768-770 depict three variants of the same cell. FIGS. 769(A)-(C) show the nominal case, whereas the other figures represent intentionally misaligned conditions.

FIGS. 771-773 depict three variants of the same cell. FIGS. 772(A)-(C) show the nominal case, whereas the other figures represent intentionally misaligned conditions.

FIGS. 774-776 depict three variants of the same cell. FIGS. 774(A)-(C) show the nominal case, whereas the other figures represent intentionally misaligned conditions.

FIGS. 777-779 depict three variants of the same cell. FIGS. 779(A)-(C) show the nominal case, whereas the other figures represent intentionally misaligned conditions.

FIGS. 780-782 depict three variants of the same cell. FIGS. 780(A)-(C) show the nominal case, whereas the other figures represent intentionally misaligned conditions.

FIGS. 783-785 depict three variants of the same cell. FIGS. 785(A)-(C) show the nominal case, whereas the other figures represent intentionally misaligned conditions.

FIGS. 799-801 depict three variants of the same cell. FIGS. 800(A)-(C) show the nominal case, whereas the other figures represent intentionally misaligned conditions.

FIGS. 802-804 depict three variants of the same cell. FIGS. 803(A)-(C) show the nominal case, whereas the other figures represent intentionally misaligned conditions.

FIGS. 805-807 depict three variants of the same cell. FIGS. 806(A)-(C) show the nominal case, whereas the other figures represent intentionally misaligned conditions.

FIGS. 808-810 depict three variants of the same cell. FIGS. 809(A)-(C) show the nominal case, whereas the other figures represent intentionally misaligned conditions.

FIGS. 811-813 depict three variants of the same cell. FIGS. 812(A)-(C) show the nominal case, whereas the other figures represent intentionally misaligned conditions.

FIGS. 814-816 depict three variants of the same cell. FIGS. 815(A)-(C) show the nominal case, whereas the other figures represent intentionally misaligned conditions.

FIGS. 817-819 depict three variants of the same cell. FIGS. 818(A)-(C) show the nominal case, whereas the other figures represent intentionally misaligned conditions.

FIGS. 820-822 depict three variants of the same cell. FIGS. 821(A)-(C) show the nominal case, whereas the other figures represent intentionally misaligned conditions.

FIGS. 830-832 depict three variants of the same cell. FIGS. 831(A)-(C) show the nominal case, whereas the other figures represent intentionally misaligned conditions.

FIGS. 860-862 depict three variants of the same cell. FIGS. 861(A)-(C) show the nominal case, whereas the other figures represent intentionally misaligned conditions.

FIGS. 863-865 depict three variants of the same cell. FIGS. 864(A)-(C) show the nominal case, whereas the other figures represent intentionally misaligned conditions.

FIGS. 866-867 depict two variants of the same cell. The figure set represents intentionally misaligned conditions.

FIGS. 868-869 depict two variants of the same cell. The figure set represents intentionally misaligned conditions.

FIGS. 870-872 depict three variants of the same cell. FIGS. 871(A)-(C) show the nominal case, whereas the other figures represent intentionally misaligned conditions.

FIGS. 873-875 depict three variants of the same cell. FIGS. 874(A)-(C) show the nominal case, whereas the other figures represent intentionally misaligned conditions.

FIGS. 876-878 depict three variants of the same cell. FIGS. 877(A)-(C) show the nominal case, whereas the other figures represent intentionally misaligned conditions.

FIGS. 880-882 depict three variants of the same cell. FIGS. 881(A)-(C) show the nominal case, whereas the other figures represent intentionally misaligned conditions.

FIGS. 883-885 depict three variants of the same cell. FIGS. 884(A)-(C) show the nominal case, whereas the other figures represent intentionally misaligned conditions.

FIGS. 886-888 depict three variants of the same cell. FIGS. 887(A)-(C) show the nominal case, whereas the other figures represent intentionally misaligned conditions.

FIGS. 889-891 depict three variants of the same cell. FIGS. 890(A)-(C) show the nominal case, whereas the other figures represent intentionally misaligned conditions.

FIGS. 892-894 depict three variants of the same cell. FIGS. 893(A)-(C) show the nominal case, whereas the other figures represent intentionally misaligned conditions.

FIGS. 895-897 depict three variants of the same cell. FIGS. 896(A)-(C) show the nominal case, whereas the other figures represent intentionally misaligned conditions.

FIGS. 898-900 depict three variants of the same cell. FIGS. 899(A)-(C) show the nominal case, whereas the other figures represent intentionally misaligned conditions.

FIGS. 901-903 depict three variants of the same cell. FIGS. 902(A)-(C) show the nominal case, whereas the other figures represent intentionally misaligned conditions.

FIGS. 1003-1005 depict three variants of the same cell. FIGS. 1004(A)-(C) show the nominal case, whereas the other figures represent intentionally misaligned conditions.

FIGS. 1006-1008 depict three variants of the same cell. FIGS. 1007(A)-(C) show the nominal case, whereas the other figures represent intentionally misaligned conditions.

FIGS. 1009-1011 depict three variants of the same cell. FIGS. 1010(A)-(C) show the nominal case, whereas the other figures represent intentionally misaligned conditions.

FIGS. 1081-1082 depict two variants of the same cell. FIGS. 1081(A)-(C) show the nominal case, whereas the other figures represent intentionally misaligned conditions.

FIGS. 1096-1098 depict three variants of the same cell. FIGS. 1097(A)-(C) show the nominal case, whereas the other figures represent intentionally misaligned conditions.

FIGS. 1099-1101 depict three variants of the same cell. FIGS. 1100(A)-(C) show the nominal case, whereas the other figures represent intentionally misaligned conditions.

FIGS. 1102-1104 depict three variants of the same cell. FIGS. 1103(A)-(C) show the nominal case, whereas the other figures represent intentionally misaligned conditions.

FIGS. 1105-1107 depict three variants of the same cell. FIGS. 1106(A)-(C) show the nominal case, whereas the other figures represent intentionally misaligned conditions.

FIGS. 1108-1110 depict three variants of the same cell. FIGS. 1109(A)-(C) show the nominal case, whereas the other figures represent intentionally misaligned conditions.

FIGS. 1111-1113 depict three variants of the same cell. FIGS. 1112(A)-(C) show the nominal case, whereas the other figures represent intentionally misaligned conditions.

FIGS. 1114-1116 depict three variants of the same cell. FIGS. 1115(A)-(C) show the nominal case, whereas the other figures represent intentionally misaligned conditions.

FIGS. 1117-1119 depict three variants of the same cell. FIGS. 1118(A)-(C) show the nominal case, whereas the other figures represent intentionally misaligned conditions.

FIGS. 1138-1140 depict three variants of the same cell. FIGS. 1139(A)-(C) show the nominal case, whereas the other figures represent intentionally misaligned conditions.

FIGS. 1141-1143 depict three variants of the same cell. FIGS. 1142(A)-(C) show the nominal case, whereas the other figures represent intentionally misaligned conditions.

FIGS. 1144-1145 depict two variants of the same cell. The figure set represents intentionally misaligned conditions.

FIGS. 1146-1147 depict two variants of the same cell. The figure set represents intentionally misaligned conditions.

FIGS. 1150-1152 depict three variants of the same cell. FIGS. 1151(A)-(C) show the nominal case, whereas the other figures represent intentionally misaligned conditions.

FIGS. 1153-1155 depict three variants of the same cell. FIGS. 1154(A)-(C) show the nominal case, whereas the other figures represent intentionally misaligned conditions.

FIGS. 1156-1158 depict three variants of the same cell. FIGS. 1157(A)-(C) show the nominal case, whereas the other figures represent intentionally misaligned conditions.

FIGS. 1159-1161 depict three variants of the same cell. FIGS. 1160(A)-(C) show the nominal case, whereas the other figures represent intentionally misaligned conditions.

FIGS. 1162-1164 depict three variants of the same cell. FIGS. 1163(A)-(C) show the nominal case, whereas the other figures represent intentionally misaligned conditions.

FIGS. 1165-1167 depict three variants of the same cell. FIGS. 1166(A)-(C) show the nominal case, whereas the other figures represent intentionally misaligned conditions.

FIGS. 1168-1170 depict three variants of the same cell. FIGS. 1169(A)-(C) show the nominal case, whereas the other figures represent intentionally misaligned conditions.

FIGS. 1171-1173 depict three variants of the same cell. FIGS. 1172(A)-(C) show the nominal case, whereas the other figures represent intentionally misaligned conditions.

FIGS. 1174-1176 depict three variants of the same cell. FIGS. 1175(A)-(C) show the nominal case, whereas the other figures represent intentionally misaligned conditions.

FIGS. 1177-1179 depict three variants of the same cell. FIGS. 1178(A)-(C) show the nominal case, whereas the other figures represent intentionally misaligned conditions.

FIGS. 1189-1191 depict three variants of the same cell. FIGS. 1190(A)-(C) show the nominal case, whereas the other figures represent intentionally misaligned conditions.

FIGS. 1192-1194 depict three variants of the same cell. FIGS. 1193(A)-(C) show the nominal case, whereas the other figures represent intentionally misaligned conditions.

FIGS. 1195-1197 depict three variants of the same cell. FIGS. 1196(A)-(C) show the nominal case, whereas the other figures represent intentionally misaligned conditions.

FIGS. 1198-1200 depict three variants of the same cell. FIGS. 1199(A)-(C) show the nominal case, whereas the other figures represent intentionally misaligned conditions.

FIGS. 1201-1203 depict two variants of the same cell. FIGS. 1202(A)-(C) show the nominal case, whereas the other figures represent intentionally misaligned conditions.

FIGS. 1204-1206 depict three variants of the same cell. FIGS. 1205(A)-(C) show the nominal case, whereas the other figures represent intentionally misaligned conditions.

FIGS. 1207-1209 depict three variants of the same cell. FIGS. 1207(A)-(C) show the nominal case, whereas the other figures represent intentionally misaligned conditions.

FIGS. 1210-1212 depict three variants of the same cell. FIGS. 1210(A)-(C) show the nominal case, whereas the other figures represent intentionally misaligned conditions.

FIGS. 1213-1215 depict three variants of the same cell. FIGS. 1213(A)-(C) show the nominal case, whereas the other figures represent intentionally misaligned conditions.

FIGS. 1216-1218 depict three variants of the same cell. FIGS. 1216(A)-(C) show the nominal case, whereas the other figures represent intentionally misaligned conditions.

FIGS. 1219-1221 depict three variants of the same cell. FIGS. 1220(A)-(C) show the nominal case, whereas the other figures represent intentionally misaligned conditions.

FIGS. 1222-1224 depict three variants of the same cell. FIGS. 1223(A)-(C) show the nominal case, whereas the other figures represent intentionally misaligned conditions.

FIGS. 1225-1227 depict three variants of the same cell. FIGS. 1226(A)-(C) show the nominal case, whereas the other figures represent intentionally misaligned conditions.

FIGS. 1228-1230 depict three variants of the same cell. FIGS. 1229(A)-(C) show the nominal case, whereas the other figures represent intentionally misaligned conditions.

FIGS. 1231-1233 depict three variants of the same cell. FIGS. 1232(A)-(C) show the nominal case, whereas the other figures represent intentionally misaligned conditions.

FIGS. 1236-1238 depict three variants of the same cell. FIGS. 1237(A)-(C) show the nominal case, whereas the other figures represent intentionally misaligned conditions.

FIGS. 1239-1242 depict variants of the same cell. FIGS. 1242(A)-(C) show the nominal case, whereas the other figures represent intentionally misaligned conditions.

FIGS. 1240-1241 depict two variants of the same cell. FIGS. 1240(A)-(C) show the nominal case, whereas the other figures represent intentionally misaligned conditions.

FIGS. 1249-1251 depict three variants of the same cell. FIGS. 1250(A)-(C) show the nominal case, whereas the other figures represent intentionally misaligned conditions.

FIGS. 1252-1254 depict three variants of the same cell. FIGS. 1253(A)-(C) show the nominal case, whereas the other figures represent intentionally misaligned conditions.

FIGS. 1255-1257 depict three variants of the same cell. FIGS. 1256(A)-(C) show the nominal case, whereas the other figures represent intentionally misaligned conditions.

FIGS. 1258-1260 depict three variants of the same cell. FIGS. 1259(A)-(C) show the nominal case, whereas the other figures represent intentionally misaligned conditions.

FIGS. 1261-1263 depict three variants of the same cell. FIGS. 1262(A)-(C) show the nominal case, whereas the other figures represent intentionally misaligned conditions.

FIGS. 1293-1294 depict two variants of the same cell. FIGS. 1294(A)-(C) show the nominal case, whereas the other figures represent intentionally misaligned conditions.

FIGS. 1295-1296 depict two variants of the same cell. FIGS. 1296(A)-(C) show the nominal case, whereas the other figures represent intentionally misaligned conditions.

FIGS. 1367-1368 depict two variants of the same cell. FIGS. 1368(A)-(C) show the nominal case, whereas the other figures represent intentionally misaligned conditions.

FIGS. 1369-1370 depict two variants of the same cell. FIGS. 1370(A)-(C) show the nominal case, whereas the other figures represent intentionally misaligned conditions.

FIGS. 1371-1372 depict two variants of the same cell. FIGS. 1372(A)-(C) show the nominal case, whereas the other figures represent intentionally misaligned conditions.

FIGS. 1373-1375 depict three variants of the same cell. FIGS. 1374(A)-(C) show the nominal case, whereas the other figures represent intentionally misaligned conditions.

FIGS. 1376-1377 depict two variants of the same cell. FIGS. 1377(A)-(C) show the nominal case, whereas the other figures represent intentionally misaligned conditions.

FIGS. 1378-1379 depict two variants of the same cell. FIGS. 1379(A)-(C) show the nominal case, whereas the other figures represent intentionally misaligned conditions.

FIGS. 1386-1387 depict two variants of the same cell. FIGS. 1386(A)-(C) show the nominal case, whereas the other figures represent intentionally misaligned conditions.

FIGS. 1388-1389 depict two variants of the same cell. FIGS. 1389(A)-(C) show the nominal case, whereas the other figures represent intentionally misaligned conditions.

FIGS. 1390-1391 depict two variants of the same cell. The figure set represents intentionally misaligned conditions.

FIGS. 1392-1394 depict three variants of the same cell. FIGS. 1392(A)-(C) show the nominal case, whereas the other figures represent intentionally misaligned conditions.

FIGS. 1399-1401 depict three variants of the same cell. FIGS. 1400(A)-(C) show the nominal case, whereas the other figures represent intentionally misaligned conditions.

FIGS. 1402-1404 depict three variants of the same cell. FIGS. 1403(A)-(C) show the nominal case, whereas the other figures represent intentionally misaligned conditions.

FIGS. 1406-1407 depict two variants of the same cell. FIGS. 1407(A)-(C) show the nominal case, whereas the other figures represent intentionally misaligned conditions.

FIGS. 1410-1412 depict three variants of the same cell. FIGS. 1411(A)-(C) show the nominal case, whereas the other figures represent intentionally misaligned conditions.

FIGS. 1451-1452 depict two variants of the same cell. FIGS. 1452(A)-(C) show the nominal case, whereas the other figures represent intentionally misaligned conditions.

FIGS. 1456-1458 depict three variants of the same cell. FIGS. 1457(A)-(C) show the nominal case, whereas the other figures represent intentionally misaligned conditions.

FIGS. 1510-1512 depict three variants of the same cell. FIGS. 1511(A)-(C) show the nominal case, whereas the other figures represent intentionally misaligned conditions.

FIGS. 1513-1515 depict three variants of the same cell. FIGS. 1514(A)-(C) show the nominal case, whereas the other figures represent intentionally misaligned conditions.

FIGS. 1516-1518 depict three variants of the same cell. FIGS. 1517(A)-(C) show the nominal case, whereas the other figures represent intentionally misaligned conditions.

FIGS. 1522-1524 depict three variants of the same cell. FIGS. 1523(A)-(C) show the nominal case, whereas the other figures represent intentionally misaligned conditions.

FIGS. 1525-1527 depict three variants of the same cell. FIGS. 1526(A)-(C) show the nominal case, whereas the other figures represent intentionally misaligned conditions.

FIGS. 1528-1530 depict three variants of the same cell. FIGS. 1528(A)-(C) show the nominal case, whereas the other figures represent intentionally misaligned conditions.

FIGS. 1531-1533 depict three variants of the same cell. FIGS. 1531(A)-(C) show the nominal case, whereas the other figures represent intentionally misaligned conditions.

FIGS. 1534-1536 depict three variants of the same cell. FIGS. 1534(A)-(C) show the nominal case, whereas the other figures represent intentionally misaligned conditions.

FIGS. 1537-1539 depict three variants of the same cell. FIGS. 1537(A)-(C) show the nominal case, whereas the other figures represent intentionally misaligned conditions.

FIGS. 1543-1545 depict three variants of the same cell. FIGS. 1544(A)-(C) show the nominal case, whereas the other figures represent intentionally misaligned conditions.

FIGS. 1546-1548 depict three variants of the same cell. FIGS. 1547(A)-(C) show the nominal case, whereas the other figures represent intentionally misaligned conditions.

FIGS. 1553-1554 depict two variants of the same cell. FIGS. 1554(A)-(C) show the nominal case, whereas the other figures represent intentionally misaligned conditions.

FIGS. 1555-1556 depict two variants of the same cell. FIGS. 1556(A)-(C) show the nominal case, whereas the other figures represent intentionally misaligned conditions.

FIGS. 1557-1559 depict three variants of the same cell. FIGS. 1558(A)-(C) show the nominal case, whereas the other figures represent intentionally misaligned conditions.

FIGS. 1560-1562 depict three variants of the same cell. FIGS. 1561(A)-(C) show the nominal case, whereas the other figures represent intentionally misaligned conditions.

FIGS. 1563-1565 depict three variants of the same cell. FIGS. 1564(A)-(C) show the nominal case, whereas the other figures represent intentionally misaligned conditions.

FIGS. 1566-1568 depict three variants of the same cell. FIGS. 1567(A)-(C) show the nominal case, whereas the other figures represent intentionally misaligned conditions.

FIGS. 1569-1571 depict three variants of the same cell. FIGS. 1570(A)-(C) show the nominal case, whereas the other figures represent intentionally misaligned conditions.

FIGS. 1572-1574 depict three variants of the same cell. FIGS. 1573(A)-(C) show the nominal case, whereas the other figures represent intentionally misaligned conditions.

FIGS. 1575-1577 depict three variants of the same cell. FIGS. 1576(A)-(C) show the nominal case, whereas the other figures represent intentionally misaligned conditions.

FIGS. 1578-1580 depict three variants of the same cell. FIGS. 1579(A)-(C) show the nominal case, whereas the other figures represent intentionally misaligned conditions.

FIGS. 1581-1583 depict three variants of the same cell. FIGS. 1582(A)-(C) show the nominal case, whereas the other figures represent intentionally misaligned conditions.

FIGS. 1584-1586 depict three variants of the same cell. FIGS. 1585(A)-(C) show the nominal case, whereas the other figures represent intentionally misaligned conditions.

FIGS. 1587-1589 depict three variants of the same cell. FIGS. 1588(A)-(C) show the nominal case, whereas the other figures represent intentionally misaligned conditions.

FIGS. 1590-1592 depict three variants of the same cell. FIGS. 1591(A)-(C) show the nominal case, whereas the other figures represent intentionally misaligned conditions.

FIGS. 1593-1595 depict three variants of the same cell. FIGS. 1594(A)-(C) show the nominal case, whereas the other figures represent intentionally misaligned conditions.

FIGS. 1596-1598 depict three variants of the same cell. FIGS. 1597(A)-(C) show the nominal case, whereas the other figures represent intentionally misaligned conditions.

FIGS. 1599-1601 depict three variants of the same cell. FIGS. 1600(A)-(C) show the nominal case, whereas the other figures represent intentionally misaligned conditions.

FIGS. 1602-1604 depict three variants of the same cell. FIGS. 1603(A)-(C) show the nominal case, whereas the other figures represent intentionally misaligned conditions.

FIGS. 1605-1607 depict three variants of the same cell. FIGS. 1606(A)-(C) show the nominal case, whereas the other figures represent intentionally misaligned conditions.

FIGS. 1608-1610 depict three variants of the same cell. FIGS. 1609(A)-(C) show the nominal case, whereas the other figures represent intentionally misaligned conditions.

FIGS. 1611-1613 depict three variants of the same cell. FIGS. 1612(A)-(C) show the nominal case, whereas the other figures represent intentionally misaligned conditions.

FIGS. 1614-1616 depict three variants of the same cell. FIGS. 1615(A)-(C) show the nominal case, whereas the other figures represent intentionally misaligned conditions.

FIGS. 1617-1619 depict three variants of the same cell. FIGS. 1618(A)-(C) show the nominal case, whereas the other figures represent intentionally misaligned conditions.

FIGS. 1620-1622 depict three variants of the same cell. FIGS. 1621(A)-(C) show the nominal case, whereas the other figures represent intentionally misaligned conditions.

FIGS. 1623-1625 depict three variants of the same cell. FIGS. 1624(A)-(C) show the nominal case, whereas the other figures represent intentionally misaligned conditions.

FIGS. 1626-1628 depict three variants of the same cell. FIGS. 1627(A)-(C) show the nominal case, whereas the other figures represent intentionally misaligned conditions.

FIGS. 1646-1647 depict two variants of the same cell. FIGS. 1646(A)-(C) show the nominal case, whereas the other figures represent intentionally misaligned conditions.

FIGS. 1648-1649 depict two variants of the same cell. FIGS. 1648(A)-(C) show the nominal case, whereas the other figures represent intentionally misaligned conditions.

FIGS. 1650-1652 depict three variants of the same cell. FIGS. 1651(A)-(C) show the nominal case, whereas the other figures represent intentionally misaligned conditions.

FIGS. 1653-1655 depict three variants of the same cell. FIGS. 1654(A)-(C) show the nominal case, whereas the other figures represent intentionally misaligned conditions.

FIGS. 1656-1658 depict three variants of the same cell. FIGS. 1657(A)-(C) show the nominal case, whereas the other figures represent intentionally misaligned conditions.

FIGS. 1659-1661 depict three variants of the same cell. FIGS. 1660(A)-(C) show the nominal case, whereas the other figures represent intentionally misaligned conditions.

FIGS. 1663-1664 depict two variants of the same cell. FIGS. 1663(A)-(C) show the nominal case, whereas the other figures represent intentionally misaligned conditions.

FIGS. 1665-1667 depict three variants of the same cell. FIGS. 1666(A)-(C) show the nominal case, whereas the other figures represent intentionally misaligned conditions.

FIGS. 1669-1670 depict two variants of the same cell. FIGS. 1669(A)-(C) show the nominal case, whereas the other figures represent intentionally misaligned conditions.

FIGS. 1671-1673 depict three variants of the same cell. FIGS. 1672(A)-(C) show the nominal case, whereas the other figures represent intentionally misaligned conditions.

FIGS. 1674-1676 depict three variants of the same cell. FIGS. 1675(A)-(C) show the nominal case, whereas the other figures represent intentionally misaligned conditions.

FIGS. 1677-1679 depict three variants of the same cell. FIGS. 1678(A)-(C) show the nominal case, whereas the other figures represent intentionally misaligned conditions.

FIGS. 1680-1682 depict three variants of the same cell. FIGS. 1681(A)-(C) show the nominal case, whereas the other figures represent intentionally misaligned conditions.

FIGS. 1687-1689 depict three variants of the same cell. FIGS. 1688(A)-(C) show the nominal case, whereas the other figures represent intentionally misaligned conditions.

FIGS. 1690-1692 depict three variants of the same cell. FIGS. 1691(A)-(C) show the nominal case, whereas the other figures represent intentionally misaligned conditions.

FIGS. 1693-1695 depict three variants of the same cell. FIGS. 1694(A)-(C) show the nominal case, whereas the other figures represent intentionally misaligned conditions.

FIGS. 1696-1698 depict three variants of the same cell. FIGS. 1697(A)-(C) show the nominal case, whereas the other figures represent intentionally misaligned conditions.

FIGS. 1715-1717 depict three variants of the same cell. FIGS. 1716(A)-(C) show the nominal case, whereas the other figures represent intentionally misaligned conditions.

FIGS. 1718-1720 depict three variants of the same cell. FIGS. 1719(A)-(C) show the nominal case, whereas the other figures represent intentionally misaligned conditions.

FIGS. 1800-1802 depict three variants of the same cell. FIGS. 1801(A)-(C) show the nominal case, whereas the other figures represent intentionally misaligned conditions.

FIGS. 1813-1815 depict three variants of the same cell. FIGS. 1814(A)-(C) show the nominal case, whereas the other figures represent intentionally misaligned conditions.

FIGS. 1816-1818 depict three variants of the same cell. FIGS. 1817(A)-(C) show the nominal case, whereas the other figures represent intentionally misaligned conditions.

FIGS. 1819-1821 depict three variants of the same cell. FIGS. 1820(A)-(C) show the nominal case, whereas the other figures represent intentionally misaligned conditions.

FIGS. 1822-1824 depict three variants of the same cell. FIGS. 1823(A)-(C) show the nominal case, whereas the other figures represent intentionally misaligned conditions.

FIGS. 1825-1827 depict three variants of the same cell. FIGS. 1826(A)-(C) show the nominal case, whereas the other figures represent intentionally misaligned conditions.

FIGS. 1828-1830 depict three variants of the same cell. FIGS. 1829(A)-(C) show the nominal case, whereas the other figures represent intentionally misaligned conditions.

FIGS. 1831-1832 depict two variants of the same cell. FIGS. 1831(A)-(C) show the nominal case, whereas the other figures represent intentionally misaligned conditions.

FIGS. 1833-1835 depict three variants of the same cell. FIGS. 1833(A)-(C) show the nominal case, whereas the other figures represent intentionally misaligned conditions.

FIGS. 1836-1838 depict three variants of the same cell. FIGS. 1836(A)-(C) show the nominal case, whereas the other figures represent intentionally misaligned conditions.

FIGS. 1839-1841 depict three variants of the same cell. FIGS. 1839(A)-(C) show the nominal case, whereas the other figures represent intentionally misaligned conditions.

FIGS. 1842-1844 depict three variants of the same cell. FIGS. 1842(A)-(C) show the nominal case, whereas the other figures represent intentionally misaligned conditions.

FIGS. 1845-1847 depict three variants of the same cell. FIGS. 1845(A)-(C) show the nominal case, whereas the other figures represent intentionally misaligned conditions.

FIGS. 1848-1849 depict two variants of the same cell. FIGS. 1848(A)-(C) show the nominal case, whereas the other figures represent intentionally misaligned conditions.

FIGS. 1850-1852 depict three variants of the same cell. FIGS. 1850(A)-(C) show the nominal case, whereas the other figures represent intentionally misaligned conditions.

FIGS. 1853-1855 depict three variants of the same cell. FIGS. 1853(A)-(C) show the nominal case, whereas the other figures represent intentionally misaligned conditions.

FIGS. 1856-1858 depict three variants of the same cell. FIGS. 1856(A)-(C) show the nominal case, whereas the other figures represent intentionally misaligned conditions.

FIGS. 1859-1861 depict three variants of the same cell. FIGS. 1859(A)-(C) show the nominal case, whereas the other figures represent intentionally misaligned conditions.

FIGS. 1867-1869 depict three variants of the same cell. FIGS. 1868(A)-(C) show the nominal case, whereas the other figures represent intentionally misaligned conditions.

FIGS. 1870-1872 depict three variants of the same cell. FIGS. 1871(A)-(C) show the nominal case, whereas the other figures represent intentionally misaligned conditions.

FIGS. 1873-1875 depict three variants of the same cell. FIGS. 1874(A)-(C) show the nominal case, whereas the other figures represent intentionally misaligned conditions.

FIGS. 1876-1878 depict three variants of the same cell. FIGS. 1877(A)-(C) show the nominal case, whereas the other figures represent intentionally misaligned conditions.

FIGS. 1879-1881 depict three variants of the same cell. FIGS. 1880(A)-(C) show the nominal case, whereas the other figures represent intentionally misaligned conditions.

FIGS. 1882-1884 depict three variants of the same cell. FIGS. 1883(A)-(C) show the nominal case, whereas the other figures represent intentionally misaligned conditions.

FIGS. 1885-1887 depict three variants of the same cell. FIGS. 1886(A)-(C) show the nominal case, whereas the other figures represent intentionally misaligned conditions.

FIGS. 1888-1890 depict three variants of the same cell. FIGS. 1889(A)-(C) show the nominal case, whereas the other figures represent intentionally misaligned conditions.

FIGS. 1891-1893 depict three variants of the same cell. FIGS. 1892(A)-(C) show the nominal case, whereas the other figures represent intentionally misaligned conditions.

FIGS. 1894-1896 depict three variants of the same cell. FIGS. 1895(A)-(C) show the nominal case, whereas the other figures represent intentionally misaligned conditions.

FIGS. 1897-1899 depict three variants of the same cell. FIGS. 1898(A)-(C) show the nominal case, whereas the other figures represent intentionally misaligned conditions.

FIGS. 1900-1902 depict three variants of the same cell. FIGS. 1901(A)-(C) show the nominal case, whereas the other figures represent intentionally misaligned conditions.

FIGS. 1903-1905 depict three variants of the same cell. FIGS. 1904(A)-(C) show the nominal case, whereas the other figures represent intentionally misaligned conditions.

FIGS. 1906-1908 depict three variants of the same cell. FIGS. 1907(A)-(C) show the nominal case, whereas the other figures represent intentionally misaligned conditions.

FIGS. 1909-1911 depict three variants of the same cell. FIGS. 1910(A)-(C) show the nominal case, whereas the other figures represent intentionally misaligned conditions.

FIGS. 1912-1914 depict three variants of the same cell. FIGS. 1913(A)-(C) show the nominal case, whereas the other figures represent intentionally misaligned conditions.

FIGS. 1915-1917 depict three variants of the same cell. FIGS. 1916(A)-(C) show the nominal case, whereas the other figures represent intentionally misaligned conditions.

FIGS. 1918-1920 depict three variants of the same cell. FIGS. 1919(A)-(C) show the nominal case, whereas the other figures represent intentionally misaligned conditions.

FIGS. 1921-1923 depict three variants of the same cell. FIGS. 1922(A)-(C) show the nominal case, whereas the other figures represent intentionally misaligned conditions.

FIGS. 1924-1926 depict three variants of the same cell. FIGS. 1925(A)-(C) show the nominal case, whereas the other figures represent intentionally misaligned conditions.

FIGS. 1927-1929 depict three variants of the same cell. FIGS. 1928(A)-(C) show the nominal case, whereas the other figures represent intentionally misaligned conditions.

FIGS. 1930-1932 depict three variants of the same cell. FIGS. 1931(A)-(C) show the nominal case, whereas the other figures represent intentionally misaligned conditions.

FIGS. 1933-1935 depict three variants of the same cell. FIGS. 1934(A)-(C) show the nominal case, whereas the other figures represent intentionally misaligned conditions.

FIGS. 1936-1938 depict three variants of the same cell. FIGS. 1937(A)-(C) show the nominal case, whereas the other figures represent intentionally misaligned conditions.

FIGS. 1939-1941 depict three variants of the same cell. FIGS. 1940(A)-(C) show the nominal case, whereas the other figures represent intentionally misaligned conditions.

FIGS. 1943-1944 depict two variants of the same cell. FIGS. 1943(A)-(C) show the nominal case, whereas the other figures represent intentionally misaligned conditions.

FIGS. 1945-1947 depict three variants of the same cell. FIGS. 1946(A)-(C) show the nominal case, whereas the other figures represent intentionally misaligned conditions.

FIGS. 1948-1950 depict three variants of the same cell. FIGS. 1949(A)-(C) show the nominal case, whereas the other figures represent intentionally misaligned conditions.

FIGS. 1951-1953 depict three variants of the same cell. FIGS. 1952(A)-(C) show the nominal case, whereas the other figures represent intentionally misaligned conditions.

FIGS. 1954-1956 depict three variants of the same cell. FIGS. 1955(A)-(C) show the nominal case, whereas the other figures represent intentionally misaligned conditions.

FIGS. 1957-1959 depict three variants of the same cell. FIGS. 1958(A)-(C) show the nominal case, whereas the other figures represent intentionally misaligned conditions.

FIGS. 1960-1962 depict three variants of the same cell. FIGS. 1961(A)-(C) show the nominal case, whereas the other figures represent intentionally misaligned conditions.

FIGS. 1963-1965 depict three variants of the same cell. FIGS. 1964(A)-(C) show the nominal case, whereas the other figures represent intentionally misaligned conditions.

FIGS. 1966-1968 depict three variants of the same cell. FIGS. 1967(A)-(C) show the nominal case, whereas the other figures represent intentionally misaligned conditions.

FIGS. 1969-1971 depict three variants of the same cell. FIGS. 1970(A)-(C) show the nominal case, whereas the other figures represent intentionally misaligned conditions.

FIGS. 1972-1974 depict three variants of the same cell. FIGS. 1973(A)-(C) show the nominal case, whereas the other figures represent intentionally misaligned conditions.

FIGS. 1975-1977 depict three variants of the same cell. FIGS. 1976(A)-(C) show the nominal case, whereas the other figures represent intentionally misaligned conditions.

FIGS. 1978-1980 depict three variants of the same cell. FIGS. 1979(A)-(C) show the nominal case, whereas the other figures represent intentionally misaligned conditions.

FIGS. 1981-1983 depict three variants of the same cell. FIGS. 1982(A)-(C) show the nominal case, whereas the other figures represent intentionally misaligned conditions.

FIGS. 1984-1986 depict three variants of the same cell. FIGS. 1985(A)-(C) show the nominal case, whereas the other figures represent intentionally misaligned conditions.

FIGS. 1987-1989 depict three variants of the same cell. FIGS. 1988(A)-(C) show the nominal case, whereas the other figures represent intentionally misaligned conditions.

FIGS. 1990-1993 depict variants of the same cell. FIGS. 1991(A)-(C) show the nominal case, whereas the other figures represent intentionally misaligned conditions.

FIGS. 1994-1996 depict three variants of the same cell. FIGS. 1995(A)-(C) show the nominal case, whereas the other figures represent intentionally misaligned conditions.

FIGS. 1997-1999 depict three variants of the same cell. FIGS. 1998(A)-(C) show the nominal case, whereas the other figures represent intentionally misaligned conditions.

FIGS. 2000-2002 depict three variants of the same cell. FIGS. 2001(A)-(C) show the nominal case, whereas the other figures represent intentionally misaligned conditions.

FIGS. 2003-2005 depict three variants of the same cell. FIGS. 2003(A)-(C) show the nominal case, whereas the other figures represent intentionally misaligned conditions.

FIGS. 2006-2008 depict three variants of the same cell. FIGS. 2007(A)-(C) show the nominal case, whereas the other figures represent intentionally misaligned conditions.

FIGS. 2009-2011 depict three variants of the same cell. FIGS. 2010(A)-(C) show the nominal case, whereas the other figures represent intentionally misaligned conditions.

FIGS. 2012-2014 depict three variants of the same cell. FIGS. 2013(A)-(C) show the nominal case, whereas the other figures represent intentionally misaligned conditions.

FIGS. 2015-2017 depict three variants of the same cell. FIGS. 2016(A)-(C) show the nominal case, whereas the other figures represent intentionally misaligned conditions.

FIGS. 2018-2020 depict three variants of the same cell. FIGS. 2019(A)-(C) show the nominal case, whereas the other figures represent intentionally misaligned conditions.

FIGS. 2021-2023 depict three variants of the same cell. FIGS. 2022(A)-(C) show the nominal case, whereas the other figures represent intentionally misaligned conditions.

FIGS. 2024-2026 depict three variants of the same cell. FIGS. 2025(A)-(C) show the nominal case, whereas the other figures represent intentionally misaligned conditions.

FIGS. 2027-2029 depict three variants of the same cell. FIGS. 2028(A)-(C) show the nominal case, whereas the other figures represent intentionally misaligned conditions.

FIGS. 2030-2032 depict three variants of the same cell. FIGS. 2031(A)-(C) show the nominal case, whereas the other figures represent intentionally misaligned conditions.

FIGS. 2033-2035 depict three variants of the same cell. FIGS. 2034(A)-(C) show the nominal case, whereas the other figures represent intentionally misaligned conditions.

FIGS. 2036-2038 depict three variants of the same cell. FIGS. 2037(A)-(C) show the nominal case, whereas the other figures represent intentionally misaligned conditions.

FIGS. 2039-2041 depict three variants of the same cell. FIGS. 2040(A)-(C) show the nominal case, whereas the other figures represent intentionally misaligned conditions.

FIGS. 2042-2044 depict three variants of the same cell. FIGS. 2043(A)-(C) show the nominal case, whereas the other figures represent intentionally misaligned conditions.

FIGS. 2045-2047 depict three variants of the same cell. FIGS. 2046(A)-(C) show the nominal case, whereas the other figures represent intentionally misaligned conditions.

FIGS. 2048-2050 depict three variants of the same cell. FIGS. 2049(A)-(C) show the nominal case, whereas the other figures represent intentionally misaligned conditions.

FIGS. 2051-2053 depict three variants of the same cell. FIGS. 2052(A)-(C) show the nominal case, whereas the other figures represent intentionally misaligned conditions.

FIGS. 2054-2056 depict three variants of the same cell. FIGS. 2055(A)-(C) show the nominal case, whereas the other figures represent intentionally misaligned conditions.

FIGS. 2057-2059 depict three variants of the same cell. FIGS. 2058(A)-(C) show the nominal case, whereas the other figures represent intentionally misaligned conditions.

FIGS. 2111-2113 depict three variants of the same cell. FIGS. 2112(A)-(C) show the nominal case, whereas the other figures represent intentionally misaligned conditions.

FIGS. 2114-2116 depict three variants of the same cell. FIGS. 2115(A)-(C) show the nominal case, whereas the other figures represent intentionally misaligned conditions.

FIGS. 2117-2118 depict two variants of the same cell. The figure set represents intentionally misaligned conditions.

FIGS. 2219-2220 depict two variants of the same cell. The figure set represents intentionally misaligned conditions.

FIGS. 2121-22123 depict three variants of the same cell. FIGS. 2122(A)-(C) show the nominal case, whereas the other figures represent intentionally misaligned conditions.

FIGS. 2124-2126 depict three variants of the same cell. FIGS. 2125(A)-(C) show the nominal case, whereas the other figures represent intentionally misaligned conditions.

FIGS. 2127-2129 depict three variants of the same cell. FIGS. 2128(A)-(C) show the nominal case, whereas the other figures represent intentionally misaligned conditions.

FIGS. 2130-2132 depict three variants of the same cell. FIGS. 2131(A)-(C) show the nominal case, whereas the other figures represent intentionally misaligned conditions.

FIGS. 2133-2135 depict three variants of the same cell. FIGS. 2133(A)-(C) show the nominal case, whereas the other figures represent intentionally misaligned conditions.

FIGS. 2136-2138 depict two variants of the same cell. FIGS. 2136(A)-(C) show the nominal case, whereas the other figures represent intentionally misaligned conditions.

FIGS. 2138-2139 depict two variants of the same cell. FIGS. 2138(A)-(C) show the nominal case, whereas the other figures represent intentionally misaligned conditions.

FIGS. 2140-2141 depict two variants of the same cell. FIGS. 2140(A)-(C) show the nominal case, whereas the other figures represent intentionally misaligned conditions.

FIGS. 2142-2143 depict two variants of the same cell. FIGS. 2142(A)-(C) show the nominal case, whereas the other figures represent intentionally misaligned conditions.

FIGS. 2144-2145 depict two variants of the same cell. FIGS. 2144(A)-(C) show the nominal case, whereas the other figures represent intentionally misaligned conditions.

FIGS. 2146-2147 depict two variants of the same cell. FIGS. 2146(A)-(C) show the nominal case, whereas the other figures represent intentionally misaligned conditions.

FIGS. 2148-2150 depict three variants of the same cell. FIGS. 2148(A)-(C) show the nominal case, whereas the other figures represent intentionally misaligned conditions.

FIGS. 2151-2153 depict three variants of the same cell. FIGS. 2151(A)-(C) show the nominal case, whereas the other figures represent intentionally misaligned conditions.

FIGS. 2154-2156 depict three variants of the same cell. FIGS. 2154(A)-(C) show the nominal case, whereas the other figures represent intentionally misaligned conditions.

FIGS. 2157-2159 depict three variants of the same cell. FIGS. 2158(A)-(C) show the nominal case, whereas the other figures represent intentionally misaligned conditions.

FIGS. 2160-2162 depict three variants of the same cell. FIGS. 2161(A)-(C) show the nominal case, whereas the other figures represent intentionally misaligned conditions.

FIGS. 2163-2165 depict three variants of the same cell. FIGS. 2164(A)-(C) show the nominal case, whereas the other figures represent intentionally misaligned conditions.

FIGS. 2166-2168 depict three variants of the same cell. FIGS. 2167(A)-(C) show the nominal case, whereas the other figures represent intentionally misaligned conditions.

FIGS. 2171-2173 depict three variants of the same cell. FIGS. 2172(A)-(C) show the nominal case, whereas the other figures represent intentionally misaligned conditions.

FIGS. 2174-2176 depict three variants of the same cell. FIGS. 2175(A)-(C) show the nominal case, whereas the other figures represent intentionally misaligned conditions.

FIGS. 2177-2179 depict three variants of the same cell. FIGS. 2178(A)-(C) show the nominal case, whereas the other figures represent intentionally misaligned conditions.

FIGS. 2180-2182 depict three variants of the same cell. FIGS. 2181(A)-(C) show the nominal case, whereas the other figures represent intentionally misaligned conditions.

FIGS. 2183-2185 depict three variants of the same cell. FIGS. 2184(A)-(C) show the nominal case, whereas the other figures represent intentionally misaligned conditions.

FIGS. 2186-2188 depict three variants of the same cell. FIGS. 2187(A)-(C) show the nominal case, whereas the other figures represent intentionally misaligned conditions.

FIGS. 2189-2191 depict three variants of the same cell. FIGS. 2190(A)-(C) show the nominal case, whereas the other figures represent intentionally misaligned conditions.

FIGS. 2192-2194 depict three variants of the same cell. FIGS. 2193(A)-(C) show the nominal case, whereas the other figures represent intentionally misaligned conditions.

FIGS. 2195-2197 depict three variants of the same cell. FIGS. 2196(A)-(C) show the nominal case, whereas the other figures represent intentionally misaligned conditions.

FIGS. 2200-2202 depict three variants of the same cell. FIGS. 2201(A)-(C) show the nominal case, whereas the other figures represent intentionally misaligned conditions.

FIGS. 2203-2205 depict three variants of the same cell. FIGS. 2204(A)-(C) show the nominal case, whereas the other figures represent intentionally misaligned conditions.

FIGS. 2206-2208 depict three variants of the same cell. FIGS. 2207(A)-(C) show the nominal case, whereas the other figures represent intentionally misaligned conditions.

FIGS. 2209-2211 depict three variants of the same cell. FIGS. 2210(A)-(C) show the nominal case, whereas the other figures represent intentionally misaligned conditions.

FIGS. 2212-2214 depict three variants of the same cell. FIGS. 2213(A)-(C) show the nominal case, whereas the other figures represent intentionally misaligned conditions.

FIGS. 2215-2217 depict three variants of the same cell. FIGS. 2216(A)-(C) show the nominal case, whereas the other figures represent intentionally misaligned conditions.

FIGS. 2218-2220 depict three variants of the same cell. FIGS. 2219(A)-(C) show the nominal case, whereas the other figures represent intentionally misaligned conditions.

FIGS. 2221-2223 depict three variants of the same cell. FIGS. 2222(A)-(B) show the nominal case, whereas the other figures represent intentionally misaligned conditions.

FIGS. 2224-2226 depict three variants of the same cell. FIGS. 2225(A)-(B) show the nominal case, whereas the other figures represent intentionally misaligned conditions.

FIGS. 2227-2229 depict three variants of the same cell. FIGS. 2228(A)-(B) show the nominal case, whereas the other figures represent intentionally misaligned conditions.

FIGS. 2230-2232 depict three variants of the same cell. FIGS. 2231(A)-(B) show the nominal case, whereas the other figures represent intentionally misaligned conditions.

FIGS. 2233-2235 depict three variants of the same cell. FIGS. 2234(A)-(B) show the nominal case, whereas the other figures represent intentionally misaligned conditions.

FIGS. 2236-2238 depict three variants of the same cell. FIGS. 2237(A)-(B) show the nominal case, whereas the other figures represent intentionally misaligned conditions.

FIGS. 2239-2241 depict three variants of the same cell. FIGS. 2240(A)-(B) show the nominal case, whereas the other figures represent intentionally misaligned conditions.

FIGS. 2242-2244 depict three variants of the same cell. FIGS. 2243(A)-(B) show the nominal case, whereas the other figures represent intentionally misaligned conditions.

FIGS. 2245-2247 depict three variants of the same cell. FIGS. 2246(A)-(B) show the nominal case, whereas the other figures represent intentionally misaligned conditions.

FIGS. 2248-2250 depict three variants of the same cell. FIGS. 2249(A)-(B) show the nominal case, whereas the other figures represent intentionally misaligned conditions.

FIGS. 2251-2253 depict three variants of the same cell. FIGS. 2252(A)-(B) show the nominal case, whereas the other figures represent intentionally misaligned conditions.

FIGS. 2254-2256 depict three variants of the same cell. FIGS. 2255(A)-(B) show the nominal case, whereas the other figures represent intentionally misaligned conditions.

FIGS. 2257-2259 depict three variants of the same cell. FIGS. 2258(A)-(B) show the nominal case, whereas the other figures represent intentionally misaligned conditions.

FIGS. 2260-2262 depict three variants of the same cell. FIGS. 2261(A)-(B) show the nominal case, whereas the other figures represent intentionally misaligned conditions.

FIGS. 2263-2265 depict three variants of the same cell. FIGS. 2264(A)-(B) show the nominal case, whereas the other figures represent intentionally misaligned conditions.

FIGS. 2266-2268 depict three variants of the same cell. FIGS. 2267(A)-(B) show the nominal case, whereas the other figures represent intentionally misaligned conditions.

FIGS. 2269-2271 depict three variants of the same cell. FIGS. 2270(A)-(B) show the nominal case, whereas the other figures represent intentionally misaligned conditions.

FIGS. 2272-2274 depict three variants of the same cell. FIGS. 2273(A)-(B) show the nominal case, whereas the other figures represent intentionally misaligned conditions.

FIGS. 2275-2277 depict three variants of the same cell. FIGS. 2276(A)-(B) show the nominal case, whereas the other figures represent intentionally misaligned conditions.

FIGS. 2278-2280 depict three variants of the same cell. FIGS. 2279(A)-(B) show the nominal case, whereas the other figures represent intentionally misaligned conditions.

FIGS. 2281-2282 depict two variants of the same cell. FIGS. 2282(A)-(B) show the nominal case, whereas the other figures represent intentionally misaligned conditions.

FIGS. 2283-2285 depict three variants of the same cell. FIGS. 2284(A)-(B) show the nominal case, whereas the other figures represent intentionally misaligned conditions.

FIGS. 2286-2288 depict three variants of the same cell. FIGS. 2287(A)-(B) show the nominal case, whereas the other figures represent intentionally misaligned conditions.

FIGS. 2289-2290 depict two variants of the same cell. FIGS. 2290(A)-(B) show the nominal case, whereas the other figures represent intentionally misaligned conditions.

FIGS. 2291-2293 depict three variants of the same cell. FIGS. 2292(A)-(B) show the nominal case, whereas the other figures represent intentionally misaligned conditions.

FIGS. 2294-2296 depict three variants of the same cell. FIGS. 2295(A)-(B) show the nominal case, whereas the other figures represent intentionally misaligned conditions.

FIGS. 2297-2299 depict three variants of the same cell. FIGS. 2298(A)-(B) show the nominal case, whereas the other figures represent intentionally misaligned conditions.

FIGS. 2300-2302 depict three variants of the same cell. FIGS. 2301(A)-(B) show the nominal case, whereas the other figures represent intentionally misaligned conditions.

FIGS. 2303-2305 depict three variants of the same cell. FIGS. 2304(A)-(B) show the nominal case, whereas the other figures represent intentionally misaligned conditions.

FIGS. 2306-2308 depict three variants of the same cell. FIGS. 2307(A)-(B) show the nominal case, whereas the other figures represent intentionally misaligned conditions.

FIGS. 2309-2311 depict three variants of the same cell. FIGS. 2310(A)-(B) show the nominal case, whereas the other figures represent intentionally misaligned conditions.

FIGS. 2312-2314 depict three variants of the same cell. FIGS. 2313(A)-(B) show the nominal case, whereas the other figures represent intentionally misaligned conditions.

FIGS. 2345-2347 depict three variants of the same cell. FIGS. 2346(A)-(C) show the nominal case, whereas the other figures represent intentionally misaligned conditions.

FIGS. 2348-2350 depict three variants of the same cell. FIGS. 2349(A)-(C) show the nominal case, whereas the other figures represent intentionally misaligned conditions.

FIGS. 2351-2353 depict three variants of the same cell. FIGS. 2351(A)-(C) show the nominal case, whereas the other figures represent intentionally misaligned conditions.

FIGS. 2354-2356 depict three variants of the same cell. FIGS. 2354(A)-(C) show the nominal case, whereas the other figures represent intentionally misaligned conditions.

FIGS. 2357-2359 depict three variants of the same cell. FIGS. 2358(A)-(C) show the nominal case, whereas the other figures represent intentionally misaligned conditions.

FIGS. 2360-2362 depict three variants of the same cell. FIGS. 2361(A)-(C) show the nominal case, whereas the other figures represent intentionally misaligned conditions.

FIGS. 2363-2365 depict three variants of the same cell. FIGS. 2364(A)-(C) show the nominal case, whereas the other figures represent intentionally misaligned conditions.

FIGS. 2366-2368 depict three variants of the same cell. FIGS. 2367(A)-(C) show the nominal case, whereas the other figures represent intentionally misaligned conditions.

FIGS. 2369-2371 depict three variants of the same cell. FIGS. 2370(A)-(C) show the nominal case, whereas the other figures represent intentionally misaligned conditions.

FIGS. 2372-2374 depict three variants of the same cell. FIGS. 2373(A)-(C) show the nominal case, whereas the other figures represent intentionally misaligned conditions.

FIGS. 2375-2377 depict three variants of the same cell. FIGS. 2376(A)-(C) show the nominal case, whereas the other figures represent intentionally misaligned conditions.

FIGS. 2378-2380 depict three variants of the same cell. FIGS. 2379(A)-(C) show the nominal case, whereas the other figures represent intentionally misaligned conditions.

FIGS. 2381-2383 depict three variants of the same cell. FIGS. 2382(A)-(C) show the nominal case, whereas the other figures represent intentionally misaligned conditions.

FIGS. 2384-2386 depict three variants of the same cell. FIGS. 2385(A)-(C) show the nominal case, whereas the other figures represent intentionally misaligned conditions.

FIGS. 2387-2389 depict three variants of the same cell. FIGS. 2388(A)-(C) show the nominal case, whereas the other figures represent intentionally misaligned conditions.

FIGS. 2390-2392 depict three variants of the same cell. FIGS. 2391(A)-(C) show the nominal case, whereas the other figures represent intentionally misaligned conditions.

FIGS. 2399-2401 depict three variants of the same cell. FIGS. 2399(A)-(C) show the nominal case, whereas the other figures represent intentionally misaligned conditions.

FIGS. 2402-2403 depict two variants of the same cell. The figure set represents intentionally misaligned conditions.

FIGS. 2404-2406 depict three variants of the same cell. FIGS. 2405(A)-(C) show the nominal case, whereas the other figures represent intentionally misaligned conditions.

FIGS. 2407-2409 depict three variants of the same cell. FIGS. 2408(A)-(C) show the nominal case, whereas the other figures represent intentionally misaligned conditions.

FIGS. 2410-2412 depict three variants of the same cell. FIGS. 2411(A)-(C) show the nominal case, whereas the other figures represent intentionally misaligned conditions.

FIGS. 2413-2415 depict three variants of the same cell. FIGS. 2414(A)-(C) show the nominal case, whereas the other figures represent intentionally misaligned conditions.

FIGS. 2416-2418 depict three variants of the same cell. FIGS. 2417(A)-(C) show the nominal case, whereas the other figures represent intentionally misaligned conditions.

FIGS. 2419-2421 depict three variants of the same cell. FIGS. 2420(A)-(C) show the nominal case, whereas the other figures represent intentionally misaligned conditions.

FIGS. 2422-2424 depict three variants of the same cell. FIGS. 2423(A)-(C) show the nominal case, whereas the other figures represent intentionally misaligned conditions.

FIGS. 2425-2427 depict three variants of the same cell. FIGS. 2426(A)-(C) show the nominal case, whereas the other figures represent intentionally misaligned conditions.

FIGS. 2428-2430 depict three variants of the same cell. FIGS. 2429(A)-(C) show the nominal case, whereas the other figures represent intentionally misaligned conditions.

FIGS. 2431-2433 depict three variants of the same cell. FIGS. 2432(A)-(C) show the nominal case, whereas the other figures represent intentionally misaligned conditions.

FIGS. 2434-2436 depict three variants of the same cell. FIGS. 2435(A)-(C) show the nominal case, whereas the other figures represent intentionally misaligned conditions.

FIGS. 2437-2439 depict three variants of the same cell. FIGS. 2438(A)-(C) show the nominal case, whereas the other figures represent intentionally misaligned conditions.

FIGS. 2442-2444 depict three variants of the same cell. FIGS. 2443(A)-(C) show the nominal case, whereas the other figures represent intentionally misaligned conditions.

FIGS. 2445-2447 depict three variants of the same cell. FIGS. 2446(A)-(C) show the nominal case, whereas the other figures represent intentionally misaligned conditions.

FIGS. 2448-2450 depict three variants of the same cell. FIGS. 2449(A)-(C) show the nominal case, whereas the other figures represent intentionally misaligned conditions.

FIGS. 2451-2453 depict three variants of the same cell. FIGS. 2452(A)-(C) show the nominal case, whereas the other figures represent intentionally misaligned conditions.

FIGS. 2454-2456 depict three variants of the same cell. FIGS. 2455(A)-(C) show the nominal case, whereas the other figures represent intentionally misaligned conditions.

FIGS. 2457-2459 depict three variants of the same cell. FIGS. 2458(A)-(C) show the nominal case, whereas the other figures represent intentionally misaligned conditions.

FIGS. 203-223, 236-286, 389-397, 404-409, 485-494, 546-548, 552-554, 621-632, 682, 691, 731-734, 762-785, 848-859, 880-903, 1014-1040, 1096-1119, 1189-1200, 1222-1224, 1234-1238, 1249-1263, 1543-1548, 1687-1698, 1870-1872, 1876-1881, 1885-1902, 1912-1947, 1954-1980, 1984-1993, 2003-2005, 2157-2314, 2343-2344, 2357-2374, and 2404-2461 show depictions of NCEM-enabled fill cells without NCEM pads. Persons skilled in the art will understand that pads of any design (e.g., FIGS. 9A-9IIII, etc.) would be added, either at the left edge with a corresponding leftward extension of the supply rails, or overlying or partially overlying the depicted portion of the cells.

Certain of the claims that follow may contain one or more means-plus-function limitations of the form, "a <cell name> means for enabling NC detection of a GATE-tip-to-tip short." It is applicant's intent that such limitations be construed, pursuant to 35 U.S.C. §112(f), as "the structure of the named cell, or an equivalent structure, that enables detection of a GATE-tip-to-tip short by non-contact measurement."

Additionally, certain of the claims that follow may contain one or more step-plus-function limitations of the form, "a <cell name> step for enabling NC detection of a GATE-tip-to-tip short." It is applicant's intent that such limitations be construed, pursuant to 35 U.S.C. §112(f), as "enabling voltage contrast detection of a GATE-tip-to-tip short by patterning an instance of the named cell, or an equivalent cell."

While the invention has been illustrated with respect to one or more specific implementations, numerous alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular application. Furthermore, to the extent that the terms "including," "includes," "having," "has," "with," or variants thereof are used in either the detailed description or the claims, such terms are intended to be inclusive in a manner similar to the term "comprising." As used herein, the phrase "X comprises one or more of A, B, and C" means that X can include any of the following: either A, B, or C alone; or combinations of two, such as A and B, B and C, and A and C; or combinations of three A, B and C.

What we claim in this application is:

1. On a semiconductor substrate a mesh-style non-contact electrical measurement (NCEM) pad that includes a mask-patterned gate (GATE), a source/drain (AA), a source/drain silicide (TS), a gate contact (GATECNT), and source/drain contact (AACNT) features, comprising:

at least two parallel, elongated AACNT features extending longitudinally in a first direction; and at least two parallel, elongated GATECNT features extending longitudinally in a second direction perpendicular to the first direction, wherein said features are positioned such that each of said AANCT features intersects each of said GATECNT features.

2. A mesh-style NCEM pad, as defined in claim 1, wherein said pad includes at least three parallel, elongated AACNT features that extend longitudinally in the first direction.

3. A mesh-style NCEM pad, as defined in claim 1, wherein said pad includes at least four parallel, elongated AACNT features that extend longitudinally in the first direction.

4. A mesh-style NCEM pad, as defined in claim 1, wherein said pad includes at least five parallel, elongated AACNT features that extend longitudinally in the first direction.

5. A mesh-style NCEM pad, as defined in claim 1, wherein said pad includes at least three parallel, elongated GATECNT features that extend longitudinally in the second direction.

6. A mesh-style NCEM pad, as defined in claim 1, wherein said pad includes at least four parallel, elongated GATECNT features that extend longitudinally in the second direction.

7. A mesh-style NCEM pad, as defined in claim 1, wherein said pad includes at least five parallel, elongated GATECNT features that extend longitudinally in the second direction.

8. A mesh-style NCEM pad, as defined in claim 1, wherein said AACNT features are multi-patterned, with at least some of said elongated AACNT features patterned by a first color (AACNTm1) mask, and at least some of said elongated AACNT features patterned by a second color (AACNTm2) mask.

9. A mesh-style NCEM pad, as defined in claim 1, wherein said AACNT features are multi-patterned, with at least some of said elongated AACNT features patterned by a first color (AACNTm1) mask, at least some of said elongated AACNT features patterned by a second color (AACNTm2) mask, and at least some of said elongated AACNT features patterned by a third color (AACNTm3) mask.

10. A mesh-style NCEM pad, as defined in claim 1, wherein said GATECNT features are multi-patterned, with at least some of said elongated GATECNT features patterned by a first color (GATECNTm1) mask, and at least some of said elongated GATECNT features patterned by a second color (GATECNTm2) mask.

11. A mesh-style NCEM pad, as defined in claim 1, wherein said GATECNT features are multi-patterned, with at least some of said elongated GATECNT features patterned by a first color (GATECNTm1) mask, at least some of said elongated GATECNT features patterned by a second color (GATECNTm2) mask, and at least some of said elongated GATECNT features patterned by a third color (GATECNTm3) mask.

12. A mesh-style NCEM pad, as defined in claim 1, wherein said pad is contained within a fill cell selected from the list the consists of:

AA-tip-to-tip-short-configured, NCEM-enabled fill cells;
AACNT-tip-to-tip-short-configured, NCEM-enabled fill cells;
AACNT-AA-tip-to-tip-short-configured, NCEM-enabled fill cells;
AACNT-TS-tip-to-tip-short-configured, NCEM-enabled fill cells;
TS-tip-to-tip-short-configured, NCEM-enabled fill cells;
GATE-tip-to-tip-short-configured, NCEM-enabled fill cells;
GATECNT-GATE-tip-to-tip-short-configured, NCEM-enabled fill cells;
GATECNT-tip-to-tip-short-configured, NCEM-enabled fill cells;
GATECNT-AACNT-tip-to-tip-short-configured, NCEM-enabled fill cells;
M1-tip-to-tip-short-configured, NCEM-enabled fill cells;
V0-tip-to-tip-short-configured, NCEM-enabled fill cells;
M1-V0-tip-to-tip-short-configured, NCEM-enabled fill cells;
first interconnect via layer (V1)-M1-tip-to-tip-short-configured, NCEM-enabled fill cells;
V1-tip-to-tip-short-configured, NCEM-enabled fill cells;
second wiring layer (M2)-tip-to-tip-short-configured, NCEM-enabled fill cells;
M2-V1-tip-to-tip-short-configured, NCEM-enabled fill cells;
second interconnect via layer (V2)-M2-tip-to-tip-short-configured, NCEM-enabled fill cells;
third wiring layer (M3)-tip-to-tip-short-configured, NCEM-enabled fill cells;
V2-tip-to-tip-short-configured, NCEM-enabled fill cells;
M3-V2-tip-to-tip-short-configured, NCEM-enabled fill cells;
AA-tip-to-side-short-configured, NCEM-enabled fill cells;
AACNT-tip-to-side-short-configured, NCEM-enabled fill cells;
AACNT-AA-tip-to-side-short-configured, NCEM-enabled fill cells;
GATE-AA-tip-to-side-short-configured, NCEM-enabled fill cells;
GATECNT-GATE-tip-to-side-short-configured, NCEM-enabled fill cells;
GATECNT-tip-to-side-short-configured, NCEM-enabled fill cells;
TS-GATECNT-tip-to-side-short-configured, NCEM-enabled fill cells;
GATECNT-AACNT-tip-to-side-short-configured, NCEM-enabled fill cells;
GATECNT-AACNT-TS-tip-to-side-short-configured, NCEM-enabled fill cells;
M1-tip-to-side-short-configured, NCEM-enabled fill cells;
V0-tip-to-side-short-configured, NCEM-enabled fill cells;
M1-V0-tip-to-side-short-configured, NCEM-enabled fill cells;
V1-M1-tip-to-side-short-configured, NCEM-enabled fill cells;
V1-tip-to-side-short-configured, NCEM-enabled fill cells;
M2-tip-to-side-short-configured, NCEM-enabled fill cells;
M2-V1-tip-to-side-short-configured, NCEM-enabled fill cells;
V2-M2-tip-to-side-short-configured, NCEM-enabled fill cells;
M3-tip-to-side-short-configured, NCEM-enabled fill cells;
V2-tip-to-side-short-configured, NCEM-enabled fill cells;
M3-V2-tip-to-side-short-configured, NCEM-enabled fill cells;
AA-side-to-side-short-configured, NCEM-enabled fill cells;
AACNT-side-to-side-short-configured, NCEM-enabled fill cells;
AACNT-AA-side-to-side-short-configured, NCEM-enabled fill cells;
AACNT-GATE-side-to-side-short-configured, NCEM-enabled fill cells;
GATE-side-to-side-short-configured, NCEM-enabled fill cells;
GATECNT-GATE-side-to-side-short-configured, NCEM-enabled fill cells;
TS-GATE-side-to-side-short-configured, NCEM-enabled fill cells;
GATECNT-side-to-side-short-configured, NCEM-enabled fill cells;
GATECNT-AACNT-side-to-side-short-configured, NCEM-enabled fill cells;
M1-side-to-side-short-configured, NCEM-enabled fill cells;
V0-side-to-side-short-configured, NCEM-enabled fill cells;
M1-V0-side-to-side-short-configured, NCEM-enabled fill cells;
V1-M1-side-to-side-short-configured, NCEM-enabled fill cells;
V1-side-to-side-short-configured, NCEM-enabled fill cells;
M2-side-to-side-short-configured, NCEM-enabled fill cells;
M2-V1-side-to-side-short-configured, NCEM-enabled fill cells;
V2-M2-side-to-side-short-configured, NCEM-enabled fill cells;
M3-side-to-side-short-configured, NCEM-enabled fill cells;
V2-side-to-side-short-configured, NCEM-enabled fill cells;
M3-V2-side-to-side-short-configured, NCEM-enabled fill cells;
AA-L-shape-interlayer-short-configured, NCEM-enabled fill cells;
AACNT-L-shape-interlayer-short-configured, NCEM-enabled fill cells;
AACNT-AA-L-shape-interlayer-short-configured, NCEM-enabled fill cells;
GATE-AA-L-shape-interlayer-short-configured, NCEM-enabled fill cells;
GATE-TS-L-shape-interlayer-short-configured, NCEM-enabled fill cells;
GATECNT-GATE-L-shape-interlayer-short-configured, NCEM-enabled fill cells;
GATECNT-AA-L-shape-interlayer-short-configured, NCEM-enabled fill cells;
GATECNT-TS-L-shape-interlayer-short-configured, NCEM-enabled fill cells;
GATECNT-AACNT-L-shape-interlayer-short-configured, NCEM-enabled fill cells;

V0-AA-L-shape-interlayer-short-configured, NCEM-enabled fill cells;
V0-TS-L-shape-interlayer-short-configured, NCEM-enabled fill cells;
V0-AACNT-L-shape-interlayer-short-configured, NCEM-enabled fill cells;
V0-GATE-L-shape-interlayer-short-configured, NCEM-enabled fill cells;
V0-GATECNT-L-shape-interlayer-short-configured, NCEM-enabled fill cells;
M1-AACNT-L-shape-interlayer-short-configured, NCEM-enabled fill cells;
M1-GATECNT-L-shape-interlayer-short-configured, NCEM-enabled fill cells;
M1-V0-L-shape-interlayer-short-configured, NCEM-enabled fill cells;
V1-M1-L-shape-interlayer-short-configured, NCEM-enabled fill cells;
V1-V0-L-shape-interlayer-short-configured, NCEM-enabled fill cells;
M2-M1-L-shape-interlayer-short-configured, NCEM-enabled fill cells;
M2-V1-L-shape-interlayer-short-configured, NCEM-enabled fill cells;
V2-V1-L-shape-interlayer-short-configured, NCEM-enabled fill cells;
V2-M2-L-shape-interlayer-short-configured, NCEM-enabled fill cells;
M3-M2-L-shape-interlayer-short-configured, NCEM-enabled fill cells;
M3-V2-L-shape-interlayer-short-configured, NCEM-enabled fill cells;
AA-diagonal-short-configured, NCEM-enabled fill cells;
TS-diagonal-short-configured, NCEM-enabled fill cells;
AACNT-diagonal-short-configured, NCEM-enabled fill cells;
AACNT-AA-diagonal-short-configured, NCEM-enabled fill cells;
GATE-diagonal-short-configured, NCEM-enabled fill cells;
GATE-AACNT-diagonal-short-configured, NCEM-enabled fill cells;
GATECNT-GATE-diagonal-short-configured, NCEM-enabled fill cells;
GATECNT-diagonal-short-configured, NCEM-enabled fill cells;
GATECNT-AACNT-diagonal-short-configured, NCEM-enabled fill cells;
M1-diagonal-short-configured, NCEM-enabled fill cells;
V0-diagonal-short-configured, NCEM-enabled fill cells;
M1-V0-diagonal-short-configured, NCEM-enabled fill cells;
V1-M1-diagonal-short-configured, NCEM-enabled fill cells;
V1-diagonal-short-configured, NCEM-enabled fill cells;
M2-diagonal-short-configured, NCEM-enabled fill cells;
M2-V1-diagonal-short-configured, NCEM-enabled fill cells;
M3-diagonal-short-configured, NCEM-enabled fill cells;
V2-M2-diagonal-short-configured, NCEM-enabled fill cells;
V2-diagonal-short-configured, NCEM-enabled fill cells;
M3-V2-diagonal-short-configured, NCEM-enabled fill cells;
AA-corner-short-configured, NCEM-enabled fill cells;
AACNT-corner-short-configured, NCEM-enabled fill cells;
AACNT-AA-corner-short-configured, NCEM-enabled fill cells;
GATE-corner-short-configured, NCEM-enabled fill cells;
GATECNT-GATE-corner-short-configured, NCEM-enabled fill cells;
GATECNT-TS-corner-short-configured, NCEM-enabled fill cells;
GATECNT-corner-short-configured, NCEM-enabled fill cells;
GATECNT-AA-corner-short-configured, NCEM-enabled fill cells;
GATECNT-AACNT-corner-short-configured, NCEM-enabled fill cells;
M1-corner-short-configured, NCEM-enabled fill cells;
V0-corner-short-configured, NCEM-enabled fill cells;
M1-V0-corner-short-configured, NCEM-enabled fill cells;
V1-M1-corner-short-configured, NCEM-enabled fill cells;
V1-corner-short-configured, NCEM-enabled fill cells;
M2-corner-short-configured, NCEM-enabled fill cells;
M2-V1-corner-short-configured, NCEM-enabled fill cells;
M3-corner-short-configured, NCEM-enabled fill cells;
V2-M2-corner-short-configured, NCEM-enabled fill cells;
V2-corner-short-configured, NCEM-enabled fill cells;
M3-V2-corner-short-configured, NCEM-enabled fill cells;
GATE-AA-interlayer-overlap-short-configured, NCEM-enabled fill cells;
GATE-AACNT-interlayer-overlap-short-configured, NCEM-enabled fill cells;
GATE-TS-interlayer-overlap-short-configured, NCEM-enabled fill cells;
GATECNT-TS-interlayer-overlap-short-configured, NCEM-enabled fill cells;
GATECNT-AA-interlayer-overlap-short-configured, NCEM-enabled fill cells;
V0-AA-interlayer-overlap-short-configured, NCEM-enabled fill cells;
V0-AACNT-interlayer-overlap-short-configured, NCEM-enabled fill cells;
V0-TS-interlayer-overlap-short-configured, NCEM-enabled fill cells;
V0-GATE-interlayer-overlap-short-configured, NCEM-enabled fill cells;
M1-GATECNT-interlayer-overlap-short-configured, NCEM-enabled fill cells;
M1-AACNT-interlayer-overlap-short-configured, NCEM-enabled fill cells;
V1-V0-interlayer-overlap-short-configured, NCEM-enabled fill cells;
M2-M1-interlayer-overlap-short-configured, NCEM-enabled fill cells;
V2-V1-interlayer-overlap-short-configured, NCEM-enabled fill cells;
M3-M2-interlayer-overlap-short-configured, NCEM-enabled fill cells;
V0-GATECNT-via-chamfer-short-configured, NCEM-enabled fill cells;
V0-AACNT-via-chamfer-short-configured, NCEM-enabled fill cells;
V1-M1-via-chamfer-short-configured, NCEM-enabled fill cells;
V2-M2-via-chamfer-short-configured, NCEM-enabled fill cells;

third interconnect via layer (V3)-M3-via-chamfer-short-configured, NCEM-enabled fill cells;
V0-merged-via-short-configured, NCEM-enabled fill cells;
V1-merged-via-short-configured, NCEM-enabled fill cells;
V2-merged-via-short-configured, NCEM-enabled fill cells;
AA-snake-open-configured, NCEM-enabled fill cells;
TS-snake-open-configured, NCEM-enabled fill cells;
AACNT-snake-open-configured, NCEM-enabled fill cells;
GATE-snake-open-configured, NCEM-enabled fill cells;
GATECNT-snake-open-configured, NCEM-enabled fill cells;
V0-snake-open-configured, NCEM-enabled fill cells;
M1-snake-open-configured, NCEM-enabled fill cells;
M1-V0-AACNT-snake-open-configured, NCEM-enabled fill cells;
V1-snake-open-configured, NCEM-enabled fill cells;
M2-snake-open-configured, NCEM-enabled fill cells;
V2-snake-open-configured, NCEM-enabled fill cells;
M3-snake-open-configured, NCEM-enabled fill cells;
AA-stitch-open-configured, NCEM-enabled fill cells;
TS-stitch-open-configured, NCEM-enabled fill cells;
AACNT-stitch-open-configured, NCEM-enabled fill cells;
GATECNT-stitch-open-configured, NCEM-enabled fill cells;
V0-stitch-open-configured, NCEM-enabled fill cells;
M1-stitch-open-configured, NCEM-enabled fill cells;
V1-stitch-open-configured, NCEM-enabled fill cells;
M2-stitch-open-configured, NCEM-enabled fill cells;
V2-stitch-open-configured, NCEM-enabled fill cells;
M3-stitch-open-configured, NCEM-enabled fill cells;
AACNT-TS-via-open-configured, NCEM-enabled fill cells;
AACNT-AA-via-open-configured, NCEM-enabled fill cells;
TS-AA-via-open-configured, NCEM-enabled fill cells;
GATECNT-GATE-via-open-configured, NCEM-enabled fill cells;
GATECNT-AACNT-via-open-configured, NCEM-enabled fill cells;
GATECNT-AACNT-GATE-via-open-configured, NCEM-enabled fill cells;
V0-GATECNT-via-open-configured, NCEM-enabled fill cells;
V0-AA-via-open-configured, NCEM-enabled fill cells;
V0-TS-via-open-configured, NCEM-enabled fill cells;
V0-AACNT-via-open-configured, NCEM-enabled fill cells;
V0-GATE-via-open-configured, NCEM-enabled fill cells;
V0-via-open-configured, NCEM-enabled fill cells;
M1-V0-via-open-configured, NCEM-enabled fill cells;
V1-via-open-configured, NCEM-enabled fill cells;
V1-M1-via-open-configured, NCEM-enabled fill cells;
V1-M2-via-open-configured, NCEM-enabled fill cells;
M1-GATECNT-via-open-configured, NCEM-enabled fill cells;
M1-AANCT-via-open-configured, NCEM-enabled fill cells;
V2-M2-via-open-configured, NCEM-enabled fill cells;
V2-M3-via-open-configured, NCEM-enabled fill cells;
V3-via-open-configured, NCEM-enabled fill cells;
fourth wiring layer (M4)-V3-via-open-configured, NCEM-enabled fill cells;
fifth wiring layer (M5)-fourth interconnect via layer (V4)-via-open-configured, NCEM-enabled fill cells;
M1-metal-island-open-configured, NCEM-enabled fill cells;
M2-metal-island-open-configured, NCEM-enabled fill cells;
M3-metal-island-open-configured, NCEM-enabled fill cells;
V0-merged-via-open-configured, NCEM-enabled fill cells;
V0-AACNT-merged-via-open-configured, NCEM-enabled fill cells;
V0-GATECNT-merged-via-open-configured, NCEM-enabled fill cells;
V1-merged-via-open-configured, NCEM-enabled fill cells;
V2-merged-via-open-configured, NCEM-enabled fill cells;
V1-M1-merged-via-open-configured, NCEM-enabled fill cells; and,
V2-M2-merged-via-open-configured, NCEM-enabled fill cells.

13. An NCEM pad assembly that includes:
a mesh-style NCEM pad as defined in claim 1; and
an upper layer NCEM pad overlying the mesh-style NCEM pad, said upper layer NCEM pad comprising:
one or more mask-patterned features, in a first wiring layer (M1), that substantially cover the mesh-style NCEM pad; and
one or more mask-patterned features, in a via to interconnect stack (VO) layer, that provide electrical connection(s) between the M1 feature(s) and the mesh-style NCEM pad.

14. An NCEM pad assembly, as defined in claim 13, wherein said V0 features are positioned at the intersections of the underlying AACNT and GATECNT features.

15. An NCEM pad assembly, as defined in claim 13, wherein said V0 features are positioned to avoid intersections of the underlying AACNT and GATECNT features.

16. An NCEM pad assembly, as defined in claim 13, wherein said one or more M1 features include multiple parallel, elongated M1 features.

17. An NCEM pad assembly, as defined in claim 16, wherein said elongated M1 features are multi-patterned, with at least some of said elongated M1 features patterned by a first color (M1m1) mask, and at least some of said elongated M1 features patterned by a second color (M1m2) mask.

18. An NCEM pad assembly, as defined in claim 16, wherein said elongated M1 features are multi-patterned, with at least some of said elongated M1 features patterned by a first color (M1m1) mask, at least some of said elongated M1 features patterned by a second color (M1m2) mask, and at least some of said elongated M1 features patterned by a third color (M1m3) mask.

* * * * *